(12) United States Patent
Kotian et al.

(10) Patent No.: US 11,021,458 B2
(45) Date of Patent: Jun. 1, 2021

(54) SUBSTITUTED BENZOFURAN, BENZOPYRROLE, BENZOTHIOPHENE, AND STRUCTURALLY RELATED COMPLEMENT INHIBITORS

(71) Applicant: BioCryst Pharmaceuticals, Inc., Durham, NC (US)

(72) Inventors: Pravin L. Kotian, Hoover, AL (US); Yarlagadda S. Babu, Birmingham, AL (US); Weihe Zhang, Vestavia, AL (US); Peng-Cheng Lu, Hoover, AL (US); Minwan Wu, Vestavia Hills, AL (US); Wei Lv, Hoover, AL (US); Trung Xuan Nguyen, Hoover, AL (US); Zhao Dang, Vestavia Hills, AL (US); Venkat R. Chintareddy, Vestavia Hills, AL (US); V. Satish Kumar, Birmingham, AL (US); Krishnan Raman, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 9 days.

(21) Appl. No.: 16/511,642

(22) Filed: Jul. 15, 2019

(65) Prior Publication Data

US 2019/0345135 A1 Nov. 14, 2019

Related U.S. Application Data

(63) Continuation of application No. PCT/US2019/026054, filed on Apr. 5, 2019.

(60) Provisional application No. 62/654,108, filed on Apr. 6, 2018.

(51) Int. Cl.
| | |
|---|---|
| *C07D 401/10* | (2006.01) |
| *C07D 209/12* | (2006.01) |
| *C07D 261/20* | (2006.01) |
| *C07D 307/80* | (2006.01) |
| *C07D 333/64* | (2006.01) |
| *C07D 401/12* | (2006.01) |
| *C07D 405/10* | (2006.01) |

(52) U.S. Cl.
CPC ......... *C07D 401/10* (2013.01); *C07D 209/12* (2013.01); *C07D 261/20* (2013.01); *C07D 307/80* (2013.01); *C07D 333/64* (2013.01); *C07D 401/12* (2013.01); *C07D 405/10* (2013.01)

(58) Field of Classification Search
CPC .................................................... C07D 401/10
See application file for complete search history.

(56) References Cited

U.S. PATENT DOCUMENTS

| | | |
|---|---|---|
| 3,377,387 A | 4/1968 | Bachman et al. |
| 6,369,227 B1 | 4/2002 | Lam et al. |
| 6,403,583 B1 | 6/2002 | Lam et al. |
| 6,500,855 B1 | 12/2002 | Lam et al. |
| 6,602,871 B2 | 8/2003 | Lam et al. |

(Continued)

FOREIGN PATENT DOCUMENTS

| | | | |
|---|---|---|---|
| AR | 2016-292970 | * | 2/2016 |
| WO | WO-2000/038683 A1 | | 7/2000 |

(Continued)

OTHER PUBLICATIONS

Wermuth, Camille G. "Molecular Variation Based on Isosteric Replacements" in Chapter 13, The Practice of Medicinal Chemistry, Academic: 1996, pp. 203-237.*
International Search Report and Written Opinion for International Application No. PCT/US2019/26054 dated Aug. 2, 2019.
Shagufta et al., "An insight into the therapeutic potential of quinazoline derivatives as anticancer agents," MedChemComm, 8: 871-885 (2017).

(Continued)

*Primary Examiner* — David K O'Dell
(74) *Attorney, Agent, or Firm* — Dana M. Gordon; Foley Hoag LLP

(57) ABSTRACT

Disclosed are compounds of formulae I and II, and pharmaceutically acceptable salts and prodrugs thereof, which are inhibitors of the complement system. Also provided are pharmaceutical compositions comprising such a compound, and methods of using the compounds and compositions in the treatment or prevention of a disease or condition characterized by aberrant complement system activity.

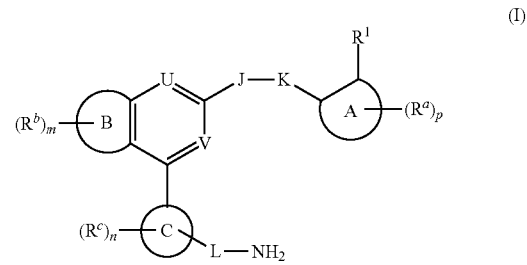

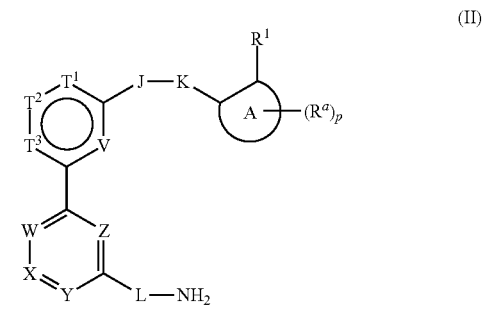

12 Claims, No Drawings

(56) References Cited

U.S. PATENT DOCUMENTS

| | | |
|---|---|---|
| 7,442,808 B2 | 10/2008 | Ge et al. |
| 9,056,874 B2 | 6/2015 | Adams et al. |
| 2016/0145247 A1 | 5/2016 | Belanger et al. |

FOREIGN PATENT DOCUMENTS

| | | | |
|---|---|---|---|
| WO | WO-2000/039102 A1 | 7/2000 | |
| WO | WO-2000/039108 A1 | 7/2000 | |
| WO | WO-2008027483 A1 * | 3/2008 | ........... C07D 405/04 |
| WO | WO-2015/009977 A1 | 1/2015 | |
| WO | WO-2016/088082 A1 | 6/2016 | |
| WO | WO-2017/136395 A1 | 8/2017 | |
| WO | WO-2019/057946 A1 | 3/2019 | |
| WO | WO-2019/195720 A1 | 10/2019 | |

OTHER PUBLICATIONS

Certified priority document file history U.S. Appl. No. 62/562,843, filed Sep. 25, 2017.
Invitation to Pay Additional Fees and, Where Applicable, Protest Fee, dated Jun. 10, 2019, in International Application No. PCT/US19/26054.
Pubchem CID 14528241 (Create Date: Feb. 9, 2007).

* cited by examiner

SUBSTITUTED BENZOFURAN, BENZOPYRROLE, BENZOTHIOPHENE, AND STRUCTURALLY RELATED COMPLEMENT INHIBITORS

RELATED APPLICATIONS

This application is a continuation of International Patent Application No. PCT/US2019/26054, filed Apr. 5, 2019, which claims the benefit of priority to U.S. Provisional Patent Application Ser. No. 62/654,108, filed Apr. 6, 2018.

BACKGROUND OF THE INVENTION

The complement system is a branch of an organism's immune system that enhances the ability of antibodies and phagocytic cells to destroy and remove foreign particles (e.g., pathogens) from the organism. The complement system comprises a set of plasma proteins that act together to attack extracellular forms of pathogens and induce a series of inflammatory responses to help fight infection. Complement activation can occur through several pathways. For example, complement activation can occur spontaneously in response to certain pathogens or by antibody binding to a pathogen. When complement proteins are activated a cascade is triggered by which one complement protein induces the activation of the next protein in the sequence. The activation of a small number of complement proteins at the start of the pathway is hugely amplified by each successive enzymatic reaction, resulting in the rapid generation of a disproportionately large complement response. (Marrides, S. *Pharmacological Reviews* 1998, Vol. 50, pages 59-88). In healthy organisms there are regulatory mechanisms to prevent uncontrolled complement activation.

When activated, complement proteins can bind to a pathogen, opsonizing them for engulfment by phagocytes bearing receptors for complement. Then, small fragments of some complement proteins act as chemoattractants to recruit more phagocytes to the site of complement activation, and also to activate these phagocytes. Next, the complement proteins create holes or pores in the invading organisms, leading to their destruction. While complement plays an important role in protecting the body from foreign organisms, it can also destroy healthy cells and tissue. The inappropriate activation of complement is implicated in a long list of disease pathologies (Morgan, B. *Eur J Clin Invest* 1994, Vol. 24, pages 219-228) affecting the immune, renal, cardiovascular, and neurological systems. Accordingly, there exists a need to develop further complement inhibitors, which have therapeutic potential in the treatment of numerous disorders.

SUMMARY OF THE INVENTION

In certain aspects, the invention provides compounds having the structure of formula (I), and pharmaceutically acceptable salts and prodrugs thereof:

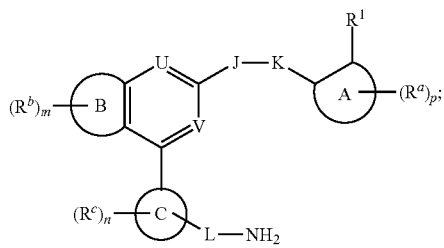

(I)

wherein:
ring

is aryl, heteroaryl, cycloalkyl, or heterocycloalkyl;
ring

is aryl, heteroaryl, heterocycloalkyl, or cycloalkyl;
ring

is aryl or heteroaryl;

$R^a$, independently for each occurrence, is halogen, cyano, hydroxy, —NH$_2$, —NH(Ac), —NH(alkyl), —NH(cycloalkyl), —NH(heterocycloalkyl), —NH(aryl), —NH(heteroaryl), —N(alkyl)$_2$, —NHC(O)(alkyl), —CH(alkyl)NH$_2$, —CH(hydroxyalkyl)NH$_2$, —CH(haloalkyl)NH$_2$, —CH(cycloalkyl)NH$_2$, —CH(heterocycloalkyl)NH$_2$, —CH(aryl)NH$_2$, —CH(heteroaryl)NH$_2$, —CH$_2$NHC(O)(alkyl), —C(O)NH$_2$, —C(O)(alkyl), —SO$_2$NH$_2$, —SO$_2$(cycloalkyl), —SO$_2$(heterocycloalkyl), —SO$_2$(alkyl), —SO$_2$(aryl), or —SO$_2$(heteroaryl); or is selected from the group consisting of substituted or unsubstituted aryl, heteroaryl, arylalkyl, heteroarylalkyl, cycloalkyl, heterocycloalkyl, alkoxy, alkyl, (cycloalkyl)alkyl, (heterocycloalkyl)alkyl, hydroxyalkyl, aminoalkyl, and haloalkyl;

$R^b$, independently for each occurrence, is halogen, cyano, —CH$_2$(OCH$_2$CH$_2$)$_q$OCH$_3$, -alkylene-(branched or unbranched polyethylene glycol), -alkylene-O-(branched or unbranched polyethylene glycol), or —NR$^j$R$^k$; or is selected from the group consisting of substituted or unsubstituted alkyl, haloalkyl, hydroxyalkyl, alkoxyalkyl, (hydroxy)haloalkyl, hydroxy(cycloalkyl)alkyl, (cycloalkyl)alkyl, (heterocycloalkyl)alkyl, arylalkyl, heteroarylalkyl, (heteroarylalkoxy)alkyl, (arylalkoxy)alkyl, (aryloxy)alkyl, ((cycloalkyl)alkoxy)alkyl, ((heterocycloalkyl)alkoxy)alkyl, cycloalkyl, heterocycloalkyl, aryl, heteroaryl, -alkylene-NR$^j$R$^k$, tosyl, —SO$_2$(alkyl), —SO$_2$(cycloalkyl), —CO(alkyl), —CO(aryl), —CO(heteroaryl), —CO(cycloalkyl), —CO(heterocycloalkyl), —CONH(alkyl), —CONH(arylalkyl), —CONH(heteroarylalkyl), —CON(alkyl)$_2$, —CONH(heterocycloalkyl), and —CONH(cycloalkyl);

$R^c$, independently for each occurrence, is selected from the group consisting of halogen, —OH, —NR$^j$R$^k$, alkoxy, alkyl, cycloalkyl, and heterocycloalkyl;

$R^1$ is selected from the group consisting of —NH$_2$, —COOH, —CH$_2$COOH, —CH(NH(CO)(alkyl))COOH, —CH(NH(CO)(arylalkyl))COOH, —CH(NH(CO)(cycloalkyl))COOH, —CH(NH(CO)(aryl substituted cycloalkyl))COOH, —CH(NH(CO)(heteroaryl substituted cycloalkyl))COOH, —CH(S(alkyl))COOH, —CO(NH)CH$_2$(substituted or unsubstituted aryl), —CO(NH)CH₂(substituted or unsubstituted heteroaryl), —CO(NH)(substituted or unsubstituted aryl), —CO(NH)(substituted or unsubstituted heteroaryl), and —CH₂(tetrazolyl);

n is 0, 1, 2, 3, or 4;
m is 0, 1, 2, 3, or 4;
p is 0, 1, 2, 3, or 4;
q is an integer from 1-20;
J is —C(O)—, —NH—, —CH₂—, —O—, —S—, —S(O)—, —SO₂—, —N(alkyl)-, —CH(alkyl)-, —CH(cycloalkyl)-, —N((C(O)O)arylalkyl)-, —N((C(O)O)heteroarylalkyl)-, or —N(C(O)arylalkyl)-;
K is —C(O)—, —NH—, —CH₂—, —O—, —S—, —S(O)—, —SO₂—, —N(alkyl)-, —CH(alkyl)-, —CH(cycloalkyl)-, —N((C(O)O)arylalkyl)-, —N((C(O)O)heteroarylalkyl)-, or —N(C(O)arylalkyl)-;
wherein at least one of J and K is —C(O)—, —CH₂—, or —CH(alkyl)-;
L is selected from the group consisting of a bond, —CH₂—, —CH₂CH₂—, —CHR²—, —CF₂—, —CFR²—, —C(O)—, —C(=NR$^L$)—, —C(=CHR$^L$)—, —S(O)₂—, and —S(O)—;
wherein R$^L$ is H or alkyl;
or wherein R$^L$ and an occurrence of R$^c$ taken together with the intervening atoms form a substituted or unsubstituted heteroaryl ring;
R² is alkyl, cycloalkyl, hydroxyalkyl, or haloalkyl;
R$^j$ and R$^k$ are each independently H or are selected from the group consisting of substituted or unsubstituted alkyl, aminoalkyl, (heterocycloalkyl)alkyl, heterocycloalkyl, aryl, arylalkyl, heteroaryl, heteroarylalkyl, —CO(aryl), —CO(arylalkyl), —CO(heteroarylalkyl), and —CO((heterocycloalkyl)alkyl);
U is N or CR³;
R³ is H, halogen, alkyl, cycloalkyl, aryl, heteroaryl, alkoxy, haloalkyl, —CN, —CONH₂, —CO₂H, —CH₂CO₂H, —NH₂, hydroxyalkyl, aminoalkyl, —OH, —NH(alkyl), —N(alkyl)₂, thioalkyl, or —S(alkyl);
V is N, CH, C(halogen), or C(alkyl); and
the stereochemical configuration at any chiral center is R, S, or a mixture of R and S.

In certain aspects, the invention provides compounds having the structure of formula (II-g), and pharmaceutically acceptable salts and prodrugs thereof:

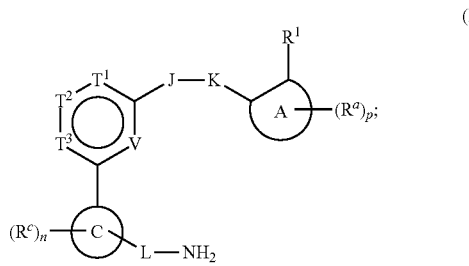

(II-g)

wherein:
ring

is aryl, heteroaryl, cycloalkyl, or heterocycloalkyl;

ring

is aryl or heteroaryl;
R$^a$, independently for each occurrence, is halogen, cyano, hydroxy, —NH₂, —NH(Ac), —NH(alkyl), —NH(cycloalkyl), —NH(heterocycloalkyl), —NH(aryl), —NH(heteroaryl), —N(alkyl)₂, —NHC(O)(alkyl), —CH(alkyl)NH₂, —CH(hydroxyalkyl)NH₂, —CH(haloalkyl)NH₂, —CH(cycloalkyl)NH₂, —CH(heterocycloalkyl)NH₂, —CH(aryl)NH₂, —CH(heteroaryl)NH₂, —CH₂NHC(O)(alkyl), —C(O)NH₂, —C(O)(alkyl), —SO₂NH₂, —SO₂(cycloalkyl), —SO₂(heterocycloalkyl), —SO₂(alkyl), —SO₂(aryl), or —SO₂(heteroaryl);
or is selected from the group consisting of substituted or unsubstituted aryl, heteroaryl, arylalkyl, heteroarylalkyl, cycloalkyl, heterocycloalkyl, alkoxy, alkyl, (cycloalkyl)alkyl, (heterocycloalkyl)alkyl, hydroxyalkyl, aminoalkyl, and haloalkyl;
T¹ is N, CH, NR$^{T1}$, or CR$^{T1}$;
T² is NR$^{T2}$ or CR$^{T2}$;
T³ is N, CH, NR$^{T3}$, or CR$^{T3}$;
wherein:
(a) T¹ is CR$^{T1}$ or NR$^{T1}$, wherein R$^{T1}$ and R$^{T2}$, taken together with the intervening atoms, form an optionally substituted cycloalkyl, aryl, or heteroaryl ring; and T³ is N or CH; or
(b) T³ is CR$^{T3}$ or NR$^{T3}$; wherein R$^{T3}$ and R$^{T2}$, taken together with the intervening atoms, form an optionally substituted heteroaryl ring; and
T¹ is N or CH; and
at least one of (a) T² is NR$^{T2}$, (b) T³ is N, or (c) T¹ is NR$^{T1}$;
R¹ is selected from the group consisting of —NH₂, —COOH, —CH₂COOH, —CH(NH(CO)(alkyl))COOH, —CH(NH(CO)(arylalkyl))COOH, —CH(NH(CO)(cycloalkyl))COOH, —CH(NH(CO)(aryl substituted cycloalkyl))COOH, —CH(NH(CO)(heteroaryl substituted cycloalkyl))COOH, —CH(S(alkyl))COOH, —CO(NH)CH₂(substituted or unsubstituted aryl), —CO(NH)CH₂(substituted or unsubstituted heteroaryl), —CO(NH)(substituted or unsubstituted aryl), —CO(NH)(substituted or unsubstituted heteroaryl), and —CH₂(tetrazolyl);
n is 0, 1, 2, 3, or 4;
p is 0, 1, 2, 3, or 4;
J is —C(O)—, —NH—, —CH₂—, —O—, —S—, —S(O)—, —SO₂—, —N(alkyl)-, —CH(alkyl)-, —CH(cycloalkyl)-, —N((C(O)O)arylalkyl)-, —N((C(O)O)heteroarylalkyl)-, or —N(C(O)arylalkyl)-;
K is —C(O)—, —NH—, —CH₂—, —O—, —S—, —S(O)—, —SO₂—, —N(alkyl)-, —CH(alkyl)-, —CH(cycloalkyl)-, —N((C(O)O)arylalkyl)-, —N((C(O)O)heteroarylalkyl)-, or —N(C(O)arylalkyl)-;
R$^c$, independently for each occurrence, is selected from the group consisting of halogen, —OH, —NR$^j$R$^k$, alkoxy, alkyl, cycloalkyl, and heterocycloalkyl;
L is selected from the group consisting of a bond, —CH₂—, —CH₂CH₂—, —CHR²—, —CF₂—, —CFR²—, —C(O)—, —C(=NR$^L$)—, —C(=CHR$^L$)—, —S(O)₂—, and —S(O)—;
wherein R$^L$ is H or alkyl;

or wherein $R^L$ and an occurrence of $R^c$ taken together with the intervening atoms form a substituted or unsubstituted heteroaryl ring;
$R^2$ is alkyl, cycloalkyl, hydroxyalkyl, or haloalkyl;
V is N or CH; and
the stereochemical configuration at any chiral center is R, S, or a mixture of R and S.

In further aspects, the invention provides compounds having the structure of formula (II), and pharmaceutically acceptable salts and prodrugs thereof:

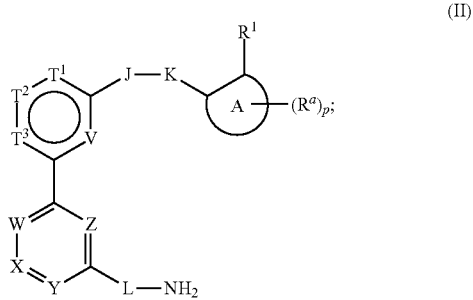

(II)

wherein:
ring

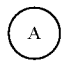

is aryl, heteroaryl, cycloalkyl, or heterocycloalkyl;
$R^a$, independently for each occurrence, is selected from the group consisting of halogen, cyano, hydroxy, —$NH_2$, —NH(Ac), —NH(alkyl), —N(alkyl)$_2$, —NHC(O)(alkyl), —$CH_2$NHC(O)(alkyl), —C(O)$NH_2$, —C(O)(alkyl), optionally substituted aryl, optionally substituted heteroaryl, cycloalkyl, alkoxy, alkyl, (cycloalkyl)alkyl, hydroxyalkyl, aminoalkyl, and haloalkyl;
$T^1$ is N, CH, $NR^{T1}$, or $CR^{T1}$;
$T^2$ is $NR^{T2}$ or $CR^{T2}$;
$T^3$ is N, CH, $NR^{T3}$, or $CR^{T3}$;
wherein:
(a) $T^1$ is $CR^{T1}$ or $NR^{T1}$, wherein $R^{T1}$ and $R^{T2}$, taken together with the intervening atoms, form an optionally substituted cycloalkyl, aryl, or heteroaryl ring; and
$T^3$ is N or CH; or
(b) $T^3$ is $CR^{T3}$ or $NR^{T3}$; wherein $R^{T3}$ and $R^{T2}$, taken together with the intervening atoms, form an optionally substituted heteroaryl ring; and
$T^1$ is N or CH; and
at least one of (a) $T^2$ is $NR^{T2}$, (b) $T^3$ is N, or (c) $T^1$ is $NR^{T1}$;
$R^1$ is selected from the group consisting of —$NH_2$, —$CH_2$COOH, —CH(NH(CO)(alkyl))COOH, —CH(NH(CO)(cycloalkyl))COOH, —CO(NH)$CH_2$aryl, —CO(NH)$CH_2$heteroaryl, —CO(NH)aryl, and —CO(NH)heteroaryl;
p is 0, 1, or 2;
J is —C(O)—, —NH—, —$CH_2$—, —O—, —S—, —S(O)—, —$SO_2$—, —N(alkyl)-, or —CH(alkyl)-;
K is —C(O)—, —NH—, —O—, —$CH_2$—, —S—, —S(O)—, —$SO_2$—, —N(alkyl)-, or —CH(alkyl)-;

wherein at least one of J and K is —C(O)—, —$CH_2$—, or —CH(alkyl)-;
W is N, CH, or $CR^c$;
X is N, CH, or $CR^c$;
Y is N, CH, or $CR^c$;
Z is N, CH, or $CR^c$;
$R^c$, independently for each occurrence, is selected from the group consisting of halogen, —OH, —$NR^jR^k$, alkoxy, and alkyl;
L is selected from the group consisting of a bond, —$CH_2$—, —$CH_2CH_2$—, —$CHR^2$—, —$CF_2$—, —$CFR^2$—, —C(O)—, —C(=$NR^L$)—, and —C(=$CHR^L$)—;
wherein $R^L$ is H or alkyl;
or wherein $R^L$ and an occurrence of $R^c$ taken together with the intervening atoms form a substituted or unsubstituted heteroaryl ring;
$R^2$ is alkyl, hydroxyalkyl, or haloalkyl;
V is N or CH; and
the stereochemical configuration at any chiral center is R, S, or a mixture of R and S.

In certain aspects, the invention provides a pharmaceutical composition, comprising a compound of the invention, or a pharmaceutically acceptable salt or prodrug thereof; and a pharmaceutically acceptable carrier.

In certain aspects, the invention provides methods of treating a disease or condition characterized by aberrant complement system activity, comprising administering to a subject in need thereof a therapeutically effective amount of a compound the invention, or a pharmaceutically acceptable salt or prodrug thereof. In certain embodiments, the disease or condition characterized by aberrant complement system activity is an immunological disorder.

In certain embodiments, the disease or condition characterized by aberrant complement system activity is a disease of the central nervous system. In certain embodiments, the disease or condition characterized by aberrant complement system activity is a neurodegenerative disease or neurological disease. In certain embodiments, the disease or condition characterized by aberrant complement system activity is a renal disease. In certain embodiments, the disease or condition characterized by aberrant complement system activity is a cardiovascular disease. In certain embodiments, the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, and catastrophic antiphospholipid syndrome.

DETAILED DESCRIPTION

Inhibitors of the complement system are useful in therapeutic methods and compositions suitable for use in treating disorders of the immune, renal, cardiovascular, and neurological systems. Provided herein are compounds of formulae (I) and (II) and pharmaceutically acceptable salts and prodrugs thereof that are useful in treating or preventing a disease or condition characterized by aberrant activity of the complement system.

Definitions

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium, and alternatively oxygen, nitrogen or sulfur.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ alkyl group. In certain embodiments, the term "alkyl" refers to a $C_1$-$C_6$ alkyl group, for example a $C_1$-$C_6$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "cycloalkyl" means mono- or bicyclic or bridged saturated carbocyclic rings, each having from 3 to 12 carbon atoms. Certain cycloalkyls have from 5-12 carbon atoms in their ring structure, and may have 6-10 carbons in the ring structure. Preferably, cycloalkyl is ($C_3$-$C_7$)cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "(cycloalkyl)alkyl" as used herein refers to an alkyl group substituted with one or more cycloalkyl groups. An example of cycloalkylalkyl is cyclohexylmethyl group.

The term "heterocycloalkyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2-azobicyclo[3.1.0]hexane. A heterocycloalkyl group is optionally substituted by one or more substituents as described below.

The term "(heterocycloalkyl)alkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, arylalkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as triflurormethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

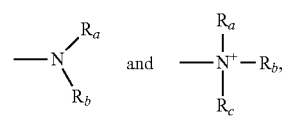

wherein $R_a$, $R_b$, and $R_c$ each independently represent a hydrogen, an alkyl, an alkenyl, —$(CH_2)_x$—$R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally Re) each independently represent a hydrogen, an alkyl, an alkenyl, or —$(CH_2)_x$—$R_d$. In certain embodiments, the term "amino" refers to —$NH_2$.

In certain embodiments, the term "alkylamino" refers to —NH(alkyl).

In certain embodiments, the term "dialkylamino" refers to —$N(alkyl)_2$.

The term "amido", as used herein, means —NHC(=O)—, wherein the amido group is bound to the parent molecular moiety through the nitrogen. Examples of amido include alkylamido such as $CH_3C$(=O)N(H)— and $CH_3CH_2C$(=O)N(H)—.

The term "acyl" is a term of art and as used herein refers to any group or radical of the form RCO— where R is any organic group, e.g., alkyl, aryl, heteroaryl, arylalkyl, and heteroarylalkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group, i.e., —$CH_2NH_2$.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

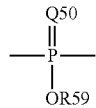

wherein Q50 represents S or O, and R59 represents hydrogen, a lower alkyl or an aryl; for example, —P(O)(OMe)- or —$P(O)(OH)_2$. When used to substitute, e.g., an alkyl, the phosphoryl group of the phosphorylalkyl may be represented by the general formulas:

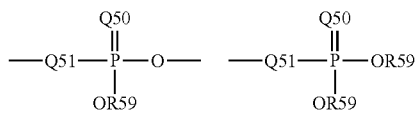

wherein Q50 and R59, each independently, are defined above, and Q51 represents O, S or N; for example, —O—P(O)(OH)OMe or —NH—$P(O)(OH)_2$. When Q50 is S, the phosphoryl moiety is a "phosphorothioate."

The term "aminophosphoryl" as used herein refers to a phosphoryl group substituted with at least one amino group, as defined herein; for example, —$P(O)(OH)NMe_2$.

The term "azide" or "azido", as used herein, means an —$N_3$ group.

The term "carbonyl" as used herein refers to —C(=O)—.

The term "thiocarbonyl" as used herein refers to —C(=S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—. The term "(alkylthio)alkyl" refers to an alkyl group substituted by an alkylthio group.

The term "carboxy", as used herein, means a —$CO_2H$ group.

The term "aryl" is a term of art and as used herein refers to includes monocyclic, bicyclic and polycyclic aromatic hydrocarbon groups, for example, benzene, naphthalene, anthracene, and pyrene. Typically, an aryl group contains from 6-10 carbon ring atoms (i.e., ($C_6$-$C_{10}$)aryl). The aromatic ring may be substituted at one or more ring positions with one or more substituents, such as halogen, azide, alkyl, arylalkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group.

The term "heteroaryl" is a term of art and as used herein refers to a monocyclic, bicyclic, and polycyclic aromatic group having 3 to 12 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, arylalkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "aralkyl" or "arylalkyl" is a term of art and as used herein refers to an alkyl group substituted with an aryl group, wherein the moiety is appended to the parent molecule through the alkyl group.

The term "heteroaralkyl" or "heteroarylalkyl" is a term of art and as used herein refers to an alkyl group substituted with a heteroaryl group, appended to the parent molecular moiety through the alkyl group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" refers to an alkyl group substituted by an alkoxy group.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH—CH_2—O—$) and vinyloxy (i.e., $CH_2=CH—O—$).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "cyano" is a term of art and as used herein refers to —CN.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3Si—$) group (i.e., (hydrocarbyl)$_3Si—$), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

As used herein, the term "substituted or unsubstituted" when it precedes a list of chemical moieties means that the list of chemical moieties that follow are each substituted or unsubstituted. For example, "substituted or unsubstituted aryl, heteroaryl, and cycloalkyl" means substituted or unsubstituted aryl, substituted or unsubstituted heteroaryl, and substituted or unsubstituted cycloalkyl.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

The term "prodrug" as used herein refers to a compound that can be metabolized in vivo to provide a compound of formula I or II. Thus prodrugs include compounds that can be prepared by modifying one or more functional groups in a compound of formula I or II to provide a corresponding compound that can be metabolized in vivo to provide a compound of formula I or II. Such modifications are known in the art. For example, one or more hydroxyl groups or amine groups in a compound of formula I or II can be acylated with alkyl-C(=O)— groups or with residues from amino acids to provide a prodrug.

Prodrug forms of a compound bearing various nitrogen-containing functional groups (amino, hydroxyamino, amide, etc.) may include the following types of derivatives, where each $R_p$ group individually may be hydrogen, substituted or unsubstituted alkyl, aryl, alkenyl, alkynyl, heterocycle, alkylaryl, arylalkyl, aralkenyl, aralkynyl, cycloalkyl or cyclo alkenyl (a) Carboxamides, represented as —NHC(O)$R_p$ (b) Carbamates, represented as —NHC(O)O$R_p$ (c) (Acyloxy)alkyl Carbamates, represented as NHC(O)OROC(O)$R_p$ (d) Enamines, represented as —NHCR(=CHCO$_2$$R_p$) or —NHCR(=CHCONR$_p$$R_p$)

(e) Schiff Bases, represented as —N=CR$_p$R$_p$ (f) Mannich Bases (from carboximide compounds), represented as RCONHCH$_2$NR$_p$R$_p$ Preparations of such prodrug derivatives are discussed in various literature sources (examples are: Alexander et al., J. Med. Chem, 1988, 31, 318; Aligas-Martin et al., PCT WO0041531, p. 30).

Prodrug forms of carboxyl-bearing compounds include esters (—CO$_2$R$_m$), where the R$_m$ group corresponds to any alcohol whose release in the body through enzymatic or hydrolytic processes would be at pharmaceutically acceptable levels. Another prodrug derived from a carboxylic acid form of the disclosure may be a quaternary salt type of structure described by Bodor et al., J. Med. Chem. 1980, 23, 469.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In one embodiment, a subject is a human.

Compounds

The present invention provides compounds having the structure of Formula (I), and pharmaceutically acceptable salts or prodrugs thereof:

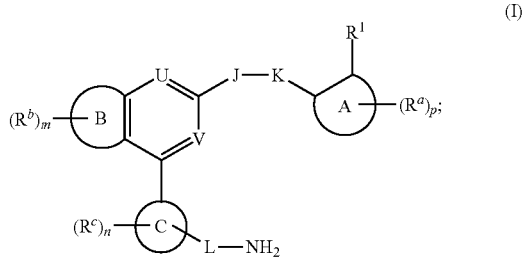

wherein:

ring

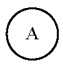

is aryl, heteroaryl, cycloalkyl, or heterocycloalkyl;

ring

is aryl, heteroaryl, heterocycloalkyl, or cycloalkyl;

ring

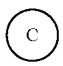

is aryl or heteroaryl;

$R^a$, independently for each occurrence, is halogen, cyano, hydroxy, —NH$_2$, —NH(Ac), —NH(alkyl), —NH(cycloalkyl), —NH(heterocycloalkyl), —NH(aryl), —NH(heteroaryl), —N(alkyl)$_2$, —NHC(O)(alkyl), —CH(alkyl)NH$_2$, —CH(hydroxyalkyl)NH$_2$, —CH(haloalkyl)NH$_2$, —CH(cycloalkyl)NH$_2$, —CH(heterocycloalkyl)NH$_2$, —CH(aryl)NH$_2$, —CH(heteroaryl)NH$_2$, —CH$_2$NHC(O)(alkyl), —C(O)NH$_2$, —C(O)(alkyl), —SO$_2$NH$_2$, —SO$_2$(cycloalkyl), —SO$_2$(heterocycloalkyl), —SO$_2$(alkyl), —SO$_2$(aryl), or —SO$_2$(heteroaryl); or is selected from the group consisting of substituted or unsubstituted aryl, heteroaryl, arylalkyl, heteroarylalkyl, cycloalkyl, heterocycloalkyl, alkoxy, alkyl, (cycloalkyl)alkyl, (heterocycloalkyl)alkyl, hydroxyalkyl, aminoalkyl, and haloalkyl;

$R^b$, independently for each occurrence, is halogen, cyano, —CH$_2$(OCH$_2$CH$_2$)$_q$OCH$_3$, -alkylene-(branched or unbranched polyethylene glycol), -alkylene-O-(branched or unbranched polyethylene glycol), or —NR$^j$R$^k$; or is selected from the group consisting of substituted or unsubstituted alkyl, haloalkyl, hydroxyalkyl, alkoxyalkyl, (hydroxy)haloalkyl, hydroxy(cycloalkyl)alkyl, (cycloalkyl)alkyl, (heterocycloalkyl)alkyl, arylalkyl, heteroarylalkyl, (heteroarylalkoxy)alkyl, (arylalkoxy)alkyl, (aryloxy)alkyl, ((cycloalkyl)alkoxy)alkyl, ((heterocycloalkyl)alkoxy)alkyl, cycloalkyl, heterocycloalkyl, aryl, heteroaryl, -alkylene-NR$^j$R$^k$, tosyl, —SO$_2$(alkyl), —SO$_2$(cycloalkyl), —CO(alkyl), —CO(aryl), —CO(heteroaryl), —CO(cycloalkyl), —CO(heterocycloalkyl), —CONH(alkyl), —CONH(arylalkyl), —CONH(heteroarylalkyl), —CON(alkyl)$_2$, —CONH(heterocycloalkyl), and —CONH(cycloalkyl);

$R^c$, independently for each occurrence, is selected from the group consisting of halogen, —OH, —NR$^j$R$^k$, alkoxy, alkyl, cycloalkyl, and heterocycloalkyl;

$R^1$ is selected from the group consisting of —NH$_2$, —COOH, —CH$_2$COOH, —CH(NH(CO)(alkyl))COOH, —CH(NH(CO)(arylalkyl))COOH, —CH(NH(CO)(cycloalkyl))COOH, —CH(NH(CO)(aryl substituted cycloalkyl))COOH, —CH(NH(CO)(heteroaryl substituted cycloalkyl))COOH, —CH(S(alkyl))COOH, —CO(NH)CH$_2$(substituted or unsubstituted aryl), —CO(NH)CH$_2$(substituted or unsubstituted heteroaryl), —CO(NH)(substituted or unsubstituted aryl), —CO(NH)(substituted or unsubstituted heteroaryl), and —CH$_2$(tetrazolyl);

n is 0, 1, 2, 3, or 4;

m is 0, 1, 2, 3, or 4;

p is 0, 1, 2, 3, or 4;

q is an integer from 1-20;

J is —C(O)—, —NH—, —CH$_2$—, —O—, —S—, —S(O)—, —SO$_2$—, —N(alkyl)-, —CH(alkyl)-, —CH(cycloalkyl)-, —N((C(O)O)arylalkyl)-, —N((C(O)O)heteroarylalkyl)-, or —N(C(O)arylalkyl)-;

K is —C(O)—, —NH—, —CH$_2$—, —O—, —S—, —S(O)—, —SO$_2$—, —N(alkyl)-, —CH(alkyl)-, —CH(cycloalkyl)-, —N((C(O)O)arylalkyl)-, —N((C(O)O)heteroarylalkyl)-, or —N(C(O)arylalkyl)-;

wherein at least one of J and K is —C(O)—, —CH$_2$—, or —CH(alkyl)-;

L is selected from the group consisting of a bond, —CH$_2$—, —CH$_2$CH$_2$—, —CHR$^2$—, —CF$_2$—, —CFR$^2$—, —C(O)—, —C(=NR$^L$)—, —C(=CHR$^L$)—, —S(O)$_2$—, and —S(O)—;

wherein R$^L$ is H or alkyl;

or wherein R$^L$ and an occurrence of R$^c$ taken together with the intervening atoms form a substituted or unsubstituted heteroaryl ring;

$R^2$ is alkyl, cycloalkyl, hydroxyalkyl, or haloalkyl;

$R^j$ and $R^k$ are each independently H or are selected from the group consisting of substituted or unsubstituted alkyl, aminoalkyl, (heterocycloalkyl)alkyl, heterocycloalkyl, aryl, arylalkyl, heteroaryl, heteroarylalkyl, —CO(aryl), —CO(arylalkyl), —CO(heteroarylalkyl), and —CO((heterocycloalkyl)alkyl);

U is N or CR$^3$;

$R^3$ is H, halogen, alkyl, cycloalkyl, aryl, heteroaryl, alkoxy, haloalkyl, —CN, —CONH$_2$, —CO$_2$H, —CH$_2$CO$_2$H, —NH$_2$, hydroxyalkyl, aminoalkyl, —OH, —NH(alkyl), —N(alkyl)$_2$, thioalkyl, or —S(alkyl);

V is N, CH, C(halogen), or C(alkyl); and the stereochemical configuration at any chiral center is R, S, or a mixture of R and S.

In some embodiments, the compound of formula (I) has the structure of formula (Ia):

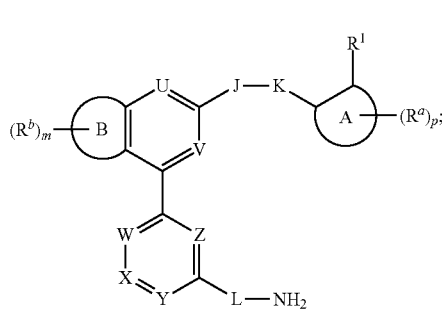

wherein:
W is N, CH, or CR$^c$;
X is N, CH, or CR$^c$;
Y is N, CH, or CR$^c$; and
Z is N, CH, or CR$^c$.
In certain embodiments, ring

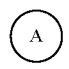

is napthyl, indenyl, cyclopentyl, pyrrolidinyl, phenyl, benzofuranyl, thiophenyl, or pyridinyl.
In certain embodiments, ring

is phenyl, thiophenyl, or pyridinyl, preferably phenyl.
In certain embodiments, the compound of formula (I) has the structure of formula (Ib):

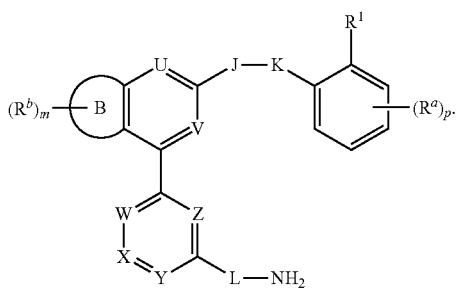

In certain embodiments, p is 1.
In certain such embodiments, R$^a$ is halogen, cyano, hydroxy, —NH$_2$, —NH(Ac), —NH(alkyl), —N(alkyl)$_2$, —NHC(O)(alkyl), —CH$_2$NHC(O)(alkyl), —C(O)NH$_2$, or —C(O)(alkyl); or is selected from the group consisting of substituted or unsubstituted aryl, heteroaryl, cycloalkyl, alkoxy, alkyl, (cycloalkyl)alkyl, hydroxyalkyl, aminoalkyl, and haloalkyl.
In other such embodiments, R$^a$ is halogen, cyano, —NH$_2$, —NH(Ac), —C(O)CH$_3$, —C(O)NH$_2$, hydroxymethyl, or substituted or unsubstituted aryl, heteroaryl, cycloalkyl, alkoxy, alkyl, or aminoalkyl.

In other such embodiments, R$^a$ is halogen, —NH(Ac), —C(O)CH$_3$, or substituted or unsubstituted aryl, heteroaryl, cycloalkyl, alkoxy, alkyl, or aminoalkyl. In further such embodiments, R$^a$ is alkyl, cycloalkyl, or halogen.
Alternatively, in some embodiments, p is 0.
In certain embodiments, R$^1$ is —CH$_2$COOH.
Alternatively, in some embodiments, R$^1$ is —CO(NH) CH$_2$(substituted or unsubstituted aryl).
In certain embodiments:

J is —C(O)—, —NH—, —CH$_2$—, —O—, —S—, —S(O)—, —SO$_2$—, —N(alkyl)-, —CH(alkyl)-, or —N(C(O)arylalkyl)-; and K is —C(O)—, —NH—, —O—, —CH$_2$—, —S—, —S(O)—, —SO$_2$—, —N(alkyl)-, —CH(alkyl)-, or —N(C(O)arylalkyl)-.

In some embodiments, -J-K— is selected from the group consisting of —C(O)—NH—, —NH—C(O)—, and —CH$_2$O—, preferably —CH$_2$O—.
In certain embodiments, U is N or CR$^3$, and R$^3$ is H, halogen, alkyl, cycloalkyl, aryl, heteroaryl, alkoxy, or haloalkyl.
In certain embodiments, U is CH. In further embodiments, V is CH.
Alternatively, in some embodiments, U is CR$^3$ and R$^3$ is H, halogen, alkyl, alkoxy, or haloalkyl.
In some embodiments, the compound of formula (I) has the structure of formula (Ic):

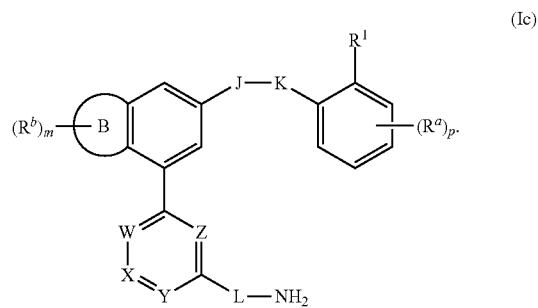

Alternatively, in some embodiments, the compound of formula (I) has the structure of formula (Id):

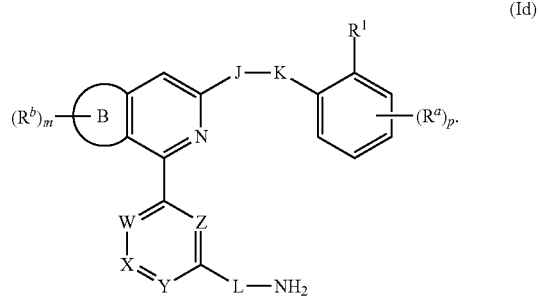

In still further embodiments, the compound of formula (I) has the structure of formula (Ie):

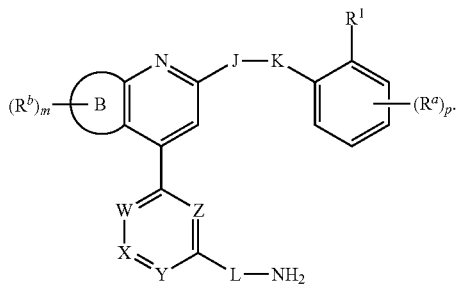

(Ie)

In yet further embodiments, the compound of formula (I) has the structure of formula (If):

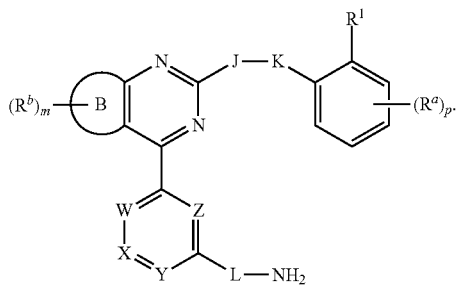

(If)

In any of the foregoing embodiments, ring

B may be heteroaryl. For example, in some embodiments, ring

B is furyl, oxazolyl, isoxazolyl, thiophenyl, pyrrolyl, pyrazolyl, or imidazolyl. In further embodiments, ring

B is furyl, thiophenyl, or pyrrolyl, preferably furyl.

In some embodiments, m is 0.

In alternative embodiments, m is 1. In certain such embodiments, $R^b$, independently for each occurrence, is halogen, cyano, —CH$_2$(OCH$_2$CH$_2$)$_q$OCH$_3$, or —NR$^j$R$^k$; or is selected from the group consisting of substituted or unsubstituted alkyl, haloalkyl, hydroxyalkyl, alkoxyalkyl, (hydroxy)haloalkyl, hydroxy(cycloalkyl)alkyl, (cycloalkyl)alkyl, (heterocycloalkyl)alkyl, arylalkyl, heteroarylalkyl, (heteroarylalkoxy)alkyl, (arylalkoxy)alkyl, (aryloxy)alkyl, cycloalkyl, heterocycloalkyl, aryl, heteroaryl, -alkylene-NR$^j$R$^k$, tosyl, —SO$_2$(alkyl), —SO$_2$(cycloalkyl), —CO(alkyl), —CO(cycloalkyl), —CONH(alkyl), —CONH(arylalkyl), —CON(alkyl)$_2$, and —CONH(cycloalkyl).

In certain embodiments, q is an integer from 1-5.

In other such embodiments, $R^b$ is selected from the group consisting of substituted or unsubstituted alkyl, cycloalkyl, hydroxyalkyl, alkoxyalkyl, haloalkyl, and (cycloalkyl)alkyl. In alternative embodiments, $R^b$ is substituted or unsubstituted -alkylene-NR$^j$R$^k$.

In other alternative embodiments, m is 2. In certain such embodiments, each $R^b$ is alkyl.

In certain embodiments, each of W, X, Y, and Z is CH.

In certain embodiments, at least one of W, X, Y, and Z is CR$^c$. For example, Z may be CR$^c$ and/or Y may be CR$^c$. In certain such embodiments, R$^c$ is selected from the group consisting of halogen, —OH, —NR$^j$R$^k$, alkoxy, and alkyl. In certain preferred embodiments, R$^c$ is halogen, e.g., fluoride.

Alternatively, at least one of W, X, Y, and Z is N. For example, Z may be N.

Alternatively, Y may be N.

In some embodiments, L is selected from the group consisting of a bond, —CH$_2$—, —CH$_2$CH$_2$—, —CHR$^2$—, —CF$_2$—, —CFR$^2$—, —C(O)—, —C(=NR$^L$)—, and —C(=CHR$^L$)—.

In some embodiments, L is —CH$_2$—.

In certain embodiments of the compounds of formula (I): ring

A is aryl, heteroaryl, cycloalkyl, or heterocycloalkyl; ring

B is aryl, heteroaryl, heterocycloalkyl, or cycloalkyl; ring

C is aryl or heteroaryl;
$R^a$, independently for each occurrence, is selected from the group consisting of halogen, cyano, hydroxy, —NH$_2$, —NH(Ac), —NH(alkyl), —N(alkyl)$_2$, —NHC(O)(alkyl), —CH$_2$NHC(O)(alkyl), —C(O)NH$_2$, —C(O)(alkyl), optionally substituted aryl, optionally substituted heteroaryl, cycloalkyl, alkoxy, alkyl, (cycloalkyl)alkyl, hydroxyalkyl, aminoalkyl, and haloalkyl; $R^b$, independently for each occurrence, is selected from the group consisting of halogen, cyano, —NR$^j$R$^k$, alkyl, haloalkyl, hydroxyalkyl, alkoxyalkyl, (hydroxy)haloalkyl, hydroxy(cycloalkyl)alkyl, (cycloalkyl)alkyl, (heterocycloalkyl)alkyl, arylalkyl, heteroarylalkyl, cycloalkyl, heterocycloalkyl, optionally substituted aryl, optionally substituted heteroaryl, -alkylene-NR$^j$R$^k$, tosyl, —SO$_2$(alkyl), —SO$_2$(cycloalkyl), —CO(alkyl), —CO(cycloalkyl), —CONH(alkyl), —CON(alkyl)$_2$, and —CONH(cycloalkyl);
$R^c$, independently for each occurrence, is selected from the group consisting of halogen, —OH, —NR$^j$R$^k$, alkoxy, and alkyl;

R¹ is selected from the group consisting of —NH₂, —CH₂COOH, —CH(NH(CO)(alkyl))COOH, —CH(NH(CO)(arylalkyl))COOH, —CH(NH(CO)(cycloalkyl))COOH, —CH(NH(CO)(aryl substituted cycloalkyl))COOH, —CO(NH)CH₂aryl, —CO(NH)CH₂heteroaryl, —CO(NH)heteroaryl, —CO(NH)aryl, and —CO(NH)heteroaryl;

n is 0, 1, or 2;
m is 0, 1, or 2;
p is 0, 1, or 2;
J is —C(O)—, —NH—, —CH₂—, —O—, —S—, —S(O)—, —SO₂—, —N(alkyl)-, or —CH(alkyl)-;
K is —C(O)—, —NH—, —O—, —CH₂—, —S—, —S(O)—, —SO₂—, —N(alkyl)-, or —CH(alkyl)-;
wherein at least one of J and K is —C(O)—, —CH₂—, or —CH(alkyl)-;

L is selected from the group consisting of a bond, —CH₂—, —CH₂CH₂—, —CHR²—, —CF₂—, —CFR²—, —C(O)—, —C(=NR^L)—, and —C(=CHR^L)—;
wherein R^L is H or alkyl;
or wherein R^L and an occurrence of R^c taken together with the intervening atoms form a substituted or unsubstituted heteroaryl ring;
R² is alkyl, hydroxyalkyl, or haloalkyl;
R^j and R^k are each independently selected from the group consisting of H, alkyl, aminoalkyl, (heterocycloalkyl)alkyl, and heterocycloalkyl;
U is N or CR³;
R³ is H, halogen, alkyl, alkoxy, or haloalkyl; and
V is N or CH.

In certain embodiments, the compound of formula (I) is selected from the following table of compounds, and pharmaceutically acceptable salts and prodrugs thereof:

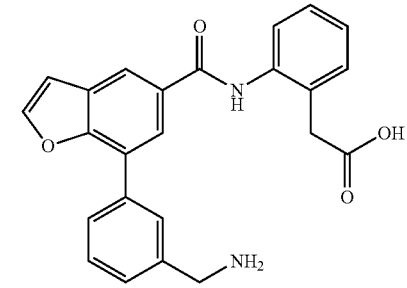 [SMILES: NCc1cccc(-c2cc(C(=O)Nc3ccccc3CC(=O)O)cc3ccoc23)c1]

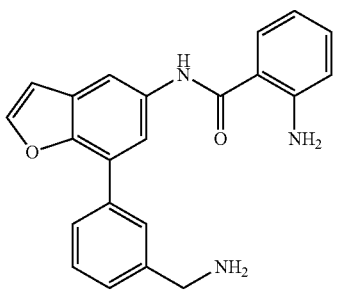 [SMILES: NCc1cccc(-c2cc(NC(=O)c3ccccc3N)cc3ccoc23)c1]

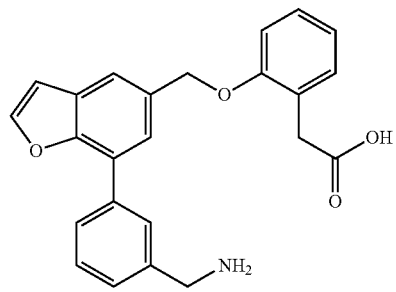 [SMILES: NCc1cccc(-c2cc(COc3ccccc3CC(=O)O)cc3ccoc23)c1]

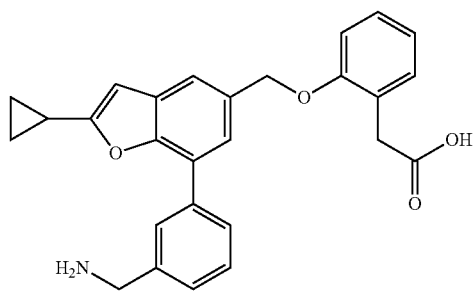 [SMILES: NCc1cccc(-c2cc(COc3ccccc3CC(=O)O)cc3cc(C4CC4)oc23)c1]

-continued
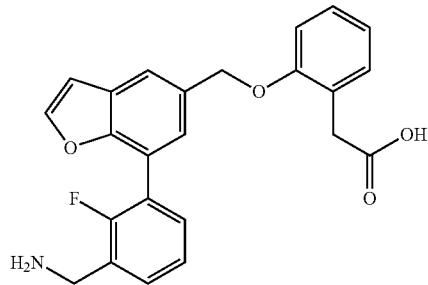 [SMILES: NCc1cccc(-c2cc(COc3ccccc3CC(=O)O)cc3ccoc23)c1F]
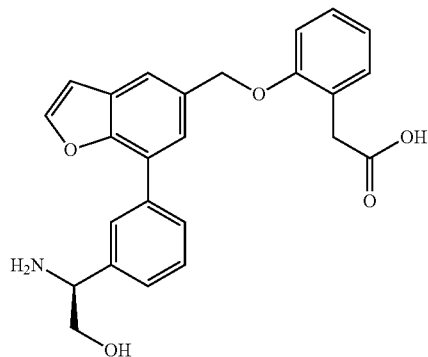 [SMILES: N[C@H](CO)c1cccc(-c2cc(COc3ccccc3CC(=O)O)cc3ccoc23)c1]
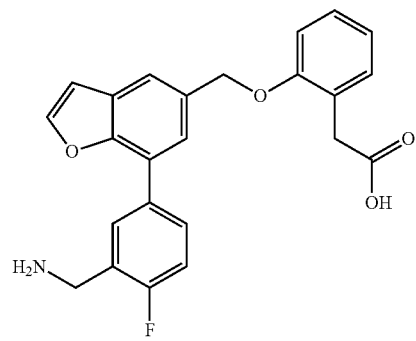 [SMILES: NCc1cc(-c2cc(COc3ccccc3CC(=O)O)cc3ccoc23)ccc1F]
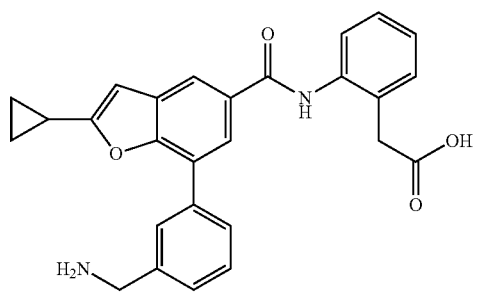 [SMILES: NCc1cccc(-c2cc(C(=O)Nc3ccccc3CC(=O)O)cc3cc(C4CC4)oc23)c1]
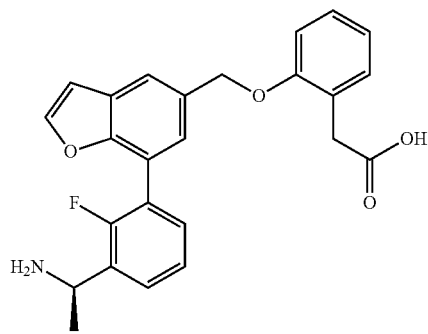 [SMILES: C[C@@H](N)c1cccc(-c2cc(COc3ccccc3CC(=O)O)cc3ccoc23)c1F]

-continued
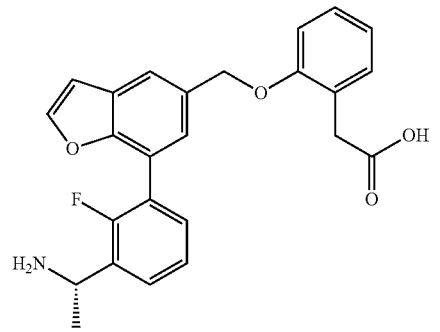 [SMILES: C[C@H](N)c1cccc(-c2cc(COc3ccccc3CC(=O)O)cc3ccoc23)c1F]
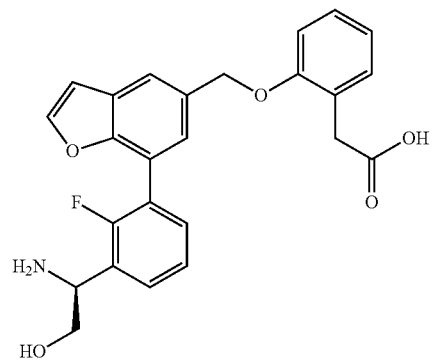 [SMILES: N[C@H](CO)c1cccc(-c2cc(COc3ccccc3CC(=O)O)cc3ccoc23)c1F]
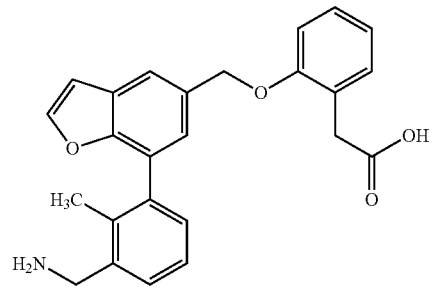 [SMILES: Cc1c(CN)cccc1-c1cc(COc2ccccc2CC(=O)O)cc2ccoc12]
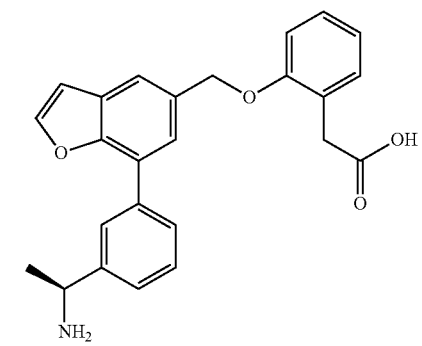 [SMILES: C[C@H](N)c1cccc(-c2cc(COc3ccccc3CC(=O)O)cc3ccoc23)c1]
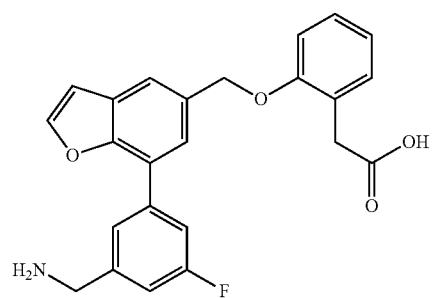 [SMILES: NCc1cc(F)cc(-c2cc(COc3ccccc3CC(=O)O)cc3ccoc23)c1]

-continued
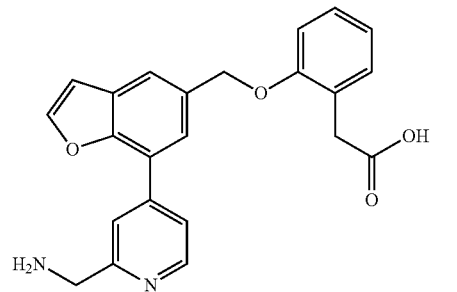 [SMILES: NCc1cc(-c2cc(COc3ccccc3CC(=O)O)cc3ccoc23)ccn1]
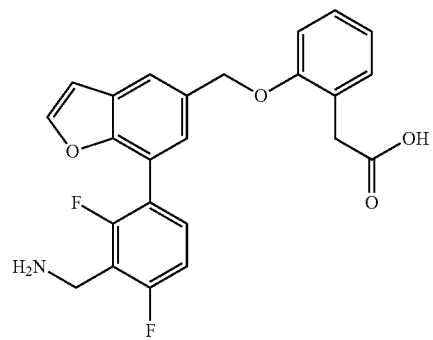 [SMILES: NCc1c(F)ccc(-c2cc(COc3ccccc3CC(=O)O)cc3ccoc23)c1F]
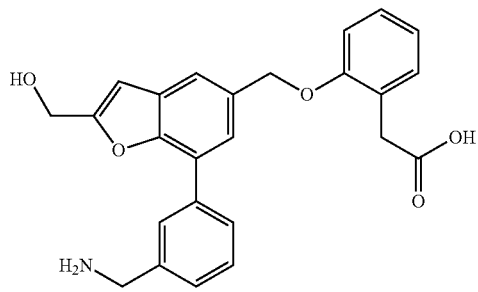 [SMILES: NCc1cccc(-c2cc(COc3ccccc3CC(=O)O)cc3cc(CO)oc23)c1]
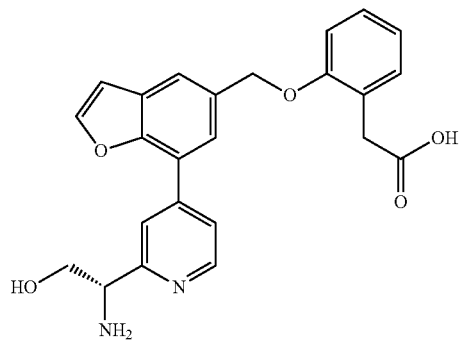 [SMILES: N[C@H](CO)c1cc(-c2cc(COc3ccccc3CC(=O)O)cc3ccoc23)ccn1]
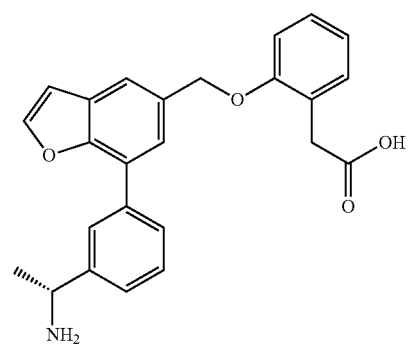 [SMILES: C[C@@H](N)c1cccc(-c2cc(COc3ccccc3CC(=O)O)cc3ccoc23)c1]

-continued
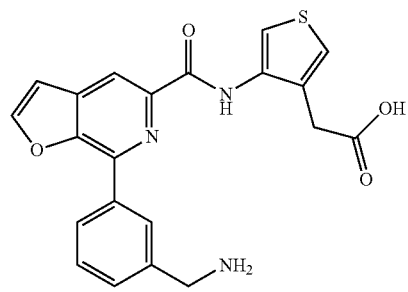 [SMILES: NCc1cccc(-c2nc(C(=O)Nc3cscc3CC(=O)O)cc3ccoc23)c1]
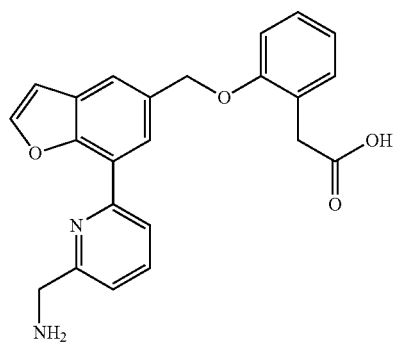 [SMILES: NCc1cccc(-c2cc(COc3ccccc3CC(=O)O)cc3ccoc23)n1]
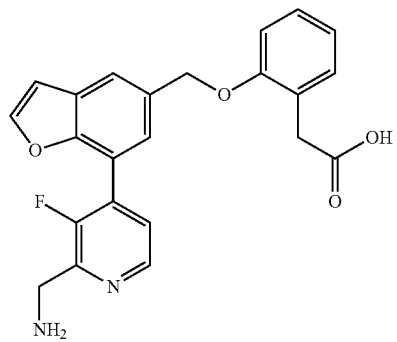 [SMILES: NCc1nccc(-c2cc(COc3ccccc3CC(=O)O)cc3ccoc23)c1F]
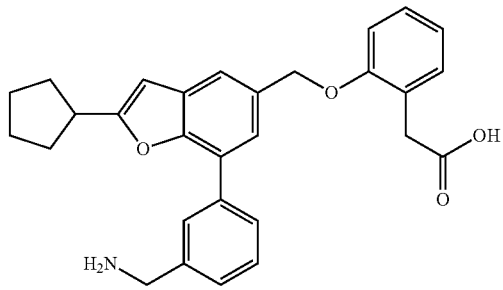 [SMILES: NCc1cccc(-c2cc(COc3ccccc3CC(=O)O)cc3cc(C4CCCC4)oc23)c1]
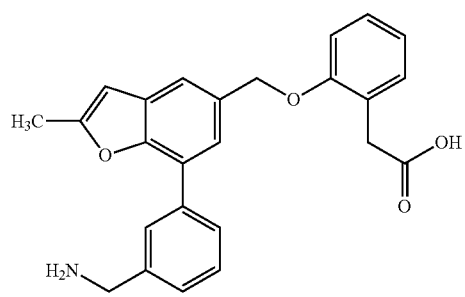

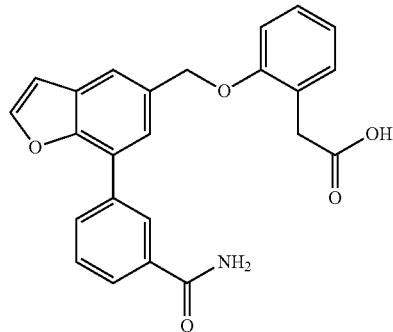 [SMILES: NC(=O)c1cccc(-c2cc(COc3ccccc3CC(=O)O)cc3ccoc23)c1]
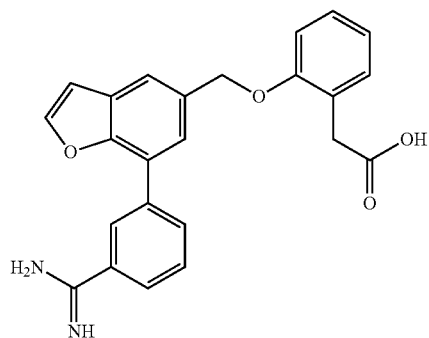 [SMILES: N=C(N)c1cccc(-c2cc(COc3ccccc3CC(=O)O)cc3ccoc23)c1]
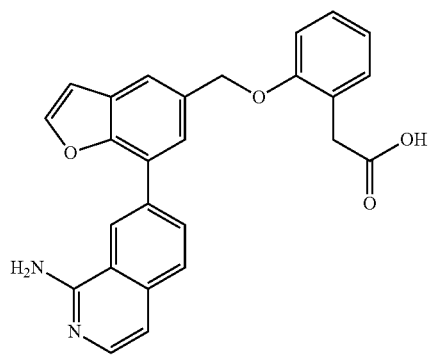 [SMILES: Nc1nccc2ccc(-c3cc(COc4ccccc4CC(=O)O)cc4ccoc34)cc12]
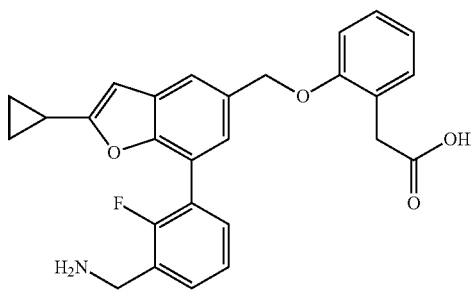 [SMILES: NCc1cccc(-c2cc(COc3ccccc3CC(=O)O)cc3cc(C4CC4)oc23)c1F]
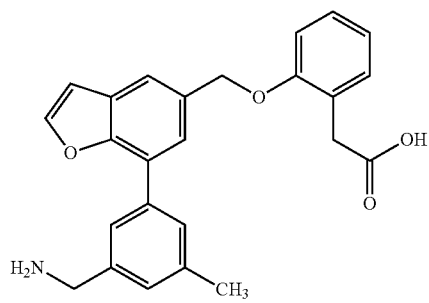 [SMILES: Cc1cc(CN)cc(-c2cc(COc3ccccc3CC(=O)O)cc3ccoc23)c1]

-continued
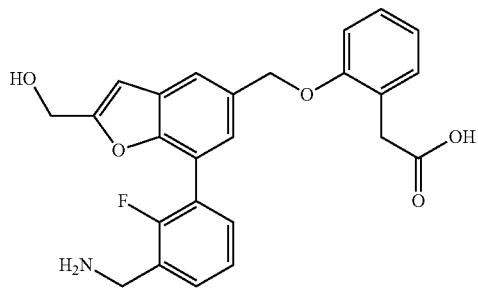 [SMILES: NCc1cccc(-c2cc(COc3ccccc3CC(=O)O)cc3cc(CO)oc23)c1F]
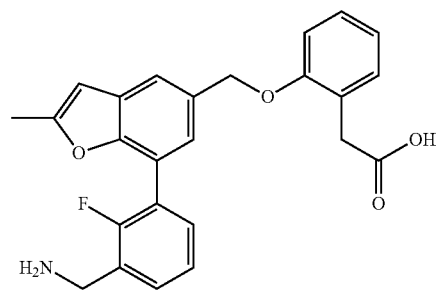 [SMILES: Cc1cc2cc(COc3ccccc3CC(=O)O)cc(-c3cccc(CN)c3F)c2o1]
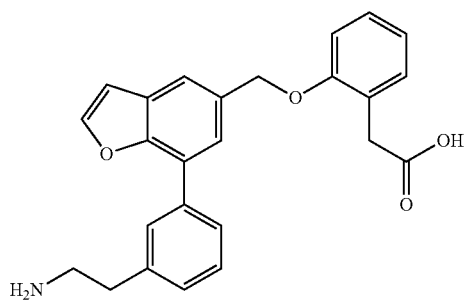 [SMILES: NCCc1cccc(-c2cc(COc3ccccc3CC(=O)O)cc3ccoc23)c1]
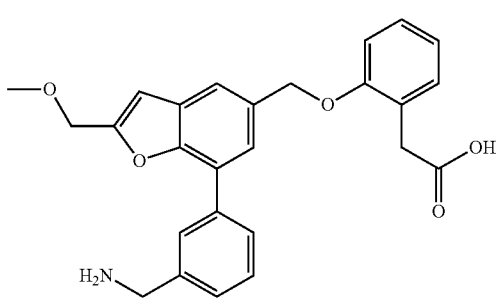 [SMILES: COCc1cc2cc(COc3ccccc3CC(=O)O)cc(-c3cccc(CN)c3)c2o1]
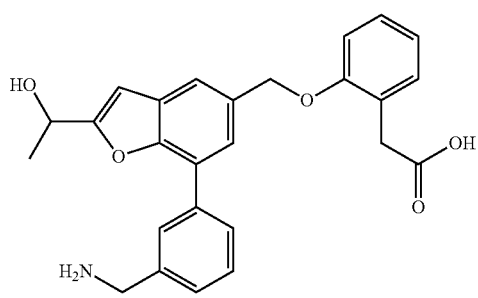 [SMILES: CC(O)c1cc2cc(COc3ccccc3CC(=O)O)cc(-c3cccc(CN)c3)c2o1]

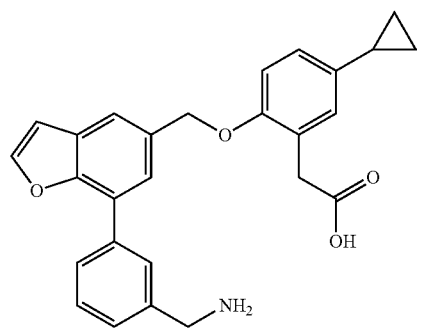 [SMILES: NCc1cccc(-c2cc(COc3ccc(C4CC4)cc3CC(=O)O)cc3ccoc23)c1]
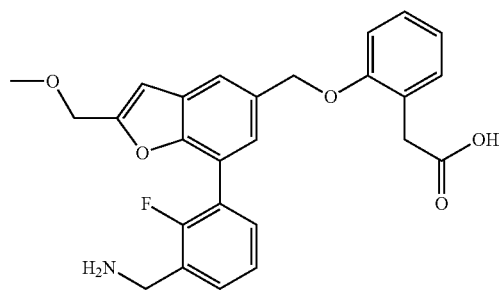
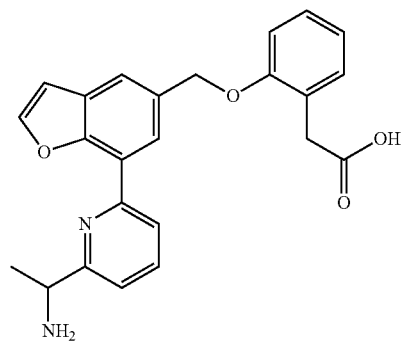 [SMILES: CC(N)c1cccc(-c2cc(COc3ccccc3CC(=O)O)cc3ccoc23)n1]
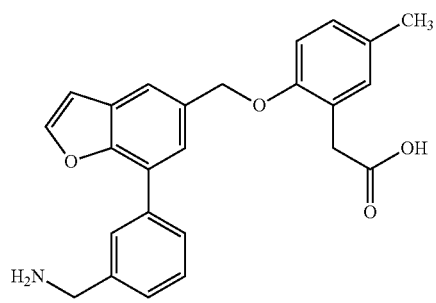 [SMILES: Cc1ccc(OCc2cc(-c3cccc(CN)c3)c3occc3c2)c(CC(=O)O)c1]
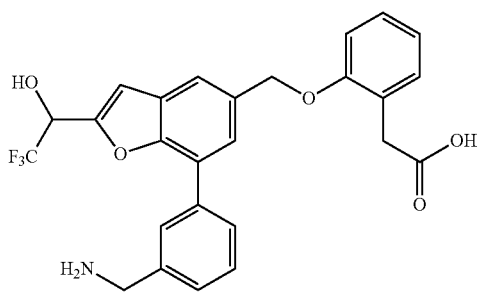

-continued
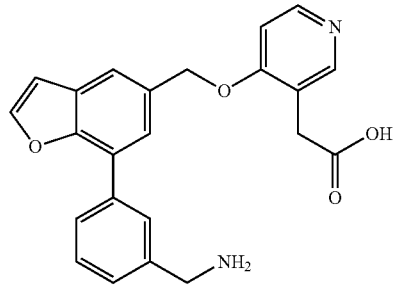 [SMILES: NCc1cccc(-c2cc(COc3ccncc3CC(=O)O)cc3ccoc23)c1]
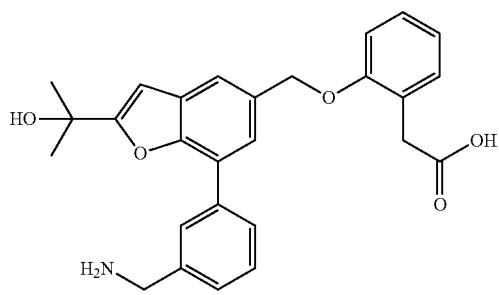 [SMILES: CC(C)(O)c1cc2cc(COc3ccccc3CC(=O)O)cc(-c3cccc(CN)c3)c2o1]
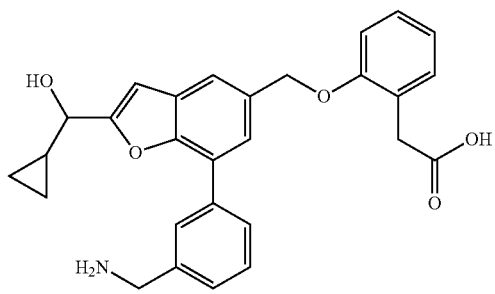 [SMILES: NCc1cccc(-c2cc(COc3ccccc3CC(=O)O)cc3cc(C(O)C4CC4)oc23)c1]
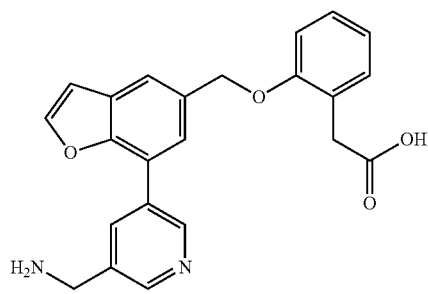 [SMILES: NCc1cncc(-c2cc(COc3ccccc3CC(=O)O)cc3ccoc23)c1]
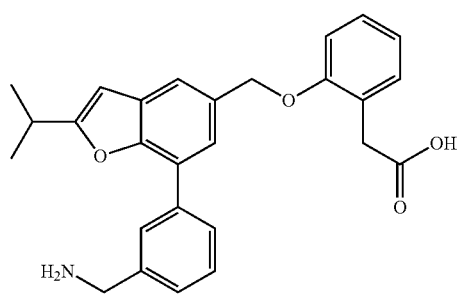 [SMILES: CC(C)c1cc2cc(COc3ccccc3CC(=O)O)cc(-c3cccc(CN)c3)c2o1]

-continued
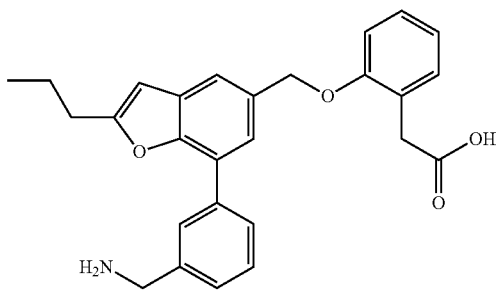 [SMILES: CCCc1cc2cc(COc3ccccc3CC(=O)O)cc(-c3cccc(CN)c3)c2o1]
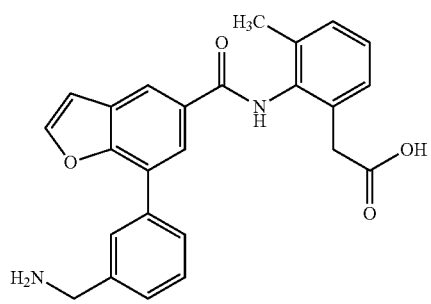 [SMILES: Cc1cccc(CC(=O)O)c1NC(=O)c1cc(-c2cccc(CN)c2)c2occc2c1]
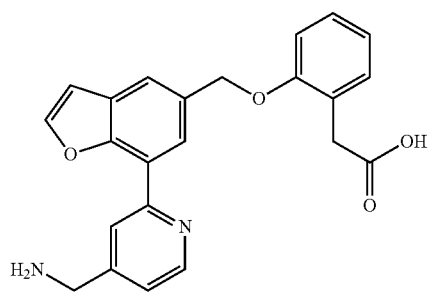 [SMILES: NCc1ccnc(-c2cc(COc3ccccc3CC(=O)O)cc3ccoc23)c1]
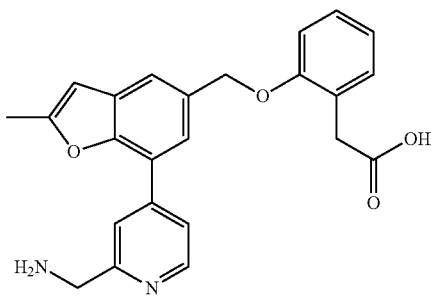 [SMILES: Cc1cc2cc(COc3ccccc3CC(=O)O)cc(-c3ccnc(CN)c3)c2o1]
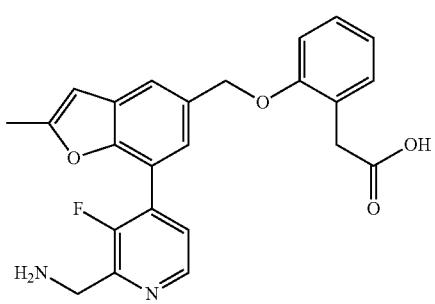 [SMILES: Cc1cc2cc(COc3ccccc3CC(=O)O)cc(-c3ccnc(CN)c3F)c2o1]

-continued
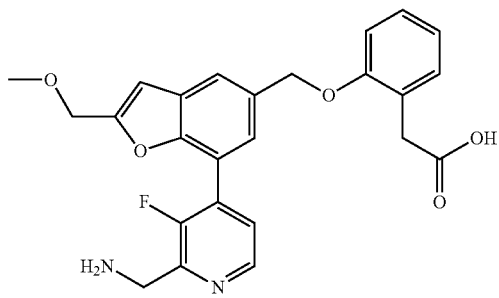 [SMILES: COCc1cc2cc(COc3ccccc3CC(=O)O)cc(-c3ccnc(CN)c3F)c2o1]
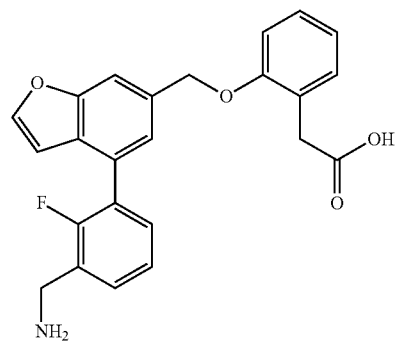 [SMILES: NCc1cccc(-c2cc(COc3ccccc3CC(=O)O)cc3occc23)c1F]
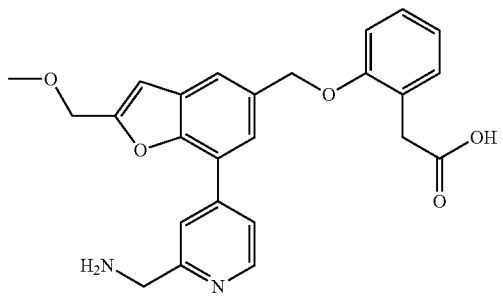 [SMILES: COCc1cc2cc(COc3ccccc3CC(=O)O)cc(-c3ccnc(CN)c3)c2o1]
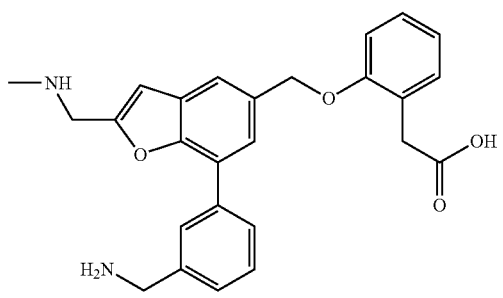 [SMILES: CNCc1cc2cc(COc3ccccc3CC(=O)O)cc(-c3cccc(CN)c3)c2o1]
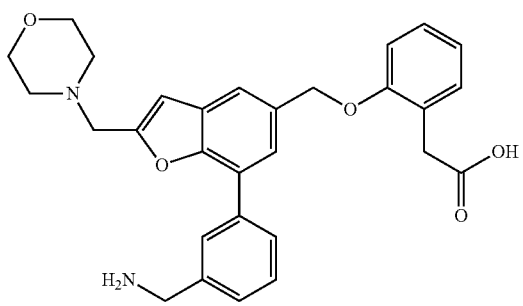 [SMILES: NCc1cccc(-c2cc(COc3ccccc3CC(=O)O)cc3cc(CN4CCOCC4)oc23)c1]

-continued
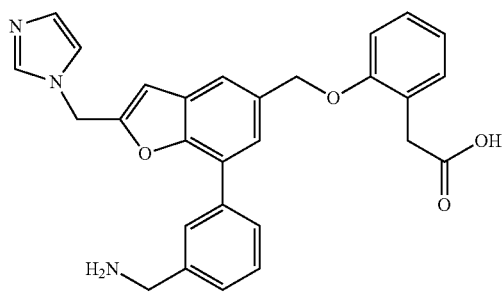 [SMILES: NCc1cccc(-c2cc(COc3ccccc3CC(=O)O)cc3cc(Cn4ccnc4)oc23)c1]
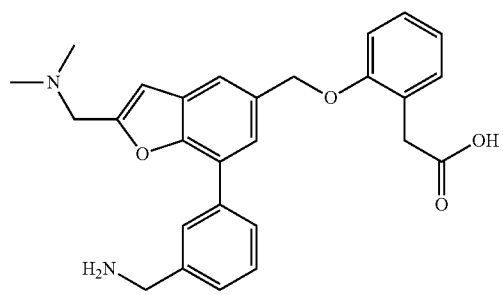 [SMILES: CN(C)Cc1cc2cc(COc3ccccc3CC(=O)O)cc(-c3cccc(CN)c3)c2o1]
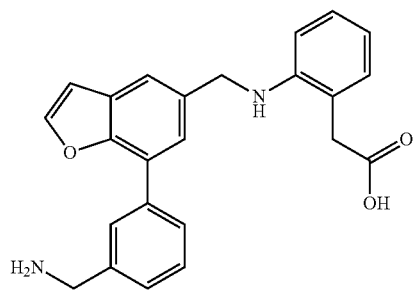 [SMILES: NCc1cccc(-c2cc(CNc3ccccc3CC(=O)O)cc3ccoc23)c1]
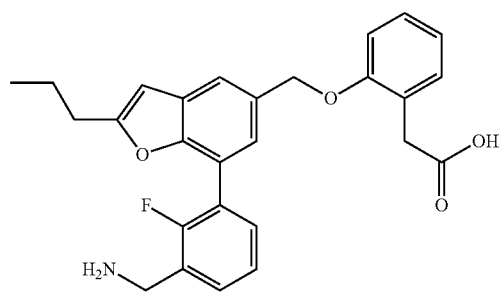 [SMILES: CCCc1cc2cc(COc3ccccc3CC(=O)O)cc(-c3cccc(CN)c3F)c2o1]
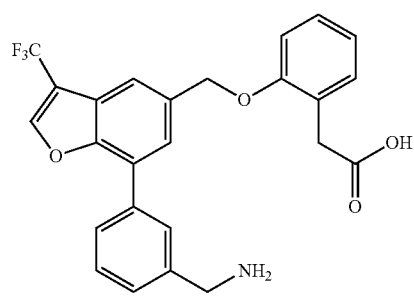 [SMILES: NCc1cccc(-c2cc(COc3ccccc3CC(=O)O)cc3c(C(F)(F)F)coc23)c1]

-continued
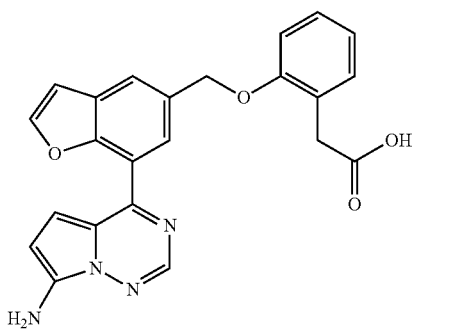 [SMILES: Nc1ccc2c(-c3cc(COc4ccccc4CC(=O)O)cc4ccoc34)ncnn12]
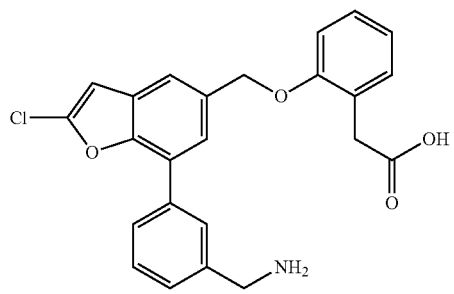 [SMILES: NCc1cccc(-c2cc(COc3ccccc3CC(=O)O)cc3cc(Cl)oc23)c1]
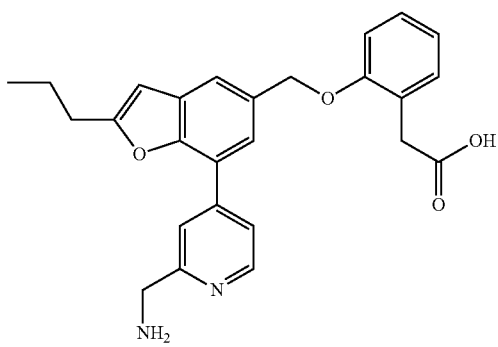 [SMILES: CCCc1cc2cc(COc3ccccc3CC(=O)O)cc(-c3ccnc(CN)c3)c2o1]
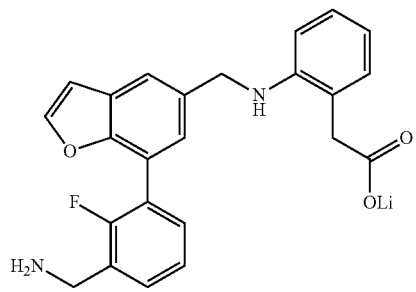
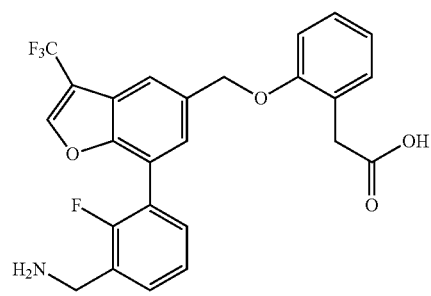 [SMILES: NCc1cccc(-c2cc(COc3ccccc3CC(=O)O)cc3c(C(F)(F)F)coc23)c1F]

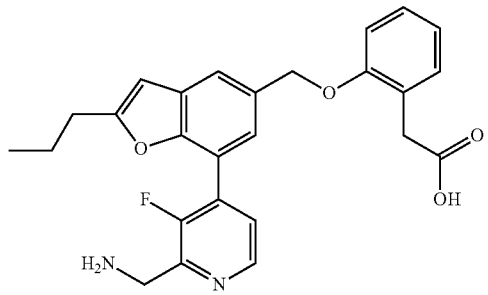 [SMILES: CCCc1cc2cc(COc3ccccc3CC(=O)O)cc(-c3ccnc(CN)c3F)c2o1]
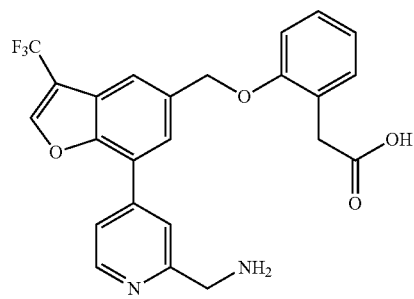 [SMILES: NCc1cc(-c2cc(COc3ccccc3CC(=O)O)cc3c(C(F)(F)F)coc23)ccn1]
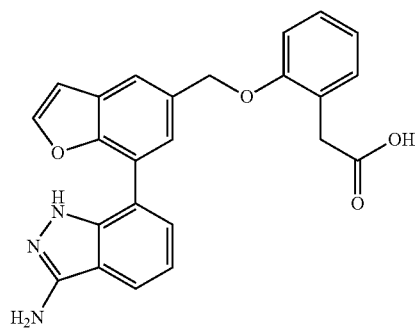 [SMILES: Nc1n[nH]c2c(-c3cc(COc4ccccc4CC(=O)O)cc4ccoc34)cccc12]
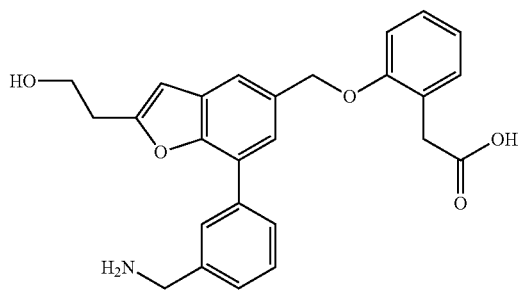 [SMILES: NCc1cccc(-c2cc(COc3ccccc3CC(=O)O)cc3cc(CCO)oc23)c1]
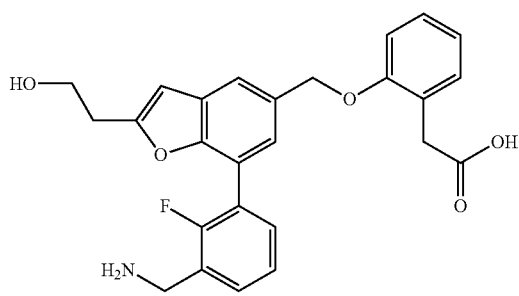 [SMILES: NCc1cccc(-c2cc(COc3ccccc3CC(=O)O)cc3cc(CCO)oc23)c1F]

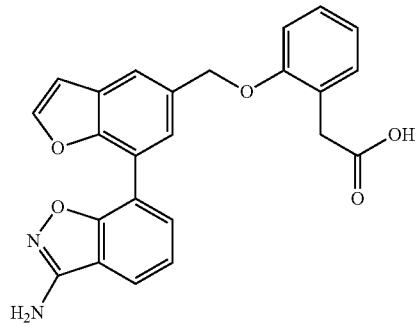 [SMILES: Nc1noc2c(-c3cc(COc4ccccc4CC(=O)O)cc4ccoc34)cccc12]
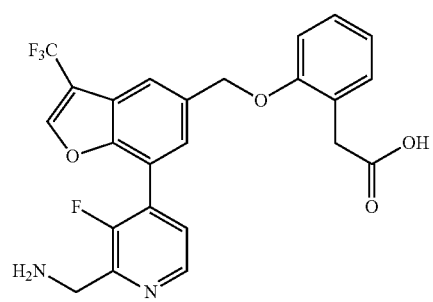 [SMILES: NCc1nccc(-c2cc(COc3ccccc3CC(=O)O)cc3c(C(F)(F)F)coc23)c1F]
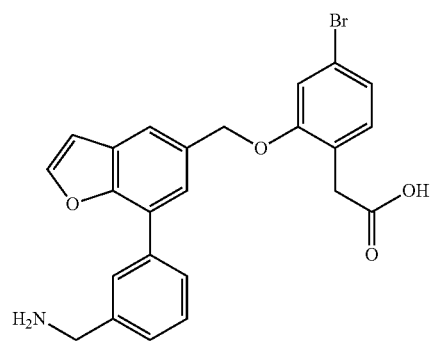 [SMILES: NCc1cccc(-c2cc(COc3cc(Br)ccc3CC(=O)O)cc3ccoc23)c1]
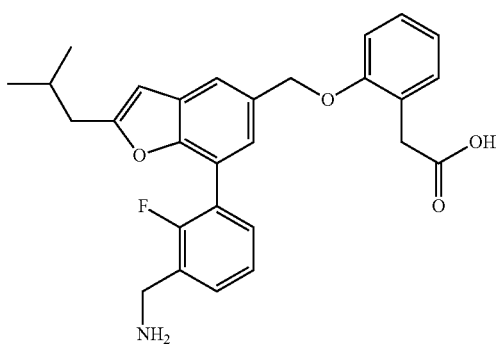 [SMILES: CC(C)Cc1cc2cc(COc3ccccc3CC(=O)O)cc(-c3cccc(CN)c3F)c2o1]
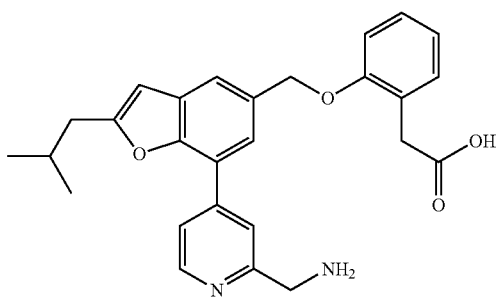 [SMILES: CC(C)Cc1cc2cc(COc3ccccc3CC(=O)O)cc(-c3ccnc(CN)c3)c2o1]

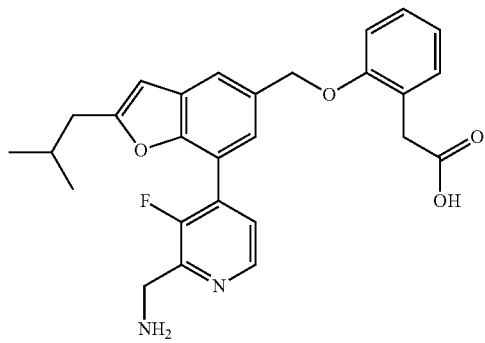 [SMILES: CC(C)Cc1cc2cc(COc3ccccc3CC(=O)O)cc(-c3ccnc(CN)c3F)c2o1]
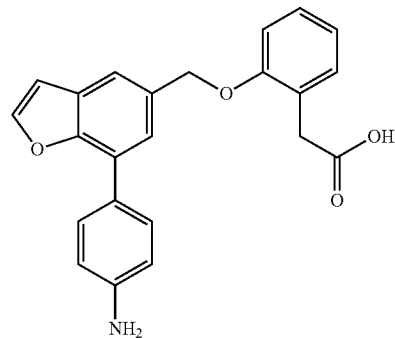 [SMILES: Nc1ccc(-c2cc(COc3ccccc3CC(=O)O)cc3ccoc23)cc1]
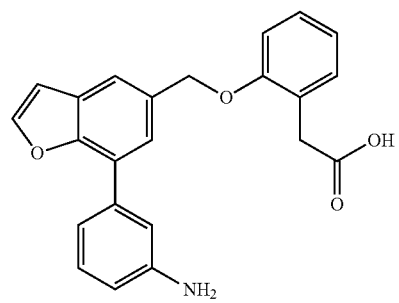 [SMILES: Nc1cccc(-c2cc(COc3ccccc3CC(=O)O)cc3ccoc23)c1]
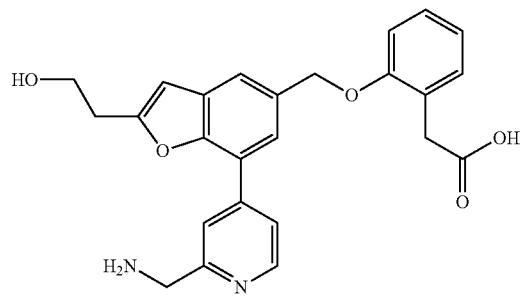 [SMILES: NCc1cc(-c2cc(COc3ccccc3CC(=O)O)cc3cc(CCO)oc23)ccn1]

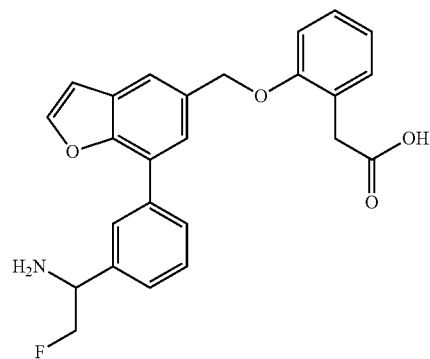 [SMILES: NC(CF)c1cccc(-c2cc(COc3ccccc3CC(=O)O)cc3ccoc23)c1]
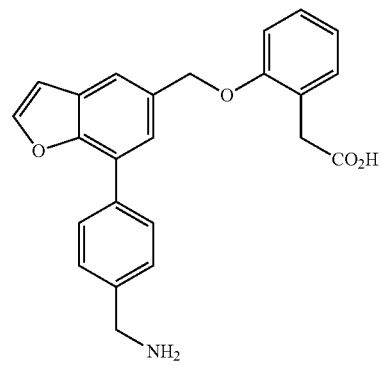 [SMILES: NCc1ccc(-c2cc(COc3ccccc3CC(=O)O)cc3ccoc23)cc1]
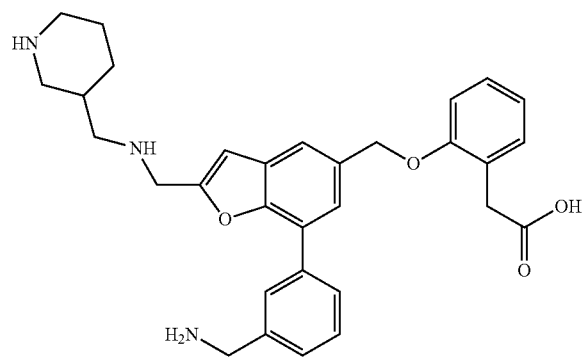 [SMILES: NCc1cccc(-c2cc(COc3ccccc3CC(=O)O)cc3cc(CNCC4CCCNC4)oc23)c1]
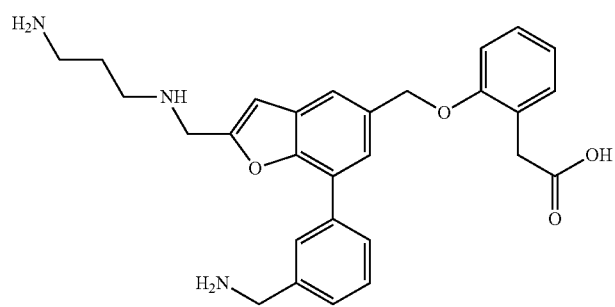 [SMILES: NCCCNCc1cc2cc(COc3ccccc3CC(=O)O)cc(-c3cccc(CN)c3)c2o1]

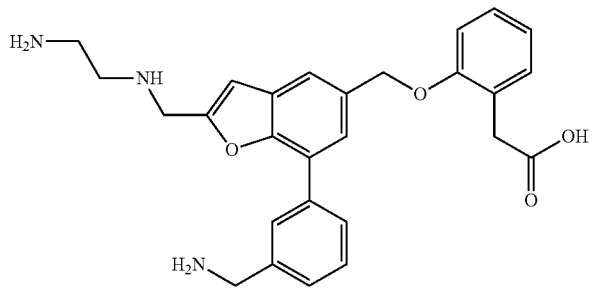 [SMILES: NCCNCc1cc2cc(COc3ccccc3CC(=O)O)cc(-c3cccc(CN)c3)c2o1]
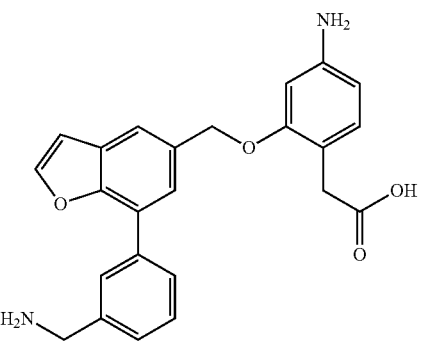
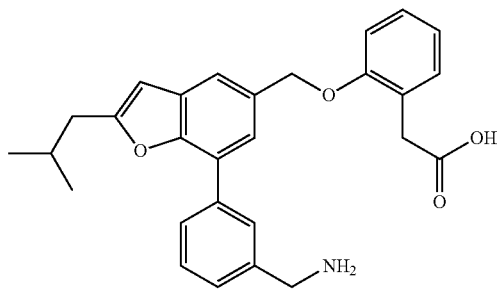 [SMILES: CC(C)Cc1cc2cc(COc3ccccc3CC(=O)O)cc(-c3cccc(CN)c3)c2o1]
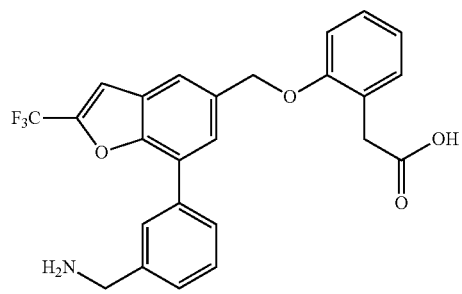
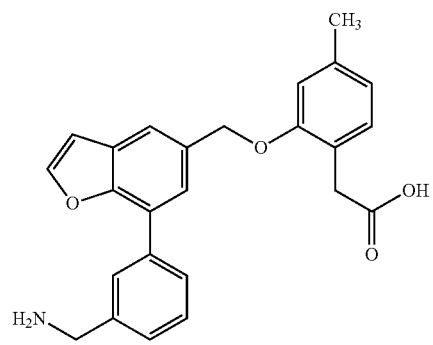 [SMILES: Cc1ccc(CC(=O)O)c(OCc2cc(-c3cccc(CN)c3)c3occc3c2)c1]

-continued
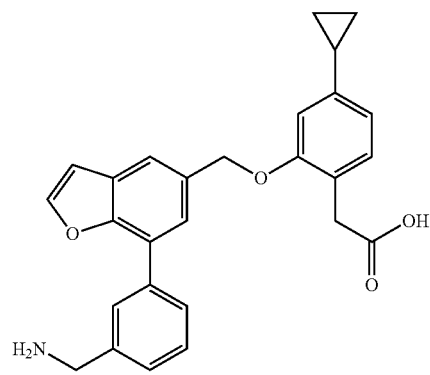 [SMILES: NCc1cccc(-c2cc(COc3cc(C4CC4)ccc3CC(=O)O)cc3ccoc23)c1]
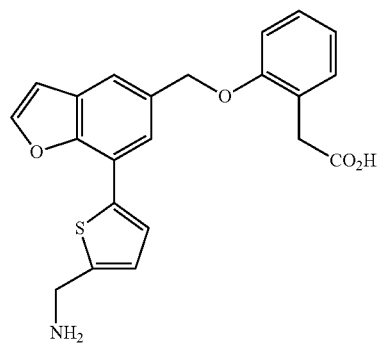 [SMILES: NCc1ccc(-c2cc(COc3ccccc3CC(=O)O)cc3ccoc23)s1]
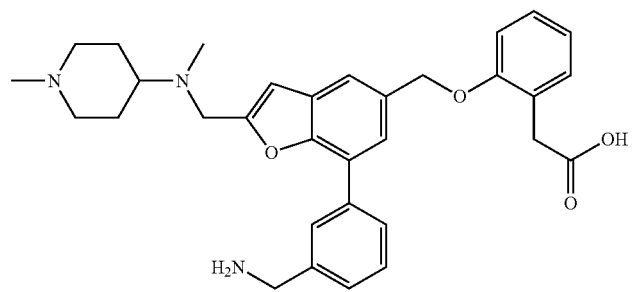 [SMILES: CN1CCC(N(C)Cc2cc3cc(COc4ccccc4CC(=O)O)cc(-c4cccc(CN)c4)c3o2)CC1]

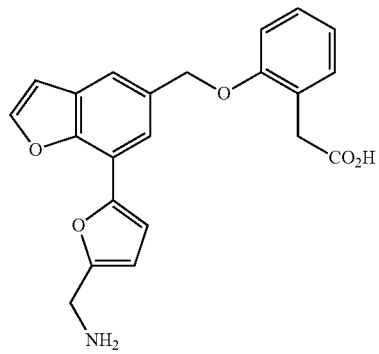 [SMILES: NCc1ccc(-c2cc(COc3ccccc3CC(=O)O)cc3ccoc23)o1]
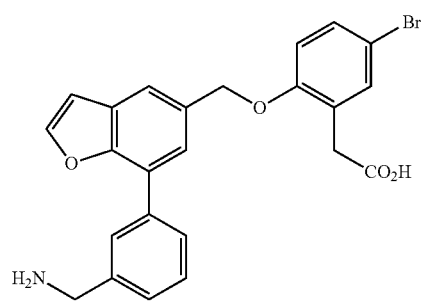 [SMILES: NCc1cccc(-c2cc(COc3ccc(Br)cc3CC(=O)O)cc3ccoc23)c1]
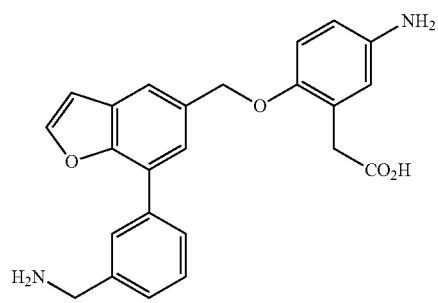 [SMILES: NCc1cccc(-c2cc(COc3ccc(N)cc3CC(=O)O)cc3ccoc23)c1]
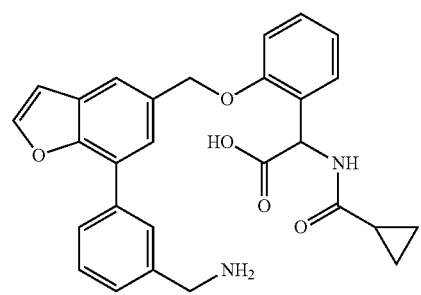 [SMILES: NCc1cccc(-c2cc(COc3ccccc3C(NC(=O)C3CC3)C(=O)O)cc3ccoc23)c1]
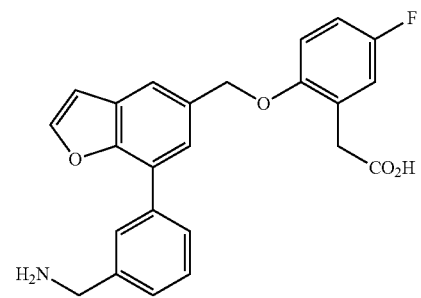 [SMILES: NCc1cccc(-c2cc(COc3ccc(F)cc3CC(=O)O)cc3ccoc23)c1]

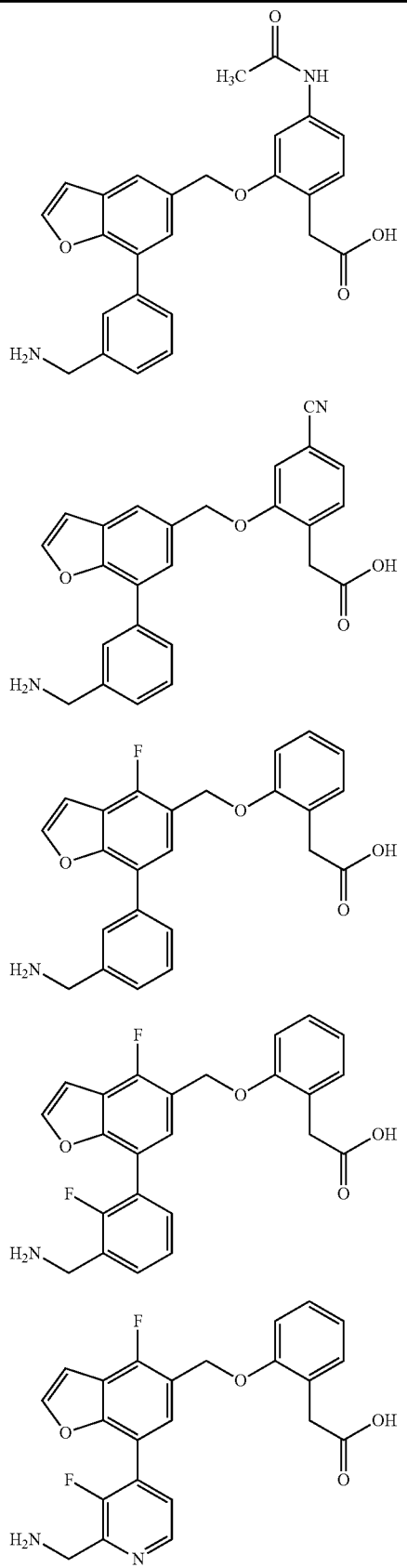

-continued
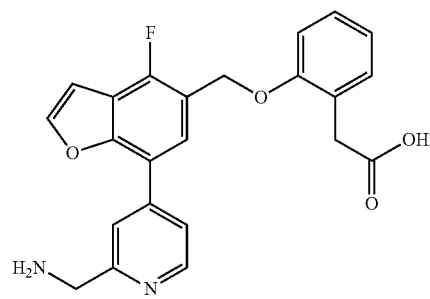 [SMILES: NCc1cc(-c2cc(COc3ccccc3CC(=O)O)c(F)c3ccoc23)ccn1]
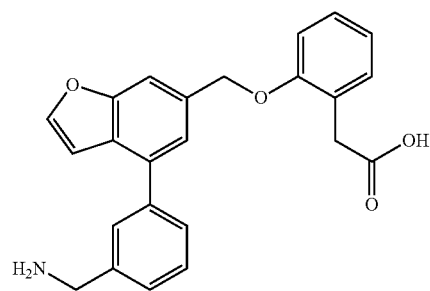 [SMILES: NCc1cccc(-c2cc(COc3ccccc3CC(=O)O)cc3occc23)c1]
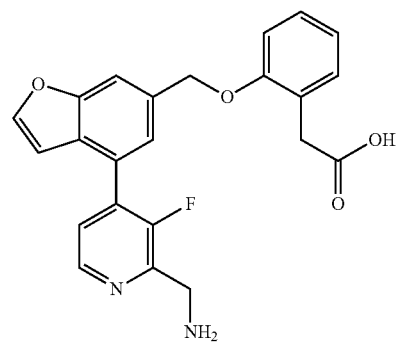 [SMILES: NCc1nccc(-c2cc(COc3ccccc3CC(=O)O)cc3occc23)c1F]
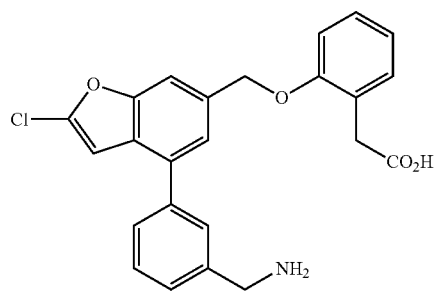 [SMILES: NCc1cccc(-c2cc(COc3ccccc3CC(=O)O)cc3oc(Cl)cc23)c1]
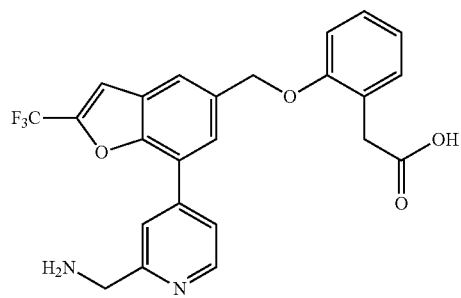

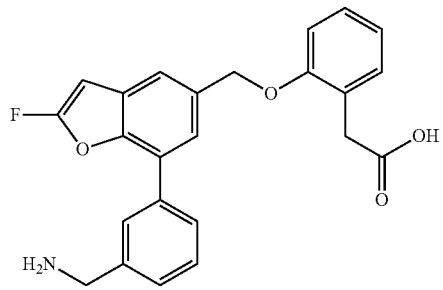 [SMILES: NCc1cccc(-c2cc(COc3ccccc3CC(=O)O)cc3cc(F)oc23)c1]
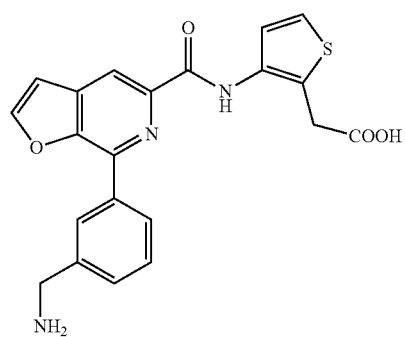 [SMILES: NCc1cccc(-c2nc(C(=O)Nc3ccsc3CC(=O)O)cc3ccoc23)c1]
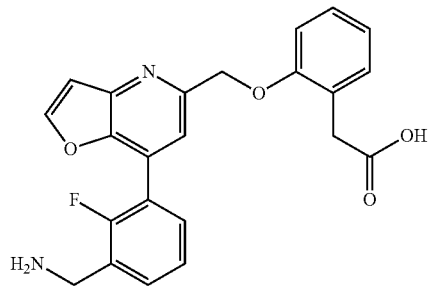 [SMILES: NCc1cccc(-c2cc(COc3ccccc3CC(=O)O)nc3ccoc23)c1F]
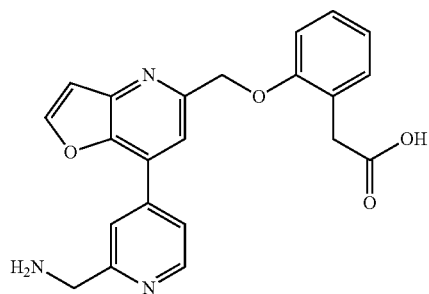 [SMILES: NCc1cc(-c2cc(COc3ccccc3CC(=O)O)nc3ccoc23)ccn1]
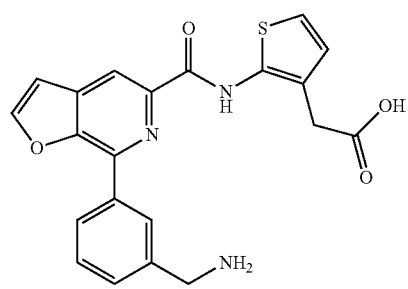 [SMILES: NCc1cccc(-c2nc(C(=O)Nc3sccc3CC(=O)O)cc3ccoc23)c1]

-continued
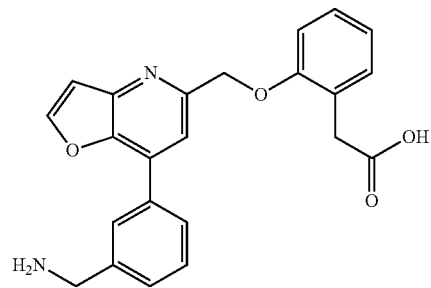 [SMILES: NCc1cccc(-c2cc(COc3ccccc3CC(=O)O)nc3ccoc23)c1]
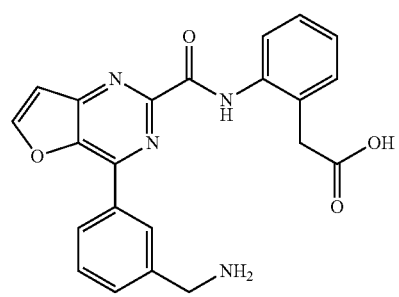 [SMILES: NCc1cccc(-c2nc(C(=O)Nc3ccccc3CC(=O)O)nc3ccoc23)c1]
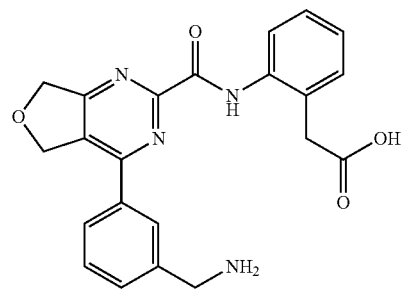 [SMILES: NCc1cccc(-c2nc(C(=O)Nc3ccccc3CC(=O)O)nc3c2COC3)c1]
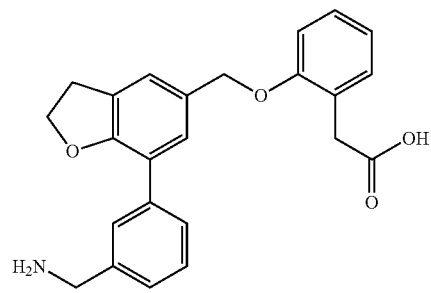 [SMILES: NCc1cccc(-c2cc(COc3ccccc3CC(=O)O)cc3c2OCC3)c1]
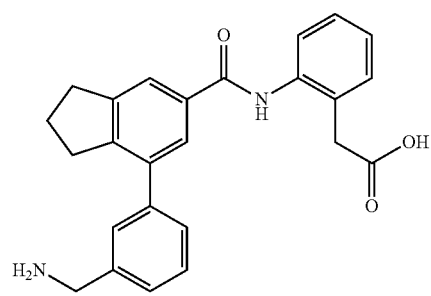 [SMILES: NCc1cccc(-c2cc(C(=O)Nc3ccccc3CC(=O)O)cc3c2CCC3)c1]

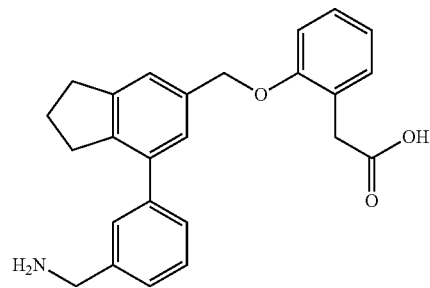 [SMILES: NCc1cccc(-c2cc(COc3ccccc3CC(=O)O)cc3c2CCC3)c1]
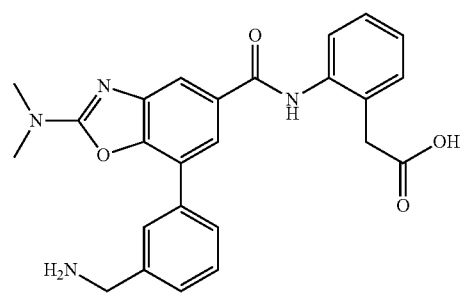 [SMILES: CN(C)c1nc2cc(C(=O)Nc3ccccc3CC(=O)O)cc(-c3cccc(CN)c3)c2o1]
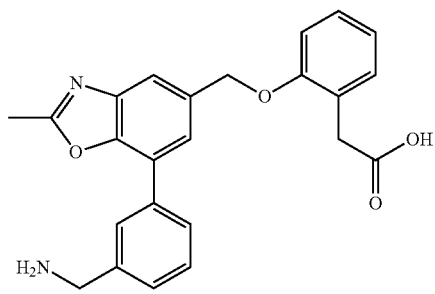 [SMILES: Cc1nc2cc(COc3ccccc3CC(=O)O)cc(-c3cccc(CN)c3)c2o1]
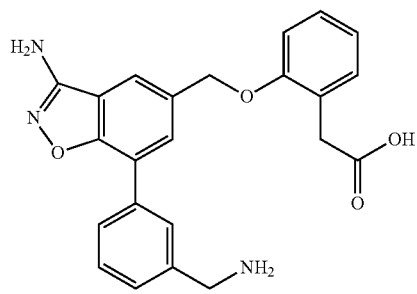 [SMILES: NCc1cccc(-c2cc(COc3ccccc3CC(=O)O)cc3c(N)noc23)c1]
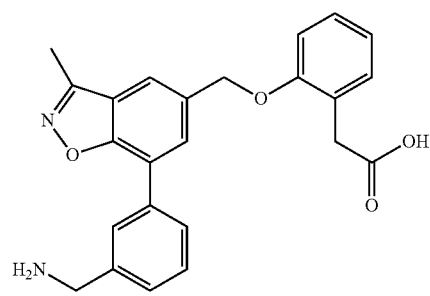 [SMILES: Cc1noc2c(-c3cccc(CN)c3)cc(COc3ccccc3CC(=O)O)cc12]

-continued
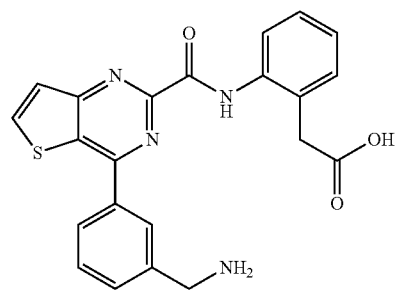 [SMILES: NCc1cccc(-c2nc(C(=O)Nc3ccccc3CC(=O)O)nc3ccsc23)c1]
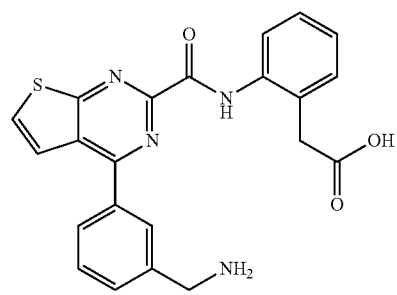 [SMILES: NCc1cccc(-c2nc(C(=O)Nc3ccccc3CC(=O)O)nc3sccc23)c1]
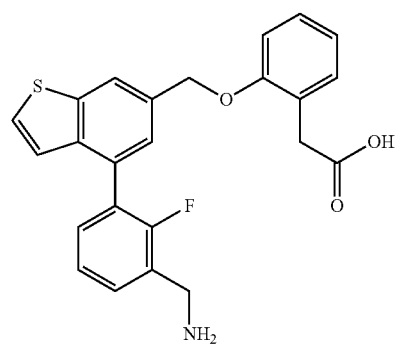 [SMILES: NCc1cccc(-c2cc(COc3ccccc3CC(=O)O)cc3sccc23)c1F]
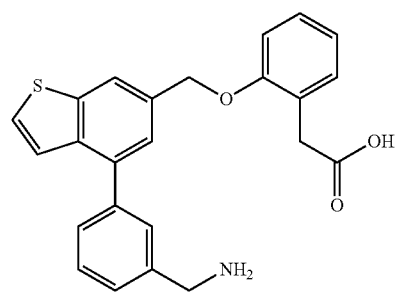 [SMILES: NCc1cccc(-c2cc(COc3ccccc3CC(=O)O)cc3sccc23)c1]
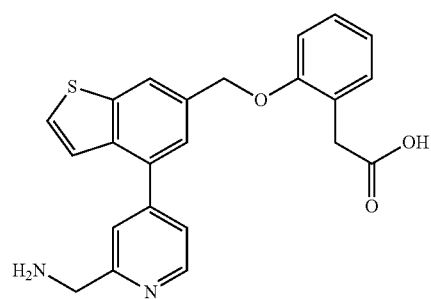 [SMILES: NCc1cc(-c2cc(COc3ccccc3CC(=O)O)cc3sccc23)ccn1]

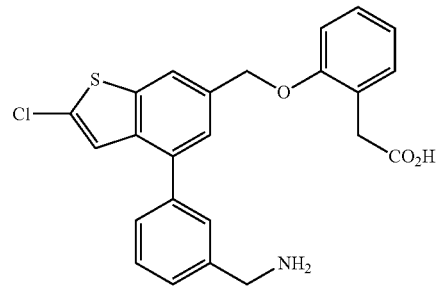
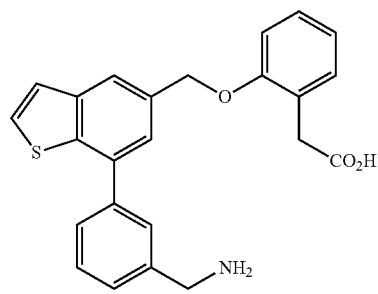 [SMILES: NCc1cccc(-c2cc(COc3ccccc3CC(=O)O)cc3ccsc23)c1]
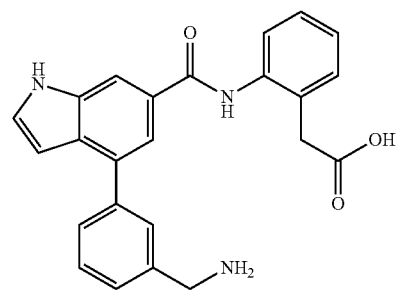 [SMILES: NCc1cccc(-c2cc(C(=O)Nc3ccccc3CC(=O)O)cc3[nH]ccc23)c1]
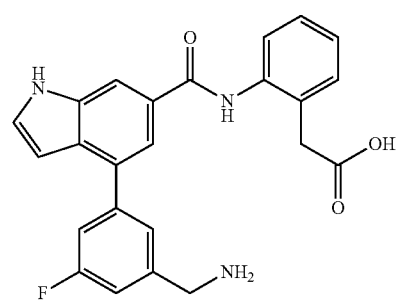 [SMILES: NCc1cc(F)cc(-c2cc(C(=O)Nc3ccccc3CC(=O)O)cc3[nH]ccc23)c1]
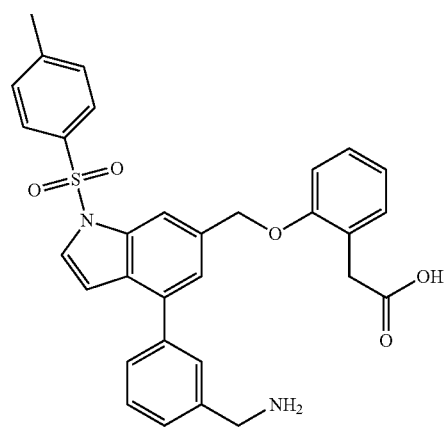 [SMILES: Cc1ccc(S(=O)(=O)n2ccc3c(-c4cccc(CN)c4)cc(COc4ccccc4CC(=O)O)cc32)cc1]

-continued
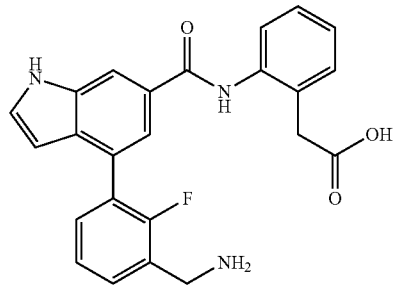 [SMILES: NCc1cccc(-c2cc(C(=O)Nc3ccccc3CC(=O)O)cc3[nH]ccc23)c1F]
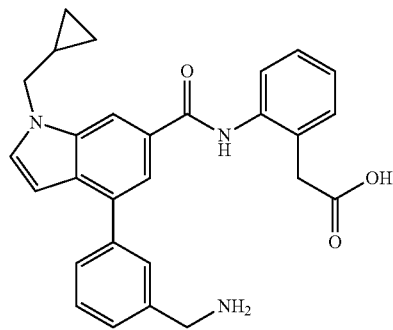 [SMILES: NCc1cccc(-c2cc(C(=O)Nc3ccccc3CC(=O)O)cc3c2ccn3CC2CC2)c1]
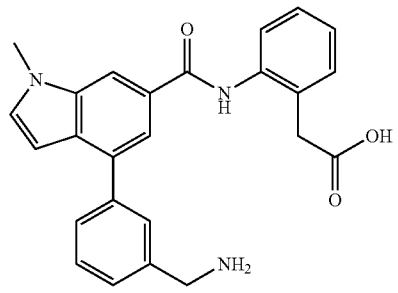 [SMILES: Cn1ccc2c(-c3cccc(CN)c3)cc(C(=O)Nc3ccccc3CC(=O)O)cc21]
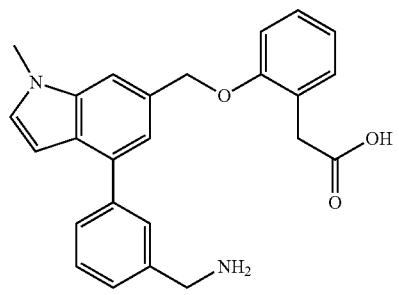 [SMILES: Cn1ccc2c(-c3cccc(CN)c3)cc(COc3ccccc3CC(=O)O)cc21]
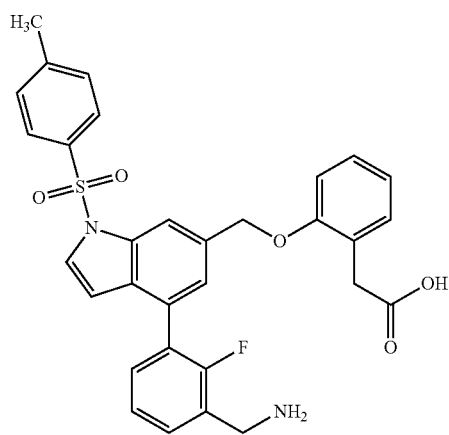 [SMILES: Cc1ccc(S(=O)(=O)n2ccc3c(-c4cccc(CN)c4F)cc(COc4ccccc4CC(=O)O)cc32)cc1]

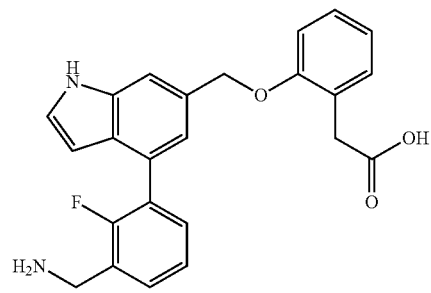 [SMILES: NCc1cccc(-c2cc(COc3ccccc3CC(=O)O)cc3[nH]ccc23)c1F]
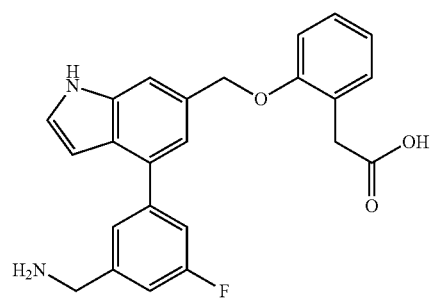 [SMILES: NCc1cc(F)cc(-c2cc(COc3ccccc3CC(=O)O)cc3[nH]ccc23)c1]
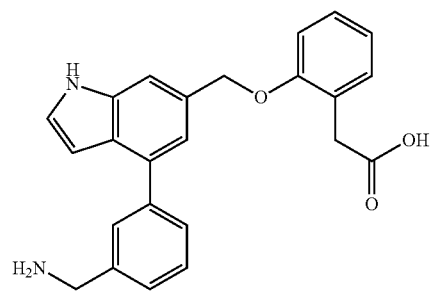 [SMILES: NCc1cccc(-c2cc(COc3ccccc3CC(=O)O)cc3[nH]ccc23)c1]
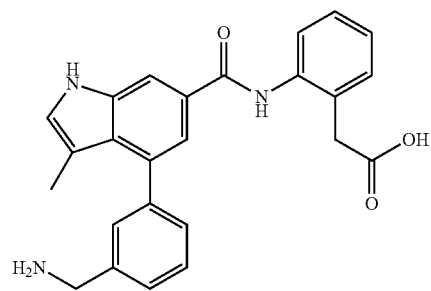 [SMILES: Cc1c[nH]c2cc(C(=O)Nc3ccccc3CC(=O)O)cc(-c3cccc(CN)c3)c12]
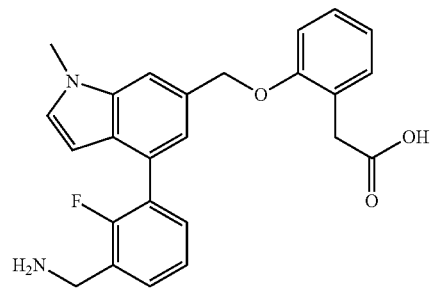 [SMILES: Cn1ccc2c(-c3cccc(CN)c3F)cc(COc3ccccc3CC(=O)O)cc21]

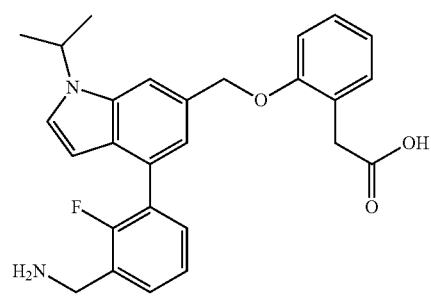 [SMILES: CC(C)n1ccc2c(-c3cccc(CN)c3F)cc(COc3ccccc3CC(=O)O)cc21]
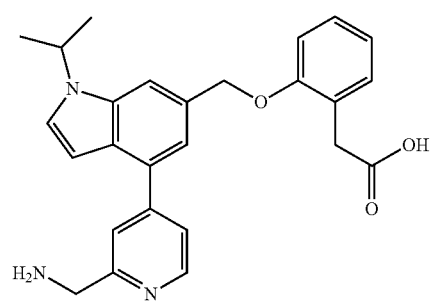 [SMILES: CC(C)n1ccc2c(-c3ccnc(CN)c3)cc(COc3ccccc3CC(=O)O)cc21]

-continued
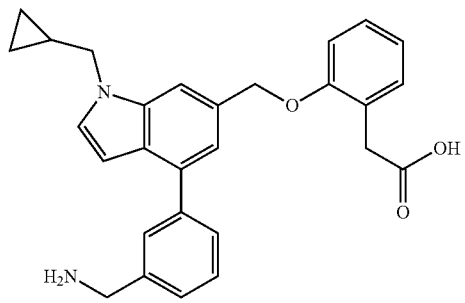 [SMILES: NCc1cccc(-c2cc(COc3ccccc3CC(=O)O)cc3c2ccn3CC2CC2)c1]
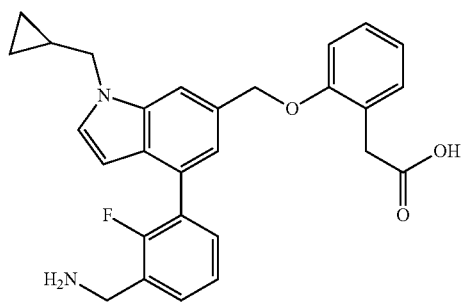 [SMILES: NCc1cccc(-c2cc(COc3ccccc3CC(=O)O)cc3c2ccn3CC2CC2)c1F]
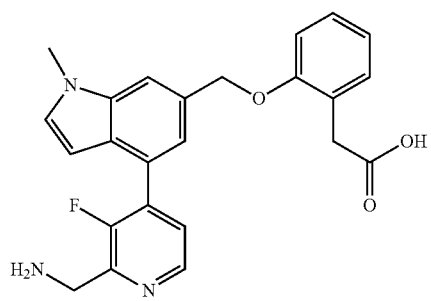 [SMILES: Cn1ccc2c(-c3ccnc(CN)c3F)cc(COc3ccccc3CC(=O)O)cc21]
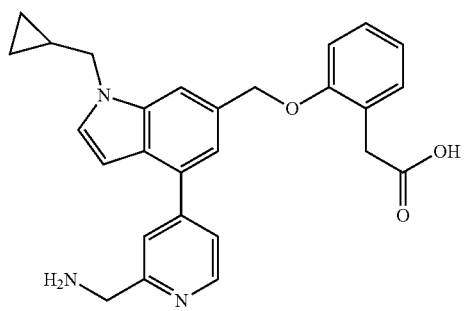 [SMILES: NCc1cc(-c2cc(COc3ccccc3CC(=O)O)cc3c2ccn3CC2CC2)ccn1]
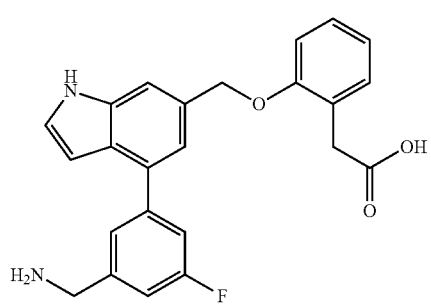 [SMILES: NCc1cc(F)cc(-c2cc(COc3ccccc3CC(=O)O)cc3[nH]ccc23)c1]

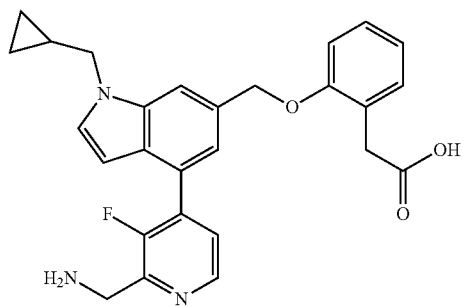 [SMILES: NCc1nccc(-c2cc(COc3ccccc3CC(=O)O)cc3c2ccn3CC2CC2)c1F]
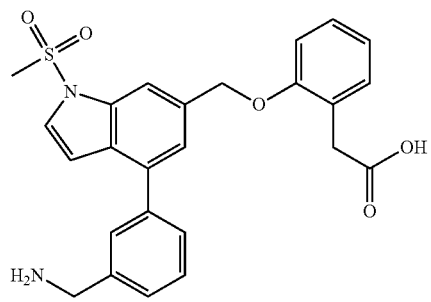 [SMILES: CS(=O)(=O)n1ccc2c(-c3cccc(CN)c3)cc(COc3ccccc3CC(=O)O)cc21]
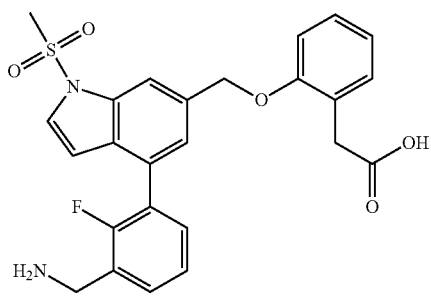 [SMILES: CS(=O)(=O)n1ccc2c(-c3cccc(CN)c3F)cc(COc3ccccc3CC(=O)O)cc21]
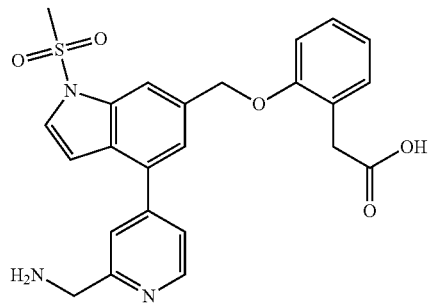 [SMILES: CS(=O)(=O)n1ccc2c(-c3ccnc(CN)c3)cc(COc3ccccc3CC(=O)O)cc21]
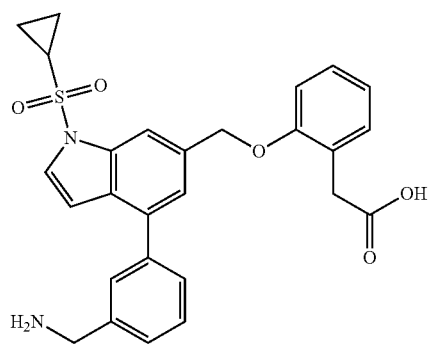 [SMILES: NCc1cccc(-c2cc(COc3ccccc3CC(=O)O)cc3c2ccn3S(=O)(=O)C2CC2)c1]

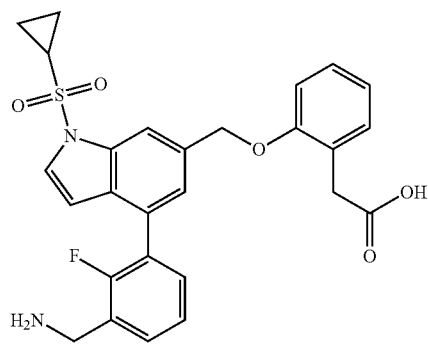 [SMILES: NCc1cccc(-c2cc(COc3ccccc3CC(=O)O)cc3c2ccn3S(=O)(=O)C2CC2)c1F]
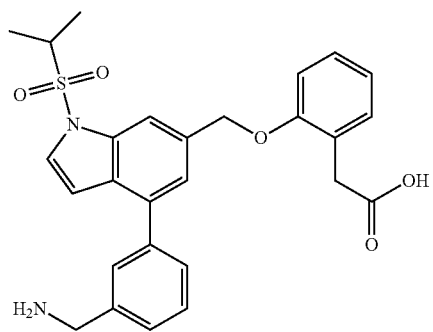 [SMILES: CC(C)S(=O)(=O)n1ccc2c(-c3cccc(CN)c3)cc(COc3ccccc3CC(=O)O)cc21]
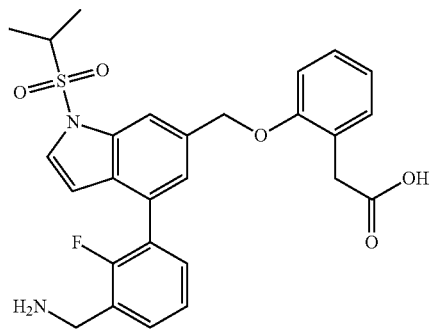 [SMILES: CC(C)S(=O)(=O)n1ccc2c(-c3cccc(CN)c3F)cc(COc3ccccc3CC(=O)O)cc21]
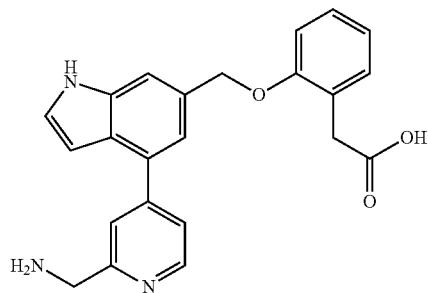 [SMILES: NCc1cc(-c2cc(COc3ccccc3CC(=O)O)cc3[nH]ccc23)ccn1]
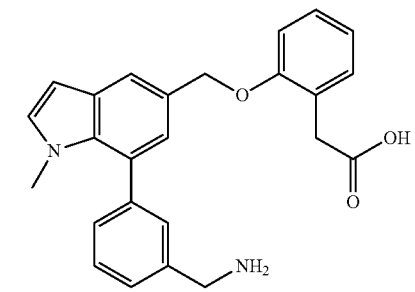 [SMILES: Cn1ccc2cc(COc3ccccc3CC(=O)O)cc(-c3cccc(CN)c3)c21]

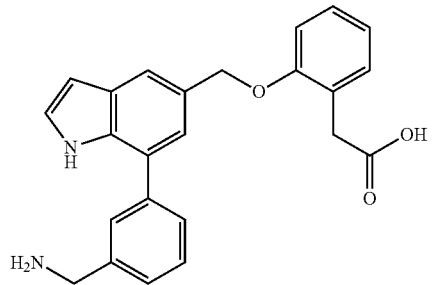 [SMILES: NCc1cccc(-c2cc(COc3ccccc3CC(=O)O)cc3cc[nH]c23)c1]
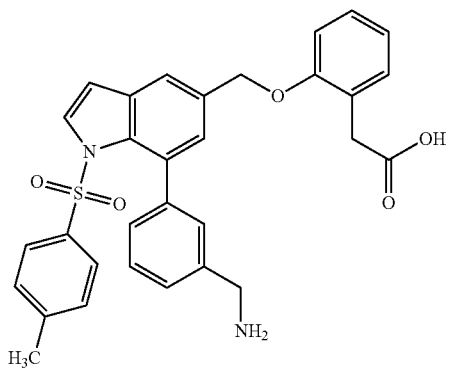 [SMILES: Cc1ccc(S(=O)(=O)n2ccc3cc(COc4ccccc4CC(=O)O)cc(-c4cccc(CN)c4)c32)cc1]
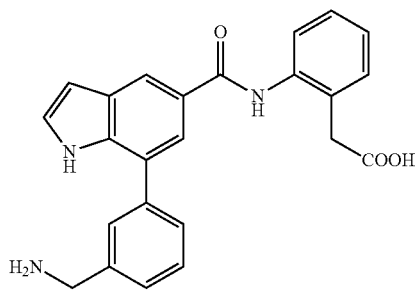 [SMILES: NCc1cccc(-c2cc(C(=O)Nc3ccccc3CC(=O)O)cc3cc[nH]c23)c1]
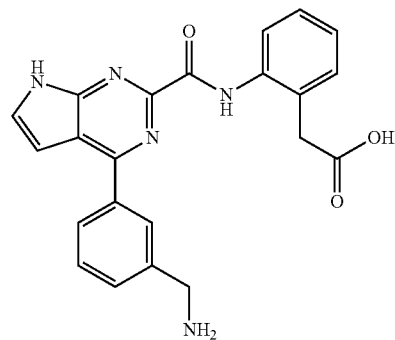 [SMILES: NCc1cccc(-c2nc(C(=O)Nc3ccccc3CC(=O)O)nc3[nH]ccc23)c1]
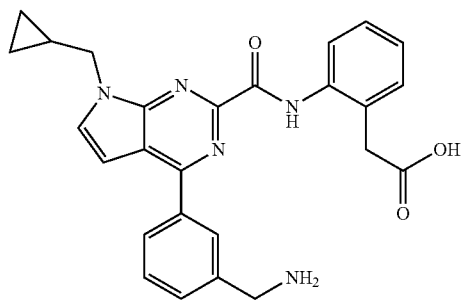 [SMILES: NCc1cccc(-c2nc(C(=O)Nc3ccccc3CC(=O)O)nc3c2ccn3CC2CC2)c1]

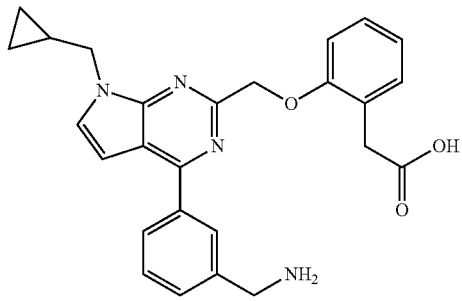 [SMILES: NCc1cccc(-c2nc(COc3ccccc3CC(=O)O)nc3c2ccn3CC2CC2)c1]
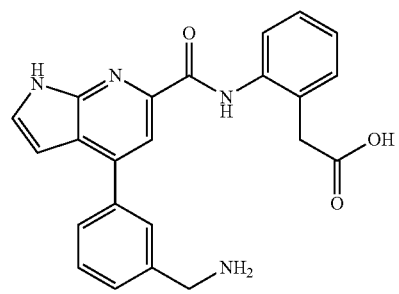 [SMILES: NCc1cccc(-c2cc(C(=O)Nc3ccccc3CC(=O)O)nc3[nH]ccc23)c1]
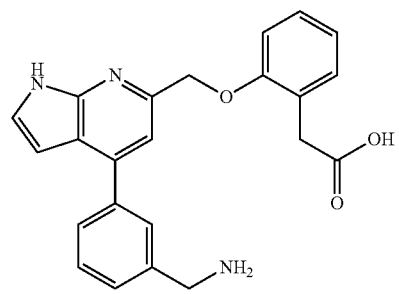 [SMILES: NCc1cccc(-c2cc(COc3ccccc3CC(=O)O)nc3[nH]ccc23)c1]
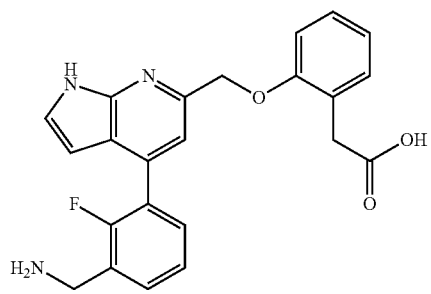 [SMILES: NCc1cccc(-c2cc(COc3ccccc3CC(=O)O)nc3[nH]ccc23)c1F]
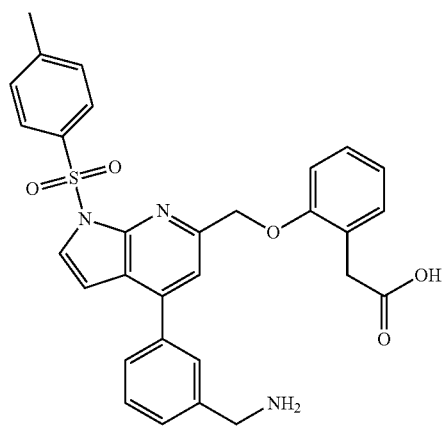 [SMILES: Cc1ccc(S(=O)(=O)n2ccc3c(-c4cccc(CN)c4)cc(COc4ccccc4CC(=O)O)nc32)cc1]

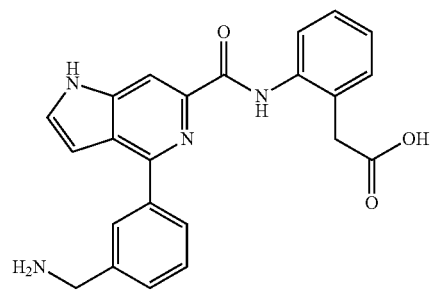 [SMILES: NCc1cccc(-c2nc(C(=O)Nc3ccccc3CC(=O)O)cc3[nH]ccc23)c1]
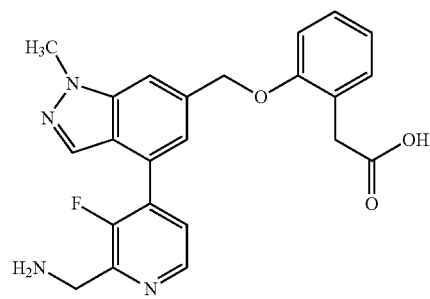 [SMILES: Cn1ncc2c(-c3ccnc(CN)c3F)cc(COc3ccccc3CC(=O)O)cc21]
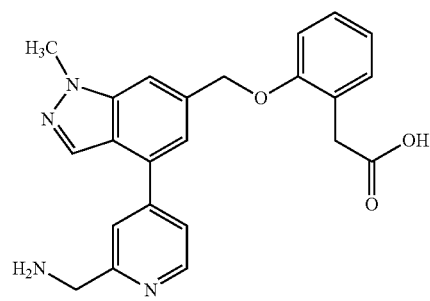 [SMILES: Cn1ncc2c(-c3ccnc(CN)c3)cc(COc3ccccc3CC(=O)O)cc21]
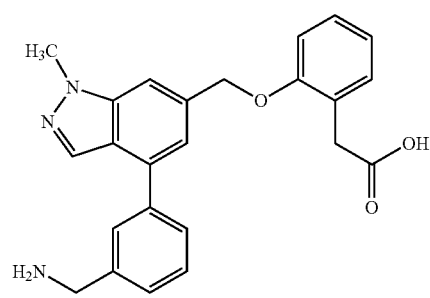 [SMILES: Cn1ncc2c(-c3cccc(CN)c3)cc(COc3ccccc3CC(=O)O)cc21]
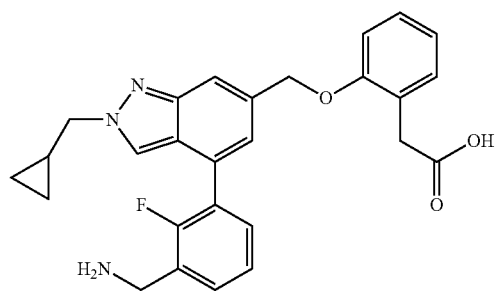 [SMILES: NCc1cccc(-c2cc(COc3ccccc3CC(=O)O)cc3nn(CC4CC4)cc23)c1F]

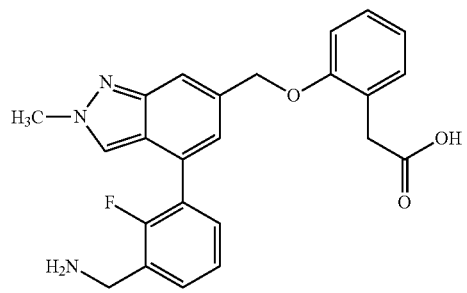 [SMILES: Cn1cc2c(-c3cccc(CN)c3F)cc(COc3ccccc3CC(=O)O)cc2n1]
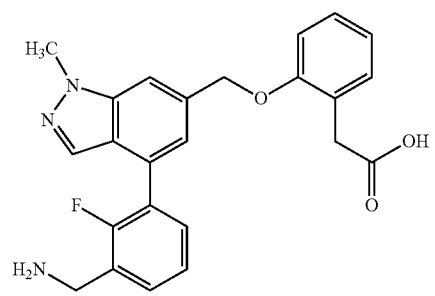 [SMILES: Cn1ncc2c(-c3cccc(CN)c3F)cc(COc3ccccc3CC(=O)O)cc21]
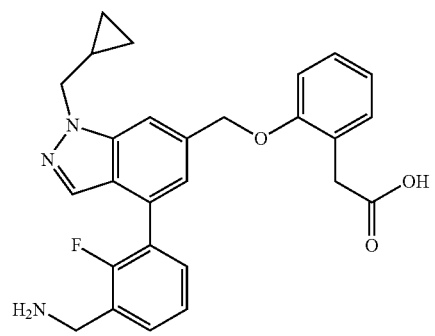 [SMILES: NCc1cccc(-c2cc(COc3ccccc3CC(=O)O)cc3c2cnn3CC2CC2)c1F]
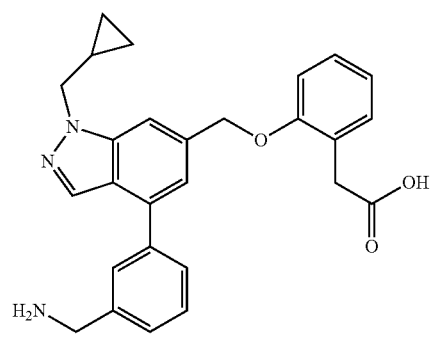 [SMILES: NCc1cccc(-c2cc(COc3ccccc3CC(=O)O)cc3c2cnn3CC2CC2)c1]
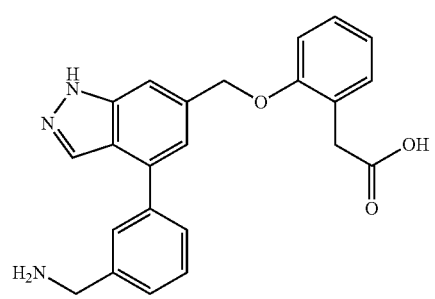 [SMILES: NCc1cccc(-c2cc(COc3ccccc3CC(=O)O)cc3[nH]ncc23)c1]

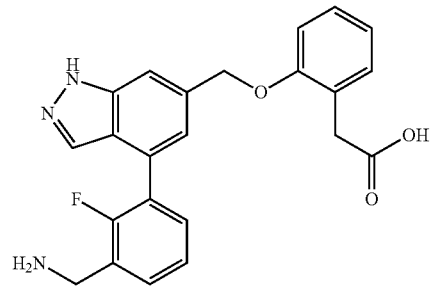 [SMILES: NCc1cccc(-c2cc(COc3ccccc3CC(=O)O)cc3[nH]ncc23)c1F]
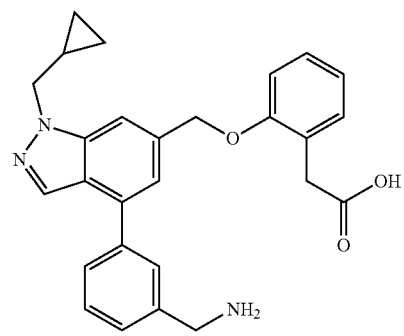 [SMILES: NCc1cccc(-c2cc(COc3ccccc3CC(=O)O)cc3c2cnn3CC2CC2)c1]
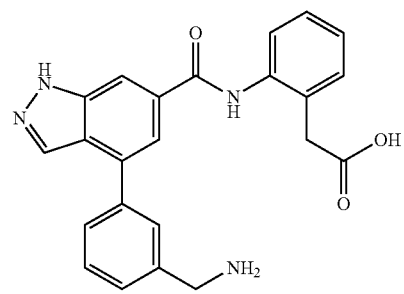 [SMILES: NCc1cccc(-c2cc(C(=O)Nc3ccccc3CC(=O)O)cc3[nH]ncc23)c1]
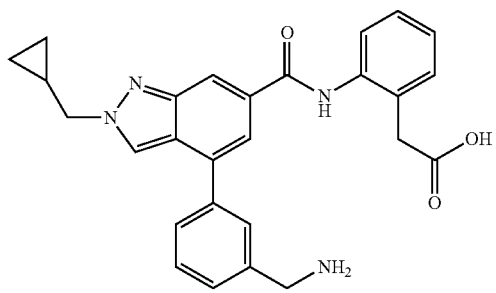 [SMILES: NCc1cccc(-c2cc(C(=O)Nc3ccccc3CC(=O)O)cc3nn(CC4CC4)cc23)c1]
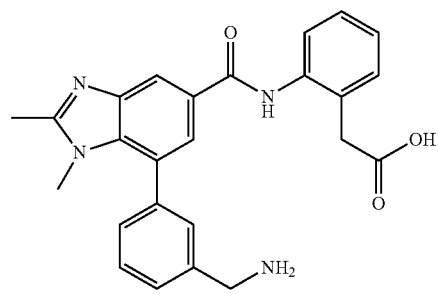 [SMILES: Cc1nc2cc(C(=O)Nc3ccccc3CC(=O)O)cc(-c3cccc(CN)c3)c2n1C]

-continued
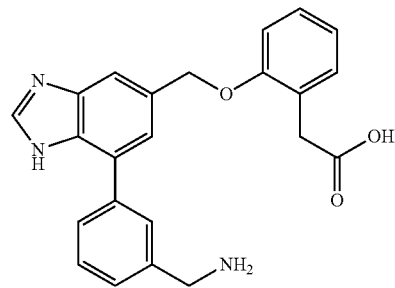 [SMILES: NCc1cccc(-c2cc(COc3ccccc3CC(=O)O)cc3nc[nH]c23)c1]
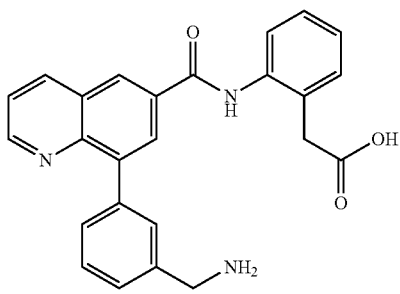 [SMILES: NCc1cccc(-c2cc(C(=O)Nc3ccccc3CC(=O)O)cc3cccnc23)c1]
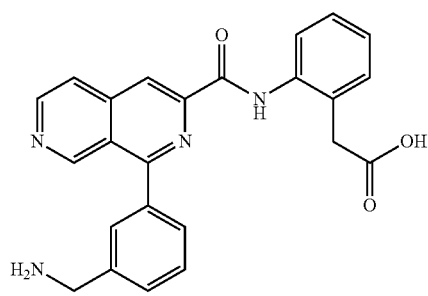 [SMILES: NCc1cccc(-c2nc(C(=O)Nc3ccccc3CC(=O)O)cc3ccncc23)c1]
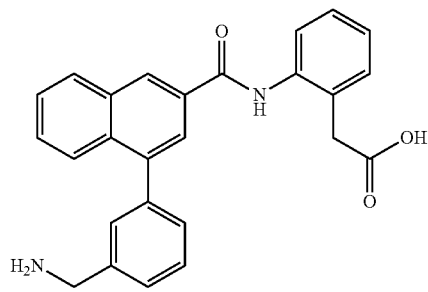 [SMILES: NCc1cccc(-c2cc(C(=O)Nc3ccccc3CC(=O)O)cc3ccccc23)c1]
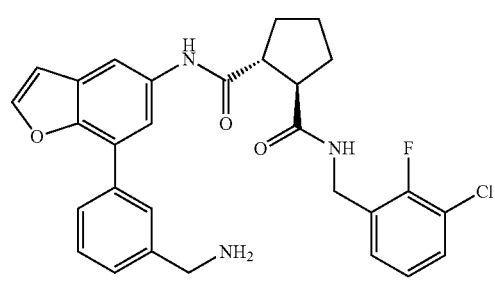 [SMILES: NCc1cccc(-c2cc(NC(=O)[C@@H]3CCC[C@H]3C(=O)NCc3cccc(Cl)c3F)cc3ccoc23)c1]

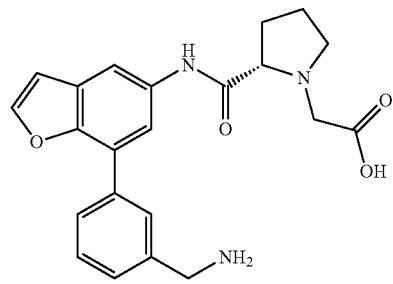 [SMILES: NCc1cccc(-c2cc(NC(=O)[C@@H]3CCCN3CC(=O)O)cc3ccoc23)c1]
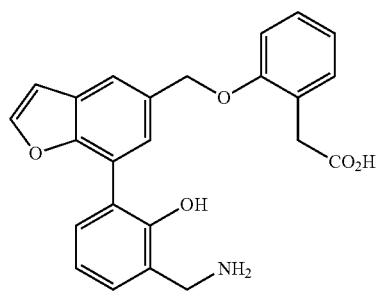 [SMILES: NCc1cccc(-c2cc(COc3ccccc3CC(=O)O)cc3ccoc23)c1O]
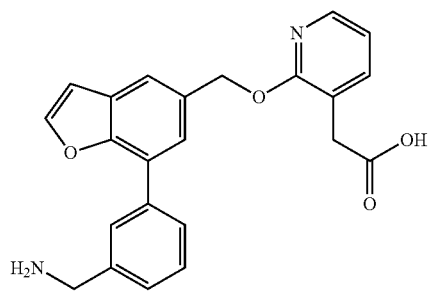 [SMILES: NCc1cccc(-c2cc(COc3ncccc3CC(=O)O)cc3ccoc23)c1]
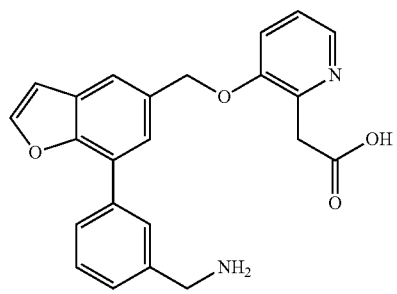 [SMILES: NCc1cccc(-c2cc(COc3cccnc3CC(=O)O)cc3ccoc23)c1]
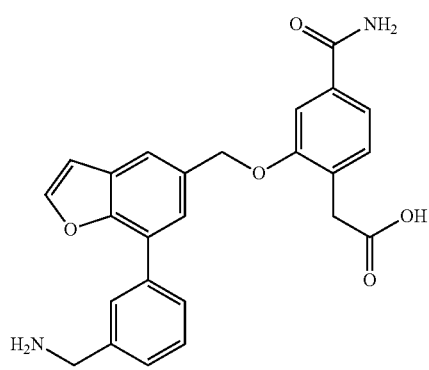 [SMILES: NCc1cccc(-c2cc(COc3cc(C(N)=O)ccc3CC(=O)O)cc3ccoc23)c1]

-continued
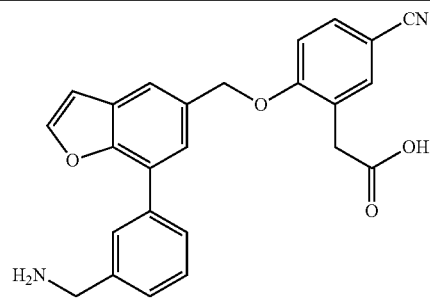
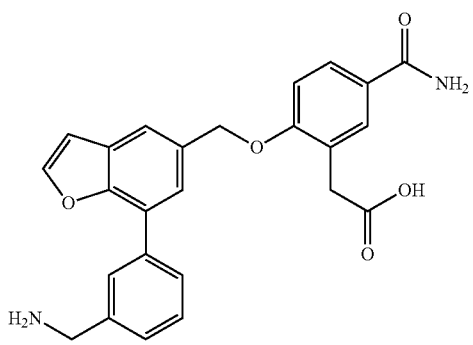 [SMILES: NCc1cccc(-c2cc(COc3ccc(C(N)=O)cc3CC(=O)O)cc3ccoc23)c1]
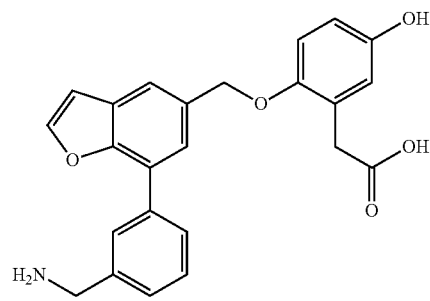 [SMILES: NCc1cccc(-c2cc(COc3ccc(O)cc3CC(=O)O)cc3ccoc23)c1]
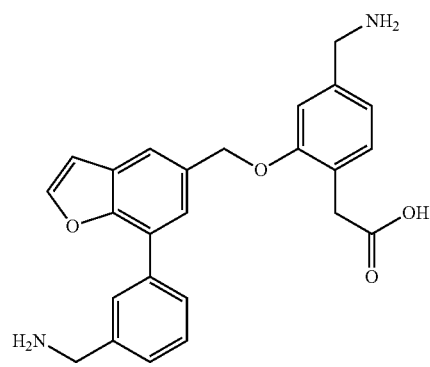 [SMILES: NCc1cccc(-c2cc(COc3cc(CN)ccc3CC(=O)O)cc3ccoc23)c1]
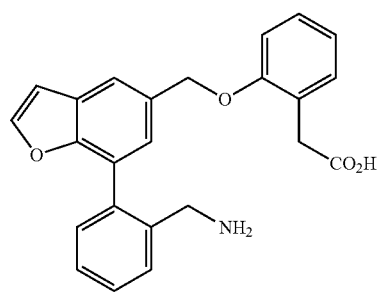 [SMILES: NCc1ccccc1-c1cc(COc2ccccc2CC(=O)O)cc2ccoc12]

-continued
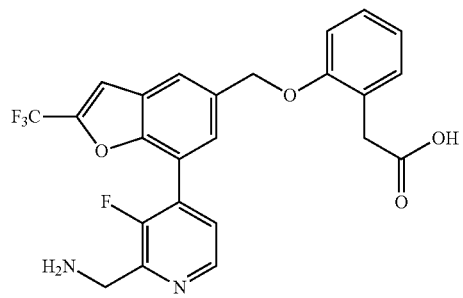 [SMILES: NCc1nccc(-c2cc(COc3ccccc3CC(=O)O)cc3cc(C(F)(F)F)oc23)c1F]
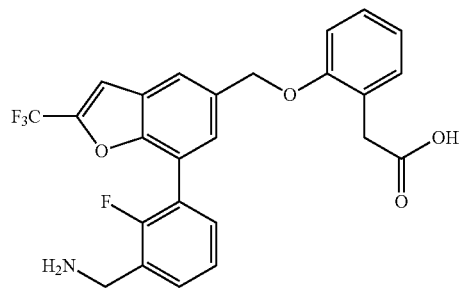
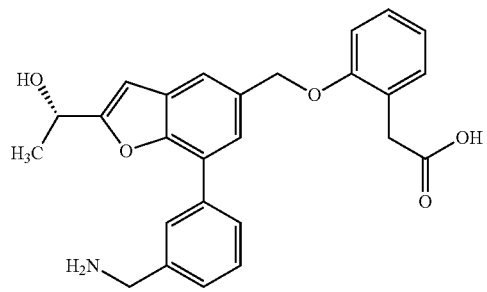
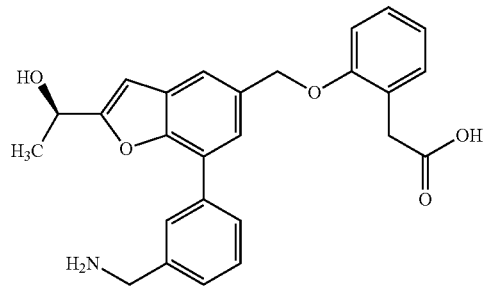 [SMILES: C[C@@H](O)c1cc2cc(COc3ccccc3CC(=O)O)cc(-c3cccc(CN)c3)c2o1]
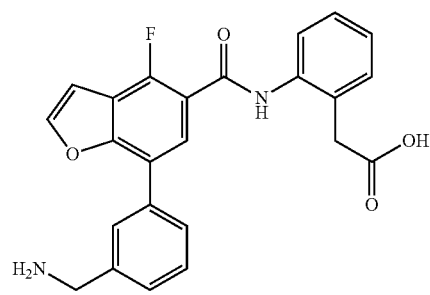

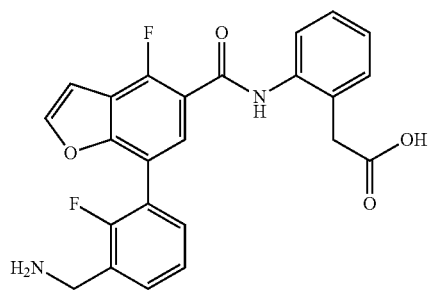 [SMILES: NCc1cccc(-c2cc(C(=O)Nc3ccccc3CC(=O)O)c(F)c3ccoc23)c1F]
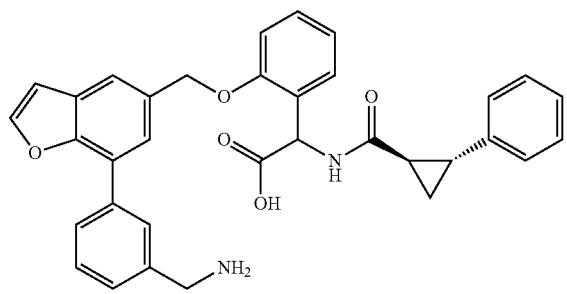 [SMILES: NCc1cccc(-c2cc(COc3ccccc3C(NC(=O)[C@@H]3C[C@H]3c3ccccc3)C(=O)O)cc3ccoc23)c1]
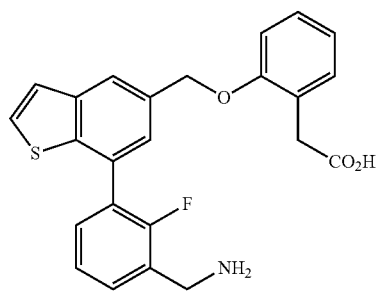 [SMILES: NCc1cccc(-c2cc(COc3ccccc3CC(=O)O)cc3ccsc23)c1F]
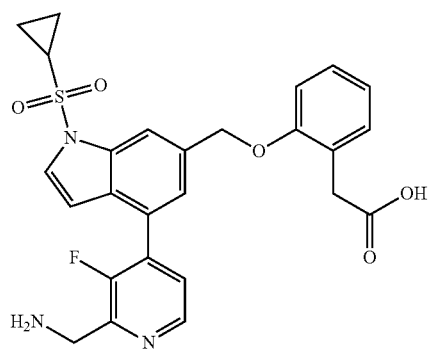 [SMILES: NCc1nccc(-c2cc(COc3ccccc3CC(=O)O)cc3c2ccn3S(=O)(=O)C2CC2)c1F]
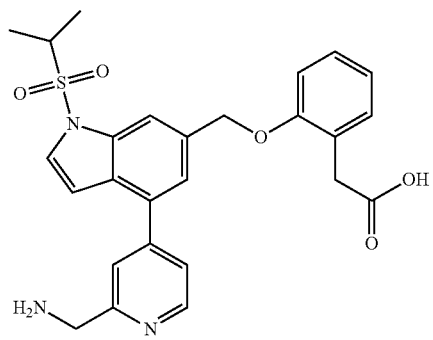 [SMILES: CC(C)S(=O)(=O)n1ccc2c(-c3ccnc(CN)c3)cc(COc3ccccc3CC(=O)O)cc21]

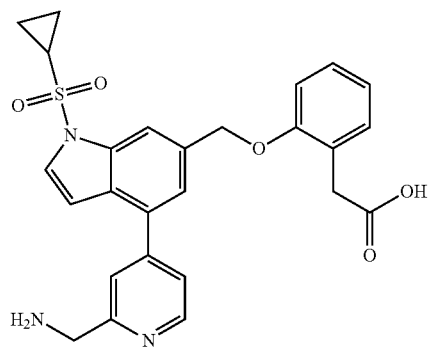 [SMILES: NCc1cc(-c2cc(COc3ccccc3CC(=O)O)cc3c2ccn3S(=O)(=O)C2CC2)ccn1]
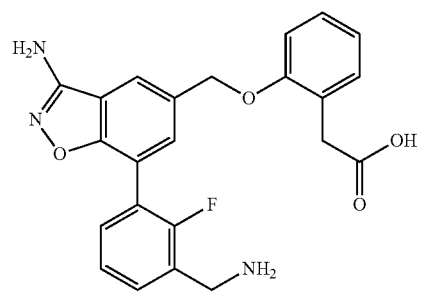 [SMILES: NCc1cccc(-c2cc(COc3ccccc3CC(=O)O)cc3c(N)noc23)c1F]
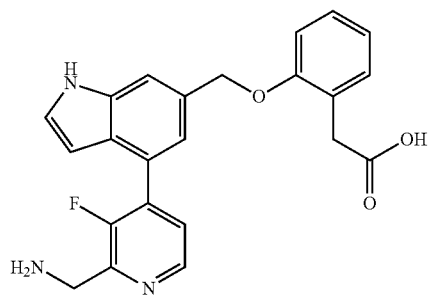 [SMILES: NCc1nccc(-c2cc(COc3ccccc3CC(=O)O)cc3[nH]ccc23)c1F]
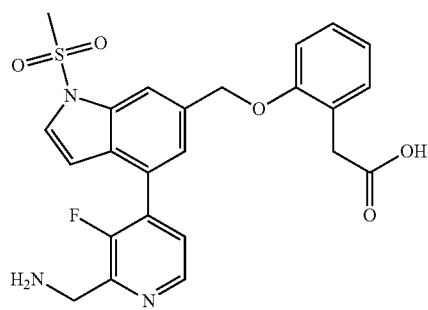 [SMILES: CS(=O)(=O)n1ccc2c(-c3ccnc(CN)c3F)cc(COc3ccccc3CC(=O)O)cc21]
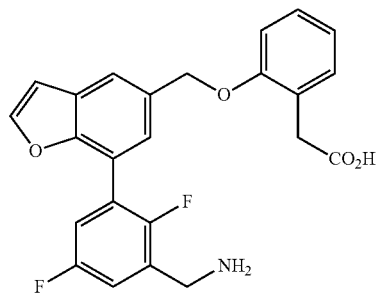 [SMILES: NCc1cc(F)cc(-c2cc(COc3ccccc3CC(=O)O)cc3ccoc23)c1F]

-continued
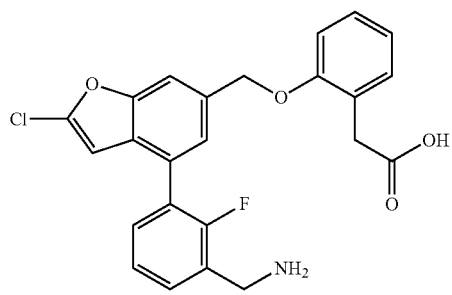 [SMILES: NCc1cccc(-c2cc(COc3ccccc3CC(=O)O)cc3oc(Cl)cc23)c1F]
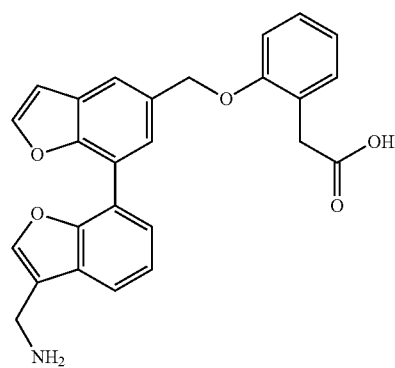 [SMILES: NCc1coc2c(-c3cc(COc4ccccc4CC(=O)O)cc4ccoc34)cccc12]
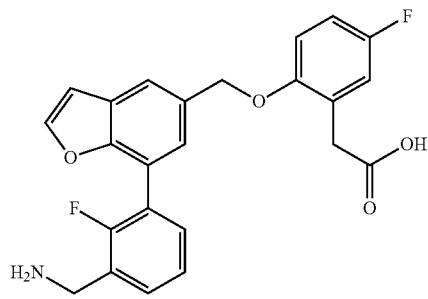 [SMILES: NCc1cccc(-c2cc(COc3ccc(F)cc3CC(=O)O)cc3ccoc23)c1F]
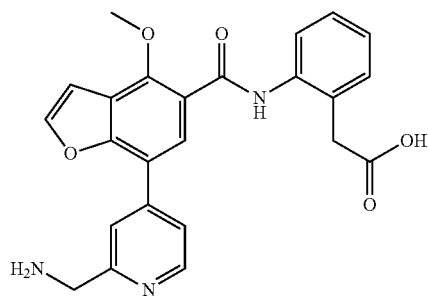 [SMILES: COc1c(C(=O)Nc2ccccc2CC(=O)O)cc(-c2ccnc(CN)c2)c2occc12]
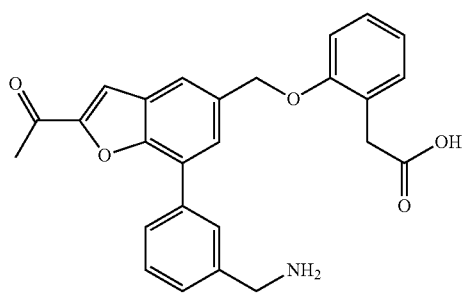 [SMILES: CC(=O)c1cc2cc(COc3ccccc3CC(=O)O)cc(-c3cccc(CN)c3)c2o1]

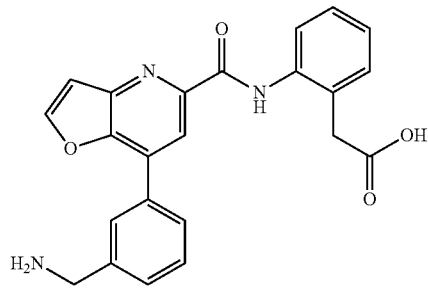 [SMILES: NCc1cccc(-c2cc(C(=O)Nc3ccccc3CC(=O)O)nc3ccoc23)c1]
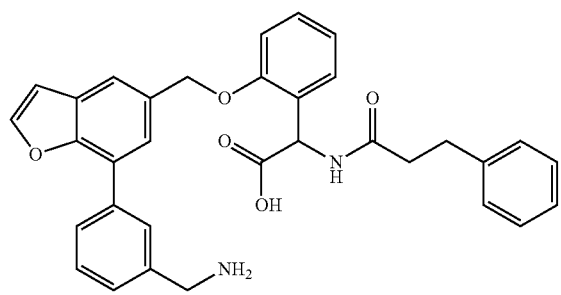 [SMILES: NCc1cccc(-c2cc(COc3ccccc3C(NC(=O)CCc3ccccc3)C(=O)O)cc3ccoc23)c1]
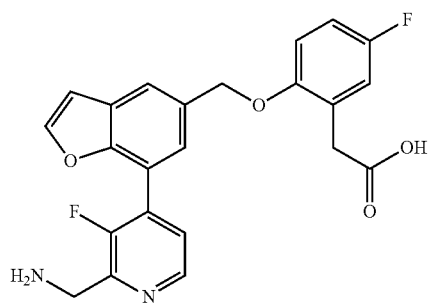 [SMILES: NCc1nccc(-c2cc(COc3ccc(F)cc3CC(=O)O)cc3ccoc23)c1F]
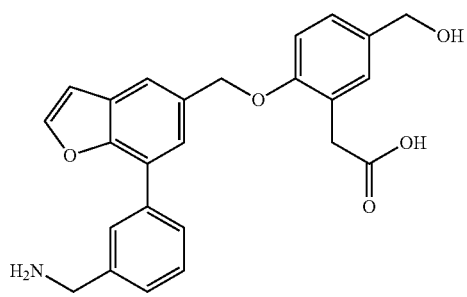 [SMILES: NCc1cccc(-c2cc(COc3ccc(CO)cc3CC(=O)O)cc3ccoc23)c1]
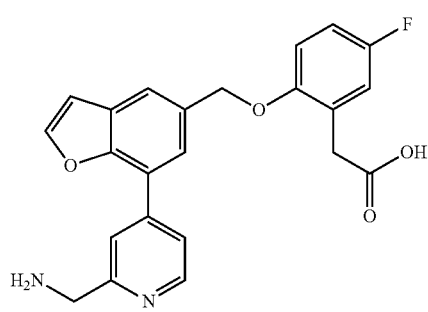 [SMILES: NCc1cc(-c2cc(COc3ccc(F)cc3CC(=O)O)cc3ccoc23)ccn1]

-continued
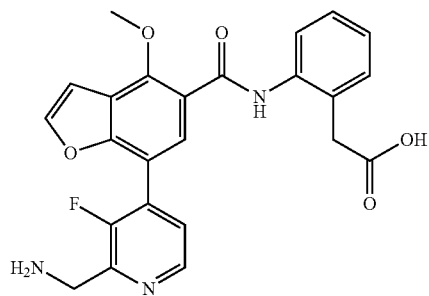 [SMILES: COc1c(C(=O)Nc2ccccc2CC(=O)O)cc(-c2ccnc(CN)c2F)c2occc12]
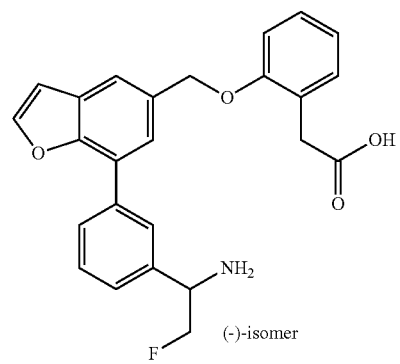 [SMILES: NC(CF)c1cccc(-c2cc(COc3ccccc3CC(=O)O)cc3ccoc23)c1]
(-)-isomer
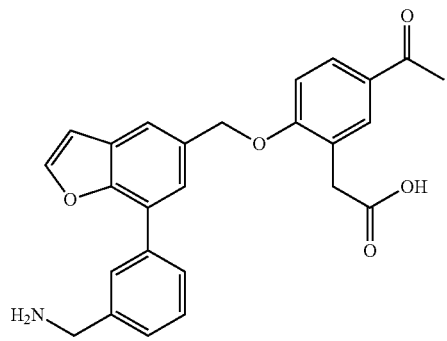 [SMILES: CC(=O)c1ccc(OCc2cc(-c3cccc(CN)c3)c3occc3c2)c(CC(=O)O)c1]
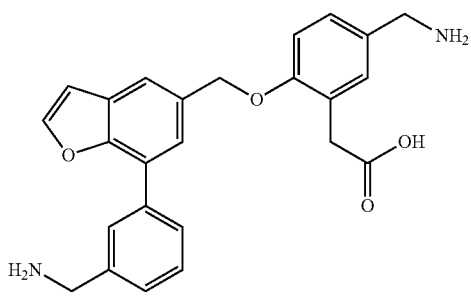 [SMILES: NCc1cccc(-c2cc(COc3ccc(CN)cc3CC(=O)O)cc3ccoc23)c1]

-continued
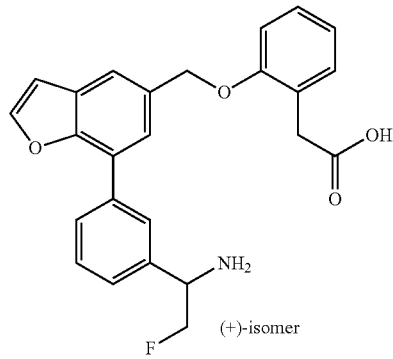 [SMILES: NC(CF)c1cccc(-c2cc(COc3ccccc3CC(=O)O)cc3ccoc23)c1]
(+)-isomer
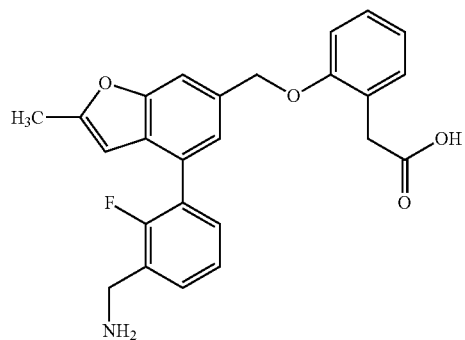 [SMILES: Cc1cc2c(-c3cccc(CN)c3F)cc(COc3ccccc3CC(=O)O)cc2o1]
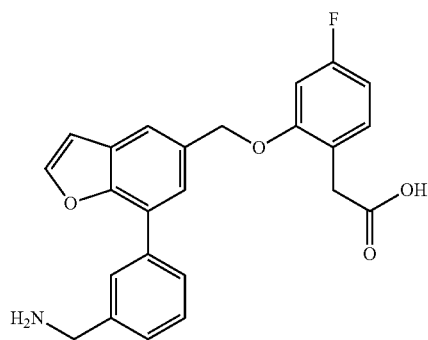 [SMILES: NCc1cccc(-c2cc(COc3cc(F)ccc3CC(=O)O)cc3ccoc23)c1]
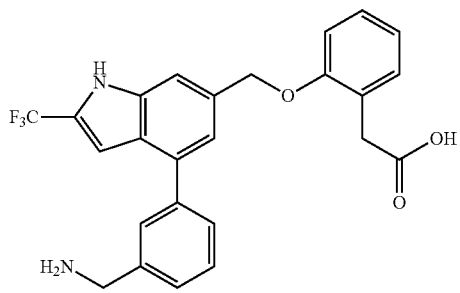 [SMILES: NCc1cccc(-c2cc(COc3ccccc3CC(=O)O)cc3[nH]c(C(F)(F)F)cc23)c1]
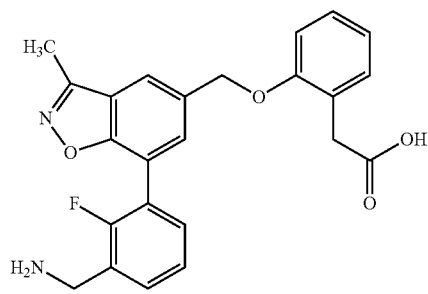 [SMILES: Cc1noc2c(-c3cccc(CN)c3F)cc(COc3ccccc3CC(=O)O)cc12]

-continued
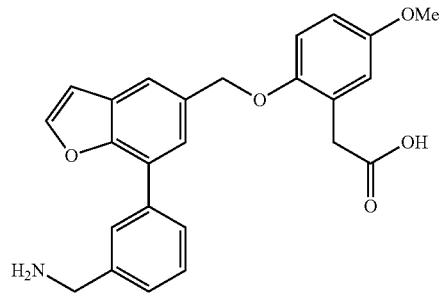 [SMILES: COc1ccc(OCc2cc(-c3cccc(CN)c3)c3occc3c2)c(CC(=O)O)c1]
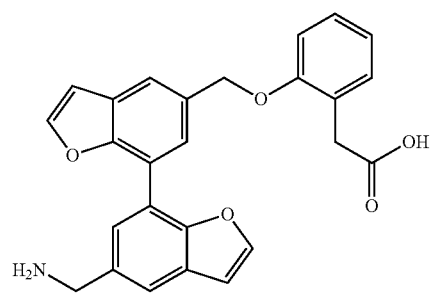 [SMILES: NCc1cc(-c2cc(COc3ccccc3CC(=O)O)cc3ccoc23)c2occc2c1]
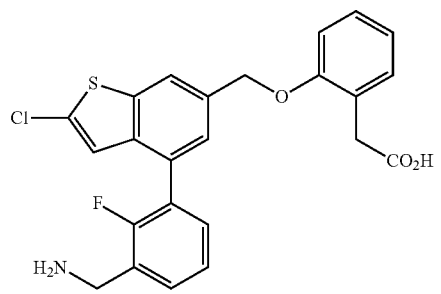 [SMILES: NCc1cccc(-c2cc(COc3ccccc3CC(=O)O)cc3sc(Cl)cc23)c1F]
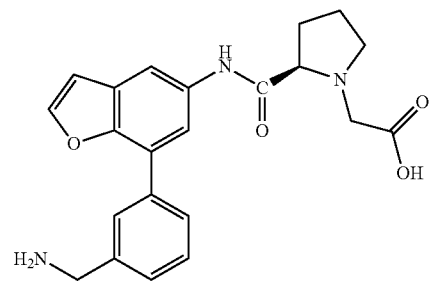 [SMILES: NCc1cccc(-c2cc(NC(=O)[C@H]3CCCN3CC(=O)O)cc3ccoc23)c1]
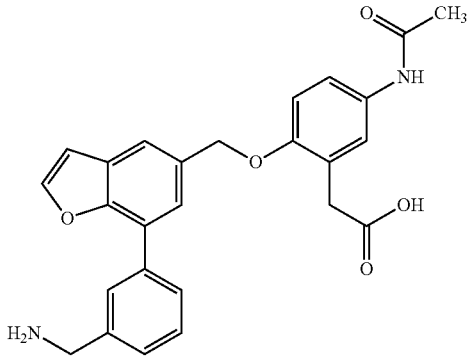 [SMILES: CC(=O)Nc1ccc(OCc2cc(-c3cccc(CN)c3)c3occc3c2)c(CC(=O)O)c1]

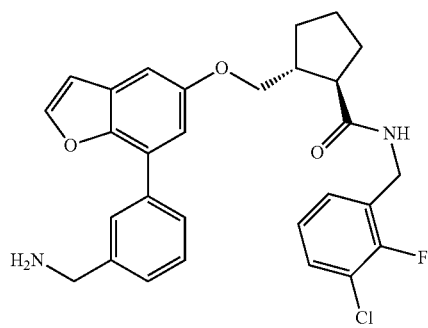 [SMILES: NCc1cccc(-c2cc(OC[C@@H]3CCC[C@H]3C(=O)NCc3cccc(Cl)c3F)cc3ccoc23)c1]
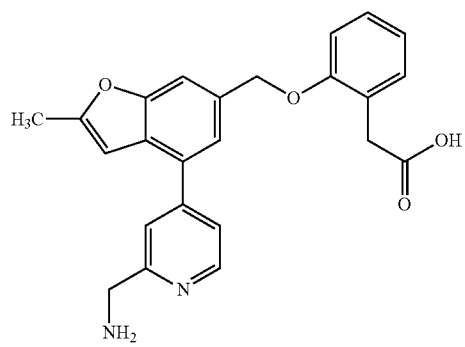 [SMILES: Cc1cc2c(-c3ccnc(CN)c3)cc(COc3ccccc3CC(=O)O)cc2o1]
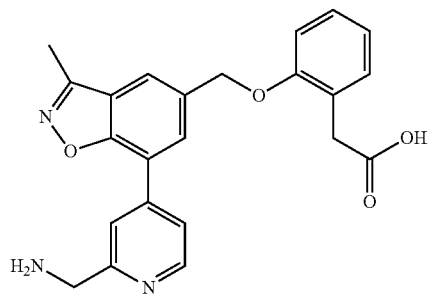 [SMILES: Cc1noc2c(-c3ccnc(CN)c3)cc(COc3ccccc3CC(=O)O)cc12]
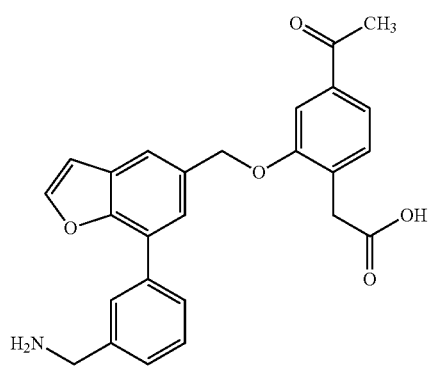 [SMILES: CC(=O)c1ccc(CC(=O)O)c(OCc2cc(-c3cccc(CN)c3)c3occc3c2)c1]

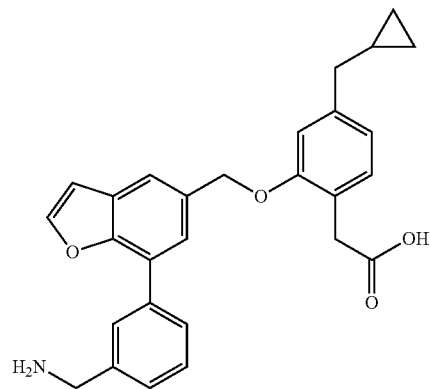 [SMILES: NCc1cccc(-c2cc(COc3cc(CC4CC4)ccc3CC(=O)O)cc3ccoc23)c1]
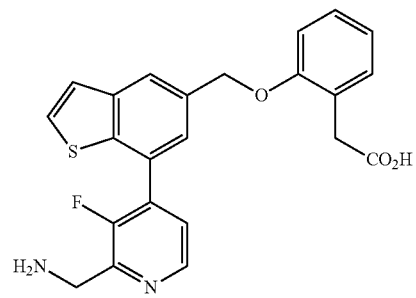 [SMILES: NCc1nccc(-c2cc(COc3ccccc3CC(=O)O)cc3ccsc23)c1F]
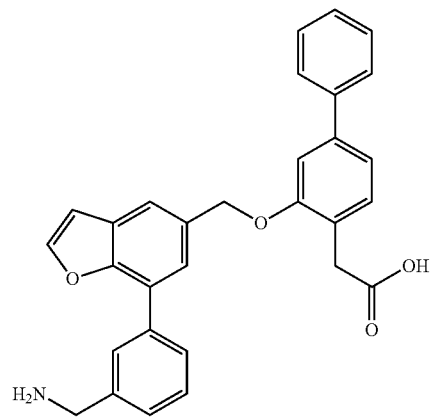 [SMILES: NCc1cccc(-c2cc(COc3cc(-c4ccccc4)ccc3CC(=O)O)cc3ccoc23)c1]
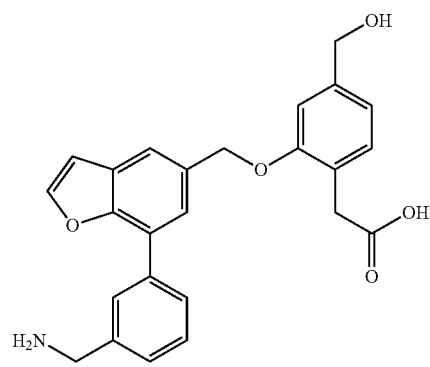 [SMILES: NCc1cccc(-c2cc(COc3cc(CO)ccc3CC(=O)O)cc3ccoc23)c1]

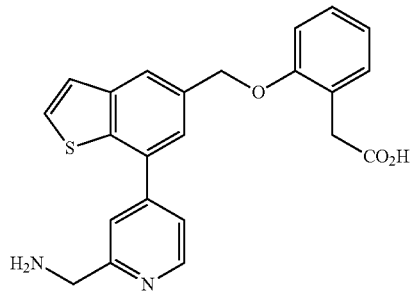 [SMILES: NCc1cc(-c2cc(COc3ccccc3CC(=O)O)cc3ccsc23)ccn1]
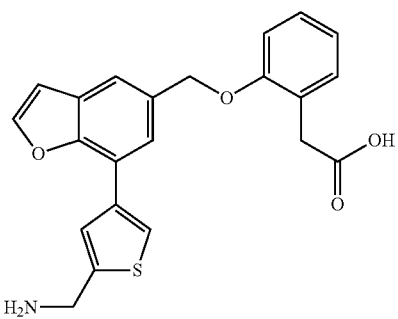 [SMILES: NCc1cc(-c2cc(COc3ccccc3CC(=O)O)cc3ccoc23)cs1]
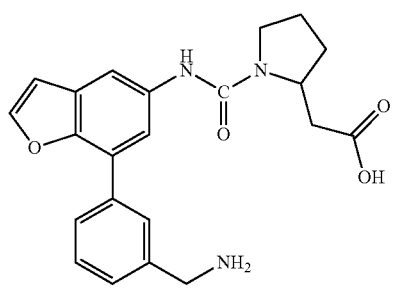 [SMILES: NCc1cccc(-c2cc(NC(=O)N3CCCC3CC(=O)O)cc3ccoc23)c1]
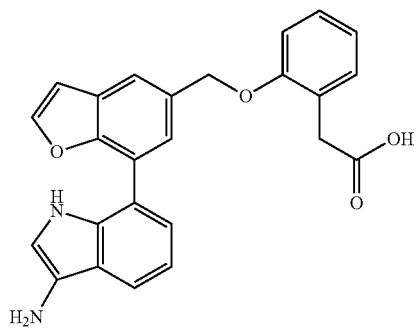
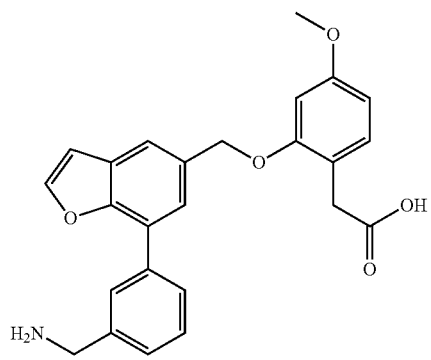 [SMILES: COc1ccc(CC(=O)O)c(OCc2cc(-c3cccc(CN)c3)c3occc3c2)c1]

-continued
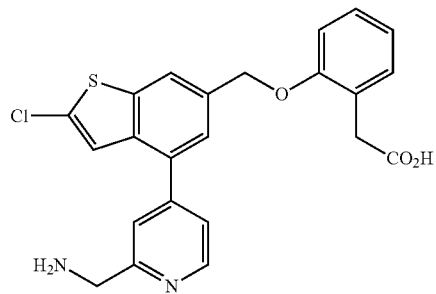 [SMILES: NCc1cc(-c2cc(COc3ccccc3CC(=O)O)cc3sc(Cl)cc23)ccn1]
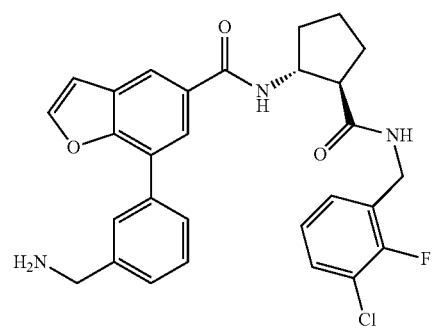 [SMILES: NCc1cccc(-c2cc(C(=O)N[C@@H]3CCC[C@H]3C(=O)NCc3cccc(Cl)c3F)cc3ccoc23)c1]
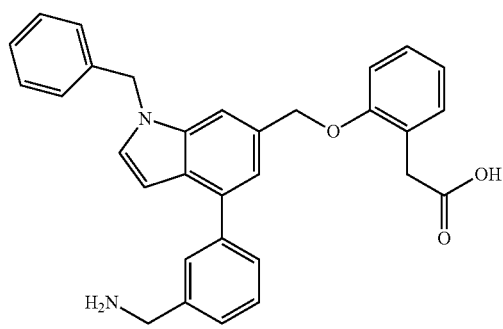 [SMILES: NCc1cccc(-c2cc(COc3ccccc3CC(=O)O)cc3c2ccn3Cc2ccccc2)c1]
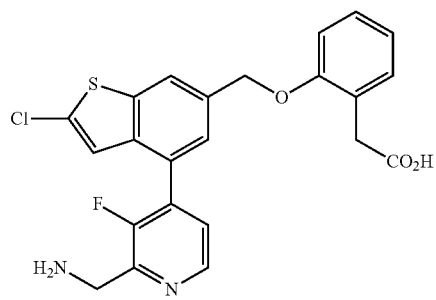 [SMILES: NCc1nccc(-c2cc(COc3ccccc3CC(=O)O)cc3sc(Cl)cc23)c1F]
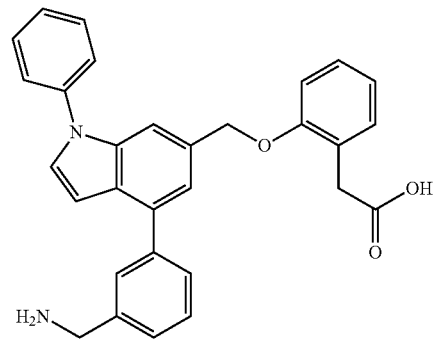 [SMILES: NCc1cccc(-c2cc(COc3ccccc3CC(=O)O)cc3c2ccn3-c2ccccc2)c1]

-continued
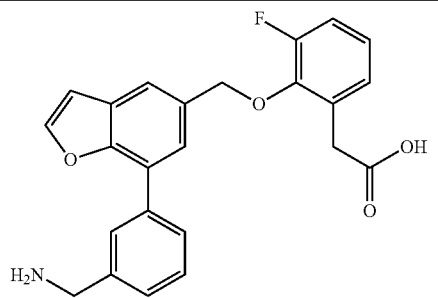
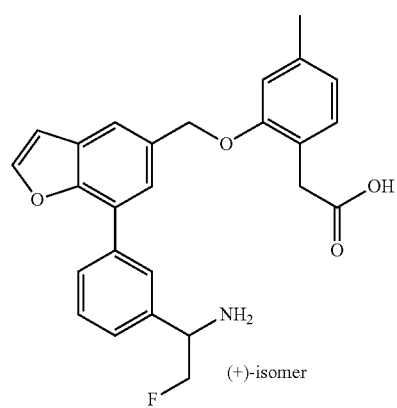 [SMILES: Cc1ccc(CC(=O)O)c(OCc2cc(-c3cccc(C(N)CF)c3)c3occc3c2)c1]
(+)-isomer
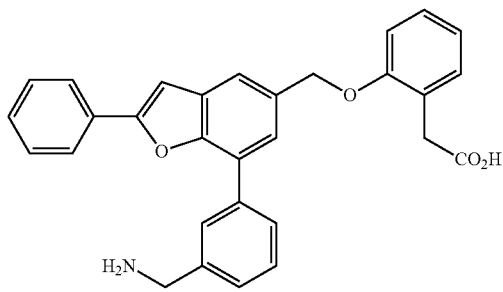 [SMILES: NCc1cccc(-c2cc(COc3ccccc3CC(=O)O)cc3cc(-c4ccccc4)oc23)c1]
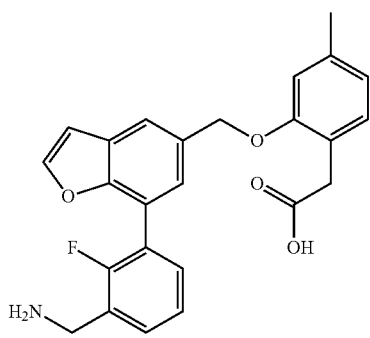 [SMILES: Cc1ccc(CC(=O)O)c(OCc2cc(-c3cccc(CN)c3F)c3occc3c2)c1]
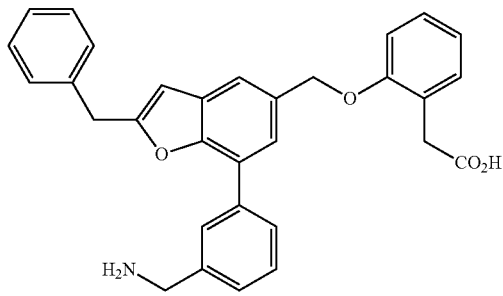 [SMILES: NCc1cccc(-c2cc(COc3ccccc3CC(=O)O)cc3cc(Cc4ccccc4)oc23)c1]

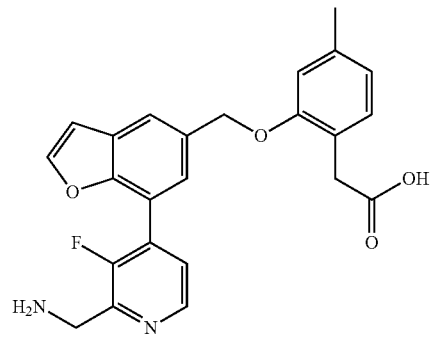 [SMILES: Cc1ccc(CC(=O)O)c(OCc2cc(-c3ccnc(CN)c3F)c3occc3c2)c1]
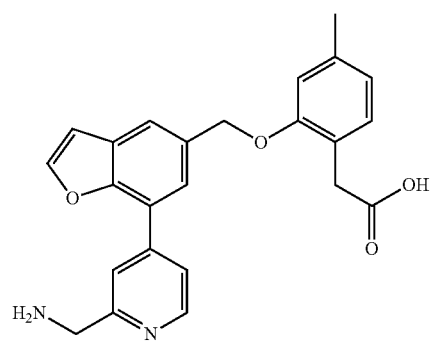 [SMILES: Cc1ccc(CC(=O)O)c(OCc2cc(-c3ccnc(CN)c3)c3occc3c2)c1]
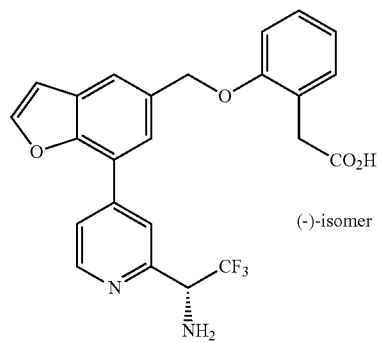 [SMILES: N[C@H](c1cc(-c2cc(COc3ccccc3CC(=O)O)cc3ccoc23)ccn1)C(F)(F)F]
(-)-isomer
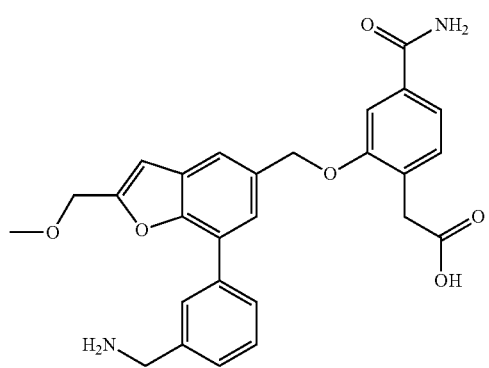 [SMILES: COCc1cc2cc(COc3cc(C(N)=O)ccc3CC(=O)O)cc(-c3cccc(CN)c3)c2o1]

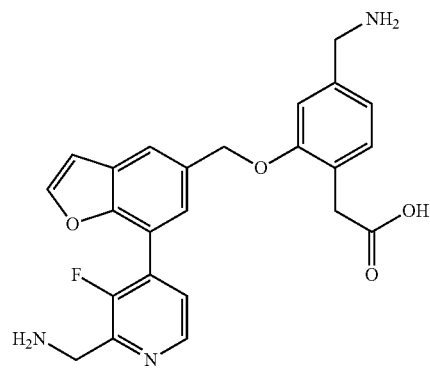 [SMILES: NCc1ccc(CC(=O)O)c(OCc2cc(-c3ccnc(CN)c3F)c3occc3c2)c1]
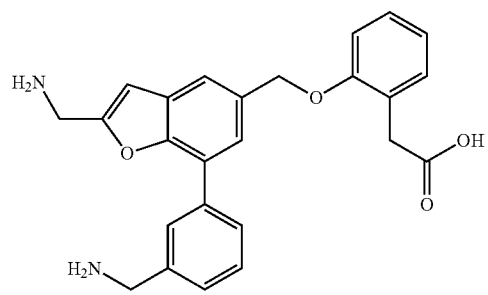 [SMILES: NCc1cccc(-c2cc(COc3ccccc3CC(=O)O)cc3cc(CN)oc23)c1]
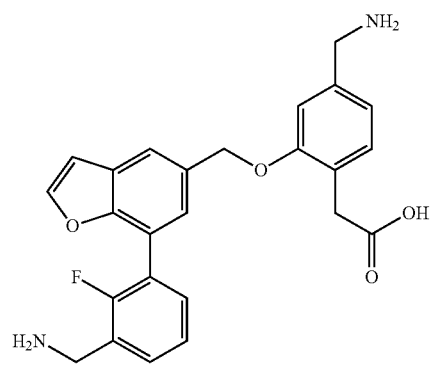 [SMILES: NCc1ccc(CC(=O)O)c(OCc2cc(-c3cccc(CN)c3F)c3occc3c2)c1]
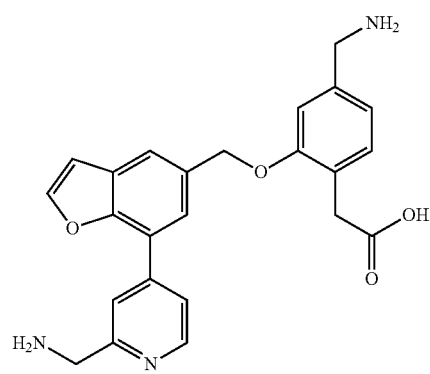 [SMILES: NCc1ccc(CC(=O)O)c(OCc2cc(-c3ccnc(CN)c3)c3occc3c2)c1]

-continued
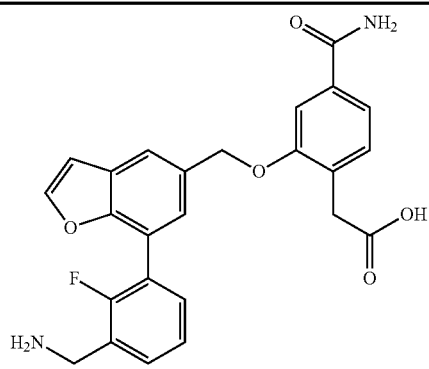
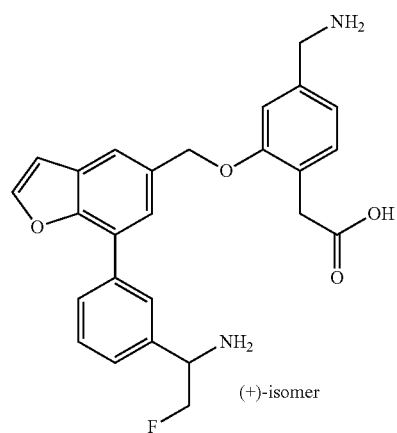
(+)-isomer
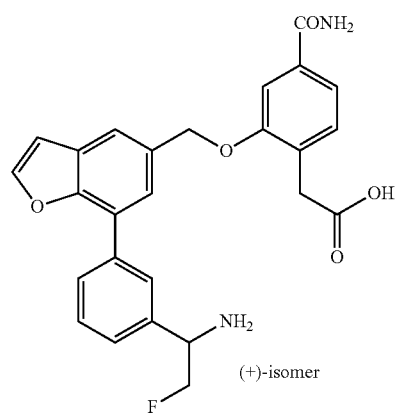
(+)-isomer
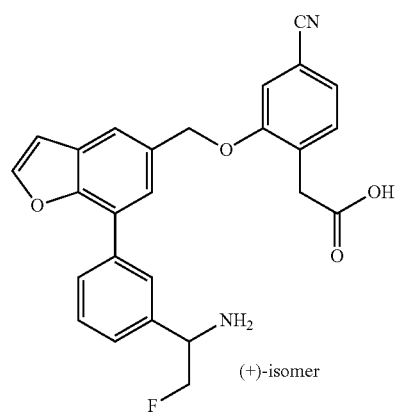
(+)-isomer

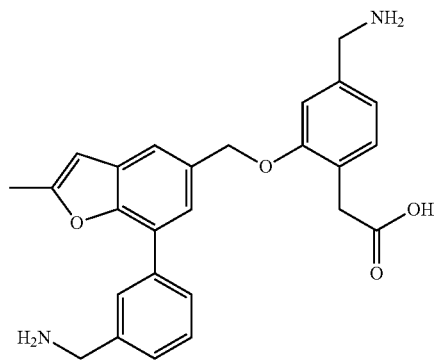 [SMILES: Cc1cc2cc(COc3cc(CN)ccc3CC(=O)O)cc(-c3cccc(CN)c3)c2o1]
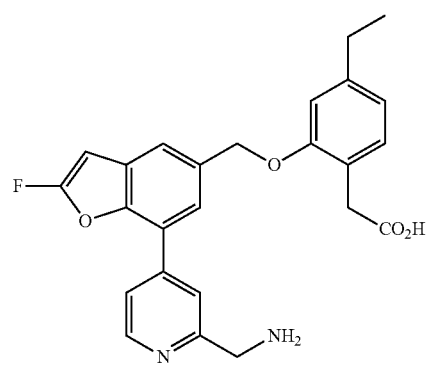 [SMILES: CCc1ccc(CC(=O)O)c(OCc2cc(-c3ccnc(CN)c3)c3oc(F)cc3c2)c1]
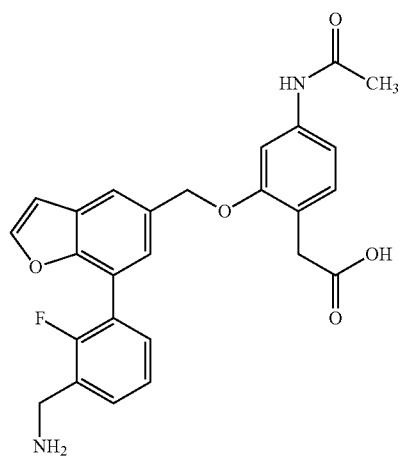 [SMILES: CC(=O)Nc1ccc(CC(=O)O)c(OCc2cc(-c3cccc(CN)c3F)c3occc3c2)c1]
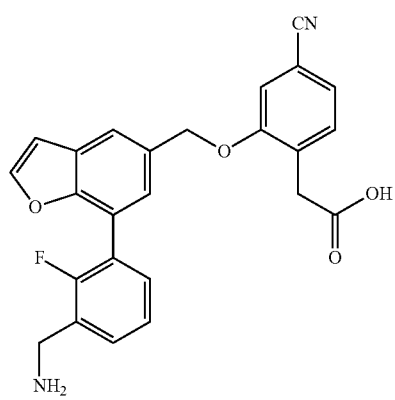 [SMILES: N#Cc1ccc(CC(=O)O)c(OCc2cc(-c3cccc(CN)c3F)c3occc3c2)c1]

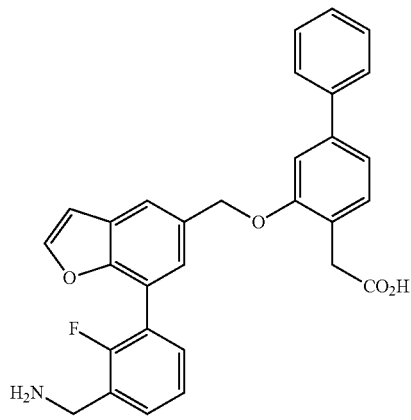 [SMILES: NCc1cccc(-c2cc(COc3cc(-c4ccccc4)ccc3CC(=O)O)cc3ccoc23)c1F]
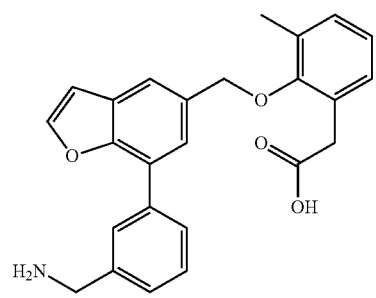 [SMILES: Cc1cccc(CC(=O)O)c1OCc1cc(-c2cccc(CN)c2)c2occc2c1]
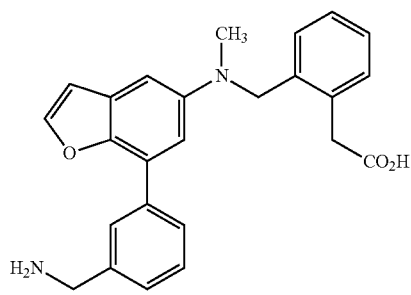 [SMILES: CN(Cc1ccccc1CC(=O)O)c1cc(-c2cccc(CN)c2)c2occc2c1]
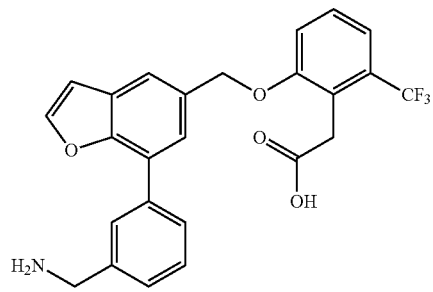 [SMILES: NCc1cccc(-c2cc(COc3cccc(C(F)(F)F)c3CC(=O)O)cc3ccoc23)c1]
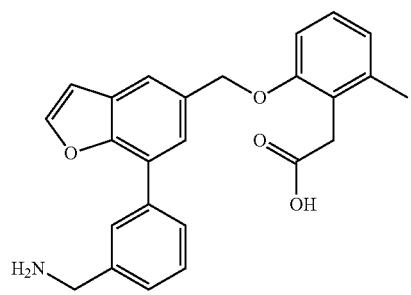 [SMILES: Cc1cccc(OCc2cc(-c3cccc(CN)c3)c3occc3c2)c1CC(=O)O]

-continued
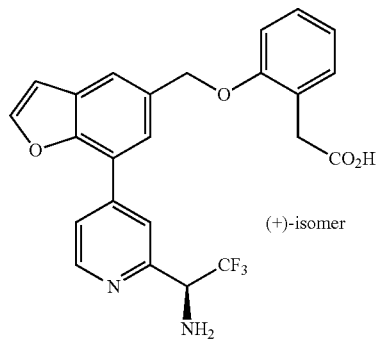 [SMILES: N[C@@H](c1cc(-c2cc(COc3ccccc3CC(=O)O)cc3ccoc23)ccn1)C(F)(F)F]
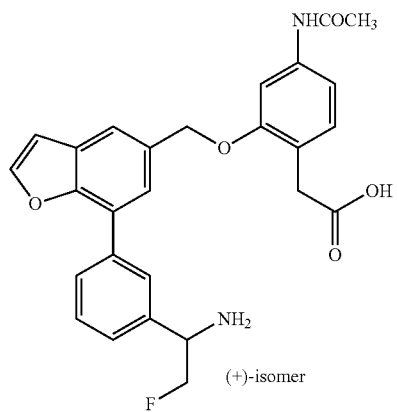
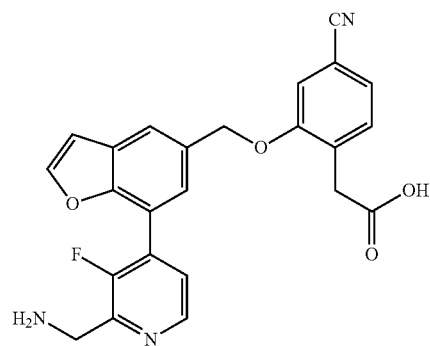 [SMILES: N#Cc1ccc(CC(=O)O)c(OCc2cc(-c3ccnc(CN)c3F)c3occc3c2)c1]
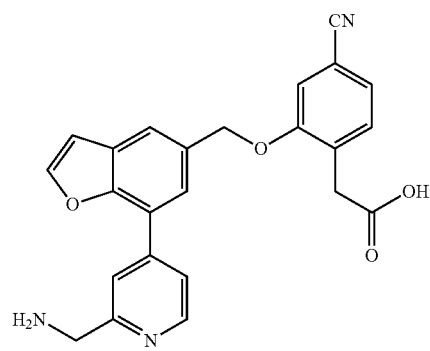 [SMILES: N#Cc1ccc(CC(=O)O)c(OCc2cc(-c3ccnc(CN)c3)c3occc3c2)c1]

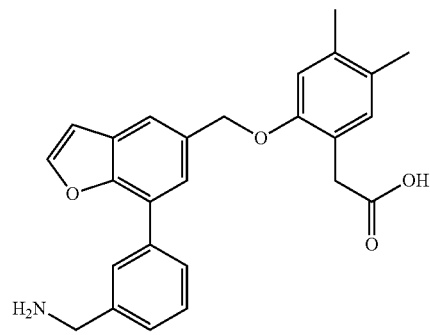 [SMILES: Cc1cc(CC(=O)O)c(OCc2cc(-c3cccc(CN)c3)c3occc3c2)cc1C]
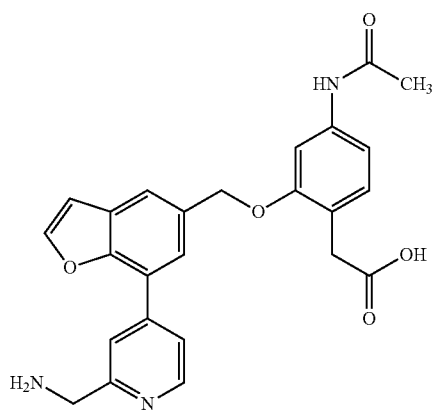 [SMILES: CC(=O)Nc1ccc(CC(=O)O)c(OCc2cc(-c3ccnc(CN)c3)c3occc3c2)c1]
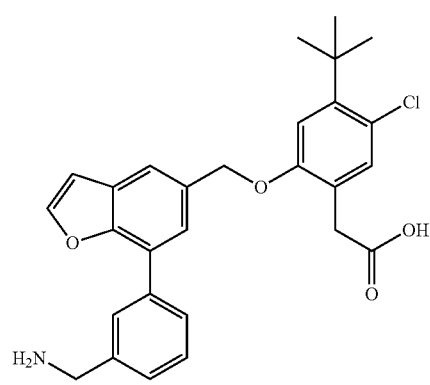 [SMILES: CC(C)(C)c1cc(OCc2cc(-c3cccc(CN)c3)c3occc3c2)c(CC(=O)O)cc1Cl]
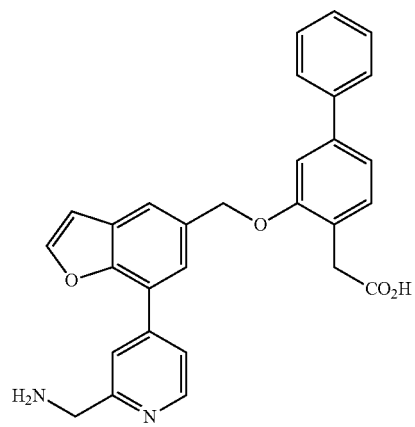 [SMILES: NCc1cc(-c2cc(COc3cc(-c4ccccc4)ccc3CC(=O)O)cc3ccoc23)ccn1]

-continued
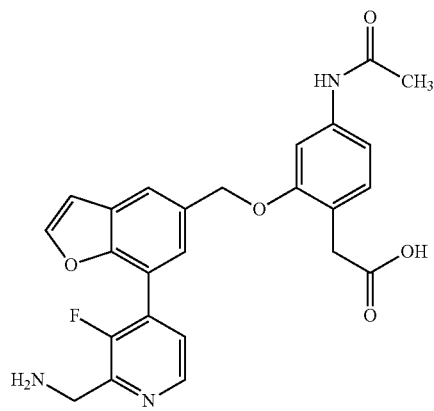 [SMILES: CC(=O)Nc1ccc(CC(=O)O)c(OCc2cc(-c3ccnc(CN)c3F)c3occc3c2)c1]
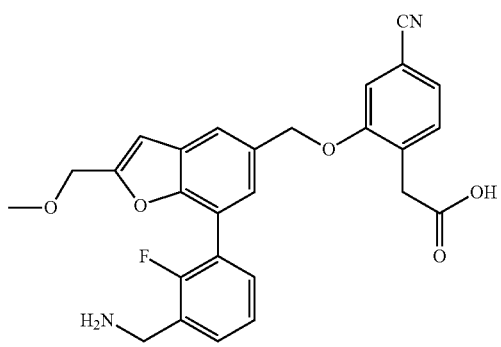 [SMILES: COCc1cc2cc(COc3cc(C#N)ccc3CC(=O)O)cc(-c3cccc(CN)c3F)c2o1]
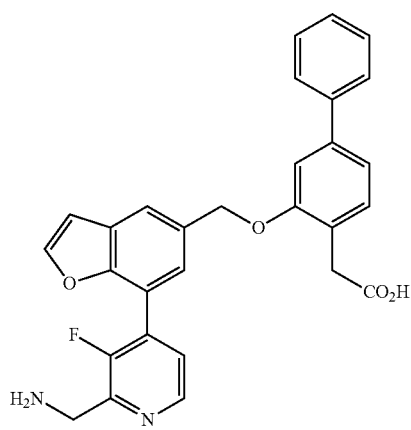 [SMILES: NCc1nccc(-c2cc(COc3cc(-c4ccccc4)ccc3CC(=O)O)cc3ccoc23)c1F]
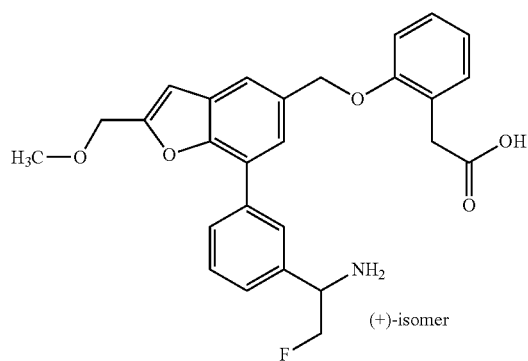 [SMILES: COCc1cc2cc(COc3ccccc3CC(=O)O)cc(-c3cccc(C(N)CF)c3)c2o1]
(+)-isomer

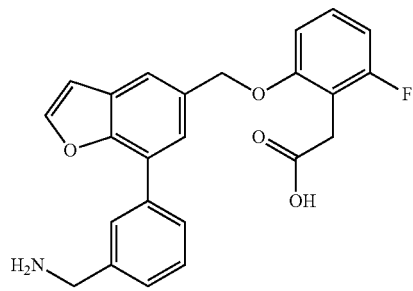 [SMILES: NCc1cccc(-c2cc(COc3cccc(F)c3CC(=O)O)cc3ccoc23)c1]
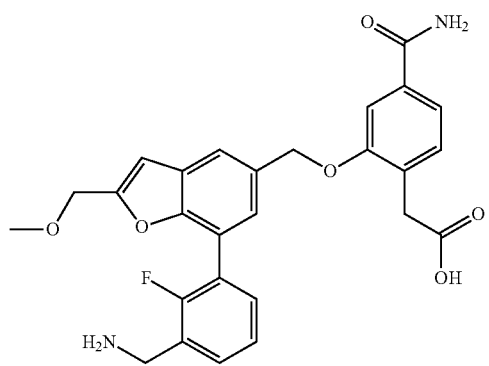 [SMILES: COCc1cc2cc(COc3cc(C(N)=O)ccc3CC(=O)O)cc(-c3cccc(CN)c3F)c2o1]
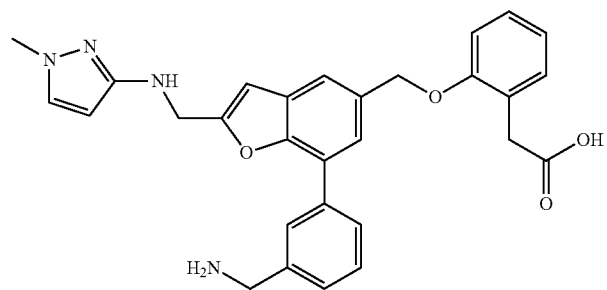 [SMILES: Cn1ccc(NCc2cc3cc(COc4ccccc4CC(=O)O)cc(-c4cccc(CN)c4)c3o2)n1]
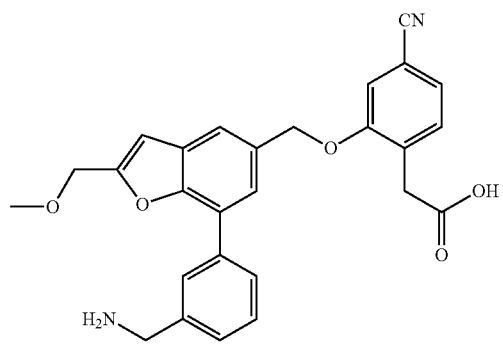 [SMILES: COCc1cc2cc(COc3cc(C#N)ccc3CC(=O)O)cc(-c3cccc(CN)c3)c2o1]

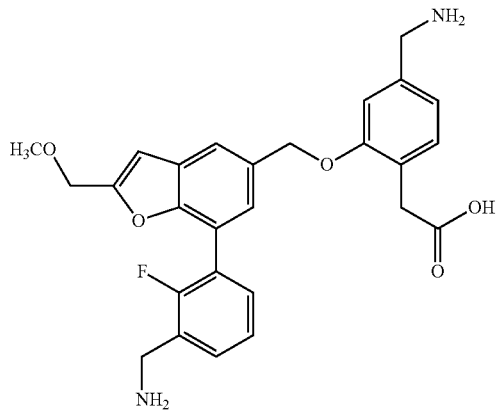 [SMILES: COCc1cc2cc(COc3cc(CN)ccc3CC(=O)O)cc(-c3cccc(CN)c3F)c2o1]
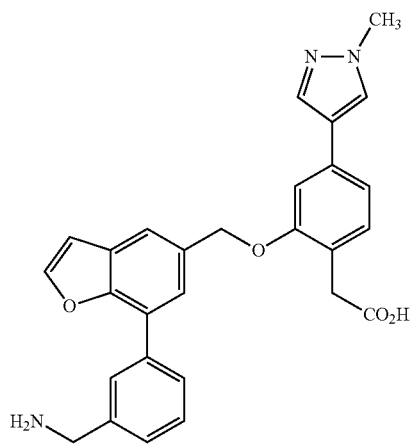 [SMILES: Cn1cc(-c2ccc(CC(=O)O)c(OCc3cc(-c4cccc(CN)c4)c4occc4c3)c2)cn1]
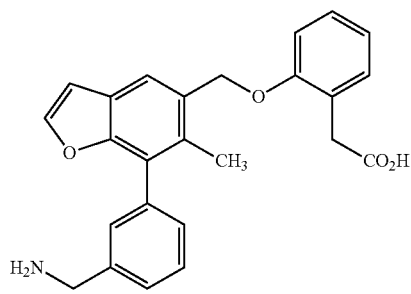 [SMILES: Cc1c(COc2ccccc2CC(=O)O)cc2ccoc2c1-c1cccc(CN)c1]
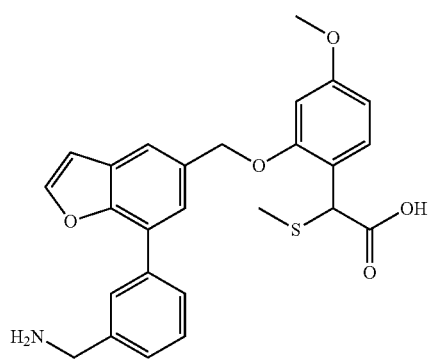 [SMILES: COc1ccc(C(SC)C(=O)O)c(OCc2cc(-c3cccc(CN)c3)c3occc3c2)c1]

-continued
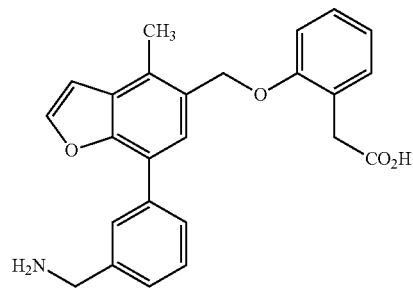 [SMILES: Cc1c(COc2ccccc2CC(=O)O)cc(-c2cccc(CN)c2)c2occc12]
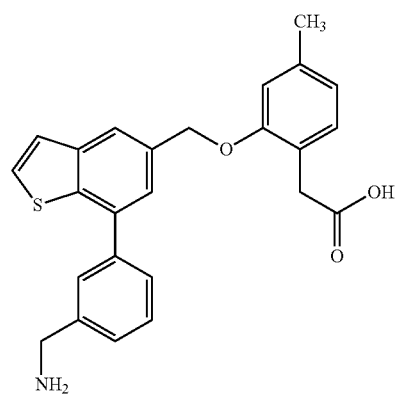 [SMILES: Cc1ccc(CC(=O)O)c(OCc2cc(-c3cccc(CN)c3)c3sccc3c2)c1]
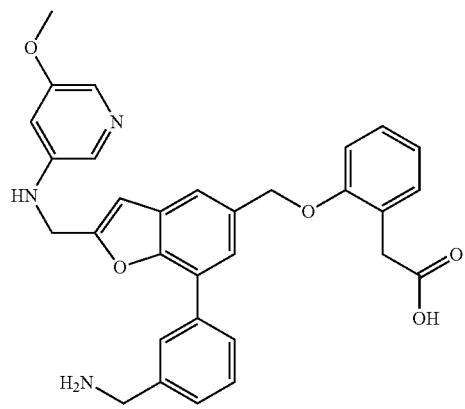 [SMILES: COc1cncc(NCc2cc3cc(COc4ccccc4CC(=O)O)cc(-c4cccc(CN)c4)c3o2)c1]
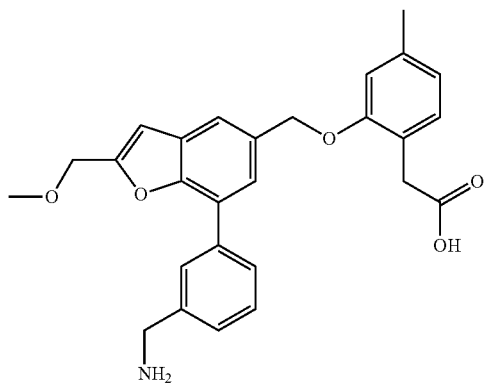 [SMILES: COCc1cc2cc(COc3cc(C)ccc3CC(=O)O)cc(-c3cccc(CN)c3)c2o1]

-continued
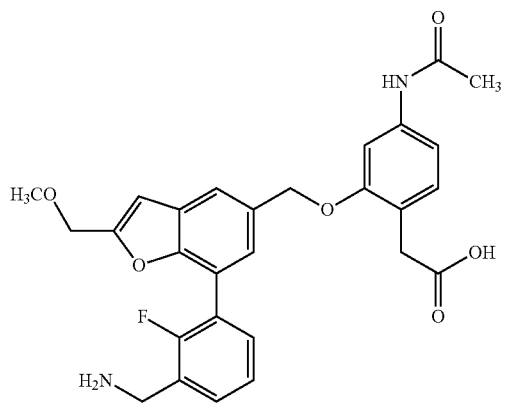 [SMILES: COCc1cc2cc(COc3cc(NC(C)=O)ccc3CC(=O)O)cc(-c3cccc(CN)c3F)c2o1]
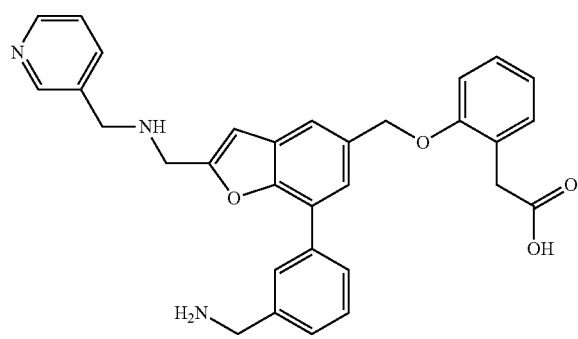 [SMILES: NCc1cccc(-c2cc(COc3ccccc3CC(=O)O)cc3cc(CNCc4cccnc4)oc23)c1]
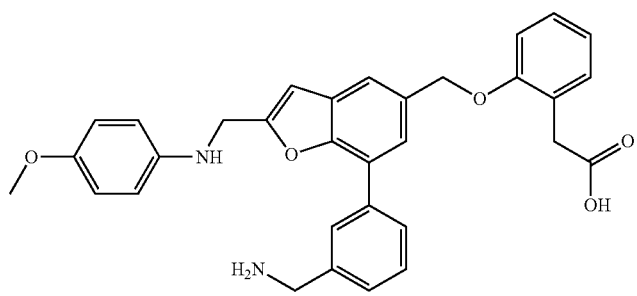 [SMILES: COc1ccc(NCc2cc3cc(COc4ccccc4CC(=O)O)cc(-c4cccc(CN)c4)c3o2)cc1]
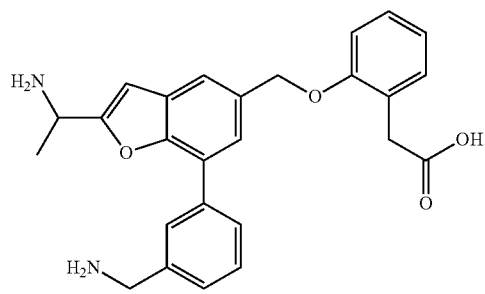
(-)-isomer

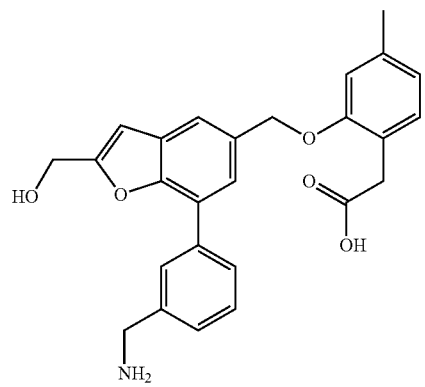 [SMILES: Cc1ccc(CC(=O)O)c(OCc2cc(-c3cccc(CN)c3)c3oc(CO)cc3c2)c1]
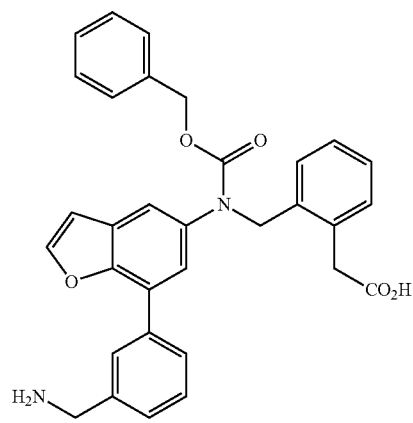 [SMILES: NCc1cccc(-c2cc(N(Cc3ccccc3CC(=O)O)C(=O)OCc3ccccc3)cc3ccoc23)c1]
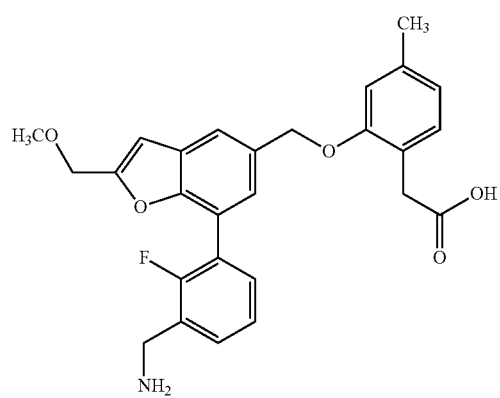 [SMILES: COCc1cc2cc(COc3cc(C)ccc3CC(=O)O)cc(-c3cccc(CN)c3F)c2o1]

-continued
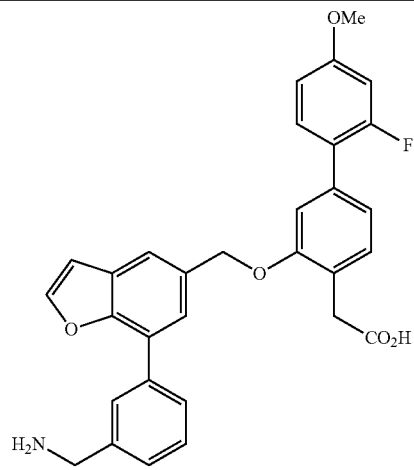
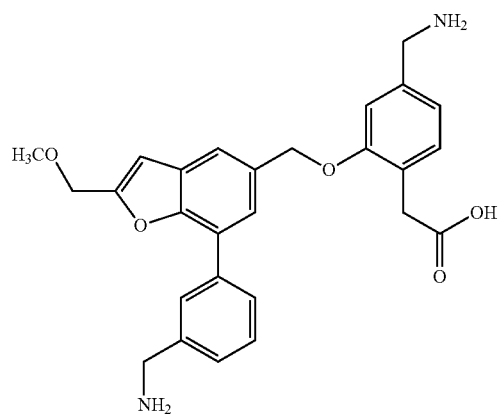 [SMILES: COCc1cc2cc(COc3cc(CN)ccc3CC(=O)O)cc(-c3cccc(CN)c3)c2o1]
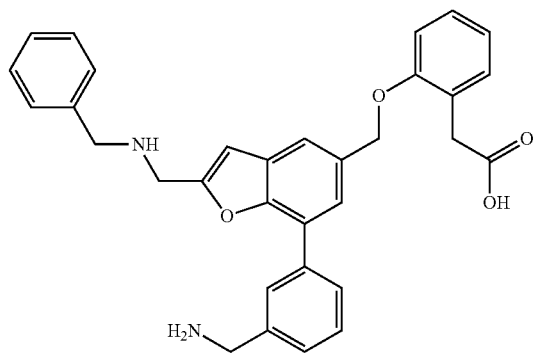 [SMILES: NCc1cccc(-c2cc(COc3ccccc3CC(=O)O)cc3cc(CNCc4ccccc4)oc23)c1]

-continued
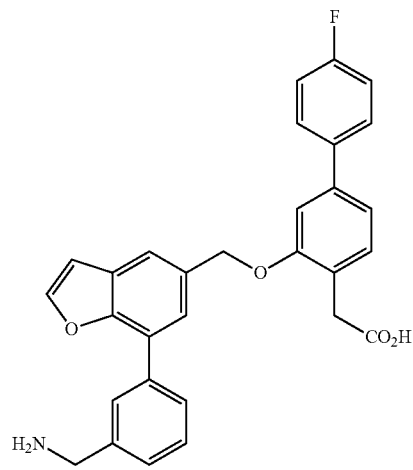 [SMILES: NCc1cccc(-c2cc(COc3cc(-c4ccc(F)cc4)ccc3CC(=O)O)cc3ccoc23)c1]
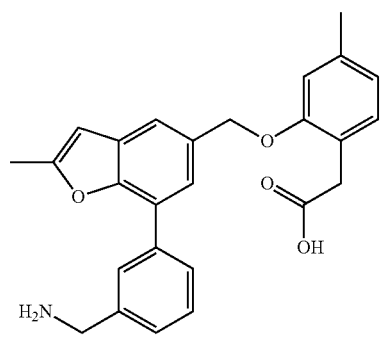 [SMILES: Cc1ccc(CC(=O)O)c(OCc2cc(-c3cccc(CN)c3)c3oc(C)cc3c2)c1]
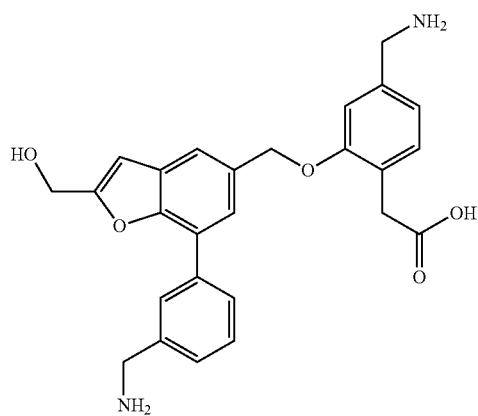 [SMILES: NCc1cccc(-c2cc(COc3cc(CN)ccc3CC(=O)O)cc3cc(CO)oc23)c1]
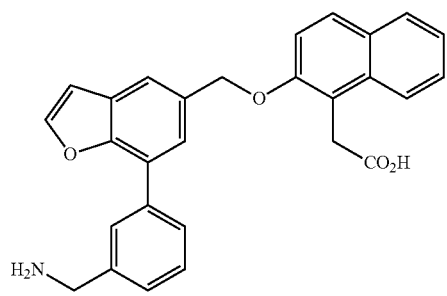 [SMILES: NCc1cccc(-c2cc(COc3ccc4ccccc4c3CC(=O)O)cc3ccoc23)c1]

-continued
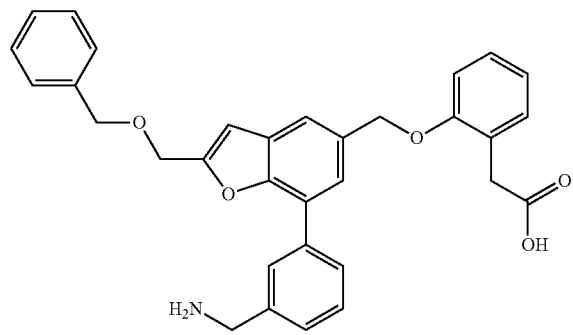 [SMILES: NCc1cccc(-c2cc(COc3ccccc3CC(=O)O)cc3cc(COCc4ccccc4)oc23)c1]
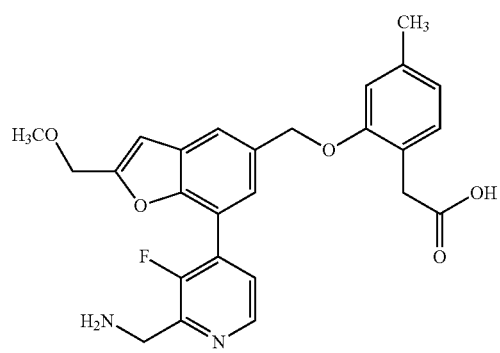 [SMILES: COCc1cc2cc(COc3cc(C)ccc3CC(=O)O)cc(-c3ccnc(CN)c3F)c2o1]
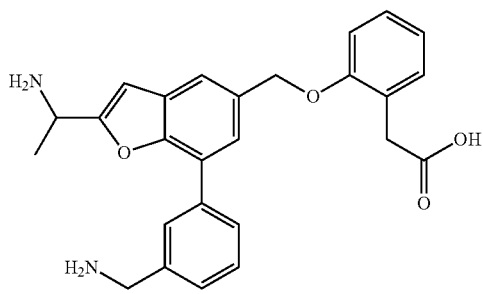 [SMILES: CC(N)c1cc2cc(COc3ccccc3CC(=O)O)cc(-c3cccc(CN)c3)c2o1]
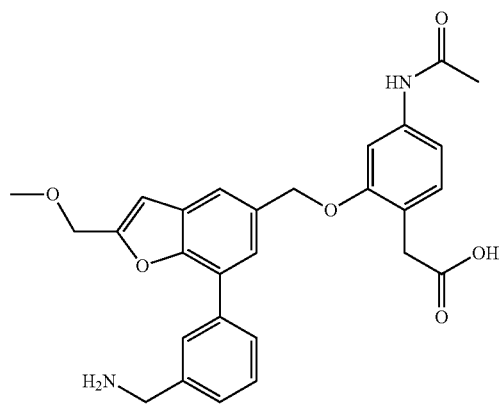 [SMILES: COCc1cc2cc(COc3cc(NC(C)=O)ccc3CC(=O)O)cc(-c3cccc(CN)c3)c2o1]

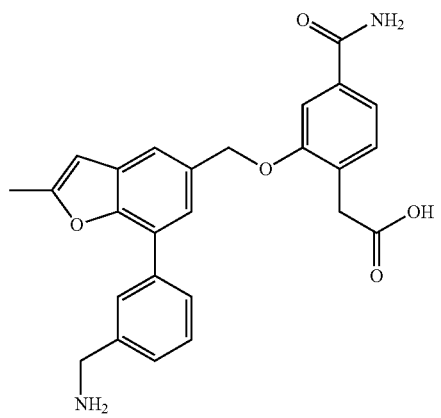 [SMILES: Cc1cc2cc(COc3cc(C(N)=O)ccc3CC(=O)O)cc(-c3cccc(CN)c3)c2o1]
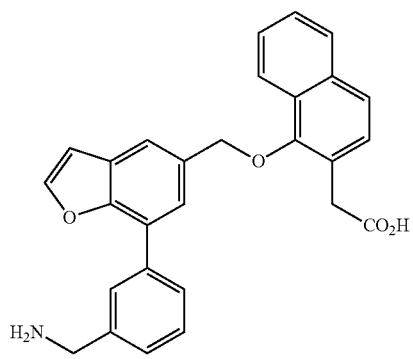 [SMILES: NCc1cccc(-c2cc(COc3c(CC(=O)O)ccc4ccccc34)cc3ccoc23)c1]
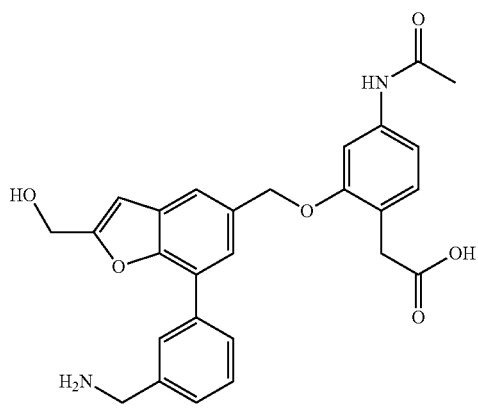 [SMILES: CC(=O)Nc1ccc(CC(=O)O)c(OCc2cc(-c3cccc(CN)c3)c3oc(CO)cc3c2)c1]
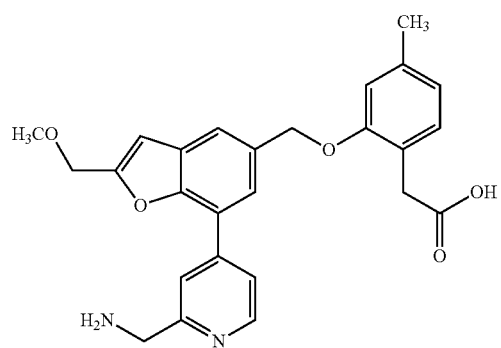 [SMILES: COCc1cc2cc(COc3cc(C)ccc3CC(=O)O)cc(-c3ccnc(CN)c3)c2o1]

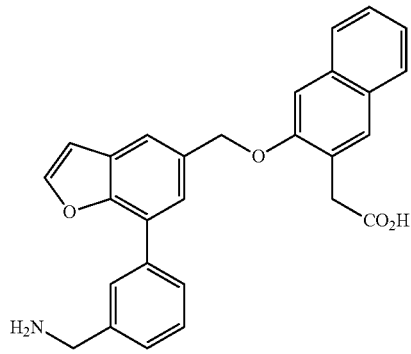 [SMILES: NCc1cccc(-c2cc(COc3cc4ccccc4cc3CC(=O)O)cc3ccoc23)c1]
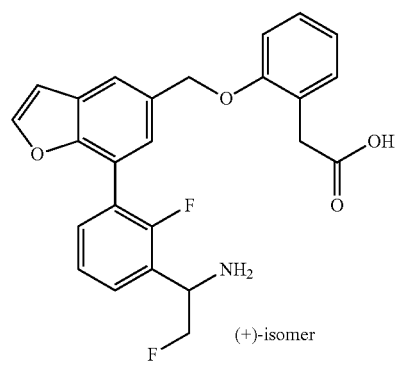 [SMILES: NC(CF)c1cccc(-c2cc(COc3ccccc3CC(=O)O)cc3ccoc23)c1F]
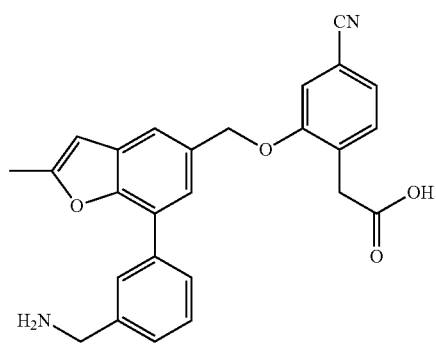 [SMILES: Cc1cc2cc(COc3cc(C#N)ccc3CC(=O)O)cc(-c3cccc(CN)c3)c2o1]
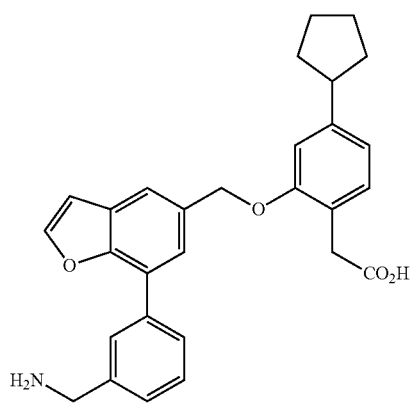 [SMILES: NCc1cccc(-c2cc(COc3cc(C4CCCC4)ccc3CC(=O)O)cc3ccoc23)c1]

-continued
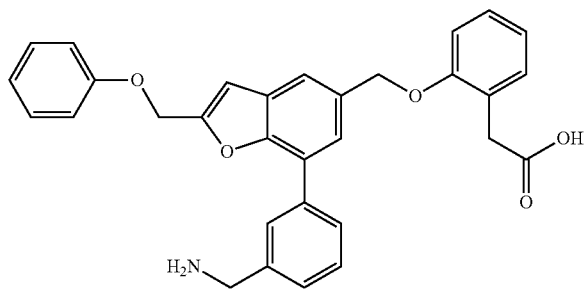 [SMILES: NCc1cccc(-c2cc(COc3ccccc3CC(=O)O)cc3cc(COc4ccccc4)oc23)c1]
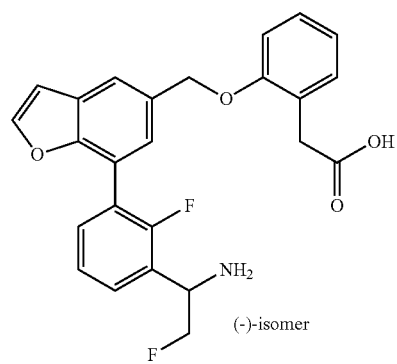 [SMILES: NC(CF)c1cccc(-c2cc(COc3ccccc3CC(=O)O)cc3ccoc23)c1F]
(-)-isomer
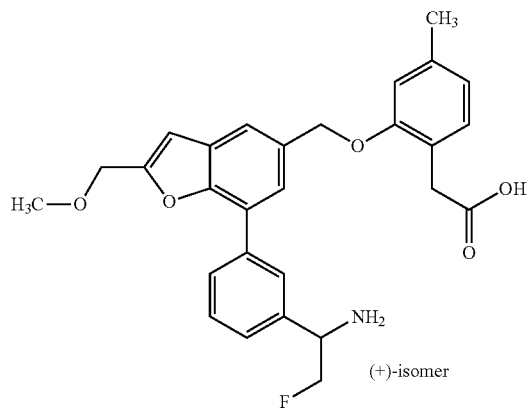 [SMILES: COCc1cc2cc(COc3cc(C)ccc3CC(=O)O)cc(-c3cccc(C(N)CF)c3)c2o1]
(+)-isomer
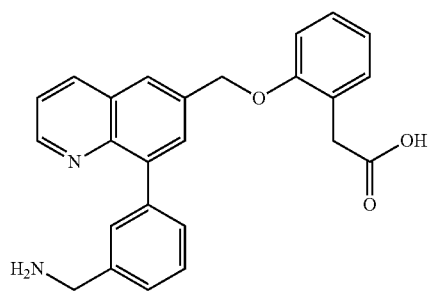 [SMILES: NCc1cccc(-c2cc(COc3ccccc3CC(=O)O)cc3cccnc23)c1]

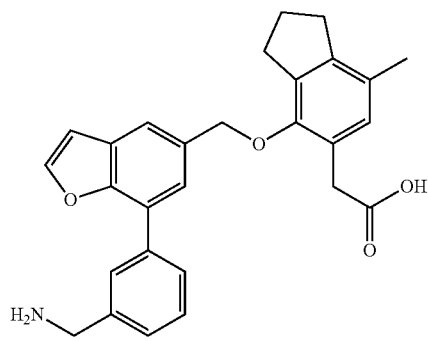 [SMILES: Cc1cc(CC(=O)O)c(OCc2cc(-c3cccc(CN)c3)c3occc3c2)c2c1CCC2]
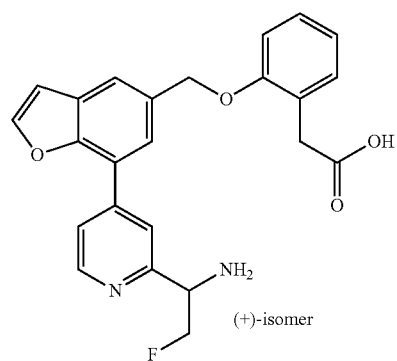 [SMILES: NC(CF)c1cc(-c2cc(COc3ccccc3CC(=O)O)cc3ccoc23)ccn1]
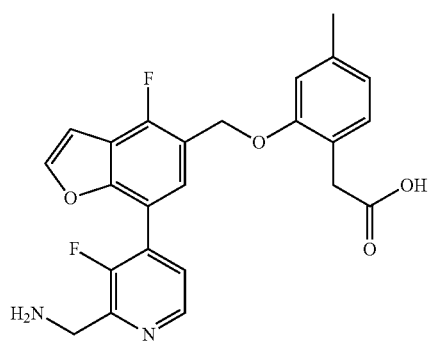 [SMILES: Cc1ccc(CC(=O)O)c(OCc2cc(-c3ccnc(CN)c3F)c3occc3c2F)c1]
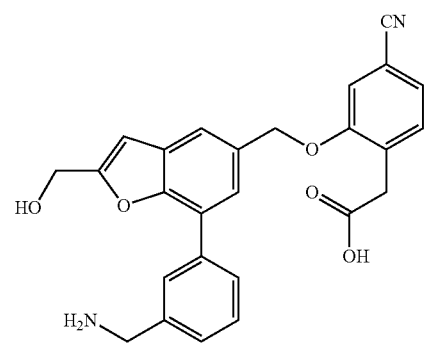 [SMILES: N#Cc1ccc(CC(=O)O)c(OCc2cc(-c3cccc(CN)c3)c3oc(CO)cc3c2)c1]

-continued
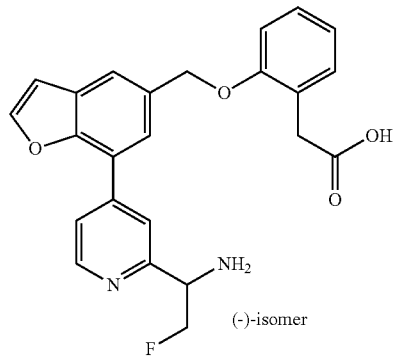 [SMILES: NC(CF)c1cc(-c2cc(COc3ccccc3CC(=O)O)cc3ccoc23)ccn1]
(-)-isomer
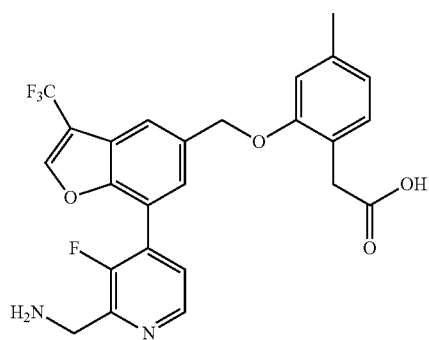 [SMILES: Cc1ccc(CC(=O)O)c(OCc2cc(-c3ccnc(CN)c3F)c3occ(C(F)(F)F)c3c2)c1]
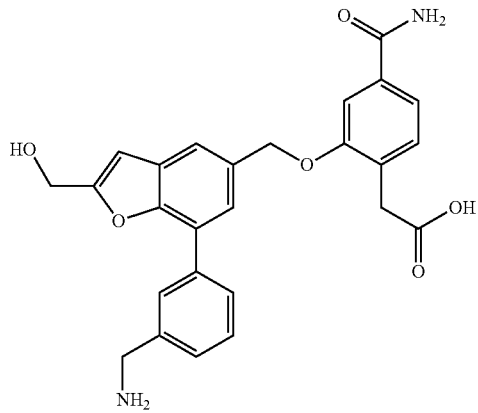 [SMILES: NCc1cccc(-c2cc(COc3cc(C(N)=O)ccc3CC(=O)O)cc3cc(CO)oc23)c1]
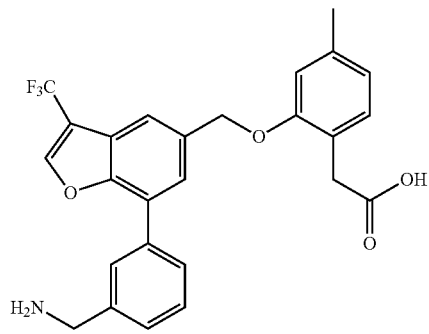 [SMILES: Cc1ccc(CC(=O)O)c(OCc2cc(-c3cccc(CN)c3)c3occ(C(F)(F)F)c3c2)c1]

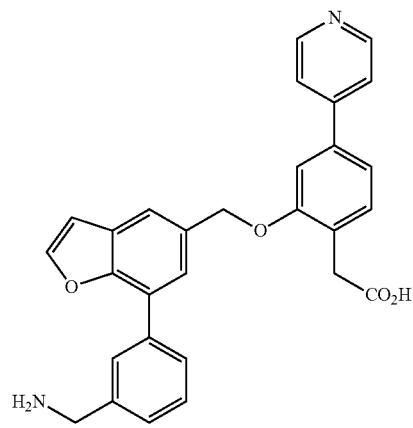 [SMILES: NCc1cccc(-c2cc(COc3cc(-c4ccncc4)ccc3CC(=O)O)cc3ccoc23)c1]
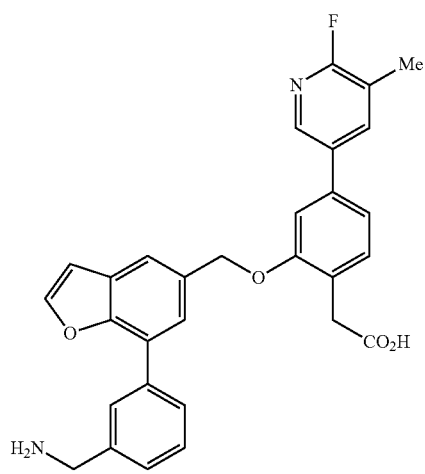 [SMILES: Cc1cc(-c2ccc(CC(=O)O)c(OCc3cc(-c4cccc(CN)c4)c4occc4c3)c2)cnc1F]
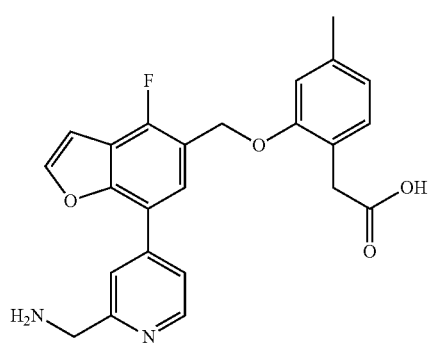 [SMILES: Cc1ccc(CC(=O)O)c(OCc2cc(-c3ccnc(CN)c3)c3occc3c2F)c1]
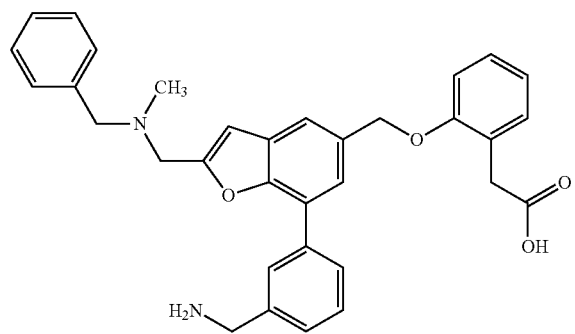 [SMILES: CN(Cc1ccccc1)Cc1cc2cc(COc3ccccc3CC(=O)O)cc(-c3cccc(CN)c3)c2o1]

-continued
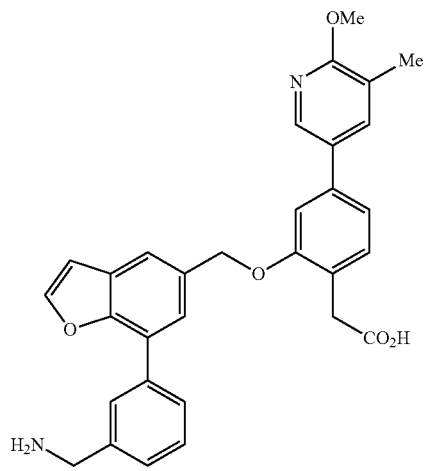 [SMILES: COc1ncc(-c2ccc(CC(=O)O)c(OCc3cc(-c4cccc(CN)c4)c4occc4c3)c2)cc1C]
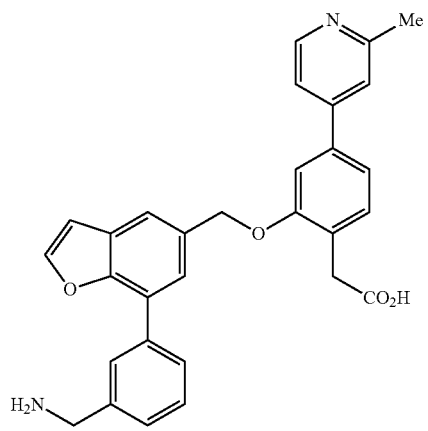 [SMILES: Cc1cc(-c2ccc(CC(=O)O)c(OCc3cc(-c4cccc(CN)c4)c4occc4c3)c2)ccn1]
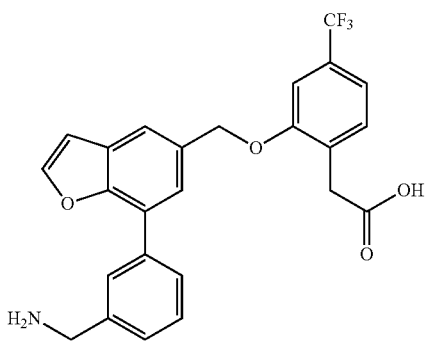 [SMILES: NCc1cccc(-c2cc(COc3cc(C(F)(F)F)ccc3CC(=O)O)cc3ccoc23)c1]
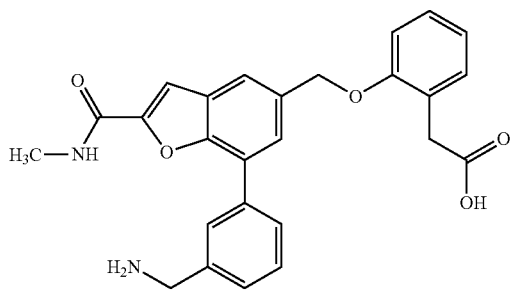 [SMILES: CNC(=O)c1cc2cc(COc3ccccc3CC(=O)O)cc(-c3cccc(CN)c3)c2o1]

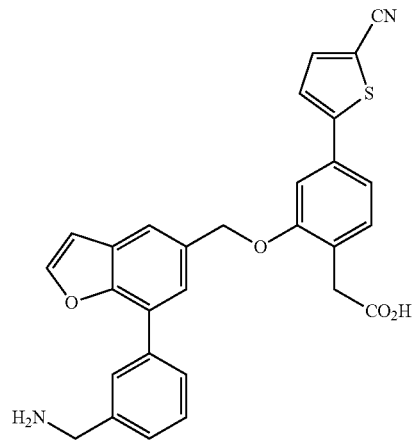 [SMILES: N#Cc1ccc(-c2ccc(CC(=O)O)c(OCc3cc(-c4cccc(CN)c4)c4occc4c3)c2)s1]
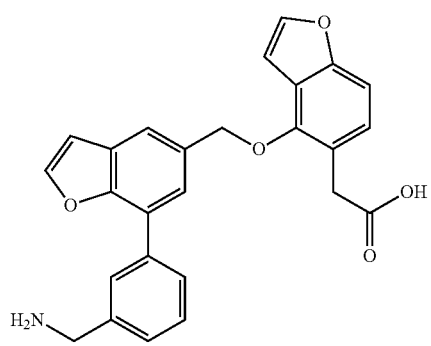 [SMILES: NCc1cccc(-c2cc(COc3c(CC(=O)O)ccc4occc34)cc3ccoc23)c1]
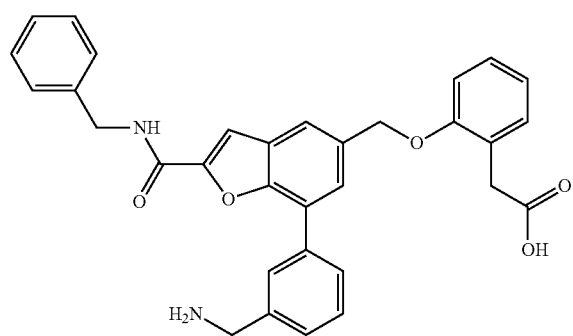 [SMILES: NCc1cccc(-c2cc(COc3ccccc3CC(=O)O)cc3cc(C(=O)NCc4ccccc4)oc23)c1]
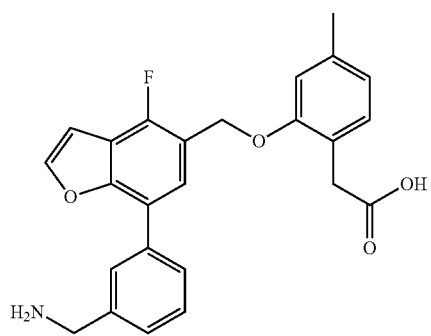 [SMILES: Cc1ccc(CC(=O)O)c(OCc2cc(-c3cccc(CN)c3)c3occc3c2F)c1]

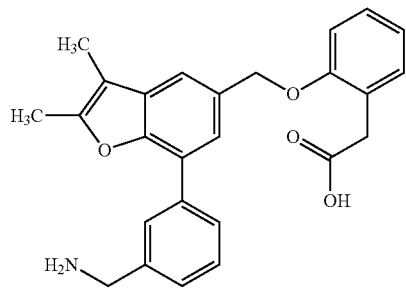 [SMILES: Cc1oc2c(-c3cccc(CN)c3)cc(COc3ccccc3CC(=O)O)cc2c1C]
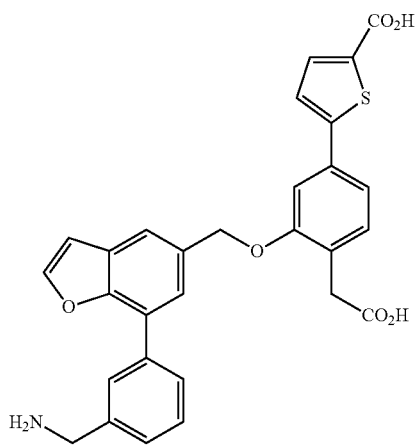 [SMILES: NCc1cccc(-c2cc(COc3cc(-c4ccc(C(=O)O)s4)ccc3CC(=O)O)cc3ccoc23)c1]
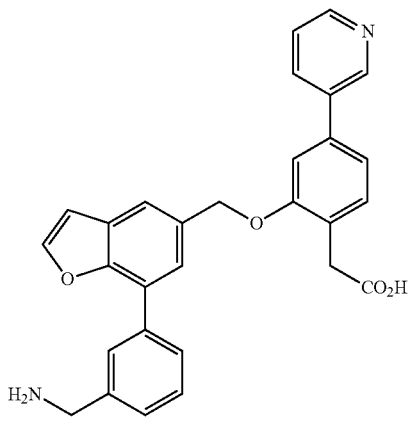 [SMILES: NCc1cccc(-c2cc(COc3cc(-c4cccnc4)ccc3CC(=O)O)cc3ccoc23)c1]
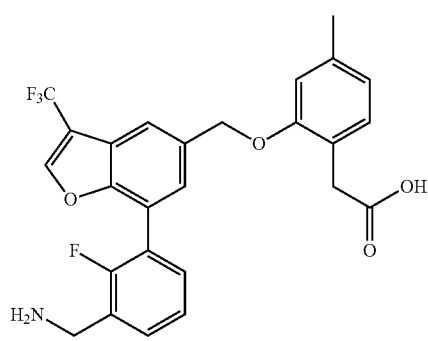 [SMILES: Cc1ccc(CC(=O)O)c(OCc2cc(-c3cccc(CN)c3F)c3occ(C(F)(F)F)c3c2)c1]

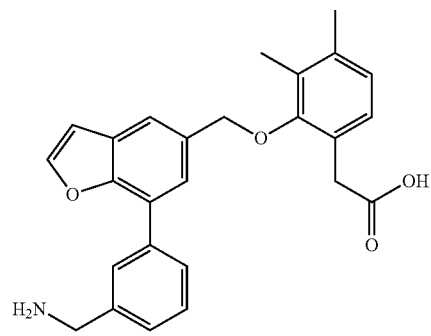 [SMILES: Cc1ccc(CC(=O)O)c(OCc2cc(-c3cccc(CN)c3)c3occc3c2)c1C]
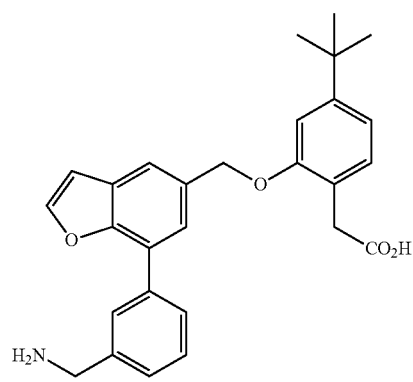 [SMILES: CC(C)(C)c1ccc(CC(=O)O)c(OCc2cc(-c3cccc(CN)c3)c3occc3c2)c1]
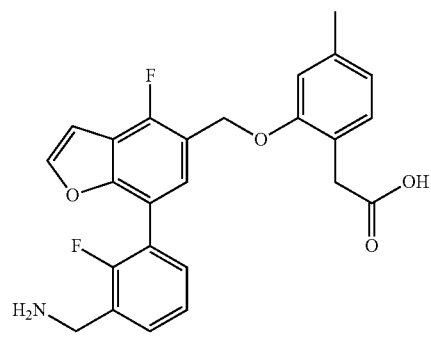 [SMILES: Cc1ccc(CC(=O)O)c(OCc2cc(-c3cccc(CN)c3F)c3occc3c2F)c1]
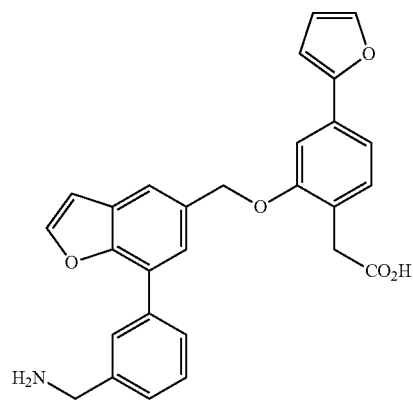 [SMILES: NCc1cccc(-c2cc(COc3cc(-c4ccco4)ccc3CC(=O)O)cc3ccoc23)c1]

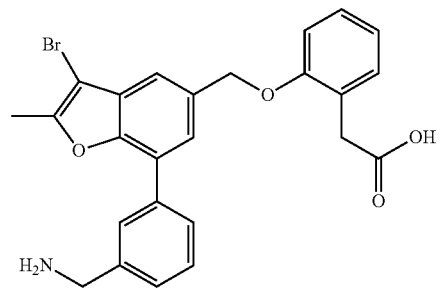 [SMILES: Cc1oc2c(-c3cccc(CN)c3)cc(COc3ccccc3CC(=O)O)cc2c1Br]
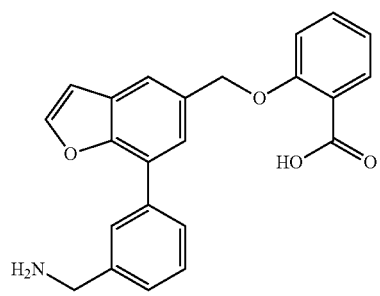 [SMILES: NCc1cccc(-c2cc(COc3ccccc3C(=O)O)cc3ccoc23)c1]
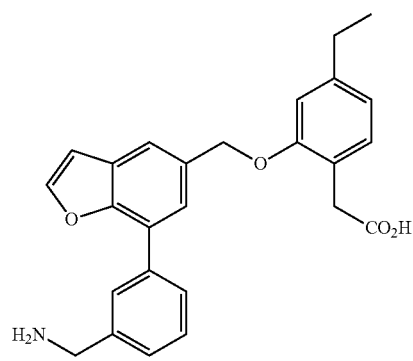 [SMILES: CCc1ccc(CC(=O)O)c(OCc2cc(-c3cccc(CN)c3)c3occc3c2)c1]
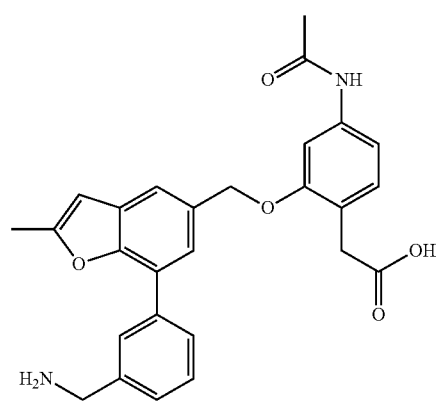 [SMILES: CC(=O)Nc1ccc(CC(=O)O)c(OCc2cc(-c3cccc(CN)c3)c3oc(C)cc3c2)c1]

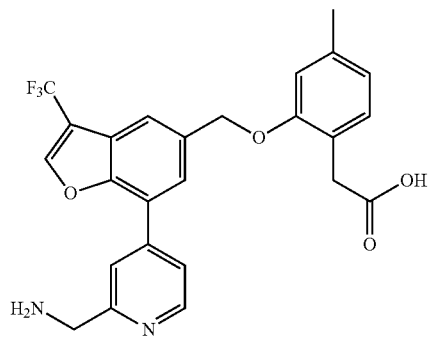 [SMILES: Cc1ccc(CC(=O)O)c(OCc2cc(-c3ccnc(CN)c3)c3occ(C(F)(F)F)c3c2)c1]
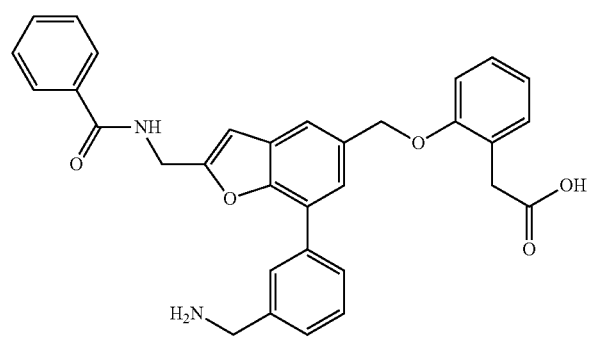 [SMILES: NCc1cccc(-c2cc(COc3ccccc3CC(=O)O)cc3cc(CNC(=O)c4ccccc4)oc23)c1]
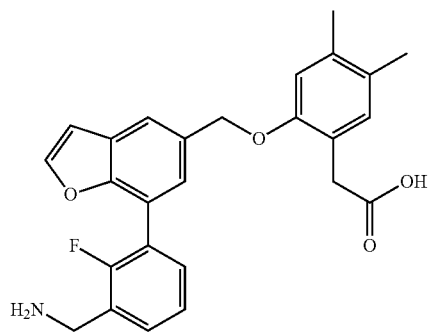 [SMILES: Cc1cc(CC(=O)O)c(OCc2cc(-c3cccc(CN)c3F)c3occc3c2)cc1C]
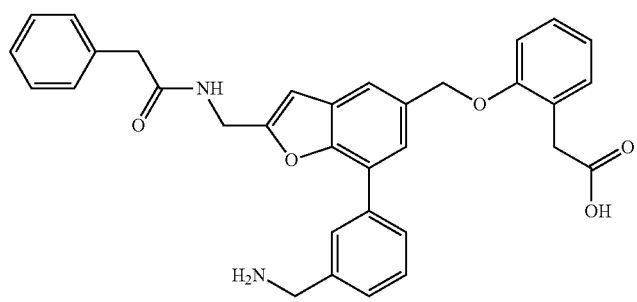 [SMILES: NCc1cccc(-c2cc(COc3ccccc3CC(=O)O)cc3cc(CNC(=O)Cc4ccccc4)oc23)c1]

-continued
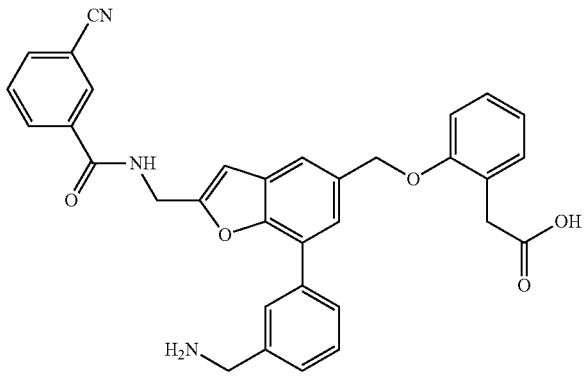 [SMILES: N#Cc1cccc(C(=O)NCc2cc3cc(COc4ccccc4CC(=O)O)cc(-c4cccc(CN)c4)c3o2)c1]
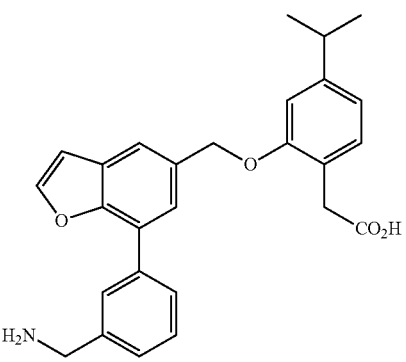 [SMILES: CC(C)c1ccc(CC(=O)O)c(OCc2cc(-c3cccc(CN)c3)c3occc3c2)c1]
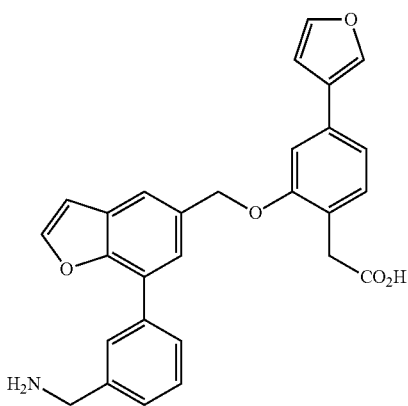 [SMILES: NCc1cccc(-c2cc(COc3cc(-c4ccoc4)ccc3CC(=O)O)cc3ccoc23)c1]
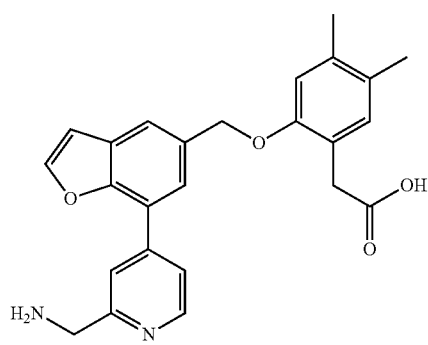 [SMILES: Cc1cc(CC(=O)O)c(OCc2cc(-c3ccnc(CN)c3)c3occc3c2)cc1C]

-continued
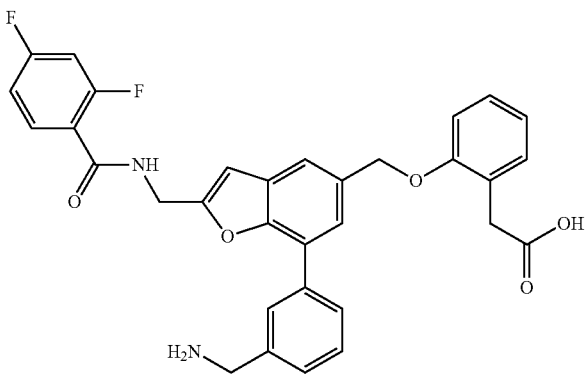 [SMILES: NCc1cccc(-c2cc(COc3ccccc3CC(=O)O)cc3cc(CNC(=O)c4ccc(F)cc4F)oc23)c1]
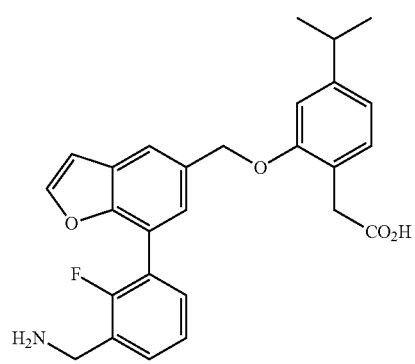 [SMILES: CC(C)c1ccc(CC(=O)O)c(OCc2cc(-c3cccc(CN)c3F)c3occc3c2)c1]
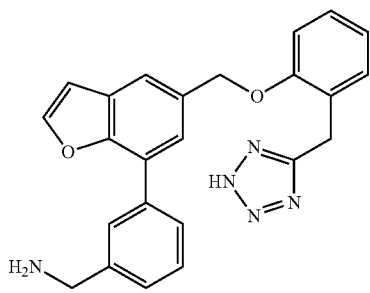 [SMILES: NCc1cccc(-c2cc(COc3ccccc3Cc3nn[nH]n3)cc3ccoc23)c1]
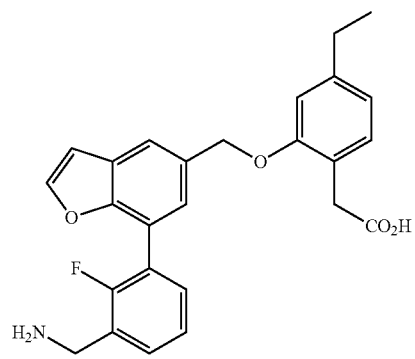 [SMILES: CCc1ccc(CC(=O)O)c(OCc2cc(-c3cccc(CN)c3F)c3occc3c2)c1]

-continued
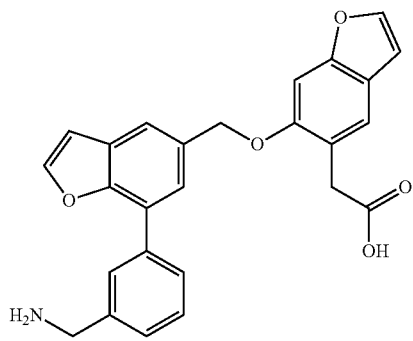 [SMILES: NCc1cccc(-c2cc(COc3cc4occc4cc3CC(=O)O)cc3ccoc23)c1]
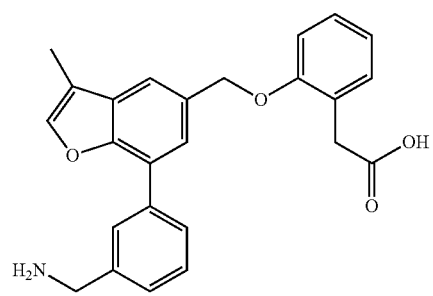 [SMILES: Cc1coc2c(-c3cccc(CN)c3)cc(COc3ccccc3CC(=O)O)cc12]
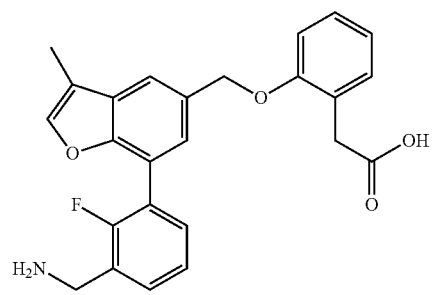 [SMILES: Cc1coc2c(-c3cccc(CN)c3F)cc(COc3ccccc3CC(=O)O)cc12]
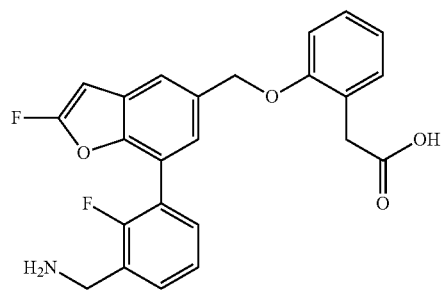 [SMILES: NCc1cccc(-c2cc(COc3ccccc3CC(=O)O)cc3cc(F)oc23)c1F]
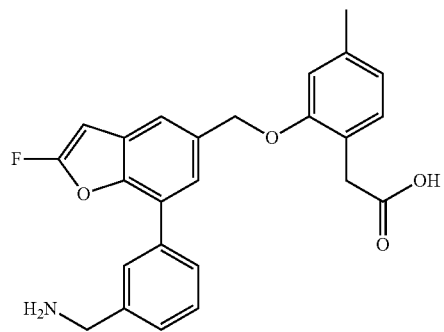 [SMILES: Cc1ccc(CC(=O)O)c(OCc2cc(-c3cccc(CN)c3)c3oc(F)cc3c2)c1]

-continued
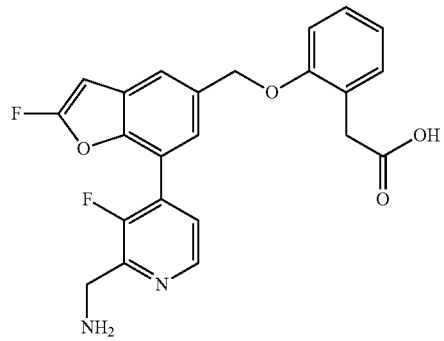 [SMILES: NCc1cc(-c2cc(COc3ccccc3CC(=O)O)cc3cc(F)oc23)ccn1]
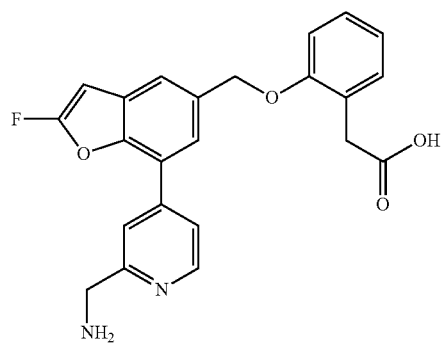
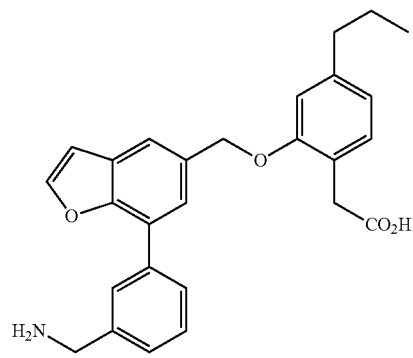 [SMILES: CCCc1ccc(CC(=O)O)c(OCc2cc(-c3cccc(CN)c3)c3occc3c2)c1]
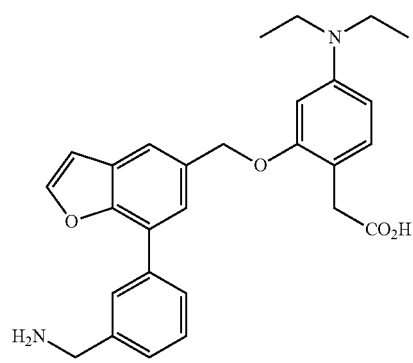 [SMILES: CCN(CC)c1ccc(CC(=O)O)c(OCc2cc(-c3cccc(CN)c3)c3occc3c2)c1]

-continued
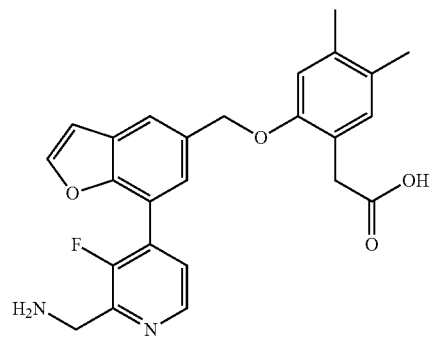 [SMILES: Cc1cc(CC(=O)O)c(OCc2cc(-c3ccnc(CN)c3F)c3occc3c2)cc1C]
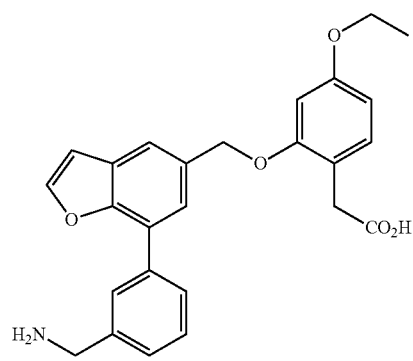 [SMILES: CCOc1ccc(CC(=O)O)c(OCc2cc(-c3cccc(CN)c3)c3occc3c2)c1]
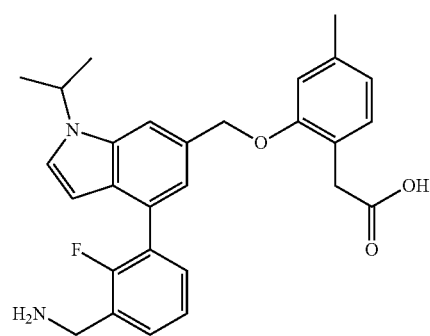 [SMILES: Cc1ccc(CC(=O)O)c(OCc2cc(-c3cccc(CN)c3F)c3ccn(C(C)C)c3c2)c1]
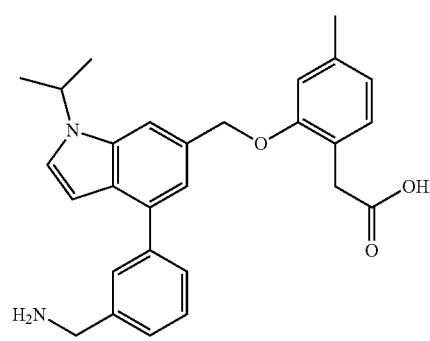 [SMILES: Cc1ccc(CC(=O)O)c(OCc2cc(-c3cccc(CN)c3)c3ccn(C(C)C)c3c2)c1]

-continued
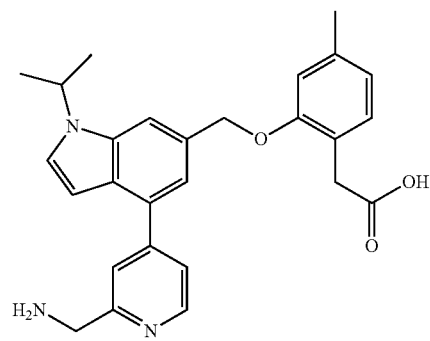 [SMILES: Cc1ccc(CC(=O)O)c(OCc2cc(-c3ccnc(CN)c3)c3ccn(C(C)C)c3c2)c1]
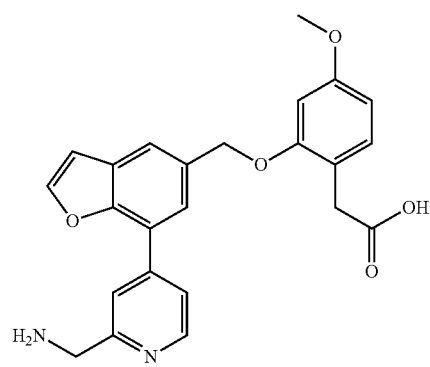 [SMILES: COc1ccc(CC(=O)O)c(OCc2cc(-c3ccnc(CN)c3)c3occc3c2)c1]
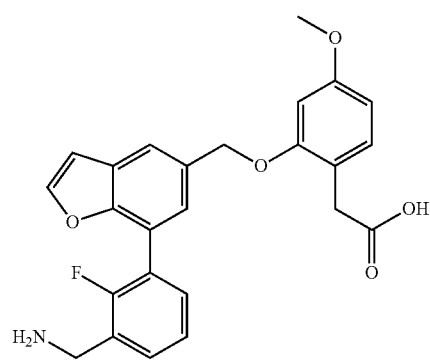 [SMILES: COc1ccc(CC(=O)O)c(OCc2cc(-c3cccc(CN)c3F)c3occc3c2)c1]
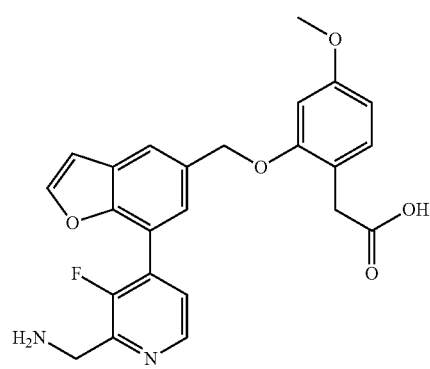 [SMILES: COc1ccc(CC(=O)O)c(OCc2cc(-c3ccnc(CN)c3F)c3occc3c2)c1]

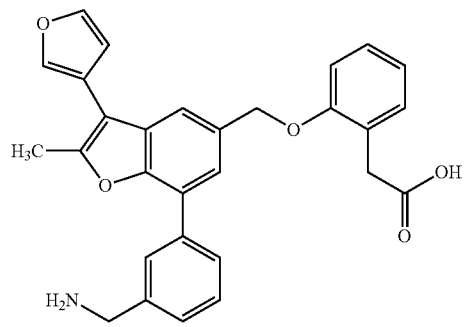 [SMILES: Cc1oc2c(-c3cccc(CN)c3)cc(COc3ccccc3CC(=O)O)cc2c1-c1ccoc1]
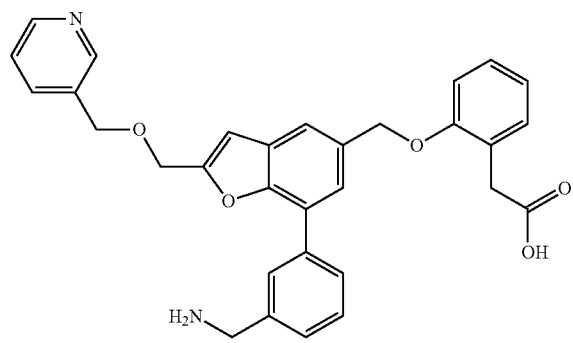 [SMILES: NCc1cccc(-c2cc(COc3ccccc3CC(=O)O)cc3cc(COCc4cccnc4)oc23)c1]
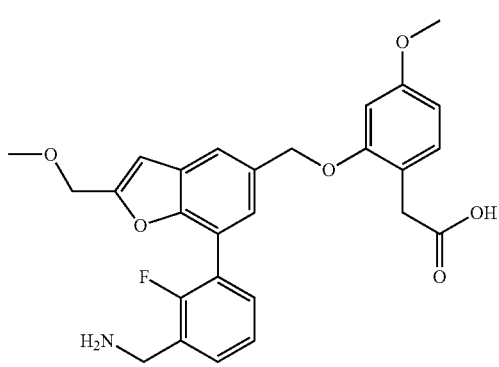 [SMILES: COCc1cc2cc(COc3cc(OC)ccc3CC(=O)O)cc(-c3cccc(CN)c3F)c2o1]
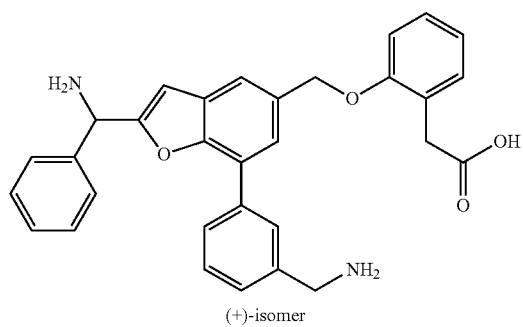 [SMILES: NCc1cccc(-c2cc(COc3ccccc3CC(=O)O)cc3cc(C(N)c4ccccc4)oc23)c1]

-continued
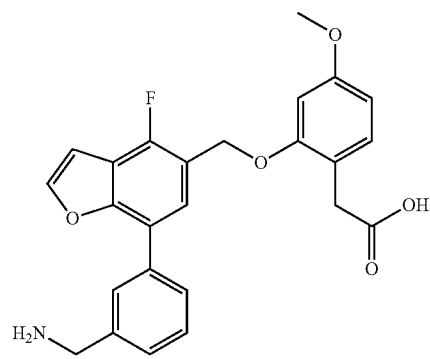 [SMILES: COc1ccc(CC(=O)O)c(OCc2cc(-c3cccc(CN)c3)c3occc3c2F)c1]
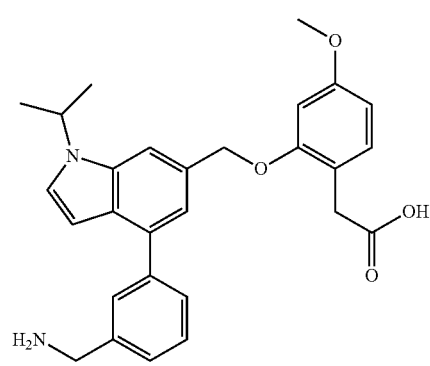 [SMILES: COc1ccc(CC(=O)O)c(OCc2cc(-c3cccc(CN)c3)c3ccn(C(C)C)c3c2)c1]
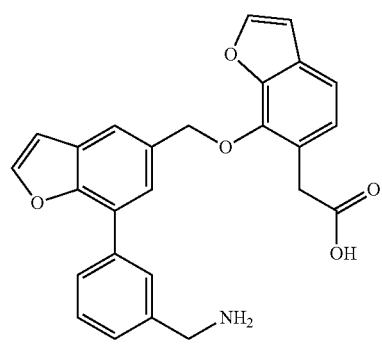 [SMILES: NCc1cccc(-c2cc(COc3c(CC(=O)O)ccc4ccoc34)cc3ccoc23)c1]
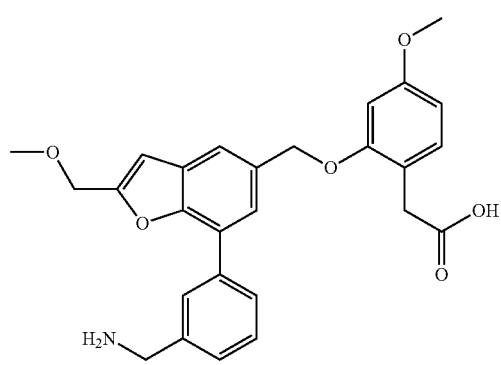 [SMILES: COCc1cc2cc(COc3cc(OC)ccc3CC(=O)O)cc(-c3cccc(CN)c3)c2o1]

-continued
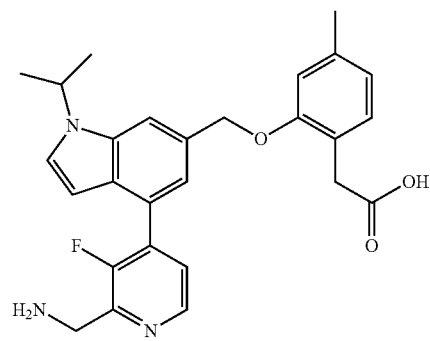 [SMILES: Cc1ccc(CC(=O)O)c(OCc2cc(-c3ccnc(CN)c3F)c3ccn(C(C)C)c3c2)c1]
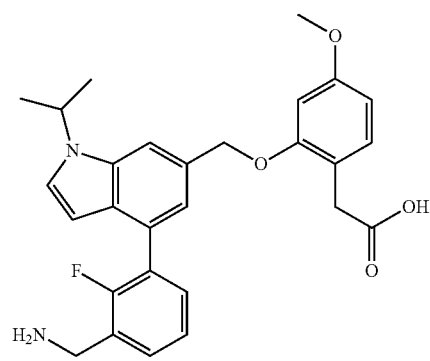 [SMILES: COc1ccc(CC(=O)O)c(OCc2cc(-c3cccc(CN)c3F)c3ccn(C(C)C)c3c2)c1]
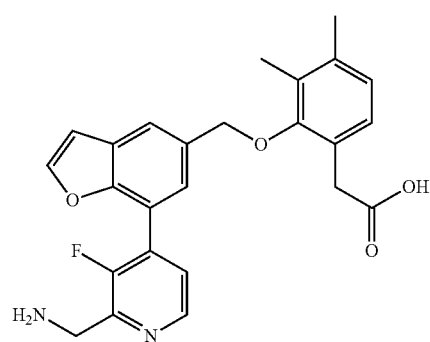 [SMILES: Cc1ccc(CC(=O)O)c(OCc2cc(-c3ccnc(CN)c3F)c3occc3c2)c1C]
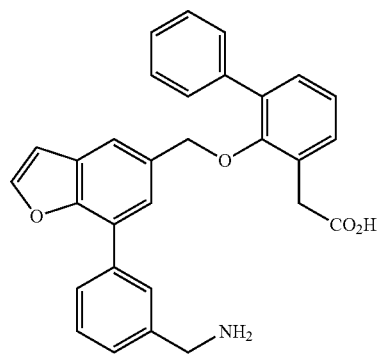 [SMILES: NCc1cccc(-c2cc(COc3c(CC(=O)O)cccc3-c3ccccc3)cc3ccoc23)c1]

-continued
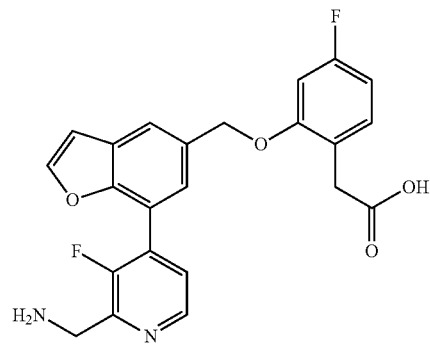 [SMILES: NCc1nccc(-c2cc(COc3cc(F)ccc3CC(=O)O)cc3ccoc23)c1F]
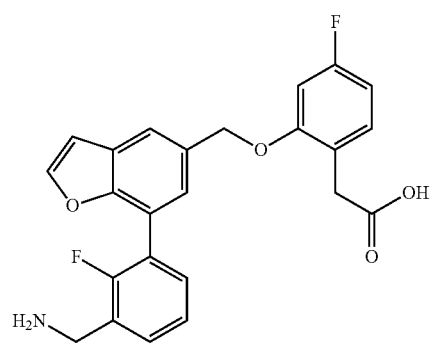 [SMILES: NCc1cccc(-c2cc(COc3cc(F)ccc3CC(=O)O)cc3ccoc23)c1F]
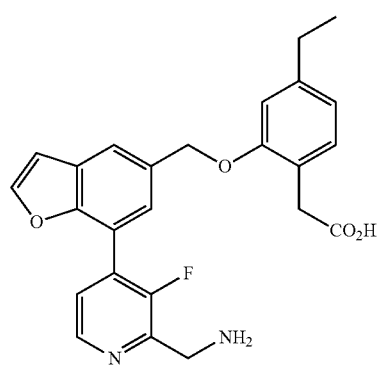 [SMILES: CCc1ccc(CC(=O)O)c(OCc2cc(-c3ccnc(CN)c3F)c3occc3c2)c1]
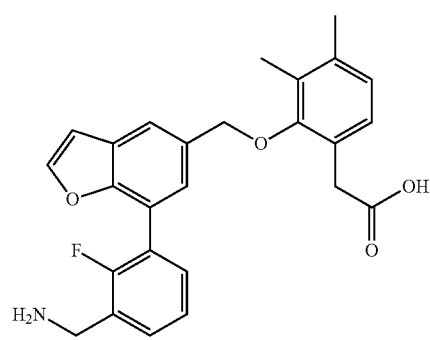 [SMILES: Cc1ccc(CC(=O)O)c(OCc2cc(-c3cccc(CN)c3F)c3occc3c2)c1C]

-continued
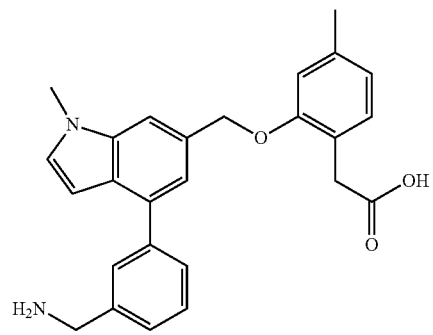 [SMILES: Cc1ccc(CC(=O)O)c(OCc2cc(-c3cccc(CN)c3)c3ccn(C)c3c2)c1]
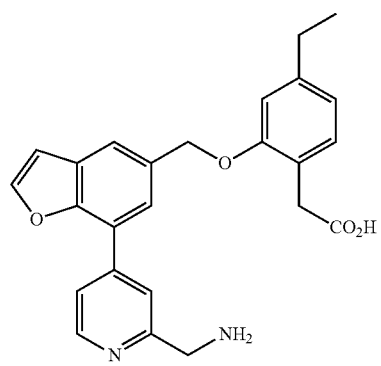 [SMILES: CCc1ccc(CC(=O)O)c(OCc2cc(-c3ccnc(CN)c3)c3occc3c2)c1]
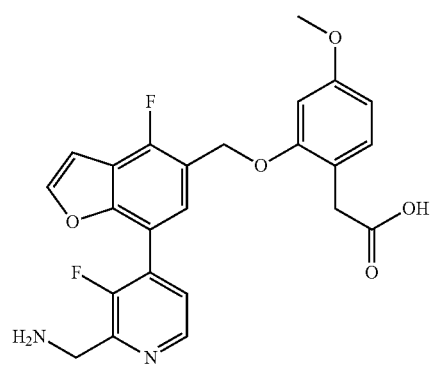 [SMILES: COc1ccc(CC(=O)O)c(OCc2cc(-c3ccnc(CN)c3F)c3occc3c2F)c1]
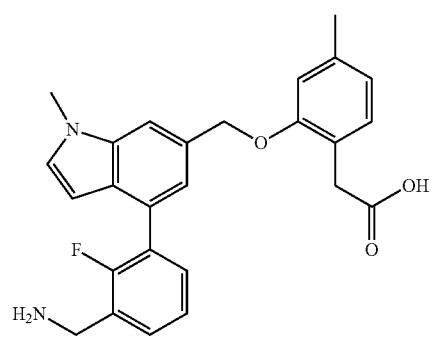 [SMILES: Cc1ccc(CC(=O)O)c(OCc2cc(-c3cccc(CN)c3F)c3ccn(C)c3c2)c1]

-continued
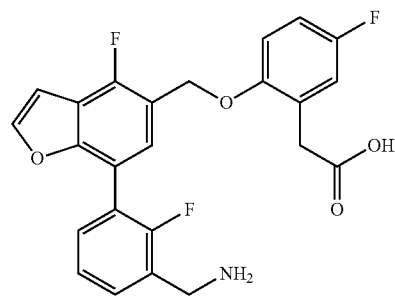 [SMILES: NCc1cccc(-c2cc(COc3ccc(F)cc3CC(=O)O)c(F)c3ccoc23)c1F]
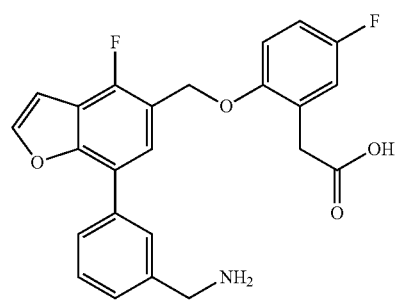 [SMILES: NCc1cccc(-c2cc(COc3ccc(F)cc3CC(=O)O)c(F)c3ccoc23)c1]
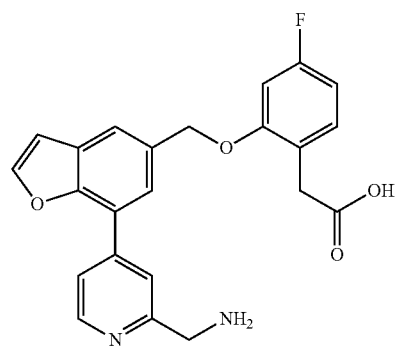 [SMILES: NCc1cc(-c2cc(COc3cc(F)ccc3CC(=O)O)cc3ccoc23)ccn1]
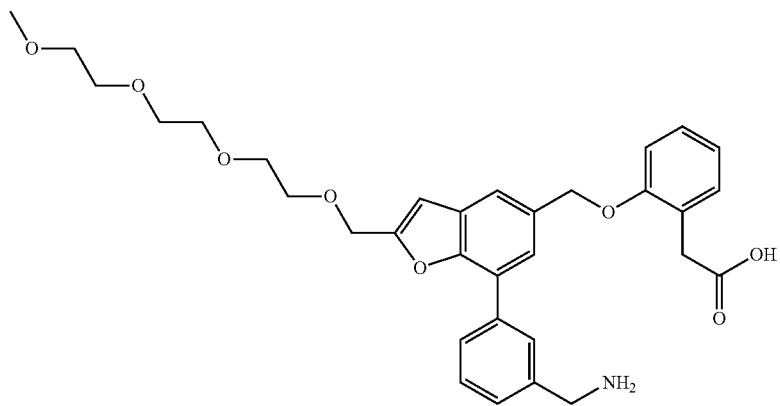 [SMILES: COCCOCCOCCOCc1cc2cc(COc3ccccc3CC(=O)O)cc(-c3cccc(CN)c3)c2o1]

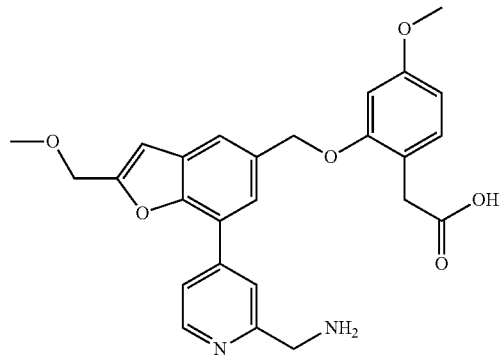 [SMILES: COCc1cc2cc(COc3cc(OC)ccc3CC(=O)O)cc(-c3ccnc(CN)c3)c2o1]
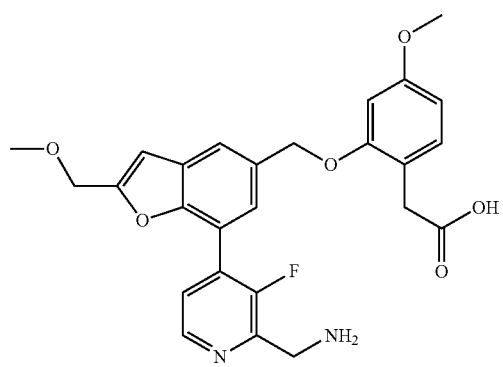 [SMILES: COCc1cc2cc(COc3cc(OC)ccc3CC(=O)O)cc(-c3ccnc(CN)c3F)c2o1]
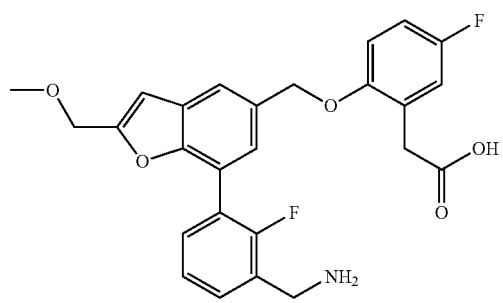 [SMILES: COCc1cc2cc(COc3ccc(F)cc3CC(=O)O)cc(-c3cccc(CN)c3F)c2o1]
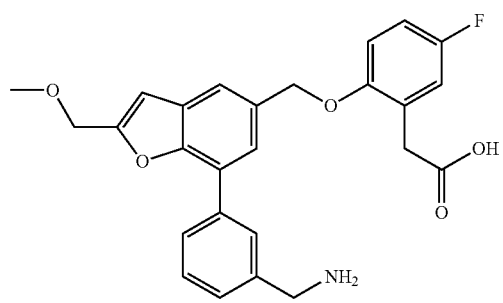 [SMILES: COCc1cc2cc(COc3ccc(F)cc3CC(=O)O)cc(-c3cccc(CN)c3)c2o1]

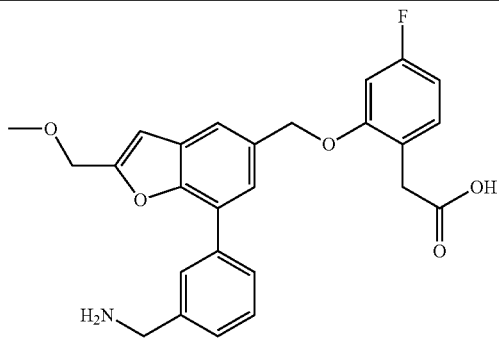
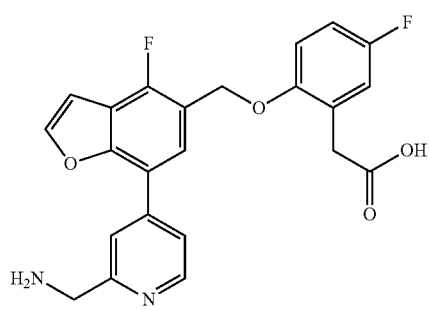 [SMILES: NCc1cc(-c2cc(COc3ccc(F)cc3CC(=O)O)c(F)c3ccoc23)ccn1]
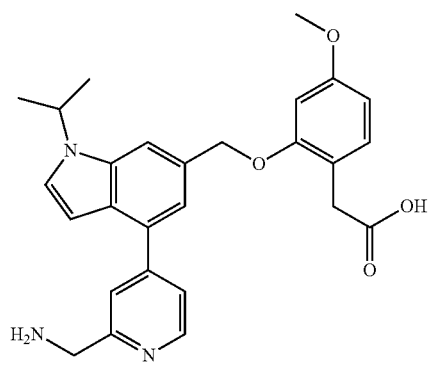 [SMILES: COc1ccc(CC(=O)O)c(OCc2cc(-c3ccnc(CN)c3)c3ccn(C(C)C)c3c2)c1]
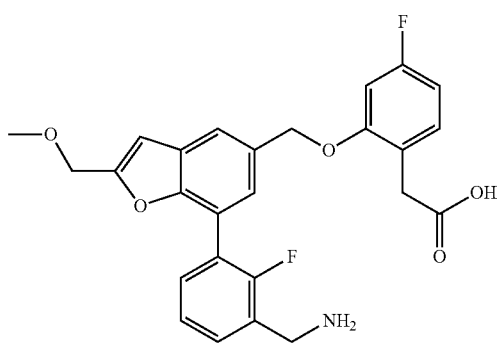 [SMILES: COCc1cc2cc(COc3cc(F)ccc3CC(=O)O)cc(-c3cccc(CN)c3F)c2o1]
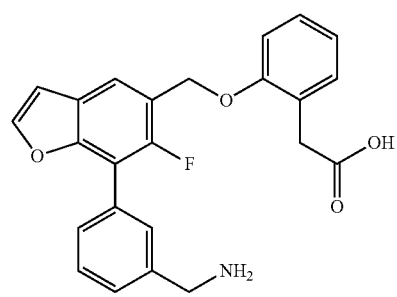 [SMILES: NCc1cccc(-c2c(F)c(COc3ccccc3CC(=O)O)cc3ccoc23)c1]

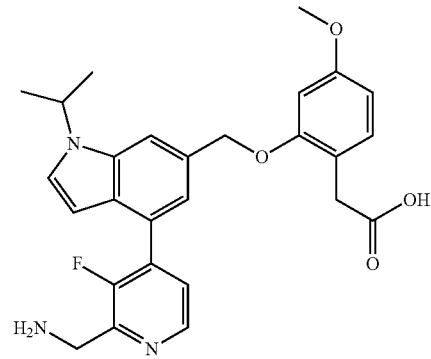 [SMILES: COc1ccc(CC(=O)O)c(OCc2cc(-c3ccnc(CN)c3F)c3ccn(C(C)C)c3c2)c1]
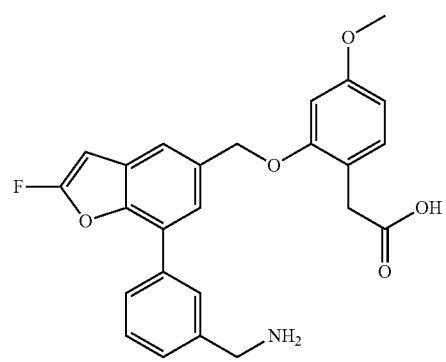 [SMILES: COc1ccc(CC(=O)O)c(OCc2cc(-c3cccc(CN)c3)c3oc(F)cc3c2)c1]
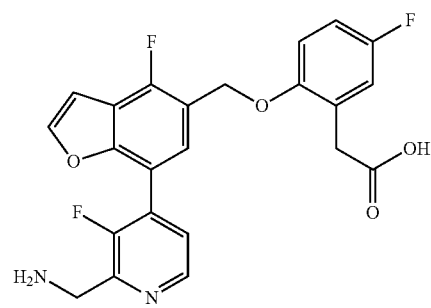 [SMILES: NCc1nccc(-c2cc(COc3ccc(F)cc3CC(=O)O)c(F)c3ccoc23)c1F]
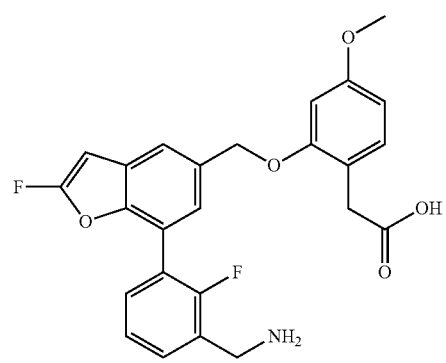 [SMILES: COc1ccc(CC(=O)O)c(OCc2cc(-c3cccc(CN)c3F)c3oc(F)cc3c2)c1]

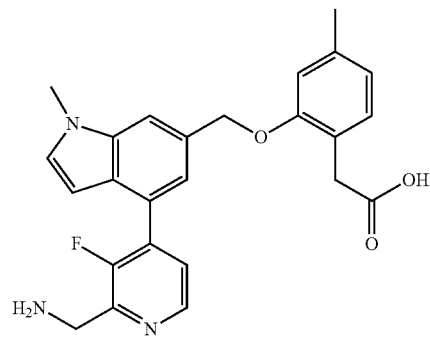 [SMILES: Cc1ccc(CC(=O)O)c(OCc2cc(-c3ccnc(CN)c3F)c3ccn(C)c3c2)c1]
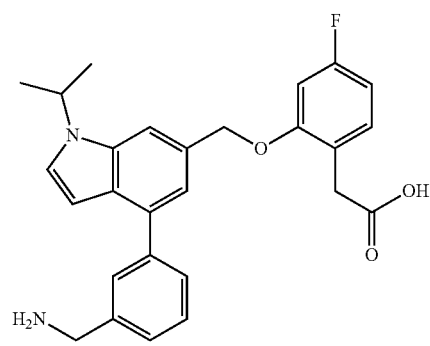 [SMILES: CC(C)n1ccc2c(-c3cccc(CN)c3)cc(COc3cc(F)ccc3CC(=O)O)cc21]
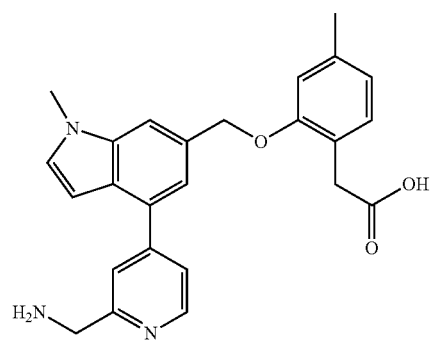 [SMILES: Cc1ccc(CC(=O)O)c(OCc2cc(-c3ccnc(CN)c3)c3ccn(C)c3c2)c1]
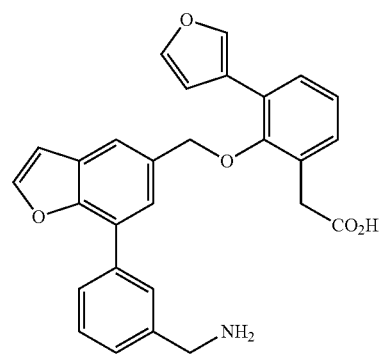 [SMILES: NCc1cccc(-c2cc(COc3c(CC(=O)O)cccc3-c3ccoc3)cc3ccoc23)c1]

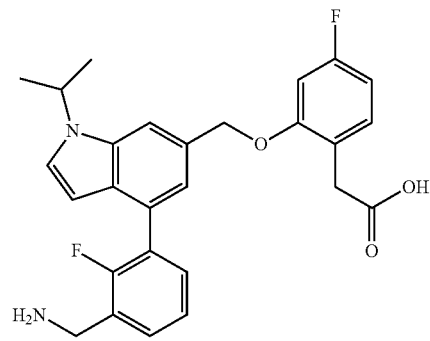 [SMILES: CC(C)n1ccc2c(-c3cccc(CN)c3F)cc(COc3cc(F)ccc3CC(=O)O)cc21]
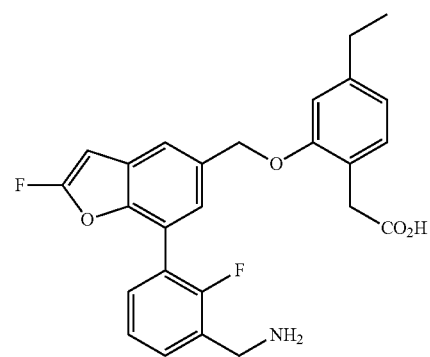 [SMILES: CCc1ccc(CC(=O)O)c(OCc2cc(-c3cccc(CN)c3F)c3oc(F)cc3c2)c1]
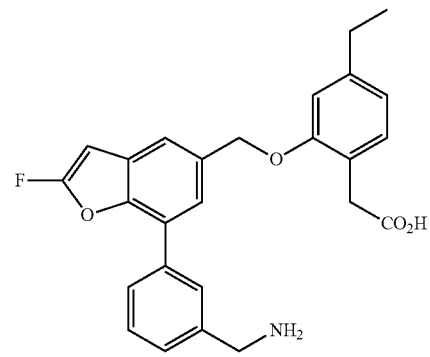 [SMILES: CCc1ccc(CC(=O)O)c(OCc2cc(-c3cccc(CN)c3)c3oc(F)cc3c2)c1]
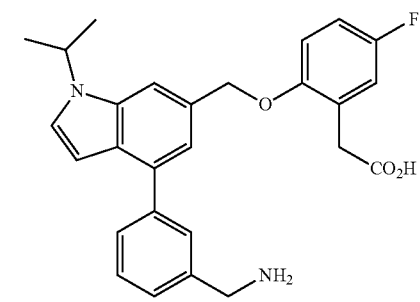 [SMILES: CC(C)n1ccc2c(-c3cccc(CN)c3)cc(COc3ccc(F)cc3CC(=O)O)cc21]

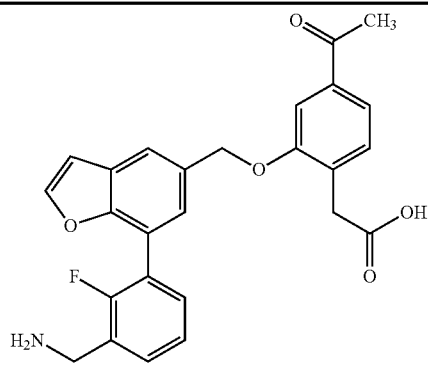
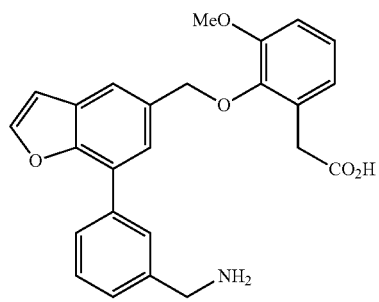 [SMILES: COc1cccc(CC(=O)O)c1OCc1cc(-c2cccc(CN)c2)c2occc2c1]
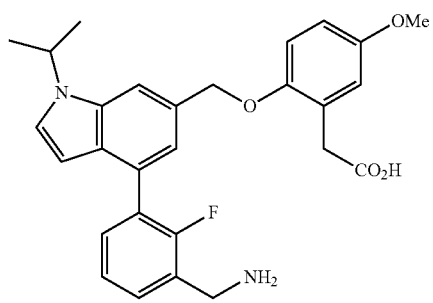 [SMILES: COc1ccc(OCc2cc(-c3cccc(CN)c3F)c3ccn(C(C)C)c3c2)c(CC(=O)O)c1]
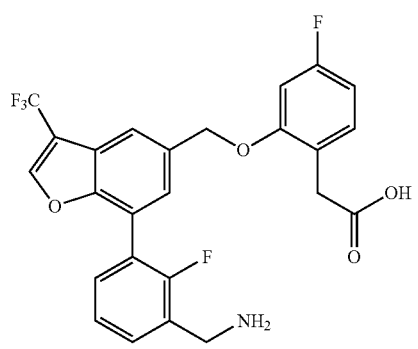 [SMILES: NCc1cccc(-c2cc(COc3cc(F)ccc3CC(=O)O)cc3c(C(F)(F)F)coc23)c1F]
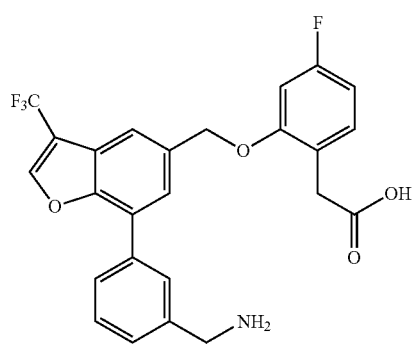 [SMILES: NCc1cccc(-c2cc(COc3cc(F)ccc3CC(=O)O)cc3c(C(F)(F)F)coc23)c1]

-continued
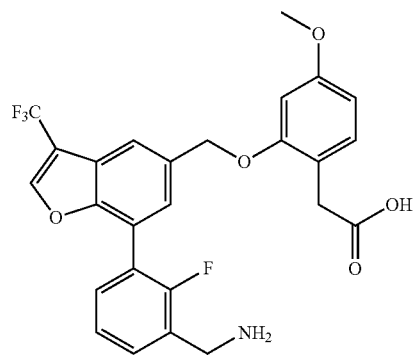 [SMILES: COc1ccc(CC(=O)O)c(OCc2cc(-c3cccc(CN)c3F)c3occ(C(F)(F)F)c3c2)c1]
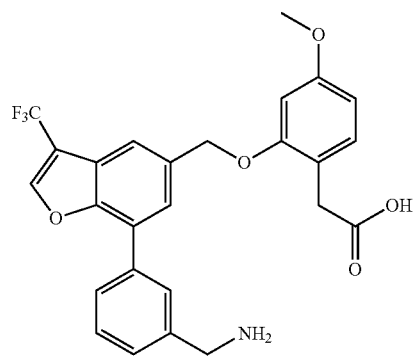 [SMILES: COc1ccc(CC(=O)O)c(OCc2cc(-c3cccc(CN)c3)c3occ(C(F)(F)F)c3c2)c1]

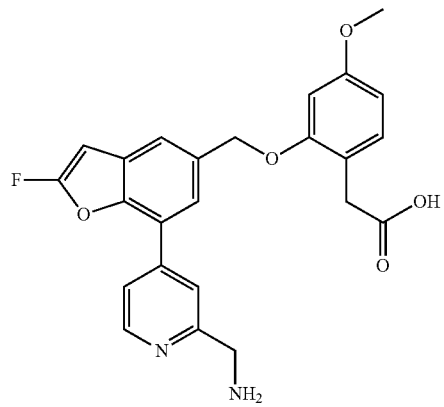 [SMILES: COc1ccc(CC(=O)O)c(OCc2cc(-c3ccnc(CN)c3)c3oc(F)cc3c2)c1]
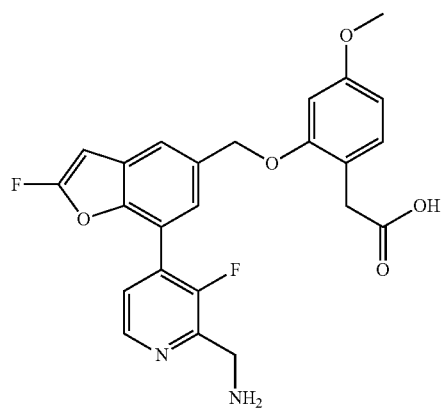 [SMILES: COc1ccc(CC(=O)O)c(OCc2cc(-c3ccnc(CN)c3F)c3oc(F)cc3c2)c1]

-continued
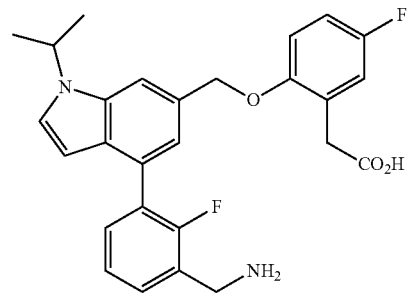 [SMILES: CC(C)n1ccc2c(-c3cccc(CN)c3F)cc(COc3ccc(F)cc3CC(=O)O)cc21]
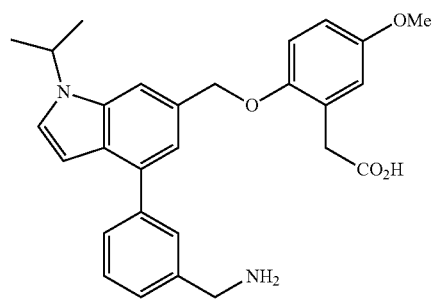 [SMILES: COc1ccc(OCc2cc(-c3cccc(CN)c3)c3ccn(C(C)C)c3c2)c(CC(=O)O)c1]
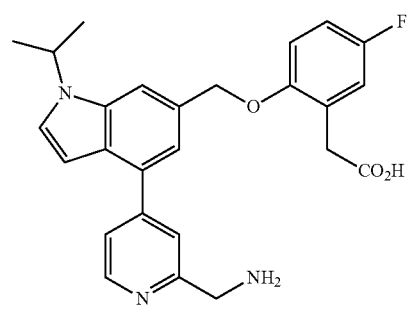 [SMILES: CC(C)n1ccc2c(-c3ccnc(CN)c3)cc(COc3ccc(F)cc3CC(=O)O)cc21]
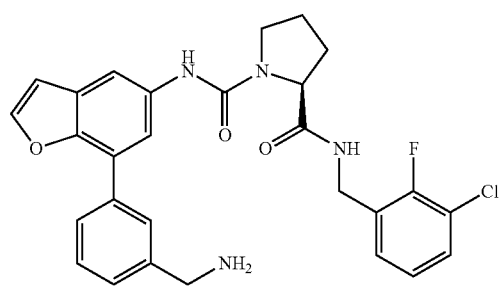 [SMILES: NCc1cccc(-c2cc(NC(=O)N3CCC[C@H]3C(=O)NCc3cccc(Cl)c3F)cc3ccoc23)c1]
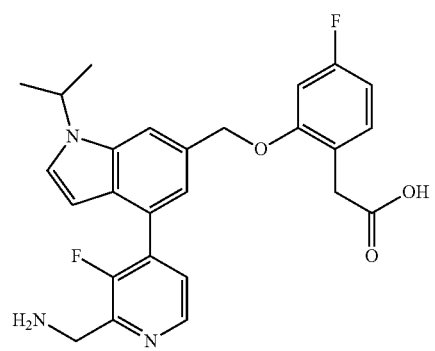 [SMILES: CC(C)n1ccc2c(-c3ccnc(CN)c3F)cc(COc3cc(F)ccc3CC(=O)O)cc21]

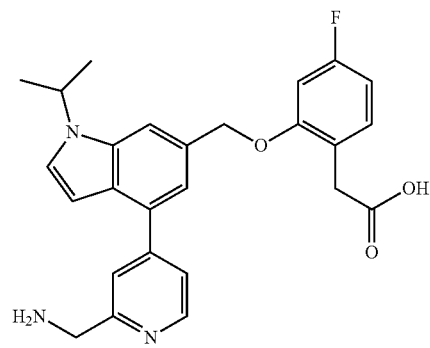 [SMILES: CC(C)n1ccc2c(-c3ccnc(CN)c3)cc(COc3cc(F)ccc3CC(=O)O)cc21]
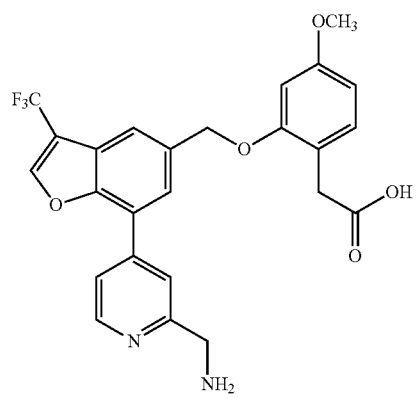
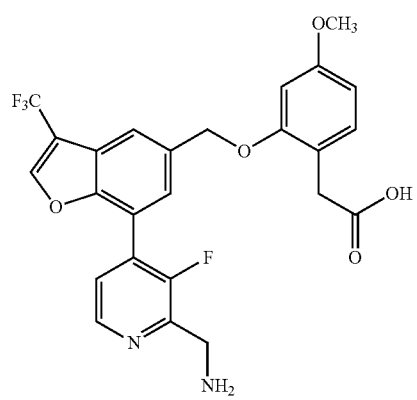 [SMILES: COc1ccc(CC(=O)O)c(OCc2cc(-c3ccnc(CN)c3F)c3occ(C(F)(F)F)c3c2)c1]
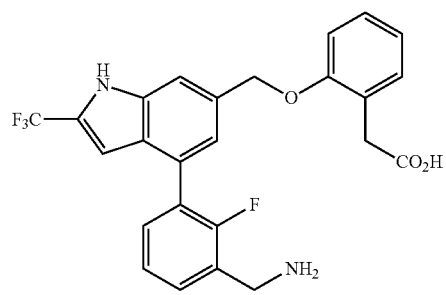 [SMILES: NCc1cccc(-c2cc(COc3ccccc3CC(=O)O)cc3[nH]c(C(F)(F)F)cc23)c1F]

-continued
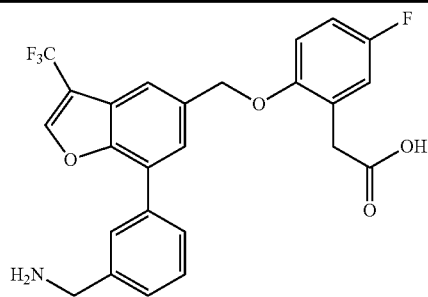
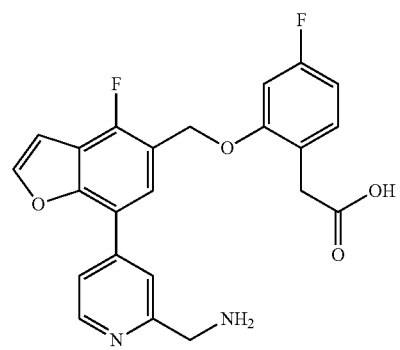 [SMILES: NCc1cc(-c2cc(COc3cc(F)ccc3CC(=O)O)c(F)c3ccoc23)ccn1]
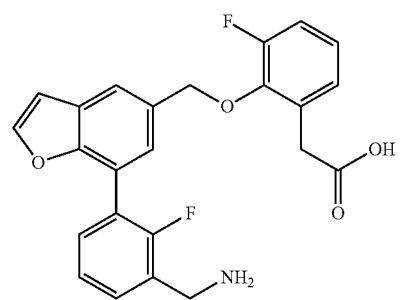 [SMILES: NCc1cccc(-c2cc(COc3c(F)cccc3CC(=O)O)cc3ccoc23)c1F]
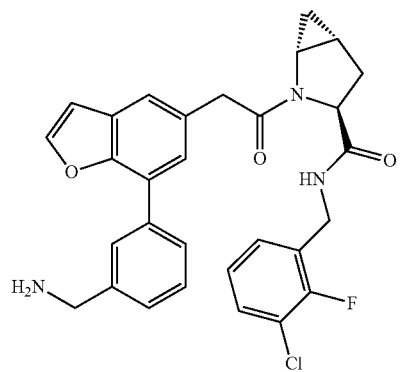 [SMILES: NCc1cccc(-c2cc(CC(=O)N3[C@@H]4C[C@@H]4C[C@H]3C(=O)NCc3cccc(Cl)c3F)cc3ccoc23)c1]
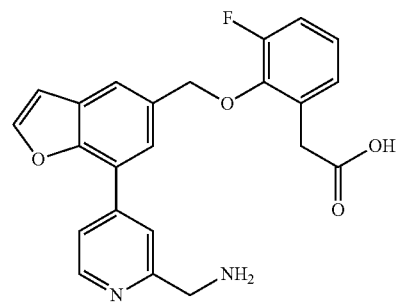 [SMILES: NCc1cc(-c2cc(COc3c(F)cccc3CC(=O)O)cc3ccoc23)ccn1]

-continued
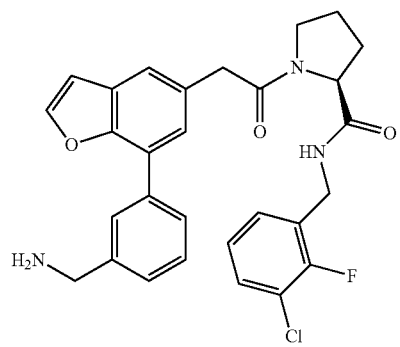 [SMILES: NCc1cccc(-c2cc(CC(=O)N3CCC[C@H]3C(=O)NCc3cccc(Cl)c3F)cc3ccoc23)c1]
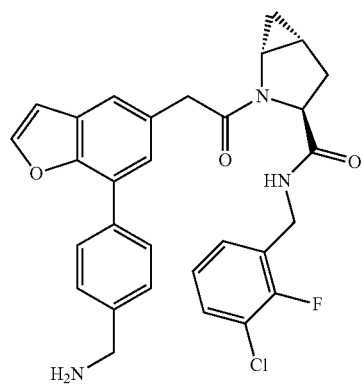 [SMILES: NCc1ccc(-c2cc(CC(=O)N3[C@@H]4C[C@@H]4C[C@H]3C(=O)NCc3cccc(Cl)c3F)cc3ccoc23)cc1]
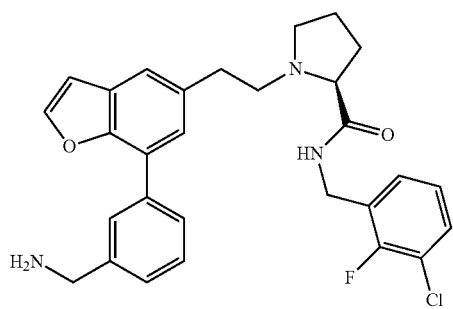 [SMILES: NCc1cccc(-c2cc(CCN3CCC[C@H]3C(=O)NCc3cccc(Cl)c3F)cc3ccoc23)c1]
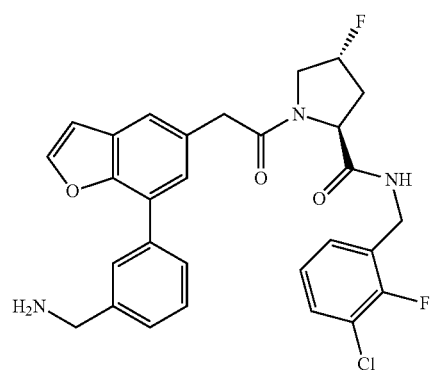 [SMILES: NCc1cccc(-c2cc(CC(=O)N3C[C@H](F)C[C@H]3C(=O)NCc3cccc(Cl)c3F)cc3ccoc23)c1]

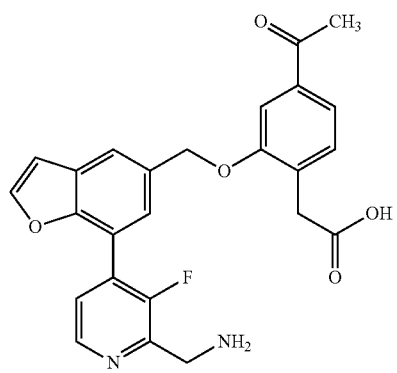 [SMILES: CC(=O)c1ccc(CC(=O)O)c(OCc2cc(-c3ccnc(CN)c3F)c3occc3c2)c1]
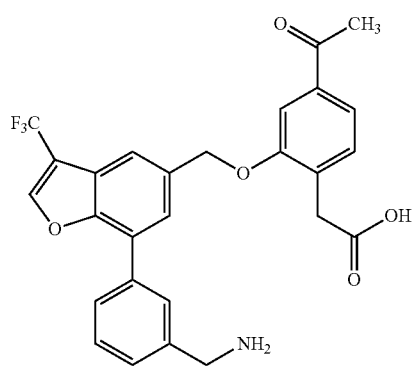 [SMILES: CC(=O)c1ccc(CC(=O)O)c(OCc2cc(-c3cccc(CN)c3)c3occ(C(F)(F)F)c3c2)c1]
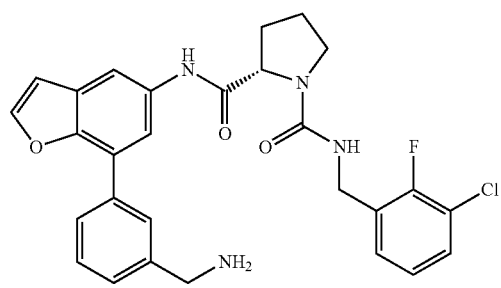 [SMILES: NCc1cccc(-c2cc(NC(=O)[C@@H]3CCCN3C(=O)NCc3cccc(Cl)c3F)cc3ccoc23)c1]
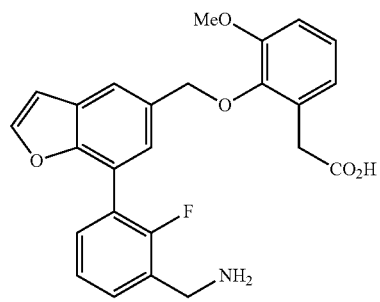 [SMILES: COc1cccc(CC(=O)O)c1OCc1cc(-c2cccc(CN)c2F)c2occc2c1]

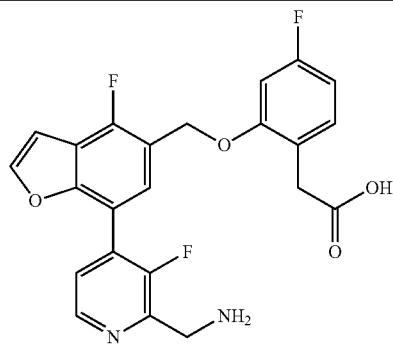
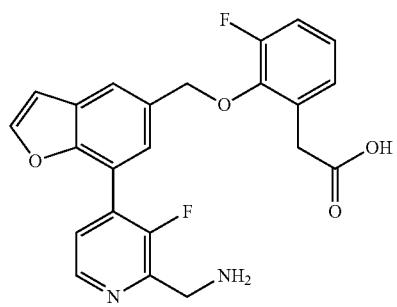 [SMILES: NCc1nccc(-c2cc(COc3c(F)cccc3CC(=O)O)cc3ccoc23)c1F]
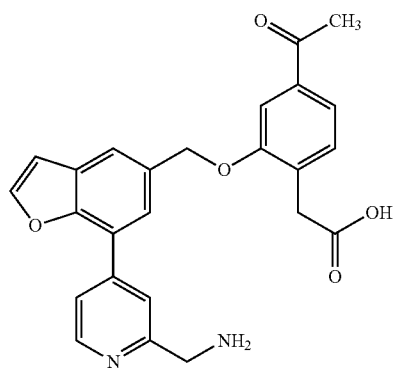 [SMILES: CC(=O)c1ccc(CC(=O)O)c(OCc2cc(-c3ccnc(CN)c3)c3occc3c2)c1]
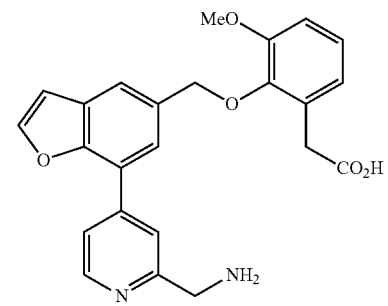 [SMILES: COc1cccc(CC(=O)O)c1OCc1cc(-c2ccnc(CN)c2)c2occc2c1]
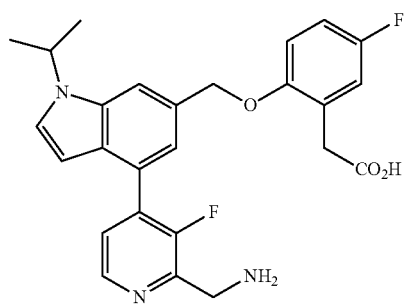 [SMILES: CC(C)n1ccc2c(-c3ccnc(CN)c3F)cc(COc3ccc(F)cc3CC(=O)O)cc21]

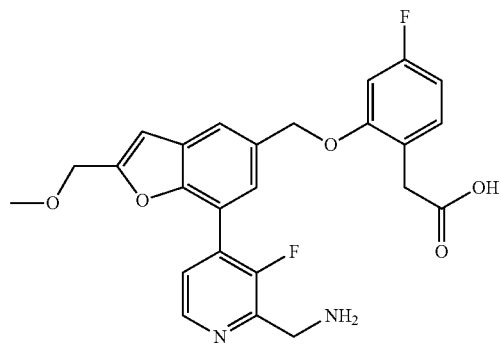 [SMILES: COCc1cc2cc(COc3cc(F)ccc3CC(=O)O)cc(-c3ccnc(CN)c3F)c2o1]
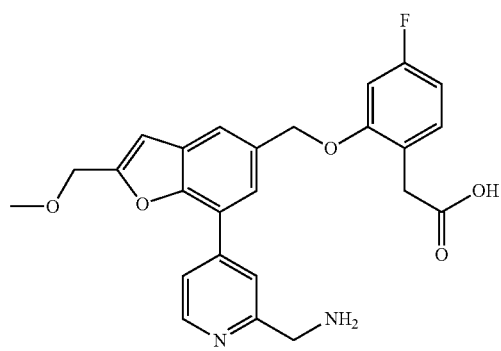 [SMILES: COCc1cc2cc(COc3cc(F)ccc3CC(=O)O)cc(-c3ccnc(CN)c3)c2o1]
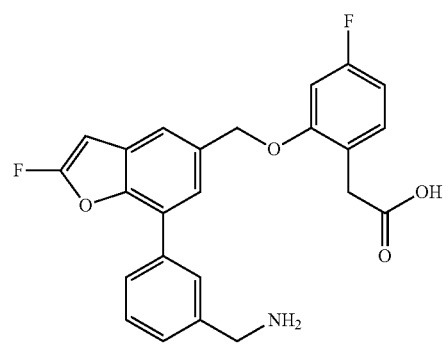 [SMILES: NCc1cccc(-c2cc(COc3cc(F)ccc3CC(=O)O)cc3cc(F)oc23)c1]
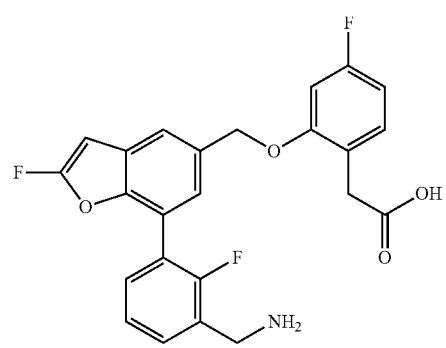 [SMILES: NCc1cccc(-c2cc(COc3cc(F)ccc3CC(=O)O)cc3cc(F)oc23)c1F]

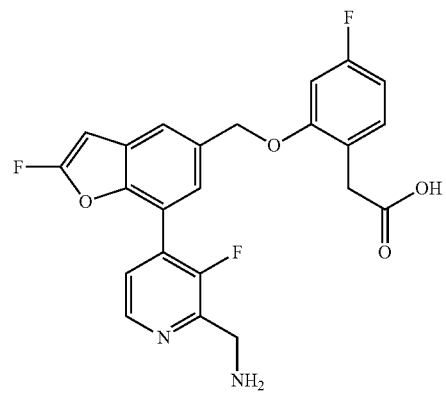 [SMILES: NCc1nccc(-c2cc(COc3cc(F)ccc3CC(=O)O)cc3cc(F)oc23)c1F]
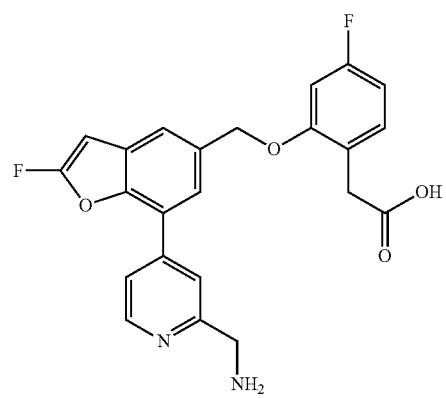 [SMILES: NCc1cc(-c2cc(COc3cc(F)ccc3CC(=O)O)cc3cc(F)oc23)ccn1]
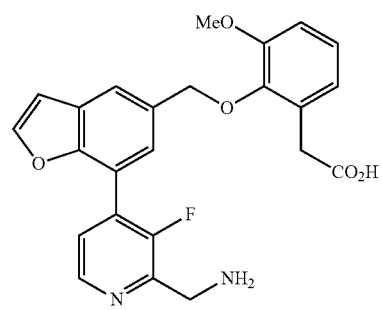 [SMILES: COc1cccc(CC(=O)O)c1OCc1cc(-c2ccnc(CN)c2F)c2occc2c1]
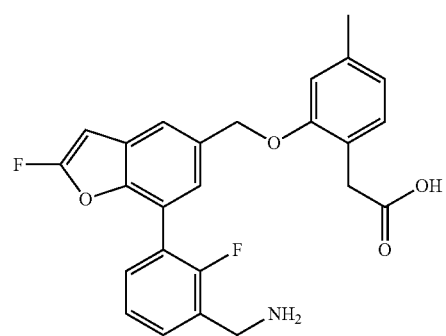 [SMILES: Cc1ccc(CC(=O)O)c(OCc2cc(-c3cccc(CN)c3F)c3oc(F)cc3c2)c1]

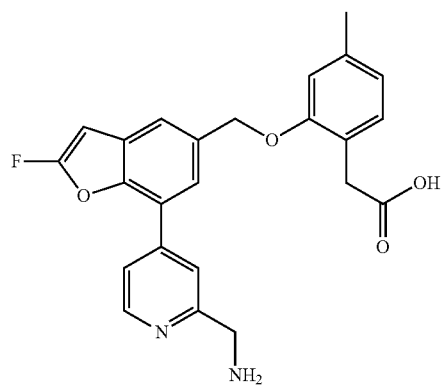 [SMILES: Cc1ccc(CC(=O)O)c(OCc2cc(-c3ccnc(CN)c3)c3oc(F)cc3c2)c1]
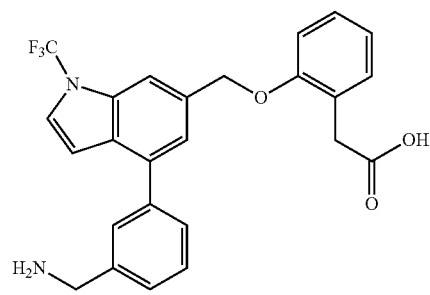 [SMILES: NCc1cccc(-c2cc(COc3ccccc3CC(=O)O)cc3c2ccn3C(F)(F)F)c1]
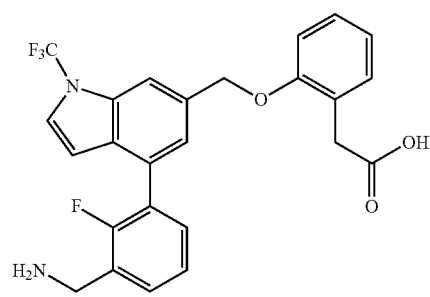 [SMILES: NCc1cccc(-c2cc(COc3ccccc3CC(=O)O)cc3c2ccn3C(F)(F)F)c1F]

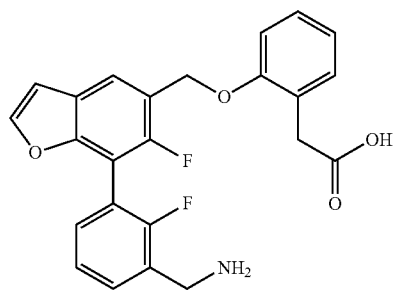 [SMILES: NCc1cccc(-c2c(F)c(COc3ccccc3CC(=O)O)cc3ccoc23)c1F]
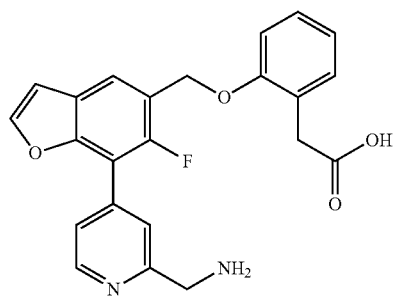 [SMILES: NCc1cc(-c2c(F)c(COc3ccccc3CC(=O)O)cc3ccoc23)ccn1]
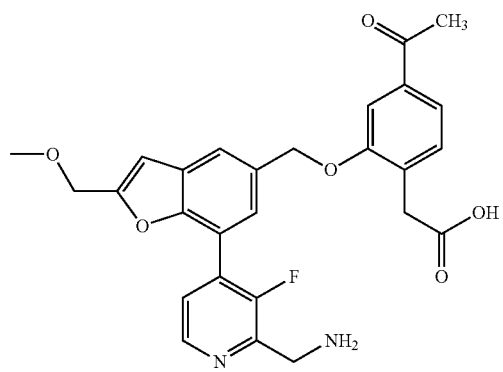 [SMILES: COCc1cc2cc(COc3cc(C(C)=O)ccc3CC(=O)O)cc(-c3ccnc(CN)c3F)c2o1]
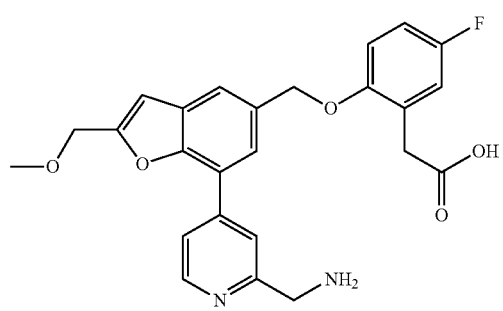 [SMILES: COCc1cc2cc(COc3ccc(F)cc3CC(=O)O)cc(-c3ccnc(CN)c3)c2o1]
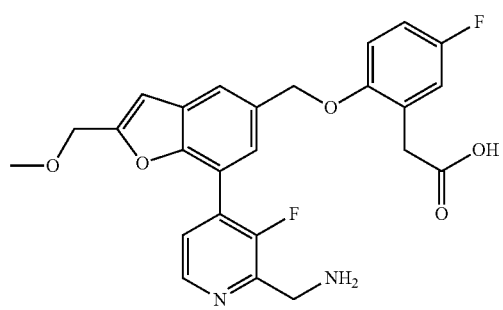 [SMILES: COCc1cc2cc(COc3ccc(F)cc3CC(=O)O)cc(-c3ccnc(CN)c3F)c2o1]

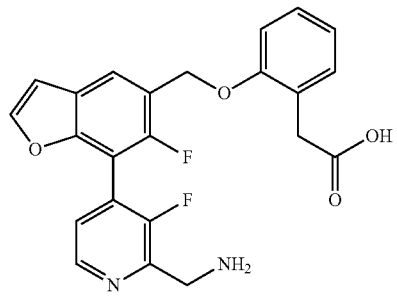 [SMILES: NCc1nccc(-c2c(F)c(COc3ccccc3CC(=O)O)cc3ccoc23)c1F]
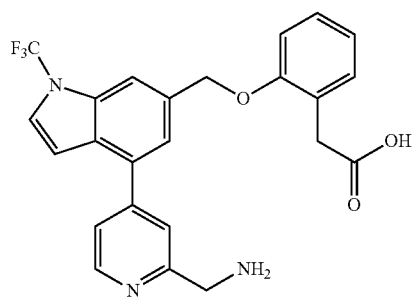 [SMILES: NCc1cc(-c2cc(COc3ccccc3CC(=O)O)cc3c2ccn3C(F)(F)F)ccn1]
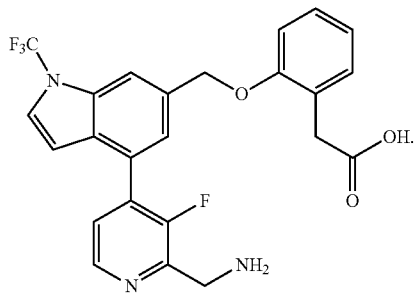 [SMILES: NCc1nccc(-c2cc(COc3ccccc3CC(=O)O)cc3c2ccn3C(F)(F)F)c1F]
In other aspects, the invention provides compounds having the structure of Formula (II-g), or a pharmaceutically acceptable salt or prodrug thereof:
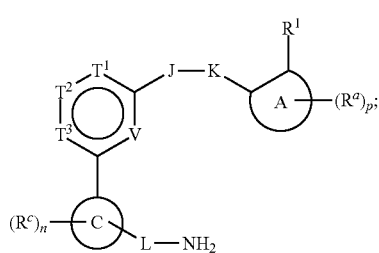
(II-g)
wherein:
ring A is aryl, heteroaryl, cycloalkyl, or heterocycloalkyl;
ring C is aryl or heteroaryl;
$R^a$, independently for each occurrence, is halogen, cyano, hydroxy, —$NH_2$, —NH(Ac), —NH(alkyl), —NH(cycloalkyl), —NH(heterocycloalkyl), —NH(aryl), —NH(heteroaryl), —N(alkyl)$_2$, —NHC(O)(alkyl), —CH(alkyl)NH$_2$, —CH(hydroxyalkyl)NH$_2$, —CH(haloalkyl)NH$_2$, —CH(cycloalkyl)NH$_2$, —CH(heterocycloalkyl)NH$_2$, —CH(aryl)NH$_2$, —CH(heteroaryl)NH$_2$, —CH$_2$NHC(O)(alkyl), —C(O)NH$_2$, —C(O)(alkyl), —SO$_2$NH$_2$, —SO$_2$(cycloalkyl), —SO$_2$(heterocycloalkyl), —SO$_2$(alkyl), —SO$_2$(aryl), or —SO$_2$(heteroaryl); or is selected from the group consisting of substituted or unsubstituted aryl, heteroaryl, arylalkyl, heteroarylalkyl, cycloalkyl, heterocycloalkyl, alkoxy, alkyl, (cycloalkyl)alkyl, (heterocycloalkyl)alkyl, hydroxyalkyl, aminoalkyl, and haloalkyl;

T$^1$ is N, CH, NR$^{T1}$, or CR$^{T1}$;

T$^2$ is NR$^{T2}$ or CR$^{T2}$;

T$^3$ is N, CH, NR$^{T3}$, or CR$^{T3}$;

wherein:
(a) T$^1$ is CR$^{T1}$ or NR$^{T1}$, wherein R$^{T1}$ and R$^{T2}$, taken together with the intervening atoms, form an optionally substituted cycloalkyl, aryl, or heteroaryl ring; and T$^3$ is N or CH; or
(b) T$^3$ is CR$^{T3}$ or NR$^{T3}$; wherein R$^{T3}$ and R$^{T2}$, taken together with the intervening atoms, form an optionally substituted heteroaryl ring; and
T$^1$ is N or CH; and at least one of (a) T$^2$ is NR$^{T2}$, (b) T$^3$ is N, or (c) T$^1$ is NR$^{T1}$;

R$^1$ is selected from the group consisting of —NH$_2$, —COOH, —CH$_2$COOH, —CH(NH(CO)(alkyl))COOH, —CH(NH(CO)(arylalkyl))COOH, —CH(NH(CO)(cycloalkyl))COOH, —CH(NH(CO)(aryl substituted cycloalkyl))COOH, —CH(NH(CO)(heteroaryl substituted cycloalkyl))COOH, —CH(S(alkyl))COOH, —CO(NH)CH$_2$(substituted or unsubstituted aryl), —CO(NH)CH$_2$(substituted or unsubstituted heteroaryl), —CO(NH)(substituted or unsubstituted aryl), —CO(NH)(substituted or unsubstituted heteroaryl), and —CH$_2$(tetrazolyl);

n is 0, 1, 2, 3, or 4;

p is 0, 1, 2, 3, or 4;

J is —C(O)—, —NH—, —CH$_2$—, —O—, —S—, —S(O)—, —SO$_2$—, —N(alkyl)-, —CH(alkyl)-, —CH(cycloalkyl)-, —N((C(O)O)arylalkyl)-, —N((C(O)O)heteroarylalkyl)-, or —N(C(O)arylalkyl)-;

K is —C(O)—, —NH—, —CH$_2$—, —O—, —S—, —S(O)—, —SO$_2$—, —N(alkyl)-, —CH(alkyl)-, —CH(cycloalkyl)-, —N((C(O)O)arylalkyl)-, —N((C(O)O)heteroarylalkyl)-, or —N(C(O)arylalkyl)-;

R$^c$, independently for each occurrence, is selected from the group consisting of halogen, —OH, —NR$^j$R$^k$, alkoxy, alkyl, cycloalkyl, and heterocycloalkyl;

L is selected from the group consisting of a bond, —CH$_2$—, —CH$_2$CH$_2$—, —CHR$^2$—, —CF$_2$—, —CFR$^2$—, —C(O)—, —C(=NR$^L$)—, —C(=CHR$^L$)—, —S(O)$_2$—, and —S(O)—;

wherein R$^L$ is H or alkyl;

or wherein R$^L$ and an occurrence of R$^c$ taken together with the intervening atoms form a substituted or unsubstituted heteroaryl ring;

R$^2$ is alkyl, cycloalkyl, hydroxyalkyl, or haloalkyl;

V is N or CH; and the stereochemical configuration at any chiral center is R, S, or a mixture of R and S.

In other aspects, the invention provides compounds having the structure of Formula (II), or a pharmaceutically acceptable salt or prodrug thereof:

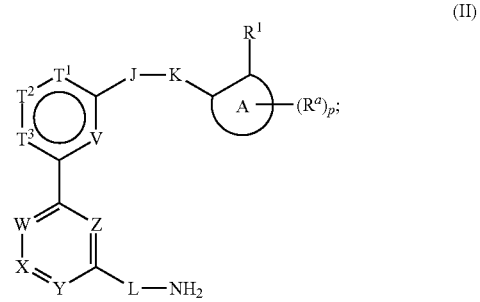

(II)

wherein:

ring

is aryl, heteroaryl, cycloalkyl, or heterocycloalkyl;

R$^a$, independently for each occurrence, is selected from the group consisting of halogen, cyano, hydroxy, —NH$_2$, —NH(Ac), —NH(alkyl), —N(alkyl)$_2$, —NHC(O)(alkyl), —CH$_2$NHC(O)(alkyl), —C(O)NH$_2$, —C(O)(alkyl), optionally substituted aryl, optionally substituted heteroaryl, cycloalkyl, alkoxy, alkyl, (cycloalkyl)alkyl, hydroxyalkyl, aminoalkyl, and haloalkyl;

T$^1$ is N, CH, NR$^{T1}$, or CR$^{T1}$;

T$^2$ is NR$^{T2}$ or CR$^{T2}$;

T$^3$ is N, CH, NR$^{T3}$, or CR$^{T3}$;

wherein:
(a) T$^1$ is CR$^{T1}$ or NR$^{T1}$, wherein R$^{T1}$ and R$^{T2}$, taken together with the intervening atoms, form an optionally substituted cycloalkyl, aryl, or heteroaryl ring; and
T$^3$ is N or CH; or
(b) T$^3$ is CR$^{T3}$ or NR$^{T3}$; wherein R$^{T3}$ and R$^{T2}$, taken together with the intervening atoms, form an optionally substituted heteroaryl ring; and
T$^1$ is N or CH; and at least one of (a) T$^2$ is NR$^{T2}$, (b) T$^3$ is N, or (c) T$^1$ is NR$^{T1}$;

R$^1$ is selected from the group consisting of —NH$_2$, —CH$_2$COOH, —CH(NH(CO)(alkyl))COOH, —CH(NH(CO)(cycloalkyl))COOH, —CO(NH)CH$_2$aryl, —CO(NH)CH$_2$heteroaryl, —CO(NH)aryl, and —CO(NH)heteroaryl;

p is 0, 1, or 2;

J is —C(O)—, —NH—, —CH$_2$—, —O—, —S—, —S(O)—, —SO$_2$—, —N(alkyl)-, or —CH(alkyl)-;

K is —C(O)—, —NH—, —O—, —CH$_2$—, —S—, —S(O)—, —SO$_2$—, —N(alkyl)-, or —CH(alkyl)-;

wherein at least one of J and K is —C(O)—, —CH$_2$—, or —CH(alkyl)-;

W is N, CH, or CR$^c$;

X is N, CH, or CR$^c$;

Y is N, CH, or CR$^c$;

Z is N, CH, or CR$^c$;

R$^c$, independently for each occurrence, is selected from the group consisting of halogen, —OH, —NR$^j$R$^k$, alkoxy, and alkyl;

L is selected from the group consisting of a bond, —CH₂—, —CH₂CH₂—, —CHR²—, —CF₂—, —CFR²—, —C(O)—, —C(=NR^L)—, and —C(=CHR^L)—;

wherein R^L is H or alkyl;

or wherein R^L and an occurrence of R^c taken together with the intervening atoms form a substituted or unsubstituted heteroaryl ring;

R² is alkyl, hydroxyalkyl, or haloalkyl;

V is N or CH; and the stereochemical configuration at any chiral center is R, S, or a mixture of R and S.

In certain embodiments, ring $$\text{A}$$

is phenyl, thiophenyl, furyl, pyrazole, or pyridinyl, preferably phenyl.

In certain embodiments, the compound of formula (II) has the structure of formula (IIa):

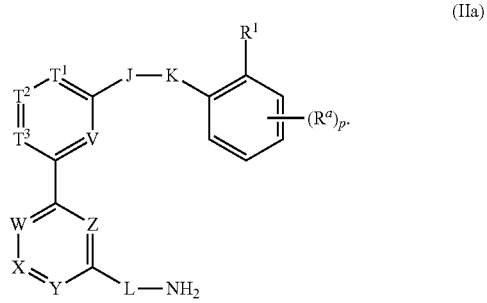

(IIa)

In certain embodiments of formula (II) or (IIa), p is 1. In certain such embodiments, R^a is alkyl or alkoxy.

In certain embodiments, p is 0.

In certain embodiments, R¹ is —CH₂COOH.

In some embodiments, -J-K— is selected from the group consisting of —C(O)—NH—, —NH—C(O)—, and —CH₂O—, preferably —CH₂O—.

In certain embodiments, U is CH. In further embodiments, V is CH.

In certain embodiments, each of W, X, Y, and Z is CH.

In certain embodiments, at least one of W, X, Y, and Z is CR^c. For example, Z may be CR^c and/or Y may be CR^c. In certain such embodiments, R^c is halogen, e.g., fluoride.

Alternatively, at least one of W, X, Y, and Z is N. For example, Z may be N. Alternatively, Y may be N.

In some embodiments, L is —CH₂—.

In certain embodiments of the compound of formula (II) or (IIa), T¹ is CR^{T1}; and R^{T1} and R^{T2}, taken together with the intervening atoms, form an optionally substituted heteroaryl ring, such as pyrrole, imidazole, or 1,2,4-triazole.

In alternative embodiments of the compound of formula (II) or (IIa), T³ is CR^{T3}; and R^{T3} and R^{T2}, taken together with the intervening atoms, form an optionally substituted heteroaryl ring, such as pyrrole, imidazole, 1,2,4-triazole, or pyridine.

In certain embodiments, the compound of formula (II) is selected from the following table of compounds, and pharmaceutically acceptable salts and prodrugs thereof:

| 251 -continued | 252 -continued |
|---|---|
| 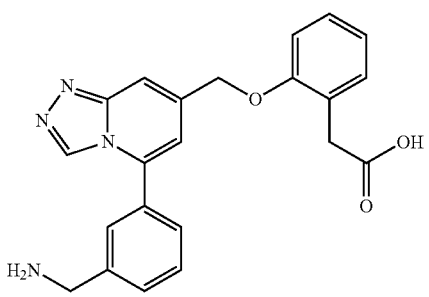 [SMILES: NCc1cccc(-c2cc(COc3ccccc3CC(=O)O)cc3nncn23)c1] | 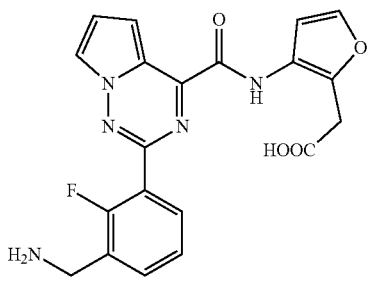 [SMILES: NCc1cccc(-c2nc(C(=O)Nc3ccoc3CC(=O)O)c3cccn3n2)c1F] |
| | 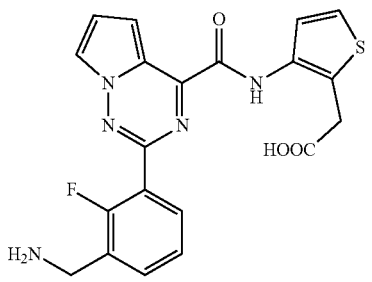 [SMILES: NCc1cccc(-c2nc(C(=O)Nc3ccsc3CC(=O)O)c3cccn3n2)c1F] |
| 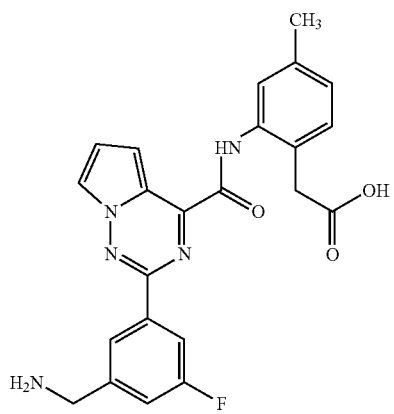 [SMILES: Cc1ccc(CC(=O)O)c(NC(=O)c2nc(-c3cc(F)cc(CN)c3)nn3cccc23)c1] (spans) | 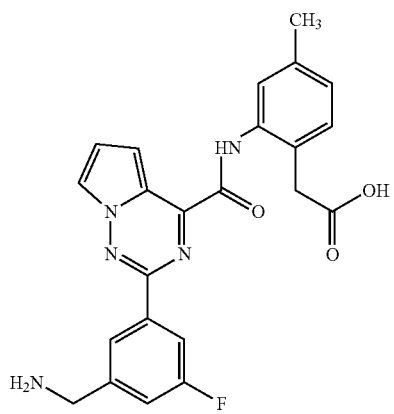 [SMILES: Cc1ccc(CC(=O)O)c(NC(=O)c2nc(-c3cc(F)cc(CN)c3)nn3cccc23)c1] |
| | 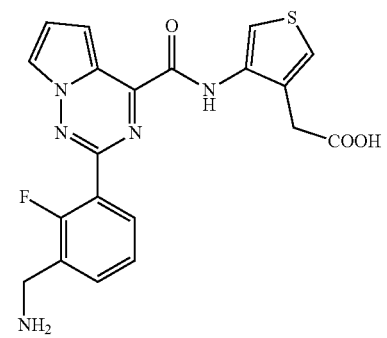 [SMILES: NCc1cccc(-c2nc(C(=O)Nc3cscc3CC(=O)O)c3cccn3n2)c1F] |
| | 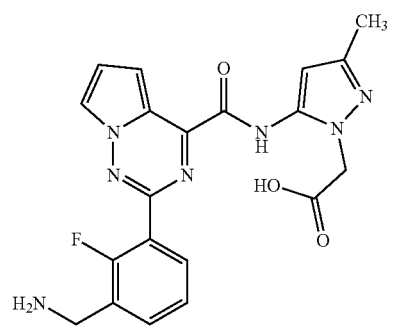 [SMILES: Cc1cc(NC(=O)c2nc(-c3cccc(CN)c3F)nn3cccc23)n(CC(=O)O)n1] |

253
-continued
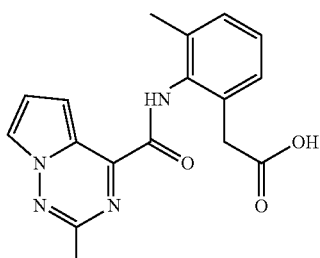
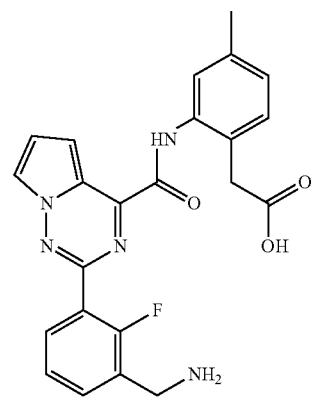 [SMILES: Cc1ccc(CC(=O)O)c(NC(=O)c2nc(-c3cccc(CN)c3F)nn3cccc23)c1]
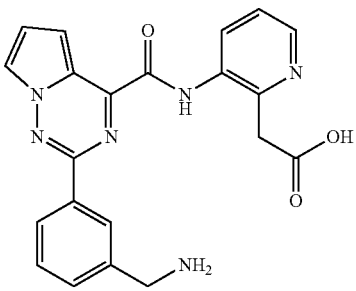 [SMILES: NCc1cccc(-c2nc(C(=O)Nc3cccnc3CC(=O)O)c3cccn3n2)c1]
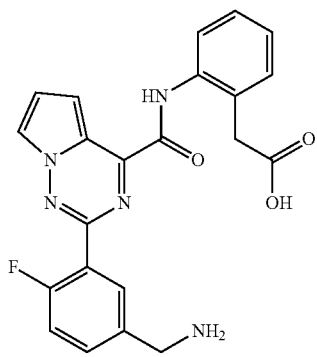 [SMILES: NCc1ccc(F)c(-c2nc(C(=O)Nc3ccccc3CC(=O)O)c3cccn3n2)c1]
254
-continued
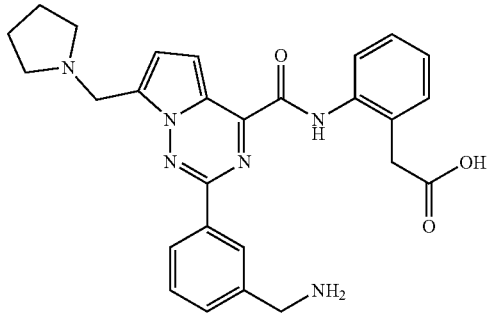 [SMILES: NCc1cccc(-c2nc(C(=O)Nc3ccccc3CC(=O)O)c3ccc(CN4CCCC4)n3n2)c1]
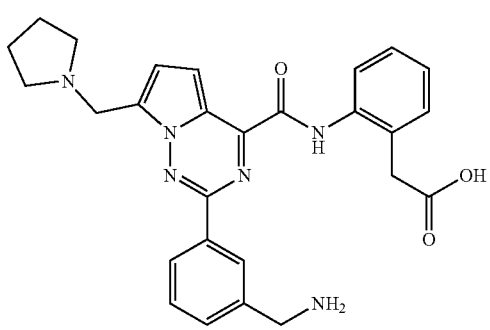 [SMILES: NCc1cccc(-c2nc(C(=O)Nc3ccccc3CC(=O)O)c3ccc(CN4CCCC4)n3n2)c1]
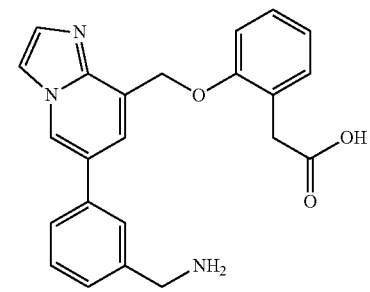 [SMILES: NCc1cccc(-c2cc(COc3ccccc3CC(=O)O)c3nccn3c2)c1]
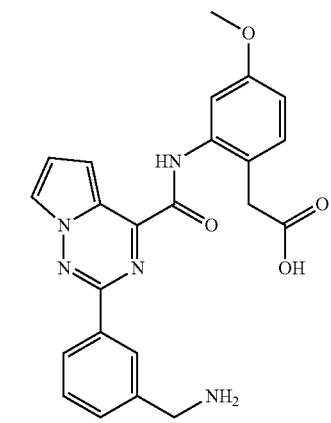 [SMILES: COc1ccc(CC(=O)O)c(NC(=O)c2nc(-c3cccc(CN)c3)nn3cccc23)c1]

255
-continued
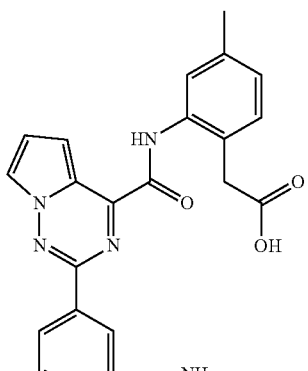
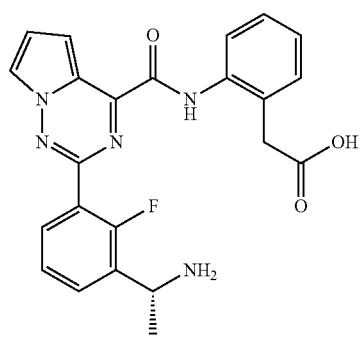 [SMILES: C[C@@H](N)c1cccc(-c2nc(C(=O)Nc3ccccc3CC(=O)O)c3cccn3n2)c1F]
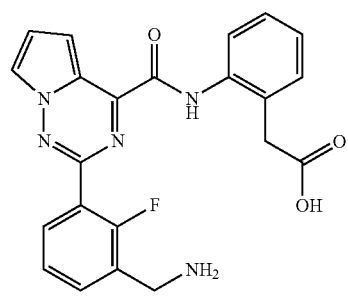 [SMILES: NCc1cccc(-c2nc(C(=O)Nc3ccccc3CC(=O)O)c3cccn3n2)c1F]
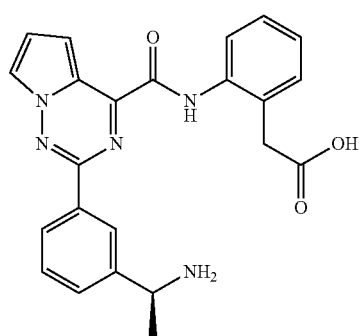 [SMILES: C[C@H](N)c1cccc(-c2nc(C(=O)Nc3ccccc3CC(=O)O)c3cccn3n2)c1]
256
-continued
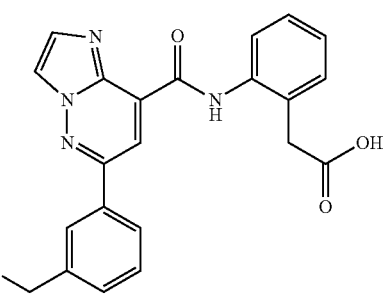
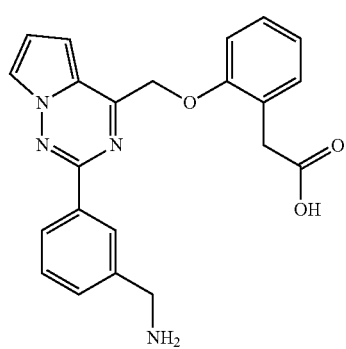 [SMILES: NCc1cccc(-c2nc(COc3ccccc3CC(=O)O)c3cccn3n2)c1]
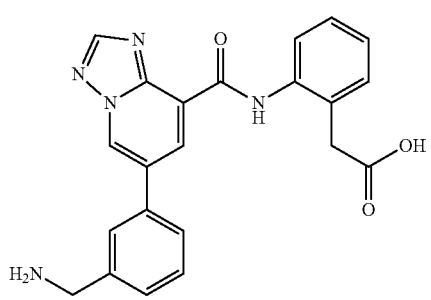 [SMILES: NCc1cccc(-c2cc(C(=O)Nc3ccccc3CC(=O)O)c3ncnn3c2)c1]
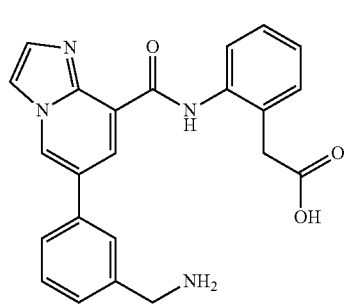 [SMILES: NCc1cccc(-c2cc(C(=O)Nc3ccccc3CC(=O)O)c3nccn3c2)c1]

-continued

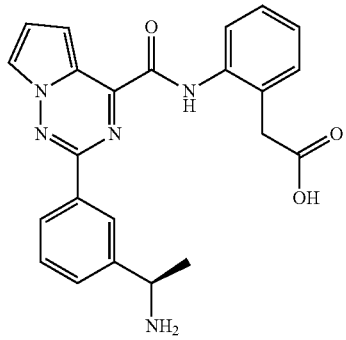 [SMILES: C[C@@H](N)c1cccc(-c2nc(C(=O)Nc3ccccc3CC(=O)O)c3cccn3n2)c1]

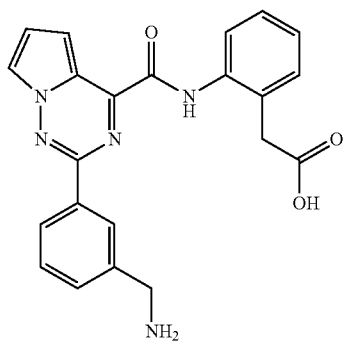 [SMILES: NCc1cccc(-c2nc(C(=O)Nc3ccccc3CC(=O)O)c3cccn3n2)c1]

Pharmaceutical Compositions

The invention provides pharmaceutical compositions, each comprising one or more compounds of the invention, or pharmaceutically acceptable salts or prodrugs thereof, and a pharmaceutically acceptable carrier. In certain embodiments, the pharmaceutical composition comprises a compound of the invention, or a pharmaceutically acceptable salt or prodrug thereof, and a pharmaceutically acceptable carrier. In certain embodiments, the pharmaceutical composition comprises a plurality of compounds of the invention, which may include pharmaceutically acceptable salts and/or prodrugs thereof, and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of a disease or condition characterized by aberrant complement system activity.

Pharmaceutical compositions of the invention can be prepared by combining one or more compounds of the invention with a pharmaceutically acceptable carrier and, optionally, one or more additional pharmaceutically active agents.

Methods of Use

The present invention provides compounds, and pharmaceutically acceptable salts and prodrugs thereof, that are useful for treating or preventing a disease or condition characterized by aberrant complement system activity.

In certain aspects, the invention provides a compound of the invention, or a pharmaceutically acceptable salt or prodrug thereof, for use as a medicament.

In certain aspects, the invention provides methods of treating or preventing a disease or condition characterized by aberrant complement system activity. The method includes the step of administering to a subject in need thereof a therapeutically effective amount of a compound of the invention, or a pharmaceutically acceptable salt or prodrug thereof, thereby treating or preventing the disease or condition characterized by aberrant complement system activity. By reducing complement system activity in the subject, the disease or condition characterized by aberrant complement system activity is treated.

Alternatively, in certain aspects, the invention provides a compound of the invention, or a pharmaceutically acceptable salt or prodrug thereof, for treatment of a disease or condition characterized by aberrant complement system activity.

Alternatively, in certain aspects, the invention provides the use of a compound of the invention, or a pharmaceutically acceptable salt or prodrug thereof, for the manufacture of a medicament for use in treatment of a disease or condition characterized by aberrant complement system activity.

As used herein, a "disease or condition characterized by aberrant complement system activity" refers to any disease or condition in which it is desirable to reduce complement system activity. For example, it may be desirable to reduce complement system activity in the setting of inappropriate activation or hyperactivation of the complement system.

In certain embodiments, the disease or condition characterized by aberrant complement system activity is an immunological disorder.

In certain embodiments, the disease or condition characterized by aberrant complement system activity is a disease of the central nervous system.

In certain embodiments, the disease or condition characterized by aberrant complement system activity is a renal disease.

In certain embodiments, the disease or condition characterized by aberrant complement system activity is a cardiovascular disease.

In certain embodiments, the disease or condition characterized by aberrant complement system activity is a neurodegenerative disease or neurological disease In certain embodiments, the disease or condition characterized by aberrant complement system activity is selected from the group consisting of paroxysmal nocturnal hemoglobinuria, atypical hemolytic uremic syndrome, organ transplant rejection, myasthenia gravis, neuromyelitis optica, membranoproliferative glomerulonephritis, dense-deposit disease, cold agglutinin disease, and catastrophic antiphospholipid syndrome.

In certain embodiments, the disease or condition is paroxysmal nocturnal hemoglobinuria.

In certain embodiments, the disease or condition is atypical hemolytic uremic syndrome.

In certain embodiments, the disease or condition is organ transplant rejection.

In certain embodiments, the disease or condition is myasthenia gravis.

In certain embodiments, the disease or condition is neuromyelitis optica.

In certain embodiments, the disease or condition is membranoproliferative glomerulonephritis.

In certain embodiments, the disease or condition is dense-deposit disease.

In certain embodiments, the disease or condition is cold agglutinin disease.

In certain embodiments, the disease or condition is catastrophic antiphospholipid syndrome.

In other embodiments, the disease or condition characterized by aberrant complement system activity is adult respiratory distress syndrome, myocardial infarct, lung inflammation, hyperacute rejection (transplantation rejection), sepsis, cardiopulmonary bypass, burns, asthma, restenosis, multiple organ dysfunction syndrome, Guillain-Barre syndrome, hemorrhagic shock, paroxysmal nocturnal hemoglobinuria, glomerulonephritis, systemic lupus erythematosus, rheumatoid arthritis, infertility, Alzheimer's disease, organ rejection (transplantation), myasthenia gravis, multiple sclerosis, platelet storage, or hemodialysis.

In other embodiments, the disease or condition characterized by aberrant complement system activity is selected from the group consisting of antineutrophil cytoplasmic antibody (ANCA)-associated vasculitis (AAV), warm autoimmune hemolytic anemia, IgA nephropathy, C3 glomerulonephritis, and focal segmental glomerulosclerosis.

In certain embodiments, the disease or condition characterized by aberrant complement system activity is a hematological disorder.

In other embodiments, the disease or condition characterized by aberrant complement system activity is an ocular disorder or an eye disorder.

In certain embodiments, the disease or condition characterized by aberrant complement system activity is macular degeneration, age-related macular degeneration (AMD), macular edema, diabetic macular edema, choroidal neovascularization (CNV), uveitis, Behcet's uveitis, proliferative diabetic retinopathy, non-proliferative diabetic retinopathy, glaucoma, hypertensive retinopathy, a corneal neovascularization disease, post-corneal transplant rejection, a corneal dystrophic disease, an autoimmune dry eye disease, Stevens-Johnson syndrome, Sjogren's syndrome, an environmental dry eye disease, Fuchs' endothelial dystrophy, retinal vein occlusion, or post-operative inflammation.

Formulations, Routes of Administration, and Dosing

The compounds of the invention, and pharmaceutically acceptable salts or prodrugs thereof, can be formulated as pharmaceutical compositions and administered to a mammalian host, such as a human patient, in a variety of forms adapted to the chosen route of administration, e.g., orally or parenterally, by intravenous, intraperitoneal, intramuscular, topical, or subcutaneous routes. Additional routes of administration are also contemplated by the invention.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known in the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the compounds of the invention can be determined, at least initially, by comparing their in vitro activity and in vivo activity in animal models. Methods for the extrapolation of effective dosages in mice, and other animals, to humans are known in the art; for example, see U.S. Pat. No. 4,938,949 (incorporated herein by reference).

The amount of the compound, or pharmaceutically acceptable salt or prodrug thereof, required for use in treatment will vary not only with the particular compound, salt, or prodrug selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram of body weight per day, from about of 10 to about 60 mg/kg of body weight per day, or from about 15 to about 50 mg/kg of body weight per day.

Compounds of the invention, or pharmaceutically acceptable salts or prodrugs thereof, can be conveniently formulated in unit dosage form; for example, containing 5 to 1000 mg, 10 to 750 mg, or 50 to 500 mg of active ingredient per unit dosage form. In one embodiment, the invention provides a composition comprising a compound of the invention, or pharmaceutically acceptable salts or prodrugs thereof, formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations.

Compounds of the invention, or pharmaceutically acceptable salts or prodrugs thereof, can also be administered in combination with other therapeutic agents, for example, other agents that are useful for treating or preventing ischemia, blood loss, or reperfusion injury. In certain embodiments, compounds of the invention, and pharmaceutically acceptable salts or prodrugs thereof, can also be administered in combination with one or more other therapeutic agents that are useful for treating or preventing an ocular disorder or eye disorder.

Other delivery systems can include time-release, delayed release, or sustained release delivery systems such as are well-known in the art. Such systems can avoid repeated administrations of the active compound, increasing convenience to the subject and the physician. Many types of release delivery systems are available and known to those of ordinary skill in the art. Use of a long-term sustained release implant may be desirable. Long-term release, as used herein, means that the delivery system or is implant constructed and arranged to deliver therapeutic levels of the active ingredient for at least 30 days, and preferably 60 days.

In certain embodiments, a compound of the invention is formulated for intraocular administration, for example direct injection or insertion within or in association with an intraocular medical device. In certain embodiments, a compound of the invention is formulated as an ophthalmic solution. In certain embodiments, a compound of the invention can be administered via ocular delivery, for example, by local ocular administration, including topical, intravitreal, periocular, transscleral, retrobulbar, juxtascleral, suprachoroidal, or sub-tenon administration. A compound of the invention can be administered via ocular delivery either alone or in combination with one or more additional therapeutic agents.

The compounds of the invention may be formulated for depositing into a medical device, which may include any of a variety of conventional grafts, stents, including stent grafts, catheters, balloons, baskets, or other device that can be deployed or permanently implanted within a body lumen. As a particular example, it would be desirable to have devices and methods which can deliver compounds of the invention to the region of a body which has been treated by interventional technique.

In exemplary embodiment, a compound of the invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz), U.S. Pat. No. 5,419,760 (Narciso, Jr.), U.S. Pat. No. 5,429,634 (Narciso, Jr.), and in International Patent Application Nos. WO 91/12779 (Medtronic, Inc.) and WO 90/13332 (Cedars-Sanai Medical Center), for example.

The term "deposited" means that the compound is coated, adsorbed, placed, or otherwise incorporated into the device by methods known in the art. For example, the compound may be embedded and released from within ("matrix type") or surrounded by and released through ("reservoir type") polymer materials that coat or span the medical device. In the latter example, the compound may be entrapped within the polymer materials or coupled to the polymer materials using one or more the techniques for generating such materials known in the art. In other formulations, the compound may be linked to the surface of the medical device without the need for a coating, for example by means of detachable bonds, and release with time or can be removed by active mechanical or chemical processes. In other formulations, the compound may be in a permanently immobilized form that presents the compound at the implantation site.

In certain embodiments, the compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but frequently a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D, L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable polymers known in the art. Also, biostable polymers with a relatively low chronic tissue response such as polyurethanes, silicones, and polyesters could be used, and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In certain embodiments of the invention, the compound of the invention is coupled to a polymer or semipermeable polymer matrix that is formed as a stent or stent-graft device.

Typically, polymers are applied to the surface of an implantable device by spin coating, dipping, or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In certain embodiments of the invention, the compound is formulated for release from the polymer coating into the environment in which the medical device is placed. Preferably, the compound is released in a controlled manner over an extended time frame (e.g., months) using at least one of several well-known techniques involving polymer carriers or layers to control elution. Some of these techniques are described in U.S. Patent Application 2004/0243225A1, the entire disclosure of which is incorporated herein in its entirety.

Moreover, as described for example in U.S. Pat. No. 6,770,729, which is incorporated herein in its entirety, the reagents and reaction conditions of the polymer compositions can be manipulated so that the release of the compound from the polymer coating can be controlled. For example, the diffusion coefficient of the one or more polymer coatings can be modulated to control the release of the compound from the polymer coating. In a variation on this theme, the diffusion coefficient of the one or more polymer coatings can be controlled to modulate the ability of an analyte that is present in the environment in which the medical device is placed (e.g., an analyte that facilitates the breakdown or hydrolysis of some portion of the polymer) to access one or more components within the polymer composition (and for example, thereby modulate the release of the compound from the polymer coating). Yet another embodiment of the invention includes a device having a plurality of polymer coatings, each having a plurality of diffusion coefficients. In such embodiments of the invention, the release of the compound from the polymer coating can be modulated by the plurality of polymer coatings.

In yet another embodiment of the invention, the release of the compound from the polymer coating is controlled by modulating one or more of the properties of the polymer composition, such as the presence of one or more endogenous or exogenous compounds, or alternatively, the pH of the polymer composition. For example, certain polymer compositions can be designed to release a compound in response to a decrease in the pH of the polymer composition.

Kits

The invention also provides a kit, comprising a compound of the invention, or a pharmaceutically acceptable salt or prodrug thereof, at least one other therapeutic agent, packaging material, and instructions for administering the compound of the invention or the pharmaceutically acceptable salt or prodrug thereof and the other therapeutic agent or agents to a mammal to treat or prevent a disease or condition characterized by aberrant complement activity. In one embodiment, the mammal is a human.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXAMPLES

Having now described the present invention in detail, the same will be more clearly understood by reference to the following examples, which are included herewith for purposes of illustration only and are not intended to be limiting of the invention.

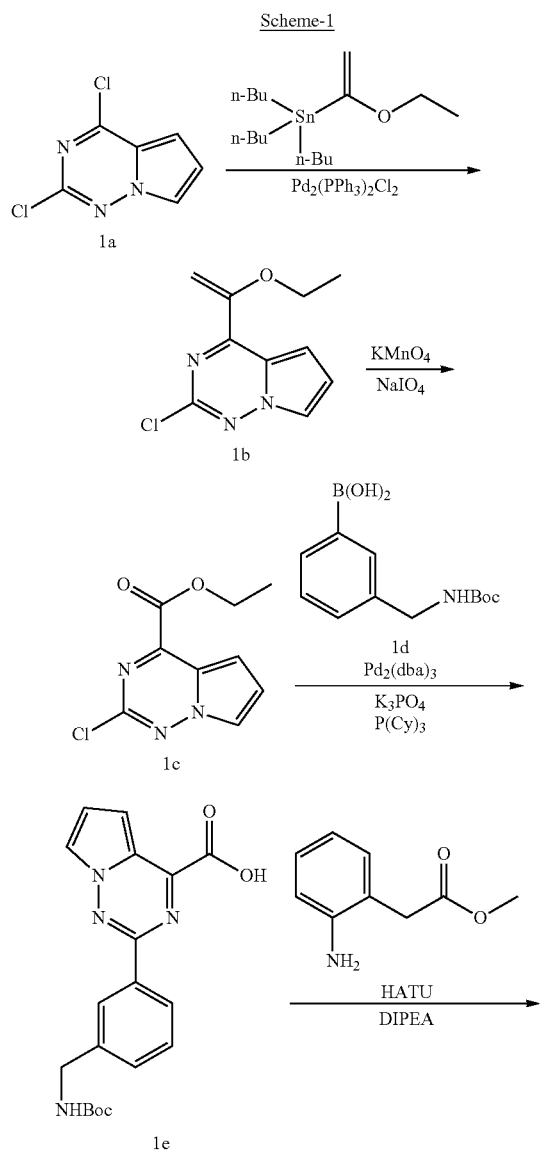

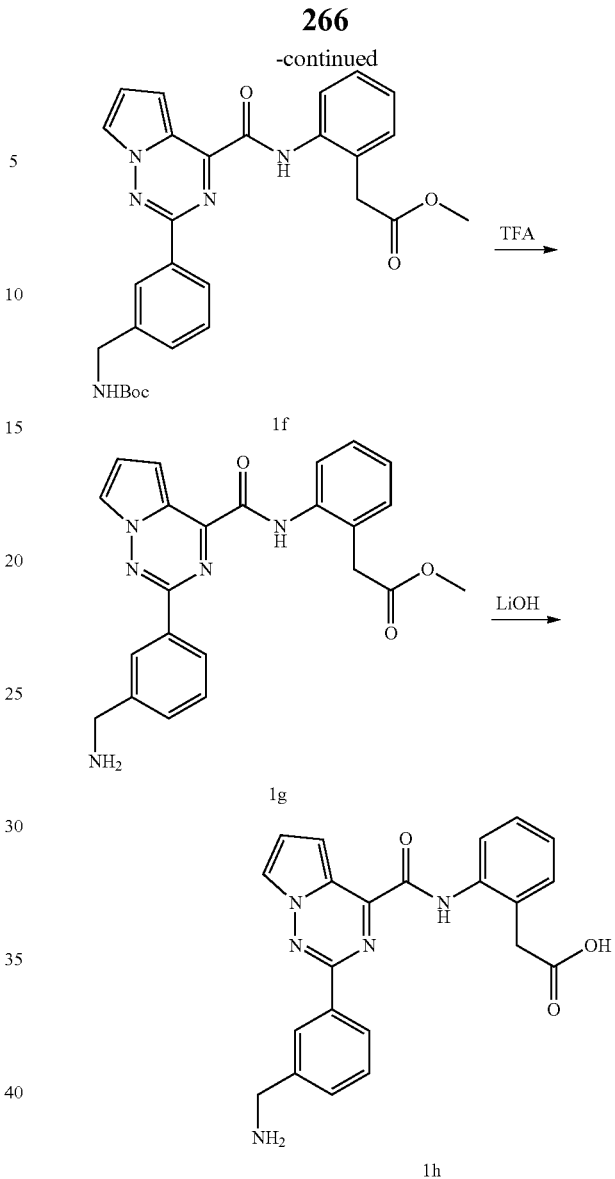

Preparation of 2-(2-(2-(3-(aminomethyl)phenyl) pyrrolo[2,1-f][1,2,4]triazine-4-carboxamido)phenyl) acetic Acid (1h)

Step-1: Preparation of 2-chloro-4-(1-ethoxyvinyl) pyrrolo[2,1-f][1,2,4]triazine (1b)

To a solution of 2,4-dichloropyrrolo[2,1-f][1,2,4]triazine (1a) (3 g, 15.96 mmol, CAS #918538-05-3) in DMF (50 mL) under Ar atmosphere was added 1-ethoxyvinyltri-n-butyltin (7.07 mL, 20.74 mmol, CAS #97674-02-7) and bis(triphenylphosphine)Palladium(II)chloride (0.56 g, 0.8 mmol). The mixture was heated with stirring at 100° C. for 30 min, cooled to room temp and diluted with EtOAc (150 mL). The reaction mixture was washed with water (50 mL), brine (30 mL), dried, filtered and concentrated in vacuum to dryness. The residue obtained was purified by flash column chromatography [silica (24 g), eluting with EtOAc in hexane from 0-50%] to afford 2-chloro-4-(1-ethoxyvinyl)pyrrolo[2,1-f][1,2,4]triazine (1b) (2.2 g, 62% yield) as an orange oil; $^1$H NMR (300 MHz, DMSO-$d_6$) δ 8.23 (dd, J=2.6, 1.4 Hz, 1H), 7.34 (dd, J=4.7, 1.4 Hz, 1H), 7.11 (dd, J=4.7, 2.6 Hz, 1H), 5.64 (d, J=2.4 Hz, 1H), 4.88 (d, J=2.4 Hz, 1H), 4.03 (q, J=7.0 Hz, 2H), 1.44 (t, J=7.0 Hz, 3H).

Step-2: Preparation of Ethyl 2-chloropyrrolo[2,1-f][1,2,4]triazine-4-carboxylate (1c)

Sodium periodate (1.17 g, 5.47 mmol) was suspended in water (9 mL) and sonicated until a clear solution (pH ~4) was obtained. This solution was added to a solution of 2-chloro-4-(1-ethoxyvinyl)pyrrolo[2,1-f][1,2,4]triazine (1b) (612 mg, 2.74 mmol) in 1,4-dioxane (40 mL). $KMnO_4$ (43 mg, 0.27 mmol) was added and the reaction mixture was stirred at room temp for 2 h. The pH of reaction mixture was adjusted between 7-8 using saturated aqueous $K_2CO_3$ solution. The precipitate was filtered off, rinsed thoroughly with DCM (4×20 mL). The combined filtrates were washed with water, brine, dried, filtered and concentrated in vacuum to dryness. The residue obtained was purified by flash column chromatography [silica (12 g), eluting with EtOAc in hexane from 0-60%] to afford ethyl 2-chloropyrrolo[2,1-f][1,2,4]triazine-4-carboxylate (1c) (212 mg, 34% yield) as a yellow solid; $^1$H NMR (300 MHz, DMSO-$d_6$) δ 8.43 (dd, J=2.5, 1.3 Hz, 1H), 7.45 (dd, J=4.8, 1.3 Hz, 1H), 7.30 (dd, J=4.8, 2.5 Hz, 1H), 4.47 (q, J=7.1 Hz, 2H), 1.39 (t, J=7.1 Hz, 3H).

Step-3: Preparation of 2-(3-(((tert-butoxycarbonyl)amino)methyl)phenyl)pyrrolo[2,1-f][1,2,4]triazine-4-carboxylic Acid (1e)

To a solution of ethyl 2-chloropyrrolo[2,1-f][1,2,4]triazine-4-carboxylate (1c) (150 mg, 0.67 mmol) in dioxane (6 mL) was added 3-((tert-butoxycarbonylamino)methyl)phenylboronic acid (1d) (192 mg, 0.77 mmol; CAS #199609-62-6), potassium triphosphate (282 mg, 1.33 mmol) in water (1 mL), tricyclohexylphosphine (56 mg, 0.2 mmol) and $Pd_2(dba)_3$ (61 mg, 0.07 mmol). The mixture was degassed and filled with Ar, then heated at 125° C. for 30 min. The mixture was cooled to room temperature, diluted with EtOAc, washed with water, brine, filtered and concentrated in vacuum to dryness. The residue obtained was purified by flash column chromatography [silica (12 g), eluting with MeOH in DCM from 0-30%] to afford 2-(3-(((tert-butoxycarbonyl)amino)methyl)phenyl)pyrrolo[2,1-f][1,2,4]triazine-4-carboxylic acid (1e) (150 mg, 61% yield) as a yellow solid; $^1$H NMR (300 MHz, DMSO-$d_6$) δ 8.21-8.08 (m, 3H), 7.53 (dd, J=11.2, 5.0 Hz, 1H), 7.46 (d, J=7.6 Hz, 1H), 7.38 (d, J=7.8 Hz, 1H), 7.14-7.08 (m, 1H), 7.06-7.00 (m, 1H), 4.22 (d, J=6.2 Hz, 2H), 1.41 (s, 9H).

Step-4: Preparation of methyl 2-(2-(2-(3-(((tert-butoxycarbonyl)amino)methyl)phenyl)pyrrolo[2,1-f][1,2,4]triazine-4-carboxamido)phenyl)acetate (1f)

To a solution of 2-(3-(((tert-butoxycarbonyl)amino)methyl)phenyl)pyrrolo[2,1-f][1,2,4]triazine-4-carboxylic acid (1e) (95 mg, 0.26 mmol) in DMF (8 mL) was added methyl 2-(2-aminophenyl)acetate (51 mg, 0.31 mmol, CAS #35613-44-6), DIPEA (0.14 mL, 0.77 mmol) and HATU (118 mg, 0.31 mmol). The resulting mixture was stirred at RT overnight, diluted with EtOAc (60 mL), washed with water (3×s), brine, filtered and concentrated in vacuum to dryness. The residue obtained was purified by flash column chromatography [silica (12 g), eluting with 0-60% EtOAc/MeOH (9:1) in hexane from 0-100%] to afford methyl 2-(2-(2-(3-(((tert-butoxycarbonyl)amino)methyl)phenyl)pyrrolo[2,1-f][1,2,4]triazine-4-carboxamido)phenyl)acetate (1f) (98 mg, 74% yield) as a white solid; $^1$H NMR (300 MHz, DMSO-$d_6$) δ 10.78 (s, 1H), 8.44 (d, J=7.8 Hz, 1H), 8.41-8.31 (m, 2H), 7.82-7.75 (m, 1H), 7.58-7.48 (m, 3H), 7.46-7.37 (m, 3H), 7.31-7.23 (m, 2H), 4.27 (d, J=6.1 Hz, 2H), 3.89 (s, 2H), 3.56 (s, 3H), 1.41 (s, 9H).

Step-5: Preparation of methyl 2-(2-(2-(3-(aminomethyl)phenyl)pyrrolo[2,1-f][1,2,4]triazine-4-carboxamido)phenyl)acetate (1g)

To a solution of methyl 2-(2-(2-(3-(((tert-butoxycarbonyl)amino)methyl)phenyl)pyrrolo[2,1-f][1,2,4]triazine-4-carboxamido)phenyl)acetate (1f) (92 mg, 0.18 mmol) in DCM (8 mL) was added TFA (0.28 mL, 3.57 mmol). The resulting mixture was stirred at RT for 2 h and concentrated in vacuum to dryness. The residue obtained was purified by flash column chromatography [silica (12 g), eluting with DMA80 in DCM from 0-60%] to afford compound (1g) (73 mg, 98% yield) as a yellow solid, 23 mg was converted into HCl salt and lyophilized to give methyl 2-(2-(2-(3-(aminomethyl)phenyl)pyrrolo[2,1-f][1,2,4]triazine-4-carboxamido)phenyl)acetate (1g) (25 mg) HCl salt as a yellow solid; $^1$H NMR (300 MHz, DMSO-$d_6$) δ 10.80 (s, 1H, $D_2O$ exchangeable), 8.69-8.62 (m, 1H), 8.58 (d, J=7.5, 1.6 Hz, 1H), 8.50-8.39 (m, 3H, $D_2O$ exchangeable), 8.39-8.33 (m, 1H), 7.77-7.56 (m, 4H), 7.47-7.36 (m, 2H), 7.34-7.24 (m, 2H), 4.23-4.11 (m, 2H), 3.90 (s, 2H), 3.55 (s, 3H); MS (ES+): 416.3 (M+1); (ES−): 414.4 (M−1), 450.3 (M+Cl); HPLC, purity 92.70%.

Step-6: Preparation of 2-(2-(2-(3-(aminomethyl)phenyl)pyrrolo[2,1-f][1,2,4]triazine-4-carboxamido)phenyl)acetic Acid (1h)

To a solution of methyl 2-(2-(2-(3-(aminomethyl)phenyl)pyrrolo[2,1-f][1,2,4]triazine-4-carboxamido)phenyl)acetate (1g) (62 mg, 0.15 mmol) in THF (10 mL) was added lithium hydroxide hydrate (63 mg, 1.49 mmol) in water (2 mL). The resulting mixture was stirred at RT overnight. THF was removed under vacuum, the residue obtained was acidified to pH 4 with HCl (2N), the solid obtained was collected by filtration, washed with water (3×2 mL) and dried in vacuum to afford 2-(2-(2-(3-(aminomethyl)phenyl)pyrrolo[2,1-f][1,2,4]triazine-4-carboxamido)phenyl)acetic acid (1h) (36 mg, 61% yield) as a yellow solid; $^1$H NMR (300 MHz, DMSO-$d_6$) δ 12.51 (s, 1H, $D_2O$ exchangeable), 9.36 (s, 1H), 9.19 (s, 3H, $D_2O$ exchangeable), 8.43-8.33 (m, 1H), 8.33-8.21 (m, 1H), 8.00-7.84 (m, 1H), 7.72-7.61 (m, 1H), 7.60-7.48 (m, 2H), 7.34-7.22 (m, 3H), 7.19-7.05 (m, 1H), 4.13 (s, 2H), 3.50 (s, 2H); MS (ES+): 402.4 (M+1); (ES−): 400.4 (M−1); HPLC purity, 90.46%.

Scheme-2

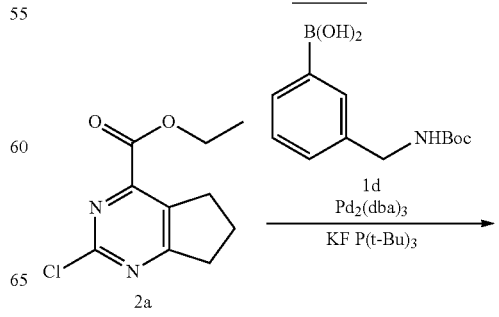

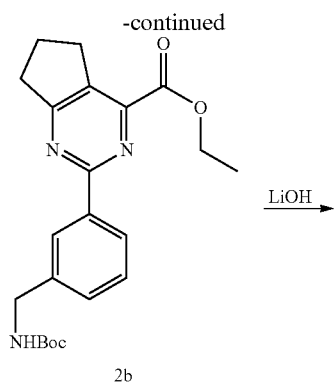

2b

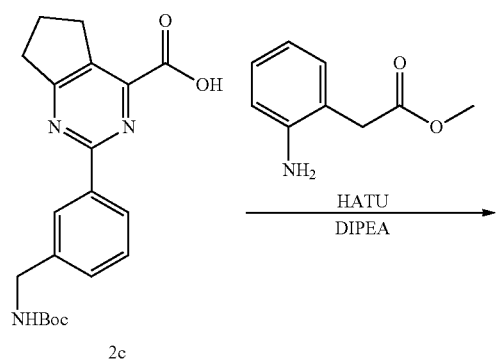

2c

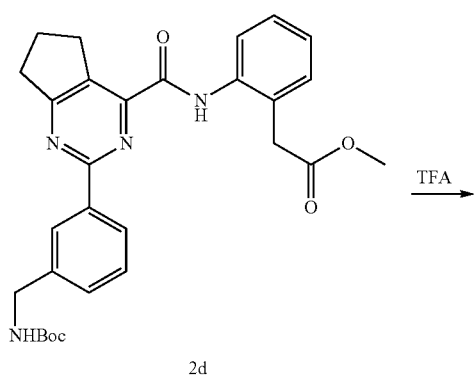

2d

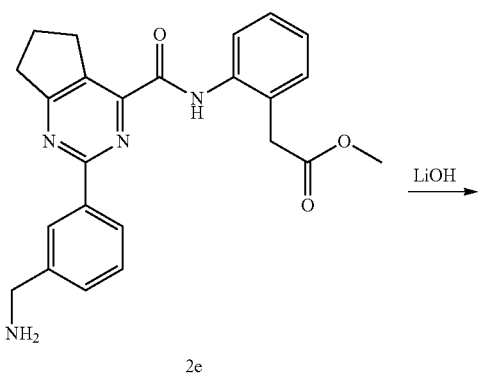

2e

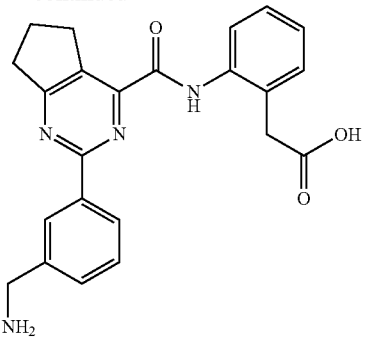

2f

Preparation of 2-(2-(2-(3-(aminomethyl)phenyl)-6,7-dihydro-5H-cyclopenta[d]pyrimidine-4-carboxamido)phenyl)acetic Acid (2f)

Step-1: Preparation of Ethyl 2-(3-(((tert-butoxycarbonyl)amino)methyl)phenyl)-6,7-dihydro-5H-cyclopenta[d]pyrimidine-4-carboxylate (2b)

Compound 2b was prepared according to the procedure reported in step-3 of Scheme-1, from ethyl 2-chloro-6,7-dihydro-5H-cyclopenta[d]pyrimidine-4-carboxylate (2a) (200 mg, 0.88 mmol; CAS #1660116-32-4; prepared according to the procedure reported by Blaquiere, Nicole et al in PCT Int. Appl., 2015025026, 26 Feb. 2015) in DMF (20 mL) using 3-((tert-butoxycarbonylamino)methyl)phenylboronic acid (Id) (251 mg, 0.97 mmol), potassium fluoride (169 mg, 2.91 mmol), tri-tert-butylphosphine (1.59 mL, 1.59 mmol) and $Pd_2(dba)_3$ (162 mg, 0.18 mmol) under a nitrogen atmosphere by heating at 120° C. for 14 h. This gave after workup and purification by flash column chromatography [silica (12 g), eluting with hexanes/ethyl acetate (1:0 to 4:1)] ethyl 2-(3-(((tert-butoxycarbonyl)amino)methyl)phenyl)-6,7-dihydro-5H-cyclopenta[d]pyrimidine-4-carboxylate (2b) (128 mg, 37% yield) as a colorless gum; $^1$H NMR (300 MHz, DMSO-$d_6$) δ 8.32-8.22 (m, 2H), 7.57-7.33 (m, 3H), 4.40 (q, J=7.1 Hz, 2H), 4.22 (d, J=6.2 Hz, 2H), 3.22 (t, J=7.5 Hz, 2H), 3.07 (t, J=7.8 Hz, 2H), 2.12 (p, J=7.7 Hz, 2H), 1.46-1.30 (m, 12H); MS (ES+): 420.3 (M+Na).

Step-2: Preparation of 2-(3-(((tert-butoxycarbonyl)amino)methyl)phenyl)-6,7-dihydro-5H-cyclopenta[d]pyrimidine-4-carboxylic Acid (2c)

Compound 2c was prepared according to the procedure reported in step-6 of Scheme-1, from ethyl 2-(3-(((tert-butoxycarbonyl)amino)methyl)phenyl)-6,7-dihydro-5H-cyclopenta[d]pyrimidine-4-carboxylate (2b) (125 mg, 0.31 mmol) in THF (10 mL) and MeOH (10 mL) using a solution of lithium hydroxide hydrate (81 mg, 1.89 mmol) in water (10 mL) This gave after workup 2-(3-(((tert-butoxycarbonyl)amino)methyl)phenyl)-6,7-dihydro-5H-cyclopenta[d]pyrimidine-4-carboxylic acid (2c), which was used as such for next step; MS (ES−) 368.4 (M−1).

Step-3: Preparation of methyl 2-(2-(2-(3-(((tert-butoxycarbonyl)amino)methyl)phenyl)-6,7-dihydro-5H-cyclopenta[d]pyrimidine-4-carboxamido)phenyl)acetate (2d)

Compound 2d was prepared according to the procedure reported in step-4 of Scheme-1, from 2-(3-(((tert-butoxycarbonyl)amino)methyl)phenyl)-6,7-dihydro-5H-cyclopenta[d]pyrimidine-4-carboxylic acid (2c) using methyl 2-(2-aminophenyl)acetate (104 mg, 0.63 mmol), DIPEA (0.22 mL, 1.26 mmol) and HATU (239 mg, 0.63 mmol). This gave after workup and purification by flash column chromatography [silica (12 g), eluting with hexanes/ethyl acetate (1:0 to 2:1)]methyl 2-(2-(2-(3-(((tert-butoxycarbonyl)amino)methyl)phenyl)-6,7-dihydro-5H-cyclopenta[d]pyrimidine-4-carboxamido)phenyl)acetate (2d) (127 mg) as a yellow solid, which was used as such for next step; MS (ES+): 517.4 (M+1), 539.4 (M+Na); (ES−): 515.4 (M−1).

Step-4: Preparation of methyl 2-(2-(2-(3-(aminomethyl)phenyl)-6,7-dihydro-5H-cyclopenta[d]pyrimidine-4-carboxamido)phenyl)acetate (2e)

Compound 2e was prepared according to the procedure reported in step-5 of Scheme-1, from methyl 2-(2-(2-(3-(((tert-butoxycarbonyl)amino)methyl)phenyl)-6,7-dihydro-5H-cyclopenta[d]pyrimidine-4-carboxamido)phenyl)acetate (2d) (127 mg, 0.25 mmol) using TFA (0.57 mL, 7.38 mmol) in DCM (20 mL). This gave after workup and purification by flash column chromatography [silica (12 g), eluting with DCM/DMA-80 (1:0 to 4:1)] methyl 2-(2-(2-(3-(aminomethyl)phenyl)-6,7-dihydro-5H-cyclopenta[d]pyrimidine-4-carboxamido)phenyl)acetate (2e) (68 mg, 66% yield for three steps) as a white solid; $^1$H NMR (300 MHz, DMSO-$d_6$) δ 10.67 (s, 1H), 8.58-8.54 (m, 1H), 8.47-8.42 (m, 1H), 7.91-7.67 (m, 1H), 7.56-7.43 (m, 2H), 7.42-7.34 (m, 2H), 7.29-7.17 (m, 1H), 3.87 (s, 2H), 3.84 (s, 2H), 3.55 (s, 3H), 3.09 (t, J=7.8 Hz, 2H), 2.21-2.07 (m, 2H); MS (ES+): 417.3 (M+1); (ES−) 415.3 (M−1).

Step-5: Preparation of 2-(2-(2-(3-(aminomethyl)phenyl)-6,7-dihydro-5H-cyclopenta[d]pyrimidine-4-carboxamido)phenyl)acetic Acid (2f)

Compound 2f was prepared according to the procedure reported in step-6 of Scheme-1, from methyl 2-(2-(2-(3-(aminomethyl)phenyl)-6,7-dihydro-5H-cyclopenta[d]pyrimidine-4-carboxamido)phenyl)acetate (2e) (34 mg, 0.082 mmol) in THF (5 mL) and MeOH (5 mL) using a solution of lithium hydroxide hydrate (21 mg, 0.49 mmol) in water (5 mL) This gave after workup 2-(2-(2-(3-(aminomethyl)phenyl)-6,7-dihydro-5H-cyclopenta[d]pyrimidine-4-carboxamido)phenyl)acetic acid (2f) (24 mgs, 73% yield) as a white solid; $^1$H NMR (300 MHz, DMSO-$d_6$) δ 12.35 (s, 1H), 9.46 (s, 1H), 9.27 (s, 3H), 8.46-8.23 (m, 1H), 7.87-7.77 (m, 1H), 7.55-7.47 (m, 2H), 7.30-7.19 (m, 2H), 7.13-7.05 (m, 1H), 4.11 (s, 2H), 3.42 (s, 2H), 3.08 (t, J=7.8 Hz, 2H), 2.22-2.05 (m, 2H); MS (ES+): 403.3 (M+1); (ES−): 401.4 (M−1).

Scheme-3

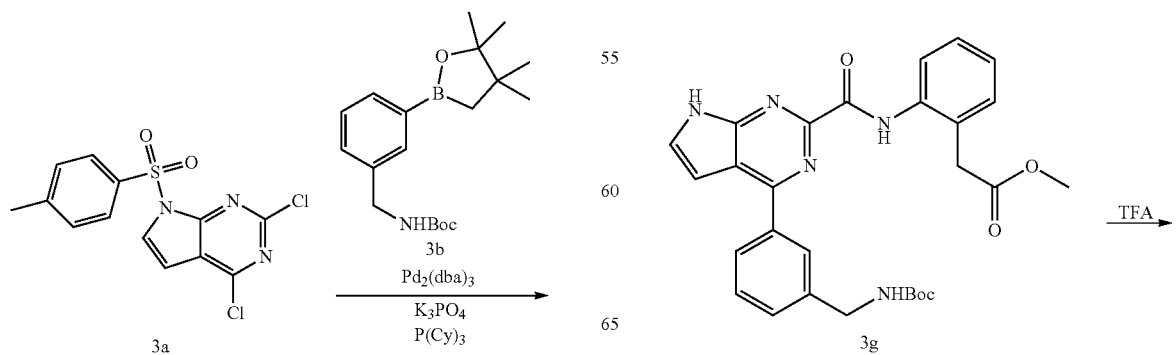

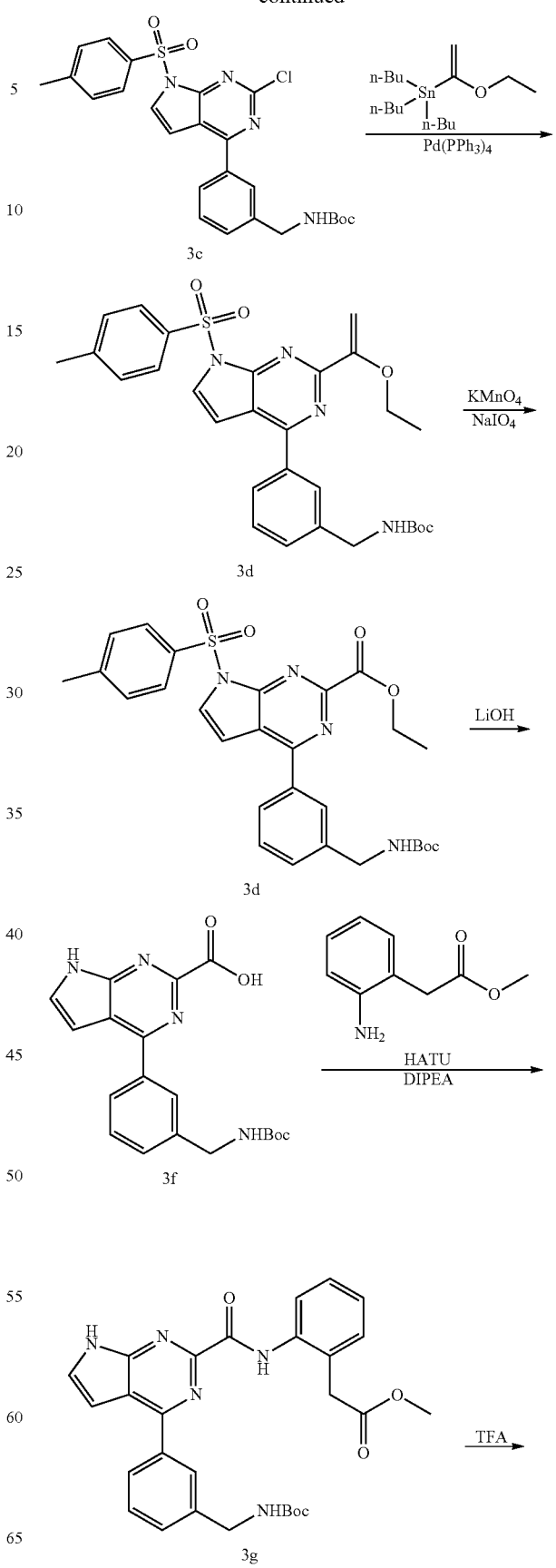

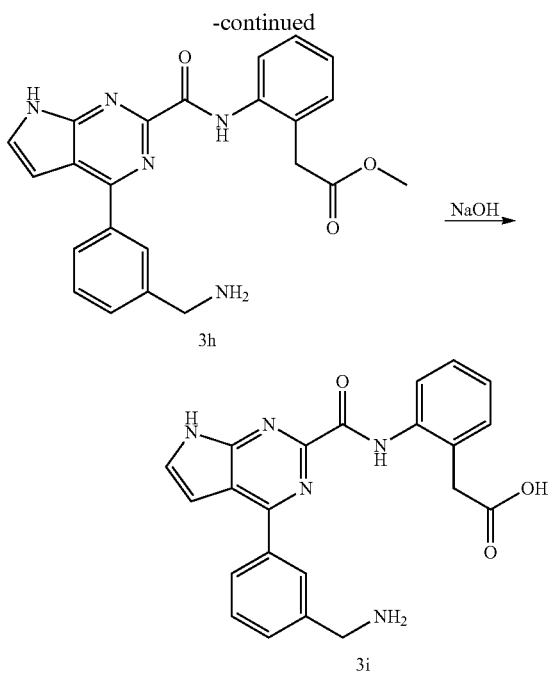

Preparation of 2-(2-(4-(3-(aminomethyl)phenyl)-7H-pyrrolo[2,3-d]pyrimidine-2-carboxamido)phenyl) acetic Acid (3i)

Step-1: Preparation of tert-butyl 3-(2-chloro-7-tosyl-7H-pyrrolo[2,3-d]pyrimidin-4-yl)benzylcarbamate (3c)

Compound 3c was prepared according to the procedure reported in step-3 of Scheme-1 from 2,4-dichloro-7-tosyl-7H-pyrrolo[2,3-d]pyrimidine (3a) (5 g, 14.61 mmol; CAS #934524-10-4; prepared according to the procedure reported by Su, Qibin et al; in Journal of Medicinal Chemistry, 57(1), 144-158; 2014) in dioxane (100 mL) using tert-butyl 3-(4,4,5,5-tetramethyl-1,3,2-dioxaborolan-2-yl)benzylcarbamate (3b) (3.25 g, 9.74 mmol; CAS #: 832114-05-3), tripotassium phosphate (4.55 g, 21.43 mmol) in water (1 mL), tricyclohexylphosphine (0.82 g, 2.92 mmol) and Pd$_2$(dba)$_3$ (0.89 g, 0.97 mmol) in argon atmosphere and heating at 120° C. for 1 h. This gave after workup and purification by flash column chromatography [silica (40 g), eluting with EtOAc in hexane from 0-70%] tert-butyl 3-(2-chloro-7-tosyl-7H-pyrrolo[2,3-d]pyrimidin-4-yl)benzylcarbamate) (3c) (2.9 g, 58.0% yield) as a yellow solid; $^1$H NMR (300 MHz, DMSO-d$_6$) δ 8.14 (d, J=4.1 Hz, 1H), 8.10-8.07 (m, 1H), 8.06-8.04 (m, 1H), 7.96-7.90 (m, 2H), 7.58-7.44 (m, 5H), 7.24 (d, J=4.1 Hz, 1H), 4.23 (d, J=6.2 Hz, 2H), 2.39 (s, 3H), 1.40 (s, 9H); MS (ES+): 535.3, 537.3 (M+Na); (ES−): 511.3, 513.3 (M−1).

Step-2: Preparation of tert-butyl 3-(2-(1-ethoxyvinyl)-7-tosyl-7H-pyrrolo[2,3-d]pyrimidin-4-yl)benzylcarbamate (3d)

Compound 3d was prepared according to the procedure reported in step-1 of Scheme-1 from tert-butyl 3-(2-chloro-7-tosyl-7H-pyrrolo[2,3-d]pyrimidin-4-yl)benzylcarbamate (3c) (2.5 g, 4.87 mmol) in DMF (100 mL) using 1-ethoxyvinyltri-n-butyltin (2.16 mL, 6.34 mmol) and Pd(Ph$_3$P)$_4$ (0.28 g, 0.24 mmol) in argon atmosphere and heating at 110° C. for 4 h. This gave after workup and purification by flash column chromatography [silica (24 g), eluting with EtOAc in hexane from 0-70%] tert-butyl 3-(2-(1-ethoxyvinyl)-7-tosyl-7H-pyrrolo[2,3-d]pyrimidin-4-yl)benzylcarbamate (3d) (1.7 g, 64% yield) as a white solid; $^1$H NMR (300 MHz, DMSO-d$_6$) δ 8.24 (d, J=8.4 Hz, 2H), 8.07 (d, J=4.0 Hz, 1H), 8.01-7.94 (m, 2H), 7.59-7.50 (m, 2H), 7.50-7.40 (m, 3H), 7.18 (d, J=4.1 Hz, 1H), 5.72 (d, J=1.7 Hz, 1H), 4.73 (d, J=1.7 Hz, 1H), 4.24 (d, J=6.2 Hz, 2H), 4.02 (q, J=6.9 Hz, 2H), 2.38 (s, 3H), 1.52 (t, J=6.9 Hz, 3H), 1.40 (s, 9H); MS (ES+): 571.4 (M+Na); (ES−): 547.4 (M−1).

Step-3: Preparation of Ethyl 4-(3-((tert-butoxycarbonylamino)methyl)phenyl)-7-tosyl-7H-pyrrolo[2,3-d]pyrimidine-2-carboxylate (3e)

Compound 3e was prepared according to the procedure reported in step-2 of Scheme-1 from tert-butyl 3-(2-(1-ethoxyvinyl)-7-tosyl-7H-pyrrolo[2,3-d]pyrimidin-4-yl)benzylcarbamate (3d) (1.5 g, 2.73 mmol) in 1,4-dioxane (50 mL) using sodium periodate solution (1.17 g, 5.47 mmol) in water (10 mL) and KMnO$_4$ (2×86 mg, 2×0.55 mmol, second dosing after 12 h). This gave after workup and purification by flash column chromatography [silica (40 g), eluting with EtOAc in hexane from 0-60%] ethyl 4-(3-((tert-butoxycarbonylamino)methyl)phenyl)-7-tosyl-7H-pyrrolo[2,3-d]pyrimidine-2-carboxylate (3e) (500 mg, 33% yield) as a yellow solid; MS (ES+): 551.3 (M+1), 573.3 (M+Na); (ES−): 549.4 (M−1).

Step-4: Preparation of 4-(3-((tert-butoxycarbonylamino)methyl)phenyl)-7H-pyrrolo[2,3-d]pyrimidine-2-carboxylic Acid (3f)

Compound 3f was prepared according to the procedure reported in step-6 of Scheme-1 from ethyl 4-(3-((tert-butoxycarbonylamino)methyl)phenyl)-7-tosyl-7H-pyrrolo[2,3-d]pyrimidine-2-carboxylate (3e) (500 mg, 0.91 mmol) in THF (10 mL) using lithium hydroxide hydrate (76 mg, 1.82 mmol) in water (4 mL). This gave after workup 4-(3-((tert-butoxycarbonylamino)methyl)phenyl)-7H-pyrrolo[2,3-d]pyrimidine-2-carboxylic acid (3f) (145 mg, 43% yield) as a white solid; $^1$H NMR (300 MHz, DMSO-d$_6$) δ 13.18 (s, 1H, D$_2$O exchangeable), 12.69 (d, J=21.6 Hz, 1H, D$_2$O exchangeable), 8.18-8.05 (m, 2H), 7.97-7.88 (m, 1H), 7.62-7.53 (m, 2H), 7.48-7.40 (m, 1H), 7.05-6.97 (m, 1H), 4.27 (d, J=6.3 Hz, 2H), 1.41 (s, 9H); MS (ES−): 367.3 (M−1).

Step-5: Preparation of methyl 2-(2-(4-(3-((tert-butoxycarbonylamino)methyl)phenyl)-7H-pyrrolo[2,3-d]pyrimidine-2-carboxamido)phenyl)acetate (3g)

Compound 3g was prepared according to the procedure reported in step-4 of Scheme-1 from 4-(3-((tert-butoxycarbonylamino)methyl)phenyl)-7H-pyrro[2,3-d]pyrimidine-2-carboxylic acid (3f) (120 mg, 0.33 mmol) in DMF (5 mL) using methyl 2-(2-aminophenyl)acetate (161 mg, 0.98 mmol), DIPEA (0.11 mL, 0.65 mmol) and HATU (186 mg, 0.49 mmol). This gave after workup and purification by flash column chromatography [silica (12 g), eluting with 0-60% EtOAc/MeOH (9:1) in hexane from 0-100%] methyl 2-(2-(4-(3-((tert-butoxycarbonylamino)methyl)phenyl)-7H-pyrrolo[2,3-d]pyrimidine-2-carboxamido)phenyl)acetate (3g) (42 mg, 25% yield) as a white solid; MS (ES+) 538.3 (M+1).

Step-6: Preparation of methyl 2-(2-(4-(3-(aminomethyl)phenyl)-7H-pyrrolo[2,3-d]pyrimidine-2-carboxamido)phenyl)acetate (3h)

Compound 3h was prepared according to the procedure reported in step-5 of Scheme-1 from methyl 2-(2-(4-(3-((tert-butoxycarbonylamino)methyl)phenyl)-7H-pyrro[2,3-d]pyrimidine-2-carboxamido)phenyl)acetate (3g) (40 mg, 0.078 mmol) in DCM (8 mL) using TFA (0.06 mL, 0.78 mmol). This gave methyl 2-(2-(4-(3-(aminomethyl)phenyl)-7H-pyrrolo[2,3-d]pyrimidine-2-carboxamido)phenyl)acetate (3h) (13 mg, 40% yield) which was used as such for next step.

Step-7: Preparation of 2-(2-(4-(3-(aminomethyl)phenyl)-7H-pyrrolo[2,3-d]pyrimidine-2-carboxamido)phenyl)acetic Acid (3i)

To a solution of methyl 2-(2-(4-(3-(aminomethyl)phenyl)-7H-pyrrolo[2,3-d]pyrimidine-2-carboxamido)phenyl)acetate (3h) (13 mg from above step) in MeOH (5 mL) was added NaOH (12 mg, 0.31 mmol) in water (1 mL) and stirred at RT for 2 h. MeOH was removed under vacuum, the residue was acidified to pH 3 and purified by reverse phase chromatography [C18 (50 g), eluting with ACN in water (containing 0.1% HCl) from 0-100%] to give 2-(2-(4-(3-(aminomethyl)phenyl)-7H-pyrrolo[2,3-d]pyrimidine-2-carboxamido)phenyl)acetic acid (3i) (2 mg, 6% yield) as a white solid; $^1$H NMR (300 MHz, DMSO-$d_6$) δ 12.78 (s, 1H, $D_2O$ exchangeable), 10.83 (s, 1H, $D_2O$ exchangeable), 8.49-8.23 (m, 5H, partially $D_2O$ exchangeable), 8.01-7.92 (m, 2H), 7.69 (d, J=4.8 Hz, 2H), 7.43-7.32 (m, 2H), 7.27-7.12 (m, 2H), 4.28-4.14 (m, 2H), 3.77 (s, 2H); MS (ES+): 402.3 (M+1); (ES−): 436.3 (M+Cl); HPLC purity 98.03%.

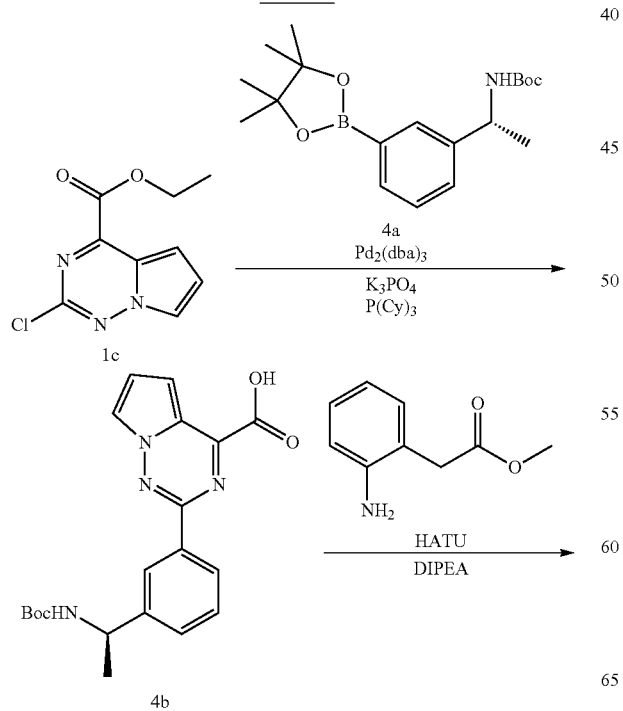

Scheme-4

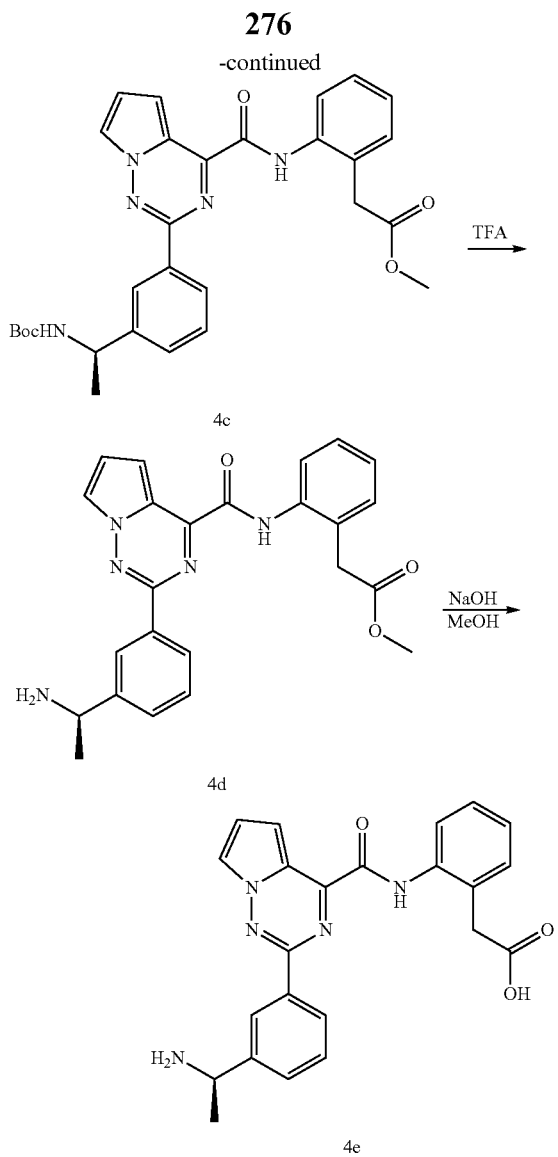

Preparation of (R)-2-(2-(2-(3-(1-aminoethyl)phenyl)pyrrolo[2,1-f][1,2,4]triazine-4-carboxamido)phenyl)acetic Acid (4e)

Step-1: Preparation of (R)-2-(3-(1-(tert-butoxycarbonylamino)ethyl)phenyl)pyrrolo[2,1-f][1,2,4]triazine-4-carboxylic Acid (4b)

Compound 4b was prepared according to the procedure reported in step-3 of Scheme-1 from ethyl 2-chloropyrrolo[2,1-f][1,2,4]triazine-4-carboxylate (1c) (300 mg, 1.33 mmol) in dioxane (6 mL) using (R)-tert-butyl 1-(3-(4,4,5,5-tetramethyl-1,3,2-dioxaborolan-2-yl)phenyl)ethylcarbamate (4a) (600 mg, 1.73 mmol; CAS #887254-66-2, prepared according to procedure reported in PCT Int. Appl., 2015009977, 22 Jan. 2015), solution of tripotassium phosphate (564 mg, 2.66 mmol) in water (1 mL), tricyclohexylphosphine (112 mg, 0.4 mmol) and $Pd_2(dba)_3$ (122 mg, 0.13 mmol) in argon atmosphere and heating at 125° C. for 30 min. This gave after workup and purification by flash column chromatography [silica (12 g), eluting with MeOH in DCM from 0-30%] (R)-2-(3-(1-(tert-butoxycarbonylamino)ethyl)phenyl)pyrrolo[2,1-f][1,2,4]triazine-4-carboxylic acid (4b) (150 mg, 30% yield) as a yellow solid; MS (ES–): 381.3 (M–1).

Step-2: Preparation of (R)-methyl 2-(2-(2-(3-(1-(tert-butoxycarbonylamino)ethyl)phenyl)pyrrolo[2,1-f][1,2,4]triazine-4-carboxamido)phenyl)acetate (4c)

Compound 4c was prepared according to the procedure reported in step-4 of Scheme-1 from (R)-2-(3-(1-(tert-butoxycarbonylamino)ethyl)phenyl)pyrrolo[2,1-f][1,2,4]triazine-4-carboxylic acid (4b) (150 mg, 0.39 mmol) in DMF (8 mL) using methyl 2-(2-aminophenyl)acetate (78 mg, 0.47 mmol), DIPEA (0.21 mL, 1.18 mmol) and HATU (179 mg, 0.47 mmol). This gave after workup and purification by flash column chromatography [silica (12 g), eluting with 0-60% EtOAc/MeOH (9:1) in hexane from 0-100%] (R)-methyl 2-(2-(2-(3-(1-(tert-butoxycarbonylamino)ethyl)phenyl)pyrrolo[2,1-f][1,2,4]triazine-4-carboxamido)phenyl)acetate (4c) (60 mg, 29% yield) as a yellow solid; MS (ES+): 552.4 (M+1).

Step-3: Preparation of (R)-methyl 2-(2-(2-(3-(1-aminoethyl)phenyl)pyrrolo[2,1-f][1,2,4]triazine-4-carboxamido)phenyl)acetate (4d)

Compound 4d was prepared according to the procedure reported in step-5 of Scheme-1 from (R)-methyl 2-(2-(2-(3-(1-(tert-butoxycarbonylamino)ethyl)phenyl)pyrrolo[2,1-f][1,2,4]triazine-4-carboxamido)phenyl)acetate (4c) (60 mg, 0.11 mmol) in DCM (8 mL) using TFA (0.087 mL, 1.13 mmol). This gave after workup and purification by flash column chromatography [silica (12 g), eluting with DMA80 in DCM from 0-100%] (R)-methyl 2-(2-(2-(3-(1-aminoethyl)phenyl)pyrrolo[2,1-f][1,2,4]triazine-4-carboxamido)phenyl)acetate (4d) (12 mg, 25% yield), MS (ES+): 452.3 (M+Na); (ES–): 428.3 (M–1).

Step-4: Preparation of (R)-2-(2-(2-(3-(1-aminoethyl)phenyl)pyrrolo[2,1-f][1,2,4]triazine-4-carboxamido)phenyl)acetic Acid (4e)

To a solution of (R)-methyl 2-(2-(2-(3-(1-aminoethyl)phenyl)pyrrolo[2,1-f][1,2,4]triazine-4-carboxamido)phenyl)acetate (4d) (12 mg, 0.028 mmol) in MeOH (5 mL) was added a solution of NaOH (18 mg, 0.45 mmol) in water (1 mL). The resulting mixture was stirred for 2 h at RT and concentrated in vacuum to remove MeOH. The residue was acidified to PH~3 and purified by reverse phase chromatography [C18 (50 g), eluting with ACN in water (containing 0.1% HCl) from 0-100%] to afford (R)-2-(2-(2-(3-(1-aminoethyl)phenyl)pyrrolo[2,1-f][1,2,4]triazine-4-carboxamido)phenyl)acetic acid (4e) (7 mg, 15% yield) as a yellow solid; $^1$H NMR (300 MHz, DMSO-$d_6$) δ 12.74 (s, 1H, D$_2$O exchangeable), 10.89 (s, 1H, D$_2$O exchangeable), 8.70-8.46 (m, 5H, partially D$_2$O exchangeable), 8.42-8.35 (m, 1H), 7.89-7.81 (m, 1H), 7.78-7.69 (m, 1H, D$_2$O exchangeable), 7.69-7.58 (m, 2H), 7.46-7.35 (m, 2H), 7.33-7.21 (m, 2H), 4.65-4.47 (m, 1H), 3.81 (s, 2H), 1.60 (d, J=6.7 Hz, 3H); MS (ES+): 438.3 (M+Na); (ES–): 414.4 (M–1); HPLC purity, 98.78%.

Scheme-5

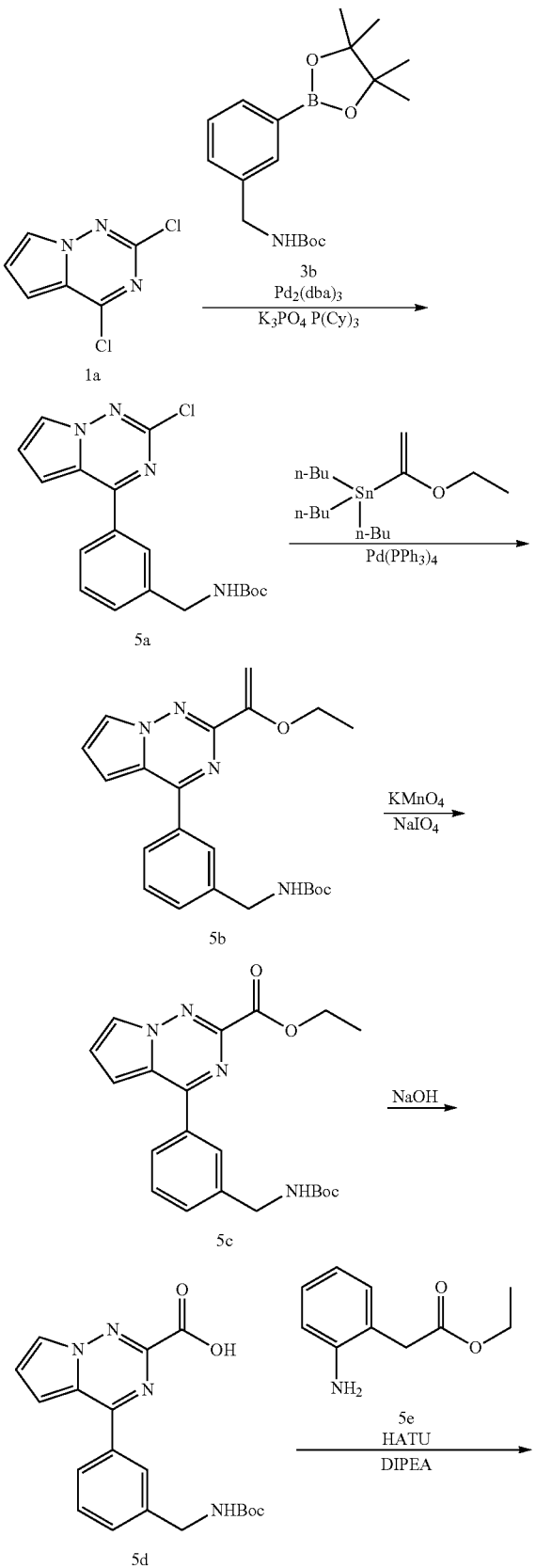

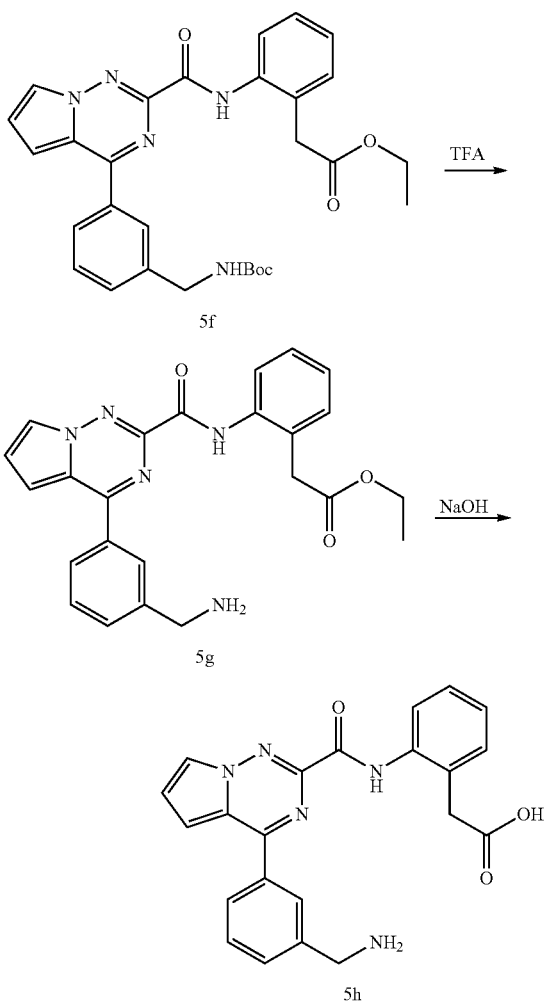

Preparation of 2-(2-(4-(3-(aminomethyl)phenyl)pyrrolo[2,1-f][1,2,4]triazine-2-carboxamido)phenyl)acetic Acid (5h)

Step-1: Preparation of tert-butyl 3-(2-chloropyrrolo[2,1-f][1,2,4]triazin-4-yl)benzylcarbamate (5a)

Compound 5a was prepared according to the procedure reported in step-3 of Scheme-1 from 2,4-dichloropyrrolo[2,1-f][1,2,4]triazine (1a) (1 g, 5.32 mmol) in dioxane (50 mL) using tert-butyl 3-(4,4,5,5-tetramethyl-1,3,2-dioxaborolan-2-yl)benzylcarbamate (3b) (1.48 g, 4.43 mmol), tripotassium phosphate (1.88 g, 8.86 mmol) in water (5 mL), tricyclohexylphosphine (373 mg, 1.33 mmol) and Pd$_2$(dba)$_3$ (0.406 g, 0.44 mmol) in Ar atmosphere and heating at 75° C. for 60 min. This gave after workup and purification by flash column chromatography [silica (12 g), eluting with MeOH in DCM from 0-30%] tert-butyl 3-(2-chloropyrrolo[2,1-f][1,2,4]triazin-4-yl)benzylcarbamate (5a) (1 g, 63% yield) as a yellow solid; $^1$H NMR (300 MHz, DMSO-d$_6$) δ 8.34-8.27 (m, 1H), 8.08-7.98 (m, 2H), 7.65-7.50 (m, 3H), 7.40-7.30 (m, 1H), 7.24-7.14 (m, 1H), 4.27 (d, J=6.2 Hz, 2H), 1.41 (s, 9H).

Step-2: Preparation of tert-butyl 3-(2-(1-ethoxyvinyl)pyrrolo[2,1-f][1,2,4]triazin-4-yl)benzylcarbamate (5b)

Compound 5b was prepared according to the procedure reported in step-1 of Scheme-1 from tert-butyl 3-(2-chloropyrrolo[2,1-f][1,2,4]triazin-4-yl)benzylcarbamate (5a) (3.2 g, 8.92 mmol) in DMF (60 mL) using 1-ethoxyvinyltri-n-butyltin (3.65 mL, 10.70 mmol) and Pd(PPh$_3$)$_4$ (0.515 g, 0.45 mmol) in argon atmosphere and heating at 110° C. for 10 h. This gave after workup and purification by flash column chromatography [silica (40 g), eluting with EtOAc in hexane from 0-70%] tert-butyl 3-(2-(1-ethoxyvinyl)pyrrolo[2,1-f][1,2,4]triazin-4-yl)benzylcarbamate (5b) (3.1 g, 88% yield) as a yellow solid; $^1$H NMR (300 MHz, DMSO-d$_6$) δ 8.28-8.21 (m, 1H), 8.11-8.00 (m, 2H), 7.64-7.47 (m, 3H), 7.22 (dd, J=4.6, 1.4 Hz, 1H), 7.12-7.04 (m, 1H), 5.74 (d, J=1.8 Hz, 1H), 4.79 (d, J=1.8 Hz, 1H), 4.28 (d, J=6.2 Hz, 2H), 3.99 (q, J=6.9 Hz, 2H), 1.46-1.31 (m, 12H).

Step-3: Preparation of Ethyl 4-(3-(((tert-butoxycarbonyl)amino)methyl)phenyl)pyrrolo[2,1-f][1,2,4]triazine-2-carboxylate (5c)

Compound 5c was prepared according to the procedure reported in step-2 of Scheme-1 from tert-butyl 3-(2-(1-ethoxyvinyl)pyrrolo[2,1-f][1,2,4]triazin-4-yl)benzylcarbamate (5b) (500 mg, 1.27 mmol) in 1,4-dioxane (50 mL) using sodium periodate solution (542 mg, 2.54 mmol) in water (20 mL) and KMnO$_4$ (120 mg, 0.76 mmol, first dosing and second dosing 40 mg, 0.25 mmol after 12 h). This gave after workup and purification by flash column chromatography [silica (40 g), eluting with EtOAc in hexane from 0-60%] ethyl 4-(3-(((tert-butoxycarbonyl)amino)methyl)phenyl)pyrrolo[2,1-f][1,2,4]triazine-2-carboxylate (5c) (255 mg, 51% yield) as a yellow solid; $^1$H NMR (300 MHz, DMSO-d$_6$) δ 8.45-8.39 (m, 1H), 8.10-8.01 (m, 2H), 7.64-7.49 (m, 3H), 7.38-7.33 (m, 1H), 7.33-7.26 (m, 1H), 4.42 (q, J=7.1 Hz, 2H), 4.27 (d, J=6.2 Hz, 2H), 1.47-1.31 (m, 12H); MS (ES+): 397.3 (M+1); (ES−): 395.4 (M−1)

Step-4: Preparation of 4-(3-(((tert-butoxycarbonyl)amino)methyl)phenyl)pyrrolo[2,1-f][1,2,4]triazine-2-carboxylic Acid (5d)

Compound 5d was prepared according to the procedure reported in step-4 of Scheme-4 from ethyl 4-(3-(((tert-butoxycarbonyl)amino)methyl)phenyl)pyrrolo[2,1-f][1,2,4]triazine-2-carboxylate (5c) (1.6 g, 4.04 mmol) in MeOH/THF (20 mL, 1:1) using sodium hydroxide (258 mg, 6.46 mmol) in water (3 mL). This gave after workup and purification by flash column chromatography [silica (24 g), eluting with MeOH in DCM from 0-10%] 4-(3-(((tert-butoxycarbonyl)amino)methyl)phenyl)pyrrolo[2,1-f][1,2,4]triazine-2-carboxylic acid (5d) (960 mg, 65% yield) as a yellow solid; $^1$H NMR (300 MHz, DMSO-d$_6$) δ 13.71 (s, 1H), 8.43-8.33 (m, 1H), 8.11-8.02 (m, 2H), 7.64-7.47 (m, 3H), 7.34 (dd, J=4.6, 1.4 Hz, 1H), 7.32-7.25 (m, 1H), 4.27 (d, J=6.2 Hz, 2H), 1.41 (s, 9H); MS (ES+): 369.3 (M+1); (ES−): 367.3 (M−1).

Step-5: Preparation of Ethyl 2-(2-(4-(3-(((tert-butoxycarbonyl)amino)methyl)phenyl)pyrrolo[2,1-f][1,2,4]triazine-2-carboxamido)phenyl)acetate (5f)

Compound 5f was prepared according to the procedure reported in step-4 of Scheme-1 from 4-(3-(((tert-butoxycarbonyl)amino)methyl)phenyl)pyrrolo[2,1-f][1,2,4]triazine-2-carboxylic acid (5d) (200 mg, 0.54 mmol) in DMF (10 mL) using ethyl 2-(2-aminophenyl)acetate (5e) (117 mg, 0.65 mmol), DIPEA (0.142 mL, 0.81 mmol) and HATU (248 mg, 0.65 mmol). This gave after workup and purification by flash column chromatography [silica (12 g), eluting with DMA80 in DCM from 0-100%] followed by reverse column [C18 (50 g), eluting with ACN in water (containing 0.1% HCl) from 0-100%] ethyl 2-(2-(4-(3-(((tert-butoxycarbonyl)amino)methyl)phenyl)pyrrolo[2,1-f][1,2,4]triazine-2-carboxamido)phenyl)acetate (5f) (212 mg, 74% yield) as a yellow solid; $^1$H NMR (300 MHz, DMSO-d$_6$) δ 10.64 (s, 1H), 8.44 (dd, J=2.7, 1.3 Hz, 1H), 8.29-8.18 (m, 2H), 7.85-7.75 (m, 1H), 7.66-7.53 (m, 3H), 7.47-7.41 (m, 1H), 7.38 (d, J=7.5 Hz, 2H), 7.34-7.29 (m, 1H), 7.28-7.19 (m, 1H), 4.30 (d, J=6.2 Hz, 2H), 3.98 (q, J=7.1 Hz, 2H), 3.84 (s, 2H), 1.40 (s, 9H), 0.99 (t, J=7.1 Hz, 3H); MS (ES+): 530.4 (M+1); (ES−): 528.5 (M−1).

Step-6: Preparation of Ethyl 2-(2-(4-(3-(aminomethyl)phenyl)pyrrolo[2,1-f][1,2,4]triazine-2-carboxamido)phenyl)acetate (5g)

Compound 5g was prepared according to the procedure reported in step-5 of Scheme-1 from ethyl 2-(2-(4-(3-(((tert-butoxycarbonyl)amino)methyl)phenyl)pyrrolo[2,1-f][1,2,4]triazine-2-carboxamido)phenyl)acetate (5f) (210 mg, 0.4 mmol) in DCM (10 mL) using TFA (0.31 mL, 3.97 mmol). This gave after work up and purification by flash column chromatography [silica (12 g), eluting with DMA80 in DCM from 0-100%] followed by reverse phase column [C18 (50 g), eluting with ACN in water (containing 0.1% HCl) from 0-100%] ethyl 2-(2-(4-(3-(aminomethyl)phenyl)pyrrolo[2,1-f][1,2,4]triazine-2-carboxamido)phenyl)acetate (5g) (152 mg, 89% yield) as a yellow solid; $^1$H NMR (300 MHz, DMSO-d$_6$) δ 10.64 (s, 1H, D$_2$O exchangeable), 8.62 (s, 3H, D$_2$O exchangeable), 8.51-8.44 (m, 2H), 8.42-8.35 (m, 1H), 7.86-7.80 (m, 1H), 7.80-7.64 (m, 3H), 7.43-7.31 (m, 3H), 7.28-7.20 (m, 1H), 4.23-4.17 (m, 2H), 3.98 (q, J=7.1 Hz, 2H), 3.84 (s, 2H), 1.00 (t, J=7.1 Hz, 3H); MS (ES+): 430.3 (M+1), 452.3 (M+Na); HPLC purity, 99.46%.

Step-7: Preparation of 2-(2-(4-(3-(aminomethyl)phenyl)pyrrolo[2,1-f][1,2,4]triazine-2-carboxamido)phenyl)acetic Acid (5h)

Compound 5h was prepared according to the procedure reported in step-4 of Scheme-4 from ethyl 2-(2-(4-(3-(aminomethyl)phenyl)pyrrolo[2,1-f][1,2,4]triazine-2-carboxamido)phenyl)acetate (5g) (70 mg, 0.16 mmol) in MeOH (10 mL) using sodium hydroxide (33 mg, 0.82 mmol) in water (2 mL). This gave after workup and purification by reverse phase column chromatography [C18 (50 g), eluting with ACN in water (containing 0.1% HCl) from 0-100%] 2-(2-(4-(3-(aminomethyl)phenyl)pyrrolo[2,1-f][1,2,4]triazine-2-carboxamido)phenyl)acetic acid (5h) (39 mg, 60% yield) as a yellow solid; $^1$H NMR (300 MHz, DMSO-d$_6$) δ 12.75 (s, 1H, D$_2$O exchangeable), 10.78 (s, 1H, D$_2$O exchangeable), 8.59-8.32 (m, 6H), 7.90-7.83 (m, 1H), 7.84-7.77 (m, 1H), 7.72 (t, J=7.7 Hz, 1H), 7.64 (dd, J=4.7, 1.3 Hz, 1H), 7.42-7.31 (m, 3H), 7.27-7.18 (m, 1H), 4.22 (s, 2H), 3.75 (s, 2H); MS (ES+): 402.3 (M+1); (ES−): 400.4 (M−1), 436.3 (M+Cl); HPLC purity, 99.40%.

Scheme-6

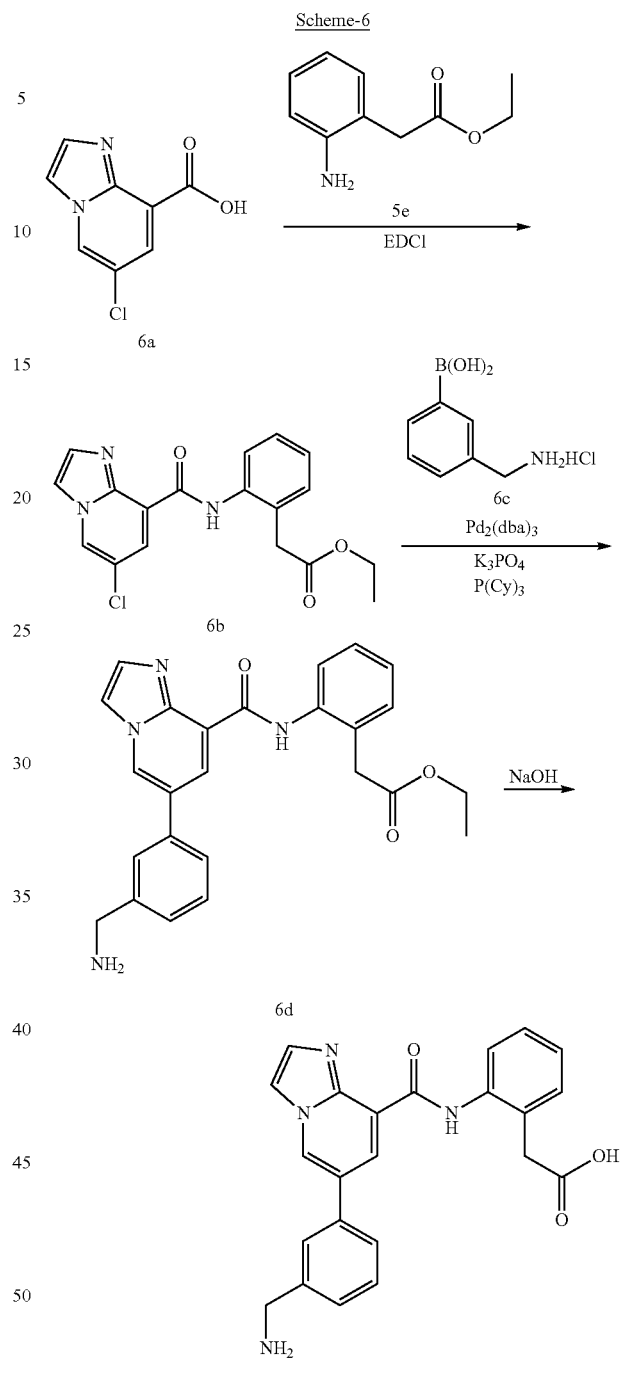

Preparation of 2-(2-(6-(3-(aminomethyl)phenyl)imidazo[1,2-a]pyridine-8-carboxamido)phenyl)acetic Acid (6e)

Step-1: Preparation of Ethyl 2-(2-(6-chloroimidazo[1,2-a]pyridine-8-carboxamido)phenyl)acetate (6b)

To a solution of 6-chloroimidazo[1,2-a]pyridine-8-carboxylic acid (6a) (650 mg, 3.31 mmol; CAS #155735-02-7) in MeOH (10 mL) was added ethyl 2-(2-aminophenyl)acetate (5e) (593 mg, 3.31 mmol; CAS #87-25-2) and N1-((ethylimino)methylene)-N3,N3-dimethylpropane-1,3-diamine hydrochloride (EDCI, 697 mg, 3.64 mmol), the resulting mixture was stirred at RT overnight and diluted with EtOAc (60 mL). The organic layer was separated washed with water (3×s), brine, dried, filtered and concentrated in vacuum. The residue obtained was purified by flash column chromatography [silica (12 g), eluting with DMA80 in DCM from 0-100%], followed by reverse phase column chromatography[C18 (50 g), eluting with ACN in water (containing 0.1% HCl) from 0-100%] to afford ethyl 2-(2-(6-chloroimidazo[1,2-a]pyridine-8-carboxamido)phenyl)acetate (6b) (770 mg, 65% yield) as an off white solid; $^1$H NMR (300 MHz, DMSO-$d_6$) δ 12.05 (s, 1H), 9.15 (d, J=2.1 Hz, 1H), 8.22-8.08 (m, 2H), 8.03 (d, J=2.0 Hz, 1H), 7.74 (d, J=1.3 Hz, 1H), 7.40-7.32 (m, 2H), 7.17 (td, J=7.5, 1.3 Hz, 1H), 4.02 (q, J=7.1 Hz, 2H), 3.94 (s, 2H), 1.07 (t, J=7.1 Hz, 3H); MS (ES+): 358.2 (M+1), 380.2 (M+Na).

Step-2: Preparation of Ethyl 2-(2-(6-(3-(aminomethyl)phenyl)imidazo[1,2-a]pyridine-8-carboxamido)phenyl)acetate (6d)

Compound 6d was prepared according to the procedure reported in step-3 of Scheme-1 from ethyl 2-(2-(6-chloroimidazo[1,2-a]pyridine-8-carboxamido)phenyl)acetate (6b) (250 mg, 0.70 mmol) in dioxane (3 mL) using 3-(aminomethyl)phenylboronic acid hydrochloride (6c) (196 mg, 1.05 mmol; CAS #146285-80-5), tripotassium phosphate (1.3 M solution) (1.61 mL, 2.10 mmol), tricyclohexylphosphine (58.8 mg, 0.210 mmol) and Pd$_2$(dba)$_3$ (64.0 mg, 0.07 mmol) under an Ar atmosphere and heating at 125° C. for 30 min in a microwave. This gave after workup, purification by flash column chromatography [silica (12 g), eluting with DMA80 in DCM from 0-60%], followed by reverse phase column chromatography [C18 (50 g), eluting with ACN in water (containing 0.1% HCl) from 0-100%] ethyl 2-(2-(6-(3-(aminomethyl)phenyl)imidazo[1,2-a]pyridine-8-carboxamido)phenyl)acetate (6d) (195 mg, 65% yield) as a white solid; $^1$H NMR (300 MHz, DMSO-$d_6$ with D$_2$O) δ 9.29 (s, 1H), 8.73 (s, 1H), 8.33-8.26 (m, 1H), 7.99-7.89 (m, 2H), 7.86 (d, J=7.9 Hz, 1H), 7.71 (d, J=7.7 Hz, 1H), 7.67-7.60 (m, 1H), 7.60-7.52 (m, 1H), 7.43-7.33 (m, 2H), 7.33-7.22 (m, 1H), 4.16-4.09 (m, 2H), 3.93-3.92 (m, 2H), 3.83 (s, 2H), 0.99-0.89 (m, 3H); MS (ES+): 429.3 (M+1); 451.3 (M+Na); (ES−): 463.4 (M+Cl); HPLC purity 99.56%.

Step-3: Preparation of 2-(2-(6-(3-(aminomethyl)phenyl)imidazo[1,2-a]pyridine-8-carboxamido)phenyl)acetic Acid (6e)

Compound 6e was prepared according to the procedure reported in step-4 of Scheme-4 from ethyl 2-(2-(6-(3-(aminomethyl)phenyl)imidazo[1,2-a]pyridine-8-carboxamido)phenyl)acetate (6d) (108 mg, 0.25 mmol) in MeOH (10 mL) using sodium hydroxide (50.4 mg, 1.26 mmol) in water (2.0 mL). This gave after workup and purification by reverse phase column chromatography [C18 (50 g), eluting with ACN in water (containing 0.1% HCl) from 0-100%] 2-(2-(6-(3-(aminomethyl)phenyl)imidazo[1,2-a]pyridine-8-carboxamido)phenyl)acetic acid (6e) (90 mg, 89% yield) as a white solid; $^1$H NMR (300 MHz, DMSO-$d_6$ with D$_2$O) δ 9.29 (d, J=1.7 Hz, 1H), 8.73 (d, J=1.7 Hz, 1H), 8.28 (d, J=1.9 Hz, 1H), 7.95 (d, J=1.8 Hz, 1H), 7.91 (s, 1H), 7.86 (d, J=7.7 Hz, 1H), 7.73 (d, J=7.9 Hz, 1H), 7.63 (t, J=7.6 Hz, 1H), 7.59-7.52 (m, 1H), 7.42-7.31 (m, 2H), 7.31-7.21 (m, 1H), 4.12 (s, 2H), 3.77 (s, 2H); MS (ES+): 401.3 (M+1); (ES−): 399.4 (M−1), 435.4 (M+Cl); HPLC purity, 100%.

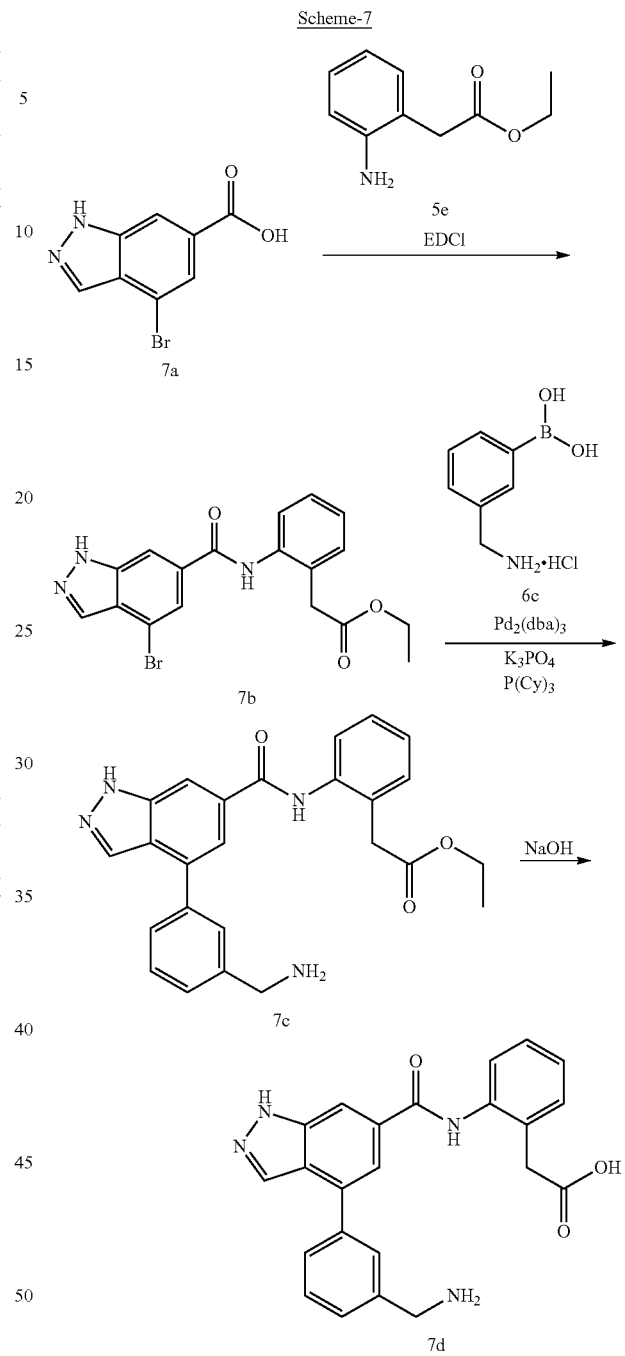

Preparation of 2-(2-(4-(3-(aminomethyl)phenyl)-1H-indazole-6-carboxamido)phenyl)acetic Acid (7d)

Step-1: Preparation of Ethyl 2-(2-(4-bromo-1H-indazole-6-carboxamido)phenyl)acetate (7b)

To a solution of 4-bromo-1H-indazole-6-carboxylic acid (7a) (500 mg, 2.07 mmol; CAS #885523-43-3) in MeOH (10 mL) was added ethyl 2-(2-aminophenyl)acetate (5e) (372 mg, 2.07 mmol) and N1-((ethylimino)methylene)-N3,N3-dimethylpropane-1,3-diamine hydrochloride (EDCI, 437 mg, 2.28 mmol), stirred at RT overnight and concentrated in vacuum to remove MeOH. The residue obtained was taken up in water (5 mL) and TBME (3 mL), stirred at RT for 30 min at RT and the solid was collected via filtration to afford ethyl 2-(2-(4-bromo-1H-indazole-6-carboxamido)phenyl) acetate (7b) (650 mg, 78% yield) as a tan solid; $^1$H NMR (300 MHz, DMSO-$d_6$) δ 13.87 (s, 1H), 10.22 (s, 1H), 8.17 (s, 2H), 7.86 (s, 1H), 7.44-7.20 (m, 4H), 3.96 (q, J=7.1 Hz, 2H), 3.75 (s, 2H), 1.01 (t, J=7.1 Hz, 3H).

Step-2: Preparation of Ethyl 2-(2-(4-(3-(aminomethyl)phenyl)-1H-indazole-6-carboxamido)phenyl) acetate (7c)

Compound 7c was prepared according to the procedure reported in step-3 of Scheme-1 from ethyl 2-(2-(4-bromo-1H-indazole-6-carboxamido)phenyl)acetate (7b) (300 mg, 0.75 mmol) in dioxane (3 mL) using 3-(aminomethyl) phenylboronic acid hydrochloride (6c) (210 mg, 1.12 mmol), tripotassium phosphate (1.3 M solution) (1.72 mL, 2.24 mmol), tricyclohexylphosphine (63 mg, 0.22 mmol) and Pd$_2$(dba)$_3$ (68 mg, 0.075 mmol) under an Ar atmosphere and heating at 125° C. for 30 min in a microwave. This gave after workup, purification by flash column chromatography [silica (12 g), eluting with DMA80 in DCM from 0-60%] ethyl 2-(2-(4-(3-(aminomethyl)phenyl)-1H-indazole-6-carboxamido)phenyl)acetate (7c) (210 mg, 66% yield) as a white solid; 110 mg product was taken and further purified by reverse phase column [C18 (50 g), eluting with ACN in water (containing 0.1% HCl) from 0-100%] to give ethyl 2-(2-(4-(3-(aminomethyl)phenyl)-1H-indazole-6-carboxamido)phenyl)acetate (7c) (57 mg) HCl salt as a white solid; $^1$H NMR (300 MHz, DMSO-$d_6$ with D$_2$O) δ 10.28 (s, 1H, D$_2$O exchangeable), 8.56 (s, 3H, D$_2$O exchangeable), 8.47 (d, J=1.0 Hz, 1H), 8.18 (s, 1H), 8.01 (d, J=2.0 Hz, 1H), 7.91-7.81 (m, 2H), 7.68-7.54 (m, 2H), 7.46-7.39 (m, 1H), 7.39-7.31 (m, 2H), 7.31-7.22 (m, 1H), 4.15 (t, J=5.9 Hz, 3H), 3.95 (q, J=7.1 Hz, 2H), 3.79 (s, 2H), 0.97 (t, J=7.1 Hz, 3H); MS (ES+): 429.3 (M+1); 451.3 (M+Na); (ES−): 463.4 (M+Cl); HPLC, purity 99.41%.

Step-3: Preparation of 2-(2-(4-(3-(aminomethyl) phenyl)-1H-indazole-6-carboxamido)phenyl)acetic Acid (7d)

Compound 7d was prepared according to the procedure reported in step-4 of Scheme-4 from ethyl 2-(2-(4-(3-(aminomethyl)phenyl)-1H-indazole-6-carboxamido)phenyl)acetate (7c) (95 mg, 0.22 mmol) in MeOH (10 mL) using sodium hydroxide (44 mg, 1.11 mmol) in water (2 mL). This gave after workup and purification by reverse phase column chromatography [C18 (50 g), eluting with ACN in water (containing 0.1% HCl) from 0-100%] 2-(2-(4-(3-(aminomethyl)phenyl)-1H-indazole-6-carboxamido)phenyl)acetic acid (7d) (40 mg, 45% yield) as a white solid; $^1$H NMR (300 MHz, DMSO-$d_6$) δ 13.75 (brs, 1H, D$_2$O exchangeable), 10.28 (s, 1H, D$_2$O exchangeable), 8.59-8.43 (m, 4H, partially D$_2$O exchangeable), 8.19 (s, 1H), 8.00 (s, 1H), 7.91-7.82 (m, 2H), 7.67-7.54 (m, 2H), 7.51-7.44 (m, 1H), 7.40-7.30 (m, 2H), 7.30-7.19 (m, 1H), 4.20-4.15 (m, 2H), 3.72 (s, 2H); MS (ES+): 401.3 (M+1); 423.3 (M+Na); (ES−): 399.3 (M−1), 435.3 (M+Cl); HPLC, purity, 100%.

Scheme-8

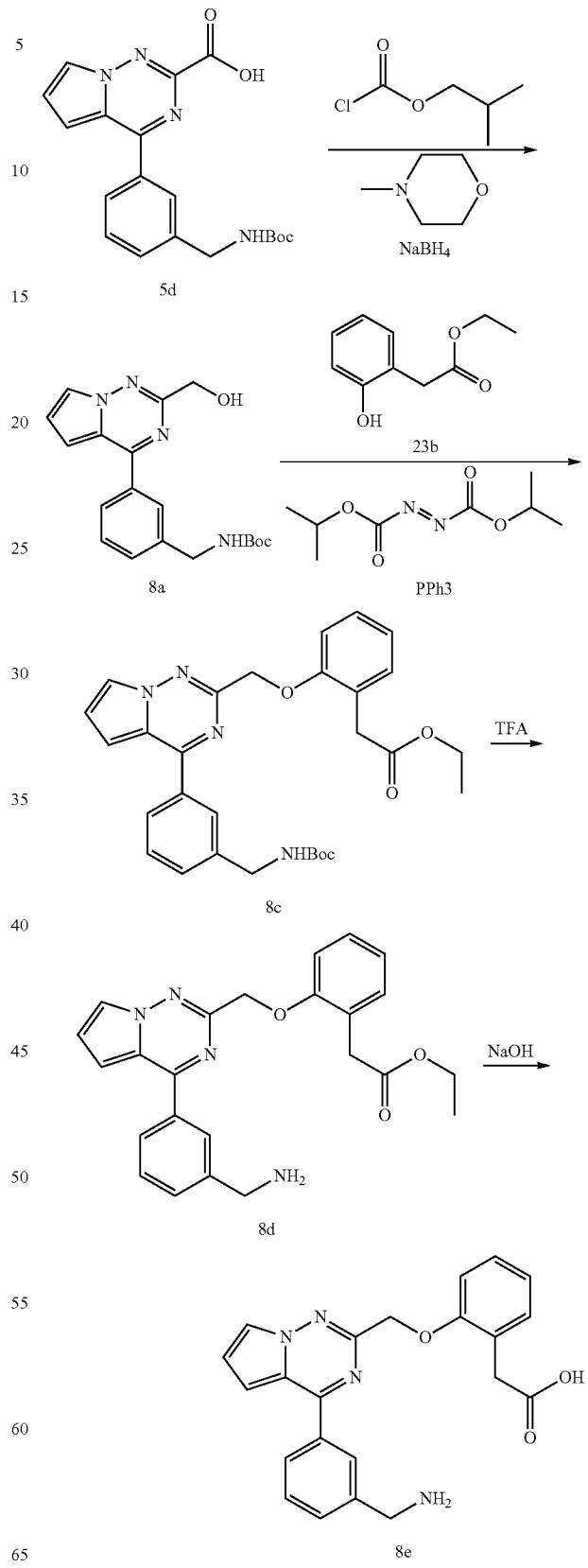

Preparation of 2-(2-((4-(3-(aminomethyl)phenyl) pyrrolo[2,1-f][1,2,4]triazin-2-yl)methoxy)phenyl) acetic Acid (8e)

Step-1: Preparation of tert-butyl 3-(2-(hydroxymethyl)pyrrolo[2,1-f][1,2,4]triazin-4-yl)benzylcarbamate (8a)

To the stirred solution of 4-(3-(((tert-butoxycarbonyl)amino)methyl)phenyl)pyrrolo[2,1-f][1,2,4]triazine-2-carboxylic acid (5d) (390 mg, 1.06 mmol) and N-methylmorpholine (0.13 mL, 1.17 mmol) in THF (5 mL) was added isobutyl chloroformate (0.15 mL, 1.17 mmol) at −5° C. After 10 min, the mixture was filtered over Celite and the precipitate was washed with THF (3×5 mL). The filtrate was cooled to 0° C. and added carefully dropwise a solution of NaBH$_4$ (60 mg, 1.59 mmol) in water (0.5 mL). The reaction mixture was diluted with water (10 mL) and extracted with EtOAc (3×). The organic layers were combined dried, filtered and concentrated in vacuum to afford tert-butyl 3-(2-(hydroxymethyl)pyrrolo[2,1-f][1,2,4]triazin-4-yl)benzylcarbamate (8a) (300 mg, 80% yield) as a yellow oil; $^1$H NMR (300 MHz, DMSO-d$_6$) δ 8.19-8.11 (m, 1H), 8.07-7.95 (m, 2H), 7.63-7.45 (m, 3H), 7.21-7.13 (m, 1H), 7.11-7.03 (m, 1H), 5.51 (t, J=6.3 Hz, 1H), 4.60 (d, J=5.7 Hz, 2H), 4.26 (d, J=6.2 Hz, 2H), 1.41 (s, 9H); MS (ES+): 355.3 (M+1); (ES−): 353.3 (M−1).

Step-2: Preparation of Ethyl 2-(2-((4-(3-(((tert-butoxycarbonyl)amino)methyl)phenyl)pyrrolo[2,1-f][1,2,4]triazin-2-yl)methoxy)phenyl)acetate (8c)

To a solution of tert-butyl 3-(2-(hydroxymethyl)pyrrolo[2,1-f][1,2,4]triazin-4-yl)benzylcarbamate (8a) (250 mg, 0.71 mmol) in THF (5 mL) at 0° C. was added DIAD (0.18 mL, 0.92 mmol), ethyl 2-(2-hydroxyphenyl)acetate (23b) (165 mg, 0.917 mmol; CAS #41873-65-8) and triphenylphosphine (241 mg, 0.92 mmol). The resulting mixture was stirred at RT overnight. The reaction mixture was quenched with water and extracted with EtOAc (3×). The organic layers were combined, washed with saturated aqueous NH$_4$Cl, water, brine, dried and concentrated in vacuum. The residue obtained was purified by flash column chromatography [silica (12 g), eluting with EtOAc in hexane from 0-60%] to afford ethyl 2-(2-((4-(3-(((tert-butoxycarbonyl)amino)methyl)phenyl)pyrrolo[2,1-f][1,2,4]triazin-2-yl)methoxy)phenyl)acetate (8c) (300 mg, 82% yield) as a yellow oil; $^1$H NMR (300 MHz, DMSO-d$_6$) δ 8.23-8.17 (m, 1H), 8.08-7.94 (m, 2H), 7.63-7.48 (m, 3H), 7.31-7.16 (m, 4H), 7.15-7.09 (m, 1H), 6.93 (td, J=7.3, 1.3 Hz, 1H), 5.22 (s, 2H), 4.26 (d, J=6.2 Hz, 2H), 3.92 (q, J=7.1 Hz, 2H), 3.34 (s, 2H), 1.39 (s, 9H), 0.96 (t, J=7.1 Hz, 3H); MS (ES+): 517.4 (M+1); (ES−): 515.4 (M−1).

Step-3: Preparation of Ethyl 2-(2-((4-(3-(aminomethyl)phenyl)pyrrolo[2,1-f][1,2,4]triazin-2-yl)methoxy)phenyl)acetate (8d)

Compound 8d was prepared according to the procedure reported in step-5 of Scheme-1 from ethyl 2-(2-((4-(3-(((tert-butoxycarbonyl)amino)methyl)phenyl)pyrrolo[2,1-f][1,2,4]triazin-2-yl)methoxy)phenyl)acetate (8c) (300 mg, 0.58 mmol) in DCM (10 mL) using TFA (0.45 mL, 5.81 mmol). This gave after workup and purification by flash column chromatography [silica (12 g), eluting with DMA80 in DCM from 0-100%] followed by reverse phase column chromatography [C18 (50 g), eluting with ACN in water (containing 0.1% HCl) from 0-100%] ethyl 2-(2-((4-(3-(aminomethyl)phenyl)pyrrolo[2,1-f][1,2,4]triazin-2-yl)methoxy)phenyl)acetate (8d) (200 mg, 83% yield) as a yellow solid; $^1$H NMR (300 MHz, DMSO-d$_6$) δ 13.75 (brs, 1H, D$_2$O exchangeable), 10.28 (s, 1H, D$_2$O exchangeable), 8.59-8.43 (m, 4H, partially D$_2$O exchangeable), 8.19 (s, 1H), 8.00 (s, 1H), 7.91-7.82 (m, 2H), 7.67-7.54 (m, 2H), 7.51-7.44 (m, 1H), 7.40-7.30 (m, 2H), 7.30-7.19 (m, 1H), 4.20-4.15 (m, 2H), 3.72 (s, 2H); MS (ES+): 417.3 (M+1); 439.3 (M+Na); HPLC purity, 99.88%.

Step-4: Preparation of 2-(2-((4-(3-(aminomethyl)phenyl)pyrrolo[2,1-f][1,2,4]triazin-2-yl)methoxy)phenyl)acetic Acid (8e)

Compound 8e was prepared according to the procedure reported in step-4 of Scheme-4 from ethyl 2-(2-((4-(3-(aminomethyl)phenyl)pyrrolo[2,1-f][1,2,4]triazin-2-yl)methoxy)phenyl)acetate (8d) (100 mg, 0.24 mmol) in MeOH/THF (10 mL, 1:1) using sodium hydroxide (48 mg, 1.2 mmol) in water (2 mL). This gave after workup and purification by reverse phase column chromatography [C18 (50 g), eluting with ACN in water (containing 0.1% HCl) from 0-100%] 2-(2-((4-(3-(aminomethyl)phenyl)pyrrolo[2,1-f][1,2,4]triazin-2-yl)methoxy)phenyl)acetic acid (8e) (71 mg, 76% yield) as a yellow solid; $^1$H NMR (300 MHz, DMSO-d$_6$) δ 8.57 (s, 3H, D$_2$O exchangeable), 8.30-8.20 (m, 2H), 8.19-8.11 (m, 1H), 7.84-7.74 (m, 1H), 7.67 (t, J=7.7 Hz, 1H), 7.43 (dd, J=4.7, 1.3 Hz, 1H), 7.28-7.11 (m, 4H), 6.92 (t, J=7.2, 1.4 Hz, 1H), 5.26 (s, 2H), 4.22-4.14 (m, 2H), 3.61 (s, 2H); MS (ES+): 389.4 (M+1); (ES−): 387.4 (M−1); 423.4 (M+Cl); HPLC purity, 100%.

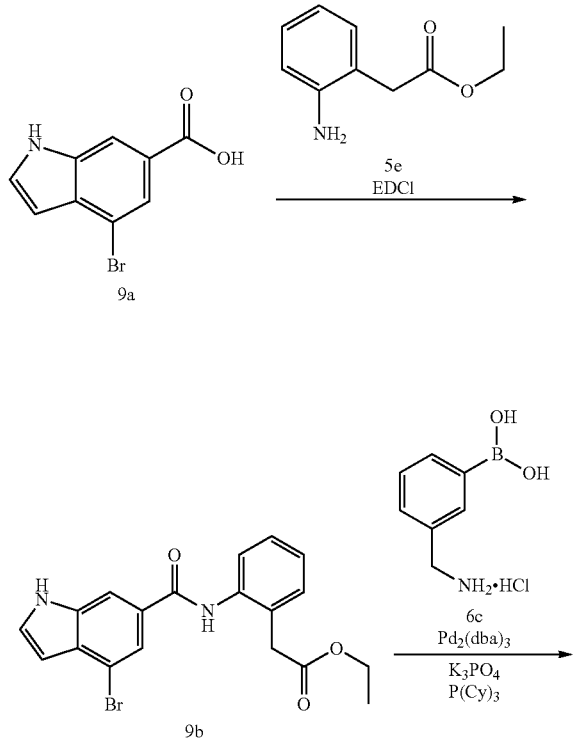

Scheme-9

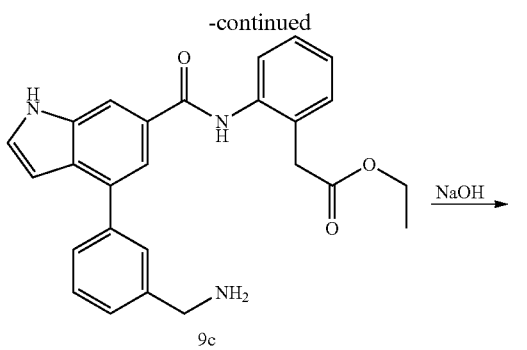

Preparation of 2-(2-(4-(3-(aminomethyl)phenyl)-1H-indole-6-carboxamido)phenyl)acetic Acid (9d)

Step-1: Preparation of Ethyl 2-(2-(4-bromo-1H-indole-6-carboxamido)phenyl)acetate (9b)

Compound 9b was prepared according to the procedure reported in step-1 of Scheme-7 from 4-bromo-1H-indole-6-carboxylic acid (9a) (500 mg, 2.08 mmol; CAS #374633-27-9) in MeOH (10 mL) using ethyl 2-(2-aminophenyl)acetate (5e) (411 mg, 2.29 mmol) and EDCI (479 mg, 2.5 mmol). This gave after workup, purification by flash column chromatography [silica (12 g), eluting with EtOAc in hexane from 0-60%] ethyl 2-(2-(4-bromo-1H-indole-6-carboxamido)phenyl)acetate (9b) (320 mg, 38% yield) as an off white solid; $^1$H NMR (300 MHz, DMSO-$d_6$) δ 11.89 (s, 1H), 10.02 (s, 1H), 8.10-8.02 (m, 1H), 7.83 (d, J=1.3 Hz, 1H), 7.68 (t, J=2.8 Hz, 1H), 7.42-7.28 (m, 3H), 7.28-7.19 (m, 1H), 6.54-6.44 (m, 1H), 3.96 (q, J=7.1 Hz, 2H), 3.74 (s, 2H), 1.01 (t, J=7.1 Hz, 3H).

Step-2: Preparation of Ethyl 2-(2-(4-(3-(aminomethyl)phenyl)-1H-indole-6-carboxamido)phenyl) acetate (9c)

Compound 9c was prepared according to the procedure reported in step-3 of Scheme-1 from ethyl 2-(2-(4-bromo-1H-indole-6-carboxamido)phenyl)acetate (9b) (300 mg, 0.75 mmol) in dioxane (3 mL) using 3-(aminomethyl)phenylboronic acid hydrochloride (6c) (210 mg, 1.12 mmol), tripotassium phosphate (1.3 M solution) (1.72 mL, 2.24 mmol), tricyclohexylphosphine (63 mg, 0.22 mmol) and Pd$_2$(dba)$_3$ (69 mg, 0.075 mmol) under an Ar atmosphere and heating at 125° C. for 30 min in a microwave. This gave after workup, purification by flash column chromatography [silica (12 g), eluting with DMA80 in DCM from 0-60%] followed by purification by reverse phase column [C18 (50 g), eluting with ACN in water (containing 0.1% HCl) from 0-100%] ethyl 2-(2-(4-(3-(aminomethyl)phenyl)-1H-indole-6-carboxamido)phenyl)acetate (9c) (133 mg, 42% yield) as a white solid; $^1$H NMR (300 MHz, DMSO-$d_6$) δ 11.74 (s, 1H), 10.03 (s, 1H), 8.38 (s, 3H, D$_2$O exchangeable), 8.08 (s, 1H), 7.90 (s, 1H), 7.82-7.72 (m, 2H), 7.65 (t, J=2.8 Hz, 1H), 7.59 (t, J=7.6 Hz, 1H), 7.54-7.48 (m, 1H), 7.46-7.39 (m, 1H), 7.37-7.29 (m, 2H), 7.27-7.20 (m, 1H), 6.76 (t, J=2.4 Hz, 1H), 4.23-4.08 (m, 2H), 3.96 (q, J=7.1 Hz, 2H), 3.77 (s, 2H), 0.99 (t, J=7.1 Hz, 3H); MS (ES+): 428.3 (M+1); 450.3 (M+Na); (ES−): 426.4 (M−1); HPLC purity, 97.82%.

Step-3: Preparation of 2-(2-(4-(3-(aminomethyl)phenyl)-1H-indole-6-carboxamido)phenyl)acetic Acid (9d)

Compound 9d was prepared according to the procedure reported in step-4 of Scheme-4 from ethyl 2-(2-(4-(3-(aminomethyl)phenyl)-1H-indole-6-carboxamido)phenyl)acetate (9c) (70 mg, 0.16 mmol) in MeOH (10 mL) using sodium hydroxide (66 mg, 1.61 mmol) in water (2 mL). This gave after workup and purification by reverse phase column chromatography [C18 (50 g), eluting with ACN in water (containing 0.1% HCl) from 0-100%] 2-(2-(4-(3-(aminomethyl)phenyl)-1H-indole-6-carboxamido)phenyl)acetic acid (9d) (23 mg, 35% yield) as a white solid; $^1$H NMR (300 MHz, DMSO-$d_6$) δ 12.28 (s, 1H, D$_2$O exchangeable), 11.76 (t, 1H), 10.08 (s, 1H, D$_2$O exchangeable), 8.48 (s, 3H, D$_2$O exchangeable), 8.10 (s, 1H), 7.91 (s, 1H), 7.83-7.74 (m, 2H), 7.65 (t, J=2.8 Hz, 1H), 7.61-7.46 (m, 3H), 7.37-7.27 (m, 2H), 7.25-7.17 (m, 1H), 6.79-6.72 (m, 1H), 4.20-4.08 (m, 2H), 3.70 (s, 2H); MS (ES$^+$) 400.3 (M+1); 422.3 (M+Na); (ES−) 398.4 (M−1); 434.4 (M+Cl); HPLC purity, 99.02%.

Scheme-10

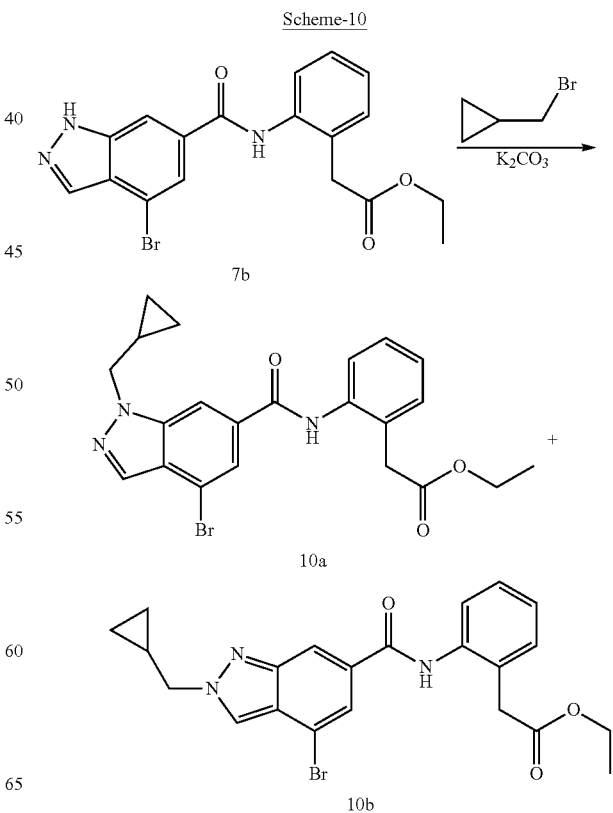

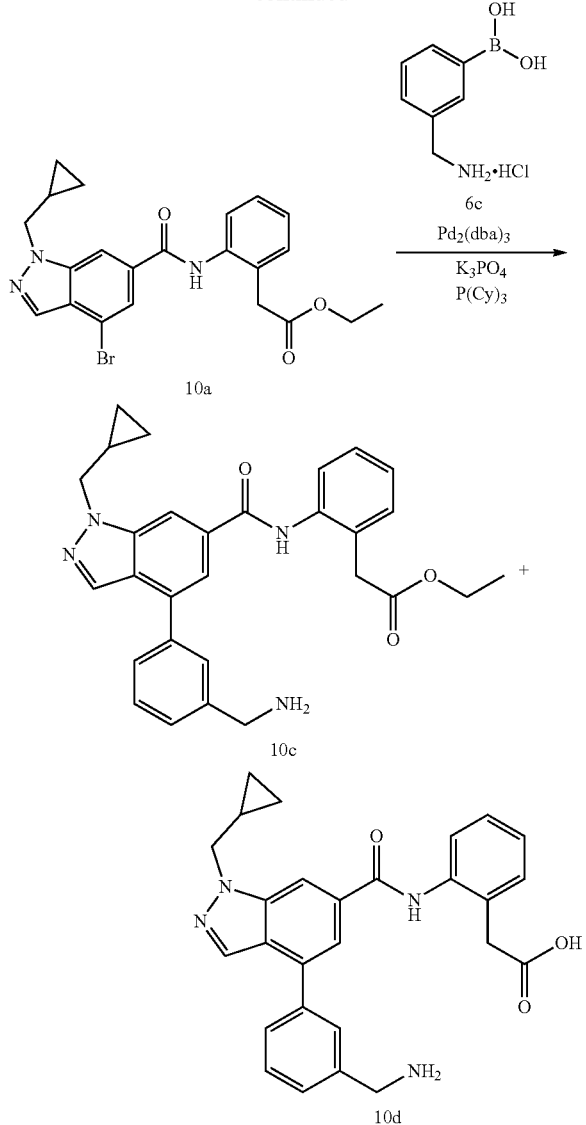

Preparation of 2-(2-(4-(3-(aminomethyl)phenyl)-1-(cyclopropylmethyl)-1H-indazole-6-carboxamido)phenyl)acetic Acid (10d)

Step-1: Preparation of Ethyl 2-(2-(4-bromo-1-(cyclopropylmethyl)-1H-indazole-6-carboxamido)phenyl)acetate (10a) and ethyl 2-(2-(4-bromo-2-(cyclopropylmethyl)-2H-indazole-6-carboxamido)phenyl)acetate (10b)

To a solution of ethyl 2-(2-(4-bromo-1H-indazole-6-carboxamido)phenyl)acetate (7b) (300 mg, 0.75 mmol) in DMF was added (bromomethyl)cyclopropane (151 mg, 1.12 mmol) and potassium carbonate (206 mg, 1.49 mmol). The resulting mixture was stirred at 60° C. overnight, cooled to RT, diluted with EtOAc (100 mL), washed with water (3×), brine, dried and concentrated in vacuum. The residue obtained was purified by flash column chromatography [silica (12 g), eluting with EtOAc in hexane from 0-60%] afforded ethyl 2-(2-(4-bromo-1-(cyclopropylmethyl)-1H-indazole-6-carboxamido)phenyl)acetate (10a) (106 mg, 31% yield); $^1$H NMR (300 MHz, DMSO-$d_6$) δ 8.28 (s, 1H), 8.14 (s, 1H), 7.83 (s, 1H), 7.44-7.15 (m, 4H), 4.34 (d, J=7.0 Hz, 2H), 3.96-3.89 (m, 2H), 3.71 (s, 2H), 1.37-1.23 (m, 1H), 0.94 (t, J=7.1 Hz, 3H), 0.53-0.32 (m, 4H); further elution gave ethyl 2-(2-(4-bromo-2-(cyclopropylmethyl)-2H-indazole-6-carboxamido)phenyl)acetate (10b) (86 mg, 25% yield); $^1$H NMR (300 MHz, DMSO-$d_6$) δ 10.10 (s, 1H), 8.58 (s, 1H), 8.32 (s, 1H), 7.79-7.73 (m, 1H), 7.41 (d, J=6.9 Hz, 1H), 7.38-7.29 (m, 2H), 7.28-7.21 (m, 1H), 4.37 (d, J=7.3 Hz, 2H), 3.96 (q, J=7.1 Hz, 2H), 3.77 (s, 2H), 1.53-1.31 (m, 1H), 1.02 (t, J=7.1, 2.1 Hz, 3H), 0.68-0.41 (m, 4H).

Step-2: Preparation of 2-(2-(4-(3-(aminomethyl)phenyl)-1-(cyclopropylmethyl)-1H-indazole-6-carboxamido)phenyl)acetic Acid (10d)

Compound 10d was prepared according to the procedure reported in step-3 of Scheme-1 from ethyl 2-(2-(4-bromo-1-(cyclopropylmethyl)-1H-indazole-6-carboxamido)phenyl)acetate (10a) (95 mg, 0.21 mmol) in dioxane (3 mL) using 3-(aminomethyl)phenylboronic acid hydrochloride (6c) (59 mg, 0.31 mmol), tripotassium phosphate (1.3 M solution) (0.48 mL, 0.63 mmol), tricyclohexylphosphine (18 mg, 0.06 mmol) and Pd$_2$(dba)$_3$ (19 mg, 0.021 mmol) under an Ar atmosphere and heating at 125° C. for 30 min in a microwave. This gave after workup, purification by flash column chromatography [silica (12 g), eluting with DMA80 in DCM from 0-60%] followed by reverse phase column [C18 (50 g), eluting with ACN in water (containing 0.1% HCl) from 0-100%] ethyl 2-(2-(4-(3-(aminomethyl)phenyl)-1-(cyclopropylmethyl)-1H-indazole-6-carboxamido)phenyl)acetate (10c) (26 mg, 0.054 mmol, 25.9% yield) as a white solid; $^1$H NMR (300 MHz, DMSO-$d_6$) δ 10.27 (s, 1H, D$_2$O exchangeable), 8.52 (s, 3H, D$_2$O exchangeable), 8.46-8.36 (m, 2H), 8.00 (s, 1H), 7.93-7.78 (m, 2H), 7.67-7.53 (m, 2H), 7.50-7.41 (m, 1H), 7.41-7.32 (m, 2H), 7.32-7.22 (m, 1H), 4.44 (d, J=7.0 Hz, 2H), 4.21-4.11 (m, 2H), 3.94 (q, J=7.1 Hz, 2H), 3.80 (s, 2H), 1.45-1.32 (m, 1H), 0.96 (t, J=7.1 Hz, 3H), 0.59-0.38 (m, 4H); MS (ES+): 483.4 (M+1); (ES−): 517.5 (M+Cl); HPLC purity, 97.36%, and 2-(2-(4-(3-(aminomethyl)phenyl)-1-(cyclopropylmethyl)-1H-indazole-6-carboxamido)phenyl)acetic acid (10d) (7 mg, 0.015 mmol, 7.40% yield) as a white solid; $^1$H NMR (300 MHz, DMSO-$d_6$) δ 10.25 (s, 1H, D$_2$O exchangeable), 8.55-8.33 (m, 5H), 7.98 (d, J=1.7 Hz, 1H, partially D$_2$O exchangeable), 7.91-7.80 (m, 2H), 7.67-7.54 (m, 2H), 7.54-7.45 (m, 1H), 7.41-7.30 (m, 2H), 7.30-7.18 (m, 1H), 4.44 (d, J=7.0 Hz, 2H), 4.22-4.09 (m, 2H), 3.72 (s, 2H), 1.50-1.33 (m, 1H), 0.64-0.38 (m, 4H); MS (ES+): 455.4 (M+1); (ES−): 453.4 (M−1), 489.4 (M+Cl); HPLC purity, 99.31%.

Scheme-11

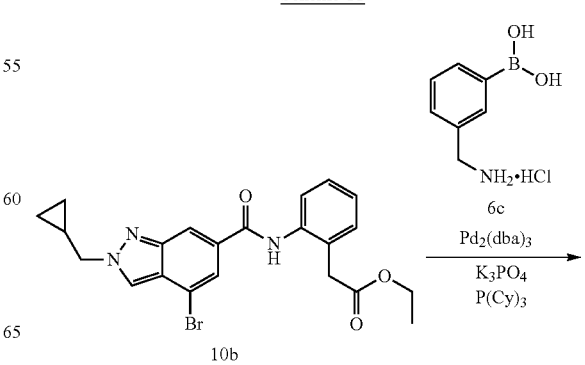

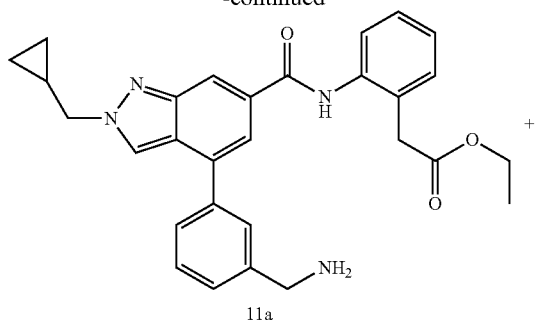

11a

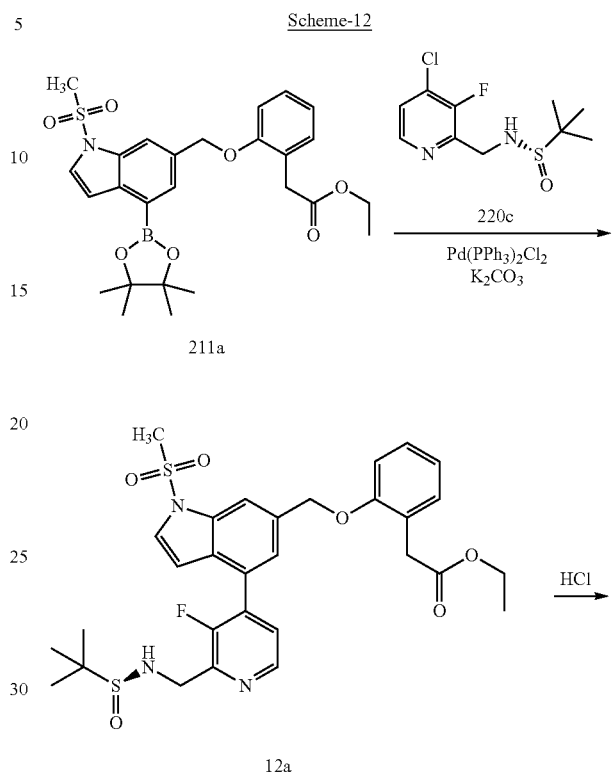

11b

Preparation of Ethyl 2-(2-(4-(3-(aminomethyl)phenyl)-2-(cyclopropylmethyl)-2H-indazole-6-carboxamido)phenyl)acetate (11a) and 2-(2-(4-(3-(aminomethyl)phenyl)-2-(cyclopropylmethyl)-2H-indazole-6-carboxamido)phenyl)acetic Acid (11b)

Compounds 11a and 11b were prepared according to the procedure reported in step-3 of Scheme-1 from ethyl 2-(2-(4-bromo-2-(cyclopropylmethyl)-2H-indazole-6-carboxamido)phenyl)acetate (10b) (86 mg, 0.19 mmol) in dioxane (3 mL) using 3-(aminomethyl)phenylboronic acid hydrochloride (6c) (53 mg, 0.28 mmol), tripotassium phosphate (1.3 M solution) (0.44 mL, 0.57 mmol), tricyclohexylphosphine (16 mg, 0.06 mmol) and Pd$_2$(dba)$_3$ (17 mg, 0.02 mmol) under an Ar atmosphere and heating at 125° C. for 30 min in a microwave. This gave after workup, purification by flash column chromatography [silica (12 g), eluting with DMA80 in DCM from 0-60%] followed by reverse phase column [C18 (50 g), eluting with ACN in water (containing 0.1% HCl) from 0-100%] ethyl 2-(2-(4-(3-(aminomethyl)phenyl)-2-(cyclopropylmethyl)-2H-indazole-6-carboxamido)phenyl)acetate (11a) (10 mg, 11% yield) as a white solid; $^1$H NMR (300 MHz, DMSO-d$_6$) δ 10.13 (s, 1H, D$_2$O exchangeable), 8.94 (s, 1H), 8.55 (s, 3H, D$_2$O exchangeable), 8.33 (s, 1H), 7.96 (s, 1H), 7.87-7.72 (m, 2H), 7.68-7.52 (m, 2H), 7.48-7.41 (m, 1H), 7.39-7.30 (m, 2H), 7.30-7.21 (m, 1H), 4.39 (d, J=7.2 Hz, 2H), 4.16 (q, J=6.0 Hz, 2H), 3.96 (q, J=7.1 Hz, 2H), 3.80 (s, 2H), 1.53-1.39 (m, 1H), 1.01 (t, J=7.1 Hz, 3H), 0.62-0.44 (m, 4H); MS (ES+): 483.4 (M+1); 505.4 (M+Na); (ES−): 481.4 (M−1); HPLC purity, 95.20% and 2-(2-(4-(3-(aminomethyl)phenyl)-2-(cyclopropylmethyl)-2H-indazole-6-carboxamido)phenyl)acetic acid (11b) (13 mg, 15% yield) as an off white solid; $^1$H NMR (300 MHz, DMSO-d$_6$) δ 10.17 (s, 1H, D$_2$O exchangeable), 8.96 (s, 1H), 8.59 (s, 3H, D$_2$O exchangeable), 8.33 (s, 1H), 7.97 (s, 1H), 7.86-7.80 (m, 1H), 7.80-7.74 (m, 1H), 7.66-7.48 (m, 3H), 7.39-7.29 (m, 2H), 7.28-7.19 (m, 1H), 4.38 (d, J=7.3 Hz, 2H), 4.21-4.09 (m, 2H), 3.73 (s, 2H), 1.57-1.38 (m, 1H), 0.61-0.45 (m, 4H); MS (ES+): 455.4 (M+1); 477.4 (M+Na); (ES−): 453.4 (M−1); HPLC purity, 98.50%.

Scheme-12

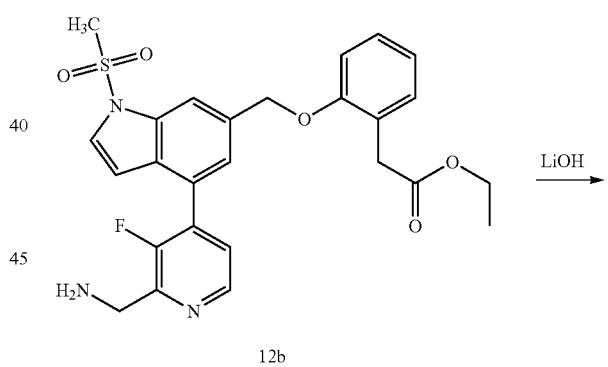

211a

220c
Pd(PPh$_3$)$_2$Cl$_2$
K$_2$CO$_3$
→

12a

HCl
→

12b

LiOH
→

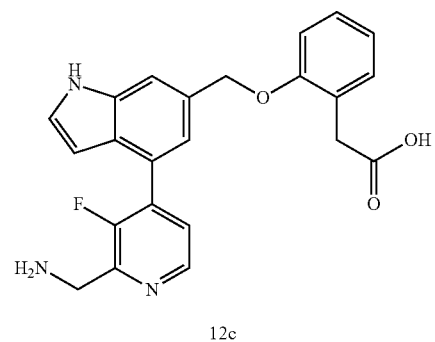

12c

Preparation of 2-(2-((4-(2-(aminomethyl)-3-fluoro-pyridin-4-yl)-1H-indol-6-yl)methoxy)phenyl)acetic Acid (12c)

Step-1: Preparation of (S)-ethyl 2-(2-((4-(2-((1,1-dimethylethylsulfinamido)methyl)-3-fluoropyridin-4-yl)-1-(methylsulfonyl)-1H-indol-6-yl)methoxy)phenyl)acetate (12a)

Compound 12a was prepared according to the procedure reported in step-3 of Scheme-1 from ethyl 2-(2-((1-(methylsulfonyl)-4-(4,4,5,5-tetramethyl-1,3,2-dioxaborolan-2-yl)-1H-indol-6-yl)methoxy)phenyl)acetate (211a) (0.6 g, 1.17 mmol) in dioxane (5 mL) using (S)—N-((4-chloro-3-fluoropyridin-2-yl)methyl)-2-methylpropane-2-sulfinamide (220c) (0.46 g, 1.75 mmol), bis(triphenylphosphine)palladium(II) chloride (0.12 g, 0.18 mmol) and a solution of K$_2$CO$_3$ (0.40 g, 2.92 mmol) in water (0.5 mL) under an Ar atmosphere and heating at 90° C. for 4 h on oil bath. This gave after workup, purification by flash column chromatography [silica (12 g), eluting with EtOAc/MeOH=9:1 in DCM from 0-70%] (S)-ethyl 2-(2-((4-(2-((1,1-dimethylethylsulfinamido)methyl)-3-fluoropyridin-4-yl)-1-(methylsulfonyl)-1H-indol-6-yl)methoxy)phenyl)acetate (12a) (0.33 g, 46% yield) as a yellow solid; MS (ES+): 616.0 (M+1).

Step-2: Preparation of Ethyl 2-(2-((4-(2-(aminomethyl)-3-fluoropyridin-4-yl)-1-(methylsulfonyl)-1H-indol-6-yl)methoxy)phenyl)acetate (12b)

Compound 12b was prepared according to the procedure reported in step-5 of Scheme-220 from (S)-ethyl 2-(2-((4-(2-((1,1-dimethylethylsulfinamido)methyl)-3-fluoropyridin-4-yl)-1-(methylsulfonyl)-1H-indol-6-yl)methoxy)phenyl)acetate (12a) (0.33 g, 0.54 mmol) in methanol (10 mL) using hydrochloric acid (4 M in 1,4-dioxane, 0.40 mL, 1.61 mmol). This gave after workup compound 12b (0.26 g, 95% yield) as a yellow solid. This was subjected to purification using reverse phase column chromatography [C18 (50 g), eluting with ACN in water (containing 0.1% HCl) from 0-100%] to afford ethyl 2-(2-((4-(2-(aminomethyl)-3-fluoropyridin-4-yl)-1-(methylsulfonyl)-1H-indol-6-yl)methoxy)phenyl)acetate (12b) HCl salt as a yellow solid; $^1$H NMR (300 MHz, DMSO-d$_6$) δ 8.68 (s, 3H), 8.61 (d, J=4.9 Hz, 1H), 8.10 (t, J=1.0 Hz, 1H), 7.75 (d, J=3.8 Hz, 1H), 7.67 (t, J=5.3 Hz, 1H), 7.54-7.52 (m, 1H), 7.31-7.19 (m, 2H), 7.14 (dd, J=8.3, 1.1 Hz, 1H), 6.91 (td, J=7.4, 1.1 Hz, 1H), 6.81-6.76 (m, 1H), 5.32 (s, 2H), 4.34 (d, J=6.0 Hz, 2H), 3.91 (q, J=7.1 Hz, 2H), 3.63 (s, 2H), 3.55 (s, 3H), 0.97 (t, J=7.1 Hz, 3H); $^{19}$F NMR (282 MHz, DMSO-d$_6$) δ−128.70; MS (ES+): 512.9 (M+1).

Step-3: Preparation of 2-(2-((4-(2-(aminomethyl)-3-fluoropyridin-4-yl)-1H-indol-6-yl)methoxy)phenyl)acetic Acid (12c)

Compound 12c was prepared according to the procedure reported in step-6 of Scheme-1 from ethyl 2-(2-((4-(2-(aminomethyl)-3-fluoropyridin-4-yl)-1-(methylsulfonyl)-1H-indol-6-yl)methoxy)phenyl)acetate (12b) (0.15 g, 0.29 mmol) in MeOH/THF (4 mL, each) using lithium hydroxide hydrate (123 mg, 2.93 mmol) in water (1 mL). This gave after workup and purification by reverse phase column [C18 (50 g), eluting with ACN in water (containing 0.1% HCl) from 0-100%] 2-(2-((4-(2-(aminomethyl)-3-fluoropyridin-4-yl)-1H-indol-6-yl)methoxy)phenyl)acetic acid (12c) (0.06 g, 52% yield) HCl salt as a yellow solid; $^1$H NMR (300 MHz, DMSO-d$_6$) δ 11.51 (s, 1H), 8.57 (s, 3H), 8.56-8.54 (m, 1H), 7.69 (t, J=5.4 Hz, 1H), 7.65 (d, J=1.1 Hz, 1H), 7.49 (t, J=2.8 Hz, 1H), 7.27 (d, J=1.2 Hz, 1H), 7.26-7.18 (m, 2H), 7.14-7.08 (m, 1H), 6.89 (td, J=7.4, 1.1 Hz, 1H), 6.39 (t, J=2.7 Hz, 1H), 5.26 (s, 2H), 4.44-4.30 (m, 2H), 3.57 (s, 2H); $^{19}$F NMR (282 MHz, DMSO-d$_6$) δ−128.77; MS (ES+): 406.0 (M+1). HPLC purity: 98.02%.

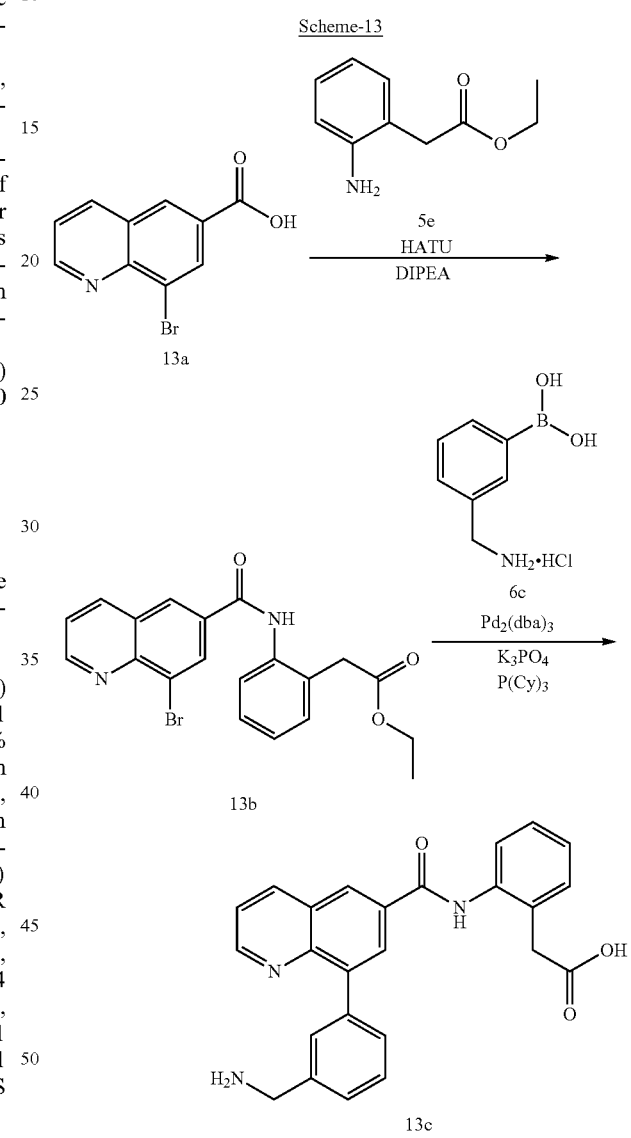

Scheme-13

Preparation of 2-(2-(8-(3-(aminomethyl)phenyl)quinoline-6-carboxamido)phenyl)acetic Acid (13c)

Step-1: Preparation of Ethyl 2-(2-(8-bromoquinoline-6-carboxamido)phenyl)acetate (13b)

Compound 13b was prepared according to the procedure reported in step-4 of Scheme-1, from 8-bromoquinoline-6-carboxylic acid (13a) (250 mg, 0.992 mmol, CAS #791632-21-8) using ethyl 2-(2-aminophenyl)acetate (5e) (213 mg, 1.19 mmol), DIPEA (0.52 mL, 2.98 mmol) and HATU (453 mg, 1.19 mmol). This gave after workup and purification by flash column chromatography [silica (12 g), eluting with MeOH:EtOAc (9:1) in hexanes 0 to 60%] ethyl 2-(2-(8-bromoquinoline-6-carboxamido)phenyl)acetate (13b) (315 mg, 77% yield) as a white solid; $^1$H NMR (300 MHz, DMSO-d$_6$) δ 10.35 (s, 1H), 9.13 (dd, J=4.2, 1.6 Hz, 1H), 8.66 (d, J=1.9 Hz, 1H), 8.62 (td, J=4.1, 1.7 Hz, 2H), 7.75 (dd, J=8.3, 4.2 Hz, 1H), 7.45-7.23 (m, 4H), 3.96 (q, J=7.1 Hz, 2H), 3.78 (s, 2H), 1.00 (t, J=7.1 Hz, 3H).

Step-2: Preparation of 2-(2-(8-(3-(aminomethyl) phenyl)quinoline-6-carboxamido)phenyl)acetic Acid (13c)

Compound 13c was prepared according to the procedure reported in step-3 of Scheme-1 from ethyl 2-(2-(8-bromo-quinoline-6-carboxamido)phenyl)acetate (13b) (150 mg, 0.36 mmol) in dioxane (2 mL) using 3-(aminomethyl) phenylboronic acid hydrochloride (6c) (68 mg, 0.363 mmol), tripotassium phosphate (1.3 M solution) (0.84 mL, 1.09 mmol), tricyclohexylphosphine (31 mg, 0.11 mmol) and Pd$_2$(dba)$_3$ (33 mg, 0.036 mmol) under an Ar atmosphere and heating at 125° C. for 1 h in a microwave. This gave after workup, purification by flash column chromatography [silica (40 g), eluting with ethyl acetate in hexanes (0 to 40%)] followed by reverse phase column [C18 (50 g), eluting with ACN in water (containing 0.1% HCl) from 0-100%] 2-(2-(8-(3-(aminomethyl)phenyl)quinoline-6-carboxamido)phenyl)acetic acid (13c) (18 mg, 12% yield) as a white powder; $^1$H NMR (300 MHz, DMSO-d$_6$) δ 10.43 (s, 1H, D$_2$O exchangeable), 9.04 (dd, J=4.2, 1.7 Hz, 1H), 8.70 (s, 1H), 8.65 (dt, J=8.5, 1.8 Hz, 1H), 8.50 (s, 3H, D$_2$O exchangeable), 8.35 (t, J=1.6 Hz, 1H), 7.87 (s, 1H), 7.82-7.76 (m, 1H), 7.76-7.69 (m, 1H), 7.60-7.55 (m, 2H), 7.48 (d, J=7.6 Hz, 1H), 7.40-7.30 (m, 2H), 7.30-7.21 (m, 1H), 4.14 (q, J=5.9 Hz, 2H), 3.73 (s, 2H); MS (ES+): 412.3 (M+1); MS (ES−): 410.4 (M−1); HPLC purity: 93.59%.

Scheme-14

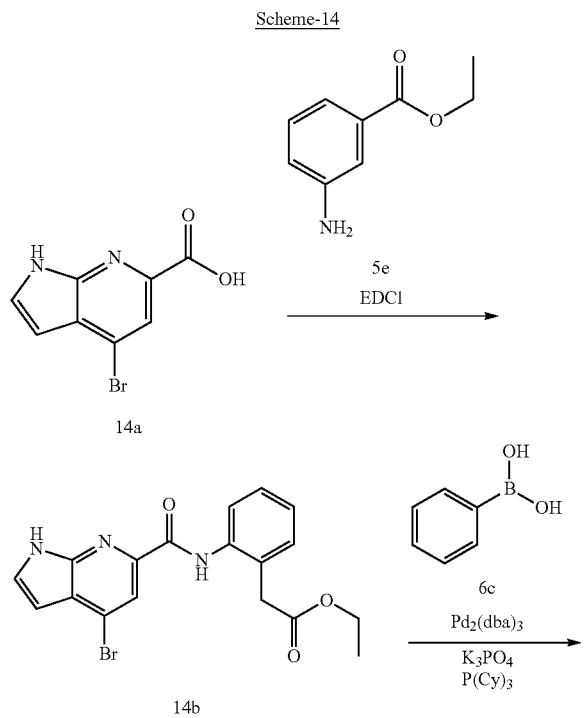

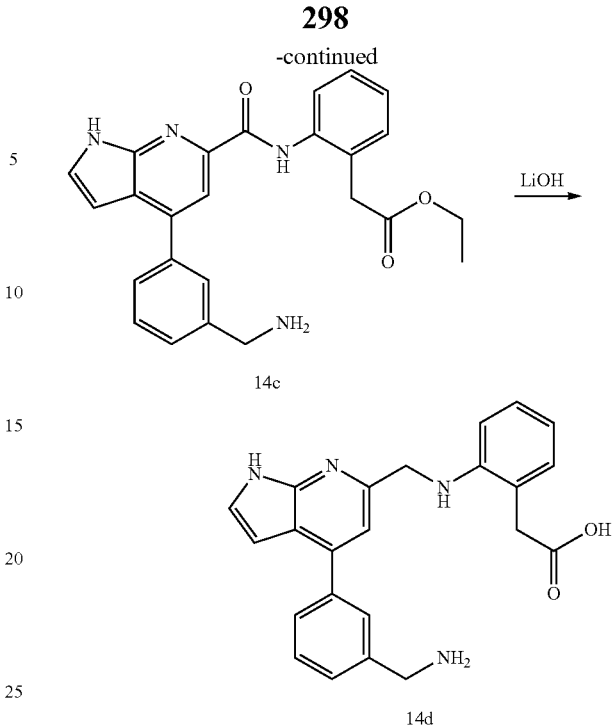

Preparation of 2-(2-(4-(3-(aminomethyl)phenyl)-1H-pyrrolo[2,3-b]pyridine-6-carboxamido)phenyl)acetic Acid (14d)

Step-1: Preparation of Ethyl 2-(2-(4-bromo-1H-pyrrolo[2,3-b]pyridine-6-carboxamido)phenyl)acetate (14b)

Compound 14b was prepared according to the procedure reported in step-1 of Scheme-7 from 4-bromo-1H-pyrrolo [2,3-b]pyridine-6-carboxylic acid (14a) (300 mg, 1.25 mmol; CAS #1190321-81-3) in MeOH (10 mL) using ethyl 2-(2-aminophenyl)acetate (5e) (268 mg, 1.49 mmol) and EDCI (286 mg, 1.49 mmol). This gave after workup, purification by flash column chromatography [silica (12 g), eluting with EtOAc in hexane from 0-60%] ethyl 2-(2-(4-bromo-1H-pyrrolo[2,3-b]pyridine-6-carboxamido)phenyl) acetate (14b) (356 mg, 71% yield) as an off white solid; MS (ES+): 424.2, 426.2 (M+Na), (ES−): 400.2, 402.3 (M−1).

Step-2: Preparation of Ethyl 2-(2-(4-(3-(aminomethyl)phenyl)-1H-pyrrolo[2,3-b]pyridine-6-carboxamido)phenyl)acetate (14c)

Compound 14c was prepared according to the procedure reported in step-3 of Scheme-1 from ethyl 2-(2-(4-bromo-1H-pyrrolo[2,3-b]pyridine-6-carboxamido)phenyl)acetate (14b) (200 mg, 0.55 mmol) in dioxane (3 mL) using 3-(aminomethyl)phenylboronic acid hydrochloride (6c) (154 mg, 0.82 mmol), tripotassium phosphate (1.3 M solution) (0.72 mL, 0.93 mmol), tricyclohexylphosphine (46 mg, 0.16 mmol) and Pd$_2$(dba)$_3$ (50 mg, 0.055 mmol) under an Ar atmosphere and heating at 125° C. for 1 h in a microwave. This gave after workup, purification by flash column chromatography [silica (12 g), eluting with DMA80 in DCM from 0-70%] followed by purification by reverse column [C18 (50 g), eluting with ACN in water (containing 0.1% HCl) from 0-100%] ethyl 2-(2-(4-(3-(aminomethyl)

phenyl)-1H-pyrrolo[2,3-b]pyridine-6-carboxamido)phenyl) acetate (14c) (108 mg, 46% yield) as a white solid; ¹H NMR (300 MHz, DMSO-d₆) δ 12.14 (s, 1H, D₂O exchangeable), 10.31 (s, 1H, D₂O exchangeable), 8.55 (s, 3H, D₂O exchangeable), 8.06 (s, 1H), 7.98 (s, 1H), 7.89-7.76 (m, 3H), 7.64 (d, J=4.5 Hz, 2H), 7.42-7.29 (m, 2H), 7.27-7.14 (m, 1H), 6.93-6.82 (m, 1H), 4.23-4.12 (m, 2H), 4.08 (q, J=7.1 Hz, 2H), 3.81 (s, 2H), 1.06 (t, J=7.1 Hz, 3H); MS (ES+): 429.4 (M+1); (ES−): 427.4 (M−1), 463.4 (M+Cl); HPLC purity, 99.45%.

Step-3: Preparation of 2-(2-(4-(3-(aminomethyl) phenyl)-1H-pyrrolo[2,3-b]pyridine-6-carboxamido) phenyl)acetic Acid (14d)

Compound 14d was prepared according to the procedure reported in step-6 of Scheme-1 from ethyl 2-(2-(4-(3-(aminomethyl)phenyl)-1H-pyrrolo[2,3-b]pyridine-6-carboxamido)phenyl)acetate (14c) (16 mg, 0.038 mmol) in MeOH/THF (3 mL) using lithium hydroxide hydrate (7.98 mg, 0.19 mmol) in water (1 mL). This gave after workup and purification by reverse phase column chromatography [C18 (50 g), eluting with ACN in water (containing 0.1% HCl) from 0-100%] 2-(2-(4-(3-(aminomethyl)phenyl)-1H-pyrrolo[2,3-b]pyridine-6-carboxamido)phenyl)acetic acid (14d) (12 mg, 79% yield) as a yellow solid; ¹H NMR (300 MHz, DMSO-d₆) δ 12.15 (s, 1H, D₂O exchangeable), 10.35 (s, 1H, D₂O exchangeable), 8.39 (s, 3H, D₂O exchangeable), 8.07 (s, 1H), 7.98 (s, 1H), 7.90-7.78 (m, 3H), 7.70-7.57 (m, 2H), 7.43-7.30 (m, 2H), 7.26-7.13 (m, 1H), 6.90-6.80 (m, 1H), 4.18 (q, J=5.9 Hz, 2H), 3.73 (s, 2H); MS (ES+): 401.3 (M+1); (ES−): 399.3 (M−1), 435.4 (M+Cl); HPLC purity, 96.09%.

Scheme-15

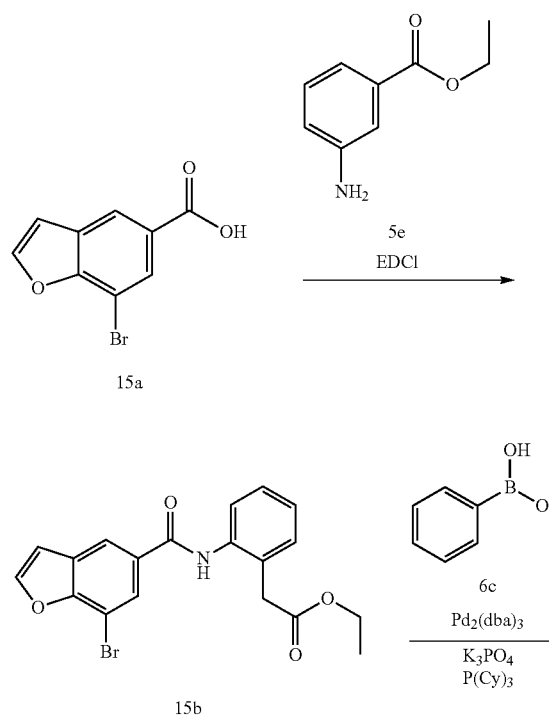

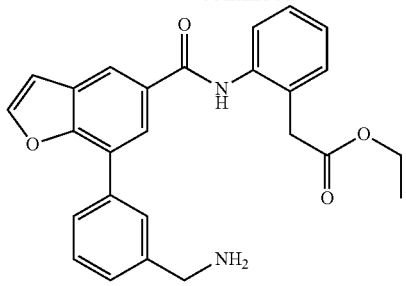

15c

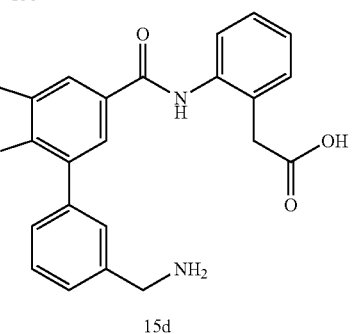

15d

Preparation of 2-(2-(7-(3-(aminomethyl)phenyl) benzofuran-5-carboxamido)phenyl)acetic Acid (15d)

Step-1: Preparation of Ethyl 2-(2-(7-bromobenzofuran-5-carboxamido)phenyl)acetate (15b)

Compound 15b was prepared according to the procedure reported in step-1 of Scheme-7 from 7-bromobenzofuran-5-carboxylic acid (15a) (100 mg, 0.42 mmol; CAS #286836-25-7) in MeOH (10 mL) using ethyl 2-(2-aminophenyl) acetate (5e) (89 mg, 0.5 mmol) and EDCI (95 mg, 0.5 mmol). This gave after workup, purification by flash column chromatography [silica (12 g), eluting with EtOAc in hexane from 0-60%] ethyl 2-(2-(7-bromobenzofuran-5-carboxamido)phenyl)acetate (15b) (80 mg, 48% yield) as an pink semi-solid; MS (ES+): 424.2, 426.2 (M+Na), (ES−): 400.2, 402.2 (M−1)

Step-2: Preparation of 2-(2-(7-(3-(aminomethyl) phenyl)benzofuran-5-carboxamido)phenyl)acetic Acid (15d)

Compound 15d was prepared according to the procedure reported in step-3 of Scheme-1 from ethyl 2-(2-(7-bromobenzofuran-5-carboxamido)phenyl)acetate (15b) (80 mg, 0.2 mmol) in dioxane (3 mL) using 3-(aminomethyl)phenylboronic acid hydrochloride (6c) (56 mg, 0.3 mmol), tripotassium phosphate (1.3 M solution) (0.26 mL, 0.34 mmol), tricyclohexylphosphine (17 mg, 0.06 mmol) and Pd₂(dba)₃ (18 mg, 0.02 mmol) under an Ar atmosphere and heating at 125° C. for 1 h in a microwave. This gave after workup, purification by flash column chromatography [silica (12 g), eluting with DMA80 in DCM from 0-70%] followed by purification by reverse phase column [C18 (50 g), eluting with ACN in water (containing 0.1% HCl) from 0-100%] ethyl 2-(2-(7-(3-(aminomethyl)phenyl)benzofuran-5-carboxamido)phenyl)acetate (15c) (21 mg, 25% yield) as a white solid; ¹H NMR (300 MHz, DMSO-d₆) δ 10.17 (s, 1H, D<sub>2</sub>O exchangeable), 8.43 (s, 3H, D₂O exchangeable), 8.33-8.27 (m, 1H), 8.22 (d, J=2.2 Hz, 1H), 8.21-8.18 (m, 1H), 8.08 (s, 1H), 8.03-7.94 (m, 1H), 7.67-7.54 (m, 2H), 7.45-7.39 (m, 1H), 7.38-7.30 (m, 2H), 7.30-7.18 (m, 2H), 4.16 (s, 2H), 3.95 (q, J=7.1 Hz, 2H), 3.79 (s, 2H), 0.98 (t, J=7.1 Hz, 3H); MS (ES+): 429.3 (M+1); 451.3 (M+Na); (ES−): 463.3 (M+Cl); HPLC purity, 99.50% and 2-(2-(7-(3-(aminomethyl)phenyl)benzofuran-5-carboxamido)phenyl)acetic acid (15d) (25 mg, 31% yield) as a white solid; $^1$H NMR (300 MHz, DMSO-d$_6$) δ 12.31 (s, 1H, D$_2$O exchangeable), 10.20 (s, 1H, D$_2$O exchangeable), 8.41 (s, 3H, D$_2$O exchangeable), 8.34-8.29 (m, 1H), 8.24-8.20 (m, 1H), 8.20-8.16 (m, 1H), 8.09-8.04 (m, 1H), 8.02-7.96 (m, 1H), 7.66-7.55 (m, 2H), 7.51-7.44 (m, 1H), 7.38-7.28 (m, 2H), 7.27-7.19 (m, 2H), 4.21-4.09 (m, 2H), 3.71 (s, 2H); MS (ES+): 401.3 (M+1); 423.3 (M+Na); (ES−): 399.3 (M−1), 435.3 (M+Cl); HPLC purity, 92.60%.

Scheme-16

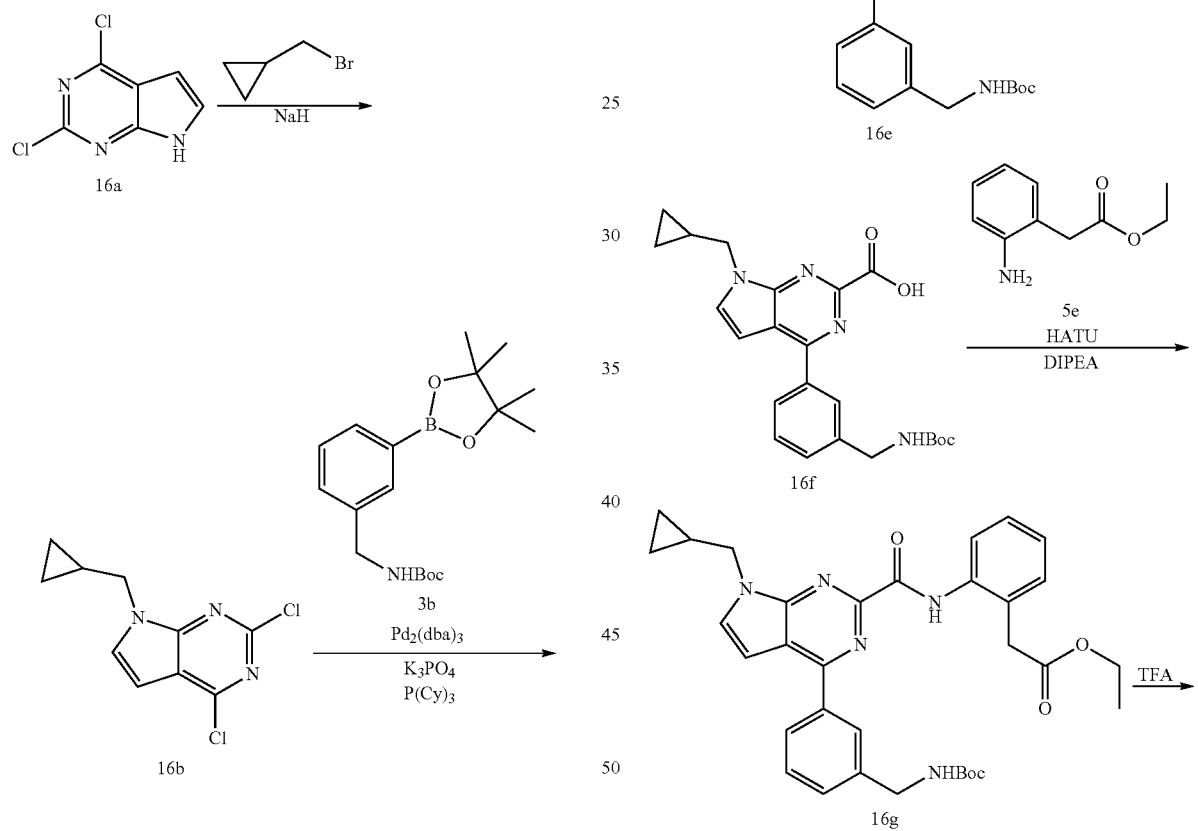

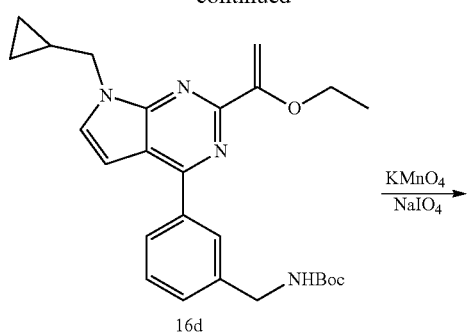

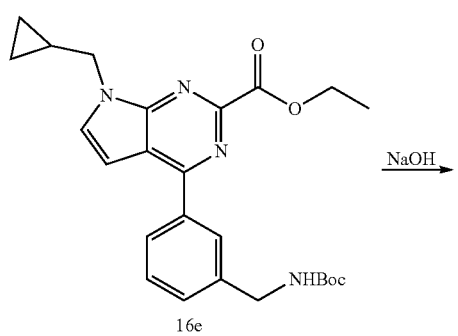

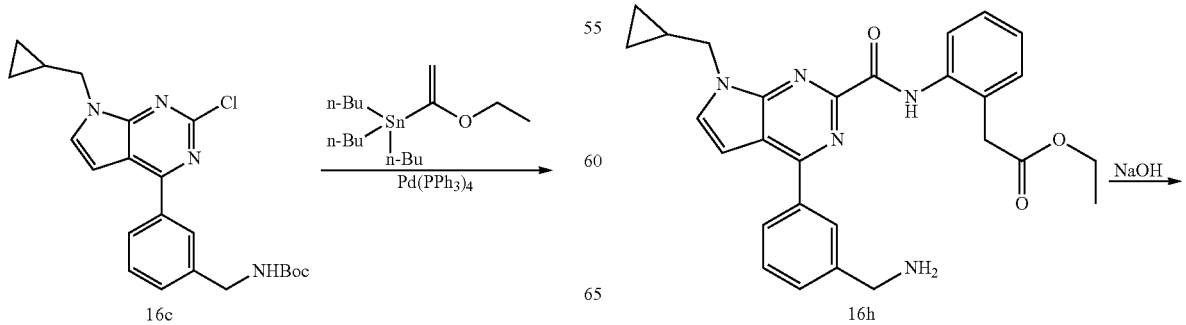

-continued

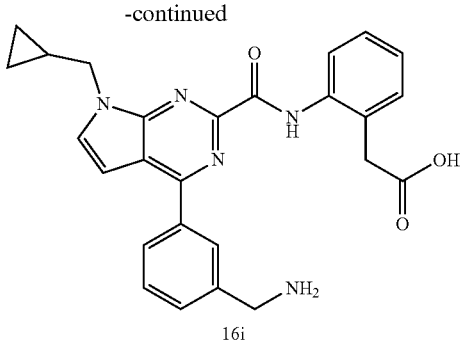

16i

Preparation of 2-(2-(4-(3-(aminomethyl)phenyl)-7-(cyclopropylmethyl)-7H-pyrrolo[2,3-d]pyrimidine-2-carboxamido)phenyl)acetic Acid (16i)

Step-1: Preparation of 2,4-dichloro-7-(cyclopropylmethyl)-7H-pyrrolo[2,3-d]pyrimidine (16b)

To a solution of 2,4-dichloro-7H-pyrrolo[2,3-d]pyrimidine (16a) (1 g, 5.32 mmol; CAS #90213-66-4) in acetonitrile (35 mL) at 0° C. was added sodium hydride (319 mg, 7.98 mmol) portion-wise. The reaction mixture was stirred at room temperature for 30 minutes until gas evolution ceased. Then (bromomethyl)cyclopropane (1.62 g, 11.97 mmol) was added and the resulting mixture was stirred at RT overnight. The reaction mixture was poured into water and extracted with EtOAc (3×). The organic layers were combined, dried, filtered and concentrated in vacuum. The residue obtained was purified by flash column chromatography [silica (24 g), eluting with EtOAc in hexane from 0-60%] to afford 2,4-dichloro-7-(cyclopropylmethyl)-7H-pyrrolo[2,3-d]pyrimidine (16b) (998 mg, 78% yield) as a white solid; $^1$H NMR (300 MHz, DMSO-d$_6$) δ 7.88 (d, J=3.6 Hz, 1H), 6.71 (d, J=3.6 Hz, 1H), 4.09 (d, J=7.2 Hz, 2H), 1.34-1.17 (m, 1H), 0.58-0.48 (m, 2H), 0.48-0.37 (m, 2H); MS (ES+): 265.3 (M+Na).

Step-2: Preparation of tert-butyl 3-(2-chloro-7-(cyclopropylmethyl)-7H-pyrrolo[2,3-d]pyrimidin-4-yl)benzylcarbamate (16c)

Compound 16c was prepared according to the procedure reported in step-3 of Scheme-1 from 2,4-dichloro-7-(cyclopropylmethyl)-7H-pyrrolo[2,3-d]pyrimidine (16b) (4.5 g, 18.59 mmol) in dioxane (100 mL) using tert-butyl 3-(4,4,5,5-tetramethyl-1,3,2-dioxaborolan-2-yl)benzylcarbamate (3b) (4.42 g, 13.28 mmol), tripotassium phosphate (22.47 mL, 29.2 mmol, 1.3 M solution in water), tricyclohexylphosphine (1.12 g, 3.98 mmol) and Pd$_2$(dba)$_3$ (1.22 g, 1.33 mmol) in Ar atmosphere and heating at 120° C. for 60 min on oil bath. This gave after workup and purification by flash column chromatography [silica (80 g), eluting with EtOAc in hexane from 0-70%] tert-butyl 3-(2-chloro-7-(cyclopropylmethyl)-7H-pyrrolo[2,3-d]pyrimidin-4-yl)benzylcarbamate (16c) (3.2 g, 58% yield) as a white solid; $^1$H NMR (300 MHz, DMSO-d$_6$) δ 8.10-7.97 (m, 2H), 7.87 (d, J=3.7 Hz, 1H), 7.61-7.50 (m, 2H), 7.49-7.41 (m, 1H), 6.99 (d, J=3.7 Hz, 1H), 4.25 (d, J=6.2 Hz, 2H), 4.11 (d, J=7.2 Hz, 2H), 1.41 (s, 9H), 1.35-1.31 (m, 1H), 0.58-0.49 (m, 2H), 0.49-0.40 (m, 2H); MS (ES+): 413.4 (M+1); 435.3 (M+Na); (ES−): 411.4 (M−1)

Step-3: Preparation of tert-butyl 3-(7-(cyclopropylmethyl)-2-(1-ethoxyvinyl)-7H-pyrrolo[2,3-d]pyrimidin-4-yl)benzylcarbamate (16d)

Compound 16d was prepared according to the procedure reported in step-1 of Scheme-1 from tert-butyl 3-(2-chloro-7-(cyclopropylmethyl)-7H-pyrrolo[2,3-d]pyrimidin-4-yl)benzylcarbamate (16c) (3.2 g, 7.75 mmol) in DMF (35 mL) using 1-ethoxyvinyltri-n-butyltin (3.17 mL, 9.30 mmol) and Pd(PPh$_3$)$_4$ (0.448 g, 0.39 mmol) in argon atmosphere and heating at 110° C. for 12 h. This gave after workup and purification by flash column chromatography [silica (24 g), eluting with EtOAc in hexane from 0-60%] tert-butyl 3-(7-(cyclopropylmethyl)-2-(1-ethoxyvinyl)-7H-pyrrolo[2,3-d]pyrimidin-4-yl)benzylcarbamate (16d) (2.5 g, 72% yield) as a white solid; 1H NMR (300 MHz, DMSO-d$_6$) δ 8.14-8.02 (m, 2H), 7.83 (d, J=3.6 Hz, 1H), 7.55 (q, J=7.8, 7.0 Hz, 2H), 7.45-7.36 (m, 1H), 6.92 (d, J=3.6 Hz, 1H), 5.63 (d, J=1.4 Hz, 1H), 4.61 (d, J=1.5 Hz, 1H), 4.26 (d, J=6.2 Hz, 2H), 4.16 (d, J=7.2 Hz, 2H), 3.98 (q, J=7.0 Hz, 2H), 1.45-1.25 (m, 13H), 0.57-0.46 (m, 4H); MS (ES+) 449.4 (M+1); (ES−) 447.4 (M−1).

Step-4: Preparation of Ethyl 4-(3-(((tert-butoxycarbonyl)amino)methyl)phenyl)-7-(cyclopropylmethyl)-7H-pyrrolo[2,3-d]pyrimidine-2-carboxylate (16e)

Compound 16e was prepared according to the procedure reported in step-2 of Scheme-1 from tert-butyl 3-(7-(cyclopropylmethyl)-2-(1-ethoxyvinyl)-7H-pyrrolo[2,3-d]pyrimidin-4-yl)benzylcarbamate (16d) (2.5 g, 5.57 mmol) in 1,4-dioxane (50 mL) using sodium periodate solution (2.384 g, 11.15 mmol) in water (20 mL) and KMnO$_4$ (0.881 g, 5.57 mmol in 4 mL water as first dose and second dose of 528 mg, 3.34 mmol after 12 h). This gave after workup and purification by flash column chromatography [silica (40 g), eluting with EtOAc in hexane from 0-60%] ethyl 4-(3-(((tert-butoxycarbonyl)amino)methyl)phenyl)-7-(cyclopropylmethyl)-7H-pyrrolo[2,3-d]pyrimidine-2-carboxylate (16e) (1.06 g, 42% yield) as a yellow solid; $^1$H NMR (300 MHz, DMSO-d$_6$) δ 8.12-8.03 (m, 3H), 7.62-7.52 (m, 2H), 7.45 (d, J=7.6 Hz, 1H), 7.04 (d, J=3.5 Hz, 1H), 4.42 (q, J=7.1 Hz, 2H), 4.27 (d, J=6.2 Hz, 2H), 4.22 (d, J=7.2 Hz, 2H), 1.45-1.30 (m, 13H), 0.57-0.45 (m, 4H).

Step-5: Preparation of 4-(3-(((tert-butoxycarbonyl)amino)methyl)phenyl)-7-(cyclopropylmethyl)-7H-pyrrolo[2,3-d]pyrimidine-2-carboxylic Acid (16f)

Compound 16f was prepared according to the procedure reported in step-4 of Scheme-4 from ethyl 4-(3-(((tert-butoxycarbonyl)amino)methyl)phenyl)-7-(cyclopropylmethyl)-7H-pyrrolo[2,3-d]pyrimidine-2-carboxylate (16e) (1.06 g, 2.353 mmol) in MeOH/THF (15 mL, 1:1) using sodium hydroxide (235 mg, 5.88 mmol) in water (3 mL). This gave after workup and purification by flash column chromatography [silica (24 g), eluting with MeOH in DCM from 0-20%] 4-(3-(((tert-butoxycarbonyl)amino)methyl)phenyl)-7-(cyclopropylmethyl)-7H-pyrrolo[2,3-d]pyrimidine-2-carboxylic acid (16f) (650 mg, 65% yield) as a yellow solid; 1H NMR (300 MHz, DMSO-d$_6$) δ 8.11-8.00 (m, 2H), 7.89 (d, J=3.6 Hz, 1H), 7.60-7.48 (m, 2H), 7.46-7.38 (m, 1H), 6.94 (d, J=3.5 Hz, 1H), 4.26 (d, J=6.2 Hz, 2H), 4.18 (d, J=7.2 Hz, 2H), 1.41 (s, 9H), 1.34-1.30 (m, 1H), 0.56-0.43 (m, 4H); MS (ES+) 423.3 (M+1); 445.3 (M+Na); (ES−), 421.4 (M−1), 457.4 (M+Cl).

Step-6: Preparation of Ethyl 2-(2-(4-(3-(((tert-butoxycarbonyl)amino)methyl)phenyl)-7-(cyclopropylmethyl)-7H-pyrrolo[2,3-d]pyrimidine-2-carboxamido)phenyl)acetate (16g)

Compound 16g was prepared according to the procedure reported in step-4 of Scheme-1 from 4-(3-(((tert-butoxycarbonyl)amino)methyl)phenyl)-7-(cyclopropylmethyl)-7H-pyrrolo[2,3-d]pyrimidine-2-carboxylic acid (16f) (150 mg, 0.536 mmol) in DMF (5 mL) using ethyl 2-(2-aminophenyl) acetate (5e) (95 mg, 0.533 mmol), DIPEA (0.12 mL, 0.71 mmol) and HATU (203 mg, 0.533 mmol). This gave after workup and purification by flash column chromatography [silica (12 g), eluting with EtOAc/MeOH (9:1) in hexane from 0-100%] ethyl 2-(2-(4-(3-(((tert-butoxycarbonyl) amino)methyl)phenyl)-7-(cyclopropylmethyl)-7H-pyrrolo [2,3-d]pyrimidine-2-carboxamido)phenyl)acetate (16g) (152 mg, 73% yield) as a white solid; MS (ES+) 584.5 (M+1).

Step-7: Preparation of Ethyl 2-(2-(4-(3-(aminomethyl)phenyl)-7-(cyclopropylmethyl)-7H-pyrrolo[2,3-d]pyrimidine-2-carboxamido)phenyl)acetate (16h)

Compound 16h was prepared according to the procedure reported in step-5 of Scheme-1 from ethyl 2-(2-(4-(3-(((tert-butoxycarbonyl)amino)methyl)phenyl)-7-(cyclopropylmethyl)-7H-pyrrolo[2,3-d]pyrimidine-2-carboxamido)phenyl)acetate (16g) (150 mg, 0.26 mmol) in DCM (10 mL) using TFA (0.4 mL, 5.14 mmol). This gave after work up and purification by flash column chromatography [silica (12 g), eluting with DMA80 in DCM from 0-100%] followed by reverse phase column [C18 (50 g), eluting with ACN in water (containing 0.1% HCl) from 0-100%] ethyl 2-(2-(4-(3-(aminomethyl)phenyl)-7-(cyclopropylmethyl)-7H-pyrrolo[2,3-d]pyrimidine-2-carboxamido)phenyl)acetate (16h) (88 mg, 71% yield) as a yellow solid; $^1$H NMR (300 MHz, DMSO-$d_6$) δ 10.79 (s, 1H, $D_2O$ exchangeable), 8.68 (s, 3H, $D_2O$ exchangeable), 8.46 (d, J=1.7 Hz, 1H), 8.43-8.35 (m, 1H), 8.11 (d, J=3.6 Hz, 1H), 7.93-7.87 (m, 1H), 7.79-7.73 (m, 1H), 7.73-7.61 (m, 1H), 7.44-7.36 (m, 2H), 7.34 (d, J=3.6 Hz, 1H), 7.27-7.15 (m, 1H), 4.37-4.25 (m, 2H), 4.17 (s, 2H), 4.00 (q, J=7.1 Hz, 2H), 3.88 (s, 2H), 1.46-1.32 (m, 1H), 1.00 (t, J=7.1 Hz, 3H), 0.60-0.45 (m, 4H); MS (ES+): 484.5 (M+1); (ES−): 482.5 (M−1); 518.5 (M+Cl); HPLC purity, 99.46%.

Step-8: Preparation of 2-(2-(4-(3-(aminomethyl)phenyl)-7-(cyclopropylmethyl)-7H-pyrrolo[2,3-d]pyrimidine-2-carboxamido)phenyl)acetic Acid (16i)

Compound 16i was prepared according to the procedure reported in step-4 of Scheme-4 from ethyl 2-(2-(4-(3-(aminomethyl)phenyl)-7-(cyclopropylmethyl)-7H-pyrrolo[2,3-d]pyrimidine-2-carboxamido)phenyl)acetate (16h) (50 mg, 0.10 mmol) in MeOH (10 mL) using sodium hydroxide (21 mg, 0.52 mmol) in water (2 mL). This gave after workup and purification by reverse phase column chromatography [C18 (50 g), eluting with ACN in water (containing 0.1% HCl) from 0-100%] 2-(2-(4-(3-(aminomethyl)phenyl)-7-(cyclopropylmethyl)-7H-pyrrolo[2,3-d]pyrimidine-2-carboxamido)phenyl)acetic acid (16i) (24 mg, 51% yield) as a yellow solid; $^1$H NMR (300 MHz, DMSO-$d_6$) δ 10.85 (s, 1H, $D_2O$ exchangeable), 8.56 (s, 3H, $D_2O$ exchangeable), 8.46-8.40 (m, 1H), 8.40-8.32 (m, 1H), 8.11 (d, J=3.6 Hz, 1H), 7.98 (dd, J=8.4, 1.3 Hz, 1H), 7.78-7.63 (m, 2H), 7.44-7.33 (m, 2H), 7.31 (d, J=3.6 Hz, 1H), 7.27-7.13 (m, 1H), 4.29 (d, J=7.2 Hz, 2H), 4.23-4.18 (m, 2H), 3.78 (s, 2H), 1.44-1.31 (m, 1H), 0.59-0.47 (m, 4H); MS (ES+): 456.3 (M+1); 478.3 (M+Na); (ES−): 454.3 (M−1); 490.3 (M+Cl); HPLC, purity, 99.60%.

Scheme-17

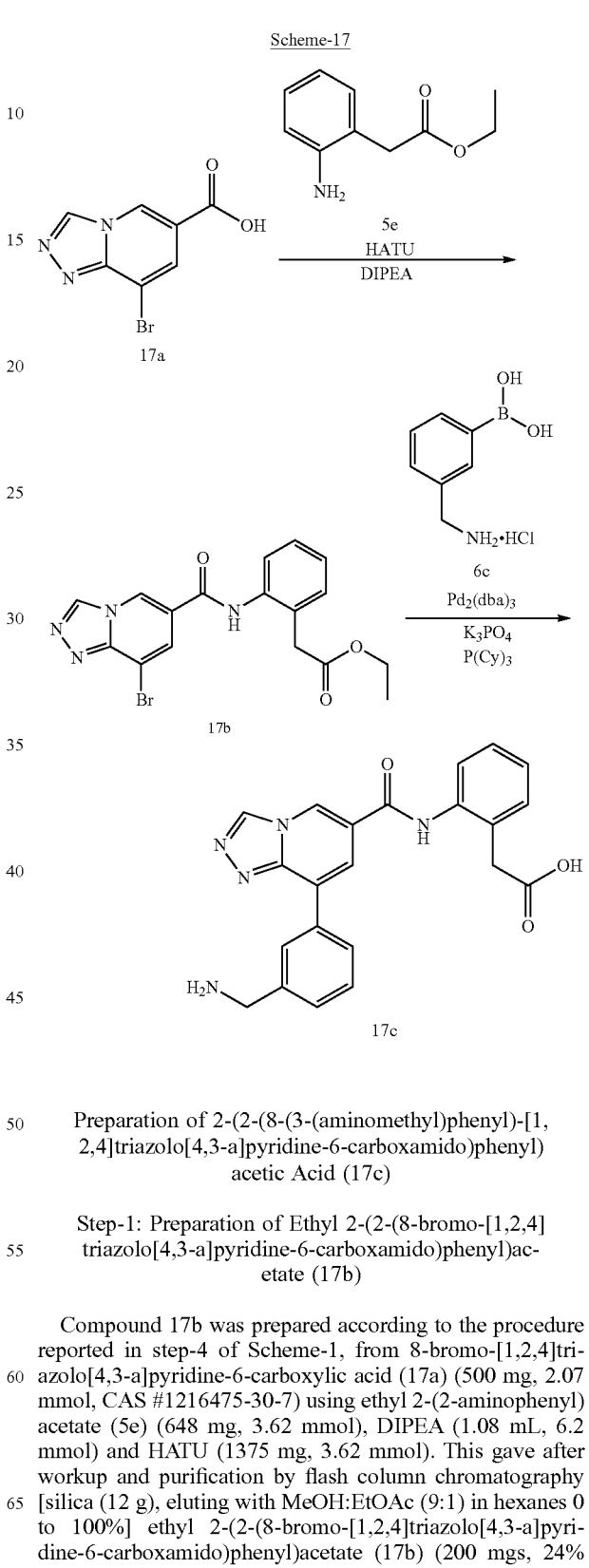

Preparation of 2-(2-(8-(3-(aminomethyl)phenyl)-[1,2,4]triazolo[4,3-a]pyridine-6-carboxamido)phenyl) acetic Acid (17c)

Step-1: Preparation of Ethyl 2-(2-(8-bromo-[1,2,4]triazolo[4,3-a]pyridine-6-carboxamido)phenyl)acetate (17b)

Compound 17b was prepared according to the procedure reported in step-4 of Scheme-1, from 8-bromo-[1,2,4]triazolo[4,3-a]pyridine-6-carboxylic acid (17a) (500 mg, 2.07 mmol, CAS #1216475-30-7) using ethyl 2-(2-aminophenyl) acetate (5e) (648 mg, 3.62 mmol), DIPEA (1.08 mL, 6.2 mmol) and HATU (1375 mg, 3.62 mmol). This gave after workup and purification by flash column chromatography [silica (12 g), eluting with MeOH:EtOAc (9:1) in hexanes 0 to 100%] ethyl 2-(2-(8-bromo-[1,2,4]triazolo[4,3-a]pyridine-6-carboxamido)phenyl)acetate (17b) (200 mgs, 24% yield) as a white solid; $^1$H NMR (300 MHz, DMSO-$d_6$) δ 10.27 (s, 1H), 9.56 (s, 1H), 9.25 (s, 1H), 8.20 (s, 1H), 7.41-7.23 (m, 4H), 3.98 (q, J=7.1 Hz, 2H), 3.74 (s, 2H), 1.05 (t, J=7.1 Hz, 3H).

Step-2: Preparation of 2-(2-(8-(3-(aminomethyl) phenyl)-[1,2,4]triazolo[4,3-a]pyridine-6-carboxamido)phenyl)acetic Acid (17c)

Compound 17c was prepared according to the procedure reported in step-3 of Scheme-1 from ethyl 2-(2-(8-bromo-[1,2,4]triazolo[4,3-a]pyridine-6-carboxamido)phenyl)acetate (17b) (200 mg, 0.5 mmol) in dioxane (3 mL) using 3-(aminomethyl)phenylboronic acid hydrochloride (6c) (139 mg, 0.74 mmol), tripotassium phosphate (1.3 M solution) (1.145 mL, 1.49 mmol), tricyclohexylphosphine (42 mg, 0.15 mmol) and Pd$_2$(dba)$_3$ (45 mg, 0.05 mmol) under an Ar atmosphere and heating at 120° C. for 1 h in a microwave. This gave after workup, purification by reverse phase column [C18 (50 g), eluting with ACN in water (containing 0.1% HCl) from 0-100%] 2-(2-(8-(3-(aminomethyl)phenyl)-[1,2,4]triazolo[4,3-a]pyridine-6-carboxamido)phenyl)acetic acid (17c) (41 mg, 21% yield) as a white solid; $^1$H NMR (300 MHz, DMSO-$d_6$) δ 10.52 (s, 1H, D$_2$O exchangeable), 9.66-9.54 (m, 1H), 9.39-9.28 (m, 1H), 8.56 (s, 3H, D$_2$O exchangeable), 8.41 (s, 1H), 8.39-8.30 (m, 2H), 7.64 (d, J=4.4 Hz, 2H), 7.48-7.38 (m, 1H), 7.42-7.31 (m, 2H), 7.33-7.23 (m, 1H), 4.32-4.02 (m, 2H), 3.72 (d, J=2.3 Hz, 2H); MS (ES+): 402.3 (M+1); MS (ES−): 400.4 (M−1); HPLC purity: 93.65%.

Scheme-18

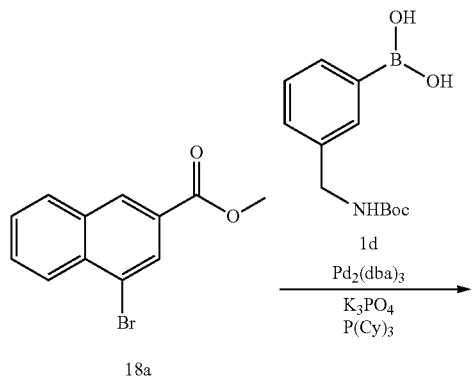

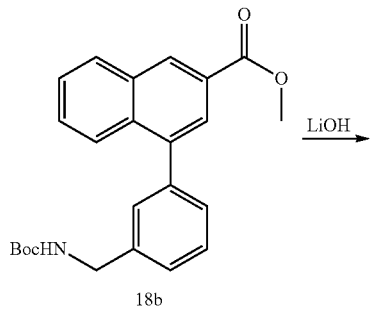

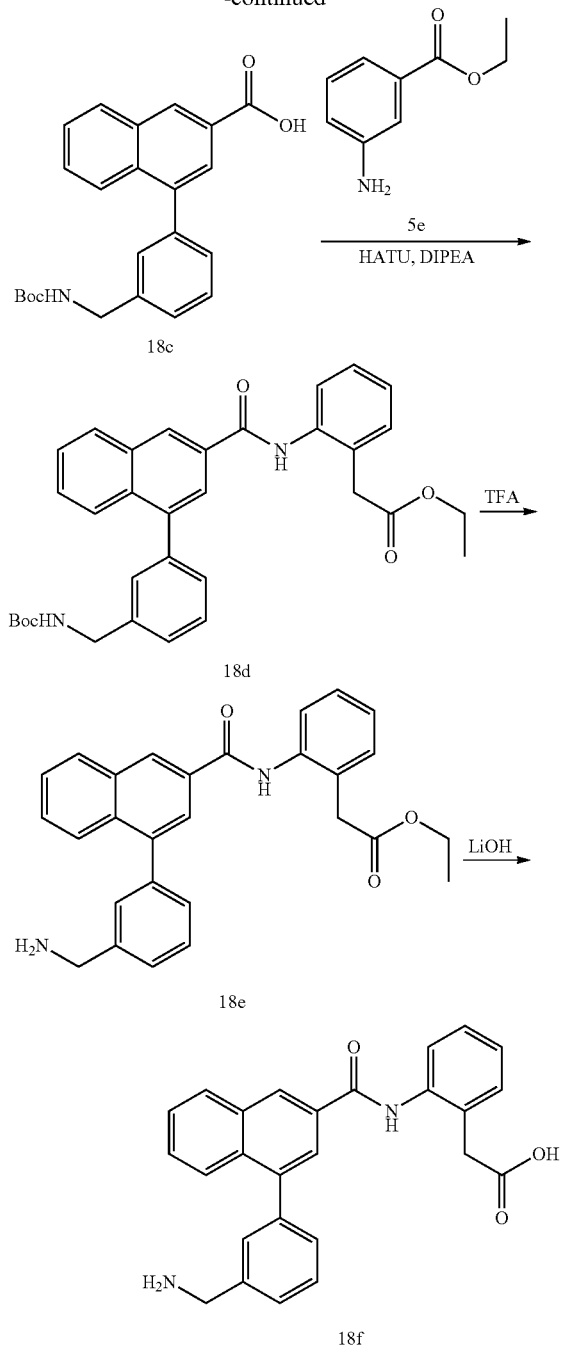

Preparation of 2-(2-(4-(3-(aminomethyl)phenyl)-2-naphthamido)phenyl)acetic Acid (18f)

Step-1: Preparation of methyl 4-(3-(((tert-butoxycarbonyl)amino)methyl)phenyl)-2-naphthoate (18b)

Compound 18b was prepared according to the procedure reported in step-3 of Scheme-1, from methyl 4-bromo-2-naphthoate (18a) (250 mg, 0.94 mmol; CAS #1013-80-5) in DMF (3 mL) using 3-((tert-butoxycarbonylamino)methyl) phenylboronic acid (1d) (355 mg, 1.42 mmol), tripotassium phosphate (1.3 M solution, 1.45 mL, 1.89 mmol), tricylcohexylphosphine (79 mg, 0.28 mmol) and Pd$_2$(dba)$_3$ (86 mg, 0.09 mmol) under a nitrogen atmosphere by heating at 120° C. for 14 h. This gave after workup and purification by flash column chromatography [silica (40 g), eluting with hexanes/ethyl acetate 0% to 100%] methyl 4-(3-(((tert-butoxycarbonyl)amino)methyl)phenyl)-2-naphthoate (18b) (257 mg, 70% yield) as an oil; $^1$H NMR (300 MHz, DMSO-d$_6$) δ 8.69 (s, 1H), 8.32-8.19 (m, 1H), 7.95-7.81 (m, 2H), 7.72-7.61 (m, 2H), 7.57-7.47 (m, 2H), 7.44-7.27 (m, 3H), 4.27-4.16 (m, 2H), 3.93 (s, 3H), 1.38 (s, 9H).

Step-2: Preparation of 4-(3-(((tert-butoxycarbonyl)amino)methyl)phenyl)-2-naphthoic Acid (18c)

Compound 18c was prepared according to the procedure reported in step-6 of Scheme-1, from methyl 4-(3-(((tert-butoxycarbonyl)amino)methyl)phenyl)-2-naphthoate (18b) (240 mg, 0.613 mmol) in THF (10 mL) using a solution of lithium hydroxide hydrate (29 mg, 1.23 mmol) in water (2 mL) This gave after workup 4-(3-(((tert-butoxycarbonyl)amino)methyl)phenyl)-2-naphthoic acid (18c) (150 mgs, 65%), which was used as such for next step; $^1$H NMR (300 MHz, DMSO-d$_6$) δ 8.61 (s, 1H), 8.24-8.11 (m, 1H), 7.89-7.77 (m, 2H), 7.67-7.56 (m, 2H), 7.48 (m, 2H), 7.35 (m, 3H), 4.22 (d, J=6.1 Hz, 2H), 1.35 (s, 9H).

Step-3: Preparation of Ethyl 2-(2-(4-(3-(((tert-butoxycarbonyl)amino)methyl)phenyl)-2-naphthamido)phenyl)acetate (18d)

Compound 18d was prepared according to the procedure reported in step-4 of Scheme-1, from 4-(3-(((tert-butoxycarbonyl)amino)methyl)phenyl)-2-naphthoic acid (18c) (150 mg, 0.397 mmol) in DMF (8 mL) using ethyl 2-(2-aminophenyl)acetate (5e) (125 mg, 0.695 mmol), DIPEA (0.21 mL, 1.2 mmol) and HATU (264 mg, 0.695 mmol). This gave after workup and purification by flash column chromatography [silica (12 g), eluting with 0-60% EtOAc/MeOH (9:1) in hexane from 0-100%] ethyl 2-(2-(4-(3-(((tert-butoxycarbonyl)amino)methyl)phenyl)-2-naphthamido)phenyl)acetate (18d) (169 mg, 79% yield) as a white solid; $^1$H NMR (300 MHz, DMSO-d$_6$) δ 10.24 (s, 1H), 8.59 (s, 1H), 8.13 (dd, J=20.3, 7.9 Hz, 1H), 7.97-7.83 (m, 2H), 7.64 (p, J=7.0 Hz, 2H), 7.52 (d, J=7.5 Hz, 1H), 7.46-7.29 (m, 7H), 7.30-7.08 (m, 1H), 4.25 (d, J=6.2 Hz, 2H), 3.94 (q, J=7.1 Hz, 2H), 3.77 (s, 2H), 1.38 (s, 9H), 0.96 (t, J=7.1 Hz, 3H).

Step-4: Preparation of Ethyl 2-(2-(4-(3-(aminomethyl)phenyl)-2-naphthamido)phenyl)acetate (18e)

Compound 18e was prepared according to the procedure reported in step-5 of Scheme-1, from ethyl 2-(2-(4-(3-(((tert-butoxycarbonyl)amino)methyl)phenyl)-2-naphthamido)phenyl)acetate (18d) (150 mg, 0.28 mmol) using TFA (0.22 mL, 2.78 mmol) in DCM (10 mL). This gave after workup ethyl 2-(2-(4-(3-(aminomethyl)phenyl)-2-naphthamido)phenyl)acetate (18e) (84 mg, 69%) which was used as such for next step; MS (ES+): 439.4 (M+1).

Step-5: Preparation of 2-(2-(4-(3-(aminomethyl)phenyl)-2-naphthamido)phenyl)acetic Acid (18f)

Compound 18f was prepared according to the procedure reported in step-6 of Scheme-1, from ethyl 2-(2-(4-(3-(aminomethyl)phenyl)-2-naphthamido)phenyl)acetate (18e) (70 mg, 0.16 mmol) in THF (5 mL) using a solution of lithium hydroxide hydrate (19 mg, 0.8 mmol) in water (2 mL) This gave after workup and purification by reverse phase column [C18 (50 g), eluting with ACN in water (containing 0.1% HCl) from 0-100%] 2-(2-(4-(3-(aminomethyl)phenyl)-2-naphthamido)phenyl)acetic acid (18f) (43 mg, 66% yield) as a white solid; $^1$H NMR (300 MHz, DMSO-d$_6$) δ 12.39 (s, 1H, D$_2$O exchangeable), 10.41 (s, 1H, D$_2$O exchangeable), 8.64 (s, 1H), 8.34 (s, 3H, D$_2$O exchangeable), 8.17 (d, J=7.7 Hz, 1H), 7.99 (d, J=1.9 Hz, 1H), 7.93 (d, J=7.8 Hz, 1H), 7.74-7.56 (m, 6H), 7.50 (d, J=7.7 Hz, 1H), 7.39-7.28 (m, 2H), 7.28-7.20 (m, 1H), 4.16 (s, 2H), 3.70 (s, 2H); MS (ES+): 411.3 (M+1), 433.3 (M+Na), (ES−): 409.4 (M−1), 445.4 (M+Cl); HPLC purity: 93.35%.

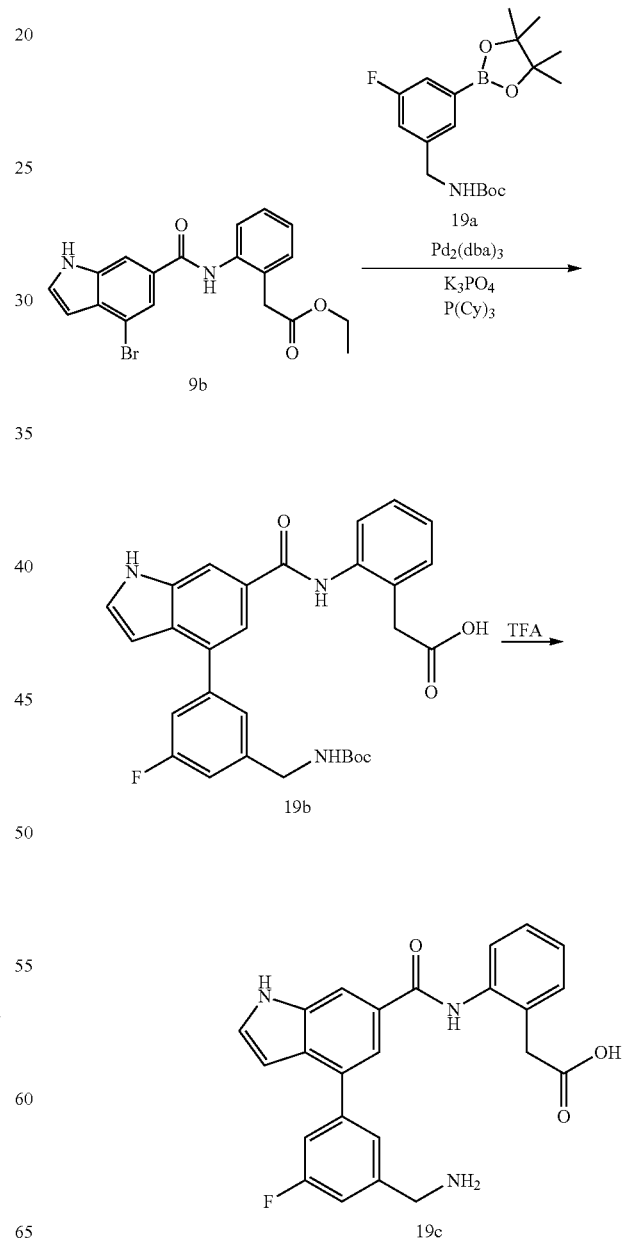

Scheme-19

Preparation of 2-(2-(4-(3-(aminomethyl)-5-fluorophenyl)-1H-indole-6-carboxamido)phenyl)acetic Acid (19c)

Step-1: Preparation of 2-(2-(4-(3-(((tert-butoxycarbonyl)amino)methyl)-5-fluorophenyl)-1H-indole-6-carboxamido)phenyl)acetic Acid (19b)

Compound 19b was prepared according to the procedure reported in step-3 of Scheme-1 from ethyl 2-(2-(4-bromo-1H-indole-6-carboxamido)phenyl)acetate (9b) (320 mg, 0.80 mmol) in dioxane (3 mL) using tert-butyl 3-fluoro-5-(4,4,5,5-tetramethyl-1,3,2-dioxaborolan-2-yl)benzylcarbamate (19a) (420 mg, 1.2 mmol; CAS #1421773-36-5), tripotassium phosphate (1.3 M solution) (1.23 mL, 1.60 mmol), tricyclohexylphosphine (67 mg, 0.24 mmol) and Pd$_2$(dba)$_3$ (73 mg, 0.08 mmol) under an Ar atmosphere and heating at 120° C. for 60 min in a microwave. This gave after workup, purification by flash column chromatography [silica (12 g), eluting with DMA80 in DCM from 0-90%] 2-(2-(4-(3-(((tert-butoxycarbonyl)amino)methyl)-5-fluorophenyl)-1H-indole-6-carboxamido)phenyl)acetic acid (19b) (175 mg, 42% yield) as a yellow solid; MS (ES+): 518.4 (M+1); (ES–): 516.4 (M–1).

Step-2: Preparation of 2-(2-(4-(3-(aminomethyl)-5-fluorophenyl)-1H-indole-6-carboxamido)phenyl)acetic Acid (19c)

Compound 19c was prepared according to the procedure reported in step-5 of Scheme-1 from 2-(2-(4-(3-(((tert-butoxycarbonyl)amino)methyl)-5-fluorophenyl)-1H-indole-6-carboxamido)phenyl)acetic acid (19b) (170 mg, 0.33 mmol) in DCM (10 mL) using TFA (0.25 mL, 3.28 mmol). This gave after workup and purification by flash column chromatography [silica (12 g), eluting with DMA80 in DCM from 0-100%] followed by reverse phase column chromatography [C18 (50 g), eluting with ACN in water (containing 0.1% HCl) from 0-100%] 2-(2-(4-(3-(aminomethyl)-5-fluorophenyl)-1H-indole-6-carboxamido)phenyl)acetic acid (19c) (69 mg, 50% yield) as an off white solid; $^1$H NMR (300 MHz, DMSO-d$_6$) δ 12.37 (s, 1H, D$_2$O exchangeable), 11.80 (t, J=2.2 Hz, 1H), 10.08 (s, 1H, D$_2$O exchangeable), 8.52 (s, 3H, D$_2$O exchangeable), 8.12 (s, 1H), 7.86-7.81 (m, 1H), 7.80-7.75 (m, 1H), 7.68 (t, J=2.8 Hz, 1H), 7.64-7.56 (m, 1H), 7.53-7.39 (m, 2H), 7.38-7.28 (m, 2H), 7.27-7.18 (m, 1H), 6.84-6.76 (m, 1H), 4.17 (s, 2H), 3.70 (s, 2H); $^{19}$F NMR (282 MHz, DMSO-d$_6$) δ–112.22; MS (ES+): 418.4 (M+1); (ES–): 416.4 (M–1); 452.4 (M+Cl); HPLC purity; 98.96%.

Scheme-20

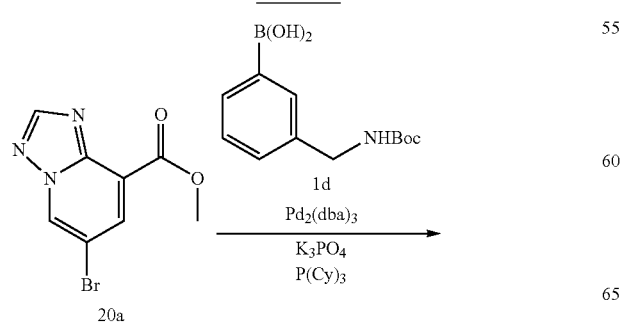

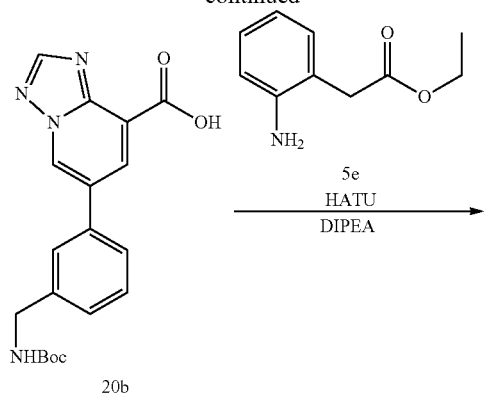

20b

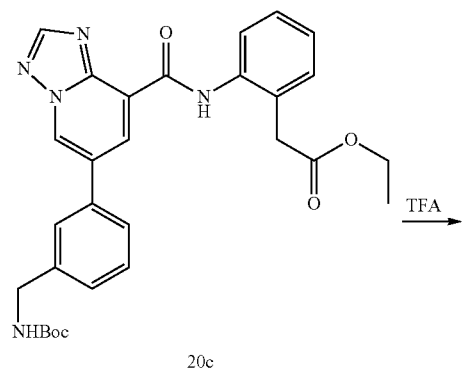

20c

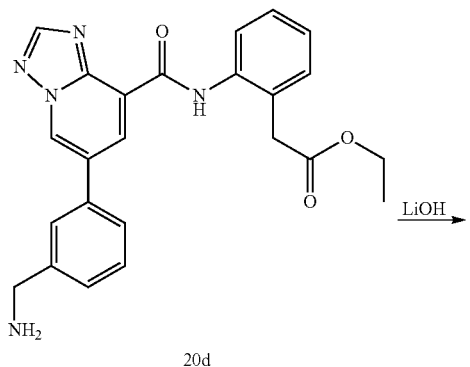

20d

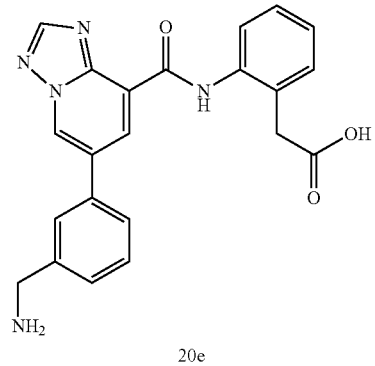 [SMILES: NCc1cccc(-c2cc(C(=O)Nc3ccccc3CC(=O)O)c3ncnn3c2)c1]

20e

Preparation of 2-(2-(6-(3-(aminomethyl)phenyl)-[1,2,4]triazolo[1,5-a]pyridine-8-carboxamido)phenyl)acetic Acid (20e)

Step-1: Preparation of 6-(3-(((tert-butoxycarbonyl)amino)methyl)phenyl)-[1,2,4]triazolo[1,5-a]pyridine-8-carboxylic Acid (20b)

Compound 20b was prepared according to the procedure reported in step-3 of Scheme-1, from methyl 6-bromo-[1,2,4]triazolo[1,5-a]pyridine-8-carboxylate (20a) (500 mg, 1.953 mmol; CAS #1801262-20-3) in dioxane (3 mL) using 3-((tert-butoxycarbonylamino)methyl)phenylboronic acid (1d) (735 mg, 2.93 mmol), tripotassium phosphate (1.3 M solution, 3.0 mL, 3.91 mmol), tricylcohexylphosphine (164 mg, 0.59 mmol) and $Pd_2(dba)_3$ (179 mg, 0.2 mmol) under a nitrogen atmosphere by heating at 120° C. for 1 h in microwave. This gave after workup and purification by flash column chromatography [silica (40 g), eluting with ethyl acetate in hexanes 0% to 100%] 6-(3-(((tert-butoxycarbonyl)amino)methyl)phenyl)-[1,2,4]triazolo[1,5-a]pyridine-8-carboxylic acid (20b) (200 mg, 28%) as an oil; MS (ES−) 367.3 (M−1)

Step-2: Preparation of Ethyl 2-(2-(6-(3-(((tert-butoxycarbonyl)amino)methyl)phenyl)-[1,2,4]triazolo[1,5-a]pyridine-8-carboxamido)phenyl)acetate (20c)

Compound 20c was prepared according to the procedure reported in step-4 of Scheme-1, from 6-(3-(((tert-butoxycarbonyl)amino)methyl)phenyl)-[1,2,4]triazolo[1,5-a]pyridine-8-carboxylic acid (20b) (200 mg, 0.54 mmol) in DMF (8 mL) using ethyl 2-(2-aminophenyl)acetate (5e) (170 mg, 0.95 mmol), DIPEA (0.28 mL, 1.63 mmol) and HATU (361 mg, 0.95 mmol). This gave after workup and purification by flash column chromatography [silica (12 g), eluting with 0-60% EtOAc/MeOH (9:1) in hexane from 0-100%] ethyl 2-(2-(6-(3-(((tert-butoxycarbonyl)amino)methyl)phenyl)-[1,2,4]triazolo[1,5-a]pyridine-8-carboxamido)phenyl)acetate (20c) (153 mg, 53% yield) as a white solid; $^1$H NMR (300 MHz, DMSO-$d_6$) δ 11.27 (s, 1H), 9.63 (d, J=1.8 Hz, 1H), 8.78 (s, 1H), 8.70 (d, J=1.8 Hz, 1H), 8.19-8.09 (m, 1H), 7.77 (m, 2H), 7.51 (m, 2H), 7.38 (m, 3H), 7.23 (m, 1H), 4.26 (d, J=6.1 Hz, 2H), 4.06 (q, J=7.1 Hz, 2H), 3.96 (s, 2H), 1.40 (s, 9H), 1.09 (t, J=7.1 Hz, 3H).

Step-3: Preparation of Ethyl 2-(2-(6-(3-(aminomethyl)phenyl)-[1,2,4]triazolo[1,5-a]pyridine-8-carboxamido)phenyl)acetate (20d)

Compound 20d was prepared according to the procedure reported in step-5 of Scheme-1, from ethyl 2-(2-(6-(3-(((tert-butoxycarbonyl)amino)methyl)phenyl)-[1,2,4]triazolo[1,5-a]pyridine-8-carboxamido)phenyl)acetate (20c) (140 mg, 0.264 mmol) using TFA (0.41 mL, 5.29 mmol) in DCM (2 mL). This gave after workup ethyl 2-(2-(6-(3-(aminomethyl)phenyl)-[1,2,4]triazolo[1,5-a]pyridine-8-carboxamido)phenyl)acetate (20d) (65 mg, 57%) which was used as such for next step; $^1$H NMR (300 MHz, DMSO-$d_6$) δ 11.27 (s, 1H), 9.64 (d, J=1.8 Hz, 1H), 8.77 (s, 1H), 8.71 (d, J=1.8 Hz, 1H), 8.13 (dd, J=7.3, 2.0 Hz, 1H), 7.87 (s, 1H), 7.76-7.68 (m, 1H), 7.49 (t, J=7.5 Hz, 1H), 7.46-7.40 (m, 1H), 7.40-7.35 (m, 2H), 7.26-7.16 (m, 1H), 4.06 (q, J=7.1 Hz, 2H), 3.95 (s, 2H), 3.82 (s, 2H), 2.11 (s, 2H), 1.09 (t, J=7.1 Hz, 3H); MS (ES+): 430.4 (M+1).

Step-4: Preparation of 2-(2-(6-(3-(aminomethyl)phenyl)-[1,2,4]triazolo[1,5-a]pyridine-8-carboxamido)phenyl)acetic Acid (20e)

Compound 20e was prepared according to the procedure reported in step-6 of Scheme-1, from ethyl 2-(2-(6-(3-(aminomethyl)phenyl)-[1,2,4]triazolo[1,5-a]pyridine-8-carboxamido)phenyl)acetate (20d) (60 mg, 0.14 mmol) in THF (5 mL) using a solution of lithium hydroxide hydrate (17 mg, 0.7 mmol) in water (1 mL) This gave after workup and purification by reverse phase column [C18 (50 g), eluting with ACN in water (containing 0.1% HCl) from 0-100%] 2-(2-(6-(3-(aminomethyl)phenyl)-[1,2,4]triazolo[1,5-a]pyridine-8-carboxamido)phenyl)acetic acid (20e) (53 mg, 95% yield) as a white solid; $^1$H NMR (300 MHz, DMSO-$d_6$) δ 11.39 (s, 1H), 9.69 (d, J=1.8 Hz, 1H), 8.79 (d, J=1.8 Hz, 1H), 8.76 (s, 1H), 8.48 (s, 3H, $D_2O$ exchangeable), 8.21-8.13 (m, 1H), 8.09 (s, 1H), 7.95 (dt, J=6.5, 2.3 Hz, 1H), 7.66-7.55 (m, 2H), 7.43-7.31 (m, 2H), 7.25-7.16 (m, 1H), 4.16 (d, J=5.8 Hz, 2H), 3.89 (s, 2H); MS (ES+) 402.3 (M+1), (ES−) 400.4 (M−1), 436.4 (M+Cl); HPLC purity: 98.75%.

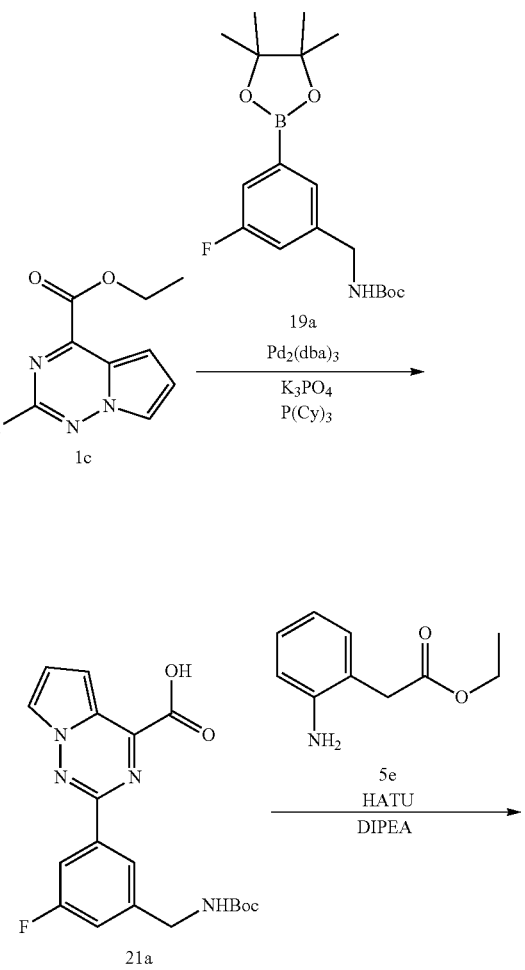

Scheme-21

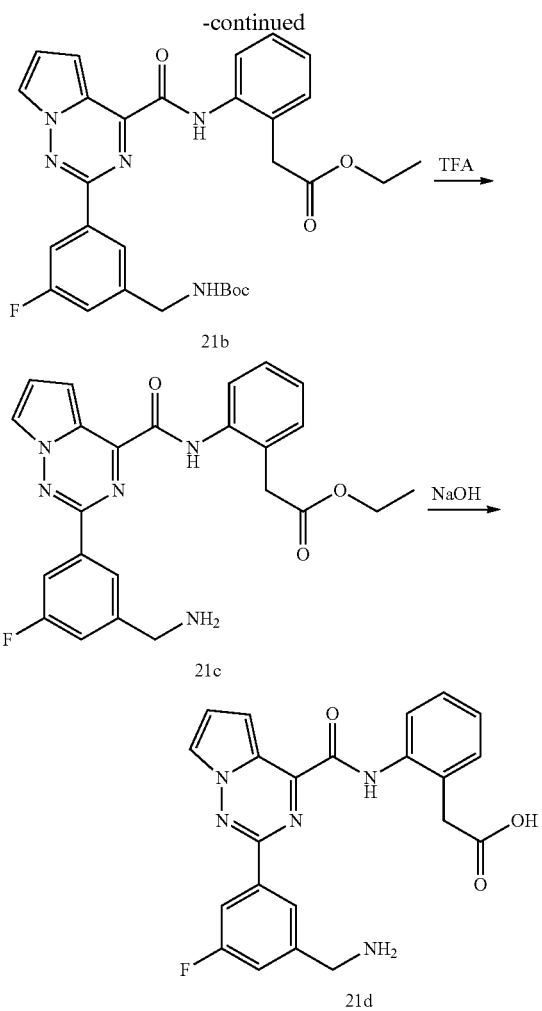

Preparation of 2-(2-(2-(3-(aminomethyl)-5-fluorophenyl)pyrrolo[2,1-f][1,2,4]triazine-4-carboxamido)phenyl)acetic Acid (21d)

Step-1: Preparation of 2-(3-(((tert-butoxycarbonyl)amino)methyl)-5-fluorophenyl)pyrrolo[2,1-f][1,2,4]triazine-4-carboxylic Acid (21a)

Compound 21a was prepared according to the procedure reported in step-3 of Scheme-1, from ethyl 2-chloropyrrolo[2,1-f][1,2,4]triazine-4-carboxylate (1c) (200 mg, 0.89 mmol) in dioxane (3 mL) using tert-butyl 3-fluoro-5-(4,4,5,5-tetramethyl-1,3,2-dioxaborolan-2-yl)benzylcarbamate (19a) (467 mg, 1.33 mmol), tripotassium phosphate (1.3 M solution, 1.36 mL, 0.089 mmol), tricylcohexylphosphine (75 mg, 0.27 mmol) and Pd$_2$(dba)$_3$ (81 mg, 0.089 mmol) under a nitrogen atmosphere by heating at 120° C. for 1 h in microwave. This gave after workup and purification by flash column chromatography [silica (12 g), eluting with DMA80 in DCM from 0-90%] 2-(3-(((tert-butoxycarbonyl)amino)methyl)-5-fluorophenyl)pyrrolo[2,1-f][1,2,4]triazine-4-carboxylic acid (21a) (118 mg, 35% yield) as a yellow solid; $^1$H NMR (300 MHz, DMSO-d$_6$) δ 8.04 (s, 1H), 8.01 (t, J=2.0 Hz, 1H), 7.90-7.83 (m, 1H), 7.58 (t, J=6.2 Hz, 1H), 7.17 (dt, J=9.8, 2.0 Hz, 1H), 6.99-6.93 (m, 2H), 4.23 (d, J=6.2 Hz, 2H), 1.41 (s, 9H).

Step-2: Preparation of Ethyl 2-(2-(2-(3-(((tert-butoxycarbonyl)amino)methyl)-5-fluorophenyl)pyrrolo[2,1-f][1,2,4]triazine-4-carboxamido)phenyl)acetate (21b)

Compound 21b was prepared according to the procedure reported in step-4 of Scheme-1 from 2-(3-(((tert-butoxycarbonyl)amino)methyl)-5-fluorophenyl)pyrrolo[2,1-f][1,2,4]triazine-4-carboxylic acid (21a) (110 mg, 0.29 mmol) in DMF (5 mL) using ethyl 2-(2-aminophenyl)acetate (5e) (77 mg, 0.43 mmol), DIPEA (0.1 mL, 0.57 mmol) and HATU (162 mg, 0.43 mmol). This gave after workup and purification by flash column chromatography [silica (12 g), eluting with 0-60% EtOAc/MeOH (9:1) in hexane from 0-100%] ethyl 2-(2-(2-(3-(((tert-butoxycarbonyl)amino)methyl)-5-fluorophenyl)pyrrolo[2,1-f][1,2,4]triazine-4-carboxamido)phenyl)acetate (21b) (125 mg, 80% yield) as a yellow solid; MS (ES−): 546.5 (M−1).

Step-3: Preparation of Ethyl 2-(2-(2-(3-(aminomethyl)-5-fluorophenyl)pyrrolo[2,1-f][1,2,4]triazine-4-carboxamido)phenyl)acetate (21c)

Compound 21c was prepared according to the procedure reported in step-5 of Scheme-1 from ethyl 2-(2-(2-(3-(((tert-butoxycarbonyl)amino)methyl)-5-fluorophenyl)pyrrolo[2,1-f][1,2,4]triazine-4-carboxamido)phenyl)acetate (21b) (42 mg, 0.08 mmol) using TFA (0.06 mL, 0.77 mmol) in DCM (10 mL). This gave after workup followed by purification by flash chromatography [silica (12 g), eluting with DMA80 in DCM from 0-100%] then reverse phase column chromatography [C18 (50 g), eluting with ACN in water (containing 0.1% HCl) from 0-100%] ethyl 2-(2-(2-(3-(aminomethyl)-5-fluorophenyl)pyrrolo[2,1-f][1,2,4]triazine-4-carboxamido)phenyl)acetate (21c) (33 mg, 96% yield) as a yellow solid; $^1$H NMR (300 MHz, DMSO-d$_6$) δ 10.92 (s, 1H), 8.58-8.49 (m, 1H), 8.45-8.36 (m, 2H), 8.26 (s, 3H), 7.71 (d, J=7.9 Hz, 1H), 7.65-7.60 (m, 1H), 7.60-7.53 (m, 1H), 7.46-7.38 (m, 2H), 7.35-7.25 (m, 2H), 4.20 (s, 2H), 4.01 (q, J=7.1 Hz, 2H), 3.86 (s, 2H), 1.00 (t, J=7.1 Hz, 3H).

Step-4: Preparation of 2-(2-(2-(3-(aminomethyl)-5-fluorophenyl)pyrrolo[2,1-f][1,2,4]triazine-4-carboxamido)phenyl)acetic Acid (21d)

Compound 21d was prepared according to the procedure reported in step-4 of Scheme-4 from ethyl 2-(2-(2-(3-(aminomethyl)-5-fluorophenyl)pyrrolo[2,1-f][1,2,4]triazine-4-carboxamido)phenyl)acetate (21c) (19 mg, 0.042 mmol) in MeOH (10 mL) using sodium hydroxide (17 mg, 0.43 mmol) in water (2 mL). This gave after workup and purification by reverse phase column chromatography [C18 (50 g), eluting with ACN in water (containing 0.1% HCl) from 0-100%] 2-(2-(2-(3-(aminomethyl)-5-fluorophenyl)pyrrolo[2,1-f][1,2,4]triazine-4-carboxamido)phenyl)acetic acid (21d) (15 mg, 84% yield) as a yellow solid; $^1$H NMR (300 MHz, DMSO-d$_6$) δ 12.68 (s, 1H, D$_2$O exchangeable), 10.94 (s, 1H, D$_2$O exchangeable), 8.52 (s, 3H, D$_2$O exchangeable), 8.48-8.45 (m, 1H), 8.45-8.35 (m, 2H), 7.81-7.74 (m, 1H), 7.65-7.57 (m, 2H), 7.45-7.35 (m, 2H), 7.34-7.24 (m, 2H), 4.27-4.13 (m, 2H), 3.78 (s, 2H); $^{19}$F NMR (282 MHz, DMSO-d$_6$) δ −112.09; MS (ES$^+$) 420.3 (M+1); (ES−) 418.4 (M−1); HPLC purity, 98.34%.

Scheme-22

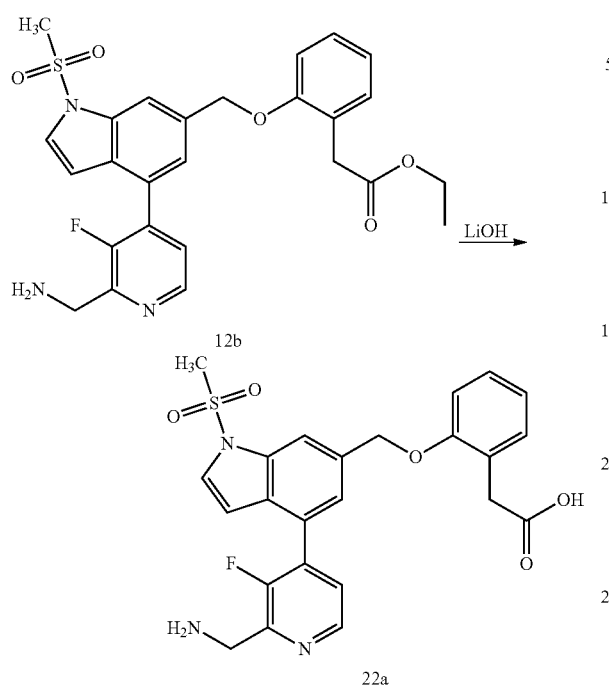

Preparation of 2-(2-((4-(2-(aminomethyl)-3-fluoro-pyridin-4-yl)-1-(methylsulfonyl)-1H-indol-6-yl)methoxy)phenyl)acetic Acid (22a)

Compound 22a was prepared according to the procedure reported in step-6 of Scheme-1 from ethyl 2-(2-((4-(2-(aminomethyl)-3-fluoropyridin-4-yl)-1-(methylsulfonyl)-1H-indol-6-yl)methoxy)phenyl)acetate (12b) (0.1 g, 0.20 mmol) in MeOH/THF (4 mL, each) using lithium hydroxide hydrate (8 mg, 0.2 mmol) in water (1 mL). This gave after workup and purification by reverse phase column [C18 (50 g), eluting with ACN in water (containing 0.1% HCl) from 0-100%] 2-(2-((4-(2-(aminomethyl)-3-fluoropyridin-4-yl)-1-(methylsulfonyl)-1H-indol-6-yl)methoxy)phenyl)acetic acid (22a) (0.03 g, 36% yield) HCl salt as a yellow solid; $^1$H NMR (300 MHz, DMSO-$d_6$) δ 8.60 (d, J=4.9 Hz, 1H), 8.53 (s, 3H), 8.12 (s, 1H), 7.75 (d, J=3.8 Hz, 1H), 7.71-7.64 (m, 1H), 7.57 (d, J=1.2 Hz, 1H), 7.29-7.18 (m, 2H), 7.16-7.07 (m, 1H), 6.92 (td, J=7.4, 1.1 Hz, 1H), 6.76 (t, J=3.3 Hz, 1H), 5.34 (s, 2H), 4.37 (d, J=6.0 Hz, 2H), 3.59 (s, 2H), 3.55 (s, 3H); $^{19}$F NMR (282 MHz, DMSO-$d_6$) δ−128.61; MS (ES+): 484.9 (M+1); MS (ES−): 482.9 (M−1). HPLC purity: 93.84%.

Scheme-23

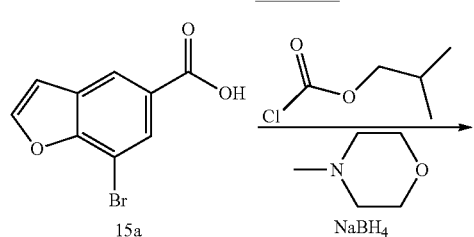

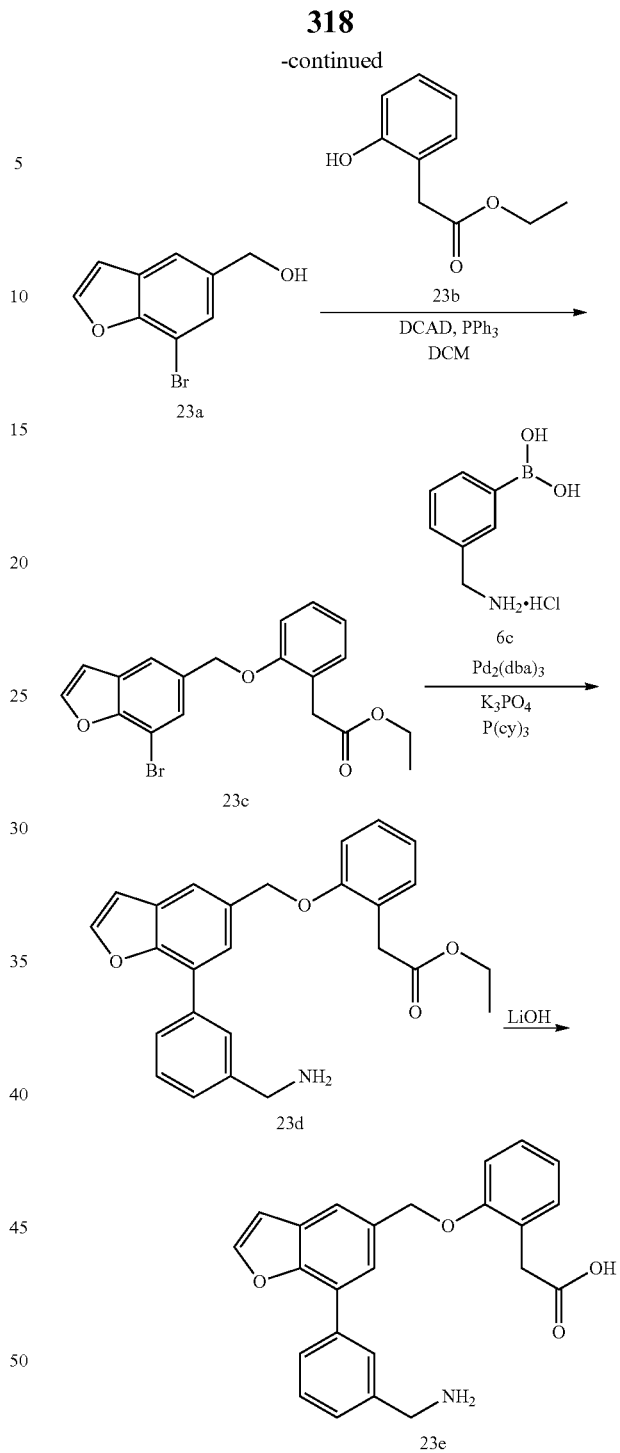

Preparation of 2-(2-((7-(3-(aminomethyl) Phenyl) benzofuran-5-yl) Methoxy) Phenyl) Acetic Acid (23e)

Step-1: Preparation of (7-bromobenzofuran-5-yl) Methanol (23a)

To the stirred solution of 7-bromobenzofuran-5-carboxylic acid (15a) (10 g, 41.5 mmol) and N-methylmorpholine (5.47 mL, 49.8 mmol) in THF (200 mL) at −5° C. was added isobutyl chloroformate (6.54 mL, 49.8 mmol). The reaction mixture was stirred for 15 min, filtered over a Celite pad and the precipitate was washed with THF (3×20 mL). The filtrate was cooled to 0° C. and added carefully (gas released rapidly) a solution of NaBH$_4$ (4.71 g, 124 mmol) in water (10 mL). The reaction mixture was stirred for 30 mins, diluted with water (20 mL), washed with ethyl acetate (3×). The organic layers were combined, dried, filtered and concentrated in vacuum to afford (7-bromobenzofuran-5-yl) methanol (23a) (9 g, 96% yield) as a white solid; $^1$H NMR (300 MHz, DMSO-d$_6$) δ 8.09 (d, J=2.2 Hz, 1H), 7.59 (d, J=1.4 Hz, 1H), 7.49 (d, J=1.4 Hz, 1H), 7.07 (d, J=2.2 Hz, 1H), 5.34 (t, J=5.8 Hz, 1H), 4.57 (d, J=5.8 Hz, 2H).

Step-2: Preparation of Ethyl 2-(2-((7-bromobenzofuran-5-yl) methoxy) phenyl)acetate (23c)

To a solution of (7-bromobenzofuran-5-yl) methanol (23a) (9 g, 39.6 mmol), triphenylphosphine (11.44 g, 43.6 mmol) and ethyl 2-(2-hydroxyphenyl)acetate (23b) (7.86 g, 43.6 mmol; CAS #41873-65-8) in DCM (180 mL) at 0° C. was added dropwise a solution of bis(4-chlorobenzyl)azodicarboxylate (DCAD, 16.01 g, 43.6 mmol; CAS #: 916320-82-6) in DCM (40 mL). The resulting mixture was stirred at RT for 30 min and filtered to remove solid. The filtrate was concentrated in vacuum and residue obtained was purified by flash column chromatography [silica (80 g), eluting with EtOAc in hexane from 0-50%] to give ethyl 2-(2-((7-bromobenzofuran-5-yl)methoxy)phenyl)acetate (23c) (11.5 g, 75% yield) as a white solid; $^1$H NMR (300 MHz, DMSO-d$_6$) δ 8.15 (d, J=2.2 Hz, 1H), 7.72 (s, 1H), 7.60 (s, 1H), 7.30-7.19 (m, 2H), 7.11 (d, J=2.2 Hz, 1H), 7.07 (d, J=8.1 Hz, 1H), 6.91 (td, J=7.4, 1.1 Hz, 1H), 5.18 (s, 2H), 4.01 (q, J=7.1 Hz, 2H), 3.62 (s, 2H), 1.07 (t, J=7.1 Hz, 3H).

Step-3: Preparation of Ethyl 2-(2-((7-(3-(aminomethyl) phenyl) benzofuran-5-yl) methoxy) phenyl) Acetate (23d)

Compound 23d was prepared according to the procedure reported in step-3 of Scheme-1 from ethyl 2-(2-((7-bromobenzofuran-5-yl)methoxy)phenyl)acetate (23c) (300 mg, 0.77 mmol) in dioxane (6 mL) using 3-(aminomethyl) phenylboronic acid hydrochloride (6c) (217 mg, 1.16 mmol), tripotassium phosphate (1.3 M solution) (0.77 mL, 2.31 mmol), tricyclohexylphosphine (65 mg, 0.23 mmol) and Pd$_2$(dba)$_3$ (71 mg, 0.077 mmol) under an Ar atmosphere and heating at 125° C. for 45 min in a microwave. This gave after workup, purification by flash column chromatography [silica (12 g), eluting with DMA80 in DCM from 0-60%] followed by purification by reverse phase column [C18 (30 g), eluting with ACN in water (containing 0.1% HCl) from 0-100%] ethyl 2-(2-((7-(3-(aminomethyl)phenyl)benzofuran-5-yl)methoxy)phenyl)acetate (23d) (107 mg, 33% yield) as a white solid; $^1$H NMR (300 MHz, DMSO-d$_6$) δ 8.20 (s, 3H, D$_2$O exchangeable), 8.14-8.09 (m, 1H), 7.98 (s, 1H), 7.91 (d, J=7.3 Hz, 1H), 7.81-7.71 (m, 1H), 7.67-7.47 (m, 3H), 7.34-7.19 (m, 2H), 7.17-7.06 (m, 2H), 6.92 (t, J=7.5 Hz, 1H), 5.25 (s, 2H), 4.13 (s, 2H), 4.01-3.86 (m, 2H), 3.63 (s, 2H), 1.04-0.93 (m, 3H); MS (ES+): 416.3 (M+1); 831.5 (2M+1); MS (ES−): 450.4 (M+Cl); HPLC purity: 96.49%

Step-4: Preparation of 2-(2-((7-(3-(aminomethyl) phenyl) benzofuran-5-yl) methoxy) Phenyl) Acetic Acid (23e)

Compound 23e was prepared according to the procedure reported in step-6 of Scheme-1, from ethyl 2-(2-((7-(3-(aminomethyl)phenyl)benzofuran-5-yl)methoxy)phenyl)acetate (23d) (2.25 g, 5.42 mmol) in MeOH/THF (30 mL) using a solution of lithium hydroxide hydrate (682 mg, 16.25 mmol) in water (5 mL) This gave after workup and purification by reverse phase column [C18 (50 g), eluting with ACN in water (containing 0.1% HCl) from 0-100%] 2-(2-((7-(3-(aminomethyl)phenyl)benzofuran-5-yl) methoxy)phenyl)acetic acid (23e) (1.5 g, 72% yield) as a white solid; $^1$H NMR (300 MHz, DMSO-d$_6$) δ 12.25 (s, 1H, D$_2$O exchangeable), 8.53 (s, 3H, D$_2$O exchangeable), 8.11 (d, J=2.2 Hz, 1H), 8.04-7.99 (m, 1H), 7.97-7.89 (m, 1H), 7.77 (d, J=1.6 Hz, 1H), 7.66 (d, J=1.7 Hz, 1H), 7.61-7.54 (m, 2H), 7.23 (d, J=7.4 Hz, 2H), 7.13-7.04 (m, 2H), 6.91 (td, J=7.4, 1.1 Hz, 1H), 5.27 (s, 2H), 4.13 (s, 2H), 3.61 (s, 2H); MS (ES+): 388.3 (M+1); (ES−): 386.3 (M−1); 422.3 (M+Cl); HPLC purity: 99.44%.

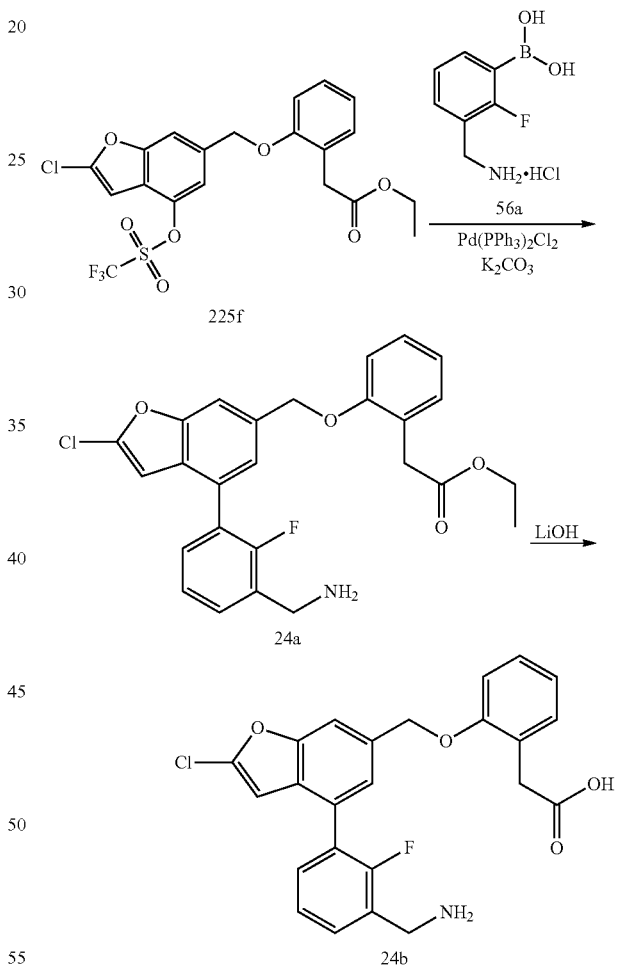

Scheme-24

Preparation of 2-(2-((4-(3-(aminomethyl)-2-fluorophenyl)-2-chlorobenzofuran-6-yl)methoxy)phenyl) acetic Acid (24b)

Step-1: Preparation of Ethyl 2-(2-((4-(3-(aminomethyl)-2-fluorophenyl)-2-chlorobenzofuran-6-yl) methoxy)phenyl)acetate (24a)

Compound 24a was prepared according to the procedure reported in step-3 of Scheme-1 from ethyl 2-(2-((2-chloro- 4-(((trifluoromethyl)sulfonyl)oxy)benzofuran-6-yl) methoxy)phenyl)acetate (225f) (191 mg, 0.388 mmol) in dioxane (5 mL) using (3-(aminomethyl)-2-fluorophenyl) boronic acid hydrochloride (56a) (117 mg, 0.692 mmol), a solution of K₂CO₃ (186 mg, 1.346 mmol) in water (0.5 mL), Pd(PPh₃)₂Cl₂ (55 mg, 0.078 mmol) and heating under an Ar atmosphere at 100° C. for 3 h. This gave after workup, purification by flash column chromatography (silica gel 12 g, eluting with DMA80 in DCM from 0-50%) ethyl 2-(2-((4-(3-(aminomethyl)-2-fluorophenyl)-2-chlorobenzofuran-6-yl)methoxy)phenyl)acetate (24a) (181 mg, 100% yield) as a pale-yellow oil. MS (ES+): 467.9 (M+1).

Step-2: Preparation of 2-(2-((4-(3-(aminomethyl)-2-fluorophenyl)-2-chlorobenzofuran-6-yl)methoxy) phenyl)acetic Acid (24b)

Compound 24b was prepared according to the procedure reported in step-6 of Scheme-1, from ethyl 2-(2-((4-(3-(aminomethyl)-2-fluorophenyl)-2-chlorobenzofuran-6-yl) methoxy)phenyl)acetate (24a) (205 mg, 0.438 mmol) in MeOH/THF (6 mL) using a solution of lithium hydroxide (132 mg, 3.15 mmol) in water (2 mL). This gave after workup and purification by reverse phase column (C18, 100 g, 0-60% MeCN in H₂O containing 0.1% HCl) 2-(2-((4-(3-(aminomethyl)-2-fluorophenyl)-2-chlorobenzofuran-6-yl) methoxy)phenyl)acetic acid (24b) (60 mg, 31% yield) HCl salt as a white solid. ¹H NMR (300 MHz, DMSO-d₆) δ 8.59 (s, 2H), 7.70 (s, 1H), 7.62 (t, J=7.1 Hz, 1H), 7.54 (t, J=7.4 Hz, 1H), 7.42 (s, 1H), 7.34 (t, J=7.6 Hz, 1H), 7.16 (d, J=7.4 Hz, 2H), 7.02 (dd, J=13.9, 5.9 Hz, 2H), 6.84 (t, J=7.3 Hz, 1H), 5.23 (s, 2H), 4.09 (s, 2H), 3.53 (s, 2H). MS (ES+): 439.9 (M+1); MS(ES−): 437.9 (M−1).

Scheme-25

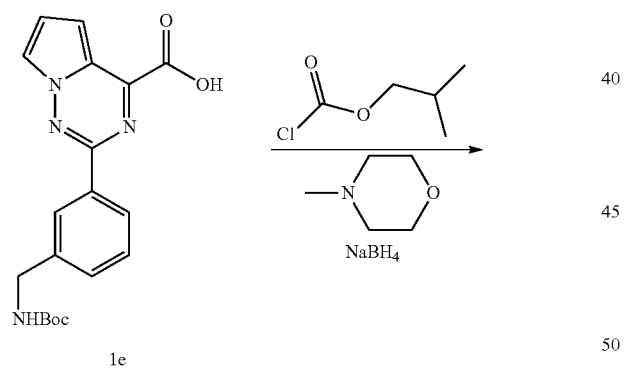

1e

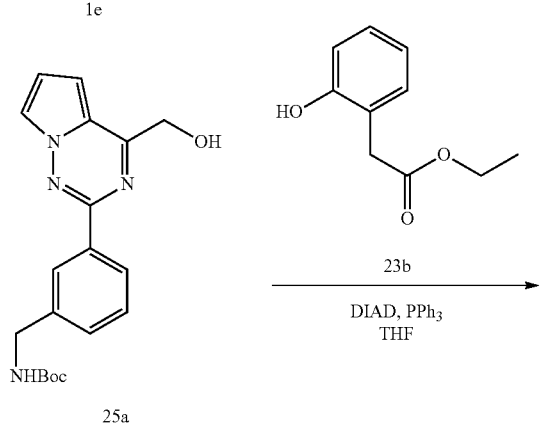

25a

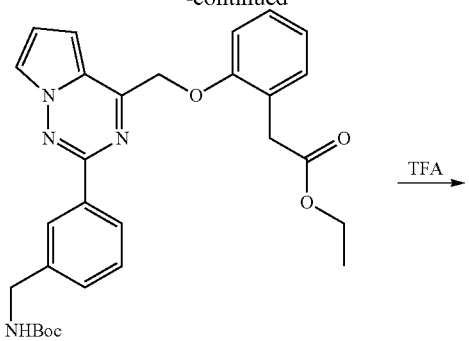

25b

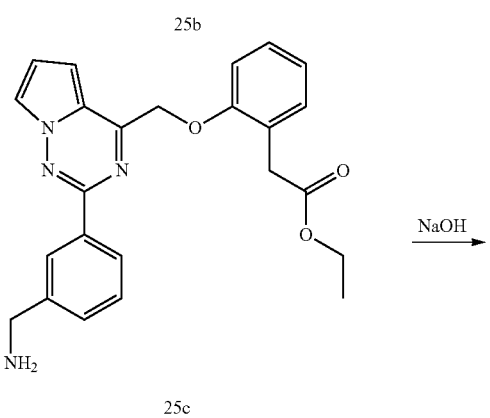

25c

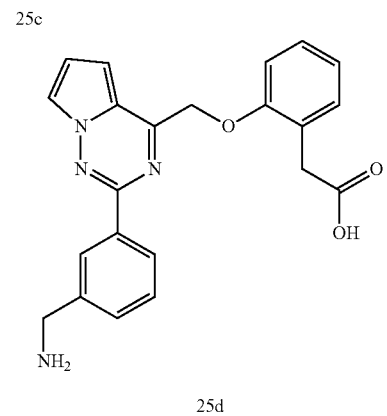

25d

Preparation of 2-(2-((2-(3-(aminomethyl)phenyl) pyrrolo[2,1-f][1,2,4]triazin-4-yl)methoxy)phenyl) acetic Acid (25d)

Step-1: Preparation of tert-butyl 3-(4-(hydroxymethyl)pyrrolo[2,1-f][1,2,4]triazin-2-yl)benzylcarbamate (25a)

Compound 25a was prepared according to the procedure reported in step-1 of Scheme-23, from 2-(3-(((tert-butoxycarbonyl)amino)methyl)phenyl)pyrrolo[2,1-f][1,2,4]triazine-4-carboxylic acid (1e) (570 mg, 1.55 mmol) in THF (30 mL), using N-methylmorpholine (0.2 mL, 1.86 mmol), isobutyl chloroformate (0.24 mL, 1.86 mmol) and NaBH₄ (176 mg, 4.64 mmol) in water (0.8 mL). This gave after workup tert-butyl 3-(4-(hydroxymethyl)pyrrolo[2,1-f][1,2, 4]triazin-2-yl)benzylcarbamate (25a) (100 mg, 18% yield) as a yellow oil; ¹H NMR (300 MHz, DMSO-d₆) δ 8.23-8.17 (m, 2H), 8.12 (s, 1H), 7.57-7.43 (m, 2H), 7.38 (d, J=7.6 Hz, 1H), 7.20 (d, J=4.5 Hz, 1H), 7.02 (dd, J=4.5, 2.5 Hz, 1H), 5.77 (d, J=5.7 Hz, 1H), 4.87 (d, J=6.1 Hz, 2H), 4.22 (d, J=6.2 Hz, 2H), 1.42 (s, 9H); MS (ES+): 355.3 (M+1), 377.3 (M+Na), (ES−): 353.4 (M−1).

Step-2: Preparation of Ethyl 2-(2-((2-(3-(((tert-butoxycarbonyl)amino)methyl)phenyl)pyrrolo[2,1-f][1,2,4]triazin-4-yl)methoxy)phenyl)acetate (25b)

Compound 25b was prepared according to the procedure reported in step-2 of Scheme-23, from tert-butyl 3-(4-(hydroxymethyl)pyrrolo[2,1-f][1,2,4]triazin-2-yl)benzylcarbamate (25a) (95 mg, 0.27 mmol) in THF (5 mL) using triphenylphosphine (91 mg, 0.35 mmol), ethyl 2-(2-hydroxyphenyl) acetate (23b) (63 mg, 0.35 mmol) and diisopropyl azodicarboxylate (DIAD, 71 mg, 0.35 mmol). This gave after workup and purification by flash column chromatography [silica (12 g), eluting with EtOAc in hexane from 0-40%] ethyl 2-(2-((2-(3-(((tert-butoxycarbonyl)amino)methyl)phenyl)pyrrolo[2,1-f][1,2,4]triazin-4-yl)methoxy)phenyl)acetate (25b) (42 mg, 30% yield) as a solid; MS (ES+): 539.4, 540.5 (M+Na), (ES−): 515.4, 516.5 (M−1).

Step-3: Preparation of Ethyl 2-(2-((2-(3-(aminomethyl)phenyl)pyrrolo[2,1-f][1,2,4]triazin-4-yl)methoxy)phenyl)acetate (25c)

Compound 25c was prepared according to the procedure reported in step-5 of Scheme-1, from ethyl 2-(2-((2-(3-(((tert-butoxycarbonyl)amino)methyl)phenyl)pyrrolo[2,1-f][1,2,4]triazin-4-yl)methoxy)phenyl)acetate (25b) (140 mg, 0.27 mmol) using TFA (0.21 mL, 2.71 mmol) in DCM (5 mL). This gave after workup followed by purification by reverse phase column chromatography [C18 (50 g), eluting with ACN in water (containing 0.1% HCl) from 0-100%] ethyl 2-(2-((2-(3-(aminomethyl)phenyl)pyrrolo[2,1-f][1,2,4]triazin-4-yl)methoxy)phenyl)acetate (25c) (26 mg, 23% yield) as a yellow solid; $^1$H NMR (300 MHz, DMSO-$d_6$) δ 8.45-8.40 (m, 1H), 8.40-8.27 (m, 4H, partially $D_2O$ exchangeable), 8.22-8.16 (m, 1H), 7.68-7.54 (m, 2H), 7.30-7.20 (m, 2H), 7.20-7.14 (m, 2H), 7.12-7.07 (m, 1H), 7.00-6.91 (m, 1H), 5.54 (s, 2H), 4.21-4.08 (m, 2H), 3.97 (q, J=7.1 Hz, 2H), 3.72 (s, 2H), 1.04 (t, J=7.1 Hz, 3H); MS (ES+): 417.3 (M+1); 439.3 (M+Na); HPLC purity: 97.50%.

Step-4: Preparation of 2-(2-((2-(3-(aminomethyl)phenyl)pyrrolo[2,1-f][1,2,4]triazin-4-yl)methoxy)phenyl)acetic Acid (25d)

Compound 25d was prepared according to the procedure reported in step-4 of Scheme-4 from ethyl 2-(2-((2-(3-(aminomethyl)phenyl)pyrrolo[2,1-f][1,2,4]triazin-4-yl)methoxy)phenyl)acetate (25c) (38 mg, 0.09 mmol) in MeOH (5 mL) using sodium hydroxide (15.49 mg, 0.39 mmol) in water (0.5 mL). This gave after workup and purification by reverse phase column chromatography [C18 (30 g), eluting with ACN in water (containing 0.1% HCl) from 0-100%] 2-(2-((2-(3-(aminomethyl)phenyl)pyrrolo[2,1-f][1,2,4]triazin-4-yl)methoxy)phenyl)acetic acid (25d) (3.6 mg, 12% yield) as a yellow solid; $^1$H NMR (300 MHz, Methanol-$d_4$) δ 8.50 (s, 1H), 8.44-8.36 (m, 1H), 8.08-8.03 (m, 1H), 7.63-7.56 (m, 2H), 7.31-7.19 (m, 3H), 7.11-7.02 (m, 2H), 7.01-6.92 (m, 1H), 5.58 (s, 2H), 4.23 (s, 2H), 3.75 (s, 2H); MS (ES+): 389.3 (M+1); 411.3 (M+Na); (ES−): 387.2 (M−1); 423.4 (M+Cl); HPLC, purity: 87.71%.

Scheme-26

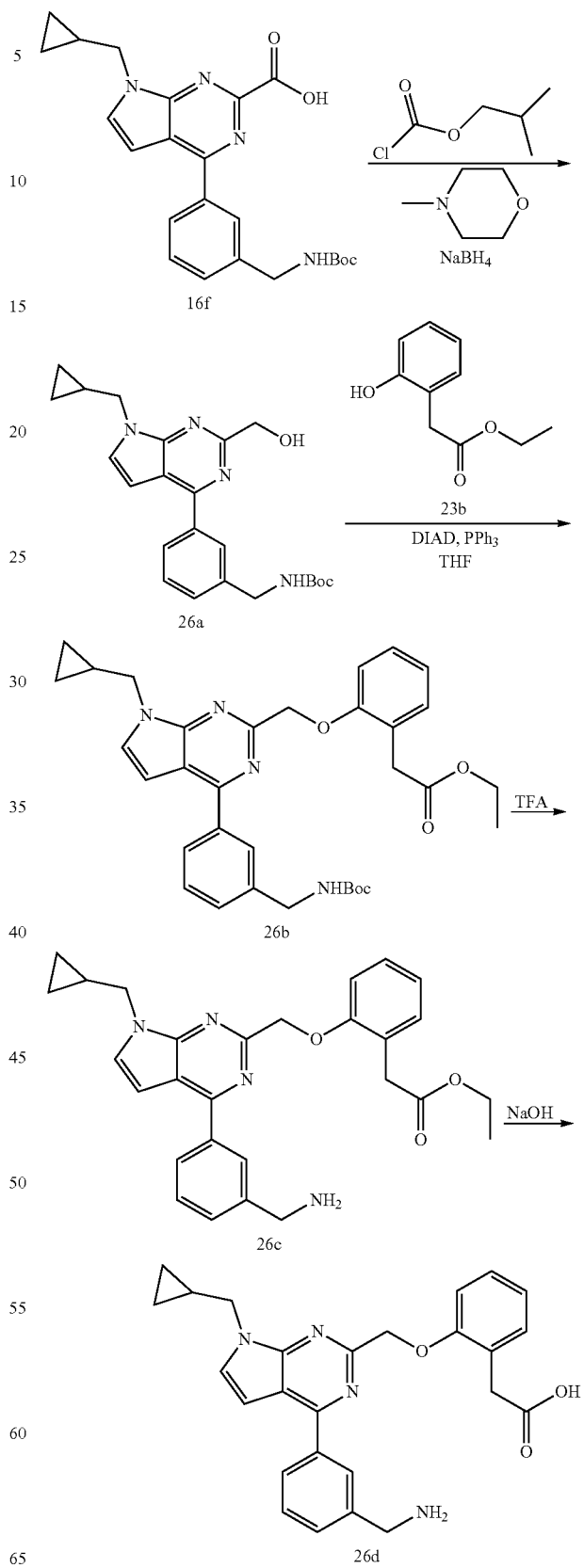

Preparation of 2-(2-((4-(3-(aminomethyl)phenyl)-7-(cyclopropylmethyl)-7H-pyrrolo[2,3-d]pyrimidin-2-yl)methoxy)phenyl)acetic Acid (26d)

Step-1: Preparation of tert-butyl 3-(7-(cyclopropylmethyl)-2-(hydroxymethyl)-7H-pyrrolo[2,3-d]pyrimidin-4-yl)benzylcarbamate (26a)

Compound 26a was prepared according to the procedure reported in step-1 of Scheme-23, from 4-(3-(((tert-butoxycarbonyl)amino)methyl)phenyl)-7-(cyclopropylmethyl)-7H-pyrrolo[2,3-d]pyrimidine-2-carboxylic acid (16f) (500 mg, 1.18 mmol) in THF (30 mL), using N-methylmorpholine (0.14 mL, 1.3 mmol), isobutyl chloroformate (0.17 mL, 1.3 mmol) and NaBH$_4$ (90 mg, 2.37 mmol) in water (0.8 mL). This gave after workup tert-butyl 3-(7-(cyclopropylmethyl)-2-(hydroxymethyl)-7H-pyrro[2,3-d]pyrimidin-4-yl)benzylcarbamate (26a) (330 mg, 68% yield) as a yellow oil; $^1$H NMR (300 MHz, DMSO-d$_6$) δ 8.10-8.03 (m, 2H), 7.78 (d, J=3.6 Hz, 1H), 7.61-7.48 (m, 2H), 7.41 (d, J=7.6 Hz, 1H), 6.89 (d, J=3.6 Hz, 1H), 5.17 (t, J=6.1 Hz, 1H), 4.71 (d, J=6.1 Hz, 2H), 4.25 (d, J=6.3 Hz, 2H), 4.16 (d, J=7.2 Hz, 2H), 1.41 (s, 9H), 1.34-1.21 (m, 1H), 0.58-0.40 (m, 4H); $^1$H NMR (300 MHz, DMSO-d$_6$/D$_2$O) δ 8.05-7.96 (m, 2H), 7.70 (d, J=3.6 Hz, 1H), 7.57-7.43 (m, 1H), 7.39 (d, J=7.6 Hz, 1H), 6.85 (d, J=3.6 Hz, 1H), 4.69 (s, 2H), 4.23 (d, J=4.8 Hz, 2H), 4.13 (d, J=7.2 Hz, 2H), 1.37 (s, 9H), 1.31-1.17 (m, 1H), 0.54-0.36 (m, 4H).

Step-2: Preparation of Ethyl 2-(2-((4-(3-(((tert-butoxycarbonyl)amino)methyl)phenyl)-7-(cyclopropylmethyl)-7H-pyrrolo[2,3-d]pyrimidin-2-yl)methoxy)phenyl)acetate (26b)

Compound 26b was prepared according to the procedure reported in step-2 of Scheme-23, from tert-butyl 3-(7-(cyclopropylmethyl)-2-(hydroxymethyl)-7H-pyrrolo[2,3-d]pyrimidin-4-yl)benzylcarbamate (26a) (327 mg, 0.8 mmol) in THF (8 mL) using triphenylphosphine (273 mg, 1.04 mmol), ethyl 2-(2-hydroxyphenyl) acetate (23b) (188 mg, 1.04 mmol) and (E)-diisopropyl diazene-1,2-dicarboxylate (DIAD, 210 mg, 1.04 mmol). This gave after workup and by flash column chromatography [silica (12 g), eluting with EtOAc in hexane from 0-60%] ethyl 2-(2-((4-(3-(((tert-butoxycarbonyl)amino)methyl)phenyl)-7-(cyclopropylmethyl)-7H-pyrrolo[2,3-d]pyrimidin-2-yl)methoxy)phenyl)acetate (26b) (352 mg, 77% yield) as an off white solid; $^1$H NMR (300 MHz, DMSO-d$_6$) δ 8.90 (s, 2H), 8.08-7.98 (m, 2H), 7.82 (d, J=3.6 Hz, 1H), 7.58-7.48 (m, 2H), 7.41 (d, J=7.6 Hz, 1H), 7.24-7.13 (m, 3H), 6.96-6.83 (m, 2H), 5.35 (s, 2H), 4.25 (d, J=6.2 Hz, 2H), 4.13 (d, J=7.2 Hz, 2H), 3.96 (q, J=7.1 Hz, 2H), 1.40 (s, 9H), 1.34-1.19 (m, 1H), 1.01 (t, J=7.1 Hz, 3H), 0.51-0.34 (m, 4H).

Step-3: Preparation of Ethyl 2-(2-((4-(3-(aminomethyl)phenyl)-7-(cyclopropylmethyl)-7H-pyrrolo[2,3-d]pyrimidin-2-yl)methoxy)phenyl)acetate (26c)

Compound 26c was prepared according to the procedure reported in step-5 of Scheme-1, from ethyl 2-(2-((4-(3-(((tert-butoxycarbonyl)amino)methyl)phenyl)-7-(cyclopropylmethyl)-7H-pyrrolo[2,3-d]pyrimidin-2-yl)methoxy)phenyl)acetate (26b) (350 mg, 0.61 mmol) using TFA (0.47 mL, 6.13 mmol) in DCM (25 mL). This gave after workup followed by purification by flash column chromatography [silica (12 g), eluting with DMA-80 in DCM from 0-100%] followed by reverse phase column chromatography [C18 (50 g), eluting with ACN in water (containing 0.1% HCl) from 0-100%] ethyl 2-(2-((4-(3-(aminomethyl)phenyl)-7-(cyclopropylmethyl)-7H-pyrrolo[2,3-d]pyrimidin-2-yl)methoxy)phenyl)acetate (26c) (256 mg, 89% yield) as a white solid; $^1$H NMR (300 MHz, DMSO-d$_6$) δ 8.54 (s, 3H, D$_2$O exchangeable), 8.27 (s, 1H), 8.18 (dt, J=7.4, 1.6 Hz, 1H), 7.88 (d, J=3.6 Hz, 1H), 7.75-7.59 (m, 2H), 7.27-7.10 (m, 4H), 6.90 (td, J=7.2, 1.3 Hz, 1H), 5.38 (s, 2H), 4.16 (t, J=7.1 Hz, 4H), 3.97 (q, J=7.1 Hz, 2H), 3.70 (s, 2H), 1.36-1.19 (m, 1H), 1.02 (t, J=7.1 Hz, 3H), 0.55-0.34 (m, 4H); MS (ES+): 471.4 (M+1); 493.4 (M+Na); (ES−): 505.4 (M+Cl); HPLC purity: 99.60%.

Step-4: Preparation of 2-(2-((4-(3-(aminomethyl)phenyl)-7-(cyclopropylmethyl)-7H-pyrrolo[2,3-d]pyrimidin-2-yl)methoxy)phenyl)acetic Acid (26d)

Compound 26d was prepared according to the procedure reported in step-4 of Scheme-4 from ethyl 2-(2-((4-(3-(aminomethyl)phenyl)-7-(cyclopropylmethyl)-7H-pyrrolo[2,3-d]pyrimidin-2-yl)methoxy)phenyl)acetate (26c) (105 mg, 0.22 mmol) in MeOH (10 mL) using sodium hydroxide (44.6 mg, 1.12 mmol) in water (2 mL). This gave after workup and purification by reverse phase column chromatography [C18 (50 g), eluting with ACN in water (containing 0.1% HCl) from 0-100%] 2-(2-((4-(3-(aminomethyl)phenyl)-7-(cyclopropylmethyl)-7H-pyrrolo[2,3-d]pyrimidin-2-yl)methoxy)phenyl)acetic acid (26d) (23 mg, 23% yield) as a white solid; $^1$H NMR (300 MHz, DMSO-d$_6$) δ 8.54 (s, 3H, D$_2$O exchangeable), 8.26 (d, J=2.1 Hz, 1H), 8.18 (dd, J=7.6, 1.6 Hz, 1H), 7.87 (d, J=3.6 Hz, 1H), 7.73-7.58 (m, 2H), 7.25-7.09 (m, 4H), 6.92-6.84 (m, 1H), 5.40 (s, 2H), 4.22-4.09 (m, 4H), 3.67 (s, 2H), 1.32-1.21 (m, 1H), 0.52-0.31 (m, 4H); MS (ES+): 443.4 (M+1); 465.4 (M+Na); (ES−): 441.5 (M−1); 477.4 (M+Cl); HPLC purity: 99.44%

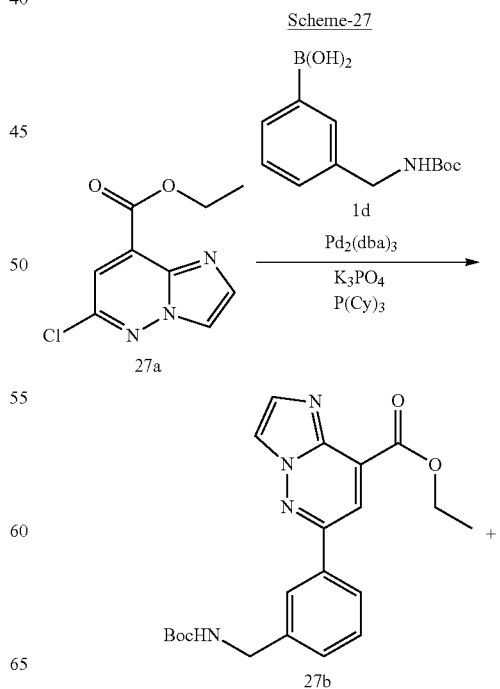

Scheme-27

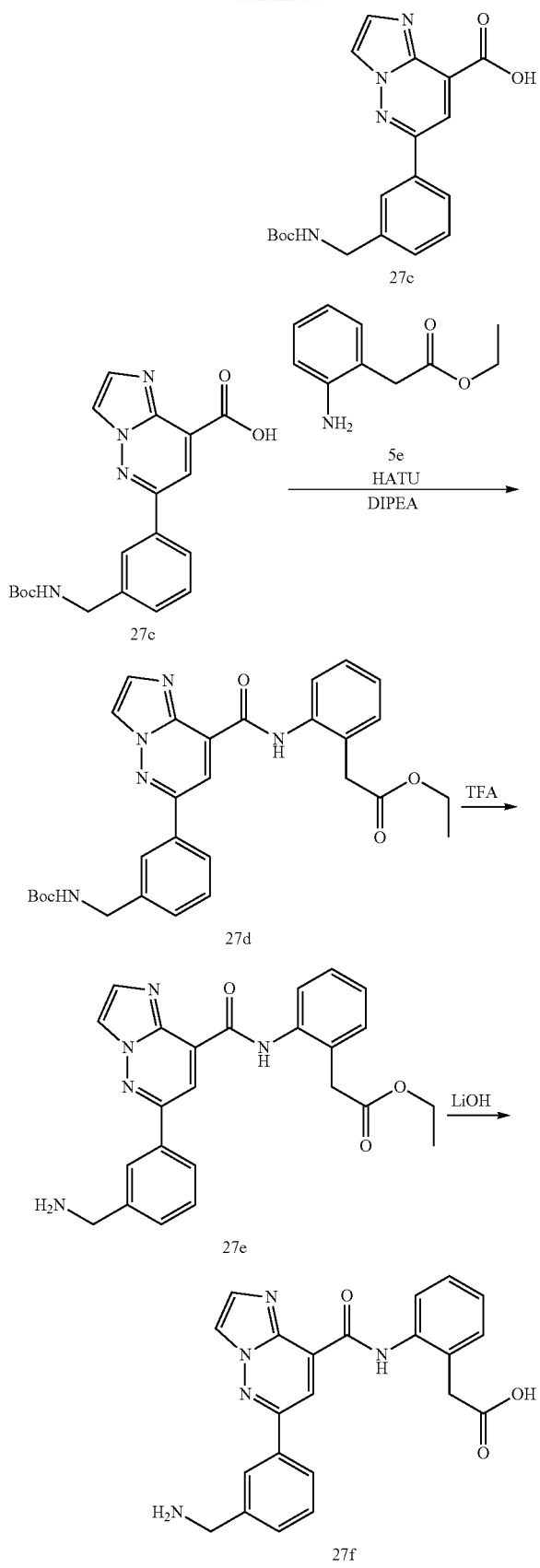

Preparation of 2-(2-(6-(3-(aminomethyl)phenyl)imidazo[1,2-b]pyridazine-8-carboxamido)phenyl)acetic Acid (27f)

Step-1: Preparation of 6-(3-(((tert-butoxycarbonyl)amino)methyl)phenyl)imidazo[1,2-b]pyridazine-8-carboxylic Acid (27c)

Compound 27c was prepared according to the procedure reported in step-3 of Scheme-1, from ethyl 6-chloroimidazo[1,2-b]pyridazine-8-carboxylate (27a) (500 mg, 2.22 mmol; CAS #1161847-33-1) in dioxane (6 mL) using 3-((tert-butoxycarbonylamino)methyl)phenylboronic acid (Id) (835 mg, 3.32 mmol), tripotassium phosphate (1.5 mL, 4.43 mmol, 1.3 M aqueous solution), tricyclohexylphosphine (186 mg, 0.67 mmol) and Pd$_2$(dba)$_3$ (203 mg, 0.22 mmol) under a nitrogen atmosphere by heating at 120° C. for 1 h in a microwave. This gave after workup and purification by flash column chromatography [silica (40 g), eluting with hexanes in ethyl acetate 0-100%] ethyl 6-(3-(((tert-butoxycarbonyl)amino)methyl)phenyl)imidazo[1,2-b]pyridazine-8-carboxylate (27b) (123 mg, 14% yield) as a colorless gum; $^1$H NMR (300 MHz, DMSO-d$_6$) δ 8.47 (d, J=1.2 Hz, 1H), 8.09 (s, 1H), 7.99-7.94 (m, 2H), 7.92 (d, J=1.2 Hz, 1H), 7.58-7.39 (m, 3H), 4.47 (q, J=7.1 Hz, 2H), 4.24 (d, J=6.2 Hz, 2H), 1.43-1.30 (m, 12H); MS (ES+): 397.3 (M+1), further elution gave 6-(3-(((tert-butoxycarbonyl)amino)methyl)phenyl)imidazo[1,2-b]pyridazine-8-carboxylic acid (27c) (60 mg, 7% yield) as an oil; $^1$H NMR (300 MHz, DMSO-d$_6$) δ 8.47 (s, 1H), 8.05 (s, 1H), 8.00-7.94 (m, 2H), 7.91 (d, J=1.3 Hz, 1H), 7.59-7.38 (m, 3H), 4.24 (d, J=6.2 Hz, 2H), 1.41 (s, 9H).

Step-2: Preparation of Ethyl 2-(2-(6-(3-(((tert-butoxycarbonyl)amino)methyl)phenyl)imidazo[1,2-b]pyridazine-8-carboxamido)phenyl)acetate (27d)

Compound 27d was prepared according to the procedure reported in step-4 of Scheme-1, from 6-(3-(((tert-butoxycarbonyl)amino)methyl)phenyl)imidazo[1,2-b]pyridazine-8-carboxylic acid (27c) (180 mg, 0.489 mmol) using ethyl 2-(2-aminophenyl)acetate (5e) (153 mg, 0.86 mmol), DIPEA (0.26 mL, 1.47 mmol) and HATU (325 mg, 0.87 mmol). This gave after workup and purification by flash column chromatography [silica (12 g), eluting with EtOAc/MeOH (9:1) in hexane from 0-100%] ethyl 2-(2-(6-(3-(((tert-butoxycarbonyl)amino)methyl)phenyl)imidazo[1,2-b]pyridazine-8-carboxamido)phenyl)acetate (27d) (140 mg, 54% yield) as a white solid; $^1$H NMR (300 MHz, DMSO-d$_6$) δ 11.76 (s, 1H), 8.59 (s, 1H), 8.34 (s, 1H), 8.20-8.13 (m, 1H), 8.05-7.97 (m, 2H), 7.93 (s, 1H), 7.62-7.52 (m, 2H), 7.45 (d, J=8.3 Hz, 1H), 7.41 (s, 1H), 7.38 (s, 1H), 7.22 (t, J=7.5 Hz, 1H), 4.26 (d, J=6.2 Hz, 2H), 4.06 (q, J=7.1 Hz, 2H), 3.98 (s, 2H), 1.41 (s, 9H), 1.10 (t, J=7.1 Hz, 3H); MS (ES+): 530.4 (M+1).

Step-3: Preparation of Ethyl 2-(2-(6-(3-(aminomethyl)phenyl)imidazo[1,2-b]pyridazine-8-carboxamido)phenyl)acetate (27e)

Compound 27e was prepared according to the procedure reported in step-5 of Scheme-1, from ethyl 2-(2-(6-(3-(((tert-butoxycarbonyl)amino)methyl)phenyl)imidazo[1,2-b]pyridazine-8-carboxamido)phenyl)acetate (27d) (125 mg, 0.24 mmol) using TFA (0.18 mL, 2.36 mmol) in DCM (5 mL). This gave after workup and purification by flash column chromatography [silica (12 g), eluting with DMA80 in DCM from 0-100%] followed by reverse phase column chromatography [C18 (50 g), eluting with ACN in water (containing 0.1% HCl) from 0-100%] ethyl 2-(2-(6-(3-(aminomethyl)phenyl)imidazo[1,2-b]pyridazine-8-carboxamido)phenyl)acetate (27e) (100 mg, 99% yield) as an pale yellow solid; $^1$H NMR (300 MHz, DMSO-d$_6$) δ 11.78 (s, 1H, D$_2$O exchangeable), 8.61 (d, J=1.4 Hz, 1H), 8.51-8.35 (m, 4H, 3H D$_2$O exchangeable), 8.31 (s, 1H), 8.18 (dd, J=7.9, 4.2 Hz, 2H), 7.97 (d, J=1.4 Hz, 1H), 7.75-7.61 (m, 2H), 7.47-7.37 (m, 2H), 7.24 (t, J=7.4 Hz, 1H), 4.20 (q, J=5.9 Hz, 2H), 4.06 (q, J=7.1 Hz, 2H), 3.99 (s, 2H), 1.10 (t, J=7.1 Hz, 3H); MS (ES+) 430.5 (M+1), 452.4 (M+Na), (ES−): 464.5 (M+Cl); HPLC purity: 97.66%.

Step-4: Preparation of 2-(2-(6-(3-(aminomethyl)phenyl)imidazo[1,2-b]pyridazine-8-carboxamido)phenyl)acetic Acid (27f)

Compound 27f was prepared according to the procedure reported in step-6 of Scheme-1, from ethyl 2-(2-(6-(3-(aminomethyl)phenyl)imidazo[1,2-b]pyridazine-8-carboxamido)phenyl)acetate (27e) (61 mg, 0.142 mmol) in THF (5 mL) using a solution of lithium hydroxide hydrate (10 mg, 0.43 mmol) in water (1 mL). This gave after workup and purification by reverse phase column chromatography [C18 (50 g), eluting with ACN in water (containing 0.1% HCl) from 0-100%] 2-(2-(6-(3-(aminomethyl)phenyl)imidazo[1,2-b]pyridazine-8-carboxamido)phenyl)acetic acid (27f) (65 mg, 100% yield) as a light yellow solid; $^1$H NMR (300 MHz, DMSO-d$_6$) δ 11.87 (s, 1H, D$_2$O exchangeable), 8.61 (d, J=1.4 Hz, 1H), 8.58-8.43 (m, 4H, 3H D$_2$O exchangeable), 8.32 (d, J=1.9 Hz, 1H), 8.22-8.10 (m, 2H), 8.00 (d, J=1.4 Hz, 1H), 7.75-7.62 (m, 2H), 7.39 (m, 2H), 7.22 (td, J=7.5, 1.3 Hz, 1H), 4.18 (q, J=5.5 Hz, 2H), 3.90 (s, 2H); MS (ES+): 402.4 (M+1), 424.4 (M+Na); (ES−): 400.5 (M−1); HPLC purity: 97.80%.

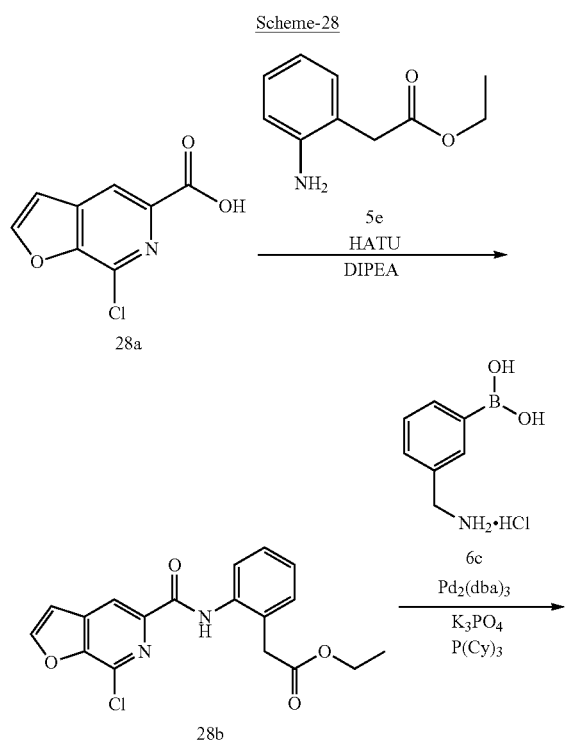

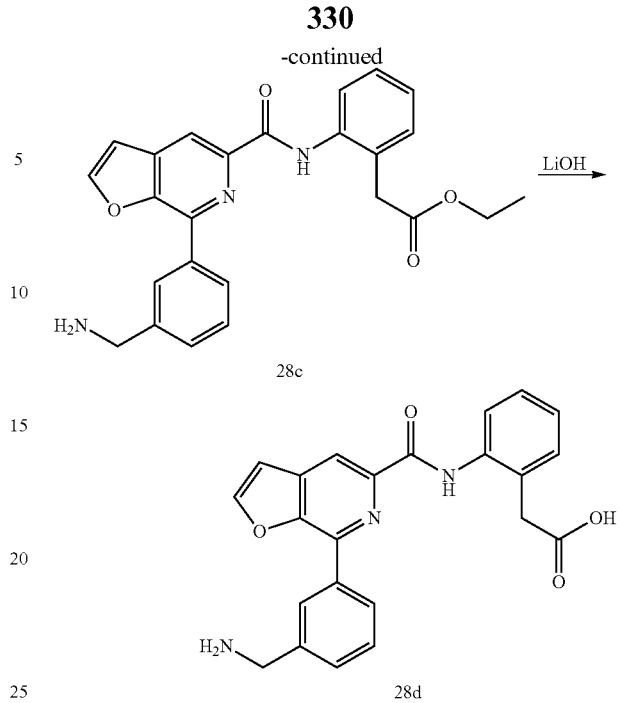

Preparation of 2-(2-(7-(3-(aminomethyl)phenyl)furo[2,3-c]pyridine-5-carboxamido)phenyl)acetic Acid (28d)

Step-1: Preparation of Ethyl 2-(2-(7-chlorofuro[2,3-c]pyridine-5-carboxamido)phenyl)acetate (28b)

Compound 28b was prepared according to the procedure reported in step-4 of Scheme-1 from 7-chlorofuro[2,3-c]pyridine-5-carboxylic acid (28a) (500 mg, 2.53 mmol; CAS #478148-53-7) in DMF (4 mL) using ethyl 2-(2-aminophenyl)acetate (5e) (794 mg, 4.43 mmol), DIPEA (1.33 mL, 7.59 mmol) and HATU (1684 mg, 4.43 mmol). This gave after workup and purification by flash column chromatography [silica (12 g), eluting with EtOAc/MeOH (9:1) in hexane from 0-60%] ethyl 2-(2-(7-chlorofuro[2,3-c]pyridine-5-carboxamido)phenyl)acetate (28b) (500 mg, 55% yield) as a white solid; $^1$H NMR (300 MHz, DMSO-d$_6$) δ 10.26 (s, 1H), 8.53 (s, 1H), 8.49 (d, J=2.1 Hz, 1H), 7.79-7.72 (m, 1H), 7.39-7.32 (m, 3H), 7.25-7.15 (m, 1H), 4.08 (q, J=7.1 Hz, 2H), 3.79 (s, 2H), 1.11 (t, J=7.1 Hz, 3H); MS (ES+): 359.2 (M+1); (ES−) 357.3 (M−1).

Step-2: Preparation of Ethyl 2-(2-(7-(3-(aminomethyl)phenyl)furo[2,3-c]pyridine-5-carboxamido)phenyl)acetate (28c)

Compound 28c was prepared according to the procedure reported in step-3 of Scheme-1 from ethyl 2-(2-(7-chlorofuro[2,3-c]pyridine-5-carboxamido)phenyl)acetate (28b) (500 mg, 1.394 mmol) in dioxane (11 mL) using 3-(aminomethyl)phenylboronic acid hydrochloride (6c) (261 mg, 1.394 mmol), tripotassium phosphate (1.3 M solution) (1.394 mL, 4.18 mmol), tricyclohexylphosphine (117 mg, 0.418 mmol) and Pd$_2$(dba)$_3$ (128 mg, 0.139 mmol) under an Ar atmosphere and heating at 125° C. for 1 h in a microwave. This gave after workup, purification by flash column chromatography [silica (40 g), eluting with ethyl acetate in hexanes from 0-100%] ethyl 2-(2-(7-(3-(aminomethyl)phenyl)furo[2,3-c]pyridine-5-carboxamido)phenyl)acetate (28c) (0.304 g, 51% yield) as a white solid; $^1$H NMR (300 MHz, DMSO-$d_6$) δ 10.60 (s, 1H), 8.69 (s, 1H), 8.61-8.56 (m, 1H), 8.54 (d, J=1.2 Hz, 1H), 8.49 (d, J=2.2 Hz, 1H), 7.86 (d, J=8.2 Hz, 1H), 7.69 (d, J=4.6 Hz, 2H), 7.44-7.33 (m, 3H), 7.27-7.18 (m, 1H), 4.20 (s, 2H), 3.93 (q, J=7.2 Hz, 2H), 3.86 (s, 2H), 0.93 (t, J=7.1 Hz, 3H); MS (ES+): 430.3 (M+1); MS (ES−): 428.3 (M−1), 474.4 (M+Cl); HPLC purity: 96.63%.

Step-3: Preparation of 2-(2-(7-(3-(aminomethyl)phenyl)furo[2,3-c]pyridine-5-carboxamido)phenyl)acetic Acid (28d)

Compound 28d was prepared according to the procedure reported in step-6 of Scheme-1, from ethyl 2-(2-(7-(3-(aminomethyl)phenyl)furo[2,3-c]pyridine-5-carboxamido)phenyl)acetate (28c) (61 mg, 0.142 mmol) in THF (8 mL) using a solution of lithium hydroxide hydrate (41 mg, 1.71 mmol) in water (2 mL). This gave after workup and purification by reverse phase column chromatography [C18 (50 g), eluting with ACN in water (containing 0.1% HCl) from 0-100%] 2-(2-(7-(3-(aminomethyl)phenyl)furo[2,3-c]pyridine-5-carboxamido)phenyl)acetic acid (28d) (140 mgs, 61% yield) as a white solid; $^1$H NMR (300 MHz, DMSO-$d_6$) δ 12.78 (s, 1H), 10.75 (s, 1H), 8.69 (s, 1H), 8.59-8.56 (m, 1H), 8.55 (s, 1H), 8.50 (d, J=2.2 Hz, 1H), 8.43 (s, 3H), 7.96 (d, J=7.6 Hz, 1H), 7.71-7.66 (m, 2H), 7.41-7.34 (m, 3H), 7.24-7.17 (m, 1H), 4.21 (d, J=5.7 Hz, 2H), 3.78 (s, 2H); MS (ES+): 402.3 (M+1); 424.3 (M+Na), (ES−): 400.3 (M−1); HPLC purity 98.75.

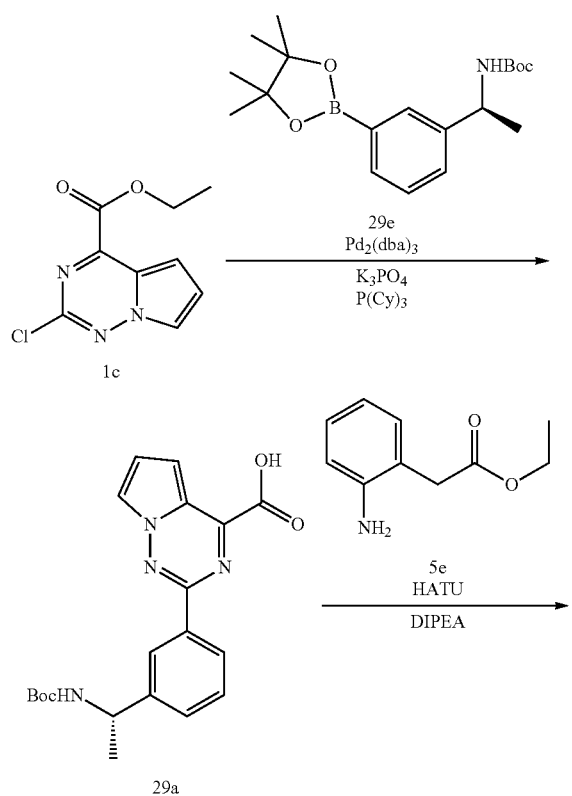

Scheme-29

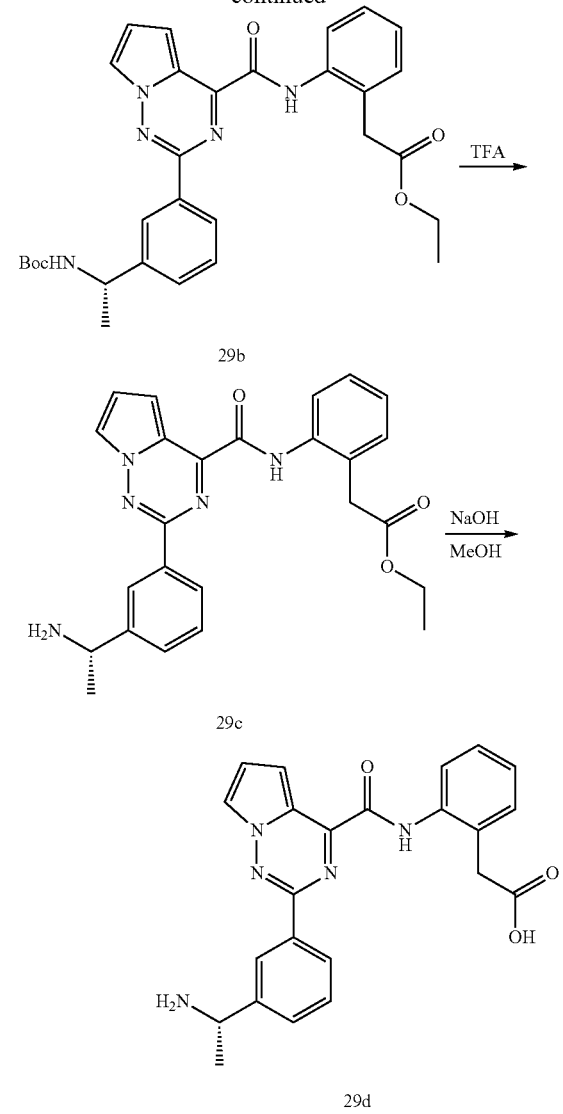

Preparation of (S)-2-(2-(2-(3-(1-aminoethyl)phenyl)pyrrolo[2,1-f][1,2,4]triazine-4-carboxamido)phenyl)acetic Acid (29d)

Step-1: Preparation of (S)-2-(3-(1-((tert-butoxycarbonyl)amino)ethyl)phenyl)pyrrolo[2,1-f][1,2,4]triazine-4-carboxylic Acid (29a)

Compound 29a was prepared according to the procedure reported in step-3 of Scheme-1 from ethyl 2-chloropyrrolo[2,1-f][1,2,4]triazine-4-carboxylate (1c) (300 mg, 1.33 mmol) in dioxane (6 mL) using (S)-tert-butyl 1-(3-(4,4,5,5-tetramethyl-1,3,2-dioxaborolan-2-yl)phenyl)ethylcarbamate (29e) (693 mg, 1.99 mmol; CAS #887254-65-1, prepared according to procedure reported in PCT Int. Appl., 2015009977, 22 Jan. 2015), tripotassium phosphate (0.753 mL, 2.26 mmol, 3 M aqueous solution) tricyclohexylphosphine (112 mg, 0.4 mmol) and Pd$_2$(dba)$_3$ (122 mg, 0.13 mmol) in argon atmosphere and heating at 125° C. for 1 h in a microwave. This gave after workup and purification by flash column chromatography [silica (12 g), eluting with MeOH in DCM from 0-30%] (S)-2-(3-(1-(tert-butoxycarbonylamino)ethyl)phenyl)pyrrolo[2,1-f][1,2,4]triazine-4-carboxylic acid (29a) (110 mg, 15% yield) as a solid; MS (ES−): 381.4, 382.4 (M−1).

Step-2: Preparation of (S)-ethyl 2-(2-(2-(3-(1-((tert-butoxycarbonyl)amino)ethyl)phenyl)pyrrolo[2,1-f][1,2,4]triazine-4-carboxamido)phenyl)acetate (29b)

Compound 29b was prepared according to the procedure reported in step-4 of Scheme-1 from (S)-2-(3-(1-((tert-butoxycarbonyl)amino)ethyl)phenyl)pyrrolo[2,1-f][1,2,4]triazine-4-carboxylic acid (29a) (110 mg, 0.29 mmol) in DMF (5 mL) using ethyl 2-(2-aminophenyl)acetate (5e) (77 mg, 0.43 mmol), DIPEA (0.1 mL, 0.575 mmol) and HATU (164 mg, 0.431 mmol). This gave after workup and purification by flash column chromatography [silica (12 g), eluting with 0-60% EtOAc/MeOH (9:1) in hexane from 0-100%] (S)-ethyl 2-(2-(2-(3-(1-((tert-butoxycarbonyl)amino)ethyl)phenyl)pyrrolo[2,1-f][1,2,4]triazine-4-carboxamido)phenyl)acetate (29b) (103 mg, 66% yield) as a white solid; MS (ES+): 566.4 (M+Na); (ES−) 542.5, 543.5 (M−1).

Step-3: Preparation of (S)-ethyl 2-(2-(2-(3-(1-aminoethyl)phenyl)pyrrolo[2,1-f][1,2,4]triazine-4-carboxamido)phenyl)acetate (29c)

Compound 29c was prepared according to the procedure reported in step-5 of Scheme-1 from (S)-ethyl 2-(2-(2-(3-(1-((tert-butoxycarbonyl)amino)ethyl)phenyl)pyrrolo[2,1-f][1,2,4]triazine-4-carboxamido)phenyl)acetate (29b) (103 mg, 0.19 mmol) in DCM (5 mL) using TFA (0.15 mL, 1.90 mmol). This gave after workup (S)-ethyl 2-(2-(2-(3-(1-aminoethyl)phenyl)pyrrolo[2,1-f][1,2,4]triazine-4-carboxamido)phenyl)acetate (29c) (29 mg, 35% yield) as a yellow solid, MS (ES+): 444.4 (M+1).

Step-4: Preparation of (S)-2-(2-(2-(3-(1-aminoethyl)phenyl)pyrrolo[2,1-f][1,2,4]triazine-4-carboxamido)phenyl)acetic Acid (29d)

Compound 29d was prepared according to the procedure reported in step-4 of Scheme-4 from (S)-ethyl 2-(2-(2-(3-(1-aminoethyl)phenyl)pyrrolo[2,1-f][1,2,4]triazine-4-carboxamido)phenyl)acetate (29c) (29 mg, 0.065 mmol) in MeOH (5 mL) using a solution of NaOH (38 mg, 0.95 mmol) in water (0.5 mL). This gave after workup and purification by reverse phase column chromatography [C18 (50 g), eluting with ACN in water (containing 0.1% HCl) from 0-100%] (S)-2-(2-(2-(3-(1-aminoethyl)phenyl)pyrrolo[2,1-f][1,2,4]triazine-4-carboxamido)phenyl)acetic acid (29d) (28 mg, 35% yield) as a yellow solid; $^1$H NMR (300 MHz, DMSO-$d_6$) δ 12.77 (s, 1H, $D_2O$ exchangeable), 10.91 (s, 1H), 8.66 (s, 1H), 8.60 (s, 3H, $D_2O$ exchangeable), 8.55-8.50 (m, 1H), 8.39 (dd, J=2.5, 1.4 Hz, 1H), 7.90-7.80 (m, 1H), 7.77-7.71 (m, 1H), 7.70-7.57 (m, 2H), 7.48-7.35 (m, 2H), 7.34-7.21 (m, 2H), 4.67-4.45 (m, 1H), 3.81 (s, 2H), 1.61 (d, J=6.7 Hz, 3H); MS (ES+): 416.3 (M+1); (ES−): 414.4 (M−1); 450.4 (M+Cl); HPLC purity; 99.56%.

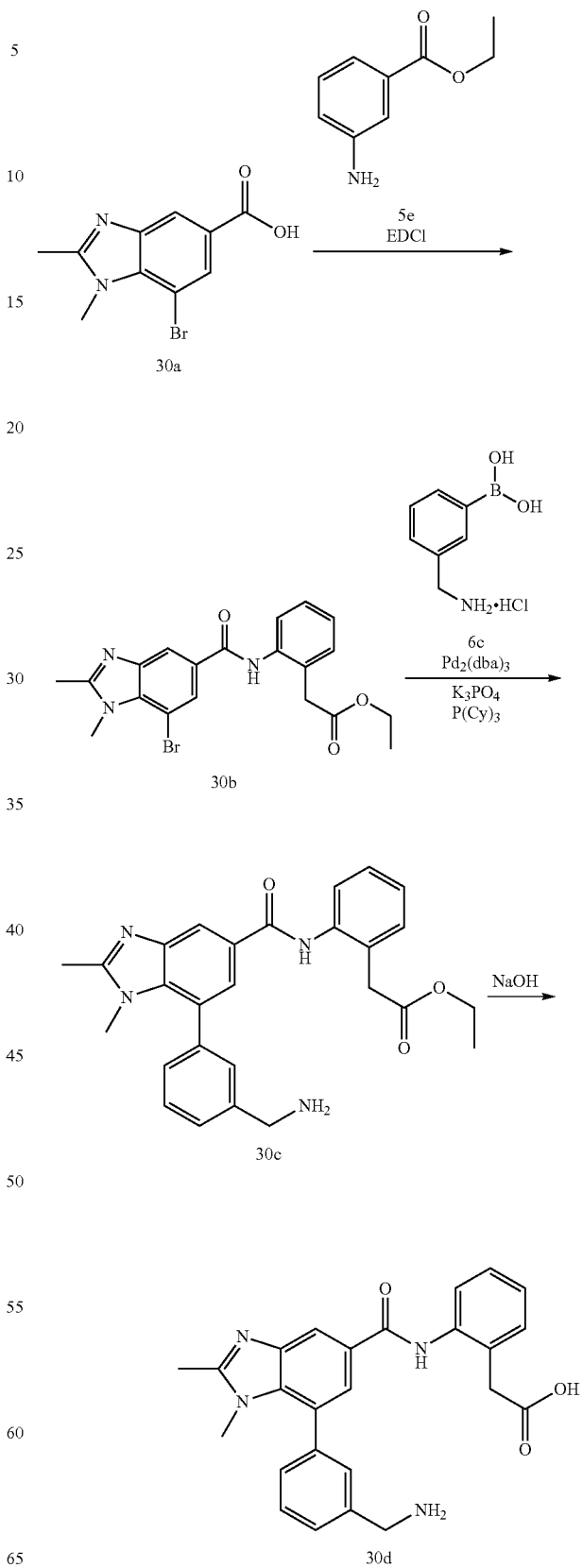

Scheme-30

Preparation of 2-(2-(7-(3-(aminomethyl)phenyl)-1,2-dimethyl-1H-benzo[d]imidazole-5-carboxamido)phenyl)acetic Acid (30d)

Step-1: Preparation of Ethyl 2-(2-(7-bromo-1,2-dimethyl-1H-benzo[d]imidazole-5-carboxamido)phenyl)acetate (30b)

Compound 30b was prepared according to the procedure reported in step-1 of Scheme-7 from 7-bromo-1,2-dimethyl-1H-benzo[d]imidazole-5-carboxylic acid (30a) (500 mg, 2.53 mmol; CAS #1420800-25-4) in MeOH (10 mL) using ethyl 2-(2-aminophenyl)acetate (5e) (549 mg, 3.07 mmol) and EDCI (641 mg, 3.34 mmol). This gave after workup and purification by flash column chromatography [silica (12 g), eluting with EtOAc in hexane from 0-60%] ethyl 2-(2-(7-bromo-1,2-dimethyl-1H-benzo[d]imidazole-5-carboxamido)phenyl)acetate (30b) (300 mg, 28% yield) as an off white solid. MS (ES+): 432.3 (M+1); (ES−) 464.3, 466.3 (M+Cl).

Step-2: Preparation of Ethyl 2-(2-(7-(3-(aminomethyl)phenyl)-1,2-dimethyl-1H-benzo[d]imidazole-5-carboxamido)phenyl)acetate (30c)

Compound 30c was prepared according to the procedure reported in step-3 of Scheme-1 from ethyl 2-(2-(7-bromo-1,2-dimethyl-1H-benzo[d]imidazole-5-carboxamido)phenyl)acetate (30b) (300 mg, 0.697 mmol) in dioxane (3 mL) using 3-(aminomethyl)phenylboronic acid hydrochloride (6c) (196 mg, 1.046 mmol), tripotassium phosphate (1.3 M solution) (0.697 mL, 2.092 mmol), tricyclohexylphosphine (59 mg, 0.209 mmol) and $Pd_2(dba)_3$ (64 mg, 0.07 mmol) under an Ar atmosphere and heating at 125° C. for 45 min in a microwave. This gave after workup, purification by flash column chromatography [silica (12 g), eluting with DMA80 in DCM from 0-60%] followed by reverse phase column chromatography [C18 (50 g), eluting with ACN in water (containing 0.1% HCl) from 0-100%] ethyl 2-(2-(7-(3-(aminomethyl)phenyl)-1,2-dimethyl-1H-benzo[d]imidazole-5-carboxamido)phenyl)acetate (30c) (220 mg, 69% yield) as a white solid; $^1$H NMR (300 MHz, DMSO-$d_6$) δ 10.46 (s, 1H), 8.70 (s, 3H), 8.43 (d, J=1.6 Hz, 1H), 7.97 (d, J=1.5 Hz, 1H), 7.75 (d, J=1.8 Hz, 1H), 7.72-7.51 (m, 3H), 7.41-7.21 (m, 4H), 4.13 (d, J=5.8 Hz, 3H), 3.93 (q, J=7.1 Hz, 2H), 2.84 (s, 3H), 3.45 (s, 3H), 0.97 (t, J=7.1 Hz, 3H).

Step-3: Preparation of 2-(2-(7-(3-(aminomethyl)phenyl)-1,2-dimethyl-1H-benzo[d]imidazole-5-carboxamido)phenyl)acetic Acid (30d)

Compound 30d was prepared according to the procedure reported in step-4 of Scheme-4, from ethyl 2-(2-(7-(3-(aminomethyl)phenyl)-1,2-dimethyl-1H-benzo[d]imidazole-5-carboxamido)phenyl)acetate (30c) (125 mg, 0.27 mmol) in MeOH (10 mL) using a solution of sodium hydroxide (110 mg, 2.74 mmol) in water (2 mL). This gave after workup and purification by reverse phase column chromatography [C18 (50 g), eluting with ACN in water (containing 0.1% HCl) from 0-100%] 2-(2-(7-(3-(aminomethyl)phenyl)-1,2-dimethyl-1H-benzo[d]imidazole-5-carboxamido)phenyl)acetic acid (30d) (81 mg, 69% yield) as a white solid; $^1$H NMR (300 MHz, DMSO-$d_6$) δ 10.49 (s, 1H, $D_2O$ exchangeable), 8.71 (s, 3H, $D_2O$ exchangeable), 8.45 (d, J=1.6 Hz, 1H), 7.99 (d, J=1.6 Hz, 1H), 7.77 (d, J=2.1 Hz, 1H), 7.74-7.68 (m, 1H), 7.67-7.54 (m, 2H), 7.43-7.20 (m, 4H), 4.13 (q, J=5.9 Hz, 2H), 3.68 (s, 2H), 3.46 (s, 3H), 2.85 (s, 3H); MS (ES+): 429.4 (M+1); (ES−): 427.4 (M−1); 463.4 (M+Cl); HPLC purity: 100%.

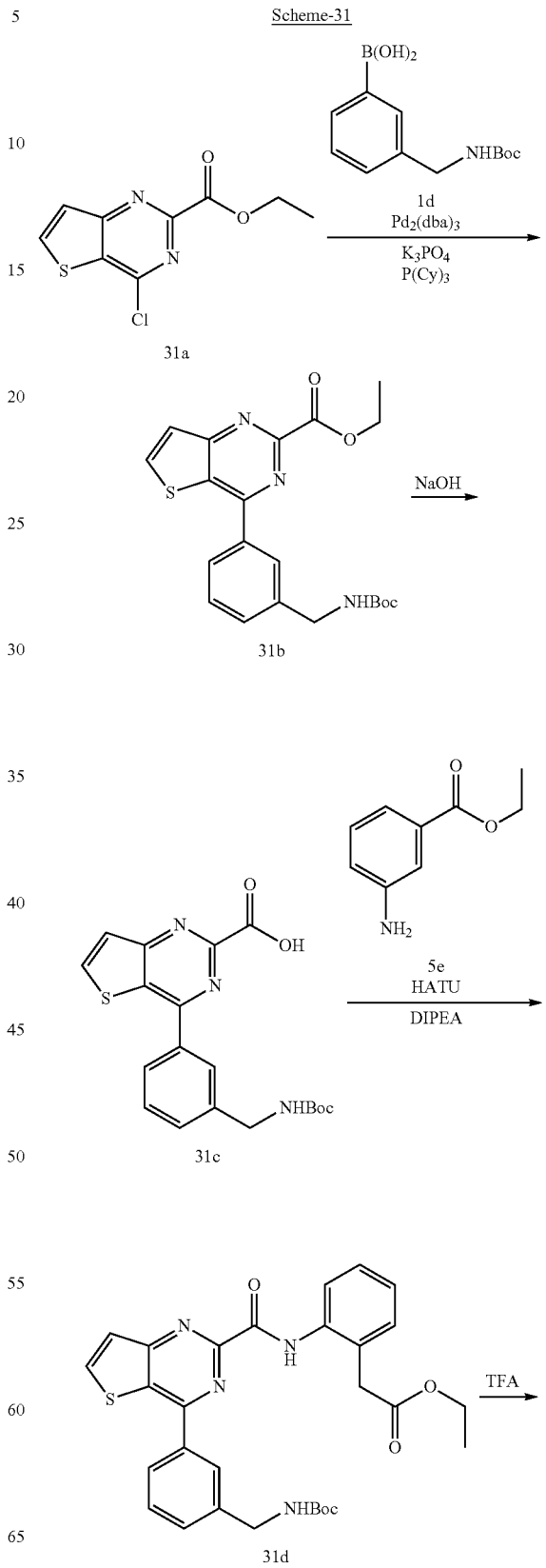

Scheme-31

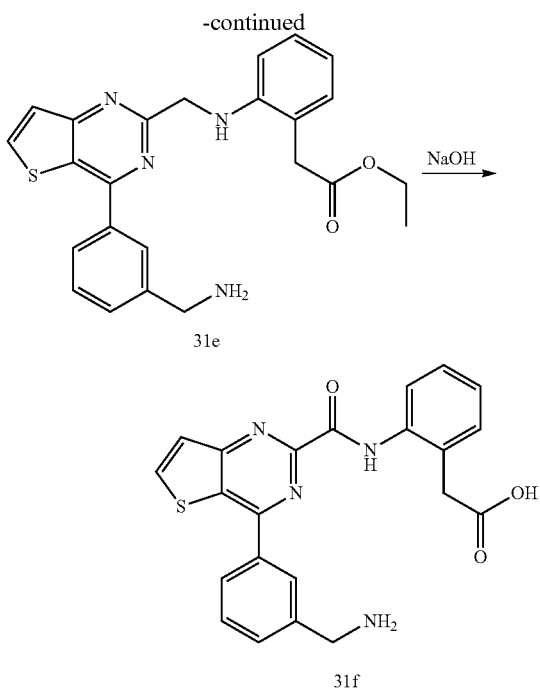

Preparation of 2-(2-(4-(3-(aminomethyl)phenyl)thieno[3,2-d]pyrimidine-2-carboxamido)phenyl)acetic Acid (31f)

Step-1: Preparation of Ethyl 4-(3-(((tert-butoxycarbonyl)amino)methyl)phenyl)thieno[3,2-d]pyrimidine-2-carboxylate (31b)

Compound 31b was prepared according to the procedure reported in step-3 of Scheme-1 from ethyl 4-chlorothieno[3,2-d]pyrimidine-2-carboxylate (31a) (350 mg, 1.44 mmol; CAS #319442-18-7) in dioxane (3 mL) using (3-(((tert-butoxycarbonyl)amino)methyl)phenyl)boronic acid (Id) (543 mg, 2.16 mmol), tripotassium phosphate (0.82 mL, 2.452 mmol, 3 M aqueous solution), tricyclohexylphosphine (81 mg, 0.288 mmol) and $Pd_2(dba)_3$ (73 mg, 0.079 mmol) in argon atmosphere and heating at 125° C. for 30 min in a microwave. This gave after workup and purification by flash column chromatography [silica (12 g), eluting with EtOAc in hexane from 0-70%] ethyl 4-(3-(((tert-butoxycarbonyl)amino)methyl)phenyl)thieno[3,2-d]pyrimidine-2-carboxylate (31b) (400 mg, 67% yield) as a yellow solid.

Step-2: Preparation of 4-(3-(((tert-butoxycarbonyl)amino)methyl)phenyl)thieno[3,2-d]pyrimidine-2-carboxylic Acid (31c)

Compound 31c was prepared according to the procedure reported in step-4 of Scheme-4 from ethyl 4-(3-(((tert-butoxycarbonyl)amino)methyl)phenyl)thieno[3,2-d]pyrimidine-2-carboxylate (31b) (400 mg, 0.97 mmol) in MeOH (10 mL) using a solution of NaOH (193 mg, 4.84 mmol) in water (2 mL). This gave after workup and purification by reverse phase column chromatography [C18 (50 g), eluting with ACN in water (containing 0.1% HCl) from 0-100%] 4-(3-(((tert-butoxycarbonyl)amino)methyl)phenyl)thieno[3,2-d]pyrimidine-2-carboxylic acid (31c) (365 mg, 98% yield) as a white solid; $^1H$ NMR (300 MHz, DMSO-$d_6$) δ 13.46 (s, 1H), 8.72 (d, J=5.6 Hz, 1H), 8.19-7.99 (m, 2H), 7.86 (d, J=5.6 Hz, 1H), 7.69-7.47 (m, 3H), 4.28 (d, J=6.2 Hz, 2H), 1.41 (s, 9H).

Step-3: Preparation of Ethyl 2-(2-(4-(3-(((tert-butoxycarbonyl)amino)methyl)phenyl)thieno[3,2-d]pyrimidine-2-carboxamido)phenyl)acetate (31d)

Compound 31d was prepared according to the procedure reported in step-4 of Scheme-1 from 4-(3-(((tert-butoxycarbonyl)amino)methyl)phenyl)thieno[3,2-d]pyrimidine-2-carboxylic acid (31c) (365 mg, 0.95 mmol) in DMF (5 mL) using ethyl 2-(2-aminophenyl)acetate (5e) (204 mg, 1.14 mmol), DIPEA (0.331 mL, 1.894 mmol) and HATU (432 mg, 1.14 mmol). This gave after workup and purification by flash column chromatography [silica (12 g), eluting with 0-60% EtOAc/MeOH (9:1) in hexane from 0-100%] ethyl 2-(2-(4-(3-(((tert-butoxycarbonyl)amino)methyl)phenyl)thieno[3,2-d]pyrimidine-2-carboxamido)phenyl)acetate (31d) (425 mg, 82% yield) as a white solid; $^1H$ NMR (300 MHz, DMSO-$d_6$) δ 10.72 (s, 1H), 8.77 (d, J=5.5 Hz, 1H), 8.27-8.19 (m, 2H), 7.90 (d, J=5.5 Hz, 1H), 7.86-7.81 (m, 1H), 7.70-7.61 (m, 1H), 7.60-7.51 (m, 2H), 7.44-7.34 (m, 2H), 7.28-7.19 (m, 1H), 4.30 (d, J=6.2 Hz, 2H), 3.98 (q, J=7.1 Hz, 2H), 3.86 (s, 2H), 1.40 (s, 9H), 0.98 (t, J=7.1 Hz, 3H).

Step-4: Preparation of Ethyl 2-(2-(4-(3-(aminomethyl)phenyl)thieno[3,2-d]pyrimidine-2-carboxamido)phenyl)acetate (31e)

Compound 31e was prepared according to the procedure reported in step-5 of Scheme-1 from ethyl 2-(2-(4-(3-(((tert-butoxycarbonyl)amino)methyl)phenyl)thieno[3,2-d]pyrimidine-2-carboxamido)phenyl)acetate (31d) (400 mg, 0.73 mmol) in DCM (5 mL) using TFA (0.56 mL, 7.32 mmol). This gave after workup and purification by reverse phase column purification [C18 (50 g), eluting with ACN in water (containing 0.1% HCl) from 0-100%] ethyl 2-(2-(4-(3-(aminomethyl)phenyl)thieno[3,2-d]pyrimidine-2-carboxamido)phenyl)acetate (31e) (308 mg, 94% yield) as a white solid; $^1H$ NMR (300 MHz, DMSO-$d_6$) δ 10.72 (s, 1H, $D_2O$ exchangeable), 8.80 (d, J=5.4 Hz, 1H), 8.60 (s, 3H, $D_2O$ exchangeable), 8.51 (s, 1H), 8.39-8.31 (m, 1H), 7.93 (d, J=5.5 Hz, 1H), 7.89-7.72 (m, 3H), 7.45-7.35 (m, 2H), 7.32-7.21 (m, 1H), 4.22 (s, 2H), 3.98 (q, J=7.1 Hz, 2H), 3.87 (s, 2H), 1.00 (t, J=7.1 Hz, 3H); MS (ES+): 447.3 (M+1); (ES−): 481.3 (M+Cl); HPLC purity, 99.72%.

Step-5: Preparation of 2-(2-(4-(3-(aminomethyl)phenyl)thieno[3,2-d]pyrimidine-2-carboxamido)phenyl)acetic Acid (31f)

Compound 31f was prepared according to the procedure reported in step-4 of Scheme-4 from ethyl 2-(2-(4-(3-(aminomethyl)phenyl)thieno[3,2-d]pyrimidine-2-carboxamido)phenyl)acetate (31e) (256 mg, 0.57 mmol) in MeOH/THF (10 mL, 1:1) using a solution of NaOH (92 mg, 2.29 mmol) in water (2 mL). This gave after workup and purification by reverse phase column chromatography [C18 (50 g), eluting with ACN in water (containing 0.1% HCl) from 0-100%] 2-(2-(4-(3-(aminomethyl)phenyl)thieno[3,2-d]pyrimidine-2-carboxamido)phenyl)acetic acid (31f) (112 mg, 47% yield) as a yellow solid; $^1H$ NMR (300 MHz, DMSO-$d_6$) δ 10.82 (s, 1H, $D_2O$ exchangeable), 8.80 (d, J=5.5 Hz, 1H), 8.60-8.42 (m, 4H, partially $D_2O$ exchangeable), 8.39-8.30 (m, 1H), 7.95-7.70 (m, 4H), 7.45-7.33 (m, 2H), 7.23 (t, J=7.4

Hz, 1H), 4.27-4.20 (m, 2H), 3.79 (s, 2H); MS (ES+) 419.3 (M+1); 441.3 (M+Na); (ES−) 417.3 (M−1), 453.3 (M+Cl); HPLC, 0.395 min, 98.46%.

Scheme-32

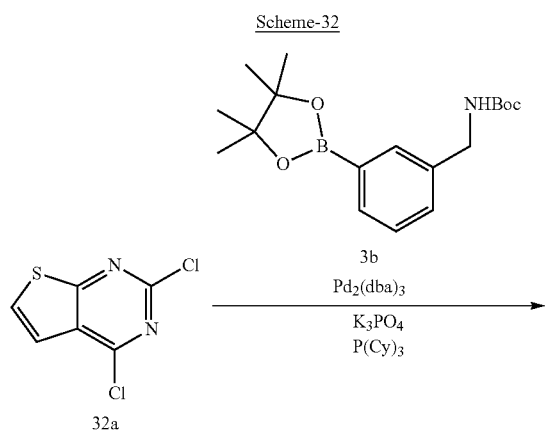

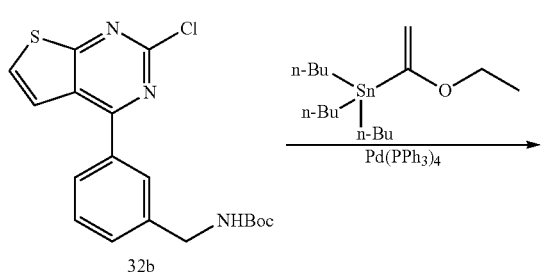

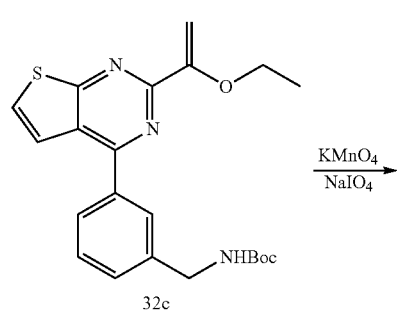

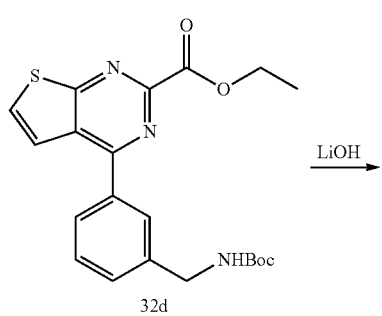

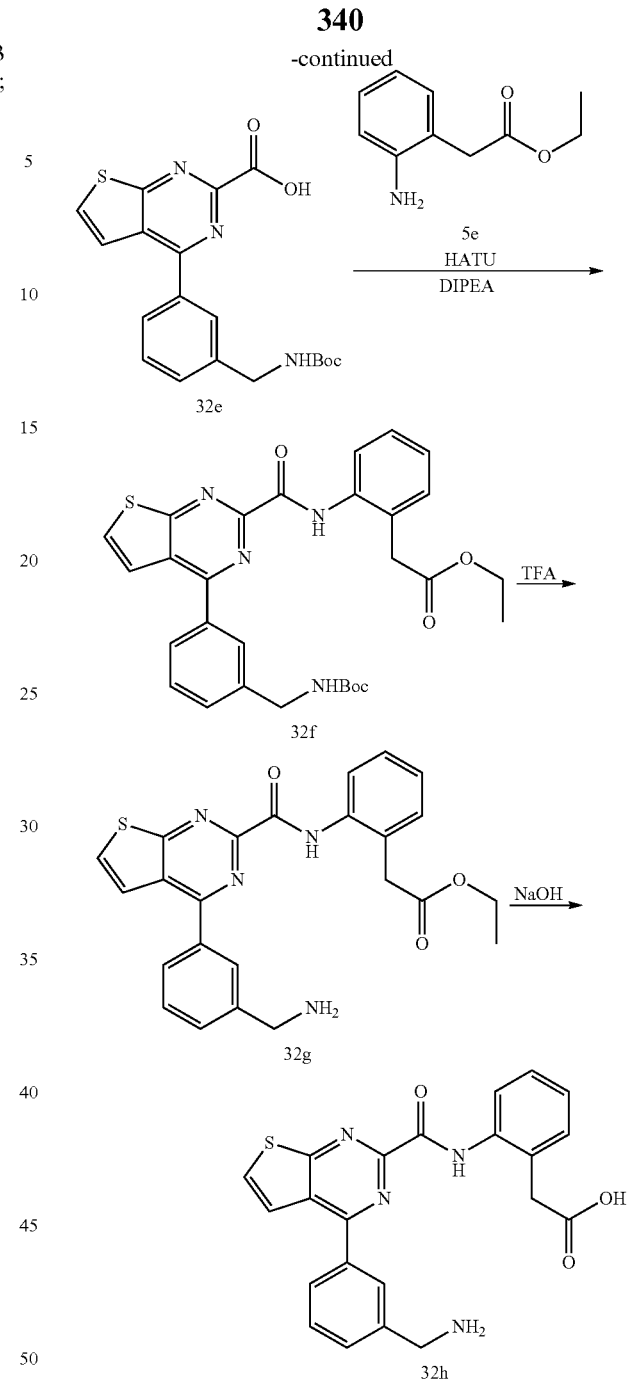

Preparation of 2-(2-(4-(3-(aminomethyl)phenyl)thieno[2,3-d]pyrimidine-2-carboxamido)phenyl)acetic Acid (32h)

Step-1: Preparation of tert-butyl 3-(2-chlorothieno[2,3-d]pyrimidin-4-yl)benzylcarbamate (32b)

Compound 32b was prepared according to the procedure reported in step-3 of Scheme-1 from 2,4-dichlorothieno[2,3-d]pyrimidine (32a) (4.5 g, 21.94 mmol; CAS #18740-39-1) in dioxane (100 mL) using tert-butyl 3-(4,4,5,5-tetramethyl-1,3,2-dioxaborolan-2-yl)benzylcarbamate (3b) (5.63 g, 16.88 mmol), tripotassium phosphate (22.07 mL, 28.7 mmol) in water (1 mL), tricyclohexylphosphine (0.95 g, 3.38 mmol) and Pd$_2$(dba)$_3$ (0.85 g, 0.93 mmol) in argon atmosphere and heating in an oil bath at 120° C. for 1 h. This gave after workup and purification by flash column chromatography [silica (80 g), eluting with EtOAc in hexane from 0-70%] tert-butyl 3-(2-chlorothieno[2,3-d]pyrimidin-4-yl)benzylcarbamate (32b) (4.5 g, 71% yield) as a yellow solid; $^1$H NMR (300 MHz, DMSO-d$_6$) δ 8.08 (d, J=6.0 Hz, 1H), 7.89-7.83 (m, 2H), 7.74 (d, J=6.1 Hz, 1H), 7.62-7.47 (m, 3H), 4.25 (d, J=6.2 Hz, 2H), 1.40 (s, 9H).

Step-2: Preparation of tert-butyl 3-(2-(1-ethoxyvinyl)thieno[2,3-d]pyrimidin-4-yl)benzylcarbamate (32c)

Compound 32c was prepared according to the procedure reported in step-1 of Scheme-1 from tert-butyl 3-(2-chlorothieno[2,3-d]pyrimidin-4-yl)benzylcarbamate (32b) (4.5 g, 11.97 mmol) in DMF (60 mL) using 1-ethoxyvinyltri-n-butyltin (4.89 mL, 14.37 mmol) and Pd(PPh$_3$)$_4$ (0.692 g, 0.599 mmol) in argon atmosphere and heating at 110° C. for 10 h. This gave after workup and purification by flash column chromatography [silica (80 g), eluting with EtOAc in hexane from 0-70%] tert-butyl 3-(2-(1-ethoxyvinyl)thieno[2,3-d]pyrimidin-4-yl)benzylcarbamate (32c) (4.4 g, 89% yield) as a yellow solid; MS (ES+): 412.2 (M+1).

Step-3: Preparation of Ethyl 4-(3-(((tert-butoxycarbonyl)amino)methyl)phenyl)thieno[2,3-d]pyrimidine-2-carboxylate (32d)

Compound 32d was prepared according to the procedure reported in step-2 of Scheme-1 from tert-butyl 3-(2-(1-ethoxyvinyl)thieno[2,3-d]pyrimidin-4-yl)benzylcarbamate (32c) (4.4 g, 10.69 mmol) in 1,4-dioxane (50 mL) using sodium periodate solution (4.57 g, 21.38 mmol) in water (20 mL) and KMnO$_4$ (0.676 g, 4.28 mmol, and second dosing of 0.338 g, 2.138 mmol after 12 h). This gave after workup and purification by flash column chromatography [silica (40 g), eluting with EtOAc in hexane from 0-60%] ethyl 4-(3-(((tert-butoxycarbonyl)amino)methyl)phenyl)thieno[2,3-d]pyrimidine-2-carboxylate (32d) (1.6 g, 36% yield) as a yellow solid; MS (ES+): 414.2 (M+1), 436.1 (M+Na).

Step-4: Preparation of 4-(3-(((tert-butoxycarbonyl)amino)methyl)phenyl)thieno[2,3-d]pyrimidine-2-carboxylic Acid (32e)

Compound 32e was prepared according to the procedure reported in step-6 of Scheme-1 from ethyl 4-(3-(((tert-butoxycarbonyl)amino)methyl)phenyl)thieno[2,3-d]pyrimidine-2-carboxylate (32d) (1.6 g, 3.87 mmol) in THF/MeOH (30 mL, 1:1) using lithium hydroxide hydrate (0.812 g, 19.35 mmol) in water (5 mL). This gave after workup and purification by reverse phase column [C18 (50 g), eluting with ACN in water (containing 0.1% HCl) from 0-100%] 4-(3-(((tert-butoxycarbonyl)amino)methyl)phenyl)thieno[2,3-d]pyrimidine-2-carboxylic acid (32e) (0.55 g, 37% yield) as a white solid; $^1$H NMR (300 MHz, DMSO-d$_6$) δ 13.62 (s, 1H), 8.26 (d, J=6.0 Hz, 1H), 7.93-7.87 (m, 2H), 7.82 (d, J=6.1 Hz, 1H), 7.64-7.44 (m, 3H), 4.26 (d, J=6.2 Hz, 2H), 1.40 (s, 9H).

Step-5: Preparation of Ethyl 2-(2-(4-(3-(((tert-butoxycarbonyl)amino)methyl)phenyl)thieno[2,3-d]pyrimidine-2-carboxamido)phenyl)acetate (32f)

Compound 32f was prepared according to the procedure reported in step-4 of Scheme-1 from 4-(3-(((tert-butoxycarbonyl)amino)methyl)phenyl)thieno[2,3-d]pyrimidine-2-carboxylic acid (32e) (547 mg, 1.42 mmol) in DMF (5 mL) using ethyl 2-(2-aminophenyl)acetate (5e) (305 mg, 1.703 mmol), DIPEA (0.5 mL, 2.84 mmol) and HATU (648 mg, 1.703 mmol). This gave after workup and purification by flash column chromatography [silica (12 g), eluting with 0-60% EtOAc/MeOH (9:1) in hexane from 0-100%] ethyl 2-(2-(4-(3-(((tert-butoxycarbonyl)amino)methyl)phenyl)thieno[2,3-d]pyrimidine-2-carboxamido)phenyl)acetate (32f) (620 mg, 1.134 mmol, 80% yield) as a white solid; $^1$H NMR (300 MHz, DMSO-d$_6$) δ 10.71 (s, 1H), 8.29 (d, J=6.1 Hz, 1H), 8.12-7.99 (m, 2H), 7.89 (d, J=6.1 Hz, 1H), 7.86-7.78 (m, 1H), 7.65-7.48 (m, 3H), 7.38 (d, J=7.5 Hz, 2H), 7.29-7.18 (m, 1H), 4.29 (d, J=6.1 Hz, 2H), 3.96 (q, J=7.1 Hz, 2H), 3.85 (s, 2H), 1.40 (s, 9H), 0.98 (t, J=7.1 Hz, 3H); MS (ES+): 569.4 (M+Na); (ES−): 545.5 (M−1).

Step-6: Preparation of Ethyl 2-(2-(4-(3-(aminomethyl)phenyl)thieno[2,3-d]pyrimidine-2-carboxamido)phenyl)acetate (32g)

Compound 32g was prepared according to the procedure reported in step-5 of Scheme-1 from ethyl 2-(2-(4-(3-(((tert-butoxycarbonyl)amino)methyl)phenyl)thieno[2,3-d]pyrimidine-2-carboxamido)phenyl)acetate (32f) (600 mg, 1.10 mmol) in DCM (10 mL) using TFA (0.85 mL, 10.98 mmol). This gave after workup and purification by flash column chromatography [silica (12 g), eluting with DMA80 in DCM from 0-50%] followed by reverse phase column chromatography [C18 (50 g), eluting with ACN in water (containing 0.1% HCl) from 0-100%] ethyl 2-(2-(4-(3-(aminomethyl)phenyl)thieno[2,3-d]pyrimidine-2-carboxamido)phenyl)acetate (32g) (385 mg, 79% yield) as a white solid; $^1$H NMR (300 MHz, DMSO-d$_6$) δ 10.72 (s, 1H, D$_2$O exchangeable), 8.58 (s, 3H, D$_2$O exchangeable), 8.35-8.27 (m, 2H), 8.24 (d, J=7.6 Hz, 1H), 8.10 (d, J=6.1 Hz, 1H), 7.84-7.75 (m, 2H), 7.75-7.68 (m, 1H), 7.42-7.34 (m, 2H), 7.29-7.20 (m, 1H), 4.30-4.14 (m, 2H), 3.98 (q, J=7.2 Hz, 2H), 3.85 (s, 2H), 1.01 (t, J=7.1 Hz, 3H); MS (ES+): 447.3 (M+1); (ES−): 481.3 (M+Cl); HPLC purity, 99.41%.

Step-7: Preparation of 2-(2-(4-(3-(aminomethyl)phenyl)thieno[2,3-d]pyrimidine-2-carboxamido)phenyl)acetic Acid (32h)

Compound 32h was prepared according to the procedure reported in step-4 of Scheme-4 from ethyl 2-(2-(4-(3-(aminomethyl)phenyl)thieno[2,3-d]pyrimidine-2-carboxamido)phenyl)acetate (32g) (200 mg, 0.448 mmol) in MeOH/THF (10 mL, 1:1) using a solution of NaOH (72 mg, 1.79 mmol) in water (2 mL). This gave after workup and purification by reverse phase column chromatography [C18 (50 g), eluting with ACN in water (containing 0.1% HCl) from 0-100%] 2-(2-(4-(3-(aminomethyl)phenyl)thieno[2,3-d]pyrimidine-2-carboxamido)phenyl)acetic acid (32h) (150 mg, 80% yield) as a yellow solid; $^1$H NMR (300 MHz, DMSO-d$_6$) δ 12.79 (s, 1H, D$_2$O exchangeable), 10.81 (s, 1H, D$_2$O exchangeable), 8.60 (s, 3H, D$_2$O exchangeable), 8.35-8.27 (m, 2H), 8.27-8.20 (m, 1H), 8.17-8.07 (m, 1H), 7.95-7.84 (m, 1H), 7.83-7.77 (m, 1H), 7.77-7.67 (m, 1H), 7.44-7.33 (m, 2H), 7.29-7.17 (m, 1H), 4.26-4.17 (m, 2H), 3.78 (s, 2H); MS (ES+): 419.3 (M+1); 441.3 (M+Na); (ES−): 417.3 (M−1), 453.3 (M+Cl); HPLC, 0.406 min, 100%.

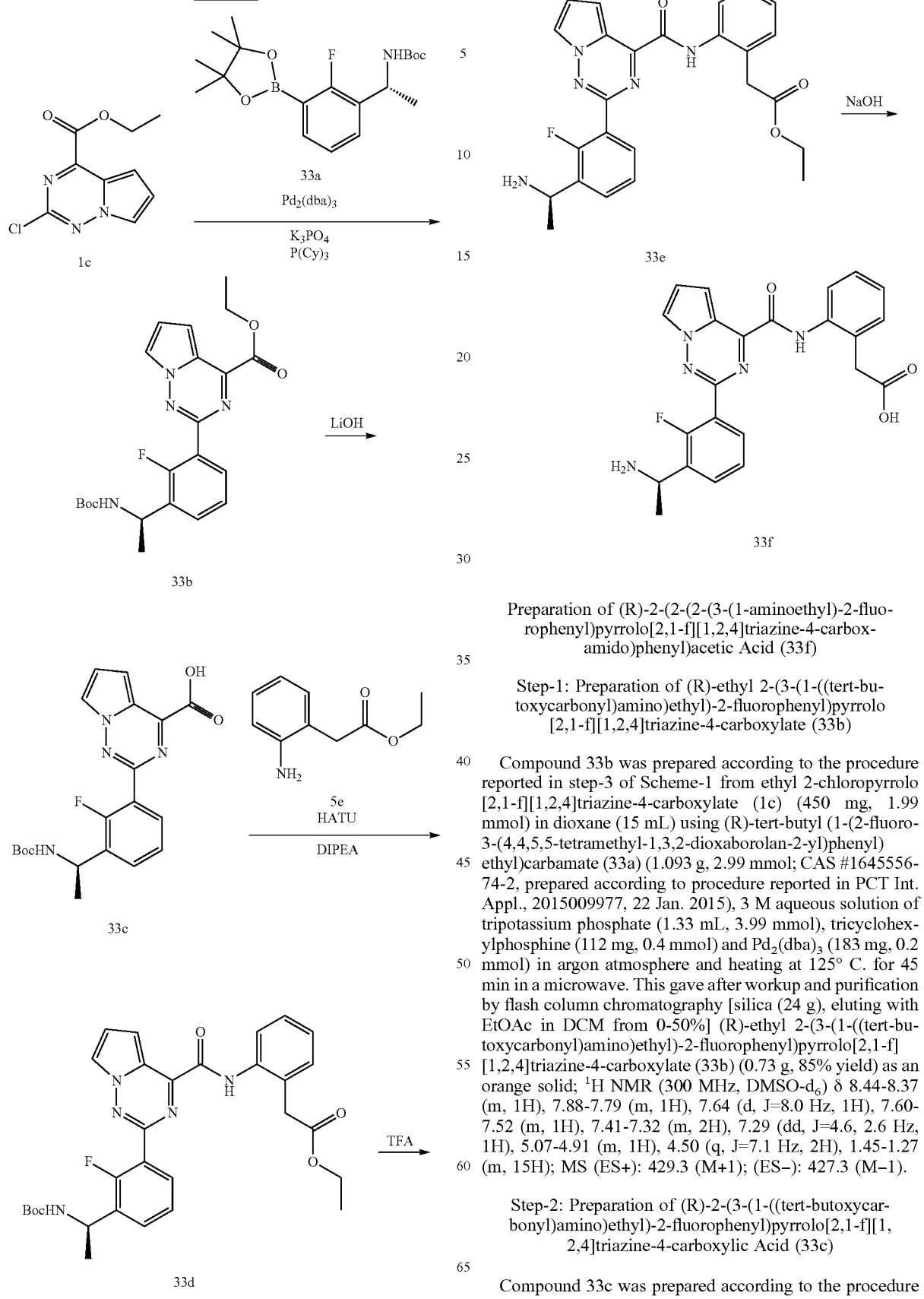

Preparation of (R)-2-(2-(2-(3-(1-aminoethyl)-2-fluorophenyl)pyrrolo[2,1-f][1,2,4]triazine-4-carboxamido)phenyl)acetic Acid (33f)

Step-1: Preparation of (R)-ethyl 2-(3-(1-((tert-butoxycarbonyl)amino)ethyl)-2-fluorophenyl)pyrrolo[2,1-f][1,2,4]triazine-4-carboxylate (33b)

Compound 33b was prepared according to the procedure reported in step-3 of Scheme-1 from ethyl 2-chloropyrrolo[2,1-f][1,2,4]triazine-4-carboxylate (1c) (450 mg, 1.99 mmol) in dioxane (15 mL) using (R)-tert-butyl (1-(2-fluoro-3-(4,4,5,5-tetramethyl-1,3,2-dioxaborolan-2-yl)phenyl)ethyl)carbamate (33a) (1.093 g, 2.99 mmol; CAS #1645556-74-2, prepared according to procedure reported in PCT Int. Appl., 2015009977, 22 Jan. 2015), 3 M aqueous solution of tripotassium phosphate (1.33 mL, 3.99 mmol), tricyclohexylphosphine (112 mg, 0.4 mmol) and Pd$_2$(dba)$_3$ (183 mg, 0.2 mmol) in argon atmosphere and heating at 125° C. for 45 min in a microwave. This gave after workup and purification by flash column chromatography [silica (24 g), eluting with EtOAc in DCM from 0-50%] (R)-ethyl 2-(3-(1-((tert-butoxycarbonyl)amino)ethyl)-2-fluorophenyl)pyrrolo[2,1-f][1,2,4]triazine-4-carboxylate (33b) (0.73 g, 85% yield) as an orange solid; $^1$H NMR (300 MHz, DMSO-d$_6$) δ 8.44-8.37 (m, 1H), 7.88-7.79 (m, 1H), 7.64 (d, J=8.0 Hz, 1H), 7.60-7.52 (m, 1H), 7.41-7.32 (m, 2H), 7.29 (dd, J=4.6, 2.6 Hz, 1H), 5.07-4.91 (m, 1H), 4.50 (q, J=7.1 Hz, 2H), 1.45-1.27 (m, 15H); MS (ES+): 429.3 (M+1); (ES−): 427.3 (M−1).

Step-2: Preparation of (R)-2-(3-(1-((tert-butoxycarbonyl)amino)ethyl)-2-fluorophenyl)pyrrolo[2,1-f][1,2,4]triazine-4-carboxylic Acid (33c)

Compound 33c was prepared according to the procedure reported in step-6 of Scheme-1 from (R)-ethyl 2-(3-(1-((tert-butoxycarbonyl)amino)ethyl)-2-fluorophenyl)pyrrolo[2,1-f][1,2,4]triazine-4-carboxylate (33b) (0.73 g, 1.704 mmol) in THF (15 mL) using lithium hydroxide hydrate (0.107 g, 2.56 mmol) in water (3 mL). This gave after workup (R)-2-(3-(1-((tert-butoxycarbonyl)amino)ethyl)-2-fluorophenyl)pyrrolo[2,1-f][1,2,4]triazine-4-carboxylic acid (33c) (0.67 g, 98% yield) as a light orange foam; $^1$H NMR (300 MHz, DMSO-$d_6$) δ 14.37 (s, 1H), 8.39-8.34 (m, 1H), 7.87 (t, J=7.2 Hz, 1H), 7.63 (d, J=8.0 Hz, 1H), 7.59-7.51 (m, 1H), 7.40-7.31 (m, 2H), 7.25 (dd, J=4.6, 2.6 Hz, 1H), 4.99 (t, J=7.4 Hz, 1H), 1.46-1.24 (m, 12H); MS (ES+): 423.3 (M+Na); (ES−): 399.4 (M−1).

Step-3: Preparation of (R)-ethyl 2-(2-(2-(3-(1-((tert-butoxycarbonyl)amino)ethyl)-2-fluorophenyl)pyrrolo[2,1-f][1,2,4]triazine-4-carboxamido)phenyl)acetate (33d)

Compound 33d was prepared according to the procedure reported in step-4 of Scheme-1 from (R)-2-(3-(1-((tert-butoxycarbonyl)amino)ethyl)-2-fluorophenyl)pyrrolo[2,1-f][1,2,4]triazine-4-carboxylic acid (33c) (200 mg, 0.499 mmol) in DMF (3 mL) using ethyl 2-(2-aminophenyl)acetate (5e) (134 mg, 0.75 mmol), DIPEA (0.174 mL, 1.00 mmol) and HATU (228 mg, 0.6 mmol). This gave after workup and purification by flash column chromatography [silica (12 g), eluting with EtOAc in hexane from 0-100%] (R)-ethyl 2-(2-(2-(3-(1-((tert-butoxycarbonyl)amino)ethyl)-2-fluorophenyl)pyrrolo[2,1-f][1,2,4]triazine-4-carboxamido)phenyl)acetate (33d) (0.22 g, 78% yield) as an orange solid; $^1$H NMR (300 MHz, DMSO-$d_6$) δ 10.67 (s, 1H), 8.42 (d, J=2.4 Hz, 1H), 8.16 (t, J=7.4 Hz, 1H), 7.78 (d, J=8.1 Hz, 1H), 7.64 (d, J=8.1 Hz, 1H), 7.61-7.51 (m, 2H), 7.44-7.32 (m, 3H), 7.32-7.20 (m, 2H), 5.09-4.93 (m, 1H), 3.95 (q, J=7.1 Hz, 2H), 3.83 (s, 2H), 1.43-1.19 (m, 12H), 1.02-0.90 (m, 3H); MS (ES+): 584.4 (M+Na); (ES−): 560.5 (M−1).

Step-4: Preparation of (R)-ethyl 2-(2-(2-(3-(1-aminoethyl)-2-fluorophenyl)pyrrolo[2,1-f][1,2,4]triazine-4-carboxamido)phenyl)acetate (33e)

Compound 33e was prepared according to the procedure reported in step-5 of Scheme-1 from (R)-ethyl 2-(2-(2-(3-(1-((tert-butoxycarbonyl)amino)ethyl)-2-fluorophenyl)pyrrolo[2,1-f][1,2,4]triazine-4-carboxamido)phenyl)acetate (33d) (200 mg, 0.356 mmol) in DCM (2 mL) using TFA (0.274 mL, 3.56 mmol). This gave after workup and purification by reverse column chromatography [C18 (50 g), eluting with ACN in water (containing 0.1% HCl) from 0-100%] (R)-ethyl 2-(2-(2-(3-(1-aminoethyl)-2-fluorophenyl)pyrrolo[2,1-f][1,2,4]triazine-4-carboxamido)phenyl)acetate (33e) (0.164 g, 100% yield) HCl salt as an orange solid. $^1$H NMR (300 MHz, DMSO-$d_6$) δ 10.71 (s, 1H), 8.48-8.35 (m, 5H), 7.83-7.72 (m, 2H), 7.64-7.57 (m, 1H), 7.50 (t, J=7.8 Hz, 1H), 7.46-7.36 (m, 2H), 7.36-7.23 (m, 2H), 4.85-4.69 (m, 1H), 3.97 (q, J=7.1 Hz, 2H), 3.84 (s, 2H), 1.58 (d, J=6.7 Hz, 3H), 0.98 (t, J=7.1 Hz, 3H); $^{19}$F NMR (282 MHz, DMSO-$d_6$) δ−118.34; MS (ES+): 462.3 (M+1), 484.3 (M+Na); HPLC purity 99.38%

Step-5: Preparation of (R)-2-(2-(2-(3-(1-aminoethyl)-2-fluorophenyl)pyrrolo[2,1-f][1,2,4]triazine-4-carboxamido)phenyl)acetic Acid (33f)

Compound 33f was prepared according to the procedure reported in step-4 of Scheme-4 from (R)-ethyl 2-(2-(2-(3-(1-aminoethyl)-2-fluorophenyl)pyrrolo[2,1-f][1,2,4]triazine-4-carboxamido)phenyl)acetate (33e) (120 mg, 0.26 mmol) in THF (4 mL) using a 2 M aqueous solution of NaOH (0.52 mL, 1.04 mmol). This gave after workup and purification by reverse phase column chromatography [C18 (50 g), eluting with ACN in water (containing 0.1% HCl) from 0-100%] (R)-2-(2-(2-(3-(1-aminoethyl)-2-fluorophenyl)pyrrolo[2,1-f][1,2,4]triazine-4-carboxamido)phenyl)acetic acid (33f) (0.06 g, 53% yield) HCl salt as an orange solid; $^1$H NMR (300 MHz, DMSO-$d_6$) δ 12.73 (s, 1H), 10.74 (s, 1H), 8.62 (s, 3H), 8.46-8.32 (m, 2H), 7.92-7.78 (m, 2H), 7.66-7.58 (m, 1H), 7.50 (t, J=7.8 Hz, 1H), 7.44-7.35 (m, 2H), 7.32 (dd, J=4.6, 2.6 Hz, 1H), 7.25 (t, J=7.5 Hz, 1H), 4.84-4.70 (m, 1H), 3.76 (s, 2H), 1.60 (d, J=6.7 Hz, 3H); $^{19}$F NMR (282 MHz, DMSO-$d_6$) δ−118.36; MS (ES+): 434.3 (M+1), MS (ES−): 432.4 (M−1); HPLC purity 99.62%.

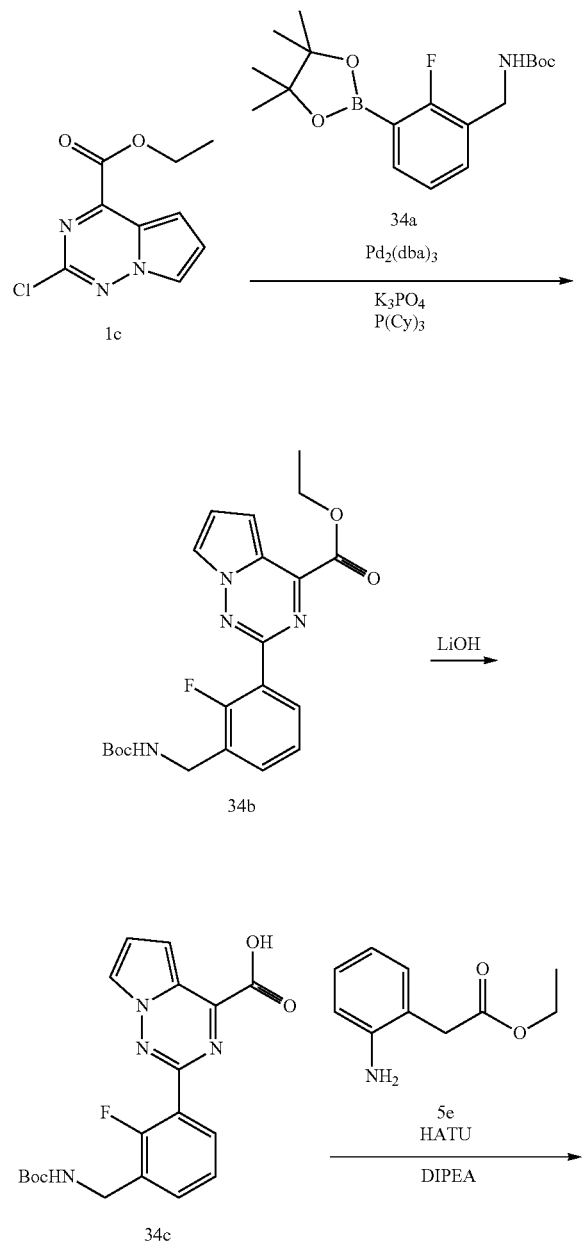

Scheme-34

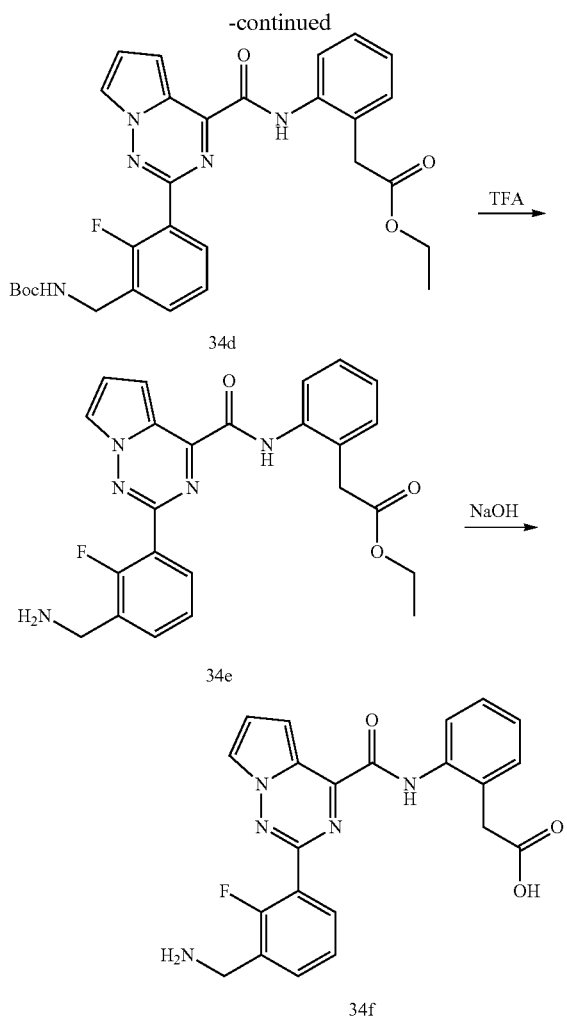

Preparation of 2-(2-(2-(3-(aminomethyl)-2-fluorophenyl)pyrrolo[2,1-f][1,2,4]triazine-4-carboxamido)phenyl)acetic Acid (34f)

Step-1: Preparation of Ethyl 2-(3-(((tert-butoxycarbonyl)amino)methyl)-2-fluorophenyl)pyrrolo[2,1-f][1,2,4]triazine-4-carboxylate (34b)

Compound 34b was prepared according to the procedure reported in step-3 of Scheme-1 from ethyl 2-chloropyrrolo[2,1-f][1,2,4]triazine-4-carboxylate (1c) (400 mg, 1.77 mmol) in dioxane (15 mL) using tert-butyl 2-fluoro-3-(4,4,5,5-tetramethyl-1,3,2-dioxaborolan-2-yl)benzylcarbamate (34a) (1.093 g, 2.99 mmol; CAS #1360819-53-9), 3 M aqueous solution of tripotassium phosphate (1.18 mL, 3.55 mmol), tricyclohexylphosphine (99 mg, 0.36 mmol) and Pd$_2$(dba)$_3$ (162 mg, 0.18 mmol) in argon atmosphere and heating at 125° C. for 45 min in a microwave. This gave after workup and purification by flash column chromatography [silica (12 g), eluting with EtOAc in hexane from 0-50%] ethyl 2-(3-(((tert-butoxycarbonyl)amino)methyl)-2-fluorophenyl)pyrrolo[2,1-f][1,2,4]triazine-4-carboxylate (34b) (0.61 g, 83% yield) as an orange solid; $^1$H NMR (300 MHz, DMSO-d$_6$) δ 8.40 (dd, J=2.6, 1.4 Hz, 1H), 7.91-7.83 (m, 1H), 7.57-7.42 (m, 2H), 7.41-7.31 (m, 2H), 7.29 (dd, J=4.6, 2.5 Hz, 1H), 4.50 (q, J=7.1 Hz, 2H), 4.26 (d, J=6.0 Hz, 2H), 1.47-1.30 (m, 12H); MS (ES+): 415.3 (M+1); (ES−): 413.4 (M−1).

Step-2: Preparation of 2-(3-(((tert-butoxycarbonyl)amino)methyl)-2-fluorophenyl)pyrrolo[2,1-f][1,2,4]triazine-4-carboxylic Acid (34c)

Compound 34c was prepared according to the procedure reported in step-6 of Scheme-1 from ethyl 2-(3-(((tert-butoxycarbonyl)amino)methyl)-2-fluorophenyl)pyrrolo[2,1-f][1,2,4]triazine-4-carboxylate (34b) (0.6 g, 1.448 mmol) in THF (15 mL) using lithium hydroxide hydrate (0.122 g, 2.90 mmol) in water (1 mL). This gave after workup 2-(3-(((tert-butoxycarbonyl)amino)methyl)-2-fluorophenyl)pyrrolo[2,1-f][1,2,4]triazine-4-carboxylic acid (34c) (0.54 g, 97% yield) as a light orange foam; $^1$H NMR (300 MHz, DMSO-d$_6$) δ 14.37 (s, 1H), 8.36 (dd, J=2.6, 1.4 Hz, 1H), 7.95-7.87 (m, 1H), 7.57-7.42 (m, 2H), 7.39-7.31 (m, 2H), 7.25 (dd, J=4.6, 2.5 Hz, 1H), 4.26 (d, J=6.1 Hz, 2H), 1.40 (s, 9H); MS (ES−): 385.3 (M−1).

Step-3: Preparation of Ethyl 2-(2-(2-(3-(((tert-butoxycarbonyl)amino)methyl)-2-fluorophenyl)pyrrolo[2,1-f][1,2,4]triazine-4-carboxamido)phenyl)acetate (34d)

Compound 34d was prepared according to the procedure reported in step-4 of Scheme-1 from 2-(3-(((tert-butoxycarbonyl)amino)methyl)-2-fluorophenyl)pyrrolo[2,11-f][1,2,4]triazine-4-carboxylic acid (34c) (250 mg, 0.647 mmol) in DMF (4 mL) using ethyl 2-(2-aminophenyl)acetate (5e) (125 mg, 0.7 mmol), DIPEA (0.23 mL, 1.29 mmol) and HATU (295 mg, 0.776 mmol). This gave after workup and purification by flash column chromatography [silica (12 g), eluting with EtOAc in hexane from 0-100%] ethyl 2-(2-(2-(3-(((tert-butoxycarbonyl)amino)methyl)-2-fluorophenyl)pyrrolo[2,1-f][1,2,4]triazine-4-carboxamido)phenyl)acetate (34d) (0.31 g, 87% yield) as an orange solid. $^1$H NMR (300 MHz, DMSO-d$_6$) δ 10.68 (s, 1H), 8.40 (dd, J=2.7, 1.4 Hz, 1H), 8.22 (t, J=7.5 Hz, 1H), 7.81-7.75 (m, 1H), 7.61-7.55 (m, 2H), 7.50 (dt, J=13.5, 6.3 Hz, 1H), 7.44-7.32 (m, 3H), 7.32-7.21 (m, 2H), 4.28 (d, J=6.1 Hz, 2H), 3.96 (q, J=7.0 Hz, 2H), 3.83 (s, 2H), 1.41 (s, 9H), 0.97 (t, J=7.1 Hz, 3H); MS (ES+): 570.4 (M+Na); (ES−): 546.5 (M−1).

Step-4: Preparation of Ethyl 2-(2-(2-(3-(aminomethyl)-2-fluorophenyl)pyrrolo[2,1-f][1,2,4]triazine-4-carboxamido)phenyl)acetate (34e)

Compound 34e was prepared according to the procedure reported in step-5 of Scheme-1 from ethyl 2-(2-(2-(3-(((tert-butoxycarbonyl)amino)methyl)-2-fluorophenyl)pyrrolo[2,1-f][1,2,4]triazine-4-carboxamido)phenyl)acetate (34d) (200 mg, 0.365 mmol) in DCM (5 mL) using TFA (0.281 mL, 3.65 mmol). This gave after workup and purification by reverse phase column chromatography [C18 (50 g), eluting with ACN in water (containing 0.1% HCl) from 0-100%] ethyl 2-(2-(2-(3-(aminomethyl)-2-fluorophenyl)pyrrolo[2,1-f][1,2,4]triazine-4-carboxamido)phenyl)acetate (34e) (0.16 g, 98% yield) as a HCl salt; $^1$H NMR (300 MHz, DMSO-d$_6$) δ 10.72 (s, 1H), 8.53-8.36 (m, 5H), 7.81-7.71 (m, 2H), 7.60 (dd, J=4.6, 1.4 Hz, 1H), 7.52-7.36 (m, 3H), 7.34-7.23 (m, 2H), 4.20 (s, 2H), 3.97 (q, J=7.1 Hz, 2H), 3.84 (s, 2H), 0.99 (t, J=7.1 Hz, 3H); $^{19}$F NMR (282 MHz, DMSO-d$_6$)

δ −116.67; MS (ES+): 448.3 (M+1), MS (ES−): 482.4 (M+Cl); HPLC purity 98.75%

Step-5: Preparation of 2-(2-(2-(3-(aminomethyl)-2-fluorophenyl)pyrrolo[2,1-f][1,2,4]triazine-4-carboxamido)phenyl)acetic Acid (34f)

Compound 34f was prepared according to the procedure reported in step-4 of Scheme-4 from ethyl 2-(2-(2-(3-(aminomethyl)-2-fluorophenyl)pyrrolo[2,1-f][1,2,4]triazine-4-carboxamido)phenyl)acetate (34e) (110 mg, 0.246 mmol) in THF (4 mL) using a 2 M aqueous solution of NaOH (0.62 mL, 1.23 mmol). This gave after workup and purification by reverse phase column chromatography [C18 (50 g), eluting with ACN in water (containing 0.1% HCl) from 0-40%] 2-(2-(2-(3-(aminomethyl)-2-fluorophenyl)pyrrolo[2,1-f][1,2,4]triazine-4-carboxamido)phenyl)acetic acid (34f) (0.072 g, 70% yield) as a HCl salt; $^1$H NMR (300 MHz, DMSO-d$_6$) δ 12.75 (s, 1H), 10.76 (s, 1H), 8.57-8.34 (m, 5H), 7.86 (d, J=8.1 Hz, 1H), 7.76 (t, J=7.1 Hz, 1H), 7.62 (d, J=4.5 Hz, 1H), 7.47 (t, J=7.8 Hz, 1H), 7.45-7.33 (m, 2H), 7.32 (dd, J=4.6, 2.6 Hz, 1H), 7.25 (t, J=7.4 Hz, 1H), 4.20 (s, 2H), 3.76 (s, 2H); $^{19}$F NMR (282 MHz, DMSO-d$_6$) δ −116.66; MS (ES+): 420.3 (M+1), MS (ES−): 418.3 (M−1); HPLC purity 99.49%.

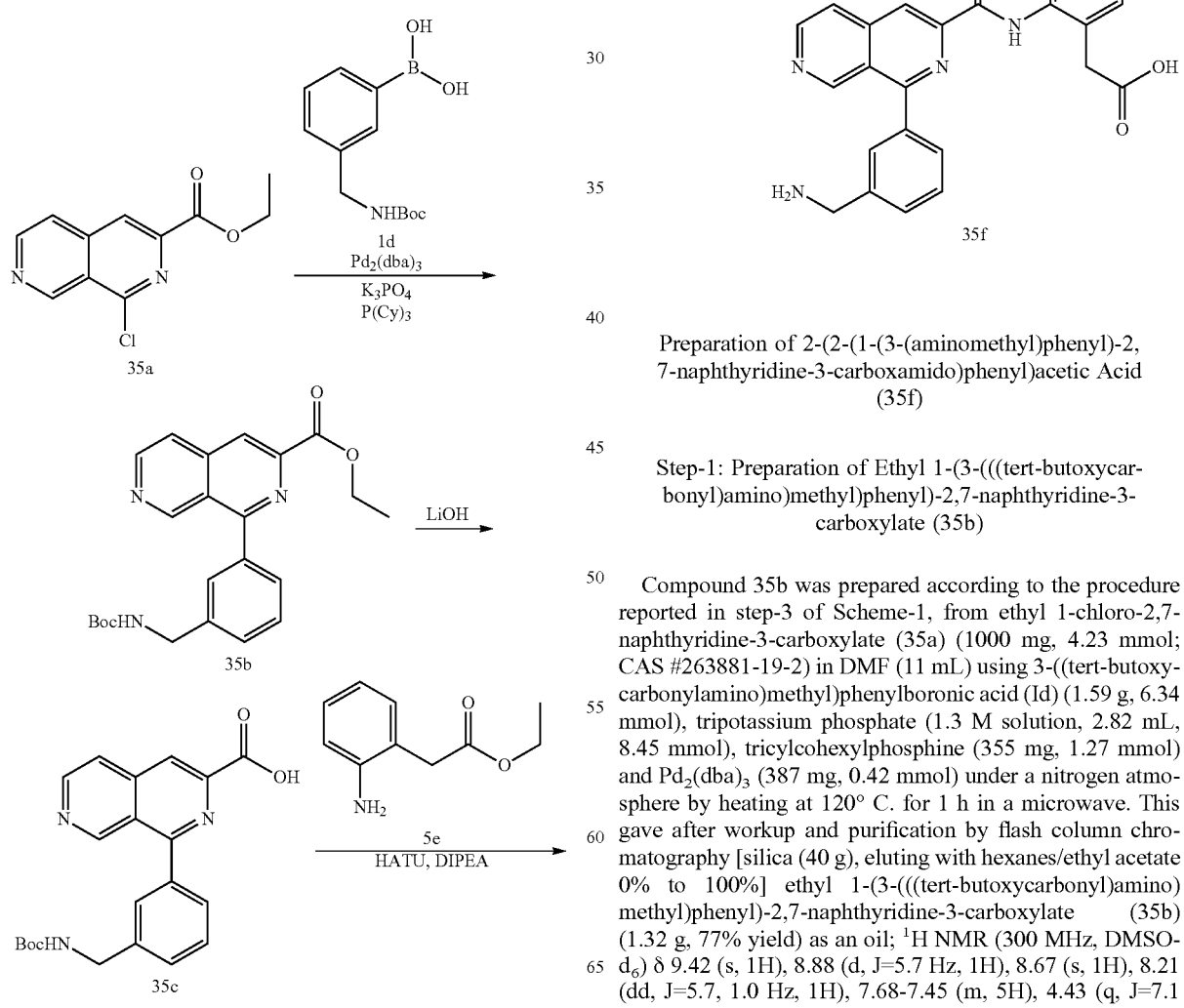

Scheme-35

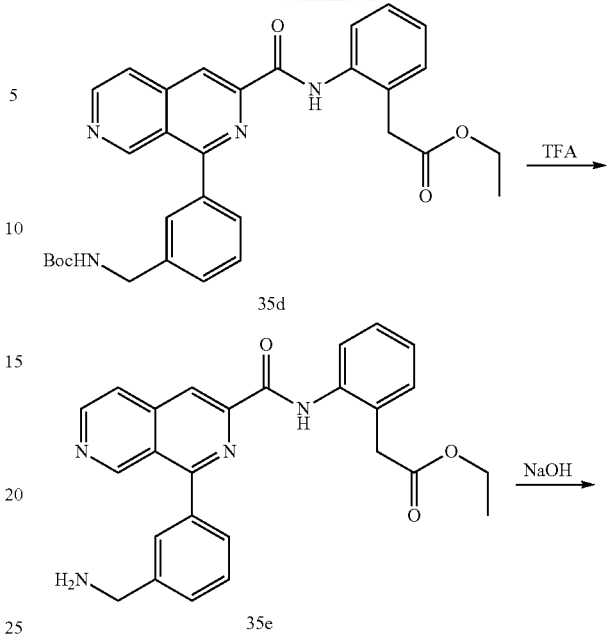

Preparation of 2-(2-(1-(3-(aminomethyl)phenyl)-2,7-naphthyridine-3-carboxamido)phenyl)acetic Acid (35f)

Step-1: Preparation of Ethyl 1-(3-(((tert-butoxycarbonyl)amino)methyl)phenyl)-2,7-naphthyridine-3-carboxylate (35b)

Compound 35b was prepared according to the procedure reported in step-3 of Scheme-1, from ethyl 1-chloro-2,7-naphthyridine-3-carboxylate (35a) (1000 mg, 4.23 mmol; CAS #263881-19-2) in DMF (11 mL) using 3-((tert-butoxycarbonylamino)methyl)phenylboronic acid (1d) (1.59 g, 6.34 mmol), tripotassium phosphate (1.3 M solution, 2.82 mL, 8.45 mmol), tricylcohexylphosphine (355 mg, 1.27 mmol) and Pd$_2$(dba)$_3$ (387 mg, 0.42 mmol) under a nitrogen atmosphere by heating at 120° C. for 1 h in a microwave. This gave after workup and purification by flash column chromatography [silica (40 g), eluting with hexanes/ethyl acetate 0% to 100%] ethyl 1-(3-(((tert-butoxycarbonyl)amino)methyl)phenyl)-2,7-naphthyridine-3-carboxylate (35b) (1.32 g, 77% yield) as an oil; $^1$H NMR (300 MHz, DMSO-d$_6$) δ 9.42 (s, 1H), 8.88 (d, J=5.7 Hz, 1H), 8.67 (s, 1H), 8.21 (dd, J=5.7, 1.0 Hz, 1H), 7.68-7.45 (m, 5H), 4.43 (q, J=7.1 Hz, 2H), 4.27 (d, J=6.2 Hz, 2H), 1.40-1.28 (m, 12H).

Step-2: Preparation of 1-(3-(((tert-butoxycarbonyl)amino)methyl)phenyl)-2,7-naphthyridine-3-carboxylic Acid (35c)

Compound 35c was prepared according to the procedure reported in step-6 of Scheme-1, from ethyl 1-(3-(((tert-butoxycarbonyl)amino)methyl)phenyl)-2,7-naphthyridine-3-carboxylate (35b) (1250 mg, 3.07 mmol) in THF (20 mL) using a solution of lithium hydroxide hydrate (220 mg, 9.2 mmol) in water (4 mL) This gave after workup 1-(3-(((tert-butoxycarbonyl)amino)methyl)phenyl)-2,7-naphthyridine-3-carboxylic acid (35c) (300 mgs, 26%), which was used as such for next step; $^1$H NMR (300 MHz, DMSO-$d_6$) δ 9.43 (s, 1H), 8.86 (d, J=5.7 Hz, 1H), 8.62 (s, 1H), 8.17 (d, J=5.8 Hz, 1H), 7.72-7.41 (m, 5H), 4.27 (d, J=6.2 Hz, 2H), 1.38 (s, 9H).

Step-3: Preparation of Ethyl 2-(2-(1-(3-(((tert-butoxycarbonyl)amino)methyl)phenyl)-2,7-naphthyridine-3-carboxamido)phenyl)acetate (35d)

Compound 35d was prepared according to the procedure reported in step-4 of Scheme-1, from 1-(3-(((tert-butoxycarbonyl)amino)methyl)phenyl)-2,7-naphthyridine-3-carboxylic acid (35c) (300 mg, 0.79 mmol) in DMF (4 mL) using ethyl 2-(2-aminophenyl)acetate (5e) (248 mg, 1.38 mmol), DIPEA (0.41 mL, 2.37 mmol) and HATU (526 mg, 1.38 mmol). This gave after workup and purification by flash column chromatography [silica (12 g), eluting with 0-60% EtOAc/MeOH (9:1) in hexane from 0-100%] ethyl 2-(2-(1-(3-(((tert-butoxycarbonyl)amino)methyl)phenyl)-2,7-naphthyridine-3-carboxamido)phenyl)acetate (35d) (300 mg, 70% yield) as a white solid; $^1$H NMR (300 MHz, DMSO-$d_6$) δ 10.68 (s, 1H), 9.55 (s, 1H), 8.90 (d, J=5.7 Hz, 1H), 8.74 (s, 1H), 8.26 (d, J=5.7 Hz, 1H), 7.92 (d, J=8.0 Hz, 1H), 7.86 (d, J=7.6 Hz, 1H), 7.80 (s, 1H), 7.61 (t, J=7.6 Hz, 1H), 7.57-7.46 (m, 2H), 7.44-7.32 (m, 2H), 7.21 (t, J=7.4 Hz, 1H), 4.29 (d, J=6.2 Hz, 2H), 3.87-3.73 (m, 4H), 1.37 (s, 9H), 0.88 (t, J=7.1 Hz, 3H).

Step-4: Preparation of Ethyl 2-(2-(1-(3-(aminomethyl)phenyl)-2,7-naphthyridine-3-carboxamido)phenyl)acetate (35e)

Compound 35e was prepared according to the procedure reported in step-5 of Scheme-1, from ethyl 2-(2-(1-(3-(((tert-butoxycarbonyl)amino)methyl)phenyl)-2,7-naphthyridine-3-carboxamido)phenyl)acetate (35d) (300 mg, 0.56 mmol) using TFA (0.43 mL, 5.55 mmol) in DCM (5 mL). This gave after workup and purification by flash column chromatography [silica (12 g), eluting with DMA80 in DCM from 0-50%] followed by reverse phase column chromatography [C18 (50 g), eluting with ACN in water (containing 0.1% HCl) from 0-100%] ethyl 2-(2-(1-(3-(aminomethyl)phenyl)-2,7-naphthyridine-3-carboxamido)phenyl)acetate (35e) (0.21 g, 86% yield) as a yellow solid; $^1$H NMR (300 MHz, DMSO-$d_6$) δ 10.71 (s, 1H), 9.74 (s, 1H), 8.94 (d, J=5.6 Hz, 1H), 8.81 (s, 1H), 8.64 (s, 2H), 8.39 (d, J=5.7 Hz, 1H), 8.13 (s, 1H), 8.05 (d, J=7.5 Hz, 1H), 7.89 (d, J=8.0 Hz, 1H), 7.80 (d, J=7.7 Hz, 1H), 7.72 (t, J=7.6 Hz, 1H), 7.39 (t, J=8.3 Hz, 2H), 7.23 (td, J=7.3, 1.3 Hz, 1H), 4.19 (q, J=5.8 Hz, 2H), 3.96-3.69 (m, 4H), 0.92 (t, J=7.1 Hz, 3H); MS (ES+): 441.3 (M+1), 463.3 (M+Na); (ES−): 475.3 (M+Cl); HPLC purity: 98.24%.

Step-5: Preparation of 2-(2-(1-(3-(aminomethyl)phenyl)-2,7-naphthyridine-3-carboxamido)phenyl)acetic Acid (35f)

Compound 35f was prepared according to the procedure reported in step-4 of Scheme-4, from ethyl 2-(2-(1-(3-(aminomethyl)phenyl)-2,7-naphthyridine-3-carboxamido)phenyl)acetate (35e) (150 mg, 0.34 mmol) in MeOH/THF (10 mL, 1:1) using a solution of sodium hydroxide (54 mg, 1.36 mmol) in water (2 mL) This gave after workup and purification by reverse phase column [C18 (50 g), eluting with ACN in water (containing 0.1% HCl) from 0-100%] 2-(2-(1-(3-(aminomethyl)phenyl)-2,7-naphthyridine-3-carboxamido)phenyl)acetic acid (35f) (0.12 g, 85% yield) as a yellow solid; $^1$H NMR (300 MHz, DMSO-$d_6$) δ 10.79 (s, 1H), 9.81 (s, 1H), 8.96 (s, 1H), 8.84 (s, 1H), 8.71 (d, J=6.4 Hz, 3H), 8.47 (d, J=5.5 Hz, 1H), 8.16 (s, 1H), 8.07 (d, J=7.6 Hz, 1H), 8.02-7.92 (m, 1H), 7.82 (d, J=7.7 Hz, 1H), 7.73 (t, J=7.6 Hz, 1H), 7.44-7.32 (m, 2H), 7.28-7.13 (m, 1H), 4.20 (q, J=5.9 Hz, 2H), 3.74 (s, 2H); MS (ES+): 413.3 (M+1), 435.3 (M+Na); (ES−): 411.4 (M−1), 447.3 (M+Cl); HPLC purity: 94.81%.

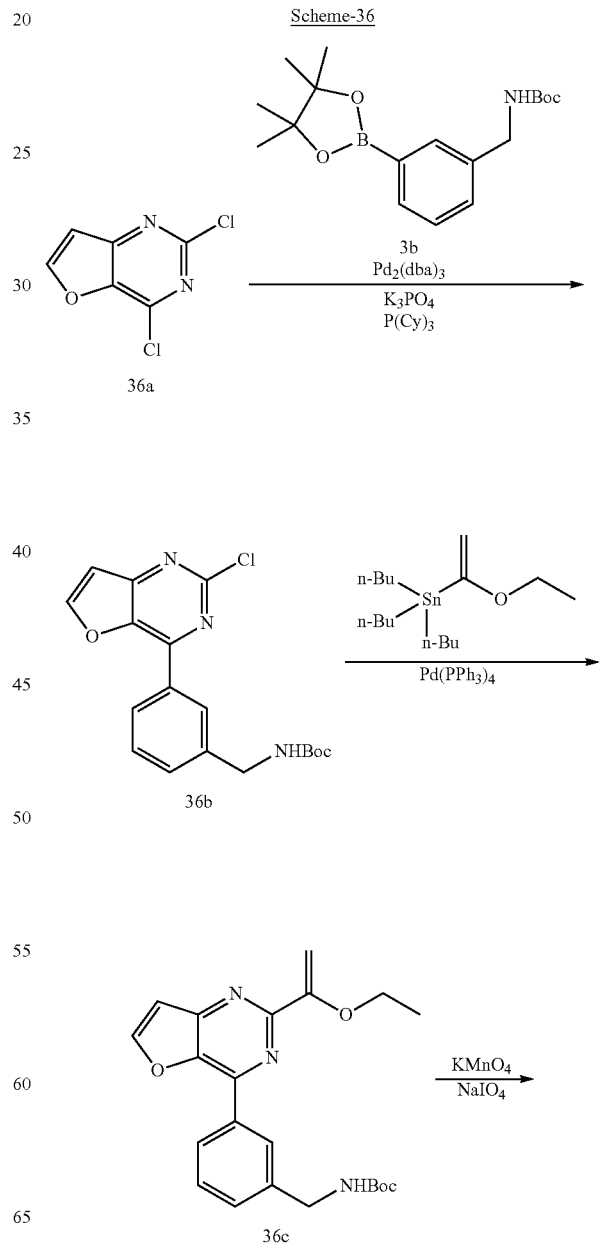

Scheme-36

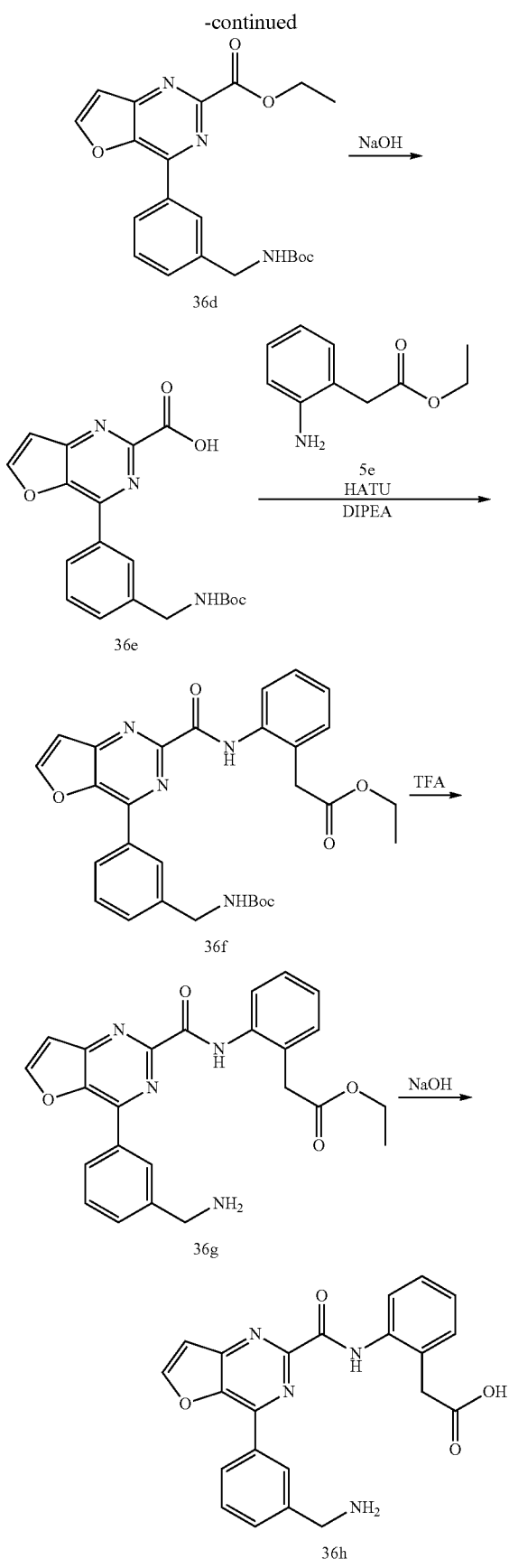

Preparation of 2-(2-(4-(3-(aminomethyl)phenyl)furo[3,2-d]pyrimidine-2-carboxamido)phenyl)acetic Acid (36h)

Step-1: Preparation of tert-butyl 3-(2-chlorofuro[3,2-d]pyrimidin-4-yl)benzylcarbamate (36b)

Compound 36b was prepared according to the procedure reported in step-3 of Scheme-1 from 2,4-dichlorofuro[3,2-d]pyrimidine (36a) (3 g, 15.87 mmol; CAS #956034-07-4) in dioxane (100 mL) using tert-butyl 3-(4,4,5,5-tetramethyl-1,3,2-dioxaborolan-2-yl)benzylcarbamate (3b) (3.78 g, 11.34 mmol), tripotassium phosphate (8.31 mL, 24.94 mmol, 3 M aqueous solution) in water (1 mL), tricyclohexylphosphine (0.95 g, 3.38 mmol) and $Pd_2(dba)_3$ (1.04 g, 1.13 mmol) in argon atmosphere and heating in an oil bath at 120° C. for 1.5 h. This gave after workup and purification by flash column chromatography [silica (40 g), eluting with EtOAc in hexane from 0-70%] tert-butyl 3-(2-chlorofuro[3,2-d]pyrimidin-4-yl)benzylcarbamate (36b) (2.65 g, 65% yield) as a white solid; $^1$H NMR (300 MHz, DMSO-$d_6$) δ 8.74 (d, J=2.3 Hz, 1H), 8.29 (d, J=7.5 Hz, 2H), 7.66-7.47 (m, 3H), 7.33 (d, J=2.3 Hz, 1H), 4.26 (d, J=6.2 Hz, 2H), 1.42 (s, 9H); MS (ES-): 358.3 & 360.3 (M-1).

Step-2: Preparation of tert-butyl 3-(2-(1-ethoxyvinyl)furo[3,2-d]pyrimidin-4-yl)benzylcarbamate (36c)

Compound 36c was prepared according to the procedure reported in step-1 of Scheme-1 from tert-butyl 3-(2-chlorofuro[3,2-d]pyrimidin-4-yl)benzylcarbamate (36b) (2 g, 5.56 mmol) in DMF (30 mL) using 1-ethoxyvinyltri-n-butyltin (2.46 mL, 7.23 mmol) and $Pd(PPh_3)_4$ (0.64 g, 0.56 mmol) in argon atmosphere and heating at 110° C. for 4 h. This gave after workup and purification by flash column chromatography [silica (40 g), eluting with EtOAc in hexane from 0-50%] tert-butyl 3-(2-(1-ethoxyvinyl)furo[3,2-d]pyrimidin-4-yl)benzylcarbamate (36c) (1.80 g, 82% yield) as a white solid; $^1$H NMR (300 MHz, DMSO-$d_6$) δ 8.63 (d, J=2.2 Hz, 1H), 8.36 (d, J=7.4 Hz, 2H), 7.66-7.46 (m, 3H), 7.35 (d, J=2.2 Hz, 1H), 5.68 (d, J=1.7 Hz, 1H), 4.68 (d, J=1.7 Hz, 1H), 4.27 (d, J=6.2 Hz, 2H), 3.99 (p, J=7.0 Hz, 2H), 1.55-1.24 (m, 12H); MS (ES+): 396.3 (M+1); MS (ES-): 430.4 (M+Cl).

Step-3: Preparation of Ethyl 4-(3-(((tert-butoxycarbonyl)amino)methyl)phenyl)furo[3,2-d]pyrimidine-2-carboxylate (36d)

Compound 36d was prepared according to the procedure reported in step-2 of Scheme-1 from tert-butyl 3-(2-(1-ethoxyvinyl)furo[3,2-d]pyrimidin-4-yl)benzylcarbamate (36c) (1.7 g, 4.30 mmol) in 1,4-dioxane (100 mL) using sodium periodate solution (1.839 g, 8.60 mmol) in water (10 mL) and $KMnO_4$ (0.41 g, 2.58 mmol, and second dosing of 0.41 g, 2.58 mmol after 12 h). This gave after workup and purification by flash column chromatography [silica (24 g), eluting with EtOAc in hexane from 0-60%] ethyl 4-(3-(((tert-butoxycarbonyl)amino)methyl)phenyl)furo[3,2-d]pyrimidine-2-carboxylate (36d) (0.55 g, 32% yield) as a yellow solid; MS (ES-) 396.4 (M-1).

Step-4: Preparation of 4-(3-(((tert-butoxycarbonyl)amino)methyl)phenyl)furo[3,2-d]pyrimidine-2-carboxylic Acid (36e)

Compound 36e was prepared according to the procedure reported in step-4 of Scheme-4 from ethyl 4-(3-(((tert-butoxycarbonyl)amino)methyl)phenyl)furo[3,2-d]pyrimidine-2-carboxylate (36d) (0.35 g, 0.88 mmol) in THF/MeOH (10 mL, 1:1) using sodium hydroxide (0.14 g, 3.52 mmol) in water (2 mL). This gave after workup and purification by reverse phase column [C18 (50 g), eluting with ACN in water (containing 0.1% HCl) from 0-100%] 4-(3-(((tert-butoxycarbonyl)amino)methyl)phenyl)furo[3,2-d]pyrimidine-2-carboxylic acid (36e) (0.22 g, 68% yield) as a yellow solid; $^1$H NMR (300 MHz, DMSO-$d_6$) δ 8.53 (d, J=2.3 Hz, 1H), 8.36-8.24 (m, 2H), 7.57 (dd, J=9.4, 6.6 Hz, 2H), 7.45 (d, J=7.6 Hz, 1H), 7.20 (d, J=2.3 Hz, 1H), 4.25 (d, J=6.2 Hz, 2H), 1.40 (s, 9H); MS (ES-): 368.3 (M-1).

Step-5: Preparation of Ethyl 2-(2-(4-(3-(((tert-butoxycarbonyl)amino)methyl)phenyl)furo[3,2-d]pyrimidine-2-carboxamido)phenyl)acetate (36f)

Compound 36f was prepared according to the procedure reported in step-4 of Scheme-1 from 4-(3-(((tert-butoxycarbonyl)amino)methyl)phenyl)furo[3,2-d]pyrimidine-2-carboxylic acid (36e) (0.2 g, 0.54 mmol) in DMF (5 mL) using ethyl 2-(2-aminophenyl)acetate (5e) (120 mg, 0.65 mmol), DIPEA (0.19 mL, 1.08 mmol) and HATU (250 mg, 0.65 mmol). This gave after workup and purification by flash column chromatography [silica (12 g), eluting with 0-60% EtOAc/MeOH (9:1) in hexane from 0-100%] ethyl 2-(2-(4-(3-(((tert-butoxycarbonyl)amino)methyl)phenyl)furo[3,2-d]pyrimidine-2-carboxamido)phenyl)acetate (36f) (0.17 g, 59% yield) as a white solid; MS (ES+): 553.5 (M+Na).

Step-6: Preparation of Ethyl 2-(2-(4-(3-(aminomethyl)phenyl)furo[3,2-d]pyrimidine-2-carboxamido)phenyl)acetate (36g)

Compound 36g was prepared according to the procedure reported in step-5 of Scheme-1 from ethyl 2-(2-(4-(3-(((tert-butoxycarbonyl)amino)methyl)phenyl)furo[3,2-d]pyrimidine-2-carboxamido)phenyl)acetate (36f) (170 mg, 0.32 mmol) in DCM (5 mL) using TFA (0.25 mL, 3.2 mmol). This gave after workup and purification by flash column chromatography [silica (12 g), eluting with DMA80 in DCM from 0-50%] followed by reverse phase column chromatography [C18 (50 g), eluting with ACN in water (containing 0.1% HCl) from 0-100%] ethyl 2-(2-(4-(3-(aminomethyl)phenyl)furo[3,2-d]pyrimidine-2-carboxamido)phenyl)acetate (36g) (0.12 g, 87% yield) as a yellow solid; $^1$H NMR (300 MHz, DMSO-$d_6$) δ 10.68 (s, 1H), 8.88-8.77 (m, 2H), 8.69 (s, 2H), 8.66-8.61 (m, 1H), 7.85 (m, 1H), 7.80-7.69 (m, 2H), 7.53-7.46 (m, 1H), 7.43-7.35 (m, 2H), 7.30-7.21 (m, 1H), 4.20 (q, J=5.8 Hz, 2H), 3.99 (q, J=7.1 Hz, 2H), 3.87 (s, 2H), 1.00 (t, J=7.1 Hz, 3H); MS (ES+): 431.3 (M+1); HPLC purity: 97.05%.

Step-7: Preparation of 2-(2-(4-(3-(aminomethyl)phenyl)furo[3,2-d]pyrimidine-2-carboxamido)phenyl)acetic Acid (36h)

Compound 36h was prepared according to the procedure reported in step-4 of Scheme-4 from ethyl 2-(2-(4-(3-(aminomethyl)phenyl)furo[3,2-d]pyrimidine-2-carboxamido)phenyl)acetate (36g) (600 mg, 0.14 mmol) in MeOH/THF (10 mL, 1:1) using a solution of NaOH (20 mg, 0.56 mmol) in water (2 mL). This gave after workup and purification by reverse phase column chromatography [C18 (50 g), eluting with ACN in water (containing 0.1% HCl) from 0-100%] 2-(2-(4-(3-(aminomethyl)phenyl)furo[3,2-d]pyrimidine-2-carboxamido)phenyl)acetic acid (36h) (0.03 g, 57% yield) as a yellow solid; $^1$H NMR (300 MHz, DMSO-$d_6$) δ 10.76 (s, 1H), 8.84 (d, J=2.2 Hz, 1H), 8.75 (s, 1H), 8.63 (d, J=7.6 Hz, 1H), 8.52 (s, 2H), 7.94-7.70 (m, 3H), 7.50 (d, J=2.3 Hz, 1H), 7.38 (t, J=7.0 Hz, 2H), 7.23 (t, J=7.3 Hz, 1H), 4.22 (d, J=5.8 Hz, 2H), 3.79 (s, 2H); MS (ES+): 403.3 (M+1), 425.3 (M+Na); MS (ES-): 401.3 (M-1), 437.3 (M+Cl).

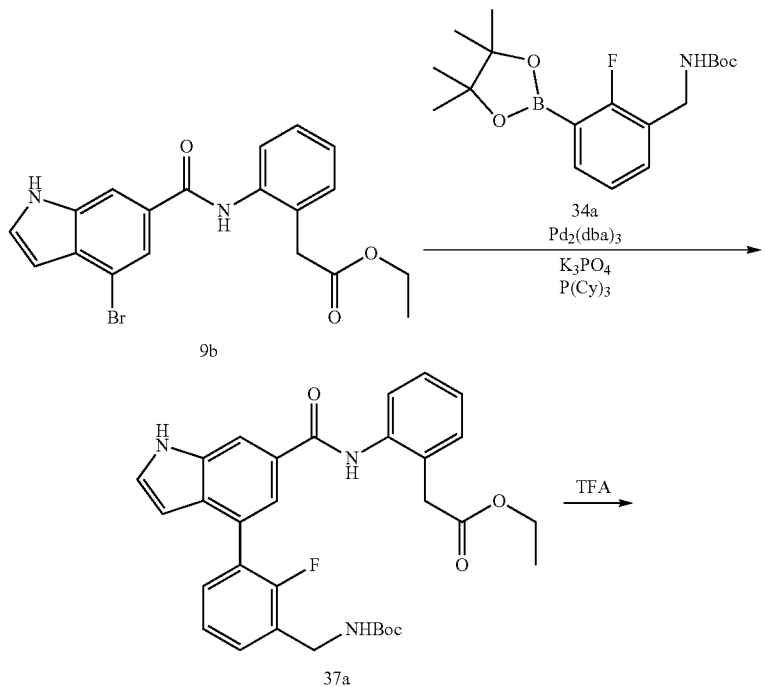

Scheme-37

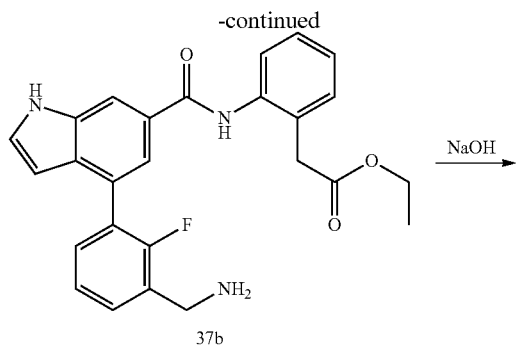

37b

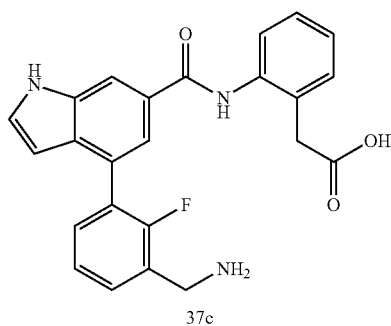

37c

Preparation of 2-(2-(4-(3-(aminomethyl)-2-fluorophenyl)-1H-indole-6-carboxamido)phenyl)acetic Acid (37c)

Step-1: Preparation of Ethyl 2-(2-(4-(3-(((tert-butoxycarbonyl)amino)methyl)-2-fluorophenyl)-1H-indole-6-carboxamido)phenyl)acetate (37a)

Compound 37a was prepared according to the procedure reported in step-3 of Scheme-1 from ethyl 2-(2-(4-bromo-1H-indole-6-carboxamido)phenyl)acetate (9b) (0.23 g, 0.57 mmol) in dioxane (30 mL) using tert-butyl 2-fluoro-3-(4,4,5,5-tetramethyl-1,3,2-dioxaborolan-2-yl)benzylcarbamate (34a) (200 mg, 0.57 mmol), tripotassium phosphate (0.42 mL, 1.25 mmol, 3 M aqueous solution) in water (1 mL), tricyclohexylphosphine (0.05 g, 0.06 mmol) and Pd$_2$(dba)$_3$ (0.05 g, 0.06 mmol) in argon atmosphere and heating in an oil bath at 120° C. for 1 h. This gave after workup and purification by flash column chromatography [silica (12 g), eluting with EtOAc in hexane from 0-70%] ethyl 2-(2-(4-(3-(((tert-butoxycarbonyl)amino)methyl)-2-fluorophenyl)-1H-indole-6-carboxamido)phenyl)acetate (37a) (0.21 g, 68% yield) as a white solid. MS (ES−): 544.5 (M−1).

Step-2: Preparation of Ethyl 2-(2-(4-(3-(aminomethyl)-2-fluorophenyl)-1H-indole-6-carboxamido)phenyl)acetate (37b)

Compound 37b was prepared according to the procedure reported in step-5 of Scheme-1 from ethyl 2-(2-(4-(3-(((tert-butoxycarbonyl)amino)methyl)-2-fluorophenyl)-1H-indole-6-carboxamido)phenyl)acetate (37a) (150 mg, 0.28 mmol) in DCM (5 mL) using TFA (0.21 mL, 2.75 mmol). This gave after workup and purification by flash column chromatography [silica (12 g), eluting with DMA80 in DCM from 0-50%] followed by reverse phase column chromatography [C18 (50 g), eluting with ACN in water (containing 0.1% HCl) from 0-100%] ethyl 2-(2-(4-(3-(aminomethyl)-2-fluorophenyl)-1H-indole-6-carboxamido)phenyl)acetate (37b) (0.09 g, 74% yield) as a yellow solid; $^1$H NMR (300 MHz, DMSO-d$_6$) δ 11.74 (s, 1H), 10.01 (s, 1H), 8.50 (s, 3H), 8.17-8.07 (m, 1H), 7.74-7.58 (m, 4H), 7.49-7.38 (m, 1H), 7.32 (m, 2H), 7.29-7.18 (m, 1H), 6.50-6.36 (m, 1H), 4.18 (d, J=6.0 Hz, 2H), 4.02-3.90 (m, 2H), 3.75 (s, 2H), 1.14-0.86 (m, 3H); $^{19}$F NMR (282 MHz, DMSO-d$_6$) δ−118.67; MS (ES+): 446.3 (M+1), 448.3 (M+Na); MS (ES−): 480.4 (M+Cl). HPLC purity: 93.30%.

Step-3: Preparation of 2-(2-(4-(3-(aminomethyl)-2-fluorophenyl)-1H-indole-6-carboxamido)phenyl)acetic Acid (37c)

Compound 37c was prepared according to the procedure reported in step-4 of Scheme-4 from ethyl 2-(2-(4-(3-(aminomethyl)-2-fluorophenyl)-1H-indole-6-carboxamido)phenyl)acetate (37b) (80 mg, 0.17 mmol) in MeOH/THF (5 mL, 1:1) using a solution of NaOH (30 mg, 0.67 mmol) in water (2 mL). This gave after workup and purification by reverse phase column chromatography [C18 (50 g), eluting with ACN in water (containing 0.1% HCl) from 0-100%] of 2-(2-(4-(3-(aminomethyl)-2-fluorophenyl)-1H-indole-6-carboxamido)phenyl)acetic acid (37c) (0.04 g, 54% yield) as a yellow solid; $^1$H NMR (300 MHz, DMSO-d$_6$) δ 12.42 (s, 1H), 11.74 (s, 1H), 10.05 (s, 1H), 8.50 (s, 3H), 8.15 (s, 1H), 7.71 (s, 1H), 7.69-7.59 (m, 2H), 7.54-7.38 (m, 2H), 7.32 (m, 2H), 7.26-7.17 (m, 1H), 6.45 (d, J=2.8 Hz, 1H), 4.18 (d, J=5.9 Hz, 2H), 3.68 (s, 2H); $^{19}$F NMR (282 MHz, DMSO-d$_6$) δ−118.51; MS (ES+): 418.3 (M+1); MS (ES−): 416.4 (M−1), 452.3 (M+Cl). HPLC purity: 97.67%.

Scheme-38
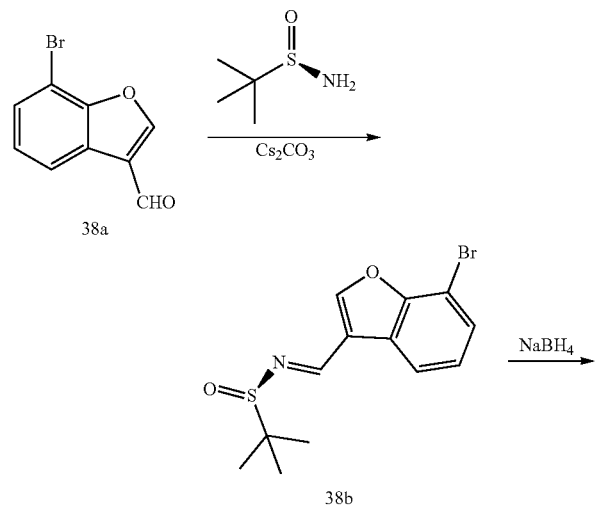
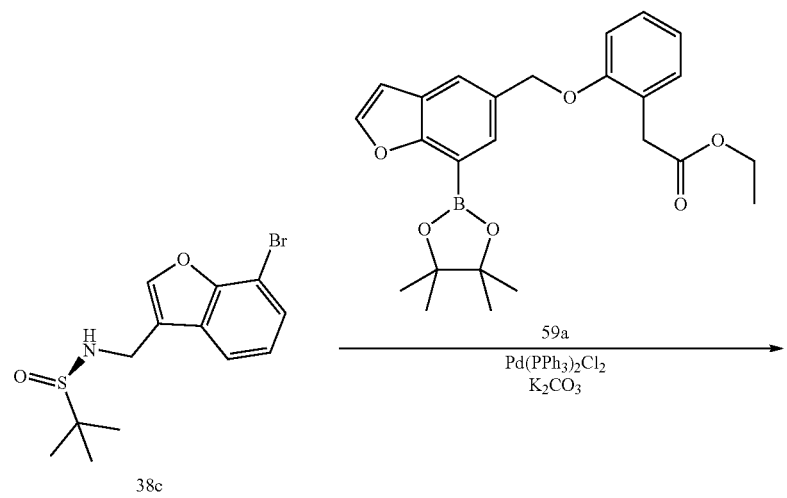
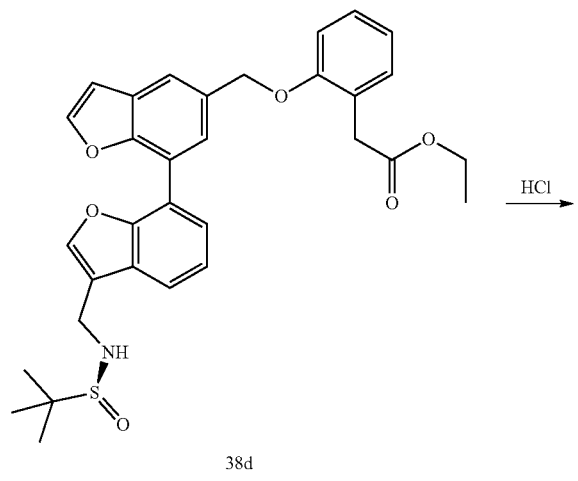

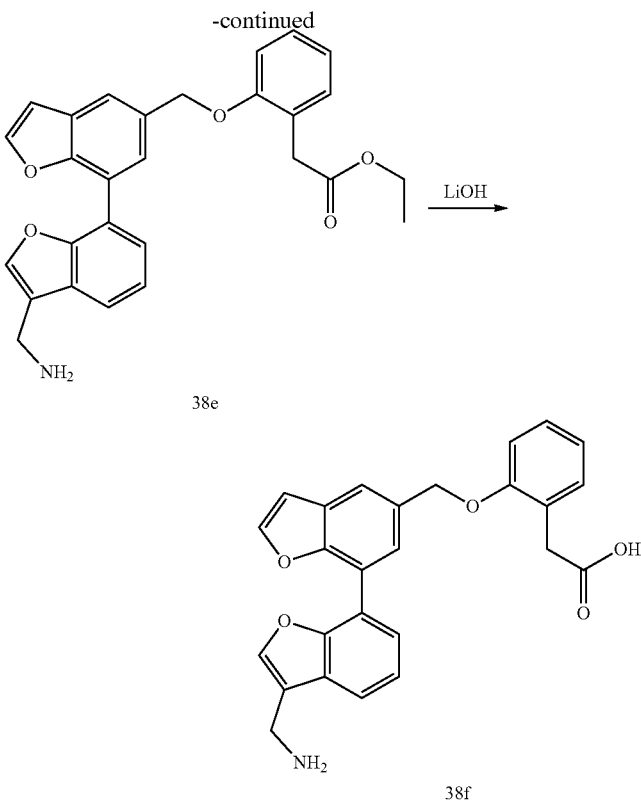

38e

38f

Preparation of 2-(2-((3'-(aminomethyl)-[7,7'-bibenzofuran]-5-yl)methoxy)phenyl)acetic Acid (38f)

Step-1: Preparation of (S)—N-((7-bromobenzofuran-3-yl)methylene)-2-methylpropane-2-sulfinamide (38b)

Compound 38b was prepared according to the procedure reported in step-1 of Scheme-220 from 7-bromobenzofuran-3-carbaldehyde (38a) (110 mg, 0.489 mmol; CAS #1368142-94-2) in DCM (20 mL) using $Cs_2CO_3$ (381 mg, 1.169 mmol) and (S)-2-methylpropane-2-sulfinamide (119 mg, 0.982 mmol). This gave after workup (S)—N-((7-bromobenzofuran-3-yl)methylene)-2-methylpropane-2-sulfinamide (38b) (160 mg, 100% yield) which was used as such in next step without further purification. MS (ES+): 328.0 (M+1).

Step-2: Preparation of (S)—N-((7-bromobenzofuran-3-yl)methyl)-2-methylpropane-2-sulfinamide (38c)

Compound 38c was prepared according to the procedure reported in step-2 of Scheme-220 from (S)—N-((7-bromobenzofuran-3-yl)methylene)-2-methylpropane-2-sulfinamide (38b) (160 mg, 0.487 mmol) in DCM (12 mL) and methanol (4 mL) using $NaBH_4$ (83 mg, 2.194 mmol). This gave after workup and purification by flash column chromatography (silica gel, 12 g, eluting with 30-100% ethyl acetate in hexanes) (S)—N-((7-bromobenzofuran-3-yl)methyl)-2-methylpropane-2-sulfinamide (38c) (120 mg, 75% yield) as a colorless oil. $^1$H NMR (300 MHz, DMSO-$d_6$) δ 8.05 (d, J=1.1 Hz, 1H), 7.72 (dd, J=7.8, 1.1 Hz, 1H), 7.56 (dd, J=7.8, 1.0 Hz, 1H), 7.23 (t, J=7.8 Hz, 1H), 5.77 (t, J=5.5 Hz, 1H), 4.28 (dt, J=5.6, 1.1 Hz, 2H), 1.11 (s, 9H).

Step-3: Preparation of (S)-ethyl 2-(2-((3'-((1,1-dimethylethylsulfinamido)methyl)-[7,7'-bibenzofuran]-5-yl)methoxy)phenyl)acetate (38d)

Compound 38d was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (178 mg, 0.408 mmol) in dioxane (5 mL) using (S)—N-((7-bromobenzofuran-3-yl)methyl)-2-methylpropane-2-sulfinamide (38c) (120 mg, 0.363 mmol), bis(triphenylphosphine)palladium(II) chloride (45 mg, 0.064 mmol) and a solution of $K_2CO_3$ (158 mg, 1.143 mmol) in water (0.5 mL) under an Ar atmosphere and heating at 100° C. for 3 h on oil bath. This gave after workup, purification by flash column chromatography (silica gel 12 g, eluting with 30-100% hexanes in ethyl acetate) (S)-ethyl 2-(2-((3'-((1,1-dimethylethylsulfinamido)methyl)-[7,7'-bibenzofuran]-5-yl)methoxy)phenyl)acetate (38d) (189 mg, 83% yield) as a pale-yellow oil. MS (ES+): 560.0 (M+1).

Step-4: Preparation of Ethyl 2-(2-((3'-(aminomethyl)-[7,7'-bibenzofuran]-5-yl)methoxy)phenyl)acetate (38e)

Compound 38e was prepared according to the procedure reported in step-5 of Scheme-220 from (S)-ethyl 2-(2-((3'-((1,1-dimethylethylsulfinamido)methyl)-[7,7'-bibenzofuran]-5-yl)methoxy)phenyl)acetate (38d) (182 mg, 0.325 mmol) in methanol (8 mL) using hydrochloric acid (4 M in 1,4-dioxane, 0.35 mL, 1.400 mmol). This gave after workup, purification by flash column chromatography (silica gel 12 g, eluting with DMA80/DCM, from 0-80%) ethyl 2-(2-((3'-(aminomethyl)-[7,7'-bibenzofuran]-5-yl)methoxy)phenyl)acetate (38e) (96 mg, 45% yield) as a yellow foam. (ES+): 456.0 (M+1).

Step-5: Preparation of 2-(2-((3'-(aminomethyl)-[7,7'-bibenzofuran]-5-yl)methoxy)phenyl)acetic Acid (38f)

Compound 38f was prepared according to the procedure reported in step-6 of Scheme-1 from ethyl 2-(2-((3'-(aminomethyl)-[7,7'-bibenzofuran]-5-yl)methoxy)phenyl)acetate (38e) (94 mg, 0.206 mmol) in THF/methanol (6 mL each) using lithium hydroxide hydrate (84 mg, 2.0 mmol) in water (2 mL). This gave after workup and purification by reverse phase column [C18 (50 g), eluting with ACN in water (containing 0.1% HCl) from 0-100%] 2-(2-((3'-(aminomethyl)-[7,7'-bibenzofuran]-5-yl)methoxy)phenyl)acetic acid (38f) (61 mg, 69% yield) HCl salt as a white solid. $^1$H NMR (300 MHz, DMSO-$d_6$) δ 8.64 (s, 2H), 8.12 (s, 1H), 8.00 (d, J=2.2 Hz, 1H), 7.93 (dd, J=7.9, 1.2 Hz, 1H), 7.76 (d, J=1.7 Hz, 1H), 7.66 (dd, J=4.7, 3.0 Hz, 2H), 7.42 (t, J=7.7 Hz, 1H), 7.17 (dd, J=9.4, 6.7 Hz, 2H), 7.05 (d, J=8.0 Hz, 1H), 7.00 (d, J=2.2 Hz, 1H), 6.83 (t, J=7.3 Hz, 1H), 5.22 (s, 2H), 4.18 (s, 2H), 3.53 (s, 2H). MS (ES+): 427.9 (M+1); MS(ES−): 425.9 (M−1). HPLC purity 99.10%.

Scheme-39

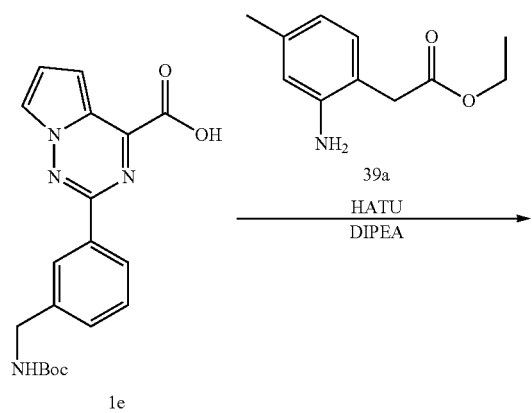

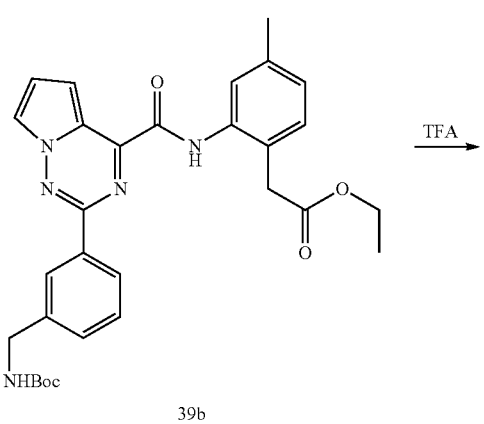

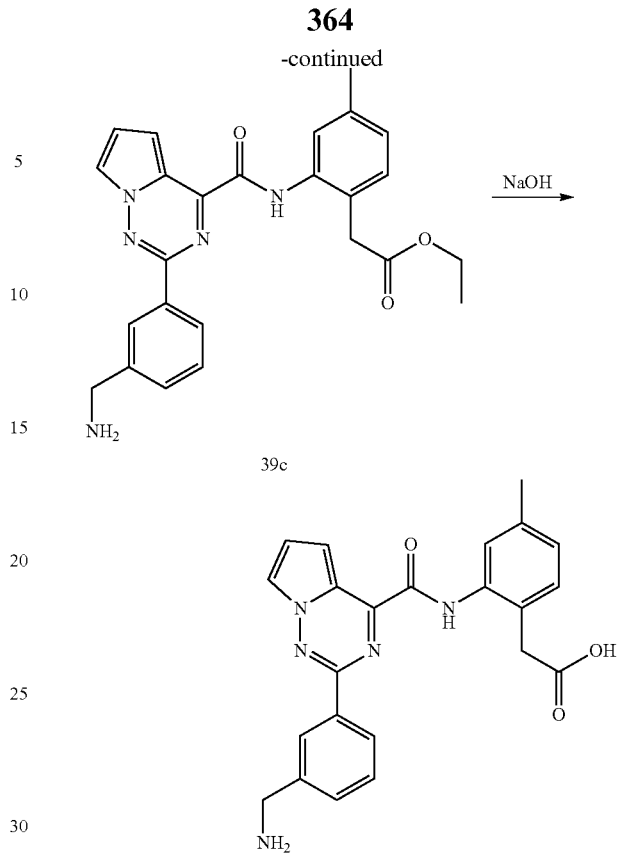

Preparation of 2-(2-(2-(3-(aminomethyl)phenyl)pyrrolo[2,1-f][1,2,4]triazine-4-carboxamido)-4-methylphenyl)acetic Acid (39d)

Step-1: Preparation of Ethyl 2-(2-(2-(3-(((tert-butoxycarbonyl)amino)methyl)phenyl)pyrrolo[2,1-f][1,2,4]triazine-4-carboxamido)-4-methylphenyl)acetate (39b)

Compound 39b was prepared according to the procedure reported in step-4 of Scheme-1 from 2-(3-(((tert-butoxycarbonyl)amino)methyl)phenyl)pyrrolo[2,1-f][1,2,4]triazine-4-carboxylic acid (1e) (0.15 g, 0.41 mmol) in DMF (3 mL) using ethyl 2-(2-amino-4-methylphenyl)acetate (39a) (118 mg, 0.611 mmol, CAS #1261742-93-1), DIPEA (0.213 mL, 1.22 mmol) and HATU (186 mg, 0.489 mmol). This gave after workup and purification by flash column chromatography [silica (12 g), eluting with 0-60% EtOAc in hexane] ethyl 2-(2-(2-(3-(((tert-butoxycarbonyl)amino)methyl)phenyl)pyrrolo[2,1-f][1,2,4]triazine-4-carboxamido)-4-methylphenyl)acetate (39b) (0.18 g, 81% yield) as an orange colored foam; $^1$H NMR (300 MHz, DMSO-$d_6$) δ 10.76 (s, 1H), 8.44 (d, J=7.9 Hz, 1H), 8.40-8.32 (m, 2H), 7.63 (d, J=1.6 Hz, 1H), 7.60-7.47 (m, 3H), 7.43 (d, J=7.6 Hz, 1H), 7.33-7.22 (m, 2H), 7.12-7.03 (m, 1H), 4.26 (d, J=6.1 Hz, 2H), 4.00 (q, J=7.1 Hz, 2H), 3.82 (s, 2H), 2.36 (s, 3H), 1.41 (s, 9H), 1.00 (t, J=7.1 Hz, 3H); MS (ES+): 544.5 (M+1).

Step-2: Preparation of Ethyl 2-(2-(2-(3-(aminomethyl)phenyl)pyrrolo[2,1-f][1,2,4]triazine-4-carboxamido)-4-methylphenyl)acetate (39c)

Compound 39c was prepared according to the procedure reported in step-5 of Scheme-1 from ethyl 2-(2-(2-(3-(((tert-butoxycarbonyl)amino)methyl)phenyl)pyrrolo[2,1-f][1,2,4]triazine-4-carboxamido)-4-methylphenyl)acetate (39b) (180 mg, 0.33 mmol) in DCM (5 mL) using TFA (0.255 mL, 3.31 mmol). This gave after workup and purification by reverse phase column chromatography [C18 (50 g), eluting with ACN in water (containing 0.1% HCl) from 0-100%] ethyl 2-(2-(2-(3-(aminomethyl)phenyl)pyrrolo[2,1-f][1,2,4]triazine-4-carboxamido)-4-methylphenyl)acetate (39c) (0.055 g, 38% yield) HCl salt as a solid. $^1$H NMR (300 MHz, DMSO-$d_6$) δ 10.77 (s, 1H), 8.66-8.55 (m, 2H), 8.43-8.27 (m, 4H), 7.74-7.54 (m, 4H), 7.33-7.25 (m, 2H), 7.15-7.06 (m, 1H), 4.18 (s, 2H), 4.00 (q, J=7.1 Hz, 2H), 3.82 (s, 2H), 2.36 (s, 3H), 1.00 (t, J=7.1 Hz, 3H); MS (ES+) 444.4 (M+1), MS (ES−) 478.4 (M+Cl); HPLC purity: 94.27%

Step-3: Preparation of 2-(2-(2-(3-(aminomethyl)phenyl)pyrrolo[2,1-f][1,2,4]triazine-4-carboxamido)-4-methylphenyl)acetic Acid (39d)

Compound 39d was prepared according to the procedure reported in step-4 of Scheme-4 from ethyl 2-(2-(2-(3-(aminomethyl)phenyl)pyrrolo[2,1-f][1,2,4]triazine-4-carboxamido)-4-methylphenyl)acetate (39c) (0.11 g, 0.248 mmol) in THF (30 mL) using sodium hydroxide (0.62 mL, 1.24 mmol, 2 M aqueous). This gave after workup and purification by reverse phase column [C18 (50 g), eluting with ACN in water (containing 0.1% HCl) from 0-100%] 2-(2-(2-(3-(aminomethyl)phenyl)pyrrolo[2,1-f][1,2,4]triazine-4-carboxamido)-4-methylphenyl)acetic acid (39d) (0.05 g, 48.5% yield) HCl salt as a solid; $^1$H NMR (300 MHz, DMSO-$d_6$) δ 12.76 (s, 1H), 10.85 (s, 1H), 8.61 (s, 1H), 8.54 (dt, J=7.1, 1.8 Hz, 1H), 8.44-8.30 (m, 4H), 7.73-7.59 (m, 4H), 7.32-7.25 (m, 2H), 7.08 (dd, J=7.6, 1.7 Hz, 1H), 4.24-4.12 (m, 2H), 3.74 (s, 2H), 2.36 (s, 3H). MS (ES+) 416.3 (M+1), MS (ES−) 414.4 (M−1), 829.7 (2M−1); HPLC purity: 97.48%.

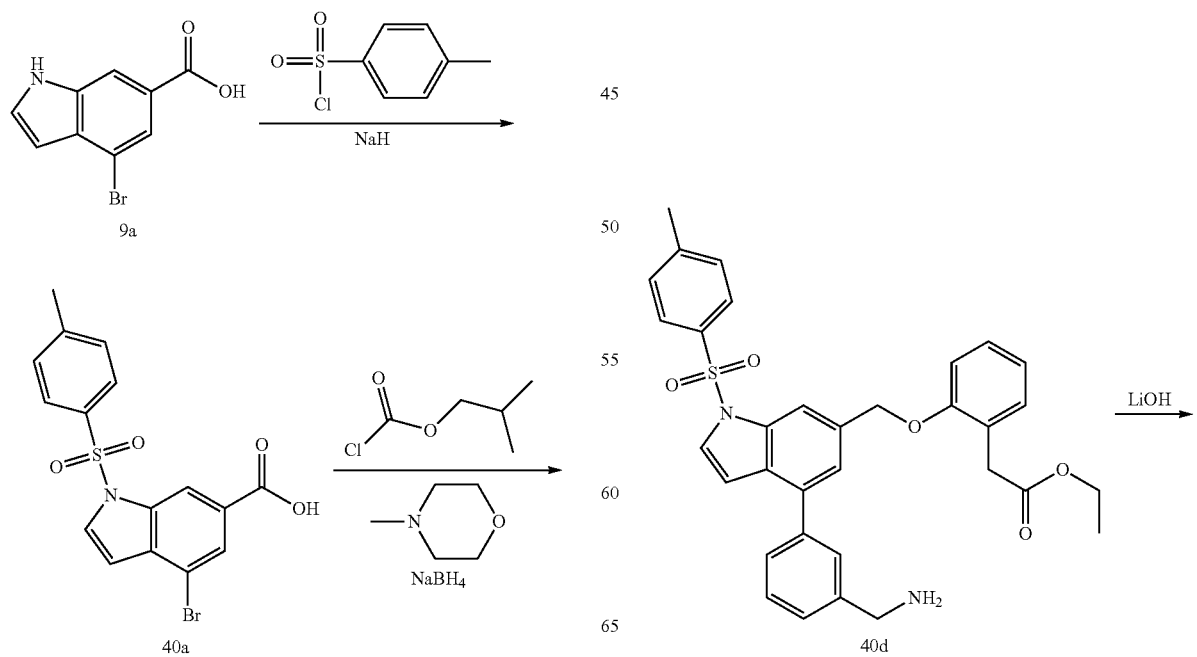

-continued

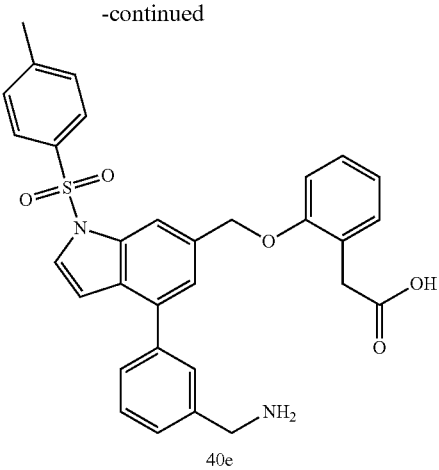

40e

Preparation of 2-(2-((4-(3-(aminomethyl)phenyl)-1-tosyl-1H-indol-6-yl)methoxy)phenyl)acetic Acid (40e)

Step-1: Preparation of 4-bromo-1-tosyl-1H-indole-6-carboxylic Acid (40a)

To a solution of 4-bromo-1H-indole-6-carboxylic acid (9a) (1.5 g, 6.25 mmol) in DMF (9.5 mL) at 0° C. was added NaH (60% in mineral oil, 0.625 g, 15.62 mmol). After 15 min stirring at 0° C., Tosyl-Cl (1.43 g, 7.50 mmol) was added in 1 g portions at 0° C. every 15 min and the reaction was warmed slowly in the ice bath to 10° C. After stirring for 2 h, the mixture was dumped into $H_2O$ and the mixture was acidified with 5 M HCl. The precipitate was collected by filtration, washed with water and dried to give 4-bromo-1-tosyl-1H-indole-6-carboxylic acid (40a) (1.85 g, 4.69 mmol, 75% yield) as a tan solid, which was used in the next step without further purification; H NMR (300 MHz, DMSO-$d_6$) δ 13.42 (s, 1H), 8.54-8.48 (m, 1H), 8.19 (d, J=3.8 Hz, 1H), 8.01-7.94 (m, 1H), 7.93-7.84 (m, 2H), 7.44 (d, J=8.1 Hz, 2H), 6.92-6.84 (m, 1H), 2.33 (s, 3H).

Step-2: Preparation of (4-bromo-1-tosyl-1H-indol-6-yl)methanol (40b)

Compound 40b was prepared according to the procedure reported in step-1 of Scheme-23 from 4-bromo-1-tosyl-1H-indole-6-carboxylic acid (40a) (1.5 g, 3.8 mmol) using N-methylmorpholine (0.5 mL, 4.57 mmol) in THF (30 mL), isobutyl chloroformate (0.6 mL, 4.57 mmol) and $NaBH_4$ (0.43 g, 11.41 mmol) in water (0.8 mL). This gave after workup (4-bromo-1-tosyl-1H-indol-6-yl)methanol (40b) (1.2 g, 82% yield) as a clear oil which was used as such for next step without further purification; MS (ES+) 402.1, 404.1 (M+Na), (ES−) 378.2, 380.2 (M−1).

Step-3: Preparation of Ethyl 2-(2-((4-bromo-1-tosyl-1H-indol-6-yl)methoxy)phenyl)acetate (40c)

Compound 40c was prepared according to the procedure reported in step-2 of Scheme-23 from (4-bromo-1-tosyl-1H-indol-6-yl)methanol (40b) (1.2 g, 3.16 mmol) in THF (15 mL) using triphenylphosphine (1.07 g, 4.1 mmol), ethyl 2-(2-hydroxyphenyl) acetate (23b) (0.739 g, 4.1 mmol) and DIAD (0.83 g, 4.1 mmol). This gave after workup and purification by flash column chromatography [silica (12 g), eluting with EtOAc in hexane from 0-60%] ethyl 2-(2-((4-bromo-1-tosyl-1H-indol-6-yl)methoxy)phenyl)acetate (40c) (0.4 g, 23% yield) as a white solid; $^1$H NMR (300 MHz, DMSO-$d_6$) δ 8.04 (s, 1H), 7.94 (d, J=3.7 Hz, 1H), 7.89 (s, 1H), 7.87 (s, 1H), 7.54 (s, 1H), 7.36 (s, 1H), 7.33 (s, 1H), 6.94 (t, J=7.4 Hz, 1H), 6.81-6.69 (m, 4H), 5.26 (s, 2H), 4.07-4.01 (m, 2H), 3.66 (s, 2H), 2.31 (s, 3H), 1.03 (t, J=7.1 Hz, 3H).

Step-4: Preparation of Ethyl 2-(2-((4-(3-(aminomethyl)phenyl)-1-tosyl-1H-indol-6-yl)methoxy)phenyl)acetate (40d)

Compound 40d was prepared according to the procedure reported in step-3 of Scheme-1 from ethyl 2-(2-((4-bromo-1-tosyl-1H-indol-6-yl)methoxy)phenyl)acetate (40c) (400 mg, 0.74 mmol) in dioxane (3 mL) using 3-(aminomethyl)phenylboronic acid hydrochloride (6c) (207 mg, 1.11 mmol), tripotassium phosphate (1.3 M solution, 0.42 mL, 1.25 mmol), tricyclohexylphosphine (62 mg, 0.22 mmol) and $Pd_2(dba)_3$ (68 mg, 0.074 mmol) under an Ar atmosphere and heating at 125° C. for 20 min in a microwave. This gave after workup, purification by flash column chromatography [silica (12 g), eluting with DMA80 in DCM from 0-70%] followed by purification by reverse phase column [C18 (30 g), eluting with ACN in water (containing 0.1% HCl) from 0-100%] of ethyl 2-(2-((4-(3-(aminomethyl)phenyl)-1-tosyl-1H-indol-6-yl)methoxy)phenyl)acetate (40d) (48 mg, 11% yield) as a white solid; $^1$H NMR (300 MHz, DMSO-$d_6$) δ 8.37 (s, 3H, $D_2O$ exchangeable), 8.07 (s, 1H), 7.94-7.85 (m, 3H), 7.70 (s, 1H), 7.61-7.48 (m, 3H), 7.41 (s, 1H), 7.36 (d, J=8.2 Hz, 2H), 7.28-7.19 (m, 2H), 7.12-7.04 (m, 1H), 7.00 (d, J=3.8 Hz, 1H), 6.93 (t, J=7.4 Hz, 1H), 5.32 (s, 2H), 4.15-4.04 (m, 2H), 3.90 (q, J=7.1 Hz, 2H), 3.66 (s, 2H), 2.32 (s, 3H), 0.94 (t, J=7.1 Hz, 3H); MS (ES+): 569.4 (M+1); 591.4 (M+Na); (ES−): 603.4 (M+Cl); HPLC purity: 95.30%.

Step-5: Preparation of 2-(2-((4-(3-(aminomethyl)phenyl)-1-tosyl-1H-indol-6-yl)methoxy)phenyl)acetic Acid (40e)

Compound 40e was prepared according to the procedure reported in step-6 of Scheme-1, from ethyl 2-(2-((4-(3-(aminomethyl)phenyl)-1-tosyl-1H-indol-6-yl)methoxy)phenyl)acetate (40d) (150 mg, 0.26 mmol) in MeOH/THF (10 mL, 1:1) using a solution of lithium hydroxide hydrate (11 mg, 0.26 mmol) in water (1 mL). This gave after workup and purification by reverse phase column [C18 (50 g), eluting with ACN in water (containing 0.1% HCl) from 0-100%] 2-(2-((4-(3-(aminomethyl)phenyl)-1-tosyl-1H-indol-6-yl)methoxy)phenyl)acetic acid (40e) (50 mg, 35% yield) HCl salt as a white solid; $^1$H NMR (300 MHz, DMSO-$d_6$) δ 12.24 (s, 1H, $D_2O$ exchangeable), 8.35 (s, 3H, $D_2O$ exchangeable), 8.08 (s, 1H), 7.94-7.89 (m, 2H), 7.88 (s, 1H), 7.70 (s, 1H), 7.61-7.48 (m, 3H), 7.45 (d, J=1.3 Hz, 1H), 7.36 (d, J=8.2 Hz, 2H), 7.29-7.18 (m, 2H), 7.09-7.02 (m, 1H), 6.99 (d, J=3.8 Hz, 1H), 6.96-6.90 (m, 1H), 5.34 (s, 2H), 4.10 (s, 2H), 3.64 (s, 2H), 2.32 (s, 3H); MS (ES+): 541.4 (M+1); 563.3 (M+Na); (ES−): 539.4 (M−1), 575.4 (M+Cl).

Scheme-41

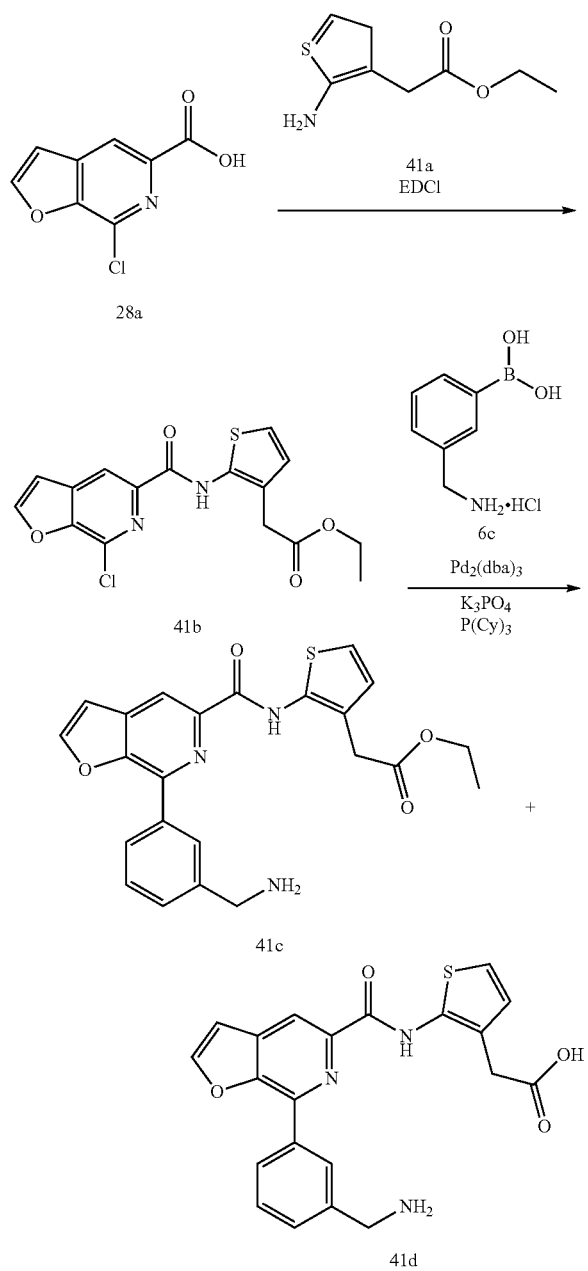

Preparation of 2-(2-(7-(3-(aminomethyl)phenyl)furo[2,3-c]pyridine-5-carboxamido)thiophen-3-yl)acetic Acid (41d)

Step-1: Preparation of Ethyl 2-(2-(7-chlorofuro[2,3-c]pyridine-5-carboxamido)thiophen-3-yl)acetate (41b)

Compound 41b was prepared according to the procedure reported in step-1 of Scheme-6 from 7-chlorofuro[2,3-c]pyridine-5-carboxylic acid (28a) (200 mg, 1.01 mmol) in MeOH (10 mL) using ethyl 2-(2-aminothiophen-3-yl)acetate (41a) (225 mg, 1.22 mmol, CAS #387390-67-2, prepared according to the procedure reported by Adrian Liam and Harris, William in PCT Int. Appl., 2002002567, 10 Jan. 2002), and EDCI (233 mg, 1.22 mmol). This gave after workup and purification by flash column chromatography [silica (12 g), eluting with EtOAc in hexane from 0-60%] ethyl 2-(2-(7-chlorofuro[2,3-c]pyridine-5-carboxamido)thiophen-3-yl)acetate (41b) (320 mg, 0.877 mmol, 87% yield) as a yellow solid; $^1$H NMR (300 MHz, DMSO-$d_6$) δ 10.84 (s, 1H), 8.58-8.45 (m, 2H), 7.42-7.33 (m, 1H), 7.16 (d, J=5.5 Hz, 1H), 6.91 (d, J=5.5 Hz, 1H), 4.15 (q, J=7.1 Hz, 2H), 3.79 (s, 2H), 1.21 (t, J=7.1 Hz, 3H).

Step-2: Preparation of 2-(2-(7-(3-(aminomethyl)phenyl)furo[2,3-c]pyridine-5-carboxamido)thiophen-3-yl)acetic Acid (41d)

Compound 41d was prepared according to the procedure reported in step-3 of Scheme-1 from ethyl 2-(2-(7-chlorofuro[2,3-c]pyridine-5-carboxamido)thiophen-3-yl)acetate (41b) (140 mg, 0.38 mmol) in dioxane (3 mL) using 3-(aminomethyl)phenylboronic acid hydrochloride (6c) (108 mg, 0.58 mmol), tripotassium phosphate (1.3 M solution, 0.22 mL, 0.65 mmol), tricyclohexylphosphine (32 mg, 0.12 mmol) and $Pd_2(dba)_3$ (35 mg, 0.038 mmol) under an Ar atmosphere and heating at 125° C. for 1 h in a microwave. This gave after workup, purification by flash column chromatography [silica (12 g), eluting with DMA80 in DCM from 0-70%] followed by reverse phase column chromatography [C18 (50 g), eluting with ACN in water (containing 0.1% HCl) from 0-100%] ethyl 2-(2-(7-(3-(aminomethyl)phenyl)furo[2,3-c]pyridine-5-carboxamido)thiophen-3-yl)acetate (41c) (37 mg, 22% yield) as a white solid; $^1$H NMR (300 MHz, DMSO-$d_6$) δ 11.18 (s, 1H, $D_2O$ exchangeable), 8.73 (s, 1H), 8.64-8.57 (m, 1H), 8.57-8.43 (m, 5H, partially $D_2O$ exchangeable), 7.75-7.66 (m, 2H), 7.38 (d, J=2.2 Hz, 1H), 7.17 (d, J=5.5 Hz, 1H), 6.94 (d, J=5.5 Hz, 1H), 6.55 (s, 1H), 4.19 (s, 2H), 4.08 (q, J=7.1 Hz, 2H), 3.86 (s, 2H), 1.10 (t, J=7.1 Hz, 3H); MS (ES+): 436.3 (M+1); (ES−): 470.3 (M+Cl); HPLC purity: 98.86%. Followed by 2-(2-(7-(3-(aminomethyl)phenyl)furo[2,3-c]pyridine-5-carboxamido)thiophen-3-yl)acetic acid (41d) (19 mg, 12% yield) as a white solid; $^1$H NMR (300 MHz, DMSO-$d_6$) δ 12.84 (s, 1H, $D_2O$ exchangeable), 11.28 (s, 1H, $D_2O$ exchangeable), 8.73 (s, 1H), 8.65-8.57 (m, 1H), 8.56-8.37 (m, 5H, partially $D_2O$ exchangeable), 7.75-7.65 (m, 2H), 7.38 (d, J=2.2 Hz, 1H), 7.15 (d, J=5.5 Hz, 1H), 6.93 (d, J=5.5 Hz, 1H), 4.20 (q, J=5.7 Hz, 2H), 3.79 (s, 2H); MS (ES$^+$) 408.3 (M+1); (ES−) 406.3 (M−1), 442.3 (M+Cl); HPLC purity: 99.41%.

Scheme-42

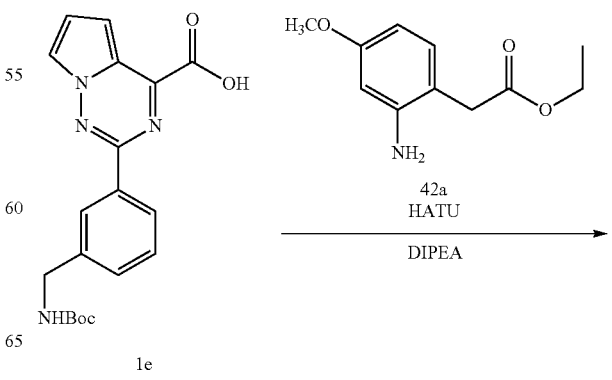

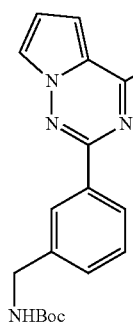

42b

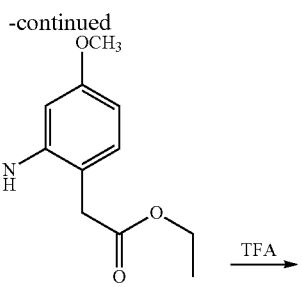

TFA →

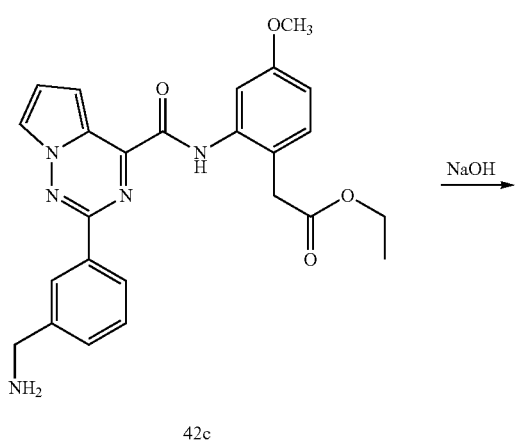

42c

NaOH →

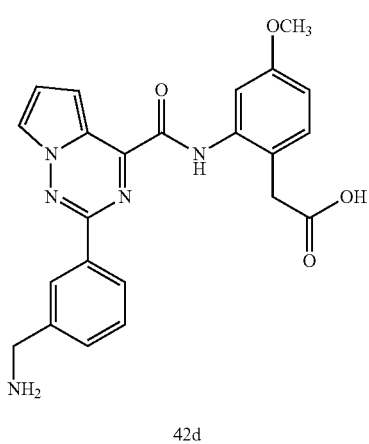

42d

Preparation of 2-(2-(2-(3-(aminomethyl)phenyl)pyrrolo[2,1-f][1,2,4]triazine-4-carboxamido)-4-methoxyphenyl)acetic Acid (42d)

Step-1: Preparation of Ethyl 2-(2-(2-(3-(((tert-butoxycarbonyl)amino)methyl)phenyl)pyrrolo[2,1-f][1,2,4]triazine-4-carboxamido)-4-methoxyphenyl)acetate (42b)

Compound 42b was prepared according to the procedure reported in step-4 of Scheme-1 from 2-(3-(((tert-butoxycarbonyl)amino)methyl)phenyl)pyrrolo[2,1-f][1,2,4]triazine-4-carboxylic acid (1e) (0.18 g, 0.49 mmol) in DMF (4 mL) using ethyl 2-(2-amino-4-methoxyphenyl)acetate (42a) (123 mg, 0.586 mmol, CAS #138344-20-4), DIPEA (0.26 mL, 1.47 mmol) and HATU (223 mg, 0.59 mmol). This gave after workup and purification by flash column chromatography [silica (12 g), eluting with 0-100% EtOAc in hexane] ethyl 2-(2-(2-(3-(((tert-butoxycarbonyl)amino)methyl)phenyl)pyrrolo[2,1-f][1,2,4]triazine-4-carboxamido)-4-methoxyphenyl)acetate (42b) (0.19 g, 70% yield) as an orange solid; $^1$H NMR (300 MHz, DMSO-$d_6$) δ 10.79 (s, 1H), 8.44 (d, J=7.8 Hz, 1H), 8.36 (d, J=2.3 Hz, 2H), 7.61-7.39 (m, 5H), 7.32 (d, J=8.5 Hz, 1H), 7.25 (dd, J=4.6, 2.5 Hz, 1H), 6.86 (dd, J=8.5, 2.7 Hz, 1H), 4.26 (d, J=6.1 Hz, 2H), 4.01 (q, J=7.1 Hz, 2H), 3.87-3.71 (m, 5H), 1.41 (s, 9H), 1.00 (t, J=7.1 Hz, 3H); MS (ES+): 560.4 (M+1), 582.4 (M+Na); (ES−): 558.5 (M−1).

Step-2: Preparation of Ethyl 2-(2-(2-(3-(aminomethyl)phenyl)pyrrolo[2,1-f][1,2,4]triazine-4-carboxamido)-4-methoxyphenyl)acetate (42c)

Compound 42c was prepared according to the procedure reported in step-5 of Scheme-1 from ethyl 2-(2-(2-(3-(((tert-butoxycarbonyl)amino)methyl)phenyl)pyrrolo[2,1-f][1,2,4]triazine-4-carboxamido)-4-methoxyphenyl)acetate (42b) (190 mg, 0.34 mmol) in DCM (5 mL) using TFA (0.26 mL, 3.4 mmol). This gave after workup and purification by reverse phase column chromatography [C18 (30 g), eluting with ACN in water (containing 0.1% HCl) from 0-60%] ethyl 2-(2-(2-(3-(aminomethyl)phenyl)pyrrolo[2,1-f][1,2,4]triazine-4-carboxamido)-4-methoxyphenyl)acetate (42c) (0.05 g, 32.0% yield) as a HCl salt; $^1$H NMR (300 MHz, DMSO-$d_6$) δ 10.79 (s, 1H), 8.66-8.55 (m, 2H), 8.45-8.32 (m, 4H), 7.73-7.56 (m, 3H), 7.41 (d, J=2.7 Hz, 1H), 7.33 (d, J=8.5 Hz, 1H), 7.29 (dd, J=4.6, 2.5 Hz, 1H), 6.88 (dd, J=8.5, 2.7 Hz, 1H), 4.18 (s, 2H), 4.00 (q, J=7.1 Hz, 2H), 3.86-3.75 (m, 5H), 1.01 (t, J=7.1 Hz, 3H); MS (ES+): 460.3 (M+1), MS (ES−): 494.3 (M+Cl); HPLC purity: 96.26%

Step-3: Preparation of 2-(2-(2-(3-(aminomethyl)phenyl)pyrrolo[2,1-f][1,2,4]triazine-4-carboxamido)-4-methoxyphenyl)acetic Acid (42d)

Compound 42d was prepared according to the procedure reported in step-4 of Scheme-4 from ethyl 2-(2-(2-(3-(aminomethyl)phenyl)pyrrolo[2,1-f][1,2,4]triazine-4-carboxamido)-4-methoxyphenyl)acetate (42c) (0.11 g, 0.239 mmol) in THF (2 mL) using sodium hydroxide (0.24 mL, 0.48 mmol, 2 M aqueous). This gave after workup and purification by reverse phase column [C18 (30 g), eluting with ACN in water (containing 0.1% HCl) from 0-40%] 2-(2-(2-(3-(aminomethyl)phenyl)pyrrolo[2,1-f][1,2,4]triazine-4-carboxamido)-4-methoxyphenyl)acetic acid (42d) (0.045 g, 44% yield) as a HCl salt; $^1$H NMR (300 MHz, DMSO-$d_6$) δ 12.77 (s, 1H), 10.88 (s, 1H), 8.62 (s, 1H), 8.57-8.34 (m, 5H), 7.74-7.59 (m, 3H), 7.52 (d, J=2.7 Hz, 1H), 7.36-7.25 (m, 2H), 6.85 (dd, J=8.5, 2.7 Hz, 1H), 4.23-4.12 (m, 2H), 3.80 (s, 3H), 3.73 (s, 2H); MS (ES+): 432.3 (M+1); MS (ES−): 430.4 (M−1); HPLC purity: 98.05%.

Scheme-43

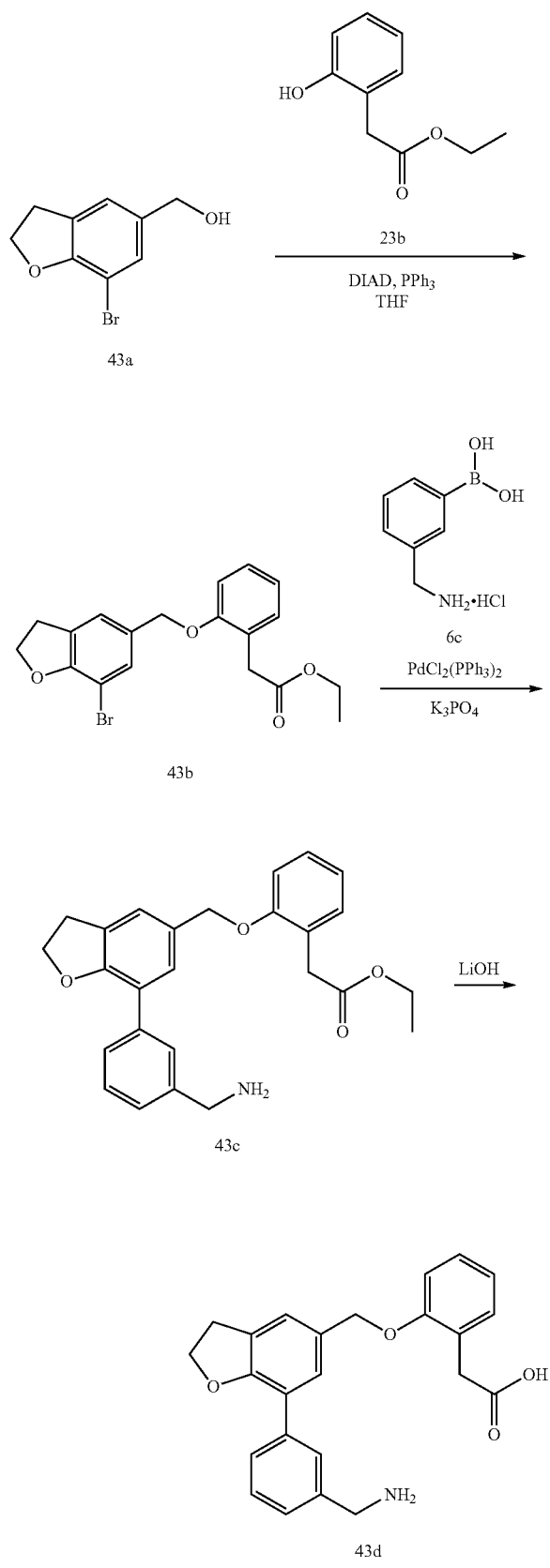

Preparation of 2-(2-((7-(3-(aminomethyl)phenyl)-2, 3-dihydrobenzofuran-5-yl)methoxy)phenyl)acetic Acid (43d)

Step-1: Preparation of Ethyl 2-(2-((7-bromo-2,3-dihydrobenzofuran-5-yl)methoxy)phenyl)acetate (43b)

Compound 43b was prepared according to the procedure reported in step-2 of Scheme-23 from (7-bromo-2,3-dihydrobenzofuran-5-yl)methanol (43a) (200 mg, 0.87 mmol; CAS #501430-83-7) in THF (15 mL) using triphenylphosphine (0.30 g, 1.135 mmol) ethyl 2-(2-hydroxyphenyl)acetate (23b) (205 mg, 1.14 mmol) and DIAD (0.23 g, 1.14 mmol). This gave after workup and purification by flash column chromatography [silica (12 g), eluting with EtOAc in hexane from 0-60%] ethyl 2-(2-((7-bromo-2,3-dihydrobenzofuran-5-yl)methoxy)phenyl)acetate (43b) (0.27 g, 78% yield) as colorless oil; MS (ES−): 389.3, 391.3 (M−1).

Step-2: Preparation of Ethyl 2-(2-((7-(3-(aminomethyl)phenyl)-2,3-dihydrobenzofuran-5-yl)methoxy)phenyl)acetate (43c)

Compound 43c was prepared according to the procedure reported in step-3 of Scheme-1 from ethyl 2-(2-((7-bromo-2,3-dihydrobenzofuran-5-yl)methoxy)phenyl)acetate (43b) (0.52 g, 1.33 mmol) in dioxane (6 mL) using 3-(aminomethyl)phenylboronic acid hydrochloride (6c) (0.37 g, 2.0 mmol), a solution of potassium carbonate (0.55 g, 4.0 mmol) in water (2 mL), and $PdCl_2(PPh_3)_2$ (0.140 g, 0.2 mmol) under an Ar atmosphere and heating at 100° C. for 2 h on oil bath. This gave after workup, purification by flash column chromatography [silica (12 g), eluting with MeOH in DCM from 0-20%] followed by purification by reverse phase column [C18 (50 g), eluting with ACN in water (containing 0.1% HCl) from 0-100%] ethyl 2-(2-((7-(3-(aminomethyl)phenyl)-2,3-dihydrobenzofuran-5-yl)methoxy)phenyl)acetate (43c) (0.23 g, 42% yield) HCl salt as a white solid; $^1$H NMR (300 MHz, DMSO-$d_6$) δ 8.26 (s, 3H), 7.79 (s, 1H), 7.75-7.70 (m, 1H), 7.54-7.40 (m, 2H), 7.38 (s, 1H), 7.31-7.18 (m, 3H), 7.08 (d, J=8.1 Hz, 1H), 6.90 (td, J=7.4, 1.1 Hz, 1H), 5.05 (s, 2H), 4.60 (t, J=8.7 Hz, 2H), 4.08 (s, 2H), 3.95 (q, J=7.1 Hz, 2H), 3.60 (s, 2H), 3.25 (t, J=8.7 Hz, 2H), 1.04 (t, J=7.1 Hz, 3H); MS (ES+) 418.4 (M+1); (ES−) 416.4 (M−1).

Step-3: Preparation of 2-(2-((7-(3-(aminomethyl)phenyl)-2,3-dihydrobenzofuran-5-yl)methoxy)phenyl)acetic Acid (43d)

Compound 43d was prepared according to the procedure reported in step-6 of Scheme-1 from ethyl 2-(2-((7-(3-(aminomethyl)phenyl)-2,3-dihydrobenzofuran-5-yl)methoxy)phenyl)acetate (43c) (0.12 g, 0.29 mmol) in THF/MeOH (4 mL) using lithium hydroxide hydrate (60 mg, 1.44 mmol) in water (0.8 mL). This gave after workup and purification by reverse phase column chromatography [C18 (50 g), eluting with ACN in water (containing 0.1% HCl) from 0-100%] 2-(2-((7-(3-(aminomethyl)phenyl)-2,3-dihydrobenzofuran-5-yl)methoxy)phenyl)acetic acid (43d) (40 mgs, 31% yield) as a white solid; $^1$H NMR (300 MHz, DMSO-$d_6$) δ 12.22 (s, 1H), 8.38 (s, 3H), 7.80 (s, 1H), 7.74 (dt, J=7.2, 1.8 Hz, 1H), 7.52-7.41 (m, 3H), 7.32 (d, J=1.6 Hz, 1H), 7.27-7.18 (m, 2H), 7.06 (dd, J=8.2, 1.1 Hz, 1H), 6.89 (td, J=7.4, 1.1 Hz, 1H), 5.07 (s, 2H), 4.60 (t, J=8.7 Hz, 2H), 4.07 (d, J=5.3 Hz, 2H), 3.56 (s, 2H), 3.25 (t, J=8.7 Hz, 2H);

MS (ES+): 390.4 (M+1); MS (ES−): 388.5 (M−1), 424.4 (M+Cl). HPLC purity: 91.28%.

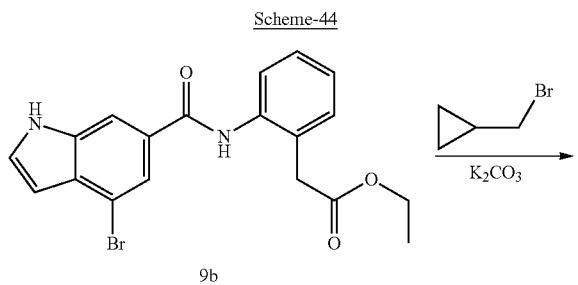

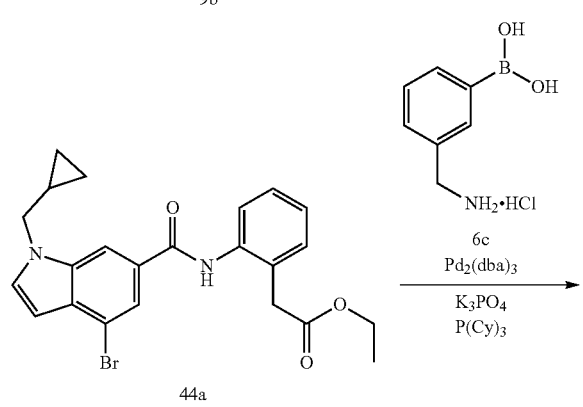

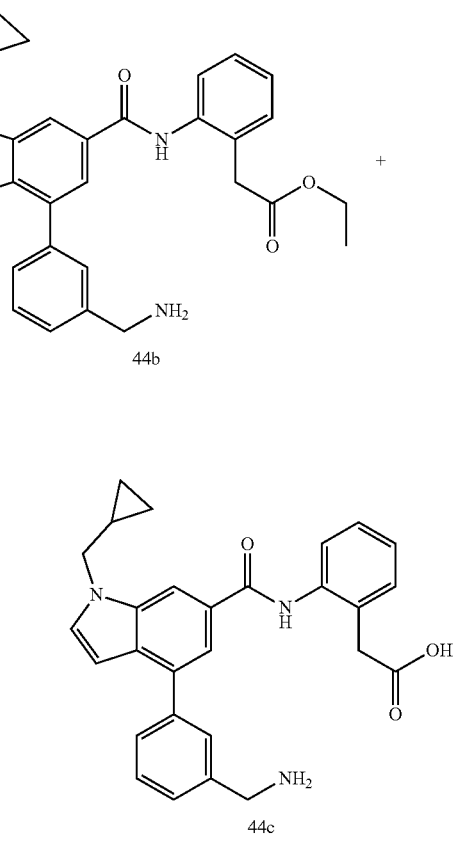

Preparation of 2-(2-(4-(3-(aminomethyl)phenyl)-1-(cyclopropylmethyl)-1H-indole-6-carboxamido)phenyl)acetic Acid (44c)

Step-1: Preparation of Ethyl 2-(2-(4-bromo-1-(cyclopropylmethyl)-1H-indole-6-carboxamido)phenyl)acetate (44a)

To a solution of ethyl 2-(2-(4-bromo-1H-indole-6-carboxamido)phenyl)acetate (9b) (0.2 g, 0.50 mmol) in DMF was added (bromomethyl)cyclopropane (0.07 mL, 0.75 mmol) and potassium carbonate (0.14 g, 1.0 mmol) and stirred at 60° C. overnight. The reaction mixture was diluted with EtOAc (100 mL), washed with water (3×), brine, dried, filtered and concentrated in vacuum. The residue obtained was purified by flash column chromatography [silica (12 g), eluting with EtOAc in hexane from 0-60%] to give ethyl 2-(2-(4-bromo-1-(cyclopropylmethyl)-1H-indole-6-carboxamido)phenyl)acetate (44a) (0.15 g, 64% yield); 1H NMR (300 MHz, DMSO-$d_6$) δ 10.02 (s, 1H), 8.24 (s, 1H), 7.85 (s, 1H), 7.78 (d, J=3.1 Hz, 1H), 7.47-7.19 (m, 4H), 6.50 (d, J=3.1 Hz, 1H), 4.15 (d, J=7.1 Hz, 2H), 3.96 (m, 2H), 3.75 (s, 2H), 1.32 (m, 1H), 1.00 (t, J=7.1 Hz, 3H), 0.58-0.31 (m, 4H). MS (ES+): 455.3 & 457.3 (M+1).

Step-2: Preparation of 2-(2-(4-(3-(aminomethyl)phenyl)-1-(cyclopropylmethyl)-1H-indole-6-carboxamido)phenyl)acetic Acid (44c)

Compound 44c was prepared according to the procedure reported in step-3 of Scheme-1 from ethyl 2-(2-(4-bromo-1-(cyclopropylmethyl)-1H-indole-6-carboxamido)phenyl)acetate (44a) (140 mg, 0.31 mmol) in dioxane (3 mL) using 3-(aminomethyl)phenylboronic acid hydrochloride (6c) (90 mg, 0.46 mmol), tripotassium phosphate (1.3 M solution) (0.71 mL, 0.92 mmol), tricyclohexylphosphine (30 mg, 0.09 mmol) and Pd$_2$(dba)$_3$ (30 mg, 0.03 mmol) under an Ar atmosphere and heating at 125° C. for 45 min in a microwave. This gave after workup, purification by flash column chromatography [silica (12 g), eluting with DMA80 in DCM from 0-60%] followed by purification by reverse phase column [C18 (50 g), eluting with ACN in water (containing 0.1% HCl) from 0-100%] ethyl 2-(2-(4-(3-(aminomethyl)phenyl)-1-(cyclopropylmethyl)-1H-indole-6-carboxamido)phenyl)acetate (44b) (0.06 g, 37% yield) as a white solid; $^1$H NMR (300 MHz, DMSO-$d_6$) δ 10.04 (s, 1H), 8.32 (s, 2H), 8.25 (s, 1H), 7.88 (s, 1H), 7.80 (d, J=1.3 Hz, 1H), 7.77 (s, 1H), 7.75 (d, J=3.0 Hz, 2H), 7.59 (t, J=7.6 Hz, 1H), 7.55-7.40 (m, 2H), 7.35 (t, J=7.5 Hz, 2H), 7.25 (td, J=7.2, 1.5 Hz, 1H), 6.74 (d, J=3.2 Hz, 1H), 4.18 (m, 2H), 4.15 (s, 2H), 3.95 (m, 2H), 3.78 (s, 2H), 1.37 (m, 1H), 0.98 (t, J=7.1 Hz, 3H), 0.62-0.39 (m, 4H); MS (ES+): 482.4 (M+1); MS (ES−): 516.5 (M+Cl). HPLC purity: 96.64%; followed by 2-(2-(4-(3-(aminomethyl)phenyl)-1-(cyclopropylmethyl)-1H-indole-6-carboxamido)phenyl)acetic acid (44c) (0.01 g, 7% yield) as a white solid; $^1$H NMR (300 MHz, DMSO-$d_6$): δ 8.37 (s, 2H), 8.24 (s, 1H), 7.91 (s, 1H), 7.85 (s, 1H), 7.79 (d, J=7.7 Hz, 1H), 7.75 (d, J=3.2 Hz, 1H), 7.58 (t, J=7.7 Hz, 2H), 7.49 (d, J=7.7 Hz, 1H), 7.32 (t, J=8.0 Hz, 2H), 7.20 (t, J=7.4 Hz, 1H), 6.74 (d, J=3.2 Hz, 1H), 6.56 (s, 1H), 4.25-4.09 (m, 4H), 3.69 (s, 2H), 1.48-1.29 (m, 1H), 0.60-0.37 (m, 4H); MS (ES+): 454.4 (M+1); MS (ES−): 452.4 (M−1), 488.4 (M+Cl). HPLC purity: 97.36%.

Scheme-45

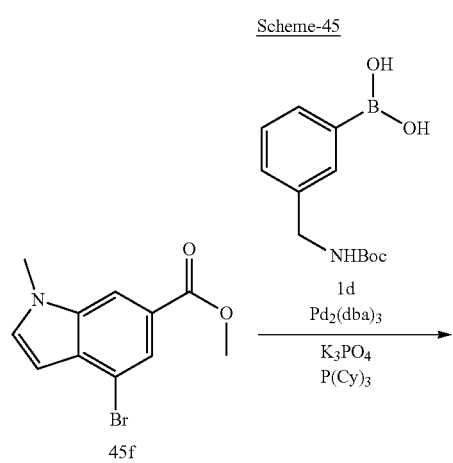

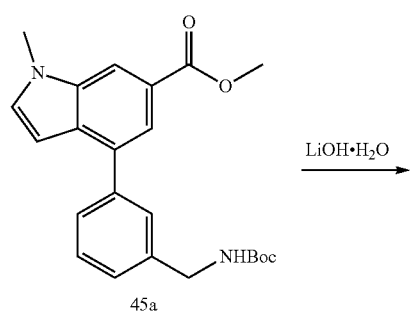

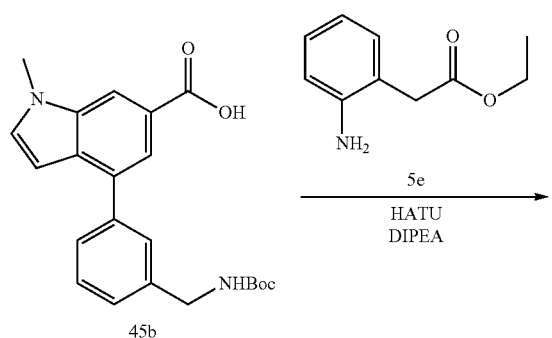

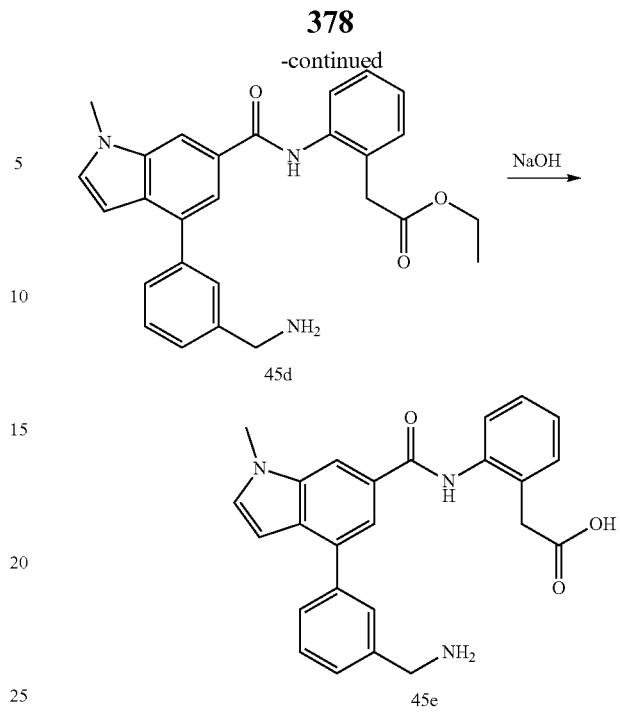

Preparation of 2-(2-(4-(3-(aminomethyl)phenyl)-1-methyl-1H-indole-6-carboxamido)phenyl)acetic Acid (45e)

Step-1: Preparation of methyl 4-(3-(((tert-butoxycarbonyl)amino)methyl)phenyl)-1-methyl-1H-indole-6-carboxylate (45a)

Compound 45a was prepared according to the procedure reported in step-3 of Scheme-1, from methyl 4-bromo-1-methyl-1H-indole-6-carboxylate (45f) (500 mg, 1.87 mmol; CAS #: 1246867-53-7) in dioxane (11 mL) using 3-((tert-butoxycarbonylamino)methyl)phenylboronic acid (Id) (702 mg, 2.80 mmol), tripotassium phosphate (1.3 M solution, 1.1 mL, 3.17 mmol), tricylcohexylphosphine (157 mg, 0.56 mmol) and Pd$_2$(dba)$_3$ (171 mg, 0.19 mmol) under a nitrogen atmosphere by heating at 120° C. for 45 min in a microwave. This gave after workup and purification by flash column chromatography [silica (12 g), eluting with hexanes/ethyl acetate 0% to 100%] methyl 4-(3-(((tert-butoxycarbonyl)amino)methyl)phenyl)-1-methyl-1H-indole-6-carboxylate (45a) (620 mg, 84% yield) as a yellow solid; MS (ES+): 417.3 (M+Na).

Step-2: Preparation of 4-(3-(((tert-butoxycarbonyl)amino)methyl)phenyl)-1-methyl-1H-indole-6-carboxylic Acid (45b)

Compound 45b was prepared according to the procedure reported in step-6 of Scheme-1, from methyl 4-(3-(((tert-butoxycarbonyl)amino)methyl)phenyl)-1-methyl-1H-indole-6-carboxylate (45a) (600 mg, 1.52 mmol) in THF/MeOH (15 mL) using a solution of lithium hydroxide hydrate (383 mg, 9.13 mmol) in water (1 mL) This gave after workup 4-(3-(((tert-butoxycarbonyl)amino)methyl)phenyl)-1-methyl-1H-indole-6-carboxylic acid (45b) (500 mg, 86% yield) as an off white solid, which was used in the next step without further purification. $^1$H NMR (300 MHz, DMSO-d$_6$) δ 12.73 (s, 1H, D$_2$O exchangeable), 8.09 (s, 1H), 7.73 (d, J=1.3 Hz, 1H), 7.63 (d, J=3.1 Hz, 1H), 7.60-7.42 (m, 4H), 7.27 (d, J=7.6 Hz, 1H), 6.63 (d, J=3.2 Hz, 1H), 4.22 (d, J=6.2 Hz, 2H), 3.91 (s, 3H), 1.40 (s, 9H).

Step-3: Preparation of Ethyl 2-(2-(4-(3-(((tert-butoxycarbonyl)amino)methyl)phenyl)-1-methyl-1H-indole-6-carboxamido)phenyl)acetate (45c)

Compound 45c was prepared according to the procedure reported in step-4 of Scheme-1, from 4-(3-(((tert-butoxycarbonyl)amino)methyl)phenyl)-1-methyl-1H-indole-6-carboxylic acid (45b) (300 mg, 0.79 mmol) in DMF (10 mL) using ethyl 2-(2-aminophenyl)acetate (5e) (184 mg, 1.03 mmol), DIPEA (0.28 mL, 1.58 mmol) and HATU (360 mg, 0.79 mmol). This gave after workup and purification by flash column chromatography [silica (12 g), eluting with 0-60% EtOAc in hexane] ethyl 2-(2-(4-(3-(((tert-butoxycarbonyl)amino)methyl)phenyl)-1-methyl-1H-indole-6-carboxamido)phenyl)acetate (45c) (211 mg, 49% yield) as a pink semi-solid; $^1$H NMR (300 MHz, DMSO-$d_6$) δ 10.02 (s, 1H, D$_2$O exchangeable), 8.11 (s, 1H), 7.77 (d, J=1.4 Hz, 1H), 7.65 (s, 1H), 7.63-7.57 (m, 2H), 7.54-7.40 (m, 3H), 7.37-7.31 (m, 2H), 7.30-7.22 (m, 2H), 6.64 (d, J=3.1 Hz, 1H), 4.23 (d, J=6.2 Hz, 2H), 3.98-3.88 (m, 5H), 3.77 (s, 2H), 1.40 (s, 9H), 0.98 (t, J=7.1 Hz, 3H); MS (ES+): 564.5 (M+Na); (ES−): 540.5 (M−1).

Step-4: Preparation of Ethyl 2-(2-(4-(3-(aminomethyl)phenyl)-1-methyl-1H-indole-6-carboxamido)phenyl)acetate (45d)

Compound 45d was prepared according to the procedure reported in step-5 of Scheme-1, from ethyl 2-(2-(4-(3-(((tert-butoxycarbonyl)amino)methyl)phenyl)-1-methyl-1H-indole-6-carboxamido)phenyl)acetate (45c) (210 mg, 0.39 mmol) using TFA (0.3 mL, 3.88 mmol) in DCM (5 mL). This gave after workup and purification by flash column chromatography [silica (12 g), eluting with DMA80 in DCM from 0-50%] followed by reverse phase column chromatography [C18 (50 g), eluting with ACN in water (containing 0.1% HCl) from 0-100%] ethyl 2-(2-(4-(3-(aminomethyl)phenyl)-1-methyl-1H-indole-6-carboxamido)phenyl)acetate (45d) (114 mg, 67% yield) as a white solid. $^1$H NMR (300 MHz, DMSO-$d_6$) δ 10.08 (s, 1H, D$_2$O exchangeable), 8.45 (s, 3H, D$_2$O exchangeable), 8.18 (s, 1H), 7.90 (d, J=1.7 Hz, 1H), 7.84 (d, J=1.4 Hz, 1H), 7.80-7.72 (m, 1H), 7.65 (d, J=3.1 Hz, 1H), 7.62-7.49 (m, 2H), 7.44 (dd, J=7.6, 1.7 Hz, 1H), 7.38-7.29 (m, 2H), 7.25 (td, J=7.1, 1.5 Hz, 1H), 6.75 (d, J=3.1 Hz, 1H), 4.14 (s, 2H), 4.04-3.89 (m, 5H), 3.79 (s, 2H), 0.99 (t, J=7.1 Hz, 3H).

Step-5: Preparation of 2-(2-(4-(3-(aminomethyl)phenyl)-1-methyl-1H-indole-6-carboxamido)phenyl)acetic Acid (45e)

Compound 45e was prepared according to the procedure reported in step-4 of Scheme-4, from ethyl 2-(2-(4-(3-(aminomethyl)phenyl)-1-methyl-1H-indole-6-carboxamido)phenyl)acetate (45d) (65 mg, 0.15 mmol) in MeOH/THF (10 mL, 1:1) using a solution of sodium hydroxide (35 mg, 0.88 mmol) in water (2 mL). This gave after workup and purification by reverse phase column [C18 (50 g), eluting with ACN in water (containing 0.1% HCl) from 0-100%] 2-(2-(4-(3-(aminomethyl)phenyl)-1-methyl-1H-indole-6-carboxamido)phenyl)acetic acid (45e) (29 mg, 48% yield) as a white solid; $^1$H NMR (300 MHz, DMSO-$d_6$) δ 12.42 (s, 1H, D$_2$O exchangeable), 10.10 (s, 1H, D$_2$O exchangeable), 8.43 (s, 3H, D$_2$O exchangeable), 8.18 (s, 1H), 7.92-7.87 (m, 1H), 7.86-7.80 (m, 1H), 7.80-7.73 (m, 1H), 7.65 (d, J=3.1 Hz, 1H), 7.59 (t, J=7.6 Hz, 1H), 7.55-7.49 (m, 2H), 7.39-7.29 (m, 2H), 7.22 (td, J=7.4, 1.4 Hz, 1H), 6.74 (d, J=3.1 Hz, 1H), 4.14 (s, 2H), 3.93 (s, 3H), 3.71 (s, 2H); MS (ES+): 414.3 (M+1); 436.3 (M+Na); (ES−): 412.4 (M−1), 448.4 (M+Cl).

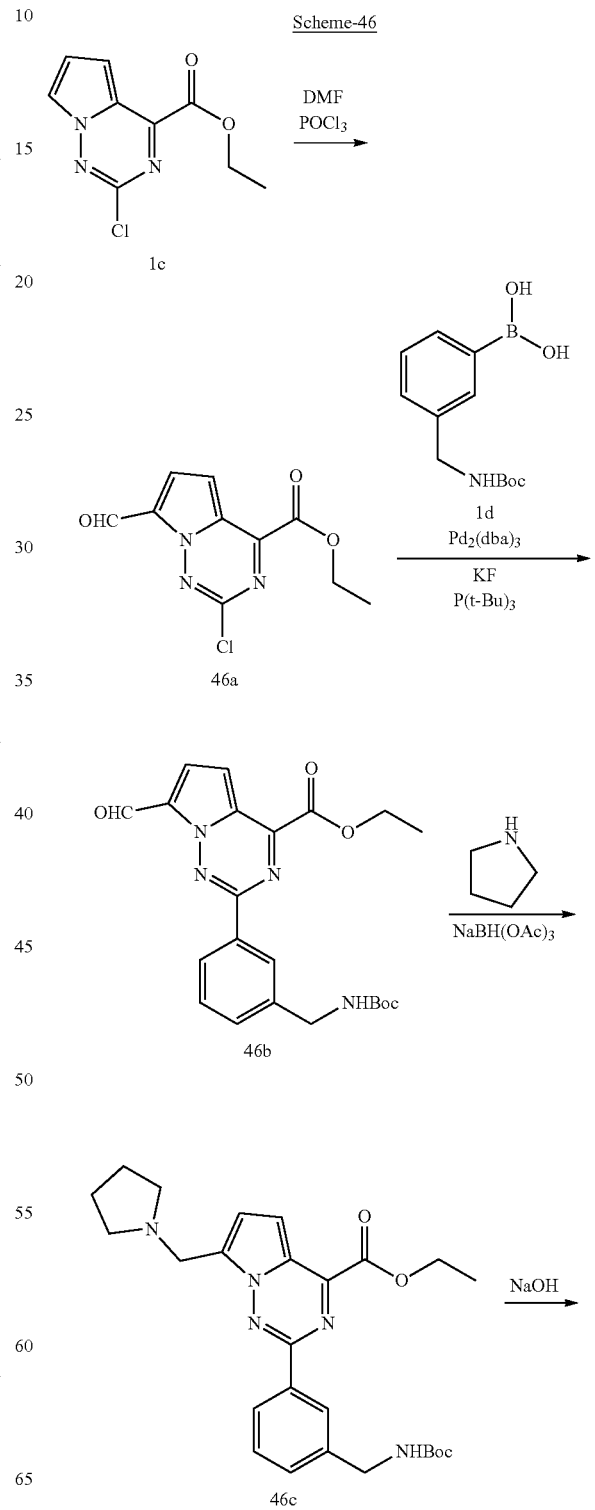

Scheme-46

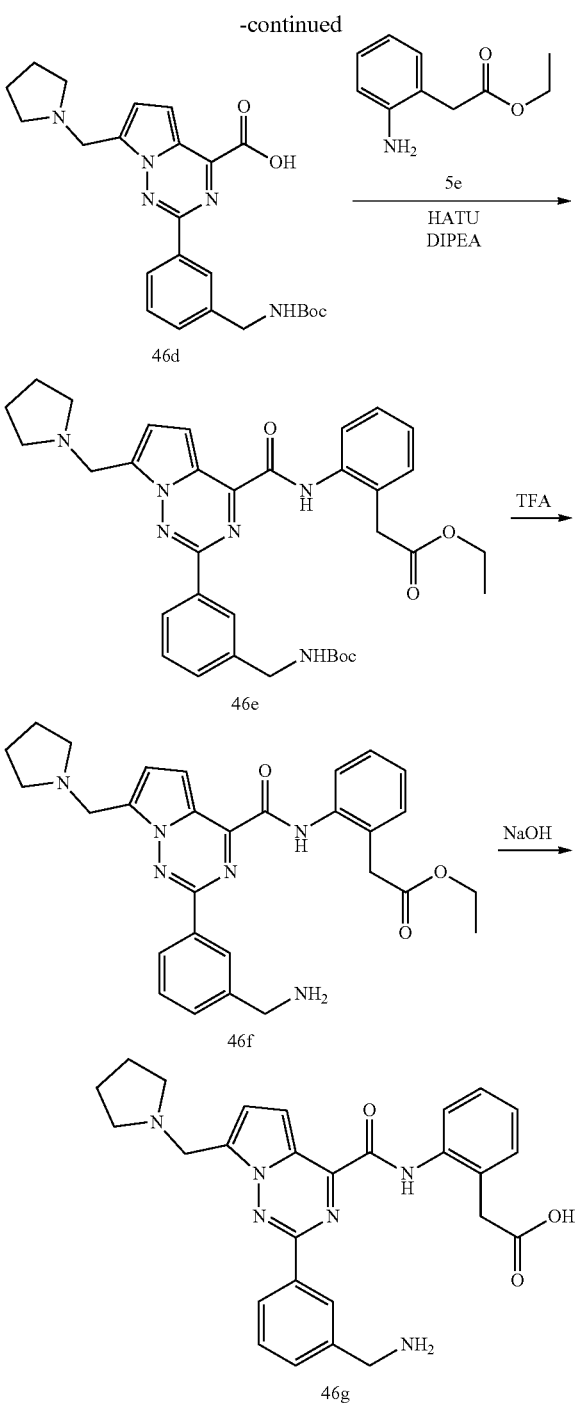

Preparation of 2-(2-(2-(3-(aminomethyl)phenyl)-7-(pyrrolidin-1-ylmethyl)pyrrolo[2,1-f][1,2,4]triazine-4-carboxamido)phenyl)acetic Acid (46g)

Step-1: Preparation of Ethyl 2-chloro-7-formylpyrrolo[2,1-f][1,2,4]triazine-4-carboxylate (46a)

To POCl₃ (1.239 mL, 13.30 mmol) in a sealed tube cooled with ice-water was added DMF (0.515 mL, 6.65 mmol) and stirred until the reaction mixture was homogeneous. The reaction mixture was warmed to room temperature and added ethyl 2-chloropyrrolo[2,1-f][1,2,4]triazine-4-car-boxylate (1c) (300 mg, 1.33 mmol) and heated at 95° C. in a sealed tube for 5 h. The reaction mixture was cooled to room temperature and poured into an ice-cooled sat. aq. NaHCO₃ (60 mL), extracted with ethyl acetate (2×50 mL). The combined organic extracts were washed with water (40 mL), brine (40 mL), dried, filtered and concentrated in vacuum. The residue obtained was purified by flash column chromatography [silica gel eluting with hexanes/ethyl acetate (1:0 to 9:1)] to afford ethyl 2-chloro-7-formylpyrrolo[2,1-f][1,2,4]triazine-4-carboxylate (46a) (224 mg, 66% yield) as a yellow solid; ¹H NMR (300 MHz, DMSO-d₆) δ 10.38 (s, 1H), 7.78 (d, J=5.1 Hz, 1H), 7.51 (d, J=5.1 Hz, 1H), 4.50 (q, J=7.1 Hz, 2H), 1.41 (t, J=7.1 Hz, 3H).

Step-2: Preparation of Ethyl 2-(3-(((tert-butoxycarbonyl)amino)methyl)phenyl)-7-formylpyrrolo[2,1-f][1,2,4]triazine-4-carboxylate (46b)

Compound 46b was prepared according to the procedure reported in step-3 of Scheme-1, from ethyl 2-chloro-7-formylpyrrolo[2,1-f][1,2,4]triazine-4-carboxylate (46a) (250 mg, 0.99 mmol) in DMF (10 mL) using 3-((tert-butoxycarbonylamino)methyl)phenylboronic acid (Id) (371 mg, 1.48 mmol), potassium fluoride (189 mg, 3.25 mmol), tri-tert-butylphosphine (1.281 mL, 1.28 mmol) and Pd₂(dba)₃ (90 mg, 0.099 mmol) under an argon atmosphere by heating at 120° C. overnight. This gave after workup and purification by flash column chromatography [silica (12 g), eluting with hexanes/ethyl acetate 0% to 50%] ethyl 2-(3-(((tert-butoxycarbonyl)amino)methyl)phenyl)-7-formylpyrrolo[2,1-f][1,2,4]triazine-4-carboxylate (46b) (339 mg, 81% yield) as a yellow solid; ¹H NMR (300 MHz, DMSO-d₆) δ 10.62 (s, 1H), 8.34-8.27 (m, 2H), 7.73 (d, J=5.0 Hz, 1H), 7.61-7.51 (m, 2H), 7.51-7.44 (m, 1H), 7.41 (d, J=5.0 Hz, 1H), 4.54 (q, J=7.1 Hz, 2H), 4.26 (d, J=6.2 Hz, 2H), 1.49-1.39 (m, 12H); MS (ES+): 447.3 (M+1).

Step-3: Preparation of Ethyl 2-(3-(((tert-butoxycarbonyl)amino)methyl)phenyl)-7-(pyrrolidin-1-ylmethyl)pyrrolo[2,1-f][1,2,4]triazine-4-carboxylate (46c)

To a solution of ethyl 2-(3-(((tert-butoxycarbonyl)amino)methyl)phenyl)-7-formylpyrrolo[2,1-f][1,2,4]triazine-4-carboxylate (46b) (150 mg, 0.35 mmol) in DCE (10 mL) was added pyrrolidine (27.6 mg, 0.39 mmol) and acetic acid (0.020 mL, 0.35 mmol). The resulting mixture was stirred at RT for 2 h followed by the addition of sodium triacetoxyborohydride (90 mg, 0.42 mmol). The resulting mixture was stirred at RT for 2 h, diluted with EtOAc, washed with water, dried, filtered and concentrated in vacuum. The residue obtained was purified by chromatography [silica (12 g), eluting with EtOAc in hexane from 0-60%] to give ethyl 2-(3-(((tert-butoxycarbonyl)amino)methyl)phenyl)-7-(pyrrolidin-1-ylmethyl)pyrrolo[2,1-f][1,2,4]triazine-4-carboxylate (46c) (140 mg, 83% yield) as a yellow semi-solid; ¹H NMR (300 MHz, DMSO-d₆) δ 8.23 (d, J=6.2 Hz, 2H), 7.59-7.47 (m, 2H), 7.41 (d, J=7.7 Hz, 1H), 7.35 (d, J=4.6 Hz, 1H), 7.20 (d, J=4.6 Hz, 1H), 4.51 (q, J=7.1 Hz, 2H), 4.25 (d, J=6.2 Hz, 2H), 4.18 (s, 2H), 2.64-2.55 (m, 4H), 1.75-1.63 (m, 4H), 1.50-1.29 (m, 12H); MS (ES+): 480.4 (M+1); 502.4 (M+Na); (ES−): 478.5 (M−1).

Step-4: Preparation of 2-(3-(((tert-butoxycarbonyl)amino)methyl)phenyl)-7-(pyrrolidin-1-ylmethyl)pyrrolo[2,1-f][1,2,4]triazine-4-carboxylic Acid (46d)

Compound 46d was prepared according to the procedure reported in step-4 of Scheme-4, from ethyl 2-(3-(((tert-butoxycarbonyl)amino)methyl)phenyl)-7-(pyrrolidin-1-yl-methyl)pyrrolo[2,1-f][1,2,4]triazine-4-carboxylate (46c) (140 mg, 1.52 mmol) in THF/MeOH (10 mL) using a solution of sodium hydroxide (70 mg, 1.75 mmol) in water (2 mL). This gave after workup followed by purification by flash column chromatography [silica (4 g), eluting with MeOH in DCM from 0-100%] 2-(3-(((tert-butoxycarbonyl)amino)methyl)phenyl)-7-(pyrrolidin-1-ylmethyl)pyrrolo[2,1-f][1,2,4]triazine-4-carboxylic acid (46d) (60 mg, 46% yield) as a yellow solid; $^1$H NMR (300 MHz, DMSO-$d_6$) δ 8.40-8.27 (m, 2H), 7.60-7.49 (m, 2H), 7.46-7.30 (m, 3H), 4.95 (s, 2H), 4.26 (d, J=6.1 Hz, 2H), 3.57-3.36 (m, 4H), 2.08-1.83 (m, 4H), 1.41 (s, 9H); MS (ES+): 452.4 (M+1); 474.4 (M+Na); (ES−): 450.4 (M−1); 486.4 (M+Cl).

Step-5: Preparation of Ethyl 2-(2-(2-(3-(((tert-butoxycarbonyl)amino)methyl)phenyl)-7-(pyrrolidin-1-ylmethyl)pyrrolo[2,1-f][1,2,4]triazine-4-carboxamido)phenyl)acetate (46e)

Compound 46e was prepared according to the procedure reported in step-4 of Scheme-1, from 2-(3-(((tert-butoxycarbonyl)amino)methyl)phenyl)-7-(pyrrolidin-1-ylmethyl)pyrrolo[2,1-f][1,2,4]triazine-4-carboxylic acid (46d) (56 mg, 0.12 mmol) in DMF (10 mL) using ethyl 2-(2-aminophenyl)acetate (5e) (29 mg, 0.16 mmol), DIPEA (0.043 mL, 0.25 mmol) and HATU (57 mg, 0.15 mmol). This gave after workup and purification by flash column chromatography [silica (12 g), eluting with 0-60% EtOAc in hexane] ethyl 2-(2-(2-(3-(((tert-butoxycarbonyl)amino)methyl)phenyl)-7-(pyrrolidin-1-ylmethyl)pyrrolo[2,1-f][1,2,4]triazine-4-carboxamido)phenyl)acetate (46e) (53 mg, 70% yield) as a pink semi-solid; MS (ES+): 613.4 (M+1); 635.4 (M+Na); (ES−): 611.5 (M−1).

Step-6: Preparation of Ethyl 2-(2-(2-(3-(aminomethyl)phenyl)-7-(pyrrolidin-1-ylmethyl)pyrrolo[2,1-f][1,2,4]triazine-4-carboxamido)phenyl)acetate (46f)

Compound 46f was prepared according to the procedure reported in step-5 of Scheme-1, from ethyl 2-(2-(2-(3-(((tert-butoxycarbonyl)amino)methyl)phenyl)-7-(pyrrolidin-1-ylmethyl)pyrrolo[2,1-f][1,2,4]triazine-4-carboxamido)phenyl)acetate (46e) (53 mg, 0.086 mmol) using TFA (0.067 mL, 0.87 mmol) in DCM (5 mL). This gave after workup and purification by flash column chromatography [silica (12 g), eluting with DMA80 in DCM from 0-50%] ethyl 2-(2-(2-(3-(aminomethyl)phenyl)-7-(pyrrolidin-1-ylmethyl)pyrrolo[2,1-f][1,2,4]triazine-4-carboxamido)phenyl)acetate (46f) (27 mg, 61% yield) as a yellow solid; $^1$H NMR (300 MHz, DMSO-$d_6$) δ 10.88 (s, 1H, D$_2$O exchangeable), 9.00 (s, 1H, D$_2$O exchangeable), 8.71 (d, J=7.6 Hz, 3H), 7.72 (t, J=7.9 Hz, 2H), 7.68-7.61 (m, 2H), 7.53 (d, J=4.7 Hz, 1H), 7.42 (t, J=7.3 Hz, 2H), 7.31 (td, J=7.5, 7.1, 1.4 Hz, 1H), 5.07 (s, 2H), 4.19 (d, J=5.1 Hz, 2H), 4.01 (q, J=7.1 Hz, 2H), 3.88 (s, 2H), 3.58-3.43 (m, 2H), 3.33-3.25 (m, 2H), 2.14-1.97 (m, 2H), 1.95-1.80 (m, 2H), 1.02 (t, J=7.1 Hz, 3H); MS (ES+): 513.4 (M+1); 535.4 (M+Na).

Step-7: Preparation of 2-(2-(2-(3-(aminomethyl)phenyl)-7-(pyrrolidin-1-ylmethyl)pyrrolo[2,1-f][1,2,4]triazine-4-carboxamido)phenyl)acetic Acid (46g)

Compound 46g was prepared according to the procedure reported in step-4 of Scheme-4, from ethyl 2-(2-(2-(3-(aminomethyl)phenyl)-7-(pyrrolidin-1-ylmethyl)pyrrolo[2,1-f][1,2,4]triazine-4-carboxamido)phenyl)acetate (46f) (25 mg, 0.049 mmol) in MeOH/THF (10 mL, 1:1) using a solution of sodium hydroxide (12 mg, 0.29 mmol) in water (2 mL). This gave after workup and purification by reverse phase column [C18 (50 g), eluting with ACN in water (containing 0.1% HCl) from 0-100%] 2-(2-(2-(3-(aminomethyl)phenyl)-7-(pyrrolidin-1-ylmethyl)pyrrolo[2,1-f][1,2,4]triazine-4-carboxamido)phenyl)acetic acid (46g) (11 mg, 47% yield) as a yellow solid; $^1$H NMR (300 MHz, DMSO-$d_6$) δ 12.81 (s, 1H, D$_2$O exchangeable), 11.09 (s, 1H, D$_2$O exchangeable), 10.94 (s, 1H), 8.97 (d, J=1.7 Hz, 1H), 8.80-8.60 (m, 4H, partially D$_2$O exchangeable), 7.83 (d, J=8.1 Hz, 1H), 7.73-7.60 (m, 3H), 7.55 (d, J=4.7 Hz, 1H), 7.47-7.37 (m, 2H), 7.28 (td, J=7.4, 1.3 Hz, 1H), 5.08 (d, J=4.5 Hz, 2H), 4.26-4.12 (m, 2H), 3.81 (s, 2H), 3.59-3.41 (m, 4H), 2.16-1.97 (m, 2H), 1.95-1.78 (m, 2H); MS (ES$^+$) 485.4 (M+1); (ES−) 483.4 (M−1); HPLC purity, 93.69%.

Scheme-47

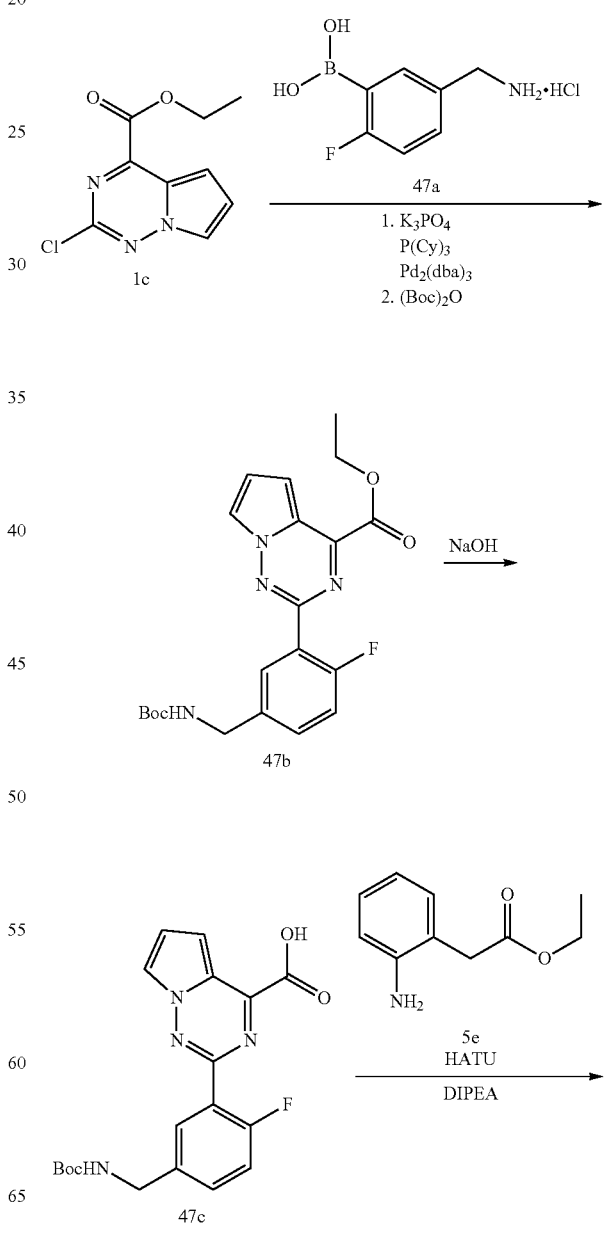

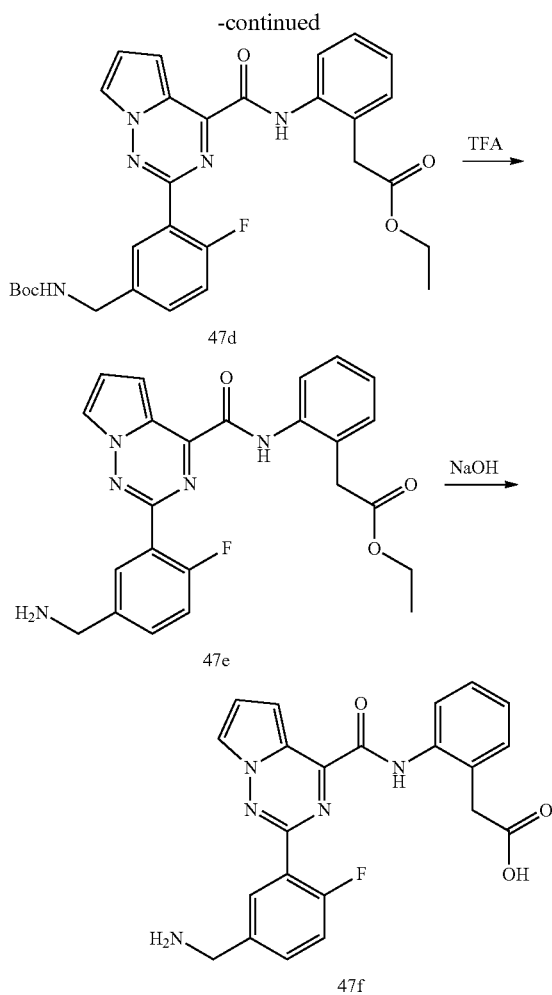

Preparation of 2-(2-(2-(5-(aminomethyl)-2-fluorophenyl)pyrrolo[2,1-f][1,2,4]triazine-4-carboxamido)phenyl)acetic Acid (47f)

Step-1: Preparation of Ethyl 2-(5-(((tert-butoxycarbonyl)amino)methyl)-2-fluorophenyl)pyrrolo[2,1-f][1,2,4]triazine-4-carboxylate (47b)

To a solution of ethyl 2-chloropyrrolo[2,1-f][1,2,4]triazine-4-carboxylate (1c) (400 mg, 1.77 mmol) in dioxane (12 mL) was added (5-(aminomethyl)-2-fluorophenyl)boronic acid hydrochloride (47a) (546 mg, 2.66 mmol; CAS #1072946-46-3), 3 M aqueous potassium triphosphate (1.182 mL, 3.55 mmol), tricyclohexylphosphine (99 mg, 0.355 mmol) and Pd$_2$(dba)$_3$ (162 mg, 0.177 mmol). The mixture was degassed and filled with Ar, then heated at 125° C. for 30 min in a microwave. The mixture was cooled to room temperature, diluted with water (60 mL) and EtOAc (60 mL). To the biphasic layer was added BOC-anhydride (580 mg, 2.66 mmol) and stirred at room temperature for 3 h. The organic layer was separated and aqueous layer was extracted with EtOAc (50 mL). The organic layers were combined washed with washed with water, brine, filtered and concentrated in vacuum to dryness. The residue obtained was purified by flash column chromatography [silica (12 g), eluting with EtOAc in hexanes 0 to 60%] to afford ethyl 2-(5-(((tert-butoxycarbonyl)amino)methyl)-2-fluorophenyl)pyrrolo[2,1-f][1,2,4]triazine-4-carboxylate (47b) (0.32 g, 0.772 mmol, 43.6% yield) as an orange colored foam; $^1$H NMR (300 MHz, DMSO-d$_6$) δ 8.40 (s, 1H), 7.87 (d, J=7.3 Hz, 1H), 7.53 (t, J=6.1 Hz, 1H), 7.49-7.24 (m, 4H), 4.50 (q, J=7.1 Hz, 2H), 4.19 (d, J=6.2 Hz, 2H), 1.44-1.33 (m, 12H); MS (ES+): 437.3 (M+Na)

Step-2: Preparation of 2-(5-(((tert-butoxycarbonyl)amino)methyl)-2-fluorophenyl)pyrrolo[2,1-f][1,2,4]triazine-4-carboxylic Acid (47c)

Compound 47c was prepared according to the procedure reported in step-4 of Scheme-4 from ethyl 2-(5-(((tert-butoxycarbonyl)amino)methyl)-2-fluorophenyl)pyrrolo[2,1-f][1,2,4]triazine-4-carboxylate (47b) (0.32 g, 0.772 mmol) in THF (10 mL) using sodium hydroxide (0.772 mL, 1.544 mmol, 2 M aqueous solution). This gave after workup 2-(5-(((tert-butoxycarbonyl)amino)methyl)-2-fluorophenyl)pyrrolo[2,1-f][1,2,4]triazine-4-carboxylic acid (47c) (0.29 g, 97% yield) as a light orange foam. $^1$H NMR (300 MHz, DMSO-d$_6$) δ 14.43 (s, 1H), 8.36 (dd, J=2.6, 1.4 Hz, 1H), 7.92 (dd, J=7.5, 2.2 Hz, 1H), 7.53 (t, J=6.1 Hz, 1H), 7.47-7.39 (m, 1H), 7.39-7.32 (m, 2H), 7.24 (dd, J=4.6, 2.5 Hz, 1H), 4.19 (d, J=6.2 Hz, 2H), 1.39 (s, 9H); MS (ES−): 385.3 (M−1).

Step-3: Preparation of Ethyl 2-(2-(2-(5-(((tert-butoxycarbonyl)amino)methyl)-2-fluorophenyl)pyrrolo[2,1-f][1,2,4]triazine-4-carboxamido)phenyl)acetate (47d)

Compound 47d was prepared according to the procedure reported in step-4 of Scheme-1 from 2-(5-(((tert-butoxycarbonyl)amino)methyl)-2-fluorophenyl)pyrrolo[2,1-f][1,2,4]triazine-4-carboxylic acid (47c) (180 mg, 0.47 mmol) in DMF (3 mL) using ethyl 2-(2-aminophenyl)acetate (5e) (125 mg, 0.7 mmol), DIPEA (0.24 mL, 1.4 mmol) and HATU (213 mg, 0.56 mmol). This gave after workup and purification by flash column chromatography [silica (12 g), eluting with EtOAc in hexane from 0-60%] ethyl 2-(2-(2-(5-(((tert-butoxycarbonyl)amino)methyl)-2-fluorophenyl)pyrrolo[2,1-f][1,2,4]triazine-4-carboxamido)phenyl)acetate (47d) (0.19 g, 75% yield) as an orange colored foam; $^1$H NMR (300 MHz, DMSO-d$_6$) δ 10.61 (s, 1H), 8.41 (dd, J=2.6, 1.4 Hz, 1H), 8.18 (dd, J=7.6, 2.2 Hz, 1H), 7.82 (d, J=7.7 Hz, 1H), 7.59 (dd, J=4.6, 1.4 Hz, 1H), 7.55-7.33 (m, 5H), 7.37-7.20 (m, 2H), 4.23 (d, J=6.1 Hz, 2H), 3.94 (q, J=7.1 Hz, 2H), 3.84 (s, 2H), 1.38 (s, 9H), 0.96 (t, J=7.1 Hz, 3H); MS (ES+): 548.3 (M+1), 570.3 (M+Na); (ES−): 582.4 (M+Cl).

Step-4: Preparation of Ethyl 2-(2-(2-(5-(aminomethyl)-2-fluorophenyl)pyrrolo[2,1-f][1,2,4]triazine-4-carboxamido)phenyl)acetate (47e)

Compound 47e was prepared according to the procedure reported in step-5 of Scheme-1 from ethyl 2-(2-(2-(5-(((tert-butoxycarbonyl)amino)methyl)-2-fluorophenyl)pyrrolo[2,1-f][1,2,4]triazine-4-carboxamido)phenyl)acetate (47d) (180 mg, 0.329 mmol) in DCM (5 mL) using TFA (0.025 mL, 0.329 mmol). This gave after workup and purification by reverse phase column chromatography [C18 (30 g), eluting with ACN in water (containing 0.1% HCl) from 0-100%] ethyl 2-(2-(2-(5-(aminomethyl)-2-fluorophenyl)pyrrolo[2,1-f][1,2,4]triazine-4-carboxamido)phenyl)acetate (47e) (0.045 g, 31% yield) as a HCl salt; $^1$H NMR (300 MHz, DMSO-d$_6$) δ 10.61 (s, 1H), 8.53 (d, J=7.1 Hz, 1H), 8.49-8.32 (m, 4H), 7.81-7.70 (m, 2H), 7.61 (dd, J=4.6, 1.3 Hz, 1H), 7.51 (dd, J=11.1, 8.5 Hz, 1H), 7.45-7.37 (m, 2H), 7.35-7.24 (m, 2H), 4.21-4.10 (m, 2H), 3.94 (q, J=7.1 Hz, 2H), 3.84 (s, 2H), 0.97 (t, J=7.1 Hz, 3H); $^{19}$F NMR (282 MHz, DMSO-$d_6$) δ −113.01; MS (ES+): 448.3 (M+1), MS (ES−): 482.3 (M+Cl); HPLC purity 94.88%.

Step-5: Preparation of 2-(2-(2-(5-(aminomethyl)-2-fluorophenyl)pyrrolo[2,1-f][1,2,4]triazine-4-carboxamido)phenyl)acetic Acid (47f)

Compound 47f was prepared according to the procedure reported in step-4 of Scheme-4 from ethyl 2-(2-(2-(5-(aminomethyl)-2-fluorophenyl)pyrrolo[2,1-f][1,2,4]triazine-4-carboxamido)phenyl)acetate (47e) (110 mg, 0.246 mmol) in THF (4 mL) using a 2 M aqueous solution of NaOH (0.246 mL, 0.492 mmol). This gave after workup and purification by reverse phase column chromatography [C18 (30 g), eluting with ACN in water (containing 0.1% HCl) from 0-40%] 2-(2-(2-(5-(aminomethyl)-2-fluorophenyl)pyrrolo[2,1-f][1,2,4]triazine-4-carboxamido)phenyl)acetic acid (47f) (0.045 g, 44% yield) as a HCl salt; $^1$H NMR (300 MHz, DMSO-$d_6$) δ 12.70 (s, 1H), 11.12-10.76 (m, 1H), 8.66-8.55 (m, 1H), 8.51-8.33 (m, 4H), 7.90-7.82 (m, 1H), 7.75-7.65 (m, 1H), 7.63 (dd, J=4.6, 1.3 Hz, 1H), 7.49 (dd, J=11.1, 8.5 Hz, 1H), 7.43-7.34 (m, 2H), 7.31 (dd, J=4.6, 2.6 Hz, 1H), 7.24 (t, J=7.5 Hz, 1H), 4.23-4.08 (m, 2H), 3.74 (s, 2H); $^{19}$F NMR (282 MHz, DMSO-$d_6$) δ −112.49; MS (ES+) 420.3 (M+1), MS (ES−) 418.3 (M−1); HPLC purity: 97.95%.

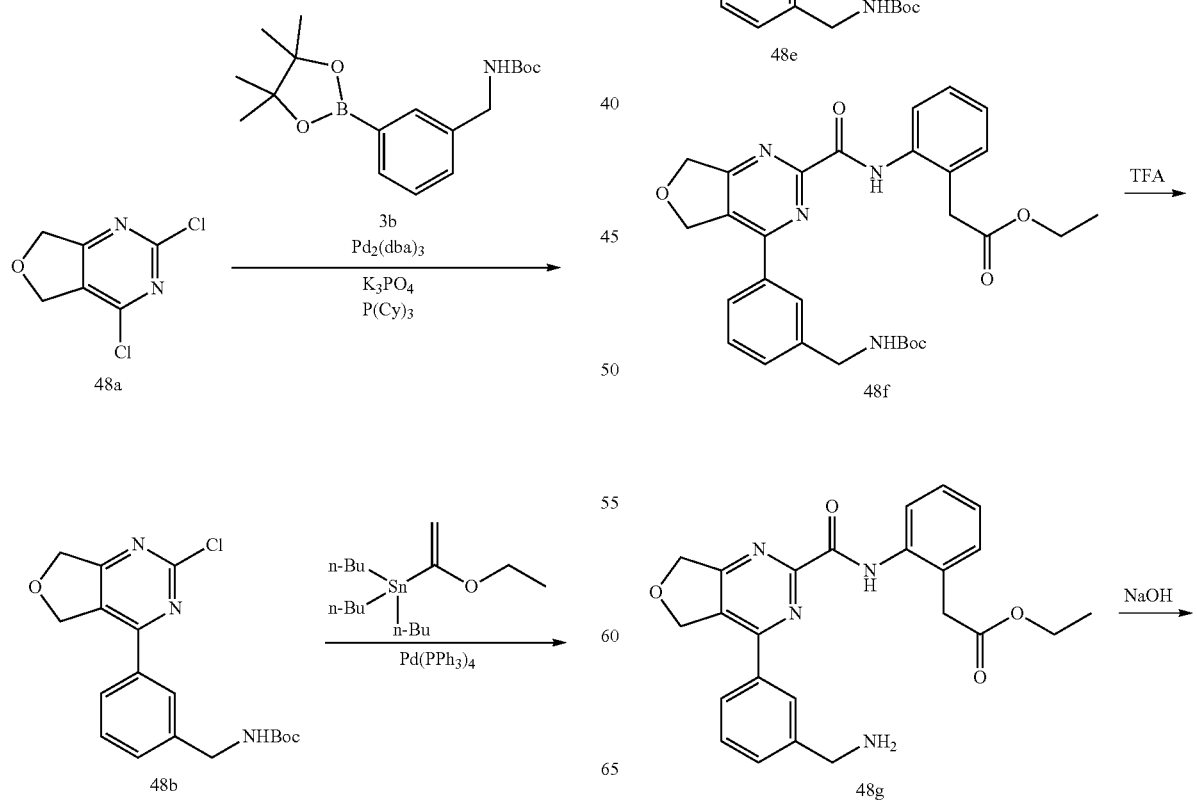

Scheme-48

-continued

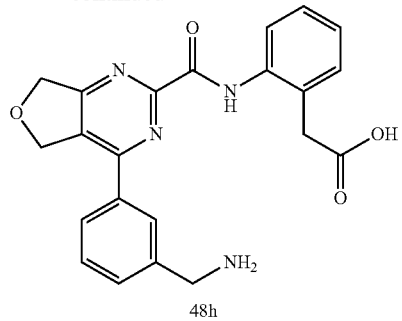

48h

Preparation of 2-(2-(4-(3-(aminomethyl)phenyl)-5,7-dihydrofuro[3,4-d]pyrimidine-2-carboxamido)phenyl)acetic Acid (48h)

Step-1: Preparation of tert-butyl 3-(2-chloro-5,7-dihydrofuro[3,4-d]pyrimidin-4-yl)benzylcarbamate (48b)

Compound 48b was prepared according to the procedure reported in step-3 of Scheme-1 from 2,4-dichloro-5,7-dihydrofuro[3,4-d]pyrimidine (48a) (2 g, 10.47 mmol; CAS #848398-41-4) in dioxane (100 mL) using tert-butyl 3-(4,5,5-tetramethyl-1,3,2-dioxaborolan-2-yl)benzylcarbamate (3b) (2.49 g, 7.48 mmol), tripotassium phosphate (5.48 mL, 16.45 mmol, 3 M aqueous solution), tricyclohexylphosphine (0.63 g, 2.24 mmol) and $Pd_2(dba)_3$ (0.69 g, 0.75 mmol) in argon atmosphere and heating in an oil bath at 120° C. for 1.5 h. This gave after workup and purification by flash column chromatography [silica (40 g), eluting with EtOAc in hexane from 0-70%] tert-butyl 3-(2-chloro-5,7-dihydrofuro[3,4-d]pyrimidin-4-yl)benzylcarbamate (48b) (0.72 g, 27% yield) as a white solid; $^1$H NMR (300 MHz, DMSO-$d_6$) δ 7.81 (d, J=2.0 Hz, 1H), 7.74-7.68 (m, 1H), 7.59-7.44 (m, 3H), 5.40 (t, J=1.8 Hz, 2H), 5.02 (d, J=1.8 Hz, 2H), 4.22 (d, J=6.2 Hz, 2H), 1.41 (s, 9H). MS (ES−): 360.4 & 362.3 (M−1).

Step-2: Preparation of tert-butyl 3-(2-(1-ethoxyvinyl)-5,7-dihydrofuro[3,4-d]pyrimidin-4-yl)benzylcarbamate (48c)

Compound 48c was prepared according to the procedure reported in step-1 of Scheme-1 from tert-butyl 3-(2-chloro-5,7-dihydrofuro[3,4-d]pyrimidin-4-yl)benzylcarbamate (48b) (0.7 g, 1.94 mmol) in DMF (20 mL) using 1-ethoxyvinyltri-n-butyltin (0.86 mL, 2.52 mmol) and $Pd(PPh_3)_4$ (0.22 g, 0.19 mmol) in argon atmosphere and heating at 110° C. for 4 h. This gave after workup and purification by flash column chromatography [silica (40 g), eluting with EtOAc in hexane from 0-50%] tert-butyl 3-(2-(1-ethoxyvinyl)-5,7-dihydrofuro[3,4-d]pyrimidin-4-yl)benzylcarbamate (48c) (0.51 g, 66% yield) as a white solid; MS (ES+): 398.4 (M+1), 420.3 (M+Na); MS (ES−): 396.4 (M−1), 432.4 (M+Cl).

Step-3: Preparation of Ethyl 4-(3-(((tert-butoxycarbonyl)amino)methyl)phenyl)-5,7-dihydrofuro[3,4-d]pyrimidine-2-carboxylate (48d)

Compound 48d was prepared according to the procedure reported in step-2 of Scheme-1 from tert-butyl 3-(2-(1-ethoxyvinyl)-5,7-dihydrofuro[3,4-d]pyrimidin-4-yl)benzylcarbamate (48c) (0.5 g, 1.258 mmol) in 1,4-dioxane (100 mL) using sodium periodate solution (0.54 g, 2.52 mmol) in water (10 mL) and $KMnO_4$ (0.12 g, 0.76 mmol, and second dosing of 0.12 g, 0.76 mmol after 12 h). This gave after workup and purification by flash column chromatography [silica (12 g), eluting with EtOAc in hexane from 0-60%] ethyl 4-(3-(((tert-butoxycarbonyl)amino)methyl)phenyl)-5,7-dihydrofuro[3,4-d]pyrimidine-2-carboxylate (48d) (0.28 g, 56% yield) as a yellow solid; MS (ES+): 400.3 (M+1), 422.3 (M+Na); MS (ES−): 398.4 (M−1).

Step-4: Preparation of 4-(3-(((tert-butoxycarbonyl)amino)methyl)phenyl)-5,7-dihydrofuro[3,4-d]pyrimidine-2-carboxylic Acid (48e)

Compound 48e was prepared according to the procedure reported in step-4 of Scheme-4 from ethyl 4-(3-(((tert-butoxycarbonyl)amino)methyl)phenyl)-5,7-dihydrofuro[3,4-d]pyrimidine-2-carboxylate (48d) (0.28 g, 0.70 mmol) in THF/MeOH (5 mL, 1:1) using sodium hydroxide (0.11 g, 2.80 mmol) in water (2 mL). This gave after workup 4-(3-(((tert-butoxycarbonyl)amino)methyl)phenyl)-5,7-dihydrofuro[3,4-d]pyrimidine-2-carboxylic acid (48e) (0.16 g, 62% yield) as a yellow solid; $^1$H NMR (300 MHz, DMSO-$d_6$) δ 7.86 (s, 1H), 7.81 (d, J=7.8 Hz, 1H), 7.54 (t, J=7.7 Hz, 2H), 7.45 (d, J=7.7 Hz, 1H), 5.47 (s, 2H), 5.08 (d, J=1.8 Hz, 2H), 4.23 (d, J=6.2 Hz, 2H), 1.41 (s, 9H); MS (ES−): 370.3 (M−1).

Step-5: Preparation of Ethyl 2-(2-(4-(3-(((tert-butoxycarbonyl)amino)methyl)phenyl)-5,7-dihydrofuro[3,4-d]pyrimidine-2-carboxamido)phenyl)acetate (48f)

Compound 48f was prepared according to the procedure reported in step-4 of Scheme-1 from 4-(3-(((tert-butoxycarbonyl)amino)methyl)phenyl)-5,7-dihydrofuro[3,4-d]pyrimidine-2-carboxylic acid (48e) (0.16 g, 0.43 mmol) in DMF (5 mL) using ethyl 2-(2-aminophenyl)acetate (5e) (0.09 g, 0.52 mmol), DIPEA (0.15 mL, 0.86 mmol) and HATU (0.20 g, 0.52 mmol). This gave after workup and purification by flash column chromatography [silica (12 g), eluting with 0-60% EtOAc/MeOH (9:1) in hexane from 0-100%] ethyl 2-(2-(4-(3-(((tert-butoxycarbonyl)amino)methyl)phenyl)-5,7-dihydrofuro[3,4-d]pyrimidine-2-carboxamido)phenyl)acetate (48f) (0.17 g, 72% yield) as a white solid; MS (ES+): 555.3 (M+Na); MS (ES−): 531.6 (M−1).

Step-6: Preparation of Ethyl 2-(2-(4-(3-(aminomethyl)phenyl)-5,7-dihydrofuro[3,4-d]pyrimidine-2-carboxamido)phenyl)acetate (48g)

Compound 48g was prepared according to the procedure reported in step-5 of Scheme-1 from ethyl 2-(2-(4-(3-(((tert-butoxycarbonyl)amino)methyl)phenyl)-5,7-dihydrofuro[3,4-d]pyrimidine-2-carboxamido)phenyl)acetate (48f) (160 mg, 0.30 mmol) in DCM (5 mL) using TFA (0.23 mL, 3.0 mmol). This gave after workup and purification by flash column chromatography [silica (12 g), eluting with DMA80 in DCM from 0-50%] followed by reverse phase column chromatography [C18 (50 g), eluting with ACN in water (containing 0.1% HCl) from 0-100%] ethyl 2-(2-(4-(3-(aminomethyl)phenyl)-5,7-dihydrofuro[3,4-d]pyrimidine-2-carboxamido)phenyl)acetate (48g) (0.11 g, 85% yield) as a yellow solid; $^1$H NMR (300 MHz, DMSO-$d_6$) δ 10.63 (s, 1H), 8.62 (s, 3H), 8.19 (m, 2H), 7.79-7.71 (m, 2H), 7.66 (t, J=7.6 Hz, 1H), 7.38 (m, 2H), 7.24 (t, J=7.2 Hz, 1H), 5.61 (s, 2H), 5.14 (s, 2H), 4.17 (d, J=5.8 Hz, 2H), 3.98 (q, J=7.0 Hz, 2H), 3.84 (s, 2H), 1.01 (t, J=7.1 Hz, 3H); MS (ES+): 433.3 (M+1), 455.3 (M+Na). HPLC purity: 94.03%.

Step-7: Preparation of 2-(2-(4-(3-(aminomethyl)phenyl)-5,7-dihydrofuro[3,4-d]pyrimidine-2-carboxamido)phenyl)acetic Acid (48h)

Compound 48h was prepared according to the procedure reported in step-4 of Scheme-4 from ethyl 2-(2-(4-(3-(aminomethyl)phenyl)-5,7-dihydrofuro[3,4-d]pyrimidine-2-carboxamido)phenyl)acetate (48g) (50 mg, 0.116 mmol) in MeOH/THF (5 mL, 1:1) using a solution of NaOH (18 mg, 0.462 mmol) in water (2 mL). This gave after workup and purification by reverse phase column chromatography [C18 (50 g), eluting with ACN in water (containing 0.1% HCl) from 0-100%] 2-(2-(4-(3-(aminomethyl)phenyl)-5,7-dihydrofuro[3,4-d]pyrimidine-2-carboxamido)phenyl)acetic acid (48h) (0.016 g, 34% yield) as a yellow solid; $^1$H NMR (300 MHz, DMSO-$d_6$) δ 10.71 (s, 1H), 8.51 (s, 3H), 8.20 (s, 1H), 8.14 (d, J=7.5, Hz, 1H), 7.82 (d, J=7.5, Hz, 1H), 7.78-7.72 (m, 1H), 7.67 (t, J=7.6 Hz, 1H), 7.38 (m, 2H), 7.27-7.18 (m, 1H), 5.60 (s, 2H), 5.15 (s, 2H), 4.18 (q, J=5.8 Hz, 2H), 3.76 (s, 2H); MS (ES+): 405.3 (M+1), 427.3 (M+Na); MS (ES−): 403.3 (M−1), 439.3 (M+Cl). HPLC purity: 96.60%.

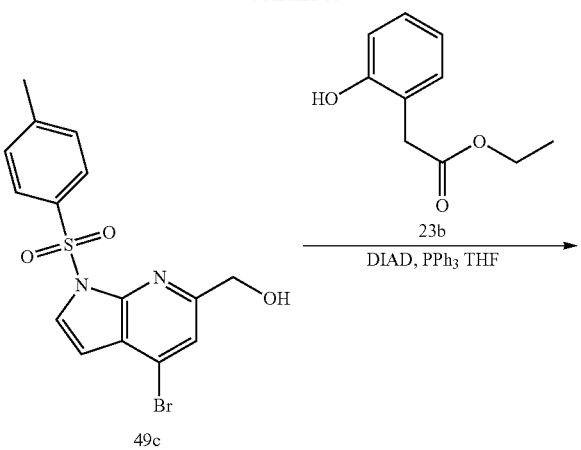

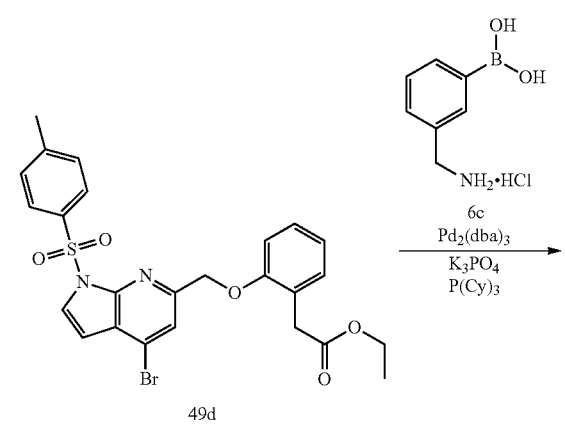

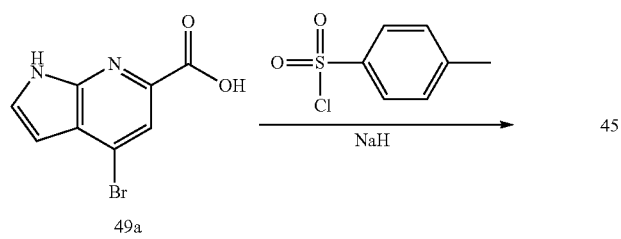

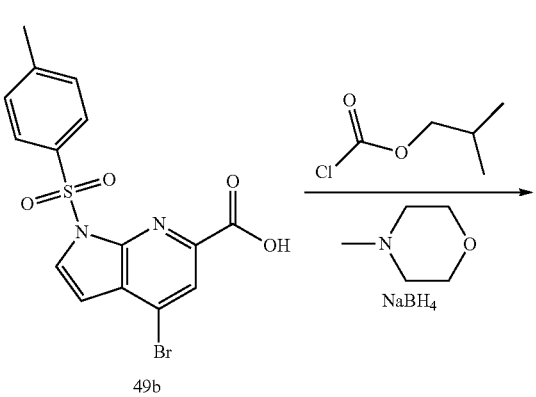

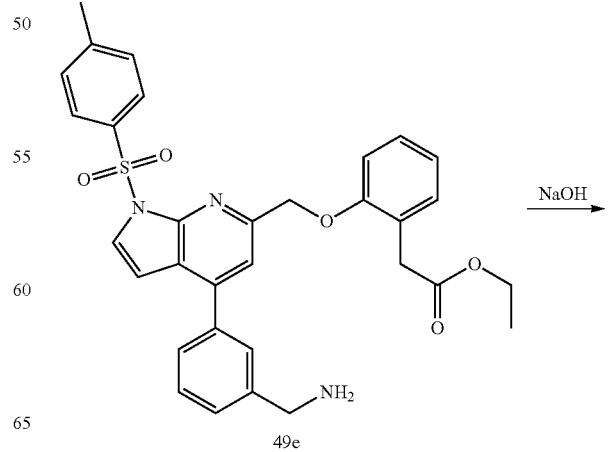

-continued

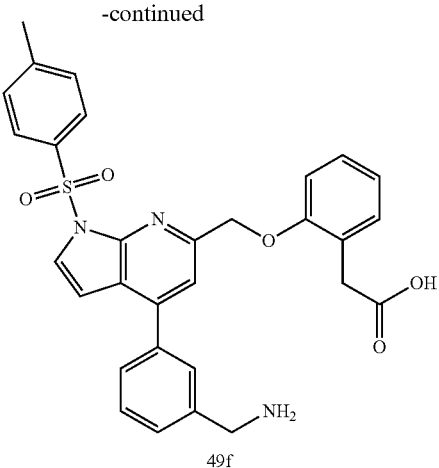

49f

Preparation of 2-(2-((4-(3-(aminomethyl)phenyl)-1-tosyl-1H-pyrrolo[2,3-b]pyridin-6-yl)methoxy)phenyl)acetic Acid (49f)

Step-1: Preparation of 4-bromo-1-tosyl-1H-pyrrolo[2,3-b]pyridine-6-carboxylic Acid (49b)

Compound 49b was prepared according to the procedure reported in step-1 of Scheme-40 from 4-bromo-1H-pyrrolo[2,3-b]pyridine-6-carboxylic acid (49a) (0.7 g, 2.90 mmol; CAS #: 1190321-81-3) in DMF (9.5 mL) using NaH (60% in mineral oil, 0.29 g, 7.26 mmol) and tosyl-Cl (0.66 g, 3.48 mmol). This gave after work up 4-bromo-1-tosyl-1H-pyrrolo[2,3-b]pyridine-6-carboxylic acid (49b) (0.79 g, 69% yield) as a tan solid, which was used in the next step without further purification. MS (ES−): 393.2 & 395.1 (M−1).

Step-2: Preparation of (4-bromo-1-tosyl-1H-pyrrolo[2,3-b]pyridin-6-yl)methanol (49c)

Compound 49c was prepared according to the procedure reported in step-1 of Scheme-23 from 4-bromo-1-tosyl-1H-pyrrolo[2,3-b]pyridine-6-carboxylic acid (49b) (0.6 g, 1.52 mmol) using N-methylmorpholine (0.20 mL, 1.82 mmol) in THF (30 mL), isobutyl chloroformate (0.24 mL, 1.82 mmol) and NaBH$_4$ (0.17 g, 4.55 mmol) in water (0.8 mL). This gave after workup (4-bromo-1-tosyl-1H-pyrrolo[2,3-b]pyridin-6-yl)methanol (49c) (0.27 g, 49% yield) as a clear oil. MS (ES+): 382.5 (M+1); MS (ES−): 415.2 & 417.2 (M+Cl).

Step-3: Preparation of Ethyl 2-(2-((4-bromo-1-tosyl-1H-pyrrolo[2,3-b]pyridin-6-yl)methoxy)phenyl)acetate (49d)

Compound 49d was prepared according to the procedure reported in step-2 of Scheme-23 from (4-bromo-1-tosyl-1H-pyrrolo[2,3-b]pyridin-6-yl)methanol (49c) (0.28 g, 0.73 mmol) in THF (15 mL) using triphenylphosphine (0.25 g, 0.96 mmol), ethyl 2-(2-hydroxyphenyl) acetate (23b) (0.17 g, 0.96 mmol) and DIAD (0.19 mL, 0.96 mmol). This gave after workup and purification by flash column chromatography [silica (12 g), eluting with EtOAc in hexane from 0-60%] ethyl 2-(2-((4-bromo-1-tosyl-1H-pyrrolo[2,3-b]pyridin-6-yl)methoxy)phenyl)acetate (49d) (0.31 g, 78% yield) as colorless oil. MS (ES+): 543.1 & 545.2 (M+1).

Step-4: Preparation of Ethyl 2-(2-((4-(3-(aminomethyl)phenyl)-1-tosyl-1H-pyrrolo[2,3-b]pyridin-6-yl)methoxy)phenyl)acetate (49e)

Compound 49e was prepared according to the procedure reported in step-3 of Scheme-1 from ethyl 2-(2-((4-bromo-1-tosyl-1H-pyrrolo[2,3-b]pyridin-6-yl)methoxy)phenyl)acetate (49d) (0.2 g, 0.368 mmol) in dioxane (3 mL) using 3-(aminomethyl)phenylboronic acid hydrochloride (6c) (0.103 g, 0.552 mmol), tripotassium phosphate (1.3 M solution, 0.849 mL, 1.104 mmol), tricyclohexylphosphine (0.031 g, 0.11 mmol) and Pd$_2$(dba)$_3$ (0.034 g, 0.037 mmol) under an Ar atmosphere and heating at 125° C. for 30 min in a microwave. This gave after workup, purification by flash column chromatography [silica (12 g), eluting with DMA80 in DCM from 0-60%] followed by purification by reverse phase column [C18 (50 g), eluting with ACN in water (containing 0.1% HCl) from 0-100%] ethyl 2-(2-((4-(3-(aminomethyl)phenyl)-1-tosyl-1H-pyrrolo[2,3-b]pyridin-6-yl)methoxy)phenyl)acetate (49e) (0.152 g, 73% yield) as a white solid; $^1$H NMR (300 MHz, DMSO-d$_6$) δ 8.51 (s, 3H), 8.16-8.05 (m, 2H), 8.00 (d, J=4.1 Hz, 1H), 7.84 (s, 1H), 7.73-7.65 (m, 1H), 7.61 (m, 2H), 7.54 (s, 1H), 7.42 (d, J=8.0 Hz, 2H), 7.29-7.14 (m, 2H), 7.11 (d, J=4.1 Hz, 1H), 7.03 (d, J=8.1 Hz, 1H), 6.92 (t, J=7.4 Hz, 1H), 5.35 (s, 2H), 4.11 (q, J=5.9 Hz, 2H), 3.88 (q, J=7.1 Hz, 2H), 3.69 (s, 2H), 2.36 (s, 3H), 0.91 (t, J=7.1 Hz, 3H); MS (ES+): 570.4 (M+1), 592.3 (M+Na); MS (ES−): 604.4 (M+Cl). HPLC purity: 90.90%.

Step-5: Preparation of 2-(2-((4-(3-(aminomethyl)phenyl)-1-tosyl-1H-pyrrolo[2,3-b]pyridin-6-yl)methoxy)phenyl)acetic Acid (49f)

Compound 49f was prepared according to the procedure reported in step-4 of Scheme-4, from ethyl 2-(2-((4-(3-(aminomethyl)phenyl)-1-tosyl-1H-pyrrolo[2,3-b]pyridin-6-yl)methoxy)phenyl)acetate (49e) (0.05 g, 0.088 mmol) in MeOH/THF (5 mL, 1:1) using a solution of sodium hydroxide (4 mg, 0.088 mmol) in water (1 mL). This gave after workup and purification by reverse phase column [C18 (50 g), eluting with ACN in water (containing 0.1% HCl) from 0-100%] 2-(2-((4-(3-(aminomethyl)phenyl)-1-tosyl-1H-pyrrolo[2,3-b]pyridin-6-yl)methoxy)phenyl)acetic acid (49f) (0.01 g, 21% yield) as a white solid; $^1$H NMR (300 MHz, DMSO-d$_6$) δ 12.29 (s, 1H), 8.47 (s, 3H), 8.09 (d, J=8.0 Hz, 2H), 8.00 (d, J=4.1 Hz, 1H), 7.83 (s, 1H), 7.70 (d, J=6.5 Hz, 1H), 7.59 (m, 3H), 7.43 (d, J=8.1 Hz, 2H), 7.24 (d, J=7.3 Hz, 1H), 7.16 (t, J=7.8 Hz, 1H), 7.10 (d, J=4.1 Hz, 1H), 7.00 (d, J=8.2 Hz, 1H), 6.91 (t, J=7.3 Hz, 1H), 5.36 (s, 2H), 4.10 (d, J=5.9 Hz, 2H), 3.64 (s, 2H), 2.35 (s, 3H); MS (ES+): 542.3 (M+1), 564.3 (M+Na); MS (ES−): 576.4 (M+Cl). HPLC purity: 88.38%.

Scheme-50

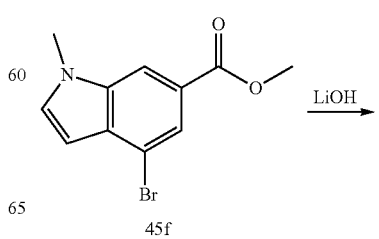

45f

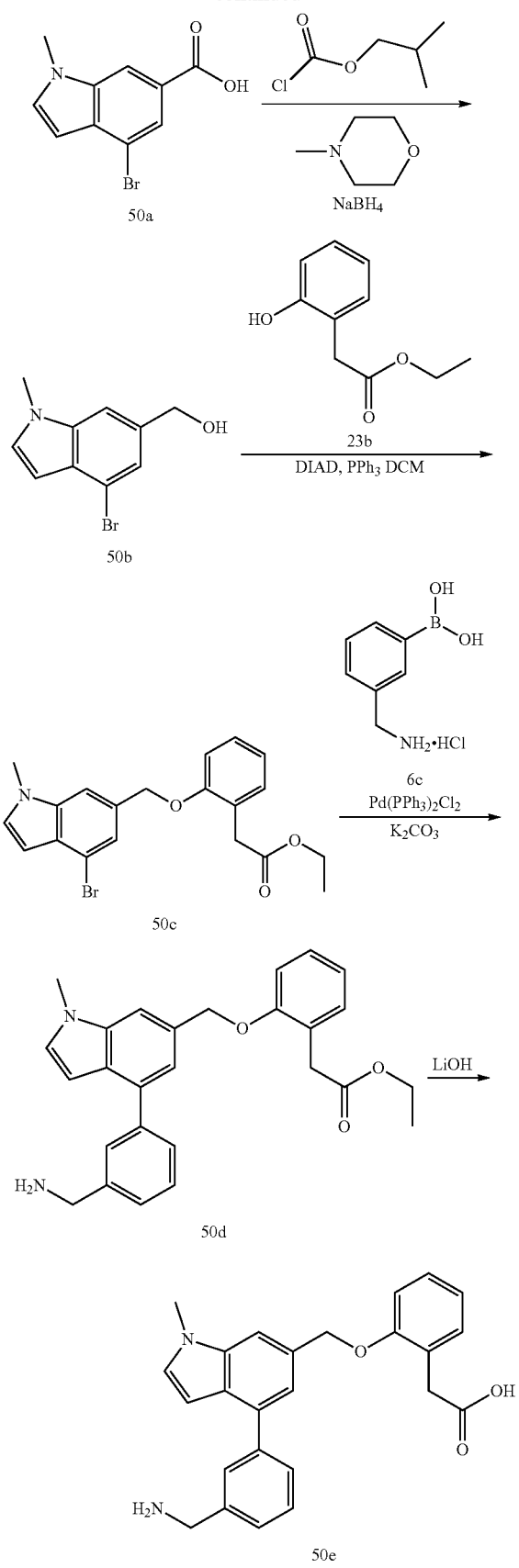

Preparation of 2-(2-((4-(3-(aminomethyl)phenyl)-1-methyl-1H-indol-6-yl)methoxy)phenyl)acetic Acid (50e)

Step-1: Preparation of 4-bromo-1-methyl-1H-indole-6-carboxylic Acid (50a)

Compound 50a was prepared according to the procedure reported in step-6 of Scheme-1, from methyl 4-bromo-1-methyl-1H-indole-6-carboxylate (45f) (3 g, 11.19 mmol) in THF/MeOH (30 mL) using a solution of lithium hydroxide hydrate (2.82 g, 67.1 mmol) in water (3 mL). This gave after workup 4-bromo-1-methyl-1H-indole-6-carboxylic acid (50a) (2.2 g, 77% yield) as a white solid; $^1$H NMR (300 MHz, DMSO-$d_6$) δ 12.96 (s, 1H), 8.10 (s, 1H), 7.78 (s, 1H), 7.69 (d, J=3.1 Hz, 1H), 6.52-6.42 (m, 1H), 3.89 (s, 3H). MS (ES−): 252.1 (M−1).

Step-2: Preparation of (4-bromo-1-methyl-1H-indol-6-yl)methanol (50b)

Compound 50b was prepared according to the procedure reported in step-1 of Scheme-23 from 4-bromo-1-methyl-1H-indole-6-carboxylic acid (50a) (3.7 g, 14.56 mmol) using N-methylmorpholine (1.92 mL, 17.47 mmol) in THF (100 mL), isobutyl chloroformate (2.30 mL, 17.47 mmol) and NaBH$_4$ (1.65 g, 43.7 mmol) in water. This gave after workup and purification by flash column chromatography [silica (24 g), eluting with EtOAc/MeOH=9:1 in Hexane from 0-100%] (4-bromo-1-methyl-1H-indol-6-yl)methanol (50b) (2.1 g, 60% yield) as a yellow solid; $^1$H NMR (300 MHz, DMSO-$d_6$) δ 7.41 (d, J=3.2 Hz, 2H), 7.22 (s, 1H), 6.34 (dd, J=3.1, 0.9 Hz, 1H), 5.27 (t, J=5.8 Hz, 1H), 4.59 (d, J=5.7 Hz, 2H), 3.79 (s, 3H).

Step-3: Preparation of Ethyl 2-(2-((4-bromo-1-methyl-1H-indol-6-yl)methoxy)phenyl)acetate (50c)

Compound 50c was prepared according to the procedure reported in step-2 of Scheme-23 from (4-bromo-1-methyl-1H-indol-6-yl)methanol (50b) (1 g, 4.16 mmol) in DCM (50 mL) using triphenylphosphine (1.42 g, 5.41 mmol), ethyl 2-(2-hydroxyphenyl) acetate (23b) (0.98 g, 5.41 mmol) and di-(4-chlorobenzyl)azodicarboxylate (DCAD, 1.99 g, 5.41 mmol). This gave after workup and purification by flash column chromatography [silica (12 g), eluting with EtOAc/MeOH (9:1) in hexane from 0-60%] ethyl 2-(2-((4-bromo-1-methyl-1H-indol-6-yl)methoxy)phenyl)acetate (50c) (0.66 g, 39% yield) as a colorless oil; MS (ES+): 424.2 & 426.1 (M+Na).

Step-4: Preparation of Ethyl 2-(2-((4-(3-(aminomethyl)phenyl)-1-methyl-1H-indol-6-yl)methoxy)phenyl)acetate (50d)

Compound 50d was prepared according to the procedure reported in step-3 of Scheme-1 from ethyl 2-(2-((4-bromo-1-methyl-1H-indol-6-yl)methoxy)phenyl)acetate (50c) (0.65 g, 1.62 mmol) in dioxane (15 mL) using 3-(aminomethyl)phenylboronic acid hydrochloride (6c) (0.45 g, 2.42 mmol), K$_2$CO$_3$ (0.67 g, 4.85 mmol) in water (2 mL) and bis(triphenylphosphine)Palladium(II) chloride (0.17 g, 0.24 mmol) under an Ar atmosphere and heating at 100° C. for 2 h in an oil bath. This gave after workup, purification by flash column chromatography [silica (12 g), eluting with DMA80 in DCM from 0-50%] ethyl 2-(2-((4-(3-(aminomethyl)phenyl)-1-methyl-1H-indol-6-yl)methoxy)phenyl)acetate (50d) (0.16 g, 23% yield) as a white solid; MS (ES+): 429.3 (M+1).

Step-5: Preparation of 2-(2-((4-(3-(aminomethyl) phenyl)-1-methyl-1H-indol-6-yl)methoxy)phenyl) acetic Acid (50e)

Compound 50e was prepared according to the procedure reported in step-6 of Scheme-1, from ethyl 2-(2-((4-(3-(aminomethyl)phenyl)-1-methyl-1H-indol-6-yl)methoxy) phenyl)acetate (50d) (0.16 g, 0.373 mmol) in THF/MeOH (8 mL) using a solution of lithium hydroxide hydrate (0.078 g, 1.867 mmol) in water (2 mL). This gave after workup and purification by reverse phase column [C18 (50 g), eluting with ACN in water (containing 0.1% HCl) from 0-100%] 2-(2-((4-(3-(aminomethyl)phenyl)-1-methyl-1H-indol-6-yl) methoxy)phenyl)acetic acid (50e) (0.045 g, 30% yield) as a white solid; $^1$H NMR (300 MHz, DMSO-$d_6$) δ 8.34 (s, 3H), 7.81 (s, 1H), 7.72-7.65 (m, 1H), 7.59 (m, 2H), 7.54 (d, J=7.6 Hz, 1H), 7.51-7.46 (m, 1H), 7.45 (d, J=3.1 Hz, 1H), 7.27-7.22 (m, 2H), 7.21 (s, 1H), 7.11 (d, J=8.1 Hz, 1H), 6.93-6.86 (m, 1H), 6.64 (d, J=3.2 Hz, 1H), 5.28 (s, 2H), 4.13 (s, 2H), 3.84 (s, 3H), 3.60 (s, 2H); MS (ES+): 401.3 (M+1), 423.3 (M+Na); MS (ES−): 399.3 (M−1), 435.3 (M+Cl). HPLC purity: 98.50%.

Scheme-51

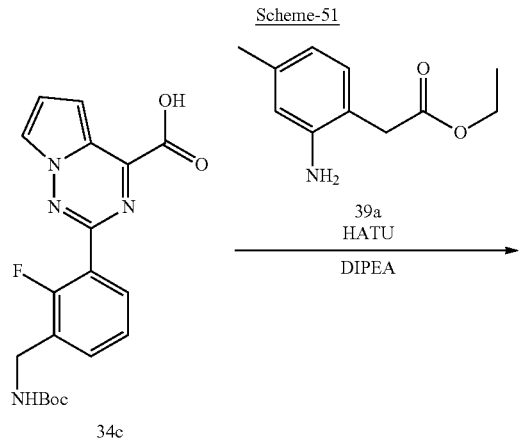

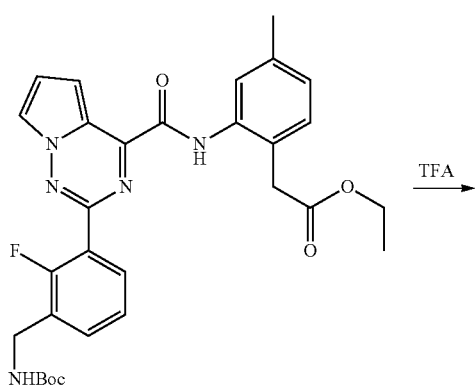

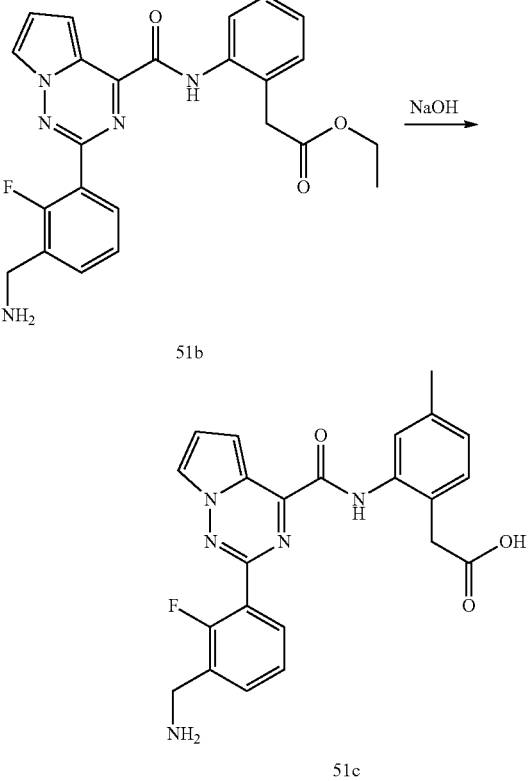

Preparation of 2-(2-(2-(3-(aminomethyl)-2-fluorophenyl)pyrrolo[2,1-f][1,2,4]triazine-4-carboxamido)-4-methylphenyl)acetic Acid (51c)

Step-1: Preparation of Ethyl 2-(2-(2-(3-(((tert-butoxycarbonyl)amino)methyl)-2-fluorophenyl)pyrrolo [2,1-f][1,2,4]triazine-4-carboxamido)-4-methylphenyl)acetate (51a)

Compound 51a was prepared according to the procedure reported in step-4 of Scheme-1 from 2-(3-(((tert-butoxycarbonyl)amino)methyl)-2-fluorophenyl)pyrrolo[2,1-f][1,2,4]triazine-4-carboxylic acid (34c) (0.1 g, 0.259 mmol) in DMF (3 mL) using ethyl 2-(2-amino-4-methylphenyl)acetate (39a) (118 mg, 0.611 mmol), DIPEA (0.136 mL, 0.776 mmol) and HATU (118 mg, 0.311 mmol). This gave after workup and purification by flash column chromatography [silica (12 g), eluting with 0-60% EtOAc in hexane] ethyl 2-(2-(2-(3-(((tert-butoxycarbonyl)amino)methyl)-2-fluorophenyl)pyrrolo[2,1-f][1,2,4]triazine-4-carboxamido)-4-methylphenyl)acetate (51a) (0.1 g, 69% yield) as an orange colored foam; $^1$HNMR (300 MHz, DMSO-$d_6$) δ 10.63 (s, 1H), 8.40 (d, J=2.6 Hz, 1H), 8.26-8.17 (m, 1H), 7.65-7.61 (m, 1H), 7.59 (d, J=4.6 Hz, 1H), 7.56-7.43 (m, 2H), 7.36 (t, J=7.7 Hz, 1H), 7.31-7.23 (m, 2H), 7.07 (dd, J=7.8, 1.8 Hz, 1H), 4.28 (d, J=6.1 Hz, 2H), 3.95 (q, J=7.1 Hz, 2H), 3.77 (s, 2H), 2.35 (s, 3H), 1.40 (s, 9H), 0.97 (t, J=7.1 Hz, 3H).

Step-2: Preparation of Ethyl 2-(2-(2-(3-(aminomethyl)-2-fluorophenyl)pyrrolo[2,1-f][1,2,4]triazine-4-carboxamido)-4-methylphenyl)acetate (51b)

Compound 51b was prepared according to the procedure reported in step-5 of Scheme-1 from ethyl 2-(2-(2-(3-(((tert-butoxycarbonyl)amino)methyl)-2-fluorophenyl)pyrrolo[2,1-f][1,2,4]triazine-4-carboxamido)-4-methylphenyl)acetate (51a) (0.1 g, 0.178 mmol) in DCM (3 mL) using TFA (0.137 mL, 1.78 mmol). This gave after workup and purification by reverse phase column chromatography [C18 (30 g), eluting with ACN in water (containing 0.1% HCl) from 0-100%] ethyl 2-(2-(2-(3-(aminomethyl)-2-fluorophenyl)pyrrolo[2,1-f][1,2,4]triazine-4-carboxamido)-4-methylphenyl)acetate (51b) (0.028 g, 34% yield) as a HCl salt; $^1$H NMR (300 MHz, DMSO-d$_6$) δ 10.67 (s, 1H), 8.52-8.32 (m, 5H), 7.75 (t, J=7.1 Hz, 1H), 7.63-7.58 (m, 2H), 7.47 (t, J=7.8 Hz, 1H), 7.32 (dd, J=4.6, 2.5 Hz, 1H), 7.27 (d, J=7.8 Hz, 1H), 7.08 (d, J=7.6 Hz, 1H), 4.20 (s, 2H), 3.96 (q, J=7.1 Hz, 2H), 3.78 (s, 2H), 2.35 (s, 3H), 0.99 (t, J=7.1 Hz, 3H); $^{19}$F NMR (282 MHz, DMSO-d$_6$) δ −116.69; MS (ES+): 462.3 (M+1), 484.3 (M+Na); MS (ES−): 460.4 (M−1), 496.4 (M+Cl); HPLC purity 99.65%

Step-3: Preparation of 2-(2-(2-(3-(aminomethyl)-2-fluorophenyl)pyrrolo[2,1-f][1,2,4]triazine-4-carboxamido)-4-methylphenyl)acetic Acid (51c)

Compound 51c was prepared according to the procedure reported in step-4 of Scheme-4 from ethyl 2-(2-(2-(3-(aminomethyl)-2-fluorophenyl)pyrrolo[2,1-f][1,2,4]triazine-4-carboxamido)-4-methylphenyl)acetate (51b) (0.07 g, 0.152 mmol) in THF (4 mL) using sodium hydroxide (0.152 mL, 0.303 mmol, 2 M aqueous). This gave after workup and purification by reverse phase column [C18 (30 g), eluting with ACN in water (containing 0.1% HCl) from 0-100%] 2-(2-(2-(3-(aminomethyl)-2-fluorophenyl)pyrrolo[2,1-f][1,2,4]triazine-4-carboxamido)-4-methylphenyl)acetic acid (51c) (0.025 g, 38.0% yield) as a HCl salt; $^1$H NMR (300 MHz, DMSO-d$_6$) δ 12.71 (s, 1H), 10.74 (s, 1H), 8.52-8.31 (m, 4H), 7.81-7.67 (m, 3H), 7.63 (dd, J=4.7, 1.4 Hz, 1H), 7.47 (t, J=7.8 Hz, 1H), 7.32 (dd, J=4.6, 2.5 Hz, 1H), 7.26 (d, J=7.8 Hz, 1H), 7.06 (dd, J=7.8, 1.7 Hz, 1H), 4.20 (s, 2H), 3.69 (s, 2H), 2.35 (s, 3H); $^{19}$F NMR (282 MHz, DMSO-d$_6$) δ −116.59; MS (ES+): 434.3 (M+1), MS (ES−): 432.3 (M+Cl); HPLC purity 97.76%.

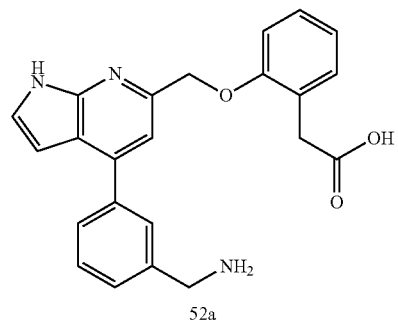

Preparation of 2-(2-((4-(3-(aminomethyl)phenyl)-1H-pyrrolo[2,3-b]pyridin-6-yl)methoxy)phenyl)acetic Acid (52a)

Compound 52a was prepared according to the procedure reported in step-4 of Scheme-4, from ethyl 2-(2-((4-(3-(aminomethyl)phenyl)-1-tosyl-1H-pyrrolo[2,3-b]pyridin-6-yl)methoxy)phenyl)acetate (49e) (0.04 g, 0.070 mmol) in THF (5 mL) using a solution of sodium hydroxide (0.028 g, 0.702 mmol) in water (1 mL). This gave after workup and purification by reverse phase column [C18 (50 g), eluting with ACN in water (containing 0.1% HCl) from 0-100%] 2-(2-((4-(3-(aminomethyl)phenyl)-1H-pyrrolo[2,3-b]pyridin-6-yl)methoxy)phenyl)acetic acid (52a) (0.012 g, 44% yield) as a white solid; $^1$H NMR (300 MHz, DMSO-d$_6$) δ 11.91 (s, 1H), 8.36 (s, 3H), 7.92 (s, 1H), 7.79 (dt, J=6.9, 1.9 Hz, 1H), 7.59 (m, 3H), 7.42 (s, 1H), 7.22 (m, 2H), 7.08 (m, 1H), 6.90 (t, J=7.3 Hz, 1H), 6.76 (m, 1H), 5.28 (s, 2H), 4.15 (d, J=5.8 Hz, 2H), 3.63 (s, 2H); MS (ES+): 388.3 (M+1); MS (ES−): 386.4 (M−1), 422.3 (M+Cl). HPLC purity: 91.49%.

Scheme-52

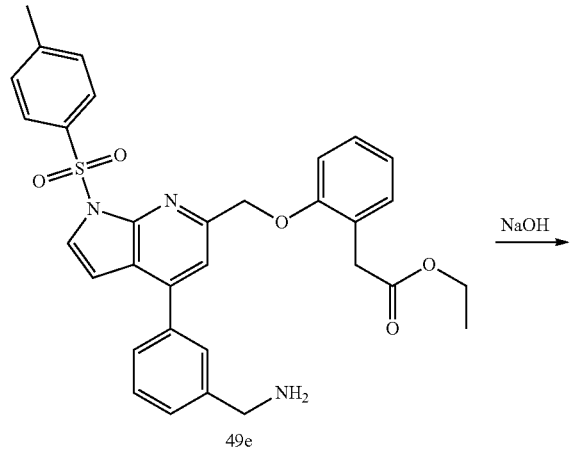

49e

Scheme-53

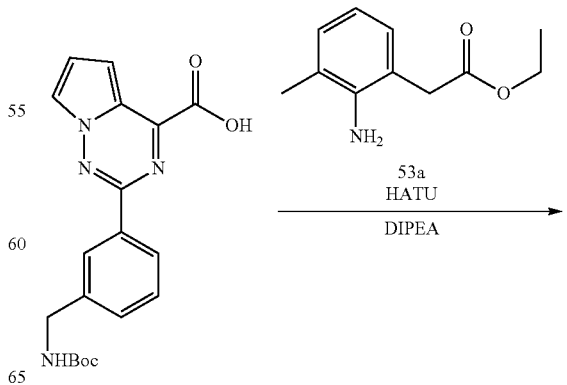

1e

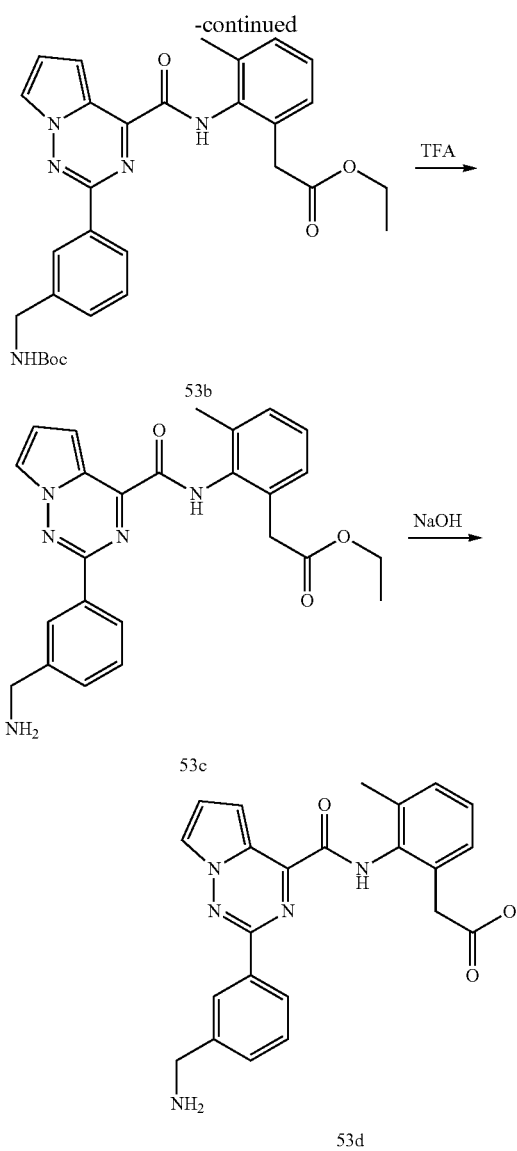

Preparation of 2-(2-(2-(3-(aminomethyl)phenyl)
pyrrolo[2,1-f][1,2,4]triazine-4-carboxamido)-3-
methylphenyl)acetic Acid (53d)

Step-1: Preparation of Ethyl 2-(2-(2-(3-(((tert-butoxycarbonyl)amino)methyl)phenyl)pyrrolo[2,1-f][1,2,4]triazine-4-carboxamido)-3-methylphenyl)acetate (53b)

Compound 53b was prepared according to the procedure reported in step-4 of Scheme-1 from 2-(3-(((tert-butoxycarbonyl)amino)methyl)phenyl)pyrrolo[2,1-f][1,2,4]triazine-4-carboxylic acid (1e) (0.18 g, 0.489 mmol) in DMF (3 mL) using ethyl 2-(2-amino-3-methylphenyl)acetate (53a) (113 mg, 0.586 mmol, CAS #1261751-05-6), DIPEA (0.256 mL, 1.466 mmol) and HATU (223 mg, 0.586 mmol). This gave after workup and purification by flash column chromatography [silica (12 g), eluting with 0-60% EtOAc in hexane] ethyl 2-(2-(2-(3-(((tert-butoxycarbonyl)amino)methyl)phenyl)pyrrolo[2,1-f][1,2,4]triazine-4-carboxamido)-3-methylphenyl)acetate (53b) (0.21 g, 79% yield) as an orange colored foam; $^1$H NMR (300 MHz, DMSO-$d_6$) δ 10.61 (s, 1H), 8.51 (d, J=7.8 Hz, 1H), 8.40 (s, 1H), 8.37-8.32 (m, 1H), 7.56-7.47 (m, 3H), 7.43 (d, J=7.6 Hz, 1H), 7.32-7.20 (m, 4H), 4.26 (d, J=6.2 Hz, 2H), 3.91 (q, J=7.1 Hz, 2H), 3.74 (s, 2H), 2.29 (s, 3H), 1.41 (s, 9H), 0.89 (t, J=7.1 Hz, 3H).

Step-2: Preparation of Ethyl 2-(2-(2-(3-(aminomethyl)phenyl)pyrrolo[2,1-f][1,2,4]triazine-4-carboxamido)-3-methylphenyl)acetate (53c)

Compound 53c was prepared according to the procedure reported in step-5 of Scheme-1 from ethyl 2-(2-(2-(3-(((tert-butoxycarbonyl)amino)methyl)phenyl)pyrrolo[2,1-f][1,2,4]triazine-4-carboxamido)-3-methylphenyl)acetate (53b) (200 mg, 0.368 mmol) in DCM (5 mL) using TFA (0.283 mL, 3.68 mmol). This gave after workup and purification by reverse phase column chromatography [C18 (30 g), eluting with ACN in water (containing 0.1% HCl) from 0-100%] ethyl 2-(2-(2-(3-(aminomethyl)phenyl)pyrrolo[2,1-f][1,2,4]triazine-4-carboxamido)-3-methylphenyl)acetate (53c) (0.035 g, 22% yield) as a HCl salt; 1H NMR (300 MHz, DMSO-$d_6$) δ 10.65 (s, 1H), 8.69 (d, J=1.8 Hz, 1H), 8.67-8.60 (m, 1H), 8.47 (s, 4H), 8.36 (dt, J=2.9, 1.5 Hz, 1H), 7.73-7.58 (m, 2H), 7.54 (dd, J=4.6, 1.4 Hz, 1H), 7.32-7.22 (m, 3H), 4.23-4.10 (m, 2H), 3.95-3.84 (m, 2H), 3.74 (s, 2H), 2.29 (s, 3H), 0.93-0.84 (m, 3H).

Step-3: Preparation of 2-(2-(2-(3-(aminomethyl)phenyl)pyrrolo[2,1-f][1,2,4]triazine-4-carboxamido)-3-methylphenyl)acetic Acid (53d)

Compound 53d was prepared according to the procedure reported in step-4 of Scheme-4 from ethyl 2-(2-(2-(3-(aminomethyl)phenyl)pyrrolo[2,1-f][1,2,4]triazine-4-carboxamido)-3-methylphenyl)acetate (53c) (0.12 g, 0.271 mmol) in THF (4 mL) using sodium hydroxide (0.135 mL, 0.271 mmol, 2 M aqueous). This gave after workup and purification by reverse phase column [C18 (30 g), eluting with ACN in water (containing 0.1% HCl) from 0-100%] 2-(2-(2-(3-(aminomethyl)phenyl)pyrrolo[2,1-f][1,2,4]triazine-4-carboxamido)-3-methylphenyl)acetic acid (53d) (0.07 g, 0.168 mmol, 62.3% yield) as a HCl salt; $^1$H NMR (300 MHz, DMSO-$d_6$) δ 12.42 (s, 1H), 10.64 (s, 1H), 8.67-8.56 (m, 2H), 8.44-8.28 (m, 4H), 7.71-7.58 (m, 2H), 7.55 (dd, J=4.6, 1.4 Hz, 1H), 7.31-7.23 (m, 4H), 4.23-4.13 (m, 2H), 3.68 (s, 2H), 2.29 (s, 3H). MS (ES+) 416.3 (M+1), MS (ES−) 414.4 (M−1); HPLC purity 98.00%.

Scheme-54

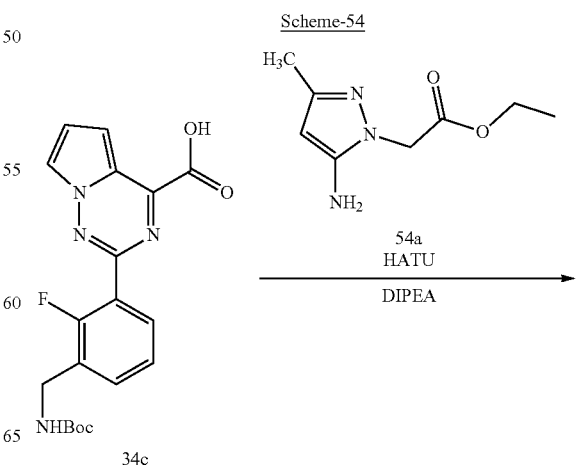

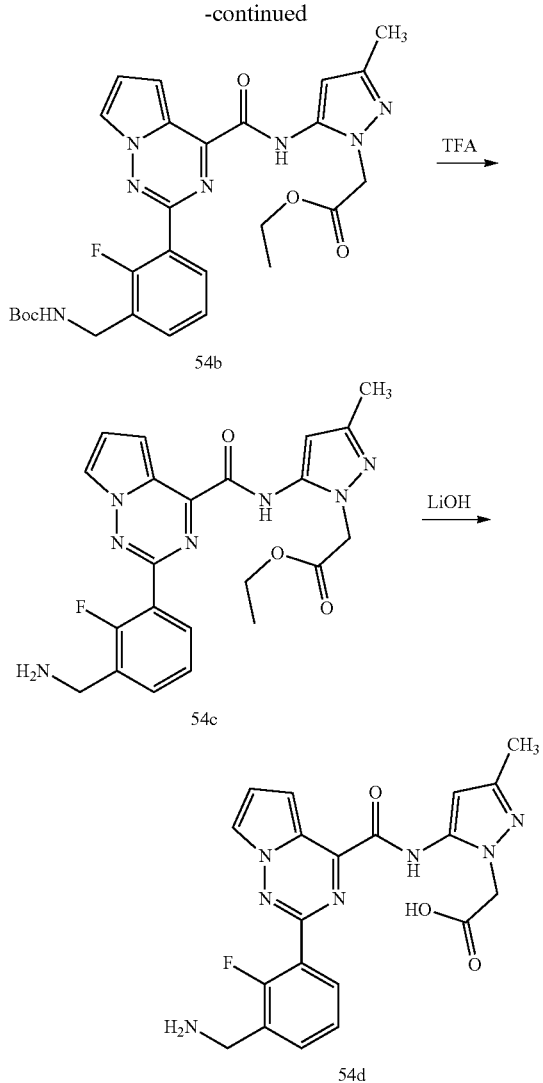

Preparation of 2-(5-(2-(3-(aminomethyl)-2-fluorophenyl)pyrrolo[2,1-f][1,2,4]triazine-4-carboxamido)-3-methyl-1H-pyrazol-1-yl)acetic Acid (54d)

Step-1: Preparation of Ethyl 2-(5-(2-(3-(((tert-butoxycarbonyl)amino)methyl)-2-fluorophenyl)pyrrolo[2,1-f][1,2,4]triazine-4-carboxamido)-3-methyl-1H-pyrazol-1-yl)acetate (54b)

Compound 54b was prepared according to the procedure reported in step-4 of Scheme-1 from 2-(3-(((tert-butoxycarbonyl)amino)methyl)-2-fluorophenyl)pyrrolo[2,1-f][1,2,4]triazine-4-carboxylic acid (34c) (150 mg, 0.388 mmol) in DMF (10 mL) using ethyl 2-(5-amino-3-methyl-1H-pyrazol-1-yl)acetate (54a) (75 mg, 0.388 mmol; CAS #956440-82-7), DIPEA (0.203 mL, 1.165 mmol) and HATU (221 mg, 0.582 mmol). This gave after workup and purification by flash column chromatography [silica (12 g), eluting with DCM/methanol (1:0 to 19:1)] ethyl 2-(5-(2-(3-(((tert-butoxycarbonyl)amino)methyl)-2-fluorophenyl)pyrrolo[2,1-f][1,2,4]triazine-4-carboxamido)-3-methyl-1H-pyrazol-1-yl)acetate (54b) (0.19 g, 89% yield) as a brown solid; $^1$H NMR (300 MHz, DMSO-$d_6$) δ 10.85 (s, 1H), 8.40 (s, 1H), 8.26-8.15 (m, 1H), 7.57-7.42 (m, 3H), 7.36 (t, J=7.7 Hz, 1H), 7.32-7.24 (m, 1H), 6.29 (s, 1H), 5.01 (s, 2H), 4.28 (d, J=6.3 Hz, 2H), 4.08 (q, J=7.1 Hz, 2H), 2.17 (s, 3H), 1.40 (s, 9H), 1.11 (t, J=7.1 Hz, 3H); $^{19}$F NMR (282 MHz, DMSO-$d_6$) δ−119.39; MS (ES+) 552.3 (M+1); (ES−) 550.4 (M−1).

Step-2: Preparation of Ethyl 2-(5-(2-(3-(aminomethyl)-2-fluorophenyl)pyrrolo[2,1-f][1,2,4]triazine-4-carboxamido)-3-methyl-1H-pyrazol-1-yl)acetate (54c)

Compound 54c was prepared according to the procedure reported in step-5 of Scheme-1 from ethyl 2-(5-(2-(3-(((tert-butoxycarbonyl)amino)methyl)-2-fluorophenyl)pyrrolo[2,1-f][1,2,4]triazine-4-carboxamido)-3-methyl-1H-pyrazol-1-yl)acetate (54b) (0.18 g, 0.326 mmol) in DCM (15 mL) using TFA (1.01 mL, 13.05 mmol). This gave after workup and purification by flash column chromatography [silica (12 g), eluting with DCM/methanol (1:0 to 9:1)] ethyl 2-(5-(2-(3-(aminomethyl)-2-fluorophenyl)pyrrolo[2,1-f][1,2,4]triazine-4-carboxamido)-3-methyl-1H-pyrazol-1-yl)acetate (54c) (0.14 g, 95% yield) as a yellow solid; $^1$H NMR (300 MHz, DMSO-$d_6$) δ 10.87 (s, 1H), 8.52-8.42 (m, 1H), 8.38 (d, J=2.6 Hz, 1H), 8.29 (s, 3H), 7.77-7.67 (m, 1H), 7.52-7.44 (m, 2H), 7.32 (dd, J=4.6, 2.6 Hz, 1H), 6.29 (s, 1H), 5.01 (s, 2H), 4.22 (s, 2H), 4.09 (q, J=7.0 Hz, 2H), 2.18 (s, 3H), 1.11 (t, J=7.1 Hz, 3H); $^{19}$F NMR (282 MHz, DMSO-$d_6$) δ−116.54; MS (ES+): 452.3 (M+1), 474.3 (M+Na); MS (ES−): 450.4 (M−1).

Step-3: Preparation of 2-(5-(2-(3-(aminomethyl)-2-fluorophenyl)pyrrolo[2,1-f][1,2,4]triazine-4-carboxamido)-3-methyl-1H-pyrazol-1-yl)acetic Acid (54d)

Compound 54d was prepared according to the procedure reported in step-6 of Scheme-1 from ethyl 2-(5-(2-(3-(aminomethyl)-2-fluorophenyl)pyrrolo[2,1-f][1,2,4]triazine-4-carboxamido)-3-methyl-1H-pyrazol-1-yl)acetate (54c) (0.129 g, 0.286 mmol) in THF/MeOH (20 mL, 1:1) using lithium hydroxide hydrate (73.4 mg, 1.714 mmol) in water (10 mL). This gave after workup and purification by reverse phase column [C18 (30 g), eluting with ACN in water (containing 0.1% HCl) from 0-100%] 2-(5-(2-(3-(aminomethyl)-2-fluorophenyl)pyrrolo[2,1-f][1,2,4]triazine-4-carboxamido)-3-methyl-1H-pyrazol-1-yl)acetic acid (54d) (47 mg, 39% yield) as a white solid; $^1$H NMR (300 MHz, DMSO-$d_6$) δ 11.63 (s, 1H), 8.80 (s, 3H), 8.49-8.39 (m, 1H), 8.16 (t, J=7.3 Hz, 1H), 7.71 (t, J=7.0 Hz, 1H), 7.61-7.55 (m, 1H), 7.43 (t, J=7.7 Hz, 1H), 7.32 (dd, J=4.6, 2.6 Hz, 1H), 6.30 (s, 1H), 4.66 (s, 2H), 4.14 (s, 2H), 2.15 (s, 3H); $^{19}$F NMR (282 MHz, DMSO-$d_6$) δ−115.10; MS (ES−): 422.4 (M−1).

Scheme-55

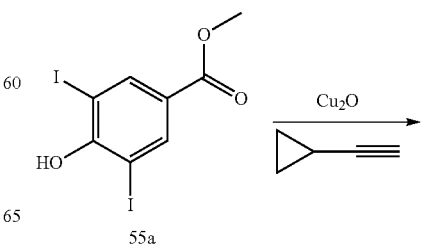

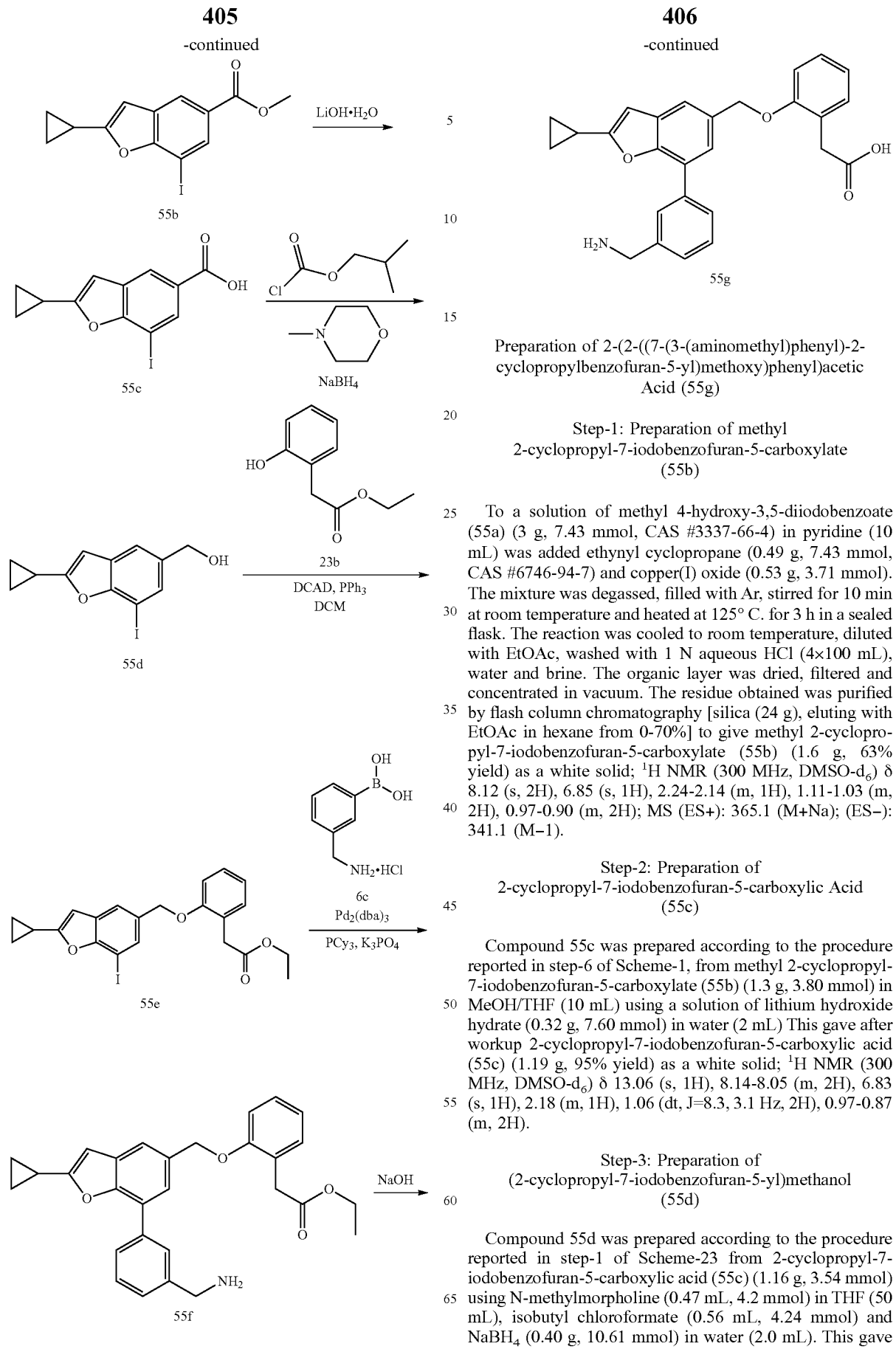

Preparation of 2-(2-((7-(3-(aminomethyl)phenyl)-2-cyclopropylbenzofuran-5-yl)methoxy)phenyl)acetic Acid (55g)

Step-1: Preparation of methyl 2-cyclopropyl-7-iodobenzofuran-5-carboxylate (55b)

To a solution of methyl 4-hydroxy-3,5-diiodobenzoate (55a) (3 g, 7.43 mmol, CAS #3337-66-4) in pyridine (10 mL) was added ethynyl cyclopropane (0.49 g, 7.43 mmol, CAS #6746-94-7) and copper(I) oxide (0.53 g, 3.71 mmol). The mixture was degassed, filled with Ar, stirred for 10 min at room temperature and heated at 125° C. for 3 h in a sealed flask. The reaction was cooled to room temperature, diluted with EtOAc, washed with 1 N aqueous HCl (4×100 mL), water and brine. The organic layer was dried, filtered and concentrated in vacuum. The residue obtained was purified by flash column chromatography [silica (24 g), eluting with EtOAc in hexane from 0-70%] to give methyl 2-cyclopropyl-7-iodobenzofuran-5-carboxylate (55b) (1.6 g, 63% yield) as a white solid; $^1$H NMR (300 MHz, DMSO-$d_6$) δ 8.12 (s, 2H), 6.85 (s, 1H), 2.24-2.14 (m, 1H), 1.11-1.03 (m, 2H), 0.97-0.90 (m, 2H); MS (ES+): 365.1 (M+Na); (ES−): 341.1 (M−1).

Step-2: Preparation of 2-cyclopropyl-7-iodobenzofuran-5-carboxylic Acid (55c)

Compound 55c was prepared according to the procedure reported in step-6 of Scheme-1, from methyl 2-cyclopropyl-7-iodobenzofuran-5-carboxylate (55b) (1.3 g, 3.80 mmol) in MeOH/THF (10 mL) using a solution of lithium hydroxide hydrate (0.32 g, 7.60 mmol) in water (2 mL) This gave after workup 2-cyclopropyl-7-iodobenzofuran-5-carboxylic acid (55c) (1.19 g, 95% yield) as a white solid; $^1$H NMR (300 MHz, DMSO-$d_6$) δ 13.06 (s, 1H), 8.14-8.05 (m, 2H), 6.83 (s, 1H), 2.18 (m, 1H), 1.06 (dt, J=8.3, 3.1 Hz, 2H), 0.97-0.87 (m, 2H).

Step-3: Preparation of (2-cyclopropyl-7-iodobenzofuran-5-yl)methanol (55d)

Compound 55d was prepared according to the procedure reported in step-1 of Scheme-23 from 2-cyclopropyl-7-iodobenzofuran-5-carboxylic acid (55c) (1.16 g, 3.54 mmol) using N-methylmorpholine (0.47 mL, 4.2 mmol) in THF (50 mL), isobutyl chloroformate (0.56 mL, 4.24 mmol) and NaBH$_4$ (0.40 g, 10.61 mmol) in water (2.0 mL). This gave after workup and purification by flash column chromatography [silica (24 g), eluting with EtOAc in hexane from 0-50%] (2-cyclopropyl-7-iodobenzofuran-5-yl)methanol (55d) (1.02 g, 92% yield) as a clear oil; $^1$H NMR (300 MHz, DMSO-$d_6$) δ 7.52 (d, J=1.5 Hz, 1H), 7.40 (d, J=1.4 Hz, 1H), 6.68 (s, 1H), 5.25 (t, J=5.8 Hz, 1H, $D_2O$ exchangeable), 4.51 (d, J=5.8 Hz, 2H), 2.19-2.07 (m, 1H), 1.09-0.98 (m, 2H), 0.93-0.85 (m, 2H); MS (ES+): 337.3 (M+Na).

Step-4: Preparation of Ethyl 2-(2-((2-cyclopropyl-7-iodobenzofuran-5-yl)methoxy)phenyl)acetate (55e)

Compound 55e was prepared according to the procedure reported in step-2 of Scheme-23 from (2-cyclopropyl-7-iodobenzofuran-5-yl)methanol (55d) (850 mg, 2.71 mmol) in DCM (10 mL) using triphenylphosphine (781 mg, 2.98 mmol), ethyl 2-(2-hydroxyphenyl) acetate (23b) (536 mg, 2.98 mmol) and di-(4-chlorobenzyl)azodicarboxylate (DCAD, 1093 mg, 2.98 mmol). This gave after workup and purification by flash column chromatography [silica (24 g), eluting with EtOAc in hexane from 0-50%] ethyl 2-(2-((2-cyclopropyl-7-iodobenzofuran-5-yl)methoxy)phenyl)acetate (55e) (800 mg, 62% yield) as a clear oil; $^1$H NMR (300 MHz, DMSO-$d_6$) δ 7.62 (d, J=1.5 Hz, 1H), 7.52 (d, J=1.5 Hz, 1H), 7.29-7.18 (m, 2H), 7.05 (d, J=8.1 Hz, 1H), 6.91 (td, J=7.4, 1.0 Hz, 1H), 6.72 (s, 1H), 5.11 (s, 2H), 4.03 (q, J=7.1 Hz, 2H), 3.61 (s, 2H), 2.23-2.05 (m, 1H), 1.14-0.98 (m, 5H), 0.96-0.83 (m, 3H); MS (ES+): 499.1 (M+Na); (ES−): 475.3 (M−1).

Step-5: Preparation of Ethyl 2-(2-((7-(3-(aminomethyl)phenyl)-2-cyclopropylbenzofuran-5-yl)methoxy)phenyl)acetate (55f)

Compound 55f was prepared according to the procedure reported in step-3 of Scheme-1 from ethyl 2-(2-((2-cyclopropyl-7-iodobenzofuran-5-yl)methoxy)phenyl)acetate (55e) (250 mg, 0.53 mmol) in dioxane (3 mL) using 3-(aminomethyl)phenylboronic acid hydrochloride (6c) (148 mg, 0.787 mmol), tripotassium phosphate (3 M aqueous solution, 0.30 mL, 0.89 mmol), tricyclohexylphosphine (44.2 mg, 0.16 mmol) and $Pd_2(dba)_3$ (48 mg, 0.052 mmol) under an Ar atmosphere and heating at 125° C. for 45 min in a microwave. This gave after workup, purification by flash column chromatography [silica (12 g), eluting with EtOAc/MeOH (9:1, v/v) in hexane from 0-70%] ethyl 2-(2-((7-(3-(aminomethyl)phenyl)-2-cyclopropylbenzofuran-5-yl)methoxy)phenyl)acetate (55f) (120 mg, 32% yield) as a free base. 70 mg of free base was further purified by reverse phase column chromatography [C18 (50 g), eluting with ACN in water (containing 0.1% HCl) from 0-100%] to afford ethyl 2-(2-((7-(3-(aminomethyl)phenyl)-2-cyclopropylbenzofuran-5-yl)methoxy)phenyl)acetate (55f) (25 mg, 30% yield) HCl salt as a white solid; $^1$H NMR (300 MHz, DMSO-$d_6$) δ 8.44 (s, 3H, $D_2O$ exchangeable), 7.95 (s, 1H), 7.92-7.83 (m, 1H), 7.66-7.45 (m, 5H), 7.32-7.17 (m, 2H), 7.15-7.06 (m, 1H), 6.97-6.86 (m, 1H), 6.67 (s, 1H), 5.20 (s, 2H), 4.12 (s, 2H), 3.94 (q, J=7.1 Hz, 2H), 3.62 (s, 2H), 2.22-2.09 (m, 1H), 1.07-0.96 (m, 5H), 0.96-0.90 (m, 2H); MS (ES+): 456.3 (M+1); (ES−): 490.3 (M+Cl).

Step-6: Preparation of 2-(2-((7-(3-(aminomethyl)phenyl)-2-cyclopropylbenzofuran-5-yl)methoxy)phenyl)acetic Acid (55g)

Compound 55g was prepared according to the procedure reported in step-4 of Scheme-4, from ethyl 2-(2-((7-(3-(aminomethyl)phenyl)-2-cyclopropylbenzofuran-5-yl)methoxy)phenyl)acetate (55f) (50 mg, 0.11 mmol) in MeOH/THF (3 mL) using a solution of sodium hydroxide (21.9 mg, 0.55 mmol) in water (1 mL). This gave after workup and purification by reverse phase column [C18 (50 g), eluting with ACN in water (containing 0.1% HCl) from 0-100%]2-(2-((7-(3-(aminomethyl)phenyl)-2-cyclopropylbenzofuran-5-yl)methoxy)phenyl)acetic acid (55g) (21 mg, 45% yield) as a white solid; $^1$H NMR (300 MHz, DMSO-$d_6$) δ 12.27 (s, 1H, $D_2O$ exchangeable), 8.43 (s, 2H, $D_2O$ exchangeable), 7.95 (d, J=1.6 Hz, 1H), 7.90 (dt, J=7.5, 1.6 Hz, 1H), 7.63-7.49 (m, 4H), 7.29-7.17 (m, 2H), 7.08 (d, J=8.1 Hz, 1H), 6.94-6.85 (m, 1H), 6.66 (s, 1H), 5.23 (s, 2H), 4.13 (s, 2H), 3.59 (s, 2H), 2.22-2.12 (m, 1H), 1.10-0.97 (m, 2H), 0.97-0.88 (m, 2H); MS (ES+): 428.3 (M+1); 450.4 (M+Na); (ES−): 426.4 (M−1), 462.3 (M+Cl).

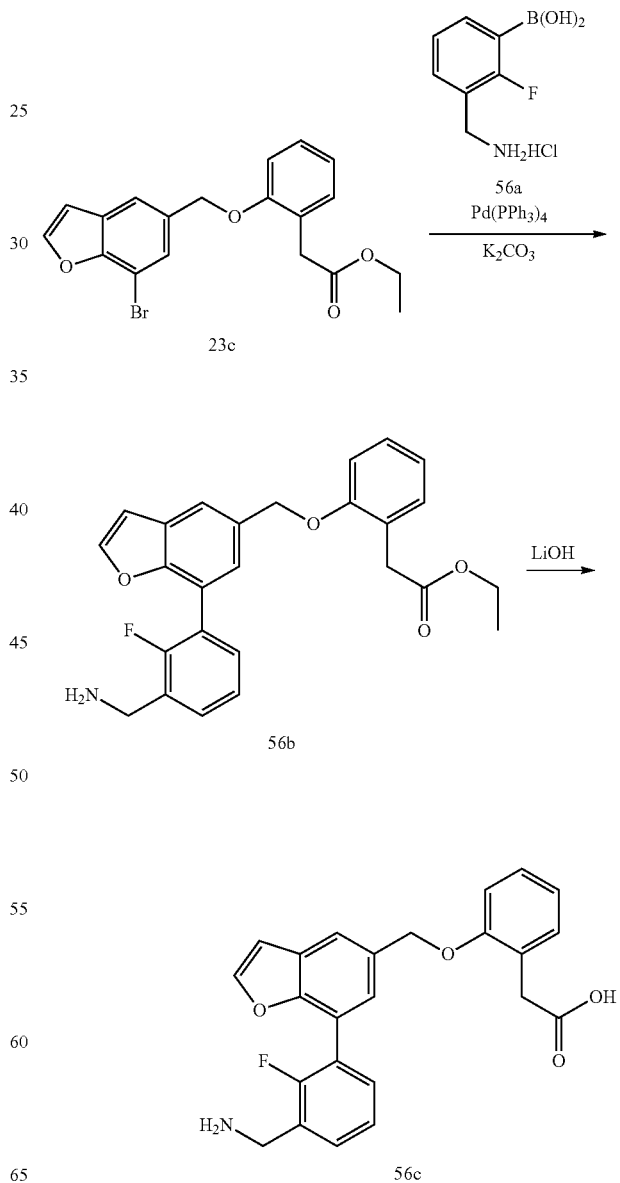

Scheme-56

Preparation of 2-(2-((7-(3-(aminomethyl)-2-fluoro-phenyl)benzofuran-5-yl)methoxy)phenyl)acetic Acid (56c)

Step-1: Preparation of Ethyl 2-(2-((7-(3-(aminomethyl)-2-fluorophenyl)benzofuran-5-yl)methoxy)phenyl)acetate (56b)

Compound 56b was prepared according to the procedure reported in step-3 of Scheme-1 from ethyl 2-(2-((7-bromobenzofuran-5-yl)methoxy)phenyl)acetate (23c) (250 mg, 0.64 mmol) in dioxane (3 mL) using (3-(aminomethyl)-2-fluorophenyl)boronic acid hydrochloride (56a) (198 mg, 0.96 mmol; CAS #1072946-44-1), tetrakis(triphenylphosphine)palladium(0) (148 mg, 0.128 mmol), potassium carbonate (266 mg, 1.93 mmol) in water (1 mL) under an Ar atmosphere and heating at 150° C. for 55 min in a microwave. This gave after workup, purification by flash column chromatography [silica (12 g), eluting with EtOAc/MeOH (9:1, v/v) in hexane from 0-100%] followed by reverse phase column chromatography [C18 (50 g), eluting with ACN in water (containing 0.1% HCl) from 0-100%] ethyl 2-(2-((7-(3-(aminomethyl)-2-fluorophenyl)benzofuran-5-yl)methoxy)phenyl)acetate (56b) (125 mg, 45% yield) as a white solid; $^1$H NMR (300 MHz, DMSO-$d_6$) δ 8.52 (s, 3H, $D_2O$ exchangeable), 8.06 (d, J=2.2 Hz, 1H), 7.79 (d, J=1.6 Hz, 1H), 7.74-7.62 (m, 2H), 7.46-7.39 (m, 2H), 7.30-7.19 (m, 2H), 7.11 (d, J=8.2 Hz, 1H), 7.08 (d, J=2.2 Hz, 1H), 6.91 (td, J=7.4, 1.0 Hz, 1H), 5.24 (s, 2H), 4.17 (s, 2H), 3.92 (q, J=7.1 Hz, 2H), 3.62 (s, 2H), 0.99 (t, J=7.1 Hz, 3H); $^{19}$F NMR (282 MHz, DMSO-$d_6$) δ −118.52; MS (ES+): 434.3 (M+1).

Step-2: Preparation of 2-(2-((7-(3-(aminomethyl)-2-fluorophenyl)benzofuran-5-yl)methoxy)phenyl)acetic Acid (56c)

Compound 56c was prepared according to the procedure reported in step-6 of Scheme-1, from ethyl 2-(2-((7-(3-(aminomethyl)-2-fluorophenyl)benzofuran-5-yl)methoxy)phenyl)acetate (56b) (65 mg, 0.15 mmol) in MeOH/THF (3 mL) using a solution of lithium hydroxide hydrate (25.2 mg, 0.60 mmol) in water (1 mL). This gave after workup and purification by reverse phase column [C18 (50 g), eluting with ACN in water (containing 0.1% HCl) from 0-100%] 2-(2-((7-(3-(aminomethyl)-2-fluorophenyl)benzofuran-5-yl)methoxy)phenyl)acetic acid (56c) (26 mg, 43% yield) as a white solid; $^1$H NMR (300 MHz, DMSO-$d_6$) δ 9.13-8.08 (m, 1H, $D_2O$ exchangeable), 8.06 (d, J=2.2 Hz, 1H), 7.83 (d, J=1.6 Hz, 1H), 7.73-7.61 (m, 2H), 7.50-7.39 (m, 2H), 7.28-7.18 (m, 2H), 7.12-7.02 (m, 2H), 6.90 (t, J=7.4 Hz, 1H), 5.26 (s, 2H), 4.18 (s, 2H), 3.58 (s, 2H); MS (ES+): 406.3 (M+1); 428.3 (M+Na); (ES−): 404.4 (M−1), 440.3 (M+Cl).

Scheme-57

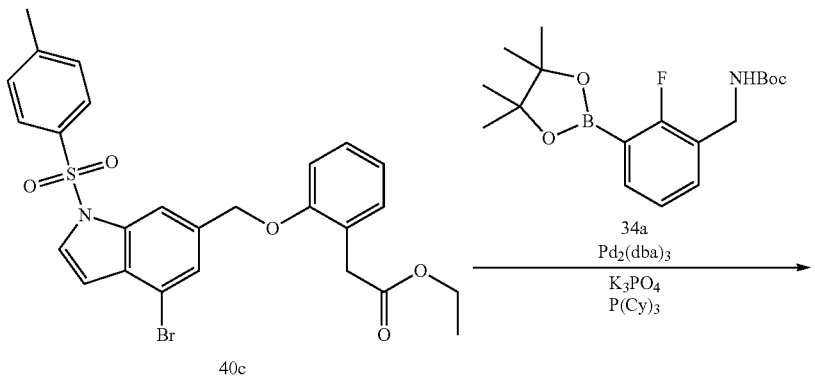

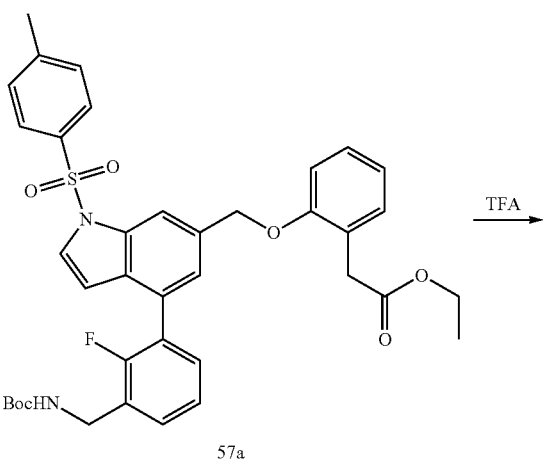

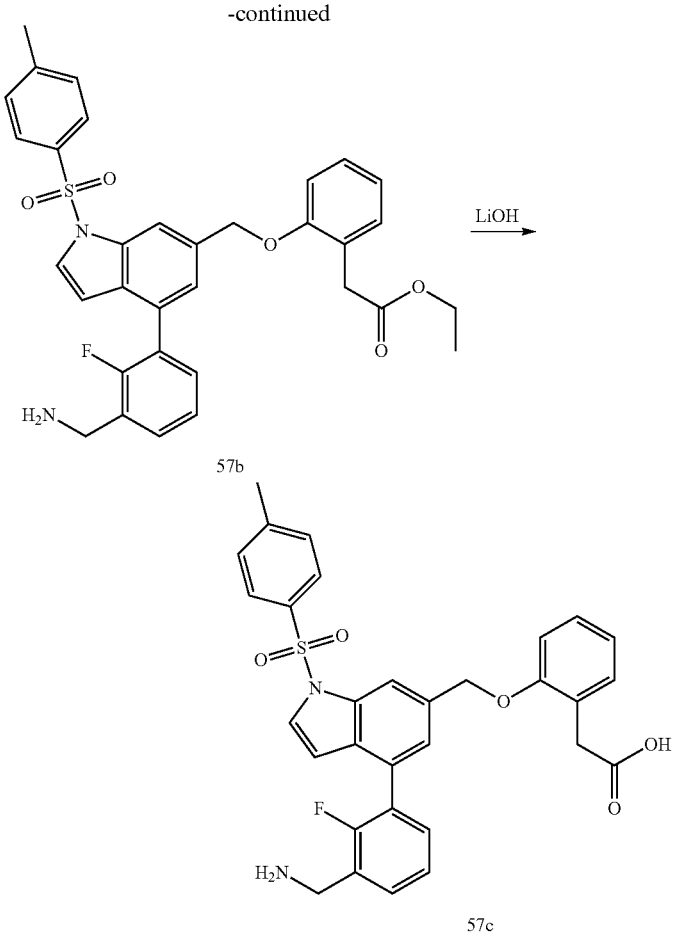

Preparation of 2-(2-((4-(3-(aminomethyl)-2-fluorophenyl)-1-tosyl-1H-indol-6-yl)methoxy)phenyl)acetic Acid (57c)

Step-1: Preparation of Ethyl 2-(2-((4-(3-(((tert-butoxycarbonyl)amino)methyl)-2-fluorophenyl)-1-tosyl-1H-indol-6-yl)methoxy)phenyl)acetate (57a)

Compound 57a was prepared according to the procedure reported in step-3 of Scheme-1 from ethyl 2-(2-((4-bromo-1-tosyl-1H-indol-6-yl)methoxy)phenyl)acetate (40c) (500 mg, 0.92 mmol) in dioxane (5 mL) using tert-butyl 2-fluoro-3-(4,4,5,5-tetramethyl-1,3,2-dioxaborolan-2-yl)benzylcarbamate (34a) (0.49 g, 1.38 mmol), 3 M aqueous solution of tripotassium phosphate (0.52 mL, 1.57 mmol), tricyclohexylphosphine (78 mg, 0.277 mmol) and Pd$_2$(dba)$_3$ (80 mg, 0.09 mmol) in argon atmosphere and heating at 125° C. for 60 min in a microwave. This gave after workup and purification by flash column chromatography [silica (24 g), eluting with EtOAc in hexane from 0-70%] followed by reverse phase column chromatography [C18 (50 g), eluting with ACN in water (containing 0.1% HCl) from 0-100%] ethyl 2-(2-((4-(3-(((tert-butoxycarbonyl)amino)methyl)-2-fluorophenyl)-1-tosyl-1H-indol-6-yl)methoxy)phenyl)acetate (57a) (0.36 g, 57% yield) as a white solid; MS (ES+): 709.4 (M+Na), MS (ES−): 685.4 (M−1), 721.5 (M+Cl).

Step-2: Preparation of Ethyl 2-(2-((4-(3-(aminomethyl)-2-fluorophenyl)-1-tosyl-1H-indol-6-yl)methoxy)phenyl)acetate (57b)

Compound 57b was prepared according to the procedure reported in step-5 of Scheme-1 from ethyl ethyl 2-(2-((4-(3-(((tert-butoxycarbonyl)amino)methyl)-2-fluorophenyl)-1-tosyl-1H-indol-6-yl)methoxy)phenyl)acetate (57a) (0.35 g, 0.51 mmol) in DCM (5 mL) using TFA (0.39 mL, 5.1 mmol). This gave after workup and purification by flash column chromatography [silica (12 g), eluting with DMA80 in DCM from 0-50%] followed by reverse phase column chromatography [C18 (50 g), eluting with ACN in water (containing 0.1% HCl) from 0-100%] ethyl 2-(2-((4-(3-(aminomethyl)-2-fluorophenyl)-1-tosyl-1H-indol-6-yl)methoxy)phenyl)acetate (57b) (0.15 g, 50% yield) as a yellow solid; MS (ES+): 587.3 (M+1), MS (ES−): 621.4 (M+Cl).

Step-3: Preparation of 2-(2-((4-(3-(aminomethyl)-2-fluorophenyl)-1-tosyl-1H-indol-6-yl)methoxy)phenyl)acetic Acid (57c)

Compound 57c was prepared according to the procedure reported in step-6 of Scheme-1, from ethyl 2-(2-((4-(3-(aminomethyl)-2-fluorophenyl)-1-tosyl-1H-indol-6-yl) methoxy)phenyl)acetate (57b) (100 mg, 0.17 mmol) in MeOH/THF (10 mL, 1:1) using a solution of lithium hydroxide hydrate (40 mg, 1.02 mmol) in water (2 mL). This gave after workup 2-(2-((4-(3-(aminomethyl)-2-fluorophenyl)-1-tosyl-1H-indol-6-yl)methoxy)phenyl)acetic acid (57c) (0.02 g, 16% yield) as a yellow solid; $^1$H NMR (300 MHz, DMSO-$d_6$) δ 8.58 (s, 3H), 8.13 (m, 2H), 8.00-7.86 (m, 3H), 7.71-7.62 (m, 1H), 7.52 (m, 1H), 7.45-7.33 (m, 4H), 7.23 (m, 1H), 7.07 (m, 1H), 6.93 (t, J=7.4 Hz, 1H), 6.82-6.68 (m, 1H), 5.34 (s, 2H), 4.11 (q, J=5.9 Hz, 2H), 3.63 (s, 2H), 2.32 (s, 3H); $^{19}$F NMR (282 MHz, DMSO-$d_6$) δ−118.79; MS (ES+): 559.2 (M+1), 581.3 (M+Na); MS (ES−): 557.4 (M−1).

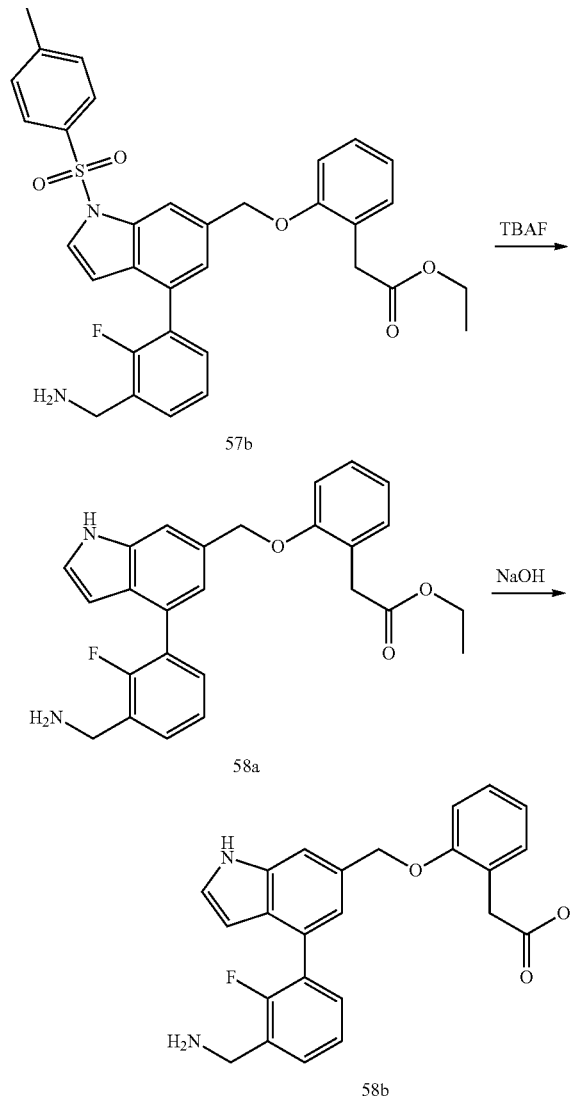

Preparation of 2-(2-((4-(3-(aminomethyl)-2-fluorophenyl)-1H-indol-6-yl)methoxy)phenyl)acetic Acid (58b)

Step-1: Preparation of Ethyl 2-(2-((4-(3-(aminomethyl)-2-fluorophenyl)-1H-indol-6-yl)methoxy)phenyl)acetate (58a)

To a solution of ethyl 2-(2-((4-(3-(aminomethyl)-2-fluorophenyl)-1-tosyl-1H-indol-6-yl)methoxy)phenyl)acetate (57b) (0.31 g, 0.53 mmol) in THF (5 mL) was added tetrabutylammonium fluoride (1.38 g, 5.28 mmol). The mixture was heated at 90° C. in THF for 6 h cooled to room temperature, diluted with EtOAc (60 mL), washed with water (3×), brine, dried and concentrated in vacuum. The residue obtained was purified by flash column chromatography [silica (12 g), eluting with 0-60% EtOAc/MeOH (9:1) in hexane from 0-100%] followed by purification by reverse phase column chromatography [C18 (50 g), eluting with ACN in water (containing 0.1% HCl) from 0-100%] to give ethyl 2-(2-((4-(3-(aminomethyl)-2-fluorophenyl)-1H-indol-6-yl)methoxy)phenyl)acetate (58a) (0.12 g, 53% yield) as a purple solid; $^1$H NMR (300 MHz, DMSO-$d_6$) δ 11.39 (s, 1H), 8.52 (bs, 3H), 7.61 (m, 2H), 7.53 (s, 1H), 7.42 (m, 1H), 7.37 (m, 1H), 7.30-7.17 (m, 2H), 7.13 (m, 2H), 6.90 (t, J=7.3 Hz, 1H), 6.36 (t, J=2.6 Hz, 1H), 5.22 (s, 2H), 4.15 (d, J=5.5 Hz, 2H), 3.91 (q, J=7.1 Hz, 2H), 3.60 (s, 2H), 0.97 (t, J=7.1 Hz, 3H); $^{19}$F NMR (282 MHz, DMSO-$d_6$) δ−118.80; MS (ES+): 433.3 (M+1), 455.3 (M+Na); MS (ES−): 467.3 (M+Cl). HPLC purity: 92.85%.

Step-2: Preparation of Preparation of 2-(2-((4-(3-(aminomethyl)-2-fluorophenyl)-1H-indol-6-yl)methoxy)phenyl)acetic Acid (58b)

Compound 58b was prepared according to the procedure reported in step-4 of Scheme-4, from ethyl 2-(2-((4-(3-(aminomethyl)-2-fluorophenyl)-1H-indol-6-yl)methoxy)phenyl)acetate (58a) (30 mg, 0.07 mmol) in MeOH/THF (5 mL, 1:1) using a solution of sodium hydroxide (10 mg, 0.28 mmol) in water (2 mL). This gave after workup and purification by flash column chromatography [silica (4 g), eluting with DMA80 in DCM from 0-100%] 2-(2-((4-(3-(aminomethyl)-2-fluorophenyl)-1H-indol-6-yl)methoxy)phenyl)acetic acid (58b) (0.01 g, 43% yield) as a white solid; $^1$H NMR (300 MHz, DMSO-$d_6$) δ 12.1082 (bs, 1H); 11.31 (s, 1H), 8.34 (s, 3H), 7.65-7.57 (m, 2H), 7.56 (s, 1H), 7.50-7.33 (m, 2H), 7.21 (m, 2H), 7.18-7.07 (m, 2H), 6.89 (t, J=7.3 Hz, 1H), 6.35 (s, 1H), 5.24 (s, 2H), 4.17 (s, 2H), 3.57 (s, 2H); $^{19}$F NMR (282 MHz, DMSO-$d_6$) δ−118.65; MS (ES$^+$) 405.3 (M+1), 427.2 (M+Na); MS (ES−): 439.3 (M+Cl). HPLC purity: 94.55%.

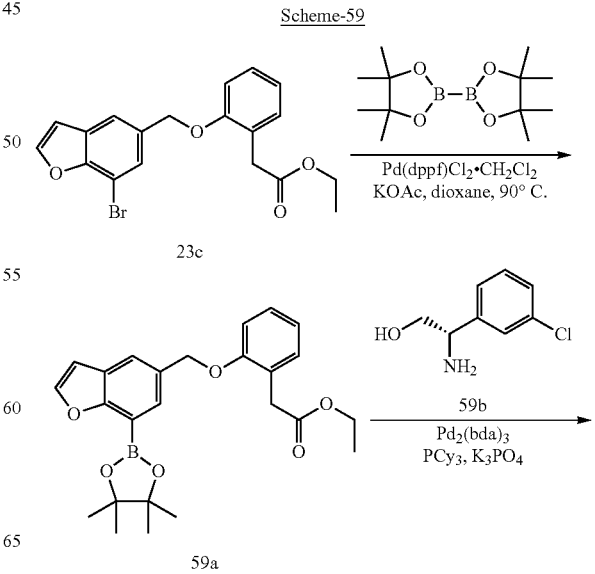

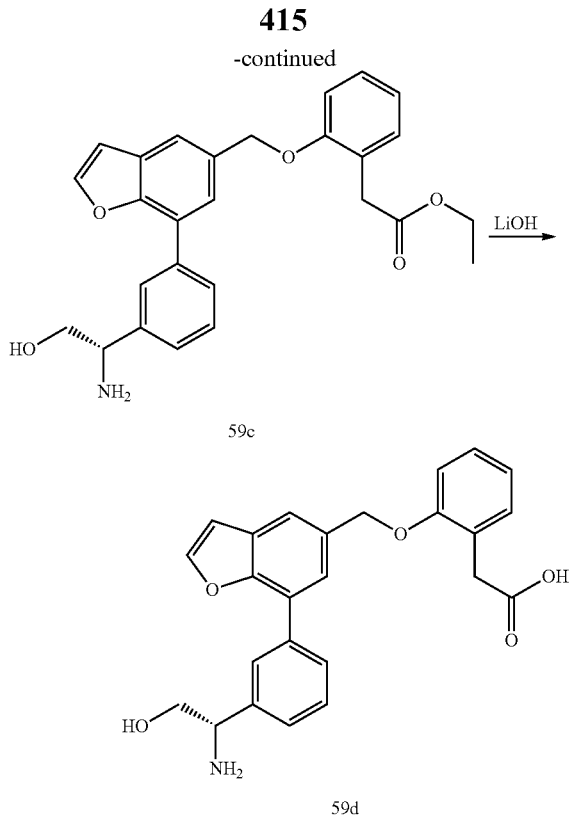

59c

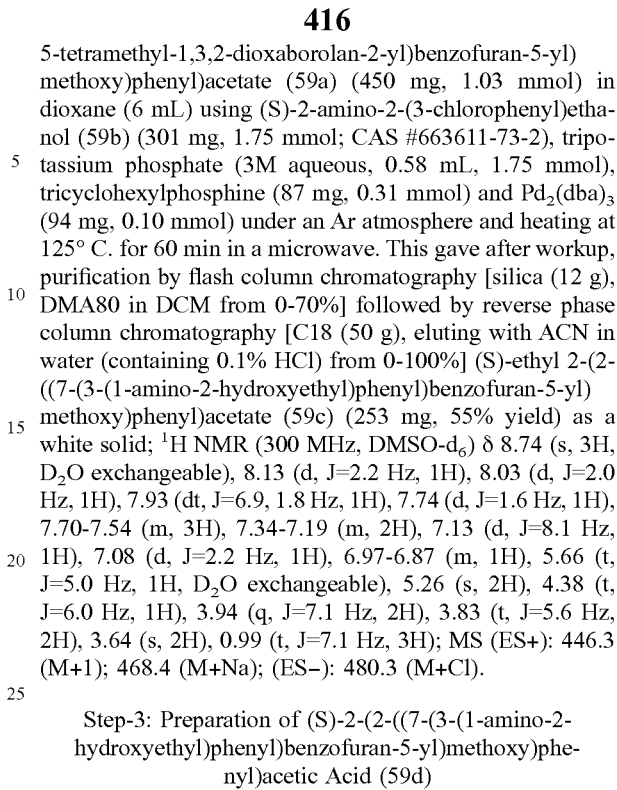

59d

Preparation of (S)-2-(2-((7-(3-(1-amino-2-hydroxyethyl)phenyl)benzofuran-5-yl)methoxy)phenyl)acetic Acid (59d)

Step-1: Preparation of Ethyl 2-(2-((7-(4,4,5,5-tetramethyl-1,3,2-dioxaborolan-2-yl)benzofuran-5-yl)methoxy)phenyl)acetate (59a)

To a degassed solution of ethyl 2-(2-((7-bromobenzofuran-5-yl)methoxy)phenyl)acetate (23c) (8.9 g, 22.87 mmol), bis(pinacolato)diboron (8.71 g, 34.3 mmol, CAS #: 73183-34-3) and potassium acetate (6.73 g, 68.6 mmol) in anhydrous dioxane (150 mL) was added Pd(dppf)Cl$_2$—CH$_2$Cl$_2$ (1.87 g, 2.29 mmol). The resulting mixture was degassed, filled with Ar and stirred at 90° C. overnight. The reaction mixture was then diluted with EtOAc (400 mL) and washed with water (100 mL). The aqueous layer was re-extracted with EtOAc (100 mL×2). The organic layers were combined washed with water (100 mL), brine (100 mL), dried and concentrated in vacuum. The residue obtained was purified by flash column chromatography [silica (80 g), eluting with EtOAc in hexane from 0-40%] to give ethyl 2-(2-((7-(4,4,5,5-tetramethyl-1,3,2-dioxaborolan-2-yl)benzofuran-5-yl)methoxy)phenyl)acetate (59a) (9 g, 90% yield) as an off white solid; $^1$H NMR (300 MHz, DMSO-d$_6$) δ 8.05 (d, J=2.2 Hz, 1H), 7.84 (d, J=1.8 Hz, 1H), 7.65 (d, J=1.8 Hz, 1H), 7.34-7.17 (m, 2H), 7.10 (d, J=8.1 Hz, 1H), 6.98-6.87 (m, 2H), 5.17 (s, 2H), 4.00 (q, J=7.1 Hz, 2H), 3.59 (s, 2H), 1.34 (s, 12H), 1.05 (t, J=7.1 Hz, 3H).

Step-2: Preparation of (S)-ethyl 2-(2-((7-(3-(1-amino-2-hydroxyethyl)phenyl)phenyl)benzofuran-5-yl)methoxy)phenyl)acetate (59c)

Compound 59c was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (450 mg, 1.03 mmol) in dioxane (6 mL) using (S)-2-amino-2-(3-chlorophenyl)ethanol (59b) (301 mg, 1.75 mmol; CAS #663611-73-2), tripotassium phosphate (3M aqueous, 0.58 mL, 1.75 mmol), tricyclohexylphosphine (87 mg, 0.31 mmol) and Pd$_2$(dba)$_3$ (94 mg, 0.10 mmol) under an Ar atmosphere and heating at 125° C. for 60 min in a microwave. This gave after workup, purification by flash column chromatography [silica (12 g), DMA80 in DCM from 0-70%] followed by reverse phase column chromatography [C18 (50 g), eluting with ACN in water (containing 0.1% HCl) from 0-100%] (S)-ethyl 2-(2-((7-(3-(1-amino-2-hydroxyethyl)phenyl)benzofuran-5-yl)methoxy)phenyl)acetate (59c) (253 mg, 55% yield) as a white solid; $^1$H NMR (300 MHz, DMSO-d$_6$) δ 8.74 (s, 3H, D$_2$O exchangeable), 8.13 (d, J=2.2 Hz, 1H), 8.03 (d, J=2.0 Hz, 1H), 7.93 (dt, J=6.9, 1.8 Hz, 1H), 7.74 (d, J=1.6 Hz, 1H), 7.70-7.54 (m, 3H), 7.34-7.19 (m, 2H), 7.13 (d, J=8.1 Hz, 1H), 7.08 (d, J=2.2 Hz, 1H), 6.97-6.87 (m, 1H), 5.66 (t, J=5.0 Hz, 1H, D$_2$O exchangeable), 5.26 (s, 2H), 4.38 (t, J=6.0 Hz, 1H), 3.94 (q, J=7.1 Hz, 2H), 3.83 (t, J=5.6 Hz, 2H), 3.64 (s, 2H), 0.99 (t, J=7.1 Hz, 3H); MS (ES+): 446.3 (M+1); 468.4 (M+Na); (ES−): 480.3 (M+Cl).

Step-3: Preparation of (S)-2-(2-((7-(3-(1-amino-2-hydroxyethyl)phenyl)benzofuran-5-yl)methoxy)phenyl)acetic Acid (59d)

Compound 59d was prepared according to the procedure reported in step-6 of Scheme-1, from (S)-ethyl 2-(2-((7-(3-(1-amino-2-hydroxyethyl)phenyl)benzofuran-5-yl)methoxy)phenyl)acetate (59c) (96 mg, 0.22 mmol) in MeOH/THF (5 mL) using a solution of lithium hydroxide hydrate (36 mg, 0.86 mmol) in water (1 mL). This gave after workup and purification by reverse phase column [C18 (50 g), eluting with ACN in water (containing 0.1% HCl) from 0-100%] (S)-2-(2-((7-(3-(1-amino-2-hydroxyethyl)phenyl)benzofuran-5-yl)methoxy)phenyl)acetic acid (59d) (65 mg, 72% yield) as a white solid; $^1$H NMR (300 MHz, DMSO-d$_6$) δ 12.25 (s, 1H, D$_2$O exchangeable), 8.59 (s, 3H, D$_2$O exchangeable), 8.11 (d, J=2.2 Hz, 1H), 8.00 (d, J=1.8 Hz, 1H), 7.97-7.87 (m, 1H), 7.77 (d, J=1.5 Hz, 1H), 7.66 (d, J=1.6 Hz, 1H), 7.64-7.54 (m, 2H), 7.28-7.20 (m, 2H), 7.14-7.03 (m, 2H), 6.97-6.78 (m, 1H), 5.62 (bs, 1H, D$_2$O exchangeable), 5.28 (s, 2H), 4.46-4.33 (m, 1H), 3.86-3.73 (m, 2H), 3.60 (s, 2H); MS (ES+): 418.3 (M+1); 440.3 (M+Na); (ES−): 416.4 (M−1), 452.3 (M+Cl).

Scheme-60

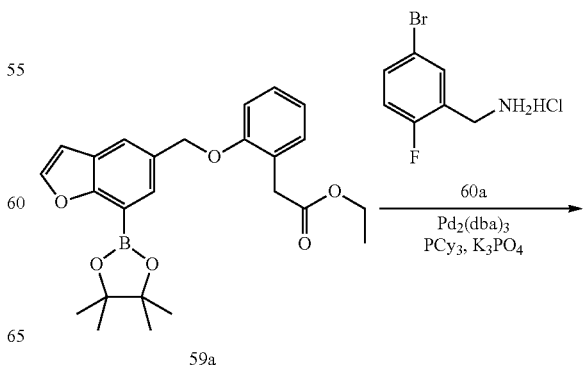

59a

60a

Pd$_2$(dba)$_3$
PCy$_3$, K$_3$PO$_4$

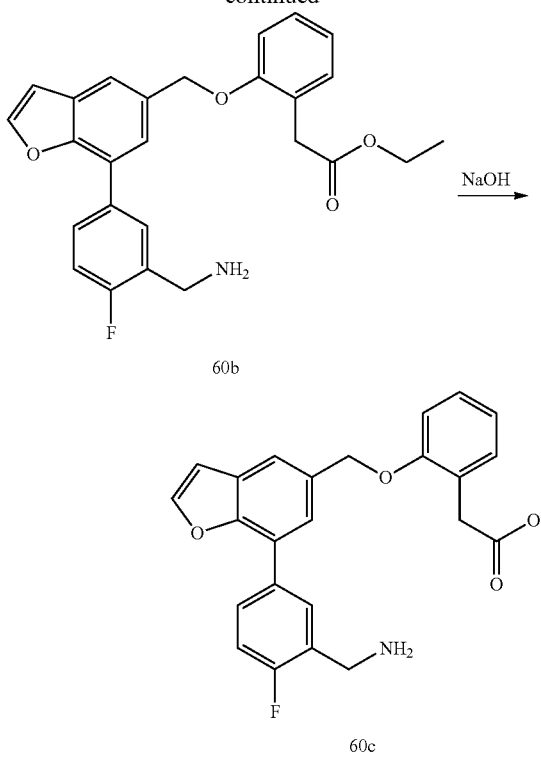

Preparation of 2-(2-((7-(3-(aminomethyl)-4-fluorophenyl)benzofuran-5-yl)methoxy)phenyl)acetic Acid (60c)

Step-1: Preparation of Ethyl 2-(2-((7-(3-(aminomethyl)-4-fluorophenyl)benzofuran-5-yl)methoxy)phenyl)acetate (60b)

Compound 60b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (300 mg, 0.69 mmol) in dioxane (3 mL) using (5-bromo-2-fluorophenyl)methanamine hydrochloride (60a) (248 mg, 1.03 mmol, CAS #202865-69-8), tripotassium phosphate (3M aqueous, 0.85 mL, 2.54 mmol), tricyclohexylphosphine (58 mg, 0.21 mmol) and Pd$_2$(dba)$_3$ (63 mg, 0.069 mmol) under an Ar atmosphere and heating at 125° C. for 90 min in a microwave. This gave after workup, purification by flash column chromatography [silica (12 g), EtOAc in hexane from 0-70%] followed by reverse phase column chromatography [C18 (50 g), eluting with ACN in water (containing 0.1% HCl) from 0-100%] ethyl 2-(2-((7-(3-(aminomethyl)-4-fluorophenyl)benzofuran-5-yl)methoxy)phenyl)acetate (60b) (165 mg, 55% yield) as a yellow solid; $^1$H NMR (300 MHz, DMSO-d$_6$) δ 8.54 (s, 3H, D$_2$O exchangeable), 8.16-8.07 (m, 2H), 8.03-7.92 (m, 1H), 7.76-7.70 (m, 1H), 7.65-7.58 (m, 1H), 7.52-7.41 (m, 1H), 7.30-7.19 (m, 2H), 7.15-7.05 (m, 2H), 6.96-6.87 (m, 1H), 5.24 (s, 2H), 4.16 (s, 2H), 3.94 (q, J=7.1 Hz, 2H), 3.63 (s, 2H), 0.99 (t, J=7.1 Hz, 3H); $^{19}$F NMR (282 MHz, DMSO-d$_6$) δ–117.93; MS (ES+): 434.3 (M+1); 476.4 (M+Na); (ES–): 468.3 (M+Cl).

Step-2: Preparation of 2-(2-((7-(3-(aminomethyl)-4-fluorophenyl)benzofuran-5-yl)methoxy)phenyl)acetic Acid (60c)

Compound 60c was prepared according to the procedure reported in step-4 of Scheme-4, from ethyl 2-(2-((7-(3-(aminomethyl)-4-fluorophenyl)benzofuran-5-yl)methoxy)phenyl)acetate (60b) (65 mg, 0.15 mmol) in MeOH/THF (3 mL) using a solution of sodium hydroxide (24 mg, 0.6 mmol) in water (1 mL). This gave after workup and purification by reverse phase column [C18 (50 g), eluting with ACN in water (containing 0.1% HCl) from 0-100%] 2-(2-((7-(3-(aminomethyl)-4-fluorophenyl)benzofuran-5-yl)methoxy)phenyl)acetic acid (60c) (36 mg, 59% yield) as a white solid; $^1$H NMR (300 MHz, DMSO-d$_6$) δ 8.61 (s, 3H, D$_2$O exchangeable), 8.18-8.10 (m, 2H), 8.05-7.96 (m, 1H), 7.77 (d, J=1.5 Hz, 1H), 7.66 (d, J=1.6 Hz, 1H), 7.52-7.41 (m, 1H), 7.29-7.19 (m, 2H), 7.14-7.05 (m, 2H), 6.96-6.87 (m, 1H), 5.27 (s, 2H), 4.17 (s, 2H), 3.60 (s, 2H); $^{19}$F NMR (282 MHz, DMSO-d$_6$) δ–118.03; MS (ES+): 406.3 (M+1); (ES–): 404.3 (M–1); 440.3 (M+Cl).

Scheme-61

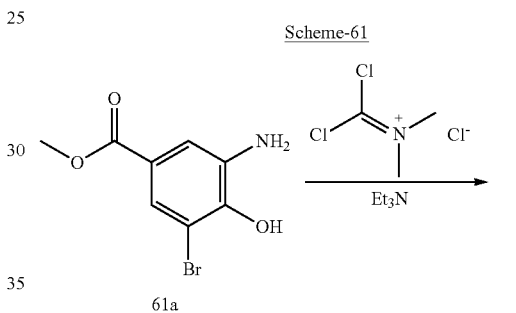

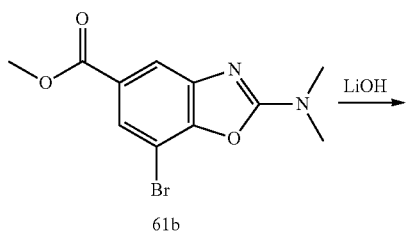

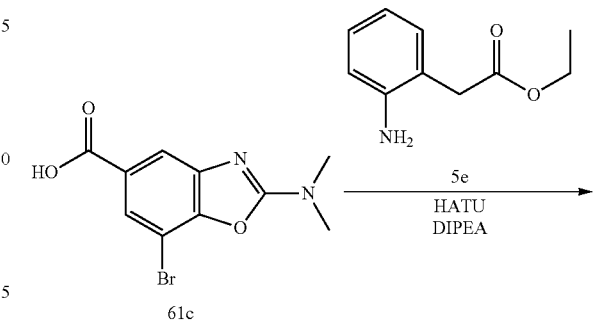

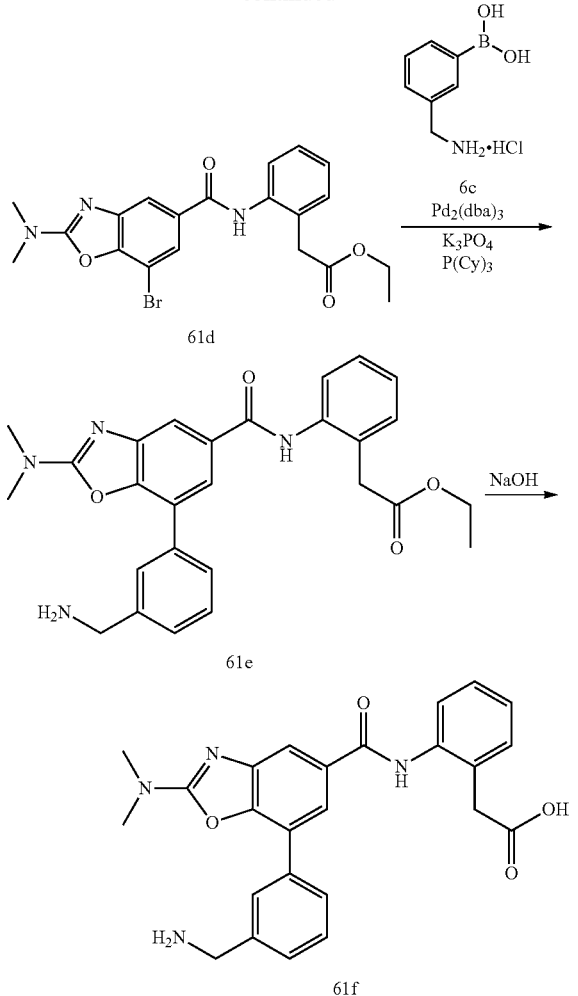

Preparation of 2-(2-(7-(3-(aminomethyl)phenyl)-2-(dimethylamino)benzo[d]oxazole-5-carboxamido)phenyl)acetic Acid (61f)

Step-1: Preparation of methyl 7-bromo-2-(dimethylamino)benzo[d]oxazole-5-carboxylate (61b)

To a solution of methyl 3-amino-5-bromo-4-hydroxybenzoate (61a) (0.2 g, 0.81 mmol; CAS #260249-10-3) in DCM (10 mL) was added N-(dichloromethylene)-N-methylmethanaminium chloride (0.26 g, 1.63 mmol) and triethylamine (0.34 mL, 2.44 mmol). The reaction mixture was heated reflux for 2 h, cooled to room temperature and concentrated in vacuum. The residue obtained was dissolved in EtOAc, washed with water, dried and concentrated. The residue obtained was purified by flash column chromatography [silica (12 g), eluting with EtOAc in hexane from 0-60%] to give methyl 7-bromo-2-(dimethylamino)benzo[d]oxazole-5-carboxylate (61b) (0.22 g, 90% yield) as a white solid; $^1$H NMR (300 MHz, DMSO-$d_6$) δ 7.72 (d, J=1.5 Hz, 1H), 7.70 (d, J=1.5 Hz, 1H), 3.85 (s, 3H), 3.15 (s, 6H); MS (ES+): 299.1 & 301.1 (M+1).

Step-2: Preparation of 7-bromo-2-(dimethylamino)benzo[d]oxazole-5-carboxylic Acid (61c)

Compound 61c was prepared according to the procedure reported in step-6 of Scheme-1, from methyl 7-bromo-2-(dimethylamino)benzo[d]oxazole-5-carboxylate (61b) (220 mg, 0.735 mmol) in MeOH (10 mL) using a solution of lithium hydroxide hydrate (0.185 g, 4.41 mmol) in water (2 mL). This gave after workup 7-bromo-2-(dimethylamino)benzo[d]oxazole-5-carboxylic acid (61c) (0.18 g, 86% yield) as a white solid; $^1$H NMR (300 MHz, DMSO-$d_6$) δ 13.14 (s, 1H), 7.73 (d, J=1.5 Hz, 1H), 7.71 (d, J=1.5 Hz, 1H), 3.16 (s, 6H); MS (ES−): 283.1 (M−1).

Step-3: Preparation of Ethyl 2-(2-(7-bromo-2-(dimethylamino)benzo[d]oxazole-5-carboxamido)phenyl)acetate (61d)

Compound 61d was prepared according to the procedure reported in step-4 of Scheme-1 from 7-bromo-2-(dimethylamino)benzo[d]oxazole-5-carboxylic acid (61c) (180 mg, 0.76 mmol) in DMF (5 mL) using ethyl 2-(2-aminophenyl)acetate (5e) (0.14 g, 0.76 mmol), HATU (0.29 g, 0.76 mmol) and DIPEA (0.22 mL, 1.26 mmol). This gave after workup and purification by flash column chromatography [silica (12 g), eluting with EtOAc in hexane from 0-60%] ethyl 2-(2-(7-bromo-2-(dimethylamino)benzo[d]oxazole-5-carboxamido)phenyl)acetate (61d) (0.17 g, 60% yield) as a white solid; MS (ES−): 444.3 & 446.2 (M−1), 482.2 & 484.1 (M+Cl).

Step-4: Preparation of Ethyl 2-(2-(7-(3-(aminomethyl)phenyl)-2-(dimethylamino)benzo[d] oxazole-5-carboxamido)phenyl)acetate (61e)

Compound 61e was prepared according to the procedure reported in step-3 of Scheme-1 from ethyl 2-(2-(7-bromo-2-(dimethylamino)benzo[d]oxazole-5-carboxamido)phenyl)acetate (61d) (90 mg, 0.2 mmol) in dioxane (3 mL) using 3-(aminomethyl)phenylboronic acid hydrochloride (6c) (60 mg, 0.3 mmol), tripotassium phosphate (3M aqueous, 0.2 mL, 0.61 mmol), tricyclohexylphosphine (20 mg, 0.06 mmol) and $Pd_2(dba)_3$ (20 mg, 0.06 mmol) under an Ar atmosphere and heating at 125° C. for 90 min in a microwave. This gave after workup, purification by flash column chromatography [silica (12 g), eluting with DMA80 in DCM from 0-60%] followed by reverse phase column chromatography [C18 (50 g), eluting with ACN in water (containing 0.1% HCl) from 0-100%] ethyl 2-(2-(7-(3-(aminomethyl)phenyl)-2-(dimethylamino)benzo[d]oxazole-5-carboxamido)phenyl)acetate (61e) (0.03 g, 30% yield) as a white solid; MS (ES+): 473.3 (M+1), MS (ES−): 471.4 (M−1).

Step-5: Preparation of 2-(2-(7-(3-(aminomethyl)phenyl)-2-(dimethylamino)benzo[d]oxazole-5-carboxamido)phenyl)acetic Acid (61f)

Compound 61f was prepared according to the procedure reported in step-4 of Scheme-4, from ethyl 2-(2-(7-(3-(aminomethyl)phenyl)-2-(dimethylamino)benzo[d] oxazole-5-carboxamido)phenyl)acetate (61e) (20 mg, 0.04 mmol) in MeOH (5 mL) using a solution of sodium hydroxide (7 mg, 0.17 mmol) in water (2 mL). This gave after workup and purification by reverse phase column chromatography [C18 (50 g), eluting with ACN in water (containing 0.1% HCl) from 0-100%] 2-(2-(7-(3-(aminomethyl)phenyl)-2-(dimethylamino)benzo[d]oxazole-5-carboxamido)phenyl) acetic acid (61f) (0.01 g, 59% yield) as a white solid; $^1$H NMR (300 MHz, DMSO-$d_6$) δ 10.12 (s, 1H), 8.60 (s, 3H), 8.08 (s, 1H), 7.99 (d, J=1.6 Hz, 1H), 7.94 (dd, J=5.3, 2.8 Hz, 1H), 7.85 (d, J=1.5 Hz, 1H), 7.60 (m, 2H), 7.49 (d, J=7.7 Hz, 1H), 7.38-7.28 (m, 2H), 7.22 (m, 1H), 4.14 (q, J=5.8 Hz, 2H), 3.71 (s, 2H), 3.21 (s, 6H); MS (ES+): 445.3 (M+1), 467.3 (M+Na); MS (ES−): 443.3 (M−1), 439.3 (M+Cl). HPLC purity: 98.13%.

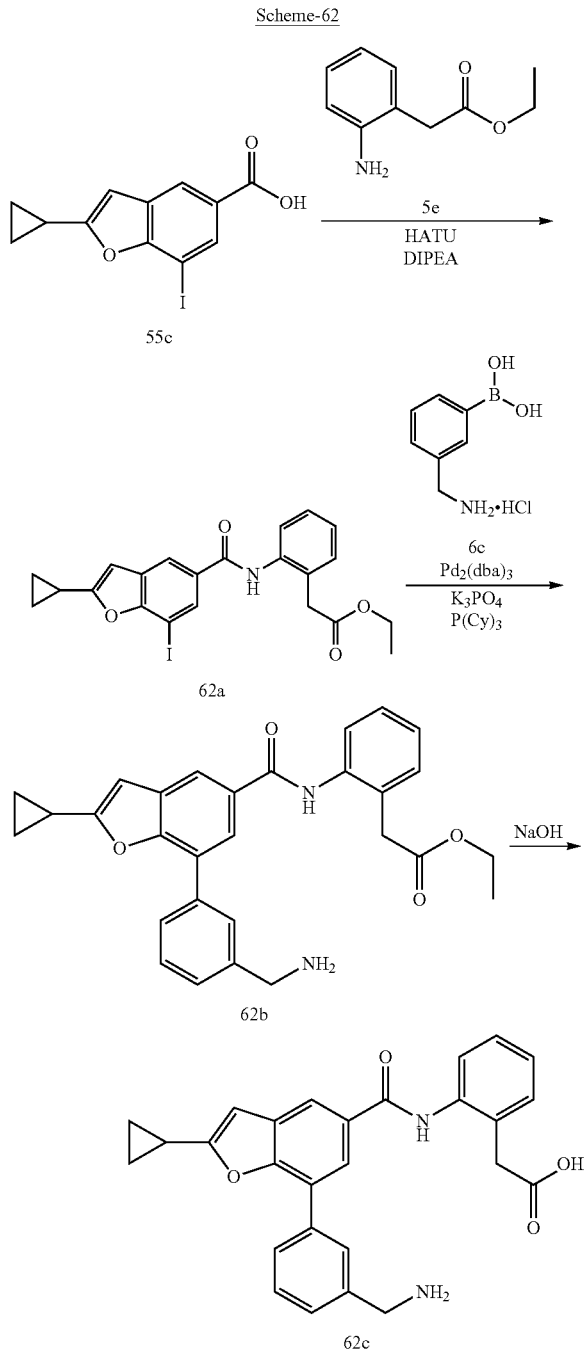

Preparation of 2-(2-(7-(3-(aminomethyl)phenyl)-2-cyclopropylbenzofuran-5-carboxamido)phenyl)acetic Acid (62c)

Step-1: Preparation of Ethyl 2-(2-(2-cyclopropyl-7-iodobenzofuran-5-carboxamido)phenyl)acetate (62a)

Compound 62a was prepared according to the procedure reported in step-4 of Scheme-1 from 2-cyclopropyl-7-iodo-benzofuran-5-carboxylic acid (55c) (185 mg, 0.56 mmol) in DMF (10 mL) using ethyl 2-(2-aminophenyl)acetate (5e) (121 mg, 0.68 mmol), HATU (257 mg, 0.68 mmol) and DIPEA (0.20 mL, 1.13 mmol). This gave after workup and purification by flash column chromatography [silica (12 g), eluting with EtOAc in hexane from 0-60%] ethyl 2-(2-(2-cyclopropyl-7-iodobenzofuran-5-carboxamido)phenyl)acetate (62a) (145 mg, 53% yield) as a semisolid; MS (ES+): 490.2 (M+1); 512.2 (M+Na); (ES−): 488.2 (M−1).

Step-2: Preparation of Ethyl 2-(2-(7-(3-(aminomethyl)phenyl)-2-cyclopropylbenzofuran-5-carboxamido)phenyl)acetate (62b)

Compound 62b was prepared according to the procedure reported in step-3 of Scheme-1 from ethyl 2-(2-(2-cyclopropyl-7-iodobenzofuran-5-carboxamido)phenyl)acetate (62a) (160 mg, 0.33 mmol) in dioxane (3 mL) using 3-(aminomethyl)phenylboronic acid hydrochloride (6c) (92 mg, 0.49 mmol), tripotassium phosphate (3M aqueous, 0.40 mL, 1.21 mmol), tricyclohexylphosphine (28 mg, 0.098 mmol) and $Pd_2(dba)_3$ (30 mg, 0.033 mmol) under an Ar atmosphere and heating at 125° C. for 60 min in a microwave. This gave after workup, purification by flash column chromatography [silica (12 g), eluting with DMA80 in DCM from 0-70%] followed by reverse phase column chromatography [C18 (50 g), eluting with ACN in water (containing 0.1% HCl) from 0-100%] ethyl 2-(2-(7-(3-(aminomethyl)phenyl)-2-cyclopropylbenzofuran-5-carboxamido)phenyl)acetate (62b) (86 mg, 56% yield) as a white solid; $^1$H NMR (300 MHz, DMSO-$d_6$) δ 10.12 (s, 1H, $D_2O$ exchangeable), 8.44 (s, 3H, $D_2O$ exchangeable), 8.15-8.11 (m, 1H), 8.11-8.07 (m, 1H), 8.04 (s, 1H), 7.99-7.92 (m, 1H), 7.68-7.52 (m, 2H), 7.44-7.38 (m, 1H), 7.38-7.30 (m, 2H), 7.29-7.21 (m, 1H), 6.82 (s, 1H), 4.15 (s, 2H), 3.95 (q, J=7.1 Hz, 2H), 3.78 (s, 2H), 2.28-2.16 (m, 1H), 1.12-1.03 (m, 2H), 1.03-0.93 (m, 5H); MS (ES+): 469.3 (M+1); (ES−): 503.4 (M+Cl).

Step-3: Preparation of 2-(2-(7-(3-(aminomethyl)phenyl)-2-cyclopropylbenzofuran-5-carboxamido)phenyl)acetic Acid (62c)

Compound 62c was prepared according to the procedure reported in step-4 of Scheme-4, from ethyl 2-(2-(7-(3-(aminomethyl)phenyl)-2-cyclopropylbenzofuran-5-carboxamido)phenyl)acetate (62b) (53 mg, 0.11 mmol) in MeOH/THF (3 mL) using a solution of sodium hydroxide (18 mg, 0.45 mmol) in water (1 mL). This gave after workup and purification by reverse phase column chromatography [C18 (50 g), eluting with ACN in water (containing 0.1% HCl) from 0-100%] 2-(2-(7-(3-(aminomethyl)phenyl)-2-cyclopropylbenzofuran-5-carboxamido)phenyl)acetic acid (62c) (15 mg, 31% yield) as a white solid; $^1$H NMR (300 MHz, DMSO-$d_6$) δ 12.37 (s, 1H, $D_2O$ exchangeable), 10.17 (s, 1H, $D_2O$ exchangeable), 8.41 (s, 3H, $D_2O$ exchangeable), 8.14 (d, J=1.7 Hz, 1H), 8.08 (d, J=1.8 Hz, 1H), 8.05-8.00 (m, 1H), 8.00-7.92 (m, 1H), 7.67-7.52 (m, 2H), 7.51-7.44 (m, 1H), 7.37-7.28 (m, 2H), 7.22 (td, J=7.4, 1.4 Hz, 1H), 6.81 (s, 1H), 4.15 (s, 2H), 3.69 (s, 2H), 2.28-2.13 (m, 1H), 1.11-1.01 (m, 2H), 1.01-0.92 (m, 2H); MS (ES+): 441.3 (M+1); 463.3 (M+Na); (ES−): 439.4 (M−1); HPLC purity: 98.99%.

Scheme-63

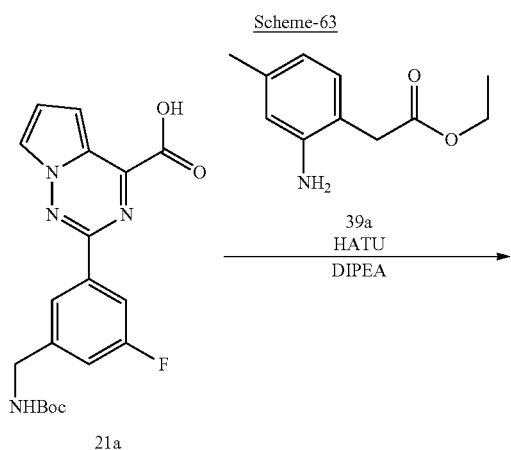

21a + 39a →(HATU, DIPEA)

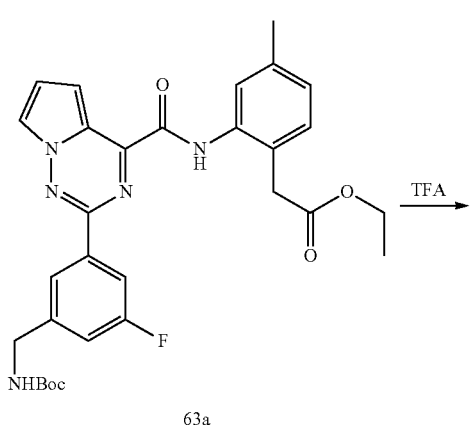

63a →(TFA)

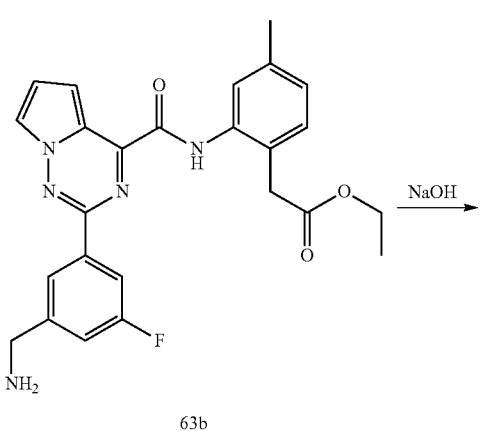

63b →(NaOH)

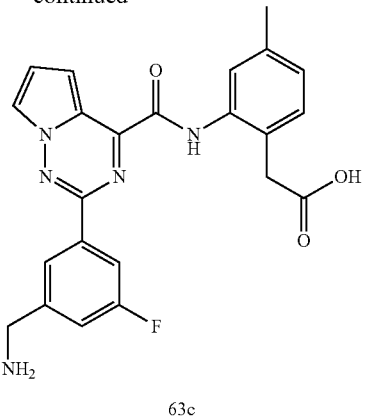

63c

Preparation of 2-(2-(2-(3-(aminomethyl)-5-fluorophenyl)pyrrolo[2,1-f][1,2,4]triazine-4-carboxamido)-4-methylphenyl)acetic Acid (63c)

Step-1: Preparation of Ethyl 2-(2-(2-(3-(((tert-butoxycarbonyl)amino)methyl)-5-fluorophenyl)pyrrolo[2,1-f][1,2,4]triazine-4-carboxamido)-4-methylphenyl)acetate (63a)

Compound 63a was prepared according to the procedure reported in step-4 of Scheme-1 from 2-(3-(((tert-butoxycarbonyl)amino)methyl)-5-fluorophenyl)pyrrolo[2,1-f][1,2,4]triazine-4-carboxylic acid (21a) (0.15 g, 0.388 mmol) in DMF (3 mL) using ethyl 2-(2-amino-4-methylphenyl)acetate (39a) (90 mg, 0.466 mmol), DIPEA (0.20 mL, 1.165 mmol) and HATU (0.177 g, 0.466 mmol). This gave after workup and purification by flash column chromatography [silica (12 g), eluting with 0-60% EtOAc in hexane] ethyl 2-(2-(2-(3-(((tert-butoxycarbonyl)amino)methyl)-5-fluorophenyl)pyrrolo[2,1-f][1,2,4]triazine-4-carboxamido)-4-methylphenyl)acetate (63a) (0.17 g, 78% yield) as an orange colored foam; $^1$H NMR (300 MHz, DMSO-$d_6$) δ 10.85 (s, 1H), 8.37 (d, J=2.6 Hz, 1H), 8.33 (d, J=10.3 Hz, 1H), 8.19 (s, 1H), 7.62-7.54 (m, 3H), 7.33-7.19 (m, 3H), 7.13-7.06 (m, 1H), 4.27 (d, J=6.2 Hz, 2H), 4.01 (q, J=7.1 Hz, 2H), 3.80 (s, 2H), 2.36 (s, 3H), 1.42 (s, 9H), 1.00 (t, J=7.1 Hz, 3H); $^{19}$F NMR (282 MHz, DMSO-$d_6$) δ−113.24; MS (ES+): 562.4 (M+1), 584.3 (M+Na), (ES−): 560.5 (M−1).

Step-2: Preparation of Ethyl 2-(2-(2-(3-(aminomethyl)-5-fluorophenyl)pyrrolo[2,1-f][1,2,4]triazine-4-carboxamido)-4-methylphenyl)acetate (63b)

Compound 63b was prepared according to the procedure reported in step-5 of Scheme-1 from ethyl 2-(2-(2-(3-(((tert-butoxycarbonyl)amino)methyl)-5-fluorophenyl)pyrrolo[2,1-f][1,2,4]triazine-4-carboxamido)-4-methylphenyl)acetate (63a) (0.17 g, 0.303 mmol) in DCM (3 mL) using TFA (0.02 mL, 0.30 mmol). This gave after workup and purification by reverse phase column chromatography [C18 (30 g), eluting with ACN in water (containing 0.1% HCl) from 0-100%] ethyl 2-(2-(2-(3-(aminomethyl)-5-fluorophenyl)pyrrolo[2,1-f][1,2,4]triazine-4-carboxamido)-4-methylphenyl)acetate (63b) (0.036 g, 26% yield) as a HCl salt; $^1$H NMR (300 MHz, DMSO-$d_6$) δ 10.87 (s, 1H), 8.58-8.47 (m, 1H), 8.45-8.34 (m, 2H), 8.27 (s, 3H), 7.63 (dd, J=4.6, 1.4 Hz, 1H), 7.60-7.52 (m, 2H), 7.34-7.27 (m, 2H), 7.11 (d, J=7.7 Hz, 1H), 4.20 (s, 2H), 4.00 (q, J=7.1 Hz, 2H), 3.80 (s, 2H), 2.36 (s, 3H), 0.99 (t, J=7.1 Hz, 3H); $^{19}$F NMR (282 MHz, DMSO-d$_6$) δ−112.48; MS (ES+): 462.3 (M+1); MS (ES−): 496.3 (M+Cl).

Step-3: Preparation of 2-(2-(2-(3-(aminomethyl)-5-fluorophenyl)pyrrolo[2,1-f][1,2,4]triazine-4-carboxamido)-4-methylphenyl)acetic Acid (63c)

Compound 63c was prepared according to the procedure reported in step-4 of Scheme-4 from ethyl 2-(2-(2-(3-(aminomethyl)-5-fluorophenyl)pyrrolo[2,1-f][1,2,4]triazine-4-carboxamido)-4-methylphenyl)acetate (63b) (0.08 g, 0.173 mmol) in THF (2 mL) using sodium hydroxide (0.173 mL, 0.347 mmol, 2 M aqueous). This gave after workup and purification by reverse phase column [C18 (30 g), eluting with ACN in water (containing 0.1% HCl) from 0-100%] 2-(2-(2-(3-(aminomethyl)-5-fluorophenyl)pyrrolo[2,1-f][1,2,4]triazine-4-carboxamido)-4-methylphenyl)acetic acid (63c)

(0.026 g, 35% yield) as a HCl salt; $^1$H NMR (300 MHz, DMSO-d$_6$) δ 12.64 (s, 1H), 10.93 (s, 1H), 8.51-8.35 (m, 6H), 7.66-7.60 (m, 2H), 7.60-7.54 (m, 1H), 7.34-7.25 (m, 2H), 7.09 (dd, J=7.8, 1.8 Hz, 1H), 4.26-4.15 (m, 2H), 3.72 (s, 2H), 2.36 (s, 3H); $^{19}$F NMR (282 MHz, DMSO-d$_6$) δ−112.08; MS (ES+) 434.3 (M+1); MS (ES−) 432.4 (M−1); HPLC purity: 94.02%.

Scheme-64

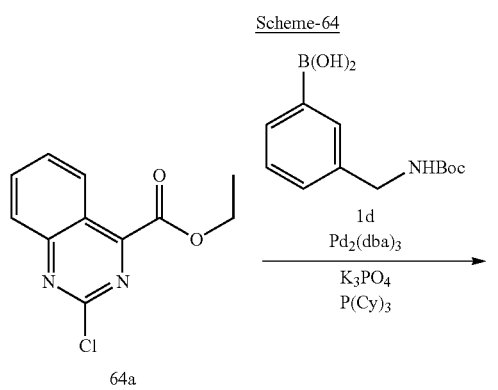

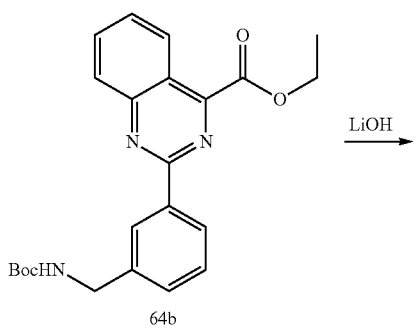

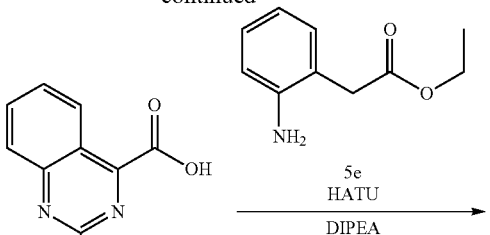

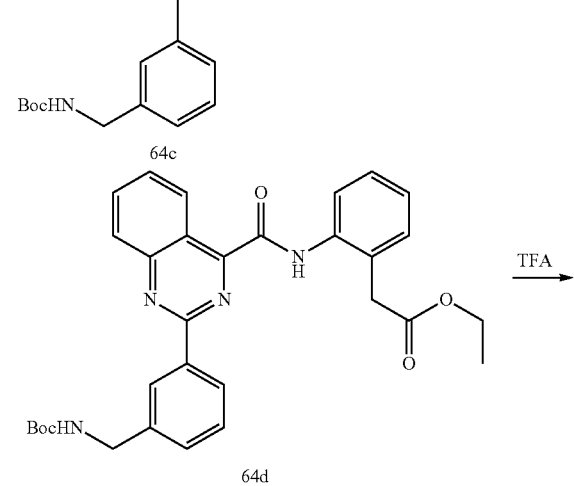

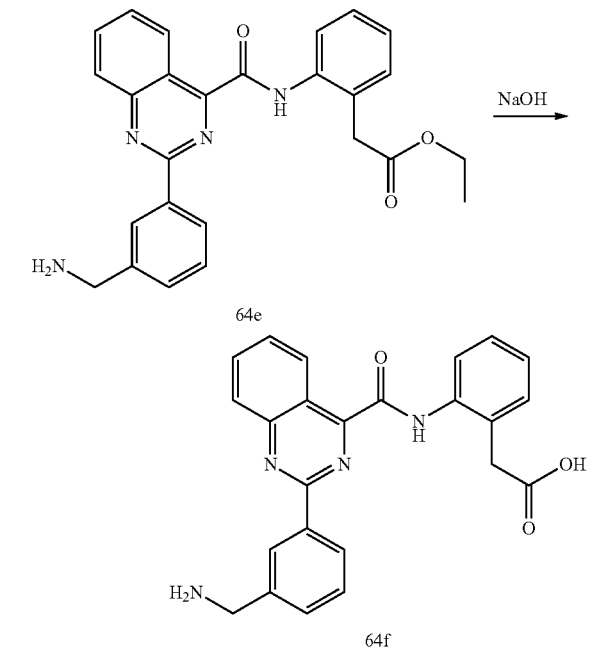

Preparation of 2-(2-(2-(3-(aminomethyl)phenyl)quinazoline-4-carboxamido)phenyl)acetic Acid (64f)

Step-1: Preparation of Ethyl 2-(3-(((tert-butoxycarbonyl)amino)methyl)phenyl)quinazoline-4-carboxylate (64b)

Compound 64b was prepared according to the procedure reported in step-3 of Scheme-1 from ethyl 2-chloroquinazoline-4-carboxylate (64a) (0.4 g, 1.69 mmol; CAS #1092352-52-7) in dioxane (5 mL) using 3-((tert-butoxycarbonylamino)methyl)phenylboronic acid (1d) (0.64 g, 2.54 mmol), tripotassium phosphate (3M aqueous, 0.96 mL, 2.87 mmol), tricyclohexylphosphine 100 mg, 0.34 mmol) and Pd$_2$(dba)$_3$ (90 mg, 0.09 mmol) under an Ar atmosphere and heating at 125° C. for 60 min in a microwave. This gave after workup, purification by flash column chromatography [silica (12 g), eluting with EtOAc in hexane from 0-70%] ethyl 2-(3-(((tert-butoxycarbonyl)amino)methyl)phenyl)quinazoline-4-carboxylate (64b) (0.6 g, 87% yield) as a yellow solid; MS (ES+): 430.3 (M+Na), MS (ES−): 406.4 (M−1).

Step-2: Preparation of 2-(3-(((tert-butoxycarbonyl)amino)methyl)phenyl)quinazoline-4-carboxylic Acid (64c)

Compound 64c was prepared according to the procedure reported in step-6 of Scheme-1 from ethyl 2-(3-(((tert-butoxycarbonyl)amino)methyl)phenyl)quinazoline-4-carboxylate (64b) (0.6 g, 1.47 mmol) in THF/MeOH (5 mL) using lithium hydroxide (0.35 g, 14.73 mmol) in water (2 mL). This gave after workup and purification by reverse phase column chromatography [C18 (30 g), eluting with ACN in water (containing 0.1% HCl) from 0-100%]2-(3-(((tert-butoxycarbonyl)amino)methyl)phenyl)quinazoline-4-carboxylic acid (64c) (0.44 g, 79% yield) as a white solid; $^1$H NMR (300 MHz, DMSO-d$_6$) δ 14.56 (s, 1H), 8.44 (d, J=8.0 Hz, 2H), 8.37 (d, J=8.4 Hz, 1H), 8.11 (d, J=7.0 Hz, 2H), 7.80 (t, J=7.3 Hz, 1H), 7.55 (m, 2H), 7.44 (d, J=7.5 Hz, 1H), 4.26 (d, J=6.0 Hz, 2H), 1.43 (s, 9H); MS (ES−): 378.4 (M−1).

Step-3: Preparation of Ethyl 2-(2-(2-(3-(((tert-butoxycarbonyl)amino)methyl)phenyl)quinazoline-4-carboxamido)phenyl)acetate (64d)

Compound 64d was prepared according to the procedure reported in step-4 of Scheme-1 from 2-(3-(((tert-butoxycarbonyl)amino)methyl)phenyl)quinazoline-4-carboxylic acid (64c) (0.2 g, 0.53 mmol) in DMF (5 mL) using ethyl 2-(2-aminophenyl)acetate (5e) (0.11 g, 0.63 mmol), DIPEA (0.18 mL, 1.05 mmol) and HATU (0.24 g, 0.63 mmol). This gave after workup and purification by flash column chromatography [silica (12 g), eluting with 0-60% EtOAc/ MeOH (9:1) in hexane from 0-100%] ethyl 2-(2-(2-(3-(((tert-butoxycarbonyl)amino)methyl)phenyl)quinazoline-4-carboxamido)phenyl)acetate (64d) (0.26 g, 91% yield) as a white solid; MS (ES+): 541.4 (M−1); MS (ES−): 539.5 (M−1).

Step-4: Preparation of Ethyl 2-(2-(2-(3-(aminomethyl)phenyl)quinazoline-4-carboxamido)phenyl)acetate (64e)

Compound 64e was prepared according to the procedure reported in step-5 of Scheme-1 from ethyl 2-(2-(2-(3-(((tert-butoxycarbonyl)amino)methyl)phenyl)quinazoline-4-carboxamido)phenyl)acetate (64d) (0.13 g, 0.24 mmol) in DCM (5 mL) using TFA (0.19 mL, 2.41 mmol). This gave after workup and purification by reverse column chromatography [C18 (30 g), eluting with ACN in water (containing 0.1% HCl) from 0-100%] ethyl 2-(2-(2-(3-(aminomethyl)phenyl)quinazoline-4-carboxamido)phenyl)acetate (64e) (0.1 g, 94% yield) as a yellow solid; MS (ES+): 441.4 (M+1).

Step-5: Preparation of 2-(2-(2-(3-(aminomethyl)phenyl)quinazoline-4-carboxamido)phenyl)acetic Acid (64f)

Compound 64f was prepared according to the procedure reported in step-4 of Scheme-4 from ethyl 2-(2-(2-(3-(aminomethyl)phenyl)quinazoline-4-carboxamido)phenyl)acetate (64e) (100 mg, 0.227 mmol) in MeOH/THF (5 mL) using a solution of NaOH ((0.036 g, 0.908 mmol) in water (2 mL). This gave after workup and purification by reverse phase column chromatography [C18 (30 g), eluting with ACN in water (containing 0.1% HCl) from 0-40%] 2-(2-(2-(3-(aminomethyl)phenyl)quinazoline-4-carboxamido)phenyl)acetic acid (64f) (0.042 g, 45% yield) as a yellow solid; $^1$H NMR (300 MHz, DMSO-d$_6$) δ 10.85 (d, J=2.9 Hz, 1H), 9.07-8.94 (m, 1H), 8.82 (t, J=1.8 Hz, 1H), 8.73 (d, J=7.7 Hz, 1H), 8.54 (s, 3H), 8.24-8.08 (m, 2H), 7.84 (m, 2H), 7.74 (m, 1H), 7.67 (t, J=7.7 Hz, 1H), 7.41 (m, 2H), 7.28 (t, J=7.5 Hz, 1H), 4.20 (q, J=5.8 Hz, 2H), 3.83 (s, 2H); MS (ES+): 413.2 (M+1); MS (ES−): 411.3 (M−1). HPLC purity: 96.86%.

Scheme-65

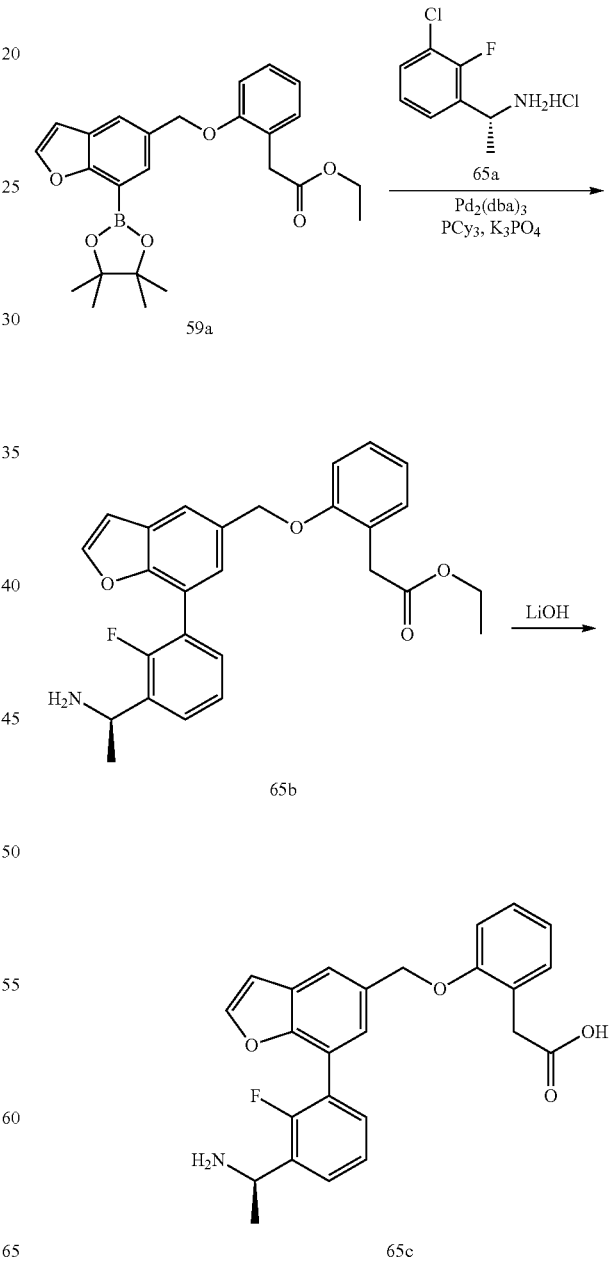

Preparation of (R)-2-(2-((7-(3-(1-aminoethyl)-2-fluorophenyl)benzofuran-5-yl)methoxy)phenyl)acetic Acid (65c)

Step-1: Preparation of (R)-ethyl 2-(2-((7-(3-(1-aminoethyl)-2-fluorophenyl)benzofuran-5-yl)methoxy)phenyl)acetate (65b)

Compound 65b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (300 mg, 0.69 mmol) in dioxane (5 mL) using (R)-1-(3-chloro-2-fluorophenyl)ethanamine hydrochloride (65a) (289 mg, 1.38 mmol, CAS #1253792-97-0), tripotassium phosphate (3M aqueous, 0.92 mL, 2.75 mmol), tricyclohexylphosphine (58 mg, 0.21 mmol) and Pd$_2$(dba)$_3$ (63 mg, 0.069 mmol) under an Ar atmosphere and heating at 130° C. for 30 min in a microwave. This gave after workup, purification by flash column chromatography [silica (12 g), EtOAc in hexane from 0-70%] followed by reverse phase column chromatography [C18 (50 g), eluting with ACN in water (containing 0.1% HCl) from 0-100%] (R)-ethyl 2-(2-((7-(3-(1-aminoethyl)-2-fluorophenyl)benzofuran-5-yl)methoxy)phenyl)acetate (65b) (256 mg, 83% yield) as a white solid; $^1$H NMR (300 MHz, DMSO-d$_6$) δ 8.73 (s, 3H, D$_2$O exchangeable), 8.07 (d, J=2.2 Hz, 1H), 7.84-7.74 (m, 2H), 7.66 (td, J=7.4, 1.7 Hz, 1H), 7.51-7.41 (m, 2H), 7.31-7.20 (m, 2H), 7.16-7.09 (m, 1H), 7.08 (d, J=2.2 Hz, 1H), 6.92 (td, J=7.4, 1.1 Hz, 1H), 5.24 (s, 2H), 4.79-4.62 (m, 1H), 3.92 (q, J=7.1 Hz, 2H), 3.62 (s, 2H), 1.59 (d, J=6.8 Hz, 3H), 0.99 (t, J=7.1 Hz, 3H); MS (ES+): 448.3 (M+1); (ES−): 482.4 (M+Cl).

Step-2: Preparation of (R)-2-(2-((7-(3-(1-aminoethyl)-2-fluorophenyl)benzofuran-5-yl)methoxy)phenyl)acetic Acid (65c)

Compound 65c was prepared according to the procedure reported in step-6 of Scheme-1, from (R)-ethyl 2-(2-((7-(3-(1-aminoethyl)-2-fluorophenyl)benzofuran-5-yl)methoxy)phenyl)acetate (65b) (58 mg, 0.13 mmol) in MeOH/THF (3 mL) using a solution of lithium hydroxide monohydrate (21.76 mg, 0.52 mmol) in water (1 mL). This gave after workup and purification by reverse phase column [C18 (50 g), eluting with ACN in water (containing 0.1% HCl) from 0-100%] (R)-2-(2-((7-(3-(1-aminoethyl)-2-fluorophenyl)benzofuran-5-yl)methoxy)phenyl)acetic acid (65c) (17 mg, 31% yield) as a white solid; $^1$H NMR (300 MHz, DMSO-d$_6$) δ 12.22 (s, 1H, D$_2$O exchangeable), 8.68 (s, 3H, D$_2$O exchangeable), 8.06 (d, J=2.2 Hz, 1H), 7.85-7.73 (m, 2H), 7.71-7.61 (m, 1H), 7.51-7.41 (m, 2H), 7.27-7.18 (m, 2H), 7.13-7.02 (m, 2H), 6.90 (t, J=7.4 Hz, 1H), 5.26 (s, 2H), 4.71 (d, J=7.2 Hz, 1H), 3.58 (s, 2H), 1.59 (d, J=6.8 Hz, 3H); $^{19}$F NMR (282 MHz, DMSO-d$_6$) δ −119.76; MS (ES+): 420.3 (M+1); (ES−): 418.3 (M−1); 454.3 (M+Cl).

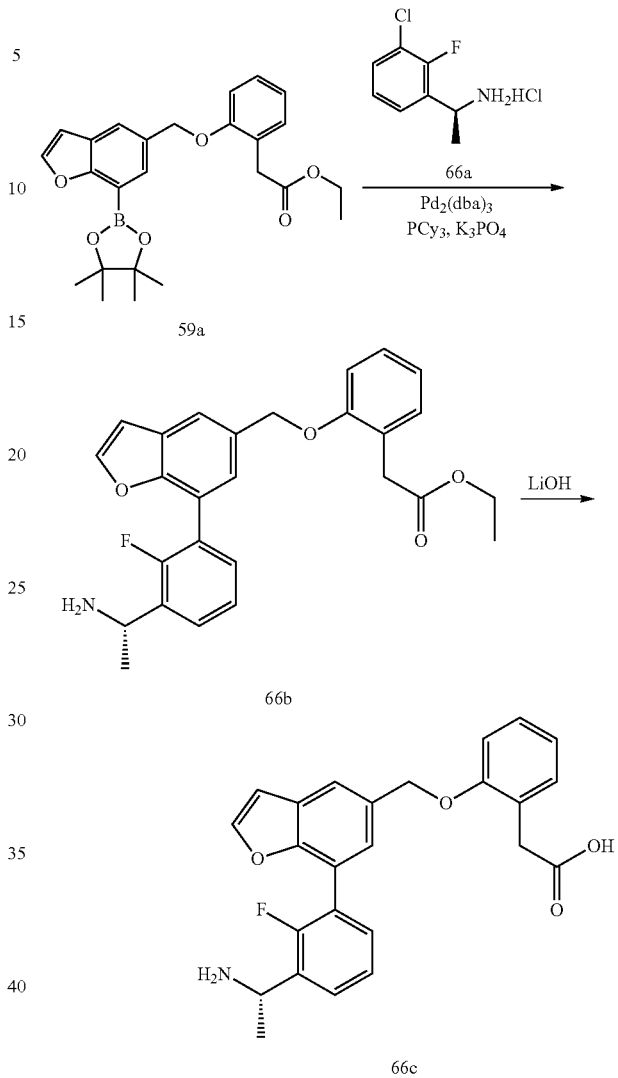

Scheme-66

Preparation of (S)-2-(2-((7-(3-(1-aminoethyl)-2-fluorophenyl)benzofuran-5-yl)methoxy)phenyl)acetic Acid (66c)

Step-1: Preparation of (S)-ethyl 2-(2-((7-(3-(1-aminoethyl)-2-fluorophenyl)benzofuran-5-yl)methoxy)phenyl)acetate (66b)

Compound 66b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (300 mg, 0.69 mmol) in dioxane (5 mL) using (S)-1-(3-chloro-2-fluorophenyl)ethanamine hydrochloride (66a) (253 mg, 1.20 mmol, CAS #1313593-59-7), tripotassium phosphate (3M aqueous, 0.92 mL, 2.75 mmol), tricyclohexylphosphine (58 mg, 0.21 mmol) and Pd$_2$(dba)$_3$ (63 mg, 0.069 mmol) under an Ar atmosphere and heating at 130° C. for 60 min in a microwave. This gave after workup, purification by flash column chromatography [silica (12 g), DMA80 in DCM from 0-70%] followed by reverse phase column chromatography

[C18 (50 g), eluting with ACN in water (containing 0.1% HCl) from 0-100%] (S)-ethyl 2-(2-((7-(3-(1-aminoethyl)-2-fluorophenyl)benzofuran-5-yl)methoxy)phenyl)acetate (66b) (130 mg, 42% yield) as a white solid; $^1$H NMR (300 MHz, DMSO-$d_6$) δ 8.79 (s, 3H, $D_2O$ exchangeable), 8.07 (d, J=2.2 Hz, 1H), 7.88-7.75 (m, 2H), 7.69-7.59 (m, 1H), 7.51-7.39 (m, 2H), 7.30-7.19 (m, 2H), 7.16-7.03 (m, 2H), 6.91 (t, J=7.3 Hz, 1H), 5.24 (s, 2H), 4.70 (q, J=6.5 Hz, 1H), 3.91 (q, J=7.1 Hz, 2H), 3.62 (s, 2H), 1.59 (d, J=6.8 Hz, 3H), 0.98 (t, J=7.1 Hz, 3H); $^{19}$F NMR (282 MHz, DMSO-$d_6$) δ−120.02; MS (ES+): 448.3 (M+1); (ES−): 482.3 (M+Cl); HPLC purity: 98.77%.

Step-2: Preparation of (S)-2-(2-((7-(3-(1-aminoethyl)-2-fluorophenyl)benzofuran-5-yl)methoxy)phenyl)acetic Acid (66c)

Compound 66c was prepared according to the procedure reported in step-6 of Scheme-1, from (S)-ethyl 2-(2-((7-(3-(1-aminoethyl)-2-fluorophenyl)benzofuran-5-yl)methoxy)phenyl)acetate (66b) (72 mg, 0.16 mmol) in MeOH/THF (3 mL) using a solution of lithium hydroxide monohydrate (27 mg, 0.64 mmol) in water (1 mL). This gave after workup and purification by reverse phase column [C18 (50 g), eluting with ACN in water (containing 0.1% HCl) from 0-100%] (S)-2-(2-((7-(3-(1-aminoethyl)-2-fluorophenyl)benzofuran-5-yl)methoxy)phenyl)acetic acid (66c) (26 mg, 39% yield) as a white solid; $^1$H NMR (300 MHz, DMSO-$d_6$) δ 8.78 (s, 2H, $D_2O$ exchangeable), 8.06 (d, J=2.2 Hz, 1H), 7.82 (d, J=1.6 Hz, 1H), 7.77 (t, J=7.2 Hz, 1H), 7.66 (t, J=7.4 Hz, 1H), 7.51-7.38 (m, 2H), 7.30-7.16 (m, 2H), 7.14-7.02 (m, 2H), 6.90 (t, J=7.4 Hz, 1H), 5.26 (s, 2H), 4.72 (q, J=6.8 Hz, 1H), 3.58 (s, 2H), 1.59 (d, J=6.7 Hz, 3H); $^{19}$F NMR (282 MHz, DMSO-$d_6$) δ−119.75; MS (ES+): 420.3 (M+1); (ES−): 418.3 (M−1), 454.3 (M+Cl); HPLC purity: 99.82%.

Scheme-67

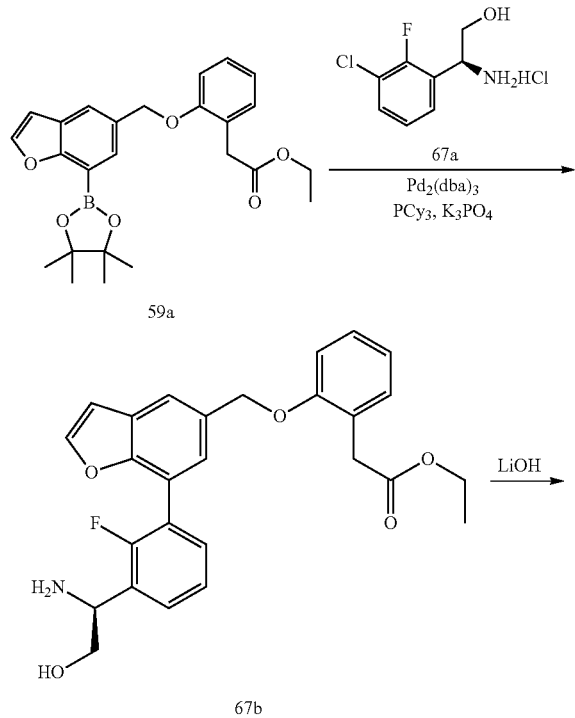

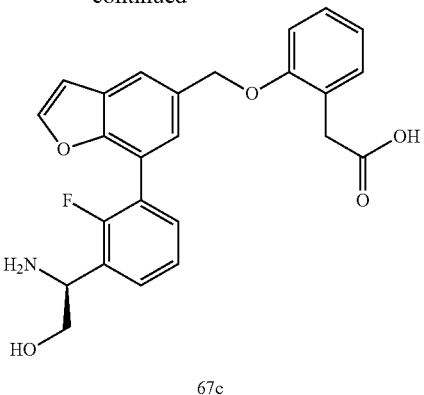

67c

Preparation of (S)-2-(2-((7-(3-(1-amino-2-hydroxyethyl)-2-fluorophenyl)benzofuran-5-yl)methoxy)phenyl)acetic Acid (67c)

Step-1: Preparation of (S)-ethyl 2-(2-((7-(3-(1-amino-2-hydroxyethyl)-2-fluorophenyl)benzofuran-5-yl)methoxy)phenyl)acetate (67b)

Compound 67b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (316 mg, 0.72 mmol) in dioxane (5 mL) using (S)-2-amino-2-(3-chloro-2-fluorophenyl)ethanol hydrochloride (67a) (327 mg, 1.45 mmol, CAS #1391506-22-1), tripotassium phosphate (3M aqueous, 0.41 mL, 1.23 mmol), tricyclohexylphosphine (61 mg, 0.22 mmol) and $Pd_2(dba)_3$ (66 mg, 0.072 mmol) under an Ar atmosphere and heating at 125° C. for 60 min in a microwave. This gave after workup, purification by flash column chromatography [silica (12 g), DMA80 in DCM from 0-70%] followed by reverse phase column chromatography [C18 (50 g), eluting with ACN in water (containing 0.1% HCl) from 0-100%] (S)-ethyl 2-(2-((7-(3-(1-amino-2-hydroxyethyl)-2-fluorophenyl)benzofuran-5-yl)methoxy)phenyl)acetate (67b) (142 mg, 42% yield) as a white solid; $^1$H NMR (300 MHz, DMSO-$d_6$) δ 8.70 (s, 3H, $D_2O$ exchangeable), 8.07 (d, J=2.1 Hz, 1H), 7.83-7.72 (m, 2H), 7.67 (td, J=7.4, 1.6 Hz, 1H), 7.52-7.41 (m, 2H), 7.31-7.18 (m, 2H), 7.12 (dd, J=8.3, 1.2 Hz, 1H), 7.08 (d, J=2.2 Hz, 1H), 6.92 (td, J=7.4, 1.1 Hz, 1H), 5.68 (t, J=5.2 Hz, 1H, $D_2O$ exchangeable), 5.24 (s, 2H), 4.60 (t, J=5.9 Hz, 1H), 3.92 (q, J=7.1 Hz, 2H), 3.85-3.72 (m, 2H), 3.62 (s, 2H), 0.99 (t, J=7.1 Hz, 3H); $^{19}$F NMR (282 MHz, DMSO-$d_6$) δ−119.52; MS (ES+): 464.3 (M+1); 486.3 (M+Na); (ES−): 498.3 (M+Cl); HPLC purity: 98.65%.

Step-2: Preparation of (S)-2-(2-((7-(3-(1-amino-2-hydroxyethyl)-2-fluorophenyl)benzofuran-5-yl)methoxy)phenyl)acetic Acid (67c)

Compound 67c was prepared according to the procedure reported in step-6 of Scheme-1, from (S)-ethyl 2-(2-((7-(3-(1-amino-2-hydroxyethyl)-2-fluorophenyl)benzofuran-5-yl)methoxy)phenyl)acetate (67b) (65 mg, 0.14 mmol) in MeOH/THF (5 mL) using a solution of lithium hydroxide monohydrate (24 mg, 0.56 mmol) in water (1 mL). This gave after workup and purification by reverse phase column [C18 (50 g), eluting with ACN in water (containing 0.1% HCl)

from 0-100%] (S)-2-(2-((7-(3-(1-amino-2-hydroxyethyl)-2-fluorophenyl)benzofuran-5-yl)methoxy)phenyl)acetic acid (67c) (31 mg, 51% yield) as a white solid; $^1$H NMR (300 MHz, DMSO-$d_6$) δ 8.75 (s, 2H, D$_2$O exchangeable), 8.07 (d, J=2.2 Hz, 1H), 7.85-7.80 (m, 1H), 7.76 (t, J=7.3 Hz, 1H), 7.67 (t, J=7.3 Hz, 1H), 7.50-7.42 (m, 2H), 7.27-7.17 (m, 2H), 7.13-7.04 (m, 2H), 6.95-6.86 (m, 1H), 5.67 (s, 1H, D$_2$O exchangeable), 5.27 (s, 2H), 4.60 (t, J=5.7 Hz, 1H), 3.87-3.71 (m, 2H), 3.58 (s, 2H); $^{19}$F NMR (282 MHz, DMSO-$d_6$) δ−119.34; MS (ES$^+$)436.3 (M+1); (ES−), 434.3 (M−1); 470.3 (M+Cl); HPLC purity: 99.26%.

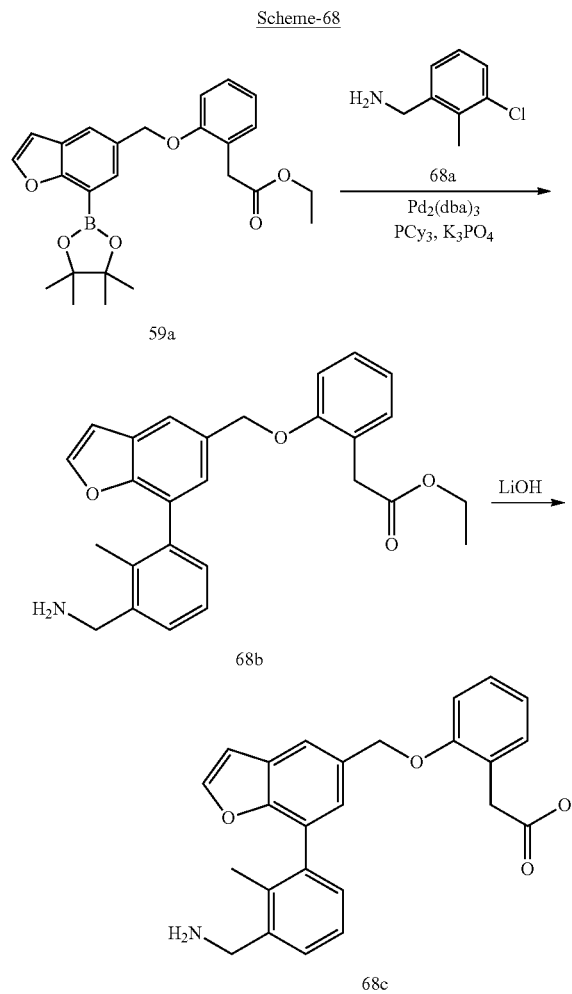

Preparation of 2-(2-((7-(3-(aminomethyl)-2-methylphenyl)benzofuran-5-yl)methoxy)phenyl)acetic Acid (68c)

Step-1: Preparation of Ethyl 2-(2-((7-(3-(aminomethyl)-2-methylphenyl)benzofuran-5-yl)methoxy)phenyl)acetate (68b)

Compound 68b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (315 mg, 0.72 mmol) in dioxane (5 mL) using (3-chloro-2-methylphenyl)methanamine (68a) (225 mg, 1.44 mmol, CAS #226565-61-3), tripotassium phosphate (3M aqueous, 0.41 mL, 1.23 mmol), tricyclohexylphosphine (61 mg, 0.22 mmol) and Pd$_2$(dba)$_3$ (66 mg, 0.072 mmol) under an Ar atmosphere and heating at 130° C. for 60 min in a microwave. This gave after workup, purification by flash column chromatography [silica (12 g), DMA80 in DCM from 0-70%] followed by reverse phase column chromatography [C18 (50 g), eluting with ACN in water (containing 0.1% HCl) from 0-100%] ethyl 2-(2-((7-(3-(aminomethyl)-2-methylphenyl)benzofuran-5-yl)methoxy)phenyl)acetate (68b) (188 mg, 61% yield) as a white solid; $^1$H NMR (300 MHz, DMSO-$d_6$) δ 8.49 (s, 3H, D$_2$O exchangeable), 7.99 (d, J=2.2 Hz, 1H), 7.74 (d, J=1.6 Hz, 1H), 7.52 (dd, J=7.4, 1.7 Hz, 1H), 7.42-7.31 (m, 2H), 7.31-7.17 (m, 3H), 7.12 (d, J=8.0 Hz, 1H), 7.05 (d, J=2.2 Hz, 1H), 6.97-6.86 (m, 1H), 5.23 (s, 2H), 4.13 (s, 2H), 3.91 (q, J=7.1 Hz, 2H), 3.62 (s, 2H), 2.11 (s, 3H), 0.99 (t, J=7.1 Hz, 3H); MS (ES+): 430.4 (M+1); 452.3 (M+Na).

Step-2: Preparation of 2-(2-((7-(3-(aminomethyl)-2-methylphenyl)benzofuran-5-yl)methoxy)phenyl) acetic Acid (68c)

Compound 68c was prepared according to the procedure reported in step-6 of Scheme-1, from ethyl 2-(2-((7-(3-(aminomethyl)-2-methylphenyl)benzofuran-5-yl)methoxy)phenyl)acetate (68b) (55 mg, 0.13 mmol) in MeOH/THF (5 mL) using a solution of lithium hydroxide monohydrate (22 mg, 0.51 mmol) in water (1 mL). This gave after workup and purification by reverse phase column [C18 (50 g), eluting with ACN in water (containing 0.1% HCl) from 0-100%] 2-(2-((7-(3-(aminomethyl)-2-methylphenyl)benzofuran-5-yl)methoxy)phenyl)acetic acid (68c) (23 mg, 45% yield) as a white solid; $^1$H NMR (300 MHz, DMSO-$d_6$) δ 8.59 (s, 1H, D$_2$O exchangeable), 7.98 (d, J=2.2 Hz, 1H), 7.78 (d, J=1.6 Hz, 1H), 7.51 (dd, J=7.0, 1.9 Hz, 1H), 7.42-7.29 (m, 2H), 7.27-7.18 (m, 3H), 7.09 (d, J=8.0 Hz, 1H), 7.03 (d, J=2.2 Hz, 1H), 6.90 (t, J=7.4 Hz, 1H), 5.25 (s, 2H), 4.12 (s, 2H), 3.57 (s, 2H), 2.11 (s, 3H); MS (ES+): 402.3 (M+1); 424.3 (M+Na); (ES−): 400.4 (M−1), 436.4 (M+Cl).

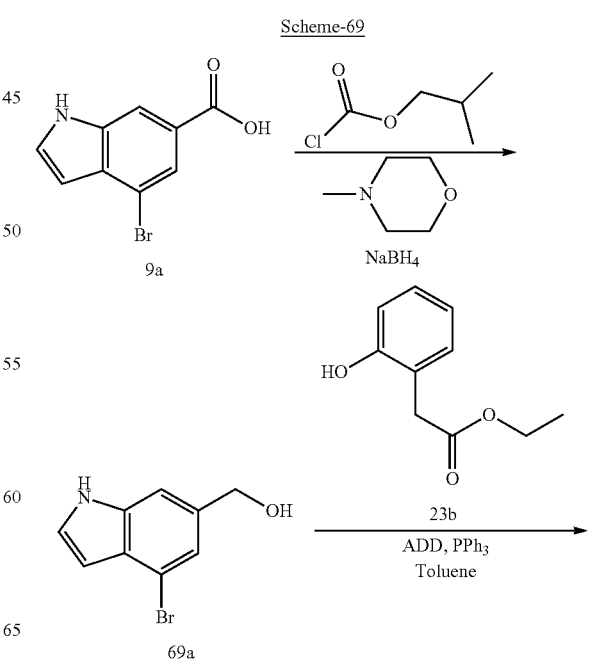

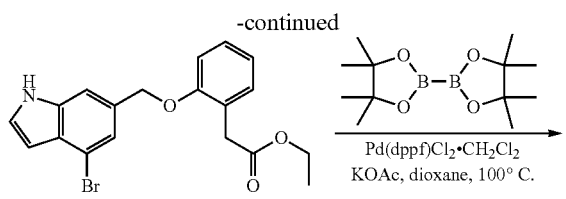

69b

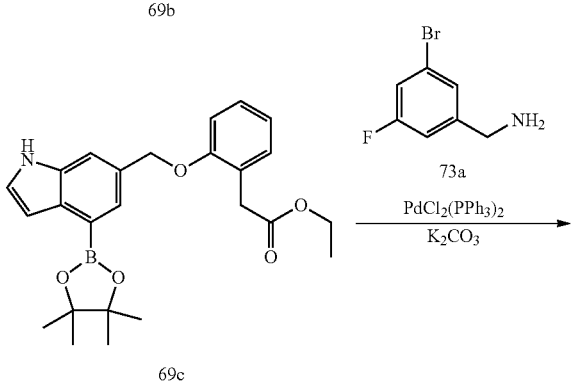

69c

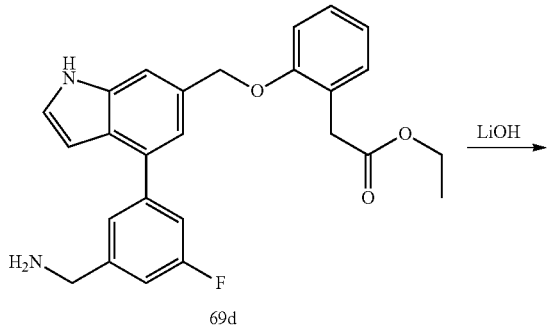

69d

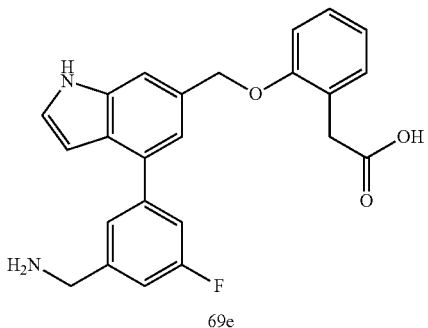

69e

Preparation of 2-(2-((4-(3-(aminomethyl)-5-fluorophenyl)-1H-indol-6-yl)methoxy)phenyl)acetic Acid (69e)

Step-1: Preparation of (4-bromo-1H-indol-6-yl)methanol (69a)

Compound 69a was prepared according to the procedure reported in step-1 of Scheme-23 from 4-bromo-1H-indole-6-carboxylic acid (9a) (10 g, 41.7 mmol) in THF (100 mL), using N-methylmorpholine (5.50 mL, 50.0 mmol), isobutyl chloroformate (6.56 mL, 50.0 mmol) and NaBH$_4$ (4.73 g, 125 mmol) in water (0.8 mL). This gave after workup and purification by flash column chromatography [silica (12 g), eluting with ethyl acetate/MeOH (9:1) in hexane from 0-100%] (4-bromo-1H-indol-6-yl)methanol (69a) (6.1 g, 65% yield) as a yellow solid; $^1$H NMR (300 MHz, DMSO-d$_6$) δ 11.41 (s, 1H), 7.42 (t, J=2.8 Hz, 1H), 7.36 (t, J=1.1 Hz, 1H), 7.18 (d, J=1.2 Hz, 1H), 6.35 (m, 1H), 5.22 (t, J=5.9 Hz, 1H), 4.56 (d, J=5.6 Hz, 2H).

Step-2: Preparation of Ethyl 2-(2-((4-bromo-1H-indol-6-yl)methoxy)phenyl)acetate (69b)

Compound 69b was prepared according to the procedure reported in step-2 of Scheme-23 from (4-bromo-1H-indol-6-yl)methanol (69a) (3 g, 13.27 mmol) in toluene (50 mL) using triphenylphosphine (4.52 g, 17.25 mmol), ethyl 2-(2-hydroxyphenyl) acetate (23b) (3.11 g, 17.25 mmol) and a solution of (E)-diazene-1,2-diylbis(piperidin-1-ylmethanone) (ADD, 4.35 g, 17.25 mmol) in toluene (50 mL). This gave after workup and purification by flash column chromatography [silica (48 g), eluting with EtOAc/MeOH (9:1) in hexane from 0-10% for 40 min, then 10%-50%] ethyl 2-(2-((4-bromo-1H-indol-6-yl)methoxy)phenyl)acetate (69b) (1.3 g, 25% yield) as a yellow oil; $^1$H NMR (300 MHz, DMSO-d$_6$) δ 11.54 (s, 1H), 7.51-7.44 (m, 2H), 7.27 (d, J=1.2 Hz, 1H), 7.26-7.18 (m, 2H), 7.08 (dd, J=8.3, 1.1 Hz, 1H), 6.90 (td, J=7.4, 1.1 Hz, 1H), 6.39 (m, 1H), 5.16 (s, 2H), 4.02 (q, J=7.1 Hz, 2H), 3.60 (s, 2H), 1.07 (t, J=7.1 Hz, 3H).

Step-3: Preparation of Ethyl 2-(2-((4-(4,4,5,5-tetramethyl-1,3,2-dioxaborolan-2-yl)-1H-indol-6-yl)methoxy)phenyl)acetate (69c)

Compound 69c was prepared according to the procedure reported in step-1 of Scheme-59 from ethyl 2-(2-((4-bromo-1H-indol-6-yl)methoxy)phenyl)acetate (69b) (1.3 g, 3.35 mmol) in anhydrous dioxane (20 mL), using bis(pinacolato)diboron (1.28 g, 5.02 mmol), potassium acetate (0.986 g, 10.04 mmol), Pd(dppf)Cl$_2$—CH$_2$Cl$_2$ (0.41 g, 0.50 mmol) and heating under an argon atmosphere at 90° C. overnight. This gave after workup and purification by flash column chromatography [silica (24 g), eluting with EtOAc/MeOH=9:1 in hexane from 0-10%] ethyl 2-(2-((4-(4,4,5,5-tetramethyl-1,3,2-dioxaborolan-2-yl)-1H-indol-6-yl)methoxy)phenyl)acetate (69c) (0.98 g, 67% yield) as a yellow oil; MS (ES$^+$) 458.2 (M+Na).

Step-4: Preparation of Ethyl 2-(2-((4-(3-(aminomethyl)-5-fluorophenyl)-1H-indol-6-yl)methoxy)phenyl)acetate (69d)

Compound 69d was prepared according to the procedure reported in step-3 of Scheme-1 from ethyl 2-(2-((4-(4,4,5,5-tetramethyl-1,3,2-dioxaborolan-2-yl)-1H-indol-6-yl)methoxy)phenyl)acetate (69c) (0.98 g, 2.25 mmol) in dioxane (7 mL) using (3-bromo-5-fluorophenyl)methanamine (73a) (0.20 mL, 1.50 mmol), a solution of potassium carbonate (0.52 g, 3.75 mmol) in water (0.7 mL), bis(triphenylphosphine)Palladium(II)chloride (0.16 g, 0.23 mmol) under an Ar atmosphere and heating at 100° C. for 2 h in an oil bath. This gave after workup, purification by flash column chromatography [silica (12 g), eluting with MeOH in DCM from 0-50%] followed by purification by reverse phase column chromatography[C18 (50 g), eluting with ACN in water (containing 0.1% HCl) from 0-100%] ethyl 2-(2-((4-(3-(aminomethyl)-5-fluorophenyl)-1H-indol-6-yl)methoxy)phenyl)acetate (69d) (0.19 g, 29% yield) as a yellow solid; $^1$H NMR (300 MHz, DMSO-d$_6$) δ 11.44 (s, 1H), 8.34 (s, 3H), 7.68 (d, J=1.5 Hz, 1H), 7.54-7.45 (m, 3H), 7.37 (d, J=9.7 Hz, 1H), 7.28-7.18 (m, 3H), 7.12 (d, J=8.1 Hz, 1H), 6.91 (dd, J=7.4, 1.1 Hz, 1H), 6.68 (d, J=2.9 Hz, 1H), 5.23 (s, 2H), 4.15 (d, J=5.8 Hz, 2H), 3.94 (q, J=7.1 Hz, 2H), 3.61 (s, 2H), 0.98 (t, J=7.1 Hz, 3H); ¹⁹F NMR (282 MHz, DMSO-d₆) δ −112.87; MS (ES⁺) 433.2 (M+1); MS (ES−) 431.3 (M−1). HPLC: 97.87%.

Step-5: Preparation of 2-(2-((4-(3-(aminomethyl)-5-fluorophenyl)-1H-indol-6-yl)methoxy)phenyl)acetic Acid (69e)

Compound 69e was prepared according to the procedure reported in step-6 of Scheme-1, from ethyl 2-(2-((4-(3-(aminomethyl)-5-fluorophenyl)-1H-indol-6-yl)methoxy)phenyl)acetate (69d) (0.15 g, 0.35 mmol) in MeOH/THF (4 mL) using a solution of lithium hydroxide hydrate (73 mg, 1.73 mmol) in water (0.8 mL). This gave after workup and purification by reverse phase column [C18 (50 g), eluting with ACN in water (containing 0.1% HCl) from 0-100%] 2-(2-((4-(3-(aminomethyl)-5-fluorophenyl)-1H-indol-6-yl)methoxy)phenyl)acetic acid (69e) (0.02 g, 15% yield) as a white solid; ¹H NMR (300 MHz, DMSO-d₆) δ 12.14 (s, 1H), 11.41 (s, 1H), 8.41 (s, 3H), 7.68 (s, 1H), 7.57-7.43 (m, 3H), 7.37 (d, J=9.4 Hz, 1H), 7.26 (d, J=1.3 Hz, 1H), 7.22 (s, 1H), 7.20 (s, 1H), 7.10 (d, J=8.0 Hz, 1H), 6.89 (t, J=7.3 Hz, 1H), 6.67 (d, J=2.6 Hz, 1H), 5.25 (s, 2H), 4.15 (s, 2H), 3.58 (s, 2H). ¹⁹F NMR (282 MHz, DMSO-d₆) δ −112.73; MS (ES⁺) 405.1 (M+1). HPLC purity: 95.81%.

nyl)acetate (40d) (0.08 g, 0.141 mmol) in MeOH/THF (5 mL, 1:1) using a solution of sodium hydroxide (56 mg, 1.41 mmol) in water (2 mL). This gave after workup and purification by reverse phase column [C18 (50 g), eluting with ACN in water (containing 0.1% HCl) from 0-100%] 2-(2-((4-(3-(aminomethyl)phenyl)-1H-indol-6-yl)methoxy)phenyl)acetic acid (70a) (0.021 g, 39% yield) as a white solid; ¹H NMR (300 MHz, DMSO-d₆) δ 12.19 (s, 1H), 11.37 (s, 1H), 8.34 (s, 4H), 7.82 (t, J=1.7 Hz, 1H), 7.70 (dt, J=7.7, 1.5 Hz, 1H), 7.56 (m, 1H), 7.51 (m, 1H), 7.48-7.43 (m, 1H), 7.27-7.17 (m, 2H), 7.11 (d, J=8.1 Hz, 1H), 6.89 (td, J=7.4, 1.2 Hz, 1H), 6.66 (d, J=2.7 Hz, 1H), 5.25 (s, 2H), 4.13 (s, 2H), 3.58 (s, 2H); MS (ES+): 387.3 (M+1); MS (ES−): 421.4 (M+Cl).

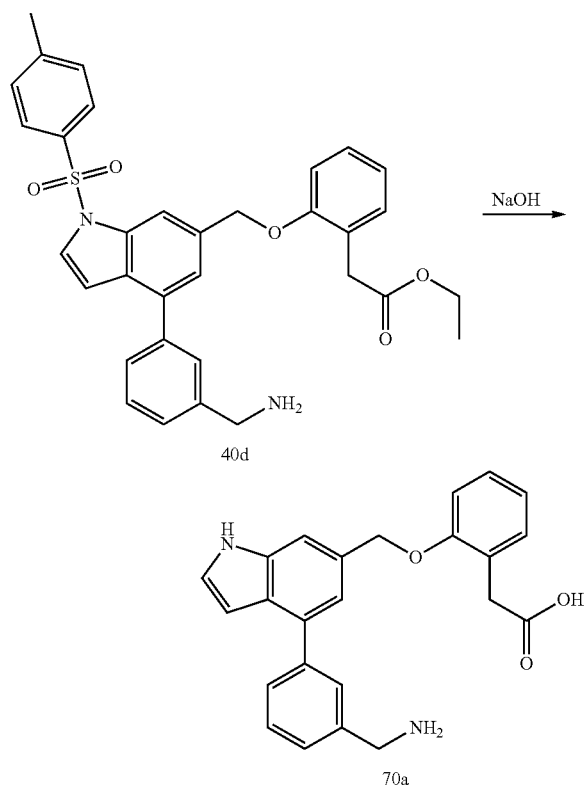

Scheme 70

Preparation of 2-(2-((4-(3-(aminomethyl)phenyl)-1H-indol-6-yl)methoxy)phenyl)acetic Acid (70a)

Compound 70a was prepared according to the procedure reported in step-4 of Scheme-4, from ethyl 2-(2-((4-(3-(aminomethyl)phenyl)-1-tosyl-1H-indol-6-yl)methoxy)phe-

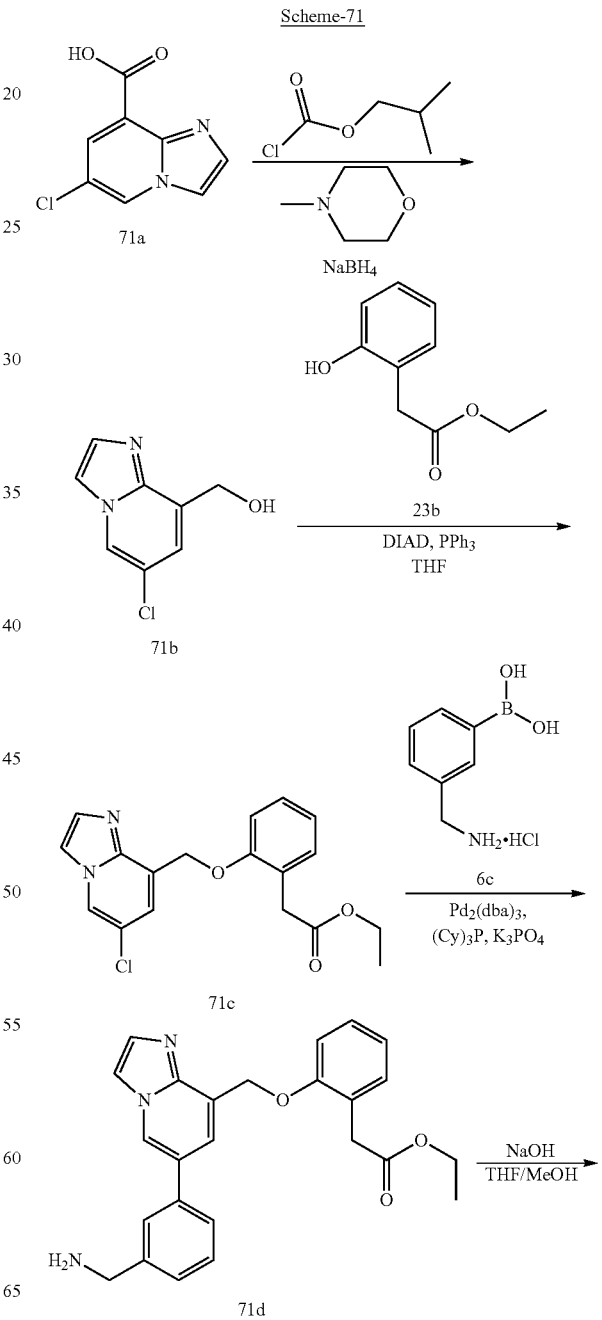

Scheme-71

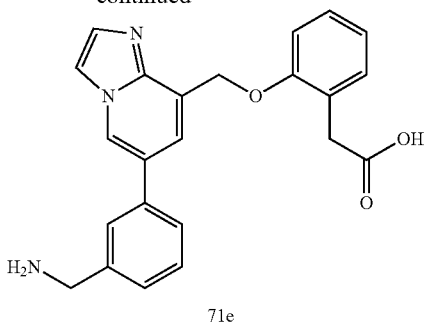

71e

Preparation of 2-(2-((6-(3-(aminomethyl)phenyl)imidazo[1,2-a]pyridin-8-yl)methoxy)phenyl)acetic Acid (71e)

Step-1: Preparation of (6-chloroimidazo[1,2-a]pyridin-8-yl)methanol (71b)

Compound 71b was prepared according to the procedure reported in step-1 of Scheme-23 from 6-chloroimidazo[1,2-a]pyridine-8-carboxylic acid (71a) (1.0 g, 5.09 mmol; CAS #155735-02-7) using N-methylmorpholine (0.615 mL, 5.60 mmol) in THF (20 mL), isobutyl chloroformate (0.735 mL, 5.60 mmol) and NaBH$_4$ (0.289 g, 7.63 mmol) in water. This gave after workup and purification by flash column chromatography [silica (12 g), eluting with ethyl acetate in hexane from 0-100%] (6-chloroimidazo[1,2-a]pyridin-8-yl)methanol (71b) (0.401 g, 43% yield) as a pale yellow solid; $^1$H NMR (300 MHz, DMSO-d$_6$) δ 8.76-8.73 (m, 1H), 7.99-7.91 (m, 1H), 7.60-7.54 (m, 1H), 7.28-7.13 (m, 1H), 5.54 (s, 1H, D$_2$O exchangeable), 4.84 (s, 2H).

Step-2: Preparation of Ethyl 2-(2-((6-chloroimidazo[1,2-a]pyridin-8-yl)methoxy)phenyl)acetate (71c)

Compound 71c was prepared according to the procedure reported in step-2 of Scheme-23 from (6-chloroimidazo[1,2-a]pyridin-8-yl)methanol (71b) (0.4 g, 2.19 mmol) in THF (25 mL) using triphenylphosphine (0.747 g, 2.85 mmol), ethyl 2-(2-hydroxyphenyl) acetate (23b) (0.513 g, 2.85 mmol) and DIAD (0.554 mL, 2.85 mmol). This gave after workup and purification by flash column chromatography [silica (12 g), eluting with EtOAc in hexane from 0-100%] ethyl 2-(2-((6-chloroimidazo[1,2-a]pyridin-8-yl)methoxy)phenyl)acetate (71c) (0.66 g, 87% yield) as a yellow solid. MS (ES+): 367.2 (M+Na).

Step-3: Preparation of Ethyl 2-(2-((6-(3-(aminomethyl)phenyl)imidazo[1,2-a]pyridin-8-yl)methoxy)phenyl)acetate (71d)

Compound 71d was prepared according to the procedure reported in step-3 of Scheme-1 from ethyl 2-(2-((6-chloroimidazo[1,2-a]pyridin-8-yl)methoxy)phenyl)acetate (71c) (0.65 g, 1.89 mmol) in dioxane (6 mL) using 3-(aminomethyl)phenylboronic acid hydrochloride (6c) (0.530 g, 2.83 mmol), tripotassium phosphate (1.3M, 1.885 mL, 5.66 mmol), tricyclohexylphosphine (0.159 g, 0.566 mmol) and Pd$_2$(dba)$_3$ (0.173 g, 0.189 mmol) under an Ar atmosphere and heating at 125° C. for 45 min in an oil bath. This gave after workup, purification by flash column chromatography [silica (12 g), eluting with DMA80 in DCM from 0-60%] ethyl 2-(2-((6-(3-(aminomethyl)phenyl)imidazo[1,2-a]pyridin-8-yl)methoxy)phenyl)acetate (71d) (0.151 g, 19% yield) HCl salt as a white solid; $^1$H NMR (300 MHz, DMSO-d$_6$) δ 9.39-9.35 (m, 1H), 8.64 (s, 3H, D$_2$O exchangeable), 8.42 (d, J=2.0 Hz, 1H), 8.40-8.26 (m, 2H), 8.05 (s, 1H), 7.90-7.76 (m, 1H), 7.69-7.58 (m, 2H), 7.38-7.18 (m, 3H), 7.05-6.93 (m, 1H), 5.58 (s, 2H), 4.21-4.03 (m, 2H), 3.86 (q, J=7.1 Hz, 2H), 3.69 (s, 2H), 0.91 (t, J=7.1 Hz, 3H); MS (ES+): 416.3 (M+1); MS (ES−): 450.4 (M+Cl); HPLC purity: 97.21%. Analysis Calculated for: C$_{25}$H$_{25}$N$_3$O$_3$·3H$_2$O.2HCl: C, 55.35; H, 6.13; Cl, 13.07; N, 7.75; Found: C, 55.41; H, 5.96; Cl, 13.01; N, 7.79.

Step-4: Preparation of 2-(2-((6-(3-(aminomethyl)phenyl)imidazo[1,2-a]pyridin-8-yl)methoxy)phenyl)acetic Acid (71e)

Compound 71e was prepared according to the procedure reported in step-4 of Scheme-4, from ethyl 2-(2-((6-(3-(aminomethyl)phenyl)imidazo[1,2-a]pyridin-8-yl)methoxy)phenyl)acetate (71d) (0.040 g, 0.096 mmol) in THF (4 mL) and methanol (8 mL) using a 2 M aqueous solution of sodium hydroxide (0.193 mL, 0.385 mmol). This gave after workup and purification by reverse phase column [C18 (50 g), eluting with ACN in water (containing 0.1% HCl) from 0-100%] 2-(2-((6-(3-(aminomethyl)phenyl)imidazo[1,2-a]pyridin-8-yl)methoxy)phenyl)acetic acid (71e) (0.026 g, 70% yield) HCl salt as a white solid; $^1$H NMR (300 MHz, DMSO-d$_6$) δ 9.35 (s, 1H), 8.62 (s, 3H, D$_2$O exchangeable, 2H), 8.45-8.39 (m, 1H), 8.33 (d, J=12.0 Hz, 2H), 8.05 (s, 1H), 7.88-7.76 (m, 1H), 7.64 (d, J=4.7 Hz, 2H), 7.40-7.16 (m, 3H), 7.04-6.94 (m, 1H), 5.58 (s, 2H), 4.20-4.02 (m, 2H), 3.72 (s, 2H); MS (ES+): 388.3 (M+1); MS (ES−): 386.4 (M−1); 422.3 (M+Cl); Analysis calculated for: C$_{23}$H$_{21}$N$_3$O$_3$·2.0H$_2$O.2.0HCl: C, 55.65; H, 5.48; N, 8.47; Found: C, 55.53; H, 5.71; N, 8.15.

Scheme-72

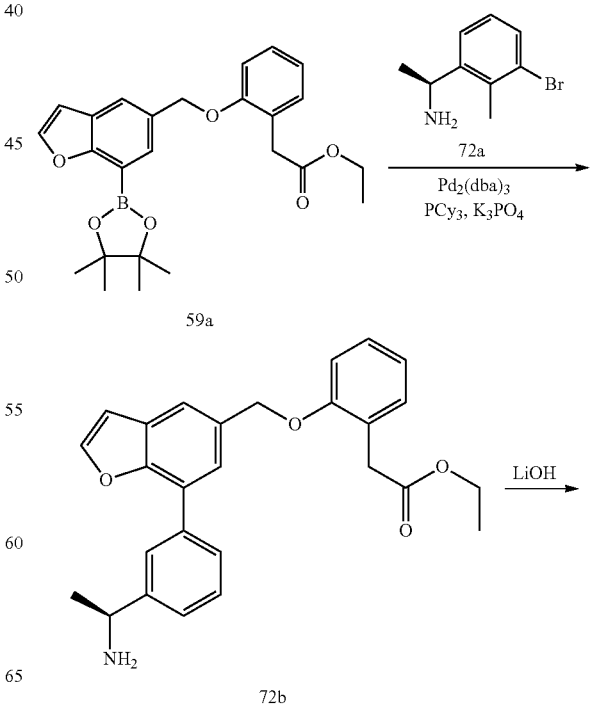

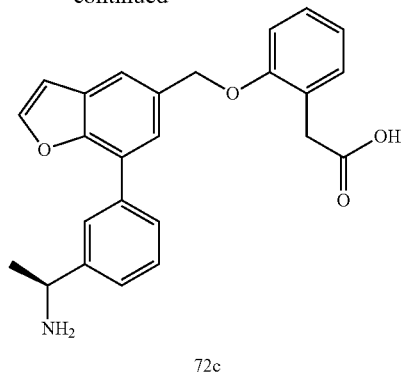

72c

Preparation of (S)-2-(2-((7-(3-(1-aminoethyl)phenyl)benzofuran-5-yl)methoxy)phenyl)acetic Acid (72c)

Step-1: Preparation of (S)-ethyl 2-(2-((7-(3-(1-aminoethyl)phenyl)benzofuran-5-yl)methoxy)phenyl) acetate (72b)

Compound 72b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (450 mg, 1.03 mmol) in dioxane (6 mL) using (S)-1-(3-bromophenyl)ethanamine (72a) (351 mg, 1.75 mmol; CAS #139305-96-7), tripotassium phosphate (3M aqueous, 0.58 mL, 1.75 mmol), tricyclohexylphosphine (87 mg, 0.31 mmol) and Pd$_2$(dba)$_3$ (94 mg, 0.10 mmol) under an Ar atmosphere and heating at 120° C. for 90 min in a microwave. This gave after workup, purification by flash column chromatography [silica (12 g), DMA80 in DCM from 0-70%] followed by reverse phase column chromatography [C18 (50 g), eluting with ACN in water (containing 0.1% HCl) from 0-100%] (S)-ethyl 2-(2-((7-(3-(1-aminoethyl)phenyl)benzofuran-5-yl)methoxy)phenyl)acetate (72b) (312 mg, 70% yield) HCl salt as a white solid; $^1$H NMR (300 MHz, DMSO-d$_6$) δ 8.65 (s, 3H, D$_2$O exchangeable), 8.12 (d, J=2.2 Hz, 1H), 8.02 (d, J=2.0 Hz, 1H), 7.96-7.85 (m, 1H), 7.74 (d, J=1.5 Hz, 1H), 7.67-7.58 (m, 3H), 7.31-7.19 (m, 2H), 7.17-7.10 (m, 1H), 7.08 (d, J=2.2 Hz, 1H), 6.92 (td, J=7.4, 1.0 Hz, 1H), 5.25 (s, 2H), 4.50 (q, J=6.7 Hz, 1H), 3.93 (q, J=7.1 Hz, 2H), 3.64 (s, 2H), 1.60 (d, J=6.7 Hz, 3H), 0.98 (t, J=7.1 Hz, 3H); MS (ES+): 430.3 (M+1); (ES−): 464.3 (M+Cl).

Step-2: Preparation of (S)-2-(2-((7-(3-(1-aminoethyl)phenyl)benzofuran-5-yl)methoxy)phenyl)acetic Acid (72c)

Compound 72c was prepared according to the procedure reported in step-6 of Scheme-1, from (S)-ethyl 2-(2-((7-(3-(1-aminoethyl)phenyl)benzofuran-5-yl)methoxy)phenyl)acetate (72b) (145 mg, 0.34 mmol) in MeOH/THF (5 mL) using a solution of lithium hydroxide monohydrate (57 mg, 1.35 mmol) in water (1 mL). This gave after workup and purification by reverse phase column [C18 (50 g), eluting with ACN in water (containing 0.1% HCl) from 0-100%] (S)-2-(2-((7-(3-(1-aminoethyl)phenyl)benzofuran-5-yl)methoxy)phenyl)acetic acid (72c) (114 mg, 84% yield) HCl salt as a white solid; $^1$H NMR (300 MHz, DMSO-d$_6$) δ 12.26 (s, 1H, D$_2$O exchangeable), 8.66 (s, 3H, D$_2$O exchangeable), 8.11 (d, J=2.2 Hz, 1H), 8.02 (s, 1H), 7.96-7.86 (m, 1H), 7.76 (d, J=1.5 Hz, 1H), 7.68 (d, J=1.6 Hz, 1H), 7.65-7.54 (m, 2H), 7.30-7.16 (m, 2H), 7.15-7.03 (m, 2H), 6.90 (t, J=7.3 Hz, 1H), 5.27 (s, 2H), 4.57-4.41 (m, 1H), 3.60 (s, 2H), 1.60 (d, J=6.7 Hz, 3H); MS (ES+): 402.3 (M+1); 424.3 (M+Na); (ES−): 400.4 (M−1), 436.3 (M+Cl).

Scheme-73

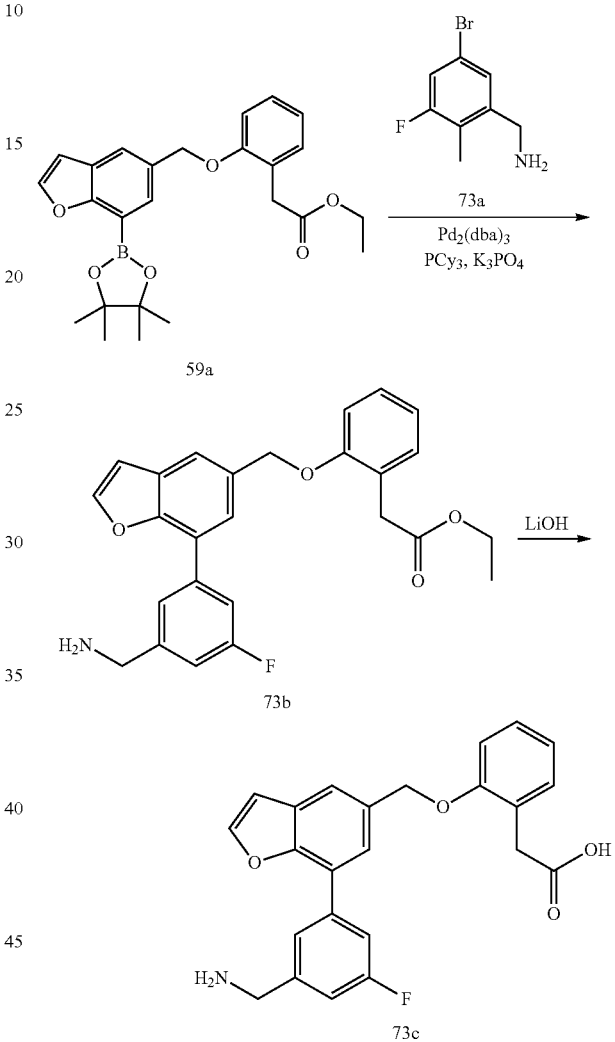

Preparation of 2-(2-((7-(3-(aminomethyl)-5-fluorophenyl)benzofuran-5-yl)methoxy)phenyl)acetic Acid (73c)

Step-1: Preparation of Ethyl 2-(2-((7-(3-(aminomethyl)-5-fluorophenyl)benzofuran-5-yl)methoxy) phenyl)acetate (73b)

Compound 73b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (400 mg, 0.92 mmol) in dioxane (5 mL) using (3-bromo-5-fluorophenyl)methanamine (73a) (374 mg, 1.83 mmol; CAS #1094555-68-6), tripotassium phosphate (3M aqueous, 0.52 mL, 1.56 mmol), tricyclohexylphosphine (77 mg, 0.28 mmol) and Pd$_2$(dba)$_3$ (84 mg, 0.092 mmol) under an Ar atmosphere and heating at 120° C. for 90 min in a microwave. This gave after workup, purification by flash column chromatography [silica (12 g), DMA80 in DCM from 0-70%] ethyl 2-(2-((7-(3-(aminomethyl)-5-fluorophenyl)benzofuran-5-yl)methoxy)phenyl)acetate (73b) (223 mg, 56% yield) as a white solid; $^1$H NMR (300 MHz, DMSO-$d_6$) δ 8.62 (s, 3H, $D_2O$ exchangeable), 8.14 (d, J=2.2 Hz, 1H), 7.91 (d, J=1.7 Hz, 1H), 7.80-7.72 (m, 2H), 7.68 (d, J=1.6 Hz, 1H), 7.54-7.46 (m, 1H), 7.30-7.19 (m, 2H), 7.14-7.06 (m, 2H), 6.95-6.87 (m, 1H), 5.25 (s, 2H), 4.15 (s, 2H), 3.95 (q, J=7.1 Hz, 2H), 3.64 (s, 2H), 1.00 (t, J=7.1 Hz, 3H); MS (ES+): 434.3 (M+1); (ES−): 468.3 (M+Cl);

Step-2: Preparation of 2-(2-((7-(3-(aminomethyl)-5-fluorophenyl)benzofuran-5-yl)methoxy)phenyl)acetic Acid (73c)

Compound 73c was prepared according to the procedure reported in step-6 of Scheme-1, from ethyl 2-(2-((7-(3-(aminomethyl)-5-fluorophenyl)benzofuran-5-yl)methoxy)phenyl)acetate (73b) (89 mg, 0.21 mmol) in MeOH/THF (5 mL) using a solution of lithium hydroxide monohydrate (35 mg, 0.82 mmol) in water (1 mL). This gave after workup and purification by reverse phase column [C18 (50 g), eluting with ACN in water (containing 0.1% HCl) from 0-100%] 2-(2-((7-(3-(aminomethyl)-5-fluorophenyl)benzofuran-5-yl)methoxy)phenyl)acetic acid (73c) (64 mg, 77% yield) as a white solid; $^1$H NMR (300 MHz, DMSO-$d_6$) δ 12.26 (s, 1H, $D_2O$ exchangeable), 8.59 (s, 3H, $D_2O$ exchangeable), 8.13 (d, J=2.1 Hz, 1H), 7.90 (d, J=1.8 Hz, 1H), 7.83-7.74 (m, 2H), 7.72 (d, J=1.6 Hz, 1H), 7.54-7.45 (m, 1H), 7.28-7.18 (m, 2H), 7.13-7.04 (m, 2H), 6.90 (t, J=7.3 Hz, 1H), 5.27 (s, 2H), 4.16 (s, 2H), 3.60 (s, 2H); $^{19}$F NMR (282 MHz, DMSO-$d_6$) δ−112.57; MS (ES+): 406.3 (M+1); (ES−): 404.4 (M−1), 440.3 (M+Cl).

Scheme-74

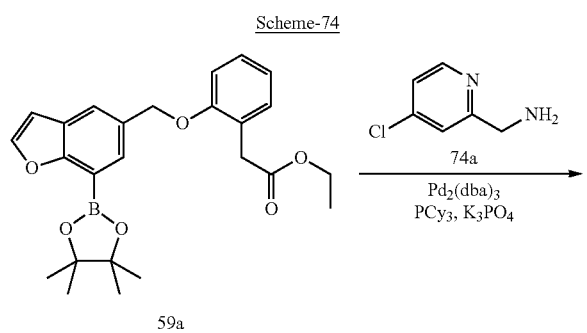

59a

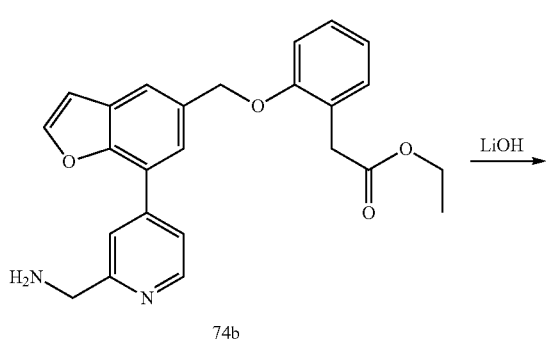

74b

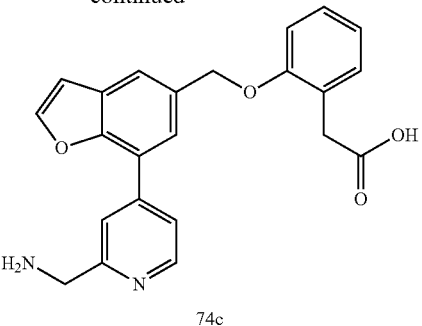

74c

Preparation of 2-(2-((7-(2-(aminomethyl)pyridin-4-yl)benzofuran-5-yl)methoxy)phenyl)acetic Acid (74c)

Step-1: Preparation of Ethyl 2-(2-((7-(2-(aminomethyl)pyridin-4-yl)benzofuran-5-yl)methoxy)phenyl)acetate (74b)

Compound 74b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (300 mg, 0.69 mmol) in dioxane (3 mL) using (4-chloropyridin-2-yl)methanamine (74a) (196 mg, 1.38 mmol; CAS #180748-30-5), tripotassium phosphate (3M aqueous, 0.39 mL, 1.169 mmol), tricyclohexylphosphine (58 mg, 0.21 mmol) and $Pd_2(dba)_3$ (63 mg, 0.069 mmol) under an Ar atmosphere and heating at 120° C. for 90 min in a microwave. This gave after workup, purification by flash column chromatography [silica (12 g), DMA80 in DCM from 0-70%] followed by purification by reverse phase column chromatography [C18 (50 g), eluting with ACN in water (containing 0.1% HCl) from 0-100%] ethyl 2-(2-((7-(2-(aminomethyl)pyridin-4-yl)benzofuran-5-yl)methoxy)phenyl)acetate (74b) (98 mg, 34% yield) HCl salt as a white solid; $^1$H NMR (300 MHz, DMSO-$d_6$) δ 8.82 (d, J=5.4 Hz, 1H), 8.74 (s, 3H, $D_2O$ exchangeable), 8.25 (s, 1H), 8.19 (d, J=2.2 Hz, 1H), 8.08 (dd, J=5.5, 1.8 Hz, 1H), 7.89-7.81 (m, 2H), 7.31-7.18 (m, 2H), 7.17-7.07 (m, 2H), 6.91 (t, J=7.4 Hz, 1H), 5.27 (s, 2H), 4.34 (q, J=5.8 Hz, 2H), 3.94 (q, J=7.1 Hz, 2H), 3.64 (s, 2H), 0.98 (t, J=7.1 Hz, 3H); MS (ES+): 417.3 (M+1); 439.3 (M+Na); (ES−): 451.3 (M+Cl).

Step-2: Preparation of 2-(2-((7-(2-(aminomethyl)pyridin-4-yl)benzofuran-5-yl)methoxy)phenyl)acetic Acid (74c)

Compound 74c was prepared according to the procedure reported in step-6 of Scheme-1, from ethyl 2-(2-((7-(2-(aminomethyl)pyridin-4-yl)benzofuran-5-yl)methoxy)phenyl)acetate (74b) (66 mg, 0.16 mmol) in MeOH/THF (5 mL) using a solution of lithium hydroxide monohydrate (27 mg, 0.63 mmol) in water (1 mL). This gave after workup and purification by reverse phase column [C18 (50 g), eluting with ACN in water (containing 0.1% HCl) from 0-100%] 2-(2-((7-(2-(aminomethyl)pyridin-4-yl)benzofuran-5-yl)methoxy)phenyl)acetic acid (74c) (36 mg, 59% yield) HCl salt as a white solid; $^1$H NMR (300 MHz, DMSO-$d_6$) δ 8.89-8.70 (m, 4H, $D_2O$ exchangeable), 8.33 (d, J=1.6 Hz, 1H), 8.19 (d, J=2.1 Hz, 1H), 8.15 (dd, J=5.6, 1.7 Hz, 1H), 7.91 (s, 2H), 7.22 (d, J=7.4 Hz, 2H), 7.16-7.04 (m, 2H), 6.90

(t, J=7.3 Hz, 1H), 5.29 (s, 2H), 4.38 (d, J=5.4 Hz, 2H), 3.61 (s, 2H); MS (ES+): 489.3 (M+1); 411.3 (M+Na); (ES−): 387.3 (M−1), 423.3 (M+Cl).

Scheme-75

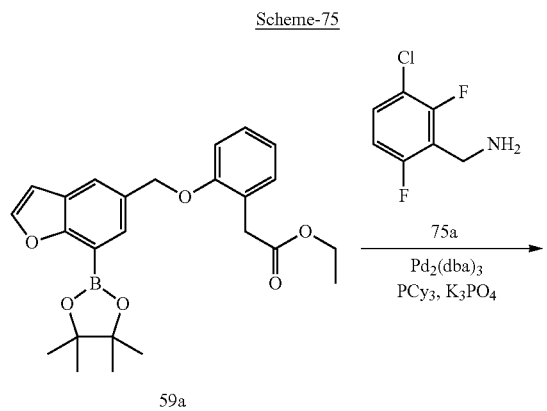

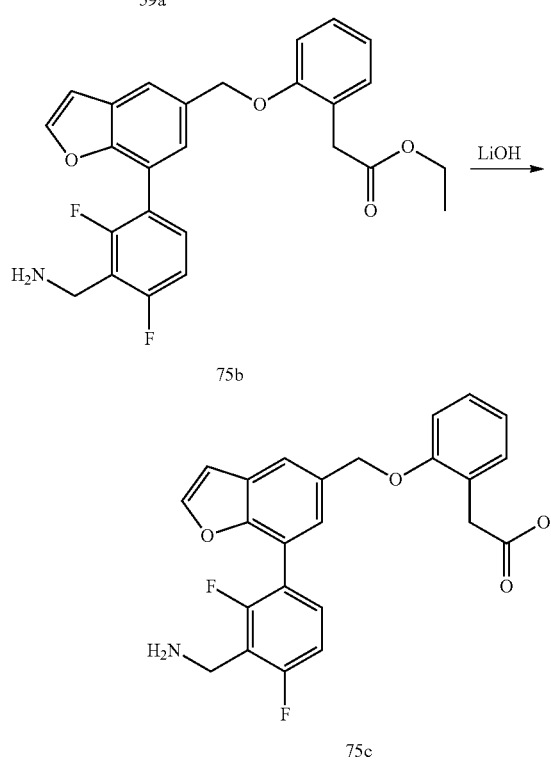

Preparation of 2-(2-((7-(3-(aminomethyl)-2,4-difluorophenyl)benzofuran-5-yl)methoxy)phenyl)acetic Acid (75c)

Step-1: Preparation of Ethyl 2-(2-((7-(3-(aminomethyl)-2,4-difluorophenyl)benzofuran-5-yl)methoxy)phenyl)acetate (75b)

Compound 75b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (400 mg, 0.917 mmol) in dioxane (6 mL) using (3-chloro-2,6-difluorophenyl)methanamine (75a) (244 mg, 1.38 mmol; CAS #261762-46-3), tripotassium phosphate (3M aqueous, 0.52 mL, 1.56 mmol), tricyclohexylphosphine (77 mg, 0.28 mmol) and Pd$_2$(dba)$_3$ (84 mg, 0.092 mmol) under an Ar atmosphere and heating at 120° C. for 90 min in a microwave. This gave after workup, purification by flash column chromatography [silica (12 g), eluting with EtOAc in hexane from 0-70%] followed by purification by reverse phase column chromatography [C18 (50 g), eluting with ACN in water (containing 0.1% HCl) from 0-100%] ethyl 2-(2-((7-(3-(aminomethyl)-2,4-difluorophenyl)benzofuran-5-yl)methoxy)phenyl)acetate (75b) (96.8 mg) as a white solid; $^1$H NMR (300 MHz, DMSO-d$_6$) δ 8.58 (s, 3H, D$_2$O exchangeable), 8.08 (d, J=2.2 Hz, 1H), 7.84-7.73 (m, 2H), 7.46-7.37 (m, 2H), 7.32-7.19 (m, 2H), 7.17-7.06 (m, 2H), 6.97-6.88 (m, 1H), 5.24 (s, 2H), 4.16 (s, 2H), 3.94 (q, J=7.1 Hz, 2H), 3.63 (s, 2H), 1.00 (t, J=7.1 Hz, 3H); $^{19}$F NMR (282 MHz, DMSO-d$_6$) δ−112.50, −113.05; MS (ES+): 452.3 (M+1); (ES−): 486.3 (M+Cl).

Step-2: Preparation of 2-(2-((7-(3-(aminomethyl)-2,4-difluorophenyl)benzofuran-5-yl)methoxy)phenyl) acetic Acid (75c)

Compound 75c was prepared according to the procedure reported in step-6 of Scheme-1, from ethyl 2-(2-((7-(3-(aminomethyl)-2,4-difluorophenyl)benzofuran-5-yl)methoxy)phenyl)acetate (75b) (130 mg, 0.29 mmol) in MeOH/THF (10 mL) using a solution of lithium hydroxide monohydrate (36 mg, 0.86 mmol) in water (1 mL). This gave after workup and purification by reverse phase column [C18 (50 g), eluting with ACN in water (containing 0.1% HCl) from 0-100%] 2-(2-((7-(3-(aminomethyl)-2,4-difluorophenyl)benzofuran-5-yl)methoxy)phenyl)acetic acid (75c) (79 mg, 65% yield) as a white solid; $^1$H NMR (300 MHz, DMSO-d$_6$) δ 8.89 (s, 2H, D$_2$O exchangeable), 8.07 (d, J=2.2 Hz, 1H), 7.84 (d, J=1.6 Hz, 1H), 7.82-7.73 (m, 1H), 7.47 (s, 1H), 7.44-7.34 (m, 1H), 7.27-7.18 (m, 2H), 7.13-7.04 (m, 2H), 6.95-6.86 (m, 1H), 5.27 (s, 2H), 4.16 (s, 2H), 3.59 (s, 2H); $^{19}$F NMR (282 MHz, DMSO-d$_6$) δ−112.64, −112.92; MS (ES+): 424.3 (M+1); 446.3 (M+Na); (ES−): 422.3 (M−1), 458.3 (M+Cl).

Scheme-76

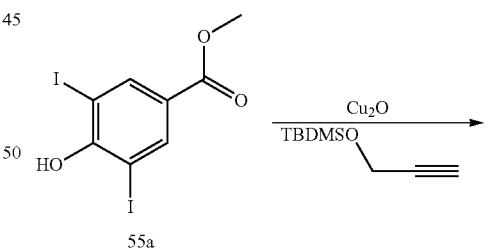

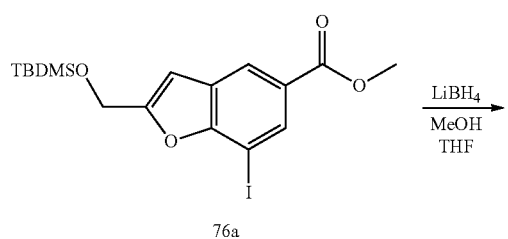

-continued

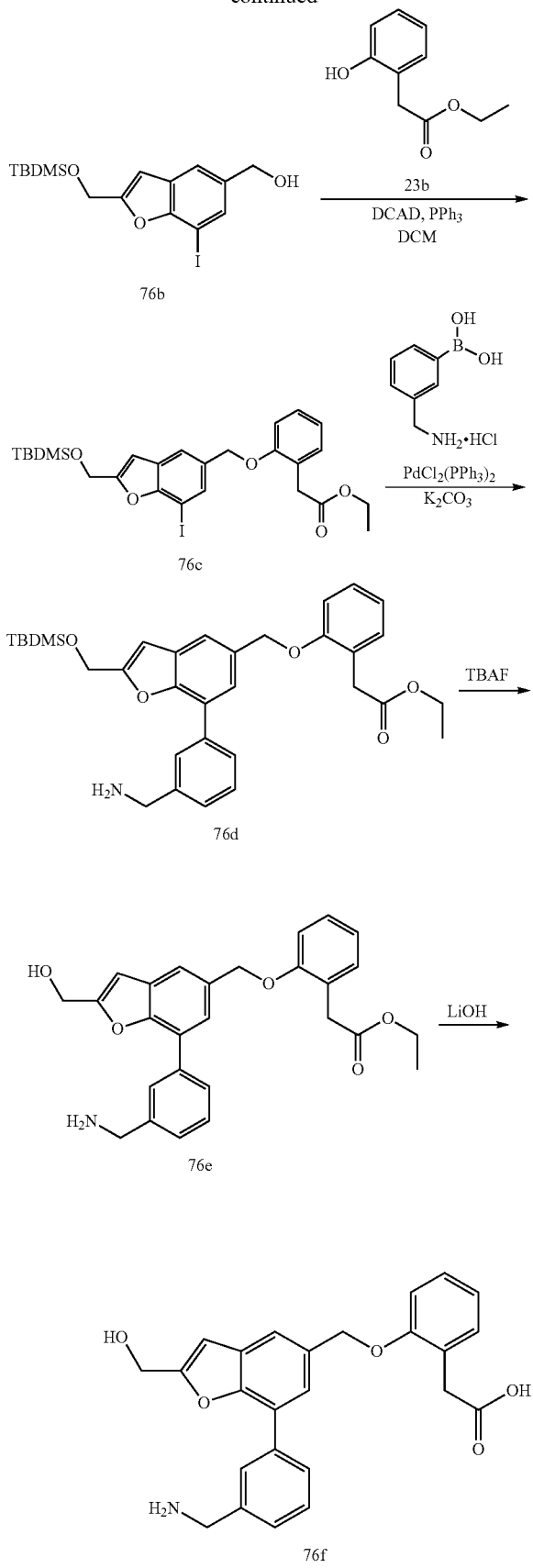

Preparation of 2-(2-((7-(3-(aminomethyl)phenyl)-2-(hydroxymethyl)benzofuran-5-yl)methoxy)phenyl) acetic Acid (76f)

Step-1: Preparation of methyl 2-(((tert-butyldimethylsilyl)oxy)methyl)-7-iodobenzofuran-5-carboxylate (76a)

Compound 76a was prepared according to the procedure reported in step-1 of Scheme-55, from methyl 4-hydroxy-3,5-diiodobenzoate (55a) (5 g, 12.38 mmol) in pyridine (10 mL) using tert-butyldimethyl(prop-2-ynyloxy)silane (2.11 g, 12.38 mmol; CAS #76782-82-6) and copper(I) oxide (0.89 g, 6.19 mmol). This gave after workup and purification by flash column chromatography [silica (80 g), eluting with EtOAc in hexane from 0-70%] methyl 2-(((tert-butyldimethylsilyl)oxy)methyl)-7-iodobenzofuran-5-carboxylate (76a) (3.2 g, 58% yield) as a clear oil; $^1$H NMR (300 MHz, DMSO-$d_6$) δ 8.13 (d, J=1.6 Hz, 1H), 8.07 (d, J=1.6 Hz, 1H), 6.95 (s, 1H), 4.72 (s, 2H), 3.74 (s, 3H), 0.76 (s, 9H), −0.00 (s, 6H); MS (ES+): 469.1 (M+Na).

Step-2: Preparation of (2-(((tert-butyldimethylsilyl)oxy)methyl)-7-iodobenzofuran-5-yl)methanol (76b)

To a solution of methyl 2-(((tert-butyldimethylsilyl)oxy)methyl)-7-iodobenzofuran-5-carboxylate (76a) (12 g, 26.9 mmol) in THF (150 mL) at −78° C. was added LiBH$_4$ (26.9 mL, 53.8 mmol, 2 M solution in THF) and MeOH (2.2 mL, 53.8 mmol). The reaction mixture was stirred at RT for 24 h, quenched with saturated aqueous NH$_4$Cl solution and extracted with EtOAc. The organic layer was washed with brine, dried, filtered and concentrated in vacuum. The residue obtained was purified by flash column chromatography [silica (80 g), eluting with EtOAc in hexane from 0-60%] to afford (2-(((tert-butyldimethylsilyl)oxy)methyl)-7-iodobenzofuran-5-yl)methanol (76b) (10.4 g, 92% yield) as a clear oil; $^1$H NMR (300 MHz, DMSO-$d_6$) δ 7.62 (d, J=1.5 Hz, 1H), 7.52 (d, J=1.4 Hz, 1H), 6.92 (d, J=1.2 Hz, 1H), 5.25 (t, J=5.8, 1.2 Hz, 1H, D$_2$O exchangeable), 4.81 (s, 2H), 4.53 (d, J=5.8 Hz, 2H), 0.89 (s, 9H), 0.12 (s, 6H); MS (ES+): 441.2 (M+Na); (ES−): 417.2 (M−1).

Step-3: Preparation of Ethyl 2-(2-((2-(((tert-butyldimethylsilyl)oxy)methyl)-7-iodobenzofuran-5-yl) methoxy)phenyl)acetate (76c)

Compound 76c was prepared according to the procedure reported in step-2 of Scheme-23 from (2-(((tert-butyldimethylsilyl)oxy)methyl)-7-iodobenzofuran-5-yl)methanol (76b) (2.6 g, 6.22 mmol) in DCM (50 mL) using triphenylphosphine (1.79 g, 6.84 mmol), ethyl 2-(2-hydroxyphenyl) acetate (23b) (1.23 g, 6.84 mmol) and di-(4-chlorobenzyl)azodicarboxylate (DCAD, 2.51 g, 6.84 mmol) in DCM (20 mL). This gave after workup and purification by flash column chromatography [silica (40 g), eluting with EtOAc in hexane from 0-50%] ethyl 2-(2-((2-(((tert-butyldimethyl silyl)oxy)methyl)-7-iodobenzofuran-5-yl)methoxy)phenyl) acetate (76c) (2.86 g, 79% yield) as a clear oil; $^1$H NMR (300 MHz, DMSO-$d_6$) δ 7.71 (d, J=1.5 Hz, 1H), 7.64 (d, J=1.5 Hz, 1H), 7.28-7.18 (m, 2H), 7.07 (d, J=8.1 Hz, 1H), 6.96 (s, 1H), 6.95-6.87 (m, 1H), 5.13 (s, 2H), 4.82 (s, 2H), 4.01 (q, J=7.1 Hz, 2H), 3.61 (s, 2H), 1.07 (t, J=7.1 Hz, 3H), 0.89 (s, 9H), 0.12 (s, 6H).

Step-4: Preparation of Ethyl 2-(2-((7-(3-(aminomethyl)phenyl)-2-(((tert-butyldimethylsilyl)oxy) methyl)benzofuran-5-yl)methoxy)phenyl)acetate (76d)

Compound 76d was prepared according to the procedure reported in step-3 of Scheme-1 from ethyl 2-(2-((2-(((tert-butyldimethyl silyl)oxy)methyl)-7-iodobenzofuran-5-yl) methoxy)phenyl)acetate (76c) (1.2 g, 2.07 mmol) in dioxane (20 mL) using 3-(aminomethyl)phenylboronic acid hydrochloride (6c) (0.58 g, 3.10 mmol), a solution of K₂CO₃ (0.86 g, 6.20 mmol) in water (4 mL), bis(triphenylphosphine) palladium(II) chloride (0.218 g, 0.310 mmol) and heating at 100° C. for 3 h on oil bath. This gave after workup, purification by flash column chromatography [silica (12 g), eluting with EtOAc/MeOH (9:1, v/v) in hexane from 0-70%] followed by purification by reverse phase column chromatography [C18 (50 g), eluting with ACN in water (containing 0.1% HCl) from 0-100%] ethyl 2-(2-((7-(3-(aminomethyl)phenyl)-2-(((tert-butyldimethylsilyl)oxy) methyl)benzofuran-5-yl)methoxy)phenyl)acetate (76d) (1.01 g, 87% yield) as a white solid; MS (ES+): 560.4 (M+1).

Step-5: Preparation of Ethyl 2-(2-((7-(3-(aminomethyl)phenyl)-2-(hydroxymethyl)benzofuran-5-yl) methoxy)phenyl)acetate (76e)

To a solution of ethyl 2-(2-((7-(3-(aminomethyl)phenyl)-2-(((tert-butyldimethylsilyl)oxy)methyl)benzofuran-5-yl) methoxy)phenyl)acetate (76d) (175 mg, 0.31 mmol) in THF (20 mL) at 0° C. was added TBAF (102 mg, 0.39 mmol). The reaction mixture was allowed to warm to RT over a period of 1 h and quenched with saturated aqueous NH₄Cl solution. The reaction mixture was extracted with EtOAc and the combined organic layers were dried, filtered and concentrated in vacuum. The residue obtained was purified by flash column chromatography [silica (12 g), eluting with DMA80 in DCM from 0-70%] followed by purification using reverse phase column chromatography [C18 (50 g), eluting with ACN in water (containing 0.1% HCl) from 0-100%] to afford ethyl 2-(2-((7-(3-(aminomethyl)phenyl)-2-(hydroxymethyl)benzofuran-5-yl)methoxy)phenyl)acetate (76e) (70 mg, 50% yield) HCl salt as a white solid; ¹H NMR (300 MHz, DMSO-d₆) δ 8.41 (s, 3H, D₂O exchangeable), 7.98 (s, 1H), 7.92 (dt, J=7.5, 1.7 Hz, 1H), 7.66 (d, J=1.6 Hz, 1H), 7.64-7.51 (m, 3H), 7.31-7.18 (m, 2H), 7.11 (d, J=8.1 Hz, 1H), 6.96-6.87 (m, 1H), 6.85 (s, 1H), 5.55 (t, J=5.9 Hz, 1H, D₂O exchangeable), 5.23 (s, 2H), 4.61 (d, J=5.9 Hz, 2H), 4.13 (s, 2H), 3.94 (q, J=7.1 Hz, 2H), 3.63 (s, 2H), 1.00 (t, J=7.1 Hz, 3H); MS (ES+): 446.3 (M+1); 468.3 (M+Na); (ES−): 480.4 (M+Cl).

Step-6: Preparation of 2-(2-((7-(3-(aminomethyl) phenyl)-2-(hydroxymethyl)benzofuran-5-yl) methoxy)phenyl)acetic Acid (76f)

Compound 76f was prepared according to the procedure reported in step-6 of Scheme-1, from ethyl 2-(2-((7-(3-(aminomethyl)phenyl)-2-(hydroxymethyl)benzofuran-5-yl) methoxy)phenyl)acetate (76e) (700 mg, 1.57 mmol) in MeOH/THF (30 mL) using a solution of lithium hydroxide monohydrate (165 mg, 3.93 mmol) in water (3.0 mL). This gave after workup and purification by reverse phase column [C18 (50 g), eluting with ACN in water (containing 0.1% HCl) from 0-100%] 2-(2-((7-(3-(aminomethyl)phenyl)-2-(hydroxymethyl)benzofuran-5-yl)methoxy)phenyl)acetic acid (76f) (455 mg, 69% yield) HCl salt as a white solid; ¹H NMR (300 MHz, DMSO-d₆) δ 12.21 (s, 1H, D₂O exchangeable), 8.61 (s, 3H, D₂O exchangeable), 8.02 (s, 1H), 7.96-7.89 (m, 1H), 7.69 (d, J=1.6 Hz, 1H), 7.62 (d, J=1.7 Hz, 1H), 7.60-7.54 (m, 2H), 7.28-7.18 (m, 2H), 7.09 (d, J=8.1 Hz, 1H), 6.90 (t, J=7.4 Hz, 1H), 6.84 (s, 1H), 5.66-5.49 (m, 1H, D₂O exchangeable), 5.25 (s, 2H), 4.62 (d, J=4.2 Hz, 2H), 4.13 (s, 2H), 3.60 (s, 2H); MS (ES+): 418.3 (M+1); (ES−): 416.3 (M−1), 452.3 (M+Cl).

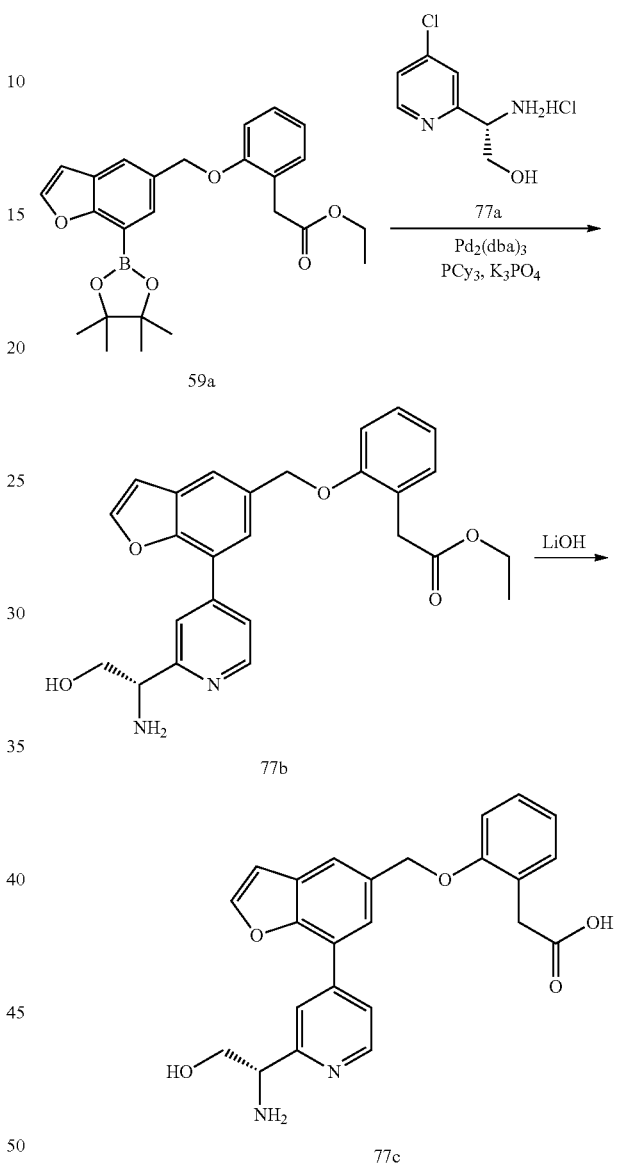

Scheme-77

Preparation of (S)-2-(2-((7-(2-(1-amino-2-hydroxyethyl)pyridin-4-yl)benzofuran-5-yl)methoxy)phenyl) acetic Acid (77c)

Step-1: Preparation of (S)-ethyl 2-(2-((7-(2-(1-amino-2-hydroxyethyl)pyridin-4-yl)benzofuran-5-yl) methoxy)phenyl)acetate (77b)

Compound 77b was prepared according to the procedure reported in step-3 of Scheme-1 from ethyl 2-(2-((7-(4,4,5,5-tetramethyl-1,3,2-dioxaborolan-2-yl)benzofuran-5-yl) methoxy)phenyl)acetate (59a) (400 mg, 0.917 mmol) in dioxane (6 mL) using (S)-2-amino-2-(4-chloropyridin-2-yl) ethanol hydrochloride (77a) (288 mg, 1.38 mmol; CAS #1213411-99-4), tripotassium phosphate (3M aqueous, 1.13 mL, 3.39 mmol), tricyclohexylphosphine (77 mg, 0.28 mmol) and Pd$_2$(dba)$_3$ (84 mg, 0.092 mmol) under an Ar atmosphere and heating at 120° C. for 90 min in a microwave. This gave after workup, purification by flash column chromatography [silica (12 g), eluting with DMA80 in DCM from 0-70%] followed by purification by reverse phase column chromatography [C18 (50 g), eluting with ACN in water (containing 0.1% HCl) from 0-100%] (S)-ethyl 2-(2-((7-(2-(1-amino-2-hydroxyethyl)pyridin-4-yl)benzofuran-5-yl)methoxy)phenyl)acetate (77b) (215 mg, 53% yield) HCl salt as a white solid; $^1$H NMR (300 MHz, DMSO-d$_6$) δ 8.79 (d, J=5.3 Hz, 1H), 8.64 (d, J=5.4 Hz, 3H, D$_2$O exchangeable), 8.19 (d, J=2.2 Hz, 1H), 8.15 (d, J=1.6 Hz, 1H), 8.03 (dd, J=5.3, 1.6 Hz, 1H), 7.88-7.80 (m, 2H), 7.32-7.19 (m, 2H), 7.16-7.09 (m, 2H), 6.92 (t, J=7.4 Hz, 1H), 5.27 (s, 2H), 4.61-4.49 (m, 1H), 3.99-3.82 (m, 4H), 3.65 (s, 2H), 0.99 (t, J=7.1 Hz, 3H); MS (ES+): 447.3 (M+1); 469.3 (M+Na); (ES−): 481.3 (M+Cl).

Step-2: Preparation of (S)-2-(2-((7-(2-(1-amino-2-hydroxyethyl)pyridin-4-yl)benzofuran-5-yl) methoxy)phenyl)acetic Acid (77c)

Compound 77c was prepared according to the procedure reported in step-6 of Scheme-1, from (S)-ethyl 2-(2-((7-(2-(1-amino-2-hydroxyethyl)pyridin-4-yl)benzofuran-5-yl) methoxy)phenyl)acetate (77b) (88 mg, 0.20 mmol) in MeOH/THF (10 mL) using a solution of lithium hydroxide monohydrate (25 mg, 0.59 mmol) in water (1 mL). This gave after workup and purification by reverse phase column [C18 (50 g), eluting with ACN in water (containing 0.1% HCl) from 0-100%] (S)-2-(2-((7-(2-(1-amino-2-hydroxyethyl) pyridin-4-yl)benzofuran-5-yl)methoxy)phenyl)acetic acid (77c) (31 mg, 38% yield) HCl salt as a white solid; $^1$H NMR (300 MHz, DMSO-d$_6$) δ 8.77 (d, J=5.3 Hz, 1H), 8.63-8.41 (m, 3H, D$_2$O exchangeable), 8.17 (d, J=2.1 Hz, 1H), 8.10 (s, 1H), 8.00 (dd, J=5.3, 1.6 Hz, 1H), 7.88 (s, 1H), 7.83 (d, J=1.6 Hz, 1H), 7.28-7.19 (m, 2H), 7.14-7.05 (m, 2H), 6.91 (t, J=7.3 Hz, 1H), 5.29 (s, 2H), 4.60-4.51 (m, 1H), 3.91-3.85 (m, 2H), 3.60 (s, 2H); MS (ES+): 419.3 (M+1); 441.3 (M+Na); (ES−): 417.3 (M−1), 453.3 (M+Cl).

Scheme-78

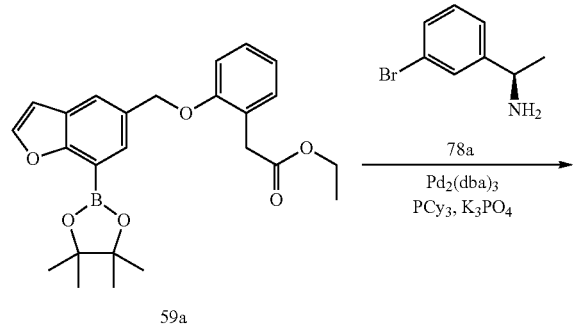

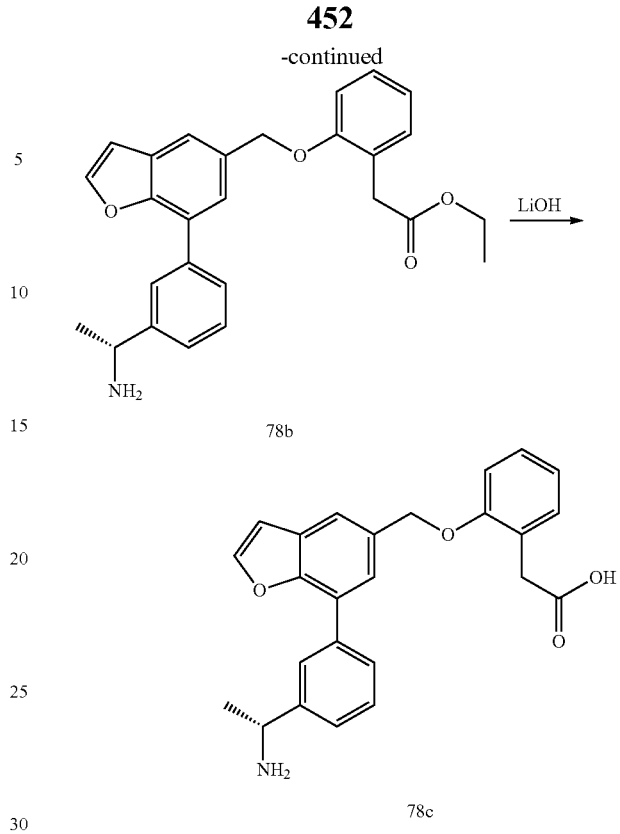

Preparation of (R)-2-(2-((7-(3-(1-aminoethyl)phenyl)benzofuran-5-yl)methoxy)phenyl)acetic Acid (78c)

Step-1: Preparation of (R)-ethyl 2-(2-((7-(3-(1-aminoethyl)phenyl)benzofuran-5-yl)methoxy)phenyl) acetate (78b)

Compound 78b was prepared according to the procedure reported in step-3 of Scheme-1 from ethyl 2-(2-((7-(4,4,5,5-tetramethyl-1,3,2-dioxaborolan-2-yl)benzofuran-5-yl) methoxy)phenyl)acetate (59a) (450 mg, 1.03 mmol) in dioxane (6 mL) using (R)-1-(3-bromophenyl)ethanamine (78a) (351 mg, 1.75 mmol; CAS #176707-77-0), tripotassium phosphate (3M aqueous, 0.58 mL, 1.75 mmol), tricyclohexylphosphine (87 mg, 0.31 mmol) and Pd$_2$(dba)$_3$ (94 mg, 0.10 mmol) under an Ar atmosphere and heating at 120° C. for 90 min in a microwave. This gave after workup, purification by flash column chromatography [silica (12 g), eluting with DMA80 in DCM from 0-70%] followed by purification by reverse phase column chromatography [C18 (50 g), eluting with ACN in water (containing 0.1% HCl) from 0-100%] (R)-ethyl 2-(2-((7-(3-(1-aminoethyl)phenyl) benzofuran-5-yl)methoxy)phenyl)acetate (78b) (300 mg, 68% yield) HCl salt as a white solid; $^1$H NMR (300 MHz, DMSO-d$_6$) δ 8.60 (s, 3H, D$_2$O exchangeable), 8.12 (d, J=2.2 Hz, 1H), 8.01 (s, 1H), 7.94-7.87 (m, 1H), 7.74 (d, J=1.5 Hz, 1H), 7.67-7.55 (m, 3H), 7.31-7.20 (m, 2H), 7.16-7.10 (m, 1H), 7.08 (d, J=2.2 Hz, 1H), 6.92 (td, J=7.4, 1.1 Hz, 1H), 5.25 (s, 2H), 4.57-4.43 (m, 1H), 3.93 (q, J=7.1 Hz, 2H), 3.64 (s, 2H), 1.59 (d, J=6.8 Hz, 3H), 0.98 (t, J=7.1 Hz, 3H); MS (ES+): 430.3 (M+1); 452.3 (M+Na); (ES−): 464.4 (M+Cl).

Step-2: Preparation of (R)-2-(2-((7-(3-(1-amino-ethyl)phenyl)benzofuran-5-yl)methoxy)phenyl)acetic Acid (78c)

Compound 78c was prepared according to the procedure reported in step-6 of Scheme-1, from (R)-ethyl 2-(2-((7-(3-(1-aminoethyl)phenyl)benzofuran-5-yl)methoxy)phenyl)acetate (78b) (156 mg, 0.36 mmol) in MeOH/THF (10 mL) using a solution of lithium hydroxide monohydrate (46 mg, 1.09 mmol) in water (1 mL). This gave after workup and purification by reverse phase column [C18 (50 g), eluting with ACN in water (containing 0.1% HCl) from 0-100%] (R)-2-(2-((7-(3-(1-aminoethyl)phenyl)benzofuran-5-yl)methoxy)phenyl)acetic acid (78c) (108 mg, 74% yield) HCl salt as a white solid; $^1$H NMR (300 MHz, DMSO-$d_6$) δ 12.24 (s, 1H, D$_2$O exchangeable), 8.62 (s, 3H, D$_2$O exchangeable), 8.11 (d, J=2.2 Hz, 1H), 8.02 (s, 1H), 7.95-7.88 (m, 1H), 7.76 (d, J=1.5 Hz, 1H), 7.68 (d, J=1.6 Hz, 1H), 7.64-7.56 (m, 2H), 7.28-7.18 (m, 2H), 7.10 (d, J=8.1 Hz, 1H), 7.06 (d, J=2.2 Hz, 1H), 6.90 (t, J=7.3 Hz, 1H), 5.27 (s, 2H), 4.50 (q, J=5.9 Hz, 1H), 3.60 (s, 2H), 1.60 (d, J=6.7 Hz, 3H); MS (ES+): 402.3 (M+1); (ES−): 400.4 (M−1), 436.3 (M+Cl).

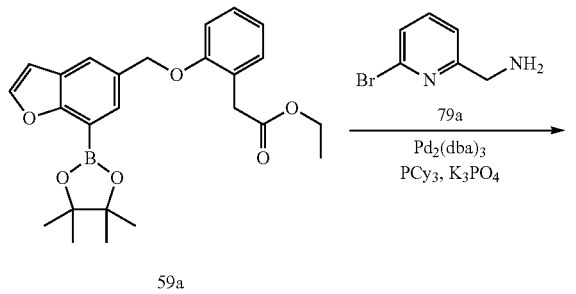

Scheme-79

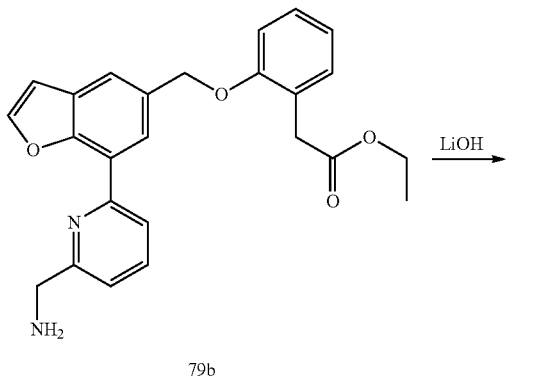

Preparation of 2-(2-((7-(6-(aminomethyl)pyridin-2-yl)benzofuran-5-yl)methoxy)phenyl)acetic Acid (79c)

Step-1: Preparation of Ethyl 2-(2-((7-(6-(aminomethyl)pyridin-2-yl)benzofuran-5-yl)methoxy)phenyl)acetate (79b)

Compound 79b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (450 mg, 1.03 mmol) in dioxane (6 mL) using (6-bromopyridin-2-yl)methanamine (79a) (289 mg, 1.55 mmol; CAS #188637-63-0), tripotassium phosphate (3M aqueous, 0.58 mL, 1.75 mmol), tricyclohexylphosphine (87 mg, 0.31 mmol) and Pd$_2$(dba)$_3$ (94 mg, 0.10 mmol) under an Ar atmosphere and heating at 120° C. for 45 min in a microwave. This gave after workup, purification by flash column chromatography [silica (12 g), eluting with EtOAc in hexane from 0-70%] followed by purification by reverse phase column chromatography [C18 (50 g), eluting with ACN in water (containing 0.1% HCl) from 0-100%] ethyl 2-(2-((7-(6-(aminomethyl)pyridin-2-yl)benzofuran-5-yl)methoxy)phenyl)acetate (79b) (146 mg, 34% yield) HCl salt as a white solid; $^1$H NMR (300 MHz, DMSO-$d_6$) δ 8.69 (s, 3H, D$_2$O exchangeable), 8.50 (d, J=1.6 Hz, 1H), 8.39-8.31 (m, 1H), 8.17 (d, J=2.1 Hz, 1H), 8.06 (t, J=7.8 Hz, 1H), 7.82 (d, J=1.7 Hz, 1H), 7.55 (d, J=7.7 Hz, 1H), 7.32-7.19 (m, 2H), 7.17-7.06 (m, 2H), 6.92 (t, J=7.4 Hz, 1H), 5.28 (s, 2H), 4.30 (q, J=5.9 Hz, 2H), 3.97 (q, J=7.1 Hz, 2H), 3.64 (s, 2H), 1.01 (t, J=7.1 Hz, 3H); MS (ES+): 417.3 (M+1); 439.3 (M+Na).

Step-2: Preparation of 2-(2-((7-(6-(aminomethyl)pyridin-2-yl)benzofuran-5-yl)methoxy)phenyl)acetic Acid (79c)

Compound 79c was prepared according to the procedure reported in step-6 of Scheme-1, from ethyl 2-(2-((7-(6-(aminomethyl)pyridin-2-yl)benzofuran-5-yl)methoxy)phenyl)acetate (79b) (66 mg, 0.16 mmol) in MeOH/THF (10 mL) using a solution of lithium hydroxide monohydrate (20 mg, 0.48 mmol) in water (1 mL). This gave after workup and purification by reverse phase column [C18 (50 g), eluting with ACN in water (containing 0.1% HCl) from 0-100%] 2-(2-((7-(6-(aminomethyl)pyridin-2-yl)benzofuran-5-yl)methoxy)phenyl)acetic acid (79c) (36 mg, 59% yield) HCl salt as a white solid; $^1$H NMR (300 MHz, DMSO-$d_6$) δ 8.56 (s, 3H, D$_2$O exchangeable), 8.48 (d, J=1.7 Hz, 1H), 8.35 (d, J=7.9 Hz, 1H), 8.16 (d, J=2.2 Hz, 1H), 8.05 (t, J=7.8 Hz, 1H), 7.86 (d, J=1.7 Hz, 1H), 7.53 (d, J=7.7 Hz, 1H), 7.29-7.19 (m, 2H), 7.14-7.05 (m, 2H), 6.91 (t, J=7.4, 1.1 Hz, 1H), 5.30 (s, 2H), 4.35-4.28 (m, 2H), 3.61 (s, 2H); MS (ES+): 389.3 (M+1); (ES−): 387.3.3 (M−1); 423.3 (M+Cl).

Scheme-80

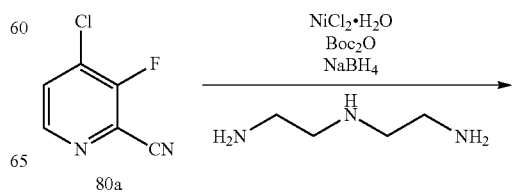

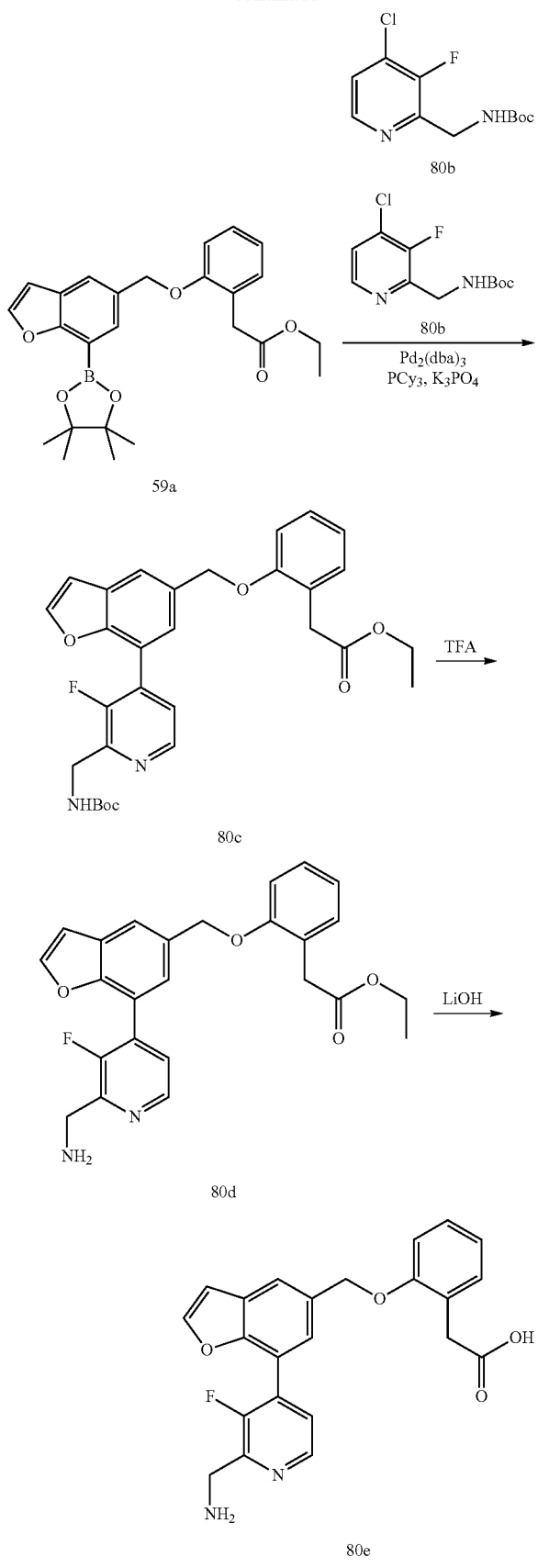

Preparation of 2-(2-((7-(2-(aminomethyl)-3-fluoropyridin-4-yl)benzofuran-5-yl)methoxy)phenyl)acetic Acid (80e)

Step-1: Preparation of tert-butyl ((4-chloro-3-fluoropyridin-2-yl)methyl)carbamate (80b)

To a solution of 4-chloro-3-fluoropicolinonitrile (80a) (0.26 g, 1.661 mmol; CAS #1155847-43-0) in Methanol (15 mL) was added BOC-Anhydride (0.54 g, 2.49 mmol), nickel(II) chloride hydrate (0.025 g, 0.17 mmol). To the reaction mixture was added sodium borohydride (0.19 g, 4.98 mmol) over a period of 2 h. The reaction mixture was quenched with N1-(2-aminoethyl)ethane-1,2-diamine (0.9 mL, 8.30 mmol) and continued stirring at RT for 2 h. The reaction mixture was concentrated in vacuum and the residue obtained was partitioned between water (60 mL) and EtOAc (60 mL). The organic layer was separated and aqueous layer was extracted with EtOAc (40 mL). The combined organic layers were washed with brine, dried, filtered and concentrated in vacuum. The residue obtained was purified by flash column chromatography [silica gel 12 g, eluting with EtOAc in hexanes 0 to 60%] to afford tert-butyl ((4-chloro-3-fluoropyridin-2-yl)methyl)carbamate (80b)(0.26 g, 60% yield) as a crystalline solid.

Step-2: Preparation of Ethyl 2-(2-((7-(2-(((tert-butoxycarbonyl)amino)methyl)-3-fluoropyridin-4-yl)benzofuran-5-yl)methoxy)phenyl)acetate (80c)

Compound 80c was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (243 mg, 0.56 mmol) in dioxane (6 mL) using tert-butyl ((4-chloro-3-fluoropyridin-2-yl)methyl)carbamate (80b) (145 mg, 0.56 mmol), tripotassium phosphate (3M aqueous, 0.32 mL, 0.95 mmol), tricyclohexylphosphine (47 mg, 0.17 mmol) and Pd$_2$(dba)$_3$ (51 mg, 0.056 mmol) under an Ar atmosphere and heating at 120° C. for 90 min in a microwave. This gave after workup, purification by flash column chromatography [silica (12 g), eluting with EtOAc in hexane from 0-70%] ethyl 2-(2-((7-(2-(((tert-butoxycarbonyl)amino)methyl)-3-fluoropyridin-4-yl)benzofuran-5-yl)methoxy)phenyl)acetate (80c) (185 mg, 62% yield) as a white solid; $^1$H NMR (300 MHz, DMSO-d$_6$) δ 8.50 (d, J=5.0 Hz, 1H), 8.11 (d, J=2.1 Hz, 1H), 7.85 (d, J=1.5 Hz, 1H), 7.63 (t, J=5.3 Hz, 1H), 7.53 (s, 1H), 7.34-7.28 (m, 1H), 7.28-7.19 (m, 2H), 7.15-7.08 (m, 2H), 6.91 (td, J=7.3, 1.3 Hz, 1H), 5.25 (s, 2H), 3.95-3.86 (m, 2H), 3.62 (s, 2H), 3.34 (s, 2H), 1.39 (s, 9H), 1.00-0.92 (m, 3H); MS (ES+): 535.4 (M+1); 557.4 (M+Na); (ES-): 534.3 (M-1).

Step-3: Preparation of Ethyl 2-(2-((7-(2-(aminomethyl)-3-fluoropyridin-4-yl)benzofuran-5-yl)methoxy)phenyl)acetate (80d)

Compound 80d was prepared according to the procedure reported in step-5 of Scheme-1 from ethyl 2-(2-((7-(2-(((tert-butoxycarbonyl)amino)methyl)-3-fluoropyridin-4-yl)benzofuran-5-yl)methoxy)phenyl)acetate (80c) (182 mg, 0.34 mmol) in DCM (5 mL) using TFA (0.26 mL, 3.40 mmol). This gave after workup and purification by flash column chromatography [silica (12 g), eluting with DMA80 in DCM from 0-50%] followed by reverse phase column purification [C18 (50 g), eluting with ACN in water (containing 0.1% HCl) from 0-100%] ethyl 2-(2-((7-(2-(aminomethyl)-3-fluoropyridin-4-yl)benzofuran-5-yl)methoxy) phenyl)acetate (80d) (136 mg, 92% yield) HCl salt as a white solid; $^1$H NMR (300 MHz, DMSO-d$_6$) δ 8.63 (d, J=5.0 Hz, 4H, partially D$_2$O exchangeable), 8.12 (d, J=2.2 Hz, 1H), 7.89 (d, J=1.6 Hz, 1H), 7.80 (t, J=5.3 Hz, 1H), 7.57 (s, 1H), 7.31-7.19 (m, 2H), 7.16-7.09 (m, 2H), 6.92 (td, J=7.4, 1.1 Hz, 1H), 5.27 (s, 2H), 4.36 (s, 2H), 3.94 (q, J=7.1, 1.3 Hz, 2H), 3.63 (s, 2H), 1.00 (t, J=7.1, 1.3 Hz, 3H); $^{19}$F NMR (282 MHz, DMSO-d$_6$) δ−128.52; MS (ES+): 435.3 (M+1); (ES−): 469.3 (M+Cl).

Step-4: Preparation of 2-(2-((7-(2-(aminomethyl)-3-fluoropyridin-4-yl)benzofuran-5-yl)methoxy)phenyl) acetic Acid (80e)

Compound 80e was prepared according to the procedure reported in step-6 of Scheme-1, from ethyl 2-(2-((7-(2-(aminomethyl)-3-fluoropyridin-4-yl)benzofuran-5-yl) methoxy)phenyl)acetate (80d) (61 mg, 0.14 mmol) in MeOH/THF (10 mL) using a solution of lithium hydroxide monohydrate (18 mg, 0.42 mmol) in water (1 mL). This gave after workup and purification by reverse phase column [C18 (50 g), eluting with ACN in water (containing 0.1% HCl) from 0-100%] 2-(2-((7-(2-(aminomethyl)-3-fluoropyridin-4-yl)benzofuran-5-yl)methoxy)phenyl)acetic acid (80e) (32 mg, 56% yield) HCl salt as a white solid; $^1$H NMR (300 MHz, DMSO-d$_6$) δ 8.73-8.58 (m, 4H, partially D$_2$O exchangeable), 8.11 (d, J=2.1 Hz, 1H), 7.92 (d, J=1.6 Hz, 1H), 7.80 (t, J=5.3 Hz, 1H), 7.61 (s, 1H), 7.28-7.19 (m, 2H), 7.14-7.06 (m, 2H), 6.91 (t, J=7.3 Hz, 1H), 5.29 (s, 2H), 4.39-4.33 (m, 2H), 3.59 (s, 2H); $^{19}$F NMR (282 MHz, DMSO-d$_6$) δ−128.34; MS (ES+): 407.2 (M+1); 429.2 (M+Na); (ES−): 405.3 (M−1); 441.3 (M+Cl).

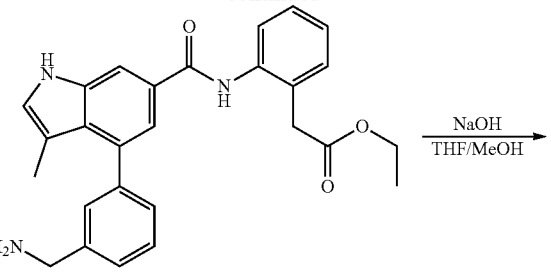

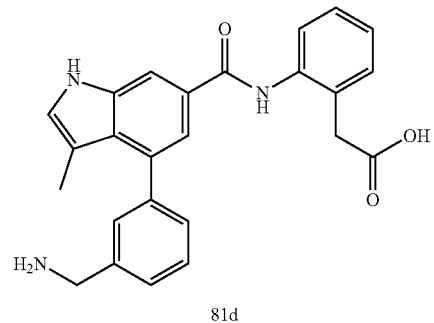

Preparation of 2-(2-(4-(3-(aminomethyl)phenyl)-3-methyl-1H-indole-6-carboxamido)phenyl)acetic Acid (81d)

Step-1: Preparation of Ethyl 2-(2-(4-bromo-3-methyl-1H-indole-6-carboxamido)phenyl)acetate (81b)

Compound 81b was prepared according to the procedure reported in step-4 of Scheme-1 from 4-bromo-3-methyl-1H-indole-6-carboxylic acid (81a) (0.3 g, 1.18 mmol; CAS #1360890-98-7) in methanol (10 mL) using ethyl 2-(2-aminophenyl)acetate (5e) (233 mg, 1.30 mmol) and EDCI.HCl (272 mg, 1.42 mmol). This gave after workup and purification by flash column chromatography [silica (12 g), eluting with 0-60% EtOAc/MeOH (9:1) in hexane from 0-100%] ethyl 2-(2-(4-bromo-3-methyl-1H-indole-6-carboxamido)phenyl)acetate (81b) (0.11 g, 22% yield) as an off white solid; MS (ES+): 437.1 & 439.1 (M+Na), MS (ES−): 449.2 & 451.1 (M+Cl).

Step-2: Preparation of Ethyl 2-(2-(4-(3-(aminomethyl)phenyl)-3-methyl-1H-indole-6-carboxamido) phenyl)acetate (81c)

Compound 81c was prepared according to the procedure reported in step-3 of Scheme-1 from ethyl 2-(2-(4-bromo-3-methyl-1H-indole-6-carboxamido)phenyl)acetate (81b) (60 mg, 0.14 mmol) in dioxane (3 mL) using 3-(aminomethyl)phenylboronic acid hydrochloride (6c) (41 mg, 0.22 mmol), tripotassium phosphate (1.3M, 0.33 mL, 0.43 mmol), tricyclohexylphosphine (12 mg, 0.04 mmol) and Pd$_2$(dba)$_3$ (13 mg, 0.01 mmol) under an Ar atmosphere and heating at 125° C. for 90 min in a microwave. This gave after workup, purification by flash column chromatography [silica (12 g), eluting with DMA80 in DCM from 0-60%] followed by purification by reverse phase column chromatography [C18 (50 g), eluting with ACN in water (containing 0.1% HCl) from 0-100%] ethyl 2-(2-(4-(3-(aminomethyl)phenyl)-

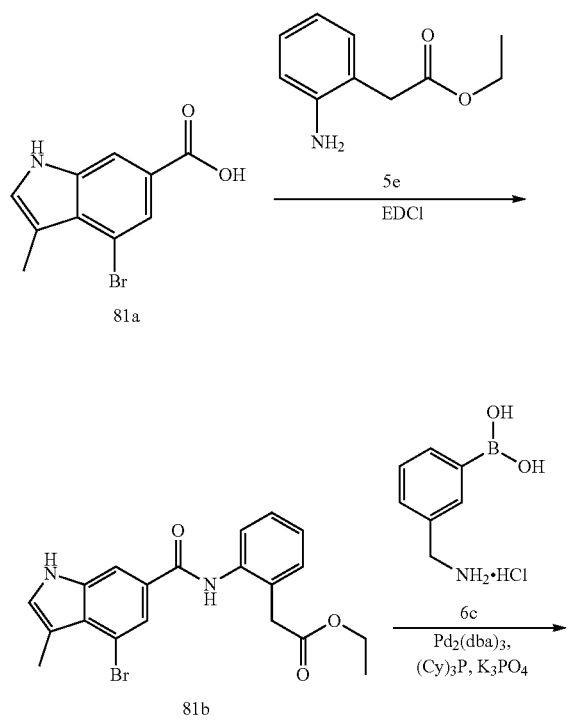

3-methyl-1H-indole-6-carboxamido)phenyl)acetate (81c) (0.03 g, 39% yield) HCl salt as a white solid; MS (ES+): 442.3 (M+1), MS (ES−): 440.4 (M−1).

Step-3: Preparation of 2-(2-(4-(3-(aminomethyl) phenyl)-3-methyl-1H-indole-6-carboxamido)phenyl) acetic Acid (81d)

Compound 81d was prepared according to the procedure reported in step-4 of Scheme-4, from ethyl 2-(2-(4-(3-(aminomethyl)phenyl)-3-methyl-1H-indole-6-carboxamido)phenyl)acetate (81c) (0.02 g, 0.05 mmol) in THF/MeOH (5 mL) using a solution of sodium hydroxide (0.02 g, 0.45 mmol) in water (2 mL). This gave after workup and purification by reverse phase column [C18 (50 g), eluting with ACN in water (containing 0.1% HCl) from 0-100%] 2-(2-(4-(3-(aminomethyl)phenyl)-3-methyl-1H-indole-6-carboxamido)phenyl)acetic acid (81d) (0.01 g, 43% yield) HCl salt as a white solid; $^1$H NMR (300 MHz, DMSO-$d_6$) δ 12.33 (s, 1H), 11.38 (s, 1H), 9.98 (s, 1H), 8.25 (bs, 3H), 8.06 (s, 1H), 7.57 (m, 1H), 7.54-7.44 (m, 4H), 7.39-7.24 (m, 3H), 7.21 (m, 1H), 4.13 (d, J=5.5 Hz, 2H), 3.66 (s, 2H), 1.85 (s, 3H); MS (ES+): 414.3 (M+1), 436.3 (M+Na); MS (ES−): 412.4 (M−1), 448.3 (M+Cl). HPLC purity: 97.98%.

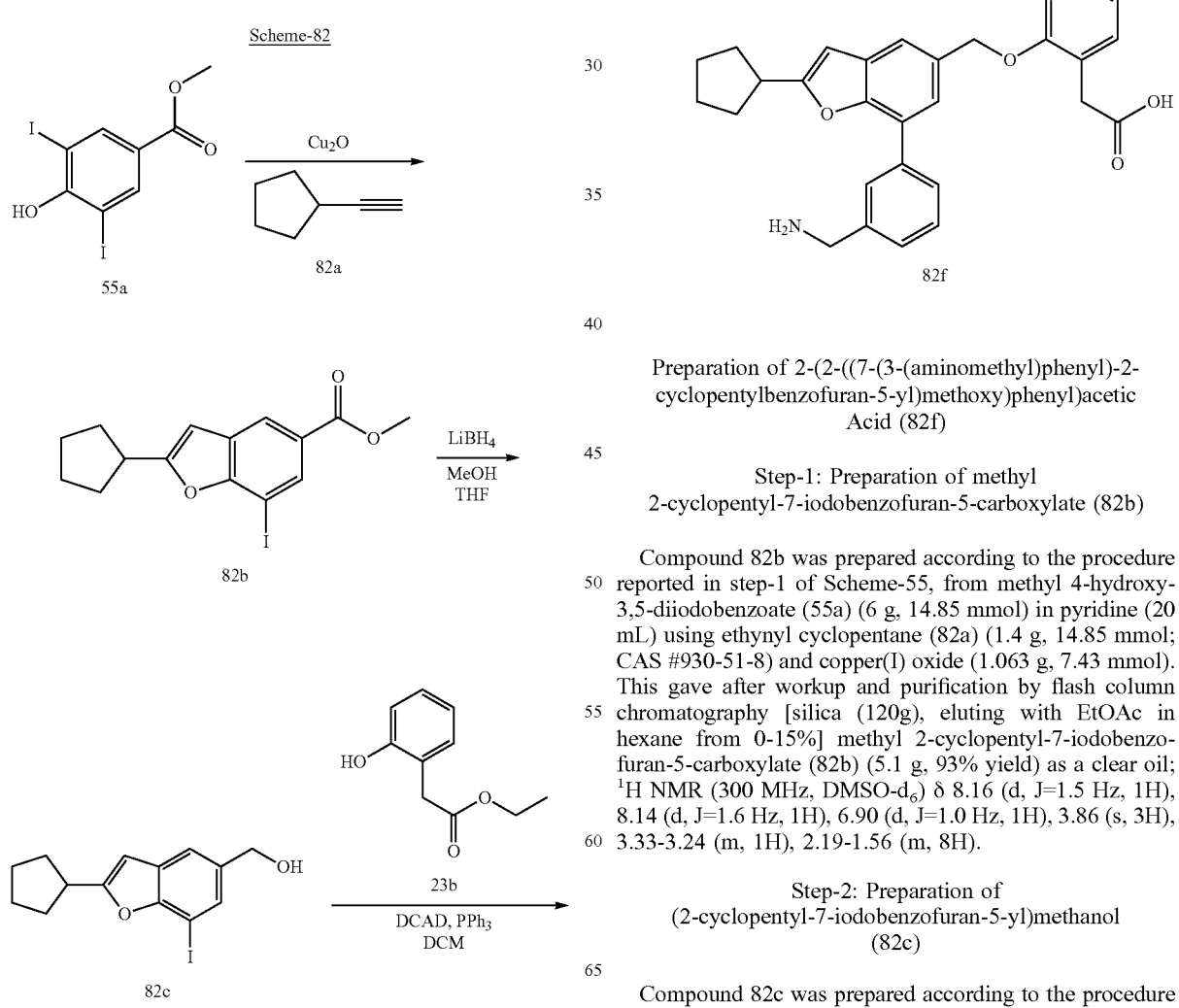

Preparation of 2-(2-((7-(3-(aminomethyl)phenyl)-2-cyclopentylbenzofuran-5-yl)methoxy)phenyl)acetic Acid (82f)

Step-1: Preparation of methyl 2-cyclopentyl-7-iodobenzofuran-5-carboxylate (82b)

Compound 82b was prepared according to the procedure reported in step-1 of Scheme-55, from methyl 4-hydroxy-3,5-diiodobenzoate (55a) (6 g, 14.85 mmol) in pyridine (20 mL) using ethynyl cyclopentane (82a) (1.4 g, 14.85 mmol; CAS #930-51-8) and copper(I) oxide (1.063 g, 7.43 mmol). This gave after workup and purification by flash column chromatography [silica (120g), eluting with EtOAc in hexane from 0-15%] methyl 2-cyclopentyl-7-iodobenzofuran-5-carboxylate (82b) (5.1 g, 93% yield) as a clear oil; $^1$H NMR (300 MHz, DMSO-$d_6$) δ 8.16 (d, J=1.5 Hz, 1H), 8.14 (d, J=1.6 Hz, 1H), 6.90 (d, J=1.0 Hz, 1H), 3.86 (s, 3H), 3.33-3.24 (m, 1H), 2.19-1.56 (m, 8H).

Step-2: Preparation of (2-cyclopentyl-7-iodobenzofuran-5-yl)methanol (82c)

Compound 82c was prepared according to the procedure reported in step-2 of Scheme-76 from methyl 2-cyclopentyl- 7-iodobenzofuran-5-carboxylate (82b) (4.48 g, 12.10 mmol) in THF (30 mL) using LiBH₄ (18.15 mL, 36.3 mmol, 2 M solution in THF) and MeOH (1.47 mL, 36.3 mmol). This gave after workup and purification by flash column chromatography [silica (24 g), eluting with EtOAc in hexane from 0-60%] (2-cyclopentyl-7-iodobenzofuran-5-yl)methanol (82c) (3.4 g, 82% yield) as a clear oil; $^1$H NMR (300 MHz, DMSO-d₆) δ 7.55 (d, J=1.5 Hz, 1H), 7.44 (d, J=1.4 Hz, 1H), 6.72 (d, J=1.0 Hz, 1H), 5.27 (t, J=5.8 Hz, 1H, D₂O exchangeable), 4.52 (d, J=5.8 Hz, 2H), 3.31-3.18 (m, 1H), 2.11-2.00 (m, 2H), 1.79-1.64 (m, 6H).

Step-3: Preparation of Ethyl 2-(2-((2-cyclopentyl-7-iodobenzofuran-5-yl)methoxy)phenyl)acetate (82d)

Compound 82d was prepared according to the procedure reported in step-2 of Scheme-23 from (2-cyclopentyl-7-iodobenzofuran-5-yl)methanol (82c) (3.4 g, 9.94 mmol) in DCM (15 mL) using triphenylphosphine (2.87 g, 10.93 mmol), ethyl 2-(2-hydroxyphenyl) acetate (23b) (1.970 g, 10.93 mmol) and di-(4-chlorobenzyl)azodicarboxylatedi-(4-chlorobenzyl)azodicarboxylate (DCAD, 4.01 g, 10.93 mmol) in DCM (20 mL). This gave after workup and purification by flash column chromatography [silica (40 g), eluting with EtOAc in hexane from 0-50%] ethyl 2-(2-((2-cyclopentyl-7-iodobenzofuran-5-yl)methoxy)phenyl)acetate (82d) (3.2 g, 64% yield) as a white solid; $^1$H NMR (300 MHz, DMSO-d₆) δ 7.64 (d, J=1.5 Hz, 1H), 7.56 (d, J=1.5 Hz, 1H), 7.28-7.19 (m, 2H), 7.06 (d, J=8.0 Hz, 1H), 6.91 (td, J=7.4, 1.0 Hz, 1H), 6.76 (d, J=1.0 Hz, 1H), 5.12 (s, 2H), 4.03 (q, J=7.1 Hz, 2H), 3.61 (s, 2H), 3.31-3.20 (m, 1H), 2.12-1.98 (m, 2H), 1.80-1.64 (m, 6H), 1.09 (t, J=7.1 Hz, 3H); MS (ES+): 527.2 (M+Na); (ES−): 503.3 (M−1).

Step-4: Preparation of Ethyl 2-(2-((7-(3-(aminomethyl)phenyl)-2-cyclopentylbenzofuran-5-yl)methoxy)phenyl)acetate (82e)

Compound 82e was prepared according to the procedure reported in step-3 of Scheme-1 from ethyl 2-(2-((2-cyclopentyl-7-iodobenzofuran-5-yl)methoxy)phenyl)acetate (82d) (500 mg, 0.99 mmol) in dioxane (20 mL) using 3-(aminomethyl)phenylboronic acid hydrochloride (6c) (279 mg, 1.49 mmol), a 3 M solution of tripotassium phosphate (1.223 mL, 3.67 mmol) in water (1 mL), tricyclohexylphosphine (83 mg, 0.30 mmol) and Pd₂(dba)₃ (91 mg, 0.1 mmol) and heating at 125° C. for 60 min on a microwave. This gave after workup, purification by flash column chromatography [silica (12 g), eluting with DMA80 in DCM from 0-70%] followed by purification by reverse phase column chromatography [C18 (50 g), eluting with ACN in water (containing 0.1% HCl) from 0-100%] ethyl 2-(2-((7-(3-(aminomethyl)phenyl)-2-cyclopentylbenzofuran-5-yl)methoxy)phenyl)acetate (82e) (223 mg, 47% yield) HCl salt as an off white solid; $^1$H NMR (300 MHz, DMSO-d₆) δ 8.47 (s, 3H, D₂O exchangeable), 7.99-7.95 (m, 1H), 7.92 (dt, J=7.3, 1.8 Hz, 1H), 7.63-7.51 (m, 4H), 7.29-7.18 (m, 2H), 7.11 (d, J=8.1 Hz, 1H), 6.91 (t, J=7.3 Hz, 1H), 6.71-6.66 (m, 1H), 5.22 (s, 2H), 4.12 (s, 2H), 3.95 (q, J=7.1 Hz, 2H), 3.62 (s, 2H), 2.13-1.98 (m, 2H), 1.85-1.59 (m, 7H), 1.01 (t, J=7.1 Hz, 3H); MS (ES+): 484.4 (M+1).

Step-5: Preparation of 2-(2-((7-(3-(aminomethyl)phenyl)-2-cyclopentylbenzofuran-5-yl)methoxy)phenyl)acetic Acid (82f)

Compound 82f was prepared according to the procedure reported in step-6 of Scheme-1, from ethyl 2-(2-((7-(3-(aminomethyl)phenyl)-2-cyclopentylbenzofuran-5-yl)methoxy)phenyl)acetate (82e) (150 mg, 0.31 mmol) in MeOH/THF (10 mL) using a solution of lithium hydroxide monohydrate (39 mg, 0.93 mmol) in water (1.0 mL). This gave after workup and purification by reverse phase column [C18 (50 g), eluting with ACN in water (containing 0.1% HCl) from 0-100%] 2-(2-((7-(3-(aminomethyl)phenyl)-2-cyclopentylbenzofuran-5-yl)methoxy)phenyl)acetic acid (82f) (52 mg, 37% yield) as a white solid; $^1$H NMR (300 MHz, DMSO-d₆) δ 12.13 (s, 1H, D₂O exchangeable), 8.40 (s, 2H, D₂O exchangeable), 7.98-7.89 (m, 2H), 7.64-7.60 (m, 1H), 7.60-7.50 (m, 3H), 7.22 (d, J=7.4 Hz, 2H), 7.08 (d, J=8.1 Hz, 1H), 6.90 (t, J=7.3 Hz, 1H), 6.68 (s, 1H), 5.23 (s, 2H), 4.13 (s, 2H), 3.59 (s, 2H), 2.50-2.49 (m, 1H), 2.13-1.98 (m, 2H), 1.83-1.61 (m, 6H); MS (ES+): 456.3 (M+1); (ES−): 454.3 (M−1); 490.3 (M+Cl).

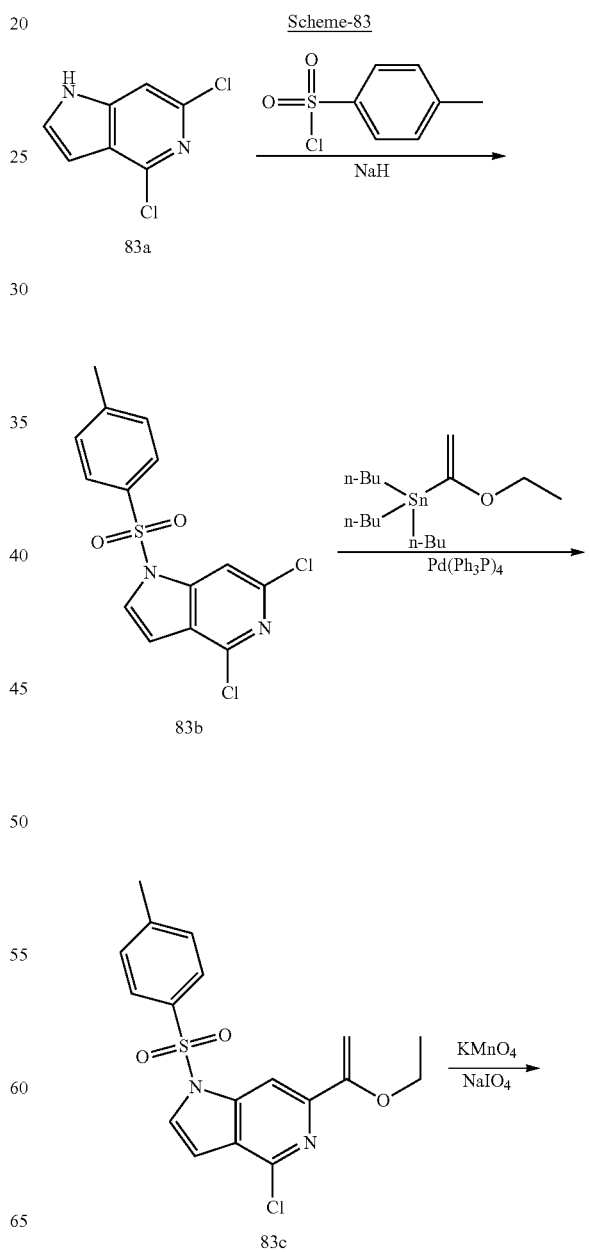

-continued

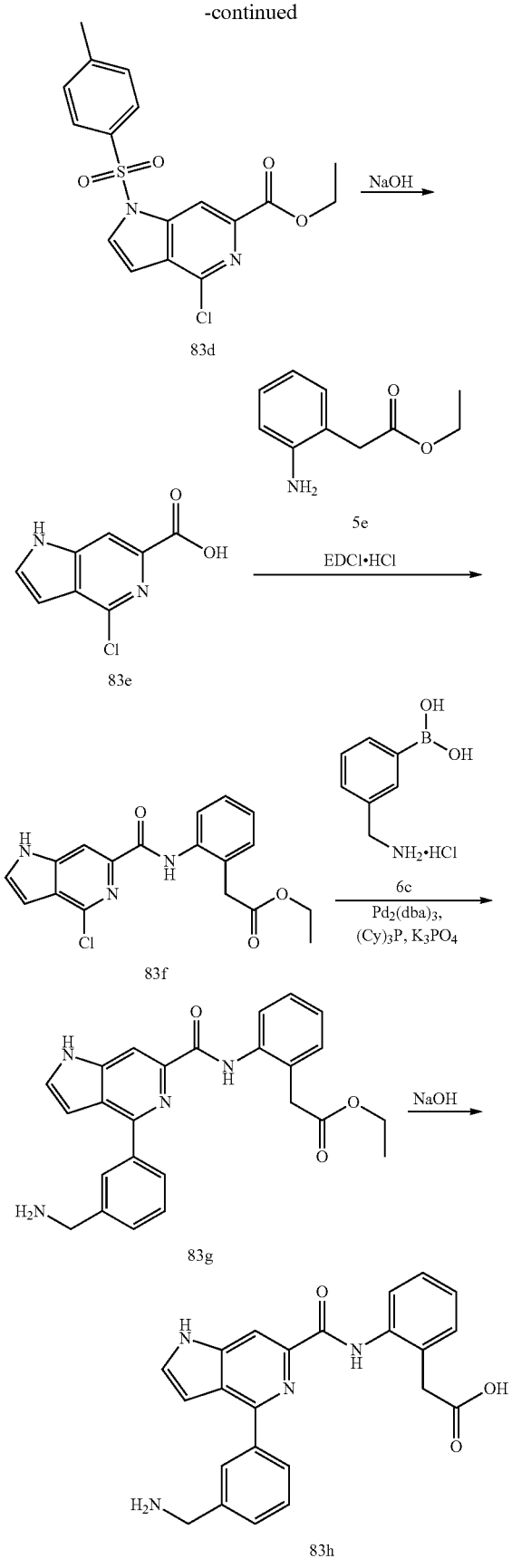

Preparation of 2-(2-(4-(3-(aminomethyl)phenyl)-1H-pyrrolo[3,2-c]pyridine-6-carboxamido)phenyl)acetic Acid (83h)

Step-1: Preparation of 4,6-dichloro-1-tosyl-1H-pyrrolo[3,2-c]pyridine (83b)

Compound 83b was prepared according to the procedure reported in step-1 of Scheme-40 from 4,6-dichloro-1H-pyrrolo[3,2-c]pyridine (83a) (4 g, 21.39 mmol; CAS #67139-79-1) in DMF (30 mL) using NaH (60% in mineral oil, 2.14 g, 53.5 mmol) and tosyl-Cl (4.89 g, 25.7 mmol). This gave after workup 4,6-dichloro-1-tosyl-1H-pyrrolo[3,2-c]pyridine (83b) (6.8 g, 93% yield) as a tan solid, which was used in the next step without further purification. $^1$H NMR (300 MHz, DMSO-$d_6$) δ 8.11 (d, J=3.8 Hz, 1H), 8.09-8.02 (d, J=8.4 Hz, 2H), 7.98 (s, 1H), 7.46 (d, J=8.2 Hz, 2H), 6.96 (d, J=3.8 Hz, 1H), 2.36 (s, 3H).

Step-2: Preparation of 4-chloro-6-(1-ethoxyvinyl)-1-tosyl-1H-pyrrolo[3,2-c]pyridine (83c)

Compound 83c was prepared according to the procedure reported in step-1 of Scheme-1 from 4,6-dichloro-1-tosyl-1H-pyrrolo[3,2-c]pyridine (83b) (3 g, 8.79 mmol) in DMF (20 mL) using 1-ethoxyvinyltri-n-butyltin (3.89 mL, 11.43 mmol) and Pd(Ph$_3$P)$_4$ (1.02 g, 0.88 mmol) in argon atmosphere and heating at 110° C. for 2 h. This gave after workup and purification by flash column chromatography [silica (80 g), eluting with EtOAc in hexane from 0-50%] 4-chloro-6-(1-ethoxyvinyl)-1-tosyl-1H-pyrrolo[3,2-c]pyridine (83c) (1.6 g, 48% yield) as a white solid; MS (ES+): 377.2 (M+1), 399.2 (M+Na).

Step-3: Preparation of Ethyl 4-chloro-1-tosyl-H-pyrrolo[3,2-c]pyridine-6-carboxylate (83d)

Compound 83d was prepared according to the procedure reported in step-2 of Scheme-1 from 4-chloro-6-(1-ethoxyvinyl)-1-tosyl-1H-pyrrolo[3,2-c]pyridine (83c) (1 g, 2.65 mmol) in 1,4-dioxane (100 mL) using sodium periodate solution (1.14 g, 5.31 mmol) in water (10 mL) and KMnO$_4$ (0.252 g, 1.592 mmol, and second dosing of 0.25 g, 1.59 mmol after 12 h). This gave after workup and purification by flash column chromatography [silica (40 g), eluting with EtOAc in hexane from 0-60%] ethyl 4-chloro-1-tosyl-1H-pyrrolo[3,2-c]pyridine-6-carboxylate (83d) (0.21 g, 21% yield) as a yellow solid; MS (ES+): 379.1 (M+1), 401.2 (M+Na).

Step-4: Preparation of 4-chloro-1H-pyrrolo[3,2-c]pyridine-6-carboxylic Acid (83e)

Compound 83e was prepared according to the procedure reported in step-4 of Scheme-4 from ethyl 4-chloro-1-tosyl-1H-pyrrolo[3,2-c]pyridine-6-carboxylate (83d) (0.2 g, 0.53 mmol) in THF/MeOH (5 mL) using sodium hydroxide (0.13 g, 3.17 mmol) in water (2 mL). This gave after workup and purification by reverse phase column [C18 (50 g), eluting with ACN in water (containing 0.1% HCl) from 0-100%] 4-chloro-1H-pyrrolo[3,2-c]pyridine-6-carboxylic acid (83e) (0.07 g, 63% yield) HCl salt as a yellow solid; $^1$H NMR (300 MHz, DMSO-$d_6$) δ 13.22 (s, 1H), 11.93 (s, 1H), 7.66 (s, 2H), 6.97 (s, 1H). MS (ES−): 195.1 (M−1), 231.1 (M+Cl).

Step-5: Preparation of Ethyl 2-(2-(4-chloro-1H-pyrrolo[3,2-c]pyridine-6-carboxamido)phenyl)acetate (83f)

Compound 83f was prepared according to the procedure reported in step-4 of Scheme-1 from 4-chloro-1H-pyrrolo[3,2-c]pyridine-6-carboxylic acid (83e) (0.06 g, 0.31 mmol) in MeOH (5 mL) using ethyl 2-(2-aminophenyl)acetate (5e) (0.06 g, 0.34 mmol), and EDCI.HCl (0.07 g, 0.37 mmol). This gave after workup and purification by flash column chromatography [silica (12 g), eluting with EtOAc in hexane from 0-60%] ethyl 2-(2-(4-chloro-1H-pyrrolo[3,2-c]pyridine-6-carboxamido)phenyl)acetate (83f) (0.02 g, 18% yield) as an off white solid; MS (ES+): 358.3 (M+1), 380.2 (M+Na); MS (ES−): 356.2 (M−1), 392.3 (M+Cl).

Step-6: Preparation of Ethyl 2-(2-(4-(3-(aminomethyl)phenyl)-1H-pyrrolo[3,2-c]pyridine-6-carboxamido)phenyl)acetate (83g)

Compound 83g was prepared according to the procedure reported in step-3 of Scheme-1 from ethyl 2-(2-(4-chloro-1H-pyrrolo[3,2-c]pyridine-6-carboxamido)phenyl)acetate (83f) (0.02 g, 0.06 mmol) in dioxane (4 mL) using 3-(aminomethyl)phenylboronic acid hydrochloride (6c) (0.02 g, 0.08 mmol), tripotassium phosphate (1.3M, 0.03 mL, 0.10 mmol), tricyclohexylphosphine (5 mg, 0.02 mmol) and $Pd_2(dba)_3$ (5 mg, 5.59 µmol) under an Ar atmosphere and heating at 125° C. for 90 min in a microwave. This gave after workup, purification by flash column chromatography [silica (24 g), eluting with hexane in ethyl acetate from 0-70%] followed by purification by reverse phase column [C18 (50 g), eluting with ACN in water (containing 0.1% HCl) from 0-100%] ethyl 2-(2-(4-(3-(aminomethyl)phenyl)-1H-pyrrolo[3,2-c]pyridine-6-carboxamido)phenyl)acetate (83g) (0.02 g, 84% yield) as a white solid; MS (ES+): 429.3 (M+1); MS (ES−): 427.4 (M−1), 463.5 (M+Cl).

Step-7: Preparation of 2-(2-(4-(3-(aminomethyl)phenyl)-1H-pyrrolo[3,2-c]pyridine-6-carboxamido)phenyl)acetic Acid (83h)

Compound 83h was prepared according to the procedure reported in step-4 of Scheme-4 from ethyl 2-(2-(4-(3-(aminomethyl)phenyl)-1H-pyrrolo[3,2-c]pyridine-6-carboxamido)phenyl)acetate (83g) (0.02 g, 0.05 mmol) in MeOH/THF (5 mL) using a solution of NaOH (0.15 mL, 0.37 mmol, 2.5 M) in water (2 mL). This gave after workup and purification by reverse phase column chromatography [C18 (50 g), eluting with ACN in water (containing 0.1% HCl) from 0-100%] 2-(2-(4-(3-(aminomethyl)phenyl)-1H-pyrrolo[3,2-c]pyridine-6-carboxamido)phenyl)acetic acid (83h) (0.01 g, 59% yield) HCl salt as a white solid; $^1$H NMR (300 MHz, DMSO-$d_6$) δ 12.24 (s, 1H), 10.80 (s, 1H), 8.69 (s, 3H), 8.47 (s, 1H), 8.26 (t, J=5.0 Hz, 1H), 8.23 (s, 1H), 8.05 (d, J=7.9 Hz, 1H), 7.68 (t, J=2.7 Hz, 1H), 7.55 (m, 2H), 7.37 (m, 2H), 7.23 (s, 1H), 7.18 (t, J=7.3 Hz, 1H), 4.15 (d, J=5.8 Hz, 2H), 3.80 (s, 2H); MS (ES+): 401.3 (M+1), 423.3 (M+Na); MS (ES−): 399.4 (M−1), 435.3 (M+Cl). HPLC purity: 98.19%.

Scheme-84

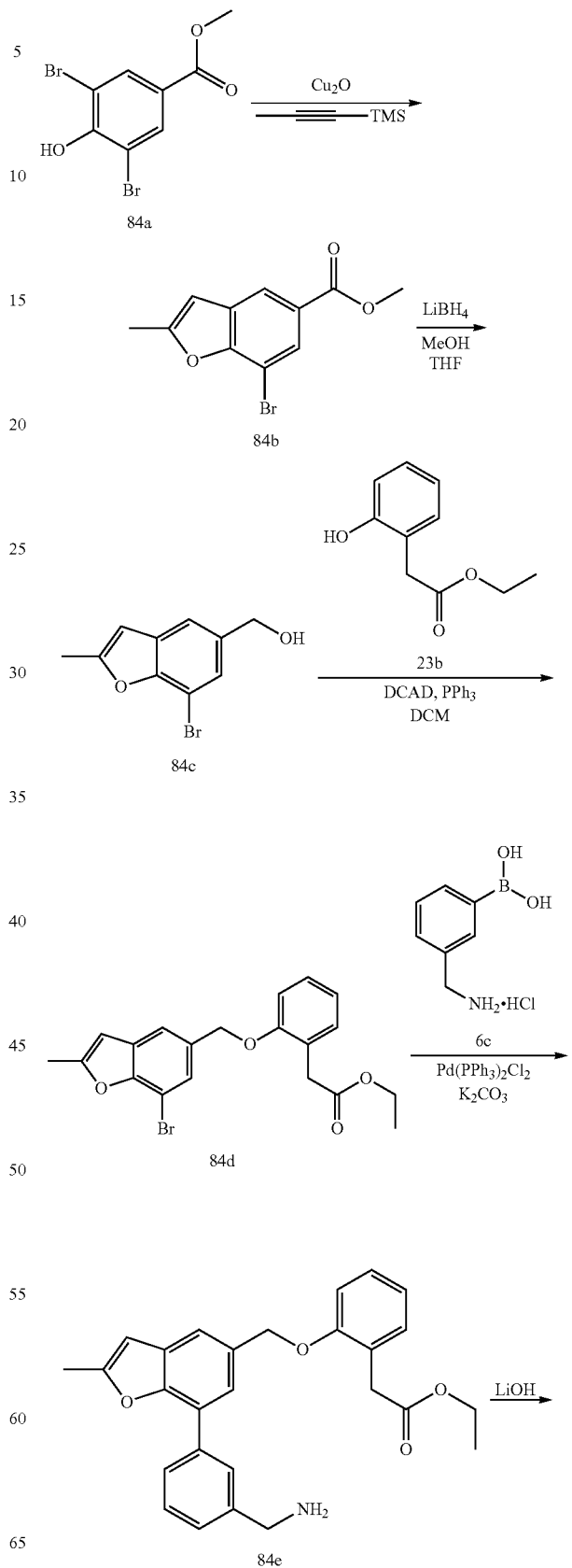

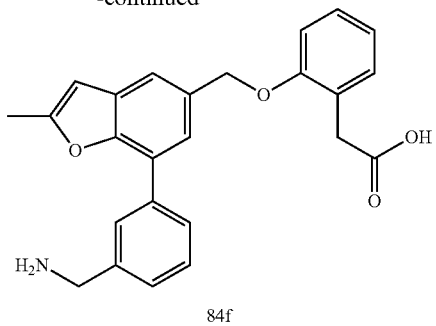

84f

Preparation of 2-(2-((7-(3-(aminomethyl)phenyl)-2-methylbenzofuran-5-yl)methoxy)phenyl)acetic Acid (84f)

Step-1: Preparation of methyl 7-bromo-2-methylbenzofuran-5-carboxylate (84b)

Compound 84b was prepared according to the procedure reported in step-1 of Scheme-55, from methyl 3,5-dibromo-4-hydroxybenzoate (84a) (150 g, 484 mmol; CAS #41727-47-3) in pyridine (500 mL) using 1-(trimethylsilyl)-1-propyne (54.3 g, 484 mmol; CAS #6224-91-5) and copper(I) oxide (69.3 g, 484 mmol). This gave after workup and purification by flash column chromatography [silica (330g), eluting with EtOAc in hexane from 0-70%] methyl 7-bromo-2-methylbenzofuran-5-carboxylate (84b) (76 g, 58% yield) as a white solid; $^1$H NMR (300 MHz, DMSO-$d_6$) δ 8.18 (d, J=1.5 Hz, 1H), 7.97 (d, J=1.5 Hz, 1H), 6.85 (d, J=1.3 Hz, 1H), 3.88 (s, 3H), 2.52 (s, 3H).

Step-2: Preparation of (7-bromo-2-methylbenzofuran-5-yl)methanol (84c)

Compound 84c was prepared according to the procedure reported in step-2 of Scheme-76 from methyl 7-bromo-2-methylbenzofuran-5-carboxylate (84b) (67 g, 249 mmol) in THF (500 mL) using LiBH$_4$ (2 M in THF, 311 mL, 622 mmol) and MeOH (25.2 mL, 622 mmol). This gave after workup (7-bromo-2-methylbenzofuran-5-yl)methanol (84c) (60 g, 100% yield) as a clear oil, which turned into a white solid after standing at RT. This compound was used in the next step without further purification; $^1$H NMR (300 MHz, DMSO-$d_6$) δ 7.46 (d, J=1.4 Hz, 1H), 7.39 (d, J=1.5 Hz, 1H), 6.68 (d, J=1.3 Hz, 1H), 5.31 (t, J=5.8 Hz, 1H), 4.55 (d, J=5.7 Hz, 2H), 2.48 (s, 3H).

Step-3: Preparation of Ethyl 2-(2-((7-bromo-2-methylbenzofuran-5-yl)methoxy)phenyl)acetate (84d)

Compound 84d was prepared according to the procedure reported in step-2 of Scheme-23 from (7-bromo-2-methylbenzofuran-5-yl)methanol (84c) (2.2 g, 9.13 mmol) in DCM (15 mL) using triphenylphosphine (2.87 g, 10.93 mmol), ethyl 2-(2-hydroxyphenyl) acetate (23b) (1.81 g, 10.04 mmol) and di-(4-chlorobenzyl)azodicarboxylate (DCAD, 3.69 g, 10.04 mmol) in DCM (20 mL). This gave after workup and purification by flash column chromatography [silica (24 g), eluting with EtOAc in hexane from 0-50%] ethyl 2-(2-((7-bromo-2-methylbenzofuran-5-yl)methoxy)phenyl)acetate (84d) (2.2 g, 60% yield) as a white solid; $^1$H NMR (300 MHz, Chloroform-d) δ 7.50-7.43 (m, 2H), 7.31-7.19 (m, 2H), 7.03-6.91 (m, 2H), 6.49-6.41 (m, 1H), 5.12 (s, 2H), 4.15 (q, J=7.1 Hz, 2H), 3.69 (s, 2H), 2.53 (d, J=1.1 Hz, 3H), 1.22 (t, J=7.1 Hz, 3H).

Step-4: Preparation of Ethyl 2-(2-((7-(3-(aminomethyl)phenyl)-2-methylbenzofuran-5-yl)methoxy)phenyl)acetate (84e)

Compound 84e was prepared according to the procedure reported in step-3 of Scheme-1 from ethyl 2-(2-((7-bromo-2-methylbenzofuran-5-yl)methoxy)phenyl)acetate (84d) (500 mg, 1.24 mmol) in dioxane (15 mL) using 3-(aminomethyl)phenylboronic acid hydrochloride (6c) (302 mg, 1.61 mmol), bis(triphenylphosphine)palladium(II) chloride (131 mg, 0.186 mmol), a solution of K$_2$CO$_3$ (514 mg, 3.72 mmol) in water (3 mL) and heating under an argon atmosphere at 100° C. for 3h on an oil bath. This gave after workup, purification by flash column chromatography [silica (12 g), eluting with DMA80 in DCM from 0-50%] followed by purification by reverse phase column chromatography [C18 (50 g), eluting with ACN in water (containing 0.1% HCl) from 0-100%] ethyl 2-(2-((7-(3-(aminomethyl)phenyl)-2-methylbenzofuran-5-yl)methoxy)phenyl)acetate (84e) (160 mg, 30% yield) as a white solid; $^1$H NMR (300 MHz, DMSO-$d_6$) δ 8.45 (s, 3H, D$_2$O exchangeable), 7.99-7.93 (m, 1H), 7.93-7.85 (m, 1H), 7.62-7.53 (m, 3H), 7.52-7.48 (m, 1H), 7.30-7.19 (m, 2H), 7.17-7.07 (m, 1H), 6.97-6.86 (m, 1H), 6.67 (d, J=1.4 Hz, 1H), 5.21 (s, 2H), 4.13 (s, 2H), 3.95 (q, J=7.1 Hz, 2H), 3.69 (s, 2H), 2.49 (s, 3H), 1.01 (t, J=7.1, 1.6 Hz, 3H); MS (ES+): 430.3 (M+1).

Step-5: Preparation of 2-(2-((7-(3-(aminomethyl)phenyl)-2-methylbenzofuran-5-yl)methoxy)phenyl)acetic Acid (84f)

Compound 84f was prepared according to the procedure reported in step-6 of Scheme-1, from ethyl 2-(2-((7-(3-(aminomethyl)phenyl)-2-methylbenzofuran-5-yl)methoxy)phenyl)acetate (84e) (46 mg, 0.11 mmol) in MeOH/THF (10 mL) using a solution of lithium hydroxide monohydrate (14 mg, 0.32 mmol) in water (1.0 mL). This gave after workup and purification by reverse phase column [C18 (50 g), eluting with ACN in water (containing 0.1% HCl) from 0-100%] 2-(2-((7-(3-(aminomethyl)phenyl)-2-methylbenzofuran-5-yl)methoxy)phenyl)acetic acid (84f) (17 mg, 40% yield) HCl salt as a white solid; $^1$H NMR (300 MHz, DMSO-$d_6$) δ 12.21 (s, 1H, D$_2$O exchangeable), 8.40 (s, 3H, D$_2$O exchangeable), 8.02-7.86 (m, 2H), 7.65-7.50 (m, 4H), 7.29-7.17 (m, 2H), 7.09 (d, J=8.1 Hz, 1H), 6.90 (t, J=7.4 Hz, 1H), 6.66 (s, 1H), 5.23 (s, 2H), 4.14 (s, 2H), 3.59 (s, 2H), 2.50 (s, 3H); MS (ES+): 402.3 (M+1); (ES−): 400.4 (M−1), 436.3 (M+Cl).

Scheme-85

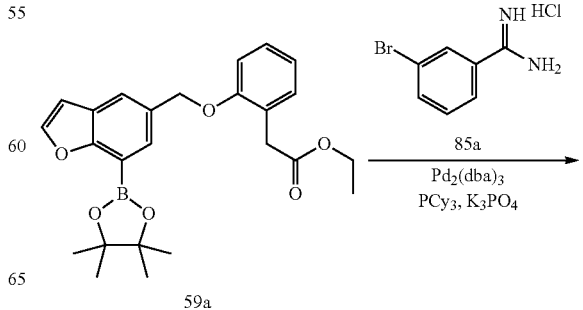

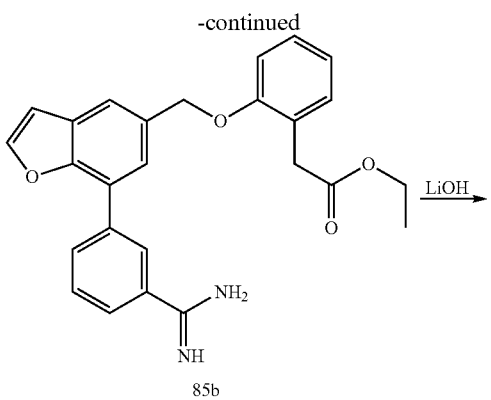

85b

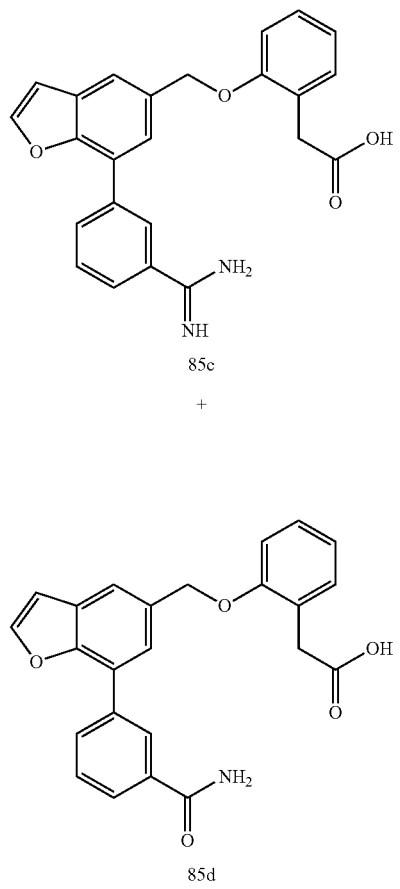

85c

+

85d

Preparation of 2-(2-((7-(3-carbamimidoylphenyl)benzofuran-5-yl)methoxy)phenyl)acetic Acid (85c) and 2-(2-((7-(3-carbamoylphenyl)benzofuran-5-yl)methoxy)phenyl)acetic Acid (85d)

Step-1: Preparation of Ethyl 2-(2-((7-(3-carbamimidoylphenyl)benzofuran-5-yl)methoxy)phenyl)acetate (85b)

Compound 85b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (400 mg, 0.92 mmol) in dioxane (6 mL) using 3-bromobenzimidamide hydrochloride (85a) (367 mg, 1.56 mmol; CAS #16796-52-4), tripotassium phosphate (3M aqueous, 0.92 mL, 2.75 mmol), tricyclohexylphosphine (77 mg, 0.28 mmol) and $Pd_2(dba)_3$ (84 mg, 0.092 mmol) under an Ar atmosphere and heating at 120° C. for 90 min in a microwave. This gave after workup, purification by flash column chromatography [silica (12 g), eluting with EtOAc in hexane from 0-70%] ethyl 2-(2-((7-(3-carbamimidoylphenyl)benzofuran-5-yl)methoxy)phenyl)acetate (85b) (120 mg, 31% yield) as a yellow solid; MS (ES+): 429.3 (M+1).

Step-2: Preparation of 2-(2-((7-(3-carbamimidoylphenyl)benzofuran-5-yl)methoxy)phenyl)acetic Acid (85c) and 2-(2-((7-(3-carbamoylphenyl)benzofuran-5-yl)methoxy)phenyl)acetic Acid (85d)

Compounds 85c and 85d were prepared according to the procedure reported in step-6 of Scheme-1, from ethyl 2-(2-((7-(3-carbamimidoylphenyl)benzofuran-5-yl)methoxy)phenyl)acetate (85b) (120 mg, 0.28 mmol) in MeOH/THF (10 mL) using a solution of lithium hydroxide monohydrate (35 mg, 0.84 mmol) in water (1 mL). This gave after workup and purification by reverse phase column [C18 (50 g), eluting with ACN in water (containing 0.1% HCl) from 0-100%] 2-(2-((7-(3-carbamimidoylphenyl)benzofuran-5-yl)methoxy)phenyl)acetic acid (85c) (10 mg, 9% yield) HCl salt as a white solid; $^1$H NMR (300 MHz, DMSO-$d_6$) δ 12.20 (s, 1H, $D_2O$ exchangeable), 9.45 (s, 2H, $D_2O$ exchangeable), 9.19 (s, 2H, $D_2O$ exchangeable), 8.35-8.21 (m, 2H), 8.12 (d, J=2.2 Hz, 1H), 7.92-7.83 (m, 1H), 7.83-7.74 (m, 3H), 7.29-7.17 (m, 2H), 7.16-7.03 (m, 2H), 6.91 (t, J=7.3 Hz, 1H), 5.29 (s, 2H), 3.60 (s, 2H); MS (ES+): 401.3 (M+1); 423.3 (M+Na); (ES−): 435.4 (M+Cl); and 2-(2-((7-(3-carbamoylphenyl)benzofuran-5-yl)methoxy)phenyl)acetic acid (85d) (37 mg, 33% yield) as a white solid; $^1$H NMR (300 MHz, DMSO-$d_6$) δ 12.19 (s, 1H, $D_2O$ exchangeable), 8.38 (t, J=1.8 Hz, 1H), 8.11 (d, J=2.2 Hz, 1H), 8.09-8.02 (m, 2H, $D_2O$ exchangeable, 1H), 7.97-7.88 (m, 1H), 7.77 (d, J=1.6 Hz, 1H), 7.69 (d, J=1.6 Hz, 1H), 7.62 (t, J=7.8 Hz, 1H), 7.47 (s, 1H), 7.28-7.17 (m, 2H), 7.11 (d, J=8.0 Hz, 1H), 7.05 (d, J=2.2 Hz, 1H), 6.96-6.84 (m, 1H), 5.28 (s, 2H), 3.60 (s, 2H); MS (ES+) 402.2 (M+1); 424.3 (M+Na); (ES−) 400.3 (M−1), 436.3 (M+Cl).

Scheme-86

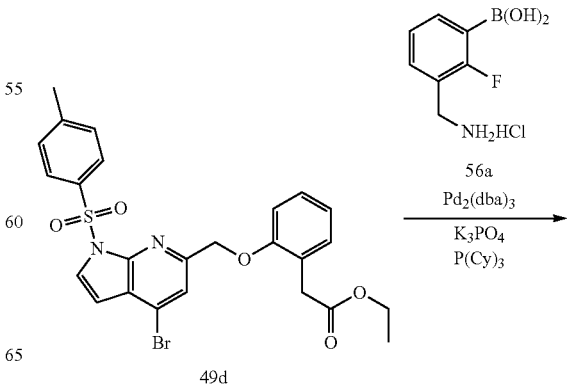

-continued

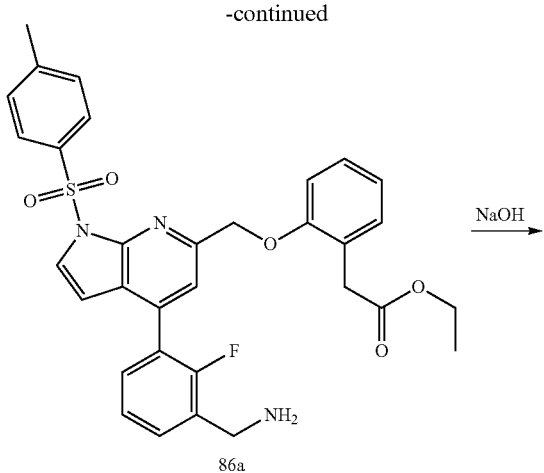

86a

↓ NaOH

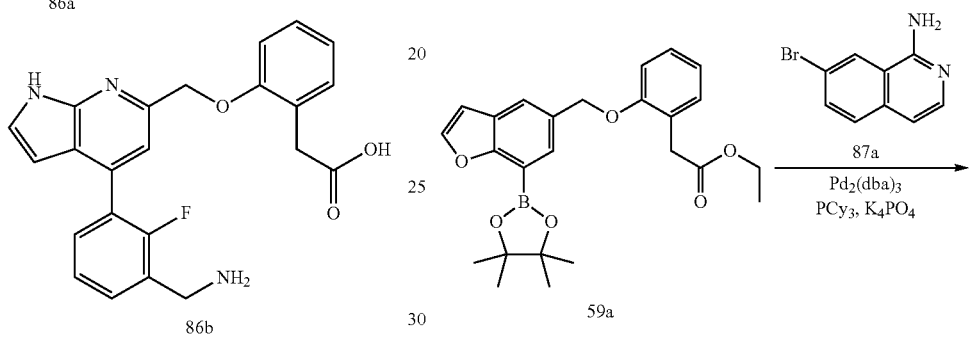

86b

Preparation of 2-(2-((4-(3-(aminomethyl)-2-fluoro-phenyl)-1H-pyrrolo[2,3-b]pyridin-6-yl)methoxy)phenyl)acetic Acid (86b)

Step-1: Preparation of Ethyl 2-(2-((4-(3-(aminomethyl)-2-fluorophenyl)-1-tosyl-1H-pyrrolo[2,3-b]pyridin-6-yl)methoxy)phenyl)acetate (86a)

Compound 86a was prepared according to the procedure reported in step-3 of Scheme-1 from ethyl 2-(2-((4-bromo-1-tosyl-1H-pyrrolo[2,3-b]pyridin-6-yl)methoxy)phenyl)acetate (49d) (0.08 g, 0.15 mmol) in dioxane (4 mL) using 3-(aminomethyl)-2-fluorophenylboronic acid hydrochloride (56a) (0.045 g, 0.221 mmol), tripotassium phosphate (1.3 M solution, 0.08 mL, 0.25 mmol), tricyclohexylphosphine (0.01 g, 0.04 mmol) and Pd$_2$(dba)$_3$ (0.01 g, 0.02 mmol) under an Ar atmosphere and heating at 125° C. for 90 min in a microwave. This gave after workup, purification by flash column chromatography [silica (12 g), eluting with DMA80 in DCM from 0-60%] followed by purification by reverse phase column [C18 (50 g), eluting with ACN in water (containing 0.1% HCl) from 0-100%] ethyl 2-(2-((4-(3-(aminomethyl)-2-fluorophenyl)-1-tosyl-1H-pyrrolo[2,3-b]pyridin-6-yl)methoxy)phenyl)acetate (86a) (0.06 g, 71% yield) as a white solid, which was used as such for next step.

Step-2: Preparation of 2-(2-((4-(3-(aminomethyl)-2-fluorophenyl)-1H-pyrrolo[2,3-b]pyridin-6-yl)methoxy)phenyl)acetic Acid (86b)

Compound 86b was prepared according to the procedure reported in step-4 of Scheme-4, from ethyl 2-(2-((4-(3-(aminomethyl)-2-fluorophenyl)-1-tosyl-1H-pyrrolo[2,3-b]pyridin-6-yl)methoxy)phenyl)acetate (86a) (0.06 g, 0.10 mmol) in MeOH/THF (6 mL, 1:1) using a solution of sodium hydroxide (0.41 mL, 1.02 mmol, 2.5 M) in water (1 mL). This gave after workup and purification by reverse phase column [C18 (50 g), eluting with ACN in water (containing 0.1% HCl) from 0-100%] 2-(2-((4-(3-(aminomethyl)-2-fluorophenyl)-1H-pyrrolo[2,3-b]pyridin-6-yl)methoxy)phenyl)acetic acid (86b) (0.02 g, 44% yield) HCl salt as a white solid; $^1$H NMR (300 MHz, DMSO-d$_6$) δ 11.89 (s, 1H), 8.55 (s, 3H), 7.67 (m, 2H), 7.56 (t, J=2.9 Hz, 1H), 7.44 (m, 1H), 7.34 (s, 1H), 7.21 (m, 2H), 7.09 (m, 1H), 6.90 (t, J=7.3 Hz, 1H), 6.45 (q, J=2.7 Hz, 1H), 5.29 (s, 2H), 4.16 (q, J=5.9 Hz, 2H), 3.60 (s, 2H). $^{19}$F NMR (282 MHz, DMSO-d$_6$) δ −118.12; MS (ES+): 406.3 (M+1); MS (ES−): 404.3 (M−1), 440.3 (M+Cl). HPLC purity: 98.61%.

Scheme-87

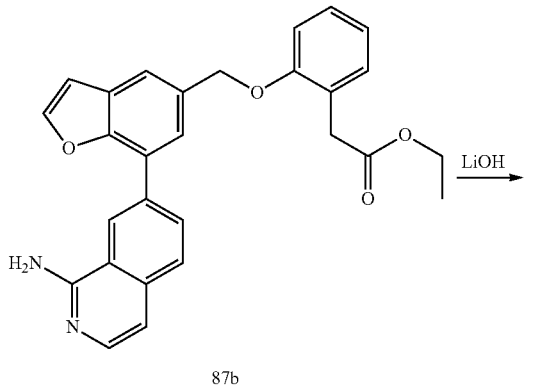

↓

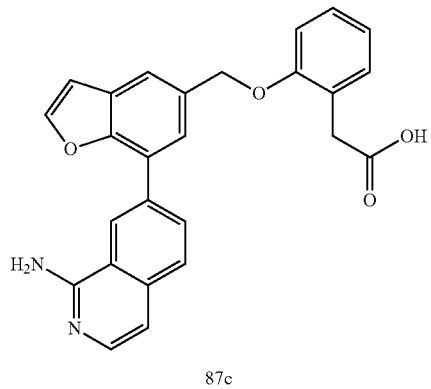

87b

↓ LiOH

87c

473

Preparation of 2-(2-((7-(1-aminoisoquinolin-7-yl)benzofuran-5-yl)methoxy)phenyl)acetic Acid (87c)

Step-1: Preparation of Ethyl 2-(2-((7-(1-aminoisoquinolin-7-yl)benzofuran-5-yl)methoxy)phenyl)acetate (87b)

Compound 87b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (400 mg, 0.92 mmol) in dioxane (3 mL) using 7-bromoisoquinolin-1-amine (87a) (307 mg, 1.38 mmol; CAS #215453-53-5), tripotassium phosphate (3M aqueous, 0.52 mL, 1.56 mmol), tricyclohexylphosphine (77 mg, 0.28 mmol) and Pd$_2$(dba)$_3$ (84 mg, 0.092 mmol) under an Ar atmosphere and heating at 120° C. for 60 min in a microwave. This gave after workup, purification by flash column chromatography [silica (12 g), eluting with EtOAc in hexane from 0-70%] ethyl 2-(2-((7-(1-aminoisoquinolin-7-yl)benzofuran-5-yl)methoxy)phenyl)acetate (87b) (154 mg, 37% yield) HCl salt as a white solid; $^1$H NMR (300 MHz, DMSO-d$_6$) δ 13.39 (s, 1H, D$_2$O exchangeable), 9.21 (s, 2H, D$_2$O exchangeable), 9.05 (d, J=1.7 Hz, 1H), 8.50 (dd, J=8.5, 1.6 Hz, 1H), 8.17-8.09 (m, 2H), 7.84-7.78 (m, 2H), 7.75 (d, J=6.8 Hz, 1H), 7.31 (d, J=6.8 Hz, 1H), 7.29-7.20 (m, 2H), 7.14 (d, J=8.5 Hz, 1H), 7.12-7.10 (m, 1H), 6.92 (t, J=7.4, 1.1 Hz, 1H), 5.29 (s, 2H), 3.90 (q, J=7.1, 1.5 Hz, 2H), 3.65 (s, 2H), 0.94 (t, J=7.1, 1.4 Hz, 3H); MS (ES+): 453.3 (M+1); (ES−): 487.3 (M+Cl).

Step-2: Preparation of 2-(2-((7-(1-aminoisoquinolin-7-yl)benzofuran-5-yl)methoxy)phenyl)acetic Acid (87c)

Compound 87c was prepared according to the procedure reported in step-6 of Scheme-1, from ethyl 2-(2-((7-(1-aminoisoquinolin-7-yl)benzofuran-5-yl)methoxy)phenyl)acetate (87b) (114 mg, 0.25 mmol) in MeOH/THF (10 mL) using a solution of lithium hydroxide monohydrate (32 mg, 0.76 mmol) in water (1 mL). This gave after workup and purification by reverse phase column [C18 (50 g), eluting with ACN in water (containing 0.1% HCl) from 0-100%] 2-(2-((7-(1-aminoisoquinolin-7-yl)benzofuran-5-yl)methoxy)phenyl)acetic acid (87c) (32 mg, 30% yield) as a white solid; $^1$H NMR (300 MHz, DMSO-d$_6$) δ 13.28 (s, 1H, D$_2$O exchangeable), 12.20 (s, 1H, D$_2$O exchangeable), 9.10 (s, 2H, D$_2$O exchangeable), 9.02 (s, 1H), 8.49 (dd, J=8.4, 1.6 Hz, 1H), 8.17-8.06 (m, 2H), 7.86-7.78 (m, 2H), 7.74 (d, J=6.9 Hz, 1H), 7.34-7.26 (m, 1H), 7.23 (d, J=7.6 Hz, 2H), 7.17-7.06 (m, 2H), 6.91 (t, J=7.2 Hz, 1H), 5.31 (s, 2H), 3.61 (s, 2H); MS (ES+): 425.3 (M+1); (ES−): 423.3 (M−1), 459.3 (M+Cl).

Scheme-88

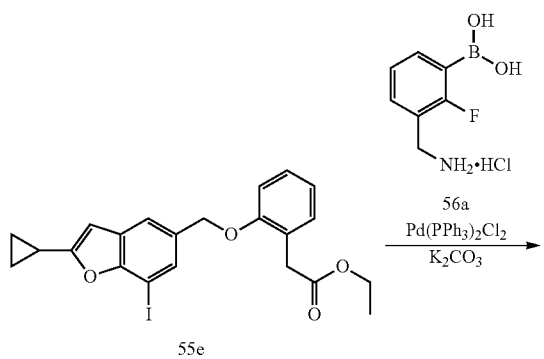

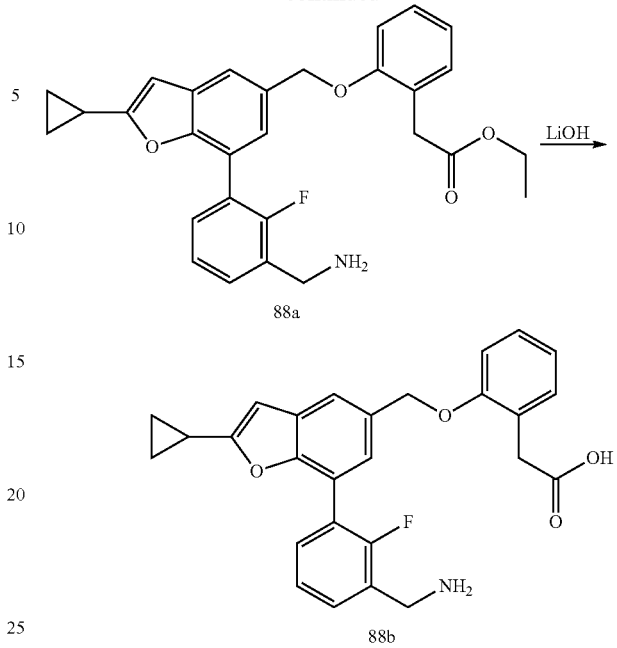

Preparation of 2-(2-((7-(3-(aminomethyl)-2-fluorophenyl)-2-cyclopropylbenzofuran-5-yl)methoxy)phenyl)acetic Acid (88b)

Step-1: Preparation of Ethyl 2-(2-((7-(3-(aminomethyl)-2-fluorophenyl)-2-cyclopropylbenzofuran-5-yl)methoxy)phenyl)acetate (88a)

Compound 88a was prepared according to the procedure reported in step-3 of Scheme-1 from ethyl 2-(2-((2-cyclopropyl-7-iodobenzofuran-5-yl)methoxy)phenyl)acetate (55e) (500 mg, 1.05 mmol) in dioxane (15 mL) using 3-(aminomethyl)-2-fluorophenylboronic acid hydrochloride (56a) (345 mg, 1.68 mmol), bis(triphenylphosphine)palladium(II) chloride (111 mg, 0.16 mmol) and a solution of K$_2$CO$_3$ (435 mg, 3.15 mmol) in water (3 mL) under an Ar atmosphere and heating at 100° C. for 3h on oil bath. This gave after workup, purification by flash column chromatography [silica (40 g), eluting with DMA80 in DCM from 0-50%] followed by purification by reverse phase column chromatography [C18 (50 g), eluting with ACN in water (containing 0.1%) HCl) from 0-100%] ethyl 2-(2-((7-(3-(aminomethyl)-2-fluorophenyl)-2-cyclopropylbenzofuran-5-yl)methoxy)phenyl)acetate (88a) (299 mg, 60% yield) HCl salt as a white solid; $^1$H NMR (300 MHz, DMSO-d$_6$) δ 8.57 (s, 3H, D$_2$O exchangeable), 7.73-7.57 (m, 3H), 7.42 (t, J=7.7 Hz, 1H), 7.31 (s, 1H), 7.28-7.17 (m, 2H), 7.10 (d, J=8.2 Hz, 1H), 6.91 (t, J=7.4 Hz, 1H), 6.65 (s, 1H), 5.20 (s, 2H), 4.17 (s, 2H), 3.94 (q, J=7.1 Hz, 2H), 3.61 (s, 2H), 2.15-2.03 (m, 1H), 1.07-0.93 (m, 5H), 0.89-0.81 (m, 2H); $^{19}$F NMR (282 MHz, DMSO-d$_6$) δ−118.85; MS (ES+): 474.3 (M+1).

Step-2: Preparation of 2-(2-((7-(3-(aminomethyl)-2-fluorophenyl)-2-cyclopropylbenzofuran-5-yl)methoxy)phenyl)acetic Acid (88b)

Compound 88b was prepared according to the procedure reported in step-6 of Scheme-1, from ethyl 2-(2-((7-(3-

(aminomethyl)-2-fluorophenyl)-2-cyclopropylbenzofuran-5-yl)methoxy)phenyl)acetate (88a) (185 mg, 0.39 mmol) in MeOH/THF (10 mL) using a solution of lithium hydroxide monohydrate (49 mg, 1.17 mmol) in water (1 mL). This gave after workup and purification by reverse phase column [C18 (50 g), eluting with ACN in water (containing 0.1% HCl) from 0-100%] 2-(2-((7-(3-(aminomethyl)-2-fluorophenyl)-2-cyclopropylbenzofuran-5-yl)methoxy)phenyl)acetic acid (88b) (135 mg, 78% yield) as a white solid; $^1$H NMR (300 MHz, DMSO-$d_6$) δ 8.66 (s, 2H, D$_2$O exchangeable), 7.73-7.59 (m, 3H), 7.42 (t, J=7.6 Hz, 1H), 7.34 (d, J=1.4 Hz, 1H), 7.26-7.17 (m, 2H), 7.07 (d, J=8.0 Hz, 1H), 6.89 (t, J=7.4, 1.1 Hz, 1H), 6.63 (s, 1H), 5.21 (s, 2H), 4.17 (s, 2H), 3.57 (s, 2H), 2.14-2.06 (m, 1H), 1.06-0.93 (m, 2H), 0.89-0.80 (m, 2H); $^{19}$F NMR (282 MHz, DMSO-$d_6$) δ −118.64; MS (ES+): 446.3 (M+1); 468.3 (M+Na); (ES−): 444.4 (M−1), 480.3 (M+Cl).

Scheme-89

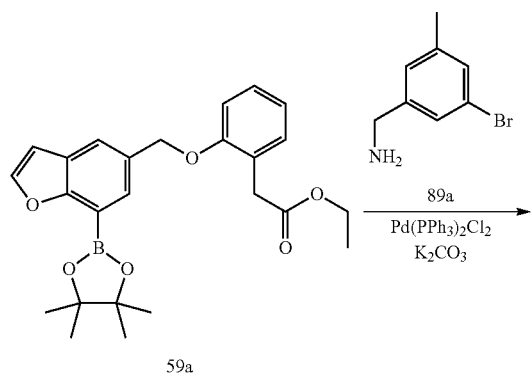

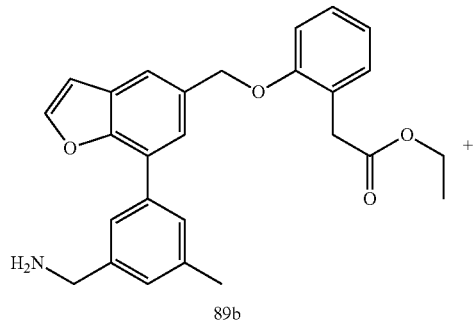

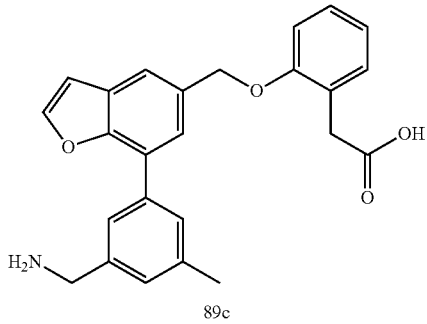

Preparation of 2-(2-((7-(3-(aminomethyl)-5-methylphenyl)benzofuran-5-yl)methoxy)phenyl)acetic Acid (89c)

Compound 89c was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (327 mg, 0.75 mmol) in dioxane (15 mL) using (3-bromo-5-methylphenyl)methanamine (89a) (150 mg, 0.75 mmol; CAS #1177558-42-7), bis(triphenylphosphine)palladium(II) chloride (79 mg, 0.112 mmol), a solution of K$_2$CO$_3$ (311 mg, 2.25 mmol) in water (3 mL) under an Ar atmosphere and heating at 100° C. for 13h on an oil bath. This gave after workup, purification by flash column chromatography [silica (12 g), eluting with DMA80 in DCM from 0-50%] followed by purification by reverse phase column chromatography [C18 (50 g), eluting with ACN in water (containing 0.1%) HCl from 0-100%] ethyl 2-(2-((7-(3-(aminomethyl)-5-methylphenyl)benzofuran-5-yl)methoxy)phenyl)acetate (89b) (83 mg, 26% yield) HCl salt as a white solid; $^1$H NMR (300 MHz, DMSO-$d_6$) δ 8.46 (s, 3H, D$_2$O exchangeable), 8.10 (d, J=2.3 Hz, 1H), 7.80 (d, J=1.9 Hz, 1H), 7.72 (d, J=1.7 Hz, 2H), 7.60 (d, J=1.7 Hz, 1H), 7.39 (s, 1H), 7.29-7.18 (m, 2H), 7.15-7.08 (m, 1H), 7.08-7.03 (m, 1H), 6.96-6.85 (m, 1H), 5.24 (s, 2H), 4.08 (s, 2H), 3.95 (q, J=7.1 Hz, 2H), 3.63 (s, 2H), 2.43 (s, 3H), 1.01 (t, J=7.1 Hz, 3H); MS (ES+): 430.3 (M+1); and 2-(2-((7-(3-(aminomethyl)-5-methylphenyl)benzofuran-5-yl)methoxy)phenyl)acetic acid (89c) (18 mg, 6% yield) HCl salt as a white solid: $^1$H NMR (300 MHz, DMSO-$d_6$) δ 12.19 (s, 1H, D$_2$O exchangeable), 8.25 (s, 3H, D$_2$O exchangeable), 8.11-8.07 (m, 1H), 7.82-7.77 (m, 1H), 7.77-7.71 (m, 2H), 7.65-7.59 (m, 1H), 7.36 (s, 1H), 7.22 (d, J=7.4 Hz, 2H), 7.14-7.07 (m, 1H), 7.07-7.02 (m, 1H), 6.95-6.85 (m, 1H), 5.26 (s, 2H), 4.09 (s, 2H), 3.60 (s, 2H), 2.43 (s, 3H); MS (ES+): 402.3 (M+1); 425.3 (M+Na); (ES−): 400.3 (M−1); 436.3 (M+Cl).

Scheme-90

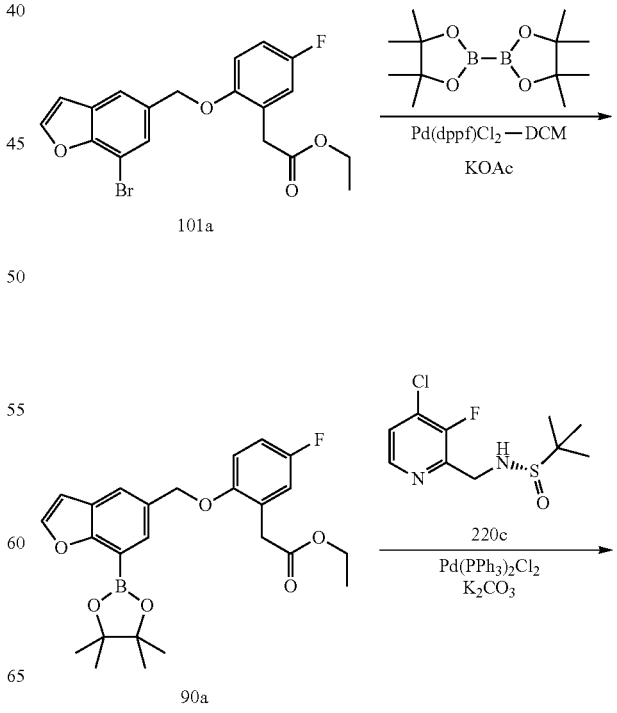

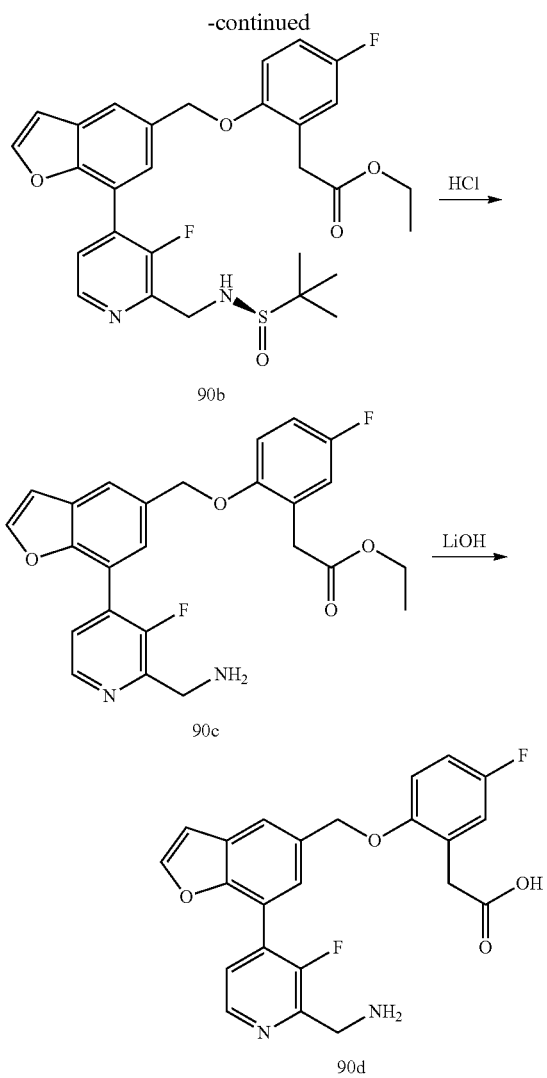

Preparation of 2-(2-((7-(2-(aminomethyl)-3-fluoropyridin-4-yl)benzofuran-5-yl)methoxy)-5-fluorophenyl)acetic Acid (90d)

Step-1: Preparation of Ethyl 2-(5-fluoro-2-((7-(4,4,5,5-tetramethyl-1,3,2-dioxaborolan-2-yl)benzofuran-5-yl)methoxy)phenyl)acetate (90a)

Compound 90a was prepared according to the procedure reported in step-1 of Scheme-59 from ethyl 2-(2-((7-bromobenzofuran-5-yl)methoxy)-5-fluorophenyl)acetate (101a) (0.2 g, 0.49 mmol), using bis(pinacolato)diboron (0.19 g, 0.74 mmol), potassium acetate (0.10 g, 0.98 mmol) and Pd(dppf)Cl$_2$—CH$_2$Cl$_2$ (0.06 g, 0.07 mmol) in anhydrous dioxane (5 mL) under an Ar atmosphere and heating at 100° C. overnight. This gave after workup and purification by flash column chromatography [silica (12 g), eluting with EtOAc/MeOH=9:1 in hexane from 0-10%] ethyl 2-(5-fluoro-2-((7-(4,4,5,5-tetramethyl-1,3,2-dioxaborolan-2-yl)benzofuran-5-yl)methoxy)phenyl)acetate (90a) (0.21 g, 94% yield) as a white oil; $^1$H NMR (300 MHz, DMSO-d$_6$) δ 8.06 (d, J=2.2 Hz, 1H), 7.82 (d, J=1.9 Hz, 1H), 7.64 (d, J=1.8 Hz, 1H), 7.16-7.06 (m, 3H), 6.97 (d, J=2.2 Hz, 1H), 5.15 (s, 2H), 4.01 (q, J=7.1 Hz, 2H), 3.61 (s, 2H), 1.34 (s, 12H), 1.08-1.04 (m, 3H); MS (ES-): 453.2 (M-1).

Step-2: Preparation of (S)-ethyl 2-(2-((7-(2-((1,1-dimethylethylsulfinamido)methyl)-3-fluoropyridin-4-yl)benzofuran-5-yl)methoxy)-5-fluorophenyl)acetate (90b)

Compound 90b was prepared according to the procedure reported in step-3 of Scheme-1 from ethyl 2-(5-fluoro-2-((7-(4,4,5,5-tetramethyl-1,3,2-dioxaborolan-2-yl)benzofuran-5-yl)methoxy)phenyl)acetate (90a) (0.21 g, 0.46 mmol) in dioxane (4 mL) using (S)—N-((4-chloro-3-fluoropyridin-2-yl)methyl)-2-methylpropane-2-sulfinamide (220c) (0.18 g, 0.69 mmol), bis(triphenylphosphine)palladium(II) chloride (0.05 g, 0.07 mmol) and a solution of K$_2$CO$_3$ (0.16 g, 1.16 mmol) in water (0.5 mL) under an Ar atmosphere and heating at 90° C. for 3 h on oil bath. This gave after workup, purification by flash column chromatography [silica (12 g), eluting with MeOH in DCM from 0-50%] (S)-ethyl 2-(2-((7-(2-((1,1-dimethylethylsulfinamido)methyl)-3-fluoropyridin-4-yl)benzofuran-5-yl)methoxy)-5-fluorophenyl)acetate (90b) (0.2 g, 78% yield) as a white solid; MS (ES+): 557.2 (M+1); MS (ES-): 555.2 (M-1).

Step-3: Preparation of Ethyl 2-(2-((7-(2-(aminomethyl)-3-fluoropyridin-4-yl)benzofuran-5-yl)methoxy)-5-fluorophenyl)acetate (90c)

Compound 90c was prepared according to the procedure reported in step-5 of Scheme-220 from (S)-ethyl 2-(2-((7-(2-((1,1-dimethylethylsulfinamido)methyl)-3-fluoropyridin-4-yl)benzofuran-5-yl)methoxy)-5-fluorophenyl)acetate (90b) (0.2 g, 0.36 mmol) in methanol (5 mL) using hydrochloric acid (4 M in 1,4-dioxane, 0.27 mL, 1.08 mmol). This gave after workup ethyl 2-(2-((7-(2-(aminomethyl)-3-fluoropyridin-4-yl)benzofuran-5-yl)methoxy)-5-fluorophenyl)acetate (90c) (0.15 g, 92% yield) as a white solid; MS (ES+): 453.2 (M+1); MS (ES-): 451.0 (M-1).

Step-4: Preparation of 2-(2-((7-(2-(aminomethyl)-3-fluoropyridin-4-yl)benzofuran-5-yl)methoxy)-5-fluorophenyl)acetic Acid (90d)

Compound 90d was prepared according to the procedure reported in step-6 of Scheme-1 from ethyl 2-(2-((7-(2-(aminomethyl)-3-fluoropyridin-4-yl)benzofuran-5-yl)methoxy)-5-fluorophenyl)acetate (90c) (0.19 g, 0.42 mmol) in MeOH/THF (4 mL, each) using lithium hydroxide hydrate (0.14 g, 3.36 mmol) in water (1 mL). This gave after workup and purification by reverse phase column [C18 (50 g), eluting with ACN in water (containing 0.1% HCl) from 0-100%] 2-(2-((7-(2-(aminomethyl)-3-fluoropyridin-4-yl)benzofuran-5-yl)methoxy)-5-fluorophenyl)acetic acid (90d) (0.06 g, 31% yield) HCl salt as a white solid; $^1$H NMR (300 MHz, DMSO-d$_6$) δ 8.63 (d, J=5.0 Hz, 1H), 8.57 (s, 3H), 8.12 (d, J=2.2 Hz, 1H), 7.90 (d, J=1.6 Hz, 1H), 7.80 (t, J=5.3 Hz, 1H), 7.58 (d, J=1.4 Hz, 1H), 7.17-7.01 (m, 4H), 5.26 (s, 2H), 4.38 (d, J=5.9 Hz, 2H), 3.60 (s, 2H); $^{19}$F NMR (282 MHz, DMSO-d$_6$) δ-128.36, 124.02; MS (ES+): 425.1 (M+1); MS (ES-): 423.0 (M-1).

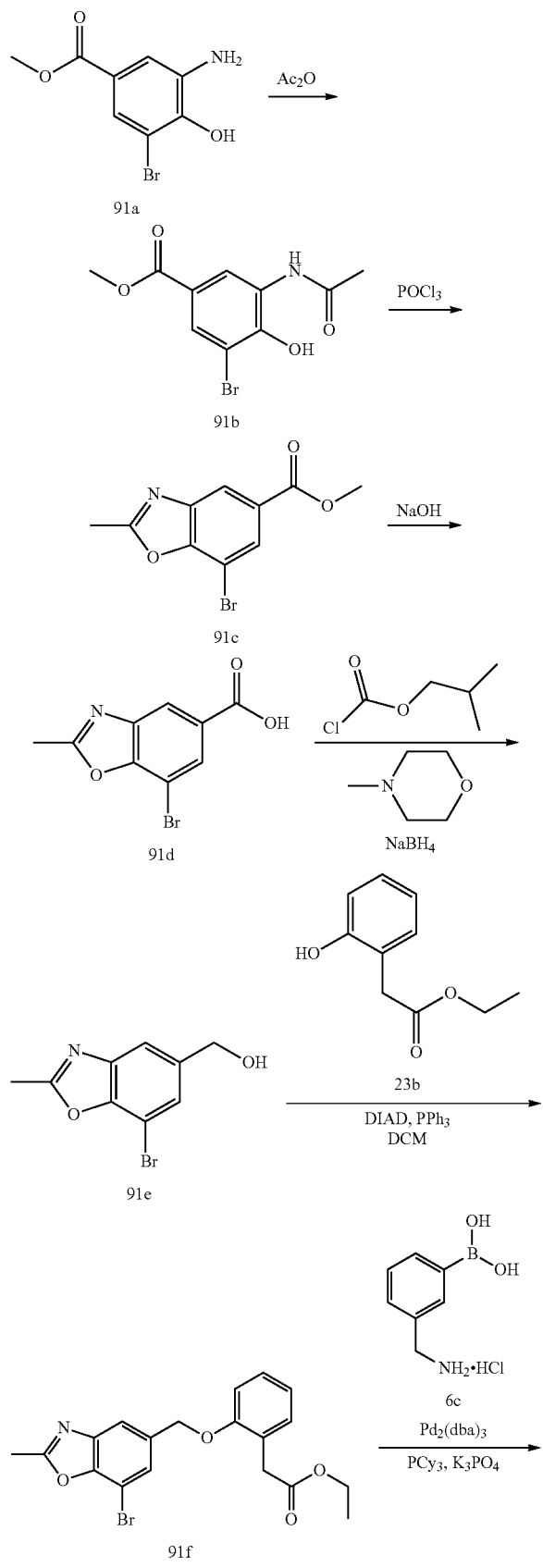
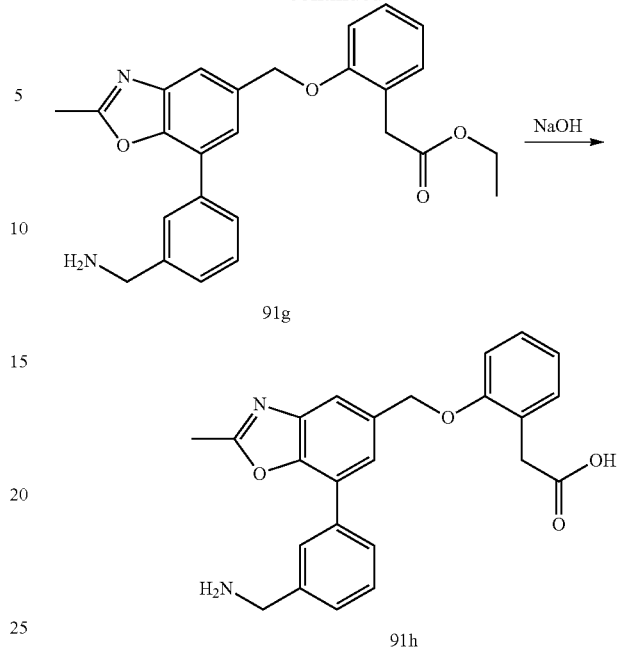

Preparation of 2-(2-((7-(3-(aminomethyl)phenyl)-2-methylbenzo[d]oxazol-5-yl)methoxy)phenyl)acetic Acid (91h)

Step-1: Preparation of methyl 3-acetamido-5-bromo-4-hydroxybenzoate (91b)

To a solution of methyl 3-amino-5-bromo-4-hydroxybenzoate (91a) (0.3 g, 1.22 mmol; CAS #260249-10-3) in THF (5 mL) was added acetic anhydride (0.14 mL, 1.46 mmol). The resulting mixture was stirred at RT for 3 h, diluted with water and extracted with EtOAc. The organic layer was separated washed with water, brine, filtered and concentrated in vacuum. The residue obtained was purified by flash column chromatography [silica (12 g), eluting with hexane in ethyl acetate from 0-70%] to give methyl 3-acetamido-5-bromo-4-hydroxybenzoate (91b) (0.12 g, 34% yield) as a white solid; $^1$H NMR (300 MHz, DMSO-$d_6$) δ 9.91 (s, 1H), 8.06 (d, J=2.1 Hz, 1H), 7.85 (d, J=2.1 Hz, 1H), 7.32-7.19 (m, 1H), 3.81 (s, 3H), 2.13 (s, 3H); MS (ES−): 286.1 & 288.2 (M−1).

Step-2: Preparation of methyl 7-bromo-2-methylbenzo[d]oxazole-5-carboxylate (91c)

To a 50-mL flask equipped with a condenser and an anhydrous $CaCl_2$ dried tube were added methyl 3-acetamido-5-bromo-4-hydroxybenzoate (91b) (0.28 g, 0.97 mmol), phosphoryl trichloride (1.81 mL, 19.44 mmol), and $CHCl_3$ (5 mL). The reaction mixture was heated at 90° C. for 40 h, cooled to room temperature, diluted with EtOAc (10 mL) and ice-water (10 mL). The reaction mixture was basified to pH 8 with aqueous NaOH and extracted with EtOAc (3×100 mL). The organic layers were combined, dried, filtered, and concentrated in vacuum. The residue obtained was purified by flash column chromatography [silica (12 g), eluting with EtOAc/MeOH (9:1) in hexane from 0-50%] to give methyl 7-bromo-2-methylbenzo[d]oxazole-5-carboxylate (91c) (0.1 g, 38% yield) as a white solid; $^1$H NMR (300 MHz, DMSO-d$_6$) δ 8.17 (s, 1H), 8.09 (s, 1H), 3.89 (s, 3H), 2.69 (s, 3H); MS (ES+): 270.0 & 272.0 (M+1).

Step-3: Preparation of 7-bromo-2-methylbenzo[d]oxazole-5-carboxylic Acid (91d)

Compound 91d was prepared according to the procedure reported in step-4 of Scheme-4, from methyl 7-bromo-2-methylbenzo[d]oxazole-5-carboxylate (91c) (0.1 g, 0.37 mmol) in MeOH/THF (5 mL) using a solution of sodium hydroxide (1.48 mL, 3.70 mmol, 2.5 M) in water (2 mL). This gave after workup and purification by reverse phase column chromatography [C18 (50 g), eluting with ACN in water (containing 0.1% HCl) from 0-100%] 7-bromo-2-methylbenzo[d]oxazole-5-carboxylic acid (91d) (0.08 g, 79% yield) as a white solid; MS (ES–): 254.1 (M–1).

Step-4: Preparation of (7-bromo-2-methylbenzo[d]oxazol-5-yl)methanol (91e)

Compound 91e was prepared according to the procedure reported in step-1 of Scheme-23 from 7-bromo-2-methylbenzo[d]oxazole-5-carboxylic acid (91d) (0.12 g, 0.46 mmol) using N-methylmorpholine (0.06 mL, 0.55 mmol) in THF (10 mL), isobutyl chloroformate (0.07 mL, 0.55 mmol) and NaBH$_4$ (0.05 g, 1.37 mmol) in water (0.8 mL). This gave after workup and purification by flash column chromatography [silica (12 g), eluting with EtOAc in hexane from 0-100%] (7-bromo-2-methylbenzo[d]oxazol-5-yl)methanol (91e) (0.08 g, 68% yield) as a clear oil; MS (ES+): 242.0 & 244.1 (M+1).

Step-5: Preparation of Ethyl 2-(2-((7-bromo-2-methylbenzo[d]oxazol-5-yl)methoxy)phenyl)acetate (91f)

Compound 91f was prepared according to the procedure reported in step-2 of Scheme-23 from (7-bromo-2-methyl-benzo[d]oxazol-5-yl)methanol (91e) (0.12 g, 0.50 mmol) in DCM (10 mL) using triphenylphosphine (0.17 g, 0.64 mmol) ethyl 2-(2-hydroxyphenyl) acetate (23b) (0.12 g, 0.64 mmol) and di-(4-chlorobenzyl)azodicarboxylate (DIAD, 0.24 g, 0.64 mmol). This gave after workup and purification by flash column chromatography [silica (12 g), eluting with EtOAc in hexane from 0-50%] ethyl 2-(2-((7-bromo-2-methylbenzo[d]oxazol-5-yl)methoxy)phenyl)acetate (91f) (0.07 g, 32% yield) as a colorless oil; MS (ES+): 426.1 & 428.1 (M+Na).

Step-6: Preparation of Ethyl 2-(2-((7-(3-(aminomethyl)phenyl)-2-methylbenzo[d]oxazol-5-yl)methoxy)phenyl)acetate (91g)

Compound 91g was prepared according to the procedure reported in step-3 of Scheme-1 from ethyl 2-(2-((7-bromo-2-methylbenzo[d]oxazol-5-yl)methoxy)phenyl)acetate (91f) (0.06 g, 0.15 mmol) in dioxane (4 mL) using 3-(aminomethyl)phenylboronic acid hydrochloride (6c) (0.04 g, 0.22 mmol), tripotassium phosphate (3 M aqueous solution, 0.19 mL, 0.25 mmol), tricyclohexylphosphine (0.01 g, 0.05 mmol) and Pd$_2$(dba)$_3$ (0.01 g, 0.02 mmol) under an Ar atmosphere and heating at 125° C. for 90 min in a microwave. This gave after workup, purification by flash column chromatography [silica (12 g), eluting with DMA80 in DCM from 0-50%] ethyl 2-(2-((7-(3-(aminomethyl)phenyl)-2-methylbenzo[d]oxazol-5-yl)methoxy)phenyl)acetate (91g) (0.02 g, 31% yield) as a white solid; MS (ES+): 431.2 (M+1).

Step-7: Preparation of 2-(2-((7-(3-(aminomethyl)phenyl)-2-methylbenzo[d]oxazol-5-yl)methoxy)phenyl)acetic Acid (91h)

Compound 91h was prepared according to the procedure reported in step-4 of Scheme-4, from ethyl 2-(2-((7-(3-(aminomethyl)phenyl)-2-methylbenzo[d]oxazol-5-yl)methoxy)phenyl)acetate (91g) (0.02 g, 0.05 mmol) in MeOH/THF (4 mL) using a solution of sodium hydroxide (0.15 mL, 0.37 mmol, 2.5 M) in water (1 mL). This gave after workup and purification by reverse phase column [C18 (50 g), eluting with ACN in water (containing 0.1% HCl) from 0-100%] 2-(2-((7-(3-(aminomethyl)phenyl)-2-methylbenzo[d]oxazol-5-yl)methoxy)phenyl)acetic acid (91h) (0.01 g, 32% yield) as a white solid; $^1$H NMR (500 MHz, DMSO-d$_6$) δ 8.37 (s, 3H), 8.00 (s, 1H), 7.94 (d, J=7.5 Hz, 1H), 7.75 (s, 1H), 7.72 (s, 1H), 7.62 (m, 1H), 7.56 (m, 1H), 7.23 (m, 2H), 7.08 (d, J=8.0 Hz, 1H), 6.91 (t, J=7.4 Hz, 1H), 5.28 (s, 2H), 4.15 (d, J=5.8 Hz, 2H), 3.60 (s, 2H), 2.66 (s, 3H); MS (ES+): 403.3 (M+1), 425.3 (M+Na); MS (ES–): 401.3 (M–1). HPLC purity: 87.37%.

Scheme-92

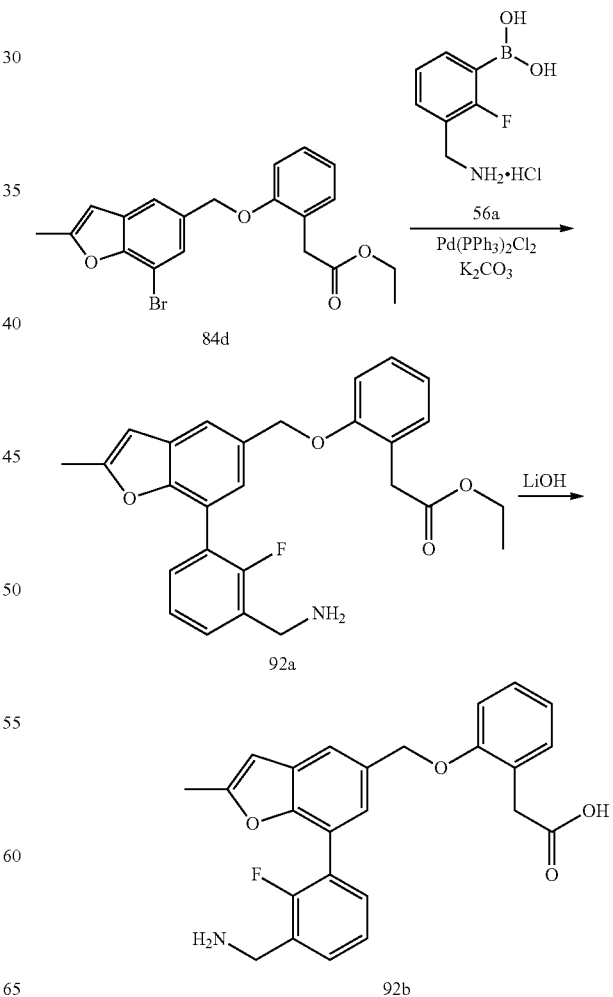

Preparation of 2-(2-((7-(3-(aminomethyl)-2-fluorophenyl)-2-methylbenzofuran-5-yl)methoxy)phenyl) acetic Acid (92b)

Step-1: Preparation of Ethyl 2-(2-((7-(3-(aminomethyl)-2-fluorophenyl)-2-methylbenzofuran-5-yl) methoxy)phenyl)acetate (92a)

Compound 92a was prepared according to the procedure reported in step-3 of Scheme-1 from ethyl 2-(2-((7-bromo-2-methylbenzofuran-5-yl)methoxy)phenyl)acetate (84d) (500 mg, 1.24 mmol) in dioxane (15 mL) using 3-(aminomethyl)-2-fluorophenylboronic acid hydrochloride (56a) (331 mg, 1.61 mmol), bis(triphenylphosphine)palladium(II) chloride (131 mg, 0.186 mmol), a solution of $K_2CO_3$ (514 mg, 3.72 mmol) in water (3 mL) and heating under an argon atmosphere at 100° C. for 3h on an oil bath. This gave after workup, purification by flash column chromatography [silica (12 g), eluting with DMA80 in DCM from 0-50%] followed by purification by reverse phase column chromatography [C18 (50 g), eluting with ACN in water (containing 0.1% HCl) from 0-100%] ethyl 2-(2-((7-(3-(aminomethyl)-2-fluorophenyl)-2-methylbenzofuran-5-yl)methoxy)phenyl)acetate (92a) (336 mg, 61% yield) as a white solid; $^1$H NMR (300 MHz, DMSO-$d_6$) δ 8.74-8.30 (m, 3H, $D_2O$ exchangeable), 7.76-7.57 (m, 3H), 7.42 (t, J=7.7 Hz, 1H), 7.31 (s, 1H), 7.29-7.18 (m, 2H), 7.11 (d, J=8.1 Hz, 1H), 6.91 (t, J=7.4 Hz, 1H), 6.67 (s, 1H), 5.20 (s, 2H), 4.16 (s, 2H), 3.94 (q, J=7.1 Hz, 2H), 3.61 (s, 2H), 2.43 (s, 3H), 1.01 (t, J=7.1 Hz, 3H); $^{19}$F NMR (282 MHz, DMSO-$d_6$) δ−118.71; MS (ES+): 448.3 (M+1).

Step-2: Preparation of 2-(2-((7-(3-(aminomethyl)-2-fluorophenyl)-2-methylbenzofuran-5-yl)methoxy) phenyl)acetic Acid (92b)

Compound 92b was prepared according to the procedure reported in step-6 of Scheme-1, from ethyl 2-(2-((7-(3-(aminomethyl)-2-fluorophenyl)-2-methylbenzofuran-5-yl) methoxy)phenyl)acetate (92a) (256 mg, 0.57 mmol) in MeOH/THF (10 mL) using a solution of lithium hydroxide monohydrate (72.0 mg, 1.72 mmol) in water (1.0 mL). This gave after workup and purification by reverse phase column [C18 (50 g), eluting with ACN in water (containing 0.1% HCl) from 0-100%] 2-(2-((7-(3-(aminomethyl)-2-fluorophenyl)-2-methylbenzofuran-5-yl)methoxy)phenyl)acetic acid (92b) (123 mg, 51% yield) as a white solid; $^1$H NMR (300 MHz, DMSO-$d_6$) δ 12.04 (s, 1H, $D_2O$ exchangeable), 8.58 (s, 3H, $D_2O$ exchangeable), 7.76-7.58 (m, 3H), 7.41 (t, J=7.7 Hz, 1H), 7.36 (s, 1H), 7.27-7.18 (m, 2H), 7.09 (d, J=8.0 Hz, 1H), 6.90 (t, J=7.4 Hz, 1H), 6.66 (t, J=1.1 Hz, 1H), 5.22 (s, 2H), 4.17 (s, 2H), 3.57 (s, 2H), 2.43 (s, 3H); $^{19}$F NMR (282 MHz, DMSO-$d_6$) δ−118.56; MS (ES+): 420.3 (M+1); (ES−): 418.3 (M−1), 456.3 (M+Cl); HPLC purity: 100%.

Scheme-93

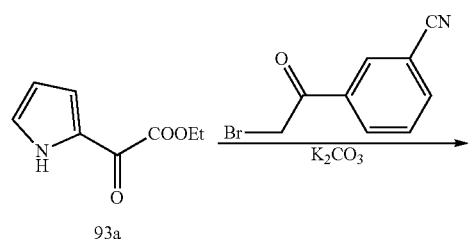

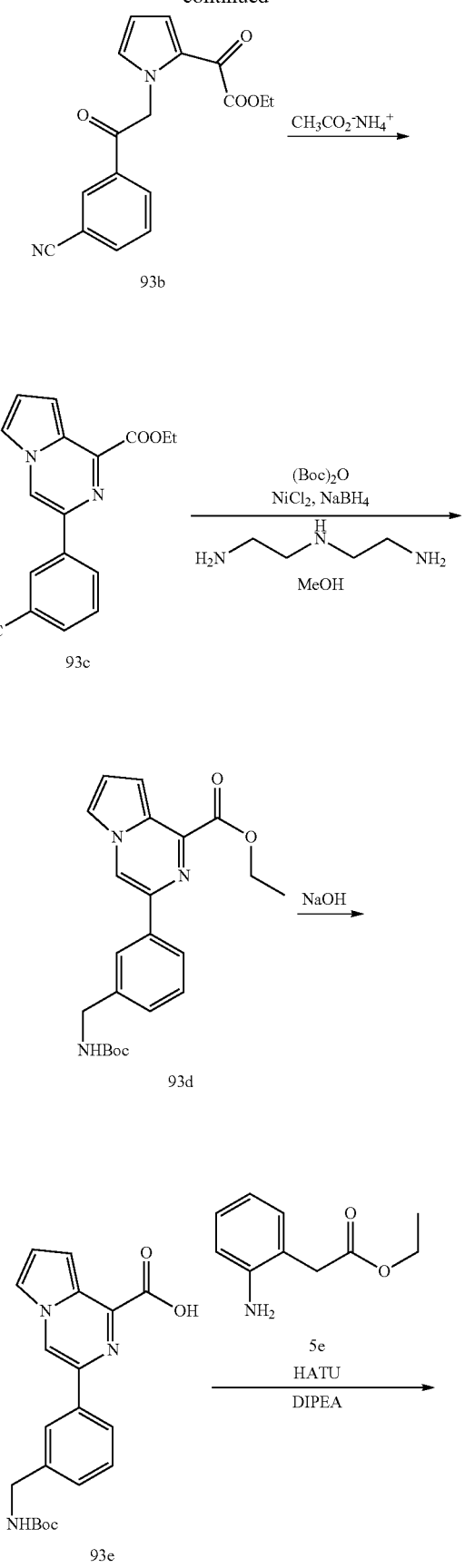

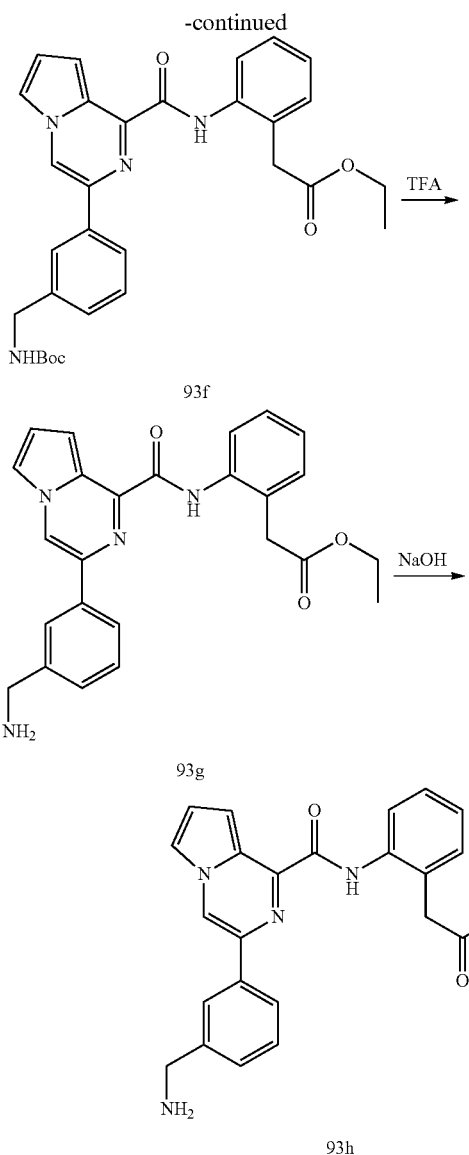

Preparation of 2-(2-(3-(3-(aminomethyl)phenyl)pyrrolo[1,2-a]pyrazine-1-carboxamido)phenyl)acetic Acid (93h)

Step-1: Preparation of Ethyl 2-(1-(2-(3-cyanophenyl)-2-oxoethyl)-1H-pyrrol-2-yl)-2-oxoacetate (93b)

To a solution of ethyl 2-oxo-2-(1H-pyrrol-2-yl)acetate (93a) (1 g, 5.98 mmol; CAS #27472-43-1), 3-(2-bromoacetyl)benzonitrile (1.608 g, 7.18 mmol) in acetonitrile (20 mL) was added potassium carbonate (1.240 g, 8.97 mmol) and the suspension was stirred at room temperature for 6 h. The reaction mixture was diluted with EtOAc (30 mL), filtered over a Celite pad, pad was washed with EtOAc (2×15 mL) and the filtrate was concentrated in vacuum. The residue obtained was purified by flash column chromatography [silica gel 24g, eluting with EtOAc in hexanes 0 to 60%] to afford ethyl 2-(1-(2-(3-cyanophenyl)-2-oxoethyl)-1H-pyrrol-2-yl)-2-oxoacetate (93b) (900 mg, 49% yield) as an off-white solid; $^1$H NMR (300 MHz, DMSO-$d_6$) δ 8.19 (t, J=1.8 Hz, 1H), 8.04 (d, J=7.8 Hz, 1H), 7.98-7.91 (m, 1H), 7.58 (t, J=7.9 Hz, 1H), 7.43 (t, J=2.0 Hz, 1H), 7.25 (dd, J=4.3, 1.6 Hz, 1H), 6.37 (dd, J=4.3, 2.4 Hz, 1H), 5.93 (s, 2H), 4.30 (q, J=7.2 Hz, 2H), 1.28 (t, J=7.1 Hz, 3H).

Step-2: Preparation of Ethyl 3-(3-cyanophenyl)pyrrolo[1,2-a]pyrazine-1-carboxylate (93c)

To a solution of ethyl 2-(1-(2-(3-cyanophenyl)-2-oxoethyl)-1H-pyrrol-2-yl)-2-oxoacetate (93b) (0.7 g, 2.26 mmol) in ethanol (30 mL) was added ammonium acetate (1.74 g, 22.56 mmol) and was stirred at 90° C. for 16 h. The reaction mixture was partitioned between water (100 mL) and EtOAc (80 mL) and layers were separated. The aqueous layer was extracted with EtOAc (60 mL) and the combined organics were washed with brine, dried, filtered, concentrated in vacuum. The residue obtained was purified by flash column chromatography [silica gel 24g, eluting with EtOAc in hexane 0 to 60%] to afford ethyl 3-(3-cyanophenyl)pyrrolo[1,2-a]pyrazine-1-carboxylate (93c) (250 mg, 38% yield) as a light orange solid; $^1$H NMR (300 MHz, DMSO-$d_6$) δ 9.37 (s, 1H), 8.44 (d, J=1.7 Hz, 1H), 8.38 (dt, J=8.1, 1.5 Hz, 1H), 7.95 (dd, J=2.6, 1.3 Hz, 1H), 7.87 (dt, J=7.7, 1.4 Hz, 1H), 7.74 (t, J=7.8 Hz, 1H), 7.29 (d, J=4.2 Hz, 1H), 7.14 (dd, J=4.1, 2.6 Hz, 1H), 4.48 (q, J=7.1 Hz, 2H), 1.42 (t, J=7.1 Hz, 3H); MS (ES+): 292.2 (M+1), 314.2 (M+Na).

Step-3: Preparation of Ethyl 3-(3-(((tert-butoxycarbonyl)amino)methyl)phenyl)pyrrolo[1,2-a]pyrazine-1-carboxylate (93d)

Compound 93d was prepared according to the procedure reported in step-1 of Scheme-80 from ethyl 3-(3-cyanophenyl)pyrrolo[1,2-a]pyrazine-1-carboxylate (93c) (210 mg, 0.721 mmol) in methanol (20 mL), THF (5 mL) using BOC-anhydride (0.251 mL, 1.08 mmol), nickel(II) chloride (9 mg, 0.072 mmol), sodium borohydride (82 mg, 2.16 mmol) and N1-(2-aminoethyl)ethane-1,2-diamine (372 mg, 3.60 mmol). This gave after workup and purification by flash column chromatography [silica (24 g), eluting with EtOAc in hexanes 0 to 65%] ethyl 3-(3-(((tert-butoxycarbonyl)amino)methyl)phenyl)pyrrolo[1,2-a]pyrazine-1-carboxylate (93d) (80 mg, 28% yield) as a white solid.

Step-4: Preparation of 3-(3-(((tert-butoxycarbonyl)amino)methyl)phenyl)pyrrolo[1,2-a]pyrazine-1-carboxylic Acid (93e)

Compound 93e was prepared according to the procedure reported in step-4 of Scheme-4 from ethyl 3-(3-(((tert-butoxycarbonyl)amino)methyl)phenyl)pyrrolo[1,2-a]pyrazine-1-carboxylate (93d) (75 mg, 0.19 mmol) in THF (5 mL) using an aqueous solution of NaOH (0.759 mL, 0.759 mmol, 1 M). This gave after workup and purification by flash column chromatography [silica (12 g), eluting with DCM-80 in DCM] 3-(3-(((tert-butoxycarbonyl)amino)methyl)phenyl)pyrrolo[1,2-a]pyrazine-1-carboxylic acid (93e) (40 mg, 57% yield) as a colorless solid; $^1$H NMR (300 MHz, DMSO-$d_6$) δ 9.11 (s, 1H), 8.04-7.84 (m, 3H), 7.44 (t, J=7.7 Hz, 2H), 7.25 (t, J=5.8 Hz, 2H), 7.06 (dd, J=4.1, 2.6 Hz, 1H), 4.22 (d, J=6.1 Hz, 2H), 1.40 (d, J=4.9 Hz, 9H); MS (ES+): 390.3 (M+Na), (ES−): 366.3 (M−1).

Step-5: Preparation of Ethyl 2-(2-(3-(3-(((tert-butoxycarbonyl)amino)methyl)phenyl)pyrrolo[1,2-a]pyrazine-1-carboxamido)phenyl)acetate (93f)

Compound 93f was prepared according to the procedure reported in step-4 of Scheme-1 from 3-(3-(((tert-butoxycarbonyl)amino)methyl)phenyl)pyrrolo[1,2-a]pyrazine-1-carboxylic acid (93e) (34 mg, 0.093 mmol) in DMF (2 mL) using ethyl 2-(2-aminophenyl)acetate (5e) (25 mg, 0.14 mmol), DIPEA (0.05 mL, 0.278 mmol) and HATU (53 mg, 0.14 mmol). This gave after workup and purification by flash column chromatography [silica (12 g), eluting with 0-60% EtOAc in hexane] ethyl 2-(2-(3-(3-(((tert-butoxycarbonyl)amino)methyl)phenyl)pyrrolo[1,2-a]pyrazine-1-carboxamido)phenyl)acetate (93f) (34 mg, 70% yield) as a semisolid; $^1$H NMR (300 MHz, DMSO-$d_6$) δ 10.58 (s, 1H), 9.18 (s, 1H), 8.06 (d, J=9.8 Hz, 2H), 7.97 (dd, J=2.6, 1.3 Hz, 1H), 7.89 (d, J=8.5 Hz, 1H), 7.51 (d, J=4.1 Hz, 1H), 7.45 (t, J=7.6 Hz, 1H), 7.39 (dd, J=5.5, 1.8 Hz, 3H), 7.31-7.16 (m, 2H), 7.11 (dd, J=4.2, 2.5 Hz, 1H), 4.25 (d, J=6.1 Hz, 2H), 3.98 (q, J=7.2 Hz, 2H), 3.87 (s, 2H), 1.39 (s, 9H), 0.97 (t, J=7.1 Hz, 3H); MS (ES+): 551.3 (M+Na).

Step-6: Preparation of Ethyl 2-(2-(3-(3-(aminomethyl)phenyl)pyrrolo[1,2-a]pyrazine-1-carboxamido)phenyl)acetate (93g)

Compound 93g was prepared according to the procedure reported in step-5 of Scheme-1 from ethyl 2-(2-(3-(3-(((tert-butoxycarbonyl)amino)methyl)phenyl)pyrrolo[1,2-a]pyrazine-1-carboxamido)phenyl)acetate (93f) (30 mg, 0.057 mmol) in DCM (2 mL) using TFA (0.044 mL, 0.568 mmol). This gave after workup and purification by flash column chromatography [silica (12 g), eluting with DMA80 in DCM from 0-50%] ethyl 2-(2-(3-(3-(aminomethyl)phenyl)pyrrolo[1,2-a]pyrazine-1-carboxamido)phenyl)acetate (93g) (25 mg, 103% yield) TFA salt as a brown syrup. This was used in the next reaction without further purification; MS (ES+): 429.3 (M+1), 451.3 (M+Na).

Step-7: Preparation of 2-(2-(3-(3-(aminomethyl)phenyl)pyrrolo[1,2-a]pyrazine-1-carboxamido)phenyl)acetic Acid (93h)

Compound 93h was prepared according to the procedure reported in step-4 of Scheme-4 from ethyl 2-(2-(3-(3-(aminomethyl)phenyl)pyrrolo[1,2-a]pyrazine-1-carboxamido)phenyl)acetate (93g) (25 mg, 0.057 mmol) in THF (5 mL) using an aqueous solution of NaOH (0.114 mL, 0.228 mmol, 2 M). This gave after workup and purification by reverse phase column chromatography [C18 (50 g), eluting with ACN in water (containing 0.1% HCl) from 0-100%] 2-(2-(3-(3-(aminomethyl)phenyl)pyrrolo[1,2-a]pyrazine-1-carboxamido)phenyl)acetic acid (93h) (14 mg, 61% yield) hydrochloride salt as a white solid; 1H NMR (300 MHz, DMSO-$d_6$) δ 10.67 (s, 1H, D$_2$O exchangeable), 9.26 (s, 1H), 8.51-8.24 (m, 4H, 3H D$_2$O exchangeable), 8.16 (d, J=7.5 Hz, 1H), 8.01-7.97 (m, 1H), 7.94 (d, J=8.2 Hz, 1H), 7.63-7.47 (m, 4H), 7.43-7.34 (m, 2H), 7.27-7.18 (m, 1H), 7.16-7.10 (m, 1H), 4.15 (q, J=5.9 Hz, 2H), 3.79 (s, 2H); MS (ES+): 401.3 (M+1), 423.3 (M+Na), (ES−): 399.3 (M−1); HPLC purity: 97.62%.

Scheme-94

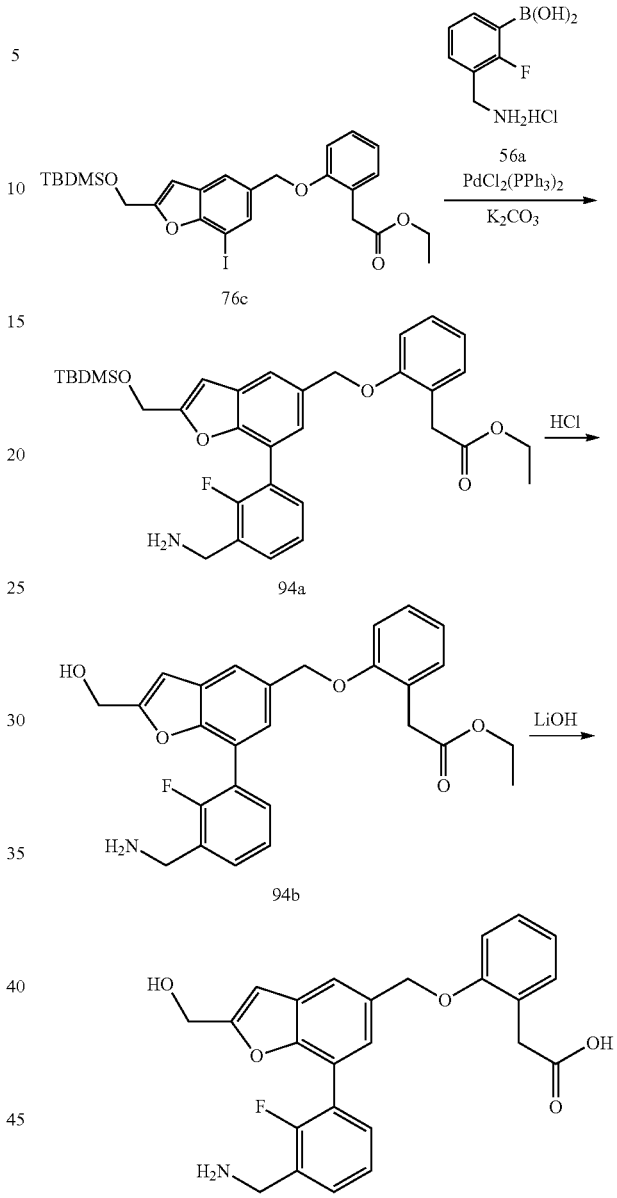

Preparation of 2-(2-((7-(3-(aminomethyl)-2-fluorophenyl)-2-(hydroxymethyl)benzofuran-5-yl)methoxy)phenyl)acetic Acid (94c)

Step-1: Preparation of Ethyl 2-(2-((7-(3-(aminomethyl)-2-fluorophenyl)-2-(((tert-butyldimethyl silyl)oxy)methyl)benzofuran-5-yl)methoxy)phenyl)acetate (94a)

Compound 94a was prepared according to the procedure reported in step-3 of Scheme-1 from ethyl 2-(2-((2-(((tert-butyldimethyl silyl)oxy)methyl)-7-iodobenzofuran-5-yl)methoxy)phenyl)acetate (76c) (7.2 g, 12.40 mmol) in dioxane (50 mL) using 3-(aminomethyl)-2-fluorophenylboronic acid hydrochloride (56a) (3.82 g, 18.60 mmol), a solution of K₂CO₃ (5.14 g, 37.2 mmol) in water (10 mL), bis(triphenylphosphine)palladium(II) chloride (1.31 g, 1.86 mmol) and heating at 100° C. for 3h on oil bath. This gave after workup, purification by flash column chromatography [silica (80 g), eluting with DMA80 in DCM from 0-50%] ethyl 2-(2-((7-(3-(aminomethyl)-2-fluorophenyl)-2-(((tert-butyldimethylsilyl)oxy)methyl)benzofuran-5-yl)methoxy)phenyl)acetate (94a) (5.4 g, 75% yield) as a clear oil; ¹H NMR (300 MHz, DMSO-d₆) δ 7.64 (d, J=1.7 Hz, 1H), 7.58-7.49 (m, 3H), 7.41-7.35 (m, 1H), 7.33 (s, 1H), 7.27-7.13 (m, 3H), 7.06 (d, J=8.1 Hz, 1H), 6.89-6.79 (m, 2H), 5.15 (s, 2H), 4.71 (s, 2H), 3.84 (q, J=7.1 Hz, 2H), 3.77 (s, 2H), 3.56 (s, 2H), 0.92 (t, J=7.1, 2.3 Hz, 3H), 0.80 (s, 9H), 0.00 (s, 6H).

Step-2: Preparation of Ethyl 2-(2-((7-(3-(aminomethyl)-2-fluorophenyl)-2-(hydroxymethyl)benzofuran-5-yl)methoxy)phenyl)acetate (94b)

To a solution of ethyl 2-(2-((7-(3-(aminomethyl)-2-fluorophenyl)-2-(((tert-butyldimethyl silyl)oxy)methyl)benzofuran-5-yl)methoxy)phenyl)acetate (94a) (700 mg, 1.21 mmol) in THF (10 mL) was added HCl (2N aqueous) (1.82 mL, 3.63 mmol). The resulting mixture was stirred at RT for 12h, concentrated in vacuum to dryness and the residue obtained. After TLC showed the reaction went completion, the organic solvent was then removed, the residue was purified by reverse phase column chromatography [C18 (50 g), eluting with ACN in water (containing 0.1% HCl) from 01-00%] to afford ethyl 2-(2-((7-(3-(aminomethyl)-2-fluorophenyl)-2-(hydroxymethyl)benzofuran-5-yl)methoxy)phenyl)acetate (94b) (173 mg, 31% yield) HCl salt as a white solid; ¹H NMR (300 MHz, DMSO-d₆) δ 8.62 (s, 3H, D₂O exchangeable), 7.75-7.69 (m, 2H), 7.69-7.61 (m, 1H), 7.44 (d, J=7.6 Hz, 1H), 7.40-7.35 (m, 1H), 7.30-7.18 (m, 2H), 7.15-7.07 (m, 1H), 6.91 (t, J=7.4, 1.2 Hz, 1H), 6.85 (s, 1H), 5.50 (t, J=5.8 Hz, 1H, D₂O exchangeable), 5.22 (s, 2H), 4.55 (d, J=4.8 Hz, 2H), 4.16 (s, 2H), 3.94 (q, J=7.1 Hz, 2H), 3.62 (s, 2H), 1.01 (t, J=7.1 Hz, 3H); ¹⁹F NMR (282 MHz, DMSO-d₆) δ−118.74; MS (ES+): 464.3 (M+1); (ES−): 498.3 (M+Cl).

Step-3: Preparation of 2-(2-((7-(3-(aminomethyl)-2-fluorophenyl)-2-(hydroxymethyl)benzofuran-5-yl)methoxy)phenyl)acetic Acid (94c)

Compound 94c was prepared according to the procedure reported in step-6 of Scheme-1, from ethyl 2-(2-((7-(3-(aminomethyl)-2-fluorophenyl)-2-(hydroxymethyl)benzofuran-5-yl)methoxy)phenyl)acetate (94b) (420 mg, 0.73 mmol) in MeOH/THF (10 mL) using a solution of lithium hydroxide monohydrate (92 mg, 2.18 mmol) in water (1.0 mL). This gave after workup and purification by reverse phase column [C18 (50 g), eluting with ACN in water (containing 0.1% HCl) from 0-100%] 2-(2-((7-(3-(aminomethyl)-2-fluorophenyl)-2-(hydroxymethyl)benzofuran-5-yl)methoxy)phenyl)acetic acid (94c) (249 mg, 79% yield) HCl salt as a white solid; ¹H NMR (300 MHz, DMSO-d₆) δ 12.21 (s, 1H, D₂O exchangeable), 8.63 (s, 3H, D₂O exchangeable), 7.75 (d, J=1.6 Hz, 1H), 7.73-7.62 (m, 2H), 7.46-7.37 (m, 2H), 7.28-7.17 (m, 2H), 7.09 (d, J=8.1 Hz, 1H), 6.90 (t, J=7.4 Hz, 1H), 6.84 (s, 1H), 5.24 (s, 2H), 4.55 (s, 2H), 4.16 (d, J=5.7 Hz, 2H), 3.58 (s, 2H); ¹⁹F NMR (282 MHz, DMSO-d₆) δ−118.57; MS (ES+): 436.3 (M+1); (ES−): 470.3 (M+Cl).

Scheme-95

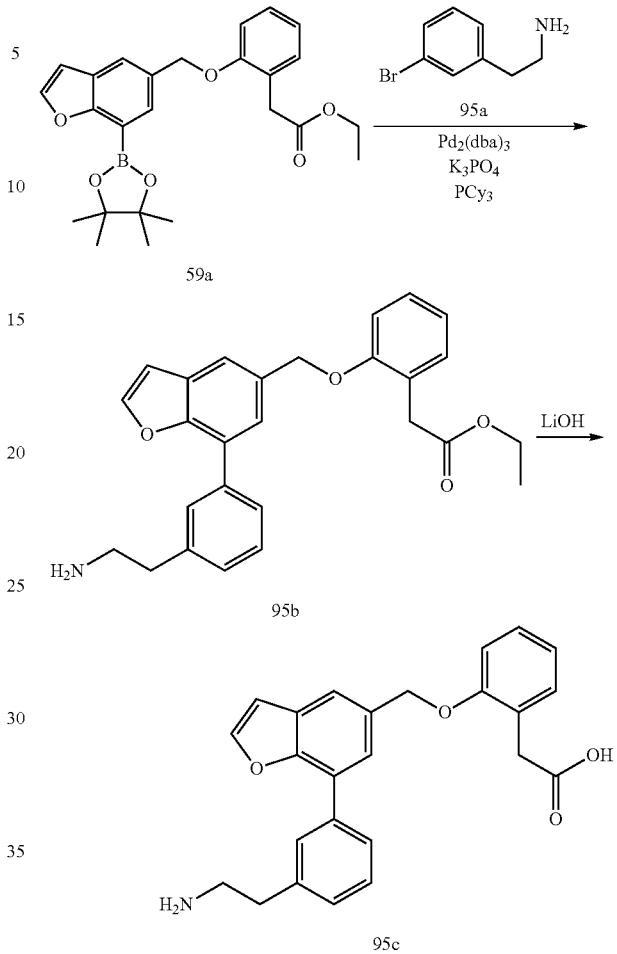

Preparation of 2-(2-((7-(3-(2-aminoethyl)phenyl)benzofuran-5-yl)methoxy)phenyl)acetic acid (95c)

Step-1: Preparation of Ethyl 2-(2-((7-(3-(2-aminoethyl)phenyl)benzofuran-5-yl)methoxy)phenyl)acetate (95b)

Compound 95b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (450 mg, 1.03 mmol) in dioxane (6 mL) using 3-bromophenethylamine (95a) (351 mg, 1.75 mmol; CAS #58971-11-2), tripotassium phosphate (3M, 0.584 mL, 1.75 mmol), tricyclohexylphosphine (87 mg, 0.31 mmol) and Pd₂(dba)₃ (94 mg, 0.10 mmol) under an Ar atmosphere and heating at 120° C. for 90 min in a microwave. This gave after workup, purification by flash column chromatography [silica (12 g), eluting with DMA80 in DCM from 0-70%] followed by purification by reverse phase column [C18 (50 g), eluting with ACN in water (containing 0.1% HCl) from 0-100%] ethyl 2-(2-((7-(3-(2-aminoethyl)phenyl)benzofuran-5-yl)methoxy)phenyl)acetate (95b) (252 mg, 57% yield) as a white solid; ¹H NMR (300 MHz, DMSO-d₆) δ 8.27-7.92 (m, 4H, partially D₂O exchangeable), 7.81-7.73 (m, 2H), 7.72 (d, J=1.5 Hz, 1H), 7.60 (d, J=1.6 Hz, 1H), 7.51 (t, J=7.6 Hz, 1H), 7.34 (d, J=7.6

Hz, 1H), 7.30-7.19 (m, 2H), 7.12 (d, J=8.1 Hz, 1H), 7.08-7.02 (m, 1H), 6.91 (t, J=7.4 Hz, 1H), 5.25 (s, 2H), 3.93 (q, J=7.1 Hz, 2H), 3.63 (s, 2H), 3.18-3.05 (m, 2H), 3.05-2.96 (m, 2H), 0.99 (t, J=7.1 Hz, 3H); MS (ES+): 430.3 (M+1); (ES−): 464.3 (M+Cl).

Step-2: Preparation of 2-(2-((7-(3-(2-aminoethyl)phenyl)benzofuran-5-yl)methoxy)phenyl)acetic Acid (95c)

Compound 95c was prepared according to the procedure reported in step-6 of Scheme-1, from ethyl 2-(2-((7-(3-(2-aminoethyl)phenyl)benzofuran-5-yl)methoxy)phenyl)acetate (95b) (160 mg, 0.37 mmol) in MeOH/THF (10 mL) using a solution of lithium hydroxide monohydrate (47 mg, 1.12 mmol) in water (1 mL). This gave after workup and purification by reverse phase column [C18 (50 g), eluting with ACN in water (containing 0.1% HCl) from 0-100%] 2-(2-((7-(3-(2-aminoethyl)phenyl)benzofuran-5-yl)methoxy)phenyl)acetic acid (95c) (82 mg, 55% yield) HCl salt as a white solid; $^1$H NMR (300 MHz, DMSO-$d_6$) δ 12.18 (s, 1H, D$_2$O exchangeable), 8.16-7.96 (m, 4H, D$_2$O exchangeable), 7.83-7.72 (m, 3H), 7.64 (d, J=1.7 Hz, 1H), 7.50 (t, J=7.6 Hz, 1H), 7.37-7.29 (m, 1H), 7.28-7.20 (m, 2H), 7.13-7.06 (m, 1H), 7.04 (d, J=2.2 Hz, 1H), 6.90 (t, J=7.4, 1.1 Hz, 1H), 5.27 (s, 2H), 3.60 (s, 2H), 3.18-3.06 (m, 2H), 3.06-2.94 (m, 2H); MS (ES+): 402.3 (M+1); (ES−): 400.3 (M−1), 436.3 (M+Cl).

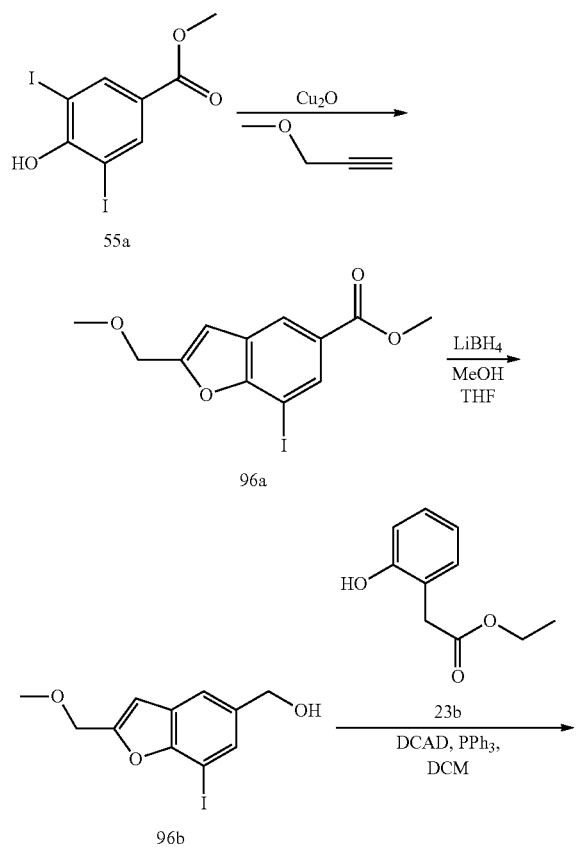

Scheme-96

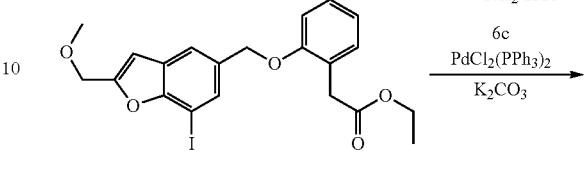

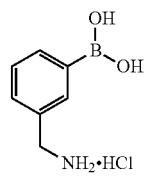

Preparation of 2-(2-((7-(3-(aminomethyl)phenyl)-2-(methoxymethyl)benzofuran-5-yl)methoxy)phenyl)acetic Acid (96e)

Step-1: Preparation of methyl 7-iodo-2-(methoxymethyl)benzofuran-5-carboxylate (96a)

Compound 96a was prepared according to the procedure reported in step-1 of Scheme-55, from methyl 4-hydroxy-3,5-diiodobenzoate (55a) (7 g, 17.33 mmol) in pyridine (15 mL) using methyl propargyl ether (1.22 g, 17.33 mmol) and copper(I) oxide (1.24 g, 8.66 mmol). This gave after workup and purification by flash column chromatography [silica (24 g), eluting with EtOAc in hexane from 0-70%] methyl 7-iodo-2-(methoxymethyl)benzofuran-5-carboxylate (96a) (3.45 g, 58% yield) as a white solid; $^1$H NMR (300 MHz, DMSO-$d_6$) δ 8.27 (d, J=1.5 Hz, 1H), 8.22 (d, J=1.5 Hz, 1H), 7.18 (d, J=0.8 Hz, 1H), 4.60 (s, 2H), 3.88 (s, 3H), 3.36 (s, 3H).

Step-2: Preparation of (7-iodo-2-(methoxymethyl)benzofuran-5-yl)methanol (96b)

Compound 96b was prepared according to the procedure reported in step-2 of Scheme-76 from methyl 7-iodo-2-

(methoxymethyl)benzofuran-5-carboxylate (96a) (3.45 g, 9.97 mmol) in THF (60 mL) using LiBH$_4$ (14.95 mL, 29.9 mmol, 2 M solution in THF) and MeOH (0.96 g, 29.9 mmol). This gave after workup and purification by flash column chromatography [silica (24 g), eluting with EtOAc in hexane from 0-60%] (7-iodo-2-(methoxymethyl)benzofuran-5-yl)methanol (96b) (2.94 g, 93% yield) as a white solid; $^1$H NMR (300 MHz, DMSO-d$_6$) δ 7.66-7.62 (m, 1H), 7.56-7.51 (m, 1H), 7.02 (t, J=0.9 Hz, 1H), 5.26 (t, J=5.8, 1.1 Hz, 1H), 4.58-4.50 (m, 4H), 3.33 (s, 3H).

Step-3: Preparation of Ethyl 2-(2-((7-iodo-2-(methoxymethyl)benzofuran-5-yl)methoxy)phenyl) acetate (96c)

Compound 96c was prepared according to the procedure reported in step-2 of Scheme-23 from (7-iodo-2-(methoxymethyl)benzofuran-5-yl)methanol (96b) (2.94 g, 9.24 mmol) in DCM (180 mL) using triphenylphosphine (2.67 g, 10.17 mmol), ethyl 2-(2-hydroxyphenyl) acetate (23b) (1.83 g, 10.17 mmol) and di-(4-chlorobenzyl)azodicarboxylate (DCAD, 3.73 g, 10.17 mmol) in DCM (20 mL). This gave after workup and purification by flash column chromatography [silica (40 g), eluting with EtOAc in hexane from 0-50%] ethyl 2-(2-((7-iodo-2-(methoxymethyl)benzofuran-5-yl)methoxy)phenyl)acetate (96c) (3.92 g, 88% yield) as a clear oil, which became a white solid after standing at RT. $^1$H NMR (300 MHz, DMSO-d$_6$) δ 7.74 (d, J=1.5 Hz, 1H), 7.67 (d, J=1.5 Hz, 1H), 7.29-7.18 (m, 2H), 7.10-7.04 (m, 2H), 6.91 (t, J=7.4 Hz, 1H), 5.14 (s, 2H), 4.56 (s, 2H), 4.03 (q, J=7.1 Hz, 2H), 3.61 (s, 2H), 3.34 (s, 3H), 1.09 (t, J=7.1 Hz, 3H).

Step-4: Preparation of Ethyl 2-(2-((7-(3-(aminomethyl)phenyl)-2-(methoxymethyl)benzofuran-5-yl) methoxy)phenyl)acetate (96d)

Compound 96d was prepared according to the procedure reported in step-3 of Scheme-1 from ethyl 2-(2-((7-iodo-2-(methoxymethyl)benzofuran-5-yl)methoxy)phenyl)acetate (96c) (500 mg, 1.04 mmol) in dioxane (15 mL) using 3-(aminomethyl)phenylboronic acid hydrochloride (6c) (254 mg, 1.35 mmol), a solution of K$_2$CO$_3$ (432 mg, 3.12 mmol) in water (3 mL), bis(triphenylphosphine)palladium (II) chloride (110 mg, 0.16 mmol) and heating at 100° C. for 3h on oil bath. This gave after workup, purification by flash column chromatography [silica (12 g), eluting with DMA80 in DCM from 0-50%] followed by purification by reverse phase column chromatography [C18 (50 g), eluting with ACN in water (containing 0.1% HCl) from 0-100%] ethyl 2-(2-((7-(3-(aminomethyl)phenyl)-2-(methoxymethyl)benzofuran-5-yl)methoxy)phenyl)acetate (96d) (262 mg, 55% yield) as a white solid; $^1$H NMR (300 MHz, DMSO-d$_6$) δ 8.61 (s, 3H, D$_2$O exchangeable), 7.98 (s, 1H), 7.95-7.85 (m, 1H), 7.70 (d, J=1.6 Hz, 1H), 7.66-7.56 (m, 3H), 7.30-7.18 (m, 2H), 7.15-7.09 (m, 1H), 7.00 (s, 1H), 6.92 (t, J=7.4, 1.1 Hz, 1H), 5.24 (s, 2H), 4.59 (s, 2H), 4.12 (s, 2H), 3.95 (q, J=7.2 Hz, 2H), 3.57 (s, 2H), 3.33 (s, 3H), 1.00 (t, J=7.1, 1.4 Hz, 3H); MS (ES+): 460.3 (M+1); (ES−): 494.3 (M+Cl).

Step-5: Preparation of 2-(2-((7-(3-(aminomethyl) phenyl)-2-(methoxymethyl)benzofuran-5-yl) methoxy)phenyl)acetic Acid (96e)

Compound 96e was prepared according to the procedure reported in step-6 of Scheme-1, from ethyl 2-(2-((7-(3-(aminomethyl)phenyl)-2-(methoxymethyl)benzofuran-5-yl) methoxy)phenyl)acetate (96d) (152 mg, 0.33 mmol) in MeOH/THF (10 mL) using a solution of lithium hydroxide monohydrate (42 mg, 0.99 mmol) in water (1.0 mL). This gave after workup and purification by reverse phase column [C18 (50 g), eluting with ACN in water (containing 0.1% HCl) from 0-100%] 2-(2-((7-(3-(aminomethyl)phenyl)-2-(methoxymethyl)benzofuran-5-yl)methoxy)phenyl)acetic acid (96e) (95 mg, 67% yield) as a white solid; $^1$H NMR (300 MHz, DMSO-d$_6$) δ 12.22 (s, 1H, D$_2$O exchangeable), 8.53 (s, 3H, D$_2$O exchangeable), 7.97 (s, 1H), 7.95-7.88 (m, 1H), 7.75-7.70 (m, 1H), 7.64 (d, J=1.7 Hz, 1H), 7.61-7.53 (m, 2H), 7.27-7.17 (m, 2H), 7.10 (d, J=8.1 Hz, 1H), 6.99 (s, 1H), 6.90 (t, J=7.3 Hz, 1H), 5.26 (s, 2H), 4.58 (s, 2H), 4.13 (s, 2H), 3.60 (s, 2H), 3.33 (s, 3H); MS (ES+): 432.3 (M+1); (ES−): 430.3 (M−1), 466.3 (M+Cl).

Scheme-97

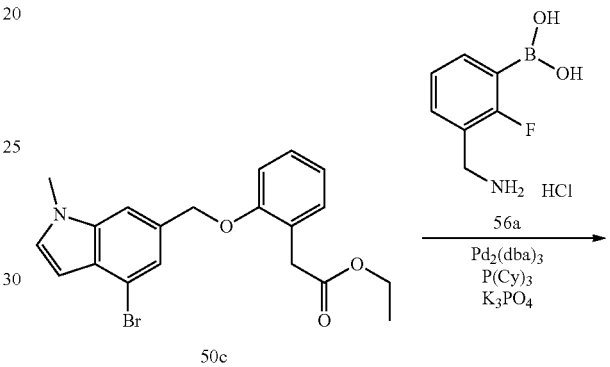

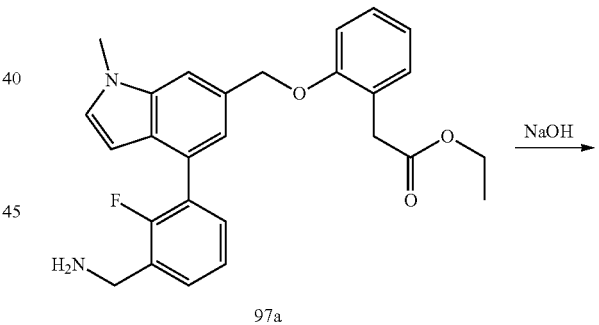

97a

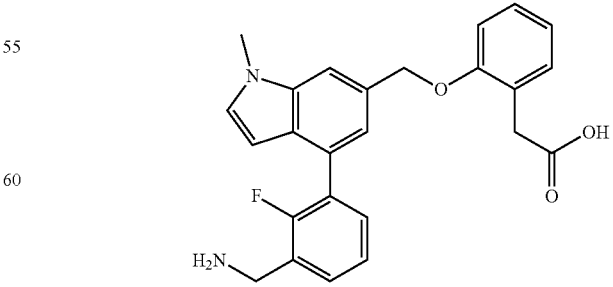

97b

Preparation of 2-(2-((4-(3-(aminomethyl)-2-fluoro-phenyl)-1-methyl-1H-indol-6-yl)methoxy)phenyl) acetic Acid (97b)

Step-1: Preparation of Ethyl 2-(2-((4-(3-(aminomethyl)-2-fluorophenyl)-1-methyl-1H-indol-6-yl) methoxy)phenyl)acetate (97a)

Compound 97a was prepared according to the procedure reported in step-3 of Scheme-1 from ethyl 2-(2-((4-bromo-1-methyl-1H-indol-6-yl)methoxy)phenyl)acetate (50c) (0.5 g, 1.24 mmol) in dioxane (5 mL) using 3-(aminomethyl)-2-fluorophenylboronic acid hydrochloride (56a) (0.38 g, 1.86 mmol), tripotassium phosphate (3 M aqueous solution, 0.70 mL, 2.11 mmol), tricyclohexylphosphine (0.11 g, 0.37 mmol) and Pd$_2$(dba)$_3$ (0.11 g, 0.12 mmol) under an Ar atmosphere and heating at 125° C. for 90 min in a microwave. This gave after workup, purification by flash column chromatography [silica (24 g), eluting with hexane in ethyl acetate from 0-70%] followed by purification by reverse phase column [C18 (50 g), eluting with ACN in water (containing 0.1% HCl) from 0-100%] ethyl 2-(2-((4-(3-(aminomethyl)-2-fluorophenyl)-1-methyl-1H-indol-6-yl) methoxy)phenyl)acetate (97a) (0.26 g, 47% yield) as a white solid; $^1$H NMR (300 MHz, DMSO-d$_6$) δ 8.44 (s, 3H), 7.68-7.54 (m, 3H), 7.44-7.34 (m, 2H), 7.29-7.18 (m, 2H), 7.18-7.10 (m, 2H), 6.90 (t, J=7.4 Hz, 1H), 6.35 (t, J=2.9 Hz, 1H), 5.25 (s, 2H), 4.16 (s, 2H), 3.93 (q, J=7.0 Hz, 2H), 3.85 (s, 3H), 3.63 (s, 2H), 1.00 (t, J=7.1 Hz, 3H); $^{19}$F NMR (282 MHz, DMSO-d$_6$) δ−118.88; MS (ES+): 447.3 (M+1); MS (ES−): 481.3 (M+Cl). HPLC purity: 98.44%.

Step-2: Preparation of 2-(2-((4-(3-(aminomethyl)-2-fluorophenyl)-1-methyl-1H-indol-6-yl)methoxy) phenyl)acetic Acid (97b)

Compound 97b was prepared according to the procedure reported in step-4 of Scheme-4, from ethyl 2-(2-((4-(3-(aminomethyl)-2-fluorophenyl)-1-methyl-1H-indol-6-yl) methoxy)phenyl)acetate (97a) (0.08 g, 0.18 mmol) in MeOH/THF (4 mL) using a solution of sodium hydroxide (0.57 mL, 1.43 mmol, 2.5 M) in water (1 mL). This gave after workup and purification by reverse phase column [C18 (50 g), eluting with ACN in water (containing 0.1% HCl) from 0-100%] 2-(2-((4-(3-(aminomethyl)-2-fluorophenyl)-1-methyl-1H-indol-6-yl)methoxy)phenyl)acetic acid (97b) (0.02 g, 21% yield) HCl salt as a white solid; $^1$H NMR (300 MHz, DMSO-d$_6$) δ 12.17 (s, 1H), 8.41 (s, 4H), 7.64 (s, 1H), 7.63-7.54 (m, 1H), 7.45-7.35 (m, 2H), 7.29-7.15 (m, 3H), 7.11 (d, J=8.1 Hz, 1H), 6.95-6.86 (m, 1H), 6.34 (t, J=3.0 Hz, 1H), 5.27 (s, 2H), 4.17 (s, 2H), 3.84 (s, 3H), 3.60 (s, 2H); $^{19}$F NMR (282 MHz, DMSO-d$_6$) δ−118.79; MS (ES+): 419.3 (M+1); MS (ES−): 417.4 (M−1), 453.3 (M+Cl). HPLC purity: 94.07%.

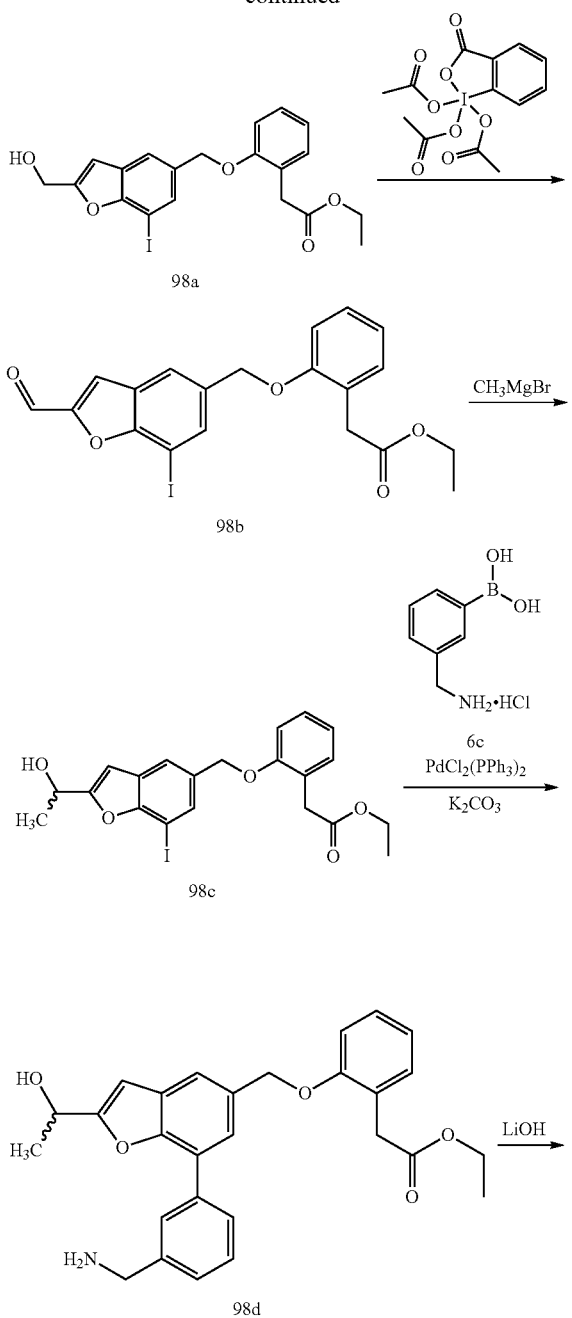

Scheme-98

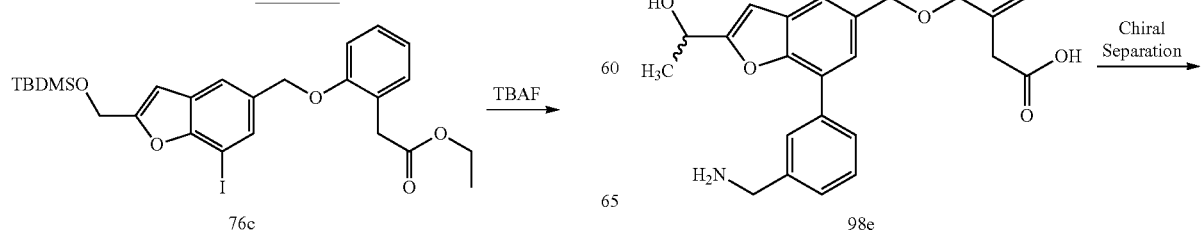

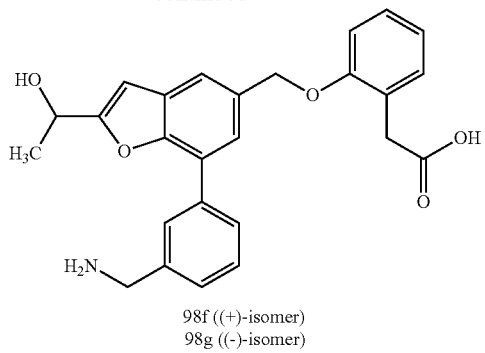

98f ((+)-isomer)
98g ((−)-isomer)

Preparation of racemic 2-(2-((7-(3-(aminomethyl)phenyl)-2-(1-hydroxyethyl)benzofuran-5-yl)methoxy)phenyl)acetic Acid (98e), (+)-isomer (98f) and (−)-isomer (98g)

Step-1: Preparation of Ethyl 2-(2-((2-(hydroxymethyl)-7-iodobenzofuran-5-yl)methoxy)phenyl)acetate (98a)

Compound 98a was prepared according to the procedure reported in step-5 of Scheme-76 from ethyl 2-(2-((2-(((tert-butyldimethylsilyl)oxy)methyl)-7-iodobenzofuran-5-yl)methoxy)phenyl)acetate (76c) (4 g, 6.89 mmol) in THF (60 mL) using added TBAF (2.25 g, 8.61 mmol). This gave after workup, purification by flash column chromatography [silica (24 g), eluting with EtOAc in hexane from 0-70%] ethyl 2-(2-((2-(hydroxymethyl)-7-iodobenzofuran-5-yl)methoxy)phenyl)acetate (98a) (2.5 g, 78% yield) as a clear oil; $^1$H NMR (300 MHz, DMSO-$d_6$) δ 7.70 (d, J=1.6 Hz, 1H), 7.63 (d, J=1.5 Hz, 1H), 7.29-7.18 (m, 2H), 7.07 (d, J=8.1 Hz, 1H), 6.95-6.87 (m, 2H), 5.54 (t, J=5.9 Hz, 1H), 5.14 (s, 2H), 4.60 (d, J=5.9 Hz, 2H), 4.04 (q, J=7.1 Hz, 2H), 3.61 (s, 2H), 1.09 (t, J=7.1 Hz, 3H); MS (ES+): 489.1 (M+Na).

Step-2: Preparation of Ethyl 2-(2-((2-formyl-7-iodobenzofuran-5-yl)methoxy)phenyl)acetate (98b)

To a solution of ethyl 2-(2-((2-(hydroxymethyl)-7-iodobenzofuran-5-yl)methoxy)phenyl)acetate (98a) (500 mg, 1.07 mmol) in DCM (20 mL) was added Dess-Martin Periodinane (546 mg, 1.29 mmol). The resulting mixture was stirred at RT for 3h, diluted with dichloromethane, washed with saturated aqueous sodium bicarbonate, dried, filtered, and evaporated in vacuo. The crude product was purified by flash column chromatography [silica gel (24 g)] to afford ethyl 2-(2-((2-formyl-7-iodobenzofuran-5-yl)methoxy)phenyl)acetate (98b) (410 mg, 82% yield) as a white solid; $^1$H NMR (300 MHz, DMSO-$d_6$) δ 9.88 (s, 1H), 8.12 (s, 1H), 8.02 (d, J=1.6 Hz, 1H), 7.93 (d, J=1.6 Hz, 1H), 7.31-7.18 (m, 2H), 7.08 (d, J=8.0 Hz, 1H), 6.93 (t, J=7.4, 1.1 Hz, 1H), 5.20 (s, 2H), 4.03 (q, J=7.1, 1.7 Hz, 2H), 3.63 (s, 2H), 1.09 (t, J=7.1, 1.7 Hz, 3H).

Step-3: Preparation of Ethyl 2-(2-((2-(1-hydroxyethyl)-7-iodobenzofuran-5-yl)methoxy)phenyl)acetate (98c)

To a solution of ethyl 2-(2-((2-formyl-7-iodobenzofuran-5-yl)methoxy)phenyl)acetate (98b) (410 mg, 0.88 mmol) in THF (20 mL) at −78° C. was added methylmagnesium bromide (1.4M in THF) (0.63 mL, 0.88 mmol). The resulting mixture was stirred at −78° C. for 1 h, quenched with saturated NH$_4$Cl solution and extracted with EtOAc (3×). The combined organic layers were washed with saturated aqueous sodium bicarbonate, dried, filtered and evaporated in vacuo. The crude product was purified by flash column chromatography [silica gel (24 g), eluting with EtOAc in hexane from 0-60%] to afford ethyl 2-(2-((2-(1-hydroxyethyl)-7-iodobenzofuran-5-yl)methoxy)phenyl)acetate (98c) (290 mg, 68% yield) as a yellow semi-solid; $^1$H NMR (300 MHz, DMSO-$d_6$) δ 7.69 (d, J=1.5 Hz, 1H), 7.62 (d, J=1.6 Hz, 1H), 7.29-7.18 (m, 2H), 7.06 (d, J=8.0 Hz, 1H), 6.91 (t, J=7.3 Hz, 2H), 6.85 (s, 1H), 5.61-5.53 (m, 1H), 5.13 (s, 2H), 4.92-4.80 (m, 1H), 4.03 (q, J=7.1 Hz, 2H), 3.61 (s, 2H), 1.47 (d, J=6.6 Hz, 3H), 1.10 (t, J=7.1 Hz, 3H); MS (ES+): 503.2 (M+Na).

Step-4: Preparation of Ethyl 2-(2-((7-(3-(aminomethyl)phenyl)-2-(1-hydroxyethyl)benzofuran-5-yl)methoxy)phenyl)acetate (98d)

Compound 98d was prepared according to the procedure reported in step-3 of Scheme-1 from ethyl 2-(2-((2-(1-hydroxyethyl)-7-iodobenzofuran-5-yl)methoxy)phenyl)acetate (98c) (285 mg, 0.59 mmol) in dioxane (15 mL) using 3-(aminomethyl)phenylboronic acid hydrochloride (6c) (145 mg, 0.77 mmol), a solution of K$_2$CO$_3$ (246 mg, 1.78 mmol) in water (3 mL), bis(triphenylphosphine)palladium (II) chloride (63 mg, 0.089 mmol) and heating at 100° C. for 3h on an oil bath. This gave after workup, purification by flash column chromatography [silica (12 g), eluting with DMA80 in DCM from 0-50%] followed by purification by reverse phase column chromatography [C18 (50 g), eluting with ACN in water (containing 0.1% HCl) from 0-100%] ethyl 2-(2-((7-(3-(aminomethyl)phenyl)-2-(1-hydroxyethyl)benzofuran-5-yl)methoxy)phenyl)acetate (98d) (156 mg, 57% yield) as a white solid; $^1$H NMR (300 MHz, DMSO-$d_6$) δ 8.51 (s, 3H, D$_2$O exchangeable), 8.01 (d, J=2.3 Hz, 1H), 7.97-7.88 (m, 1H), 7.65 (d, J=1.7 Hz, 1H), 7.61-7.52 (m, 3H), 7.31-7.18 (m, 2H), 7.11 (d, J=8.1 Hz, 1H), 6.96-6.85 (m, 1H), 6.79 (s, 1H), 5.58 (s, 1H, D$_2$O exchangeable), 5.23 (s, 2H), 4.88 (d, J=6.9 Hz, 1H), 4.13 (s, 2H), 3.95 (q, J=7.1 Hz, 2H), 3.63 (s, 2H), 1.49 (d, J=6.5 Hz, 3H), 1.01 (t, J=7.1, 1.5 Hz, 3H); MS (ES+): 460.3 (M+1); (ES−): 494.3 (M+Cl).

Step-5: Preparation of racemic 2-(2-((7-(3-(aminomethyl)phenyl)-2-(1-hydroxyethyl)benzofuran-5-yl)methoxy)phenyl)acetic Acid (98e)

Compound 98e was prepared according to the procedure reported in step-6 of Scheme-1, from ethyl 2-(2-((7-(3-(aminomethyl)phenyl)-2-(1-hydroxyethyl)benzofuran-5-yl)methoxy)phenyl)acetate (98d) (92 mg, 0.20 mmol) in MeOH/THF (10 mL) using a solution of lithium hydroxide monohydrate (25 mg, 0.6 mmol) in water (1.0 mL). This gave after workup and purification by reverse phase column

[C18 (50 g), eluting with ACN in water (containing 0.1% HCl) from 0-100%] racemic 2-(2-((7-(3-(aminomethyl)phenyl)-2-(1-hydroxyethyl)benzofuran-5-yl)methoxy)phenyl)acetic acid (98e) (53 mg, 61% yield) HCl salt as a white solid; $^1$H NMR (300 MHz, DMSO-$d_6$) δ 12.10 (s, 1H, $D_2O$ exchangeable), 8.49 (s, 3H, $D_2O$ exchangeable), 8.05-7.90 (m, 2H), 7.73-7.66 (m, 1H), 7.64-7.52 (m, 3H), 7.27-7.18 (m, 2H), 7.13-7.05 (m, 1H), 6.90 (t, J=7.4 Hz, 1H), 6.78 (s, 1H), 5.26 (s, 2H), 4.88 (q, J=6.6 Hz, 1H), 4.13 (d, J=5.9 Hz, 2H), 3.60 (s, 2H), 1.49 (d, J=6.6 Hz, 3H); MS (ES+): 432.3 (M+1); (ES−): 430.4 (M−1), 466.3 (M+Cl).

Step-6: Preparation of (+)-isomer 2-(2-((7-(3-(aminomethyl)phenyl)-2-(1-hydroxyethyl)benzofuran-5-yl)methoxy)phenyl)acetic Acid (98f) and (−)-isomer 2-(2-((7-(3-(aminomethyl)phenyl)-2-(1-hydroxyethyl)benzofuran-5-yl)methoxy)phenyl)acetic Acid (98g)

Racemic compound 2-(2-((7-(3-(aminomethyl)phenyl)-2-(1-hydroxyethyl)benzofuran-5-yl)methoxy)phenyl)acetic acid (98e) (30 mgs) was subjected to chiral separation using a chiral column (CHIRALPAK IBN), eluting with Hexane/Ethanol/TEA (85/15/0.1) to afford:

1. Peak-1 (17.2 mg) as a white wax. This sample from chiral separation was dissolved in acetonitrile and water and lyophilized to dryness to afford (+)-2-(2-((7-(3-(aminomethyl)phenyl)-2-(1-hydroxyethyl)benzofuran-5-yl)methoxy)phenyl)acetic acid (98f) (9 mg) as a white solid; $^1$H NMR (300 MHz, DMSO-$d_6$) δ 8.35-8.28 (m, 1H), 8.12 (d, J=7.9 Hz, 1H), 7.87 (d, J=1.7 Hz, 1H), 7.61 (d, J=1.6 Hz, 1H), 7.50 (t, J=7.7 Hz, 1H), 7.36 (d, J=7.8 Hz, 1H), 7.15-7.05 (m, 2H), 6.95 (d, J=8.0 Hz, 1H), 6.85-6.76 (m, 2H), 5.59 (s, 1H, $D_2O$ exchangeable), 5.25 (s, 2H), 4.88 (q, J=6.5 Hz, 1H), 4.02 (s, 2H), 3.40 (s, 2H), 1.49 (d, J=6.5 Hz, 3H); MS (ES+): 432.2 (M+1), MS (ES−): 430.2 (M−1); Enantiomeric purity: (% ee)=93.7%; Optical rotation: $[α]_D$=(+) 28.0 [DMSO/CH$_3$OH (1:1), 0.05].

2. Peak-2 (71.3 mg) as a yellow wax. This sample from chiral separation was dissolved in acetonitrile and water and lyophilized to dryness to afford (−)-2-(2-((7-(3-(aminomethyl)phenyl)-2-(1-hydroxyethyl)benzofuran-5-yl)methoxy)phenyl)acetic acid (98g) (26 mg); This was further purified by reverse-phase column chromatography [EZ-PREP, C-18 column, 50 g, eluting with 0.1% aq. HCl in water and acetonitrile from 0-100%] to afford (−)-2-(2-((7-(3-(aminomethyl)phenyl)-2-(1-hydroxyethyl)benzofuran-5-yl)methoxy)phenyl)acetic acid (98g) (2.1 mg) HCl salt as a white solid; $^1$H NMR (300 MHz, DMSO-$d_6$) δ 12.23 (s, 1H, $D_2O$ exchangeable), 8.31 (bs, 3H, $D_2O$ exchangeable), 8.00-7.91 (m, 2H), 7.68 (d, J=1.6 Hz, 1H), 7.64-7.57 (m, 2H), 7.56-7.49 (m, 1H), 7.23 (s, 1H), 7.21 (s, 1H), 7.08 (d, J=8.1 Hz, 1H), 6.90 (t, J=7.3 Hz, 1H), 6.79 (d, J=0.9 Hz, 1H), 5.58 (s, 1H, $D_2O$ exchangeable), 5.25 (s, 2H), 4.95-4.82 (m, 1H), 4.29-4.05 (m, 2H), 3.59 (s, 2H), 1.49 (d, J=6.6 Hz, 3H); MS (ES+): 432.3 (M+1), MS (ES−): 430.3 (M−1); Enantiomeric purity: (% ee)=70.85; Optical rotation: $[α]_D$=(−) 24.0 [DMSO/CH$_3$OH (1:1), 0.05].

Scheme-99

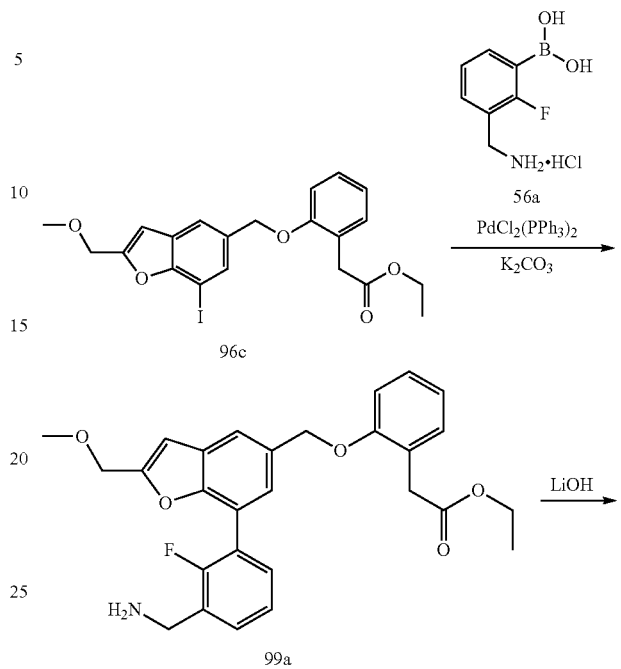

Preparation of 2-(2-((7-(3-(aminomethyl)-2-fluorophenyl)-2-(methoxymethyl)benzofuran-5-yl)methoxy)phenyl)acetic Acid (99b)

Step-1: Preparation of Ethyl 2-(2-((7-(3-(aminomethyl)-2-fluorophenyl)-2-(methoxymethyl)benzofuran-5-yl)methoxy)phenyl)acetate (99a)

Compound 99a was prepared according to the procedure reported in step-3 of Scheme-1 from ethyl 2-(2-((7-iodo-2-(methoxymethyl)benzofuran-5-yl)methoxy)phenyl)acetate (96c) (500 mg, 1.04 mmol) in dioxane (15 mL) using 3-(aminomethyl)-2-fluorophenylboronic acid hydrochloride (56a) (278 mg, 1.35 mmol), a solution of K$_2$CO$_3$ (432 mg, 3.12 mmol) in water (3 mL), bis(triphenylphosphine)palladium(II) chloride (110 mg, 0.16 mmol) and heating at 100° C. for 3h on oil bath. This gave after workup, purification by flash column chromatography [silica (12 g), eluting with DMA80 in DCM from 0-50%] followed by purification by reverse phase column chromatography [C18 (50 g), eluting with ACN in water (containing 0.1% HCl) from 0-100%] ethyl 2-(2-((7-(3-(aminomethyl)-2-fluorophenyl)-2-(methoxymethyl)benzofuran-5-yl)methoxy)phenyl)acetate (99a) (386 mg, 78% yield) HCl salt as a white solid; $^1$H NMR (300 MHz, DMSO-$d_6$) δ 8.66 (s, 3H, $D_2O$ exchangeable), 7.79-7.69 (m, 2H), 7.69-7.59 (m, 1H), 7.49-7.38 (m, 2H), 7.31-7.18 (m, 2H), 7.15-7.07 (m, 1H), 7.02 (s, 1H), 6.91 (t, J=7.4, 1.0 Hz, 1H), 5.23 (s, 2H), 4.52 (s, 2H), 4.16 (s, 2H), 3.92 (q, J=7.1 Hz, 2H), 3.62 (s, 2H), 3.28 (s, 3H), 0.99 (t, J=7.1 Hz, 3H); MS (ES+): 478.3 (M+1); (ES−): 512.3 (M+Cl).

Step-2: Preparation of 2-(2-((7-(3-(aminomethyl)-2-fluorophenyl)-2-(methoxymethyl)benzofuran-5-yl)methoxy)phenyl)acetic Acid (99b)

Compound 99b was prepared according to the procedure reported in step-6 of Scheme-1, from ethyl 2-(2-((7-(3-(aminomethyl)-2-fluorophenyl)-2-(methoxymethyl)benzofuran-5-yl)methoxy)phenyl)acetate (99a) (120 mg, 0.251 mmol) in MeOH/THF (10 mL) using a solution of lithium hydroxide monohydrate (32 mg, 0.75 mmol) in water (1.0 mL). This gave after workup and purification by reverse phase column [C18 (50 g), eluting with ACN in water (containing 0.1% HCl) from 0-100%] 2-(2-((7-(3-(aminomethyl)-2-fluorophenyl)-2-(methoxymethyl)benzofuran-5-yl)methoxy)phenyl)acetic acid (99b) (63 mg, 56% yield) HCl salt as a white solid; $^1$H NMR (300 MHz, DMSO-$d_6$) δ 12.17 (s, 1H, $D_2O$ exchangeable), 8.60 (s, 3H, $D_2O$ exchangeable), 7.79 (d, J=1.6 Hz, 1H), 7.75-7.62 (m, 2H), 7.48-7.39 (m, 2H), 7.28-7.18 (m, 2H), 7.09 (d, J=8.1 Hz, 1H), 7.00 (s, 1H), 6.90 (t, J=7.3, 1.0 Hz, 1H), 5.25 (s, 2H), 4.52 (s, 2H), 4.16 (s, 2H), 3.58 (s, 2H), 3.29 (s, 3H); $^{19}$F NMR (282 MHz, DMSO-$d_6$) δ−118.67; MS (ES+): 450.3 (M+1); 472.3 (M+Na); (ES−): 448.3 (M−1), 484.3 (M+Cl).

Scheme-100

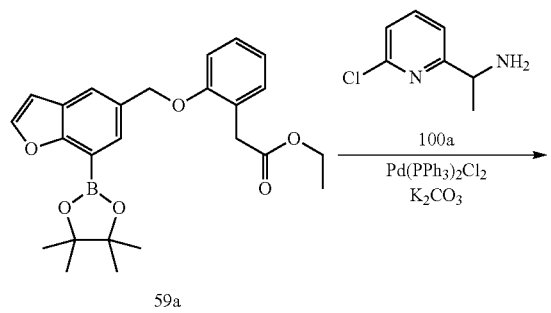

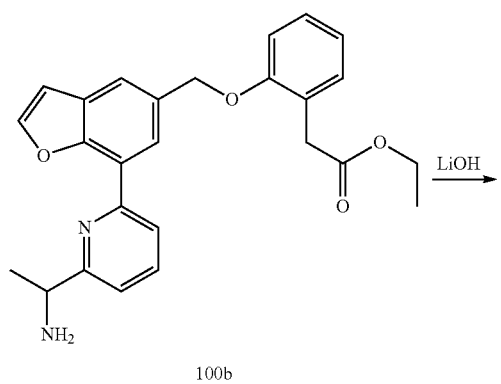

100b

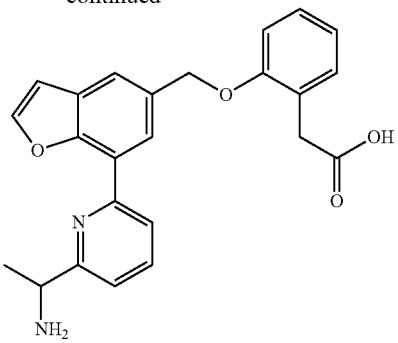

100c

Preparation of 2-(2-((7-(6-(1-aminoethyl)pyridin-2-yl)benzofuran-5-yl)methoxy)phenyl)acetic Acid (100c)

Step-1: Preparation of Ethyl 2-(2-((7-(6-(1-aminoethyl)pyridin-2-yl)benzofuran-5-yl)methoxy)phenyl)acetate (100b)

Compound 100b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (300 mg, 0.69 mmol) in dioxane (6 mL) using 1-(6-chloropyridin-2-yl)ethanamine (100a) (108 mg, 0.69 mmol; CAS #1060811-97-3), potassium carbonate (190 mg, 1.38 mmol) and bis(triphenylphosphine)palladium(II) chloride (97 mg, 0.14 mmol) under an Ar atmosphere and heating at 100° C. for 90 min on an oil bath. This gave after workup, purification by flash column chromatography [silica (12 g), eluting with DMA80 in DCM from 0-50%] followed by purification by reverse phase column [C18 (50 g), eluting with ACN in water (containing 0.1% HCl) from 0-100%] ethyl 2-(2-((7-(6-(1-aminoethyl)pyridin-2-yl)benzofuran-5-yl)methoxy)phenyl)acetate (100b) (82 mg, 28% yield) as a white solid; MS (ES+): 431.3 (M+1).

Step-2: Preparation of 2-(2-((7-(6-(1-aminoethyl)pyridin-2-yl)benzofuran-5-yl)methoxy)phenyl)acetic Acid (100c)

Compound 100c was prepared according to the procedure reported in step-6 of Scheme-1, from ethyl 2-(2-((7-(6-(1-aminoethyl)pyridin-2-yl)benzofuran-5-yl)methoxy)phenyl)acetate (100b) (82 mg, 0.19 mmol) in MeOH/THF (10 mL) using a solution of lithium hydroxide monohydrate (24 mg, 0.57 mmol) in water (1 mL). This gave after workup and purification by reverse phase column [C18 (50 g), eluting with ACN in water (containing 0.1% HCl) from 0-100%] 2-(2-((7-(6-(1-aminoethyl)pyridin-2-yl)benzofuran-5-yl)methoxy)phenyl)acetic acid (100c) (29 mg, 38% yield) as a white solid; $^1$H NMR (300 MHz, DMSO-$d_6$) δ 8.68 (s, 3H, $D_2O$ exchangeable), 8.53 (d, J=1.6 Hz, 1H), 8.35 (d, J=7.9 Hz, 1H), 8.16 (d, J=2.2 Hz, 1H), 8.07 (t, J=7.9 Hz, 1H), 7.86 (d, J=1.6 Hz, 1H), 7.58 (d, J=7.7 Hz, 1H), 7.23 (d, J=7.4 Hz, 2H), 7.16-7.06 (m, 2H), 6.91 (t, J=7.4 Hz, 1H), 5.32 (s, 2H), 4.70-4.54 (m, 1H), 3.61 (s, 2H), 1.62 (d, J=6.8 Hz, 3H); MS (ES+): 403.3 (M+1); 425.3 (M+Na); (ES−): 401.3 (M−1), 437.3 (M+Cl).

Scheme-101

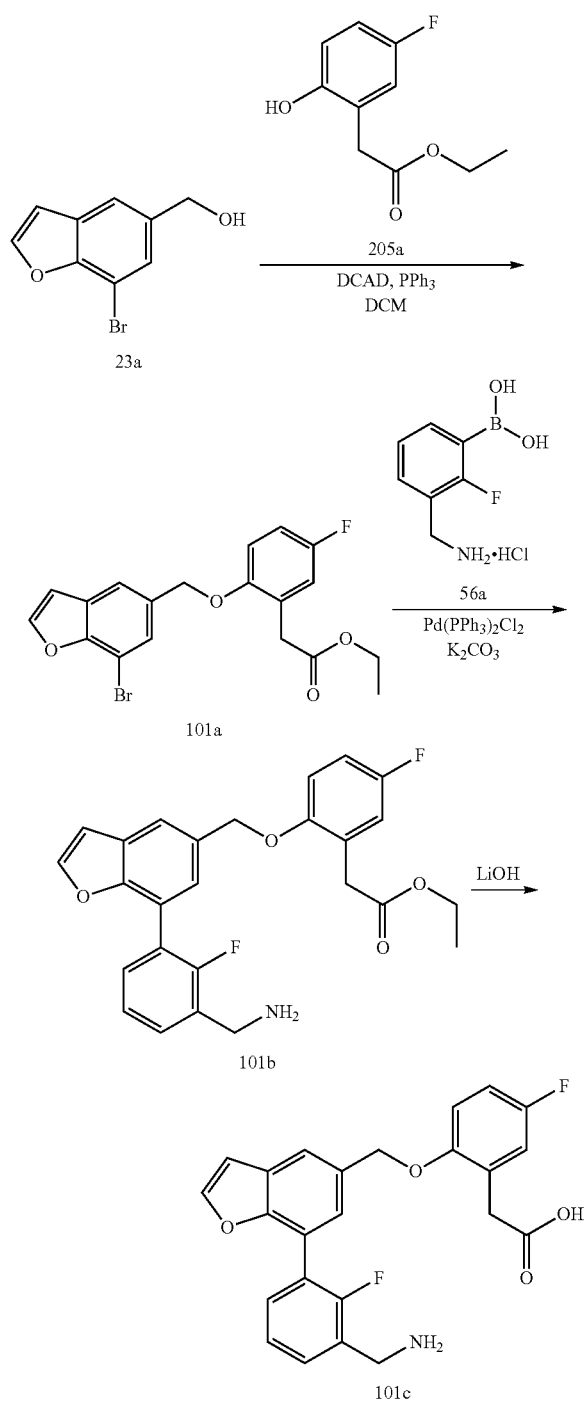

Preparation of 2-(2-((7-(3-(aminomethyl)-2-fluorophenyl)benzofuran-5-yl)methoxy)-5-fluorophenyl)acetic Acid (101c)

Step-1: Preparation of Ethyl 2-(2-((7-bromobenzofuran-5-yl)methoxy)-5-fluorophenyl)acetate (101a)

Compound 101a was prepared according to the procedure reported in step-2 of Scheme-23 from (7-bromobenzofuran-5-yl)methanol (23a) (2 g, 8.81 mmol) in DCM (30 mL) using triphenylphosphine (3.00 g, 11.45 mmol), ethyl 2-(5-fluoro-2-hydroxyphenyl)acetate (205a) (2.27 g, 11.45 mmol) and a solution of di-(4-chlorobenzyl)azodicarboxylate (DCAD, 4.20 g, 11.45 mmol) in DCM (20 mL). This gave after workup and purification by flash column chromatography [silica (24 g), eluting with EtOAc/MeOH (9:1) in hexanes from 0-50%] ethyl 2-(2-((7-bromobenzofuran-5-yl)methoxy)-5-fluorophenyl)acetate (101a) (1.04 g, 29% yield) as a white solid; $^1$H NMR (300 MHz, DMSO-$d_6$) δ 8.15 (d, J=2.2 Hz, 1H), 7.70 (d, J=1.5 Hz, 1H), 7.59 (d, J=1.5 Hz, 1H), 7.20-7.02 (m, 4H), 5.16 (s, 2H), 4.02 (q, J=7.1 Hz, 2H), 3.64 (s, 2H), 1.08 (t, J=7.1 Hz, 3H); MS (ES−): 406.9 (M−1).

Step-2: Preparation of Ethyl 2-(2-((7-(3-(aminomethyl)-2-fluorophenyl)benzofuran-5-yl)methoxy)-5-fluorophenyl)acetate (101b)

Compound 101b was prepared according to the procedure reported in step-3 of Scheme-1 from ethyl 2-(2-((7-bromobenzofuran-5-yl)methoxy)-5-fluorophenyl)acetate (101a) (0.3 g, 0.74 mmol) in dioxane (4 mL) using (3-(aminomethyl)-2-fluorophenyl)boronic acid hydrochloride (56a) (0.23 g, 1.11 mmol), a solution of $K_2CO_3$ (0.20 g, 1.47 mmol) in water (0.5 mL), Pd(PPh$_3$)$_2$Cl$_2$ (0.08 g, 0.11 mmol) and heating under an Ar atmosphere at 90° C. for 3 h. This gave after workup, purification by flash column chromatography [silica (12 g), eluting with MeOH in DCM from 0-50%] ethyl 2-(2-((7-(3-(aminomethyl)-2-fluorophenyl)benzofuran-5-yl)methoxy)-5-fluorophenyl)acetate (101b) (0.21 g, 63% yield) as a white solid; this was then purified by reverse phase column chromatography [C18 (50 g), eluting with ACN in water (containing 0.1% HCl) from 0-100%] to furnish compound 101b HCl salt as a white solid; $^1$H NMR (300 MHz, DMSO-$d_6$) δ 8.51 (s, 3H), 8.06 (d, J=2.2 Hz, 1H), 7.78 (d, J=1.6 Hz, 1H), 7.74-7.62 (m, 2H), 7.47-7.39 (m, 2H), 7.17-7.04 (m, 4H), 5.22 (s, 2H), 4.17 (s, 2H), 3.93 (q, J=7.1 Hz, 2H), 3.64 (s, 2H), 1.00 (t, J=7.1 Hz, 3H). $^{19}$F NMR (282 MHz, DMSO-$d_6$) δ−118.53, 124.00; MS (ES+): 452.9 (M+1); MS (ES−): 450.9 (M−1).

Step-3: Preparation of 2-(2-((7-(3-(aminomethyl)-2-fluorophenyl)benzofuran-5-yl)methoxy)-5-fluorophenyl)acetic Acid (101c)

Compound 101c was prepared according to the procedure reported in step-6 of Scheme-1 from ethyl 2-(2-((7-(3-(aminomethyl)-2-fluorophenyl)benzofuran-5-yl)methoxy)-5-fluorophenyl)acetate (101b) (0.16 g, 0.35 mmol) in THF/methanol (6 mL each) using a solution of lithium hydroxide hydrate (0.12 g, 2.84 mmol) in water (1 mL). This gave after workup and purification by reverse phase column chromatography [C18 (50 g), eluting with ACN in water (containing 0.1% HCl) from 0-100%] 2-(2-((7-(3-(aminomethyl)-2-fluorophenyl)benzofuran-5-yl)methoxy)-5-fluorophenyl) acetic acid (101c) (0.08 g, 53% yield) HCl salt as a white solid; $^1$H NMR (300 MHz, DMSO-$d_6$) δ 8.54 (s, 3H), 8.06 (d, J=2.2 Hz, 1H), 7.81 (d, J=1.6 Hz, 1H), 7.68 (td, J=7.1, 5.1 Hz, 2H), 7.48-7.38 (m, 2H), 7.12 (dd, J=7.6, 2.2 Hz, 1H), 7.11-7.07 (m, 2H), 7.06 (d, J=2.2 Hz, 1H), 5.24 (s, 2H), 4.17 (s, 2H), 3.60 (s, 2H); $^{19}$F NMR (282 MHz, DMSO-$d_6$) δ−118.40, 124.07; MS (ES+): 424.9 (M+1); MS (ES−): 422.9 (M−1).

Scheme-102

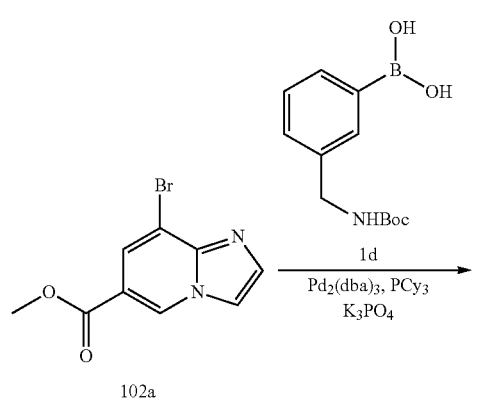

102a

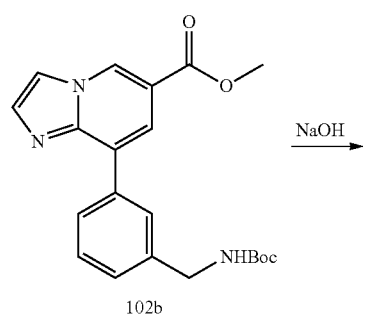

102b

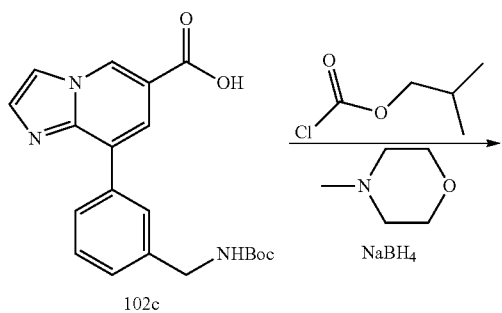

102c

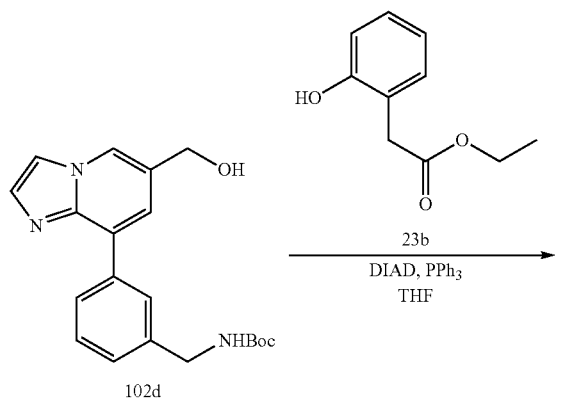

102d

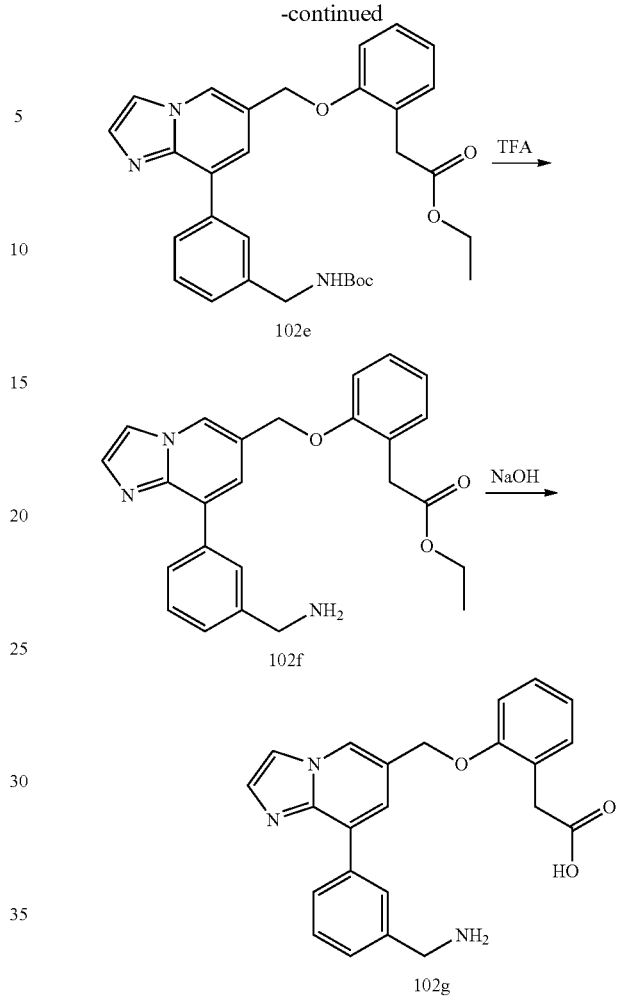

Preparation of 2-(2-((8-(3-(aminomethyl)phenyl)imidazo[1,2-a]pyridin-6-yl)methoxy)phenyl)acetic Acid (102g)

Step-1: Preparation of methyl 8-(3-(((tert-butoxycarbonyl)amino)methyl)phenyl)imidazo[1,2-a]pyridine-6-carboxylate (102b)

Compound 102b was prepared according to the procedure reported in step-3 of Scheme-1 from methyl 8-bromoimidazo[1,2-a]pyridine-6-carboxylate (102a) (1.00 g, 3.92 mmol; CAS #1234616-08-0) in dioxane (20 mL) using 3-((tert-butoxycarbonylamino)methyl)phenylboronic acid (1d) (0.984 g, 3.92 mmol), tripotassium phosphate (2.222 mL, 6.66 mmol; 3 M solution) in water (1 mL), tricyclohexylphosphine (0.220 g, 0.784 mmol) and Pd$_2$(dba)$_3$ (0.197 g, 0.216 mmol) under a nitrogen atmosphere and heating at 90° C. for 12 h on an oil bath. This gave after workup, purification by flash column chromatography [silica (40 g), eluting with EtOAc/methanol (9:1) in hexane from 0-100%] methyl 8-(3-(((tert-butoxycarbonyl)amino)methyl)phenyl)imidazo[1,2-a]pyridine-6-carboxylate (102b) (1.289 g, 86% yield) as a pale yellow solid; $^1$H NMR (300 MHz, DMSO-d$_6$) δ 9.38 (d, J=1.6 Hz, 1H), 8.24-8.21 (m, 1H), 8.05 (d, J=7.7 Hz, 1H), 7.91 (s, 1H), 7.81-7.68 (m, 2H), 7.59-7.41 (m, 2H), 7.32 (d, J=7.6 Hz, 1H), 4.30-4.13 (m, 2H), 3.92 (s, 3H), 1.41 (s, 9H); MS (ES+): 382.3 (M+1).

Step-2: Preparation of 8-(3-(((tert-butoxycarbonyl)amino)methyl)phenyl)imidazo[1,2-a]pyridine-6-carboxylic Acid (102c)

Compound 102c was prepared according to the procedure reported in step-4 of Scheme-4, from methyl 8-(3-(((tert-butoxycarbonyl)amino)methyl)phenyl)imidazo[1,2-a]pyridine-6-carboxylate (102b) (1.25 g, 3.28 mmol) in THF (10 mL) and methanol (20 mL) using sodium hydroxide (2 M aq.) (6.55 mL, 13.11 mmol). This gave after workup 8-(3-(((tert-butoxycarbonyl)amino)methyl)phenyl)imidazo[1,2-a]pyridine-6-carboxylic acid (102c) (1.06 g, 88% yield) as an off-white solid; $^1$H NMR (300 MHz, DMSO-$d_6$) δ 13.50 (s, 1H), 9.36 (d, J=1.6 Hz, 1H), 8.27 (s, 1H), 8.00 (d, J=7.8 Hz, 1H), 7.93-7.77 (m, 3H), 7.57-7.43 (m, 2H), 7.34 (d, J=7.6 Hz, 1H), 4.23 (d, J=6.1 Hz, 2H), 1.40 (s, 9H).

Step-3: Preparation of tert-butyl 3-(6-(hydroxymethyl)imidazo[1,2-a]pyridin-8-yl)benzylcarbamate (102d)

Compound 102d was prepared according to the procedure reported in step-1 of Scheme-23 from 8-(3-(((tert-butoxycarbonyl)amino)methyl)phenyl)imidazo[1,2-a]pyridine-6-carboxylic acid (102c) (0.60 g, 1.633 mmol) using N-methylmorpholine (0.215 mL, 1.960 mmol) in THF (20 mL), isobutyl chloroformate (0.257 mL, 1.960 mmol) and NaBH$_4$ (0.185 g, 4.90 mmol) in water (3 mL). This gave after workup and purification by flash column chromatography [silica (24 g), eluting with EtOAc/MeOH (9:1) in hexanes from 0-40%] tert-butyl 3-(6-(hydroxymethyl)imidazo[1,2-a]pyridin-8-yl)benzylcarbamate (102d) (0.443 g, 77% yield) as a pale-yellow solid; $^1$H NMR (300 MHz, DMSO-$d_6$) δ 8.52-8.44 (m, 1H), 8.08-7.99 (m, 2H), 7.95 (s, 1H), 7.59 (d, J=1.2 Hz, 1H), 7.53-7.37 (m, 3H), 7.28 (d, J=7.6 Hz, 1H), 5.40 (t, J=5.6 Hz, 1H), 4.57 (d, J=5.6, 1.1 Hz, 2H), 4.21 (d, J=6.2 Hz, 2H), 1.40 (s, 9H); MS (ES+): 354.3 (M+1), 376.3 (M+Na); MS (ES−): 352.3 (M−1).

Step-4: Preparation of Ethyl 2-(2-((8-(3-(((tert-butoxycarbonyl)amino)methyl)phenyl)imidazo[1,2-a]pyridin-6-yl)methoxy)phenyl)acetate (102e)

Compound 102e was prepared according to the procedure reported in step-2 of Scheme-23 from tert-butyl 3-(6-(hydroxymethyl)imidazo[1,2-a]pyridin-8-yl)benzylcarbamate (102d) (0.300 g, 0.849 mmol) in THF (25 mL) using triphenylphosphine (0.289 g, 1.104 mmol), ethyl 2-(2-hydroxyphenyl) acetate (23b) (0.199 g, 1.104 mmol) and DIAD (0.215 mL, 1.104 mmol). This gave after workup and purification by flash column chromatography [silica (24 g), eluting with EtOAc in hexane from 0-100%] ethyl 2-(2-((8-(3-(((tert-butoxycarbonyl)amino)methyl)phenyl)imidazo[1,2-a]pyridin-6-yl)methoxy)phenyl)acetate (102e) (0.328 g, 75% yield) as a pale-yellow solid; MS (ES+): 516.4 (M+1), 538.3 (M+Na); MS (ES−): 514.5 (M−1), 550.4 (M+Cl).

Step-5: Preparation of Ethyl 2-(2-((8-(3-(aminomethyl)phenyl)imidazo[1,2-a]pyridin-6-yl)methoxy)phenyl)acetate (102f)

Compound 102f was prepared according to the procedure reported in step-5 of Scheme-1 from ethyl 2-(2-((8-(3-(((tert-butoxycarbonyl)amino)methyl)phenyl)imidazo[1,2-a]pyridin-6-yl)methoxy)phenyl)acetate (102e) (0.318 g, 0.617 mmol) in DCM (10 mL) using TFA (0.713 mL, 9.25 mmol). This gave after workup and purification by reverse phase column [C18 (30 g), eluting with ACN in water (containing 0.1% HCl) from 0-100%] ethyl 2-(2-((8-(3-(aminomethyl)phenyl)imidazo[1,2-a]pyridin-6-yl)methoxy)phenyl)acetate (102f) (0.172 g, 67% yield) as a white solid; $^1$H NMR (300 MHz, DMSO-$d_6$) δ 9.01 (s, 1H), 8.65 (s, 3H), 8.53-8.45 (m, 1H), 8.18 (s, 1H), 8.09-7.97 (m, 2H), 7.89-7.76 (m, 1H), 7.73-7.64 (m, 2H), 7.35-7.22 (m, 2H), 7.18 (d, J=8.1 Hz, 1H), 6.97 (td, J=7.4, 1.1 Hz, 1H), 5.32 (s, 2H), 4.24-4.07 (m, 2H), 3.90 (q, J=7.1 Hz, 2H), 3.68 (s, 2H), 0.97 (t, J=7.1 Hz, 3H); MS (ES+): 416.3 (M+1); MS (ES−): 450.3 (M+Cl).

Step-6: Preparation of 2-(2-((8-(3-(aminomethyl)phenyl)imidazo[1,2-a]pyridin-6-yl)methoxy)phenyl)acetic Acid (102g)

Compound 102g was prepared according to the procedure reported in step-4 of Scheme-4 from ethyl 2-(2-((8-(3-(aminomethyl)phenyl)imidazo[1,2-a]pyridin-6-yl)methoxy)phenyl)acetate (102f) (0.055 g, 0.132 mmol) in THF (4 mL) and methanol (8 mL) using sodium hydroxide (0.265 mL, 0.530 mmol, 2 M aqueous). This gave after workup and purification by reverse phase column [C18 (30 g), eluting with ACN in water (containing 0.1% HCl) from 0-100%] 2-(2-((8-(3-(aminomethyl)phenyl)imidazo[1,2-a]pyridin-6-yl)methoxy)phenyl)acetic acid (102g) (0.023 g, 45% yield) as a white solid; $^1$H NMR (300 MHz, DMSO-$d_6$) δ 12.30 (s, 1H, D$_2$O exchangeable), 9.01 (s, 1H), 8.66 (s, 3H, D$_2$O exchangeable), 8.55-8.44 (m, 1H), 8.17 (s, 1H), 8.04 (d, J=6.1 Hz, 2H), 7.89-7.77 (m, 1H), 7.72-7.62 (m, 2H), 7.34-7.21 (m, 2H), 7.15 (d, J=8.1 Hz, 1H), 6.96 (t, J=7.4 Hz, 1H), 5.34 (s, 2H), 4.15 (q, J=5.9 Hz, 2H), 3.64 (s, 2H); MS (ES+): 388.3 (M+1); MS (ES−): 386.3 (M−1), 422.3 (M+Cl), 773.5 (2M−1); HPLC purity: 98.95%

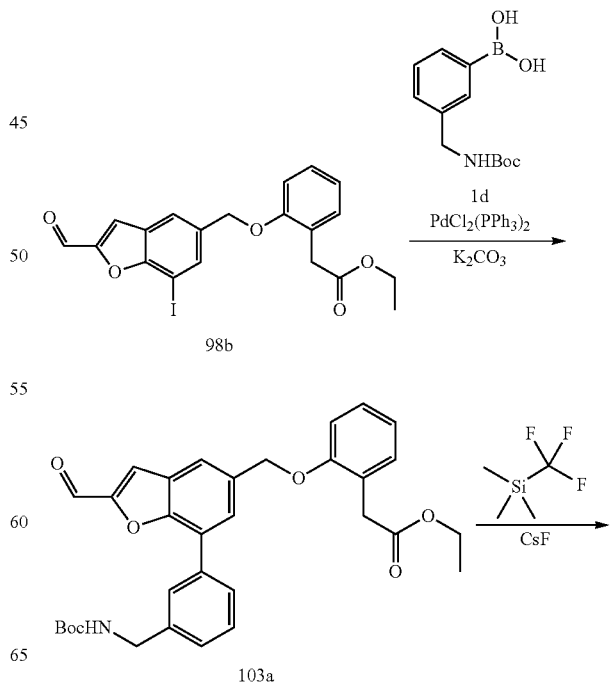

Scheme-103

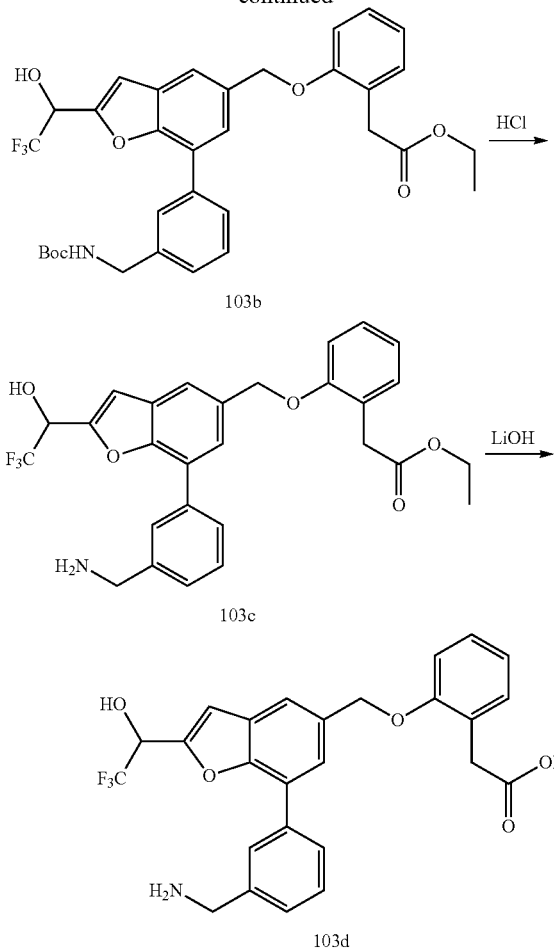

Preparation of 2-(2-((7-(3-(aminomethyl)phenyl)-2-(2,2,2-trifluoro-1-hydroxyethyl)benzofuran-5-yl)methoxy)phenyl)acetic Acid (103d)

Step-1: Preparation of Ethyl 2-(2-((7-(3-(((tert-butoxycarbonyl)amino)methyl)phenyl)-2-formylbenzofuran-5-yl)methoxy)phenyl)acetate (103a)

Compound 103a was prepared according to the procedure reported in step-3 of Scheme-1 from ethyl 2-(2-((2-formyl-7-iodobenzofuran-5-yl)methoxy)phenyl)acetate (98b) (2.2 g, 4.74 mmol) in dioxane (15 mL) using (3-((tert-butoxycarbonyl)amino)methyl)phenylboronic acid (id) (1.79 g, 7.11 mmol), a solution of K$_2$CO$_3$ (1.965 g, 14.22 mmol) in water (3 mL), bis(triphenylphosphine)palladium(II) chloride (0.50 g, 0.71 mmol) and heating at 100° C. for 3h on an oil bath. This gave after workup, purification by flash column chromatography [silica (12 g), eluting with DMA80 in DCM from 0-50%] ethyl 2-(2-((7-(3-(((tert-butoxycarbonyl)amino)methyl)phenyl)-2-formylbenzofuran-5-yl)methoxy)phenyl)acetate (103a) (1.52 g, 59% yield) as a brown semi-solid; $^1$H NMR (300 MHz, DMSO-d$_6$) δ 9.90 (s, 1H), 8.07 (d, J=1.3 Hz, 1H), 7.93 (d, J=1.6 Hz, 1H), 7.81-7.71 (m, 3H), 7.52 (t, J=7.7 Hz, 1H), 7.49-7.39 (m, 1H), 7.35 (d, J=7.6 Hz, 1H), 7.30-7.20 (m, 2H), 7.12 (d, J=8.2 Hz, 1H), 6.92 (t, J=7.4 Hz, 1H), 5.28 (s, 2H), 4.24 (d, J=6.2 Hz, 2H), 3.92 (q, J=7.1 Hz, 2H), 3.64 (s, 2H), 1.38 (s, 9H), 0.97 (t, J=7.1 Hz, 3H); MS (ES+): 566.3 (M+Na); (ES−) 542.5 (M−1).

Step-2: Preparation of Ethyl 2-(2-((7-(3-(((tert-butoxycarbonyl)amino)methyl)phenyl)-2-(2,2,2-trifluoro-1-hydroxyethyl)benzofuran-5-yl)methoxy)phenyl)acetate (103b)

Trimethyl(trifluoromethyl)silane (CAS #: 81290-20-2) (283 mg, 1.99 mmol) and CsF (233 mg, 1.53 mmol) were added to a solution of ethyl 2-(2-((7-(3-(((tert-butoxycarbonyl)amino)methyl)phenyl)-2-formylbenzofuran-5-yl)methoxy)phenyl)acetate (103a) (833 mg, 1.53 mmol) in anhydrous THF (20 mL) at room temperature under Ar and the mixture was sonicated for 20 min to initiate the reaction. The mixture was stirred at room temp for 12 h, after which aqueous HCl (1 M, 15 mL) was added and the mixture stirred for a further 15 min. The mixture was extracted with EtOAc, washed with saturated NaHCO$_3$, brine, dried and evaporated in vacuo. The residue obtained was purified by flash column chromatography [silica (24 g), eluting with (EtOAc/hexane 7:3)] to afford ethyl 2-(2-((7-(3-(((tert-butoxycarbonyl)amino)methyl)phenyl)-2-(2,2,2-trifluoro-1-hydroxyethyl)benzofuran-5-yl)methoxy)phenyl)acetate (103b) (312 mg, 33% yield) as a yellow solid; $^1$H NMR (300 MHz, DMSO-d$_6$) δ 7.81-7.69 (m, 3H), 7.60 (d, J=1.6 Hz, 1H), 7.55-7.41 (m, 2H), 7.36-7.18 (m, 4H), 7.17-7.07 (m, 2H), 6.91 (t, J=7.4, 1.1 Hz, 1H), 5.56-5.42 (m, 1H), 5.24 (s, 2H), 4.23 (d, J=6.1 Hz, 2H), 3.91 (q, J=7.1 Hz, 2H), 3.62 (s, 2H), 1.39 (s, 9H), 0.96 (t, J=7.1 Hz, 3H); $^{19}$F NMR (282 MHz, DMSO-d$_6$) δ−75.90; MS (ES+): 636.3 (M+Na).

Step-3: Preparation of Ethyl 2-(2-((7-(3-(aminomethyl)phenyl)-2-(2,2,2-trifluoro-1-hydroxyethyl)benzofuran-5-yl)methoxy)phenyl)acetate (103c)

Compound 103c was prepared according to the procedure reported in step-2 of Scheme-94, from ethyl 2-(2-((7-(3-(((tert-butoxycarbonyl)amino)methyl)phenyl)-2-(2,2,2-trifluoro-1-hydroxyethyl)benzofuran-5-yl)methoxy)phenyl)acetate (103b) (300 mg, 0.49 mmol) in THF (10 mL) using hydrochloric acid (2.45 mL, 4.89 mmol) and heating at 60° C. for 2 h. This gave after workup and purification by flash column chromatography [silica gel (12 g), eluting with DMA80 in DCM from 0-60%] followed by purification by reverse phase column [C18 (50 g), eluting with ACN in water (containing 0.1% HCl) from 0-100%] ethyl 2-(2-((7-(3-(aminomethyl)phenyl)-2-(2,2,2-trifluoro-1-hydroxyethyl)benzofuran-5-yl)methoxy)phenyl)acetate (103c) (109 mg, 43% yield) as a white solid; $^1$H NMR (300 MHz, DMSO-d$_6$) δ 8.38 (s, 3H, D$_2$O exchangeable), 7.98 (s, 1H), 7.94 (d, J=7.4 Hz, 1H), 7.75 (d, J=1.6 Hz, 1H), 7.67 (d, J=1.6 Hz, 1H), 7.65-7.52 (m, 2H), 7.34-7.27 (m, 1H), 7.27-7.19 (m, 2H), 7.16 (s, 1H), 7.11 (d, J=8.3 Hz, 1H), 6.91 (t, J=7.3 Hz, 1H), 5.53 (p, J=6.9 Hz, 1H), 5.24 (s, 2H), 4.12 (s, 2H), 3.92 (q, J=7.1 Hz, 2H), 3.63 (s, 2H), 0.97 (t, J=7.1 Hz, 3H); $^{19}$F NMR (282 MHz, DMSO-d$_6$) δ−75.83; MS (ES+): 514.3 (M+1); (ES−): 512.3 (M+1); 548.3 (M+Cl).

Step-4: Preparation of 2-(2-((7-(3-(aminomethyl)phenyl)-2-(2,2,2-trifluoro-1-hydroxyethyl)benzofuran-5-yl)methoxy)phenyl)acetic Acid (103d)

Compound 103d was prepared according to the procedure reported in step-6 of Scheme-1, from ethyl 2-(2-((7-(3-(aminomethyl)phenyl)-2-(2,2,2-trifluoro-1-hydroxyethyl)

benzofuran-5-yl)methoxy)phenyl)acetate (103c) (78 mg, 0.15 mmol) in MeOH/THF (10 mL) using a solution of lithium hydroxide monohydrate (19 mg, 0.46 mmol) in water (1.0 mL). This gave after workup and purification by reverse phase column [C18 (50 g), eluting with ACN in water (containing 0.1% HCl) from 0-100%] 2-(2-((7-(3-(aminomethyl)phenyl)-2-(2,2,2-trifluoro-1-hydroxyethyl) benzofuran-5-yl)methoxy)phenyl)acetic acid (103d) (39 mg, 53% yield) as a white solid; $^1$H NMR (300 MHz, DMSO-$d_6$) δ 12.20 (s, 1H, D$_2$O exchangeable), 8.41 (s, 2H, D$_2$O exchangeable), 8.03-7.92 (m, 2H), 7.78 (d, J=1.5 Hz, 1H), 7.71 (d, J=1.6 Hz, 1H), 7.65-7.53 (m, 2H), 7.31 (d, J=6.5 Hz, 1H), 7.28-7.19 (m, 2H), 7.15 (s, 1H), 7.09 (d, J=8.1 Hz, 1H), 6.91 (t, J=7.3 Hz, 1H), 5.60-5.47 (m, 1H), 5.27 (s, 2H), 4.13 (s, 2H), 3.60 (s, 2H); $^{19}$F NMR (282 MHz, DMSO-$d_6$) δ−75.81; MS (ES+): 486.3 (M+1); (ES−): 484.3 (M−1), 520.3 (M+Cl).

Scheme-104

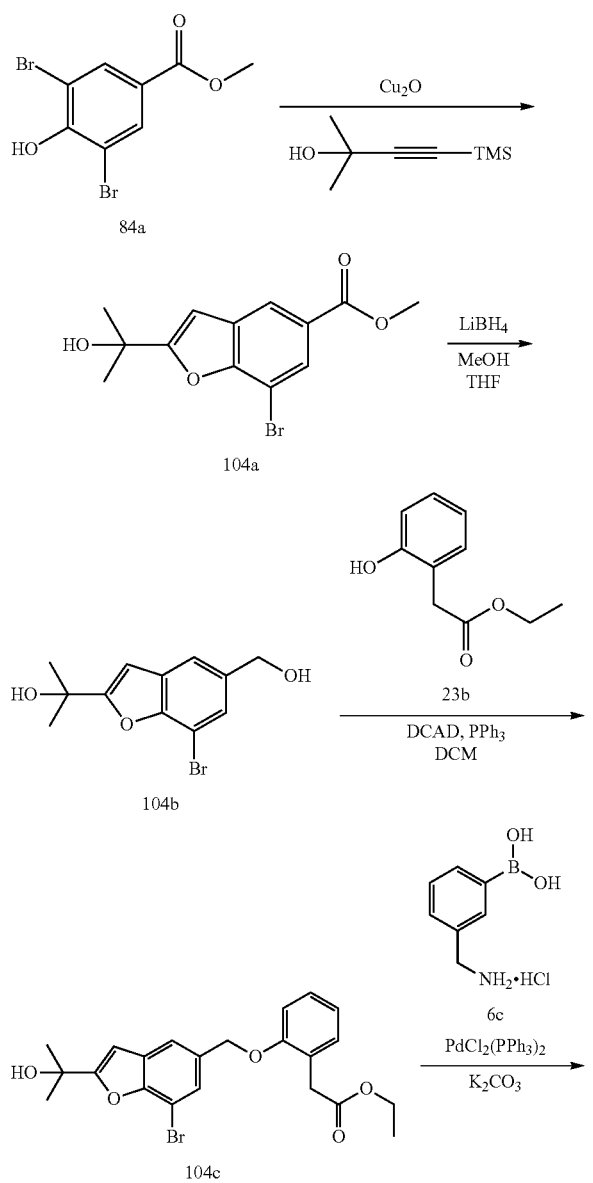

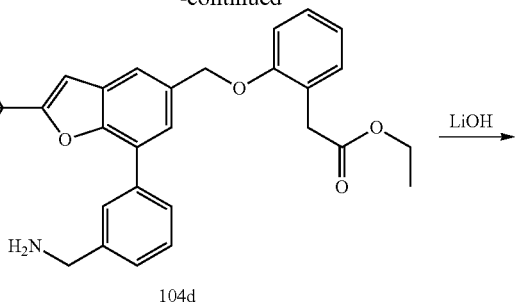

Preparation of 2-(2-((7-(3-(aminomethyl)phenyl)-2-(2-hydroxypropan-2-yl)benzofuran-5-yl)methoxy) phenyl)acetic Acid (104e)

Step-1: Preparation of methyl 7-bromo-2-(2-hydroxypropan-2-yl)benzofuran-5-carboxylate (104a)

Compound 104a was prepared according to the procedure reported in step-1 of Scheme-55, from methyl 3,5-dibromo-4-hydroxybenzoate (84a) (7 g, 22.59 mmol) in pyridine (20 mL) using 2-methyl-4-(trimethylsilyl)but-3-yn-2-ol (3.53 g, 22.59 mmol; CAS #: 5272-33-3) and copper(I) oxide (3.23 g, 22.59 mmol). This gave after workup and purification by flash column chromatography [silica (24 g), eluting with EtOAc in hexane from 0-70%] methyl 7-bromo-2-(2-hydroxypropan-2-yl)benzofuran-5-carboxylate (104a) (5 g, 71% yield) as a yellow oil; $^1$H NMR (300 MHz, DMSO-$d_6$) δ 8.25 (d, J=1.6 Hz, 1H), 8.01 (d, J=1.6 Hz, 1H), 6.95 (d, J=0.9 Hz, 1H), 5.56 (s, 1H, D$_2$O exchangeable), 3.89 (s, 3H), 1.55 (s, 6H).

Step-2: Preparation of 2-(7-bromo-5-(hydroxymethyl)benzofuran-2-yl)propan-2-ol (104b)

Compound 104b was prepared according to the procedure reported in step-2 of Scheme-76 from methyl 7-bromo-2-(2-hydroxypropan-2-yl)benzofuran-5-carboxylate (104a) (4 g, 12.77 mmol) in THF (60 mL) using LiBH$_4$ (19.16 mL, 38.3 mmol, 2 M solution in THF) and MeOH (1.23 g, 38.3 mmol). This gave after workup and purification by flash column chromatography [silica (24 g), eluting with EtOAc in hexane from 0-60%] 2-(7-bromo-5-(hydroxymethyl)benzofuran-2-yl)propan-2-ol (104b) (2.86 g, 79% yield) as a clear oil; $^1$H NMR (300 MHz, DMSO-$d_6$) δ 7.50 (d, J=1.2 Hz, 1H), 7.42 (d, J=1.4 Hz, 1H), 6.77 (d, J=1.1 Hz, 1H), 5.44 (s, 1H, D$_2$O exchangeable), 5.28 (t, J=5.8, 1.1 Hz, 1H, D$_2$O exchangeable), 4.55 (d, J=5.8 Hz, 2H), 1.53 (s, 6H).

Step-3: Preparation of Ethyl 2-(2-((7-bromo-2-(2-hydroxypropan-2-yl)benzofuran-5-yl)methoxy)phenyl)acetate (104c)

Compound 104c was prepared according to the procedure reported in step-2 of Scheme-23 from 2-(7-bromo-5-(hydroxymethyl)benzofuran-2-yl)propan-2-ol (104b) (2.82 g, 9.89 mmol) in DCM (180 mL) using triphenylphosphine (2.85 g, 10.88 mmol), ethyl 2-(2-hydroxyphenyl) acetate (23b) (1.87 g, 10.38 mmol) and di-(4-chlorobenzyl)azodicarboxylate (DCAD, 3.99 g, 10.88 mmol) in DCM (20 mL). This gave after workup and purification by flash column chromatography [silica (40 g), eluting with EtOAc in hexane from 0-50%] ethyl 2-(2-((7-bromo-2-(2-hydroxypropan-2-yl)benzofuran-5-yl)methoxy)phenyl)acetate (104c) (1.8 g, 41% yield) as a clear oil, which became a white solid on standing; $^1$H NMR (300 MHz, DMSO-$d_6$) δ 7.63 (d, J=1.4 Hz, 1H), 7.53 (d, J=1.4 Hz, 1H), 7.28-7.18 (m, 2H), 7.06 (d, J=8.1 Hz, 1H), 6.91 (t, J=7.4 Hz, 1H), 6.80 (s, 1H), 5.47 (d, J=1.1 Hz, 1H), 5.16 (s, 2H), 4.03 (q, J=7.1 Hz, 3H), 1.53 (s, 6H), 1.09 (t, J=7.1 Hz, 3H).

Step-4: Preparation of Ethyl 2-(2-((7-(3-(aminomethyl)phenyl)-2-(2-hydroxypropan-2-yl)benzofuran-5-yl)methoxy)phenyl)acetate (104d)

Compound 104d was prepared according to the procedure reported in step-3 of Scheme-1 from ethyl 2-(2-((7-bromo-2-(2-hydroxypropan-2-yl)benzofuran-5-yl)methoxy)phenyl)acetate (104c) (700 mg, 1.57 mmol) in dioxane (25 mL) using 3-(aminomethyl)phenylboronic acid hydrochloride (6c) (381 mg, 2.03 mmol), a solution of $K_2CO_3$ (649 mg, 4.69 mmol) in water (3 mL), bis(triphenylphosphine)palladium(II) chloride (165 mg, 0.24 mmol) and heating at 100° C. for 3h on oil bath. This gave after workup, purification by flash column chromatography [silica (12 g), eluting with DMA80 in DCM from 0-50%] followed by purification by reverse phase column chromatography [C18 (50 g), eluting with ACN in water (containing 0.1% HCl) from 0-100%] ethyl 2-(2-((7-(3-(aminomethyl)phenyl)-2-(2-hydroxypropan-2-yl)benzofuran-5-yl)methoxy)phenyl)acetate (104d) (585 mg, 79% yield) HCl salt as a white solid; $^1$H NMR (300 MHz, DMSO-$d_6$) δ 8.46 (s, 3H, $D_2O$ exchangeable), 8.01-7.93 (m, 2H), 7.64 (d, J=1.6 Hz, 1H), 7.62-7.53 (m, 3H), 7.29-7.19 (m, 2H), 7.11 (d, J=8.0 Hz, 1H), 6.91 (t, J=7.2 Hz, 1H), 6.76 (s, 1H), 5.48 (s, 1H, $D_2O$ exchangeable), 5.23 (s, 2H), 4.13 (d, J=5.7 Hz, 2H), 3.94 (q, J=7.1 Hz, 2H), 3.63 (s, 2H), 1.55 (s, 6H), 1.00 (t, J=7.1 Hz, 3H); MS (ES+): 474.3 (M+1); (ES−): 508.3 (M+Cl)

Step-5: Preparation of 2-(2-((7-(3-(aminomethyl)phenyl)-2-(2-hydroxypropan-2-yl)benzofuran-5-yl)methoxy)phenyl)acetic Acid (104e)

Compound 104e was prepared according to the procedure reported in step-6 of Scheme-1, from ethyl 2-(2-((7-(3-(aminomethyl)phenyl)-2-(2-hydroxypropan-2-yl)benzofuran-5-yl)methoxy)phenyl)acetate (104d) (70 mg, 0.15 mmol) in MeOH/THF (5 mL) using a solution of lithium hydroxide monohydrate (12.41 mg, 0.30 mmol) in water (1.0 mL). This gave after workup and purification by flash column chromatography [silica (4g), eluting with DMA80 in DCM from 0-80%] 2-(2-((7-(3-(aminomethyl)phenyl)-2-(2-hydroxypropan-2-yl)benzofuran-5-yl)methoxy)phenyl)acetic acid (104e) (20 mg, 30% yield) as a white solid; $^1$H NMR (300 MHz, DMSO-$d_6$) δ 8.35 (s, 1H), 8.15 (d, J=8.0 Hz, 1H), 7.89 (s, 1H), 7.60 (s, 1H), 7.50 (t, J=7.7 Hz, 1H), 7.35 (d, J=7.5 Hz, 1H), 7.15-7.03 (m, 2H), 6.93 (d, J=8.1 Hz, 1H), 6.88-6.67 (m, 2H), 5.50 (s, 1H, $D_2O$ exchangeable), 5.25 (s, 2H), 4.01 (s, 2H), 3.39 (s, 2H), 1.55 (s, 6H); $^1$H NMR (300 MHz, Methanol-$d_4$) δ 8.25-8.13 (m, 2H), 7.89 (s, 1H), 7.55-7.40 (m, 2H), 7.29 (d, J=7.6 Hz, 1H), 7.16 (t, J=7.8 Hz, 2H), 6.96 (d, J=8.1 Hz, 1H), 6.87 (t, J=7.4 Hz, 1H), 6.70 (s, 1H), 5.21 (s, 2H), 4.09 (s, 2H), 3.59 (s, 2H), 1.64 (s, 6H); MS (ES+): 446.3 (M+1); (ES−): 444.4 (M−1), 480.3 (M+Cl).

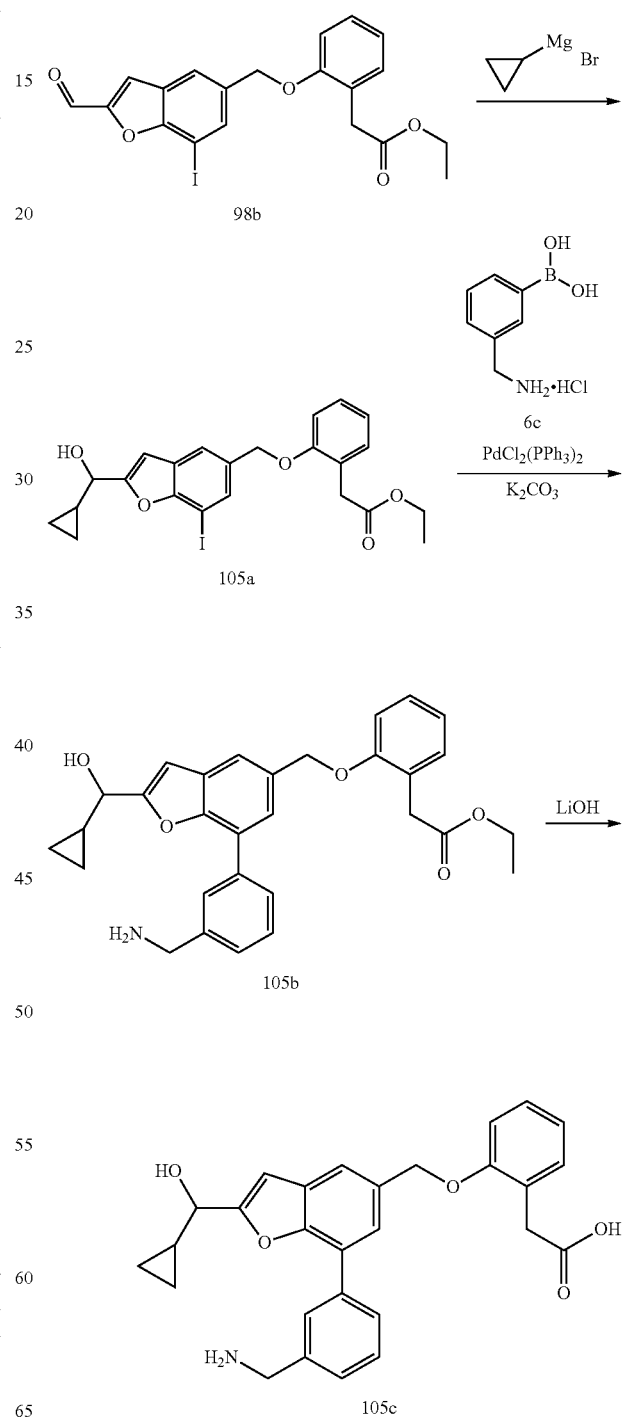

Scheme-105

Preparation of 2-(2-((7-(3-(aminomethyl)phenyl)-2-(cyclopropyl(hydroxy)methyl)benzofuran-5-yl)methoxy)phenyl)acetic Acid (105c)

Step-1: Preparation of Ethyl 2-(2-((2-(cyclopropyl(hydroxy)methyl)-7-iodobenzofuran-5-yl)methoxy)phenyl)acetate (105a)

Compound 105a was prepared according to the procedure reported in step-3 of Scheme-98, from ethyl 2-(2-((2-formyl-7-iodobenzofuran-5-yl)methoxy)phenyl)acetate (98b) (500 mg, 1.08 mmol) in THF (20 mL) using cyclopropyl magnesium bromide (1.0 M in THF, 1.185 mL, 1.185 mmol) at −78° C. This gave after workup and purification by flash column chromatography [silica gel (12 g), eluting with EtOAc in hexane from 0-60%] ethyl 2-(2-((2-(cyclopropyl(hydroxy)methyl)-7-iodobenzofuran-5-yl)methoxy)phenyl)acetate (105a) (227 mg, 42% yield) as a clear oil; $^1$H NMR (300 MHz, DMSO-$d_6$) δ 7.69 (s, 1H), 7.63 (s, 1H), 7.29-7.16 (m, 2H), 7.06 (d, J=8.1 Hz, 1H), 6.97-6.80 (m, 2H), 5.64 (d, J=5.5 Hz, 1H), 5.14 (s, 2H), 4.16 (t, J=6.6 Hz, 1H), 4.03 (q, J=7.2 Hz, 2H), 3.61 (s, 2H), 1.34-1.18 (m, 1H), 1.09 (t, J=7.0 Hz, 3H), 0.59-0.28 (m, 4H).

Step-2: Preparation of Ethyl 2-(2-((7-(3-(aminomethyl)phenyl)-2-(cyclopropyl(hydroxy)methyl)benzofuran-5-yl)methoxy)phenyl)acetate (105b)

Compound 105b was prepared according to the procedure reported in step-3 of Scheme-1 from ethyl 2-(2-((2-(cyclopropyl(hydroxy)methyl)-7-iodobenzofuran-5-yl)methoxy)phenyl)acetate (105a) (227 mg, 0.45 mmol) in dioxane (15 mL) using 3-(aminomethyl)phenylboronic acid hydrochloride (6c) (109 mg, 0.58 mmol), a solution of $K_2CO_3$ (186 mg, 1.35 mmol) in water (3 mL), bis(triphenylphosphine)palladium(II) chloride (47 mg, 0.067 mmol) and heating at 100° C. for 3h on an oil bath. This gave after workup, purification by flash column chromatography [silica (12 g), eluting with DMA80 in DCM from 0-50%] ethyl 2-(2-((7-(3-(aminomethyl)phenyl)-2-(cyclopropyl(hydroxy)methyl)benzofuran-5-yl)methoxy)phenyl)acetate (105b) (150 mg, 69% yield) as a white solid; $^1$H NMR (300 MHz, DMSO-$d_6$) δ 7.86 (s, 1H), 7.77 (dt, J=7.5, 1.5 Hz, 1H), 7.62 (d, J=1.5 Hz, 1H), 7.55 (d, J=1.6 Hz, 1H), 7.47 (t, J=7.5 Hz, 1H), 7.39 (d, J=7.6 Hz, 1H), 7.30-7.19 (m, 2H), 7.11 (d, J=8.1 Hz, 1H), 6.94-6.86 (m, 1H), 6.81 (s, 1H), 5.55 (s, 1H), 5.23 (s, 2H), 4.16 (d, J=7.6 Hz, 1H, $D_2O$ exchangeable), 3.94 (q, J=7.1 Hz, 2H), 3.82 (s, 2H), 3.63 (s, 2H), 1.32-1.16 (m, 1H), 1.00 (t, J=7.1 Hz, 3H), 0.58-0.48 (m, 2H), 0.48-0.37 (m, 2H); MS (ES+): 486.3 (M+1); (ES−): 484.3 (M−1), 520.4 (M+Cl).

Step-3: Preparation of 2-(2-((7-(3-(aminomethyl)phenyl)-2-(cyclopropyl(hydroxy)methyl)benzofuran-5-yl)methoxy)phenyl)acetic Acid (105c)

Compound 105c was prepared according to the procedure reported in step-6 of Scheme-1, from ethyl 2-(2-((7-(3-(aminomethyl)phenyl)-2-(cyclopropyl(hydroxy)methyl)benzofuran-5-yl)methoxy)phenyl)acetate (105b) (96 mg, 0.20 mmol) in MeOH/THF (10 mL) using a solution of lithium hydroxide monohydrate (25 mg, 0.6 mmol) in water (1.0 mL). This gave after workup and purification by reverse phase column [C18 (50 g), eluting with ACN in water (containing 0.1% HCl) from 0-100%] 2-(2-((7-(3-(aminomethyl)phenyl)-2-(cyclopropyl(hydroxy)methyl)benzofuran-5-yl)methoxy)phenyl)acetic acid (105c) (50 mg, 55% yield) HCl salt as a white solid; $^1$H NMR (300 MHz, DMSO-$d_6$) δ 8.34 (s, 1H), 8.15 (d, J=7.8 Hz, 1H), 7.89 (s, 1H), 7.62 (s, 1H), 7.49 (t, J=7.7 Hz, 1H), 7.35 (d, J=7.6 Hz, 1H), 7.13-7.05 (m, 2H), 6.94 (d, J=8.1 Hz, 1H), 6.87-6.77 (m, 2H), 5.26 (s, 2H), 4.17 (d, J=7.6 Hz, 2H), 4.01 (s, 2H), 3.40 (s, 2H), 1.33-1.21 (m, 1H), 0.59-0.48 (m, 2H), 0.48-0.33 (m, 2H); MS (ES+): 458.3 (M+1); 480.3 (M+Na); (ES−): 456.4 (M−1), 492.3 (M+Cl).

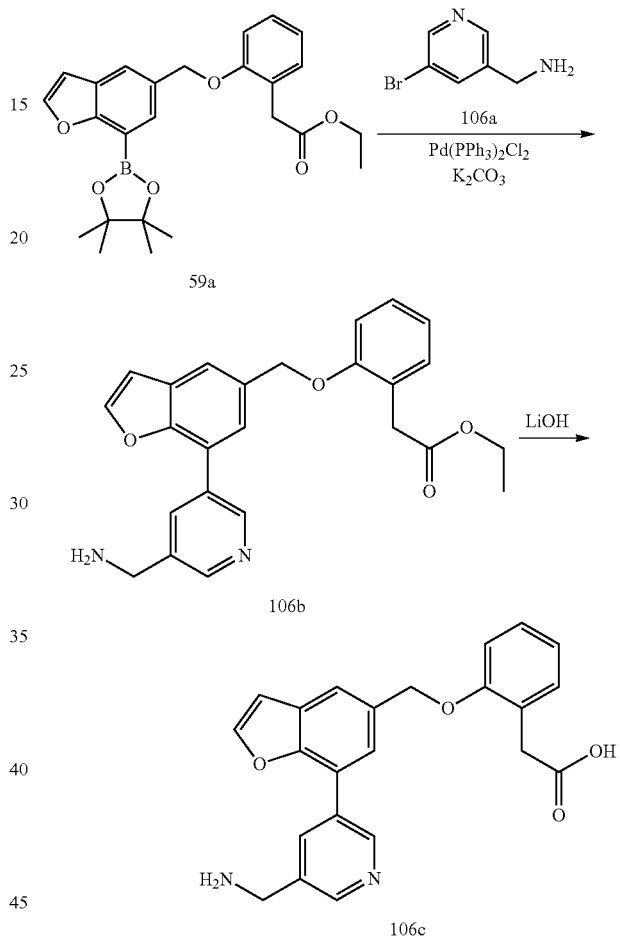

Scheme-106

Preparation of 2-(2-((7-(5-(aminomethyl)pyridin-3-yl)benzofuran-5-yl)methoxy)phenyl)acetic Acid (106c)

Step-1: Preparation of Ethyl 2-(2-((7-(5-(aminomethyl)pyridin-3-yl)benzofuran-5-yl)methoxy)phenyl)acetate (106b)

Compound 106b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (382 mg, 0.88 mmol) in dioxane (10 mL) using (5-bromopyridin-3-yl)methanamine (106a) (246 mg, 1.31 mmol), bis(triphenylphosphine)palladium(II) chloride (92 mg, 0.13 mmol) and a solution of $K_2CO_3$ (363 mg, 2.63 mmol) in water (1 mL) under an Ar atmosphere and heating at 95° C. for 2 h on oil bath. This gave after workup, purification by flash column chromatography [silica (12 g), eluting with DMA80 in DCM from 0-70%] ethyl 2-(2-((7-(5-(aminomethyl)pyridin-3-yl)benzofuran-5-yl)methoxy)phenyl)acetate (106b) (112 mg, 31% yield) as a white solid; MS (ES+): 417.3 (M+1).

Step-2: Preparation of 2-(2-((7-(5-(aminomethyl)pyridin-3-yl)benzofuran-5-yl)methoxy)phenyl)acetic Acid (106c)

Compound 106c was prepared according to the procedure reported in step-6 of Scheme-1, from ethyl 2-(2-((7-(5-(aminomethyl)pyridin-3-yl)benzofuran-5-yl)methoxy)phenyl)acetate (106b) (112 mg, 0.27 mmol) in MeOH/THF (10 mL) using a solution of lithium hydroxide monohydrate (34 mg, 0.81 mmol) in water (1 mL). This gave after workup and purification by reverse phase column [C18 (50 g), eluting with ACN in water (containing 0.1% HCl) from 0-100%] 2-(2-((7-(5-(aminomethyl)pyridin-3-yl)benzofuran-5-yl)methoxy)phenyl)acetic acid (106c) (55 mg, 53% yield) HCl salt as a white solid; $^1$H NMR (300 MHz, DMSO-$d_6$) δ 9.26 (d, J=1.8 Hz, 1H), 8.72 (s, 1H), 8.58 (d, J=1.7 Hz, 1H), 8.15 (t, J=1.7 Hz, 1H), 7.90 (s, 1H), 7.76 (d, J=1.5 Hz, 1H), 7.16-7.06 (m, 3H), 6.98 (d, J=8.1 Hz, 1H), 6.86-6.77 (m, 1H), 5.29 (s, 2H), 4.07 (s, 2H), 3.43 (s, 2H); MS (ES+): 389.3 (M+1); 411.2 (M+Na); (ES−): 387.3 (M−1), 423.3 (M+Cl).

Scheme-107

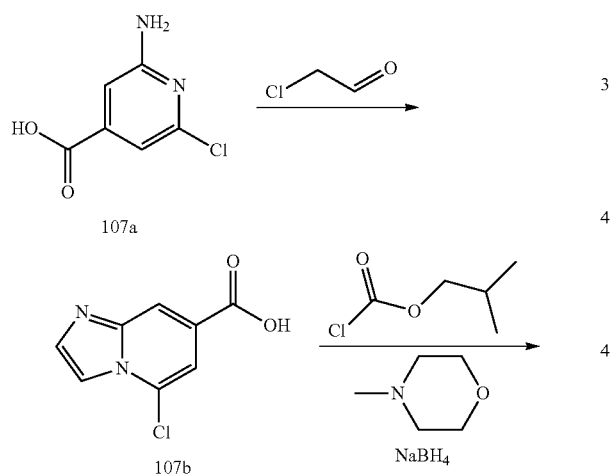

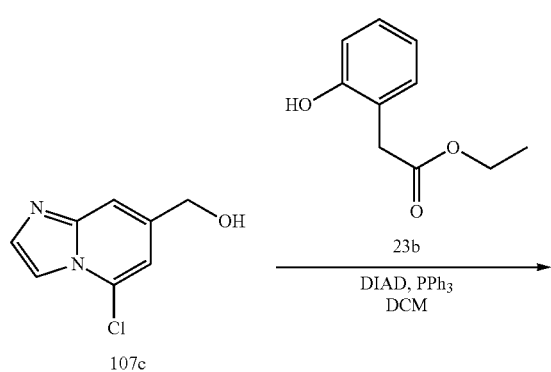

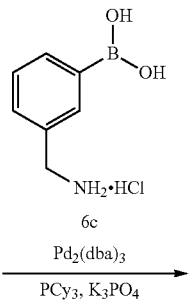

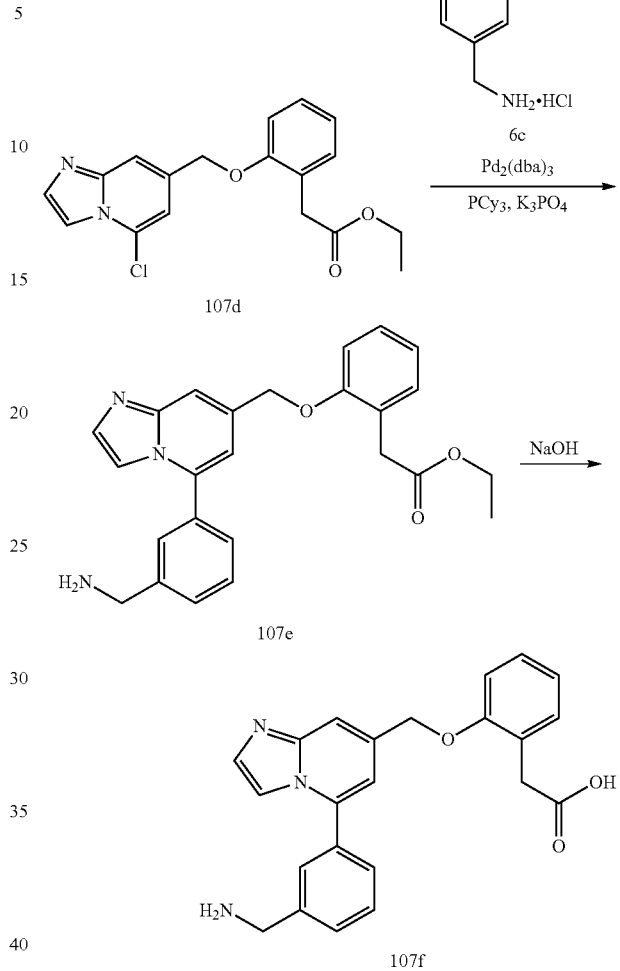

Preparation of 2-(2-((5-(3-(aminomethyl)phenyl)imidazo[1,2-a]pyridin-7-yl)methoxy)phenyl)acetic Acid (107f)

Step-1: Preparation of 5-chloroimidazo[1,2-a]pyridine-7-carboxylic acid (107b)

To a solution of 2-amino-6-chloroisonicotinic acid (107a) (0.5 g, 2.90 mmol; CAS #6313-55-9) in EtOH (20 mL) was added 2-chloroacetaldehyde (1.47 mL, 11.59 mmol) and heated at reflux overnight. The reaction mixture was cooled to RT diluted with EtOAc, washed with water, brine, dried, filtered and concentrated in vacuum. The residue obtained was purified by flash column chromatography [silica (12 g), eluting with DMA80 in DCM from 0-100%] to afford 5-chloroimidazo[1,2-a]pyridine-7-carboxylic acid (107b) (0.45 g, 79% yield) as a white solid; $^1$H NMR (300 MHz, DMSO-$d_6$) δ 8.03 (s, 1H), 7.95 (s, 1H), 7.77 (d, J=1.3 Hz, 1H), 7.50 (d, J=1.2 Hz, 1H); MS (ES+): 197.0 & 199.1 (M+1); MS (ES−): 195.1 & 197.1 (M−1).

Step-2: Preparation of (5-chloroimidazo[1,2-a]pyridin-7-yl)methanol (107c)

Compound 107c was prepared according to the procedure reported in step-1 of Scheme-23 from 5-chloroimidazo[1,2- a]pyridine-7-carboxylic acid (107b) (0.6 g, 3.05 mmol) using N-methylmorpholine (0.40 mL, 3.66 mmol) in THF (50 mL), isobutyl chloroformate (0.48 mL, 3.66 mmol) and NaBH$_4$ (0.35 g, 9.16 mmol) in water (0.8 mL). This gave after workup and purification by flash column chromatography [silica (12 g), eluting with DMA80 in DCM from 0-50%] (5-chloroimidazo[1,2-a]pyridin-7-yl)methanol (107c) (0.3 g, 54% yield) as a yellow solid; $^1$H NMR (300 MHz, DMSO-d$_6$) δ 7.96 (s, 1H), 7.67 (s, 1H), 7.51 (s, 1H), 7.12 (s, 1H), 5.51 (t, J=5.8 Hz, 1H), 4.55 (dd, J=5.8, 1.1 Hz, 2H); MS (ES+): 183.1 (M+1).

Step-3: Preparation of Ethyl 2-(2-((5-chloroimidazo [1,2-a]pyridin-7-yl)methoxy)phenyl)acetate (107d)

Compound 107d was prepared according to the procedure reported in step-2 of Scheme-23 from (5-chloroimidazo[1, 2-a]pyridin-7-yl)methanol (107c) (0.15 g, 0.82 mmol) in DCM (10 mL) using triphenylphosphine (0.28 g, 1.07 mmol), ethyl 2-(2-hydroxyphenyl) acetate (23b) (0.19 g, 1.07 mmol) and di-(4-chlorobenzyl)azodicarboxylate (DIAD, 0.39 g, 1.07 mmol). This gave after workup and purification by flash column chromatography [silica (24 g), eluting with EtOAc in hexane from 0-60%] ethyl 2-(2-((5-chloroimidazo[1,2-a]pyridin-7-yl)methoxy)phenyl)acetate (107d) (0.2 g, 71% yield) as a colorless oil; MS (ES−): 343.2 (M−1).

Step-4: Preparation of Ethyl 2-(2-((5-(3-(aminomethyl)phenyl)imidazo[1,2-a]pyridin-7-yl)methoxy) phenyl)acetate (107e)

Compound 107e was prepared according to the procedure reported in step-3 of Scheme-1 from ethyl 2-(2-((5-chloroimidazo[1,2-a]pyridin-7-yl)methoxy)phenyl)acetate (107d) (0.15 g, 0.44 mmol) in dioxane (4 mL) using 3-(aminomethyl)phenylboronic acid hydrochloride (6c) (0.12 g, 0.65 mmol), tripotassium phosphate (3 M aqueous solution, 0.25 mL, 0.74 mmol), tricyclohexylphosphine (0.04 g, 0.13 mmol) and Pd$_2$(dba)$_3$ (0.04 g, 0.04 mmol) under an Ar atmosphere and heating at 125° C. for 120 min in a microwave. This gave after workup, purification by flash column chromatography [silica (12 g), eluting with DMA80 in DCM from 0-50%] ethyl 2-(2-((5-(3-(aminomethyl)phenyl)imidazo[1,2-a]pyridin-7-yl)methoxy)phenyl)acetate (107e) (0.08 g, 44% yield) as a white solid; MS (ES+): 416.3 (M+1).

Step-5: Preparation of 2-(2-((5-(3-(aminomethyl) phenyl)imidazo[1,2-a]pyridin-7-yl)methoxy)phenyl) acetic Acid (107f)

Compound 107f was prepared according to the procedure reported in step-4 of Scheme-4, from ethyl 2-(2-((5-(3-(aminomethyl)phenyl)imidazo[1,2-a]pyridin-7-yl)methoxy) phenyl)acetate (107e) 0.07 g, 0.17 mmol) in MeOH/THF (4 mL) using a solution of sodium hydroxide (0.61 mL, 1.52 mmol, 2.5 M) in water (1 mL). This gave after workup and purification by reverse phase column [C18 (50 g), eluting with ACN in water (containing 0.1% HCl) from 0-100%] 2-(2-((5-(3-(aminomethyl)phenyl)imidazo[1,2-a]pyridin-7-yl)methoxy)phenyl)acetic acid (107f) (0.01 g, 9% yield) HCl salt as a white solid; $^1$H NMR (300 MHz, DMSO-d$_6$) δ 11.89 (s, 1H), 8.55 (s, 3H), 7.67 (dt, J=14.6, 6.9 Hz, 2H), 7.56 (t, J=2.9 Hz, 1H), 7.44 (dt, J=15.3, 7.7 Hz, 1H), 7.34 (s, 1H), 7.21 (d, J=7.3 Hz, 2H), 7.09 (d, J=8.4 Hz, 1H), 6.90 (t, J=7.3 Hz, 1H), 6.45 (q, J=2.7 Hz, 1H), 5.29 (s, 2H), 4.16 (q, J=5.9 Hz, 2H), 3.60 (s, 2H); MS (ES+): 388.3 (M+1); MS (ES−): 386.3 (M−1), 422.3 (M+Cl). HPLC purity: 95.72%.

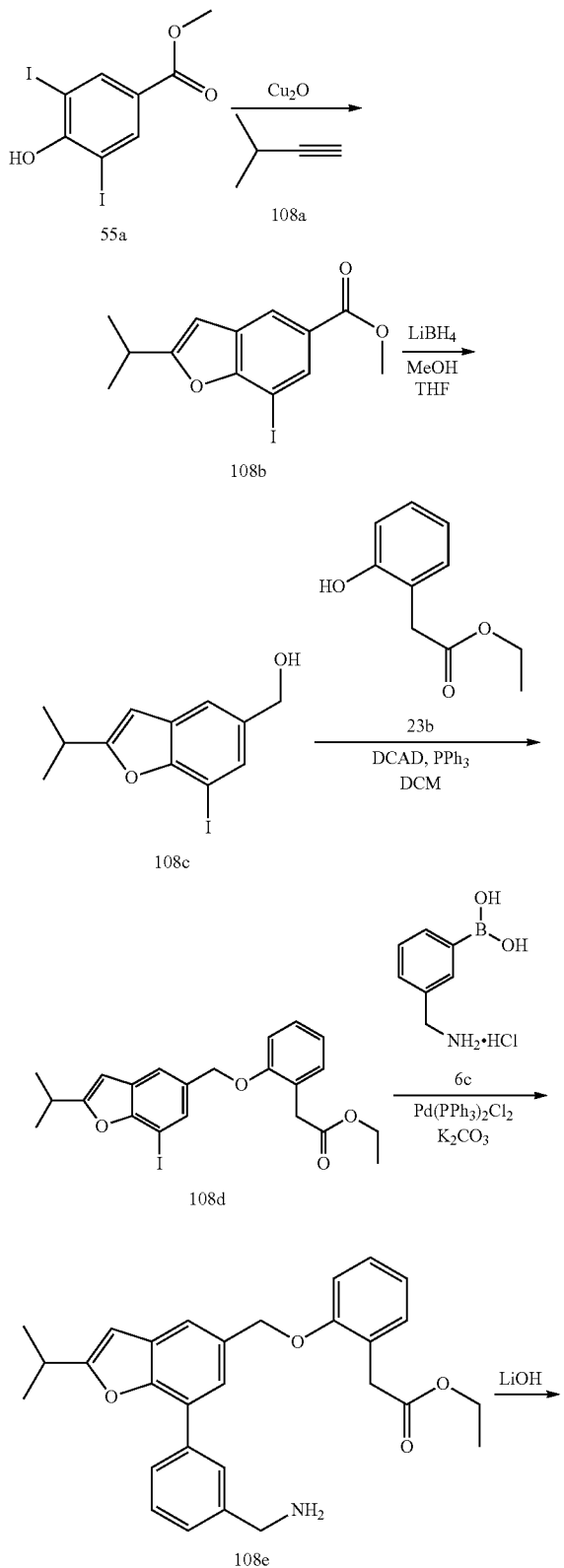

Scheme-108

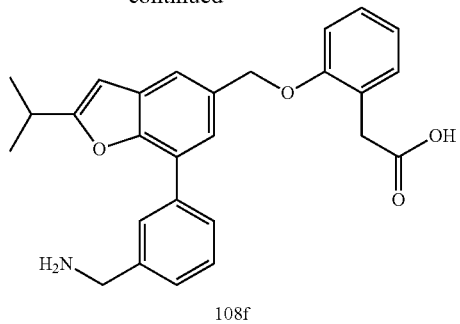

108f

Preparation of 2-(2-((7-(3-(aminomethyl)phenyl)-2-isopropylbenzofuran-5-yl)methoxy)phenyl)acetic Acid (108f)

Step-1: Preparation of methyl 7-iodo-2-isopropylbenzofuran-5-carboxylate (108b)

Compound 108b was prepared according to the procedure reported in step-1 of Scheme-55, from methyl 4-hydroxy-3,5-diiodobenzoate (55a) (10 g, 24.76 mmol) in pyridine (10 mL) using 3-methylbut-1-yne (108a) (1.69 g, 24.76 mmol; CAS #: 598-23-2) and copper(I) oxide (1.77 g, 12.38 mmol). This gave after workup and purification by flash column chromatography [silica (80 g), eluting with EtOAc in hexane from 0-70%] methyl 7-iodo-2-isopropylbenzofuran-5-carboxylate (108b) (5.77 g, 68% yield) as a white solid; $^1$H NMR (300 MHz, DMSO-$d_6$) δ 8.18 (d, J=1.6 Hz, 1H), 8.15 (d, J=1.6 Hz, 1H), 6.86 (d, J=1.1 Hz, 1H), 3.87 (s, 3H), 3.20-3.07 (m, 1H), 1.32 (d, J=6.9 Hz, 6H).

Step-2: Preparation of (7-iodo-2-isopropylbenzofuran-5-yl)methanol (108c)

Compound 108c was prepared according to the procedure reported in step-2 of Scheme-76 from methyl 7-iodo-2-isopropylbenzofuran-5-carboxylate (108b) (4.77 g, 13.86 mmol) in THF (200 mL) using LiBH$_4$ (13.86 mL, 27.7 mmol, 2 M solution in THF) and MeOH (1.12 mL, 27.7 mmol). This gave after workup and purification by flash column chromatography [silica (24 g), eluting with EtOAc in hexane from 0-60%] (7-iodo-2-isopropylbenzofuran-5-yl)methanol (108c) (2.7 g, 62% yield) as a clear oil; $^1$H NMR (300 MHz, DMSO-$d_6$) δ 7.56 (d, J=1.5 Hz, 1H), 7.46 (d, J=1.5 Hz, 1H), 6.69 (d, J=1.1 Hz, 1H), 5.27 (t, J=5.8 Hz, 1H), 4.52 (d, J=5.8 Hz, 2H), 3.16-3.00 (m, 1H), 1.30 (d, J=6.9 Hz, 6H).

Step-3: Preparation of Ethyl 2-(2-((7-iodo-2-isopropylbenzofuran-5-yl)methoxy)phenyl)acetate (108d)

Compound 108d was prepared according to the procedure reported in step-2 of Scheme-23 from (7-iodo-2-isopropylbenzofuran-5-yl)methanol (108c) (2.7 g, 8.54 mmol) in DCM (50 mL) using triphenylphosphine (2.46 g, 9.39 mmol), ethyl 2-(2-hydroxyphenyl) acetate (23b) (1.69 g, 9.39 mmol) and di-(4-chlorobenzyl)azodicarboxylate (DCAD, 3.45 g, 9.39 mmol) in DCM (20 mL). This gave after workup and purification by flash column chromatography [silica (40 g), eluting with EtOAc in hexane from 0-50%] ethyl 2-(2-((7-iodo-2-isopropylbenzofuran-5-yl)methoxy)phenyl)acetate (108d) (2.8 g, 69% yield) as a clear oil; $^1$H NMR (300 MHz, DMSO-$d_6$) δ 7.65 (d, J=1.5 Hz, 1H), 7.58 (d, J=1.5 Hz, 1H), 7.28-7.17 (m, 2H), 7.06 (d, J=8.1 Hz, 1H), 6.91 (t, J=7.4 Hz, 1H), 6.73 (d, J=1.0 Hz, 1H), 5.13 (s, 2H), 4.03 (q, J=7.1 Hz, 2H), 3.61 (s, 2H), 3.18-2.99 (m, 1H), 1.29 (s, 7H), 1.09 (t, J=7.1 Hz, 3H).

Step-4: Preparation of Ethyl 2-(2-((7-(3-(aminomethyl)phenyl)-2-isopropylbenzofuran-5-yl)methoxy)phenyl)acetate (108e)

Compound 108e was prepared according to the procedure reported in step-3 of Scheme-1 from ethyl 2-(2-((7-iodo-2-isopropylbenzofuran-5-yl)methoxy)phenyl)acetate (108d) (850 mg, 1.78 mmol) in dioxane (20 mL) using 3-(aminomethyl)phenylboronic acid hydrochloride (6c) (433 mg, 2.31 mmol), a solution of K$_2$CO$_3$ (737 mg, 5.33 mmol) in water (5 mL), bis(triphenylphosphine)palladium(II) chloride (187 mg, 0.27 mmol) and heating at 100° C. for 3h on oil bath. This gave after workup, purification by flash column chromatography [silica (12 g), eluting with DMA80 in DCM from 0-50%] followed by purification by reverse phase column chromatography [C18 (50 g), eluting with ACN in water (containing 0.1% HCl) from 0-100%] ethyl 2-(2-((7-(3-(aminomethyl)phenyl)-2-isopropylbenzofuran-5-yl)methoxy)phenyl)acetate (108e) (468 mg, 58% yield) HCl salt as a white solid; $^1$H NMR (300 MHz, DMSO-$d_6$) δ 8.44 (s, 3H, D$_2$O exchangeable), 7.97 (d, J=2.3 Hz, 1H), 7.93 (dt, J=7.4, 1.7 Hz, 1H), 7.65-7.59 (m, 2H), 7.59-7.56 (m, 1H), 7.54 (d, J=1.7 Hz, 1H), 7.29-7.19 (m, 2H), 7.10 (d, J=8.1 Hz, 1H), 6.91 (td, J=7.4, 1.0 Hz, 1H), 6.67 (d, J=1.0 Hz, 1H), 5.22 (s, 2H), 4.13 (s, 2H), 3.94 (q, J=7.1 Hz, 2H), 3.63 (s, 2H), 3.18-3.04 (m, 1H), 1.32 (d, J=6.9 Hz, 6H), 1.00 (t, J=7.1 Hz, 3H); MS (ES+): 458.3 (M+1); (ES−): 492.3 (M+Cl).

Step-5: Preparation of 2-(2-((7-(3-(aminomethyl)phenyl)-2-isopropylbenzofuran-5-yl)methoxy)phenyl)acetic Acid (108f)

Compound 108f was prepared according to the procedure reported in step-6 of Scheme-1, from ethyl 2-(2-((7-(3-(aminomethyl)phenyl)-2-isopropylbenzofuran-5-yl)methoxy)phenyl)acetate (108e) (225 mg, 0.49 mmol) in MeOH/THF (10 mL) using a solution of lithium hydroxide monohydrate (62 mg, 1.48 mmol) in water (1.0 mL). This gave after workup 2-(2-((7-(3-(aminomethyl)phenyl)-2-isopropylbenzofuran-5-yl)methoxy)phenyl)acetic acid (108f) (165 mg, 78% yield) as a white solid; $^1$H NMR (300 MHz, DMSO-$d_6$) δ 9.16 (s, 3H, D$_2$O exchangeable), 8.01 (d, J=1.9 Hz, 1H), 7.96 (d, J=7.8 Hz, 1H), 7.64-7.62 (m, 1H), 7.62-7.55 (m, 2H), 7.55-7.49 (m, 1H), 7.23-7.16 (m, 2H), 7.06 (d, J=8.3 Hz, 1H), 6.89 (t, J=7.3 Hz, 1H), 6.66 (d, J=1.0 Hz, 1H), 5.24 (s, 2H), 4.12 (s, 2H), 3.57 (s, 2H), 3.19-3.06 (m, 1H), 1.33 (d, J=6.9 Hz, 6H); MS (ES+): 430.3 (M+1); (ES−): 428.4 (M+1); 464.4 (M+Cl).

Scheme-109

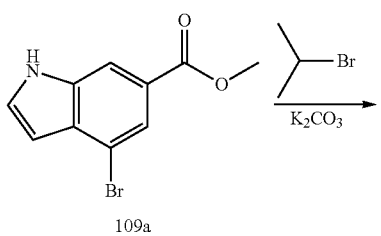

109a

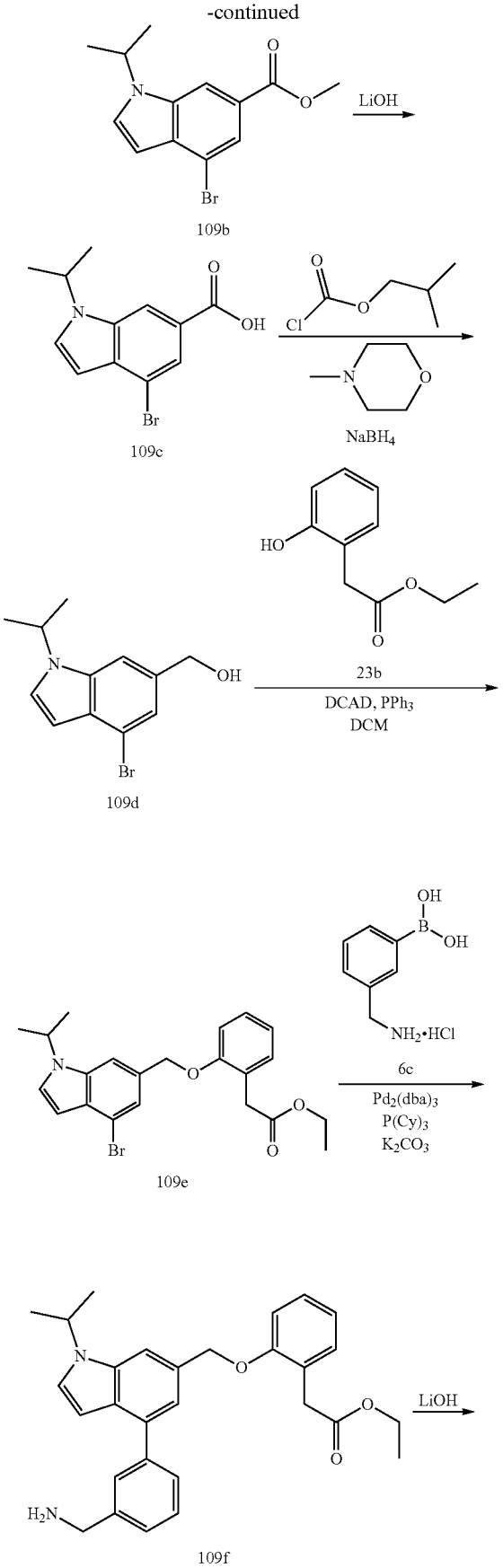

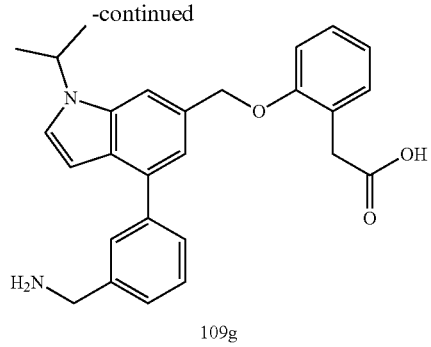

Preparation of 2-(2-((4-(3-(aminomethyl)phenyl)-1-isopropyl-1H-indol-6-yl)methoxy)phenyl)acetic Acid (109g)

Step-1: Preparation of methyl 4-bromo-1-isopropyl-1H-indole-6-carboxylate (109b)

To a solution of methyl 4-bromo-1H-indole-6-carboxylate (109a) (1.5 g, 5.90 mmol; CAS #882679-96-1) in DMF (10 mL) was added 2-bromopropane (1.3 mL, 14.76 mmol), potassium carbonate (2.86 g, 20.66 mmol) and heated at 60° C. for 3 days. The reaction mixture was diluted with EtOAc (100 mL), washed with water (3×), brine, dried, filtered and concentrated in vacuum. The residue obtained was purified by flash column chromatography [silica (12 g), eluting with EtOAc in hexane from 0-60%] to afford methyl 4-bromo-1-isopropyl-1H-indole-6-carboxylate (109b) (0.85 g, 49% yield) as a white solid; $^1$H NMR (300 MHz, DMSO-$d_6$) δ 8.20 (s, 1H), 7.90 (d, J=3.2 Hz, 1H), 7.79 (s, 1H), 6.54 (d, J=3.2 Hz, 1H), 4.92 (m Hz, 1H), 3.88 (s, 3H), 1.47 (d, J=6.6 Hz, 6H); MS (ES+): 297.4 (M+1).

Step-2: Preparation of 4-bromo-1-isopropyl-1H-indole-6-carboxylic Acid (109c)

Compound 109c was prepared according to the procedure reported in step-6 of Scheme-1, from methyl 4-bromo-1-isopropyl-1H-indole-6-carboxylate (109b) (0.8 g, 2.70 mmol) in THF/MeOH (20 mL) using a solution of lithium hydroxide hydrate (0.68 g, 16.21 mmol) in water (3 mL). This gave after workup 4-bromo-1-isopropyl-1H-indole-6-carboxylic acid (109c) (0.7 g, 92% yield) as a white solid; $^1$H NMR (300 MHz, DMSO-$d_6$) δ 12.96 (s, 1H), 8.17 (s, 1H), 7.88 (d, J=3.3 Hz, 1H), 7.77 (s, 1H), 6.52 (d, J=3.2 Hz, 1H), 4.90 (m, 1H), 1.47 (d, J=6.6 Hz, 6H); MS (ES−): 282.2 (M−1).

Step-3: Preparation of (4-bromo-1-isopropyl-1H-indol-6-yl)methanol (109d)

Compound 109d was prepared according to the procedure reported in step-1 of Scheme-23 from 4-bromo-1-isopropyl-1H-indole-6-carboxylic acid (109c) (0.75 g, 2.66 mmol) using N-methylmorpholine (0.35 mL, 3.19 mmol) in THF (100 mL), isobutyl chloroformate (0.42 mL, 3.19 mmol) and NaBH$_4$ (0.30 g, 7.97 mmol) in water (0.8 mL). This gave after workup and purification by flash column chromatography [silica (24 g), eluting with EtOAc/MeOH=9:1 in hexane from 0-100%] (4-bromo-1-isopropyl-1H-indol-6-yl)

methanol (109d) (0.65 g, 91% yield) as a yellow solid; $^1$H NMR (300 MHz, DMSO-d$_6$) δ 7.58 (d, J=3.3 Hz, 1H), 7.47 (s, 1H), 7.21 (s, 1H), 6.37 (d, J=3.3 Hz, 1H), 5.24 (t, J=5.8 Hz, 1H), 4.73 (m, 1H), 4.58 (d, J=5.8 Hz, 2H), 1.45 (d, J=6.7 Hz, 6H).

Step-4: Preparation of Ethyl 2-(2-((4-bromo-1-isopropyl-1H-indol-6-yl)methoxy)phenyl)acetate (109e)

Compound 109e was prepared according to the procedure reported in step-2 of Scheme-23 from (4-bromo-1-isopropyl-1H-indol-6-yl)methanol (109d) (0.65 g, 2.42 mmol) in DCM (10 mL) using triphenylphosphine (0.83 g, 3.15 mmol), ethyl 2-(2-hydroxyphenyl) acetate (23b) (0.57 g, 3.15 mmol) and di-(4-chlorobenzyl)azodicarboxylate (DCAD, 1.16 g, 3.15 mmol). This gave after workup and purification by flash column chromatography [silica (12 g), eluting with EtOAc/MeOH (9:1) in hexane from 0-60%] ethyl 2-(2-((4-bromo-1-isopropyl-1H-indol-6-yl)methoxy) phenyl)acetate (109e) (0.12 g, 12% yield) as a colorless oil; MS (ES−): 428.3 & 430.2 (M−1).

Step-5: Preparation of Ethyl 2-(2-((4-(3-(aminomethyl)phenyl)-1-isopropyl-1H-indol-6-yl)methoxy) phenyl)acetate (109f)

Compound 109f was prepared according to the procedure reported in step-3 of Scheme-1 from ethyl 2-(2-((4-bromo-1-isopropyl-1H-indol-6-yl)methoxy)phenyl)acetate (109e) (0.3 g, 0.70 mmol) in dioxane (15 mL) using 3-(aminomethyl)phenylboronic acid hydrochloride (6c) (0.2 g, 1.05 mmol), K$_2$CO$_3$ (0.29 g, 2.09 mmol) in water (2 mL) and bis(triphenylphosphine)Palladium(II) chloride (0.07 g, 0.11 mmol) under an Ar atmosphere and heating at 100° C. for 4 h in an oil bath. This gave after workup, purification by flash column chromatography [silica (12 g), eluting with MeOH in DCM from 0-20%] followed by purification by reverse phase column [C18 (50 g), eluting with ACN in water (containing 0.1% HCl) from 0-100%] ethyl 2-(2-((4-(3-(aminomethyl)phenyl)-1-isopropyl-1H-indol-6-yl)methoxy) phenyl)acetate (109f) (0.25 g, 79% yield) HCl salt as a white solid; $^1$H NMR (300 MHz, DMSO-d$_6$) δ 8.29 (s, 3H), 7.80 (d, J=1.7 Hz, 1H), 7.67 (dt, J=7.7, 1.4 Hz, 1H), 7.64 (s, 1H), 7.61 (d, J=3.3 Hz, 1H), 7.56 (t, J=7.6 Hz, 1H), 7.48 (d, J=7.7 Hz, 1H), 7.27-7.20 (m, 2H), 7.19 (d, J=1.2 Hz, 1H), 7.13 (d, J=8.2 Hz, 1H), 6.90 (td, J=7.4, 1.1 Hz, 1H), 6.67 (d, J=3.3 Hz, 1H), 5.25 (s, 2H), 4.81 (p, J=6.7 Hz, 1H), 4.13 (s, 2H), 3.92 (q, J=7.1 Hz, 2H), 3.63 (s, 2H), 1.50 (d, J=6.6 Hz, 6H), 0.98 (t, J=7.1 Hz, 3H); MS (ES+): 457.5 (M+1); MS (ES−): 491.6 (M+Cl). HPLC purity: 97.55%.

Step-6: Preparation of 2-(2-((4-(3-(aminomethyl) phenyl)-1-isopropyl-1H-indol-6-yl)methoxy)phenyl) acetic Acid (109g)

Compound 109g was prepared according to the procedure reported in step-6 of Scheme-1, from ethyl 2-(2-((4-(3-(aminomethyl)phenyl)-1-isopropyl-1H-indol-6-yl)methoxy) phenyl)acetate (109f) (0.04 g, 0.09 mmol) in THF/MeOH (4 mL) using a solution of lithium hydroxide hydrate (0.02 g, 0.53 mmol) in water (1 mL). This gave after workup and purification by reverse phase column [C18 (50 g), eluting with ACN in water (containing 0.1% HCl) from 0-100%] 2-(2-((4-(3-(aminomethyl)phenyl)-1-isopropyl-1H-indol-6-yl)methoxy)phenyl)acetic acid (109g) (0.02 g, 56% yield) as a white solid; $^1$H NMR (300 MHz, DMSO-d$_6$) δ 12.21 (s, 1H), 8.33 (s, 4H), 7.80 (s, 1H), 7.68 (m, 2H), 7.61 (d, J=3.3 Hz, 1H), 7.55 (t, J=7.6 Hz, 1H), 7.48 (d, J=7.6 Hz, 1H), 7.25-7.20 (m, 3H), 7.11 (m, 1H), 6.94-6.86 (m, 1H), 6.67 (d, J=3.3 Hz, 1H), 5.27 (s, 2H), 4.81 (p, J=6.8 Hz, 1H), 4.13 (s, 2H), 3.60 (s, 2H), 1.49 (d, J=6.6 Hz, 6H); MS (ES−): 427.5 (M−1).

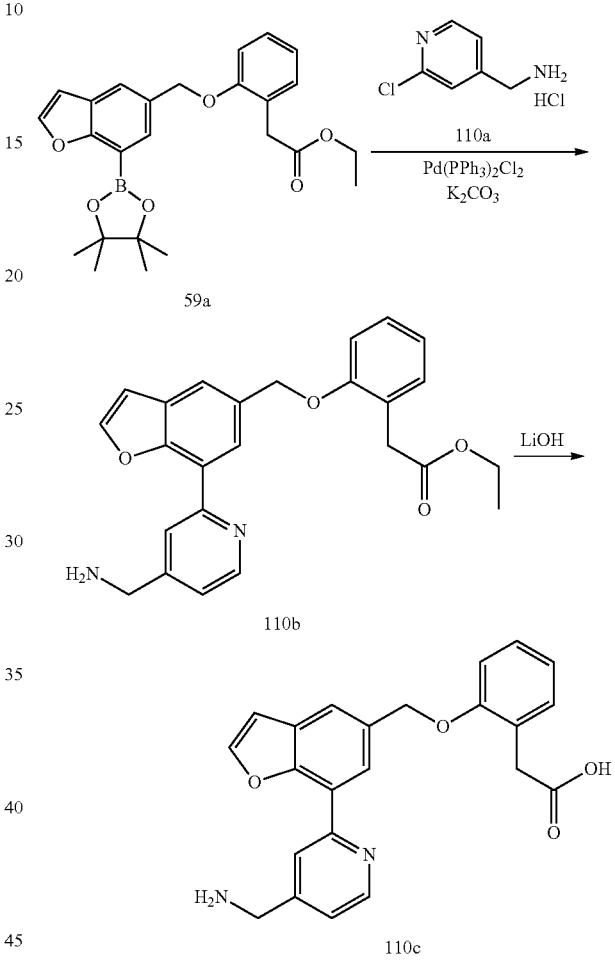

Scheme-110

Preparation of 2-(2-((7-(4-(aminomethyl)pyridin-2-yl)benzofuran-5-yl)methoxy)phenyl)acetic Acid (110c)

Step-1: Preparation of Ethyl 2-(2-((7-(4-(aminomethyl)pyridin-2-yl)benzofuran-5-yl)methoxy)phenyl) acetate (110b)

Compound 110b was prepared according to the procedure reported in step-3 of Scheme-1 from ethyl 2-(2-((7-(4,4,5,5-tetramethyl-1,3,2-dioxaborolan-2-yl)benzofuran-5-yl) methoxy)phenyl)acetate (59a) (330 mg, 0.76 mmol) in dioxane (10 mL) using (2-chloropyridin-4-yl)methanamine hydrochloride (110a) (203 mg, 1.14 mmol), bis(triphenylphosphine)palladium(II) chloride (80 mg, 0.11 mmol) and a solution of K$_2$CO$_3$ (314 mg, 2.27 mmol) in water (1 mL) under an Ar atmosphere and heating at 100° C. for 3 h on oil bath. This gave after workup, purification by flash column chromatography [silica (12 g), eluting with DMA80 in DCM from 0-70%] followed by purification by reverse phase column [C18 (50 g), eluting with ACN in water (containing 0.1% HCl) from 0-100%] ethyl 2-(2-((7-(4-(aminomethyl)pyridin-2-yl)benzofuran-5-yl)methoxy)phenyl)acetate (110b) (220 mg, 70% yield) HCl salt as an off white solid; $^1$H NMR (300 MHz, DMSO-$d_6$) δ 8.82 (d, J=5.1 Hz, 1H), 8.73 (s, 3H, $D_2O$ exchangeable), 8.41 (s, 1H), 8.18 (d, J=2.2 Hz, 1H), 8.14 (d, J=1.7 Hz, 1H), 7.84 (d, J=1.6 Hz, 1H), 7.63 (dd, J=5.2, 1.5 Hz, 1H), 7.32-7.18 (m, 2H), 7.17-7.10 (m, 2H), 6.92 (td, J=7.4, 1.1 Hz, 1H), 5.27 (s, 2H), 4.23 (q, J=6.0 Hz, 2H), 3.97 (q, J=7.1 Hz, 2H), 3.62 (s, 2H), 1.00 (t, J=7.1 Hz, 3H); MS (ES+): 417.3 (M+1); (ES−): 451.4 (M+Cl).

Step-2: Preparation of 2-(2-((7-(4-(aminomethyl)pyridin-2-yl)benzofuran-5-yl)methoxy)phenyl)acetic Acid (110c)

Compound 110c was prepared according to the procedure reported in step-6 of Scheme-1, from ethyl 2-(2-((7-(4-(aminomethyl)pyridin-2-yl)benzofuran-5-yl)methoxy)phenyl)acetate (110b) (133 mg, 0.32 mmol) in MeOH/THF (20 mL) using a solution of lithium hydroxide monohydrate (27 mg, 0.64 mmol) in water (2 mL). This gave after workup and purification by reverse phase column [C18 (50 g), eluting with ACN in water (containing 0.1% HCl) from 0-100%] 2-(2-((7-(4-(aminomethyl)pyridin-2-yl)benzofuran-5-yl)methoxy)phenyl)acetic acid (110c) (72 mg, 58% yield) HCl salt as a white solid; $^1$H NMR (300 MHz, DMSO-$d_6$) δ 8.83 (d, J=5.1 Hz, 1H), 8.68 (s, 3H, $D_2O$ exchangeable), 8.39 (d, J=1.5 Hz, 1H), 8.17 (d, J=2.2 Hz, 1H), 8.14 (d, J=1.7 Hz, 1H), 7.87 (d, J=1.6 Hz, 1H), 7.63 (dd, J=5.3, 1.5 Hz, 1H), 7.26-7.19 (m, 2H), 7.14-7.06 (m, 2H), 6.90 (t, J=7.4 Hz, 1H), 5.30 (s, 2H), 4.23 (q, J=5.9 Hz, 2H), 3.59 (s, 2H); MS (ES+): 389.3 (M+1); (ES−): 387.3 (M−1); 423.3 (M+Cl).

Scheme-111

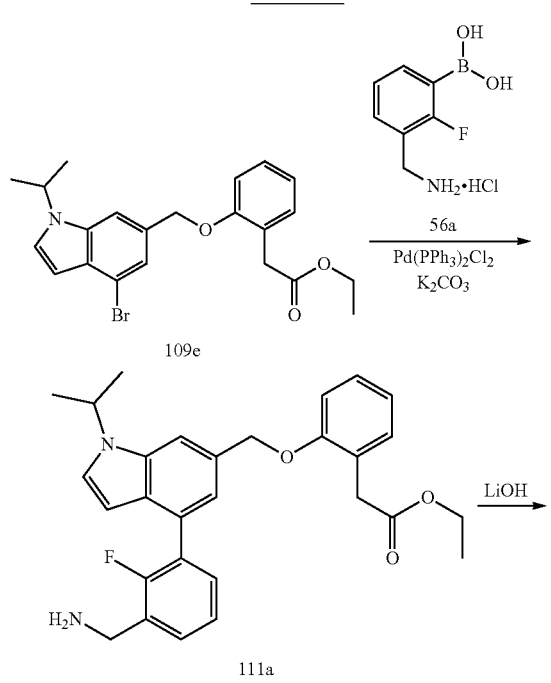

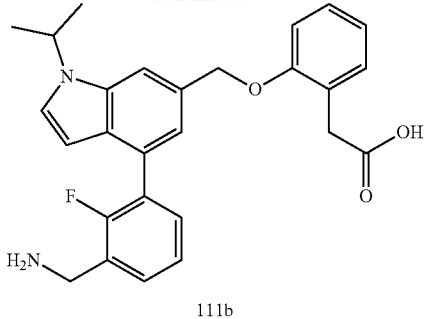 [SMILES: Cn1ccc2c(-c3cccc(CN)c3)cc(COc3ccccc3CC(=O)O)cc21]

Preparation of 2-(2-((4-(3-(aminomethyl)-2-fluorophenyl)-1-isopropyl-1H-indol-6-yl)methoxy)phenyl)acetic Acid (111b)

Step-1: Preparation of Ethyl 2-(2-((4-(3-(aminomethyl)-2-fluorophenyl)-1-isopropyl-1H-indol-6-yl)methoxy)phenyl)acetate (111a)

Compound 111a was prepared according to the procedure reported in step-3 of Scheme-1 from ethyl 2-(2-((4-bromo-1-isopropyl-1H-indol-6-yl)methoxy)phenyl)acetate (109e) (0.4 g, 0.93 mmol) in dioxane (15 mL) using 3-(aminomethyl)-2-fluorophenylboronic acid hydrochloride (56a) (0.29 g, 1.39 mmol), $K_2CO_3$ (0.39 g, 2.79 mmol) in water (2 mL) and bis(triphenylphosphine)Palladium(II) chloride (0.10 g, 0.14 mmol) under an Ar atmosphere and heating at 100° C. for 2 h in an oil bath. This gave after workup, purification by flash column chromatography [silica (12 g), eluting with MeOH in DCM from 0-20%] followed by purification by reverse phase column [C18 (50 g), eluting with ACN in water (containing 0.1% HCl) from 0-100%] ethyl 2-(2-((4-(3-(aminomethyl)-2-fluorophenyl)-1-isopropyl-1H-indol-6-yl)methoxy)phenyl)acetate (111a) (0.31 g, 70% yield) HCl salt as a white solid; $^1$H NMR (300 MHz, DMSO-$d_6$) δ 8.44 (s, 4H), 7.68 (s, 1H), 7.62-7.55 (m, 3H), 7.39 (t, J=7.6 Hz, 1H), 7.29-7.17 (m, 2H), 7.16-7.10 (m, 2H), 6.90 (td, J=7.4, 1.1 Hz, 1H), 6.38 (t, J=3.0 Hz, 1H), 5.24 (s, 2H), 4.81 (m, 1H), 4.16 (s, 2H), 3.91 (q, J=7.1 Hz, 2H), 3.62 (s, 2H), 1.49 (d, J=6.6 Hz, 6H), 0.98 (t, J=7.1 Hz, 3H); $^{19}$F NMR (282 MHz, DMSO-$d_6$) δ−118.90; MS (ES+): 475.4 (M+1); MS (ES−): 509.5 (M+Cl). HPLC purity: 91.15%.

Step-2: Preparation of 2-(2-((4-(3-(aminomethyl)-2-fluorophenyl)-1-isopropyl-1H-indol-6-yl)methoxy)phenyl)acetic Acid (111b)

Compound 111b was prepared according to the procedure reported in step-6 of Scheme-1, from ethyl 2-(2-((4-(3-(aminomethyl)-2-fluorophenyl)-1-isopropyl-1H-indol-6-yl)methoxy)phenyl)acetate (111a) (0.15 g, 0.32 mmol) in THF/MeOH (8 mL) using a solution of lithium hydroxide hydrate (0.066 g, 1.58 mmol) in water (2 mL). This gave after workup and purification by reverse phase column [C18 (50 g), eluting with ACN in water (containing 0.1% HCl) from 0-100%] 2-(2-((4-(3-(aminomethyl)-2-fluorophenyl)-1-isopropyl-1H-indol-6-yl)methoxy)phenyl)acetic acid (111b) (0.03 g, 23% yield) as a white solid; $^1$H NMR (300 MHz, DMSO-$d_6$) δ 12.20 (s, 1H), 8.46 (s, 4H), 7.71 (s, 1H), 7.66-7.56 (m, 3H), 7.38 (t, J=7.6 Hz, 1H), 7.25-7.19 (m, 2H), 7.17-7.08 (m, 2H), 6.90 (t, J=7.4 Hz, 1H), 6.37 (t, J=3.0 Hz, 1H), 5.26 (s, 2H), 4.82 (m, 1H), 4.16 (d, J=5.7 Hz, 2H), 3.59 (s, 2H), 1.49 (d, J=6.6 Hz, 6H); $^{19}$F NMR (282 MHz, DMSO-$d_6$) δ −118.84; MS (ES+): 447.3 (M+1); MS (ES−): 445.4 (M−1), 481.4 (M+Cl). HPLC purity: 90.91%.

yield) as a clear oil; $^1$H NMR (300 MHz, DMSO-$d_6$) δ 7.69 (d, J=1.8 Hz, 1H), 7.55 (d, J=1.8 Hz, 1H), 7.29-7.17 (m, 2H), 7.09 (d, J=8.1 Hz, 1H), 6.96-6.85 (m, 1H), 6.58 (d, J=1.3 Hz,

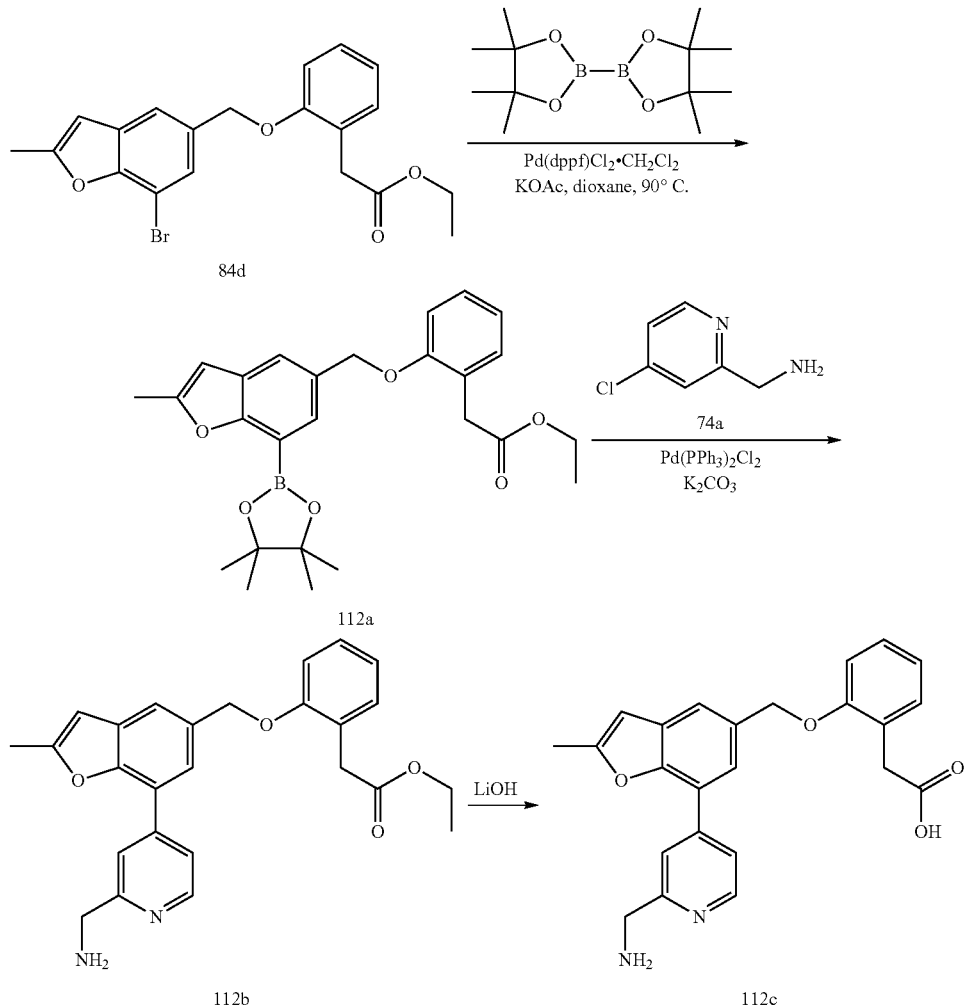

1H), 5.13 (s, 2H), 4.00 (q, J=7.2 Hz, 2H), 3.59 (s, 2H), 2.47 (s, 3H), 1.33 (s, 12H), 1.06 (t, J=7.1 Hz, 3H).

Preparation of 2-(2-((7-(2-(aminomethyl)pyridin-4-yl)-2-methylbenzofuran-5-yl)methoxy)phenyl)acetic Acid (112c)

Step-1: Preparation of Ethyl 2-(2-((2-methyl-7-(4,4,5,5-tetramethyl-1,3,2-dioxaborolan-2-yl)benzofuran-5-yl)methoxy)phenyl)acetate (112a)

Compound 112a was prepared according to the procedure reported in step-1 of Scheme-59 from ethyl 2-(2-((7-bromo-2-methylbenzofuran-5-yl)methoxy)phenyl)acetate (84d) (5 g, 12.40 mmol), using bis(pinacolato)diboron (4.72 g, 18.60 mmol, CAS #: 73183-34-3), potassium acetate (3.65 g, 37.2 mmol) and Pd(dppf)Cl$_2$—CH$_2$Cl$_2$ (1.01 g, 1.240 mmol) in anhydrous dioxane (100 mL) under an Ar atmosphere and heating at 90° C. overnight. This gave after workup and purification by flash column chromatography [silica (40 g), eluting with EtOAc in hexane from 0-40%] ethyl 2-(2-((2-methyl-7-(4,4,5,5-tetramethyl-1,3,2-dioxaborolan-2-yl)benzofuran-5-yl)methoxy)phenyl)acetate (112a) (5.2 g, 93%

Step-2: Preparation of Ethyl 2-(2-((7-(2-(aminomethyl)pyridin-4-yl)-2-methylbenzofuran-5-yl)methoxy)phenyl)acetate (112b)

Compound 112b was prepared according to the procedure reported in step-3 of Scheme-1 from ethyl 2-(2-((2-methyl-7-(4,4,5,5-tetramethyl-1,3,2-dioxaborolan-2-yl)benzofuran-5-yl)methoxy)phenyl)acetate (112a) (1.5 g, 3.33 mmol) in dioxane (30 mL) using (4-chloropyridin-2-yl)methanamine (74a) (0.71 g, 5.00 mmol), bis(triphenylphosphine)palladium(II) chloride (0.35 g, 0.500 mmol) and a solution of K$_2$CO$_3$ (1.38 g, 9.99 mmol) in water (5 mL) under an Ar atmosphere and heating at 100° C. for 2 h on oil bath. This gave after workup, purification by flash column chromatography [silica (40 g), eluting with DMA80 in DCM from 0-70%] followed by purification by reverse phase column [C18 (50 g), eluting with ACN in water (containing 0.1% HCl) from 0-100%]

ethyl 2-(2-((7-(2-(aminomethyl)pyridin-4-yl)-2-methylbenzofuran-5-yl)methoxy)phenyl)acetate (112b) (616 mg, 43% yield) as a white solid; ¹H NMR (300 MHz, DMSO-d₆) δ 8.77 (d, J=5.2 Hz, 1H), 8.59 (s, 3H, D₂O exchangeable), 8.09-8.03 (m, 1H), 7.96 (dd, J=5.3, 1.7 Hz, 1H), 7.72-7.65 (m, 2H), 7.30-7.19 (m, 2H), 7.14-7.08 (m, 1H), 6.92 (td, J=7.4, 1.1 Hz, 1H), 6.73 (d, J=1.3 Hz, 1H), 5.24 (s, 2H), 4.36-4.23 (m, 2H), 3.95 (q, J=7.1 Hz, 2H), 3.64 (s, 2H), 2.52 (s, 3H), 1.00 (t, J=7.1 Hz, 3H); MS (ES+): 431.3 (M+1); (ES-): 465.4 (M+Cl)

Step-3: Preparation of 2-(2-((7-(2-(aminomethyl)pyridin-4-yl)-2-methylbenzofuran-5-yl)methoxy)phenyl)acetic Acid (112c)

Compound 112c was prepared according to the procedure reported in step-6 of Scheme-1, from ethyl 2-(2-((7-(2-(aminomethyl)pyridin-4-yl)-2-methylbenzofuran-5-yl)methoxy)phenyl)acetate (112b) (332 mg, 0.77 mmol) in MeOH/THF (10 mL) using a solution of lithium hydroxide monohydrate (65 mg, 1.54 mmol) in water (2 mL). This gave after workup and purification by reverse phase column [C18 (50 g), eluting with ACN in water (containing 0.1% HCl) from 0-100%] 2-(2-((7-(2-(aminomethyl)pyridin-4-yl)-2-methylbenzofuran-5-yl)methoxy)phenyl)acetic acid (112c) (278 mg, 90% yield) HCl salt as a white solid; ¹H NMR (300 MHz, DMSO-d₆) δ 8.73 (d, J=5.2 Hz, 1H), 8.13 (s, 1H), 8.01 (dd, J=5.4, 1.6 Hz, 1H), 7.78 (d, J=1.6 Hz, 1H), 7.71 (d, J=1.5 Hz, 1H), 7.26-7.16 (m, 2H), 7.04 (d, J=8.4 Hz, 1H), 6.88 (t, J=7.4 Hz, 1H), 6.72 (s, 1H), 5.25 (s, 2H), 4.25 (s, 2H), 3.54 (s, 2H), 2.52 (s, 3H); MS (ES+): 403.3 (M+1); (ES-): 401.3 (M-1), 437.3 (M+Cl).

Scheme-113

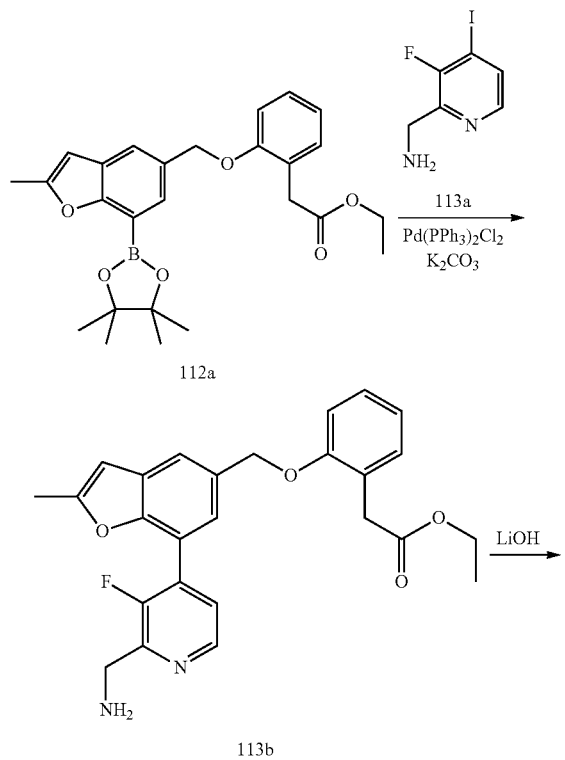

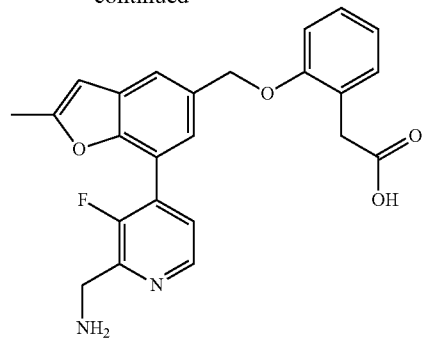

Preparation of 2-(2-((7-(2-(aminomethyl)-3-fluoropyridin-4-yl)-2-methylbenzofuran-5-yl)methoxy)phenyl)acetic Acid (113c)

Step-1: Preparation of Ethyl 2-(2-((7-(2-(aminomethyl)-3-fluoropyridin-4-yl)-2-methylbenzofuran-5-yl)methoxy)phenyl)acetate (113b)

Compound 113b was prepared according to the procedure reported in step-3 of Scheme-1 from ethyl 2-(2-((2-methyl-7-(4,4,5,5-tetramethyl-1,3,2-dioxaborolan-2-yl)benzofuran-5-yl)methoxy)phenyl)acetate (112a) (500 mg, 1.11 mmol) in dioxane (8 mL) using (3-fluoro-4-iodopyridin-2-yl)methanamine (113a) (200 mg, 0.79 mmol; CAS #1805589-86-9), bis(triphenylphosphine)palladium(II) chloride (83 mg, 0.12 mmol) and a solution of K₂CO₃ (329 mg, 2.38 mmol) in water (2 mL) under an Ar atmosphere and heating at 100° C. for 1 h on oil bath. This gave after workup, purification by flash column chromatography [silica (40 g), eluting with DMA80 in DCM from 0-70%] followed by purification by reverse phase column [C18 (50 g), eluting with ACN in water (containing 0.1% HCl) from 0-100%] ethyl 2-(2-((7-(2-(aminomethyl)-3-fluoropyridin-4-yl)-2-methylbenzofuran-5-yl)methoxy)phenyl)acetate (113b) (170 mg, 48% yield) HCl salt as a white solid. ¹H NMR (300 MHz, DMSO-d₆) δ 8.63 (d, J=5.0 Hz, 1H), 8.58 (s, 3H, D₂O exchangeable), 7.78 (t, J=5.3 Hz, 1H), 7.74 (d, J=1.6 Hz, 1H), 7.44 (s, 1H), 7.29-7.18 (m, 2H), 7.11 (d, J=8.0 Hz, 1H), 6.91 (td, J=7.3, 1.0 Hz, 1H), 6.73 (d, J=1.3 Hz, 1H), 5.22 (s, 2H), 4.37 (s, 2H), 3.93 (q, J=7.1 Hz, 2H), 3.62 (s, 2H), 2.45 (s, 4H), 1.00 (t, J=7.1 Hz, 3H); ¹⁹F NMR (282 MHz, DMSO-d₆) δ-128.74; MS (ES+): 449.3 (M+1); (ES-): 483.3 (M+Cl).

Step-2: Preparation of 2-(2-((7-(2-(aminomethyl)-3-fluoropyridin-4-yl)-2-methylbenzofuran-5-yl)methoxy)phenyl)acetic Acid (113c)

Compound 113c was prepared according to the procedure reported in step-6 of Scheme-1, from ethyl 2-(2-((7-(2-(aminomethyl)-3-fluoropyridin-4-yl)-2-methylbenzofuran-5-yl) methoxy)phenyl)acetate (113b) (112 mg, 0.25 mmol) in MeOH/THF (10 mL) using a solution of lithium hydroxide monohydrate (21 mg, 0.50 mmol) in water (2 mL). This gave after workup and purification by reverse phase column [C18 (50 g), eluting with ACN in water (containing 0.1% HCl) from 0-100%] 2-(2-((7-(2-(aminomethyl)-3-fluoropyridin-4-yl)-2-methylbenzofuran-5-yl)methoxy)phenyl) acetic acid (113c) (67 mg, 64% yield) HCl salt as a white solid; $^1$H NMR (300 MHz, DMSO-$d_6$) δ 12.28 (s, 1H, D$_2$O exchangeable), 8.69-8.54 (m, 4H, partially D$_2$O exchangeable), 7.82-7.74 (m, 2H), 7.49 (s, 1H), 7.28-7.19 (m, 2H), 7.09 (d, J=8.1 Hz, 1H), 6.91 (td, J=7.4, 1.1 Hz, 1H), 6.72 (d, J=1.3 Hz, 1H), 5.25 (s, 2H), 4.45-4.28 (m, 2H), 3.58 (s, 2H), 2.45 (s, 4H); $^{19}$F NMR (282 MHz, DMSO-$d_6$) δ−128.55; MS (ES+): 421.3 (M+1); (ES−): 455.3 (M+Cl).

Scheme-114

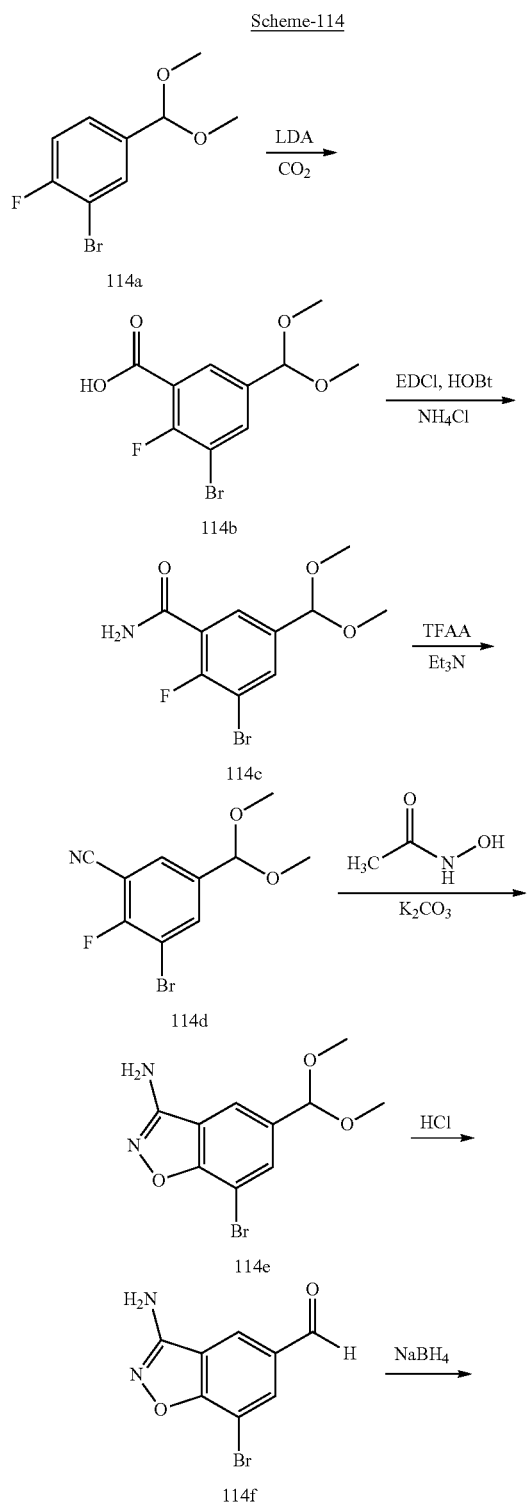

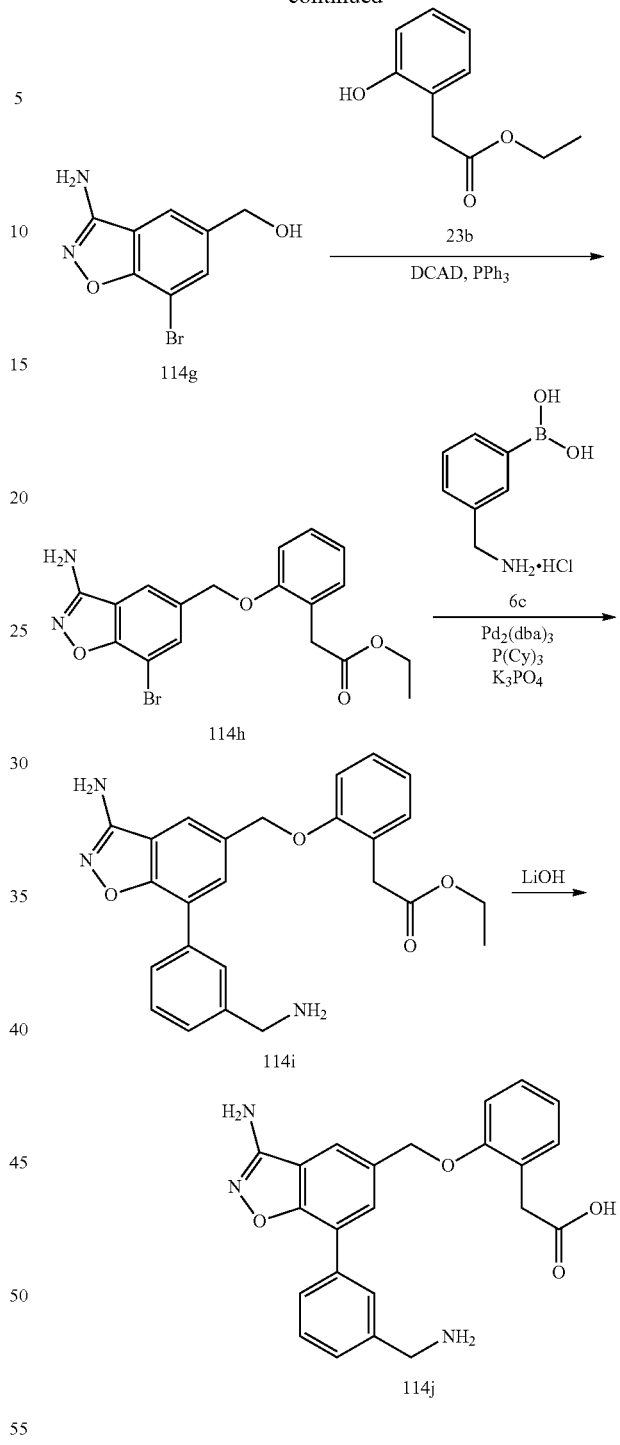

Preparation of 2-(2-((3-amino-7-(3-(aminomethyl)phenyl)benzo[d]isoxazol-5-yl)methoxy)phenyl)acetic Acid (114j)

Step-1: Preparation of 3-bromo-5-(dimethoxymethyl)-2-fluorobenzoic Acid (114b)

To a solution of lithium diisopropylamide (7.23 mL, 14.45 mmol) in THF (30 mL) cooled to −78° C. was added a solution of 2-bromo-4-(dimethoxymethyl)-1-fluorobenzene (114a) (3 g, 12.04 mmol; CAS #81358-65-8) in THF (10 mL) and stirred at −78° C. for 25 min. The reaction mixture was quenched with dry ice and stirred at −78° C. for 1 h and allowed to warm to RT over a period of 0.5 h. The reaction mixture was diluted with water (50 mL), ethyl acetate (100 mL) and acidified with 4 N HCl to pH 4. The aqueous layer was separated and extracted with ethyl acetate (75 mL). The organic layers were combined washed with brine (75 mL), dried, filtered and concentrated in vacuum to afford 3-bromo-5-(dimethoxymethyl)-2-fluorobenzoic acid (114b) (2.56 g, 73% yield) as a yellow solid which was used as such for next step; MS (ES−): 291.1 & 293.1 (M−1).

Step-2: Preparation of 3-bromo-5-(dimethoxymethyl)-2-fluorobenzamide (114c)

To a suspension of 3-bromo-5-(dimethoxymethyl)-2-fluorobenzoic acid (114b) (2.4 g, 8.19 mmol), ammonium chloride (1.314 g, 24.57 mmol), and 1H-benzo[d][1,2,3]triazol-1-ol (0.111 g, 0.819 mmol) in DMF (35 mL) was added N1-((ethylimino)methylene)-N3,N3-dimethylpropane-1,3-diamine hydrochloride (2.355 g, 12.28 mmol), N-ethyl-N-isopropylpropan-2-amine (2.85 mL, 16.38 mmol) and stirred at RT for 15 h. The reaction mixture was diluted with ethyl acetate (150 mL), washed with water (2×75 mL), brine (75 mL), dried, filtered and concentrated in vacuum. The residue obtained purified by flash column chromatography [silica gel eluting with hexanes/ethyl acetate (1:0 to 1:1)] to afford 3-bromo-5-(dimethoxymethyl)-2-fluorobenzamide (114c) (435 mg, 18% yield) as a white solid; $^1$H NMR (300 MHz, DMSO-$d_6$) δ 7.89 (s, 1H), 7.78-7.70 (m, 2H), 7.60 (dd, J=6.2, 2.1 Hz, 1H), 5.42 (s, 1H), 3.27 (d, J=0.7 Hz, 6H); $^{19}$F NMR (282 MHz, DMSO-$d_6$) δ−108.83; MS (ES−): 326.1 & 328.1 (M+Cl).

Step-3: Preparation of 3-bromo-5-(dimethoxymethyl)-2-fluorobenzonitrile (114d)

To a solution of 3-bromo-5-(dimethoxymethyl)-2-fluorobenzamide (114c) (418 mg, 1.431 mmol) and triethylamine (0.598 mL, 4.29 mmol) in DCM (20 mL) cooled to 0° C. was added dropwise 2,2,2-trifluoroacetic anhydride (0.298 mL, 2.147 mmol) and stirred at 0° C. for 2 h. The reaction mixture was diluted with dichloromethane (75 mL), washed with 1 N NaHCO$_3$ (50 mL), brine (50 mL), dried, filtered and concentrated in vacuum. The residue obtained purified by flash column chromatography [silica gel eluting with hexanes/ethyl acetate (1:0 to 3:1)] to afford 3-bromo-5-(dimethoxymethyl)-2-fluorobenzonitrile (114d) (366 mg, 93%) as a white solid; $^1$H NMR (300 MHz, DMSO-$d_6$) δ 8.01 (dd, J=6.7, 2.0 Hz, 1H), 7.90 (dd, J=5.8, 2.0 Hz, 1H), 5.43 (s, 1H), 3.28 (s, 6H); $^{19}$F NMR (282 MHz, DMSO-$d_6$) δ−103.08.

Step-4: Preparation of 7-bromo-5-(dimethoxymethyl)benzo[d]isoxazol-3-amine (114e)

To a solution of 3-bromo-5-(dimethoxymethyl)-2-fluorobenzonitrile (114d) (350 mg, 1.277 mmol) in DMF (12 mL) was added N-hydroxyacetamide (288 mg, 3.83 mmol), potassium carbonate (529 mg, 3.83 mmol) and heated at 90° C. for 5 h. The reaction mixture was cooled to RT, diluted with ethyl acetate (100 mL) and washed with water (50 mL). The aqueous phase was extracted with ethyl acetate (50 mL). The organic layers were combined washed with brine, dried, filtered and concentrated in vacuum. The residue obtained purified by flash column chromatography [silica gel eluting with hexanes/ethyl acetate (1:0 to 2:1)] to afford 7-bromo-5-(dimethoxymethyl)benzo[d]isoxazol-3-amine (114e) (162 mg, 44%) as an off-white solid. $^1$H NMR (300 MHz, DMSO-$d_6$) δ 7.95 (d, J=1.3 Hz, 1H), 7.72 (d, J=1.3 Hz, 1H), 6.65 (s, 2H), 5.51 (s, 1H), 3.26 (s, 6H); MS (ES−): 321.1 (M+Cl).

Step-5: Preparation of 3-amino-7-bromobenzo[d]isoxazole-5-carbaldehyde (114f)

To a solution of 7-bromo-5-(dimethoxymethyl)benzo[d]isoxazol-3-amine (114e) (155 mg, 0.540 mmol) in THF (4 mL) was added conc. hydrogen chloride (0.112 mL, 1.350 mmol) and stirred at RT for 6 h. Additional conc. HCl (0.25 mL) was added and the reaction was continued stirring at RT for 24 h. The reaction mixture was diluted with ethyl acetate (100 mL) washed with 1 N NaHCO$_3$ (40 mL), brine (40 mL), dried, filtered and concentrated in vacuum to afford 3-amino-7-bromobenzo[d]isoxazole-5-carbaldehyde (114f) (137 mg) as an off-white solid. $^1$H NMR (300 MHz, DMSO-$d_6$) δ 9.99 (s, 1H), 8.49 (d, J=1.3 Hz, 1H), 8.32 (d, J=1.3 Hz, 1H), 6.90 (s, 2H); MS (ES−): 239.1 (M−1).

Step-6: Preparation of (3-amino-7-bromobenzo[d]isoxazol-5-yl)methanol (114g)

To a solution of 3-amino-7-bromobenzo[d]isoxazole-5-carbaldehyde (114f) (135 mg, 0.560 mmol) in THF (15 mL) cooled to 0° C. was added sodium borohydride (42.4 mg, 1.120 mmol) and stirred at RT for 21 h. The reaction mixture was diluted with ethyl acetate (100 mL), washed with water (40 mL), brine (40 mL), dried, filtered and concentrated in vacuum. The residue obtained purified by flash column chromatography [silica gel eluting with hexanes/ethyl acetate (1:0 to 0:1)] to afford (3-amino-7-bromobenzo[d]isoxazol-5-yl)methanol (114g) (101 mg, 78% yield) as a white solid; $^1$H NMR (300 MHz, DMSO-$d_6$) δ 7.81 (s, 1H), 7.69 (s, 1H), 6.57 (s, 2H), 5.42 (t, J=5.6 Hz, 1H), 4.57 (d, J=5.4 Hz, 2H); MS (ES−): 241.2 (M−1).

Step-7: Preparation of Ethyl 2-(2-((3-amino-7-bromobenzo[d]isoxazol-5-yl)methoxy)phenyl)acetate (114h)

Compound 114h was prepared according to the procedure reported in step-2 of Scheme-23 (3-amino-7-bromobenzo[d]isoxazol-5-yl)methanol (114g) (95 mg, 0.39 mmol) in DCM (5 mL) using triphenylphosphine (154 mg, 0.59 mmol), ethyl 2-(2-hydroxyphenyl) acetate (23b) (176 mg, 0.98 mmol) and di-(4-chlorobenzyl)azodicarboxylate (DCAD, 215 mg, 0.59 mmol). This gave after workup and purification by flash column chromatography [silica (12 g), eluting with hexanes/ethyl acetate (1:0 to 2:1)] ethyl 2-(2-((3-amino-7-bromobenzo[d]isoxazol-5-yl)methoxy)phenyl)acetate (114h) (189 mg) as a white solid; MS (ES−): 439.2 (M+Cl).

Step-8: Preparation of Ethyl 2-(2-((3-amino-7-(3-(aminomethyl)phenyl)benzo[d]isoxazol-5-yl)methoxy)phenyl)acetate (114i)

Compound 114i was prepared according to the procedure reported in step-3 of Scheme-1 from ethyl 2-(2-((3-amino-7-bromobenzo[d]isoxazol-5-yl)methoxy)phenyl)acetate (114h) (100 mg, 0.25 mmol) in dioxane (3 mL) using 3-(aminomethyl)phenylboronic acid hydrochloride (6c) (69 mg, 0.37 mmol), tricyclohexylphosphine (41.5 mg, 0.148 mmol), a solution of tripotassium phosphate (0.14 mL, 0.42 mmol, 3 M), water (0.1 mL) and Pd$_2$(dba)$_3$ (68 mg, 0.074 mmol) and heating under an Ar atmosphere in a microwave at 125° C. for 2 h. This gave after workup, purification by flash column chromatography [silica (12 g), eluting with dichloromethane/methanol (1:0 to 9:1)] ethyl 2-(2-((3-amino-7-(3-(aminomethyl)phenyl)benzo[d]isoxazol-5-yl)methoxy)phenyl)acetate (114i) (5 mg, 5% yield) as a white solid; MS (ES+): 432.3 (M+1) & 454.3 (M+Na).

Step-9: Preparation of 2-(2-((3-amino-7-(3-(aminomethyl)phenyl)benzo[d]isoxazol-5-yl)methoxy)phenyl)acetic Acid (114j)

Compound 114j was prepared according to the procedure reported in step-6 of Scheme-1, from ethyl 2-(2-((3-amino-7-(3-(aminomethyl)phenyl)benzo[d]isoxazol-5-yl)methoxy)phenyl)acetate (114i) (5 mg, 0.012 mmol) in THF (3 mL) and MeOH (3 mL) using a solution of lithium hydroxide hydrate (5 mg, 0.12 mmol) in water (3 mL). This gave after workup and purification by flash column chromatography [silica gel, eluting with dichloromethane/DMA 80 (1:0 to 1:2)]2-(2-((3-amino-7-(3-(aminomethyl)phenyl)benzo[d]isoxazol-5-yl)methoxy)phenyl)acetic acid (114j) (3 mg, 64%) as a white solid; $^1$H NMR (300 MHz, Methanol-d$_4$) δ 8.26 (s, 1H), 8.19 (s, 1H), 8.14 (d, J=8.0 Hz, 1H), 7.76 (s, 1H), 7.51 (t, J=7.7 Hz, 1H), 7.39 (d, J=7.6 Hz, 1H), 7.24-7.14 (m, 2H), 7.00 (d, J=8.4 Hz, 1H), 6.90 (t, J=7.3 Hz, 1H), 5.27 (s, 2H), 4.21 (s, 2H), 3.61 (s, 2H); MS (ES+): 404.2 (M+1); HPLC purity: 91.21%.

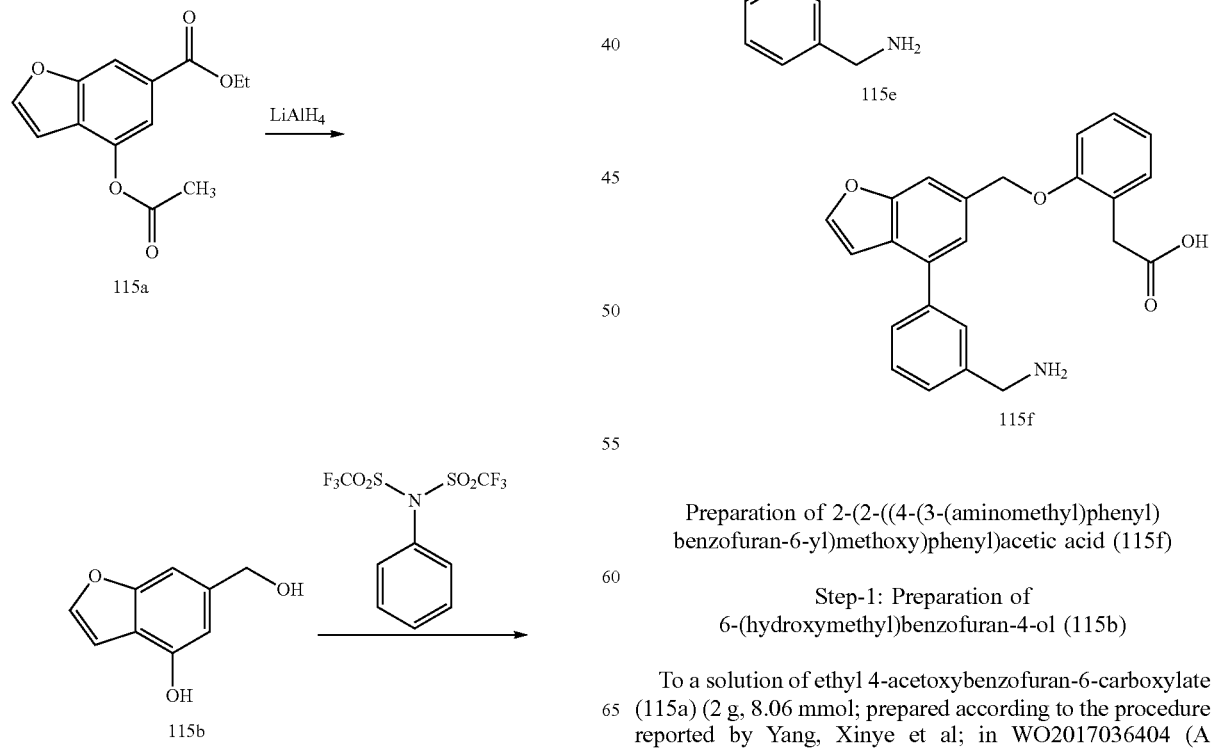

Preparation of 2-(2-((4-(3-(aminomethyl)phenyl)benzofuran-6-yl)methoxy)phenyl)acetic acid (115f)

Step-1: Preparation of 6-(hydroxymethyl)benzofuran-4-ol (115b)

To a solution of ethyl 4-acetoxybenzofuran-6-carboxylate (115a) (2 g, 8.06 mmol; prepared according to the procedure reported by Yang, Xinye et al; in WO2017036404 (A1)-2017-03-09) in THF (30 mL) cooled to 0° C. was added lithium aluminum hydride (0.612 g, 16.11 mmol) and stirred at RT for 24 h. The reaction mixture was quenched carefully with 20% aqueous Na$_2$SO$_4$ (20 mL), water (100 mL) and extracted with ethyl acetate (150 and 100 mL). The combined organic layer was washed with water (100 mL), brine (100 mL), dried, filtered and concentrated in vacuum. The residue obtained purified by flash column chromatography [silica gel eluting with hexanes/ethyl acetate (1:0 to 1:1)] to afford 6-(hydroxymethyl)benzofuran-4-ol (115b) (883 mg, 67% yield) as a white solid; $^1$H NMR (300 MHz, DMSO-d$_6$) δ 9.85 (s, 1H), 7.76 (d, J=2.2 Hz, 1H), 6.96 (p, J=0.9 Hz, 1H), 6.89 (dd, J=2.2, 1.0 Hz, 1H), 6.60-6.58 (m, 1H), 5.17 (bs, 1H), 4.49 (bs, 2H); MS (ES−): 163.1 (M−1).

Step-2: Preparation of 6-(hydroxymethyl)benzofuran-4-yl trifluoromethanesulfonate (115c)

To a solution of 6-(hydroxymethyl)benzofuran-4-ol (115b) (860 mg, 5.24 mmol) in DMF (20 mL) was added 1,1,1-trifluoro-N-phenyl-N-(trifluoromethyl sulfonyl)methanesulfonamide (1910 mg, 5.24 mmol), triethylamine (1.460 mL, 10.48 mmol) and stirred at RT for 14 h. The reaction mixture was diluted with ethyl acetate (150 mL), washed with water (2×60 mL), brine (60 mL), dried, filtered and concentrated in vacuum. The residue obtained purified by flash column chromatography [silica gel eluting with hexanes/ethyl acetate (1:0 to 3:1)] to afford 6-(hydroxymethyl)benzofuran-4-yl trifluoromethanesulfonate (115c) (1.239 g, 80% yield) as a light brown oil. $^1$H NMR (300 MHz, DMSO-d$_6$) δ 8.16 (d, J=2.3 Hz, 1H), 7.71 (p, J=0.9 Hz, 1H), 7.36 (bs, 1H), 7.02 (dd, J=2.3, 0.9 Hz, 1H), 5.58-5.47 (m, 1H), 4.68-4.62 (m, 2H); $^{19}$F NMR (282 MHz, DMSO-d$_6$) δ−72.88; MS (ES−): 331.1 (M+Cl).

Step-3: Preparation of Ethyl 2-(2-((4-(((trifluoromethyl)sulfonyl)oxy)benzofuran-6-yl)methoxy)phenyl)acetate (115d)

Compound 115d was prepared according to the procedure reported in step-2 of Scheme-23 from 6-(hydroxymethyl)benzofuran-4-yl trifluoromethanesulfonate (115c) (1.18 g, 3.98 mmol) in DCM (30 mL) using triphenylphosphine (1.567 g, 5.98 mmol), ethyl 2-(2-hydroxyphenyl) acetate (23b) (1.077 g, 5.98 mmol) and di-(4-chlorobenzyl)azodicarboxylate (DCAD, 2.194 g, 5.98 mmol). This gave after workup and purification by flash column chromatography [silica (12 g), eluting with hexanes/ethyl acetate (1:0 to 5:1)] ethyl 2-(2-((4-(((trifluoromethyl)sulfonyl)oxy)benzofuran-6-yl)methoxy)phenyl)acetate (115d) (1.624 g, 89% yield) as a light brown gum; $^1$H NMR (300 MHz, DMSO-d$_6$) δ 8.23 (d, J=2.3 Hz, 1H), 7.86 (s, 1H), 7.50 (s, 1H), 7.24 (d, J=7.6 Hz, 2H), 7.10-7.01 (m, 2H), 6.96-6.89 (m, 1H), 5.29 (s, 2H), 4.00 (q, J=7.1 Hz, 2H), 3.66 (s, 2H), 1.07 (t, J=7.1 Hz, 3H); $^{19}$F NMR (282 MHz, DMSO-d$_6$) δ−72.74; (ES+): 481.2 (M+Na).

Step-4: Preparation of Ethyl 2-(2-((4-(3-(aminomethyl)phenyl)benzofuran-6-yl)methoxy)phenyl)acetate (115e)

Compound 115e was prepared according to the procedure reported in step-3 of Scheme-1 from ethyl 2-(2-((4-(((trifluoromethyl)sulfonyl)oxy)benzofuran-6-yl)methoxy)phenyl)acetate (115d) (500 mg, 1.091 mmol) in dioxane (10 mL) using 3-(aminomethyl)phenylboronic acid hydrochloride (6c) (307 mg, 1.636 mmol), a solution of sodium bicarbonate (275 mg, 3.27 mmol) in water (1 mL), Pd(PPh$_3$)$_2$Cl$_2$ (230 mg, 0.327 mmol) and heating under an Ar atmosphere at 100° C. for 3 h. This gave after workup, purification by flash column chromatography [silica (12 g), eluting with dichloromethane/methanol (1:0 to 9:1)] ethyl 2-(2-((4-(3-(aminomethyl)phenyl)benzofuran-6-yl)methoxy)phenyl)acetate (115e) (295 mg, 65% yield) as a brown gum; $^1$H NMR (300 MHz, DMSO-d$_6$) δ 8.10 (d, J=2.2 Hz, 1H), 7.66 (s, 2H), 7.56-7.33 (m, 4H), 7.30-7.18 (m, 2H), 7.13-7.06 (m, 2H), 6.91 (t, J=7.4 Hz, 1H), 5.28 (s, 2H), 3.95 (q, J=7.1 Hz, 2H), 3.84 (s, 2H), 3.65 (s, 2H), 1.02 (t, J=7.1 Hz, 3H); MS (ES+): 416.3 (M+1).

Step-5: Preparation of 2-(2-((4-(3-(aminomethyl)phenyl)benzofuran-6-yl)methoxy)phenyl)acetic Acid (115f)

Compound 115f was prepared according to the procedure reported in step-6 of Scheme-1, from ethyl 2-(2-((4-(3-(aminomethyl)phenyl)benzofuran-6-yl)methoxy)phenyl)acetate (115e) (200 mg, 0.48 mmol) in THF (10 mL) and MeOH (10 mL) using a solution of lithium hydroxide hydrate (124 mg, 2.89 mmol) in water (10 mL). This gave after workup and purification by flash column chromatography [silica gel, eluting with dichloromethane/methanol (1:0 to 9:1)] 2-(2-((4-(3-(aminomethyl)phenyl)benzofuran-6-yl)methoxy)phenyl)acetic acid (115f) (125 mg, yield: 67%) as a white solid; $^1$H NMR (300 MHz, DMSO-d$_6$) δ 8.17 (s, 1H), 8.09 (d, J=2.2 Hz, 1H), 7.75-7.67 (m, 3H), 7.48 (t, J=7.6 Hz, 1H), 7.36 (d, J=7.6 Hz, 1H), 7.15-7.14 (m, 1H), 7.12-7.05 (m, 2H), 6.96 (d, J=8.0 Hz, 1H), 6.83-6.77 (m, 1H), 5.28 (s, 2H), 4.00 (s, 2H), 3.39 (s, 2H); MS (ES+): 388.3 (M+1), 410.3 (M+Na); MS (ES−): 386.3 (M−1), 422.2 (M+Cl); HPLC purity: 99.26%.

Scheme-116

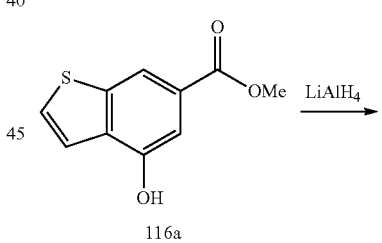

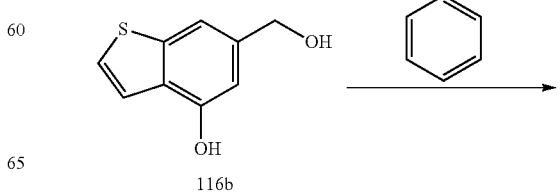

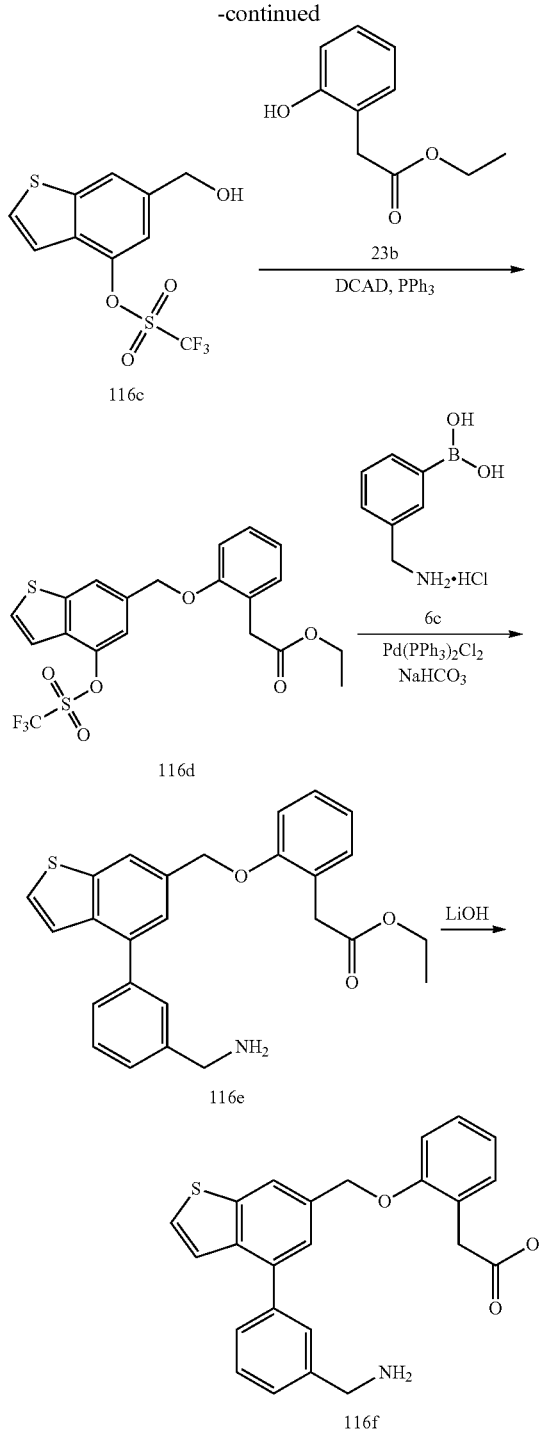

mmol; CAS #314725-14-9) in THF (15 using lithium aluminum hydride (260 mg, 6.84 mmol). This gave after workup and purification by flash column chromatography [silica gel, eluting with hexanes/ethyl acetate (1:0 to 1:1)] 6-(hydroxymethyl)benzo[b]thiophen-4-ol (116b) (545 mg, 66% yield) as a white solid; $^1$H NMR (300 MHz, DMSO-$d_6$) δ 9.92 (s, 1H), 7.50 (d, J=5.5 Hz, 1H), 7.40 (dd, J=5.5, 0.8 Hz, 1H), 7.33-7.30 (m, 1H), 6.72-6.70 (m, 1H), 5.20 (t, J=5.8 Hz, 1H), 4.53-4.49 (m, 2H); MS (ES+): 181.05 (M+1), 203.05 (M+Na); MS (ES−): 179.10 (M−1).

Step-2: Preparation of 6-(hydroxymethyl)benzo[b]thiophen-4-yl trifluoromethanesulfonate (116c)

Compound 116c was prepared according to the procedure reported in step-2 of Scheme-116 from 6-(hydroxymethyl)benzo[b]thiophen-4-ol (116b) (535 mg, 2.97 mmol) in DMF (12 mL) using 1,1,1-trifluoro-N-phenyl-N-(trifluoromethyl sulfonyl)methanesulfonamide (1082 mg, 2.97 mmol) and triethylamine (0.828 mL, 5.94 mmol). This gave after workup and purification by flash column chromatography [silica gel, eluting with hexanes/ethyl acetate (1:0 to 3:1)] 6-(hydroxymethyl)benzo[b]thiophen-4-yl trifluoromethanesulfonate (116c) (720 mg, 78% yield) as a white solid; $^1$H NMR (300 MHz, DMSO-$d_6$) δ 8.09 (m, 1H), 7.99 (d, J=5.6 Hz, 1H), 7.45 (d, J=1.1 Hz, 1H), 7.41 (dd, J=5.6, 0.8 Hz, 1H), 5.54 (t, J=5.8 Hz, 1H), 4.67 (d, J=5.7 Hz, 2H); $^{19}$F NMR (282 MHz, DMSO-$d_6$) δ−73.06; MS (ES+): MS (ES−): 311.10 (M−1).

Step-3: Preparation of Ethyl 2-(2-((4-(((trifluoromethyl)sulfonyl)oxy)benzo[b]thiophen-6-yl)methoxy)phenyl)acetate (116d)

Compound 116d was prepared according to the procedure reported in step-2 of Scheme-23 from 6-(hydroxymethyl)benzo[b]thiophen-4-yl trifluoromethanesulfonate (116c) (110 mg, 0.352 mmol) in DCM (4 mL) using triphenylphosphine (139 mg, 0.53 mmol), ethyl 2-(2-hydroxyphenyl)acetate (23b) (95 mg, 0.53 mmol) and di-(4-chlorobenzyl)azodicarboxylate (DCAD, 194 mg, 0.53 mmol). This gave after workup and purification by flash column chromatography [silica (12 g), eluting with hexanes/ethyl acetate (1:0 to 1:1)] ethyl 2-(2-((4-(((trifluoromethyl)sulfonyl)oxy)benzo[b]thiophen-6-yl)methoxy)phenyl)acetate (116d) (115 mg, 69% yield) as a colorless oil. $^1$H NMR (300 MHz, DMSO-$d_6$) δ 8.23 (s, 1H), 8.06 (d, J=5.6 Hz, 1H), 7.58 (s, 1H), 7.46 (d, J=5.6 Hz, 1H), 7.31-7.19 (m, 2H), 7.08 (d, J=8.1 Hz, 1H), 6.93 (t, J=7.4 Hz, 1H), 5.30 (s, 2H), 4.00 (q, J=7.1 Hz, 2H), 3.66 (s, 2H), 1.06 (t, J=7.1 Hz, 3H); $^{19}$F NMR (282 MHz, DMSO-$d_6$) δ−72.96; MS (ES+): 497.1 (M+Na); MS (ES−): 473.1 (M−1).

Step-4: Preparation of Ethyl 2-(2-((4-(3-(aminomethyl)phenyl)benzo[b]thiophen-6-yl)methoxy)phenyl)acetate (116e)

Compound 116e was prepared according to the procedure reported in step-3 of Scheme-1 from ethyl 2-(2-((4-(((trifluoromethyl)sulfonyl)oxy)benzo[b]thiophen-6-yl)methoxy)phenyl)acetate (116d) (172 mg, 0.363 mmol) in dioxane (4 mL) using 3-(aminomethyl)phenylboronic acid hydrochloride (6c) (102 mg, 0.544 mmol), a solution of sodium bicarbonate (91 mg, 1.088 mmol) in water (1 mL), Pd(PPh$_3$)$_2$Cl$_2$ (76 mg, 0.109 mmol) and heating under an Ar atmosphere at 95° C. for 3 h. This gave after workup, Preparation of 2-(2-((4-(3-(aminomethyl)phenyl)benzo[b]thiophen-6-yl)methoxy)phenyl)acetic Acid (116f)

Step-1: Preparation of 6-(hydroxymethyl)benzo[b]thiophen-4-ol (116b)

Compound 116b was prepared according to the procedure reported in step-1 of Scheme-115 from methyl 4-hydroxybenzo[b]thiophene-6-carboxylate (116a) (950 mg, 4.56 purification by flash column chromatography [silica (12 g), eluting with dichloromethane/methanol (1:0 to 9:1)] ethyl 2-(2-((4-(3-(aminomethyl)phenyl)benzo[b]thiophen-6-yl)methoxy)phenyl)acetate (116e) (38 mg, 24% yield) as a colorless gum; MS (ES+): 432.2 (M+1).

Step-5: Preparation of 2-(2-((4-(3-(aminomethyl)phenyl)benzo[b]thiophen-6-yl)methoxy)phenyl)acetic Acid (116f)

Compound 116f was prepared according to the procedure reported in step-6 of Scheme-1, from ethyl 2-(2-((4-(3-(aminomethyl)phenyl)benzo[b]thiophen-6-yl)methoxy)phenyl)acetate (116e) (35 mg, 0.081 mmol) in THF (4 mL) and MeOH (4 mL) using a solution of lithium hydroxide hydrate (21 mg, 0.49 mmol) in water (4 mL). This gave after workup 2-(2-((4-(3-(aminomethyl)phenyl)benzo[b]thiophen-6-yl)methoxy)phenyl)acetic acid (116f) (24 mg, 74% yield) as an off-white solid $^1$H NMR (500 MHz, DMSO-$d_6$) δ 8.07 (s, 1H), 7.92 (s, 1H), 7.80 (d, J=5.5 Hz, 1H), 7.67-7.63 (m, 1H), 7.61 (d, J=1.4 Hz, 1H), 7.55-7.48 (m, 2H), 7.42 (d, J=7.6 Hz, 1H), 7.16-7.09 (m, 2H), 6.99 (d, J=8.3 Hz, 1H), 6.83 (t, J=7.3 Hz, 1H), 5.28 (s, 2H), 4.06 (s, 2H), 3.45 (s, 2H); MS (ES+): 404.3 (M+1), 426.3 (M+Na); MS (ES−): 402.3 (M−1); HPLC purity: 90.05%.

Preparation of 2-(2-((4-(3-(aminomethyl)-2-fluorophenyl)benzo[b]thiophen-6-yl)methoxy)phenyl)acetic Acid (117b)

Step-1: Preparation of Ethyl 2-(2-((4-(3-(aminomethyl)-2-fluorophenyl)benzo[b]thiophen-6-yl)methoxy)phenyl)acetate (117a)

Compound 117a was prepared according to the procedure reported in step-3 of Scheme-1 from ethyl 2-(2-((4-(((trifluoromethyl)sulfonyl)oxy)benzo[b]thiophen-6-yl)methoxy)phenyl)acetate (116d) (300 mg, 0.632 mmol) in dioxane (8 mL) using (3-(aminomethyl)-2-fluorophenyl)boronic acid hydrochloride (56a) (195 mg, 0.95 mmol), a solution of sodium bicarbonate (159 mg, 1.9 mmol) in water (0.8 mL), Pd(PPh$_3$)$_2$Cl$_2$ (133 mg, 0.19 mmol) and heating under an nitrogen atmosphere at 100° C. for 3 h. This gave after workup, purification by flash column chromatography [silica (12 g), eluting with dichloromethane/methanol (1:0 to 19:1)] ethyl 2-(2-((4-(3-(aminomethyl)-2-fluorophenyl)benzo[b]thiophen-6-yl)methoxy)phenyl)acetate (117a) (225 mg, 79% yield) as a brown gum; $^1$H NMR (300 MHz, DMSO-$d_6$) δ 8.11-8.08 (m, 1H), 7.80 (d, J=5.6 Hz, 1H), 7.59 (td, J=7.0, 2.5 Hz, 1H), 7.41-7.39 (m, 1H), 7.38-7.19 (m, 4H), 7.18-7.08 (m, 2H), 6.91 (td, J=7.4, 1.1 Hz, 1H), 5.27 (s, 2H), 3.91 (q, J=7.1 Hz, 2H), 3.83 (s, 2H), 3.64 (s, 2H), 1.00 (t, J=7.1 Hz, 3H); $^{19}$F NMR (282 MHz, DMSO-$d_6$) δ−122.29; MS (ES+): 450.20 (M+1).

Step-2: Preparation of 2-(2-((4-(3-(aminomethyl)-2-fluorophenyl)benzo[b]thiophen-6-yl)methoxy)phenyl)acetic Acid (117b)

Compound 117b was prepared according to the procedure reported in step-6 of Scheme-1, from ethyl 2-(2-((4-(3-(aminomethyl)-2-fluorophenyl)benzo[b]thiophen-6-yl)methoxy)phenyl)acetate (117a) (200 mg, 0.445 mmol) in THF (10 mL) and MeOH (10 mL) using a solution of lithium hydroxide hydrate (114 mg, 2.67 mmol) in water (10 mL). This gave after workup and purification by reverse phase column [C18 (50 g), eluting with ACN in water (containing 0.1% HCl) from 0-100%] 2-(2-((4-(3-(aminomethyl)-2-fluorophenyl)benzo[b]thiophen-6-yl)methoxy)phenyl)acetic acid (117b) (91 mg, 43% yield) HCl salt as a white solid; $^1$H NMR (300 MHz, DMSO-$d_6$) δ 8.61 (s, 3H), 8.17 (s, 1H), 7.83 (d, J=5.5 Hz, 1H), 7.69 (td, J=7.3, 1.9 Hz, 1H), 7.56 (td, J=7.4, 1.8 Hz, 1H), 7.47-7.36 (m, 2H), 7.29-7.18 (m, 3H), 7.08 (d, J=8.1 Hz, 1H), 6.91 (t, J=7.3 Hz, 1H), 5.31 (s, 2H), 4.16 (s, 2H), 3.60 (s, 2H); $^{19}$F NMR (282 MHz, DMSO-$d_6$) δ−118.48; MS (ES+): 422.1 (M+1); HPLC purity: 99.60%; Analysis calculated for $C_{24}H_{20}FNO_3S \cdot 1.0\ HCl \cdot 1.0\ H_2O$: C, 60.56; H, 4.87; N, 2.94; Cl, 7.45; Found: C, 60.69; H, 4.66; N, 2.95; Cl, 7.22.

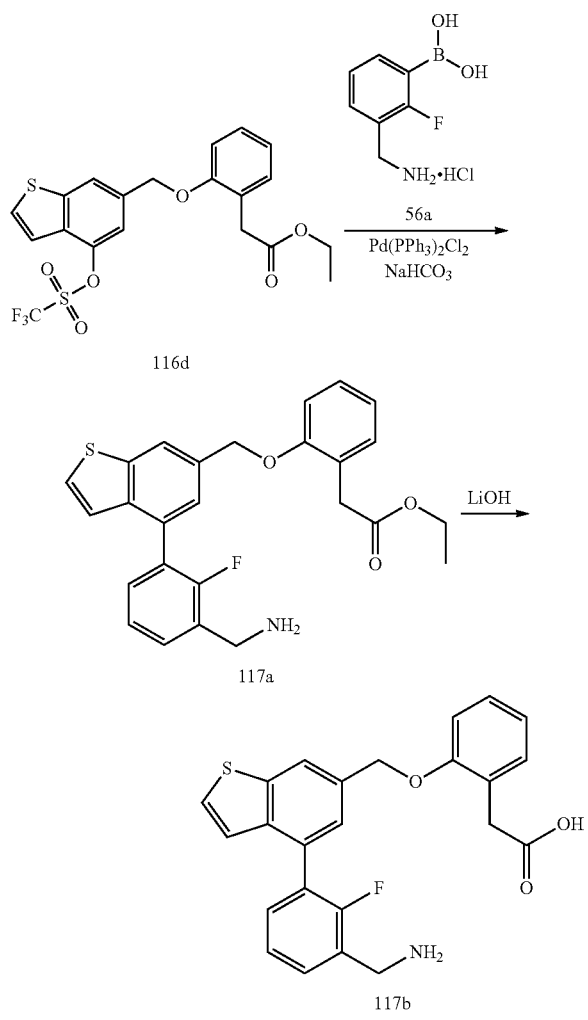

Scheme-117

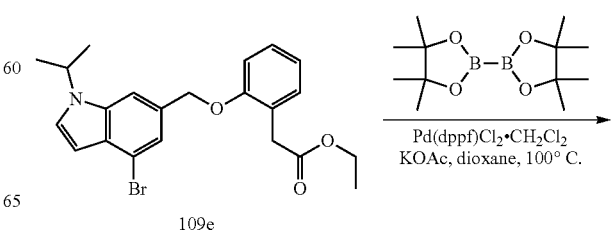

Scheme-118

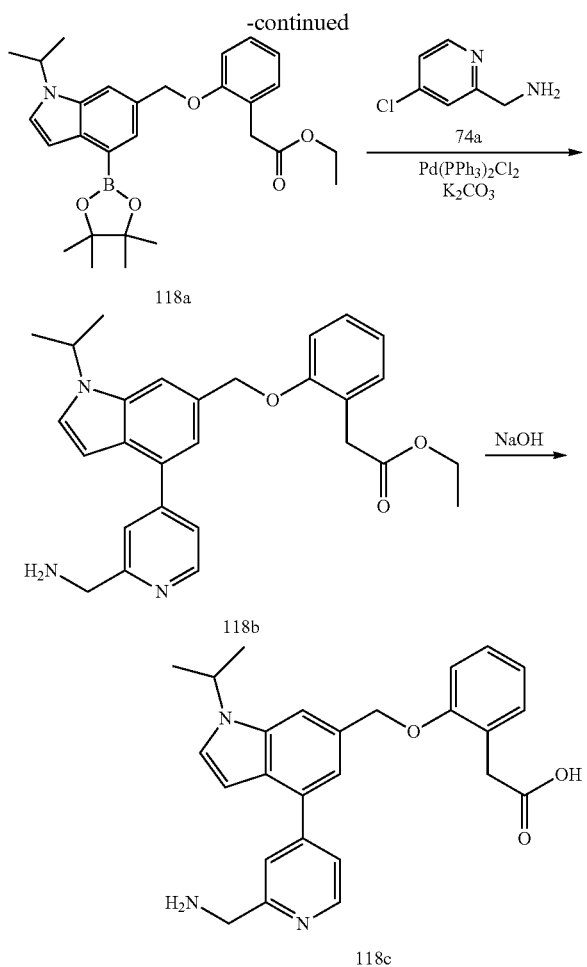

Preparation of 2-(2-((4-(2-(aminomethyl)pyridin-4-yl)-1-isopropyl-1H-indol-6-yl)methoxy)phenyl)acetic Acid (118c)

Step-1: Preparation of Ethyl 2-(2-((1-isopropyl-4-(4,4,5,5-tetramethyl-1,3,2-dioxaborolan-2-yl)-1H-indol-6-yl)methoxy)phenyl)acetate (118a)

Compound 118a was prepared according to the procedure reported in step-1 of Scheme-59 from ethyl 2-(2-((4-bromo-1-isopropyl-1H-indol-6-yl)methoxy)phenyl)acetate (109e) (0.9 g, 2.09 mmol), using bis(pinacolato)diboron (0.80 g, 3.14 mmol, CAS #: 73183-34-3), potassium acetate (0.62 g, 6.27 mmol) and Pd(dppf)Cl$_2$—CH$_2$Cl$_2$ (0.26 g, 0.31 mmol) in anhydrous dioxane (30 mL) under an Ar atmosphere and heating at 100° C. overnight. This gave after workup and purification by flash column chromatography [silica (12 g), eluting with EtOAc/MeOH 9:1 in hexane from 0-10%] ethyl 2-(2-((1-isopropyl-4-(4,4,5,5-tetramethyl-1,3,2-dioxaborolan-2-yl)-1H-indol-6-yl)methoxy)phenyl)acetate (118a) (0.6 g, 60% yield) as a clear oil; $^1$H NMR (300 MHz, DMSO-d$_6$) δ 7.70 (s, 1H), 7.53 (d, J=3.2 Hz, 1H), 7.46 (d, J=1.3 Hz, 1H), 7.29-7.17 (m, 2H), 7.11 (d, J=8.1 Hz, 1H), 6.89 (t, J=7.4 Hz, 1H), 6.76 (d, J=3.3 Hz, 1H), 5.18 (s, 2H), 4.76 (p, J=6.7 Hz, 1H), 4.00 (q, J=7.1 Hz, 2H), 3.60 (s, 2H), 1.44 (d, J=6.6 Hz, 6H), 1.32 (d, J=2.0 Hz, 12H), 1.04 (t, J=7.1 Hz, 3H); MS (ES+) 479.4 (M+1).

Step-2: Preparation of Ethyl 2-(2-((4-(2-(aminomethyl)pyridin-4-yl)-1-isopropyl-1H-indol-6-yl)methoxy)phenyl)acetate (118b)

Compound 118b was prepared according to the procedure reported in step-3 of Scheme-1 from ethyl 2-(2-((1-isopropyl-4-(4,4,5,5-tetramethyl-1,3,2-dioxaborolan-2-yl)-1H-indol-6-yl)methoxy)phenyl)acetate (118a) (0.6 g, 1.26 mmol) in dioxane (10 mL) using (4-chloropyridin-2-yl)methanamine (74a) (0.216 mL, 1.885 mmol), bis(triphenylphosphine)palladium(II) chloride (0.13 g, 0.19 mmol) and a solution of K$_2$CO$_3$ (0.43 g, 3.14 mmol) in water (1 mL) under an Ar atmosphere and heating at 100° C. for 2 h on oil bath. This gave after workup, purification by flash column chromatography [silica (12 g), eluting with MeOH in DCM from 0-50%] followed by purification by reverse phase column [C18 (50 g), eluting with ACN in water (containing 0.1% HCl) from 0-100%] ethyl 2-(2-((4-(2-(aminomethyl)pyridin-4-yl)-1-isopropyl-1H-indol-6-yl)methoxy)phenyl)acetate (118b) (0.3 g, 52% yield) as a yellow solid; $^1$H NMR (300 MHz, DMSO-d$_6$) δ 8.72 (d, J=5.2 Hz, 1H), 8.38 (s, 3H), 7.83 (s, 1H), 7.75 (s, 1H), 7.72 (d, J=5.2 Hz, 1H), 7.69 (d, J=3.3 Hz, 1H), 7.33 (s, 1H), 7.28-7.20 (m, 2H), 7.13 (d, J=8.2 Hz, 1H), 6.91 (t, J=7.4 Hz, 1H), 6.73 (d, J=3.3 Hz, 1H), 5.27 (s, 2H), 4.92-4.77 (m, 1H), 4.30 (q, J=6.0 Hz, 2H), 3.92 (q, J=7.1 Hz, 2H), 3.64 (s, 2H), 1.50 (d, J=6.7 Hz, 6H), 0.97 (t, J=7.1 Hz, 3H); MS (ES+): 458.5 (M+1); MS (ES−): 492.5 (M+Cl). HPLC purity: 96.70%.

Step-3: Preparation of 2-(2-((4-(2-(aminomethyl)pyridin-4-yl)-1-isopropyl-1H-indol-6-yl)methoxy)phenyl)acetic Acid (118c)

Compound 118c was prepared according to the procedure reported in step-4 of Scheme-4, from ethyl 2-(2-((4-(2-(aminomethyl)pyridin-4-yl)-1-isopropyl-1H-indol-6-yl)methoxy)phenyl)acetate (118b) (0.15 g, 0.33 mmol) in MeOH/THF (6 mL) using a solution of sodium hydroxide (0.07 g, 1.64 mmol) in water (2 mL). This gave after workup and purification by reverse phase column [C18 (50 g), eluting with ACN in water (containing 0.1% HCl) from 0-100%] 2-(2-((4-(2-(aminomethyl)pyridin-4-yl)-1-isopropyl-1H-indol-6-yl)methoxy)phenyl)acetic acid (118c) (0.04 g, 27% yield) as a yellow solid; $^1$H NMR (500 MHz, DMSO-d$_6$) δ 8.72 (d, J=5.2 Hz, 1H), 8.44 (s, 3H), 7.86 (d, J=1.6 Hz, 1H), 7.78 (s, 1H), 7.74 (dd, J=5.2, 1.7 Hz, 1H), 7.68 (d, J=3.3 Hz, 1H), 7.37 (d, J=1.2 Hz, 1H), 7.27-7.21 (m, 2H), 7.12 (d, J=8.1 Hz, 1H), 6.90 (td, J=7.3, 1.0 Hz, 1H), 6.74 (d, J=3.2 Hz, 1H), 5.29 (s, 2H), 4.84 (p, J=6.6 Hz, 1H), 4.30 (s, 2H), 3.61 (s, 2H), 1.50 (d, J=6.6 Hz, 6H). MS (ES+): 430.5 (M+1); MS (ES−): 428.5 (M−1), 464.5 (M+Cl). HPLC purity: 96.70%.

Scheme-119

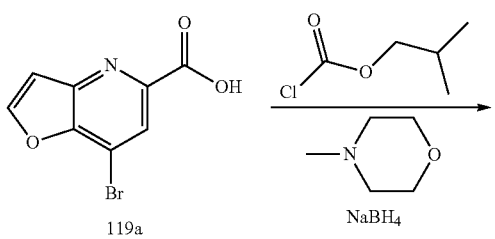

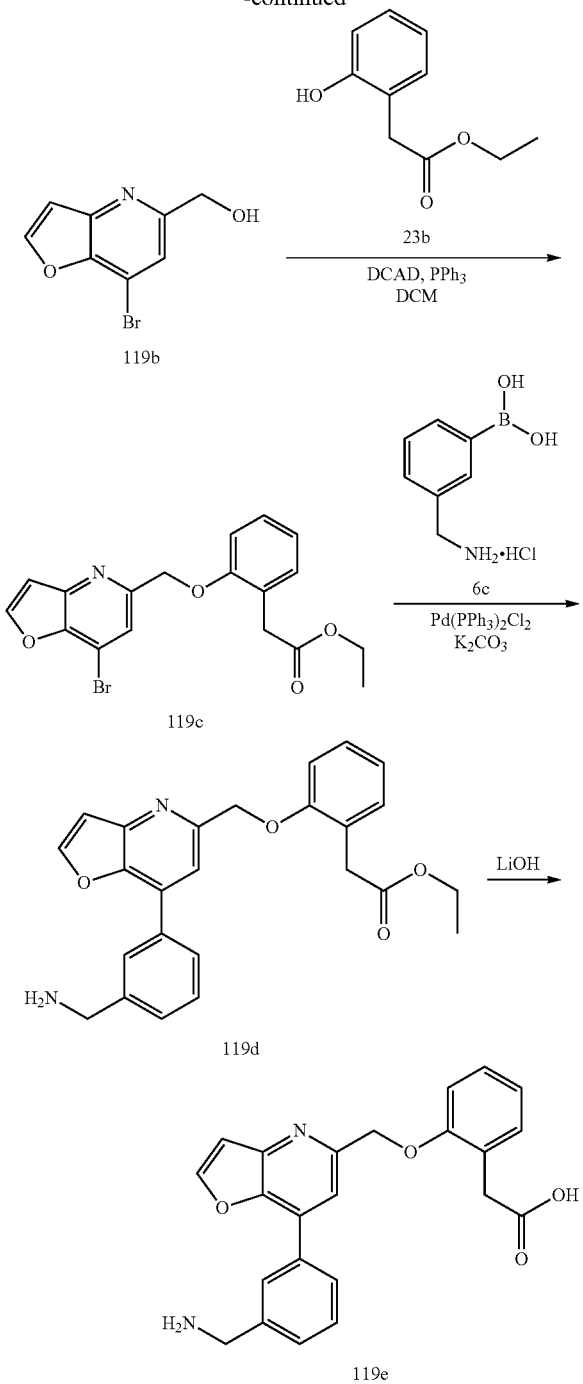

Preparation of 2-(2-((7-(3-(aminomethyl)phenyl)furo[3,2-b]pyridin-5-yl)methoxy)phenyl)acetic Acid (119e)

Step-1: Preparation of (7-bromofuro[3,2-b]pyridin-5-yl)methanol (119b)

Compound 119b was prepared according to the procedure reported in step-1 of Scheme-23 from 7-bromofuro[3,2-b]pyridine-5-carboxylic acid (119a) (800 mg, 3.31 mmol, purchased from PharmaBlock, PB95208) using N-methylmorpholine (0.44 mL, 3.97 mmol) in THF (10 mL), isobutyl chloroformate (0.52 mL, 3.97 mmol) and NaBH$_4$ (375 mg, 9.92 mmol) in water (5 mL). This gave after workup (7-bromofuro[3,2-b]pyridin-5-yl)methanol (119b) (580 mg, 77% yield) as a white solid; $^1$H NMR (300 MHz, DMSO-d$_6$) δ 8.41 (d, J=2.3 Hz, 1H), 7.66 (s, 1H), 7.20 (d, J=2.3 Hz, 1H), 5.59 (t, J=6.0 Hz, 1H, D$_2$O exchangeable), 4.64 (d, J=6.0 Hz, 2H); MS (ES−): 226.0, 227.0 (M−1).

Step-2: Preparation of Ethyl 2-(2-((7-bromofuro[3,2-b]pyridin-5-yl)methoxy)phenyl)acetate (119c)

Compound 119c was prepared according to the procedure reported in step-2 of Scheme-23 from (7-bromofuro[3,2-b]pyridin-5-yl)methanol (119b) (380 mg, 1.67 mmol) in DCM (15 mL) using triphenylphosphine (481 mg, 1.83 mmol), ethyl 2-(2-hydroxyphenyl) acetate (23b) (330 mg, 1.83 mmol) and di-(4-chlorobenzyl)azodicarboxylate (DCAD, 673 mg, 1.83 mmol) in DCM (20 mL). This gave after workup and purification by flash column chromatography [silica (40 g), eluting with EtOAc in hexane from 0-50%] ethyl 2-(2-((7-bromofuro[3,2-b]pyridin-5-yl)methoxy)phenyl)acetate (119c) (450 mg, 69% yield) as a clear oil; $^1$H NMR (300 MHz, DMSO-d$_6$) δ 8.48 (d, J=2.3 Hz, 1H), 7.70 (s, 1H), 7.28 (d, J=2.2 Hz, 1H), 7.25 (d, J=7.3 Hz, 2H), 7.07 (d, J=8.4 Hz, 1H), 6.94 (t, J=7.4 Hz, 1H), 5.26 (s, 2H), 4.05 (q, J=7.1 Hz, 2H), 3.68 (s, 2H), 1.11 (t, J=7.1 Hz, 3H); MS (ES+): 412.1, 414.1 (M+Na).

Step-3: Preparation of Ethyl 2-(2-((7-(3-(aminomethyl)phenyl)furo[3,2-b]pyridin-5-yl)methoxy)phenyl)acetate (119d)

Compound 119d was prepared according to the procedure reported in step-3 of Scheme-1 from ethyl 2-(2-((7-bromofuro[3,2-b]pyridin-5-yl)methoxy)phenyl)acetate (119c) (110 mg, 0.28 mmol) in dioxane (5 mL) using 3-(aminomethyl)phenylboronic acid hydrochloride (6c) (79 mg, 0.42 mmol), bis(triphenylphosphine)palladium(II) chloride (39.6 mg, 0.056 mmol) and K$_2$CO$_3$ (117 mg, 0.85 mmol) in water (1 mL) under an Ar atmosphere and heating at 100° C. for 3 h on an oil bath. This gave after workup, purification by flash column chromatography [silica (12 g), eluting with DMA80 in DCM from 0-50%] followed by purification by reverse phase column [C18 (50 g), eluting with ACN in water (containing 0.1% HCl) from 0-100%] ethyl 2-(2-((7-(3-(aminomethyl)phenyl)furo[3,2-b]pyridin-5-yl)methoxy)phenyl)acetate (119d) (95 mg, 81% yield) HCl salt as an off white solid; $^1$H NMR (500 MHz, DMSO-d$_6$) δ 8.45 (d, J=2.3 Hz, 1H), 8.37 (s, 3H, D$_2$O exchangeable), 8.13 (s, 1H), 8.06-8.00 (m, 1H), 7.73 (s, 1H), 7.68-7.63 (m, 2H), 7.27-7.21 (m, 3H), 7.10 (d, J=8.1 Hz, 1H), 6.92 (td, J=7.4, 1.1 Hz, 1H), 5.31 (s, 2H), 4.15 (q, J=5.8 Hz, 2H), 3.93 (q, J=7.1 Hz, 2H), 3.69 (s, 2H), 0.96 (t, J=7.1 Hz, 3H); MS (ES+): 417.2 (M+1); (ES−): 415.3 (M−1); 451.2 (M+Cl).

Step-4: Preparation of 2-(2-((7-(3-(aminomethyl)phenyl)furo[3,2-b]pyridin-5-yl)methoxy)phenyl)acetic Acid (119e)

Compound 119e was prepared according to the procedure reported in step-6 of Scheme-1, from ethyl 2-(2-((7-(3-(aminomethyl)phenyl)furo[3,2-b]pyridin-5-yl)methoxy)phenyl)acetate (119d) (60 mg, 0.14 mmol) in MeOH/THF (6 mL) using a solution of lithium hydroxide monohydrate (15 mg, 0.36 mmol) in water (1.0 mL). This gave after workup and purification by reverse phase column [C18 (50 g), eluting with ACN in water (containing 0.1% HCl) from 0-100%] 2-(2-((7-(3-(aminomethyl)phenyl)furo[3,2-b]pyridin-5-yl)methoxy)phenyl)acetic acid (119e) (36 mg, 64% yield) HCl salt as a white solid; $^1$H NMR (500 MHz, DMSO-d$_6$) δ 8.52-8.34 (m, 4H, partially D$_2$O exchangeable), 8.14 (s, 1H), 8.06 (dt, J=6.6, 2.0 Hz, 1H), 7.79 (s, 1H), 7.69-7.62 (m, 2H), 7.27-7.20 (m, 3H), 7.08 (d, J=8.1 Hz, 1H), 6.92 (td, J=7.4, 1.0 Hz, 1H), 5.34 (s, 2H), 4.16 (q, J=5.9 Hz, 2H), 3.66 (s, 2H); MS (ES+): 389.4 (M+1); (ES−): 387.4 (M−1); 423.4 (M+Cl).

and Pd(dppf)Cl$_2$—CH$_2$Cl$_2$ (0.77 g, 0.94 mmol) in anhydrous dioxane (30 mL) under an Ar atmosphere and heating at 100° C. overnight. This gave after workup and purification by flash column chromatography [silica (40 g), eluting with EtOAc in hexane from 0-40%] ethyl 2-(2-((2-(methoxymethyl)-7-(4,4,5,5-tetramethyl-1,3,2-dioxaborolan-2-yl)benzofuran-5-yl)methoxy)phenyl)acetate (120a) (1.8 g, 60% yield) as a clear oil; $^1$H NMR (300 MHz, DMSO-d$_6$) δ 7.96 (s, 1H), 7.80 (d, J=1.8 Hz, 1H), 7.65 (d, J=1.8 Hz, 1H),

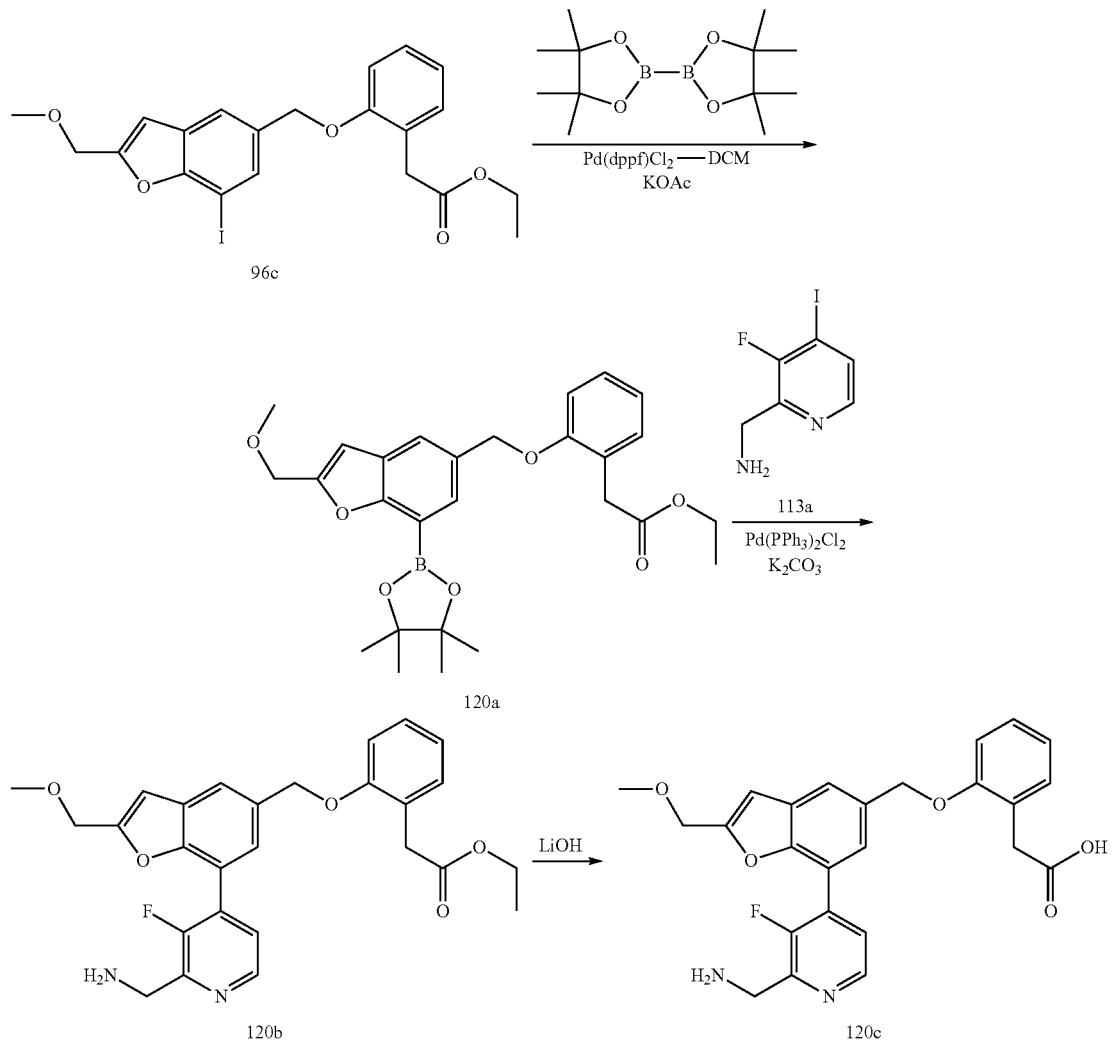

Scheme-120

Preparation of 2-(2-((7-(2-(aminomethyl)-3-fluoropyridin-4-yl)-2-(methoxymethyl)benzofuran-5-yl)methoxy)phenyl)acetic Acid (120c)

Step-1: Preparation of Ethyl 2-(2-((2-(methoxymethyl)-7-(4,4,5,5-tetramethyl-1,3,2-dioxaborolan-2-yl)benzofuran-5-yl)methoxy)phenyl)acetate (120a)

Compound 120a was prepared according to the procedure reported in step-1 of Scheme-59 from ethyl 2-(2-((7-iodo-2-(methoxymethyl)benzofuran-5-yl)methoxy)phenyl)acetate (96c) (3 g, 6.25 mmol), using bis(pinacolato)diboron (2.38 g, 9.37 mmol), potassium acetate (1.84 g, 18.74 mmol)

7.29-7.18 (m, 2H), 7.09 (d, J=7.8 Hz, 1H), 6.92-6.90 (m, 1H), 5.16 (s, 2H), 4.55 (s, 2H), 4.04-3.98 (m, 2H), 3.59 (s, 2H), 3.33 (s, 3H), 1.34 (s, 12H), 1.05-1.01 (m, 3H); MS (ES+): 503.4 (M+Na).

Step-2: Preparation of Ethyl 2-(2-((7-(2-(aminomethyl)-3-fluoropyridin-4-yl)-2-(methoxymethyl)benzofuran-5-yl)methoxy)phenyl)acetate (120b)

Compound 120b was prepared according to the procedure reported in step-3 of Scheme-1 from ethyl 2-(2-((2-(methoxymethyl)-7-(4,4,5,5-tetramethyl-1,3,2-dioxaborolan-2-yl)benzofuran-5-yl)methoxy)phenyl)acetate (120a)

(1334 mg, 2.78 mmol) in dioxane (10 mL) using (3-fluoro-4-iodopyridin-2-yl)methanamine (113a) 500 mg, 1.99 mmol), bis(triphenylphosphine)palladium(II) chloride (209 mg, 0.30 mmol) and a solution of $K_2CO_3$ (823 mg, 5.95 mmol) in water (3 mL) under an Ar atmosphere and heating at 100° C. for 3 h on oil bath. This gave after workup, purification by flash column chromatography [silica (80 g), eluting with DMA80 in DCM from 0-70%] followed by purification by reverse phase column [C18 (50 g), eluting with ACN in water (containing 0.1% HCl) from 0-100%] ethyl 2-(2-((7-(2-(aminomethyl)-3-fluoropyridin-4-yl)-2-(methoxymethyl)benzofuran-5-yl)methoxy)phenyl)acetate (120b) (455 mg, 48% yield) as an off white solid; $^1$H NMR (300 MHz, DMSO-$d_6$) δ 8.65 (d, J=4.9 Hz, 1H), 8.56 (s, 3H, $D_2O$ exchangeable), 7.86 (d, J=1.6 Hz, 1H), 7.79 (t, J=5.3 Hz, 1H), 7.54 (d, J=1.5 Hz, 1H), 7.31-7.19 (m, 2H), 7.15-7.09 (m, 1H), 7.07 (s, 1H), 6.92 (td, J=7.4, 1.1 Hz, 1H), 5.25 (s, 2H), 4.54 (s, 2H), 4.38 (d, J=6.1 Hz, 2H), 3.93 (q, J=7.1 Hz, 2H), 3.63 (s, 2H), 3.30 (s, 3H), 0.99 (t, J=7.1 Hz, 3H); $^{19}$F NMR (339 MHz, DMSO) δ−128.76; MS (ES+): 479.2 (M+1); 501.2 (M+Na); (ES−): 477.3 (M−1).

Step-3: Preparation of 2-(2-((7-(2-(aminomethyl)-3-fluoropyridin-4-yl)-2-(methoxymethyl)benzofuran-5-yl)methoxy)phenyl)acetic Acid (120c)

Compound 120c was prepared according to the procedure reported in step-6 of Scheme-1, from ethyl 2-(2-((7-(2-(aminomethyl)-3-fluoropyridin-4-yl)-2-(methoxymethyl)benzofuran-5-yl)methoxy)phenyl)acetate (120b) (255 mg, 0.53 mmol) in MeOH/THF (8 mL) using a solution of lithium hydroxide monohydrate (56 mg, 1.33 mmol) in water (1.0 mL). This gave after workup and purification by reverse phase column [C18 (50 g), eluting with ACN in water (containing 0.1% HCl) from 0-100%] 2-(2-((7-(2-(aminomethyl)-3-fluoropyridin-4-yl)-2-(methoxymethyl)benzofuran-5-yl)methoxy)phenyl)acetic acid (120c) (140 mg, 58% yield) as a white solid; $^1$H NMR (500 MHz, DMSO-$d_6$) δ 12.17 (s, 1H, $D_2O$ exchangeable), 8.63 (dd, J=4.9, 1.3 Hz, 1H), 8.49 (s, 3H, $D_2O$ exchangeable), 7.88 (d, J=1.7 Hz, 1H), 7.79 (t, J=5.3 Hz, 1H), 7.57 (s, 1H), 7.27-7.18 (m, 2H), 7.09 (d, J=8.1 Hz, 1H), 7.04 (d, J=1.4 Hz, 1H), 6.90 (t, J=7.4 Hz, 1H), 5.27 (s, 2H), 4.53 (s, 2H), 4.37 (d, J=5.9 Hz, 2H), 3.58 (s, 2H), 3.29 (s, 3H); $^{19}$F NMR (339 MHz, DMSO) δ−128.57; MS (ES+): 451.2 (M+1); (ES−): 449.3 (M−1).

Scheme-121

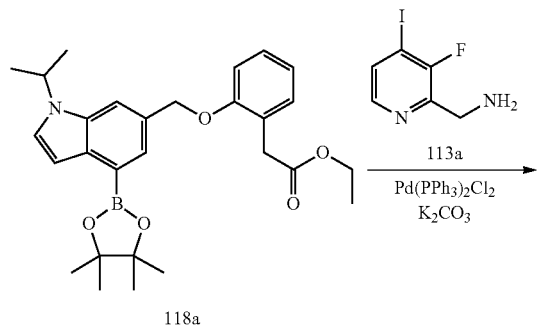

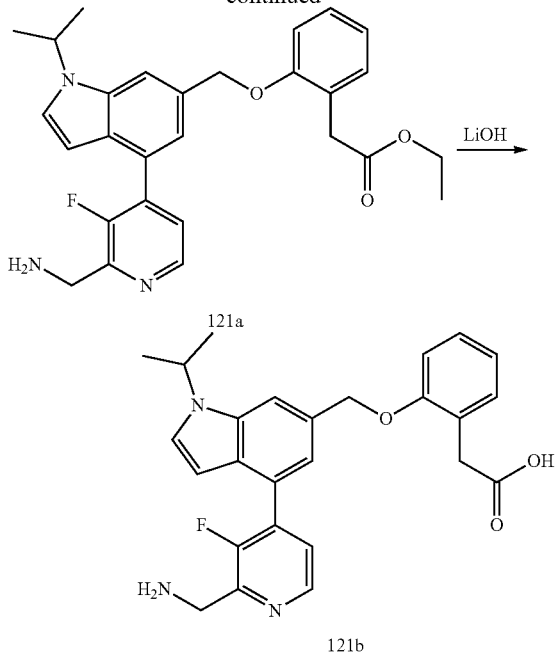

Preparation of 2-(2-((4-(2-(aminomethyl)-3-fluoropyridin-4-yl)-1-isopropyl-1H-indol-6-yl)methoxy)phenyl)acetic Acid (121b)

Step-1: Preparation of Ethyl 2-(2-((4-(2-(aminomethyl)-3-fluoropyridin-4-yl)-1-isopropyl-1H-indol-6-yl)methoxy)phenyl)acetate (121a)

Compound 121a was prepared according to the procedure reported in step-3 of Scheme-1 from ethyl 2-(2-((1-isopropyl-4-(4,4,5,5-tetramethyl-1,3,2-dioxaborolan-2-yl)-1H-indol-6-yl)methoxy)phenyl)acetate (118a) (0.85 g, 1.79 mmol) in dioxane (10 mL) using (3-fluoro-4-iodopyridin-2-yl)methanamine (113a) (0.3 g, 1.19 mmol), bis(triphenylphosphine)palladium(II) chloride (0.13 g, 0.18 mmol) and a solution of $K_2CO_3$ (0.41 g, 2.98 mmol) in water (1.0 mL) under an Ar atmosphere and heating at 100° C. for 2 h on oil bath. This gave after workup, purification by flash column chromatography [silica (24 g), eluting with MeOH in DCM from 0-50%] followed by purification by reverse phase column [C18 (50 g), eluting with ACN in water (containing 0.1% HCl) from 0-100%] ethyl 2-(2-((4-(2-(aminomethyl)-3-fluoropyridin-4-yl)-1-isopropyl-1H-indol-6-yl)methoxy)phenyl)acetate (121a) (0.1 g, 18% yield) as a yellow solid; MS (ES+): 475.5 (M+1); MS (ES−): 474.5 (M−1).

Step-2: Preparation 2-(2-((4-(2-(aminomethyl)-3-fluoropyridin-4-yl)-1-isopropyl-1H-indol-6-yl)methoxy)phenyl)acetic Acid (121b)

Compound 121b was prepared according to the procedure reported in step-6 of Scheme-1, from ethyl 2-(2-((4-(2-(aminomethyl)-3-fluoropyridin-4-yl)-1-isopropyl-1H-indol-6-yl)methoxy)phenyl)acetate (121a) (0.1 g, 0.210 mmol) in MeOH/THF (4 mL) using a solution of lithium hydroxide monohydrate (44 mg, 1.05 mmol) in water (1.0 mL). This gave after workup and purification by reverse phase column [C18 (50 g), eluting with ACN in water (containing 0.1% HCl) from 0-100%] 2-(2-((4-(2-(aminomethyl)-3-fluoropyridin-4-yl)-1-isopropyl-1H-indol-6-yl)methoxy)phenyl) acetic acid (121b) (0.04 g, 43% yield) as a yellow solid; $^1$H NMR (500 MHz, DMSO-$d_6$) δ 8.57 (d, J=4.9 Hz, 1H), 8.52-8.46 (bs, 3H), 7.81 (s, 1H), 7.69 (t, J=5.3 Hz, 1H), 7.65 (d, J=3.3 Hz, 1H), 7.27 (s, 1H), 7.26-7.20 (m, 2H), 7.12 (d, J=8.1 Hz, 1H), 6.90 (td, J=7.3, 1.1 Hz, 1H), 6.40 (t, J=3.0 Hz, 1H), 5.28 (s, 2H), 4.84 (p, J=6.7 Hz, 1H), 4.36 (m, 2H), 3.59 (s, 2H), 1.49 (d, J=6.6 Hz, 6H); $^{19}F$ NMR (282 MHz, DMSO-$d_6$) δ −129.76; MS (ES+): 448.5 (M+1); MS (ES−): 446.5 (M−1), 482.5 (M+Cl). HPLC purity: 95.70%.

Scheme-122

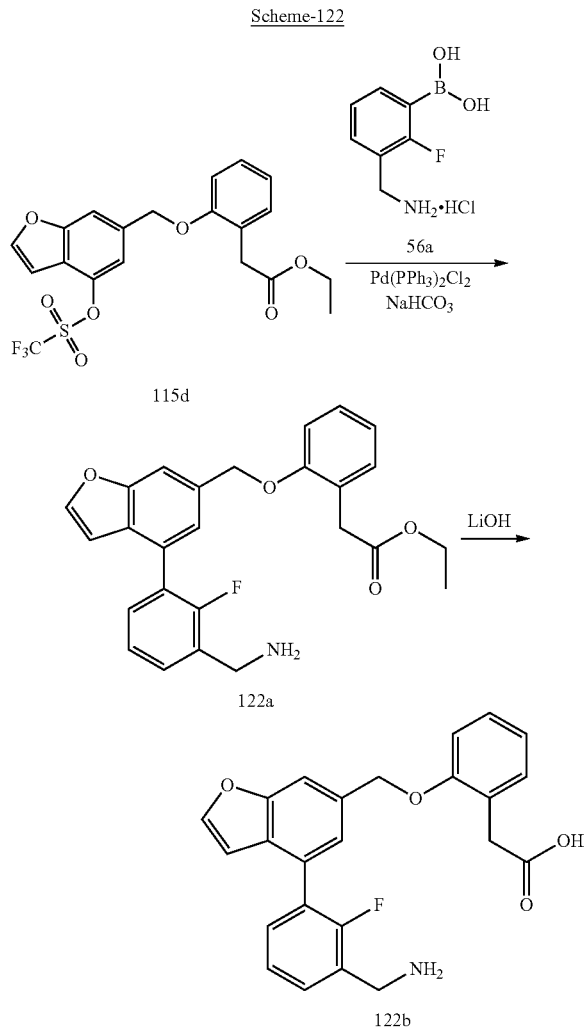

Preparation of 2-(2-((4-(3-(aminomethyl)-2-fluorophenyl)benzofuran-6-yl)methoxy)phenyl)acetic Acid (122b)

Step-1: Preparation of Ethyl 2-(2-((4-(3-(aminomethyl)-2-fluorophenyl)benzofuran-6-yl)methoxy)phenyl)acetate (122a)

Compound 122a was prepared according to the procedure reported in step-3 of Scheme-1 from ethyl 2-(2-((4-(((trifluoromethyl)sulfonyl)oxy)benzofuran-6-yl)methoxy)phenyl)acetate (115d) (500 mg, 1.091 mmol) in dioxane (10 mL) using (3-(aminomethyl)-2-fluorophenyl)boronic acid hydrochloride (56a) (336 mg, 1.636 mmol), a solution of sodium bicarbonate (275 mg, 3.27 mmol) in water (1 mL) and bis(triphenylphosphine)palladium(II) chloride (230 mg, 0.327 mmol) and heating under an nitrogen atmosphere at 95° C. for 3 h. This gave after workup, purification by flash column chromatography [silica (12 g), eluting with dichloromethane/methanol (1:0 to 9:1)] ethyl 2-(2-((4-(3-(aminomethyl)-2-fluorophenyl)benzofuran-6-yl)methoxy)phenyl)acetate (122a) (147 mg) as a yellow gum (147 mg, 31%). MS (ES+): 434.4 (M+1).

Step-2: Preparation of 2-(2-((4-(3-(aminomethyl)-2-fluorophenyl)benzofuran-6-yl)methoxy)phenyl)acetic Acid (122b)

Compound 122b was prepared according to the procedure reported in step-6 of Scheme-1, from ethyl 2-(2-((4-(3-(aminomethyl)-2-fluorophenyl)benzofuran-6-yl)methoxy)phenyl)acetate (122a) (147 mg, 0.339 mmol) in THF (7 mL) and MeOH (7 mL) using a solution of lithium hydroxide hydrate (87 mg, 2.04 mmol) in water (7 mL). This gave after workup and purification by flash column chromatography [silica gel, eluting with dichloromethane/methanol (1:0 to 9:1)] 2-(2-((4-(3-(aminomethyl)-2-fluorophenyl)benzofuran-6-yl)methoxy)phenyl)acetic acid (122b) (44 mg, 32% yield) as a white solid $^1H$ NMR (500 MHz, DMSO-$d_6$) δ 8.06 (d, J=2.2 Hz, 1H), 7.72 (s, 1H), 7.55 (t, J=7.2 Hz, 1H), 7.48 (s, 1H), 7.47-7.43 (m, 1H), 7.32 (t, J=7.6 Hz, 1H), 7.25-7.18 (m, 2H), 7.06 (d, J=8.3 Hz, 1H), 6.92-6.86 (m, 1H), 6.86-6.82 (m, 1H), 5.30 (s, 2H), 3.89 (s, 2H), 3.56 (s, 2H); MS (ES+): 406.4 (M+1), 428.4 (M+Na); MS (ES−): 404.5 (M−1); HPLC purity: 96.40%.

Scheme-123

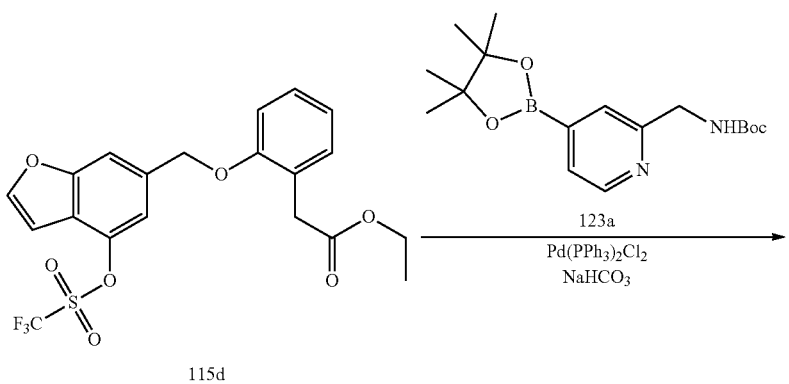

-continued

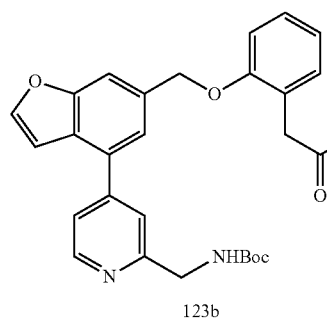

123b

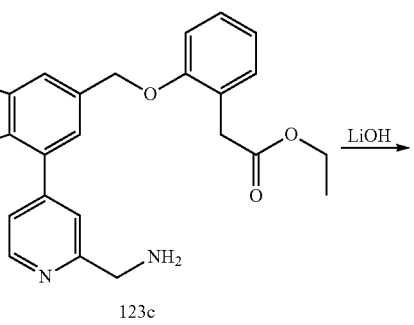

123c

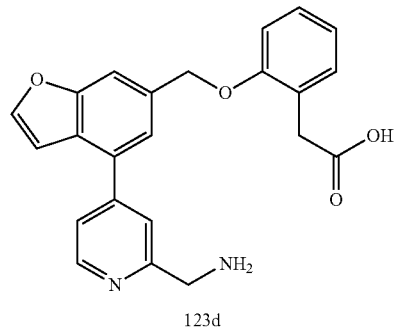

123d

Preparation of 2-(2-((4-(2-(aminomethyl)pyridin-4-yl)benzofuran-6-yl)methoxy)phenyl)acetic Acid (123d)

Step-1: Preparation of Ethyl 2-(2-((4-(2-(((tert-butoxycarbonyl)amino)methyl)pyridin-4-yl)benzofuran-6-yl)methoxy)phenyl)acetate (123b)

Compound 123b was prepared according to the procedure reported in step-3 of Scheme-1 from ethyl 2-(2-((4-(((trifluoromethyl)sulfonyl)oxy)benzofuran-6-yl)methoxy)phenyl)acetate (115d) (500 mg, 1.09 mmol) in dioxane (10 mL) using tert-butyl (4-(4,4,5,5-tetramethyl-1,3,2-dioxaborolan-2-yl)pyridin-2-yl)methylcarbamate (123a) (547 mg, 1.64 mmol; CAS #1425334-54-8), a solution of sodium bicarbonate (275 mg, 3.27 mmol) in water (1 mL) and bis(triphenylphosphine)palladium(II) chloride (230 mg, 0.327 mmol) and heating under an nitrogen atmosphere at 95° C. for 3 h. This gave after workup, purification by flash column chromatography [silica (24 g), eluting with hexanes/ethyl acetate (1:0 to 1:1)] ethyl 2-(2-((4-(2-(((tert-butoxycarbonyl)amino)methyl)pyridin-4-yl)benzofuran-6-yl)methoxy)phenyl)acetate (123b) (177 mg, 31%) as a white solid; $^1$H NMR (300 MHz, DMSO-$d_6$) δ 8.62 (dd, J=5.0, 0.9 Hz, 1H), 8.18 (d, J=2.3 Hz, 1H), 7.79-7.77 (m, 1H), 7.59-7.49 (m, 4H), 7.31-7.19 (m, 2H), 7.15-7.06 (m, 2H), 6.92 (td, J=7.4, 1.1 Hz, 1H), 5.29 (s, 2H), 4.32 (d, J=6.1 Hz, 2H), 3.93 (q, J=7.1 Hz, 2H), 3.65 (s, 2H), 1.40 (s, 9H), 0.99 (t, J=7.1 Hz, 3H); MS (ES+): 539.5 (M+Na); MS (ES−): 515.5 (M−1).

Step-2: Preparation of Ethyl 2-(2-((4-(2-(aminomethyl)pyridin-4-yl)benzofuran-6-yl)methoxy)phenyl)acetate (123c)

Compound 123c was prepared according to the procedure reported in step-5 of Scheme-1 ethyl 2-(2-((4-(2-(((tert-butoxycarbonyl)amino)methyl)pyridin-4-yl)benzofuran-6-yl)methoxy)phenyl)acetate (123b) (160 mg, 0.31 mmol) in DCM (10 mL) using TFA (0.24 mL, 3.10 mmol). This gave after workup and purification by flash column chromatography [silica (12 g), eluting with DCM/methanol (1:0 to 9:1)] ethyl 2-(2-((4-(2-(aminomethyl)pyridin-4-yl)benzofuran-6-yl)methoxy)phenyl)acetate (123c) (136 mg, 83% yield) as a light brown gum. $^1$H NMR (300 MHz, DMSO-$d_6$) δ 8.76 (d, J=5.1 Hz, 1H), 8.36 (s, 3H), 8.21 (d, J=2.3 Hz, 1H), 7.82 (d, J=5.8 Hz, 2H), 7.74 (dd, J=5.2, 1.7 Hz, 1H), 7.61 (d, J=1.3 Hz, 1H), 7.33-7.18 (m, 3H), 7.10 (d, J=8.1 Hz, 1H), 6.95-6.88 (m, 1H), 5.30 (s, 2H), 4.33 (s, 2H), 3.96 (q, J=7.1 Hz, 2H), 3.66 (s, 2H), 1.02 (t, J=7.1 Hz, 3H); MS (ES+): 417.4 (M+1).

Step-3: Preparation of 2-(2-((4-(2-(aminomethyl)pyridin-4-yl)benzofuran-6-yl)methoxy)phenyl)acetic Acid (123d)

Compound 123d was prepared according to the procedure reported in step-6 of Scheme-1, from ethyl 2-(2-((4-(2-(aminomethyl)pyridin-4-yl)benzofuran-6-yl)methoxy)phenyl)acetate (123c) (100 mg, 0.19 mmol) in THF (6 mL) and MeOH (6 mL) using a solution of lithium hydroxide hydrate (62 mg, 1.44 mmol) in water (7 mL). This gave after workup and purification by flash column chromatography [silica gel, eluting with dichloromethane/methanol (1:0 to 9:1)] 2-(2-((4-(2-(aminomethyl)pyridin-4-yl)benzofuran-6-yl)methoxy)phenyl)acetic acid (123d) (25 mg, 33% yield) as an off-white solid. $^1$H NMR (500 MHz, DMSO-$d_6$) δ 8.62 (d, J=5.2 Hz, 1H), 8.16 (d, J=2.3 Hz, 1H), 8.15 (s, 1H), 7.81 (d, J=13.5 Hz, 2H), 7.72 (dd, J=5.1, 1.7 Hz, 1H), 7.26-7.25 (m, 1H), 7.15-7.10 (m, 2H), 6.99 (d, J=8.1 Hz, 1H), 6.83 (t, J=7.3 Hz, 1H), 5.31 (s, 2H), 4.09 (s, 2H), 3.45 (s, 2H); MS (ES+): 389.4 (M+1); MS (ES−): 387.3 (M−1), 423.3 (M+Cl).

Scheme-124
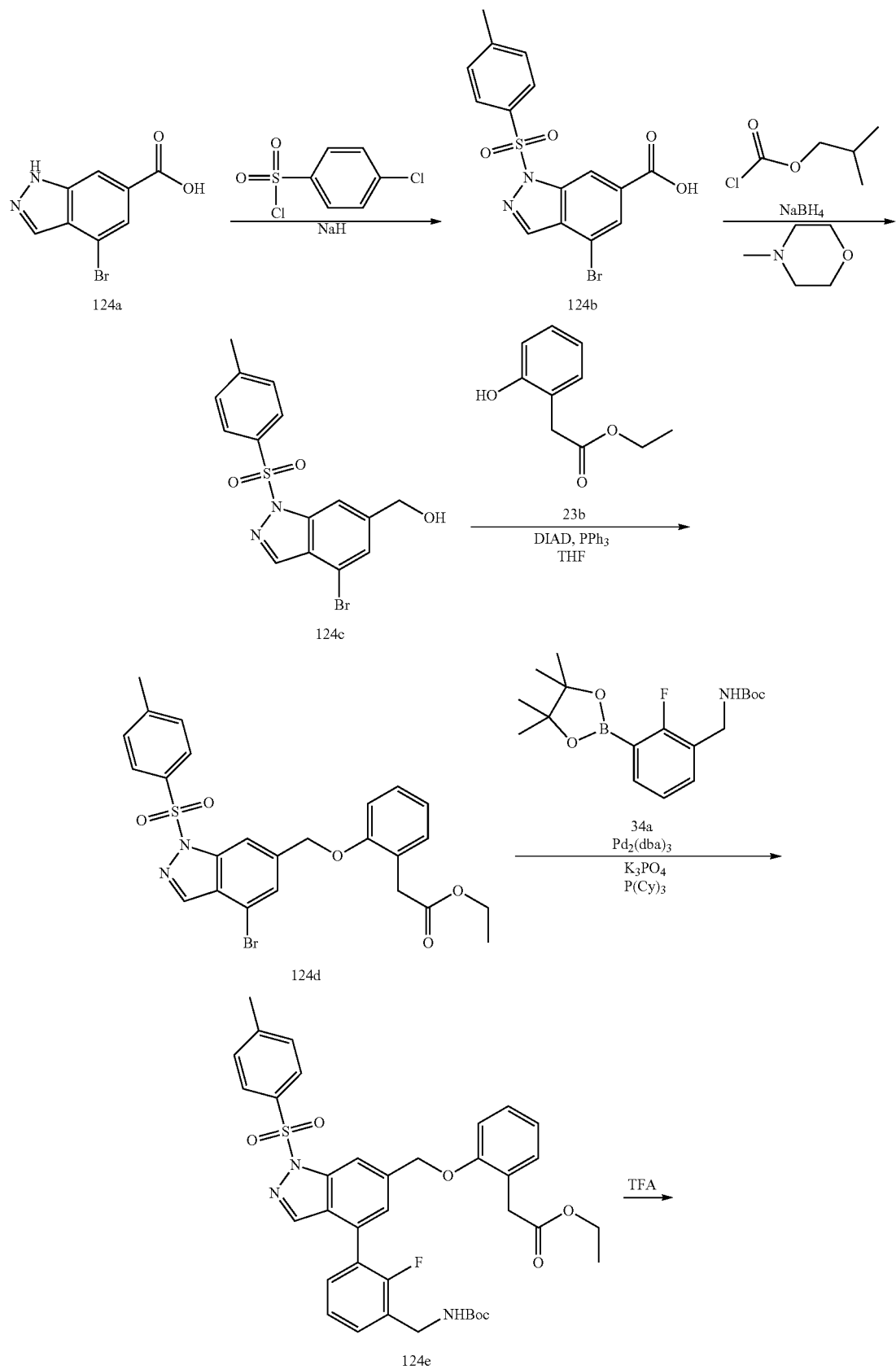

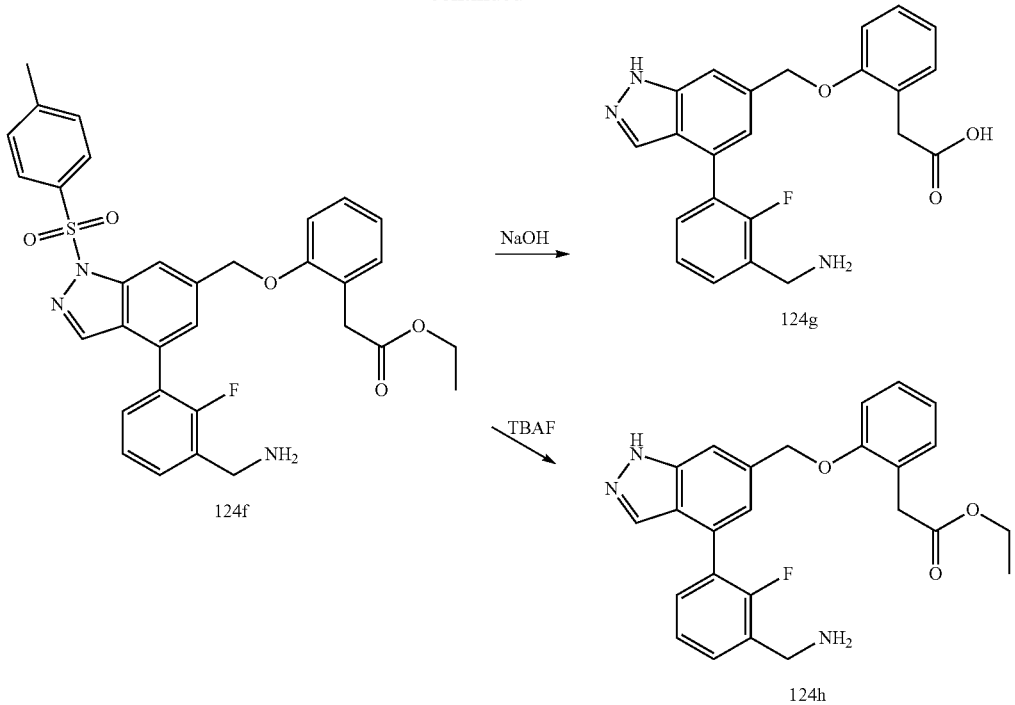

Preparation of 2-(2-((4-(3-(aminomethyl)-2-fluorophenyl)-1H-indazol-6-yl)methoxy)phenyl)acetic Acid (124g) and ethyl 2-(2-((4-(3-(aminomethyl)-2-fluorophenyl)-1H-indazol-6-yl)methoxy)phenyl)acetate (124h)

Step-1: Preparation of 4-bromo-1-tosyl-1H-indazole-6-carboxylic Acid (124b)

Compound 124b was prepared according to the procedure reported in step-1 of Scheme-40 from 4-bromo-1H-indazole-6-carboxylic acid (124a) (1.00 g, 4.15 mmol; CAS #885523-43-3) in DMF (25 mL) using NaH (60% in mineral oil, 0.332 g, 8.30 mmol), tosyl-Cl (0.870 g, 4.56 mmol). This gave after workup 4-bromo-1-tosyl-1H-indazole-6-carboxylic acid (124b) (1.292 g, 79% yield) as a white solid; MS (ES+): 395.0, 397.0 (M+2).

Step-2: Preparation of (4-bromo-1-tosyl-1H-indazol-6-yl)methanol (124c)

Compound 124c was prepared according to the procedure reported in step-1 of Scheme-23 from 4-bromo-1-tosyl-1H-indazole-6-carboxylic acid (124b) (1.28 g, 3.24 mmol) using N-methylmorpholine (0.427 mL, 3.89 mmol) in THF (30 mL), isobutyl chloroformate (0.51 mL, 3.89 mmol) and NaBH$_4$ (0.368 g, 9.72 mmol) in water (3 mL). This gave after workup and purification by flash column chromatography [silica gel 24 g, eluting with ethyl acetate in hexanes from 0-100%] (4-bromo-1-tosyl-1H-indazol-6-yl)methanol (124c) (0.438 g, 36% yield) as a white solid; $^1$H NMR (300 MHz, DMSO-d$_6$) δ 8.49 (d, J=0.9 Hz, 1H), 8.16-8.09 (m, 1H), 7.88-7.77 (m, 2H), 7.59 (d, J=1.0 Hz, 1H), 7.49-7.36 (m, 2H), 5.64 (t, J=5.8 Hz, 1H), 4.71 (d, J=5.8 Hz, 2H), 2.34 (s, 3H); MS (ES+): 403.1, 405.1 (M+Na); MS (ES−): 479.1, 481.1 (M+Cl), 415.1, 417.1 (M+Cl).

Step-3: Preparation of Ethyl 2-(2-((4-bromo-1-tosyl-1H-indazol-6-yl)methoxy)phenyl)acetate (124d)

Compound 124d was prepared according to the procedure reported in step-2 of Scheme-23 from (4-bromo-1-tosyl-1H-indazol-6-yl)methanol (124c) (0.422 g, 1.107 mmol) in THF (25 mL) using triphenylphosphine (0.377 g, 1.439 mmol) ethyl 2-(2-hydroxyphenyl) acetate (23b) (0.259 g, 1.439 mmol) and DIAD (0.280 mL, 1.439 mmol). This gave after workup and purification by flash column chromatography [silica gel 25 g, eluting with ethyl acetate in hexanes from 0-100%] ethyl 2-(2-((4-bromo-1-tosyl-1H-indazol-6-yl)methoxy)phenyl)acetate (124d) (0.406 g, 68% yield) as a pale-yellow solid; MS (ES+): 543.1, 545.1 (M+2).

Step-4: Preparation of Ethyl 2-(2-((4-(3-(((tert-butoxycarbonyl)amino)methyl)-2-fluorophenyl)-1-tosyl-1H-indazol-6-yl)methoxy)phenyl)acetate (124e)

Compound 124e was prepared according to the procedure reported in step-3 of Scheme-1 from ethyl 2-(2-((4-bromo-1-tosyl-1H-indazol-6-yl)methoxy)phenyl)acetate (124d) (400 mg, 0.74 mmol) in dioxane (6 mL) using tert-butyl 2-fluoro-3-(4,4,5,5-tetramethyl-1,3,2-dioxaborolan-2-yl)benzylcarbamate (34a) (0.388 g, 1.104 mmol), tripotassium phosphate (1.3 M solution, 0.736 mL, 2.208 mmol), tricyclohexylphosphine (0.062 g, 0.221 mmol) and Pd$_2$(dba)$_3$ (0.067 g, 0.074 mmol) under an Ar atmosphere and heating at 125° C. for 45 min in a microwave. This gave after workup, purification by flash column chromatography [silica gel, 25g, eluting with methanol in DCM from 0-100%] ethyl 2-(2-((4-(3-(((tert-butoxycarbonyl)amino)methyl)-2-fluorophenyl)-1-tosyl-1H-indazol-6-yl)methoxy)phenyl)acetate (124e) (0.175 g, 35% yield) as a yellow solid; MS (ES+): 710.3 (M+Na); MS (ES−): 722.2 (M+Cl).

Step-5: Preparation of Ethyl 2-(2-((4-(3-(aminomethyl)-2-fluorophenyl)-1-tosyl-1H-indazol-6-yl)methoxy)phenyl)acetate (124f)

Compound 124f was prepared according to the procedure reported in step-5 of Scheme-1 from ethyl 2-(2-((4-(3-(((tert-butoxycarbonyl)amino)methyl)-2-fluorophenyl)-1-tosyl-1H-indazol-6-yl)methoxy)phenyl)acetate (124e) (0.17 g, 0.247 mmol) in DCM (10 mL) using TFA (0.29 mL, 3.71 mmol). This gave after workup and purification by reverse phase column chromatography [C18 (50 g), eluting with ACN in water (containing 0.1% HCl) from 0-100%] ethyl 2-(2-((4-(3-(aminomethyl)-2-fluorophenyl)-1-tosyl-1H-indazol-6-yl)methoxy)phenyl)acetate (124f) (0.061 g, 42% yield) HCl salt as a white solid; $^1$H NMR (300 MHz, DMSO-$d_6$) δ 8.52 (d, J=3.4 Hz, 1H), 8.43-8.10 (m, 3H), 7.84 (d, J=8.3 Hz, 2H), 7.71-7.57 (m, 2H), 7.53 (s, 1H), 7.45 (d, J=7.7 Hz, 1H), 7.39 (d, J=8.3 Hz, 2H), 7.32-7.21 (m, 2H), 7.12 (d, J=8.0 Hz, 1H), 6.96 (t, J=7.4 Hz, 1H), 5.42 (s, 2H), 4.14 (s, 2H), 3.91 (q, J=7.1 Hz, 2H), 3.69 (s, 2H), 2.34 (s, 3H), 0.94 (t, J=7.1 Hz, 3H); MS (ES+): 588.3 (M+1); MS (ES−): 622.4 (M+Cl).

Step-6: Preparation of 2-(2-((4-(3-(aminomethyl)-2-fluorophenyl)-1H-indazol-6-yl)methoxy)phenyl)acetic Acid (124g)

Compound 124g was prepared according to the procedure reported in step-4 of Scheme-4, from ethyl 2-(2-((4-(3-(aminomethyl)-2-fluorophenyl)-1-tosyl-1H-indazol-6-yl)methoxy)phenyl)acetate (124f) (0.058 g, 0.099 mmol) in THF (3 mL) and methanol (6 mL) using a solution of sodium hydroxide (2 M aqueous, 0.493 mL, 0.987 mmol). This gave after workup and purification by reverse phase column [C18 (50 g), eluting with ACN in water (containing 0.1% HCl) from 0-100%] 2-(2-((4-(3-(aminomethyl)-2-fluorophenyl)-1H-indazol-6-yl)methoxy)phenyl)acetic acid (124g) (0.027 g, 68% yield) HCl salt as a white solid; $^1$H NMR (300 MHz, DMSO-$d_6$) δ 13.30 (s, 1H), 8.39 (s, 3H), 8.05 (d, J=3.1 Hz, 1H), 7.70 (s, 1H), 7.69-7.61 (m, 2H), 7.43 (t, J=7.7 Hz, 1H), 7.28 (s, 1H), 7.25-7.19 (m, 2H), 7.09 (d, J=8.2 Hz, 1H), 6.91 (t, J=7.4 Hz, 1H), 5.33 (s, 2H), 4.25-4.13 (m, 2H), 3.60 (s, 2H); $^{19}$F NMR (282 MHz, DMSO-$d_6$) δ −118.45; MS (ES+): 406.3 (M+1), 811.4 (2M+1); MS (ES−): 404.4 (M−1), 440.3 (M+Cl), 809.5 (2M−1); HPLC purity: 92.19%.

Step-7: Preparation of Ethyl 2-(2-((4-(3-(aminomethyl)-2-fluorophenyl)-1H-indazol-6-yl)methoxy)phenyl)acetate (124h)

Compound 124h was prepared according to the procedure reported in step-1 of Scheme-58, from ethyl 2-(2-((4-(3-(aminomethyl)-2-fluorophenyl)-1-tosyl-1H-indazol-6-yl)methoxy)phenyl)acetate (124f) in THF (20 mL) using tetrabutylammonium fluoride (1.415 g, 5.41 mmol). This gave after workup and purification by reverse phase column [C18 (50 g), eluting with ACN in water (containing 0.1% HCl) from 0-100%] ethyl 2-(2-((4-(3-(aminomethyl)-2-fluorophenyl)-1H-indazol-6-yl)methoxy)phenyl)acetate (124h) (0.014 g, 6% yield) as a white solid; $^1$H NMR (300 MHz, DMSO-$d_6$) δ 13.32 (s, 1H, D$_2$O exchangeable), 8.38 (s, 4H, D$_2$O exchangeable, 3H), 8.06 (d, J=3.0 Hz, 1H), 7.71-7.61 (m, 3H), 7.44 (t, J=7.6 Hz, 1H), 7.28-7.20 (m, 3H), 7.12 (d, J=8.2 Hz, 1H), 6.92 (t, J=7.3 Hz, 1H), 5.30 (s, 2H), 4.31-4.10 (m, 2H), 3.93 (q, J=7.1 Hz, 2H), 3.64 (s, 2H), 0.98 (t, J=7.1 Hz, 2H); $^{19}$F NMR (282 MHz, DMSO-$d_6$) δ −118.55; MS (ES+): 434.4 (M+1); 456.3 (M+Na); MS (ES−): 468.4 (M+Cl); 901.6 (2M+Cl).

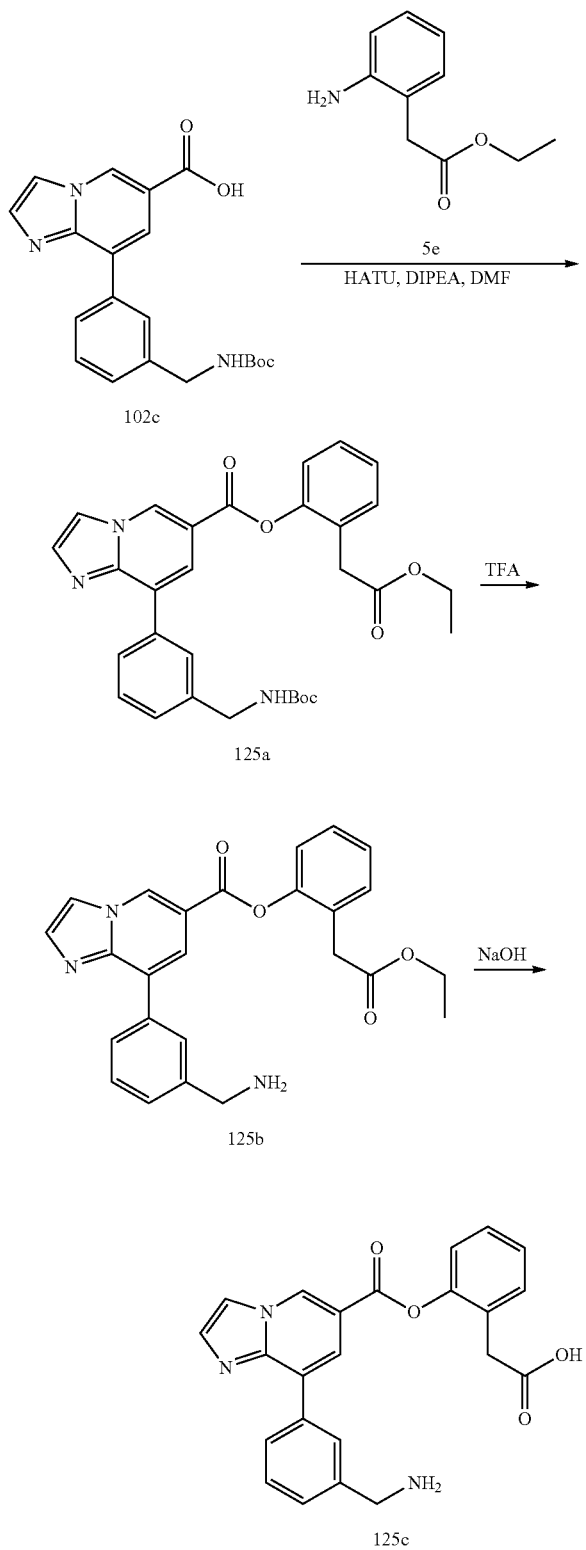

Scheme-125

Preparation of 2-(2-(8-(3-(aminomethyl)phenyl)
imidazo[1,2-a]pyridine-6-carboxamido)phenyl)acetic Acid (125c)

Step-1: Preparation of Ethyl 2-(2-(8-(3-(((tert-butoxycarbonyl)amino)methyl)phenyl)imidazo[1,2-a]pyridine-6-carboxamido)phenyl)acetate (125a)

Compound 125a was prepared according to the procedure reported in step-4 of Scheme-1 from 8-(3-(((tert-butoxycarbonyl)amino)methyl)phenyl)imidazo[1,2-a]pyridine-6-carboxylic acid (102c) (0.350 g, 0.953 mmol) in DMF (10 mL) using ethyl 2-(2-aminophenyl)acetate (5e) (0.205 g, 1.143 mmol), DIPEA (0.830 mL, 4.76 mmol) and HATU (0.543 g, 1.429 mmol). This gave after workup and purification by flash column chromatography (Silica gel, 24 g eluting with methanol in DCM from 0-20%) ethyl 2-(2-(8-(3-(((tert-butoxycarbonyl)amino)methyl)phenyl)imidazo[1,2-a]pyridine-6-carboxamido)phenyl)acetate (125a) (0.388 g, 77% yield) as a yellow syrup; MS (ES−): 527.4 (M−1).

Step-2: Preparation of Ethyl 2-(2-(8-(3-(aminomethyl)phenyl)imidazo[1,2-a]pyridine-6-carboxamido)phenyl)acetate (125b)

Compound 125b was prepared according to the procedure reported in step-5 of Scheme-1 from ethyl 2-(2-(8-(3-(((tert-butoxycarbonyl)amino)methyl)phenyl)imidazo[1,2-a]pyridine-6-carboxamido)phenyl)acetate (125a) (0.371 g, 0.702 mmol) in DCM (10 mL) using TFA (0.811 mL, 10.53 mmol). This gave after workup and purification by reverse phase column chromatography [C18 (50 g), eluting with ACN in water (containing 0.1% HCl) from 0-100%] ethyl 2-(2-(8-(3-(aminomethyl)phenyl)imidazo[1,2-a]pyridine-6-carboxamido)phenyl)acetate (125b) (0.138 g, 46% yield) as a white solid; $^1$HNMR (300 MHz, DMSO-$d_6$) δ 10.67 (s, 1H), 9.54 (s, 1H), 8.63 (s, 3H), 8.57-8.50 (m, 2H), 8.25-8.12 (m, 2H), 8.07-7.92 (m, 1H), 7.76-7.61 (m, 2H), 7.43-7.27 (m, 4H), 4.25-4.12 (m, 2H), 3.96 (q, J=7.1 Hz, 2H), 3.80 (s, 2H), 1.01 (t, J=7.1 Hz, 3H); MS (ES+): 429.4 (M+1); MS (ES−): 463.3 (M+Cl).

Step-3: Preparation of 2-(2-(8-(3-(aminomethyl)phenyl)imidazo[1,2-a]pyridine-6-carboxamido)phenyl)acetic Acid (125c)

Compound 125c was prepared according to the procedure reported in step-4 of Scheme-4, from ethyl 2-(2-(8-(3-(aminomethyl)phenyl)imidazo[1,2-a]pyridine-6-carboxamido)phenyl)acetate (125b) (0.065 g, 0.152 mmol) in THF (3 mL) and methanol (6 mL) using a solution of sodium hydroxide (2 M aqueous, 0.379 mL, 0.758 mmol). This gave after workup and purification by reverse phase column [C18 (50 g), eluting with ACN in water (containing 0.1% HCl) from 0-100%] 2-(2-(8-(3-(aminomethyl)phenyl)imidazo[1,2-a]pyridine-6-carboxamido)phenyl)acetic acid (125c) (0.027 g, 44% yield) HCl salt as a white solid; $^1$H NMR (300 MHz, DMSO-$d_6$) δ 12.3 (bs, 1H, D$_2$O exchangeable), 10.61 (s, 1H, D$_2$O exchangeable), 9.52 (s, 1H), 8.61 (s, 3H, D$_2$O exchangeable), 8.52 (s, 1H), 8.48 (s, 1H), 8.17 (s, 1H), 8.14 (s, 1H), 8.01 (s, 1H), 7.75-7.62 (m, 2H), 7.48-7.22 (m, 4H), 4.24-4.13 (m, 2H), 3.72 (s, 2H); MS (ES+): 401.3 (M+1); 801.5 (2M+1); MS (ES−): 399.3 (M−1); 799.5 (2M−1); HPLC purity: 98.60%.

Scheme-126

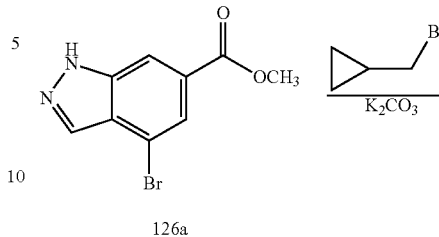

126a

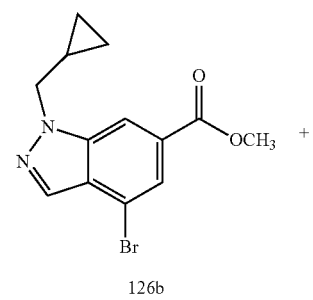

126b

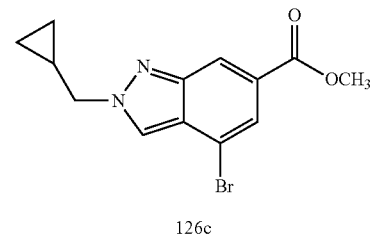

126c

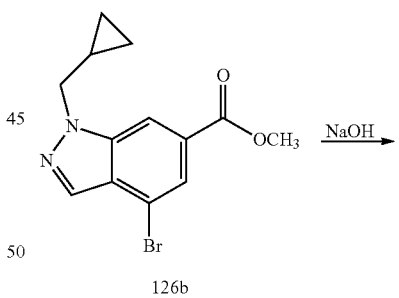

126b

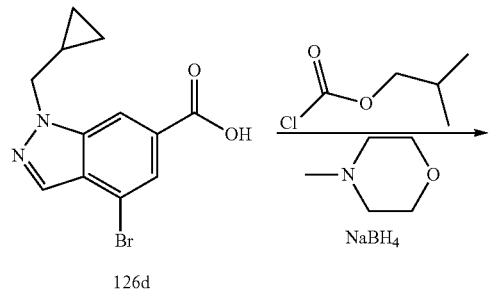

126d

565

-continued

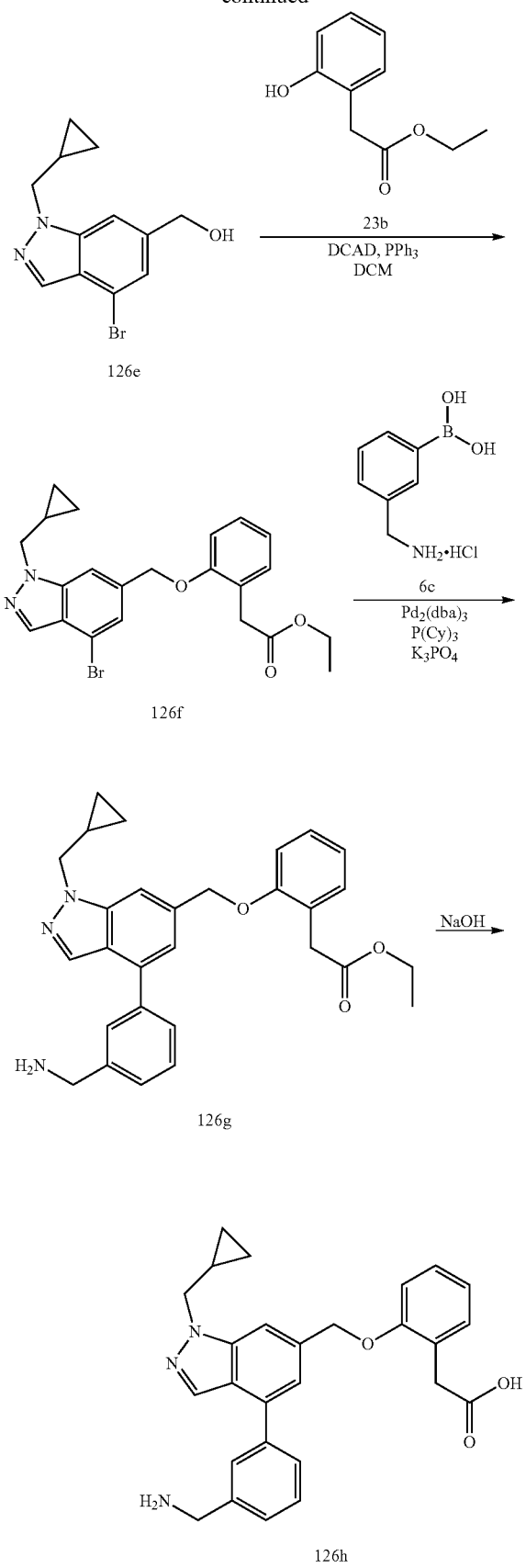

566

Preparation of 2-(2-((4-(3-(aminomethyl)phenyl)-1-(cyclopropylmethyl)-1H-indazol-6-yl)methoxy)phenyl)acetic Acid (126h)

Step-1: Preparation of methyl 4-bromo-1-(cyclopropylmethyl)-1H-indazole-6-carboxylate (126b) and methyl 4-bromo-2-(cyclopropylmethyl)-2H-indazole-6-carboxylate (126c)

Compounds 126b and 126c were prepared according to the procedure reported in step-1 of Scheme-109, from methyl 4-bromo-1H-indazole-6-carboxylate (126a) (2.103 g, 8.24 mmol; CAS #885518-47-8) in DMF using (bromomethyl)cyclopropane (1.201 mL, 12.37 mmol) and potassium carbonate (2.279 g, 16.49 mmol). This gave after workup and purification by flash column chromatography [silica gel, 40 g, eluting with EtOAc in hexane from 0-50%] methyl 4-bromo-1-(cyclopropylmethyl)-1H-indazole-6-carboxylate (126b) (0.952 g, 37% yield) as a white solid; $^1$H NMR (300 MHz, DMSO-$d_6$) δ 8.43 (s, 1H), 8.18 (d, J=1.0 Hz, 1H), 7.83 (d, J=1.0 Hz, 1H), 4.46 (d, J=7.0 Hz, 2H), 3.92 (s, 3H), 1.39-1.21 (m, 1H), 0.56-0.36 (m, 4H) and methyl 4-bromo-2-(cyclopropylmethyl)-2H-indazole-6-carboxylate (126c) (0.821 g, 32% yield) as an off-white solid; $^1$H NMR (300 MHz, DMSO-$d_6$) δ 8.61 (d, J=0.9 Hz, 1H), 8.31 (d, J=1.0 Hz, 1H), 7.73 (d, J=1.1 Hz, 1H), 4.37 (d, J=7.3 Hz, 2H), 3.90 (s, 3H), 1.55-1.32 (m, 1H), 0.67-0.44 (m, 4H).

Step-2: Preparation of 4-bromo-1-(cyclopropylmethyl)-1H-indazole-6-carboxylic Acid (126d)

Compound 126d was prepared according to the procedure reported in step-4 of Scheme-4, from methyl 4-bromo-1-(cyclopropylmethyl)-1H-indazole-6-carboxylate (126b) (0.930 g, 3.01 mmol) in THF (5 mL) and methanol (10 mL) using a solution of sodium hydroxide (2 M aqueous, 6.02 mL, 12.03 mmol). This gave after workup 4-bromo-1-(cyclopropylmethyl)-1H-indazole-6-carboxylic acid (126d) (0.839 g, 95% yield) as a white solid; $^1$H NMR (300 MHz, DMSO-$d_6$) δ 13.43 (s, 1H), 8.40 (d, J=1.2 Hz, 1H), 8.16 (d, J=0.9 Hz, 1H), 7.82 (d, J=1.0 Hz, 1H), 4.44 (d, J=7.1 Hz, 2H), 1.39-1.19 (m, 1H), 0.56-0.45 (m, 2H), 0.45-0.35 (m, 2H); MS (ES+): 293.2 (M−2).

Step-3: Preparation of (4-bromo-1-(cyclopropylmethyl)-1H-indazol-6-yl)methanol (126e)

Compound 126e was prepared according to the procedure reported in step-1 of Scheme-23 from 4-bromo-1-(cyclopropylmethyl)-1H-indazole-6-carboxylic acid (126d) (0.821 g, 2.78 mmol) using N-methylmorpholine (0.367 mL, 3.34 mmol) in THF (20 mL), isobutyl chloroformate (0.438 mL, 3.34 mmol) and NaBH$_4$ (0.316 g, 8.35 mmol) in water (2 mL). This gave after workup and purification by flash column chromatography [silica gel 24 g, eluting with ethyl acetate in hexanes from 0-100%] (4-bromo-1-(cyclopropylmethyl)-1H-indazol-6-yl)methanol (126e) (0.735 g, 94% yield) as a thick yellow syrup; $^1$H NMR (300 MHz, DMSO-$d_6$) δ 8.00-7.94 (m, 1H), 7.68-7.62 (m, 1H), 7.36-7.29 (m, 1H), 5.44 (t, J=5.8 Hz, 1H), 4.62 (dd, J=5.8, 0.9 Hz, 2H), 4.30 (d, J=7.0 Hz, 2H), 1.33-1.21 (m, 1H), 0.53-0.43 (m, 2H), 0.42-0.34 (m, 2H); MS (ES+): 303.1 (M+Na).

Step-4: Preparation of Ethyl 2-(2-((4-bromo-1-(cyclopropylmethyl)-1H-indazol-6-yl)methoxy)phenyl)acetate (126f)

Compound 126f was prepared according to the procedure reported in step-2 of Scheme-23 (4-bromo-1-(cyclopropylmethyl)-1H-indazol-6-yl)methanol (126e) (0.722 g, 2.57 mmol) in DCM (30 mL) using triphenylphosphine (0.741 g, 2.82 mmol) ethyl 2-(2-hydroxyphenyl) acetate (23b) (0.509 g, 2.82 mmol) and di-(4-chlorobenzyl)azodicarboxylate (1.037 g, 2.82 mmol) in DCM (20 mL). This gave after workup and purification by flash column chromatography [silica gel, 40g, eluting with EtOAc in hexanes from 0-50%] ethyl 2-(2-((4-bromo-1-(cyclopropylmethyl)-1H-indazol-6-yl)methoxy)phenyl)acetate (126f) (1.01 g, 89% yield) as a white solid; MS (ES+): 465.2, 467.2 (M+Na).

Step-5: Preparation of Ethyl 2-(2-((4-(3-(aminomethyl)phenyl)-1-(cyclopropylmethyl)-1H-indazol-6-yl)methoxy)phenyl)acetate (126g)

Compound 126g was prepared according to the procedure reported in step-3 of Scheme-1 from ethyl 2-(2-((4-bromo-1-(cyclopropylmethyl)-1H-indazol-6-yl)methoxy)phenyl)acetate (126f) (0.500 g, 1.128 mmol) in dioxane (6 mL) using 3-(aminomethyl)phenylboronic acid hydrochloride (6c) (0.255 g, 1.692 mmol), tripotassium phosphate (1.3M, 2.60 mL, 3.38 mmol), tricyclohexylphosphine (0.190 g, 0.677 mmol) and Pd$_2$(dba)$_3$ (0.207 g, 0.226 mmol) under an nitrogen atmosphere and heating at 125° C. for 45 min in a microwave. This gave after workup, purification by flash column chromatography [silica (24 g), eluting with MeOH in DCM from 0-40%] followed by purification by reverse phase column [C18 (50 g), eluting with ACN in water (containing 0.1% HCl) from 0-100%] ethyl 2-(2-((4-(3-(aminomethyl)phenyl)-1-(cyclopropylmethyl)-1H-indazol-6-yl)methoxy)phenyl)acetate (126g) (119 mg, 79% yield) HCl salt as a white solid; $^1$H NMR (300 MHz, DMSO-d$_6$) δ 8.38 (s, 3H, D$_2$O exchangeable), 8.33-8.27 (m, 1H), 7.91 (s, 1H), 7.80 (s, 1H), 7.78-7.72 (m, 1H), 7.65-7.51 (m, 2H), 7.36-7.30 (m, 1H), 7.26-7.20 (m, 2H), 7.11 (d, J=7.9 Hz, 1H), 6.96-6.86 (m, 1H), 5.32 (s, 2H), 4.35 (d, J=6.9 Hz, 2H), 4.21-4.09 (m, 2H), 4.02-3.87 (m, 2H), 3.67 (s, 2H), 1.41-1.20 (m, 1H), 1.06-0.93 (m, 3H), 0.56-0.34 (m, 4H); MS (ES+): 470.4 (M+1); 939.6 (2M+1); MS (ES-): 504.4 (M+Cl), 973.7 (2M+Cl); Analysis calculated for C$_{29}$H$_{31}$N$_3$O$_3$.HCl.1.25H$_2$O: C, 65.90; H, 6.58; Cl, 6.71; N, 7.95; Found C, 65.92; H, 6.46; Cl, 7.14; N, 7.94.

Step-6: Preparation of 2-(2-((4-(3-(aminomethyl)phenyl)-1-(cyclopropylmethyl)-1H-indazol-6-yl)methoxy)phenyl)acetic Acid (126h)

Compound 126h was prepared according to the procedure reported in step-4 of Scheme-4, from ethyl 2-(2-((4-(3-(aminomethyl)phenyl)-1-(cyclopropylmethyl)-1H-indazol-6-yl)methoxy)phenyl)acetate (126g) (0.056 g, 0.119 mmol) in THF (3 mL) and methanol (6 mL) using a solution of sodium hydroxide (2 M aqueous, 0.298 mL, 0.596 mmol). This gave after workup and purification by reverse phase column [C18 (50 g), eluting with ACN in water (containing 0.1% HCl) from 0-100%] 2-(2-((4-(3-(aminomethyl)phenyl)-1-(cyclopropylmethyl)-1H-indazol-6-yl)methoxy)phenyl)acetic acid (126h) (0.016 g, 30% yield) as a white solid; $^1$H NMR (300 MHz, DMSO-d$_6$) δ 12.1 (bs, 1H, D$_2$O exchangeable), 8.42-8.29 (m, 3H, D$_2$O exchangeable), 8.30 (s, 1H), 7.91 (s, 1H), 7.82 (s, 1H), 7.77 (d, J=7.4 Hz, 1H), 7.60 (t, J=7.5 Hz, 1H), 7.54 (d, J=7.6 Hz, 1H), 7.36 (s, 1H), 7.29-7.19 (m, 2H), 7.13-7.06 (m, 1H), 6.92 (t, J=7.4 Hz, 1H), 5.34 (s, 2H), 4.35 (d, J=6.9 Hz, 2H), 4.22-4.06 (m, 2H), 3.64 (s, 2H), 1.40-1.20 (m, 1H), 0.53-0.35 (m, 4H); MS (ES+): 442.3 (M+1); 883.5 (2M+1); MS (ES-): 440.4 (M-1); 476.3 (M+Cl), 881.7 (2M-1); HPLC purity: 94.67%.

Scheme-127

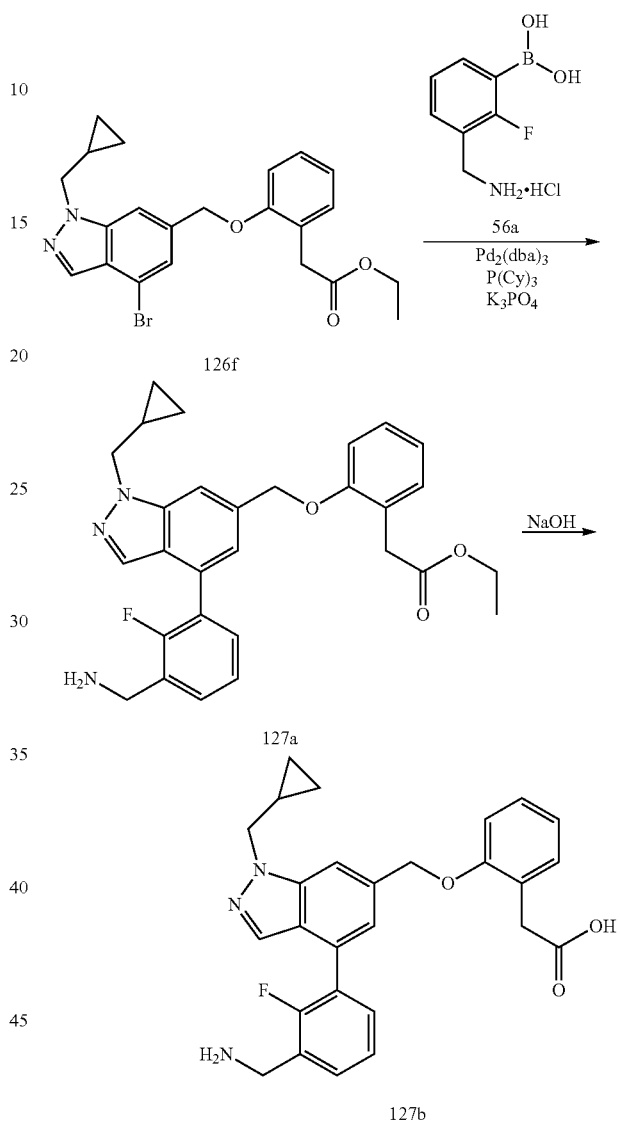

Preparation of 2-(2-((4-(3-(aminomethyl)-2-fluorophenyl)-1-(cyclopropylmethyl)-1H-indazol-6-yl)methoxy)phenyl)acetic Acid (127b)

Step-1: Preparation of Ethyl 2-(2-((4-(3-(aminomethyl)-2-fluorophenyl)-1-(cyclopropylmethyl)-1H-indazol-6-yl)methoxy)phenyl)acetate (127a)

Compound 127a was prepared according to the procedure reported in step-3 of Scheme-1 from ethyl 2-(2-((4-bromo-1-(cyclopropylmethyl)-1H-indazol-6-yl)methoxy)phenyl)acetate (126f) (0.45 g, 1.015 mmol) in dioxane (6 mL) using 3-(aminomethyl)-2-fluorophenylboronic acid (56a) (0.257 g, 1.523 mmol), tripotassium phosphate (1.3M, 2.342 mL, 3.05 mmol), tricyclohexylphosphine (0.171 g, 0.609 mmol) and Pd$_2$(dba)$_3$ (0.186 g, 0.203 mmol) under a nitrogen atmosphere and heating at 125° C. for 45 min in a microwave. This gave after workup, purification by flash column chromatography [silica (24 g), eluting with MeOH in DCM from 0-40%] compound 127a (0.255 g, 52% yield) as a free base, 120 mgs of this free base was subjected to reverse phase column chromatography [C18 (30 g), eluting with ACN in water (containing 0.1% HCl) from 0-100%] to afford ethyl 2-(2-((4-(3-(aminomethyl)-2-fluorophenyl)-1-(cyclopropylmethyl)-1H-indazol-6-yl)methoxy)phenyl)acetate (127a) (44 mg, 37%) HCl salt as a white solid; $^1$H NMR (300 MHz, DMSO-$d_6$) δ 8.43 (s, 3H, D$_2$O exchangeable), 8.02 (d, J=2.9 Hz, 1H), 7.85 (s, 1H), 7.66 (t, J=7.4 Hz, 2H), 7.43 (t, J=7.7 Hz, 1H), 7.31-7.17 (m, 3H), 7.11 (d, J=8.0 Hz, 1H), 6.92 (t, J=7.4 Hz, 1H), 5.32 (s, 2H), 4.35 (d, J=7.0 Hz, 2H), 4.24-4.12 (m, 2H), 3.93 (q, J=7.1 Hz, 2H), 3.66 (s, 2H), 1.39-1.21 (m, 1H), 0.99 (t, J=7.1 Hz, 3H), 0.56-0.36 (m, 4H); $^{19}$F NMR (282 MHz, DMSO-$d_6$) δ−118.61; MS (ES+): 488.3 (M+1); 975.6 (2M+1); MS (ES−): 522.4 (M+Cl); HPLC purity: 99.48%; Analysis calculated for: $C_{29}H_{30}FN_3O_3$.2.0$H_2O$.1.0HCl: C, 62.19; H, 6.30; N, 7.50; Found: C, 62.22; H, 6.23; N, 7.54.

Step-2: Preparation of 2-(2-((4-(3-(aminomethyl)-2-fluorophenyl)-1-(cyclopropylmethyl)-1H-indazol-6-yl)methoxy)phenyl)acetic Acid (127b)

Compound 127b was prepared according to the procedure reported in step-4 of Scheme-4, from ethyl 2-(2-((4-(3-(aminomethyl)-2-fluorophenyl)-1-(cyclopropylmethyl)-1H-indazol-6-yl)methoxy)phenyl)acetate (127a) (0.132 g, 0.271 mmol) in THF (3 mL) and methanol (6 mL) using a solution of sodium hydroxide (2 M aqueous, 0.677 mL, 1.354 mmol). This gave after workup and purification by reverse phase column [C18 (50 g), eluting with ACN in water (containing 0.1% HCl) from 0-100%] 2-(2-((4-(3-(aminomethyl)-2-fluorophenyl)-1-(cyclopropylmethyl)-1H-indazol-6-yl)methoxy)phenyl)acetic acid (127b) (0.050 g, 40% yield) HCl salt as a white solid; $^1$H NMR (300 MHz, DMSO-$d_6$) δ 12.2 (bs, 1H, D$_2$O exchangeable), 8.44 (s, 3H, D$_2$O exchangeable), 8.01 (d, J=2.9 Hz, 1H), 7.87 (s, 1H), 7.74-7.61 (m, 2H), 7.43 (t, J=7.7 Hz, 1H), 7.31-7.20 (m, 3H), 7.09 (d, J=8.4 Hz, 1H), 6.92 (t, J=7.3 Hz, 1H), 5.33 (s, 2H), 4.34 (d, J=7.0 Hz, 2H), 4.27-4.08 (m, 2H), 3.63 (s, 2H), 1.41-1.17 (m, 1H), 0.59-0.33 (m, 4H); $^{19}$F NMR (282 MHz, DMSO-$d_6$) δ−118.56; MS (ES+): 460.3 (M+1); 919.5 (2M+1); MS (ES−): 458.4 (M−1); 494.3 (M+Cl); 917.7 (2M−1); HPLC purity: 98.97%.

Scheme-128

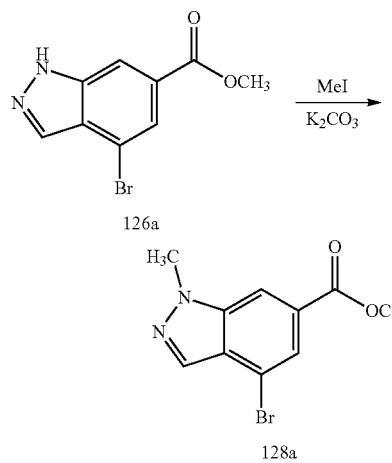

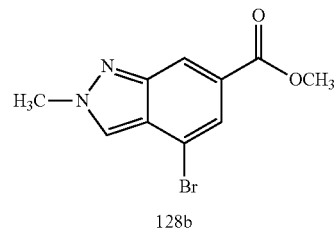

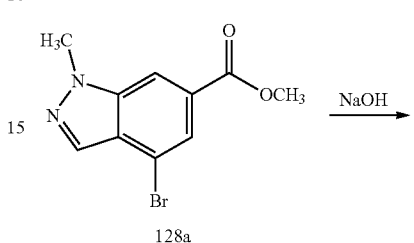

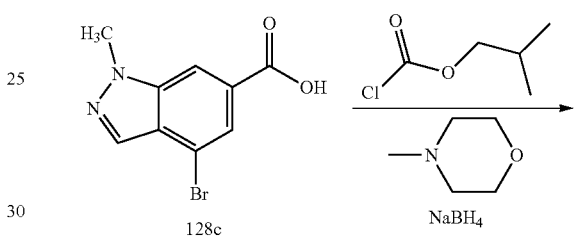

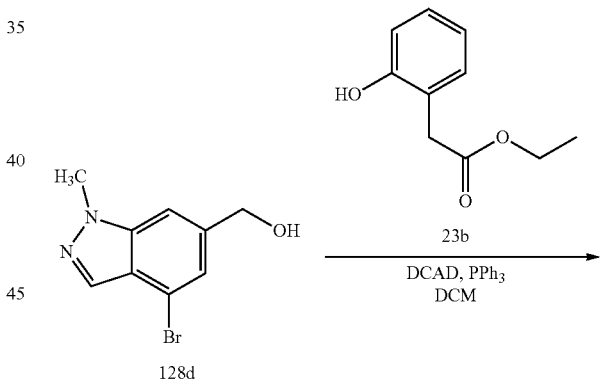

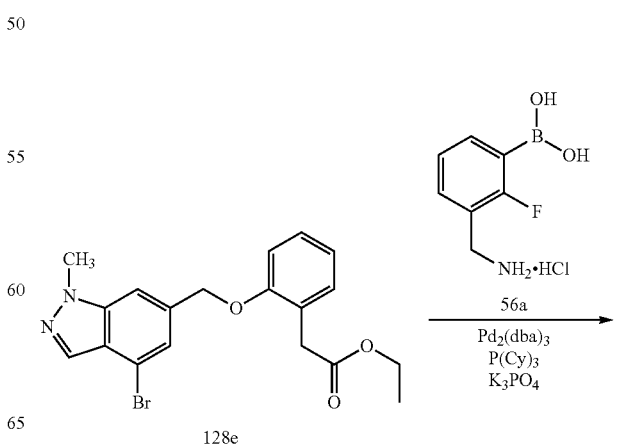

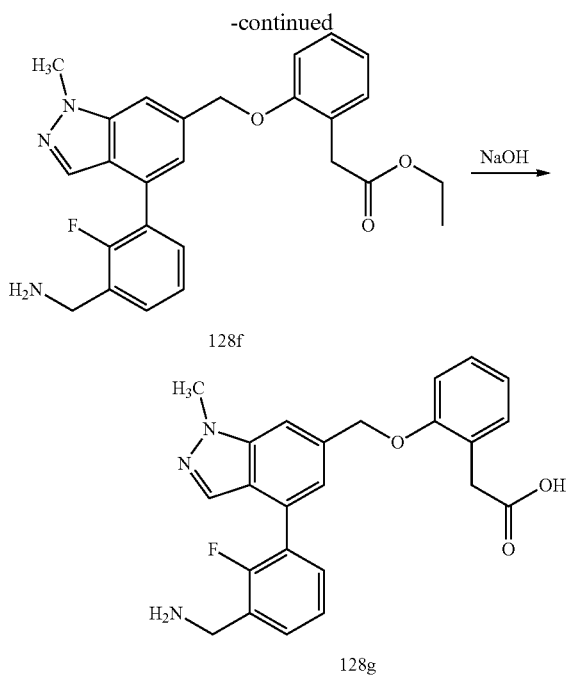

Preparation of 2-(2-((4-(3-(aminomethyl)-2-fluorophenyl)-1-methyl-1H-indazol-6-yl)methoxy)phenyl)acetic Acid (128g)

Step-1: Preparation of methyl 4-bromo-1-methyl-1H-indazole-6-carboxylate (128a) and methyl 4-bromo-2-methyl-2H-indazole-6-carboxylate (128b)

Compounds 128a and 128b were prepared according to the procedure reported in step-1 of Scheme-109, from methyl 4-bromo-1H-indazole-6-carboxylate (126a) (2.00 g, 8.30 mmol) in DMF using iodomethane (1.291 mL, 20.74 mmol) and potassium carbonate (4.01 g, 29.0 mmol). This gave after workup and purification by flash column chromatography [silica gel, 40 g, eluting with EtOAc in hexane from 0-60%] methyl 4-bromo-1-methyl-1H-indazole-6-carboxylate (128a) (1.003 g, 45% yield) as a white solid; $^1$H NMR (300 MHz, DMSO-$d_6$) δ 8.38-8.33 (m, 1H), 8.17-8.11 (m, 1H), 7.86-7.81 (m, 1H), 4.16 (s, 3H), 3.92 (s, 3H) and methyl 4-bromo-2-methyl-2H-indazole-6-carboxylate (128b) (0.591 g, 27% yield) as an off-white solid; $^1$H NMR (300 MHz, DMSO-$d_6$) δ 8.55 (s, 1H), 8.35-8.22 (m, 1H), 7.71 (d, J=1.1 Hz, 1H), 4.25 (s, 3H), 3.89 (s, 3H).

Step-2: Preparation of 4-bromo-1-methyl-1H-indazole-6-carboxylic Acid (128c)

Compound 128c was prepared according to the procedure reported in step-4 of Scheme-4, from methyl 4-bromo-1-methyl-1H-indazole-6-carboxylate (128a) (1.655 g, 6.15 mmol) in THF (15 mL) and methanol (30 mL) using a solution of sodium hydroxide (2 M aqueous, 12.30 mL, 24.60 mmol). This gave after workup 4-bromo-1-methyl-1H-indazole-6-carboxylic acid (128c) (1.479 g, 94% yield) as an off-white solid; $^1$H NMR (300 MHz, DMSO-$d_6$) δ 13.36 (s, 1H), 8.32 (s, 1H), 8.12 (s, 1H), 7.82 (s, 1H), 4.15 (s, 3H); MS (ES−): 255.1, 253.0 (M−2).

Step-3: Preparation of (4-bromo-1-methyl-1H-indazol-6-yl)methanol (128d)

Compound 128d was prepared according to the procedure reported in step-1 of Scheme-23 from 4-bromo-1-methyl-1H-indazole-6-carboxylic acid (128c) (1.43 g, 5.61 mmol) using N-methylmorpholine (0.74 mL, 6.73 mmol) in THF (20 mL), isobutyl chloroformate ((0.883 mL, 6.73 mmol) and NaBH$_4$ (0.636 g, 16.82 mmol) in water (20 mL). This gave after workup and purification by flash column chromatography [silica gel 40 g, eluting with ethyl acetate in hexanes from 0-100%] (4-bromo-1-methyl-1H-indazol-6-yl)methanol (128d) (1.21 g, 5.02 mmol, 90% yield) as a yellow oil; $^1$H NMR (300 MHz, DMSO-$d_6$) δ 7.99-7.91 (m, 1H), 7.63-7.53 (m, 1H), 7.36-7.30 (m, 1H), 5.41 (td, J=5.8, 1.0 Hz, 1H), 4.63 (d, J=5.7 Hz, 2H), 4.04 (s, 3H); MS (ES−): 241.1, 239.1 (M−2).

Step-4: Preparation of Ethyl 2-(2-((4-bromo-1-methyl-1H-indazol-6-yl)methoxy)phenyl)acetate (128e)

Compound 128e was prepared according to the procedure reported in step-2 of Scheme-23 from (4-bromo-1-methyl-1H-indazol-6-yl)methanol (128d) (1.2 g, 4.98 mmol) in DCM (30 mL) using triphenylphosphine (1.436 g, 5.48 mmol), ethyl 2-(2-hydroxyphenyl) acetate (23b) (0.987 g, 5.48 mmol) and di-(4-chlorobenzyl)azodicarboxylate (DCAD, 2.010 g, 5.48 mmol) in DCM (10 mL). This gave after workup and purification by flash column chromatography [silica gel, 40g, eluting with EtOAc in hexanes from 0-100%] ethyl 2-(2-((4-bromo-1-methyl-1H-indazol-6-yl)methoxy)phenyl)acetate (128e) (1.22 g, 3.03 mmol, 60.8% yield) as a yellow solid; $^1$H NMR (300 MHz, DMSO-$d_6$) δ 8.09-7.94 (m, 1H), 7.81-7.70 (m, 1H), 7.46-7.35 (m, 1H), 7.32-7.20 (m, 2H), 7.08 (d, J=8.0 Hz, 1H), 6.93 (td, J=7.4, 1.0 Hz, 1H), 5.24 (s, 2H), 4.10-3.99 (m, 5H), 3.67 (s, 2H), 1.08 (t, 3H); MS (ES+): 425.1 (M+Na); MS (ES−): 401.2 (M−2).

Step-5: Preparation of Ethyl 2-(2-((4-(3-(aminomethyl)-2-fluorophenyl)-1-methyl-1H-indazol-6-yl)methoxy)phenyl)acetate (128f)

Compound 128f was prepared according to the procedure reported in step-3 of Scheme-1 from ethyl 2-(2-((4-bromo-1-methyl-1H-indazol-6-yl)methoxy)phenyl)acetate (128e) (0.609 g, 1.510 mmol) in dioxane (6 mL) using (3-(aminomethyl)-2-fluorophenyl)boronic acid hydrochloride (56a) (0.383 g, 2.265 mmol), tripotassium phosphate (1.3M, 3.48 mL, 4.53 mmol), tricyclohexylphosphine (0.254 g, 0.906 mmol) and Pd$_2$(dba)$_3$ (0.277 g, 0.302 mmol) under an nitrogen atmosphere and heating at 125° C. for 45 min in a microwave. This gave after workup, purification by flash column chromatography [silica (24 g), eluting with MeOH in DCM from 0-40%] followed by purification by reverse phase column [C18 (50 g), eluting with ACN in water (containing 0.1% HCl) from 0-100%] ethyl 2-(2-((4-(3-(aminomethyl)-2-fluorophenyl)-1-methyl-1H-indazol-6-yl)methoxy)phenyl)acetate (128f) (0.358 g, 53% yield) HCl salt as a white solid; $^1$H NMR (300 MHz, DMSO-$d_6$) δ 8.50-8.36 (m, 3H), 8.02 (d, J=3.0 Hz, 1H), 7.80 (s, 1H), 7.66 (t, J=7.1 Hz, 2H), 7.43 (t, J=7.7 Hz, 1H), 7.32-7.19 (m, 3H), 7.12 (d, J=8.1 Hz, 1H), 6.92 (t, J=7.3 Hz, 1H), 5.32 (s, 2H), 4.22-4.15 (m, 2H), 4.10 (s, 3H), 3.93 (q, J=7.1 Hz, 2H), 3.67 (s, 2H), 0.99 (t, J=7.1 Hz, 3H); $^{19}$F NMR (282 MHz, DMSO-$d_6$) δ−118.62; MS (ES+): 448.3 (M+1); MS (ES−):

482.3 (M+Cl); HPLC purity: 98.19%; Analysis calculated for: $C_{26}H_{26}FN_3O_3 \cdot 0.25H_2O \cdot 1.0HCl$: C, 63.93; H, 5.67; Cl, 7.26; N, 8.60; Found: C, 63.81; H, 5.77; Cl, 7.11; N, 8.62.

Step-6: Preparation of 2-(2-((4-(3-(aminomethyl)-2-fluorophenyl)-1-methyl-1H-indazol-6-yl)methoxy)phenyl)acetic Acid (128g)

Compound 128g was prepared according to the procedure reported in step-4 of Scheme-4, from ethyl 2-(2-((4-(3-(aminomethyl)-2-fluorophenyl)-1-methyl-1H-indazol-6-yl)methoxy)phenyl)acetate (128f) (0.179 g, 0.40 mmol) in THF (3 mL) and methanol (6 mL) using a solution of sodium hydroxide (2 M aqueous, 1.0 mL, 2.0 mmol). This gave after workup and purification by reverse phase column [C18 (50 g), eluting with ACN in water (containing 0.1% HCl) from 0-100%] 2-(2-((4-(3-(aminomethyl)-2-fluorophenyl)-1-methyl-1H-indazol-6-yl)methoxy)phenyl)acetic acid (128g) (0.079 g, 47% yield) as a white solid; $^1$H NMR (300 MHz, DMSO-$d_6$) δ 12.2 (bs, 1H, $D_2O$ exchangeable), 8.44 (s, 3H, $D_2O$ exchangeable), 8.02 (d, J=3.0 Hz, 1H), 7.83 (s, 1H), 7.66 (t, J=7.3 Hz, 2H), 7.42 (t, J=7.6 Hz, 1H), 7.29 (s, 1H), 7.24 (d, J=7.2 Hz, 2H), 7.10 (d, J=8.4 Hz, 1H), 6.92 (t, J=7.4 Hz, 1H), 5.34 (s, 2H), 4.24-4.13 (m, 2H), 4.09 (s, 3H), 3.63 (s, 2H); $^{19}$F NMR (282 MHz, DMSO-$d_6$) δ−118.58; MS (ES+): 420.3 (M+1); 839.5 (2M+1); MS (ES-): 418.3 (M−1); 454.3 (M+Cl), 837.6 (2M−1); HPLC purity: 98.76%; Analysis calculated for: $C_{24}H_{22}FN_3O_3 \cdot 2.0H_2O \cdot 1.05HCl$: C, 58.38; H, 5.52; Cl, 7.54; N, 8.51; Found: C, 58.32; H, 5.45; Cl, 7.76; N, 8.56.

Scheme-129

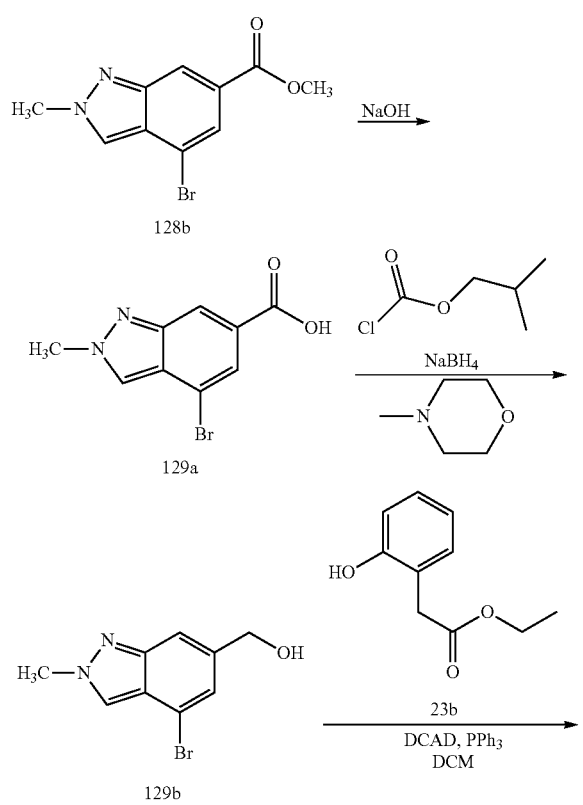

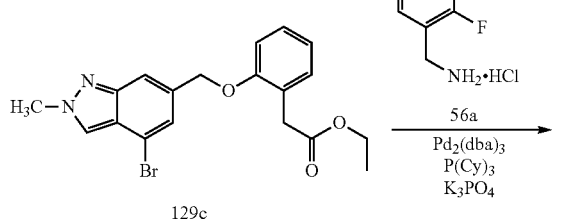

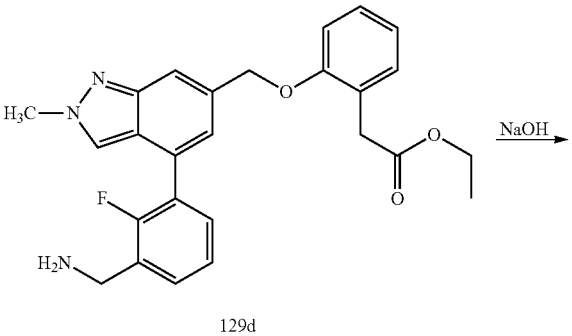

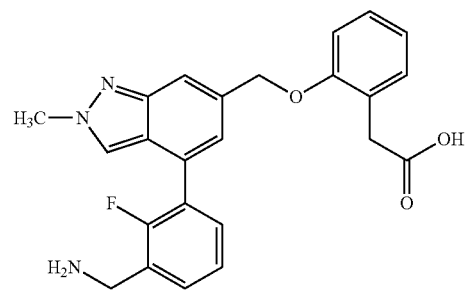

Preparation of 2-(2-((4-(3-(aminomethyl)-2-fluorophenyl)-2-methyl-2H-indazol-6-yl)methoxy)phenyl)acetic Acid (129e)

Step-1: Preparation of 4-bromo-2-methyl-2H-indazole-6-carboxylic acid (129a)

Compound 129a was prepared according to the procedure reported in step-4 of Scheme-4, from methyl 4-bromo-2-methyl-2H-indazole-6-carboxylate (128b) (1.2 g, 4.46 mmol) in THF (15 mL) and methanol (30 mL) using a solution of sodium hydroxide (2 M aqueous, 8.92 mL, 17.84 mmol). This gave after workup 4-bromo-2-methyl-2H-indazole-6-carboxylic acid (129a) (1.06 g, 93% yield) as an off-white solid; $^1$H NMR (300 MHz, DMSO-$d_6$) δ 13.15 (s, 1H), 8.53 (s, 1H), 8.25 (s, 1H), 7.77-7.61 (m, 1H), 4.24 (s, 3H).

Step-2: Preparation of (4-bromo-2-methyl-2H-indazol-6-yl)methanol (129b)

Compound 129b was prepared according to the procedure reported in step-1 of Scheme-23 from 4-bromo-2-methyl-2H-indazole-6-carboxylic acid (129a) (1.00 g, 3.92 mmol) using N-methylmorpholine (0.517 mL, 4.70 mmol) in THF (20 mL), isobutyl chloroformate (0.618 mL, 4.70 mmol) and NaBH$_4$ (0.445 g, 11.76 mmol) in water (20 mL). This gave after workup and purification by flash column chromatography [silica gel 24 g, eluting with ethyl acetate in hexanes from 0-100%] (4-bromo-2-methyl-2H-indazol-6-yl)methanol (129b) (0.684 g, 72% yield) as an off-white solid; $^1$H NMR (300 MHz, DMSO-d$_6$) δ 8.48-8.24 (m, 1H), 7.65-7.38 (m, 1H), 7.32-7.15 (m, 1H), 5.43-5.22 (m, 1H), 4.55 (d, J=5.5 Hz, 2H), 4.34-4.02 (m, 3H).

Step-3: Preparation of Ethyl 2-(2-((4-bromo-2-methyl-2H-indazol-6-yl)methoxy)phenyl)acetate (129c)

Compound 129c was prepared according to the procedure reported in step-2 of Scheme-23 from (4-bromo-2-methyl-2H-indazol-6-yl)methanol (129b) (0.670 g, 2.78 mmol) in DCM (30 mL) using triphenylphosphine (0.802 g, 3.06 mmol) ethyl 2-(2-hydroxyphenyl) acetate (23b) (0.551 g, 3.06 mmol) and di-(4-chlorobenzyl)azodicarboxylate (1.122 g, 3.06 mmol) in DCM (20 mL). This gave after workup and purification by flash column chromatography [silica gel 24g, eluting with EtOAc in hexanes from 0-100%] ethyl 2-(2-((4-bromo-2-methyl-2H-indazol-6-yl)methoxy)phenyl)acetate (129c) (0.681 g, 61% yield) as a white waxy solid; $^1$H NMR (300 MHz, DMSO-d$_6$) δ 8.39 (s, 1H), 7.73-7.65 (m, 1H), 7.30-7.28 (m, 1H), 7.26-7.21 (m, 2H), 7.07 (d, J=8.0 Hz, 1H), 6.91 (td, J=7.4, 1.1 Hz, 1H), 5.17 (s, 2H), 4.18 (d, J=1.4 Hz, 3H), 4.05 (q, J=7.1 Hz, 2H), 3.64 (s, 2H), 1.12 (t, J=7.2 Hz, 3H); MS (ES+): 425.2, 427.2 (M+Na).

Step-4: Preparation of Ethyl 2-(2-((4-(3-(aminomethyl)-2-fluorophenyl)-2-methyl-2H-indazol-6-yl)methoxy)phenyl)acetate (129d)

Compound 129d was prepared according to the procedure reported in step-3 of Scheme-1 from ethyl 2-(2-((4-bromo-2-methyl-2H-indazol-6-yl)methoxy)phenyl)acetate (129c) (0.655 g, 1.624 mmol) in dioxane (6 mL) using (3-(aminomethyl)-2-fluorophenyl)boronic acid hydrochloride (56a) (0.412 g, 2.436 mmol), tripotassium phosphate (1.3M, 3.75 mL, 4.87 mmol), tricyclohexylphosphine (0.273 g, 0.975 mmol) and Pd$_2$(dba)$_3$ (0.297 g, 0.325 mmol) under a nitrogen atmosphere and heating at 125° C. for 45 min in a microwave. This gave after workup, purification by flash column chromatography [silica (24 g), eluting with MeOH in DCM from 0-40%] followed by purification by reverse phase column [C18 (50 g), eluting with ACN in water (containing 0.1% HCl) from 0-100%] ethyl 2-(2-((4-(3-(aminomethyl)-2-fluorophenyl)-2-methyl-2H-indazol-6-yl)methoxy)phenyl)acetate (129d) (0.458 g, 63% yield) as a white solid; $^1$H NMR (300 MHz, DMSO-d$_6$) δ 8.54 (s, 3H, D$_2$O exchangeable), 8.43-8.35 (m, 1H), 7.73 (s, 1H), 7.73-7.51 (m, 2H), 7.41 (t, J=7.7 Hz, 1H), 7.29-7.18 (m, 2H), 7.16 (s, 1H), 7.11 (d, J=8.2 Hz, 1H), 6.96-6.85 (m, 1H), 5.24 (s, 2H), 4.17 (s, 5H), 3.95 (q, J=7.1 Hz, 2H), 3.68-3.59 (m, 2H), 1.03 (t, J=7.1 Hz, 3H); $^{19}$F NMR (282 MHz, DMSO-d$_6$) δ−118.09; MS (ES+): 448.3 (M+1), 895.6 (2M+1); MS (ES−): 482.3 (M+Cl); Analysis calculated for: C$_{26}$H$_{26}$FN$_3$O$_3$.1.75H$_2$O.1.25HCl: C, 59.53; H, 5.91; Cl, 8.45; N, 8.01; Found: C, 59.50; H, 5.69; Cl, 9.05; N, 8.01.

Step-5: Preparation of 2-(2-((4-(3-(aminomethyl)-2-fluorophenyl)-2-methyl-2H-indazol-6-yl)methoxy)phenyl)acetic Acid (129e)

Compound 129e was prepared according to the procedure reported in step-4 of Scheme-4, from ethyl 2-(2-((4-(3-(aminomethyl)-2-fluorophenyl)-2-methyl-2H-indazol-6-yl)methoxy)phenyl)acetate (129d) (0.219 g, 0.489 mmol) in THF (4 mL) and methanol (8 mL) using a solution of sodium hydroxide (2 M aqueous, 1.223 mL, 2.447 mmol). This gave after workup and purification by reverse phase column [C18 (50 g), eluting with ACN in water (containing 0.1% HCl) from 0-100%] 2-(2-((4-(3-(aminomethyl)-2-fluorophenyl)-2-methyl-2H-indazol-6-yl)methoxy)phenyl)acetic acid (129e) (0.060 g, 29% yield) as a white solid; $^1$H NMR (300 MHz, DMSO-d$_6$) δ 8.68-8.49 (m, 3H, D$_2$O exchangeable), 8.44-8.38 (m, 1H), 7.74 (s, 1H), 7.71-7.59 (m, 2H), 7.40 (t, J=7.6 Hz, 1H), 7.28-7.18 (m, 3H), 7.09 (d, J=8.1 Hz, 1H), 6.90 (t, J=7.4 Hz, 1H), 5.25 (s, 2H), 4.27-4.08 (m, 5H), 3.59 (s, 2H); $^{19}$F NMR (282 MHz, DMSO-d$_6$) δ−117.96; MS (ES+): 420.3 (M+1); 839.5 (2M+1); MS (ES−): 454.3 (M+Cl), 837.7 (2M−1), 873.5 (2M+Cl); HPLC purity: 98.12%.

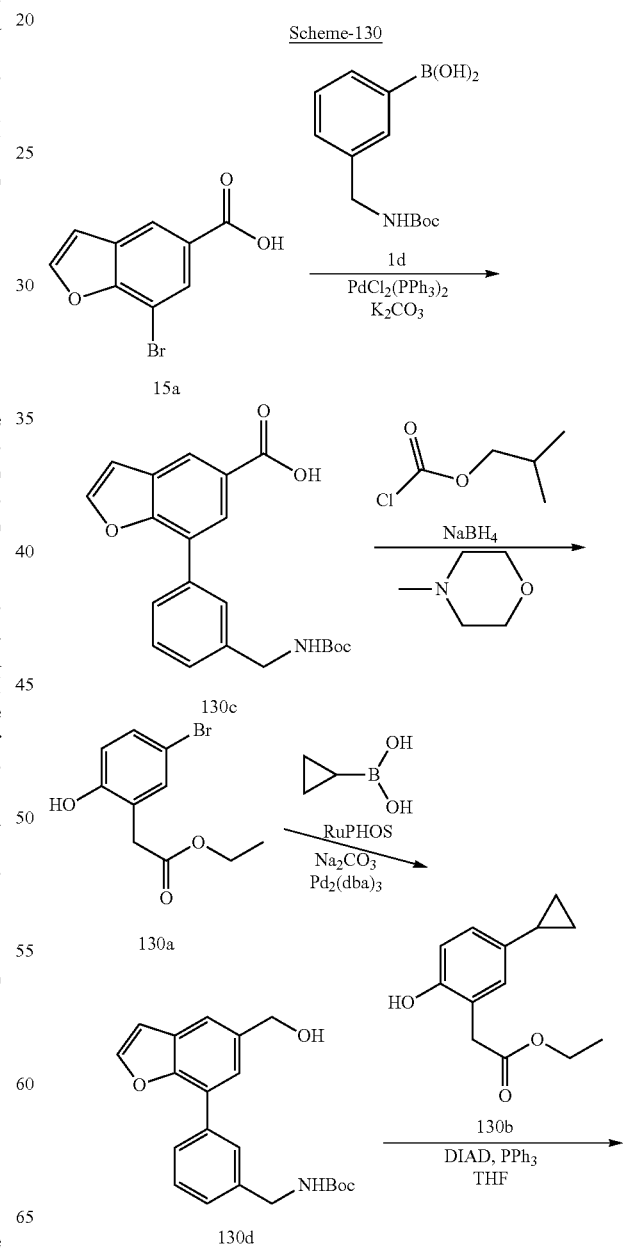

Scheme-130

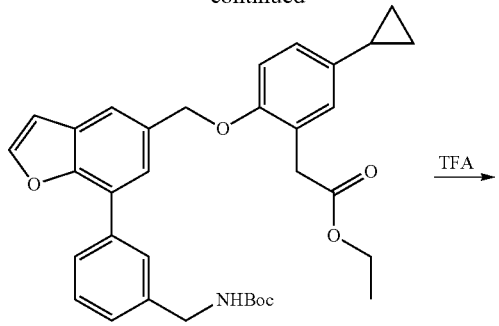

130e

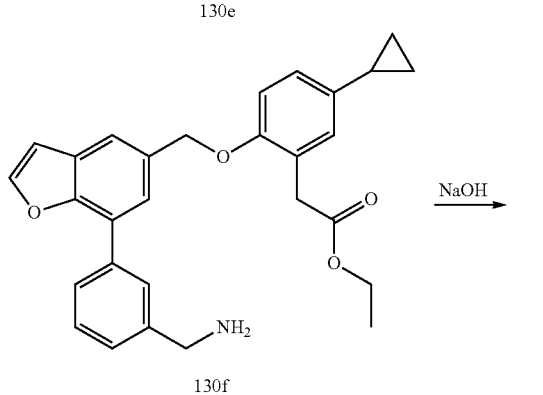

130f

130g

Preparation of 2-(2-((7-(3-(aminomethyl)phenyl) benzofuran-5-yl)methoxy)-5-cyclopropylphenyl) acetic Acid (130g)

Step-1: Preparation of Ethyl 2-(5-cyclopropyl-2-hydroxyphenyl)acetate (130b)

To a solution of ethyl 2-(5-bromo-2-hydroxyphenyl)acetate (130a) (0.5 g, 1.93 mmol; CAS #220801-65-0) in toluene (20 mL) was added cyclopropyl boronic acid (0.249 g, 2.89 mmol), dicyclohexyl(2',6'-diisopropoxybiphenyl-2-yl)phosphine (RuPHOS) (0.090 g, 0.193 mmol), Pd$_2$(dba)$_3$ (0.088 g, 0.096 mmol) and a solution of Na$_2$CO$_3$ (0.82 g, 7.72 mmol) in water (2 mL) under a nitrogen atmosphere and heated at 100° C. for 2.5 h. The reaction mixture was cooled to RT, diluted with EtOAc (100 mL), washed with brine (50 mL), dried, filtered and evaporated to dryness. The residue obtained was purified by flash column chromatography [silica gel 24 g, eluting with EtOAc in hexanes from 0-40%] to afford ethyl 2-(5-cyclopropyl-2-hydroxyphenyl) acetate (130b) (0.256 g, 1.162 mmol, 60.2% yield) as thick yellow oil; $^1$H NMR (300 MHz, DMSO-d$_6$) δ 9.17 (s, 1H), 6.86-6.73 (m, 2H), 6.66 (d, J=8.2 Hz, 1H), 4.05 (q, J=8.8, 8.0 Hz, 2H), 3.48 (s, 2H), 1.86-1.70 (m, 1H), 1.17 (t, J=7.1 Hz, 3H), 0.91-0.74 (m, 2H), 0.62-0.42 (m, 2H).

Step-2: Preparation of 7-(3-(((tert-butoxycarbonyl) amino)methyl)phenyl)benzofuran-5-carboxylic Acid (130c)

Compound 130c was prepared according to the procedure reported in step-3 of Scheme-1 from 7-bromobenzofuran-5-carboxylic acid (15a) (3 g, 12.45 mmol) in dioxane (100 mL) using (3-((tert-butoxycarbonyl)amino)methyl)phenylboronic acid (id) (4.38 g, 17.42 mmol), a solution of potassium carbonate (5.16 g, 37.3 mmol) in water (10 mL) and bis(triphenylphosphine)palladium(II) chloride (1.310 g, 1.867 mmol) and heating under a nitrogen atmosphere at 100° C. for 3 h on an oil bath. This gave after workup, purification by flash column chromatography [silica (40 g), eluting with DMA80 in DCM from 0-50%] 7-(3-(((tert-butoxycarbonyl)amino)methyl)phenyl)benzofuran-5-carboxylic acid (130c) (2.7 g, 7.35 mmol, 59.0% yield) as a clear oil; $^1$H NMR (300 MHz, DMSO-d$_6$) δ 8.22 (d, J=1.5 Hz, 1H), 8.12-8.05 (m, 2H), 7.76-7.68 (m, 2H), 7.56-7.43 (m, 2H), 7.29 (d, J=7.6 Hz, 1H), 7.10 (d, J=2.2 Hz, 1H), 4.23 (d, J=6.2 Hz, 2H), 1.39 (s, 9H); MS (ES−) 366.3 (M−1).

Step-3: Preparation of tert-butyl 3-(5-(hydroxymethyl)benzofuran-7-yl)benzylcarbamate (130d)

Compound 130d was prepared according to the procedure reported in step-1 of Scheme-23 from 7-(3-(((tert-butoxycarbonyl)amino)methyl)phenyl)benzofuran-5-carboxylic acid (130c) (1.7 g, 4.63 mmol) using N-methylmorpholine (0.610 mL, 5.55 mmol) in THF (40 mL), isobutyl chloroformate (0.729 mL, 5.55 mmol) and NaBH$_4$ (0.525 g, 13.88 mmol) in water (5 mL). This gave after workup tert-butyl 3-(5-(hydroxymethyl)benzofuran-7-yl)benzylcarbamate (130d) (1.1 g, 3.11 mmol, 67.3% yield) as a white solid; $^1$H NMR (300 MHz, DMSO-d$_6$) δ 8.02 (d, J=2.2 Hz, 1H), 7.73 (m, 2H), 7.59 (d, J=1.6 Hz, 1H), 7.52-7.38 (m, 3H), 7.28 (d, J=7.6 Hz, 1H), 7.01 (d, J=2.1 Hz, 1H), 5.23 (t, J=5.7 Hz, 1H), 4.64 (d, J=5.7 Hz, 2H), 4.22 (d, J=6.2 Hz, 2H), 1.40 (s, 9H).

Step-4: Preparation of Ethyl 2-(2-((7-(3-(((tert-butoxycarbonyl)amino)methyl)phenyl)benzofuran-5-yl)methoxy)-5-cyclopropylphenyl)acetate (130e)

Compound 130e was prepared according to the procedure reported in step-2 of Scheme-23 from tert-butyl 3-(5-(hydroxymethyl)benzofuran-7-yl)benzylcarbamate (130d) (0.400 g, 1.132 mmol) in THF (15 mL) using triphenylphosphine (0.327 g, 1.245 mmol), ethyl 2-(5-cyclopropyl-2-hydroxyphenyl)acetate (130b) (0.249 g, 1.132 mmol) and DIAD (0.252 g, 1.245 mmol). This gave after workup and purification by flash column chromatography [silica gel 24 g, eluting with ethyl acetate in hexanes from 0-100%] ethyl 2-(2-((7-(3-(((tert-butoxycarbonyl)amino)methyl)phenyl) benzofuran-5-yl)methoxy)-5-cyclopropylphenyl)acetate (130e) (0.113 mmol, 10% yield) as a pale-yellow waxy solid; $^1$H NMR (300 MHz, DMSO-d$_6$) δ 8.06 (d, J=2.2 Hz, 1H), 7.79-7.64 (m, 3H), 7.56-7.40 (m, 3H), 7.30 (d, J=7.7 Hz, 1H), 7.04 (d, J=2.2 Hz, 1H), 6.99-6.91 (m, 3H), 5.18 (s, 2H), 4.22 (d, J=6.1 Hz, 2H), 3.92 (q, J=7.1 Hz, 2H), 3.58 (s, 2H), 1.91-1.77 (m, 1H), 1.39 (s, 9H), 0.98 (t, J=7.1 Hz, 3H), 0.91-0.81 (m, 2H), 0.66-0.50 (m, 2H); MS (ES+): 578.4 (M+Na); MS (ES−): 590.4 (M+Cl).

Step-5: Preparation of Ethyl 2-(2-((7-(3-(aminomethyl)phenyl)benzofuran-5-yl)methoxy)-5-cyclopropylphenyl)acetate (130f)

Compound 130f was prepared according to the procedure reported in step-5 of Scheme-1 from ethyl 2-(2-((7-(3-(((tert-butoxycarbonyl)amino)methyl)phenyl)benzofuran-5-yl)methoxy)-5-cyclopropylphenyl)acetate (130e) (0.062 g, 0.112 mmol) in DCM (5 mL) using TFA (0.172 mL, 2.232 mmol). This gave after workup and purification by flash column chromatography [silica gel 12 g, eluting with methanol in DCM from 0-100%] ethyl 2-(2-((7-(3-(aminomethyl)phenyl)benzofuran-5-yl)methoxy)-5-cyclopropylphenyl)acetate (130f) (0.031 g, 61% yield) as a white solid; MS (ES+): 456.3 (M+1).

Step-6: Preparation of 2-(2-((7-(3-(aminomethyl)phenyl)benzofuran-5-yl)methoxy)-5-cyclopropylphenyl)acetic Acid (130g)

Compound 130g was prepared according to the procedure reported in step-4 of Scheme-4, from ethyl 2-(2-((7-(3-(aminomethyl)phenyl)benzofuran-5-yl)methoxy)-5-cyclopropylphenyl)acetate (130f) (0.030 g, 0.066 mmol) in THF (3 mL) and methanol (6 mL) using a solution of sodium hydroxide (2 M aqueous, 0.165 mL, 0.329 mmol). This gave after workup and purification by reverse phase column [C18 (30 g), eluting with ACN in water (containing 0.1% HCl) from 0-100%] 2-(2-((7-(3-(aminomethyl)phenyl)benzofuran-5-yl)methoxy)-5-cyclopropylphenyl)acetic acid (130g) (0.008 g, 28% yield) HCl salt as a white solid; $^1$H NMR (300 MHz, DMSO-$d_6$) δ 12.2 (bs, 1H, D$_2$O exchangeable), 8.36 (bs, 3H, D$_2$O exchangeable), 8.13-8.05 (m, 1H), 7.99 (s, 1H), 7.97-7.89 (m, 1H), 7.75 (s, 1H), 7.69-7.50 (m, 3H), 7.05 (t, J=1.8 Hz, 1H), 7.02-6.88 (m, 3H), 5.22 (s, 2H), 4.14 (s, 2H), 3.56 (s, 2H), 1.93-1.76 (m, 1H), 0.94-0.80 (m, 2H), 0.69-0.46 (m, 2H); MS (ES+): 428.3 (M+1), 855.5 (2M+1); MS (ES−): 426.4 (M−1), 462.3 (M+Cl).

Scheme-131

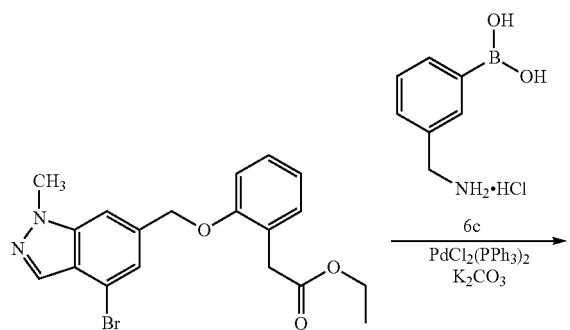

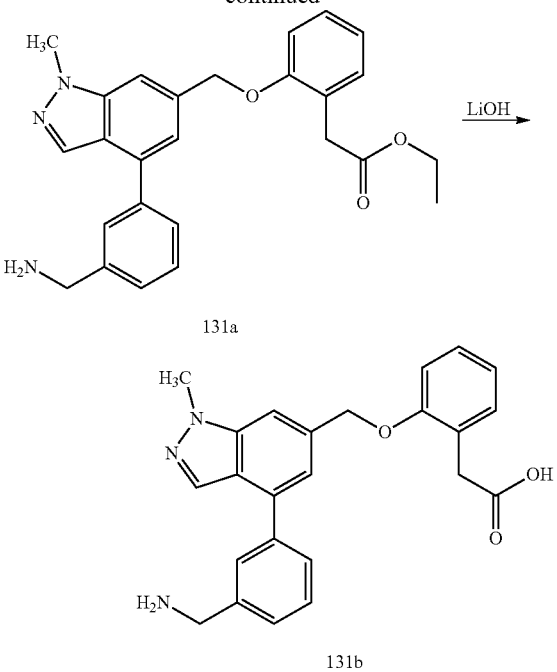

Preparation of 2-(2-((4-(3-(aminomethyl)phenyl)-1-methyl-1H-indazol-6-yl)methoxy)phenyl)acetic Acid (131b)

Step-1: Preparation of Ethyl 2-(2-((4-(3-(aminomethyl)phenyl)-1-methyl-1H-indazol-6-yl)methoxy)phenyl)acetate (131a)

Compound 131a was prepared according to the procedure reported in step-3 of Scheme-1 from ethyl 2-(2-((4-bromo-1-methyl-1H-indazol-6-yl)methoxy)phenyl)acetate (128e) (0.750 g, 1.860 mmol) in dioxane (30 mL) using (3-(aminomethyl)phenyl)boronic acid hydrochloride (6c) (0.453 g, 2.418 mmol), bis(triphenylphosphine)palladium(II) chloride (PdCl$_2$(PPh$_3$)$_2$, 0.196 g, 0.279 mmol) and a solution of potassium carbonate (0.771 g, 5.58 mmol) in water (5 mL) under an nitrogen atmosphere and heating at 100° C. for 3h on an oil bath. This gave after workup, purification by flash column chromatography [silica (40 g), eluting with MeOH in DCM from 0-100%] compound 131a (0.395 g, 49% yield) free base as an off-white solid. The free base (216 mgs) was subjected to further purification by reverse phase column chromatography [C18 (100 g), eluting with ACN in water (containing 0.1% HCl) from 0-100%] to afford ethyl 2-(2-((4-(3-(aminomethyl)phenyl)-1-methyl-1H-indazol-6-yl)methoxy)phenyl)acetate (131a) (0.215 mg, 89% yield) HCl salt as a white solid; $^1$H NMR (500 MHz, DMSO-$d_6$) δ 8.35 (bs, 3H, D$_2$O exchangeable), 8.31 (s, 1H), 7.93-7.86 (m, 1H), 7.78-7.72 (m, 2H), 7.60 (t, J=7.6 Hz, 1H), 7.57-7.52 (m, 1H), 7.35 (d, J=1.2 Hz, 1H), 7.29-7.20 (m, 2H), 7.15-7.09 (m, 1H), 6.92 (td, J=7.4, 1.0 Hz, 1H), 5.32 (s, 2H), 4.15 (q, J=5.8 Hz, 2H), 4.10 (s, 3H), 3.94 (q, J=7.1 Hz, 2H), 3.67 (s, 2H), 0.98 (t, J=7.1 Hz, 3H); MS (ES+): 430.4 (M+1), 859.9 (2M+1); MS (ES−): 464.4 (M+Cl); HPLC purity: 98.8%.

581

Step-2: Preparation of 2-(2-((4-(3-(aminomethyl)phenyl)-1-methyl-1H-indazol-6-yl)methoxy)phenyl)acetic Acid (131b)

Compound 131b was prepared according to the procedure reported in step-6 of Scheme-1, from ethyl 2-(2-((4-(3-(aminomethyl)phenyl)-1-methyl-1H-indazol-6-yl)methoxy)phenyl)acetate (131a) (0.175 g, 0.407 mmol) in THF (2 mL) and methanol (4 mL) using a solution of lithium hydroxide monohydrate (0.051 g, 1.22 mmol) in water (2 mL). This gave after workup and purification by reverse phase column [C18 (50 g), eluting with ACN in water (containing 0.1% HCl) from 0-100%] 2-(2-((4-(3-(aminomethyl)phenyl)-1-methyl-1H-indazol-6-yl)methoxy)phenyl)acetic acid (131b) (0.102 g, 62% yield) HCl salt as a white solid; $^1$H NMR (500 MHz, DMSO-$d_6$) δ 12.24 (bs, 1H, $D_2O$ exchangeable), 8.37 (bs, 3H, $D_2O$ exchangeable), 8.30 (s, 1H), 7.90 (s, 1H), 7.80-7.74 (m, 2H), 7.59 (t, J=7.6 Hz, 1H), 7.56-7.52 (m, 1H), 7.38 (d, J=1.1 Hz, 1H), 7.29-7.20 (m, 2H), 7.10 (d, J=8.4 Hz, 1H), 6.92 (t, J=7.4 Hz, 1H), 5.34 (s, 2H), 4.15 (q, J=5.9 Hz, 2H), 4.10 (s, 3H), 3.64 (s, 2H); MS (ES+): 402.2 (M+1), 803.8 (2M+1); MS (ES−): 400.5 (M−1), 436.4 (M+Cl), 801.8 (2M−1); HPLC purity: 97.33%; Analysis calculated for $C_{24}H_{23}N_3O_3 \cdot 2H_2O \cdot 1.25HCl$: C, 59.67; H, 5.89; Cl, 9.17; N, 8.70; Found: C, 59.63; H, 5.53; Cl, 9.64; N, 8.76.

Scheme-132

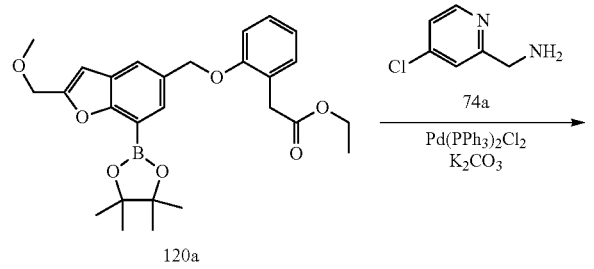

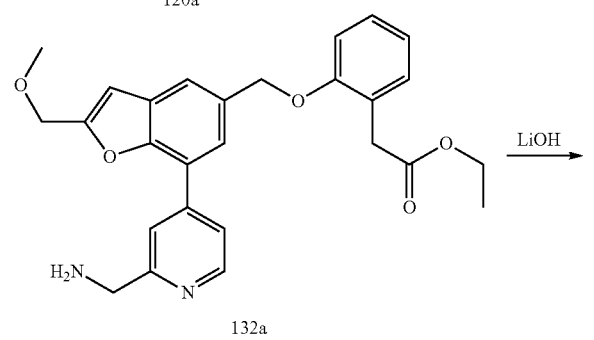

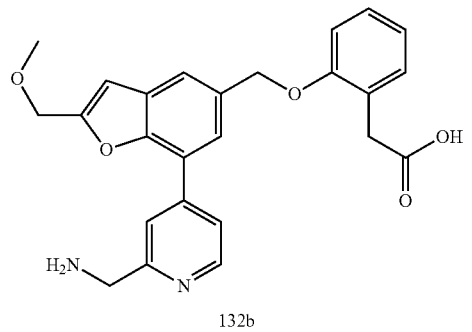

582

Preparation of 2-(2-((7-(2-(aminomethyl)pyridin-4-yl)-2-(methoxymethyl)benzofuran-5-yl)methoxy)phenyl)acetic Acid (132b)

Step-1: Preparation of Ethyl 2-(2-((7-(2-(aminomethyl)pyridin-4-yl)-2-(methoxymethyl)benzofuran-5-yl)methoxy)phenyl)acetate (132a)

Compound 132a was prepared according to the procedure reported in step-3 of Scheme-1 from ethyl 2-(2-((2-(methoxymethyl)-7-(4,4,5,5-tetramethyl-1,3,2-dioxaborolan-2-yl)benzofuran-5-yl)methoxy)phenyl)acetate (120a) (600 mg, 1.25 mmol) in dioxane (6 mL) using (4-chloropyridin-2-yl)methanamine (74a) (267 mg, 1.874 mmol), bis(triphenylphosphine)palladium(II) chloride (132 mg, 0.19 mmol) and a solution of $K_2CO_3$ (432 mg, 3.12 mmol) in water (3 mL) under an Ar atmosphere and heating at 100° C. for 2 h on oil bath. This gave after workup, purification by flash column chromatography [silica (40 g), eluting with DMA80 in DCM from 0-70%] followed by purification by reverse phase column [C18 (50 g), eluting with ACN in water (containing 0.1% HCl) from 0-100%] ethyl 2-(2-((7-(2-(aminomethyl)pyridin-4-yl)-2-(methoxymethyl)benzofuran-5-yl)methoxy)phenyl)acetate (132a) (223 mg, 39% yield) HCl salt as a yellow solid; $^1$H NMR (500 MHz, DMSO-$d_6$) δ 8.79 (d, J=5.3 Hz, 1H), 8.51 (s, 3H, $D_2O$ exchangeable), 8.05 (d, J=1.6 Hz, 1H), 7.97 (dd, J=5.4, 1.7 Hz, 1H), 7.81 (d, J=1.6 Hz, 1H), 7.77 (d, J=1.6 Hz, 1H), 7.28-7.19 (m, 2H), 7.11 (d, J=8.1 Hz, 1H), 7.06 (s, 1H), 6.91 (t, J=7.3 Hz, 1H), 5.25 (s, 2H), 4.60 (s, 2H), 4.30 (q, J=5.9 Hz, 2H), 3.94 (q, J=7.1 Hz, 2H), 3.64 (s, 2H), 3.33 (s, 3H), 0.99 (t, J=7.1 Hz, 3H); MS (ES+): 461.5 (M+1); (ES−): 495.5 (M+Cl).

Step-2: Preparation of 2-(2-((7-(2-(aminomethyl)pyridin-4-yl)-2-(methoxymethyl)benzofuran-5-yl)methoxy)phenyl)acetic Acid (132b)

Compound 132b was prepared according to the procedure reported in step-6 of Scheme-1, from ethyl 2-(2-((7-(2-(aminomethyl)pyridin-4-yl)-2-(methoxymethyl)benzofuran-5-yl)methoxy)phenyl)acetate (132a) (156 mg, 0.34 mmol) in MeOH/THF (10 mL) using a solution of lithium hydroxide monohydrate (43 mg, 1.02 mmol) in water (2.0 mL). This gave after workup and purification by reverse phase column [C18 (50 g), eluting with ACN in water (containing 0.1% HCl) from 0-100%] 2-(2-((7-(2-(aminomethyl)pyridin-4-yl)-2-(methoxymethyl)benzofuran-5-yl)methoxy)phenyl)acetic acid (132b) (105 mg, 72% yield) HCl salt as a white solid; $^1$H NMR (500 MHz, DMSO-$d_6$) δ 8.79 (d, J=5.3 Hz, 1H), 8.47 (s, 3H, $D_2O$ exchangeable), 8.04 (s, 1H), 7.98 (dd, J=5.2, 1.7 Hz, 1H), 7.84 (d, J=1.7 Hz, 1H), 7.80 (d, J=1.7 Hz, 1H), 7.26-7.20 (m, 2H), 7.09 (d, J=8.1 Hz, 1H), 7.05 (s, 1H), 6.91 (td, J=7.3, 1.0 Hz, 1H), 5.28 (s, 2H), 4.61 (s, 2H), 4.33-4.29 (m, 2H), 3.61 (s, 2H), 3.34 (s, 3H); MS (ES+): 433.2 (M+1); (ES−): 431.3 (M−1).

Scheme-133

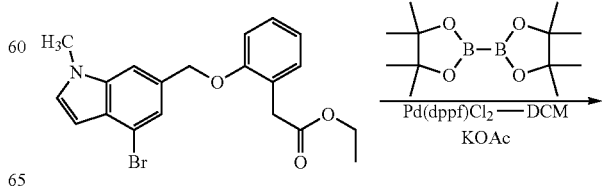

-continued

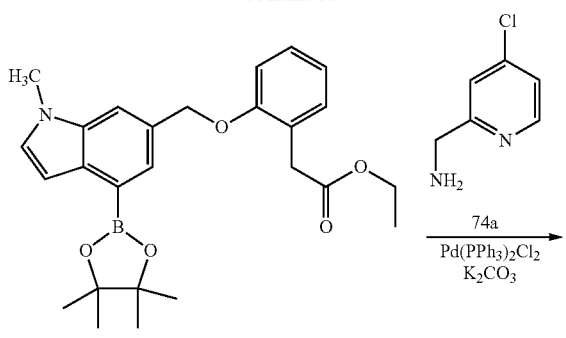

133a

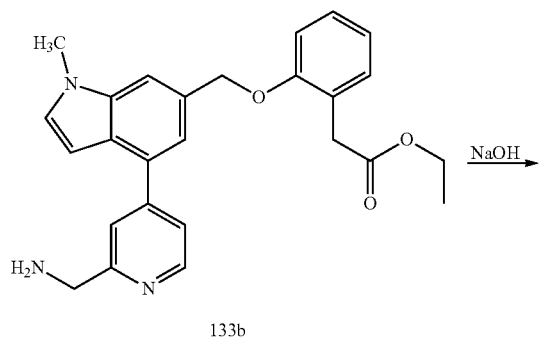

133b

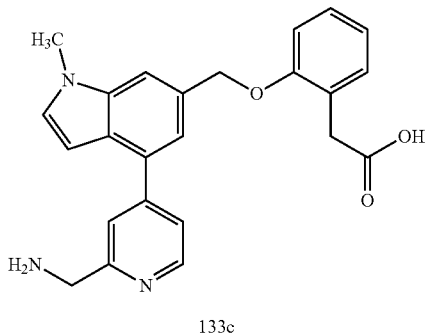

133c

Preparation of 2-(2-((4-(2-(aminomethyl)pyridin-4-yl)-1-methyl-1H-indol-6-yl)methoxy)phenyl)acetic Acid (133c)

Step-1: Preparation of Ethyl 2-(2-((1-methyl-4-(4,4,5,5-tetramethyl-1,3,2-dioxaborolan-2-yl)-1H-indol-6-yl)methoxy)phenyl)acetate (133a)

Compound 133a was prepared according to the procedure reported in step-1 of Scheme-59 from ethyl 2-(2-((4-bromo-1-methyl-1H-indol-6-yl)methoxy)phenyl)acetate (50c) (0.78 g, 1.94 mmol), using bis(pinacolato)diboron (0.74 g, 2.91 mmol), potassium acetate (0.57 g, 5.82 mmol) and Pd(dppf)Cl$_2$—CH$_2$Cl$_2$ (0.24 g, 0.29 mmol) in anhydrous dioxane (12 mL) under an Ar atmosphere and heating at 100° C. overnight. This gave after workup and purification by flash column chromatography [silica (12 g), eluting with EtOAc/MeOH (9:1) in hexane from 0-10%] ethyl 2-(2-((1-methyl-4-(4,4,5,5-tetramethyl-1,3,2-dioxaborolan-2-yl)-1H-indol-6-yl)methoxy)phenyl)acetate (133a) (0.58 g, 67% yield) as a clear oil; MS (ES+): 450.4 (M+1), 472.5 (M+Na).

Step-2: Preparation of Ethyl 2-(2-((4-(2-(aminomethyl)pyridin-4-yl)-1-methyl-1H-indol-6-yl)methoxy)phenyl)acetate (133b)

Compound 133b was prepared according to the procedure reported in step-3 of Scheme-1 from ethyl 2-(2-((1-methyl-4-(4,4,5,5-tetramethyl-1,3,2-dioxaborolan-2-yl)-1H-indol-6-yl)methoxy)phenyl)acetate (133a) (0.65 g, 1.45 mmol) in dioxane (6 mL) using (4-chloropyridin-2-yl)methanamine (74a) (0.22 mL, 1.88 mmol), bis(triphenylphosphine)palladium(II) chloride (0.15 g, 0.22 mmol) and a solution of K$_2$CO$_3$ (0.50 g, 3.62 mmol) in water (0.8 mL) under an Ar atmosphere and heating at 100° C. for 2 h on oil bath. This gave after workup, purification by flash column chromatography [silica (24 g), eluting with MeOH in DCM from 0-50%] followed by purification by reverse phase column [C18 (50 g), eluting with ACN in water (containing 0.1% HCl) from 0-100%] ethyl 2-(2-((4-(2-(aminomethyl)pyridin-4-yl)-1-methyl-1H-indol-6-yl)methoxy)phenyl)acetate (133b) (0.1 g, 16% yield) as a yellow solid; MS (ES+): 430.5 (M+1); MS (ES−): 428.5 (M−1).

Step-3: Preparation of 2-(2-((4-(2-(aminomethyl)pyridin-4-yl)-1-methyl-1H-indol-6-yl)methoxy)phenyl)acetic Acid (133c)

Compound 133c was prepared according to the procedure reported in step-6 of Scheme-1, from ethyl 2-(2-((4-(2-(aminomethyl)pyridin-4-yl)-1-methyl-1H-indol-6-yl)methoxy)phenyl)acetate (133b) (0.1 g, 0.23 mmol) in MeOH/THF (4 mL) using a solution of lithium hydroxide monohydrate (0.05 g, 1.16 mmol) in water (0.8 mL). This gave after workup and purification by reverse phase column [C18 (50 g), eluting with ACN in water (containing 0.1% HCl) from 0-100%] 2-(2-((4-(2-(aminomethyl)pyridin-4-yl)-1-methyl-1H-indol-6-yl)methoxy)phenyl)acetic acid (133c) (0.04 g, 39% yield) as a yellow solid; $^1$H NMR (500 MHz, DMSO-d$_6$) δ 8.71 (d, J=5.1 Hz, 1H), 8.35 (s, 3H), 7.83 (d, J=1.5 Hz, 1H), 7.73 (dd, J=5.2, 1.7 Hz, 1H), 7.70 (s, 1H), 7.52 (d, J=3.1 Hz, 1H), 7.39 (d, J=1.3 Hz, 1H), 7.26-7.21 (m, 2H), 7.11 (d, J=8.0 Hz, 1H), 6.91 (td, J=7.4, 1.1 Hz, 1H), 6.70 (dd, J=3.1, 0.9 Hz, 1H), 5.30 (s, 2H), 4.30 (s, 2H), 3.86 (s, 3H), 3.61 (s, 2H); MS (ES+): 402.4 (M+1); MS (ES−): 400.5 (M−1), 436.4 (M+Cl). HPLC purity: 98.98%.

Scheme-134

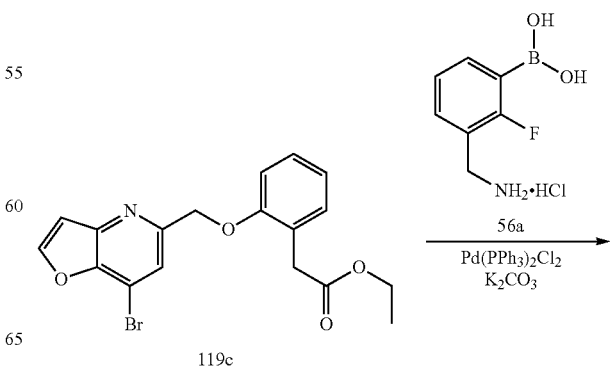

119c

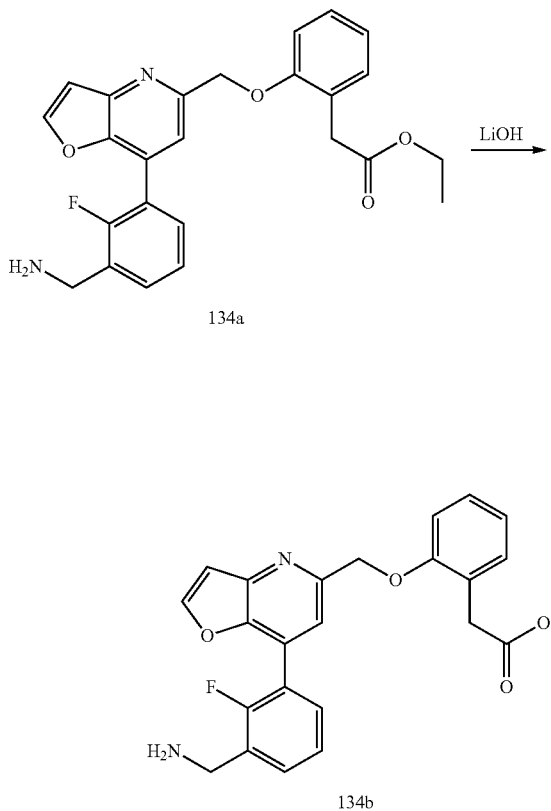

Preparation of 2-(2-((7-(3-(aminomethyl)-2-fluorophenyl)furo[3,2-b]pyridin-5-yl)methoxy)phenyl)acetic Acid (134b)

Step-1: Preparation of Ethyl 2-(2-((7-(3-(aminomethyl)-2-fluorophenyl)furo[3,2-b]pyridin-5-yl)methoxy)phenyl)acetate (134a)

Compound 134a was prepared according to the procedure reported in step-3 of Scheme-1 from ethyl 2-(2-((7-bromofuro[3,2-b]pyridin-5-yl)methoxy)phenyl)acetate (119c) (120 mg, 0.31 mmol) in dioxane (5 mL) using (3-(aminomethyl)-2-fluorophenyl)boronic acid hydrochloride (56a) (95 mg, 0.46 mmol), bis(triphenylphosphine)palladium(II) chloride (43 mg, 0.062 mmol) and $K_2CO_3$ (127 mg, 0.92 mmol) in water (1 mL) under an Ar atmosphere and heating at 100° C. for 3 h on an oil bath. This gave after workup, purification by flash column chromatography [silica (12 g), eluting with DMA80 in DCM from 0-50%] followed by purification by reverse phase column [C18 (50 g), eluting with ACN in water (containing 0.1% HCl) from 0-100%] ethyl 2-(2-((7-(3-(aminomethyl)-2-fluorophenyl)furo[3,2-b]pyridin-5-yl)methoxy)phenyl)acetate (134a) (102 mg, 76% yield) HCl salt as a white solid; $^1H$ NMR (300 MHz, DMSO-$d_6$) δ 8.55 (s, 3H, $D_2O$ exchangeable), 8.42 (d, J=2.3 Hz, 1H), 7.83-7.72 (m, 2H), 7.55 (s, 1H), 7.50 (t, J=7.7 Hz, 1H), 7.29-7.19 (m, 3H), 7.11 (dd, J=8.3, 1.1 Hz, 1H), 6.93 (td, J=7.4, 1.1 Hz, 1H), 5.33 (s, 2H), 4.24-4.12 (m, 2H), 3.90 (q, J=7.1 Hz, 2H), 3.66 (s, 2H), 0.96 (t, J=7.1 Hz, 3H); $^{19}F$ NMR (282 MHz, DMSO-$d_6$) δ−117.89; MS (ES+): 435.2 (M+1); (ES−): 433.3 (M−1).

Step-2: Preparation of 2-(2-((7-(3-(aminomethyl)-2-fluorophenyl)furo[3,2-b]pyridin-5-yl)methoxy)phenyl)acetic Acid (134b)

Compound 134b was prepared according to the procedure reported in step-6 of Scheme-1 from ethyl 2-(2-((7-(3-(aminomethyl)-2-fluorophenyl)furo[3,2-b]pyridin-5-yl)methoxy)phenyl)acetate (134a) (60 mg, 0.14 mmol) in MeOH/THF (6 mL) using a solution of lithium hydroxide monohydrate (15 mg, 0.36 mmol) in water (1.0 mL). This gave after workup and purification by reverse phase column [C18 (50 g), eluting with ACN in water (containing 0.1% HCl) from 0-100%] 2-(2-((7-(3-(aminomethyl)-2-fluorophenyl)furo[3,2-b]pyridin-5-yl)methoxy)phenyl)acetic acid (134b) (50 mg, 89% yield) HCl salt as a white solid; $^1H$ NMR (500 MHz, DMSO-$d_6$) δ 12.17 (s, 1H, $D_2O$ exchangeable), 8.46-8.34 (m, 4H, $D_2O$ exchangeable, 3H), 7.78-7.71 (m, 2H), 7.61-7.58 (m, 1H), 7.47 (t, J=7.7 Hz, 1H), 7.26-7.24 (m, 1H), 7.23 (d, J=1.7 Hz, 1H), 7.21 (s, 1H), 7.09-7.05 (m, 1H), 6.91 (td, J=7.4, 1.1 Hz, 1H), 5.34 (s, 2H), 4.19 (q, J=5.9 Hz, 2H), 3.60 (s, 2H); MS (ES+): 407.2 (M+1); (ES−): 405.3 (M−1).

Scheme-135

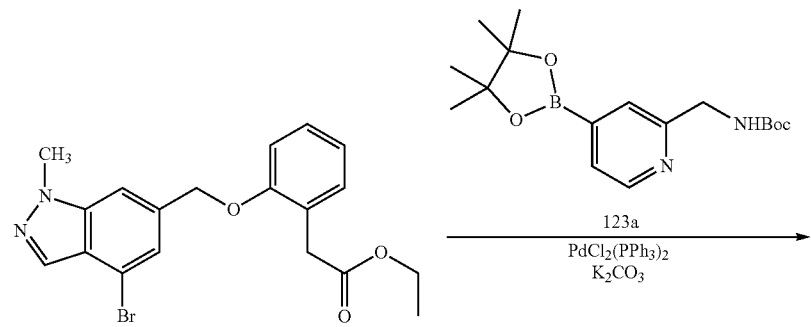

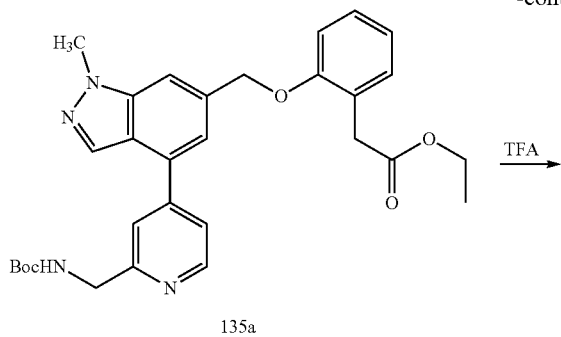

135a

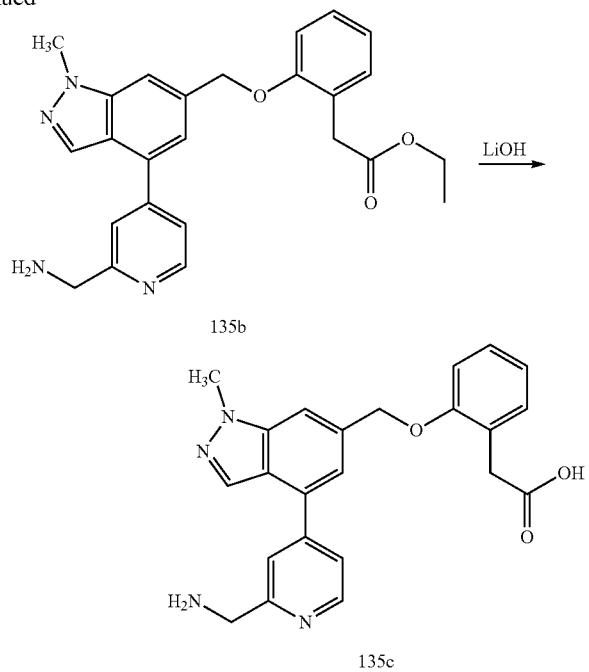

135b

135c

Preparation of 2-(2-((4-(2-(aminomethyl)pyridin-4-yl)-1-methyl-1H-indazol-6-yl)methoxy)phenyl)acetic Acid (135c)

Step-1: Preparation of Ethyl 2-(2-((4-(2-(((tert-butoxycarbonyl)amino)methyl)pyridin-4-yl)-1-methyl-1H-indazol-6-yl)methoxy)phenyl)acetate (135a)

Compound 135a was prepared according to the procedure reported in step-3 of Scheme-1 from ethyl 2-(2-((4-bromo-1-methyl-1H-indazol-6-yl)methoxy)phenyl)acetate (128e) (700 mg, 1.736 mmol) in dioxane (30 mL) using tert-butyl (4-(4,4,5,5-tetramethyl-1,3,2-dioxaborolan-2-yl)pyridin-2-yl)methylcarbamate (123a) (1.160 g, 3.47 mmol), $K_2CO_3$ (0.720 g, 5.21 mmol) in water (5 mL), bis(triphenylphosphine)palladium(II) chloride (0.183 g, 0.260 mmol) and heating under a nitrogen atmosphere at 100° C. for 3 h on an oil bath. This gave after workup, purification by flash column chromatography [silica (24 g), eluting with methanol in DCM from 0-50%] ethyl 2-(2-((4-(2-(((tert-butoxycarbonyl)amino)methyl)pyridin-4-yl)-1-methyl-1H-indazol-6-yl)methoxy)phenyl)acetate (135a) (0.539 g, 59% yield) as a white solid; MS (ES+): 553.5 (M+Na); MS (ES−): 529.6 (M−1).

Step-2: Preparation of Ethyl 2-(2-((4-(2-(aminomethyl)pyridin-4-yl)-1-methyl-1H-indazol-6-yl)methoxy)phenyl)acetate (135b)

Compound 135b was prepared according to the procedure reported in step-5 of Scheme-1 from ethyl 2-(2-((4-(2-(((tert-butoxycarbonyl)amino)methyl)pyridin-4-yl)-1-methyl-1H-indazol-6-yl)methoxy)phenyl)acetate (135a) (0.523 g, 0.986 mmol) in DCM (30 mL) using TFA (0.759 mL, 9.86 mmol). This gave after workup compound 135b (0.537 g, 100% yield) TFA salt as a yellow waxy solid. 239 mgs of this TFA salt of 135b was subjected to purification by reverse phase column chromatography [C18 (50 g), eluting with ACN in water (containing 0.1% HCl) from 0-100%] to afford ethyl 2-(2-((4-(2-(aminomethyl)pyridin-4-yl)-1-methyl-1H-indazol-6-yl)methoxy)phenyl)acetate (135b) (0.073 g, 43% yield) HCl salt as a white solid; $^1H$ NMR (300 MHz, DMSO-$d_6$) δ 8.80-8.74 (m, 1H), 8.43 (s, 3H, $D_2O$ exchangeable), 8.38-8.35 (m, 1H), 7.93 (s, 1H), 7.87 (s, 1H), 7.80 (dd, J=5.2, 1.7 Hz, 1H), 7.51 (s, 1H), 7.31-7.22 (m, 2H), 7.12 (d, J=8.0 Hz, 1H), 6.98-6.88 (m, 1H), 5.34 (s, 2H), 4.34 (t, J=5.9 Hz, 2H), 4.13 (s, 3H), 3.94 (q, J=7.1 Hz, 2H), 3.68 (s, 2H), 0.98 (t, J=7.1 Hz, 3H); MS (ES+): 431.4 (M+1), 861.8 (2M+1); MS (ES−): 465.5 (M+Cl); HPLC purity: 97.33%.

Step-3: Preparation of 2-(2-((4-(2-(aminomethyl)pyridin-4-yl)-1-methyl-1H-indazol-6-yl)methoxy)phenyl)acetic Acid (135c)

Compound 135c was prepared according to the procedure reported in step-6 of Scheme-1 from ethyl 2-(2-((4-(2-(aminomethyl)pyridin-4-yl)-1-methyl-1H-indazol-6-yl)methoxy)phenyl)acetate (135b) (0.238 g, 0.437 mmol) in THF (4 mL) and MeOH (8 mL) using a solution of lithium hydroxide hydrate (0.092 g, 2.185 mmol) in water (4 mL). This gave after workup and purification by flash column chromatography [silica gel, eluting with methanol in DCM from 0-100%] followed by reverse-phase column chromatography [C18 (50 g), eluting with ACN in water (containing 0.1% HCl) from 0-100%] 2-(2-((4-(2-(aminomethyl)pyridin-4-yl)-1-methyl-1H-indazol-6-yl)methoxy)phenyl)acetic Acid (135c) (0.092 g, 0.229 mmol, 52.3% yield) HCl salt as a yellow solid; $^1H$ NMR (300 MHz, DMSO-$d_6$) δ 12.2 (bs, 1H, $D_2O$ exchangeable), 8.81-8.72 (m, 1H), 8.44 (s, 3H, $D_2O$ exchangeable), 8.37 (d, J=1.0 Hz, 1H), 7.95-7.92 (m, 1H), 7.92-7.88 (m, 1H), 7.81 (dd, J=5.2, 1.7 Hz, 1H), 7.54 (d, J=1.2 Hz, 1H), 7.30-7.19 (m, 2H), 7.14-7.05 (m, 1H), 6.92 (t, J=7.3 Hz, 1H), 5.36 (s, 2H), 4.38-4.30 (m, 2H), 4.12 (s, 3H), 3.65 (s, 2H); MS (ES+): 403.4 (M+1), 805.7 (2M+1); MS (ES−): 401.4 (M−1), 437.4 (M+Cl), 803.7

(2M−1); HPLC purity: 94.73%; Analysis calculated for: $C_{23}H_{22}N_4O_3 \cdot 2.0H_2O \cdot 2.0HCl$: C, 54.02; H, 5.52; Cl, 13.87; N, 10.96; Found: C, 53.79; H, 5.52; Cl, 13.62; N, 10.90.

Scheme-136

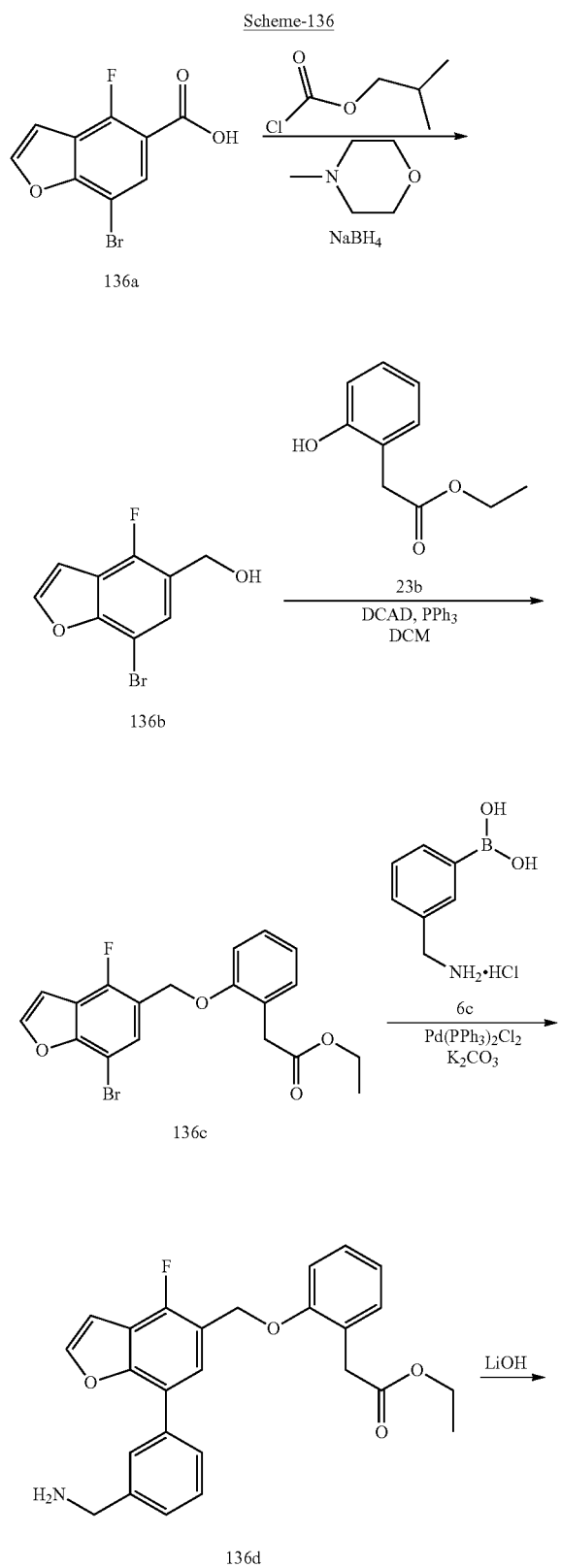

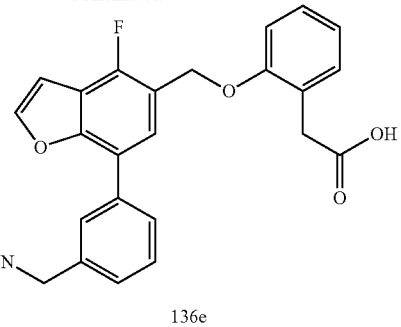

136e

Preparation of 2-(2-((7-(3-(aminomethyl)phenyl)-4-fluorobenzofuran-5-yl)methoxy)phenyl)acetic Acid (136e)

Step-1: Preparation of (7-bromo-4-fluorobenzofuran-5-yl)methanol (136b)

Compound 136b was prepared according to the procedure reported in step-1 of Scheme-23 from 7-bromo-4-fluorobenzofuran-5-carboxylic acid (136a) (900 mg, 3.47 mmol, purchased from PharmaBlock, PB95207) using N-methylmorpholine (0.44 mL, 3.97 mmol) in THF (10 mL), isobutyl chloroformate (0.55 mL, 4.17 mmol) and $NaBH_4$ (394 mg, 10.42 mmol) in water (5 mL). This gave after workup and purification by flash chromatography [silica (12 g), eluting with EtOAc in hexane from 0-60%] (7-bromo-4-fluorobenzofuran-5-yl)methanol (136b) (760 mg, 89% yield) as a white solid; $^1$HNMR (300 MHz, DMSO-$d_6$) δ 8.17 (dt, J=2.2, 0.5 Hz, 1H), 7.60 (dt, J=6.4, 0.6 Hz, 1H), 7.21 (d, J=2.2 Hz, 1H), 5.39 (t, J=5.8 Hz, 1H), 4.65-4.57 (m, 2H); $^{19}$F NMR (282 MHz, DMSO-$d_6$) δ−126.62.

Step-2: Preparation of Ethyl 2-(2-((7-bromo-4-fluorobenzofuran-5-yl)methoxy)phenyl)acetate (136c)

Compound 136c was prepared according to the procedure reported in step-2 of Scheme-23 from (7-bromo-4-fluorobenzofuran-5-yl)methanol (136b) (760 mg, 3.10 mmol) in DCM (15 mL) using triphenylphosphine (895 mg, 3.41 mmol), ethyl 2-(2-hydroxyphenyl) acetate (23b) (615 mg, 3.41 mmol) and di-(4-chlorobenzyl)azodicarboxylate (DCAD, 1253 mg, 3.41 mmol) in DCM (20 mL). This gave after workup and purification by flash column chromatography [silica (40 g), eluting with EtOAc in hexane from 0-50%] ethyl 2-(2-((7-bromo-4-fluorobenzofuran-5-yl)methoxy)phenyl)acetate (136c) (758 mg, 60% yield) as a clear oil; $^1$H NMR (300 MHz, DMSO-$d_6$) δ 8.22 (d, J=2.2 Hz, 1H), 7.71 (d, J=6.1 Hz, 1H), 7.30-7.25 (m, 2H), 7.22 (dd, J=7.5, 1.7 Hz, 1H), 7.15 (dd, J=8.3, 1.1 Hz, 1H), 6.94 (td, J=7.4, 1.1 Hz, 1H), 5.21 (d, J=1.4 Hz, 2H), 3.96 (q, J=7.1 Hz, 2H), 3.57 (s, 2H), 1.02 (t, J=7.1 Hz, 3H); $^{19}$F NMR (282 MHz, DMSO-$d_6$) δ−124.63; MS (ES+): 407.0 and 409.0 (M+1).

Step-3: Preparation of Ethyl 2-(2-((7-(3-(aminomethyl)phenyl)-4-fluorobenzofuran-5-yl)methoxy)phenyl)acetate (136d)

Compound 136d was prepared according to the procedure reported in step-3 of Scheme-1 from ethyl 2-(2-((7-bromo-4-fluorobenzofuran-5-yl)methoxy)phenyl)acetate (136c)

(120 mg, 0.29 mmol) in dioxane (5 mL) using 3-(aminomethyl)phenylboronic acid hydrochloride (6c) (83 mg, 0.44 mmol), bis(triphenylphosphine)palladium(II) chloride (41 mg, 0.059 mmol) and K$_2$CO$_3$ (122 mg, 0.88 mmol) in water (1 mL) under an Ar atmosphere and heating at 100° C. for 3 h on an oil bath. This gave after workup, purification by flash column chromatography [silica (12 g), eluting with DMA80 in DCM from 0-50%] followed by purification by reverse phase column [C18 (50 g), eluting with ACN in water (containing 0.1% HCl) from 0-100%] ethyl 2-(2-((7-(3-(aminomethyl)phenyl)-4-fluorobenzofuran-5-yl)methoxy)phenyl)acetate (136d) (98 mg, 77% yield) HCl salt as a white solid; $^1$H NMR (500 MHz, DMSO-d$_6$) δ 8.32 (s, 3H, D$_2$O exchangeable), 8.19 (d, J=2.3 Hz, 1H), 7.96 (s, 1H), 7.90-7.85 (m, 1H), 7.70 (d, J=6.8 Hz, 1H), 7.64-7.57 (m, 1H), 7.57-7.51 (m, 1H), 7.33-7.16 (m, 4H), 6.93 (td, J=7.3, 1.2 Hz, 1H), 5.27 (s, 2H), 4.18-4.07 (m, 2H), 3.86 (q, J=7.1 Hz, 2H), 3.57 (s, 2H), 0.91 (t, J=7.1 Hz, 3H); $^{19}$F NMR (282 MHz, DMSO-d$_6$) δ−124.64; MS (ES+): 434.1 (M+1).

Step-4: Preparation of 2-(2-((7-(3-(aminomethyl)phenyl)-4-fluorobenzofuran-5-yl)methoxy)phenyl)acetic Acid (136e)

Compound 136e was prepared according to the procedure reported in step-6 of Scheme-1 from ethyl 2-(2-((7-(3-(aminomethyl)phenyl)-4-fluorobenzofuran-5-yl)methoxy)phenyl)acetate (136d) (60 mg, 0.14 mmol) in MeOH/THF (6 mL) using a solution of lithium hydroxide monohydrate (15 mg, 0.36 mmol) in water (1.0 mL). This gave after workup and purification by reverse phase column [C18 (50 g), eluting with ACN in water (containing 0.1% HCl) from 0-100%] 2-(2-((7-(3-(aminomethyl)phenyl)-4-fluorobenzofuran-5-yl)methoxy)phenyl)acetic acid (136e) (28 mg, 50% yield) HCl salt as a white solid; $^1$H NMR (300 MHz, DMSO-d$_6$) δ 12.21 (s, 1H, D$_2$O exchangeable), 8.42 (s, 3H, D$_2$O exchangeable), 8.19 (d, J=2.2 Hz, 1H), 7.97 (d, J=1.9 Hz, 1H), 7.89 (dt, J=7.1, 1.8 Hz, 1H), 7.74 (d, J=6.8 Hz, 1H), 7.64-7.50 (m, 2H), 7.33-7.13 (m, 4H), 6.92 (td, J=7.3, 1.2 Hz, 1H), 5.30 (s, 2H), 4.22-4.03 (m, 2H), 3.55 (s, 2H); $^{19}$F NMR (282 MHz, DMSO-d$_6$) δ−124.69; MS (ES+): 406.2 (M+1); (ES−): 404.2 (M−1).

Scheme-137

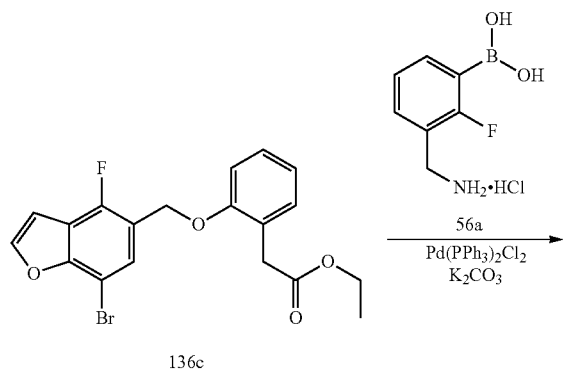

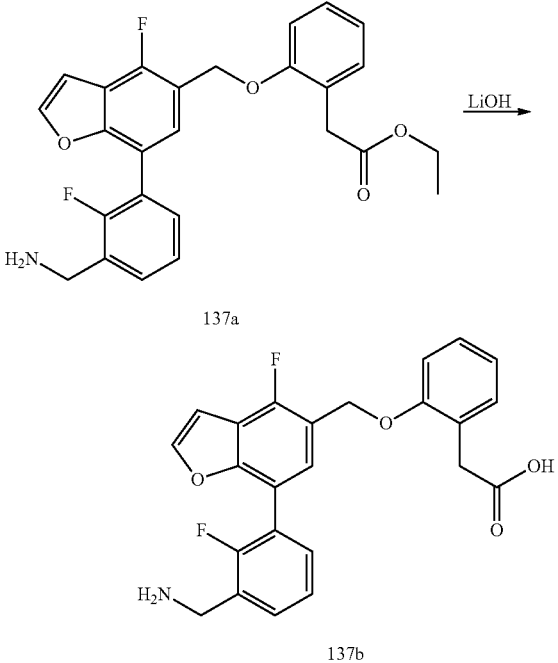

Preparation of 2-(2-((7-(3-(aminomethyl)-2-fluorophenyl)-4-fluorobenzofuran-5-yl)methoxy)phenyl)acetic Acid (137b)

Step-1: Preparation of Ethyl 2-(2-((7-(3-(aminomethyl)-2-fluorophenyl)-4-fluorobenzofuran-5-yl)methoxy)phenyl)acetate (137a)

Compound 137a was prepared according to the procedure reported in step-3 of Scheme-1 from ethyl 2-(2-((7-bromo-4-fluorobenzofuran-5-yl)methoxy)phenyl)acetate (136c) (140 mg, 0.34 mmol) in dioxane (5 mL) using (3-(aminomethyl)-2-fluorophenyl)boronic acid hydrochloride (56a) (106 mg, 0.52 mmol), bis(triphenylphosphine)palladium(II) chloride (48 mg, 0.069 mmol) and K$_2$CO$_3$ (143 mg, 1.03 mmol) in water (1 mL) under an Ar atmosphere and heating at 100° C. for 3 h on an oil bath. This gave after workup, purification by flash column chromatography [silica (12 g), eluting with DMA80 in DCM from 0-50%] followed by purification by reverse phase column [C18 (50 g), eluting with ACN in water (containing 0.1% HCl) from 0-100%] ethyl 2-(2-((7-(3-(aminomethyl)-2-fluorophenyl)-4-fluorobenzofuran-5-yl)methoxy)phenyl)acetate (137a) (112 mg, 72% yield) HCl salt as a white solid; $^1$H NMR (300 MHz, DMSO-d$_6$) δ 300 MHz, DMSO-d$_6$) δ 8.55 (s, 3H, D$_2$O exchangeable), 8.15 (d, J=2.3 Hz, 1H), 7.76-7.68 (m, 1H), 7.65 (td, J=7.5, 1.8 Hz, 1H), 7.54 (d, J=6.7 Hz, 1H), 7.44 (t, J=7.7 Hz, 1H), 7.34-7.25 (m, 1H), 7.25-7.16 (m, 3H), 6.93 (td, J=7.4, 1.2 Hz, 1H), 5.27 (s, 2H), 4.17 (s, 2H), 3.85 (q, J=7.1 Hz, 2H), 3.56 (s, 2H), 0.92 (t, J=7.1 Hz, 3H); $^{19}$F NMR (282 MHz, DMSO-d$_6$) δ−118.67, −123.58; MS (ES+): 452.2 (M+1); HPLC purity: 96.40%.

Step-2: Preparation of 2-(2-((7-(3-(aminomethyl)-2-fluorophenyl)-4-fluorobenzofuran-5-yl)methoxy)phenyl)acetic Acid (137b)

Compound 137b was prepared according to the procedure reported in step-6 of Scheme-1 from ethyl 2-(2-((7-(3-

(aminomethyl)-2-fluorophenyl)-4-fluorobenzofuran-5-yl) methoxy)phenyl)acetate (137a) (75 mg, 0.17 mmol) in MeOH/THF (6 mL) using a solution of lithium hydroxide monohydrate (17 mg, 0.42 mmol) in water (2.0 mL). This gave after workup and purification by reverse phase column [C18 (50 g), eluting with ACN in water (containing 0.1% HCl) from 0-100%] 2-(2-((7-(3-(aminomethyl)-2-fluorophenyl)-4-fluorobenzofuran-5-yl)methoxy)phenyl)acetic acid (137b) (41 mg, 58% yield) HCl salt as a white solid; $^1$H NMR (300 MHz, DMSO-$d_6$) δ 12.16 (s, 1H, D$_2$O exchangeable), 8.55 (s, 3H, D$_2$O exchangeable), 8.14 (d, J=2.3 Hz, 1H), 7.74-7.61 (m, 2H), 7.58 (d, J=6.7 Hz, 1H), 7.42 (t, J=7.7 Hz, 1H), 7.30-7.12 (m, 4H), 6.92 (td, J=7.3, 1.2 Hz, 1H), 5.29 (s, 2H), 4.16 (s, 2H), 3.52 (s, 2H); $^{19}$F NMR (282 MHz, DMSO-$d_6$) δ−118.47, −123.58; MS (ES+): 424.2 (M+1); (ES−): 422.2 (M−1).

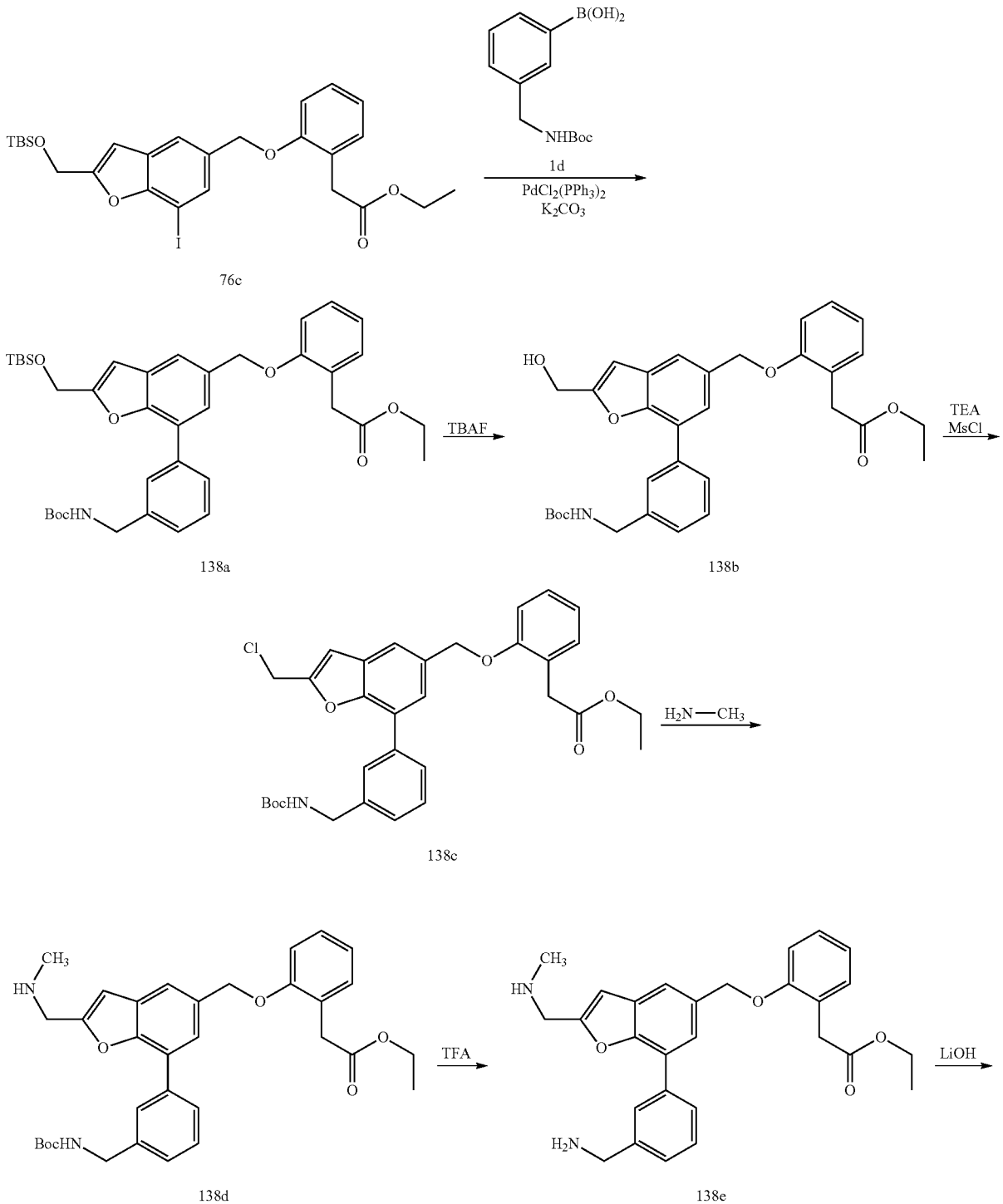

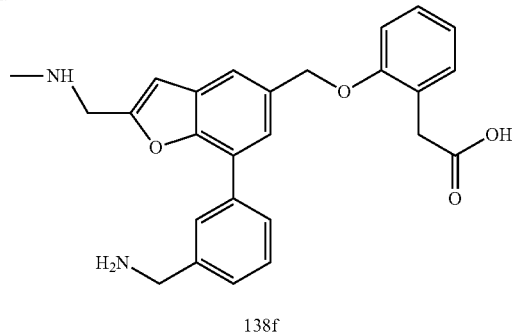 [SMILES: CNCc1cc2cc(COc3ccccc3CC(=O)O)cc(-c3cccc(CN)c3)c2o1]

138f

Preparation of 2-(2-((7-(3-(aminomethyl)phenyl)-2-((methylamino)methyl)benzofuran-5-yl)methoxy)phenyl)acetic Acid (138f)

Step-1: Preparation of Ethyl 2-(2-((7-(3-(((tert-butoxycarbonyl)amino)methyl)phenyl)-2-(((tert-butyldimethyl silyl)oxy)methyl)benzofuran-5-yl)methoxy)phenyl)acetate (138a)

Compound 138a was prepared according to the procedure reported in step-3 of Scheme-1 from ethyl 2-(2-((2-(((tert-butyldimethylsilyl)oxy)methyl)-7-iodobenzofuran-5-yl)methoxy)phenyl)acetate (76c) (9.2 g, 15.85 mmol) in dioxane (80 mL) using (3-(((tert-butoxycarbonyl)amino)methyl)phenyl)boronic acid (Id) (7.92 g, 23.77 mmol), a solution of potassium carbonate (6.57 g, 47.5 mmol) in water (30 mL) and bis(triphenylphosphine)palladium(II) chloride (1.11 g, 1.59 mmol) and heating under a nitrogen atmosphere at 100° C. for 3 h on an oil bath. This gave after workup, purification by flash column chromatography [silica (80 g), eluting with DMA80 in DCM from 0-50%] ethyl 2-(2-((7-(3-(((tert-butoxycarbonyl)amino)methyl)phenyl)-2-(((tert-butyldimethylsilyl)oxy)methyl)benzofuran-5-yl)methoxy)phenyl)acetate (138a) (9.1 g, 13.79 mmol, 87% yield) as a yellow oil.

Step-2: Preparation of Ethyl 2-(2-((7-(3-(((tert-butoxycarbonyl)amino)methyl)phenyl)-2-(hydroxymethyl)benzofuran-5-yl)methoxy)phenyl)acetate (138b)

Compound 138b was prepared according to the procedure reported in step-1 of Scheme-58 from ethyl 2-(2-((7-(3-(((tert-butoxycarbonyl)amino)methyl)phenyl)-2-(((tert-butyldimethylsilyl)oxy)methyl)benzofuran-5-yl)methoxy)phenyl)acetate (138a) (9.1 g, 13.79 mmol) in THF (60 mL) using TBAF (1M in THF) (17.2 mL, 17.24 mmol). This gave after workup and purification by flash column chromatography [silica (80 g), eluting with EtOAc in hexane from 0-70%] ethyl 2-(2-((7-(3-(((tert-butoxycarbonyl)amino)methyl)phenyl)-2-(hydroxymethyl)benzofuran-5-yl)methoxy)phenyl)acetate (138b) (5.58 g, 74% yield) as a semi-solid; $^1$H NMR (300 MHz, DMSO-$d_6$) δ 7.78-7.68 (m, 2H), 7.64 (d, J=1.6 Hz, 1H), 7.53-7.43 (m, 3H), 7.34-7.25 (m, 2H), 7.25-7.17 (m, 1H), 7.11 (dd, J=8.2, 1.1 Hz, 1H), 6.91 (td, J=7.4, 1.1 Hz, 1H), 6.84 (s, 1H), 5.51 (t, J=5.9 Hz, 1H), 5.22 (s, 2H), 4.60 (dd, J=5.9, 0.8 Hz, 2H), 4.23 (d, J=6.2 Hz, 2H), 3.92 (q, J=7.1 Hz, 2H), 3.62 (s, 2H), 1.39 (s, 9H), 0.98 (t, J=7.1 Hz, 3H).

Step-3: Preparation of Ethyl 2-(2-((7-(3-(((tert-butoxycarbonyl)amino)methyl)phenyl)-2-(chloromethyl)benzofuran-5-yl)methoxy)phenyl)acetate (138c)

To a solution of ethyl 2-(2-((7-(3-(((tert-butoxycarbonyl)amino)methyl)phenyl)-2-(hydroxymethyl)benzofuran-5-yl)methoxy)phenyl)acetate (138b) (2.39 g, 4.38 mmol) in DCM (50 mL) at 0° C. was added methanesulfonyl chloride (0.38 mL, 4.82 mmol) and TEA (0.92 mL, 6.57 mmol). The mixture was stirred for 1 h at 0° C. and allowed to warm to RT and stirred for 2 days. The reaction mixture was diluted with DCM, washed with brine (2×), dried, filtered and concentrated in vacuum. The residue obtained was purified by flash column chromatography [silica (40 g), eluting with EtOAc in hexane from 0-100%] to afford ethyl 2-(2-((7-(3-(((tert-butoxycarbonyl)amino)methyl)phenyl)-2-(chloromethyl)benzofuran-5-yl)methoxy)phenyl)acetate (138c) (2.2 g, 89% yield) as a white solid; 1H NMR (300 MHz, DMSO-$d_6$) δ 7.79-7.66 (m, 3H), 7.57 (d, J=1.7 Hz, 1H), 7.53-7.44 (m, 2H), 7.35-7.28 (m, 1H), 7.28-7.18 (m, 2H), 7.14-7.06 (m, 2H), 6.91 (td, J=7.4, 1.1 Hz, 1H), 5.23 (s, 2H), 5.02 (s, 2H), 4.23 (d, J=6.1 Hz, 2H), 3.91 (q, J=7.1 Hz, 2H), 3.62 (s, 2H), 1.39 (s, 9H), 0.97 (t, J=7.1 Hz, 3H); MS (ES+): 586.3 (M+Na).

Step-4: Preparation of Ethyl 2-(2-((7-(3-(((tert-butoxycarbonyl)amino)methyl)phenyl)-2-((methylamino)methyl)benzofuran-5-yl)methoxy)phenyl)acetate (138d)

A solution of ethyl 2-(2-((7-(3-(((tert-butoxycarbonyl)amino)methyl)phenyl)-2-(chloromethyl)benzofuran-5-yl)methoxy)phenyl)acetate (138c) (400 mg, 0.71 mmol) and methanamine (2 M in THF, 7.0 mL, 14.18 mmol) was heated at 80° C. for 4h. The reaction mixture was cooled to room temperature and concentrated in vacuum. The residue obtained was purified by flash column chromatography [silica (12 g), eluting with DMA80 in DCM from 0-50%] to afford ethyl 2-(2-((7-(3-(((tert-butoxycarbonyl)amino)methyl)phenyl)-2-((methylamino)methyl)benzofuran-5-yl)methoxy)phenyl)acetate (138d) (320 mg, 81% yield) as a clear oil; $^1$H NMR (300 MHz, DMSO-$d_6$) δ 7.79-7.69 (m, 2H), 7.62 (d, J=1.6 Hz, 1H), 7.52-7.44 (m, 3H), 7.33-7.25 (m, 2H), 7.25-7.19 (m, 1H), 7.14-7.07 (m, 1H), 6.91 (td, J=7.4, 1.1 Hz, 1H), 6.80 (s, 1H), 5.21 (s, 2H), 4.23 (d, J=6.2 Hz, 2H), 3.92 (q, J=7.2 Hz, 2H), 3.83 (s, 2H), 3.62 (s, 2H), 2.34 (s, 3H), 1.39 (s, 9H), 0.97 (t, J=7.1 Hz, 3H); MS (ES+): 559.3 (M+1).

Step-5: Preparation of Ethyl 2-(2-((7-(3-(aminomethyl)phenyl)-2-((methylamino)methyl)benzofuran-5-yl)methoxy)phenyl)acetate (138e)

Compound 138e was prepared according to the procedure reported in step-5 of Scheme-1 from ethyl 2-(2-((7-(3-(((tert-butoxycarbonyl)amino)methyl)phenyl)-2-((methylamino)methyl)benzofuran-5-yl)methoxy)phenyl)acetate (138d) (320 mg, 0.57 mmol) in DCM (10 mL) using TFA (0.88 mL, 11.46 mmol). This gave after workup and purification by flash column chromatography [silica gel 24 g, eluting with methanol in DCM from 0-100%] followed by purification by reverse phase column [C18 (50 g), eluting with ACN in water (containing 0.1% HCl) from 0-100%] ethyl 2-(2-((7-(3-(aminomethyl)phenyl)-2-((methylamino)methyl)benzofuran-5-yl)methoxy)phenyl)acetate (138e) (220 mg, 84% yield) HCl salt as a white solid; $^1$H NMR (300 MHz, DMSO-$d_6$) δ 9.68 (s, 2H, $D_2O$ exchangeable), 8.57 (s, 3H, $D_2O$ exchangeable), 8.24 (d, J=1.8 Hz, 1H), 7.95 (dt, J=7.3, 1.8 Hz, 1H), 7.76 (d, J=1.6 Hz, 1H), 7.68 (d, J=1.7 Hz, 1H), 7.63-7.52 (m, 2H), 7.30-7.18 (m, 3H), 7.11 (dd, J=8.3, 1.1 Hz, 1H), 6.92 (td, J=7.4, 1.1 Hz, 1H), 5.26 (s, 2H), 4.43 (s, 2H), 4.18 (s, 2H), 3.94 (q, J=7.1 Hz, 2H), 3.64 (s, 2H), 2.62 (s, 3H), 1.01 (t, J=7.1 Hz, 3H); MS (ES+): 459.2 (M+1); (ES−): 457.3 (M−1).

Step-6: Preparation of 2-(2-((7-(3-(aminomethyl)phenyl)-2-((methylamino)methyl)benzofuran-5-yl)methoxy)phenyl)acetic Acid (138f)

Compound 138f was prepared according to the procedure reported in step-6 of Scheme-1 from ethyl 2-(2-((7-(3-(aminomethyl)phenyl)-2-((methylamino)methyl)benzofuran-5-yl)methoxy)phenyl)acetate (138e) (144 mg, 0.31 mmol) in THF (6 mL) and methanol (6 mL) using a solution of lithium hydroxide monohydrate (33 mg, 0.79 mmol) in water (2.0 mL). This gave after workup and purification by reverse phase column [C18 (30 g), eluting with ACN in water (containing 0.1% HCl) from 0-100%] 2-(2-((7-(3-(aminomethyl)phenyl)-2-((methylamino)methyl)benzofuran-5-yl)methoxy)phenyl)acetic acid (138f) (69 mg, 51% yield) HCl salt as a white solid; $^1$H NMR (300 MHz, DMSO-$d_6$) δ 12.26 (s, 1H, $D_2O$ exchangeable), 9.83 (s, 2H, $D_2O$ exchangeable), 8.65 (s, 3H, $D_2O$ exchangeable), 8.26 (s, 1H), 8.01-7.89 (m, 1H), 7.78 (d, J=1.6 Hz, 1H), 7.74-7.67 (m, 1H), 7.61-7.48 (m, 2H), 7.29-7.14 (m, 3H), 7.14-7.03 (m, 1H), 6.90 (t, J=7.3 Hz, 1H), 5.27 (s, 2H), 4.42 (s, 2H), 4.17 (s, 2H), 3.60 (s, 2H), 2.60 (s, 3H); MS (ES+): 431.2 (M+1); (ES−): 429.3 (M−1).

Scheme-139

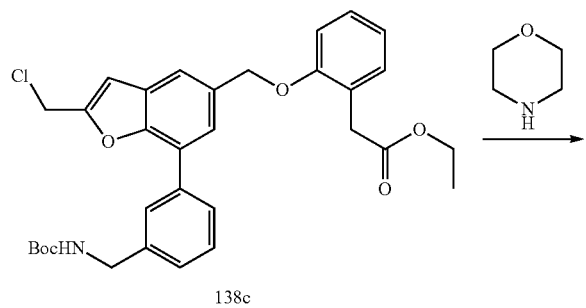

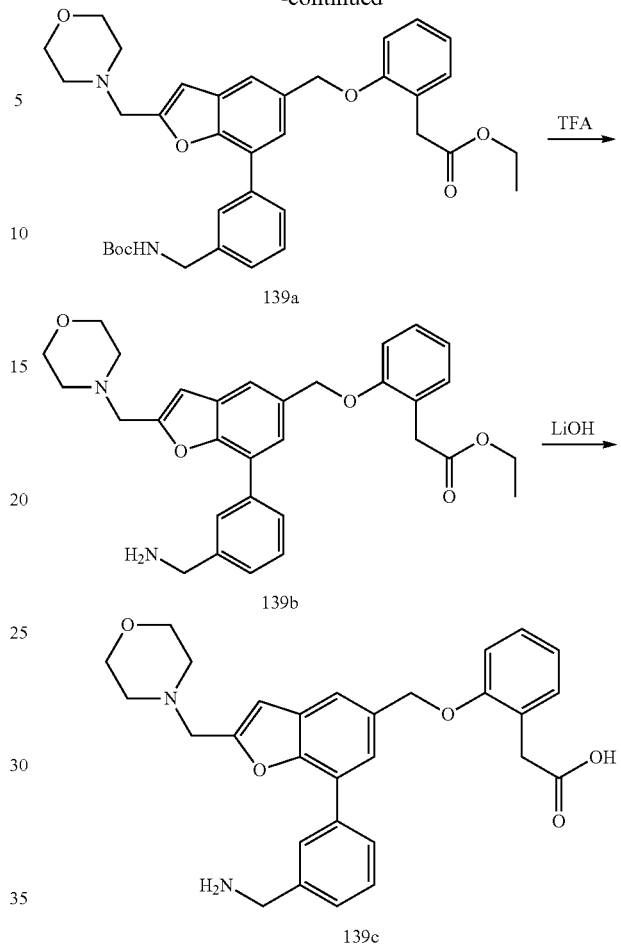

Preparation of 2-(2-((7-(3-(aminomethyl)phenyl)-2-(morpholinomethyl)benzofuran-5-yl)methoxy)phenyl)acetic Acid (139c)

Step-1: Preparation of Ethyl 2-(2-((7-(3-(((tert-butoxycarbonyl)amino)methyl)phenyl)-2-(morpholinomethyl)benzofuran-5-yl)methoxy)phenyl)acetate (139a)

Compound 139a was prepared according to the procedure reported in step-4 of Scheme-138 from ethyl 2-(2-((7-(3-(((tert-butoxycarbonyl)amino)methyl)phenyl)-2-(chloromethyl)benzofuran-5-yl)methoxy)phenyl)acetate (138c) (500 mg, 0.89 mmol) and morpholine (0.77 mL, 8.86 mmol) in ACN (10 mL). This gave after workup and purification by flash column chromatography [silica (24 g), eluting with DMA80 in DCM from 0-50%] ethyl 2-(2-((7-(3-(((tert-butoxycarbonyl)amino)methyl)phenyl)-2-(morpholinomethyl)benzofuran-5-yl)methoxy)phenyl)acetate (139a) (400 mg, 73% yield) as a clear oil; $^1$H NMR (300 MHz, DMSO-$d_6$) δ 7.76-7.70 (m, 2H), 7.63 (d, J=1.6 Hz, 1H), 7.53-7.44 (m, 3H), 7.33-7.19 (m, 3H), 7.14-7.08 (m, 1H), 6.91 (td, J=7.4, 1.1 Hz, 1H), 6.87 (s, 1H), 5.21 (s, 2H), 4.22 (d, J=6.2 Hz, 2H), 3.91 (q, J=7.1 Hz, 2H), 3.72 (s, 2H), 3.62 (s, 2H), 3.61-3.55 (m, 4H), 2.49-2.43 (m, 4H), 1.39 (s, 9H), 0.97 (t, J=7.1 Hz, 3H); MS (ES+): 615.3 (M+1).

Step-2: Preparation of Ethyl 2-(2-((7-(3-(aminomethyl)phenyl)-2-(morpholinomethyl)benzofuran-5-yl)methoxy)phenyl)acetate (139b)

Compound 139b was prepared according to the procedure reported in step-5 of Scheme-1 from ethyl 2-(2-((7-(3-(((tert-butoxycarbonyl)amino)methyl)phenyl)-2-(morpholinomethyl)benzofuran-5-yl)methoxy)phenyl)acetate (139a) (400 mg, 0.65 mmol) in DCM (10 mL) using TFA (1.0 mL, 13.01 mmol). This gave after workup and purification by flash column chromatography [silica gel 24 g, eluting with methanol in DCM from 0-100%] followed by purification by reverse phase column [C18 (50 g), eluting with ACN in water (containing 0.1% HCl) from 0-100%] ethyl 2-(2-((7-(3-(aminomethyl)phenyl)-2-(morpholinomethyl)benzofuran-5-yl)methoxy)phenyl)acetate (139b) (202 mg, 60% yield) HCl salt as an off white solid; $^1$H NMR (500 MHz, DMSO-$d_6$) δ 12.14 (s, 1H, $D_2O$ exchangeable), 8.70 (s, 3H, $D_2O$ exchangeable), 8.29 (s, 1H), 8.00-7.89 (m, 1H), 7.77 (d, J=1.6 Hz, 1H), 7.71 (d, J=1.7 Hz, 1H), 7.57 (d, J=4.7 Hz, 2H), 7.33 (s, 1H), 7.28-7.18 (m, 2H), 7.11 (d, J=8.1 Hz, 1H), 6.91 (t, J=7.3 Hz, 1H), 5.26 (s, 2H), 4.69 (s, 2H), 4.17 (q, J=5.8 Hz, 2H), 4.01-3.85 (m, 6H), 3.64 (s, 2H), 3.43-3.35 (m, 2H), 3.31-3.13 (m, 2H), 1.01 (t, J=7.1 Hz, 3H); MS (ES+): 515.3 (M+1); (ES−): 513.3 (M−1).

Step-3: Preparation of 2-(2-((7-(3-(aminomethyl)phenyl)-2-(morpholinomethyl)benzofuran-5-yl)methoxy)phenyl)acetic Acid (139c)

Compound 139c was prepared according to the procedure reported in step-6 of Scheme-1 ethyl 2-(2-((7-(3-(aminomethyl)phenyl)-2-(morpholinomethyl)benzofuran-5-yl)methoxy)phenyl)acetate (139b) (154 mg, 0.30 mmol) in THF (6 mL) and methanol (6 mL) using a solution of lithium hydroxide monohydrate (32 mg, 0.75 mmol) in water (2.0 mL). This gave after workup and purification by reverse phase column [C18 (30 g), eluting with ACN in water (containing 0.1% HCl) from 0-100%] 2-(2-((7-(3-(aminomethyl)phenyl)-2-(morpholinomethyl)benzofuran-5-yl)methoxy)phenyl)acetic acid (139c) (70 mg, 48% yield) HCl salt as a white solid; $^1$H NMR (300 MHz, DMSO-$d_6$) δ 12.05 (s, 1H, $D_2O$ exchangeable), 8.62 (s, 3H, $D_2O$ exchangeable), 8.27 (d, J=1.8 Hz, 1H), 7.97 (dt, J=6.7, 2.1 Hz, 1H), 7.80 (d, J=1.6 Hz, 1H), 7.74 (d, J=1.6 Hz, 1H), 7.64-7.51 (m, 2H), 7.31 (s, 1H), 7.27-7.17 (m, 2H), 7.12-7.04 (m, 1H), 6.90 (td, J=7.4, 1.1 Hz, 1H), 5.28 (s, 2H), 4.68 (s, 2H), 4.18 (q, J=5.8 Hz, 2H), 4.06-3.77 (m, 4H), 3.60 (s, 2H), 3.45-3.35 (m, 2H), 3.31-3.11 (m, 2H); MS (ES+): 487.2 (M+1); (ES−): 485.3 (M−1).

Scheme-140

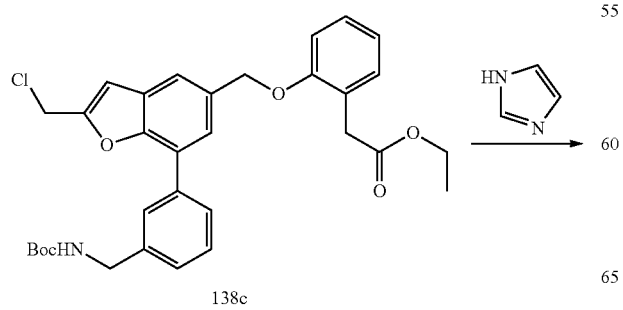

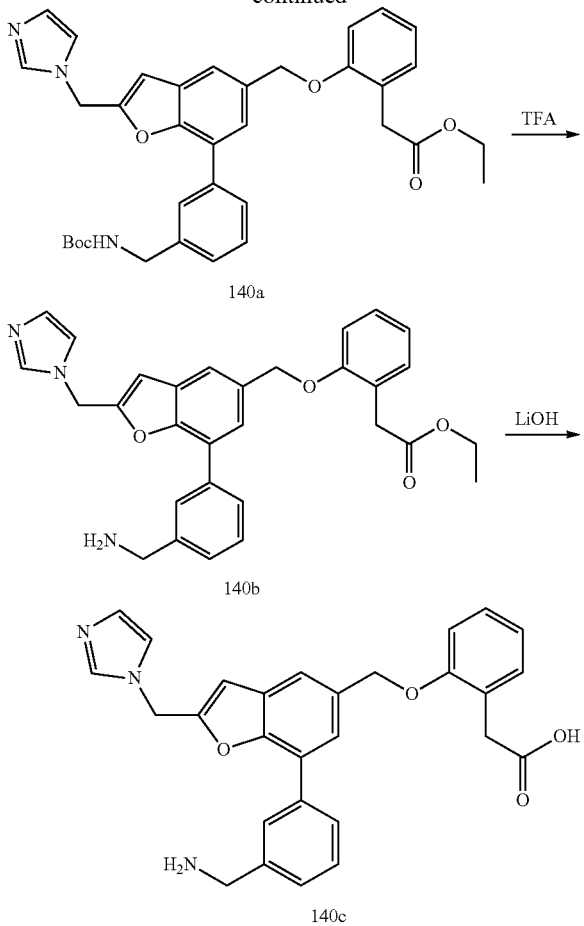

Preparation of 2-(2-((2-((1H-imidazol-1-yl)methyl)-7-(3-(aminomethyl)phenyl)benzofuran-5-yl)methoxy)phenyl)acetic Acid (140c)

Step-1: Preparation of Ethyl 2-(2-((2-((1H-imidazol-1-yl)methyl)-7-(3-(((tert-butoxycarbonyl)amino)methyl)phenyl)benzofuran-5-yl)methoxy)phenyl)acetate (140a)

Compound 140a was prepared according to the procedure reported in step-4 of Scheme-138 from ethyl 2-(2-((7-(3-(((tert-butoxycarbonyl)amino)methyl)phenyl)-2-(chloromethyl)benzofuran-5-yl)methoxy)phenyl)acetate (138c) (350 mg, 0.62 mmol) and imidazole (211 mg, 3.10 mmol) in ACN (10 mL). This gave after workup and purification by flash column chromatography [silica (24 g), eluting with DMA80 in DCM from 0-50%] ethyl 2-(2-((2-((1H-imidazol-1-yl)methyl)-7-(3-(((tert-butoxycarbonyl)amino)methyl)phenyl)benzofuran-5-yl)methoxy)phenyl)acetate (140a) (280 mg, 76% yield) as a yellow oil; MS (ES+): 596.3 (M+1).

Step-2: Preparation of Ethyl 2-(2-((2-((1H-imidazol-1-yl)methyl)-7-(3-(aminomethyl)phenyl)benzofuran-5-yl)methoxy)phenyl)acetate (140b)

Compound 140b was prepared according to the procedure reported in step-5 of Scheme-1 ethyl 2-(2-((2-((1H-imidazol-1-yl)methyl)-7-(3-(((tert-butoxycarbonyl)amino)

methyl)phenyl)benzofuran-5-yl)methoxy)phenyl)acetate (140a) (280 mg, 0.47 mmol) in DCM (10 mL) using TFA (0.72 mL, 9.40 mmol). This gave after workup and purification by flash column chromatography [silica gel 24 g, eluting with methanol in DCM from 0-100%] followed by purification by reverse phase column [C18 (50 g), eluting with ACN in water (containing 0.1% HCl) from 0-100%] ethyl 2-(2-((2-((1H-imidazol-1-yl)methyl)-7-(3-(aminomethyl)phenyl)benzofuran-5-yl)methoxy)phenyl)acetate (140b) (133 mg, 57% yield) HCl salt as a white solid; $^1$H NMR (500 MHz, DMSO-$d_6$) δ 15.11 (s, 1H, $D_2O$ exchangeable), 9.55 (t, J=1.5 Hz, 1H), 8.82 (s, 3H, $D_2O$ exchangeable), 8.08 (d, J=1.8 Hz, 1H), 7.96 (t, J=1.7 Hz, 1H), 7.86 (dt, J=6.7, 1.9 Hz, 1H), 7.78-7.71 (m, 2H), 7.69 (d, J=1.6 Hz, 1H), 7.64-7.51 (m, 2H), 7.29-7.16 (m, 3H), 7.14-7.07 (m, 1H), 6.91 (td, J=7.4, 1.1 Hz, 1H), 5.87 (s, 2H), 5.25 (s, 2H), 4.18-4.08 (m, 2H), 3.95 (q, J=7.1 Hz, 2H), 3.64 (s, 2H), 1.00 (t, J=7.1 Hz, 3H); MS (ES+): 496.2 (M+1); (ES−): 494.3 (M−1).

Step-3: Preparation of 2-(2-((2-((1H-imidazol-1-yl)methyl)-7-(3-(aminomethyl)phenyl)benzofuran-5-yl)methoxy)phenyl)acetic Acid (140c)

Compound 140c was prepared according to the procedure reported in step-6 of Scheme-1 ethyl 2-(2-((2-((1H-imidazol-1-yl)methyl)-7-(3-(aminomethyl)phenyl)benzofuran-5-yl)methoxy)phenyl)acetate (140b) (85 mg, 0.17 mmol) in THF (6 mL) and methanol (6 mL) using a solution of lithium hydroxide monohydrate (18 mg, 0.43 mmol) in water (2.0 mL). This gave after workup and purification by reverse phase column [C18 (50 g), eluting with ACN in water (containing 0.1% HCl) from 0-100%] 2-(2-((2-((1H-imidazol-1-yl)methyl)-7-(3-(aminomethyl)phenyl)benzofuran-5-yl)methoxy)phenyl)acetic acid (140c) (37 mg, 46% yield) HCl salt as an off white solid; $^1$H NMR (300 MHz, DMSO-$d_6$) δ 15.00 (s, 1H, $D_2O$ exchangeable), 9.50 (t, J=1.5 Hz, 1H), 8.72 (s, 3H, $D_2O$ exchangeable), 8.09-8.02 (m, 1H), 7.94 (t, J=1.7 Hz, 1H), 7.92-7.83 (m, 1H), 7.80-7.69 (m, 3H), 7.62-7.52 (m, 2H), 7.27-7.19 (m, 2H), 7.17 (s, 1H), 7.12-7.04 (m, 1H), 6.95-6.79 (m, 1H), 5.84 (s, 2H), 5.27 (s, 2H), 4.13 (q, J=6.0 Hz, 3H), 3.60 (s, 2H); MS (ES+): 468.2 (M+1); (ES−): 466.3 (M−1).

Scheme-141

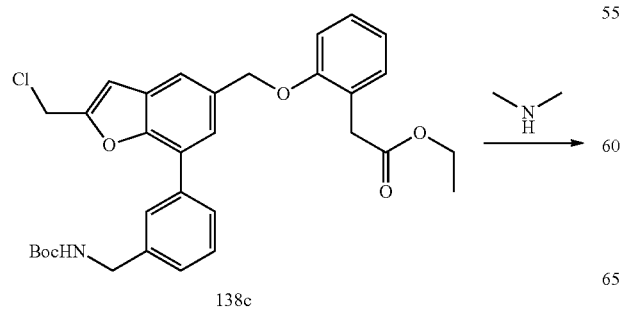

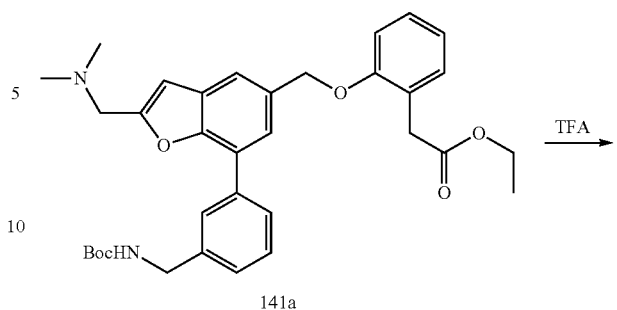

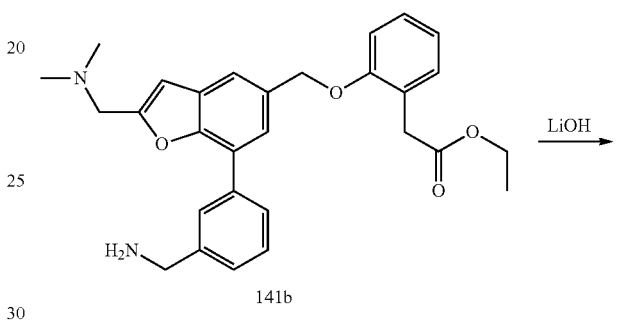

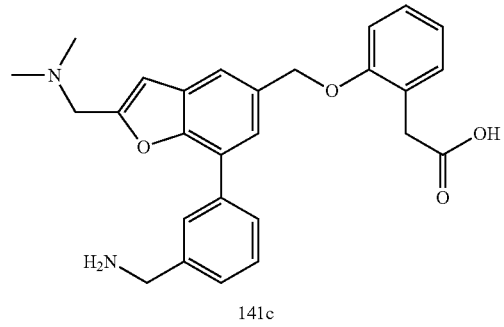

Preparation of 2-(2-((7-(3-(aminomethyl)phenyl)-2-((dimethylamino)methyl)benzofuran-5-yl)methoxy)phenyl)acetic Acid (141c)

Step-1: Preparation of Ethyl 2-(2-((7-(3-(((tert-butoxycarbonyl)amino)methyl)phenyl)-2-((dimethylamino)methyl)benzofuran-5-yl)methoxy)phenyl)acetate (141a)

Compound 141a was prepared according to the procedure reported in step-4 of Scheme-138 from ethyl 2-(2-((7-(3-(((tert-butoxycarbonyl)amino)methyl)phenyl)-2-(chloromethyl)benzofuran-5-yl)methoxy)phenyl)acetate (138c) (350 mg, 0.62 mmol) and dimethylamine (2 M in THF, 1.6 mL, 3.10 mmol) in ACN (10 mL). This gave after workup and purification by flash column chromatography [silica (24 g), eluting with EtOAc/MeOH (9:1) in hexane from 0-100%] ethyl 2-(2-((7-(3-(((tert-butoxycarbonyl)amino)methyl)phenyl)-2-((dimethylamino)methyl)benzofuran-5-yl)methoxy)phenyl)acetate (141a) (260 mg, 73% yield) as a clear oil; $^1$H NMR (300 MHz, DMSO-$d_6$) δ 7.77-7.68 (m, 2H), 7.65-7.59 (m, 1H), 7.53-7.39 (m, 3H), 7.33-7.25 (m, 2H), 7.25-7.18 (m, 1H), 7.11 (dd, J=8.3, 1.1 Hz, 1H), 6.91 (td, J=7.4, 1.1 Hz, 1H), 6.84 (s, 1H), 5.21 (s, 2H), 4.22 (d, J=6.1 Hz, 2H), 3.92 (t, J=7.1 Hz, 2H), 3.63 (d, J=8.0 Hz, 4H), 2.23 (s, 6H), 1.39 (s, 9H), 0.96 (t, J=7.1 Hz, 3H); MS (ES+): 573.3 (M+1).

Step-2: Preparation of Ethyl 2-(2-((7-(3-(aminomethyl)phenyl)-2-((dimethylamino)methyl)benzofuran-5-yl)methoxy)phenyl)acetate (141b)

Compound 141b was prepared according to the procedure reported in step-5 of Scheme-1 ethyl 2-(2-((7-(3-(((tert-butoxycarbonyl)amino)methyl)phenyl)-2-((dimethylamino)methyl)benzofuran-5-yl)methoxy)phenyl)acetate (141a) (260 mg, 0.45 mmol) in DCM (10 mL) using TFA (0.70 mL, 9.08 mmol). This gave after workup and purification by flash column chromatography [silica gel 24 g, eluting with DMA80 in DCM from 0-50%] followed by purification by reverse phase column [C18 (50 g), eluting with ACN in water (containing 0.1% HCl) from 0-100%] ethyl 2-(2-((7-(3-(aminomethyl)phenyl)-2-((dimethylamino)methyl)benzofuran-5-yl)methoxy)phenyl)acetate (141b) (215 mg, 87% yield) HCl salt as a white solid; $^1$H NMR (300 MHz, DMSO-$d_6$) δ 300 MHz, DMSO-$d_6$) δ 11.49 (s, 1H, D$_2$O exchangeable), 8.67 (s, 3H, D$_2$O exchangeable), 8.25 (q, J=1.2 Hz, 1H), 7.99-7.90 (m, 1H), 7.78 (d, J=1.6 Hz, 1H), 7.71 (d, J=1.6 Hz, 1H), 7.62-7.53 (m, 2H), 7.31 (s, 1H), 7.28-7.19 (m, 2H), 7.12 (dd, J=8.3, 1.1 Hz, 1H), 6.92 (td, J=7.4, 1.1 Hz, 1H), 5.26 (s, 2H), 4.62 (s, 2H), 4.25-4.10 (m, 2H), 3.95 (q, J=7.1 Hz, 2H), 3.64 (s, 2H), 2.81 (s, 6H), 1.01 (t, J=7.1 Hz, 3H); MS (ES+): 473.3 (M+1); (ES−): 471.3 (M−1).

Step-3: Preparation of 2-(2-((7-(3-(aminomethyl)phenyl)-2-((dimethylamino)methyl)benzofuran-5-yl)methoxy)phenyl)acetic Acid (141c)

Compound 141c was prepared according to the procedure reported in step-6 of Scheme-1 from ethyl 2-(2-((7-(3-(aminomethyl)phenyl)-2-((dimethylamino)methyl)benzofuran-5-yl)methoxy)phenyl)acetate (141b) (155 mg, 0.33 mmol) in THF (6 mL) and methanol (6 mL) using a solution of lithium hydroxide monohydrate (34 mg, 0.82 mmol) in water (2.0 mL). This gave after workup and purification by reverse phase column [C18 (50 g), eluting with ACN in water (containing 0.1% HCl) from 0-100%] 2-(2-((7-(3-(aminomethyl)phenyl)-2-((dimethylamino)methyl)benzofuran-5-yl)methoxy)phenyl)acetic acid (141c) (89 mg, 61% yield) as a white solid; $^1$H NMR (300 MHz, DMSO-$d_6$) δ 11.46 (s, 1H, D$_2$O exchangeable), 8.63 (s, 3H, D$_2$O exchangeable), 8.23 (d, J=1.8 Hz, 1H), 8.00-7.92 (m, 1H), 7.81 (d, J=1.6 Hz, 1H), 7.74 (d, J=1.6 Hz, 1H), 7.61-7.51 (m, 2H), 7.29 (s, 1H), 7.22 (d, J=7.4 Hz, 2H), 7.13-7.04 (m, 1H), 6.90 (td, J=7.4, 1.1 Hz, 1H), 5.28 (s, 2H), 4.62 (d, J=4.4 Hz, 2H), 4.17 (q, J=5.8 Hz, 2H), 3.60 (s, 2H), 2.81 (d, J=4.3 Hz, 6H); MS (ES+): 445.2 (M+1); (ES−): 443.3 (M−1).

Scheme-142

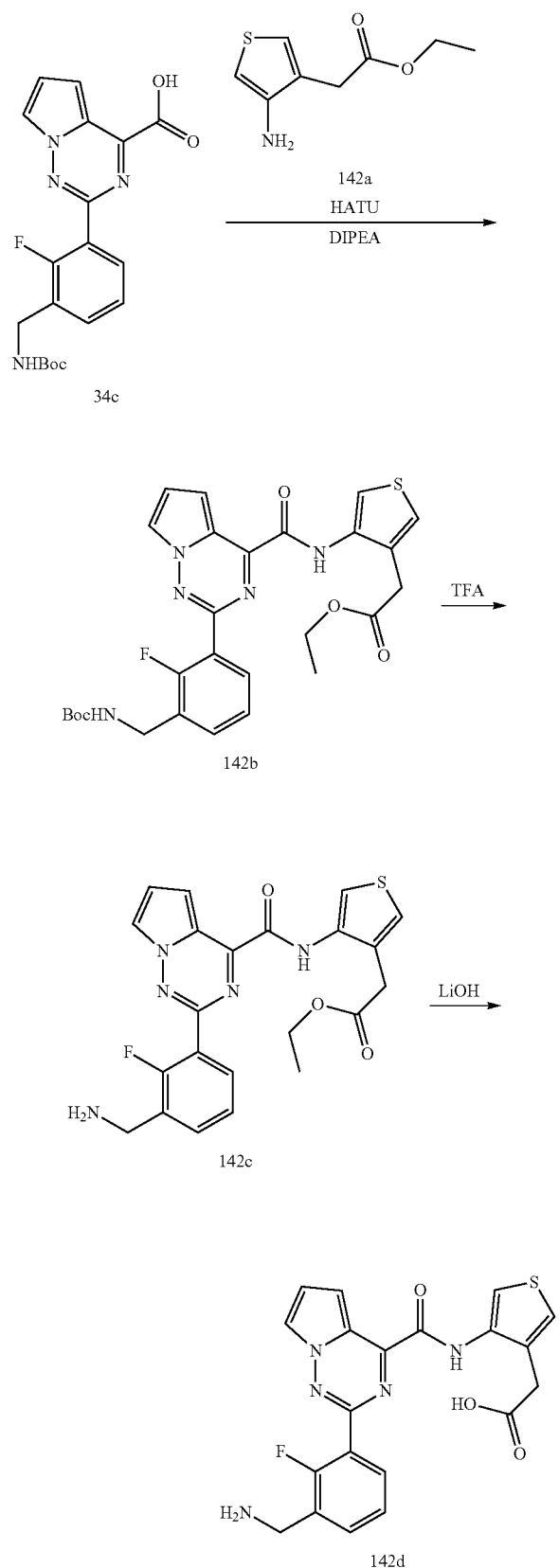

Preparation of 2-(4-(2-(3-(aminomethyl)-2-fluorophenyl)pyrrolo[2,1-f][1,2,4]triazine-4-carboxamido)thiophen-3-yl)acetic Acid (142d)

Step-1: Preparation of Ethyl 2-(4-(2-(3-(((tert-butoxycarbonyl)amino)methyl)-2-fluorophenyl)pyrrolo[2,1-f][1,2,4]triazine-4-carboxamido)thiophen-3-yl)acetate (142b)

Compound 142b was prepared according to the procedure reported in step-4 of Scheme-1 from 2-(3-(((tert-butoxycarbonyl)amino)methyl)-2-fluorophenyl)pyrrolo[2,1-f][1,2,4]triazine-4-carboxylic acid (34c) (150 mg, 0.388 mmol) in DMF (8 mL) using ethyl 2-(4-aminothiophen-3-yl)acetate (142a) (223 mg, prepared according to the procedure reported by Kenda, Benoit et al, in PCT Int. Appl., 2008132139, 6 Nov. 2008; CAS #1076191-69-6), DIPEA (0.338 mL, 1.941 mmol) and HATU (369 mg, 0.971 mmol). This gave after workup and purification by flash column chromatography [silica (12 g), eluting with hexanes/ethyl acetate (1:0 to 3:1)] ethyl 2-(4-(2-(3-(((tert-butoxycarbonyl)amino)methyl)-2-fluorophenyl)pyrrolo[2,1-f][1,2,4]triazine-4-carboxamido)thiophen-3-yl)acetate (142b) (180 mg, 84% yield) as a yellow gum; $^1$H NMR (300 MHz, DMSO-$d_6$) δ 10.77 (s, 1H), 8.43-8.39 (m, 1H), 8.25-8.15 (m, 1H), 7.92 (d, J=3.4 Hz, 1H), 7.61 (dd, J=4.6, 1.4 Hz, 1H), 7.56-7.43 (m, 3H), 7.36 (t, J=7.6 Hz, 1H), 7.30 (dd, J=4.6, 2.6 Hz, 1H), 4.28 (d, J=6.0 Hz, 2H), 4.03 (q, J=7.1 Hz, 2H), 3.84 (s, 2H), 1.41 (s, 9H), 1.06 (t, J=7.1 Hz, 3H); $^{19}$F NMR (282 MHz, DMSO-$d_6$) δ−119.38; MS (ES+): 576.4 (M+Na); MS (ES−): 552.4 (M−1).

Step-2: Preparation of Ethyl 2-(4-(2-(3-(aminomethyl)-2-fluorophenyl)pyrrolo[2,1-f][1,2,4]triazine-4-carboxamido)thiophen-3-yl)acetate (142c)

Compound 142c was prepared according to the procedure reported in step-5 of Scheme-1 from ethyl 2-(4-(2-(3-(((tert-butoxycarbonyl)amino)methyl)-2-fluorophenyl)pyrrolo[2,1-f][1,2,4]triazine-4-carboxamido)thiophen-3-yl)acetate (142b) (170 mg, 0.307 mmol) in DCM (15 mL) using TFA (0.95 mL, 12.28 mmol). This gave after workup and purification by flash column chromatography [silica (12 g), eluting with dichloromethane/methanol (1:0 to 9:1) ethyl 2-(4-(2-(3-(aminomethyl)-2-fluorophenyl)pyrrolo[2,1-f][1,2,4]triazine-4-carboxamido)thiophen-3-yl)acetate (142c) (152 mg) as a yellow solid; $^1$H NMR (300 MHz, DMSO-$d_6$) δ 10.80 (s, 1H), 8.48-8.41 (m, 1H), 8.39 (dd, J=2.6, 1.3 Hz, 1H), 8.28 (s, 3H), 7.92 (d, J=3.4 Hz, 1H), 7.75-7.68 (m, 1H), 7.63 (dd, J=4.6, 1.3 Hz, 1H), 7.52-7.43 (m, 2H), 7.33 (dd, J=4.6, 2.6 Hz, 1H), 4.22 (s, 2H), 4.05 (q, J=7.1 Hz, 2H), 3.85 (s, 2H), 1.08 (t, J=7.1 Hz, 3H); $^{19}$F NMR (282 MHz, DMSO-$d_6$) δ−116.62; MS (ES+): 454.3 (M+1) & 476.3 (M+Na).

Step-3: Preparation of 2-(4-(2-(3-(aminomethyl)-2-fluorophenyl)pyrrolo[2,1-f][1,2,4]triazine-4-carboxamido)thiophen-3-yl)acetic Acid (142d)

Compound 142d was prepared according to the procedure reported in step-6 of Scheme-1 from ethyl 2-(4-(2-(3-(aminomethyl)-2-fluorophenyl)pyrrolo[2,1-f][1,2,4]triazine-4-carboxamido)thiophen-3-yl)acetate (142c) (110 mg, 0.243 mmol) in THF/MeOH (20 mL, 1:1) using lithium hydroxide hydrate (62 mg, 1.455 mmol) in water (10 mL). This gave after workup 2-(4-(2-(3-(aminomethyl)-2-fluorophenyl)pyrrolo[2,1-f][1,2,4]triazine-4-carboxamido)thiophen-3-yl)

acetic acid (142d) (35 mg, 37% for two steps) as a yellow solid. $^1$H NMR (300 MHz, DMSO-$d_6$) δ 11.72 (s, 1H), 8.41 (dd, J=2.6, 1.4 Hz, 1H), 8.18 (t, J=7.5 Hz, 1H), 7.88 (d, J=3.4 Hz, 1H), 7.73-7.61 (m, 2H), 7.42 (t, J=7.7 Hz, 1H), 7.34-7.25 (m, 2H), 4.12 (s, 2H), 3.55 (s, 2H); $^{19}$F NMR (282 MHz, DMSO-$d_6$) δ−114.80; MS (ES+): 426.2 (M+1); MS (ES−): 424.3 (M−1); HPLC purity: 99.74%.

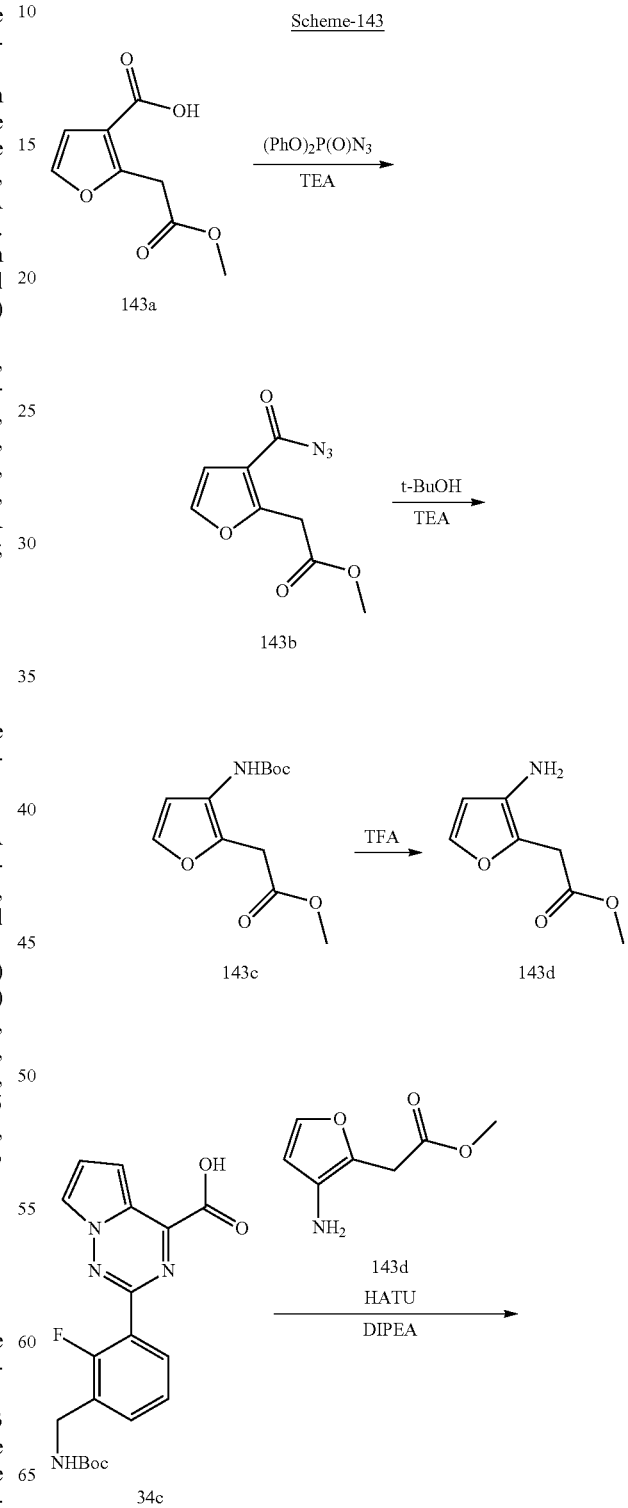

Scheme-143

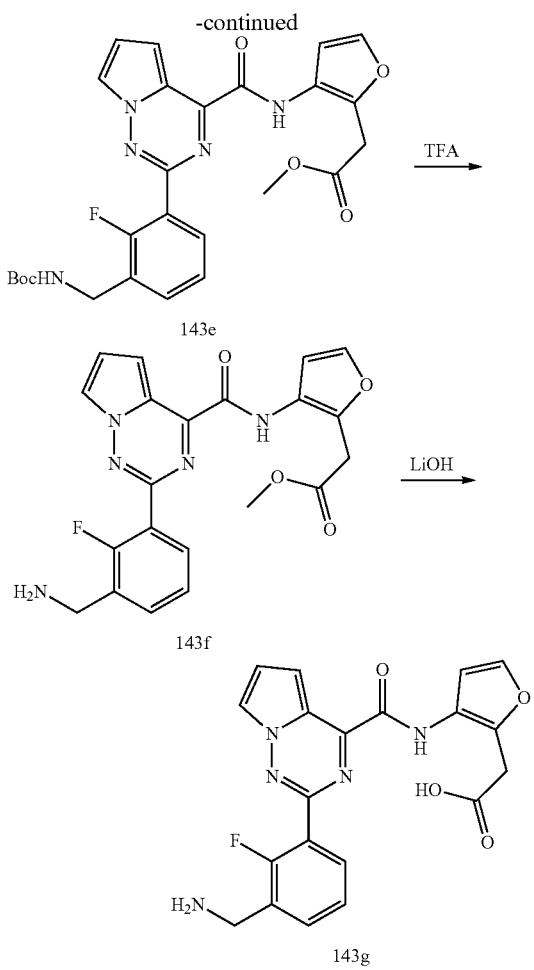

Preparation of 2-(3-(2-(3-(aminomethyl)-2-fluorophenyl)pyrrolo[2,1-f][1,2,4]triazine-4-carboxamido)furan-2-yl)acetic Acid (143g)

Step-1: Preparation of methyl 2-(3-((tert-butoxycarbonyl)amino)furan-2-yl)acetate (143c)

To a solution of 2-(2-methoxy-2-oxoethyl)furan-3-carboxylic acid (143a) (900 mg, 4.64 mmol; CAS #1479004-17-5) in THF (30 mL) was added triethylamine (0.647 mL, 4.64 mmol) and diphenyl phosphorazidate (1.035 mL, 4.64 mmol). The reaction mixture was stirred at RT overnight and concentrated in vacuum to afford methyl 2-(3-(azidocarbonyl)furan-2-yl)acetate (143b) (970 mg), which was used as such for next step.

A solution of methyl 2-(3-(azidocarbonyl)furan-2-yl)acetate (143b) (970 mg, 4.64 mmol) in toluene (30 mL) was refluxed for 0.5 h. The reaction mixture was cooled to RT and added 2-methylpropan-2-ol (2.66 mL, 27.8 mmol), triethylamine (1.293 mL, 9.28 mmol) followed by heating at reflux for 2 h. The reaction mixture was cooled to RT and diluted with ethyl acetate (150 mL) and water (75 mL). The organic layer was separated and aqueous layer was extracted with ethyl acetate (75 mL). The combined extracts were washed with brine (75 mL), dried, filtered and concentrated in vacuum. The residue obtained was purified by flash column chromatography on silica gel with hexanes/ethyl acetate (1:0 to 4:1, then 1:1) to afford methyl 2-(3-((tert-butoxycarbonyl)amino)furan-2-yl)acetate (143c) (756 mg, 64% for two steps) as a yellow gum; $^1$H NMR (300 MHz, DMSO-$d_6$) δ 8.90 (s, 1H), 7.43 (d, J=2.0 Hz, 1H), 6.67 (s, 1H), 3.78 (s, 2H), 3.60 (s, 3H), 1.44 (s, 9H); MS (ES−): 254.3 (M−1).

Step-2: Preparation of methyl 2-(3-aminofuran-2-yl)acetate (143d)

Compound 143d was prepared according to the procedure reported in step-5 of Scheme-1 from methyl 2-(3-((tert-butoxycarbonyl)amino)furan-2-yl)acetate (143c) (400 mg, 1.567 mmol) in DCM (25 mL) using TFA (2.415 mL, 31.3 mmol). This gave after workup methyl 2-(3-aminofuran-2-yl)acetate (143d) (614 mg) as dark-brown gum, which was used as such for next step.

Step-3: Preparation of methyl 2-(3-(2-(3-(((tert-butoxycarbonyl)amino)methyl)-2-fluorophenyl)pyrrolo[2,1-f][1,2,4]triazine-4-carboxamido)furan-2-yl)acetate (143e)

Compound 143e was prepared according to the procedure reported in step-4 of Scheme-1 from 2-(3-(((tert-butoxycarbonyl)amino)methyl)-2-fluorophenyl)pyrrolo[2,1-f][1,2,4]triazine-4-carboxylic acid (34c) (115 mg, 0.298 mmol) in DMF (6 mL) using methyl 2-(3-aminofuran-2-yl)acetate (143d) (175 mg), DIPEA (0.259 mL, 1.488 mmol) and HATU (283 mg, 0.744 mmol). This gave after workup and purification by flash column chromatography [silica (12 g), eluting with hexanes/ethyl acetate (1:0 to 2:1)] methyl 2-(3-(2-(3-(((tert-butoxycarbonyl)amino)methyl)-2-fluorophenyl)pyrrolo[2,1-f][1,2,4]triazine-4-carboxamido)furan-2-yl)acetate (143e) (18 mg, 12%) as a yellow gum; MS (ES+): 524.4 (M+1) & 546.3 (M+Na); MS (ES−): 522.3 (M−1) & 558.4 (M+Cl).

Step-4: Preparation of methyl 2-(3-(2-(3-(aminomethyl)-2-fluorophenyl)pyrrolo[2,1-f][1,2,4]triazine-4-carboxamido)furan-2-yl)acetate (143f)

Compound 143f was prepared according to the procedure reported in step-5 of Scheme-1 from methyl 2-(3-(2-(3-(((tert-butoxycarbonyl)amino)methyl)-2-fluorophenyl)pyrrolo[2,1-f][1,2,4]triazine-4-carboxamido)furan-2-yl)acetate (143e) (18 mg, 0.034 mmol) in DCM (6 mL) using TFA (0.318 mL, 4.13 mmol). This gave after workup and purification by flash column chromatography [silica (12 g), eluting with dichloromethane/methanol (1:0 to 9:1)] methyl 2-(3-(2-(3-(aminomethyl)-2-fluorophenyl)pyrrolo[2,1-f][1,2,4]triazine-4-carboxamido)furan-2-yl)acetate (143f) (14 mg, 96%) as a yellow gum; MS (ES+): 424.2 (M+1) & 446.3 (M+Na).

Step-5: Preparation of 2-(3-(2-(3-(aminomethyl)-2-fluorophenyl)pyrrolo[2,1-f][1,2,4]triazine-4-carboxamido)furan-2-yl)acetic Acid (143g)

Compound 143g was prepared according to the procedure reported in step-6 of Scheme-1 from methyl 2-(3-(2-(3-(aminomethyl)-2-fluorophenyl)pyrrolo[2,1-f][1,2,4]triazine-4-carboxamido)furan-2-yl)acetate (143f) (14 mg, 0.033 mmol) in THF/MeOH (4 mL each) using lithium hydroxide hydrate (9 mg, 0.198 mmol) in water (10 mL). This gave after workup and purification by flash column chromatography [silica gel with dichloromethane/methanol (1:0 to 9:1)] 2-(3-(2-(3-(aminomethyl)-2-fluorophenyl)pyrrolo[2,1- f][1,2,4]triazine-4-carboxamido)furan-2-yl)acetic acid (143g) (11 mg, 81%) as a yellow solid; $^1$H NMR (300 MHz, DMSO-d$_6$) δ 12.44 (s, 1H), 8.40 (s, 1H), 8.17-8.03 (m, 1H), 7.71-7.64 (m, 1H), 7.61 (d, J=4.5 Hz, 1H), 7.46 (s, 1H), 7.42-7.31 (m, 1H), 7.30-7.23 (m, 1H), 7.11 (s, 1H), 4.05 (s, 2H); $^{19}$F NMR (282 MHz, DMSO-d$_6$) δ−113.61; MS (ES+): 410.27 (M+1) & 432.28 (M+Na); MS (ES−): 408.34 (M−1); HPLC purity: 92.67%.

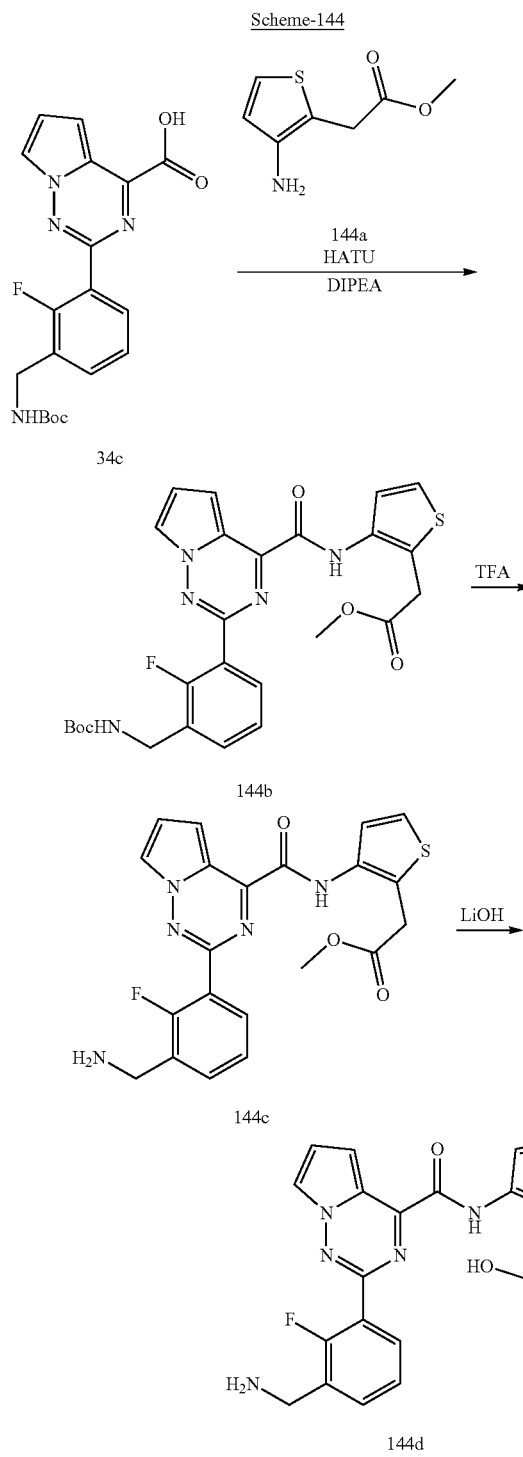

Scheme-144

Preparation of 2-(3-(2-(3-(aminomethyl)-2-fluorophenyl)pyrrolo[2,1-f][1,2,4]triazine-4-carboxamido)thiophen-2-yl)acetic Acid (144d)

Step-1: Preparation of methyl 2-(3-(2-(3-(((tert-butoxycarbonyl)amino)methyl)-2-fluorophenyl)pyrrolo[2,1-f][1,2,4]triazine-4-carboxamido)thiophen-2-yl)acetate (144b)

Compound 144b was prepared according to the procedure reported in step-4 of Scheme-1 from 2-(3-(((tert-butoxycarbonyl)amino)methyl)-2-fluorophenyl)pyrrolo[2,1-f][1,2,4]triazine-4-carboxylic acid (34c) (140 mg, 0.362 mmol) in DMF (8 mL) using methyl 2-(3-aminothiophen-2-yl)acetate (144a) (120 mg, 0.701 mmol, prepared according to the procedure reported by Kenda., Benoit et al, in PCT Int. Appl., 2008132139, 6 Nov. 2008; CAS #22288-78-4), DIPEA (0.244 mL, 1.402 mmol) and HATU (266 mg, 0.701 mmol). This gave after workup and purification by flash column chromatography [silica (12 g), eluting with hexanes/ethyl acetate (1:0 to 3:1)] methyl 2-(3-(2-(3-(((tert-butoxycarbonyl)amino)methyl)-2-fluorophenyl)pyrrolo[2,1-f][1,2,4]triazine-4-carboxamido)thiophen-2-yl)acetate (144b) (102 mg, 52%) as yellow solid. $^1$H NMR (300 MHz, DMSO-d$_6$) δ 10.67 (s, 1H), 8.41-8.37 (m, 1H), 8.29-8.18 (m, 1H), 7.57-7.40 (m, 5H), 7.37 (t, J=7.8 Hz, 1H), 7.28 (dd, J=4.5, 2.6 Hz, 1H), 4.28 (d, J=6.1 Hz, 2H), 3.96 (s, 2H), 3.61 (s, 3H), 1.40 (s, 9H); $^{19}$F NMR (282 MHz, DMSO-d$_6$) δ−119.32; MS (ES+): 540.3 (M+1), MS (ES−): 538.4 (M−1).

Step-2: Preparation of methyl 2-(3-(2-(3-(aminomethyl)-2-fluorophenyl)pyrrolo[2,1-f][1,2,4]triazine-4-carboxamido)thiophen-2-yl)acetate (144c)

Compound 144c was prepared according to the procedure reported in step-5 of Scheme-1 from methyl 2-(3-(2-(3-(((tert-butoxycarbonyl)amino)methyl)-2-fluorophenyl)pyrrolo[2,1-f][1,2,4]triazine-4-carboxamido)thiophen-2-yl)acetate (144b) (85 mg, 0.158 mmol) in DCM (8 mL) using TFA (0.485 mL, 6.30 mmol). This gave after workup and purification by flash column chromatography [silica (12 g), eluting with dichloromethane/methanol (1:0 to 9:1)]methyl 2-(3-(2-(3-(aminomethyl)-2-fluorophenyl)pyrrolo[2,1-f][1,2,4]triazine-4-carboxamido)thiophen-2-yl)acetate (144c) (109 mg) as a yellow solid; $^1$H NMR (500 MHz, DMSO-d$_6$) δ 10.67 (s, 1H), 8.47 (td, J=7.6, 1.8 Hz, 1H), 8.37 (dd, J=2.6, 1.3 Hz, 1H), 8.32 (s, 3H), 7.75-7.70 (m, 1H), 7.56 (dd, J=4.6, 1.3 Hz, 1H), 7.51 (d, J=5.4 Hz, 1H), 7.48 (t, J=7.8 Hz, 1H), 7.42 (d, J=5.4 Hz, 1H), 7.31 (dd, J=4.6, 2.5 Hz, 1H), 4.22 (s, 2H), 3.97 (s, 2H), 3.62 (s, 3H); MS (ES+): 440.3 (M+1) & 462.3 (M+Na).

Step-3: Preparation of 2-(3-(2-(3-(aminomethyl)-2-fluorophenyl)pyrrolo[2,1-f][1,2,4]triazine-4-carboxamido)thiophen-2-yl)acetic Acid (144d)

Compound 144d was prepared according to the procedure reported in step-6 of Scheme-1 from methyl 2-(3-(2-(3-(aminomethyl)-2-fluorophenyl)pyrrolo[2,1-f][1,2,4]triazine-4-carboxamido)thiophen-2-yl)acetate (144c) (79 mg, 0.180 mmol) in THF/MeOH (8 mL, each) using lithium hydroxide hydrate (46 mg, 1.08 mmol) in water (8 mL). This gave after workup 2-(3-(2-(3-(aminomethyl)-2-fluorophenyl)pyrrolo[2,1-f][1,2,4]triazine-4-carboxamido)thiophen-2-yl)acetic acid (144d) (43 mg, 89% for two steps) as a yellow solid; $^1$H NMR (300 MHz, DMSO-d$_6$) δ 12.37 (s, 1H), 8.42 (dd, J=2.6, 1.4 Hz, 1H), 7.96 (td, J=7.4, 1.7 Hz, 1H), 7.68-7.59 (m, 3H), 7.37 (t, J=7.6 Hz, 1H), 7.31-7.27 (m, 2H), 4.05 (s, 2H), 3.43 (s, 2H); $^{19}$F NMR (282 MHz, DMSO-$d_6$) δ −112.88; MS (ES+): 426.2 (M+1); HPLC purity: 95.25%.

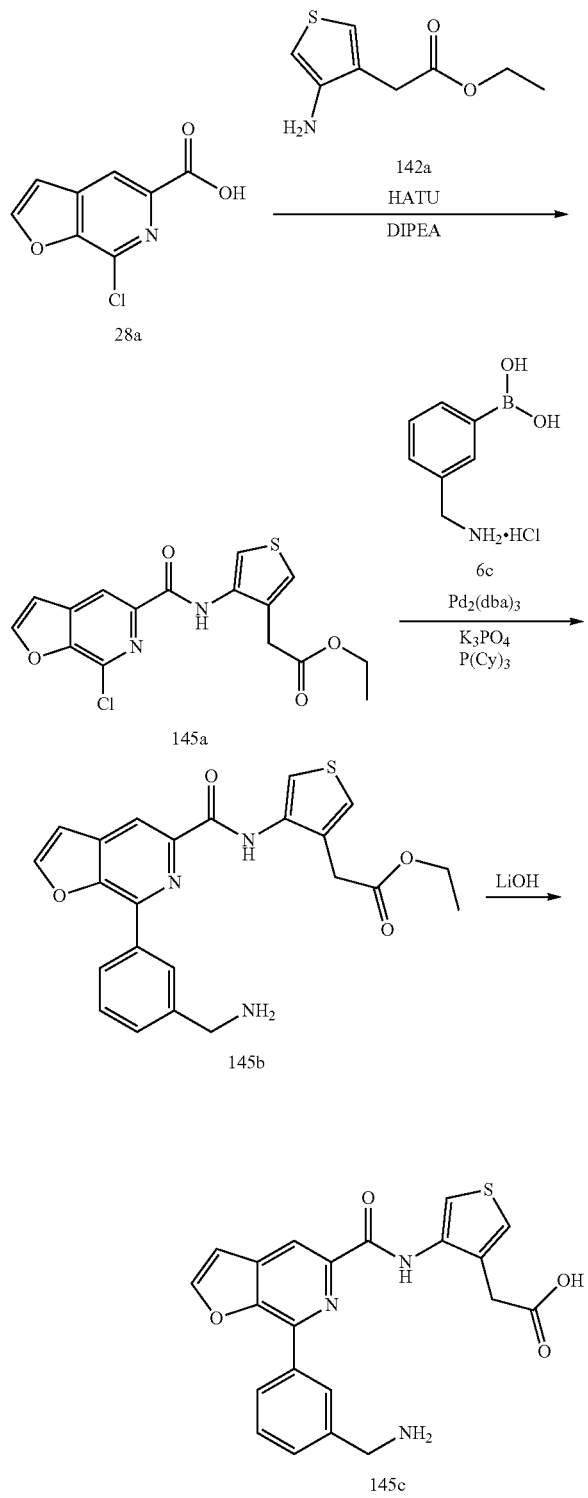

Scheme-145

Preparation of 2-(4-(7-(3-(aminomethyl)phenyl)furo[2,3-c]pyridine-5-carboxamido)thiophen-3-yl)acetic Acid (145c)

Step-1: Preparation of Ethyl 2-(4-(7-chlorofuro[2,3-c]pyridine-5-carboxamido)thiophen-3-yl)acetate (145a)

Compound 145a was prepared according to the procedure reported in step-4 of Scheme-1 from 7-chlorofuro[2,3-c]pyridine-5-carboxylic acid (28a) (140 mg, 0.673 mmol) in DMF using ethyl 2-(4-aminothiophen-3-yl)acetate (142a) (387 mg), DIPEA (0.586 mL, 3.37 mmol) and HATU (640 mg, 1.683 mmol). This gave after workup and purification by flash column chromatography [silica (12 g), eluting with hexanes/ethyl acetate (1:0 to 3:1)] ethyl 2-(4-(7-chlorofuro[2,3-c]pyridine-5-carboxamido)thiophen-3-yl)acetate (145a) (168 mg, 68%) as a white solid; $^1$H NMR (300 MHz, DMSO-$d_6$) δ 10.31 (s, 1H), 8.54 (s, 1H), 8.50 (d, J=2.1 Hz, 1H), 7.83 (d, J=3.5 Hz, 1H), 7.44 (d, J=3.5 Hz, 1H), 7.37 (d, J=2.1 Hz, 1H), 4.15 (q, J=7.1 Hz, 2H), 3.81 (s, 2H), 1.18 (t, J=7.1 Hz, 3H); MS (ES+): 387.1 & 389.1 (M+Na), MS (ES−): 363.2 & 365.2 (M−1).

Step-2: Preparation of Ethyl 2-(4-(7-(3-(aminomethyl)phenyl)furo[2,3-c]pyridine-5-carboxamido)thiophen-3-yl)acetate (145b)

Compound 145b was prepared according to the procedure reported in step-3 of Scheme-1 from ethyl 2-(4-(7-chlorofuro[2,3-c]pyridine-5-carboxamido)thiophen-3-yl)acetate (145a) (100 mg, 0.274 mmol) in dioxane (4 mL) using 3-(aminomethyl)phenylboronic acid hydrochloride (6c) (77 mg, 0.411 mmol), tripotassium phosphate (1.3 M solution, 0.155 mL, 0.466 mmol), tricyclohexylphosphine (46 mg, 0.164 mmol) and Pd$_2$(dba)$_3$ (75 mg, 0.082 mmol) under an Ar atmosphere and heating at 125° C. for 2 h in a microwave. This gave after workup, purification by flash column chromatography [silica (12 g), eluting with dichloromethane/methanol (1:0 to 9:1)] ethyl 2-(4-(7-(3-(aminomethyl)phenyl)furo[2,3-c]pyridine-5-carboxamido)thiophen-3-yl)acetate (145b) (52 mg, 44%) as a brown gum. $^1$H NMR (300 MHz, DMSO-$d_6$) δ 10.76 (s, 1H), 8.53-8.51 (m, 1H), 8.51 (s, 1H), 8.48 (d, J=2.2 Hz, 1H), 8.41-8.32 (m, 1H), 7.92 (d, J=3.5 Hz, 1H), 7.54 (d, J=4.8 Hz, 2H), 7.47 (d, J=3.5 Hz, 1H), 7.34 (d, J=2.2 Hz, 1H), 4.01 (q, J=7.1 Hz, 2H), 3.90 (s, 2H), 3.87 (s, 2H), 1.01 (t, J=7.1 Hz, 3H); MS (ES+): 436.3 (M+1), MS (ES−): 434.3 (M−1).

Step-3: Preparation of 2-(4-(7-(3-(aminomethyl)phenyl)furo[2,3-c]pyridine-5-carboxamido)thiophen-3-yl)acetic Acid (145c)

Compound 145c was prepared according to the procedure reported in step-6 of Scheme-1 from ethyl 2-(4-(7-(3-(aminomethyl)phenyl)furo[2,3-c]pyridine-5-carboxamido)thiophen-3-yl)acetate (145b) (52 mg, 0.119 mmol) in THF/MeOH (5 mL, each) using lithium hydroxide hydrate (31 mg, 0.72 mmol) in water (5 mL). This gave after workup 2-(4-(7-(3-(aminomethyl)phenyl)furo[2,3-c]pyridine-5-carboxamido)thiophen-3-yl)acetic acid (145c) (47 mg, 97%) as an off-white solid; $^1$H NMR (300 MHz, DMSO-$d_6$) δ 12.69 (s, 1H), 9.29 (s, 1H), 8.55 (d, J=7.7 Hz, 1H), 8.48-8.44 (m, 3H), 7.76 (d, J=3.4 Hz, 1H), 7.61-7.44 (m, 2H), 7.32 (d, J=2.2 Hz, 1H), 7.13 (d, J=3.4 Hz, 1H), 4.04 (s, 2H), 3.37 (s, 2H); MS (ES+): 408.2 (M+1) & 430.2 (M+Na); HPLC purity: 94.80%.

613

Scheme-146

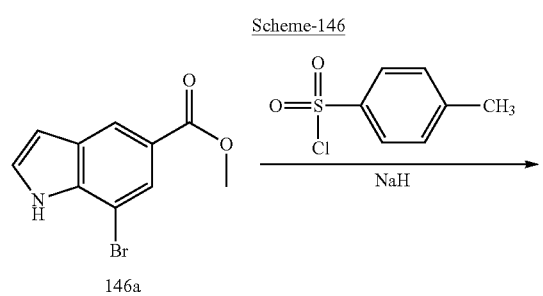

146a

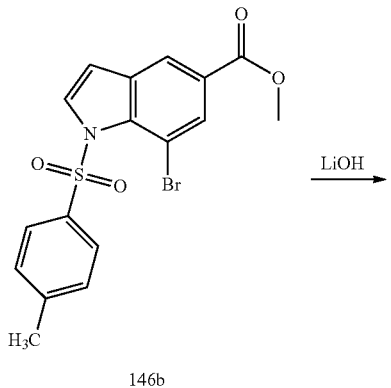

146b

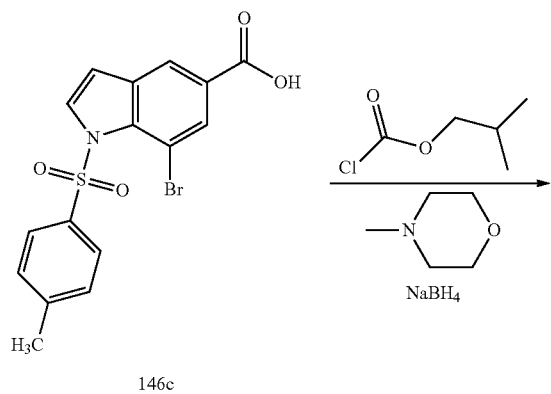

146c

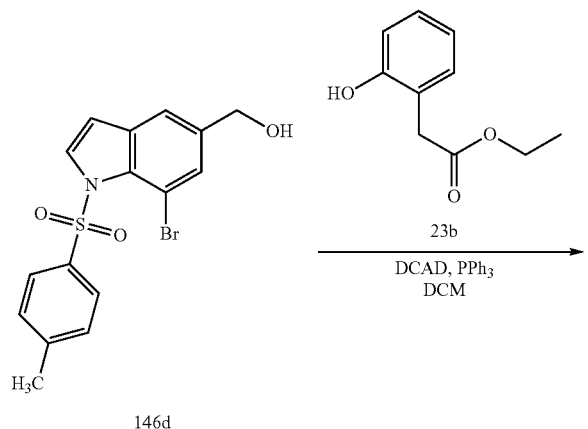

146d

614

-continued

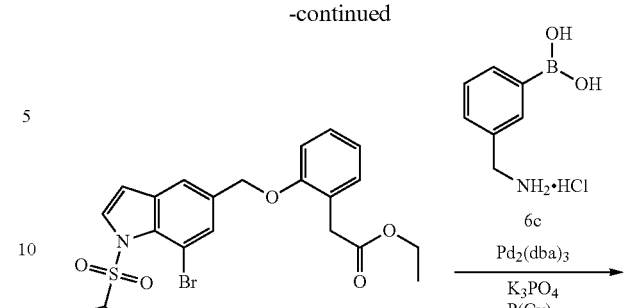

146e

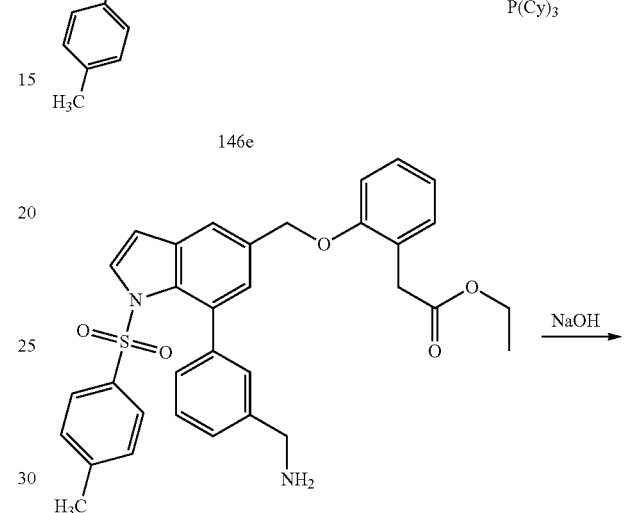

146f

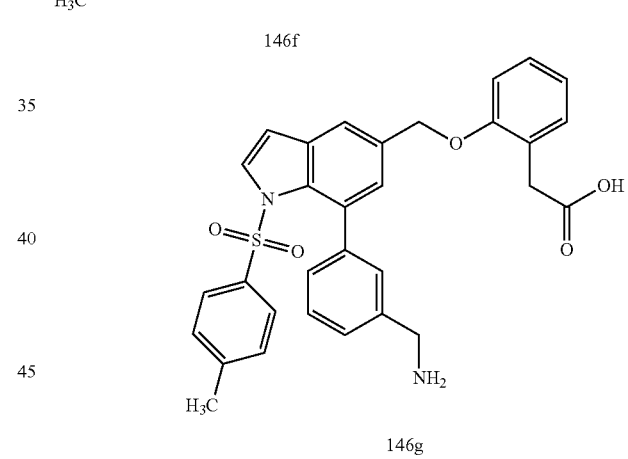

146g

Preparation of 2-(2-((7-(3-(aminomethyl)phenyl)-1-tosyl-1H-indol-5-yl)methoxy)phenyl)acetic Acid (146g)

Step-1: Preparation of methyl 7-bromo-1-tosyl-1H-indole-5-carboxylate (146b)

Compound 146b was prepared according to the procedure reported in step-1 of Scheme-40 from methyl 7-bromo-1H-indole-5-carboxylate (146a) (0.6 g, 2.361 mmol; CAS #885523-35-3) in DMF (9.5 mL) using NaH (60% in mineral oil, 0.236 g, 5.90 mmol) and Tosyl-Cl (0.540 g, 2.83 mmol). This gave after workup methyl 7-bromo-1-tosyl-1H-indole-5-carboxylate (146b) (0.83 g, 86% yield) as a tan solid which was used as such in next step; $^1$H NMR (300 MHz, DMSO-$d_6$) δ 8.31 (d, J=1.6 Hz, 1H), 8.12 (d, J=3.8

Hz, 1H), 7.97 (d, J=1.7 Hz, 1H), 7.78 (d, J=8.4 Hz, 2H), 7.43 (d, J=8.2 Hz, 2H), 7.12 (d, J=3.9 Hz, 1H), 3.86 (s, 3H), 2.37 (s, 3H).

Step-2: Preparation of 7-bromo-1-tosyl-1H-indole-5-carboxylic Acid (146c)

Compound 146c was prepared according to the procedure reported in step-6 of Scheme-1, from methyl 7-bromo-1-tosyl-1H-indole-5-carboxylate (146b) (800 mg, 1.960 mmol) in MeOH/THF (30 mL, each) using a solution of lithium hydroxide hydrate (329 mg, 7.84 mmol) in water (30 mL). This gave after workup 7-bromo-1-tosyl-1H-indole-5-carboxylic acid (146c) (738 mg, 96%) as an off-white solid; $^1$H NMR (300 MHz, DMSO-$d_6$) δ 13.27 (s, 1H), 8.27 (d, J=1.6 Hz, 1H), 8.11 (d, J=3.8 Hz, 1H), 7.96 (d, J=1.6 Hz, 1H), 7.82-7.72 (m, 2H), 7.43 (d, J=8.2 Hz, 2H), 7.10 (d, J=3.8 Hz, 1H), 2.38 (s, 3H); MS (ES−): 392.1 & 394.1 (M−1).

Step-3: Preparation of (7-bromo-1-tosyl-1H-indol-5-yl)methanol (146d)

Compound 146d was prepared according to the procedure reported in step-1 of Scheme-23 from 7-bromo-1-tosyl-1H-indole-5-carboxylic acid (146c) (218 mg, 0.553 mmol) using N-methylmorpholine (0.073 mL, 0.664 mmol) in THF (10 mL), isobutyl chloroformate (0.087 mL, 0.664 mmol) and NaBH$_4$ (63 mg, 1.659 mmol) in water (0.8 mL). This gave after workup (7-bromo-1-tosyl-1H-indol-5-yl)methanol (146d) (251 mg) as a colorless gum, which was used as such for next step; MS (ES+): 402.1 (M+Na), MS (ES−): 378.2 & 380.2 (M−1).

Step-4: Preparation of Ethyl 2-(2-((7-bromo-1-tosyl-1H-indol-5-yl)methoxy)phenyl)acetate (146e)

Compound 146e was prepared according to the procedure reported in step-2 of Scheme-23 from (7-bromo-1-tosyl-1H-indol-5-yl)methanol (146d) (179 mg, 0.995 mmol) in DCM (5 mL) using triphenylphosphine (189 mg, 0.719 mmol), ethyl 2-(2-hydroxyphenyl) acetate (23b) (0.739 g, 4.1 mmol) and a solution of di-(4-chlorobenzyl)azodicarboxylate (264 mg, 0.719 mmol) in DCM (5 mL). This gave after workup and purification by flash column chromatography [silica (12 g), eluting with hexanes/ethyl acetate (1:0 to 2:1)] ethyl 2-(2-((7-bromo-1-tosyl-1H-indol-5-yl)methoxy)phenyl)acetate (146e) (190 mg, 63% for two steps) as a white solid; $^1$H NMR (300 MHz, DMSO-$d_6$) δ 8.02 (d, J=3.9 Hz, 1H), 7.76-7.68 (m, 3H), 7.56-7.50 (m, 1H), 7.42 (d, J=8.1 Hz, 2H), 7.28-7.16 (m, 2H), 7.03 (d, J=8.1 Hz, 1H), 6.96 (d, J=3.8 Hz, 1H), 6.90 (t, J=7.4 Hz, 1H), 5.12 (s, 2H), 3.97 (q, J=7.1 Hz, 2H), 3.60 (s, 2H), 2.37 (s, 3H), 1.01 (t, J=7.1 Hz, 3H).

Step-5: Preparation of Ethyl 2-(2-((7-(3-(aminomethyl)phenyl)-1-tosyl-1H-indol-5-yl)methoxy)phenyl)acetate (146f)

Compound 146f was prepared according to the procedure reported in step-3 of Scheme-1 from ethyl 2-(2-((7-bromo-1-tosyl-1H-indol-5-yl)methoxy)phenyl)acetate (146e) (180 mg, 0.332 mmol) in dioxane (4 mL) using 3-(aminomethyl) phenylboronic acid hydrochloride (6c) (93 mg, 0.498 mmol), tripotassium phosphate (1.3 M solution, 0.188 mL, 0.564 mmol), tricyclohexylphosphine (55.8 mg, 0.199 mmol) and Pd$_2$(dba)$_3$ (91 mg, 0.100 mmol) under an Ar atmosphere and heating at 125° C. for 2 h in a microwave. This gave after workup, purification by flash column chromatography [silica (12 g), eluting with dichloromethane/methanol (1:0 to 9:1)] ethyl 2-(2-((7-(3-(aminomethyl)phenyl)-1-tosyl-1H-indol-5-yl)methoxy)phenyl)acetate (146f) (74 mg, 39%) as a colorless gum; $^1$H NMR (300 MHz, DMSO-$d_6$) δ 7.79 (d, J=3.8 Hz, 1H), 7.59 (s, 1H), 7.36-6.99 (m, 12H), 6.95-6.83 (m, 2H), 5.13 (s, 2H), 3.85 (q, J=7.1 Hz, 2H), 3.67 (s, 2H), 3.58 (s, 2H), 2.31 (s, 3H), 0.96 (t, J=7.1 Hz, 3H); MS (ES+): 569.3 (M+1), MS (ES−): 567.5 (M−1).

Step-6: Preparation of 2-(2-((7-(3-(aminomethyl)phenyl)-1-tosyl-1H-indol-5-yl)methoxy)phenyl)acetic Acid (146g)

Compound 146g was prepared according to the procedure reported in step-4 of Scheme-4, from ethyl 2-(2-((7-(3-(aminomethyl)phenyl)-1-tosyl-1H-indol-5-yl)methoxy)phenyl)acetate (146f) (37 mg, 0.065 mmol) in MeOH (10 mL) using a solution of sodium hydroxide (0.325 mL, 0.651 mmol, 2 M aqueous) in water (3 mL). This gave after workup and purification by flash column chromatography [silica gel, eluting with dichloromethane/methanol (1:0 to 9:1, then 3:2)] 2-(2-((7-(3-(aminomethyl)phenyl)-1-tosyl-1H-indol-5-yl)methoxy)phenyl)acetic acid (146g) (12 mg, 34%) as an off-white solid; $^1$H NMR (300 MHz, DMSO-$d_6$) δ 7.78 (s, 1H), 7.70 (d, J=3.8 Hz, 1H), 7.48 (d, J=8.2 Hz, 2H), 7.37 (d, J=7.2 Hz, 1H), 7.31-7.00 (m, 8H), 6.92-6.86 (m, 2H), 6.80 (t, J=7.3 Hz, 1H), 5.15 (s, 2H), 3.95 (s, 2H), 3.34 (s, 2H), 2.29 (s, 3H); MS (ES+): 541.3 (M+1).

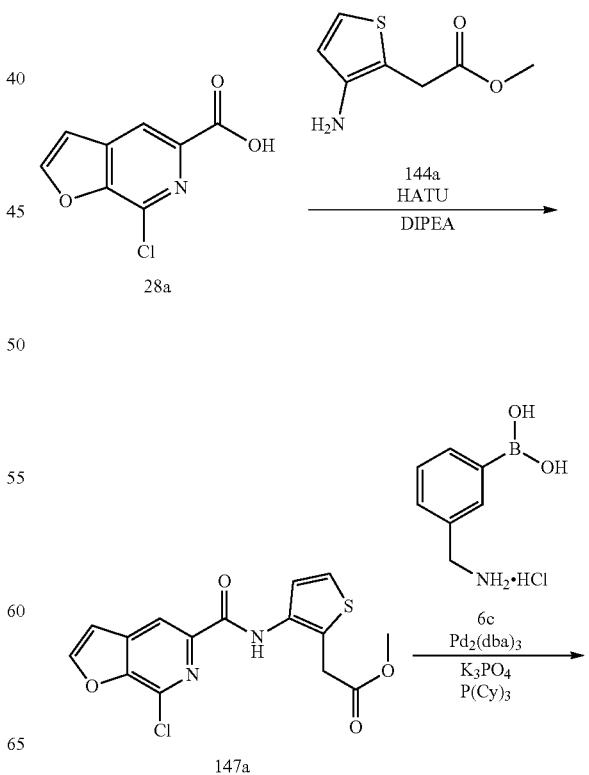

Scheme-147

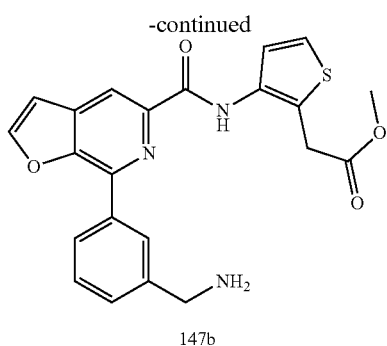

147b

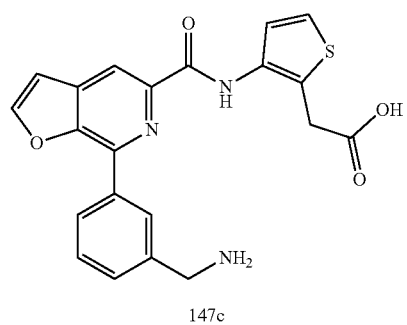

147c

Preparation of 2-(3-(7-(3-(aminomethyl)phenyl)furo[2,3-c]pyridine-5-carboxamido)thiophen-2-yl)acetic Acid (147c)

Step-1: Preparation of methyl 2-(3-(7-chlorofuro[2,3-c]pyridine-5-carboxamido)thiophen-2-yl)acetate (147a)

Compound 147a was prepared according to the procedure reported in step-4 of Scheme-1 from 7-chlorofuro[2,3-c]pyridine-5-carboxylic acid (28a) (100 mg, 0.481 mmol) in DMF (10 mL) using methyl 2-(3-aminothiophen-2-yl)acetate (144a) (140 mg, 0.817 mmol), DIPEA (0.335 mL, 1.923 mmol) and HATU (366 mg, 0.962 mmol). This gave after workup and purification by flash column chromatography [silica (12 g), eluting with hexanes/ethyl acetate (1:0 to 2:1)]methyl 2-(3-(7-chlorofuro[2,3-c]pyridine-5-carboxamido)thiophen-2-yl)acetate (147a) (112 mg, 66%) as a yellow solid; $^1$H NMR (300 MHz, DMSO-$d_6$) δ 10.28 (s, 1H), 8.50 (s, 1H), 8.48 (d, J=2.1 Hz, 1H), 7.44 (d, J=5.4 Hz, 1H), 7.38-7.34 (m, 2H), 3.91 (s, 2H), 3.67 (s, 3H); MS (ES+): 373.1 (M+Na), MS (ES−): 349.1 (M−1).

Step-2: Preparation of 2-(3-(7-(3-(aminomethyl)phenyl)furo[2,3-c]pyridine-5-carboxamido)thiophen-2-yl)acetic Acid (147c)

Compound 147c was prepared according to the procedure reported in step-3 of Scheme-1 from methyl 2-(3-(7-chlorofuro[2,3-c]pyridine-5-carboxamido)thiophen-2-yl)acetate (147a) (0.108 g, 0.308 mmol) in dioxane (6 mL) using 3-(aminomethyl)phenylboronic acid hydrochloride (6c) (0.070 g, 0.462 mmol), tripotassium phosphate (1.3 M solution, 0.711 mL, 0.924 mmol), tricyclohexylphosphine (0.052 g, 0.185 mmol) and Pd$_2$(dba)$_3$ (0.056 g, 0.062 mmol) under an Ar atmosphere and heating at 125° C. for 45 min in a microwave. This gave after workup, purification by flash column chromatography [silica gel 8 g, eluting with methanol in DCM from 0-40%] followed by purification by reverse phase column [C18 (50 g), eluting with ACN in water (containing 0.1% HCl) from 0-100%] methyl 2-(3-(7-(3-(aminomethyl)phenyl)furo[2,3-c]pyridine-5-carboxamido)thiophen-2-yl)acetate (147b) (0.027 g, 0.064 mmol, 21% yield); MS (ES+): 422.2 (M+1); MS (ES−): 456.3 (M+Cl) and 2-(3-(7-(3-(aminomethyl)phenyl)furo[2,3-c]pyridine-5-carboxamido)thiophen-2-yl)acetic acid (147c) (0.012 g, 10% yield) as white solid; $^1$H NMR (300 MHz, DMSO-$d_6$) δ 12.78 (s, 1H, D$_2$O exchangeable), 10.60 (s, 1H, D$_2$O exchangeable), 8.73 (s, 1H), 8.63-8.56 (m, 1H), 8.52 (s, 1H), 8.48 (d, J=2.2 Hz, 1H), 8.50-8.37 (m, 3H, D$_2$O exchangeable), 7.74-7.63 (m, 2H), 7.56 (d, J=5.5 Hz, 1H), 7.46 (d, J=5.4 Hz, 1H), 7.35 (d, J=2.2 Hz, 1H), 4.31-4.10 (m, 2H), 3.89 (s, 2H); MS (ES+): 408.2 (M+1); MS (ES−): 406.3 (M−1); 442.2 (M+Cl), 813.4 (2M−1).

Scheme-148

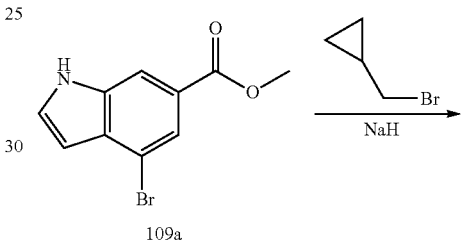

109a

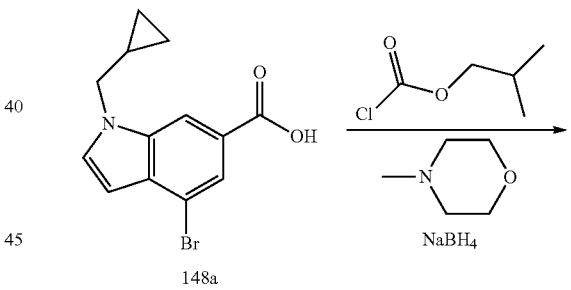

148a

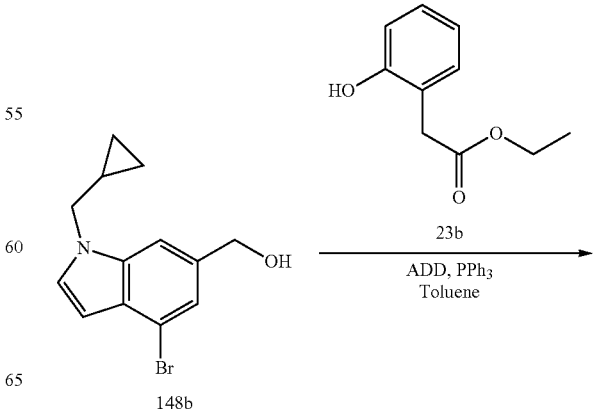

148b

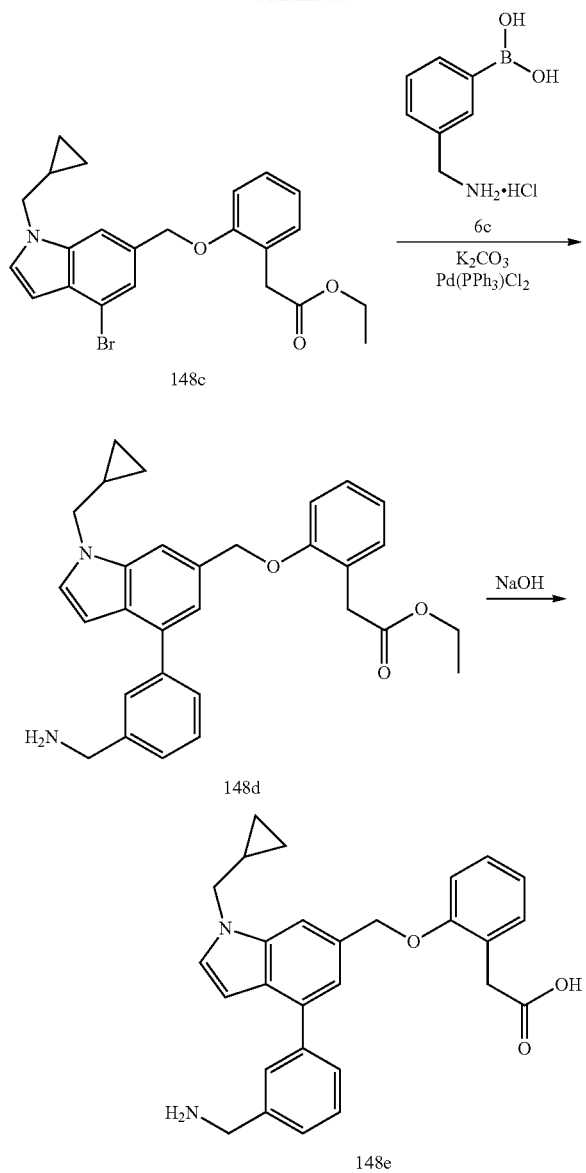

Preparation of 2-(2-((4-(3-(aminomethyl)phenyl)-1-(cyclopropylmethyl)-1H-indol-6-yl)methoxy)phenyl) acetic Acid (148e)

Step-1: Preparation of 4-bromo-1-(cyclopropylmethyl)-1H-indole-6-carboxylic Acid (148a)

Compound 148a was prepared according to the procedure reported in step-1 of Scheme-40 from methyl 4-bromo-1H-indole-6-carboxylate (109a) (15 g, 59.0 mmol) in DMF (50 mL) using NaH (60% in mineral oil) (5.90 g, 148 mmol) and (bromomethyl)cyclopropane (16.69 mL, 177 mmol). This gave after workup and purification by flash column chromatography [silica (80 g), eluting with EtOAc/MeOH=9:1 in hexane from 0-50%] 4-bromo-1-(cyclopropylmethyl)-1H-indole-6-carboxylic acid (148a) (10 g, 58% yield) as a white solid; MS (ES−): 292.2, 294.2 (M−1).

Step-2: Preparation of (4-bromo-1-(cyclopropylmethyl)-1H-indol-6-yl)methanol (148b)

Compound 148b was prepared according to the procedure reported in step-1 of Scheme-23 from 4-bromo-1-(cyclopropylmethyl)-1H-indole-6-carboxylic acid (148a) (15 g, 51.0 mmol) using N-methylmorpholine (6.73 mL, 61.2 mmol) in THF (100 mL), isobutyl chloroformate (8.04 mL, 61.2 mmol) and NaBH$_4$ (5.79 g, 153 mmol) in water (8 mL). This gave after workup and purification by flash column chromatography [silica (80 g), eluting with EtOAc/MeOH=9:1 in hexane from 0-100%] (4-bromo-1-(cyclopropylmethyl)-1H-indol-6-yl)methanol (148b) (9.7 g, 68% yield) as a colorless oil; $^1$H NMR (300 MHz, DMSO-d$_6$): δ 7.51 (d, J=3.2 Hz, 1H), 7.48 (t, J=1.0 Hz, 1H), 7.22 (d, J=1.1 Hz, 1H), 6.35 (dd, J=3.1, 0.9 Hz, 1H), 5.24 (t, J=5.7 Hz, 1H), 4.58 (d, J=4.3 Hz, 2H), 4.04 (d, J=7.0 Hz, 2H), 1.33-1.11 (m, 1H), 0.57-0.32 (m, 4H); MS (ES+): 280.1 (M+1).

Step-3: Preparation of Ethyl 2-(2-((4-bromo-1-(cyclopropylmethyl)-1H-indol-6-yl)methoxy)phenyl) acetate (148c)

Compound 148c was prepared according to the procedure reported in step-2 of Scheme-23 from ((4-bromo-1-(cyclopropylmethyl)-1H-indol-6-yl)methanol (148b) (2.51 g, 13.92 mmol) in toluene (30 mL) using triphenylphosphine (3.65 g, 13.92 mmol), ethyl 2-(2-hydroxyphenyl) acetate (23b) 2.51 g, 13.92 mmol) and a solution of (E)-diazene-1,2-diylbis(piperidin-1-ylmethanone) (3.51 g, 13.92 mmol) in toluene (20 mL). This gave after workup and purification by flash column chromatography [silica (40 g), eluting with EtOAc/MeOH (9:1) in hexane from 0-10% for 40 min, then 10%-50%] ethyl 2-(2-((4-bromo-1-(cyclopropylmethyl)-1H-indol-6-yl)methoxy)phenyl)acetate (148c) (1.68 g, 36% yield) as a colorless oil; $^1$H NMR (300 MHz, DMSO-d$_6$): δ 7.65 (t, J=1.0 Hz, 1H), 7.57 (dd, J=5.3, 3.2 Hz, 1H), 7.30 (d, J=1.1 Hz, 1H), 7.28-7.19 (m, 2H), 7.08 (dd, J=8.3, 1.1 Hz, 1H), 6.90 (td, J=7.4, 1.1 Hz, 1H), 6.39 (td, J=3.2, 0.8 Hz, 1H), 5.19 (s, 2H), 4.09-4.01 (m, 4H), 3.63 (s, 2H), 1.31-1.21 (m, 1H), 1.08 (t, J=7.1 Hz, 3H), 0.54-0.34 (m, 4H); MS (ES+): 442.3, 444.3 (M+1); MS (ES−): 440.1, 442.0 (M−1).

Step-4: Preparation of Ethyl 2-(2-((4-(3-(aminomethyl)phenyl)-1-(cyclopropylmethyl)-1H-indol-6-yl)methoxy)phenyl)acetate (148d)

Compound 148d was prepared according to the procedure reported in step-3 of Scheme-1 from ethyl 2-(2-((4-bromo-1-(cyclopropylmethyl)-1H-indol-6-yl)methoxy)phenyl)acetate (148c) (0.64 g, 1.45 mmol) in dioxane (7 mL) using 3-(aminomethyl)phenylboronic acid hydrochloride (6c) (0.41 g, 2.17 mmol), K$_2$CO$_3$ (0.60 g, 4.34 mmol) in water (2 mL) and bis(triphenylphosphine)Palladium(II) chloride (0.15 g, 0.22 mmol) under an Ar atmosphere and heating at 100° C. for 4 h in an oil bath. This gave after workup, purification by flash column chromatography [silica (12 g), eluting with MeOH in DCM from 0-20%] followed by purification by reverse phase column [C18 (50 g), eluting with ACN in water (containing 0.1% HCl) from 0-100%] ethyl 2-(2-((4-(3-(aminomethyl)phenyl)-1-(cyclopropylmethyl)-1H-indol-6-yl)methoxy)phenyl)acetate (148d) (0.26 g, 38% yield) HCl salt as a white solid; $^1$H NMR (300 MHz, DMSO-d$_6$) δ 8.35 (s, 3H), 7.81 (s, 1H), 7.72-7.63 (m, 2H), 7.60-7.52 (m, 2H), 7.52-7.45 (m, 1H), 7.28-7.18 (m, 3H), 7.16-7.09 (m, 1H), 6.89 (td, J=7.4, 1.1 Hz, 1H), 6.66 (dd, J=3.2, 0.8 Hz, 1H), 5.26 (s, 2H), 4.18-4.05 (m, 4H), 3.93 (q, J=7.1 Hz, 2H), 3.63 (s, 2H), 1.37-1.13 (m, 1H), 0.99 (t, J=7.1 Hz, 3H), 0.56-0.34 (m, 4H). MS (ES+): 469.5 (M+1); MS (ES−): 503.4 (M+Cl).

Step-5: Preparation of 2-(2-((4-(3-(aminomethyl)phenyl)-1-(cyclopropylmethyl)-1H-indol-6-yl)methoxy)phenyl)acetic Acid (148e)

Compound 148e was prepared according to the procedure reported in step-4 of Scheme-4, from ethyl 2-(2-((4-(3-(aminomethyl)phenyl)-1-(cyclopropylmethyl)-1H-indol-6-yl)methoxy)phenyl)acetate (148d) (0.16 g, 0.34 mmol) in THF/MeOH (4 mL, each) using a solution of sodium hydroxide (0.07 g, 1.71 mmol) in water (1 mL). This gave after workup and purification by reverse phase column [C18 (50 g), eluting with ACN in water (containing 0.1% HCl) from 0-100%] 2-(2-((4-(3-(aminomethyl)phenyl)-1-(cyclopropylmethyl)-1H-indol-6-yl)methoxy)phenyl)acetic acid (148e) (0.07 g, 47% yield) HCl salt as a white solid; $^1$H NMR (300 MHz, DMSO-$d_6$) δ 8.44 (s, 3H), 7.82 (s, 1H), 7.75-7.64 (m, 2H), 7.62-7.46 (m, 3H), 7.29-7.17 (m, 3H), 7.11 (d, J=8.2 Hz, 1H), 6.95-6.85 (m, 1H), 6.65 (d, J=3.2 Hz, 1H), 5.27 (s, 2H), 4.17-4.04 (m, 4H), 3.60 (s, 2H), 1.36-1.19 (m, 1H), 0.57-0.29 (m, 4H). MS (ES+): 441.4 (M+1); MS (ES−): 439.4 (M−1), 475.4 (M+Cl). HPLC purity: 88.53%.

Scheme-149

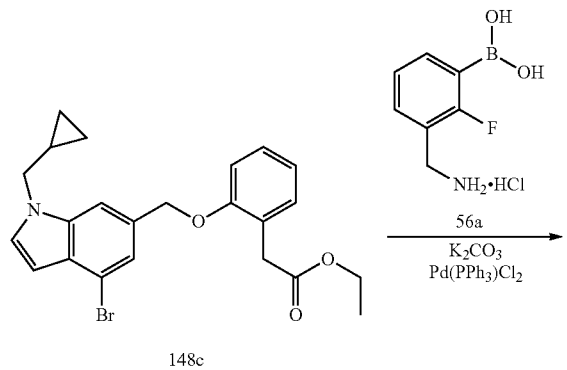

148c

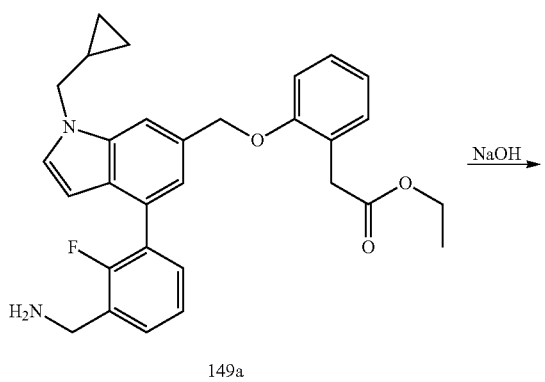

149a

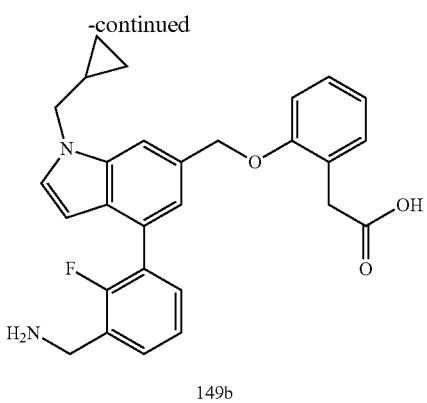

149b

Preparation of 2-(2-((4-(3-(aminomethyl)-2-fluorophenyl)-1-(cyclopropylmethyl)-1H-indol-6-yl)methoxy)phenyl)acetic Acid (149b)

Step-1: Preparation of Ethyl 2-(2-((4-(3-(aminomethyl)-2-fluorophenyl)-1-(cyclopropylmethyl)-1H-indol-6-yl)methoxy)phenyl)acetate (149a)

Compound 149a was prepared according to the procedure reported in step-3 of Scheme-1 from ethyl 2-(2-((4-bromo-1-(cyclopropylmethyl)-1H-indol-6-yl)methoxy)phenyl)acetate (148c) (0.64 g, 1.45 mmol) in dioxane (7 mL) using (3-(aminomethyl)-2-fluorophenyl)boronic acid hydrochloride (56a) (0.45 g, 2.17 mmol), $K_2CO_3$ (0.60 g, 4.34 mmol) in water (0.7 mL) and bis(triphenylphosphine)Palladium(II) chloride (0.15 g, 0.22 mmol) under an Ar atmosphere and heating at 100° C. for 2 h in an oil bath. This gave after workup, purification by flash column chromatography [silica (24 g), eluting with MeOH in DCM from 0-20%] followed by purification by reverse phase column [C18 (50 g), eluting with ACN in water (containing 0.1% HCl) from 0-100%] ethyl 2-(2-((4-(3-(aminomethyl)-2-fluorophenyl)-1-(cyclopropylmethyl)-1H-indol-6-yl)methoxy)phenyl)acetate (149a) (0.36 g, 51% yield) HCl salt as a white solid; $^1$H NMR (300 MHz, DMSO-$d_6$) δ 8.38 (s, 3H), 7.69 (s, 1H), 7.65-7.55 (m, 2H), 7.52 (d, J=3.2 Hz, 1H), 7.39 (t, J=7.6 Hz, 1H), 7.29-7.17 (m, 2H), 7.16-7.09 (m, 2H), 6.90 (td, J=7.3, 1.1 Hz, 1H), 6.35 (t, J=2.7 Hz, 1H), 5.25 (s, 2H), 4.17 (s, 2H), 4.10 (d, J=7.0 Hz, 2H), 3.92 (q, J=7.1 Hz, 2H), 3.63 (s, 2H), 1.34-1.21 (m, 1H), 0.99 (t, J=7.1 Hz, 3H), 0.57-0.35 (m, 4H); $^{19}$F NMR (282 MHz, DMSO-$d_6$) δ−118.84; MS (ES+): 487.4 (M+1); MS (ES−): 521.5 (M+Cl). HPLC purity: 96.57%.

Step-2: Preparation of 2-(2-((4-(3-(aminomethyl)-2-fluorophenyl)-1-(cyclopropylmethyl)-1H-indol-6-yl)methoxy)phenyl)acetic Acid (149b)

Compound 149b was prepared according to the procedure reported in step-4 of Scheme-4, from ethyl 2-(2-((4-(3-(aminomethyl)-2-fluorophenyl)-1-(cyclopropylmethyl)-1H-indol-6-yl)methoxy)phenyl)acetate (149a) (0.24 g, 0.49 mmol) in THF/MeOH (4 mL, each) using a solution of sodium hydroxide (0.10 g, 2.47 mmol) in water (0.8 mL). This gave after workup and purification by reverse phase column [C18 (50 g), eluting with ACN in water (containing 0.1% HCl) from 0-100%] 2-(2-((4-(3-(aminomethyl)-2-fluorophenyl)-1-(cyclopropylmethyl)-1H-indol-6-yl)methoxy)phenyl)acetic acid (149b) (0.08 g, 35% yield) HCl salt as a white solid. $^1$H NMR (300 MHz, DMSO-$d_6$) δ 8.79 (s, 3H), 7.71 (s, 1H), 7.66-7.54 (m, 2H), 7.52 (d, J=3.2 Hz, 1H), 7.38 (t, J=7.6 Hz, 1H), 7.23 (t, J=7.7 Hz, 2H), 7.19-7.07 (m, 2H), 6.89 (td, J=7.4, 1.1 Hz, 1H), 6.35 (t, J=2.9 Hz, 1H), 5.27 (s, 2H), 4.16 (s, 2H), 4.09 (d, J=7.0 Hz, 2H), 3.59 (s, 2H), 1.35-1.19 (m, 1H), 0.56-0.34 (m, 4H); $^{19}$F NMR (282 MHz, DMSO-$d_6$) δ –118.79; MS (ES+): 459.4 (M+1); MS (ES–): 457.3 (M–1), 493.4 (M+Cl). HPLC purity: 92.06%.

Scheme-150

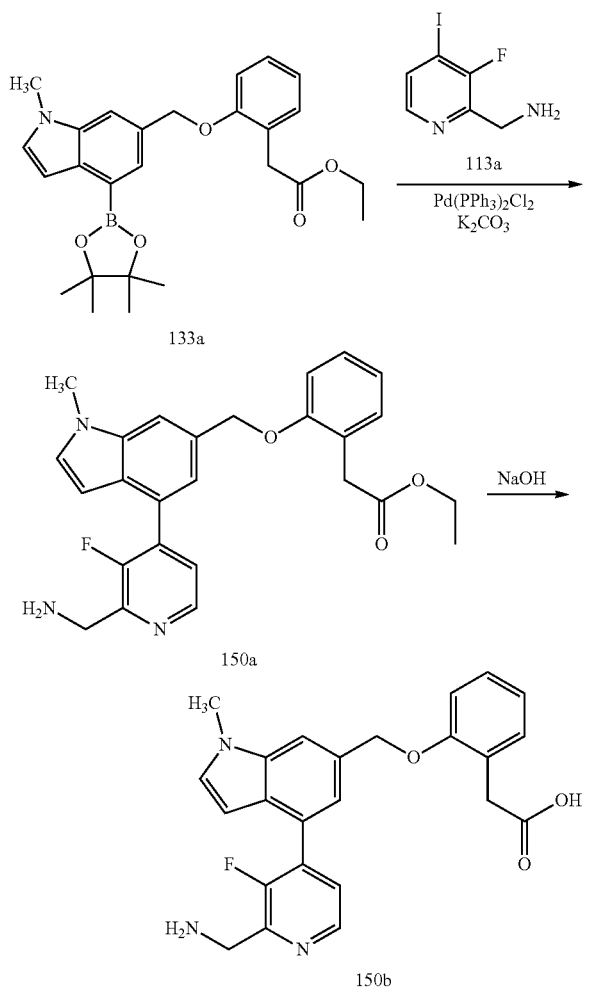

Preparation of 2-(2-((4-(2-(aminomethyl)-3-fluoropyridin-4-yl)-1-methyl-1H-indol-6-yl)methoxy)phenyl)acetic Acid (150b)

Step-1: Preparation of Ethyl 2-(2-((4-(2-(aminomethyl)-3-fluoropyridin-4-yl)-1-methyl-1H-indol-6-yl)methoxy)phenyl)acetate (150a)

Compound 150a was prepared according to the procedure reported in step-3 of Scheme-1 from ethyl 2-(2-((1-methyl-4-(4,4,5,5-tetramethyl-1,3,2-dioxaborolan-2-yl)-1H-indol-6-yl)methoxy)phenyl)acetate (133a) (0.65 g, 1.45 mmol) in dioxane (6 mL) using (3-fluoro-4-iodopyridin-2-yl)methanamine (113a) (0.30 g, 1.21 mmol), bis(triphenylphosphine)palladium(II) chloride 0.13 g, 0.18 mmol) and a solution of K$_2$CO$_3$ (0.42 g, 3.01 mmol) in water (1.0 mL) under an Ar atmosphere and heating at 100° C. for 2 h on oil bath. This gave after workup, purification by flash column chromatography [silica (24 g), eluting with MeOH in DCM from 0-50%] followed by purification by reverse phase column [C18 (50 g), eluting with ACN in water (containing 0.1% HCl) from 0-100%] ethyl 2-(2-((4-(2-(aminomethyl)-3-fluoropyridin-4-yl)-1-methyl-1H-indol-6-yl)methoxy)phenyl)acetate (150a) (0.12 g, 22% yield) as a yellow solid; MS (ES+): 448.5 (M+1).

Step-2: Preparation of 2-(2-((4-(2-(aminomethyl)-3-fluoropyridin-4-yl)-1-methyl-1H-indol-6-yl)methoxy)phenyl)acetic Acid (150b)

Compound 150b was prepared according to the procedure reported in step-4 of Scheme-4, from ethyl 2-(2-((4-(2-(aminomethyl)-3-fluoropyridin-4-yl)-1-methyl-1H-indol-6-yl)methoxy)phenyl)acetate (150a) (0.12 g, 0.27 mmol) in MeOH/THF (4 mL, each) using a solution of sodium hydroxide (0.05 g, 1.34 mmol) in water (0.8 mL). This gave after workup and purification by reverse phase column [C18 (50 g), eluting with ACN in water (containing 0.1% HCl) from 0-100%] 2-(2-((4-(2-(aminomethyl)-3-fluoropyridin-4-yl)-1-methyl-1H-indol-6-yl)methoxy)phenyl)acetic acid (150b) (0.03 g, 23% yield) HCl salt as a yellow solid; $^1$H NMR (500 MHz, DMSO-$d_6$) δ 8.57 (d, J=4.9 Hz, 1H), 8.46 (bs, 4H), 7.73 (s, 1H), 7.68 (t, J=5.3 Hz, 1H), 7.48 (d, J=3.1 Hz, 1H), 7.29 (s, 1H), 7.27-7.20 (m, 2H), 7.11 (d, J=8.1 Hz, 1H), 6.90 (m, 1H), 6.37 (t, J=3.0 Hz, 1H), 5.29 (s, 2H), 4.37 (d, J=6.0 Hz, 2H), 3.86 (s, 3H), 3.60 (s, 2H); MS (ES+): 420.4 (M+1), 442.3 (M+Na); MS (ES–): 418.4 (M–1), 454.4 (M+Cl). HPLC purity: 92.20%.

Scheme-151

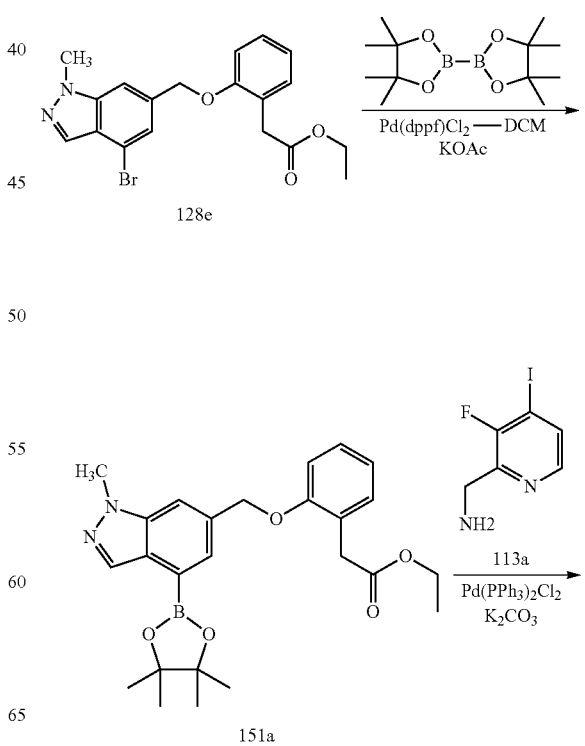

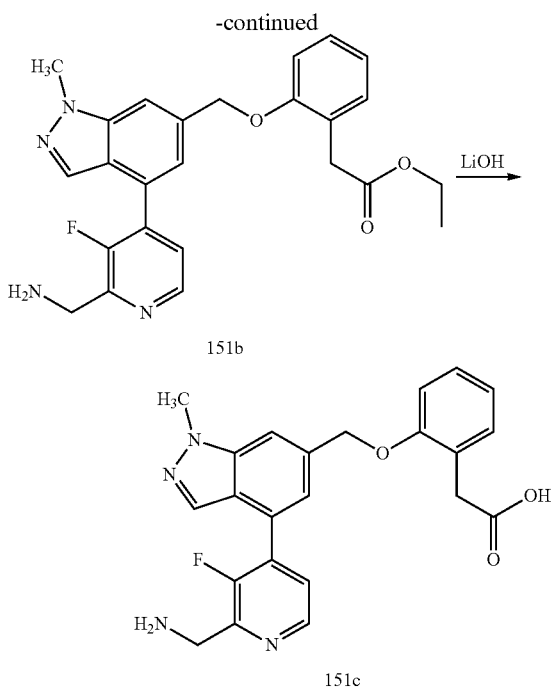

Preparation of 2-(2-((4-(2-(aminomethyl)-3-fluoro-pyridin-4-yl)-1-methyl-1H-indazol-6-yl)methoxy)phenyl)acetic Acid (151c)

Step-1: Preparation of Ethyl 2-(2-((1-methyl-4-(4,4,5,5-tetramethyl-1,3,2-dioxaborolan-2-yl)-1H-indazol-6-yl)methoxy)phenyl)acetate (151a)

Compound 151a was prepared according to the procedure reported in step-1 of Scheme-59 from ethyl 2-(2-((4-bromo-1-methyl-1H-indazol-6-yl)methoxy)phenyl)acetate (128e) (2.00 g, 4.96 mmol), using bis(pinacolato)diboron (1.889 g, 7.44 mmol), potassium acetate (1.460 g, 14.88 mmol) and Pd(dppf)Cl$_2$—CH$_2$Cl$_2$ (0.608 g, 0.744 mmol) in anhydrous dioxane (30 mL) under an Ar atmosphere and heating at 100° C. overnight. This gave after workup and purification by flash column chromatography [silica gel, 40g, eluting with EtOAc in hexane from 0-100%] ethyl 2-(2-((1-methyl-4-(4,4,5,5-tetramethyl-1,3,2-dioxaborolan-2-yl)-1H-indazol-6-yl)methoxy)phenyl)acetate (151a) (1.105 g, 50% yield) as a white solid; MS (ES+): 451.5 (M+1), 473.5 (M+Na).

Step-2: Preparation of Ethyl 2-(2-((4-(2-(aminomethyl)-3-fluoropyridin-4-yl)-1-methyl-1H-indazol-6-yl)methoxy)phenyl)acetate (151b)

Compound 151b was prepared according to the procedure reported in step-3 of Scheme-1 from ethyl 2-(2-((1-methyl-4-(4,4,5,5-tetramethyl-1,3,2-dioxaborolan-2-yl)-1H-indazol-6-yl)methoxy)phenyl)acetate (151a) (0.7 g, 1.554 mmol) in dioxane (30 mL) using (3-fluoro-4-iodopyridin-2-yl)methanamine (113a) (0.47 g, 1.865 mmol), bis(triphenylphosphine)palladium(II) chloride (0.164 g, 0.233 mmol) and a solution of K$_2$CO$_3$ (0.644 g, 4.66 mmol) in water (5 mL) under an Ar atmosphere and heating at 100° C. for 3 h on oil bath. This gave after workup, purification by flash column chromatography [silica (24 g), eluting with MeOH in DCM from 0-40%] compound 151b (0.219 g, 31% yield) free base as a yellow waxy solid. 105 mg of free-base was further purified by reverse-phase column chromatography [C18 (50 g), eluting with ACN in water (containing 0.1% HCl) from 0-100%] to afford ethyl 2-(2-((4-(2-(aminomethyl)-3-fluoropyridin-4-yl)-1-methyl-1H-indazol-6-yl)methoxy)phenyl)acetate (151b) (0.060 g, 57% yield) HCl salt as a yellow solid; $^1$H NMR (300 MHz, DMSO-d$_6$) δ 8.62 (d, J=4.9 Hz, 1H), 8.49 (s, 3H, D$_2$O exchangeable), 8.06 (dd, J=3.1, 1.0 Hz, 1H), 7.91 (s, 1H), 7.76 (t, J=5.3 Hz, 1H), 7.40 (s, 1H), 7.31-7.21 (m, 2H), 7.17-7.08 (m, 1H), 6.93 (td, J=7.4, 1.1 Hz, 1H), 5.33 (s, 2H), 4.47-4.31 (m, 2H), 4.12 (s, 3H), 3.93 (q, J=7.1 Hz, 2H), 3.67 (s, 2H), 0.98 (t, J=7.1 Hz, 3H); $^{19}$F NMR (282 MHz, DMSO-d$_6$) δ−128.80; MS (ES+): 449.2 (M+1); MS (ES−): 447.3 (M−1); HPLC purity: 89.52%.

Step-3: Preparation of 2-(2-((4-(2-(aminomethyl)-3-fluoropyridin-4-yl)-1-methyl-1H-indazol-6-yl)methoxy)phenyl)acetic Acid (151c)

Compound 151c was prepared according to the procedure reported in step-6 of Scheme-1, from ethyl 2-(2-((4-(2-(aminomethyl)-3-fluoropyridin-4-yl)-1-methyl-1H-indazol-6-yl)methoxy)phenyl)acetate (151b) (0.107 g, 0.239 mmol) in THF (4 mL) and MeOH (8 mL) using 2M LiOH (0.596 mL, 1.193 mmol). This gave after workup and purification by reverse phase column [C18 (50 g), eluting with ACN in water (containing 0.1% HCl) from 0-100%] 2-(2-((4-(2-(aminomethyl)-3-fluoropyridin-4-yl)-1-methyl-1H-indazol-6-yl)methoxy)phenyl)acetic acid (151c) (0.052 g, 52% yield) HCl salt as a yellow solid; $^1$H NMR (300 MHz, DMSO-d$_6$) δ 12.2 (bs, 1H, D$_2$O exchangeable), 8.61 (d, J=5.0 Hz, 1H), 8.55 (bs, 3H, D$_2$O exchangeable), 8.06 (dd, J=3.2, 1.0 Hz, 1H), 7.97-7.90 (m, 1H), 7.76 (t, J=5.3 Hz, 1H), 7.43 (s, 1H), 7.30-7.20 (m, 2H), 7.14-7.05 (m, 1H), 6.96-6.88 (m, 1H), 5.35 (s, 2H), 4.46-4.30 (m, 2H), 4.11 (s, 3H), 3.64 (s, 2H); $^{19}$F NMR (282 MHz, DMSO-d$_6$) δ−128.67; MS (ES+): 421.3 (M+1), 841.6 (2M+1); MS (ES−): 419.4 (M−1), 455.3 (M+Cl), 839.6 (2M−1); HPLC purity: 94.47%.

Scheme-152

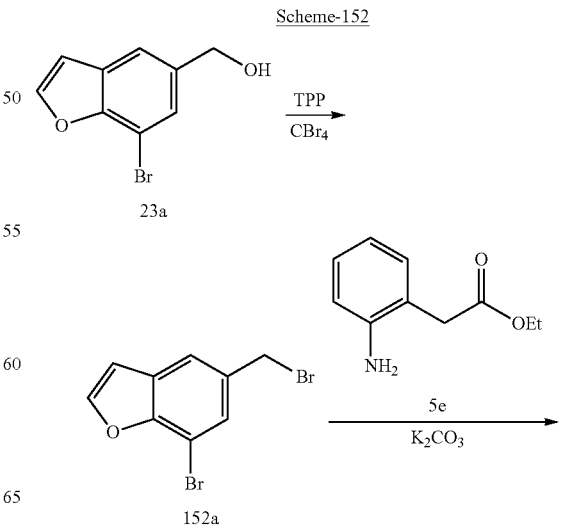

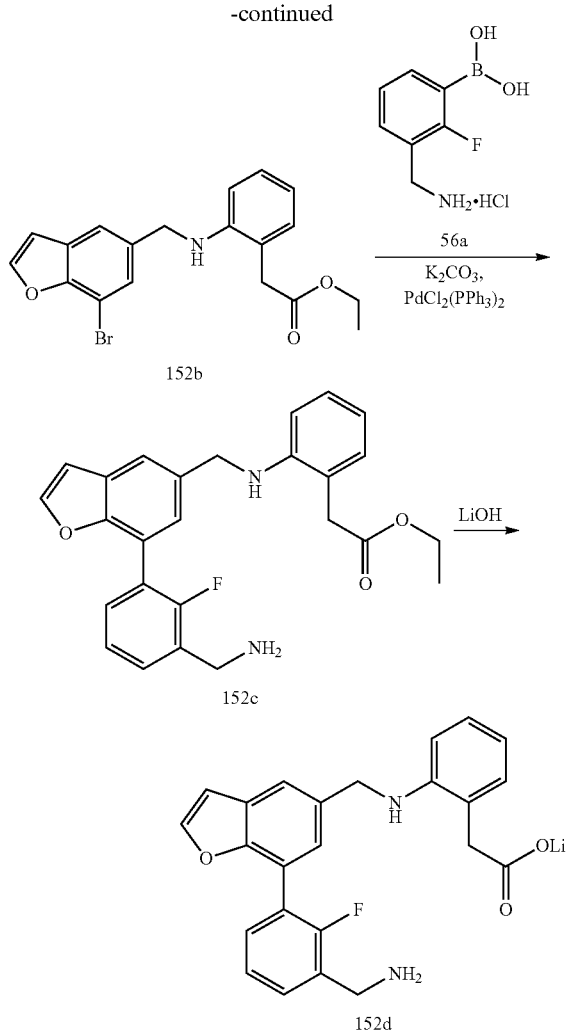

Preparation of lithium 2-(2-(((7-(3-(aminomethyl)-2-fluorophenyl)benzofuran-5-yl)methyl)amino)phenyl)acetate (152d)

Step-1: Preparation of 7-bromo-5-(bromomethyl)benzofuran (152a)

To a solution of (7-bromobenzofuran-5-yl)methanol (23a) (3.00 g, 13.21 mmol), CBr₄ (8.76 g, 26.4 mmol) in DCM (100 mL) was added at 0° C. a solution of triphenylphosphine (6.93 g, 26.4 mmol) in DCM (50 mL) over a period of 15 mins and stirred at 0° C. for 2 h. The reaction mixture diluted with water (200 mL) and extracted with DCM (2×150 mL). The combined organic layers were dried, filtered and evaporated to dryness. The residue obtained was purified by flash column chromatography [silica gel 40 g, eluting with ethyl acetate in hexanes from 0-100%] to furnish 7-bromo-5-(bromomethyl)benzofuran (152a) (2.38 g, 62% yield) as a pale yellow solid; $^1$H NMR (300 MHz, DMSO-$d_6$) δ 8.16 (d, J=2.2 Hz, 1H), 7.78 (d, J=1.6 Hz, 1H), 7.68 (d, J=1.6 Hz, 1H), 7.12 (d, J=2.2 Hz, 1H), 4.84 (s, 2H).

Step-2: Preparation of Ethyl 2-(2-(((7-bromobenzofuran-5-yl)methyl)amino)phenyl)acetate (152b)

To a stirred solution of ethyl 2-(2-aminophenyl)acetate (5e) (1.125 g, 6.28 mmol) in DMF (10 mL) was added K₂CO₃ (4.34 g, 31.4 mmol) followed by 7-bromo-5-(bromomethyl)benzofuran (152a) (1.82 g, 6.28 mmol). The resultant mixture was stirred at room temperature for 12 h and diluted with EtOAc (100 mL) and brine (100 mL). The organic layers were dried, filtered, evaporated to dryness. The residue obtained was purified by flash column chromatography [silica gel 40 g, eluting with ethyl acetate in hexanes from 0-100%] to furnish ethyl 2-(2-(((7-bromobenzofuran-5-yl)methyl)amino)phenyl)acetate (152b) (1.9 g, 4.89 mmol, 78% yield) as a thick yellow oil; $^1$H NMR (300 MHz, DMSO-$d_6$) δ 8.08 (d, J=2.2 Hz, 1H), 7.63 (d, J=1.4 Hz, 1H), 7.56 (d, J=1.4 Hz, 1H), 7.04 (d, J=2.2 Hz, 1H), 7.02-6.93 (m, 2H), 6.52 (td, J=7.4, 1.2 Hz, 1H), 6.45 (dd, J=8.1, 1.1 Hz, 1H), 5.83 (t, J=5.9 Hz, 1H), 4.42 (d, J=5.9 Hz, 2H), 4.11 (q, J=7.1 Hz, 2H), 3.65 (s, 2H), 1.20 (t, J=7.1 Hz, 3H).

Step-3: Preparation of Ethyl 2-(2-(((7-(3-(aminomethyl)-2-fluorophenyl)benzofuran-5-yl)methyl)amino)phenyl)acetate (152c)

Compound 152c was prepared according to the procedure reported in step-3 of Scheme-1 from ethyl 2-(2-(((7-bromobenzofuran-5-yl)methyl)amino)phenyl)acetate (152b) (0.700 g, 1.803 mmol) in dioxane (30 mL) using (3-(aminomethyl)-2-fluorophenyl)boronic acid hydrochloride (56a) (0.481 g, 2.344 mmol), bis(triphenylphosphine)palladium (II) chloride (PdCl₂(PPh₃)₂) (0.190 g, 0.270 mmol) and K₂CO₃ (0.748 g, 5.41 mmol) in water (3 mL) under an Ar atmosphere heating at 125° C. for 3h on oil bath. This gave after workup, purification by flash column chromatography [silica gel 40 g, eluting with methanol in DCM from 0-40%] ethyl 2-(2-(((7-(3-(aminomethyl)-2-fluorophenyl)benzofuran-5-yl)methyl)amino)phenyl)acetate (152c) (0.503 g, 65% yield) as greasy off-white solid; MS (ES+): 433.2 (M+1).

Step-4: Preparation of lithium 2-(2-(((7-(3-(aminomethyl)-2-fluorophenyl)benzofuran-5-yl)methyl)amino)phenyl)acetate (152d)

To a solution of ethyl 2-(2-(((7-(3-(aminomethyl)-2-fluorophenyl)benzofuran-5-yl)methyl)amino)phenyl)acetate (152c) (0.165 g, 0.382 mmol) in THF (10 mL) and MeOH (20 mL) was added lithium hydroxide monohydrate (2M, 0.954 mL, 1.908 mmol). The resulting mixture was stirred at room temperature for 12 h and evaporated in vacuum. The residue was purified by flash column chromatography [silica gel 40 g, eluting with methanol in DCM from 0-100%] and product was lyophilized to afford lithium 2-(2-(((7-(3-(aminomethyl)-2-fluorophenyl)benzofuran-5-yl)methyl)amino)phenyl)acetate (152d) (0.033 g, 0.080 mmol, 21.08% yield) as an off-white solid; $^1$H NMR (300 MHz, DMSO-$d_6$) δ 7.98 (s, 1H), 7.69 (s, 1H), 7.62-7.47 (m, 3H), 7.37-7.21 (m, 1H), 7.06-6.84 (m, 3H), 6.58-6.39 (m, 2H), 4.45 (s, 2H), 3.89 (s, 2H), 3.41 (s, 2H); $^{19}$F NMR (282 MHz, DMSO-$d_6$) δ −119.51; MS (ES+): 405.2 (M+1); MS (ES−): 403.3 (M−1); HPLC purity: 87.33%; Analysis calculated for: $C_{24}H_{20}FLiN_2O_3 \cdot 0.75H_2O$: C, 68.00; H, 5.11; N, 6.61; Found: C, 67.69; H, 5.44; N, 6.48.

Scheme-153

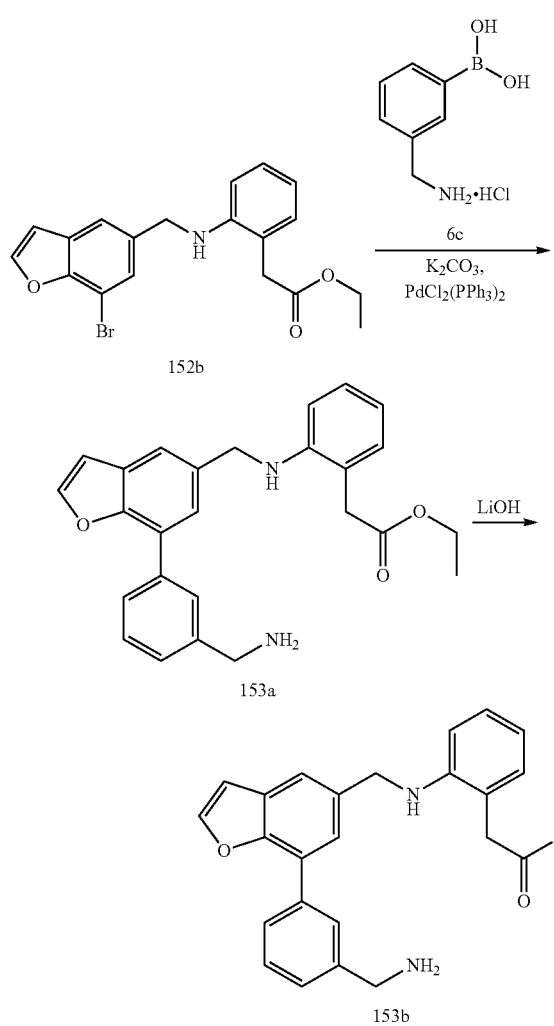

Preparation of lithium 2-(2-(((7-(3-(aminomethyl) phenyl)benzofuran-5-yl)methyl)amino)phenyl)acetate (153b)

Step-1: Preparation of Ethyl 2-(2-(((7-(3-(aminomethyl)phenyl)benzofuran-5-yl)methyl)amino)phenyl) acetate (153a)

Compound 153a was prepared according to the procedure reported in step-3 of Scheme-1 from ethyl 2-(2-(((7-bromobenzofuran-5-yl)methyl)amino)phenyl)acetate (152b) (0.600 g, 1.545 mmol) in dioxane (30 mL) using (3-(aminomethyl)phenyl)boronic acid hydrochloride (6c) (0.377 g, 2.009 mmol), bis(triphenylphosphine)palladium(II) chloride (PdCl$_2$(PPh$_3$)$_2$) (0.163 g, 0.232 mmol) and K$_2$CO$_3$ (0.641 g, 4.64 mmol) in water (3 mL) under an Ar atmosphere heating at 125° C. for 3h on oil bath. This gave after workup, purification by flash column chromatography [silica gel 40 g, eluting with methanol in DCM from 0-40%] ethyl 2-(2-(((7-(3-(aminomethyl)phenyl)benzofuran-5-yl)methyl) amino)phenyl)acetate (153a) (0.531 g, 1.281 mmol, 83% yield) as a waxy off-white solid; MS (ES+): 415.2 (M+1).

Step-2: Preparation of lithium 2-(2-(((7-(3-(aminomethyl)phenyl)benzofuran-5-yl)methyl)amino) phenyl)acetate (153b)

To a solution of ethyl 2-(2-(((7-(3-(aminomethyl)phenyl) benzofuran-5-yl)methyl)amino)phenyl)acetate (153a) (0.251 g, 0.606 mmol) in THF (10 mL) and MeOH (20 mL) was added lithium hydroxide monohydrate (1.514 mL, 3.03 mmol). The resulting mixture was stirred at room temperature for 12 h and evaporated to dryness. The residue was purified by flash column chromatography [silica gel 40 g, eluting with methanol in DCM from 0-100%] and product was lyophilized to afford lithium 2-(2-(((7-(3-(aminomethyl)phenyl)benzofuran-5-yl)methyl)amino)phenyl)acetate (153b) (0.051 g, 22% yield) as a yellow solid; $^1$H NMR (300 MHz, DMSO-d$_6$) δ 8.28 (s, 1H), 8.14-8.08 (m, 1H), 8.05 (d, J=2.2 Hz, 1H), 7.98 (d, J=1.7 Hz, 1H), 7.67 (d, J=1.5 Hz, 1H), 7.46 (t, J=7.7 Hz, 1H), 7.36-7.28 (m, 1H), 7.01 (d, J=2.2 Hz, 1H), 6.89 (dd, J=7.3, 1.6 Hz, 1H), 6.80 (td, J=7.7, 1.6 Hz, 1H), 6.51-6.35 (m, 2H), 4.51 (d, J=5.8 Hz, 2H), 4.02 (s, 2H), 3.33 (s, 2H); MS (ES+): 387.3 (M+1); MS (ES-): 385.4 (M-1); HPLC purity: 92.66%; Analysis calculated for: C$_{24}$H$_{21}$LiN$_2$O$_3$ 0.25H$_2$O: C, 72.63; H, 5.46; N, 7.06; Found: C, 72.62; H, 5.45; N, 6.95.

Scheme-154

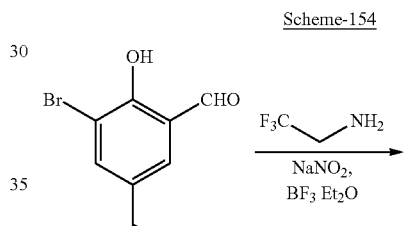

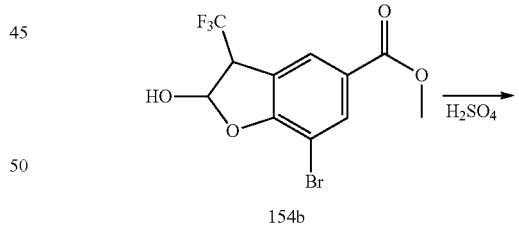

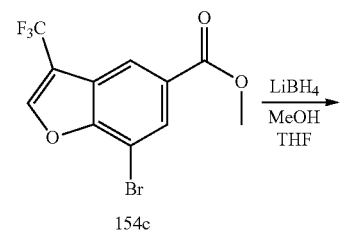

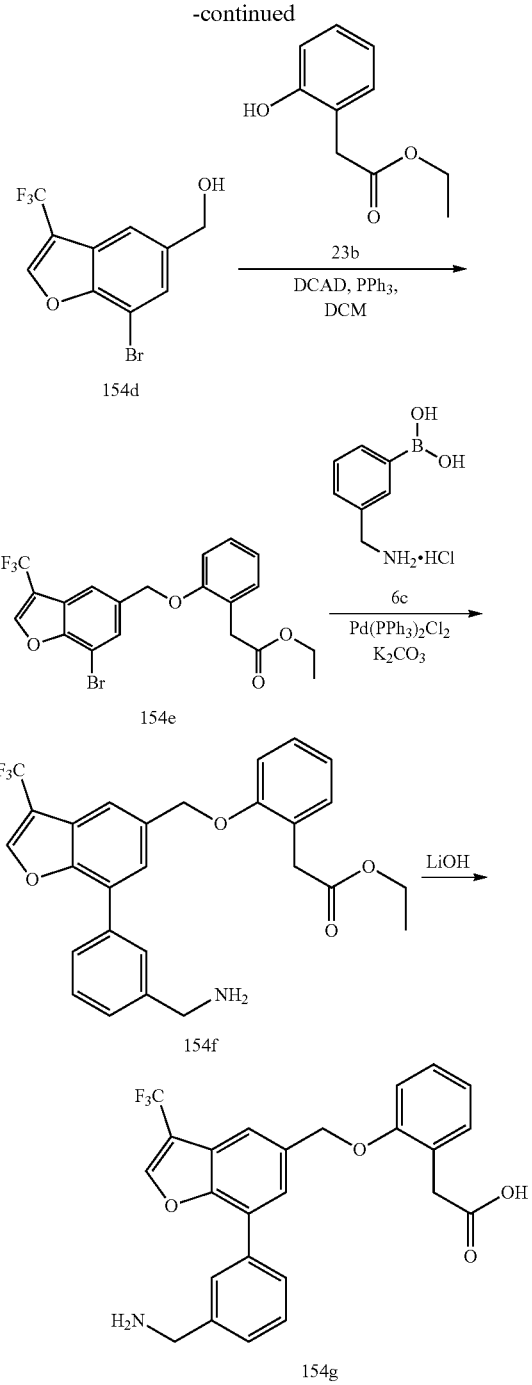

Preparation of 2-(2-((7-(3-(aminomethyl)phenyl)-3-(trifluoromethyl)benzofuran-5-yl)methoxy)phenyl) acetic Acid (154g)

Step-1: Preparation of methyl 7-bromo-2-hydroxy-3-(trifluoromethyl)-2,3-dihydrobenzofuran-5-carboxylate (154b)

To a solution of 2,2,2-trifluoroethanamine HCl (1.71 g, 17.26 mmol; CAS #373-88-6) in DCM (15 mL) at 0° C., was added a solution of sodium nitrite (1.27 g, 18.41 mmol) in water (1.5 mL). The mixture was kept at ice bath for 1 h, cooled to −78° C. and added methyl 3-bromo-5-formyl-4-hydroxybenzoate (154a) (0.522 g, 2.015 mmol; CAS #706820-79-3) and boron trifluoride etherate (1.2 mL, 9.47 mmol) was added. The mixture was stirred at −78° C. for 12 h, warmed to room temperature over a 12 h period. The reaction was quenched with methanol (8 mL), diluted with saturated aqueous NaHCO$_3$, and extracted with ethyl acetate. The organic layers were combined, washed with brine, dried, filtered and concentrated in vacuum. The residue obtained was purified by flash column chromatography [silica (24 g), eluting with ethyl acetate/hexanes, 0-30%] to afford methyl 7-bromo-2-hydroxy-3-(trifluoromethyl)-2,3-dihydrobenzofuran-5-carboxylate (154b) (503 mg, 73% yield) as white solid; $^1$H NMR (300 MHz, DMSO-d$_6$) δ 8.60 (d, J=6.0 Hz, 1H), 8.11 (dd, J=1.7, 0.6 Hz, 1H), 7.91 (dt, J=1.8, 0.9 Hz, 1H), 6.28 (dd, J=5.9, 2.4 Hz, 1H), 4.67-4.46 (m, 1H), 3.85 (s, 3H); $^{19}$F NMR (282 MHz, DMSO-d$_6$) δ−69.45.

Step-2: Preparation of methyl 7-bromo-3-(trifluoromethyl)benzofuran-5-carboxylate (154c)

A solution of methyl 7-bromo-2-hydroxy-3-(trifluoromethyl)-2,3-dihydrobenzofuran-5-carboxylate (154b) (495 mg, 1.451 mmol) in sulfuric acid (5 mL, 94 mmol) was stirred at room temperature for 30 min. The mixture was poured into ice water and the white solid obtained was collected by filtration, dried in vacuum to provide methyl 7-bromo-3-(trifluoromethyl)benzofuran-5-carboxylate (154c) (462 mg, 99% yield). $^1$H NMR (300 MHz, DMSO-d$_6$) δ 9.11 (t, J=1.7 Hz, 1H), 8.23 (d, J=1.5 Hz, 1H), 8.20 (dt, J=1.5, 0.9 Hz, 1H), 3.92 (s, 3H).

Step-3: Preparation of (7-bromo-3-(trifluoromethyl)benzofuran-5-yl)methanol (154d)

Compound 154d was prepared according to the procedure reported in step-2 of Scheme-76 from methyl 7-bromo-3-(trifluoromethyl)benzofuran-5-carboxylate (154c) (927 mg, 2.87 mmol) in THF (12 mL) using LiBH$_4$ (2.20 mL, 8.80 mmol, 2 M solution in THF) and MeOH (385 μl, 9.52 mmol). This gave after workup (7-bromo-3-(trifluoromethyl)benzofuran-5-yl)methanol (154d) (836 mg, 99% yield) as a white solid. $^1$H NMR (300 MHz, Methanol-d$_4$) δ 8.41 (d, J=1.7 Hz, 1H), 7.61 (q, J=1.6 Hz, 2H), 4.69 (s, 2H).

Step-4: Preparation of Ethyl 2-(2-((7-bromo-3-(trifluoromethyl)benzofuran-5-yl)methoxy)phenyl)acetate (154e)

Compound 154e was prepared according to the procedure reported in step-2 of Scheme-23 from (7-bromo-3-(trifluoromethyl)benzofuran-5-yl)methanol (154d) (80 mg, 0.271 mmol) in DCM (6 mL) using triphenylphosphine (82 mg, 0.313 mmol), ethyl 2-(2-hydroxyphenyl) acetate (23b) (74 mg, 0.411 mmol) and di-(4-chlorobenzyl)azodicarboxylate (117 mg, 0.319 mmol) in DCM (2 mL). This gave after workup and purification by flash column chromatography [silica (12 g), eluting with ethyl acetate/hexanes, 0-40%] ethyl 2-(2-((7-bromo-3-(trifluoromethyl)benzofuran-5-yl)methoxy)phenyl)acetate (154e) (67 mg, 54% yield) as white solid. $^1$H NMR (300 MHz, DMSO-d$_6$) δ 8.97 (q, J=1.6 Hz, 1H), 7.81 (s, 2H), 7.37-7.17 (m, 2H), 7.08 (dd, J=8.3, 1.1 Hz, 1H), 6.93 (td, J=7.4, 1.1 Hz, 1H), 5.25 (s, 2H), 4.01 (q, J=7.1 Hz, 2H), 3.63 (s, 2H), 1.07 (t, J=7.1 Hz, 3H); $^{19}$F NMR (282 MHz, DMSO-d$_6$) δ−58.25.

Step-5: Preparation of Ethyl 2-(2-((7-(3-(aminomethyl)phenyl)-3-(trifluoromethyl)benzofuran-5-yl)methoxy)phenyl)acetate (154f)

Compound 154f was prepared according to the procedure reported in step-3 of Scheme-1 from ethyl 2-(2-((7-bromo-3-(trifluoromethyl)benzofuran-5-yl)methoxy)phenyl)acetate (154e) (220 mg, 0.481 mmol) in dioxane (5 mL) using 3-(aminomethyl)phenylboronic acid hydrochloride (6c) (111 mg, 0.735 mmol), a solution of $K_2CO_3$ (206 mg, 1.491 mmol) in water (0.5 mL), bis(triphenylphosphine)palladium (II) chloride (60 mg, 0.085 mmol) and heating at 100° C. for 3h on oil bath. This gave after workup and purification by flash column chromatography [silica (24 g), eluting with DMA80 in DCM from 0-50%] ethyl 2-(2-((7-(3-(aminomethyl)phenyl)-3-(trifluoromethyl)benzofuran-5-yl)methoxy)phenyl)acetate (154f) (145 mg, 62% yield) as a dark oil. An analytical sample was obtained by further purification by reverse phase column chromatography [C18 (50 g), eluting with ACN in water (containing 0.1% HCl) from 0-100%] to afford compound 154f HCl salt as white solid. $^1$H NMR (300 MHz, Methanol-$d_4$) δ 8.47 (q, J=1.6 Hz, 1H), 8.07-7.89 (m, 2H), 7.88-7.74 (m, 2H), 7.71-7.45 (m, 2H), 7.34-7.14 (m, 2H), 7.09 (dd, J=8.3, 1.1 Hz, 1H), 6.94 (td, J=7.4, 1.1 Hz, 1H), 5.29 (s, 2H), 4.25 (s, 2H), 3.96 (q, J=7.1 Hz, 2H), 3.67 (s, 2H), 1.02 (t, J=7.1 Hz, 3H); MS (ES+): 484.2 (M+1); (ES−): 482.3 (M−1); HPLC purity 98.43%.

Step-6: Preparation of 2-(2-((7-(3-(aminomethyl)phenyl)-3-(trifluoromethyl)benzofuran-5-yl)methoxy)phenyl)acetic Acid (154g)

Compound 154g was prepared according to the procedure reported in step-6 of Scheme-1, from ethyl 2-(2-((7-(3-(aminomethyl)phenyl)-3-(trifluoromethyl)benzofuran-5-yl)methoxy)phenyl)acetate (154f) (96 mg, 0.199 mmol) in MeOH/THF (6 mL, each) using a solution of lithium hydroxide monohydrate (40 mg, 1.670 mmol) in water (2 mL). This gave after workup and purification by reverse phase column chromatography [C18 (50 g), eluting with ACN in water (containing 0.1% HCl) from 0-100%] 2-(2-((7-(3-(aminomethyl)phenyl)-3-(trifluoromethyl)benzofuran-5-yl)methoxy)phenyl)acetic acid (154g) (67 mg, 74% yield) HCl salt as a white solid. $^1$H NMR (300 MHz, Methanol-$d_4$) δ 8.45 (q, J=1.6 Hz, 1H), 8.05-7.96 (m, 2H), 7.81 (dd, J=9.7, 1.6 Hz, 2H), 7.61 (t, J=7.9 Hz, 1H), 7.53 (dt, J=7.7, 1.5 Hz, 1H), 7.30-7.19 (m, 2H), 7.06 (d, J=8.0 Hz, 1H), 6.93 (td, J=7.4, 1.1 Hz, 1H), 5.30 (s, 2H), 4.23 (s, 2H), 3.70 (s, 2H); MS (ES+): 456.1 (M+1); MS (ES−): 454.2 (M−1). HPLC purity 97.47%. Analysis calculated for $C_{25}H_{20}F_3NO_4 \cdot HCl$: C, 61.04; H, 4.30; Cl, 7.21; N, 2.85; Found: C, 60.83; H, 4.63; Cl, 7.61; N, 2.65.

Scheme-155

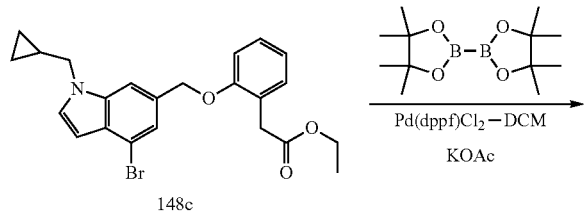

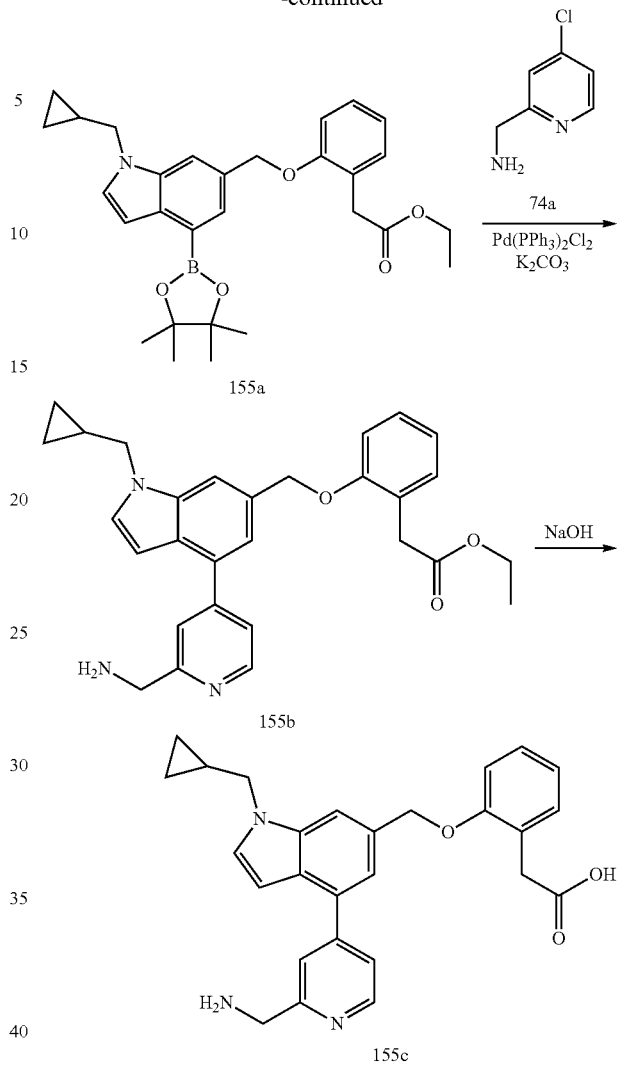

Preparation of 2-(2-((4-(2-(aminomethyl)pyridin-4-yl)-1-(cyclopropylmethyl)-1H-indol-6-yl)methoxy)phenyl)acetic Acid (155c)

Step-1: Preparation of Ethyl 2-(2-((1-(cyclopropylmethyl)-4-(4,4,5,5-tetramethyl-1,3,2-dioxaborolan-2-yl)-1H-indol-6-yl)methoxy)phenyl)acetate (155a)

Compound 155a was prepared according to the procedure reported in step-1 of Scheme-59 from ethyl 2-(2-((4-bromo-1-(cyclopropylmethyl)-1H-indol-6-yl)methoxy)phenyl)acetate (148c) (3.5 g, 7.91 mmol), using bis(pinacolato)diboron (3.01 g, 11.87 mmol), potassium acetate (2.33 g, 23.74 mmol) and $Pd(dppf)Cl_2$—$CH_2Cl_2$ (0.97 g, 1.19 mmol) in anhydrous dioxane (50 mL) under an Ar atmosphere and heating at 100° C. overnight. This gave after workup and purification by flash column chromatography [silica gel, 40g, eluting with EtOAc/MeOH=9:1 in hexane from 0-10%] ethyl 2-(2-((1-(cyclopropylmethyl)-4-(4,4,5,5-tetramethyl-1,3,2-dioxaborolan-2-yl)-1H-indol-6-yl)methoxy)phenyl)acetate (155a) (1.9 g, 49% yield) as a yellow oil; $^1$H NMR (300 MHz, DMSO-$d_6$) δ 7.71 (q, J=1.7, 1.0 Hz, 1H), 7.53-7.41 (m, 2H), 7.22 (ddd, J=7.2, 3.6, 1.6 Hz, 2H), 7.09

(dd, J=8.3, 1.1 Hz, 1H), 6.89 (td, J=7.4, 1.1 Hz, 1H), 6.73 (dd, J=3.1, 0.8 Hz, 1H), 5.19 (s, 2H), 4.12-3.94 (m, 4H), 3.60 (s, 2H), 1.33 (s, 12H), 1.26-1.18 (m, 1H), 1.05 (t, J=7.1 Hz, 3H), 0.52-0.28 (m, 4H); MS (ES+): 490.3 (M+1).

Step-2: Preparation of Ethyl 2-(2-((4-(2-(aminomethyl)pyridin-4-yl)-1-(cyclopropylmethyl)-1H-indol-6-yl)methoxy)phenyl)acetate (155b)

Compound 155b was prepared according to the procedure reported in step-3 of Scheme-1 from ethyl 2-(2-((1-(cyclopropylmethyl)-4-(4,4,5,5-tetramethyl-1,3,2-dioxaborolan-2-yl)-1H-indol-6-yl)methoxy)phenyl)acetate (155a) (0.7 g, 1.43 mmol) in dioxane (6 mL) using (4-chloropyridin-2-yl)methanamine (74a) (0.13 mL, 1.10 mmol), bis(triphenylphosphine)palladium(II) chloride (0.12 g, 0.17 mmol) and a solution of $K_2CO_3$ (0.38 g, 2.75 mmol) in water (0.7 mL) under an Ar atmosphere and heating at 100° C. for 2 h on oil bath. This gave after workup, purification by flash column chromatography [silica (12 g), eluting with DMA80 in DCM from 0-50%] followed by purification by reverse-phase column chromatography [C18 (50 g), eluting with ACN in water (containing 0.1% HCl) from 0-100%] ethyl 2-(2-((4-(2-(aminomethyl)pyridin-4-yl)-1-(cyclopropylmethyl)-1H-indol-6-yl)methoxy)phenyl)acetate (155b) (0.07 g, 14% yield) HCl salt as a yellow solid; MS (ES+): 470.2 (M+1).

Step-3: Preparation of 2-(2-((4-(2-(aminomethyl)pyridin-4-yl)-1-(cyclopropylmethyl)-1H-indol-6-yl)methoxy)phenyl)acetic Acid (155c)

Compound 155c was prepared according to the procedure reported in step-4 of Scheme-4, from ethyl 2-(2-((4-(2-(aminomethyl)pyridin-4-yl)-1-(cyclopropylmethyl)-1H-indol-6-yl)methoxy)phenyl)acetate (155b) (0.07 g, 0.15 mmol) in THF (3 mL) and MeOH (3 mL) using sodium hydroxide (0.02 g, 0.45 mmol) in water (0.6 mL). This gave after workup and purification by reverse phase column [C18 (50 g), eluting with ACN in water (containing 0.1% HCl) from 0-100%] 2-(2-((4-(2-(aminomethyl)pyridin-4-yl)-1-(cyclopropylmethyl)-1H-indol-6-yl)methoxy)phenyl)acetic acid (155c) (0.05 g, 70% yield) HCl salt as a yellow solid; $^1$H NMR (300 MHz, DMSO-$d_6$) δ 8.72 (d, J=5.2 Hz, 1H), 8.40 (s, 3H), 7.85 (d, J=1.5 Hz, 1H), 7.78 (s, 1H), 7.74 (dd, J=5.2, 1.6 Hz, 1H), 7.63 (d, J=3.2 Hz, 1H), 7.37 (d, J=1.3 Hz, 1H), 7.22 (d, J=7.4 Hz, 2H), 7.11 (d, J=8.1 Hz, 1H), 6.94-6.86 (m, 1H), 6.71 (d, J=3.2 Hz, 1H), 5.29 (s, 2H), 4.31 (s, 2H), 4.12 (d, J=7.0 Hz, 2H), 3.60 (s, 2H), 1.34-1.20 (m, 1H), 0.57-0.33 (m, 4H); MS (ES-): 440.3 (M-1). HPLC purity: 98.99%.

Scheme-156

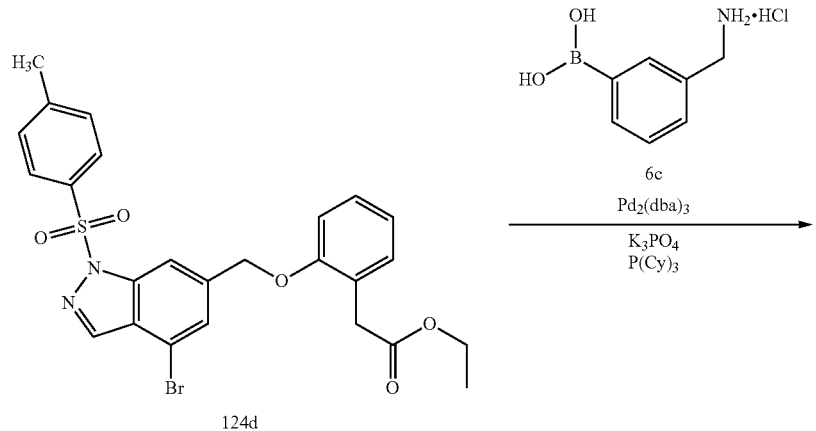

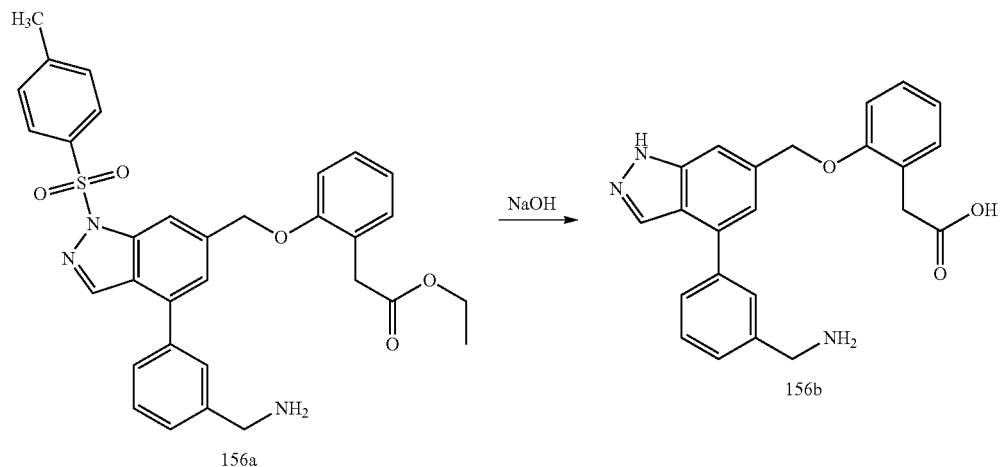

Preparation of 2-(2-((4-(3-(aminomethyl)phenyl)-1H-indazol-6-yl)methoxy)phenyl)acetic acid (156b)

Step-1: Preparation of Ethyl 2-(2-((4-(3-(aminomethyl)phenyl)-1-tosyl-1H-indazol-6-yl)methoxy)phenyl)acetate (156a)

Compound 156a was prepared according to the procedure reported in step-3 of Scheme-1 from ethyl 2-(2-((4-bromo-1-tosyl-1H-indazol-6-yl)methoxy)phenyl)acetate (124d) (0.335 g, 0.616 mmol) in dioxane (6 mL) using 3-(aminomethyl)phenylboronic acid hydrochloride (6c) (0.140 g, 0.925 mmol), tripotassium phosphate (1.3 M solution, 1.423 mL, 1.849 mmol), tricyclohexylphosphine (0.052 g, 0.185 mmol) and $Pd_2(dba)_3$ (0.056 g, 0.062 mmol) under a nitrogen atmosphere and heating at 125° C. for 45 min in a microwave. This gave after workup, purification by flash column chromatography [silica gel, 25g, eluting with methanol in DCM from 0-40%] ethyl 2-(2-((4-(3-(aminomethyl)phenyl)-1-tosyl-1H-indazol-6-yl)methoxy)phenyl)acetate (156a) (0.266 g, 76% yield) as an off-white solid; MS (ES+): 570.3 (M+Na).

Step-2: Preparation of 2-(2-((4-(3-(aminomethyl)phenyl)-1H-indazol-6-yl)methoxy)phenyl)acetic Acid (156b)

To a solution of ethyl 2-(2-((4-(3-(aminomethyl)phenyl)-1-tosyl-1H-indazol-6-yl)methoxy)phenyl)acetate (156a) (0.075 g, 0.132 mmol) in THF (3.0 mL) and methanol (6.0 mL) was added sodium hydroxide (2 M aq.) (0.658 mL, 1.317 mmol) and stirred at room temperature for 6 h and concentrated in vacuum to remove THF/MeOH. The aqueous layer was acidified with cold 2N aq. HCl and the residue was purified by reverse-phase column chromatography [C-18 column, 50 g, eluting with 0.1% aq. HCl in water and acetonitrile from 0-100%] to afford on lyophilization 2-(2-((4-(3-(aminomethyl)phenyl)-1H-indazol-6-yl)methoxy)phenyl)acetic acid (156b) (0.034 g, 0.088 mmol, 66.7% yield) HCl salt as a white solid; $^1$H NMR (300 MHz, DMSO-$d_6$) δ 13.31 (s, 1H, $D_2O$ exchangeable), 8.44-8.22 (m, 4H, $D_2O$ exchangeable, 3H), 7.91 (s, 1H), 7.77 (d, J=7.6 Hz, 1H), 7.65 (s, 1H), 7.60 (t, J=7.5 Hz, 1H), 7.56-7.50 (m, 1H), 7.40-7.33 (m, 1H), 7.28-7.19 (m, 2H), 7.09 (d, J=8.4 Hz, 1H), 6.91 (t, J=7.4 Hz, 1H), 5.33 (s, 2H), 4.24-4.09 (m, 2H), 3.62 (s, 2H); MS (ES+): 388.3 (M+1); 775.5 (2M+1); MS (ES−): 386.3 (M−1); 422.4 (M+Cl); 773.6 (2M−1); HPLC purity: 93.41%; Analysis calculated for $C_{23}H_{21}N_3O_3 \cdot 2.25H_2O \cdot 2.0HCl$: C, 55.15; H, 5.53; N, 8.39; Found: C, 54.94; H, 5.34; N, 8.00.

Scheme-157

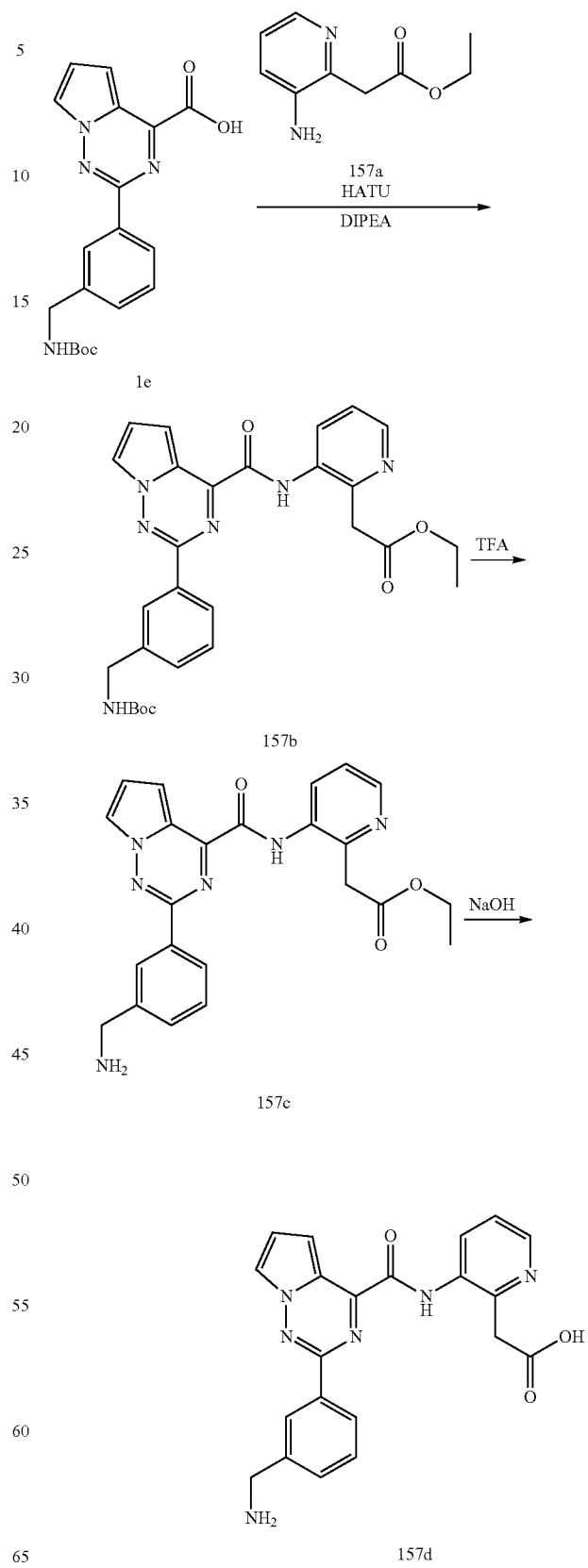

Preparation of 2-(3-(2-(3-(aminomethyl)phenyl) pyrrolo[2,1-f][1,2,4]triazine-4-carboxamido)pyridin-2-yl)acetic Acid (157d)

Step-1: Preparation of Ethyl 2-(3-(2-(3-(((tert-butoxycarbonyl)amino)methyl)phenyl)pyrrolo[2,1-f][1,2,4]triazine-4-carboxamido)pyridin-2-yl)acetate (157b)

Compound 157b was prepared according to the procedure reported in step-4 of Scheme-1 from 2-(3-(((tert-butoxycarbonyl)amino)methyl)phenyl)pyrrolo[2,1-f][1,2,4]triazine-4-carboxylic acid (1e) (0.144 g, 0.391 mmol) in DMF (2 mL) using ethyl 2-(3-aminopyridin-2-yl)acetate (157a) (0.13 g, 0.469 mmol; prepared according to the procedure reported by Mikami, Satoshi et al; in Journal of Medicinal Chemistry, 60(18), 7677-7702; 2017), DIPEA (0.341 mL, 1.954 mmol) and HATU (0.781 g, 0.469 mmol). This gave after workup and purification by flash column chromatography [silica 12 g, eluting with MeOH:EtOAc (9:1) in hexanes from 0 to 100%] ethyl 2-(3-(2-(3-(((tert-butoxycarbonyl)amino)methyl)phenyl)pyrrolo[2,1-f][1,2,4]triazine-4-carboxamido)pyridin-2-yl)acetate (157b) (0.15 g, 0.283 mmol, 72.3% yield) as an orange solid; $^1$H NMR (300 MHz, DMSO-$d_6$) δ 10.90 (s, 1H), 8.50-8.41 (m, 2H), 8.41-8.32 (m, 2H), 8.15 (dd, J=8.2, 1.6 Hz, 1H), 7.59-7.39 (m, 4H), 7.26 (dd, J=4.6, 2.5 Hz, 1H), 4.27 (d, J=6.2 Hz, 2H), 4.10-3.97 (m, 4H), 1.41 (s, 9H), 1.02 (t, J=7.1 Hz, 3H); MS (ES+): 531.4 (M+1), 553.4 (M+Na).

Step-2: Preparation of Ethyl 2-(3-(2-(3-(aminomethyl)phenyl)pyrrolo[2,1-f][1,2,4]triazine-4-carboxamido)pyridin-2-yl)acetate (157c)

Compound 157c was prepared according to the procedure reported in step-5 of Scheme-1 from ethyl 2-(3-(2-(3-(((tert-butoxycarbonyl)amino)methyl)phenyl)pyrrolo[2,1-f][1,2,4]triazine-4-carboxamido)pyridin-2-yl)acetate (157b) (0.15 g, 0.283 mmol) in DCM (4 mL) using TFA (0.218 mL, 2.83 mmol). This gave after workup and purification by reverse phase column chromatography [C-18 column, 30 g, eluting with 0.1% aq. HCl in water and acetonitrile from 0-100%] ethyl 2-(3-(2-(3-(aminomethyl)phenyl)pyrrolo[2,1-f][1,2,4]triazine-4-carboxamido)pyridin-2-yl)acetate (157c) (0.028 g, 23% yield) as HCl salt; MS (ES+): 431.4 (M+1).

Step-3: Preparation of 2-(3-(2-(3-(aminomethyl)phenyl)pyrrolo[2,1-f][1,2,4]triazine-4-carboxamido)pyridin-2-yl)acetic Acid (157d)

Compound 157d was prepared according to the procedure reported in step-4 of Scheme-4 from ethyl 2-(3-(2-(3-(aminomethyl)phenyl)pyrrolo[2,1-f][1,2,4]triazine-4-carboxamido)pyridin-2-yl)acetate (157c) (0.1 g, 0.232 mmol) in THF (3 mL) and methanol (3 mL) using sodium hydroxide (2 M, 0.348 mL, 0.697 mmol). This gave after workup and purification by reverse phase column [C18 (30 g), eluting with ACN in water (containing 0.1% HCl) from 0-100%] followed by flash column chromatography [silica gel 12 g, eluting with methanol in DCM from 0-100%] 2-(3-(2-(3-(aminomethyl)phenyl)pyrrolo [2,1-f][1,2,4]triazine-4-carboxamido)pyridin-2-yl)acetic acid (157d) (0.007 g, 8% yield) as a yellow solid; $^1$H NMR (300 MHz, DMSO-$d_6$) δ 12.61 (s, 1H, D$_2$O exchangeable), 9.33 (s, 1H, D$_2$O exchangeable), 8.42-8.36 (m, 1H), 8.34-8.22 (m, 3H), 7.62 (dd, J=4.6, 1.3 Hz, 1H), 7.56 (d, J=4.8 Hz, 2H), 7.35 (dd, J=8.1, 4.7 Hz, 1H), 7.26 (dd, J=4.6, 2.6 Hz, 1H), 4.14 (s, 2H), 3.74 (s, 2H); MS (ES+): 403.3 (M+1), 425.3 (M+Na); MS (ES−): 401.4 (M−1), 803.5 (2M−1); HPLC purity: 90.71%.

Scheme-158

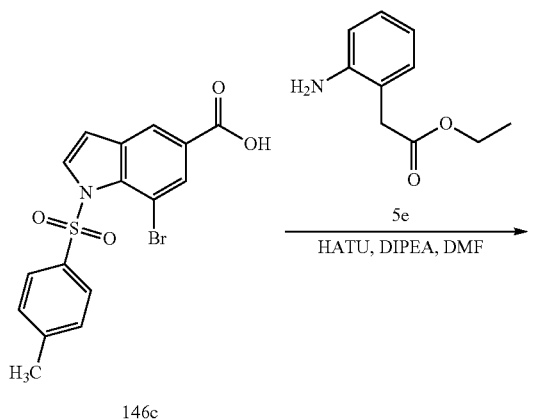

146c

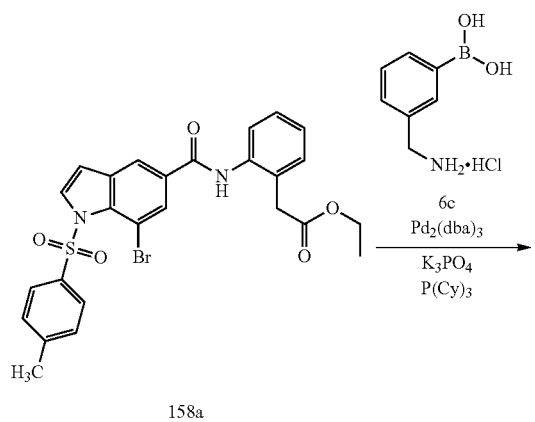

158a

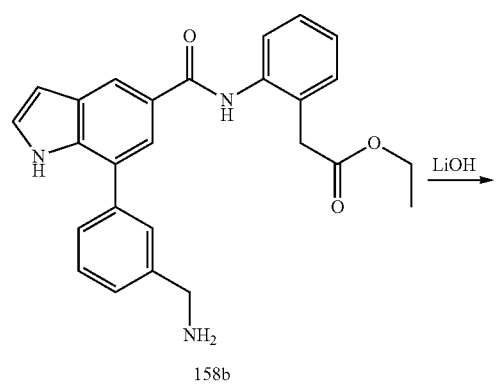

158b

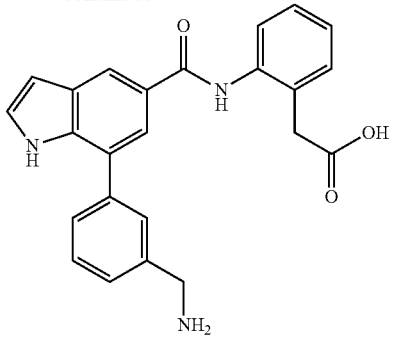

158c

Preparation of 2-(2-(7-(3-(aminomethyl)phenyl)-1H-indole-5-carboxamido)phenyl)acetic acid (158c)

Step-1: Preparation of Ethyl 2-(2-(7-bromo-1-tosyl-1H-indole-5-carboxamido)phenyl)acetate (158a)

Compound 158a was prepared according to the procedure reported in step-4 of Scheme-1 from 7-bromo-1-tosyl-1H-indole-5-carboxylic acid (146c) (200 mg, 0.507 mmol) in DMF (15 mL) using ethyl 2-(2-aminophenyl)acetate (5e) (182 mg, 1.015 mmol), DIPEA (0.353 mL, 2.029 mmol) and HATU (386 mg, 1.015 mmol). This gave after workup and purification by flash column chromatography [silica 12 g, eluting with hexanes/ethyl acetate (1:0 to 2:1)] ethyl 2-(2-(7-bromo-1-tosyl-1H-indole-5-carboxamido)phenyl)acetate (158a) (102 mg) as a brown gum MS (ES+): 555.10 & 557.10 (M+1); MS (ES−): 553.20 & 555.20 (M−1).

Step-2: Preparation of Ethyl 2-(2-(7-(3-(aminomethyl)phenyl)-1H-indole-5-carboxamido)phenyl)acetate (158b)

Compound 158b was prepared according to the procedure reported in step-3 of Scheme-1 from ethyl 2-(2-(7-bromo-1-tosyl-1H-indole-5-carboxamido)phenyl)acetate (158a) (90 mg, 0.162 mmol) in dioxane (4 mL) using 3-(aminomethyl)phenylboronic acid hydrochloride (6c) (46 mg, 0.243 mmol), tripotassium phosphate (1.3 M solution, 0.092 mL, 0.275 mmol), tricyclohexylphosphine (0.027 g, 0.097 mmol) and Pd$_2$(dba)$_3$ (0.045 g, 0.049 mmol) under a nitrogen atmosphere and heating at 125° C. for 2 h in a microwave. This gave after workup, purification by flash column chromatography [silica gel, 25g, eluting with dichloromethane/methanol (1:0 to 9:1)] ethyl 2-(2-(7-(3-(aminomethyl)phenyl)-1H-indole-5-carboxamido)phenyl)acetate (158b) (5 mg, 3% for two steps) as a white solid. MS (ES+): 428.3 (M+1) & 450.3 (M+Na); MS (ES−): 426.5 (M−1) & 462.4 (M+Cl).

Step-3: Preparation of 2-(2-(7-(3-(aminomethyl)phenyl)-1H-indole-5-carboxamido)phenyl)acetic Acid (158c)

Compound 158c was prepared according to the procedure reported in step-6 of Scheme-1 from ethyl 2-(2-(7-(3-(aminomethyl)phenyl)-1H-indole-5-carboxamido)phenyl)acetate (158b) (5 mg, 0.012 mmol) in THF (2 mL) and methanol (2 mL) using lithium hydroxide hydrate (5.01 mg, 0.117 mmol) in water (2 mL). This gave after workup and purification by flash column chromatography [silica gel, eluting with dichloromethane/methanol (1:0 to 3:1)] 2-(2-(7-(3-(aminomethyl)phenyl)-1H-indole-5-carboxamido)phenyl)acetic acid (158c) (4 mg, 86%) as a light brown solid; $^1$H NMR (300 MHz, DMSO-d$_6$) δ 12.54 (s, 1H), 11.44 (s, 1H), 8.27 (s, 1H), 8.22 (s, 1H), 8.13 (s, 1H), 8.02 (d, J=7.9 Hz, 1H), 7.87 (d, J=7.7 Hz, 1H), 7.54 (t, J=7.6 Hz, 1H), 7.49-7.38 (m, 2H), 7.25-7.15 (m, 2H), 7.01 (t, J=7.4 Hz, 1H), 6.71 (s, 1H), 4.10 (s, 2H), 3.47 (s, 2H); MS (ES−): 398.4 (M−1).

Scheme-159

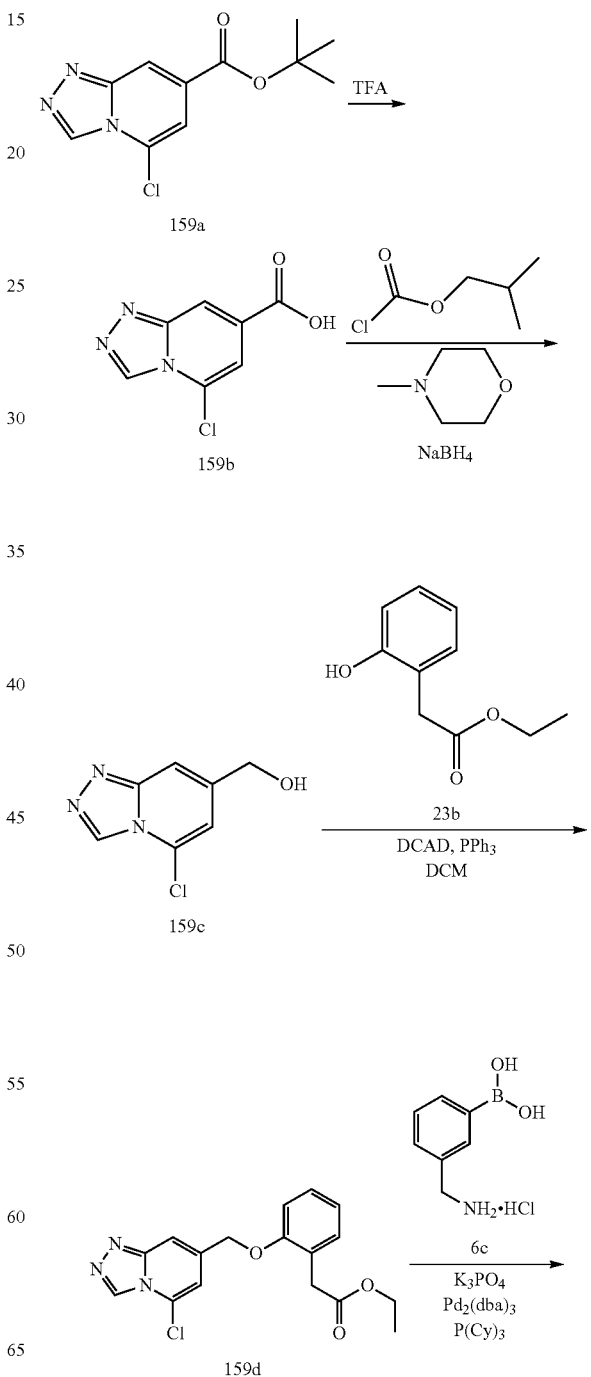

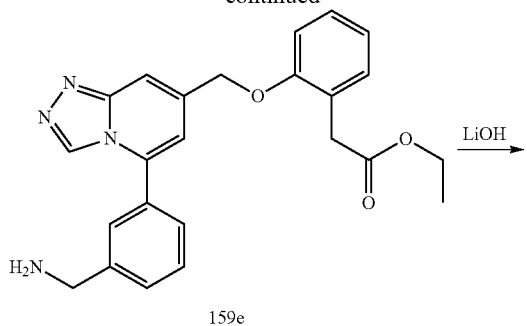

Preparation of 2-(2-((5-(3-(aminomethyl)phenyl)-[1,2,4]triazolo[4,3-a]pyridin-7-yl)methoxy)phenyl)acetic Acid (159f)

Step-1: Preparation of 5-chloro-[1,2,4]triazolo[4,3-a]pyridine-7-carboxylic Acid (159b)

To a solution of tert-butyl 5-chloro-[1,2,4]triazolo[4,3-a]pyridine-7-carboxylate (159a) (950 mg, 3.67 mmol; CAS #1246759-50-1) in $CH_2Cl_2$ (30 mL) was added 2,2,2-trifluoroacetic acid (4.24 mL, 55.0 mmol) and stirred at RT for 17 h. The reaction mixture was concentrated to dryness to afford 5-chloro-[1,2,4]triazolo[4,3-a]pyridine-7-carboxylic acid (159b), which was used as such for next step. MS (ES−): 196.1 & 198.1 (M−1).

Step-2: Preparation of (5-chloro-[1,2,4]triazolo[4,3-a]pyridin-7-yl)methanol (159c)

Compound 159c was prepared according to the procedure reported in step-1 of Scheme-23 from 5-chloro-[1,2,4]triazolo[4,3-a]pyridine-7-carboxylic acid (159b) (1.84 mmol) using N-methylmorpholine (0.726 mL, 6.61 mmol) in THF (30 mL), isobutyl chloroformate (0.868 mL, 6.61 mmol) and $NaBH_4$ (278 mg, 7.34 mmol) in water (1 mL). This gave after workup and purification by flash column chromatography [silica (24 g), eluting with dichloromethane/methanol (1:0 to 19:1)] (5-chloro-[1,2,4]triazolo[4,3-a]pyridin-7-yl)methanol (159c) (84 mg, 25% for two steps) as a white solid. $^1H$ NMR (300 MHz, DMSO-$d_6$) δ 9.36 (s, 1H), 7.68-7.62 (m, 1H), 7.16 (s, 1H), 5.60 (t, J=5.7 Hz, 1H), 4.59-4.53 (m, 2H).

Step-3: Preparation of Ethyl 2-(2-((5-chloro-[1,2,4]triazolo[4,3-a]pyridin-7-yl)methoxy)phenyl)acetate (159d)

Compound 159d was prepared according to the procedure reported in step-2 of Scheme-23 (5-chloro-[1,2,4]triazolo[4,3-a]pyridin-7-yl)methanol (159c) (80 mg, 0.436 mmol) in DCM (5 mL) and THF (5 mL) using triphenylphosphine (149 mg, 0.566 mmol) ethyl 2-(2-hydroxyphenyl) acetate (23b) 2.51 g, 13.92 mmol) and a solution of di-(4-chlorobenzyl)azodicarboxylate (DCAD, 208 mg, 0.566 mmol) in DCM (5 mL). This gave after workup and purification by flash column chromatography [silica (12 g), eluting with hexanes/10% methanol in ethyl acetate (1:0 to 1:1)] ethyl 2-(2-((5-chloro-[1,2,4]triazolo[4,3-a]pyridin-7-yl)methoxy)phenyl)acetate (159d) (140 mg, 93%) as a white solid. $^1H$ NMR (300 MHz, DMSO-$d_6$) δ 9.45 (s, 1H), 7.83 (s, 1H), 7.53-7.22 (m, 3H), 7.04 (d, J=8.4 Hz, 1H), 6.95 (t, J=7.4 Hz, 1H), 5.22 (s, 2H), 4.06 (q, J=7.1 Hz, 2H), 3.71 (s, 2H), 1.15 (t, J=7.1 Hz, 3H); MS (ES+): 368.1 & 370.1 (M+Na); MS (ES−): 344.2 (M−1).

Step-4: Preparation of Ethyl 2-(2-((5-(3-(aminomethyl)phenyl)-[1,2,4]triazolo[4,3-a]pyridin-7-yl)methoxy)phenyl)acetate (159e)

Compound 159e was prepared according to the procedure reported in step-3 of Scheme-1 from ethyl 2-(2-((5-chloro-[1,2,4]triazolo[4,3-a]pyridin-7-yl)methoxy)phenyl)acetate (159d) (116 mg, 0.335 mmol) in dioxane (3 mL) using 3-(aminomethyl)phenylboronic acid hydrochloride (6c) (94 mg, 0.503 mmol), tripotassium phosphate (0.190 mL, 0.570 mmol, 3 M solution), water (0.05 mL), and $Pd_2(dba)_3$ (92 mg, 0.101 mmol) under an Ar atmosphere and heating at 125° C. for 2 h in a microwave. This gave after workup, purification by flash column chromatography [silica (12 g), eluting with dichloromethane/DMA 80 (1:0 to 1:1)] ethyl 2-(2-((5-(3-(aminomethyl)phenyl)-[1,2,4]triazolo[4,3-a]pyridin-7-yl)methoxy)phenyl)acetate (159e) (25 mg, 18%) as a colorless gum; MS (ES+): 417.3 (M+1) & 439.3 (M+Na); MS (ES−): 451.4 (M+Cl).

Step-5: Preparation of 2-(2-((5-(3-(aminomethyl)phenyl)-[1,2,4]triazolo[4,3-a]pyridin-7-yl)methoxy)phenyl)acetic Acid (159f)

Compound 159f was prepared according to the procedure reported in step-6 of Scheme-1, from ethyl 2-(2-((5-(3-(aminomethyl)phenyl)-[1,2,4]triazolo[4,3-a]pyridin-7-yl)methoxy)phenyl)acetate (159e) (25 mg, 0.060 mmol) in THF/MeOH (4 mL, each) using a solution of lithium hydroxide hydrate (15 mg, 0.36 mmol) in water (4 mL). This gave after workup and purification by flash column chromatography [silica (12 g), eluting with dichloromethane/methanol (1:0 to 3:1)] 2-(2-((5-(3-(aminomethyl)phenyl)-[1,2,4]triazolo[4,3-a]pyridin-7-yl)methoxy)phenyl)acetic acid (159f) (12 mg, 52%) as a white solid; $^1H$ NMR (300 MHz, DMSO-$d_6$) δ 9.40 (s, 1H), 8.05 (s, 1H), 7.88 (s, 1H), 7.85-7.79 (m, 1H), 7.69-7.60 (m, 2H), 7.27-7.19 (m, 2H), 7.16 (bs, 1H), 7.04 (d, J=8.5 Hz, 1H), 6.91 (t, J=7.3 Hz, 1H), 5.28 (s, 2H), 4.11 (s, 2H), 3.58 (s, 2H); MS (ES+): 389.3 (M+1) & 411.3 (M+Na); MS (ES−): 387.2 (M−1) & 423.2 (M+Cl).

Scheme-160

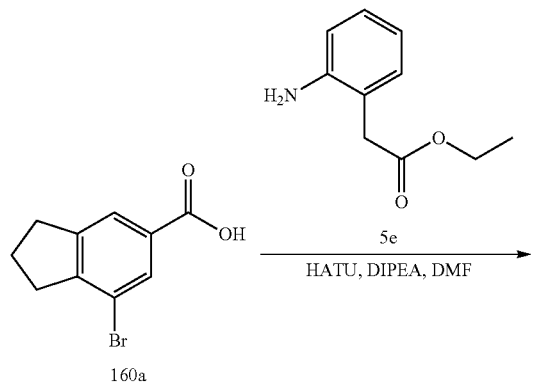

160a

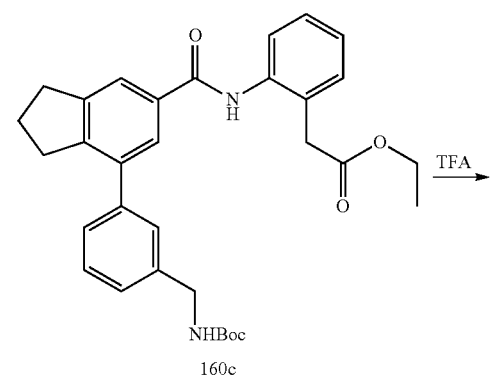

160b

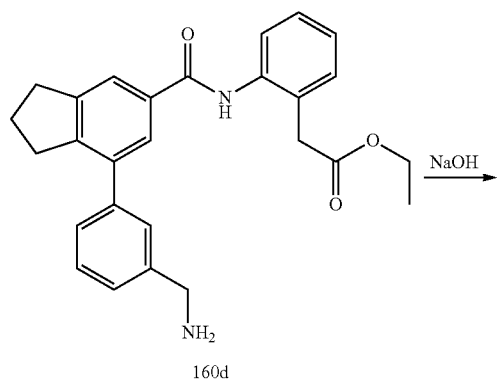

160c

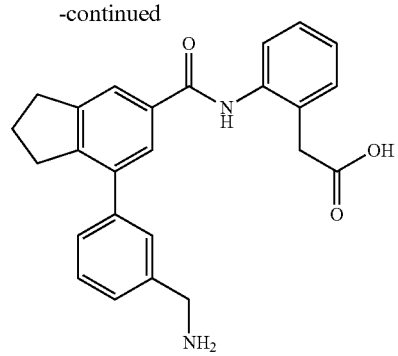

160e

Preparation of 2-(2-(7-(3-(aminomethyl)phenyl)-2,3-dihydro-1H-indene-5-carboxamido)phenyl)acetic Acid (160e)

Step-1: Preparation of Ethyl 2-(2-(7-bromo-2,3-dihydro-1H-indene-5-carboxamido)phenyl)acetate (160b)

Compound 160b was prepared according to the procedure reported in step-4 of Scheme-1 from 7-bromo-2,3-dihydro-1H-indene-5-carboxylic acid (160a) (2.0 g, 8.29 mmol; Prepared according to the procedure reported by Johansson, Anders and Persson, Joachim in PCT Int Appl., 2004110344, 23 Dec. 2004) in DMF (40 mL) using ethyl 2-(2-aminophenyl)acetate (5e) (1.78 g, 9.95 mmol), DIPEA (3.21 g, 24.88 mmol) and HATU (3.78 g, 9.95 mmol). This gave after workup and purification by flash column chromatography [silica, eluting with ethyl acetate in n-hexane (0-20%)] ethyl 2-(2-(7-bromo-2,3-dihydro-1H-indene-5-carboxamido)phenyl)acetate (160b) (1.2 g, 36%) as a white solid; $^1$H NMR (300 MHz, DMSO-$d_6$) δ 10.00 (s, 1H), 7.90 (d, J=1.5 Hz, 1H), 7.78 (s, 1H), 7.33 (dd, J=8.2, 1.7 Hz, 1H), 7.09-6.87 (m, 1H), 6.65 (dd, J=7.8, 1.3 Hz, 1H), 6.51 (td, J=7.4, 1.3 Hz, 1H), 4.87 (s, 2H), 4.08 (t, J=7.1 Hz, 2H), 3.49 (s, 2H), 3.06 (t, J=7.5 Hz, 3H): MS (ES+) 404.0 (M+1); (ES−) 401.9 (M−1).

Step-2: Preparation of Ethyl 2-(2-(7-(3-(((tert-butoxycarbonyl)amino)methyl)phenyl)-2,3-dihydro-1H-indene-5-carboxamido)phenyl)acetate (160c)

Compound 160c was prepared according to the procedure reported in step-3 of Scheme-1 from ethyl 2-(2-(7-bromo-2,3-dihydro-1H-indene-5-carboxamido)phenyl)acetate (160b) (0.5 g, 1.24 mmol) in dioxane (3 mL) using (3-(((tert-butoxycarbonyl)amino)methyl)phenyl)boronic acid (1d) (0.37 g, 1.49 mmol), Na$_2$CO$_3$ (0.39 g, 3.72 mmol) and Pd(dppf)Cl$_2$ (0.10 g, 0.12 mmol) under a nitrogen atmosphere and heating at 60° C. for 6 h in an oil bath. This gave after workup, purification by flash column chromatography [silica gel, eluting with 0-30% EtOAc in n-hexane] ethyl 2-(2-(7-(3-(((tert-butoxycarbonyl)amino)methyl)phenyl)-2,3-dihydro-1H-indene-5-carboxamido)phenyl)acetate (160c) (0.15 g, 22.90%) as an oil; $^1$H NMR (300 MHz, CDCl$_3$) δ 9.60 (s, 1H), 7.96 (dd, J=8.2, 1.3 Hz, 1H), 7.83-7.67 (m, 2H), 7.44-7.26 (m, 4H), 7.26-7.17 (m, 1H), 7.06 (td, J=7.5, 1.3 Hz, 1H), 4.89 (s, 1H), 4.30 (d, J=5.9 Hz, 2H), 4.10 (q, J=7.1 Hz, 2H), 3.60 (s, 2H), 2.96 (dt, J=10.4, 7.4 Hz, 4H), 2.10-1.91 (m, 2H), 1.39 (s, 9H), 1.24-1.06 (m, 3H).

Step-3: Preparation of Ethyl 2-(2-(7-(3-(aminomethyl)phenyl)-2,3-dihydro-1H-indene-5-carboxamido)phenyl)acetate (160d)

Compound 160d was prepared according to the procedure reported in step-5 of Scheme-1 from ethyl 2-(2-(7-(3-(((tert-butoxycarbonyl)amino)methyl)phenyl)-2,3-dihydro-1H-indene-5-carboxamido)phenyl)acetate (160c) (0.070 g, 0.132 mmol) in DCM (3 mL) using TFA (0.204 mL, 2.65 mmol). This gave after workup ethyl 2-(2-(7-(3-(aminomethyl)phenyl)-2,3-dihydro-1H-indene-5-carboxamido)phenyl)acetate (160d) (0.057 g, 100% yield) TFA salt as a yellow solid; MS (ES+): 429.3 (M+1).

Step-4: Preparation of 2-(2-(7-(3-(aminomethyl)phenyl)-2,3-dihydro-1H-indene-5-carboxamido)phenyl)acetic Acid (160e)

Compound 160e was prepared according to the procedure reported in step-4 of Scheme-4 from ethyl 2-(2-(7-(3-(aminomethyl)phenyl)-2,3-dihydro-1H-indene-5-carboxamido)phenyl)acetate (160d) (0.056 g, 0.131 mmol) in THF (2 mL) and methanol (4 mL) using sodium hydroxide (2 M aqueous, 0.457 mL, 0.915 mmol). This gave after workup and purification by reverse phase column chromatography [C-18 column, 30 g, eluting with 0.1% aq. HCl in water and acetonitrile from 0-100%] 2-(2-(7-(3-(aminomethyl)phenyl)-2,3-dihydro-1H-indene-5-carboxamido)phenyl)acetic acid (160e) (0.012 g, 23% yield) as a white solid; $^1$H NMR (300 MHz, DMSO-$d_6$) δ 12.35 (s, 1H, $D_2O$ exchangeable), 10.04 (s, 1H, $D_2O$ exchangeable), 8.34 (bs, 3H, $D_2O$ exchangeable), 7.89-7.81 (m, 2H), 7.69 (s, 1H), 7.62-7.42 (m, 4H), 7.37-7.26 (m, 2H), 7.21 (td, J=7.5, 1.5 Hz, 1H), 4.12 (s, 2H), 3.66 (s, 2H), 3.01 (t, J=7.3 Hz, 4H), 2.15-1.98 (m, 2H); MS (ES+): 401.3 (M+1), 801.5 (2M+1); MS (ES−): 399.4 (M−1), 799.6 (2M−1); HPLC purity: 99.35%.

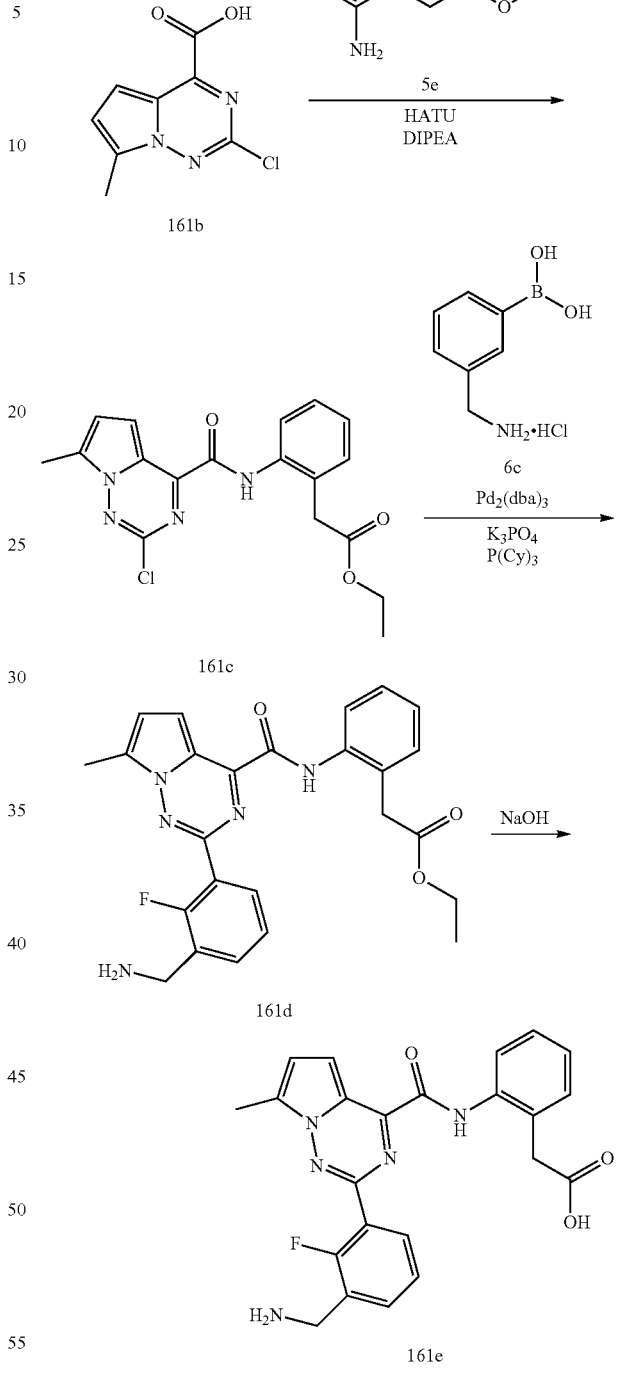

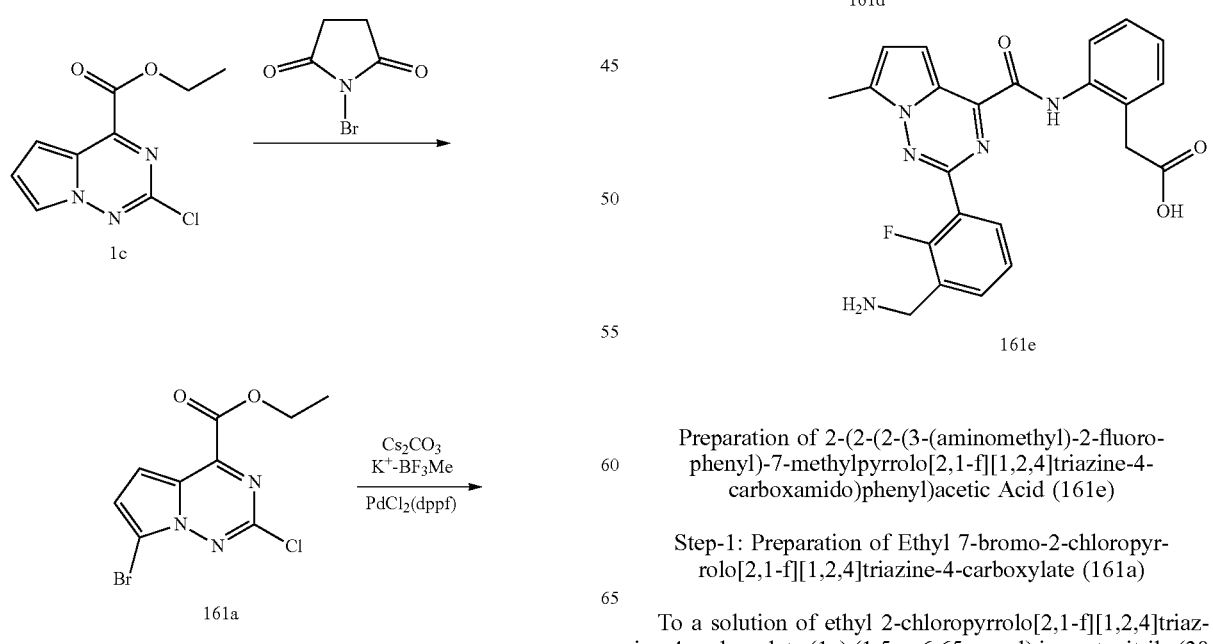

Scheme-161

Preparation of 2-(2-(2-(3-(aminomethyl)-2-fluorophenyl)-7-methylpyrrolo[2,1-f][1,2,4]triazine-4-carboxamido)phenyl)acetic Acid (161e)

Step-1: Preparation of Ethyl 7-bromo-2-chloropyrrolo[2,1-f][1,2,4]triazine-4-carboxylate (161a)

To a solution of ethyl 2-chloropyrrolo[2,1-f][1,2,4]triazine-4-carboxylate (1c) (1.5 g, 6.65 mmol) in acetonitrile (30 mL) at 0° C. was added a solution of NBS (1.302 g, 7.31 mmol) in acetonitrile (10 mL) and stirred at room temperature for 16 h. The reaction mixture was concentrated in vacuum and the residue obtained was purified by flash column chromatography (silica gel, 25 g eluting with ethyl acetate and hexanes) to afford ethyl 7-bromo-2-chloropyrrolo[2,1-f][1,2,4]triazine-4-carboxylate (161a) (650 mg, 32% yield) as an orange solid; $^1$H NMR (300 MHz, DMSO-$d_6$) δ 7.55 (d, J=5.0 Hz, 1H), 7.48 (d, J=5.1 Hz, 1H), 4.48 (q, J=7.1 Hz, 2H), 1.40 (t, J=7.1 Hz, 3H).

Step-2: Preparation of 2-chloro-7-methylpyrrolo[2,1-f][1,2,4]triazine-4-carboxylic Acid (161b)

To a solution of ethyl 7-bromo-2-chloropyrrolo[2,1-f][1,2,4]triazine-4-carboxylate (161a) (0.5 g, 1.642 mmol) in 1,4-Dioxane (10 mL) was added a solution of cesium carbonate (1.605 g, 4.93 mmol) in water (1 mL), potassium trifluoro(methyl)borate (0.400 g, 3.28 mmol), PdCl$_2$(dppf) (0.120 g, 0.164 mmol) and heated with stirring at 100° C. for 16 h. The reaction mixture was cooled to RT, partitioned between water (100 mL) and EtOAc (80 mL). The aqueous layer was extracted with EtOAc (40 mL). The combined organics were washed with brine, dried, filtered, concentrated in vacuum. The residue obtained was purified by flash column chromatography [silica gel 24 g, eluting with EtOAc in hexanes 0 to 60%] to afford 2-chloro-7-methylpyrrolo[2,1-f][1,2,4]triazine-4-carboxylic acid (161b) (410 mg) as a dark brown solid; MS (ES−): 210.1 (M−1).

Step-3: Preparation of Ethyl 2-(2-(2-chloro-7-methylpyrrolo[2,1-f][1,2,4]triazine-4-carboxamido)phenyl)acetate (161c)

Compound 161c was prepared according to the procedure reported in step-4 of Scheme-1 from 2-chloro-7-methylpyrrolo[2,1-f][1,2,4]triazine-4-carboxylic acid (161b) (400 mg, 1.890 mmol) in DMF (5 mL) using ethyl 2-(2-aminophenyl)acetate (5e) (508 mg, 2.84 mmol), DIPEA (0.990 mL, 5.67 mmol) and HATU (1078 mg, 2.84 mmol). This gave after workup and purification by flash column chromatography [silica 24 g, eluting with EtOAc/MeOH (9:1) in hexane from 0-60%] ethyl 2-(2-(2-chloro-7-methylpyrrolo[2,1-f][1,2,4]triazine-4-carboxamido)phenyl)acetate (161c) (125 mg, 18% yield) as a white solid; $^1$H NMR (300 MHz, DMSO-$d_6$) δ 10.44 (s, 1H), 7.72-7.62 (m, 1H), 7.59 (d, J=4.7 Hz, 1H), 7.40-7.31 (m, 2H), 7.23 (m, 2H), 4.07 (q, J=7.1 Hz, 2H), 3.78 (s, 2H), 2.60 (s, 3H), 1.13 (t, J=7.1 Hz, 3H); MS (ES+) 395.2 (M+Na).

Step-4: Preparation of Ethyl 2-(2-(2-(3-(aminomethyl)-2-fluorophenyl)-7-methylpyrrolo[2,1-f][1,2,4]triazine-4-carboxamido)phenyl)acetate (161d)

Compound 161d was prepared according to the procedure reported in step-3 of Scheme-1 from ethyl 2-(2-(2-chloro-7-methylpyrrolo[2,1-f][1,2,4]triazine-4-carboxamido)phenyl)acetate (161c) (60 mg, 0.161 mmol) in dioxane (3 mL) using 3-(aminomethyl)phenylboronic acid hydrochloride (6c) (50 mg, 0.241 mmol), tripotassium phosphate (1.3 M solution, 0.134 mL, 0.402 mmol), tricyclohexylphosphine (0.014 g, 0.048 mmol) and Pd$_2$(dba)$_3$ (0.015 g, 0.016 mmol) under a nitrogen atmosphere and heating at 125° C. for 90 min in a microwave. This gave after workup, purification by flash column chromatography [silica gel, 25g, eluting with ethyl acetate in hexanes (0 to 40 to 100%)] ethyl 2-(2-(2-(3-(aminomethyl)-2-fluorophenyl)-7-methylpyrrolo[2,1-f][1,2,4]triazine-4-carboxamido)phenyl)acetate (161d) (25 mg, 34% yield) as a sticky material; 1H NMR (300 MHz, DMSO-$d_6$) δ 10.62 (s, 1H), 8.23-8.10 (m, 1H), 7.83 (d, J=8.2 Hz, 1H), 7.74-7.63 (m, 1H), 7.57 (m, 1H), 7.38 (m, 3H), 7.26 (d, J=7.1 Hz, 1H), 7.17 (d, J=4.5 Hz, 1H), 3.96 (q, J=6.9 Hz, 2H), 3.87 (d, J=4.1 Hz, 2H), 3.83 (s, 2H), 2.65 (s, 3H), 0.99 (t, J=7.1 Hz, 3H); MS (ES+): 462.3 (M+1).

Step-5: Preparation of 2-(2-(2-(3-(aminomethyl)-2-fluorophenyl)-7-methylpyrrolo[2,1-f][1,2,4]triazine-4-carboxamido)phenyl)acetic Acid (161e)

Compound 161e was prepared according to the procedure reported in step-4 of Scheme-4 from ethyl 2-(2-(2-(3-(aminomethyl)-2-fluorophenyl)-7-methylpyrrolo[2,1-f][1,2,4]triazine-4-carboxamido)phenyl)acetate (161d) (24 mg, 0.052 mmol) in THF (2 mL) and ethanol (1 mL) using sodium hydroxide (2.5 M aqueous solution) in water (1 mL). This gave after workup and purification by reverse phase column [C18 (50 g), eluting with ACN in water (containing 0.1% HCl) from 0-100%] 2-(2-(2-(3-(aminomethyl)-2-fluorophenyl)-7-methylpyrrolo[2,1-f][1,2,4]triazine-4-carboxamido)phenyl)acetic acid (161e) (22 mg, 98% yield) HCl salt as a light orange solid; 1H NMR (300 MHz, DMSO-$d_6$) δ 10.77 (s, 1H, D$_2$O exchangeable), 8.42 (t, J=7.6 Hz, 1H), 7.92-7.83 (m, 1H), 7.75 (t, J=7.0 Hz, 1H), 7.61 (d, J=4.5 Hz, 1H), 7.47 (t, J=7.7 Hz, 1H), 7.42-7.34 (m, 2H), 7.25 (d, J=7.4 Hz, 1H), 7.20 (d, J=4.7 Hz, 1H), 4.21 (s, 2H), 3.74 (s, 2H), 2.66 (s, 3H); MS (ES+): 434.3 (M+1), 456.2 (M+Na), (ES−): 432.4 (M−1).

Scheme-162

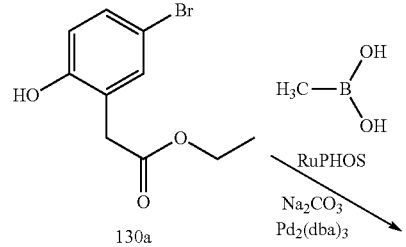

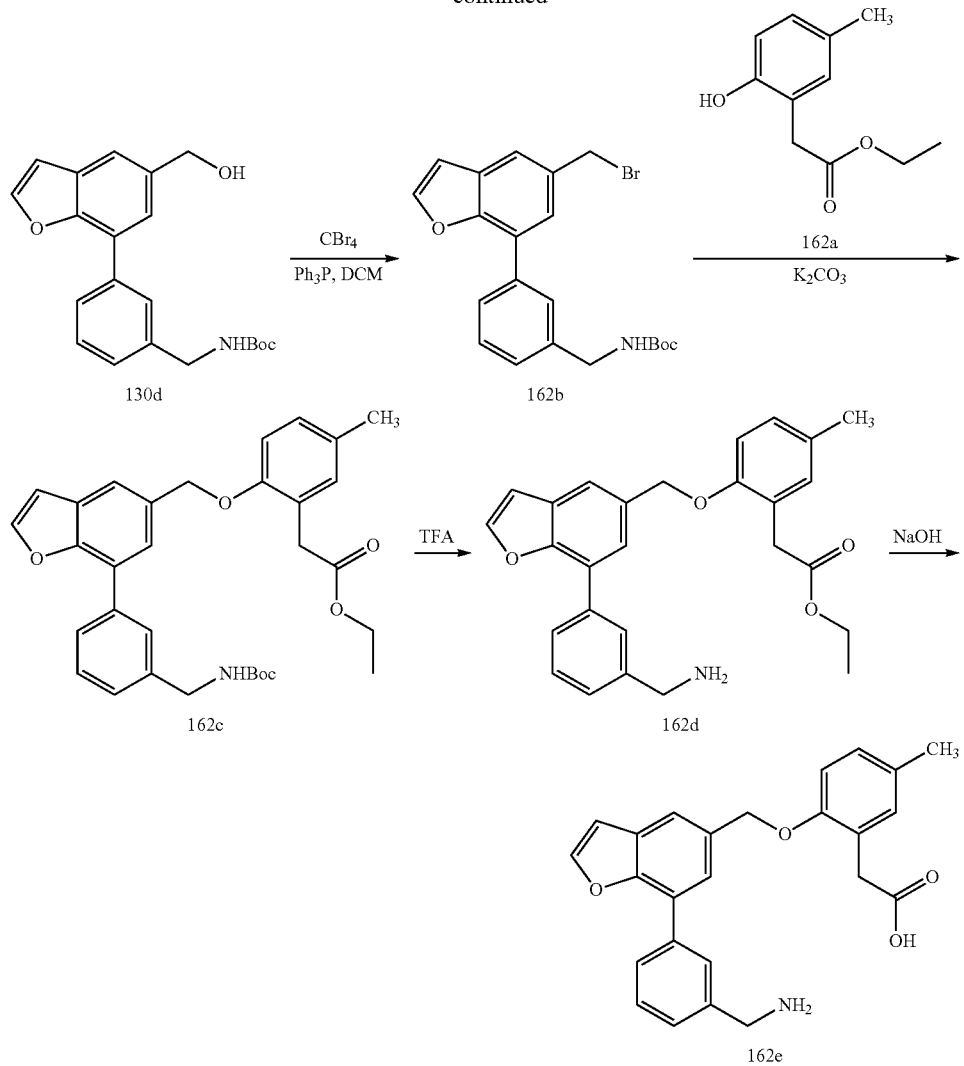

Preparation of 2-(2-((7-(3-(aminomethyl)phenyl)benzofuran-5-yl)methoxy)-5-methylphenyl)acetic Acid (162e)

Step-1: Preparation of Ethyl 2-(2-hydroxy-5-methylphenyl)acetate (162a)

Compound 162a was prepared according to the procedure reported in step-1 of Scheme-130 from ethyl 2-(5-bromo-2-hydroxyphenyl)acetate (130a) (0.750 g, 2.89 mmol) in toluene (20 mL) using methylboronic acid (0.260 g, 4.34 mmol), dicyclohexyl(2',6'-diisopropoxybiphenyl-2-yl)phosphine (RuPHOS) (0.135 g, 0.289 mmol), Pd$_2$(dba)$_3$ (0.133 g, 0.145 mmol) and a solution of Na$_2$CO$_3$ (1.23 g, 11.58 mmol) in water (2 mL) under a nitrogen atmosphere and heated at 100° C. for 1.5 h. This gave after workup and purification by flash column chromatography [silica gel 24 g, eluting with EtOAc in hexanes from 0-30%] ethyl 2-(2-hydroxy-5-methylphenyl)acetate (162a) (0.242 g, 43% yield) as thick clear oil; $^1$H NMR (300 MHz, DMSO-d$_6$) δ 9.16 (s, 1H), 6.92-6.82 (m, 2H), 6.67 (d, J=8.0 Hz, 1H), 4.05 (q, J=7.0 Hz, 2H), 3.48 (s, 2H), 2.17 (s, 3H), 1.17 (t, J=7.1 Hz, 3H).

Step-2: Preparation of tert-butyl 3-(5-(bromomethyl)benzofuran-7-yl)benzylcarbamate (162b)

Compound 162b was prepared according to the procedure reported in step-1 of Scheme-152 from tert-butyl 3-(5-(hydroxymethyl)benzofuran-7-yl)benzylcarbamate (130d) (0.398 g, 1.126 mmol) in DCM (10 mL) using CBr$_4$ (0.747 g, 2.252 mmol) and triphenylphosphine (0.591 g, 2.252 mmol). This gave after workup and purification by flash column chromatography [silica gel 12 g, eluting with ethyl acetate in hexanes from 0-30%] tert-butyl 3-(5-(bromomethyl)benzofuran-7-yl)benzylcarbamate (162b) (0.328 g, 70% yield) as a thick pale-yellow syrup; $^1$H NMR (300 MHz, DMSO-d$_6$) δ 8.08 (d, J=2.2 Hz, 1H), 7.79-7.68 (m, 3H), 7.58 (d, J=1.8 Hz, 1H), 7.48 (t, J=7.6 Hz, 1H), 7.31 (d, J=7.7 Hz, 1H), 7.09-7.02 (m, 1H), 4.90 (s, 2H), 4.23 (d, J=6.1 Hz, 2H), 1.40 (s, 9H).

Step-3: Preparation of Ethyl 2-(2-((7-(3-(((tert-butoxycarbonyl)amino)methyl)phenyl)benzofuran-5-yl)methoxy)-5-methylphenyl)acetate (162c)

Compound 162c was prepared according to the procedure reported in step-2 of Scheme-152 from tert-butyl 3-(5-

(bromomethyl)benzofuran-7-yl)benzylcarbamate (162b) (0.309 g, 0.742 mmol) in DMF (10 mL) using potassium carbonate (0.256 g, 1.856 mmol) and ethyl 2-(2-hydroxy-5-methylphenyl)acetate (162a) (0.144 g, 0.742 mmol). This gave after workup and purification by flash column chromatography [silica gel 24 g, eluting with ethyl acetate in hexanes from 0-100%] ethyl 2-(2-((7-(3-(((tert-butoxycarbonyl)amino)methyl)phenyl)benzofuran-5-yl)methoxy)-5-methylphenyl)acetate (162c) (0.228 g, 58% yield) as a white solid; MS (ES+): 552.3 (M+Na); MS (ES−): 528.4 (M−1).

Step-4: Preparation of Ethyl 2-(2-((7-(3-(aminomethyl)phenyl)benzofuran-5-yl)methoxy)-5-methylphenyl)acetate (162d)

Compound 162d was prepared according to the procedure reported in step-5 of Scheme-1 from ethyl 2-(2-((7-(3-(((tert-butoxycarbonyl)amino)methyl)phenyl)benzofuran-5-yl)methoxy)-5-methylphenyl)acetate (162c) (0.223 g, 0.421 mmol) in DCM (10 mL) using TFA (0.649 mL, 8.42 mmol). This gave after workup and purification by flash column chromatography [silica gel 12 g, eluting with methanol in DCM from 0-100%] ethyl 2-(2-((7-(3-(aminomethyl)phenyl)benzofuran-5-yl)methoxy)-5-methylphenyl)acetate (162d) (0.221 g, 97% yield) TFA salt as a yellow wax; MS (ES+): 430.3 (M+1), 452.3 (M+Na).

Step-5: Preparation of 2-(2-((7-(3-(aminomethyl)phenyl)benzofuran-5-yl)methoxy)-5-methylphenyl)acetic Acid (162e)

Compound 162e was prepared according to the procedure reported in step-4 of Scheme-4, from ethyl 2-(2-((7-(3-(aminomethyl)phenyl)benzofuran-5-yl)methoxy)-5-methylphenyl)acetate (162d) (0.108 g, 0.199 mmol) in THF (5 mL) and methanol (10 mL) using a solution of sodium hydroxide (2 M aqueous, 0.497 mL, 0.994 mmol). This gave after workup and purification by reverse phase column [C18 (30 g), eluting with ACN in water (containing 0.1% HCl) from 0-100%] 2-(2-((7-(3-(aminomethyl)phenyl)benzofuran-5-yl)methoxy)-5-methylphenyl)acetic acid (162e) (0.005 g, 6% yield) HCl salt as a white solid; $^1$H NMR (300 MHz, DMSO-$d_6$) δ 12.23 (s, 1H, $D_2O$ exchangeable), 8.28 (s, 3H, $D_2O$ exchangeable), 8.11 (d, J=2.2 Hz, 1H), 7.98 (s, 1H), 7.95-7.89 (m, 1H), 7.75 (d, J=1.6 Hz, 1H), 7.62 (dd, J=6.8, 5.0 Hz, 2H), 7.55 (t, J=8.5 Hz, 1H), 7.06 (d, J=2.2 Hz, 1H), 7.05-6.95 (m, 3H), 5.23 (s, 2H), 4.15 (s, 2H), 3.55 (s, 2H), 2.22 (s, 3H); MS (ES+): 402.3 (M+1), 803.5 (2M+1); MS (ES−): 400.3 (M−1), 436.3 (M+Cl).

Scheme-163

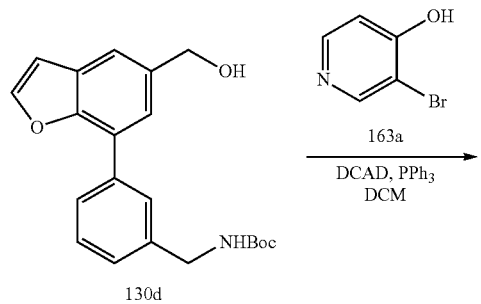

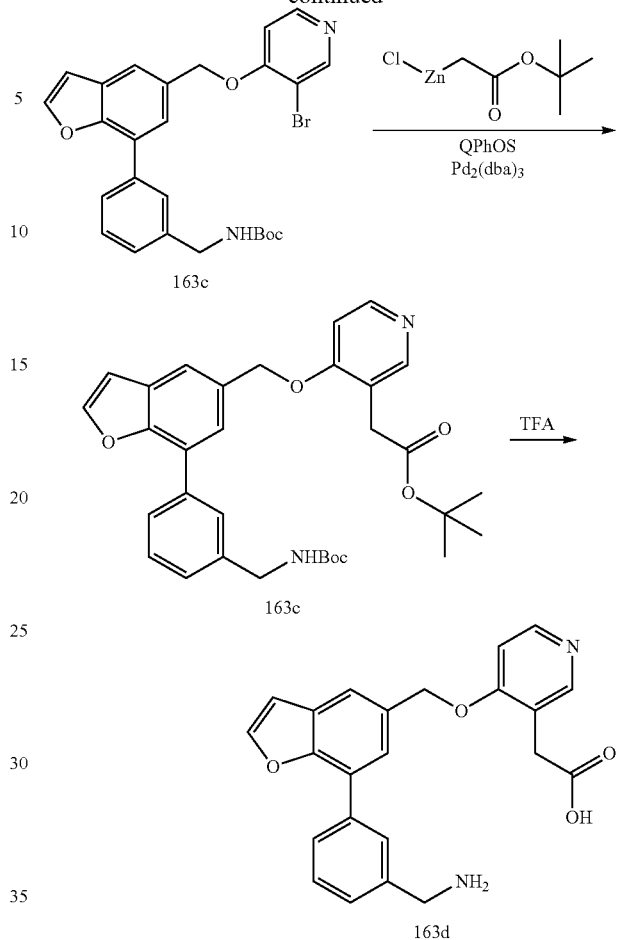

Preparation of 2-(4-((7-(3-(aminomethyl)phenyl)benzofuran-5-yl)methoxy)pyridin-3-yl)acetic Acid (163d)

Step-1: Preparation of tert-butyl 3-(5-(((3-bromopyridin-4-yl)oxy)methyl)benzofuran-7-yl)benzylcarbamate (163b)

Compound 163b was prepared according to the procedure reported in step-2 of Scheme-23 from tert-butyl 3-(5-(hydroxymethyl)benzofuran-7-yl)benzylcarbamate (130d) (0.5 g, 1.415 mmol) in DCM (30 mL) using triphenylphosphine (0.408 g, 1.556 mmol), 3-bromopyridin-4-ol (163a) (0.295 g, 1.698 mmol; CAS #36953-41-0) and a solution of di-(4-chlorobenzyl)azodicarboxylate (DCAD, 0.571 g, 1.556 mmol) in DCM (20 mL). This gave after workup and purification by flash column chromatography [silica gel 24 g, eluting with ethyl acetate in hexanes from 0-100%] tert-butyl 3-(5-(((3-bromopyridin-4-yl)oxy)methyl)benzofuran-7-yl)benzylcarbamate (163b) (320 mg, 44% yield) as a white wax; $^1$H NMR (300 MHz, DMSO-$d_6$) δ 8.60 (s, 1H), 8.43 (d, J=5.6 Hz, 1H), 8.09 (d, J=2.2 Hz, 1H), 7.78 (d, J=1.7 Hz, 1H), 7.74 (m, 2H), 7.63 (d, J=1.7 Hz, 1H), 7.47 (m, 2H), 7.35 (d, J=5.7 Hz, 1H), 7.31 (d, J=7.7 Hz, 1H), 7.09 (d, J=2.2 Hz, 1H), 5.46 (s, 2H), 4.23 (d, J=6.1 Hz, 2H), 1.39 (s, 9H); MS (ES+): 531.2, 533.2 (M+Na).

Step-2: Preparation of tert-butyl 2-(4-((7-(3-(((tert-butoxycarbonyl)amino)methyl)phenyl)benzofuran-5-yl)methoxy)pyridin-3-yl)acetate (163c)

To a stirred solution of tert-butyl 3-(5-(((3-bromopyridin-4-yl)oxy)methyl)benzofuran-7-yl)benzylcarbamate (163b) (150 mg, 0.294 mmol) in THF (4 mL) was added Pd$_2$(dba)$_3$ (27.0 mg, 0.029 mmol), Q-Phos (20.93 mg, 0.029 mmol), (2-tert-butoxy-2-oxoethyl)zinc(II) chloride (0.5 M solution in ether) (1.178 mL, 0.589 mmol), degassed for 4 minutes and heated at 70° C. for 4 h. The reaction was cooled to room temperature diluted with ethyl acetate (30 mL) and brine (5 mL). The mixture was stirred for 10 min and filtered through a small pad of Celite. The aqueous layer was separated and extracted with ethyl acetate (50 mL). The organic layers were combined washed with brine (25 mL), dried, filtered and concentrated in vacuum. The obtained crude residue was purified by flash column chromatography [silica gel 24 g, eluting with ethyl acetate in hexanes (0-40 to 100%)] to afford tert-butyl 2-(4-((7-(3-(((tert-butoxycarbonyl)amino)methyl)phenyl)benzofuran-5-yl)methoxy)pyridin-3-yl)acetate (163c) (100 mg, 62% yield) as a sticky material; $^1$H NMR (300 MHz, DMSO-d$_6$) δ 8.38 (d, J=5.6 Hz, 1H), 8.26 (s, 1H), 8.09 (d, J=2.2 Hz, 1H), 7.84-7.66 (m, 3H), 7.58 (s, 1H), 7.49 (m, 1H), 7.30 (d, J=7.5 Hz, 1H), 7.16 (d, J=5.8 Hz, 1H), 7.04 (d, J=2.3 Hz, 1H), 5.34 (s, 2H), 4.22 (d, J=6.2 Hz, 2H), 3.55 (s, 2H), 1.39 (s, 9H), 1.22 (s, 9H); MS (ES+): 545.5 (M+1), 567.3 (M+Na), (ES−): 579.5 (M+Cl).

Step-3: Preparation of 2-(4-((7-(3-(aminomethyl)phenyl)benzofuran-5-yl)methoxy)pyridin-3-yl)acetic Acid (163d)

Compound 163d was prepared according to the procedure reported in step-5 of Scheme-1 from tert-butyl 2-(4-((7-(3-(((tert-butoxycarbonyl)amino)methyl)phenyl)benzofuran-5-yl)methoxy)pyridin-3-yl)acetate (163c) (100 mg, 0.184 mmol) in DCM (5 mL) using TFA (0.424 mL, 5.51 mmol). This gave after workup and purification by flash column chromatography [silica gel 12 g, eluting with DMA80 in DCM from 0-100%] followed by reverse phase column chromatography [C18 (50 g), eluting with ACN in water (containing 0.1% HCl) from 0-100%] 2-(4-((7-(3-(aminomethyl)phenyl)benzofuran-5-yl)methoxy)pyridin-3-yl)acetic acid (163d) (32 mg, 45% yield) HCl salt as off white solid; $^1$H NMR (300 MHz, DMSO-d$_6$) δ 8.83 (d, J=6.8 Hz, 1H), 8.75 (s, 1H), 8.62 (bs, 3H), 8.14 (d, J=2.2 Hz, 1H), 8.03 (s, 1H), 7.97-7.87 (m, 1H), 7.83-7.75 (m, 2H), 7.71 (d, J=1.6 Hz, 1H), 7.59 (s, 1H), 7.58 (s, 1H), 7.09 (d, J=2.2 Hz, 1H), 5.66 (s, 2H), 4.12 (q, J=5.8 Hz, 2H), 3.81 (s, 2H); MS (ES+): 389.2 (M+1), 411.3 (M+Na), (ES−): 387.3 (M−1), 423.3 (M+Cl).

Scheme-164

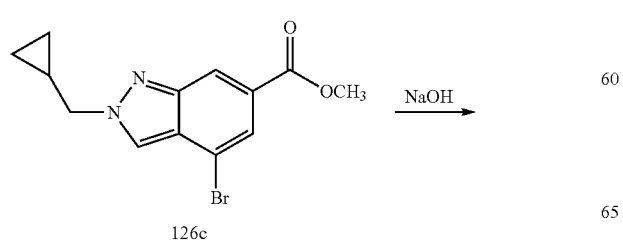

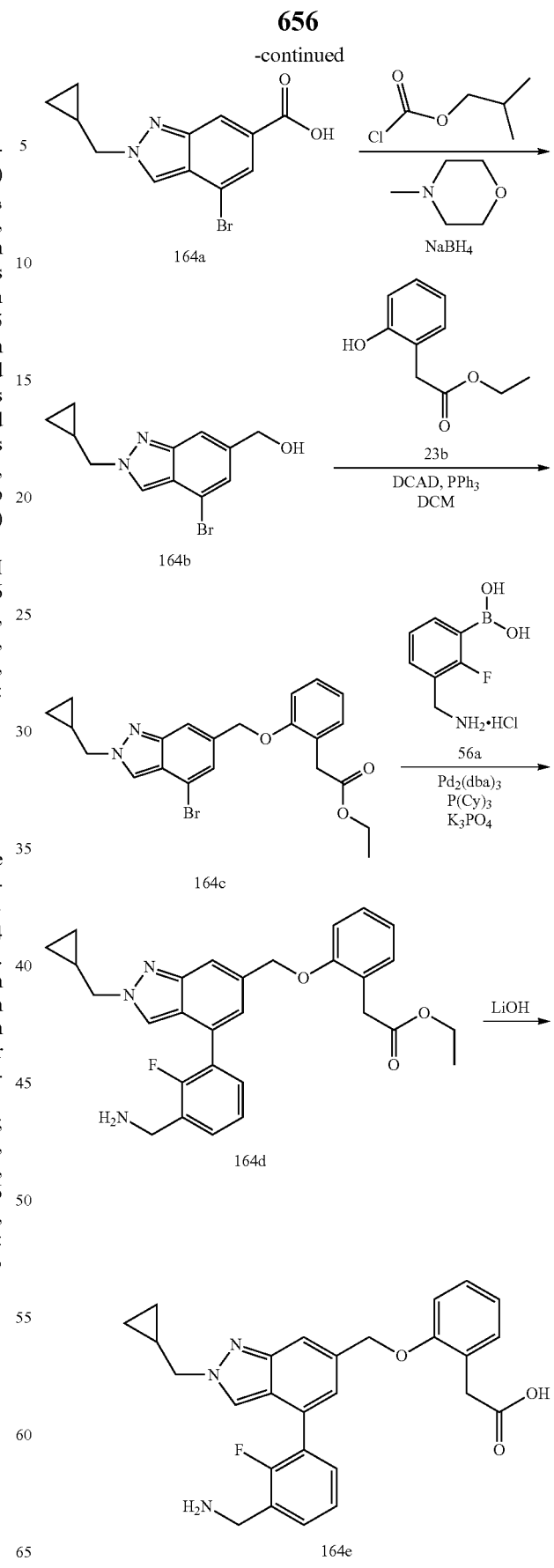

Preparation of 2-(2-((4-(3-(aminomethyl)-2-fluorophenyl)-2-(cyclopropylmethyl)-2H-indazol-6-yl)methoxy)phenyl)acetic Acid (164e)

Step-1: Preparation of 4-bromo-2-(cyclopropylmethyl)-2H-indazole-6-carboxylic Acid (164a)

Compound 164a was prepared according to the procedure reported in step-4 of Scheme-4, from methyl 4-bromo-2-(cyclopropylmethyl)-2H-indazole-6-carboxylate (126c) (0.802 g, 2.59 mmol) in THF (10 mL) and methanol (20 mL) using a solution of sodium hydroxide (2 M aqueous, 5.19 mL, 10.38 mmol). This gave after workup 4-bromo-2-(cyclopropylmethyl)-2H-indazole-6-carboxylic acid (164a) (0.755 g, 99% yield) as an off-white solid; $^1$H NMR (300 MHz, DMSO-$d_6$) δ 13.24 (s, 1H), 8.68-8.55 (m, 1H), 8.33-8.23 (m, 1H), 7.72 (d, J=1.1 Hz, 1H), 4.36 (d, J=7.3 Hz, 2H), 1.43 (m, 1H), 0.62-0.53 (m, 2H), 0.52-0.45 (m, 2H); MS (ES+): 297.1, 295.1 (M+2); MS (ES−): 295.2, 293.2 (M−2).

Step-2: Preparation of (4-bromo-2-(cyclopropylmethyl)-2H-indazol-6-yl)methanol (164b)

Compound 164b was prepared according to the procedure reported in step-1 of Scheme-23 from 4-bromo-2-(cyclopropylmethyl)-2H-indazole-6-carboxylic acid (164a) (0.731 g, 2.477 mmol) using N-methylmorpholine (0.327 mL, 2.97 mmol) in THF (20 mL), isobutyl chloroformate (0.390 mL, 2.97 mmol) and NaBH$_4$ (0.281 g, 7.43 mmol) in water (2 mL). This gave after workup and purification by flash column chromatography [silica gel 24 g, eluting with ethyl acetate in hexanes from 0-100%] (4-bromo-2-(cyclopropylmethyl)-2H-indazol-6-yl)methanol (164b) (0.377 g, 54% yield) as a yellow syrup; $^1$H NMR (300 MHz, DMSO-$d_6$) δ 8.38 (s, 1H), 7.58-7.42 (m, 1H), 7.23 (s, 1H), 5.29 (t, J=5.8 Hz, 1H), 4.55 (d, J=5.8 Hz, 2H), 4.28 (d, J=7.2 Hz, 2H), 1.53-1.28 (m, 1H), 0.64-0.51 (m, 2H), 0.49-0.41 (m, 2H).

Step-3: Preparation of Ethyl 2-(2-((4-bromo-2-(cyclopropylmethyl)-2H-indazol-6-yl)methoxy)phenyl)acetate (164c)

Compound 164c was prepared according to the procedure reported in step-2 of Scheme-23 from (4-bromo-2-(cyclopropylmethyl)-2H-indazol-6-yl)methanol (164b) (0.361 g, 1.284 mmol) in DCM (30 mL) using triphenylphosphine (0.370 g, 1.412 mmol) ethyl 2-(2-hydroxyphenyl) acetate (23b) (0.255 g, 1.412 mmol) and di-(4-chlorobenzyl)azodicarboxylate (DCAD, 0.519 g, 1.412 mmol) in DCM (20 mL). This gave after workup and purification by flash column chromatography [silica gel, 24g, eluting with EtOAc in hexanes from 0-50%] ethyl 2-(2-((4-bromo-2-(cyclopropylmethyl)-2H-indazol-6-yl)methoxy)phenyl)acetate (164c) (0.232 g, 41% yield) as a white wax; $^1$H NMR (300 MHz, DMSO-$d_6$) δ 8.53-8.37 (m, 1H), 7.80-7.56 (m, 1H), 7.31-7.26 (m, 1H), 7.23 (d, J=7.8 Hz, 2H), 7.06 (d, J=8.1 Hz, 1H), 6.91 (t, J=7.4 Hz, 1H), 5.18 (s, 2H), 4.29 (d, J=7.2 Hz, 2H), 4.14-3.97 (m, 2H), 3.64 (s, 2H), 1.51-1.32 (m, 1H), 1.20-1.01 (m, 3H), 0.62-0.50 (m, 2H), 0.50-0.39 (m, 2H); MS (ES+): 465.2, 467.1 (M+Na).

Step-4: Preparation of Ethyl 2-(2-((4-(3-(aminomethyl)-2-fluorophenyl)-2-(cyclopropylmethyl)-2H-indazol-6-yl)methoxy)phenyl)acetate (164d)

Compound 164d was prepared according to the procedure reported in step-3 of Scheme-1 from ethyl 2-(2-((4-bromo-2-(cyclopropylmethyl)-2H-indazol-6-yl)methoxy)phenyl)acetate (164c) (0.223 g, 0.503 mmol) in dioxane (6 mL) using 3-(aminomethyl)-2-fluorophenylboronic acid hydrochloride (56a) (0.127 g, 0.755 mmol), tripotassium phosphate (1.3M, 1.161 mL, 1.509 mmol), tricyclohexylphosphine (0.085 g, 0.302 mmol) and Pd$_2$(dba)$_3$ (0.092 g, 0.101 mmol) under an nitrogen atmosphere and heating at 125° C. for 45 min in a microwave. This gave after workup, purification by flash column chromatography [silica (24 g), eluting with MeOH in DCM from 0-40%] followed by purification by reverse phase column [C18 (50 g), eluting with ACN in water (containing 0.1% HCl) from 0-100%] ethyl 2-(2-((4-(3-(aminomethyl)-2-fluorophenyl)-2-(cyclopropylmethyl)-2H-indazol-6-yl)methoxy)phenyl)acetate (164d) (0.125 g, 51.0% yield) HCl salt as a white solid; $^1$H NMR (300 MHz, DMSO-$d_6$) δ 8.54-8.37 (m, 4H), 7.75 (s, 1H), 7.72-7.58 (m, 2H), 7.42 (t, J=7.7 Hz, 1H), 7.30-7.20 (m, 2H), 7.16 (s, 1H), 7.11 (d, J=8.2 Hz, 1H), 6.91 (t, J=7.3 Hz, 1H), 5.25 (s, 2H), 4.28 (d, J=7.2 Hz, 2H), 4.22-4.11 (m, 2H), 3.94 (q, J=7.1 Hz, 2H), 3.65 (s, 2H), 1.46-1.31 (m, 1H), 1.03 (t, J=7.1 Hz, 3H), 0.60-0.48 (m, 2H), 0.48-0.38 (m, 2H); $^{19}$F NMR (282 MHz, DMSO-$d_6$) δ−118.24; MS (ES+): 488.3 (M+1); 975.6 (2M+1); MS (ES−): 522.4 (M+Cl); HPLC purity: 97.03%.

Step-5: Preparation of 2-(2-((4-(3-(aminomethyl)-2-fluorophenyl)-2-(cyclopropylmethyl)-2H-indazol-6-yl)methoxy)phenyl)acetic Acid (164e)

Compound 164e was prepared according to the procedure reported in step-6 of Scheme-1 from ethyl 2-(2-((4-(3-(aminomethyl)-2-fluorophenyl)-2-(cyclopropylmethyl)-2H-indazol-6-yl)methoxy)phenyl)acetate (164d) (0.061 g, 0.125 mmol) in THF (3 mL) and methanol (7 mL) using a solution of lithium hydroxide hydrate (0.026 g, 0.626 mmol) in water (1.5 mL). This gave after workup and purification by reverse phase column [C18 (30 g), eluting with ACN in water (containing 0.1% HCl) from 0-100%] 2-(2-((4-(3-(aminomethyl)-2-fluorophenyl)-2-(cyclopropylmethyl)-2H-indazol-6-yl)methoxy)phenyl)acetic acid (164e) (0.037 g, 64% yield) HCl salt as a white solid; $^1$H NMR (300 MHz, DMSO-$d_6$) δ 8.58-8.48 (m, 3H, D$_2$O exchangeable), 8.48-8.41 (m, 1H), 7.76 (s, 1H), 7.73-7.60 (m, 2H), 7.41 (t, J=7.7 Hz, 1H), 7.29-7.18 (m, 3H), 7.09 (d, J=8.2 Hz, 1H), 6.98-6.83 (m, 1H), 5.26 (s, 2H), 4.28 (d, J=7.2 Hz, 2H), 4.21-4.12 (m, 2H), 3.60 (s, 2H), 1.51-1.31 (m, 1H), 0.61-0.47 (m, 2H), 0.48-0.40 (m, 2H); $^{19}$F NMR (282 MHz, DMSO-$d_6$) δ−118.03; MS (ES+): 460.3 (M+1); 919.5 (2M+1); MS (ES−): 458.4 (M−1), 494.3 (M+Cl).

Scheme-165

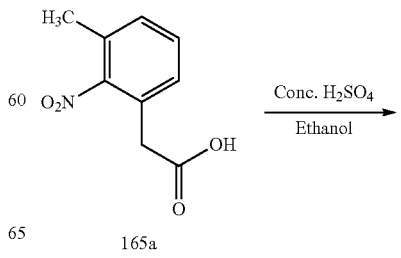

165a

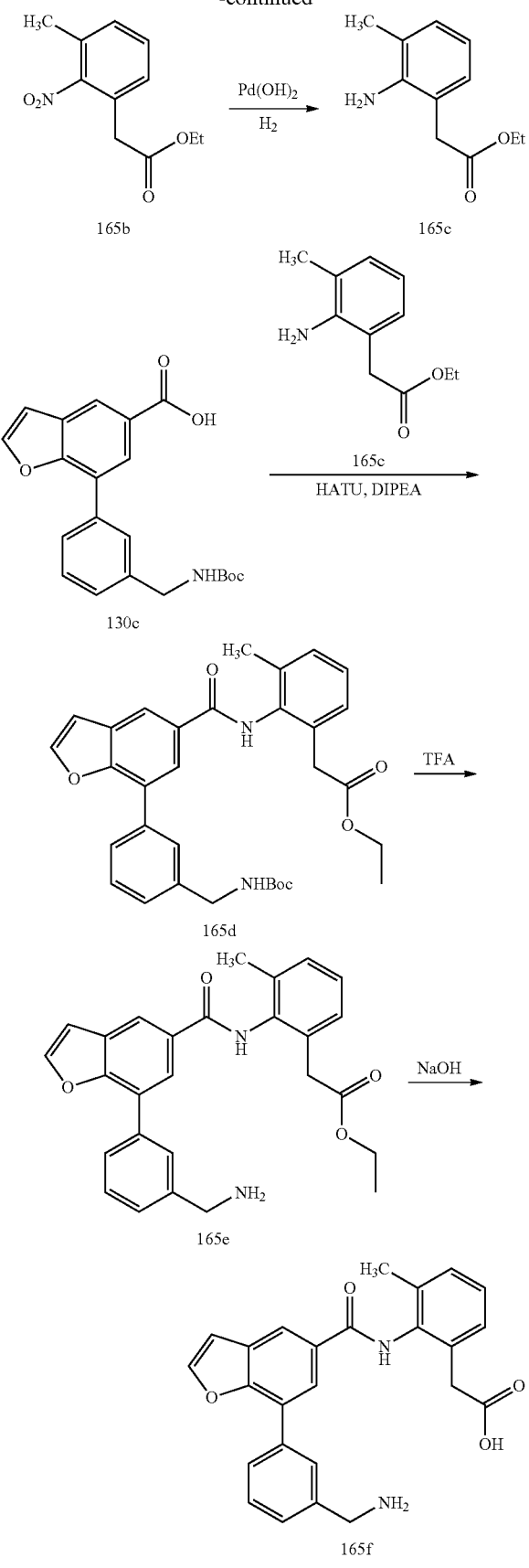

Preparation of 2-(2-(7-(3-(aminomethyl)phenyl) benzofuran-5-carboxamido)-3-methylphenyl)acetic Acid (165f)

Step-1: Preparation of Ethyl 2-(3-methyl-2-nitrophenyl)acetate (165b)

To a solution of 2-(3-methyl-2-nitrophenyl)acetic acid (165a) (1.00 g, 5.12 mmol CAS #18710-86-6) in ethanol (30 mL) was added $H_2SO_4$ (0.273 mL, 5.12 mmol) and heated at 80° C. for 16 h. The reaction mixture was cooled to RT and resultant residue was diluted with aq. sat. $NaHCO_3$ solution. The aqueous layer was extracted with EtOAc (2×50 mL), the combined organic layers were dried over anhydrous $MgSO_4$, filtered, evaporated to dryness. The residue obtained was purified by flash column chromatography [silica gel 25 g, eluting with ethyl acetate in hexanes from 0-100%] to furnish ethyl 2-(3-methyl-2-nitrophenyl)acetate (165b) (1.023 g, 89% yield) as thick yellow syrup; $^1$H NMR (300 MHz, DMSO-$d_6$) δ 7.54-7.47 (m, 1H), 7.45-7.34 (m, 2H), 4.07 (q, J=7.1 Hz, 2H), 3.77 (s, 2H), 2.31 (s, 3H), 1.17 (t, J=7.1 Hz, 3H).

Step-2: Preparation of Ethyl 2-(2-amino-3-methylphenyl)acetate (165c)

To a solution of ethyl 2-(3-methyl-2-nitrophenyl)acetate (165b) (0.500 g, 2.240 mmol) in EtOAc (15 mL) was added palladium hydroxide on carbon (0.315 g, 2.240 mmol) and stirred under hydrogen atmosphere (balloon) for 3h. The reaction mixture was filtered over Celite pad, the pad was rinsed with EtOAc (3×25 mL) and combined filtrate was concentrated and dried under vacuum to afford ethyl 2-(2-amino-3-methylphenyl)acetate (165c) (0.079 g, 18% yield) as a yellow oil; $^1$H NMR (300 MHz, DMSO-$d_6$) δ 6.87 (dd, J=7.2, 1.5 Hz, 1H), 6.81 (dd, J=7.6, 1.6 Hz, 1H), 6.45 (t, J=7.4 Hz, 1H), 4.61 (s, 2H), 4.06 (q, J=7.1 Hz, 2H), 3.53 (s, 2H), 2.08 (s, 3H), 1.18 (t, J=7.1 Hz, 3H).

Step-3: Preparation of Ethyl 2-(2-(7-(3-(((tert-butoxycarbonyl)amino)methyl)phenyl)benzofuran-5-carboxamido)-3-methylphenyl)acetate (165d)

Compound 165d was prepared according to the procedure reported in step-4 of Scheme-1 from 7-(3-(((tert-butoxycarbonyl)amino)methyl)phenyl)benzofuran-5-carboxylic acid (130c) (0.12 g, 0.327 mmol) in DMF (5 mL) using ethyl 2-(2-amino-3-methylphenyl)acetate (165c) (0.076 g, 0.392 mmol), DIPEA (0.171 mL, 0.980 mmol) and HATU (0.149 g, 0.392 mmol). This gave after workup and purification by flash column chromatography [silica gel, 25 g eluting with ethyl acetate/methanol (9:1) in hexanes from 0-100%] to furnish ethyl 2-(2-(7-(3-(((tert-butoxycarbonyl)amino)methyl)phenyl)benzofuran-5-carboxamido)-3-methylphenyl)acetate (165d) (0.142 g, 80% yield) as a pale yellow solid; MS (ES+): 565.4 (M+Na); MS (ES−): 577.4 (M+Cl).

Step-4: Preparation of Ethyl 2-(2-(7-(3-(aminomethyl)phenyl)benzofuran-5-carboxamido)-3-methylphenyl)acetate (165e)

Compound 165e was prepared according to the procedure reported in step-5 of Scheme-1 from ethyl 2-(2-(7-(3-(((tert-butoxycarbonyl)amino)methyl)phenyl)benzofuran-5-carboxamido)-3-methylphenyl)acetate (165d) (0.139 g, 0.256 mmol) in DCM (5 mL) using TFA (0.395 mL, 5.12 mmol). This gave after workup and purification by flash column chromatography [silica gel 12 g, eluting with methanol in DCM from 0-30%] ethyl 2-(2-(7-(3-(aminomethyl)phenyl)benzofuran-5-carboxamido)-3-methylphenyl)acetate (165e) (0.088 g, 62% yield) as a TFA adduct; MS (ES+): 443.3 (M+1); MS (ES−): 477.4 (M+Cl).

Step-5: Preparation of 2-(2-(7-(3-(aminomethyl)phenyl)benzofuran-5-carboxamido)-3-methylphenyl)acetic Acid (165f)

Compound 165f was prepared according to the procedure reported in step-4 of Scheme-4, from ethyl 2-(2-(7-(3-(aminomethyl)phenyl)benzofuran-5-carboxamido)-3-methylphenyl)acetate (165e) (0.108 g, 0.199 mmol) in THF (3 mL) and methanol (6 mL) using a solution of sodium hydroxide (2 M aqueous, 0.288 mL, 0.576 mmol). This gave after workup and purification by reverse phase column [C18 (30 g), eluting with ACN in water (containing 0.1% HCl) from 0-100%] 2-(2-(7-(3-(aminomethyl)phenyl)benzofuran-5-carboxamido)-3-methylphenyl)acetic acid (165f) (0.004 g, 8% yield) HCl salt as a white solid. $^1$H NMR (300 MHz, DMSO-$d_6$) δ 12.2 (bs, 1H, $D_2O$ exchangeable), 10.05 (s, 1H, $D_2O$ exchangeable), 8.35 (d, J=1.7 Hz, 1H), 8.26-8.19 (m, 2H), 8.10-8.05 (m, 1H), 8.04-7.97 (m, 1H), 7.69-7.53 (m, 2H), 7.45-6.95 (m, 6H, $D_2O$ exchangeable, 2H), 4.16 (s, 2H), 3.59 (s, 2H), 2.24 (s, 3H); $^1$H NMR (300 MHz, DMSO-$d_6$ $D_2O$) δ 8.28 (d, J=1.7 Hz, 1H), 8.17-8.08 (m, 2H), 8.01-7.93 (m, 2H), 7.61 (t, J=7.7 Hz, 1H), 7.51 (d, J=7.7 Hz, 1H), 7.26-7.13 (m, 4H), 4.12 (s, 2H), 3.54 (s, 2H), 2.20 (s, 3H); MS (ES+): 415.3 (M+1), 437.2 (M+Na); 829.4 (2M+1); MS (ES−): 413.3 (M−1), 449.3 (M+Cl), 827.5 (2M−1); HPLC purity: 93.27%.

Scheme-166

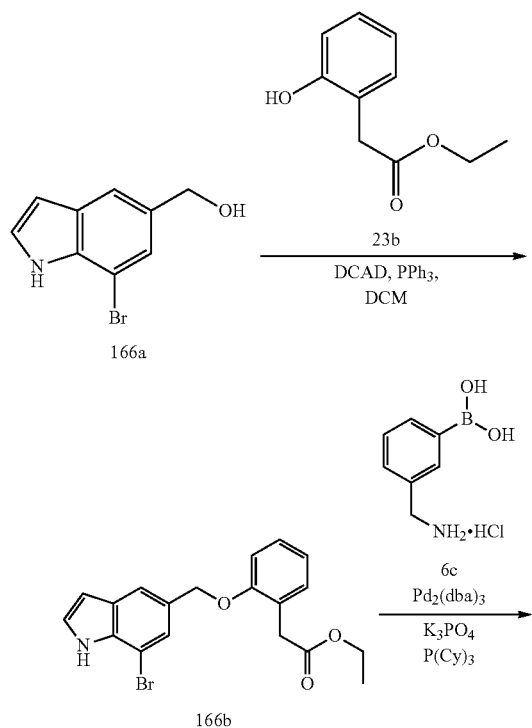

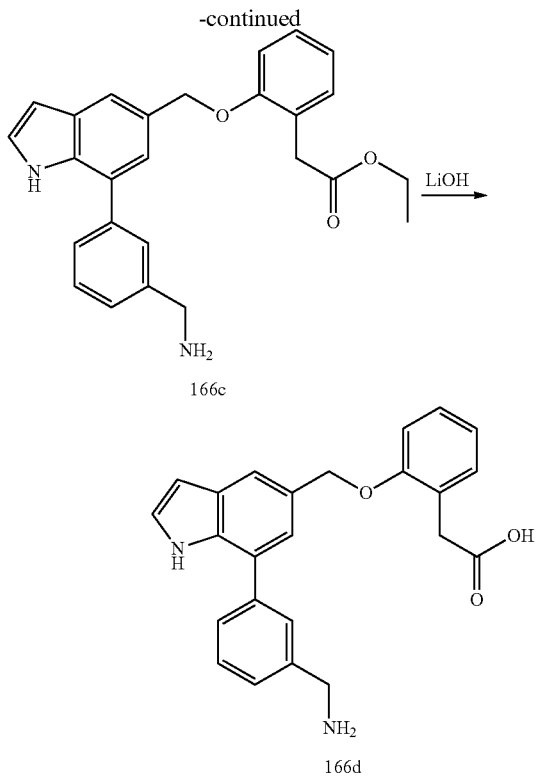

Preparation of 2-(2-((7-(3-(aminomethyl)phenyl)-1H-indol-5-yl)methoxy)phenyl)acetic acid (166d)

Step-1: Preparation of Ethyl 2-(2-((7-bromo-1H-indol-5-yl)methoxy)phenyl)acetate (166b)

Compound 166b was prepared according to the procedure reported in step-2 of Scheme-23 from (7-bromo-1H-indol-5-yl)methanol (166a) (440 mg, 1.946 mmol; prepared according to the procedure reported by Fairfax, David John et al; in U.S. Pat. Appl. Publ., 2014/0140956 (incorporated by reference), 22 May 2014) in DCM (20 mL) using triphenylphosphine (766 mg, 2.92 mmol) ethyl 2-(2-hydroxyphenyl) acetate (23b) (877 mg, 4.87 mmol) and a solution of di-(4-chlorobenzyl)azodicarboxylate (1072 mg, 2.92 mmol) in DCM (20 mL). This gave after workup and purification by flash column chromatography [silica (12 g), eluting with hexanes/ethyl acetate (1:0 to 4:1, then 0:1)] ethyl 2-(2-((7-bromo-1H-indol-5-yl)methoxy)phenyl)acetate (166b) (350 mg) as a brown gum; MS (ES+): 410.1 & 412.1 (M+Na); MS (ES−): 386.2 & 388.2 (M−1).

Step-2: Preparation of Ethyl 2-(2-((7-(3-(aminomethyl)phenyl)-1H-indol-5-yl)methoxy)phenyl)acetate (166c)

Compound 166c was prepared according to the procedure reported in step-3 of Scheme-1 from ethyl 2-(2-((7-bromo-1H-indol-5-yl)methoxy)phenyl)acetate (166b) (240 mg, 0.618 mmol) in dioxane (4 mL) using 3-(aminomethyl)phenylboronic acid hydrochloride (6c) (174 mg, 0.927 mmol), tripotassium phosphate (1.3 M solution, 0.350 mL, 1.051 mmol), tricyclohexylphosphine (104 mg, 0.371 mmol) and Pd$_2$(dba)$_3$ (170 mg, 0.185 mmol) under an Ar atmosphere and heating at 125° C. for 2 h in a microwave.

This gave after workup, purification by flash column chromatography [silica (24 g), eluting with dichloromethane/methanol (1:0 to 9:1)] ethyl 2-(2-((7-(3-(aminomethyl)phenyl)-1H-indol-5-yl)methoxy)phenyl)acetate (166c) (60 mg) as a brown solid; MS (ES+): 415.4 (M+1) & 437.3 (M+Na); MS (ES−): 449.3 (M+Cl).

Step-3: Preparation of 2-(2-((7-(3-(aminomethyl)phenyl)-1H-indol-5-yl)methoxy)phenyl)acetic Acid (166d)

Compound 166d was prepared according to the procedure reported in step-6 of Scheme-1 from ethyl 2-(2-((7-(3-(aminomethyl)phenyl)-1H-indol-5-yl)methoxy)phenyl)acetate (166c) (55 mg, 0.133 mmol) in THF (6 mL) and MeOH (6 mL) using a solution of lithium hydroxide hydrate (34 mg, 0.796 mmol) in water (6 mL). This gave after workup and purification by flash column chromatography [silica gel, eluting with dichloromethane/methanol (1:0 to 9:1)] 2-(2-((7-(3-(aminomethyl)phenyl)-1H-indol-5-yl)methoxy)phenyl)acetic acid (166d) (11 mg, 2.3% for three steps) as a light brown solid; $^1$H NMR (300 MHz, DMSO-$d_6$) δ 11.10 (s, 1H), 8.15 (s, 1H), 7.76 (d, J=7.7 Hz, 1H), 7.59 (s, 1H), 7.52-7.41 (m, 2H), 7.38-7.28 (m, 2H), 7.13-7.02 (m, 2H), 6.97 (d, J=8.2 Hz, 1H), 6.78 (t, J=7.2 Hz, 1H), 6.52 (s, 1H), 5.21 (s, 2H), 3.98 (s, 2H), 3.37 (s, 2H); MS (ES−): 771.7 (2M−1).

Scheme-167

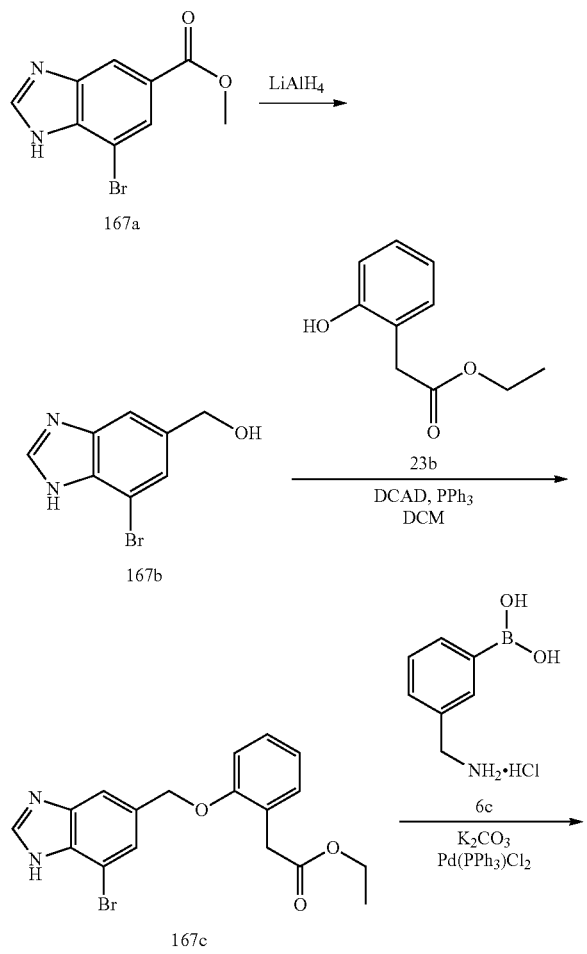

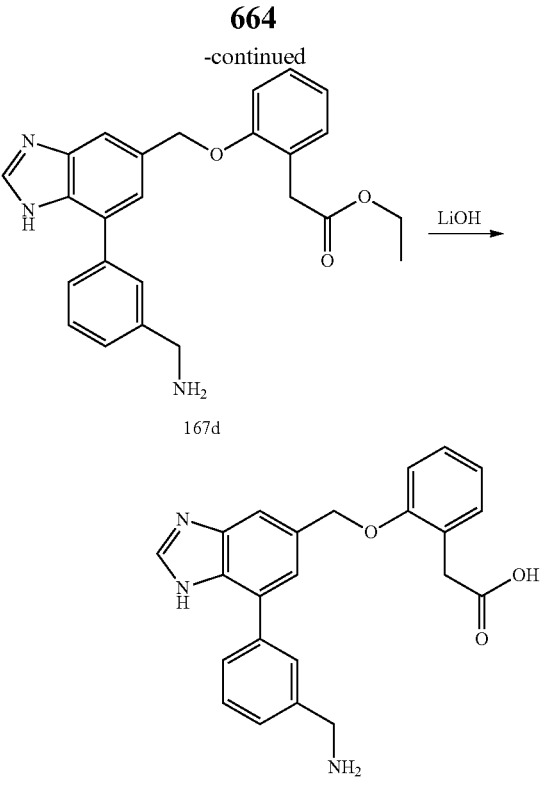

Preparation of 2-(2-((7-(3-(aminomethyl)phenyl)-1H-benzo[d]imidazol-5-yl)methoxy)phenyl)acetic Acid (167e)

Step-1: Preparation of (7-bromo-1H-benzo[d]imidazol-5-yl)methanol (167b)

To a solution of methyl 7-bromo-1H-benzo[d]imidazole-5-carboxylate (167a) (300 mg, 1.176 mmol; CAS #1354756-19-6) in THF (10 mL) cooled to 0° C. was added lithium aluminum hydride (44.6 mg, 1.176 mmol) and stirred at RT for 18 h. Additional lithium aluminum hydride (90 mg) was added and reaction was continued stirring at RT for 6 h. The reaction was quenched carefully with 20% aqueous Na$_2$SO$_4$ (10 mL), water (40 mL) and extracted with ethyl acetate (100 mL, 50 mL). The combined organic extracts were washed with brine (50 mL), dried, filtered and concentrated in vacuum. The crude product was purified by flash column chromatography [silica gel, eluting with dichloromethane/methanol (1:0 to 9:1)] to afford (7-bromo-1H-benzo[d]imidazol-5-yl)methanol (167b) (195 mg, 73%) as a white solid; $^1$H NMR (300 MHz, DMSO-$d_6$) δ 12.69 (bs, 1H), 8.26 (s, 1H), 7.49 (bs, 1H), 7.36 (bs, 1H), 5.30 (bs, 1H), 4.58 (s, 2H); MS (ES+): 249.1 (M+Na).

Step-2: Preparation of Ethyl 2-(2-((7-bromo-1H-benzo[d]imidazol-5-yl)methoxy)phenyl)acetate (167c)

Compound 167c was prepared according to the procedure reported in step-2 of Scheme-23 from (7-bromo-1H-benzo[d]imidazol-5-yl)methanol (167b) (180 mg, 0.793 mmol) in DCM (9 mL), THF (4 mL) and DMF (4 mL) using triphenylphosphine ((312 mg, 1.189 mmol) ethyl 2-(2-hydroxyphenyl) acetate (23b) (357 mg, 1.982 mmol) and a solution of di-(4-chlorobenzyl)azodicarboxylate (437 mg, 1.189 mmol in DCM (9 mL). This gave after workup and purification by flash column chromatography [silica (24 g), eluting with dichloromethane/methanol (1:0 to 19:1)] ethyl 2-(2-((7-bromo-1H-benzo[d]imidazol-5-yl)methoxy)phenyl)acetate (167c) (54 mg) as a light brown gum; MS (ES−): 387.2 & 389.2 (M−1).

Step-3: Preparation of Ethyl 2-(2-((7-(3-(aminomethyl)phenyl)-1H-benzo[d]imidazol-5-yl)methoxy)phenyl)acetate (167d)

Compound 167d was prepared according to the procedure reported in step-3 of Scheme-1 from ethyl 2-(2-((7-bromo-1H-benzo[d]imidazol-5-yl)methoxy)phenyl)acetate (167c) (50 mg, 0.128 mmol) in dioxane (4 mL) using 3-(aminomethyl)phenylboronic acid hydrochloride (6c) (36.1 mg, 0.193 mmol), Pd(PPh$_3$)$_2$Cl$_2$ (27.0 mg, 0.039 mmol) and potassium carbonate (35.5 mg, 0.257 mmol) in water (0.6 mL) under an Ar atmosphere and heating at 95° C. for 3 h in an oil bath. This gave after workup, purification by flash column chromatography [silica (24 g), eluting with dichloromethane/DMA 80 (1:0 to 1:1)] ethyl 2-(2-((7-(3-(aminomethyl)phenyl)-1H-benzo[d]imidazol-5-yl)methoxy)phenyl)acetate (167d) (7 mg, 2% for two steps) as a colorless gum; MS (ES+): 416.2 (M+1).

Step-4: Preparation of 2-(2-((7-(3-(aminomethyl)phenyl)-1H-benzo[d]imidazol-5-yl)methoxy)phenyl)acetic Acid (167e)

Compound 167e was prepared according to the procedure reported in step-6 of Scheme-1 from ethyl 2-(2-((7-(3-(aminomethyl)phenyl)-1H-benzo[d]imidazol-5-yl)methoxy)phenyl)acetate (167d) (7 mg, 0.017 mmol) in THF (3 mL) and MeOH (3 mL) using a solution of lithium hydroxide hydrate (7.21 mg, 0.168 mmol) in water (5 mL). This gave after workup and purification by flash column chromatography [silica gel, eluting with dichloromethane/DMA 50 (1:0 to 1:1)] 2-(2-((7-(3-(aminomethyl)phenyl)-1H-benzo[d]imidazol-5-yl)methoxy)phenyl)acetic acid (167e) (4 mg, 61%) as a white solid; $^1$H NMR (300 MHz, Methanol-d$_4$) δ 8.26 (s, 1H), 8.09 (s, 1H), 7.93 (d, J=7.7 Hz, 1H), 7.78-7.64 (m, 3H), 7.57 (t, J=7.7 Hz, 1H), 7.45 (t, J=8.9 Hz, 1H), 7.26-7.17 (m, 2H), 7.07-7.02 (m, 1H), 6.93-6.87 (m, 1H), 5.30 (d, J=3.0 Hz, 2H), 4.20 (s, 2H), 3.66 (s, 2H); MS (ES+): 388.3 (M+1); MS (ES−): 386.3 (M−1); HPLC purity: 87.87%.

Scheme-168

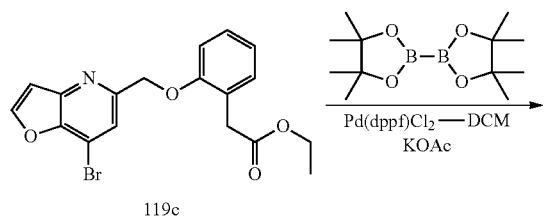

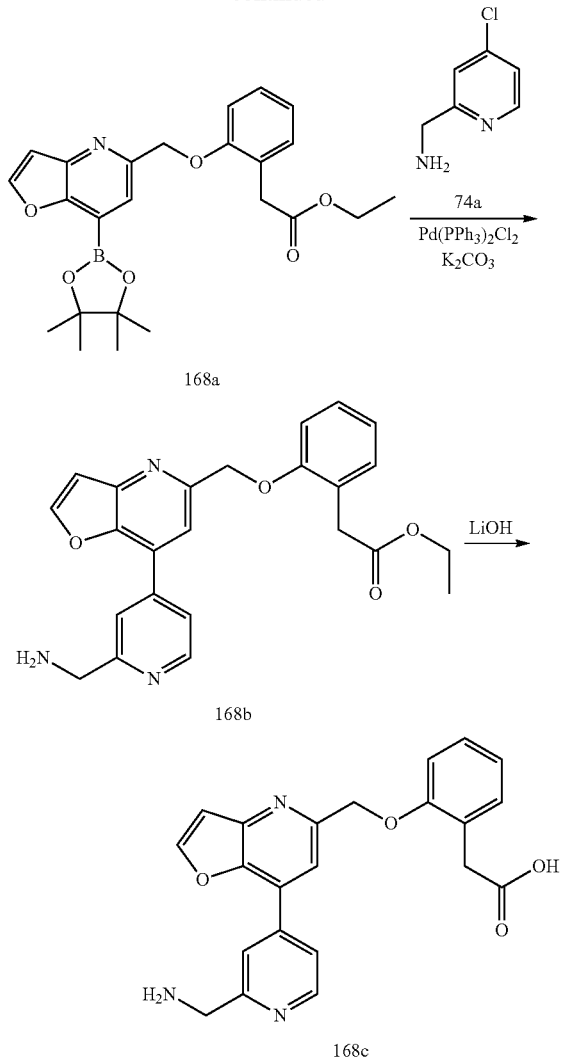

Preparation of 2-(2-((7-(2-(aminomethyl)pyridin-4-yl)furo[3,2-b]pyridin-5-yl)methoxy)phenyl)acetic Acid (168c)

Step-1: Preparation of Ethyl 2-(2-((7-(4,4,5,5-tetramethyl-1,3,2-dioxaborolan-2-yl)furo[3,2-b]pyridin-5-yl)methoxy)phenyl)acetate (168a)

Compound 168a was prepared according to the procedure reported in step-1 of Scheme-59 from ethyl 2-(2-((7-bromo-furo[3,2-b]pyridin-5-yl)methoxy)phenyl)acetate (119c) (430 mg, 1.102 mmol), using bis(pinacolato)diboron (420 mg, 1.65 mmol), potassium acetate (324 mg, 3.31 mmol) and PdCl$_2$(dppf)-CH$_2$Cl$_2$ (135 mg, 0.17 mmol) in anhydrous dioxane (10 mL) under an Ar atmosphere and heating at 100° C. overnight. This gave after workup and purification by flash column chromatography [silica gel, 40g, eluting with EtOAc in hexane from 0-40%] ethyl 2-(2-((7-(4,4,5,5-tetramethyl-1,3,2-dioxaborolan-2-yl)furo[3,2-b]pyridin-5-yl)methoxy)phenyl)acetate (168a) (150 mg, 31% yield) as a clear oil; MS (ES+): 460.4 (M+Na).

Step-2: Preparation of Ethyl 2-(2-((7-(2-(aminomethyl)pyridin-4-yl)furo[3,2-b]pyridin-5-yl)methoxy)phenyl)acetate (168b)

Compound 168b was prepared according to the procedure reported in step-3 of Scheme-1 from ethyl 2-(2-((7-(4,4,5,5-tetramethyl-1,3,2-dioxaborolan-2-yl)furo[3,2-b]pyridin-5-yl)methoxy)phenyl)acetate (168a) (70 mg, 0.16 mmol) in dioxane (6 mL) using (4-chloropyridin-2-yl)methanamine (74a) (34 mg, 0.24 mmol), bis(triphenylphosphine)palladium(II) chloride (17 mg, 0.02 mmol) and a solution of $K_2CO_3$ (55 mg, 0.40 mmol) in water (3 mL) under an Ar atmosphere and heating at 100° C. for 3 h on oil bath. This gave after workup, purification by flash column chromatography [silica (40 g), eluting with DMA80 in DCM from 0-70%] ethyl 2-(2-((7-(2-(aminomethyl)pyridin-4-yl)furo[3,2-b]pyridin-5-yl)methoxy)phenyl)acetate (168b) (21 mg, 31% yield) as a yellow oil; MS (ES+): 418.2 (M+1).

Step-3: Preparation of 2-(2-((7-(2-(aminomethyl)pyridin-4-yl)furo[3,2-b]pyridin-5-yl)methoxy)phenyl)acetic Acid (168c)

Compound 168c was prepared according to the procedure reported in step-6 of Scheme-1 from ethyl 2-(2-((7-(2-(aminomethyl)pyridin-4-yl)furo[3,2-b]pyridin-5-yl)methoxy)phenyl)acetate (168b) (21 mg, 0.050 mmol) THF/MeOH (6 mL each) using lithium hydroxide monohydrate (12.67 mg, 0.30 mmol) in water (2.0 mL). This gave after workup and purification by reverse phase column [C18 (50 g), eluting with ACN in water (containing 0.1% HCl) from 0-100%] 2-(2-((7-(2-(aminomethyl)pyridin-4-yl)furo[3,2-b]pyridin-5-yl)methoxy)phenyl)acetic acid (168c) (3 mg, 14% yield) HCl salt as an off white solid; $^1$H NMR (300 MHz, DMSO-$d_6$) δ 8.88 (d, J=5.2 Hz, 1H), 8.50 (d, J=2.3 Hz, 1H), 8.25-8.19 (m, 2H), 8.17 (dd, J=5.2, 1.7 Hz, 1H), 7.33-7.23 (m, 3H), 7.11-7.04 (m, 1H), 6.99 (td, J=7.4, 1.0 Hz, 1H), 5.55 (s, 2H), 4.45 (s, 2H), 3.78 (s, 2H); MS (ES+): 390.2 (M+1); (ES-): 388.2 (M-1).

Scheme-169

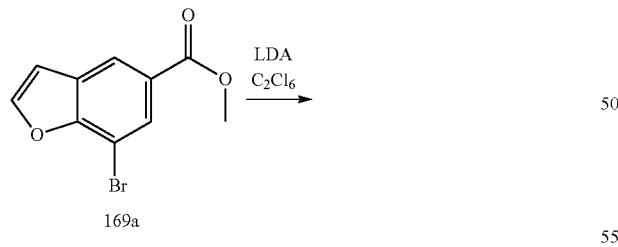

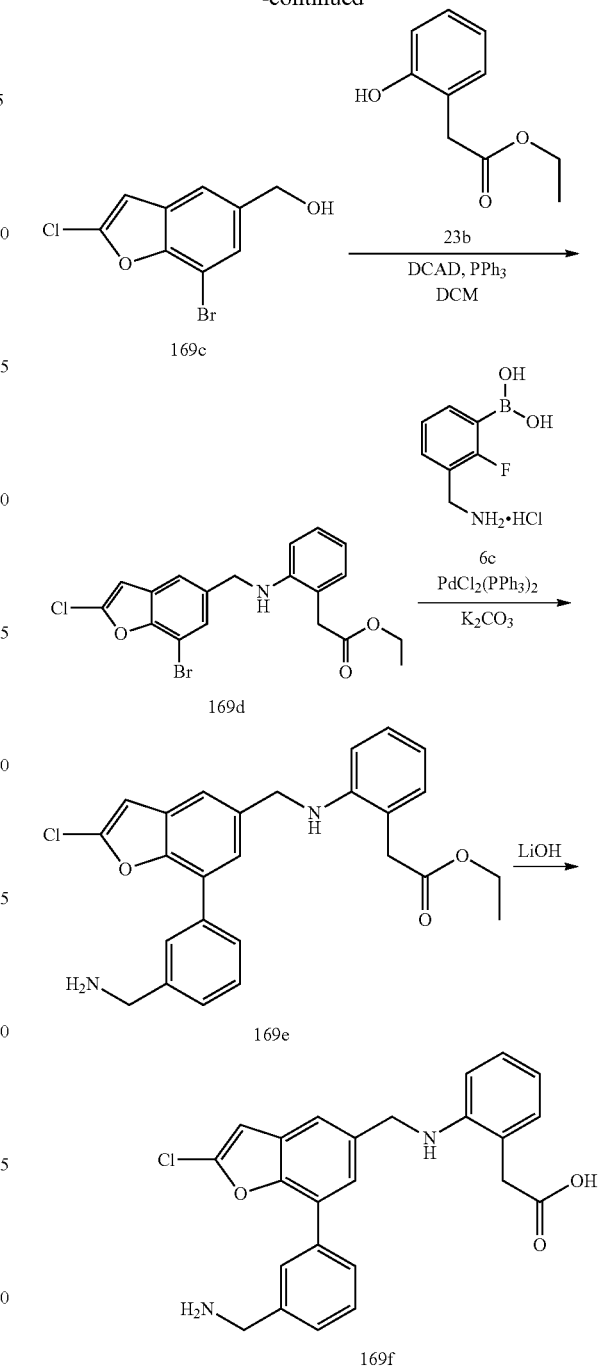

Preparation of 2-(2-((7-(3-(aminomethyl)phenyl)-2-chlorobenzofuran-5-yl)methoxy)phenyl)acetic Acid (169f)

Step-1: Preparation of methyl 7-bromo-2-chlorobenzofuran-5-carboxylate (169b)

To a stirred solution of methyl 7-bromobenzofuran-5-carboxylate (169a) (3.06 g, 12.00 mmol; CAS #286836-79-1) in dry THF (10 mL) at −78° C. under $N_2$ was added dropwise LDA (1.5 M in THF, 11 mL, 16.50 mmol). The mixture was kept at −78° C. for 1.5 h followed by the addition of a solution of perchloroethane (4.06 g, 17.15 mmol) in dry THF (8 mL). The mixture was slowly warmed to room temperature and stirred overnight. The reaction was quenched with saturated NH$_4$Cl aqueous solution and extracted with ethyl acetate. The organic layers were combined, washed with brine, dried over Na$_2$SO$_4$ and concentrated. The residue was purified by flash column chromatography [silica (40 g), eluting with ethyl acetate/hexanes, 0-30%] to afford methyl 7-bromo-2-chlorobenzofuran-5-carboxylate (169b) (1.56 g, 45% yield) as white solid; $^1$H NMR (300 MHz, DMSO-d$_6$) δ 8.25 (d, J=1.6 Hz, 1H), 8.07 (d, J=1.6 Hz, 1H), 7.31 (s, 1H), 3.89 (s, 3H).

Step-2: Preparation of (7-bromo-2-chlorobenzofuran-5-yl)methanol (169c)

Compound 169c was prepared according to the procedure reported in step-2 of Scheme-76 from methyl 7-bromo-2-chlorobenzofuran-5-carboxylate (169b) (1.67 g, 5.77 mmol) in THF (20 mL) using LiBH$_4$ (4.25 mL, 4 M, 17.00 mmol) and MeOH (0.7 mL, 17.30 mmol). This gave after workup and purification by flash column chromatography [silica (24 g), eluting with EtOAc in hexane from 0-50%] (7-bromo-2-chlorobenzofuran-5-yl)methanol (169c) (1.01 g, 67.0% yield) as a white solid; $^1$H NMR (300 MHz, DMSO-d$_6$) δ 7.53 (m, 2H), 7.17 (s, 1H), 5.39 (t, J=5.7 Hz, 1H), 4.56 (d, J=5.6 Hz, 2H).

Step-3: Preparation of Ethyl 2-(2-((7-bromo-2-chlorobenzofuran-5-yl)methoxy)phenyl)acetate (169d)

Compound 169d was prepared according to the procedure reported in step-2 of Scheme-23 from (7-bromo-2-chlorobenzofuran-5-yl)methanol (169c) (1.02 g, 3.90 mmol) in DCM (30 mL) using triphenylphosphine (1.12 g, 4.27 mmol), ethyl 2-(2-hydroxyphenyl) acetate (23b) (862 mg, 4.78 mmol) and di-(4-chlorobenzyl)azodicarboxylate (DCAD, 1.55 g, 4.22 mmol) in DCM (2 mL). This gave after workup and purification by flash column chromatography [silica (24 g), eluting with EtOAc in hexane from 0-40%] ethyl 2-(2-((7-bromo-2-chlorobenzofuran-5-yl)methoxy)phenyl)acetate (169d) (839 mg, 51% yield) as a white solid. $^1$H NMR (300 MHz, DMSO-d$_6$) δ 7.69-7.60 (m, 2H), 7.30-7.19 (m, 3H), 7.06 (dd, J=8.2, 1.1 Hz, 1H), 6.92 (td, J=7.4, 1.1 Hz, 1H), 5.18 (s, 2H), 4.02 (q, J=7.1 Hz, 2H), 3.63 (s, 2H), 1.09 (t, J=7.1 Hz, 3H).

Step-4: Preparation of Ethyl 2-(2-((7-(3-(aminomethyl)phenyl)-2-chlorobenzofuran-5-yl)methoxy)phenyl)acetate (169e)

Compound 169e was prepared according to the procedure reported in step-3 of Scheme-1 from ethyl 2-(2-((7-bromo-2-chlorobenzofuran-5-yl)methoxy)phenyl)acetate (169d) (230 mg, 0.543 mmol) in dioxane (5 mL) using 3-(aminomethyl)phenylboronic acid hydrochloride (6c) (142 mg, 0.941 mmol), a solution of K$_2$CO$_3$ (231 mg, 1.671 mmol) in water (0.5 mL), bis(triphenylphosphine)palladium(II) chloride (61 mg, 0.087 mmol) and heating at 100° C. for 3h on oil bath. This gave after workup, purification by flash column chromatography [silica (24 g), eluting with DMA80 in DCM from 0-50%] compound 169e (160 mg, 66% yield) as a clear oil. An analytical sample was obtained by purification using reverse phase column chromatography [C18 (50 g), eluting with ACN in water (containing 0.1% HCl) from 0-100%] to afford ethyl 2-(2-((7-(3-(aminomethyl)phenyl)-2-chlorobenzofuran-5-yl)methoxy)phenyl)acetate (169e) HCl salt as white solid. $^1$H NMR (300 MHz, DMSO-d$_6$) δ 8.53 (s, 3H), 7.89 (d, J=1.8 Hz, 1H), 7.84-7.73 (m, 1H), 7.60 (d, J=1.6 Hz, 1H), 7.58-7.50 (m, 3H), 7.24-7.12 (m, 2H), 7.10 (s, 1H), 7.04 (dd, J=8.2, 1.1 Hz, 1H), 6.85 (td, J=7.4, 1.1 Hz, 1H), 5.17 (s, 2H), 4.06 (s, 2H), 3.87 (q, J=7.1 Hz, 2H), 3.57 (s, 2H), 0.93 (t, J=7.1 Hz, 3H); MS(ES+): 450.2 (M+1); HPLC purity 100%. Analysis calculated for C$_{26}$H$_{24}$ClNO$_4$.HCl.H$_2$O: C, 61.91; H, 5.40; N, 2.78; Found: C, 62.28; H, 5.13; N, 2.82.

Step-5: Preparation of 2-(2-((7-(3-(aminomethyl)phenyl)-2-chlorobenzofuran-5-yl)methoxy)phenyl)acetic Acid (169f)

Compound 169f was prepared according to the procedure reported in step-6 of Scheme-1, from ethyl 2-(2-((7-(3-(aminomethyl)phenyl)-2-chlorobenzofuran-5-yl)methoxy)phenyl)acetate (169e) (112 mg, 0.249 mmol) in MeOH/THF (6 mL each) using a solution of lithium hydroxide monohydrate (60 mg, 2.505 mmol) in water (2 mL). This gave after workup and purification by reverse phase column [C18 (50 g), eluting with ACN in water (containing 0.1% HCl) from 0-100%] 2-(2-((7-(3-(aminomethyl)phenyl)-2-chlorobenzofuran-5-yl)methoxy)phenyl)acetic acid (169f) (68 mg, 65% yield) as a white solid; $^1$H NMR (300 MHz, DMSO-d$_6$) δ 8.52 (s, 3H), 7.95 (s, 1H), 7.87 (s, 1H), 7.73-7.56 (m, 4H), 7.22 (d, J=7.8 Hz, 2H), 7.11 (d, J=13.2 Hz, 2H), 6.91 (s, 1H), 5.26 (s, 2H), 4.13 (s, 2H), 3.60 (s, 2H); 1H NMR (300 MHz, DMSO-d$_6$, D$_2$O exchange) δ 8.01-7.78 (m, 2H), 7.78-7.43 (m, 4H), 7.36-7.14 (m, 2H), 7.06 (d, J=8.1 Hz, 2H), 6.91 (d, J=7.5 Hz, 1H), 5.23 (s, 2H), 4.12 (s, 2H), 3.58 (s, 2H); MS (ES+): 422.1 (M+1); MS(ES−): 420.2 (M−1). HPLC purity 100%. Analysis calculated for C$_{24}$H$_{20}$ClNO$_4$HCl.H$_2$O: C, 60.51; H, 4.87; Cl, 14.89; N, 2.94; Found: C, 60.81; H, 4.75; Cl, 14.95; N, 3.04.

Scheme-170

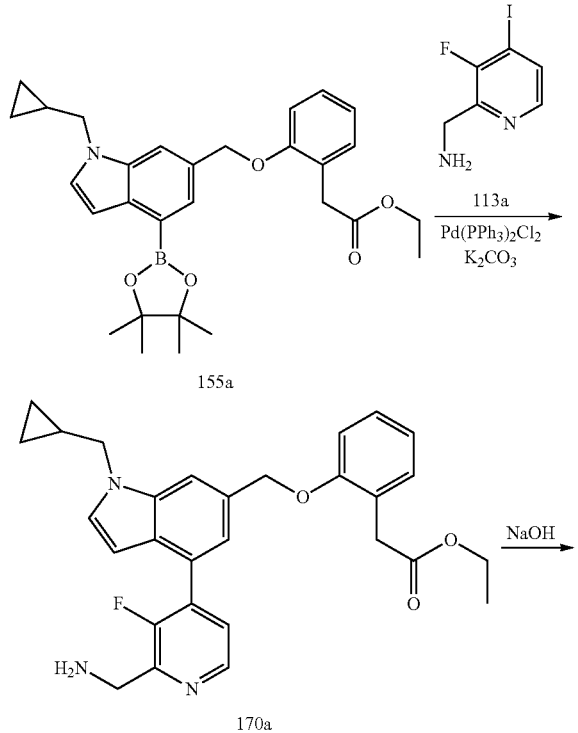

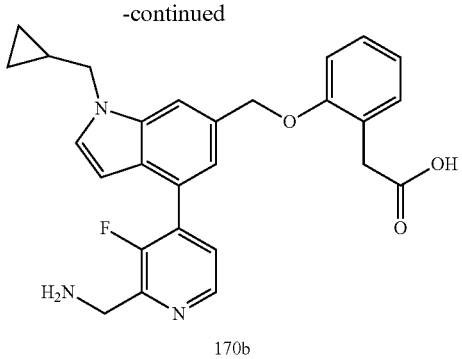

170b

Preparation of 2-(2-((4-(2-(aminomethyl)-3-fluoro-pyridin-4-yl)-1-(cyclopropylmethyl)-1H-indol-6-yl)methoxy)phenyl)acetic Acid (170b)

Step-1: Preparation of Ethyl 2-(2-((4-(2-(aminomethyl)-3-fluoropyridin-4-yl)-1-(cyclopropylmethyl)-1H-indol-6-yl)methoxy)phenyl)acetate (170a)

Compound 170a was prepared according to the procedure reported in step-3 of Scheme-1 from ethyl 2-(2-((1-(cyclopropylmethyl)-4-(4,4,5,5-tetramethyl-1,3,2-dioxaborolan-2-yl)-1H-indol-6-yl)methoxy)phenyl)acetate (155a) (0.7 g, 1.43 mmol) in dioxane (7 mL) using (3-fluoro-4-iodopyridin-2-yl)methanamine (113a) (0.28 g, 1.10 mmol), bis(triphenylphosphine)palladium(II) chloride (0.12 g, 0.17 mmol) and a solution of $K_2CO_3$ (0.38 g, 2.75 mmol) in water (0.7 mL) under an Ar atmosphere and heating at 100° C. for 2 h on oil bath. This gave after workup, purification by flash column chromatography [silica (12 g), eluting with MeOH in DCM from 0-50%] followed by purification by reverse-phase column chromatography [C18 (50 g), eluting with ACN in water (containing 0.1% HCl) from 0-100%] ethyl 2-(2-((4-(2-(aminomethyl)-3-fluoropyridin-4-yl)-1-(cyclopropylmethyl)-1H-indol-6-yl)methoxy)phenyl)acetate (170a) (0.1 g, 19% yield) as a yellow solid; MS (ES+): 488.3 (M+1).

Step-2: Preparation of 2-(2-((4-(2-(aminomethyl)-3-fluoropyridin-4-yl)-1-(cyclopropylmethyl)-1H-indol-6-yl)methoxy)phenyl)acetic Acid (170b)

Compound 170b was prepared according to the procedure reported in step-4 of Scheme-4, ethyl 2-(2-((4-(2-(aminomethyl)-3-fluoropyridin-4-yl)-1-(cyclopropylmethyl)-1H-indol-6-yl)methoxy)phenyl)acetate (170a) (0.1 g, 0.21 mmol) THF (4 mL) and MeOH (4 mL) using sodium hydroxide (0.04 g, 1.03 mmol) in Water (1 mL). This gave after workup and purification by reverse phase column [C18 (50 g), eluting with ACN in water (containing 0.1% HCl) from 0-100%] 2-(2-((4-(2-(aminomethyl)-3-fluoropyridin-4-yl)-1-(cyclopropylmethyl)-1H-indol-6-yl)methoxy)phenyl)acetic acid (170b) (0.01 g, 12% yield) HCl salt as a yellow solid; $^1$H NMR (300 MHz, DMSO-$d_6$) δ 8.57 (d, J=4.9 Hz, 1H), 8.50 (s, 3H), 7.81 (s, 1H), 7.70 (t, J=5.3 Hz, 1H), 7.59 (d, J=3.2 Hz, 1H), 7.30-7.25 (m, 1H), 7.22 (d, J=7.4 Hz, 2H), 7.11 (d, J=8.1 Hz, 1H), 6.90 (td, J=7.4, 1.1 Hz, 1H), 6.38 (t, J=3.1 Hz, 1H), 5.29 (s, 2H), 4.37 (d, J=5.8 Hz, 2H), 4.11 (d, J=7.0 Hz, 2H), 3.59 (s, 2H), 1.38-1.16 (m, 1H), 0.58-0.31 (m, 4H); $^{19}$F NMR (282 MHz, DMSO-$d_6$) δ−128.89; MS (ES+): 460.3 (M+1); MS (ES−): 458.3 (M−1). HPLC purity: 96.70%.

Scheme-171

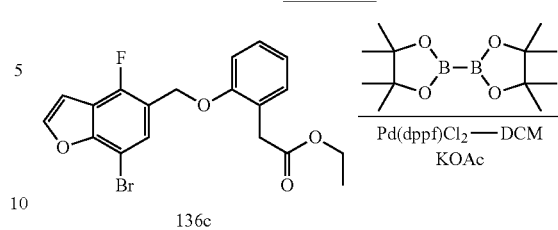

136c

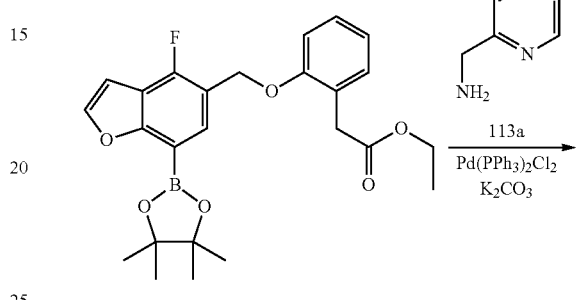

171a

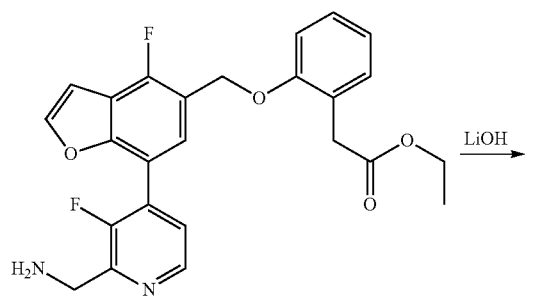

171b

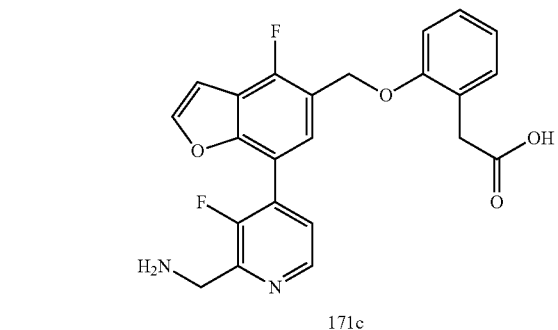

171c

Preparation of 2-(2-((7-(2-(aminomethyl)-3-fluoro-pyridin-4-yl)-4-fluorobenzofuran-5-yl)methoxy)phenyl)acetic Acid (171c)

Step-1: Preparation of Ethyl 2-(2-((4-fluoro-7-(4,4,5,5-tetramethyl-1,3,2-dioxaborolan-2-yl)benzofuran-5-yl)methoxy)phenyl)acetate (171a)

Compound 171a was prepared according to the procedure reported in step-1 of Scheme-59 from ethyl 2-(2-((7-bromo-4-fluorobenzofuran-5-yl)methoxy)phenyl)acetate (136c) (510 mg, 1.25 mmol), using bis(pinacolato)diboron (477 mg, 1.88 mmol), potassium acetate (369 mg, 3.76 mmol) and Pd(dppf)Cl$_2$—CH$_2$Cl$_2$ (153 mg, 0.19 mmol) in anhydrous dioxane (10 mL) under an Ar atmosphere and heating at 100° C. overnight. This gave after workup and purification by flash column chromatography [silica gel, 40g, eluting with EtOAc in hexane from 0-40%] ethyl 2-(2-((4-fluoro-7-(4,4,5,5-tetramethyl-1,3,2-dioxaborolan-2-yl) benzofuran-5-yl)methoxy)phenyl)acetate (171a) (400 mg, 70% yield) as a white solid; MS (ES+): 477.2 (M+Na); (ES−): 453.3 (M−1).

Step-2: Preparation of Ethyl 2-(2-((7-(2-(aminomethyl)-3-fluoropyridin-4-yl)-4-fluorobenzofuran-5-yl)methoxy)phenyl)acetate (171b)

Compound 171b was prepared according to the procedure reported in step-3 of Scheme-1 from ethyl 2-(2-((4-fluoro-7-(4,4,5,5-tetramethyl-1,3,2-dioxaborolan-2-yl)benzofuran-5-yl)methoxy)phenyl)acetate (171a) (190 mg, 0.42 mmol) in dioxane (6 mL) using (3-fluoro-4-iodopyridin-2-yl)methanamine (113a) (137 mg, 0.54 mmol), bis(triphenylphosphine)palladium(II) chloride (44 mg, 0.063 mmol) and a solution of K$_2$CO$_3$ (173 mg, 1.26 mmol) in water (2 mL) under an Ar atmosphere and heating at 100° C. for 3 h on oil bath. This gave after workup, purification by flash column chromatography [silica (12 g), eluting with DMA80 in DCM from 0-70%] followed by purification by reverse-phase column chromatography [C18 (50 g), eluting with ACN in water (containing 0.1% HCl) from 0-100%] ethyl 2-(2-((7-(2-(aminomethyl)-3-fluoropyridin-4-yl)-4-fluorobenzofuran-5-yl)methoxy)phenyl)acetate (171b) (88 mg, 47% yield) as a white solid; $^1$H NMR (300 MHz, DMSO-d$_6$) δ 8.70-8.56 (m, 4H, Partially D$_2$O exchangeable), 8.21 (d, J=2.3 Hz, 1H), 7.79 (t, J=5.3 Hz, 1H), 7.70 (d, J=6.6 Hz, 1H), 7.34-7.26 (m, 2H), 7.26-7.17 (m, 2H), 6.94 (td, J=7.3, 1.2 Hz, 1H), 5.30 (s, 2H), 4.43-4.29 (m, 2H), 3.86 (q, J=7.1 Hz, 2H), 3.57 (s, 2H), 0.92 (t, J=7.1 Hz, 3H); $^{19}$F NMR (282 MHz, DMSO-d$_6$) δ−121.23, −128.69; MS (ES+): 453.2 (M+1).

Step-3: Preparation of 2-(2-((7-(2-(aminomethyl)-3-fluoropyridin-4-yl)-4-fluorobenzofuran-5-yl)methoxy)phenyl)acetic Acid (171c)

Compound 171c was prepared according to the procedure reported in step-6 of Scheme-1 from ethyl 2-(2-((7-(2-(aminomethyl)-3-fluoropyridin-4-yl)-4-fluorobenzofuran-5-yl)methoxy)phenyl)acetate (171b) (60 mg, 0.13 mmol) THF (6 mL) and MeOH (6 mL) using lithium hydroxide monohydrate (7.23 mg, 0.17 mmol) in water (2.0 mL). This gave after workup and purification by reverse phase column [C18 (50 g), eluting with ACN in water (containing 0.1% HCl) from 0-100%] 2-(2-((7-(2-(aminomethyl)-3-fluoropyridin-4-yl)-4-fluorobenzofuran-5-yl)methoxy)phenyl)acetic acid (171c) (22 mg, 39% yield) HCl salt as a white solid; $^1$H NMR (300 MHz, DMSO-d$_6$) δ 8.69-8.51 (m, 4H, partially D$_2$O exchangeable), 8.21 (d, J=2.3 Hz, 1H), 7.79 (t, J=5.3 Hz, 1H), 7.74 (d, J=6.6 Hz, 1H), 7.30-7.15 (m, 4H), 6.93 (td, J=7.3, 1.2 Hz, 1H), 5.32 (s, 2H), 4.42-4.30 (m, 2H), 3.54 (s, 2H); $^{19}$F NMR (282 MHz, DMSO-d$_6$) δ−121.30, −128.46; MS (ES+): 425.2 (M+1); (ES−): 423.3 (M−1).

Scheme-172

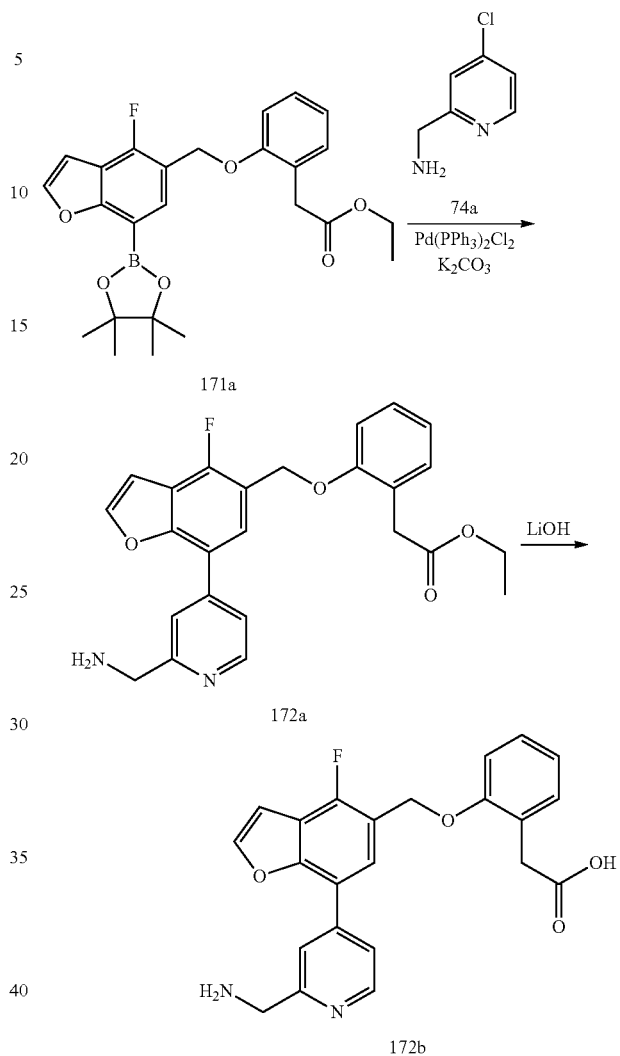

Preparation of 2-(2-((7-(2-(aminomethyl)pyridin-4-yl)-4-fluorobenzofuran-5-yl)methoxy)phenyl)acetic Acid (172b)

Step-1: Preparation of Ethyl 2-(2-((7-(2-(aminomethyl)pyridin-4-yl)-4-fluorobenzofuran-5-yl)methoxy)phenyl)acetate (172a)

Compound 172a was prepared according to the procedure reported in step-3 of Scheme-1 from ethyl 2-(2-((4-fluoro-7-(4,4,5,5-tetramethyl-1,3,2-dioxaborolan-2-yl)benzofuran-5-yl)methoxy)phenyl)acetate (171a) (190 mg, 0.42 mmol) in dioxane (6 mL) using (4-chloropyridin-2-yl)methanamine (74a) (78 mg, 0.54 mmol), bis(triphenylphosphine)palladium(II) chloride (44.0 mg, 0.063 mmol) and a solution of K$_2$CO$_3$ (173 mg, 1.26 mmol) in water (2 mL) under an Ar atmosphere and heating at 100° C. for 3 h on oil bath. This gave after workup, purification by flash column chromatography [silica (12 g), eluting with DMA80 in DCM from 0-70%] followed by purification by reverse-phase column chromatography [C18 (50 g), eluting with ACN in water (containing 0.1% HCl) from 0-100%] ethyl 2-(2-((7-(2-

(aminomethyl)pyridin-4-yl)-4-fluorobenzofuran-5-yl)methoxy)phenyl)acetate (172a) (70 mg, 39% yield) as a white solid; $^1$H NMR (300 MHz, DMSO-$d_6$) δ 8.78 (dd, J=5.3, 0.7 Hz, 1H), 8.51 (s, 3H, D$_2$O exchangeable), 8.26 (d, J=2.3 Hz, 1H), 8.09-8.05 (m, 1H), 7.98-7.89 (m, 2H), 7.34-7.26 (m, 2H), 7.25-7.17 (m, 2H), 6.94 (td, J=7.3, 1.2 Hz, 1H), 5.29 (s, 2H), 4.30 (q, J=5.7 Hz, 2H), 3.87 (q, J=7.1 Hz, 2H), 3.58 (s, 2H), 0.91 (t, J=7.1 Hz, 3H); $^{19}$F NMR (282 MHz, DMSO-$d_6$) δ−121.63; MS (ES+): 435.2 (M+1).

Step-2: Preparation of 2-(2-((7-(2-(aminomethyl)pyridin-4-yl)-4-fluorobenzofuran-5-yl)methoxy)phenyl)acetic Acid (172b)

Compound 172b was prepared according to the procedure reported in step-6 of Scheme-1 from ethyl 2-(2-((7-(2-(aminomethyl)pyridin-4-yl)-4-fluorobenzofuran-5-yl)methoxy)phenyl)acetate (172a) (56 mg, 0.13 mmol) THF (6 mL) and MeOH (6 mL) using lithium hydroxide monohydrate (7.03 mg, 0.17 mmol) in water (2.0 mL). This gave after workup and purification by reverse phase column [C18 (50 g), eluting with ACN in water (containing 0.1% HCl) from 0-100%] 2-(2-((7-(2-(aminomethyl)pyridin-4-yl)-4-fluorobenzofuran-5-yl)methoxy)phenyl)acetic acid (172b) (15 mg, 27% yield) HCl salt as a white solid; $^1$H NMR (300 MHz, DMSO-$d_6$) δ 8.80 (d, J=5.3 Hz, 1H), 8.64 (s, 3H, D$_2$O exchangeable), 8.26 (d, J=2.3 Hz, 1H), 8.17-8.10 (m, 1H), 8.05-7.93 (m, 2H), 7.34-7.16 (m, 4H), 6.94 (td, J=7.3, 1.2 Hz, 1H), 5.32 (s, 2H), 4.39-4.24 (m, 2H), 3.57 (s, 2H); $^{19}$F NMR (282 MHz, DMSO-$d_6$) δ−121.35; MS (ES+): 407.2 (M+1); (ES−): 405.3 (M−1).

Scheme-173

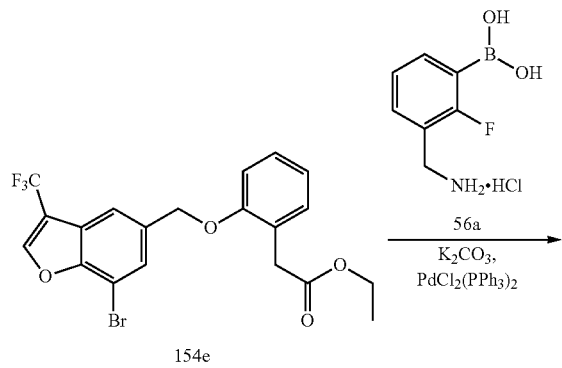

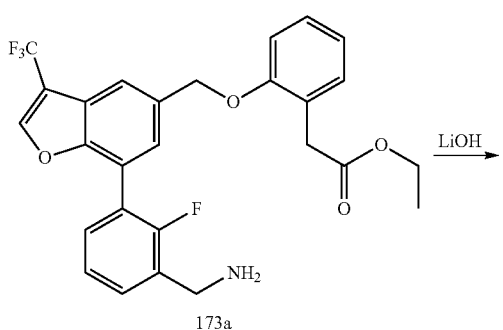

173a

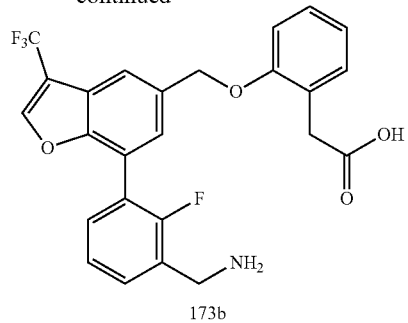

173b

Preparation of 2-(2-((7-(3-(aminomethyl)-2-fluorophenyl)-3-(trifluoromethyl)benzofuran-5-yl)methoxy)phenyl)acetic Acid (173b)

Step-1: Preparation of Ethyl 2-(2-((7-(3-(aminomethyl)-2-fluorophenyl)-3-(trifluoromethyl)benzofuran-5-yl)methoxy)phenyl)acetate (173a)

Compound 173a was prepared according to the procedure reported in step-3 of Scheme-1 from ethyl 2-(2-((7-bromo-3-(trifluoromethyl)benzofuran-5-yl)methoxy)phenyl)acetate (154e) (222 mg, 0.486 mmol) in dioxane (30 mL) using 3-(aminomethyl)-2-fluorophenylboronic acid hydrochloride (56a) (165 mg, 0.805 mmol), bis(triphenylphosphine)palladium(II) chloride (PdCl$_2$(PPh$_3$)$_2$) (55 mg, 0.078 mmol) and K$_2$CO$_3$ (220 mg, 1.592 mmol) in water (0.5 mL) under an Ar atmosphere heating at 100° C. for 3h on oil bath. This gave after workup, purification by flash column chromatography [silica gel 24 g, eluting with DMA80 in DCM from 0-50%] compound 173a (181 mg, 74% yield) free base as a clear oil. An analytical sample was obtained by purification of free base using reverse phase column chromatography [C18 (50 g), eluting with ACN in water (containing 0.1% HCl) from 0-100%] to afford ethyl 2-(2-((7-(3-(aminomethyl)-2-fluorophenyl)-3-(trifluoromethyl)benzofuran-5-yl)methoxy)phenyl)acetate (173a) HCl salt as white solid. $^1$H NMR (300 MHz, DMSO-$d_6$) δ 8.83 (s, 1H), 8.66 (s, 3H), 7.82 (s, 1H), 7.73 (t, J=7.4 Hz, 1H), 7.68-7.43 (m, 2H), 7.39 (t, J=7.7 Hz, 1H), 7.19 (q, J=7.8 Hz, 2H), 7.06 (d, J=8.2 Hz, 1H), 6.85 (t, J=7.4 Hz, 1H), 5.25 (s, 2H), 4.10 (s, 2H), 3.85 (q, J=7.1 Hz, 2H), 3.56 (s, 2H), 0.91 (t, J=7.1 Hz, 3H); $^{19}$F NMR (282 MHz, DMSO-$d_6$) δ−58.08, −118.78. MS (ES+): 502.2 (M+1).

Step-2: Preparation of 2-(2-((7-(3-(aminomethyl)-2-fluorophenyl)-3-(trifluoromethyl)benzofuran-5-yl)methoxy)phenyl)acetic Acid (173b)

Compound 173b was prepared according to the procedure reported in step-6 of Scheme-1 from ethyl 2-(2-((7-(3-(aminomethyl)-2-fluorophenyl)-3-(trifluoromethyl)benzofuran-5-yl)methoxy)phenyl)acetate (173a) (121 mg, 0.241 mmol) THF/MeOH (6 mL each) using lithium hydroxide (75 mg, 3.13 mmol) in water (2 mL). This gave after workup and purification by reverse phase column chromatography [C18 (50 g), eluting with ACN in water (containing 0.1% HCl) from 0-100%] 2-(2-((7-(3-(aminomethyl)-2-fluorophenyl)-3-(trifluoromethyl)benzofuran-5-yl)methoxy)phenyl)acetic acid (173b) (53 mg, 46% yield) HCl salt as a white solid. $^1$H NMR (300 MHz, DMSO-$d_6$) δ 8.81 (d, J=2.0 Hz, 1H), 8.66 (s, 2H), 7.85 (s, 1H), 7.79-7.67 (m, 1H), 7.67-7.52 (m, 2H), 7.38 (t, J=7.7 Hz, 1H), 7.26-7.09 (m, 2H), 7.03 (d, J=8.1 Hz, 1H), 6.85 (t, J=7.3 Hz, 1H), 5.26 (s, 2H), 4.10 (s, 2H), 3.52 (s, 2H); 19F NMR (282 MHz, DMSO-d$_6$) δ −58.02, −118.61. MS (ES+): 474.1 (M+1); MS(ES−): 472.2 (M−1). HPLC purity 99.28%. Analysis calculated for C$_{25}$H$_{19}$F$_4$NO$_4$.HCl.0.25H$_2$O: C, 58.37; H, 4.02; Cl, 6.89; N, 2.72; Found: C, 58.34; H, 3.88; Cl, 6.80; N, 2.78.

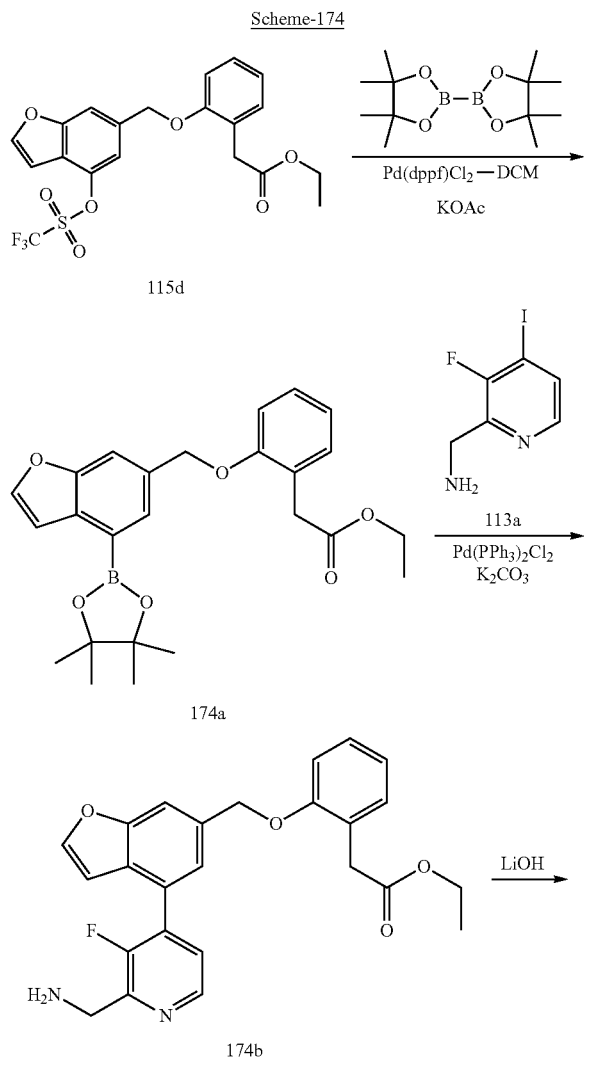

Scheme-174

Preparation of 2-(2-((4-(2-(aminomethyl)-3-fluoropyridin-4-yl)benzofuran-6-yl)methoxy)phenyl)acetic Acid (174c)

Step-1: Preparation of Ethyl 2-(2-((4-(4,4,5,5-tetramethyl-1,3,2-dioxaborolan-2-yl)benzofuran-6-yl)methoxy)phenyl)acetate (174a)

Compound 174a was prepared according to the procedure reported in step-1 of Scheme-59 from ethyl 2-(2-((4-(((trifluoromethyl)sulfonyl)oxy)benzofuran-6-yl)methoxy)phenyl)acetate (115d) (500 mg, 1.091 mmol), using bis(pinacolato)diboron (415 mg, 1.636 mmol), potassium acetate (321 mg, 3.27 mmol) and Pd(dppf)Cl$_2$—CH$_2$Cl$_2$ (134 mg, 0.164 mmol) in anhydrous dioxane (20 mL) under an Ar atmosphere and heating at 100° C. for 15 h. This gave after workup and purification by flash column chromatography [silica gel, 24g, eluting with hexanes/ethyl acetate (1:0 to 5:1)] ethyl 2-(2-((4-(4,4,5,5-tetramethyl-1,3,2-dioxaborolan-2-yl)benzofuran-6-yl)methoxy)phenyl)acetate (174a) (235 mg) as a colorless gum; MS (ES+): 459.4 (M+Na).

Step-2: Preparation of Ethyl 2-(2-((4-(2-(aminomethyl)-3-fluoropyridin-4-yl)benzofuran-6-yl)methoxy)phenyl)acetate (174b)

Compound 174b was prepared according to the procedure reported in step-3 of Scheme-1 from ethyl 2-(2-((4-(4,4,5,5-tetramethyl-1,3,2-dioxaborolan-2-yl)benzofuran-6-yl)methoxy)phenyl)acetate (174a) (220 mg, 0.504 mmol) in dioxane (4 mL) using (3-fluoro-4-iodopyridin-2-yl)methanamine (113a) (191 mg, 0.756 mmol), bis(triphenylphosphine)palladium(II) chloride (106 mg, 0.151 mmol) and a solution of K$_2$CO3 (209 mg, 1.513 mmol) in water (1 mL) under an Ar atmosphere and heating at 100° C. for 3 h on oil bath. This gave after workup, purification by flash column chromatography [silica (24 g), eluting with dichloromethane/methanol (1:0 to 9:1)] ethyl 2-(2-((4-(2-(aminomethyl)-3-fluoropyridin-4-yl)benzofuran-6-yl)methoxy)phenyl)acetate (174b) (51 mg) as a light brown gum; MS (ES+): 435.20 (M+1).

Step-3: Preparation of 2-(2-((4-(2-(aminomethyl)-3-fluoropyridin-4-yl)benzofuran-6-yl)methoxy)phenyl) acetic Acid (174c)

Compound 174c was prepared according to the procedure reported in step-6 of Scheme-1 from ethyl 2-(2-((4-(2-(aminomethyl)-3-fluoropyridin-4-yl)benzofuran-6-yl)methoxy)phenyl)acetate (174b) (48 mg, 0.110 mmol) THF/MeOH (3 mL each) using lithium hydroxide monohydrate (28 mg, 0.663 mmol) in water (3.0 mL). This gave after workup and purification by reverse phase column [C18 (50 g), eluting with ACN in water (containing 0.1% HCl) from 0-100%] 2-(2-((4-(2-(aminomethyl)-3-fluoropyridin-4-yl)benzofuran-6-yl)methoxy)phenyl)acetic acid (174c) (5 mg, 1.3% for three steps) HCl salt as a white solid. $^1$H NMR (300 MHz, DMSO-d$_6$) δ 8.60 (d, J=4.9 Hz, 1H), 8.50 (s, 3H), 8.16 (d, J=2.3 Hz, 1H), 7.87 (s, 1H), 7.71 (t, J=5.4 Hz, 1H), 7.56 (s, 1H), 7.28-7.19 (m, 2H), 7.08 (d, J=8.0 Hz, 1H), 6.99-6.95 (m, 1H), 6.94-6.87 (m, 1H), 5.32 (s, 2H), 4.43-4.32 (m, 2H), 3.60 (s, 2H); $^{19}$F NMR (282 MHz, DMSO-d$_6$) δ −128.89; MS (ES+): 407.2 (M+1); MS (ES−): 405.2 (M−1); HPLC purity: 92.60%.

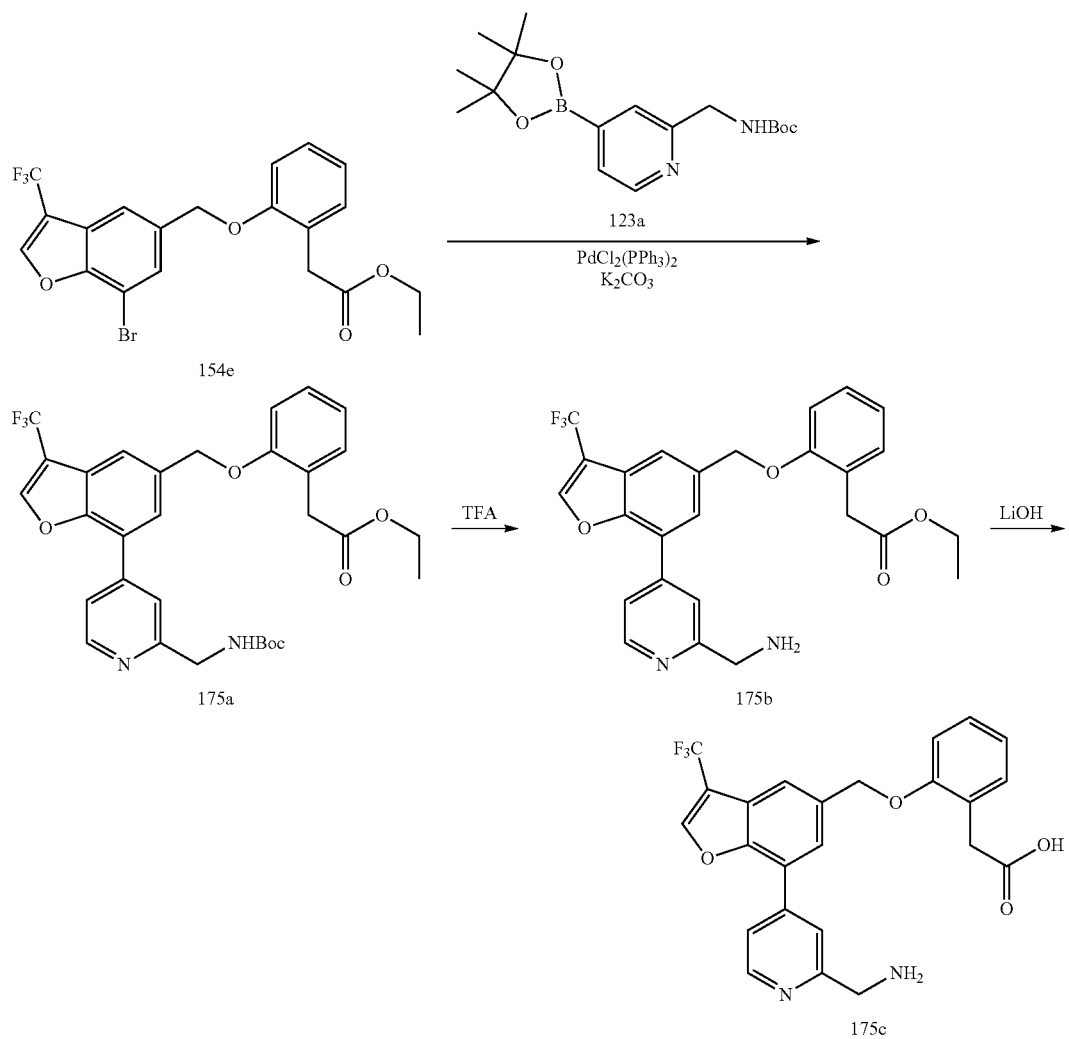

Preparation of 2-(2-((7-(2-(aminomethyl)pyridin-4-yl)-3-(trifluoromethyl)benzofuran-5-yl)methoxy)phenyl)acetic Acid (175c)

Step-1: Preparation of Ethyl 2-(2-((7-(2-(((tert-butoxycarbonyl)amino)methyl)pyridin-4-yl)-3-(trifluoromethyl)benzofuran-5-yl)methoxy)phenyl)acetate (175a)

Compound 175a was prepared according to the procedure reported in step-3 of Scheme-1 from ethyl 2-(2-((7-bromo-3-(trifluoromethyl)benzofuran-5-yl)methoxy)phenyl)acetate (154e) (229 mg, 0.501 mmol) in dioxane (5 mL) using tert-butyl (4-(4,4,5,5-tetramethyl-1,3,2-dioxaborolan-2-yl)pyridin-2-yl)methylcarbamate (123a) (380 mg, 1.137 mmol), K$_2$CO$_3$ (245 mg, 1.773 mmol) in water (0.5 mL), bis(triphenylphosphine)palladium(II) chloride (56 mg, 0.080 mmol) and heating under an nitrogen atmosphere at 100° C. for 3 h on an oil bath. This gave after workup, purification by flash column chromatography [silica (24 g), eluting with ethyl acetate in hexane from 20-100%] ethyl 2-(2-((7-(2-(((tert-butoxycarbonyl)amino)methyl)pyridin-4-yl)-3-(trifluoromethyl)benzofuran-5-yl)methoxy)phenyl)ac- etate (175a) (263 mg, 90% yield) as a pale-yellow oil. MS (ES+): 585.3 (M+1). Step-2: Preparation of ethyl 2-(2-((7-(2-(aminomethyl)pyridin-4-yl)-3-(trifluoromethyl)benzofuran-5-yl)methoxy)phenyl)acetate (175b)

Compound 175b was prepared according to the procedure reported in step-5 of Scheme-1 from ethyl 2-(2-((7-(2-(((tert-butoxycarbonyl)amino)methyl)pyridin-4-yl)-3-(trifluoromethyl)benzofuran-5-yl)methoxy)phenyl)acetate (175a) (263 mg, 0.450 mmol) in DCM (6 mL) using TFA (0.5 mL, 6.49 mmol). This gave after workup and purification by flash column chromatography [silica (24 g), eluting DMA/DCM (0-80%)] compound 175b (205 mg, 94% yield) free base as a white solid. An analytical sample was obtained by further purification using reverse phase column chromatography [C18 (50 g), eluting with ACN in water (containing 0.1% HCl) from 0-100%] to afford ethyl 2-(2-((7-(2-(aminomethyl)pyridin-4-yl)-3-(trifluoromethyl)benzofuran-5-yl)methoxy)phenyl)acetate (175b) HCl salt as a white solid. $^1$H NMR (300 MHz, DMSO-d$_6$) δ 9.00 (q, J=1.6 Hz, 1H), 8.83 (dd, J=5.3, 0.7 Hz, 1H), 8.68 (s, 3H), 8.18-8.09 (m, 1H), 8.06-7.83 (m, 3H), 7.36-7.18 (m, 2H), 7.13 (dd, J=8.3, 1.1 Hz, 1H), 6.93 (td, J=7.4, 1.1 Hz, 1H), 5.34 (s, 2H), 4.32 (q, J=5.8 Hz, 2H), 3.94 (q, J=7.1 Hz, 2H), 3.66 (s, 2H), 0.98 (t, J=7.1 Hz, 3H); MS (ES+): 485.2 (M+1).

Step-3: Preparation of 2-(2-((7-(2-(aminomethyl)pyridin-4-yl)-3-(trifluoromethyl)benzofuran-5-yl)methoxy)phenyl)acetic Acid (175c)

Compound 175c was prepared according to the procedure reported in step-6 of Scheme-1 from ethyl 2-(2-((7-(2-(aminomethyl)pyridin-4-yl)-3-(trifluoromethyl)benzofuran-5-yl)methoxy)phenyl)acetate (175b) (140 mg, 0.289 mmol) in THF/MeOH (6 mL each) using a solution of lithium hydroxide hydrate (81 mg, 3.38 mmol) in water (2 mL). This gave after workup and purification by reverse-phase column chromatography [C18 (50 g), eluting with ACN in water (containing 0.1% HCl) from 0-100%] 2-(2-((7-(2-(aminomethyl)pyridin-4-yl)-3-(trifluoromethyl)benzofuran-5-yl)methoxy)phenyl)acetic acid (175c) (71 mg, 54% yield) as a white solid. $^1$H NMR (300 MHz, DMSO-$d_6$) δ 8.99 (d, J=1.8 Hz, 1H), 8.82 (d, J=5.3 Hz, 1H), 8.65 (bs, 3H), 8.11 (d, J=1.6 Hz, 1H), 8.07-7.92 (m, 3H), 7.34-7.18 (m, 2H), 7.11 (d, J=8.0 Hz, 1H), 6.93 (t, J=7.4 Hz, 1H), 5.36 (s, 2H), 4.32 (d, J=5.5 Hz, 2H), 3.62 (s, 2H); MS (ES+): 457.2 (M+1); MS(ES−): 455.3 (M−1). HPLC purity 97.6%.

Scheme-176

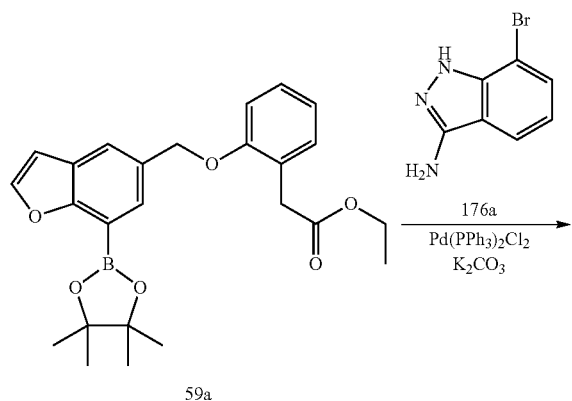

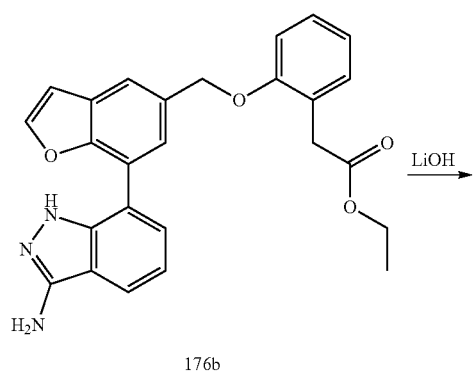

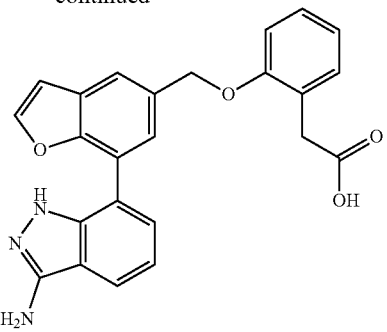

176c

Preparation of 2-(2-((7-(3-amino-1H-indazol-7-yl)benzofuran-5-yl)methoxy)phenyl)acetic Acid (176c)

Step-1: Preparation of Ethyl 2-(2-((7-(3-amino-1H-indazol-7-yl)benzofuran-5-yl)methoxy)phenyl)acetate (176b)

Compound 176b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (241 mg, 0.552 mmol) in dioxane (5 mL) using 7-bromo-1H-indazol-3-amine (176a) (160 mg, 0.755 mmol; CAS #1234616-28-4), bis(triphenylphosphine)palladium(II) chloride (72 mg, 0.103 mmol) and a solution of $K_2CO_3$ (355 mg, 2.57 mmol) in water (0.5 mL) under an Ar atmosphere and heating at 100° C. for 3 h on oil bath. This gave after workup, purification by flash column chromatography [silica (24 g), eluting with ethyl acetate in hexane from 40-100%] compound 176b (209 mg, 86% yield) free base as a pale-yellow oil. An analytical sample was prepared by purification using reverse phase column chromatography [C18 (50 g), eluting with ACN in water (containing 0.1% HCl) from 0-100%] to afford ethyl 2-(2-((7-(3-amino-1H-indazol-7-yl)benzofuran-5-yl)methoxy)phenyl)acetate (176b) HCl salt as white solid. $^1$H NMR (300 MHz, DMSO-$d_6$) δ 12.91 (s, 1H), 8.12 (d, J=8.2 Hz, 1H), 8.06 (d, J=2.2 Hz, 1H), 7.90-7.73 (m, 2H), 7.67-7.57 (m, 1H), 7.35 (t, J=7.7 Hz, 1H), 7.31-7.19 (m, 2H), 7.15 (d, J=8.2 Hz, 1H), 7.08 (d, J=2.2 Hz, 1H), 6.91 (t, J=7.3 Hz, 1H), 5.29 (s, 2H), 3.85 (q, J=7.1 Hz, 2H), 3.63 (s, 2H), 0.93 (t, J=7.1 Hz, 3H); MS (ES+): 442.2 (M+1); MS (ES−): 440.3 (M−1).

Step-2: Preparation of 2-(2-((7-(3-amino-1H-indazol-7-yl)benzofuran-5-yl)methoxy)phenyl)acetic Acid (176c)

Compound 176c was prepared according to the procedure reported in step-6 of Scheme-1 from ethyl 2-(2-((7-(3-amino-1H-indazol-7-yl)benzofuran-5-yl)methoxy)phenyl)acetate (176b) (159 mg, 0.360 mmol) in MeOH/THF (6 mL each) using a solution of lithium hydroxide monohydrate (92 mg, 2.19 mmol) in water (2 mL). This gave after workup and purification by reverse phase column [C18 (50 g), eluting with ACN in water (containing 0.1% HCl) from 0-100%] 2-(2-((7-(3-amino-1H-indazol-7-yl)benzofuran-5-yl)methoxy)phenyl)acetic acid (176c) (79 mg, 53% yield) as a white solid. $^1$H NMR (300 MHz, DMSO-$d_6$) δ 12.66 (s, 2H), 8.06-7.92 (m, 2H), 7.76 (s, 1H), 7.67 (d, J=7.1 Hz, 1H), 7.57

(s, 1H), 7.35-7.10 (m, 3H), 7.05 (d, J=8.2 Hz, 1H), 6.99 (d, J=2.2 Hz, 1H), 6.84 (t, J=7.4 Hz, 1H), 5.24 (s, 2H), 3.53 (s, 2H); MS (ES+): 414.2 (M+1); MS(ES−): 412.2 (M−1).

Scheme-177

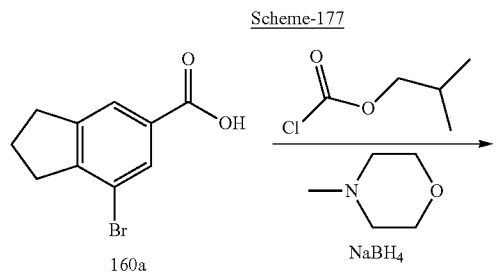

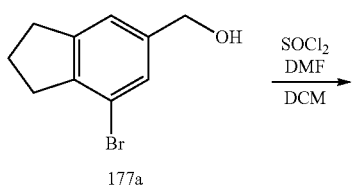

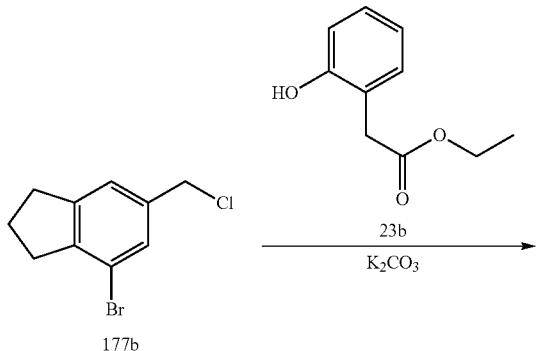

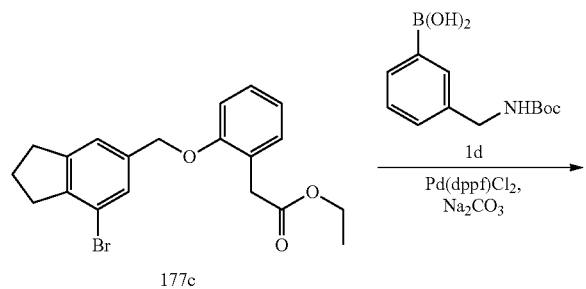

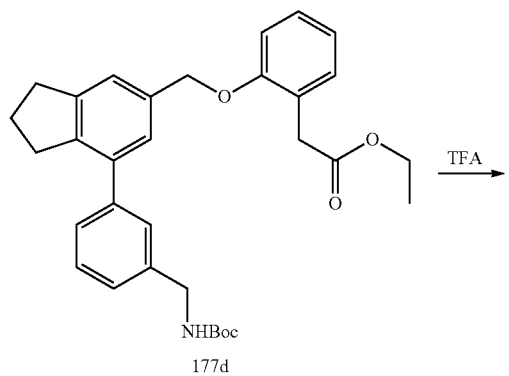

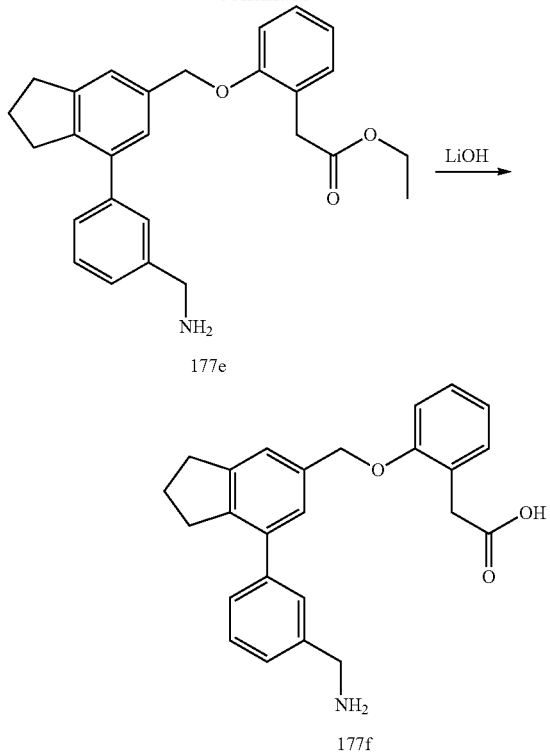

Preparation of 2-(2-((7-(3-(aminomethyl)phenyl)-2,3-dihydro-1H-inden-5-yl)methoxy)phenyl)acetic Acid (177f)

Step-1: Preparation of (7-bromo-2,3-dihydro-1H-inden-5-yl)methanol (177a)

Compound 177a was prepared according to the procedure reported in step-1 of Scheme-23 from 7-bromo-2,3-dihydro-1H-indene-5-carboxylic acid (160a) ((5.0 g, 20.74 mmol) using N-methylmorpholine ((2.30 g, 22.81 mmol) in THF (50 mL), isobutyl chloroformate (3.11 g, 22.81 mmol) and NaBH$_4$ (1.17 g, 31.11 mmol) in water (6.5 mL). This gave after workup and purification by flash column chromatography [silica gel, eluting with 0-30% ethyl acetate in n-hexane] (7-bromo-2,3-dihydro-1H-inden-5-yl)methanol (177a) (1.9 g, 42%) as an off white solid; $^1$H NMR (300 MHz, DMSO-d$_6$) δ 7.26 (s, 1H), 7.14 (s, 1H), 5.26 (t, J=5.7 Hz, 1H), 4.44 (d, J=5.1 Hz, 2H), 2.95 (t, J=7.5 Hz, 2H), 2.83 (t, J=7.4 Hz, 2H), 2.10-1.96 (m, 2H).

Step-2: Preparation of 4-bromo-6-(chloromethyl)-2,3-dihydro-1H-indene (177b)

To a stirred solution of (7-bromo-2,3-dihydro-1H-inden-5-yl)methanol (177a) (2.0 g, 8.80 mmol) in DCM (40.0 mL) was added at 0° C. thionyl chloride (3.1 g, 26.42 mmol), a drop of DMF and stirred for 2 h at room temperature. The reaction mixture was concentrated under vacuum to afford 4-bromo-6-(chloromethyl)-2,3-dihydro-1H-indene (177b) (1.93 g, 89%) as a colorless oil.

Step-3: Preparation of Ethyl 2-(2-((7-bromo-2,3-dihydro-1H-inden-5-yl)methoxy)phenyl)acetate (177c)

To a stirred solution of 4-bromo-6-(chloromethyl)-2,3-dihydro-1H-indene (177b) (crude from above step, 1.9 g, 7.73 mmol) in DMF (19.0 mL) was added at room temperature potassium carbonate (5.3 g, 38.69 mmol) and ethyl 2-(2-hydroxyphenyl)acetate (23b) (2.0 g, 11.59 mmol), stirred for 14 h and quenched with water (100 mL). The reaction mixture was extracted with ethyl acetate (2×200.0 mL) and the combined organic extracts was washed with brine (100 mL), dried, filtered and concentrated under vacuum. The residue obtained was purified by flash column chromatography eluting with 0-20% ethyl acetate in n-hexane to obtain ethyl 2-(2-((7-bromo-2,3-dihydro-1H-inden-5-yl)methoxy)phenyl)acetate (177c) (1.4 g, 49.12%) as an oil; $^1$H NMR (300 MHz, DMSO-$d_6$) δ 7.37 (s, 1H), 7.24 (m, 3H), 7.02 (d, J=8.1 Hz, 1H), 6.91 (t, J=7.4 Hz, 1H), 5.04 (s, 2H), 4.03 (m, 2H), 3.57 (s, 2H), 2.98 (m, 2H), 2.85 (t, J=7.5 Hz, 2H), 2.04 (p, J=7.7 Hz, 2H), 1.12 (t, J=7.1 Hz, 3H).

Step-4: Preparation of Ethyl 2-(2-((7-(3-(((tert-butoxycarbonyl)amino)methyl)phenyl)-2,3-dihydro-1H-inden-5-yl)methoxy)phenyl)acetate (177d)

Compound 177d was prepared according to the procedure reported in step-3 of Scheme-1 from ethyl 2-(2-((7-bromo-2,3-dihydro-1H-inden-5-yl)methoxy)phenyl)acetate (177c) (0.5 g, 1.28 mmol) in acetonitrile (14 mL), dioxane (6 mL) using (3-(((tert-butoxycarbonyl)amino)methyl)phenyl)boronic acid (Id) (0.48 g, 1.92 mmol), Na$_2$CO$_3$ (0.40 g, 3.85 mmol) and Pd(dppf)Cl$_2$ (0.10 g, 0.12 mmol) under a nitrogen atmosphere and heating at 90° C. for 14 h in an oil bath. This gave after workup, purification by flash column chromatography [silica gel, eluting with 0-20% EtOAc in n-hexane] ethyl 2-(2-((7-(3-(((tert-butoxycarbonyl)amino)methyl)phenyl)-2,3-dihydro-1H-inden-5-yl)methoxy)phenyl)acetate (177d) (0.13 g, 20%) as an colorless liquid; $^1$H NMR (300 MHz, DMSO-$d_6$) δ 7.45 (m, 1H), 7.35 (m, 2H), 7.29-7.17 (m, 6H), 7.07 (d, J=8.1 Hz, 1H), 6.90 (t, J=7.4 Hz, 1H), 5.09 (s, 2H), 4.18 (d, J=6.2 Hz, 2H), 3.92 (q, J=7.1 Hz, 2H), 3.60 (s, 2H), 3.03-2.82 (m, 4H), 2.00 (t, J=7.3 Hz, 2H), 1.39 (s, 9H), 1.03 (t, J=7.0 Hz, 3H).

Step-5: Preparation of Ethyl 2-(2-((7-(3-(aminomethyl)phenyl)-2,3-dihydro-1H-inden-5-yl)methoxy)phenyl)acetate (177e)

Compound 177e was prepared according to the procedure reported in step-5 of Scheme-1 from ethyl 2-(2-((7-(3-(((tert-butoxycarbonyl)amino)methyl)phenyl)-2,3-dihydro-1H-inden-5-yl)methoxy)phenyl)acetate (177d) (0.1 g, 0.194 mmol) in DCM (7 mL) using TFA (0.223 mL, 2.91 mmol). This gave after workup ethyl 2-(2-((7-(3-(aminomethyl)phenyl)-2,3-dihydro-1H-inden-5-yl)methoxy)phenyl)acetate (177e) (0.103 g, 100% yield) TFA salt as a solid; MS (ES+): 416.3 (M+1).

Step-6: Preparation of 2-(2-((7-(3-(aminomethyl)phenyl)-2,3-dihydro-1H-inden-5-yl)methoxy)phenyl)acetic Acid (177f)

Compound 177f was prepared according to the procedure reported in step-6 of Scheme-1 from ethyl 2-(2-((7-(3-(aminomethyl)phenyl)-2,3-dihydro-1H-inden-5-yl)methoxy)phenyl)acetate (177e) (0.194 mmol) in THF/methanol (3:1 mL) using lithium hydroxide hydrate (163 mg, 3.88 mmol) in water (3.9 mL, 1 N). This gave after workup and purification by reverse phase column chromatography [C-18 column, 30 g, eluting with 0.1% aq. HCl in water and acetonitrile from 0-100%] and [C18 (12 g), eluting with ACN in water (containing 0.1% HCl) from 0-60%] 2-(2-((7-(3-(aminomethyl)phenyl)-2,3-dihydro-1H-inden-5-yl)methoxy)phenyl)acetic acid (177f) (1 mg, 1.2% yield) HCl salt as a white solid; $^1$H NMR (300 MHz, DMSO-$d_6$) δ 7.61 (s, 1H), 7.53-7.49 (m, 2H), 7.48-7.41 (m, 1H), 7.34 (s, 1H), 7.28 (s, 1H), 7.26-7.18 (m, 2H), 7.04 (d, J=8.1 Hz, 1H), 6.89 (t, J=7.2 Hz, 1H), 5.13 (s, 2H), 4.10 (s, 2H), 3.56 (s, 2H), 2.93 (t, J=7.2 Hz, 4H), 2.01 (t, J=7.3 Hz, 2H); MS (ES+): 388.2 (M+1); (ES−): 386.30 (M−1).

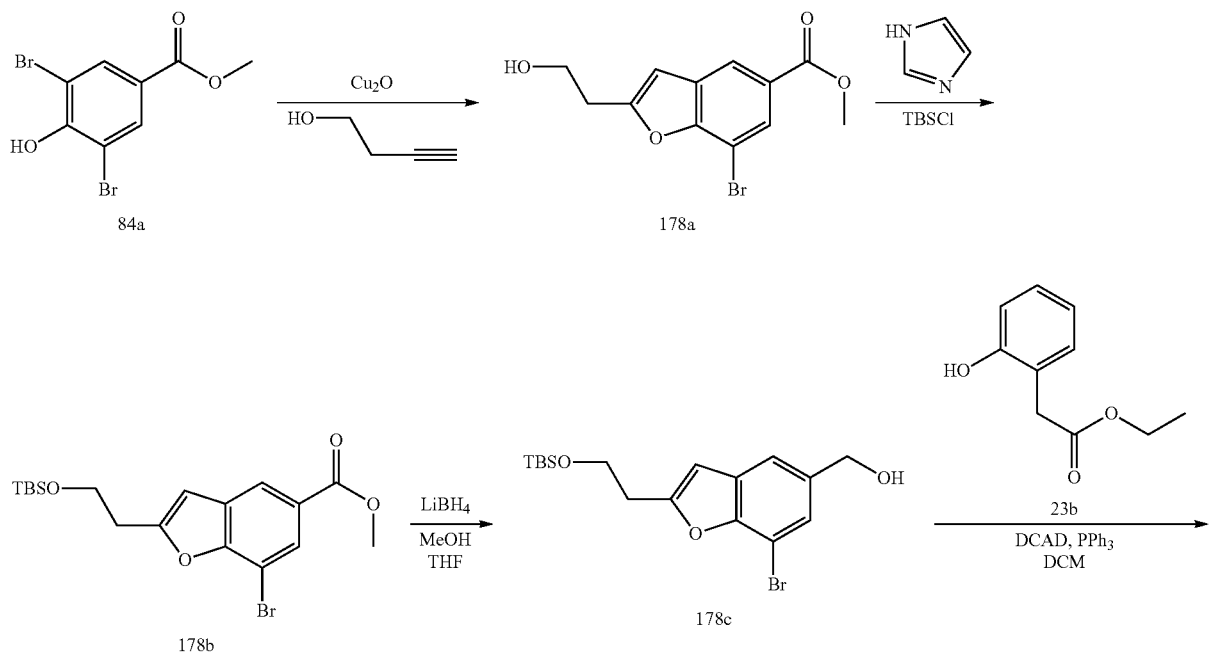

Scheme-178

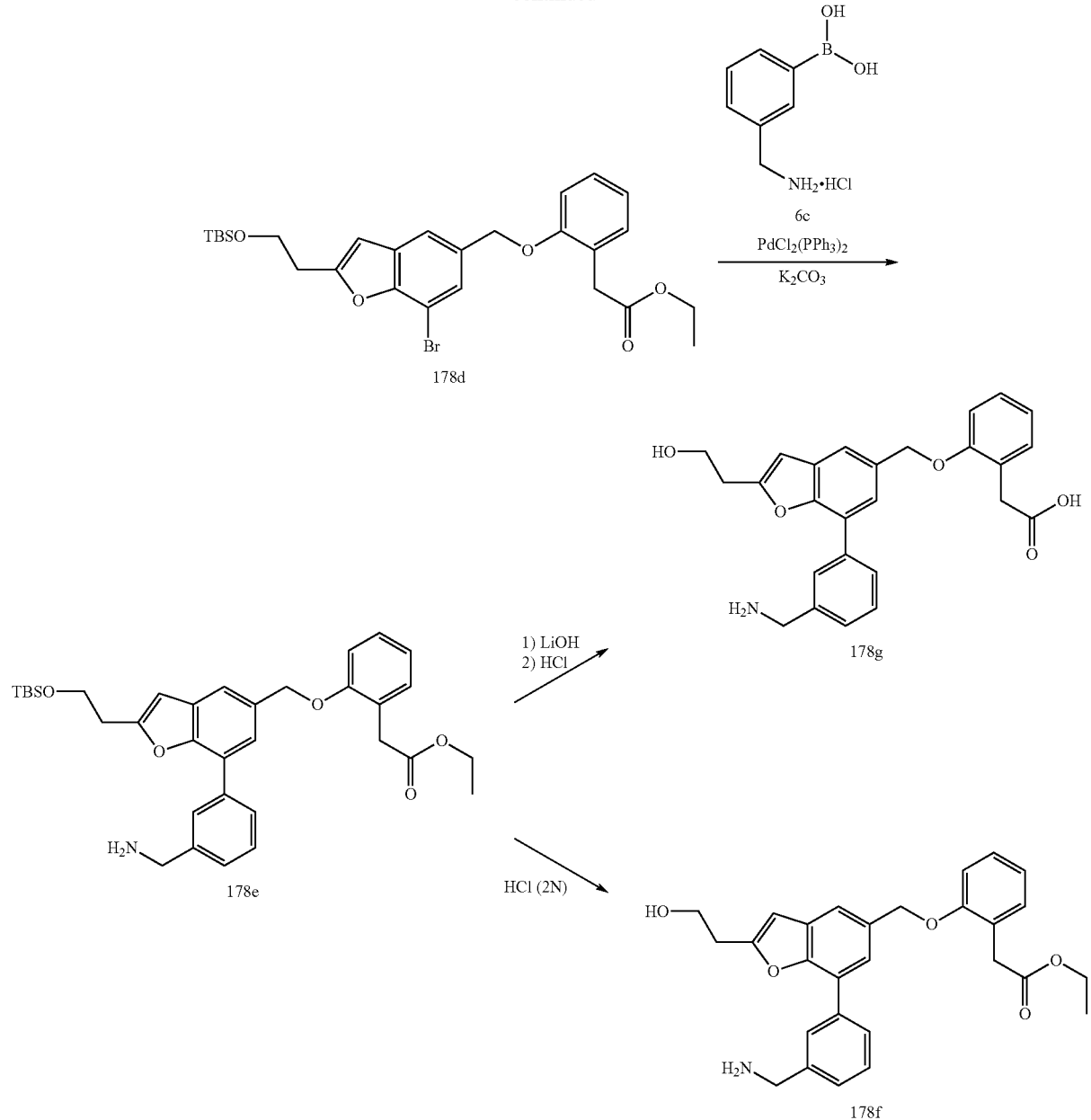

Preparation of 2-(2-((7-(3-(aminomethyl)phenyl)-2-(2-hydroxyethyl)benzofuran-5-yl)methoxy)phenyl) acetic Acid (178g)

Step-1: Preparation of methyl 7-bromo-2-(2-hydroxyethyl)benzofuran-5-carboxylate (178a)

Compound 178a was prepared according to the procedure reported in step-1 of Scheme-55, from methyl 3,5-dibromo-4-hydroxybenzoate (84a) (15 g, 48.4 mmol) in pyridine (500 mL) using but-3-yn-1-ol (3.39 g, 48.4 mmol) and copper(I) oxide (3.46 g, 24.20 mmol). This gave after workup and purification by flash column chromatography [silica (80 g), eluting with EtOAc in hexane from 0-80%] methyl 7-bromo-2-(2-hydroxyethyl)benzofuran-5-carboxylate (178a) (8.1 g, 56% yield) as a white solid; $^1$H NMR (300 MHz, DMSO-$d_6$) δ 8.21 (d, J=1.6 Hz, 1H), 7.99 (d, J=1.6 Hz, 1H), 6.94-6.90 (m, 1H), 4.95-4.82 (m, 1H, $D_2O$ exchangeable), 3.88 (s, 3H), 3.78 (t, J=6.5 Hz, 2H), 2.99 (td, J=6.4, 1.0 Hz, 2H); MS (ES+): 299.0 (M+1).

Step-2: Preparation of methyl 7-bromo-2-(2-((tert-butyldimethylsilyl)oxy)ethyl)benzofuran-5-carboxylate (178b)

To a solution of methyl 7-bromo-2-(2-hydroxyethyl)benzofuran-5-carboxylate (178a) (6 g, 20.06 mmol) and imidazole (1.37 g, 20.06 mmol) in anhydrous DCM (120 mL) at 0° C. was added TBS-Cl (3.02 g, 20.06 mmol). The mixture was stirred at 0° C. for 2 hours and overnight at RT. The reaction was diluted with DCM and water. The aqueous layer was separated and extracted with DCM (2×). The combined organic layers were washed with water and brine, dried, filtered and concentrated in vacuum. The residue obtained was purified by flash column chromatography [silica (80 g), eluting with EtOAc in hexane from 0-50%] to give methyl 7-bromo-2-(2-((tert-butyldimethylsilyl)oxy) ethyl)benzofuran-5-carboxylate (178b) (7.5 g, 90% yield) as a clear oil; $^1$H NMR (300 MHz, DMSO-d$_6$) δ 8.19 (d, J=1.6 Hz, 1H), 7.96 (d, J=1.5 Hz, 1H), 6.93-6.86 (m, 1H), 3.94 (t, J=6.1 Hz, 2H), 3.86 (s, 3H), 3.02 (t, J=6.1 Hz, 2H), 0.77 (s, 9H), −0.05 (s, 6H).

Step-3: Preparation of (7-bromo-2-(2-((tert-butyldimethylsilyl)oxy)ethyl)benzofuran-5-yl)methanol (178c)

Compound 178c was prepared according to the procedure reported in step-2 of Scheme-76 from methyl 7-bromo-2-(2-((tert-butyldimethylsilyl)oxy)ethyl)benzofuran-5-carboxylate (178b) (7.32 g, 17.71 mmol) in THF (60 mL) using LiBH$_4$ (17.71 mL, 53.1 mmol, 3 M solution in THF) and MeOH (2.2 mL, 53.1 mmol). This gave after workup and purification by flash column chromatography [silica (40 g), eluting with EtOAc in hexane from 0-60%] (7-bromo-2-(2-((tert-butyldimethylsilyl)oxy)ethyl)benzofuran-5-yl)methanol (178c) (6.36 g, 93% yield) as a clear oil; $^1$H NMR (300 MHz, DMSO-d$_6$) δ 7.49-7.45 (m, 1H), 7.40-7.37 (m, 1H), 6.75-6.71 (m, 1H), 5.29 (t, J=5.8 Hz, 1H, D$_2$O exchangeable), 4.54 (d, J=5.8 Hz, 2H), 3.94 (t, J=6.1 Hz, 2H), 2.98 (t, J=6.1 Hz, 2H), 0.79 (s, 9H), −0.04 (s, 6H); MS (ES+) 387.1 (M+1).

Step-4: Preparation of Ethyl 2-(2-((7-bromo-2-(2-((tert-butyldimethylsilyl)oxy)ethyl)benzofuran-5-yl) methoxy)phenyl)acetate (178d)

Compound 178d was prepared according to the procedure reported in step-2 of Scheme-23 from (7-bromo-2-(2-((tert-butyldimethylsilyl)oxy)ethyl)benzofuran-5-yl)methanol (178c) (6.11 g, 15.85 mmol) in DCM (100 mL) using triphenylphosphine (4.16 g, 15.85 mmol), ethyl 2-(2-hydroxyphenyl) acetate (23b) (2.86 g, 15.85 mmol) and di-(4-chlorobenzyl)azodicarboxylate (DCAD, 5.82 g, 15.85 mmol) in DCM (20 mL). This gave after workup and purification by flash column chromatography [silica (40 g), eluting with EtOAc in hexane from 0-20%] ethyl 2-(2-((7-bromo-2-(2-((tert-butyldimethyl silyl)oxy)ethyl)benzofuran-5-yl)methoxy)phenyl)acetate (178d) (6.5 g, 75% yield) as a clear oil; $^1$H NMR (300 MHz, DMSO-d$_6$) δ 7.63 (s, 1H), 7.53 (s, 1H), 7.32-7.22 (m, 2H), 7.10 (d, J=8.1 Hz, 1H), 6.94 (t, J=7.4 Hz, 1H), 6.81 (s, 1H), 5.18 (s, 2H), 4.12-3.90 (m, 4H), 3.65 (s, 2H), 3.03 (t, J=6.1 Hz, 2H), 1.11 (t, J=7.0 Hz, 3H), 0.83 (d, J=0.9 Hz, 9H), 0.00 (s, 6H);

Step-5: Preparation of Ethyl 2-(2-((7-(3-(aminomethyl)phenyl)-2-(2-((tert-butyldimethyl silyl)oxy) ethyl)benzofuran-5-yl)methoxy)phenyl)acetate (178e)

Compound 178e was prepared according to the procedure reported in step-3 of Scheme-1 from ethyl 2-(2-((7-bromo-2-(2-((tert-butyldimethyl silyl)oxy)ethyl)benzofuran-5-yl) methoxy)phenyl)acetate (178d) (650 mg, 1.19 mmol) in dioxane (20 mL) using 3-(aminomethyl)phenylboronic acid hydrochloride (6c) (334 mg, 1.78 mmol), a solution of K$_2$CO$_3$ (492 mg, 3.56 mmol) in water (3 mL), bis(triphenylphosphine)palladium(II) chloride (125 mg, 0.18 mmol) and heating at 100° C. for 3h on oil bath. This gave after workup, purification by flash column chromatography [silica (24 g), eluting with DMA80 in DCM from 0-70%] ethyl 2-(2-((7-(3-(aminomethyl)phenyl)-2-(2-((tert-butyldimethylsilyl)oxy)ethyl)benzofuran-5-yl)methoxy)phenyl)acetate (178e) (441 mg, 65% yield) as a clear oil; MS (ES+): 574.3 (M+1).

Step-6: Preparation of Ethyl 2-(2-((7-(3-(aminomethyl)phenyl)-2-(2-hydroxyethyl)benzofuran-5-yl) methoxy)phenyl)acetate (178f)

To a solution of ethyl 2-(2-((7-(3-(aminomethyl)phenyl)-2-(2-((tert-butyldimethylsilyl)oxy)ethyl)benzofuran-5-yl) methoxy)phenyl)acetate (178e) (200 mg, 0.349 mmol) in THF (10 mL) was added HCl (2N, 1.5 mL), stirred at RT for 3h and concentrated in vacuum. The residue was taken up with EtOAc and washed with water and brine. The organic layer was dried, filtered and concentrated in vacuum. The residue obtained was purified by flash column chromatography [silica (24 g), eluting with DMA80 in DCM from 0-70%] followed by further purification by reverse phase column chromatography [C18 (50 g), eluting with ACN in water (containing 0.1% HCl) from 0-100%] to give ethyl 2-(2-((7-(3-(aminomethyl)phenyl)-2-(2-hydroxyethyl)benzofuran-5-yl)methoxy)phenyl)acetate (178f) (114 mg, 65% yield) HCl salt as a white solid; $^1$H NMR (300 MHz, DMSO-d$_6$) δ 8.49 (s, 3H, D$_2$O exchangeable), 7.98 (t, J=1.6 Hz, 1H), 7.91 (dt, J=7.1, 1.9 Hz, 1H), 7.65-7.48 (m, 4H), 7.31-7.18 (m, 2H), 7.14-7.05 (m, 1H), 6.91 (td, J=7.4, 1.1 Hz, 1H), 6.72 (s, 1H), 5.22 (s, 2H), 4.89 (t, J=5.4 Hz, 1H, D$_2$O exchangeable), 4.12 (s, 2H), 3.94 (q, J=7.1 Hz, 2H), 3.84-3.71 (m, 2H), 3.63 (s, 2H), 2.96 (t, J=6.6 Hz, 2H), 1.01 (t, J=7.1 Hz, 3H); MS (ES+): 460.3 (M+1).

Step-7: Preparation of 2-(2-((7-(3-(aminomethyl) phenyl)-2-(2-hydroxyethyl)benzofuran-5-yl) methoxy)phenyl)acetic Acid (178g)

To a solution of ethyl 2-(2-((7-(3-(aminomethyl)phenyl)-2-(2-((tert-butyldimethylsilyl)oxy)ethyl)benzofuran-5-yl) methoxy)phenyl)acetate (178e) (212 mg, 0.369 mmol) in MeOH/THF (6 mL each) was added lithium hydroxide monohydrate (20 mg, 0.480 mmol) in water (2.0 mL). The resulting mixture was stirred at RT for 12h and was acidified to PH~4. The residue obtained was purified by reverse phase column chromatography [C18 (50 g), eluting with ACN in water (containing 0.1% HCl) from 0-100%] to give 2-(2-((7-(3-(aminomethyl)phenyl)-2-(2-hydroxyethyl)benzofuran-5-yl)methoxy)phenyl)acetic acid (178g) (120 mg, 75% yield) as a white solid; $^1$H NMR (300 MHz, DMSO-d$_6$) δ 12.25 (s, 1H, D$_2$O exchangeable), 8.48 (s, 3H, D$_2$O exchangeable), 8.01-7.96 (m, 1H), 7.93 (dt, J=7.2, 1.8 Hz, 1H), 7.66-7.60 (m, 1H), 7.60-7.52 (m, 3H), 7.27-7.18 (m, 2H), 7.08 (d, J=8.1 Hz, 1H), 6.90 (td, J=7.4, 1.1 Hz, 1H), 6.72 (s, 1H), 5.24 (s, 2H), 4.88 (t, J=5.4 Hz, 1H), 4.13 (s, 2H), 3.78 (q, J=6.1 Hz, 2H), 3.59 (s, 2H), 2.96 (t, J=6.6 Hz, 2H); MS (ES+): 432.2 (M+1); (ES−): 430.3 (M−1).

Scheme-179

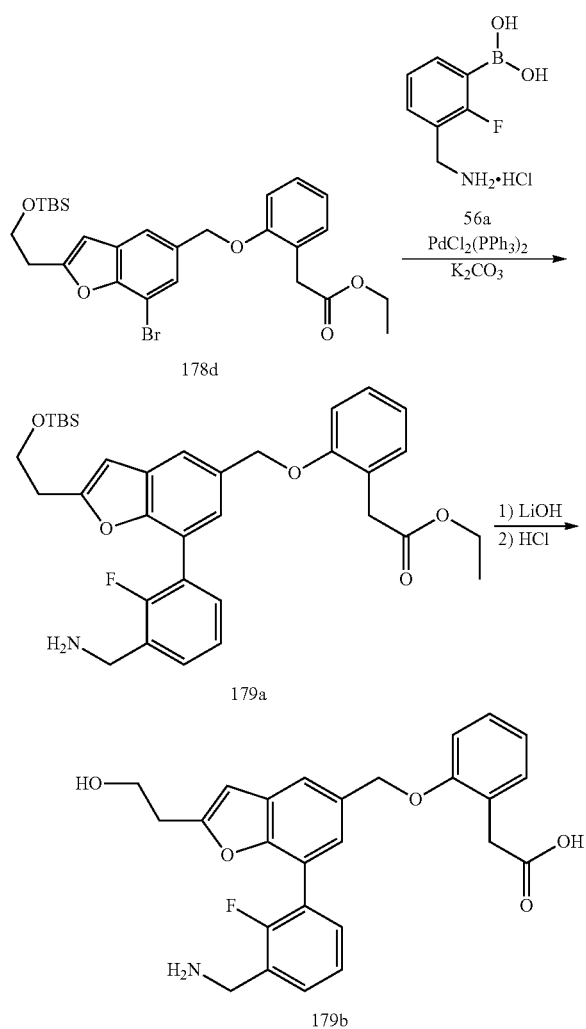

Preparation of 2-(2-((7-(3-(aminomethyl)-2-fluoro-phenyl)-2-(2-hydroxyethyl)benzofuran-5-yl)methoxy)phenyl)acetic Acid (179b)

Step-1: Preparation of Ethyl 2-(2-((7-(3-(aminomethyl)-2-fluorophenyl)-2-(2-((tert-butyldimethylsilyl)oxy)ethyl)benzofuran-5-yl)methoxy)phenyl)acetate (179a)

Compound 179a was prepared according to the procedure reported in step-3 of Scheme-1 from ethyl 2-(2-((7-bromo-2-(2-((tert-butyldimethylsilyl)oxy)ethyl)benzofuran-5-yl)methoxy)phenyl)acetate (178d) (225 mg, 1.10 mmol) in dioxane (5 mL) using 3-(aminomethyl)-2-fluorophenylboronic acid hydrochloride (56a) (225 mg, 1.10 mmol), a solution of $K_2CO_3$ (303 mg, 2.19 mmol) in water (1 mL), bis(triphenylphosphine)palladium(II) chloride (103 mg, 0.15 mmol) and heating at 100° C. for 3h on oil bath. This gave after workup, purification by flash column chromatography [silica (24 g), eluting with DMA80 in DCM from 0-70%] followed by further purification using reverse phase column chromatography [C18 (50 g), eluting with ACN in water (containing 0.1% HCl) from 0-100%] ethyl 2-(2-((7-(3-(aminomethyl)-2-fluorophenyl)-2-(2-((tert-butyldimethylsilyl)oxy)ethyl)benzofuran-5-yl)methoxy)phenyl)acetate (179a) (330 mg, 76% yield) as a white solid; $^1$H NMR (300 MHz, DMSO-$d_6$) δ 7.70-7.58 (m, 3H), 7.48 (td, J=7.4, 1.8 Hz, 1H), 7.38-7.32 (m, 2H), 7.32-7.23 (m, 2H), 7.18-7.12 (m, 1H), 6.95 (td, J=7.4, 1.1 Hz, 1H), 5.24 (s, 2H), 3.98-3.90 (m, 4H), 3.87 (s, 2H), 3.65 (s, 2H), 2.98 (t, J=6.2 Hz, 2H), 1.03 (t, J=7.1 Hz, 3H), 0.83 (s, 9H), 0.00 (s, 6H); $^{19}$F NMR (282 MHz, DMSO-$d_6$) δ−121.84; MS (ES+): 592.4 (M+1).

Step-2: Preparation of 2-(2-((7-(3-(aminomethyl)-2-fluorophenyl)-2-(2-hydroxyethyl)benzofuran-5-yl)methoxy)phenyl)acetic Acid (179b)

Compound 179b was prepared according to the procedure reported in step-7 of Scheme-178 from ethyl 2-(2-((7-(3-(aminomethyl)-2-fluorophenyl)-2-(2-((tert-butyldimethylsilyl)oxy)ethyl)benzofuran-5-yl)methoxy)phenyl)acetate (179a) (175 mg, 0.30 mmol) in MeOH/THF (6 mL each) using lithium hydroxide monohydrate (50 mg, 1.18 mmol) in water (2.0 mL). This gave after workup, purification by reverse phase column chromatography [C18 (50 g), eluting with ACN in water (containing 0.1% HCl) from 0-100%] 2-(2-((7-(3-(aminomethyl)-2-fluorophenyl)-2-(2-hydroxyethyl)benzofuran-5-yl)methoxy)phenyl)acetic acid (179b) (80 mg, 60% yield) as a white solid; $^1$H NMR (300 MHz, DMSO-$d_6$) δ 12.12 (s, 1H, $D_2O$ exchangeable), 8.54 (s, 2H, $D_2O$ exchangeable), 7.74-7.62 (m, 3H), 7.42 (t, J=7.7 Hz, 1H), 7.39-7.33 (m, 1H), 7.27-7.16 (m, 2H), 7.08 (d, J=7.9 Hz, 1H), 6.89 (td, J=7.4, 1.1 Hz, 1H), 6.76-6.67 (m, 1H), 5.23 (s, 2H), 4.85 (t, J=5.4 Hz, 1H, $D_2O$ exchangeable), 4.17 (s, 2H), 3.72 (q, J=6.3 Hz, 2H), 3.57 (s, 2H), 2.95-2.82 (m, 2H); $^{19}$F NMR (282 MHz, DMSO-$d_6$) δ−118.65; MS (ES+): 450.2 (M+1); (ES−): 448.3 (M−1).

Scheme-180

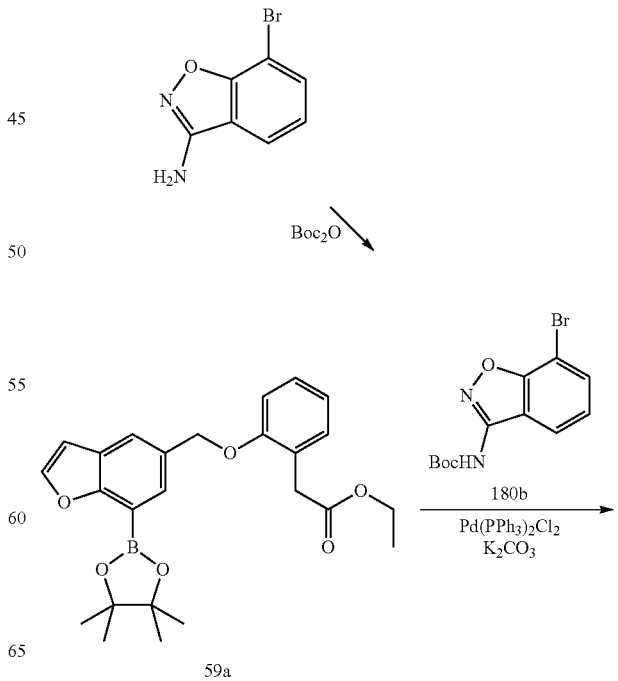

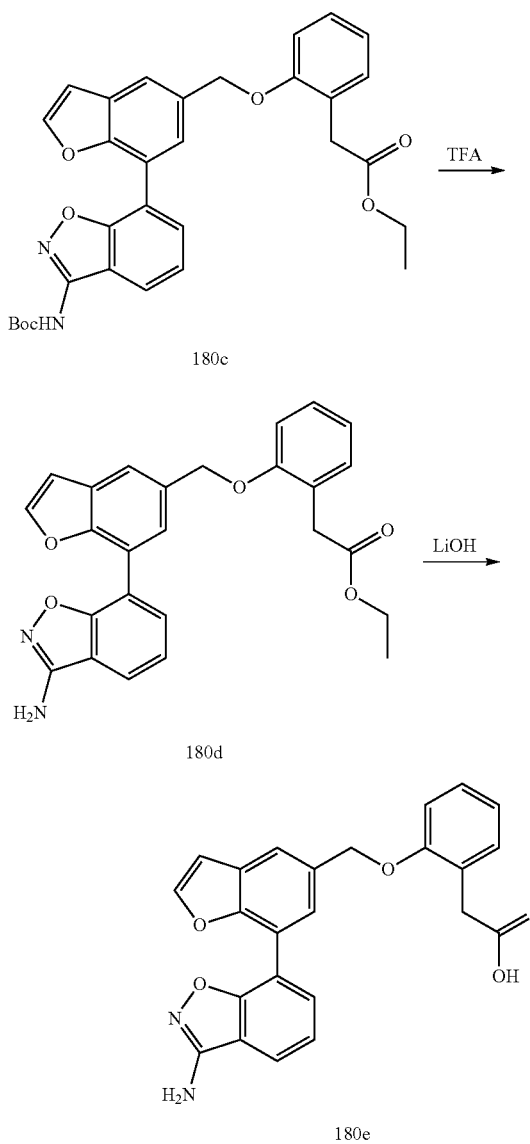

Preparation of 2-(2-((7-(3-aminobenzo[d]isoxazol-7-yl)benzofuran-5-yl)methoxy)phenyl)acetic Acid (180e)

Step-1: Preparation of tert-butyl (7-bromobenzo[d]isoxazol-3-yl)carbamate (180b)

A mixture of 7-bromobenzo[d]isoxazol-3-amine (90 mg, 0.422 mmol; CAS #1260860-32-9), Boc$_2$O (0.298 mL, 1.283 mmol), DMAP (17 mg, 0.139 mmol) in THF (3 mL) was stirred at room temperature overnight. Solvent was removed under vacuum and residue obtained was purified by flash column chromatography [silica (12 g), eluting with EtOAc in hexane from 0-25%] to give tert-butyl (7-bromobenzo[d]isoxazol-3-yl)carbamate (180b) (132 mg, 100% yield) as a white solid. $^1$H NMR (300 MHz, DMSO-d$_6$) δ 8.06 (dd, J=8.1, 1.0 Hz, 1H), 7.90 (dd, J=8.1, 1.0 Hz, 1H), 7.35-7.26 (m, 1H), 1.51 (s, 9H).

Step-2: Preparation of Ethyl 2-(2-((7-(3-((tert-butoxycarbonyl)amino)benzo[d]isoxazol-7-yl)benzofuran-5-yl)methoxy)phenyl)acetate (180c)

Compound 180c was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (153 mg, 0.351 mmol) in dioxane (5 mL) using tert-butyl (7-bromobenzo[d]isoxazol-3-yl)carbamate (180b) (130 mg, 0.415 mmol), bis(triphenylphosphine)palladium(II) chloride (41 mg, 0.058 mmol) and a solution of K$_2$CO$_3$ (162 mg, 1.172 mmol) in water (0.5 mL) under an Ar atmosphere and heating at 100° C. for 3 h on oil bath. This gave after workup and purification by flash column chromatography [silica (12 g), eluting with ethyl acetate in hexane from 0-50%] ethyl 2-(2-((7-(3-((tert-butoxycarbonyl)amino)benzo[d]isoxazol-7-yl)benzofuran-5-yl)methoxy)phenyl)acetate (180c) (168 mg, 0.310 mmol, 88% yield) as pale-yellow oil; MS (ES+): 543.2 (M+1).

Step-3: Preparation of Ethyl 2-(2-((7-(3-aminobenzo[d]isoxazol-7-yl)benzofuran-5-yl)methoxy)phenyl)acetate (180d)

Compound 180d was prepared according to the procedure reported in step-5 of Scheme-1 from ethyl 2-(2-((7-(3-((tert-butoxycarbonyl)amino)benzo[d]isoxazol-7-yl)benzofuran-5-yl)methoxy)phenyl)acetate (180c) (168 mg, 0.310 mmol) in DCM (5 mL) using TFA (0.3 mL, 3.89 mmol). This gave after workup and purification by flash column chromatography [silica (12 g), eluting with EtOAc in hexane from 40-100%] ethyl 2-(2-((7-(3-aminobenzo[d]isoxazol-7-yl)benzofuran-5-yl)methoxy)phenyl)acetate (180d) (55 mg, 40% yield) as pale-yellow oil. $^1$H NMR (300 MHz, Chloroform-d) δ 8.14 (dd, J=7.4, 1.1 Hz, 1H), 7.95 (d, J=1.6 Hz, 1H), 7.74 (d, J=1.6 Hz, 1H), 7.70 (d, J=2.2 Hz, 1H), 7.59-7.51 (m, 1H), 7.36 (t, J=7.6 Hz, 1H), 7.32-7.22 (m, 2H), 7.05-6.92 (m, 2H), 6.85 (d, J=2.2 Hz, 1H), 5.26 (s, 2H), 4.51 (s, 2H), 4.08 (q, J=7.2 Hz, 2H), 3.74 (s, 2H), 1.13 (t, J=7.1 Hz, 3H); MS (ES+): 443.2 (M+1).

Step-3: Preparation of 2-(2-((7-(3-aminobenzo[d]isoxazol-7-yl)benzofuran-5-yl)methoxy)phenyl)acetic Acid (180e)

Compound 180e was prepared according to the procedure reported in step-6 of Scheme-1 from ethyl 2-(2-((7-(3-aminobenzo[d]isoxazol-7-yl)benzofuran-5-yl)methoxy)phenyl)acetate (180d) (55 mg, 0.124 mmol) in MeOH/THF (6 mL each) using a solution of lithium hydroxide monohydrate (31 mg, 0.74 mmol) in water (2 mL). This gave after workup and purification by reverse phase column [C18 (50 g), eluting with ACN in water (containing 0.1% HCl) from 0-100%] 2-(2-((7-(3-aminobenzo[d]isoxazol-7-yl)benzofuran-5-yl)methoxy)phenyl)acetic acid (180e) (26 mg, 51% yield) as a white solid. $^1$H NMR (300 MHz, DMSO-d$_6$, D$_2$O exchange) δ 8.01 (d, J=2.2 Hz, 1H), 7.91 (dd, J=7.4, 1.2 Hz, 1H), 7.85 (dd, J=7.9, 1.1 Hz, 1H), 7.79-7.69 (m, 2H), 7.37 (t, J=7.6 Hz, 1H), 7.22-7.10 (m, 2H), 7.09-7.01 (m, 1H), 7.00 (d, J=2.2 Hz, 1H), 6.84 (td, J=7.3, 1.1 Hz, 1H), 5.22 (s, 2H), 3.53 (s, 2H); MS (ES+): 415.1 (M+1); MS (ES−): 413.2 (M−1).

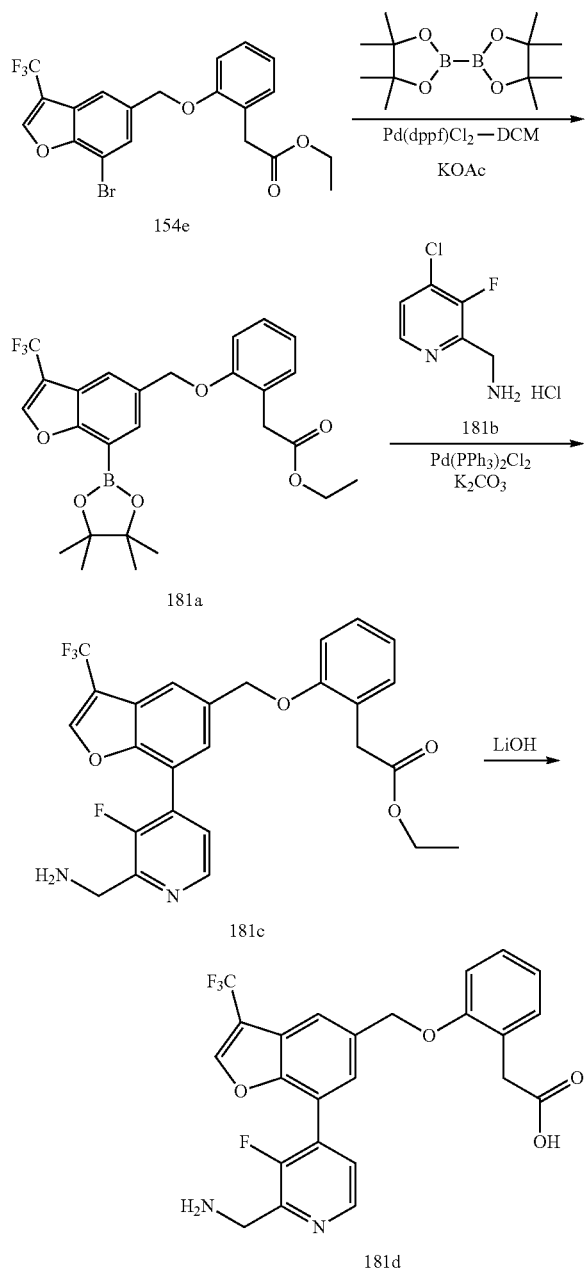

Preparation of 2-(2-((7-(2-(aminomethyl)-3-fluoro-pyridin-4-yl)-3-(trifluoromethyl)benzofuran-5-yl)methoxy)phenyl)acetic Acid (181d)

Step-1: Preparation of Ethyl 2-(2-((7-(4,4,5,5-tetramethyl-1,3,2-dioxaborolan-2-yl)-3-(trifluoromethyl)benzofuran-5-yl)methoxy)phenyl)acetate (181a)

Compound 181a was prepared according to the procedure reported in step-1 of Scheme-59 from ethyl 2-(2-((7-bromo-3-(trifluoromethyl)benzofuran-5-yl)methoxy)phenyl)acetate (154e) (250 mg, 0.547 mmol), using bis(pinacolato)diboron (212 mg, 0.835 mmol), potassium acetate (175 mg, 1.783 mmol) and Pd(dppf)Cl$_2$—CH$_2$Cl$_2$ (51 mg, 0.062 mmol) in anhydrous dioxane (6 mL) under an Ar atmosphere and heating at 90° C. overnight. This gave after workup and purification by flash column chromatography [silica gel, (12 g), eluting with ethyl acetate in hexane from 0-40%] ethyl 2-(2-((7-(4,4,5,5-tetramethyl-1,3,2-dioxaborolan-2-yl)-3-(trifluoromethyl)benzofuran-5-yl)methoxy)phenyl)acetate (181a) (146 mg, 53% yield) as a pale yellow oil. $^1$H NMR (300 MHz, Chloroform-d) δ 8.09 (q, J=1.6 Hz, 1H), 7.95-7.87 (m, 2H), 7.32-7.19 (m, 2H), 7.03-6.93 (m, 2H), 5.19 (s, 2H), 4.13 (p, J=7.1 Hz, 3H), 3.69 (s, 2H), 1.44 (s, 12H), 1.16 (t, J=7.1 Hz, 3H); $^{19}$F NMR (282 MHz, Chloroform-d) 6-59.32.

Step-2: Preparation of Ethyl 2-(2-((7-(2-(aminomethyl)-3-fluoropyridin-4-yl)-3-(trifluoromethyl)benzofuran-5-yl)methoxy)phenyl)acetate (181c)

Compound 181c was prepared according to the procedure reported in step-3 of Scheme-1 from ethyl 2-(2-((7-(4,4,5,5-tetramethyl-1,3,2-dioxaborolan-2-yl)-3-(trifluoromethyl)benzofuran-5-yl)methoxy)phenyl)acetate (181a) (142 mg, 0.282 mmol) in dioxane (5 mL) using (4-chloro-3-fluoropyridin-2-yl)methanamine hydrochloride (181b) (80 mg, 0.404 mmol; CAS #1646565-99-2), bis(triphenylphosphine)palladium(II) chloride (35 mg, 0.050 mmol) and a solution of K$_2$CO$_3$ (220 mg, 1.592 mmol) in water (0.5 mL) under an Ar atmosphere and heating at 100° C. for 4 h on oil bath. This gave after workup, purification by flash column chromatography [silica gel (12 g), eluting with DMA80/DCM from 0-80%] ethyl 2-(2-((7-(2-(aminomethyl)-3-fluoropyridin-4-yl)-3-(trifluoromethyl)benzofuran-5-yl)methoxy)phenyl)acetate (181c) (147 mg, 72% yield) as pale yellow oil. MS (ES+): 503.2 (M+1).

Step-3: Preparation of 2-(2-((7-(2-(aminomethyl)-3-fluoropyridin-4-yl)-3-(trifluoromethyl)benzofuran-5-yl)methoxy)phenyl)acetic Acid (181d)

Compound 181d was prepared according to the procedure reported in step-6 of Scheme-1 from ethyl 2-(2-((7-(2-(aminomethyl)-3-fluoropyridin-4-yl)-3-(trifluoromethyl)benzofuran-5-yl)methoxy)phenyl)acetate (181c) (147 mg, 0.293 mmol) THF/MeOH (6 mL each) using lithium hydroxide monohydrate (65 mg, 1.55 mmol) in Water (2 mL). This gave after workup and purification by reverse phase column [C18 (50 g), eluting with ACN in water (containing 0.1% HCl) from 0-100%] 2-(2-((7-(2-(aminomethyl)-3-fluoropyridin-4-yl)-3-(trifluoromethyl)benzofuran-5-yl)methoxy)phenyl)acetic acid (181d) (14 mg, 10% yield) HCl salt as a white solid. $^1$H NMR (300 MHz, DMSO-d$_6$, D$_2$O Exchange) δ 8.84 (d, J=1.9 Hz, 1H), 8.60 (d, J=5.0 Hz, 1H), 7.94 (s, 1H), 7.75 (dd, J=10.5, 5.2 Hz, 2H), 7.25-7.13 (m, 2H), 7.05 (d, J=8.1 Hz, 1H), 6.87 (t, J=7.3 Hz, 1H), 5.28 (s, 2H), 4.33 (s, 2H), 3.53 (s, 2H); $^{19}$F NMR (282 MHz, DMSO-d$_6$) δ−58.02, −128.49. MS (ES+): 475.2 (M+1); MS(ES−): 473.3 (M−1).

Scheme-182

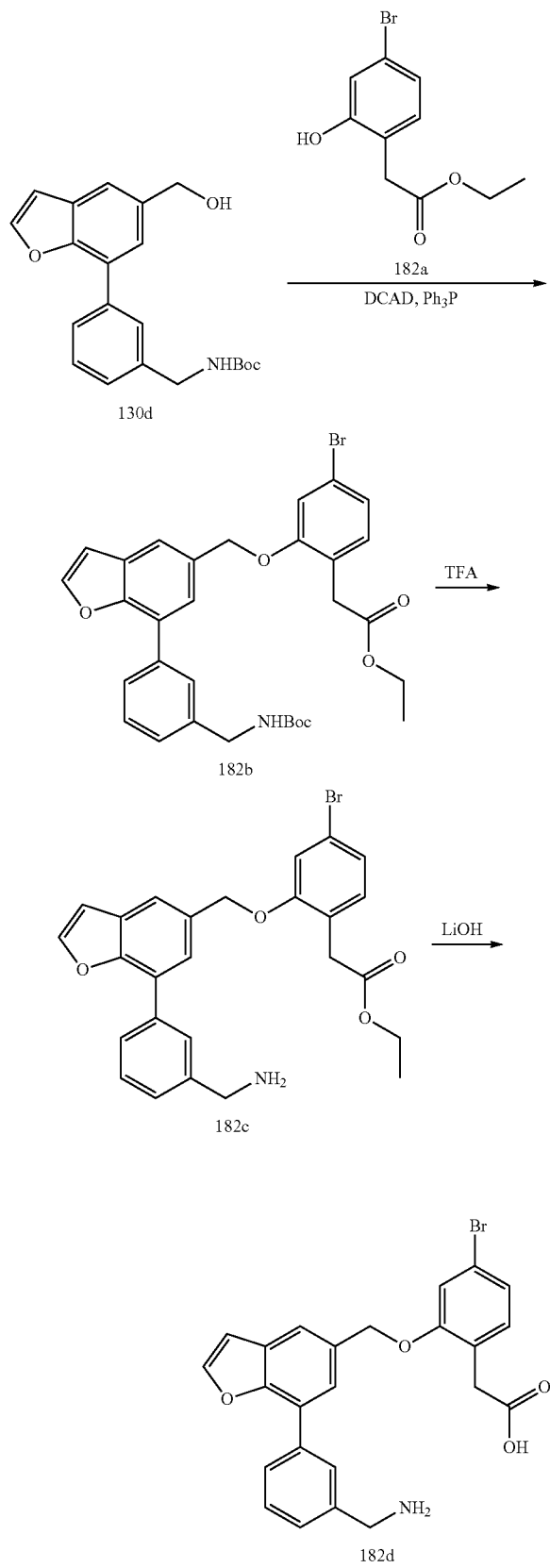

Preparation of 2-(2-((7-(3-(aminomethyl)phenyl) benzofuran-5-yl)methoxy)-4-bromophenyl)acetic Acid (182d)

Step-1: Preparation of Ethyl 2-(4-bromo-2-((7-(3-(((tert-butoxycarbonyl)amino)methyl)phenyl)benzo-furan-5-yl)methoxy)phenyl)acetate (182b)

Compound 182b was prepared according to the procedure reported in step-2 of Scheme-23 from tert-butyl 3-(5-(hy-droxymethyl)benzofuran-7-yl)benzylcarbamate (130d) (1.910 g, 5.40 mmol) in DCM (20 mL) using triphenylphos-phine (1.559 g, 5.94 mmol), ethyl 2-(4-bromo-2-hydroxy-phenyl)acetate (182a) (1.4 g, 5.40 mmol) and E)-bis(4-chlorobenzyl) diazene-1,2-dicarboxylate (DCAD, 2.182 g, 5.94 mmol). This gave after workup and purification by flash column chromatography [silica gel 80 g, eluting with ethyl acetate in hexanes from 0-100%] to ethyl 2-(4-bromo-2-((7-(3-(((tert-butoxycarbonyl)amino)methyl)phenyl)benzo-furan-5-yl)methoxy)phenyl)acetate (182b) (1.97 g, 61% yield) as a white solid; $^1$H NMR (300 MHz, DMSO-$d_6$) δ 8.09 (d, J=2.2 Hz, 1H), 7.78-7.66 (m, 3H), 7.54 (d, J=1.7 Hz, 1H), 7.55-7.43 (m, 1H), 7.35 (d, J=1.8 Hz, 1H), 7.31 (dt, J=7.6, 1.3 Hz, 1H), 7.23-7.17 (m, 1H), 7.16-7.10 (m, 1H), 7.07 (d, J=2.2 Hz, 1H), 5.27 (s, 2H), 4.23 (d, J=6.2 Hz, 2H), 3.90 (q, J=7.1 Hz, 2H), 3.60 (s, 2H), 1.39 (s, 9H), 0.95 (t, J=7.1 Hz, 3H); MS (ES+): 494.10, 496.10 (M+2, loss of Boc).

Step-2: Preparation of Ethyl 2-(2-((7-(3-(aminom-ethyl)phenyl)benzofuran-5-yl)methoxy)-4-brom-ophenyl)acetate (182c)

Compound 182c was prepared according to the procedure reported in step-5 of Scheme-1 from ethyl 2-(4-bromo-2-((7-(3-(((tert-butoxycarbonyl)amino)methyl)phenyl)benzo-furan-5-yl)methoxy)phenyl)acetate (182b) (0.250 g, 0.421 mmol) in DCM (10 mL) using TFA (0.324 mL, 4.21 mmol). This gave after workup and purification by flash column chromatography [silica gel 12 g, eluting with methanol in DCM from 0-40%] ethyl 2-(2-((7-(3-(aminomethyl)phenyl) benzofuran-5-yl)methoxy)-4-bromophenyl)acetate (182c) (0.126 g, 49% yield) TFA salt as a white solid; $^1$H NMR (300 MHz, DMSO-$d_6$) δ 8.25 (s, 3H, D$_2$O exchangeable), 8.12 (d, J=2.2 Hz, 1H), 8.00-7.96 (m, 1H), 7.91 (dt, J=7.7, 1.5 Hz, 1H), 7.73 (d, J=1.6 Hz, 1H), 7.65-7.51 (m, 3H), 7.35 (d, J=1.8 Hz, 1H), 7.23-7.18 (m, 1H), 7.16-7.11 (m, 1H), 7.10 (d, J=2.2 Hz, 1H), 5.28 (s, 2H), 4.16 (s, 2H), 3.92 (q, J=7.1 Hz, 2H), 3.61 (s, 2H), 0.97 (t, J=7.1 Hz, 3H); MS (ES+): 496.10, 494.10 (M+2); $^{19}$F NMR (282 MHz, DMSO-$d_6$) δ−73.47; MS (ES−): 494.20, 492.20 (M−2); HPLC purity: 84.72%.

Step-3: Preparation of 2-(2-((7-(3-(aminomethyl) phenyl)benzofuran-5-yl)methoxy)-4-bromophenyl) acetic Acid (182d)

Compound 182d was prepared according to the procedure reported in step-6 of Scheme-1 from ethyl 2-(2-((7-(3-(aminomethyl)phenyl)benzofuran-5-yl)methoxy)-4-brom-ophenyl)acetate (182c) (0.100 g, 0.202 mmol) in THF (4 mL) and methanol (8 mL) using 2M LiOH (0.506 mL, 1.011 mmol). This gave after workup and purification by flash column chromatography [silica gel 12 g, eluting with metha-nol in DCM from 0-100%] followed by reverse phase column [C18 (30 g), eluting with ACN in water (containing 0.1% HCl) from 0-100%] 2-(2-((7-(3-(aminomethyl)phenyl)

benzofuran-5-yl)methoxy)-4-bromophenyl)acetic acid (182d) (0.076 g, 81% yield) HCl salt as a white solid; $^1$H NMR (300 MHz, DMSO-d$_6$) δ 12.34 (bs, 1H, D$_2$O exchangeable), 8.33 (bs, 3H, D$_2$O exchangeable), 8.12 (d, J=2.2 Hz, 1H), 8.01-7.97 (m, 1H), 7.97-7.87 (m, 1H), 7.75 (d, J=1.6 Hz, 1H), 7.65-7.62 (m, 1H), 7.61-7.52 (m, 2H), 7.32 (d, J=1.8 Hz, 1H), 7.24-7.17 (m, 1H), 7.12 (dd, J=8.0, 1.8 Hz, 1H), 7.08 (d, J=2.2 Hz, 1H), 5.30 (s, 2H), 4.24-4.06 (m, 2H), 3.57 (s, 2H); MS (ES+): 468.10, 466.10 (M+2); MS (ES−): 466.15, 464.20 (M−2); HPLC purity: 90.92%.

Scheme-183

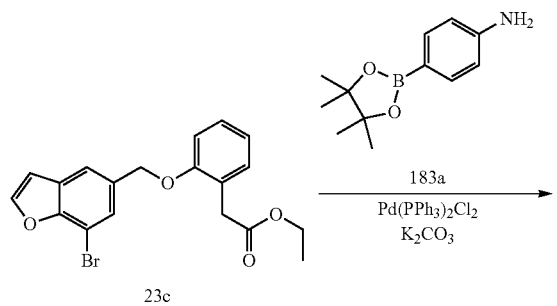

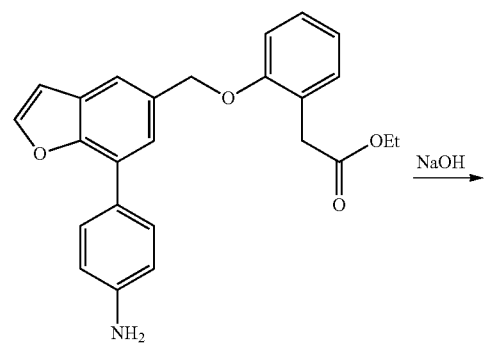

Preparation of 2-(2-((7-(4-aminophenyl)benzofuran-5-yl)methoxy)phenyl)acetic Acid (183c)

Step-1: Preparation of Ethyl 2-(2-((7-(4-aminophenyl)benzofuran-5-yl)methoxy)phenyl)acetate (183b)

Compound 183b was prepared according to the procedure reported in step-1 of Scheme-59 from ethyl 2-(2-((7-bromobenzofuran-5-yl)methoxy)phenyl)acetate (23c) (500 mg, 1.285 mmol) in dioxane (10 mL) using 4-(4,4,5,5-tetramethyl-1,3,2-dioxaborolan-2-yl)aniline (183a) (310 mg, 1.413 mmol; CAS #214360-73-3), bis(triphenylphosphine)palladium(II) chloride (90 mg, 0.128 mmol) and K$_2$CO$_3$ (533 mg, 3.85 mmol) under a nitrogen atmosphere and heating at 80° C. for 16 h on an oil bath. This gave after workup, purification by flash column chromatography [silica gel eluting with 0-30% EtOAc in hexane] ethyl 2-(2-((7-(4-aminophenyl)benzofuran-5-yl)methoxy)phenyl)acetate (183b) (0.38 g, 74% yield) as a yellow oil. $^1$H NMR (300 MHz, Chloroform-d) δ 7.81-7.67 (m, 3H), 7.59 (d, J=1.7, 0.8 Hz, 1H), 7.48 (d, J=1.7 Hz, 1H), 7.34-7.19 (m, 2H), 7.06-6.92 (m, 2H), 6.92-6.80 (m, 3H), 5.22 (s, 2H), 4.07 (q, J=7.1 Hz, 2H), 3.70 (s, 2H), 1.13 (t, J=7.1 Hz, 3H); MS (ES+): 402 (M+1).

Step-2: Preparation of 2-(2-((7-(4-aminophenyl) benzofuran-5-yl)methoxy)phenyl)acetic acid (183c)

Compound 183c was prepared according to the procedure reported in step-4 of Scheme-4 from ethyl 2-(2-((7-(4-aminophenyl)benzofuran-5-yl)methoxy)phenyl)acetate (183b) (0.22 g, 0.548 mmol) in THF (1 mL) and MeOH (2 mL each) using NaOH (0.088 g, 2.192 mmol) in water (1 mL). This gave after workup and purification by reverse phase column [C18 (100 g), eluting with ACN in water (containing 0.1% HCl) from 0-100%] 2-(2-((7-(4-aminophenyl)benzofuran-5-yl)methoxy)phenyl)acetic acid (183c) (73 mg, 36% yield) HCl salt as an off-white solid. $^1$H NMR (300 MHz, DMSO-d$_6$) δ 8.10 (d, J=2.2 Hz, 1H), 8.00-7.86 (m, 2H), 7.73 (d, J=1.6 Hz, 1H), 7.62 (d, J=1.6 Hz, 1H), 7.41-7.30 (m, 2H), 7.24 (t, J=7.7 Hz, 2H), 7.10 (d, J=8.0 Hz, 1H), 7.04 (d, J=2.2 Hz, 1H), 6.90 (td, J=7.4, 1.1 Hz, 1H), 5.26 (s, 2H), 3.59 (s, 2H); HPLC purity: 98.9; MS (ES−): 372 (M−1).

Scheme-184

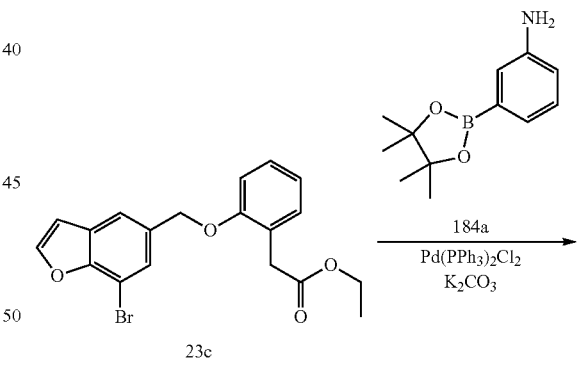

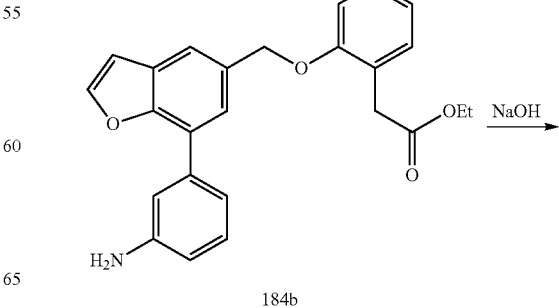

-continued

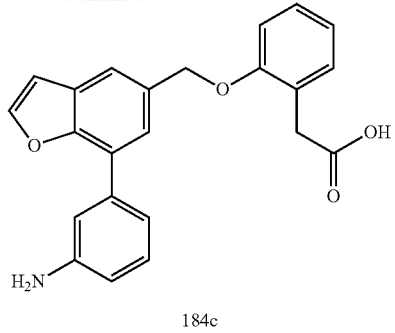

184c

Preparation of 2-(2-((7-(3-aminophenyl)benzofuran-5-yl)methoxy)phenyl)acetic Acid (184c)

Step-1: Preparation of Ethyl 2-(2-((7-(3-aminophenyl)benzofuran-5-yl)methoxy)phenyl)acetate (184b)

Compound 184b was prepared according to the procedure reported in step-1 of Scheme-59 from ethyl 2-(2-((7-bromobenzofuran-5-yl)methoxy)phenyl)acetate (23c) (200 mg, 0.514 mmol) in dioxane (2 mL) using 3-(4,4,5,5-tetramethyl-1,3,2-dioxaborolan-2-yl)aniline (184a) (124 mg, 0.565 mmol; CAS #210907-84-9), bis(triphenylphosphine)palladium(II) chloride (36 mg, 0.051 mmol) and K$_2$CO$_3$ (213 mg, 1.541 mmol) in water (1 mL) under a nitrogen atmosphere and heating at 80° C. for 16 h on an oil bath. This gave after workup, purification by flash column chromatography [silica gel eluting with 0-30% EtOAc in hexane] ethyl 2-(2-((7-(3-aminophenyl)benzofuran-5-yl)methoxy)phenyl)acetate (184b) (134 mg, 65.0% yield) as a thick opaque yellow oil. $^1$H NMR (300 MHz, Chloroform-d) δ 7.72 (d, J=2.2 Hz, 1H), 7.64 (d, 1H), 7.52 (d, J=1.7 Hz, 1H), 7.37-7.21 (m, 6H), 7.04-6.93 (m, 2H), 6.84 (d, J=2.2 Hz, 1H), 6.82-6.74 (m, 1H), 5.23 (s, 2H), 4.07 (q, J=7.1 Hz, 2H), 3.71 (s, 2H), 1.13 (t, J=7.1 Hz, 7H); MS (ES+): 424 (M+Na).

Step-2: Preparation of 2-(2-((7-(3-aminophenyl)benzofuran-5-yl)methoxy)phenyl)acetic acid (184c)

Compound 184c was prepared according to the procedure reported in step-4 of Scheme-4 from ethyl 2-(2-((7-(3-aminophenyl)benzofuran-5-yl)methoxy)phenyl)acetate (184b) (130 mg, 0.324 mmol) in THF (1 mL) and MeOH (2 mL each) using NaOH (52 mg, 1.295 mmol) in Water (1 mL). This gave after workup and purification by reverse phase column [C18 (100 g), eluting with ACN in water (containing 0.1% HCl) from 0-100%] 2-(2-((7-(3-aminophenyl)benzofuran-5-yl)methoxy)phenyl)acetic acid (184c) (34 mg, 28% yield) HCl salt as an off-white solid. $^1$H NMR (300 MHz, DMSO-d$_6$) δ 8.12 (d, J=2.2 Hz, 1H), 7.77 (d, J=1.6 Hz, 1H), 7.75-7.65 (m, 2H), 7.61 (d, J=1.6 Hz, 1H), 7.55 (t, J=7.8 Hz, 1H), 7.23 (dd, J=8.4, 6.9 Hz, 3H), 7.14-7.04 (m, 2H), 6.90 (td, J=7.4, 1.1 Hz, 1H), 5.27 (s, 2H), 3.59 (s, 2H); MS (ES−): 372 (M−1).

Scheme-185

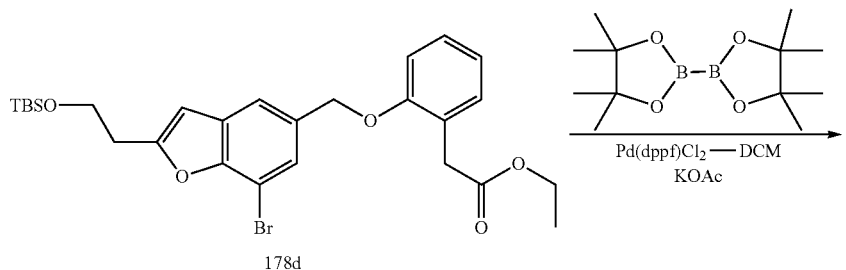

178d

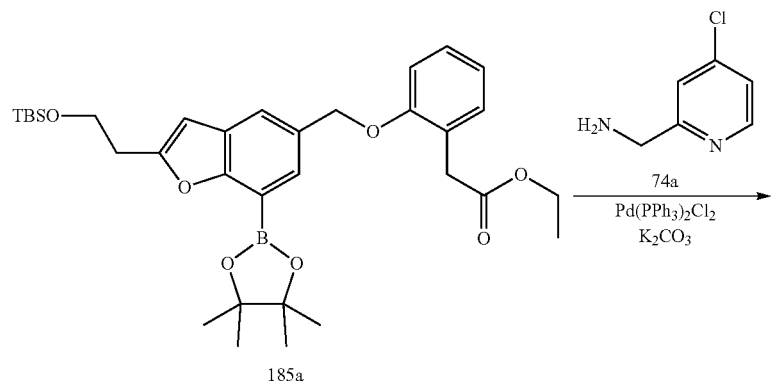

185a

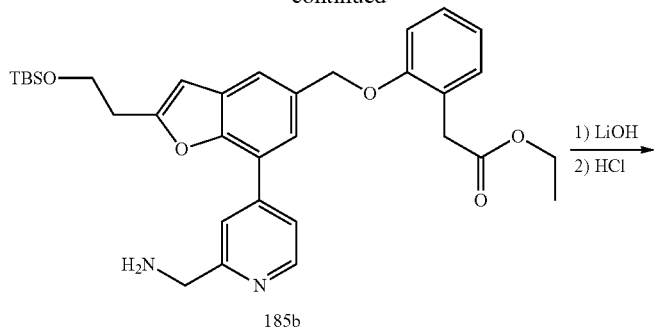

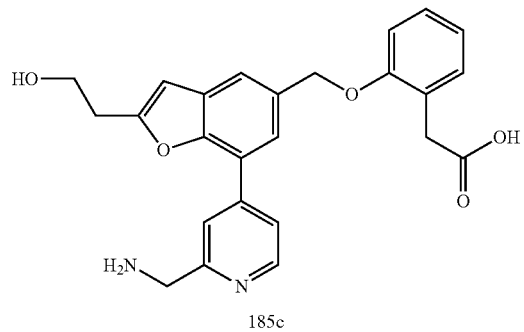

Preparation of 2-(2-((7-(2-(aminomethyl)pyridin-4-yl)-2-(2-hydroxyethyl)benzofuran-5-yl)methoxy)phenyl)acetic Acid (185c)

Step-1: Preparation of Ethyl 2-(2-((2-(2-((tert-butyldimethylsilyl)oxy)ethyl)-7-(4,4,5,5-tetramethyl-1,3,2-dioxaborolan-2-yl)benzofuran-5-yl)methoxy)phenyl)acetate (185a)

Compound 185a was prepared according to the procedure reported in step-1 of Scheme-59 from ethyl 2-(2-((7-bromo-2-(2-((tert-butyldimethylsilyl)oxy)ethyl)benzofuran-5-yl)methoxy)phenyl)acetate (178d) (1.4 g, 2.56 mmol), using bis(pinacolato)diboron (0.97 g, 3.84 mmol), potassium acetate (0.75 g, 7.67 mmol) and Pd(dppf)Cl$_2$—CH$_2$Cl$_2$ (0.31 g, 0.38 mmol) in anhydrous dioxane (20 mL) under an Ar atmosphere and heating at 100° C. overnight. This gave after workup and purification by flash column chromatography [silica gel, (40 g), eluting with ethyl acetate in hexane from 0-40%] ethyl 2-(2-((2-(2-((tert-butyldimethylsilyl)oxy)ethyl)-7-(4,4,5,5-tetramethyl-1,3,2-dioxaborolan-2-yl)benzofuran-5-yl)methoxy)phenyl)acetate (185a) (1.04 g, 68% yield) as a clear oil; $^1$H NMR (300 MHz, DMSO-d$_6$) δ 7.72 (d, J=1.9 Hz, 1H), 7.57 (d, J=1.9 Hz, 1H), 7.31-7.20 (m, 2H), 7.11 (dd, J=8.3, 1.1 Hz, 1H), 6.92 (td, J=7.3, 1.1 Hz, 1H), 6.67-6.62 (m, 1H), 5.15 (s, 2H), 4.07-3.93 (m, 4H), 3.61 (s, 2H), 3.01 (t, J=6.2 Hz, 2H), 1.19 (s, 12H), 1.07 (t, J=7.1 Hz, 3H), 0.82 (s, 9H), 0.00 (s, 6H).

Step-2: Preparation of Ethyl 2-(2-((7-(2-(aminomethyl)pyridin-4-yl)-2-(2-((tert-butyldimethylsilyl)oxy)ethyl)benzofuran-5-yl)methoxy)phenyl)acetate (185b)

Compound 185b was prepared according to the procedure reported in step-3 of Scheme-1 from ethyl 2-(2-((2-(2-((tert-butyldimethylsilyl)oxy)ethyl)-7-(4,4,5,5-tetramethyl-1,3,2-dioxaborolan-2-yl)benzofuran-5-yl)methoxy)phenyl)acetate (185a) (500 mg, 0.84 mmol) in dioxane (6 mL) using (4-chloropyridin-2-yl)methanamine (74a) (180 mg, 1.26 mmol), bis(triphenylphosphine)palladium(II) chloride (89 mg, 0.13 mmol) and a solution of K$_2$CO$_3$ (291 mg, 2.10 mmol) in water (3 mL) under an Ar atmosphere and heating at 100° C. for 3 h on oil bath. This gave after workup, purification by flash column chromatography [silica gel (40 g), eluting with DMA80/DCM from 0-70%] ethyl 2-(2-((7-(2-(aminomethyl)pyridin-4-yl)-2-(2-((tert-butyldimethylsilyl)oxy)ethyl)benzofuran-5-yl)methoxy)phenyl)acetate (185b) (320 mg, 66% yield) as a clear oil; MS (ES+): 575.4 (M+1).

Step-3: Preparation of 2-(2-((7-(2-(aminomethyl)pyridin-4-yl)-2-(2-hydroxyethyl)benzofuran-5-yl)methoxy)phenyl)acetic Acid (185c)

Compound 185c was prepared according to the procedure reported in step-7 of Scheme-178 from ethyl 2-(2-((7-(2-(aminomethyl)pyridin-4-yl)-2-(2-((tert-butyldimethylsilyl)oxy)ethyl)benzofuran-5-yl)methoxy)phenyl)acetate (185b) (212 mg, 0.37 mmol) THF/MeOH (6 mL each) using lithium hydroxide monohydrate (20 mg, 0.48 mmol) in water (2 mL). This gave after workup and purification by reverse phase column [C18 (50 g), eluting with ACN in water (containing 0.1% HCl) from 0-100%] 2-(2-((7-(2-(aminomethyl)pyridin-4-yl)-2-(2-hydroxyethyl)benzofuran-5-yl)methoxy)phenyl)acetic acid (185c) (28 mg, 18% yield over 2 steps) as a yellow solid; $^1$H NMR (300 MHz, DMSO-d$_6$) δ 8.82 (d, J=5.5 Hz, 1H), 8.75 (s, 3H, D$_2$O exchangeable), 8.26 (s, 1H), 8.13 (dd, J=5.5, 1.7 Hz, 1H), 7.82-7.75 (m, 2H), 7.28-7.17 (m, 2H), 7.12-7.04 (m, 1H), 6.90 (td, J=7.4, 1.1 Hz, 1H), 6.78 (d, J=1.0 Hz, 1H), 5.26 (s, 2H), 4.43-4.28 (m, 2H), 3.80 (t, J=6.5 Hz, 2H), 3.60 (s, 2H), 3.00 (t, J=6.5 Hz, 2H); MS (ES+): 433.2 (M+1); (ES−): 431.3 (M−1).

Scheme-186

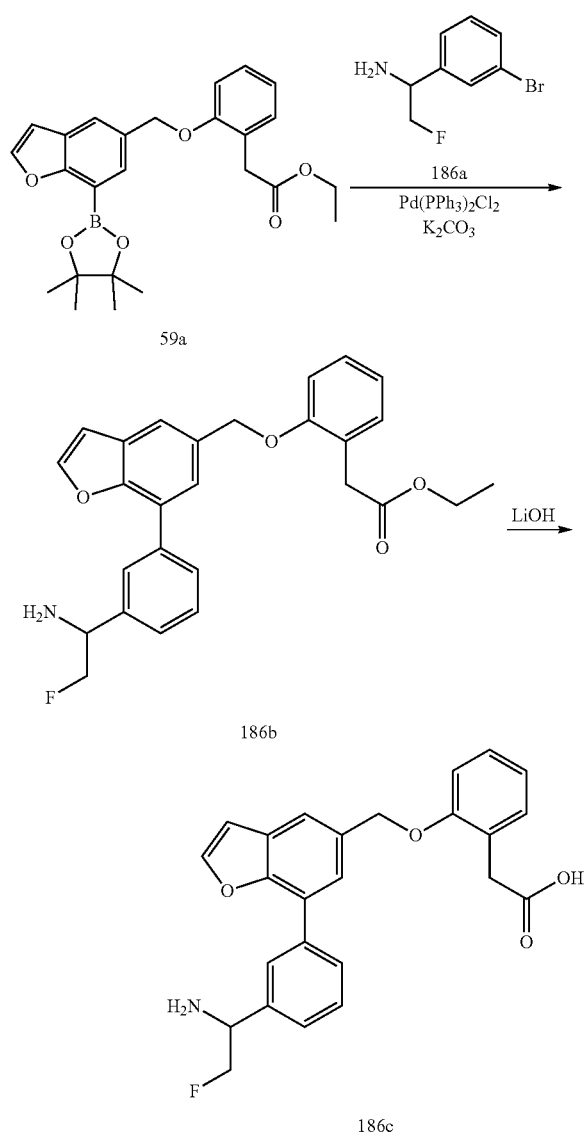

Preparation of 2-(2-((7-(3-(1-amino-2-fluoroethyl)phenyl)benzofuran-5-yl)methoxy)phenyl)acetic Acid (186c)

Step-1: Preparation of Ethyl 2-(2-((7-(3-(1-amino-2-fluoroethyl)phenyl)benzofuran-5-yl)methoxy)phenyl)acetate (186b)

Compound 186b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (400 mg, 0.92 mmol) in dioxane (10 mL) using 1-(3-bromophenyl)-2-fluoroethanamine (186a) (180 mg, 1.26 mmol; CAS #929972-40-7), bis(triphenylphosphine)palladium(II) chloride (97 mg, 0.14 mmol) and a solution of K$_2$CO$_3$ (380 mg, 2.75 mmol) in water (3 mL) under an Ar atmosphere and heating at 100° C. for 3 h on oil bath. This gave after workup, purification by flash column chromatography [silica gel (24 g), eluting with DMA80/DCM from 0-70%] followed by purification by reverse phase column [C18 (50 g), eluting with ACN in water (containing 0.1% HCl) from 0-100%] ethyl 2-(2-((7-(3-(1-amino-2-fluoroethyl)phenyl)benzofuran-5-yl)methoxy)phenyl)acetate (186b) (246 mg, 60% yield) as a clear oil); MS (ES+): 448.2 (M+1).

Step-2: Preparation of 2-(2-((7-(3-(1-amino-2-fluoroethyl)phenyl)benzofuran-5-yl)methoxy)phenyl)acetic Acid (186c)

Compound 186c was prepared according to the procedure reported in step-6 of Scheme-1 from ethyl 2-(2-((7-(3-(1-amino-2-fluoroethyl)phenyl)benzofuran-5-yl)methoxy)phenyl)acetate (186b) (166 mg, 0.37 mmol) THF/MeOH (6 mL each) using lithium hydroxide monohydrate (31 mg, 0.74 mmol) in water (2 mL). This gave after workup and purification by reverse phase column [C18 (50 g), eluting with ACN in water (containing 0.1% HCl) from 0-100%] 2-(2-((7-(3-(1-amino-2-fluoroethyl)phenyl)benzofuran-5-yl)methoxy)phenyl)acetic acid (186c) (110 mg, 71% yield) HCl salt as a white solid; $^1$H NMR (300 MHz, DMSO-d$_6$) δ 9.29 (s, 2H, D$_2$O exchangeable), 8.11 (d, J=2.2 Hz, 1H), 8.08 (s, 1H), 7.98 (dt, J=6.6, 1.9 Hz, 1H), 7.77 (d, J=1.5 Hz, 1H), 7.71-7.60 (m, 3H), 7.28-7.18 (m, 2H), 7.13-7.08 (m, 1H), 7.07 (d, J=2.2 Hz, 1H), 6.91 (td, J=7.4, 1.1 Hz, 1H), 5.28 (s, 2H), 4.99-4.90 (m, 1H), 4.89-4.72 (m, 2H), 3.61 (s, 2H); $^{19}$F NMR (282 MHz, DMSO-d$_6$) δ −222.55; MS (ES+): 420.2 (M+1); (ES−): 418.3 (M−1).

Scheme-187

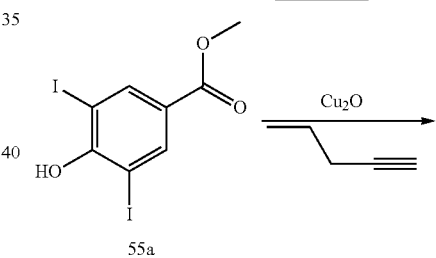

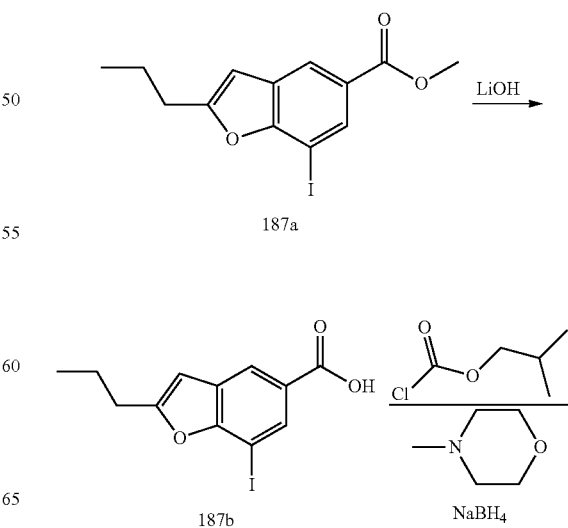

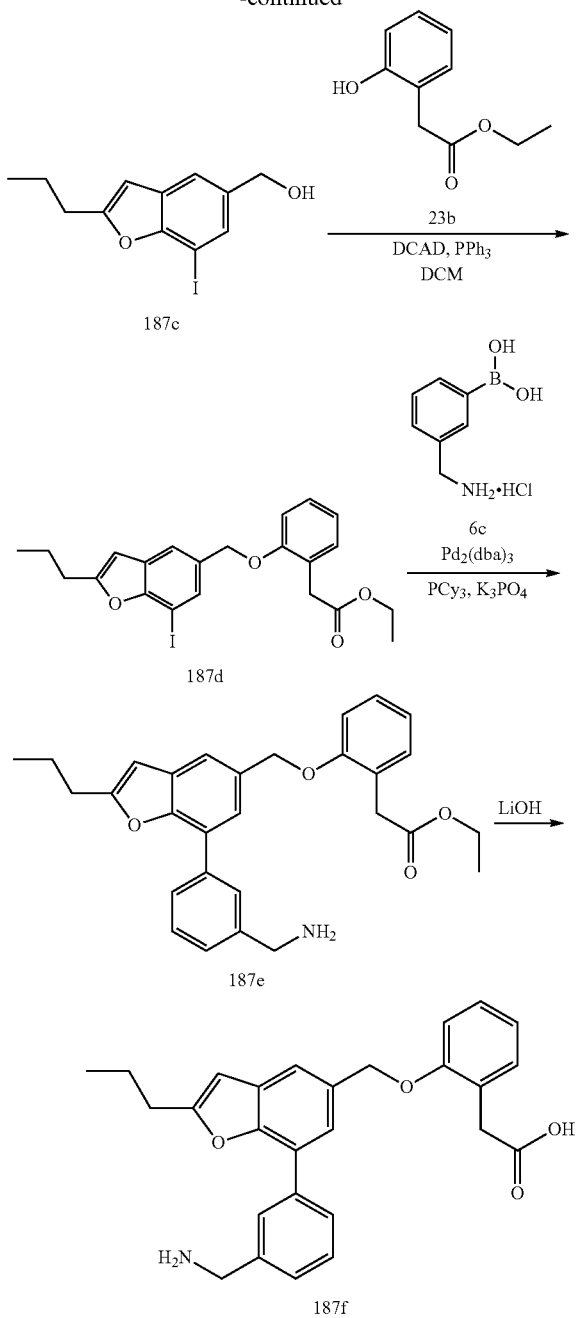

Preparation of 2-(2-((7-(3-(aminomethyl)phenyl)-2-propylbenzofuran-5-yl)methoxy)phenyl)acetic Acid (187f)

Step-1: Preparation of methyl 7-iodo-2-propylbenzofuran-5-carboxylate (187a)

Compound 187a was prepared according to the procedure reported in step-1 of Scheme-55, from methyl 4-hydroxy-3,5-diiodobenzoate (55a) (12.00 g, 29.71 mmol) in pyridine (30 mL) using 1-pentyne (2.93 mL, 29.71 mmol) and copper(I) oxide (2.13 g, 14.85 mmol). This gave after workup and purification by flash column chromatography [silica gel, eluting with EtOAc in hexane from 0-10%] methyl 7-iodo-2-propylbenzofuran-5-carboxylate (187a) (3.36 g, 33% yield). $^1$H NMR (300 MHz, DMSO-$d_6$) δ 8.18 (d, J=1.6 Hz, 1H), 8.15 (d, J=1.6 Hz, 1H), 6.89 (s, 1H), 3.86 (s, 3H), 2.81 (t, J=7.4 Hz, 2H), 1.84-1.57 (m, 2H), 0.98 (t, J=7.4 Hz, 3H).

Step-2: Preparation of 7-iodo-2-propylbenzofuran-5-carboxylic Acid (187b)

Compound 187b was prepared according to the procedure reported in step-6 of Scheme-1, from methyl 7-iodo-2-propylbenzofuran-5-carboxylate (187a) ((3.30g, 9.59 mmol) in MeOH/THF (20 mL each) using a solution of lithium hydroxide hydrate (805 mg, 19.18 mmol) in water (3 mL) This gave after workup 7-iodo-2-propylbenzofuran-5-carboxylic acid (187b) (3.08 g, 97% yield) as a white solid; $^1$H NMR (300 MHz, DMSO-$d_6$) δ 13.05 (s, 1H), 8.15 (d, J=1.6 Hz, 1H), 8.13 (d, J=1.6 Hz, 1H), 6.88 (s, 1H), 2.80 (t, J=7.4 Hz, 2H), 1.87-1.55 (m, 2H), 0.98 (t, J=7.4 Hz, 3H); MS (ES−): 329.1 (M−1).

Step-3: Preparation of (7-iodo-2-propylbenzofuran-5-yl)methanol (187c)

Compound 187c was prepared according to the procedure reported in step-1 of Scheme-23 from 7-iodo-2-propylbenzofuran-5-carboxylic acid (187b) (2.50 g, 7.57 mmol) using N-methylmorpholine (1.00 mL, 9.09 mmol) in THF (50 mL), isobutyl chloroformate (1.18 mL, 9.09 mmol) and NaBH$_4$ (860 mg, 22.72 mmol) in water (4.0 mL). This gave after workup and purification by flash column chromatography [silica gel, eluting with EtOAc in hexane from 0-20%] (7-iodo-2-propylbenzofuran-5-yl)methanol (187c) (1.65 g, 69% yield) as a white solid; $^1$H NMR (300 MHz, DMSO-$d_6$) δ 7.54 (d, J=1.4 Hz, 1H), 7.44 (d, J=1.4 Hz, 1H), 6.72 (s, 1H), 5.26 (t, J=5.8 Hz, 1H), 4.51 (d, J=5.8 Hz, 2H), 2.76 (t, J=7.4 Hz, 2H), 1.86-1.53 (m, 2H), 0.97 (t, J=7.4 Hz, 3H).

Step-4: Preparation of Ethyl 2-(2-((7-iodo-2-propylbenzofuran-5-yl)methoxy)phenyl)acetate (187d)

Compound 187d was prepared according to the procedure reported in step-2 of Scheme-23 from (7-iodo-2-propylbenzofuran-5-yl)methanol (187c)(1.60 g, 5.06 mmol) in DCM (20 mL) using triphenylphosphine (1.86 g, 7.08 mmol) ethyl 2-(2-hydroxyphenyl) acetate (23b) (1.28 g, 7.08 mmol) and di-(4-chlorobenzyl)azodicarboxylate (DCAD, 2.60 g, 7.08 mmol) in DCM (40 mL). This gave after workup and purification by flash column chromatography [silica gel, eluting with EtOAc in hexane from 0-15%] ethyl 2-(2-((7-iodo-2-propylbenzofuran-5-yl)methoxy)phenyl)acetate (187d) (2.10 g, 87% yield) as a white solid; $^1$H NMR (300 MHz, DMSO-$d_6$) δ 7.64 (d, J=1.5 Hz, 1H), 7.57 (d, J=1.5 Hz, 1H), 7.33-7.17 (m, 2H), 7.06 (d, J=8.1 Hz, 1H), 6.95-6.86 (m, 1H), 6.76 (s, 1H), 5.12 (s, 2H), 4.02 (q, J=7.1 Hz, 2H), 3.60 (s, 2H), 2.78 (t, J=7.4 Hz, 2H), 1.86-1.57 (m, 2H), 1.08 (t, J=7.1 Hz, 3H), 0.97 (t, J=7.4 Hz, 3H); MS (ES+): 501.2 (M+Na).

Step-5: Preparation of Ethyl 2-(2-((7-(3-(aminomethyl)phenyl)-2-propylbenzofuran-5-yl)methoxy)phenyl)acetate (187e)

Compound 187e was prepared according to the procedure reported in step-3 of Scheme-1 from ethyl 2-(2-((7-iodo-2-propylbenzofuran-5-yl)methoxy)phenyl)acetate (187d) (500 mg, 1.05 mmol) in dioxane (5 mL) using 3-(aminomethyl) phenylboronic acid hydrochloride (6c) (294 mg, 1.57 mmol), tripotassium phosphate (378 mg, 1.78 mmol) in water (0.6 mL), tricyclohexylphosphine (92 mg, 0.35 mmol) and $Pd_2(dba)_3$ (96 mg, 0.105 mmol) under an Ar atmosphere and heating at 125° C. for 45 min in a microwave. This gave after workup, purification by flash column chromatography [silica gel, eluting with 0 to 10% methanol in DCM] ethyl 2-(2-((7-(3-(aminomethyl)phenyl)-2-propylbenzofuran-5-yl)methoxy)phenyl)acetate (187e) (32 mg, 7% yield) as a white solid; $^1$H NMR (300 MHz, DMSO-$d_6$) δ 7.80 (s, 1H), 7.71 (d, J=7.8 Hz, 1H), 7.56 (d, J=1.6 Hz, 1H), 7.50-7.42 (m, 2H), 7.38 (d, J=7.7 Hz, 1H), 7.30-7.18 (m, 2H), 7.11 (d, J=8.2 Hz, 1H), 6.90 (t, J=7.7 Hz, 1H), 6.67 (s, 1H), 5.21 (s, 2H), 3.93 (q, J=7.1 Hz, 2H), 3.80 (s, 2H), 3.62 (s, 2H), 2.78 (t, J=7.4 Hz, 2H), 1.84-1.64 (m, 2H), 1.02-0.93 (m, 6H); MS (ES+): 458.3 (M+1).

Step-6: Preparation of 2-(2-((7-(3-(aminomethyl) phenyl)-2-propylbenzofuran-5-yl)methoxy)phenyl) acetic Acid (187f)

Compound 187f was prepared according to the procedure reported in step-6 of Scheme-1, from ethyl 2-(2-((7-(3-(aminomethyl)phenyl)-2-propylbenzofuran-5-yl)methoxy) phenyl)acetate (187e) (30 mg, 0.066 mmol) in MeOH/THF (12 mL each) using a solution of lithium hydroxide hydrate (10 mg, 0.238 mmol) in water (4 mL). This gave after workup and purification flash column chromatography (silica gel, eluting with 0 to 10% MeOH in DCM) 2-(2-((7-(3-(aminomethyl)phenyl)-2-propylbenzofuran-5-yl) methoxy)phenyl)acetic acid (187f) (17 mg, 60% yield) as a white solid; $^1$H NMR (300 MHz, DMSO-$d_6$) δ 8.32 (s, 1H), 8.08 (d, J=7.8 Hz, 1H), 7.83 (d, J=1.6 Hz, 1H), 7.56 (d, J=1.5 Hz, 1H), 7.48 (t, J=7.7 Hz, 1H), 7.34 (d, J=7.5 Hz, 1H), 7.16-7.00 (m, 2H), 6.94 (d, J=8.1 Hz, 1H), 6.81 (t, J=7.3 Hz, 1H), 6.68 (s, 1H), 5.24 (s, 2H), 4.00 (s, 2H), 3.38 (s, 2H), 2.79 (t, J=7.4 Hz, 2H), 1.83-1.62 (m, 2H), 0.98 (t, J=7.4 Hz, 3H); MS (ES+): 430.3 (M+1); MS (ES−): 464.3 (M+Cl); HPLC purity: 98.33%.

Scheme-188

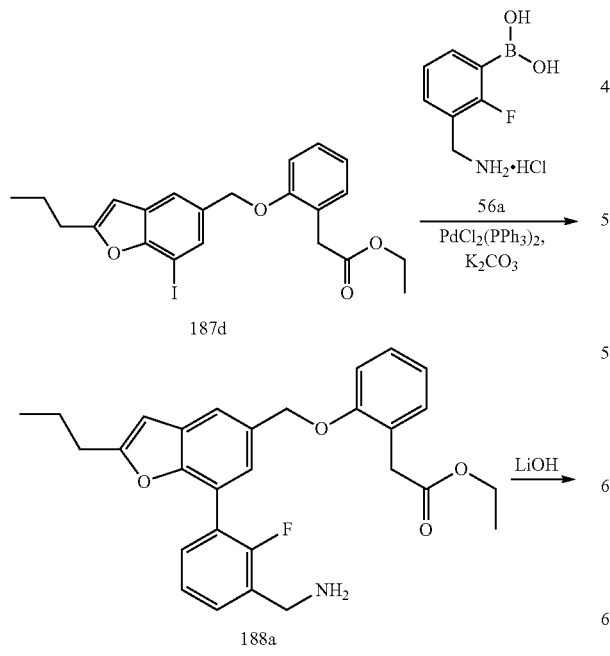

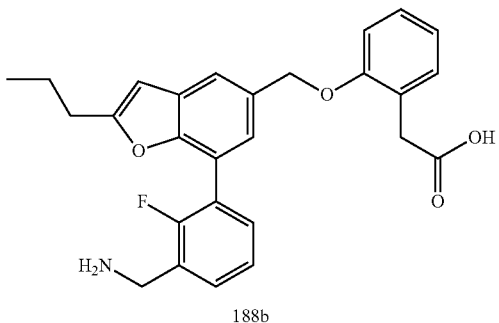 [SMILES: CCCc1cc2cc(COc3ccccc3CC(=O)O)cc(-c3cccc(CN)c3)c2o1]

Preparation of 2-(2-((7-(3-(aminomethyl)-2-fluorophenyl)-2-propylbenzofuran-5-yl)methoxy)phenyl) acetic Acid (188b)

Step-1: Preparation of Ethyl 2-(2-((7-(3-(aminomethyl)-2-fluorophenyl)-2-propylbenzofuran-5-yl) methoxy)phenyl)acetate (188a)

Compound 188a was prepared according to the procedure reported in step-3 of Scheme-1 from ethyl 2-(2-((7-iodo-2-propylbenzofuran-5-yl)methoxy)phenyl)acetate (187d) (2.00 g, 4.18 mmol) in dioxane (30 mL) using 3-(aminomethyl)-2-fluorophenylboronic acid hydrochloride (56a) (1.41 g, 6.88 mmol), a solution of $K_2CO_3$ (1.90 g, 13.75 mmol) in water (5 mL), bis(triphenylphosphine)palladium(II) chloride (484 mg, 0.69 mmol) and heating at 100° C. for 3h on oil bath. This gave after workup, purification by flash column chromatography [silica gel, eluting with methanol in DCM from 0-10%] ethyl 2-(2-((7-(3-(aminomethyl)-2-fluorophenyl)-2-propylbenzofuran-5-yl)methoxy)phenyl)acetate (188a) (1.85 g); MS (ES+): 476.4 (M+1).

Step-2: Preparation of 2-(2-((7-(3-(aminomethyl)-2-fluorophenyl)-2-propylbenzofuran-5-yl)methoxy) phenyl)acetic Acid (188b)

Compound 188b was prepared according to the procedure reported in step-6 of Scheme-1 from ethyl 2-(2-((7-(3-(aminomethyl)-2-fluorophenyl)-2-propylbenzofuran-5-yl) methoxy)phenyl)acetate (188a) ((880 mg, 2.03 mmol) in MeOH/THF (30 mL each) using lithium hydroxide monohydrate (341 mg, 8.12 mmol) in water (7 mL). This gave after workup, purification by reverse phase column chromatography [C18 (50 g), eluting with ACN in water (containing 0.1% HCl) from 0-100%] 2-(2-((7-(3-(aminomethyl)-2-fluorophenyl)-2-propylbenzofuran-5-yl)methoxy)phenyl) acetic acid (188b) (220 mg, 25% yield for two steps) HCl salt as a white solid; $^1$H NMR (300 MHz, DMSO-$d_6$) δ 9.35 (s, 3H), 7.74-7.61 (m, 3H), 7.42 (t, J=7.7 Hz, 1H), 7.37 (t, J=1.3 Hz, 1H), 7.28-7.15 (m, 2H), 7.08 (d, J=8.0 Hz, 1H), 6.89 (td, J=7.4, 1.1 Hz, 1H), 6.69-6.67 (m, 1H), 5.23 (s, 2H), 4.16 (s, 2H), 3.57 (s, 2H), 2.73 (t, J=7.4 Hz, 2H), 1.69 (h, J=7.4 Hz, 2H), 0.95 (t, J=7.4 Hz, 3H); $^{19}$F NMR (282 MHz, DMSO-$d_6$) δ−118.66; MS (ES+): 448.4 (M+1); MS (ES−): 446.3 (M−1) & 482.4 (M+Cl); HPLC purity: 99.20%.

Scheme-189
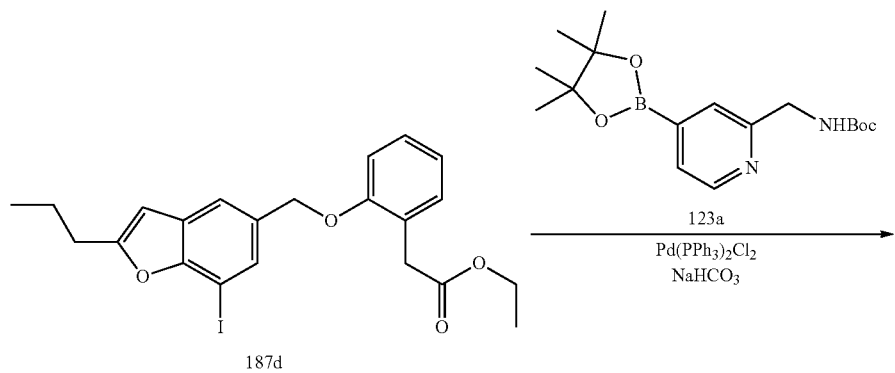
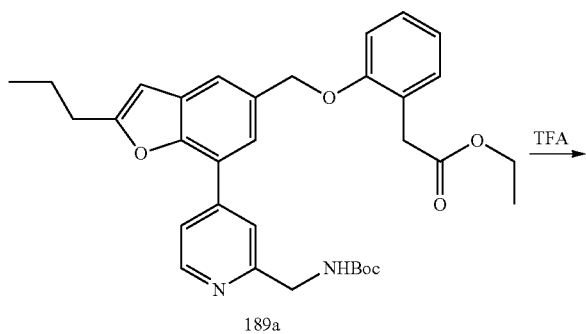
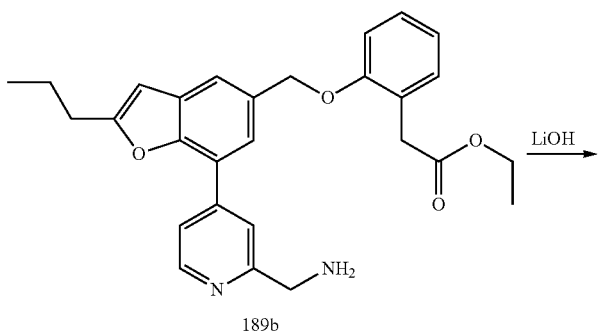
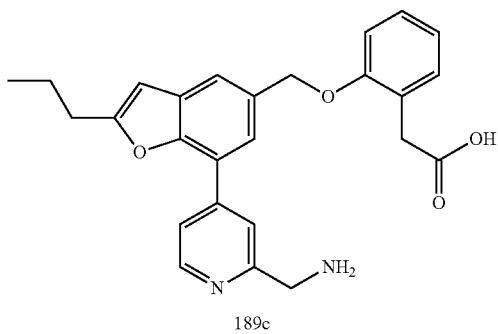

Preparation of 2-(2-((7-(2-(aminomethyl)pyridin-4-yl)-2-propylbenzofuran-5-yl)methoxy)phenyl)acetic Acid (189c)

Step-1: Preparation of Ethyl 2-(2-((7-(2-(((tert-butoxycarbonyl)amino)methyl)pyridin-4-yl)-2-propyl-benzofuran-5-yl)methoxy)phenyl)acetate (189a)

Compound 189a was prepared according to the procedure reported in step-3 of Scheme-1 from ethyl 2-(2-((7-iodo-2-propylbenzofuran-5-yl)methoxy)phenyl)acetate (187d) (844 mg, 1.76 mmol) in dioxane (30 mL) using tert-butyl (4-(4,4,5,5-tetramethyl-1,3,2-dioxaborolan-2-yl)pyridin-2-yl)methylcarbamate (123a) (1.18 g, 3.53 mmol), $K_2CO_3$ (732 mg, 5.30 mmol) in water (5 mL), bis(triphenylphosphine) palladium(II) chloride (186 mg, 0.265 mmol) and heating under an nitrogen atmosphere at 100° C. for 3.5 h on an oil bath. This gave after workup, purification by flash column chromatography [silica gel, eluting with 0 to 2.5% methanol in DCM] ethyl 2-(2-((7-(2-(((tert-butoxycarbonyl)amino)methyl)pyridin-4-yl)-2-propylbenzofuran-5-yl)methoxy)phenyl)acetate (189a) (597 mg, 61% yield); $^1$H NMR (300 MHz, DMSO-$d_6$) δ 8.62 (dd, J=5.2, 0.8 Hz, 1H), 7.82 (s, 1H), 7.75 (dd, J=5.2, 1.7 Hz, 1H), 7.68 (d, J=1.6 Hz, 1H), 7.65-7.53 (m, 1H), 7.49 (t, J=6.2 Hz, 1H), 7.33-7.17 (m, 2H), 7.13-7.08 (m, 1H), 6.91 (td, J=7.4, 1.1 Hz, 1H), 6.73-6.72 (m, 1H), 5.22 (s, 2H), 4.32 (d, J=6.1 Hz, 2H), 3.91 (q, J=7.1 Hz, 2H), 3.62 (s, 2H), 2.80 (t, J=7.4 Hz, 2H), 1.76 (h, J=7.3 Hz, 2H), 1.39 (s, 9H), 1.04-0.90 (m, 6H); MS (ES+): 559.3 (M+1).

Step-2: Preparation of Ethyl 2-(2-((7-(2-(aminomethyl)pyridin-4-yl)-2-propylbenzofuran-5-yl)methoxy)phenyl)acetate (189b)

Compound 189b was prepared according to the procedure reported in step-5 of Scheme-1 from ethyl 2-(2-((7-(2-(((tert-butoxycarbonyl)amino)methyl)pyridin-4-yl)-2-propylbenzofuran-5-yl)methoxy)phenyl)acetate (189a) (575 mg, 1.029 mmol) in DCM (30 mL) using TFA (0.8 mL, 10.29 mmol). This gave after workup and purification by flash column chromatography (silica gel, eluting with 0-10% methanol in DCM) ethyl 2-(2-((7-(2-(aminomethyl)pyridin-4-yl)-2-propylbenzofuran-5-yl)methoxy)phenyl)acetate (189b) (402 mg, 85% yield) as a gummy, brown solid. $^1$H NMR (300 MHz, DMSO-$d_6$) δ 8.78 (dd, J=5.2, 0.8 Hz, 1H), 8.36 (s, 3H), 8.02-8.00 (m, 1H), 7.97 (dd, J=5.3, 1.7 Hz, 1H), 7.70 (dd, J=13.0, 1.6 Hz, 2H), 7.32-7.18 (m, 2H), 7.10 (d, J=8.2 Hz, 1H), 6.91 (td, J=7.4, 1.1 Hz, 1H), 6.75 (d, J=1.0 Hz, 1H), 5.23 (s, 2H), 4.40-4.23 (m, 2H), 3.94 (q, J=7.1 Hz, 2H), 3.63 (s, 2H), 2.82 (t, J=7.4 Hz, 2H), 1.76 (h, J=7.4 Hz, 2H), 1.02-0.95 (m, 6H); MS (ES+): 459.2 (M+1).

Step-3: Preparation of 2-(2-((7-(2-(aminomethyl)pyridin-4-yl)-2-propylbenzofuran-5-yl)methoxy)phenyl)acetic Acid (189c)

Compound 189c was prepared according to the procedure reported in step-6 of Scheme-1 from ethyl 2-(2-((7-(2-(aminomethyl)pyridin-4-yl)-2-propylbenzofuran-5-yl)methoxy)phenyl)acetate (189b) (385 mg, 0.840 mmol) in THF/MeOH (10 mL each) using a solution of lithium hydroxide hydrate (141 mg, 3.36 mmol) in water (10 mL). This gave after workup and purification by reverse-phase column chromatography [C18 (50 g), eluting with ACN in water (containing 0.1% HCl) from 0-100%] 2-(2-((7-(2-(aminomethyl)pyridin-4-yl)-2-propylbenzofuran-5-yl)methoxy)phenyl)acetic acid (189c) (123 mg, 34% yield) HCl salt as a white solid; $^1$H NMR (300 MHz, DMSO-$d_6$) δ 8.79 (d, J=5.3 Hz, 1H), 8.63 (s, 3H), 8.13 (s, 1H), 8.04 (dd, J=5.4, 1.7 Hz, 1H), 7.75 (s, 2H), 7.31-7.17 (m, 2H), 7.11-7.04 (m, 1H), 6.90 (td, J=7.4, 1.1 Hz, 1H), 6.75-6.73 (m, 1H), 5.26 (s, 2H), 4.40-4.27 (m, 2H), 3.60 (s, 2H), 2.82 (t, J=7.4 Hz, 2H), 1.76 (h, J=7.4 Hz, 2H), 0.99 (t, J=7.4 Hz, 3H); MS (ES+): 431.2 (M+1); MS (ES−): 429.3 (M−1); HPLC purity: 96.66%.

Scheme-190

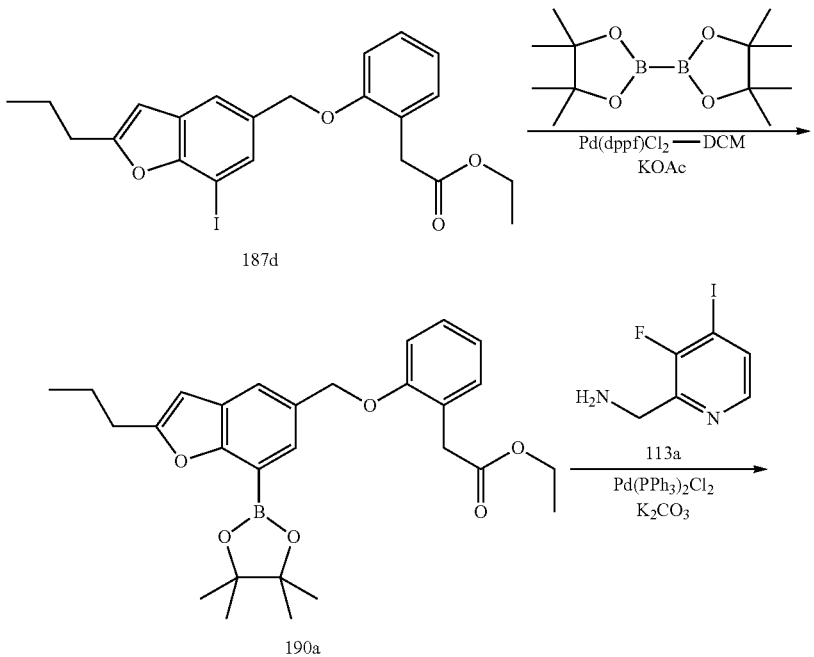

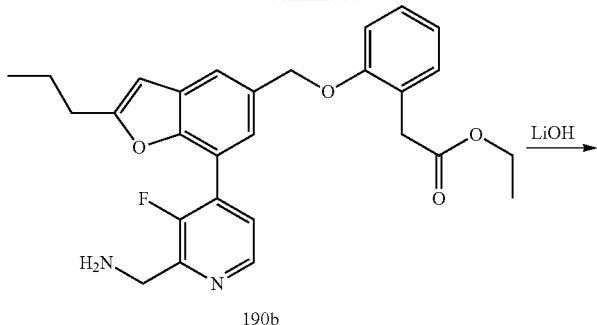

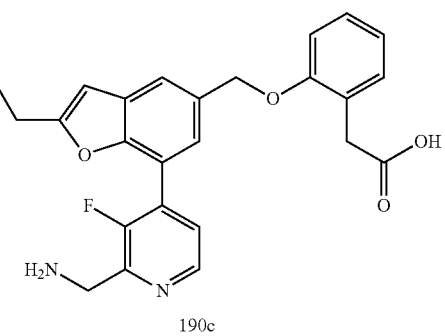

Preparation of 2-(2-((7-(2-(aminomethyl)-3-fluoro-pyridin-4-yl)-2-propylbenzofuran-5-yl)methoxy)phenyl)acetic Acid (190c)

Step-1: Preparation of Ethyl 2-(2-((2-propyl-7-(4,4,5,5-tetramethyl-1,3,2-dioxaborolan-2-yl)benzofuran-5-yl)methoxy)phenyl)acetate (190a)

Compound 190a was prepared according to the procedure reported in step-1 of Scheme-59 from ethyl 2-(2-((7-iodo-2-propylbenzofuran-5-yl)methoxy)phenyl)acetate (187d) (5.00 g, 10.45 mmol), using bis(pinacolato)diboron (3.98 g, 15.68 mmol), potassium acetate (3.08 g, 31.36 mmol) and Pd(dppf)Cl$_2$—CH$_2$Cl$_2$ (761 mg, 1.04 mmnol) in anhydrous dioxane (120 mL) under an Ar atmosphere and heating at 90° C. for 14 h. This gave after workup and purification by flash column chromatography [silica gel, eluting with ethyl acetate in hexane from 0-10%] ethyl 2-(2-((2-propyl-7-(4,4,5,5-tetramethyl-1,3,2-dioxaborolan-2-yl)benzofuran-5-yl)methoxy)phenyl)acetate (190a) (1.84 g, not very pure, used as such for next step).

Step-2: Preparation of Ethyl 2-(2-((7-(2-(aminomethyl)-3-fluoropyridin-4-yl)-2-propylbenzofuran-5-yl)methoxy)phenyl)acetate (190b)

Compound 190b was prepared according to the procedure reported in step-3 of Scheme-1 ethyl 2-(2-((2-propyl-7-(4,4,5,5-tetramethyl-1,3,2-dioxaborolan-2-yl)benzofuran-5-yl)methoxy)phenyl)acetate (190a) (1.162 g, 2.428 mmol) in dioxane (30 mL) using (3-fluoro-4-iodopyridin-2-yl)methanamine (113a) (0.510 g, 2.024 mmol), bis(triphenylphosphine)palladium(II) chloride (245 mg, 0.304 mmol) and a solution of K$_2$CO$_3$ (839 mg, 6.07 mmol) in water (5 mL) under an Ar atmosphere and heating at 100° C. for 3.5 h on oil bath. This gave after workup, purification by flash column chromatography [silica gel, eluting with DMA80 in DCM from 0-20%] ethyl 2-(2-((7-(2-(aminomethyl)-3-fluoropyridin-4-yl)-2-propylbenzofuran-5-yl)methoxy)phenyl)acetate (190b) (70 mg, 2.7% for two steps); $^1$H NMR (300 MHz, DMSO-d$_6$) δ 8.52 (d, J=5.0 Hz, 1H), 7.72 (d, J=1.6 Hz, 1H), 7.60 (t, J=5.3 Hz, 1H), 7.44-7.42 (m, 1H), 7.34-7.19 (m, 2H), 7.13-7.09 (m, 1H), 6.91 (td, J=7.4, 1.1 Hz, 1H), 6.73-6.71 (m, 1H), 5.22 (s, 2H), 3.99-3.87 (m, 4H), 3.61 (s, 2H), 2.75 (t, J=7.3 Hz, 2H), 1.70 (h, J=7.3 Hz, 2H), 1.02-0.88 (m, 6H); MS (ES+): 477.25 (M+1).

Step-3: Preparation of 2-(2-((7-(2-(aminomethyl)-3-fluoropyridin-4-yl)-2-propylbenzofuran-5-yl)methoxy)phenyl)acetic Acid (190c)

Compound 190c was prepared according to the procedure reported in step-6 of Scheme-1 from ethyl 2-(2-((7-(2-(aminomethyl)-3-fluoropyridin-4-yl)-2-propylbenzofuran-5-yl)methoxy)phenyl)acetate (190b) (23 mg, 0.546 mmol) THF/MeOH (3 mL each) using lithium hydroxide monohydrate (20 mg, 0.48 mmol) in Water (3 mL). This gave after workup and purification by reverse phase column [C18 (50 g), eluting with ACN in water (containing 0.1% HCl) from 0-100%] 2-(2-((7-(2-(aminomethyl)-3-fluoropyridin-4-yl)-2-propylbenzofuran-5-yl)methoxy)phenyl)acetic acid (190c) (2 mg, 3.27%) HCl salt as a fluffy white solid; $^1$H NMR (300 MHz, DMSO-d$_6$) δ 8.63 (d, J=5.0 Hz, 1H), 8.42 (s, 3H), 7.84-7.74 (m, 2H), 7.49 (s, 1H), 7.27-7.17 (m, 2H), 7.09 (d, J=8.1 Hz, 1H), 6.90 (t, J=7.3 Hz, 1H), 6.73 (s, 1H), 5.25 (s, 2H), 4.46-4.32 (m, 2H), 3.57 (s, 2H), 2.78-2.73 (m, 2H), 1.86-1.56 (m, 2H), 0.95 (t, J=7.4 Hz, 3H); $^{19}$F NMR (282 MHz, DMSO-d$_6$) δ−128.55; 449.2 (M+1); HPLC purity: 91.91%.

Scheme-191

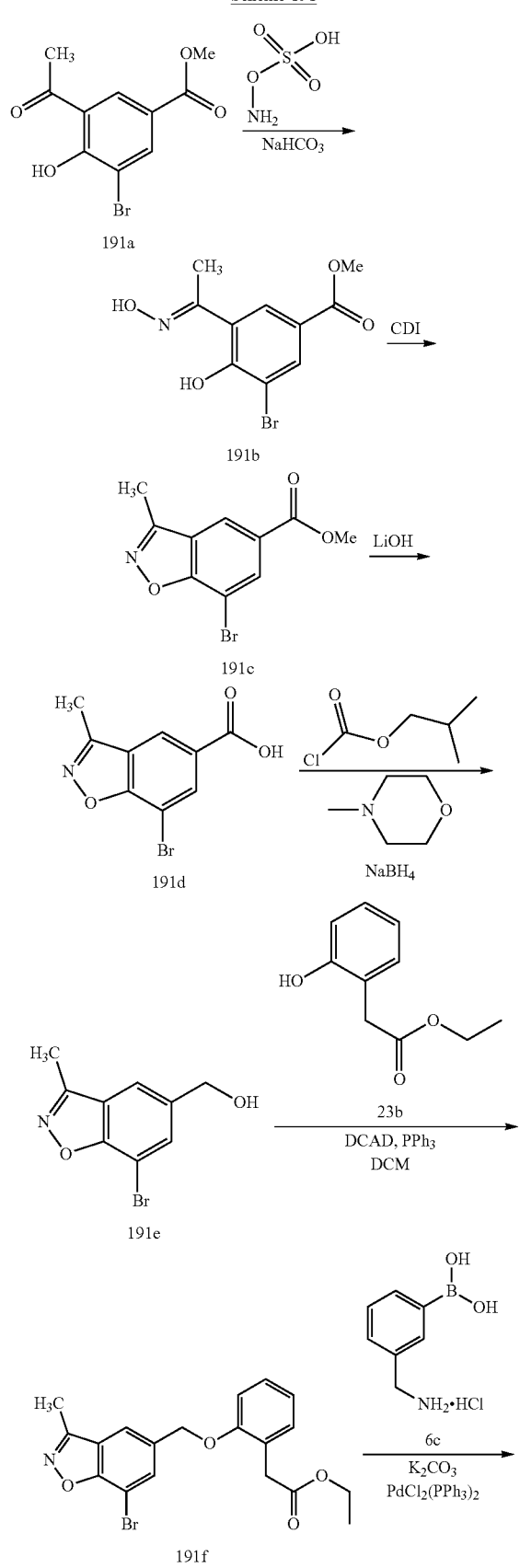

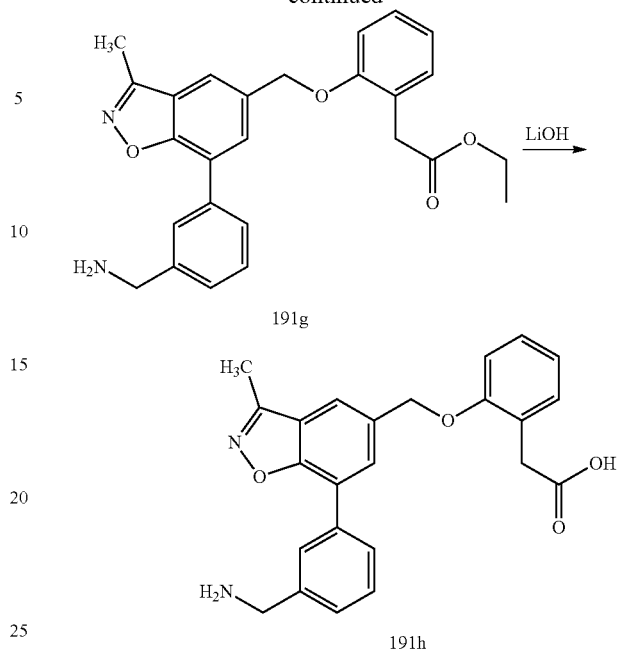

Preparation of 2-(2-((7-(3-(aminomethyl)phenyl)-3-methylbenzo[d]isoxazol-5-yl)methoxy)phenyl)acetic Acid (191h)

Step-1, b: Preparation of (E/Z)-methyl 3-bromo-4-hydroxy-5-(1-(hydroxyimino)ethyl)benzoate (191 b)

To a solution of methyl 3-acetyl-5-bromo-4-hydroxybenzoate (191a) (1 g, 3.66 mmol; CAS #160753-84-4) in ethanol (30 mL) and dichloromethane (30 mL) at room temperature was added aminooxysulfonic acid (0.621 g, 5.49 mmol) and stirred for 24 h. The reaction mixture was quenched with a solution of sodium bicarbonate (1.538 g, 18.31 mmol) in water (20 mL) and stirred at RT for 6 h. The reaction mixture was filtered to remove separated solid and the filtrate was extracted with ethyl acetate (3×50 mL). The organic layers were combined washed with water, brine, dried, filtered and concentrated in vacuum to furnish (E/Z)-methyl 3-bromo-4-hydroxy-5-(1-(hydroxyimino)ethyl)benzoate (191b) (700 mg, 66.4% yield) which was used as such in next step without further purification; $^1$H NMR (300 MHz, DMSO-$d_6$) δ 13.48 (s, 1H), 12.16 (d, J=19.2 Hz, 1H), 8.07 (d, J=2.0 Hz, 1H), 8.06 (s, 1H), 3.84 (s, 3H), 2.33 (s, 3H); MS (ES+): 290.00, 288.00 (M+1), (ES−): 288.10, 286.10 (M−1).

Step-2: Preparation of methyl 7-bromo-3-methylbenzo[d]isoxazole-5-carboxylate (191c)

A solution of (E/Z)-methyl 3-bromo-4-hydroxy-5-(1-(hydroxyimino)ethyl)benzoate (191b) (640 mg, 2.221 mmol) and carbonyl diimidazole (720 mg, 4.44 mmol) in tetrahydrofuran (10 mL) was heated at reflux for 90 min. The reaction mixture was cooled to room temperature, partitioned between EtOAc and water and acidified with conc HCl. The solution was extracted three times with EtOAc. The organic layers were combined washed with water, brine, dried filtered and concentrated in vacuum. The residue obtained was purified by flash column chromatography

[silica gel (40 g), eluting with ethyl acetate and hexanes] to afford methyl 7-bromo-3-methylbenzo[d]isoxazole-5-carboxylate (191c) (369 mg, 62% yield) as a white solid; 1H NMR (300 MHz, DMSO-$d_6$) δ 8.52 (d, J=1.4 Hz, 1H), 8.35 (d, J=1.4 Hz, 1H), 3.91 (s, 3H), 2.63 (s, 3H).

Step-3: Preparation of 7-bromo-3-methylbenzo[d]isoxazole-5-carboxylic Acid (191d)

Compound 191d was prepared according to the procedure reported in step-6 of Scheme-1 from methyl 7-bromo-3-methylbenzo[d]isoxazole-5-carboxylate (191c) (340 mg, 1.259 mmol) in MeOH/THF (10 mL each) using a solution of lithium hydroxide hydrate (90 mg, 3.78 mmol) in water (2 mL) This gave after workup 7-bromo-3-methylbenzo[d]isoxazole-5-carboxylic acid (191d) (313 mg, 97% yield) as a white solid; $^1$H NMR (300 MHz, DMSO-$d_6$) δ 13.48 (s, 1H), 8.45 (d, J=1.4 Hz, 1H), 8.31 (d, J=1.4 Hz, 1H), 2.62 (s, 3H).

Step-4: Preparation of (7-bromo-3-methylbenzo[d]isoxazol-5-yl)methanol (191e)

Compound 191e was prepared according to the procedure reported in step-1 of Scheme-23 from 7-bromo-3-methylbenzo[d]isoxazole-5-carboxylic acid (191d) (300 mg, 1.172 mmol) using N-methylmorpholine (0.155 mL, 1.406 mmol) in THF (10 mL), isobutyl chloroformate (0.185 mL, 1.406 mmol) and NaBH$_4$ (133 mg, 3.51 mmol) in water (1 mL). This gave after workup and purification by flash column chromatography [silica gel (25 g), eluting with methanol in DCM from 0-100%] (7-bromo-3-methylbenzo[d]isoxazol-5-yl)methanol (191e) (190 mg, 67% yield) as a white solid; 1H NMR (300 MHz, DMSO-$d_6$) δ 7.83 (m, 1H), 7.78 (m, 1H), 5.47 (t, J=5.7 Hz, 1H), 4.62 (dt, J=5.7, 0.8 Hz, 2H), 2.56 (s, 3H).

Step-5: Preparation of Ethyl 2-(2-((7-bromo-3-methylbenzo[d]isoxazol-5-yl)methoxy)phenyl)acetate (191f)

Compound 191f was prepared according to the procedure reported in step-2 of Scheme-23 from (7-bromo-3-methylbenzo[d]isoxazol-5-yl)methanol (191e) (180 mg, 0.744 mmol) in DCM (15 mL) using triphenylphosphine (215 mg, 0.818 mmol), ethyl 2-(2-hydroxyphenyl) acetate (23b) (167 mg, 0.929 mmol) and di-(4-chlorobenzyl)azodicarboxylate (DCAD, 300 mg, 0.818 mmol) in DCM (15 mL). This gave after workup and purification by flash column chromatography [silica gel, eluting with EtOAc in hexane from 0-50%] ethyl 2-(2-((7-bromo-3-methylbenzo[d]isoxazol-5-yl)methoxy)phenyl)acetate (191f) (190 mg, 63% yield) as a white solid; $^1$H NMR (300 MHz, DMSO-$d_6$) δ 7.94 (s, 2H), 7.31-7.19 (m, 2H), 7.08 (dd, J=8.2, 1.1 Hz, 1H), 6.93 (td, J=7.4, 1.1 Hz, 1H), 5.23 (s, 2H), 4.01 (q, J=7.1 Hz, 2H), 3.64 (s, 2H), 2.58 (s, 3H), 1.06 (t, J=7.1 Hz, 3H); MS (ES+): 406.10, 404.05 (M+1).

Step-6: Preparation of Ethyl 2-(2-((7-(3-(aminomethyl)phenyl)-3-methylbenzo[d]isoxazol-5-yl)methoxy)phenyl)acetate (191g)

Compound 191g was prepared according to the procedure reported in step-3 of Scheme-1 from ethyl 2-(2-((7-bromo-3-methylbenzo[d]isoxazol-5-yl)methoxy)phenyl)acetate (191f) (187 mg, 0.463 mmol) in dioxane (10 mL) using 3-(aminomethyl)phenylboronic acid hydrochloride (6c) (139 mg, 0.740 mmol), bis(triphenylphosphine)palladium (ll)chloride (48.7 mg, 0.069 mmol) and potassium carbonate (192 mg, 1.388 mmol) in water (1 mL) under an Ar atmosphere and heating at 100° C. for 5 h in an oil bath. This gave after workup, purification by flash column chromatography [silica gel (25 g), eluting with DMA80 in DCM from 0-50%] ethyl 2-(2-((7-(3-(aminomethyl)phenyl)-3-methylbenzo[d]isoxazol-5-yl)methoxy)phenyl)acetate (191g) (30 mg, 15% yield); MS (ES+): 431.20 (M+1).

Step-7: Preparation of 2-(2-((7-(3-(aminomethyl)phenyl)-3-methylbenzo[d]isoxazol-5-yl)methoxy)phenyl)acetic Acid (191h)

Compound 191h was prepared according to the procedure reported in step-6 of Scheme-1 from ethyl 2-(2-((7-(3-(aminomethyl)phenyl)-3-methylbenzo[d]isoxazol-5-yl)methoxy)phenyl)acetate (191g) (25 mg, 0.058 mmol) in MeOH/THF (5 mL each) using a solution of lithium hydroxide hydrate (6 mg, 0.232 mmol) in water (1 mL). This gave after workup and purification by reverse phase column chromatography [C18 (50 g), eluting with ACN in water (containing 0.1% HCl) from 0-100%] 2-(2-((7-(3-(aminomethyl)phenyl)-3-methylbenzo[d]isoxazol-5-yl)methoxy)phenyl)acetic acid (191h) (8 mg, 34% yield) HCl salt as a white solid; $^1$H NMR (300 MHz, DMSO-$d_6$) δ 8.31 (bs, 3H), 8.06 (d, J=1.8 Hz, 1H), 7.97 (m, 3H), 7.69-7.53 (m, 2H), 7.25 (m, 2H), 7.10 (d, J=8.0 Hz, 1H), 6.92 (td, J=7.4, 1.1 Hz, 1H), 5.32 (s, 2H), 4.16 (s, 2H), 3.62 (s, 2H), 2.61 (s, 3H); MS (ES+): 403.2 (M+1), (ES−): 401.3 (M−1).

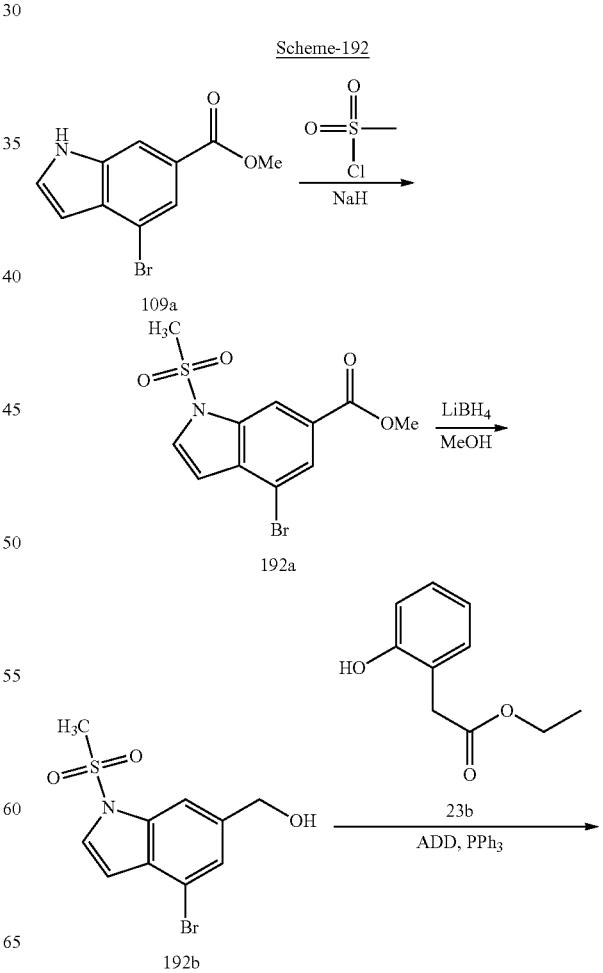

Scheme-192

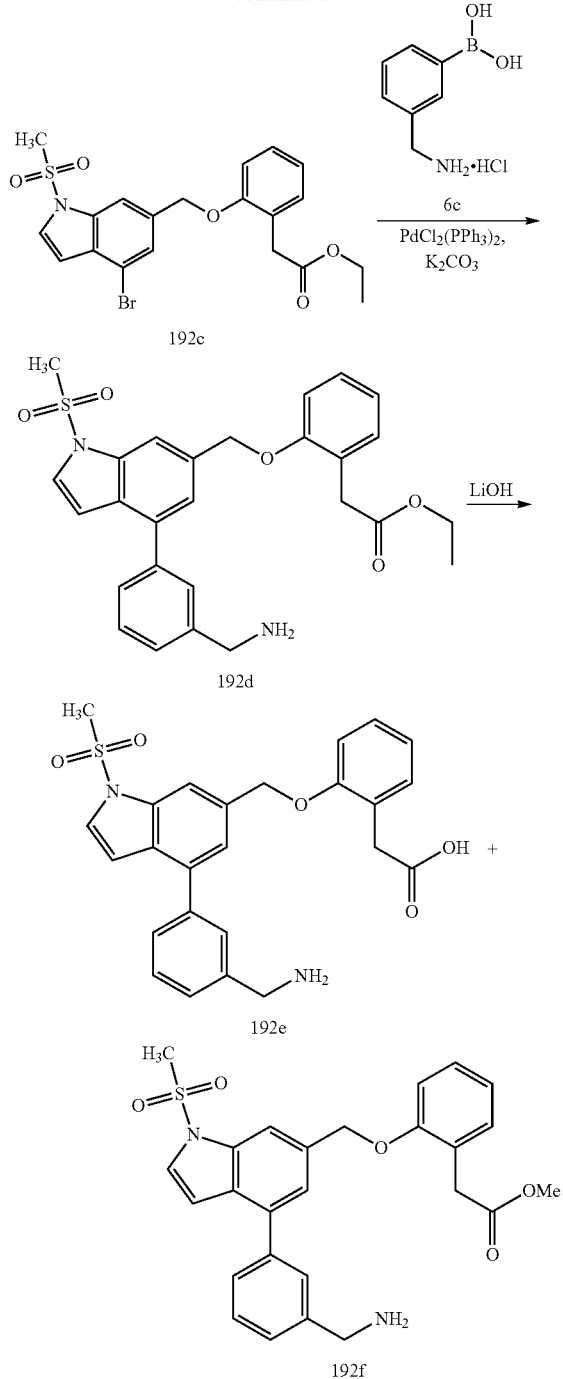

Preparation of 2-(2-((4-(3-(aminomethyl)phenyl)-1-(methylsulfonyl)-1H-indol-6-yl)methoxy)phenyl) acetic Acid (192e)

Step-1: Preparation of methyl 4-bromo-1-(methylsulfonyl)-1H-indole-6-carboxylate (192a)

Compound 192a was prepared according to the procedure reported in step-1 of Scheme-40 from methyl 4-bromo-1H-indole-6-carboxylate (109a) (2 g, 7.87 mmol) in DMF (15 mL) using NaH (60% in mineral oil, 0.94 g, 23.61 mmol) and methanesulfonyl chloride (1.83 mL, 23.61 mmol). This gave after work-up and purification by flash column chromatography [silica (12 g), eluting with EtOAc/MeOH=9:1 in Hexane from 0-50%] methyl 4-bromo-1-(methylsulfonyl)-1H-indole-6-carboxylate (192a) (1.4 g, 54% yield) as a white solid; $^1$H NMR (300 MHz, DMSO-$d_6$) δ 8.48 (t, J=1.0 Hz, 1H), 8.04 (d, J=1.3 Hz, 1H), 7.96 (d, J=3.7 Hz, 1H), 6.90 (dd, J=3.7, 0.9 Hz, 1H), 3.91 (s, 3H), 3.59 (s, 3H); MS (ES−): 334.0, 332.1 (M−1).

Step-2: Preparation of (4-bromo-1-(methylsulfonyl)-1H-indol-6-yl)methanol (192b)

Compound 192b was prepared according to the procedure reported in step-2 of Scheme-76 from methyl 4-bromo-1-(methylsulfonyl)-1H-indole-6-carboxylate (192a) (0.8 g, 2.41 mmol) in THF (8 mL) using LiBH$_4$ (2.41 mL, 7.23 mmol) and MeOH (0.29 mL, 7.23 mmol). This gave after workup (4-bromo-1-(methylsulfonyl)-1H-indol-6-yl)methanol (192b) (0.57 g, 78% yield) as a clear oil; $^1$H NMR (300 MHz, DMSO-$d_6$) δ 7.84 (p, J=0.9 Hz, 1H), 7.67 (d, J=3.7 Hz, 1H), 7.50 (d, J=1.2 Hz, 1H), 6.74 (dd, J=3.7, 0.8 Hz, 1H), 5.42 (t, J=5.8 Hz, 1H), 4.63 (d, J=5.7 Hz, 2H), 3.48 (s, 3H).

Step-3: Preparation of Ethyl 2-(2-((4-bromo-1-(methylsulfonyl)-1H-indol-6-yl)methoxy)phenyl) acetate (192c)

Compound 192c was prepared according to the procedure reported in step-2 of Scheme-23 from (4-bromo-1-(methylsulfonyl)-1H-indol-6-yl)methanol (192b) (0.57 g, 1.87 mmol) in toluene (8 mL) using triphenylphosphine (0.639 g, 2.436 mmol), ethyl 2-(2-hydroxyphenyl) acetate (23b) (0.44 g, 2.44 mmol) and (E)-diazene-1,2-diylbis(piperidin-1-yl-methanone) (0.62 g, 2.44 mmol) in toluene (5 mL). This gave after workup and purification by flash column chromatography [silica (24 g), eluting with EtOAc/MeOH (9:1) in hexane from 0-10% for 40 min, then 10%-50%] ethyl 2-(2-((4-bromo-1-(methylsulfonyl)-1H-indol-6-yl)methoxy)phenyl)acetate (192c) (0.68 g, 78% yield) as a yellow oil; $^1$H NMR (300 MHz, DMSO-$d_6$) δ 7.95 (t, J=1.0 Hz, 1H), 7.74 (d, J=3.7 Hz, 1H), 7.61 (d, J=1.2 Hz, 1H), 7.30-7.19 (m, 2H), 7.10 (dd, J=8.2, 1.1 Hz, 1H), 6.92 (td, J=7.4, 1.1 Hz, 1H), 6.78 (dd, J=3.7, 0.8 Hz, 1H), 5.24 (s, 2H), 4.03 (q, J=7.1 Hz, 2H), 3.63 (s, 2H), 3.52 (s, 3H), 1.08 (t, J=7.1 Hz, 3H). MS (ES−): 466.1, 464.2 (M−1).

Step-4: Preparation of Ethyl 2-(2-((4-(3-(aminomethyl)phenyl)-1-(methylsulfonyl)-1H-indol-6-yl)methoxy)phenyl)acetate (192d)

Compound 192d was prepared according to the procedure reported in step-3 of Scheme-1 from ethyl 2-(2-((4-bromo-1-(methylsulfonyl)-1H-indol-6-yl)methoxy)phenyl)acetate (192c) (0.23 g, 0.49 mmol) in dioxane (4 mL) using 3-(aminomethyl)phenylboronic acid hydrochloride (6c) (0.14 g, 0.74 mmol), K$_2$CO$_3$ (0.10 g, 0.74 mmol) in water (2 mL) and bis(triphenylphosphine)palladium(ll)chloride (0.05 g, 0.07 mmol) under an Ar atmosphere and heating at 90° C. for 2 h on oil bath. This gave after workup, purification by flash column chromatography [silica (12 g), eluting with MeOH in DCM from 0-20%] ethyl 2-(2-((4-(3-(aminomethyl)phenyl)-1-(methylsulfonyl)-1H-indol-6-yl)methoxy)phenyl)acetate (192d) (0.04 g, 15% yield) as a white solid; MS (ES+): 493.2 (M+1).

Step-5: Preparation of 2-(2-((4-(3-(aminomethyl)phenyl)-1-(methylsulfonyl)-1H-indol-6-yl)methoxy)phenyl)acetic Acid (192e)

Compound 192e was prepared according to the procedure reported in step-6 of Scheme-1 from ethyl 2-(2-((4-(3-(aminomethyl)phenyl)-1-(methylsulfonyl)-1H-indol-6-yl)methoxy)phenyl)acetate (192d) (0.04 g, 0.08 mmol) in MeOH/THF (3 mL, 1:1) using a solution of lithium hydroxide hydrate (3 mg, 0.08 mmol) in water (0.5 mL). This gave after workup and purification by flash column chromatography [silica (4 g), eluting with MeOH in DCM from 0-50%] 2-(2-((4-(3-(aminomethyl)phenyl)-1-(methylsulfonyl)-1H-indol-6-yl)methoxy)phenyl)acetic acid (192e) (0.02 g, 43% yield) as a white solid; $^1$H NMR (300 MHz, DMSO-$d_6$) δ 8.12 (s, 1H), 7.94 (s, 1H), 7.73 (s, 1H), 7.72-7.64 (m, 2H), 7.49 (t, J=7.5 Hz, 1H), 7.38 (d, J=7.9 Hz, 1H), 7.15-7.05 (m, 2H), 7.02 (s, 1H), 6.97 (m, 1H), 6.81 (t, J=7.2 Hz, 1H), 5.31 (s, 2H), 4.01 (s, 2H), 3.51 (s, 3H), 3.40 (s, 2H); MS (ES+): 465.2 (M+1), MS (ES−): 463.2 (M−1) and methyl 2-(2-((4-(3-(aminomethyl)phenyl)-1-(methylsulfonyl)-1H-indol-6-yl)methoxy)phenyl)acetate (192f) (0.02 g, 58% yield) as a white solid; $^1$H NMR (300 MHz, DMSO-$d_6$) δ 7.95 (s, 1H), 7.70-7.65 (m, 3H), 7.55-7.49 (m, 2H), 7.49-7.40 (m, 1H), 7.30-7.19 (m, 2H), 7.17-7.12 (m, 1H), 6.96-6.87 (m, 2H), 5.30 (s, 2H), 3.92 (s, 2H), 3.66 (s, 2H), 3.50 (s, 3H), 3.45 (s, 3H); MS (ES+) 479.2 (M+1).

Scheme-193

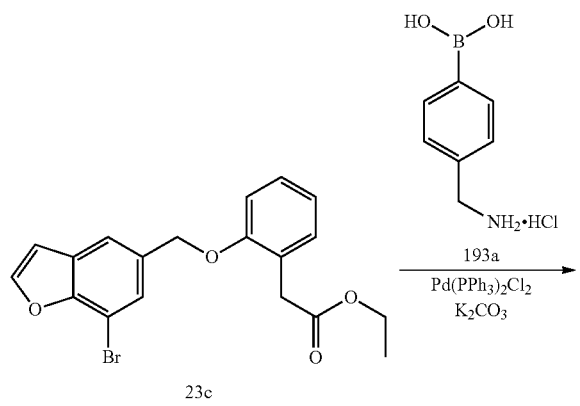

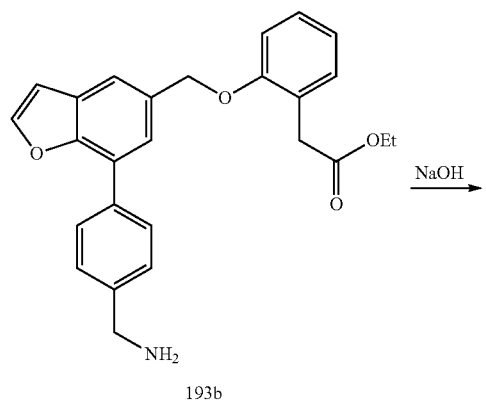

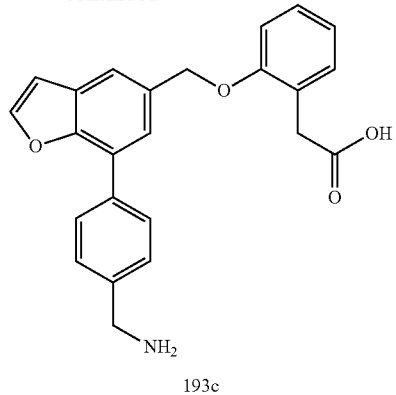

Preparation of 2-(2-((7-(4-(aminomethyl)phenyl)benzofuran-5-yl)methoxy)phenyl)acetic acid (193c)

Step-1: Preparation of Ethyl 2-(2-((7-(4-(aminomethyl)phenyl)benzofuran-5-yl)methoxy)phenyl)acetate (193b)

Compound 193b was prepared according to the procedure reported in step-1 of Scheme-59 from ethyl 2-(2-((7-bromobenzofuran-5-yl)methoxy)phenyl)acetate (23c) (200 mg, 0.514 mmol) in dioxane (2 mL) and H$_2$O (1 mL) using (4-(aminomethyl)phenyl)boronic acid hydrochloride (193a) (106 mg, 0.565 mmol; CAS #75705-21-4), bis(triphenylphosphine)palladium(II) chloride (36.1 mg, 0.051 mmol) and K$_2$CO$_3$ (213 mg, 1.541 mmol) under a nitrogen atmosphere and heating at 80° C. for 16 h on oil bath. This gave after workup, purification by flash column chromatography [silica gel eluting with 0-15% MeOH in DCM] ethyl 2-(2-((7-(4-(aminomethyl)phenyl)benzofuran-5-yl)methoxy)phenyl)acetate (193b) (73 mg, 34% yield) as a pale-yellow semisolid. $^1$H NMR (300 MHz, DMSO-$d_6$) δ 8.09 (d, J=2.2 Hz, 1H), 7.86-7.79 (m, 2H), 7.68 (d, J=1.7 Hz, 1H), 7.57 (d, J=1.7 Hz, 1H), 7.49 (d, J=8.0 Hz, 2H), 7.32-7.19 (m, 2H), 7.12 (d, J=8.1 Hz, 1H), 7.04 (d, J=2.2 Hz, 1H), 6.91 (td, J=7.4, 1.1 Hz, 1H), 5.24 (s, 2H), 3.93 (q, J=7.1 Hz, 2H), 3.79 (s, 2H), 3.63 (s, 2H), 0.99 (t, J=7.1 Hz, 3H). MS (ES+): 416 (M+1), 438 (M+Na).

Step-2: Preparation of 2-(2-((7-(4-(aminomethyl)phenyl)benzofuran-5-yl)methoxy)phenyl)acetic Acid (193c)

Compound 193c was prepared according to the procedure reported in step-4 of Scheme-4 from ethyl 2-(2-((7-(4-(aminomethyl)phenyl)benzofuran-5-yl)methoxy)phenyl)acetate (193b) (70 mg, 0.168 mmol) in THF (1 mL) and MeOH (2 mL) using NaOH (34 mg, 0.842 mmol) in water (1 mL). This gave after workup and purification by reverse phase column [C18 (100 g), eluting with ACN in water (containing 0.1% HCl) from 0-100%] 2-(2-((7-(4-(aminomethyl)phenyl)benzofuran-5-yl)methoxy)phenyl)acetic acid (193c) (50 mg, 77% yield) as an off-white solid; $^1$H NMR (300 MHz, DMSO-$d_6$) δ 8.45 (s, 3H), 8.10 (d, J=2.2 Hz, 1H), 8.02-7.89 (m, 2H), 7.75 (d, J=1.6 Hz, 1H), 7.69-7.59 (m, 3H), 7.31-7.18 (m, 2H), 7.10 (d, J=7.8 Hz, 1H), 7.05 (d, J=2.2 Hz, 1H), 6.90 (td, J=7.4, 1.1 Hz, 1H), 5.27 (s, 2H), 4.11 (s, 2H), 3.59 (s, 2H). MS (ES+): 388 (M+1).

Scheme-194

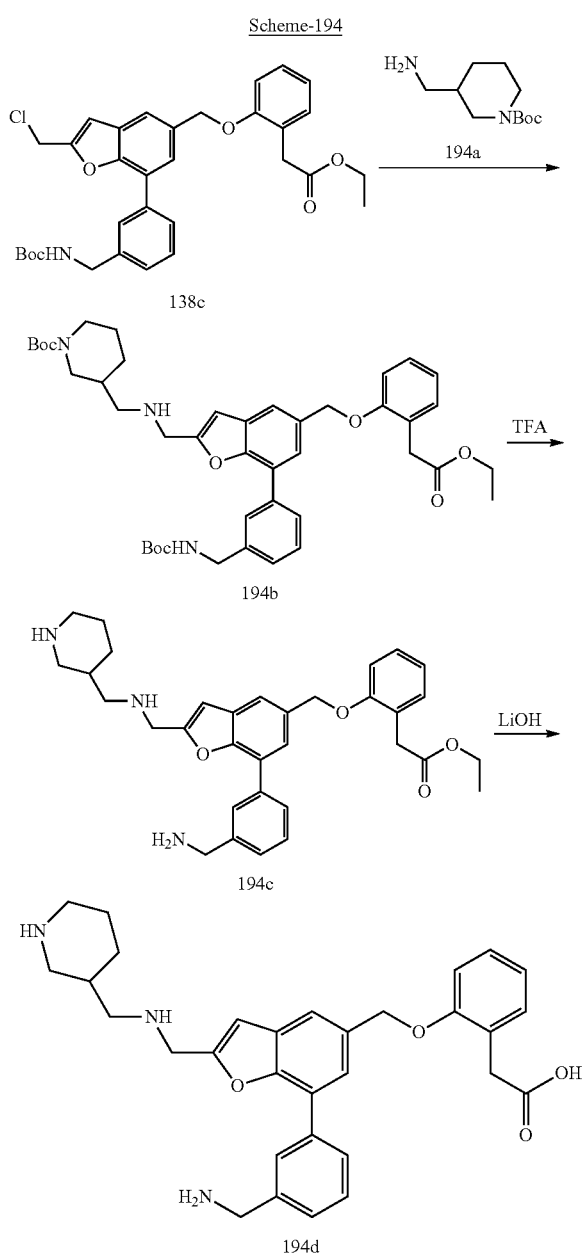

Preparation of 2-(2-((7-(3-(aminomethyl)phenyl)-2-(((piperidin-3-ylmethyl)amino)methyl)benzofuran-5-yl)methoxy)phenyl)acetic Acid (194d)

Step-1: Preparation of tert-butyl 3-((((7-(3-(((tert-butoxycarbonyl)amino)methyl)phenyl)-5-((2-(2-ethoxy-2-oxoethyl)phenoxy)methyl)benzofuran-2-yl)methyl)amino)methyl)piperidine-1-carboxylate (194b)

Compound 194b was prepared according to the procedure reported in step-4 of Scheme-138 from 2-(2-((7-(3-(((tert-butoxycarbonyl)amino)methyl)phenyl)-2-(chloromethyl)benzofuran-5-yl)methoxy)phenyl)acetate (138c) (400 mg, 0.71 mmol) and tert-butyl 3-(aminomethyl)piperidine-1-carboxylate (194a) (608 mg, 2.84 mmol; CAS #162167-97-7) in ACN (5 mL). This gave after workup and purification by flash column chromatography [silica (12 g), eluting with DMA80 in DCM from 0-50%] tert-butyl 3-((((7-(3-(((tert-butoxycarbonyl)amino)methyl)phenyl)-5-((2(2-ethoxy-2-oxoethyl)phenoxy)methyl)benzofuran-2-yl)methyl)amino)methyl)piperidine-1-carboxylate (194b) (330 mg, 63% yield) as a clear oil; $^1$H NMR (300 MHz, DMSO-$d_6$) δ 7.78-7.71 (m, 2H), 7.62-7.59 (m, 1H), 7.52-7.43 (m, 3H), 7.32-7.19 (m, 3H), 7.13-7.08 (m, 1H), 6.91 (td, J=7.4, 1.1 Hz, 1H), 6.78 (s, 1H), 5.21 (s, 2H), 4.22 (d, J=6.2 Hz, 2H), 3.96-3.83 (m, 5H), 3.77-3.68 (m, 1H), 3.62 (s, 2H), 2.82-2.70 (m, 1H), 2.46-2.40 (m, 2H), 2.33-2.21 (m, 1H), 1.79-1.68 (m, 1H), 1.61-1.48 (m, 2H), 1.37 (d, J=8.7 Hz, 18H), 1.32-1.20 (m, 2H), 1.17-1.04 (m, 1H), 0.98 (t, J=7.1 Hz, 3H); MS (ES+): 742.4 (M+1).

Step-2: Preparation of Ethyl 2-(2-((7-(3-(aminomethyl)phenyl)-2-(((piperidin-3-ylmethyl)amino)methyl)benzofuran-5-yl)methoxy)phenyl)acetate (194c)

Compound 194c was prepared according to the procedure reported in step-5 of Scheme-1 from tert-butyl 3-((((7-(3-(((tert-butoxycarbonyl)amino)methyl)phenyl)-5-((2-(2-ethoxy-2-oxoethyl)phenoxy)methyl)benzofuran-2-yl)methyl)amino)methyl)piperidine-1-carboxylate (194b) (320 mg, 0.43 mmol) in DCM (10 mL) using TFA (0.332 mL, 4.31 mmol). This gave after workup ethyl 2-(2-((7-(3-(aminomethyl)phenyl)-2-(((piperidin-3-ylmethyl)amino)methyl)benzofuran-5-yl)methoxy)phenyl)acetate (194c) (211 mg, 90% yield) as a yellow oil; MS (ES+): 542.4 (M+1).

Step-3: Preparation of 2-(2-((7-(3-(aminomethyl)phenyl)-2-(((piperidin-3-ylmethyl)amino)methyl)benzofuran-5-yl)methoxy)phenyl)acetic Acid (194d)

Compound 194d was prepared according to the procedure reported in step-6 of Scheme-1 from ethyl 2-(2-((7-(3-(aminomethyl)phenyl)-2-(((piperidin-3-ylmethyl)amino)methyl)benzofuran-5-yl)methoxy)phenyl)acetate (194c) (169 mg, 0.31 mmol) in THF (6 mL) and methanol (6 mL) using a solution of lithium hydroxide monohydrate (17 mg, 0.41 mmol) in water (2.0 mL). This gave after workup and purification by reverse phase column [C18 (50 g), eluting with ACN in water (containing 0.1% HCl) from 0-100%] 2-(2-((7-(3-(aminomethyl)phenyl)-2-(((piperidin-3-ylmethyl)amino)methyl)benzofuran-5-yl)methoxy)phenyl)acetic acid (194d) (58 mg, 36% yield) as a white solid; $^1$H NMR (300 MHz, DMSO-$d_6$) δ 12.26 (s, 1H, D$_2$O exchangeable), 10.03 (s, 2H, D$_2$O exchangeable), 9.40-9.26 (m, 1H, D$_2$O exchangeable), 9.23-9.04 (m, 1H, D$_2$O exchangeable), 8.66 (s, 3H, D$_2$O exchangeable), 8.30-8.22 (m, 1H), 7.97 (dt, J=6.8, 2.1 Hz, 1H), 7.78 (d, J=1.6 Hz, 1H), 7.72 (d, J=1.6 Hz, 1H), 7.61-7.52 (m, 2H), 7.28-7.17 (m, 3H), 7.09 (d, J=8.1 Hz, 1H), 6.90 (td, J=7.4, 1.1 Hz, 1H), 5.28 (s, 2H), 4.44 (s, 2H), 4.17 (d, J=5.8 Hz, 2H), 3.60 (s, 2H), 3.47 (d, J=10.9 Hz, 2H), 3.15 (d, J=12.1 Hz, 1H), 3.07-2.87 (m, 2H), 2.79-2.64 (m, 2H), 2.45-2.29 (m, 1H), 1.95-1.85 (m, 1H), 1.83-1.60 (m, 2H), 1.36-1.17 (m, 1H); MS (ES+): 514.3 (M+1); (ES−): 512.4 (M−1).

Scheme-195

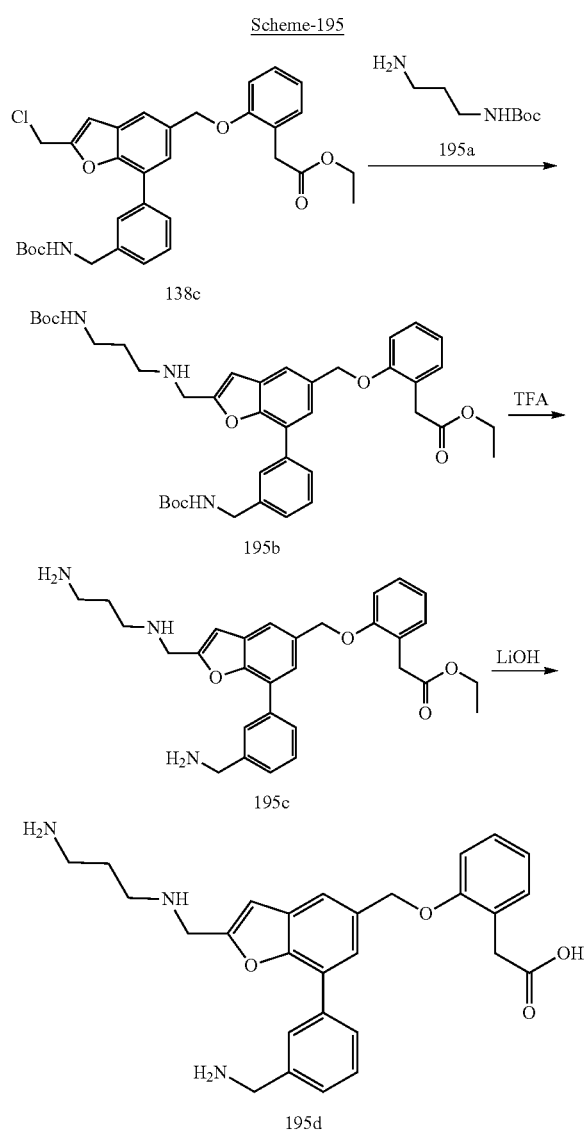

Preparation of 2-(2-((7-(3-(aminomethyl)phenyl)-2-(((3-aminopropyl)amino)methyl)benzofuran-5-yl)methoxy)phenyl)acetic Acid (195d)

Step-1: Preparation of Ethyl 2-(2-((7-(3-(((tert-butoxycarbonyl)amino)methyl)phenyl)-2-(((3-((tert-butoxycarbonyl)amino)propyl)amino)methyl)benzofuran-5-yl)methoxy)phenyl)acetate (195b)

Compound 195b was prepared according to the procedure reported in step-4 of Scheme-138 from 2-(2-((7-(3-(((tert-butoxycarbonyl)amino)methyl)phenyl)-2-(chloromethyl)benzofuran-5-yl)methoxy)phenyl)acetate (138c) (400 mg, 0.71 mmol) and tert-butyl (3-aminopropyl)carbamate (195a) (494 mg, 2.84 mmol; CAS #75178-96-0) in ACN (5 mL). This gave after workup and purification by flash column chromatography [silica (12 g), eluting with DMA80 in DCM from 0-50%] ethyl 2-(2-((7-(3-(((tert-butoxycarbonyl)amino)methyl)phenyl)-2-(((3-((tert-butoxycarbonyl)amino)propyl)amino)methyl)benzofuran-5-yl)methoxy)phenyl)acetate (195b) (368 mg, 74% yield) as a clear oil; $^1$H NMR (300 MHz, DMSO-$d_6$) δ 7.78-7.70 (m, 2H), 7.60 (s, 1H), 7.52-7.43 (m, 3H), 7.32-7.24 (m, 2H), 7.24-7.18 (m, 1H), 7.11 (d, J=8.0 Hz, 1H), 6.95-6.87 (m, 1H), 6.82-6.75 (m, 2H), 5.76 (s, 1H), 5.21 (s, 2H), 4.22 (d, J=6.2 Hz, 2H), 3.92 (q, J=7.1 Hz, 2H), 3.84 (s, 2H), 3.62 (s, 2H), 2.96 (q, J=6.5 Hz, 2H), 2.61-2.52 (m, 2H), 1.55 (q, J=6.9 Hz, 2H), 1.39 (s, 9H), 1.34 (s, 9H), 0.98 (t, J=7.1 Hz, 3H); MS (ES+): 702.4 (M+1).

Step-2: Preparation of Ethyl 2-(2-((7-(3-(aminomethyl)phenyl)-2-(((3-aminopropyl)amino)methyl)benzofuran-5-yl)methoxy)phenyl)acetate (195c)

Compound 195c was prepared according to the procedure reported in step-5 of Scheme-1 from ethyl 2-(2-((7-(3-(((tert-butoxycarbonyl)amino)methyl)phenyl)-2-(((3-((tert-butoxycarbonyl)amino)propyl)amino)methyl)benzofuran-5-yl)methoxy)phenyl)acetate (195b) (365 mg, 0.52 mmol) in DCM (10 mL) using TFA (0.40 mL, 5.20 mmol). This gave after workup ethyl 2-(2-((7-(3-(aminomethyl)phenyl)-2-(((3-aminopropyl)amino)methyl)benzofuran-5-yl)methoxy)phenyl)acetate (195c) as a clear oil which was used as such for next step; MS (ES+) 502.3 (M+1).

Step-3: Preparation of 2-(2-((7-(3-(aminomethyl)phenyl)-2-(((3-aminopropyl)amino)methyl)benzofuran-5-yl)methoxy)phenyl)acetic Acid (195d)

Compound 195d was prepared according to the procedure reported in step-6 of Scheme-1 from ethyl 2-(2-((7-(3-(aminomethyl)phenyl)-2-(((3-aminopropyl)amino)methyl)benzofuran-5-yl)methoxy)phenyl)acetate (195c) (266 mg, 0.53 mmol) in THF (6 mL) and methanol (6 mL) using a solution of lithium hydroxide monohydrate (28.9 mg, 0.69 mmol) in water (2.0 mL). This gave after workup and purification by reverse phase column [C18 (50 g), eluting with ACN in water (containing 0.1% HCl) from 0-100%] 2-(2-((7-(3-(aminomethyl)phenyl)-2-(((3-aminopropyl)amino)methyl)benzofuran-5-yl)methoxy)phenyl)acetic acid (195d) (138 mg, 55% yield) HCl salt as a white solid; $^1$H NMR (300 MHz, DMSO-$d_6$) δ 12.26 (s, 1H, $D_2O$ exchangeable), 9.82 (s, 2H, $D_2O$ exchangeable), 8.52 (s, 3H, $D_2O$ exchangeable), 8.16-8.13 (m, 1H, $D_2O$ exchangeable), 8.12-7.98 (m, 3H), 7.79 (d, J=1.6 Hz, 1H), 7.71 (d, J=1.6 Hz, 1H), 7.65-7.47 (m, 2H), 7.29-7.18 (m, 3H), 7.12-7.03 (m, 1H), 6.91 (td, J=7.4, 1.1 Hz, 1H), 5.28 (s, 2H), 4.46 (s, 2H), 4.18 (d, J=5.1 Hz, 2H), 3.60 (s, 2H), 3.10 (s, 2H), 2.98-2.81 (m, 2H), 2.07-1.93 (m, 2H); MS (ES+): 474.3 (M+1); (ES−): 472.4 (M−1).

Scheme-196

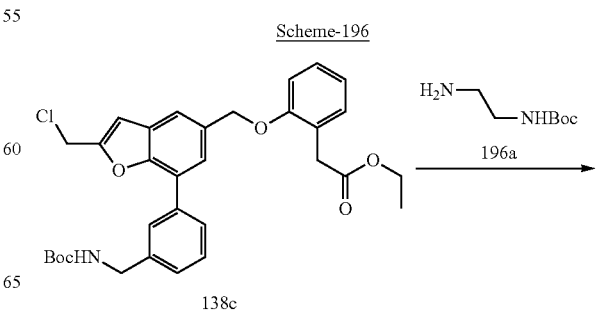

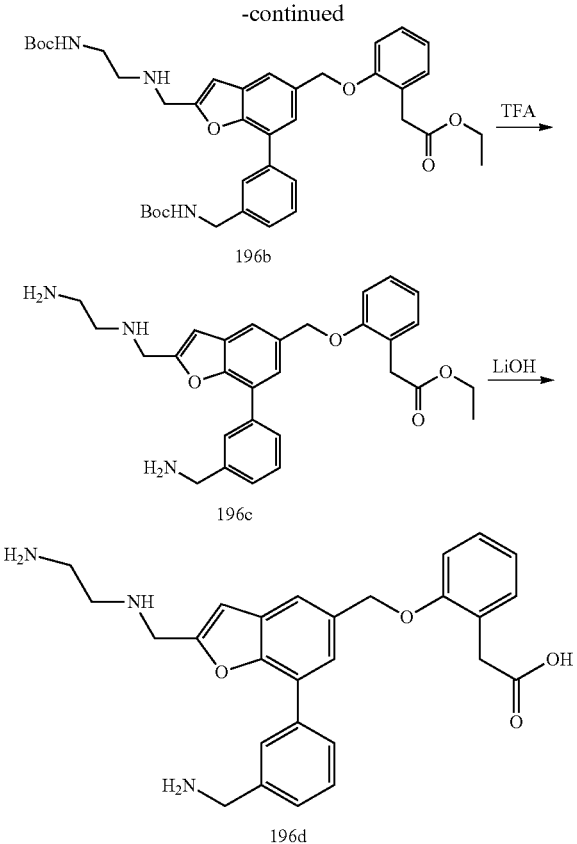

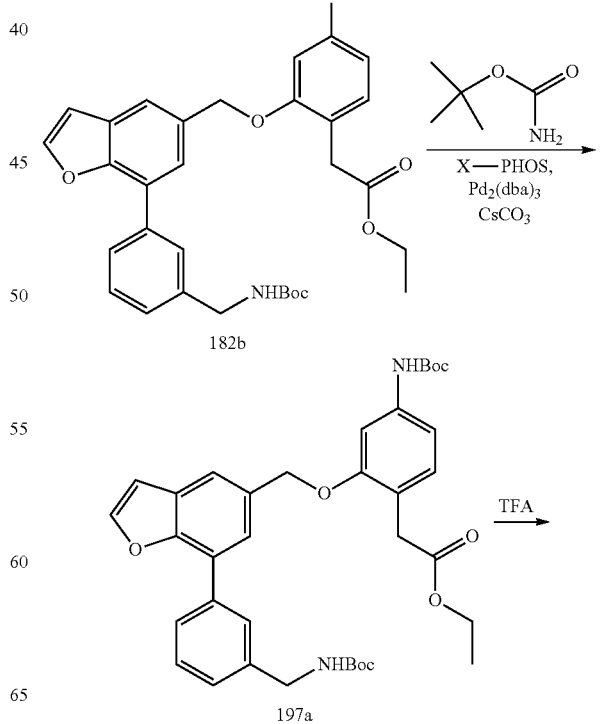

Preparation of 2-(2-((2-(((2-aminoethyl)amino)
methyl)-7-(3-(aminomethyl)phenyl)benzofuran-5-yl)
methoxy)phenyl)acetic Acid (196d)

Step-1: Preparation of Ethyl 2-(2-((2-(((2-((tert-butoxycarbonyl)amino)ethyl)amino)methyl)-7-(3-(((tert-butoxycarbonyl)amino)methyl)phenyl)benzo-furan-5-yl)methoxy)phenyl)acetate (196b)

Compound 196b was prepared according to the procedure reported in step-4 of Scheme-138 from 2-(2-((7-(3-(((tert-butoxycarbonyl)amino)methyl)phenyl)-2-(chloromethyl) benzofuran-5-yl)methoxy)phenyl)acetate (138c) (400 mg, 0.709 mmol) and tert-butyl (2-aminoethyl)carbamate (196a) (454 mg, 2.84 mmol; CAS #57260-73-8) in ACN (5 mL). This gave after workup and purification by flash column chromatography [silica (12 g), eluting with DMA80 in DCM from 0-50%] ethyl 2-(2-((2-(((2-((tert-butoxycarbonyl) amino)ethyl)amino)methyl)-7-(3-(((tert-butoxycarbonyl) amino)methyl)phenyl)benzofuran-5-yl)methoxy)phenyl)ac-etate (196b) (323 mg, 66% yield) as a clear oil; $^1$H NMR (300 MHz, DMSO-$d_6$) δ 7.79-7.70 (m, 2H), 7.61 (d, J=1.6 Hz, 1H), 7.52-7.43 (m, 3H), 7.32-7.25 (m, 2H), 7.25-7.19 (m, 1H), 7.11 (dd, J=8.3, 1.1 Hz, 1H), 6.91 (td, J=7.4, 1.1 Hz, 1H), 6.83-6.72 (m, 2H), 5.21 (s, 2H), 4.23 (d, J=6.2 Hz, 2H), 3.99-3.79 (m, 4H), 3.62 (s, 2H), 3.04 (q, J=6.2 Hz, 2H), 2.61 (t, J=6.4 Hz, 2H), 2.29 (s, 1H), 1.39 (s, 9H), 1.34 (s, 9H), 0.98 (t, J=7.1 Hz, 3H); MS (ES+): 688.4 (M+1).

Step-2: Preparation of Ethyl 2-(2-((2-(((2-amino-ethyl)amino)methyl)-7-(3-(aminomethyl)phenyl) benzofuran-5-yl)methoxy)phenyl)acetate (196c)

Compound 196c was prepared according to the procedure reported in step-5 of Scheme-1 from ethyl 2-(2-((2-(((2-((tert-butoxycarbonyl)amino)ethyl)amino)methyl)-7-(3-(((tert-butoxycarbonyl)amino)methyl)phenyl)benzofuran-5-yl)methoxy)phenyl)acetate (196b) (318 mg, 0.46 mmol) in DCM (10 mL) using TFA (0.36 mL, 4.62 mmol). This gave after workup ethyl 2-(2-((2-(((2-aminoethyl)amino)methyl)-7-(3-(aminomethyl)phenyl)benzofuran-5-yl)methoxy)phe-nyl)acetate (196c) (224 mg, 99% yield) as a clear oil; MS (ES+): 488.3 (M+1).

Step-3: Preparation of 2-(2-((2-(((2-aminoethyl) amino)methyl)-7-(3-(aminomethyl)phenyl)benzo-furan-5-yl)methoxy)phenyl)acetic Acid (196d)

Compound 196d was prepared according to the procedure reported in step-6 of Scheme-1 from ethyl 2-(2-((2-(((2-aminoethyl)amino)methyl)-7-(3-(aminomethyl)phenyl)ben-zofuran-5-yl)methoxy)phenyl)acetate (196c) (185 mg, 0.38 mmol) in THF (6 mL) and methanol (6 mL) using a solution of lithium hydroxide monohydrate (20.70 mg, 0.49 mmol) in water (2.0 mL). This gave after workup and purification by reverse phase column [C18 (50 g), eluting with ACN in water (containing 0.1% HCl) from 0-100%] 2-(2-((2-(((2-aminoethyl)amino)methyl)-7-(3-(aminomethyl)phenyl)ben-zofuran-5-yl)methoxy)phenyl)acetic acid (196d) (90 mg, 52% yield) HCl salt as a white solid; $^1$H NMR (300 MHz, DMSO-$d_6$) δ 12.29 (s, 1H, $D_2O$ exchangeable), 10.45 (s, 2H, $D_2O$ exchangeable), 8.61 (d, J=30.3 Hz, 6H, $D_2O$ exchange-able), 8.31 (d, J=1.9 Hz, 1H), 8.03-7.93 (m, 1H), 7.79 (d, J=1.6 Hz, 1H), 7.73 (d, J=1.6 Hz, 1H), 7.63-7.51 (m, 2H), 7.28-7.20 (m, 3H), 7.09 (d, J=8.1 Hz, 1H), 6.90 (td, J=7.4, 1.0 Hz, 1H), 5.28 (s, 2H), 4.54 (s, 2H), 4.21 (q, J=5.7 Hz, 2H), 3.61 (s, 2H), 3.33 (s, 4H); MS (ES+): 460.2 (M+1); (ES−): 458.4 (M−1).

Scheme-197

Preparation of 2-(4-amino-2-((7-(3-(aminomethyl)phenyl)benzofuran-5-yl)methoxy)phenyl)acetic Acid (197c)

Step-1: Preparation of Ethyl 2-(4-((tert-butoxycarbonyl)amino)-2-((7-(3-(((tert-butoxycarbonyl)amino)methyl)phenyl)benzofuran-5-yl)methoxy)phenyl)acetate (197a)

To a degassed solution of ethyl 2-(4-bromo-2-((7-(3-((tert-butoxycarbonylamino)methyl)phenyl)benzofuran-5-yl)methoxy)phenyl)acetate (182b) (0.250 g, 0.421 mmol) in toluene (10 mL) was added dicyclohexyl(2',4',6'-triisopropylbiphenyl-2-yl)phosphine (X-PHOS, 0.020 g, 0.042 mmol), tert-butyl carbamate (0.074 g, 0.631 mmol), Pd$_2$(dba)$_3$ (0.019 g, 0.021 mmol), cesium carbonate (0.137 g, 0.421 mmol) and the mixture was heated at 95° C. for 16 h. The reaction was cooled to room temperature, diluted with EtOAc (50 mL), filtered over Celite pad, the Celite pad was rinsed with EtOAc (2×50 mL). The combined organic layers were dried, filtered and evaporated to dryness. The residue obtained was purified by flash column chromatography [silica gel 24 g, eluting with ethyl acetate in hexanes from 0-100%] to furnish ethyl 2-(4-((tert-butoxycarbonyl)amino)-2-((7-(3-(((tert-butoxycarbonyl)amino)methyl)phenyl)benzofuran-5-yl)methoxy)phenyl)acetate (197a) (0.221 g, 83% yield) as a pale-brown wax; MS (ES+): 531.3 (M+1, -Boc).

Step-2: Preparation of Ethyl 2-(4-amino-2-((7-(3-(aminomethyl)phenyl)benzofuran-5-yl)methoxy)phenyl)acetate (197b)

Compound 197b was prepared according to the procedure reported in step-5 of Scheme-1 from ethyl 2-(4-((tert-butoxycarbonyl)amino)-2-((7-(3-(((tert-butoxycarbonyl)amino)methyl)phenyl)benzofuran-5-yl)methoxy)phenyl)acetate (197a) (0.201 g, 0.319 mmol) in DCM (10 mL) using TFA (0.491 mL, 6.37 mmol). This gave after workup and purification by flash column chromatography [silica gel 12 g, eluting with methanol in DCM from 0-100%] ethyl 2-(4-amino-2-((7-(3-(aminomethyl)phenyl)benzofuran-5-yl)methoxy)phenyl)acetate (197b) (0.102 g, 59% yield) pale-yellow solid as TFA salt; $^1$H NMR (300 MHz, DMSO-d$_6$) δ 8.25 (bs, 3H, D$_2$O exchangeable), 8.12 (d, J=2.2 Hz, 1H), 8.02-7.97 (m, 1H), 7.95-7.88 (m, 1H), 7.73 (d, J=1.6 Hz, 1H), 7.67-7.49 (m, 3H), 7.08 (d, J=2.2 Hz, 1H), 6.96 (d, J=8.0 Hz, 1H), 6.53 (s, 1H), 6.32 (d, J=8.0 Hz, 1H), 5.16 (s, 2H), 4.16 (d, J=5.7 Hz, 2H), 3.92 (q, J=7.1 Hz, 2H), 3.49 (s, 2H), 0.99 (t, J=7.1 Hz, 3H); $^{19}$F NMR (282 MHz, DMSO-d$_6$) δ −73.82; MS (ES+): 431.20 (M+1).

Step-3: Preparation of 2-(4-amino-2-((7-(3-(aminomethyl)phenyl)benzofuran-5-yl)methoxy)phenyl) acetic Acid (197c)

Compound 197c was prepared according to the procedure reported in step-6 of Scheme-1 from ethyl 2-(4-amino-2-((7-(3-(aminomethyl)phenyl)benzofuran-5-yl)methoxy)phenyl)acetate (197b) (0.090 g, 0.209 mmol) in THF (4 mL) and methanol (8 mL) using 2M LiOH (0.523 mL, 1.045 mmol). This gave after workup and purification by flash column chromatography [silica gel 12 g, eluting with methanol in DCM from 0-100%] followed by reverse phase column chromatography [C18 (50 g), eluting with ACN in water (containing 0.1% HCl) from 0-100%] 2-(4-amino-2-((7-(3-(aminomethyl)phenyl)benzofuran-5-yl)methoxy)phenyl)acetic acid (197c) (0.036 g, 43% yield) HCl salt as a white solid; $^1$H NMR (300 MHz, DMSO-d$_6$) δ 12.32 (bs, 1H, D$_2$O exchangeable), 10.12 (bs, 2H, D$_2$O exchangeable), 8.53 (s, 3H, D$_2$O exchangeable), 8.11 (d, J=2.2 Hz, 1H), 8.09-8.02 (m, 1H), 7.99-7.90 (m, 1H), 7.77 (d, J=1.6 Hz, 1H), 7.67 (d, J=1.7 Hz, 1H), 7.63-7.53 (m, 2H), 7.29 (d, J=8.0 Hz, 1H), 7.11 (d, J=2.0 Hz, 1H), 7.06 (d, J=2.2 Hz, 1H), 6.86 (dd, J=7.9, 1.9 Hz, 1H), 5.27 (s, 2H), 4.14 (q, J=5.8 Hz, 2H), 3.61 (s, 2H); MS (ES+): 403.2 (M+1); MS (ES−): 401.3 (M−1); HPLC purity: 99.34%.

Scheme-198

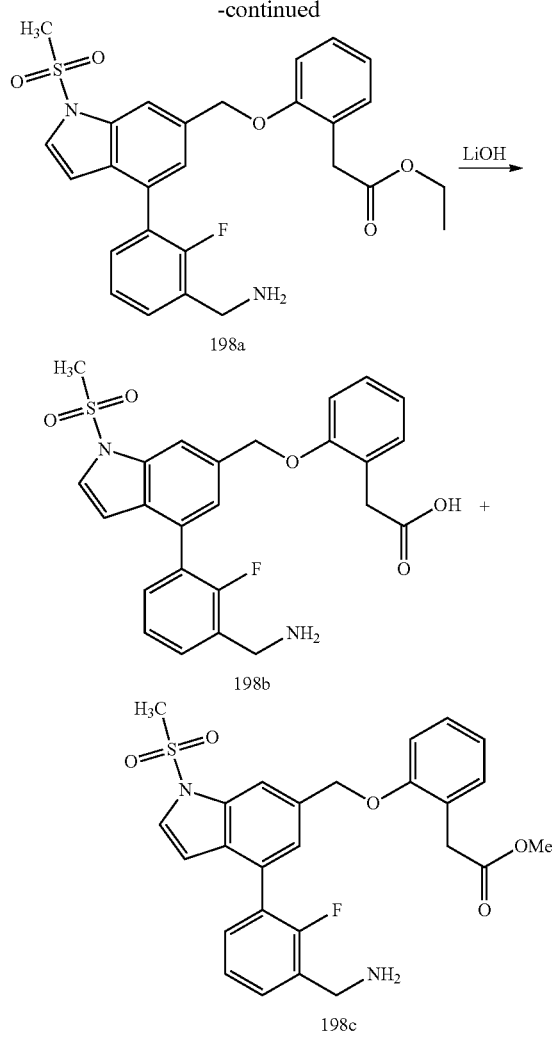

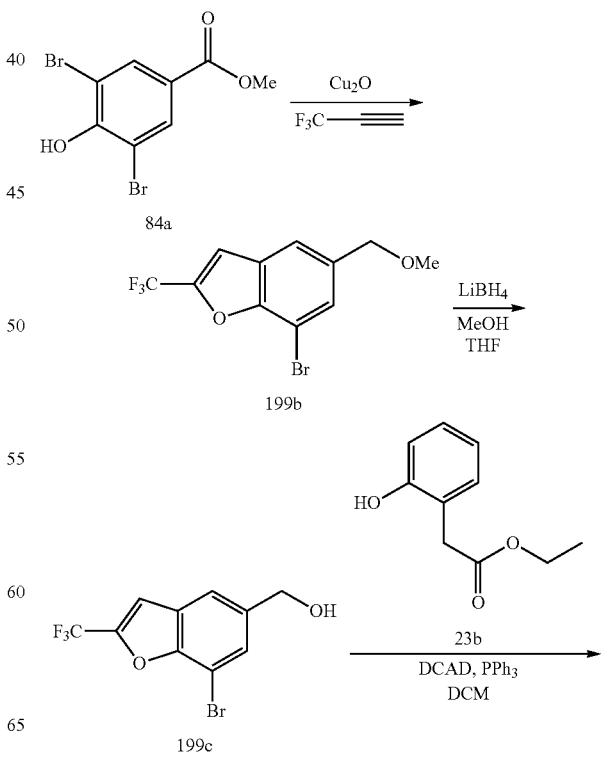

J=3.3 Hz, 1H), 5.29 (s, 2H), 3.93-3.78 (m, 4H), 3.61 (s, 2H), 3.51 (s, 3H), 0.95 (t, J=7.1 Hz, 3H); MS (ES+): 511.2 (M+1); MS (ES−): 509.3 (M−1).

Step-2: Preparation of 2-(2-((4-(3-(aminomethyl)-2-fluorophenyl)-1-(methylsulfonyl)-1H-indol-6-yl)methoxy)phenyl)acetic Acid (198b)

Compound 198b was prepared according to the procedure reported in step-6 of Scheme-1 from ethyl 2-(2-((4-(3-(aminomethyl)-2-fluorophenyl)-1-(methylsulfonyl)-1H-indol-6-yl)methoxy)phenyl)acetate (198a) (0.13 g, 0.25 mmol) in MeOH/THF (4 mL, 1:1) using a solution of lithium hydroxide hydrate (0.02 g, 0.50 mmol) in water (1.0 mL). This gave after workup and purification by flash column chromatography [silica (4 g), eluting with MeOH in DCM from 0-50%] 2-(2-((4-(3-(aminomethyl)-2-fluorophenyl)-1-(methylsulfonyl)-1H-indol-6-yl)methoxy)phenyl) acetic acid (198b) (0.05 g, 40% yield) as a white solid; $^1$H NMR (300 MHz, DMSO-$d_6$) δ 8.00 (s, 1H), 7.66 (d, J=3.7 Hz, 1H), 7.58 (t, J=7.3 Hz, 1H), 7.52 (s, 1H), 7.48 (t, J=7.2 Hz, 1H), 7.34 (t, J=7.6 Hz, 1H), 7.20 (d, J=7.6 Hz, 2H), 7.09 (d, J=8.0 Hz, 1H), 6.89 (t, J=7.3 Hz, 1H), 6.68 (s, 1H), 5.32 (s, 2H), 3.97 (s, 2H), 3.54 (s, 2H), 3.51 (s, 3H). $^{19}$F NMR (282 MHz, DMSO-$d_6$) δ−120.18; MS (ES+) 483.2 (M+1), MS (ES−) 481.3 (M−1). and methyl 2-(2-((4-(3-(aminomethyl)-2-fluorophenyl)-1-(methylsulfonyl)-1H-indol-6-yl)methoxy)phenyl)acetate (198c) (0.03 g, 22% yield) as a white solid; $^1$H NMR (300 MHz, DMSO-$d_6$) δ 8.00 (s, 1H), 7.67 (d, J=3.7 Hz, 1H), 7.61 (t, J=7.0 Hz, 1H), 7.49 (t, J=6.7 Hz, 1H), 7.41 (s, 1H), 7.37 (d, J=7.6 Hz, 1H), 7.31-7.19 (m, 2H), 7.18-7.10 (m, 1H), 6.96-6.87 (m, 1H), 6.67 (t, J=3.4 Hz, 1H), 5.30 (s, 2H), 4.03 (s, 2H), 3.65 (s, 2H), 3.52 (s, 3H), 3.44 (s, 3H); $^{19}$F NMR (282 MHz, DMSO-$d_6$) δ−120.43; MS (ES+): 497.2 (M+1).

Preparation of 2-(2-((4-(3-(aminomethyl)-2-fluorophenyl)-1-(methylsulfonyl)-1H-indol-6-yl)methoxy)phenyl)acetic Acid (198b)

Step-1: Preparation of Ethyl 2-(2-((4-(3-(aminomethyl)-2-fluorophenyl)-1-(methylsulfonyl)-1H-indol-6-yl)methoxy)phenyl)acetate (198a)

Compound 198a was prepared according to the procedure reported in step-3 of Scheme-1 from ethyl 2-(2-((4-bromo-1-(methylsulfonyl)-1H-indol-6-yl)methoxy)phenyl)acetate (192c) (0.23 g, 0.49 mmol) in dioxane (4 mL) using (3-(aminomethyl)-2-fluorophenyl)boronic acid hydrochloride (56a) (0.15 g, 0.74 mmol), $K_2CO_3$ (0.10 g, 0.74 mmol) in water (2 mL) and bis(triphenylphosphine)palladium(ll)chloride (0.05 g, 0.07 mmol) under an Ar atmosphere and heating at 85° C. for 2 h on oil bath. This gave after workup, purification by flash column chromatography [silica (12 g), eluting with MeOH in DCM from 0-20%] ethyl 2-(2-((4-(3-(aminomethyl)-2-fluorophenyl)-1-(methyl sulfonyl)-1H-indol-6-yl)methoxy)phenyl)acetate (198a) (0.17 g, 67% yield) as a white solid; $^1$H NMR (300 MHz, DMSO-$d_6$) δ 7.99 (s, 1H), 7.64 (d, J=3.7 Hz, 1H), 7.58 (t, J=7.4 Hz, 1H), 7.41 (s, 1H), 7.38-7.09 (m, 5H), 6.95-6.85 (m, 1H), 6.61 (t,

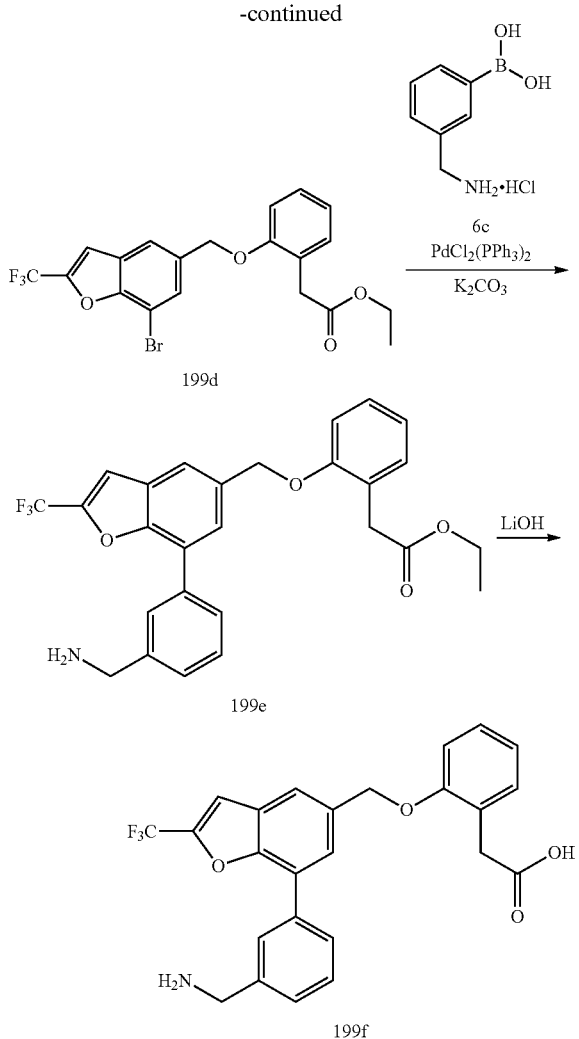

Preparation of 2-(2-((7-(3-(aminomethyl)phenyl)-2-(trifluoromethyl)benzofuran-5-yl)methoxy)phenyl) acetic Acid (199f)

Step-1: Preparation of methyl 7-bromo-2-(trifluoromethyl)benzofuran-5-carboxylate (199b)

Compound 199b was prepared according to the procedure reported in step-1 of Scheme-55 from methyl 3,5-dibromo-4-hydroxybenzoate (84a) (25 g, 81 mmol; CAS: 41727-47-3) in pyridine (100 mL) using 3,3,3-trifluoroprop-1-yne (8 g, 85 mmol; CAS #661-54-1) and copper(I) oxide (11.5 g, 80 mmol). This gave after workup and purification by flash column chromatography [silica (220g), eluting with EtOAc in hexane from 0-40%] methyl 7-bromo-2-(trifluoromethyl) benzofuran-5-carboxylate (199b) (9.4 g, 36% yield) as a white solid. $^1$H NMR (300 MHz, DMSO-$d_6$) δ 8.45 (d, J=1.5 Hz, 1H), 8.25 (d, J=1.6 Hz, 1H), 8.03 (m, 1H), 3.92 (s, 3H); $^{19}$F NMR (282 MHz, DMSO-$d_6$) δ−63.74.

Step-2: Preparation of (7-bromo-2-(trifluoromethyl) benzofuran-5-yl)methanol (199c)

Compound 199c was prepared according to the procedure reported in step-2 of Scheme-76 from methyl 7-bromo-2-(trifluoromethyl)benzofuran-5-carboxylate (199b) (3 g, 9.29 mmol) in THF (36 mL) using LiBH$_4$ (7 mL, 4 M, 28.0 mmol) and MeOH (1.12 mL, 27.7 mmol). This gave after workup and purification by flash column chromatography [silica (80 g), eluting with EtOAc in hexane from 10-60%] followed by purification by reverse phase column chromatography [C18 (150g), eluting with ACN in water (containing 0.1% HCl) from 0-100%] (7-bromo-2-(trifluoromethyl) benzofuran-5-yl)methanol (199c) (1.85 g, 68% yield) as a white solid. $^1$H NMR (300 MHz, DMSO-$d_6$) δ 7.92 (q, J=1.2 Hz, 1H), 7.76 (d, J=1.3 Hz, 1H), 7.73 (d, J=1.4 Hz, 1H), 5.47 (s, 1H), 4.62 (s, 2H); $^{19}$F NMR (282 MHz, DMSO-$d_6$) δ−63.49.

Step-3: Preparation of Ethyl 2-(2-((7-bromo-2-(trifluoromethyl)benzofuran-5-yl)methoxy)phenyl)acetate (199d)

Compound 199d was prepared according to the procedure reported in step-2 of Scheme-23 from (7-bromo-2-(trifluoromethyl)benzofuran-5-yl)methanol (199c) (1.80 g, 6.10 mmol) in DCM (35 mL) using triphenylphosphine ((1.67 g, 6.37 mmol), ethyl 2-(2-hydroxyphenyl) acetate (23b) (1.40 g, 7.77 mmol) and di-(4-chlorobenzyl)azodicarboxylate (DCAD, 2.53 g, 6.89 mmol) in DCM (8 mL). This gave after workup and purification by flash column chromatography [silica (40 g), eluting with EtOAc in hexane from 0-40%] ethyl 2-(2-((7-bromo-2-(trifluoromethyl)benzofuran-5-yl) methoxy)phenyl)acetate (199d) (2.28 g, 82% yield) as a white solid. $^1$H NMR (300 MHz, DMSO-$d_6$) δ 7.97 (q, J=1.2 Hz, 1H), 7.88 (d, J=1.4 Hz, 1H), 7.85 (d, J=1.4 Hz, 1H), 7.32-7.20 (m, 2H), 7.08 (dd, J=8.2, 1.1 Hz, 1H), 6.93 (td, J=7.4, 1.1 Hz, 1H), 5.24 (s, 2H), 4.03 (q, J=7.1 Hz, 2H), 3.64 (s, 2H), 1.08 (t, J=7.1 Hz, 3H); $^{19}$F NMR (282 MHz, DMSO-$d_6$) δ−63.53.

Step-4: Preparation of Ethyl 2-(2-((7-(3-(aminomethyl)phenyl)-2-(trifluoromethyl)benzofuran-5-yl) methoxy)phenyl)acetate (199e)

Compound 199e was prepared according to the procedure reported in step-3 of Scheme-1 from ethyl 2-(2-((7-bromo-2-(trifluoromethyl)benzofuran-5-yl)methoxy)phenyl)acetate (199d) (360 mg, 0.787 mmol) in dioxane (5 mL) using 3-(aminomethyl)phenylboronic acid hydrochloride (6c) (159 mg, 1.053 mmol), a solution of K$_2$CO$_3$ (345 mg, 2.496 mmol) in water (0.5 mL), bis(triphenylphosphine)palladium (II) chloride (84 mg, 0.120 mmol) and heating at 100° C. for 3h on oil bath. This gave after workup, purification by flash column chromatography [silica (24 g), eluting with DMA80 in DCM from 0-70%] ethyl 2-(2-((7-(3-(aminomethyl)phenyl)-2-(trifluoromethyl)benzofuran-5-yl)methoxy)phenyl) acetate (199e) (297 mg, 78% yield) as a pale-yellow oil. An analytical sample was obtained by further purification by reverse phase column chromatography [C18 (50 g), eluting with ACN in water (containing 0.1% HCl) from 0-100%] to afford Compound 199e HCl salt as white solid. $^1$H NMR (300 MHz, DMSO-$d_6$) δ 8.46 (s, 3H), 7.90 (q, J=1.2 Hz, 1H), 7.87-7.79 (m, 3H), 7.76 (d, J=1.6 Hz, 1H), 7.62-7.54 (m, 2H), 7.25-7.12 (m, 2H), 7.05 (dd, J=8.2, 1.1 Hz, 1H), 6.86 (td, J=7.4, 1.1 Hz, 1H), 5.23 (s, 2H), 4.07 (s, 2H), 3.87 (q, J=7.1 Hz, 2H), 3.58 (s, 2H), 0.92 (t, J=7.1 Hz, 3H); $^{19}$F NMR (282 MHz, DMSO-$d_6$) δ−63.34. MS (ES+): 484.2 (M+1).

Step-5: Preparation of 2-(2-((7-(3-(aminomethyl) phenyl)-2-(trifluoromethyl)benzofuran-5-yl) methoxy)phenyl)acetic Acid (199f)

Compound 199f was prepared according to the procedure reported in step-6 of Scheme-1 from ethyl 2-(2-((7-(3-

(aminomethyl)phenyl)-2-(trifluoromethyl)benzofuran-5-yl)methoxy)phenyl)acetate (199e) (200 mg, 0.414 mmol) in MeOH/THF (6 mL each) using a solution of lithium hydroxide monohydrate (84 mg, 2.0 mmol) in water (2.0 mL). This gave after workup and purification by reverse phase column [C18 (50 g), eluting with ACN in water (containing 0.1% HCl) from 0-100%] of 2-(2-((7-(3-(aminomethyl)phenyl)-2-(trifluoromethyl)benzofuran-5-yl)methoxy)phenyl)acetic acid (199f) (43 mg, 23% yield) HCl salt as a white solid. $^1$H NMR (300 MHz, DMSO-d$_6$) δ 12.13 (s, 1H), 8.66 (s, 3H), 7.98 (s, 1H), 7.95-7.83 (m, 4H), 7.71-7.56 (m, 2H), 7.28-7.19 (m, 2H), 7.09 (d, J=8.3 Hz, 1H), 6.91 (t, J=7.3 Hz, 1H), 5.31 (s, 2H), 4.13 (s, 2H), 3.62 (s, 2H); $^{19}$F NMR (282 MHz, DMSO-d$_6$) δ−63.37. MS (ES+): 456.2 (M+1); MS (ES−): 454.3 (M−1).

Scheme-200

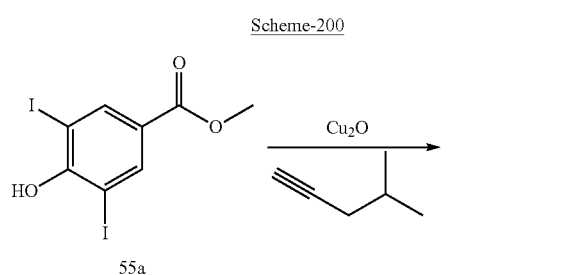

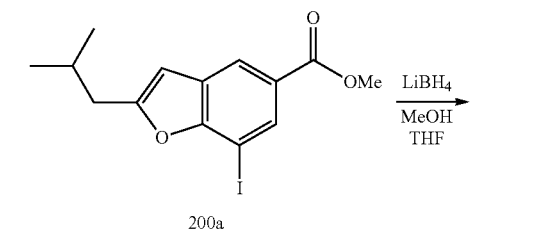

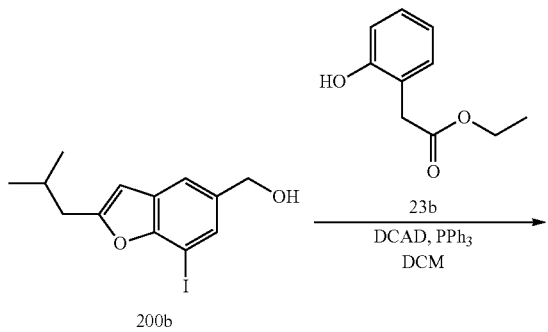

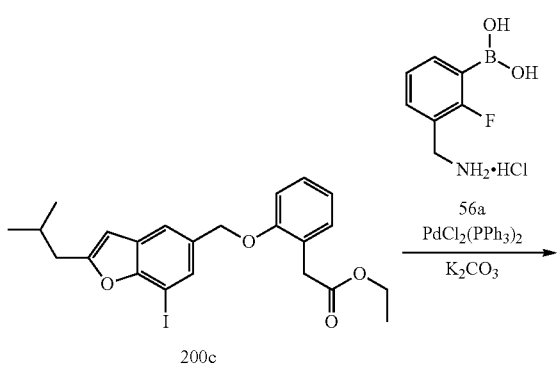

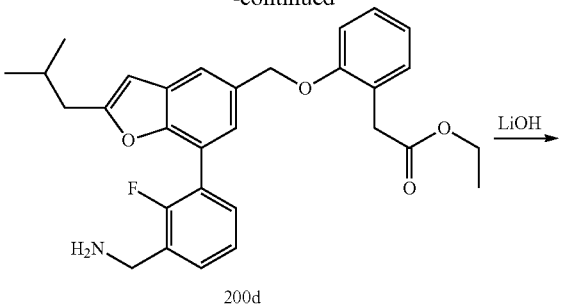

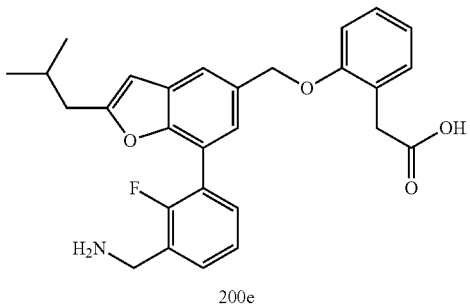

Preparation of 2-(2-((7-(3-(aminomethyl)-2-fluorophenyl)-2-isobutylbenzofuran-5-yl)methoxy)phenyl)acetic Acid (200e)

Step-1: Preparation of methyl 7-iodo-2-isobutylbenzofuran-5-carboxylate (200a)

Compound 200a was prepared according to the procedure reported in step-1 of Scheme-55 from methyl 4-hydroxy-3,5-diiodobenzoate (55a) (16.80 g, 41.6 mmol) in pyridine (50 mL) using 4-methylpent-1-yne (4.90 mL, 41.6 mmol) and copper(I) oxide (2.98 g, 20.8 mmol). This gave after workup and purification by flash column chromatography [silica gel, eluting with EtOAc in hexane from 0-10%] methyl 7-iodo-2-isobutylbenzofuran-5-carboxylate (200a) (6.57 g, 44% yield); $^1$H NMR (500 MHz, DMSO-d$_6$) δ 8.19 (d, J=1.6 Hz, 1H), 8.15 (d, J=1.6 Hz, 1H), 6.91-6.88 (m, 1H), 3.87 (s, 3H), 2.73-2.70 (m, 2H), 2.13-1.95 (m, 1H), 0.97 (d, J=6.7 Hz, 6H).

Step-2: Preparation of (7-iodo-2-isobutylbenzofuran-5-yl)methanol (200b)

Compound 200b was prepared according to the procedure reported in step-2 of Scheme-76 from methyl 7-iodo-2-isobutylbenzofuran-5-carboxylate (200a) (6.28 g, 17.53 mmol) in THF (60 mL) using LiBH$_4$ (17.53 mL, 35.1 mmol) and MeOH (1.419 mL, 35.1 mmol). This gave after workup and purification by flash column chromatography [silica gel, eluting with EtOAc in hexane from 0 to 25%] (7-iodo-2-isobutylbenzofuran-5-yl)methanol (200b) (5.73 g, 99% yield) as a clear oil. $^1$H NMR (300 MHz, DMSO-d$_6$) δ 7.56-7.51 (m, 1H), 7.46-7.44 (m, 1H), 6.73-6.72 (m, 1H), 5.25 (t, J=5.8 Hz, 1H), 4.51 (d, J=5.7 Hz, 2H), 2.66 (dd, J=7.0, 0.8 Hz, 2H), 2.12-1.94 (m, 1H), 0.95 (d, J=6.7 Hz, 6H).

Step-3: Preparation of Ethyl 2-(2-((7-iodo-2-isobutylbenzofuran-5-yl)methoxy)phenyl)acetate (200c)

Compound 200c was prepared according to the procedure reported in step-2 of Scheme-23 from (7-iodo-2-isobutyl-benzofuran-5-yl)methanol (200b) (5.60 g, 16.96 mmol) in DCM (100 mL) using triphenylphosphine (6.23 g, 23.75 mmol), ethyl 2-(2-hydroxyphenyl) acetate (23b) (4.28 g, 23.75 mmol) and di-(4-chlorobenzyl)azodicarboxylate (DCAD, 8.72 g, 23.75 mmol) in DCM (10 mL). This gave after workup and purification by flash column chromatography [silica gel, eluting with EtOAc in hexane from 0-20%] ethyl 2-(2-((7-iodo-2-isobutylbenzofuran-5-yl)methoxy) phenyl)acetate (200c) (6.17 g, 74% yield) as an off-white solid. $^1$H NMR (300 MHz, DMSO-$d_6$) δ 7.64 (d, J=1.5 Hz, 1H), 7.57 (d, J=1.5 Hz, 1H), 7.32-7.17 (m, 2H), 7.06 (d, J=8.1 Hz, 1H), 6.91 (td, J=7.3, 1.0 Hz, 1H), 6.76 (s, 1H), 5.12 (s, 2H), 4.01 (q, J=7.1 Hz, 2H), 3.60 (s, 2H), 2.68 (d, J=7.0 Hz, 2H), 2.13-1.95 (m, 1H), 1.07 (t, J=7.1 Hz, 3H), 0.96 (d, J=6.6 Hz, 6H); MS (ES+): 515.1 (M+Na).

Step-4: Preparation of Ethyl 2-(2-((7-(3-(aminomethyl)-2-fluorophenyl)-2-isobutylbenzofuran-5-yl)methoxy)phenyl)acetate (200d)

Compound 200d was prepared according to the procedure reported in step-3 of Scheme-1 from ethyl 2-(2-((7-iodo-2-isobutylbenzofuran-5-yl)methoxy)phenyl)acetate (200c) (750 mg, 1.523 mmol) in dioxane (20 mL) using 3-(aminomethyl)-2-fluorophenylboronic acid hydrochloride (56a) (469 mg, 2.285 mmol), a solution of $K_2CO_3$ (632 mg, 4.57 mmol) in water (5 mL), bis(triphenylphosphine)palladium (II) chloride (1.231 g, 1.523 mmol) and heating at 100° C. for 3.5 h on oil bath. This gave after workup, purification by flash column chromatography [silica gel, eluting with DMA80 in DCM from 0-20%] ethyl 2-(2-((7-(3-(aminomethyl)-2-fluorophenyl)-2-isobutylbenzofuran-5-yl)methoxy) phenyl)acetate (200d) (79 mg). MS (ES+): 490.3 (M+1).

Step-5: Preparation of 2-(2-((7-(3-(aminomethyl)-2-fluorophenyl)-2-isobutylbenzofuran-5-yl)methoxy)phenyl)acetic Acid (200e)

Compound 200e was prepared according to the procedure reported in step-6 of Scheme-1 from ethyl 2-(2-((7-(3-(aminomethyl)-2-fluorophenyl)-2-isobutylbenzofuran-5-yl) methoxy)phenyl)acetate (200d) (70 mg, 0.143 mmol) in MeOH/THF (5 mL each) using a solution of lithium hydroxide monohydrate (24 mg, 0.572 mmol) in water (5 mL). This gave after workup and purification by reverse phase column [C18 (50 g), eluting with ACN in water (containing 0.1% HCl) from 0-100%] 2-(2-((7-(3-(aminomethyl)-2-fluorophenyl)-2-isobutylbenzofuran-5-yl)methoxy)phenyl)acetic acid (200e) (16 mg, 2.5% for two steps) HCl salt as a fluffy white solid; $^1$H NMR (300 MHz, DMSO-$d_6$) δ 9.22 (s, 3H), 7.72-7.60 (m, 3H), 7.42 (t, J=7.7 Hz, 1H), 7.37 (s, 1H), 7.28-7.16 (m, 2H), 7.08 (d, J=8.0 Hz, 1H), 6.90 (td, J=7.4, 1.1 Hz, 1H), 6.69 (s, 1H), 5.23 (s, 2H), 4.15 (s, 2H), 3.57 (s, 2H), 2.63 (d, J=7.0 Hz, 2H), 2.16-1.87 (m, 1H), 0.93 (d, J=6.6 Hz, 6H); $^{19}$F NMR (282 MHz, DMSO-$d_6$) δ −118.68; MS (ES+): 462.2 (M+1); HPLC purity: 99.57%.

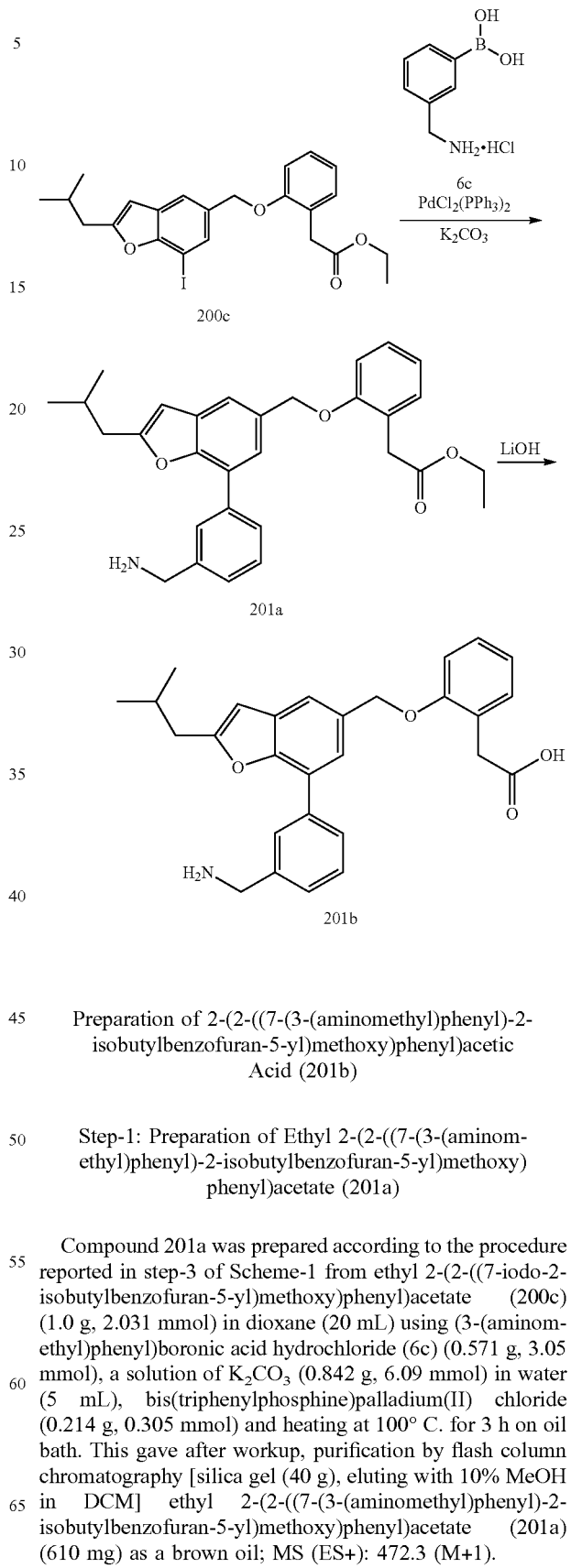

Scheme-201

Preparation of 2-(2-((7-(3-(aminomethyl)phenyl)-2-isobutylbenzofuran-5-yl)methoxy)phenyl)acetic Acid (201b)

Step-1: Preparation of Ethyl 2-(2-((7-(3-(aminomethyl)phenyl)-2-isobutylbenzofuran-5-yl)methoxy)phenyl)acetate (201a)

Compound 201a was prepared according to the procedure reported in step-3 of Scheme-1 from ethyl 2-(2-((7-iodo-2-isobutylbenzofuran-5-yl)methoxy)phenyl)acetate (200c) (1.0 g, 2.031 mmol) in dioxane (20 mL) using (3-(aminomethyl)phenyl)boronic acid hydrochloride (6c) (0.571 g, 3.05 mmol), a solution of $K_2CO_3$ (0.842 g, 6.09 mmol) in water (5 mL), bis(triphenylphosphine)palladium(II) chloride (0.214 g, 0.305 mmol) and heating at 100° C. for 3 h on oil bath. This gave after workup, purification by flash column chromatography [silica gel (40 g), eluting with 10% MeOH in DCM] ethyl 2-(2-((7-(3-(aminomethyl)phenyl)-2-isobutylbenzofuran-5-yl)methoxy)phenyl)acetate (201a) (610 mg) as a brown oil; MS (ES+): 472.3 (M+1).

Step-2: Preparation of 2-(2-((7-(3-(aminomethyl)phenyl)-2-isobutylbenzofuran-5-yl)methoxy)phenyl)acetic Acid (201b)

Compound 201b was prepared according to the procedure reported in step-6 of Scheme-1 from ethyl 2-(2-((7-(3-(aminomethyl)phenyl)-2-isobutylbenzofuran-5-yl)methoxy)phenyl)acetate (201a) (560 mg, 1.187 mmol) in MeOH/THF (10 mL each) using a solution of lithium hydroxide monohydrate (199 mg, 4.75 mmol) in water (10 mL). This gave after workup and purification by reverse phase column [C18 (50 g), eluting with ACN in water (containing 0.1% HCl) from 0-100%] 2-(2-((7-(3-(aminomethyl)phenyl)-2-isobutylbenzofuran-5-yl)methoxy)phenyl)acetic acid (201b) (93 mg, 11% for two steps) HCl salt as a white solid; $^1$H NMR (300 MHz, DMSO-d$_6$) δ 12.25 (s, 1H), 8.55 (s, 3H), 7.99-7.95 (m, 1H), 7.92 (dt, J=6.6, 2.2 Hz, 1H), 7.63 (d, J=1.6 Hz, 1H), 7.62-7.53 (m, 3H), 7.28-7.17 (m, 2H), 7.11-7.07 (m, 1H), 6.90 (td, J=7.4, 1.1 Hz, 1H), 6.69 (s, 1H), 5.24 (s, 2H), 4.12 (s, 2H), 3.60 (s, 2H), 2.70 (d, J=7.0 Hz, 2H), 2.20-1.89 (m, 1H), 0.96 (d, J=6.6 Hz, 6H); MS (ES+): 444.3 (M+1), MS (ES-): 442.3 (M-1); HPLC purity: 99.80%.

Scheme-202

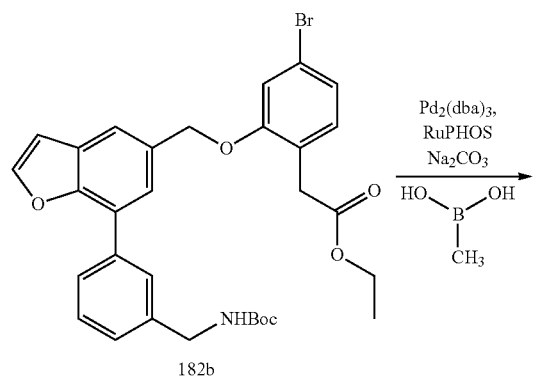

182b

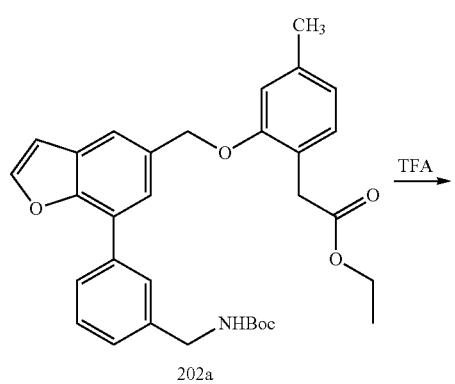

202a

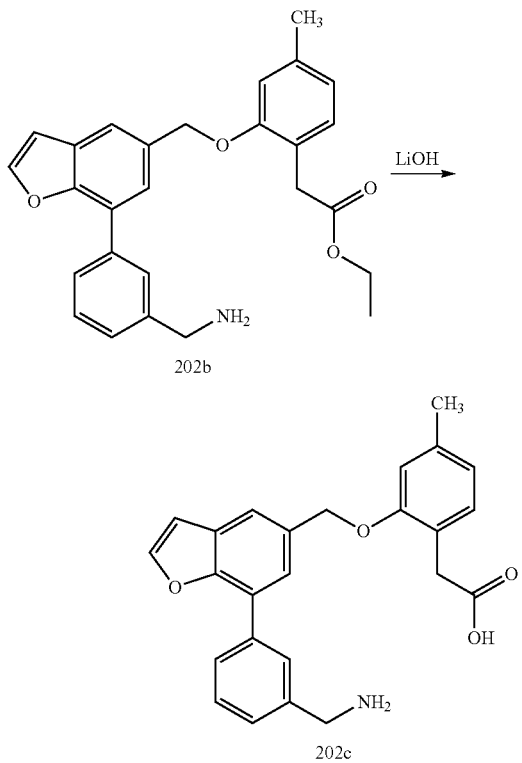

Preparation of 2-(2-((7-(3-(aminomethyl)phenyl)benzofuran-5-yl)methoxy)-4-methylphenyl)acetic Acid (202c)

Step-1: Preparation of Ethyl 2-(2-((7-(3-(((tert-butoxycarbonyl)amino)methyl)phenyl)benzofuran-5-yl)methoxy)-4-methylphenyl)acetate (202a)

A mixture of ethyl 2-(4-bromo-2-((7-(3-((tert-butoxycarbonylamino)methyl)phenyl)benzofuran-5-yl)methoxy)phenyl)acetate (182b) (0.306 g, 0.515 mmol), methylboronic acid (0.046 g, 0.772 mmol), dicyclohexyl(2',6'-diisopropoxybiphenyl-2-yl)phosphine (RuPHOS) (0.024 g, 0.051 mmol), Pd$_2$(dba)$_3$ (0.024 g, 0.026 mmol) in toluene (20 mL) and a solution of Na$_2$CO$_3$ (0.214 g, 2.02 mmol) in water (2 mL) was degassed and filled with nitrogen. The reaction mixture was heated at 100° C. for 10 h, cooled to room temperature, diluted with EtOAc (100 mL) and brine (50 mL). The aqueous layer was separated, dried, filtered and evaporated to dryness. The residue obtained was purified by flash column chromatography [silica gel 24 g, eluting with EtOAc in hexanes from 0-100%] to afford ethyl 2-(2-((7-(3-(((tert-butoxycarbonyl)amino)methyl)phenyl)benzofuran-5-yl)methoxy)-4-methylphenyl)acetate (202a) (0.183 g, 67% yield) as a pale-yellow wax; $^1$H NMR (300 MHz, DMSO-d$_6$) δ 8.08 (d, J=2.2 Hz, 1H), 7.79-7.66 (m, 3H), 7.54 (d, J=1.6 Hz, 1H), 7.54-7.42 (m, 1H), 7.30 (d, J=7.6 Hz, 1H), 7.08 (d, J=7.5 Hz, 1H), 7.06 (d, J=2.2 Hz, 1H), 7.00-6.93 (m, 1H), 6.77-6.68 (m, 1H), 5.21 (s, 2H), 4.23 (d, J=6.2 Hz, 2H), 3.90 (q, J=7.1 Hz, 2H), 3.56 (s, 2H), 2.30 (s, 3H), 1.39 (s, 9H), 0.95 (t, J=7.1 Hz, 3H); MS (ES+): 430.2 (M+1, -Boc).

Step-2: Preparation of Ethyl 2-(2-((7-(3-(aminomethyl)phenyl)benzofuran-5-yl)methoxy)-4-methylphenyl)acetate (202b)

Compound 202b was prepared according to the procedure reported in step-5 of Scheme-1 from ethyl 2-(2-((7-(3-(((tert-butoxycarbonyl)amino)methyl)phenyl)benzofuran-5-yl)methoxy)-4-methylphenyl)acetate (202a) (0.172 g, 0.325 mmol) in DCM (20 mL) using TFA (0.5 mL, 6.5 mmol). This gave after workup and purification by flash column chromatography [silica gel 12 g, eluting with methanol in DCM from 0-100%] ethyl 2-(2-((7-(3-(aminomethyl)phenyl)benzofuran-5-yl)methoxy)-4-methylphenyl)acetate (202b) (0.053 g, 0.123 mmol, 38.0% yield) as a white solid; $^1$H NMR (300 MHz, DMSO-$d_6$) δ 8.11 (d, J=2.2 Hz, 1H), 7.99-7.87 (m, 2H), 7.73 (d, J=1.6 Hz, 1H), 7.61-7.57 (m, 2H), 7.56-7.50 (m, 1H), 7.13-7.05 (m, 2H), 6.98-6.94 (m, 1H), 6.74 (d, J=7.5 Hz, 1H), 5.22 (s, 2H), 4.13 (s, 2H), 3.91 (q, J=7.1 Hz, 2H), 3.57 (s, 2H), 2.30 (s, 3H), 0.97 (t, J=7.1 Hz, 3H); MS (ES+): 430.25 (M+1); MS (ES−): 428.30 (M−1).

Step-3: Preparation of 2-(2-((7-(3-(aminomethyl)phenyl)benzofuran-5-yl)methoxy)-4-methylphenyl)acetic Acid (202c)

Compound 202c was prepared according to the procedure reported in step-6 of Scheme-1 from ethyl 2-(2-((7-(3-(aminomethyl)phenyl)benzofuran-5-yl)methoxy)-4-methylphenyl)acetate (202b) (0.05 g, 0.116 mmol) in THF (4 mL) and methanol (8 mL) using LiOH (2M, 0.582 mL, 1.164 mmol). This gave after workup and purification by flash column chromatography [silica gel 12 g, eluting with methanol in DCM from 0-100%] followed by reverse phase column chromatography [C18 (50 g), eluting with ACN in water (containing 0.1% HCl) from 0-100%] 2-(2-((7-(3-(aminomethyl)phenyl)benzofuran-5-yl)methoxy)-4-methylphenyl)acetic acid (202c) (0.022 g, 47% yield) as a white solid; $^1$H NMR (300 MHz, DMSO-$d_6$) δ 8.37 (bs, 3H, D$_2$O exchangeable), 8.11 (d, J=2.2 Hz, 1H), 8.05-7.98 (m, 1H), 7.93 (dt, J=7.6, 1.6 Hz, 1H), 7.76 (d, J=1.6 Hz, 1H), 7.65 (d, J=1.7 Hz, 1H), 7.63-7.51 (m, 2H), 7.15-7.03 (m, 2H), 6.94 (d, J=1.5 Hz, 1H), 6.72 (d, J=7.4 Hz, 1H), 5.24 (s, 2H), 4.14 (s, 2H), 3.53 (s, 2H), 2.29 (s, 3H); MS (ES+): 402.20 (M+1); MS (ES−): 400.30 (M−1).

Scheme-203

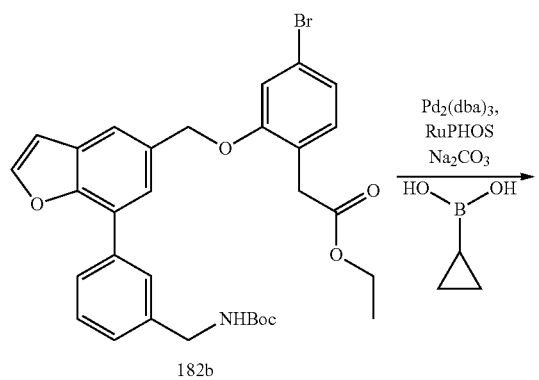

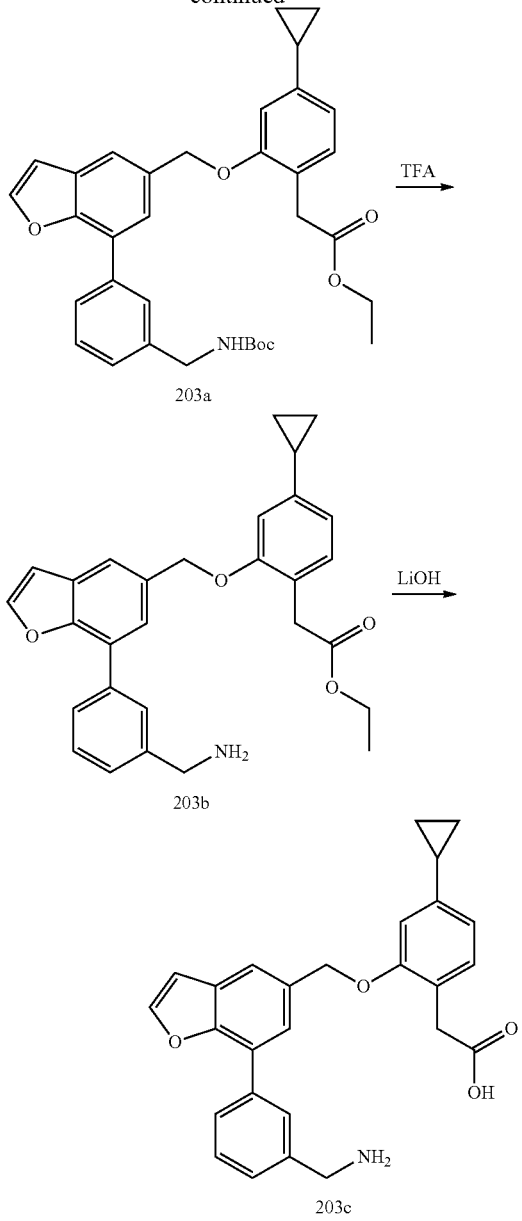

Preparation of 2-(2-((7-(3-(aminomethyl)phenyl)benzofuran-5-yl)methoxy)-4-cyclopropylphenyl)acetic Acid (203c)

Step-1: Preparation of Ethyl 2-(2-((7-(3-(((tert-butoxycarbonyl)amino)methyl)phenyl)benzofuran-5-yl)methoxy)-4-cyclopropylphenyl)acetate (203a)

Compound 203a was prepared according to the procedure reported in step-5 of Scheme-1 from ethyl 2-(4-bromo-2-((7-(3-((tert-butoxycarbonylamino)methyl)phenyl)benzofuran-5-yl)methoxy)phenyl)acetate (182b) (0.250 g, 0.421 mmol) in toluene (20 mL) and a solution of Na$_2$CO$_3$ (0.178 g, 1.682 mmol) in water (2 mL) using cyclopropylboronic acid (0.054 g, 0.631 mmol), dicyclohexyl(2',6'-diisopropoxybiphenyl-2-yl)phosphine (RuPHOS) (0.020 g, 0.042 mmol), Pd$_2$(dba)$_3$ (0.019 g, 0.021 mmol) and heating at 100°

C. for 10 h. This gave after workup and purification by flash column chromatography [silica gel 24 g, eluting with EtOAc in hexanes from 0-70%] ethyl 2-(2-((7-(3-(((tert-butoxycarbonyl)amino)methyl)phenyl)benzofuran-5-yl)methoxy)-4-cyclopropylphenyl)acetate (203a) (0.208 g, 89% yield) as a waxy white solid; $^1$H NMR (300 MHz, DMSO-d$_6$) δ 8.08 (d, J=2.2 Hz, 1H), 7.77-7.73 (m, 2H), 7.73-7.69 (m, 1H), 7.55 (d, J=1.7 Hz, 1H), 7.54-7.43 (m, 1H), 7.30 (d, J=7.6 Hz, 1H), 7.11-7.01 (m, 2H), 6.82 (d, J=1.6 Hz, 1H), 6.62 (dd, J=7.7, 1.6 Hz, 1H), 5.22 (s, 2H), 4.22 (d, J=6.2 Hz, 2H), 3.89 (q, J=7.1 Hz, 2H), 3.55 (s, 2H), 1.97-1.81 (m, 1H), 1.39 (s, 9H), 1.22-1.13 (m, 3H), 0.95-0.89 (m, 2H), 0.73-0.64 (m, 2H); MS (ES+): 456.30 (M+1, loss of Boc).

Step-3: Preparation of Ethyl 2-(2-((7-(3-(aminomethyl)phenyl)benzofuran-5-yl)methoxy)-4-cyclopropylphenyl)acetate (203b)

Compound 203b was prepared according to the procedure reported in step-5 of Scheme-1 from ethyl 2-(2-((7-(3-(((tert-butoxycarbonyl)amino)methyl)phenyl)benzofuran-5-yl)methoxy)-4-cyclopropylphenyl)acetate (203a) (0.200 g, 0.360 mmol) in DCM (20 mL) using TFA (0.555 mL, 7.20 mmol). This gave after workup and purification by reverse phase column chromatography [C-18 column, 30 g, eluting with 0.1% aq. HCl in water and acetonitrile from 0-100%], ethyl 2-(2-((7-(3-(aminomethyl)phenyl)benzofuran-5-yl)methoxy)-4-cyclopropylphenyl)acetate (203b) (0.102 g, 62% yield) HCl salt as a white solid; $^1$H NMR (300 MHz, DMSO-d$_6$) δ 8.31 (bs, 3H, D$_2$O exchangeable), 8.11 (d, J=2.2 Hz, 1H), 7.99 (s, 1H), 7.94-7.88 (m, 1H), 7.73 (d, J=1.6 Hz, 1H), 7.66-7.50 (m, 3H), 7.11-7.04 (m, 2H), 6.82 (d, J=1.6 Hz, 1H), 6.63 (dd, J=7.8, 1.6 Hz, 1H), 5.23 (s, 2H), 4.14 (s, 2H), 3.91 (q, J=7.1 Hz, 2H), 3.55 (s, 2H), 1.96-1.82 (m, 1H), 1.02-0.87 (m, 5H), 0.73-0.62 (m, 2H); MS (ES+): 456.27 (M+1), MS (ES−): 454.20 (M−1); HPLC purity: 93.97%.

Step-3: Preparation of 2-(2-((7-(3-(aminomethyl)phenyl)benzofuran-5-yl)methoxy)-4-cyclopropylphenyl)acetic Acid (203c)

Compound 203c was prepared according to the procedure reported in step-6 of Scheme-1 from ethyl 2-(2-((7-(3-(aminomethyl)phenyl)benzofuran-5-yl)methoxy)-4-cyclopropylphenyl)acetate (203b) (0.083 g, 0.182 mmol) in THF (4 mL) and methanol (8 mL) using 2M LiOH (0.455 mL, 0.911 mmol). This gave after workup and purification by flash column chromatography [silica gel 12 g, eluting with methanol in DCM from 0-50%] followed by reverse phase column chromatography [C18 (50 g), eluting with ACN in water (containing 0.1% HCl) from 0-100%] 2-(2-((7-(3-(aminomethyl)phenyl)benzofuran-5-yl)methoxy)-4-cyclopropylphenyl)acetic acid (203c) (0.003 g, 3.85% yield) HCl salt as a white solid; $^1$H NMR (300 MHz, DMSO-d$_6$) δ 8.31 (s, 1H), 8.14-8.06 (m, 2H), 7.89 (s, 1H), 7.69 (s, 1H), 7.49 (t, J=7.7 Hz, 1H), 7.37 (d, J=7.6 Hz, 1H), 7.07 (d, J=2.2 Hz, 1H), 6.95 (d, J=7.5 Hz, 1H), 6.73-6.63 (m, 1H), 6.52 (d, J=7.5 Hz, 1H), 5.25 (s, 2H), 4.01 (s, 2H), 3.33 (s, 2H), 1.90-1.75 (m, 1H), 0.94-0.80 (m, 2H), 0.67-0.57 (m, 2H); MS (ES+): 428.2 (M+1); MS (ES−): 426.30 (M−1).

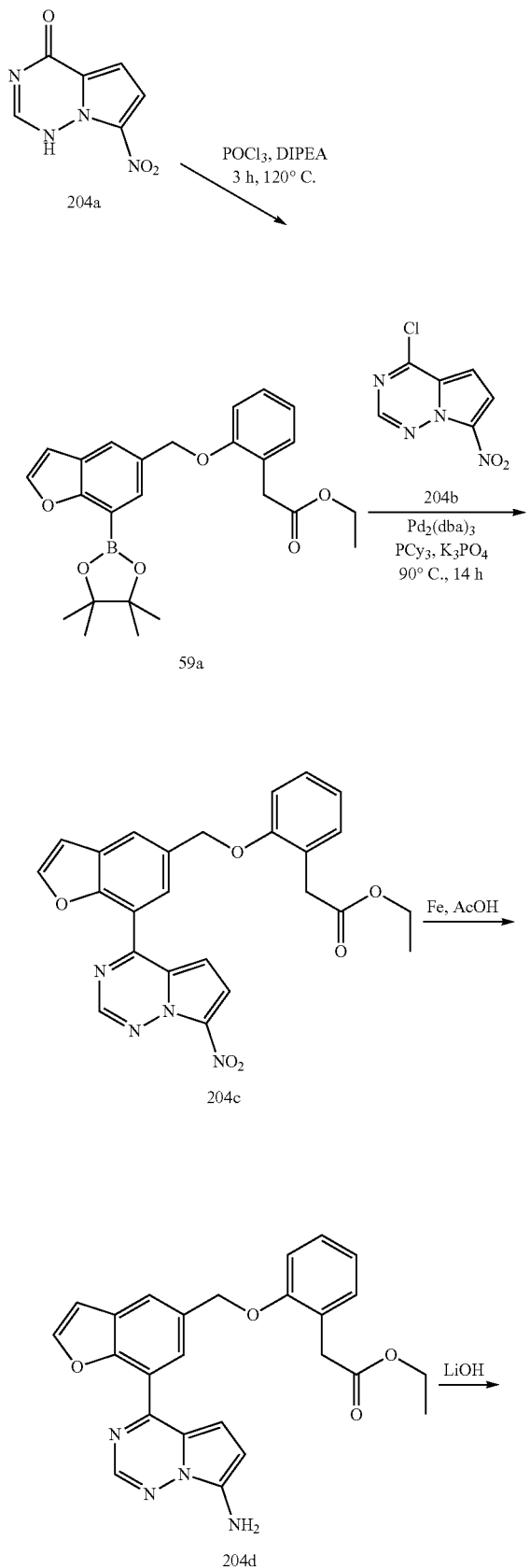

Scheme-204

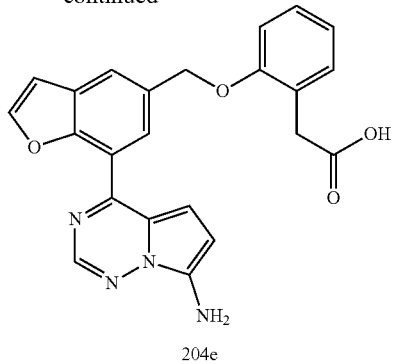

204e

Preparation of 2-(2-((7-(7-aminopyrrolo[2,1-f][1,2,4]triazin-4-yl)benzofuran-5-yl)methoxy)phenyl)acetic Acid (204e)

Step-1: Preparation of 4-chloro-7-nitropyrrolo[2,1-f][1,2,4]triazine (204b)

To a stirred solution of 7-nitropyrrolo[2,1-J][1,2,4]triazin-4(1H)-one (204a) (1.0 g, 5.55 mmol, CAS #1620778-25-7; prepared according to the procedure reported by Kumrnar, Pradeep et al; in PCT Int. Appl., 2014115171) in toluene (20.0 mL) was added POCl$_3$ (3.0 mL), DIPEA (6.0 mL) and heated at 120° C. for 3 h. The reaction mixture was cooled to RT, poured into ice water (20 mL) and extracted with EtOAc (2×100 mL). The combined organic extracts were washed with saturated NaHCO$_3$ solution (50.0 mL), dried, filtered and concentrated under vacuum. The residue obtained was purified by flash column chromatography [silica gel, eluting with (0-20%) EtOAc in n-hexane] to afford 4-chloro-7-nitropyrrolo[2,1-J][1,2,4]triazine (204b) (0.63 g, 57%) as an off white solid; $^1$H NMR (300 MHz, DMSO-d$_6$) δ 9.24 (d, J=1.8 Hz, 1H), 8.72 (s, 1H), 7.76 (d, J=1.9 Hz, 1H).

Step-2: Preparation of Ethyl 2-(2-((7-(7-nitropyrrolo[2,1-f][1,2,4]triazin-4-yl)benzofuran-5-yl)methoxy)phenyl)acetate (204c)

Compound 204c was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (1.0 g, 2.29 mmol) in dioxane (20 mL) using 4-chloro-7-nitropyrrolo[2,1-f][1,2,4]triazine (204b) (0.54 g, 2.75 mmol; CAS #58971-11-2), a solution of tripotassium phosphate (0.9 g, 4.58 mmol) in DMW (2.0 mL), tricyclohexylphosphine (0.12 g, 0.45 mmol) and Pd$_2$(dba)$_3$ (0.31 g, 0.34 mmol) under a nitrogen atmosphere heating at 90° C. for 14 h in a sealed tube. This gave after workup, purification by flash column chromatography [silica gel, eluting with EtOAc in n-hexane (0-20%)] ethyl 2-(2-((7-(7-nitropyrrolo[2,1-f][1,2,4]triazin-4-yl)benzofuran-5-yl)methoxy)phenyl)acetate (204c) (0.135 g, 13%) as an off-white solid; $^1$H NMR (300 MHz, DMSO-d$_6$) δ 9.21 (d, J=1.8 Hz, 1H), 9.00 (s, 1H), 8.20 (d, J=2.2 Hz, 1H), 8.04 (d, J=1.6 Hz, 1H), 7.99 (d, J=1.7 Hz, 1H), 7.60 (d, J=1.8 Hz, 1H), 7.33-7.20 (m, 2H), 7.20-7.11 (m, 2H), 6.93 (td, J=7.4, 1.1 Hz, 1H), 5.34 (s, 2H), 3.90 (q, J=7.1 Hz, 2H), 3.64 (s, 2H), 0.95 (t, J=7.1 Hz, 3H); MS (ES+): 473.2 (M+1).

Step-3: Preparation of Ethyl 2-(2-((7-(7-aminopyrrolo[2,1-f][1,2,4]triazin-4-yl)benzofuran-5-yl)methoxy)phenyl)acetate (204d)

To a solution of ethyl 2-(2-((7-(7-nitropyrrolo[2,1-f][1,2,4]triazin-4-yl)benzofuran-5-yl)methoxy)phenyl)acetate (204c) (19 mg, 0.04 mmol) in AcOH (1 mL) at 0° C. was added iron powder (19 mg, 0.34 mmol). The mixture was warmed to room temperature and stirred for two hours. The mixture was poured into saturated NaHCO$_3$ aqueous solution, extracted with ethyl acetate. The organic layers were combined, dried and concentrated. The crude residue was purified by chromatography [silica (12 g), eluting with DMA/DCM, 0-30%] to give ethyl 2-(2-((7-(7-aminopyrrolo[2,1-f][1,2,4]triazin-4-yl)benzofuran-5-yl)methoxy)phenyl)acetate (204d) (8 mg, 45%) as yellow foam. $^1$H NMR (300 MHz, DMSO-d$_6$) δ 8.32 (s, 1H), 7.91-7.78 (m, 3H), 7.66 (d, J=1.7 Hz, 1H), 7.30-7.16 (m, 2H), 7.07 (dd, J=8.3, 1.2 Hz, 1H), 6.98 (d, J=2.2 Hz, 1H), 6.96-6.88 (m, 1H), 6.28 (d, J=1.7 Hz, 1H), 5.25 (s, 2H), 3.91 (q, J=7.1 Hz, 2H), 3.65 (s, 2H), 0.98 (t, J=7.1 Hz, 3H); MS (ES+): 443.2 (M+1).

Step-4: Preparation of 2-(2-((7-(7-aminopyrrolo[2,1-f][1,2,4]triazin-4-yl)benzofuran-5-yl)methoxy)phenyl)acetic Acid (204e)

Compound 204e was prepared according to the procedure reported in step-6 of Scheme-1, from ethyl 2-(2-((7-(7-aminopyrrolo[2,1-f][1,2,4]triazin-4-yl)benzofuran-5-yl)methoxy)phenyl)acetate (204d) (94 mg, 0.212 mmol) in MeOH/THF (6 mL, each) using a solution of lithium hydroxide monohydrate (51 mg, 2.13 mmol) in water (2 mL). This gave after workup and purification by reverse phase column [C18 (50 g), eluting with ACN in water (containing 0.1% HCl) from 0-100%] 2-(2-((7-(7-aminopyrrolo[2,1-f][1,2,4]triazin-4-yl)benzofuran-5-yl)methoxy)phenyl)acetic acid (204e) (17 mg, 9% yield) HCl salt as orange solid. $^1$H NMR (300 MHz, DMSO-d$_6$, D$_2$O exchange) δ 8.72 (s, 1H), 8.15 (d, J=22.3 Hz, 2H), 7.96 (d, J=42.4 Hz, 2H), 7.36-6.99 (m, 4H), 6.91 (t, J=7.4 Hz, 1H), 6.68 (s, 1H), 5.30 (s, 2H), 3.58 (s, 2H); $^1$H NMR (300 MHz, DMSO-d$_6$) δ 8.75 (s, 1H), 8.19 (s, 2H), 8.16 (s, 1H), 8.03 (s, 1H), 7.91 (s, 1H), 7.34-7.19 (m, 3H), 7.16-7.05 (m, 2H), 6.91 (t, J=7.5 Hz, 1H), 6.71 (s, 1H), 5.32 (s, 2H), 3.59 (s, 2H); MS (ES+): 415.1 (M+1); MS(ES-): 413.2 (M-1). HPLC purity: 97.4%.

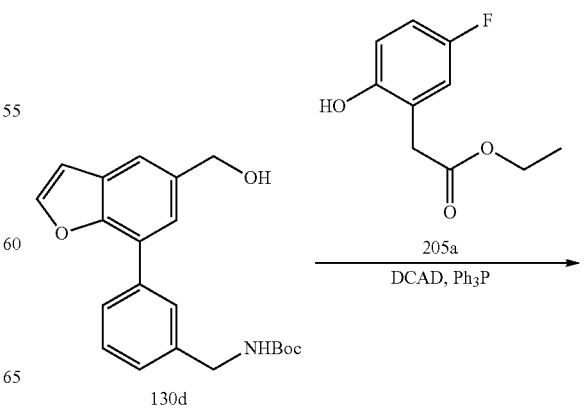

Scheme-205

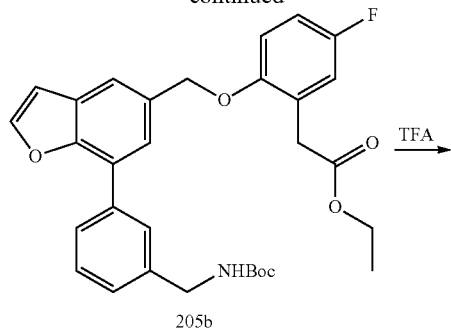

205b

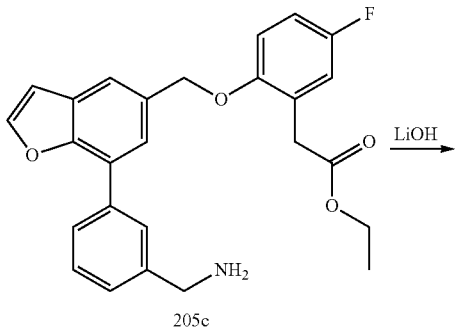

205c

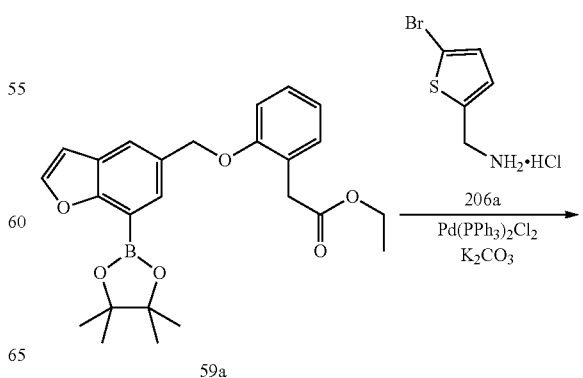

205d

Preparation of 2-(2-((7-(3-(aminomethyl)phenyl)
benzofuran-5-yl)methoxy)-5-fluorophenyl)acetic
Acid (205d)

Step-1: Preparation of Ethyl 2-(2-((7-(3-(((tert-butoxycarbonyl)amino)methyl)phenyl)benzofuran-5-yl)methoxy)-5-fluorophenyl)acetate (205b)

Compound 205b was prepared according to the procedure reported in step-2 of Scheme-23 from tert-butyl 3-(5-(hydroxymethyl)benzofuran-7-yl)benzylcarbamate (130d) (250 mg, 0.707 mmol) in DCM (8 mL) using triphenylphosphine (195 mg, 0.743 mmol), ethyl 2-(5-fluoro-2-hydroxyphenyl) acetate (205a) (147 mg, 0.743 mmol) and E)-bis(4-chlorobenzyl) diazene-1,2-dicarboxylate (DCAD, 273 mg, 0.743 mmol). This gave after workup and purification by flash column chromatography [silica gel 40 g, eluting with ethyl acetate in hexanes from 0-40%] ethyl 2-(2-((7-(3-(((tert-butoxycarbonyl)amino)methyl)phenyl)benzofuran-5-yl) methoxy)-5-fluorophenyl)acetate (205b) (220 mg, 58% yield) as a brownish solid; $^1$H NMR (300 MHz, DMSO-$d_6$) δ 8.08 (d, J=2.2 Hz, 1H), 7.76-7.67 (m, 3H), 7.53 (d, J=1.7 Hz, 1H), 7.52-7.44 (m, 2H), 7.30 (d, J=7.6 Hz, 1H), 7.17-7.08 (m, 3H), 7.05 (d, J=2.2 Hz, 1H), 5.21 (s, 2H), 4.22 (d, J=6.2 Hz, 2H), 3.92 (q, J=7.1 Hz, 2H), 3.64 (s, 2H), 1.39 (s, 9H), 0.97 (t, J=7.1 Hz, 3H).

Step-2: Preparation of Ethyl 2-(2-((7-(3-(aminomethyl)phenyl)benzofuran-5-yl)methoxy)-5-fluorophenyl)acetate (205c)

Compound 205c was prepared according to the procedure reported in step-5 of Scheme-1 from ethyl 2-(2-((7-(3-(((tert-butoxycarbonyl)amino)methyl)phenyl)benzofuran-5-yl)methoxy)-5-fluorophenyl)acetate (205b) (140 mg, 0.262 mmol) in DCM (5 mL) using TFA (121 μl, 1.574 mmol). This gave after workup and purification by flash column chromatography [silica gel 12 g, eluting with methanol in DCM from 0-40%] ethyl 2-(2-((7-(3-(aminomethyl)phenyl) benzofuran-5-yl)methoxy)-5-fluorophenyl)acetate (205c) (0.14 g, 98% % yield) TFA salt as a solid; $^1$H NMR (300 MHz, DMSO-$d_6$) δ 8.24 (s, 3H), 8.12 (d, J=2.2 Hz, 1H), 8.01-7.94 (m, 1H), 7.91 (dt, J=7.8, 1.5 Hz, 1H), 7.73 (d, J=1.6 Hz, 1H), 7.66-7.47 (m, 3H), 7.20-7.03 (m, 4H), 5.23 (s, 2H), 4.15 (s, 2H), 3.94 (q, J=7.1 Hz, 2H), 3.65 (s, 2H), 0.99 (t, J=7.1 Hz, 3H).

Step-3: Preparation of 2-(2-((7-(3-(aminomethyl) phenyl)benzofuran-5-yl)methoxy)-5-fluorophenyl) acetic Acid (205d)

Compound 205d was prepared according to the procedure reported in step-6 of Scheme-1 from ethyl 2-(2-((7-(3-(aminomethyl)phenyl)benzofuran-5-yl)methoxy)-5-fluorophenyl)acetate (205c) (0.14 g, 0.256 mmol) in THF (3 mL) and methanol (2.25 mL) using lithium hydroxide hydrate (107 mg, 2.56 mmol) in Water (3.00 mL). This gave after workup and purification by reverse phase column [C18 (50 g), eluting with ACN in water (containing 0.1% HCl) from 0-100%] 2-(2-((7-(3-(aminomethyl)phenyl)benzofuran-5-yl)methoxy)-5-fluorophenyl)acetic acid (205d) (60 mg, 0.136 mmol, 53.1% yield) HCl salt as a white solid; $^1$H NMR (300 MHz, DMSO-$d_6$) δ 12.35 (s, 1H), 8.35 (s, 3H), 8.11 (d, J=2.2 Hz, 1H), 7.99 (s, 1H), 7.92 (dt, J=7.5, 1.6 Hz, 1H), 7.75 (d, J=1.6 Hz, 1H), 7.63 (d, J=1.8 Hz, 1H), 7.58 (d, J=7.5 Hz, 1H), 7.56-7.50 (m, 1H), 7.16-7.07 (m, 3H), 7.06 (d, J=2.2 Hz, 1H), 5.25 (s, 2H), 4.14 (s, 2H), 3.61 (s, 2H); MS (ES+): 406.2 (M+1); (ES−): 404.3 (M−1).

Scheme-206

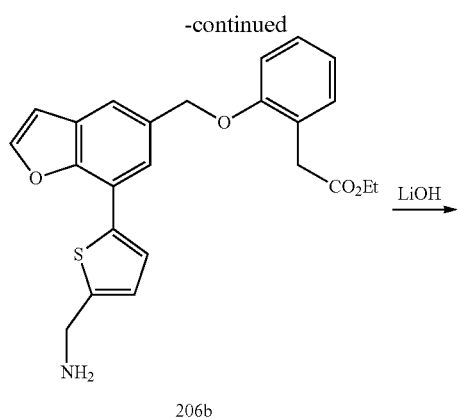

206b

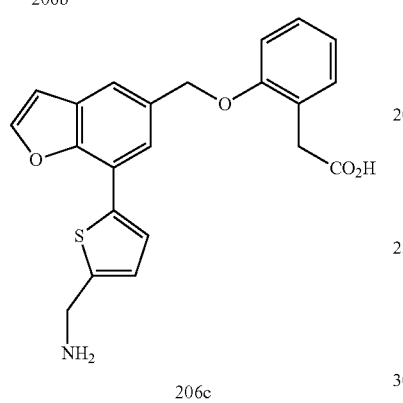

206c

Preparation of 2-(2-((7-(5-(aminomethyl)thiophen-2-yl)benzofuran-5-yl)methoxy)phenyl)acetic Acid (206c)

Step-1: Preparation of Ethyl 2-(2-((7-(5-(aminomethyl)thiophen-2-yl)benzofuran-5-yl)methoxy)phenyl)acetate (206b)

Compound 206b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (520 mg, 1.192 mmol) in dioxane (9 mL) using (5-bromothiophen-2-yl)methanamine hydrochloride (206a) (300 mg, 1.311 mmol; CAS #1001414-56-7), bis(triphenylphosphine)palladium(II) chloride (125 mg, 0.179 mmol), a solution of $K_2CO_3$ (659 mg, 4.77 mmol) in water (1 mL) under an Ar atmosphere and heating at 90° C. for 14 h on an oil bath. This gave after workup, purification by flash column chromatography [silica (24 g), eluting with EtOAc in hexane from 0-100%] ethyl 2-(2-((7-(5-(aminomethyl)thiophen-2-yl)benzofuran-5-yl)methoxy)phenyl)acetate (206b) (250 mg, 50% yield) as a brownish oily residue; $^1$H NMR (300 MHz, DMSO-$d_6$) δ 8.60 (s, 3H), 8.18 (d, J=2.2 Hz, 1H), 7.76 (d, J=3.7 Hz, 1H), 7.72 (d, J=1.6 Hz, 1H), 7.68 (d, J=1.5 Hz, 1H), 7.38 (d, J=3.7 Hz, 1H), 7.30-7.19 (m, 2H), 7.11 (dd, J=8.3, 1.1 Hz, 1H), 7.08 (d, J=2.2 Hz, 1H), 6.91 (td, J=7.4, 1.1 Hz, 1H), 5.23 (s, 2H), 4.30 (s, 2H), 3.96 (q, J=7.1 Hz, 2H), 3.63 (s, 2H), 1.01 (t, J=7.1 Hz, 3H).

Step-2: Preparation of 2-(2-((7-(5-(aminomethyl)thiophen-2-yl)benzofuran-5-yl)methoxy)phenyl)acetic Acid (206c)

Compound 206c was prepared according to the procedure reported in step-6 of Scheme-1, from ethyl 2-(2-((7-(5-(aminomethyl)thiophen-2-yl)benzofuran-5-yl)methoxy)phenyl)acetate (206b) (150 mg, 0.356 mmol) in MeOH/THF (5 mL, each) using a solution of lithium hydroxide monohydrate (149 mg, 3.56 mmol) in water (3 mL). This gave after workup and purification by reverse phase column [C18 (50 g), eluting with ACN in water (containing 0.1% HCl) from 0-100%] 2-(2-((7-(5-(aminomethyl)thiophen-2-yl)benzofuran-5-yl)methoxy)phenyl)acetic acid (206c) (118 mg, 46% yield) HCl salt as a white solid; $^1$H NMR (300 MHz, DMSO-$d_6$) δ 8.17 (d, J=2.2 Hz, 1H), 7.78 (d, J=3.7 Hz, 1H), 7.76 (d, J=1.6 Hz, 1H), 7.71 (d, J=1.5 Hz, 1H), 7.33 (d, J=3.8 Hz, 1H), 7.27-7.18 (m, 2H), 7.10 (d, J=1.1 Hz, 1H), 7.07 (d, J=2.2 Hz, 1H), 6.91 (td, J=7.6, 0.9 Hz, 1H), 5.26 (s, 2H), 4.32 (s, 2H), 3.60 (s, 2H); MS (ES-): 392.2 (M-1).

Scheme-207

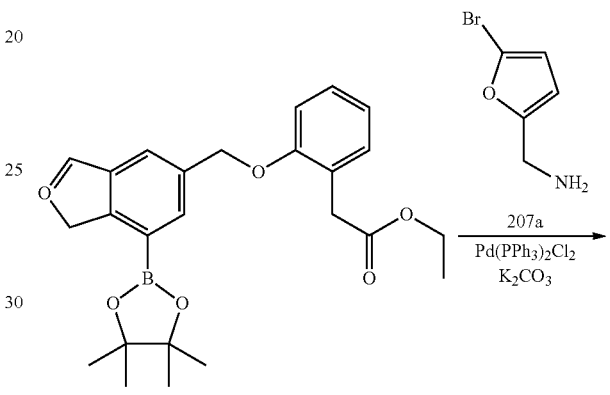

59a

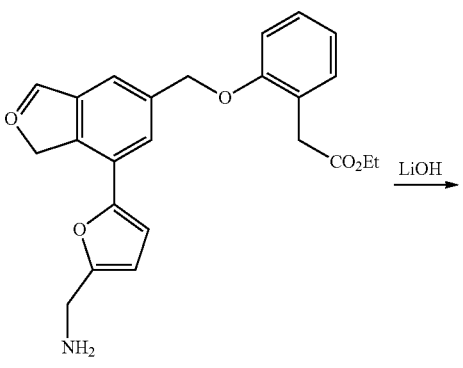

207b

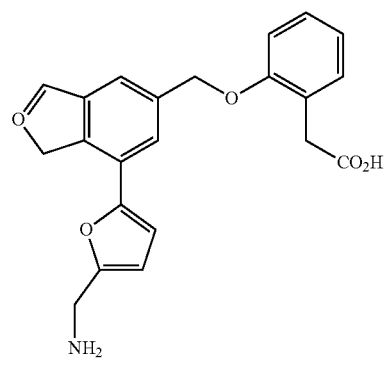

207c

Preparation of 2-(2-((7-(5-(aminomethyl)furan-2-yl)benzofuran-5-yl)methoxy)phenyl)acetic acid (207c)

Step-1: Preparation of Ethyl 2-(2-((7-(5-(aminomethyl)furan-2-yl)benzofuran-5-yl)methoxy)phenyl)acetate (207b)

Compound 207b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (458 mg, 1.050 mmol) in dioxane (9 mL) using (5-bromofuran-2-yl)methanamine (207a) (194 mg, 1.102 mmol; CAS #263169-37-5), bis(triphenylphosphine)palladium(II) chloride (111 mg, 0.157 mmol), a solution of K$_2$CO$_3$ (450 mg, 3.25 mmol) in water (1 mL) under an Ar atmosphere and heating at 90° C. for 14 h on an oil bath. This gave after workup, purification by flash column chromatography [silica (24 g), eluting with EtOAc in hexane from 0-100%] ethyl 2-(2-((7-(5-(aminomethyl)furan-2-yl)benzofuran-5-yl)methoxy)phenyl)acetate (207b) (200 mg, 47.0% yield) as a yellow foam; $^1$H NMR (300 MHz, DMSO-d$_6$) δ 8.13 (d, J=2.2 Hz, 1H), 7.72 (d, J=1.7 Hz, 1H), 7.62 (d, J=1.7 Hz, 1H), 7.30-7.20 (m, 2H), 7.13-7.06 (m, 2H), 7.04 (d, J=2.2 Hz, 1H), 6.91 (td, J=7.4, 1.1 Hz, 1H), 6.45-6.42 (m, 1H), 5.22 (s, 2H), 3.99 (q, J=7.1 Hz, 2H), 3.78 (s, 2H), 3.62 (s, 2H), 1.02 (t, J=7.1 Hz, 3H).

Step-2: Preparation of 2-(2-((7-(5-(aminomethyl)furan-2-yl)benzofuran-5-yl)methoxy)phenyl)acetic Acid (207c)

Compound 207c was prepared according to the procedure reported in step-6 of Scheme-1i, from ethyl 2-(2-((7-(5-(aminomethyl)furan-2-yl)benzofuran-5-yl)methoxy)phenyl)acetate (207b) (200 mg, 0.493 mmol) in MeOH/THF (3 mL, each) using a solution of lithium hydroxide monohydrate (207 mg, 4.93 mmol) in water (3 mL). This gave after workup and purification by reverse phase column [C18 (50 g), eluting with ACN in water (containing 0.1% HCl) from 0-100%] 2-(2-((7-(5-(aminomethyl)furan-2-yl)benzofuran-5-yl)methoxy)phenyl)acetic acid (207c) (6 mg, 3% yield) HCl salt as a white solid; $^1$H NMR (300 MHz, DMSO-d$_6$) δ 8.38 (s, 3H), 8.16 (d, J=2.2 Hz, 1H), 7.83 (d, J=1.7 Hz, 1H), 7.73 (d, J=1.6 Hz, 1H), 7.27-7.19 (m, 2H), 7.17 (d, J=3.4 Hz, 1H), 7.10-7.05 (m, 2H), 6.91 (td, J=7.4, 1.1 Hz, 1H), 6.77 (d, J=3.3 Hz, 1H), 5.25 (s, 2H), 4.23 (s, 2H), 3.60 (s, 2H).

Scheme-208

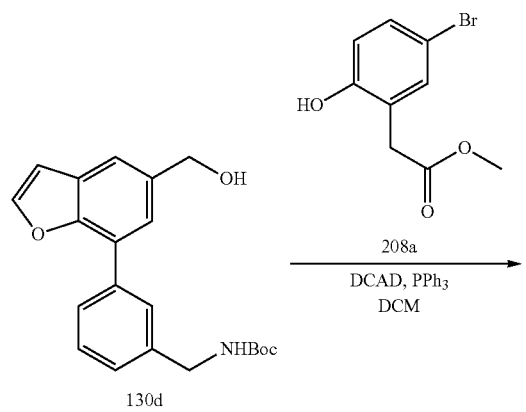

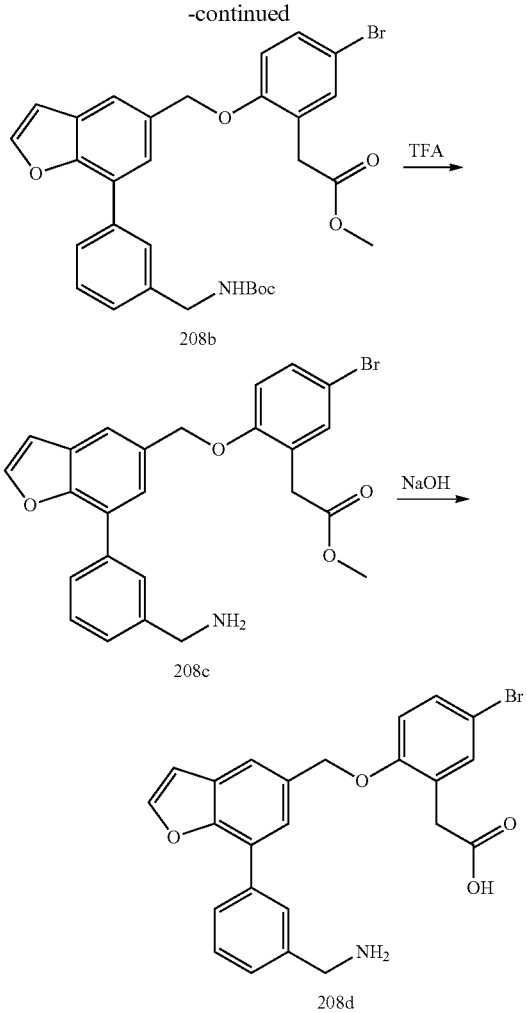

Preparation of 2-(2-((7-(3-(aminomethyl)phenyl)benzofuran-5-yl)methoxy)-5-bromophenyl)acetic Acid (208d)

Step-1: Preparation of methyl 2-(5-bromo-2-((7-(3-(((tert-butoxycarbonyl)amino)methyl)phenyl)benzofuran-5-yl)methoxy)phenyl)acetate (208b)

Compound 208b was prepared according to the procedure reported in step-2 of Scheme-23 from tert-butyl 3-(5-(hydroxymethyl)benzofuran-7-yl)benzylcarbamate (130d) (1167 mg, 3.30 mmol) in DCM (10 mL) using triphenylphosphine (953 mg, 3.63 mmol), methyl 2-(5-cyclopropyl-2-hydroxyphenyl)acetate (208a) (850 mg, 3.47 mmol) and di-(4-chlorobenzyl)azodicarboxylate (1334 mg, 3.63 mmol). This gave after workup and purification by flash column chromatography [silica gel 40 g, eluting with ethyl acetate in hexanes from 0-40%] methyl 2-(5-bromo-2-((7-(3-(((tert-butoxycarbonyl)amino)methyl)phenyl)benzofuran-5-yl)methoxy)phenyl)acetate (208b) (950 mg, 1.637 mmol, 49.5% yield) as a brownish amorphous solid; $^1$H NMR (300 MHz, DMSO-d$_6$) δ 8.08 (d, J=2.2 Hz, 1H), 7.76-7.70 (m, 2H), 7.68 (d, J=1.6 Hz, 1H), 7.50 (dd, J=13.0, 2.1 Hz, 2H), 7.47-7.41 (m, 2H), 7.34-7.27 (m, 1H), 7.13-7.08 (m, 1H), 7.07 (d, J=2.2 Hz, 1H), 5.25 (s, 2H), 4.23 (d, J=6.2 Hz, 2H), 3.67 (s, 2H), 3.47 (s, 3H), 1.39 (s, 9H).

Step-2: Preparation of methyl 2-(2-((7-(3-(aminomethyl)phenyl)benzofuran-5-yl)methoxy)-5-bromophenyl)acetate (208c)

Compound 208c was prepared according to the procedure reported in step-5 of Scheme-1 from methyl 2-(5-bromo-2-((7-(3-(((tert-butoxycarbonyl)amino)methyl)phenyl)benzofuran-5-yl)methoxy)phenyl)acetate (208b) (400 mg, 0.689 mmol) in DCM (5 mL) using TFA (531 µl, 6.89 mmol). This gave after workup and purification by flash column chromatography [silica gel 24 g, eluting with methanol in DCM from 0-20%] methyl 2-(2-((7-(3-(aminomethyl)phenyl)benzofuran-5-yl)methoxy)-5-bromophenyl)acetate (208c) (0.32 g, 78% yield) as a solid; $^1$H NMR (300 MHz, DMSO-$d_6$) δ 8.22 (s, 3H), 8.11 (d, J=2.2 Hz, 1H), 7.97 (t, J=1.7 Hz, 1H), 7.90 (dt, J=7.7, 1.5 Hz, 1H), 7.71 (d, J=1.6 Hz, 1H), 7.61 (t, J=7.7 Hz, 1H), 7.57-7.50 (m, 2H), 7.47-7.41 (m, 2H), 7.11-7.04 (m, 2H), 5.26 (s, 2H), 4.15 (s, 2H), 3.67 (s, 2H), 3.48 (d, J=1.3 Hz, 3H).

Step-3: Preparation of 2-(2-((7-(3-(aminomethyl)phenyl)benzofuran-5-yl)methoxy)-5-bromophenyl)acetic Acid (208d)

Compound 208d was prepared according to the procedure reported in step-6 of Scheme-1 from methyl 2-(2-((7-(3-(aminomethyl)phenyl)benzofuran-5-yl)methoxy)-5-bromophenyl)acetate (208c) (350 mg, 0.589 mmol) in THF (4 mL) and methanol (3 mL) using a solution of lithium hydroxide hydrate (173 mg, 4.12 mmol) in water (4.0 mL). This gave after workup and purification by reverse phase column [C18 (30 g), eluting with ACN in water (containing 0.1% HCl) from 0-100%] 2-(2-((7-(3-(aminomethyl)phenyl)benzofuran-5-yl)methoxy)-5-bromophenyl)acetic acid (208d) (200 mg, 73% yield) HCl salt as a white solid; $^1$H NMR (300 MHz, DMSO-$d_6$) δ 12.35 (s, 1H), 8.39 (s, 3H), 8.11 (d, J=2.2 Hz, 1H), 7.99 (s, 1H), 7.92 (dt, J=7.5, 1.6 Hz, 1H), 7.74 (d, J=1.6 Hz, 1H), 7.62 (d, J=1.8 Hz, 1H), 7.60-7.52 (m, 2H), 7.45-7.38 (m, 2H), 7.09-7.04 (m, 2H), 5.27 (s, 2H), 4.14 (s, 2H), 3.61 (s, 2H).

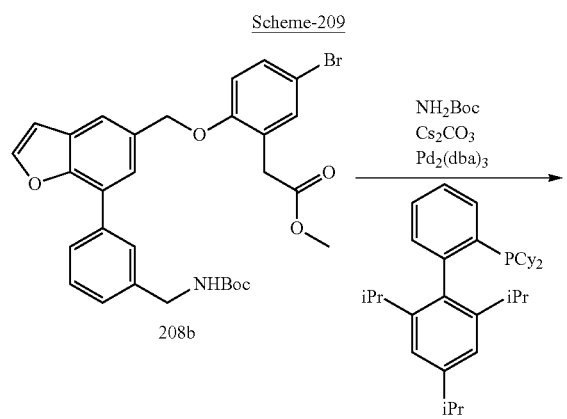

Scheme-209

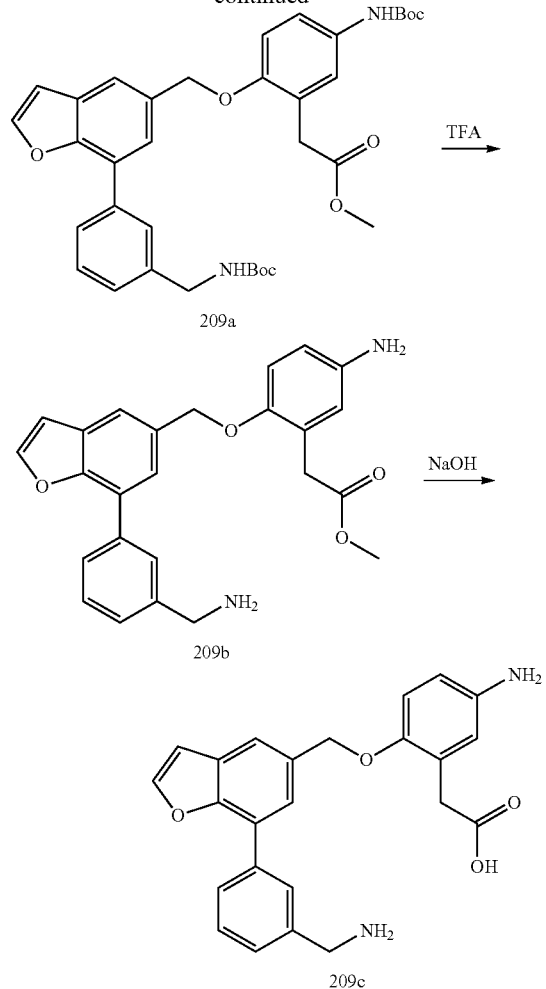

Preparation of 2-(5-amino-2-((7-(3-(aminomethyl)phenyl)benzofuran-5-yl)methoxy)phenyl)acetic Acid (209c)

Step-1: Preparation of methyl 2-(5-((tert-butoxycarbonyl)amino)-2-((7-(3-(((tert-butoxycarbonyl)amino)methyl)phenyl)benzofuran-5-yl)methoxy)phenyl)acetate (209a)

To a mixture of methyl 2-(5-bromo-2-((7-(3-((tert-butoxycarbonylamino)methyl)phenyl)benzofuran-5-yl)methoxy)phenyl)acetate (208b) (400 mg, 0.689 mmol) in Toluene (6 mL) was added dicyclohexyl(2',4',6'-triisopropylbiphenyl-2-yl)phosphine (X-PHOS, 0.032 g, 0.067 mmol), tert-butyl carbamate (121 mg, 1.034 mmol) and cesium carbonate (225 mg, 0.689 mmol) and degassed with nitrogen purge for 15 mins. Pd$_2$(dba)$_3$ (31.6 mg, 0.034 mmol) was added and the mixture was degassed for another 10 mins. The mixture was heated with stirring at 95° C. for 16 h, cooled to room temperature, diluted with EtOAc (50 mL) and filtered over a Celite pad. The Celite pad was rinsed with EtOAc (2×50 mL) and the filtrate was dried and concentrated in vacuum. The residue obtained was purified by flash column chromatography [silica gel 24 g, eluting with ethyl acetate in hexanes from 0-100%] to furnish methyl 2-(5-((tert-butoxycarbonyl)amino)-2-((7-(3-(((tert-butoxycarbonyl)amino)methyl)phenyl)benzofuran-5-yl)methoxy)phenyl)acetate (209a) (0.300 g, 71% yield) as a pale-brown foam; $^1$H NMR (300 MHz, DMSO-$d_6$) δ 9.15 (s, 1H), 8.07 (d, J=2.2 Hz, 1H), 7.77-7.70 (m, 2H), 7.67 (d, J=1.6 Hz, 1H), 7.52 (d, J=1.7 Hz, 1H), 7.51-7.43 (m, 1H), 7.37-7.21 (m, 3H), 7.06 (d, J=2.2 Hz, 1H), 7.02 (d, J=8.9 Hz, 1H), 5.18 (s, 2H), 4.22 (d, J=6.2 Hz, 2H), 3.60 (s, 2H), 3.47 (s, 3H), 1.45 (s, 9H), 1.39 (s, 9H).

Step-2: Preparation of methyl 2-(5-amino-2-((7-(3-(aminomethyl)phenyl)benzofuran-5-yl)methoxy)phenyl)acetate (209b)

Compound 209b was prepared according to the procedure reported in step-5 of Scheme-1 from methyl 2-(5-((tert-butoxycarbonyl)amino)-2-((7-(3-(((tert-butoxycarbonyl)amino)methyl)phenyl)benzofuran-5-yl)methoxy)phenyl)acetate (209a) (300 mg, 0.486 mmol) in DCM (5 mL) using TFA (0.375 mL, 4.86 mmol). This gave after workup and purification by flash column chromatography [silica gel 12 g, eluting with methanol in DCM from 0-20%] methyl 2-(5-amino-2-((7-(3-(aminomethyl)phenyl)benzofuran-5-yl)methoxy)phenyl)acetate (209b) (0.23 g, 73% yield) as a solid; $^1$H NMR (300 MHz, DMSO-$d_6$) δ 8.79 (s, 3H), 8.28 (s, 3H), 8.11 (d, J=2.2 Hz, 1H), 7.98 (t, J=1.7 Hz, 1H), 7.90 (dt, J=7.8, 1.5 Hz, 1H), 7.71 (d, J=1.6 Hz, 1H), 7.65-7.50 (m, 3H), 7.16-6.99 (m, 4H), 5.22 (s, 2H), 4.16 (s, 2H), 3.67 (s, 2H), 3.48 (s, 3H).

Step-3: Preparation of 2-(5-amino-2-((7-(3-(aminomethyl)phenyl)benzofuran-5-yl)methoxy)phenyl) acetic Acid (209c)

Compound 209c was prepared according to the procedure reported in step-6 of Scheme-1 from methyl 2-(5-amino-2-((7-(3-(aminomethyl)phenyl)benzofuran-5-yl)methoxy)phenyl)acetate (209b) (220 mg, 0.341 mmol) in THF (3 mL) and methanol (2 mL) using a solution of lithium hydroxide hydrate (143 mg, 3.41 mmol) in water (3 mL). This gave after workup and purification by reverse phase column [C18 (30 g), eluting with ACN in water (containing 0.1% HCl) from 0-100%] 2-(5-amino-2-((7-(3-(aminomethyl)phenyl)benzofuran-5-yl)methoxy)phenyl)acetic acid (209c) (130 mg, 80% yield) HCl salt as a white solid; $^1$H NMR (300 MHz, DMSO-$d_6$) δ 12.38 (s, 1H), 9.85 (s, 3H), 8.39 (s, 3H), 8.11 (d, J=2.2 Hz, 1H), 8.00 (s, 1H), 7.92 (dt, J=7.4, 1.7 Hz, 1H), 7.75 (d, J=1.6 Hz, 1H), 7.67-7.51 (m, 3H), 7.19 (d, J=2.7 Hz, 3H), 7.06 (d, J=2.2 Hz, 1H), 5.29 (s, 2H), 4.14 (d, J=5.6 Hz, 2H), 3.65 (s, 2H).

Scheme-210

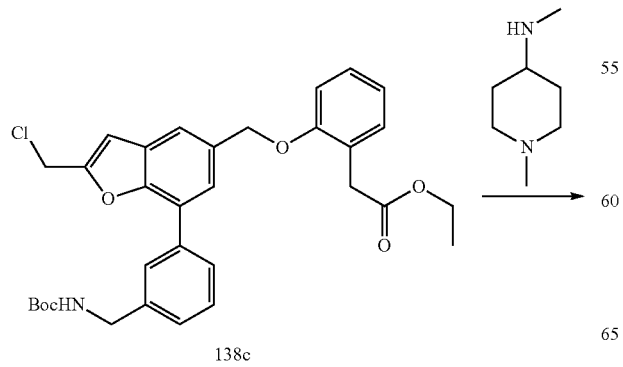

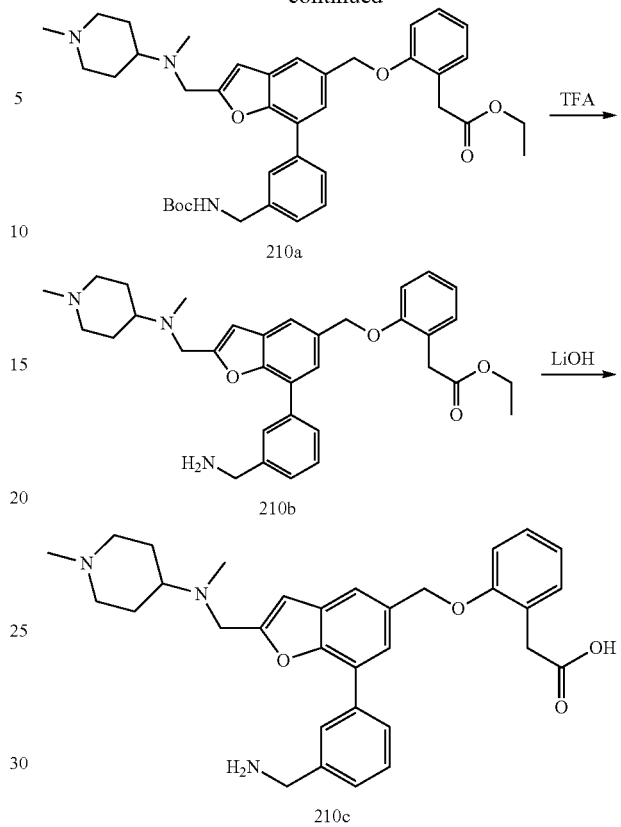

Preparation of 2-(2-((7-(3-(aminomethyl)phenyl)-2-((methyl(1-methylpiperidin-4-yl)amino)methyl)benzofuran-5-yl)methoxy)phenyl)acetic Acid (210c)

Step-1: Preparation of Ethyl 2-(2-((7-(3-(((tert-butoxycarbonyl)amino)methyl)phenyl)-2-((methyl(1-methylpiperidin-4-yl)amino)methyl)benzofuran-5-yl)methoxy)phenyl)acetate (210a)

Compound 210a was prepared according to the procedure reported in step-4 of Scheme-138 from ethyl 2-(2-((7-(3-(((tert-butoxycarbonyl)amino)methyl)phenyl)-2-(chloromethyl)benzofuran-5-yl)methoxy)phenyl)acetate (138c) (450 mg, 0.80 mmol) and N, 1-dimethylpiperidin-4-amine (113 mg, 0.88 mmol) in ACN (10 mL). This gave after workup and purification by flash column chromatography [silica (12 g), eluting with DMA80 in DCM from 0-50%] ethyl 2-(2-((7-(3-(((tert-butoxycarbonyl)amino)methyl)phenyl)-2-((methyl(1-methylpiperidin-4-yl)amino)methyl)benzofuran-5-yl)methoxy)phenyl)acetate (210a) (230 mg, 44% yield) as a clear oil; MS (ES+): 656.4 (M+1).

Step-2: Preparation of Ethyl 2-(2-((7-(3-(aminomethyl)phenyl)-2-((methyl(1-methylpiperidin-4-yl)amino)methyl)benzofuran-5-yl)methoxy)phenyl) acetate (210b)

Compound 210b was prepared according to the procedure reported in step-5 of Scheme-1 from ethyl 2-(2-((7-(3-(((tert-butoxycarbonyl)amino)methyl)phenyl)-2-((methyl(1-methylpiperidin-4-yl)amino)methyl)benzofuran-5-yl)methoxy)phenyl)acetate (210a) (223 mg, 0.34 mmol) in DCM (10 mL) using TFA (0.26 mL, 3.40 mmol). This gave after workup ethyl 2-(2-((7-(3-(aminomethyl)phenyl)-2-((methyl(1-methylpiperidin-4-yl)amino)methyl)benzofuran-5-yl)methoxy)phenyl)acetate (210b) (122 mg, 65% yield) as a clear oil; MS (ES+): 556.4 (M+1).

Step-3: Preparation of 2-(2-((7-(3-(aminomethyl)phenyl)-2-((methyl(1-methylpiperidin-4-yl)amino)methyl)benzofuran-5-yl)methoxy)phenyl)acetic Acid (210c)

Compound 210c was prepared according to the procedure reported in step-6 of Scheme-1 from ethyl 2-(2-((7-(3-(aminomethyl)phenyl)-2-((methyl(1-methylpiperidin-4-yl)amino)methyl)benzofuran-5-yl)methoxy)phenyl)acetate (210b) (120 mg, 0.22 mmol) in THF (6 mL) and methanol (6 mL) using a solution of lithium hydroxide monohydrate (21 mg, 0.86 mmol) in water (2.0 mL). This gave after workup and purification by reverse phase column [C18 (30 g), eluting with ACN in water (containing 0.1% HCl) from 0-100%] 2-(2-((7-(3-(aminomethyl)phenyl)-2-((methyl(1-methylpiperidin-4-yl)amino)methyl)benzofuran-5-yl)methoxy)phenyl)acetic acid (210c) (30 mg, 26% yield) HCl salt as a white solid; $^1$H NMR (300 MHz, DMSO-$d_6$) δ 12.27 (s, 1H, $D_2O$ exchangeable), 11.90 (s, 1H, $D_2O$ exchangeable), 10.92 (s, 1H, $D_2O$ exchangeable), 8.65 (s, 3H, $D_2O$ exchangeable), 8.23 (s, 1H), 8.01-7.93 (m, 1H), 7.81 (d, J=1.6 Hz, 1H), 7.75 (d, J=1.7 Hz, 1H), 7.62-7.53 (m, 2H), 7.39 (s, 1H), 7.27-7.19 (m, 2H), 7.10 (d, J=8.1 Hz, 1H), 6.96-6.86 (m, 1H), 5.29 (s, 2H), 4.71 (s, 2H), 4.24-4.09 (m, 2H), 3.62-3.48 (m, 6H), 3.08-2.90 (m, 2H), 2.87-2.77 (m, 3H), 2.71 (d, J=4.2 Hz, 3H), 2.42-2.32 (m, 1H), 2.30-2.13 (m, 2H); MS (ES+): 528.3 (M+1); (ES−): 526.3 (M−1).

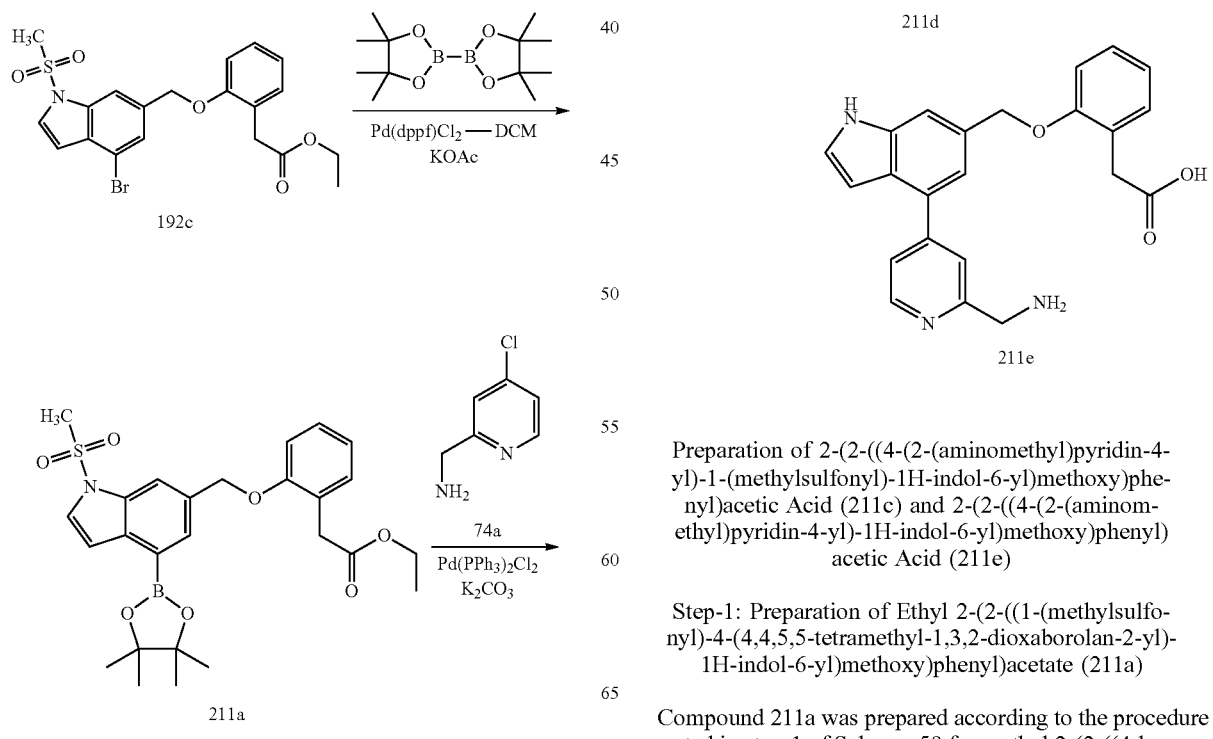

Preparation of 2-(2-((4-(2-(aminomethyl)pyridin-4-yl)-1-(methylsulfonyl)-1H-indol-6-yl)methoxy)phenyl)acetic Acid (211c) and 2-(2-((4-(2-(aminomethyl)pyridin-4-yl)-1H-indol-6-yl)methoxy)phenyl)acetic Acid (211e)

Step-1: Preparation of Ethyl 2-(2-((1-(methylsulfonyl)-4-(4,4,5,5-tetramethyl-1,3,2-dioxaborolan-2-yl)-1H-indol-6-yl)methoxy)phenyl)acetate (211a)

Compound 211a was prepared according to the procedure reported in step-1 of Scheme-59 from ethyl 2-(2-((4-bromo- 1-(methylsulfonyl)-1H-indol-6-yl)methoxy)phenyl)acetate (192c) (0.23 g, 0.49 mmol), using bis(pinacolato)diboron (0.19 g, 0.74 mmol), potassium acetate (0.01 g, 0.99 mmol) and Pd(dppf)Cl$_2$—CH$_2$Cl$_2$ (0.06 g, 0.07 mmol) in anhydrous dioxane (5 mL) under an Ar atmosphere and heating at 100° C. overnight. This gave after workup and purification by flash column chromatography [silica gel, 24 g, eluting with EtOAc/MeOH=9:1 in hexane from 0-10%] ethyl 2-(2-((1-(methylsulfonyl)-4-(4,4,5,5-tetramethyl-1,3,2-dioxaborolan-2-yl)-1H-indol-6-yl)methoxy)phenyl)acetate (211a) (0.23 g, 91% yield) as a yellow oil; $^1$H NMR (300 MHz, DMSO-d$_6$) δ 8.05 (dd, J=1.5, 0.8 Hz, 1H), 7.95 (s, 1H), 7.71 (d, J=1.5 Hz, 1H), 7.66 (d, J=3.6 Hz, 1H), 7.31-7.19 (m, 1H), 7.15-7.10 (m, 1H), 7.08 (dd, J=3.7, 0.8 Hz, 1H), 6.91 (td, J=7.4, 1.1 Hz, 1H), 5.22 (s, 2H), 4.00 (q, J=7.1 Hz, 2H), 3.59 (s, 2H), 3.41 (s, 3H), 1.11-0.98 (m, 15H); MS (ES−): 512.3 (M−1).

Step-2: Preparation of Ethyl 2-(2-((4-(2-(aminomethyl)pyridin-4-yl)-1-(methylsulfonyl)-1H-indol-6-yl)methoxy)phenyl)acetate (211b)

Compound 211b was prepared according to the procedure reported in step-3 of Scheme-1 from ethyl 2-(2-((1-(methylsulfonyl)-4-(4,4,5,5-tetramethyl-1,3,2-dioxaborolan-2-yl)-1H-indol-6-yl)methoxy)phenyl)acetate (211a) (0.22 g, 0.43 mmol) in dioxane (5 mL) using (4-chloropyridin-2-yl)methanamine (74a) (0.07 mL, 0.64 mmol), bis(triphenylphosphine)palladium(II) chloride (0.05 g, 0.06 mmol) and a solution of K$_2$CO$_3$ (0.09 g, 0.64 mmol) in water (0.5 mL) under an Ar atmosphere and heating at 85° C. for 2 h on oil bath. This gave after workup, purification by flash column chromatography [silica (12 g), eluting with DMA80 in DCM from 0-50%] followed by purification by reverse-phase column chromatography [C18 (50 g), eluting with ACN in water (containing 0.1% HCl) from 0-100%] ethyl 2-(2-((4-(2-(aminomethyl)pyridin-4-yl)-1-(methylsulfonyl)-1H-indol-6-yl)methoxy)phenyl)acetate (211b) (0.07 g, 33% yield) as a yellow solid; $^1$H NMR (300 MHz, Methanol-d$_4$) δ 8.41 (d, J=5.4 Hz, 1H), 8.06 (t, J=1.0 Hz, 1H), 7.71 (s, 1H), 7.61 (d, J=3.8 Hz, 1H), 7.58-7.47 (m, 3H), 7.32 (dd, J=5.4, 2.0 Hz, 1H), 7.25-7.12 (m, 2H), 7.02 (dd, J=8.3, 1.1 Hz, 1H), 6.93 (dd, J=3.8, 0.9 Hz, 1H), 6.87 (td, J=7.4, 1.1 Hz, 1H), 5.22 (s, 2H), 3.97-3.88 (m, 4H), 3.61 (s, 2H), 3.25 (s, 3H), 0.99 (t, J=7.1 Hz, 3H); MS (ES+): 494.2 (M+1).

Step-3: Preparation of 2-(2-((4-(2-(aminomethyl)pyridin-4-yl)-1-(methylsulfonyl)-1H-indol-6-yl)methoxy)phenyl)acetic Acid (211c) and 2-(2-((4-(2-(aminomethyl)pyridin-4-yl)-1H-indol-6-yl)methoxy)phenyl)acetic Acid (211e)

Compounds 211c and 211e were prepared according to the procedure reported in step-6 of Scheme-1 from ethyl 2-(2-((4-(2-(aminomethyl)pyridin-4-yl)-1-(methylsulfonyl)-1H-indol-6-yl)methoxy)phenyl)acetate (211b) (0.07 g, 0.14 mmol) in THF (3 mL) and MeOH (3 mL) using lithium hydroxide hydrate (0.01 g, 0.28 mmol) in water (0.5 mL). This gave after workup and purification by reverse phase column [C18 (50 g), eluting with ACN in water (containing 0.1% HCl) from 0-100%] 2-(2-((4-(2-(aminomethyl)pyridin-4-yl)-1-(methylsulfonyl)-1H-indol-6-yl)methoxy)phenyl)acetic acid (211c) (0.02 g, 35% yield) HCl salt as a yellow solid; $^1$H NMR (300 MHz, DMSO-d$_6$) δ 8.75 (d, J=5.2 Hz, 1H), 8.36 (s, 3H), 8.09 (s, 1H), 7.78 (d, J=3.9 Hz, 2H), 7.70 (d, J=4.7 Hz, 1H), 7.63 (s, 1H), 7.29-7.19 (m, 2H), 7.13 (d, J=7.9 Hz, 1H), 7.04 (d, J=3.8 Hz, 1H), 6.92 (t, J=7.5 Hz, 1H), 5.34 (s, 2H), 4.32 (s, 2H), 3.60 (s, 2H), 3.53 (s, 3H). MS (ES+): 466.2 (M+1), MS (ES−): 464.3 (M−1). HPLC purity: 99.48%; methyl 2-(2-((4-(2-(aminomethyl)pyridin-4-yl)-1-(methylsulfonyl)-1H-indol-6-yl)methoxy)phenyl)acetate (211d) (0.01 g, 9% yield) HCl salt as a yellow solid; $^1$H NMR (300 MHz, DMSO-d$_6$) δ 8.77 (d, J=5.1 Hz, 1H), 8.42 (s, 3H), 8.07 (s, 1H), 7.83-7.74 (m, 2H), 7.70 (d, J=5.3 Hz, 1H), 7.59 (s, 1H), 7.34-7.19 (m, 2H), 7.14 (d, J=8.2 Hz, 1H), 7.05 (d, J=3.8 Hz, 1H), 6.92 (t, J=7.4 Hz, 1H), 5.33 (s, 2H), 4.31 (d, J=5.8 Hz, 2H), 3.65 (s, 2H), 3.53 (s, 3H), 3.46 (s, 3H); MS (ES+): 480.2 (M+1), followed by 2-(2-((4-(2-(aminomethyl)pyridin-4-yl)-1H-indol-6-yl)methoxy)phenyl)acetic acid (211e) (0.004 g, 7% yield) HCl salt as a yellow solid; $^1$H NMR (300 MHz, DMSO-d$_6$) δ 11.49 (s, 1H), 8.71 (d, J=5.2 Hz, 1H), 8.35 (s, 3H), 7.84 (d, J=1.6 Hz, 1H), 7.74 (d, J=5.4 Hz, 1H), 7.61 (s, 1H), 7.53 (t, J=2.8 Hz, 1H), 7.36 (d, J=1.4 Hz, 1H), 7.22 (d, J=7.4 Hz, 2H), 7.11 (d, J=8.2 Hz, 1H), 6.96-6.85 (m, 1H), 6.72 (s, 1H), 5.27 (s, 2H), 4.31 (s, 2H), 3.59 (s, 2H); MS (ES+): 388.2 (M+1).

Scheme-212

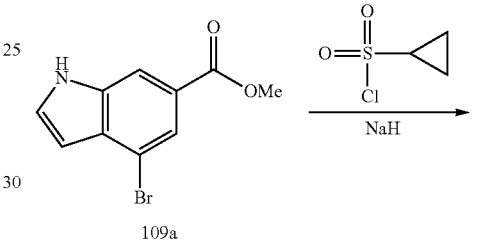

109a

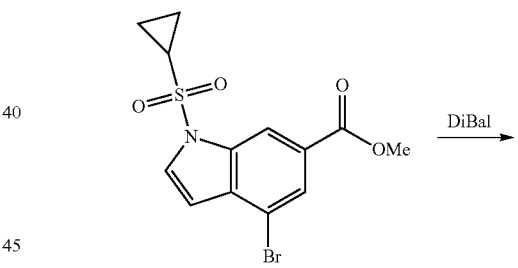

212a

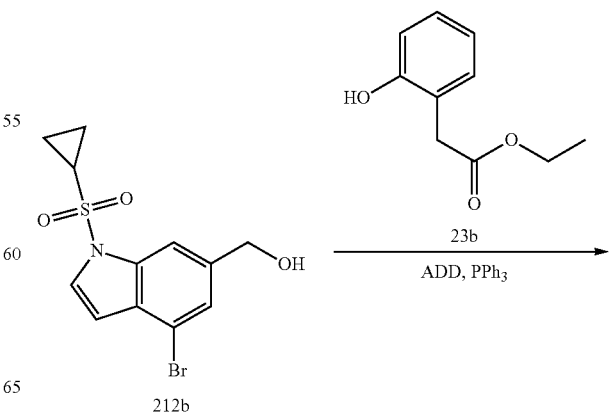

212b

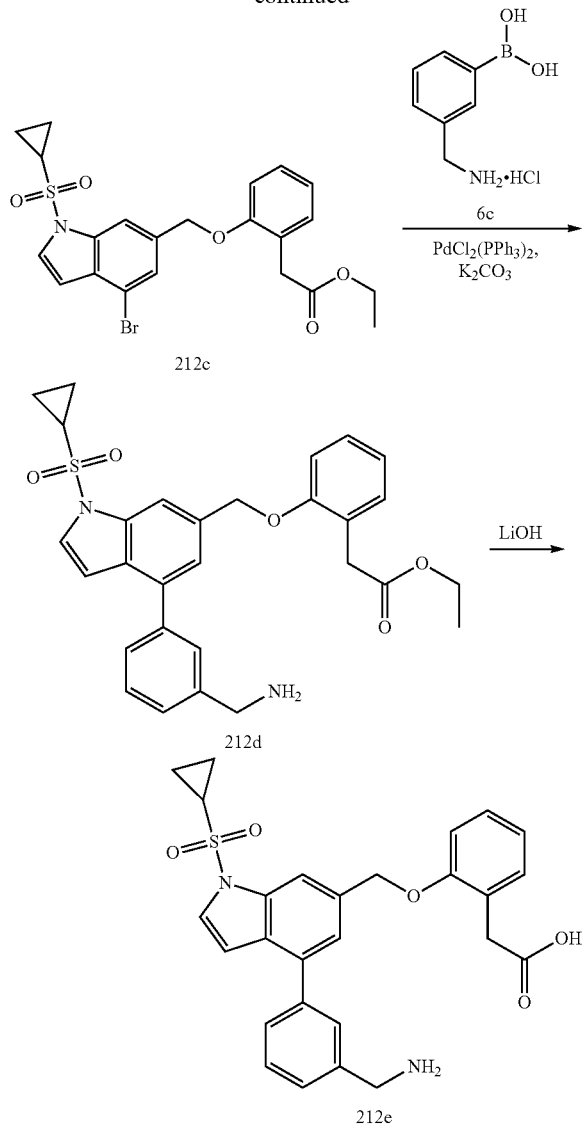

Preparation of 2-(2-((4-(3-(aminomethyl)phenyl)-1-(cyclopropylsulfonyl)-1H-indol-6-yl)methoxy)phenyl)acetic Acid (212e)

Step-1: Preparation of methyl 4-bromo-1-(cyclopropylsulfonyl)-1H-indole-6-carboxylate (212a)

Compound 212a was prepared according to the procedure reported in step-1 of Scheme-40 from methyl 4-bromo-1H-indole-6-carboxylate (109a) (2 g, 7.87 mmol) in DMF (15 mL) using NaH (60% in mineral oil, 0.94 g, 23.61 mmol) and cyclopropanesulfonyl chloride (2.41 mL, 23.61 mmol). This gave after work-up and purification by flash column chromatography [silica (12 g), eluting with EtOAc/MeOH=9:1 in Hexane from 0-50%] methyl 4-bromo-1-(cyclopropylsulfonyl)-1H-indole-6-carboxylate (212a) (2.52 g, 89% yield) as a white solid; $^1$H NMR (300 MHz, DMSO-d$_6$) δ 8.51 (t, J=1.0 Hz, 1H), 8.04 (d, J=1.2 Hz, 1H), 8.01 (d, J=3.7 Hz, 1H), 6.91 (dd, J=3.7, 0.9 Hz, 1H), 3.91 (s, 3H), 3.32-3.19 (m, 1H), 1.38-1.04 (m, 4H); MS (ES$^+$) 358.0, 360.0 (M+1); MS (ES−) 358.1, 356.1 (M−1).

Step-2: Preparation of (4-bromo-1-(cyclopropylsulfonyl)-1H-indol-6-yl)methanol (212b)

To a solution of methyl 4-bromo-1-(cyclopropylsulfonyl)-1H-indole-6-carboxylate (212a) (0.5 g, 1.40 mmol) in dichloromethane (10 mL) cooled to −78° C. was slowly added diisobutylaluminum hydride (1M solution in dichloromethane) (3.49 mL, 3.49 mmol) and allowed to warm gradually to 0 to 5° C. After 10 minutes the reaction was quenched by the addition of methanol (75 mL). The mixture was diluted with additional dichloromethane (100 mL) and stirred vigorously for about 1 hour. The organic phases were washed with brine (100 mL), dried and concentrated under reduced pressure to afford (4-bromo-1-(cyclopropylsulfonyl)-1H-indol-6-yl)methanol (212b) (0.37 g, 80% yield) as a white crystalline solid; $^1$H NMR (300 MHz, DMSO-d$_6$) δ 7.89 (p, J=0.9 Hz, 1H), 7.70 (d, J=3.7 Hz, 1H), 7.49 (dd, J=1.2, 0.6 Hz, 1H), 6.75 (dd, J=3.7, 0.8 Hz, 1H), 5.44 (t, J=5.9 Hz, 1H), 4.63 (dt, J=5.9, 0.8 Hz, 2H), 3.14-3.05 (m, 1H), 1.33-1.04 (m, 4H); MS (ES−): 364.1, 366.1 (M+Cl).

Step-3: Preparation of Ethyl 2-(2-((4-bromo-1-(cyclopropylsulfonyl)-1H-indol-6-yl)methoxy)phenyl)acetate (212c)

Compound 212c was prepared according to the procedure reported in step-2 of Scheme-23 from (4-bromo-1-(cyclopropylsulfonyl)-1H-indol-6-yl)methanol (212b) (1.2 g, 3.63 mmol) in toluene (15 mL) using triphenylphosphine (1.24 g, 4.72 mmol) ethyl 2-(2-hydroxyphenyl) acetate (23b) (0.85 g, 4.72 mmol) and (E)-diazene-1,2-diylbis(piperidin-1-yl-methanone) (1.19 g, 4.72 mmol) in toluene (15 mL). This gave after workup and purification by flash column chromatography [silica (24 g), eluting with EtOAc/MeOH (9:1) in hexane from 0-10% for 40 min, then 10%-50%] ethyl 2-(2-((4-bromo-1-(cyclopropylsulfonyl)-1H-indol-6-yl)methoxy)phenyl)acetate (212c) (1.2 g, 67% yield) as a yellow oil; $^1$H NMR (300 MHz, DMSO-d$_6$): δ 7.99 (t, J=1.0 Hz, 1H), 7.77 (d, J=3.7 Hz, 1H), 7.60 (d, J=1.1 Hz, 1H), 7.30-7.19 (m, 2H), 7.09 (dd, J=8.0, 1.0 Hz, 1H), 6.92 (td, J=7.4, 1.1 Hz, 1H), 6.79 (dd, J=3.7, 0.8 Hz, 1H), 5.26 (s, 2H), 4.03 (q, J=7.1 Hz, 2H), 3.63 (s, 2H), 3.15-3.09 (m, 1H), 1.33-1.24 (m, 2H), 1.13-1.06 (m, 5H); MS (ES−): 491.1, 493.2 (M−1).

Step-4: Preparation of Ethyl 2-(2-((4-(3-(aminomethyl)phenyl)-1-(cyclopropylsulfonyl)-1H-indol-6-yl)methoxy)phenyl)acetate (212d)

Compound 212d was prepared according to the procedure reported in step-3 of Scheme-1 from ethyl 2-(2-((4-bromo-1-(cyclopropylsulfonyl)-1H-indol-6-yl)methoxy)phenyl)acetate (212c) (0.6 g, 1.22 mmol) in dioxane (5 mL) using 3-(aminomethyl)phenylboronic acid hydrochloride (6c) (0.34 g, 1.83 mmol), K$_2$CO$_3$ (0.34 g, 2.44 mmol) in water (2 mL) and bis(triphenylphosphine)palladium(ll)chloride (0.13 g, 0.18 mmol) under an Ar atmosphere and heating at 90° C. for 2 h on oil bath. This gave after workup and purification by reverse phase column chromatography [C18 (50 g), eluting with ACN in water (containing 0.1% HCl) from 0-100%] ethyl 2-(2-((4-(3-(aminomethyl)phenyl)-1-(cyclopropylsulfonyl)-1H-indol-6-yl)methoxy)phenyl)acetate (212d) (0.28 g, 44% yield) HCl salt as a white solid. $^1$H NMR (300 MHz, DMSO-d$_6$) δ 8.33 (s, 3H), 8.03 (s, 1H), 7.78 (d, J=2.0 Hz, 1H), 7.74 (d, J=3.7 Hz, 1H), 7.69-7.61 (m, 2H), 7.61-7.50 (m, 2H), 7.47 (d, J=1.3 Hz, 1H), 7.31-7.18 (m, 2H), 7.17-7.09 (m, 1H), 7.01 (dd, J=3.7, 0.8 Hz, 1H), 6.91 (td, J=7.4, 1.1 Hz, 1H), 5.31 (s, 2H), 4.14 (s, 2H), 3.91 (q, J=7.1 Hz, 2H), 3.63 (s, 2H), 3.20-3.03 (m, 1H), 1.34-1.03 (m, 4H), 0.97 (t, J=7.1 Hz, 3H); MS (ES+): 519.2 (M+1), MS (ES−): 517.3 (M−1).

Step-5: Preparation of 2-(2-((4-(3-(aminomethyl)phenyl)-1-(cyclopropylsulfonyl)-1H-indol-6-yl)methoxy)phenyl)acetic Acid (212e)

Compound 212e was prepared according to the procedure reported in step-6 of Scheme-1 from ethyl 2-(2-((4-(3-(aminomethyl)phenyl)-1-(cyclopropylsulfonyl)-1H-indol-6-yl)methoxy)phenyl)acetate (212d) (0.21 g, 0.41 mmol) in MeOH/THF (4 mL, 1:1) using a solution of lithium hydroxide hydrate (0.14 g, 3.24 mmol) in water (1 mL). This gave after workup and purification by reverse phase column chromatography [C18 (50 g), eluting with ACN in water (containing 0.1% HCl) from 0-100%] 2-(2-((4-(3-(aminomethyl)phenyl)-1-(cyclopropylsulfonyl)-1H-indol-6-yl)methoxy)phenyl)acetic acid (212e) (0.09 g, 45% yield) HCl salt as a white solid; $^1$H NMR (300 MHz, DMSO-d$_6$) δ 12.19 (s, 1H), 8.35 (s, 3H), 8.04 (s, 1H), 7.78 (s, 1H), 7.73 (d, J=3.7 Hz, 1H), 7.70-7.63 (m, 1H), 7.59 (t, J=7.5 Hz, 1H), 7.56-7.48 (m, 2H), 7.24 (t, J=7.9 Hz, 2H), 7.12 (d, J=8.0 Hz, 1H), 7.01 (dd, J=3.8, 0.8 Hz, 1H), 6.91 (td, J=7.4, 1.1 Hz, 1H), 5.33 (s, 2H), 4.14 (d, J=5.9 Hz, 2H), 3.60 (s, 2H), 3.20-3.05 (m, 1H), 1.35-1.00 (m, 4H); MS (ES+): 491.2 (M+1), MS (ES−): 489.3 (M−1).

Scheme-213

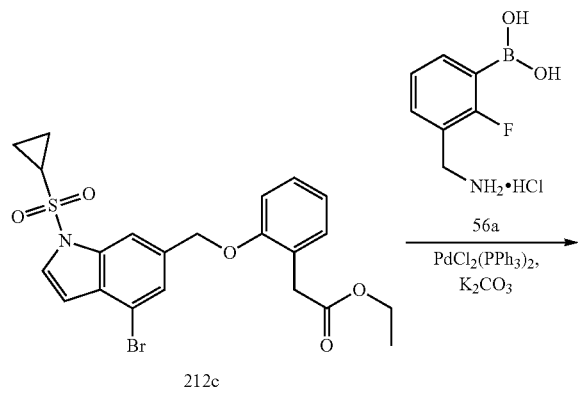

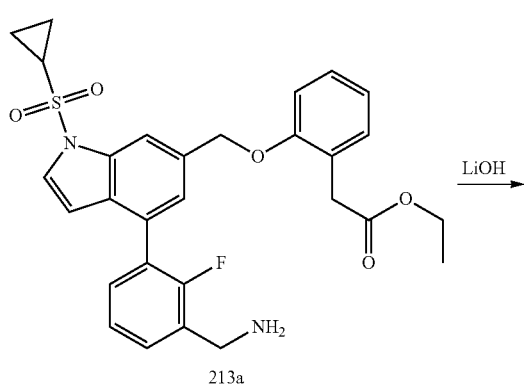

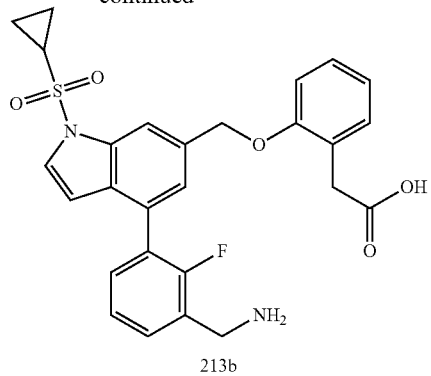

Preparation of 2-(2-((4-(3-(aminomethyl)-2-fluorophenyl)-1-(cyclopropylsulfonyl)-1H-indol-6-yl)methoxy)phenyl)acetic Acid (213b)

Step-1: Preparation of Ethyl 2-(2-((4-(3-(aminomethyl)-2-fluorophenyl)-1-(cyclopropylsulfonyl)-1H-indol-6-yl)methoxy)phenyl)acetate (213a)

Compound 213a was prepared according to the procedure reported in step-3 of Scheme-1 from ethyl 2-(2-((4-bromo-1-(cyclopropylsulfonyl)-1H-indol-6-yl)methoxy)phenyl)acetate (212c) (0.6 g, 1.22 mmol) in dioxane (5 mL) using 3-(aminomethyl)-2-fluorophenylboronic acid hydrochloride (56a) (0.38 g, 1.83 mmol), K$_2$CO$_3$ (0.34 g, 2.44 mmol) in water (2 mL) and bis(triphenylphosphine)palladium(ll)chloride (0.13 g, 0.18 mmol) under an Ar atmosphere and heating at 85° C. for 2 h on oil bath. This gave after workup and purification by reverse phase column chromatography [C18 (50 g), eluting with ACN in water (containing 0.1% HCl) from 0-100%] ethyl 2-(2-((4-(3-(aminomethyl)-2-fluorophenyl)-1-(cyclopropylsulfonyl)-1H-indol-6-yl)methoxy)phenyl)acetate (213a) (0.35 g, 54% yield) HCl salt as a white solid; $^1$H NMR (300 MHz, DMSO-d$_6$) δ 8.53 (s, 3H), 8.06 (t, J=1.0 Hz, 1H), 7.71 (d, J=3.8 Hz, 1H), 7.69-7.64 (m, 1H), 7.59 (td, J=7.5, 1.8 Hz, 1H), 7.47-7.39 (m, 2H), 7.30-7.19 (m, 2H), 7.14 (dd, J=8.3, 1.1 Hz, 1H), 6.91 (td, J=7.3, 1.1 Hz, 1H), 6.78-6.73 (m, 1H), 5.31 (s, 2H), 4.16 (s, 2H), 3.90 (q, J=7.1 Hz, 2H), 3.62 (s, 2H), 3.22-3.06 (m, 1H), 1.34-1.03 (m, 4H), 0.97 (t, J=7.1 Hz, 3H); $^{19}$F NMR (282 MHz, DMSO-d$_6$) δ−118.66; MS (ES+): 537.2 (M+1), MS (ES−): 535.3 (M−1).

Step-2: Preparation of 2-(2-((4-(3-(aminomethyl)-2-fluorophenyl)-1-(cyclopropylsulfonyl)-1H-indol-6-yl)methoxy)phenyl)acetic Acid (213b)

Compound 213b was prepared according to the procedure reported in step-6 of Scheme-1 from ethyl 2-(2-((4-(3-(aminomethyl)-2-fluorophenyl)-1-(cyclopropylsulfonyl)-1H-indol-6-yl)methoxy)phenyl)acetate (213a) (0.24 g, 0.45 mmol) in MeOH/THF (4 mL, 1:1) using a solution of lithium hydroxide hydrate (0.15 g, 3.58 mmol) in water (1 mL). This gave after workup and purification by reverse phase column chromatography [C18 (50 g), eluting with ACN in water (containing 0.1% HCl) from 0-100%] 2-(2-((4-(3-(aminomethyl)-2-fluorophenyl)-1-(cyclopropylsulfonyl)-1H-indol-6-yl)methoxy)phenyl)acetic acid (213b) (0.11 g, 46% yield) HCl salt as a white solid; $^1$H NMR (300 MHz, DMSO-d$_6$) δ 8.44 (s, 3H), 8.08 (d, J=1.2 Hz, 1H), 7.70

(d, J=3.7 Hz, 1H), 7.69-7.61 (m, 1H), 7.58 (dd, J=7.4, 1.7 Hz, 1H), 7.45 (d, J=1.5 Hz, 1H), 7.41 (d, J=7.6 Hz, 1H), 7.29-7.18 (m, 2H), 7.15-7.08 (m, 1H), 6.91 (td, J=7.4, 1.1 Hz, 1H), 6.74 (t, J=3.5 Hz, 1H), 5.33 (s, 2H), 4.17 (s, 2H), 3.59 (s, 2H), 3.21-3.07 (m, 1H), 1.36-1.01 (m, 4H); $^{19}$F NMR (282 MHz, DMSO-d$_6$) δ−118.54; MS (ES+): 509.2 (M+1), MS (ES−): 507.3 (M−1).

Scheme-214

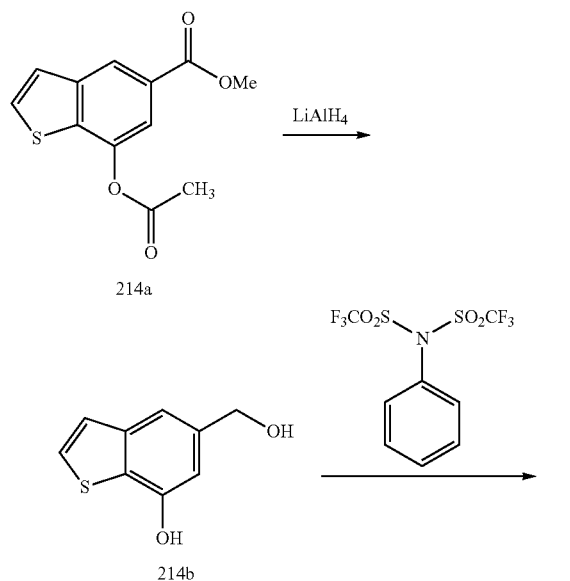

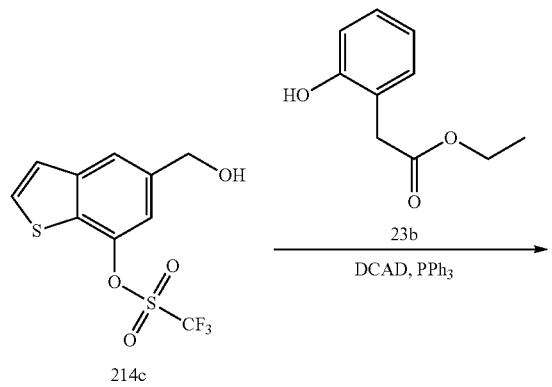

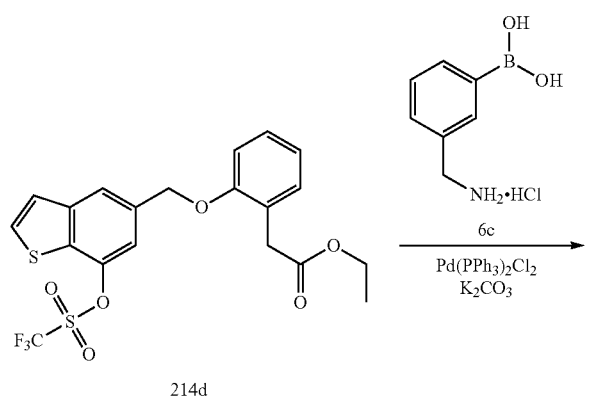

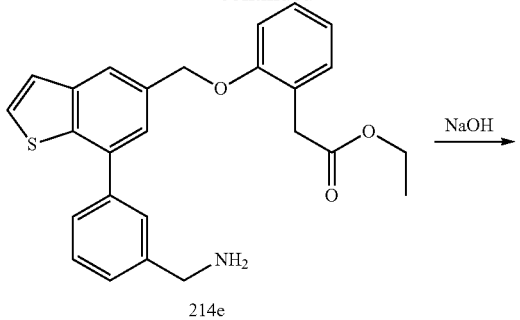

Preparation of 2-(2-((7-(3-(aminomethyl)phenyl)benzo[b]thiophen-5-yl)methoxy)phenyl)acetic Acid (214f)

Step-1: Preparation of 5-(hydroxymethyl)benzo[b]thiophen-7-ol (214b)

Compound 214b was prepared according to the procedure reported in step-1 of Scheme-115 from methyl 7-acetoxy-benzo[b]thiophene-5-carboxylate (214a) (0.66 g, 2.64 mmol; prepared according to the procedure reported by Shimizu, Kazuo et al; from PCT Int. Appl., 2010044404, 22 Apr. 2010) in THF (10 mL) using lithium aluminum hydride (0.300 g, 7.91 mmol). This gave after workup and purification by flash column chromatography [silica gel, eluting with 0-3% MeOH in DCM] 5-(hydroxymethyl)benzo[b]thiophen-7-ol (214b) (350 mg, 74% yield) as a white solid; $^1$H NMR (300 MHz, DMSO-d$_6$) δ 10.23 (s, 1H), 7.65 (d, J=5.3 Hz, 1H), 7.35 (d, J=5.3 Hz, 1H), 7.27 (d, J=1.2 Hz, 1H), 6.76 (s, 1H), 5.18 (t, J=5.7 Hz, 1H), 4.52 (d, J=4.9 Hz, 2H); MS (ES−): 179 (M−1).

Step-2: Preparation of 5-(hydroxymethyl)benzo[b]thiophen-7-yl trifluoromethanesulfonate (214c)

Compound 214c was prepared according to the procedure reported in step-2 of Scheme-115 from 5-(hydroxymethyl)benzo[b]thiophen-7-ol (214b) (340 mg, 1.887 mmol) in THF (3 mL), DMF (5 mL) using 1,1,1-trifluoro-N-phenyl-N-(trifluoromethylsulfonyl)methanesulfonamide (674 mg, 1.887 mmol) and triethylamine (0.526 mL, 3.77 mmol). This gave after workup and purification by flash column chromatography [silica gel, eluting with 0-40% EtOAc in hexane] 5-(hydroxymethyl)benzo[b]thiophen-7-yl trifluoromethanesulfonate (214c) (430 mg, 1.377 mmol, 73.0% yield) as a pale yellow thick oil; $^1$H NMR (300 MHz, DMSO-d$_6$) δ 8.01-7.90 (m, 2H), 7.61 (d, J=5.3 Hz, 1H), 7.47 (d, J=1.2 Hz, 1H), 5.53 (s, 1H), 4.68 (s, 2H); MS (ES−): 311 (M−1).

Step-3: Preparation of Ethyl 2-(2-((7-(((trifluoromethyl)sulfonyl)oxy)benzo[b]thiophen-5-yl)methoxy)phenyl)acetate (214d)

Compound 214d was prepared according to the procedure reported in step-2 of Scheme-23 from 5-(hydroxymethyl)benzo[b]thiophen-7-yl trifluoromethanesulfonate (214c) (420 mg, 1.345 mmol) in DCM (10 mL) using triphenylphosphine (388 mg, 1.479 mmol), ethyl 2-(2-hydroxyphenyl) acetate (23b) (267 mg, 1.479 mmol) and di-(4-chlorobenzyl)azodicarboxylate (DCAD, 543 mg, 1.479 mmol). This gave after workup and purification by flash column chromatography [silica, eluting with 0-15% EtOAc in hexane] ethyl 2-(2-((7-(((trifluoromethyl)sulfonyl)oxy)benzo[b]thiophen-5-yl)methoxy)phenyl)acetate (214d) (0.46 g, 72% yield) as a thick clear colorless oil, which turned to a white solid on standing; $^1$H NMR (300 MHz, DMSO-d$_6$) δ 8.09 (d, J=3.2 Hz, 1H), 8.01 (dd, J=5.6, 3.2 Hz, 1H), 7.63 (dt, J=10.4, 3.4 Hz, 2H), 7.40-7.16 (m, 2H), 7.10 (dd, J=8.2, 3.2 Hz, 1H), 6.94 (td, J=7.5, 2.9 Hz, 1H), 5.31 (d, J=3.2 Hz, 2H), 4.00 (qd, J=7.1, 3.3 Hz, 2H), 3.66 (d, J=3.3 Hz, 2H), 1.05 (td, J=7.2, 3.4 Hz, 3H); MS (ES+): 475 (M+1).

Step-4: Preparation of Ethyl 2-(2-((7-(3-(aminomethyl)phenyl)benzo[b]thiophen-5-yl)methoxy)phenyl)acetate (214e)

Compound 214e was prepared according to the procedure reported in step-3 of Scheme-1 from ethyl 2-(2-((7-(((trifluoromethyl)sulfonyl)oxy)benzo[b]thiophen-5-yl)methoxy)phenyl)acetate (214d) (103 mg, 0.217 mmol) in dioxane (2 mL) using 3-(aminomethyl)phenylboronic acid hydrochloride (6c) (49 mg, 0.261 mmol), a solution of K$_2$CO$_3$ (90 mg, 0.651 mmol) in water (1 mL), Pd(PPh$_3$)$_2$Cl$_2$ (15.24 mg, 0.022 mmol) and heating under an Ar atmosphere at 100° C. for 16 h. This gave after workup, purification by flash column chromatography (silica gel, eluting with 0-15% MeOH in DCM) ethyl 2-(2-((7-(3-(aminomethyl)phenyl)benzo[b]thiophen-5-yl)methoxy)phenyl)acetate (214e) as a pale-yellow oil which was taken as such for next step.

Step-5: Preparation of 2-(2-((7-(3-(aminomethyl)phenyl)benzo[b]thiophen-5-yl)methoxy)phenyl)acetic Acid (214f)

Compound 214f was prepared according to the procedure reported in step-4 of Scheme-4 from ethyl 2-(2-((7-(3-(aminomethyl)phenyl)benzo[b]thiophen-5-yl)methoxy)phenyl)acetate (214e) (from above step) in THF (1 mL) and MeOH (2 mL) using a solution of NaOH (87 mg, 2.171 mmol) in water (1 mL). This gave after workup and purification by reverse phase column chromatography (C18, 100 g, 0-60% MeCN in H$_2$O containing 0.1% HCl) 2-(2-((7-(3-(aminomethyl)phenyl)benzo[b]thiophen-5-yl)methoxy)phenyl)acetic acid (214f) (28 mg, 32% yield) HCl salt as a white solid; $^1$H NMR (300 MHz, DMSO-d$_6$) δ 8.00 (d, J=1.5 Hz, 1H), 7.91-7.78 (m, 3H), 7.67-7.51 (m, 4H), 7.23 (dd, J=8.0, 6.4 Hz, 2H), 7.09 (d, J=8.2 Hz, 1H), 6.90 (t, J=7.3 Hz, 1H), 5.31 (s, 2H), 4.14 (s, 2H), 3.59 (s, 2H); MS (ES+): 404 (M+1); (ES−): 402 (M−1).

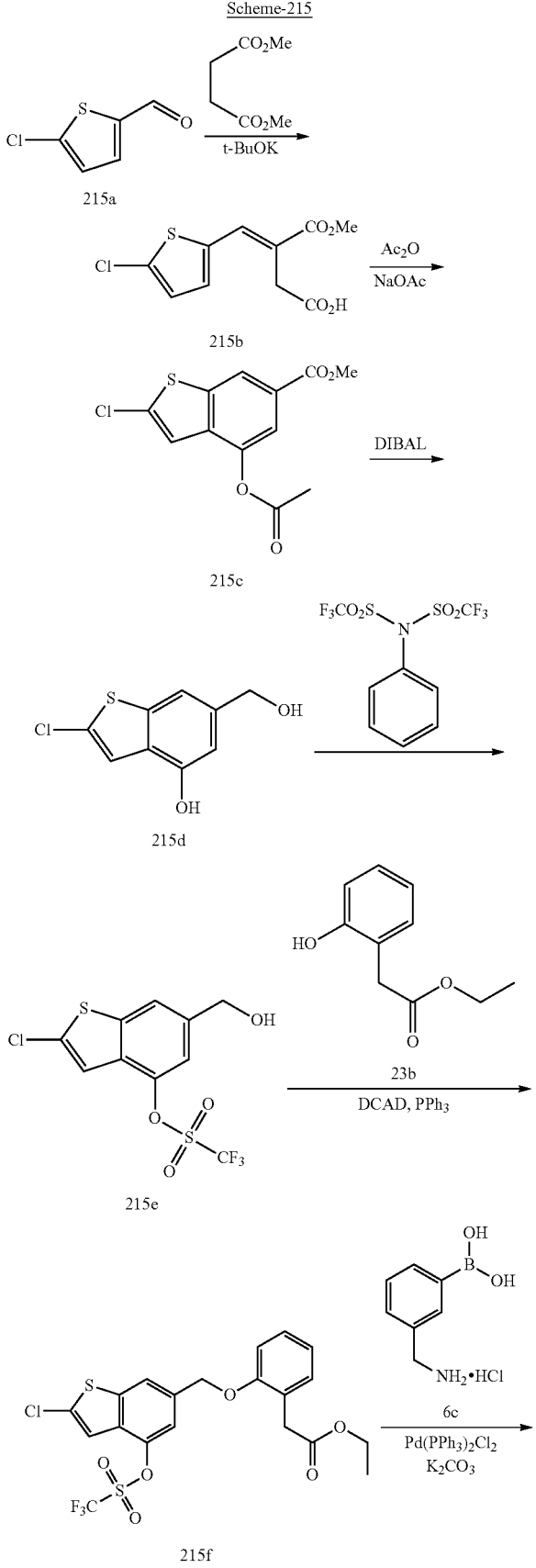

Scheme-215

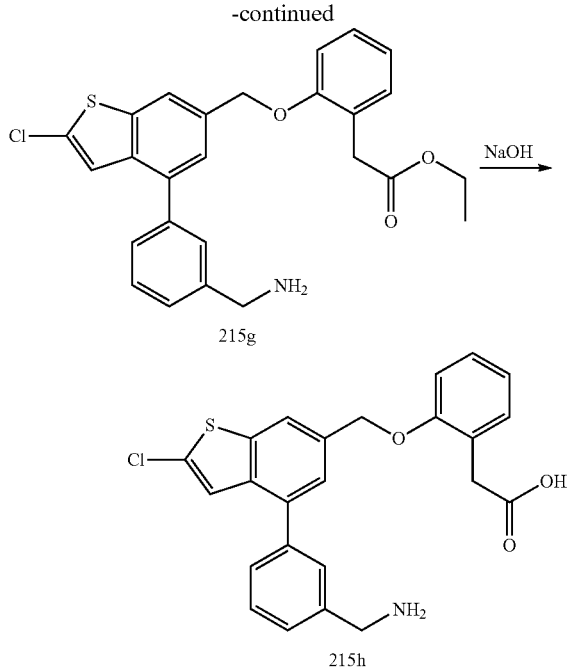

Preparation of 2-(2-((4-(3-(aminomethyl)phenyl)-2-chlorobenzo[b]thiophen-6-yl)methoxy)phenyl)acetic Acid (215h)

Step-1: Preparation of (E)-4-(5-chlorothiophen-2-yl)-3-(methoxycarbonyl)but-3-enoic acid (215b)

Potassium t-butoxide (1.148 g, 10.23 mmol) was suspended in t-BuOH (10 mL), followed by dropwise addition of dimethyl succinate (1.994 g, 13.64 mmol) in t-BuOH (5 mL). The mixture was stirred at 80° C. for 30 min, during which it turned cloudy yellow. 5-Chlorothiophene-2-carbaldehyde (215a) (1.0 g, 6.82 mmol; CAS #7283-96-7) in t-BuOH (5 mL) was then added. The mixture was stirred at 110° C. for 3 h, during which it turned deep black. The reaction mixture was concentrated in vacuum and the residue was diluted with EtOAc (25 mL) and 6 M HCl (50 mL). After 15-min stirring, the two layers were separated and the aqueous layer was extracted with EtOAc (25 mL×2). The combined organic extract was washed with $H_2O$ (25 mL×2), brine (25 mL), dried, filtered and concentrated in vacuum. The residue obtained was purified by flash column chromatography ($SiO_2$, eluting with 0-40% EtOAc in hexane) to provide (E)-4-(5-chlorothiophen-2-yl)-3-(methoxycarbonyl)but-3-enoic acid (215b) (0.82 g, 46% yield) as a thick orange oil; $^1$H NMR (300 MHz, DMSO-$d_6$) δ 7.86 (d, J=0.7 Hz, 1H), 7.46 (dd, J=4.0, 0.7 Hz, 1H), 7.28 (d, J=4.0 Hz, 1H), 3.74 (s, 3H), 3.55 (s, 2H); MS (ES+): 261/263 (M+1).

Step-2: Preparation of methyl 4-acetoxy-2-chlorobenzo[b]thiophene-6-carboxylate (215c)

To a solution of (E)-4-(5-chlorothiophen-2-yl)-3-(methoxycarbonyl)but-3-enoic acid (215b) (0.82 g, 3.15 mmol) in acetic anhydride (10 mL) was added NaOAc (1.032 g, 12.58 mmol). The orange mixture was stirred at 180° C. for 5 h, during which it turned deep black, additional acetic anhydride (10 mL×2) was added to replenish evaporated acetic anhydride. The cooled black solution was evaporated to remove acetic anhydride. The concentrate was made slightly basic (pH 8) with 15% aqueous $Na_2CO_3$ (50 mL), diluted with EtOAc (25 mL), and stirred for 15 min. The two layers were separated. The aqueous layer was extracted with EtOAc (25 mL×2). The combined organic extract was washed with brine (25 mL), dried, filtered and concentrated in vacuum. The residue obtained was purified by flash column chromatography ($SiO_2$, 0-15% EtOAc in hexane) to provide methyl 4-acetoxy-2-chlorobenzo[b]thiophene-6-carboxylate (215c) (0.47 g, 53% yield) as a yellow solid. $^1$H NMR (300 MHz, DMSO-$d_6$) δ 8.59 (s, 1H), 7.70 (s, 2H), 3.89 (s, 3H), 2.40 (s, 3H); MS (ES+): 285/287 (M+1).

Step-3: Preparation of 2-chloro-6-(hydroxymethyl)benzo[b]thiophen-4-ol (215d)

Compound 215d was prepared according to the procedure reported in step-2 of Scheme-212 from methyl 4-acetoxy-2-chlorobenzo[b]thiophene-6-carboxylate (215c) (0.47 g, 1.651 mmol) in DCM (10 mL) using 1 M DIBAL-H in DCM (8.01 mL, 8.01 mmol). This gave after workup and purification by flash column chromatography (silica gel, eluting with 0-3% MeOH in DCM) 2-chloro-6-(hydroxymethyl)benzo[b]thiophen-4-ol (215d) (140 mg, 40% yield) as a white solid. $^1$H NMR (300 MHz, DMSO-$d_6$) δ 10.11 (s, 1H), 7.39 (d, J=2.4 Hz, 1H), 7.25 (s, 1H), 6.74 (dd, J=2.4, 1.2 Hz, 1H), 5.25 (s, 1H), 4.50 (s, 2H); MS (ES–): 213/215 (M–1).

Step-4: Preparation of 2-chloro-6-(hydroxymethyl)benzo[b]thiophen-4-yl trifluoromethanesulfonate (215e)

Compound 215e was prepared according to the procedure reported in step-2 of Scheme-116 from 2-chloro-6-(hydroxymethyl)benzo[b]thiophen-4-ol (215d) (140 mg, 0.652 mmol) in DMF (2 mL) and THF (3 mL) using 1,1,1-trifluoro-N-phenyl-N-(trifluoromethylsulfonyl)methanesulfonamide (233 mg, 0.652 mmol) and triethylamine (132 mg, 1.304 mmol). This gave after workup and purification by flash column chromatography (silica gel, eluting with 0-20% EtOAc in hexane) 2-chloro-6-(hydroxymethyl)benzo[b]thiophen-4-yl trifluoromethanesulfonate (215e) (163 mg, 72% yield) as a white solid. $^1$H NMR (300 MHz, DMSO-$d_6$) δ 8.06 (s, 1H), 7.49 (s, 1H), 7.48 (s, 1H), 5.58 (t, J=5.8 Hz, 1H), 4.65 (d, J=5.8, 0.8 Hz, 2H). MS (ES–): 345 (M–1).

Step-5: Preparation of Ethyl 2-(2-((2-chloro-4-(((trifluoromethyl)sulfonyl)oxy)benzo[b]thiophen-6-yl)methoxy)phenyl)acetate (215f)

Compound 215f was prepared according to the procedure reported in step-2 of Scheme-23 from 2-chloro-6-(hydroxymethyl)benzo[b]thiophen-4-yl trifluoromethanesulfonate (215e) (163 mg, 0.470 mmol) in DCM (10 mL) using triphenylphosphine (136 mg, 0.517 mmol), ethyl 2-(2-hydroxyphenyl) acetate (23b) (93 mg, 0.517 mmol) and di-(4-chlorobenzyl)azodicarboxylate (DCAD, 190 mg, 0.517 mmol). This gave after workup and purification by flash column chromatography (silica gel, 0-15% EtOAc in hexane) ethyl 2-(2-((2-chloro-4-(((trifluoromethyl)sulfonyl)oxy)benzo[b]thiophen-6-yl)methoxy)phenyl)acetate (215f) (190 mg, 79% yield) as a thick clear colorless oil that turned to a white solid on standing; $^1$H NMR (300 MHz, DMSO-$d_6$) δ 8.18 (s, 1H), 7.62 (d, J=1.2 Hz, 1H), 7.56 (s, 1H), 7.31-7.20 (m, 2H), 7.07 (d, J=8.0 Hz, 1H), 6.93 (td, J=7.4, 1.1 Hz, 1H), 5.28 (s, 2H), 3.99 (q, J=7.1 Hz, 2H), 3.66 (s, 2H), 1.06 (t, J=7.1 Hz, 3H); MS (ES+) 509/511 (M+1).

Step-6: Preparation of Ethyl 2-(2-((4-(3-(aminomethyl)phenyl)-2-chlorobenzo[b]thiophen-6-yl)methoxy)phenyl)acetate (215g)

Compound 215g was prepared according to the procedure reported in step-3 of Scheme-1 from ethyl 2-(2-((2-chloro-4-(((trifluoromethyl)sulfonyl)oxy)benzo[b]thiophen-6-yl)methoxy)phenyl)acetate (215f) (100 mg, 0.196 mmol) in dioxane (2 mL) using 3-(aminomethyl)phenylboronic acid hydrochloride (6c) (44 mg, 0.236 mmol), a solution of $K_2CO_3$ (81 mg, 0.589 mmol) in water (1 mL), $Pd(PPh_3)_2Cl_2$ (14 mg, 0.020 mmol) and heating under an Ar atmosphere at 100° C. for 16 h. This gave after workup and purification by flash column chromatography (silica gel, eluting with 0-10% MeOH in DCM) ethyl 2-(2-((4-(3-(aminomethyl)phenyl)-2-chlorobenzo[b]thiophen-6-yl)methoxy)phenyl)acetate (215g) as a pale-yellow oil, which was used as such for the next step.

Step-7: Preparation of 2-(2-((4-(3-(aminomethyl)phenyl)-2-chlorobenzo[b]thiophen-6-yl)methoxy)phenyl)acetic Acid (215h)

Compound 215h was prepared according to the procedure reported in step-4 of Scheme-4 from ethyl 2-(2-((4-(3-(aminomethyl)phenyl)-2-chlorobenzo[b]thiophen-6-yl)methoxy)phenyl)acetate (215g) (from above step) in THF (1 mL) and MeOH (2 mL) using a solution of NaOH (39.3 mg, 0.982 mmol) in water (1 mL). This gave after workup and purification by reverse phase column (C18, 100 g, 0-60% MeCN in $H_2O$ containing 0.1% HCl) 2-(2-((4-(3-(aminomethyl)phenyl)-2-chlorobenzo[b]thiophen-6-yl)methoxy)phenyl)acetic acid (215h) (32 mg, 37% yield) HCl salt as a white solid; $^1$H NMR (300 MHz, DMSO-$d_6$) δ 8.05 (s, 1H), 7.74 (s, 1H), 7.65-7.45 (m, 5H), 7.28-7.17 (m, 2H), 7.06 (d, J=8.3 Hz, 1H), 6.97-6.84 (m, 1H), 5.29 (s, 2H), 4.14 (s, 2H), 3.60 (s, 2H). HPLC purity: 96.8%; MS (ES+): 438/440, (ES−): 436/438 (M−1).

Scheme-216

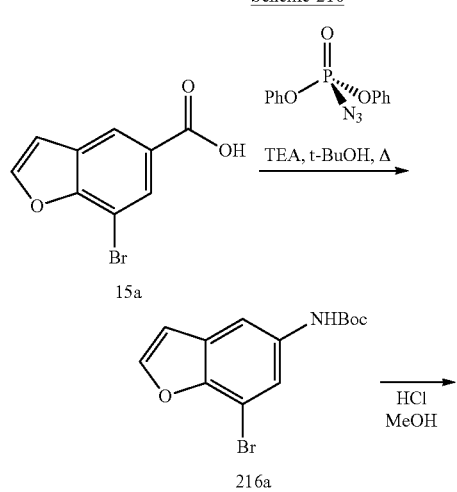

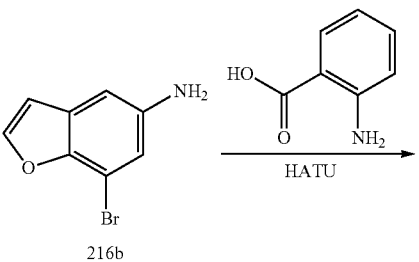

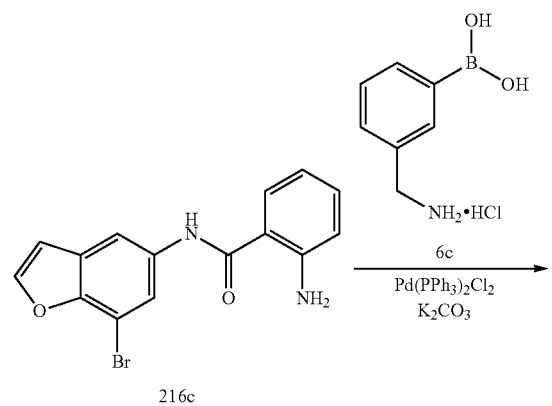

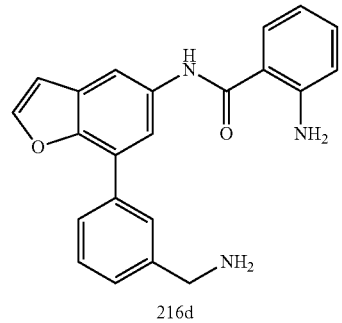

Preparation of 2-amino-N-(7-(3-(aminomethyl)phenyl)benzofuran-5-yl)benzamide (216d)

Step-1: Preparation of tert-butyl (7-bromobenzofuran-5-yl)carbamate (216a)

Diphenyl phosphoryl azide (1.256 g, 4.56 mmol) in dioxane (3 mL) was added to a suspension of 7-bromobenzofuran-5-carboxylic acid (15a) (1.0 g, 4.15 mmol), TEA (0.504 g, 4.98 mmol) and t-BuOH (9.84 mL, 104 mmol) in dioxane (17 mL) at rt. The mixture was heated at 80° C. for 16 h, cooled to rt and evaporated to dryness. The concentrate was diluted with $H_2O$ and extracted with EtOAc (25 mL×3). The extract was washed with $H_2O$ (25 mL) and brine (25 mL), dried, filtered and concentrated in vacuum. The residue obtained was purified by flash column chromatography (Silica gel, eluting with 0-5% EtOAc in hexane) to provide tert-butyl (7-bromobenzofuran-5-yl)carbamate (216a) (1.03 g) as a clear colorless oil that turned to a white solid on standing; ¹H NMR (300 MHz, CDCl₃) δ 7.68 (d, J=2.2 Hz, 1H), 7.66-7.59 (m, 1H), 7.48 (d, J=2.0 Hz, 1H), 6.80 (d, J=2.2 Hz, 1H), 6.50 (s, 1H), 1.55 (s, 9H); MS (ES–): 310/312 (M–1).

Step-2: Preparation of 7-bromobenzofuran-5-amine hydrochloride(216b)

A solution of tert-butyl (7-bromobenzofuran-5-yl)carbamate (216a) (from above) in 1 M methanolic HCl (24.89 mL, 24.89 mmol) was heated at 60° C. for 2 h, during which a white precipitate formed. The reaction mixture was cooled to room temperature and evaporated to dryness. The residue obtained was triturated with acetone and solid was collected by filtration to provide 7-bromobenzofuran-5-amine (216b) (0.7 g, 80% yield) HCl salt as a white solid. ¹H NMR (300 MHz, DMSO-d₆) δ 8.17 (d, J=2.2 Hz, 1H), 7.53 (d, J=2.0 Hz, 1H), 7.43 (d, J=2.0 Hz, 1H), 7.14 (d, J=2.2 Hz, 1H). MS (ES+): 212/214 (M+1).

Step-3: Preparation of 2-amino-N-(7-bromobenzofuran-5-yl)benzamide (216c)

Compound 216c was prepared according to the procedure reported in step-4 of Scheme-1 from 7-bromobenzofuran-5-amine hydrochloride (216b) (0.30 g, 1.207 mmol) using 2-aminobenzoic acid (0.174 g, 1.268 mmol), DIPEA (0.468 g, 3.62 mmol) and HATU (0.551 g, 1.449 mmol) in DCM (10 mL). This gave after work-up and purification by flash column chromatography (Silica gel, eluting with 0-20% EtOAc in hexane) 2-amino-N-(7-bromobenzofuran-5-yl) benzamide (216c) (290 mg, 73% yield) as a pale yellow solid; ¹H NMR (300 MHz, DMSO-d₆) δ 10.13 (s, 1H), 8.10 (d, J=2.1 Hz, 1H), 8.05 (d, J=1.9 Hz, 1H), 7.92 (d, J=1.9 Hz, 1H), 7.64 (dd, J=8.0, 1.5 Hz, 1H), 7.26-7.16 (m, 1H), 7.11 (d, J=2.2 Hz, 1H), 6.76 (dd, J=8.3, 1.2 Hz, 1H), 6.67-6.54 (m, 1H), 6.35 (s, 2H). MS (ES+): 331/333 (M+1); (ES–): 329/331 (M–1).

Step-4: Preparation of 2-amino-N-(7-(3-(aminomethyl)phenyl)benzofuran-5-yl)benzamide (216d)

Compound 216d was prepared according to the procedure reported in step-3 of Scheme-1 from 2-amino-N-(7-bromobenzofuran-5-yl)benzamide (216c) (100 mg, 0.302 mmol) in dioxane (4 mL) using 3-(aminomethyl)phenylboronic acid hydrochloride (6c) (68 mg, 0.362 mmol), a solution of K₂CO₃ (125 mg, 0.906 mmol) in water (1 mL), Pd(PPh₃)₂Cl₂ (21.19 mg, 0.030 mmol) and heating under an Ar atmosphere at 100° C. for 16 h. This gave after workup and purification by flash column chromatography (silica gel, eluting with 0-10% MeOH in DCM) followed by purification by reverse phase column (C18, 100 g, 0-60% MeCN in H₂O containing 0.1% HCl) 2-amino-N-(7-(3-(aminomethyl) phenyl)benzofuran-5-yl)benzamide (216d) (82 mg, 76% yield) HCl salt as a white solid; ¹H NMR (300 MHz, DMSO-d₆) δ 10.19 (s, 1H), 8.35 (s, 3H), 7.99 (dd, J=9.0, 2.1 Hz, 2H), 7.88 (s, 1H), 7.80 (dd, J=8.9, 1.9 Hz, 2H), 7.67 (dd, J=8.0, 1.5 Hz, 1H), 7.60-7.46 (m, 2H), 7.21 (t, J=7.6 Hz, 1H), 7.02 (d, J=2.3 Hz, 1H), 6.81 (d, J=8.2 Hz, 1H), 6.68 (t, J=7.5 Hz, 1H), 5.70 (d, J=1.0 Hz, 1H), 4.07 (q, J=5.9 Hz, 2H). MS (ES+): 358 (M+1); (ES–): 356 (M–1).

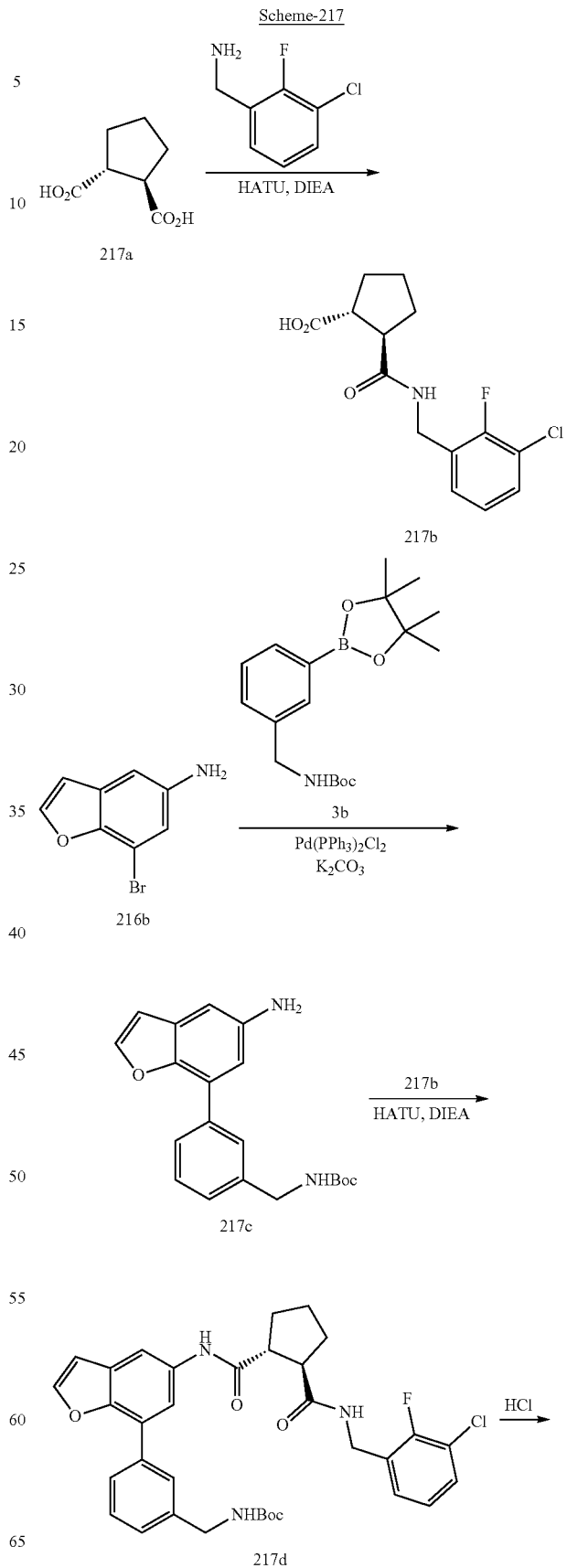

Scheme-217

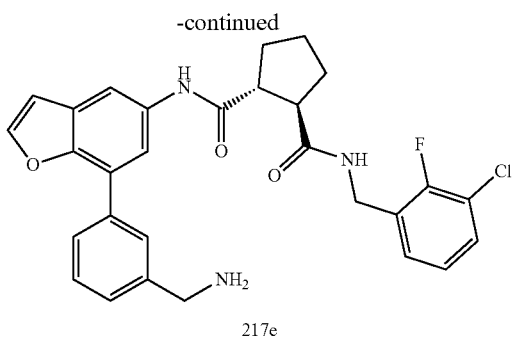

217e

Preparation of (trans)-N1-(7-(3-(aminomethyl)phenyl)benzofuran-5-yl)-N2-(3-chloro-2-fluorobenzyl)cyclopentane-1,2-dicarboxamide (217e)

Step-1: Preparation of (trans)-2-((3-chloro-2-fluorobenzyl)carbamoyl)cyclopentanecarboxylic acid (217b)

Compound 217b was prepared according to the procedure reported in step-4 of Scheme-1 from (1R,2R)-cyclopentane-1,2-dicarboxylic acid (217a) (1.00 g, 6.32 mmol; CAS #17224-73-6) using (3-chloro-2-fluorophenyl)methanamine (1.009 g, 6.32 mmol), DIEA (3.31 mL, 18.97 mmol) and HATU (2.89 g, 7.59 mmol) in DCM (10 mL). This gave after work-up and purification by flash column chromatography (Silica gel, eluting with 0-50% EtOAc in hexane) a mixture of the mono- and diamide products, as evidenced by $^1$H NMR, as a pale yellow solid. The crude solid was suspended in 1 M NaOH (20 mL) and stirred for 20 min. The mixture was washed with EtOAc (25 mL×2). The aqueous layer was separated and acidified with concentrated HCl to pH 1. The acidified aqueous layer was extracted with EtOAc (25 mL×2), washed with H$_2$O (20 mL×2), brine (20 mL), dried, filtered and concentrated to dryness to provide (trans)-2-((3-chloro-2-fluorobenzyl)carbamoyl)cyclopentanecarboxylic acid (217b) (0.55 g, 1.835 mmol, 29.0% yield) as a pale yellow solid; $^1$H NMR (300 MHz, CDCl$_3$) δ 7.36 (ddd, J=8.6, 7.1, 1.7 Hz, 1H), 7.26 (m, 1H), 7.08 (td, J=7.9, 1.2 Hz, 1H), 6.31 (s, 1H), 4.55 (d, 2H), 3.10 (q, J=8.7 Hz, 1H), 2.91 (q, J=8.7 Hz, 1H), 2.14-1.96 (m, 3H), 1.96-1.66 (m, 3H). MS (ES+): 300/302 (M+1); (ES−): 298/300 (M−1).

Step-2: Preparation of tert-butyl 3-(5-aminobenzofuran-7-yl)benzylcarbamate (217c)

Compound 217c was prepared according to the procedure reported in step-3 of Scheme-1 from 7-bromobenzofuran-5-amine (216b) (0.3 g, 1.207 mmol) in dioxane (2 mL) using tert-butyl 3-(4,4,5,5-tetramethyl-1,3,2-dioxaborolan-2-yl)benzylcarbamate (3b) (0.483 g, 1.449 mmol), a solution of K$_2$CO$_3$ (0.501 g, 3.62 mmol) in water (2 mL), Pd(PPh$_3$)$_2$Cl$_2$ (0.085 g, 0.121 mmol) and heating under an Ar atmosphere at 100° C. for 16 h. This gave after workup and purification by flash column chromatography (silica gel, eluting with 0-40% EtOAc in hexane) tert-butyl 3-(5-aminobenzofuran-7-yl)benzylcarbamate (217c) (0.37 g, 91% yield) as a pale yellow semisolid; $^1$H NMR (300 MHz, DMSO-d$_6$) δ 7.83 (d, J=2.2 Hz, 1H), 7.62 (dd, J=7.0, 1.4 Hz, 2H), 7.52-7.39 (m, 2H), 7.25 (d, J=7.6 Hz, 1H), 6.76 (dd, J=10.1, 2.2 Hz, 3H), 4.94 (s, 2H), 4.20 (d, J=6.2 Hz, 2H), 1.40 (s, 9H). MS (ES+): 339 (M+1).

Step-3: Preparation of tert-butyl 3-(5-((trans)-2-((3-chloro-2-fluorobenzyl)carbamoyl)cyclopentanecarboxamido)benzofuran-7-yl)benzylcarbamate (217d)

Compound 217d was prepared according to the procedure reported in step-4 of Scheme-1 from tert-butyl 3-(5-aminobenzofuran-7-yl)benzylcarbamate (217c) (119 mg, 0.350 mmol) using (trans)-2-((3-chloro-2-fluorobenzyl)carbamoyl)cyclopentanecarboxylic acid (217b) (100 mg, 0.334 mmol), DIEA (129 mg, 1.0 mmol) and HATU (152 mg, 0.4 mmol) in DCM (10 mL). This gave after work-up tert-butyl 3-(5-((trans)-2-((3-chloro-2-fluorobenzyl)carbamoyl)cyclopentanecarboxamido)benzofuran-7-yl)benzylcarbamate (217d) which was used as such for next step.

Step-4: Preparation of (trans)-N1-(7-(3-(aminomethyl)phenyl)benzofuran-5-yl)-N2-(3-chloro-2-fluorobenzyl)cyclopentane-1,2-dicarboxamide (217e)

The crude intermediate compound 217d from step-3 was suspended in 1.5 M methanolic HCl (25.6 mL, 38.4 mmol) and stirred at 60° C. for 1 h until the solid dissolved completely. The solution was evaporated to remove most of MeOH and purified by reverse phase column (C18, 100 g, 0-60% MeCN in H$_2$O containing 0.1% HCl) to afford (trans)-N1-(7-(3-(aminomethyl)phenyl)benzofuran-5-yl)-N2-(3-chloro-2-fluorobenzyl)cyclopentane-1,2-dicarboxamide (217e) (124 mg, 72% yield) HCl salt as a white solid; $^1$H NMR (300 MHz, DMSO-d$_6$) δ 10.14 (s, 1H), 8.54 (t, J=5.9 Hz, 1H), 8.26 (s, 3H), 8.05 (d, J=2.2 Hz, 1H), 7.99-7.86 (m, 2H), 7.86-7.74 (m, 2H), 7.68-7.51 (m, 2H), 7.47-7.34 (m, 1H), 7.21 (t, J=7.3 Hz, 1H), 7.05 (dd, J=2.2, 0.6 Hz, 1H), 6.98 (t, J=7.9 Hz, 1H), 4.45-4.23 (m, 2H), 4.13 (s, 2H), 3.11 (dt, J=16.2, 8.1 Hz, 1H), 2.14-1.93 (m, 2H), 1.72 (m, 5H); HPLC purity: 98.5%; MS (ES+): 520 (M+1); (ES−): 518 (M−1).

Scheme-218

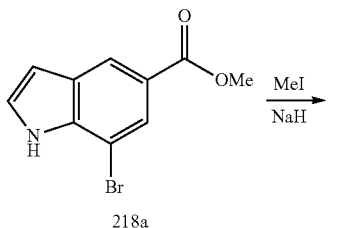

218a

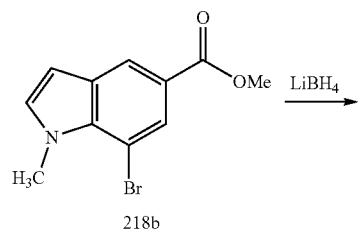

218b

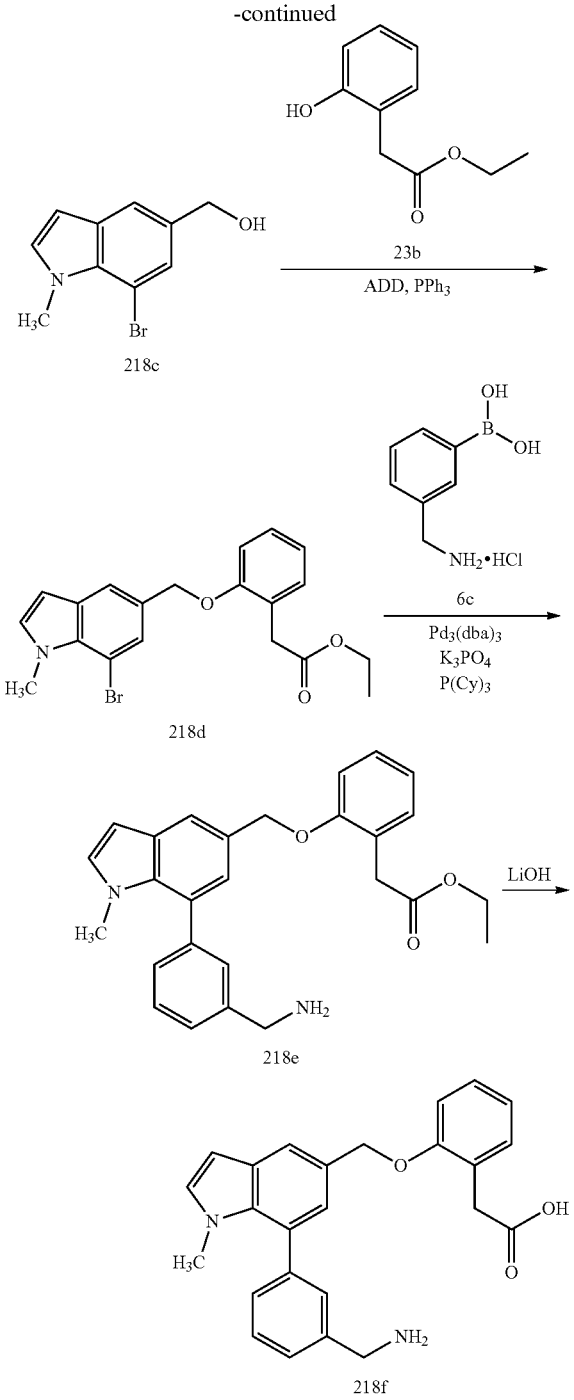

Preparation of 2-(2-((7-(3-(aminomethyl)phenyl)-1-methyl-1H-indol-5-yl)methoxy)phenyl)acetic Acid (218f)

Step-1: Preparation of methyl 7-bromo-1-methyl-1H-indole-5-carboxylate (218b)

Compound 218b was prepared according to the procedure reported in step-1 of Scheme-40 from methyl 7-bromo-1H-indole-5-carboxylate (218a) (400 mg, 1.574 mmol; CAS #885523-35-3) in DMF (5 mL) using NaH (60% in mineral oil, 157 mg, 3.94 mmol) and iodomethane (0.245 mL, 3.94 mmol). This gave after work-up and purification by flash column chromatography [silica gel, eluting with hexanes/ethyl acetate (1:0 to 6:1)] methyl 7-bromo-1-methyl-1H-indole-5-carboxylate (218b) (401 mg, 95%) as a white solid; $^1$H NMR (300 MHz, DMSO-$d_6$) δ 8.23 (d, J=1.5 Hz, 1H), 7.85 (d, J=1.5 Hz, 1H), 7.52 (d, J=3.2 Hz, 1H), 6.68 (d, J=3.2 Hz, 1H), 4.15 (s, 3H), 3.85 (s, 3H).

Step-2: Preparation of (7-bromo-1-methyl-1H-indol-5-yl)methanol (218c)

Compound 218c was prepared according to the procedure reported in step-2 of Scheme-76 from methyl 7-bromo-1-methyl-1H-indole-5-carboxylate (218b) (380 mg, 1.417 mmol) in THF (12 mL) using LiBH$_4$ (3.54 mL, 7.09 mmol) and MeOH (0.287 mL, 7.09 mmol). This gave after workup and purification by flash column chromatography [silica gel, eluting with hexanes/ethyl acetate (1:0 to 5:1)] (7-bromo-1-methyl-1H-indol-5-yl)methanol (218c) (196 mg, 58%) as a white solid; $^1$H NMR (300 MHz, DMSO-$d_6$) δ 7.46-7.44 (m, 1H), 7.34 (d, J=3.1 Hz, 1H), 7.28-7.27 (m, 1H), 6.43 (d, J=3.1 Hz, 1H), 5.16 (t, J=5.8 Hz, 1H), 4.52-4.49 (m, 2H), 4.08 (s, 3H).

Step-3: Preparation of Ethyl 2-(2-((7-bromo-1-methyl-1H-indol-5-yl)methoxy)phenyl)acetate (218d)

Compound 218d was prepared according to the procedure reported in step-2 of Scheme-23 from (7-bromo-1-methyl-1H-indol-5-yl)methanol (218c) (185 mg, 0.771 mmol) in DCM (10 mL) using triphenylphosphine (303 mg, 1.156 mmol), ethyl 2-(2-hydroxyphenyl) acetate (23b) (347 mg, 1.926 mmol) and (E)-diazene-1,2-diylbis(piperidin-1-yl-methanone) (424 mg, 1.156 mmol) in DCM (10 mL). This gave after workup and purification by flash column chromatography [silica gel, eluting with hexanes/ethyl acetate (1:0 to 5:1) ethyl 2-(2-((7-bromo-1-methyl-1H-indol-5-yl)methoxy)phenyl)acetate (218d) (112 mg) as yellow gum; MS (ES−): 400.4 & 402.3 (M−1).

Step-4: Preparation of Ethyl 2-(2-((7-(3-(aminomethyl)phenyl)-1-methyl-1H-indol-5-yl)methoxy)phenyl)acetate (218e)

Compound 218e was prepared according to the procedure reported in step-3 of Scheme-1 from ethyl 2-(2-((7-bromo-1-methyl-1H-indol-5-yl)methoxy)phenyl)acetate (218d) (108 mg, 0.268 mmol) in dioxane (3 mL) using 3-(aminomethyl)phenylboronic acid hydrochloride (6c) (75 mg, 0.403 mmol), a solution of tripotassium phosphate (0.152 mL, 0.456 mmol) in water (0.1 mL), tricyclohexylphosphine (45.2 mg, 0.161 mmol) and Pd$_2$(dba)$_3$ (74 mg, 0.081 mmol) in argon atmosphere and heating at 125° C. for 60 min in a microwave. This gave after workup and purification by flash column chromatography [silica gel, eluting with dichloromethane/methanol (1:0 to 9:1)] ethyl 2-(2-((7-(3-(aminomethyl)phenyl)-1-methyl-1H-indol-5-yl)methoxy)phenyl)acetate (218e) (12 mg) as a yellow solid; MS (ES+): 429.20 (M+1).

Step-5: Preparation of 2-(2-((7-(3-(aminomethyl)phenyl)-1-methyl-1H-indol-5-yl)methoxy)phenyl)acetic Acid (218f)

Compound 218f was prepared according to the procedure reported in step-6 of Scheme-1 from ethyl 2-(2-((7-(3-

(aminomethyl)phenyl)-1-methyl-1H-indol-5-yl)methoxy)phenyl)acetate (218e) (12 mg, 0.028 mmol) in MeOH/THF (3 mL, 1:1) using a solution of lithium hydroxide hydrate (8 mg, 0.17 mmol) in water (3 mL). This gave after workup and purification by reverse phase column chromatography [C18 (50 g), eluting with ACN in water (containing 0.1% HCl) from 0-100%] 2-(2-((7-(3-(aminomethyl)phenyl)-1-methyl-1H-indol-5-yl)methoxy)phenyl)acetic acid (218f) (2.0 mg, 18% for three steps) as pink solid; $^1$H NMR (300 MHz, DMSO-d$_6$, D$_2$O exchange) δ 7.65 (d, J=1.6 Hz, 1H), 7.56-7.39 (m, 4H), 7.28 (d, J=3.1 Hz, 1H), 7.25-7.12 (m, 2H), 7.07 (d, J=8.1 Hz, 1H), 6.98 (d, J=1.6 Hz, 1H), 6.90-6.84 (m, 1H), 6.50 (d, J=3.1 Hz, 1H), 5.16 (s, 2H), 4.09 (s, 2H), 3.53 (s, 2H), 3.27 (s, 3H); MS (ES−): 399.30 (M−1) & 435.20 (M+Cl).

Scheme-219

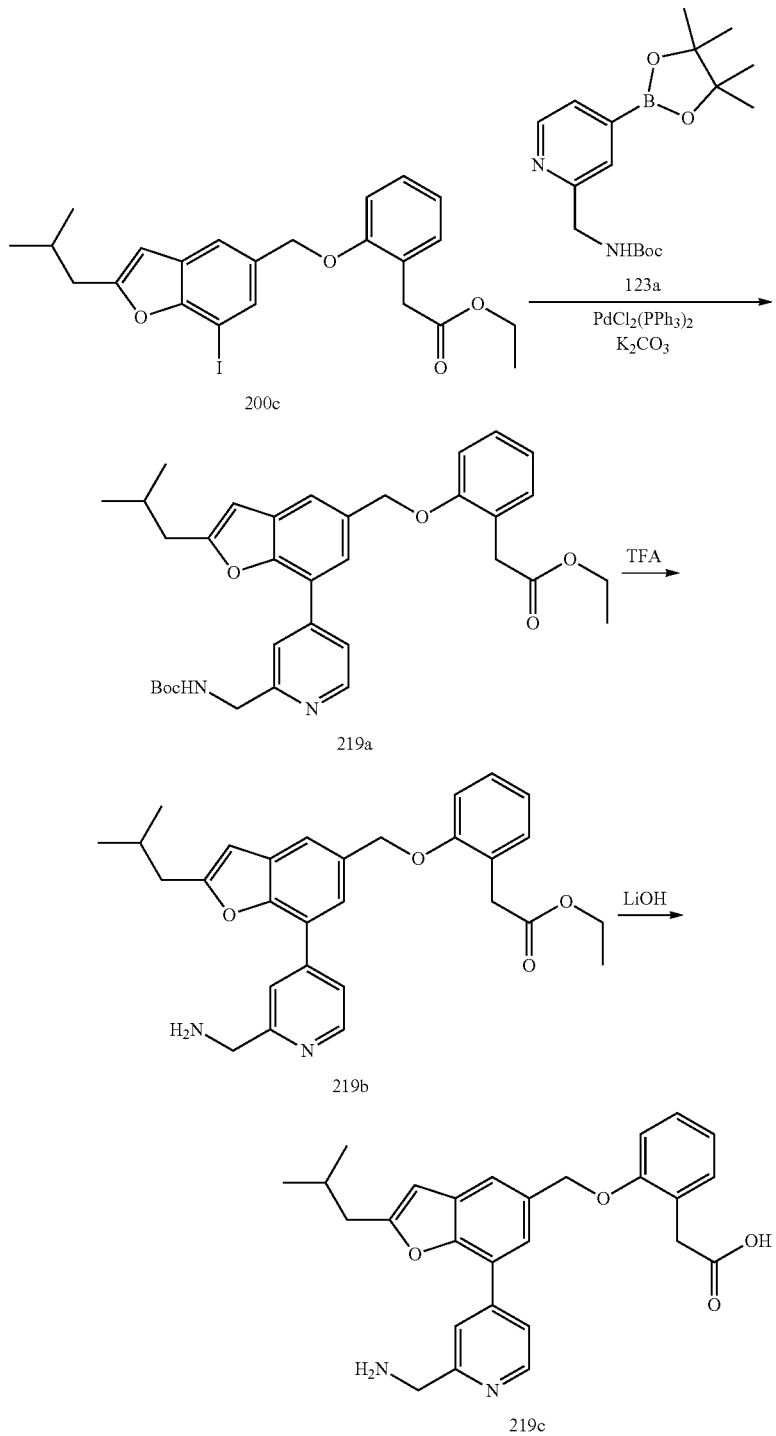

Preparation of 2-(2-((7-(2-(aminomethyl)pyridin-4-yl)-2-isobutylbenzofuran-5-yl)methoxy)phenyl)acetic Acid (219c)

Step-1: Preparation of Ethyl 2-(2-((7-(2-(((tert-butoxycarbonyl)amino)methyl)pyridin-4-yl)-2-isobutylbenzofuran-5-yl)methoxy)phenyl)acetate (219a)

Compound 219a was prepared according to the procedure reported in step-3 of Scheme-1 from ethyl 2-(2-((7-iodo-2-isobutylbenzofuran-5-yl)methoxy)phenyl)acetate (200c) (750 mg, 1.523 mmol) in dioxane (30 mL) using tert-butyl ((4-(4,4,5,5-tetramethyl-1,3,2-dioxaborolan-2-yl)pyridin-2-yl)methyl)carbamate (123a) (1018 mg, 3.05 mmol), a solution of $K_2CO_3$ (632 mg, 4.57 mmol) in water (5 mL), bis(triphenylphosphine)palladium(II) chloride (160 mg, 0.228 mmol) and heating at 100° C. for 3.5 h on oil bath. This gave after workup, purification by flash column chromatography [silica gel (24 g), eluting with methanol in DCM from 0-5%] ethyl 2-(2-((7-(2-(((tert-butoxycarbonyl)amino)methyl)pyridin-4-yl)-2-isobutylbenzofuran-5-yl)methoxy)phenyl)acetate (219a) (208 mg, 24%) as a brown gummy solid; $^1$H NMR (300 MHz, DMSO-$d_6$) δ 8.63 (dd, J=5.2, 0.8 Hz, 1H), 7.81 (s, 1H), 7.76-7.73 (m, 1H), 7.69 (d, J=1.6 Hz, 1H), 7.61-7.59 (m, 1H), 7.47 (t, J=6.1 Hz, 1H), 7.31-7.19 (m, 2H), 7.13-7.09 (m, 1H), 6.91 (td, J=7.4, 1.1 Hz, 1H), 6.73 (s, 1H), 5.21 (s, 2H), 4.32 (d, J=6.0 Hz, 2H), 3.91 (q, J=7.1 Hz, 2H), 3.61 (s, 2H), 2.71 (d, J=7.1 Hz, 2H), 2.19-1.99 (m, 1H), 1.39 (s, 9H), 1.00-0.91 (m, 9H); MS (ES+): 573.3 (M+1).

Step-2: Preparation of Ethyl 2-(2-((7-(2-(aminomethyl)pyridin-4-yl)-2-isobutylbenzofuran-5-yl)methoxy)phenyl)acetate (219b)

Compound 219b was prepared according to the procedure reported in step-5 of Scheme-1 from ethyl 2-(2-((7-(2-(((tert-butoxycarbonyl)amino)methyl)pyridin-4-yl)-2-isobutylbenzofuran-5-yl)methoxy)phenyl)acetate (219a) (200 mg, 0.349 mmol) in DCM (20 mL) using TFA (0.269 mL, 3.49 mmol). This gave after workup and purification by flash column chromatography [silica gel 12 g, eluting with methanol in DCM from 0-10%] ethyl 2-(2-((7-(2-(aminomethyl)pyridin-4-yl)-2-isobutylbenzofuran-5-yl)methoxy)phenyl)acetate (219b) (145 mg, 88% yield) as a clear oil; $^1$H NMR (300 MHz, DMSO-$d_6$) δ 8.78 (dd, J=5.3, 0.8 Hz, 1H), 8.35 (s, 3H), 8.01-7.99 (m, 1H), 7.97 (dd, J=5.2, 1.7 Hz, 1H), 7.73 (d, J=1.6 Hz, 1H), 7.68 (d, J=1.6 Hz, 1H), 7.31-7.19 (m, 2H), 7.11 (dd, J=8.2, 1.1 Hz, 1H), 6.92 (td, J=7.4, 1.1 Hz, 1H), 6.76 (d, J=0.8 Hz, 1H), 5.24 (s, 2H), 4.32 (s, 2H), 3.94 (q, J=7.1 Hz, 2H), 3.63 (s, 2H), 2.73 (d, J=6.9 Hz, 2H), 2.19-1.93 (m, 1H), 1.05-0.87 (m, 9H); MS (ES+): 473.3 (M+1).

Step-3: Preparation of 2-(2-((7-(2-(aminomethyl)pyridin-4-yl)-2-isobutylbenzofuran-5-yl)methoxy)phenyl)acetic Acid (219c)

Compound 219c was prepared according to the procedure reported in step-6 of Scheme-1 from ethyl 2-(2-((7-(2-(aminomethyl)pyridin-4-yl)-2-isobutylbenzofuran-5-yl)methoxy)phenyl)acetate (219b) (620 mg, 1.312 mmol) in MeOH/THF (10 mL each) using a solution of lithium hydroxide monohydrate (220 mg, 5.25 mmol) in water (10 mL). This gave after workup and purification by reverse phase column [C18 (50 g), eluting with ACN in water (containing 0.1% HCl) from 0-100%] 2-(2-((7-(2-(aminomethyl)pyridin-4-yl)-2-isobutylbenzofuran-5-yl)methoxy)phenyl)acetic acid (219c) (167 mg, 86%) HCl salt as a fluffy, white solid; $^1$H NMR (300 MHz, DMSO-$d_6$) δ 8.79 (d, J=5.3 Hz, 1H), 8.59 (s, 3H), 8.09 (s, 1H), 8.02 (dd, J=5.3, 1.7 Hz, 1H), 7.75 (d, J=2.3 Hz, 2H), 7.30-7.17 (m, 2H), 7.09 (d, J=8.1 Hz, 1H), 6.90 (t, J=7.4 Hz, 1H), 6.74 (s, 1H), 5.26 (s, 2H), 4.41-4.20 (m, 2H), 3.60 (s, 2H), 2.73 (d, J=7.0 Hz, 2H), 2.20-1.95 (m, 1H), 0.97 (d, J=6.6 Hz, 6H); MS (ES+): 445.2 (M+1).

Scheme-220
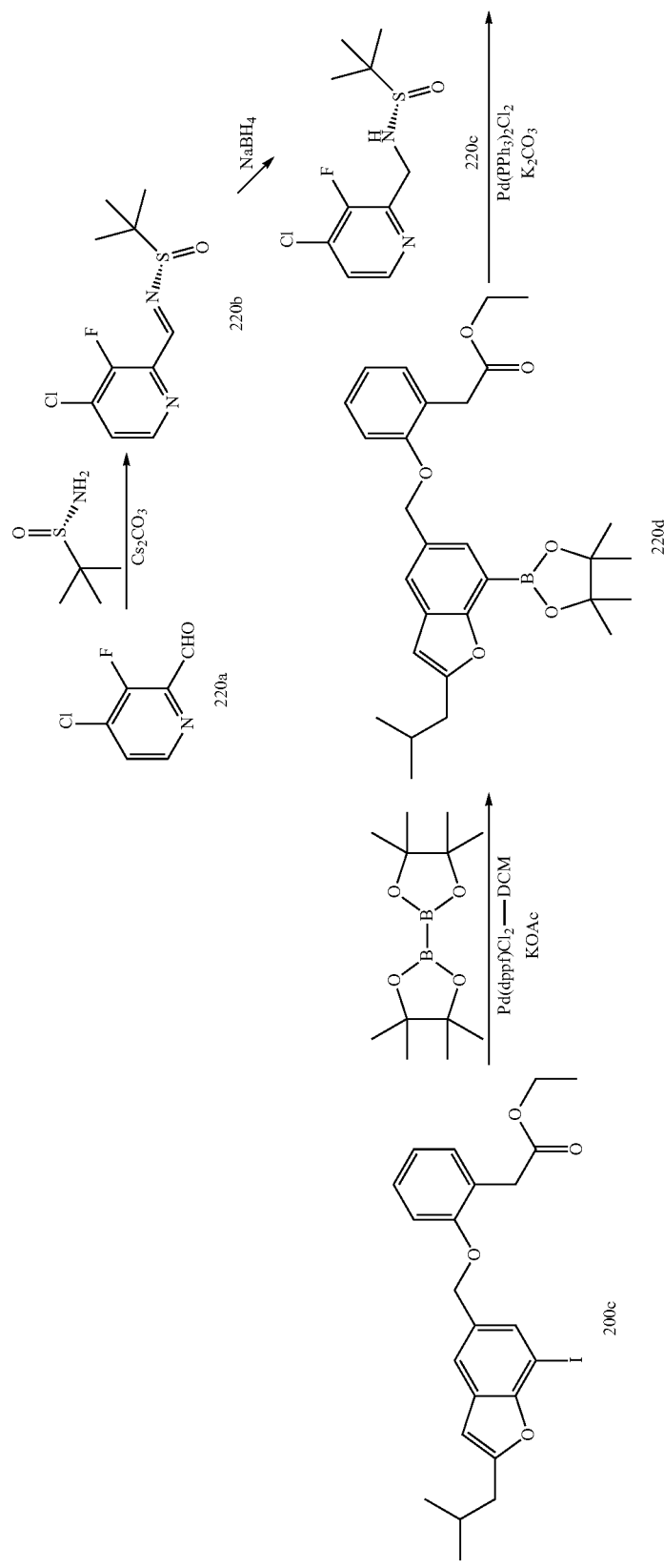

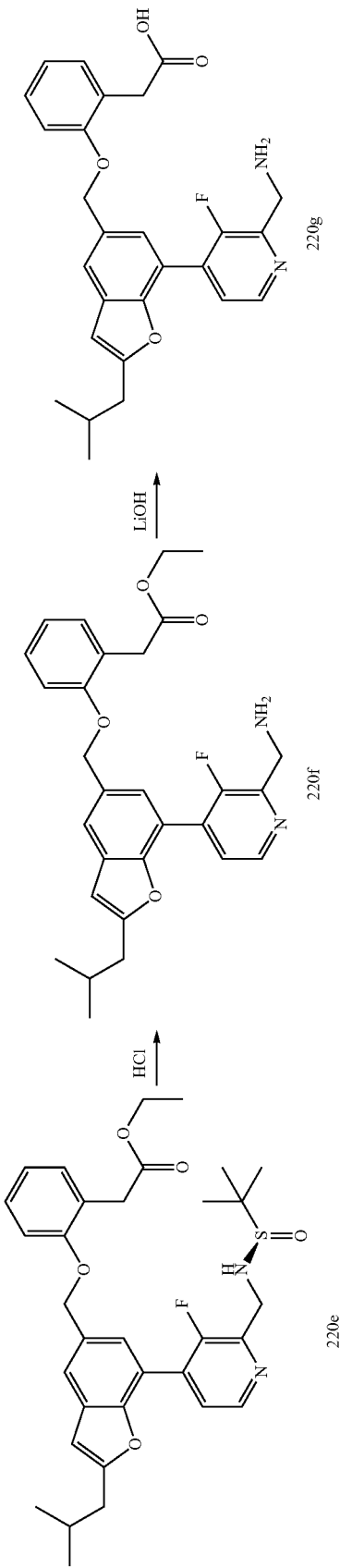

Preparation of 2-(2-((7-(2-(aminomethyl)-3-fluoropyridin-4-yl)-2-isobutylbenzofuran-5-yl)methoxy)phenyl)acetic Acid (220g)

Step-1: Preparation of (S)—N-((4-chloro-3-fluoropyridin-2-yl)methylene)-2-methylpropane-2-sulfinamide (220b)

To a solution of 4-chloro-3-fluoropicolinaldehyde (220a) (6.73 g, 42.2 mmol; CAS #1260878-78-1) and $Cs_2CO_3$ (27.5 g, 84 mmol) in DCM (350 mL) was added (S)-2-methylpropane-2-sulfinamide (5.88 g, 48.5 mmol) and stirred at rt for 1 h. The reaction mixture was diluted with DCM and washed with brine (3×200 mL). The organic layer was dried, filtered and concentrated in vacuo to afford (S)-N-((4-chloro-3-fluoropyridin-2-yl)methylene)-2-methylpropane-2-sulfinamide (220b) (11.08 g, 100% yield) which was used in the next reaction without further purification; $^1$H NMR (300 MHz, DMSO-$d_6$) δ 8.59 (d, J=5.1 Hz, 1H), 8.56 (s, 1H), 7.97 (dd, J=5.6, 5.0 Hz, 1H), 1.21 (s, 9H).

Step-2: Preparation of (+)—(S)—N-((4-chloro-3-fluoropyridin-2-yl)methyl)-2-methylpropane-2-sulfinamide (220c)

To a solution of (S)—N-((4-chloro-3-fluoropyridin-2-yl)methylene)-2-methylpropane-2-sulfinamide (220b) (11.08 g, 42.2 mmol) in methanol (211 mL) at 0° C. was added $NaBH_4$ (1.595 g, 42.2 mmol) and stirred for 0.5 h. The reaction was quenched with acetone (20 mL) and concentrated in vacuum. The residue was taken in EtOAc and saturated aqueous $NH_4Cl$. The organic layer was separated, washed with brine, dried, filtered and concentrated under vacuum. The residue obtained was purified by flash column chromatography [silica gel (120 g), eluting with a 9:1 mixture of ethyl acetate and methanol in hexanes] to afford (+)-(S)—N-((4-chloro-3-fluoropyridin-2-yl)methyl)-2-methylpropane-2-sulfinamide (220c) (9.34 g, 84% yield) as a thick clear syrup; $^1$H NMR (300 MHz, DMSO-$d_6$) δ 8.36 (d, J=5.2 Hz, 1H), 7.72-7.62 (m, 1H), 5.86 (t, J=5.9 Hz, 1H), 4.34 (dd, J=5.9, 2.2 Hz, 2H), 1.09 (s, 9H); Optical rotation [t]D=+53.88 (c=0.49, MeOH).

Step-3: Preparation of Ethyl 2-(2-((2-isobutyl-7-(4,4,5,5-tetramethyl-1,3,2-dioxaborolan-2-yl)benzofuran-5-yl)methoxy)phenyl)acetate (220d)

Compound 220d was prepared according to the procedure reported in step-1 of scheme-59 from ethyl 2-(2-((7-iodo-2-isobutylbenzofuran-5-yl)methoxy)phenyl)acetate (200c) (750 mg, 1.523 mmol), using bis(pinacolato)diboron (580 mg, 2.285 mmol), potassium acetate (449 mg, 4.57 mmol) and $PdCl_2(dppf)$-$CH_2Cl_2$ (373 mg, 0.457 mmol) in anhydrous dioxane (25 mL) under an Ar atmosphere and heating at 100° C. overnight. This gave after workup and purification by flash column chromatography [silica gel, 40 g, eluting with EtOAc in hexane from 0-10%] ethyl 2-(2-((2-isobutyl-7-(4,4,5,5-tetramethyl-1,3,2-dioxaborolan-2-yl)benzofuran-5-yl)methoxy)phenyl)acetate (220d) (370 mg) as an off-white solid.

Step-4: Preparation of (S)-ethyl 2-(2-((7-(2-((1,1-dimethylethylsulfinamido)methyl)-3-fluoropyridin-4-yl)-2-isobutylbenzofuran-5-yl)methoxy)phenyl)acetate (220e)

Compound 220e was prepared according to the procedure reported in step-3 of scheme-1 from ethyl 2-(2-((2-isobutyl-7-(4,4,5,5-tetramethyl-1,3,2-dioxaborolan-2-yl)benzofuran-5-yl)methoxy)phenyl)acetate (220d) (350 mg, 0.711 mmol) in dioxane (8 mL) using (+)-(S)—N-((4-chloro-3-fluoropyridin-2-yl)methyl)-2-methylpropane-2-sulfinamide (220c) (282 mg, 1.066 mmol), bis(triphenylphosphine)palladium(II) chloride (150 mg, 0.213 mmol) and a solution of $K_2CO_3$ (295 mg, 2.132 mmol) in water (0.8 mL) under an Ar atmosphere and heating at 100° C. for 3 h on oil bath. This gave after workup, purification by flash column chromatography [silica gel, eluting with hexanes/10% methanol in ethyl acetate (1:0 to 1:1)] (S)-ethyl 2-(2-((7-(2-((1,1-dimethylethylsulfinamido)methyl)-3-fluoropyridin-4-yl)-2-isobutylbenzofuran-5-yl)methoxy)phenyl)acetate (220e) (196 mg) as a light brown gum.

Step-5: Preparation of Ethyl 2-(2-((7-(2-(aminomethyl)-3-fluoropyridin-4-yl)-2-isobutylbenzofuran-5-yl)methoxy)phenyl)acetate (220f)

A solution of (S)-ethyl 2-(2-((7-(2-((1,1-dimethylethylsulfinamido)methyl)-3-fluoropyridin-4-yl)-2-isobutylbenzofuran-5-yl)methoxy)phenyl)acetate (220e) (186 mg, 0.313 mmol) in ethanol (5 mL) cooled to 0° C. was added hydrochloric acid (4 M in 1,4-dioxane, 0.235 mL, 0.938 mmol) and stirred at rt for 1 h. The reaction mixture was concentrated to dryness to furnish ethyl 2-(2-((7-(2-(aminomethyl)-3-fluoropyridin-4-yl)-2-isobutylbenzofuran-5-yl)methoxy)phenyl)acetate (220f) which was used as such for next step; MS (ES+): 491.3 (M+1) & 513.2 (M+Na).

Step-6: Preparation of 2-(2-((7-(2-(aminomethyl)-3-fluoropyridin-4-yl)-2-isobutylbenzofuran-5-yl)methoxy)phenyl)acetic Acid (220g)

Compound 220g was prepared according to the procedure reported in step-6 of scheme-1 from ethyl 2-(2-((7-(2-(aminomethyl)-3-fluoropyridin-4-yl)-2-isobutylbenzofuran-5-yl)methoxy)phenyl)acetate (220f) (154 mg, 0.313 mmol) in THF (8 mL) and MeOH (8 mL) using lithium hydroxide hydrate (134 mg, 3.13 mmol) in water (8 mL). This gave after workup and purification by reverse phase column [C18 (50g), eluting with ACN in water (containing 0.1% HCl) from 0-100%] 2-(2-((7-(2-(aminomethyl)-3-fluoropyridin-4-yl)-2-isobutylbenzofuran-5-yl)methoxy)phenyl)acetic acid (220g) (34 mg, 5.4% for 4 steps) as a light yellow solid; $^1$H NMR (300 MHz, DMSO-$d_6$) δ 12.22 (s, 1H), 8.63 (d, J=5.0 Hz, 1H), 8.57-8.46 (m, 3H), 7.82-7.75 (m, 2H), 7.51-7.49 (m, 1H), 7.29-7.18 (m, 2H), 7.09 (d, J=8.0 Hz, 1H), 6.91 (td, J=7.4, 1.1 Hz, 1H), 6.74 (s, 1H), 5.25 (s, 2H), 4.46-4.30 (m, 2H), 3.58 (s, 2H), 2.66 (d, J=7.0 Hz, 2H), 2.18-1.82 (m, 1H), 0.94 (d, J=6.6 Hz, 6H); 19F NMR (282 MHz, DMSO-$d_6$) δ−128.52; MS (ES+): 463.2 (M+1), MS (ES−): 461.3 (M−1); HPLC purity: 95.28%.

Scheme-221

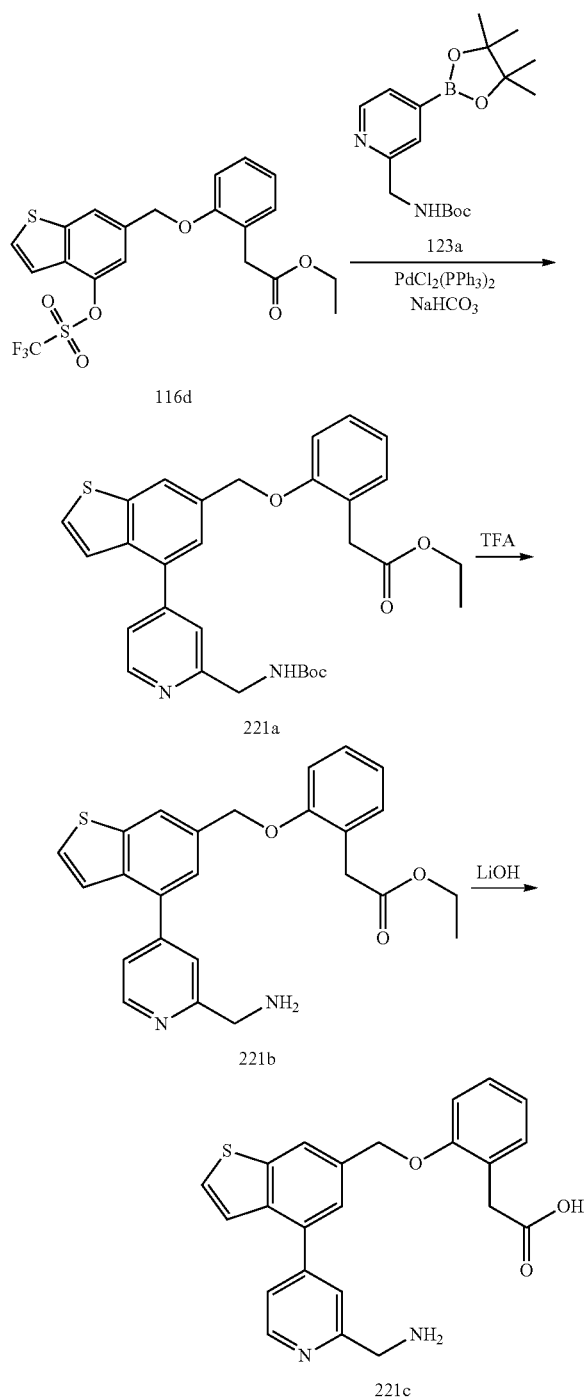

Preparation of 2-(2-((4-(2-(aminomethyl)pyridin-4-yl)benzo[b]thiophen-6-yl)methoxy)phenyl)acetic Acid (221c)

Step-1: Preparation of Ethyl 2-(2-((4-(2-(((tert-butoxycarbonyl)amino)methyl)pyridin-4-yl)benzo[b]thiophen-6-yl)methoxy)phenyl)acetate (221a)

Compound 221a was prepared according to the procedure reported in step-3 of Scheme-1 from ethyl 2-(2-((4-(((trifluoromethyl)sulfonyl)oxy)benzo[b]thiophen-6-yl)methoxy)phenyl)acetate (116d) (240 mg, 0.506 mmol) in dioxane (6 mL) using tert-butyl ((4-(4,4,5,5-tetramethyl-1,3,2-dioxaborolan-2-yl)pyridin-2-yl)methyl)carbamate (123a) (254 mg, 0.759 mmol), a solution of $NaHCO_3$ (127 mg, 1.517 mmol) in water (0.6 mL), bis(triphenylphosphine)palladium (II) chloride (107 mg, 0.152 mmol) and heating at 100° C. for 3 h on oil bath. This gave after workup, purification by flash column chromatography [silica gel, eluting with hexanes/ethyl acetate (1:0 to 1:1)] ethyl 2-(2-((4-(2-(((tert-butoxycarbonyl)amino)methyl)pyridin-4-yl)benzo[b]thiophen-6-yl)methoxy)phenyl)acetate (221a) (195 mg, 72%) as colorless gum; $^1$H NMR (300 MHz, DMSO-$d_6$) δ 8.63 (dd, J=5.0, 0.9 Hz, 1H), 8.17-8.15 (m, 1H), 7.89 (d, J=5.5 Hz, 1H), 7.57-7.44 (m, 5H), 7.30-7.18 (m, 2H), 7.13-7.09 (m, 1H), 6.95-6.89 (m, 1H), 5.29 (s, 2H), 4.32 (d, J=6.2 Hz, 2H), 3.90 (q, J=7.1 Hz, 2H), 3.64 (s, 2H), 1.39 (s, 9H), 0.97 (t, J=7.1 Hz, 3H); MS (ES+): 533.2 (M+1).

Step-2: Preparation of Ethyl 2-(2-((4-(2-(aminomethyl)pyridin-4-yl)benzo[b]thiophen-6-yl)methoxy)phenyl)acetate (221b)

Compound 221b was prepared according to the procedure reported in step-5 of Scheme-1 from ethyl 2-(2-((4-(2-(((tert-butoxycarbonyl)amino)methyl)pyridin-4-yl)benzo[b]thiophen-6-yl)methoxy)phenyl)acetate (221a) (185 mg, 0.347 mmol) in DCM (10 mL) using TFA (0.268 mL, 3.47 mmol). This gave after workup and purification by flash column chromatography [silica gel, eluting with dichloromethane/DMA 80 (1:0 to 2:1)] ethyl 2-(2-((4-(2-(aminomethyl)pyridin-4-yl)benzo[b]thiophen-6-yl)methoxy)phenyl)acetate (221b) (131 mg, 87%) as a colorless gum; $^1$H NMR (300 MHz, DMSO-$d_6$) δ 8.61 (d, J=5.1 Hz, 1H), 8.14 (s, 1H), 7.89 (d, J=5.6 Hz, 1H), 7.71-7.69 (m, 1H), 7.55-7.41 (m, 3H), 7.31-7.17 (m, 2H), 7.11 (dd, J=8.2, 1.1 Hz, 1H), 6.92 (td, J=7.4, 1.1 Hz, 1H), 5.30 (s, 2H), 4.01-3.86 (m, 4H), 3.65 (s, 2H), 1.00 (t, J=7.1 Hz, 3H); MS (ES+): 433.2 (M+1).

Step-3: Preparation of 2-(2-((4-(2-(aminomethyl)pyridin-4-yl)benzo[b]thiophen-6-yl)methoxy)phenyl)acetic Acid (221c)

Compound 221c was prepared according to the procedure reported in step-6 of Scheme-1 from ethyl 2-(2-((4-(2-(aminomethyl)pyridin-4-yl)benzo[b]thiophen-6-yl)methoxy)phenyl)acetate (221b) (120 mg, 0.277 mmol) in MeOH/THF (7 mL each) using a solution of lithium hydroxide monohydrate (71 mg, 1.67 mmol) in water (8 mL). This gave after workup and purification by reverse phase column [C18 (50 g), eluting with ACN in water (containing 0.1% HCl) from 0-100%] 2-(2-((4-(2-(aminomethyl)pyridin-4-yl)benzo[b]thiophen-6-yl)methoxy)phenyl)acetic acid (221c) (43 mg, 38%) as a white solid; $^1$H NMR (300 MHz, DMSO-$d_6$) δ 8.78-8.75 (m, 1H), 8.52 (s, 3H), 8.22-8.20 (m, 1H), 7.93 (d, J=5.6 Hz, 1H), 7.82-7.80 (m, 1H), 7.68 (dd, J=5.2, 1.7 Hz, 1H), 7.63-7.52 (m, 2H), 7.28-7.17 (m, 2H), 7.13-7.04 (m, 1H), 6.91 (td, J=7.4, 1.1 Hz, 1H), 5.32 (s, 2H), 4.35-4.26 (m, 2H); MS (ES+): 405.15 (M+1); MS (ES−): 403.30 (M−1); HPLC purity: 89.53%.

Scheme-222

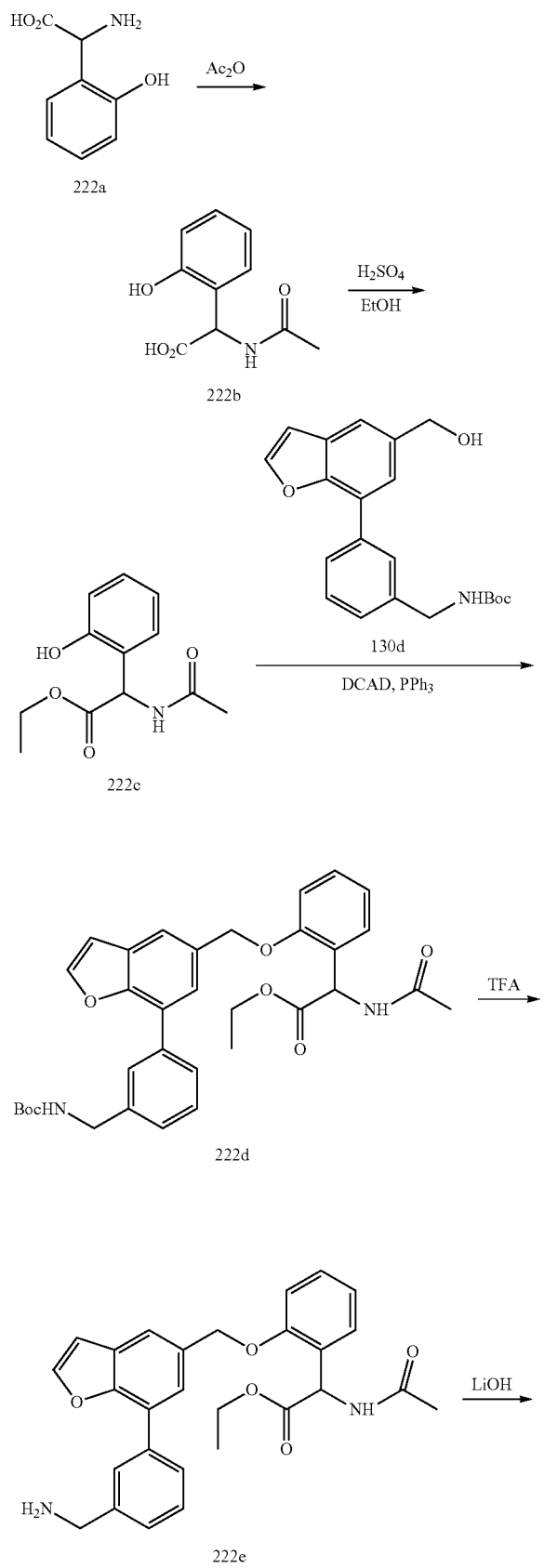

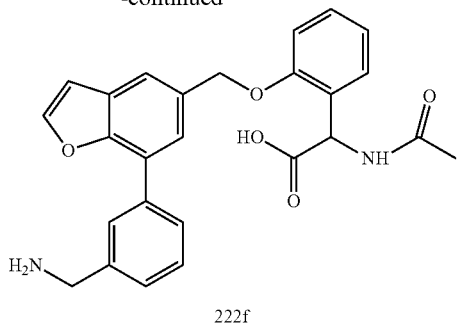

Preparation of 2-acetamido-2-(2-((7-(3-(aminomethyl)phenyl)benzofuran-5-yl)methoxy)phenyl)acetic Acid (222f)

Step-1: Preparation of 2-acetamido-2-(2-hydroxyphenyl)acetic Acid (222b)

To a solution of 2-amino-2-(2-hydroxyphenyl)acetic acid (222a) (1 g, 5.98 mmol; CAS #25178-38-5) in water (20 mL) was added sodium hydroxide (0.502 g, 12.56 mmol), acetic anhydride (1.411 mL, 14.96 mmol) and stirred for 30 minutes at rt. The solution was acidified with 3 N HCl and extracted with ethyl acetate (3×100 mL). The combined organic layers were washed with brine (50 mL), dried, filtered and concentrated in vacuum to afford 2-acetamido-2-(2-hydroxyphenyl)acetic acid (222b) (1.1 g, 88% yield) as a white solid; MS (ES+) 210.10 (M+1), (ES−) 208.20 (M−1).

Step-2: Preparation of Ethyl 2-acetamido-2-(2-hydroxyphenyl)acetate (222c)

To a solution of 2-acetamido-2-(2-hydroxyphenyl)acetic Acid (222b) (1.06 g, 5.07 mmol) in ethanol (20 mL) was added sulfuric acid (0.270 mL, 5.07 mmol) and heated to reflux for 2h. The reaction was cooled to room temperature, neutralized with sodium bicarbonate and concentrated in vacuum to remove excess ethanol. The residue was diluted with water (30 mL) and ethyl acetate (100 mL). The organic layer was separated and aqueous layer was extracted with ethyl acetate (2×50 mL). Combined organic layer was washed with water (2×20 mL), brine (20 mL), dried, filtered and concentrated in vacuum to afford ethyl 2-acetamido-2-(2-hydroxyphenyl)acetate (222c) (700 mg, 58% yield) as a thick syrup; $^1$H NMR (300 MHz, DMSO-$d_6$) δ 9.79 (s, 1H), 8.38 (d, J=7.5 Hz, 1H), 7.21-7.07 (m, 2H), 6.93-6.69 (m, 2H), 5.63 (d, J=7.5 Hz, 1H), 4.18-3.91 (m, 2H), 1.86 (s, 3H), 1.11 (t, J=7.1 Hz, 3H).

Step-3: Preparation of Ethyl 2-acetamido-2-(2-((7-(3-(((tert-butoxycarbonyl)amino)methyl)phenyl)benzofuran-5-yl)methoxy)phenyl)acetate (222d)

Compound 222d was prepared according to the procedure reported in step-2 of Scheme-23 from tert-butyl 3-(5-(hydroxymethyl)benzofuran-7-yl)benzylcarbamate (130d) (0.453 g, 1.283 mmol) in DCM (15 mL) using triphenylphosphine (0.370 g, 1.411 mmol) ethyl 2-acetamido-2-(2-hydroxyphenyl)acetate (222c) (0.35 g, 1.475 mmol) and di-(4-chlorobenzyl)azodicarboxylate (DCAD, 0.518 g, 1.411 mmol). This gave after workup and purification by flash column chromatography (silica gel 40 g, eluting with ethyl acetate in hexanes from 0-50%) ethyl 2-acetamido-2-(2-((7-(3-(((tert-butoxycarbonyl)amino)methyl)phenyl)benzofuran-5-yl)methoxy)phenyl)acetate (222d) (480 mg, 65% yield) as a white solid; $^1$H NMR (300 MHz, DMSO-$d_6$) δ 8.54 (d, J=7.8 Hz, 1H), 8.08 (d, J=2.2 Hz, 1H), 7.81-7.70 (m, 3H), 7.61 (d, J=1.6 Hz, 1H), 7.48 (t, J=7.4 Hz, 2H), 7.36-7.23 (m, 3H), 7.22-7.10 (m, 1H), 7.04 (d, J=2.2 Hz, 1H), 7.01-6.92 (m, 1H), 5.82 (d, J=7.8 Hz, 1H), 5.31 (s, 2H), 4.22 (d, J=6.2 Hz, 2H), 4.07-3.97 (m, 2H), 1.86 (d, J=0.8 Hz, 3H), 1.39 (s, 9H), 0.97 (t, J=7.1 Hz, 3H); MS (ES+): 473.25 (M+1-Boc), (ES−) 571.40 (M−1).

Step-4: Preparation of Ethyl 2-acetamido-2-(2-((7-(3-(aminomethyl)phenyl)benzofuran-5-yl)methoxy)phenyl)acetate (222e)

Compound 222e was prepared according to the procedure reported in step-5 of Scheme-1 from ethyl 2-acetamido-2-(2-((7-(3-(((tert-butoxycarbonyl)amino)methyl)phenyl)benzofuran-5-yl)methoxy)phenyl)acetate (222d) (100 mg, 0.175 mmol) in DCM (10 mL) using TFA (0.135 mL, 1.746 mmol). This gave after workup ethyl 2-acetamido-2-(2-((7-(3-(aminomethyl)phenyl)benzofuran-5-yl)methoxy)phenyl)acetate (222e) (83 mg, 100% yield) which was used in the next step without further purification; MS (ES+): 473.25 (M+1).

Step-5: Preparation of 2-acetamido-2-(2-((7-(3-(aminomethyl)phenyl)benzofuran-5-yl)methoxy)phenyl)acetic Acid (222f)

Compound 222f was prepared according to the procedure reported in step-6 of Scheme-1 from ethyl 2-acetamido-2-(2-((7-(3-(aminomethyl)phenyl)benzofuran-5-yl)methoxy)phenyl)acetate (222e) (83 mg, 0.176 mmol) in THF (5 mL) and methanol (5 mL) using a solution of lithium hydroxide monohydrate (21 mg, 0.878 mmol) in water (2 mL). This gave after workup and purification by reverse phase column [C18 (30 g), eluting with ACN in water (containing 0.1% HCl) from 0-100%] 2-acetamido-2-(2-((7-(3-(aminomethyl)phenyl)benzofuran-5-yl)methoxy)phenyl)acetic acid (222f) (43 mg, 55% yield) HCl salt as a white solid; $^1$H NMR (300 MHz, DMSO-$d_6$) δ 12.71 (s, 1H), 8.56 (d, J=7.9 Hz, 1H), 8.38 (s, 3H), 8.11 (d, J=2.2 Hz, 1H), 8.01 (d, J=1.8 Hz, 1H), 7.95 (dt, J=7.5, 1.7 Hz, 1H), 7.78 (d, J=1.6 Hz, 1H), 7.70 (d, J=1.6 Hz, 1H), 7.63-7.52 (m, 2H), 7.32 (td, J=7.4, 6.8, 1.8 Hz, 2H), 7.21-7.13 (m, 1H), 7.06 (d, J=2.2 Hz, 1H), 6.98 (td, J=7.4, 1.1 Hz, 1H), 5.87 (d, J=7.9 Hz, 1H), 5.32 (s, 2H), 4.16 (d, J=5.8 Hz, 2H), 1.86 (s, 3H); MS (ES+): 445.2 (M+1), (ES−): 443.3 (M−1).

Scheme-223

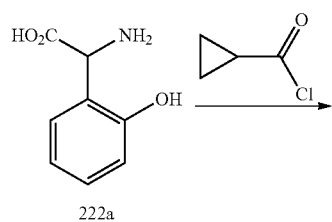

222a

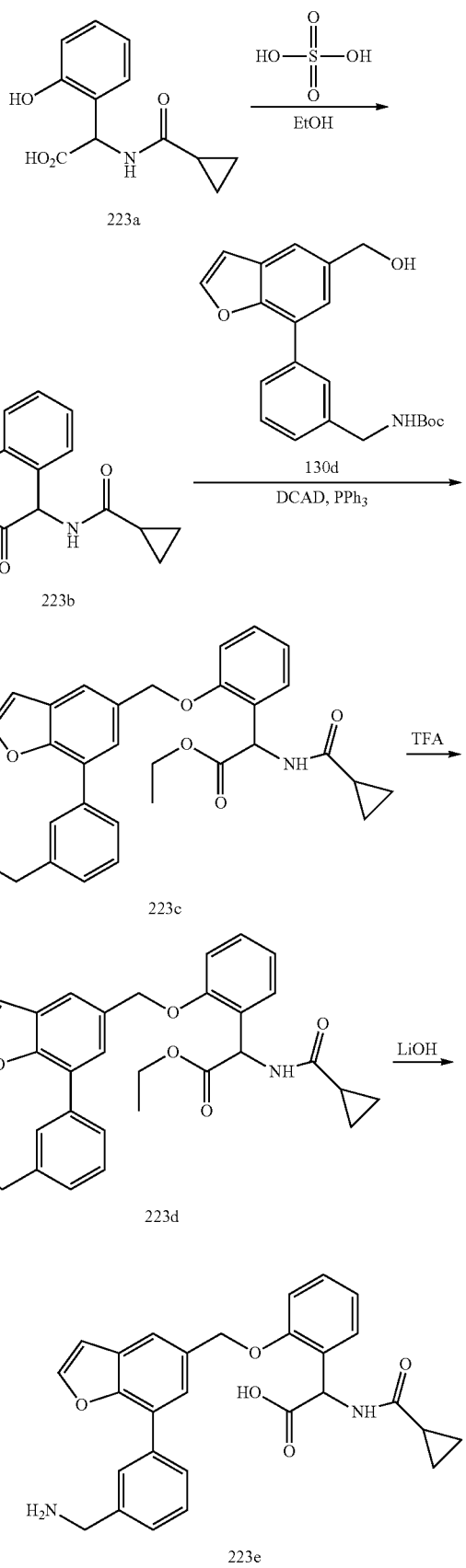

Preparation of 2-(2-((7-(3-(aminomethyl)phenyl)
benzofuran-5-yl)methoxy)phenyl)-2-(cyclopropan-
ecarboxamido)acetic Acid (223e)

Step-1: Preparation of 2-(cyclopropanecarbox-
amido)-2-(2-hydroxyphenyl)acetic Acid (223a)

To a solution of 2-amino-2-(2-hydroxyphenyl)acetic acid (222a) (1 g, 5.98 mmol; CAS #25178-38-5) in water (20 mL)/THF (10 mL) cooled to 0° C. was added sodium bicarbonate (2.010 g, 23.93 mmol) a solution of cyclopropanecarbonyl chloride (1.629 mL, 17.95 mmol) in tetrahydrofuran (10 mL) and allowed to warm to rt. The solution was acidified with 3 N HCl and extracted with ethyl acetate (3×100 mL). The combined organic layers were washed with brine (50 mL), dried, filtered and concentrated in vacuum to afford 2-(cyclopropanecarboxamido)-2-(2-hydroxyphenyl)acetic acid (223a) (2.03 g) as a thick syrup, which was used in the next step without further purification; $^1$H NMR (300 MHz, DMSO-$d_6$) δ 8.51 (d, J=7.8 Hz, 1H), 7.31-7.05 (m, 2H), 6.93-6.60 (m, 2H), 5.62 (d, J=7.8 Hz, 1H), 1.84-1.69 (m, 1H), 0.71-0.58 (m, 4H); MS (ES+): 236.1 (M+1), (ES−): 270.3 (M+Cl).

Step-2: Preparation of Ethyl 2-(cyclopropanecar-
boxamido)-2-(2-hydroxyphenyl)acetate (223b)

Compound 223b was prepared according to the procedure reported in step-2 of Scheme-222 from 2-(cyclopropanecarboxamido)-2-(2-hydroxyphenyl)acetic acid (223a) (2.03 g, 8.63 mmol) in ethanol (30 mL) using sulfuric acid (0.920 mL, 17.26 mmol). This gave after workup and purification by flash column chromatography (silica gel) ethyl 2-(cyclopropanecarboxamido)-2-(2-hydroxyphenyl)acetate (223b) (585 mg, 26% yield) as a white solid; $^1$H NMR (300 MHz, DMSO-$d_6$) δ 9.80 (s, 1H), 8.59 (d, J=7.5 Hz, 1H), 7.22-7.04 (m, 2H), 6.92-6.68 (m, 2H), 5.66 (d, J=7.5 Hz, 1H), 4.13-4.02 (m, 2H), 1.82-1.65 (m, 1H), 1.11 (t, J=7.1 Hz, 3H), 0.74-0.51 (m, 4H).

Step-3: Preparation ethyl 2-(2-((7-(3-(((tert-butoxy-
carbonyl)amino)methyl)phenyl)benzofuran-5-yl)
methoxy)phenyl)-2-(cyclopropanecarboxamido)ac-
etate (223c)

Compound 223c was prepared according to the procedure reported in step-2 of Scheme-23 from tert-butyl 3-(5-(hydroxymethyl)benzofuran-7-yl)benzylcarbamate (130d) (642 mg, 1.816 mmol) in DCM (15 mL) using triphenylphosphine (548 mg, 2.089 mmol), ethyl 2-(cyclopropanecarboxamido)-2-(2-hydroxyphenyl)acetate (223b) (550 mg, 2.089 mmol) and di-(4-chlorobenzyl)azodicarboxylate (DCAD, 800 mg, 2.180 mmol). This gave after workup and purification by flash column chromatography (silica gel 40 g, eluting with ethyl acetate in hexanes from 0-50%) ethyl 2-(2-((7-(3-(((tert-butoxycarbonyl)amino)methyl)phenyl)benzofuran-5-yl)methoxy)phenyl)-2-(cyclopropanecarboxamido)acetate (223c) (1.15 g, 106% yield) as a clear oil; $^1$H NMR (300 MHz, DMSO-$d_6$) δ 8.76 (d, J=8.0 Hz, 1H), 8.08 (d, J=2.2 Hz, 1H), 7.84-7.69 (m, 3H), 7.62 (d, J=1.6 Hz, 1H), 7.52-7.42 (m, 2H), 7.42-7.34 (m, 1H), 7.34-7.25 (m, 2H), 7.22-7.14 (m, 1H), 7.03 (d, J=2.2 Hz, 1H), 6.98 (td, J=7.5, 1.1 Hz, 1H), 5.87 (d, J=7.9 Hz, 1H), 5.31 (s, 2H), 4.22 (d, J=6.2 Hz, 2H), 3.98 (dd, J=7.1, 5.3 Hz, 2H), 1.76 (m, 1H), 1.39 (s, 9H), 0.98 (t, J=7.1 Hz, 3H), 0.63 (m, 4H); MS (ES+): 499.20 (M+1-Boc), 599.25 (M+1).

Step-4: Preparation of Ethyl 2-(2-((7-(3-(aminom-
ethyl)phenyl)benzofuran-5-yl)methoxy)phenyl)-2-
(cyclopropanecarboxamido)acetate (223d)

Compound 223d was prepared according to the procedure reported in step-5 of Scheme-1 from ethyl 2-(2-((7-(3-(((tert-butoxycarbonyl)amino)methyl)phenyl)benzofuran-5-yl)methoxy)phenyl)-2-(cyclopropanecarboxamido)acetate (223c) (1 g, 1.670 mmol) in DCM (15 mL) using TFA (1.287 mL, 16.70 mmol). This gave after workup compound 223d (840 mg, 101% yield) as a TFA salt. 100 mgs of this material was purified by reverse phase column [C18 (30 g), eluting with ACN in water (containing 0.1% HCl) from 0-100%] to afford ethyl 2-(2-((7-(3-(aminomethyl)phenyl)benzofuran-5-yl)methoxy)phenyl)-2-(cyclopropanecarboxamido)acetate (223d) hydrochloride salt as a white solid; $^1$H NMR (300 MHz, DMSO-$d_6$) δ 8.79 (d, J=7.9 Hz, 1H), 8.29 (s, 3H), 8.11 (d, J=2.2 Hz, 1H), 8.00 (s, 1H), 7.92 (d, J=7.5 Hz, 1H), 7.77 (d, J=1.6 Hz, 1H), 7.66 (d, J=1.6 Hz, 1H), 7.63-7.51 (m, 2H), 7.38-7.26 (m, 2H), 7.20 (d, J=8.2 Hz, 1H), 7.06 (d, J=2.2 Hz, 1H), 6.99 (t, J=7.5 Hz, 1H), 5.88 (d, J=7.9 Hz, 1H), 5.31 (s, 2H), 4.14 (s, 2H), 3.99 (qd, J=7.1, 4.0 Hz, 2H), 1.76 (p, J=6.5 Hz, 1H), 0.99 (t, J=7.1 Hz, 3H), 0.64 (dt, J=18.0, 6.9 Hz, 4H); MS (ES+): 499.3 (M+1), 521.2 (M+Na).

Step-5: Preparation of 2-(2-((7-(3-(aminomethyl)
phenyl)benzofuran-5-yl)methoxy)phenyl)-2-(cyclo-
propanecarboxamido)acetic Acid (223e)

Compound 223e was prepared according to the procedure reported in step-6 of Scheme-1 from ethyl 2-(2-((7-(3-(aminomethyl)phenyl)benzofuran-5-yl)methoxy)phenyl)-2-(cyclopropanecarboxamido)acetate (223d) (833 mg, 1.67 mmol) in THF (10 mL) and methanol (5 mL) using a solution of lithium hydroxide monohydrate (160 mg, 6.68 mmol) in water (3 mL). This gave after workup and purification by reverse phase column [C18 (30 g), eluting with ACN in water (containing 0.1% HCl) from 0-100%] 2-(2-((7-(3-(aminomethyl)phenyl)benzofuran-5-yl)methoxy)phenyl)-2-(cyclopropanecarboxamido)acetic acid (223e) (250 mg, 32% yield) HCl salt as a white solid; $^1$H NMR (300 MHz, DMSO-$d_6$) δ 12.73 (s, 1H), 8.73 (d, J=8.1 Hz, 1H), 8.56 (s, 3H), 8.11 (d, J=2.2 Hz, 1H), 8.03 (q, J=1.3 Hz, 1H), 7.93 (m, 1H), 7.79 (d, J=1.6 Hz, 1H), 7.72 (d, J=1.6 Hz, 1H), 7.63-7.53 (m, 2H), 7.31 (ddd, J=13.0, 7.6, 1.7 Hz, 2H), 7.16 (dd, J=8.3, 1.2 Hz, 1H), 7.04 (d, J=2.2 Hz, 1H), 6.98 (td, J=7.5, 1.1 Hz, 1H), 5.89 (d, J=8.0 Hz, 1H), 5.33 (s, 2H), 4.13 (s, 2H), 1.76 (m, 1H), 0.76-0.48 (m, 4H); MS (ES+): 471.2 (M+1), (ES−): 469.3 (M−1).

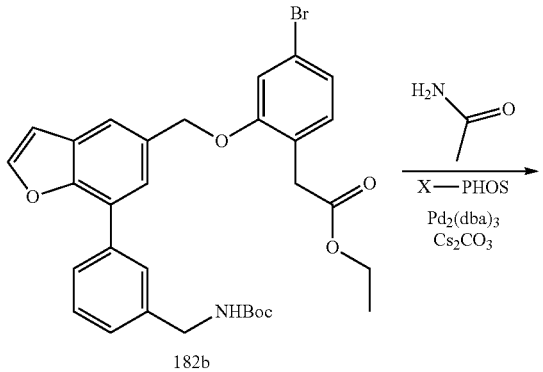

Scheme-224

-continued

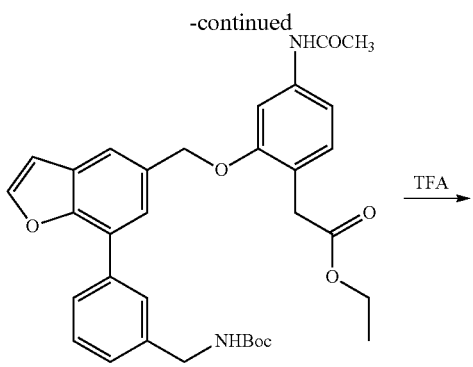

224a

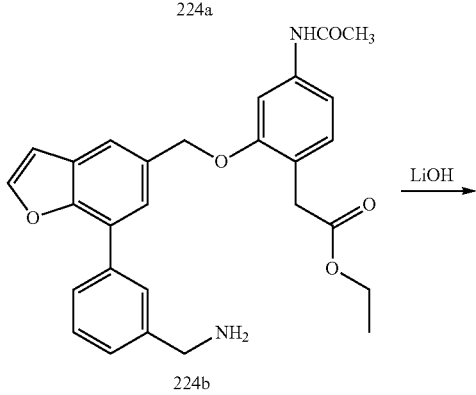

224b

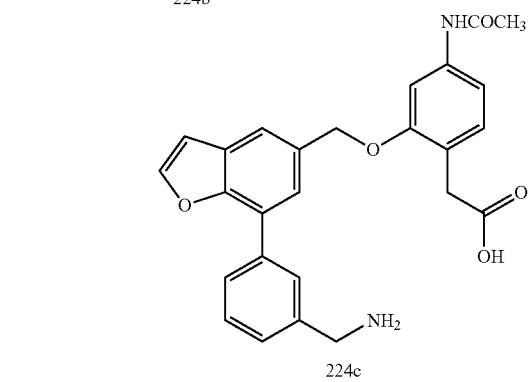

224c

Preparation of 2-(4-acetamido-2-((7-(3-(aminomethyl)phenyl)benzofuran-5-yl)methoxy)phenyl)acetic Acid (224c)

Step-1: Preparation of Ethyl 2-(4-acetamido-2-((7-(3-(((tert-butoxycarbonyl)amino)methyl)phenyl) benzofuran-5-yl)methoxy)phenyl)acetate (224a)

A mixture of ethyl 2-(4-bromo-2-((7-(3-(((tert-butoxycarbonylamino)methyl)phenyl)benzofuran-5-yl)methoxy)phenyl)acetate (182b) (0.300 g, 0.505 mmol), acetamide (0.089 g, 1.514 mmol), (Note: acetamide was dried over $P_2O_5$ prior to use), $Cs_2CO_3$ (0.164 g, 0.505 mmol), dicyclohexyl(2',4',6'-triisopropylbiphenyl-2-yl)phosphine (X-PHOS) (0.048 g, 0.101 mmol), $Pd_2(dba)_3$ (0.046 g, 0.050 mmol) was purged with positive flow of nitrogen for 10 min, followed by the addition of anhydrous toluene (10 mL) under a positive flow of nitrogen. The flask was heated at 95° C. for 4 h, cooled to room temperature, diluted with ethyl acetate (100 mL) and brine (100 mL). The aq. layer was separated and extracted with ethyl acetate (100 mL). The combined organic layer was washed with brine, dried, filtered and evaporated to dryness. The residue obtained was purified by column chromatography [silica gel 12 g, eluting with methanol in DCM from 0 to 40%] to afford ethyl 2-(4-acetamido-2-((7-(3-(((tert-butoxycarbonyl)amino)methyl)phenyl)benzofuran-5-yl)methoxy)phenyl)acetate (224a) (0.233 g, 81% yield) as an orange syrup; $^1$H NMR (300 MHz, DMSO-$d_6$) δ 9.95 (s, 1H), 8.08 (d, J=2.2 Hz, 1H), 7.75 (d, J=9.1 Hz, 2H), 7.70 (d, J=1.6 Hz, 1H), 7.56 (d, J=1.7 Hz, 1H), 7.54-7.42 (m, 2H), 7.30 (d, J=7.5 Hz, 1H), 7.15-7.08 (m, 2H), 7.06 (d, J=2.2 Hz, 1H), 5.17 (s, 2H), 4.23 (d, J=6.2 Hz, 2H), 3.91 (q, J=7.1 Hz, 2H), 3.56 (s, 2H), 2.03 (s, 3H), 1.39 (s, 9H), 0.97 (t, J=7.1 Hz, 3H); MS (ES+): 473.3 (M+1, −Boc).

Step-2: Preparation of Ethyl 2-(4-acetamido-2-((7-(3-(aminomethyl)phenyl)benzofuran-5-yl)methoxy)phenyl)acetate (224b)

Compound 224b was prepared according to the procedure reported in step-5 of Scheme-1 from ethyl 2-(4-acetamido-2-((7-(3-(((tert-butoxycarbonyl)amino)methyl)phenyl)benzofuran-5-yl)methoxy)phenyl)acetate (224a) (0.205 g, 0.358 mmol) in DCM (20 mL) using TFA (0.552 mL, 7.16 mmol). This gave after workup and purification by flash column chromatography [silica gel 12 g, eluting with methanol in DCM from 0-100%] ethyl 2-(4-acetamido-2-((7-(3-(aminomethyl)phenyl)benzofuran-5-yl)methoxy)phenyl)acetate (224b) (0.133 g, 79% yield) as a brown solid; MS (ES+): 473.25 (M+1); MS (ES−): 471.3 (M−1).

Step-3: Preparation of 2-(4-acetamido-2-((7-(3-(aminomethyl)phenyl)benzofuran-5-yl)methoxy)phenyl)acetic Acid (224c)

Compound 224c was prepared according to the procedure reported in step-6 of Scheme-1 from ethyl 2-(4-acetamido-2-((7-(3-(aminomethyl)phenyl)benzofuran-5-yl)methoxy)phenyl)acetate (224b) (0.130 g, 0.275 mmol) in THF (4 mL) and methanol (8 mL) using 2M LiOH (0.688 mL, 1.376 mmol). This gave after workup and purification by flash column chromatography [silica gel 12 g, eluting with methanol in DCM from 0-100%] followed by reverse phase column [C18 (30 g), eluting with ACN in water (containing 0.1% HCl) from 0-100%] 2-(4-acetamido-2-((7-(3-(aminomethyl)phenyl)benzofuran-5-yl)methoxy)phenyl)acetic acid (224c) (0.032 g, 26% yield) HCl salt as a white solid; $^1$H NMR (300 MHz, DMSO-$d_6$) δ 12.21 (bs, 1H, $D_2O$ exchangeable), 10.10 (s, 1H, $D_2O$ exchangeable), 8.54 (bs, 3H, $D_2O$ exchangeable), 8.11 (d, J=2.2 Hz, 1H), 8.08-8.04 (m, 1H), 7.99-7.92 (m, 1H), 7.76 (d, J=1.6 Hz, 1H), 7.67 (d, J=1.6 Hz, 1H), 7.60-7.56 (m, 2H), 7.54-7.50 (m, 1H), 7.14-7.09 (m, 2H), 7.06 (d, J=2.2 Hz, 1H), 5.21 (s, 2H), 4.13 (q, J=5.9 Hz, 2H), 3.53 (s, 2H), 2.04 (s, 3H); MS (ES+): 445.2 (M+1); MS (ES−): 443.3 (M−1); HPLC purity: 86.98%; Analysis calculated for $C_{26}H_{24}N_2O_5 \cdot HCl \cdot 1.25H_2O$: C, 62.03; H, 5.51; N, 5.56; Found: C, 61.88; H, 5.45; N, 5.51.

Scheme-225

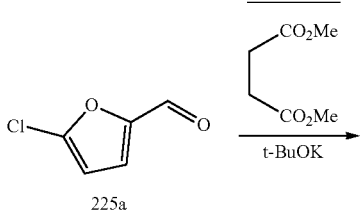

225a

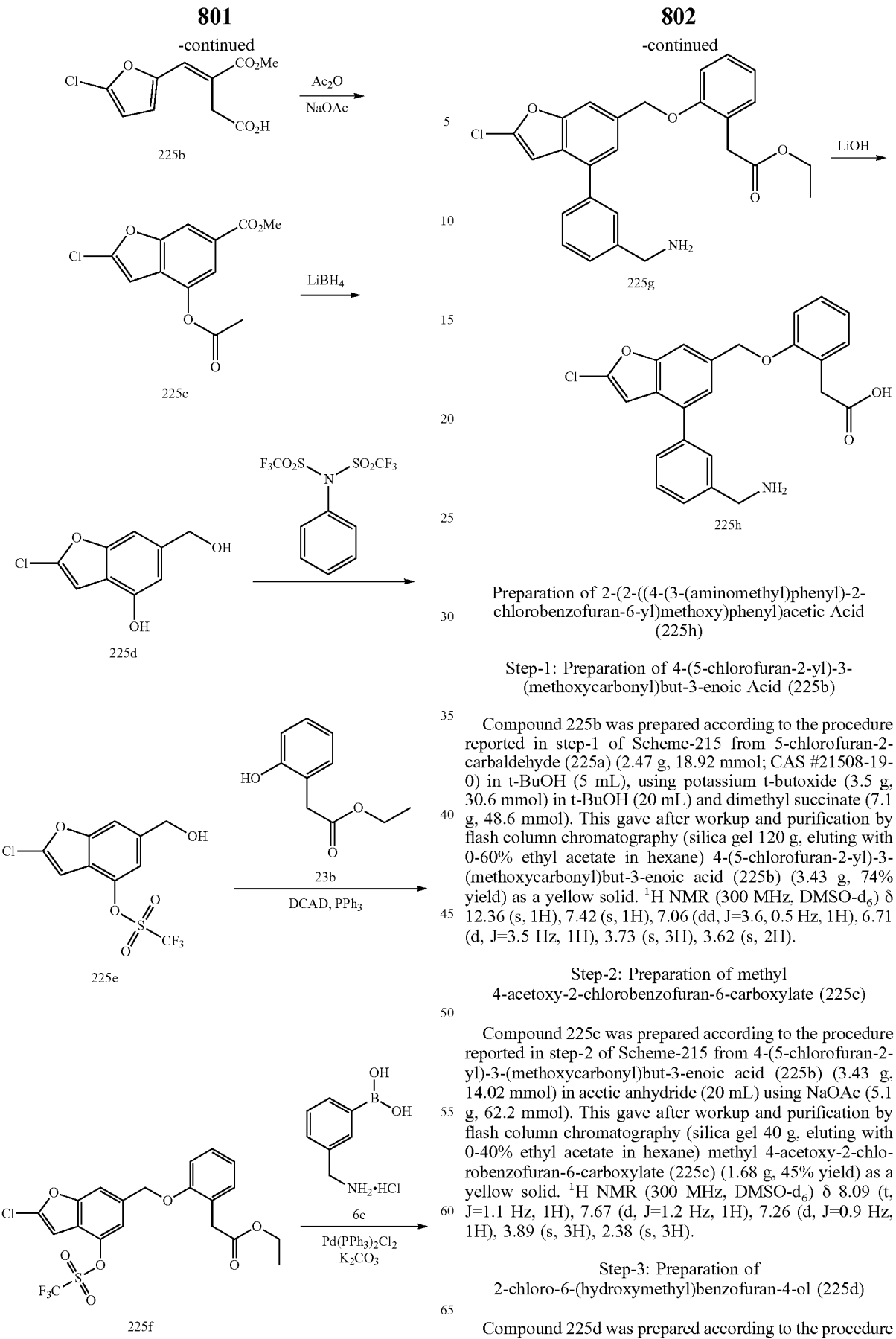

Preparation of 2-(2-((4-(3-(aminomethyl)phenyl)-2-chlorobenzofuran-6-yl)methoxy)phenyl)acetic Acid (225h)

Step-1: Preparation of 4-(5-chlorofuran-2-yl)-3-(methoxycarbonyl)but-3-enoic Acid (225b)

Compound 225b was prepared according to the procedure reported in step-1 of Scheme-215 from 5-chlorofuran-2-carbaldehyde (225a) (2.47 g, 18.92 mmol; CAS #21508-19-0) in t-BuOH (5 mL), using potassium t-butoxide (3.5 g, 30.6 mmol) in t-BuOH (20 mL) and dimethyl succinate (7.1 g, 48.6 mmol). This gave after workup and purification by flash column chromatography (silica gel 120 g, eluting with 0-60% ethyl acetate in hexane) 4-(5-chlorofuran-2-yl)-3-(methoxycarbonyl)but-3-enoic acid (225b) (3.43 g, 74% yield) as a yellow solid. $^1$H NMR (300 MHz, DMSO-$d_6$) δ 12.36 (s, 1H), 7.42 (s, 1H), 7.06 (dd, J=3.6, 0.5 Hz, 1H), 6.71 (d, J=3.5 Hz, 1H), 3.73 (s, 3H), 3.62 (s, 2H).

Step-2: Preparation of methyl 4-acetoxy-2-chlorobenzofuran-6-carboxylate (225c)

Compound 225c was prepared according to the procedure reported in step-2 of Scheme-215 from 4-(5-chlorofuran-2-yl)-3-(methoxycarbonyl)but-3-enoic acid (225b) (3.43 g, 14.02 mmol) in acetic anhydride (20 mL) using NaOAc (5.1 g, 62.2 mmol). This gave after workup and purification by flash column chromatography (silica gel 40 g, eluting with 0-40% ethyl acetate in hexane) methyl 4-acetoxy-2-chlorobenzofuran-6-carboxylate (225c) (1.68 g, 45% yield) as a yellow solid. $^1$H NMR (300 MHz, DMSO-$d_6$) δ 8.09 (t, J=1.1 Hz, 1H), 7.67 (d, J=1.2 Hz, 1H), 7.26 (d, J=0.9 Hz, 1H), 3.89 (s, 3H), 2.38 (s, 3H).

Step-3: Preparation of 2-chloro-6-(hydroxymethyl)benzofuran-4-ol (225d)

Compound 225d was prepared according to the procedure reported in step-2 of Scheme-76 from methyl 4-acetoxy-2- chlorobenzofuran-6-carboxylate (225c) (698 mg, 2.60 mmol) in THF (20 mL) using LiBH₄ (3.3 mL, 13.20 mmol) and MeOH (0.53 mL, 13.10 mmol). This gave after workup and purification by flash column chromatography [silica gel 12g, eluting with EtOAc in hexane from 20 to 75%] 2-chloro-6-(hydroxymethyl)benzofuran-4-ol (225d) (274 mg, 53% yield) as a white solid. $^1$H NMR (300 MHz, DMSO-$d_6$) δ 10.06 (s, 1H), 6.95 (p, J=0.9 Hz, 1H), 6.91 (d, J=0.9 Hz, 1H), 6.65 (t, J=0.9 Hz, 1H), 5.24 (t, J=5.8 Hz, 1H), 4.49 (d, J=5.5 Hz, 2H).

Step-4: Preparation of 2-chloro-6-(hydroxymethyl)benzofuran-4-yl trifluoromethanesulfonate (225e)

Compound 225e was prepared according to the procedure reported in step-2 of Scheme-116 from 2-chloro-6-(hydroxymethyl)benzofuran-4-ol (225d) (644 mg, 3.24 mmol) in DMF (15 mL) using 1,1,1-trifluoro-N-phenyl-N-(trifluoromethylsulfonyl)methanesulfonamide (1.19 g, 3.26 mmol) and triethylamine (1 mL, 7.17 mmol). This gave after workup and purification by flash column chromatography (silica gel 24 g, eluting with 0-50% EtOAc in hexane) 2-chloro-6-(hydroxymethyl)benzofuran-4-yl trifluoromethanesulfonate (225e) (1.01 g, 94% yield) as a white solid. $^1$H NMR (300 MHz, DMSO-$d_6$) δ 7.71 (t, J=1.0 Hz, 1H), 7.42 (d, J=0.9 Hz, 1H), 7.19 (d, J=0.9 Hz, 1H), 4.66 (s, 2H); $^{19}$F NMR (282 MHz, DMSO-$d_6$) δ −72.68.

Step-5: Preparation of Ethyl 2-(2-((2-chloro-4-(((trifluoromethyl)sulfonyl)oxy)benzofuran-6-yl)methoxy)phenyl)acetate (225f)

Compound 225f was prepared according to the procedure reported in step-2 of Scheme-23 from 2-chloro-6-(hydroxymethyl)benzofuran-4-yl trifluoromethanesulfonate (225e) ((970 mg, 2.93 mmol) in DCM (35 mL) using triphenylphosphine (778 mg, 2.97 mmol), ethyl 2-(2-hydroxyphenyl) acetate (23b) (699 mg, 3.88 mmol) and di-(4-chlorobenzyl)azodicarboxylate (1.19 g, 3.24 mmol) in DCM (8 mL). This gave after workup and purification by flash column chromatography (silica gel 40 g, 0-40% EtOAc in hexane) ethyl 2-(2-((2-chloro-4-(((trifluoromethyl)sulfonyl)oxy)benzofuran-6-yl)methoxy)phenyl)acetate (225f) (839 mg, 58% yield) as a white solid. $^1$H NMR (300 MHz, DMSO-$d_6$) δ 7.86 (t, J=1.0 Hz, 1H), 7.56 (d, J=1.1 Hz, 1H), 7.31-7.21 (m, 3H), 7.05 (d, J=7.9 Hz, 1H), 6.93 (td, J=7.4, 1.1 Hz, 1H), 5.29 (s, 2H), 4.01 (q, J=7.1 Hz, 2H), 3.66 (s, 2H), 1.08 (t, J=7.1 Hz, 3H).

Step-6: Preparation of Ethyl 2-(2-((4-(3-(aminomethyl)phenyl)-2-chlorobenzofuran-6-yl)methoxy)phenyl)acetate (225g)

Compound 225g was prepared according to the procedure reported in step-3 of Scheme-1 from ethyl 2-(2-((2-chloro-4-(((trifluoromethyl)sulfonyl)oxy)benzofuran-6-yl)methoxy)phenyl)acetate (225f) (280 mg, 0.568 mmol) in dioxane (5 mL) using 3-(aminomethyl)phenylboronic acid hydrochloride (6c) (102 mg, 0.676 mmol), a solution of K₂CO₃ (280 mg, 2.026 mmol) in water (0.5 mL), Pd(PPh₃)₂Cl₂ (62 mg, 0.088 mmol) and heating under an Ar atmosphere at 100° C. for 3 h. This gave after workup, purification by flash column chromatography (silica gel 12 g, eluting with DMA80 in DCM from 0-70%) ethyl 2-(2-((4-(3-(aminomethyl)phenyl)-2-chlorobenzofuran-6-yl)methoxy)phenyl)acetate (225g) (137 mg, 54% yield) as a transparent oil. $^1$H NMR (300 MHz, Chloroform-d) δ 7.61-7.44 (m, 4H), 7.44-7.34 (m, 2H), 7.32-7.21 (m, 2H), 6.98 (ddd, J=8.8, 5.7, 1.5 Hz, 2H), 6.78 (d, J=1.0 Hz, 1H), 5.23 (s, 2H), 4.10 (q, J=7.1 Hz, 2H), 3.98 (s, 2H), 3.72 (s, 2H), 1.17 (t, J=7.1 Hz, 3H); MS (ES+): 450.2 (M+1).

Step-7: Preparation of 2-(2-((4-(3-(aminomethyl)phenyl)-2-chlorobenzofuran-6-yl)methoxy)phenyl) acetic Acid (225h)

Compound 225h was prepared according to the procedure reported in step-6 of Scheme-1, from ethyl 2-(2-((4-(3-(aminomethyl)phenyl)-2-chlorobenzofuran-6-yl)methoxy)phenyl)acetate (225g) (137 mg, 0.304 mmol) in MeOH/THF (6 mL) using a solution of lithium hydroxide (62 mg, 1.478 mmol) in water (2 mL). This gave after workup and purification by reverse phase column (C18, 100 g, 0-60% MeCN in H₂O containing 0.1% HCl) 2-(2-((4-(3-(aminomethyl)phenyl)-2-chlorobenzofuran-6-yl)methoxy)phenyl)acetic acid (225h) (51 mg, 40% yield) HCl salt as a white solid. $^1$H NMR (300 MHz, DMSO-$d_6$, D₂O exchange) δ 7.74 (s, 1H), 7.62 (d, J=8.4 Hz, 2H), 7.50 (s, 3H), 7.27 (s, 1H), 7.16 (d, J=7.2 Hz, 2H), 7.00 (d, J=8.3 Hz, 1H), 6.84 (t, J=7.4 Hz, 1H), 5.22 (s, 2H), 4.07 (s, 2H), 3.55 (s, 2H); MS (ES+): 422.1 (M+1); MS(ES−): 420.2 (M−1).

Scheme-226

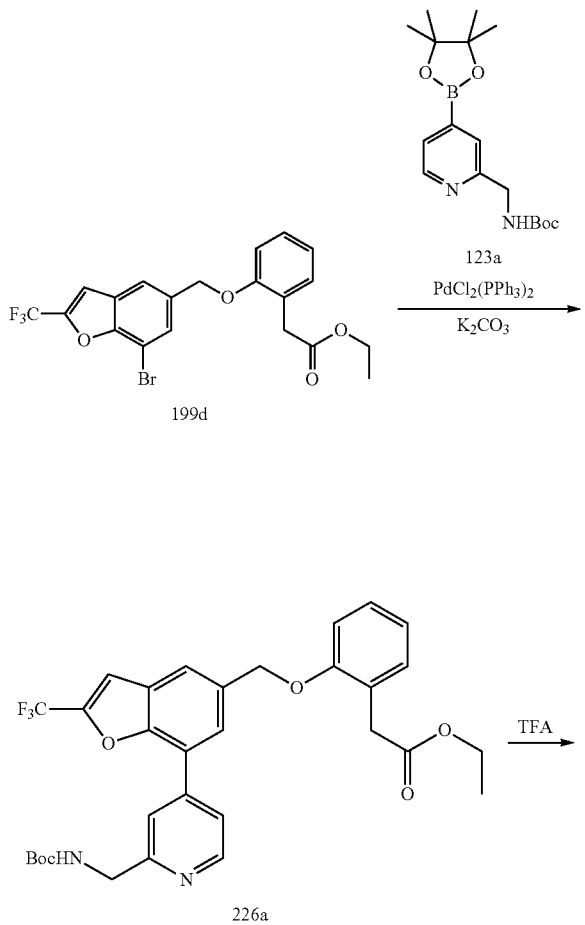

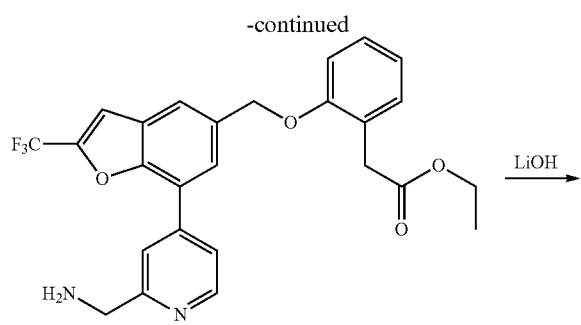

226b

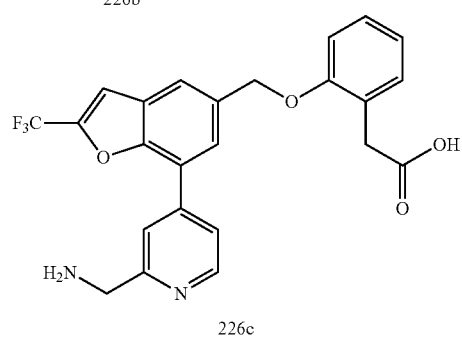

226c

Preparation of 2-(2-((7-(2-(aminomethyl)pyridin-4-yl)-2-(trifluoromethyl)benzofuran-5-yl)methoxy)phenyl)acetic Acid (226c)

Step-1: Preparation of Ethyl 2-(2-((7-(2-(((tert-butoxycarbonyl)amino)methyl)pyridin-4-yl)-2-(trifluoromethyl)benzofuran-5-yl)methoxy)phenyl)acetate (226a)

Compound 226a was prepared according to the procedure reported in step-3 of Scheme-1 from ethyl 2-(2-((7-bromo-2-(trifluoromethyl)benzofuran-5-yl)methoxy)phenyl)acetate (199d) (229 mg, 0.501 mmol) in dioxane (5 mL) using tert-butyl ((4-(4,4,5,5-tetramethyl-1,3,2-dioxaborolan-2-yl)pyridin-2-yl)methyl)carbamate (123a) (259 mg, 0.775 mmol), a solution of K$_2$CO$_3$ (214 mg, 1.548 mmol) in water (0.5 mL), bis(triphenylphosphine)palladium(II) chloride (62 mg, 0.088 mmol) and heating at 100° C. for 3h on oil bath. This gave after workup, purification by flash column chromatography [silica gel (12 g), eluting with ethyl acetate in hexanes from 20-100%] ethyl 2-(2-((7-(2-(((tert-butoxycarbonyl)amino)methyl)pyridin-4-yl)-2-(trifluoromethyl)benzofuran-5-yl)methoxy)phenyl)acetate (226a) (166 mg, 57% yield) as a pale-yellow oil. $^1$H NMR (300 MHz, Chloroform-d) δ 8.71 (dd, J=5.3, 0.9 Hz, 1H), 7.90-7.65 (m, 4H), 7.38-7.18 (m, 4H), 7.07-6.86 (m, 2H), 5.28 (s, 2H), 4.60 (d, J=5.5 Hz, 2H), 4.13-4.04 (m, 2H), 3.72 (s, 2H), 1.47 (s, 9H), 1.15 (t, J=7.1 Hz, 3H); $^{19}$F NMR (282 MHz, Chloroform-d) δ-64.74; MS(ES+): 585.3 (M+1).

Step-2: Preparation of Ethyl 2-(2-((7-(2-(aminomethyl)pyridin-4-yl)-2-(trifluoromethyl)benzofuran-5-yl)methoxy)phenyl)acetate (226b)

Compound 226b was prepared according to the procedure reported in step-5 of Scheme-1 from ethyl 2-(2-((7-(2-(((tert-butoxycarbonyl)amino)methyl)pyridin-4-yl)-2-(trifluoromethyl)benzofuran-5-yl)methoxy)phenyl)acetate (226a) (166 mg, 0.284 mmol) in DCM (5 mL) using TFA (0.3 mL, 3.89 mmol). This gave after workup and purification by flash column chromatography [silica gel 12 g, eluting with DMA80/DCM, from 0-80%] ethyl 2-(2-((7-(2-(aminomethyl)pyridin-4-yl)-2-(trifluoromethyl)benzofuran-5-yl)methoxy)phenyl)acetate (226b) (112 mg, 81% yield) as a pale-yellow oil; MS (ES+): 485.2 (M+1); MS(ES−): 483.2 (M−1).

Step-3: Preparation of 2-(2-((7-(2-(aminomethyl)pyridin-4-yl)-2-(trifluoromethyl)benzofuran-5-yl)methoxy)phenyl)acetic Acid (226c)

Compound 226c was prepared according to the procedure reported in step-6 of Scheme-1 from ethyl 2-(2-((7-(2-(aminomethyl)pyridin-4-yl)-2-(trifluoromethyl)benzofuran-5-yl)methoxy)phenyl)acetate (226b) (112 mg, 0.231 mmol) in MeOH/THF (6 mL each) using a solution of lithium hydroxide monohydrate (63 mg, 1.50 mmol) in water (2.0 mL). This gave after workup and purification by reverse phase column [C18 (50 g), eluting with ACN in water (containing 0.1% HCl) from 0-100%] 2-(2-((7-(2-(aminomethyl)pyridin-4-yl)-2-(trifluoromethyl)benzofuran-5-yl)methoxy)phenyl)acetic acid (226c) (58 mg, 55% yield) HCl salt as a white solid. $^1$H NMR (300 MHz, DMSO-d$_6$) δ 8.85 (d, J=5.3 Hz, 1H), 8.67 (s, 3H), 8.11 (d, J=1.7 Hz, 1H), 8.05 (s, 2H), 8.00 (dd, J=5.3, 1.7 Hz, 1H), 7.94 (d, J=1.4 Hz, 1H), 7.31-7.20 (m, 2H), 7.11 (d, J=8.0 Hz, 1H), 7.00-6.87 (m, 1H), 5.34 (s, 2H), 4.34 (d, J=5.6 Hz, 2H), 3.63 (s, 2H); $^{19}$F NMR (282 MHz, DMSO-d$_6$) δ−63.34. MS (ES+): 457.2 (M+1); MS(ES−): 455.2 (M−1). HPLC purity 99.24%.

Scheme-227

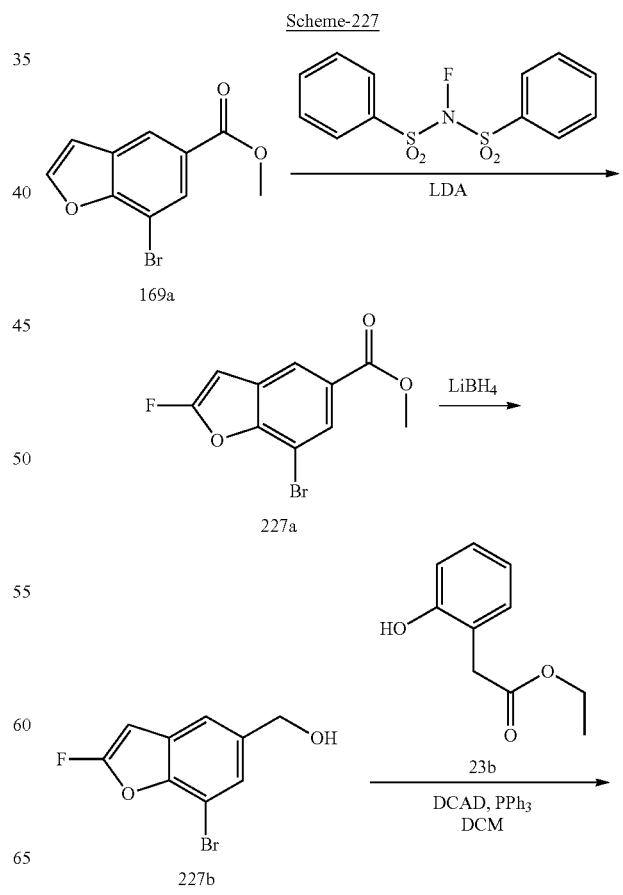

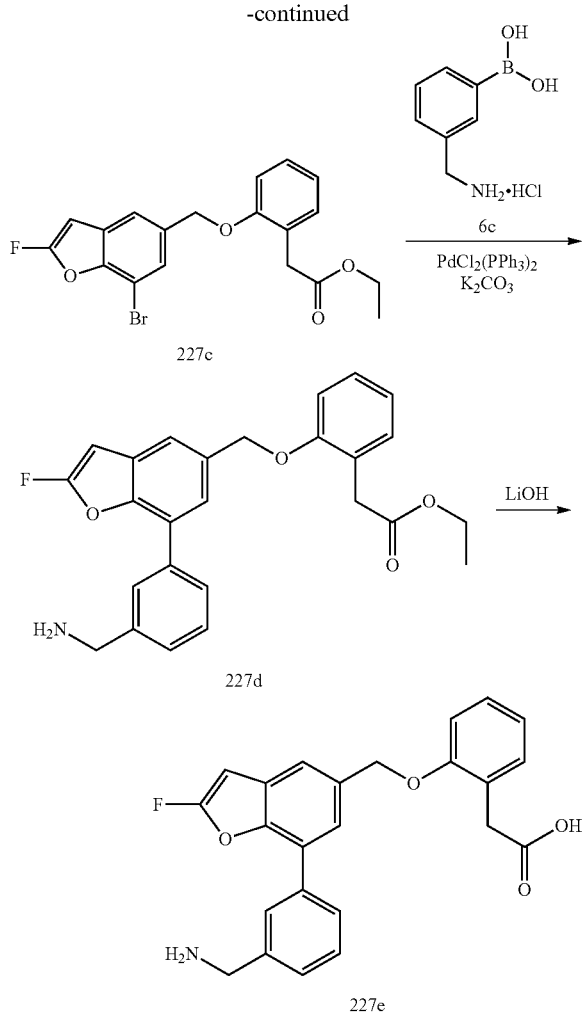

Preparation of 2-(2-((7-(3-(aminomethyl)phenyl)-2-fluorobenzofuran-5-yl)methoxy)phenyl)acetic Acid (227e)

Step-1: Preparation of methyl 7-bromo-2-fluorobenzofuran-5-carboxylate (227a)

To a stirred solution of methyl 7-bromobenzofuran-5-carboxylate (169a) (5 g, 19.60 mmol) in dry THF (90 mL) at −78° C. under $N_2$ was added dropwise LDA (19.6 mL, 1.5 M, 29.4 mmol). The mixture was kept at −78° C. for 1.5 h followed by the addition of a solution of N-fluoro-N-(phenylsulfonyl)benzenesulfonamide (12.5 g, 39.6 mmol) in THF (60 mL). The mixture was slowly warmed to room temperature and stirred overnight. The reaction was quenched with saturated $NH_4Cl$ aqueous solution and extracted with ethyl acetate. The organic layers were combined, washed with brine, dried over $Na_2SO_4$ and concentrated. The residue was purified by flash column chromatography [silica (40 g), eluting with ethyl acetate/hexanes, 0-40%] to afford methyl 7-bromo-2-fluorobenzofuran-5-carboxylate (227a) (453 mg, 9% yield) as a yellow solid. $^1$H NMR (300 MHz, DMSO-$d_6$) δ 8.24 (d, J=1.6 Hz, 1H), 8.06 (d, J=1.6 Hz, 1H), 6.64 (d, J=6.5 Hz, 1H), 3.89 (s, 3H); $^{19}$F NMR (282 MHz, DMSO-$d_6$) δ−109.09.

Step-2: Preparation of (7-bromo-2-fluorobenzofuran-5-yl)methanol (227b)

Compound 227b was prepared according to the procedure reported in step-2 of Scheme-76 from methyl 7-bromo-2-fluorobenzofuran-5-carboxylate (227a) (495 mg, 1.813 mmol) in THF (15 mL) using $LiBH_4$ (1.45 mL, 5.80 mmol) and MeOH (0.225 mL, 5.56 mmol). This gave after workup and purification by flash column chromatography [silica (12 g), eluting with EtOAc in hexane from 0-50%] followed by purification using reverse phase column chromatography [C18 (50 g), eluting with ACN in water (containing 0.1% HCl) from 0-100%] (7-bromo-2-fluorobenzofuran-5-yl)methanol (227b) (90 mg, 20% yield) as a white solid; $^1$H NMR (300 MHz, Chloroform-d) δ 7.46-7.25 (m, 2H), 5.89 (d, J=6.6 Hz, 1H), 4.65 (s, 2H), 2.84 (s, 1H); $^{19}$F NMR (282 MHz, Chloroform-d) 6-109.55.

Step-3: Preparation of Ethyl 2-(2-((7-bromo-2-fluorobenzofuran-5-yl)methoxy)phenyl)acetate (227c)

Compound 227c was prepared according to the procedure reported in step-2 of Scheme-23 from (7-bromo-2-fluorobenzofuran-5-yl)methanol (227b) (90 mg, 0.367 mmol) in DCM (8 mL) using triphenylphosphine (107 mg, 0.408 mmol), ethyl 2-(2-hydroxyphenyl) acetate (23b) (91 mg, 0.505 mmol) and di-(4-chlorobenzyl)azodicarboxylate (DCAD, 162 mg, 0.441 mmol) in DCM (2 mL). This gave after workup and purification by flash column chromatography [silica (12 g), eluting with EtOAc in hexane from 0-40%] ethyl 2-(2-((7-bromo-2-fluorobenzofuran-5-yl)methoxy)phenyl)acetate (227c) (116 mg, 78% yield) as a white solid. $^1$H NMR (300 MHz, Chloroform-d) δ 7.51 (p, J=0.9 Hz, 2H), 7.28 (t, J=7.6 Hz, 2H), 7.05-6.89 (m, 2H), 5.97 (d, J=6.6 Hz, 1H), 5.12 (s, 2H), 4.17 (q, J=7.1 Hz, 2H), 3.71 (s, 2H), 1.24 (t, J=7.1 Hz, 3H); $^{19}$F NMR (282 MHz, Chloroform-d) 6-109.43.

Step-4: Preparation of Ethyl 2-(2-((7-(3-(aminomethyl)phenyl)-2-fluorobenzofuran-5-yl)methoxy)phenyl)acetate (227d)

Compound 227d was prepared according to the procedure reported in step-3 of Scheme-1 from ethyl 2-(2-((7-bromo-2-fluorobenzofuran-5-yl)methoxy)phenyl)acetate (227c) (116 mg, 0.285 mmol) in dioxane (5 mL) using 3-(aminomethyl)phenylboronic acid hydrochloride (6c) (60 mg, 0.397 mmol), a solution of $K_2CO_3$ (121 mg, 0.876 mmol) in water (0.5 mL), bis(triphenylphosphine)palladium(II) chloride (32 mg, 0.046 mmol) and heating at 100° C. for 3h on oil bath. This gave after workup, purification by flash column chromatography [silica (24 g), eluting with DMA80 in DCM from 0-90%] ethyl 2-(2-((7-(3-(aminomethyl)phenyl)-2-fluorobenzofuran-5-yl)methoxy)phenyl)acetate (227d) (48 mg, 39% yield) as a pale-yellow oil. $^1$H NMR (300 MHz, Chloroform-d) δ 7.76-7.53 (m, 2H), 7.39 (dt, J=8.0, 1.6 Hz, 3H), 7.27 (dd, J=7.1, 1.8 Hz, 1H), 7.15 (m, 3H), 6.86 (t, J=7.0 Hz, 2H), 5.82 (dd, J=6.6, 1.8 Hz, 1H), 5.09 (d, J=3.0 Hz, 2H), 4.06-3.79 (m, 4H), 3.59 (s, 2H), 1.02 (t, J=7.1 Hz, 3H); $^{19}$F NMR (282 MHz, Chloroform-d) 6-110.82. MS (ES+): 434.2 (M+1).

Step-5: Preparation of 2-(2-((7-(3-(aminomethyl)phenyl)-2-fluorobenzofuran-5-yl)methoxy)phenyl) acetic Acid (227e)

Compound 227e was prepared according to the procedure reported in step-6 of Scheme-1, from ethyl 2-(2-((7-(3-

(aminomethyl)phenyl)-2-fluorobenzofuran-5-yl)methoxy)phenyl)acetate (227d) (48 mg, 0.111 mmol) in MeOH/THF (4 mL each) using a solution of lithium hydroxide monohydrate (32 mg, 0.763 mmol) in water (1.6 mL). This gave after workup and purification by reverse phase column [C18 (50 g), eluting with ACN in water (containing 0.1% HCl) from 0-100%] 2-(2-((7-(3-(aminomethyl)phenyl)-2-fluorobenzofuran-5-yl)methoxy)phenyl)acetic acid (227e) (25 mg, 56% yield) as a white solid. $^1$H NMR (300 MHz, DMSO-$d_6$) δ 8.56 (s, 3H), 7.89 (d, J=1.6 Hz, 1H), 7.82-7.74 (m, 1H), 7.59 (dd, J=14.2, 1.7 Hz, 2H), 7.55-7.49 (m, 2H), 7.17 (dd, J=8.2, 6.5 Hz, 2H), 7.06-6.98 (m, 1H), 6.84 (td, J=7.4, 1.1 Hz, 1H), 6.37 (d, J=6.4 Hz, 1H), 5.19 (s, 2H), 4.06 (s, 2H), 3.53 (s, 2H); $^{19}$F NMR (282 MHz, DMSO-$d_6$) δ−111.56. MS (ES+): 406.1 (M+1); MS (ES−): 404.2 (M−1). HPLC purity 97.63%.

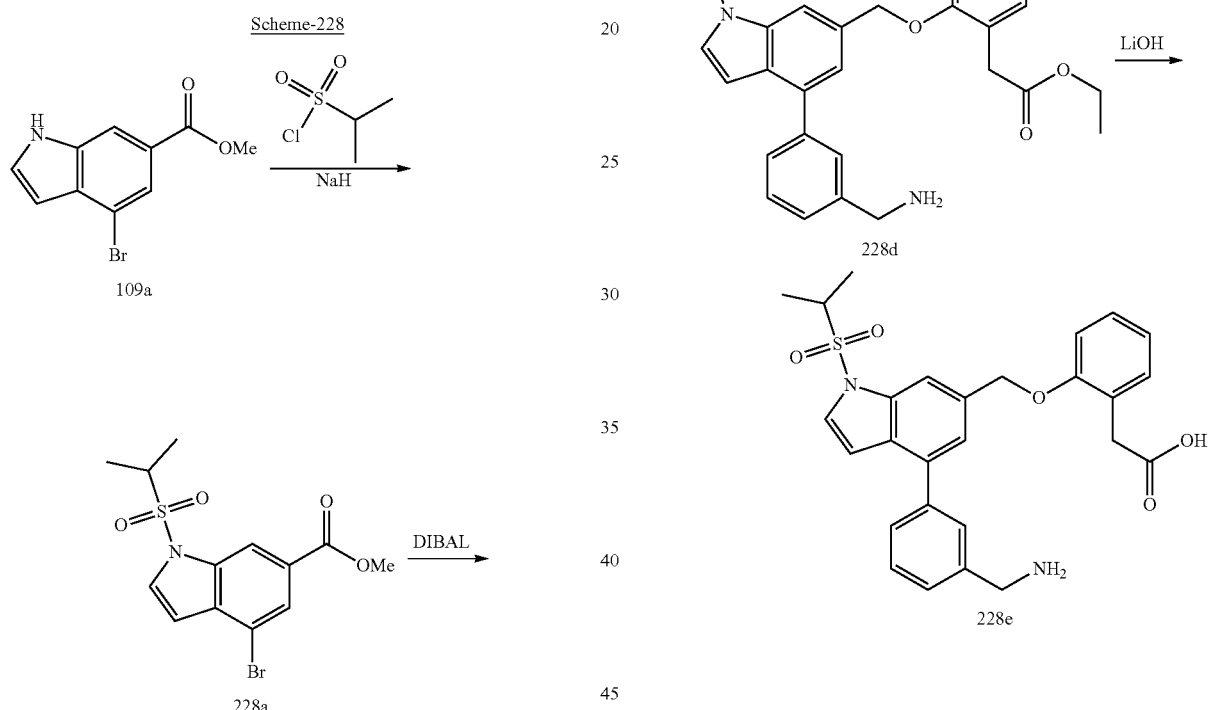

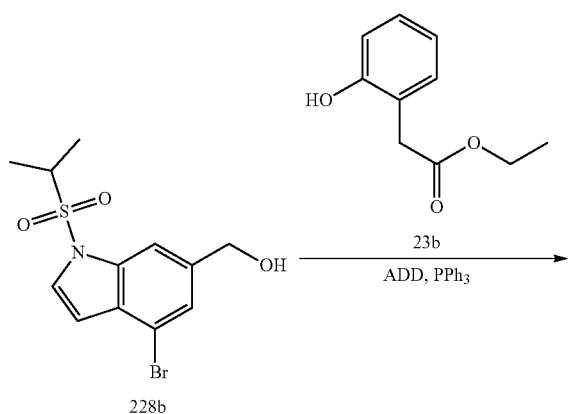

Preparation of 2-(2-((4-(3-(aminomethyl)phenyl)-1-(isopropylsulfonyl)-1H-indol-6-yl)methoxy)phenyl) acetic Acid (228e)

Step-1: Preparation of methyl 4-bromo-1-(isopropylsulfonyl)-1H-indole-6-carboxylate (228a)

Compound 228a was prepared according to the procedure reported in step-1 of Scheme-40 from methyl 4-bromo-1H-indole-6-carboxylate (109a) (2 g, 7.87 mmol) in DMF (25 mL) using NaH (60% in mineral oil, 0.94 g, 23.61 mmol) and propane-2-sulfonyl chloride (2.66 mL, 23.61 mmol). This gave after work-up and purification by flash column chromatography [silica (24 g), eluting with EtOAc/MeOH=9:1 in Hexane from 0-50%] methyl 4-bromo-1-(isopropylsulfonyl)-1H-indole-6-carboxylate (228a) (2.79 g, 98% yield) as a white solid; $^1$H NMR (300 MHz, DMSO-$d_6$) δ 8.46 (t, J=1.1 Hz, 1H), 8.04 (d, J=1.2 Hz, 1H), 7.99 (d, J=3.7 Hz, 1H), 6.91 (dd, J=3.7, 0.9 Hz, 1H), 3.99-3.92 (m, 1H), 3.91 (s, 3H), 1.22 (d, J=6.8 Hz, 6H); MS (ES+): 360.0, 362.0 (M+1); MS (ES−): 358.1, 360.2 (M−1).

Step-2: Preparation of (4-bromo-1-(isopropylsulfonyl)-1H-indol-6-yl)methanol (228b)

Compound 228b was prepared according to the procedure reported in step-2 of Scheme-212 from methyl 4-bromo-1-(isopropylsulfonyl)-1H-indole-6-carboxylate (228a) (1 g, 2.79 mmol) in dichloromethane (10 mL) using diisobutylaluminum hydride (1M solution in dichloromethane) (6.98 mL, 6.98 mmol). This gave after workup (4-bromo-1-(isopropylsulfonyl)-1H-indol-6-yl)methanol (228b) (0.88 g, 95% yield) as a white crystalline solid; $^1$H NMR (300 MHz, DMSO-$d_6$) δ 7.85 (p, J=0.9 Hz, 1H), 7.69 (d, J=3.7 Hz, 1H), 7.49 (dd, J=1.2, 0.6 Hz, 1H), 6.75 (dd, J=3.7, 0.8 Hz, 1H), 5.43 (t, J=5.9 Hz, 1H), 4.62 (dt, J=5.9, 0.7 Hz, 2H), 3.91-3.70 (m, 1H), 1.29-1.09 (m, 6H).

Step-3: Preparation of Ethyl 2-(2-((4-bromo-1-(isopropylsulfonyl)-1H-indol-6-yl)methoxy)phenyl)acetate (228c)

Compound 228c was prepared according to the procedure reported in step-2 of Scheme-23 from (4-bromo-1-(isopropylsulfonyl)-1H-indol-6-yl)methanol (228b) (0.88 g, 2.65 mmol) in toluene (15 mL) using triphenylphosphine (0.90 g, 3.44 mmol), ethyl 2-(2-hydroxyphenyl) acetate (23b) (0.621 g, 3.44 mmol) and (E)-diazene-1,2-diylbis(piperidin-1-ylmethanone) (0.87 g, 3.44 mmol) in toluene (15 mL). This gave after workup and purification by flash column chromatography [silica (24 g), eluting with EtOAc/MeOH (9:1) in hexane from 0-10% for 40 min, then 10%-50%] ethyl 2-(2-((4-bromo-1-(isopropylsulfonyl)-1H-indol-6-yl)methoxy)phenyl)acetate (228c) (1.15 g, 88% yield) as a yellow oil; MS (ES−): 493.2, 495.2 (M−1).

Step-4: Preparation of Ethyl 2-(2-((4-(3-(aminomethyl)phenyl)-1-(isopropylsulfonyl)-1H-indol-6-yl)methoxy)phenyl)acetate (228d)

Compound 228d was prepared according to the procedure reported in step-3 of Scheme-1 from ethyl 2-(2-((4-bromo-1-(isopropylsulfonyl)-1H-indol-6-yl)methoxy)phenyl)acetate (228c) (0.24 g, 0.49 mmol) in dioxane (4 mL) using 3-(aminomethyl)phenylboronic acid hydrochloride (6c) (0.14 g, 0.73 mmol), K$_2$CO$_3$ (0.13 g, 0.97 mmol) in water (2 mL) and bis(triphenylphosphine)palladium(ll)chloride (0.051 g, 0.073 mmol) under an Ar atmosphere and heating at 90° C. for 3 h on oil bath. This gave after workup and purification by reverse phase column chromatography [C18 (50 g), eluting with ACN in water (containing 0.1% HCl) from 0-100%] ethyl 2-(2-((4-(3-(aminomethyl)phenyl)-1-(isopropylsulfonyl)-1H-indol-6-yl)methoxy)phenyl)acetate (228d) (0.12 g, 48% yield) HCl salt as a white solid; $^1$H NMR (300 MHz, DMSO-$d_6$) δ 8.39 (s, 3H), 7.98 (s, 1H), 7.78 (s, 1H), 7.72 (dd, J=3.8, 0.9 Hz, 1H), 7.70-7.50 (m, 3H), 7.50-7.43 (m, 1H), 7.32-7.17 (m, 2H), 7.12 (d, J=8.2 Hz, 1H), 7.02 (d, J=3.8 Hz, 1H), 6.91 (t, J=7.3 Hz, 1H), 5.30 (s, 2H), 4.13 (s, 2H), 3.96-3.86 (m, 2H), 3.86-3.77 (m, 1H), 3.62 (s, 2H), 1.21 (d, J=6.7 Hz, 6H), 0.96 (t, J=7.1 Hz, 3H); MS (ES+): 521.3 (M+1), MS (ES−): 519.3 (M−1).

Step-5: Preparation of 2-(2-((4-(3-(aminomethyl)phenyl)-1-(isopropylsulfonyl)-1H-indol-6-yl)methoxy)phenyl)acetic Acid (228e)

Compound 228e was prepared according to the procedure reported in step-6 of Scheme-1 from ethyl 2-(2-((4-(3-(aminomethyl)phenyl)-1-(isopropylsulfonyl)-1H-indol-6-yl)methoxy)phenyl)acetate (228d) (0.09 g, 0.16 mmol) in MeOH/THF (4 mL, 1:1) using a solution of lithium hydroxide hydrate (0.06 g, 1.31 mmol) in water (1 mL). This gave after workup and purification by reverse phase column chromatography [C18 (50 g), eluting with ACN in water (containing 0.1% HCl) from 0-100%] 2-(2-((4-(3-(aminomethyl)phenyl)-1-(isopropylsulfonyl)-1H-indol-6-yl)methoxy)phenyl)acetic acid (228e) (0.05 g, 56% yield) HCl salt as a white solid; $^1$H NMR (300 MHz, DMSO-$d_6$) δ 12.16 (s, 1H), 8.38 (s, 3H), 8.00 (s, 1H), 7.79 (s, 1H), 7.71 (d, J=3.7 Hz, 1H), 7.67 (dt, J=7.4, 1.7 Hz, 1H), 7.60 (d, J=7.5 Hz, 1H), 7.58-7.54 (m, 1H), 7.51 (d, J=1.2 Hz, 1H), 7.24 (t, J=7.7 Hz, 2H), 7.11 (d, J=8.1 Hz, 1H), 7.01 (d, J=3.8 Hz, 1H), 6.91 (td, J=7.4, 1.1 Hz, 1H), 5.32 (s, 2H), 4.14 (s, 2H), 3.83 (q, J=6.8 Hz, 1H), 3.60 (s, 2H), 1.21 (d, J=6.7 Hz, 6H); MS (ES+): 493.2 (M+1), MS (ES−): 491.3 (M−1).

Scheme-229

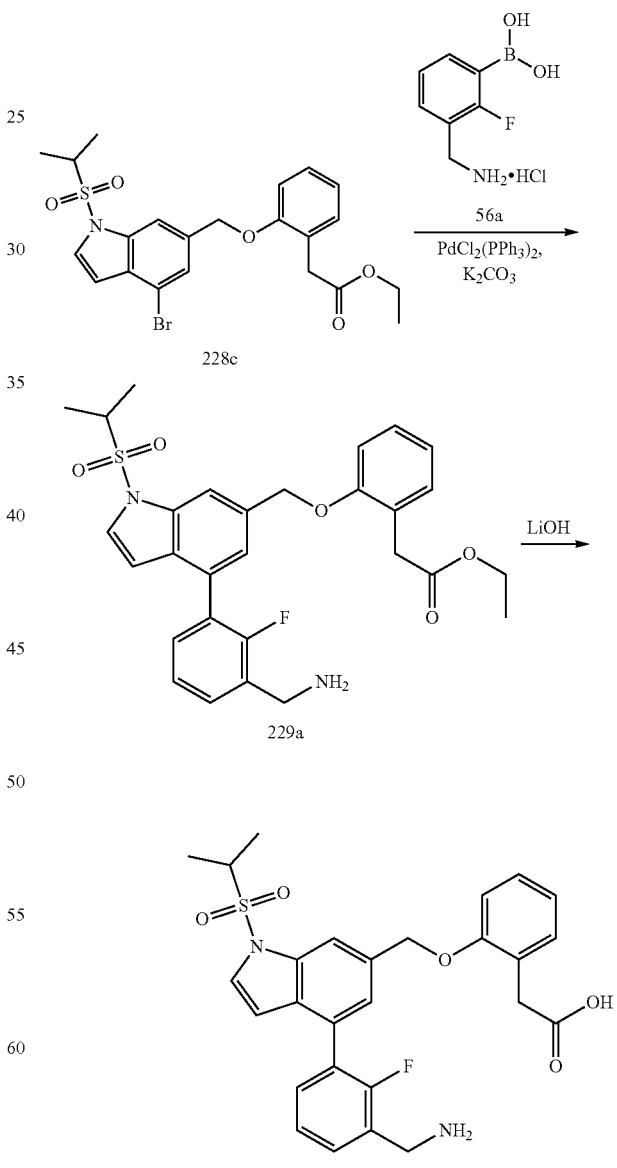

813

Preparation of 2-(2-((4-(3-(aminomethyl)-2-fluorophenyl)-1-(isopropylsulfonyl)-1H-indol-6-yl)methoxy)phenyl)acetic Acid (229b)

Step-1: Preparation of Ethyl 2-(2-((4-(3-(aminomethyl)-2-fluorophenyl)-1-(isopropylsulfonyl)-1H-indol-6-yl)methoxy)phenyl)acetate (229a)

Compound 229a was prepared according to the procedure reported in step-3 of Scheme-1 from ethyl 2-(2-((4-bromo-1-(isopropylsulfonyl)-1H-indol-6-yl)methoxy)phenyl)acetate (228c) (0.24 g, 0.49 mmol) in dioxane (4 mL) using (3-(aminomethyl)-2-fluorophenyl)boronic acid hydrochloride (56a) (0.15 g, 0.73 mmol), $K_2CO_3$ (0.13 g, 0.97 mmol) in water (2 mL) and bis(triphenylphosphine)palladium(ll) chloride (0.051 g, 0.073 mmol) under an Ar atmosphere and heating at 90° C. for 3 h on oil bath. This gave after workup and purification by flash column chromatography [silica (12 g), eluting with MeOH in DCM from 0-50%] ethyl 2-(2-((4-(3-(aminomethyl)-2-fluorophenyl)-1-(isopropylsulfonyl)-1H-indol-6-yl)methoxy)phenyl)acetate (229a) (0.14 g, 54% yield) as a white solid; $^1H$ NMR (300 MHz, DMSO-$d_6$) δ 7.98 (s, 1H), 7.65 (d, J=3.7 Hz, 1H), 7.58 (td, J=7.2, 2.0 Hz, 1H), 7.43-7.35 (m, 2H), 7.35-7.18 (m, 3H), 7.13 (dd, J=8.3, 1.1 Hz, 1H), 6.91 (td, J=7.4, 1.1 Hz, 1H), 6.61 (t, J=3.3 Hz, 1H), 5.28 (s, 2H), 3.93-3.78 (m, 5H), 3.61 (s, 2H), 1.21 (d, J=6.7 Hz, 6H), 0.95 (t, J=7.1 Hz, 3H); MS (ES+): 539.3 (M+1), MS (ES−): 537.3 (M−1). HPLC purity: 96.40%.

Step-2: Preparation of 2-(2-((4-(3-(aminomethyl)-2-fluorophenyl)-1-(isopropylsulfonyl)-1H-indol-6-yl)methoxy)phenyl)acetic Acid (229b)

Compound 229b was prepared according to the procedure reported in step-6 of Scheme-1 from ethyl 2-(2-((4-(3-(aminomethyl)-2-fluorophenyl)-1-(isopropylsulfonyl)-1H-indol-6-yl)methoxy)phenyl)acetate (229a) (0.2 g, 0.37 mmol) in MeOH/THF (4 mL, 1:1) using a solution of lithium hydroxide hydrate (0.13 g, 2.97 mmol) in water (1 mL). This gave after workup and purification by reverse phase column chromatography [C18 (50 g), eluting with ACN in water (containing 0.1% HCl) from 0-100%] 2-(2-((4-(3-(aminomethyl)-2-fluorophenyl)-1-(isopropylsulfonyl)-1H-indol-6-yl)methoxy)phenyl)acetic acid (229b) (0.12 g, 63% yield) HCl salt as a white solid; $^1H$ NMR (300 MHz, DMSO-$d_6$) δ 8.49 (s, 3H), 8.04 (t, J=1.0 Hz, 1H), 7.69 (d, J=3.7 Hz, 1H), 7.68-7.55 (m, 2H), 7.48-7.37 (m, 2H), 7.28-7.18 (m, 2H), 7.15-7.07 (m, 1H), 6.91 (td, J=7.4, 1.1 Hz, 1H), 6.75 (t, J=3.5 Hz, 1H), 5.32 (s, 2H), 4.16 (s, 2H), 3.85 (p, J=6.7 Hz, 1H), 3.58 (s, 2H), 1.21 (d, J=6.8 Hz, 6H); $^{19}F$ NMR (282 MHz, DMSO-$d_6$) δ−118.54; MS (ES+): 511.2 (M+1), MS (ES−): 509.3 (M−1).

Scheme-230

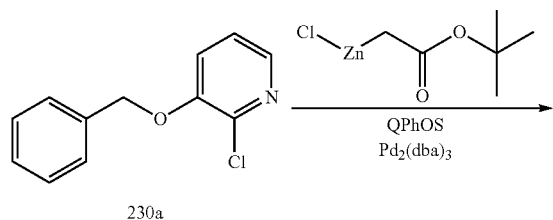

230a

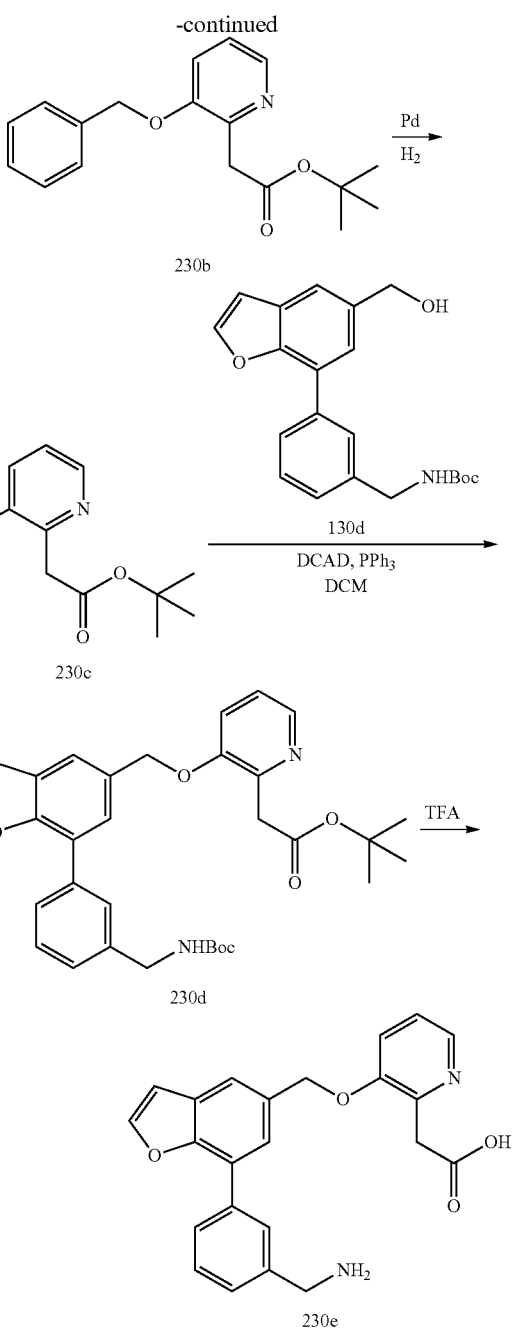

Preparation of 2-(3-((7-(3-(aminomethyl)phenyl)benzofuran-5-yl)methoxy)pyridin-2-yl)acetic Acid (230e)

Step-1: Preparation of tert-butyl 2-(3-(benzyloxy)pyridin-2-yl)acetate (230b)

Compound 230b was prepared according to the procedure reported in step-2 of Scheme-163 from 3-(benzyloxy)-2-chloropyridine (230a) (0.3 g, 1.366 mmol; CAS #108082-72-0) in THF (5 mL) using $Pd_2(dba)_3$ (0.125 g, 0.137 mmol), Q-Phos (0.097 g, 0.137 mmol) and (2-tert-butoxy-2-oxoethyl)zinc(II) chloride (0.5 M solution in ether) (5.46 mL, 2.73 mmol). This gave after workup and purification by flash column chromatography [silica gel 24 g, eluting with ethyl acetate in hexanes (0-40 to 100%)] tert-butyl 2-(3-(benzyloxy)pyridin-2-yl)acetate (230b) (165 mg, 40% yield) as an oil; ¹H NMR (300 MHz, DMSO-d₆) δ 8.06 (dd, J=4.8, 1.3 Hz, 1H), 7.48-7.41 (m, 4H), 7.40 (d, J=0.9 Hz, 1H), 7.38-7.32 (m, 1H), 7.28 (dd, J=8.3, 4.7 Hz, 1H), 5.16 (s, 2H), 3.72 (s, 2H), 1.33 (s, 9H); MS (ES+): 300.2 (M+1).

Step-2: Preparation of tert-butyl 2-(3-hydroxypyridin-2-yl)acetate (230c)

To a solution of tert-butyl 2-(3-(benzyloxy)pyridin-2-yl)acetate (230b) (160 mg, 0.534 mmol) in ethyl acetate (20 mL) was added Pd/C (10% on carbon, 57 mg, 0.053 mmol) and hydrogenated with balloon pressure for 3 h. The reaction mixture was filtered through a pad of Celite and concentrated in vacuum to afford tert-butyl 2-(3-hydroxypyridin-2-yl)acetate (230c) (112 mg, 100% yield) as a light pink solid; ¹H NMR (300 MHz, DMSO-d₆) δ 9.93 (s, 1H), 7.93 (dd, J=4.1, 2.0 Hz, 1H), 7.18-7.03 (m, 2H), 3.61 (s, 2H), 1.39 (s, 9H); MS (ES+) 210.1 (M+1), (ES−) 208.3 (M−1).

Step-3: Preparation of tert-butyl 2-(3-((7-(3-(((tert-butoxycarbonyl)amino)methyl)phenyl)benzofuran-5-yl)methoxy)pyridin-2-yl)acetate (230d)

Compound 230d was prepared according to the procedure reported in step-2 of Scheme-23 from tert-butyl 3-(5-(hydroxymethyl)benzofuran-7-yl)benzylcarbamate (130d) 169 mg, 0.478 mmol) in DCM (10 mL) using triphenylphosphine (144 mg, 0.550 mmol), tert-butyl 2-(3-hydroxypyridin-2-yl)acetate (230c) (115 mg, 0.550 mmol) and a solution of di-(4-chlorobenzyl)azodicarboxylate (DCAD, 211 mg, 0.573 mmol) in DCM (5 mL). This gave after workup and purification by flash column chromatography [silica gel 24 g, eluting with ethyl acetate in hexanes from 0-50%] tert-butyl 2-(3-((7-(3-(((tert-butoxycarbonyl)amino)methyl)phenyl)benzofuran-5-yl)methoxy)pyridin-2-yl)acetate (230d) (250 mg, 96% yield) as a colorless oil; ¹H NMR (300 MHz, DMSO-d₆) δ 8.10-8.02 (m, 2H), 7.76-7.70 (m, 3H), 7.56 (dd, J=13.9, 1.5 Hz, 1H), 7.52-7.42 (m, 3H), 7.29 (dd, J=8.1, 4.7 Hz, 2H), 7.04 (d, J=2.2 Hz, 1H), 5.30 (s, 2H), 4.22 (d, J=6.2 Hz, 2H), 3.72 (s, 2H), 1.39 (d, J=1.1 Hz, 9H), 1.24 (s, 9H); MS (ES+): 545.3 (M+1), 567.3 (M+Na).

Step-4: Preparation of 2-(3-((7-(3-(aminomethyl)phenyl)benzofuran-5-yl)methoxy)pyridin-2-yl)acetic Acid (230e)

Compound 230e was prepared according to the procedure reported in step-5 of Scheme-1 from tert-butyl 2-(3-((7-(3-(((tert-butoxycarbonyl)amino)methyl)phenyl)benzofuran-5-yl)methoxy)pyridin-2-yl)acetate (230d) (245 mg, 0.450 mmol) in DCM (5 mL) using TFA (0.347 mL, 4.50 mmol). This gave after workup and purification by reverse phase column chromatography [C18 (50 g), eluting with ACN in water (containing 0.1% HCl) from 0-100%] 2-(3-((7-(3-(aminomethyl)phenyl)benzofuran-5-yl)methoxy)pyridin-2-yl)acetic acid (230e) (200 mg, 96% yield) HCl salt as a white solid; ¹H NMR (300 MHz, Methanol-d₄) δ 8.40-8.32 (m, 2H), 8.05 (s, 1H), 7.99 (dt, J=7.7, 1.5 Hz, 1H), 7.93 (dd, J=8.7, 5.7 Hz, 1H), 7.89 (d, J=2.2 Hz, 1H), 7.78 (d, J=1.7 Hz, 1H), 7.70 (d, J=1.7 Hz, 1H), 7.63-7.56 (m, 1H), 7.55-7.49 (m, 1H), 6.96 (d, J=2.2 Hz, 1H), 5.57 (s, 2H), 4.29-4.12 (m, 4H); MS (ES+) 389.20 (M+1), (ES+): 387.25 (M−1); HPLC purity: 93.23%.

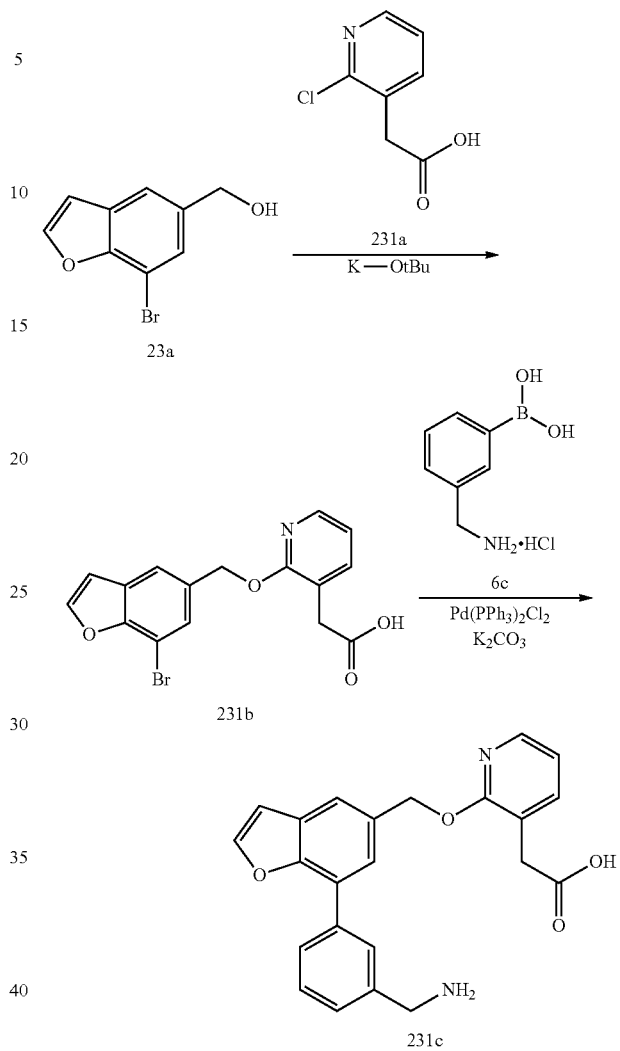

Preparation of 2-(2-((7-(3-(aminomethyl)phenyl)benzofuran-5-yl)methoxy)pyridin-3-yl)acetic Acid (231c)

Step-1: Preparation of 2-(2-((7-bromobenzofuran-5-yl)methoxy)pyridin-3-yl)acetic Acid (231b)

To a solution of (7-bromobenzofuran-5-yl)methanol (23a) (500 mg, 2.202 mmol) and 2-(2-chloropyridin-3-yl)acetic acid (231a) (378 mg, 2.202 mmol; CAS #61494-55-1) in 1,4-Dioxane (10 mL) was added potassium tert-butoxide (741 mg, 6.61 mmol) and heated at 110° C. for 2 h. The reaction was cooled to rt, diluted with water and acidified to pH 6. The reaction mixture was extracted with ethyl acetate (3×50 mL) and the combined organic layers was washed with brine, dried and concentrated in vacuum. The residue obtained was purified by flash column chromatography [silica gel 25 g, eluting with a 9:1 mixture (ethyl acetate and methanol) in hexanes (0 to 100%)] to afford 2-(2-((7-bromobenzofuran-5-yl)methoxy)pyridin-3-yl)acetic acid (231b) (380 mg, 48% yield) as a white solid; ¹H NMR (300 MHz, DMSO-d₆) δ 12.40 (s, 1H), 8.13 (d, J=2.2 Hz, 1H), 8.07 (dd, J=5.0, 1.9 Hz, 1H), 7.73 (d, J=1.5 Hz, 1H), 7.67-7.60 (m, 2H), 7.08 (d, J=2.2 Hz, 1H), 6.98 (dd, J=7.2, 5.0 Hz, 1H), 5.45 (s, 2H), 3.59 (s, 2H); MS (ES+): 362.00, 364.00 (M+1).

Step-2: Preparation of 2-(2-((7-(3-(aminomethyl) phenyl)benzofuran-5-yl)methoxy)pyridin-3-yl)acetic Acid (231c)

Compound 231c was prepared according to the procedure reported in step-3 of Scheme-1 from 2-(2-((7-bromobenzofuran-5-yl)methoxy)pyridin-3-yl)acetic acid (231b) (300 mg, 0.828 mmol) in dioxane (5 mL) using 3-(aminomethyl) phenylboronic acid hydrochloride (6c) (233 mg, 1.242 mmol), K$_2$CO$_3$ (343 mg, 2.485 mmol) in water (2 mL) and bis(triphenylphosphine)palladium(ll)chloride (87 mg, 0.124 mmol) under a nitrogen atmosphere and heating at 100° C. for 3 h on oil bath. This gave after workup and purification by flash column chromatography [silica (25 g), eluting with DMA80 in DCM from 0-50%] 2-(2-((7-(3-(aminomethyl) phenyl)benzofuran-5-yl)methoxy)pyridin-3-yl)acetic acid (231c) (102 mg, 32% yield) as a buff solid; $^1$H NMR (300 MHz, DMSO-d$_6$) δ 8.35 (d, J=2.0 Hz, 1H), 8.14-8.06 (m, 2H), 7.93 (dd, J=5.0, 1.9 Hz, 1H), 7.87 (d, J=1.6 Hz, 1H), 7.65 (d, J=1.5 Hz, 1H), 7.52-7.43 (m, 2H), 7.39-7.31 (m, 1H), 7.04 (d, J=2.2 Hz, 1H), 6.88 (dd, J=7.1, 5.0 Hz, 1H), 5.55 (s, 2H), 4.03 (s, 2H), 3.37 (s, 2H); MS (ES+): 389.20 (M+1), (ES−): 387.30 (M−1).

Scheme-232

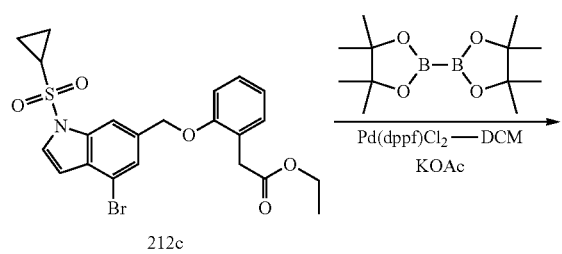

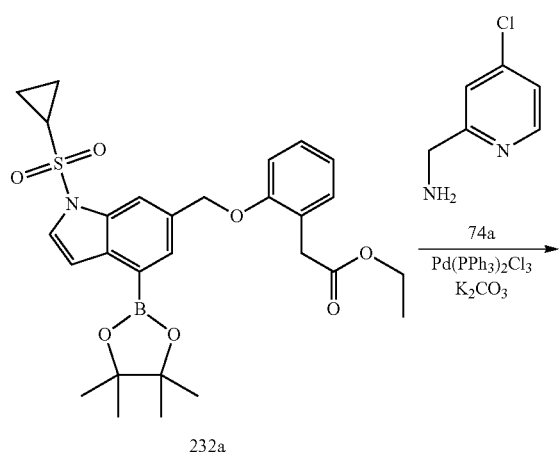

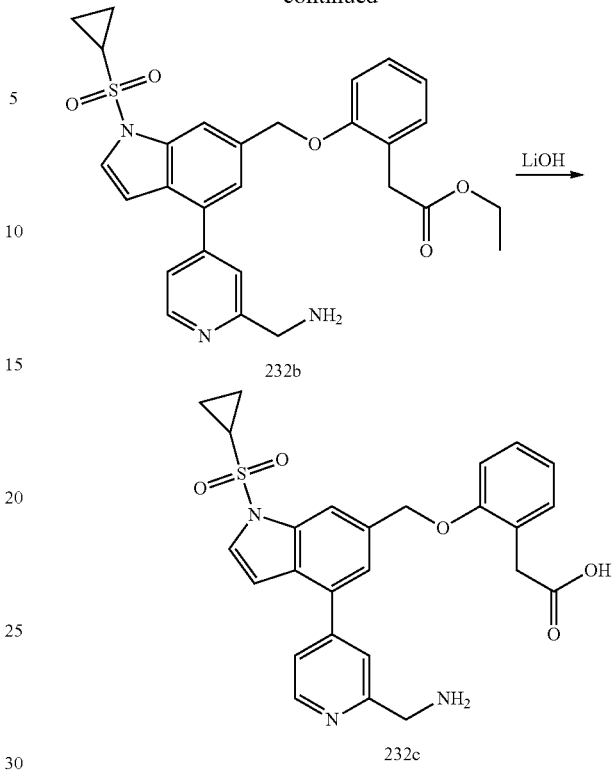

Preparation of 2-(2-((4-(2-(aminomethyl)pyridin-4-yl)-1-(cyclopropylsulfonyl)-1H-indol-6-yl)methoxy) phenyl)acetic Acid (232c)

Step-1: Preparation of Ethyl 2-(2-((1-(cyclopropylsulfonyl)-4-(4,4,5,5-tetramethyl-1,3,2-dioxaborolan-2-yl)-1H-indol-6-yl)methoxy)phenyl)acetate (232a)

Compound 232a was prepared according to the procedure reported in step-1 of Scheme-59 from ethyl 2-(2-((4-bromo-1-(cyclopropylsulfonyl)-1H-indol-6-yl)methoxy)phenyl)acetate (212c) (0.9 g, 1.83 mmol), using bis(pinacolato)diboron (0.70 g, 2.74 mmol), potassium acetate (0.36 g, 3.66 mmol) and Pd(dppf)Cl$_2$—CH$_2$Cl$_2$ (0.22 g, 0.27 mmol) in anhydrous dioxane (7 mL) under an Ar atmosphere and heating at 100° C. overnight. This gave after workup and purification by flash column chromatography [silica gel, 24 g, eluting with EtOAc/MeOH=9:1 in hexane from 0-10%] ethyl 2-(2-((1-(cyclopropylsulfonyl)-4-(4,4,5,5-tetramethyl-1,3,2-dioxaborolan-2-yl)-1H-indol-6-yl)methoxy)phenyl) acetate (232a) (0.67 g, 67% yield) as a yellow oil; $^1$H NMR (300 MHz, DMSO-d$_6$) δ 8.09 (s, 1H), 7.70 (d, J=1.5 Hz, 1H), 7.67 (d, J=3.6 Hz, 1H), 7.29-7.17 (m, 2H), 7.15-7.06 (m, 2H), 6.91 (td, J=7.3, 1.1 Hz, 1H), 5.24 (s, 2H), 4.00 (q, J=7.1 Hz, 2H), 3.59 (s, 2H), 3.08-2.93 (m, 1H), 1.34 (s, 12H), 1.25-1.11 (m, 2H), 1.11-0.93 (m, 5H).

Step-2: Preparation of Ethyl 2-(2-((4-(2-(aminomethyl)pyridin-4-yl)-1-(cyclopropylsulfonyl)-1H-indol-6-yl)methoxy)phenyl)acetate (232b)

Compound 232b was prepared according to the procedure reported in step-3 of Scheme-1 from ethyl 2-(2-((1-(cyclopropylsulfonyl)-4-(4,4,5,5-tetramethyl-1,3,2-dioxaborolan- 2-yl)-1H-indol-6-yl)methoxy)phenyl)acetate (232a) (0.3 g, 0.56 mmol) in dioxane (4 mL) using (4-chloropyridin-2-yl)methanamine (74a) (0.10 mL, 0.83 mmol), bis(triphenylphosphine)palladium(II) chloride (0.06 g, 0.08 mmol) and a solution of $K_2CO_3$ (0.12 g, 0.83 mmol) in water (0.4 mL) under an Ar atmosphere and heating at 90° C. for 4 h on oil bath. This gave after workup, purification by flash column chromatography [silica (12 g), eluting with DMA80 in DCM from 0-50%] followed by purification by reverse-phase column chromatography [C18 (50 g), eluting with ACN in water (containing 0.1% HCl) from 0-100%] ethyl 2-(2-((4-(2-(aminomethyl)pyridin-4-yl)-1-(cyclopropylsulfonyl)-1H-indol-6-yl)methoxy)phenyl)acetate (232b) (0.1 g, 35% yield) HCl salt as a yellow solid; $^1$H NMR (300 MHz, DMSO-$d_6$) δ 8.44 (d, J=5.3 Hz, 1H), 8.08 (s, 1H), 7.78-7.71 (m, 2H), 7.62-7.54 (m, 2H), 7.36 (dd, J=5.4, 2.1 Hz, 1H), 7.30-7.19 (m, 2H), 6.99 (dd, J=3.8, 0.9 Hz, 1H), 6.91 (td, J=7.4, 1.1 Hz, 1H), 5.32 (s, 2H), 3.91-3.89 (m, 2H), 3.80 (s, 2H), 3.63 (s, 2H), 3.16-3.06 (m, 1H), 1.33-1.03 (m, 4H), 0.96 (t, J=7.1 Hz, 3H); MS (ES+): 520.2 (M+1).

Step-3: Preparation of 2-(2-((4-(2-(aminomethyl)pyridin-4-yl)-1-(cyclopropylsulfonyl)-1H-indol-6-yl)methoxy)phenyl)acetic Acid (232c)

Compound 232c was prepared according to the procedure reported in step-6 of Scheme-1 from ethyl 2-(2-((4-(2-(aminomethyl)pyridin-4-yl)-1-(cyclopropylsulfonyl)-1H-indol-6-yl)methoxy)phenyl)acetate (232b) (0.1 g, 0.19 mmol) in THF (4 mL) and MeOH (4 mL) using lithium hydroxide hydrate (0.07 g, 1.54 mmol) in water (0.4 mL). This gave after workup and purification by reverse phase column [C18 (50 g), eluting with ACN in water (containing 0.1% HCl) from 0-100%] 2-(2-((4-(2-(aminomethyl)pyridin-4-yl)-1-(cyclopropylsulfonyl)-1H-indol-6-yl)methoxy)phenyl)acetic acid (232c) (0.04 g, 44% yield) HCl salt as a yellow solid; $^1$H NMR (300 MHz, DMSO-$d_6$) δ 8.76 (dd, J=5.2, 0.7 Hz, 1H), 8.58 (s, 3H), 8.13 (t, J=1.0 Hz, 1H), 7.87 (t, J=1.1 Hz, 1H), 7.80 (d, J=3.7 Hz, 1H), 7.73 (dd, J=5.2, 1.7 Hz, 1H), 7.64 (d, J=1.3 Hz, 1H), 7.24 (dd, J=9.0, 6.6 Hz, 2H), 7.16-7.06 (m, 2H), 6.91 (td, J=7.3, 1.1 Hz, 1H), 5.35 (s, 2H), 4.31 (s, 2H), 3.61 (s, 2H), 3.24-3.05 (m, 1H), 1.37-0.99 (m, 4H); MS (ES+): 492.2 (M+1), MS (ES−): 490.2 (M−1).

Scheme-233

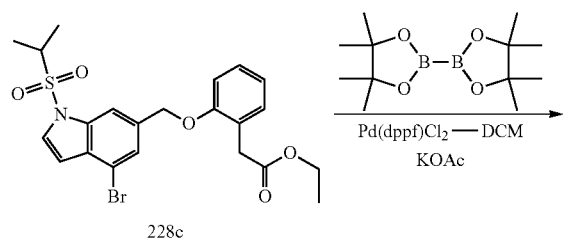

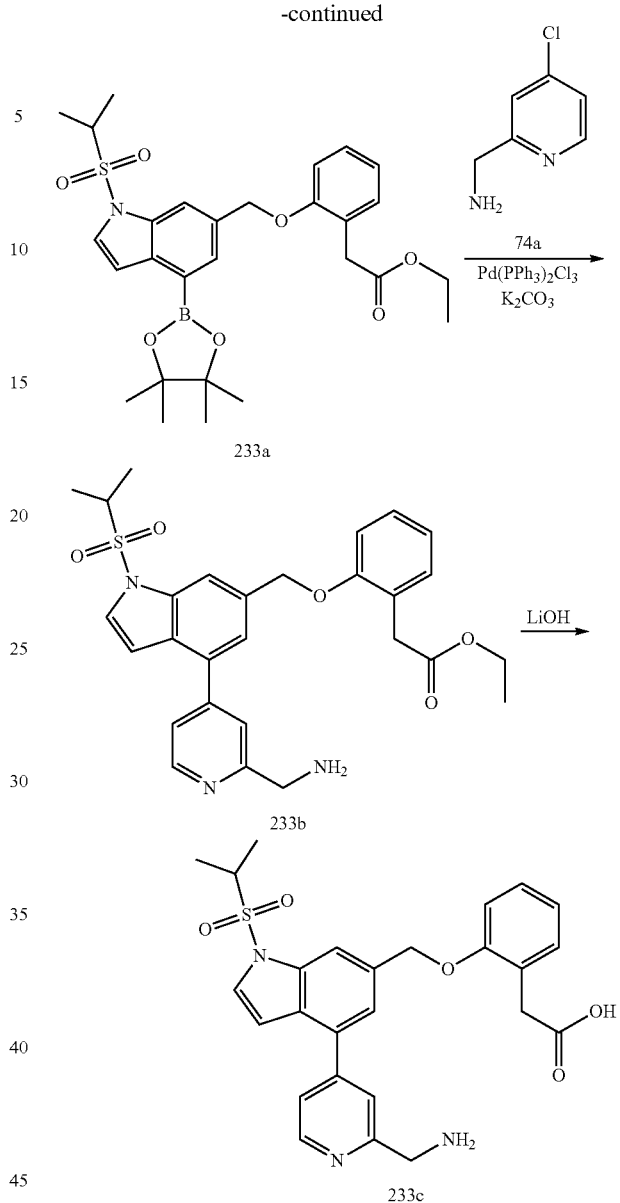

Preparation of 2-(2-((4-(2-(aminomethyl)pyridin-4-yl)-1-(isopropylsulfonyl)-1H-indol-6-yl)methoxy)phenyl)acetic Acid (233c)

Step-1: Preparation of Ethyl 2-(2-((1-(isopropylsulfonyl)-4-(4,4,5,5-tetramethyl-1,3,2-dioxaborolan-2-yl)-1H-indol-6-yl)methoxy)phenyl)acetate (233a)

Compound 233a was prepared according to the procedure reported in step-1 of Scheme-59 from ethyl 2-(2-((4-bromo-1-(isopropylsulfonyl)-1H-indol-6-yl)methoxy)phenyl)acetate (228c) (0.6 g, 1.21 mmol), using bis(pinacolato)diboron (0.46 g, 1.82 mmol), potassium acetate (0.24 g, 2.43 mmol) and Pd(dppf)Cl$_2$—CH$_2$Cl$_2$ (0.15 g, 0.18 mmol) in anhydrous dioxane (7 mL) under an Ar atmosphere and heating at 100° C. overnight. This gave after workup and purification by flash column chromatography [silica gel, 24 g, eluting with EtOAc/MeOH=9:1 in hexane from 0-10%]

ethyl 2-(2-((1-(isopropylsulfonyl)-4-(4,4,5,5-tetramethyl-1,3,2-dioxaborolan-2-yl)-1H-indol-6-yl)methoxy)phenyl)acetate (233a) (0.43 g, 66% yield) as a yellow oil; $^1$H NMR (300 MHz, DMSO-$d_6$) δ 8.05 (dd, J=1.5, 0.8 Hz, 1H), 7.70 (d, J=1.5 Hz, 1H), 7.66 (d, J=3.7 Hz, 1H), 7.28-7.18 (m, 2H), 7.13-7.06 (m, 2H), 6.91 (td, J=7.4, 1.1 Hz, 1H), 5.23 (s, 2H), 4.05-3.96 (m, 2H), 3.75 (p, J=6.7 Hz, 1H), 3.59 (s, 2H), 1.34 (s, 12H), 1.07 (s, 6H), 1.03 (t, J=7.2 Hz, 3H).

Step-2: Preparation of Ethyl 2-(2-((4-(2-(aminomethyl)pyridin-4-yl)-1-(isopropylsulfonyl)-1H-indol-6-yl)methoxy)phenyl)acetate (233b)

Compound 233b was prepared according to the procedure reported in step-3 of Scheme-1 from ethyl 2-(2-((1-(isopropylsulfonyl)-4-(4,4,5,5-tetramethyl-1,3,2-dioxaborolan-2-yl)-1H-indol-6-yl)methoxy)phenyl)acetate (233a) (0.2 g, 0.37 mmol) in dioxane (4 mL) using (4-chloropyridin-2-yl)methanamine (74a) (0.064 mL, 0.554 mmol), bis(triphenylphosphine)palladium(II) chloride (0.04 g, 0.06 mmol) and a solution of $K_2CO_3$ (0.08 g, 0.55 mmol) in water (0.4 mL) under an Ar atmosphere and heating at 90° C. for 4 h on oil bath. This gave after workup, purification by flash column chromatography [silica (12 g), eluting with DMA80 in DCM from 0-50%] followed by purification by reverse-phase column chromatography [C18 (50 g), eluting with ACN in water (containing 0.1% HCl) from 0-100%] ethyl 2-(2-((4-(2-(aminomethyl)pyridin-4-yl)-1-(isopropylsulfonyl)-1H-indol-6-yl)methoxy)phenyl)acetate (233b) (0.06 g, 29% yield) HCl salt as a yellow solid; $^1$H NMR (300 MHz, DMSO-$d_6$) δ 8.44 (d, J=5.3 Hz, 1H), 8.04 (s, 1H), 7.77-7.70 (m, 2H), 7.57 (dd, J=10.0, 1.7 Hz, 2H), 7.30-7.19 (m, 2H), 7.12 (dd, J=8.3, 1.1 Hz, 1H), 6.99 (dd, J=3.8, 0.8 Hz, 1H), 6.91 (td, J=7.4, 1.1 Hz, 1H), 5.31 (s, 2H), 3.94-3.89 (m, 2H), 3.88-3.82 (m, 1H), 3.80 (s, 2H), 3.63 (s, 2H), 1.21 (d, J=6.8 Hz, 6H), 0.95 (t, J=7.1 Hz, 3H); MS (ES+): 522.2 (M+1).

Step-3: Preparation of 2-(2-((4-(2-(aminomethyl)pyridin-4-yl)-1-(isopropylsulfonyl)-1H-indol-6-yl)methoxy)phenyl)acetic Acid (233c)

Compound 233c was prepared according to the procedure reported in step-6 of Scheme-1 from ethyl 2-(2-((4-(2-(aminomethyl)pyridin-4-yl)-1-(isopropylsulfonyl)-1H-indol-6-yl)methoxy)phenyl)acetate (233b) (0.05 g, 0.1 mmol) in THF (4 mL) and MeOH (4 mL) using lithium hydroxide hydrate (0.03 g, 0.77 mmol) in water (0.4 mL). This gave after workup and purification by reverse phase column [C18 (50 g), eluting with ACN in water (containing 0.1% HCl) from 0-100%] 2-(2-((4-(2-(aminomethyl)pyridin-4-yl)-1-(isopropylsulfonyl)-1H-indol-6-yl)methoxy)phenyl)acetic acid (233c) (0.03 g, 66% yield) as a yellow solid; $^1$H NMR (300 MHz, DMSO-$d_6$) δ 8.75 (d, J=5.1 Hz, 1H), 8.50 (s, 3H), 8.09 (s, 1H), 7.83 (d, J=1.6 Hz, 1H), 7.79 (d, J=3.7 Hz, 1H), 7.71 (dd, J=5.2, 1.6 Hz, 1H), 7.63 (d, J=1.3 Hz, 1H), 7.24 (t, J=7.6 Hz, 2H), 7.15-7.05 (m, 2H), 6.91 (td, J=7.4, 1.1 Hz, 1H), 5.34 (s, 2H), 4.31 (d, J=5.7 Hz, 2H), 3.87 (p, J=6.8 Hz, 1H), 3.60 (s, 2H), 1.22 (d, J=6.8 Hz, 6H); MS (ES+): 494.1 (M+1), MS (ES−): 492.3 (M−1).

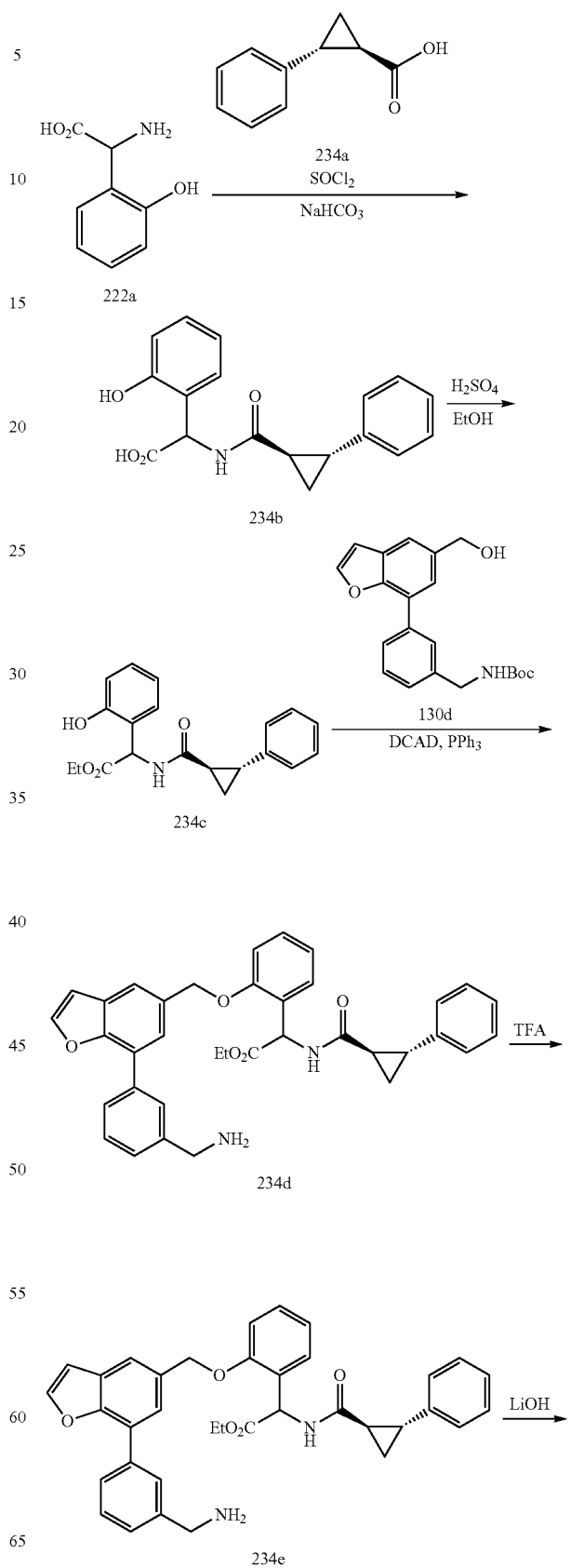

Scheme-234

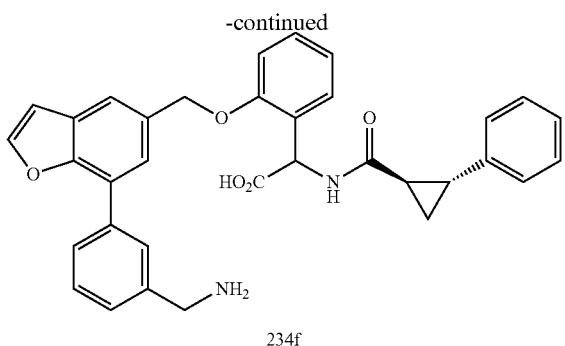

234f

Preparation of 2-(2-((7-(3-(aminomethyl)phenyl)benzofuran-5-yl)methoxy)phenyl)-2-((1R,2R)-2-phenylcyclopropanecarboxamido)acetic Acid (234f)

Step-1: Preparation of 2-(2-hydroxyphenyl)-2-((1R,2R)-2-phenylcyclopropanecarboxamido)acetic Acid (234b)

To a stirred solution of (1R,2R)-2-phenylcyclopropanecarboxylic acid (234a) (1.019 g, 6.28 mmol; CAS #939-90-2) in DCM (10 mL) was added thionyl chloride (0.504 mL, 6.91 mmol), DMF (0.02 mL) and heated at reflux for 2 h. The reaction mixture was concentrated in vacuum and the residue obtained was dissolved in THF (20 mL), added to a solution of 2-amino-2-(2-hydroxyphenyl)acetic acid (0.7 g, 4.19 mmol) and sodium bicarbonate (1.759 g, 20.94 mmol) in water (15 mL) at 0° C. The reaction was allowed to warm to room temperature and stirred for 12 h. The reaction mixture was acidified with 3 N HCl to pH 4 and extracted with ethyl acetate (3×100 mL). The combined organic layers were washed with brine (25 mL), dried and concentrated in vacuum. The residue obtained was triturated with hexanes and collected by filtration to afford 2-(2-hydroxyphenyl)-2-((1R,2R)-2-phenylcyclopropanecarboxamido)acetic acid (234b) (1.45 g, 111% yield) as a white solid. This was used as such in the next step without further purification; MS (ES+): 312.20 (M+1), (ES−): 310.2 (M−1).

Step-2: Preparation of Ethyl 2-(2-hydroxyphenyl)-2-((1R,2R)-2-phenylcyclopropanecarboxamido)acetate (234c)

Compound 234c was prepared according to the procedure reported in step-2 of Scheme-222 from 2-(2-hydroxyphenyl)-2-((1R,2R)-2-phenylcyclopropanecarboxamido)acetic acid (234b) (1.42 g, 4.56 mmol) in ethanol (30 mL) using sulfuric acid (0.486 mL, 9.12 mmol). This gave after workup and purification by flash column chromatography (silica gel) ethyl 2-(2-hydroxyphenyl)-2-((1R,2R)-2-phenylcyclopropanecarboxamido)acetate (234c) (1.14 g, 74% yield) as a white solid; $^1$H NMR (300 MHz, DMSO-d$_6$) δ 9.81 (d, J=2.8 Hz, 1H), 8.66 (t, J=7.1 Hz, 1H), 7.34-7.17 (m, 2H), 7.19-7.06 (m, 5H), 6.89-6.74 (m, 2H), 5.70 (dd, J=7.6, 1.8 Hz, 1H), 4.14-3.99 (m, 2H), 2.32-2.14 (m, 1H), 2.20-2.08 (m, 1H), 1.42-1.27 (m, 1H), 1.27-1.12 (m, 1H), 1.11 (m, 3H); MS (ES+): 340.2 (M+1), 338.3 (M−1).

Step-3: Preparation ethyl 2-(2-((7-(3-(((tert-butoxycarbonyl)amino)methyl)phenyl)benzofuran-5-yl)methoxy)phenyl)-2-((1R,2R)-2-phenylcyclopropanecarboxamido)acetate (234d)

Compound 234d was prepared according to the procedure reported in step-2 of Scheme-23 from tert-butyl 3-(5-(hydroxymethyl)benzofuran-7-yl)benzylcarbamate (130d) (600 mg, 1.698 mmol) in DCM (20 mL) using triphenylphosphine (512 mg, 1.952 mmol) ethyl 2-(2-hydroxyphenyl)-2-((1R,2R)-2-phenylcyclopropanecarboxamido)acetate (234c) (663 mg, 1.952 mmol) and a solution of di-(4-chlorobenzyl)azodicarboxylate (DCAD, 748 mg, 2.037 mmol) in DCM (15 mL). This gave after workup and purification by flash column chromatography (silica gel 24 g, eluting with ethyl acetate in hexanes from 0-50%) ethyl 2-(2-((7-(3-(((tert-butoxycarbonyl)amino)methyl)phenyl)benzofuran-5-yl)methoxy)phenyl)-2-((1R,2R)-2-phenylcyclopropanecarboxamido)acetate (234d) (855 mg, 75% yield) as a white foam; MS (ES+): 575.30 (M+1-Boc).

Step-4: Preparation of Ethyl 2-(2-((7-(3-(aminomethyl)phenyl)benzofuran-5-yl)methoxy)phenyl)-2-((1R,2R)-2-phenylcyclopropanecarboxamido)acetate (234e)

Compound 234e was prepared according to the procedure reported in step-5 of Scheme-1 from ethyl 2-(2-((7-(3-(((tert-butoxycarbonyl)amino)methyl)phenyl)benzofuran-5-yl)methoxy)phenyl)-2-((1R,2R)-2-phenylcyclopropanecarboxamido)acetate (234d) (750 mg, 1.111 mmol) in DCM (10 mL) using TFA (0.856 mL, 11.11 mmol). This gave after workup ethyl 2-(2-((7-(3-(aminomethyl)phenyl)benzofuran-5-yl)methoxy)phenyl)-2-((1R,2R)-2-phenylcyclopropanecarboxamido)acetate (234e) (639 mg, 100% yield) as a TFA salt which was used as such in the next step without further purification; MS (ES+): 575.30 (M+1).

Step-5: Preparation of 2-(2-((7-(3-(aminomethyl)phenyl)benzofuran-5-yl)methoxy)phenyl)-2-((1R,2R)-2-phenylcyclopropanecarboxamido)acetic Acid (234f)

Compound 234f was prepared according to the procedure reported in step-6 of Scheme-1 from ethyl 2-(2-((7-(3-(aminomethyl)phenyl)benzofuran-5-yl)methoxy)phenyl)-2-((1R,2R)-2-phenylcyclopropanecarboxamido)acetate (234e) (500 mg, 0.870 mmol) in THF (5 mL) and methanol (5 mL) using a solution of lithium hydroxide monohydrate (83 mg, 3.48 mmol) in water (2 mL). This gave after workup and purification by reverse phase column [C18 (30 g), eluting with ACN in water (containing 0.1% HCl) from 0-100%] 2-(2-((7-(3-(aminomethyl)phenyl)benzofuran-5-yl)methoxy)phenyl)-2-((1R,2R)-2-phenylcyclopropanecarboxamido)acetic acid (234f) (332 mg, 70% yield) hydrochloride salt as a white solid; $^1$H NMR (300 MHz, DMSO-d$_6$) δ 12.75 (s, 1H), 8.80 (dd, J=13.2, 8.1 Hz, 1H), 8.52 (s, 3H), 8.11 (t, J=2.3 Hz, 1H), 8.04 (d, J=3.0 Hz, 1H), 8.00-7.90 (m, 1H), 7.79 (dd, J=6.7, 1.6 Hz, 1H), 7.76-7.69 (m, 1H), 7.63-7.51 (m, 2H), 7.30 (ddd, J=13.1, 7.5, 2.6 Hz, 3H), 7.25-7.07 (m, 4H), 7.06-6.93 (m, 3H), 5.92 (dd, J=8.0, 1.9 Hz, 1H), 5.33 (d, J=5.5 Hz, 2H), 4.23-4.05 (m, 2H), 2.33-2.08 (m, 2H), 1.43-1.04 (m, 2H); MS (ES+): 547.2 (M+1), (ES−): 545.3 (M−1); HPLC purity: 98.60%.

Scheme-235

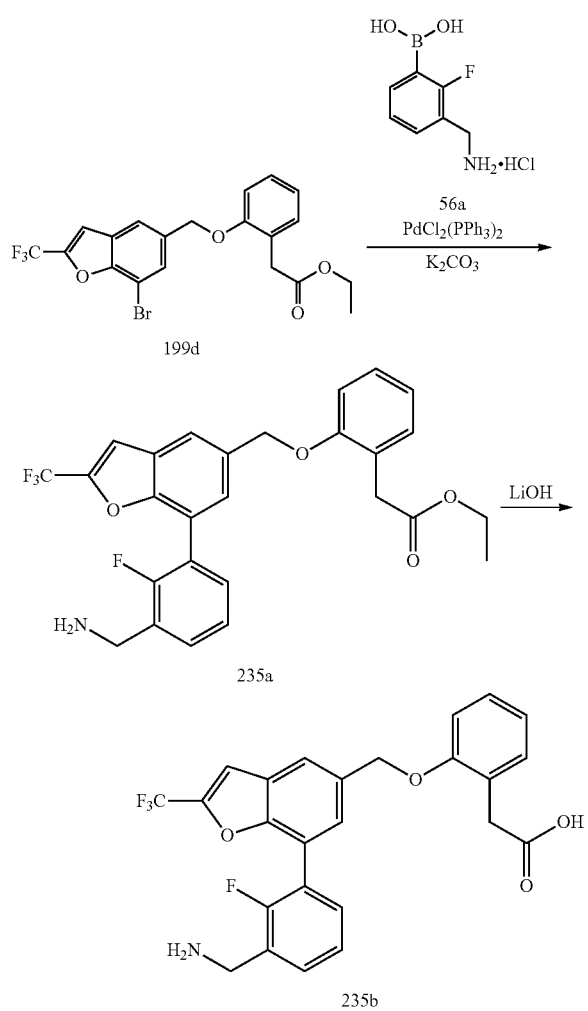

Preparation of 2-(2-((7-(3-(aminomethyl)-2-fluorophenyl)-2-(trifluoromethyl)benzofuran-5-yl)methoxy)phenyl)acetic Acid (235b)

Step-1: Preparation of Ethyl 2-(2-((7-(3-(aminomethyl)-2-fluorophenyl)-2-(trifluoromethyl)benzofuran-5-yl)methoxy)phenyl)acetate (235a)

Compound 235a was prepared according to the procedure reported in step-3 of Scheme-1 from ethyl 2-(2-((7-bromo-2-(trifluoromethyl)benzofuran-5-yl)methoxy)phenyl)acetate (199d) (198 mg, 0.433 mmol) in dioxane (5 mL) using (3-(aminomethyl)-2-fluorophenyl)boronic acid hydrochloride (56a) (125 mg, 0.610 mmol) a solution of K$_2$CO$_3$ (164 mg, 1.187 mmol) in water (0.5 mL), bis(triphenylphosphine) palladium(II) chloride (46 mg, 0.066 mmol) and heating at 100° C. for 3h on oil bath. This gave after workup, purification by flash column chromatography [silica gel (12 g), eluting with DMA80 in DCM from 0-60%] ethyl 2-(2-((7-(3-(aminomethyl)-2-fluorophenyl)-2-(trifluoromethyl)benzofuran-5-yl)methoxy)phenyl)acetate (235a) (156 mg, 72% yield) as a clear oil; MS (ES+): 502.2 (M+1).

Step-2: Preparation of 2-(2-((7-(3-(aminomethyl)-2-fluorophenyl)-2-(trifluoromethyl)benzofuran-5-yl)methoxy)phenyl)acetic Acid (235b)

Compound 235b was prepared according to the procedure reported in step-6 of Scheme-1 from ethyl 2-(2-((7-(3-(aminomethyl)-2-fluorophenyl)-2-(trifluoromethyl)benzofuran-5-yl)methoxy)phenyl)acetate (235a) (156 mg, 0.311 mmol) in MeOH/THF (6 mL each) using a solution of lithium hydroxide monohydrate (72 mg, 1.72 mmol) in water (2.0 mL). This gave after workup and purification by reverse phase column [C18 (50 g), eluting with ACN in water (containing 0.1% HCl) from 0-100%] 2-(2-((7-(3-(aminomethyl)-2-fluorophenyl)-2-(trifluoromethyl)benzofuran-5-yl)methoxy)phenyl)acetic acid (235b) (33 mg, 22% yield) HCl salt as a white solid. $^1$H NMR (300 MHz, DMSO-d$_6$) δ 8.61 (s, 2H), 7.92 (d, J=1.5 Hz, 1H), 7.81 (d, J=1.4 Hz, 1H), 7.76-7.59 (m, 3H), 7.40 (t, J=7.7 Hz, 1H), 7.17 (t, J=7.6 Hz, 2H), 7.03 (d, J=8.0 Hz, 1H), 6.85 (td, J=7.4, 1.1 Hz, 1H), 5.25 (s, 2H), 4.11 (s, 2H), 3.53 (s, 2H); $^{19}$F NMR (282 MHz, DMSO-d$_6$) δ−63.41, −118.91. MS (ES+): 474.1 (M+1); MS(ES−): 472.3 (M−1). HPLC purity 98.86%.

Scheme-236

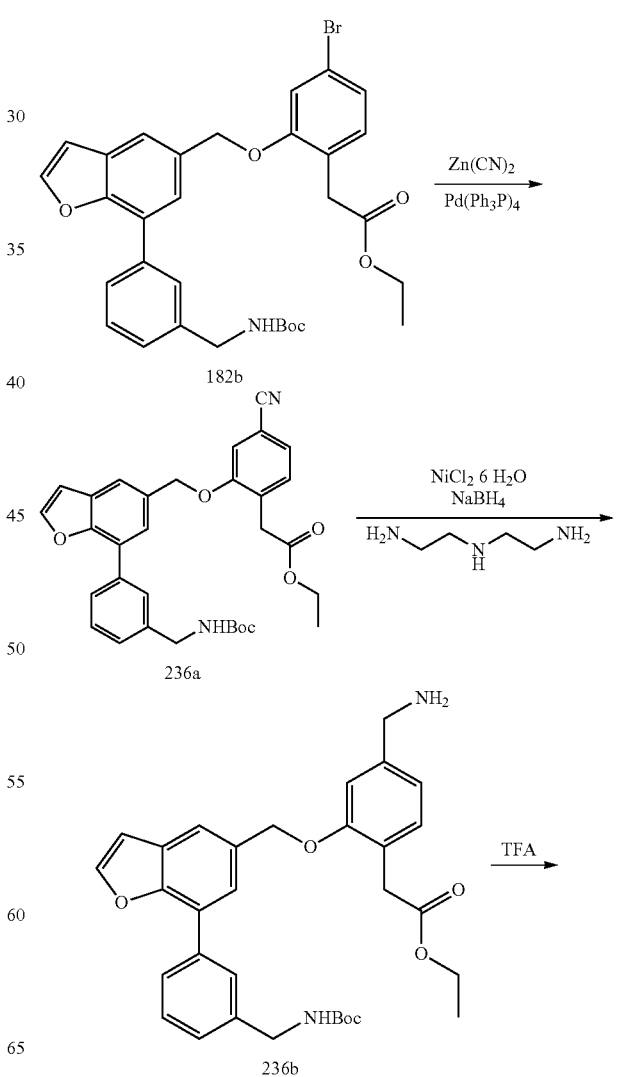

-continued

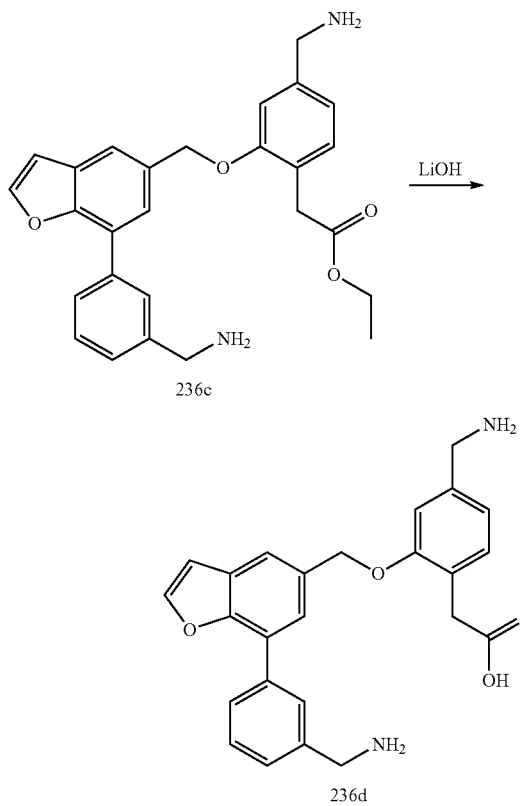

Preparation of 2-(4-(aminomethyl)-2-((7-(3-(aminomethyl)phenyl)benzofuran-5-yl)methoxy)phenyl) acetic Acid (236d)

Step-1: Preparation of Ethyl 2-(2-((7-(3-(((tert-butoxycarbonyl)amino)methyl)phenyl)benzofuran-5-yl)methoxy)-4-cyanophenyl)acetate (236a)

A mixture of ethyl 2-(4-bromo-2-((7-(3-((tert-butoxycarbonylamino)methyl)phenyl)benzofuran-5-yl)methoxy)phenyl)acetate (182b) (0.600 g, 1.009 mmol), dicyanozinc (0.142 g, 1.211 mmol), Pd(Ph$_3$P)$_4$ (0.350 g, 0.303 mmol) was purged with nitrogen for 10 min. Anhydrous DMF (6.0 mL) was added and the suspension was heated in a microwave for 40 min at 120° C. The reaction mixture was cooled to rt, diluted with ethyl acetate (100 mL) and brine (100 mL). The aqueous layer was separated and extracted with ethyl acetate (100 mL). The combined organics were washed with brine, dried, filtered and evaporated to dryness. The residue obtained was purified by flash column chromatography (silica gel 12 g, eluting with ethyl acetate in hexanes from 0 to 100%) to afford ethyl 2-(2-((7-(3-(((tert-butoxycarbonyl)amino)methyl)phenyl)benzofuran-5-yl)methoxy)-4-cyanophenyl)acetate (236a) (0.435 g, 80% yield) as a yellow solid; $^1$H NMR (300 MHz, DMSO-d$_6$) δ 8.10 (d, J=2.2 Hz, 1H), 7.73 (dd, J=9.1, 1.5 Hz, 3H), 7.64 (d, J=1.3 Hz, 1H), 7.54 (d, J=1.7 Hz, 1H), 7.55-7.37 (m, 3H), 7.30 (d, J=7.6 Hz, 1H), 7.07 (d, J=2.2 Hz, 1H), 5.31 (s, 2H), 4.23 (d, J=6.2 Hz, 2H), 3.89 (q, J=7.1 Hz, 2H), 3.72 (s, 2H), 1.39 (s, 9H), 0.93 (t, J=7.1 Hz, 3H); MS (ES−): 539.4 (M−1)

Step-2: Preparation of Ethyl 2-(4-(aminomethyl)-2-((7-(3-(((tert-butoxycarbonyl)amino)methyl)phenyl)benzofuran-5-yl)methoxy)phenyl)acetate (236b)

To a solution of ethyl 2-(2-((7-(3-(((tert-butoxycarbonyl)amino)methyl)phenyl)benzofuran-5-yl)methoxy)-4-cyanophenyl)acetate (236a) (0.150 g, 0.277 mmol) in methanol (10 mL) cooled to 0° C., was added nickel(II) chloride hexahydrate (0.016 g, 0.069 mmol), followed by sodium borohydride (0.063 g, 1.665 mmol) over a period of 10 min and stirred for 1 h. The reaction mixture was quenched with N1-(2-aminoethyl)ethane-1,2-diamine (0.060 mL, 0.555 mmol) stirred at RT for 1 h and concentrated in vacuum. The resultant residue was partitioned between brine (100 mL) and extracted with EtOAc (2×150 mL). The combined organics were dried, filtered, concentrated in vacuum. The residue obtained was purified by flash column chromatography (silica gel 24 g, eluting with methanol in DCM from 0 to 40%) to furnish ethyl 2-(4-(aminomethyl)-2-((7-(3-(((tert-butoxycarbonyl)amino)methyl)phenyl)benzofuran-5-yl)methoxy)phenyl)acetate (236b) (0.138 g, 91% yield) as a white solid; MS (ES+): 545.1 (M+1); MS (ES−): 579.0 (M+Cl).

Step-3: Preparation of Ethyl 2-(4-(aminomethyl)-2-((7-(3-(aminomethyl)phenyl)benzofuran-5-yl)methoxy)phenyl)acetate (236c)

Compound 236c was prepared according to the procedure reported in step-5 of Scheme-1 from ethyl 2-(4-(aminomethyl)-2-((7-(3-(((tert-butoxycarbonyl)amino)methyl)phenyl)benzofuran-5-yl)methoxy)phenyl)acetate (236b) (0.132 g, 0.242 mmol) in DCM (20 mL) using TFA (0.373 mL, 4.85 mmol). This gave after workup and purification by reverse phase column chromatography (C-18 column, 50 g, eluting with 0.1% aq. HCl in water and acetonitrile from 0-100%) ethyl 2-(4-(aminomethyl)-2-((7-(3-(aminomethyl)phenyl)benzofuran-5-yl)methoxy)phenyl)acetate (236c) (0.068 g, 63% yield) as a white solid; MS (ES+): 445.0 (M+1).

Step-4: Preparation of 2-(4-(aminomethyl)-2-((7-(3-(aminomethyl)phenyl)benzofuran-5-yl)methoxy)phenyl)acetic Acid (236d)

Compound 236d was prepared according to the procedure reported in step-6 of Scheme-1 from ethyl 2-(4-(aminomethyl)-2-((7-(3-(aminomethyl)phenyl)benzofuran-5-yl)methoxy)phenyl)acetate (236c) (0.065 g, 0.146 mmol) in THF (3 mL) and methanol (6 mL) using 2M LiOH (0.731 mL, 1.462 mmol). This gave after workup and purification by reverse phase column chromatography [C-18, steel column (250 mm×30 mm) eluting with 0.1% aq. HCl in water and acetonitrile from 0-100%] 2-(4-(aminomethyl)-2-((7-(3-(aminomethyl)phenyl)benzofuran-5-yl)methoxy)phenyl) acetic acid (236d) (0.032 g, 53% yield) HCl salt as a white solid; $^1$H NMR (300 MHz, DMSO-d$_6$) δ 12.24 (s, 1H, D$_2$O exchangeable), 8.54 (bs, 6H, D$_2$O exchangeable), 8.11 (d, J=2.2 Hz, 1H), 8.08-8.03 (m, 1H), 7.99-7.90 (m, 1H), 7.78 (d, J=1.6 Hz, 1H), 7.70 (d, J=1.6 Hz, 1H), 7.63-7.54 (m, 2H), 7.45 (d, J=1.6 Hz, 1H), 7.25 (d, J=7.6 Hz, 1H), 7.07 (d, J=2.2 Hz, 1H), 7.02 (dd, J=7.7, 1.5 Hz, 1H), 5.28 (s, 2H), 4.14 (s, 2H), 3.99 (s, 2H), 3.60 (s, 2H); MS (ES+): 417.00 (M+1); MS (ES−): 415.00 (M−1).

Scheme-237

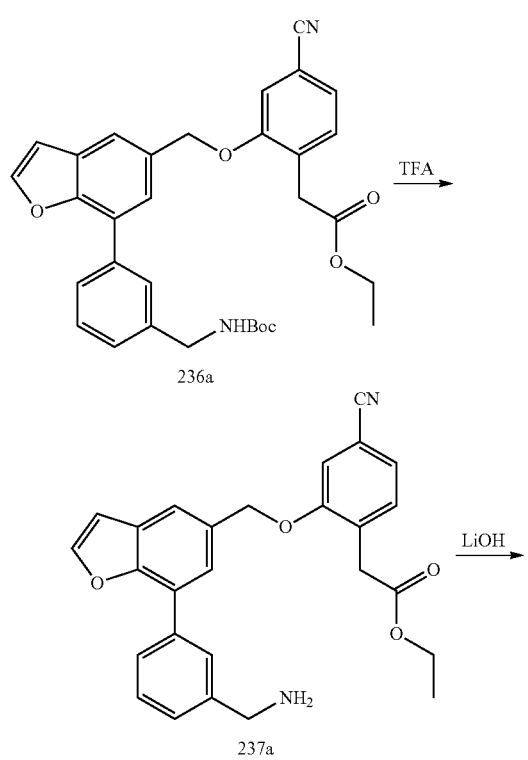

Preparation of 2-(2-((7-(3-(aminomethyl)phenyl)benzofuran-5-yl)methoxy)-4-cyanophenyl)acetic Acid (237b)

Step-1: Preparation of Ethyl 2-(2-((7-(3-(aminomethyl)phenyl)benzofuran-5-yl)methoxy)-4-cyanophenyl)acetate (237a)

Compound 237a was prepared according to the procedure reported in step-5 of Scheme-1 from ethyl 2-(2-((7-(3-(((tert-butoxycarbonyl)amino)methyl)phenyl)benzofuran-5-yl)methoxy)-4-cyanophenyl)acetate (236a) (0.210 g, 0.388 mmol) in DCM (20 mL) using TFA (0.6 mL, 7.77 mmol). This gave after workup and purification by flash column chromatography (silica gel 12 g, eluting with methanol in DCM from 0-100%) ethyl 2-(2-((7-(3-(aminomethyl)phenyl)benzofuran-5-yl)methoxy)-4-cyanophenyl)acetate (237a) (0.159 g, 0.361 mmol, 93% yield) as a white solid; MS (ES+): 441.2 (M+1); MS (ES−): 439.3 (M−1).

Step-2: Preparation of 2-(2-((7-(3-(aminomethyl)phenyl)benzofuran-5-yl)methoxy)-4-cyanophenyl)acetic Acid (237b)

Compound 237b was prepared according to the procedure reported in step-6 of Scheme-1 from ethyl 2-(2-((7-(3-(aminomethyl)phenyl)benzofuran-5-yl)methoxy)-4-cyanophenyl)acetate (237a) (0.142 g, 0.322 mmol) in THF (4 mL) and methanol (8 mL) using 2M LiOH (0.806 mL, 1.612 mmol). This gave after workup and purification by flash column chromatography (silica gel 12 g, eluting with methanol in DCM from 0-100%) followed by reverse-phase column chromatography [EZ-PREP, C-18 column, 100 g, eluting with 0.1% aq. HCl in water and acetonitrile from 0-100%] 2-(2-((7-(3-(aminomethyl)phenyl)benzofuran-5-yl)methoxy)-4-cyanophenyl)acetic acid (237b) (0.034 g, 0.082 mmol, 25.6% yield) HCl salt as a white solid; $^1$H NMR (300 MHz, DMSO-$d_6$) δ 12.48 (bs, 1H, $D_2O$ exchangeable), 8.58 (bs, 3H, $D_2O$ exchangeable), 8.12 (d, J=2.2 Hz, 1H), 8.03-7.98 (m, 1H), 7.92 (td, J=4.5, 1.8 Hz, 1H), 7.76 (d, J=1.5 Hz, 1H), 7.66 (d, J=1.6 Hz, 1H), 7.63-7.56 (m, 3H), 7.49-7.38 (m, 2H), 7.08 (d, J=2.2 Hz, 1H), 5.35 (s, 2H), 4.13 (s, 2H), 3.70 (s, 2H); MS (ES+): 413.2 (M+1); HPLC purity: 98.84%; Analysis calculated for $C_{25}H_{20}N_2O_4HCl \cdot 1.25H_2O$: C, 63.69; H, 5.02; N, 5.94; Found: C, 63.84; H, 4.96, N, 5.92.

Scheme-238

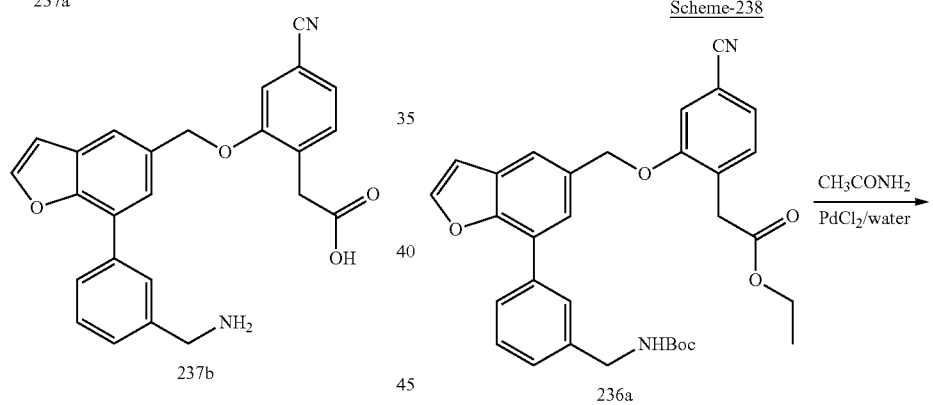

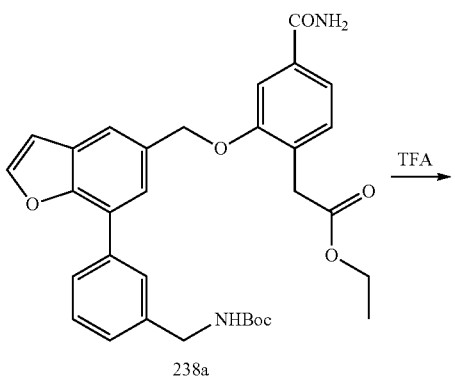

-continued

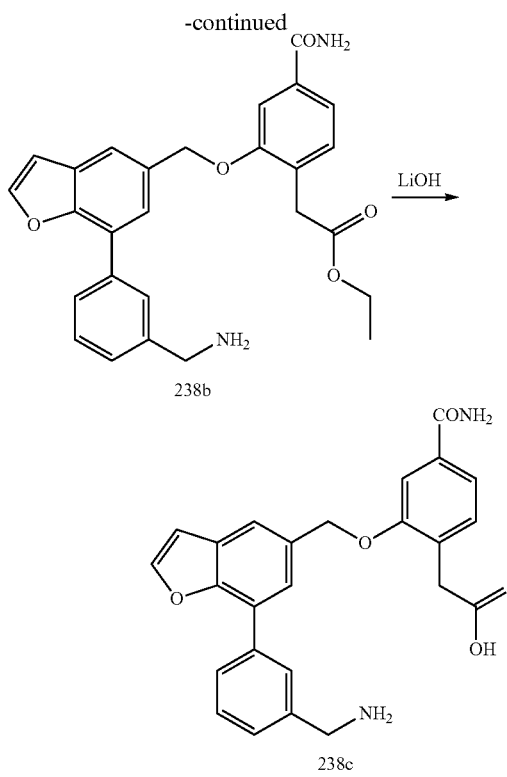

238b

238c

Preparation of 2-(2-((7-(3-(aminomethyl)phenyl)
benzofuran-5-yl)methoxy)-4-carbamoylphenyl)acetic Acid (238c)

Step-1: Preparation of Ethyl 2-(2-((7-(3-(((tert-butoxycarbonyl)amino)methyl)phenyl)benzofuran-5-yl)methoxy)-4-carbamoylphenyl)acetate (238a)

A mixture of ethyl 2-(2-((7-(3-(((tert-butoxycarbonylamino)methyl)phenyl)phenyl)benzofuran-5-yl) methoxy)-4-cyanophenyl)acetate (236a) (0.185 g, 0.342 mmol), acetamide (0.121 g, 2.053 mmol), palladium(II) chloride (9.10 mg, 0.051 mmol) in THF (2.00 mL) and water (0.25 mL) was stirred at room temperature overnight. The reaction mixture was diluted with ethyl acetate (100 mL) and brine (100 mL). The aqueous layer was separated and extracted with ethyl acetate (100 mL). The combined organics were washed with brine, dried, filtered and evaporated to dryness. The residue obtained was purified by flash column chromatography (silica gel 12g, eluting with methanol in DCM from 0 to 100%) to afford ethyl 2-(2-((7-(3-(((tert-butoxycarbonyl)amino)methyl)phenyl)benzofuran-5-yl) methoxy)-4-carbamoylphenyl)acetate (238a) (0.166 g, 87% yield) as a white solid; $^1$H NMR (300 MHz, DMSO-$d_6$) δ 8.09 (d, J=2.2 Hz, 1H), 8.00 (s, 1H), 7.81-7.69 (m, 3H), 7.63 (d, J=1.5 Hz, 1H), 7.57 (d, J=1.6 Hz, 1H), 7.55-7.41 (m, 2H), 7.39 (s, 1H), 7.31 (s, 1H), 7.29 (s, 1H), 7.07 (d, J=2.2 Hz, 1H), 5.29 (s, 2H), 4.23 (d, J=6.2 Hz, 2H), 3.91 (q, J=7.1 Hz, 2H), 3.67 (s, 2H), 1.39 (s, 9H), 0.95 (t, J=7.1 Hz, 3H); MS (ES+): 581.3 (M+Na); MS (ES−): 593.4 (M+Cl).

Step-2: Preparation of Ethyl 2-(2-((7-(3-(aminomethyl)phenyl)benzofuran-5-yl)methoxy)-4-carbamoylphenyl)acetate (238b)

Compound 238b was prepared according to the procedure reported in step-5 of Scheme-1 from ethyl 2-(2-((7-(3-(((tert-butoxycarbonyl)amino)methyl)phenyl)benzofuran-5-yl)methoxy)-4-carbamoylphenyl)acetate (238a) (0.162 g, 0.290 mmol) in DCM (20 mL) using TFA (0.447 mL, 5.80 mmol). This gave after workup and purification by flash phase column chromatography (silica gel 12 g, eluting with methanol in DCM from 0-100%) ethyl 2-(2-((7-(3-(aminomethyl)phenyl)benzofuran-5-yl)methoxy)-4-carbamoylphenyl)acetate (238b) (0.072 g, 43% yield) TFA salt as a clear wax; MS (ES+): 459.2 (M+1); MS (ES−): 457.3 (M−1).

Step-3: Preparation of 2-(2-((7-(3-(aminomethyl) phenyl)benzofuran-5-yl)methoxy)-4-carbamoylphenyl)acetic Acid (238c)

Compound 238c was prepared according to the procedure reported in step-6 of Scheme-1 from ethyl 2-(2-((7-(3-(aminomethyl)phenyl)benzofuran-5-yl)methoxy)-4-carbamoylphenyl)acetate (238b) (0.070 g, 0.122 mmol) in THF (3 mL) and methanol (6 mL) using 2M LiOH (0.306 mL, 0.611 mmol). This gave after workup and purification by flash column chromatography (silica gel 12 g, eluting with methanol in DCM from 0-100%) followed by reverse-phase column chromatography (EZ-PREP, C-18 column, 50 g, eluting with 0.1% aq. HCl in water and acetonitrile from 0-100%) 2-(2-((7-(3-(aminomethyl)phenyl)benzofuran-5-yl)methoxy)-4-carbamoylphenyl)acetic acid (238c) (0.034 g, 65% yield) HCl salt as a white solid; $^1$H NMR (300 MHz, DMSO-$d_6$) δ 12.31 (s, 1H, D$_2$O exchangeable), 8.42 (s, 3H, D$_2$O exchangeable), 8.11 (d, J=2.2 Hz, 1H), 8.01 (t, J=1.7 Hz, 2H), 7.93 (dt, J=7.3, 1.8 Hz, 1H), 7.77 (d, J=1.5 Hz, 1H), 7.68 (d, J=1.6 Hz, 1H), 7.64-7.53 (m, 3H), 7.45 (dd, J=7.7, 1.5 Hz, 1H), 7.38 (s, 1H), 7.30 (d, J=7.8 Hz, 1H), 7.07 (d, J=2.2 Hz, 1H), 5.33 (s, 2H), 4.14 (s, 2H), 3.65 (s, 2H); MS (ES+): 431.1 (M+1); Analysis calculated for C$_{25}$H$_{22}$N$_2$O$_5$·HCl·2H$_2$O: C, 59.70; H, 5.41; N, 5.57; Found: C, 59.80; H, 5.30; N, 5.70.

Scheme-239

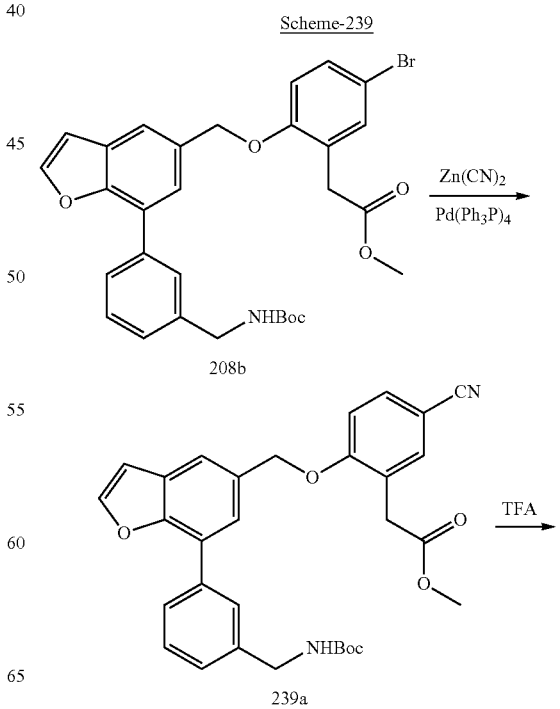

208b

239a

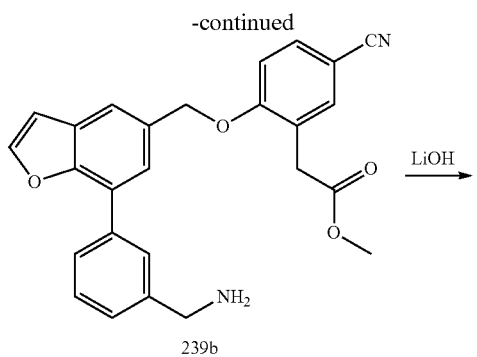

239b

239c

Preparation of 2-(2-((7-(3-(aminomethyl)phenyl)
benzofuran-5-yl)methoxy)-5-cyanophenyl)acetic
Acid (239c)

Step-1: Preparation of methyl 2-(2-((7-(3-(((tert-
butoxycarbonyl)amino)methyl)phenyl)benzofuran-5-
yl)methoxy)-5-cyanophenyl)acetate (239a)

Compound 239a was prepared according to the procedure reported in step-1 of Scheme-236 from methyl 2-(5-bromo-2-((7-(3-(((tert-butoxycarbonyl)amino)methyl)phenyl)benzofuran-5-yl)methoxy)phenyl)acetate (208b) (0.4 g, 0.69 mmol) in DMF (5 mL) using dicyanozinc (0.10 g, 0.83 mmol), Pd(Ph$_3$P)$_4$ (0.16 g, 0.14 mmol) and heating at 100° C. in an oil bath for 3 h. This gave after workup and purification by flash column chromatography (silica gel 12 g, eluting with EtOAc in hexanes from 0 to 60%) methyl 2-(2-((7-(3-(((tert-butoxycarbonyl)amino)methyl)phenyl) benzofuran-5-yl)methoxy)-5-cyanophenyl)acetate (239a) (0.3 g, 83% yield) as a yellow solid; $^1$H NMR (300 MHz, DMSO-d$_6$) δ 8.09 (d, J=2.2 Hz, 1H), 7.95 (s, 2H), 7.79 (dd, J=8.5, 2.2 Hz, 1H), 7.76-7.70 (m, 2H), 7.69 (d, J=1.6 Hz, 1H), 7.54 (d, J=1.7 Hz, 1H), 7.49 (t, J=7.8 Hz, 2H), 7.31 (dd, J=8.2, 3.5 Hz, 1H), 7.07 (d, J=2.2 Hz, 1H), 5.36 (s, 2H), 4.23 (d, J=6.2 Hz, 2H), 3.71 (s, 2H), 3.46 (s, 3H), 1.39 (s, 9H); MS (ES−): 525.3 (M−1).

Step-2: Preparation of methyl 2-(2-((7-(3-(aminom-
ethyl)phenyl)benzofuran-5-yl)methoxy)-5-cyanophe-
nyl)acetate (239b)

Compound 239b was prepared according to the procedure reported in step-5 of Scheme-1 from methyl 2-(2-((7-(3-(((tert-butoxycarbonyl)amino)methyl)phenyl)benzofuran-5-yl)methoxy)-5-cyanophenyl)acetate (239a) (0.3 g, 0.57 mmol) in DCM (8 mL) using TFA (0.88 mL, 11.39 mmol). This gave after workup and purification by flash column chromatography (silica gel 12 g, eluting with MeOH in DCM from 0-100%) compound (239b) (0.24 g, 100% yield) as a clear wax. This sample was further purified by reverse phase column chromatography [C18 (50 g), eluting with ACN in water (containing 0.1% HCl) from 0-100%] to afford methyl 2-(2-((7-(3-(aminomethyl)phenyl)benzofuran-5-yl)methoxy)-5-cyanophenyl)acetate (239b) HCl salt as a white solid; $^1$H NMR (300 MHz, DMSO-d$_6$) δ 8.32 (s, 3H), 8.12 (t, J=1.8 Hz, 1H), 7.98 (d, J=1.8 Hz, 1H), 7.93-7.87 (m, 1H), 7.80 (dt, J=8.5, 1.7 Hz, 1H), 7.73 (dt, J=3.6, 1.5 Hz, 2H), 7.64-7.49 (m, 3H), 7.32 (dd, J=8.6, 1.3 Hz, 1H), 7.10 (t, J=1.8 Hz, 1H), 5.37 (s, 2H), 4.14 (d, J=5.7 Hz, 2H), 3.71 (s, 2H), 3.47 (s, 3H); MS (ES+): 427.0 (M+1).

Step-3: Preparation of 2-(2-((7-(3-(aminomethyl)
phenyl)benzofuran-5-yl)methoxy)-5-cyanophenyl)
acetic Acid (239c)

Compound 239c was prepared according to the procedure reported in step-6 of Scheme-1 from methyl 2-(2-((7-(3-(aminomethyl)phenyl)benzofuran-5-yl)methoxy)-5-cyanophenyl)acetate (239b) (0.2 g, 0.37 mmol) in THF/methanol (4 mL, each) using a solution of lithium hydroxide hydrate (0.16 g, 3.70 mmol) in Water (1 mL). This gave after workup and purification by reverse phase column chromatography [C18 (50 g), eluting with ACN in water (containing 0.1% HCl) from 0-100%] 2-(2-((7-(3-(aminomethyl)phenyl)benzofuran-5-yl)methoxy)-5-cyanophenyl)acetic acid (239c) (0.10 g, 65% yield) as a white solid; $^1$H NMR (300 MHz, DMSO-d$_6$) δ 12.45 (s, 1H), 8.43 (s, 3H), 8.12 (d, J=2.2 Hz, 1H), 8.00 (s, 1H), 7.92 (dt, J=7.2, 1.8 Hz, 1H), 7.80-7.69 (m, 3H), 7.67-7.61 (m, 1H), 7.61-7.51 (m, 2H), 7.29 (d, J=8.6 Hz, 1H), 7.07 (d, J=2.2 Hz, 1H), 5.39 (s, 2H), 4.13 (s, 2H), 3.66 (s, 2H). MS (ES+) 413.2 (M+1), MS (ES−) 411.2 (M−1).

Scheme-240

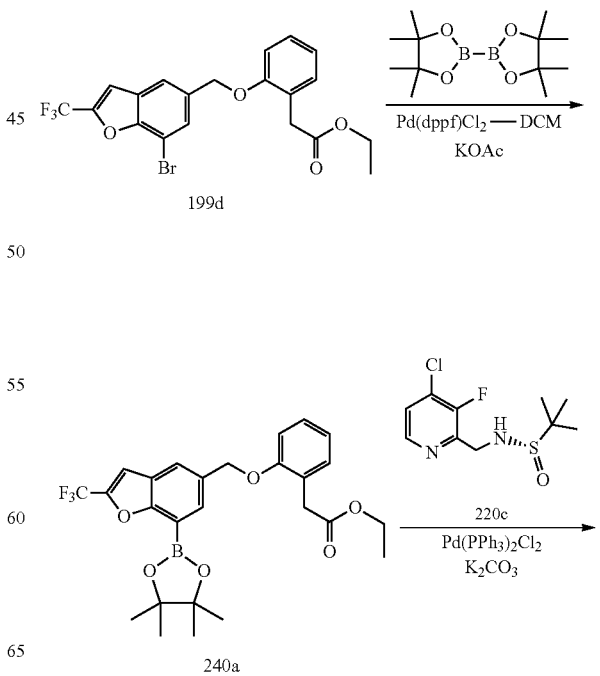

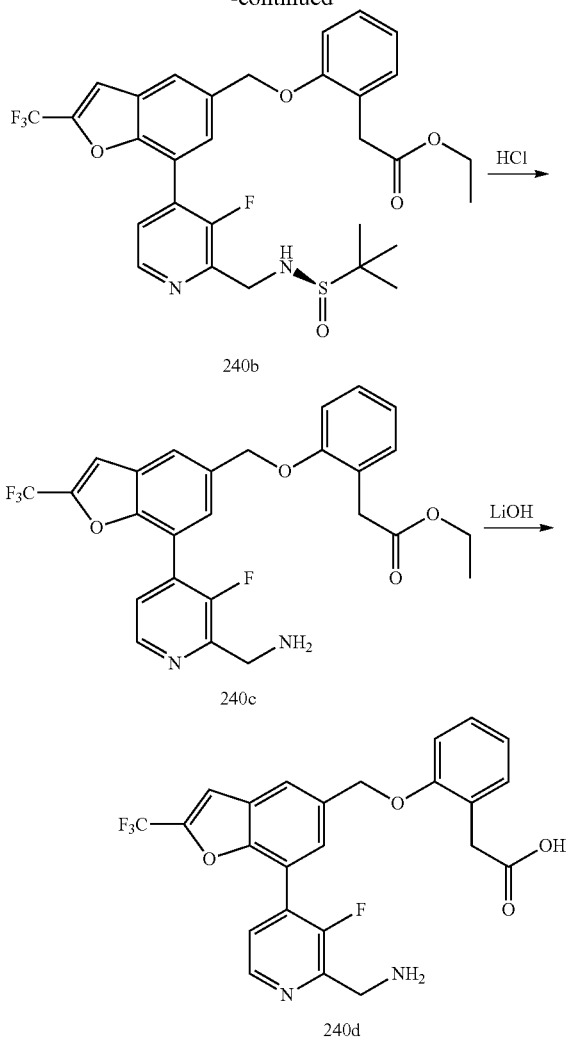

Preparation of 2-(2-((7-(2-(aminomethyl)-3-fluoropyridin-4-yl)-2-(trifluoromethyl)benzofuran-5-yl)methoxy)phenyl)acetic Acid (240d)

Step-1: Preparation of Ethyl 2-(2-((7-(4,4,5,5-tetramethyl-1,3,2-dioxaborolan-2-yl)-2-(trifluoromethyl)benzofuran-5-yl)methoxy)phenyl)acetate (240a)

Compound 240a was prepared according to the procedure reported in step-1 of Scheme-59 from ethyl 2-(2-((7-bromo-2-(trifluoromethyl)benzofuran-5-yl)methoxy)phenyl)acetate (199d) (316 mg, 0.691 mmol), using bis(pinacolato)diboron (266 mg, 1.047 mmol), potassium acetate (217 mg, 2.211 mmol) and Pd(dppf)Cl$_2$—CH$_2$Cl$_2$ (72 mg, 0.088 mmol) in anhydrous dioxane (6 mL) under an Ar atmosphere and heating at 90° C. overnight. This gave after workup and purification by flash column chromatography [silica (12 g), eluting with EtOAc in hexane from 0-50%] ethyl 2-(2-((7-(4,4,5,5-tetramethyl-1,3,2-dioxaborolan-2-yl)-2-(trifluoromethyl)benzofuran-5-yl)methoxy)phenyl)acetate (240a) (326 mg, 94% yield) as a white solid. $^1$H NMR (300 MHz, DMSO-d$_6$) δ 8.00 (d, J=1.8 Hz, 1H), 7.86 (d, J=1.8 Hz, 1H), 7.83-7.78 (m, 1H), 7.30-7.19 (m, 2H), 7.13-7.06 (m, 1H), 6.92 (td, J=7.4, 1.1 Hz, 1H), 5.23 (s, 2H), 4.00 (q, J=7.1 Hz, 2H), 3.61 (s, 2H), 1.17 (s, 12H), 1.05 (t, J=7.1 Hz, 3H); $^{19}$F NMR (282 MHz, DMSO-d$_6$) δ −63.17.

Step-2: Preparation of (S)-ethyl 2-(2-((7-(2-((1,1-dimethylethylsulfinamido)methyl)-3-fluoropyridin-4-yl)-2-(trifluoromethyl)benzofuran-5-yl)methoxy)phenyl)acetate (240b)

Compound 240b was prepared according to the procedure reported in step-3 of Scheme-1 from ethyl 2-(2-((7-(4,4,5,5-tetramethyl-1,3,2-dioxaborolan-2-yl)-2-(trifluoromethyl)benzofuran-5-yl)methoxy)phenyl)acetate (240a) (326 mg, 0.646 mmol) in dioxane (5 mL) using (S)—N-((4-chloro-3-fluoropyridin-2-yl)methyl)-2-methylpropane-2-sulfinamide (220c) (230 mg, 0.869 mmol), bis(triphenylphosphine)palladium(II) chloride (73 mg, 0.104 mmol) and a solution of K$_2$CO$_3$ (309 mg, 2.236 mmol) in water (0.5 mL) under an Ar atmosphere and heating at 100° C. for 3 h on oil bath. This gave after workup, purification by flash column chromatography [silica (12 g), eluting with DMA/DCM from 0-80%] (S)-ethyl 2-(2-((7-(2-((1,1-dimethylethylsulfinamido)methyl)-3-fluoropyridin-4-yl)-2-(trifluoromethyl)benzofuran-5-yl)methoxy)phenyl)acetate (240b) (392 mg, 100% yield) as pale-yellow oil. MS (ES+): 607.2 (M+1).

Step-3: Preparation of Ethyl 2-(2-((7-(2-(aminomethyl)-3-fluoropyridin-4-yl)-2-(trifluoromethyl)benzofuran-5-yl)methoxy)phenyl)acetate (240c)

Compound 240c was prepared according to the procedure reported in step-5 of Scheme-220 from (S)-ethyl 2-(2-((7-(2-((1,1-dimethylethylsulfinamido)methyl)-3-fluoropyridin-4-yl)-2-(trifluoromethyl)benzofuran-5-yl)methoxy)phenyl)acetate (240b) (392 mg, 0.65 mmol) in methanol (8 mL) using hydrochloric acid (4 M in 1,4-dioxane, 0.5 mL, 2 mmol). This gave after workup ethyl 2-(2-((7-(2-(aminomethyl)-3-fluoropyridin-4-yl)-2-(trifluoromethyl)benzofuran-5-yl)methoxy)phenyl)acetate (240c) (324 mg, 100% yield) HCl salt as a yellow solid. An analytical sample was obtained by further purification using reverse phase column chromatography [C18 (50 g), eluting with ACN in water (containing 0.1% HCl) from 0-100%] to afford compound 240c HCl salt as a white solid. $^1$H NMR (300 MHz, DMSO-d$_6$) δ 8.59 (q, J=6.1, 5.6 Hz, 4H), 8.03-7.95 (m, 1H), 7.90 (s, 1H), 7.75 (d, J=10.1 Hz, 2H), 7.22-7.13 (m, 2H), 7.06 (d, J=8.2 Hz, 1H), 6.86 (t, J=7.4 Hz, 1H), 5.25 (s, 2H), 4.31 (d, J=5.9 Hz, 2H), 3.87 (q, J=7.1 Hz, 2H), 3.59 (d, J=8.7 Hz, 2H), 0.92 (t, J=7.1 Hz, 3H); $^{19}$F NMR (282 MHz, DMSO-d$_6$) δ −63.44, −128.97. MS (ES+): 503.2 (M+1); MS(ES−): 501.2 (M−1).

Step-4: Preparation of 2-(2-((7-(2-(aminomethyl)-3-fluoropyridin-4-yl)-2-(trifluoromethyl)benzofuran-5-yl)methoxy)phenyl)acetic Acid (240d)

Compound 240d was prepared according to the procedure reported in step-6 of Scheme-1 from ethyl 2-(2-((7-(2-(aminomethyl)-3-fluoropyridin-4-yl)-2-(trifluoromethyl)benzofuran-5-yl)methoxy)phenyl)acetate (240c) (230 mg, 0.458 mmol) in MeOH/THF (3 mL, each) using lithium hydroxide hydrate (121 mg, 2.88 mmol) in water (2 mL). This gave after workup and purification by reverse phase column [C18 (50 g), eluting with ACN in water (containing 0.1% HCl) from 0-100%] 2-(2-((7-(2-(aminomethyl)-3-fluoropyridin-4-yl)-2-(trifluoromethyl)benzofuran-5-yl)methoxy)phenyl)acetic acid (240d) (63 mg, 29.0% yield)

HCl salt as a white solid. $^1$H NMR (300 MHz, DMSO-$d_6$) δ 8.62 (dd, J=11.0, 5.4 Hz, 4H), 8.01 (d, J=1.6 Hz, 1H), 7.86 (d, J=1.4 Hz, 1H), 7.83-7.72 (m, 2H), 7.17 (t, J=7.6 Hz, 2H), 7.03 (d, J=8.0 Hz, 1H), 6.85 (td, J=7.4, 1.1 Hz, 1H), 5.26 (s, 2H), 4.40-4.25 (m, 2H), 3.53 (s, 2H); $^{19}$F NMR (282 MHz, DMSO-$d_6$) δ –63.46, –128.80. MS (ES+): 475.2 (M+1); MS (ES–): 473.2 (M–1).

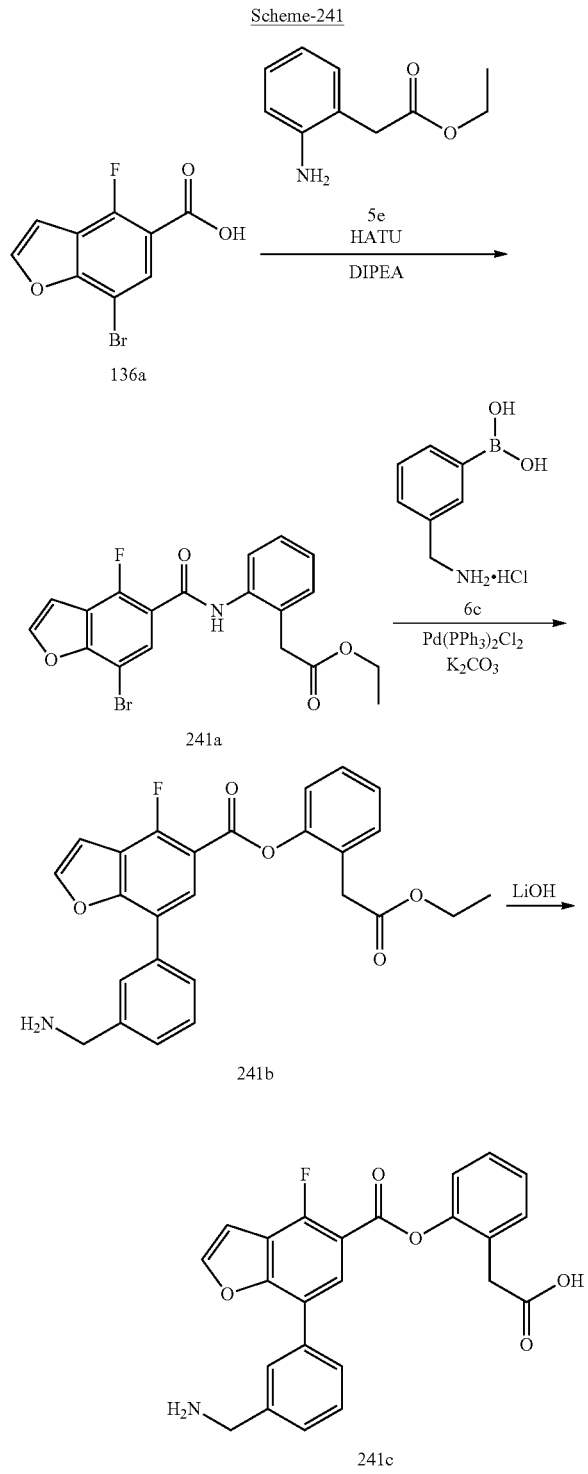

Preparation of 2-(2-(7-(3-(aminomethyl)phenyl)-4-fluorobenzofuran-5-carboxamido)phenyl)acetic Acid (241c)

Step-1: Preparation of Ethyl 2-(2-(7-bromo-4-fluorobenzofuran-5-carboxamido)phenyl)acetate (241a)

Compound 241a was prepared according to the procedure reported in step-4 of Scheme-1 from 7-bromo-4-fluorobenzofuran-5-carboxylic acid (136a) (380 mg, 1.467 mmol) in DMF (10 mL) using ethyl 2-(2-aminophenyl)acetate (5e) (334 mg, 1.864 mmol), DIPEA (1.3 mL, 7.46 mmol) and HATU (891 mg, 2.343 mmol). This gave after workup and purification by flash column chromatography (Silica gel 12 g, eluting with ethyl acetate in hexane from 0-50%) ethyl 2-(2-(7-bromo-4-fluorobenzofuran-5-carboxamido)phenyl)acetate (241a) (608 mg, 99% yield) as a yellow solid. $^1$H NMR (300 MHz, DMSO-$d_6$) δ 10.02 (s, 1H), 8.30 (d, J=2.2 Hz, 1H), 7.84 (d, J=5.9 Hz, 1H), 7.48 (d, J=7.7 Hz, 1H), 7.40-7.30 (m, 3H), 7.28-7.20 (m, 1H), 4.06 (qd, J=7.1, 2.8 Hz, 2H), 3.78 (s, 2H), 1.16 (dt, J=14.2, 7.1 Hz, 3H).

Step-2: Preparation of Ethyl 2-(2-(7-(3-(aminomethyl)phenyl)-4-fluorobenzofuran-5-carboxamido)phenyl)acetate (241b)

Compound 241b was prepared according to the procedure reported in step-3 of Scheme-1 from ethyl 2-(2-(7-bromo-4-fluorobenzofuran-5-carboxamido)phenyl)acetate (241a) (125 mg, 0.297 mmol) in dioxane (5 mL) using 3-(aminomethyl)phenylboronic acid hydrochloride (6c) (71 mg, 0.379 mmol), bis(triphenylphosphine)palladium(II) chloride (35 mg, 0.050 mmol) and a solution of $K_2CO_3$ (148 mg, 1.071 mmol) in water (0.5 mL) under an Ar atmosphere and heating at 100° C. for 3 h on oil bath. This gave after workup, purification by flash column chromatography [silica gel (12 g), eluting with DMA80/DCM, from 0-80%] ethyl 2-(2-(7-(3-(aminomethyl)phenyl)-4-fluorobenzofuran-5-carboxamido)phenyl)acetate (241b) (94 mg, 71% yield) as a pale-yellow oil. $^1$H NMR (300 MHz, DMSO-$d_6$) δ 9.99 (s, 1H), 8.25 (d, J=2.2 Hz, 1H), 7.82 (d, J=6.6 Hz, 2H), 7.72 (d, J=7.6 Hz, 1H), 7.48 (dq, J=16.2, 8.0 Hz, 3H), 7.39-7.29 (m, 3H), 7.29-7.19 (m, 1H), 4.03 (qd, J=7.1, 2.8 Hz, 2H), 3.81 (d, J=7.0 Hz, 4H), 1.09 (t, J=7.1 Hz, 3H); $^{19}$F NMR (282 MHz, DMSO-$d_6$) δ –120.55. MS (ES+): 447.2 (M+1).

Step-3: Preparation of 2-(2-(7-(3-(aminomethyl)phenyl)-4-fluorobenzofuran-5-carboxamido)phenyl)acetic Acid (241c)

Compound 241c was prepared according to the procedure reported in step-6 of Scheme-1, from ethyl 2-(2-(7-(3-(aminomethyl)phenyl)-4-fluorobenzofuran-5-carboxamido)phenyl)acetate (241b) (92 mg, 0.206 mmol) in MeOH/THF (3 mL, each) using a solution of lithium hydroxide hydrate (52 mg, 1.24 mmol) in water (2 mL). This gave after workup and purification by reverse phase column chromatography [C18 (50 g), eluting with ACN in water (containing 0.1% HCl) from 0-100%] 2-(2-(7-(3-(aminomethyl)phenyl)-4-fluorobenzofuran-5-carboxamido)phenyl)acetic acid (241c) (43 mg, 50% yield) as a white solid. $^1$H NMR (300 MHz, DMSO-$d_6$) δ 10.04 (d, J=2.2 Hz, 1H), 8.54 (s, 2H), 8.20 (d, J=2.3 Hz, 1H), 7.95 (s, 1H), 7.86 (dd, J=6.2, 3.9 Hz, 2H), 7.53 (dd, J=5.7, 3.8 Hz, 3H), 7.32-7.21 (m, 3H), 7.15 (td, J=7.3, 1.4 Hz, 1H), 4.07 (s, 2H), 3.67 (s, 2H); $^{19}$F NMR (282 MHz, DMSO-$d_6$) δ –119.62. MS (ES+): 419.0 (M+1); MS (ES–): 417.9 (M–1). HPLC purity 99.53%.

Scheme-242

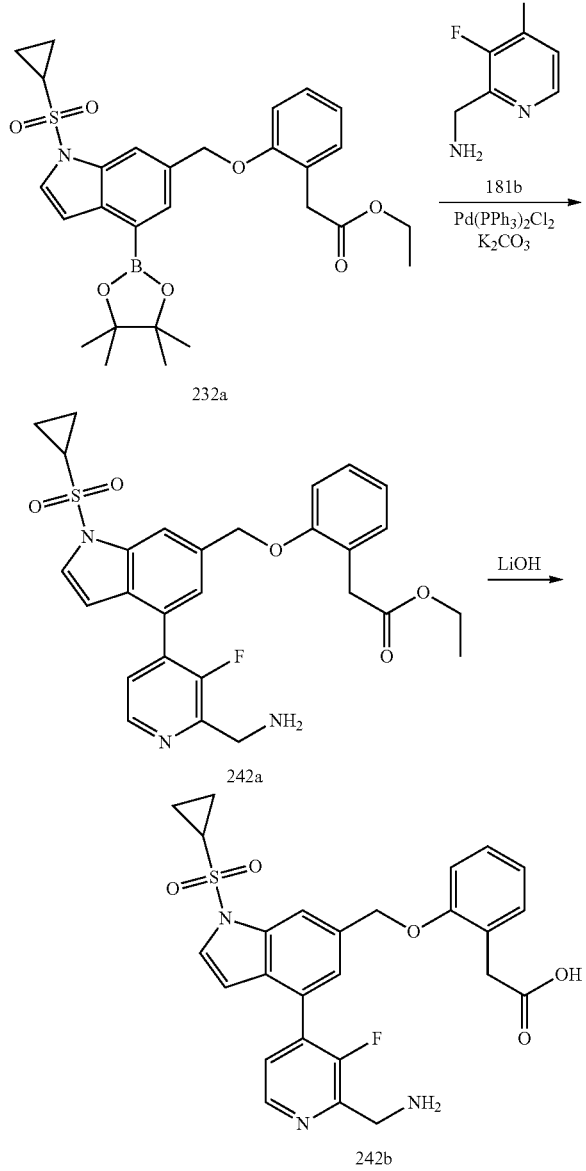

Preparation of 2-(2-((4-(2-(aminomethyl)-3-fluoro-pyridin-4-yl)-1-(cyclopropylsulfonyl)-1H-indol-6-yl)methoxy)phenyl)acetic Acid (242b)

Step-1: Preparation of Ethyl 2-(2-((4-(2-(aminomethyl)-3-fluoropyridin-4-yl)-1-(cyclopropylsulfonyl)-1H-indol-6-yl)methoxy)phenyl)acetate (242a)

Compound 242a was prepared according to the procedure reported in step-3 of Scheme-1 from ethyl 2-(2-((1-(cyclopropylsulfonyl)-4-(4,4,5,5-tetramethyl-1,3,2-dioxaborolan-2-yl)-1H-indol-6-yl)methoxy)phenyl)acetate (232a) (0.33 g, 0.61 mmol) in dioxane (5 mL) using (4-chloro-3-fluoropyridin-2-yl)methanamine (181b) (0.15 g, 0.92 mmol), bis(triphenylphosphine)palladium(II) chloride (0.06 g, 0.09 mmol) and a solution of K$_2$CO$_3$ (0.211 g, 1.53 mmol) in water (0.5 mL) under an Ar atmosphere and heating at 90° C. for 4 h on oil bath. This gave after workup, purification by flash column chromatography [silica (12 g), eluting with DMA80 in DCM from 0-50%] followed by purification by reverse-phase column chromatography [C18 (50 g), eluting with ACN in water (containing 0.1% HCl) from 0-100%] ethyl 2-(2-((4-(2-(aminomethyl)-3-fluoropyridin-4-yl)-1-(cyclopropylsulfonyl)-1H-indol-6-yl)methoxy)phenyl)acetate (242a) (0.11 g, 33% yield) HCl salt as a yellow solid; MS (ES+): 538.2 (M+1).

Step-2: Preparation of 2-(2-((4-(2-(aminomethyl)-3-fluoropyridin-4-yl)-1-(cyclopropylsulfonyl)-1H-indol-6-yl)methoxy)phenyl)acetic Acid (242b)

Compound 242b was prepared according to the procedure reported in step-6 of Scheme-1 from ethyl 2-(2-((4-(2-(aminomethyl)-3-fluoropyridin-4-yl)-1-(cyclopropylsulfonyl)-1H-indol-6-yl)methoxy)phenyl)acetate (242a) (0.11 g, 0.21 mmol) in THF/MeOH (4 mL, each) using lithium hydroxide hydrate (0.09 g, 2.05 mmol) in water (1 mL). This gave after workup and purification by reverse phase column [C18 (50 g), eluting with ACN in water (containing 0.1% HCl) from 0-100%] 2-(2-((4-(2-(aminomethyl)-3-fluoropyridin-4-yl)-1-(cyclopropylsulfonyl)-1H-indol-6-yl)methoxy)phenyl)acetic acid (242b) (0.01 g, 10% yield) HCl salt as a yellow solid; $^1$H NMR (300 MHz, DMSO-d$_6$) δ 12.17 (s, 1H), 8.61 (d, J=5.0 Hz, 1H), 8.46 (s, 3H), 8.16 (s, 1H), 7.78 (d, J=3.8 Hz, 1H), 7.70 (t, J=5.3 Hz, 1H), 7.56 (s, 1H), 7.29-7.19 (m, 2H), 7.12 (d, J=8.1 Hz, 1H), 6.92 (dd, J=7.9, 6.8 Hz, 1H), 6.75 (t, J=3.5 Hz, 1H), 5.35 (s, 2H), 4.38 (d, J=6.0 Hz, 2H), 3.59 (s, 2H), 3.25-3.07 (m, 1H), 1.35-1.06 (m, 4H); $^{19}$F NMR (282 MHz, DMSO-d$_6$) δ−128.57; MS (ES+): 510.9 (M+1), MS (ES−): 508.9 (M−1). HPLC purity: 96.58%.

Scheme-243

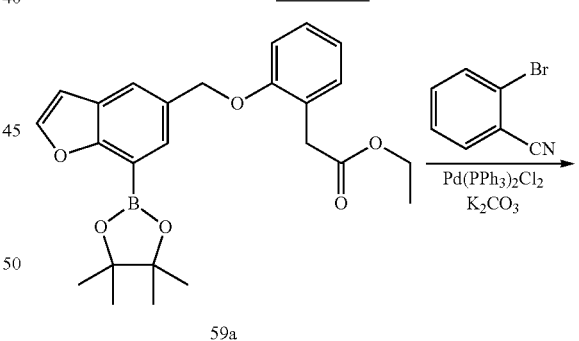

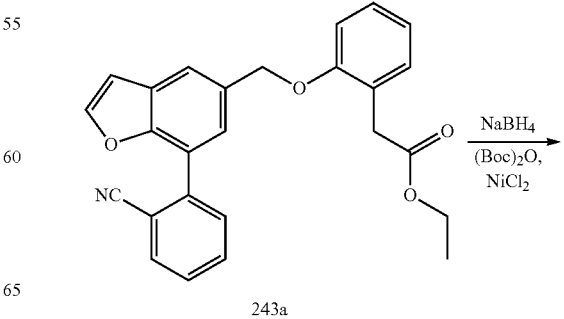

-continued

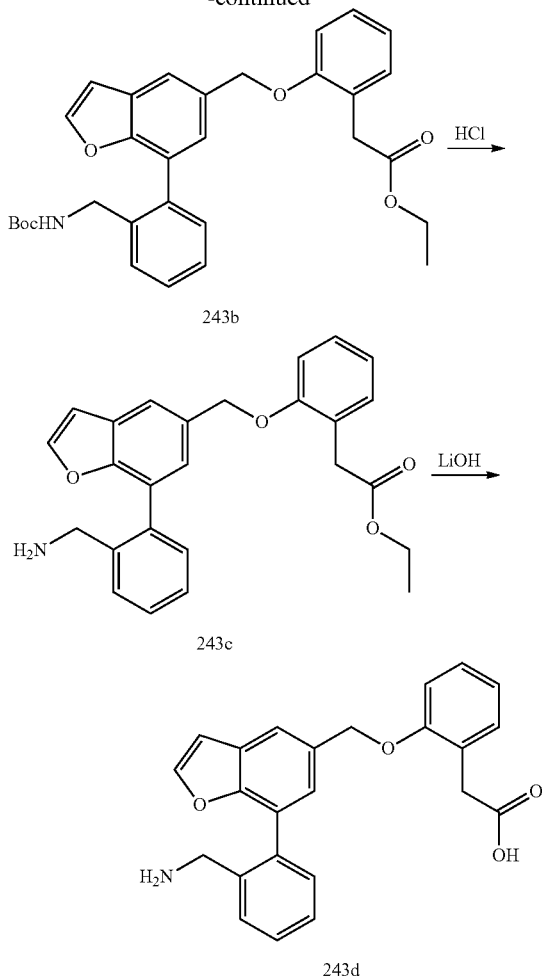

Preparation of 2-(2-((7-(2-(aminomethyl)phenyl)benzofuran-5-yl)methoxy)phenyl)acetic acid (243d)

Step-1: Preparation of Ethyl 2-(2-((7-(2-cyanophenyl)benzofuran-5-yl)methoxy)phenyl)acetate (243a)

Compound 243a was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (500 mg, 1.146 mmol) in dioxane (2 mL) using 2-bromobenzonitrile (229 mg, 1.261 mmol), Pd(PPh$_3$)$_2$Cl$_2$ (80 mg, 0.115 mmol) and a solution of K$_2$CO$_3$ (475 mg, 3.44 mmol) in water (1 mL) under a nitrogen atmosphere and heating at 100° C. for 16 h on oil bath. This gave after workup and purification by flash column chromatography (silica gel, eluting with ethyl acetate in hexane from 0-15%) ethyl 2-(2-((7-(2-cyanophenyl)benzofuran-5-yl)methoxy)phenyl)acetate (243a) (293 mg, 62% yield) as a pale magenta thick oil. $^1$H NMR (300 MHz, Chloroform-d) δ 7.90-7.83 (m, 1H), 7.81-7.68 (m, 4H), 7.58-7.49 (m, 2H), 7.28 (m, 1H), 7.25 (d, J=7.0 Hz, 1H), 7.04-6.94 (m, 2H), 6.89 (d, J=2.2 Hz, 1H), 5.26 (s, 2H), 4.07 (q, J=7.1 Hz, 2H), 3.72 (s, 2H), 1.14 (t, J=7.1 Hz, 3H); MS (ES+): 412 (M+1).

Step-2: Preparation of Ethyl 2-(2-((7-(2-(((tert-butoxycarbonyl)amino)methyl)phenyl)benzofuran-5-yl)methoxy)phenyl)acetate (243b)

Compound 243b was prepared according to the procedure reported in step-2 of Scheme-236 from ethyl 2-(2-((7-(2-cyanophenyl)benzofuran-5-yl)methoxy)phenyl)acetate (243a) (0.28 g, 0.681 mmol) in methanol (10 mL) using Boc anhydride (0.297 g, 1.361 mmol), nickel(II) chloride hexahydrate (0.016 g, 0.068 mmol), sodium borohydride (0.180 g, 4.76 mmol) and N1-(2-aminoethyl)ethane-1,2-diamine (0.147 mL, 1.361 mmol). This gave after workup and purification by flash column chromatography ethyl 2-(2-((7-(2-(((tert-butoxycarbonyl)amino)methyl)phenyl)benzofuran-5-yl)methoxy)phenyl)acetate (243b).

Step-3: Preparation of Ethyl 2-(2-((7-(2-(aminomethyl)phenyl)benzofuran-5-yl)methoxy)phenyl)acetate (243c)

Compound 243c was prepared according to the procedure reported in step-5 of Scheme-220 from ethyl 2-(2-((7-(2-(((tert-butoxycarbonyl)amino)methyl)phenyl)benzofuran-5-yl)methoxy)phenyl)acetate (243b) (from step-2) in methanol (8 mL) using hydrochloric acid (1.5 M in methanol, 24.95 mL, 37.4 mmol). This gave after workup and purification by flash column chromatography ethyl 2-(2-((7-(2-(aminomethyl)phenyl)benzofuran-5-yl)methoxy)phenyl)acetate (243c) as a thick clear colorless oil.

Step-4: Preparation of 2-(2-((7-(2-(aminomethyl)phenyl)benzofuran-5-yl)methoxy)phenyl)acetic Acid (243d)

Compound 243d was prepared according to the procedure reported in step-6 of Scheme-1 from ethyl 2-(2-((7-(2-(aminomethyl)phenyl)benzofuran-5-yl)methoxy)phenyl)acetate (243c) (from step-3) in MeOH (2 mL), THF (1 mL each) using a solution of lithium hydroxide monohydrate (0.143 g, 3.40 mmol) in water (1 mL). This gave after workup and purification by reverse phase column [C18 (50 g), eluting with ACN in water (containing 0.1% HCl) from 0-100%] 2-(2-((7-(2-(aminomethyl)phenyl)benzofuran-5-yl)methoxy)phenyl)acetic acid (243d) (75 mg, 28% yield for 3 steps) HCl salt as a white solid; $^1$H NMR (300 MHz, DMSO-d$_6$) δ 8.02 (d, J=2.2 Hz, 1H), 7.82 (d, J=1.6 Hz, 1H), 7.75 (d, J=7.5 Hz, 1H), 7.64-7.43 (m, 3H), 7.39 (d, J=1.7 Hz, 1H), 7.32-7.19 (m, 2H), 7.15-7.02 (m, 2H), 6.91 (dd, J=7.9, 6.8 Hz, 1H), 5.26 (s, 2H), 3.87 (s, 2H), 3.59 (s, 2H). HPLC purity: 98.7%; MS (ES+): 388 (M+1); MS (ES−): 386 (M−1); Analysis calculated for C$_{24}$H$_{21}$NO$_4$.HCl.1.5H$_2$O: C, 63.93; H, 5.59; N, 3.11; Cl, 7.86; Found: C, 64.11; H, 5.33; N, 3.11; Cl, 8.06.

Scheme-244

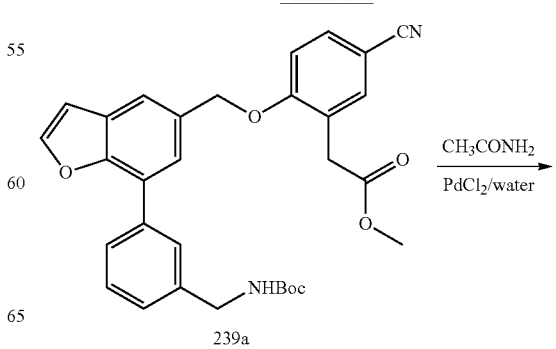

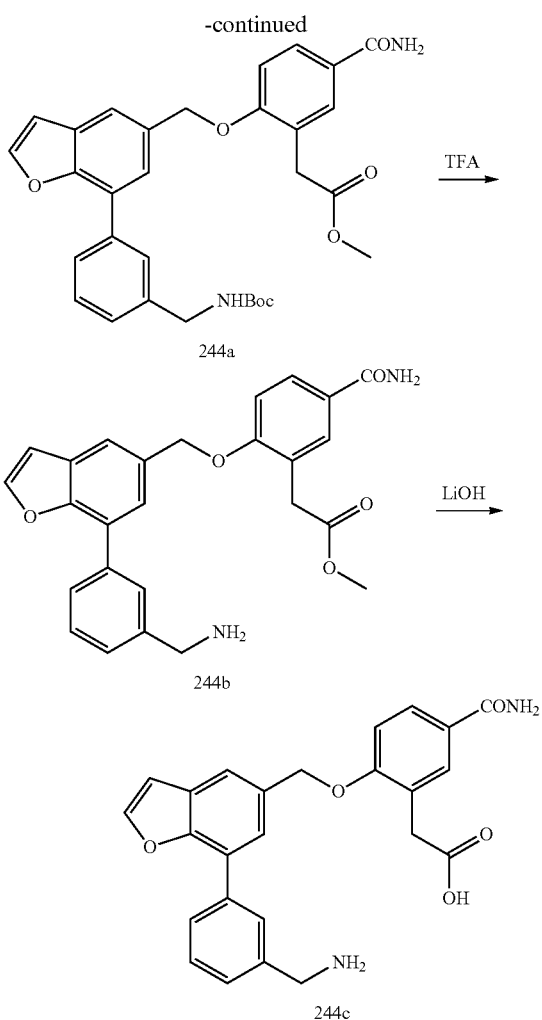

Preparation of 2-(2-((7-(3-(aminomethyl)phenyl) benzofuran-5-yl)methoxy)-5-carbamoylphenyl)acetic Acid (244c)

Step-1: Preparation of methyl 2-(2-((7-(3-(((tert-butoxycarbonyl)amino)methyl)phenyl)benzofuran-5-yl)methoxy)-5-carbamoylphenyl)acetate (244a)

Compound 244a was prepared according to the procedure reported in step-1 of Scheme-238 from methyl 2-(2-((7-(3-(((tert-butoxycarbonyl)amino)methyl)phenyl)benzofuran-5-yl)methoxy)-5-cyanophenyl)acetate (239a) (0.32 g, 0.61 mmol) using acetamide (0.22 g, 3.65 mmol), palladium(II) chloride (0.02 g, 0.09 mmol) in THF (4 mL) and water (0.4 mL). This gave after workup and purification by flash phase column chromatography (silica gel 12 g, eluting with methanol in DCM from 0 to 100%) methyl 2-(2-((7-(3-(((tert-butoxycarbonyl)amino)methyl)phenyl)benzofuran-5-yl)methoxy)-5-carbamoylphenyl)acetate (244a) (0.18 g, 54% yield) as a white solid; MS (ES+): 543.0 (M−1).

Step-2: Preparation of methyl 2-(2-((7-(3-(aminomethyl)phenyl)benzofuran-5-yl)methoxy)-5-carbamoylphenyl)acetate (244b)

Compound 244b was prepared according to the procedure reported in step-5 of Scheme-1 from methyl 2-(2-((7-(3-(((tert-butoxycarbonyl)amino)methyl)phenyl)benzofuran-5-yl)methoxy)-5-carbamoylphenyl)acetate (244a) (0.18 g, 0.33 mmol) in DCM (6 mL) using TFA (0.51 mL, 6.61 mmol). This gave after workup and purification by flash phase column chromatography (silica gel 12 g, eluting with methanol in DCM from 0-50%) methyl 2-(2-((7-(3-(aminomethyl)phenyl)benzofuran-5-yl)methoxy)-5-carbamoylphenyl)acetate (244b) (0.12 g, 82% yield) as a white wax; $^1$H NMR (300 MHz, DMSO-$d_6$) δ 8.21 (s, 4H), 8.12 (d, J=2.2 Hz, 1H), 7.98 (d, J=1.8 Hz, 1H), 7.91 (dt, J=7.8, 1.5 Hz, 1H), 7.85-7.77 (m, 3H), 7.74 (d, J=1.6 Hz, 1H), 7.65-7.57 (m, 2H), 7.57-7.50 (m, 1H), 7.24-7.14 (m, 2H), 7.10 (d, J=2.2 Hz, 1H), 5.33 (s, 2H), 4.15 (s, 2H), 3.68 (s, 2H), 3.47 (s, 3H); MS (ES+): 445.1 (M+1), MS (ES−): 443.0 (M−1).

Step-3: Preparation of 2-(2-((7-(3-(aminomethyl) phenyl)benzofuran-5-yl)methoxy)-5-carbamoylphenyl)acetic Acid (244c)

Compound 244c was prepared according to the procedure reported in step-6 of Scheme-1 from methyl 2-(2-((7-(3-(aminomethyl)phenyl)benzofuran-5-yl)methoxy)-5-carbamoylphenyl)acetate (244b) (0.11 g, 0.25 mmol) in THF/MeOH (4 mL, each) using a solution of lithium hydroxide hydrate (0.10 g, 2.48 mmol) in water (1 mL). This gave after workup and purification by reverse-phase column chromatography (EZ-PREP, C-18 column, 50 g, eluting with 0.1% aq. HCl in water and acetonitrile from 0-100%) 2-(2-((7-(3-(aminomethyl)phenyl)benzofuran-5-yl)methoxy)-5-carbamoylphenyl)acetic acid (244c) (0.06 g, 58% yield) as a white solid; $^1$H NMR (300 MHz, DMSO-$d_6$) δ 12.35 (s, 1H), 8.39 (s, 3H), 8.11 (d, J=2.2 Hz, 1H), 8.00 (d, J=1.9 Hz, 1H), 7.93 (dt, J=7.4, 1.7 Hz, 1H), 7.84-7.75 (m, 4H), 7.65 (d, J=1.6 Hz, 1H), 7.63-7.52 (m, 2H), 7.22-7.11 (m, 2H), 7.07 (d, J=2.2 Hz, 1H), 5.35 (s, 2H), 4.14 (s, 2H), 3.62 (s, 2H); MS (ES+): 431.0 (M+1), MS (ES−): 429.0 (M−1). HPLC purity: 99.75%.

Scheme-245

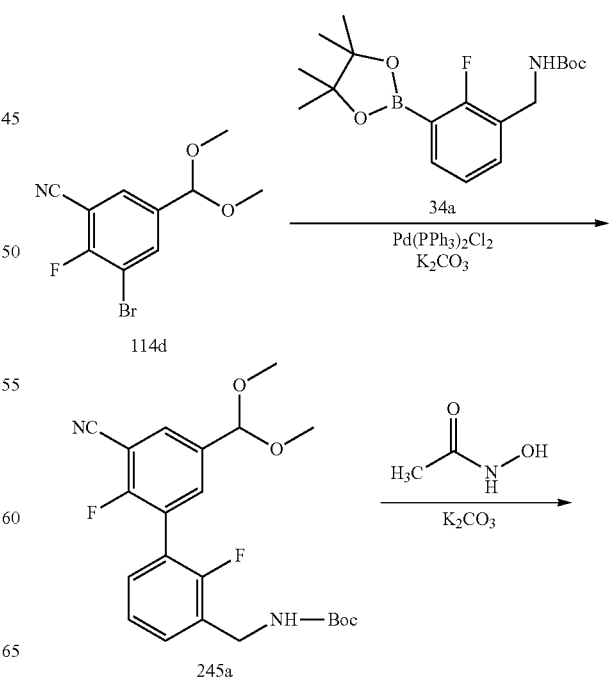

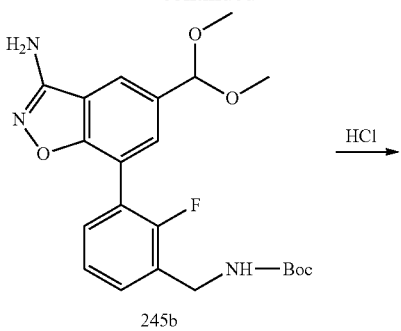

245b

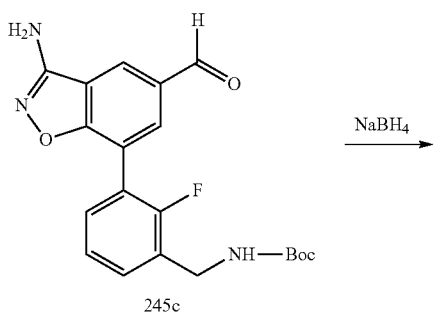

245c

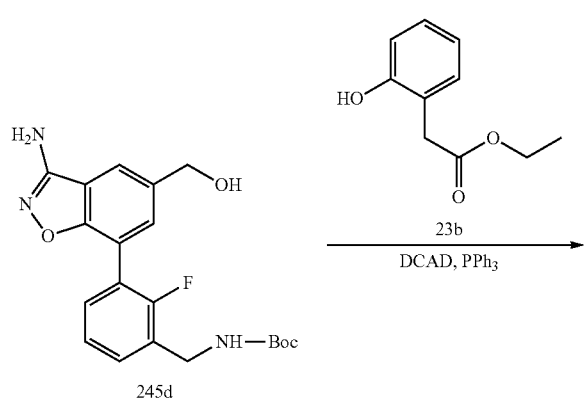

245d

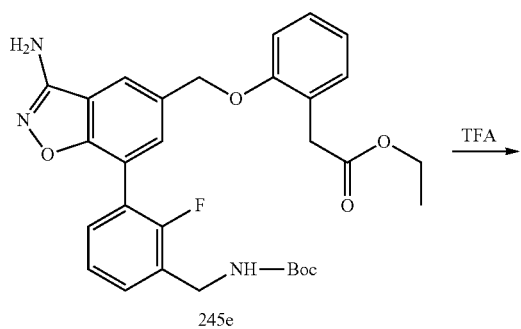

245e

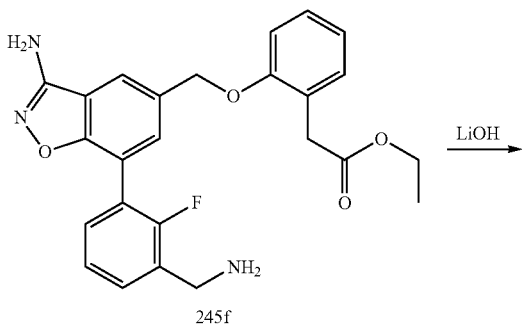

245f

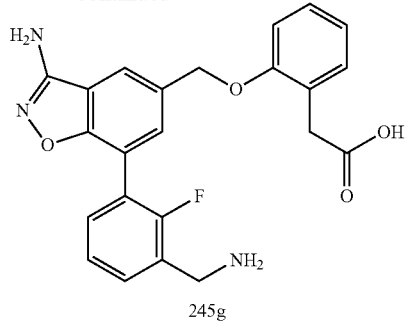

245g

Preparation of 2-(2-((3-amino-7-(3-(aminomethyl)-2-fluorophenyl)benzo[d]isoxazol-5-yl)methoxy)phenyl)acetic Acid (245g)

Step-1: Preparation of tert-butyl ((3'-cyano-5'-(dimethoxymethyl)-2,2'-difluoro-[1,1'-biphenyl]-3-yl)methyl)carbamate (245a)

Compound 245a was prepared according to the procedure reported in step-3 of Scheme-1 from 3-bromo-5-(dimethoxymethyl)-2-fluorobenzonitrile (114d) (600 mg, 2.189 mmol) in dioxane (30 mL) using tert-butyl 2-fluoro-3-(4,4,5,5-tetramethyl-1,3,2-dioxaborolan-2-yl)benzylcarbamate (34a) (1153 mg, 3.28 mmol), Pd(PPh$_3$)$_2$Cl$_2$ (307 mg, 0.438 mmol) and a solution of K$_2$CO$_3$ (908 mg, 6.57 mmol) in water (3 mL) under a nitrogen atmosphere and heating at 100° C. for 3 h on oil bath. This gave after workup and purification by flash column chromatography [silica gel, eluting with hexanes/ethyl acetate (1:0 to 3:1)] tert-butyl ((3'-cyano-5'-(dimethoxymethyl)-2,2'-difluoro-[1,1'-biphenyl]-3-yl)methyl)carbamate (245a) (549 mg, 60%) as a light yellow gum; $^1$H NMR (300 MHz, DMSO-d$_6$) δ 7.96 (ddd, J=5.9, 2.2, 0.6 Hz, 1H), 7.78 (dd, J=7.1, 2.2 Hz, 1H), 7.53-7.28 (m, 4H), 5.55-5.42 (m, 1H), 4.24 (d, J=6.1 Hz, 2H), 3.29 (s, 6H), 1.40 (s, 9H); $^{19}$F NMR (282 MHz, DMSO-d$_6$) δ−110.59 (d, J=17.5 Hz), −121.69 (d, J=17.5 Hz); MS (ES+): 441.20 (M+Na).

Step-2: Preparation of tert-butyl 3-(3-amino-5-(dimethoxymethyl)benzo[d]isoxazol-7-yl)-2-fluorobenzylcarbamate (245b)

Compound 245b was prepared according to the procedure reported in step-4 of Scheme-114 from tert-butyl ((3'-cyano-5'-(dimethoxymethyl)-2,2'-difluoro-[1,1'-biphenyl]-3-yl)methyl)carbamate (245a) (535 mg, 1.279 mmol) in DMF (15 mL) using N-hydroxyacetamide (297 mg, 3.84 mmol), potassium carbonate (530 mg, 3.84 mmol). This gave after workup and purification by flash column chromatography [silica gel, eluting with hexanes/ethyl acetate (1:0 to 1:1)] tert-butyl 3-(3-amino-5-(dimethoxymethyl)benzo[d]isoxazol-7-yl)-2-fluorobenzylcarbamate (245b) (382 mg, 69%) as white solid; $^1$H NMR (300 MHz, DMSO-d$_6$) δ 7.98 (dd, J=1.6, 0.7 Hz, 1H), 7.58-7.56 (m, 1H), 7.54-7.45 (m, 2H), 7.42-7.27 (m, 2H), 6.55 (s, 2H), 5.56 (s, 1H), 4.25 (d, J=6.1 Hz, 2H), 3.29 (s, 6H), 1.40 (s, 9H); $^{19}$F NMR (282 MHz, DMSO-d$_6$) δ−121.39; MS (ES+): 432.20 (M+1) & 454.20 (M+Na); MS (ES−): 430.20 (M−1).

Step-3: Preparation of tert-butyl 3-(3-amino-5-formylbenzo[d]isoxazol-7-yl)-2-fluorobenzylcarbamate (245c)

Compound 245c was prepared according to the procedure reported in step-5 of Scheme-114 from tert-butyl 3-(3- amino-5-(dimethoxymethyl)benzo[d]isoxazol-7-yl)-2-fluorobenzylcarbamate (245b) (300 mg, 0.695 mmol) in THF (12 mL) using conc. hydrogen chloride (0.145 mL, 1.738 mmol). This gave after workup tert-butyl 3-(3-amino-5-formylbenzo[d]isoxazol-7-yl)-2-fluorobenzylcarbamate (245c) (267 mg) as white solid, which was used as such for next step; MS (ES+): 408.10 (M+Na).

Step-4: Preparation of tert-butyl 3-(3-amino-5-(hydroxymethyl)benzo[d]isoxazol-7-yl)-2-fluorobenzylcarbamate (245d)

Compound 245d was prepared according to the procedure reported in step-6 of Scheme-114 from tert-butyl 3-(3-amino-5-formylbenzo[d]isoxazol-7-yl)-2-fluorobenzylcarbamate (245c) (264 mg, 0.685 mmol) in THF (20 mL) using sodium borohydride (52 mg, 1.370 mmol). This gave after workup and purification by flash column chromatography [silica gel, eluting with hexanes/10% methanol in ethyl acetate (1:0 to 1:1)] tert-butyl 3-(3-amino-5-(hydroxymethyl)benzo[d]isoxazol-7-yl)-2-fluorobenzylcarbamate (245d) (179 mg, 68% for 2 steps) as a white solid; $^1$H NMR (300 MHz, DMSO-$d_6$) δ 7.86-7.83 (m, 1H), 7.52-7.44 (m, 3H), 7.42-7.26 (m, 2H), 6.47 (s, 2H), 5.37 (t, J=5.6 Hz, 1H), 4.63 (d, J=5.6 Hz, 2H), 4.25 (d, J=6.1 Hz, 2H), 1.41 (s, 9H); $^{19}$F NMR (282 MHz, DMSO-$d_6$) δ−121.17; MS (ES+): 388.20 (M+1) & 410.10 (M+Na).

Step-5: Preparation of Ethyl 2-(2-((3-amino-7-(3-(((tert-butoxycarbonyl)amino)methyl)-2-fluorophenyl)benzo[d]isoxazol-5-yl)methoxy)phenyl)acetate (245e)

Compound 245e was prepared according to the procedure reported in step-2 of Scheme-23 from tert-butyl 3-(3-amino-5-(hydroxymethyl)benzo[d]isoxazol-7-yl)-2-fluorobenzylcarbamate (245d) (170 mg, 0.439 mmol) in DCM (12 mL) and THF (12 mL) using triphenylphosphine (173 mg, 0.658 mmol), ethyl 2-(2-hydroxyphenyl) acetate (23b) (198 mg, 1.097 mmol) and a solution of di-(4-chlorobenzyl)azodicarboxylate (DCAD, 242 mg, 0.658 mmol) in DCM (12 mL). This gave after workup and purification by flash column chromatography [silica gel, eluting with hexanes/ethyl acetate (1:0 to 1:1)] ethyl 2-(2-((3-amino-7-(3-(((tert-butoxycarbonyl)amino)methyl)-2-fluorophenyl)benzo[d]isoxazol-5-yl)methoxy)phenyl)acetate (245e) (240 mg, 100%) as a white solid; $^1$H NMR (300 MHz, DMSO-$d_6$) δ 7.94 (d, J=1.5 Hz, 1H), 7.65 (s, 1H), 7.55-7.17 (m, 6H), 7.15-7.11 (m, 1H), 6.97-6.87 (m, 1H), 6.52 (s, 2H), 5.20 (s, 2H), 4.25 (d, J=6.1 Hz, 2H), 3.85 (q, J=7.1 Hz, 2H), 3.61 (s, 2H), 1.40 (s, 9H), 0.93 (t, J=7.1 Hz, 3H); $^{19}$F NMR (282 MHz, DMSO-$d_6$) δ−120.90; MS (ES+): 550.20 (M+1) & 572.30 (M+Na).

Step-6: Preparation of Ethyl 2-(2-((3-amino-7-(3-(aminomethyl)-2-fluorophenyl)benzo[d]isoxazol-5-yl)methoxy)phenyl)acetate (245f)

Compound 245f was prepared according to the procedure reported in step-5 of Scheme-1 from ethyl 2-(2-((3-amino-7-(3-(((tert-butoxycarbonyl)amino)methyl)-2-fluorophenyl)benzo[d]isoxazol-5-yl)methoxy)phenyl)acetate (245e) (220 mg, 0.400 mmol) in DCM (12 mL) using TFA (0.308 mL, 4.00 mmol). This gave after workup and purification by flash column chromatography [silica gel, eluting with dichloromethane/DMA 80 (1:0 to 3:1)]ethyl 2-(2-((3-amino-7-(3-(aminomethyl)-2-fluorophenyl)benzo[d]isoxazol-5-yl)methoxy)phenyl)acetate (245f) (125 mg, 70%) as a white solid; $^1$H NMR (300 MHz, DMSO-$d_6$) δ 7.94 (d, J=1.6 Hz, 1H), 7.67-7.57 (m, 2H), 7.54-7.47 (m, 1H), 7.34 (t, J=7.6 Hz, 1H), 7.30-7.19 (m, 2H), 7.15-7.11 (m, 1H), 6.96-6.88 (m, 1H), 6.52 (s, 2H), 5.20 (s, 2H), 3.92-3.82 (m, 4H), 3.61 (s, 2H), 0.94 (t, J=7.1 Hz, 3H); MS (ES+): 450.20 (M+1) & 472.20 (M+Na).

Step-7: Preparation of 2-(2-((3-amino-7-(3-(aminomethyl)-2-fluorophenyl)benzo[d]isoxazol-5-yl)methoxy)phenyl)acetic Acid (245g)

Compound 245g was prepared according to the procedure reported in step-6 of Scheme-1, from ethyl 2-(2-((3-amino-7-(3-(aminomethyl)-2-fluorophenyl)benzo[d]isoxazol-5-yl)methoxy)phenyl)acetate (245f) (85 mg, 0.189 mmol) in THF/MeOH (6 mL, each) using a solution of lithium hydroxide hydrate (81 mg, 1.891 mmol) in water (6 mL). This gave after workup and purification by reverse phase column chromatography [C18 column, eluting with water (containing 0.1% HCl)/acetonitrile (1:0 to 0:1)] 2-(2-((3-amino-7-(3-(aminomethyl)-2-fluorophenyl)benzo[d]isoxazol-5-yl)methoxy)phenyl)acetic acid (245g) (54 mg, 68%) HCl salt as a white solid; $^1$H NMR (300 MHz, DMSO-$d_6$) δ 8.50 (s, 3H), 7.98 (d, J=1.5 Hz, 1H), 7.74-7.63 (m, 3H), 7.43 (t, J=7.7 Hz, 1H), 7.29-7.19 (m, 2H), 7.13-7.08 (m, 1H), 6.92 (td, J=7.4, 1.1 Hz, 1H), 5.24 (s, 2H), 4.21-4.11 (m, 2H), 3.59 (s, 2H); $^{19}$F NMR (282 MHz, DMSO-$d_6$) δ−118.35; MS (ES+): 422.0 (M+1); MS (ES−): 419.90 (M−1).

Scheme-246

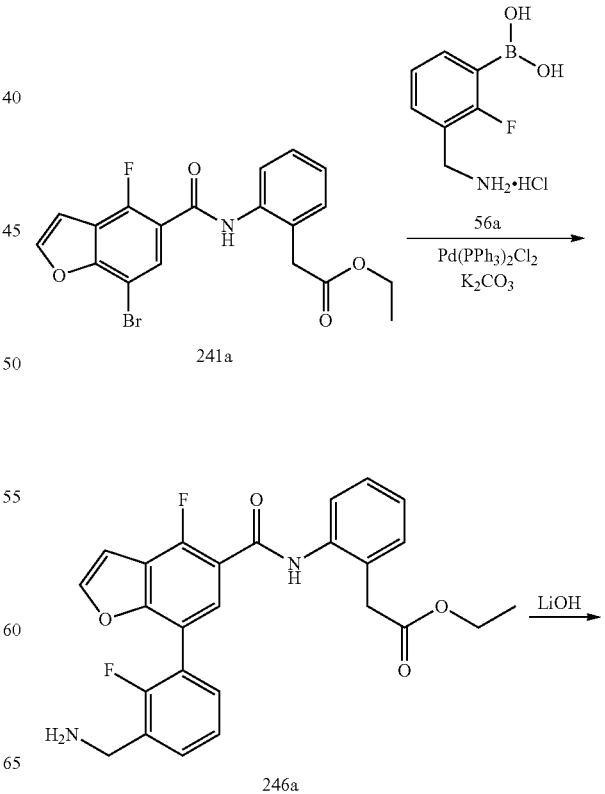

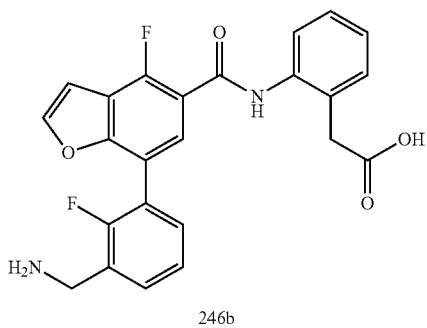

246b

Preparation of 2-(2-(7-(3-(aminomethyl)-2-fluorophenyl)-4-fluorobenzofuran-5-carboxamido)phenyl)acetic Acid (246b)

Step-1: Preparation of Ethyl 2-(2-(7-(3-(aminomethyl)-2-fluorophenyl)-4-fluorobenzofuran-5-carboxamido)phenyl)acetate (246a)

Compound 246a was prepared according to the procedure reported in step-3 of Scheme-1 from ethyl 2-(2-(7-bromo-4-fluorobenzofuran-5-carboxamido)phenyl)acetate (241a) (125 mg, 0.297 mmol) in dioxane (5 mL) using (3-(aminomethyl)-2-fluorophenyl)boronic acid hydrochloride (56a) (92 mg, 0.451 mmol), bis(triphenylphosphine)palladium(II) chloride (42 mg, 0.060 mmol) and a solution of $K_2CO_3$ (131 mg, 0.948 mmol) in water (0.5 mL) under an Ar atmosphere and heating at 100° C. for 3 h on oil bath. This gave after workup, purification by flash column chromatography [silica gel (12 g), eluting with DMA80/DCM, from 0-50%] ethyl 2-(2-(7-(3-(aminomethyl)-2-fluorophenyl)-4-fluorobenzofuran-5-carboxamido)phenyl)acetate (246a) (138 mg, 100% yield) as a pale-yellow oil; MS (ES+): 465.0 (M+1).

Step-2: Preparation of 2-(2-(7-(3-(aminomethyl)-2-fluorophenyl)-4-fluorobenzofuran-5-carboxamido)phenyl)acetic Acid (246b)

Compound 246b was prepared according to the procedure reported in step-6 of Scheme-1, from ethyl 2-(2-(7-(3-(aminomethyl)-2-fluorophenyl)-4-fluorobenzofuran-5-carboxamido)phenyl)acetate (246a) (132 mg, 0.284 mmol) in MeOH/THF (3 mL, each) using a solution of lithium hydroxide hydrate (66 mg, 1.57 mmol) in water (2 mL). This gave after workup and purification by reverse phase column chromatography [C18 (50 g), eluting with ACN in water (containing 0.1% HCl) from 0-100%] 2-(2-(7-(3-(aminomethyl)-2-fluorophenyl)-4-fluorobenzofuran-5-carboxamido)phenyl)acetic acid (246b) (48 mg, 39% yield) HCl salt as a white solid. $^1H$ NMR (300 MHz, DMSO-$d_6$) δ 12.40 (s, 1H), 9.96 (d, J=2.3 Hz, 1H), 8.56 (s, 3H), 8.16 (d, J=2.3 Hz, 1H), 7.76-7.62 (m, 3H), 7.49 (d, J=7.8 Hz, 1H), 7.38 (t, J=7.7 Hz, 1H), 7.32-7.20 (m, 3H), 7.20-7.11 (m, 1H), 4.11 (s, 2H), 3.65 (s, 2H); $^{19}F$ NMR (282 MHz, DMSO-$d_6$) δ−118.44, −118.68. MS (ES+): 437.0 (M+1); MS(ES−): 434.9 (M−1). HPLC purity 98.76%.

Scheme-247

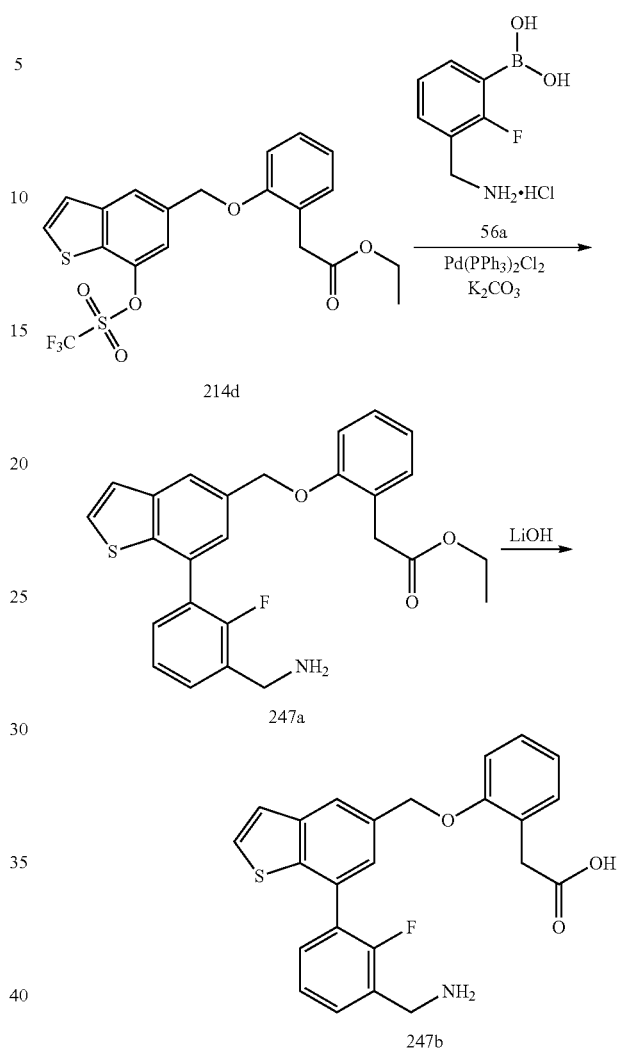

Preparation of 2-(2-((7-(3-(aminomethyl)-2-fluorophenyl)benzo[b]thiophen-5-yl)methoxy)phenyl)acetic Acid (247b)

Step-1: Preparation of Ethyl 2-(2-((7-(3-(aminomethyl)-2-fluorophenyl)benzo[b]thiophen-5-yl)methoxy)phenyl)acetate (247a)

Compound 247a was prepared according to the procedure reported in step-3 of Scheme-1 from ethyl 2-(2-((7-(((trifluoromethyl)sulfonyl)oxy)benzo[b]thiophen-5-yl)methoxy)phenyl)acetate (214d) (104 mg, 0.219 mmol) in dioxane (4 mL) using (3-(aminomethyl)-2-fluorophenyl)boronic acid hydrochloride (56a) (54.0 mg, 0.263 mmol) a solution of $K_2CO_3$ (91 mg, 0.658 mmol) in water (1 mL), Pd(PPh$_3$)$_2$Cl$_2$ (15 mg, 0.022 mmol) and heating under an Ar atmosphere at 100° C. for 16 h. This gave after workup, purification by flash column chromatography (silica gel) ethyl 2-(2-((7-(3-(aminomethyl)-2-fluorophenyl)benzo[b]thiophen-5-yl)methoxy)phenyl)acetate (247a) as a clear pale-yellow oil; MS (ES+): 450 (M+1); 472 (M+Na).

851

Step-2: Preparation of 2-(2-((7-(3-(aminomethyl)-2-fluorophenyl)benzo[b]thiophen-5-yl)methoxy)phenyl)acetic Acid (247b)

Compound 247b was prepared according to the procedure reported in step-6 of Scheme-1 from ethyl 2-(2-((7-(3-(aminomethyl)-2-fluorophenyl)benzo[b]thiophen-5-yl)methoxy)phenyl)acetate (247a) (from above step) in THF (1 mL) and MeOH (2 mL) using a solution of LiOH.H$_2$O (28 mg, 0.658 mmol) in water (1 mL). This gave after workup and purification by reverse phase column chromatography (C18, 100 g, 0-60% MeCN in H$_2$O containing 0.1% HCl) 2-(2-((7-(3-(aminomethyl)-2-fluorophenyl)benzo[b]thiophen-5-yl)methoxy)phenyl)acetic acid (247b) (53 mg, 57% yield) HCl salt as a white solid. $^1$H NMR (300 MHz, DMSO-d$_6$) δ 7.97 (d, J=5.4 Hz, 1H), 7.77 (q, J=5.6, 5.0 Hz, 1H), 7.62 (dt, J=9.6, 5.1 Hz, 2H), 7.49 (q, J=5.6, 5.0 Hz, 1H), 7.37 (q, J=7.1, 6.3 Hz, 2H), 7.15 (dd, J=8.4, 5.0 Hz, 2H), 7.02 (t, J=6.8 Hz, 1H), 6.83 (q, J=7.1 Hz, 1H), 5.22 (d, J=5.3 Hz, 2H), 4.10 (d, J=5.4 Hz, 2H), 3.51 (d, J=5.5 Hz, 2H). MS (ES+): 422 (M+1); (ES−): 420 (M−1); Analysis calculated for C$_{24}$H$_{20}$FNO$_3$S.HCl.H$_2$O: C, 60.56; H, 4.87; Cl, 7.45; N, 2.94; Found: C, 60.24; H, 4.81; Cl: 7.68; N: 2.98.

Scheme-248

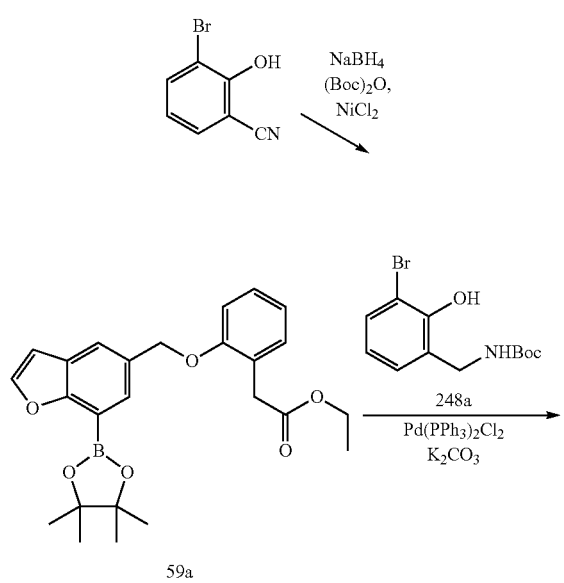

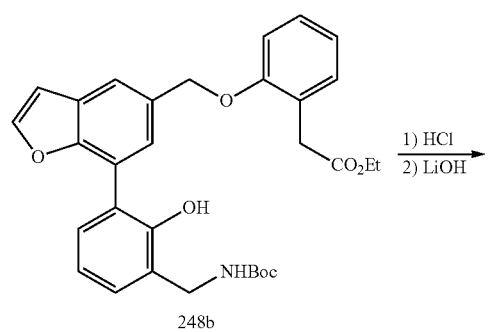

852

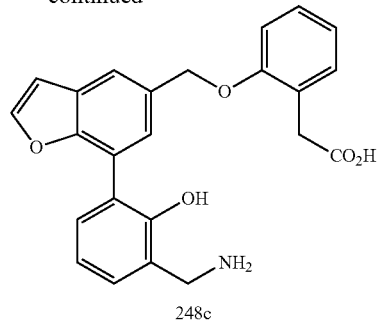

Preparation of 2-(2-((7-(3-(aminomethyl)-2-hydroxyphenyl)benzofuran-5-yl)methoxy)phenyl)acetic Acid (248c)

Step-1: Preparation of tert-butyl 3-bromo-2-hydroxybenzylcarbamate (248a)

Compound 248a was prepared according to the procedure reported in step-2 of Scheme-236 from 3-bromo-2-hydroxybenzonitrile (500 mg, 2.53 mmol; CAS #13073-28-4) in methanol (10 mL) using Boc anhydride (1102 mg, 5.05 mmol), nickel(II) chloride hexahydrate (60 mg, 0.253 mmol), sodium borohydride (669 mg, 17.68 mmol) and N1-(2-aminoethyl)ethane-1,2-diamine (0.147 mL, 1.361 mmol). This gave after workup and purification by flash column chromatography (SiO$_2$, 0-15% EtOAc in hexane) tert-butyl 3-bromo-2-hydroxybenzylcarbamate (248a) (541 mg, 71% yield) as a thick clear colorless oil; MS (ES−): 300 (M−1).

Step-2: Preparation of Ethyl 2-(2-((7-(3-(((tert-butoxycarbonyl)amino)methyl)-2-hydroxyphenyl)benzofuran-5-yl)methoxy)phenyl)acetate (248b)

Compound 248b was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (918 mg, 2.104 mmol) in dioxane (4 mL) using tert-butyl 3-bromo-2-hydroxybenzylcarbamate (248a) (763 mg, 2.52 mmol), Pd(PPh$_3$)$_2$Cl$_2$ (148 mg, 0.210 mmol) and a solution of K$_2$CO$_3$ (872 mg, 6.31 mmol) in water (1 mL) under a nitrogen atmosphere and heating at 100° C. for 16 h on oil bath. This gave after workup and purification by flash column chromatography (SiO$_2$, 0-20% EtOAc in hexane) ethyl 2-(2-((7-(3-(((tert-butoxycarbonyl)amino)methyl)-2-hydroxyphenyl)benzofuran-5-yl)methoxy)phenyl)acetate (248b) as a clear pale yellow oil; MS (ES+) 554 (M+Na), (ES−): 530 (M−1).

Step-3: Preparation of 2-(2-((7-(3-(aminomethyl)-2-hydroxyphenyl)benzofuran-5-yl)methoxy)phenyl) acetic Acid (248c)

A solution of ethyl 2-(2-((7-(3-(((tert-butoxycarbonyl)amino)methyl)-2-hydroxyphenyl)benzofuran-5-yl)methoxy)phenyl)acetate (248b) (from step-2) in 1.5 M HCl in MeOH (21.04 mL, 42.1 mmol) was heated at 60° C. for 1 h and concentrated in vacuum. The residue was purified by flash column chromatography (SiO$_2$, 0-10% MeOH in DCM) to afford ethyl 2-(2-((7-(3-(aminomethyl)-2-hydroxyphenyl)benzofuran-5-yl)methoxy)phenyl)acetate as a thick clear colorless oil. The oil and LiOH.H₂O (353 mg, 8.42 mmol) were suspended in MeOH (2 mL), THF (1 mL) and water (1 mL) and stirred at rt for 16 h. The solution was then concentrated in vacuum and the residue was purified by reverse-phase column chromatography (C18, 100 g, 0-60% MeCN in H₂O containing 0.1% HCl) to afford 2-(2-((7-(3-(aminomethyl)-2-hydroxyphenyl)benzofuran-5-yl)methoxy)phenyl)acetic acid (248c) (183 mg, 22% yield for 2 steps) HCl salt as a white solid. ¹H NMR (300 MHz, DMSO-d₆) δ 8.25 (s, 4H), 7.98 (d, J=2.2 Hz, 1H), 7.75 (d, J=1.6 Hz, 1H), 7.43 (dd, J=7.6, 1.7 Hz, 1H), 7.40-7.29 (m, 2H), 7.29-7.16 (m, 2H), 7.10 (d, J=8.0 Hz, 1H), 7.07-6.95 (m, 2H), 6.90 (td, J=7.3, 1.1 Hz, 1H), 5.24 (s, 2H), 4.09 (s, 2H), 3.58 (s, 2H). HPLC purity: 98.1%; MS (ES+): 404 (M+1).

Scheme-249

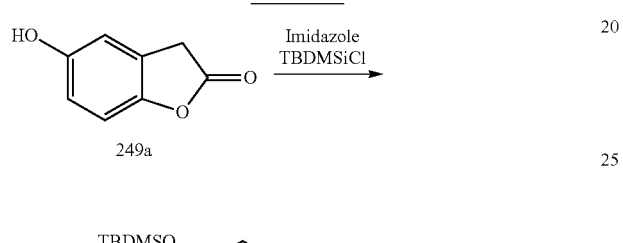

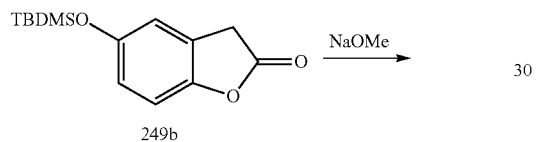

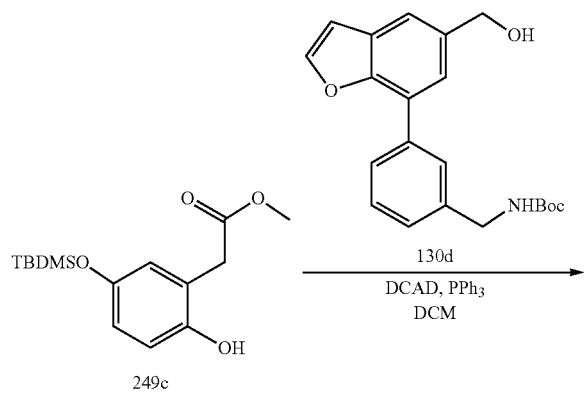

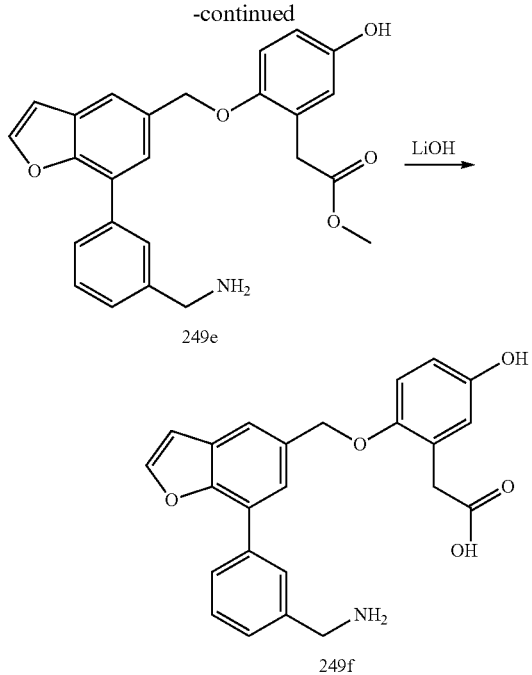

Preparation of 2-(2-((7-(3-(aminomethyl)phenyl)benzofuran-5-yl)methoxy)-5-hydroxyphenyl)acetic Acid (249f)

Step-1: Preparation of 5-(tert-butyldimethylsilyloxy)benzofuran-2(3H)-one (249b)

To a solution of 5-hydroxybenzofuran-2(3H)-one (249a) (1 g, 6.66 mmol; CAS #2688-48-4) in DMF (10 mL) was added 1H-imidazole (0.45 g, 6.66 mmol) and tert-butylchlorodimethylsilane (1.21 g, 7.99 mmol). The mixture was stirred at RT for 8 h, diluted with EtOAc and washed with water and brine. The organic layer was dried, concentrated, and the residue obtained was purified by flash column chromatography [silica (12 g), eluting with EtOAc in hexane from 0-50%] to give 5-(tert-butyldimethylsilyloxy)benzofuran-2(3H)-one (249b) (1.13 g, 64% yield) as a light yellow oil; ¹H NMR (300 MHz, DMSO-d₆) δ 7.05 (dd, J=8.6, 0.5 Hz, 1H), 6.90-6.84 (m, 1H), 6.76 (m, 1H), 3.88 (q, J=0.9 Hz, 2H), 0.95 (s, 9H), 0.17 (s, 6H); MS (ES-): 263.3 (M-1).

Step-2: Preparation of methyl 2-(5-((tert-butyldimethylsilyl)oxy)-2-hydroxyphenyl)acetate (249c)

To a solution of 5-(tert-butyldimethylsilyloxy)benzofuran-2(3H)-one (249b) (0.5 g, 1.89 mmol) in MeOH (10 mL) was added sodium methanolate (0.11 g, 2.08 mmol) at 0° C. The mixture was stirred at 0° C. for 1 h and concentrated in vacuum. The residue was dissolved in water and pH adjusted to 6 using AcOH. The mixture was diluted with DCM and washed with water and brine. The organic layer was dried, filtered and concentrated in vacuum. The residue obtained was purified by flash column chromatography [silica (12 g), eluting with EtOAc in hexane from 0-50%] to afford methyl 2-(5-((tert-butyldimethylsilyl)oxy)-2-hydroxyphenyl)acetate (249c) (0.31 g, 55% yield) as a light yellow oil; ¹H NMR (300 MHz, DMSO-d₆) δ 9.06 (s, 1H), 6.68-6.59 (m, 2H), 6.55 (dd, J=8.5, 3.0 Hz, 1H), 3.58 (s, 3H),

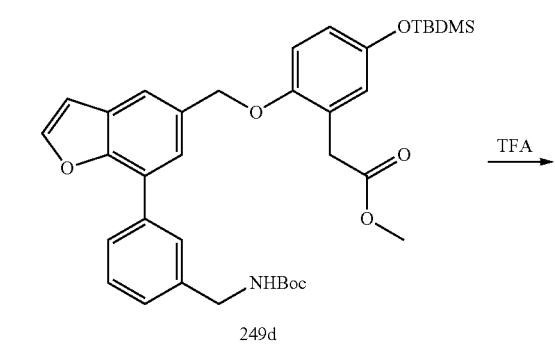

3.50 (s, 2H), 0.93 (s, 9H), 0.13 (s, 6H); MS (ES+): 297.2 (M+1), MS (ES−): 295.2 (M−1).

Step-3: Preparation of methyl 2-(2-((7-(3-(((tert-butoxycarbonyl)amino)methyl)phenyl)benzofuran-5-yl)methoxy)-5-((tert-butyldimethylsilyl)oxy)phenyl)acetate (249d)

Compound 249d was prepared according to the procedure reported in step-2 of Scheme-23 from tert-butyl 3-(5-(hydroxymethyl)benzofuran-7-yl)benzylcarbamate (130d) (0.28 g, 0.78 mmol) in DCM (10 mL) using triphenylphosphine (0.27 g, 1.01 mmol), methyl 2-(5-((tert-butyldimethylsilyl)oxy)-2-hydroxyphenyl)acetate (249c) (0.3 g, 1.01 mmol) and di-(4-chlorobenzyl)azodicarboxylatedi-(4-chlorobenzyl)azodicarboxylate (0.37 g, 1.01 mmol). This gave after workup and purification by flash column chromatography [silica gel 12 g column, eluting with EtOAc/MeOH=9:1 in hexanes from 0-30%] methyl 2-(2-((7-(3-(((tert-butoxycarbonyl)amino)methyl)phenyl)benzofuran-5-yl)methoxy)-5-((tert-butyldimethylsilyl)oxy)phenyl)acetate (249d) (0.24 g, 49% yield) as a brownish amorphous solid; MS (ES−): 530.8 (M-Boc-1).

Step-4: Preparation of methyl 2-(2-((7-(3-(aminomethyl)phenyl)benzofuran-5-yl)methoxy)-5-hydroxyphenyl)acetate (249e)

Compound 249e was prepared according to the procedure reported in step-5 of Scheme-1 from methyl 2-(2-((7-(3-(((tert-butoxycarbonyl)amino)methyl)phenyl)benzofuran-5-yl)methoxy)-5-((tert-butyldimethylsilyl)oxy)phenyl)acetate (249d) (0.24 g, 0.38 mmol) in DCM (6 mL) using TFA (0.59 mL, 7.60 mmol). This gave after workup and purification by flash column chromatography (silica gel 12 g, eluting with MeOH in DCM from 0-50%) methyl 2-(2-((7-(3-(aminomethyl)phenyl)benzofuran-5-yl)methoxy)-5-hydroxyphenyl)acetate (249e) (0.13 g, 82% yield) as a white wax; MS (ES+): 418.1 (M+1).

Step-5: Preparation of 2-(2-((7-(3-(aminomethyl)phenyl)benzofuran-5-yl)methoxy)-5-hydroxyphenyl)acetic Acid (249f)

Compound 249f was prepared according to the procedure reported in step-6 of Scheme-1 from methyl 2-(2-((7-(3-(aminomethyl)phenyl)benzofuran-5-yl)methoxy)-5-hydroxyphenyl)acetate (249e) (0.13 g, 0.31 mmol) in THF/methanol (4 mL, each) using a solution of lithium hydroxide hydrate (0.13 g, 3.11 mmol) in water (4 mL). This gave after workup and purification by reverse phase column [C18 (30 g), eluting with ACN in water (containing 0.1% HCl) from 0-100%] 2-(2-((7-(3-(aminomethyl)phenyl)benzofuran-5-yl)methoxy)-5-hydroxyphenyl)acetic acid (249f) (0.01 g, 10% yield) as a white solid; $^1$H NMR (300 MHz, DMSO-$d_6$) δ 12.23 (s, 1H), 8.96 (s, 1H), 8.35 (s, 3H), 8.09 (dd, J=4.2, 2.2 Hz, 1H), 7.98 (t, J=1.7 Hz, 1H), 7.97-7.89 (m, 2H), 7.74 (d, J=1.6 Hz, 1H), 7.62 (d, J=1.9 Hz, 1H), 7.60-7.56 (m, 1H), 7.06 (d, J=2.2 Hz, 1H), 6.90 (d, J=8.7 Hz, 1H), 6.66 (d, J=2.9 Hz, 1H), 6.60 (dd, J=8.7, 3.0 Hz, 1H), 5.14 (s, 2H), 4.14 (d, J=5.8 Hz, 2H), 3.51 (s, 2H); MS (ES+): 404.0 (M+1), MS (ES−): 402.0 (M−1). HPLC purity: 97.78%.

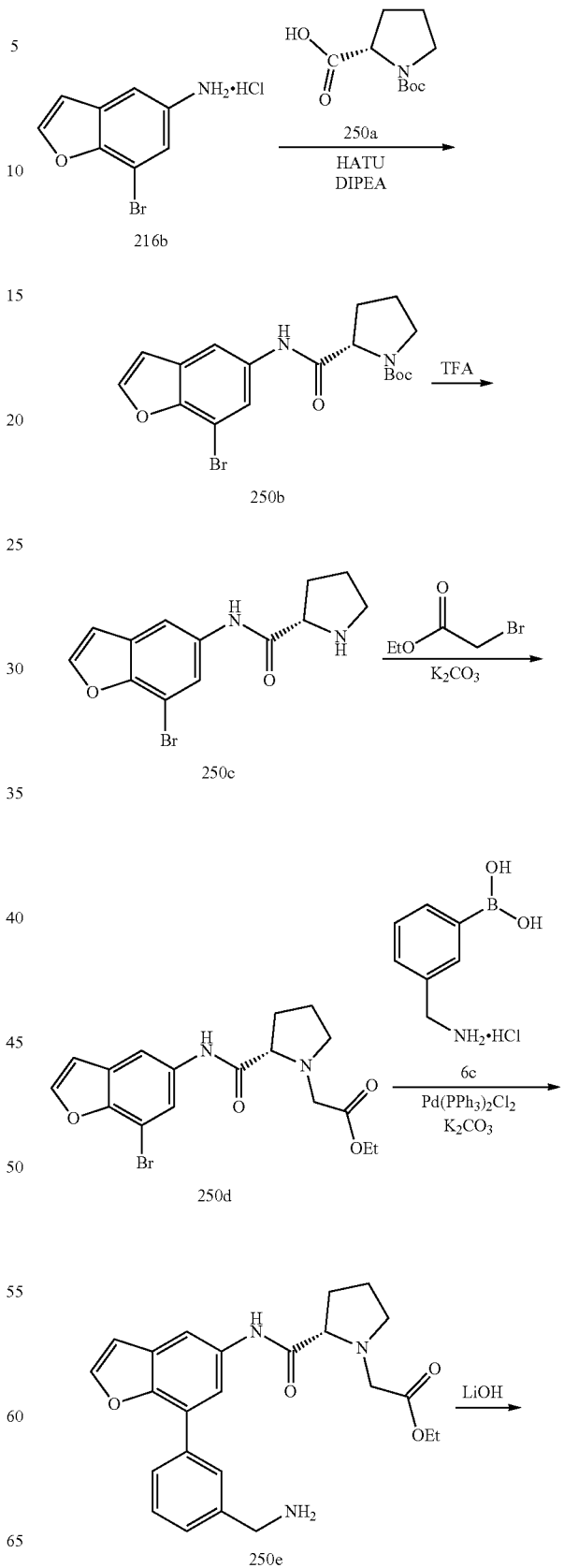

Scheme-250

-continued

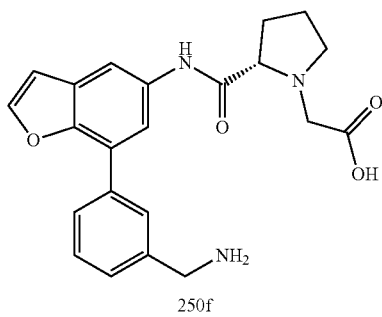

250f

Preparation of (S)-2-(2-((7-(3-(aminomethyl)phenyl)benzofuran-5-yl)carbamoyl)pyrrolidin-1-yl)acetic Acid (250f)

Step-1: Preparation of (S)-tert-butyl 2-((7-bromobenzofuran-5-yl)carbamoyl)pyrrolidine-1-carboxylate (250b)

Compound 250b was prepared according to the procedure reported in step-4 of Scheme-1 from 7-bromobenzofuran-5-amine hydrochloride (216b) (450 mg, 1.811 mmol) using (S)-1-(tert-butoxycarbonyl)pyrrolidine-2-carboxylic acid (250a) (487 mg, 2.264 mmol), DIPEA (1.262 mL, 7.24 mmol) and HATU (1033 mg, 2.72 mmol) in DMF (20 mL). This gave after work-up and purification by flash column chromatography [Silica gel, eluting with hexanes/ethyl acetate (1:0 to 2:1)] (S)-tert-butyl 2-((7-bromobenzofuran-5-yl)carbamoyl)pyrrolidine-1-carboxylate (250b) (687 mg, 93%) as a white solid; $^1$H NMR (300 MHz, DMSO-$d_6$) δ 10.13 (s, 1H), 8.08 (d, J=2.2 Hz, 1H), 7.95-7.89 (m, 1H), 7.84-7.78 (m, 1H), 7.12-7.05 (m, 1H), 4.30-4.12 (m, 1H), 3.49-3.35 (m, 2H), 2.31-2.10 (m, 1H), 1.97-1.74 (m, 3H), 1.40 (s, 3H), 1.27 (s, 6H); MS (ES−): 407.1 & 409.10 (M−1).

Step-2: Preparation of (S)—N-(7-bromobenzofuran-5-yl)pyrrolidine-2-carboxamide (250c)

Compound 250c was prepared according to the procedure reported in step-5 of Scheme-1 from (S)-tert-butyl 2-((7-bromobenzofuran-5-yl)carbamoyl)pyrrolidine-1-carboxylate (250b) (650 mg, 1.588 mmol) in DCM (25 mL) using TFA (1.224 mL, 15.88 mmol). This gave after workup (S)—N-(7-bromobenzofuran-5-yl)pyrrolidine-2-carboxamide (250c) as a brown gum, which was used as such for next step. MS (ES+): 308.95 & 310.90 (M+1).

Step-3: Preparation of (S)-ethyl 2-(2-((7-bromobenzofuran-5-yl)carbamoyl)pyrrolidin-1-yl)acetate (250d)

To a solution of (S)—N-(7-bromobenzofuran-5-yl)pyrrolidine-2-carboxamide (250c) (491 mg, 1.588 mmol) in DMF (12 mL) was added at room temperature potassium carbonate (1097 mg, 7.94 mmol), ethyl 2-bromoacetate (0.264 mL, 2.382 mmol) and stirred at RT for 15 h. The reaction mixture was diluted with ethyl acetate (110 mL), washed with water (60 mL), brine (60 mL), dried, filtered and concentrated in vacuum. The crude product was purified by flash column chromatography [silica gel, eluting with hexanes/ethyl acetate (1:0 to 2:1)] to afford (S)-ethyl 2-(2-((7-bromobenzofuran-5-yl)carbamoyl)pyrrolidin-1-yl)acetate (250d) (466 mg, 74% for 2 steps) as a colorless gum; $^1$H NMR (300 MHz, DMSO-$d_6$) δ 10.09 (s, 1H), 8.08 (d, J=2.2 Hz, 1H), 8.00 (d, J=1.9 Hz, 1H), 7.86 (dd, J=1.9, 0.5 Hz, 1H), 7.09 (d, J=2.2 Hz, 1H), 4.11 (q, J=7.1 Hz, 2H), 3.74-3.42 (m, 3H), 3.25-3.10 (m, 1H), 2.68 (td, J=9.0, 6.6 Hz, 1H), 2.25-2.06 (m, 1H), 1.96-1.65 (m, 3H), 1.18 (t, J=7.1 Hz, 3H); MS (ES+): 394.90 & 396.95 (M+1).

Step-4: Preparation of (S)-ethyl 2-(2-((7-(3-(aminomethyl)phenyl)benzofuran-5-yl)carbamoyl)pyrrolidin-1-yl)acetate (250e)

Compound 250e was prepared according to the procedure reported in step-3 of Scheme-1 from (S)-ethyl 2-(2-((7-bromobenzofuran-5-yl)carbamoyl)pyrrolidin-1-yl)acetate (250d) (460 mg, 1.164 mmol) in dioxane (16 mL) using 3-(aminomethyl)phenylboronic acid hydrochloride (6c) (327 mg, 1.746 mmol), a solution of $K_2CO_3$ (483 mg, 3.49 mmol) in water (1.6 mL), Pd(PPh$_3$)$_2$Cl$_2$ (163 mg, 0.233 mmol) and heating under an Ar atmosphere at 100° C. for 3 h. This gave after workup and purification by flash column chromatography [silica gel, eluting with (1:0 to 9:1) MeOH in DCM] (S)-ethyl 2-(2-((7-(3-(aminomethyl)phenyl)benzofuran-5-yl)carbamoyl)pyrrolidin-1-yl)acetate (250e) (321 mg, 65%) as a light brown gum; $^1$H NMR (300 MHz, DMSO-$d_6$) δ 10.06 (s, 1H), 8.06 (d, J=2.1 Hz, 1H), 8.04 (d, J=2.1 Hz, 1H), 7.80-7.75 (m, 1H), 7.71-7.65 (m, 2H), 7.51-7.36 (m, 2H), 7.03 (d, J=2.2 Hz, 1H), 4.11 (q, J=7.1 Hz, 2H), 3.81 (s, 2H), 3.75-3.44 (m, 3H), 3.24-3.17 (m, 1H), 2.69 (td, J=8.9, 6.6 Hz, 1H), 2.29-1.63 (m, 4H), 1.18 (t, J=7.1 Hz, 3H); MS (ES+): 422.00 (M+1).

Step-5: Preparation of (S)-2-(2-((7-(3-(aminomethyl)phenyl)benzofuran-5-yl)carbamoyl)pyrrolidin-1-yl)acetic Acid (250f)

Compound 250f was prepared according to the procedure reported in step-6 of Scheme-1 from (S)-ethyl 2-(2-((7-(3-(aminomethyl)phenyl)benzofuran-5-yl)carbamoyl)pyrrolidin-1-yl)acetate (250e) (300 mg, 0.712 mmol) in THF/methanol (15 mL, each) using a solution of lithium hydroxide hydrate (183 mg, 4.27 mmol) in water (15 mL). This gave after workup and purification by reverse phase column [C18 (30 g), eluting with ACN in water (containing 0.1% HCl) from 0-100%](S)-2-(2-((7-(3-(aminomethyl)phenyl)benzofuran-5-yl)carbamoyl)pyrrolidin-1-yl)acetic acid (250f) (248 mg, 89%) as a white solid; $^1$H NMR (300 MHz, DMSO-$d_6$) δ 11.18 (s, 1H), 8.58 (s, 3H), 8.08 (d, J=2.2 Hz, 1H), 8.02 (d, J=2.0 Hz, 1H), 7.92 (s, 1H), 7.85-7.76 (m, 2H), 7.65-7.54 (m, 2H), 7.08 (d, J=2.2 Hz, 1H), 4.49 (bs, 1H), 4.40-4.03 (m, 4H), 3.69 (bs, 1H), 2.67-2.55 (m, 1H), 2.16-2.01 (m, 3H), 2.00-1.86 (m, 1H); MS (ES+): 394.00 (M+1).

Scheme-251

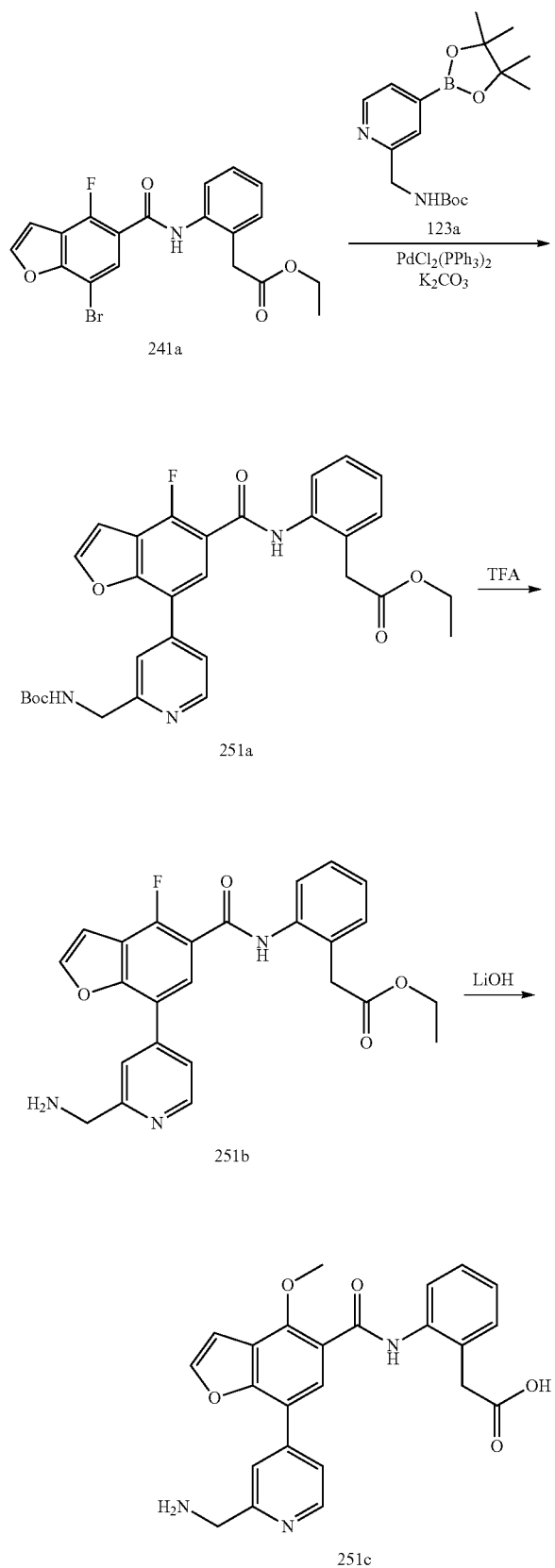

Preparation of 2-(2-(7-(2-(aminomethyl)pyridin-4-yl)-4-methoxybenzofuran-5-carboxamido)phenyl) acetic Acid (251c)

Step-1: Preparation of Ethyl 2-(2-(7-(2-(((tert-butoxycarbonyl)amino)methyl)pyridin-4-yl)-4-fluorobenzofuran-5-carboxamido)phenyl)acetate (251a)

Compound 251a was prepared according to the procedure reported in step-3 of Scheme-1 from ethyl 2-(2-(7-bromo-4-fluorobenzofuran-5-carboxamido)phenyl)acetate (241a) (153 mg, 0.364 mmol) in dioxane (5 mL) using tert-butyl ((4-(4,4,5,5-tetramethyl-1,3,2-dioxaborolan-2-yl)pyridin-2-yl)methyl)carbamate (123a) (241 mg, 0.721 mmol), a solution of $K_2CO_3$ (159 mg, 1.150 mmol) in water (0.5 mL), bis(triphenylphosphine)palladium(II) chloride (42 mg, 0.060 mmol) and heating at 100° C. for 3 h on oil bath. This gave after workup, purification by flash column chromatography [silica gel (12 g), eluting with hexanes in ethyl acetate from 30-100%] ethyl 2-(2-(7-(2-(((tert-butoxycarbonyl)amino)methyl)pyridin-4-yl)-4-fluorobenzofuran-5-carboxamido)phenyl)acetate (251a) (182 mg, 91% yield) as a yellow foam. MS (ES+): 548.0 (M+1).

Step-2: Preparation of Ethyl 2-(2-(7-(2-(aminomethyl)pyridin-4-yl)-4-fluorobenzofuran-5-carboxamido)phenyl)acetate (251b)

Compound 251b was prepared according to the procedure reported in step-5 of Scheme-1 from ethyl 2-(2-(7-(2-(((tert-butoxycarbonyl)amino)methyl)pyridin-4-yl)-4-fluorobenzofuran-5-carboxamido)phenyl)acetate (251a) (180 mg, 0.329 mmol) in DCM (8 mL) using TFA (0.3 mL, 3.89 mmol). This gave after workup and purification by flash column chromatography (silica gel 12 g, eluting with DMA-80 in DCM from 0-100%) ethyl 2-(2-(7-(2-(aminomethyl)pyridin-4-yl)-4-fluorobenzofuran-5-carboxamido)phenyl)acetate (251b) (109 mg, 74% yield) as pale yellow oil; $^1H$ NMR (300 MHz, DMSO-$d_6$) δ 10.03 (s, 1H), 8.65 (s, 1H), 8.30 (s, 1H), 7.99 (s, 2H), 7.78 (s, 1H), 7.53 (s, 1H), 7.35 (s, 2H), 4.06-4.02 (m, 2H), 3.92 (s, 2H), 3.80 (s, 2H), 1.22-1.13 (m, 3H); $^{19}F$ NMR (282 MHz, DMSO-$d_6$) δ −117.94. MS (ES+): 448.0 (M+1).

Step-3: Preparation of 2-(2-(7-(2-(aminomethyl)pyridin-4-yl)-4-methoxybenzofuran-5-carboxamido)phenyl)acetic Acid (251c)

Compound 251c was prepared according to the procedure reported in step-6 of Scheme-1 from ethyl 2-(2-(7-(2-(aminomethyl)pyridin-4-yl)-4-fluorobenzofuran-5-carboxamido)phenyl)acetate (251b) (107 mg, 0.239 mmol) in MeOH/THF (6 mL each) using a solution of lithium hydroxide monohydrate (86 mg, 2.05 mmol) in water (2 mL). This gave after workup and purification by reverse phase column [C18 (50 g), eluting with ACN in water (containing 0.1% HCl) from 0-100%] 2-(2-(7-(2-(aminomethyl)pyridin-4-yl)-4-methoxybenzofuran-5-carboxamido)phenyl)acetic acid (251c) (75 mg, 73% yield) as a yellow solid; $^1H$ NMR (300 MHz, DMSO-$d_6$) δ 10.00 (s, 1H), 8.97-8.58 (m, 4H), 8.36-8.18 (m, 3H), 8.12 (dd, J=5.6, 1.8 Hz, 1H), 7.77 (d, J=7.9 Hz, 1H), 7.59 (d, J=2.4 Hz, 1H), 7.34 (t, J=7.5 Hz, 2H), 7.26-7.06 (m, 1H), 4.36 (d, J=8.6 Hz, 5H), 3.75 (s, 2H); MS (ES+): 432.0 (M+1); MS (ES−): 430.0 (M−1).

Preparation of 2-(2-((2-acetyl-7-(3-(aminomethyl)phenyl)benzofuran-5-yl)methoxy)phenyl)acetic Acid (252d)
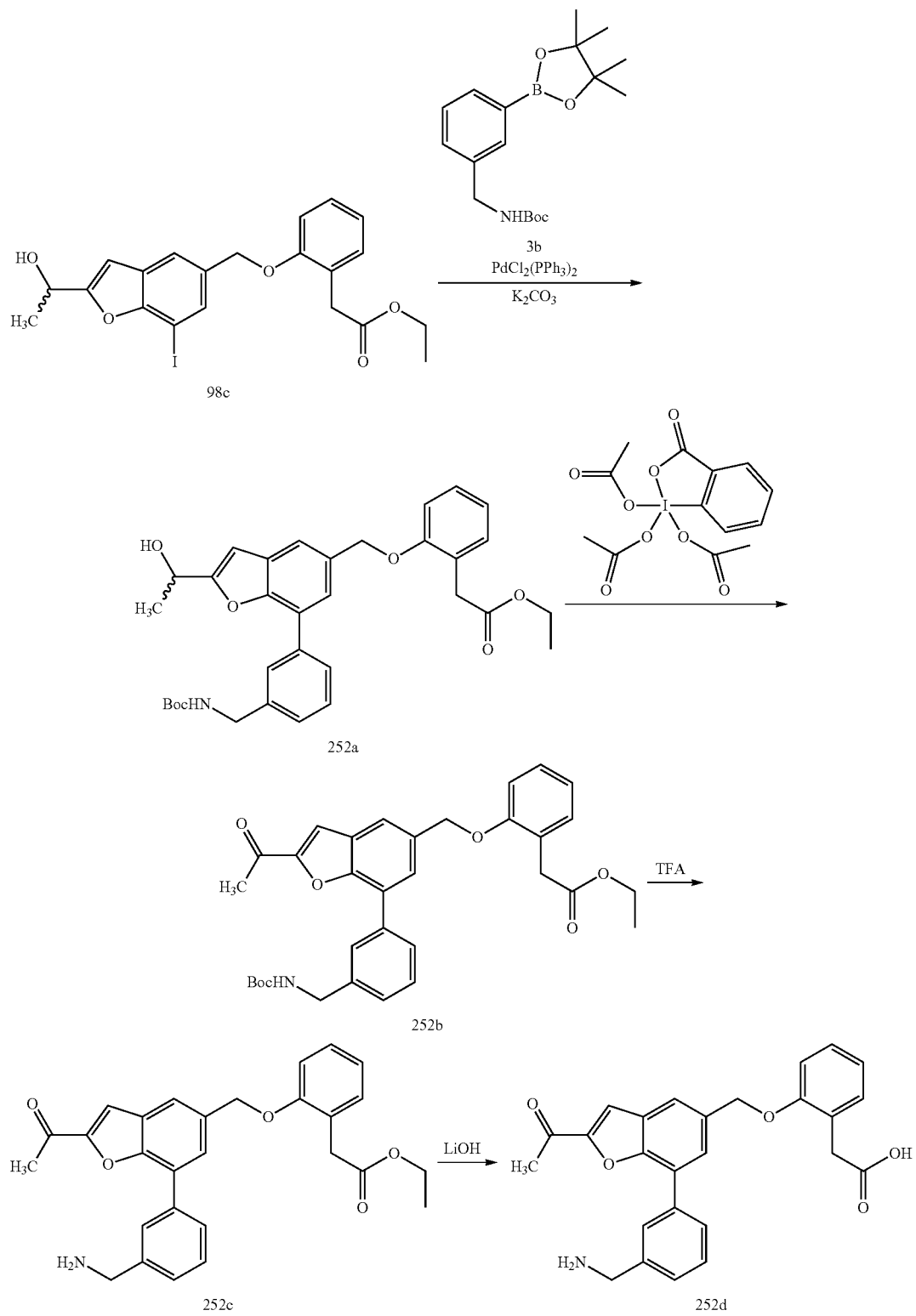

Step-1: Preparation of Ethyl 2-(2-((7-(3-(((tert-butoxycarbonyl)amino)methyl)phenyl)-2-(1-hydroxyethyl)benzofuran-5-yl)methoxy)phenyl)acetate (252a)

Compound 252a was prepared according to the procedure reported in step-3 of Scheme-1 from ethyl 2-(2-((2-(1-hydroxyethyl)-7-iodobenzofuran-5-yl)methoxy)phenyl)acetate (98c) (1.5 g, 3.12 mmol) in dioxane (40 mL) using tert-butyl 3-(4,4,5,5-tetramethyl-1,3,2-dioxaborolan-2-yl)benzylcarbamate (3b) (1.732 g, 4.68 mmol), a solution of $K_2CO_3$ (1.295 g, 9.37 mmol) in water (4 mL), bis(triphenylphosphine)palladium(II) chloride (0.438 g, 0.625 mmol) and heating at 100° C. for 3 h on oil bath. This gave after workup, purification by flash column chromatography [silica gel eluting with hexanes in ethyl acetate (1:0 to 2:1)] ethyl 2-(2-((7-(3-(((tert-butoxycarbonyl)amino)methyl)phenyl)-2-(1-hydroxyethyl)benzofuran-5-yl)methoxy)phenyl)acetate (252a) (1.115 g) as a yellow gum MS (ES+): 582.00 (M+Na);

Step-2: Preparation of Ethyl 2-(2-((2-acetyl-7-(3-(((tert-butoxycarbonyl)amino)methyl)phenyl)benzofuran-5-yl)methoxy)phenyl)acetate (252b)

To a solution of ethyl 2-(2-((7-(3-(((tert-butoxycarbonyl)amino)methyl)phenyl)-2-(1-hydroxyethyl)benzofuran-5-yl)methoxy)phenyl)acetate (252a) (500 mg, 0.893 mmol) in DCM (10 mL) was added at room temperature Dess-Martin Periodinane (798 mg, 1.787 mmol) and stirred at RT for 8 h. The reaction mixture was diluted with DCM (100 mL), washed with 1 M $NaHCO_3$ (50 mL), water (50 mL), dried, filtered and concentrated in vacuum. The crude product was purified by flash column chromatography [silica gel eluting with hexanes/ethyl acetate (1:0 to 2:1)] to afford ethyl 2-(2-((2-acetyl-7-(3-(((tert-butoxycarbonyl)amino)methyl)phenyl)benzofuran-5-yl)methoxy)phenyl)acetate (252b) (490 mg, 63% for 2 steps) as a brown gum; $^1$H NMR (300 MHz, DMSO-$d_6$) δ 7.97 (s, 1H), 7.87 (d, J=1.6 Hz, 1H), 7.81-7.73 (m, 3H), 7.58-7.44 (m, 2H), 7.37-7.31 (m, 1H), 7.30-7.19 (m, 2H), 7.14-7.10 (m, 1H), 6.92 (td, J=7.4, 1.1 Hz, 1H), 5.27 (s, 2H), 4.24 (d, J=6.2 Hz, 2H), 3.91 (q, J=7.1 Hz, 2H), 3.63 (s, 2H), 2.60 (s, 3H), 1.38 (s, 9H), 0.96 (t, J=7.1 Hz, 3H).

Step-3: Preparation of Ethyl 2-(2-((2-acetyl-7-(3-(aminomethyl)phenyl)benzofuran-5-yl)methoxy)phenyl)acetate (252c)

Compound 252c was prepared according to the procedure reported in step-5 of Scheme-1 from ethyl 2-(2-((2-acetyl-7-(3-(((tert-butoxycarbonyl)amino)methyl)phenyl)benzofuran-5-yl)methoxy)phenyl)acetate (252b) (470 mg, 0.843 mmol) in DCM (25 mL) using TFA (0.649 mL, 8.43 mmol). This gave after workup and purification by flash column chromatography [silica gel, eluting with DCM/methanol (1:0 to 9:1)] ethyl 2-(2-((2-acetyl-7-(3-(aminomethyl)phenyl)benzofuran-5-yl)methoxy)phenyl)acetate (252c) (445 mg) as a yellow solid; $^1$H NMR (300 MHz, DMSO-$d_6$) δ 8.28 (s, 3H), 8.02 (s, 1H), 7.99-7.94 (m, 2H), 7.91 (d, J=1.6 Hz, 1H), 7.80 (d, J=1.7 Hz, 1H), 7.69-7.60 (m, 1H), 7.57 (dt, J=7.8, 1.5 Hz, 1H), 7.31-7.20 (m, 2H), 7.12 (dd, J=8.3, 1.1 Hz, 1H), 6.93 (td, J=7.4, 1.1 Hz, 1H), 5.28 (s, 2H), 4.22-4.09 (m, 2H), 3.93 (q, J=7.1 Hz, 2H), 3.64 (s, 2H), 2.60 (s, 3H), 0.98 (t, J=7.1 Hz, 3H); MS (ES+): 458.00 (M+1).

Step-4: Preparation of 2-(2-((2-acetyl-7-(3-(aminomethyl)phenyl)benzofuran-5-yl)methoxy)phenyl)acetic Acid (252d)

Compound 252d was prepared according to the procedure reported in step-6 of Scheme-1 from ethyl 2-(2-((2-acetyl-7-(3-(aminomethyl)phenyl)benzofuran-5-yl)methoxy)phenyl)acetate (252c) (400 mg, 0.874 mmol) in MeOH/THF (16 mL each) using a solution of lithium hydroxide monohydrate (225 mg, 5.25 mmol) in water (16 mL). This gave after workup and purification by reverse phase column [C18 (50 g), eluting with ACN in water (containing 0.1% HCl) from 0-100%] 2-(2-((2-acetyl-7-(3-(aminomethyl)phenyl)benzofuran-5-yl)methoxy)phenyl)acetic acid (252d) (51 mg, 16% for 2 steps) HCl salt as a white solid; $^1$H NMR (300 MHz, DMSO-$d_6$) δ 12.21 (s, 1H), 8.54 (s, 3H), 8.05-8.01 (m, 1H), 8.00-7.95 (m, 2H), 7.93 (d, J=1.6 Hz, 1H), 7.87 (d, J=1.7 Hz, 1H), 7.69-7.56 (m, 2H), 7.30-7.19 (m, 2H), 7.13-7.07 (m, 1H), 6.91 (td, J=7.4, 1.1 Hz, 1H), 5.30 (s, 2H), 4.14 (s, 2H), 3.61 (s, 2H), 2.60 (s, 3H). MS (ES+): 430.0 (M+1).

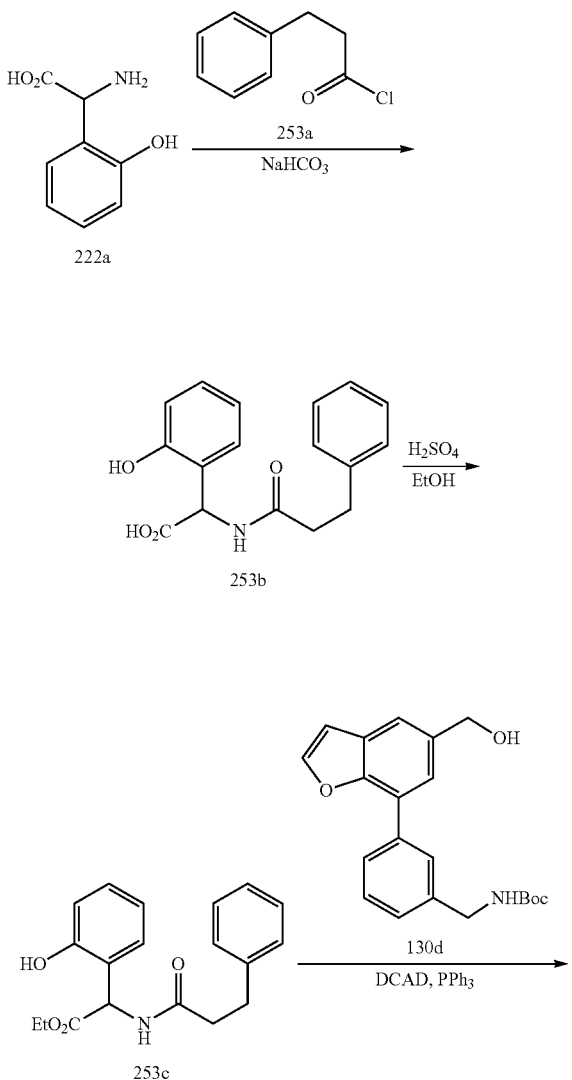

Scheme-253

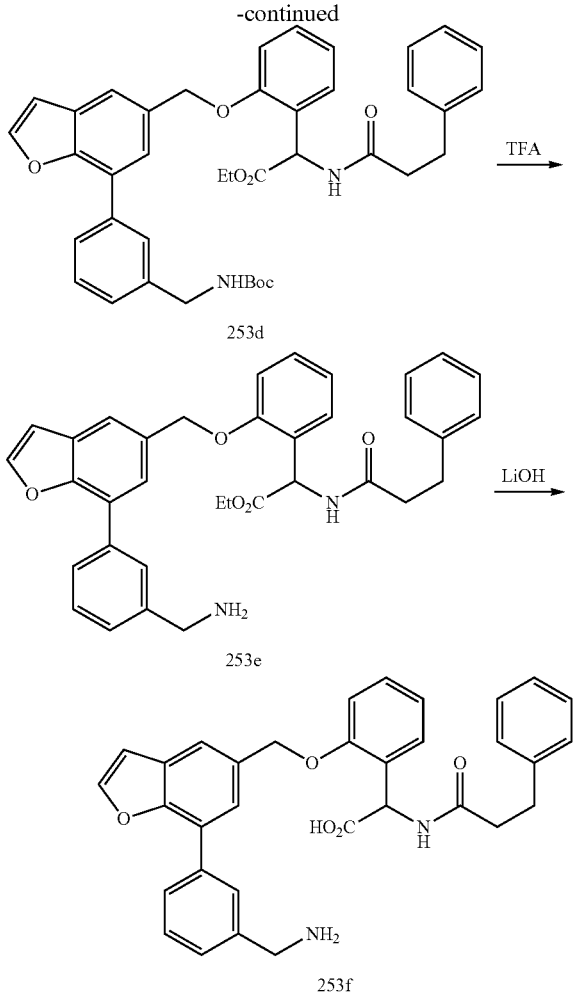

253d

253e

253f

Preparation of 2-(2-((7-(3-(aminomethyl)phenyl)benzofuran-5-yl)methoxy)phenyl)-2-(3-phenylpropanamido)acetic Acid (253f)

Step-1: Preparation of 2-(2-hydroxyphenyl)-2-(3-phenylpropanamido)acetic Acid (253b)

To a stirred solution of 2-amino-2-(2-hydroxyphenyl)acetic acid (222a) (1 g, 5.98 mmol) and sodium bicarbonate (2.010 g, 23.93 mmol) in water (20 mL)/THF (10 mL) at 0° C. was added a solution of 3-phenylpropanoyl chloride (253a) (3.03 g, 17.95 mmol) in tetrahydrofuran (10 mL). The reaction mixture was allowed to warm to room temperature stirred for 12 h and concentrated in vacuum to remove THF. The reaction mixture was acidified with 3 N HCl to pH 4 and extracted with ethyl acetate (3×100 mL). The combined organic layers were washed with brine (50 mL), dried and concentrated in vacuum to afford 2-(2-hydroxyphenyl)-2-(3-phenylpropanamido)acetic acid (253b) (2.03 g, 113% yield) as a thick syrup. The crude material was used as such in the next reaction without further purification. MS (ES+): 322.00 (M+Na), (ES−): 299.00 (M−1).

Step-2: Preparation of Ethyl 2-(2-hydroxyphenyl)-2-(3-phenylpropanamido)acetate (253c)

Compound 253c was prepared according to the procedure reported in step-2 of Scheme-222 from 2-(2-hydroxyphenyl)-2-(3-phenylpropanamido)acetic acid (253b) (2.5 g, 8.35 mmol) in ethanol (30 mL) using sulfuric acid (1.113 mL, 20.88 mmol). This gave after workup and purification by flash column chromatography (silica gel) ethyl 2-(2-hydroxyphenyl)-2-(3-phenylpropanamido)acetate (253c) (345 mg, 13% yield) as a white solid; $^1$H NMR (300 MHz, DMSO-$d_6$) δ 9.79 (s, 1H), 8.40 (d, J=7.4 Hz, 1H), 7.35-7.07 (m, 7H), 6.91-6.72 (m, 2H), 5.66 (d, J=7.4 Hz, 1H), 4.14-3.93 (m, 2H), 2.80 (t, J=7.9 Hz, 2H), 2.48-2.40 (m, 2H), 1.11 (t, J=7.1 Hz, 3H); MS (ES+): 328.00 (M+1), (ES−): 326.00 (M−1).

Step-3: Preparation ethyl 2-(2-((7-(3-(((tert-butoxycarbonyl)amino)methyl)phenyl)benzofuran-5-yl)methoxy)phenyl)-2-(3-phenylpropanamido)acetate (253d)

Compound 253d was prepared according to the procedure reported in step-2 of Scheme-23 from tert-butyl 3-(5-(hydroxymethyl)benzofuran-7-yl)benzylcarbamate (130d) (300 mg, 0.849 mmol) in DCM (20 mL) using triphenylphosphine (256 mg, 0.976 mmol), ethyl 2-(2-hydroxyphenyl)-2-(3-phenylpropanamido)acetate (253c) (320 mg, 0.976 mmol) and a solution of di-(4-chlorobenzyl)azodicarboxylate (DCAD, 374 mg, 1.019 mmol) in DCM (15 mL). This gave after workup and purification by flash column chromatography (silica gel, eluting with ethyl acetate in hexanes from 0-50%) ethyl 2-(2-((7-(3-(((tert-butoxycarbonyl)amino)methyl)phenyl)benzofuran-5-yl)methoxy)phenyl)-2-(3-phenylpropanamido)acetate (253d) (365 mg, 0.551 mmol, 64.9% yield) as a white foam; MS (ES+): 563.00 (M+1-Boc).

Step-4: Preparation of Ethyl 2-(2-((7-(3-(aminomethyl)phenyl)benzofuran-5-yl)methoxy)phenyl)-2-(3-phenylpropanamido)acetate (253e)

Compound 253e was prepared according to the procedure reported in step-5 of Scheme-1 from ethyl 2-(2-((7-(3-(((tert-butoxycarbonyl)amino)methyl)phenyl)benzofuran-5-yl)methoxy)phenyl)-2-(3-phenylpropanamido)acetate (253d) (350 mg, 0.528 mmol) in DCM (10 mL) using TFA (0.407 mL, 5.28 mmol). This gave after workup and purification by flash column chromatography (silica gel 25 g, eluting with DMA 80 in DCM) ethyl 2-(2-((7-(3-(aminomethyl)phenyl)benzofuran-5-yl)methoxy)phenyl)-2-(3-phenylpropanamido)acetate (253e) (160 mg, 54% yield) as a white solid; $^1$H NMR (300 MHz, DMSO-$d_6$) δ 8.55 (d, J=7.8 Hz, 1H), 8.09 (d, J=2.2 Hz, 1H), 7.86 (d, J=1.8 Hz, 1H), 7.80-7.69 (m, 2H), 7.64 (d, J=1.7 Hz, 1H), 7.51-7.27 (m, 3H), 7.26-7.07 (m, 7H), 7.02 (d, J=2.2 Hz, 1H), 6.97-6.91 (m, 1H), 5.83 (d, J=7.8 Hz, 1H), 5.30 (s, 2H), 4.02-3.89 (m, 2H), 3.85 (s, 2H), 2.77 (dd, J=9.1, 6.4 Hz, 2H), 2.51-2.39 (m, 2H), 0.98 (t, J=7.1 Hz, 3H); MS (ES+): 563.25 (M+1).

Step-5: Preparation of 2-(2-((7-(3-(aminomethyl)phenyl)benzofuran-5-yl)methoxy)phenyl)-2-(3-phenylpropanamido)acetic Acid (253f)

Compound 253f was prepared according to the procedure reported in step-6 of Scheme-1 from ethyl 2-(2-((7-(3-(aminomethyl)phenyl)benzofuran-5-yl)methoxy)phenyl)-2-(3-phenylpropanamido)acetate (253e) (160 mg, 0.284 mmol) in THF/MeOH (3 mL, each) using a solution of lithium hydroxide monohydrate (21 mg, 0.85 mmol) in water (1 mL). This gave after workup and purification by reverse phase column [C18 (30 g), eluting with ACN in water (containing 0.1% HCl) from 0-100%] 2-(2-((7-(3-(aminomethyl)phenyl)benzofuran-5-yl)methoxy)phenyl)-2-(3-phenylpropanamido)acetic acid (253f) (100 mg, 66% yield) hydrochloride salt as a white solid; $^1$H NMR (300 MHz, DMSO-d$_6$) δ 12.72 (s, 1H), 8.54 (d, J=7.8 Hz, 1H), 8.42 (s, 3H), 8.11 (d, J=2.2 Hz, 1H), 8.02 (s, 1H), 7.95 (dt, J=6.9, 2.1 Hz, 1H), 7.79 (d, J=1.6 Hz, 1H), 7.71 (d, J=2.0 Hz, 1H), 7.57 (d, J=6.6 Hz, 2H), 7.36-7.23 (m, 2H), 7.23-7.10 (m, 6H), 7.04 (d, J=2.2 Hz, 1H), 6.96 (t, J=7.5 Hz, 1H), 5.87 (d, J=7.9 Hz, 1H), 5.32 (s, 2H), 4.14 (s, 2H), 2.82-2.66 (m, 2H), 2.54-2.39 (m, 2H); MS (ES+): 535.2 (M+1), (ES−): 533.10 (M−1).

Scheme-254

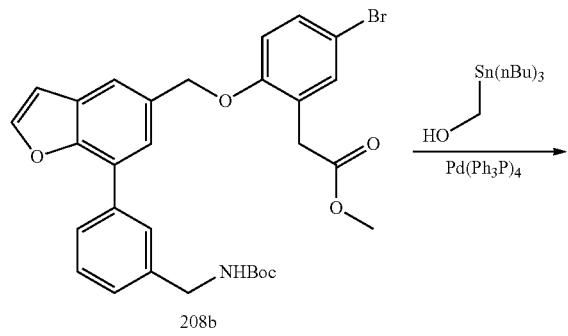

208b

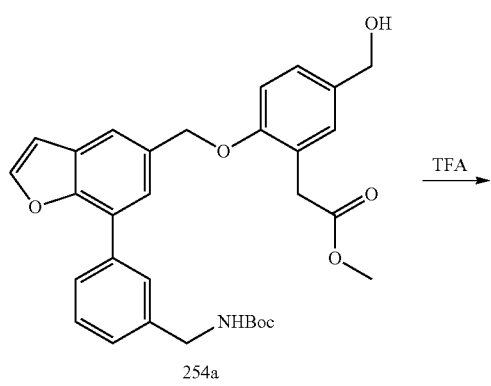

254a

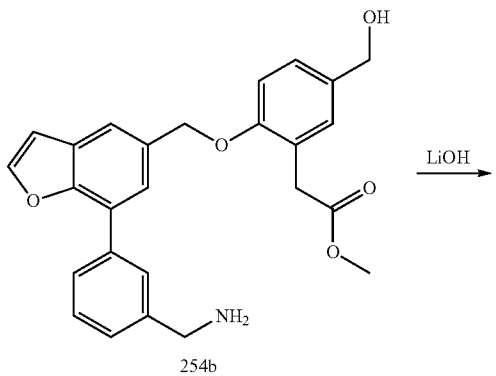

254b

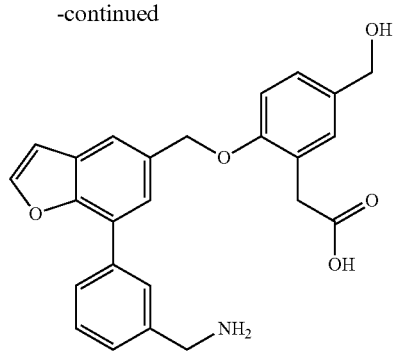

254c

Preparation of 2-(2-((7-(3-(aminomethyl)phenyl)benzofuran-5-yl)methoxy)-5-(hydroxymethyl)phenyl)acetic Acid (254c)

Step-1: Preparation of methyl 2-(2-((7-(3-(((tert-butoxycarbonyl)amino)methyl)phenyl)benzofuran-5-yl)methoxy)-5-(hydroxymethyl)phenyl)acetate (254a)

Compound 254a was prepared according to the procedure reported in step-1 of Scheme-236 from methyl 2-(5-bromo-2-((7-(3-(((tert-butoxycarbonyl)amino)methyl)phenyl)benzofuran-5-yl)methoxy)phenyl)acetate (208b) (0.1 g, 0.17 mmol) in DMF (4 mL) using (tributylstannyl)methanol (0.08 g, 0.26 mmol), Pd(Ph$_3$P)$_4$ (0.04 g, 0.03 mmol) and heating at 80° C. in an oil bath for 16 h. This gave after workup and purification by flash column chromatography (silica gel 12 g, eluting with MeOH in DCM from 0 to 60%) methyl 2-(2-((7-(3-(((tert-butoxycarbonyl)amino)methyl)phenyl)benzofuran-5-yl)methoxy)-5-(hydroxymethyl)phenyl)acetate (254a) (0.04 g, 39% yield) as a white solid; MS (ES+): 554.2 (M+Na). MS (ES−): 530.2 (M−1).

Step-2: Preparation of methyl 2-(2-((7-(3-(aminomethyl)phenyl)benzofuran-5-yl)methoxy)-5-(hydroxymethyl)phenyl)acetate (254b)

Compound 254b was prepared according to the procedure reported in step-5 of Scheme-1 from methyl 2-(2-((7-(3-(((tert-butoxycarbonyl)amino)methyl)phenyl)benzofuran-5-yl)methoxy)-5-(hydroxymethyl)phenyl)acetate (254a) (0.04 g, 0.07 mmol) in DCM (3 mL) using TFA (0.10 mL, 1.35 mmol). This gave after workup and purification by flash column chromatography (silica gel 12 g, eluting with MeOH in DCM from 0-50%) methyl 2-(2-((7-(3-(aminomethyl)phenyl)benzofuran-5-yl)methoxy)-5-(hydroxymethyl)phenyl)acetate (254b) (0.03 g, 99% yield) as a clear wax, which was used as such for next step.

Step-3: Preparation of 2-(2-((7-(3-(aminomethyl)phenyl)benzofuran-5-yl)methoxy)-5-(hydroxymethyl)phenyl)acetic Acid (254c)

Compound 254c was prepared according to the procedure reported in step-6 of Scheme-1 from methyl 2-(2-((7-(3-(aminomethyl)phenyl)benzofuran-5-yl)methoxy)-5-(hydroxymethyl)phenyl)acetate (254b) (0.03 g, 0.07 mmol) in THF/methanol (4 mL, each) using a solution of lithium hydroxide hydrate (0.02 g, 0.54 mmol) in water (1 mL). This gave after workup and purification by reverse phase column chromatography [C18 (50 g), eluting with ACN in water (containing 0.1% HCl) from 0-100%] 2-(2-((7-(3-(aminomethyl)phenyl)benzofuran-5-yl)methoxy)-5-(hydroxymethyl)phenyl)acetic acid (254c) (0.004 g, 14% yield) HCl salt as a white solid; $^1$H NMR (300 MHz, DMSO-$d_6$) δ 8.22 (s, 3H), 8.10 (d, J=2.2 Hz, 1H), 7.98 (s, 1H), 7.93 (d, J=8.0 Hz, 1H), 7.76 (s, 1H), 7.62 (d, J=1.6 Hz, 1H), 7.59 (d, J=7.7 Hz, 1H), 7.52 (d, J=7.7 Hz, 1H), 7.16 (d, J=6.8 Hz, 2H), 7.08-7.00 (m, 2H), 5.26 (s, 2H), 5.12-4.99 (m, 1H), 4.40 (d, J=4.2 Hz, 2H), 4.15 (d, J=5.5 Hz, 2H), 3.58 (s, 2H); MS (ES+): 418.1 (M+1); MS (ES−): 416.0 (M−1).

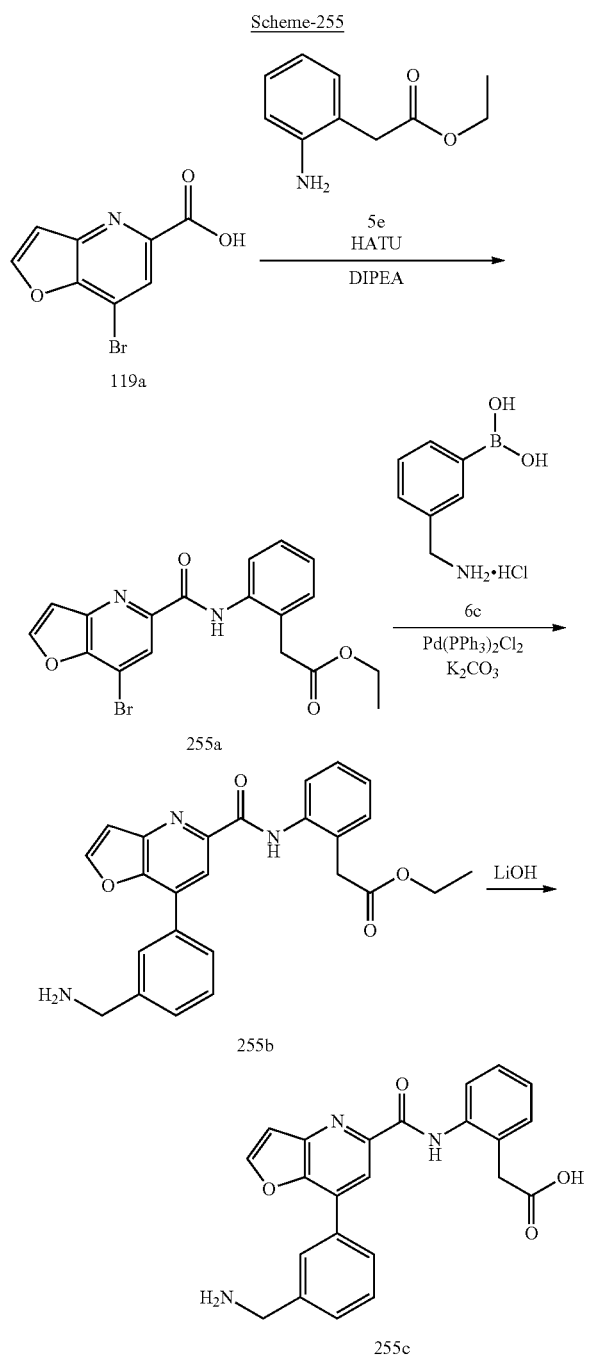

Preparation of 2-(2-(7-(3-(aminomethyl)phenyl)furo[3,2-b]pyridine-5-carboxamido)phenyl)acetic Acid (255c)

Step-1: Preparation of Ethyl 2-(2-(7-bromofuro[3,2-b]pyridine-5-carboxamido)phenyl)acetate (255a)

Compound 255a was prepared according to the procedure reported in step-4 of Scheme-1 from 7-bromofuro[3,2-b]pyridine-5-carboxylic acid (119a) (223 mg, 0.921 mmol) in DMF (6 mL) using ethyl 2-(2-aminophenyl)acetate (5e) (246 mg, 1.373 mmol), DIPEA (0.65 mL, 3.73 mmol) and HATU (546 mg, 1.436 mmol). This gave after workup and purification by flash column chromatography (Silica gel 12 g, eluting with ethyl acetate in hexane from 0-50%) ethyl 2-(2-(7-bromofuro[3,2-b]pyridine-5-carboxamido)phenyl)acetate (255a) (322 mg, 87% yield) as a white solid. $^1$H NMR (300 MHz, DMSO-$d_6$) δ 10.45 (s, 1H), 8.64 (d, J=2.3 Hz, 1H), 8.31 (s, 1H), 7.69 (dd, J=8.3, 1.3 Hz, 1H), 7.46-7.30 (m, 3H), 7.22 (td, J=7.4, 1.4 Hz, 1H), 4.04 (q, J=7.1 Hz, 2H), 3.79 (s, 2H), 1.07 (t, J=7.1 Hz, 3H); MS (ES+): 402.9 (M+1).

Step-2: Preparation of Ethyl 2-(2-(7-(3-(aminomethyl)phenyl)furo[3,2-b]pyridine-5-carboxamido)phenyl)acetate (255b)

Compound 255b was prepared according to the procedure reported in step-3 of Scheme-1 from ethyl 2-(2-(7-bromofuro[3,2-b]pyridine-5-carboxamido)phenyl)acetate (255a) (120 mg, 0.298 mmol) in dioxane (5 mL) using 3-(aminomethyl)phenylboronic acid hydrochloride (6c) (73 mg, 0.390 mmol), bis(triphenylphosphine)palladium(II) chloride (40 mg, 0.057 mmol) and a solution of $K_2CO_3$ (137 mg, 0.991 mmol) in water (0.5 mL) under an Ar atmosphere and heating at 100° C. for 3 h on oil bath. This gave after workup, purification by flash column chromatography [silica gel (12 g), eluting with DMA80/DCM, from 0-80%] ethyl 2-(2-(7-(3-(aminomethyl)phenyl)furo[3,2-b]pyridine-5-carboxamido)phenyl)acetate (255b) (47 mg, 37% yield) as a pale-yellow oil. MS (ES+): 430.0 (M+1).

Step-3: Preparation of 2-(2-(7-(3-(aminomethyl)phenyl)furo[3,2-b]pyridine-5-carboxamido)phenyl)acetic Acid (255c)

Compound 255c was prepared according to the procedure reported in step-6 of Scheme-1 from ethyl 2-(2-(7-(3-(aminomethyl)phenyl)furo[3,2-b]pyridine-5-carboxamido)phenyl)acetate (255b) (46 mg, 0.107 mmol) in MeOH/THF (6 mL, each) using a solution of lithium hydroxide hydrate (42 mg, 1.0 mmol) in water (2 mL). This gave after workup and purification by reverse phase column chromatography [C18 (50 g), eluting with ACN in water (containing 0.1% HCl) from 0-100%] 2-(2-(7-(3-(aminomethyl)phenyl)furo[3,2-b]pyridine-5-carboxamido)phenyl)acetic acid (255c) (24 mg, 56% yield) HCl salt as a white solid. $^1$H NMR (300 MHz, DMSO-$d_6$) δ 12.63 (s, 1H), 10.55 (s, 1H), 8.77-8.43 (m, 4H), 8.36 (s, 1H), 8.19-7.98 (m, 2H), 7.75 (d, J=7.9 Hz, 1H), 7.70-7.49 (m, 2H), 7.42-7.20 (m, 3H), 7.14 (t, J=7.4 Hz, 1H), 4.11 (d, J=5.7 Hz, 2H), 3.67 (s, 2H). MS (ES+): 402.0 (M+1); MS(ES−): 400.0 (M−1).

Scheme-256

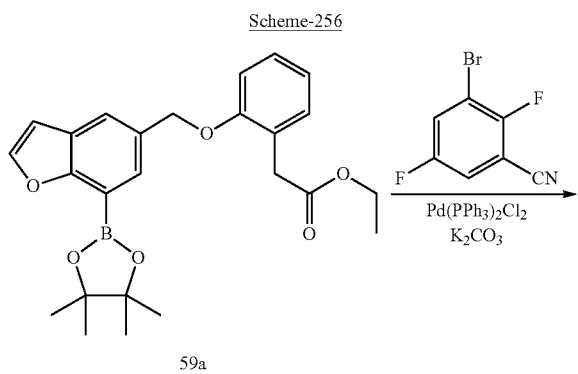

59a

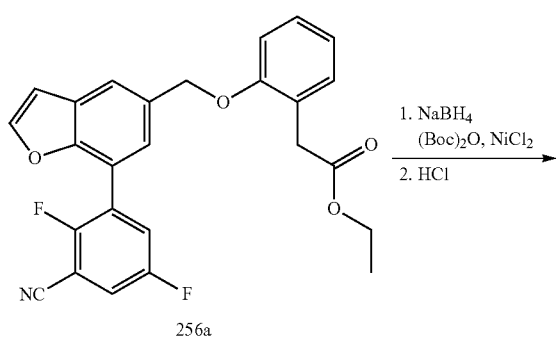

256a

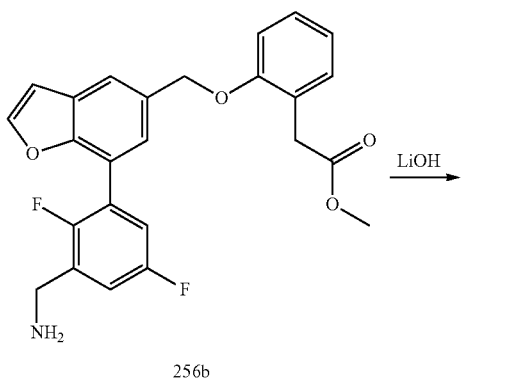

256b

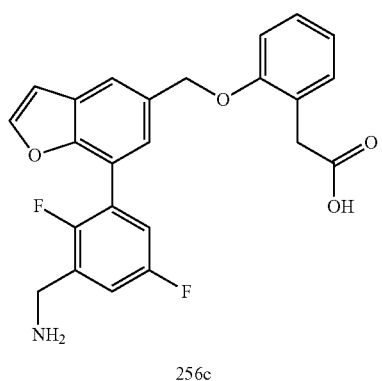

256c

Preparation of 2-(2-((7-(3-(aminomethyl)-2,5-difluorophenyl)benzofuran-5-yl)methoxy)phenyl)acetic Acid (256c)

Step-1: Preparation of Ethyl 2-(2-((7-(3-cyano-2,5-difluorophenyl)benzofuran-5-yl)methoxy)phenyl) acetate (256a)

Compound 256a was prepared according to the procedure reported in step-3 of Scheme-1 from ethyl 2-(2-((7-(4,4,5,5-tetramethyl-1,3,2-dioxaborolan-2-yl)benzofuran-5-yl)methoxy)phenyl)acetate (59a) (500 mg, 1.146 mmol) in dioxane (2 mL) using 3-bromo-2,5-difluorobenzonitrile (250 mg, 1.146 mmol; CAS #1638487-41-8), $Pd(PPh_3)_2Cl_2$ (80 mg, 0.115 mmol) and a solution of $K_2CO_3$ (475 mg, 3.44 mmol) in water (1 mL) under a nitrogen atmosphere and heating at 100° C. for 16 h on oil bath. This gave after workup and purification by flash column chromatography (silica gel 12 g, eluting with ethyl acetate in hexane from 0-15%) ethyl 2-(2-((7-(3-cyano-2,5-difluorophenyl)benzofuran-5-yl)methoxy)phenyl)acetate (256a) (0.26 g, 51% yield) as a clear colorless thick oil; $^1$H NMR (300 MHz, DMSO-$d_6$) δ 8.17-8.09 (m, 2H), 8.03 (ddd, J=8.9, 5.7, 3.2 Hz, 1H), 7.86 (d, J=1.6 Hz, 1H), 7.55 (s, 1H), 7.33-7.19 (m, 2H), 7.16-7.08 (m, 2H), 6.92 (td, J=7.4, 1.1 Hz, 1H), 5.25 (s, 2H), 3.94 (q, J=7.1 Hz, 2H), 3.64 (s, 2H), 1.01 (t, J=7.1 Hz, 3H); MS (ES+): 447.9 (M+1).

Step-2: Preparation of methyl 2-(2-((7-(3-(aminomethyl)-2,5-difluorophenyl)benzofuran-5-yl)methoxy)phenyl)acetate (256b)

To a mixture of ethyl 2-(2-((7-(3-cyano-2,5-difluorophenyl)benzofuran-5-yl)methoxy)phenyl)acetate (256a) (0.26 g, 0.581 mmol), Boc anhydride (0.254 g, 1.162 mmol) and $NiCl_2.6H_2O$ (0.014 g, 0.058 mmol) in MeOH (10 mL) at 0° C. was added portion-wise $NaBH_4$ (0.154 g, 4.07 mmol). The resulting black mixture was then stirred at rt for 16 h, quenched with diethylenetriamine (0.126 mL, 1.162 mmol) and continued stirring at rt for additional 15 min. The solution was concentrated in vacuum to remove MeOH and the residue obtained was diluted with saturated $NaHCO_3$ (25 mL) and extracted with EtOAc (20 mL×3). The combined organic extracts were washed with $H_2O$ (20 mL), brine (20 mL), dried, filtered and concentrated in vacuum. The residue was purified by flash column chromatography ($SiO_2$, 12 g, eluting with 0-20% EtOAc in hexane). The product obtained was dissolved in 2 M HCl in MeOH (0.212 g, 5.81 mmol), which was freshly prepared by adding acetyl chloride dropwise to cold MeOH at 0° C. The solution was stirred at 60° C. for 1 h and concentrated in vacuum. The residue obtained was purified by flash column chromatography ($SiO_2$, 12 g, eluting with 0-10% MeOH in DCM) to afford methyl 2-(2-((7-(3-(aminomethyl)-2,5-difluorophenyl)benzofuran-5-yl)methoxy)phenyl)acetate (256b) (0.13 g) as a thick clear colorless oil; MS (ES+): 437.9 (M+1), (ES−): 435.9 (M−1).

Step-3: Preparation of 2-(2-((7-(3-(aminomethyl)-2,5-difluorophenyl)benzofuran-5-yl)methoxy)phenyl) acetic Acid (256c)

Compound 256c was prepared according to the procedure reported in step-6 of Scheme-1 from methyl 2-(2-((7-(3-(aminomethyl)-2,5-difluorophenyl)benzofuran-5-yl) methoxy)phenyl)acetate (256b) (from step-2) in MeOH (2 mL), THF (1 mL each) using a solution of lithium hydroxide monohydrate (0.073 g, 1.743 mmol) in water (1 mL). This gave after workup and purification by reverse phase column [C18 (50 g), eluting with ACN in water (containing 0.1% HCl) from 0-100%] 2-(2-((7-(3-(aminomethyl)-2,5-difluorophenyl)benzofuran-5-yl)methoxy)phenyl)acetic acid (256c) (12 mg, 5% yield for two steps) HCl salt as a white solid; $^1$H NMR (300 MHz, DMSO-$d_6$) δ 8.58 (s, 3H), 8.08 (d, J=2.2 Hz, 1H), 7.85 (d, J=1.6 Hz, 1H), 7.69-7.53 (m, 2H), 7.51 (s, 1H), 7.23 (dd, J=8.8, 7.0 Hz, 2H), 7.15-7.01 (m, 2H), 6.91 (t, J=7.3 Hz, 1H), 5.26 (s, 2H), 4.15 (s, 2H), 3.58 (s, 2H).
Scheme-257
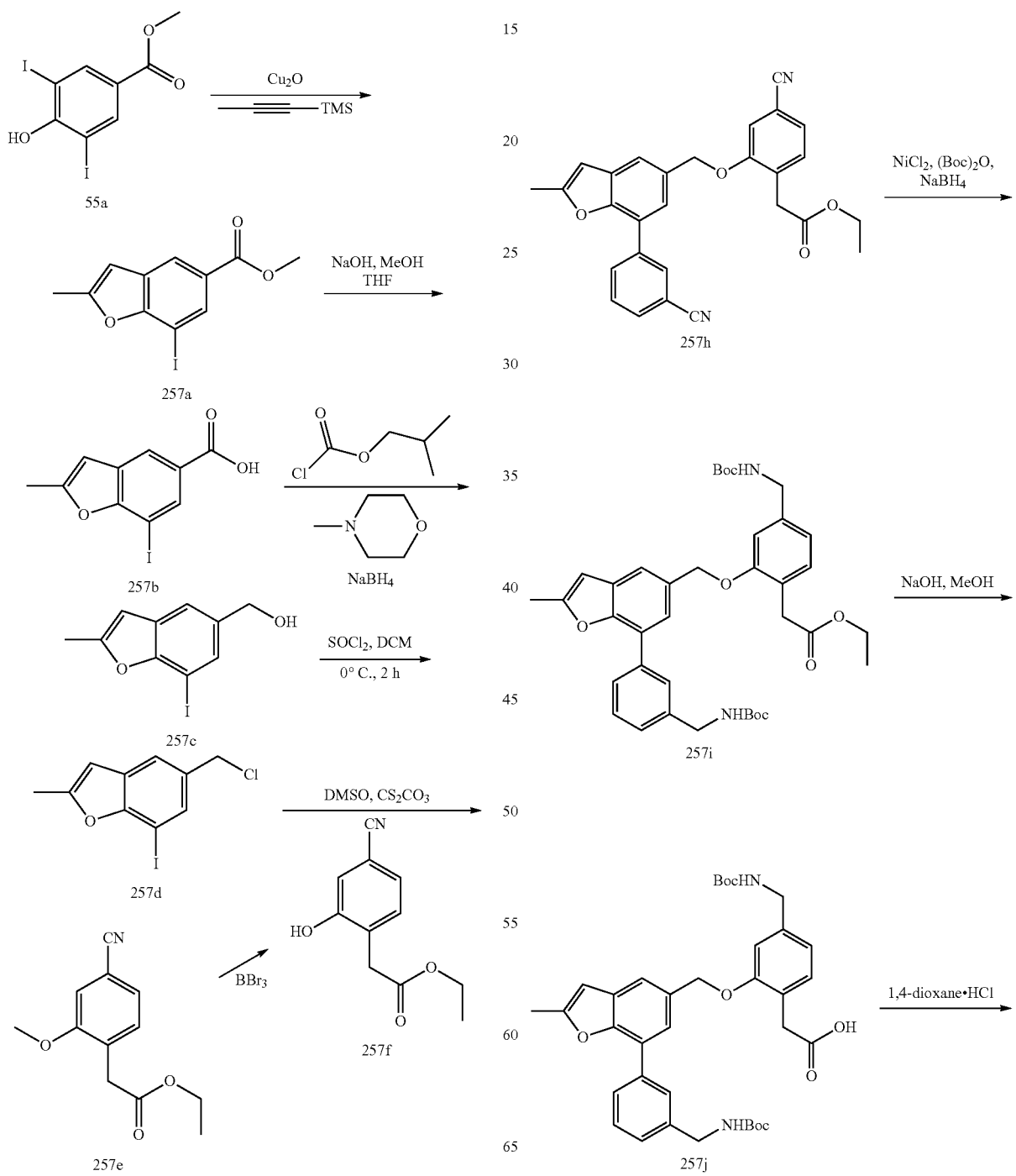

-continued

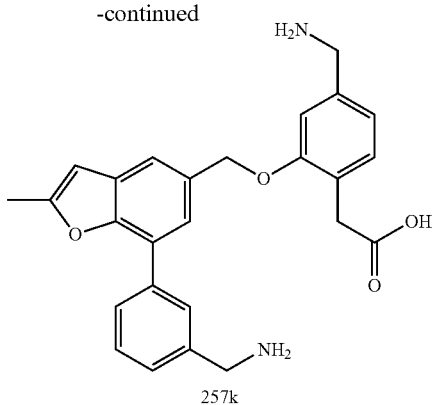

257k

Preparation of 2-(4-(aminomethyl)-2-((7-(3-(aminomethyl)phenyl)-2-methylbenzofuran-5-yl)methoxy)phenyl)acetic Acid (257k)

Step-1: Preparation of methyl 7-iodo-2-methylbenzofuran-5-carboxylate (257a)

Compound 257a was prepared according to the procedure reported in step-1 of scheme-55, from methyl 4-hydroxy-3,5-diiodobenzoate (55a) (3 g, 7.42 mmol) in pyridine (30 mL) using 1-(trimethylsilyl)-1-propyne (0.83 g, 7.42 mmol) and copper(I) oxide (0.53 g, 3.71 mmol). This gave after workup and purification by crystallization from n-heptane methyl 7-iodo-2-methylbenzofuran-5-carboxylate (257a) (1.1 g, 46%) as an off-white solid; $^1$H NMR (300 MHz, DMSO-$d_6$) δ 8.22-8.05 (m, 2H), 6.86 (d, J=1.3 Hz, 1H), 3.86 (s, 3H), 2.51 (s, 3H).

Step-2: Preparation of 7-iodo-2-methylbenzofuran-5-carboxylic acid (257b)

Compound 257b was prepared according to the procedure reported in step-4 of scheme-4 from methyl 7-iodo-2-methylbenzofuran-5-carboxylate (257a) (4.0 g, 12.65 mmol) in THF (40 mL) MeOH (120 mL) using a solution of sodium hydroxide (1015 g, 37.96 mmol) in water (40 mL). This gave after workup 7-iodo-2-methylbenzofuran-5-carboxylic acid (257b) (3.0 g, 79%) as an off-white solid. $^1$H NMR (300 MHz, DMSO-$d_6$) δ 13.06 (s, 1H), 8.14 (s, 2H), 6.86 (d, J=1.3 Hz, 1H), 2.51 (s, 3H).

Step-3: Preparation of (7-iodo-2-methylbenzofuran-5-yl)methanol (257c)

Compound 257c was prepared according to the procedure reported in step-1 of scheme-23 from 7-iodo-2-methylbenzofuran-5-carboxylic acid (257b) (3.0 g, 9.93 mmol) using N-methylmorpholine (1.2 g, 11.91 mmol) in THF (90 mL), isobutyl chloroformate (1.62 g, 11.91 mmol) and NaBH$_4$ (1.12 g, 29.79 mmol) in water (10 mL). This gave after workup and purification by flash column chromatography (silica gel, eluting with 0-30% EtOAc in n-heptane) (7-iodo-2-methylbenzofuran-5-yl)methanol (257c) (1.9 g, 66%) as a syrup. $^1$H NMR (300 MHz, DMSO-$d_6$) δ 7.54 (s, 1H), 7.43 (s, 1H), 6.70 (s, 1H), 5.25 (t, J=5.8 Hz, 1H), 4.51 (d, J=5.7 Hz, 2H), 2.46 (s, 3H).

Step-4: Preparation of 5-(chloromethyl)-7-iodo-2-methylbenzofuran (257d)

To a stirred solution of (7-iodo-2-methylbenzofuran-5-yl)methanol (257c) (1.5 g, 5.20 mmol) in DCM (30.0 mL) was added at 0° C. SOCl$_2$ (1.23 g, 10.40 mmol). The resulting reaction mixture was stirred for 2 h at 0° C., poured in saturated solution of NaHCO$_3$ (200 mL) and extracted with DCM (2×100 mL). The combined organics were washed with brine, dried, filtered and concentrated in vacuum to afford 5-(chloromethyl)-7-iodo-2-methylbenzofuran (257d) (1.5 g, 94%) as a thick oil. $^1$H NMR (300 MHz, DMSO-$d_6$) δ 7.65 (m, 2H), 6.73 (d, J=7.2 Hz, 1H), 4.83 (m, 2H), 2.48 (s, 3H).

Step-5: Preparation of Ethyl 2-(4-cyano-2-hydroxyphenyl)acetate (257f)

To a solution of ethyl 2-(4-cyano-2-methoxyphenyl)acetate (257e) (1.9 g, 8.67 mmol; CAS #1261674-45-6) in dichloromethane (35 mL) cooled to −78° C. was added boron tribromide (3.28 mL, 34.7 mmol) and allowed to warm to room temperature overnight. The reaction mixture was poured into ice/water treated with ethanol (20 mL) and concentrated in vacuum to dryness. The residue was treated again with ethanol (20 mL) and concentrated to dryness. The residue was dissolved in ethyl acetate (150 mL), washed with water (2×60 mL), brine (60 mL), dried, filtered and concentrated in vacuum to dryness. The residue obtained was purified by flash column chromatography [silica gel, eluting with hexanes/ethyl acetate (1:0 to 3:1)] to afford ethyl 2-(4-cyano-2-hydroxyphenyl)acetate (257f) (1.25 g, 70%) as an off-white solid; $^1$H NMR (300 MHz, DMSO-$d_6$) δ 10.39 (s, 1H), 7.34 (d, J=7.8 Hz, 1H), 7.22 (dd, J=7.7, 1.6 Hz, 1H), 7.10 (d, J=1.6 Hz, 1H), 4.06 (q, J=7.1 Hz, 2H), 3.64 (s, 2H), 1.17 (t, J=7.1 Hz, 3H).

Step-6: Preparation of Ethyl 2-(4-cyano-2-((7-iodo-2-methylbenzofuran-5-yl)methoxy)phenyl)acetate (257g)

To a stirred solution of 5-(chloromethyl)-7-iodo-2-methylbenzofuran (257d) (1.5 g, 4.89 mmol) in DMSO (15.0 mL) was added at room temperature ethyl 2-(4-cyano-2-hydroxyphenyl)acetate (257f) (1.00 g, 4.89 mmol), Cs$_2$CO$_3$ (4.87 g, 14.68 mmol) and stirred at room temperature for 18 h. The reaction mixture was poured in water (150 mL) and extracted ethyl acetate (2×50 mL). The combined organic layer was washed with brine, dried, filtered and concentrated in vacuum. The residue obtained was purified by flash column chromatography (silica gel, eluting with 0-10% EtOAc in n-heptane) to furnish ethyl 2-(4-cyano-2-((7-iodo-2-methylbenzofuran-5-yl)methoxy)phenyl)acetate (257g) (0.5 g, 22%) as an off-white solid; $^1$H NMR (300 MHz, DMSO-$d_6$) δ 7.66-7.49 (m, 3H), 7.51-7.34 (m, 2H), 6.75 (d, J=1.2 Hz, 1H), 5.19 (s, 2H), 4.01 (q, J=7.1 Hz, 2H), 3.70 (s, 2H), 2.48-2.47 (s, 3H), 1.06 (t, J=7.1 Hz, 3H).

Step-7: Preparation of Ethyl 2-(4-cyano-2-((7-(3-cyanophenyl)-2-methylbenzofuran-5-yl)methoxy)phenyl)acetate (257h)

Compound 257h was prepared according to the procedure reported in step-3 of scheme-1 from ethyl 2-(4-cyano-2-((7-iodo-2-methylbenzofuran-5-yl)methoxy)phenyl)acetate (257g) (1 g, 2.1 mmol) in acetonitrile (50 mL) using (3-cyanophenyl)boronic acid (0.206 g, 1.40 mmol), Pd(PPh$_3$)$_2$Cl$_2$ (0.221 g, 0.104 mmol) and a solution of Na$_2$CO$_3$ (0.668 g, 6.31 mmol) in water (5.0 mL) and heating under a nitrogen atmosphere at 90° C. for 4 h on an oil bath. This gave after workup, purification by flash column chromatography (silica gel, eluting with 0-40% EtOAc in n-heptane) ethyl 2-(4-cyano-2-((7-(3-cyanophenyl)-2-methylbenzofuran-5-yl)methoxy)phenyl)acetate (257h) (800 mg, 84% yield) as a white solid; $^1$H NMR (300 MHz, DMSO-d$_6$) δ 8.29 (t, J=1.6 Hz, 1H), 8.24 (dt, J=7.7, 1.5 Hz, 1H), 7.90 (dt, J=7.8, 1.4 Hz, 1H), 7.76 (t, J=7.8 Hz, 1H), 7.62 (dd, J=7.9, 1.5 Hz, 2H), 7.57 (d, J=1.6 Hz, 1H), 7.49-7.38 (m, 2H), 6.70 (d, J=1.3 Hz, 1H), 5.29 (s, 2H), 3.93 (q, J=7.1 Hz, 2H), 3.73 (s, 2H), 2.49 (s, 3H), 0.97 (t, J=7.1 Hz, 3H); MS (ES+): 430.3 (M+1).

Step-8: Preparation of Ethyl 2-(4-(((tert-butoxycarbonyl)amino)methyl)-2-((7-(3-(((tert-butoxycarbonyl)amino)methyl)phenyl)-2-methylbenzofuran-5-yl)methoxy)phenyl)acetate (257i)

Compound 257i was prepared according to the procedure reported in step-2 of scheme-256 from ethyl 2-(4-cyano-2-((7-(3-cyanophenyl)-2-methylbenzofuran-5-yl)methoxy)phenyl)acetate (257h) in methanol (20 mL) using Boc anhydride (1.55 g, 7.10 mmol), nickel (II) chloride hexahydrate (0.21 g, 0.88 mmol) and sodium borohydride (0.58 g, 14.2 mmol). This gave after purified by flash column chromatography (silica gel, eluting with 0-30% EtOAc in n-heptane) ethyl 2-(4-(((tert-butoxycarbonyl)amino)methyl)-2-((7-(3-(((tert-butoxycarbonyl)amino)methyl)phenyl)-2-methylbenzofuran-5-yl)methoxy)phenyl)acetate (257i) (0.5 g, 43%) as an oil; $^1$H NMR (300 MHz, DMSO-d$_6$) δ 7.71 (s, 1H), 7.64-7.53 (m, 2H), 7.52-7.34 (m, 2H), 7.28 (d, J=7.6 Hz, 1H), 7.14 (d, J=7.5 Hz, 1H), 7.01 (s, 1H), 6.78 (d, J=7.6 Hz, 1H), 6.65 (s, 1H), 5.16 (s, 2H), 4.22 (d, J=6.1 Hz, 2H), 4.11 (d, J=6.2 Hz, 2H), 3.90 (q, J=7.1 Hz, 2H), 3.57 (s, 2H), 2.48 (s, 3H), 1.46-1.27 (m, 18H), 0.96 (t, J=7.1 Hz, 3H).

Step-9: Preparation of 2-(4-(((tert-butoxycarbonyl)amino)methyl)-2-((7-(3-(((tert-butoxycarbonyl)amino)methyl)phenyl)-2-methylbenzofuran-5-yl)methoxy)phenyl)acetic acid (257j)

Compound 257j was prepared according to the procedure reported in step-4 of scheme-4 from ethyl 2-(4-(((tert-butoxycarbonyl)amino)methyl)-2-((7-(3-(((tert-butoxycarbonyl)amino)methyl)phenyl)-2-methylbenzofuran-5-yl)methoxy)phenyl)acetate (257i) (0.3 g, 0.44 mmol) in MeOH (10 mL) using a solution of NaOH (54 mg, 1.32 mmol) in water (5 mL). This gave after workup 2-(4-(((tert-butoxycarbonyl)amino)methyl)-2-((7-(3-(((tert-butoxycarbonyl)amino)methyl)phenyl)-2-methylbenzofuran-5-yl)methoxy)phenyl)acetic acid (257j) (0.2 g, 69.47%) as an off white solid; $^1$H NMR (300 MHz, DMSO-d$_6$) δ 7.78-7.69 (m, 2H), 7.65-7.56 (m, 1H), 7.54-7.40 (m, 2H), 7.40-7.23 (m, 1H), 7.14 (d, J=7.6 Hz, 1H), 7.00 (s, 1H), 6.77 (d, J=7.6 Hz, 1H), 6.66 (s, 1H), 5.18 (s, 2H), 4.23 (d, J=6.2 Hz, 1H), 4.09 (d, J=6.2 Hz, 1H), 4.02 (q, J=7.1 Hz, 2H), 3.54 (s, 2H), 2.47 (s, 3H), 1.38 (d, J=5.5 Hz, 18H), 1.17 (t, J=7.1 Hz, 3H).

Step-10: Preparation of 2-(4-(aminomethyl)-2-((7-(3-(aminomethyl)phenyl)-2-methylbenzofuran-5-yl)methoxy)phenyl)acetic Acid (257k)

To a stirred solution of 2-(4-(((tert-butoxycarbonyl)amino)methyl)-2-((7-(3-(((tert-butoxycarbonyl)amino)

methyl)phenyl)-2-methylbenzofuran-5-yl)methoxy)phenyl)acetic acid (257j) (0.2 g, 0.31 mmol) in 1,4-dioxane (2.0 mL) was added at room temperature 1,4-dioxane. HCl (28%, 2.0 mL) and stirred for 2 h. The solid obtained was collected by filtration, dried, and purified by reverse phase column chromatography [C-18, steel column (250 mm×30 mm) eluting with 0.1% aq. HCl in water and acetonitrile from 0-100%] to afford 2-(4-(aminomethyl)-2-((7-(3-(aminomethyl)phenyl)-2-methylbenzofuran-5-yl)methoxy)phenyl)acetic acid (257k) (0.045 g) as an off white solid; $^1$H NMR (300 MHz, DMSO-d$_6$) δ 8.48 (s, 5H), 8.01 (s, 1H), 7.93 (dt, J=7.3, 1.8 Hz, 1H), 7.65-7.50 (m, 4H), 7.41 (s, 1H), 7.25 (d, J=7.6 Hz, 1H), 7.01 (dd, J=7.6, 1.5 Hz, 1H), 6.67 (d, J=1.3 Hz, 1H), 5.24 (s, 2H), 4.14 (s, 2H), 3.99 (s, 2H), 3.59 (s, 2H), 2.49 (s, 3H); MS (ES+): 431.20 (M+1); (ES−) 429.20 (M−1); Analysis calculated for C$_{26}$H$_{26}$N$_2$O$_4$.2HCl.2.75H$_2$O: C, 56.47; H, 6.11; Cl, 12.82; N, 5.07; Found: C, 56.61; H, 5.93; Cl, 12.79; N, 5.11.

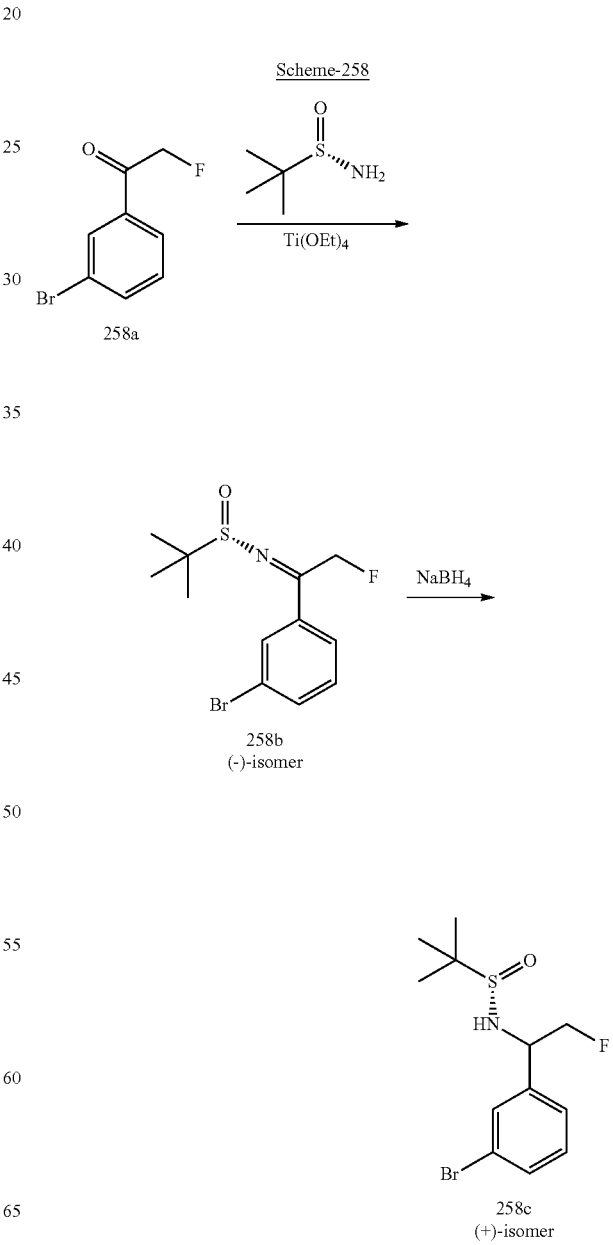

Scheme-258

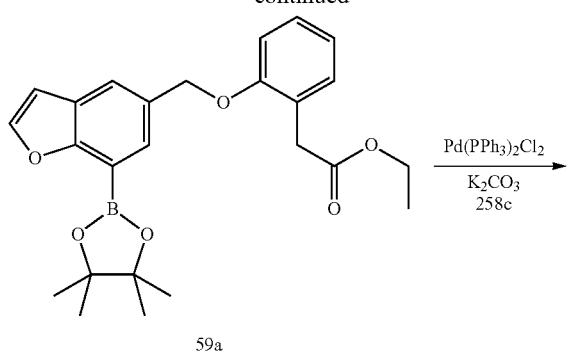

59a

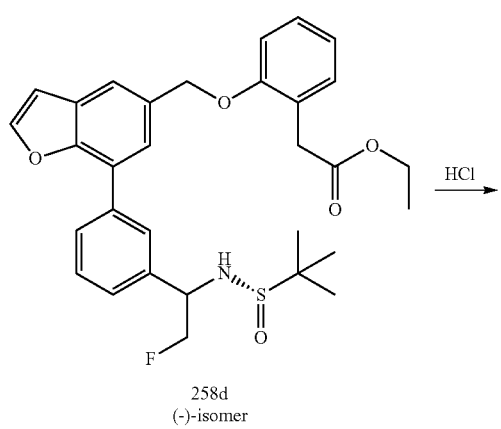

258d
(−)-isomer

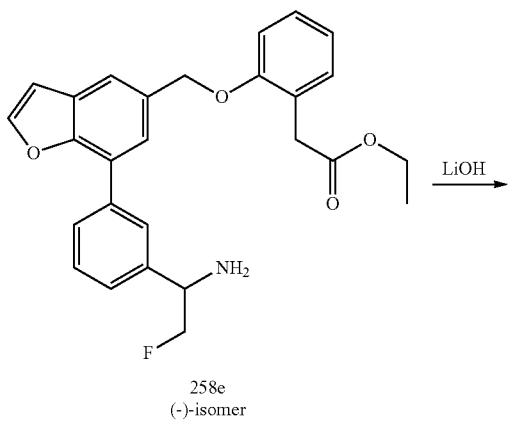

258e
(−)-isomer

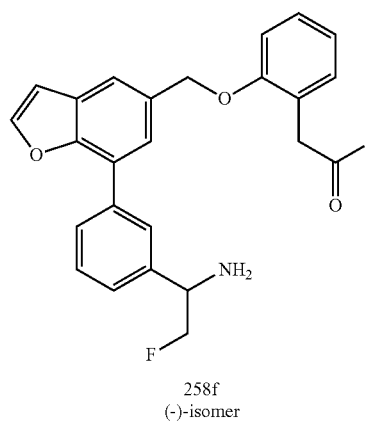

258f
(−)-isomer

Preparation of (−)-2-(2-((7-(3-(1-amino-2-fluoro-ethyl)phenyl)benzofuran-5-yl)methoxy)phenyl)acetic Acid (258f)

Step-1: Preparation of (−)-(S)—N-(1-(3-bromophenyl)-2-fluoroethylidene)-2-methylpropane-2-sulfinamide (258b)

To a solution of 1-(3-bromophenyl)-2-fluoroethanone (258a) (3 g, 13.82 mmol; CAS #1219632-64-0) and (S)-2-methylpropane-2-sulfinamide (3.35 g, 27.6 mmol) in tetrahydrofuran (50 mL) was added tetraethoxytitanium (6.31 g, 27.6 mmol) and stirred overnight at rt. Reaction was quenched with brine (20 mL) and stirred for 20 minutes. The solid separated out was removed by filter and cake was washed with ethyl acetate (200 mL). The organic layer was separated washed with brine (2×20 mL), dried and concentrated in vacuum. The crude residue was purified by flash column chromatography [(silica gel, 40 g, eluting with ethyl acetate in hexanes (0 to 20%)] to afford (−)-(S)—N-(1-(3-bromophenyl)-2-fluoroethylidene)-2-methylpropane-2-sulfinamide (258b) (2.456 g, 7.67 mmol, 56% yield) as brown syrup; MS (ES+) 320.0, 322.0 (M+1); Optical rotation $[\alpha]_D = -2.43$ (c=1.65, MeOH).

Step-2: Preparation of (+)-(S)—N-(1-(3-bromophenyl)-2-fluoroethyl)-2-methylpropane-2-sulfinamide (258c)

To a solution of (−)-(S)—N-(1-(3-bromophenyl)-2-fluoroethylidene)-2-methylpropane-2-sulfinamide (258b) (2.4 g, 7.49 mmol) in tetrahydrofuran (50 mL) and water (1 mL) was added sodium borohydride (0.851 g, 22.48 mmol) portion wise below −56° C. over a period of 2 min. The reaction was then stirred at the same temperature for 30 min and allowed to warm to −12° C. over a period of 30 min. Reaction mixture was quenched with acetone (3 mL) and stirred for 10 mins, diluted with water and concentrated in vacuum to remove organic solvents. The aqueous layer was extracted with ethyl acetate (2×100 mL) and combined organic layer was washed with (2×50 mL), brine (50 mL), dried and concentrated in vacuum to get a clear oil. The crude residue was purified by flash column chromatography [(silica gel, 80 g, eluting with ethyl acetate in hexanes (0 to 100%)] to afford (+)-(S)—N-(1-(3-bromophenyl)-2-fluoroethyl)-2-methylpropane-2-sulfinamide (258c) (1.25 g, 52% yield) as a white solid; $^1$H NMR (300 MHz, DMSO-d$_6$) δ 7.71 (t, J=1.8 Hz, 1H), 7.53-7.43 (m, 2H), 7.32 (t, J=7.8 Hz, 1H), 6.04 (d, J=8.9 Hz, 1H), 4.68-4.53 (m, 2H), 4.42 (d, J=6.3 Hz, 1H), 1.12 (s, 9H); $^{19}$F NMR (282 MHz, DMSO-d$_6$) δ−217.83; Optical rotation $[\alpha]_D = +5.26$ (c=0.69, MeOH).

Step-3: Preparation of (−)-ethyl 2-(2-((7-(3-(1-((S)-1,1-dimethylethylsulfinamido)-2-fluoroethyl)phenyl)benzofuran-5-yl)methoxy)phenyl)acetate (258d)

Compound 258d was prepared according to the procedure reported in step-3 of scheme-1 from ethyl 2-(2-((7-(4,4,5,5-tetramethyl-1,3,2-dioxaborolan-2-yl)benzofuran-5-yl)methoxy)phenyl)acetate (59a) (500 mg, 1.146 mmol) in dioxane (10 mL) using (+)-(S)—N-(1-(3-bromophenyl)-2-fluoroethyl)-2-methylpropane-2-sulfinamide (258c) (443 mg, 1.375 mmol), Pd(PPh$_3$)$_2$Cl$_2$ (121 mg, 0.172 mmol) and a solution of K$_2$CO$_3$ (475 mg, 3.44 mmol) in water (1 mL) under a nitrogen atmosphere and heating at 100° C. for 5 h on oil bath. This gave after workup and purification by flash column chromatography (silica gel, 40 g, eluting with 9:1 mixture of ethyl acetate and methanol in hexanes) (−)-ethyl 2-(2-((7-(3-(1-((S)-1,1-dimethylethylsulfinamido)-2-fluoroethyl)phenyl)benzofuran-5-yl)methoxy)phenyl)acetate (258d) (392 mg, 62% yield) as a clear oil; $^1$H NMR (300 MHz, DMSO-$d_6$) δ 8.09 (d, J=2.2 Hz, 1H), 7.93 (s, 1H), 7.83 (td, J=4.6, 1.7 Hz, 1H), 7.72 (d, J=1.6 Hz, 1H), 7.67-7.56 (m, 1H), 7.56-7.50 (m, 2H), 7.25 (ddd, J=16.0, 8.1, 1.7 Hz, 2H), 7.17-7.09 (m, 1H), 7.06 (d, J=2.2 Hz, 1H), 6.91 (td, J=7.3, 1.1 Hz, 1H), 6.05 (d, J=8.3 Hz, 1H), 5.24 (s, 2H), 4.76-4.63 (m, 2H), 4.52 (d, J=6.3 Hz, 1H), 3.96-3.86 (m, 2H), 3.63 (s, 2H), 1.13 (s, 9H), 0.97 (t, J=7.1 Hz, 3H); $^{19}$F NMR (282 MHz, DMSO-$d_6$) δ −216.98; MS (ES+): 552.2 (M+1); Optical rotation [α]$_D$=−1.78 (c=0.23, MeOH).

Step-4: Preparation of (−)-ethyl 2-(2-((7-(3-(1-amino-2-fluoroethyl)phenyl)benzofuran-5-yl)methoxy)phenyl)acetate (258e)

Compound 258e was prepared according to the procedure reported in step-10 of scheme-257 from (−)-ethyl 2-(2-((7-(3-(1-((S)-1,1-dimethylethylsulfinamido)-2-fluoroethyl)phenyl)benzofuran-5-yl)methoxy)phenyl)acetate (258d) (450 mg, 0.82 mmol) in THF (10 mL) using HCl (4 M in 1,4-dioxane) (0.408 mL, 1.63 mmol) and stirring for 30 mins. This gave after workup and purification by flash column chromatography (silica gel, 25 g eluting with DMA 80 in dichloromethane) (−)-ethyl 2-(2-((7-(3-(1-amino-2-fluoroethyl)phenyl)benzofuran-5-yl)methoxy)phenyl)acetate (258e) (260 mg, 71% yield) as a white solid; $^1$H NMR (300 MHz, DMSO-$d_6$) δ 8.10 (d, J=2.2 Hz, 1H), 7.89 (d, J=2.1 Hz, 1H), 7.82-7.75 (m, 1H), 7.70 (d, J=1.6 Hz, 1H), 7.59 (d, J=1.7 Hz, 1H), 7.51-7.46 (m, 2H), 7.29-7.19 (m, 2H), 7.12 (dd, J=8.3, 1.1 Hz, 1H), 7.05 (d, J=2.2 Hz, 1H), 6.91 (td, J=7.4, 1.1 Hz, 1H), 5.25 (s, 2H), 3.92 (q, J=7.1 Hz, 2H), 3.75-3.66 (m, 1H), 3.63 (s, 2H), 2.09 (s, 2H), 0.97 (t, J=7.1 Hz, 3H); MS (ES+): 448.0 (M+1); Optical rotation [α]$_D$=−37.78 (c=0.09, MeOH).

Step-5: Preparation of (−)-2-(2-((7-(3-(1-amino-2-fluoroethyl)phenyl)benzofuran-5-yl)methoxy)phenyl)acetic Acid (258f)

Compound 258f was prepared according to the procedure reported in step-6 of scheme-1 from (−)-ethyl 2-(2-((7-(3-(1-amino-2-fluoroethyl)phenyl)benzofuran-5-yl)methoxy)phenyl)acetate (258e) (250 mg, 0.56 mmol) in MeOH (5 mL), THF (5 mL) using a solution of lithium hydroxide monohydrate (54 mg, 2.24 mmol) in water (2 mL). This gave after workup and purification by reverse phase column [C18 (50g), eluting with ACN in water (containing 0.1% HCl) from 0-100%] (−)-2-(2-((7-(3-(1-amino-2-fluoroethyl)phenyl)benzofuran-5-yl)methoxy)phenyl)acetic acid (258f) (115 mg, 49% yield) HCl salt as a white solid; $^1$H NMR (300 MHz, DMSO-$d_6$) δ 8.11 (d, J=2.2 Hz, 1H), 8.04 (s, 1H), 8.00-7.95 (m, 1H), 7.77 (d, J=1.6 Hz, 1H), 7.68-7.63 (m, 2H), 7.63-7.56 (m, 1H), 7.24 (t, J=7.6 Hz, 2H), 7.10 (d, J=8.1 Hz, 1H), 7.07 (d, J=2.2 Hz, 1H), 6.94-6.87 (m, 1H), 5.27 (s, 2H), 4.95-4.83 (m, 1H), 4.83-4.69 (m, 2H), 3.60 (s, 2H); MS (ES+): 420.1 (M+1), (ES−): 418.1 (M−1); optical rotation [t]D=−11.76 (c=0.51; MeOH); Chiral HPLC: AD-H column; solvent: 80/20 (0.1% DEA in Heptane/0.1% DEA in ethanol); flow rate: 1.0 mL/min; UV detection 271 nm; run time=15 mins; Temperature 40° C.; R$_t$=10.033 [Peak-1 compound (258f), 96.90%]; R$_t$=11.44] peak-2;

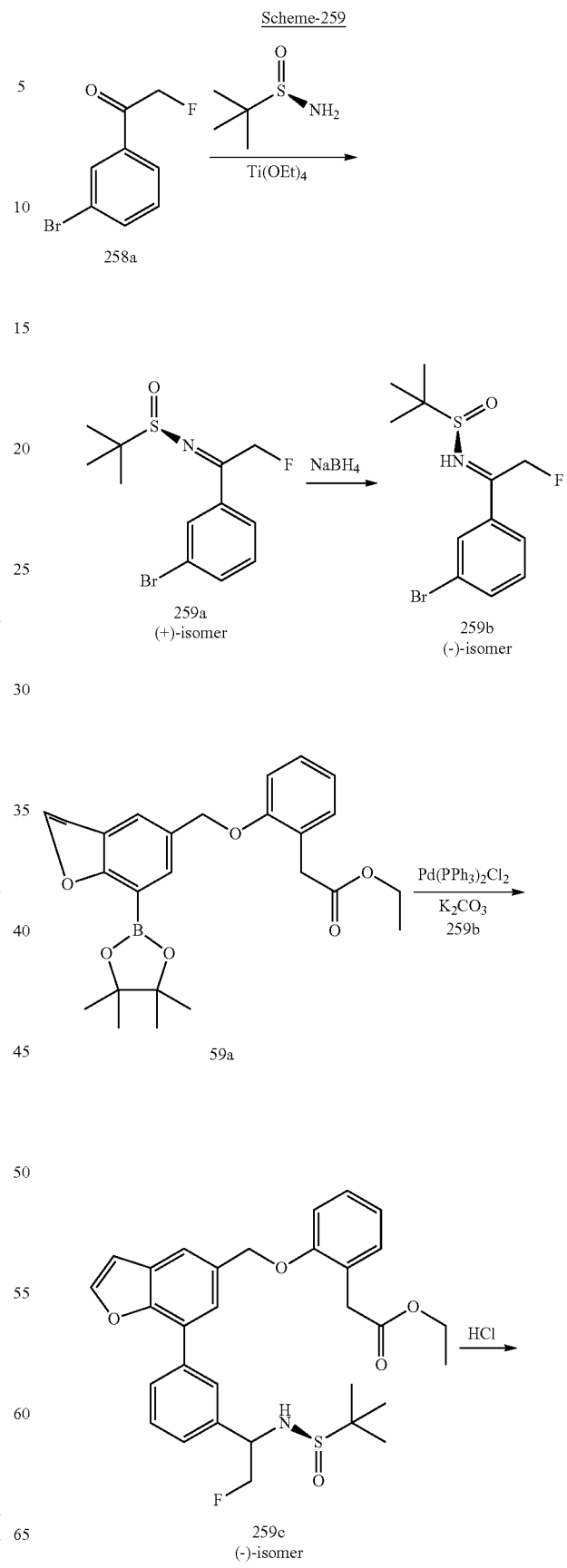

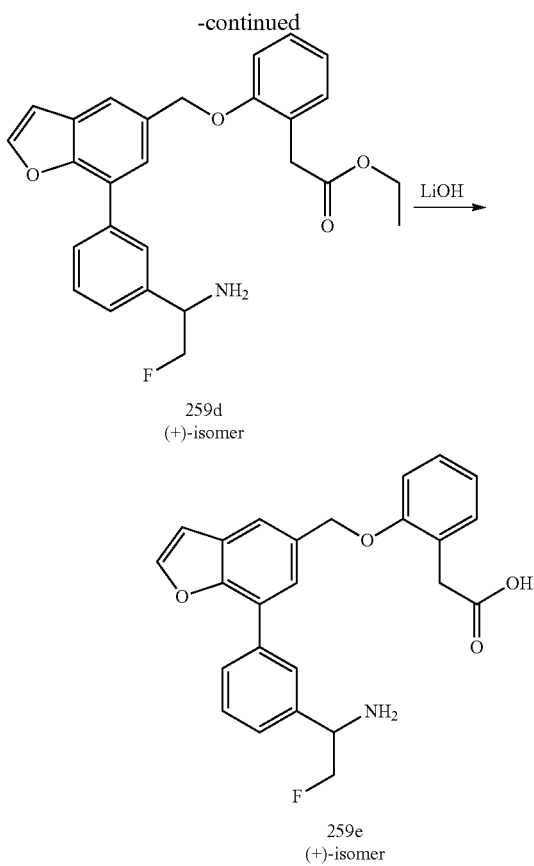

259d
(+)-isomer 259e
(+)-isomer

Preparation of (+)-2-(2-((7-(3-(1-amino-2-fluoro-ethyl)phenyl)benzofuran-5-yl)methoxy)phenyl)acetic Acid (259e)

Step-1: Preparation of (+)-(R)—N-(1-(3-bromophenyl)-2-fluoroethylidene)-2-methylpropane-2-sulfinamide (259a)

Compound 259a was prepared according to the procedure reported in step-1 of scheme-258 from 1-(3-bromophenyl)-2-fluoroethanone (258a) (3 g, 13.82 mmol; CAS #1219632-64-0) and (R)-2-methylpropane-2-sulfinamide (3.35 g, 27.6 mmol) in tetrahydrofuran (50 mL) using tetraethoxytitanium (6.31 g, 27.6 mmol). This gave after workup and purification by flash column chromatography [(silica gel, 40 g, eluting with ethyl acetate in hexanes (0 to 20%)] (+)-(R)—N-(1-(3-bromophenyl)-2-fluoroethylidene)-2-methylpropane-2-sulfinamide (259a) (2.08 g, 47% yield) as a brown syrup; MS (ES+): 320.0, 322.0 (M+1); Optical rotation $[\alpha]_D$=+2.76 (c=1.02, MeOH).

Step-2: Preparation of (−)-(R)—N-(1-(3-bromophenyl)-2-fluoroethyl)-2-methylpropane-2-sulfinamide (259b)

Compound 259b was prepared according to the procedure reported in step-2 of scheme-258 from (+)-(R)—N-(1-(3-bromophenyl)-2-fluoroethylidene)-2-methylpropane-2-sulfinamide (259a) (2.0 g, 6.25 mmol) in tetrahydrofuran (40 mL) and water (1 mL) using sodium borohydride (0.709 g, 18.74 mmol). This gave after workup and purification by flash column chromatography [(silica gel, 80 g, eluting with ethyl acetate in hexanes (0 to 100%)] (−)-(R)—N-(1-(3-bromophenyl)-2-fluoroethyl)-2-methylpropane-2-sulfinamide (259b) (1.5 g, 75% yield) as a white solid; $^1$H NMR (300 MHz, DMSO-$d_6$) δ 7.71 (t, J=1.9 Hz, 1H), 7.56-7.41 (m, 2H), 7.33 (t, J=7.8 Hz, 1H), 6.05 (d, J=8.9 Hz, 1H), 4.65-4.50 (m, 2H), 4.42 (d, J=6.3 Hz, 1H), 1.13 (s, 9H); $^{19}$F NMR (282 MHz, DMSO-$d_6$) δ−217.83; Optical rotation $[\alpha]_D$=−7.16 (c=1.01, MeOH).

Step-3: Preparation of (−)-ethyl 2-(2-((7-(3-(1-((R)-1,1-dimethylethylsulfinamido)-2-fluoroethyl)phenyl)benzofuran-5-yl)methoxy)phenyl)acetate (259c)

Compound 259c was prepared according to the procedure reported in step-3 of scheme-1 from ethyl 2-(2-((7-(4,4,5,5-tetramethyl-1,3,2-dioxaborolan-2-yl)benzofuran-5-yl)methoxy)phenyl)acetate (59a) (500 mg, 1.146 mmol) in dioxane (10 mL) using (−)-(R)—N-(1-(3-bromophenyl)-2-fluoroethyl)-2-methylpropane-2-sulfinamide (259b) (443 mg, 1.375 mmol), Pd(PPh$_3$)$_2$Cl$_2$ (121 mg, 0.172 mmol) and a solution of K$_2$CO$_3$ (475 mg, 3.44 mmol) in water (1 mL) under a nitrogen atmosphere and heating at 100° C. for 5 h on oil bath. This gave after workup and purification by flash column chromatography (silica gel, 40 g, eluting with 9:1 mixture of ethyl acetate and methanol in hexanes) (−)-ethyl 2-(2-((7-(3-(1-((R)-1,1-dimethylethylsulfinamido)-2-fluoroethyl)phenyl)benzofuran-5-yl)methoxy)phenyl)acetate (259c) (392 mg, 0.711 mmol, 62.0% yield) as a clear oil; $^1$H NMR (300 MHz, DMSO-$d_6$) δ 8.09 (d, J=2.2 Hz, 1H), 7.93 (s, 1H), 7.83 (td, J=4.6, 1.7 Hz, 1H), 7.72 (d, J=1.6 Hz, 1H), 7.67-7.56 (m, 1H), 7.56-7.50 (m, 2H), 7.25 (ddd, J=16.0, 8.1, 1.7 Hz, 2H), 7.17-7.09 (m, 1H), 7.06 (d, J=2.2 Hz, 1H), 6.91 (td, J=7.3, 1.1 Hz, 1H), 6.05 (d, J=8.3 Hz, 1H), 5.24 (s, 2H), 4.76-4.63 (m, 2H), 4.52 (d, J=6.3 Hz, 1H), 3.96-3.86 (m, 2H), 3.63 (s, 2H), 1.13 (s, 9H), 0.97 (t, J=7.1 Hz, 3H); $^{19}$F NMR (282 MHz, DMSO-$d_6$) δ−216.98; MS (ES+): 552.2 (M+1); Optical rotation $[\alpha]_D$=−6.40 (c=0.13, MeOH).

Step-4: Preparation of (+)-ethyl 2-(2-((7-(3-(1-amino-2-fluoroethyl)phenyl)benzofuran-5-yl)methoxy)phenyl)acetate (259d)

Compound 259d was prepared according to the procedure reported in step-10 of scheme-257 from (−)-ethyl 2-(2-((7-(3-(1-((R)-1,1-dimethylethylsulfinamido)-2-fluoroethyl)phenyl)benzofuran-5-yl)methoxy)phenyl)acetate (259c) (370 mg, 0.67 mmol) in THF (10 mL) using HCl (4 M in 1,4-dioxane) (0.335 mL, 1.34 mmol) and stirring for 30 mins. This gave after workup and purification by flash column chromatography (silica gel, 25 g, eluting with DMA 80 in dichloromethane) (+)-ethyl 2-(2-((7-(3-(1-amino-2-fluoroethyl)phenyl)benzofuran-5-yl)methoxy)phenyl)acetate (259d) (245 mg, 82% yield) as a white solid; $^1$H NMR (300 MHz, DMSO-$d_6$) δ 8.10 (d, J=2.2 Hz, 1H), 7.89 (d, J=2.1 Hz, 1H), 7.82-7.75 (m, 1H), 7.71 (d, J=1.6 Hz, 1H), 7.59 (d, J=1.7 Hz, 1H), 7.54-7.43 (m, 2H), 7.32-7.19 (m, 2H), 7.12 (dd, J=8.2, 1.1 Hz, 1H), 7.05 (d, J=2.2 Hz, 1H), 6.91 (td, J=7.3, 1.1 Hz, 1H), 5.25 (s, 2H), 3.92 (q, J=7.1 Hz, 2H), 3.63 (s, 2H), 3.34 (s, 1H), 2.09 (s, 2H), 0.97 (t, J=7.1 Hz, 3H); MS (ES+): 448.0 (M+1); Optical rotation $[\alpha]_D$=+10.57 (c=0.44, MeOH).

Step-5: Preparation of (+)-2-(2-((7-(3-(1-amino-2-fluoroethyl)phenyl)benzofuran-5-yl)methoxy)phenyl)acetic Acid (259e)

Compound 259e was prepared according to the procedure reported in step-6 of scheme-1 from (+)-ethyl 2-(2-((7-(3-

(1-amino-2-fluoroethyl)phenyl)benzofuran-5-yl)methoxy)phenyl)acetate (259d) (235 mg, 0.53 mmol) in MeOH (5 mL), THF (5 mL) using a solution of lithium hydroxide monohydrate (50 mg, 2.1 mmol) in water (2 mL). This gave after workup and purification by reverse phase column [C18 (50g), eluting with ACN in water (containing 0.1% HCl) from 0-100%] (+)-2-(2-((7-(3-(1-amino-2-fluoroethyl)phenyl)benzofuran-5-yl)methoxy)phenyl)acetic acid (259e) (70 mg, 0.167 mmol, 31.8% yield) as a white hydrochloride salt; $^1$H NMR (300 MHz, DMSO-$d_6$) δ 8.11 (d, J=2.2 Hz, 1H), 8.04 (s, 1H), 7.97 (dt, J=7.3, 1.7 Hz, 1H), 7.77 (d, J=1.5 Hz, 1H), 7.67-7.63 (m, 2H), 7.65-7.55 (m, 1H), 7.24 (t, J=7.6 Hz, 2H), 7.09 (d, J=7.9 Hz, 1H), 7.07 (d, J=2.2 Hz, 1H), 6.95-6.84 (m, 1H), 5.27 (s, 2H), 4.94-4.85 (m, 1H), 4.88-4.68 (m, 2H), 3.60 (s, 2H); MS (ES+): 420.1 (M+1), (ES−): 418.1 (M−1); Optical rotation [t]D=+11.83 (c=0.49, MeOH); Chiral HPLC: AD-H column; solvent: 80/20 (0.1% DEA in Heptane/0.1% DEA in ethanol); flow rate: 1.0 mL/min; UV detection 271 nm; run time=15 mins; Temperature 40° C.; $R_t$=10.05 [Peak-1 compound (258f), 6.56%]; $R_t$=11.36] peak-2; compound (259e) 93.44%] 86.88% ee.

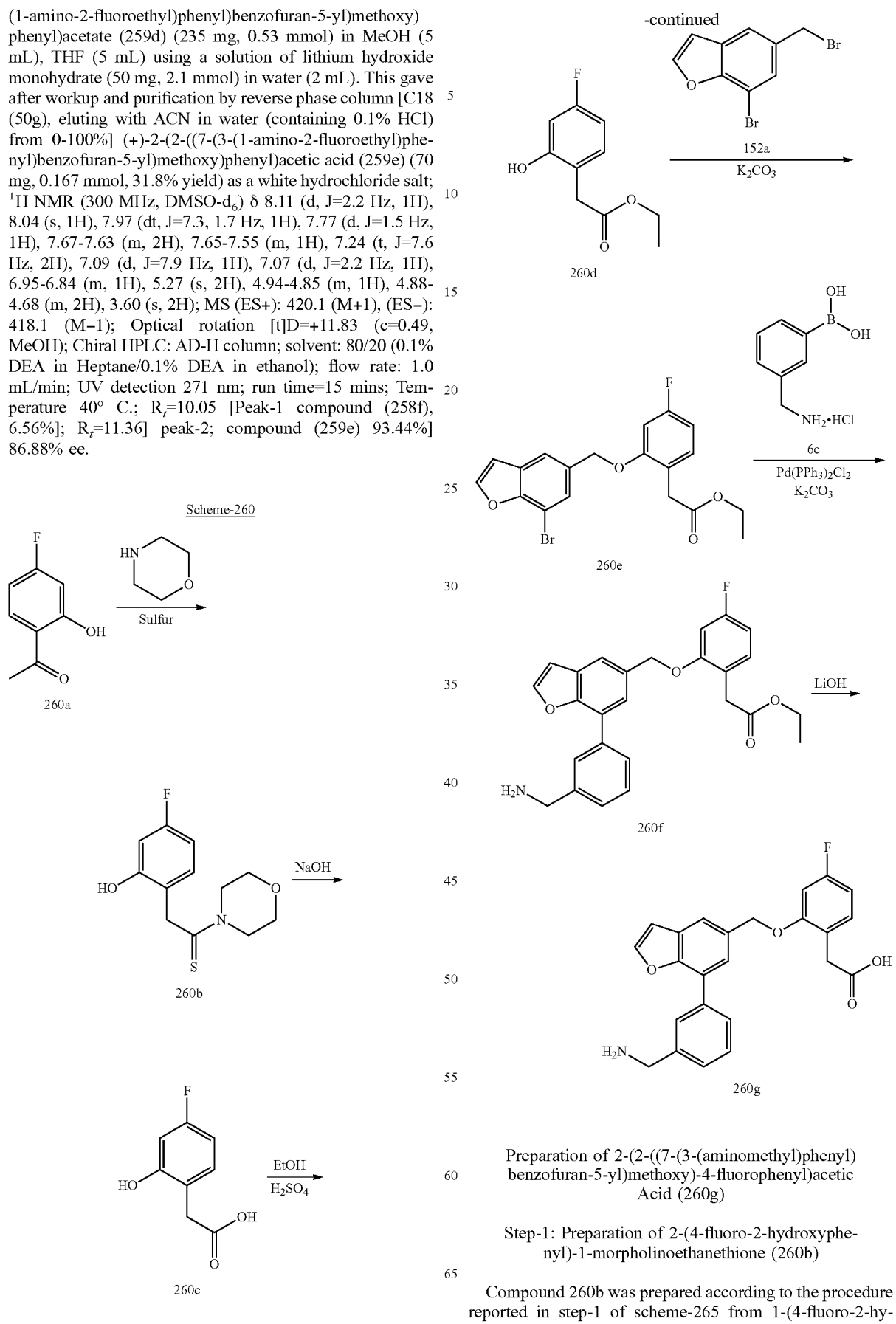

Preparation of 2-(2-((7-(3-(aminomethyl)phenyl)benzofuran-5-yl)methoxy)-4-fluorophenyl)acetic Acid (260g)

Step-1: Preparation of 2-(4-fluoro-2-hydroxyphenyl)-1-morpholinoethanethione (260b)

Compound 260b was prepared according to the procedure reported in step-1 of scheme-265 from 1-(4-fluoro-2-hydroxyphenyl)ethanone (260a) (25 g, 162 mmol; CAS #1481-27-2) in N-Methyl-2-pyrrolidinone (150 mL) using sulfur powder (10.40 g, 324 mmol), morpholine (28.0 mL, 324 mmol) and heating at 100° C. for 1.5 h. This gave after workup and purification by flash column chromatography [silica gel (220 g), eluting with 0 to 50% ethyl acetate in hexanes] 2-(4-fluoro-2-hydroxyphenyl)-1-morpholinoethanethione (260b) (21.29 g, 51% yield). $^1$H NMR (300 MHz, DMSO-$d_6$) δ 10.20 (s, 1H), 7.16 (dd, J=9.4, 6.8 Hz, 1H), 6.72-6.54 (m, 2H), 4.24 (dd, J=5.7, 4.2 Hz, 2H), 4.06 (s, 2H), 3.68-3.61 (m, 4H), 3.45 (dd, J=5.7, 4.0 Hz, 2H); $^{19}$F NMR (282 MHz, DMSO-$d_6$) δ−114.69.

Step-2: Preparation of 2-(4-fluoro-2-hydroxyphenyl)acetic Acid (260c)

Compound 260c was prepared according to the procedure reported in step-2 of scheme-265 from 2-(4-fluoro-2-hydroxyphenyl)-1-morpholinoethanethione (260b) (25.39g, 99 mmol) in ethanol (200 mL) and Water (50 mL) using sodium hydroxide (15.91 g, 398 mmol) and heating at reflux for 9 h. This gave after workup 2-(4-fluoro-2-hydroxyphenyl)acetic acid (260c) (15.5 g, 92% yield) which was used in the next reaction without further purification. $^1$H NMR (300 MHz, DMSO-$d_6$) δ 7.23-6.96 (m, 1H), 6.62-6.45 (m, 2H), 3.44 (s, 2H); $^{19}$F NMR (282 MHz, DMSO-$d_6$) δ−114.71.

Step-3: Preparation of Ethyl 2-(4-fluoro-2-hydroxyphenyl)acetate (260d)

Compound 260d was prepared according to the procedure reported in step-3 of scheme-265 from 2-(4-fluoro-2-hydroxyphenyl)acetic acid (260c) (15.5 g, 91 mmol) in ethanol (150 mL) using sulfuric acid (5.34 mL, 100 mmol) and heating at reflux for 6 h. This gave after workup and purification by flash column chromatography (silica gel, 120 g, eluting with 0 to 20% ethyl acetate and hexanes) ethyl 2-(4-fluoro-2-hydroxyphenyl)acetate (260d) (13.94 g, 77% yield). $^1$H NMR (300 MHz, DMSO-$d_6$) δ 9.99 (s, 1H), 7.29-6.96 (m, 1H), 6.71-6.37 (m, 2H), 4.05 (q, J=7.1 Hz, 2H), 3.51 (s, 2H), 1.17 (t, J=7.1 Hz, 3H); $^{19}$F NMR (282 MHz, DMSO-$d_6$) δ−114.38.

Step-4: Preparation of Ethyl 2-(2-((7-bromobenzofuran-5-yl)methoxy)-4-fluorophenyl)acetate (260e)

Compound 260e was prepared according to the procedure reported in step-2 of scheme-152 from 7-bromo-5-(bromomethyl)benzofuran (152a) (2.63 g, 9.08 mmol) using ethyl 2-(4-fluoro-2-hydroxyphenyl)acetate (260d) (1.8 g, 9.08 mmol), $K_2CO_3$ (3.77 g, 27.2 mmol) in DMF (10 mL) and stirring at room temperature for 12h. This gave after workup and purification by flash column chromatography (SiO$_2$, 40 g, eluting with 0 to 50% EtOAc in hexane) ethyl 2-(2-((7-bromobenzofuran-5-yl)methoxy)-4-fluorophenyl)acetate (260e) (3.224 g, 87% yield) as a white solid. $^1$H NMR (300 MHz, DMSO-$d_6$) δ 8.15 (d, J=2.2 Hz, 1H), 7.72 (d, J=1.5 Hz, 1H), 7.60 (d, J=1.5 Hz, 1H), 7.25 (dd, J=8.3, 6.9 Hz, 1H), 7.12 (d, J=2.2 Hz, 1H), 7.02 (dd, J=11.3, 2.5 Hz, 1H), 6.75 (td, J=8.5, 2.5 Hz, 1H), 5.20 (s, 2H), 4.01 (q, J=7.1 Hz, 2H), 3.60 (s, 2H), 1.07 (t, J=7.1 Hz, 3H); $^{19}$F NMR (282 MHz, DMSO-$d_6$) δ−112.61.

Step-5: Preparation of Ethyl 2-(2-((7-(3-(aminomethyl)phenyl)benzofuran-5-yl)methoxy)-4-fluorophenyl)acetate (260f)

Compound 260f was prepared according to the procedure reported in step-3 of scheme-1 from ethyl 2-(2-((7-bromobenzofuran-5-yl)methoxy)-4-fluorophenyl)acetate (260e) (200 mg, 0.491 mmol) in dioxane (5 mL) using 3-(aminomethyl)phenylboronic acid hydrochloride (6c) (89 mg, 0.589 mmol), bis(triphenylphosphine)palladium(II) chloride (Pd(PPh$_3$)$_2$Cl$_2$) (52 mg, 0.074 mmol), potassium carbonate (204 mg, 1.473 mmol) in water (0.5 mL) under an argon atmosphere heating at 100° C. for 3 h on oil bath. This gave after workup, purification by flash column chromatography (silica gel, 24 g, eluting with DMA-80 in DCM from 0-50%) ethyl 2-(2-((7-(3-(aminomethyl)phenyl)benzofuran-5-yl)methoxy)-4-fluorophenyl)acetate (260f) (147 mg, 69% yield) as a clear oil. $^1$H NMR (300 MHz, DMSO-$d_6$) δ 8.10 (d, J=2.2 Hz, 1H), 7.88-7.78 (m, 1H), 7.78-7.65 (m, 2H), 7.57 (d, J=1.7 Hz, 1H), 7.51-7.33 (m, 2H), 7.25 (dd, J=8.3, 6.9 Hz, 1H), 7.12-6.97 (m, 2H), 6.74 (td, J=8.5, 2.5 Hz, 1H), 5.26 (s, 2H), 3.92 (q, J=7.1 Hz, 2H), 3.82 (s, 2H), 3.60 (s, 2H), 0.97 (t, J=7.1 Hz, 3H); $^{19}$F NMR (282 MHz, DMSO-$d_6$) δ−112.66. MS (ES+): 434.2 (M+1).

Step-6: Preparation of 2-(2-((7-(3-(aminomethyl)phenyl)benzofuran-5-yl)methoxy)-4-fluorophenyl)acetic Acid (260g)

Compound 260g was prepared according to the procedure reported in step-6 of scheme-1 from ethyl 2-(2-((7-(3-(aminomethyl)phenyl)benzofuran-5-yl)methoxy)-4-fluorophenyl)acetate (260f) (145 mg, 0.335 mmol) in MeOH (5 mL), THF (5 mL) using 1 N lithium hydroxide (1.004 mL, 1.004 mmol). This gave after workup and purification by reverse phase column [C18 (50g), eluting with ACN in water (containing 0.1% HCl) from 0-100%] 2-(2-((7-(3-(aminomethyl)phenyl)benzofuran-5-yl)methoxy)-4-fluorophenyl)acetic acid (260g) (127 mg, 94% yield) hydrochloride salt as a white solid; $^1$H NMR (300 MHz, DMSO-$d_6$) δ 8.11 (d, J=2.2 Hz, 1H), 7.99 (t, J=1.8 Hz, 1H), 7.93 (dt, J=7.6, 1.6 Hz, 1H), 7.76 (d, J=1.6 Hz, 1H), 7.63 (d, J=1.6 Hz, 1H), 7.61-7.52 (m, 2H), 7.25 (dd, J=8.4, 6.9 Hz, 1H), 7.07 (d, J=2.2 Hz, 1H), 7.02 (dd, J=11.4, 2.5 Hz, 1H), 6.74 (td, J=8.5, 2.5 Hz, 1H), 5.29 (s, 2H), 4.14 (s, 2H), 3.57 (s, 2H). $^{19}$F NMR (282 MHz, DMSO-$d_6$) δ−113.00; MS (ES+): 406.1 (M+1); (ES−): 404.1 (M−1); analysis calculated for $C_{24}H_{20}FNO_4$·HCl: C, 65.23; H, 4.79; Cl, 8.02; N, 3.17; found: C, 65.11; H, 4.89; Cl, 7.79; N, 3.10.

Scheme-261

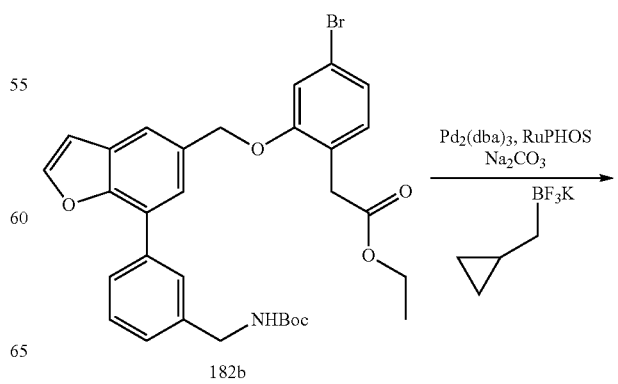

182b

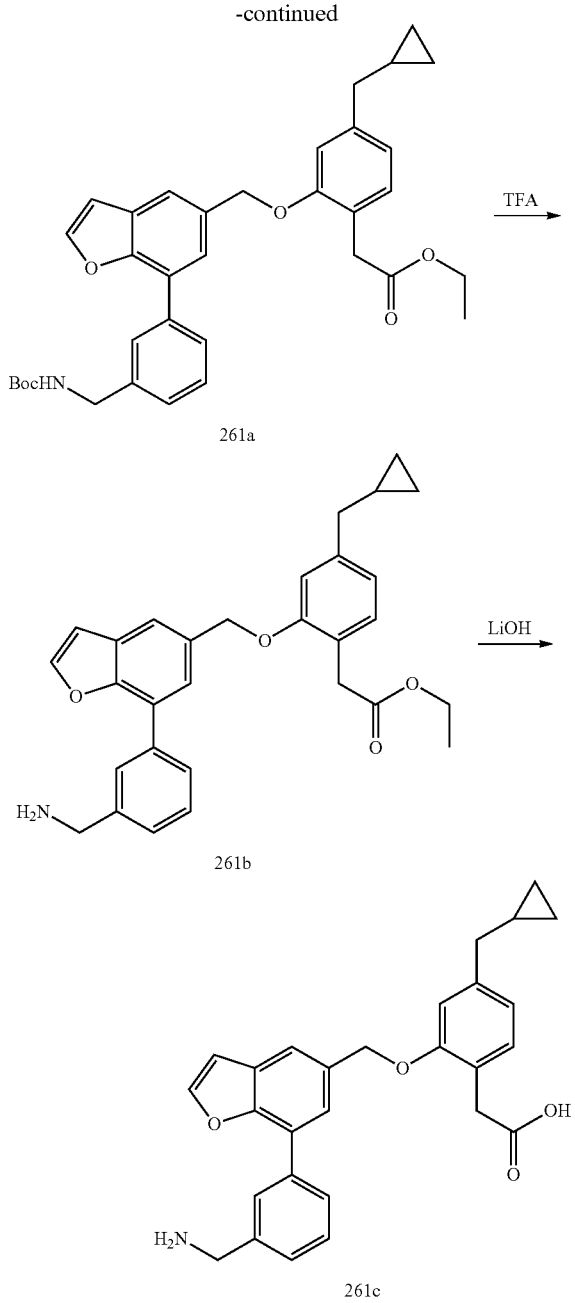

261a

261b

261c

Preparation of 2-(2-((7-(3-(aminomethyl)phenyl)
benzofuran-5-yl)methoxy)-4-(cyclopropylmethyl)
phenyl)acetic Acid (261c)

Step-1: Preparation of Ethyl 2-(2-((7-(3-(((tert-butoxycarbonyl)amino)methyl)phenyl)benzofuran-5-yl)methoxy)-4-(cyclopropylmethyl)phenyl)acetate (261a)

Compound 261a was prepared according to the procedure reported in step-5 of scheme-1 from ethyl 2-(4-bromo-2-((7-(3-((tert-butoxycarbonylamino)methyl)phenyl)benzofuran-5-yl)methoxy)phenyl)acetate (182b) (0.6 g, 1.01 mmol) in toluene (20 mL) and water (2 mL) using Potassium (cyclopropylmethyl)trifluoroborate (0.245 g, 1.514 mmol), dicyclohexyl(2',6'-diisopropoxybiphenyl-2-yl)phosphine (RuPHOS) (0.047 g, 0.101 mmol), Pd$_2$(dba)$_3$ (0.046 g, 0.050 mmol), sodium carbonate (0.43 g, 4.04 mmol) and heating at 100° C. for 10 h. This gave after workup and purification by flash column chromatography [silica gel, 24 g, eluting with EtOAc in hexanes from 0-70%] ethyl 2-(2-((7-(3-(((tert-butoxycarbonyl)amino)methyl)phenyl)benzofuran-5-yl)methoxy)-4-(cyclopropylmethyl)phenyl)acetate (261a) (0.381 g, 66% yield) as a waxy white solid. MS (ES+): 470.2 (M+1-Boc).

Step-2: Preparation of Ethyl 2-(2-((7-(3-(aminomethyl)phenyl)benzofuran-5-yl)methoxy)-4-(cyclopropylmethyl)phenyl)acetate (261b)

Compound 261b was prepared according to the procedure reported in step-5 of scheme-1 from ethyl 2-(2-((7-(3-(((tert-butoxycarbonyl)amino)methyl)phenyl)benzofuran-5-yl)methoxy)-4-(cyclopropylmethyl)phenyl)acetate (261a) (0.371 g, 0.651 mmol) in DCM (20 mL) using TFA (0.502 mL, 6.51 mmol). This gave after workup ethyl 2-(2-((7-(3-(aminomethyl)phenyl)benzofuran-5-yl)methoxy)-4-(cyclopropylmethyl)phenyl)acetate (261b) (0.38 g, 100% yield) as a yellow wax; MS (ES+): 470.10 (M+1); MS (ES−): 468.15 (M−1).

Step-3: Preparation of 2-(2-((7-(3-(aminomethyl)phenyl)benzofuran-5-yl)methoxy)-4-(cyclopropylmethyl)phenyl)acetic Acid (261c)

Compound 261c was prepared according to the procedure reported in step-6 of scheme-1 from ethyl 2-(2-((7-(3-(aminomethyl)phenyl)benzofuran-5-yl)methoxy)-4-(cyclopropylmethyl)phenyl)acetate (261b) (0.37 g, 0.634 mmol) in THF (10 mL) and methanol (20 mL) using 2M aqueous LiOH (3.17 mL, 6.34 mmol). This gave after workup and purification by flash column chromatography [silica gel 12 g, eluting with methanol in DCM from 0-50%] followed by reverse phase column chromatography [C18 (50g), eluting with ACN in water (containing 0.1% HCl) from 0-100%] 2-(2-((7-(3-(aminomethyl)phenyl)benzofuran-5-yl)methoxy)-4-(cyclopropylmethyl)phenyl)acetic acid (261c) (0.021 g, 8% yield) HCl salt as a white solid; $^1$H NMR (300 MHz, DMSO-d$_6$) δ 8.39-8.29 (m, 1H), 8.12-8.08 (m, 2H), 7.95-7.89 (m, 1H), 7.73-7.68 (m, 1H), 7.48 (t, J=7.7 Hz, 1H), 7.42-7.31 (m, 1H), 7.06 (d, J=2.2 Hz, 1H), 7.04-6.96 (m, 1H), 6.91-6.82 (m, 1H), 6.74-6.62 (m, 1H), 5.25 (s, 2H), 4.00 (s, 2H), 3.36 (s, 2H), 2.42 (d, J=7.0 Hz, 2H), 0.99-0.84 (m, 1H), 0.47-0.26 (m, 2H), 0.21-0.02 (m, 2H); MS (ES+): 442.10 (M+1); MS (ES−): 440.10 (M−1).

Scheme-262

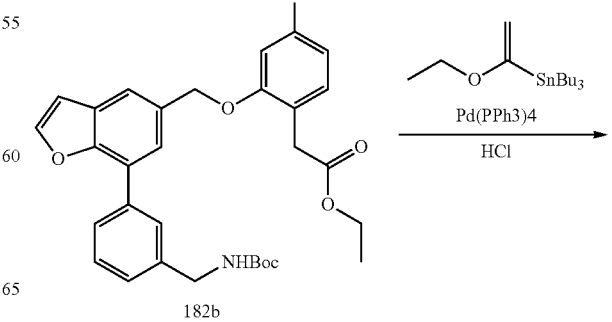

182b

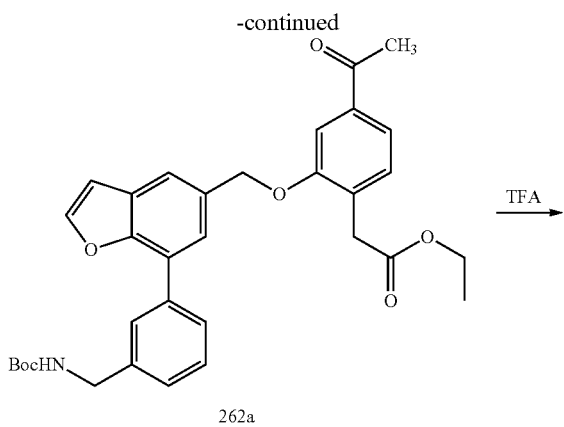

262a

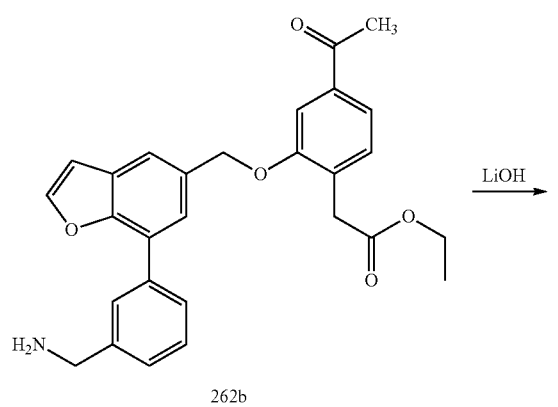

262b

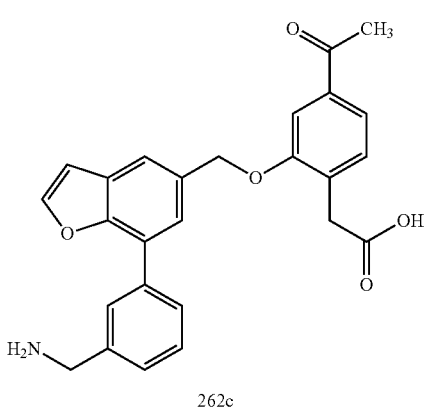

262c

Preparation of 2-(4-acetyl-2-((7-(3-(aminomethyl)phenyl)benzofuran-5-yl)methoxy)phenyl)acetic Acid (262c)

Step-1: Preparation of Ethyl 2-(4-acetyl-2-((7-(3-(((tert-butoxycarbonyl)amino)methyl)phenyl)benzofuran-5-yl)methoxy)phenyl)acetate (262a)

To a solution of ethyl 2-(4-bromo-2-((7-(3-(((tert-butoxycarbonylamino)methyl)phenyl)benzofuran-5-yl)methoxy)phenyl)acetate (182b) (0.5 g, 0.841 mmol) in toluene (150 mL) was added tributyl(1-ethoxyvinyl)stannane (0.38 g, 1.05 mmol) and Pd(Ph$_3$P)$_4$ (0.097 g, 0.084 mmol), the resulting mixture was stirred at 120° C. for 31 h under nitrogen. The reaction mixture was cooled to room temperature, diluted with EtOAc (500 mL), quenched with 6N aqueous HCl (0.421 mL, 2.52 mmol) and stirred for 10 min. The reaction mixture was diluted with water (500 mL), filtered through a Celite pad, rinsed with ethyl acetate (500 mL). The organic layer was separated, dried, filtered and evaporated to dryness. The residue obtained was purified twice by flash column chromatography [silica gel, 120 g, eluting with ethyl acetate in hexanes from 0-100%] to furnish ethyl 2-(4-acetyl-2-((7-(3-(((tert-butoxycarbonyl)amino)methyl)phenyl)benzofuran-5-yl)methoxy)phenyl)acetate (262a) (0.309 g, 66% yield) as a yellow solid; MS (ES+): 558.10 (M+1).

Step-2: Preparation of Ethyl 2-(4-acetyl-2-((7-(3-(aminomethyl)phenyl)benzofuran-5-yl)methoxy)phenyl)acetate (262b)

Compound 262b was prepared according to the procedure reported in step-5 of scheme-1 from ethyl 2-(4-acetyl-2-((7-(3-(((tert-butoxycarbonyl)amino)methyl)phenyl)benzofuran-5-yl)methoxy)phenyl)acetate (262a) (0.302 g, 0.542 mmol) in DCM (20 mL) using TFA (0.834 mL, 10.83 mmol). This gave after workup and purification by flash column chromatography (silica gel, 12 g, eluting with methanol in DCM from 0 to 100%) ethyl 2-(4-acetyl-2-((7-(3-(aminomethyl)phenyl)benzofuran-5-yl)methoxy)phenyl)acetate (262b) (0.239 g, 77% yield) as a yellow greasy wax; MS (ES+): 458.2 (M+1).

Step-3: Preparation of 2-(4-acetyl-2-((7-(3-(aminomethyl)phenyl)benzofuran-5-yl)methoxy)phenyl)acetic Acid (262c)

Compound 262c was prepared according to the procedure reported in step-6 of scheme-1 from ethyl 2-(4-acetyl-2-((7-(3-(aminomethyl)phenyl)benzofuran-5-yl)methoxy)phenyl)acetate (262b) (0.23 g, 0.4 mmol) in THF (5 mL) and methanol (10 mL) using 2M aqueous LiOH (2 mL, 4 mmol). This gave after workup and purification by flash column chromatography [silica gel 12 g, eluting with methanol in DCM from 0-50%] followed by reverse phase column chromatography [C18 (50g), eluting with ACN in water (containing 0.1% HCl) from 0-100%] 2-(4-acetyl-2-((7-(3-(aminomethyl)phenyl)benzofuran-5-yl)methoxy)phenyl) acetic acid (262c) (0.059 g, 34% yield) HCl salt as an off-white solid; $^1$H NMR (300 MHz, DMSO-d$_6$) δ 12.41 (bs, 1H, D$_2$O exchangeable), 8.41 (bs, 3H, D$_2$O exchangeable), 8.12 (d, J=2.2 Hz, 1H), 8.01 (d, J=1.8 Hz, 1H), 7.94 (dt, J=7.3, 1.7 Hz, 1H), 7.79 (d, J=1.6 Hz, 1H), 7.68 (d, J=1.6 Hz, 1H), 7.65-7.52 (m, 4H), 7.40 (d, J=7.6 Hz, 1H), 7.08 (d, J=2.2 Hz, 1H), 5.37 (s, 2H), 4.14 (s, 2H), 3.70 (s, 2H), 2.58 (s, 3H); MS (ES+): 430.1 (M+1); MS (ES−): 428.1 (M−1); Analysis calculated for C$_{26}$H$_{23}$NO$_5$.HCl.1.5H$_2$O: C, 63.35; H, 5.52; Cl, 7.19; N, 2.84; Found: C, 63.32; H, 5.28; Cl, 7.35; N, 2.82.

Scheme-263

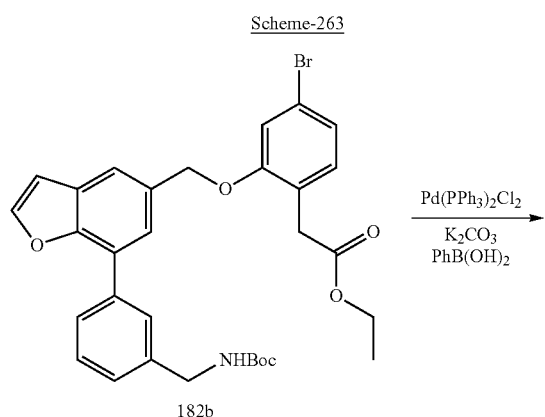

182b

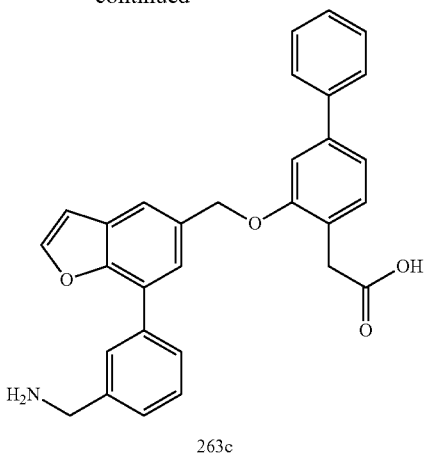

263c

Preparation of 2-(3-((7-(3-(aminomethyl)phenyl) benzofuran-5-yl)methoxy)-[1,1'-biphenyl]-4-yl)acetic Acid (263c)

Step-1: Preparation of Ethyl 2-(3-((7-(3-(((tert-butoxycarbonyl)amino)methyl)phenyl)benzofuran-5-yl)methoxy)-[1,1'-biphenyl]-4-yl)acetate (263a)

Compound 263a was prepared according to the procedure reported in step-3 of scheme-1 from ethyl 2-(4-bromo-2-((7-(3-(((tert-butoxycarbonylamino)methyl)phenyl)benzofuran-5-yl)methoxy)phenyl)acetate (182b) (530 mg, 1.248 mmol) in dioxane (20 mL) using phenylboronic acid (0.152 g, 1.248 mmol), Pd(PPh₃)₂Cl₂ (63 mg, 0.089 mmol) and a solution of K₂CO₃ (370 mg, 2.67 mmol) in water (2 mL) under a nitrogen atmosphere and heating at 90° C. for 10 h on an oil bath. This gave after workup ethyl 2-(3-((7-(3-(((tert-butoxycarbonyl)amino)methyl)phenyl)benzofuran-5-yl)methoxy)-[1,1'-biphenyl]-4-yl)acetate (263a) (0.358 g, 68% yield) as a yellow solid; MS (ES+): 492.2 (M+1, −Boc).

Step-2: Preparation of Ethyl 2-(3-((7-(3-(aminomethyl)phenyl)benzofuran-5-yl)methoxy)-[1,1'-biphenyl]-4-yl)acetate (263b)

Compound 263b was prepared according to the procedure reported in step-5 of scheme-1 from ethyl 2-(3-((7-(3-(((tert-butoxycarbonyl)amino)methyl)phenyl)benzofuran-5-yl)methoxy)-[1,1'-biphenyl]-4-yl)acetate (263a) (0.345 g, 0.583 mmol) in DCM (20 mL) using TFA (0.898 mL, 11.66 mmol). This gave after workup and purification by flash column chromatography (silica gel, 12 g, eluting with methanol in DCM from 0 to 100%) ethyl 2-(3-((7-(3-(aminomethyl)phenyl)benzofuran-5-yl)methoxy)-[1,1'-biphenyl]-4-yl)acetate (263b) (0.149 g, 42% yield) as a white solid; MS (ES+): 492.2 (M+1).

Step-3: Preparation of 2-(3-((7-(3-(aminomethyl)phenyl)benzofuran-5-yl)methoxy)-[1,1'-biphenyl]-4-yl)acetic Acid (263c)

Compound 263c was prepared according to the procedure reported in step-6 of scheme-1 from ethyl 2-(3-((7-(3-(aminomethyl)phenyl)benzofuran-5-yl)methoxy)-[1,1'-biphenyl]-4-yl)acetate (263b) (0.143 g, 0.236 mmol) in THF (5 mL) and methanol (10 mL) using 2M aqueous LiOH (1.181 mL, 2.361 mmol). This gave after workup and purification by flash column chromatography [silica gel, 25 g, eluting with methanol in DCM from 0-100%] followed by reverse phase column chromatography [C18 (50g), eluting with ACN in water (containing 0.1% HCl) from 0-100%] 2-(3-((7-(3-(aminomethyl)phenyl)benzofuran-5-yl)methoxy)-[1,1'-biphenyl]-4-yl)acetic acid (263c) (0.049 g, 45% yield) HCl salt as an off-white solid; $^1$H NMR (300 MHz, DMSO-$d_6$) δ 8.39-8.33 (m, 1H), 8.15-8.05 (m, 2H), 7.94 (d, J=1.7 Hz, 1H), 7.73 (d, J=1.6 Hz, 1H), 7.68-7.60 (m, 2H), 7.54-7.41 (m, 3H), 7.34 (dt, J=9.2, 7.2 Hz, 2H), 7.24 (d, J=1.6 Hz, 1H), 7.22-7.16 (m, 1H), 7.11 (dd, J=7.7, 1.6 Hz, 1H), 7.07 (d, J=2.2 Hz, 1H), 5.39 (s, 2H), 4.03 (s, 2H), 3.44 (s, 2H); MS (ES+): 464.1 (M+1); MS (ES−): 462.2 (M−1); Analysis calculated for $C_{30}H_{25}NO_4 \cdot HCl \cdot 0.75H_2O$: C, 70.17; H, 5.40; Cl, 6.90; N, 2.73; Found: C, 70.33; H, 5.03; Cl, 6.98; N, 2.78.

Scheme-264

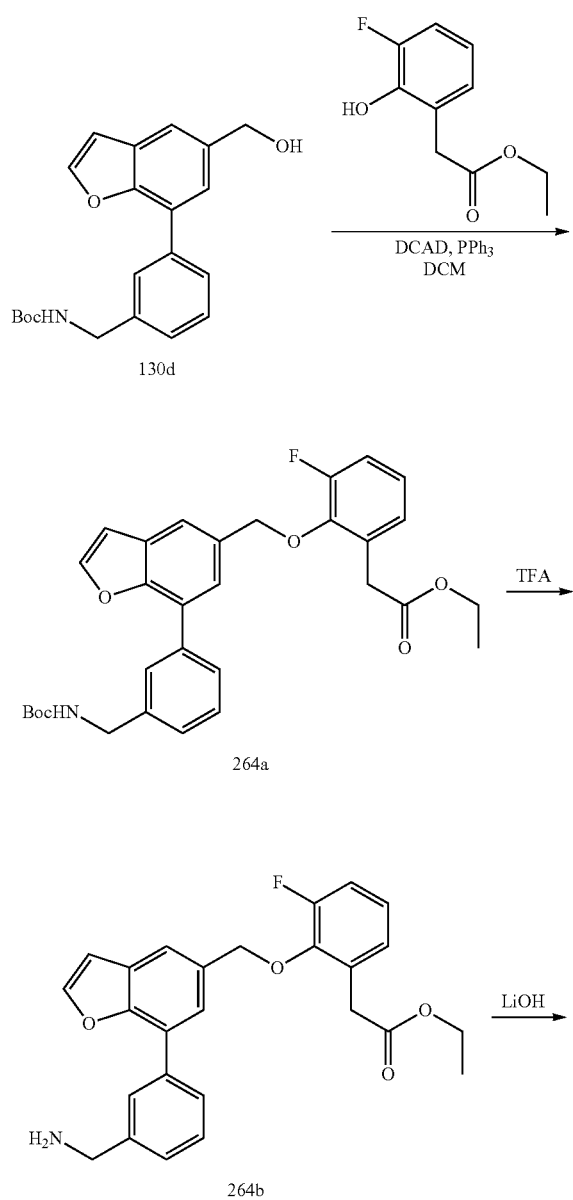

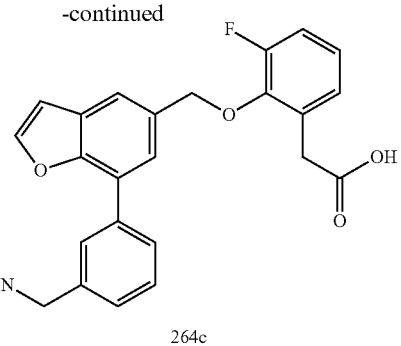

Preparation of 2-(2-((7-(3-(aminomethyl)phenyl)benzofuran-5-yl)methoxy)-3-fluorophenyl)acetic Acid (264c)

Step-1: Preparation of Ethyl 2-(2-((7-(3-(((tert-butoxycarbonyl)amino)methyl)phenyl)benzofuran-5-yl)methoxy)-3-fluorophenyl)acetate (264a)

Compound 264a was prepared according to the procedure reported in step-2 of scheme-23 from tert-butyl 3-(5-(hydroxymethyl)benzofuran-7-yl)benzylcarbamate (130d) (1.07 g, 3.303 mmol) in DCM (50 mL) using triphenylphosphine (0.73 g, 2.78 mmol), ethyl 2-(3-fluoro-2-hydroxyphenyl)acetate (0.500 g, 2.52 mmol; CAS #1261451-84-6) and a solution of (E)-bis(4-chlorobenzyl) diazene-1,2-dicarboxylate (DCAD, 1.019 g, 2.78 mmol) in DCM (5 mL). This gave after workup and purification by flash column chromatography (silica gel, 25 g, eluting with ethyl acetate in hexanes from 0-70%) ethyl 2-(2-((7-(3-(((tert-butoxycarbonyl)amino)methyl)phenyl)benzofuran-5-yl)methoxy)-3-fluorophenyl)acetate (264a) (0.719 g, 53% yield) as a yellow syrup; $^1$H NMR (300 MHz, DMSO-$d_6$) δ 8.09 (d, J=2.2 Hz, 1H), 7.78-7.67 (m, 3H), 7.57-7.43 (m, 2H), 7.36-7.20 (m, 2H), 7.13-7.06 (m, 3H), 5.19 (s, 2H), 4.23 (d, J=6.2 Hz, 2H), 3.92 (q, J=7.1 Hz, 2H), 3.65 (s, 2H), 1.40 (s, 9H), 1.00 (t, J=7.1 Hz, 3H).

Step-2: Preparation of Ethyl 2-(2-((7-(3-(aminomethyl)phenyl)benzofuran-5-yl)methoxy)-3-fluorophenyl)acetate (264b)

Compound 264b was prepared according to the procedure reported in step-5 of scheme-1 from ethyl 2-(2-((7-(3-(((tert-butoxycarbonyl)amino)methyl)phenyl)benzofuran-5-yl)methoxy)-3-fluorophenyl)acetate (264a) (0.709 g, 1.33 mmol) in DCM (30 mL) using TFA (1.024 mL, 13.29 mmol). This gave after workup and purification by flash column chromatography (silica gel, 25 g, eluting with methanol in DCM from 0 to 100%) ethyl 2-(2-((7-(3-(aminomethyl)phenyl)benzofuran-5-yl)methoxy)-3-fluorophenyl)acetate (264b) (0.259 g, 45.0% yield) as a white solid. MS (ES+): 434.1 (M+1).

Step-3: Preparation of 2-(2-((7-(3-(aminomethyl)phenyl)benzofuran-5-yl)methoxy)-3-fluorophenyl)acetic Acid (264c)

Compound 264c was prepared according to the procedure reported in step-6 of scheme-1 from ethyl 2-(2-((7-(3-(aminomethyl)phenyl)benzofuran-5-yl)methoxy)-3-fluorophenyl)acetate (264b) (0.256 g, 0.591 mmol) in MeOH (20 mL), THF (10 mL) using a 2M aqueous solution of lithium hydroxide (4.43 mL, 8.86 mmol). This gave after workup and purification by flash column chromatography (silica gel, 25 g, eluting with methanol in DCM from 0 to 100%) followed by reverse phase column [C18 (50g), eluting with ACN in water (containing 0.1% HCl) from 0-100%] 2-(2-((7-(3-(aminomethyl)phenyl)benzofuran-5-yl)methoxy)-3-fluorophenyl)acetic acid (264c) (0.021 g, 9% yield) as an off-white solid; $^1$H NMR (300 MHz, DMSO-$d_6$) δ 8.12 (d, J=2.2 Hz, 1H), 8.01-7.97 (m, 1H), 7.96-7.89 (m, 1H), 7.78-7.74 (m, 1H), 7.67-7.63 (m, 1H), 7.62-7.51 (m, 2H), 7.27-7.17 (m, 1H), 7.13-7.06 (m, 3H), 5.19 (s, 2H), 4.15 (s, 2H), 3.61 (s, 2H); $^{19}$F NMR (282 MHz, DMSO-$d_6$) δ−129.84; MS (ES+): 406.10 (M+1); MS (ES−): 404.1 (M−1).

Scheme-265

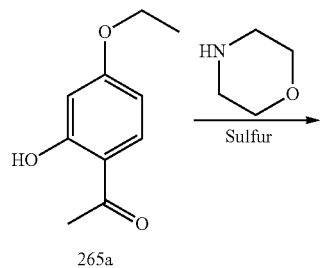

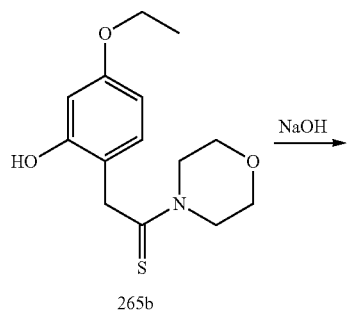

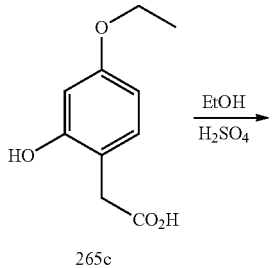

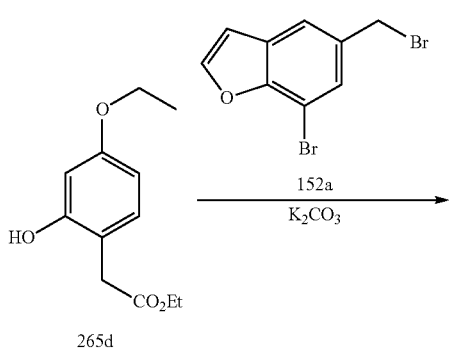

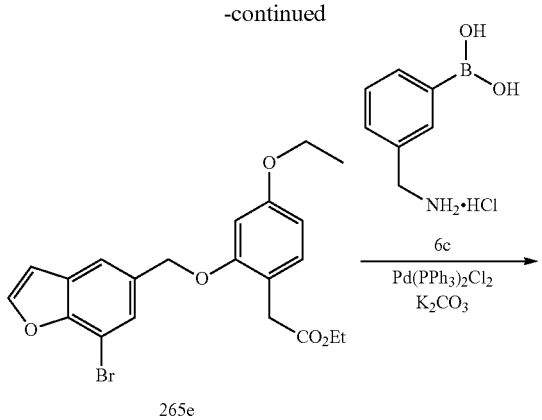

Preparation of 2-(2-((7-(3-(aminomethyl)phenyl)benzofuran-5-yl)methoxy)-4-ethoxyphenyl)acetic Acid (265g)

Step-1: Preparation of 2-(4-ethoxy-2-hydroxyphenyl)-1-morpholinoethanethione (265b)

A suspension of 1-(4-ethoxy-2-hydroxyphenyl)ethanone (265a) (2.0 g, 11.10 mmol; CAS #37470-42-1), sulfur powder (0.712 g, 22.20 mmol) and morpholine (1.934 g, 22.20 mmol) was heated at 130° C. for 16 h. The resulting black mixture was quenched with H$_2$O (25 mL) and extracted with EtOAc (3×25 mL). The combined organic extracts were washed with H$_2$O (4×25 mL), brine (25 mL), dried, filtered and concentrated in vacuum. The residue obtained was purified by flash column chromatography (SiO$_2$, 24 g, eluting with 0-30% EtOAc in hexane) to afford 2-(4-ethoxy-2-hydroxyphenyl)-1-morpholinoethanethione (265b) (1.61 g, 52% yield) as a thick deep red semisolid. $^1$H NMR (300 MHz, DMSO-$d_6$) δ 9.73 (s, 1H), 7.07 (d, J=8.3 Hz, 1H), 6.46-6.30 (m, 2H), 4.23 (t, J=5.7, 4.1 Hz, 2H), 4.04 (s, 2H), 3.92 (q, J=6.9 Hz, 2H), 3.63 (dd, J=5.9, 3.4 Hz, 4H), 3.40 (t, J=5.5, 4.0 Hz, 2H), 1.29 (t, J=7.0 Hz, 3H); MS (ES+): 282 (M+1), (ES−): 280 (M−1).

Step-2: Preparation of 2-(4-ethoxy-2-hydroxyphenyl)acetic Acid (265c)

To a solution of 2-(4-ethoxy-2-hydroxyphenyl)-1-morpholinoethanethione (265b) (1.61 g, 5.72 mmol) in EtOH (20 mL) was added 4 M aqueous NaOH (4.29 mL, 17.17 mmol) and heated at 85° C. for 16 h. The resulting mixture was concentrated to remove EtOH. The concentrate was suspended in $H_2O$ (10 mL), cooled to 0° C. and acidified with 3 M aqueous HCl until pH=1, during which a semisolid formed. The mixture was extracted with EtOAc (3×25 mL). The combined organic extract was washed with $H_2O$ (25 mL), brine (25 mL), dried, filtered and concentrated in vacuum to afford 2-(4-ethoxy-2-hydroxyphenyl)acetic acid (265c) (1.27 g) as a thick yellow oil in acceptable purity, which was used in the next step without further purification; MS (ES−): 195 (M−1).

Step-3: Preparation of Ethyl 2-(4-ethoxy-2-hydroxyphenyl)acetate (265d)

To a solution of 2-(4-ethoxy-2-hydroxyphenyl)acetic acid (265c) (1.27 g, 6.47 mmol) in ethanol (22.68 mL, 388 mmol) was added sulfuric acid (1.943 g, 19.42 mmol) and heated at 80° C. for 16 h. The reaction mixture was cooled to room temperature and concentrated in vacuum. The residue obtained was diluted with water and extracted with DCM (3×25 mL). The combined organic extracts were washed with saturated $NaHCO_3$ (25 mL), $H_2O$ (25 mL), brine (25 mL), dried, filtered and concentrated in vacuum. The residue obtained was purified by flash column chromatography ($SiO_2$, 24 g, eluting with 0-15% EtOAc in hexane) to afford ethyl 2-(4-ethoxy-2-hydroxyphenyl)acetate (265d) (0.85 g, 59% yield) as a thick yellow oil; $^1H$ NMR (300 MHz, DMSO-$d_6$) δ 9.48 (s, 1H), 6.96 (d, J=8.2 Hz, 1H), 6.35 (d, J=2.4 Hz, 1H), 6.31 (dd, J=8.2, 2.5 Hz, 1H), 4.04 (q, J=7.1 Hz, 2H), 3.92 (q, J=7.0 Hz, 2H), 3.44 (s, 2H), 1.29 (t, J=7.0 Hz, 3H), 1.16 (t, J=7.1 Hz, 3H); MS (ES+): 225 (M+1), (ES−): 223 (M−1).

Step-4: Preparation of Ethyl 2-(2-((7-bromobenzofuran-5-yl)methoxy)-4-ethoxyphenyl)acetate (265e)

Compound 265e was prepared according to the procedure reported in step-2 of scheme-152 from 7-bromo-5-(bromomethyl)benzofuran (152a) (1.099 g, 3.79 mmol) using ethyl 2-(4-ethoxy-2-hydroxyphenyl)acetate (265d) (0.85 g, 3.79 mmol) and $K_2CO_3$ (1.572 g, 11.37 mmol) in DMF (20 mL). This gave after workup and purification by flash column chromatography ($SiO_2$, 24 g, eluting with 0-10% EtOAc in hexane) ethyl 2-(2-((7-bromobenzofuran-5-yl)methoxy)-4-ethoxyphenyl)acetate (265e) (1.37 g, 83% yield) as a white solid. $^1H$ NMR (300 MHz, DMSO-$d_6$) δ 8.15 (d, J=2.2 Hz, 1H), 7.71 (d, J=1.4 Hz, 1H), 7.59 (d, J=1.5 Hz, 1H), 7.17-7.06 (m, 2H), 6.64 (d, J=2.4 Hz, 1H), 6.47 (dd, J=8.2, 2.3 Hz, 1H), 5.17 (s, 2H), 4.07-3.95 (m, 4H), 3.54 (s, 2H), 1.31 (t, J=7.0 Hz, 3H), 1.08 (dd, J=7.4, 6.7 Hz, 3H). MS (ES+): 433/435 (M+1).

Step-5: Preparation of Ethyl 2-(2-((7-(3-(aminomethyl)phenyl)benzofuran-5-yl)methoxy)-4-ethoxyphenyl)acetate (265f)

Compound 265f was prepared according to the procedure reported in step-3 of scheme-1 from ethyl 2-(2-((7-bromobenzofuran-5-yl)methoxy)-4-ethoxyphenyl)acetate (265e) (160 mg, 0.369 mmol) in dioxane (4 mL) using 3-(aminomethyl)phenylboronic acid hydrochloride (6c) (104 mg, 0.554 mmol), bis(triphenylphosphine)palladium (II) chloride ($Pd(PPh_3)_2Cl_2$) (38.9 mg, 0.055 mmol) and 3.3 M aqueous $K_2CO_3$ (0.336 mL, 1.108 mmol) under an $N_2$ atmosphere heating at 100° C. for 16 h on oil bath. This gave after workup, purification by flash column chromatography (silica gel 12 g, eluting with methanol in DCM from 0-5%) ethyl 2-(2-((7-(3-(aminomethyl)phenyl)benzofuran-5-yl)methoxy)-4-ethoxyphenyl)acetate (265f) (104 mg, 61% yield) as a clear colorless oil. $^1H$ NMR (300 MHz, DMSO-$d_6$) δ 8.10 (d, J=2.2 Hz, 1H), 7.82 (d, J=1.8 Hz, 1H), 7.71 (dt, J=7.7, 1.7 Hz, 1H), 7.68 (d, J=1.6 Hz, 1H), 7.57 (d, J=1.7 Hz, 1H), 7.46 (t, J=7.5 Hz, 1H), 7.40 (dt, J=7.6, 1.5 Hz, 1H), 7.09 (d, J=8.3 Hz, 1H), 7.05 (d, J=2.2 Hz, 1H), 6.68 (d, J=2.4 Hz, 1H), 6.46 (dd, J=8.2, 2.4 Hz, 1H), 5.23 (s, 2H), 4.01 (q, J=7.0 Hz, 2H), 3.92 (q, J=7.1 Hz, 2H), 3.81 (s, 2H), 3.54 (s, 2H), 1.31 (t, J=7.0 Hz, 3H), 0.99 (t, J=7.1 Hz, 3H); MS (ES+): 460 (M+1).

Step-6: Preparation of 2-(2-((7-(3-(aminomethyl)phenyl)benzofuran-5-yl)methoxy)-4-ethoxyphenyl)acetic Acid (265g)

Compound 265g was prepared according to the procedure reported in step-6 of scheme-1 from ethyl 2-(2-((7-(3-(aminomethyl)phenyl)benzofuran-5-yl)methoxy)-4-ethoxyphenyl)acetate (265f) (104 mg, 0.226 mmol) in MeOH (3 mL), THF (10 mL) using a 2M aqueous solution of lithium hydroxide (0.566 mL, 1.132 mmol). This gave after workup and purification by reverse phase column [C18 (100 g), eluting with ACN in water (containing 0.1% HCl) from 0-100%] 2-(2-((7-(3-(aminomethyl)phenyl)benzofuran-5-yl)methoxy)-4-ethoxyphenyl)acetic acid (265g) (70 mg, 72% yield) HCl salt as a white solid; $^1H$ NMR (300 MHz, DMSO-$d_6$) δ 8.11 (d, J=2.2 Hz, 1H), 8.01 (d, J=1.9 Hz, 1H), 7.93 (dt, J=7.4, 1.7 Hz, 1H), 7.75 (d, J=1.6 Hz, 1H), 7.65 (d, J=1.6 Hz, 1H), 7.60 (t, J=7.5 Hz, 1H), 7.57-7.52 (m, 1H), 7.09 (d, J=8.3 Hz, 1H), 7.07 (d, J=2.2 Hz, 1H), 6.65 (d, J=2.4 Hz, 1H), 6.46 (dd, J=8.3, 2.3 Hz, 1H), 5.26 (s, 2H), 4.13 (s, 2H), 4.00 (q, J=7.0 Hz, 2H), 3.50 (s, 2H), 1.30 (t, J=7.0 Hz, 3H); MS (ES+): 432 (M+1), (ES−): 430 (M−1); Analysis calculated for $C_{26}H_{25}NO_5 \cdot HCl \cdot 0.5H_2O$: C, 65.47; H, 5.71; Cl, 7.43; N, 2.94; Found: C, 65.63; H, 5.46; Cl, 7.03; N, 2.87.

Scheme-266

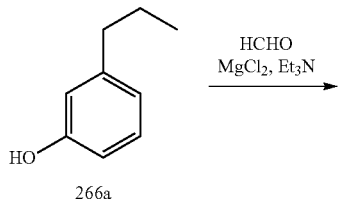

266a

HCHO
$MgCl_2$, $Et_3N$
→

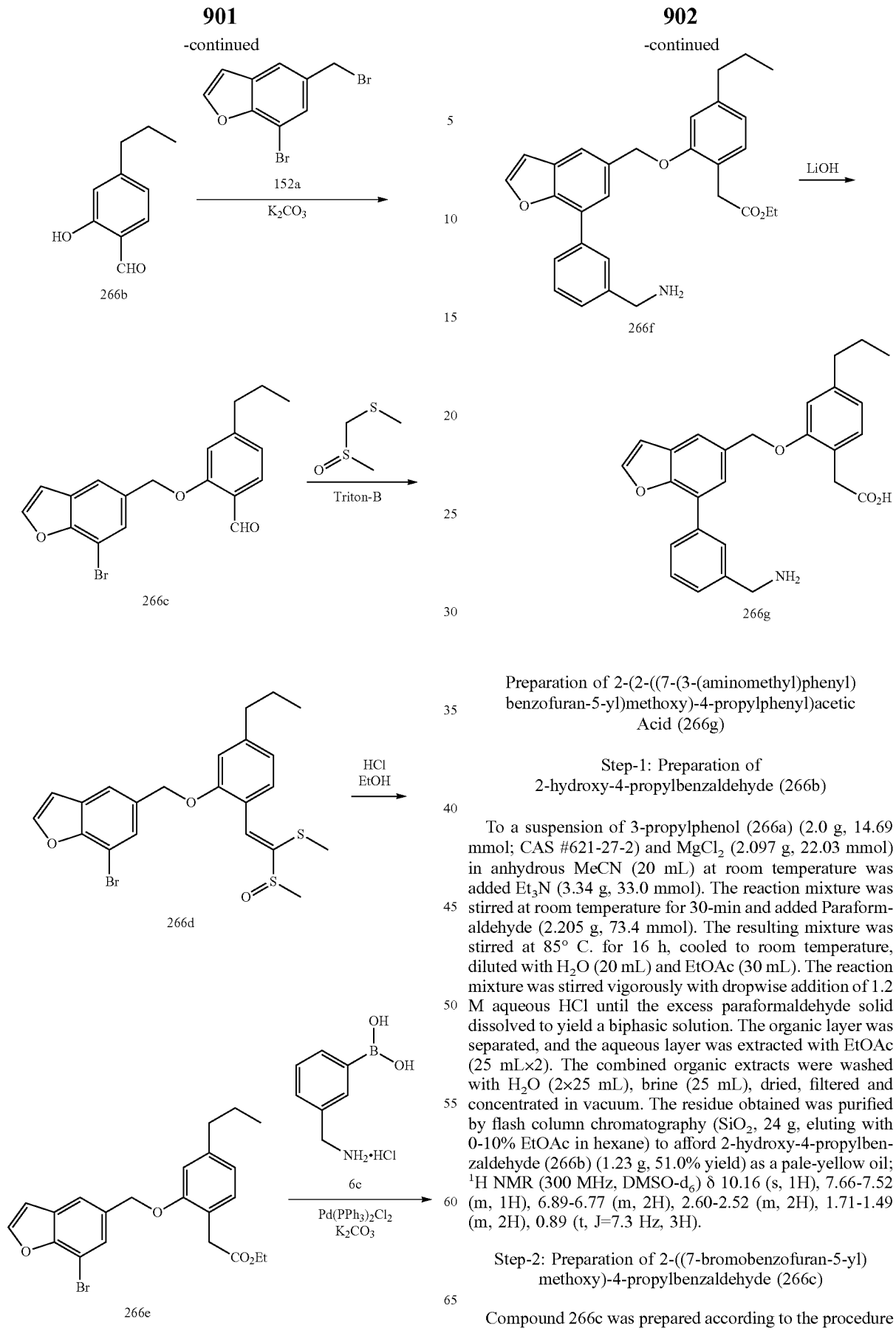

Preparation of 2-(2-((7-(3-(aminomethyl)phenyl)benzofuran-5-yl)methoxy)-4-propylphenyl)acetic Acid (266g)

Step-1: Preparation of 2-hydroxy-4-propylbenzaldehyde (266b)

To a suspension of 3-propylphenol (266a) (2.0 g, 14.69 mmol; CAS #621-27-2) and $MgCl_2$ (2.097 g, 22.03 mmol) in anhydrous MeCN (20 mL) at room temperature was added $Et_3N$ (3.34 g, 33.0 mmol). The reaction mixture was stirred at room temperature for 30-min and added Paraformaldehyde (2.205 g, 73.4 mmol). The resulting mixture was stirred at 85° C. for 16 h, cooled to room temperature, diluted with $H_2O$ (20 mL) and EtOAc (30 mL). The reaction mixture was stirred vigorously with dropwise addition of 1.2 M aqueous HCl until the excess paraformaldehyde solid dissolved to yield a biphasic solution. The organic layer was separated, and the aqueous layer was extracted with EtOAc (25 mL×2). The combined organic extracts were washed with $H_2O$ (2×25 mL), brine (25 mL), dried, filtered and concentrated in vacuum. The residue obtained was purified by flash column chromatography ($SiO_2$, 24 g, eluting with 0-10% EtOAc in hexane) to afford 2-hydroxy-4-propylbenzaldehyde (266b) (1.23 g, 51.0% yield) as a pale-yellow oil; $^1$H NMR (300 MHz, DMSO-$d_6$) δ 10.16 (s, 1H), 7.66-7.52 (m, 1H), 6.89-6.77 (m, 2H), 2.60-2.52 (m, 2H), 1.71-1.49 (m, 2H), 0.89 (t, J=7.3 Hz, 3H).

Step-2: Preparation of 2-((7-bromobenzofuran-5-yl)methoxy)-4-propylbenzaldehyde (266c)

Compound 266c was prepared according to the procedure reported in step-2 of scheme-152 from 7-bromo-5-(bromomethyl)benzofuran (152a) (2.03 g, 7.0 mmol) using 2-hydroxy-4-propylbenzaldehyde (266b) (1.150 g, 7.0 mmol) and $K_2CO_3$ (2.90 g, 21.0 mmol) in DMF (20 mL). This gave after workup and purification by flash column chromatography ($SiO_2$, 24 g, eluting with 0-5% EtOAc in hexane) 2-((7-bromobenzofuran-5-yl)methoxy)-4-propylbenzaldehyde (266c) (1.84 g, 70% yield) as a pale-yellow solid. $^1$H NMR (300 MHz, DMSO-$d_6$) δ 10.36 (d, J=0.8 Hz, 1H), 8.15 (d, J=2.2 Hz, 1H), 7.85 (d, J=1.5 Hz, 1H), 7.74 (d, J=1.5 Hz, 1H), 7.63 (d, J=7.8 Hz, 1H), 7.20 (d, J=1.4 Hz, 1H), 7.13 (d, J=2.2 Hz, 1H), 6.94 (d, J=7.9 Hz, 1H), 5.37 (s, 2H), 2.62 (dd, J=8.4, 6.7 Hz, 2H), 1.74-1.53 (m, 2H), 0.87 (t, J=7.3 Hz, 3H); MS (ES+): 395/397 (M+Na).

Step-3: Preparation of (E)-7-bromo-5-((2-(2-(methylsulfinyl)-2-(methylthio)vinyl)-5-propylphenoxy) methyl)benzofuran (266d)

To a solution of 2-((7-bromobenzofuran-5-yl)methoxy)-4-propylbenzaldehyde (266c) (1.00 g, 2.68 mmol), methyl (methylsulfinylmethyl)sulfane (0.533 g, 4.29 mmol) in THF (20 mL) was added at room temperature Triton-B (40 wt. % in methanol) (0.605 mL, 1.340 mmol) and heated at 70° C. for 16 h. The resulting black solution was cooled to room temperature diluted with $H_2O$ (30 mL) and EtOAc (30 mL). After 30-min stirring, the two layers were separated. The aqueous layer was extracted with EtOAc (2×25 mL). The combined organic extract was washed with $H_2O$ (30 mL), brine (30 mL), dried, filtered and concentrated in vacuum. The residue obtained was purified by flash column chromatography ($SiO_2$, 24 g, eluting with 0-40% EtOAc in hexane) to afford (E)-7-bromo-5-((2-(2-(methylsulfinyl)-2-(methylthio)vinyl)-5-propylphenoxy)methyl)benzofuran (266d) (0.98 g, 76% yield) as a pale-yellow oil; $^1$H NMR (300 MHz, DMSO-$d_6$) δ 8.14 (d, J=2.2 Hz, 1H), 7.97 (d, 1H), 7.83 (s, 1H), 7.75 (d, J=1.5 Hz, 1H), 7.65 (d, J=1.5 Hz, 1H), 7.10 (d, J=2.2 Hz, 1H), 7.08 (d, J=1.5 Hz, 1H), 6.90 (d, 1H), 5.29 (s, 2H), 2.71 (s, 3H), 2.57 (t, J=8.5, 6.6 Hz, 2H), 2.27 (s, 3H), 1.71-1.50 (m, 2H), 0.87 (t, J=7.3 Hz, 3H); MS (ES+): 479/481 (M+1).

Step-4: Preparation of Ethyl 2-(2-((7-bromobenzofuran-5-yl)methoxy)-4-propylphenyl)acetate (266e)

To a solution of (E)-7-bromo-5-((2-(2-(methylsulfinyl)-2-(methylthio)vinyl)-5-propylphenoxy)methyl)benzofuran (266d) (0.98 g, 2.044 mmol) in EtOH (20 mL) was added 4 M HCl in dioxane (1.533 mL, 6.13 mmol) and heated at 80° C. for 16 h. The cooled yellow solution was evaporated to remove EtOH. The concentrate was diluted with saturated $NaHCO_3$ (20 mL) and EtOAc (20 mL). After 30-min stirring, the two layers were separated. The aqueous layer was extracted with EtOAc (2×20 mL). The combined organic extract was washed with $H_2O$ (30 mL), brine (30 mL), dried, filtered and concentrated in vacuum. The residue obtained was purified by flash column chromatography ($SiO_2$, 24 g, eluting with 0-40% EtOAc in hexane) to afford ethyl 2-(2-((7-bromobenzofuran-5-yl)methoxy)-4-propylphenyl)acetate (266e) (0.59 g, 67% yield) as a clear colorless oil. $^1$H NMR (300 MHz, DMSO-$d_6$) δ 8.14 (d, J=2.1 Hz, 1H), 7.72 (t, J=1.1 Hz, 1H), 7.60 (d, J=1.4 Hz, 1H), 7.19-7.03 (m, 2H), 6.96-6.88 (m, 1H), 6.74 (dd, J=7.6, 1.5 Hz, 1H), 5.16 (s, 2H), 4.01 (qd, J=7.1, 0.8 Hz, 2H), 3.57 (s, 2H), 2.54 (d, J=7.2 Hz, 2H), 1.68-1.48 (m, 2H), 1.07 (td, J=7.1, 0.7 Hz, 3H), 0.95-0.81 (m, 3H); MS (ES+): 431/433 (M+1).

Step-5: Preparation of Ethyl 2-(2-((7-(3-(aminomethyl)phenyl)benzofuran-5-yl)methoxy)-4-propylphenyl)acetate (266f)

Compound 266f was prepared according to the procedure reported in step-3 of scheme-1 from ethyl 2-(2-((7-bromobenzofuran-5-yl)methoxy)-4-propylphenyl)acetate (266e) (160 mg, 0.371 mmol) in dioxane (4 mL) using 3-(aminomethyl)phenylboronic acid hydrochloride (6c) (174 mg, 0.93 mmol), bis(triphenylphosphine)palladium(II) chloride ($Pd(PPh_3)_2Cl_2$) (39 mg, 0.056 mmol) and 3.3 M aqueous $K_2CO_3$ (0.337 mL, 1.113 mmol) under an $N_2$ atmosphere heating at 100° C. for 16 h on oil bath. This gave after workup, purification by flash column chromatography (silica gel, 12 g, eluting with methanol in DCM from 0-5%) ethyl 2-(2-((7-(3-(aminomethyl)phenyl)benzofuran-5-yl)methoxy)-4-propylphenyl)acetate (266f) (140 mg, 82% yield) as a clear colorless oil; $^1$H NMR (300 MHz, DMSO-$d_6$) δ 8.10 (d, J=2.2 Hz, 1H), 7.82 (d, J=1.7 Hz, 1H), 7.77-7.66 (m, 2H), 7.58 (d, J=1.7 Hz, 1H), 7.47 (t, J=7.6 Hz, 1H), 7.40 (dt, J=7.6, 1.5 Hz, 1H), 7.10 (d, J=7.6 Hz, 1H), 7.05 (d, J=2.2 Hz, 1H), 6.98 (d, J=1.5 Hz, 1H), 6.73 (dd, J=7.6, 1.5 Hz, 1H), 5.22 (s, 2H), 3.91 (q, J=7.1 Hz, 2H), 3.82 (s, 2H), 3.57 (s, 2H), 2.54 (t, J=5.3 Hz, 2H), 1.69-1.50 (m, 2H), 0.98 (t, J=7.1 Hz, 3H), 0.88 (t, J=7.3 Hz, 3H); MS (ES+): 458 (M+1).

Step-6: Preparation of 2-(2-((7-(3-(aminomethyl)phenyl)benzofuran-5-yl)methoxy)-4-propylphenyl) acetic Acid (266g)

Compound 266g was prepared according to the procedure reported in step-6 of scheme-1 from ethyl 2-(2-((7-(3-(aminomethyl)phenyl)benzofuran-5-yl)methoxy)-4-propylphenyl)acetate (266f) (135 mg, 0.295 mmol) in MeOH (3 mL), using a 2M aqueous solution of lithium hydroxide (0.738 mL, 1.475 mmol). This gave after workup and purification by reverse phase column [C18 (100 g), eluting with ACN in water (containing 0.1% HCl) from 0-100%] 2-(2-((7-(3-(aminomethyl)phenyl)benzofuran-5-yl) methoxy)-4-propylphenyl)acetic acid (266g) (78 mg, 62% yield) HCl salt as a white solid; $^1$H NMR (300 MHz, DMSO-$d_6$) δ 8.11 (d, J=2.2 Hz, 1H), 8.01 (d, J=1.7 Hz, 1H), 7.94 (dt, J=7.5, 1.6 Hz, 1H), 7.76 (d, J=1.6 Hz, 1H), 7.67 (d, J=1.7 Hz, 1H), 7.60 (t, J=7.6 Hz, 1H), 7.54 (dt, J=7.7, 1.6 Hz, 1H), 7.10 (d, J=7.6 Hz, 1H), 7.07 (d, J=2.2 Hz, 1H), 6.95 (d, J=1.6 Hz, 1H), 6.73 (dd, J=7.6, 1.5 Hz, 1H), 5.25 (s, 2H), 4.13 (s, 2H), 3.53 (s, 2H), 2.57-2.52 (m, 2H), 1.68-1.48 (m, 2H), 0.87 (t, J=7.3 Hz, 3H); MS (ES+): 430 (M+1), (ES−): 428 (M−1).

Scheme-267

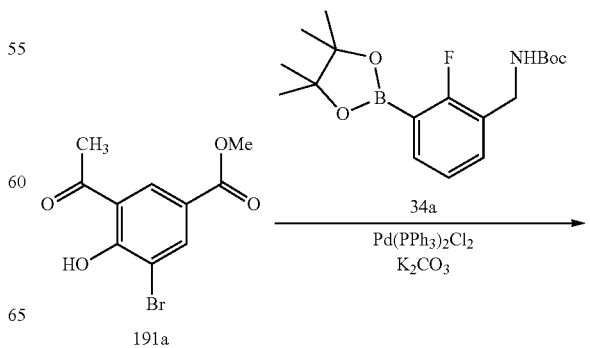

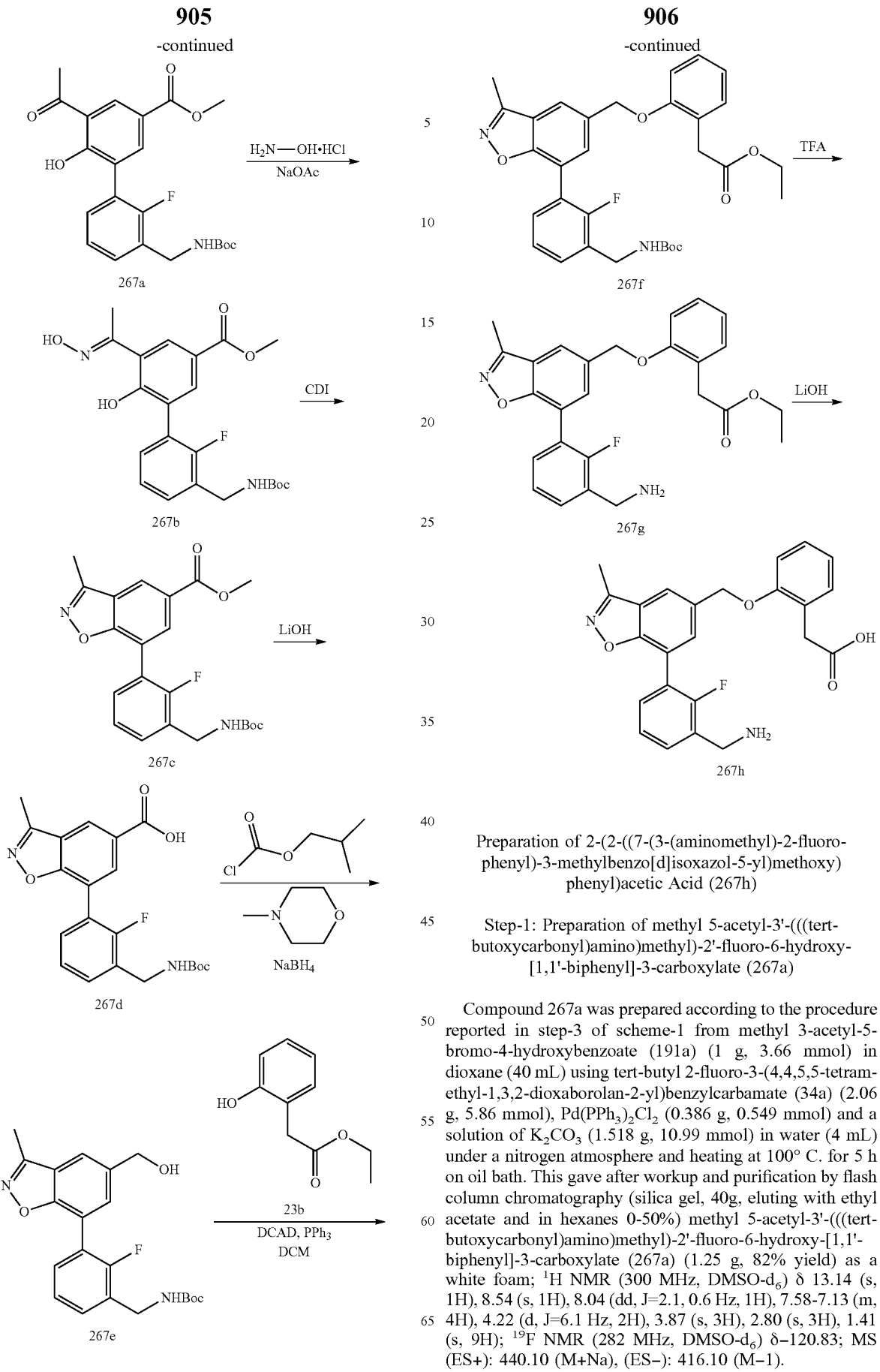

Preparation of 2-(2-((7-(3-(aminomethyl)-2-fluorophenyl)-3-methylbenzo[d]isoxazol-5-yl)methoxy)phenyl)acetic Acid (267h)

Step-1: Preparation of methyl 5-acetyl-3'-(((tert-butoxycarbonyl)amino)methyl)-2'-fluoro-6-hydroxy-[1,1'-biphenyl]-3-carboxylate (267a)

Compound 267a was prepared according to the procedure reported in step-3 of scheme-1 from methyl 3-acetyl-5-bromo-4-hydroxybenzoate (191a) (1 g, 3.66 mmol) in dioxane (40 mL) using tert-butyl 2-fluoro-3-(4,4,5,5-tetramethyl-1,3,2-dioxaborolan-2-yl)benzylcarbamate (34a) (2.06 g, 5.86 mmol), Pd(PPh$_3$)$_2$Cl$_2$ (0.386 g, 0.549 mmol) and a solution of K$_2$CO$_3$ (1.518 g, 10.99 mmol) in water (4 mL) under a nitrogen atmosphere and heating at 100° C. for 5 h on oil bath. This gave after workup and purification by flash column chromatography (silica gel, 40g, eluting with ethyl acetate and in hexanes 0-50%) methyl 5-acetyl-3'-(((tert-butoxycarbonyl)amino)methyl)-2'-fluoro-6-hydroxy-[1,1'-biphenyl]-3-carboxylate (267a) (1.25 g, 82% yield) as a white foam; $^1$H NMR (300 MHz, DMSO-d$_6$) δ 13.14 (s, 1H), 8.54 (s, 1H), 8.04 (dd, J=2.1, 0.6 Hz, 1H), 7.58-7.13 (m, 4H), 4.22 (d, J=6.1 Hz, 2H), 3.87 (s, 3H), 2.80 (s, 3H), 1.41 (s, 9H); $^{19}$F NMR (282 MHz, DMSO-d$_6$) δ−120.83; MS (ES+): 440.10 (M+Na), (ES−): 416.10 (M−1).

Step-2: Preparation of (E)-methyl 3'-(((tert-butoxy-carbonyl)amino)methyl)-2'-fluoro-6-hydroxy-5-(1-(hydroxyimino)ethyl)-[1,1'-biphenyl]-3-carboxylate (267b)

To a stirred solution of methyl 5-acetyl-3'-(((tert-butoxycarbonyl)amino)methyl)-2'-fluoro-6-hydroxy-[1,1'-biphenyl]-3-carboxylate (267a) (1.14 g, 2.73 mmol) in methanol (20 mL) was added hydroxylamine hydrochloride (0.759 g, 10.92 mmol) and sodium acetate (0.896 g, 10.92 mmol). The mixture was heated at reflux for 1 h, cooled to room temperature and concentrated in vacuum. Water (25 mL) was added to the residue and triturated. The solid separated was collected by filtration and dried to afford (E)-methyl 3'-(((tert-butoxycarbonyl)amino)methyl)-2'-fluoro-6-hydroxy-5-(1-(hydroxyimino)ethyl)-[1,1'-biphenyl]-3-carboxylate (267b) (1.15 g, 97% yield) as a white solid; $^1$H NMR (300 MHz, DMSO-$d_6$) δ 13.00 (s, 1H), 11.95 (s, 1H), 8.14 (d, J=2.2 Hz, 1H), 7.79 (d, J=2.1 Hz, 1H), 7.46 (t, J=6.2 Hz, 1H), 7.27 (dq, J=14.9, 7.8 Hz, 3H), 4.22 (d, J=6.1 Hz, 2H), 3.84 (s, 3H), 2.38 (s, 3H), 1.41 (s, 9H); $^{19}$F NMR (282 MHz, DMSO-$d_6$) δ−120.79.

Step-3: Preparation of methyl 7-(3-(((tert-butoxycarbonyl)amino)methyl)-2-fluorophenyl)-3-methylbenzo[d]isoxazole-5-carboxylate (267c)

Compound 267c was prepared according to the procedure reported in step-2 of scheme-191 from (E)-methyl 3'-(((tert-butoxycarbonyl)amino)methyl)-2'-fluoro-6-hydroxy-5-(1-(hydroxyimino)ethyl)-[1,1'-biphenyl]-3-carboxylate (267b) (1 g, 2.312 mmol) in THF (20 mL) using carbonyl diimidazole (750 mg, 4.62 mmol) and heating at reflux for 90 mins. This gave after workup and purification by flash column chromatography [silica gel (40 g), eluting with ethyl acetate and hexanes] methyl 7-(3-(((tert-butoxycarbonyl)amino)methyl)-2-fluorophenyl)-3-methylbenzo[d]isoxazole-5-carboxylate (267c) (560 mg, 58% yield) as a white solid; $^1$H NMR (300 MHz, DMSO-$d_6$) δ 8.56 (d, J=1.6 Hz, 1H), 8.24 (t, J=1.3 Hz, 1H), 7.60 (td, J=7.3, 1.9 Hz, 1H), 7.50 (q, J=5.6, 5.1 Hz, 1H), 7.47-7.39 (m, 1H), 7.37 (t, J=7.6 Hz, 1H), 4.27 (d, J=6.1 Hz, 2H), 3.93 (s, 3H), 2.67 (s, 3H), 1.41 (s, 9H); $^{19}$F NMR (282 MHz, DMSO-$d_6$) δ−121.39.

Step-4: Preparation of 7-(3-(((tert-butoxycarbonyl)amino)methyl)-2-fluorophenyl)-3-methylbenzo[d]isoxazole-5-carboxylic Acid (267d)

Compound 267d was prepared according to the procedure reported in step-6 of scheme-1, from methyl 7-(3-(((tert-butoxycarbonyl)amino)methyl)-2-fluorophenyl)-3-methylbenzo[d]isoxazole-5-carboxylate (267c) (500 mg, 1.206 mmol) in THF/MeOH (10 mL, each) using a solution of lithium hydroxide hydrate (116 mg, 4.83 mmol) in water (2 mL). This gave after workup 7-(3-(((tert-butoxycarbonyl)amino)methyl)-2-fluorophenyl)-3-methylbenzo[d]isoxazole-5-carboxylic acid (267d) (509 mg) as a white solid; $^1$H NMR (300 MHz, DMSO-$d_6$) δ 13.35 (s, 1H), 8.53 (d, J=1.6 Hz, 1H), 8.23 (t, J=1.3 Hz, 1H), 7.60 (td, J=7.3, 2.0 Hz, 1H), 7.51 (t, J=6.0 Hz, 1H), 7.48-7.39 (m, 1H), 7.37 (t, J=7.6 Hz, 1H), 4.28 (d, J=6.1 Hz, 2H), 2.66 (s, 3H), 1.41 (s, 9H); $^{19}$F NMR (282 MHz, DMSO-$d_6$) δ−121.35; MS (ES−): 399.0 (M−1).

Step-5: Preparation of tert-butyl 2-fluoro-3-(5-(hydroxymethyl)-3-methylbenzo[d]isoxazol-7-yl)benzylcarbamate (267e)

Compound 267e was prepared according to the procedure reported in step-1 of scheme-23 from 7-(3-(((tert-butoxycarbonyl)amino)methyl)-2-fluorophenyl)-3-methylbenzo[d]isoxazole-5-carboxylic acid (267d) (500 mg, 1.249 mmol) using N-methylmorpholine (0.165 mL, 1.499 mmol) in THF (10 mL), isobutyl chloroformate (0.197 mL, 1.499 mmol) and NaBH$_4$ (142 mg, 3.75 mmol) in water (1 mL). This gave after workup and purification by flash column chromatography [silica gel (25 g), eluting with a 9:1 mixture of ethyl acetate and methanol in hexanes 0-100%] tert-butyl 2-fluoro-3-(5-(hydroxymethyl)-3-methylbenzo[d]isoxazol-7-yl)benzylcarbamate (267e) (420 mg, 87% yield) as a white solid; $^1$H NMR (300 MHz, DMSO-$d_6$) δ 7.82 (dd, J=1.6, 0.8 Hz, 1H), 7.65 (t, J=1.2 Hz, 1H), 7.52 (td, J=7.3, 2.2 Hz, 2H), 7.46-7.37 (m, 1H), 7.34 (t, J=7.5 Hz, 1H), 5.43 (t, J=5.7 Hz, 1H), 4.68 (d, J=5.6 Hz, 2H), 4.27 (d, J=6.1 Hz, 2H), 2.59 (s, 3H), 1.41 (s, 9H); $^{19}$F NMR (282 MHz, DMSO-$d_6$) δ−121.14; MS (ES+): 387.00 (M+1), 409.00 (M+Na).

Step-6: Preparation of Ethyl 2-(2-((7-(3-(((tert-butoxycarbonyl)amino)methyl)-2-fluorophenyl)-3-methylbenzo[d]isoxazol-5-yl)methoxy)phenyl)acetate (267f)

Compound 267f was prepared according to the procedure reported in step-2 of scheme-23 from tert-butyl 2-fluoro-3-(5-(hydroxymethyl)-3-methylbenzo[d]isoxazol-7-yl)benzylcarbamate (267e) (400 mg, 1.035 mmol) in DCM (10 mL) using triphenylphosphine (339 mg, 1.294 mmol), ethyl 2-(2-hydroxyphenyl) acetate (23b) (233 mg, 1.294 mmol) and a solution of (E)-bis(4-chlorobenzyl) diazene-1,2-dicarboxylate (DCAD, 532 mg, 1.449 mmol) in DCM (5 mL). This gave after workup and purification by flash column chromatography (silica gel 25 g, eluting with EtOAc in hexane from 0-50%) ethyl 2-(2-((7-(3-(((tert-butoxycarbonyl)amino)methyl)-2-fluorophenyl)-3-methylbenzo[d]isoxazol-5-yl)methoxy)phenyl)acetate (267f) (550 mg, 97% yield) as a colorless oil; $^1$H NMR (300 MHz, DMSO-$d_6$) δ 7.97 (d, J=1.5 Hz, 1H), 7.76 (d, J=1.4 Hz, 1H), 7.53 (ddt, J=10.8, 7.9, 3.9 Hz, 2H), 7.38 (dt, J=11.5, 8.1 Hz, 2H), 7.31-7.20 (m, 2H), 7.13 (dd, J=8.3, 1.1 Hz, 1H), 6.92 (td, J=7.4, 1.1 Hz, 1H), 5.28 (s, 2H), 4.27 (d, J=6.1 Hz, 2H), 3.88 (q, J=7.1 Hz, 2H), 3.63 (s, 2H), 2.60 (s, 3H), 1.41 (s, 9H), 0.95 (t, J=7.1 Hz, 3H); $^{19}$F NMR (282 MHz, DMSO-$d_6$) δ−120.88.

Step-7: Preparation of Ethyl 2-(2-((7-(3-(aminomethyl)-2-fluorophenyl)-3-methylbenzo[d]isoxazol-5-yl)methoxy)phenyl)acetate (267g)

Compound 267g was prepared according to the procedure reported in step-5 of scheme-1 from ethyl 2-(2-((7-(3-(((tert-butoxycarbonyl)amino)methyl)-2-fluorophenyl)-3-methylbenzo[d]isoxazol-5-yl)methoxy)phenyl)acetate (267f) (525 mg, 0.957 mmol) in DCM (5 mL) using TFA (0.737 mL, 9.57 mmol). This gave after workup ethyl 2-(2-((7-(3-(aminomethyl)-2-fluorophenyl)-3-methylbenzo[d]isoxazol-5-yl)methoxy)phenyl)acetate (267g) (429 mg, 100% yield) which was used in the next reaction without further purification; MS (ES+): 449.1 (M+1).

Step-8: Preparation of 2-(2-((7-(3-(aminomethyl)-2-fluorophenyl)-3-methylbenzo[d]isoxazol-5-yl)methoxy)phenyl)acetic Acid (267h)

Compound 267h was prepared according to the procedure reported in step-6 of scheme-1, from ethyl 2-(2-((7-(3-(aminomethyl)-2-fluorophenyl)-3-methylbenzo[d]isoxazol-5-yl)methoxy)phenyl)acetate (267g) (429 mg, 0.957 mmol)

in THF/MeOH (10 mL, each) using a solution of lithium hydroxide hydrate (229 mg, 9.57 mmol) in water (3 mL). This gave after workup and purification by reverse phase column chromatography [C18 column, 50 g, eluting with water (containing 0.1% HCl)/acetonitrile (1:0 to 0:1)] 2-(2-((7-(3-(aminomethyl)-2-fluorophenyl)-3-methylbenzo[d]isoxazol-5-yl)methoxy)phenyl)acetic acid (267h) (250 mg, 62% yield) hydrochloride salt as a white solid; $^1$H NMR (300 MHz, DMSO-$d_6$) δ 8.04 (d, J=1.5 Hz, 1H), 7.80 (d, J=1.2 Hz, 1H), 7.71 (td, J=7.2, 1.6 Hz, 2H), 7.46 (t, J=7.7 Hz, 1H), 7.29-7.19 (m, 2H), 7.13-7.07 (m, 1H), 6.92 (td, J=7.4, 1.1 Hz, 1H), 5.32 (s, 2H), 4.19 (s, 2H), 3.60 (s, 2H), 2.61 (s, 3H); $^{19}$F NMR (282 MHz, DMSO-$d_6$) δ−118.31; MS (ES+): 421.1 (M+1), (ES−): 419.1 (M−1); Analysis calculated for $C_{24}H_{21}FN_2O_4 \cdot 1.05HCl \cdot H_2O$: C, 60.47; H, 5.08; Cl, 7.81; N, 5.88; Found: C, 60.50; H, 4.78; Cl, 8.10; N, 5.71.

Scheme-268

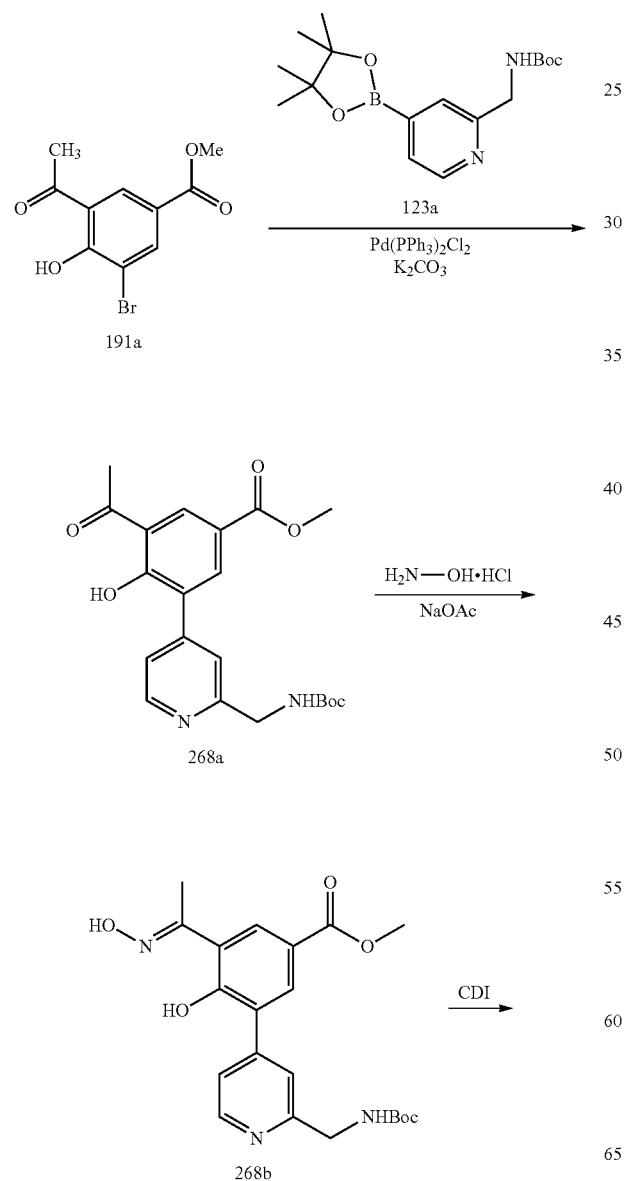

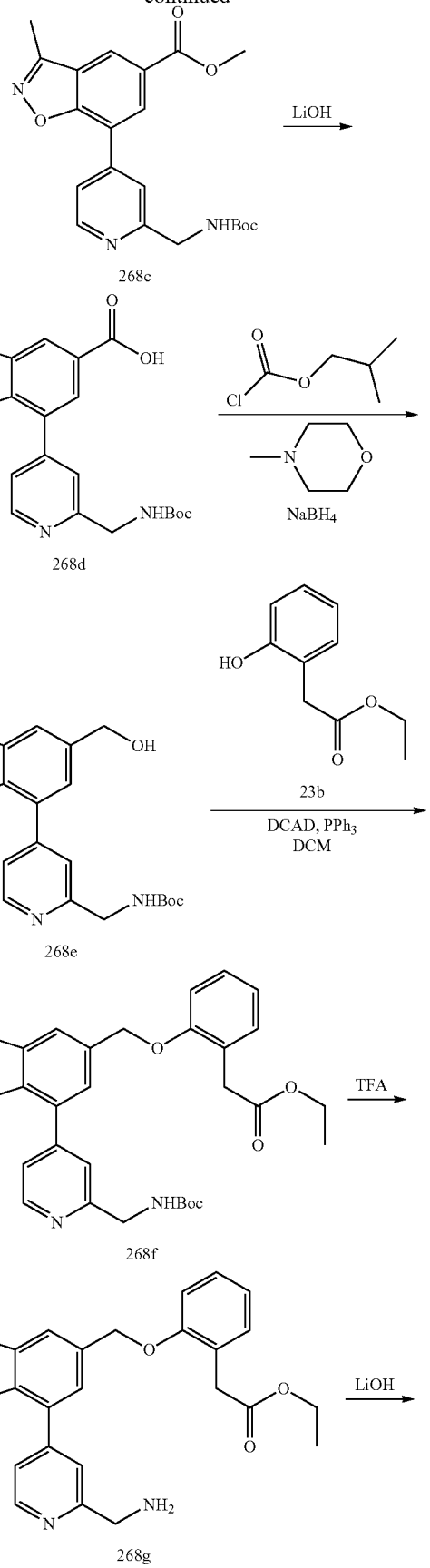

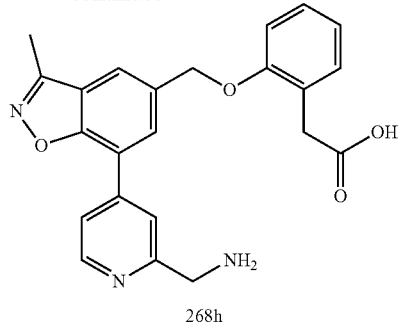

268h

Preparation of 2-(2-((7-(2-(aminomethyl)pyridin-4-yl)-3-methylbenzo[d]isoxazol-5-yl)methoxy)phenyl)acetic Acid (268h)

Step-1: Preparation of methyl 3-acetyl-5-(2-(((tert-butoxycarbonyl)amino)methyl)pyridin-4-yl)-4-hydroxybenzoate (268a)

Compound 268a was prepared according to the procedure reported in step-3 of scheme-1 from methyl 3-acetyl-5-bromo-4-hydroxybenzoate (191a) (0.5 g, 1.831 mmol) in dioxane (10 mL) using tert-butyl ((4-(4,4,5,5-tetramethyl-1,3,2-dioxaborolan-2-yl)pyridin-2-yl)methyl)carbamate (123a) (0.734 g, 2.19 mmol), Pd(PPh$_3$)$_2$Cl$_2$ (0.193 g, 0.275 mmol) and a solution of K$_2$CO$_3$ (0.759 g, 5.49 mmol) in water (2 mL) under a nitrogen atmosphere and heating at 100° C. for 5 h on oil bath. This gave after workup and purification by flash column chromatography (silica gel, 40g, eluting with ethyl acetate and in hexanes 0-50%) methyl 3-acetyl-5-(2-(((tert-butoxycarbonyl)amino)methyl)pyridin-4-yl)-4-hydroxybenzoate (268a) (406 mg, 1.014 mmol, 55.4% yield) as a white foam; $^1$H NMR (300 MHz, DMSO-d$_6$) δ 13.43 (s, 1H), 8.57 (d, J=0.8 Hz, 1H), 8.55 (d, J=2.0 Hz, 1H), 8.15 (d, J=2.1 Hz, 1H), 7.55-7.42 (m, 3H), 4.28 (d, J=6.1 Hz, 2H), 3.88 (s, 3H), 2.80 (s, 3H), 1.40 (s, 9H); MS (ES+): 401.00 (M+1).

Step-2: Preparation of (E)-methyl 3-(2-(((tert-butoxycarbonyl)amino)methyl)pyridin-4-yl)-4-hydroxy-5-(1-(hydroxyimino)ethyl)benzoate (268b)

Compound 268b was prepared according to the procedure reported in step-2 of scheme-267 from methyl 3-acetyl-5-(2-(((tert-butoxycarbonyl)amino)methyl)pyridin-4-yl)-4-hydroxybenzoate (268a) (0.4 g, 1.0 mmol) in methanol (20 mL) using hydroxylamine hydrochloride (278 mg, 4.0 mmol), sodium acetate (328 mg, 4.0 mmol) and heating at reflux for 1 h on oil bath. This gave after workup (E)-methyl 3-(2-(((tert-butoxycarbonyl)amino)methyl)pyridin-4-yl)-4-hydroxy-5-(1-(hydroxyimino)ethyl)benzoate (268b) (370 mg, 89% yield) as a white solid; $^1$H NMR (300 MHz, DMSO-d$_6$) δ 13.31 (s, 1H), 12.02 (s, 1H), 8.53 (dd, J=5.2, 0.8 Hz, 1H), 8.15 (d, J=2.1 Hz, 1H), 7.90 (d, J=2.1 Hz, 1H), 7.50 (dd, J=5.1, 1.7 Hz, 2H), 7.44 (s, 1H), 4.28 (d, J=6.2 Hz, 2H), 3.85 (s, 3H), 2.38 (s, 3H), 1.40 (s, 9H).

Step-3: Preparation of methyl 7-(2-(((tert-butoxycarbonyl)amino)methyl)pyridin-4-yl)-3-methylbenzo[d]isoxazole-5-carboxylate (268c)

Compound 268c was prepared according to the procedure reported in step-2 of scheme-191 from (E)-methyl 3-(2-(((tert-butoxycarbonyl)amino)methyl)pyridin-4-yl)-4-hydroxy-5-(1-(hydroxyimino)ethyl)benzoate (268b) (360 mg, 0.867 mmol) in THF (10 mL) using carbonyl diimidazole (703 mg, 4.33 mmol) and heating at reflux for 90 mins. This gave after workup and purification by flash column chromatography [silica gel (40 g), eluting with ethyl acetate and hexanes] methyl 7-(2-(((tert-butoxycarbonyl)amino)methyl)pyridin-4-yl)-3-methylbenzo[d]isoxazole-5-carboxylate (268c) (413 mg) as a white solid; $^1$H NMR (300 MHz, DMSO-d$_6$) δ 8.68 (dd, J=5.1, 0.9 Hz, 1H), 8.60 (d, J=1.5 Hz, 1H), 8.47 (d, J=1.5 Hz, 1H), 7.84 (dd, J=7.1, 1.9 Hz, 2H), 7.67-7.55 (m, 1H), 4.33 (d, J=6.2 Hz, 2H), 3.95 (s, 3H), 2.68 (s, 3H), 1.43 (s, 9H).

Step-4: Preparation of 7-(2-(((tert-butoxycarbonyl)amino)methyl)pyridin-4-yl)-3-methylbenzo[d]isoxazole-5-carboxylic Acid (268d)

Compound 268d was prepared according to the procedure reported in step-6 of scheme-1 from methyl 7-(2-(((tert-butoxycarbonyl)amino)methyl)pyridin-4-yl)-3-methylbenzo[d]isoxazole-5-carboxylate (268c) (400 mg, 1.006 mmol) in THF/MeOH (10 mL, each) using a solution of lithium hydroxide hydrate (96 mg, 4.03 mmol) in water (2 mL). This gave after workup 7-(2-(((tert-butoxycarbonyl)amino)methyl)pyridin-4-yl)-3-methylbenzo[d]isoxazole-5-carboxylic acid (268d) (320 mg, 83% yield) as a white solid; $^1$H NMR (300 MHz, DMSO-d$_6$) δ 8.76 (d, J=5.5 Hz, 1H), 8.61 (d, J=1.5 Hz, 1H), 8.55 (d, J=1.5 Hz, 1H), 8.08-7.96 (m, 2H), 7.67 (t, J=6.0 Hz, 1H), 4.40 (d, J=6.0 Hz, 2H), 2.68 (s, 3H), 1.42 (s, 9H); MS (ES+): 384.2 (M+1).

Step-5: Preparation of tert-butyl ((4-(5-(hydroxymethyl)-3-methylbenzo[d]isoxazol-7-yl)pyridin-2-yl)methyl)carbamate (268e)

Compound 268e was prepared according to the procedure reported in step-1 of scheme-23 from 7-(2-(((tert-butoxycarbonyl)amino)methyl)pyridin-4-yl)-3-methylbenzo[d]isoxazole-5-carboxylic acid (268d) (300 mg, 0.782 mmol) using N-methylmorpholine (0.103 mL, 0.939 mmol) in THF (10 mL), isobutyl chloroformate (0.123 mL, 0.939 mmol) and NaBH$_4$ (89 mg, 2.347 mmol) in water (1 mL). This gave after workup and purification by flash column chromatography [silica gel (25 g), eluting with a 9:1 mixture of ethyl acetate and methanol in hexanes 0-100%] tert-butyl ((4-(5-(hydroxymethyl)-3-methylbenzo[d]isoxazol-7-yl)pyridin-2-yl)methyl)carbamate (268e) (131 mg, 45% yield) as a white solid; $^1$H NMR (300 MHz, DMSO-d$_6$) δ 8.65 (dd, J=5.2, 0.8 Hz, 1H), 7.98 (d, J=1.5 Hz, 1H), 7.88 (d, J=1.4 Hz, 1H), 7.86 (s, 1H), 7.80 (dd, J=5.2, 1.8 Hz, 1H), 7.56 (t, J=6.1 Hz, 1H), 5.47 (t, J=5.6 Hz, 1H), 4.71 (d, J=5.2 Hz, 2H), 4.32 (d, J=6.2 Hz, 2H), 2.61 (s, 3H), 1.42 (s, 9H); MS (ES+): 370.1 (M+1).

Step-6: Preparation of Ethyl 2-(2-((7-(2-(((tert-butoxycarbonyl)amino)methyl)pyridin-4-yl)-3-methylbenzo[d]isoxazol-5-yl)methoxy)phenyl)acetate (268f)

Compound 268f was prepared according to the procedure reported in step-2 of scheme-23 from tert-butyl ((4-(5-(hydroxymethyl)-3-methylbenzo[d]isoxazol-7-yl)pyridin-2-yl)methyl)carbamate (268e) (125 mg, 0.338 mmol) in DCM (5 mL) using triphenylphosphine (111 mg, 0.423 mmol), ethyl 2-(2-hydroxyphenyl) acetate (23b) (76 mg, 0.423 mmol) and a solution of (E)-bis(4-chlorobenzyl) diazene-1,2-dicarboxylate (DCAD, 174 mg, 0.474 mmol) in DCM (3 mL). This gave after workup and purification by flash column chromatography (silica gel, 25 g, eluting with EtOAc in hexane from 0-50%) ethyl 2-(2-((7-(2-(((tert-butoxycarbonyl)amino)methyl)pyridin-4-yl)-3-methyl-benzo[d]isoxazol-5-yl)methoxy)phenyl)acetate (268f) (110 mg, 61% yield) as a colorless oil; $^1$H NMR (300 MHz, DMSO-$d_6$) δ 8.67 (dd, J=5.2, 0.8 Hz, 1H), 8.10 (d, J=1.5 Hz, 1H), 8.03 (d, J=1.5 Hz, 1H), 7.91 (s, 1H), 7.81 (dd, J=5.2, 1.8 Hz, 1H), 7.54 (t, J=6.1 Hz, 1H), 7.32-7.19 (m, 2H), 7.19-7.08 (m, 1H), 6.93 (td, J=7.4, 1.1 Hz, 1H), 5.30 (s, 2H), 4.33 (d, J=6.2 Hz, 2H), 3.91 (q, J=7.1 Hz, 2H), 3.65 (s, 2H), 2.63 (s, 3H), 1.41 (s, 9H), 0.94 (t, J=7.1 Hz, 3H); MS (ES+): 532.2 (M+1).

Step-7: Preparation of Ethyl 2-(2-((7-(2-(aminomethyl)pyridin-4-yl)-3-methylbenzo[d]isoxazol-5-yl)methoxy)phenyl)acetate (268g)

Compound 268g was prepared according to the procedure reported in step-5 of scheme-1 from ethyl 2-(2-((7-(2-(((tert-butoxycarbonyl)amino)methyl)pyridin-4-yl)-3-methyl-benzo[d]isoxazol-5-yl)methoxy)phenyl)acetate (268f) (110 mg, 0.207 mmol) in DCM (2 mL) using TFA (0.159 mL, 2.064 mmol). This gave after workup ethyl 2-(2-((7-(2-(aminomethyl)pyridin-4-yl)-3-methylbenzo[d]isoxazol-5-yl)methoxy)phenyl)acetate (268g) (90 mg) which was used as such in the next step without further purification; $^1$H NMR (300 MHz, DMSO-$d_6$) δ 8.82 (dd, J=5.3, 0.8 Hz, 1H), 8.37 (s, 3H), 8.16 (d, J=1.6 Hz, 1H), 8.12-8.05 (m, 2H), 8.01 (dd, J=5.2, 1.7 Hz, 1H), 7.32-7.21 (m, 2H), 7.16-7.08 (m, 1H), 6.93 (td, J=7.4, 1.1 Hz, 1H), 5.32 (s, 2H), 4.35 (q, J=5.8 Hz, 2H), 3.93 (q, J=7.1 Hz, 2H), 3.66 (s, 2H), 2.63 (s, 3H), 0.96 (t, J=7.1 Hz, 3H); MS (ES+): 432.20 (M+1).

Step-8: Preparation of 2-(2-((7-(2-(aminomethyl)pyridin-4-yl)-3-methylbenzo[d]isoxazol-5-yl)methoxy)phenyl)acetic Acid (268h)

Compound 268h was prepared according to the procedure reported in step-6 of scheme-1, from ethyl 2-(2-((7-(2-(aminomethyl)pyridin-4-yl)-3-methylbenzo[d]isoxazol-5-yl)methoxy)phenyl)acetate (268g) (89 mg, 0.207 mmol) in THF/MeOH (2 mL, each) using a solution of lithium hydroxide hydrate (20 mg, 0.828 mmol) in water (1 mL). This gave after workup and purification by reverse phase column chromatography [C18 column, 50 g, eluting with water (containing 0.1% HCl)/acetonitrile (1:0 to 0:1)] 2-(2-((7-(2-(aminomethyl)pyridin-4-yl)-3-methylbenzo[d]isoxazol-5-yl)methoxy)phenyl)acetic acid (268h) (50 mg, 60% yield) HCL salt as a white solid; $^1$H NMR (300 MHz, DMSO-$d_6$) δ 8.81 (dd, J=5.3, 0.7 Hz, 1H), 8.55 (s, 3H), 8.20 (d, J=1.5 Hz, 1H), 8.17-8.11 (m, 1H), 8.10 (s, 1H), 8.03 (dd, J=5.3, 1.7 Hz, 1H), 7.26 (t, J=7.5 Hz, 2H), 7.11 (d, J=8.1 Hz, 1H), 6.93 (td, J=7.4, 1.1 Hz, 1H), 5.34 (s, 2H), 4.33 (d, J=5.7 Hz, 2H), 3.64 (s, 2H), 2.64 (s, 3H); MS (ES+): 404.1 (M+1), (ES−): 402.1 (M−1).

Scheme-269

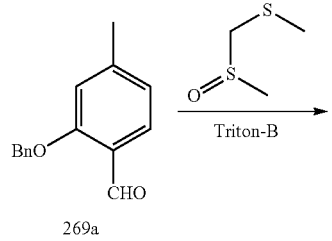

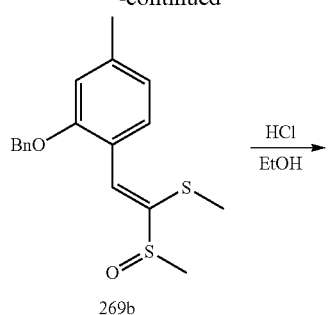

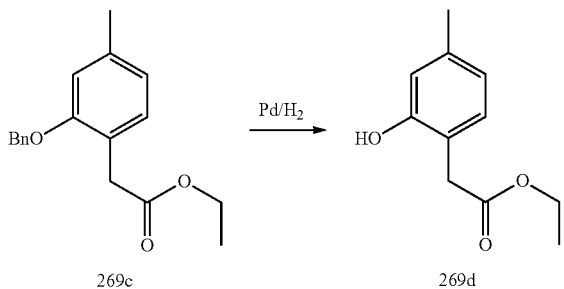

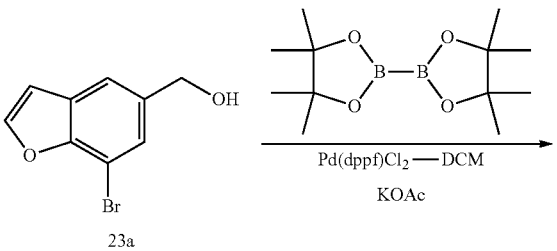

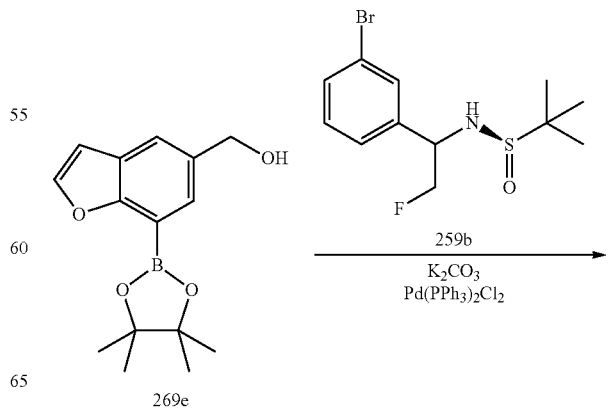

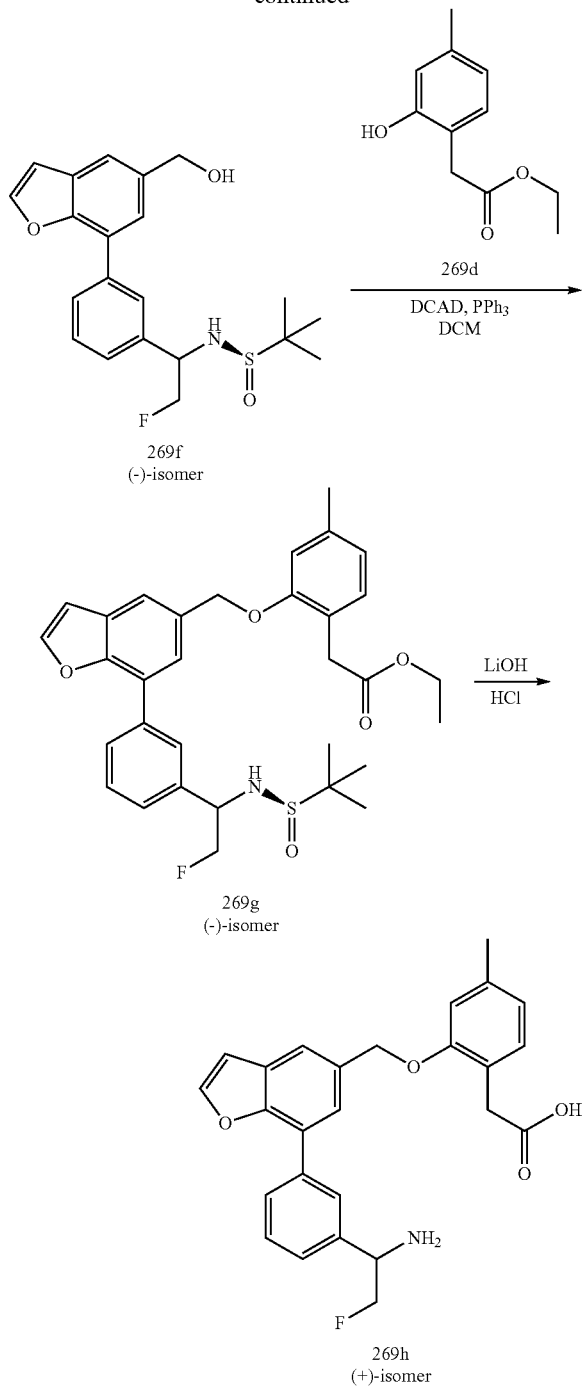

Preparation of (+)-2-(2-((7-(3-(1-amino-2-fluoroethyl)phenyl)benzofuran-5-yl)methoxy)-4-methylphenyl)acetic Acid (269h)

Step-1: Preparation of (2-(2-(benzyloxy)-4-methylphenyl)-1-(methyl sulfinyl)vinyl)(methyl)sulfane (269b)

Compound 269b was prepared according to the procedure reported in step-3 of scheme-266 from 2-(benzyloxy)-4-methylbenzaldehyde (269a) (2 g, 8.84 mmol; CAS #154478-35-0) in THF (20 mL) using methyl(methylsulfinylmethyl)sulfane (2.196 g, 17.68 mmol), Triton-B (40% methanolic solution) (2.009 mL, 4.42 mmol) and heating at reflux for 12 h. This gave after workup and purification by flash column chromatography (silica gel, 80 g, eluting with a 9:1 mixture of ethyl acetate and methanol in hexanes) (E)-(2-(2-(benzyloxy)-4-methylphenyl)-1-(methylsulfinyl)vinyl)(methyl)sulfane (269b) (2.32 g, 79% yield) as a thick syrup; $^1$H NMR (300 MHz, DMSO-$d_6$) δ 7.99 (d, J=7.9 Hz, 1H), 7.84 (s, 1H), 7.51-7.31 (m, 5H), 7.05 (t, J=1.1 Hz, 1H), 6.88 (ddt, J=8.0, 1.5, 0.7 Hz, 1H), 5.19 (s, 2H), 2.70 (s, 3H), 2.33 (s, 3H), 2.27 (s, 3H).

Step-2: Preparation of Ethyl 2-(2-(benzyloxy)-4-methylphenyl)acetate (269c)

Compound 269c was prepared according to the procedure reported in step-4 of scheme-266 from (E)-(2-(2-(benzyloxy)-4-methylphenyl)-1-(methylsulfinyl)vinyl)(methyl) sulfane (269b) (1 g, 3.01 mmol) in ethanol (10 mL) using HCl (1.25 M solution in Ethanol, 9.62 mL, 12.03 mmol) and heating at reflux for 2 h. This gave after workup and purification by flash column chromatography (silica gel, 40 g, eluting with ethyl acetate and methanol in hexanes) ethyl 2-(2-(benzyloxy)-4-methylphenyl)acetate (269c) (511 mg, 60% yield) as a colorless oil; $^1$H NMR (300 MHz, DMSO-$d_6$) δ 7.46-7.28 (m, 5H), 7.08 (d, J=7.5 Hz, 1H), 6.89 (t, J=1.1 Hz, 1H), 6.72 (ddd, J=7.5, 1.6, 0.8 Hz, 1H), 5.07 (s, 2H), 3.99 (q, J=7.1 Hz, 2H), 3.56 (s, 2H), 2.28 (s, 3H), 1.10 (t, J=7.1 Hz, 3H); MS (ES+): 285.1 (M+1).

Step-3: Preparation of Ethyl 2-(2-hydroxy-4-methylphenyl)acetate (269d)

To a solution of ethyl 2-(2-(benzyloxy)-4-methylphenyl) acetate (269c) (500 mg, 1.758 mmol) in ethanol (30 mL) was added Pd/C (187 mg, 0.176 mmol) and hydrogenated (balloon pressure) for 4 h. The reaction mixture was filtered over a Celite pad and concentrated in vacuum. The residue obtained was purified by flash column chromatography (silica gel) to afford ethyl 2-(2-hydroxy-4-methylphenyl) acetate (269d) (285 mg, 83% yield) as a colorless oil; $^1$H NMR (300 MHz, DMSO-$d_6$) δ 9.33 (s, 1H), 6.95 (d, J=7.6 Hz, 1H), 6.62-6.57 (m, 1H), 6.54 (ddd, J=7.5, 1.8, 0.8 Hz, 1H), 4.04 (q, J=7.1 Hz, 2H), 3.47 (s, 2H), 2.19 (s, 3H), 1.16 (t, J=7.1 Hz, 3H).

Step-4: Preparation of (7-(4,4,5,5-tetramethyl-1,3,2-dioxaborolan-2-yl)benzofuran-5-yl)methanol (269e)

Compound 269e was prepared according to the procedure reported in step-1 of scheme-59 from (7-bromobenzofuran-5-yl)methanol (23a) (6.5 g, 28.6 mmol), using bis(pinacolato)diboron (10.9 g, 42.9 mmol), potassium acetate (8.43 g, 86 mmol) and Pd(dppf)Cl$_2$-DCM (2.34 g, 2.86 mmol) in anhydrous dioxane (200 mL) under an Argon atmosphere and heating at 90° C. for 18h. This gave after workup and purification by flash column chromatography [silica (120g), eluting with EtOAc in hexane from 0-60%] (7-(4,4,5,5-tetramethyl-1,3,2-dioxaborolan-2-yl)benzofuran-5-yl) methanol (269e) (6.81 g, 87% yield) as an off-white solid; $^1$H NMR (300 MHz, DMSO-$d_6$) δ 8.01 (d, J=2.2 Hz, 1H), 7.71 (dd, J=1.8, 0.9 Hz, 1H), 7.59 (d, J=2.2 Hz, 1H), 6.93 (d, J=2.2 Hz, 1H), 5.22 (t, J=5.8 Hz, 1H), 4.58 (dt, J=5.8, 0.7 Hz, 2H), 1.34 (s, 12H).

Step-5: Preparation of (−)-(R)—N-(2-fluoro-1-(3-(5-(hydroxymethyl)benzofuran-7-yl)phenyl)ethyl)-2-methylpropane-2-sulfinamide (269f)

Compound 269f was prepared according to the procedure reported in step-3 of scheme-1 from (7-(4,4,5,5-tetramethyl-1,3,2-dioxaborolan-2-yl)benzofuran-5-yl)methanol (269e) (3 g, 10.94 mmol) in dioxane (40 mL) using (−)-(S)—N-(1-(3-bromophenyl)-2-fluoroethyl)-2-methylpropane-2-sulfinamide (259b) (4.23 g, 13.13 mmol), bis(triphenylphosphine)palladium(II) chloride (PdCl$_2$(PPh$_3$)$_2$) (1.152 g, 1.642 mmol) and a solution of K$_2$CO$_3$ (4.54 g, 32.8 mmol) in water (8 mL) under an N$_2$ atmosphere heating at 100° C. for 5 h on oil bath. This gave after workup, purification by flash column chromatography (silica gel, 40 g, eluting with a 9:1 mixture of ethyl acetate and methanol in hexanes) (−)-(R)—N-(2-fluoro-1-(3-(5-(hydroxymethyl)benzofuran-7-yl)phenyl)ethyl)-2-methylpropane-2-sulfinamide (269f) (2.8 g, 66% yield) as a clear oil; $^1$H NMR (300 MHz, DMSO-d$_6$) δ 8.04 (d, J=2.2 Hz, 1H), 7.90 (s, 1H), 7.81 (ddd, J=5.5, 3.7, 1.8 Hz, 1H), 7.61 (d, J=1.7 Hz, 1H), 7.55-7.44 (m, 3H), 7.03 (d, J=2.2 Hz, 1H), 6.07 (d, J=8.3 Hz, 1H), 5.28 (t, J=5.7 Hz, 1H), 4.71-4.62 (m, 4H), 4.51 (d, J=6.3 Hz, 1H), 1.14 (s, 9H); MS (ES+): 412.1 (M+Na), (ES−): 388.1 (M−1); Optical rotation [t]D=−1.10 (c=0.95, MeOH).

Step-6: Preparation of (−)-ethyl 2-(2-((7-(3-(1-((R)-1,1-dimethylethylsulfinamido)-2-fluoroethyl)phenyl)benzofuran-5-yl)methoxy)-4-methylphenyl)acetate (269g)

Compound 269g was prepared according to the procedure reported in step-2 of scheme-23 from (−)-(R)—N-(2-fluoro-1-(3-(5-(hydroxymethyl)benzofuran-7-yl)phenyl)ethyl)-2-methylpropane-2-sulfinamide (269f) (400 mg, 1.027 mmol) in DCM (15 mL) using triphenylphosphine (337 mg, 1.284 mmol), ethyl 2-(2-hydroxy-4-methylphenyl)acetate (269d) (249 mg, 1.284 mmol) and a solution of (E)-bis(4-chlorobenzyl) diazene-1,2-dicarboxylate (DCAD, 528 mg, 1.438 mmol) in DCM (10 mL). This gave after workup and purification by flash column chromatography (silica gel, 25 g, eluting with ethyl acetate in hexanes from 0-50%) (−)-ethyl 2-(2-((7-(3-(1-((R)-1,1-dimethylethylsulfinamido)-2-fluoroethyl)phenyl)benzofuran-5-yl)methoxy)-4-methylphenyl)acetate (269g) (340 mg, 59% yield) as a colorless oil; $^1$H NMR (300 MHz, DMSO-d$_6$) δ 8.10 (d, J=2.2 Hz, 1H), 7.92 (s, 1H), 7.83 (td, J=4.5, 1.7 Hz, 1H), 7.71 (d, J=1.6 Hz, 1H), 7.59 (d, J=1.7 Hz, 1H), 7.53 (d, J=4.7 Hz, 2H), 7.12-7.02 (m, 2H), 7.01-6.88 (m, 1H), 6.78-6.66 (m, 1H), 6.05 (d, J=8.2 Hz, 1H), 5.21 (s, 2H), 4.68 (s, 2H), 4.52 (d, J=6.3 Hz, 1H), 3.90 (q, J=7.1 Hz, 2H), 3.57 (s, 2H), 2.30 (s, 3H), 1.13 (s, 9H), 0.96 (t, J=7.1 Hz, 3H); MS (ES+): 566.2 (M+1), 568.2 (M+Na), (ES−): 564.2 (M−1); Optical rotation [α]$_D$=−2.29 (c=0.18, MeOH).

Step 7: Preparation of (+)-2-(2-((7-(3-(1-amino-2-fluoroethyl)phenyl)benzofuran-5-yl)methoxy)-4-methylphenyl)acetic Acid (269h)

To a stirred solution of (−)-ethyl 2-(2-((7-(3-(1-((R)-1,1-dimethylethylsulfinamido)-2-fluoroethyl)phenyl)benzofuran-5-yl)methoxy)-4-methylphenyl)acetate (269g) (331 mg, 0.585 mmol) in THF (5 mL), methanol (5 mL) and water (2 mL) was added lithium hydroxide (70.1 mg, 2.93 mmol) and stirred for 12 h. Reaction was concentrated to remove organic solvents, suspended in 1:1 THF water mixture (10 mL) added HCl (3N in water) (2.93 mL, 8.78 mmol) and stirred at room temperature for 2 h. The reaction mixture was concentrated to remove organic solvents. The mixture was purified by reverse phase column chromatography (C18, 50 g, 0-60% MeCN in H$_2$O containing 0.1% HCl) to afford (+)-2-(2-((7-(3-(1-amino-2-fluoroethyl)phenyl)benzofuran-5-yl)methoxy)-4-methylphenyl)acetic acid (269h) (25 mg, 10% yield) HCl salt as a white solid; $^1$H NMR (300 MHz, DMSO-d$_6$) δ 8.11 (d, J=2.2 Hz, 1H), 8.04 (d, J=1.8 Hz, 1H), 7.98 (dd, J=7.4, 1.7 Hz, 1H), 7.77 (d, J=1.6 Hz, 1H), 7.69-7.63 (m, 2H), 7.63-7.55 (m, 2H), 7.12-7.05 (m, 2H), 6.95 (d, J=1.5 Hz, 1H), 6.73 (d, J=7.5 Hz, 1H), 5.24 (s, 2H), 4.94-4.83 (m, 1H), 4.77 (q, J=3.8 Hz, 1H), 3.54 (s, 2H), 2.29 (s, 3H); MS (ES+): 434.1 (M+1), (ES−): 432.1 (M−1); Optical rotation [α]$_D$=+15.69 (c=0.26, MeOH).

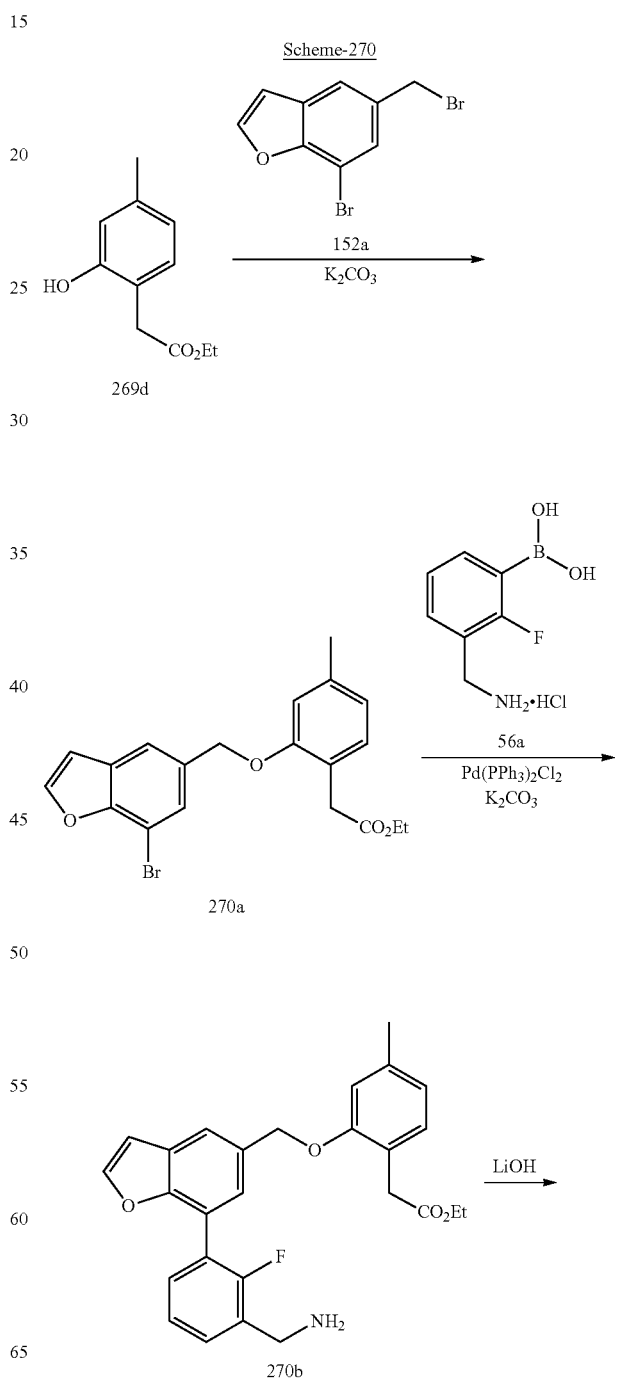

Scheme-270

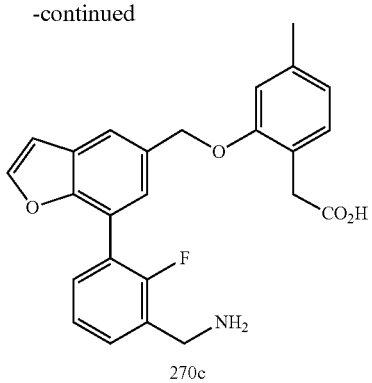

270c

Preparation of 2-(2-((7-(3-(aminomethyl)-2-fluorophenyl)benzofuran-5-yl)methoxy)-4-methylphenyl)acetic Acid (270c)

Step-1: Preparation of Ethyl 2-(2-((7-bromobenzofuran-5-yl)methoxy)-4-methylphenyl)acetate (270a)

Compound 270a was prepared according to the procedure reported in step-2 of scheme-152 from 7-bromo-5-(bromomethyl)benzofuran (152a) (0.6 g, 2.069 mmol) using ethyl 2-(2-hydroxy-4-methylphenyl)acetate (269d) (0.442 g, 2.276 mmol), $K_2CO_3$ (0.858 g, 6.21 mmol) in acetone (10 mL) and heating at reflux for 2 h. This gave after workup and purification by flash column chromatography ($SiO_2$, 40 g, eluting with EtOAc in hexane) ethyl 2-(2-((7-bromobenzofuran-5-yl)methoxy)-4-methylphenyl)acetate (270a) (628 mg, 75% yield) as a white solid; $^1$H NMR (300 MHz, DMSO-$d_6$) δ 8.15 (d, J=2.2 Hz, 1H), 7.71 (d, J=1.4 Hz, 1H), 7.60 (d, J=1.5 Hz, 1H), 7.12 (d, J=2.2 Hz, 1H), 7.09 (d, J=7.5 Hz, 1H), 6.94-6.91 (m, 1H), 6.73 (ddd, J=7.4, 1.6, 0.8 Hz, 1H), 5.15 (s, 2H), 4.00 (q, J=7.1 Hz, 2H), 3.56 (s, 2H), 2.29 (s, 3H), 1.07 (t, J=7.1 Hz, 3H); MS (ES+): 403.00, 405.00 (M, M+2).

Step-2: Preparation of Ethyl 2-(2-((7-(3-(aminomethyl)-2-fluorophenyl)benzofuran-5-yl)methoxy)-4-methylphenyl)acetate (270b)

Compound 270b was prepared according to the procedure reported in step-3 of scheme-1 from ethyl 2-(2-((7-bromobenzofuran-5-yl)methoxy)-4-methylphenyl)acetate (270a) (600 mg, 1.488 mmol) in dioxane (10 mL) using (3-(aminomethyl)-2-fluorophenyl)boronic acid hydrochloride (56a) (489 mg, 2.381 mmol), bis(triphenylphosphine)palladium(II) chloride ($Pd(PPh_3)_2Cl_2$) (157 mg, 0.223 mmol) and potassium carbonate (617 mg, 4.46 mmol) in water (3 mL) under an argon atmosphere heating at 100° C. for 3 h on oil bath. This gave after workup, purification by flash column chromatography (silica gel, 40 g, eluting with DMA80 in DCM from 0-50%) ethyl 2-(2-((7-(3-(aminomethyl)-2-fluorophenyl)benzofuran-5-yl)methoxy)-4-methylphenyl)acetate (270b) (565 mg, 85% yield) as a colorless syrup; $^1$H NMR (300 MHz, DMSO-$d_6$) δ 8.04 (d, J=2.2 Hz, 1H), 7.75 (d, J=1.7 Hz, 1H), 7.67-7.54 (m, 1H), 7.45 (td, J=7.4, 1.9 Hz, 1H), 7.40 (d, J=1.3 Hz, 1H), 7.31 (t, J=7.6 Hz, 1H), 7.08 (d, J=7.5 Hz, 1H), 7.05 (d, J=2.2 Hz, 1H), 6.97 (d, J=1.5 Hz, 1H), 6.72 (ddd, J=7.5, 1.6, 0.8 Hz, 1H), 5.20 (s, 2H), 3.89 (q, J=7.1 Hz, 2H), 3.83 (s, 2H), 3.55 (s, 2H), 2.30 (s, 3H), 1.93 (s, 2H), 0.97 (t, J=7.1 Hz, 3H); $^{19}$F NMR (282 MHz, DMSO-$d_6$) δ −121.75; MS (ES+): 448.2 (M+1).

Step-3: Preparation of 2-(2-((7-(3-(aminomethyl)-2-fluorophenyl)benzofuran-5-yl)methoxy)-4-methylphenyl)acetic Acid (270c)

Compound 270c was prepared according to the procedure reported in step-6 of scheme-1 from ethyl 2-(2-((7-(3-(aminomethyl)-2-fluorophenyl)benzofuran-5-yl)methoxy)-4-methylphenyl)acetate (270b) (550 mg, 1.229 mmol) in MeOH (10 mL), THF (10 mL) using a solution of lithium hydroxide (118 mg, 4.92 mmol) in water (5 mL). This gave after workup and purification by reverse phase column [C18 (50g), eluting with ACN in water (containing 0.1% HCl) from 0-100%] 2-(2-((7-(3-(aminomethyl)-2-fluorophenyl)benzofuran-5-yl)methoxy)-4-methylphenyl)acetic acid (270c) (187 mg, 36% yield) HCl salt as a white solid; $^1$H NMR (300 MHz, DMSO-$d_6$) δ 8.06 (d, J=2.2 Hz, 1H), 7.82 (d, J=1.6 Hz, 1H), 7.67 (td, J=7.2, 2.8 Hz, 2H), 7.46 (s, 1H), 7.42 (d, J=7.6 Hz, 1H), 7.11-7.04 (m, 2H), 6.94 (s, 1H), 6.72 (d, J=7.5 Hz, 1H), 5.23 (s, 2H), 4.18 (s, 2H), 3.52 (s, 2H), 2.29 (s, 3H); $^{19}$F NMR (282 MHz, DMSO-$d_6$) δ −118.38; MS (ES+): 420.1 (M+1), (ES−): 418.1 (M−1).

Scheme-271

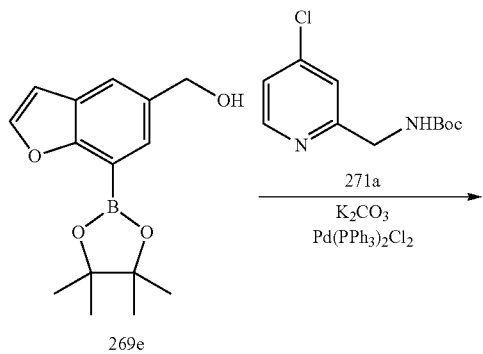

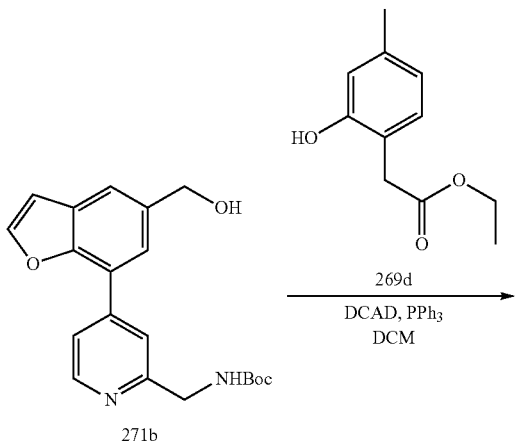

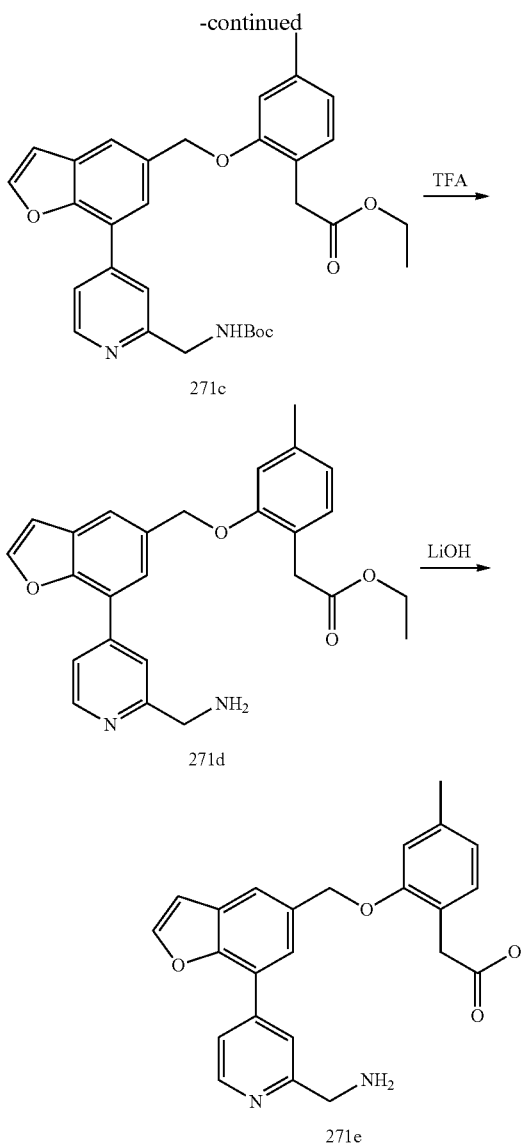

Preparation of 2-(2-((7-(2-(aminomethyl)pyridin-4-yl)benzofuran-5-yl)methoxy)-4-methylphenyl)acetic Acid (271e)

Step-1: Preparation of tert-butyl ((4-(5-(hydroxymethyl)benzofuran-7-yl)pyridin-2-yl)methyl)carbamate (271b)

Compound 271b was prepared according to the procedure reported in step-3 of scheme-1 from (7-(4,4,5,5-tetramethyl-1,3,2-dioxaborolan-2-yl)benzofuran-5-yl)methanol (269e) (0.5 g, 1.824 mmol) in dioxane (10 mL) using tert-butyl ((4-chloropyridin-2-yl)methyl)carbamate (271a) (0.531 g, 2.189 mmol; CAS #96628-86-3), bis(triphenylphosphine) palladium(II) chloride ($Pd(PPh_3)_2Cl_2$) (0.192 g, 0.274 mmol) and a solution of $K_2CO_3$ (0.756 g, 5.47 mmol) in water (2 mL) under an $N_2$ atmosphere heating at 100° C. for 5 h on oil bath. This gave after workup, purification by flash column chromatography (silica gel, 40 g, eluting with a 9:1 mixture of ethyl acetate and methanol in hexanes) tert-butyl ((4-(5-(hydroxymethyl)benzofuran-7-yl)pyridin-2-yl)methyl)carbamate (271b) (313 mg, 48% yield) as a white solid; $^1$H NMR (300 MHz, DMSO-$d_6$) δ 8.68-8.55 (m, 1H), 8.07 (d, J=2.2 Hz, 1H), 7.77 (d, J=4.9 Hz, 2H), 7.71 (d, J=1.5 Hz, 1H), 7.59 (d, J=1.6 Hz, 1H), 7.53 (t, J=6.2 Hz, 1H), 7.07 (d, J=2.2 Hz, 1H), 5.33 (t, J=5.7 Hz, 1H), 4.65 (d, J=5.7 Hz, 2H), 4.31 (d, J=6.1 Hz, 2H), 1.42 (s, 9H); MS (ES+): 355.1 (M+1).

Step-2: Preparation of Ethyl 2-(2-((7-(2-(((tert-butoxycarbonyl)amino)methyl)pyridin-4-yl)benzofuran-5-yl)methoxy)-4-methylphenyl)acetate (271c)

Compound 271c was prepared according to the procedure reported in step-2 of scheme-23 from tert-butyl ((4-(5-(hydroxymethyl)benzofuran-7-yl)pyridin-2-yl)methyl)carbamate (271b) ((330 mg, 0.931 mmol) in DCM (15 mL) using triphenylphosphine (305 mg, 1.164 mmol), ethyl 2-(2-hydroxy-4-methylphenyl)acetate (269d) (226 mg, 1.164 mmol) and a solution of (E)-bis(4-chlorobenzyl) diazene-1,2-dicarboxylate (DCAD, 479 mg, 1.304 mmol) in DCM (10 mL). This gave after workup and purification by flash column chromatography (silica gel, 25 g, eluting with ethyl acetate in hexanes from 0-50%) ethyl 2-(2-((7-(2-(((tert-butoxycarbonyl)amino)methyl)pyridin-4-yl)benzofuran-5-yl)methoxy)-4-methylphenyl)acetate (271c) (450 mg, 91% yield) as a colorless oil; MS (ES+): 531.2 (M+1).

Step-3: Preparation of Ethyl 2-(2-((7-(2-(aminomethyl)pyridin-4-yl)benzofuran-5-yl)methoxy)-4-methylphenyl)acetate (271d)

Compound 271d was prepared according to the procedure reported in step-5 of scheme-1 from ethyl 2-(2-((7-(2-(((tert-butoxycarbonyl)amino)methyl)pyridin-4-yl)benzofuran-5-yl)methoxy)-4-methylphenyl)acetate (271c) (450 mg, 0.848 mmol) in DCM (5 mL) using TFA (1.307 mL, 16.96 mmol). This gave after workup and purification by flash column chromatography (silica gel, 25 g, eluting with a 9:1 mixture of ethyl acetate and methanol in hexanes) ethyl 2-(2-((7-(2-(aminomethyl)pyridin-4-yl)benzofuran-5-yl)methoxy)-4-methylphenyl)acetate (271d) (189 mg, 52% yield) as a white solid; $^1$H NMR (300 MHz, DMSO-$d_6$) δ 8.75 (d, J=5.2 Hz, 1H), 8.17 (d, J=2.2 Hz, 1H), 8.09-7.97 (m, 1H), 7.92 (dd, J=5.2, 1.7 Hz, 1H), 7.84 (d, J=1.6 Hz, 1H), 7.76 (d, J=1.6 Hz, 1H), 7.13 (d, J=2.2 Hz, 1H), 7.10 (d, J=7.5 Hz, 1H), 6.97 (d, J=1.6 Hz, 1H), 6.74 (dd, J=7.4, 1.4 Hz, 1H), 5.24 (s, 2H), 4.22 (s, 2H), 3.92 (q, J=7.1 Hz, 2H), 3.58 (s, 2H), 2.30 (s, 3H), 0.97 (t, J=7.1 Hz, 3H); MS (ES(+): 431.2 (M+1).

Step-4: Preparation of 2-(2-((7-(2-(aminomethyl)pyridin-4-yl)benzofuran-5-yl)methoxy)-4-methylphenyl)acetic Acid (271e)

Compound 271e was prepared according to the procedure reported in step-6 of scheme-1, from ethyl 2-(2-((7-(2-(aminomethyl)pyridin-4-yl)benzofuran-5-yl)methoxy)-4-methylphenyl)acetate (271d) (185 mg, 0.430 mmol) in THF/MeOH (5 mL, each) using a solution of lithium hydroxide hydrate (41 mg, 1.719 mmol) in water (2 mL). This gave after workup and purification by reverse phase column chromatography [C18 column, 50 g, eluting with water (containing 0.1% HCl)/acetonitrile (1:0 to 0:1)] 2-(2-((7-(2-(aminomethyl)pyridin-4-yl)benzofuran-5-yl)methoxy)-4-methylphenyl)acetic acid (271e) (84 mg, 49% yield) hydrochloride salt as a light yellow solid; $^1$HNMR (300 MHz, DMSO-$d_6$) δ 8.79 (d, J=5.3 Hz, 1H), 8.53 (s, 3H), 8.18 (d, J=2.2 Hz, 1H), 8.11 (s, 1H), 8.01 (s, 1H), 7.88 (d, J=1.6 Hz, 1H), 7.83 (s, 1H), 7.12 (d, J=2.2 Hz, 1H), 7.10 (d, J=7.5 Hz, 1H), 6.95 (d, J=1.6 Hz, 1H), 6.73 (dd, J=7.4, 1.5 Hz, 1H), 5.27 (s, 2H), 4.32 (d, J=4.8 Hz, 2H), 3.55 (s, 2H), 2.29 (s, 3H); MS (ES+): 403.1 (M+1), (ES−): 401.1 (M−1); Analysis Calculated for $C_{24}H_{22}N_2O_4 \cdot 1.75HCl \cdot 1.75H_2O$: C, 57.91; H, 5.52; Cl, 12.46; N, 5.63; Found: C, 57.83; H, 5.28; Cl, 12.81; N, 5.70.

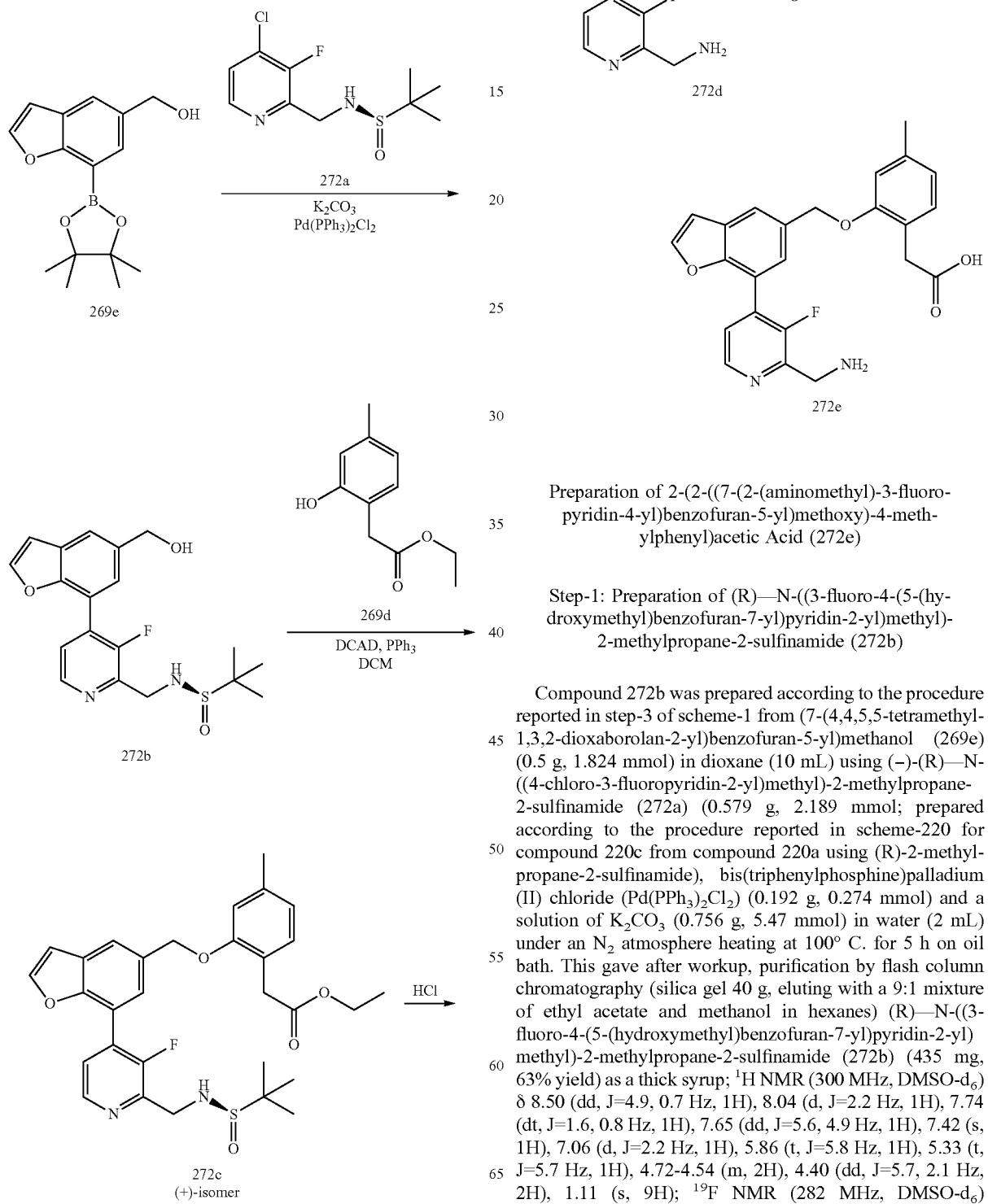

Preparation of 2-(2-((7-(2-(aminomethyl)-3-fluoropyridin-4-yl)benzofuran-5-yl)methoxy)-4-methylphenyl)acetic Acid (272e)

Step-1: Preparation of (R)—N-((3-fluoro-4-(5-(hydroxymethyl)benzofuran-7-yl)pyridin-2-yl)methyl)-2-methylpropane-2-sulfinamide (272b)

Compound 272b was prepared according to the procedure reported in step-3 of scheme-1 from (7-(4,4,5,5-tetramethyl-1,3,2-dioxaborolan-2-yl)benzofuran-5-yl)methanol (269e) (0.5 g, 1.824 mmol) in dioxane (10 mL) using (−)-(R)—N-((4-chloro-3-fluoropyridin-2-yl)methyl)-2-methylpropane-2-sulfinamide (272a) (0.579 g, 2.189 mmol; prepared according to the procedure reported in scheme-220 for compound 220c from compound 220a using (R)-2-methylpropane-2-sulfinamide), bis(triphenylphosphine)palladium (II) chloride (Pd(PPh$_3$)$_2$Cl$_2$) (0.192 g, 0.274 mmol) and a solution of K$_2$CO$_3$ (0.756 g, 5.47 mmol) in water (2 mL) under an N$_2$ atmosphere heating at 100° C. for 5 h on oil bath. This gave after workup, purification by flash column chromatography (silica gel 40 g, eluting with a 9:1 mixture of ethyl acetate and methanol in hexanes) (R)—N-((3-fluoro-4-(5-(hydroxymethyl)benzofuran-7-yl)pyridin-2-yl)methyl)-2-methylpropane-2-sulfinamide (272b) (435 mg, 63% yield) as a thick syrup; $^1$H NMR (300 MHz, DMSO-d$_6$) δ 8.50 (dd, J=4.9, 0.7 Hz, 1H), 8.04 (d, J=2.2 Hz, 1H), 7.74 (dt, J=1.6, 0.8 Hz, 1H), 7.65 (dd, J=5.6, 4.9 Hz, 1H), 7.42 (s, 1H), 7.06 (d, J=2.2 Hz, 1H), 5.86 (t, J=5.8 Hz, 1H), 5.33 (t, J=5.7 Hz, 1H), 4.72-4.54 (m, 2H), 4.40 (dd, J=5.7, 2.1 Hz, 2H), 1.11 (s, 9H); $^{19}$F NMR (282 MHz, DMSO-d$_6$) δ −128.15; MS (ES+): 377.2 (M+1).

Step-2: Preparation of (+)-(R)-ethyl 2-(2-((7-(2-((1,1-dimethylethylsulfinamido)methyl)-3-fluoropyridin-4-yl)benzofuran-5-yl)methoxy)-4-methylphenyl)acetate (272c)

Compound 272c was prepared according to the procedure reported in step-2 of scheme-23 from (R)—N-((3-fluoro-4-(5-(hydroxymethyl)benzofuran-7-yl)pyridin-2-yl)methyl)-2-methylpropane-2-sulfinamide (272b) (430 mg, 1.142 mmol) in DCM (20 mL) using triphenylphosphine (374 mg, 1.428 mmol), ethyl 2-(2-hydroxy-4-methylphenyl)acetate (269d) (277 mg, 1.428 mmol) and a solution of (E)-bis(4-chlorobenzyl) diazene-1,2-dicarboxylate (DCAD, 587 mg, 1.599 mmol) in DCM (10 mL). This gave after workup and purification by flash column chromatography (silica gel, 25 g, eluting with ethyl acetate in hexanes from 0-50%) (+)-(R)-ethyl 2-(2-((7-(2-((1,1-dimethylethylsulfinamido)methyl)-3-fluoropyridin-4-yl)benzofuran-5-yl)methoxy)-4-methylphenyl)acetate (272c) (300 mg, 48% yield) as a colorless oil; $^1$H NMR (300 MHz, DMSO-$d_6$) δ 8.52 (d, J=4.9 Hz, 1H), 8.09 (d, J=2.2 Hz, 1H), 7.85 (d, J=1.6 Hz, 1H), 7.67 (t, J=5.2 Hz, 1H), 7.52 (s, 1H), 7.12-7.05 (m, 2H), 6.97 (s, 1H), 6.73 (d, J=7.5 Hz, 1H), 5.86 (t, J=5.8 Hz, 1H), 5.22 (s, 2H), 4.48-4.35 (m, 2H), 3.89 (q, J=7.1 Hz, 2H), 3.56 (s, 2H), 2.30 (s, 3H), 1.11 (s, 9H), 0.96 (t, J=7.1 Hz, 3H); $^{19}$F NMR (282 MHz, DMSO-$d_6$) δ−127.99; MS (ES+): 553.2 (M+1); Optical rotation [t]D=+17.14 (c=0.11, MeOH).

Step-3: Preparation of Ethyl 2-(2-((7-(2-(aminomethyl)-3-fluoropyridin-4-yl)benzofuran-5-yl)methoxy)-4-methylphenyl)acetate (272d)

To a stirred solution of (+)-(R)-ethyl 2-(2-((7-(2-((1,1-dimethylethylsulfinamido)methyl)-3-fluoropyridin-4-yl)benzofuran-5-yl)methoxy)-4-methylphenyl)acetate (272c) (300 mg, 0.543 mmol) in THF (5 mL) was added 3 N aqueous HCl (0.543 mL, 1.628 mmol) at room temperature and stirred for 2 h. Reaction was concentrated in vacuum to afford ethyl 2-(2-((7-(2-(aminomethyl)-3-fluoropyridin-4-yl)benzofuran-5-yl)methoxy)-4-methylphenyl)acetate (272d) (263 mg, 0.543 mmol, 100% yield) HCl salt as a white solid which was used as such without further purification; MS (ES+): 449.2 (M+1).

Step-4: Preparation of 2-(2-((7-(2-(aminomethyl)-3-fluoropyridin-4-yl)benzofuran-5-yl)methoxy)-4-methylphenyl)acetic Acid (272e)

Compound 272e was prepared according to the procedure reported in step-6 of scheme-1, from ethyl 2-(2-((7-(2-(aminomethyl)-3-fluoropyridin-4-yl)benzofuran-5-yl)methoxy)-4-methylphenyl)acetate (272d) (260 mg, 0.536 mmol) in THF/MeOH (5 mL, each) using a solution of lithium hydroxide hydrate (51 mg, 2.145 mmol) in water (2 mL). This gave after workup and purification by reverse phase column chromatography [C18 column, 50 g, eluting with water (containing 0.1% HCl)/acetonitrile (1:0 to 0:1)] 2-(2-((7-(2-(aminomethyl)-3-fluoropyridin-4-yl)benzofuran-5-yl)methoxy)-4-methylphenyl)acetic acid (272e) (200 mg, 89%) hydrochloride salt as a white solid; $^1$H NMR (300 MHz, DMSO-$d_6$) δ 8.63 (d, J=5.0 Hz, 1H), 8.58 (t, J=6.1 Hz, 3H), 8.12 (d, J=2.2 Hz, 1H), 7.91 (d, J=1.6 Hz, 1H), 7.81 (d, J=5.3 Hz, 1H), 7.60 (s, 1H), 7.11 (d, J=2.2 Hz, 1H), 7.08 (d, J=7.5 Hz, 1H), 6.95 (d, J=1.5 Hz, 1H), 6.73 (d, J=8.3 Hz, 1H), 5.25 (s, 2H), 4.44-4.33 (m, 2H), 3.52 (s, 2H), 2.29 (s, 3H); $^{19}$F NMR (282 MHz, DMSO-$d_6$) δ−128.36; MS (ES+): 421.10 (M+1), (ES−): 419.10 (M−1); Analysis calculated for $C_{24}H_{21}FN_2O_4$·1.0 HCl·1.5 $H_2O$: C, 59.57; H, 5.21; N, 5.79; Cl, 7.33; found: C, 59.41; H, 5.09; N, 5.77; Cl, 7.54.

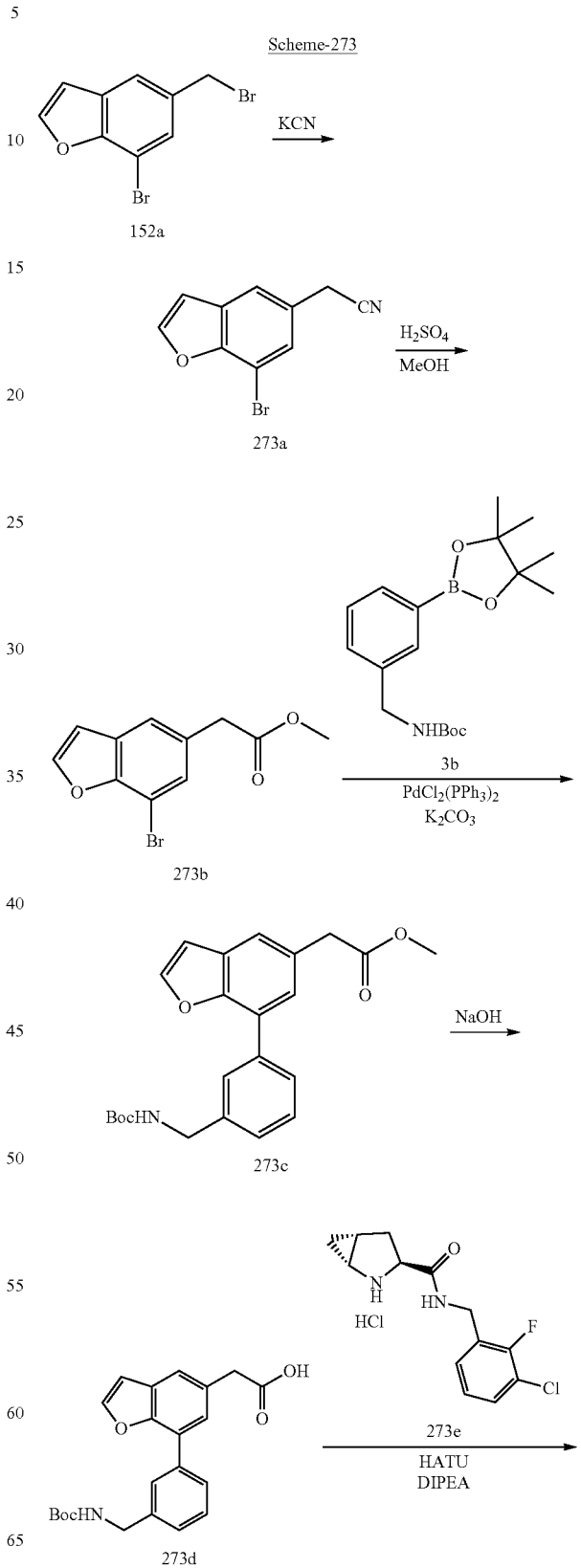

Scheme-273

-continued

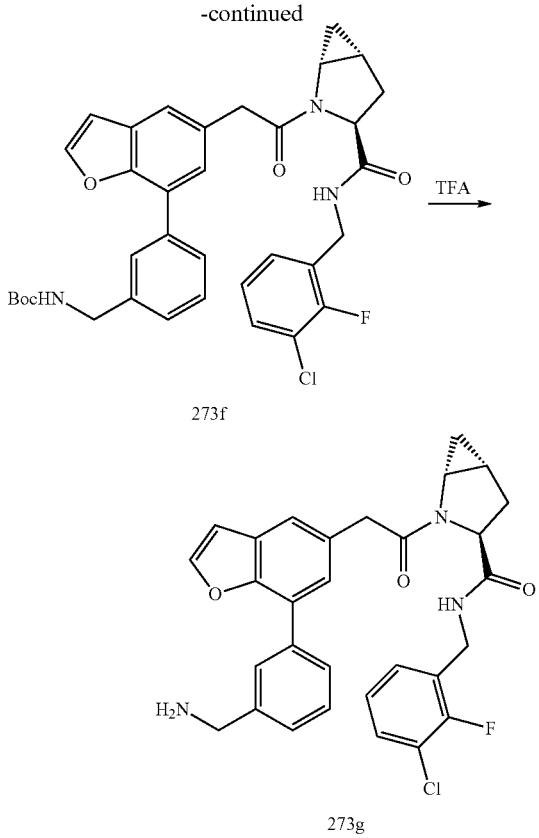

273f

273g

Preparation of (1R,3S,5R)-2-(2-(7-(3-(aminomethyl)phenyl)benzofuran-5-yl)acetyl)-N-(3-chloro-2-fluorobenzyl)-2-azabicyclo[3.1.0]hexane-3-carboxamide (273g)

Step-1: Preparation of 2-(7-bromobenzofuran-5-yl)acetonitrile (273a)

To a stirred solution of 7-bromo-5-(bromomethyl)benzofuran (152a) (2 g, 6.90 mmol) in acetonitrile (40 mL) was added potassium cyanide (0.431 g, 6.62 mmol) and stirred at room temperature for 48 h. Reaction was diluted with brine and extracted with ethyl acetate. The ethyl acetate layer was washed with brine, dried and concentrated. The crude residue was purified by flash column chromatography to afford pure 2-(7-bromobenzofuran-5-yl)acetonitrile (273a) (845 mg, 52% yield) as a white solid; $^1$H NMR (300 MHz, DMSO-$d_6$) δ 8.16 (d, J=2.2 Hz, 1H), 7.68 (dt, J=1.6, 0.7 Hz, 1H), 7.56 (dd, J=1.7, 0.5 Hz, 1H), 7.13 (d, J=2.2 Hz, 1H), 4.14 (d, J=0.7 Hz, 2H).

Step-2: Preparation of methyl 2-(7-bromobenzofuran-5-yl)acetate (273b)

To a stirred a solution of 2-(7-bromobenzofuran-5-yl)acetonitrile (273a) (800 mg, 3.39 mmol) in methanol (15 mL) was added conc. sulfuric acid (1.806 mL, 33.9 mmol) and heated at reflux for 12 h. The reaction was cooled to room temperature and concentrated to remove methanol. The residue was taken in ethyl acetate (200 mL), washed with water, brine, dried and concentrated in vacuum. The crude residue was purified by flash column chromatography to afford methyl 2-(7-bromobenzofuran-5-yl)acetate (273b) (410 mg, 45% yield) as a light brown syrup; $^1$H NMR (300 MHz, DMSO-$d_6$) δ 8.11 (d, J=2.2 Hz, 1H), 7.56 (d, J=1.5 Hz, 1H), 7.48 (d, J=1.5 Hz, 1H), 7.07 (d, J=2.2 Hz, 1H), 3.80 (s, 2H), 3.62 (s, 3H).

Step-3: Preparation of methyl 2-(7-(3-(((tert-butoxycarbonyl)amino)methyl)phenyl)benzofuran-5-yl)acetate (273c)

Compound 273c was prepared according to the procedure reported in step-3 of scheme-1 from methyl 2-(7-bromobenzofuran-5-yl)acetate (273b) (400 mg, 1.486 mmol) in dioxane (10 mL) using tert-butyl 3-(4,4,5,5-tetramethyl-1,3,2-dioxaborolan-2-yl)benzylcarbamate (3b) (594 mg, 1.784 mmol), bis(triphenylphosphine)palladium(II) chloride (Pd(PPh$_3$)$_2$Cl$_2$) (157 mg, 0.223 mmol) and a solution of K$_2$CO$_3$ (616 mg, 4.46 mmol) in water (2 mL) under an N$_2$ atmosphere heating at 100° C. for 7 h on oil bath. This gave after workup and purification by flash column chromatography (silica gel, 40 g, eluting with ethyl acetate in hexanes from 0-100%) methyl 2-(7-(3-(((tert-butoxycarbonyl)amino)methyl)phenyl)benzofuran-5-yl)acetate (273c) (470 mg, 80% yield) as a colorless syrup; $^1$H NMR (300 MHz, DMSO-$d_6$) δ 8.05 (d, J=2.2 Hz, 1H), 7.77-7.67 (m, 2H), 7.55 (d, J=1.7 Hz, 1H), 7.53-7.43 (m, 2H), 7.38 (d, J=1.7 Hz, 1H), 7.29 (d, J=7.6 Hz, 1H), 7.02 (d, J=2.2 Hz, 1H), 4.22 (d, J=6.3 Hz, 2H), 3.84 (s, 2H), 3.63 (s, 3H), 1.40 (s, 9H).

Step-4: Preparation of 2-(7-(3-(((tert-butoxycarbonyl)amino)methyl)phenyl)benzofuran-5-yl)acetic Acid (273d)

Compound 273d was prepared according to the procedure reported in step-4 of scheme-4 from methyl 2-(7-(3-(((tert-butoxycarbonyl)amino)methyl)phenyl)benzofuran-5-yl)acetate (273c) (460 mg, 1.163 mmol) in THF (5 mL) MeOH (5 mL) using a solution of sodium hydroxide (140 mg, 3.49 mmol) in water (2 mL). This gave after workup and purification by flash column chromatography (silica gel, 25 g, eluting with a 9:1 mixture of ethyl acetate and methanol in hexanes) 2-(7-(3-(((tert-butoxycarbonyl)amino)methyl)phenyl)benzofuran-5-yl)acetic acid (273d) (340 mg, 77% yield) as a thick syrup; $^1$H NMR (300 MHz, DMSO-$d_6$) δ 12.37 (s, 1H), 8.04 (d, J=2.2 Hz, 1H), 7.71 (dt, J=9.6, 1.8 Hz, 2H), 7.54 (d, J=1.7 Hz, 1H), 7.48 (td, J=7.6, 7.1, 3.6 Hz, 2H), 7.37 (d, J=1.7 Hz, 1H), 7.28 (d, J=7.6 Hz, 1H), 7.02 (d, J=2.2 Hz, 1H), 4.22 (d, J=6.2 Hz, 2H), 3.72 (s, 2H), 1.40 (s, 9H).

Step-5: Preparation of tert-butyl 3-(5-(2-((1R,3S,5R)-3-((3-chloro-2-fluorobenzyl)carbamoyl)-2-azabicyclo[3.1.0]hexan-2-yl)-2-oxoethyl)benzofuran-7-yl)benzylcarbamate (273f)

Compound 273f was prepared according to the procedure reported in step-4 of scheme-1 from 2-(7-(3-(((tert-butoxycarbonyl)amino)methyl)phenyl)benzofuran-5-yl)acetic acid (273d) (200 mg, 0.524 mmol) in DMF (4 mL) using (1R,3S,5R)—N-(3-chloro-2-fluorobenzyl)-2-azabicyclo[3.1.0]hexane-3-carboxamide hydrochloride (273e) (200 mg, 0.655 mmol; prepared according to the procedure reported by Wiles, Jason Allan et al; in PCT Int. Appl., 2017035349, 2 Mar. 2017), DIPEA (0.365 mL, 2.097 mmol) and HATU (299 mg, 0.787 mmol). This gave after workup and purification by flash column chromatography [silica (12 g), eluting with 0 to 100% EtOAc/MeOH=9:1 in hexane] tert-butyl 3-(5-(2-((1R,3S,5R)-3-((3-chloro-2-fluorobenzyl)carbamoyl)-2-azabicyclo[3.1.0]hexan-2-yl)-2-oxoethyl)benzofuran-7-yl)benzylcarbamate (273f) (410 mg) as a clear syrup. MS (ES+): 532.2 (M-Boc), (ES−): 631.2 (M−1).

Step-6: Preparation of (1R,3S,5R)-2-(2-(7-(3-(aminomethyl)phenyl)benzofuran-5-yl)acetyl)-N-(3-chloro-2-fluorobenzyl)-2-azabicyclo[3.1.0]hexane-3-carboxamide (273g)

Compound 273g was prepared according to the procedure reported in step-5 of scheme-1 from tert-butyl 3-(5-(2-((1R,3S,5R)-3-((3-chloro-2-fluorobenzyl)carbamoyl)-2-azabicyclo[3.1.0]hexan-2-yl)-2-oxoethyl)benzofuran-7-yl)benzylcarbamate (273f) (410 mg, 0.649 mmol) in DCM (10 mL) using TFA (0.5 mL, 6.49 mmol). This gave after workup and purification by reverse phase column chromatography [C18 (50 g), eluting with ACN in water (containing 0.1% HCl) from 0-100%] (1R,3S,5R)-2-(2-(7-(3-(aminomethyl)phenyl)benzofuran-5-yl)acetyl)-N-(3-chloro-2-fluorobenzyl)-2-azabicyclo[3.1.0]hexane-3-carboxamide (273g) (210 mg, 61% yield) as a white solid; $^1$H NMR (300 MHz, DMSO-$d_6$) δ 8.48 (t, J=6.0 Hz, 1H), 8.38 (s, 3H), 8.06 (d, J=2.2 Hz, 1H), 7.97 (s, 1H), 7.88 (dt, J=7.2, 1.8 Hz, 1H), 7.61-7.56 (m, 2H), 7.56-7.51 (m, 1H), 7.47 (d, J=4.8 Hz, 1H), 7.45-7.39 (m, 1H), 7.28 (t, J=7.6 Hz, 1H), 7.10 (td, J=7.9, 1.1 Hz, 1H), 7.03 (d, J=2.2 Hz, 1H), 4.34 (q, J=8.1, 7.0 Hz, 2H), 4.23 (dd, J=9.1, 4.9 Hz, 1H), 4.12 (s, 2H), 4.07-3.92 (m, 2H), 3.71-3.62 (m, 1H), 2.30-2.01 (m, 2H), 1.77 (p, J=6.8 Hz, 1H), 0.93 (dt, J=9.1, 5.3 Hz, 1H), 0.50 (dd, J=5.2, 2.4 Hz, 1H); $^{19}$F NMR (282 MHz, DMSO-$d_6$) δ−121.77; MS (ES+): 532.10, 534.10 (M+1), (ES−): 530.20, 532.20 (M−1); Analysis calculated for $C_{30}H_{27}ClFN_3O.HCl.1.25H_2O$: C, 60.97; H, 5.20; Cl, 12.00; N, 7.11; Found: C, 60.91; H, 5.01; Cl, 11.81; N, 7.04.

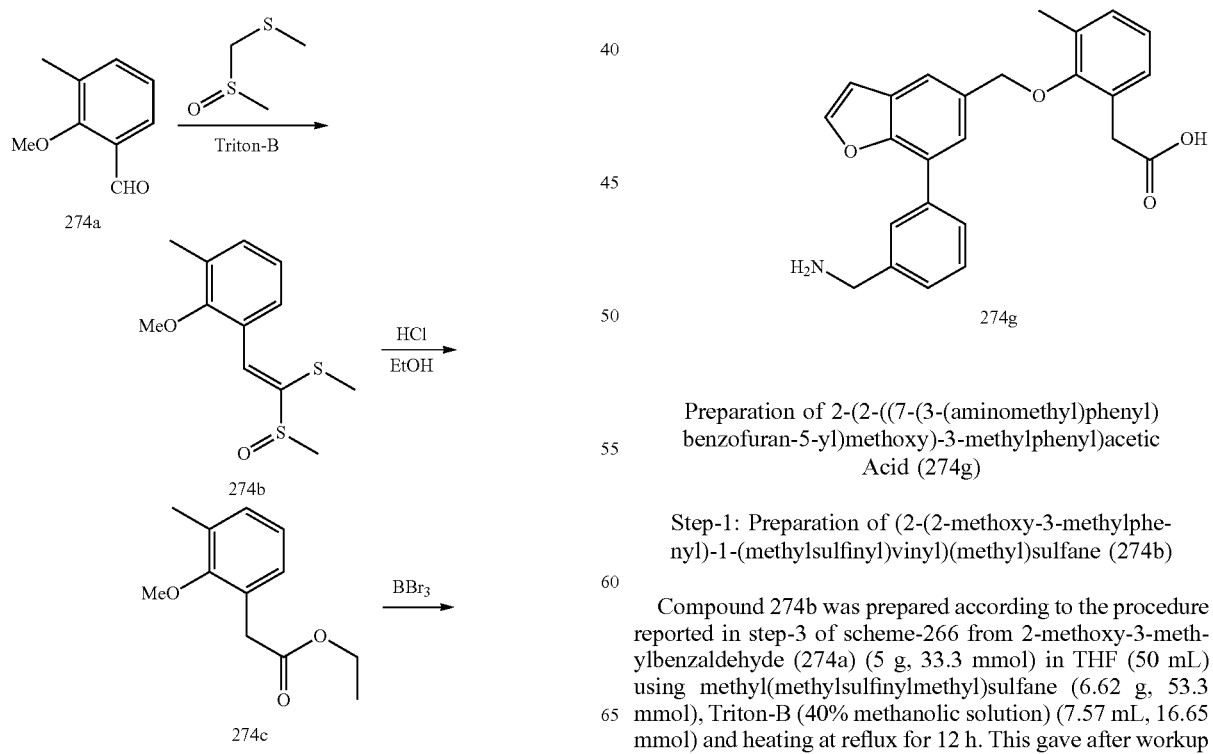

Scheme-274

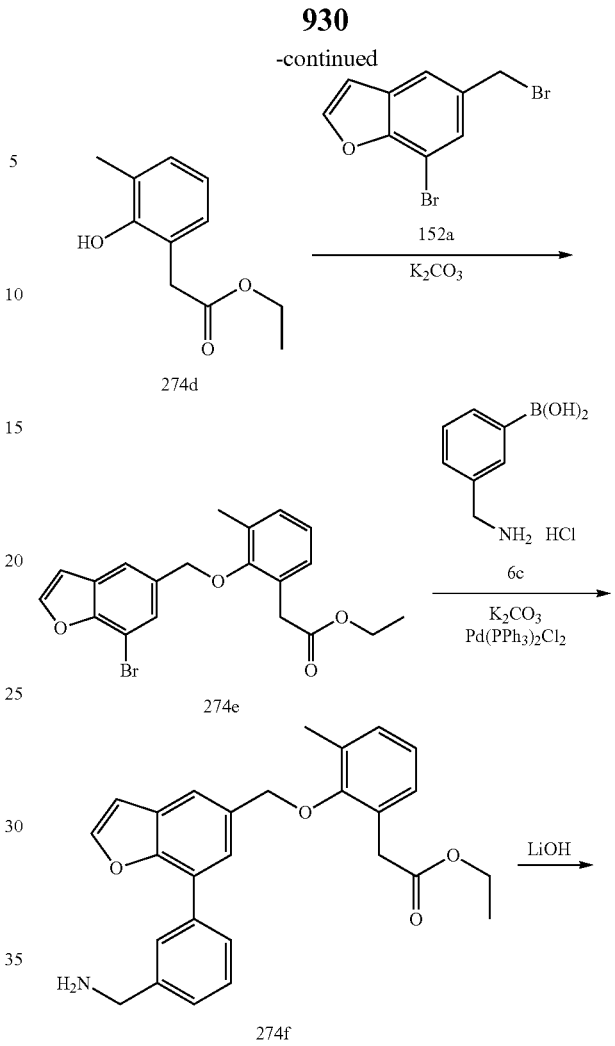

Preparation of 2-(2-((7-(3-(aminomethyl)phenyl)benzofuran-5-yl)methoxy)-3-methylphenyl)acetic Acid (274g)

Step-1: Preparation of (2-(2-methoxy-3-methylphenyl)-1-(methylsulfinyl)vinyl)(methyl)sulfane (274b)

Compound 274b was prepared according to the procedure reported in step-3 of scheme-266 from 2-methoxy-3-methylbenzaldehyde (274a) (5 g, 33.3 mmol) in THF (50 mL) using methyl(methylsulfinylmethyl)sulfane (6.62 g, 53.3 mmol), Triton-B (40% methanolic solution) (7.57 mL, 16.65 mmol) and heating at reflux for 12 h. This gave after workup (2-(2-methoxy-3-methylphenyl)-1-(methylsulfinyl)vinyl)

(methyl)sulfane (274b) (8.54 g, 100% yield) as a light brow syrup; MS (ES+): 257.0 (M+1), 279.0 (M+Na).

Step-2: Preparation of Ethyl 2-(2-methoxy-3-methylphenyl)acetate (274c)

Compound 274c was prepared according to the procedure reported in step-4 of scheme-266 from (2-(2-methoxy-3-methylphenyl)-1-(methylsulfinyl)vinyl)(methyl)sulfane (274b) (8.54 g, 33.3 mmol) in ethanol (100 mL) using conc HCl (13.88 mL, 167 mmol) and heating at reflux for 12 h. This gave after workup and purification by flash column chromatography (silica gel) ethyl 2-(2-methoxy-3-methylphenyl)acetate (274c) (2.65 g, 38% yield) as a thick syrup; $^1$H NMR (300 MHz, DMSO-$d_6$) δ 7.16-7.03 (m, 2H), 6.97 (t, J=7.5 Hz, 1H), 4.08 (q, J=7.1 Hz, 2H), 3.63 (s, 3H), 3.62 (s, 2H), 2.23 (s, 3H), 1.18 (t, J=7.1 Hz, 3H); MS (ES+): 231.1 (M+Na).

Step-3: Preparation of Ethyl 2-(2-hydroxy-3-methylphenyl)acetate (274d)

Compound 274d was prepared according to the procedure reported in step-5 of scheme-257 from ethyl 2-(2-methoxy-3-methylphenyl)acetate (274c) (2.6 g, 12.48 mmol) in dichloromethane (30 mL) using boron tribromide (4.72 mL, 49.9 mmol). This gave after workup ethyl 2-(2-hydroxy-3-methylphenyl)acetate (274d) (0.6 g, 25% yield) as clear syrup; $^1$H NMR (300 MHz, DMSO-$d_6$) δ 8.41 (s, 1H), 7.01-6.90 (m, 2H), 6.68 (t, J=7.4 Hz, 1H), 4.06 (q, J=7.1 Hz, 2H), 3.57 (s, 2H), 2.16 (s, 3H), 1.18 (t, J=7.1 Hz, 3H).

Step-4: Preparation of Ethyl 2-(2-((7-bromobenzofuran-5-yl)methoxy)-3-methylphenyl)acetate (274e)

Compound 274e was prepared according to the procedure reported in step-2 of scheme-152 from 7-bromo-5-(bromomethyl)benzofuran (152a) (0.411 g, 1.416 mmol) using ethyl 2-(2-hydroxy-3-methylphenyl)acetate (274d) (0.275 g, 1.416 mmol), $K_2CO_3$ (0.587 g, 4.25 mmol) in DMF (5 mL) and stirring at room temperature for 2 h. This gave after workup and purification by flash column chromatography (SiO$_2$, 40 g, eluting with EtOAc in hexane) ethyl 2-(2-((7-bromobenzofuran-5-yl)methoxy)-3-methylphenyl)acetate (274e) (465 mg, 81% yield) as a white solid; $^1$H NMR (300 MHz, DMSO-$d_6$) δ 8.16 (d, J=2.2 Hz, 1H), 7.77 (d, J=1.5 Hz, 1H), 7.65 (d, J=1.5 Hz, 1H), 7.22-7.08 (m, 3H), 7.03 (t, J=7.4 Hz, 1H), 4.87 (s, 2H), 4.01 (q, J=7.1 Hz, 2H), 3.66 (s, 2H), 2.30 (s, 3H), 1.10 (t, J=7.1 Hz, 3H); MS (ES+): 403.00, 405.00 (M, M+2), 425.0, 427.0 (M+Na).

Step-5: Preparation of Ethyl 2-(2-((7-(3-(aminomethyl)phenyl)benzofuran-5-yl)methoxy)-3-methylphenyl)acetate (274f)

Compound 274f was prepared according to the procedure reported in step-3 of scheme-1 from ethyl 2-(2-((7-bromobenzofuran-5-yl)methoxy)-3-methylphenyl)acetate (274e) (450 mg, 1.116 mmol) in dioxane (10 mL) using (3-(aminomethyl)phenyl)boronic acid hydrochloride (6c) (335 mg, 1.785 mmol), bis(triphenylphosphine)palladium (II) chloride (Pd(PPh$_3$)$_2$Cl$_2$) (117 mg, 0.167 mmol) and a solution of $K_2CO_3$ (463 mg, 3.35 mmol) in water (3 mL) under an $N_2$ atmosphere heating at 100° C. for 6 h on oil bath. This gave after workup, purification by flash column chromatography (silica gel 40 g, eluting with DMA80 in DCM from 0-50%] followed by purification by reverse phase column chromatography [C18 (100 g), eluting with ACN in water (containing 0.1% HCl) from 0-100%] ethyl 2-(2-((7-(3-(aminomethyl)phenyl)benzofuran-5-yl)methoxy)-3-methylphenyl)acetate (274f) (242 mg, 51% yield) as a colorless syrup; $^1$H NMR (300 MHz, DMSO-$d_6$) δ 8.10 (d, J=2.2 Hz, 1H), 7.80 (d, J=1.8 Hz, 1H), 7.75 (d, J=1.6 Hz, 1H), 7.70 (dt, J=7.5, 1.6 Hz, 1H), 7.58 (d, J=1.7 Hz, 1H), 7.47 (t, J=7.6 Hz, 1H), 7.43-7.38 (m, 1H), 7.20-7.16 (m, 1H), 7.15-7.10 (m, 1H), 7.08 (d, J=2.2 Hz, 1H), 7.03 (t, J=7.5 Hz, 1H), 4.94 (s, 2H), 3.98 (q, J=7.1 Hz, 2H), 3.82 (s, 2H), 3.68 (s, 2H), 2.33 (s, 3H), 1.05 (t, J=7.1 Hz, 3H); MS (ES+): 430.2 (M+1).

Step 6: Preparation of 2-(2-((7-(3-(aminomethyl)phenyl)benzofuran-5-yl)methoxy)-3-methylphenyl)acetic Acid (274g)

Compound 274g was prepared according to the procedure reported in step-6 of scheme-1 from ethyl 2-(2-((7-(3-(aminomethyl)phenyl)benzofuran-5-yl)methoxy)-3-methylphenyl)acetate (274f) (245 mg, 0.570 mmol) in MeOH (5 mL), THF (5 mL) using a solution of lithium hydroxide (55 mg, 2.282 mmol) in water (2 mL). This gave after workup and purification by reverse phase column [C18 (50g), eluting with ACN in water (containing 0.1% HCl) from 0-100%] 2-(2-((7-(3-(aminomethyl)phenyl)benzofuran-5-yl)methoxy)-3-methylphenyl)acetic acid (274g) (225 mg, 90% yield) HCl salt as a white solid. $^1$H NMR (300 MHz, DMSO-$d_6$) δ 8.12 (d, J=2.2 Hz, 1H), 8.00 (d, J=2.2 Hz, 1H), 7.92 (dt, J=6.6, 2.2 Hz, 1H), 7.81 (d, J=1.6 Hz, 1H), 7.68 (d, J=1.6 Hz, 1H), 7.59 (d, J=6.5 Hz, 2H), 7.19-7.11 (m, 2H), 7.10 (d, J=2.2 Hz, 1H), 7.02 (t, J=7.5 Hz, 1H), 4.94 (s, 2H), 4.14 (s, 2H), 3.64 (s, 2H), 2.32 (s, 3H); MS (ES+): 402.20 (M+1), (ES−): 400.10 (M−1); Analysis calculated for $C_{25}H_{23}NO_4$·HCl; C, 68.57; H, 5.52; Cl, 8.10; N, 3.20; Found C, 68.40; H, 5.51; Cl, 7.97; N, 3.25.

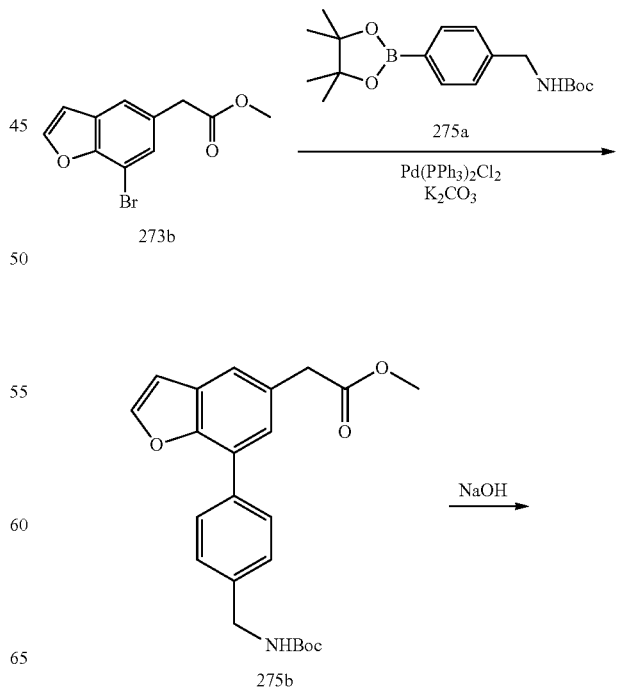

Scheme-275

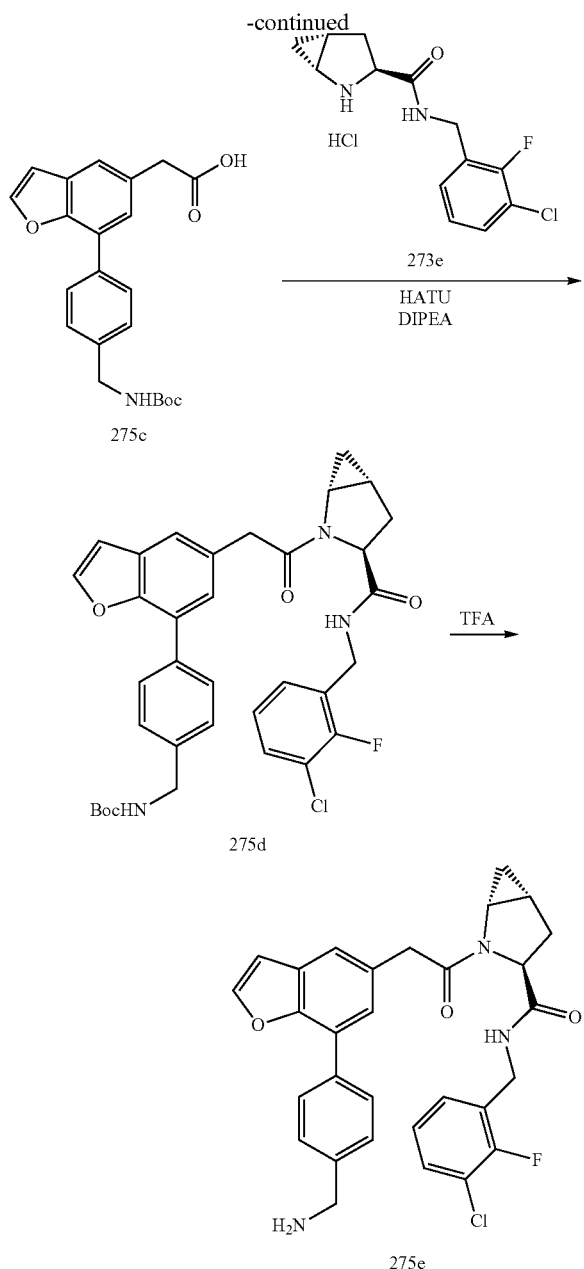

Preparation of (1R,3S,5R)-2-(2-(7-(4-(aminomethyl)phenyl)benzofuran-5-yl)acetyl)-N-(3-chloro-2-fluorobenzyl)-2-azabicyclo[3.1.0]hexane-3-carboxamide (275e)

Step-1: Preparation of methyl 2-(7-(4-(((tert-butoxycarbonyl)amino)methyl)phenyl)benzofuran-5-yl)acetate (275b)

Compound 275b was prepared according to the procedure reported in step-3 of scheme-1 from methyl 2-(7-bromobenzofuran-5-yl)acetate (273b) (200 mg, 0.743 mmol) in dioxane (10 mL) using tert-butyl 4-(4,4,5,5-tetramethyl-1,3,2-dioxaborolan-2-yl)benzylcarbamate (275a) (297 mg, 0.892 mmol; CAS #330794-35-9), bis(triphenylphosphine)palladium(II) chloride (Pd(PPh$_3$)$_2$Cl$_2$) (78 mg, 0.111 mmol) and a solution of K$_2$CO$_3$ (308 mg, 2.230 mmol) in water (2 mL) under an N$_2$ atmosphere heating at 100° C. for 7 h on oil bath. This gave after workup and purification by flash column chromatography (silica gel, 40 g, eluting with ethyl acetate in hexanes from 0-100%) methyl 2-(7-(4-(((tert-butoxycarbonyl)amino)methyl)phenyl)benzofuran-5-yl)acetate (275b) (140 mg, 48% yield) as a colorless syrup; MS (ES+): 418.1 (M+Na).

Step-2: Preparation of 2-(7-(4-(((tert-butoxycarbonyl)amino)methyl)phenyl)benzofuran-5-yl)acetic Acid (275c)

Compound 275c was prepared according to the procedure reported in step-4 of scheme-4 from methyl 2-(7-(4-(((tert-butoxycarbonyl)amino)methyl)phenyl)benzofuran-5-yl)acetate (275b) (140 mg, 0.354 mmol) in THF (5 mL) MeOH (5 mL) using a solution of sodium hydroxide (42 mg, 1.062 mmol) in water (2 mL). This gave after workup 2-(7-(4-(((tert-butoxycarbonyl)amino)methyl)phenyl)benzofuran-5-yl)acetic acid (275c) (132 mg, 98% yield) as a thick syrup; MS (ES+): 404.1 (M+Na), (ES−) 380.1 (M−1).

Step-3: Preparation of tert-butyl 4-(5-(2-((1R,3S,5R)-3-((3-chloro-2-fluorobenzyl)carbamoyl)-2-azabicyclo[3.1.0]hexan-2-yl)-2-oxoethyl)benzofuran-7-yl)benzylcarbamate (275d)

Compound 275d was prepared according to the procedure reported in step-4 of scheme-1 from 2-(7-(4-(((tert-butoxycarbonyl)amino)methyl)phenyl)benzofuran-5-yl)acetic acid (275c) (132 mg, 0.346 mmol) in DMF (4 mL) using (1R,3S,5R)—N-(3-chloro-2-fluorobenzyl)-2-azabicyclo[3.1.0]hexane-3-carboxamide hydrochloride (273e) (132 mg, 0.433 mmol), DIPEA (0.241 mL, 1.384 mmol) and HATU (197 mg, 0.519 mmol). This gave after workup and purification by flash column chromatography [silica (12 g), eluting with 0 to 100% EtOAc/MeOH=9:1 in hexane] tert-butyl 4-(5-(2-((1R,3S,5R)-3-((3-chloro-2-fluorobenzyl)carbamoyl)-2-azabicyclo[3.1.0]hexan-2-yl)-2-oxoethyl)benzofuran-7-yl)benzylcarbamate (275d) (160 mg, 73% yield) as a clear syrup; MS (ES+): 654.2, 655.2 (M+Na).

Step-4: Preparation of (1R,3S,5R)-2-(2-(7-(4-(aminomethyl)phenyl)benzofuran-5-yl)acetyl)-N-(3-chloro-2-fluorobenzyl)-2-azabicyclo[3.1.0]hexane-3-carboxamide (275e)

Compound 275e was prepared according to the procedure reported in step-5 of scheme-1 from tert-butyl 4-(5-(2-((1R,3S,5R)-3-((3-chloro-2-fluorobenzyl)carbamoyl)-2-azabicyclo[3.1.0]hexan-2-yl)-2-oxoethyl)benzofuran-7-yl)benzylcarbamate (275d) (150 mg, 0.237 mmol) in DCM (5 mL) using TFA (0.183 mL, 2.375 mmol). This gave after workup and purification by reverse phase column chromatography [C18 (50 g), eluting with ACN in water (containing 0.1% HCl) from 0-100%] (1R,3S,5R)-2-(2-(7-(4-(aminomethyl)phenyl)benzofuran-5-yl)acetyl)-N-(3-chloro-2-fluorobenzyl)-2-azabicyclo[3.1.0]hexane-3-carboxamide (275e) (65 mg, 0.122 mmol, 51.4% yield) HCl salt as a white solid; $^1$H NMR (300 MHz, DMSO-d$_6$) δ 8.46 (t, J=6.0 Hz, 1H), 8.36 (s, 3H), 8.05 (d, J=2.2 Hz, 1H), 7.90 (d, J=8.1 Hz, 2H), 7.62 (d, J=8.1 Hz, 2H), 7.57 (d, J=1.6 Hz, 1H), 7.47 (d, J=1.7 Hz, 1H), 7.43 (d, J=7.5 Hz, 1H), 7.29 (t, J=7.2 Hz, 1H), 7.10 (t, J=7.9 Hz, 1H), 7.01 (d, J=2.2 Hz, 1H), 4.37-4.28 (m, 2H), 4.23 (dd, J=9.1, 5.0 Hz, 1H), 4.10 (s, 2H), 4.00 (d, J=9.1 Hz, 2H), 3.73-3.60 (m, 1H), 2.30-2.15 (m, 1H), 2.09 (dt, J=12.9, 5.9 Hz, 1H), 1.77 (s, 1H), 0.92 (dt, J=9.3, 5.3 Hz, 1H), 0.50 (s, 1H); $^{19}$F NMR (282 MHz, DMSO-d$_6$) δ −121.79; MS (ES+): 532.3, 533.0, (ES−): 530.2, 532.0 (M−1); Analysis Calculated for $C_{30}H_{27}ClFN_3O_3 \cdot HCl \cdot 2.25H_2O$: C, 59.17; H, 5.38; Cl, 11.64; N, 6.90; Found; C, 58.96; H, 4.99; Cl, 11.54; N, 7.30.

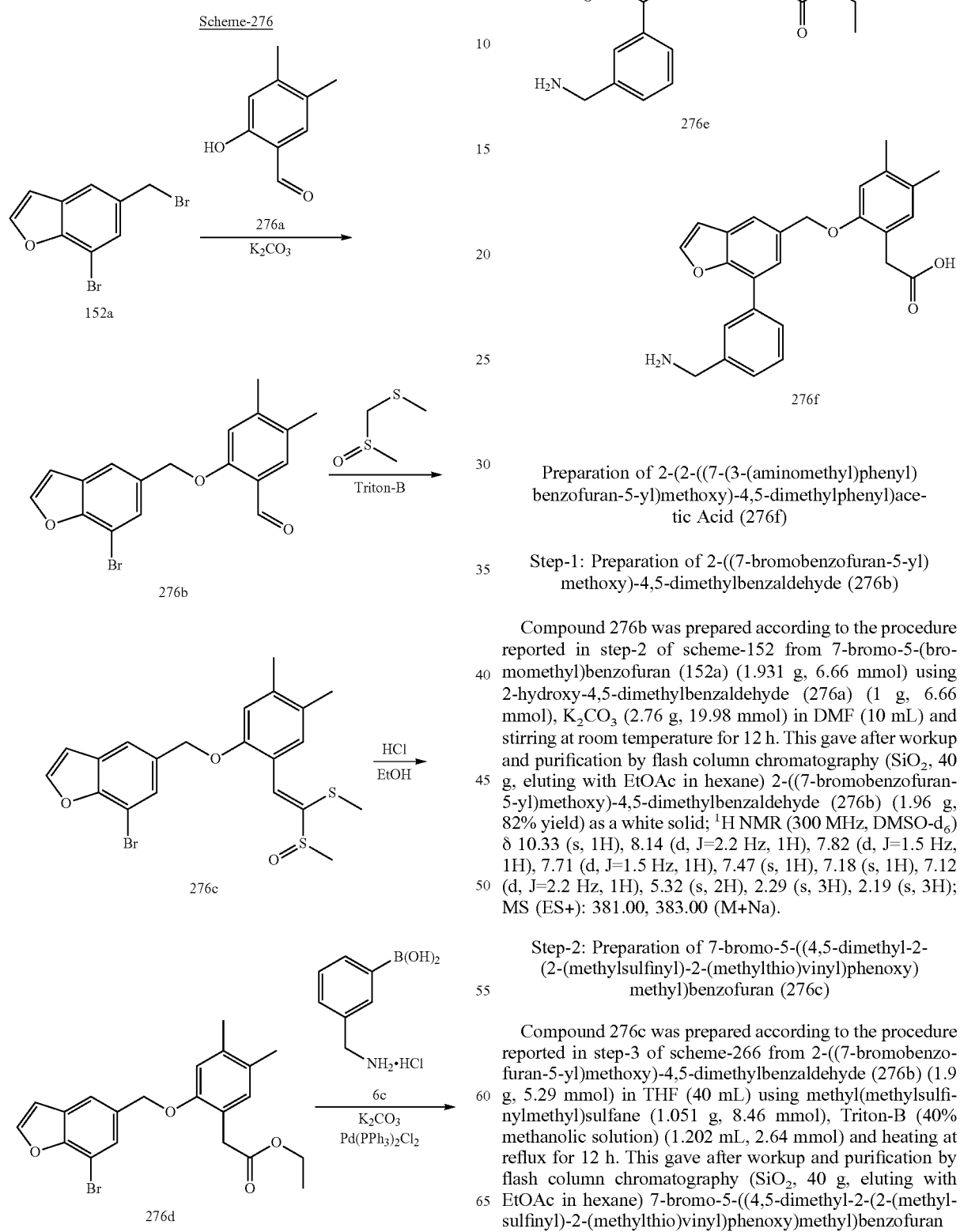

Preparation of 2-(2-((7-(3-(aminomethyl)phenyl)benzofuran-5-yl)methoxy)-4,5-dimethylphenyl)acetic Acid (276f)

Step-1: Preparation of 2-((7-bromobenzofuran-5-yl)methoxy)-4,5-dimethylbenzaldehyde (276b)

Compound 276b was prepared according to the procedure reported in step-2 of scheme-152 from 7-bromo-5-(bromomethyl)benzofuran (152a) (1.931 g, 6.66 mmol) using 2-hydroxy-4,5-dimethylbenzaldehyde (276a) (1 g, 6.66 mmol), K$_2$CO$_3$ (2.76 g, 19.98 mmol) in DMF (10 mL) and stirring at room temperature for 12 h. This gave after workup and purification by flash column chromatography (SiO$_2$, 40 g, eluting with EtOAc in hexane) 2-((7-bromobenzofuran-5-yl)methoxy)-4,5-dimethylbenzaldehyde (276b) (1.96 g, 82% yield) as a white solid; $^1$H NMR (300 MHz, DMSO-d$_6$) δ 10.33 (s, 1H), 8.14 (d, J=2.2 Hz, 1H), 7.82 (d, J=1.5 Hz, 1H), 7.71 (d, J=1.5 Hz, 1H), 7.47 (s, 1H), 7.18 (s, 1H), 7.12 (d, J=2.2 Hz, 1H), 5.32 (s, 2H), 2.29 (s, 3H), 2.19 (s, 3H); MS (ES+): 381.00, 383.00 (M+Na).

Step-2: Preparation of 7-bromo-5-((4,5-dimethyl-2-(2-(methylsulfinyl)-2-(methylthio)vinyl)phenoxy)methyl)benzofuran (276c)

Compound 276c was prepared according to the procedure reported in step-3 of scheme-266 from 2-((7-bromobenzofuran-5-yl)methoxy)-4,5-dimethylbenzaldehyde (276b) (1.9 g, 5.29 mmol) in THF (40 mL) using methyl(methylsulfinylmethyl)sulfane (1.051 g, 8.46 mmol), Triton-B (40% methanolic solution) (1.202 mL, 2.64 mmol) and heating at reflux for 12 h. This gave after workup and purification by flash column chromatography (SiO$_2$, 40 g, eluting with EtOAc in hexane) 7-bromo-5-((4,5-dimethyl-2-(2-(methylsulfinyl)-2-(methylthio)vinyl)phenoxy)methyl)benzofuran (276c) (1.62 g, 66% yield) as a light yellow solid; $^1$H NMR (300 MHz, DMSO-d$_6$) δ 8.14 (d, J=2.2 Hz, 1H), 7.82 (s, 1H), 7.80 (s, 1H), 7.73 (d, J=1.5 Hz, 1H), 7.62 (d, J=1.6 Hz, 1H), 7.09 (d, J=2.2 Hz, 1H), 7.05 (s, 1H), 5.24 (s, 2H), 2.70 (s, 3H), 2.27 (s, 3H), 2.24 (s, 3H), 2.19 (s, 3H); MS (ES+): 465.0, 467.0 (M, M+2).

Step-3: Preparation of Ethyl 2-(2-((7-bromobenzofuran-5-yl)methoxy)-4,5-dimethylphenyl)acetate (276d)

Compound 276d was prepared according to the procedure reported in step-4 of scheme-266 from 7-bromo-5-((4,5-dimethyl-2-(2-(methylsulfinyl)-2-(methylthio)vinyl)phenoxy)methyl)benzofuran (276c) (1.6 g, 3.44 mmol) in ethanol (50 mL) using HCl (4 M in 1,4-dioxane, 3.44 mL, 13.75 mmol) and heating at reflux for 12 h. This gave after workup and purification by flash column chromatography (silica gel, 40 g, eluting with ethyl acetate and hexanes) ethyl 2-(2-((7-bromobenzofuran-5-yl)methoxy)-4,5-dimethylphenyl)acetate (276d) (1.2 g, 84% yield) as a clear syrup; $^1$H NMR (300 MHz, DMSO-d$_6$) δ 8.14 (d, J=2.2 Hz, 1H), 7.70 (d, J=1.4 Hz, 1H), 7.58 (d, J=1.5 Hz, 1H), 7.11 (d, J=2.2 Hz, 1H), 6.96 (s, 1H), 6.89 (s, 1H), 5.12 (s, 2H), 4.00 (q, J=7.1 Hz, 2H), 3.53 (s, 2H), 2.19 (s, 3H), 2.13 (s, 3H), 1.08 (t, J=7.1 Hz, 3H).

Step-4: Preparation of Ethyl 2-(2-((7-(3-(aminomethyl)phenyl)benzofuran-5-yl)methoxy)-4,5-dimethylphenyl)acetate (276e)

Compound 276e was prepared according to the procedure reported in step-3 of scheme-1 from ethyl 2-(2-((7-bromobenzofuran-5-yl)methoxy)-4,5-dimethylphenyl)acetate (276d) (403 mg, 0.966 mmol) in dioxane (10 mL) using (3-(aminomethyl)phenyl)boronic acid hydrochloride (6c) (290 mg, 1.545 mmol), bis(triphenylphosphine)palladium (II) chloride (Pd(PPh$_3$)$_2$Cl$_2$) (102 mg, 0.145 mmol) and a solution of K$_2$CO$_3$ (400 mg, 2.90 mmol) in water (3 mL) under an N$_2$ atmosphere heating at 100° C. for 6 h on oil bath. This gave after workup, purification by flash column chromatography (silica gel 40 g, eluting with DMA80 in DCM from 0-50%] ethyl 2-(2-((7-(3-(aminomethyl)phenyl)benzofuran-5-yl)methoxy)-4,5-dimethylphenyl)acetate (276e) (315 mg, 74% yield) as a colorless syrup; $^1$H NMR (300 MHz, DMSO-d$_6$) δ 8.09 (d, J=2.2 Hz, 1H), 7.82 (td, J=1.8, 0.7 Hz, 1H), 7.71 (dt, J=7.5, 1.6 Hz, 1H), 7.68 (d, J=1.6 Hz, 1H), 7.56 (d, J=1.6 Hz, 1H), 7.46 (t, J=7.5 Hz, 1H), 7.39 (dt, J=7.7, 1.5 Hz, 1H), 7.04 (d, J=2.2 Hz, 1H), 6.95 (s, 1H), 6.94 (s, 1H), 5.19 (s, 2H), 3.92 (q, J=7.1 Hz, 2H), 3.81 (s, 2H), 3.54 (s, 2H), 2.20 (s, 3H), 2.13 (s, 3H), 0.99 (t, J=7.1 Hz, 3H); (MS (ES+): 444.2 (M+1), 442.18 (M−1).

Step-5: Preparation of 2-(2-((7-(3-(aminomethyl)phenyl)benzofuran-5-yl)methoxy)-4,5-dimethylphenyl)acetic Acid (276f)

Compound 276f was prepared according to the procedure reported in step-6 of scheme-1 from ethyl 2-(2-((7-(3-(aminomethyl)phenyl)benzofuran-5-yl)methoxy)-4,5-dimethylphenyl)acetate (276e) (300 mg, 0.676 mmol) in MeOH (5 mL), THF (5 mL) using a solution of lithium hydroxide (65 mg, 2.71 mmol) in water (2 mL). This gave after workup and purification by reverse phase column [C18 (50g), eluting with ACN in water (containing 0.1% HCl) from 0-100%] 2-(2-((7-(3-(aminomethyl)phenyl)benzofuran-5-yl)methoxy)-4,5-dimethylphenyl)acetic acid (276f) (150 mg, 53% yield) HCl salt as a white solid; $^1$H NMR (300 MHz, DMSO-d$_6$) δ 8.59 (s, 3H), 8.10 (d, J=2.2 Hz, 1H), 8.02 (s, 1H), 7.93 (td, J=4.5, 1.7 Hz, 1H), 7.74 (d, J=1.5 Hz, 1H), 7.66 (d, J=1.6 Hz, 1H), 7.58 (d, J=4.6 Hz, 2H), 7.06 (d, J=2.2 Hz, 1H), 6.96 (s, 1H), 6.92 (s, 1H), 5.21 (s, 2H), 4.13 (s, 2H), 3.51 (s, 2H), 2.19 (s, 3H), 2.12 (s, 3H); MS (ES+): 416.20 (M+1), (ES−): 414.2 (M−1), HPLC t=2.42 min, (97.03%); Analysis calculated for C$_{26}$H$_{25}$NO$_4$.HCl.0.75H$_2$O: C, 67.09; H, 5.96; Cl, 7.62; N, 3.01; Found: C, 67.17; H, 5.77; Cl, 7.58; N, 3.03.

Scheme-277

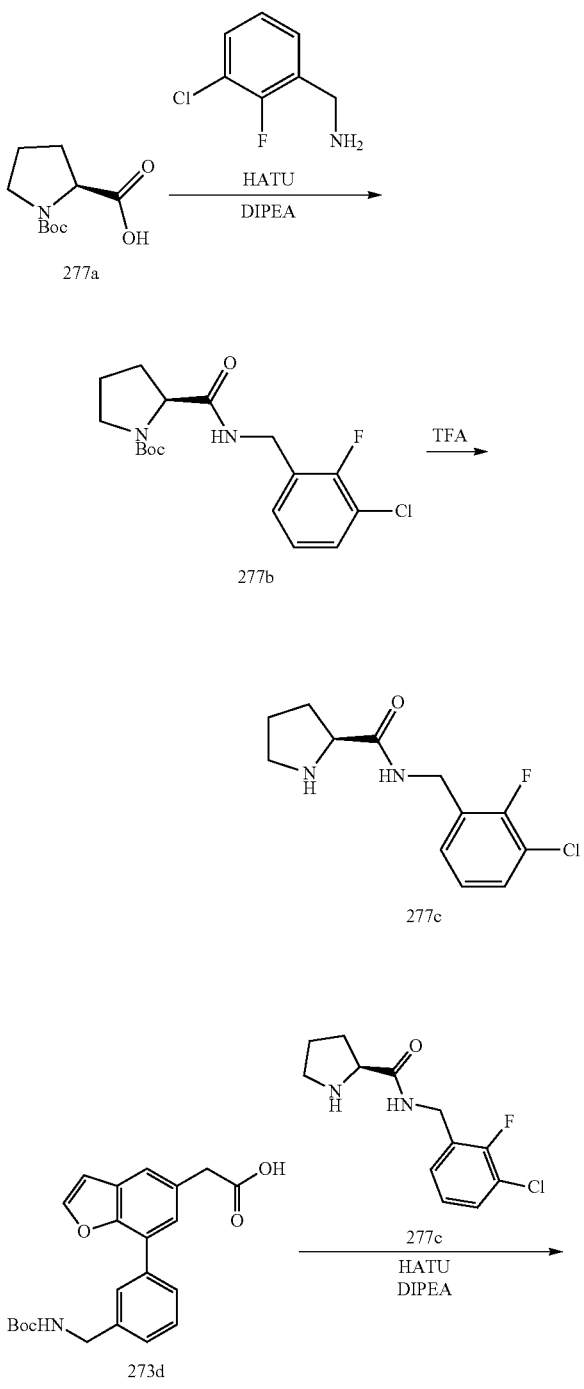

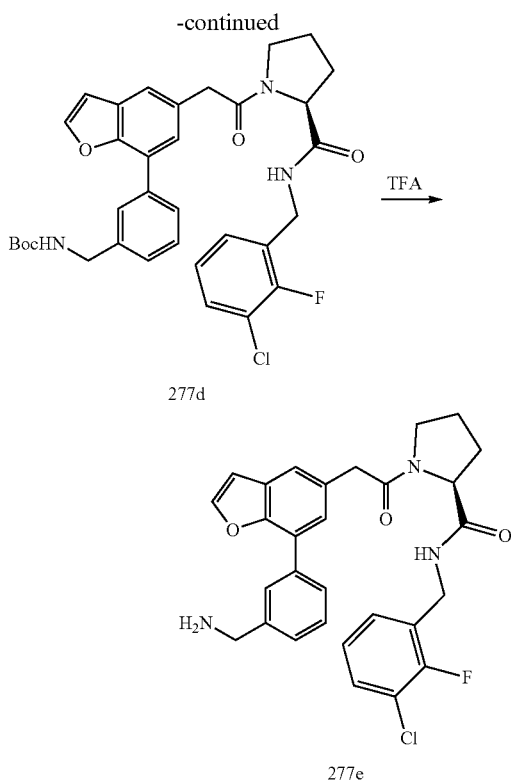

277d

277e

Preparation of (S)-1-(2-(7-(3-(aminomethyl)phenyl)benzofuran-5-yl)acetyl)-N-(3-chloro-2-fluorobenzyl)pyrrolidine-2-carboxamide (277e)

Step-1: Preparation of (S)-tert-butyl 2-((3-chloro-2-fluorobenzyl)carbamoyl)pyrrolidine-1-carboxylate (277b)

Compound 277b was prepared according to the procedure reported in step-4 of scheme-1 from (S)-1-(tert-butoxycarbonyl)pyrrolidine-2-carboxylic acid (277a) (3 g, 13.94 mmol) and (3-chloro-2-fluorophenyl)methanamine (1.927 mL, 15.33 mmol) in DMF (40 mL) using HATU (7.95 g, 20.91 mmol) and DIPEA (9.71 mL, 55.8 mmol) and stirring at room temperature for 16 h. This gave after workup and purification by flash column chromatography (silica gel, 24 g, eluting with 0 to 50% DMA 80 in DCM) (S)-tert-butyl 2-((3-chloro-2-fluorobenzyl)carbamoyl)pyrrolidine-1-carboxylate (277b) (4.08 g, 82% yield) as a light brown solid; $^1$H NMR (300 MHz, DMSO-$d_6$) δ 8.53-8.36 (m, 1H), 7.52-7.41 (m, 1H), 7.36-7.27 (m, 1H), 7.23-7.09 (m, 1H), 4.46-4.21 (m, 2H), 4.17-4.03 (m, 1H), 3.45-3.22 (m, 2H), 2.23-2.02 (m, 1H), 1.86-1.69 (m, 3H), 1.40 and 1.25 (2s, 9H).

Step-2: Preparation of (S)—N-(3-chloro-2-fluorobenzyl)pyrrolidine-2-carboxamide (277c)

Compound 277c was prepared according to the procedure reported in step-5 of scheme-1 from (S)-tert-butyl 2-((3-chloro-2-fluorobenzyl)carbamoyl)pyrrolidine-1-carboxylate (277b) (4 g, 11.21 mmol) in DCM (40 mL) using TFA (8.64 mL, 112 mmol). This gave after workup and purification by flash column chromatography (silica gel, eluting with 0 to 50% MeOH in DCM) (S)—N-(3-chloro-2-fluorobenzyl)pyrrolidine-2-carboxamide (277c) (2.0 g, 7.79 mmol, 69.5% yield) as a brown oil; $^1$H NMR (300 MHz, DMSO-$d_6$) δ 9.11 (t, J=5.7 Hz, 1H), 7.52 (ddd, J=8.9, 7.3, 1.8 Hz, 1H), 7.33 (ddd, J=8.4, 6.8, 1.8 Hz, 1H), 7.22 (td, J=7.8, 1.0 Hz, 1H), 4.42 (d, J=5.7 Hz, 2H), 4.28-4.16 (m, 1H), 3.30-3.09 (m, 3H), 2.38-2.20 (m, 1H), 1.99-1.73 (m, 3H).

Step-3: Preparation of (S)-tert-butyl 3-(5-(2-(2-((3-chloro-2-fluorobenzyl)carbamoyl)pyrrolidin-1-yl)-2-oxoethyl)benzofuran-7-yl)benzylcarbamate (277d)

Compound 277d was prepared according to the procedure reported in step-4 of scheme-1 from 2-(7-(3-(((tert-butoxycarbonyl)amino)methyl)phenyl)benzofuran-5-yl)acetic acid (273d) (200 mg, 0.524 mmol) in DMF (4 mL) using (S)—N-(3-chloro-2-fluorobenzyl)pyrrolidine-2-carboxamide (277c) (243 mg, 0.655 mmol), DIPEA (0.365 mL, 2.097 mmol) and HATU (299 mg, 0.787 mmol). This gave after workup and purification by flash column chromatography [silica (12 g), eluting with 0 to 100% EtOAc/MeOH=9:1 in hexane] (S)-tert-butyl 3-(5-(2-(2-((3-chloro-2-fluorobenzyl)carbamoyl)pyrrolidin-1-yl)-2-oxoethyl)benzofuran-7-yl)benzylcarbamate (277d) (375 mg) as a clear syrup; MS (ES+): 642.2, 644.2 (M+Na), (ES−): 618.2, 620.2 (M, M−2).

Step-4: Preparation of (S)-1-(2-(7-(3-(aminomethyl)phenyl)benzofuran-5-yl)acetyl)-N-(3-chloro-2-fluorobenzyl)pyrrolidine-2-carboxamide (277e)

Compound 277e was prepared according to the procedure reported in step-5 of scheme-1 from (S)-tert-butyl 3-(5-(2-(2-((3-chloro-2-fluorobenzyl)carbamoyl)pyrrolidin-1-yl)-2-oxoethyl)benzofuran-7-yl)benzylcarbamate (277d) (375 mg, 0.605 mmol) in DCM (10 mL) using TFA (0.466 mL, 6.05 mmol). This gave after workup and purification by reverse phase column chromatography [C18 (50 g), eluting with ACN in water (containing 0.1% HCl) from 0-100%] (S)-1-(2-(7-(3-(aminomethyl)phenyl)benzofuran-5-yl)acetyl)-N-(3-chloro-2-fluorobenzyl)pyrrolidine-2-carboxamide (277e) (142 mg, 45% yield) as a white solid; MS (ES+): 520.1 (M+1), (ES−): 518.2 (M−1).

Scheme-278

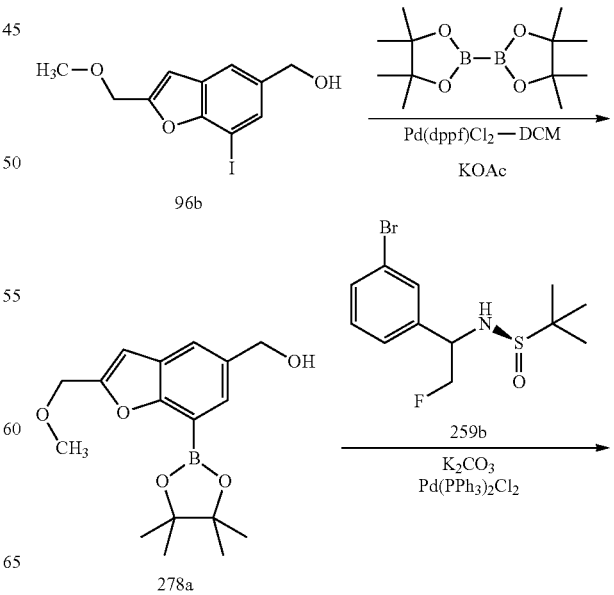

941

-continued

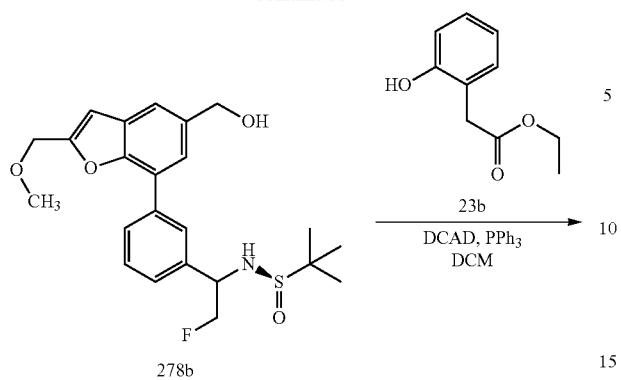

278b

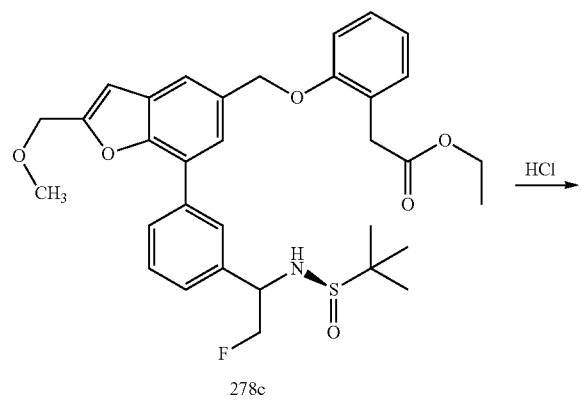

278c

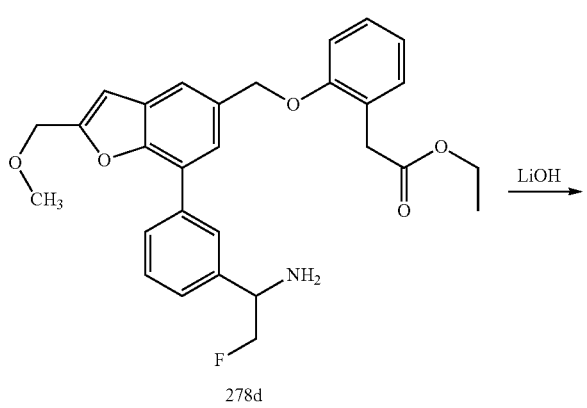

278d

942

-continued

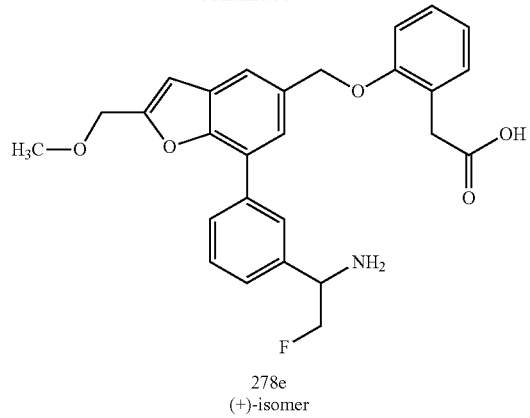

278e
(+)-isomer

Preparation of (+)-2-(2-((7-(3-(1-amino-2-fluoro-ethyl)phenyl)-2-(methoxymethyl)benzofuran-5-yl)methoxy)phenyl)acetic Acid (278e)

Step-1: Preparation of (2-(methoxymethyl)-7-(4,4,5,5-tetramethyl-1,3,2-dioxaborolan-2-yl)benzofuran-5-yl)methanol (278a)

Compound 278a was prepared according to the procedure reported in step-1 of scheme-59 from (7-iodo-2-(methoxymethyl)benzofuran-5-yl)methanol (96b) (2 g, 6.29 mmol), using bis(pinacolato)diboron (2.395 g, 9.43 mmol), potassium acetate (1.851 g, 18.86 mmol) and Pd(dppf)Cl$_2$-DCM (0.770 g, 0.943 mmol) in anhydrous dioxane (35 mL) under a nitrogen atmosphere and heating at 100° C. for 43h. This gave after workup and purification by flash column chromatography [silica (120g), eluting with hexanes/ethyl acetate (1:0 to 1:1)] (2-(methoxymethyl)-7-(4,4,5,5-tetramethyl-1,3,2-dioxaborolan-2-yl)benzofuran-5-yl)methanol (278a) (1.32 g) as a brown gum; $^1$H NMR (300 MHz, DMSO-d$_6$) δ 7.67 (d, 1H), 7.59 (d, J=1.8 Hz, 1H), 6.87 (s, 1H), 5.20 (t, J=5.8 Hz, 1H), 4.56 (d, J=5.7, 0.7 Hz, 2H), 4.53 (s, 2H), 3.33 (s, 3H), 1.34 (s, 12H).

Step-2: Preparation of (R)—N-(2-fluoro-1-(3-(5-(hydroxymethyl)-2-(methoxymethyl)benzofuran-7-yl)phenyl)ethyl)-2-methylpropane-2-sulfinamide (278b)

Compound 278b was prepared according to the procedure reported in step-3 of scheme-1 from (2-(methoxymethyl)-7-(4,4,5,5-tetramethyl-1,3,2-dioxaborolan-2-yl)benzofuran-5-yl)methanol (278a) (0.5 g, 1.571 mmol) in dioxane (10 mL) using (−)-(R)—N-(1-(3-bromophenyl)-2-fluoroethyl)-2-methylpropane-2-sulfinamide (259b) (0.608 g, 1.886 mmol), bis(triphenylphosphine)palladium(II) chloride (Pd(PPh$_3$)$_2$Cl$_2$) (0.165 g, 0.236 mmol) and a solution of K$_2$CO$_3$ (0.652 g, 4.71 mmol) in water (2 mL) under an N$_2$ atmosphere heating at 100° C. for 5 h on oil bath. This gave after workup, purification by flash column chromatography (silica gel, 40 g, eluting with a 9:1 mixture of ethyl acetate and methanol in hexanes) (R)—N-(2-fluoro-1-(3-(5-(hydroxymethyl)-2-(methoxymethyl)benzofuran-7-yl)phenyl)ethyl)-2-methylpropane-2-sulfinamide (278b) (200 mg, 29% yield) as a colorless oil; $^1$H NMR (300 MHz, DMSO-d$_6$) δ 7.87 (s, 1H), 7.85-7.75 (m, 1H), 7.59-7.55 (m, 1H), 7.54-7.48 (m, 2H), 7.46 (d, J=1.6 Hz, 1H), 6.96 (s, 1H), 6.06 (d, J=8.3 Hz, 1H), 5.76 (s, 2H), 5.27 (t, J=5.7 Hz, 1H), 4.66 (d, J=8.8 Hz, 2H), 4.55 (s, 2H), 4.51 (d, J=6.2 Hz, 1H), 3.32 (s, 3H), 1.14 (s, 9H); MS (ES+) 456.1 (M+Na), (ES−) 432.2 (M−1).

Step-3: Preparation of Ethyl 2-(2-((7-(3-(1-((R)-1,1-dimethylethylsulfinamido)-2-fluoroethyl)phenyl)-2-(methoxymethyl)benzofuran-5-yl)methoxy)phenyl)acetate (278c)

Compound 278c was prepared according to the procedure reported in step-2 of scheme-23 from (R)—N-(2-fluoro-1-(3-(5-(hydroxymethyl)-2-(methoxymethyl)benzofuran-7-yl)phenyl)ethyl)-2-methylpropane-2-sulfinamide (278b) (200 mg, 0.461 mmol) in DCM (10 mL) using triphenylphosphine (151 mg, 0.577 mmol), ethyl 2-(2-hydroxyphenyl)acetate (23b) (104 mg, 0.577 mmol) and a solution of (E)-bis(4-chlorobenzyl) diazene-1,2-dicarboxylate (DCAD, 237 mg, 0.646 mmol) in DCM (5 mL). This gave after workup and purification by flash column chromatography (silica gel, 25 g, eluting with ethyl acetate in hexanes from 0-50%) ethyl 2-(2-((7-(3-(1-((R)-1,1-dimethylethylsulfinamido)-2-fluoroethyl)phenyl)-2-(methoxymethyl)benzofuran-5-yl)methoxy)phenyl)acetate (278c) (425 mg) as a colorless oil; MS (ES+): 596.2 (M+1), 618.2 (M+Na).

Step-4: Preparation of Ethyl 2-(2-((7-(3-(1-amino-2-fluoroethyl)phenyl)-2-(methoxymethyl)benzofuran-5-yl)methoxy)phenyl)acetate (278d)

To a stirred solution of ethyl 2-(2-((7-(3-(1-((R)-1,1-dimethylethylsulfinamido)-2-fluoroethyl)phenyl)-2-(methoxymethyl)benzofuran-5-yl)methoxy)phenyl)acetate (278c) (400 mg, 0.671 mmol) in THF (10 mL) and ethanol (2 mL) was added 3 N aqueous HCl (0.895 mL, 2.69 mmol) at room temperature and stirred for 30 mins. Reaction was concentrated in vacuum and residue was purified by flash column chromatography (silica gel) to afford ethyl 2-(2-((7-(3-(1-amino-2-fluoroethyl)phenyl)-2-(methoxymethyl)benzofuran-5-yl)methoxy)phenyl)acetate (278d) (40 mg, 12% yield) as a white solid; MS (ES+): 492.2 (M+1).

Step-5: Preparation of (+)-2-(2-((7-(3-(1-amino-2-fluoroethyl)phenyl)-2-(methoxymethyl)benzofuran-5-yl)methoxy)phenyl)acetic Acid (278e)

Compound 278e was prepared according to the procedure reported in step-6 of scheme-1 from ethyl 2-(2-((7-(3-(1-amino-2-fluoroethyl)phenyl)-2-(methoxymethyl)benzofuran-5-yl)methoxy)phenyl)acetate (278d) (40 mg, 0.081 mmol) in THF/MeOH (2.5 mL, each) using a solution of lithium hydroxide hydrate (6 mg, 0.244 mmol) in water (2 mL). This gave after workup and purification by reverse phase column chromatography [C18 column, 50 g, eluting with water (containing 0.1% HCl)/acetonitrile (1:0 to 0:1)] (+)-2-(2-((7-(3-(1-amino-2-fluoroethyl)phenyl)-2-(methoxymethyl)benzofuran-5-yl)methoxy)phenyl)acetic acid (278e) (18 mg, 0.039 mmol, 47.7% yield) HCl salt as a white solid; $^1$H NMR (300 MHz, DMSO-$d_6$) δ 8.02-7.99 (m, 1H), 7.96 (dt, J=7.6, 1.5 Hz, 1H), 7.74 (s, 1H), 7.68-7.55 (m, 3H), 7.28-7.18 (m, 2H), 7.09 (d, J=8.0 Hz, 1H), 7.00 (s, 1H), 6.90 (t, J=7.4 Hz, 1H), 5.26 (s, 2H), 4.94-4.71 (m, 3H), 4.58 (s, 2H), 3.59 (s, 2H), 3.32 (s, 3H); MS (ES+): 464.20 (M+1), (ES−): 462.20 (M−1); Optical rotation [t]D=+16.84 (c=0.19, MeOH).

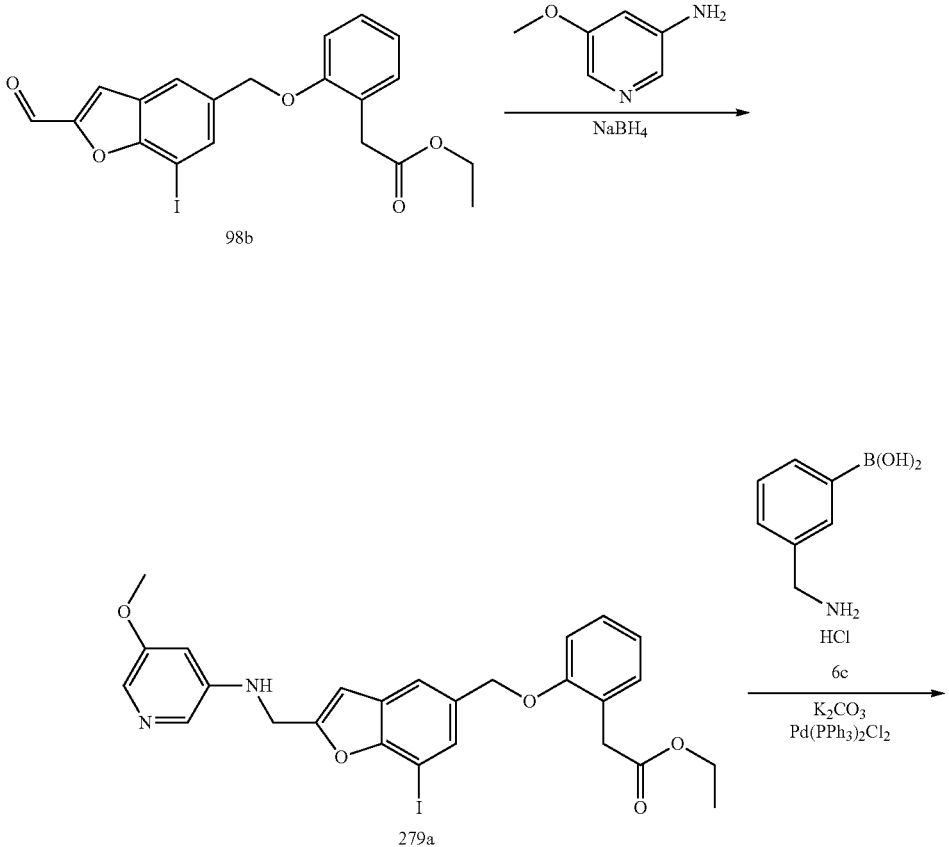

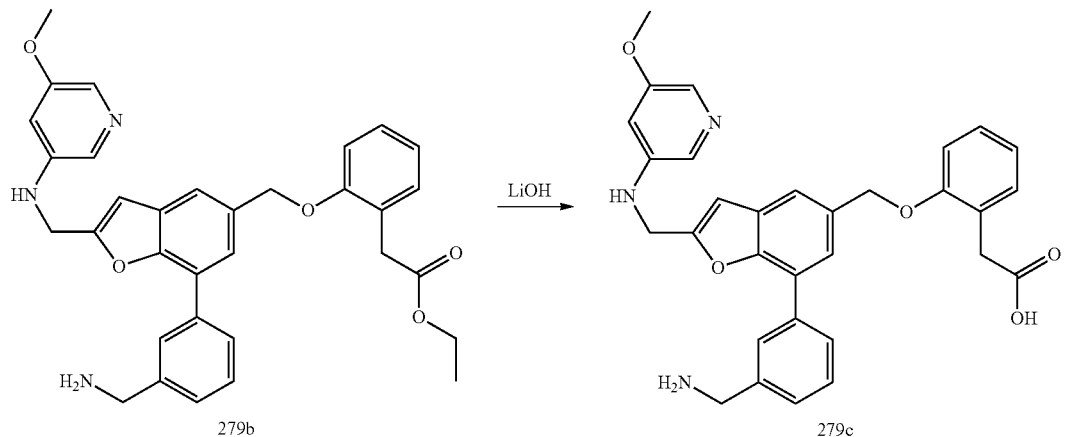

Preparation of 2-(2-((7-(3-(aminomethyl)phenyl)-2-(((5-methoxypyridin-3-yl)amino)methyl)benzofuran-5-yl)methoxy)phenyl)acetic Acid (279c)

Step-1: Preparation of Ethyl 2-(2-((7-iodo-2-(((5-methoxypyridin-3-yl)amino)methyl)benzofuran-5-yl)methoxy)phenyl)acetate (279a)

To a stirred suspension of ethyl 2-(2-((2-formyl-7-iodo-benzofuran-5-yl)methoxy)phenyl)acetate (98b) (400 mg, 0.862 mmol) in ethanol (10 mL) was added 5-methoxypyridin-3-amine (118 mg, 0.948 mmol) and stirred at room temperature for 1 h. Reaction was heated at reflux for 30 min, cooled to room temperature, added sodium borohydride (65.2 mg, 1.723 mmol) and stirred at room temperature for 1 h. Reaction was concentrated in vacuum diluted with water and extracted with ethyl acetate (200 mL). The ethyl acetate layer was washed with water (2×25 mL), brine (30 mL), dried, filtered and concentrated. The crude residue was purified by flash column chromatography to afford ethyl 2-(2-((7-iodo-2-(((5-methoxypyridin-3-yl)amino)methyl)benzofuran-5-yl)methoxy)phenyl)acetate (279a) (290 mg, 59% yield) as a gummy material; $^1$H NMR (300 MHz, DMSO-$d_6$) δ 7.71 (d, J=2.4 Hz, 1H), 7.69 (d, J=1.6 Hz, 1H), 7.61 (d, J=1.6 Hz, 1H), 7.53 (t, J=2.8 Hz, 1H), 7.26-7.17 (m, 2H), 7.06 (dd, J=8.3, 1.1 Hz, 1H), 6.93 (d, J=1.0 Hz, 1H), 6.91-6.85 (m, 1H), 6.67-6.56 (m, 2H), 5.12 (s, 2H), 4.53 (d, J=6.2 Hz, 2H), 4.09-3.91 (m, 2H), 3.74 (s, 3H), 3.60 (s, 2H), 1.05 (t, J=7.1 Hz, 3H); MS (ES+): 573.1 (M+1).

Step-2: Preparation of Ethyl 2-(2-((7-(3-(aminomethyl)phenyl)-2-(((5-methoxypyridin-3-yl)amino)methyl)benzofuran-5-yl)methoxy)phenyl)acetate (279b)

Compound 279b was prepared according to the procedure reported in step-3 of scheme-1 from ethyl 2-(2-((7-iodo-2-(((5-methoxypyridin-3-yl)amino)methyl)benzofuran-5-yl)methoxy)phenyl)acetate (279a) (290 mg, 0.507 mmol) in dioxane (10 mL) using 3-(aminomethyl)phenylboronic acid hydrochloride (6c) (152 mg, 0.811 mmol), bis(triphenylphosphine)palladium(II) chloride (Pd(PPh$_3$)$_2$Cl$_2$) (53.3 mg, 0.076 mmol) and a solution of K$_2$CO$_3$ (210 mg, 1.52 mmol) in water (3 mL) under an N$_2$ atmosphere heating at 100° C. for 6 h on oil bath. This gave after workup, purification by flash column chromatography (silica gel, 40 g, eluting with DMA80 in DCM from 0-50%) followed by purification by reverse phase flash column chromatography [C18 (100 g), eluting with ACN in water (containing 0.1% HCl) from 0-100%] ethyl 2-(2-((7-(3-(aminomethyl)phenyl)-2-(((5-methoxypyridin-3-yl)amino)methyl)benzofuran-5-yl)methoxy)phenyl)acetate (279b) (210 mg, 75% yield) as a colorless oil; $^1$H NMR (300 MHz, DMSO-$d_6$) δ 7.77 (s, 1H), 7.72 (d, J=2.3 Hz, 1H), 7.71-7.66 (m, 1H), 7.60 (d, J=1.6 Hz, 1H), 7.52 (dd, J=4.5, 2.1 Hz, 2H), 7.46-7.34 (m, 2H), 7.34-7.24 (m, 1H), 7.27-7.18 (m, 2H), 7.14-7.07 (m, 1H), 6.90 (td, J=7.4, 1.1 Hz, 1H), 6.85 (s, 1H), 6.65 (t, J=2.4 Hz, 1H), 6.58 (t, J=6.2 Hz, 1H), 5.21 (s, 2H), 4.52 (d, J=6.1 Hz, 2H), 3.91 (q, J=7.1 Hz, 2H), 3.79 (s, 2H), 3.72 (s, 3H), 3.70 (s, 1H), 3.61 (s, 2H), 0.96 (t, J=7.1 Hz, 3H).

Step-3: Preparation of 2-(2-((7-(3-(aminomethyl)phenyl)-2-(((5-methoxypyridin-3-yl)amino)methyl)benzofuran-5-yl)methoxy)phenyl)acetic Acid (279c)

Compound 279c was prepared according to the procedure reported in step-6 of scheme-1 from ethyl 2-(2-((7-(3-(aminomethyl)phenyl)-2-(((5-methoxypyridin-3-yl)amino)methyl)benzofuran-5-yl)methoxy)phenyl)acetate (279b) (210 mg, 0.381 mmol) in THF/MeOH (3 mL, each) using a solution of lithium hydroxide hydrate (37 mg, 1.523 mmol) in water (2 mL). This gave after workup and purification by reverse phase column chromatography [C18 column, 50 g, eluting with water (containing 0.1% HCl)/acetonitrile (1:0 to 0:1)] 2-(2-((7-(3-(aminomethyl)phenyl)-2-(((5-methoxypyridin-3-yl)amino)methyl)benzofuran-5-yl)methoxy)phenyl)acetic acid (279c) (155 mg, 78% yield) hydrochloride salt as a white solid; $^1$H NMR (300 MHz, DMSO-$d_6$) δ 12.23 (s, 1H), 8.53 (s, 3H), 8.02 (s, 1H), 7.95 (d, J=2.2 Hz, 1H), 7.88 (ddd, J=5.6, 3.6, 1.7 Hz, 1H), 7.85 (s, 1H), 7.79 (s, 1H), 7.69 (d, J=1.6 Hz, 1H), 7.61 (d, J=1.6 Hz, 1H), 7.56-7.51 (m, 2H), 7.35 (d, J=2.2 Hz, 1H), 7.23 (dd, J=8.1, 6.5 Hz, 2H), 7.07 (d, J=7.9 Hz, 1H), 6.94 (s, 1H), 6.93-6.85 (m, 1H), 5.24 (s, 2H), 4.70 (s, 2H), 4.13 (d, J=5.7 Hz, 2H), 3.87 (s, 3H), 3.58 (s, 2H); MS (ES+): 524.20 (M+1), (ES-): 522.2 (M-1).

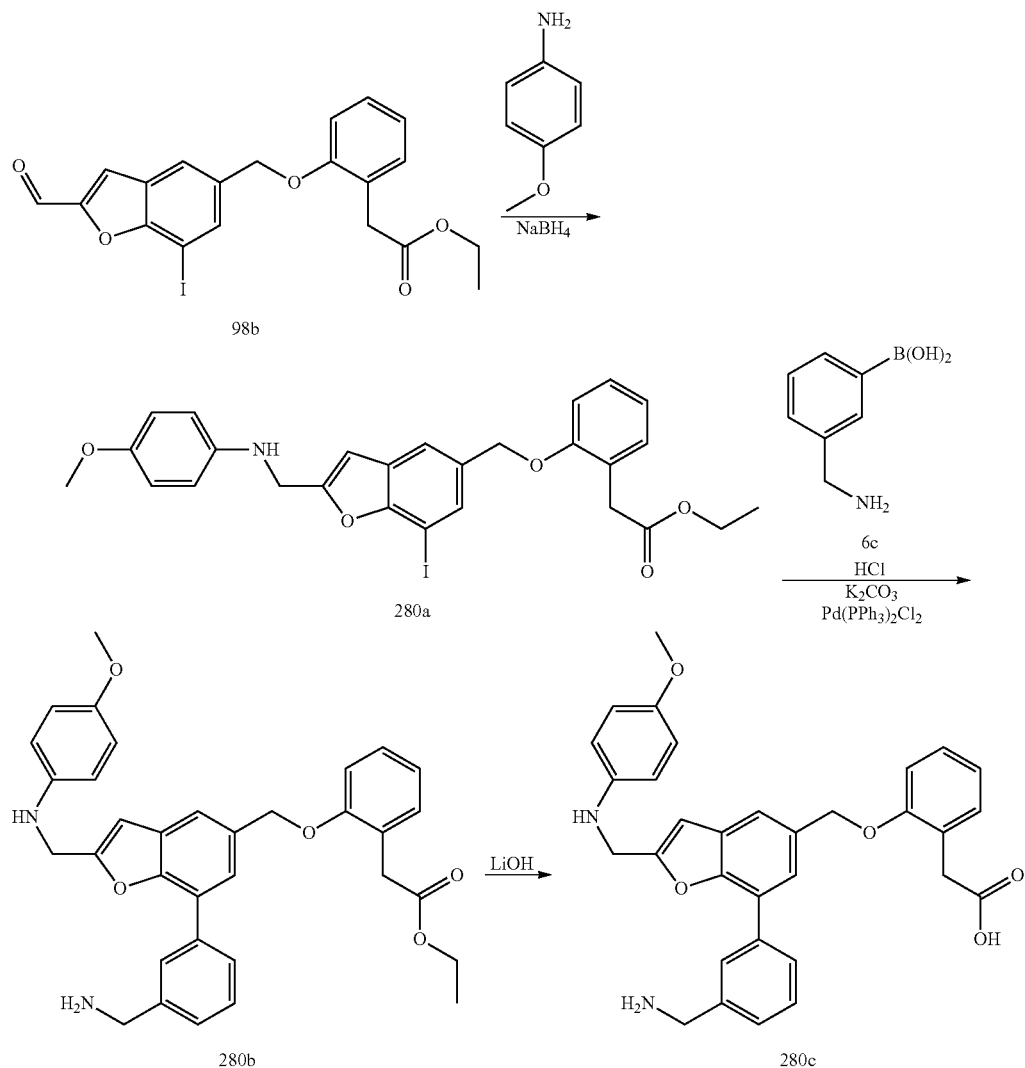

Scheme-280

Preparation of 2-(2-((7-(3-(aminomethyl)phenyl)-2-(((4-methoxyphenyl)amino)methyl)benzofuran-5-yl)methoxy)phenyl)acetic Acid (280c)

Step-1: Preparation of Ethyl 2-(2-((7-iodo-2-(((4-methoxyphenyl)amino)methyl)benzofuran-5-yl)methoxy)phenyl)acetate (280a)

Compound 280a was prepared according to the procedure reported in step-1 of scheme-279 from ethyl 2-(2-((2-formyl-7-iodobenzofuran-5-yl)methoxy)phenyl)acetate (98b) (400 mg, 0.862 mmol) in ethanol (10 mL) using 4-methoxyaniline (118 mg, 0.948 mmol) and sodium borohydride (130 mg, 3.45 mmol). This gave after workup, purification by flash column chromatography (silica gel) ethyl 2-(2-((7-iodo-2-(((4-methoxyphenyl)amino)methyl)benzofuran-5-yl)methoxy)phenyl)acetate (280a) (255 mg, 52% yield) as a brown solid; $^1$H NMR (300 MHz, DMSO-$d_6$) δ 7.67 (t, J=1.4 Hz, 1H), 7.59 (d, J=1.5 Hz, 1H), 7.25 (d, J=7.7 Hz, 1H), 7.25-7.16 (m, 1H), 7.05 (dd, J=8.2, 1.1 Hz, 1H), 6.91 (dd, J=7.4, 1.1 Hz, 1H), 6.84 (d, J=1.0 Hz, 1H), 6.74-6.68 (m, 2H), 6.68-6.61 (m, 2H), 5.90 (t, J=6.2 Hz, 1H), 5.11 (s, 2H), 4.41 (d, J=6.2 Hz, 2H), 4.00 (q, J=7.1 Hz, 2H), 3.62 (s, 3H), 1.06 (t, J=7.1 Hz, 3H).

Step-2: Preparation of Ethyl 2-(2-((7-(3-(aminomethyl)phenyl)-2-(((4-methoxyphenyl)amino)methyl)benzofuran-5-yl)methoxy)phenyl)acetate (280b)

Compound 280b was prepared according to the procedure reported in step-3 of scheme-1 from ethyl 2-(2-((7-iodo-2-(((4-methoxyphenyl)amino)methyl)benzofuran-5-yl)methoxy)phenyl)acetate (280a) (250 mg, 0.438 mmol) in dioxane (10 mL) using 3-(aminomethyl)phenylboronic acid hydrochloride (6c) (131 mg, 0.700 mmol), bis(triphenylphosphine)palladium(II) chloride (Pd(PPh$_3$)$_2$Cl$_2$) (46.1 mg, 0.066 mmol) and a solution of K$_2$CO$_3$ (181 mg, 1.313 mmol) in water (3 mL) under an N$_2$ atmosphere heating at 100° C. for 6 h on oil bath. This gave after workup and purification by flash column chromatography (silica gel, 40 g, eluting with DMA80 in DCM from 0-50%) ethyl 2-(2-((7-(3-(aminomethyl)phenyl)-2-(((4-methoxyphenyl)amino)methyl)benzofuran-5-yl)methoxy)phenyl)acetate (280b) (155 mg, 64% yield) as a colorless sticky gum; $^1$H NMR (300 MHz, DMSO-$d_6$) δ 7.78 (s, 1H), 7.74-7.66 (m, 1H), 7.57 (d, J=1.6 Hz, 1H), 7.50 (d, J=1.7 Hz, 1H), 7.44 (t, J=7.5 Hz, 1H), 7.38 (d, J=7.5 Hz, 1H), 7.26 (d, J=7.4 Hz, 1H), 7.21 (dd, J=7.5, 1.7 Hz, 1H), 7.12-7.06 (m, 1H), 6.90 (td, J=7.4, 1.1 Hz, 1H), 6.76 (s, 1H), 6.76-6.68 (m, 2H), 6.71-6.61 (m, 2H), 5.85 (t, J=6.4 Hz, 1H), 5.20 (s, 2H), 4.41 (d, J=6.3 Hz, 2H), 3.91 (q, J=7.2 Hz, 2H), 3.80 (s, 2H), 3.62 (s, 3H), 3.61 (s, 2H), 0.97 (t, J=7.1 Hz, 3H); MS (ES+): 552.2 (M+1), 573.2 (M+Na).

Step-3: Preparation of 2-(2-((7-(3-(aminomethyl) phenyl)-2-(((4-methoxyphenyl)amino)methyl)benzo-furan-5-yl)methoxy)phenyl)acetic Acid (280c)

Compound 280c was prepared according to the procedure reported in step-6 of scheme-1 from ethyl 2-(2-((7-(3-(aminomethyl)phenyl)-2-(((4-methoxyphenyl)amino) methyl)benzofuran-5-yl)methoxy)phenyl)acetate (280b) (150 mg, 0.272 mmol) in THF/MeOH (3 mL, each) using a solution of lithium hydroxide hydrate (26 mg, 1.09 mmol) in water (2 mL). This gave after workup and purification by reverse phase column chromatography [C18 column, 50 g, eluting with water (containing 0.1% HCl)/acetonitrile (1:0 to 0:1)] 2-(2-((7-(3-(aminomethyl)phenyl)-2-(((4-methoxy-phenyl)amino)methyl)benzofuran-5-yl)methoxy)phenyl) acetic acid (280c) (110 mg, 77% yield) HCl salt as a yellow solid; $^1$H NMR (300 MHz, DMSO-$d_6$) δ 8.44-8.33 (m, 3H), 8.01 (s, 1H), 7.88 (d, J=7.0 Hz, 1H), 7.67 (d, J=1.6 Hz, 1H), 7.60 (d, J=1.7 Hz, 1H), 7.58 (d, J=7.7 Hz, 1H), 7.54 (d, J=1.9 Hz, 2H), 7.24 (d, J=7.4 Hz, 2H), 7.20 (s, 1H), 7.07 (d, J=8.1 Hz, 1H), 6.99-6.76 (m, 5H), 5.23 (s, 2H), 4.54 (s, 2H), 4.15 (d, J=5.8 Hz, 2H), 3.66 (s, 3H), 3.59 (s, 2H); MS (ES+): 523.20 (M+1), (ES-): 521.3 (M-1); Analysis calculated for $C_{32}H_{30}N_2O_5 \cdot 1.75HCl \cdot 2H_2O$; C, 61.75; H, 5.79; Cl, 9.97; N, 4.50; Found; C, 61.68; H, 5.48; Cl, 9.96; N, 4.62.

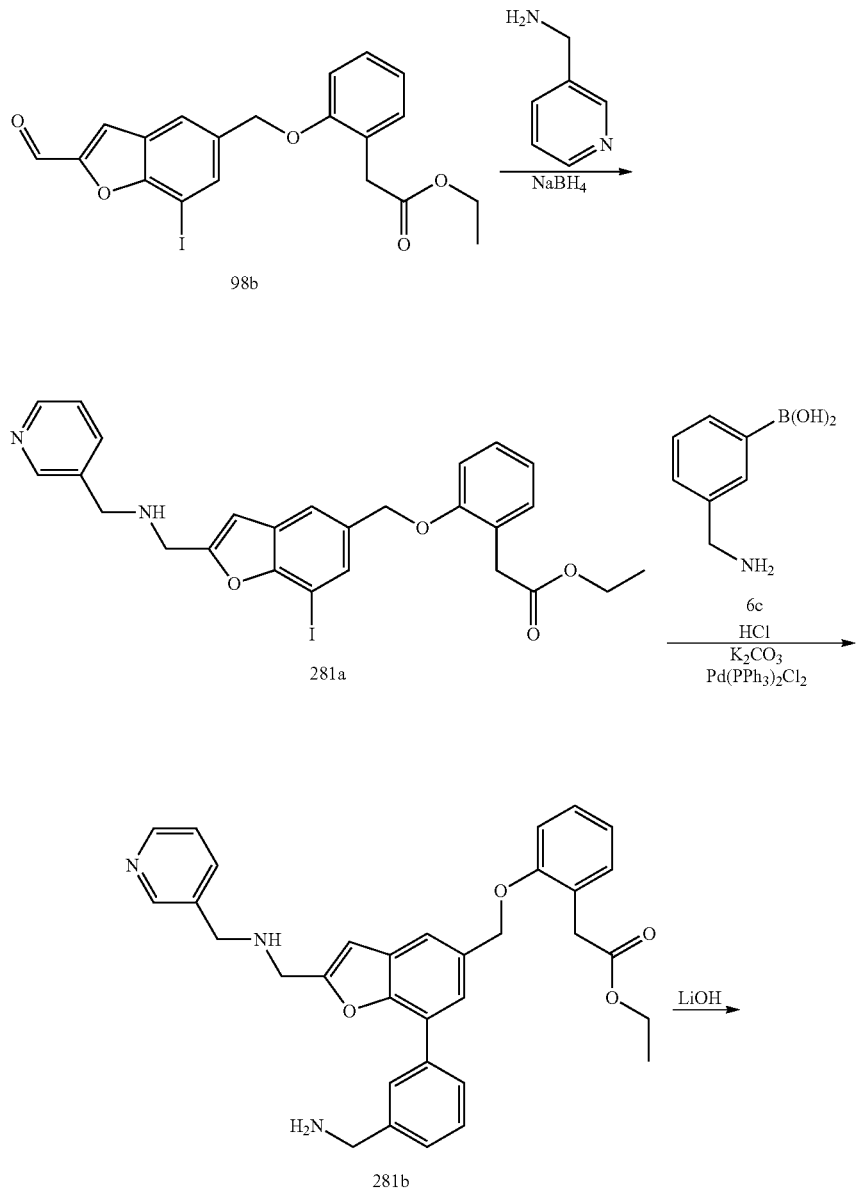

Scheme-281

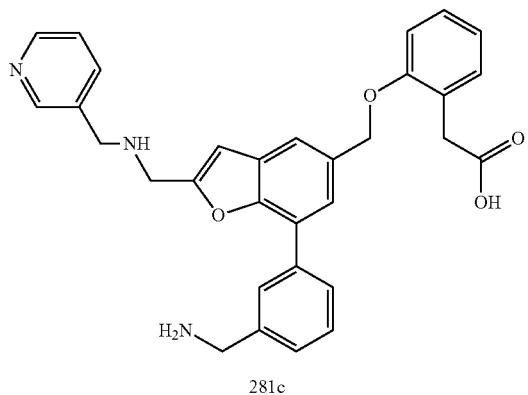

281c

Preparation of 2-(2-((7-(3-(aminomethyl)phenyl)-2-(((pyridin-3-ylmethyl)amino)methyl)benzofuran-5-yl)methoxy)phenyl)acetic Acid (281c)

Step-1: Preparation of Ethyl 2-(2-((7-iodo-2-(((pyridin-3-ylmethyl)amino)methyl)benzofuran-5-yl)methoxy)phenyl)acetate (281a)

Compound 281a was prepared according to the procedure reported in step-1 of scheme-279 from ethyl 2-(2-((2-formyl-7-iodobenzofuran-5-yl)methoxy)phenyl)acetate (98b) (400 mg, 0.862 mmol) in ethanol (10 mL) using pyridin-3-ylmethanamine (102 mg, 0.948 mmol) and sodium borohydride (130 mg, 3.45 mmol). This gave after workup, purification by flash column chromatography (silica gel) ethyl 2-(2-((7-iodo-2-(((pyridin-3-ylmethyl)amino)methyl)benzofuran-5-yl)methoxy)phenyl)acetate (281a) (190 mg, 40% yield) as a sticky material; $^1$H NMR (300 MHz, DMSO-$d_6$) δ 8.55 (dd, J=2.3, 0.9 Hz, 1H), 8.44 (dd, J=4.8, 1.7 Hz, 1H), 7.78 (dt, J=7.8, 2.0 Hz, 1H), 7.68 (d, J=1.5 Hz, 1H), 7.61 (d, J=1.5 Hz, 1H), 7.34 (ddd, J=7.8, 4.8, 0.9 Hz, 1H), 7.29-7.19 (m, 2H), 7.07 (d, J=8.1 Hz, 1H), 6.94-6.86 (m, 2H), 5.13 (s, 2H), 4.03 (q, J=7.1 Hz, 2H), 3.86 (s, 2H), 3.79 (s, 2H), 3.61 (s, 2H), 2.93 (s, 1H), 1.09 (t, J=7.1 Hz, 3H); MS (ES+): 557.1 (M+1).

Step-2: Preparation of Ethyl 2-(2-((7-(3-(aminomethyl)phenyl)-2-(((pyridin-3-ylmethyl)amino)methyl)benzofuran-5-yl)methoxy)phenyl)acetate (281b)

Compound 281b was prepared according to the procedure reported in step-3 of scheme-1 from ethyl 2-(2-((7-iodo-2-(((pyridin-3-ylmethyl)amino)methyl)benzofuran-5-yl)methoxy)phenyl)acetate (281a) (190 mg, 0.341 mmol) in dioxane (10 mL) using 3-(aminomethyl)phenylboronic acid hydrochloride (6c) (102 mg, 0.546 mmol), bis(triphenylphosphine)palladium(II) chloride (Pd(PPh$_3$)$_2$Cl$_2$) (36 mg, 0.051 mmol) and a solution of K$_2$CO$_3$ (142 mg, 1.024 mmol) in water (3 mL) under an argon atmosphere heating at 100° C. for 6 h on oil bath. This gave after workup and purification by flash column chromatography (silica gel 40 g, eluting with DMA80 in DCM from 0-50%) ethyl 2-(2-((7-(3-(aminomethyl)phenyl)-2-(((pyridin-3-ylmethyl)amino)methyl)benzofuran-5-yl)methoxy)phenyl)acetate (281b) (124 mg, 68% yield) as a colorless sticky gum; $^1$H NMR (300 MHz, DMSO-$d_6$) δ 8.55 (dd, J=2.3, 0.9 Hz, 1H), 8.44 (dd, J=4.8, 1.7 Hz, 1H), 7.81 (s, 1H), 7.80-7.71 (m, 2H), 7.61 (d, J=1.6 Hz, 1H), 7.52 (d, J=1.7 Hz, 1H), 7.46 (t, J=7.6 Hz, 1H), 7.38 (d, J=7.7 Hz, 1H), 7.33 (ddd, J=7.8, 4.8, 0.9 Hz, 1H), 7.29-7.24 (m, 1H), 7.24-7.18 (m, 1H), 7.14-7.09 (m, 1H), 6.91 (td, J=7.4, 1.1 Hz, 1H), 6.82 (d, J=0.9 Hz, 1H), 5.22 (s, 2H), 3.94 (q, J=7.1 Hz, 2H), 3.86 (s, 2H), 3.80 (d, J=3.1 Hz, 4H), 3.63 (s, 2H), 1.00 (t, J=7.1 Hz, 3H); MS (ES+): 536.2 (M+1), 558.2 (M+Na).

Step-3: Preparation of 2-(2-((7-(3-(aminomethyl)phenyl)-2-(((pyridin-3-ylmethyl)amino)methyl)benzofuran-5-yl)methoxy)phenyl)acetic Acid (281c)

Compound 281c was prepared according to the procedure reported in step-6 of scheme-1 from ethyl 2-(2-((7-(3-(aminomethyl)phenyl)-2-(((pyridin-3-ylmethyl)amino)methyl)benzofuran-5-yl)methoxy)phenyl)acetate (281b) (120 mg, 0.224 mmol) in THF/MeOH (3 mL, each) using a solution of lithium hydroxide hydrate (22 mg, 0.896 mmol) in water (2 mL). This gave after workup and purification by reverse phase column chromatography [C18 column, 50 g, eluting with water (containing 0.1% HCl)/acetonitrile (1:0 to 0:1)] 2-(2-((7-(3-(aminomethyl)phenyl)-2-(((pyridin-3-ylmethyl)amino)methyl)benzofuran-5-yl)methoxy)phenyl)acetic acid (281c) (55 mg, 49% yield) HCl salt as a white solid; $^1$H NMR (300 MHz, DMSO-$d_6$) δ 10.67-10.46 (m, 1H), 9.04 (s, 1H), 8.81 (dd, J=5.4, 1.5 Hz, 1H), 8.58 (d, J=7.6 Hz, 4H), 8.27 (s, 1H), 7.97 (dt, J=7.0, 1.9 Hz, 1H), 7.85 (dd, J=8.0, 5.3 Hz, 1H), 7.78 (d, J=1.6 Hz, 1H), 7.72 (d, J=1.7 Hz, 1H), 7.61-7.47 (m, 2H), 7.28-7.20 (m, 3H), 7.09 (d, J=8.0 Hz, 1H), 6.90 (td, J=7.4, 1.1 Hz, 1H), 5.28 (s, 2H), 4.52 (s, 2H), 4.45 (s, 2H), 4.23-4.12 (m, 2H), 3.60 (s, 2H); MS (ES+): 508.20 (M+1), (ES−): 506.2 (M−1); Analysis calculated for C$_{31}$H$_{29}$N$_3$O$_4$.3HCl3.5H$_2$O: C, 54.75; H, 5.78; Cl, 15.64; N, 6.18; Found; C, 54.66; H, 5.50; Cl, 15.72; N, 6.09.

Scheme-282

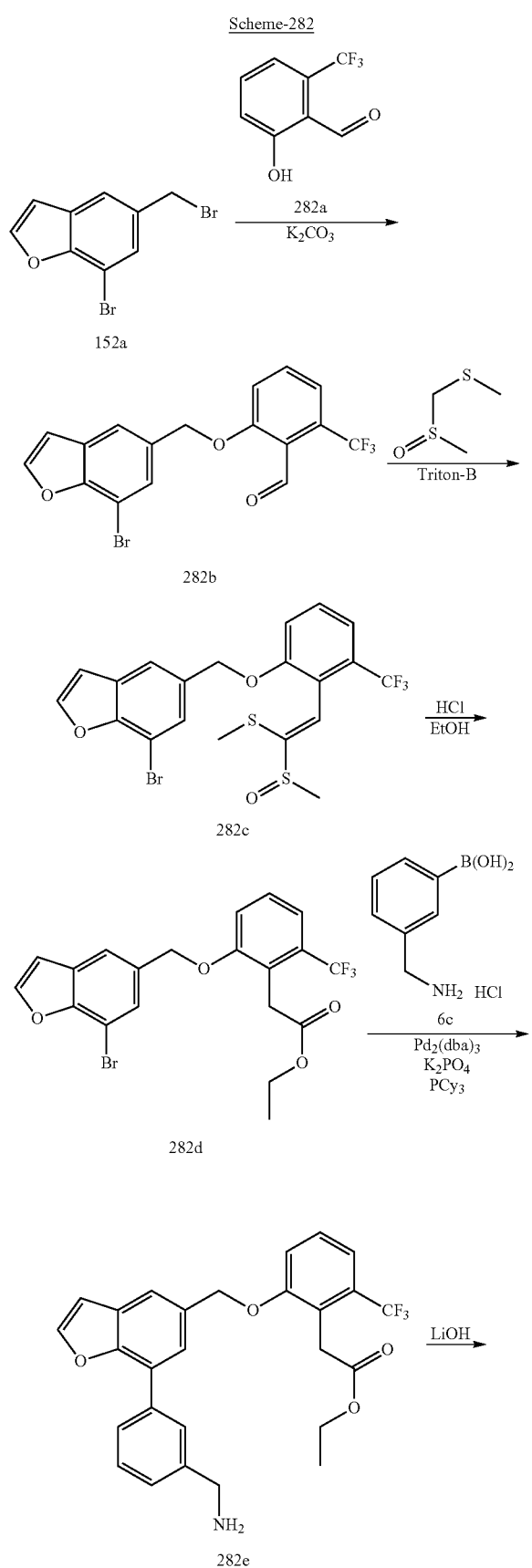

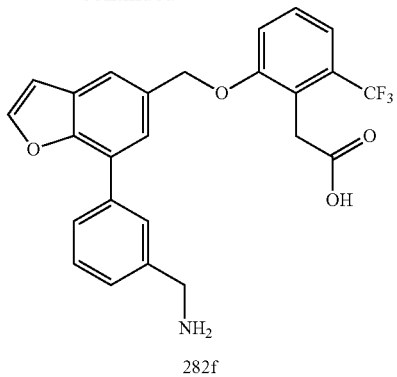 [SMILES: NCc1cccc(-c2cc(COc3cccc(C(F)(F)F)c3CC(=O)O)cc3ccoc23)c1]

Preparation of 2-(2-((7-(3-(aminomethyl)phenyl) benzofuran-5-yl)methoxy)-6-(trifluoromethyl)phenyl)acetic Acid (282f)

Step-1: Preparation of 2-((7-bromobenzofuran-5-yl) methoxy)-6-(trifluoromethyl)benzaldehyde (282b)

Compound 282b was prepared according to the procedure reported in step-2 of scheme-152 from 7-bromo-5-(bromomethyl)benzofuran (152a) (0.6613 g, 2.281 mmol) using 2-hydroxy-6-(trifluoromethyl)benzaldehyde (282a) (0.434 g, 2.281 mmol), $K_2CO_3$ (0.946 g, 6.84 mmol) in DMF (7.5 mL) and stirring at room temperature for 3 h. This gave after workup and purification by flash column chromatography (silica gel, 24 g, eluting with 0 to 20% ethyl acetate in hexanes) 2-((7-bromobenzofuran-5-yl)methoxy)-6-(trifluoromethyl)benzaldehyde (282b) (150 mg, 16% yield) as a pale yellow solid; $^1$H NMR (300 MHz, DMSO-$d_6$) δ 10.24 (d, J=0.7 Hz, 1H), 8.18 (d, J=2.2 Hz, 1H), 8.16-8.05 (m, 2H), 7.81 (d, J=1.5 Hz, 1H), 7.72 (d, J=1.5 Hz, 1H), 7.57 (t, J=7.8 Hz, 1H), 7.17 (d, J=2.2 Hz, 1H), 5.23 (s, 2H).

Step-2: Preparation of 7-bromo-5-((2-(2-(methylsulfinyl)-2-(methylthio)vinyl)-3-(trifluoromethyl) phenoxy)methyl)benzofuran (282c)

Compound 282c was prepared according to the procedure reported in step-3 of scheme-266 from 2-((7-bromobenzofuran-5-yl)methoxy)-6-(trifluoromethyl)benzaldehyde (282b) (145 mg, 0.363 mmol) in THF (40 mL) using methyl(methylsulfinylmethyl)sulfane (72.2 mg, 0.581 mmol), Triton-B (40% methanolic solution) (0.083 mL, 0.182 mmol) and heating at reflux for 2 h. This gave after workup and purification by flash column chromatography (Silica gel, 12 g, eluting with 0-100% EtOAc in hexane) 7-bromo-5-((2-(2-(methylsulfinyl)-2-(methylthio)vinyl)-3-(trifluoromethyl)phenoxy)methyl)benzofuran (282c) (105 mg, 57% yield); $^1$H NMR (300 MHz, DMSO-$d_6$) δ 8.26 (d, J=7.8 Hz, 1H), 8.17 (d, J=2.2 Hz, 1H), 7.84-7.75 (m, 2H), 7.71 (d, J=1.5 Hz, 1H), 7.50 (t, J=7.9 Hz, 1H), 7.16 (d, J=2.2 Hz, 1H), 5.76 (s, 1H), 4.93 (d, J=1.7 Hz, 2H), 2.79 (s, 3H), 2.37 (s, 3H). $^{19}$F NMR (282 MHz, DMSO-$d_6$) δ −59.48.

Step-3: Preparation of Ethyl 2-(2-((7-bromobenzofuran-5-yl)methoxy)-6-(trifluoromethyl)phenyl)acetate (282d)

Compound 282d was prepared according to the procedure reported in step-4 of scheme-266 from 7-bromo-5-((2-(2-

(methylsulfinyl)-2-(methylthio)vinyl)-3-(trifluoromethyl)phenoxy)methyl)benzofuran (282c) (100 mg, 0.198 mmol) in ethanol (10 mL) using HCl (4 M in 1,4-dioxane, 0.247 mL, 0.989 mmol) and heating at reflux for 2 h. This gave after workup and purification by flash column chromatography (silica gel, 12 g, eluting with 0 to 100% ethyl acetate and hexanes) ethyl 2-(2-((7-bromobenzofuran-5-yl)methoxy)-6-(trifluoromethyl)phenyl)acetate (282d) (37 mg, 41% yield); $^1$H NMR (300 MHz, DMSO-d$_6$) δ 8.18 (d, J=2.2 Hz, 1H), 7.76 (d, J=1.5 Hz, 1H), 7.72-7.61 (m, 3H), 7.38 (t, J=7.7 Hz, 1H), 7.18 (d, J=2.2 Hz, 1H), 4.98 (s, 2H), 4.04 (q, J=7.1 Hz, 2H), 3.86 (s, 2H), 1.10 (t, J=7.1 Hz, 3H); $^{19}$F NMR (282 MHz, DMSO) δ−59.01.

Step-4: Preparation of Ethyl 2-(2-((7-(3-(aminomethyl)phenyl)benzofuran-5-yl)methoxy)-6-(trifluoromethyl)phenyl)acetate (282e)

Compound 282e was prepared according to the procedure reported in step-3 of scheme-1 from ethyl 2-(2-((7-bromobenzofuran-5-yl)methoxy)-6-(trifluoromethyl)phenyl)acetate (282d) ((35 mg, 0.077 mmol) in dioxane (2 mL) using 3-(aminomethyl)phenylboronic acid hydrochloride (6c) (17.33 mg, 0.115 mmol), tripotassium phosphate (1.3M, 0.177 mL, 0.230 mmol), tricyclohexylphosphine (6.44 mg, 0.023 mmol) and Pd$_2$(dba)$_3$ (7 mg, 7.65 μmol) under a nitrogen atmosphere and heating at 125° C. for 45 min in a microwave. This gave after workup, purification by flash column chromatography [silica (4 g), eluting 0 to 100% DMA80 in DCM]ethyl 2-(2-((7-(3-(aminomethyl)phenyl)benzofuran-5-yl)methoxy)-6-(trifluoromethyl)phenyl)acetate (282e) (22 mg, 59% yield); $^1$H NMR (300 MHz, Chloroform-d) δ 7.90-7.81 (m, 1H), 7.78 (dt, J=7.7, 1.5 Hz, 1H), 7.72 (dd, J=6.6, 2.0 Hz, 2H), 7.61 (d, J=4.1 Hz, 1H), 7.62-7.51 (m, 2H), 7.55-7.43 (m, 1H), 7.43-7.30 (m, 1H), 7.25 (td, J=7.7, 0.9 Hz, 1H), 6.83 (dd, J=15.6, 2.2 Hz, 1H), 5.07 (s, 2H), 4.14 (q, J=7.1 Hz, 2H), 4.00 (s, 2H), 3.77 (s, 2H), 1.19 (t, J=7.1 Hz, 3H); $^{19}$F NMR (282 MHz, CDCl$_3$) δ−60.20. MS (ES+): 484.2 (M+1).

Step-5: Preparation of 2-(2-((7-(3-(aminomethyl)phenyl)benzofuran-5-yl)methoxy)-6-(trifluoromethyl)phenyl)acetic Acid (282f)

Compound 282f was prepared according to the procedure reported in step-6 of scheme-1 from ethyl 2-(2-((7-(3-(aminomethyl)phenyl)benzofuran-5-yl)methoxy)-6-(trifluoromethyl)phenyl)acetate (282e) (20 mg, 0.041 mmol) in MeOH (1 mL), THF (1 mL) using a solution of lithium hydroxide (4 mg, 0.165 mmol) in water (0.2 mL). This gave after workup and purification by reverse phase column [C18 (15 g), eluting with ACN in water (containing 0.1% HCl) from 0-100%] 2-(2-((7-(3-(aminomethyl)phenyl)benzofuran-5-yl)methoxy)-6-(trifluoromethyl)phenyl)acetic acid (282f) (11 mg, 58% yield) hydrochloride salt as a white solid; $^1$H NMR (300 MHz, DMSO-d$_6$) δ 12.58 (s, 1H), 8.54 (s, 3H), 8.14 (d, J=2.2 Hz, 1H), 8.00-7.98 (m, 1H), 7.96-7.85 (m, 1H), 7.81 (d, J=1.6 Hz, 1H), 7.74-7.57 (m, 5H), 7.37 (t, J=7.7 Hz, 1H), 7.14 (d, J=2.2 Hz, 1H), 5.05 (s, 2H), 4.14 (s, 2H), 3.83 (s, 2H); $^{19}$F NMR (282 MHz, DMSO-d$_6$) δ−58.91; MS (ES+): 456.1 (M+1), (ES−): 454.1 (M−1).

Scheme-283

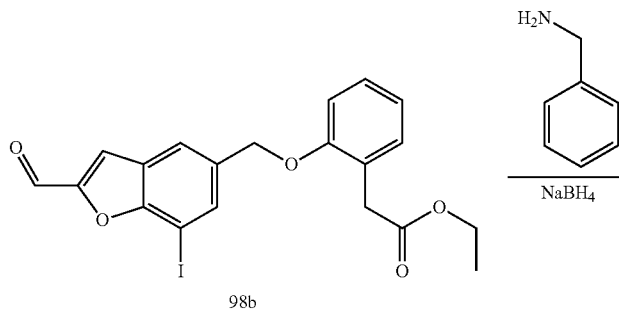

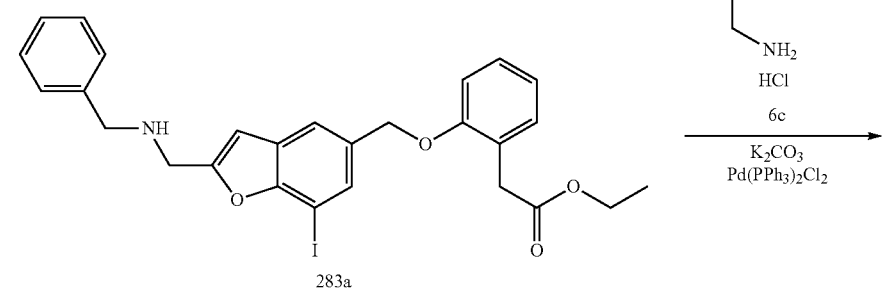

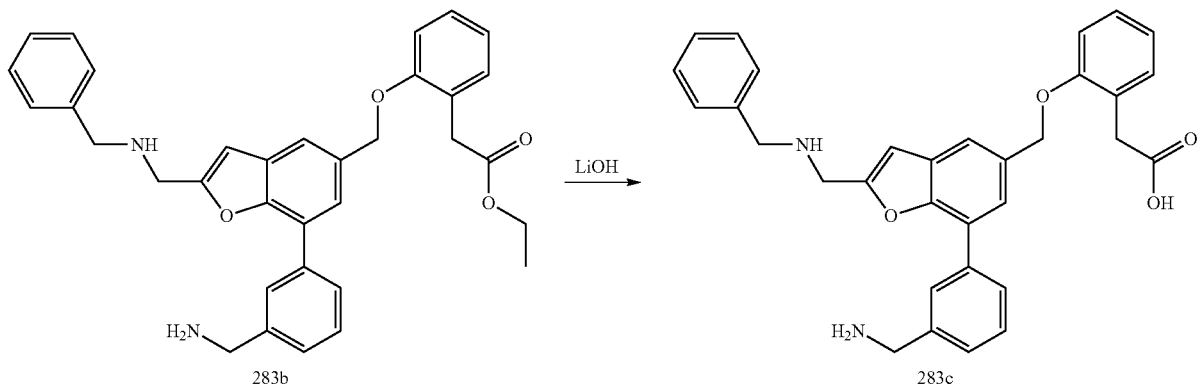

Preparation of 2-(2-((7-(3-(aminomethyl)phenyl)-2-((benzylamino)methyl)benzofuran-5-yl)methoxy)phenyl)acetic Acid (283c)

Step-1: Preparation of Ethyl 2-(2-((2-((benzylamino)methyl)-7-iodobenzofuran-5-yl)methoxy)phenyl)acetate (283a)

Compound 283a was prepared according to the procedure reported in step-1 of scheme-279 from ethyl 2-(2-((2-formyl-7-iodobenzofuran-5-yl)methoxy)phenyl)acetate (98b) (400 mg, 0.862 mmol) in DCM (10 mL) using benzylamine (0.104 mL, 0.948 mmol) and sodium borohydride (65 mg, 1.723 mmol) in ethanol (2 mL). This gave after workup, purification by flash column chromatography (silica gel, eluting with ethyl acetate and hexanes) ethyl 2-(2-((2-((benzylamino)methyl)-7-iodobenzofuran-5-yl)methoxy)phenyl)acetate (283a) (334 mg, 70% yield) as a white solid; $^1$H NMR (300 MHz, DMSO-$d_6$) δ 7.68 (d, J=1.5 Hz, 1H), 7.61 (d, J=1.5 Hz, 1H), 7.39-7.27 (m, 4H), 7.27-7.18 (m, 3H), 7.07 (d, J=8.1 Hz, 1H), 6.95-6.87 (m, 2H), 5.13 (s, 2H), 4.03 (q, J=7.1 Hz, 2H), 3.84 (s, 2H), 3.77 (s, 2H), 3.61 (s, 2H), 1.09 (t, J=7.1 Hz, 3H); MS (ES+): 556.1 (M+1), 578.00 M+Na).

Step-2: Preparation of Ethyl 2-(2-((7-(3-(aminomethyl)phenyl)-2-((benzylamino)methyl)benzofuran-5-yl)methoxy)phenyl)acetate (283b)

Compound 283b was prepared according to the procedure reported in step-3 of scheme-1 from ethyl 2-(2-((2-((benzylamino)methyl)-7-iodobenzofuran-5-yl)methoxy)phenyl)acetate (283a) (322 mg, 0.580 mmol) in dioxane (10 mL) using 3-(aminomethyl)phenylboronic acid hydrochloride (6c) (174 mg, 0.928 mmol), bis(triphenylphosphine)palladium(II) chloride (Pd(PPh$_3$)$_2$Cl$_2$) (61.0 mg, 0.087 mmol) and a solution of K$_2$CO$_3$ (240 mg, 1.739 mmol) in water (3 mL) under an argon atmosphere heating at 100° C. for 6 h on oil bath. This gave after workup and purification by flash column chromatography (silica gel, 40 g, eluting with DMA80 in DCM from 0-50%) ethyl 2-(2-((7-(3-(aminomethyl)phenyl)-2-((benzylamino)methyl)benzofuran-5-yl)methoxy)phenyl)acetate (283b) (210 mg, 68% yield) as a colorless sticky gum; $^1$H NMR (300 MHz, DMSO-$d_6$) δ 7.81 (d, J=1.8 Hz, 1H), 7.74 (dt, J=7.5, 1.6 Hz, 1H), 7.61 (d, J=1.6 Hz, 1H), 7.52 (d, J=1.7 Hz, 1H), 7.46 (t, J=7.5 Hz, 1H), 7.41-7.27 (m, 6H), 7.27-7.18 (m, 3H), 7.11 (dd, J=8.3, 1.2 Hz, 1H), 6.91 (td, J=7.4, 1.1 Hz, 1H), 6.81 (s, 1H), 5.22 (s, 2H), 3.94 (q, J=7.1 Hz, 2H), 3.84 (s, 2H), 3.81 (s, 2H), 3.77 (s, 2H), 3.63 (s, 2H), 1.00 (t, J=7.1 Hz, 3H); MS (ES+): 535.3 (M+1), (ES−): 557.2 (M+Na).

Step-3: Preparation of 2-(2-((7-(3-(aminomethyl)phenyl)-2-((benzylamino)methyl)benzofuran-5-yl)methoxy)phenyl)acetic Acid (283c)

Compound 283c was prepared according to the procedure reported in step-6 of scheme-1 from ethyl 2-(2-((7-(3-(aminomethyl)phenyl)-2-((benzylamino)methyl)benzofuran-5-yl)methoxy)phenyl)acetate (283b) (200 mg, 0.374 mmol) in THF/MeOH (10:4 mL, each) using a solution of lithium hydroxide hydrate (36 mg, 1.496 mmol) in water (2 mL). This gave after workup and purification by reverse phase column chromatography [C18 column, 50 g, eluting with water (containing 0.1% HCl)/acetonitrile (1:0 to 0:1)] 2-(2-((7-(3-(aminomethyl)phenyl)-2-((benzylamino)methyl)benzofuran-5-yl)methoxy)phenyl)acetic acid (283c) (145 mg, 77% yield) hydrochloride salt as a white solid; $^1$H NMR (300 MHz, DMSO-$d_6$) δ 12.22 (s, 1H), 10.07 (s, 2H), 8.51 (s, 3H), 8.20 (s, 1H), 7.99 (d, J=7.4 Hz, 1H), 7.78 (d, J=1.6 Hz, 1H), 7.71 (d, J=1.7 Hz, 1H), 7.65-7.57 (m, 3H), 7.57-7.51 (m, 1H), 7.42 (dd, J=5.0, 1.9 Hz, 3H), 7.24 (s, 1H), 7.21 (s, 1H), 7.20 (s, 1H), 7.09 (d, J=8.1 Hz, 1H), 6.94-6.86 (m, 1H), 5.27 (s, 2H), 4.42 (s, 2H), 4.26 (s, 2H), 4.17 (s, 2H), 3.60 (s, 2H); MS (ES+): 507.20 (M+1), (ES−): 505.30 (M−1); analysis Calculated for C$_{32}$H$_{30}$N$_2$O$_4$.2HCl.2H$_2$O: C, 62.44; H, 5.90; Cl, 11.52; N, 4.55; Found: C, 62.61; H, 5.70; Cl, 11.25; N, 4.60.

Scheme-284

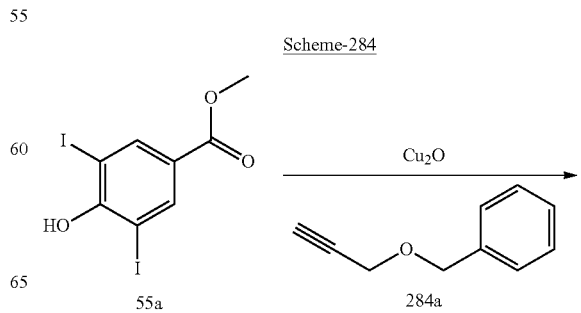

959
-continued

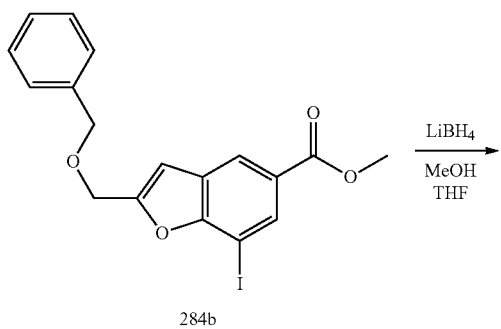

284b

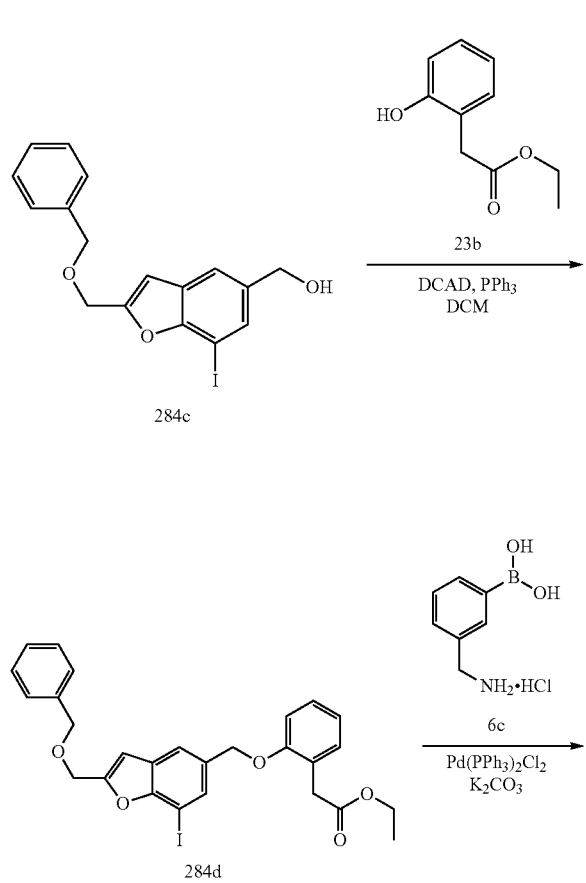

960
-continued

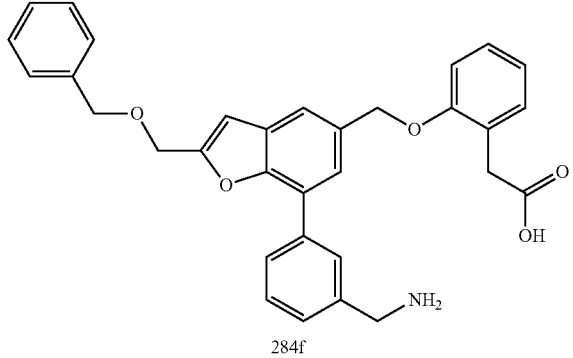

284f

Preparation of 2-(2-((7-(3-(aminomethyl)phenyl)-2-((benzyloxy)methyl)benzofuran-5-yl)methoxy)phenyl)acetic Acid (284f)

Step-1: Preparation of methyl 2-((benzyloxy)methyl)-7-iodobenzofuran-5-carboxylate (284b)

Compound 284b was prepared according to the procedure reported in step-1 of scheme-55, from methyl 4-hydroxy-3,5-diiodobenzoate (55a) (2 g, 4.95 mmol) in pyridine (8 mL) using ((prop-2-yn-1-yloxy)methyl)benzene (284a) (0.724 mmol, 4.95 mmol), copper(I) oxide (0.354 g, 2.476 mmol) and heating at 50° C. for 18 h on an oil bath. This gave after workup and purification by flash column chromatography [silica (40g), eluting with EtOAc in hexane from 0-40%] methyl 2-((benzyloxy)methyl)-7-iodobenzofuran-5-carboxylate (284b) (1.481 g, 71% yield) as an off-white solid; $^1$H NMR (300 MHz, DMSO-$d_6$) δ 8.28 (d, J=1.6 Hz, 1H), 8.23 (d, J=1.6 Hz, 1H), 7.41-7.35 (m, 4H), 7.35-7.26 (m, 1H), 7.21 (d, J=0.7 Hz, 1H), 4.71 (d, J=0.7 Hz, 2H), 4.61 (s, 2H), 3.87 (s, 3H).

Step-2: Preparation of (2-((benzyloxy)methyl)-7-iodobenzofuran-5-yl)methanol (284c)

Compound 284c was prepared according to the procedure reported in step-2 of scheme-76 from methyl 2-((benzyloxy)methyl)-7-iodobenzofuran-5-carboxylate (284b) (1 g, 2.368 mmol) in THF (20 mL) using LiBH$_4$ (2.072 mL, 8.29 mmol, 2 M solution in THF) and MeOH (0.335 mL, 8.29 mmol). This gave after workup and purification by flash column chromatography [silica (24g), eluting with EtOAc in hexane] (2-((benzyloxy)methyl)-7-iodobenzofuran-5-yl)methanol (284c) (900 mg, 96% yield) as a clear oil; $^1$H NMR (300 MHz, DMSO-$d_6$) δ 7.69-7.62 (m, 1H), 7.55 (dd, J=1.5, 0.8 Hz, 1H), 7.42-7.25 (m, 5H), 7.06 (s, 1H), 5.28 (t, J=5.8 Hz, 1H), 4.68-4.65 (m, 2H), 4.59 (s, 2H), 4.54 (dt, J=5.9, 0.7 Hz, 2H).

Step-3: Preparation of Ethyl 2-(2-((2-((benzyloxy)methyl)-7-iodobenzofuran-5-yl)methoxy)phenyl)acetate (284d)

Compound 284d was prepared according to the procedure reported in step-2 of scheme-23 from (2-((benzyloxy)methyl)-7-iodobenzofuran-5-yl)methanol (284c) (600 mg, 1.522 mmol) in DCM (30 mL) using triphenylphosphine (479 mg, 1.826 mmol), ethyl 2-(2-hydroxyphenyl) acetate (23b) (274 mg, 1.522 mmol) and bis(4-chlorobenzyl) diazene-1,2-dicarboxylate (DCAD, 754 mg, 2.055 mmol) in DCM (10 mL). This gave after workup and purification by flash column chromatography [silica (40g), eluting with EtOAc in hexane from 0-40%] ethyl 2-(2-((2-((benzyloxy)methyl)-7-iodobenzofuran-5-yl)methoxy)phenyl)acetate (284d) (358 mg, 42% yield) as a clear syrup; $^1$H NMR (300 MHz, DMSO-d$_6$) δ 7.75 (d, J=1.5 Hz, 1H), 7.67 (d, J=1.5 Hz, 1H), 7.43-7.17 (m, 7H), 7.14-7.02 (m, 2H), 6.91 (td, J=7.4, 1.1 Hz, 1H), 5.15 (s, 2H), 4.69 (s, 2H), 4.60 (s, 2H), 4.03 (q, J=7.2 Hz, 2H), 3.62 (s, 2H), 1.09 (t, J=7.1 Hz, 3H); MS (ES+): 579.0 (M+Na).

Step-4: Preparation of Ethyl 2-(2-((7-(3-(aminomethyl)phenyl)-2-((benzyloxy)methyl)benzofuran-5-yl)methoxy)phenyl)acetate (284e)

Compound 284e was prepared according to the procedure reported in step-3 of scheme-1 from ethyl 2-(2-((2-((benzyloxy)methyl)-7-iodobenzofuran-5-yl)methoxy)phenyl)acetate (284d) (350 mg, 0.629 mmol) in dioxane (10 mL) using 3-(aminomethyl)phenylboronic acid hydrochloride (6c) (118 mg, 0.629 mmol), a solution of K$_2$CO$_3$ (261 mg, 1.887 mmol) in water (2 mL), bis(triphenylphosphine)palladium (II) chloride (66 mg, 0.094 mmol) and heating at 100° C. for 12h on oil bath. This gave after workup, purification by flash column chromatography [silica (24 g), eluting with DMA80 in DCM from 0-90%] ethyl 2-(2-((7-(3-(aminomethyl)phenyl)-2-((benzyloxy)methyl)benzofuran-5-yl)methoxy)phenyl)acetate (284e) (185 mg, 55% yield) as a sticky material; $^1$H NMR (300 MHz, DMSO-d$_6$) δ 7.81 (d, J=1.7 Hz, 1H), 7.72 (dt, J=7.6, 1.6 Hz, 1H), 7.66 (d, J=1.6 Hz, 1H), 7.57 (d, J=1.7 Hz, 1H), 7.47 (t, J=7.6 Hz, 1H), 7.43-7.38 (m, 1H), 7.40-7.31 (m, 4H), 7.33-7.27 (m, 1H), 7.27-7.20 (m, 2H), 7.12 (dd, J=8.3, 1.1 Hz, 1H), 7.01 (s, 1H), 6.91 (td, J=7.4, 1.1 Hz, 1H), 5.24 (s, 2H), 4.69 (s, 2H), 4.60 (s, 2H), 3.93 (q, J=7.1 Hz, 2H), 3.81 (s, 2H), 3.63 (s, 2H), 0.99 (t, J=7.1 Hz, 3H); MS (ES+): 536.2 (M+1).

Step-5: Preparation of 2-(2-((7-(3-(aminomethyl)phenyl)-2-((benzyloxy)methyl)benzofuran-5-yl)methoxy)phenyl)acetic Acid (284f)

Compound 284f was prepared according to the procedure reported in step-6 of scheme-1 from ethyl 2-(2-((7-(3-(aminomethyl)phenyl)-2-((benzyloxy)methyl)benzofuran-5-yl)methoxy)phenyl)acetate (284e) (180 mg, 0.336 mmol) in MeOH/THF (2/10 mL) using a solution of lithium hydroxide monohydrate (24 mg, 1.008 mmol) in water (2.0 mL). This gave after workup and purification by reverse-phase column chromatography [EZ-PREP, C-18 column, 50 g, eluting with 0.1% aqueous HCl in water and acetonitrile from 0-100%] 2-(2-((7-(3-(aminomethyl)phenyl)-2-((benzyloxy)methyl)benzofuran-5-yl)methoxy)phenyl)acetic acid (284f) (29 mg, 17% yield) hydrochloride salt as a white solid; $^1$H NMR (300 MHz, DMSO-d$_6$) δ 8.74-8.02 (m, 3H), 7.94 (dd, J=7.4, 1.5 Hz, 2H), 7.74 (d, J=1.6 Hz, 1H), 7.63 (d, J=1.8 Hz, 1H), 7.60 (d, J=7.8 Hz, 1H), 7.56-7.51 (m, 1H), 7.36 (d, J=4.4 Hz, 4H), 7.33-7.25 (m, 1H), 7.24 (s, 1H), 7.21 (s, 1H), 7.09 (d, J=8.1 Hz, 1H), 7.03 (s, 1H), 6.91 (td, J=7.4, 1.1 Hz, 1H), 5.26 (s, 2H), 4.70 (s, 2H), 4.60 (s, 2H), 4.14 (s, 2H), 3.60 (s, 2H); MS (ES+) 508.20 (M+1), (ES−) 506.20 (M−1); Analysis calculated for C$_{32}$H$_{29}$NO$_5$.1.2HCl.1.5H$_2$O: C, C, 66.45; H, 5.79; Cl, 7.36; N, 2.42; Found, C, 66.80; H, 5.76; Cl, 7.00; N, 2.46.

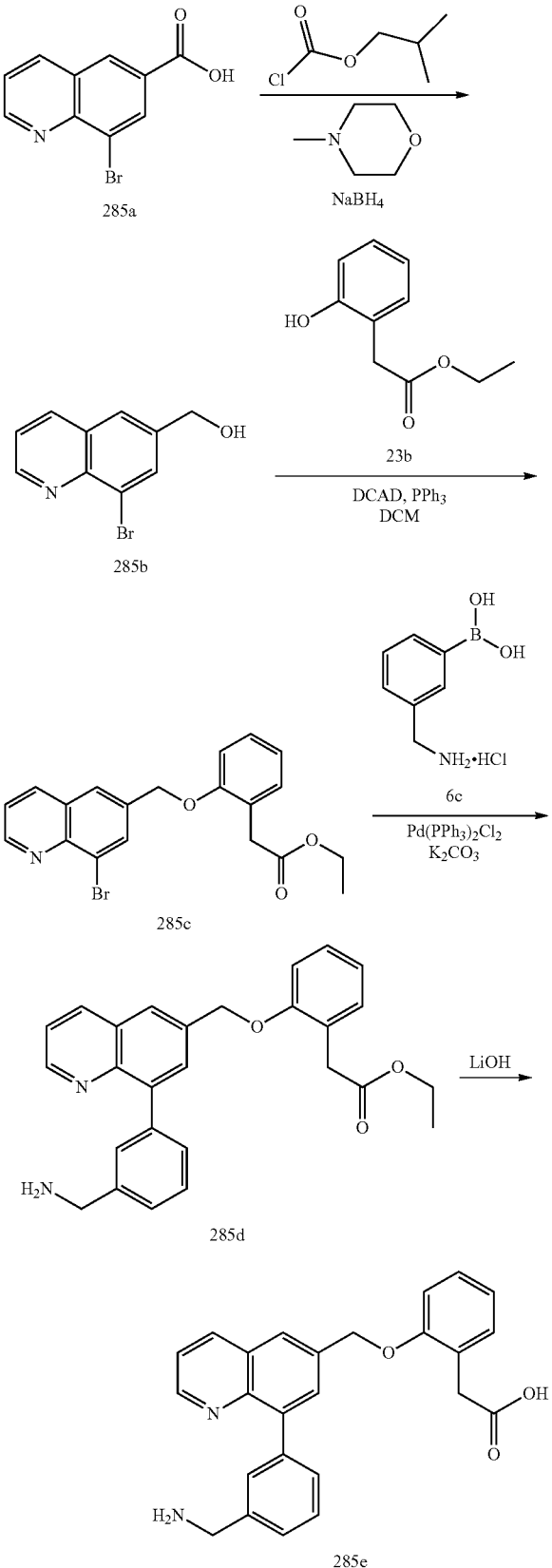

Scheme-285

Preparation of 2-(2-((8-(3-(aminomethyl)phenyl)quinolin-6-yl)methoxy)phenyl)acetic acid (285e)

Step-1: Preparation of (8-bromoquinolin-6-yl)methanol (285b)

Compound 285b was prepared according to the procedure reported in step-1 of scheme-23 from 8-bromoquinoline-6-carboxylic acid (285a) (1 g, 3.97 mmol; CAS #791632-21-8) using N-methylmorpholine (0.523 mL, 4.76 mmol) in THF (20 mL), isobutyl chloroformate (0.625 mL, 4.76 mmol) and NaBH$_4$ (0.450 g, 11.90 mmol) in water (1 mL). This gave after workup (8-bromoquinolin-6-yl)methanol (285b) (660 mg, 70% yield) as a white solid; $^1$H NMR (300 MHz, DMSO-d$_6$) δ 8.97 (dd, J=4.2, 1.7 Hz, 1H), 8.42 (dd, J=8.3, 1.7 Hz, 1H), 8.09 (d, J=1.8 Hz, 1H), 7.93 (q, J=1.2 Hz, 1H), 7.62 (dd, J=8.3, 4.2 Hz, 1H), 5.52 (t, J=5.8 Hz, 1H), 4.69 (dt, J=5.8, 0.7 Hz, 2H); MS (ES+): 240.0, 238.0 (M, M+2).

Step-2: Preparation of Ethyl 2-(2-((8-bromoquinolin-6-yl)methoxy)phenyl)acetate (285c)

Compound 285c was prepared according to the procedure reported in step-2 of scheme-23 from (8-bromoquinolin-6-yl)methanol (285b) (650 mg, 2.73 mmol) in DCM (35 mL) using triphenylphosphine (859 mg, 3.28 mmol), ethyl 2-(2-hydroxyphenyl) acetate (23b) (541 mg, 3.0 mmol) and bis(4-chlorobenzyl) diazene-1,2-dicarboxylate (DCAD, 1353 mg, 3.69 mmol) in DCM (20 mL). This gave after workup and purification by flash column chromatography [silica (40g), eluting with EtOAc in hexane from 0-40%] ethyl 2-(2-((8-bromoquinolin-6-yl)methoxy)phenyl)acetate (285c) (690 mg, 63% yield) as a clear syrup; $^1$H NMR (300 MHz, DMSO-d$_6$) δ 9.02 (dd, J=4.2, 1.7 Hz, 1H), 8.41 (dd, J=8.4, 1.7 Hz, 1H), 8.17 (d, J=1.8 Hz, 1H), 8.06 (d, J=1.7 Hz, 1H), 7.66 (dd, J=8.3, 4.2 Hz, 1H), 7.29-7.21 (m, 2H), 7.14-7.05 (m, 1H), 6.93 (td, J=7.4, 1.1 Hz, 1H), 5.31 (s, 2H), 4.03 (q, J=7.1 Hz, 2H), 3.68 (s, 2H), 1.06 (t, J=7.1 Hz, 3H).

Step-3: Preparation of Ethyl 2-(2-((8-(3-(aminomethyl)phenyl)quinolin-6-yl)methoxy)phenyl)acetate (285d)

Compound 285d was prepared according to the procedure reported in step-3 of scheme-1 from ethyl 2-(2-((8-bromoquinolin-6-yl)methoxy)phenyl)acetate (285c) (680 mg, 1.699 mmol) in dioxane (10 mL) using 3-(aminomethyl) phenylboronic acid hydrochloride (6c) (509 mg, 2.72 mmol), a solution of K$_2$CO$_3$ (704 mg, 5.10 mmol) in water (3 mL), bis(triphenylphosphine)palladium(II) chloride (179 mg, 0.255 mmol) and heating at 100° C. for 8 h on oil bath. This gave after workup, purification by flash column chromatography [silica (40 g), eluting with DMA80 in DCM from 0-50%] ethyl 2-(2-((8-(3-(aminomethyl)phenyl)quinolin-6-yl)methoxy)phenyl)acetate (285d) (290 mg, 40% yield) as a colorless syrup; $^1$H NMR (300 MHz, DMSO-d$_6$) δ 8.91 (dd, J=4.1, 1.7 Hz, 1H), 8.53-8.42 (m, 1H), 8.35 (s, 3H), 8.10 (s, 1H), 7.86 (d, J=1.9 Hz, 1H), 7.78 (s, 1H), 7.72 (d, J=4.6 Hz, 1H), 7.62 (dd, J=8.3, 4.2 Hz, 1H), 7.54 (d, J=4.7 Hz, 2H), 7.24 (d, J=7.1 Hz, 2H), 7.11 (d, J=8.4 Hz, 1H), 6.92 (t, J=7.3 Hz, 1H), 5.39 (s, 2H), 4.21-4.06 (m, 2H), 3.64 (s, 2H); MS (ES+): 427 (M+1).

Step-4: Preparation of 2-(2-((8-(3-(aminomethyl)phenyl)quinolin-6-yl)methoxy)phenyl)acetic Acid (285e)

Compound 285e was prepared according to the procedure reported in step-6 of scheme-1 from ethyl 2-(2-((8-(3-(aminomethyl)phenyl)quinolin-6-yl)methoxy)phenyl)acetate (285d) (280 mg, 0.656 mmol) in MeOH/THF (3/10 mL) using a solution of lithium hydroxide monohydrate (63 mg, 2.63 mmol) in water (3 mL). This gave after workup and purification by reverse-phase column chromatography [EZ-PREP, C-18 column, 50 g, eluting with 0.1% aqueous HCl in water and acetonitrile from 0-100%] 2-(2-((8-(3-(aminomethyl)phenyl)quinolin-6-yl)methoxy)phenyl)acetic acid (285e) (5 mg, 2% yield) hydrochloride salt as a white solid; $^1$H NMR (300 MHz, DMSO-d$_6$) δ 8.91 (dd, J=4.2, 1.7 Hz, 1H), 8.45 (dd, J=8.4, 1.8 Hz, 1H), 8.35 (s, 3H), 8.10 (d, J=1.9 Hz, 1H), 7.86 (d, J=2.0 Hz, 1H), 7.78 (s, 1H), 7.75-7.70 (m, 1H), 7.62 (dd, J=8.3, 4.2 Hz, 1H), 7.57-7.50 (m, 2H), 7.25 (dh, J=7.6, 1.8 Hz, 2H), 7.15-7.07 (m, 1H), 6.92 (t, J=7.3 Hz, 1H), 5.39 (s, 2H), 4.12 (q, J=6.0, 5.5 Hz, 2H), 3.64 (s, 2H); MS (ES+): 399.10 (M+1), (ES−): 397.20 (M−1).

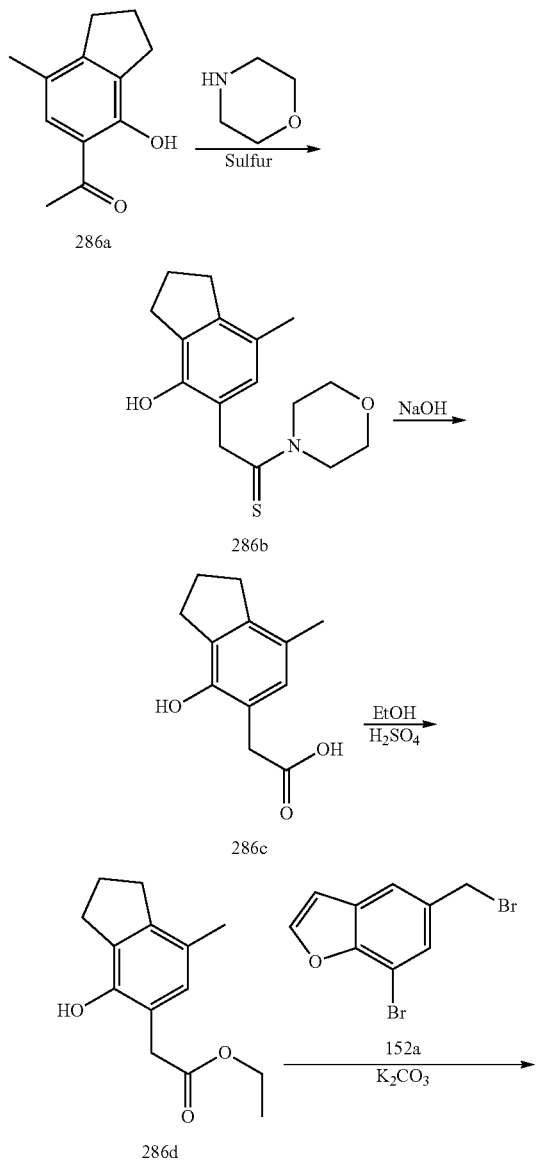

Scheme-286

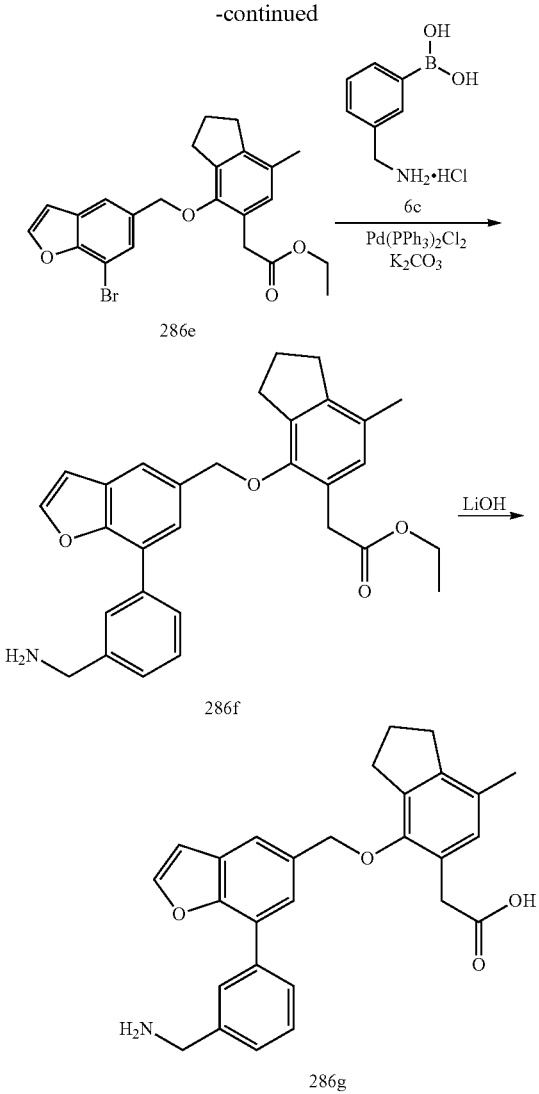

Preparation of 2-(4-((7-(3-(aminomethyl)phenyl)benzofuran-5-yl)methoxy)-7-methyl-2,3-dihydro-1H-inden-5-yl)acetic Acid (286g)

Step-1: Preparation of 2-(4-hydroxy-7-methyl-2,3-dihydro-1H-inden-5-yl)-1-morpholinoethanethione (286b)

Compound 286b was prepared according to the procedure reported in step-1 of scheme-265 from 1-(4-hydroxy-7-methyl-2,3-dihydro-1H-inden-5-yl)ethan-1-one (286a) (1 g, 5.26 mmol; CAS #175136-13-7) in N-Methyl-2-pyrrolidinone (3 mL) using sulfur powder (0.337 g, 10.51 mmol), morpholine (0.907 mL, 10.51 mmol) and heating at 130° C. for 10 h. This gave after workup and purification by flash column chromatography (silica gel) 2-(4-hydroxy-7-methyl-2,3-dihydro-1H-inden-5-yl)-1-morpholinoethanethione (286b) (1.15 g, 75% yield) as a buff solid; $^1$H NMR (300 MHz, DMSO-$d_6$) δ 8.53 (s, 1H), 6.76 (s, 1H), 4.28-4.18 (m, 2H), 4.10 (s, 2H), 3.74-3.59 (m, 4H), 3.43 (dd, J=5.7, 4.0 Hz, 2H), 2.79 (t, J=7.4 Hz, 2H), 2.72 (t, J=7.4 Hz, 2H), 2.11-2.05 (m, 3H), 2.03-1.91 (m, 2H); MS (ES+): 292.1 (M+1), 314.1 (M+Na), (ES−): 290.1 (M−1).

Step-2: Preparation of 2-(4-hydroxy-7-methyl-2,3-dihydro-1H-inden-5-yl)acetic Acid (286c)

Compound 286c was prepared according to the procedure reported in step-2 of scheme-265 from 2-(4-hydroxy-7-methyl-2,3-dihydro-1H-inden-5-yl)-1-morpholinoethanethione (286b) (1.14 g, 3.91 mmol) in ethanol (20 mL) and water (5 mL) using sodium hydroxide (0.806 g, 20.15 mmol) and heating at reflux for 12 h. This gave after workup 2-(4-hydroxy-7-methyl-2,3-dihydro-1H-inden-5-yl)acetic acid (286c) (704 mg, 87% yield) as a white solid; $^1$H NMR (300 MHz, DMSO-$d_6$) δ 12.02 (s, 1H), 8.33 (s, 1H), 6.67 (s, 1H), 3.41 (s, 2H), 2.74 (dt, J=18.2, 7.4 Hz, 4H), 2.08 (s, 3H), 1.97 (p, J=7.5 Hz, 2H); MS (ES+): 207.1 (M+1), 229.1 (M+Na), (ES−): 205.1 (M−1).

Step-3: Preparation of Ethyl 2-(4-hydroxy-7-methyl-2,3-dihydro-1H-inden-5-yl)acetate (286d)

Compound 286d was prepared according to the procedure reported in step-3 of scheme-265 from 2-(4-hydroxy-7-methyl-2,3-dihydro-1H-inden-5-yl)acetic acid (286c) (700 mg, 3.39 mmol) in ethanol (20 mL) using sulfuric acid (0.208 mL, 3.90 mmol) and heating at reflux for 4 h. This gave after workup and purification by flash column chromatography (silica gel, 40 g, eluting with ethyl acetate and hexanes) ethyl 2-(4-hydroxy-7-methyl-2,3-dihydro-1H-inden-5-yl)acetate (286d) (685 mg, 86% yield) as white solid; $^1$H NMR (300 MHz, DMSO-$d_6$) δ 8.35 (s, 1H), 6.68 (d, J=1.1 Hz, 1H), 4.04 (q, J=7.1 Hz, 2H), 3.49 (s, 2H), 2.77 (t, J=7.6 Hz, 2H), 2.71 (t, J=7.6 Hz, 2H), 2.08 (d, J=0.7 Hz, 3H), 2.03-1.91 (m, 2H), 1.17 (t, J=7.1 Hz, 3H); MS (ES+): 234.1 (M+1), 257.1 (M+Na).

Step-4: Preparation of Ethyl 2-(4-((7-bromobenzofuran-5-yl)methoxy)-7-methyl-2,3-dihydro-1H-inden-5-yl)acetate (286e)

Compound 286e was prepared according to the procedure reported in step-2 of scheme-152 from 7-bromo-5-(bromomethyl)benzofuran (152a) (842 mg, 2.90 mmol) using ethyl 2-(4-hydroxy-7-methyl-2,3-dihydro-1H-inden-5-yl)acetate (286d) (680 mg, 2.90 mmol), $K_2CO_3$ (1203 mg, 8.71 mmol) in DMF (5 mL) and stirring at room temperature for 12h. This gave after workup and purification by flash column chromatography ($SiO_2$, 40 g, eluting with EtOAc in hexane) ethyl 2-(4-((7-bromobenzofuran-5-yl)methoxy)-7-methyl-2,3-dihydro-1H-inden-5-yl)acetate (286e) (700 mg, 54% yield) as a white foam; $^1$H NMR (300 MHz, DMSO-$d_6$) δ 8.14 (d, J=2.2 Hz, 1H), 7.72 (d, J=1.5 Hz, 1H), 7.61 (d, J=1.5 Hz, 1H), 7.12 (d, J=2.2 Hz, 1H), 6.83 (s, 1H), 4.93 (s, 2H), 3.97 (q, J=7.1 Hz, 2H), 3.54 (s, 2H), 2.97 (t, J=7.4 Hz, 2H), 2.77 (t, J=7.4 Hz, 2H), 2.21-2.11 (m, 3H), 2.09-1.94 (m, 2H), 1.09 (t, J=7.1 Hz, 3H); MS (ES+): 443.1, 445.1 (M, M+2), 465.0, 467.0 (M+Na).

Step-5: Preparation of Ethyl 2-(4-((7-(3-(aminomethyl)phenyl)benzofuran-5-yl)methoxy)-7-methyl-2,3-dihydro-1H-inden-5-yl)acetate (286f)

Compound 286f was prepared according to the procedure reported in step-3 of scheme-1 from ethyl 2-(4-((7-bromobenzofuran-5-yl)methoxy)-7-methyl-2,3-dihydro-1H-inden-5-yl)acetate (286e) (690 mg, 1.556 mmol) in dioxane (10 mL) using 3-(aminomethyl)phenylboronic acid hydrochloride (6c) (467 mg, 2.490 mmol), bis(triphenylphosphine)palladium(II) chloride (Pd(PPh$_3$)$_2$Cl$_2$) (164 mg, 0.233 mmol), potassium carbonate (645 mg, 4.67 mmol) in water (3 mL) under an argon atmosphere heating at 100° C. for 8 h on oil bath. This gave after workup, purification by flash column chromatography (silica gel, 40 g, eluting with DMA-80 in DCM from 0-50%) ethyl 2-(4-((7-(3-(aminomethyl)phenyl)benzofuran-5-yl)methoxy)-7-methyl-2,3-dihydro-1H-inden-5-yl)acetate (286f) (590 mg, 81% yield) as a colorless syrup; $^1$H NMR (300 MHz, DMSO-d$_6$) δ 8.09 (d, J=2.2 Hz, 1H), 7.79 (d, J=1.7 Hz, 1H), 7.69 (tt, J=3.3, 1.6 Hz, 2H), 7.55 (d, J=1.7 Hz, 1H), 7.47 (t, J=7.6 Hz, 1H), 7.43-7.36 (m, 1H), 7.06 (d, J=2.2 Hz, 1H), 6.84 (s, 1H), 5.00 (s, 2H), 3.94 (q, J=7.1 Hz, 2H), 3.82 (s, 2H), 3.56 (s, 2H), 3.00 (t, J=7.4 Hz, 2H), 2.78 (t, J=7.4 Hz, 2H), 2.16 (s, 3H), 2.09-1.97 (m, 2H), 1.03 (t, J=7.1 Hz, 3H); MS (ES+): 470.2 (M+1).

Step-6: Preparation of 2-(4-((7-(3-(aminomethyl)phenyl)benzofuran-5-yl)methoxy)-7-methyl-2,3-dihydro-1H-inden-5-yl)acetic Acid (286g)

Compound 286g was prepared according to the procedure reported in step-6 of scheme-1 from ethyl 2-(4-((7-(3-(aminomethyl)phenyl)benzofuran-5-yl)methoxy)-7-methyl-2,3-dihydro-1H-inden-5-yl)acetate (286f) (583 mg, 1.242 mmol) in MeOH (3 mL), THF (15 mL) using lithium hydroxide monohydrate (119 mg, 4.97 mmol) in water (3 mL). This gave after workup and purification by reverse phase column [C18 (50g), eluting with ACN in water (containing 0.1% HCl) from 0-100%] 2-(4-((7-(3-(aminomethyl)phenyl)benzofuran-5-yl)methoxy)-7-methyl-2,3-dihydro-1H-inden-5-yl)acetic acid (286g) (320 mg, 58% yield) hydrochloride salt as a white solid; $^1$H NMR (300 MHz, DMSO-d$_6$) δ 8.11 (d, J=2.2 Hz, 1H), 7.98 (d, J=1.7 Hz, 1H), 7.92 (dt, J=7.4, 1.7 Hz, 1H), 7.76 (d, J=1.6 Hz, 1H), 7.64 (d, J=1.7 Hz, 1H), 7.60 (t, J=7.6 Hz, 1H), 7.55 (dt, J=7.7, 1.6 Hz, 1H), 7.09 (d, J=2.2 Hz, 1H), 6.85 (s, 1H), 5.00 (s, 2H), 4.14 (s, 2H), 3.51 (s, 2H), 2.99 (t, J=7.4 Hz, 2H), 2.77 (t, J=7.4 Hz, 2H), 2.16 (s, 3H), 2.08-1.95 (m, 2H); MS (ES+): 442.02 (M+1), (ES−): 440.2 (M−1); analysis calculated for C$_{28}$H$_{27}$NO$_4$HCl.075H$_2$O: C, 68.43; H, 6.05; Cl, 7.21; N, 2.85; Found C, 68.54; H, 6.11; Cl, 7.21; N, 2.84.

Scheme-287

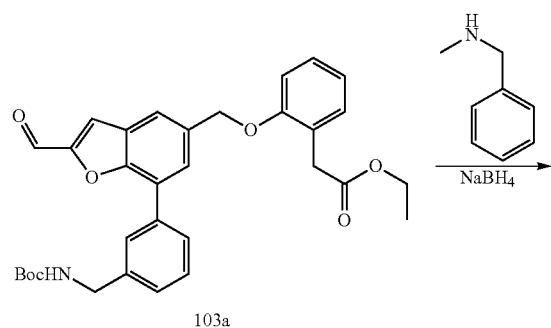

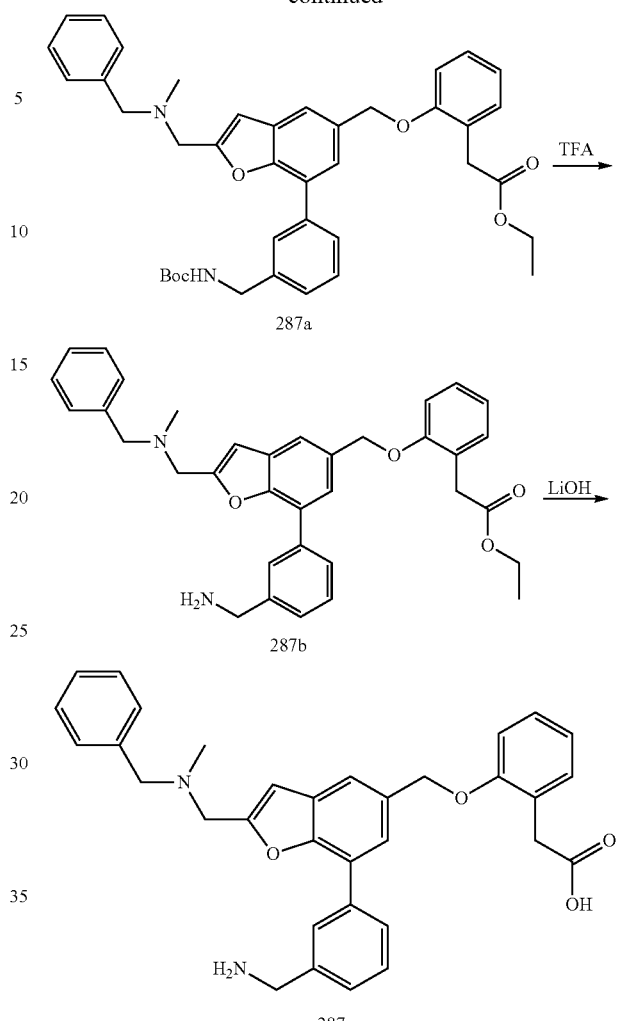

Preparation of 2-(2-((7-(3-(aminomethyl)phenyl)-2-((benzyl(methyl)amino)methyl)benzofuran-5-yl)methoxy)phenyl)acetic Acid (287c)

Step-1: Preparation of Ethyl 2-(2-((2-((benzyl(methyl)amino)methyl)-7-(3-(((tert-butoxycarbonyl)amino)methyl)phenyl)benzofuran-5-yl)methoxy)phenyl)acetate (287a)

Compound 287a was prepared according to the procedure reported in step-1 of scheme-279 from ethyl 2-(2-((7-(3-(((tert-butoxycarbonyl)amino)methyl)phenyl)-2-formylbenzofuran-5-yl)methoxy)phenyl)acetate (103a) (500 mg, 0.920 mmol) in THF (20 mL) using N-methyl-1-phenylmethanamine (139 mg, 1.150 mmol) and sodium borohydride (87 mg, 2.299 mmol) in ethanol (4 mL). This gave after workup, purification by flash column chromatography (silica gel) ethyl 2-(2-((2-((benzyl(methyl)amino)methyl)-7-(3-(((tert-butoxycarbonyl)amino)methyl)phenyl)benzofuran-5-yl)methoxy)phenyl)acetate (287a) (330 mg, 55% yield) as a light brown syrup; MS (ES+): 649.3 (M+1).

Step-2: Preparation of Ethyl 2-(2-((7-(3-(aminomethyl)phenyl)-2-((benzyl(methyl)amino)methyl)benzofuran-5-yl)methoxy)phenyl)acetate (287b)

Compound 287b was prepared according to the procedure reported in step-5 of scheme-1 from ethyl 2-(2-((2-((benzyl(methyl)amino)methyl)-7-(3-(((tert-butoxycarbonyl)amino)methyl)phenyl)benzofuran-5-yl)methoxy)phenyl)acetate (287a) (330 mg, 0.509 mmol) in DCM (10 mL) using TFA (0.392 mL, 5.09 mmol). This gave after workup ethyl 2-(2-((7-(3-(aminomethyl)phenyl)-2-((benzyl(methyl)amino)methyl)benzofuran-5-yl)methoxy)phenyl)acetate (287b) (337 mg, 100% yield) as a brown syrup. MS (ES+): 549.2 (M+1)

Step-3: Preparation of 2-(2-((7-(3-(aminomethyl)phenyl)-2-((benzyl(methyl)amino)methyl)benzofuran-5-yl)methoxy)phenyl)acetic Acid (287c)

Compound 287c was prepared according to the procedure reported in step-6 of scheme-1 from ethyl 2-(2-((7-(3-(aminomethyl)phenyl)-2-((benzyl(methyl)amino)methyl)benzofuran-5-yl)methoxy)phenyl)acetate (287b) (337 mg, 0.509 mmol) in THF/MeOH (10:2 mL, each) using a solution of lithium hydroxide hydrate (49 mg, 2.034 mmol) in water (2 mL). This gave after workup and purification by reverse phase column chromatography [C18 column, 50 g, eluting with water (containing 0.1% HCl)/acetonitrile (1:0 to 0:1)] 2-(2-((7-(3-(aminomethyl)phenyl)-2-((benzyl(methyl)amino)methyl)benzofuran-5-yl)methoxy)phenyl)acetic acid (287c) (174 mg, 66% yield) hydrochloride salt as a white solid; $^1$H NMR (300 MHz, DMSO-$d_6$) δ 12.27 (s, 1H), 11.75 (s, 1H), 8.66 (s, 3H), 8.24 (s, 1H), 7.98 (ddd, J=5.7, 3.2, 1.8 Hz, 1H), 7.80 (d, J=1.6 Hz, 1H), 7.74 (d, J=1.6 Hz, 1H), 7.70 (d, J=5.4 Hz, 2H), 7.61-7.53 (m, 2H), 7.45 (h, J=1.9 Hz, 3H), 7.34 (s, 1H), 7.24 (t, J=7.4 Hz, 2H), 7.13-7.07 (m, 1H), 6.90 (td, J=7.4, 1.1 Hz, 1H), 5.28 (s, 2H), 4.59 (s, 2H), 4.54-4.29 (m, 2H), 4.16 (d, J=5.7 Hz, 2H), 3.60 (s, 2H), 2.69 (s, 3H); MS (ES+): 521.20 (M+1), (ES−): 519.20 (M−1); analysis calculated for $C_{33}H_{32}N_2O_4 \cdot 2HCl \cdot 2H_2O$: C, 62.96; H, 6.08; Cl, 11.26; N, 4.45; Found; C, 62.59; H, 5.74; Cl, 11.27; N, 4.31.

Scheme-288

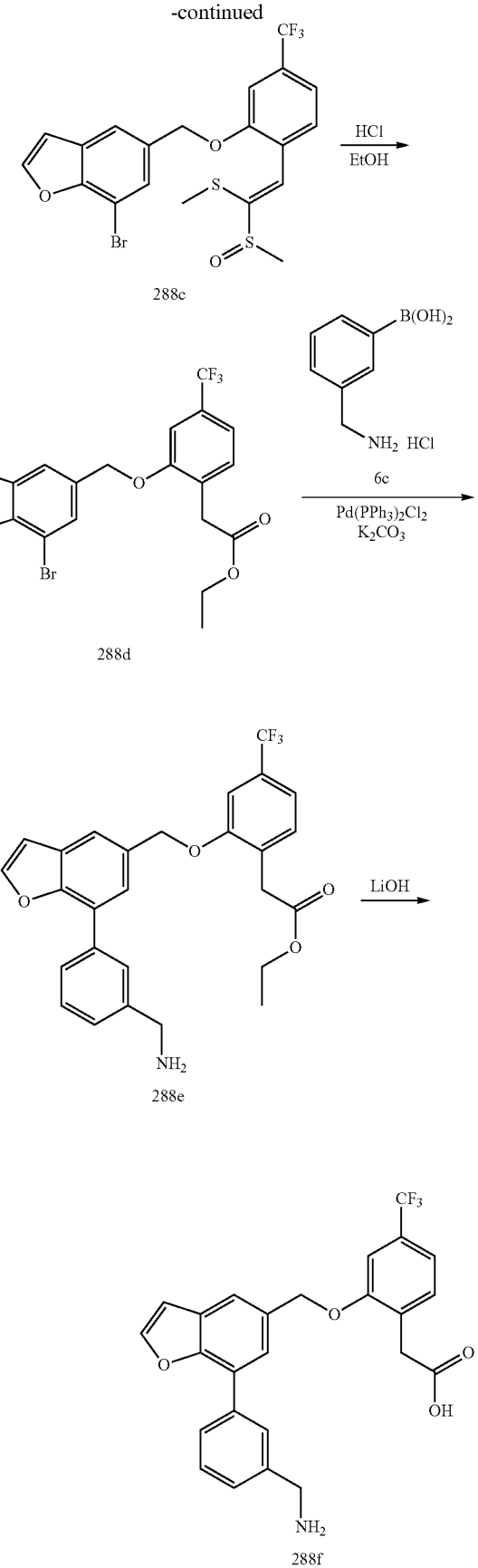

Preparation of 2-(2-((7-(3-(aminomethyl)phenyl) benzofuran-5-yl)methoxy)-4-(trifluoromethyl)phenyl)acetic Acid (288f)

Step-1: Preparation of 2-((7-bromobenzofuran-5-yl)methoxy)-4-(trifluoromethyl)benzaldehyde (288b)

Compound 288b was prepared according to the procedure reported in step-2 of scheme-152 from 7-bromo-5-(bromomethyl)benzofuran (152a) (1.525 g, 5.26 mmol) using 2-hydroxy-4-(trifluoromethyl)benzaldehyde (288a) (1 g, 5.26 mmol), $K_2CO_3$ (2.181 g, 15.78 mmol) in DMF (5 mL) and stirring at room temperature for 12 h. This gave after workup and purification by flash column chromatography (silica gel, 40 g, eluting with ethyl acetate in hexanes) 2-((7-bromobenzofuran-5-yl)methoxy)-4-(trifluoromethyl) benzaldehyde (288b) (2.1 g, 100% yield) as a white solid; $^1$H NMR (300 MHz, DMSO-$d_6$) δ 10.44 (d, J=0.8 Hz, 1H), 8.15 (d, J=2.2 Hz, 1H), 7.90 (dt, J=8.2, 1.1 Hz, 1H), 7.87 (d, J=1.5 Hz, 1H), 7.77 (d, J=1.5 Hz, 1H), 7.71 (d, J=1.5 Hz, 1H), 7.49-7.43 (m, 1H), 7.14 (d, J=2.2 Hz, 1H), 5.48 (s, 2H); $^{19}$F NMR (282 MHz, DMSO-$d_6$) δ−61.74 (d, J=4.8 Hz).

Step-2: Preparation of 7-bromo-5-((2-(2-(methylsulfinyl)-2-(methylthio)vinyl)-5-(trifluoromethyl)phenoxy)methyl)benzofuran (288c)

Compound 288c was prepared according to the procedure reported in step-3 of scheme-266 from 2-((7-bromobenzofuran-5-yl)methoxy)-4-(trifluoromethyl)benzaldehyde (288b) (2 g, 5.01 mmol) in THF (20 mL) using methyl (methylsulfinylmethyl)sulfane (0.996 g, 8.02 mmol), Triton-B (40% methanolic solution, 1.139 mL, 2.505 mmol) and heating at reflux for 12 h. This gave after workup and purification by flash column chromatography (Silica gel, 40 g, eluting with EtOAc in hexane) 7-bromo-5-((2-(2-(methylsulfinyl)-2-(methylthio)vinyl)-5-(trifluoromethyl)phenoxy)methyl)benzofuran (288c) (1.35 g, 53% yield) as a white solid; $^1$H NMR (300 MHz, DMSO-$d_6$) δ 8.15 (d, J=2.2 Hz, 1H), 7.84-7.75 (m, 2H), 7.70 (d, J=1.5 Hz, 1H), 7.43 (d, J=1.7 Hz, 1H), 7.40-7.26 (m, 1H), 7.13 (d, J=2.2 Hz, 1H), 6.75 (s, 1H), 5.33 (s, 2H), 2.41 (s, 3H), 2.32 (s, 3H).

Step-3: Preparation of Ethyl 2-(2-((7-bromobenzofuran-5-yl)methoxy)-4-(trifluoromethyl)phenyl)acetate (288d)

Compound 288d was prepared according to the procedure reported in step-4 of scheme-266 from 7-bromo-5-((2-(2-(methylsulfinyl)-2-(methylthio)vinyl)-5-(trifluoromethyl)phenoxy)methyl)benzofuran (288c) (1.34 g, 2.65 mmol) in ethanol (50 mL) using HCl (4 M in 1,4-dioxane, 1.326 mL, 5.30 mmol) and heating at reflux for 15 h. This gave after workup and purification by flash column chromatography (silica gel 40 g, eluting with ethyl acetate and hexanes) ethyl 2-(2-((7-bromobenzofuran-5-yl)methoxy)-4-(trifluoromethyl)phenyl)acetate (288d) (961 mg, 79% yield) as a white solid; $^1$H NMR (300 MHz, DMSO-$d_6$) δ 8.15 (d, J=2.2 Hz, 1H), 7.73 (d, J=1.5 Hz, 1H), 7.62 (d, J=1.5 Hz, 1H), 7.47 (d, J=7.8 Hz, 1H), 7.41 (d, J=1.7 Hz, 1H), 7.35-7.25 (m, 1H), 7.13 (d, J=2.2 Hz, 1H), 5.28 (s, 2H), 4.01 (q, J=7.1 Hz, 2H), 3.72 (s, 2H), 1.06 (t, J=7.1 Hz, 3H); $^{19}$F NMR (282 MHz, DMSO-$d_6$) δ−60.77; MS (ES+): 480.9 (M+Na).

Step-4: Preparation of Ethyl 2-(2-((7-(3-(aminomethyl)phenyl)benzofuran-5-yl)methoxy)-4-(trifluoromethyl)phenyl)acetate (288e)

Compound 288e was prepared according to the procedure reported in step-3 of scheme-1 from ethyl 2-(2-((7-bromobenzofuran-5-yl)methoxy)-4-(trifluoromethyl)phenyl)acetate (288d) (0.95 g, 2.078 mmol) in dioxane (20 mL) using 3-(aminomethyl)phenylboronic acid hydrochloride (6c) (0.623 g, 3.32 mmol), bis(triphenylphosphine)palladium(II) chloride (Pd(PPh$_3$)$_2$Cl$_2$) (0.219 g, 0.312 mmol), potassium carbonate (0.861 g, 6.23 mmol) in water (3 mL) under an argon atmosphere heating at 100° C. for 12 h on oil bath. This gave after workup, purification by flash column chromatography (silica gel, 40 g, eluting with DMA-80 in DCM from 0-50%) ethyl 2-(2-((7-(3-(aminomethyl)phenyl)benzofuran-5-yl)methoxy)-4-(trifluoromethyl)phenyl)acetate (288e) (910 mg, 91% yield) as a colorless syrup; MS (ES+): 484-2 (M+1)

Step-5: Preparation of 2-(2-((7-(3-(aminomethyl)phenyl)benzofuran-5-yl)methoxy)-4-(trifluoromethyl)phenyl)acetic Acid (288f)

Compound 288f was prepared according to the procedure reported in step-6 of scheme-1 from ethyl 2-(2-((7-(3-(aminomethyl)phenyl)benzofuran-5-yl)methoxy)-4-(trifluoromethyl)phenyl)acetate (288e) (910 mg, 1.882 mmol) in MeOH (2 mL), THF (10 mL) using a solution of lithium hydroxide (180 mg, 7.53 mmol) in water (2 mL). This gave after workup and purification by reverse phase column [C18 (100 g), eluting with ACN in water (containing 0.1% HCl) from 0-100%] 2-(2-((7-(3-(aminomethyl)phenyl)benzofuran-5-yl)methoxy)-4-(trifluoromethyl)phenyl)acetic acid (288f) (450 mg, 53% yield) hydrochloride salt as a yellowish white solid; $^1$H NMR (300 MHz, DMSO-$d_6$) δ 8.51 (s, 3H), 8.12 (d, J=2.2 Hz, 1H), 8.01 (d, J=1.8 Hz, 1H), 7.96-7.87 (m, 1H), 7.78 (d, J=1.6 Hz, 1H), 7.68 (d, J=1.7 Hz, 1H), 7.64-7.54 (m, 2H), 7.47 (d, J=7.8 Hz, 1H), 7.43 (d, J=1.7 Hz, 1H), 7.33-7.27 (m, 1H), 7.08 (d, J=2.2 Hz, 1H), 5.37 (s, 2H), 4.13 (s, 2H), 3.70 (s, 2H); $^{19}$F NMR (282 MHz, DMSO-$d_6$) δ−60.72; MS (ES+): 456.10 (M+1); analysis calculated for MF: $C_{25}H_{20}F_3NO_4$·HCl·0.75$H_2O$; C, 59.41; H, 4.49; Cl, 7.01; N, 2.77; Found; C, 59.20; H, 4.54; Cl, 6.94; N, 2.75.

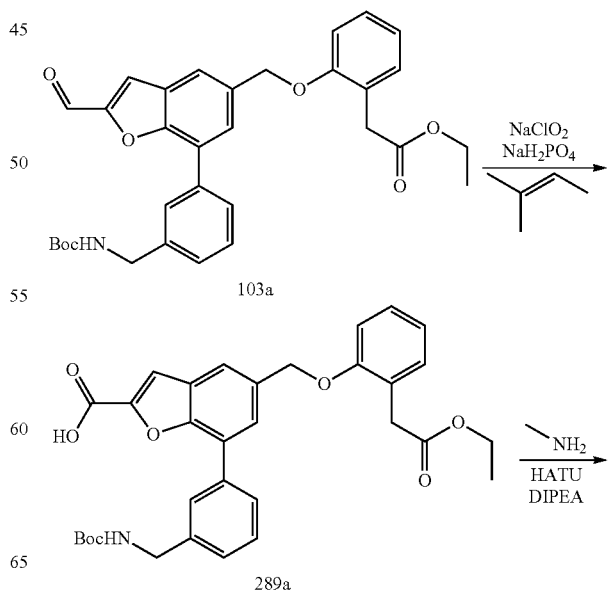

Scheme-289

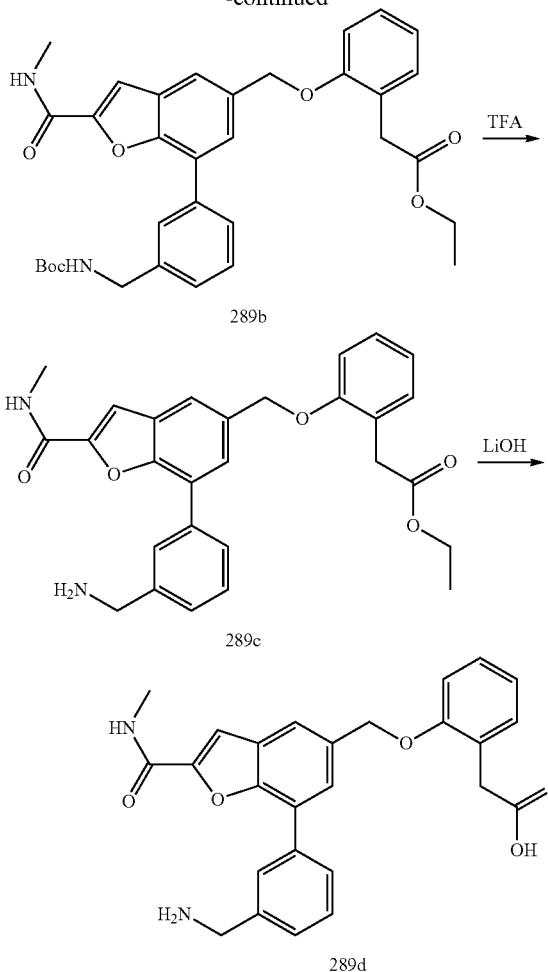

Preparation of 2-(2-((7-(3-(aminomethyl)phenyl)-2-(methylcarbamoyl)benzofuran-5-yl)methoxy)phenyl) acetic Acid (289d)

Step-1: Preparation of 7-(3-(((tert-butoxycarbonyl)amino)methyl)phenyl)-5-((2-(2-ethoxy-2-oxoethyl)phenoxy)methyl)benzofuran-2-carboxylic Acid (289a)

To a solution of ethyl 2-(2-((7-(3-((tert-butoxycarbonylamino)methyl)phenyl)-2-formylbenzofuran-5-yl)methoxy)phenyl)acetate (103a) (1.5 g, 2.76 mmol) in acetonitrile (10 mL) and t-BuOH (60 mL) was added water (5 mL), sodium dihydrogen phosphate (0.662 g, 5.52 mmol) and 2-methyl-2-butene (2.92 mL, 27.6 mmol). The reaction mixture was cooled with ice water bath and added sodium chlorite (1.560 g, 13.80 mmol) in water (5 mL) and stirred in cold for 1 h. The reaction mixture was diluted with brine (50 mL) and ethyl acetate (200 mL). The slurry was filtered through Celite and layers were separated. Aqueous layer was extracted with ethyl acetate (2×150 mL). The combined organic layers were washed with brine (2×60 mL), dried, filtered and concentrated in vacuum to afford 7-(3-(((tert-butoxycarbonyl)amino)methyl)phenyl)-5-((2-(2-ethoxy-2-oxoethyl)phenoxy)methyl)benzofuran-2-carboxylic acid (289a) (650 mg, 42% yield) as a white solid; MS (ES+): 582.2 (M+Na), (ES−): 558.2 (M−1).

Step-2: Preparation of Ethyl 2-(2-((7-(3-(((tert-butoxycarbonyl)amino)methyl)phenyl)-2-(methylcarbamoyl)benzofuran-5-yl)methoxy)phenyl)acetate (289b)

Compound 288b was prepared according to the procedure reported in step-4 of scheme-1 from 7-(3-(((tert-butoxycarbonyl)amino)methyl)phenyl)-5-((2-(2-ethoxy-2-oxoethyl)phenoxy)methyl)benzofuran-2-carboxylic acid (289a) (200 mg, 0.357 mmol) and methenamine (14 mg, 0.447 mmol) in DMF (3 mL) using HATU (204 mg, 0.536 mmol) and DIPEA (0.249 mL, 1.430 mmol) and stirring at room temperature for 16 h. This gave after workup and purification by flash column chromatography (silica gel, 12 g, eluting with 0 to 100% EtOAc/MeOH=9:1 in hexane) ethyl 2-(2-((7-(3-(((tert-butoxycarbonyl)amino)methyl)phenyl)-2-(methylcarbamoyl)benzofuran-5-yl)methoxy)phenyl)acetate (289b) (148 mg, 72% yield) as a white solid; $^1$H NMR (300 MHz, DMSO-$d_6$) δ 7.95 (s, 2H), 7.86-7.77 (m, 3H), 7.69 (d, J=1.7 Hz, 1H), 7.58 (s, 1H), 7.48 (dt, J=14.7, 6.9 Hz, 2H), 7.39-7.19 (m, 3H), 7.12 (d, J=8.1 Hz, 1H), 6.91 (td, J=7.4, 1.1 Hz, 1H), 5.25 (s, 2H), 4.26 (d, J=6.1 Hz, 2H), 3.91 (q, J=7.1 Hz, 2H), 3.63 (s, 2H), 2.83 (d, J=4.6 Hz, 3H), 1.37 (d, J=2.1 Hz, 9H), 0.96 (t, J=7.1 Hz, 3H); MS (ES+): 595.3 (M+Na).

Step-3: Preparation of Ethyl 2-(2-((7-(3-(aminomethyl)phenyl)-2-(methylcarbamoyl)benzofuran-5-yl)methoxy)phenyl)acetate (289c)

Compound 289c was prepared according to the procedure reported in step-5 of scheme-1 from ethyl 2-(2-((7-(3-(((tert-butoxycarbonyl)amino)methyl)phenyl)-2-(methylcarbamoyl)benzofuran-5-yl)methoxy)phenyl)acetate (289b) (148 mg, 0.258 mmol) in DCM (10 mL) using TFA (0.199 mL, 2.58 mmol). This gave after workup ethyl 2-(2-((7-(3-(aminomethyl)phenyl)-2-(methylcarbamoyl)benzofuran-5-yl)methoxy)phenyl)acetate (289c) (152 mg) as a brown syrup; MS (ES+): 473.2 (M+1).

Step-4: Preparation of 2-(2-((7-(3-(aminomethyl)phenyl)-2-(methylcarbamoyl)benzofuran-5-yl)methoxy)phenyl)acetic Acid (289d)

Compound 289d was prepared according to the procedure reported in step-6 of scheme-1 from ethyl 2-(2-((7-(3-(aminomethyl)phenyl)-2-(methylcarbamoyl)benzofuran-5-yl)methoxy)phenyl)acetate (289c) (152 mg, 0.259 mmol) in THF/MeOH (10:2 mL, each) using a solution of lithium hydroxide hydrate (25 mg, 1.037 mmol) in water (2 mL). This gave after workup and purification by reverse phase column chromatography [C18 column, 50 g, eluting with water (containing 0.1% HCl)/acetonitrile (1:0 to 0:1)] 2-(2-((7-(3-(aminomethyl)phenyl)-2-(methylcarbamoyl)benzofuran-5-yl)methoxy)phenyl)acetic acid (289d) (52 mg, 45% yield) hydrochloride salt as a white solid; $^1$H NMR (300 MHz, DMSO-$d_6$) δ 12.23 (s, 1H), 8.59 (d, J=4.8 Hz, 1H), 8.39 (s, 3H), 8.07 (s, 1H), 7.98 (dd, J=7.4, 1.7 Hz, 1H), 7.85 (d, J=1.6 Hz, 1H), 7.77 (d, J=1.6 Hz, 1H), 7.68-7.52 (m, 3H), 7.23 (d, J=7.5 Hz, 2H), 7.10 (d, J=8.1 Hz, 1H), 6.97-6.86 (m, 1H), 5.28 (s, 2H), 4.17 (d, J=5.7 Hz, 2H), 3.60 (s, 2H), 2.83 (d, J=4.6 Hz, 3H); MS (ES+): 445.20 (M+1), (ES−): 443.10 (M−1).

Scheme-290

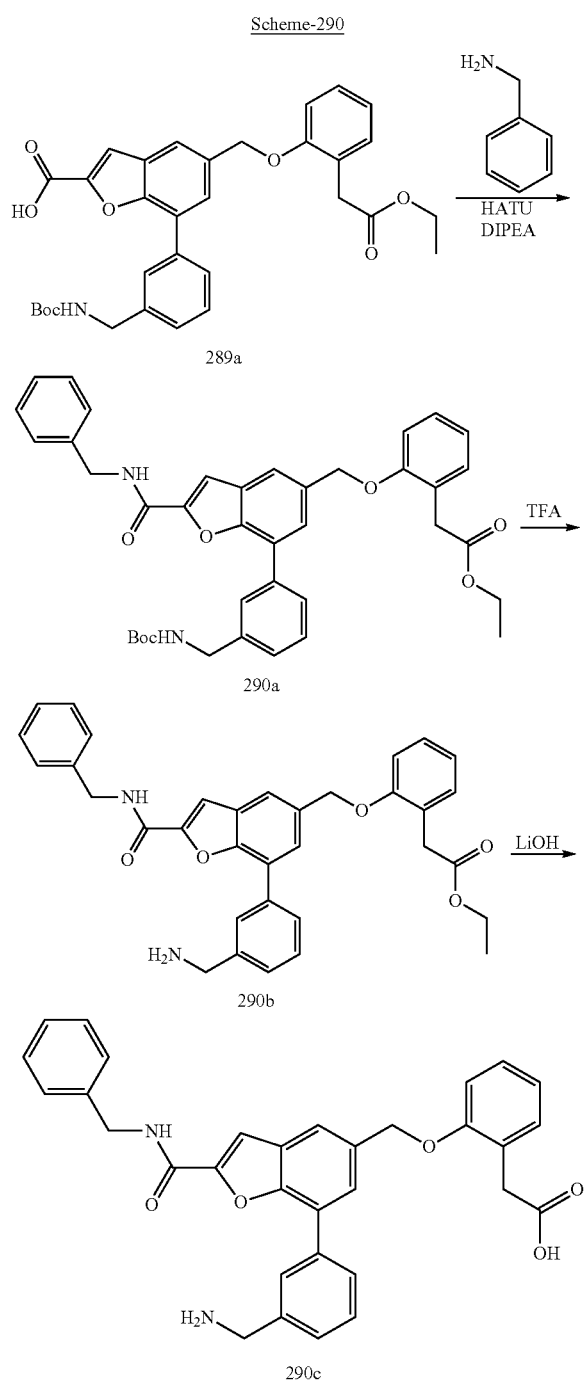

phenoxy)methyl)benzofuran-2-carboxylic acid (289a) (200 mg, 0.357 mmol) and phenylmethanamine (47.9 mg, 0.447 mmol) in DMF (3 mL) using HATU (204 mg, 0.536 mmol) and DIPEA (0.249 mL, 1.430 mmol) and stirring at room temperature for 16 h. This gave after workup and purification by flash column chromatography (silica gel, 12 g, eluting with 0 to 100% EtOAc/MeOH=9:1 in hexane) ethyl 2-(2-((2-(benzylcarbamoyl)-7-(3-(((tert-butoxycarbonyl)amino)methyl)phenyl)benzofuran-5-yl)methoxy)phenyl)acetate (290a) (520 mg) as a white solid; $^1$H NMR (300 MHz, DMSO-$d_6$) δ 9.12 (t, J=6.1 Hz, 1H), 7.95 (s, 3H), 7.86-7.76 (m, 3H), 7.69 (d, J=1.7 Hz, 1H), 7.67 (s, 1H), 7.56-7.39 (m, 1H), 7.37-7.20 (m, 6H), 7.12 (d, J=8.1 Hz, 1H), 6.97-6.87 (m, 1H), 5.25 (s, 2H), 4.52 (d, J=6.1 Hz, 2H), 4.24 (d, J=6.1 Hz, 2H), 3.92 (q, J=7.1 Hz, 2H), 3.63 (s, 2H), 1.38 (d, J=3.6 Hz, 9H), 0.97 (t, J=7.1 Hz, 3H).

Step-2: Preparation of Ethyl 2-(2-((7-(3-(aminomethyl)phenyl)-2-(benzylcarbamoyl)benzofuran-5-yl)methoxy)phenyl)acetate (290b)

Compound 290b was prepared according to the procedure reported in step-5 of scheme-1 from ethyl 2-(2-((2-(benzylcarbamoyl)-7-(3-(((tert-butoxycarbonyl)amino)methyl)phenyl)benzofuran-5-yl)methoxy)phenyl)acetate (290a) (520 g, 802 mmol) in DCM (10 mL) using TFA (618 mL, 8.015 mmol). This gave after workup ethyl 2-(2-((7-(3-(aminomethyl)phenyl)-2-(benzylcarbamoyl)benzofuran-5-yl)methoxy)phenyl)acetate (290b) (531 g) as a brow syrup; MS (ES+): 549.3 (M+1).

Step-3: Preparation of 2-(2-((7-(3-(aminomethyl)phenyl)-2-(benzylcarbamoyl)benzofuran-5-yl)methoxy)phenyl)acetic Acid (290c)

Compound 290c was prepared according to the procedure reported in step-6 of scheme-1 from ethyl 2-(2-((7-(3-(aminomethyl)phenyl)-2-(benzylcarbamoyl)benzofuran-5-yl)methoxy)phenyl)acetate (290b) (531 mg, 0.801 mmol) in THF/MeOH (10:3 mL, each) using a solution of lithium hydroxide hydrate (77 mg, 3.21 mmol) in water (3 mL). This gave after workup and purification by reverse phase column chromatography [C18 column, 100 g, eluting with water (containing 0.1% HCl)/acetonitrile (1:0 to 0:1)] 2-(2-((7-(3-(aminomethyl)phenyl)-2-(benzylcarbamoyl)benzofuran-5-yl)methoxy)phenyl)acetic acid (290c) (110 mg, 26% yield) hydrochloride salt as a white solid; $^1$H NMR (300 MHz, DMSO-$d_6$) δ 9.23 (t, J=6.2 Hz, 1H), 8.36 (s, 3H), 8.08 (s, 1H), 8.01 (d, J=7.7 Hz, 1H), 7.87 (d, J=1.6 Hz, 1H), 7.79 (d, J=1.6 Hz, 1H), 7.69 (s, 1H), 7.61 (t, J=7.6 Hz, 1H), 7.54 (d, J=7.7 Hz, 1H), 7.38-7.30 (m, 4H), 7.29-7.18 (m, 3H), 7.10 (d, J=8.0 Hz, 1H), 6.96-6.87 (m, 1H), 5.29 (s, 2H), 4.52 (d, J=6.1 Hz, 2H), 4.16 (s, 2H), 3.60 (s, 2H); MS (ES+): 521.20 (M+1), (ES−): 519.20 (M−1).

Preparation of 2-(2-((7-(3-(aminomethyl)phenyl)-2-(benzylcarbamoyl)benzofuran-5-yl)methoxy)phenyl)acetic Acid (290c)

Step-1: Preparation of Ethyl 2-(2-((2-(benzylcarbamoyl)-7-(3-(((tert-butoxycarbonyl)amino)methyl)phenyl)benzofuran-5-yl)methoxy)phenyl)acetate (290a)

Compound 290a was prepared according to the procedure reported in step-4 of scheme-1 from 7-(3-(((tert-butoxycarbonyl)amino)methyl)phenyl)-5-((2-(2-ethoxy-2-oxoethyl)

Scheme-291

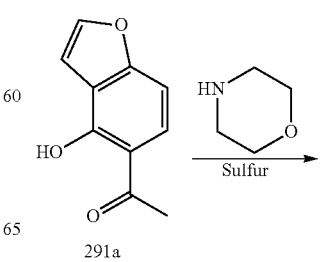

977 -continued

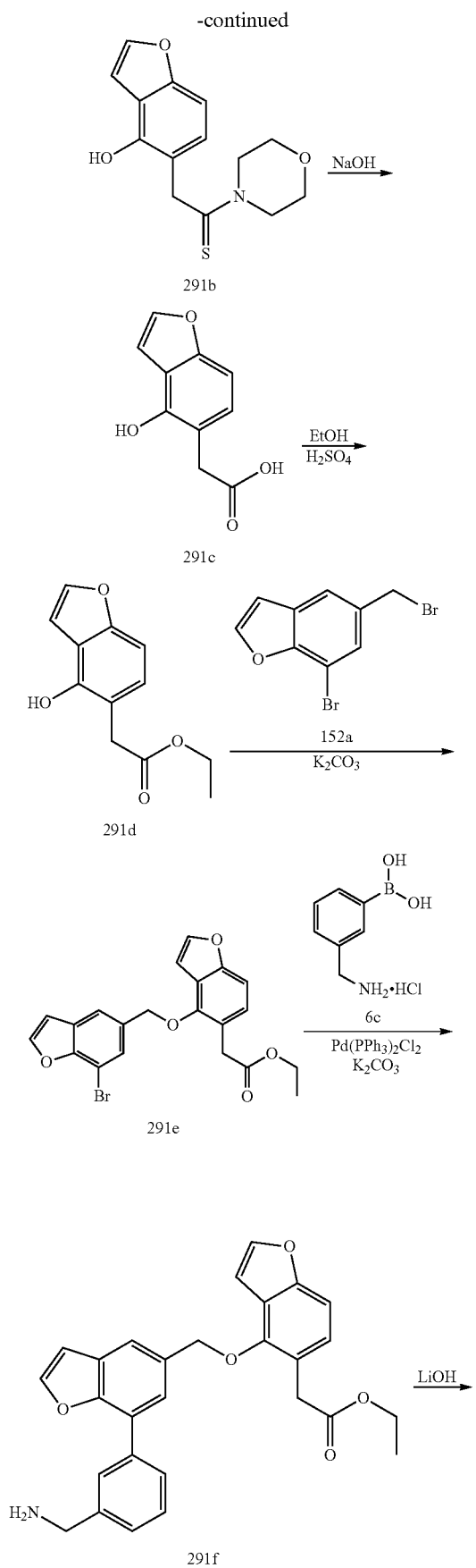

978 -continued

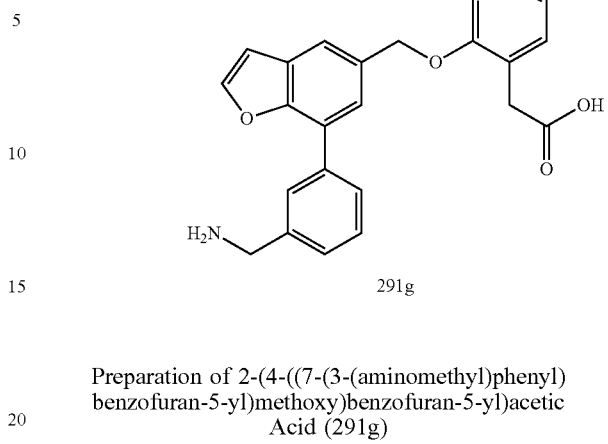

Preparation of 2-(4-((7-(3-(aminomethyl)phenyl) benzofuran-5-yl)methoxy)benzofuran-5-yl)acetic Acid (291g)

Step-1: Preparation of 2-(4-hydroxybenzofuran-5-yl)-1-morpholinoethanethione (291b)

Compound 291b was prepared according to the procedure reported in step-1 of scheme-265 from 1-(4-hydroxybenzofuran-5-yl)ethanone (291a) [(1 g, 5.68 mmol; CAS #69722-46-9; prepared according to the procedure reported by Satyavani, Susarla R. et al; in Medicinal Chemistry Research, 24(2), 842-850; 2015)] in N-Methyl-2-pyrrolidinone (3 mL) using sulfur powder (0.364 g, 11.35 mmol), morpholine (0.979 mL, 11.35 mmol) and heating at 130° C. for 10 h. This gave after workup 2-(4-hydroxybenzofuran-5-yl)-1-morpholinoethanethione (291b) (1.85 g) as buff solid; MS (ES+): 278.0 (M+1), 276.1 (M−1).

Step-2: Preparation of 2-(4-hydroxybenzofuran-5-yl)acetic Acid (291c)

Compound 291c was prepared according to the procedure reported in step-2 of scheme-265 2-(4-hydroxybenzofuran-5-yl)-1-morpholinoethanethione (291b) (1.85 g, 6.67 mmol) in ethanol (50 mL) and water (10 mL) using sodium hydroxide (1.467 g, 36.7 mmol) and heating at reflux for 10 h. This gave after workup 2-(4-hydroxybenzofuran-5-yl)acetic acid (291c) (1.2 g, 94% yield) as a white solid; MS (ES−): 190.1 (M−1).

Step-3: Preparation of Ethyl 2-(4-hydroxybenzofuran-5-yl)acetate (291d)

Compound 291d was prepared according to the procedure reported in step-3 of scheme-265 from 2-(4-hydroxybenzofuran-5-yl)acetic acid (291c) (1.18 g, 6.14 mmol) in ethanol (25 mL) using sulfuric acid (0.393 mL, 7.37 mmol) and heating at reflux for 12 h. This gave after workup and purification by flash column chromatography (silica gel, 40 g, eluting with ethyl acetate and hexanes) ethyl 2-(4-hydroxybenzofuran-5-yl)acetate (291d) (285 mg, 21% yield) as white solid; $^1$H NMR (300 MHz, DMSO-$d_6$) δ 9.77 (s, 1H), 7.79 (d, J=2.3 Hz, 1H), 7.08-7.03 (m, 2H), 6.99 (dd, J=8.3, 0.9 Hz, 1H), 4.06 (q, J=7.1 Hz, 2H), 3.64 (s, 2H), 1.18 (t, J=7.1 Hz, 3H); MS (ES+): 243.0 (M+Na).

Step-4: Preparation of Ethyl 2-(4-((7-bromobenzofuran-5-yl)methoxy)benzofuran-5-yl)acetate (291e)

Compound 291e was prepared according to the procedure reported in step-2 of scheme-152 from 7-bromo-5-(bromomethyl)benzofuran (152a) (424 mg, 1.462 mmol) using ethyl 2-(4-hydroxybenzofuran-5-yl)acetate (291d) (280 mg, 1.271 mmol), K$_2$CO$_3$ (527 mg, 3.81 mmol) in DMF (5 mL) and stirring at room temperature for 12h. This gave after workup and purification by flash column chromatography (silica gel, 40 g, eluting with ethyl acetate and hexanes) ethyl 2-(4-((7-bromobenzofuran-5-yl)methoxy)benzofuran-5-yl)acetate (291e) (407 mg, 75% yield) as a white solid; $^1$H NMR (300 MHz, DMSO-d$_6$) δ 8.15 (d, J=2.2 Hz, 1H), 7.98 (d, J=2.4 Hz, 1H), 7.78 (d, J=1.5 Hz, 1H), 7.69 (d, J=1.5 Hz, 1H), 7.31-7.24 (m, 2H), 7.18 (d, J=8.4 Hz, 1H), 7.13 (d, J=2.2 Hz, 1H), 5.37 (s, 2H), 3.98 (q, J=7.1 Hz, 2H), 3.68 (s, 2H), 1.07 (t, J=7.1 Hz, 3H).

Step-5: Preparation of Ethyl 2-(4-((7-(3-(aminomethyl)phenyl)benzofuran-5-yl)methoxy)benzofuran-5-yl)acetate (291f)

Compound 291f was prepared according to the procedure reported in step-3 of scheme-1 from ethyl 2-(4-((7-bromobenzofuran-5-yl)methoxy)benzofuran-5-yl)acetate (291e) (395 mg, 0.920 mmol) in dioxane (15 mL) using 3-(aminomethyl)phenylboronic acid hydrochloride (6c) (276 mg, 1.472 mmol), bis(triphenylphosphine)palladium (II) chloride (Pd(PPh$_3$)$_2$Cl$_2$) (97 mg, 0.138 mmol), potassium carbonate (382 mg, 2.76 mmol) in water (3 mL) under an argon atmosphere heating at 100° C. for 12 h on oil bath. This gave after workup, purification by flash column chromatography (silica gel, 40 g, eluting with DMA-80 in DCM from 0-50%) ethyl 2-(4-((7-(3-(aminomethyl)phenyl)benzofuran-5-yl)methoxy)benzofuran-5-yl)acetate (291f) (322 mg, 77% yield) as a colorless syrup; $^1$H NMR (300 MHz, DMSO-d$_6$) δ 8.10 (d, J=2.2 Hz, 1H), 7.98 (d, J=2.3 Hz, 1H), 7.81 (d, J=1.9 Hz, 1H), 7.75 (d, J=1.7 Hz, 1H), 7.72 (dt, J=7.6, 1.6 Hz, 1H), 7.63 (d, J=1.7 Hz, 1H), 7.47 (t, J=7.5 Hz, 1H), 7.40 (dt, J=7.7, 1.5 Hz, 1H), 7.29 (d, J=1.7 Hz, 1H), 7.26 (d, J=0.9 Hz, 1H), 7.18 (d, J=8.3 Hz, 1H), 7.06 (d, J=2.2 Hz, 1H), 5.45 (s, 2H), 3.91 (q, J=7.1 Hz, 2H), 3.82 (s, 2H), 3.69 (s, 2H), 3.32 (s, 2H), 0.99 (t, J=7.1 Hz, 3H); MS (ES+): 456.2 (M+1), 478.1 (M+Na).

Step-6: Preparation of 2-(4-((7-(3-(aminomethyl)phenyl)benzofuran-5-yl)methoxy)benzofuran-5-yl)acetic Acid (291g)

Compound 291g was prepared according to the procedure reported in step-6 of scheme-1 from ethyl 2-(4-((7-(3-(aminomethyl)phenyl)benzofuran-5-yl)methoxy)benzofuran-5-yl)acetate (291f) (315 mg, 0.692 mmol) in MeOH (3 mL), THF (15 mL) using lithium hydroxide monohydrate (66 mg, 2.77 mmol) in water (3 mL). This gave after workup and purification by reverse phase column [C18 (100 g), eluting with ACN in water (containing 0.1% HCl) from 0-100%] 2-(4-((7-(3-(aminomethyl)phenyl)benzofuran-5-yl)methoxy)benzofuran-5-yl)acetic acid (291g) (124 mg, 42% yield) hydrochloride salt white solid; $^1$H NMR (300 MHz, DMSO-d$_6$) δ 12.26 (s, 1H), 8.42 (s, 3H), 8.12 (d, J=2.2 Hz, 1H), 8.01 (d, J=1.9 Hz, 1H), 7.98 (d, J=2.3 Hz, 1H), 7.93 (dt, J=7.3, 1.8 Hz, 1H), 7.82 (d, J=1.6 Hz, 1H), 7.72 (d, J=1.6 Hz, 1H), 7.65-7.53 (m, 2H), 7.31-7.24 (m, 2H), 7.19 (d, J=8.4 Hz, 1H), 7.09 (d, J=2.2 Hz, 1H), 5.42 (s, 2H), 4.14 (q, J=5.8 Hz, 2H), 3.65 (s, 2H); MS (ES+): 428.20 (M+1), (ES−): 426.10 (M−1); Analysis calculated for C$_{26}$H$_{21}$NO$_5$.HCl.2H$_2$O: C, 62.46; H, 5.24; Cl, 7.09; N, 2.80; Found: C, 62.60; H, 5.00; Cl, 7.38; N, 2.81.

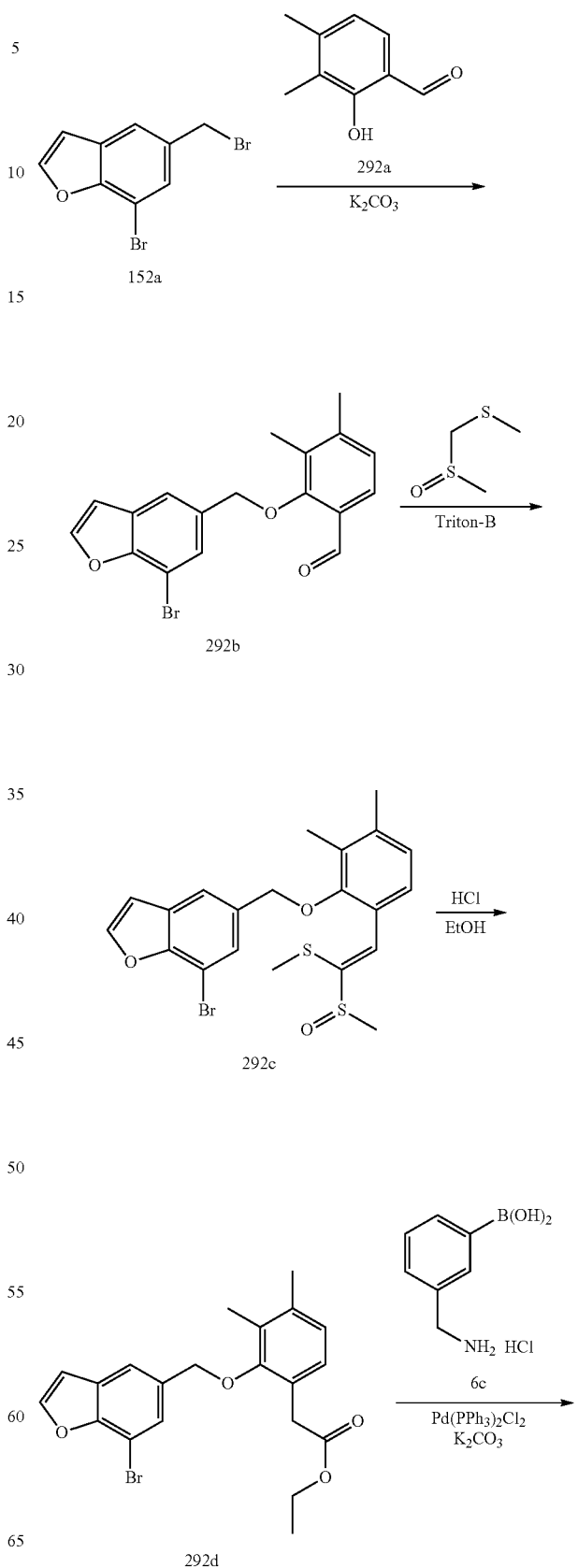

Scheme-292

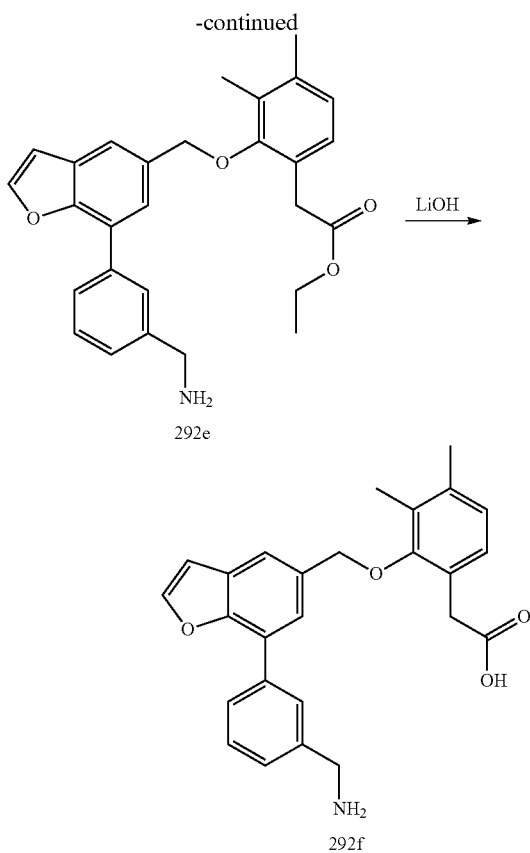

Preparation of 2-(2-((7-(3-(aminomethyl)phenyl) benzofuran-5-yl)methoxy)-3,4-dimethylphenyl)acetic Acid (292f)

Step-1: Preparation of 2-((7-bromobenzofuran-5-yl) methoxy)-3,4-dimethylbenzaldehyde (292b)

Compound 292b was prepared according to the procedure reported in step-2 of scheme-152 from 7-bromo-5-(bromomethyl)benzofuran (152a) (1.931 g, 6.66 mmol) using 2-hydroxy-3,4-dimethylbenzaldehyde (292a) (1 g, 6.66 mmol), $K_2CO_3$ (2.76 g, 19.98 mmol) in DMF (10 mL) and stirring at room temperature for 12 h. This gave after workup and purification by flash column chromatography (silica gel, 40 g, eluting with ethyl acetate in hexanes) 2-((7-bromobenzofuran-5-yl)methoxy)-3,4-dimethylbenzaldehyde (292b) (2.31 g, 97% yield) as a white solid; $^1$H NMR (300 MHz, DMSO-$d_6$) δ 10.13 (d, J=0.8 Hz, 1H), 8.16 (d, J=2.2 Hz, 1H), 7.80 (d, J=1.5 Hz, 1H), 7.70 (d, J=1.5 Hz, 1H), 7.52 (d, J=7.9 Hz, 1H), 7.17 (d, J=8.0 Hz, 1H), 7.14 (d, J=2.2 Hz, 1H), 5.04 (s, 2H), 2.34 (s, 3H), 2.24 (s, 3H).

Step-2: Preparation of 7-bromo-5-((2,3-dimethyl-6-(2-(methylsulfinyl)-2-(methylthio)vinyl)phenoxy) methyl)benzofuran (292c)

Compound 292c was prepared according to the procedure reported in step-3 of scheme-266 from 2-((7-bromobenzofuran-5-yl)methoxy)-3,4-dimethylbenzaldehyde (292b) (2.3 g, 6.40 mmol) in THF (20 mL) using methyl(methylsulfinylmethyl)sulfane (1.273 g, 10.24 mmol), Triton-B (40% methanolic solution, 1.455 mL, 3.20 mmol) and heating at reflux for 12 h. This gave after workup and purification by flash column chromatography (Silica gel, 40 g, eluting with EtOAc in hexane) 7-bromo-5-((2,3-dimethyl-6-(2-(methylsulfinyl)-2-(methylthio)vinyl)phenoxy)methyl)benzofuran (292c) (2.24 g, 75% yield) as a white solid; $^1$H NMR (300 MHz, DMSO-$d_6$) δ 8.15 (d, J=2.2 Hz, 1H), 7.88 (d, J=7.9 Hz, 1H), 7.83-7.77 (m, 2H), 7.69 (d, J=1.5 Hz, 1H), 7.15-7.05 (m, 2H), 4.89-4.70 (m, 2H), 2.70 (s, 3H), 2.30 (s, 3H), 2.26 (s, 3H), 2.23 (s, 3H); MS (ES+): 465.00, 467.00 (M, M+2).

Step-3: Preparation of Ethyl 2-(2-((7-bromobenzofuran-5-yl)methoxy)-3,4-dimethylphenyl)acetate (292d)

Compound 292d was prepared according to the procedure reported in step-4 of scheme-266 from 7-bromo-5-((2,3-dimethyl-6-(2-(methylsulfinyl)-2-(methylthio)vinyl)phenoxy)methyl)benzofuran (292c) (2.2 g, 4.73 mmol) in ethanol (50 mL) using HCl (4 M in 1,4-dioxane, 2.363 mL, 9.45 mmol) and heating at reflux for 12 h. This gave after workup and purification by flash column chromatography (silica gel 40 g, eluting with ethyl acetate and hexanes) ethyl 2-(2-((7-bromobenzofuran-5-yl)methoxy)-3,4-dimethylphenyl)acetate (292d) (645 mg, 33% yield) as a white solid; $^1$H NMR (300 MHz, DMSO-$d_6$) δ 8.16 (d, J=2.2 Hz, 1H), 7.77 (d, J=1.5 Hz, 1H), 7.65 (d, J=1.5 Hz, 1H), 7.14 (d, J=2.2 Hz, 1H), 7.05-6.88 (m, 2H), 4.81 (s, 2H), 4.01 (q, J=7.1 Hz, 2H), 3.62 (s, 2H), 2.23 (s, 3H), 2.19 (s, 3H), 1.10 (t, J=7.1 Hz, 3H); MS (ES+): 417.00, 419.00 (M, M+2).

Step-4: Preparation of Ethyl 2-(2-((7-(3-(aminomethyl)phenyl)benzofuran-5-yl)methoxy)-3,4-dimethylphenyl)acetate (292e)

Compound 292e was prepared according to the procedure reported in step-3 of scheme-1 from ethyl 2-(2-((7-bromobenzofuran-5-yl)methoxy)-3,4-dimethylphenyl)acetate (292d) (635 mg, 1.522 mmol) in dioxane (15 mL) using 3-(aminomethyl)phenylboronic acid hydrochloride (6c) (456 mg, 2.435 mmol), bis(triphenylphosphine)palladium (II) chloride (Pd(PPh$_3$)$_2$Cl$_2$) (160 mg, 0.228 mmol), potassium carbonate (631 mg, 4.57 mmol) in water (3 mL) under an argon atmosphere heating at 100° C. for 6 h on oil bath. This gave after workup, purification by flash column chromatography (silica gel, 40 g, eluting with DMA-80 in DCM from 0-50%) ethyl 2-(2-((7-(3-(aminomethyl)phenyl)benzofuran-5-yl)methoxy)-3,4-dimethylphenyl)acetate (292e) (450 mg, 67% yield) as a colorless syrup; $^1$H NMR (300 MHz, DMSO-$d_6$) δ 8.10 (d, J=2.1 Hz, 1H), 7.81 (d, J=1.8 Hz, 1H), 7.75 (d, J=1.6 Hz, 1H), 7.70 (dt, J=7.5, 1.7 Hz, 1H), 7.58 (d, J=1.7 Hz, 1H), 7.48 (t, J=7.6 Hz, 1H), 7.41 (d, J=7.4 Hz, 1H), 7.08 (d, J=2.2 Hz, 1H), 7.02 (d, J=7.7 Hz, 1H), 6.94 (d, J=7.7 Hz, 1H), 4.88 (s, 2H), 4.09-3.94 (m, 2H), 3.82 (s, 2H), 3.64 (s, 2H), 2.24 (s, 3H), 2.22 (s, 3H), 1.04 (t, J=7.1 Hz, 3H); MS (ES+): 444.2 (M+1).

Step-5: Preparation of 2-(2-((7-(3-(aminomethyl) phenyl)benzofuran-5-yl)methoxy)-3,4-dimethylphenyl)acetic Acid (292f)

Compound 292f was prepared according to the procedure reported in step-6 of scheme-1 from ethyl 2-(2-((7-(3-(aminomethyl)phenyl)benzofuran-5-yl)methoxy)-3,4-dimethylphenyl)acetate (292e) (420 mg, 0.947 mmol) in MeOH (5 mL), THF (10 mL) using a solution of lithium hydroxide (91 mg, 3.79 mmol) in water (2 mL). This gave after workup and purification by reverse phase column [C18 (100 g), eluting with ACN in water (containing 0.1% HCl) from 0-100%] 2-(2-((7-(3-(aminomethyl)phenyl)benzofuran-5-yl)methoxy)-3,4-dimethylphenyl)acetic acid (292f) (295 mg, 75% yield) hydrochloride salt as a white solid; $^1$H NMR (300 MHz, DMSO-d$_6$) δ 12.28 (s, 1H), 8.41 (s, 3H), 8.12 (d, J=2.2 Hz, 1H), 7.99 (t, J=1.7 Hz, 1H), 7.92 (dt, J=7.3, 1.8 Hz, 1H), 7.81 (d, J=1.6 Hz, 1H), 7.66 (d, J=1.6 Hz, 1H), 7.64-7.53 (m, 2H), 7.11 (d, J=2.2 Hz, 1H), 7.03 (d, J=7.7 Hz, 1H), 6.94 (d, J=7.8 Hz, 1H), 4.89 (s, 2H), 4.15 (d, J=5.5 Hz, 2H), 3.60 (s, 2H), 2.24 (s, 3H), 2.22 (s, 3H); MS (ES+): 416.10 (M+1), (ES−): 414.10 (M−1); Analysis calculated for C$_{26}$H$_{25}$NO$_4$.HCl.0.25H$_2$O: C, 68.42; H, 5.85; Cl, 7.77; N, 3.07; Found: C, 68.23; H, 5.84; Cl, 7.90; N, 3.24.

Scheme-293

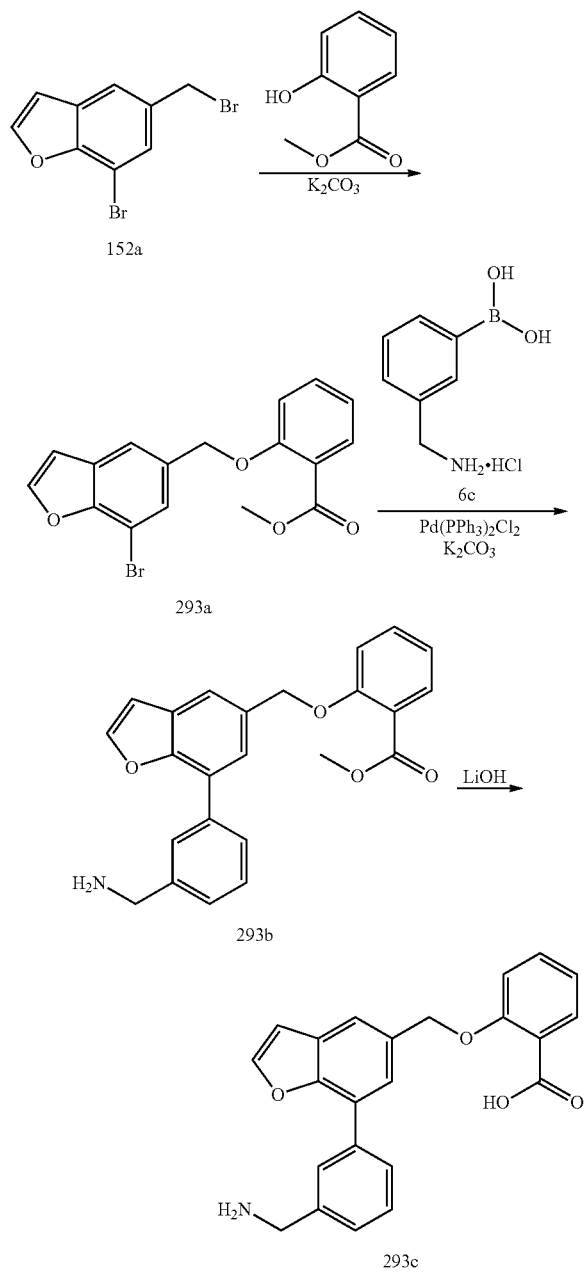

Preparation of 2-((7-(3-(aminomethyl)phenyl)benzofuran-5-yl)methoxy)benzoic Acid (293c)

Step-1: Preparation of methyl 2-((7-bromobenzofuran-5-yl)methoxy)benzoate (293a)

Compound 293a was prepared according to the procedure reported in step-2 of scheme-152 from 7-bromo-5-(bromomethyl)benzofuran (152a) (0.953 g, 3.29 mmol) using methyl 2-hydroxybenzoate (0.5 g, 3.29 mmol), K$_2$CO$_3$ (1.363 g, 9.86 mmol) in DMF (5 mL) and stirring at room temperature for 12h. This gave after workup and purification by flash column chromatography (silica gel, 40 g, eluting with ethyl acetate and hexanes) methyl 2-((7-bromobenzofuran-5-yl)methoxy)benzoate (293a) (979 mg, 82% yield) as a white solid; $^1$H NMR (300 MHz, DMSO-d$_6$) δ 8.14 (d, J=2.2 Hz, 1H), 7.78 (d, J=1.4 Hz, 1H), 7.72 (d, J=1.1 Hz, 1H), 7.69 (d, J=1.8 Hz, 1H), 7.54 (ddd, J=8.5, 7.2, 1.7 Hz, 1H), 7.26 (dd, J=8.5, 1.0 Hz, 1H), 7.14 (d, J=2.2 Hz, 1H), 7.05 (td, J=7.5, 1.0 Hz, 1H), 5.30 (s, 2H), 3.83 (s, 3H).

Step-2: Preparation of methyl 2-((7-(3-(aminomethyl)phenyl)benzofuran-5-yl)methoxy)benzoate (293b)

Compound 293b was prepared according to the procedure reported in step-3 of scheme-1 from methyl 2-((7-bromobenzofuran-5-yl)methoxy)benzoate (293a) (945 mg, 2.62 mmol) in dioxane (20 mL) using 3-(aminomethyl)phenylboronic acid hydrochloride (6c) (785 mg, 4.19 mmol), bis(triphenylphosphine)palladium(II) chloride (Pd(PPh$_3$)$_2$Cl$_2$) (275 mg, 0.392 mmol), potassium carbonate (1085 mg, 7.85 mmol) in water (3 mL) under an argon atmosphere heating at 100° C. for 6 h on oil bath. This gave after workup, purification by flash column chromatography (silica gel, 40 g, eluting with DMA-80 in DCM from 0-50%) methyl 2-((7-(3-(aminomethyl)phenyl)benzofuran-5-yl)methoxy)benzoate (293b) (750 mg, 74% yield) as a colorless syrup; $^1$H NMR (300 MHz, DMSO-d$_6$) δ 8.09 (d, J=2.2 Hz, 1H), 7.83 (td, J=1.8, 0.7 Hz, 2H), 7.76 (d, J=1.6 Hz, 1H), 7.77-7.62 (m, 4H), 7.59-7.48 (m, 1H), 7.46 (d, J=7.5 Hz, 1H), 7.42-7.36 (m, 1H), 7.30 (dd, J=8.5, 1.0 Hz, 1H), 7.09-6.98 (m, 2H), 5.36 (s, 2H), 3.82 (s, 2H), 3.80 (s, 3H); MS (ES+): 388.1 (M+1).

Step-3: Preparation of 2-((7-(3-(aminomethyl)phenyl)benzofuran-5-yl)methoxy)benzoic acid (293c)

Compound 293c was prepared according to the procedure reported in step-6 of scheme-1 from methyl 2-((7-(3-(aminomethyl)phenyl)benzofuran-5-yl)methoxy)benzoate (293b) (750 mg, 1.936 mmol) in MeOH (5 mL), THF (10 mL) using lithium hydroxide monohydrate (185 mg, 7.74 mmol) in water (5 mL). This gave after workup and purification by reverse phase column [C18 (100 g), eluting with ACN in water (containing 0.1% HCl) from 0-100%] 2-((7-(3-(aminomethyl)phenyl)benzofuran-5-yl)methoxy)benzoic acid (293c) (540 mg, 75% yield) hydrochloride salt as a white solid; $^1$H NMR (300 MHz, DMSO-d$_6$) δ 8.33 (s, 4H), 8.11 (d, J=2.2 Hz, 1H), 7.99 (d, J=1.9 Hz, 1H), 7.91 (dt, J=7.6, 1.6 Hz, 1H), 7.81 (d, J=1.6 Hz, 1H), 7.73 (d, J=1.7 Hz, 1H), 7.66 (dd, J=7.6, 1.8 Hz, 1H), 7.60 (t, J=7.6 Hz, 1H), 7.56-7.52 (m, 1H), 7.52-7.46 (m, 1H), 7.29-7.24 (m, 1H), 7.08 (d, J=2.2 Hz, 1H), 7.02 (td, J=7.5, 1.0 Hz, 1H), 5.34 (s, 2H), 4.14 (s, 2H); MS (ES+): 374.10 (M+1), (ES−): 372.10

(M–1); Analysis calculated for $C_{23}H_{19}NO_4 \cdot HCl \cdot 0.25H_2O$: C, 66.67; H, 4.99; Cl, 8.56; N, 3.38; Found: C, 66.96; H, 4.96; Cl, 8.47; N, 3.38.

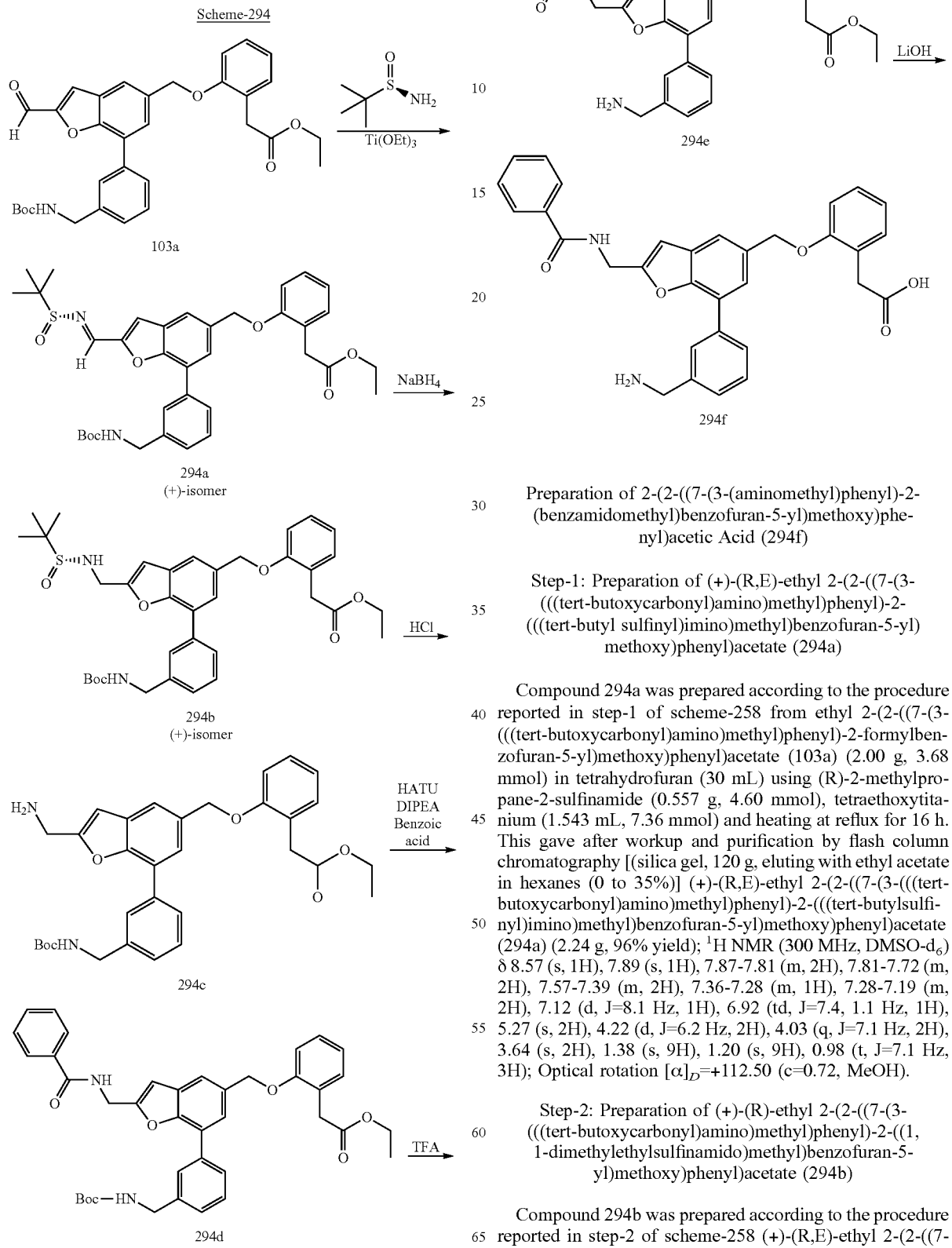

Preparation of 2-(2-((7-(3-(aminomethyl)phenyl)-2-(benzamidomethyl)benzofuran-5-yl)methoxy)phenyl)acetic Acid (294f)

Step-1: Preparation of (+)-(R,E)-ethyl 2-(2-((7-(3-(((tert-butoxycarbonyl)amino)methyl)phenyl)-2-(((tert-butyl sulfinyl)imino)methyl)benzofuran-5-yl)methoxy)phenyl)acetate (294a)

Compound 294a was prepared according to the procedure reported in step-1 of scheme-258 from ethyl 2-(2-((7-(3-(((tert-butoxycarbonyl)amino)methyl)phenyl)-2-formylbenzofuran-5-yl)methoxy)phenyl)acetate (103a) (2.00 g, 3.68 mmol) in tetrahydrofuran (30 mL) using (R)-2-methylpropane-2-sulfinamide (0.557 g, 4.60 mmol), tetraethoxytitanium (1.543 mL, 7.36 mmol) and heating at reflux for 16 h. This gave after workup and purification by flash column chromatography [(silica gel, 120 g, eluting with ethyl acetate in hexanes (0 to 35%)] (+)-(R,E)-ethyl 2-(2-((7-(3-(((tert-butoxycarbonyl)amino)methyl)phenyl)-2-(((tert-butylsulfinyl)imino)methyl)benzofuran-5-yl)methoxy)phenyl)acetate (294a) (2.24 g, 96% yield); $^1$H NMR (300 MHz, DMSO-$d_6$) δ 8.57 (s, 1H), 7.89 (s, 1H), 7.87-7.81 (m, 2H), 7.81-7.72 (m, 2H), 7.57-7.39 (m, 2H), 7.36-7.28 (m, 1H), 7.28-7.19 (m, 2H), 7.12 (d, J=8.1 Hz, 1H), 6.92 (td, J=7.4, 1.1 Hz, 1H), 5.27 (s, 2H), 4.22 (d, J=6.2 Hz, 2H), 4.03 (q, J=7.1 Hz, 2H), 3.64 (s, 2H), 1.38 (s, 9H), 1.20 (s, 9H), 0.98 (t, J=7.1 Hz, 3H); Optical rotation $[α]_D$=+112.50 (c=0.72, MeOH).

Step-2: Preparation of (+)-(R)-ethyl 2-(2-((7-(3-(((tert-butoxycarbonyl)amino)methyl)phenyl)-2-((1,1-dimethylethylsulfinamido)methyl)benzofuran-5-yl)methoxy)phenyl)acetate (294b)

Compound 294b was prepared according to the procedure reported in step-2 of scheme-258 (+)-(R,E)-ethyl 2-(2-((7-(3-(((tert-butoxycarbonyl)amino)methyl)phenyl)-2-(((tert-butylsulfinyl)imino)methyl)benzofuran-5-yl)methoxy)phenyl)acetate (294a) (1.78 g, 2.75 mmol) in tetrahydrofuran (25 mL) and methanol (10 mL) using sodium borohydride (0.312 g, 8.26 mmol). This gave after workup and purification by flash column chromatography [(silica gel, 40 g, eluting with a 9:1 mixture of ethyl acetate and methanol in hexanes (0 to 100%)] (+)-(R)-ethyl 2-(2-((7-(3-(((tert-butoxycarbonyl)amino)methyl)phenyl)-2-((1,1-dimethylethylsulfinamido)methyl)benzofuran-5-yl)methoxy)phenyl)acetate (294b) (1.45 g, 81% yield) as a white solid; $^1$H NMR (300 MHz, DMSO-$d_6$) δ 7.76 (d, J=7.4 Hz, 2H), 7.63 (d, J=1.6 Hz, 1H), 7.54-7.38 (m, 3H), 7.33-7.18 (m, 3H), 7.11 (d, J=8.1 Hz, 1H), 6.95-6.81 (m, 2H), 5.96 (t, J=5.8 Hz, 1H), 5.21 (s, 2H), 4.35 (d, J=5.6 Hz, 2H), 4.22 (d, J=6.2 Hz, 2H), 3.92 (q, J=7.1 Hz, 2H), 3.62 (s, 2H), 1.39 (s, 9H), 1.15 (s, 9H), 0.98 (t, J=7.1 Hz, 3H); MS (ES+): 671.3 (M+Na); Optical rotation [α]$_D$=+4.0 (c=0.10, MeOH).

Step-3: Preparation of Ethyl 2-(2-((2-(aminomethyl)-7-(3-(((tert-butoxycarbonyl)amino)methyl)phenyl)benzofuran-5-yl)methoxy)phenyl)acetate (294c)

To a stirred solution of (+)-(R)-ethyl 2-(2-((7-(3-(((tert-butoxycarbonyl)amino)methyl)phenyl)-2-((1,1-dimethylethylsulfinamido)methyl)benzofuran-5-yl)methoxy)phenyl)acetate (294b) (1.45 g, 2.235 mmol) in tetrahydrofuran (100 mL) was added HCl 3 N solution in water (0.745 mL, 2.235 mmol) at room temperature and stirred for 30 mins. The reaction was quenched by adding saturated sodium bicarbonate solution. The THF layer was separated washed with brine, dried, filtered and concentrated. The crude residue was purified by flash column chromatography (silica gel, 40 g) to afford ethyl 2-(2-((2-(aminomethyl)-7-(3-(((tert-butoxycarbonyl)amino)methyl)phenyl)benzofuran-5-yl)methoxy)phenyl)acetate (294c) (1.217 g, 100% yield) as a brown syrup; $^1$H NMR (300 MHz, DMSO-$d_6$) δ 7.74 (dd, J=6.4, 1.4 Hz, 2H), 7.60 (d, J=1.6 Hz, 1H), 7.51-7.41 (m, 3H), 7.32-7.24 (m, 2H), 7.22 (dd, J=7.8, 1.6 Hz, 2H), 7.11 (dd, J=8.3, 1.2 Hz, 1H), 6.91 (td, J=7.4, 1.1 Hz, 1H), 6.75 (d, J=1.0 Hz, 1H), 5.21 (s, 2H), 4.23 (d, J=6.2 Hz, 2H), 3.93 (q, J=7.1 Hz, 2H), 3.86 (s, 2H), 3.62 (s, 2H), 1.39 (s, 9H), 0.99 (t, J=7.1 Hz, 3H); MS (ES+): 567.2 (M+Na).

Step-4: Preparation of Ethyl 2-(2-((2-(benzamidomethyl)-7-(3-(((tert-butoxycarbonyl)amino)methyl)phenyl)benzofuran-5-yl)methoxy)phenyl)acetate (294d)

Compound 294d was prepared according to the procedure reported in step-4 of scheme-1 from ethyl 2-(2-((2-(aminomethyl)-7-(3-(((tert-butoxycarbonyl)amino)methyl)phenyl)benzofuran-5-yl)methoxy)phenyl)acetate (294c) (250 mg, 0.459 mmol) and benzoic acid (84 mg, 0.689 mmol) in DMF (3 mL) using HATU (262 mg, 0.689 mmol) and DIPEA (0.320 mL, 1.836 mmol) and stirring at room temperature for 16 h. This gave after workup and purification by flash column chromatography (silica gel, 40 g, eluting with 0 to 100% EtOAc in hexane) ethyl 2-(2-((2-(benzamidomethyl)-7-(3-(((tert-butoxycarbonyl)amino)methyl)phenyl)benzofuran-5-yl)methoxy)phenyl)acetate (294d) (174 mg, 58% yield) as a white solid; $^1$H NMR (300 MHz, DMSO-$d_6$) δ 9.15 (t, J=5.7 Hz, 1H), 7.97-7.85 (m, 2H), 7.84-7.70 (m, 2H), 7.62 (d, J=1.6 Hz, 1H), 7.59-7.38 (m, 5H), 7.32-7.16 (m, 4H), 7.14-7.06 (m, 1H), 6.90 (td, J=7.4, 1.1 Hz, 1H), 6.82 (d, J=0.9 Hz, 1H), 5.21 (s, 2H), 4.67 (d, J=5.6 Hz, 2H), 4.20 (d, J=6.2 Hz, 2H), 3.91 (q, J=7.1 Hz, 2H), 3.61 (s, 2H), 1.39 (s, 9H), 0.97 (t, J=7.1 Hz, 3H).

Step-5: Preparation of Ethyl 2-(2-((7-(3-(aminomethyl)phenyl)-2-(benzamidomethyl)benzofuran-5-yl)methoxy)phenyl)acetate (294e)

Compound 294e was prepared according to the procedure reported in step-5 of scheme-1 from ethyl 2-(2-((2-(benzamidomethyl)-7-(3-(((tert-butoxycarbonyl)amino)methyl)phenyl)benzofuran-5-yl)methoxy)phenyl)acetate (294d) (175 mg, 0.270 mmol) in DCM (15 mL) using TFA (0.208 mL, 2.70 mmol). This gave after workup ethyl 2-(2-((7-(3-(aminomethyl)phenyl)-2-(benzamidomethyl)benzofuran-5-yl)methoxy)phenyl)acetate (294e) (148 mg) as a light brown syrup. MS (ES+): 549.2 (M+1).

Step-6: Preparation of 2-(2-((7-(3-(aminomethyl)phenyl)-2-(benzamidomethyl)benzofuran-5-yl)methoxy)phenyl)acetic Acid (294f)

Compound 294f was prepared according to the procedure reported in step-6 of scheme-1 from ethyl 2-(2-((7-(3-(aminomethyl)phenyl)-2-(benzamidomethyl)benzofuran-5-yl)methoxy)phenyl)acetate (294e) (148 mg, 0.270 mmol) in MeOH (2 mL), THF (15 mL) using a solution of lithium hydroxide monohydrate (26 mg, 1.079 mmol) in water (2 mL). This gave after workup and purification by reverse phase column [C18 (50g), eluting with ACN in water (containing 0.1% HCl) from 0-100%] 2-(2-((7-(3-(aminomethyl)phenyl)-2-(benzamidomethyl)benzofuran-5-yl)methoxy)phenyl)acetic acid (294f) (25 mg, 18% yield) hydrochloride salt as a white solid; $^1$H NMR (300 MHz, DMSO-$d_6$) δ 12.24 (s, 1H), 9.26 (t, J=5.7 Hz, 1H), 8.46 (s, 3H), 8.03 (d, J=2.1 Hz, 1H), 7.94 (dt, J=6.7, 1.6 Hz, 3H), 7.68 (d, J=1.6 Hz, 1H), 7.61 (d, J=1.6 Hz, 1H), 7.59-7.44 (m, 5H), 7.21 (d, J=7.5 Hz, 2H), 7.08 (d, J=8.1 Hz, 1H), 6.89 (t, J=7.4 Hz, 1H), 6.83 (s, 1H), 5.24 (s, 2H), 4.68 (d, J=5.6 Hz, 2H), 4.11 (p, J=6.2 Hz, 2H), 3.58 (s, 2H); MS (ES+): 522.20 (M+1), (ES−): 519.20 (M−1).

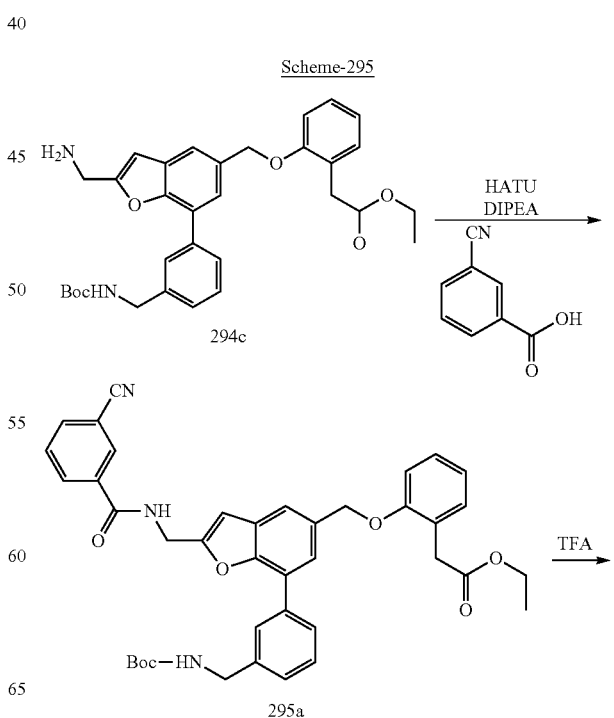

Scheme-295

-continued

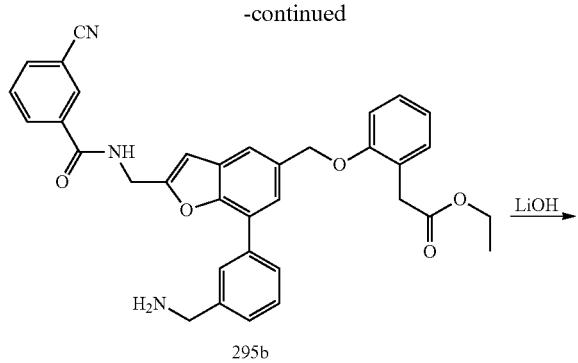

295b

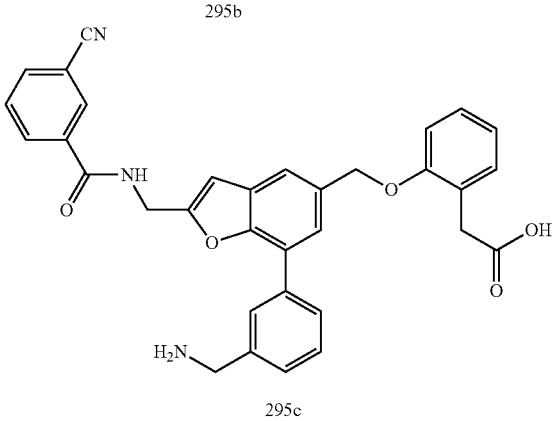

295c

Preparation of 2-(2-((7-(3-(aminomethyl)phenyl)-2-((3-cyanobenzamido)methyl)benzofuran-5-yl)methoxy)phenyl)acetic Acid (295c)

Step-1: Preparation of Ethyl 2-(2-((7-(3-(((tert-butoxycarbonyl)amino)methyl)phenyl)-2-((3-cyanobenzamido)methyl)benzofuran-5-yl)methoxy)phenyl)acetate (295a)

Compound 295a was prepared according to the procedure reported in step-4 of scheme-1 from ethyl 2-(2-((2-(aminomethyl)-7-(3-(((tert-butoxycarbonyl)amino)methyl)phenyl)benzofuran-5-yl)methoxy)phenyl)acetate (294c) (250 mg, 0.459 mmol) and 3-cyanobenzoic acid (101 mg, 0.689 mmol) in DMF (3 mL) using HATU (262 mg, 0.689 mmol) and DIPEA (0.320 mL, 1.836 mmol) and stirring at room temperature for 16 h. This gave after workup and purification by flash column chromatography (silica gel) ethyl 2-(2-((7-(3-(((tert-butoxycarbonyl)amino)methyl)phenyl)-2-((3-cyanobenzamido)methyl)benzofuran-5-yl)methoxy)phenyl)acetate (295a) (243 mg, 79% yield) as a white solid; $^1$H NMR (300 MHz, DMSO-$d_6$) δ 9.36 (t, J=5.6 Hz, 1H), 8.34 (t, J=1.6 Hz, 1H), 8.25-8.17 (m, 1H), 8.03 (dt, J=7.7, 1.3 Hz, 1H), 7.95 (s, 1H), 7.79-7.67 (m, 3H), 7.63 (d, J=1.6 Hz, 1H), 7.51 (s, 1H), 7.45 (t, J=7.5 Hz, 2H), 7.31-7.24 (m, 2H), 7.24-7.18 (m, 1H), 7.10 (d, J=8.1 Hz, 1H), 6.94-6.85 (m, 2H), 5.22 (s, 2H), 4.69 (d, J=5.5 Hz, 2H), 4.20 (d, J=6.1 Hz, 2H), 3.92 (q, J=7.1 Hz, 2H), 3.61 (s, 2H), 1.38 (s, 9H), 0.97 (t, J=7.1 Hz, 3H); MS (ES+): 574.2 (M+1-100).

Step-2: Preparation of Ethyl 2-(2-((7-(3-(aminomethyl)phenyl)-2-((3-cyanobenzamido)methyl)benzofuran-5-yl)methoxy)phenyl)acetate (295b)

Compound 295b was prepared according to the procedure reported in step-5 of scheme-1 from ethyl 2-(2-((7-(3-(((tert-butoxycarbonyl)amino)methyl)phenyl)-2-((3-cyanobenzamido)methyl)benzofuran-5-yl)methoxy)phenyl)acetate (295a) (240 mg, 0.356 mmol) in DCM (15 mL) using TFA (0.326 mL, 4.23 mmol). This gave after workup ethyl 2-(2-((7-(3-(aminomethyl)phenyl)-2-((3-cyanobenzamido)methyl)benzofuran-5-yl)methoxy)phenyl)acetate (295b) (204 mg) which was as such in the next step without further purification; MS (ES+): 574.2 (M+1), (ES-): 572.2 (M-1).

Step-3: Preparation of 2-(2-((7-(3-(aminomethyl)phenyl)-2-((3-cyanobenzamido)methyl)benzofuran-5-yl)methoxy)phenyl)acetic Acid (295c)

Compound 295c was prepared according to the procedure reported in step-6 of scheme-1 from ethyl 2-(2-((7-(3-(aminomethyl)phenyl)-2-((3-cyanobenzamido)methyl)benzofuran-5-yl)methoxy)phenyl)acetate (295b) (204 mg, 0.356 mmol) in MeOH (2 mL), THF (15 mL) using a solution of lithium hydroxide monohydrate (34 mg, 1.423 mmol) in water (2 mL). This gave after workup and purification by reverse phase column [C18 (50g), eluting with ACN in water (containing 0.1% HCl) from 0-100%] 2-(2-((7-(3-(aminomethyl)phenyl)-2-((3-cyanobenzamido)methyl)benzofuran-5-yl)methoxy)phenyl)acetic acid (295c) (30 mg, 16% yield) hydrochloride salt as a white solid; $^1$H NMR (300 MHz, DMSO-$d_6$) δ 12.19 (s, 1H), 9.46 (t, J=5.6 Hz, 1H), 8.35 (t, J=1.7 Hz, 1H), 8.23 (dt, J=7.9, 1.5 Hz, 1H), 8.04 (dt, J=7.7, 1.4 Hz, 1H), 8.00 (d, J=1.6 Hz, 1H), 7.95 (dt, J=7.4, 1.7 Hz, 1H), 7.74 (d, J=7.9 Hz, 1H), 7.70-7.66 (m, 1H), 7.63-7.48 (m, 3H), 7.23 (t, J=7.5 Hz, 2H), 7.08 (d, J=8.1 Hz, 1H), 6.95-6.84 (m, 2H), 5.25 (s, 2H), 4.70 (d, J=5.5 Hz, 2H), 4.13 (s, 2H), 3.58 (s, 2H); MS (ES+): 546.20 (M+1), (ES-): 544.20 (M-1).

Scheme-296

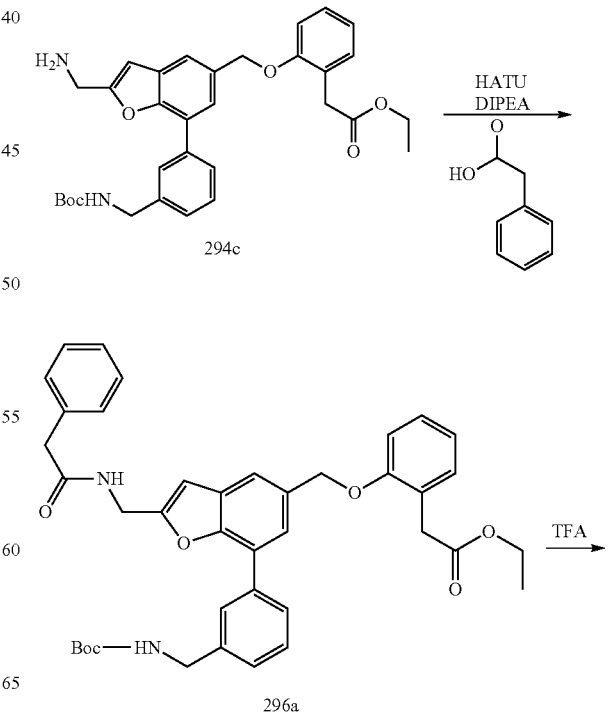

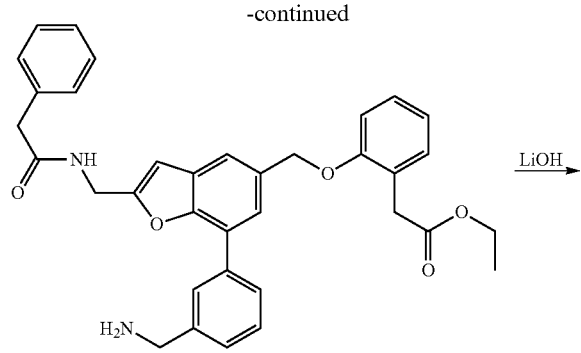

296b

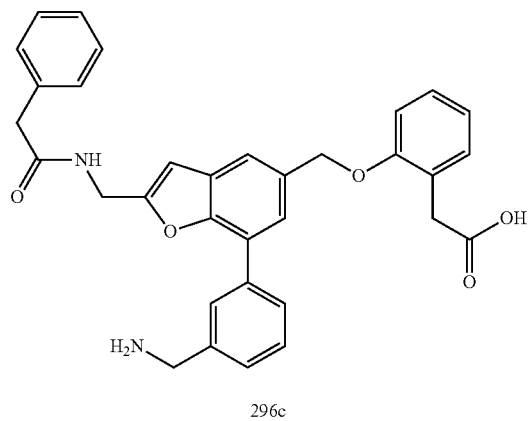

296c

Preparation of 2-(2-((7-(3-(aminomethyl)phenyl)-2-((2-phenylacetamido)methyl)benzofuran-5-yl)methoxy)phenyl)acetic Acid (296c)

Step-1: Preparation of Ethyl 2-(2-((7-(3-(((tert-butoxycarbonyl)amino)methyl)phenyl)-2-((2-phenylacetamido)methyl)benzofuran-5-yl)methoxy)phenyl)acetate (296a)

Compound 296a was prepared according to the procedure reported in step-4 of scheme-1 from ethyl 2-(2-((2-(aminomethyl)-7-(3-(((tert-butoxycarbonyl)amino)methyl)phenyl)benzofuran-5-yl)methoxy)phenyl)acetate (294c) (250 mg, 0.459 mmol) and 2-phenylacetic acid (94 mg, 0.689 mmol) in DMF (3 mL) using HATU (262 mg, 0.689 mmol) and DIPEA (0.320 mL, 1.836 mmol) and stirring at room temperature for 16 h. This gave after workup and purification by flash column chromatography (silica gel) ethyl 2-(2-((7-(3-(((tert-butoxycarbonyl)amino)methyl)phenyl)-2-((2-phenylacetamido)methyl)benzofuran-5-yl)methoxy)phenyl)acetate (296a) (300 mg, 99% yield) as a white solid; $^1$H NMR (300 MHz, DMSO-$d_6$) δ 8.69 (t, J=5.6 Hz, 1H), 7.95 (s, 1H), 7.79-7.71 (m, 2H), 7.60 (d, J=1.7 Hz, 1H), 7.55-7.40 (m, 3H), 7.34-7.17 (m, 8H), 7.10 (dd, J=8.3, 1.1 Hz, 1H), 6.91 (td, J=7.4, 1.1 Hz, 1H), 6.72 (d, J=0.9 Hz, 1H), 5.21 (s, 2H), 4.46 (d, J=5.6 Hz, 2H), 4.23 (d, J=6.2 Hz, 2H), 3.92 (q, J=7.1 Hz, 2H), 3.62 (s, 2H), 3.50 (s, 2H), 1.38 (s, 9H), 0.97 (t, J=7.1 Hz, 3H); MS (ES+): 585.2 (M−100+Na).

Step-2: Preparation of Ethyl 2-(2-((7-(3-(aminomethyl)phenyl)-2-((2-phenylacetamido)methyl)benzofuran-5-yl)methoxy)phenyl)acetate (296b)

Compound 296b was prepared according to the procedure reported in step-5 of scheme-1 from ethyl 2-(2-((7-(3-(((tert-butoxycarbonyl)amino)methyl)phenyl)-2-((2-phenylacetamido)methyl)benzofuran-5-yl)methoxy)phenyl)acetate (296a) (245 mg, 0.370 mmol) in DCM (15 mL) using TFA (0.285 mL, 3.70 mmol). This gave after workup ethyl 2-(2-((7-(3-(aminomethyl)phenyl)-2-((2-phenylacetamido)methyl)benzofuran-5-yl)methoxy)phenyl)acetate (296b) (200 mg) which was used as such in the next step without further purification; MS (ES+): 563.2 (M+1).

Step-3: Preparation of 2-(2-((7-(3-(aminomethyl)phenyl)-2-((2-phenylacetamido)methyl)benzofuran-5-yl)methoxy)phenyl)acetic Acid (296c)

Compound 296c was prepared according to the procedure reported in step-6 of scheme-1 from ethyl 2-(2-((7-(3-(aminomethyl)phenyl)-2-((2-phenylacetamido)methyl)benzofuran-5-yl)methoxy)phenyl)acetate (296b) (200 mg, 0.355 mmol) in MeOH (2 mL), THF (15 mL) using a solution of lithium hydroxide monohydrate (34 mg, 1.423 mmol) in water (2 mL). This gave after workup and purification by reverse phase column [C18 (50g), eluting with ACN in water (containing 0.1% HCl) from 0-100%] 2-(2-((7-(3-(aminomethyl)phenyl)-2-((2-phenylacetamido)methyl)benzofuran-5-yl)methoxy)phenyl)acetic acid (296c) (70 mg, 37% yield) hydrochloride salt as a white solid; $^1$H NMR (300 MHz, DMSO-$d_6$) δ 12.23 (s, 1H), 8.81 (t, J=5.6 Hz, 1H), 8.36 (s, 3H), 8.00 (s, 1H), 7.95-7.87 (m, 1H), 7.67 (d, J=1.6 Hz, 1H), 7.60 (d, J=1.8 Hz, 1H), 7.59-7.49 (m, 2H), 7.31-7.25 (m, 4H), 7.22 (dd, J=8.1, 1.8 Hz, 3H), 7.08 (d, J=8.1 Hz, 1H), 6.94-6.86 (m, 1H), 6.75 (d, J=0.9 Hz, 1H), 5.24 (s, 2H), 4.47 (d, J=5.6 Hz, 2H), 4.12 (s, 2H), 3.59 (s, 2H), 3.52 (s, 2H); MS (ES+): 535.20 (M+1), (ES−): 533.20 (M−1).

Scheme-297

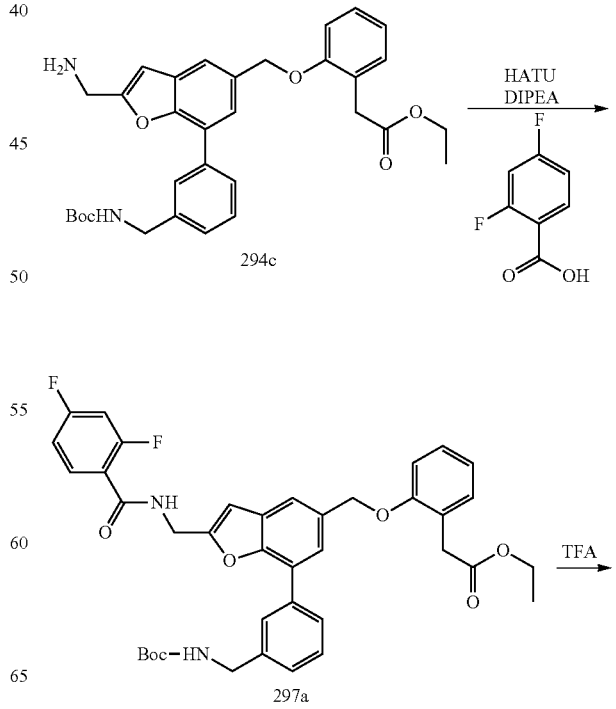

294c

297a

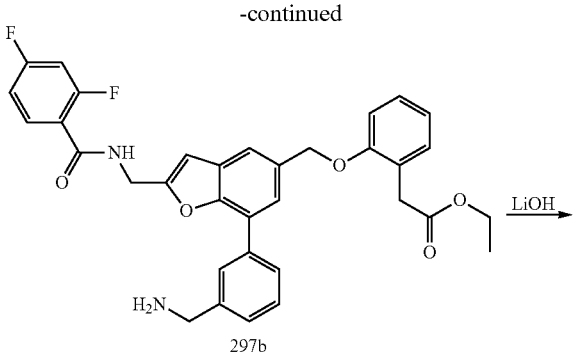

297b

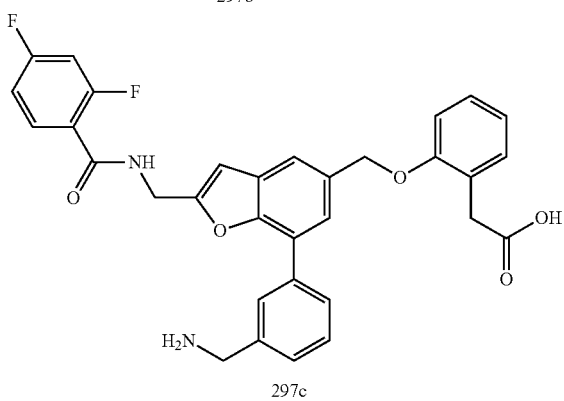

297c

Preparation of 2-(2-((7-(3-(aminomethyl)phenyl)-2-((2,4-difluorobenzamido)methyl)benzofuran-5-yl)methoxy)phenyl)acetic Acid (297c)

Step-1: Preparation of Ethyl 2-(2-((7-(3-(((tert-butoxycarbonyl)amino)methyl)phenyl)-2-((2,4-difluorobenzamido)methyl)benzofuran-5-yl)methoxy)phenyl)acetate (297a)

Compound 297a was prepared according to the procedure reported in step-4 of scheme-1 from ethyl 2-(2-((2-(aminomethyl)-7-(3-(((tert-butoxycarbonyl)amino)methyl)phenyl)benzofuran-5-yl)methoxy)phenyl)acetate (294c) (250 mg, 0.459 mmol) and 2,4-difluorobenzoic acid (109 mg, 0.689 mmol) in DMF (3 mL) using HATU (262 mg, 0.689 mmol) and DIPEA (0.320 mL, 1.836 mmol) and stirring at room temperature for 16 h. This gave after workup and purification by flash column chromatography (silica gel) ethyl 2-(2-((7-(3-(((tert-butoxycarbonyl)amino)methyl)phenyl)-2-((2,4-difluorobenzamido)methyl)benzofuran-5-yl)methoxy)phenyl)acetate (297a) (312 mg, 99% yield) as a white solid; $^1$H NMR (300 MHz, DMSO-$d_6$) δ 9.02 (t, J=5.2 Hz, 1H), 7.75 (td, J=9.0, 7.0 Hz, 3H), 7.63 (d, J=1.6 Hz, 1H), 7.55-7.33 (m, 4H), 7.33-7.14 (m, 4H), 7.10 (d, J=8.2 Hz, 1H), 6.90 (td, J=7.4, 1.1 Hz, 1H), 6.83 (s, 1H), 5.22 (s, 2H), 4.65 (d, J=5.7 Hz, 2H), 4.21 (d, J=6.2 Hz, 2H), 3.92 (q, J=7.1 Hz, 2H), 3.62 (s, 2H), 1.39 (s, 9H), 0.98 (t, J=7.1 Hz, 3H); $^{19}$F NMR (282 MHz, DMSO-$d_6$) δ−106.29 (d, J=9.3 Hz), −109.33 (d, J=9.3 Hz).

Step-2: Preparation of Ethyl 2-(2-((7-(3-(aminomethyl)phenyl)-2-((2,4-difluorobenzamido)methyl)benzofuran-5-yl)methoxy)phenyl)acetate (297b)

Compound 297b was prepared according to the procedure reported in step-5 of scheme-1 from ethyl 2-(2-((7-(3-(((tert-butoxycarbonyl)amino)methyl)phenyl)-2-((2,4-difluorobenzamido)methyl)benzofuran-5-yl)methoxy)phenyl)acetate (297a) (305 mg, 0.445 mmol) in DCM (15 mL) using TFA (0.343 mL, 4.45 mmol). This gave after workup ethyl 2-(2-((7-(3-(aminomethyl)phenyl)-2-((2,4-difluorobenzamido)methyl)benzofuran-5-yl)methoxy)phenyl)acetate (297b) (260 mg) which was used as such in the next step without further purification; MS (ES+): 585.2 (M+1), (ES−): 583.2 (M−1).

Step-3: Preparation of 2-(2-((7-(3-(aminomethyl)phenyl)-2-((2,4-difluorobenzamido)methyl)benzofuran-5-yl)methoxy)phenyl)acetic Acid (297c)

Compound 297c was prepared according to the procedure reported in step-6 of scheme-1 from ethyl 2-(2-((7-(3-(aminomethyl)phenyl)-2-((2,4-difluorobenzamido)methyl)benzofuran-5-yl)methoxy)phenyl)acetate (297b) (148 mg, 0.253 mmol) in MeOH (2 mL), THF (15 mL) using a solution of lithium hydroxide monohydrate (24 mg, 1.013 mmol) in water (2 mL). This gave after workup and purification by reverse phase column [C18 (50g), eluting with ACN in water (containing 0.1% HCl) from 0-100%] 2-(2-((7-(3-(aminomethyl)phenyl)-2-((2,4-difluorobenzamido)methyl)benzofuran-5-yl)methoxy)phenyl)acetic acid (297c) (15 mg, 11% yield) hydrochloride salt as a white solid; $^1$H NMR (300 MHz, DMSO-$d_6$) δ 9.13-9.01 (m, 1H), 8.01 (d, J=2.2 Hz, 1H), 7.97 (dt, J=7.6, 1.6 Hz, 1H), 7.75 (td, J=8.6, 6.7 Hz, 1H), 7.69 (d, J=1.6 Hz, 1H), 7.62-7.48 (m, 3H), 7.45-7.35 (m, 1H), 7.26-7.16 (m, 3H), 7.08 (d, J=8.1 Hz, 1H), 6.94-6.86 (m, 1H), 6.85 (s, 1H), 5.25 (s, 2H), 4.67 (d, J=5.8 Hz, 2H), 4.13 (s, 2H), 3.58 (s, 2H); $^{19}$F NMR (282 MHz, DMSO-$d_6$) δ−106.16 (d, J=10.2 Hz), −109.33; MS (ES+): 557.20 (M+1), (ES−): 555.20 (M−1).

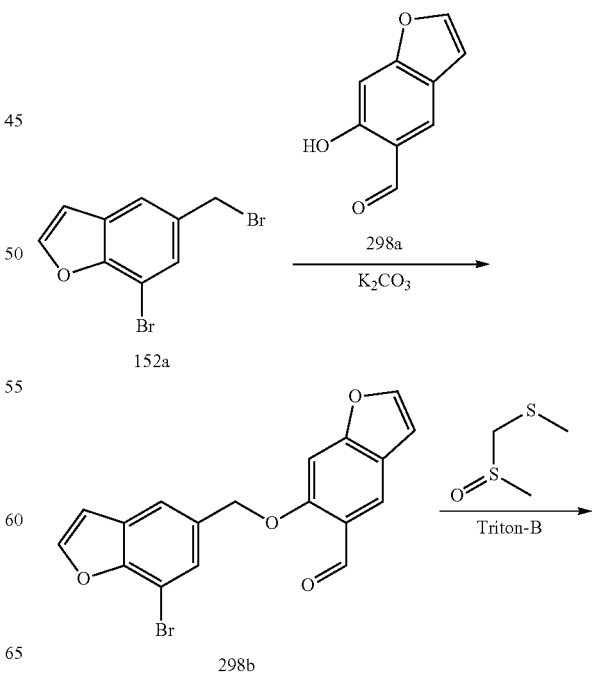

Scheme-298

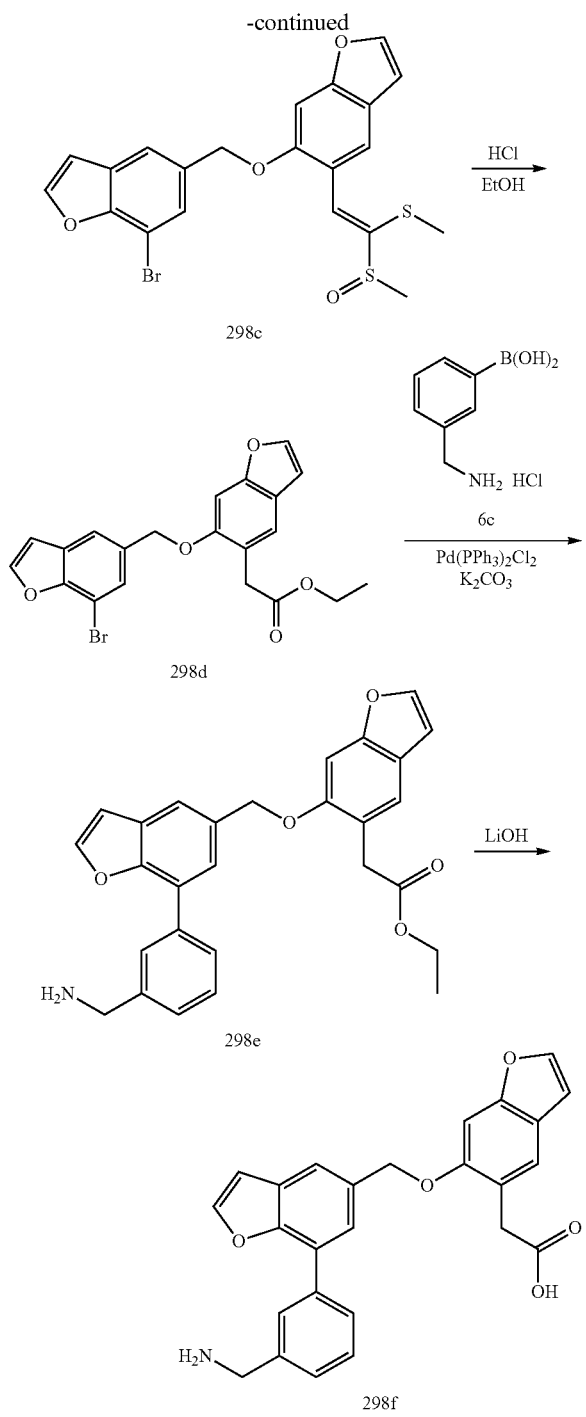

Preparation of 2-(6-((7-(3-(aminomethyl)phenyl)benzofuran-5-yl)methoxy)benzofuran-5-yl)acetic Acid (298f)

Step-1: Preparation of 6-((7-bromobenzofuran-5-yl)methoxy)benzofuran-5-carbaldehyde (298b)

Compound 298b was prepared according to the procedure reported in step-2 of scheme-152 from 7-bromo-5-(bromomethyl)benzofuran (152a) (1.413 g, 4.87 mmol) using 6-hydroxybenzofuran-5-carbaldehyde (298a) (790 mg, 4.87 mmol; CAS #20073-22-7; Prepared according to the procedure reported By Sairam, Mudulkar et al; in Tetrahedron Letters, 56(11), 1338-1343; 2015), $K_2CO_3$ (2.021 g, 14.62 mmol) in DMF (10 mL) and stirring at room temperature for 12 h. This gave after workup 6-((7-bromobenzofuran-5-yl)methoxy)benzofuran-5-carbaldehyde (298b) (1.73 g, 96% yield) as a white solid; $^1$H NMR (300 MHz, DMSO-$d_6$) δ 10.45 (s, 1H), 8.16 (d, J=2.2 Hz, 1H), 8.05 (s, 1H), 8.02 (d, J=2.3 Hz, 1H), 7.88 (d, J=1.5 Hz, 1H), 7.77 (d, J=1.5 Hz, 1H), 7.62 (d, J=0.9 Hz, 1H), 7.14 (d, J=2.2 Hz, 1H), 7.02 (dd, J=2.2, 0.9 Hz, 1H), 5.42 (s, 2H).

Step-2: Preparation of 7-bromo-5-(((5-(2-(methylsulfinyl)-2-(methylthio)vinyl)benzofuran-6-yl)oxy)methyl)benzofuran (298c)

Compound 298c was prepared according to the procedure reported in step-3 of scheme-266 from 6-((7-bromobenzofuran-5-yl)methoxy)benzofuran-5-carbaldehyde (298b) (1.70 g, 4.58 mmol) in THF (40 mL) using methyl(methylsulfinylmethyl)sulfane (0.910 g, 7.33 mmol), Triton-B (40% methanolic solution, 1.041 mL, 2.290 mmol) and heating at reflux for 12 h. This gave after workup and purification by flash column chromatography (Silica gel, 40 g, eluting with EtOAc in hexane) 7-bromo-5-(((5-(2-(methylsulfinyl)-2-(methylthio)vinyl)benzofuran-6-yl)oxy)methyl)benzofuran (298c) (1.78 g, 81% yield) as a light yellow solid; $^1$H NMR (300 MHz, DMSO-$d_6$) δ 8.27 (s, 1H), 8.14 (d, J=2.2 Hz, 1H), 7.94 (d, J=2.2 Hz, 1H), 7.91 (d, J=0.6 Hz, 1H), 7.78 (d, J=1.5 Hz, 1H), 7.67 (d, J=1.5 Hz, 1H), 7.51 (d, J=0.9 Hz, 1H), 7.10 (d, J=2.2 Hz, 1H), 6.98 (dd, J=2.2, 0.9 Hz, 1H), 5.35 (s, 2H), 2.74 (s, 3H), 2.28 (s, 3H).

Step-3: Preparation of Ethyl 2-(6-((7-bromobenzofuran-5-yl)methoxy)benzofuran-5-yl)acetate (298d)

Compound 298d was prepared according to the procedure reported in step-4 of scheme-266 from 7-bromo-5-(((5-(2-(methylsulfinyl)-2-(methylthio)vinyl)benzofuran-6-yl)oxy)methyl)benzofuran (298c) (1.7 g, 3.56 mmol) in ethanol (50 mL) using HCl (4 M in 1,4-dioxane, 3.56 mL, 14.24 mmol) and heating at reflux for 12 h. This gave after workup and purification by flash column chromatography (silica gel, 40 g, eluting with ethyl acetate and hexanes) ethyl 2-(6-((7-bromobenzofuran-5-yl)methoxy)benzofuran-5-yl)acetate (298d) (1.06 g, 69% yield) as a white solid; $^1$H NMR (300 MHz, DMSO-$d_6$) δ 8.15 (d, J=2.2 Hz, 1H), 7.87 (d, J=2.2 Hz, 1H), 7.74 (d, J=1.4 Hz, 1H), 7.62 (d, J=1.5 Hz, 1H), 7.49 (s, 1H), 7.38 (d, J=1.0 Hz, 1H), 7.12 (d, J=2.2 Hz, 1H), 6.87 (dd, J=2.2, 0.9 Hz, 1H), 5.23 (s, 2H), 4.02 (q, J=7.1 Hz, 2H), 3.69 (s, 2H), 1.07 (t, J=7.1 Hz, 3H).

Step-4: Preparation of Ethyl 2-(6-((7-(3-(aminomethyl)phenyl)benzofuran-5-yl)methoxy)benzofuran-5-yl)acetate (298e)

Compound 298e was prepared according to the procedure reported in step-3 of scheme-1 from ethyl 2-(6-((7-bromobenzofuran-5-yl)methoxy)benzofuran-5-yl)acetate (298d) (475 mg, 1.107 mmol) in dioxane (15 mL) using 3-(aminomethyl)phenylboronic acid hydrochloride (6c) (259 mg, 1.383 mmol), bis(triphenylphosphine)palladium (II) chloride (Pd(PPh$_3$)$_2$Cl$_2$) (117 mg, 0.166 mmol), potassium carbonate (459 mg, 3.32 mmol) in water (3 mL) under an argon atmosphere heating at 100° C. for 12 h on oil bath. This gave after workup, purification by flash column chromatography (silica gel, 24 g, eluting with DMA-80 in DCM from 0-50%) ethyl 2-(6-((7-(3-(aminomethyl)phenyl)benzofuran-5-yl)methoxy)benzofuran-5-yl)acetate (298e) (450 mg, 89% yield) as a sticky material; $^1$H NMR (300 MHz, DMSO-$d_6$) δ 8.10 (d, J=2.2 Hz, 1H), 7.86 (d, J=2.2 Hz, 1H), 7.83 (d, J=1.7 Hz, 1H), 7.72 (tt, J=3.6, 1.6 Hz, 2H), 7.60 (d, J=1.7 Hz, 1H), 7.50-7.43 (m, 2H), 7.42-7.37 (m, 2H), 7.06 (d, J=2.2 Hz, 1H), 6.86 (dd, J=2.2, 0.9 Hz, 1H), 5.29 (s, 2H), 3.92 (q, J=7.1 Hz, 2H), 3.81 (s, 2H), 3.70 (s, 2H), 0.97 (t, J=7.1 Hz, 3H); MS (ES+): 456.1 (M+1).

Step-5: Preparation of 2-(6-((7-(3-(aminomethyl)phenyl)benzofuran-5-yl)methoxy)benzofuran-5-yl) acetic Acid (298f)

Compound 298f was prepared according to the procedure reported in step-6 of scheme-1 from ethyl 2-(6-((7-(3-(aminomethyl)phenyl)benzofuran-5-yl)methoxy)benzofuran-5-yl)acetate (298e) (450 mg, 0.988 mmol) in MeOH (5 mL), THF (10 mL) using a solution of lithium hydroxide (95 mg, 3.95 mmol) in water (2 mL). This gave after workup and purification by reverse phase column [C18 (150g), eluting with ACN in water (containing 0.1% HCl) from 0-100%] 2-(6-((7-(3-(aminomethyl)phenyl)benzofuran-5-yl)methoxy)benzofuran-5-yl)acetic acid (298f) (250 mg, 59% yield) hydrochloride salt as a white solid; $^1$H NMR (300 MHz, DMSO-$d_6$) δ 8.46 (s, 3H), 8.11 (d, J=2.2 Hz, 1H), 8.01 (d, J=1.9 Hz, 1H), 7.93 (dt, J=7.2, 1.8 Hz, 1H), 7.85 (d, J=2.2 Hz, 1H), 7.79 (d, J=1.6 Hz, 1H), 7.68 (d, J=1.6 Hz, 1H), 7.63-7.51 (m, 2H), 7.48 (s, 1H), 7.37 (d, J=0.9 Hz, 1H), 7.07 (d, J=2.2 Hz, 1H), 6.86 (dd, J=2.2, 0.8 Hz, 1H), 5.32 (s, 2H), 4.14 (s, 2H), 3.67 (s, 2H); MS (ES+): 428.10 (M+1), (ES−): 426.10 (M−1); Analysis calculated for $C_{26}H_{21}NO_5 \cdot HCl \cdot H_2O$: C, 64.80; H, 5.02; Cl, 7.36; N, 2.91; Found: C, 65.00; H, 4.91; Cl, 7.40; N, 3.01.

Scheme-299

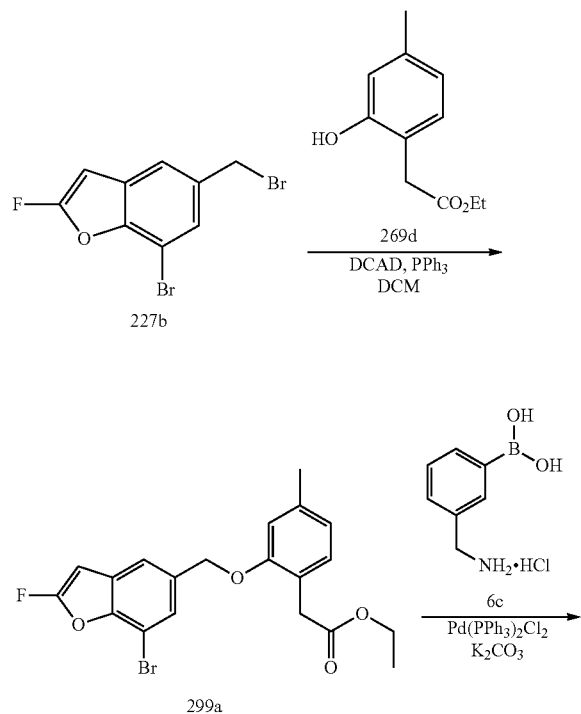

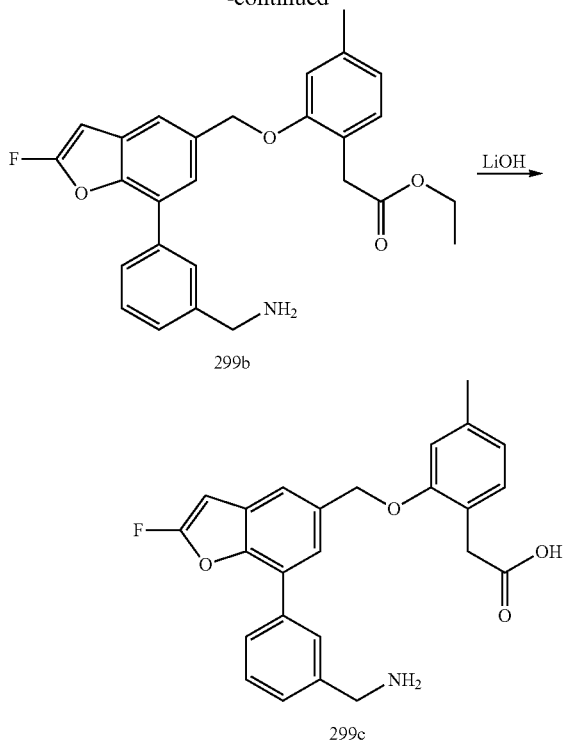

Preparation of 2-(2-((7-(3-(aminomethyl)phenyl)-2-fluorobenzofuran-5-yl)methoxy)-4-methylphenyl) acetic Acid (299c)

Step-1: Preparation of Ethyl 2-(2-((7-bromo-2-fluorobenzofuran-5-yl)methoxy)-4-methylphenyl)acetate (299a)

Compound 299a was prepared according to the procedure reported in step-2 of scheme-23 from (7-bromo-2-fluorobenzofuran-5-yl)methanol (227b) (600 mg, 2.449 mmol) in DCM (35 mL) using triphenylphosphine (771 mg, 2.94 mmol), ethyl 2-(2-hydroxy-4-methylphenyl)acetate (269d) (523 mg, 2.69 mmol) and (E)-bis(4-chlorobenzyl) diazene-1,2-dicarboxylate (DCAD, 1214 mg, 3.31 mmol) in DCM (20 mL). This gave after workup and purification by flash column chromatography [silica (40g), eluting with EtOAc in hexane from 0-40%] ethyl 2-(2-((7-bromo-2-fluorobenzofuran-5-yl)methoxy)-4-methylphenyl)acetate (299a) (425 mg, 1.009 mmol, 41.2% yield) as a white solid; $^1$H NMR (300 MHz, DMSO-$d_6$) δ 7.63 (d, J=1.5 Hz, 1H), 7.58 (d, J=1.5 Hz, 1H), 7.09 (d, J=7.5 Hz, 1H), 6.91 (t, J=1.1 Hz, 1H), 6.73 (ddd, J=7.4, 1.6, 0.8 Hz, 1H), 6.54 (d, J=6.4 Hz, 1H), 5.14 (s, 2H), 4.01 (q, J=7.1 Hz, 2H), 3.56 (s, 2H), 2.29 (s, 3H), 1.08 (t, J=7.1 Hz, 3H); $^{19}$F NMR (282 MHz, DMSO-$d_6$) δ−110.46; MS (ES+): 421.00, 423.00 (M, M+2).

Step-2: Preparation of Ethyl 2-(2-((7-(3-(aminomethyl)phenyl)-2-fluorobenzofuran-5-yl)methoxy)-4-methylphenyl)acetate (299b)

Compound 299b was prepared according to the procedure reported in step-3 of scheme-1 from ethyl 2-(2-((7-bromo-2-fluorobenzofuran-5-yl)methoxy)-4-methylphenyl)acetate (299a) (412 mg, 0.978 mmol) in dioxane (10 mL) using 3-(aminomethyl)phenylboronic acid hydrochloride (6c) (211 mg, 1.125 mmol), a solution of K₂CO₃ (406 mg, 2.93 mmol) in water (2 mL), bis(triphenylphosphine)palladium (II) chloride (103 mg, 0.147 mmol) and heating at 100° C. for 7 h on oil bath. This gave after workup, purification by flash column chromatography [silica (40 g), eluting with DMA80 in DCM from 0-50%] ethyl 2-(2-((7-(3-(aminomethyl)phenyl)-2-fluorobenzofuran-5-yl)methoxy)-4-methylphenyl)acetate (299b) (245 mg, 56% yield) as a pale yellow oil; ¹H NMR (300 MHz, DMSO-d₆) δ 7.76 (d, J=1.9 Hz, 1H), 7.65 (dt, J=7.5, 1.7 Hz, 1H), 7.61 (d, J=1.7 Hz, 1H), 7.55 (d, J=1.7 Hz, 1H), 7.47 (t, J=7.5 Hz, 1H), 7.44-7.38 (m, 1H), 7.09 (d, J=7.5 Hz, 1H), 6.99-6.91 (m, 1H), 6.77-6.69 (m, 1H), 6.44 (d, J=6.4 Hz, 1H), 5.20 (s, 2H), 3.91 (q, J=7.1 Hz, 2H), 3.81 (s, 2H), 3.57 (s, 2H), 2.29 (s, 3H), 0.98 (t, J=7.1 Hz, 3H); ¹⁹F NMR (282 MHz, DMSO-d₆) δ −111.74; MS (ES+): 448.2 (M+1), (ES−): 446.1 (M−1).

Step-3: Preparation of 2-(2-((7-(3-(aminomethyl)phenyl)-2-fluorobenzofuran-5-yl)methoxy)-4-methylphenyl)acetic Acid (299c)

Compound 299c was prepared according to the procedure reported in step-6 of scheme-1 from ethyl 2-(2-((7-(3-(aminomethyl)phenyl)-2-fluorobenzofuran-5-yl)methoxy)-4-methylphenyl)acetate (299b) (230 mg, 0.514 mmol) in MeOH/THF (2/10 mL) using a solution of lithium hydroxide monohydrate (49 mg, 2.056 mmol) in water (2 mL). This gave after workup and purification by reverse-phase column chromatography (C-18 column, 150 g, eluting with 0.1% aqueous HCl in water and acetonitrile from 0-100%) 2-(2-((7-(3-(aminomethyl)phenyl)-2-fluorobenzofuran-5-yl)methoxy)-4-methylphenyl)acetic acid (299c) (160 mg, 74% yield) hydrochloride salt as a white solid; ¹H NMR (300 MHz, DMSO-d₆) δ 7.94 (d, J=1.7 Hz, 1H), 7.86 (dt, J=7.2, 1.8 Hz, 1H), 7.68 (d, J=1.6 Hz, 1H), 7.62 (d, J=1.8 Hz, 1H), 7.61-7.53 (m, 2H), 7.09 (d, J=7.6 Hz, 1H), 6.93 (d, J=1.5 Hz, 1H), 6.72 (d, J=7.3 Hz, 1H), 6.45 (d, J=6.4 Hz, 1H), 5.22 (s, 2H), 4.14 (s, 2H), 3.53 (s, 2H), 2.28 (s, 3H); ¹⁹F NMR (282 MHz, DMSO-d₆) δ −111.57; MS (ES+): 420.10 (M+1), (ES−): 418.10 (M−1); Analysis calculated for C₂₅H₂₂FNO₄.HCl.H₂O: C, 63.36; H, 5.32; Cl, 7.48; N, 2.96; Found; C, 63.79; H, 5.57; Cl, 7.04; N, 3.03.

Scheme-300

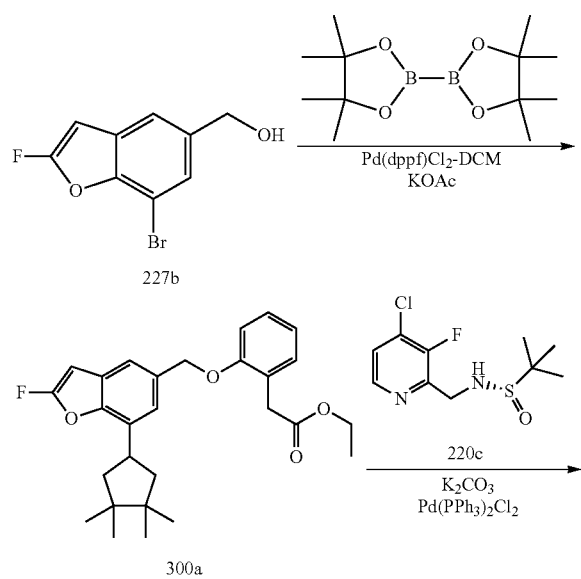

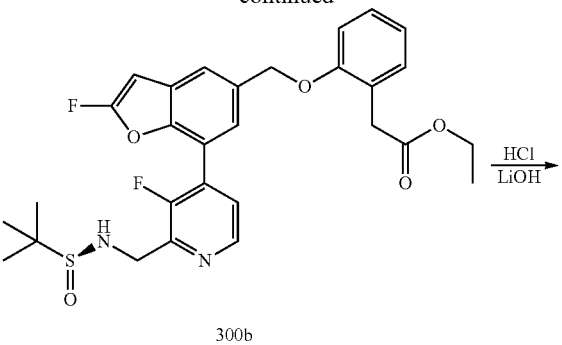

300b

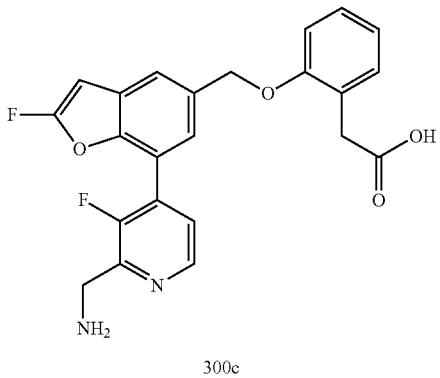

300c

Preparation of 2-(2-((7-(2-(aminomethyl)-3-fluoropyridin-4-yl)-2-fluorobenzofuran-5-yl)methoxy)phenyl)acetic Acid (300c)

Step-1: Preparation of Ethyl 2-(2-((2-fluoro-7-(4,4,5,5-tetramethyl-1,3,2-dioxaborolan-2-yl)benzofuran-5-yl)methoxy)phenyl)acetate (300a)

Compound 300a was prepared according to the procedure reported in step-1 of scheme-59 from (7-bromo-2-fluorobenzofuran-5-yl)methanol (227b) (1.00 g, 2.456 mmol), using bis(pinacolato)diboron (0.935 g, 3.68 mmol), potassium acetate (0.723 g, 7.37 mmol) and Pd(dppf)Cl₂-DCM (0.201 g, 0.246 mmol) in anhydrous dioxane (25 mL) under a nitrogen atmosphere and heating at 90° C. for 18 h. This gave after workup and purification by flash column chromatography [silica (40g), eluting with EtOAc in hexanes from 0-20%] ethyl 2-(2-((2-fluoro-7-(4,4,5,5-tetramethyl-1,3,2-dioxaborolan-2-yl)benzofuran-5-yl)methoxy)phenyl)acetate (300a) (910 mg, 82% yield) as a light brown oil; ¹H NMR (300 MHz, DMSO-d₆) δ 7.75 (d, J=1.9 Hz, 1H), 7.62 (d, J=1.9 Hz, 1H), 7.31-7.16 (m, 2H), 7.08 (dd, J=8.3, 1.1 Hz, 1H), 6.91 (td, J=7.4, 1.1 Hz, 1H), 6.35 (d, J=6.3 Hz, 1H), 5.15 (s, 2H), 4.00 (q, J=7.1 Hz, 2H), 3.59 (s, 2H), 1.33 (s, 12H), 1.06 (t, J=7.1 Hz, 3H); ¹⁹F NMR (282 MHz, DMSO-d₆) δ −111.69.

Step-2: Preparation of Ethyl 2-(2-((7-(2-((1,1-dimethylethylsulfinamido)methyl)-3-fluoropyridin-4-yl)-2-fluorobenzofuran-5-yl)methoxy)phenyl)acetate (300b)

Compound 300b was prepared according to the procedure reported in step-3 of scheme-1 from ethyl 2-(2-((2-fluoro-7-(4,4,5,5-tetramethyl-1,3,2-dioxaborolan-2-yl)benzofuran-5-yl)methoxy)phenyl)acetate (300a) (450 mg, 0.991 mmol) in dioxane (10 mL) using (+)-(S)—N-((4-chloro-3-fluoropyridin-2-yl)methyl)-2-methylpropane-2-sulfinamide (220c) (315 mg, 1.189 mmol), bis(triphenylphosphine)palladium(II) chloride (Pd(PPh$_3$)$_2$Cl$_2$) (104 mg, 0.149 mmol) and a solution of K$_2$CO$_3$ (411 mg, 2.97 mmol) in water (1 mL) under an argon atmosphere heating at 100° C. for 3 h on oil bath. This gave after workup, purification by flash column chromatography (silica gel, 24 g, eluting with MeOH/DCM from 0-15%) ethyl 2-(2-((7-(2-((1,1-dimethylethylsulfinamido)methyl)-3-fluoropyridin-4-yl)-2-fluorobenzofuran-5-yl)methoxy)phenyl)acetate (300b) (410 mg, 73.6%) as an brown oil; $^1$H NMR (300 MHz, DMSO-d$_6$) δ 8.53 (d, J=4.9 Hz, 1H), 7.78 (d, J=1.7 Hz, 1H), 7.66 (t, J=5.2 Hz, 1H), 7.55-7.48 (m, 1H), 7.31-7.20 (m, 2H), 7.11 (dd, J=8.3, 1.1 Hz, 1H), 6.92 (td, J=7.4, 1.1 Hz, 1H), 6.51 (d, J=6.4 Hz, 1H), 5.88 (t, J=5.8 Hz, 1H), 5.24 (s, 2H), 4.41 (dd, J=5.9, 2.0 Hz, 2H), 3.92 (q, J=7.1 Hz, 2H), 3.63 (s, 2H), 1.11 (s, 9H), 0.99 (t, J=7.1 Hz, 3H); $^{19}$F NMR (282 MHz, DMSO-d$_6$) δ-111.33, -127.78; MS (ES+): 557.2 (M+1), 580.2 (M+Na).

Step-3: Preparation of 2-(2-((7-(2-(aminomethyl)-3-fluoropyridin-4-yl)-2-fluorobenzofuran-5-yl)methoxy)phenyl)acetic Acid (300c)

To a stirred solution of ethyl 2-(2-((7-(2-((1,1-dimethylethylsulfinamido)methyl)-3-fluoropyridin-4-yl)-2-fluorobenzofuran-5-yl)methoxy)phenyl)acetate (300b) (400 mg, 0.719 mmol) in tetrahydrofuran (10 mL) was added 4 M HCl in 1-4-dioxane (0.359 mL, 1.437 mmol) and stirred at room temperature for 30 mins. The reaction was concentrated to dryness. The residue was dissolved in tetrahydrofuran (10 mL), acetonitrile (2 mL), water (2 mL) and added lithium hydroxide monohydrate (86 mg, 3.59 mmol) and continued stirring at room temperature for 48 h. The reaction was concentrated, diluted with water (5 mL) and acidified to pH 4 using 1M HCl. The solid separated out was collected by filtration and purified by reverse-phase column chromatography (C-18 column, 150 g, eluting with 0.1% aqueous HCl in water and acetonitrile from 0-100%) to afford 2-(2-((7-(2-(aminomethyl)-3-fluoropyridin-4-yl)-2-fluorobenzofuran-5-yl)methoxy)phenyl)acetic acid (300c) (125 mg, 41.0% yield) hydrochloride salt as a white solid; $^1$H NMR (300 MHz, DMSO-d$_6$) δ 8.64 (d, J=5.0 Hz, 1H), 8.56 (s, 4H), 7.84 (d, J=1.6 Hz, 1H), 7.80 (t, J=5.3 Hz, 1H), 7.59 (d, J=1.4 Hz, 1H), 7.24 (dd, J=9.1, 6.6 Hz, 2H), 7.08 (d, J=8.0 Hz, 1H), 6.91 (td, J=7.4, 1.1 Hz, 1H), 6.51 (d, J=6.4 Hz, 1H), 5.27 (s, 2H), 4.38 (d, J=5.3 Hz, 2H), 3.58 (s, 2H); $^{19}$F NMR (282 MHz, DMSO-d$_6$) δ-111.17, -128.47; MS (ES+): 425.10 (M+1), (ES-): 423.10 (M-1); Analysis calculated for C$_{23}$H$_{18}$F$_2$N$_2$O$_4$.1.25HCl.1.5H$_2$O: C, 55.58; H, 4.51; Cl, 8.92; N, 5.64; Found: C, 55.62; H, 4.49; Cl, 8.83; N, 5.69.

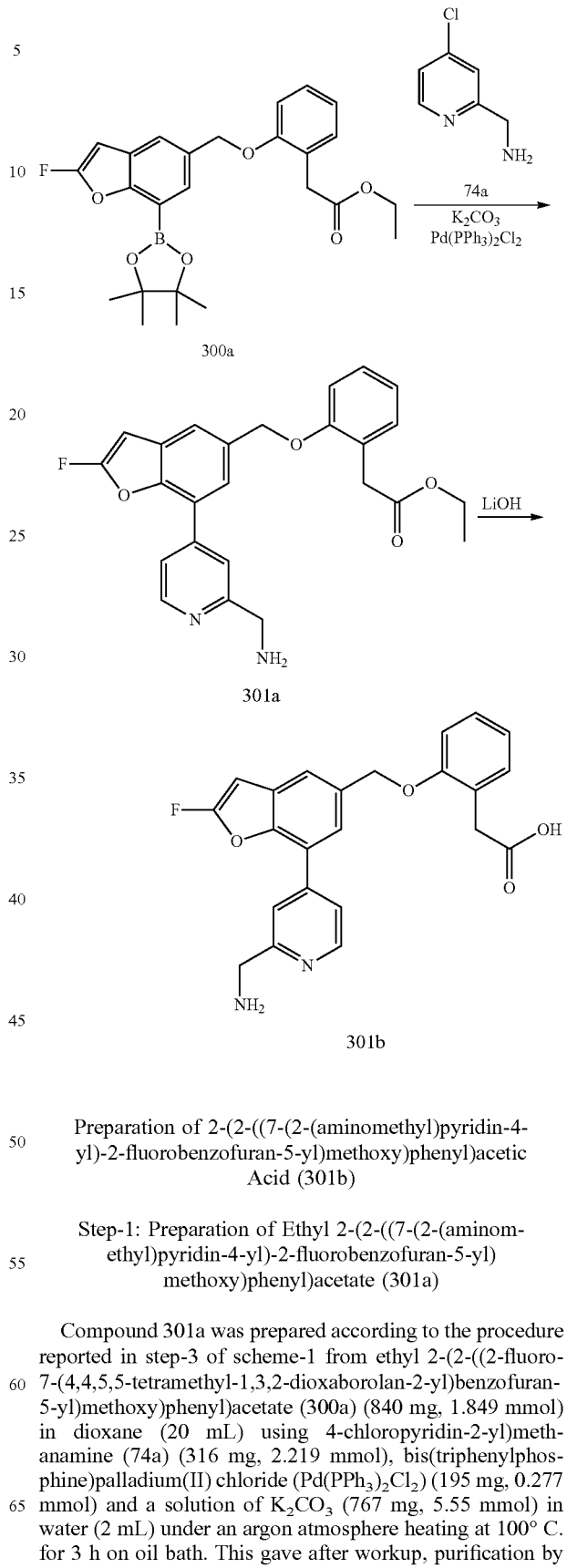

Scheme-301

Preparation of 2-(2-((7-(2-(aminomethyl)pyridin-4-yl)-2-fluorobenzofuran-5-yl)methoxy)phenyl)acetic Acid (301b)

Step-1: Preparation of Ethyl 2-(2-((7-(2-(aminomethyl)pyridin-4-yl)-2-fluorobenzofuran-5-yl)methoxy)phenyl)acetate (301a)

Compound 301a was prepared according to the procedure reported in step-3 of scheme-1 from ethyl 2-(2-((2-fluoro-7-(4,4,5,5-tetramethyl-1,3,2-dioxaborolan-2-yl)benzofuran-5-yl)methoxy)phenyl)acetate (300a) (840 mg, 1.849 mmol) in dioxane (20 mL) using 4-chloropyridin-2-yl)methanamine (74a) (316 mg, 2.219 mmol), bis(triphenylphosphine)palladium(II) chloride (Pd(PPh$_3$)$_2$Cl$_2$) (195 mg, 0.277 mmol) and a solution of K$_2$CO$_3$ (767 mg, 5.55 mmol) in water (2 mL) under an argon atmosphere heating at 100° C. for 3 h on oil bath. This gave after workup, purification by flash column chromatography (silica gel, 24 g, eluting with MeOH/DCM from 0-15%) ethyl 2-(2-((7-(2-(aminomethyl)pyridin-4-yl)-2-fluorobenzofuran-5-yl)methoxy)phenyl)acetate (301a) (324 mg, 0.746 mmol, 40.3% yield) as a thick syrup; $^1$H NMR (300 MHz, DMSO-$d_6$) δ 8.64 (d, J=5.2 Hz, 1H), 7.91 (d, J=1.7 Hz, 1H), 7.71 (td, J=5.7, 1.7 Hz, 3H), 7.25 (ddd, J=14.3, 7.3, 1.7 Hz, 2H), 7.10 (d, J=8.1 Hz, 1H), 6.92 (td, J=7.4, 1.1 Hz, 1H), 6.50 (d, J=6.4 Hz, 1H), 5.25 (s, 2H), 3.94 (dd, J=14.1, 6.9 Hz, 4H), 3.64 (s, 2H), 1.00 (t, J=7.1 Hz, 3H); $^{19}$F NMR (282 MHz, DMSO-$d_6$) δ−111.27; MS (ES+): 435.1 (M+1).

Step-2: Preparation of 2-(2-((7-(2-(aminomethyl)pyridin-4-yl)-2-fluorobenzofuran-5-yl)methoxy)phenyl)acetic Acid (301b)

Compound 301b was prepared according to the procedure reported in step-3 of scheme-300 from ethyl 2-(2-((7-(2-(aminomethyl)pyridin-4-yl)-2-fluorobenzofuran-5-yl)methoxy)phenyl)acetate (301a) (320 mg, 0.737 mmol) in THF (10 mL), ACN (2 mL), water (2 mL) using lithium hydroxide monohydrate (71 mg, 2.95 mmol) and stirring for 48 h at room temperature. This gave after workup and purification by reverse-phase column chromatography [C-18 column, 150 g, eluting with 0.1% aqueous HCl in water and acetonitrile from 0-100%] 2-(2-((7-(2-(aminomethyl)pyridin-4-yl)-2-fluorobenzofuran-5-yl)methoxy)phenyl)acetic acid (301b) (88 mg, 29% yield) hydrochloride salt as a light yellow solid; $^1$H NMR (300 MHz, DMSO-$d_6$) δ 8.82-8.72 (m, 1H), 8.54 (s, 3H), 8.07-7.95 (m, 1H), 7.92 (dd, J=5.3, 1.9 Hz, 1H), 7.83-7.74 (m, 2H), 7.24 (dd, J=8.1, 6.5 Hz, 2H), 7.13-7.04 (m, 1H), 6.91 (td, J=7.4, 1.1 Hz, 1H), 6.50 (d, J=6.4 Hz, 1H), 5.27 (s, 2H), 4.31 (d, J=5.7 Hz, 2H), 3.60 (s, 2H); $^{19}$F NMR (282 MHz, DMSO-$d_6$) δ−111.13 (d, J=3.1 Hz); MS (ES+): 407.10 (M+1), (ES−): 405.10 (M−1); Analysis calculated for $C_{23}H_{19}FN_2O_4$·1.65HCl·2H$_2$O: C, 54.96; H, 4.94; Cl, 11.64; N, 5.57; Found; C, 54.90; H, 5.02; Cl, 11.73; N, 5.54.

Scheme-302

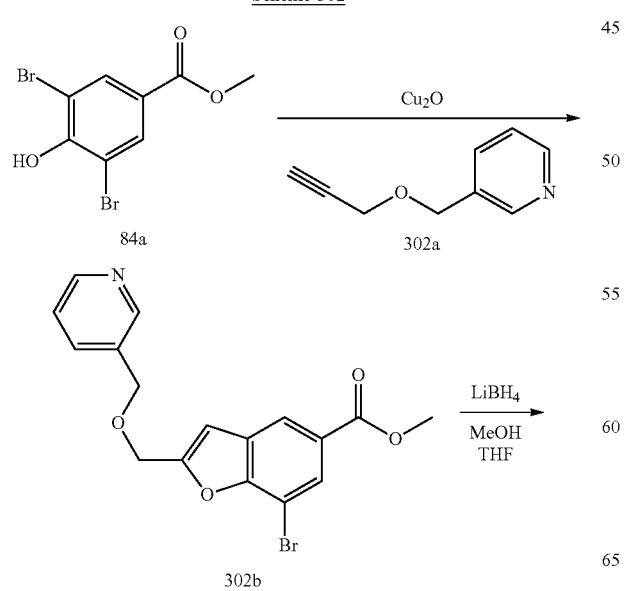

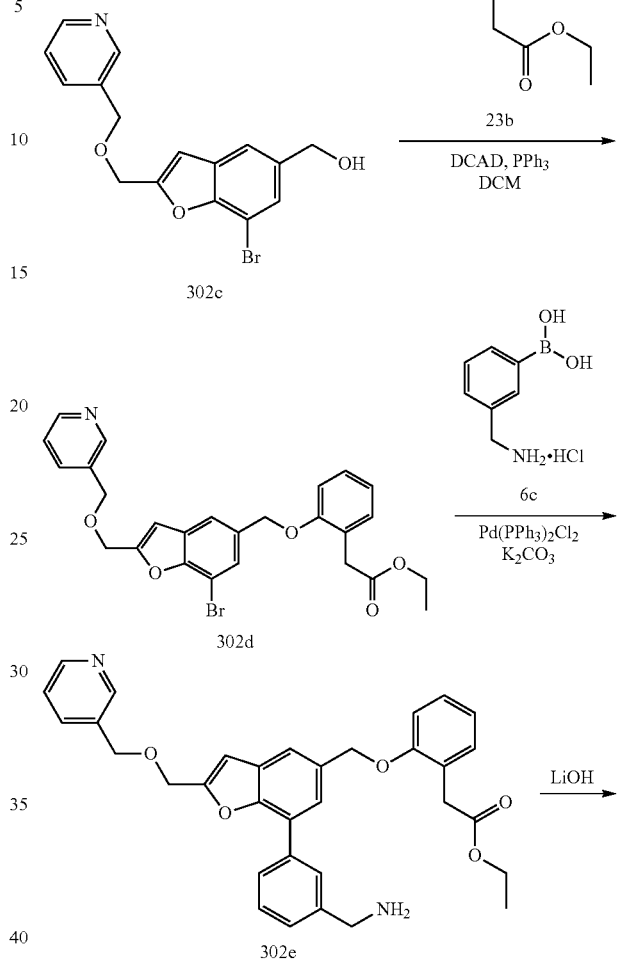

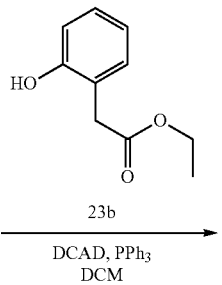

Preparation of 2-(2-((7-(3-(aminomethyl)phenyl)-2-((pyridin-3-ylmethoxy)methyl)benzofuran-5-yl)methoxy)phenyl)acetic Acid (302f)

Step-1: Preparation of methyl 7-bromo-2-((pyridin-3-ylmethoxy)methyl)benzofuran-5-carboxylate (302b)

Compound 302b was prepared according to the procedure reported in step-1 of scheme-55 from methyl 3,5-dibromo- 4-hydroxybenzoate (84a) (4.2 g, 13.55 mmol) in pyridine (20 mL) 3-((prop-2-yn-1-yloxy)methyl)pyridine (302a) (2.194 g, 14.91 mmol; CAS #72421-08-0; prepared according to the procedure reported by Fu, Boqiao et al; in Faming Zhuanli Shenqing, 104945456, 30 Sep. 2015), copper(I) oxide (0.970 g, 6.78 mmol) and heating at 50° C. for 18 h on an oil bath. This gave after workup and purification by flash column chromatography [silica (40g), eluting with EtOAc in hexane from 0-40%] methyl 7-bromo-2-((pyridin-3-ylmethoxy)methyl)benzofuran-5-carboxylate (302b) (3.2 g, 63% yield) as an light brown syrup; $^1$H NMR (300 MHz, DMSO-$d_6$) δ 8.57 (s, 1H), 8.51 (d, J=4.8 Hz, 1H), 8.30 (d, J=1.5 Hz, 1H), 8.06 (d, J=1.6 Hz, 1H), 7.82-7.75 (m, 1H), 7.39 (ddd, J=7.8, 4.8, 0.8 Hz, 1H), 7.22 (d, J=0.7 Hz, 1H), 4.76 (d, J=0.7 Hz, 2H), 4.65 (s, 2H), 3.88 (s, 3H); MS (ES+): 376.0, 378.0 (M, M+2).

Step-2: Preparation of (7-bromo-2-((pyridin-3-ylmethoxy)methyl)benzofuran-5-yl)methanol (302c)

Compound 302c was prepared according to the procedure reported in step-2 of scheme-76 from methyl 7-bromo-2-((pyridin-3-ylmethoxy)methyl)benzofuran-5-carboxylate (302b) (1.5 g, 3.99 mmol) in THF (30 mL) using LiBH$_4$ (6.98 mL, 13.96 mmol, 2 M solution in THF) and MeOH (0.565 mL, 13.96 mmol). This gave after workup and purification by flash column chromatography [silica (40g), eluting with EtOAc in hexane] (7-bromo-2-((pyridin-3-ylmethoxy)methyl)benzofuran-5-yl)methanol (302c) (935 mg, 67% yield) as a white semi solid; MS (ES+): 348.0, 350.0 (M, M+2).

Step-3: Preparation of Ethyl 2-(2-((7-bromo-2-((pyridin-3-ylmethoxy)methyl)benzofuran-5-yl)methoxy)phenyl)acetate (302d)

Compound 302d was prepared according to the procedure reported in step-2 of scheme-23 from (7-bromo-2-((pyridin-3-ylmethoxy)methyl)benzofuran-5-yl)methanol (302c) (450 mg, 1.292 mmol) in DCM (20 mL) using triphenylphosphine (407 mg, 1.551 mmol), ethyl 2-(2-hydroxyphenyl)acetate (23b) (279 mg, 1.551 mmol) and (E)-bis(4-chlorobenzyl) diazene-1,2-dicarboxylate (DCAD, 641 mg, 1.745 mmol) in DCM (10 mL). This gave after workup and purification by flash column chromatography [silica (40g), eluting with EtOAc in hexane from 0-40%] ethyl 2-(2-((7-bromo-2-((pyridin-3-ylmethoxy)methyl)benzofuran-5-yl)methoxy)phenyl)acetate (302d) (179 mg, 27% yield) as a white solid; $^1$H NMR (300 MHz, DMSO-$d_6$) δ 8.58 (s, 1H), 8.51 (d, J=5.7 Hz, 1H), 8.13 (d, J=7.9 Hz, 1H), 7.75-7.64 (m, 2H), 7.60 (d, J=1.5 Hz, 1H), 7.29-7.19 (m, 2H), 7.12 (s, 1H), 7.09-7.04 (m, 1H), 6.91 (td, J=7.4, 1.1 Hz, 1H), 5.18 (s, 2H), 4.78 (s, 2H), 4.73 (s, 2H), 4.02 (q, J=7.1 Hz, 2H), 3.62 (s, 2H), 1.08 (t, J=7.1 Hz, 3H).

Step-4: Preparation of Ethyl 2-(2-((7-(3-(aminomethyl)phenyl)-2-((pyridin-3-ylmethoxy)methyl)benzofuran-5-yl)methoxy)phenyl)acetate (302e)

Compound 302e was prepared according to the procedure reported in step-3 of scheme-1 from ethyl 2-(2-((7-bromo-2-((pyridin-3-ylmethoxy)methyl)benzofuran-5-yl)methoxy)phenyl)acetate (302d) (170 mg, 0.333 mmol) in dioxane (10 mL) using 3-(aminomethyl)phenylboronic acid hydrochloride (6c) (62 mg, 0.333 mmol), a solution of K$_2$CO$_3$ (138 mg, 1.0 mmol) in water (2 mL), bis(triphenylphosphine)palladium(II) chloride (35 mg, 0.050 mmol) and heating at 100° C. for 12h on oil bath. This gave after workup, purification by flash column chromatography [silica (24 g), eluting with DMA80 in DCM from 0-90%] ethyl 2-(2-((7-(3-(aminomethyl)phenyl)-2-((pyridin-3-ylmethoxy)methyl)benzofuran-5-yl)methoxy)phenyl)acetate (302e) (25 mg, 1 y % yield) as an oil; MS (ES+): 537.3 (M+1), 579.2 (M+Na).

Step-5: Preparation of 2-(2-((7-(3-(aminomethyl)phenyl)-2-((pyridin-3-ylmethoxy)methyl)benzofuran-5-yl)methoxy)phenyl)acetic Acid (302f)

Compound 302f was prepared according to the procedure reported in step-6 of scheme-1, from ethyl 2-(2-((7-(3-(aminomethyl)phenyl)-2-((pyridin-3-ylmethoxy)methyl)benzofuran-5-yl)methoxy)phenyl)acetate (302e) (25 mg, 0.047 mmol) in MeOH/THF (1/5 mL) using a solution of lithium hydroxide monohydrate (5 mg, 0.186 mmol) in water (1 mL). This gave after workup and purification by reverse-phase column chromatography (C-18 column, 30 g, eluting with 0.1% aqueous HCl in water and acetonitrile from 0-100%) 2-(2-((7-(3-(aminomethyl)phenyl)-2-((pyridin-3-ylmethoxy)methyl)benzofuran-5-yl)methoxy)phenyl)acetic acid (302f) (1.5 mgs) hydrochloride salt as a white solid; $^1$H NMR (300 MHz, DMSO-$d_6$) δ 8.36-8.16 (m, 4H), 7.94 (d, J=1.4 Hz, 2H), 7.95-7.83 (m, 2H), 7.74 (d, J=1.6 Hz, 1H), 7.67-7.57 (m, 2H), 7.58-7.46 (m, 2H), 7.24 (t, J=7.5 Hz, 2H), 7.08 (d, J=12.1 Hz, 2H), 6.91 (t, J=7.4 Hz, 1H), 5.26 (s, 2H), 4.75 (s, 2H), 4.67 (s, 2H), 4.15 (d, J=5.8 Hz, 2H), 3.60 (s, 2H); MS (ES+): 509.2 (M+1), (ES−): 507.1 (M−1).

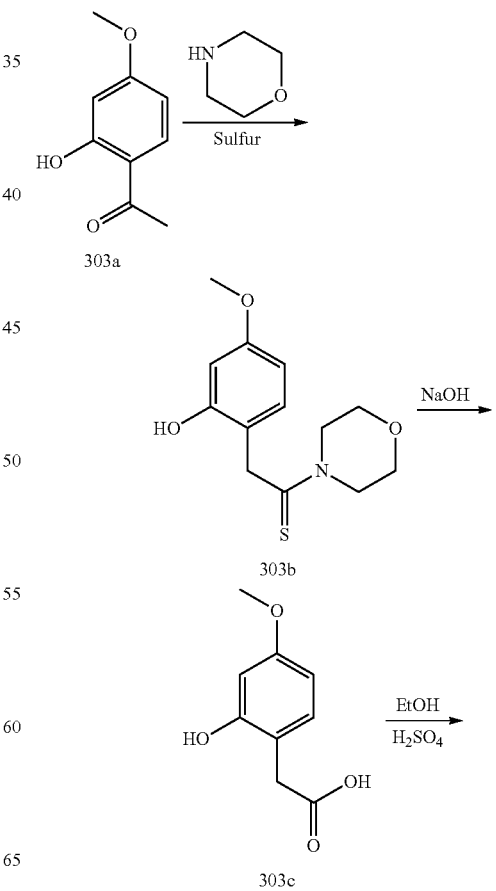

Scheme-303

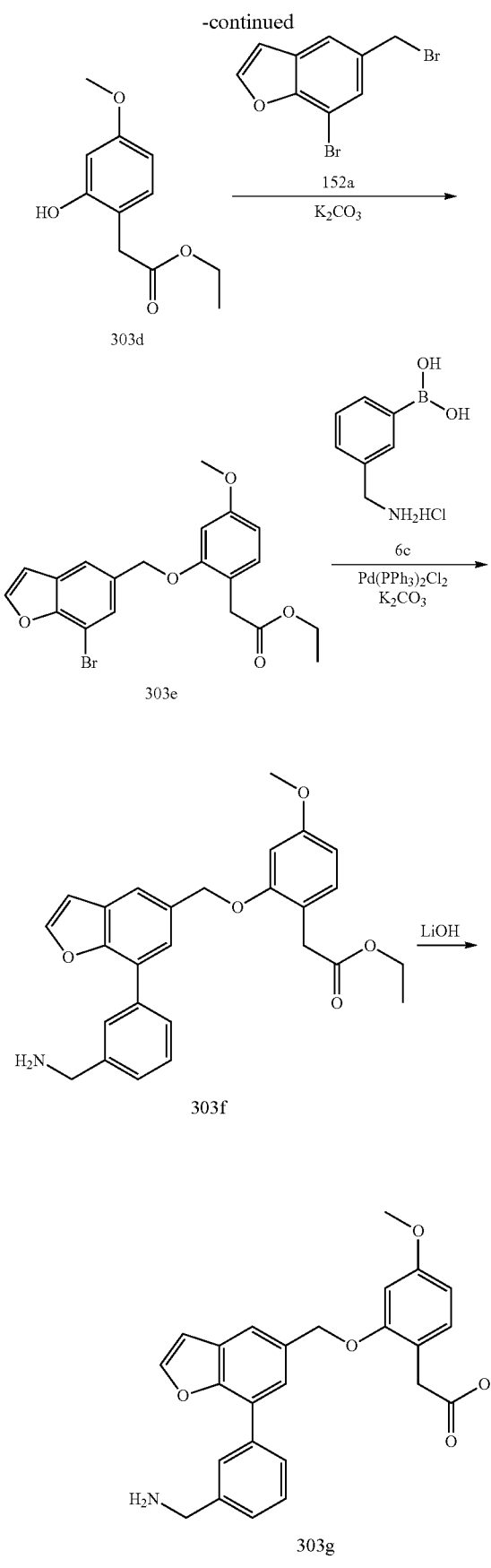

Preparation of 2-(2-((7-(3-(aminomethyl)phenyl)benzofuran-5-yl)methoxy)-4-methoxyphenyl)acetic Acid (303g)

Step-1: Preparation of 2-(2-hydroxy-4-methoxyphenyl)-1-morpholinoethanethione (303b)

Compound 303b was prepared according to the procedure reported in step-1 of scheme-265 from 1-(2-hydroxy-4-methoxyphenyl)ethanone (303a) (2 g, 12.04 mmol) in N-Methyl-2-pyrrolidinone (6 mL) using sulfur powder (0.772 g, 24.07 mmol), morpholine (2.076 mL, 24.07 mmol) and heating at 130° C. for 10 h. This gave after workup 2-(2-hydroxy-4-methoxyphenyl)-1-morpholinoethanethione (303b) (1.8 g, 56% yield) as a dark syrup; $^1$H NMR (300 MHz, DMSO-$d_6$) δ 9.75-9.64 (m, 1H), 7.08 (d, J=8.0 Hz, 1H), 6.38 (d, J=7.9 Hz, 2H), 4.22 (dd, J=5.7, 4.2 Hz, 2H), 4.05-4.01 (m, 2H), 3.67 (s, 3H), 3.64 (dt, J=6.0, 4.3 Hz, 4H), 3.44-3.37 (m, 2H); MS (ES+): 268.1 (M+1), (ES−): 266.1 (M+Na)

Step-2: Preparation of 2-(2-hydroxy-4-methoxyphenyl)acetic Acid (303c)

Compound 303c was prepared according to the procedure reported in step-2 of scheme-265 from 2-(2-hydroxy-4-methoxyphenyl)-1-morpholinoethanethione (303b) (1.79 g, 6.70 mmol) in ethanol (20 mL) and water (5 mL) using sodium hydroxide (1.379 g, 34.5 mmol) and heating at reflux for 10 h. This gave after workup 2-(2-hydroxy-4-methoxyphenyl)acetic acid (303c) (1.1 g, 90% yield) as a colorless oil; $^1$H NMR (300 MHz, DMSO-$d_6$) δ 12.00 (s, 1H), 9.43 (s, 1H), 6.97 (d, J=8.2 Hz, 1H), 6.36 (d, J=2.5 Hz, 1H), 6.32 (dd, J=8.2, 2.6 Hz, 1H), 3.67 (s, 3H), 3.37 (s, 2H).

Step-3: Preparation of Ethyl 2-(2-hydroxy-4-methoxyphenyl)acetate (303d)

Compound 303d was prepared according to the procedure reported in step-3 of scheme-265 from 2-(2-hydroxy-4-methoxyphenyl)acetic acid (303c) (1.1 g, 6.04 mmol) in ethanol (20 mL) using sulfuric acid (0.354 mL, 6.64 mmol) and heating at reflux for 4 h. This gave after workup and purification by flash column chromatography (silica gel, 40 g, eluting with ethyl acetate and hexanes) ethyl 2-(2-hydroxy-4-methoxyphenyl)acetate (303d) (1.01 g, 80% yield) as colorless oil.

Step-4: Preparation of Ethyl 2-(2-((7-bromobenzofuran-5-yl)methoxy)-4-methoxyphenyl)acetate (303e)

Compound 303e was prepared according to the procedure reported in step-2 of scheme-152 from 7-bromo-5-(bromomethyl)benzofuran (152a) (1.379 g, 4.76 mmol) using ethyl 2-(2-hydroxy-4-methoxyphenyl)acetate (303d) (1 g, 4.76 mmol), K$_2$CO$_3$ (1.972 g, 14.27 mmol) in DMF (10 mL) and stirring at room temperature for 12 h. This gave after workup ethyl 2-(2-((7-bromobenzofuran-5-yl)methoxy)-4-methoxyphenyl)acetate (303e) (1.95 g, 98% yield) as a white solid; $^1$H NMR (300 MHz, DMSO-$d_6$) δ 8.14 (d, J=2.2 Hz, 1H), 7.71 (d, J=1.5 Hz, 1H), 7.59 (d, J=1.5 Hz, 1H), 7.17-7.04 (m, 2H), 6.66 (d, J=2.4 Hz, 1H), 6.49 (dd, J=8.3, 2.4 Hz, 1H), 5.17 (s, 2H), 4.01 (q, J=7.1 Hz, 2H), 3.74 (s, 3H), 3.53 (s, 2H), 1.07 (t, J=7.1 Hz, 3H).

Step-5: Preparation of Ethyl 2-(2-((7-(3-(aminomethyl)phenyl)benzofuran-5-yl)methoxy)-4-methoxyphenyl)acetate (303f)

Compound 303f was prepared according to the procedure reported in step-3 of scheme-1 from ethyl 2-(2-((7-bromobenzofuran-5-yl)methoxy)-4-methoxyphenyl)acetate (303e) (1.94 g, 4.63 mmol) in dioxane (60 mL) using 3-(aminomethyl)phenylboronic acid hydrochloride (6c) (1.301 g, 6.94 mmol), bis(triphenylphosphine)palladium(II) chloride (Pd(PPh$_3$)$_2$Cl$_2$) (0.487 g, 0.694 mmol), potassium carbonate (1.918 g, 13.88 mmol) in water (10 mL) under a nitrogen atmosphere heating at 100° C. for 3 h on oil bath. This gave after workup, purification by flash column chromatography (silica gel, 40 g, eluting with DMA-80 in DCM from 0-50%) ethyl 2-(2-((7-(3-(aminomethyl)phenyl)benzofuran-5-yl)methoxy)-4-methoxyphenyl)acetate (303f) (1.276 g, 62% yield) as a brown syrup; $^1$H NMR (300 MHz, DMSO-d$_6$) δ 8.09 (d, J=2.2 Hz, 1H), 7.82 (d, J=2.0 Hz, 1H), 7.77-7.65 (m, 2H), 7.57 (d, J=1.7 Hz, 1H), 7.46 (t, J=7.6 Hz, 1H), 7.42-7.36 (m, 1H), 7.11 (d, J=8.3 Hz, 1H), 7.05 (d, J=2.2 Hz, 1H), 6.70 (d, J=2.4 Hz, 1H), 6.48 (dd, J=8.3, 2.4 Hz, 1H), 5.23 (s, 2H), 3.92 (q, J=7.1 Hz, 2H), 3.81 (s, 2H), 3.74 (s, 3H), 3.54 (s, 2H), 1.94 (s, 2H), 0.99 (t, J=7.1 Hz, 3H); MS (ES+): 446.2 (M+1).

Step-6: Preparation of 2-(2-((7-(3-(aminomethyl)phenyl)benzofuran-5-yl)methoxy)-4-methoxyphenyl)acetic Acid (303g)

Compound 303g was prepared according to the procedure reported in step-6 of scheme-1 from ethyl 2-(2-((7-(3-(aminomethyl)phenyl)benzofuran-5-yl)methoxy)-4-methoxyphenyl)acetate (303f) (1.26 g, 2.83 mmol) in MeOH (10 mL), THF (15 mL) using lithium hydroxide monohydrate (0.271 g, 11.31 mmol) in water (4 mL). This gave after workup and purification by reverse phase column [C18 (250g), eluting with ACN in water (containing 0.1% HCl) from 0-100%] 2-(2-((7-(3-(aminomethyl)phenyl)benzofuran-5-yl)methoxy)-4-methoxyphenyl)acetic acid (303g) (952 mg, 81% yield) hydrochloride salt as a white solid; $^1$H NMR (300 MHz, DMSO-d$_6$) δ 8.46 (s, 3H), 8.10 (d, J=2.2 Hz, 1H), 8.00 (d, J=1.8 Hz, 1H), 7.93 (dt, J=7.1, 1.9 Hz, 1H), 7.76 (d, J=1.6 Hz, 1H), 7.65 (d, J=1.7 Hz, 1H), 7.62-7.52 (m, 2H), 7.11 (d, J=8.3 Hz, 1H), 7.06 (d, J=2.2 Hz, 1H), 6.67 (s, 1H), 6.48 (dd, J=8.3, 2.4 Hz, 1H), 5.26 (s, 2H), 4.13 (s, 2H), 3.73 (s, 3H), 3.51 (s, 2H); MS (ES+): 518.10 (M+1), (ES−): 416.10 (M−1); Analysis calculated for C$_{25}$H$_{23}$NO$_5$.HCl.1.5H$_2$O: C, 62.43; H, 5.66; N, 2.91; Found: C, 62.56; H, 5.53; N, 2.90.

Scheme304

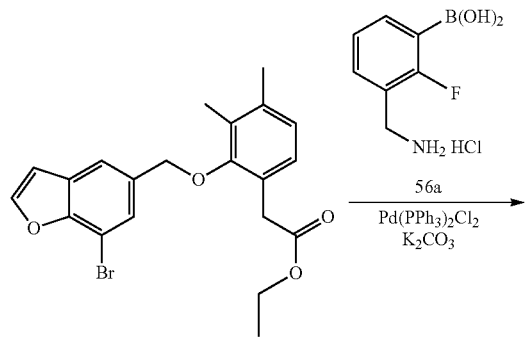

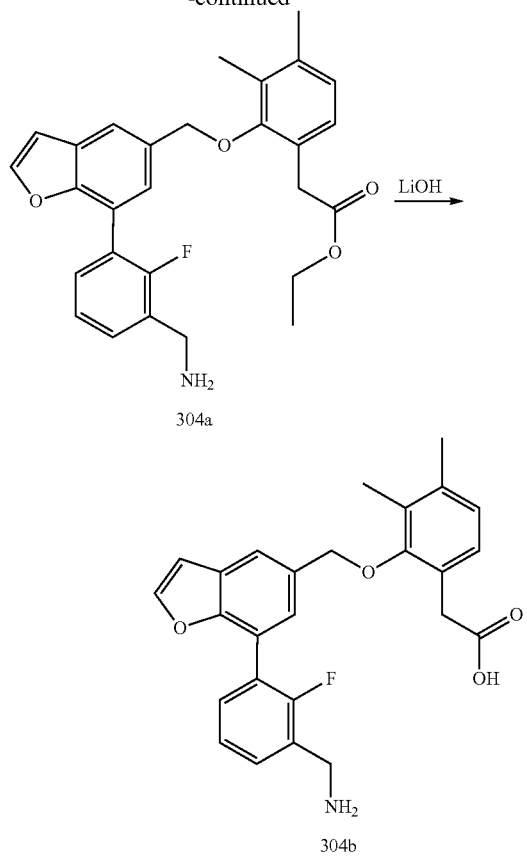

304a

304b

Preparation of 2-(2-((7-(3-(aminomethyl)-2-fluorophenyl)benzofuran-5-yl)methoxy)-3,4-dimethylphenyl)acetic Acid (304b)

Step-1: Preparation of Ethyl 2-(2-((7-(3-(aminomethyl)-2-fluorophenyl)benzofuran-5-yl)methoxy)-3,4-dimethylphenyl)acetate (304a)

Compound 304a was prepared according to the procedure reported in step-3 of scheme-1 from ethyl 2-(2-((7-bromobenzofuran-5-yl)methoxy)-3,4-dimethylphenyl)acetate (292d) (390 mg, 0.935 mmol) in dioxane (10 mL) using (3-(aminomethyl)-2-fluorophenyl)boronic acid hydrochloride (56a) (307 mg, 1.495 mmol), bis(triphenylphosphine)palladium(II) chloride (Pd(PPh$_3$)$_2$Cl$_2$) ((98 mg, 0.140 mmol), potassium carbonate (387 mg, 2.80 mmol) in water (3 mL) under an argon atmosphere heating at 100° C. for 6 h on oil bath. This gave after workup, purification by flash column chromatography (silica gel 40 g, eluting with DMA-80 in DCM from 0-50%) ethyl 2-(2-((7-(3-(aminomethyl)-2-fluorophenyl)benzofuran-5-yl)methoxy)-3,4-dimethylphenyl)acetate (304a) (268 mg, 62% yield) as a colorless syrup; $^1$H NMR (300 MHz, DMSO-d$_6$) δ 8.05 (d, J=2.2 Hz, 1H), 7.81 (d, J=1.7 Hz, 1H), 7.61 (td, J=7.4, 2.0 Hz, 1H), 7.52-7.39 (m, 2H), 7.32 (t, J=7.6 Hz, 1H), 7.08 (d, J=2.2 Hz, 1H), 7.01 (d, J=7.7 Hz, 1H), 6.93 (d, J=7.7 Hz, 1H), 4.86 (s, 2H), 3.97 (q, J=7.1 Hz, 2H), 3.84 (s, 2H), 3.64 (s, 2H), 2.23 (s, 3H), 2.21 (s, 3H), 1.91 (d, J=13.0 Hz, 2H), 1.03 (t, J=7.1 Hz, 3H); $^{19}$F NMR (282 MHz, DMSO-d$_6$) δ−121.90; MS (ES+): 462.2 (M+1), (ES−): 460.1 (M−1).

Step-2: Preparation of 2-(2-((7-(3-(aminomethyl)-2-fluorophenyl)benzofuran-5-yl)methoxy)-3,4-dimethylphenyl)acetic Acid (304b)

Compound 304b was prepared according to the procedure reported in step-6 of scheme-1 from ethyl 2-(2-((7-(3-(aminomethyl)-2-fluorophenyl)benzofuran-5-yl)methoxy)-3,4-dimethylphenyl)acetate (304a) (260 mg, 0.563 mmol) in MeOH (2 mL), THF (10 mL) using a solution of lithium hydroxide (54.0 mg, 2.253 mmol) in water (2 mL). This gave after workup and purification by reverse phase column [C18 (40 g), eluting with ACN in water (containing 0.1% HCl) from 0-100%] 2-(2-((7-(3-(aminomethyl)-2-fluorophenyl)benzofuran-5-yl)methoxy)-3,4-dimethylphenyl)acetic acid (304b) (210 mg, 86% yield) hydrochloride salt as a white solid; $^1$H NMR (300 MHz, DMSO-$d_6$) δ 9.68-8.89 (m, 4H), 8.08 (d, J=2.2 Hz, 1H), 7.87 (d, J=1.6 Hz, 1H), 7.70 (dtd, J=10.9, 7.4, 1.8 Hz, 2H), 7.51 (t, J=1.3 Hz, 1H), 7.44 (t, J=7.7 Hz, 1H), 7.11 (d, J=2.2 Hz, 1H), 7.02 (d, J=7.7 Hz, 1H), 6.93 (d, J=7.7 Hz, 1H), 4.88 (s, 2H), 4.18 (s, 2H), 3.59 (s, 2H), 2.23 (s, 3H), 2.21 (s, 3H); $^{19}$F NMR (282 MHz, DMSO-$d_6$) δ −118.60 (t, J=7.1 Hz); MS (ES+): 434.2.10 (M+1), (ES−): 432.2 (M−1); Analysis calculated for $C_{26}H_{24}FNO_4 \cdot HCl \cdot 0.75 H_2O$: C, 64.60; H, 5.53; Cl, 7.33; N, 2.90; Found: C, 64.75; H, 5.34; Cl, 7.38; N, 2.94.

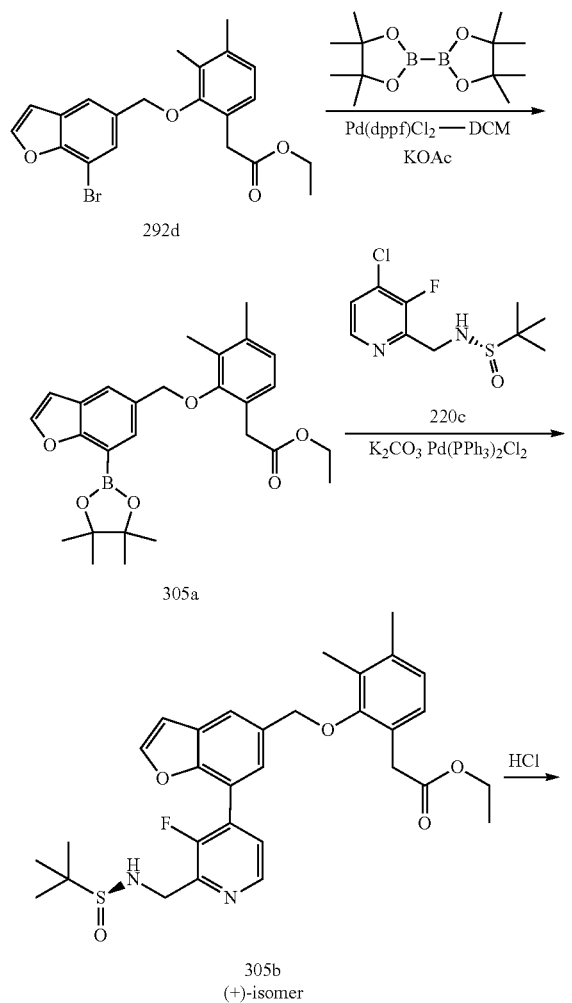

Scheme-305

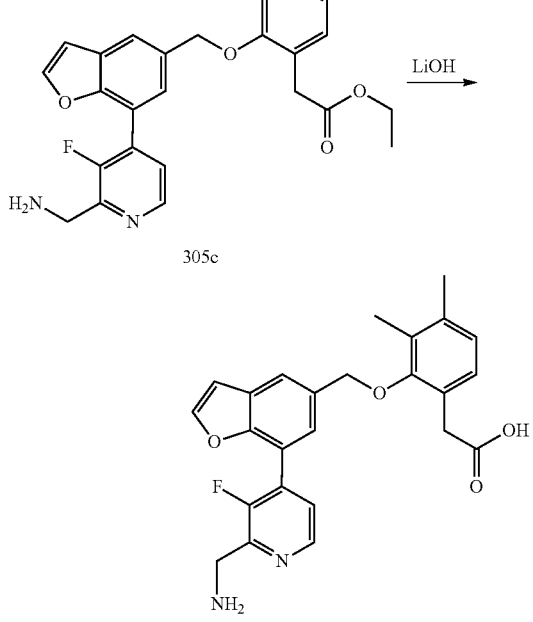

Preparation of 2-(2-((7-(2-(aminomethyl)-3-fluoropyridin-4-yl)benzofuran-5-yl)methoxy)-3,4-dimethylphenyl)acetic Acid (305d)

Step-1: Preparation of Ethyl 2-(3,4-dimethyl-2-((7-(4,4,5,5-tetramethyl-1,3,2-dioxaborolan-2-yl)benzofuran-5-yl)methoxy)phenyl)acetate (305a)

Compound 305a was prepared according to the procedure reported in step-1 of scheme-59 from ethyl 2-(2-((7-bromobenzofuran-5-yl)methoxy)-3,4-dimethylphenyl)acetate (292d) (1.00 g, 2.396 mmol), using bis(pinacolato)diboron (0.913 g, 3.59 mmol), potassium acetate (0.706 g, 7.19 mmol) and Pd(dppf)Cl$_2$-DCM (0.098 g, 0.120 mmol) in anhydrous dioxane (15 mL) under an argon atmosphere and heating at 90° C. for 18 h. This gave after workup and purification by flash column chromatography [silica (40g), eluting with EtOAc in hexanes from 0-60%] ethyl 2-(3,4-dimethyl-2-((7-(4,4,5,5-tetramethyl-1,3,2-dioxaborolan-2-yl)benzofuran-5-yl)methoxy)phenyl)acetate (305a) (430 mg, 39%) as a white solid; $^1$H NMR (300 MHz, DMSO-$d_6$) δ 8.07 (d, J=2.2 Hz, 1H), 7.90 (d, J=1.9 Hz, 1H), 7.69 (d, J=1.8 Hz, 1H), 7.04-6.89 (m, 3H), 4.82 (s, 2H), 4.02 (q, J=7.1 Hz, 2H), 3.62 (s, 2H), 2.24 (s, 3H), 2.20 (s, 3H), 1.35 (s, 12H), 1.11 (t, J=7.1 Hz, 3H); MS (ES+): 487.2 (M+Na).

Step-2: Preparation of (+)-(S)-ethyl 2-(2-((7-(2-((1,1-dimethylethylsulfinamido)methyl)-3-fluoropyridin-4-yl)benzofuran-5-yl)methoxy)-3,4-dimethylphenyl)acetate (305b)

Compound 305b was prepared according to the procedure reported in step-3 of scheme-1 from ethyl 2-(3,4-dimethyl-2-((7-(4,4,5,5-tetramethyl-1,3,2-dioxaborolan-2-yl)benzofuran-5-yl)methoxy)phenyl)acetate (305a) (400 mg, 0.861 mmol) in dioxane (20 mL) using (+)-(S)—N-((4-chloro-3- fluoropyridin-2-yl)methyl)-2-methylpropane-2-sulfinamide (220c) (342 mg, 1.292 mmol), bis(triphenylphosphine)palladium(II) chloride (Pd(PPh$_3$)$_2$Cl$_2$) (91 mg, 0.129 mmol) and a solution of K$_2$CO$_3$ (357 mg, 2.58 mmol) in water (2.4 mL) under a nitrogen atmosphere heating at 100° C. for 20 h on oil bath. This gave after workup, purification by flash column chromatography (silica gel, 24 g, eluting with MeOH/DCM from 0-15%) (+)-(S)-ethyl 2-(2-((7-(2-((1,1-dimethylethylsulfinamido)methyl)-3-fluoropyridin-4-yl)benzofuran-5-yl)methoxy)-3,4-dimethylphenyl)acetate (305b) (410 mg, 74%) as a brown oil; $^1$H NMR (300 MHz, DMSO-d$_6$) δ 8.52 (dd, J=4.9, 0.7 Hz, 1H), 8.36 (d, J=5.2 Hz, 1H), 8.10 (d, J=2.2 Hz, 1H), 7.91 (d, J=1.6 Hz, 1H), 7.72-7.63 (m, 1H), 7.56 (d, J=1.5 Hz, 1H), 7.13 (d, J=2.2 Hz, 1H), 7.01 (d, J=7.7 Hz, 1H), 6.94 (d, J=7.7 Hz, 1H), 4.88 (s, 2H), 4.42 (dd, J=5.8, 2.0 Hz, 2H), 3.96 (q, J=7.1 Hz, 2H), 3.63 (s, 2H), 2.23 (s, 3H), 2.21 (s, 3H), 1.09 (s, 9H), 1.03 (t, J=7.1 Hz, 3H); MS (ES+): 467.2 (M+1); Optical rotation [t]D=+40.0 (c=0.33, MeOH).

Step-3: Preparation of Ethyl 2-(2-((7-(2-(aminomethyl)-3-fluoropyridin-4-yl)benzofuran-5-yl)methoxy)-3,4-dimethylphenyl)acetate (305c)

To a stirred solution of (+)-(S)-ethyl 2-(2-((7-(2-((1,1-dimethylethylsulfinamido)methyl)-3-fluoropyridin-4-yl)benzofuran-5-yl)methoxy)-3,4-dimethylphenyl)acetate (305b) (420 mg, 0.741 mmol) in THF (13 mL) was added HCl (3M aqueous) (0.741 mL, 2.223 mmol) and stirred at room temperature for 5 h. The reaction was concentrated to dryness and the residue obtained was purified by flash column chromatography (silica gel, 25 g eluting with DMA 80 in dichloromethane) to afford ethyl 2-(2-((7-(2-(aminomethyl)-3-fluoropyridin-4-yl)benzofuran-5-yl)methoxy)-3,4-dimethylphenyl)acetate (305c) (120 mgs, 35% yield) as brown syrup; $^1$H NMR (300 MHz, DMSO-d$_6$) δ 8.52 (d, J=4.9 Hz, 1H), 8.10 (d, J=2.2 Hz, 1H), 7.90 (d, J=1.7 Hz, 1H), 7.64-7.52 (m, 2H), 7.12 (d, J=2.2 Hz, 1H), 7.01 (d, J=7.7 Hz, 1H), 6.93 (d, J=7.7 Hz, 1H), 4.88 (s, 2H), 4.06-3.90 (m, 4H), 3.63 (s, 2H), 2.22 (d, J=7.5 Hz, 6H), 2.03 (s, 2H), 1.98 (s, OH), 1.02 (t, J=7.1 Hz, 3H); MS (ES+): 463.2 (M+1).

Step-4: Preparation of 2-(2-((7-(2-(aminomethyl)-3-fluoropyridin-4-yl)benzofuran-5-yl)methoxy)-3,4-dimethylphenyl)acetic Acid (305d)

Compound 305d was prepared according to the procedure reported in step-6 of scheme-1 from ethyl 2-(2-((7-(2-(aminomethyl)-3-fluoropyridin-4-yl)benzofuran-5-yl)methoxy)-3,4-dimethylphenyl)acetate (305c) (120 mgs, 0.259 mmol) in MeOH (5 mL), THF (5 mL) using a solution of lithium hydroxide (67 mg, 1.557 mmol) in water (5 mL). This gave after workup and purification by reverse phase column [C18 (150 g), eluting with ACN in water (containing 0.1% HCl) from 0-100%] 2-(2-((7-(2-(aminomethyl)-3-fluoropyridin-4-yl)benzofuran-5-yl)methoxy)-3,4-dimethylphenyl)acetic acid (305d) (56 mg, 50% yield) hydrochloride salt as a white solid; $^1$H NMR (300 MHz, DMSO-d$_6$) δ 8.64 (d, J=5.0 Hz, 1H), 8.57 (s, 4H), 8.13 (d, J=2.2 Hz, 1H), 7.96 (d, J=1.6 Hz, 1H), 7.82 (t, J=5.3 Hz, 1H), 7.63 (t, J=1.3 Hz, 1H), 7.15 (d, J=2.2 Hz, 1H), 7.02 (d, J=7.7 Hz, 1H), 6.93 (d, J=7.8 Hz, 1H), 4.90 (s, 2H), 4.48-4.29 (m, 2H), 3.58 (s, 2H), 2.23 (s, 3H), 2.21 (s, 3H); $^{19}$F NMR (282 MHz, DMSO-d$_6$) δ–128.57; MS (ES+): 435.2 (M+1), (ES–): 433.2 (M–1); Analysis calculated for C$_{25}$H$_{23}$FN$_2$O$_4$.1.25HCl.1.75H$_2$O: C, 58.70; H, 5.47; Cl, 8.66; N, 5.48; Found: C, 58.60; H, 5.35; Cl, 8.93; N, 5.51.

Step-4: Preparation of 2-(2-((7-(2-(aminomethyl)-3-fluoropyridin-4-yl)-2-fluorobenzofuran-5-yl)methoxy)-3,4-dimethylphenyl)acetic Acid (305d)

Compound 305d was prepared according to the procedure reported in step-6 of scheme-1 from ethyl 2-(2-((7-(2-(aminomethyl)-3-fluoropyridin-4-yl)-2-fluorobenzofuran-5-yl)methoxy)-3,4-dimethylphenyl)acetate (305c) (120 mgs, 0.259 mmol) in MeOH (5 mL), THF (5 mL) using a solution of lithium hydroxide (67 mg, 1.557 mmol) in water (5 mL). This gave after workup and purification by reverse phase column [C18 (150 g), eluting with ACN in water (containing 0.1% HCl) from 0-100%] 2-(2-((7-(2-(aminomethyl)-3-fluoropyridin-4-yl)-2-fluorobenzofuran-5-yl)methoxy)-3,4-dimethylphenyl)acetic acid (305d) (56 mg, 50% yield) hydrochloride salt as a white solid; $^1$H NMR (300 MHz, DMSO-d$_6$) δ 8.64 (d, J=5.0 Hz, 1H), 8.57 (s, 4H), 8.13 (d, J=2.2 Hz, 1H), 7.96 (d, J=1.6 Hz, 1H), 7.82 (t, J=5.3 Hz, 1H), 7.63 (t, J=1.3 Hz, 1H), 7.15 (d, J=2.2 Hz, 1H), 7.02 (d, J=7.7 Hz, 1H), 6.93 (d, J=7.8 Hz, 1H), 4.90 (s, 2H), 4.48-4.29 (m, 2H), 3.58 (s, 2H), 2.23 (s, 3H), 2.21 (s, 3H); $^{19}$F NMR (282 MHz, DMSO-d$_6$) δ–128.57; MS (ES+): 435.2 (M+1), (ES–): 433.2 (M–1); Analysis calculated for C$_{25}$H$_{23}$FN$_2$O$_4$.1.25HCl.1.75H$_2$O: C, 58.70; H, 5.47; Cl, 8.66; N, 5.48; Found: C, 58.60; H, 5.35; Cl, 8.93; N, 5.51.

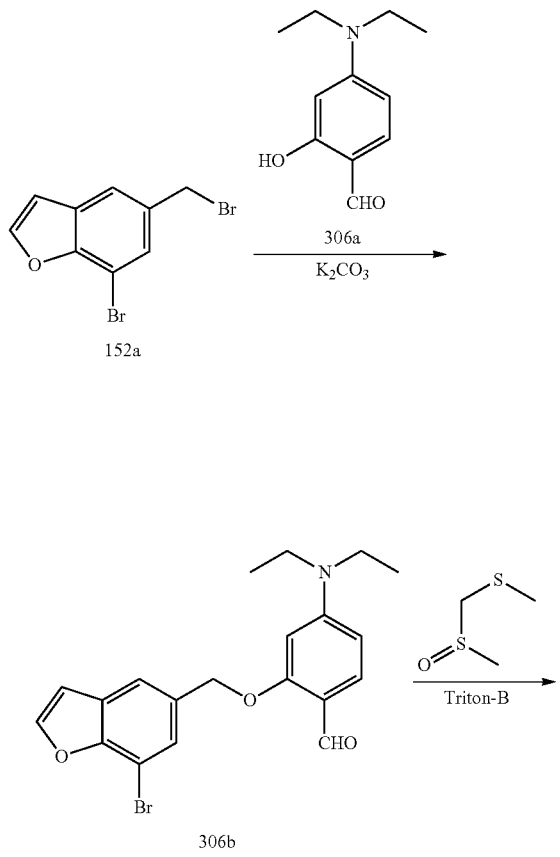

Scheme-306

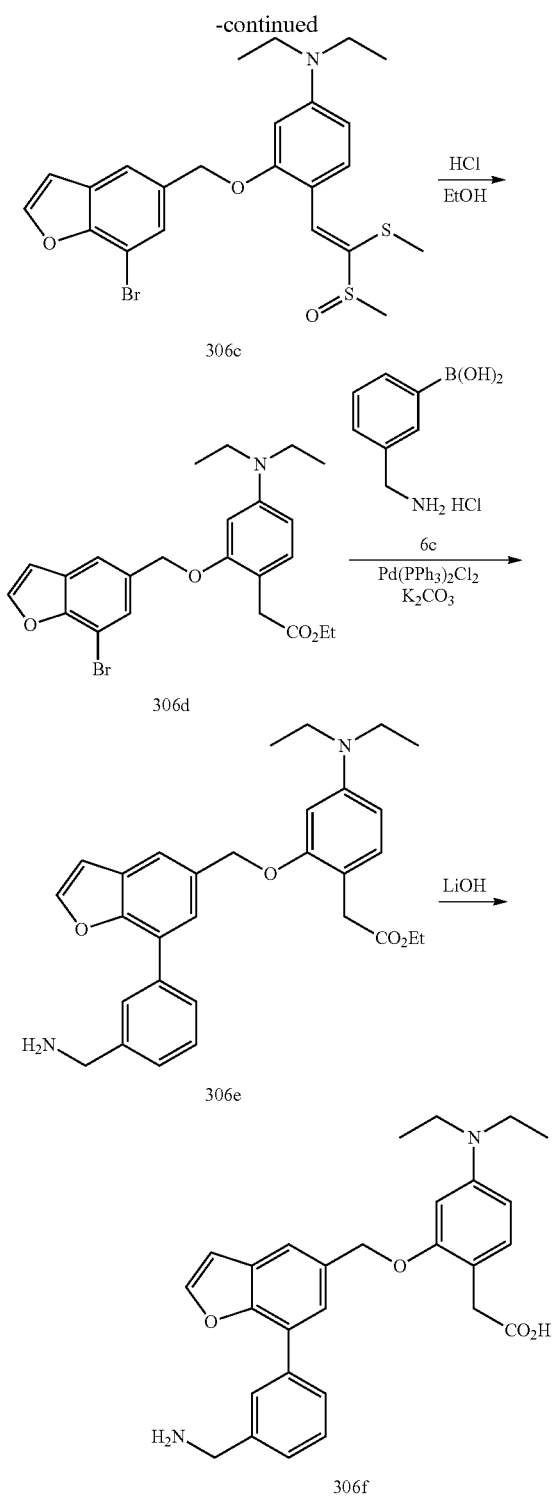

momethyl)benzofuran (152a) (1.5 g, 5.17 mmol) using 4-(diethylamino)-2-hydroxybenzaldehyde (306a) (1.0 g, 5.17 mmol; CAS #17754-90-4), $K_2CO_3$ (2.146 g, 15.52 mmol) in DMF (20 mL) and stirring at room temperature for 16 h. This gave after workup and purification by flash column chromatography (Silica gel, eluting with 0-20% EtOAc in hexane) 2-((7-bromobenzofuran-5-yl)methoxy)-4-(diethylamino)benzaldehyde (306b) (1.79 g, 86% yield) as an oily pale-yellow oil; $^1$H NMR (300 MHz, DMSO-$d_6$) δ 10.08 (s, 1H), 8.14 (d, J=2.2 Hz, 1H), 7.82 (d, J=1.5 Hz, 1H), 7.72 (d, J=1.5 Hz, 1H), 7.51 (d, J=9.0 Hz, 1H), 7.12 (dd, J=2.2, 0.7 Hz, 1H), 6.35 (dd, J=9.0, 2.2 Hz, 1H), 6.24 (d, J=2.2 Hz, 1H), 5.36 (s, 2H), 3.41 (q, J=7.0 Hz, 4H), 1.06 (t, J=7.0 Hz, 6H); MS (ES+): 402/404 (M+1).

Step-2: Preparation of 3-((7-bromobenzofuran-5-yl)methoxy)-N,N-diethyl-4-(2-(methylsulfinyl)-2-(methylthio)vinyl)aniline (306c)

Compound 306c was prepared according to the procedure reported in step-3 of scheme-266 from 2-((7-bromobenzofuran-5-yl)methoxy)-4-(diethylamino)benzaldehyde (306b) (1.79 g, 4.45 mmol) in THF (40 mL) using methyl(methylsulfinylmethyl)sulfane (2.211 g, 17.80 mmol), Triton-B (40% methanolic solution, 1.005 mL, 2.225 mmol) and heating at reflux for 3 days. This gave after workup and purification by flash column chromatography (Silica gel, 24 g, eluting with 0-40% EtOAc in hexane) 3-((7-bromobenzofuran-5-yl)methoxy)-N,N-diethyl-4-(2-(methylsulfinyl)-2-(methylthio)vinyl)aniline (306c) as a thick yellow oil (1.24 g); MS (ES+) 508/510 (M+1).

Step-3: Preparation of Ethyl 2-(2-((7-bromobenzofuran-5-yl)methoxy)-4-(diethylamino)phenyl)acetate (306d)

Compound 306d was prepared according to the procedure reported in step-4 of scheme-266 from 3-((7-bromobenzofuran-5-yl)methoxy)-N,N-diethyl-4-(2-(methylsulfinyl)-2-(methylthio)vinyl)aniline (306c) (1.24 g, from step-2) in ethanol (20 mL) using HCl (4 M in 1,4-dioxane, 5.56 mL, 22.25 mmol) and heating at reflux for 3 days. This gave after workup and purification by flash column chromatography (silica gel, 24 g, eluting with 0-8% ethyl acetate and hexanes) ethyl 2-(2-((7-bromobenzofuran-5-yl)methoxy)-4-(diethylamino)phenyl)acetate (306d) (96 mg, 5% yield) as a clear colorless oil; $^1$H NMR (300 MHz, DMSO-$d_6$) δ 8.14 (d, J=2.2 Hz, 1H), 7.72 (d, J=1.5 Hz, 1H), 7.61 (d, J=1.5 Hz, 1H), 7.10 (d, J=2.2 Hz, 1H), 6.93 (d, J=8.4 Hz, 1H), 6.27 (d, J=2.4 Hz, 1H), 6.16 (dd, J=8.3, 2.3 Hz, 1H), 5.18 (s, 2H), 4.02 (q, J=7.1 Hz, 2H), 3.46 (s, 2H), 3.29 (q, J=7.8, 7.0 Hz, 4H), 1.10 (t, J=7.1 Hz, 3H), 1.02 (t, J=6.9 Hz, 6H); MS (ES+): 460/462 (M+1).

Step-4: Preparation of Ethyl 2-(2-((7-(3-(aminomethyl)phenyl)benzofuran-5-yl)methoxy)-4-(diethylamino)phenyl)acetate (306e)

Compound 306e was prepared according to the procedure reported in step-3 of scheme-1 from ethyl 2-(2-((7-bromobenzofuran-5-yl)methoxy)-4-(diethylamino)phenyl)acetate (306d) (92 mg, 0.200 mmol) in dioxane (4 mL) using 3-(aminomethyl)phenylboronic acid hydrochloride (6c) (94 mg, 0.500 mmol), bis(triphenylphosphine)palladium(II) chloride (Pd(PPh$_3$)$_2$Cl$_2$) (21.04 mg, 0.030 mmol), potassium carbonate (0.182 mL, 0.600 mmol) in water (1 mL) under a nitrogen atmosphere heating at 100° C. for 16 h on oil bath.

Preparation of 2-(2-((7-(3-(aminomethyl)phenyl)benzofuran-5-yl)methoxy)-4-(diethylamino)phenyl)acetic Acid (306f)

Step-1: Preparation of 2-((7-bromobenzofuran-5-yl)methoxy)-4-(diethylamino)benzaldehyde (306b)

Compound 306b was prepared according to the procedure reported in step-2 of scheme-152 from 7-bromo-5-(bro- This gave after workup, purification by flash column chromatography (silica gel, 12 g, eluting with 0-5% MeOH in DCM) ethyl 2-(2-((7-(3-(aminomethyl)phenyl)benzofuran-5-yl)methoxy)-4-(diethylamino)phenyl)acetate (306e) (48 mg, 49% yield) as a clear colorless oil; $^1$H NMR (300 MHz, DMSO-$d_6$) δ 8.09 (d, J=2.2 Hz, 1H), 7.82 (d, J=1.8 Hz, 1H), 7.76-7.67 (m, 2H), 7.59 (d, J=1.7 Hz, 1H), 7.46 (t, J=7.5 Hz, 1H), 7.43-7.37 (m, 1H), 7.04 (d, J=2.2 Hz, 1H), 6.93 (d, J=8.3 Hz, 1H), 6.33 (d, J=2.3 Hz, 1H), 6.16 (dd, J=8.4, 2.4 Hz, 1H), 5.23 (s, 2H), 3.94 (q, J=7.1 Hz, 2H), 3.81 (s, 2H), 3.46 (s, 2H), 3.31-3.28 (m, 4H), 1.06-0.99 (m, 9H); MS (ES+): 487 (M+1).

Step-5: Preparation of 2-(2-((7-(3-(aminomethyl)phenyl)benzofuran-5-yl)methoxy)-4-(diethylamino)phenyl)acetic Acid (306f)

Compound 306f was prepared according to the procedure reported in step-6 of scheme-1 from ethyl 2-(2-((7-(3-(aminomethyl)phenyl)benzofuran-5-yl)methoxy)-4-(diethylamino)phenyl)acetate (306e) (48 mg, 0.099 mmol) in MeOH (3 mL) using a 2 M aqueous solution of lithium hydroxide (0.247 mL, 0.493 mmol). This gave after workup and purification by reverse phase column [C18 (100 g), eluting with ACN in water (containing 0.1% HCl) from 0-100%] 2-(2-((7-(3-(aminomethyl)phenyl)benzofuran-5-yl)methoxy)-4-(diethylamino)phenyl)acetic acid (306f) (19 mg, 42% yield) HCl salt as a white solid; $^1$H NMR (300 MHz, DMSO-$d_6$+$D_2$O) δ 8.05 (d, J=2.2 Hz, 1H), 7.97 (d, J=1.8 Hz, 1H), 7.93 (dt, J=7.8, 1.4 Hz, 1H), 7.80 (d, J=1.6 Hz, 1H), 7.69-7.58 (m, 2H), 7.54 (dt, J=7.7, 1.4 Hz, 1H), 7.42 (d, J=8.2 Hz, 1H), 7.31-7.22 (m, 1H), 7.12-6.98 (m, 2H), 5.35 (s, 2H), 4.16 (s, 2H), 3.66 (s, 2H), 3.55 (q, J=7.1 Hz, 4H), 0.97 (t, J=7.1 Hz, 6H); MS (ES+): 459 (M+1), (ES−): 457 (M−1).

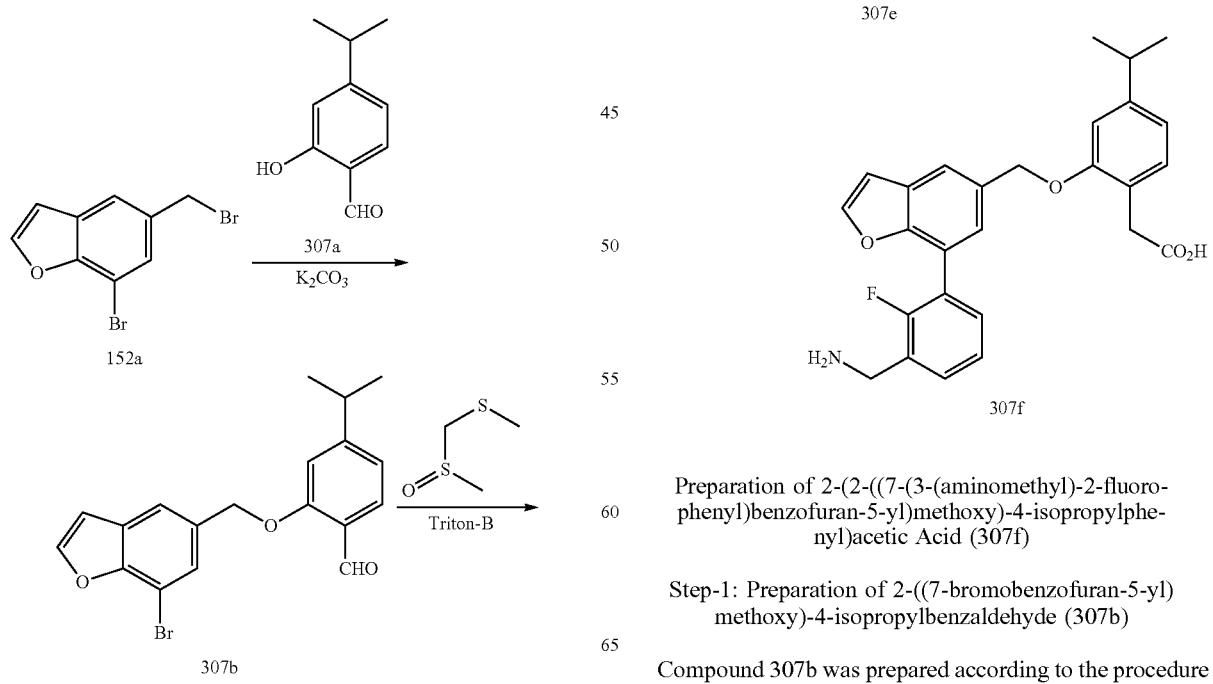

Scheme-307

Preparation of 2-(2-((7-(3-(aminomethyl)-2-fluorophenyl)benzofuran-5-yl)methoxy)-4-isopropylphenyl)acetic Acid (307f)

Step-1: Preparation of 2-((7-bromobenzofuran-5-yl)methoxy)-4-isopropylbenzaldehyde (307b)

Compound 307b was prepared according to the procedure reported in step-2 of scheme-152 from 7-bromo-5-(bromomethyl)benzofuran (152a) (1.766 g, 6.09 mmol) using 2-hydroxy-4-isopropylbenzaldehyde (307a) (1.0 g, 6.09 mmol; CAS #536-23-3), $K_2CO_3$ (2.53 g, 18.27 mmol) in DMF (20 mL) and stirring at room temperature for 16 h. This gave after workup and purification by flash column chromatography (Silica gel, eluting with 0-5% EtOAc in hexane) 2-((7-bromobenzofuran-5-yl)methoxy)-4-isopropylbenzaldehyde (307b) (2.00 g, 88% yield) as a pale-yellow solid; $^1$H NMR (300 MHz, DMSO-$d_6$) δ 10.35 (d, J=0.9 Hz, 1H), 8.14 (dd, J=2.2, 0.9 Hz, 1H), 7.86 (t, J=1.2 Hz, 1H), 7.75 (d, J=1.2 Hz, 1H), 7.65 (dd, J=7.9, 0.9 Hz, 1H), 7.23 (s, 1H), 7.13 (dd, J=2.2, 0.9 Hz, 1H), 7.00 (d, J=8.0 Hz, 1H), 5.38 (s, 2H), 2.96 (p, J=6.9 Hz, 1H), 1.22 (dd, J=6.9, 0.9 Hz, 6H); MS (ES+): 395/397 (M+Na).

Step-2: Preparation of 7-bromo-5-((5-isopropyl-2-(2-(methylsulfinyl)-2-(methylthio)vinyl)phenoxy)methyl)benzofuran (307c)

Compound 307c was prepared according to the procedure reported in step-3 of scheme-266 from 2-((7-bromobenzofuran-5-yl)methoxy)-4-isopropylbenzaldehyde (307b) (970 mg, 2.60 mmol) in THF (20 mL) using methyl(methylsulfinylmethyl)sulfane (517 mg, 4.16 mmol), Triton-B (40% methanolic solution, 0.587 mL, 1.299 mmol) and heating at reflux for 16 h. This gave after workup and purification by flash column chromatography (Silica gel, eluting with 0-30% EtOAc in hexane) 7-bromo-5-((5-isopropyl-2-(2-(methylsulfinyl)-2-(methylthio)vinyl)phenoxy)methyl)benzofuran (307c) (0.97 g) as a thick yellow syrup; MS (ES+): 479/481 (M+1).

Step-3: Preparation of Ethyl 2-(2-((7-bromobenzofuran-5-yl)methoxy)-4-isopropylphenyl)acetate (307d)

Compound 307d was prepared according to the procedure reported in step-4 of scheme-266 from 7-bromo-5-((5-isopropyl-2-(2-(methylsulfinyl)-2-(methylthio)vinyl)phenoxy)methyl)benzofuran (307c) (0.97 g, from step-2) in ethanol (20 mL) using HCl (4 M in 1,4-dioxane, 1.949 mL, 7.80 mmol) and heating at reflux for 16 h. This gave after workup and purification by flash column chromatography (silica gel, 24 g, eluting with 0-5% ethyl acetate and hexanes) ethyl 2-(2-((7-bromobenzofuran-5-yl)methoxy)-4-isopropylphenyl)acetate (307d) (0.63 g, 56% yield) as a white solid; $^1$H NMR (300 MHz, DMSO-$d_6$) δ 8.14 (t, J=2.2 Hz, 1H), 7.73 (d, J=1.5 Hz, 1H), 7.62 (d, J=1.6 Hz, 1H), 7.18-7.06 (m, 2H), 6.98 (d, J=1.7 Hz, 1H), 6.79 (dd, J=7.6, 1.6 Hz, 1H), 5.18 (s, 2H), 4.01 (qd, J=7.2, 1.9 Hz, 2H), 3.56 (s, 2H), 2.86 (p, J=6.9 Hz, 1H), 1.21 (d, J=1.8 Hz, 3H), 1.19 (d, J=1.9 Hz, 3H), 1.07 (td, J=7.1, 1.8 Hz, 3H); MS (ES+) 431/433 (M+1).

Step-4: Preparation of Ethyl 2-(2-((7-(3-(aminomethyl)-2-fluorophenyl)benzofuran-5-yl)methoxy)-4-isopropylphenyl)acetate (307e)

Compound 307e was prepared according to the procedure reported in step-3 of scheme-1 from ethyl 2-(2-((7-bromobenzofuran-5-yl)methoxy)-4-isopropylphenyl)acetate (307d) (150 mg, 0.348 mmol) in dioxane (4 mL) using (3-(aminomethyl)-2-fluorophenyl)boronic acid hydrochloride (56a) (107 mg, 0.522 mmol), bis(triphenylphosphine)palladium(II) chloride (Pd(PPh$_3$)$_2$Cl$_2$) (24 mg, 0.035 mmol), 2 M aqueous $K_2CO_3$ (0.522 mL, 1.043 mmol) under an nitrogen atmosphere heating at 100° C. for 16 h on oil bath. This gave after workup, purification by flash column chromatography (silica gel 12 g, eluting with 0-3% MeOH in DCM) ethyl 2-(2-((7-(3-(aminomethyl)-2-fluorophenyl)benzofuran-5-yl)methoxy)-4-isopropylphenyl)acetate (307e) (101 mg) as a clear colorless oil; MS (ES+): 476 (M+1).

Step-5: Preparation of 2-(2-((7-(3-(aminomethyl)-2-fluorophenyl)benzofuran-5-yl)methoxy)-4-isopropylphenyl)acetic Acid (307f)

Compound 307f was prepared according to the procedure reported in step-6 of scheme-1 from ethyl 2-(2-((7-(3-(aminomethyl)-2-fluorophenyl)benzofuran-5-yl)methoxy)-4-isopropylphenyl)acetate (307e) (101 mg, from step-4 above) in MeOH (3 mL) using a 2 M aqueous solution of lithium hydroxide (0.422 mL, 1.391 mmol). This gave after workup and purification by reverse phase column [C18 (100 g), eluting with ACN in water (containing 0.1% HCl) from 0-100%] 2-(2-((7-(3-(aminomethyl)-2-fluorophenyl)benzofuran-5-yl)methoxy)-4-isopropylphenyl)acetic acid (307f) (76 mg, 49% yield) HCl salt as a white solid; $^1$H NMR (300 MHz, DMSO-$d_6$) δ 8.06 (d, J=2.2 Hz, 1H), 7.84 (d, J=1.6 Hz, 1H), 7.67 (t, J=7.3 Hz, 2H), 7.49 (t, J=1.3 Hz, 1H), 7.43 (t, J=7.7 Hz, 1H), 7.11 (d, J=7.7 Hz, 1H), 7.07 (d, J=2.2 Hz, 1H), 7.00 (d, J=1.6 Hz, 1H), 6.78 (dd, J=7.8, 1.6 Hz, 1H), 5.25 (s, 2H), 4.17 (s, 2H), 3.52 (s, 2H), 2.94-2.80 (m, 1H), 1.21 (s, 3H), 1.18 (s, 3H). $^{19}$F NMR (300 MHz, DMSO-$d_6$) δ −118.44; MS (ES+): 448 (M+1), (ES−): 446 (M−1); Analysis calculated for $C_{27}H_{26}FNO_4$·HCl·0.75H$_2$O: C, 65.19; H, 5.77; Cl, 7.13; N, 2.82; Found: C, 65.36; H, 5.61; Cl, 7.46; N, 2.99.

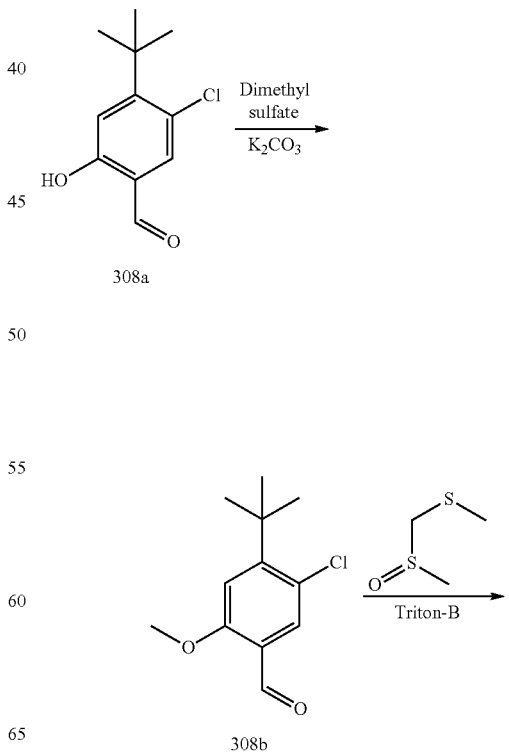

Scheme-308

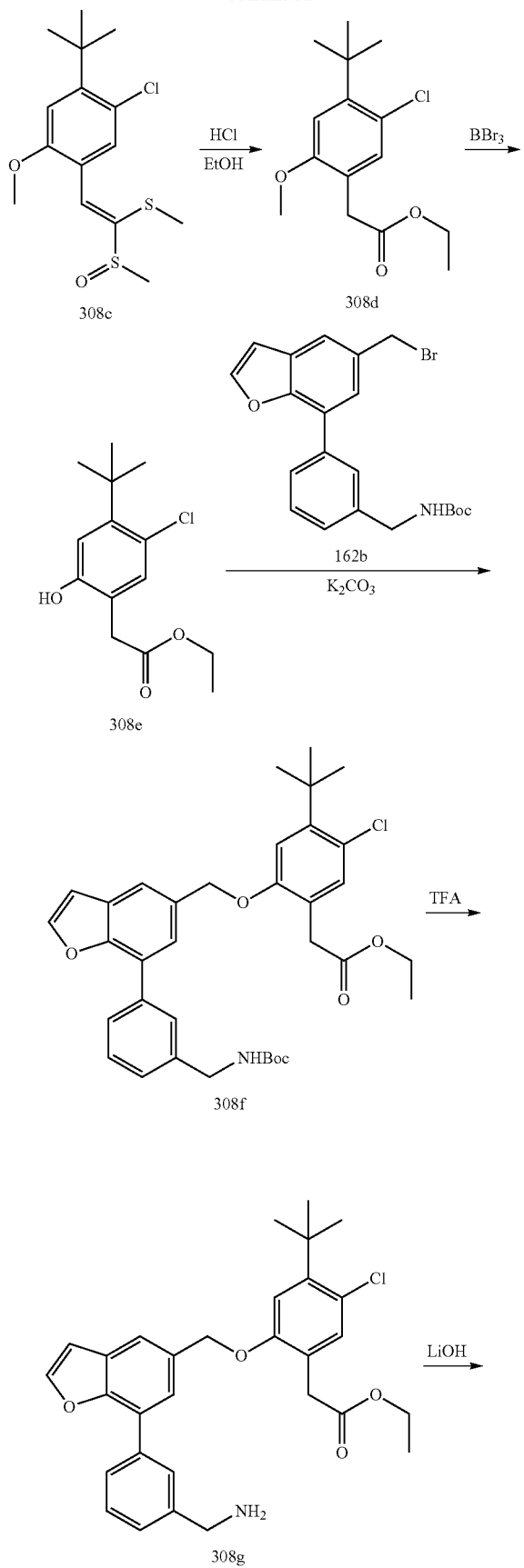

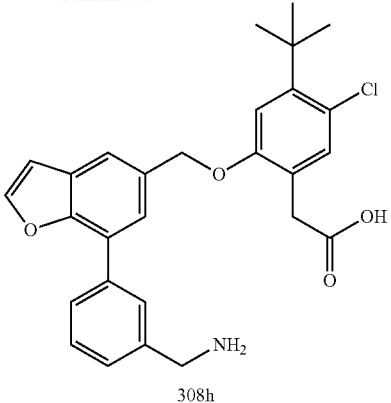

308h

Preparation of 2-(2-((7-(3-(aminomethyl)phenyl)
benzofuran-5-yl)methoxy)-4-(tert-butyl)-5-chloro-
phenyl)acetic Acid (308h)

Step-1: Preparation of 4-(tert-butyl)-5-chloro-2-
methoxybenzaldehyde (308b)

To a solution of 4-tert-butyl-5-chloro-2-hydroxybenzaldehyde (308a) (1 g, 4.70 mmol), dimethyl sulfate (0.491 mL, 5.17 mmol) and in acetone (10 mL) was added $K_2CO_3$ (3.90 g, 28.2 mmol) and heated at reflux for 2 h. The reaction was concentrated to remove acetone and diluted with ethyl acetate (50 mL), washed with water (2×20 mL), brine (20 mL), dried, filtered and concentrated. The crude residue was purified by flash column chromatography (silica gel, 40 g, eluting with ethyl acetate and hexanes) to afford 4-(tert-butyl)-5-chloro-2-methoxybenzaldehyde (308b) (298 mg, 28% yield) as a white solid; $^1$H NMR (300 MHz, DMSO-$d_6$) δ 10.24 (s, 1H), 7.59 (s, 1H), 7.19 (s, 1H), 3.33 (s, 3H), 1.48 (s, 9H). MS (ES+): 227.1 (M+1).

Step-2: Preparation of (2-(4-(tert-butyl)-5-chloro-2-
methoxyphenyl)-1-(methyl sulfinyl)vinyl)(methyl)
sulfane (308c)

Compound 308c was prepared according to the procedure reported in step-3 of scheme-266 from 4-(tert-butyl)-5-chloro-2-methoxybenzaldehyde (308b) (295 mg, 1.301 mmol) in THF (20 mL) using methyl(methylsulfinylmethyl)sulfane (259 mg, 2.082 mmol), Triton-B (40% methanolic solution) (0.296 mL, 0.651 mmol) and heating at reflux for 12 h. This gave after workup and purification by flash column chromatography (silica gel, 40 g, eluting with ethyl acetate and hexanes) (2-(4-(tert-butyl)-5-chloro-2-methoxyphenyl)-1-(methylsulfinyl)vinyl)(methyl)sulfane (308c) (237 mg, 55% yield) as a white solid; $^1$H NMR (300 MHz, DMSO-$d_6$) δ 8.03 (s, 1H), 7.64 (s, 1H), 7.07 (s, 1H), 3.88 (s, 3H), 2.74 (s, 3H), 2.32 (s, 3H), 1.47 (s, 9H).

Step-3: Preparation of Ethyl 2-(4-(tert-butyl)-5-
chloro-2-methoxyphenyl)acetate (308d)

Compound 308d was prepared according to the procedure reported in step-4 of scheme-266 from (2-(4-(tert-butyl)-5-chloro-2-methoxyphenyl)-1-(methylsulfinyl)vinyl)(methyl)sulfane (308c) (290 mg, 0.871 mmol) in ethanol (10 mL) using HCl (4 M in 1,4-dioxane) (0.871 mL, 3.48 mmol) and heating at reflux for 12 h. This gave after workup and purification by flash column chromatography (silica gel, 40 g, eluting with ethyl acetate and hexanes) ethyl 2-(4-(tert-butyl)-5-chloro-2-methoxyphenyl)acetate (308d) (170 mg, 69% yield) as a clear syrup; $^1$H NMR (300 MHz, DMSO-d$_6$) δ 7.22 (s, 1H), 6.96 (s, 1H), 4.06 (q, J=7.1 Hz, 2H), 3.77 (s, 3H), 3.54 (s, 2H), 1.45 (s, 9H), 1.17 (t, J=7.1 Hz, 3H).

Step-4: Preparation of Ethyl 2-(4-(tert-butyl)-5-chloro-2-hydroxyphenyl)acetate (308e)

Compound 308e was prepared according to the procedure reported in step-5 of scheme-257 from ethyl 2-(4-(tert-butyl)-5-chloro-2-methoxyphenyl)acetate (308d) (170 mg, 0.597 mmol) in dichloromethane (5 mL) using boron tribromide (0.226 mL, 2.388 mmol). This gave after workup ethyl 2-(4-(tert-butyl)-5-chloro-2-hydroxyphenyl)acetate (308e) (84 mg, 52% yield) as a clear syrup; $^1$H NMR (300 MHz, DMSO-d$_6$) δ 9.64 (s, 1H), 7.12 (s, 1H), 6.93 (s, 1H), 4.06 (q, J=7.1 Hz, 2H), 3.50 (s, 2H), 1.39 (s, 9H), 1.17 (t, J=7.1 Hz, 3H). MS (ES+): 271.1 (M+1).

Step-5: Preparation of Ethyl 2-(2-((7-(3-(((tert-butoxycarbonyl)amino)methyl)phenyl)benzofuran-5-yl)methoxy)-4-(tert-butyl)-5-chlorophenyl)acetate (308f)

Compound 308f was prepared according to the procedure reported in step-2 of scheme-152 from tert-butyl 3-(5-(bromomethyl)benzofuran-7-yl)benzylcarbamate (162b) (135 mg, 0.325 mmol) using ethyl 2-(4-(tert-butyl)-5-chloro-2-hydroxyphenyl)acetate (308e) (80 mg, 0.295 mmol), K$_2$CO$_3$ (123 mg, 0.886 mmol) in DMF (5 mL) and stirring at room temperature for 12 h. This gave after workup and purification by flash column chromatography (silica gel 12 g, eluting with EtOAc in hexane 0-50%) ethyl 2-(2-((7-(3-(((tert-butoxycarbonyl)amino)methyl)phenyl)benzofuran-5-yl)methoxy)-4-(tert-butyl)-5-chlorophenyl)acetate (308f) (141 mg, 79% yield) as a clear oil; $^1$H NMR (300 MHz, DMSO-d$_6$) δ 8.09 (d, J=2.2 Hz, 1H), 7.76-7.68 (m, 3H), 7.56-7.44 (m, 3H), 7.34-7.23 (m, 2H), 7.13 (s, 1H), 7.07 (d, J=2.2 Hz, 1H), 5.27 (s, 2H), 4.22 (d, J=6.2 Hz, 2H), 3.92 (q, J=7.1 Hz, 2H), 3.59 (s, 2H), 1.43 (s, 9H), 1.39 (s, 9H), 0.98 (t, J=7.1 Hz, 3H).

Step-6: Preparation of Ethyl 2-(2-((7-(3-(aminomethyl)phenyl)benzofuran-5-yl)methoxy)-4-(tert-butyl)-5-chlorophenyl)acetate (308g)

Compound 308g was prepared according to the procedure reported in step-5 of scheme-1 from ethyl 2-(2-((7-(3-(((tert-butoxycarbonyl)amino)methyl)phenyl)benzofuran-5-yl)methoxy)-4-(tert-butyl)-5-chlorophenyl)acetate (308f) (135 mg, 0.223 mmol) in DCM (5 mL) using TFA (0.343 mL, 4.45 mmol). This gave after workup ethyl 2-(2-((7-(3-(aminomethyl)phenyl)benzofuran-5-yl)methoxy)-4-(tert-butyl)-5-chlorophenyl)acetate (308g) (113 mg); MS (ES+): 506.2 (M+1).

Step 7: Preparation of 2-(2-((7-(3-(aminomethyl)phenyl)benzofuran-5-yl)methoxy)-4-(tert-butyl)-5-chlorophenyl)acetic Acid (308h)

Compound 308h was prepared according to the procedure reported in step-6 of scheme-1 from of ethyl 2-(2-((7-(3-(aminomethyl)phenyl)benzofuran-5-yl)methoxy)-4-(tert-butyl)-5-chlorophenyl)acetate (308g) (113 mg, 0.223 mmol) in MeOH (2 mL), THF (2 mL) using a solution of lithium hydroxide (22 mg, 0.893 mmol) in water (0.4 mL). This gave after workup and purification by reverse phase column [C18 (15g), eluting with ACN in water (containing 0.1% HCl) from 0-100%] 2-(2-((7-(3-(aminomethyl)phenyl)benzofuran-5-yl)methoxy)-4-(tert-butyl)-5-chlorophenyl)acetic acid (308h) (30 mg, 28% yield) hydrochloride salt as a white solid; $^1$H NMR (300 MHz, DMSO-d$_6$) δ 12.33 (s, 1H), 8.41 (s, 2H), 8.12 (d, J=2.2 Hz, 1H), 8.00 (s, 1H), 7.92 (d, J=7.2 Hz, 1H), 7.77 (s, 1H), 7.66 (s, 1H), 7.66-7.51 (m, 2H), 7.26 (s, 1H), 7.14-7.04 (m, 2H), 5.30 (s, 2H), 4.14 (s, 2H), 3.57 (s, 2H), 1.42 (s, 9H); MS (ES+): 478.1 (M+1), (ES−): 476.1 (M−1); Analysis calculated for C$_{28}$H$_{28}$ClNO$_4$·1.25H$_2$O·HCl: C, 62.63; H, 5.91; N, 2.61; Found: C, 62.59; H, 5.85; N, 2.70.

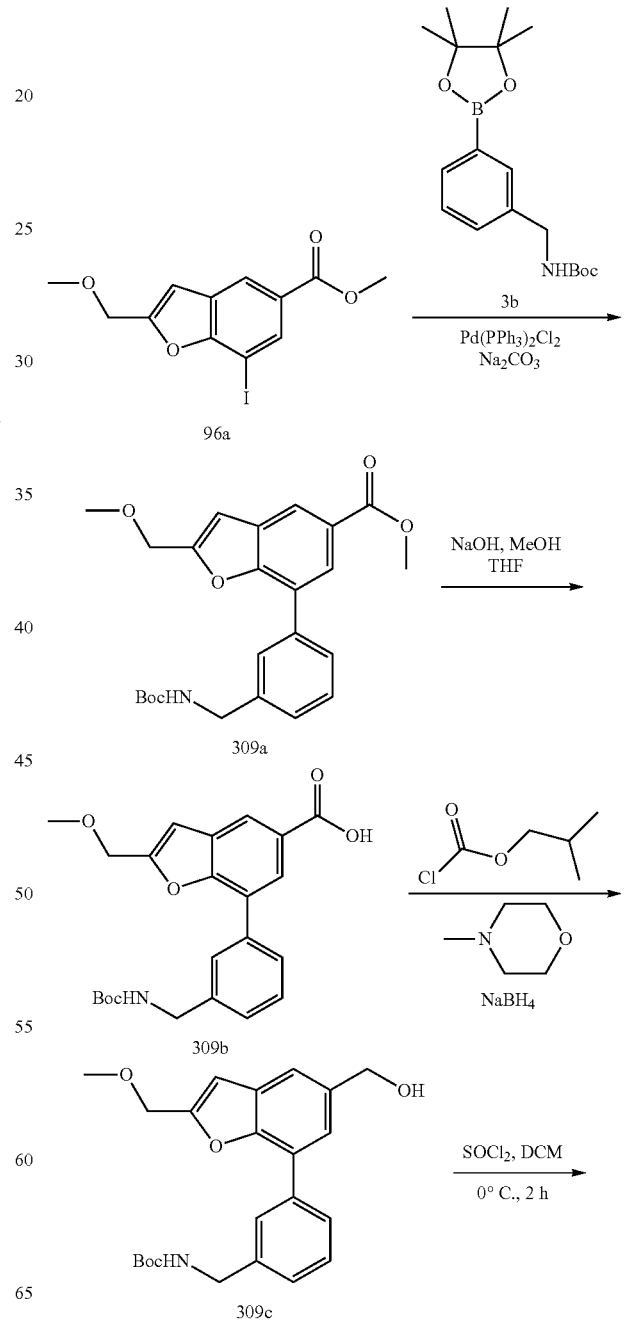

Scheme-309

1025
-continued

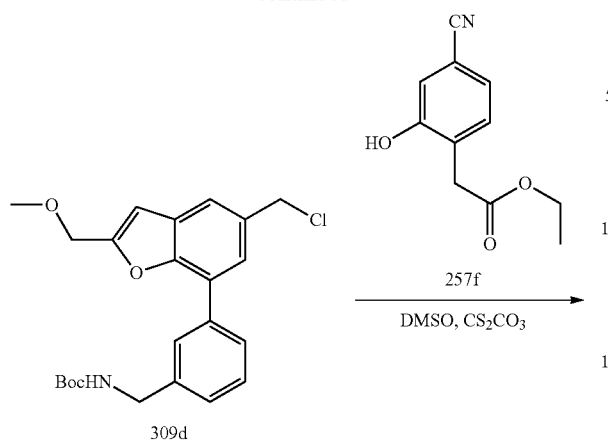

1026
-continued

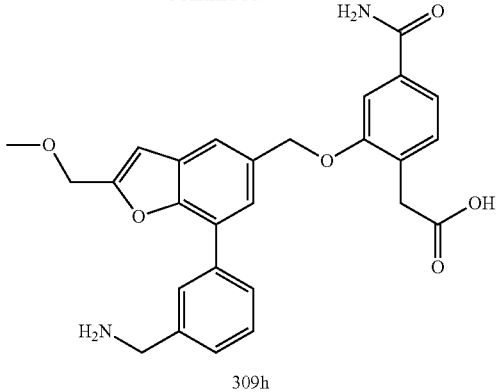 [SMILES: COCc1cc2cc(COc3cc(C(N)=O)ccc3CC(=O)O)cc(-c3cccc(CN)c3)c2o1]

Preparation of 2-(2-((7-(3-(aminomethyl)phenyl)-2-(methoxymethyl)benzofuran-5-yl)methoxy)-4-carbamoylphenyl)acetic Acid (309h)

Step-1: Preparation of methyl 7-(3-(((tert-butoxycarbonyl)amino)methyl)phenyl)-2-(methoxymethyl)benzofuran-5-carboxylate (309a)

Compound 309a was prepared according to the procedure reported in step-3 of scheme-1 from methyl 7-iodo-2-(methoxymethyl)benzofuran-5-carboxylate (96a) (500 mg, 1.44 mmol) in 1,4-dioxane (10.0 mL) using tert-butyl 3-(4,4,5,5-tetramethyl-1,3,2-dioxaborolan-2-yl)benzylcarbamate (3b) (625 mg, 1.87 mmol), Pd(PPh$_3$)$_2$Cl$_2$ (0.15 g, 0.216 mmol), K$_3$PO$_4$ (919 mg, 4.33 mmol) and heating under a nitrogen atmosphere at 90° C. for 12 h on an oil bath. This gave after workup, purification by flash column chromatography (silica gel, eluting with 0-30% EtOAc in n-heptane) methyl 7-(3-(((tert-butoxycarbonyl)amino)methyl)phenyl)-2-(methoxymethyl)benzofuran-5-carboxylate (309a) (200 mg, 32%) as an off-white solid; $^1$H NMR (300 MHz, DMSO-d$_6$) δ 8.29 (d, J=1.7 Hz, 1H), 8.03 (d, J=1.7 Hz, 1H), 7.75 (d, J=7.7 Hz, 1H), 7.67 (s, 1H), 7.51 (t, J=7.5 Hz, 2H), 7.33 (d, J=7.6 Hz, 1H), 7.13 (s, 1H), 4.59 (s, 2H), 4.23 (d, J=6.2 Hz, 2H), 3.90 (s, 3H), 3.33 (s, 3H), 1.40 (s, 9H).

Step-2: Preparation of 7-(3-(((tert-butoxycarbonyl)amino)methyl)phenyl)-2-(methoxymethyl)benzofuran-5-carboxylic Acid (309b)

Compound 309b was prepared according to the procedure reported in step-4 of scheme-4 from methyl 7-(3-(((tert-butoxycarbonyl)amino)methyl)phenyl)-2-(methoxymethyl)benzofuran-5-carboxylate (309a) (1.3 g, 3.05 mmol) in THF (13 mL) MeOH (39 mL) using an aqueous solution of sodium hydroxide (13.0 mL, 0.36 g, 9.16 mmol). This gave after workup 7-(3-(((tert-butoxycarbonyl)amino)methyl)phenyl)-2-(methoxymethyl)benzofuran-5-carboxylic acid (309b) (1.2 g, 95.45%) as an off-white solid; $^1$H NMR (300 MHz, DMSO-d$_6$) δ 13.01 (s, 1H), 8.26 (d, J=1.7 Hz, 1H), 8.05 (d, J=1.7 Hz, 1H), 7.76 (d, J=7.7 Hz, 1H), 7.68 (s, 1H), 7.50 (dd, J=8.7, 6.7 Hz, 2H), 7.32 (d, J=7.6 Hz, 1H), 7.11 (s, 1H), 4.59 (s, 2H), 4.23 (d, J=6.2 Hz, 2H), 3.33 (s, 3H), 1.40 (s, 9H).

Step-3: Preparation of tert-butyl 3-(5-(hydroxymethyl)-2-(methoxymethyl)benzofuran-7-yl)benzylcarbamate (309c)

Compound 309c was prepared according to the procedure reported in step-1 of scheme-23 from 7-(3-(((tert-butoxy-

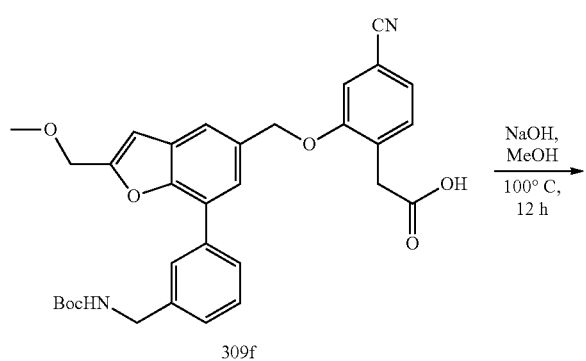

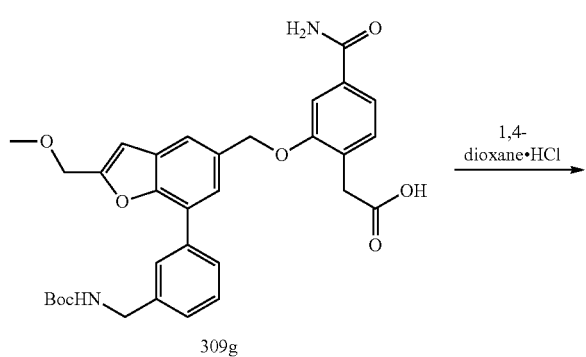

carbonyl)amino)methyl)phenyl)-2-(methoxymethyl)benzofuran-5-carboxylic acid (309b) (1.2 g, 2.91 mmol) using N-methylmorpholine (0.35 g, 3.49 mmol) in THF (24 mL), isobutyl chloroformate (0.47 g, 3.49 mmol) and NaBH$_4$ (0.33 g, 8.74 mmol) in water (10 mL). This gave after workup and purification by flash column chromatography (silica gel, eluting with 0-30% EtOAc in n-heptane) tert-butyl 3-(5-(hydroxymethyl)-2-(methoxymethyl)benzofuran-7-yl)benzylcarbamate (309c) (1.0 g, 86%) as an oil; $^1$H NMR (300 MHz, DMSO-d$_6$) δ 7.72 (d, J=7.9 Hz, 1H), 7.67 (s, 1H), 7.59-7.53 (m, 1H), 7.53-7.39 (m, 3H), 7.28 (d, J=7.7 Hz, 1H), 6.96 (s, 1H), 5.28 (t, J=5.7 Hz, 1H), 4.63 (d, J=5.5 Hz, 2H), 4.55 (s, 2H), 4.31-4.18 (m, 2H), 3.32 (s, 3H), 1.40 (s, 9H).

Step-4: Preparation of tert-butyl 3-(5-(chloromethyl)-2-(methoxymethyl)benzofuran-7-yl)benzylcarbamate (309d)

Compound 309d was prepared according to the procedure reported in step-4 of scheme-257 from tert-butyl 3-(5-(hydroxymethyl)-2-(methoxymethyl)benzofuran-7-yl)benzylcarbamate (309c) (0.8 g, 2.01 mmol) in DCM (16 mL) using SOCl$_2$ (0.47 g, 4.02 mmol) and stirring at 0° C. for 2 h. This gave after workup tert-butyl 3-(5-(chloromethyl)-2-(methoxymethyl)benzofuran-7-yl)benzylcarbamate (309d) (0.8 g, 96%) as an oil; $^1$H NMR (300 MHz, DMSO-d$_6$) δ 7.72 (d, J=7.9 Hz, 1H), 7.67 (s, 1H), 7.56 (d, J=1.6 Hz, 1H), 7.53-7.39 (m, 3H), 7.28 (d, J=7.7 Hz, 1H), 6.96 (s, 1H), 4.63 (d, J=5.5 Hz, 2H), 4.55 (s, 2H), 4.22 (d, J=6.3 Hz, 2H), 3.32 (s, 3H), 1.40 (s, 9H).

Step-5: Preparation of Ethyl 2-(2-((7-(3-(((tert-butoxycarbonyl)amino)methyl)phenyl)-2-(methoxymethyl)benzofuran-5-yl)methoxy)-4-cyanophenyl)acetate (309e)

Compound 309e was prepared according to the procedure reported in step-6 of scheme-257 from tert-butyl 3-(5-(chloromethyl)-2-(methoxymethyl)benzofuran-7-yl)benzylcarbamate (309d) (0.7 g, 1.68 mmol) in DMSO (7 mL) using ethyl 2-(4-cyano-2-hydroxyphenyl)acetate (257f) (0.35 g, 1.7 mmol), Cs$_2$CO$_3$ (0.58 g, 1.68 mmol) and stirring at room temperature for 24 h. This gave after workup and purification by flash column chromatography (silica gel, eluting with 0-10% EtOAc in n-heptane) ethyl 2-(2-((7-(3-(((tert-butoxycarbonyl)amino)methyl)phenyl)-2-(methoxymethyl)benzofuran-5-yl)methoxy)-4-cyanophenyl)acetate (309e) (0.5 g, 51%) as an oil; $^1$H NMR (300 MHz, DMSO-d$_6$) δ 7.81-7.59 (m, 4H), 7.59-7.25 (m, 6H), 7.10-6.93 (m, 1H), 5.30 (s, 2H), 4.66-4.44 (m, 2H), 4.24 (s, 2H), 3.89 (m, 2H), 3.72 (dm, 2H), 3.37 (s, 3H), 1.40 (s, 9H), 0.95 (t, 3H).

Step-6: Preparation of 2-(2-((7-(3-(((tert-butoxycarbonyl)amino)methyl)phenyl)-2-(methoxymethyl)benzofuran-5-yl)methoxy)-4-cyanophenyl)acetic Acid (309f)

Compound 309f was prepared according to the procedure reported in step-4 of scheme-4 from ethyl 2-(2-((7-(3-(((tert-butoxycarbonyl)amino)methyl)phenyl)-2-(methoxymethyl)benzofuran-5-yl)methoxy)-4-cyanophenyl)acetate (309e) (0.5 g, 0.85 mmol) in MeOH (5 mL) using a solution of NaOH (0.102 g, 2.56 mmol) in water (5 mL) and heating at 100° C. for 12 h. This gave after workup 2-(2-((7-(3-(((tert-butoxycarbonyl)amino)methyl)phenyl)-2-(methoxymethyl)benzofuran-5-yl)methoxy)-4-cyanophenyl)acetic acid (309f) (0.32 g, 67%) as an off white solid; $^1$H NMR (300 MHz, DMSO-d$_6$) δ 7.77-7.67 (m, 3H), 7.58 (d, J=9.8 Hz, 2H), 7.53-7.36 (m, 4H), 7.30 (d, J=7.7 Hz, 1H), 6.99 (s, 1H), 5.32 (s, 2H), 4.57 (s, 2H), 4.23 (d, J=6.2 Hz, 2H), 3.68 (s, 2H), 3.33 (s, 3H), 1.38 (s, 9H); MS (ES-): 555.2 (M-1).

Step-7: Preparation of 2-(2-((7-(3-(((tert-butoxycarbonyl)amino)methyl)phenyl)-2-(methoxymethyl)benzofuran-5-yl)methoxy)-4-carbamoylphenyl)acetic Acid (309g)

Compound 309g was prepared according to the procedure reported in step-4 of scheme-4 from 2-(2-((7-(3-(((tert-butoxycarbonyl)amino)methyl)phenyl)-2-(methoxymethyl)benzofuran-5-yl)methoxy)-4-cyanophenyl)acetic acid (309f) (0.3 g, 0.53 mmol) in MeOH (3 mL) using a solution of NaOH (0.043 g, 1.70 mmol) in water (3 mL) and heating at 100° C. for 12 h. This gave after workup 2-(2-((7-(3-(((tert-butoxycarbonyl)amino)methyl)phenyl)-2-(methoxymethyl)benzofuran-5-yl)methoxy)-4-carbamoylphenyl)acetic acid (309g) (0.19 g, 61%) as an off white solid; $^1$H NMR (300 MHz, DMSO-d$_6$) δ 7.98 (s, 1H), 7.72 (s, 3H), 7.61 (s, 2H), 7.54-7.23 (m, 6H), 6.98 (s, 1H), 5.31 (s, 2H), 4.57 (s, 2H), 4.23 (s, 2H), 3.70-3.59 (m, 2H), 3.33 (s, 3H), 1.39 (s, 9H).

Step-8: Preparation of 2-(2-((7-(3-(aminomethyl)phenyl)-2-(methoxymethyl)benzofuran-5-yl)methoxy)-4-carbamoylphenyl)acetic Acid (309h)

Compound 309h was prepared according to the procedure reported in step-10 of scheme-257 from 2-(2-((7-(3-(((tert-butoxycarbonyl)amino)methyl)phenyl)-2-(methoxymethyl)benzofuran-5-yl)methoxy)-4-carbamoylphenyl)acetic acid (309g) ((0.18 g, 0.31 mmol) in 1,4-dioxane (1.8 mL) was added at room temperature 1,4-dioxane. HCl (28%, 1.8 mL) and stirred for 2 h. This gave after workup 2-(2-((7-(3-(aminomethyl)phenyl)-2-(methoxymethyl)benzofuran-5-yl)methoxy)-4-carbamoylphenyl)acetic acid (309h) (0.025 g, 16%) as an off white solid; $^1$H NMR (300 MHz, DMSO-d$_6$) δ 8.24 (s, 3H), 8.02-7.89 (m, 3H), 7.74 (s, 1H), 7.66-7.26 (m, 7H), 7.01 (s, 1H), 5.31 (s, 2H), 4.58 (s, 2H), 4.20-4.08 (m, 2H), 3.64 (s, 2H), 3.32 (s, 3H). This was purified by reverse phase column chromatography [C18 steel column, 250 mm×30 mm, eluting with ACN in water (containing 0.1% TFA) from 0-100%] to afford compound 309h 14 mgs as a TFA salt; $^1$H NMR (300 MHz, DMSO-d$_6$) δ 12.32 (s, 1H), 8.20 (s, 3H), 7.98 (s, 1H), 7.96-7.91 (m, 2H), 7.74 (d, J=1.6 Hz, 1H), 7.66-7.58 (m, 3H), 7.53 (d, J=7.7 Hz, 1H), 7.48-7.43 (m, 1H), 7.37 (s, 1H), 7.30 (d, J=7.8 Hz, 1H), 5.31 (s, 2H), 4.58 (s, 2H), 4.15 (d, J=5.8 Hz, 2H), 3.64 (s, 2H), 3.32 (s, 3H); MS (ES+): 475.20 (M+1).

Scheme-310

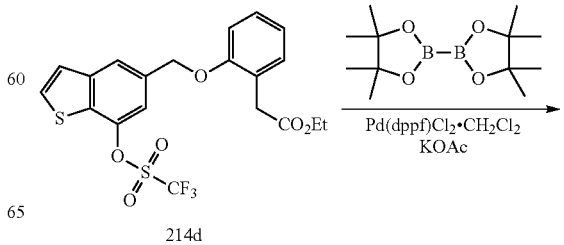

214d

Preparation of 2-(2-((7-(2-(aminomethyl)pyridin-4-yl)benzo[b]thiophen-5-yl)methoxy)phenyl)acetic Acid (310c)

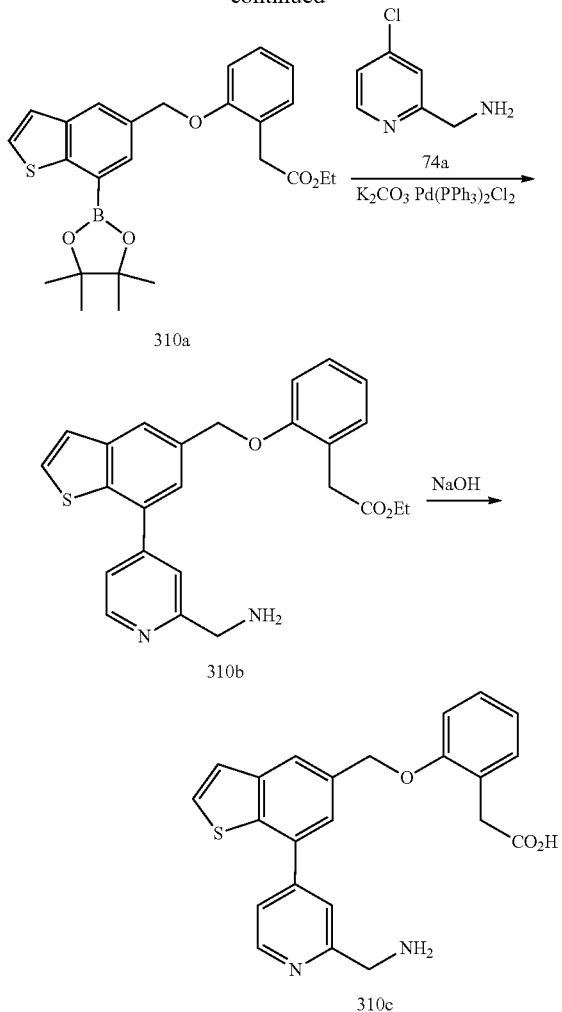

Step-1: Preparation of Ethyl 2-(2-((7-(4,4,5,5-tetramethyl-1,3,2-dioxaborolan-2-yl)benzo[b]thiophen-5-yl)methoxy)phenyl)acetate (310a)

Compound 310a was prepared according to the procedure reported in step-1 of scheme-59 from ethyl 2-(2-((7-(trifluoromethylsulfonyloxy)benzo[b]thiophen-5-yl)methoxy)phenyl)acetate (214d) (200 mg, 0.422 mmol), using bis(pinacolato)diboron (161 mg, 0.632 mmol), potassium acetate (124 mg, 1.265 mmol) and Pd(dppf)Cl$_2$—CH$_2$Cl$_2$ (34 mg, 0.042 mmol) in anhydrous dioxane (5 mL) under a nitrogen atmosphere and heating at 100° C. for 16 h. This gave after workup and purification by flash column chromatography [silica gel (24g), eluting with EtOAc in hexanes from 0-10%] ethyl 2-(2-((7-(4,4,5,5-tetramethyl-1,3,2-dioxaborolan-2-yl)benzo[b]thiophen-5-yl)methoxy)phenyl)acetate (310a) (118 mg, 62% yield) as a colorless oil. $^1$H NMR (300 MHz, Chloroform-d) δ 8.00 (dd, J=1.8, 0.9 Hz, 1H), 7.83 (d, J=1.7 Hz, 1H), 7.50 (dd, J=5.6, 0.5 Hz, 1H), 7.33 (d, J=5.5 Hz, 1H), 7.25-7.19 (m, 2H), 7.00-6.90 (m, 2H), 5.20 (s, 2H), 4.11 (q, J=7.1 Hz, 2H), 3.68 (s, 2H), 1.41 (s, 12H), 1.16 (t, J=7.1 Hz, 3H).

Step-2: Preparation of Ethyl 2-(2-((7-(2-(aminomethyl)pyridin-4-yl)benzo[b]thiophen-5-yl)methoxy)phenyl)acetate (310b)

Compound 310b was prepared according to the procedure reported in step-3 of scheme-1 from ethyl 2-(2-((7-(4,4,5,5-tetramethyl-1,3,2-dioxaborolan-2-yl)benzo[b]thiophen-5-yl)methoxy)phenyl)acetate (310a) (118 mg, 0.261 mmol) in dioxane (4 mL) using (4-chloropyridin-2-yl)methanamine (74a) (41 mg, 0.287 mmol), bis(triphenylphosphine)palladium(II) chloride (Pd(PPh$_3$)$_2$Cl$_2$) (18 mg, 0.026 mmol) and a solution of K$_2$CO$_3$ (108 mg, 0.783 mmol) in water (1.0 mL) under a nitrogen atmosphere heating at 100° C. for 16 h on oil bath. This gave after workup and purification by flash column chromatography [silica gel (12 g), eluting with 0-10% MeOH in DCM] ethyl 2-(2-((7-(2-(aminomethyl)pyridin-4-yl)benzo[b]thiophen-5-yl)methoxy)phenyl)acetate (310b) (47 mg) as a pale-yellow oil; MS (ES+): 433 (M+1).

Step-3: Preparation of 2-(2-((7-(2-(aminomethyl)pyridin-4-yl)benzo[b]thiophen-5-yl)methoxy)phenyl)acetic Acid (310c)

Compound 310c was prepared according to the procedure reported in step-4 of scheme-4 from ethyl 2-(2-((7-(2-(aminomethyl)pyridin-4-yl)benzo[b]thiophen-5-yl)methoxy)phenyl)acetate (310b) (47 mg, from above step-2) in MeOH (3 mL) water (1 mL) using NaOH (52 mg, 1.304 mmol). This gave after workup and purification by reverse phase column [C18 (100 g), eluting with water in acetonitrile from 0-60%] 2-(2-((7-(2-(aminomethyl)pyridin-4-yl)benzo[b]thiophen-5-yl)methoxy)phenyl)acetic acid (310c) (30 mg, 28% yield) HCl salt as a pale-green solid. $^1$H NMR (300 MHz, DMSO-d$_6$) δ 8.81 (d, J=5.1 Hz, 1H), 8.55-8.30 (m, 3H), 8.09 (d, J=1.5 Hz, 1H), 7.95-7.88 (m, 2H), 7.84 (dd, J=5.1, 1.8 Hz, 1H), 7.65 (d, J=1.6 Hz, 1H), 7.61 (d, J=5.5 Hz, 1H), 7.25 (dd, J=8.1, 6.6 Hz, 2H), 7.15-7.05 (m, 1H), 6.98-6.86 (m, 1H), 5.33 (s, 2H), 4.41-4.26 (m, 2H), 3.61 (s, 2H); MS (ES+): 405 (M+1), (ES−): 403 (M−1).

Scheme-311

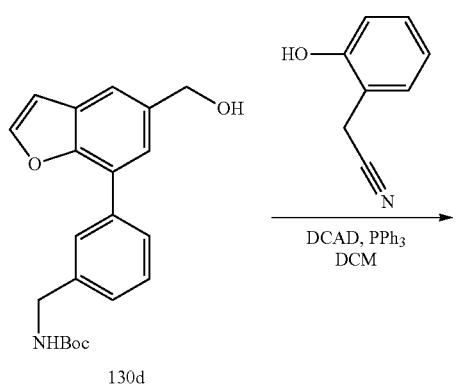

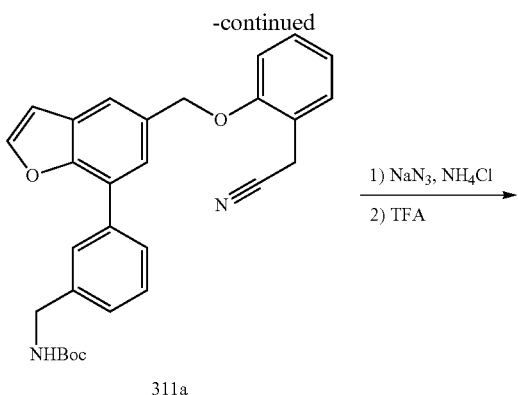

311a

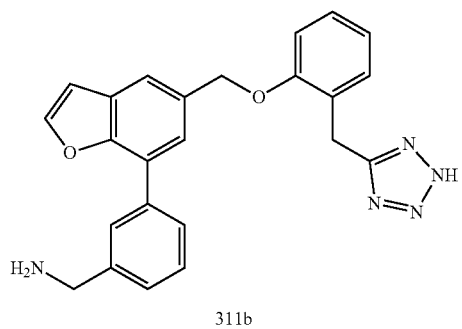

311b

Preparation of (3-(5-((2-((2H-tetrazol-5-yl)methyl)phenoxy)methyl)benzofuran-7-yl)phenyl)methanamine (311b)

Step-1: Preparation of tert-butyl 3-(5-((2-(cyanomethyl)phenoxy)methyl)benzofuran-7-yl)benzylcarbamate (311a)

Compound 311a was prepared according to the procedure reported in step-2 of scheme-23 from tert-butyl 3-(5-(hydroxymethyl)benzofuran-7-yl)benzylcarbamate (130d) (500 mg, 1.415 mmol) in DCM (15 mL) using triphenylphosphine (408 mg, 1.556 mmol), 2-(2-hydroxyphenyl)acetonitrile (188 mg, 1.415 mmol) and bis(4-chlorobenzyl) diazene-1,2-dicarboxylate (DCAD, 571 mg, 1.556 mmol) in DCM (20 mL). This gave after workup and purification by flash column chromatography [silica (40g), eluting with EtOAc in hexane from 0-50%] tert-butyl 3-(5-((2-(cyanomethyl)phenoxy)methyl)benzofuran-7-yl)benzylcarbamate (311a) (740 mg) as a clear oil; $^1$H NMR (300 MHz, DMSO-$d_6$) δ 8.09 (d, J=2.2 Hz, 1H), 7.82 (d, J=1.6 Hz, 1H), 7.79-7.73 (m, 2H), 7.67 (d, J=1.7 Hz, 1H), 7.51-7.44 (m, 2H), 7.39-7.33 (m, 2H), 7.33-7.28 (m, 1H), 7.21 (dd, J=8.3, 1.2 Hz, 1H), 7.06 (d, J=2.2 Hz, 1H), 6.98 (td, J=7.5, 1.1 Hz, 1H), 5.34 (s, 2H), 4.23 (d, J=6.2 Hz, 2H), 3.92 (s, 2H), 1.40 (s, 9H); MS (ES+) 491.2 (M+Na);

Step-2: Preparation of (3-(5-((2-((2H-tetrazol-5-yl)methyl)phenoxy)methyl)benzofuran-7-yl)phenyl)methanamine (311b)

To a solution of tert-butyl 3-(5-((2-(cyanomethyl)phenoxy)methyl)benzofuran-7-yl)benzylcarbamate (311a) (740 mg, 1.58 mmol) in DMF (15 mL) was added ammonium chloride (211 mg, 3.95 mmol), sodium azide (308 mg, 4.74 mmol) and heated at 100° C. for 6 h under nitrogen. The reaction mixture was cooled to room temperature, diluted with water (30 mL) and pH was adjusted to 5 using 2 M hydrochloric acid. The reaction mixture was extracted with EtOAc (3×) and the combined organic layers were washed with brine, dried, filtered and concentrated in vacuum to give crude of tert-butyl 3-(5-((2-((2H-tetrazol-5-yl)methyl)phenoxy)methyl)benzofuran-7-yl)benzylcarbamate. This crude material was taken in DCM (20 mL) added TFA (2.43 mL, 31.6 mmol) and stirred for 4h at RT. The reaction mixture was concentrated in vacuum and the residue obtained was purified by flash column chromatography [silica (24g), eluting with DMA80 in DCM from 0-100%] followed by purification using preparative reverse phase column chromatography [C18 steel column, eluting with ACN in water (containing 0.1% HCl) from 0-100%] to afford (3-(5-((2-((2H-tetrazol-5-yl)methyl)phenoxy)methyl)benzofuran-7-yl)phenyl)methanamine (311b) (25 mg, 4% yield) HCl salt as a white solid; $^1$H NMR (300 MHz, DMSO-$d_6$) δ 8.43 (s, 3H, D$_2$O exchangeable), 8.10 (d, J=2.2 Hz, 1H), 7.99-7.95 (m, 1H), 7.90 (dt, J=7.1, 1.9 Hz, 1H), 7.61-7.51 (m, 4H), 7.32-7.22 (m, 2H), 7.14 (dd, J=8.2, 1.2 Hz, 1H), 7.04 (d, J=2.2 Hz, 1H), 6.94 (td, J=7.4, 1.1 Hz, 1H), 5.25 (s, 2H), 4.28 (s, 2H), 4.21-4.11 (m, 2H); MS (ES+): 412.1 (M+1); (ES−): 410.1 (M−1).

Scheme-312

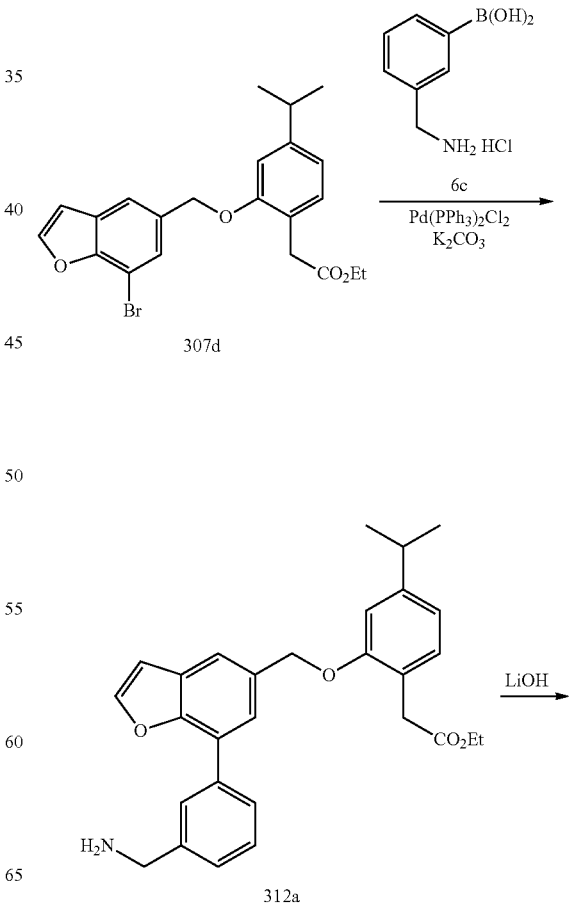

307d

312a

1033

-continued

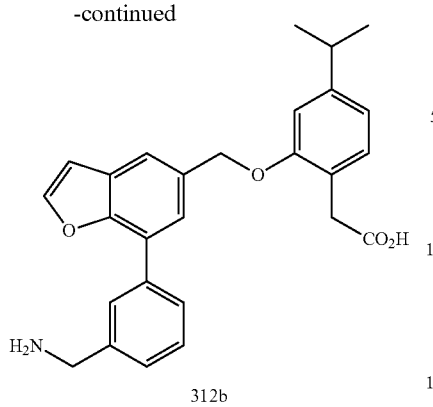

312b

Preparation of 2-(2-((7-(3-(aminomethyl)phenyl) benzofuran-5-yl)methoxy)-4-isopropylphenyl)acetic Acid (312b)

Step-1: Preparation of Ethyl 2-(2-((7-(3-(aminomethyl)phenyl)benzofuran-5-yl)methoxy)-4-isopropylphenyl)acetate (312a)

Compound 312a was prepared according to the procedure reported in step-3 of scheme-1 from ethyl 2-(2-((7-bromobenzofuran-5-yl)methoxy)-4-isopropylphenyl)acetate (307d) (150 mg, 0.348 mmol) in dioxane (4 mL) using 3-(aminomethyl)phenylboronic acid hydrochloride (6c) (98 mg, 0.522 mmol), bis(triphenylphosphine)palladium(II) chloride (Pd(PPh$_3$)$_2$Cl$_2$) (24 mg, 0.035 mmol), 2 M aqueous K$_2$CO$_3$ (0.522 mL, 1.043 mmol) under a nitrogen atmosphere heating at 100° C. for 16 h on oil bath. This gave after workup, purification by flash column chromatography (silica gel, 12 g, eluting with 0-3% MeOH in DCM) ethyl 2-(2-((7-(3-(aminomethyl)phenyl)benzofuran-5-yl)methoxy)-4-isopropylphenyl)acetate (312a) (115 mg) which was used in the next reaction without further purification; MS (ES+): 458 (M+1).

Step-2: Preparation of 2-(2-((7-(3-(aminomethyl) phenyl)benzofuran-5-yl)methoxy)-4-isopropylphenyl)acetic Acid (312b)

Compound 312b was prepared according to the procedure reported in step-6 of scheme-1 from ethyl 2-(2-((7-(3-(aminomethyl)phenyl)benzofuran-5-yl)methoxy)-4-isopropylphenyl)acetate (312a) (115 mg, from step-4 above) in MeOH (3 mL) using a 2.5 M LiOH (0.417 mL, 1.043 mmol). This gave after workup and purification by reverse phase column [C18 (100 g), eluting with ACN in water (containing 0.1% HCl) from 0-60%] 2-(2-((7-(3-(aminomethyl)phenyl) benzofuran-5-yl)methoxy)-4-isopropylphenyl)acetic acid (312b) (70 mg, 47% yield) HCl salt as a white solid. $^1$H NMR (300 MHz, DMSO-d$_6$) δ 8.11 (d, J=2.2 Hz, 1H), 8.01 (d, J=1.8 Hz, 1H), 7.94 (dt, J=7.6, 1.5 Hz, 1H), 7.78 (d, J=1.6 Hz, 1H), 7.67 (d, J=1.7 Hz, 1H), 7.60 (t, J=7.6 Hz, 1H), 7.54 (dt, J=7.8, 1.5 Hz, 1H), 7.11 (d, J=7.7 Hz, 1H), 7.08 (s, 1H), 7.00 (d, J=1.6 Hz, 1H), 6.78 (dd, J=7.7, 1.5 Hz, 1H), 5.26 (s, 2H), 4.14 (s, 2H), 3.53 (s, 2H), 2.86 (p, J=7.0 Hz, 1H), 1.21 (s, 3H), 1.19 (s, 3H); MS (ES+): 430 (M+1), (ES−): 428 (M−1).

1034

Scheme-313

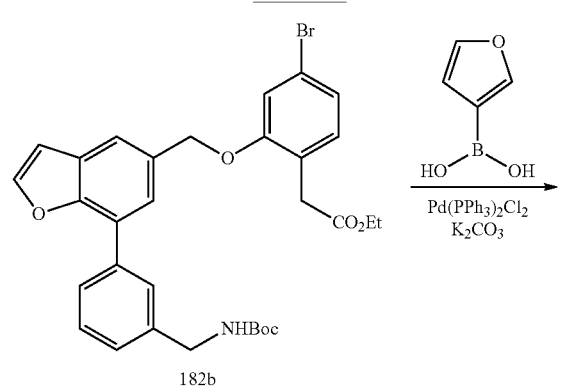

182b

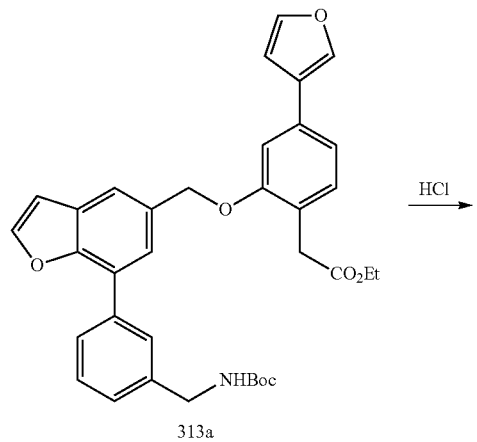

313a

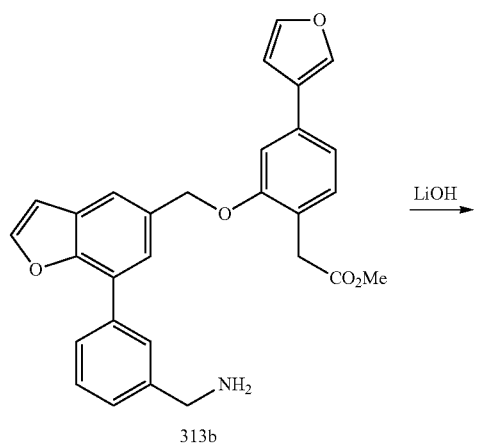

313b

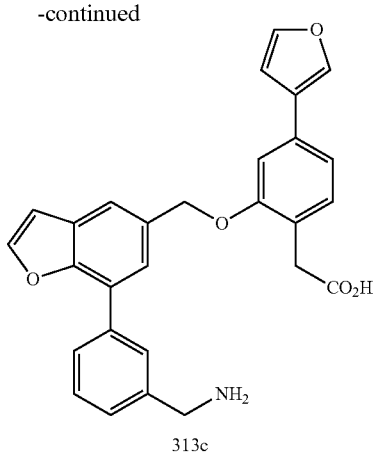

313c

Preparation of 2-(2-((7-(3-(aminomethyl)phenyl) benzofuran-5-yl)methoxy)-4-(furan-3-yl)phenyl) acetic Acid (313c)

Step-1: Preparation of Ethyl 2-(2-((7-(3-(((tert-butoxycarbonyl)amino)methyl)phenyl)benzofuran-5-yl)methoxy)-4-(furan-3-yl)phenyl)acetate (313a)

Compound 313a was prepared according to the procedure reported in step-3 of scheme-1 from ethyl 2-(4-bromo-2-((7-(3-(((tert-butoxycarbonyl)amino)methyl)phenyl)benzofuran-5-yl)methoxy)phenyl)acetate (182b) (211 mg, 0.355 mmol) in dioxane (4 mL), water (1 mL) using furan-3-ylboronic acid (59.6 mg, 0.532 mmol), Pd(PPh₃)₂Cl₂ (25 mg, 0.035 mmol) and a solution of 2 M aqueous K₂CO₃ (0.532 mL, 1.065 mmol) under a nitrogen atmosphere and heating at 100° C. for 16 h on oil bath. This gave after workup and purification by flash column chromatography (silica gel, 12 g, eluting with 0-15% ethyl acetate in hexanes) ethyl 2-(2-((7-(3-(((tert-butoxycarbonyl)amino)methyl)phenyl)benzofuran-5-yl)methoxy)-4-(furan-3-yl)phenyl)acetate (313a) (159 mg) as a clear colorless oil; MS (ES+): 604 (M+Na).

Step-2: Preparation of methyl 2-(2-((7-(3-(aminomethyl)phenyl)benzofuran-5-yl)methoxy)-4-(furan-3-yl)phenyl)acetate (313b)

Compound 313b was prepared according to the procedure reported in step-10 of scheme-257 from ethyl 2-(2-((7-(3-(((tert-butoxycarbonyl)amino)methyl)phenyl)benzofuran-5-yl)methoxy)-4-(furan-3-yl)phenyl)acetate (313a) (159 mg, from step-1) in methanol (5 mL) using HCl (4 M in 1,4-dioxane, 0.266 mL, 1.065 mmol) and stirring for 16 h at room temperature. This gave after workup a mixture methyl and ethyl 2-(2-((7-(3-(aminomethyl)phenyl)benzofuran-5-yl)methoxy)-4-(furan-3-yl)phenyl)acetate (313b) which was used as such in next step; MS (ES+) 468 (methyl) and 482 (ethyl) (M+1).

Step-3: Preparation of 2-(2-((7-(3-(aminomethyl) phenyl)benzofuran-5-yl)methoxy)-4-(furan-3-yl) phenyl)acetic Acid (313c)

Compound 313c was prepared according to the procedure reported in step-6 of scheme-1 from mixture methyl and ethyl 2-(2-((7-(3-(aminomethyl)phenyl)benzofuran-5-yl) methoxy)-4-(furan-3-yl)phenyl)acetate (313b) (from step-2 above) in MeOH (3 mL), water (1 mL) using aqueous 2.5 M LiOH (0.710 mL, 1.775 mmol) and stirring at room temperature for 16 h. This gave after workup and purification by reverse phase column [C18 (50g), eluting with ACN in water (containing 0.1% HCl) from 0-60%] 2-(2-((7-(3-(aminomethyl)phenyl)benzofuran-5-yl)methoxy)-4-(furan-3-yl)phenyl)acetic acid (313c) (45 mg, 28.0% yield) HCl salt as a white solid; ¹H NMR (300 MHz, DMSO-d₆) δ 8.21 (dd, J=1.6, 0.9 Hz, 1H), 8.11 (d, J=2.2 Hz, 1H), 8.01 (t, J=1.7 Hz, 1H), 7.94 (dt, J=7.6, 1.6 Hz, 1H), 7.80 (d, J=1.6 Hz, 1H), 7.75 (t, J=1.7 Hz, 1H), 7.69 (d, J=1.6 Hz, 1H), 7.60 (t, J=7.6 Hz, 1H), 7.54 (dt, J=7.7, 1.5 Hz, 1H), 7.36 (d, J=1.5 Hz, 1H), 7.22 (d, J=7.8 Hz, 1H), 7.16 (dd, J=7.6, 1.4 Hz, 1H), 7.08 (d, J=2.2 Hz, 1H), 6.98 (dd, J=1.9, 0.9 Hz, 1H), 5.34 (s, 2H), 4.14 (s, 2H), 3.58 (s, 2H); MS (ES+): 454 (M+1), (ES-): 452 (M-1).

Scheme-314

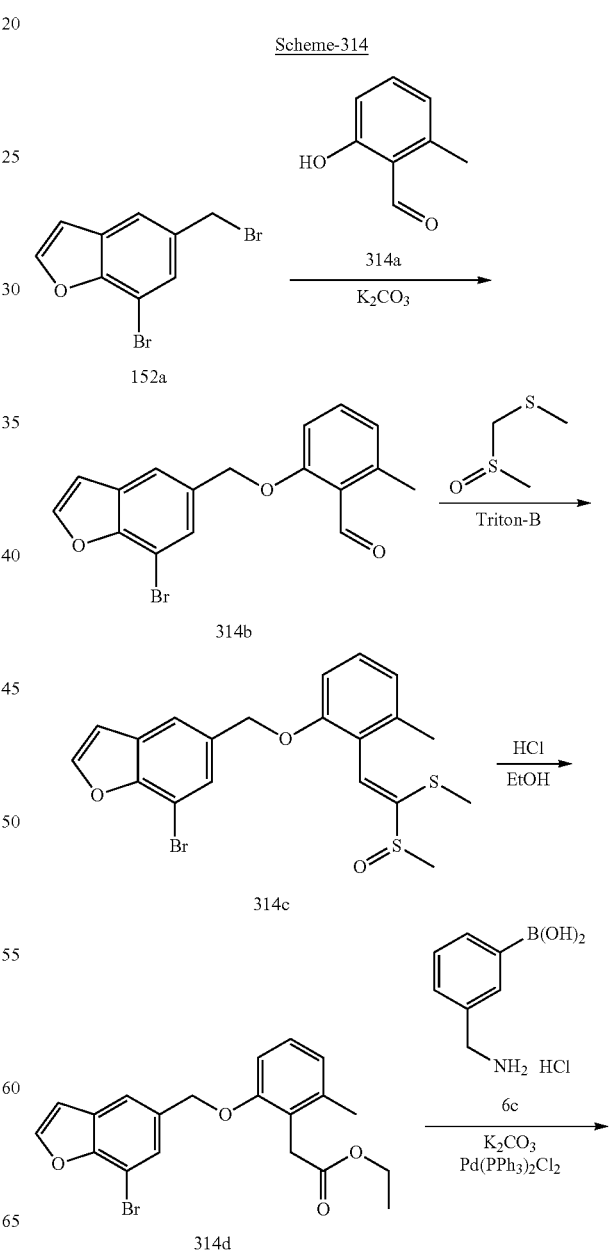

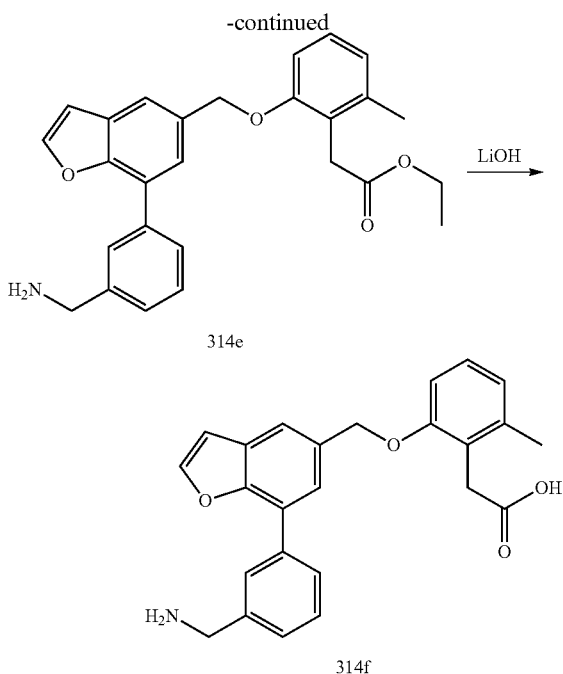

Preparation of 2-(2-((7-(3-(aminomethyl)phenyl)
benzofuran-5-yl)methoxy)-6-methylphenyl)acetic
Acid (314f)

Step-1: Preparation of 2-((7-bromobenzofuran-5-yl)
methoxy)-6-methylbenzaldehyde (314b)

Compound 314b was prepared according to the procedure reported in step-2 of scheme-152 from 7-bromo-5-(bromomethyl)benzofuran (152a) (2.13 g, 7.34 mmol) using 2-hydroxy-6-methylbenzaldehyde (314a) (1 g, 7.34 mmol), $K_2CO_3$ (3.05 g, 22.03 mmol) in DMF (10 mL) and stirring at room temperature for 12 h. This gave after workup and purification by flash column chromatography (silica gel, 40 g, eluting with EtOAc in hexane) 2-((7-bromobenzofuran-5-yl)methoxy)-6-methylbenzaldehyde (314b) (1.06 g, 42% yield) as a white solid; MS (ES+): 367.0, 369.0 (M+Na).

Step-2: Preparation of 7-bromo-5-(((3-methyl-2-(2-(methylsulfinyl)-2-(methylthio)vinyl)phenoxy)
methyl)benzofuran (314c)

Compound 314c was prepared according to the procedure reported in step-3 of scheme-266 from 2-((7-bromobenzofuran-5-yl)methoxy)-6-methylbenzaldehyde (314b) (1.0 g, 2.90 mmol) in THF (20 mL) using methyl(methylsulfinylmethyl)sulfane (0.576 g, 4.64 mmol), Triton-B (40% methanolic solution) (0.658 mL, 1.448 mmol) and heating at reflux for 12 h. This gave after workup and purification by flash column chromatography (silica gel, 40 g, eluting with EtOAc in hexane) 7-bromo-5-(((3-methyl-2-(2-(methylsulfinyl)-2-(methylthio)vinyl)phenoxy)methyl)benzofuran (314c) (579 mg, 44% yield) as a white solid; $^1$H NMR (300 MHz, DMSO-$d_6$) δ 8.13 (d, J=2.2 Hz, 1H), 7.71 (d, J=1.5 Hz, 1H), 7.61 (d, J=1.5 Hz, 1H), 7.44 (s, 1H), 7.24 (t, J=7.9 Hz, 1H), 7.09 (d, J=2.2 Hz, 1H), 6.99 (d, J=8.2 Hz, 1H), 6.89 (d, J=7.6 Hz, 1H), 5.18 (s, 2H), 3.33 (s, 3H), 2.66 (s, 3H), 2.20 (s, 3H); MS (ES+): 451.00, 452.90 (M+1).

Step-3: Preparation of Ethyl 2-(2-((7-bromobenzofuran-5-yl)methoxy)-6-methylphenyl)acetate (314d)

Compound 314d was prepared according to the procedure reported in step-4 of scheme-266 from 7-bromo-5-((3-methyl-2-(2-(methylsulfinyl)-2-(methylthio)vinyl)phenoxy)methyl)benzofuran (314c) (550 mg, 1.218 mmol) in ethanol (40 mL) using HCl (4 M in 1,4-dioxane, 1.218 mL, 4.87 mmol) and heating at reflux for 12 h. This gave after workup and purification by flash column chromatography (silica gel, eluting with ethyl acetate and hexanes) ethyl 2-(2-((7-bromobenzofuran-5-yl)methoxy)-6-methylphenyl)acetate (314d) (350 mg, 71% yield) as an oil; $^1$H NMR (300 MHz, DMSO-$d_6$) δ 8.15 (d, J=2.2 Hz, 1H), 7.72 (d, J=1.5 Hz, 1H), 7.60 (d, J=1.5 Hz, 1H), 7.17-7.09 (m, 2H), 6.93 (dd, J=8.5, 3.5 Hz, 1H), 6.84-6.79 (m, 1H), 5.17 (s, 2H), 4.03 (q, J=7.1 Hz, 2H), 3.67 (s, 2H), 2.24 (s, 3H), 1.10 (t, J=7.1 Hz, 3H).

Step-4: Preparation of Ethyl 2-(2-((7-(3-(aminomethyl)phenyl)benzofuran-5-yl)methoxy)-6-methylphenyl)acetate (314e)

Compound 314e was prepared according to the procedure reported in step-3 of scheme-1 from ethyl 2-(2-((7-bromobenzofuran-5-yl)methoxy)-6-methylphenyl)acetate (314d) (340 mg, 0.843 mmol) in dioxane (10 mL) using (3-(aminomethyl)phenyl)boronic acid hydrochloride (6c) (253 mg, 1.349 mmol), bis(triphenylphosphine)palladium (II) chloride ($Pd(PPh_3)_2Cl_2$) (89 mg, 0.126 mmol) and a solution of $K_2CO_3$ (350 mg, 2.53 mmol) in water (3 mL) under an argon atmosphere heating at 100° C. for 6 h on oil bath. This gave after workup, purification by flash column chromatography (silica gel, 40 g, eluting with DMA80 in DCM from 0-50%] ethyl 2-(2-((7-(3-(aminomethyl)phenyl)benzofuran-5-yl)methoxy)-6-methylphenyl)acetate (314e) (197 mg, 54% yield) as a colorless oil; $^1$H NMR (300 MHz, DMSO-$d_6$) δ 8.09 (d, J=2.2 Hz, 1H), 7.81 (d, J=1.7 Hz, 1H), 7.71 (dt, J=7.8, 1.6 Hz, 2H), 7.58 (d, J=1.7 Hz, 1H), 7.46 (t, J=7.5 Hz, 1H), 7.42-7.36 (m, 1H), 7.13 (t, J=7.9 Hz, 1H), 7.04 (d, J=2.2 Hz, 1H), 6.97 (d, J=8.2 Hz, 1H), 6.80 (d, J=7.5 Hz, 1H), 5.23 (s, 2H), 3.95 (q, J=7.5 Hz, 2H), 3.81 (s, 2H), 3.68 (s, 2H), 2.23 (s, 3H), 1.02 (t, J=7.1 Hz, 3H); MS (ES+): 430.2 (M+1).

Step-5: Preparation of 2-(2-((7-(3-(aminomethyl)
phenyl)benzofuran-5-yl)methoxy)-6-methylphenyl)
acetic Acid (314f)

Compound 314f was prepared according to the procedure reported in step-6 of scheme-1 from ethyl 2-(2-((7-(3-(aminomethyl)phenyl)benzofuran-5-yl)methoxy)-6-methylphenyl)acetate (314e) (190 mg, 0.442 mmol) in MeOH (5 mL), THF (5 mL) using a solution of lithium hydroxide (42 mg, 1.769 mmol) in water (2 mL). This gave after workup and purification by reverse phase column [C18 (50g), eluting with ACN in water (containing 0.1% HCl) from 0-100%] 2-(2-((7-(3-(aminomethyl)phenyl)benzofuran-5-yl)methoxy)-6-methylphenyl)acetic acid (314f) (120 mg, 68% yield) hydrochloride salt as a white solid; $^1$H NMR (300 MHz, DMSO-$d_6$) δ 8.11 (d, J=2.2 Hz, 1H), 8.00 (d, J=1.8 Hz, 1H), 7.93 (dt, J=7.5, 1.7 Hz, 1H), 7.76 (d, J=1.6 Hz, 1H), 7.64 (d, J=1.7 Hz, 1H), 7.63-7.50 (m, 2H), 7.11 (t, J=7.9 Hz, 1H), 7.06 (d, J=2.2 Hz, 1H), 6.94 (d, J=8.2 Hz, 1H), 6.80 (d, J=7.5 Hz, 1H), 5.25 (s, 2H), 4.14 (s, 2H), 3.64 (s, 2H), 2.23 (s, 3H); MS (ES+): 402.10 (M+1), (ES−): 400.10 (M−1);

Analysis calculated for $C_{25}H_{23}NO_4 \cdot HCl \cdot 0.75H_2O$: C, 66.52; H, 5.69; Cl, 7.85; N, 3.10; Found C, 66.68; H, 5.99; Cl, 7.73; N, 3.17.

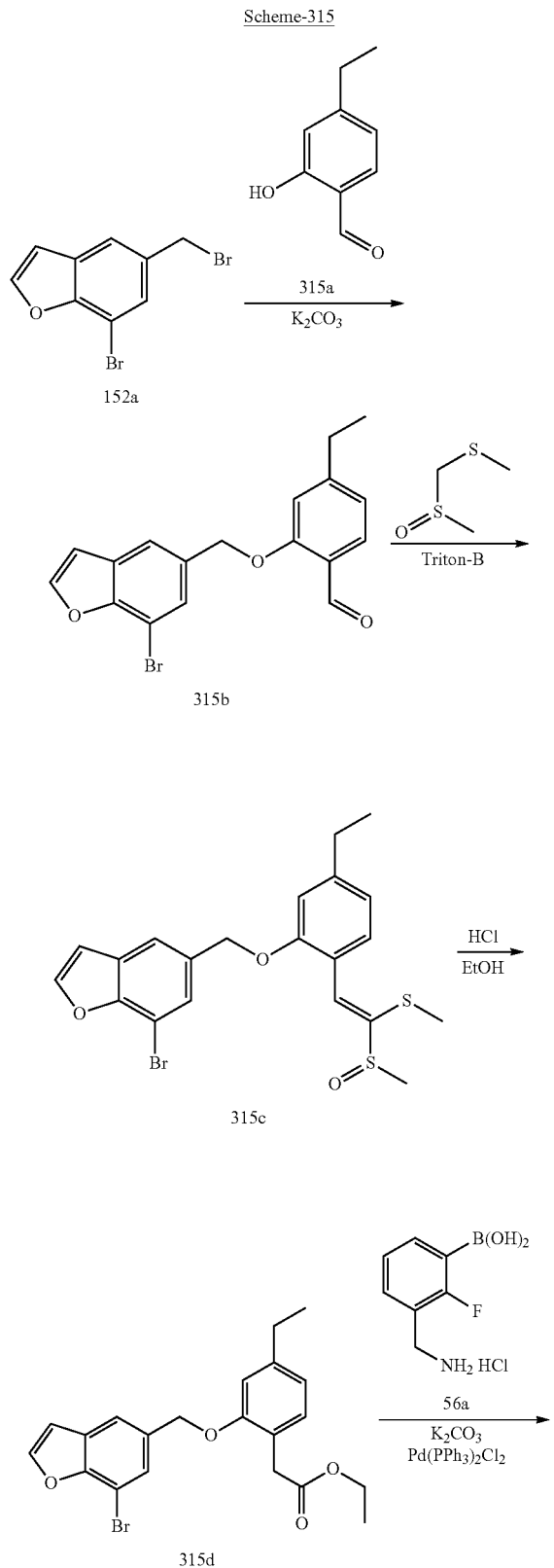

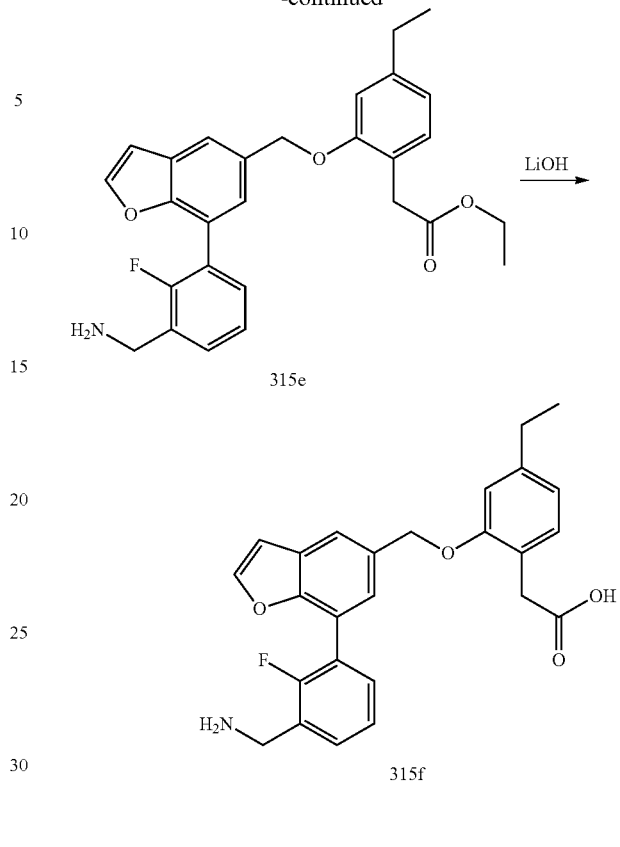

Preparation of 2-(2-((7-(3-(aminomethyl)-2-fluorophenyl)benzofuran-5-yl)methoxy)-4-ethylphenyl) acetic Acid (315f)

Step-1: Preparation of 2-((7-bromobenzofuran-5-yl)methoxy)-4-ethylbenzaldehyde (315b)

Compound 315b was prepared according to the procedure reported in step-2 of scheme-152 from 7-bromo-5-(bromomethyl)benzofuran (152a) (819 mg, 2.82 mmol) using 4-ethyl-2-hydroxybenzaldehyde (314a) (424 mg, 2.82 mmol; CAS #161876-64-8), $K_2CO_3$ (1171 mg, 8.47 mmol) in DMF (20 mL) and stirring at room temperature for 16 h. This gave after workup and purification by flash column chromatography (silica gel, 40 g, eluting with 0-7% EtOAc in hexane) 2-((7-bromobenzofuran-5-yl)methoxy)-4-ethylbenzaldehyde (315b) (615 mg, 61% yield) as a pale-yellow solid. $^1H$ NMR (300 MHz, DMSO-$d_6$) δ 10.35 (d, J=0.7 Hz, 1H), 8.15 (d, J=2.2 Hz, 1H), 7.90-7.80 (m, 1H), 7.74 (d, J=1.5 Hz, 1H), 7.64 (d, J=7.9 Hz, 1H), 7.22 (s, 1H), 7.14 (dd, J=2.2, 0.6 Hz, 1H), 6.96 (d, 1H), 5.37 (s, 2H), 2.67 (q, J=7.6 Hz, 2H), 1.20 (t, J=7.9, 7.3 Hz, 3H); MS (ES+): 381/383 (M+Na).

Step-2: Preparation of 7-bromo-5-((5-ethyl-2-(2-(methylsulfinyl)-2-(methylthio)vinyl)phenoxy) methyl)benzofuran (315c)

Compound 315c was prepared according to the procedure reported in step-3 of scheme-266 from 2-((7-bromobenzofuran-5-yl)methoxy)-4-ethylbenzaldehyde (315b) (608 mg, 1.693 mmol) in THF (20 mL) using methyl(methylsulfinylmethyl)sulfane (336 mg, 2.71 mmol), Triton-B (40% methanolic solution) (0.382 mL, 0.846 mmol) and heating at reflux for 16 h. This gave after workup 7-bromo-5-((5-ethyl-2-(2-(methyl sulfinyl)-2-(methylthio)vinyl)phenoxy)methyl)benzofuran (315c) (880 mg) as a pale-green oil; MS (ES+): 465/467 (M+1).

Step-3: Preparation of Ethyl 2-(2-((7-bromobenzofuran-5-yl)methoxy)-4-ethylphenyl)acetate (315d)

Compound 315d was prepared according to the procedure reported in step-4 of scheme-266 from 7-bromo-5-((5-ethyl-2-(2-(methyl sulfinyl)-2-(methylthio)vinyl)phenoxy)methyl)benzofuran (315c) (880 mg; from step-2 above) in ethanol (20 mL) using HCl (4 M in 1,4-dioxane, 2.116 mL, 8.46 mmol) and heating at reflux for 16 h. This gave after workup and purification by flash column chromatography (silica gel, eluting with 0-5% ethyl acetate and hexanes) ethyl 2-(2-((7-bromobenzofuran-5-yl)methoxy)-4-ethylphenyl)acetate (315d) (460 mg, 65% yield) as a yellow solid. $^1$H NMR (300 MHz, DMSO-$d_6$) δ 8.14 (d, J=2.2 Hz, 1H), 7.72 (t, J=1.1 Hz, 1H), 7.63-7.59 (m, 1H), 7.15-7.07 (m, 2H), 6.97-6.93 (m, 1H), 6.76 (dt, J=7.5, 1.0 Hz, 1H), 5.17 (s, 2H), 4.00 (q, J=7.1, 0.7 Hz, 2H), 3.57 (s, 2H), 2.59 (q, J=7.6 Hz, 2H), 1.18 (t, 3H), 1.07 (t, J=7.1, 0.7 Hz, 3H); MS (ES+): 417/419 (M+1).

Step-4: Preparation of Ethyl 2-(2-((7-(3-(aminomethyl)-2-fluorophenyl)benzofuran-5-yl)methoxy)-4-ethylphenyl)acetate (315e)

Compound 315e was prepared according to the procedure reported in step-3 of scheme-1 from ethyl 2-(2-((7-bromobenzofuran-5-yl)methoxy)-4-ethylphenyl)acetate (315d) (257 mg, 0.616 mmol) in dioxane (4 mL) and water (1 mL) using (3-(aminomethyl)-2-fluorophenyl)boronic acid hydrochloride (56a) (190 mg, 0.924 mmol), bis(triphenylphosphine)palladium(II) chloride (Pd(PPh$_3$)$_2$Cl$_2$) (43 mg, 0.062 mmol) and 3.3 M aqueous K$_2$CO$_3$ (0.560 mL, 1.848 mmol) under a nitrogen atmosphere heating at 100° C. for 16 h on oil bath. This gave after workup, purification by flash column chromatography (silica gel, 12 g, eluting with methanol in DCM from 0-3%] ethyl 2-(2-((7-(3-(aminomethyl)-2-fluorophenyl)benzofuran-5-yl)methoxy)-4-ethylphenyl)acetate (315e) (159 mg) as a colorless oil; MS (ES+): 462 (M+1).

Step-5: Preparation of 2-(2-((7-(3-(aminomethyl)-2-fluorophenyl)benzofuran-5-yl)methoxy)-4-ethylphenyl)acetic Acid (315f)

Compound 315f was prepared according to the procedure reported in step-6 of scheme-1 from ethyl 2-(2-((7-(3-(aminomethyl)-2-fluorophenyl)benzofuran-5-yl)methoxy)-4-ethylphenyl)acetate (315e) (159 mg, from step-4 above) in MeOH (3 mL), using aqueous 2.5 M LiOH (0.985 mL, 2.463 mmol). This gave after workup and purification by reverse phase column [C18 (50g), eluting with ACN in water (containing 0.1% HCl) from 0-60%] 2-(2-((7-(3-(aminomethyl)-2-fluorophenyl)benzofuran-5-yl)methoxy)-4-ethylphenyl)acetic acid (315f) (113 mg, 42% yield) HCl salt as a white solid; $^1$H NMR (300 MHz, DMSO-$d_6$) δ 8.04 (d, J=2.2 Hz, 1H), 7.83 (d, J=1.6 Hz, 1H), 7.73-7.60 (m, 2H), 7.44 (dd, J=13.9, 6.3 Hz, 2H), 7.17-7.02 (m, 2H), 6.97 (d, J=1.6 Hz, 1H), 6.82-6.71 (m, 1H), 5.24 (s, 2H), 4.18 (s, 2H), 3.53 (s, 2H), 2.59 (q, 2H), 1.18 (t, J=7.6 Hz, 3H); MS (ES+): 434 (M+1), (ES−): 432 (M−1); Analysis calculated for C$_{26}$H$_{24}$FNO$_4$.HCl.0.5H$_2$O: C, 65.20; H, 5.47; Cl, 7.40; N, 2.92; Found: C, 65.21; H, 5.43; Cl, 7.18; N, 2.91.

Scheme-316

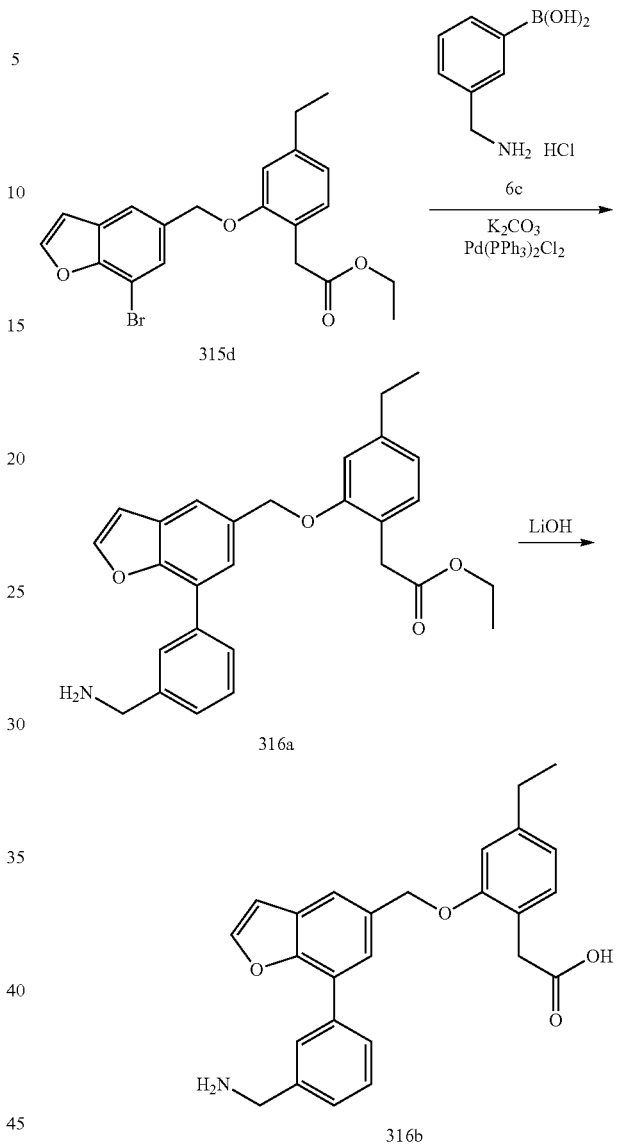

Preparation of 2-(2-((7-(3-(aminomethyl)phenyl)benzofuran-5-yl)methoxy)-4-ethylphenyl)acetic Acid (316b)

Step-1: Preparation of Ethyl 2-(2-((7-(3-(aminomethyl)phenyl)benzofuran-5-yl)methoxy)-4-ethylphenyl)acetate (316a)

Compound 316a was prepared according to the procedure reported in step-3 of scheme-1 from ethyl 2-(2-((7-bromobenzofuran-5-yl)methoxy)-4-ethylphenyl)acetate (315d) (200 mg, 0.479 mmol) in dioxane (4 mL) and water (1 mL) using (3-(aminomethyl)phenyl)boronic acid hydrochloride (6c) (117 mg, 0.623 mmol), bis(triphenylphosphine)palladium(II) chloride (Pd(PPh$_3$)$_2$Cl$_2$) (34 mg, 0.048 mmol) and 2 M aqueous K$_2$CO$_3$ (0.719 mL, 1.438 mmol) under a nitrogen atmosphere heating at 100° C. for 16 h on oil bath. This gave after workup, purification by flash column chromatography (silica gel, 12 g, eluting with methanol in DCM from 0-5%] ethyl 2-(2-((7-(3-(aminomethyl)phenyl)benzofuran-5-yl)methoxy)-4-ethylphenyl)acetate (316a) (165 mg) as a clear colorless oil; MS (ES+): 444 (M+1).

Step-2: Preparation of 2-(2-((7-(3-(aminomethyl) phenyl)benzofuran-5-yl)methoxy)-4-ethylphenyl) acetic Acid (316b)

Compound 316b was prepared according to the procedure reported in step-6 of scheme-1 from ethyl 2-(2-((7-(3-(aminomethyl)phenyl)benzofuran-5-yl)methoxy)-4-ethylphenyl)acetate (316a) (165 mg, from step-1 above) in MeOH (3 mL), using aqueous 2.5 M LiOH (0.767 mL, 1.917 mmol). This gave after workup and purification by reverse phase column [C18 (50g), eluting with ACN in water (containing 0.1% HCl) from 0-60%] 2-(2-((7-(3-(aminomethyl)phenyl)benzofuran-5-yl)methoxy)-4-ethylphenyl)acetic acid (316b) (120 mg, 60% yield) HCl salt as a white solid; $^1$H NMR (300 MHz, DMSO-$d_6$) δ 8.10 (d, J=2.2 Hz, 1H), 8.02 (t, J=1.7 Hz, 1H), 7.94 (dt, J=7.5, 1.6 Hz, 1H), 7.76 (dd, J=5.6, 1.6 Hz, 1H), 7.66 (dd, J=5.7, 1.7 Hz, 1H), 7.63-7.51 (m, 2H), 7.14-7.03 (m, 2H), 6.98 (s, 1H), 6.75 (dd, J=7.6, 1.5 Hz, 1H), 5.24 (s, 2H), 4.13 (s, 2H), 3.55 (s, 2H), 2.60 (t, J=7.6 Hz, 2H), 1.30-1.13 (m, 3H); MS (ES+): 416 (M+1), 414 (M−1); Analysis calculated for $C_{26}H_{25}NO_4 \cdot HCl \cdot 0.75H_2O$: C, 67.09; H, 5.96; Cl, 7.62; N, 3.01; Found: C, 67.20; H, 5.92; Cl, 7.58; N, 3.03.

Scheme-317

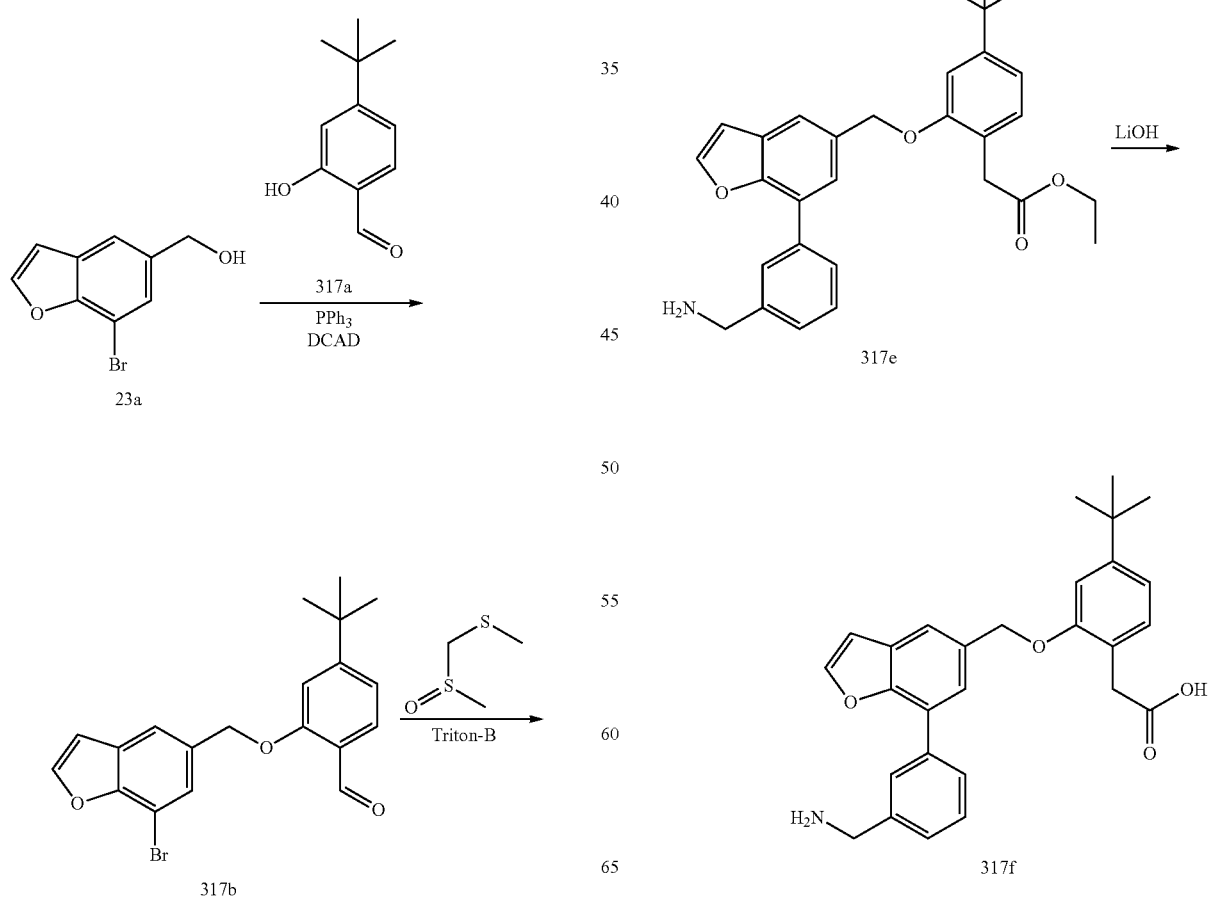

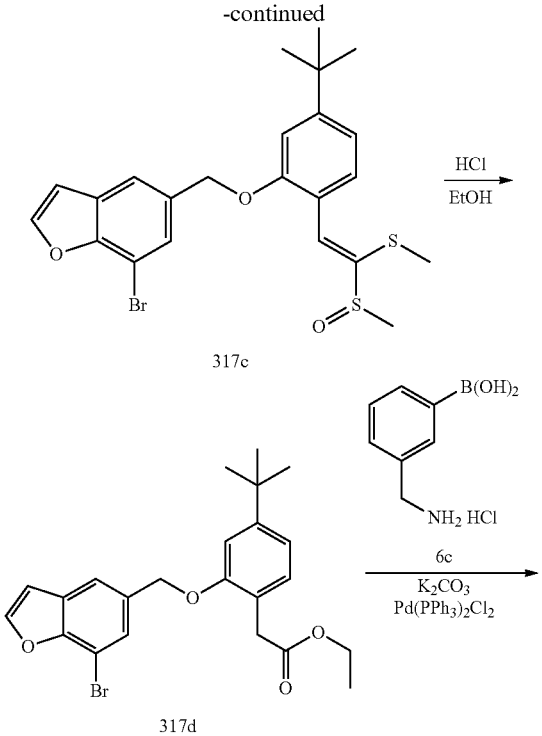

1045

Preparation of 2-(2-((7-(3-(aminomethyl)phenyl) benzofuran-5-yl)methoxy)-4-(tert-butyl)phenyl)acetic Acid (317f)

Step-1: Preparation of 2-((7-bromobenzofuran-5-yl)methoxy)-4-(tert-butyl)benzaldehyde (317b)

Compound 317b was prepared according to the procedure reported in step-2 of scheme-23 from (7-bromobenzofuran-5-yl)methanol (23a) (1.09 g, 4.80 mmol) in DCM (20 mL) using triphenylphosphine (1.637 g, 6.24 mmol), 4-(tert-butyl)-2-hydroxybenzaldehyde (317a) (0.898 g, 5.04 mmol; CAS #66232-34-6) and (E)-bis(4-chlorobenzyl) diazene-1,2-dicarboxylate (DCAD, 2.292 g, 6.24 mmol) in DCM (15 mL). This gave after workup and purification by flash column chromatography (silica gel eluting with EtOAc in hexane from 0-5%) 2-((7-bromobenzofuran-5-yl)methoxy)-4-(tert-butyl)benzaldehyde (317b) (554 mg, 30% yield) as an oil; $^1$H NMR (300 MHz, DMSO-$d_6$) δ 10.36 (d, J=0.8 Hz, 1H), 8.14 (d, J=2.2 Hz, 1H), 7.86 (d, J=1.5 Hz, 1H), 7.76 (d, J=1.5 Hz, 1H), 7.65 (d, J=8.2 Hz, 1H), 7.30 (d, J=1.7 Hz, 1H), 7.19-7.08 (m, 2H), 5.42 (s, 2H), 1.30 (s, 9H); MS (ES+): 409/411 (M+Na).

Step-2: Preparation of 7-bromo-5-((5-(tert-butyl)-2-(2-(methylsulfinyl)-2-(methylthio)vinyl)phenoxy)methyl)benzofuran (317c)

Compound 317c was prepared according to the procedure reported in step-3 of scheme-266 from 2-((7-bromobenzofuran-5-yl)methoxy)-4-(tert-butyl)benzaldehyde (317b) (554 mg, 1.431 mmol) in THF (20 mL) using methyl (methylsulfinylmethyl)sulfane (284 mg, 2.289 mmol), Triton-B (40% methanolic solution) (0.323 mL, 0.715 mmol) and heating at reflux for 16 h. This gave after workup 7-bromo-5-((5-(tert-butyl)-2-(2-(methylsulfinyl)-2-(methylthio)vinyl)phenoxy)methyl)benzofuran (317c) as a pale-green oil, which was used in the next step without further purification; MS (ES+) 493/495 (M+1).

Step-3: Preparation of Ethyl 2-(2-((7-bromobenzofuran-5-yl)methoxy)-4-(tert-butyl)phenyl)acetate (317d)

Compound 317d was prepared according to the procedure reported in step-4 of scheme-266 from 7-bromo-5-((5-(tert-butyl)-2-(2-(methylsulfinyl)-2-(methylthio)vinyl)phenoxy)methyl)benzofuran (317c) (crude from step-2 above) in ethanol (20 mL) using HCl (4 M in 1,4-dioxane, 1.431 mL, 5.72 mmol) and heating at reflux for 16 h. This gave after workup and purification by flash column chromatography (silica gel, 24 g, eluting with 0-5% ethyl acetate and hexanes) ethyl 2-(2-((7-bromobenzofuran-5-yl)methoxy)-4-(tert-butyl)phenyl)acetate (317d) (440 mg, 69% yield) as a yellow oil; $^1$H NMR (300 MHz, DMSO-$d_6$) δ 8.14 (d, J=2.2 Hz, 1H), 7.74 (d, J=1.5 Hz, 1H), 7.63 (d, J=1.5 Hz, 1H), 7.19-7.05 (m, 3H), 6.92 (dd, J=7.8, 1.8 Hz, 1H), 5.20 (s, 2H), 4.02 (dd, J=7.9, 6.4 Hz, 2H), 3.56 (s, 2H), 1.27 (s, 9H), 1.08 (td, J=7.2, 1.3 Hz, 3H); MS (ES+) 445/447(M+1).

Step-4: Preparation of Ethyl 2-(2-((7-(3-(aminomethyl)phenyl)benzofuran-5-yl)methoxy)-4-(tert-butyl)phenyl)acetate (317e)

Compound 317e was prepared according to the procedure reported in step-3 of scheme-1 from ethyl 2-(2-((7-bromobenzofuran-5-yl)methoxy)-4-(tert-butyl)phenyl)acetate (317d) (166 mg, 0.373 mmol) in dioxane (4 mL) and water (1 mL) using (3-(aminomethyl)phenyl)boronic acid hydrochloride (6c) (91 mg, 0.485 mmol), bis(triphenylphosphine) palladium(II) chloride (Pd(PPh$_3$)$_2$Cl$_2$) (26 mg, 0.037 mmol) and 2 M aqueous K$_2$CO$_3$ (0.559 mL, 1.118 mmol) under an nitrogen atmosphere heating at 100° C. for 16 h on oil bath. This gave after workup, purification by flash column chromatography (silica gel, 12 g, eluting with methanol in DCM from 0-5%] ethyl 2-(2-((7-(3-(aminomethyl)phenyl)benzofuran-5-yl)methoxy)-4-(tert-butyl)phenyl)acetate (317e) (124 mg) as a clear colorless oil; MS (ES+): 472 (M+1).

Step-5: Preparation of 2-(2-((7-(3-(aminomethyl)phenyl)benzofuran-5-yl)methoxy)-4-(tert-butyl)phenyl)acetic Acid (317f)

Compound 317f was prepared according to the procedure reported in step-6 of scheme-1 from ethyl 2-(2-((7-(3-(aminomethyl)phenyl)benzofuran-5-yl)methoxy)-4-(tert-butyl)phenyl)acetate (317e) (from step-4 above) in MeOH (3 mL), using aqueous 2.5 M LiOH (0.596 mL, 1.491 mmol). This gave after workup and purification by reverse phase column [C18 (100 g), eluting with ACN in water (containing 0.1% HCl) from 0-60%] 2-(2-((7-(3-(aminomethyl)phenyl)benzofuran-5-yl)methoxy)-4-(tert-butyl)phenyl)acetic acid (317f) (80 mg, 48% yield) HCl salt as a white solid; $^1$H NMR (300 MHz, DMSO-$d_6$) δ 8.10 (d, J=2.2 Hz, 1H), 8.02 (d, J=1.9 Hz, 1H), 7.93 (dt, J=7.0, 2.0 Hz, 1H), 7.79 (d, J=1.6 Hz, 1H), 7.68 (d, J=1.7 Hz, 1H), 7.65-7.51 (m, 2H), 7.15-7.09 (m, 2H), 7.07 (d, J=2.2 Hz, 1H), 6.91 (dd, J=7.8, 1.7 Hz, 1H), 5.28 (s, 2H), 4.13 (s, 2H), 3.54 (s, 2H), 1.27 (s, 9H); MS (ES+): 444 (M+1), 442 (M−1); Analysis calculated for C$_{28}$H$_{29}$NO$_4$.HCl.H$_2$O: C, 67.53; H, 6.48; Cl, 7.12; N, 2.81; Found: C, 67.55; H, 6.43; Cl, 6.97; N, 2.89.

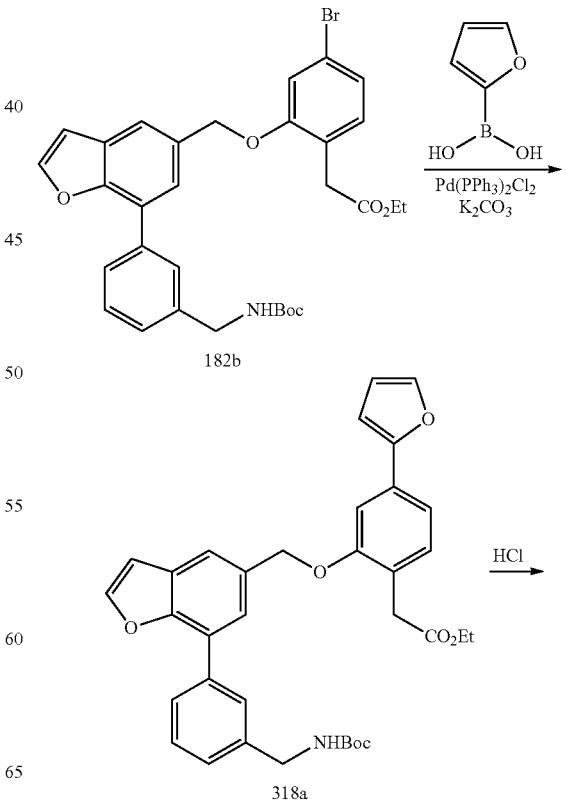

Scheme-318

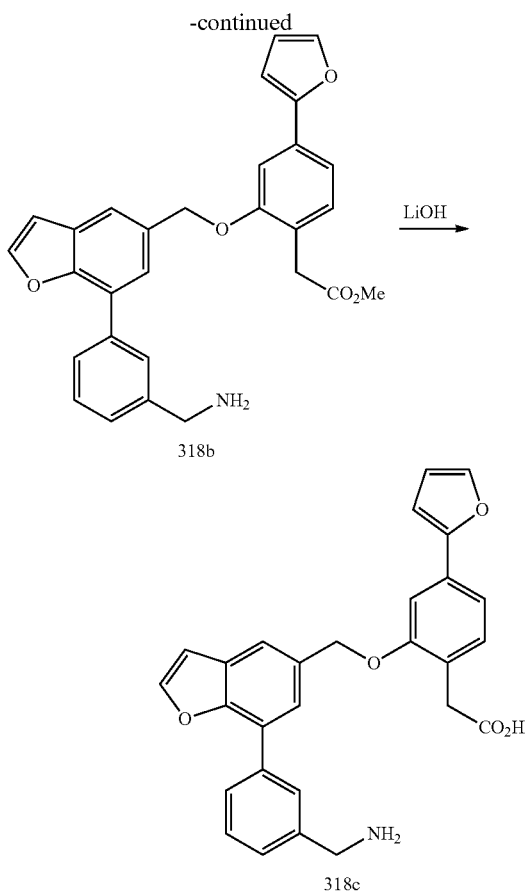

318b

318c

Preparation of 2-(2-((7-(3-(aminomethyl)phenyl)
benzofuran-5-yl)methoxy)-4-(furan-2-yl)phenyl)
acetic Acid (318c)

Step-1: Preparation of Ethyl 2-(2-((7-(3-(((tert-butoxycarbonyl)amino)methyl)phenyl)benzofuran-5-yl)methoxy)-4-(furan-2-yl)phenyl)acetate (318a)

Compound 318a was prepared according to the procedure reported in step-3 of scheme-1 from ethyl 2-(4-bromo-2-((7-(3-(((tert-butoxycarbonyl)amino)methyl)phenyl)benzofuran-5-yl)methoxy)phenyl)acetate (182b) (304 mg, 0.511 mmol) in dioxane (4 mL), water (1 mL) using furan-2-ylboronic acid (86 mg, 0.767 mmol), Pd(PPh$_3$)$_2$Cl$_2$ (36 mg, 0.051 mmol) and a solution of 2 M aqueous K$_2$CO$_3$ (0.767 mL, 1.534 mmol) under a nitrogen atmosphere and heating at 100° C. for 16 h on oil bath. This gave after workup and purification by flash column chromatography (silica gel 12 g, eluting with 0-20% ethyl acetate in hexanes) ethyl 2-(2-((7-(3-(((tert-butoxycarbonyl)amino)methyl)phenyl)benzofuran-5-yl)methoxy)-4-(furan-2-yl)phenyl)acetate (318a) (230 mg) as a clear colorless oil; MS (ES+): 604 (M+Na).

Step-2: Preparation of methyl 2-(2-((7-(3-(aminomethyl)phenyl)benzofuran-5-yl)methoxy)-4-(furan-2-yl)phenyl)acetate (318b)

Compound 318b was prepared according to the procedure reported in step-10 of scheme-257 from ethyl 2-(2-((7-(3-(((tert-butoxycarbonyl)amino)methyl)phenyl)benzofuran-5-yl)methoxy)-4-(furan-2-yl)phenyl)acetate (318a) (230 mg, from step-1) in methanol (5 mL) using HCl (4 M in 1,4-dioxane, 0.767 mL, 3.07 mmol) and stirring for 16 h at room temperature. This gave after workup a mixture methyl and ethyl esters of 2-(2-((7-(3-(aminomethyl)phenyl)benzofuran-5-yl)methoxy)-4-(furan-2-yl)phenyl)acetate (318b) which was used as such in next step; MS (ES+): 468 (methyl) and 482 (ethyl) (M+1).

Step-3: Preparation of 2-(2-((7-(3-(aminomethyl)phenyl)benzofuran-5-yl)methoxy)-4-(furan-2-yl)phenyl)acetic Acid (318c)

Compound 318c was prepared according to the procedure reported in step-6 of scheme-1 from mixture methyl and ethyl 2-(2-((7-(3-(aminomethyl)phenyl)benzofuran-5-yl)methoxy)-4-(furan-2-yl)phenyl)acetate (318b) (from step-2 above) in MeOH (3 mL), water (1 mL) using aqueous 2.5 M LiOH (1.023 mL, 2.56 mmol) and stirring at room temperature for 16 h. This gave after workup and purification by reverse phase column [C18 (50g), eluting with ACN in water (containing 0.1% HCl) from 0-60%] 2-(2-((7-(3-(aminomethyl)phenyl)benzofuran-5-yl)methoxy)-4-(furan-2-yl)phenyl)acetic acid (318c) (107 mg, 46% yield) HCl salt as a white solid; $^1$H NMR (300 MHz, DMSO-d$_6$) δ 8.11 (d, J=2.2 Hz, 1H), 8.01 (d, J=1.7 Hz, 1H), 7.94 (dt, J=7.4, 1.5 Hz, 1H), 7.80 (d, J=1.6 Hz, 1H), 7.74 (dd, J=1.8, 0.7 Hz, 1H), 7.69 (d, J=1.7 Hz, 1H), 7.60 (t, J=7.6 Hz, 1H), 7.54 (dt, J=7.8, 1.5 Hz, 1H), 7.42 (s, 1H), 7.27 (d, J=0.8 Hz, 2H), 7.08 (d, J=2.2 Hz, 1H), 6.96 (dd, J=3.4, 0.8 Hz, 1H), 6.60 (dd, J=3.4, 1.8 Hz, 1H), 5.36 (s, 2H), 4.14 (s, 2H), 3.60 (s, 2H); MS (ES+): 454 (M+1), 452 (M−1); Analysis calculated for C$_{28}$H$_{23}$NO$_5$.HCl.H$_2$O: C, 66.21; H, 5.16; Cl, 6.98; N, 2.76; Found: C, 66.50; H, 5.00; Cl, 6.57; N, 2.69.

Scheme-319

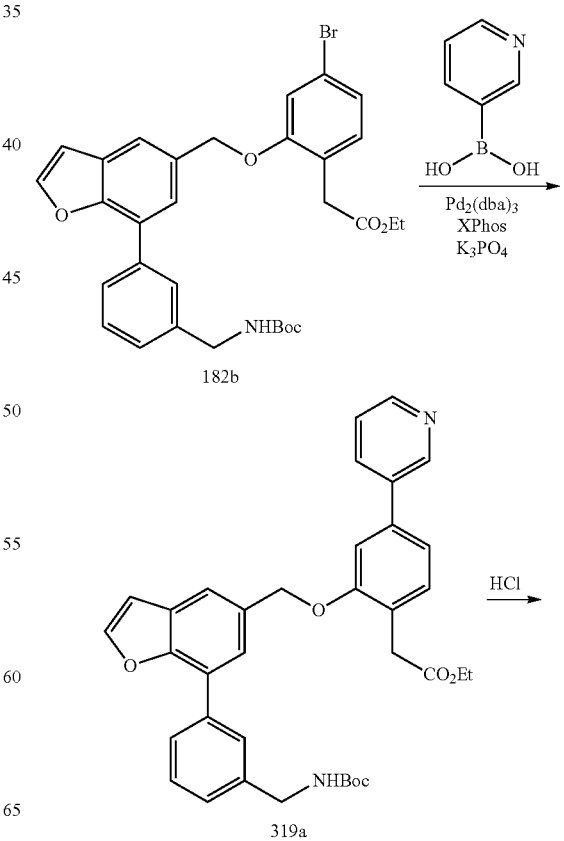

182b

319a

1049

-continued

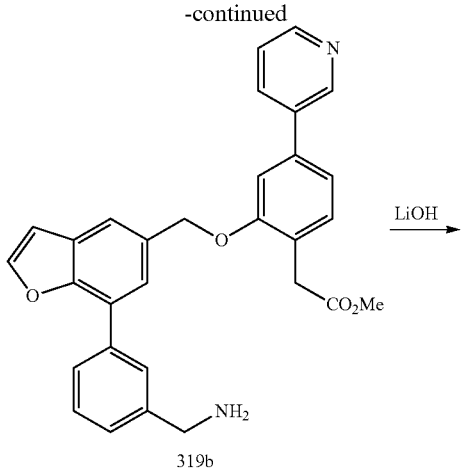

319b

LiOH →

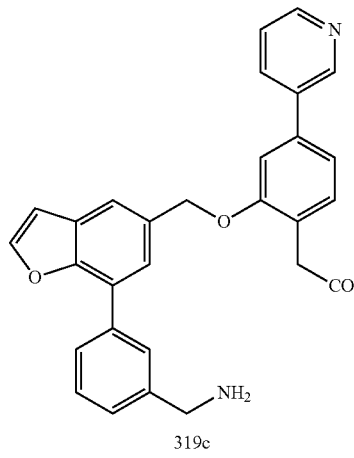

319c

Preparation of 2-(2-((7-(3-(aminomethyl)phenyl)
benzofuran-5-yl)methoxy)-4-(pyridin-3-yl)phenyl)
acetic Acid (319c)

Step-1: Preparation of Ethyl 2-(2-((7-(3-(((tert-butoxycarbonyl)amino)methyl)phenyl)benzofuran-5-yl)methoxy)-4-(pyridin-3-yl)phenyl)acetate (319a)

A solution of ethyl 2-(4-bromo-2-((7-(3-(((tert-butoxycarbonyl)amino)methyl)phenyl)benzofuran-5-yl)methoxy)phenyl)acetate (182b) (240 mg, 0.404 mmol), pyridin-3-ylboronic acid (74.4 mg, 0.606 mmol), Pd$_2$(dba)$_3$ (37.0 mg, 0.040 mmol), XPhos (38.5 mg, 0.081 mmol), and 1.27 M aqueous K$_3$PO$_4$ (0.636 mL, 0.807 mmol) in n-BuOH (4 mL) in a scintillation vial was heated at 100° C. under nitrogen for 16 h. The resulting deep red mixture was filtered and solid was washed with EtOAc (50 mL). The filtrate was concentrated in vacuum dryness to remove n-BuOH. The residue was taken in EtOAc (50 mL) washed with H$_2$O (2×25 mL), brine (25 mL), dried, filtered and concentrated in vacuum. The residue obtained was purified by flash column chromatography (silica gel, 24 g, eluting with 0-40% EtOAc in hexane) to afford ethyl 2-(2-((7-(3-(((tert-butoxycarbonyl)amino)methyl)phenyl)benzofuran-5-yl)methoxy)-4-(pyridin-3-yl)phenyl)acetate (319a) (90 mg) as a pale-yellow oil; MS (ES+): 593 (M+1).

Step-2: Preparation of methyl 2-(2-((7-(3-(aminomethyl)phenyl)benzofuran-5-yl)methoxy)-4-(pyridin-3-yl)phenyl)acetate (319b)

Compound 319b was prepared according to the procedure reported in step-10 of scheme-257 from ethyl 2-(2-((7-(3-(((tert-butoxycarbonyl)amino)methyl)phenyl)benzofuran-5-yl)methoxy)-4-(pyridin-3-yl)phenyl)acetate (319a) (90 mg, from step-1) in methanol (5 mL) using HCl (4 M in 1,4-dioxane, 0.505 mL, 2.019 mmol) and stirring at 40° C. for 1 h. This gave after workup a mixture methyl and ethyl esters of 2-(2-((7-(3-(aminomethyl)phenyl)benzofuran-5-yl)methoxy)-4-(pyridin-3-yl)phenyl)acetate (319b); MS (ES+): 479 (methyl, M+1), 493 (ethyl, M+1).

Step-3: Preparation of 2-(2-((7-(3-(aminomethyl)phenyl)benzofuran-5-yl)methoxy)-4-(pyridin-3-yl)phenyl)acetic Acid (319c)

Compound 319c was prepared according to the procedure reported in step-6 of scheme-1 from mixture methyl and ethyl esters of 2-(2-((7-(3-(aminomethyl)phenyl)benzofuran-5-yl)methoxy)-4-(pyridin-3-yl)phenyl)acetate (319b) (from step-2 above) in MeOH (3 mL), using aqueous 2.5 M LiOH (0.646 mL, 1.615 mmol) and stirring at room temperature for 16 h. This gave after workup and purification by reverse phase column [C18 (100 g), eluting with ACN in water (containing 0.1% HCl) from 0-60%] 2-(2-((7-(3-(aminomethyl)phenyl)benzofuran-5-yl)methoxy)-4-(pyridin-3-yl)phenyl)acetic acid (319c) (55 mg, 29% yield) HCl salt as a white solid; $^1$H NMR (300 MHz, DMSO-d$_6$) δ 9.13 (d, J=2.1 Hz, 1H), 8.74 (d, J=5.2 Hz, 1H), 8.51 (d, 1H), 8.38 (s, 3H), 8.11 (d, J=2.2 Hz, 1H), 8.01 (s, 1H), 7.93 (dd, J=7.7, 1.9 Hz, 1H), 7.87-7.76 (m, 2H), 7.70 (d, J=1.6 Hz, 1H), 7.66-7.52 (m, 3H), 7.45-7.35 (m, 2H), 7.08 (d, J=2.2 Hz, 1H), 5.43 (s, 2H), 4.15 (q, J=5.9 Hz, 2H), 3.67 (s, 2H); MS (ES+): 465 (M+1); Analysis calculated for C$_{29}$H$_{24}$N$_2$O$_4$.2HCl.3.75H$_2$O: C, 57.57; H, 5.58; Cl, 11.72; N, 4.63; Found: C, 57.68; H, 5.33; Cl, 11.01; N, 4.72.

Scheme-320

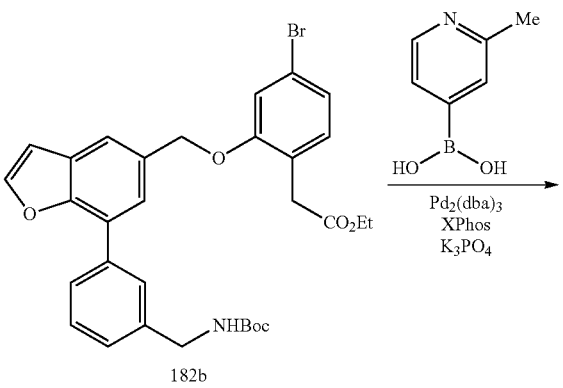

182b

-continued

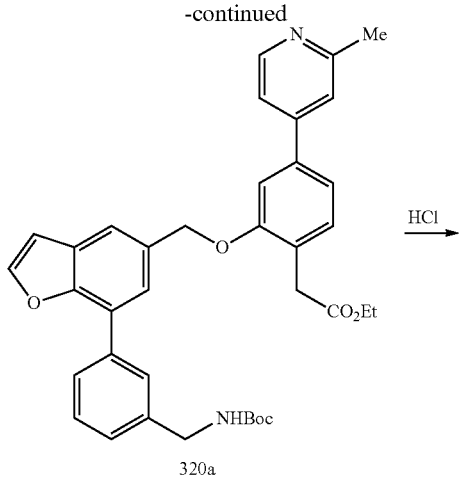
320a

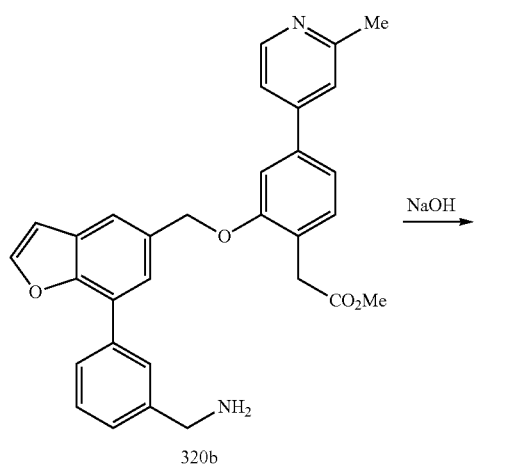
320b

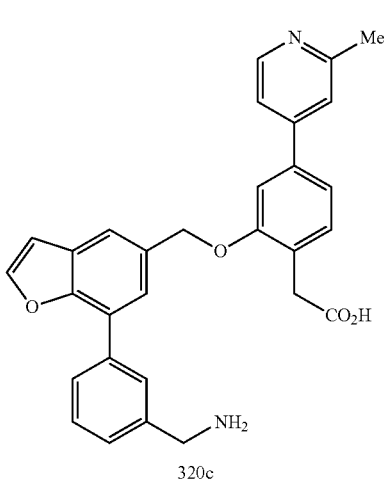
320c

Preparation of 2-(2-((7-(3-(aminomethyl)phenyl) benzofuran-5-yl)methoxy)-4-(2-methylpyridin-4-yl) phenyl)acetic Acid (320c)

Step-1: Preparation of Ethyl 2-(2-((7-(3-(((tert-butoxycarbonyl)amino)methyl)phenyl)benzofuran-5-yl)methoxy)-4-(2-methylpyridin-4-yl)phenyl)acetate (320a)

Compound 320a was prepared according to the procedure reported in step-1 of scheme-319 from ethyl 2-(4-bromo-2-((7-(3-(((tert-butoxycarbonyl)amino)methyl)phenyl)benzofuran-5-yl)methoxy)phenyl)acetate (182b) (290 mg, 0.488 mmol) using (2-methylpyridin-4-yl)boronic acid (100 mg, 0.732 mmol), $Pd_2(dba)_3$ (45 mg, 0.049 mmol), XPhos (47 mg, 0.098 mmol), and 1.27 M aqueous $K_3PO_4$ (0.768 mL, 0.976 mmol) in n-BuOH (4 mL) in a scintillation vial and heating at 100° C. under nitrogen for 16 h. This gave after workup and purification by flash column chromatography (silica gel, 24 g, eluting with 0-60% EtOAc in hexane) ethyl 2-(2-((7-(3-(((tert-butoxycarbonyl)amino)methyl)phenyl) benzofuran-5-yl)methoxy)-4-(2-methylpyridin-4-yl)phenyl) acetate (320a) (126 mg) as a pale-yellow oil; MS (ES+): 607 (M+1).

Step-2: Preparation of methyl 2-(2-((7-(3-(aminomethyl)phenyl)benzofuran-5-yl)methoxy)-4-(2-methylpyridin-4-yl)phenyl)acetate (320b)

Compound 320b was prepared according to the procedure reported in step-10 of scheme-257 from ethyl 2-(2-((7-(3-(((tert-butoxycarbonyl)amino)methyl)phenyl)benzofuran-5-yl)methoxy)-4-(2-methylpyridin-4-yl)phenyl)acetate (320a) (126 mg, from step-1) in methanol (5 mL) using HCl (4 M in 1,4-dioxane, 0.610 mL, 2.439 mmol) and stirring at 40° C. for 1 h. This gave after workup a mixture methyl and ethyl esters of 2-(2-((7-(3-(aminomethyl)phenyl)benzofuran-5-yl)methoxy)-4-(2-methylpyridin-4-yl)phenyl)acetate (320b); MS (ES+): 493 (methyl, M+1), 507 (ethyl, M+1).

Step-3: Preparation of 2-(2-((7-(3-(aminomethyl) phenyl)benzofuran-5-yl)methoxy)-4-(2-methylpyridin-4-yl)phenyl)acetic Acid (320c)

Compound 320c was prepared according to the procedure reported in step-4 of scheme-4 from mixture of methyl and ethyl esters of 2-(2-((7-(3-(aminomethyl)phenyl)benzofuran-5-yl)methoxy)-4-(2-methylpyridin-4-yl)phenyl)acetate (320b) (from step-2 above) in MeOH (3 mL) and water (1 mL), using NaOH (58.5 mg, 1.463 mmol) and stirring at room temperature for 16 h. This gave after workup and purification by reverse phase column [C18 (100 g), eluting with ACN in water (containing 0.1% HCl) from 0-60%] 2-(2-((7-(3-(aminomethyl)phenyl)benzofuran-5-yl) methoxy)-4-(2-methylpyridin-4-yl)phenyl)acetic acid (320c) (90 mg, 39% yield) HCl salt as a white solid; $^1$H NMR (300 MHz, DMSO-$d_6$) δ 8.80 (d, J=6.3 Hz, 1H), 8.74-8.48 (m, 3H), 8.36 (s, 1H), 8.31-8.20 (m, 1H), 8.12 (d, J=2.2 Hz, 1H), 8.05 (s, 1H), 7.94 (t, J=4.7 Hz, 1H), 7.87-7.70 (m, 3H), 7.69-7.55 (m, 3H), 7.48 (d, J=7.9 Hz, 1H), 7.08 (d, J=2.2 Hz, 1H), 5.46 (s, 2H), 4.14 (p, J=6.4 Hz, 2H), 3.72 (s, 2H), 2.79 (s, 3H); MS (ES+): 479 (M+1); Analysis calculated for $C_{30}H_{26}N_2O_4 \cdot 2HCl \cdot 3H_2O$: C, 59.51; H, 5.66; Cl, 11.71; N, 4.63; Found: C, 59.25; H, 5.73; Cl, 11.94; N, 4.66.

Scheme-321
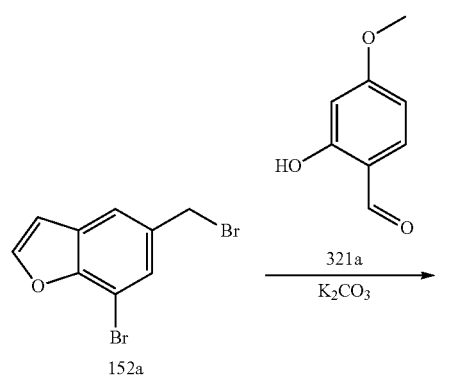
152a
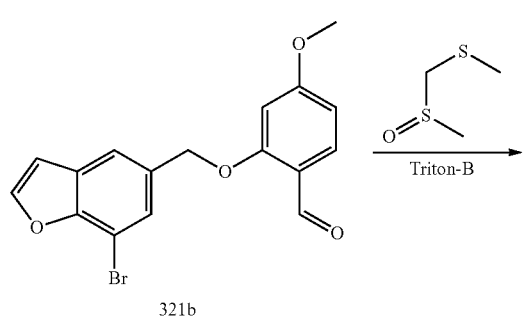
321b
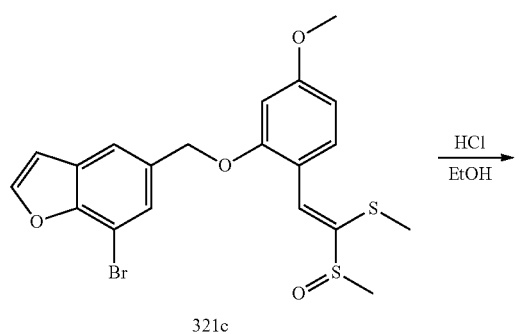
321c
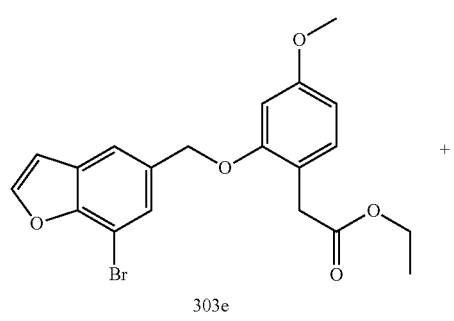
303e
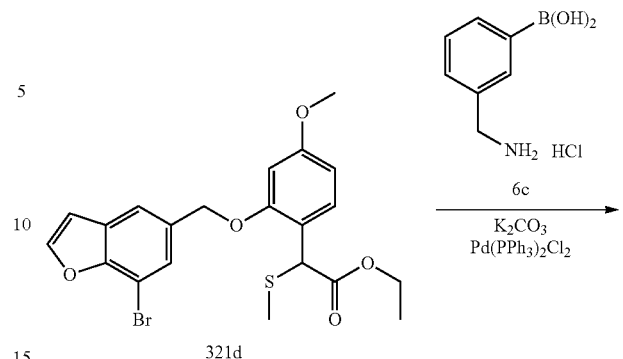
321d
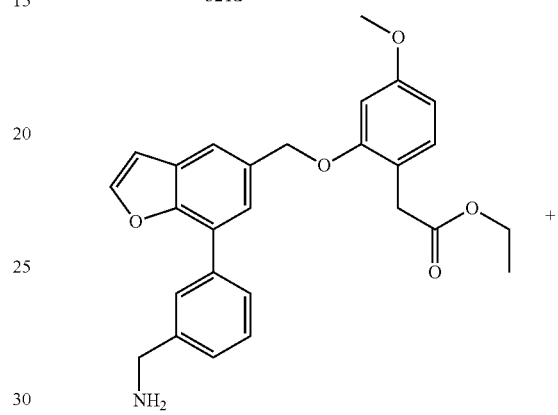
303f
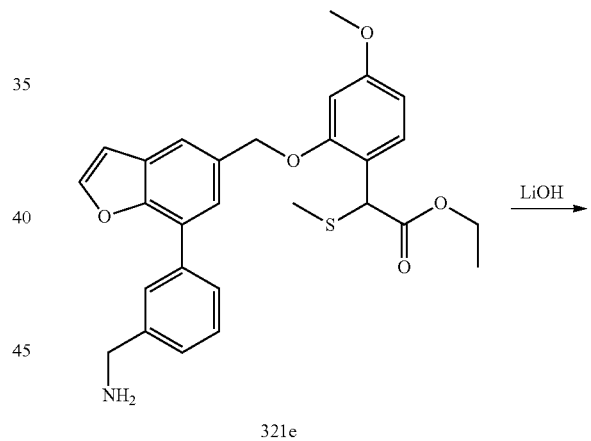
321e
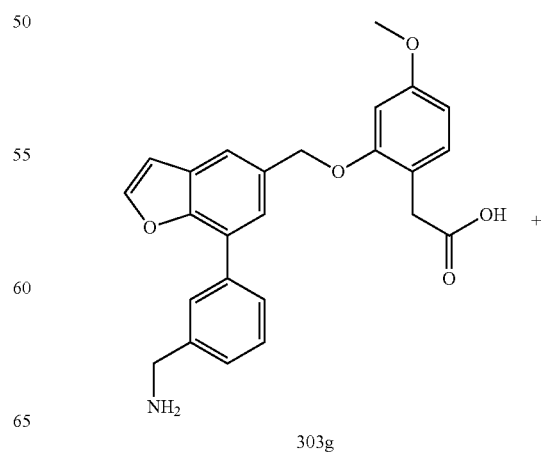
303g

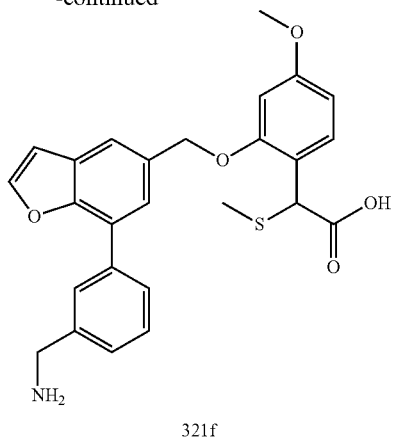

321f

Preparation of 2-(2-((7-(3-(aminomethyl)phenyl) benzofuran-5-yl)methoxy)-4-methoxyphenyl)-2-(methylthio)acetic Acid (321f)

Step-1: Preparation of 2-((7-bromobenzofuran-5-yl)methoxy)-4-methoxybenzaldehyde (321b)

Compound 321b was prepared according to the procedure reported in step-2 of scheme-152 from 7-bromo-5-(bromomethyl)benzofuran (152a) (1.5 g, 5.17 mmol) using 2-hydroxy-4-methoxybenzaldehyde (321a) (0.866 g, 5.69 mmol), $K_2CO_3$ (2.145 g, 15.52 mmol) in DMF (15 mL) and stirring at room temperature overnight. This gave after workup 2-((7-bromobenzofuran-5-yl)methoxy)-4-methoxybenzaldehyde (321b) (1.739 g, 93% yield) as white solid; $^1$H NMR (300 MHz, DMSO-$d_6$) δ 10.24 (d, J=0.8 Hz, 1H), 8.15 (d, J=2.2 Hz, 1H), 7.84 (d, J=1.5 Hz, 1H), 7.73 (d, J=1.5 Hz, 1H), 7.69 (d, J=8.7 Hz, 1H), 7.13 (d, J=2.2 Hz, 1H), 6.83 (d, J=2.3 Hz, 1H), 6.68 (ddd, J=8.7, 2.3, 0.8 Hz, 1H), 5.37 (s, 2H), 3.86 (s, 3H).

Step-2: Preparation of 7-bromo-5-((5-methoxy-2-(2-(methylsulfinyl)-2-(methylthio)vinyl)phenoxy) methyl)benzofuran (321c)

Compound 321c was prepared according to the procedure reported in step-3 of scheme-266 from 2-((7-bromobenzofuran-5-yl)methoxy)-4-methoxybenzaldehyde (321b) (1.73 g, 4.79 mmol) in THF (25 mL) using methyl(methylsulfinylmethyl)sulfane (1.19 g, 9.58 mmol), Triton-B (40% methanolic solution) (1.088 mL, 2.395 mmol) and heating at reflux for 10 h. This gave after workup and purification by flash column chromatography (silica gel, 40 g, eluting with ethyl acetate in hexanes) 7-bromo-5-((5-methoxy-2-(2-(methylsulfinyl)-2-(methylthio)vinyl)phenoxy)methyl)benzofuran (321c) (1.92 g, 86% yield) as an oil; $^1$H NMR (300 MHz, DMSO-$d_6$) δ 8.15 (d, J=0.8 Hz, 1H), 8.14-8.10 (m, 1H), 7.81 (s, 1H), 7.76 (d, J=1.5 Hz, 1H), 7.65 (d, J=1.5 Hz, 1H), 7.10 (d, J=2.2 Hz, 1H), 6.77 (d, J=2.4 Hz, 1H), 6.67 (dd, J=8.7, 2.4 Hz, 1H), 5.30 (s, 2H), 3.80 (s, 3H), 2.68 (s, 3H), 2.27 (s, 3H).

Step-3: Preparation of Ethyl 2-(2-((7-bromobenzofuran-5-yl)methoxy)-4-methoxyphenyl)acetate (303e) and ethyl 2-(2-((7-bromobenzofuran-5-yl)methoxy)-4-methoxyphenyl)-2-(methylthio)acetate (321d)

Compound 303e and 321d were prepared according to the procedure reported in step-4 of scheme-266 from 7-bromo-5-((5-methoxy-2-(2-(methylsulfinyl)-2-(methylthio)vinyl) phenoxy)methyl)benzofuran (321c) (1.9 g, 4.07 mmol) in ethanol (50 mL) using HCl (4 M in 1,4-dioxane, 4.07 mL, 16.26 mmol) and heating at reflux for 10 h. This gave after workup and purification by flash column chromatography (silica gel, 40 g, eluting with ethyl acetate in hexanes) ethyl 2-(2-((7-bromobenzofuran-5-yl)methoxy)-4-methoxyphenyl)acetate (303e) and ethyl 2-(2-((7-bromobenzofuran-5-yl)methoxy)-4-methoxyphenyl)-2-(methylthio)acetate (321d) (1.002 g, 59% yield) as an inseparable mixture which was taken as such to next step.

Step-4: Preparation of Ethyl 2-(2-((7-(3-(aminomethyl)phenyl)benzofuran-5-yl)methoxy)-4-methoxyphenyl)acetate (303f) and ethyl 2-(2-((7-(3-(aminomethyl)phenyl)benzofuran-5-yl)methoxy)-4-methoxyphenyl)-2-(methylthio)acetate (321e)

Compound 303f and 321e was prepared according to the procedure reported in step-3 of scheme-1 from mixtures of ethyl 2-(2-((7-bromobenzofuran-5-yl)methoxy)-4-methoxyphenyl)acetate (303e) and ethyl 2-(2-((7-bromobenzofuran-5-yl)methoxy)-4-methoxyphenyl)-2-(methylthio)acetate (321d) obtained from step-3 above (1.00 g, 2.385 mmol) in dioxane (15 mL) and water (1 mL) using (3-(aminomethyl) phenyl)boronic acid hydrochloride (6c) (0.671 g, 3.58 mmol), bis(triphenylphosphine)palladium(II) chloride (Pd (PPh$_3$)$_2$Cl$_2$) (0.251 g, 0.358 mmol) and $K_2CO_3$ (0.989 g, 7.16 mmol) in water (3 mL) under a nitrogen atmosphere heating at 100° C. for 11 h on oil bath. This gave after workup, purification by flash column chromatography (silica gel, eluting with DMA80 in DCM from 0-50%) an inseparable mixture of ethyl 2-(2-((7-(3-(aminomethyl)phenyl) benzofuran-5-yl)methoxy)-4-methoxyphenyl)acetate (303f) and ethyl 2-(2-((7-(3-(aminomethyl)phenyl)benzofuran-5-yl)methoxy)-4-methoxyphenyl)-2-(methylthio)acetate (321e) (800 mg, 75% yield) a brown oil; MS (ES+): 492.1 (M+1), (ES−): 490.1 (M−1).

Step-5: Preparation of 2-(2-((7-(3-(aminomethyl) phenyl)benzofuran-5-yl)methoxy)-4-methoxyphenyl)-2-(methylthio)acetic Acid (321f)

Compound 321f was prepared according to the procedure reported in step-6 of scheme-1 from mixture containing ethyl 2-(2-((7-(3-(aminomethyl)phenyl)benzofuran-5-yl) methoxy)-4-methoxyphenyl)acetate (303f) and ethyl 2-(2-((7-(3-(aminomethyl)phenyl)benzofuran-5-yl)methoxy)-4-methoxyphenyl)-2-(methylthio)acetate (321e) (883 mg, 1.796 mmol; from step-4 above) in MeOH (10 mL) THF (10 mL) water (4 mL), using lithium hydroxide monohydrate (129 mg, 5.39 mmol). This gave after workup and purification by reverse phase column [C18 (250 g), eluting with ACN in water (containing 0.1% HCl) from 0-100%] 2-(2-((7-(3-(aminomethyl)phenyl)benzofuran-5-yl)methoxy)-4-methoxyphenyl)acetic acid (303g) (50 mg, 0.120 mmol, 7% yield) and 2-(2-((7-(3-(aminomethyl)phenyl)benzofuran-5-yl)methoxy)-4-methoxyphenyl)-2-(methylthio)acetic acid (321f) (190 mg, 23% yield) hydrochloride salt as a white solid; $^1$H NMR (300 MHz, DMSO-$d_6$) δ 12.72 (s, 1H), 8.32 (s, 3H), 8.11 (d, J=2.2 Hz, 1H), 8.00 (s, 1H), 7.97-7.90 (m, 1H), 7.79 (d, J=1.6 Hz, 1H), 7.69 (d, J=1.6 Hz, 1H), 7.60 (t, J=7.6 Hz, 1H), 7.54 (d, J=7.7 Hz, 1H), 7.34 (d, J=8.5 Hz, 1H), 7.09 (d, J=2.2 Hz, 1H), 6.72 (d, J=2.4 Hz, 1H), 6.56 (dd, J=8.5, 2.4 Hz, 1H), 5.31 (s, 2H), 4.85 (s, 1H), 4.14 (s, 2H), 3.74 (s, 3H), 2.00 (s, 3H); MS (ES+): 464.20 (M+1), (ES−): 462.10 (M−1); analysis Calculated for $C_{26}H_{25}NO_5 \cdot HCl \cdot 1.5H_2O$: C, 59.25; H, 5.55; Cl, 6.73; N, 2.66; Found: C, 59.38; H, 5.18; Cl, 7.06; N, 2.76.

Scheme-322

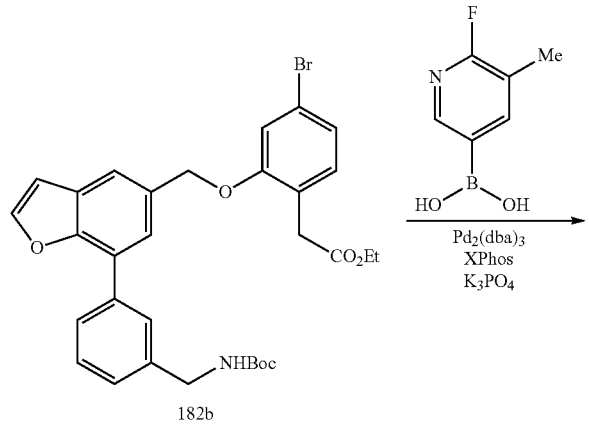

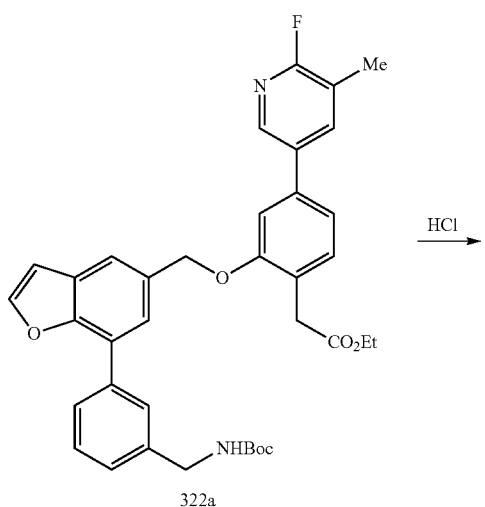

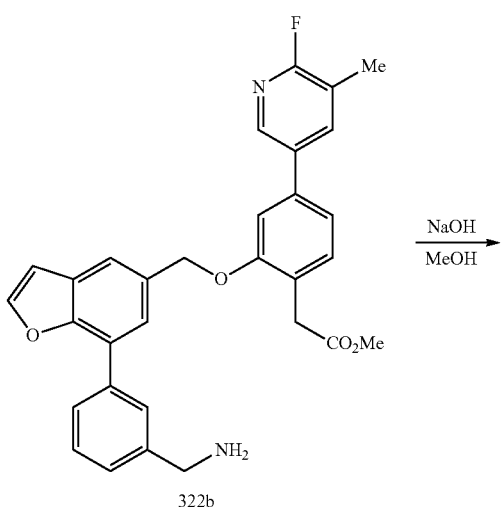

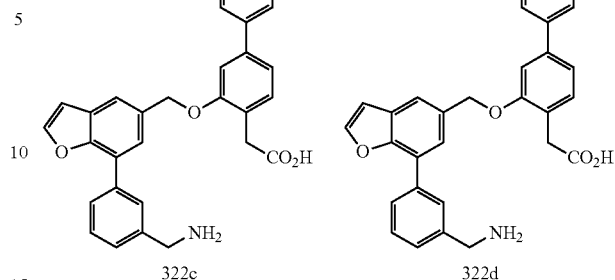

Preparation of 2-(2-((7-(3-(aminomethyl)phenyl) benzofuran-5-yl)methoxy)-4-(6-fluoro-5-methylpyridin-3-yl)phenyl)acetic Acid (322c) and 2-(2-((7-(3-(aminomethyl)phenyl)benzofuran-5-yl)methoxy)-4-(6-methoxy-5-methylpyridin-3-yl)phenyl)acetic Acid (322d)

Step-1: Preparation of Ethyl 2-(2-((7-(3-(((tert-butoxycarbonyl)amino)methyl)phenyl)benzofuran-5-yl)methoxy)-4-(6-fluoro-5-methylpyridin-3-yl)phenyl)acetate (322a)

Compound 322a was prepared according to the procedure reported in step-1 of scheme-319 from ethyl 2-(4-bromo-2-((7-(3-(((tert-butoxycarbonyl)amino)methyl)phenyl)benzofuran-5-yl)methoxy)phenyl)acetate (182b) (290 mg, 0.488 mmol) using 6-fluoro-5-methylpyridin-3-ylboronic acid (113 mg, 0.732 mmol), $Pd_2(dba)_3$ (45 mg, 0.049 mmol), XPhos (47 mg, 0.098 mmol), and 1.27 M aqueous $K_3PO_4$ (0.768 mL, 0.976 mmol) in n-BuOH (4 mL) in a scintillation vial and heating at 100° C. under nitrogen for 16 h. This gave after workup and purification by flash column chromatography (silica gel, 24 g, eluting with 0-20% EtOAc in hexane) ethyl 2-(2-((7-(3-(((tert-butoxycarbonyl)amino)methyl)phenyl)benzofuran-5-yl)methoxy)-4-(6-fluoro-5-methylpyridin-3-yl)phenyl)acetate (322a) (159 mg) as a pale-yellow oil; $^1H$ NMR (300 MHz, DMSO-$d_6$) δ 8.40 (t, J=1.6 Hz, 1H), 8.19 (ddd, J=9.6, 2.6, 0.9 Hz, 1H), 8.09 (d, J=2.2 Hz, 1H), 7.73 (dt, J=7.0, 2.0 Hz, 3H), 7.59 (d, J=1.7 Hz, 1H), 7.54-7.42 (m, 3H), 7.37-7.28 (m, 2H), 7.26 (dd, J=7.7, 1.6 Hz, 1H), 7.07 (d, J=2.2 Hz, 1H), 5.37 (s, 2H), 4.23 (d, J=6.2 Hz, 2H), 3.92 (q, J=7.1 Hz, 2H), 3.67 (s, 2H), 2.31 (s, 3H), 1.39 (s, 9H), 0.97 (t, J=7.1 Hz, 3H).

Step-2: Preparation of methyl 2-(2-((7-(3-(aminomethyl)phenyl)benzofuran-5-yl)methoxy)-4-(6-fluoro-5-methylpyridin-3-yl)phenyl)acetate (322b)

Compound 322b was prepared according to the procedure reported in step-10 of scheme-257 from ethyl 2-(2-((7-(3-(((tert-butoxycarbonyl)amino)methyl)phenyl)benzofuran-5-yl)methoxy)-4-(6-fluoro-5-methylpyridin-3-yl)phenyl)acetate (322a) (159 mg, from step-1) in methanol (5 mL) using HCl (4 M in 1,4-dioxane, 0.610 mL, 2.439 mmol) and stirring at 40° C. for 1 h. This gave after workup a mixture methyl and ethyl esters of 2-(2-((7-(3-(aminomethyl)phenyl)benzofuran-5-yl)methoxy)-4-(6-fluoro-5-methylpyridin-3-yl)phenyl)acetate (322b); MS (ES+): 511 (methyl, M+1), 525 (ethyl, M+1).

Step-3: Preparation of 2-(2-((7-(3-(aminomethyl)phenyl)benzofuran-5-yl)methoxy)-4-(6-fluoro-5-methylpyridin-3-yl)phenyl)acetic Acid (322c) and 2-(2-((7-(3-(aminomethyl)phenyl)benzofuran-5-yl)methoxy)-4-(6-methoxy-5-methylpyridin-3-yl)phenyl)acetic Acid (322d)

Compound 322c and 322d were prepared according to the procedure reported in step-4 of scheme-4 from mixture of methyl and ethyl esters of 2-(2-((7-(3-(aminomethyl)phenyl)benzofuran-5-yl)methoxy)-4-(6-fluoro-5-methylpyridin-3-yl)phenyl)acetate (322b) (from step-2 above) in MeOH (3 mL) and water (1 mL), using NaOH (58.5 mg, 1.463 mmol) and stirring at room temperature for 16 h. This gave after workup and purification by reverse phase column [C18 (100 g), eluting with ACN in water (containing 0.1% HCl) from 0-60%] 2-(2-((7-(3-(aminomethyl)phenyl)benzofuran-5-yl)methoxy)-4-(6-fluoro-5-methylpyridin-3-yl)phenyl)acetic acid (322c) (55 mg, 23% yield) HCl salt as a white solid; $^1$H NMR (300 MHz, DMSO-$d_6$) δ 8.70-8.42 (m, 3H), 8.39 (d, J=2.5 Hz, 1H), 8.19 (dd, J=9.6, 2.5 Hz, 1H), 8.11 (d, J=2.2 Hz, 1H), 8.03 (s, 1H), 7.94 (dt, J=5.5, 2.4 Hz, 1H), 7.85-7.75 (m, 1H), 7.75-7.68 (m, 1H), 7.59 (d, J=5.2 Hz, 2H), 7.51-7.41 (m, 1H), 7.34 (d, J=7.8 Hz, 1H), 7.26 (dd, J=7.6, 1.5 Hz, 1H), 7.08 (d, J=2.3 Hz, 1H), 5.41 (s, 2H), 4.14 (q, J=5.8 Hz, 2H), 3.65 (s, 2H), 2.32 (s, 3H). $^{19}$F NMR (300 MHz, DMSO-$d_6$) δ −75.59; MS (ES+): 497 (M+1), (ES−): 495 (M−1) and 2-(2-((7-(3-(aminomethyl)phenyl)benzofuran-5-yl)methoxy)-4-(6-methoxy-5-methylpyridin-3-yl)phenyl)acetic acid (322d) (16 mg, 7% yield) HCl salt as a white solid; $^1$H NMR (300 MHz, DMSO-$d_6$) δ 8.51 (s, 3H), 8.33 (d, J=2.4 Hz, 1H), 8.11 (d, J=2.2 Hz, 1H), 8.02 (s, 1H), 7.93 (dt, J=5.7, 2.3 Hz, 1H), 7.88 (d, J=2.4 Hz, 1H), 7.80 (d, J=1.6 Hz, 1H), 7.70 (dd, J=5.6, 1.6 Hz, 1H), 7.65-7.55 (m, 2H), 7.38 (d, J=1.7 Hz, 1H), 7.30 (d, J=7.7 Hz, 1H), 7.24-7.17 (m, 1H), 7.08 (d, J=2.2 Hz, 1H), 5.38 (d, J=8.2 Hz, 2H), 4.17-4.11 (m, 2H), 3.92 (s, 3H), 3.63 (s, 2H), 2.21 (s, 3H); MS (ES+): 509 (M+1), (ES−): 507 (M−1).

Scheme-323

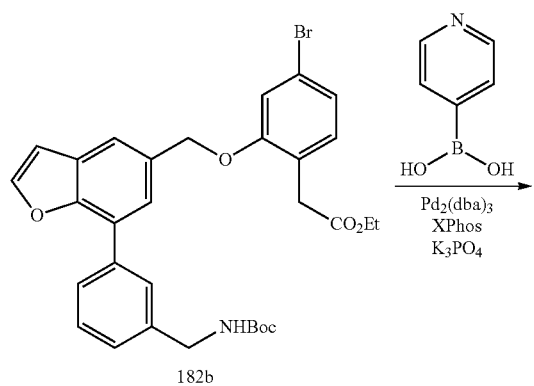

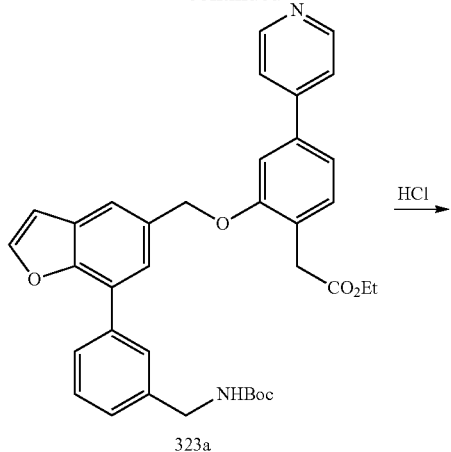

323a

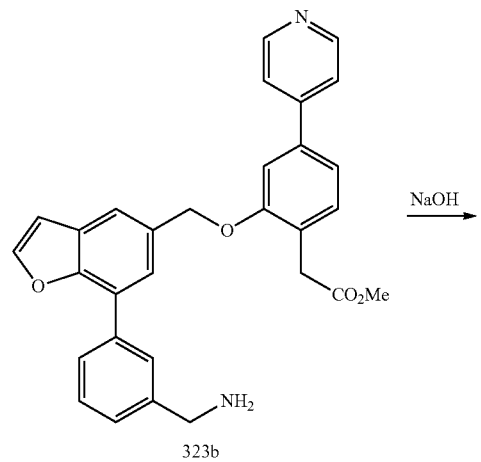

323b

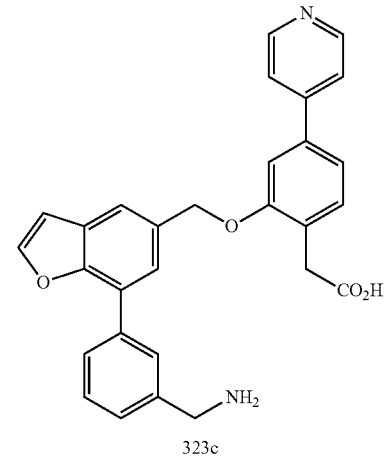

323c

Preparation of 2-(2-((7-(3-(aminomethyl)phenyl)benzofuran-5-yl)methoxy)-4-(pyridin-4-yl)phenyl)acetic Acid (323c)

Step-1: Preparation of Ethyl 2-(2-((7-(3-(((tert-butoxycarbonyl)amino)methyl)phenyl)benzofuran-5-yl)methoxy)-4-(pyridin-4-yl)phenyl)acetate (323a)

Compound 323a was prepared according to the procedure reported in step-1 of scheme-319 from ethyl 2-(4-bromo-2-((7-(3-(((tert-butoxycarbonyl)amino)methyl)phenyl)benzofuran-5-yl)methoxy)phenyl)acetate (182b) (323 mg, 0.543 mmol) using pyridin-4-ylboronic acid (100 mg, 0.815 mmol), $Pd_2(dba)_3$ (50 mg, 0.054 mmol), XPhos (52 mg, 0.109 mmol), and 1.27 M aqueous $K_3PO_4$ (0.856 mL, 1.087 mmol) in n-BuOH (4 mL) in a scintillation vial and heating at 100° C. under nitrogen for 16 h. This gave after workup and purification by flash column chromatography (silica gel, 24 g, eluting with 0-60% EtOAc in hexane) ethyl 2-(2-((7-(3-(((tert-butoxycarbonyl)amino)methyl)phenyl)benzofuran-5-yl)methoxy)-4-(pyridin-4-yl)phenyl)acetate (323a) (137 mg) as a pale-yellow oil; MS (ES+): 593 (M+1).

Step-2: Preparation of methyl 2-(2-((7-(3-(aminomethyl)phenyl)benzofuran-5-yl)methoxy)-4-(pyridin-4-yl)phenyl)acetate (323b)

Compound 323b was prepared according to the procedure reported in step-10 of scheme-257 from ethyl 2-(2-((7-(3-(((tert-butoxycarbonyl)amino)methyl)phenyl)benzofuran-5-yl)methoxy)-4-(pyridin-4-yl)phenyl)acetate (323a) (137 mg, from step-1) in methanol (5 mL) using HCl (4 M in 1,4-dioxane, 0.679 mL, 2.72 mmol) and stirring at 40° C. for 1 h. This gave after workup a mixture methyl and ethyl esters of 2-(2-((7-(3-(aminomethyl)phenyl)benzofuran-5-yl)methoxy)-4-(pyridin-4-yl)phenyl)acetate (323b); MS (ES+): 479 (methyl, M+1), 493 (ethyl, M+1).

Step-3: Preparation of 2-(2-((7-(3-(aminomethyl)phenyl)benzofuran-5-yl)methoxy)-4-(pyridin-4-yl)phenyl)acetic Acid (323c)

Compound 323c was prepared according to the procedure reported in step-4 of scheme-4 from mixture of methyl and ethyl esters of 2-(2-((7-(3-(aminomethyl)phenyl)benzofuran-5-yl)methoxy)-4-(pyridin-4-yl)phenyl)acetate (323b) (from step-2 above) in MeOH (3 mL) and water (1 mL), using NaOH (87 mg, 2.173 mmol) and stirring at room temperature for 16 h. This gave after workup and purification by reverse phase column [C18 (100 g), eluting with ACN in water (containing 0.1% HCl) from 0-60%] 2-(2-((7-(3-(aminomethyl)phenyl)benzofuran-5-yl)methoxy)-4-(pyridin-4-yl)phenyl)acetic acid (323c) (55 mg, 22% yield) HCl salt as a white solid; $^1$H NMR (300 MHz, DMSO-$d_6$) δ 8.92 (d, J=5.9 Hz, 2H), 8.52 (s, 3H), 8.36 (d, J=5.9 Hz, 2H), 8.12 (d, J=2.2 Hz, 1H), 8.03 (s, 1H), 7.93 (dt, J=6.4, 2.2 Hz, 1H), 7.81 (d, J=1.6 Hz, 1H), 7.72 (dd, J=7.3, 1.7 Hz, 2H), 7.67-7.54 (m, 3H), 7.48 (d, J=7.8 Hz, 1H), 7.09 (d, J=2.2 Hz, 1H), 5.46 (s, 2H), 4.14 (q, J=5.9 Hz, 2H), 3.71 (s, 2H); MS (ES+): 465 (M+1); Analysis calculated for $C_{29}H_{24}N_2O_4 \cdot 2.25HCl \cdot 2.5H_2O$: C, 58.88; H, 5.32; Cl, 13.48; N, 4.74; Found: C, 58.90; H, 5.13; Cl, 13.64; N, 4.75.

Scheme-324

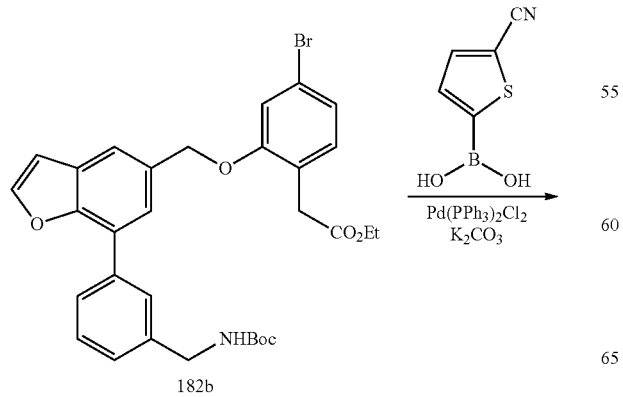

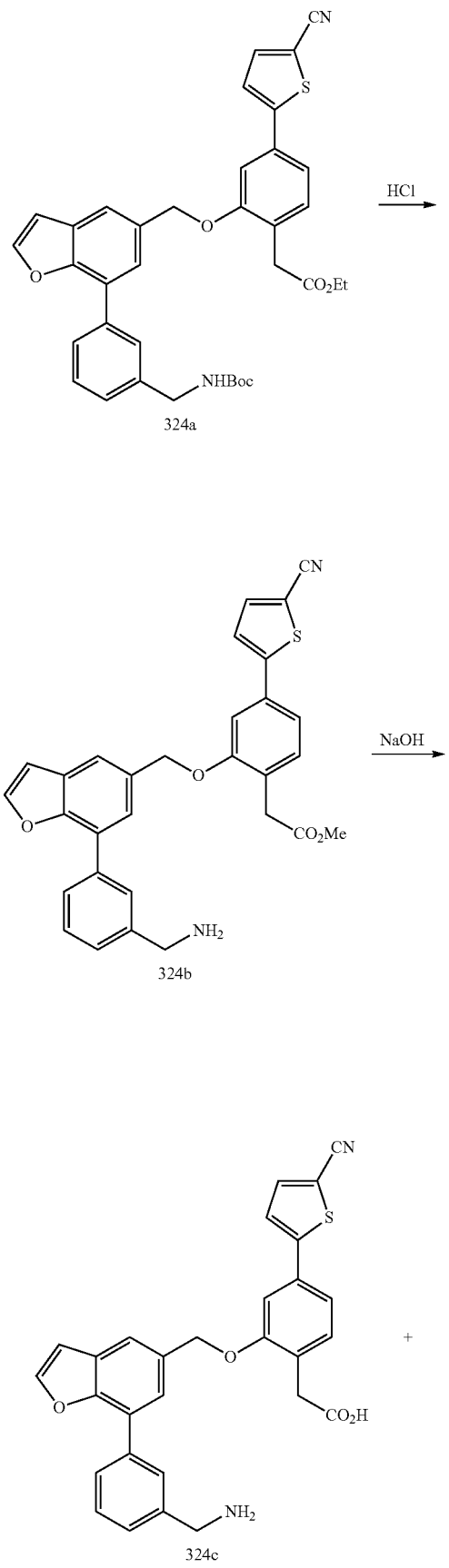

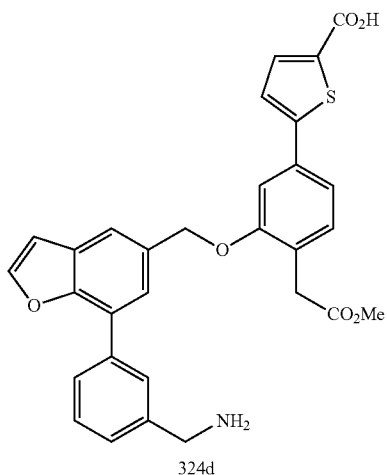

324d

Preparation of 2-(2-((7-(3-(aminomethyl)phenyl)
benzofuran-5-yl)methoxy)-4-(5-cyanothiophen-2-yl)
phenyl)acetic Acid (324c)

Step-1: Preparation of Ethyl 2-(2-((7-(3-(((tert-butoxycarbonyl)amino)methyl)phenyl)benzofuran-5-yl)methoxy)-4-(5-cyanothiophen-2-yl)phenyl)acetate (324a)

Compound 324a was prepared according to the procedure reported in step-3 of scheme-1 from ethyl 2-(4-bromo-2-((7-(3-(((tert-butoxycarbonyl)amino)methyl)phenyl)benzofuran-5-yl)methoxy)phenyl)acetate (182b) (312 mg, 0.525 mmol) in dioxane (4 mL), using (5-cyanothiophen-2-yl) boronic acid (88 mg, 0.577 mmol), Pd(PPh$_3$)$_2$Cl$_2$ (37 mg, 0.052 mmol) and a solution of 2 M aqueous K$_2$CO$_3$ (0.787 mL, 1.574 mmol) under a nitrogen atmosphere and heating at 100° C. for 16 h on oil bath. This gave after workup and purification by flash column chromatography (silica gel, 24 g, eluting with 0-25% EtOAc in hexane) ethyl 2-(2-((7-(3-(((tert-butoxycarbonyl)amino)methyl)phenyl)benzofuran-5-yl)methoxy)-4-(5-cyanothiophen-2-yl)phenyl)acetate (324a) (148 mg) as a clear colorless oil; $^1$H NMR (300 MHz, DMSO-d$_6$) δ 8.09 (d, J=2.2 Hz, 1H), 8.02 (d, J=4.0 Hz, 1H), 7.74 (dd, J=5.1, 3.6 Hz, 4H), 7.59 (d, J=1.6 Hz, 1H), 7.56-7.43 (m, 3H), 7.39-7.28 (m, 3H), 7.07 (d, J=2.2 Hz, 1H), 5.36 (s, 2H), 4.23 (d, J=6.2 Hz, 2H), 3.92 (q, J=7.1 Hz, 2H), 3.67 (s, 2H), 1.39 (s, 9H), 0.96 (t, J=7.1 Hz, 3H).

Step-2: Preparation of methyl 2-(2-((7-(3-(aminomethyl)phenyl)benzofuran-5-yl)methoxy)-4-(5-cyanothiophen-2-yl)phenyl)acetate (324b)

Compound 324b was prepared according to the procedure reported in step-10 of scheme-257 from ethyl 2-(2-((7-(3-(((tert-butoxycarbonyl)amino)methyl)phenyl)benzofuran-5-yl)methoxy)-4-(5-cyanothiophen-2-yl)phenyl)acetate (324a) (148 mg, from step-1) in methanol (5 mL) using HCl (4 M in 1,4-dioxane, 0.656 mL, 2.62 mmol) and stirring at room temperature for 16 h. This gave after workup methyl 2-(2-((7-(3-(aminomethyl)phenyl)benzofuran-5-yl) methoxy)-4-(5-cyanothiophen-2-yl)phenyl)acetate (324b); MS (ES+): 509 (M+1), (ES−): 507 (M−1).

Step-3: Preparation of 2-(2-((7-(3-(aminomethyl) phenyl)benzofuran-5-yl)methoxy)-4-(5-cyanothiophen-2-yl)phenyl)acetic Acid (324c)

Compound 324c was prepared according to the procedure reported in step-4 of scheme-4 from methyl 2-(2-((7-(3-(aminomethyl)phenyl)benzofuran-5-yl)methoxy)-4-(5-cyanothiophen-2-yl)phenyl)acetate (324b) (from step-2 above) in MeOH (3 mL) and water (1 mL), using NaOH (105 mg, 2.62 mmol) and stirring at room temperature for 16 h. This gave after workup and purification by reverse phase column [C18 (100 g), eluting with ACN in water (containing 0.1% HCl) from 0-60%] 2-(2-((7-(3-(aminomethyl)phenyl)benzofuran-5-yl)methoxy)-4-(5-cyanothiophen-2-yl)phenyl)acetic acid (324c) (20 mg, 8% yield) HCl salt as a white solid; $^1$H NMR (300 MHz, DMSO-d$_6$) δ 8.11 (d, J=2.2 Hz, 1H), 8.01 (d, J=3.9 Hz, 2H), 7.94 (dt, J=7.7, 1.5 Hz, 1H), 7.80 (d, J=1.6 Hz, 1H), 7.73 (d, J=4.0 Hz, 1H), 7.69 (d, J=1.6 Hz, 1H), 7.61 (t, J=7.6 Hz, 1H), 7.57-7.52 (m, 1H), 7.47 (d, J=1.5 Hz, 1H), 7.39-7.26 (m, 2H), 7.09 (d, J=2.2 Hz, 1H), 5.40 (s, 2H), 4.15 (s, 2H), 3.64 (s, 2H); MS (ES+): 495 (M+1) and 5-(3-((7-(3-(aminomethyl)phenyl)benzofuran-5-yl)methoxy)-4-(2-methoxy-2-oxoethyl)phenyl)thiophene-2-carboxylic acid (324d) (65 mg, 24% yield) HCl salt as a white solid; $^1$H NMR (300 MHz, DMSO-d$_6$) δ 8.11 (d, J=2.2 Hz, 1H), 8.01 (d, J=2.3 Hz, 1H), 7.94 (dt, J=7.6, 1.6 Hz, 1H), 7.86-7.78 (m, 2H), 7.69 (d, J=1.6 Hz, 1H), 7.64 (d, J=4.0 Hz, 1H), 7.59 (d, J=7.5 Hz, 1H), 7.54 (d, J=7.8 Hz, 1H), 7.46 (s, 1H), 7.31 (d, J=0.9 Hz, 2H), 7.08 (d, J=2.2 Hz, 1H), 5.40 (s, 2H), 4.14 (s, 2H), 3.84 (s, 3H), 3.63 (s, 2H); MS (ES+): 528 (M+1).

Scheme-325

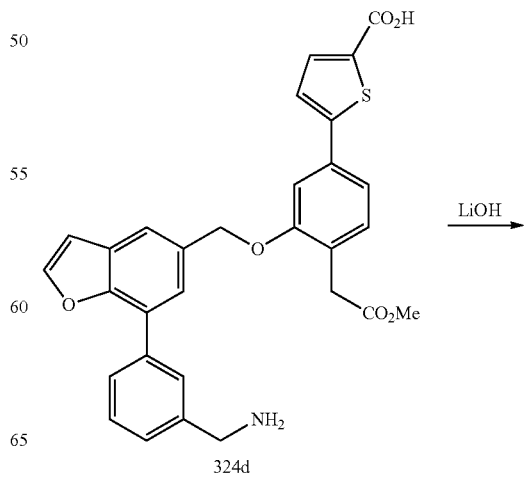

324d

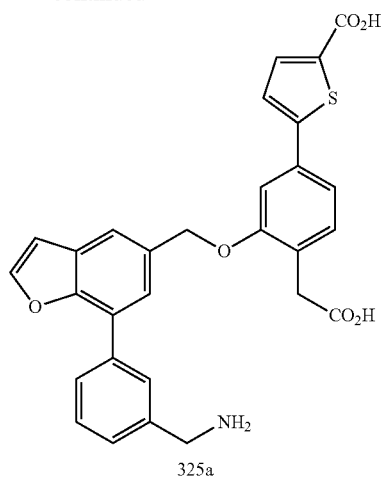

325a

Preparation of 5-(3-((7-(3-(aminomethyl)phenyl) benzofuran-5-yl)methoxy)-4-(carboxymethyl)phenyl)thiophene-2-carboxylic Acid (325a)

Compound 325a was prepared according to the procedure reported in step-6 of scheme-1 from 5-(3-((7-(3-(aminomethyl)phenyl)benzofuran-5-yl)methoxy)-4-(2-methoxy-2-oxoethyl)phenyl)thiophene-2-carboxylic acid (324d) (60 mg, 0.114 mmol) in MeOH (3 mL) using aqueous 2.5 M LiOH (0.455 mL, 1.137 mmol) and stirring at room temperature for 16 h. This gave after workup and purification by reverse phase column [C18 (100 g), eluting with ACN in water (containing 0.1% HCl) from 0-60%] 5-(3-((7-(3-(aminomethyl)phenyl)benzofuran-5-yl)methoxy)-4-(carboxymethyl)phenyl)thiophene-2-carboxylic acid (325a) (38 mg, 65% yield) HCl salt as a white solid; $^1$H NMR (300 MHz, DMSO-$d_6$) δ 8.11 (d, J=2.1 Hz, 1H), 8.01 (t, J=1.7 Hz, 1H), 7.94 (dt, J=7.5, 1.5 Hz, 1H), 7.80 (d, J=1.6 Hz, 1H), 7.75-7.67 (m, 2H), 7.66-7.51 (m, 3H), 7.44 (s, 1H), 7.35-7.25 (m, 2H), 7.08 (d, J=2.2 Hz, 1H), 5.40 (s, 2H), 4.14 (s, 2H), 3.63 (s, 2H); MS (ES+): 514 (M+1), (ES−): 512 (M−1).

Scheme-326

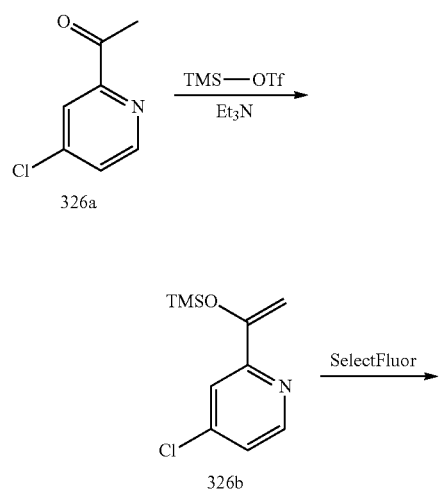

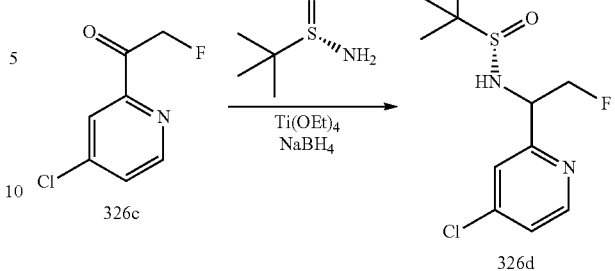

326c → 326d

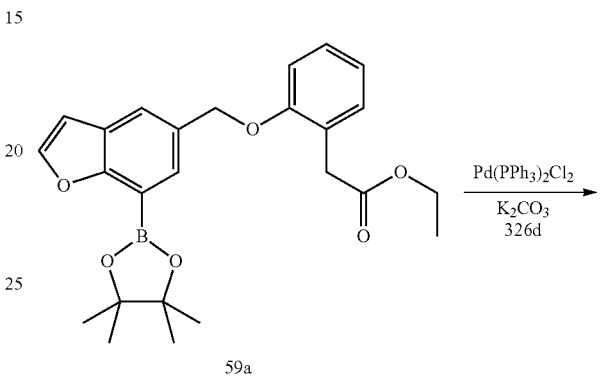

59a

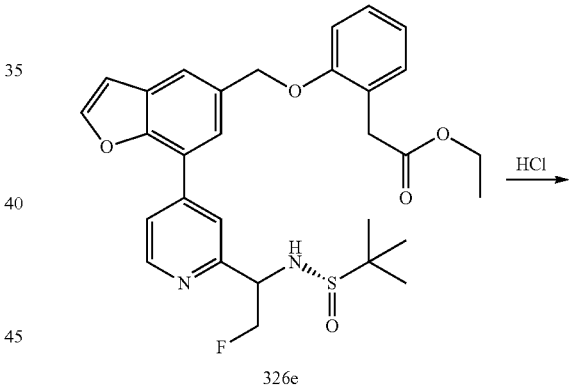

326e
(+)-isomer

326f

-continued

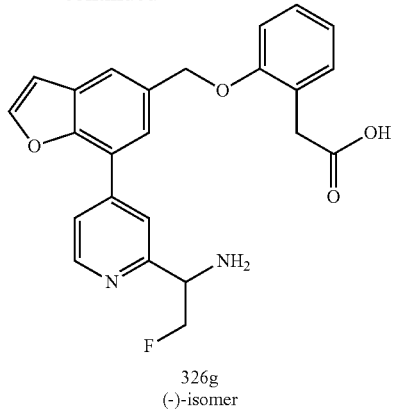 [SMILES: NC(CF)c1cc(-c2cc(COc3ccccc3CC(=O)O)cc3ccoc23)ccn1 ; "327d(+)-isomer"]

326g
(-)-isomer

Preparation of (−)-2-(2-((7-(2-(1-amino-2-fluoro-ethyl)pyridin-4-yl)benzofuran-5-yl)methoxy)phenyl)acetic Acid (326g)

Step-1: Preparation of 4-chloro-2-(1-((trimethylsilyl)oxy)vinyl)pyridine (326b)

To a solution of 1-(4-chloropyridin-2-yl)ethanone (326a) (5.0 g, 32.1 mmol; CAS #60159-37-7) and Et₃N (9.76 g, 96 mmol) in DCM (15 mL) at 0° C. was added TMS-OTf (14.29 g, 64.3 mmol) in DCM (2 mL) dropwise under a nitrogen atmosphere and stirred at 0° C. for 2 h. The solution was washed with H₂O (25 mL) and brine (25 mL), dried, filtered and concentrated in vacuum to afford 4-chloro-2-(1-((trimethylsilyl)oxy)vinyl)pyridine (326b) as an orange oil which was used as such for next step without purification; MS (ES+): 228/230 (M+1).

Step-2: Preparation of 1-(4-chloropyridin-2-yl)-2-fluoroethanone (326c)

To a solution of 4-chloro-2-(1-((trimethylsilyl)oxy)vinyl)pyridine (326b) (from above step-1) in MeCN (20 mL) was added SelectFluor (14.80 g, 41.8 mmol) and stirred at room temperature for 2 h. The reaction mixture was diluted with EtOAc (30 mL) and H₂O (30 mL) and continued stirring for 15 min. The organic layer was separated and extracted with EtOAc (2×25). The combined organic extract was washed with brine (25 mL), dried, filtered and concentrated in vacuum. The residue obtained was purified by flash column chromatography (silica gel, 80 g, eluting with 0-2% EtOAc in hexane) to afford 1-(4-chloropyridin-2-yl)-2-fluoroethanone (326c) (1.80 g, 10.37 mmol, 32.3% yield) as a white solid; ¹H NMR (300 MHz, DMSO-d₆) δ 8.69 (dd, J=5.3, 0.6 Hz, 1H), 8.01 (dt, J=2.2, 0.5 Hz, 1H), 7.89 (dd, J=5.3, 2.1 Hz, 1H), 6.00 (s, 1H), 5.85 (s, 1H). ¹⁹F NMR (282 MHz, DMSO-d₆) δ−235.43; MS (ES+): 174/176 (M+1).

Step-3: Preparation of (S)—N-(1-(4-chloropyridin-2-yl)-2-fluoroethyl)-2-methylpropane-2-sulfinamide (326d)

To a solution of 1-(4-chloropyridin-2-yl)-2-fluoroethanone (326c) (600 mg, 3.46 mmol), (S)-2-methylpropane-2-sulfinamide (838 mg, 6.91 mmol) was added a solution of Ti(OEt)₄ (2366 mg, 10.37 mmol) in THF (20 mL) and heated at 65° C. for 16 h under nitrogen. The resulting deep red solution was cooled to −48° C. and added dropwise to a solution of NaBH₄ (436 mg, 11.52 mmol) in THF (5 mL) at −48° C. and stirred at −48° C. for 16 h. The reaction mixture was quenched carefully with MeOH, poured into brine (20 mL) and vigorously stirred for 30 mins. The solid residue was removed by filtration, cake was washed with EtOAc (50 mL) and organic layer was separated. The organic layer was washed with brine (20 mL), dried, filtered and concentrated in vacuum. The residue obtained was purified by flash column chromatography (silica gel, 24 g, eluting with 0-40% EtOAc in hexane) to afford (S)—N-(1-(4-chloropyridin-2-yl)-2-fluoroethyl)-2-methylpropane-2-sulfinamide (326d) (127 mg, 13% yield) as an orange oil; ¹H NMR (300 MHz, DMSO-d₆) δ 8.54 (d, J=5.4 Hz, 1H), 7.79 (d, J=2.0 Hz, 1H), 7.50 (dd, J=5.3, 2.0 Hz, 1H), 6.05 (d, J=8.7 Hz, 1H), 4.92-4.48 (m, 3H), 1.15 (s, 9H). ¹⁹F NMR (282 MHz, DMSO-d₆) δ−222.53; MS (ES+) 279/281 (M+1).

Step-4: Preparation of (+)-ethyl 2-(2-((7-(2-(1-((S)-1,1-dimethylethylsulfinamido)-2-fluoroethyl)pyridin-4-yl)benzofuran-5-yl)methoxy)phenyl)acetate (326e)

Compound 326e was prepared according to the procedure reported in step-3 of scheme-1 from ethyl 2-(2-((7-(4,4,5,5-tetramethyl-1,3,2-dioxaborolan-2-yl)benzofuran-5-yl)methoxy)phenyl)acetate (59a) (219 mg, 0.501 mmol) in dioxane (9 mL) using (S)—N-(1-(4-chloropyridin-2-yl)-2-fluoroethyl)-2-methylpropane-2-sulfinamide (326d) (127 mg, 0.456 mmol), Pd(PPh₃)₂Cl₂ (48 mg, 0.068 mmol) and a solution of K₂CO₃ (189 mg, 1.367 mmol) in water (1 mL) under a nitrogen atmosphere and heating at 100° C. for 16 h on oil bath. This gave after workup and purification by flash column chromatography (silica gel, 40 g, eluting with 0-50% ethyl acetate in hexanes) (+)-ethyl 2-(2-((7-(2-(1-((S)-1,1-dimethylethylsulfinamido)-2-fluoroethyl)pyridin-4-yl)benzofuran-5-yl)methoxy)phenyl)acetate (326e) (98 mg) as a colorless oil; MS (ES+) 553 (M+1); Optical rotation [α]D=+40.0 (c=0.01, MeOH)

Step-5: Preparation of Ethyl 2-(2-((7-(2-(1-amino-2-fluoroethyl)pyridin-4-yl)benzofuran-5-yl)methoxy)phenyl)acetate (326f)

Compound 326f was prepared according to the procedure reported in step-10 of scheme-257 from (+)-ethyl 2-(2-((7-(2-(1-((S)-1,1-dimethylethylsulfinamido)-2-fluoroethyl)pyridin-4-yl)benzofuran-5-yl)methoxy)phenyl)acetate (326e) (98 mg; from above step-4) in MeOH (5 mL) using HCl (4 M in 1,4-dioxane; 0.569 mL, 2.278 mmol) and stirring at 40° C. for 1 h. This gave after workup and purification by flash column chromatography (silica gel, 25 g, eluting with DMA 80 in dichloromethane) ethyl 2-(2-((7-(2-(1-amino-2-fluoroethyl)pyridin-4-yl)benzofuran-5-yl)methoxy)phenyl)acetate (326f) which was used as such in next step; MS (ES+): 435 (M+1).

Step-6: Preparation of (−)-2-(2-((7-(2-(1-amino-2-fluoroethyl)pyridin-4-yl)benzofuran-5-yl)methoxy)phenyl)acetic Acid (326g)

Compound 326g was prepared according to the procedure reported in step-4 of scheme-4 from ethyl 2-(2-((7-(2-(1-amino-2-fluoroethyl)pyridin-4-yl)benzofuran-5-yl)methoxy)phenyl)acetate (326f) (from step-5 above) in MeOH (3 mL), water (1 mL) using NaOH (55 mg, 1.367 mmol). This gave after workup and purification by reverse phase column [C18 (100 g), eluting with ACN in water (containing 0.1% HCl) from 0-60%] (−)-2-(2-((7-(2-(1-amino-2-fluoroethyl)pyridin-4-yl)benzofuran-5-yl)methoxy)phenyl)acetic acid (326g) (15 mg, 8% yield) HCl salt as a white solid; $^{1}$H NMR (300 MHz, DMSO-$d_6$) δ 8.95 (s, 3H), 8.80 (d, J=5.2 Hz, 1H), 8.19 (dd, J=9.9, 1.9 Hz, 2H), 8.05 (dd, J=5.2, 1.7 Hz, 1H), 7.87 (dd, J=12.0, 1.6 Hz, 2H), 7.25 (dd, J=8.1, 6.4 Hz, 2H), 7.15-7.07 (m, 2H), 6.91 (td, J=7.4, 1.1 Hz, 1H), 5.30 (s, 2H), 5.13-4.79 (m, 3H), 3.62 (s, 2H). $^{19}$F NMR (282 MHz, DMSO-$d_6$) δ−226.50; MS (ES+): 421 (M+1), (ES−): 419 (M−1); Optical rotation [c]D=−9.23 (c=0.13, MeOH).

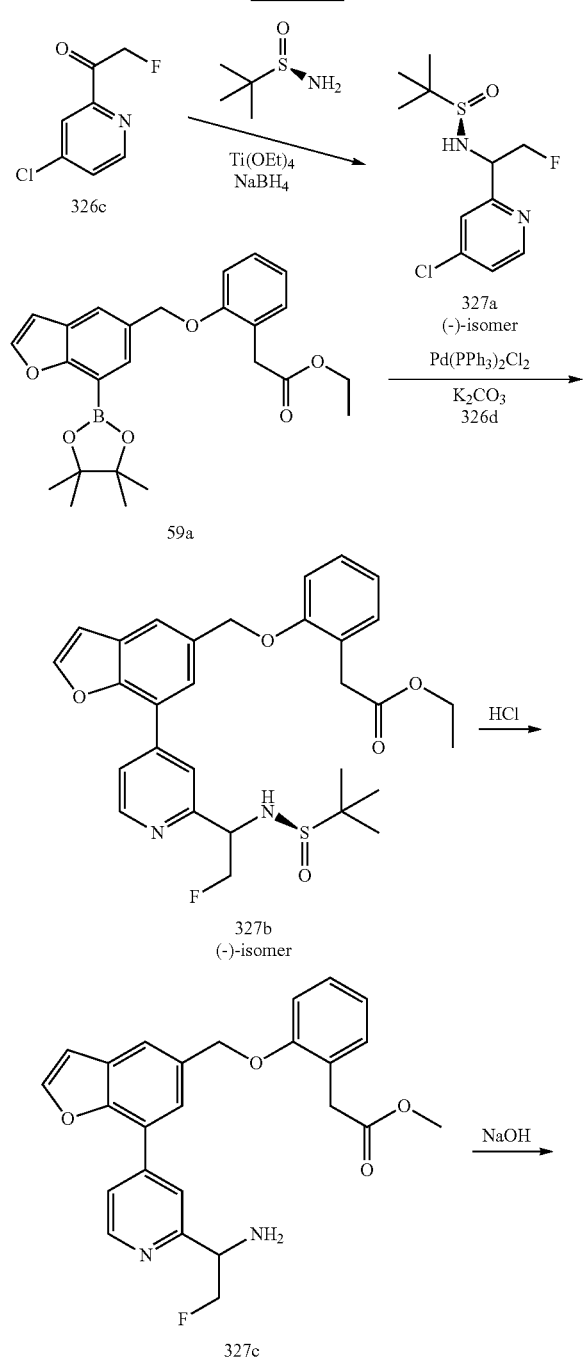

Scheme-327

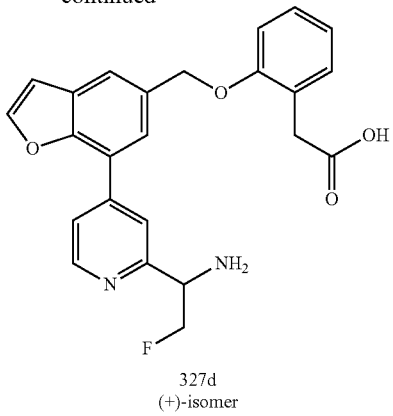

327d
(+)-isomer

Preparation of (+)-2-(2-((7-(2-(1-amino-2-fluoroethyl)pyridin-4-yl)benzofuran-5-yl)methoxy)phenyl) acetic Acid (327d)

Step-1: Preparation of (−)-N-(1-(4-chloropyridin-2-yl)-2-fluoroethyl)-2-methylpropane-2-sulfinamide (327a)

Compound 327a was prepared according to the procedure reported in step-3 of scheme-326 from 1-(4-chloropyridin-2-yl)-2-fluoroethanone (326c) (500 mg, 2.88 mmol), (R)-2-methylpropane-2-sulfinamide (367 mg, 3.02 mmol) using a solution of Ti(OEt)$_4$ (1314 mg, 5.76 mmol) in THF (20 mL) and heating at 65° C. for 16 h under nitrogen, followed by reduction of imine obtained using a solution of NaBH$_4$ (436 mg, 11.52 mmol) in THF (5 mL) and stirring at −48° C. for 16 h. This gave after workup and purification by flash column chromatography (silica gel, 24 g, eluting with 0-40% EtOAc in hexane) (−)-N-(1-(4-chloropyridin-2-yl)-2-fluoroethyl)-2-methylpropane-2-sulfinamide (327a) (82 mg, 10% yield) as an orange oil; $^{1}$H NMR (300 MHz, DMSO-$d_6$) δ 8.54 (d, J=5.3 Hz, 1H), 7.80 (d, J=2.0 Hz, 1H), 7.50 (dd, J=5.3, 2.0 Hz, 1H), 6.05 (d, J=8.8 Hz, 1H), 4.88-4.50 (m, 3H), 1.16 (s, 9H). $^{19}$F NMR (282 MHz, DMSO-$d_6$) δ−222.53; MS (ES+): 279/281 (M+1); Optical rotation [c]D=−40.00 (c=0.03, MeOH)

Step-2: Preparation of (−)-ethyl 2-(2-((7-(2-(1-(1,1-dimethylethylsulfinamido)-2-fluoroethyl)pyridin-4-yl)benzofuran-5-yl)methoxy)phenyl)acetate (327b)

Compound 327b was prepared according to the procedure reported in step-3 of scheme-1 from ethyl 2-(2-((7-(4,4,5,5-tetramethyl-1,3,2-dioxaborolan-2-yl)benzofuran-5-yl)methoxy)phenyl)acetate (59a) (141 mg, 0.324 mmol) in dioxane (9 mL) using (−)-N-(1-(4-chloropyridin-2-yl)-2-fluoroethyl)-2-methylpropane-2-sulfinamide (327a) (82 mg, 0.294 mmol), Pd(PPh$_3$)$_2$Cl$_2$ (31 mg, 0.044 mmol) and a solution of K$_2$CO$_3$ (122 mg, 0.882 mmol) in water (1 mL) under a nitrogen atmosphere and heating at 100° C. for 16 h on oil bath. This gave after workup and purification by flash column chromatography (silica gel, 40 g, eluting with 0-50% ethyl acetate in hexanes) (−)-ethyl 2-(2-((7-(2-(1-(1,1-dimethylethylsulfinamido)-2-fluoroethyl)pyridin-4-yl)benzofuran-5-yl)methoxy)phenyl)acetate (327b) (72 mg) as a clear colorless oil; MS (ES+): 553 (M+1); Optical rotation [c]D=−22.82 (c=0.035, MeOH)

Step-3: Preparation of methyl and ethyl esters of 2-(2-((7-(2-(1-amino-2-fluoroethyl)pyridin-4-yl)benzofuran-5-yl)methoxy)phenyl)acetate (327c)

Compound 327c was prepared according to the procedure reported in step-10 of scheme-257 from (−)-ethyl 2-(2-((7-(2-(1-(1,1-dimethylethylsulfinamido)-2-fluoroethyl)pyridin-4-yl)benzofuran-5-yl)methoxy)phenyl)acetate (327b) (72 mg; from above step-2 in MeOH (5 mL) using HCl (4 M in 1,4-dioxane; 0.588 mL, 2.353 mmol) and stirring at 40° C. for 1 h. This gave after workup a mixture of methyl and ethyl esters of 2-(2-((7-(2-(1-amino-2-fluoroethyl)pyridin-4-yl)benzofuran-5-yl)methoxy)phenyl)acetate (327c); MS (ES+): 435 (methyl, M+1), 449 (ethyl, M+1).

Step-4: Preparation of (+)-2-(2-((7-(2-(1-amino-2-fluoroethyl)pyridin-4-yl)benzofuran-5-yl)methoxy)phenyl)acetic Acid (327d)

Compound 327d was prepared according to the procedure reported in step-4 of scheme-4 from a mixture of methyl and ethyl esters of 2-(2-((7-(2-(1-amino-2-fluoroethyl)pyridin-4-yl)benzofuran-5-yl)methoxy)phenyl)acetate (327c) (from step-3 above) in MeOH (3 mL), water (1 mL) using NaOH (47 mg, 1.177 mmol). This gave after workup and purification by reverse phase column [C18 (100 g), eluting with ACN in water (containing 0.1% HCl) from 0-60%] (+)-2-(2-((7-(2-(1-amino-2-fluoroethyl)pyridin-4-yl)benzofuran-5-yl)methoxy)phenyl)acetic acid (327d) (19 mg, 16% yield) HCl salt as a white solid; $^1$H NMR (300 MHz, DMSO-$d_6$) δ 8.89 (s, 3H), 8.80 (dd, J=5.3, 0.7 Hz, 1H), 8.19 (dd, J=1.8, 0.8 Hz, 1H), 8.17 (d, J=2.2 Hz, 1H), 8.04 (dd, J=5.2, 1.7 Hz, 1H), 7.89 (d, J=1.6 Hz, 1H), 7.84 (d, J=1.6 Hz, 1H), 7.24 (dd, J=8.1, 6.6 Hz, 2H), 7.17-7.05 (m, 2H), 6.91 (td, J=7.4, 1.1 Hz, 1H), 5.30 (s, 2H), 5.08-4.79 (m, 3H), 3.61 (s, 2H). $^{19}$F NMR (282 MHz, DMSO-$d_6$) δ −226.26; MS (ES+): 421 (M+1), 419 (M−1); Optical rotation [α]$_D$=+10.73 (c=0.205, MeOH).

Scheme-328

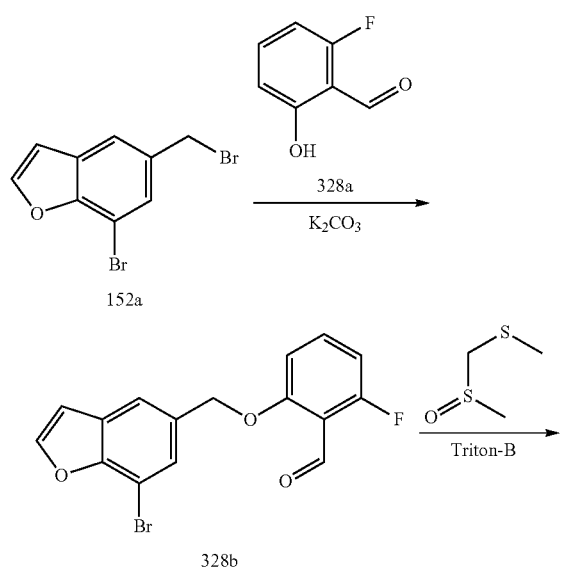

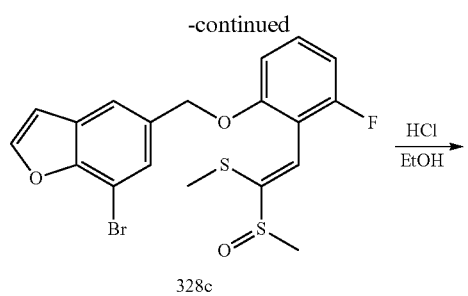

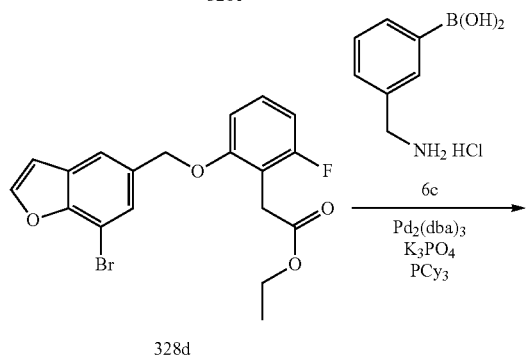

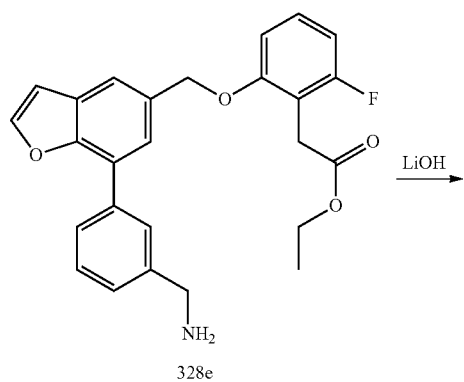

Preparation of 2-(2-((7-(3-(aminomethyl)phenyl)benzofuran-5-yl)methoxy)-6-fluorophenyl)acetic Acid (328f)

Step-1: Preparation of 2-((7-bromobenzofuran-5-yl)methoxy)-6-fluorobenzaldehyde (328b)

Compound 328b was prepared according to the procedure reported in step-2 of scheme-152 from 7-bromo-5-(bromomethyl)benzofuran (152a) (2.069 g, 7.14 mmol) using 2-fluoro-6-hydroxybenzaldehyde (328a) (1 g, 7.14 mmol), $K_2CO_3$ (2.96 g, 21.41 mmol) in DMF (10 mL) and stirring at room temperature for 12 h. This gave after workup and purification by flash column chromatography (silica gel, 40 g, eluting with 0 to 50% ethyl acetate in hexanes) 2-((7-bromobenzofuran-5-yl)methoxy)-6-fluorobenzaldehyde (328b) (2.05 g, 82% yield) as a white solid; $^1$H NMR (300 MHz, DMSO-$d_6$) δ 10.38 (dd, J=1.3, 0.6 Hz, 1H), 8.16 (d, J=2.1 Hz, 1H), 7.84 (d, J=1.5 Hz, 1H), 7.74 (d, J=1.6 Hz, 1H), 7.67 (td, J=8.5, 6.5 Hz, 1H), 7.22-7.10 (m, 2H), 6.92 (ddt, J=10.8, 8.4, 0.7 Hz, 1H), 5.38 (s, 2H); $^{19}$F NMR (282 MHz, DMSO-$d_6$) δ−115.52; MS (ES+): 370.9 (M+Na).

Step-2: Preparation of 7-bromo-5-((3-fluoro-2-(2-(methylsulfinyl)-2-(methylthio)vinyl)phenoxy)methyl)benzofuran (328c)

Compound 328c was prepared according to the procedure reported in step-3 of scheme-266 from 2-((7-bromobenzofuran-5-yl)methoxy)-6-fluorobenzaldehyde (328b) (2 g, 5.73 mmol) in THF (30 mL) using methyl(methylsulfinylmethyl)sulfane (1.139 g, 9.17 mmol), Triton-B (40% methanolic solution, 0.521 mL, 2.86 mmol) and heating at reflux for 2 h. This gave after workup and purification by flash column chromatography (Silica gel, 40 g, eluting with 0-100% EtOAc in hexane) 7-bromo-5-((3-fluoro-2-(2-(methylsulfinyl)-2-(methylthio)vinyl)phenoxy)methyl)benzofuran (328c) (795 mg, 31% yield) as a colorless gel; $^1$H NMR (300 MHz, DMSO-$d_6$) δ 8.14 (d, J=2.2 Hz, 1H), 7.73 (d, J=1.5 Hz, 1H), 7.63 (d, J=1.5 Hz, 1H), 7.48-7.34 (m, 2H), 7.10 (d, J=2.2 Hz, 1H), 7.05 (d, J=8.4 Hz, 1H), 6.91 (t, J=8.8 Hz, 1H), 5.28 (s, 2H), 2.73 (s, 3H), 2.19 (s, 3H); $^{19}$F NMR (282 MHz, DMSO) δ−110.68.

Step-3: Preparation of Ethyl 2-(2-((7-bromobenzofuran-5-yl)methoxy)-6-fluorophenyl)acetate (328d)

Compound 328d was prepared according to the procedure reported in step-4 of scheme-266 from 7-bromo-5-((3-fluoro-2-(2-(methylsulfinyl)-2-(methylthio)vinyl)phenoxy)methyl)benzofuran (328c) (790 mg, 1.735 mmol) in ethanol (20 mL) using HCl (4 M in 1,4-dioxane, 2.169 mL, 8.67 mmol) and heating at reflux for 2 h. This gave after workup and purification by flash column chromatography (silica gel, 12 g, eluting with 0 to 100% ethyl acetate and hexanes) ethyl 2-(2-((7-bromobenzofuran-5-yl)methoxy)-6-fluorophenyl)acetate (328d) (626 mg, 89% yield). $^1$H NMR (300 MHz, DMSO-$d_6$) δ 8.15 (d, J=2.2 Hz, 1H), 7.73 (d, J=1.5 Hz, 1H), 7.61 (d, J=1.5 Hz, 1H), 7.31 (td, J=8.4, 7.0 Hz, 1H), 7.12 (d, J=2.2 Hz, 1H), 7.02-6.93 (m, 1H), 6.84 (ddd, J=9.3, 8.3, 0.9 Hz, 1H), 5.23 (s, 2H), 4.04 (q, J=7.1 Hz, 2H), 3.64 (s, 2H), 1.09 (t, J=7.1 Hz, 3H); $^{19}$F NMR (282 MHz, DMSO-$d_6$) δ−116.82.

Step-4: Preparation of Ethyl 2-(2-((7-(3-(aminomethyl)phenyl)benzofuran-5-yl)methoxy)-6-fluorophenyl)acetate (328e)

Compound 328e was prepared according to the procedure reported in step-3 of scheme-1 from ethyl 2-(2-((7-bromobenzofuran-5-yl)methoxy)-6-fluorophenyl)acetate (328d) (300 mg, 0.737 mmol) in dioxane (10 mL) using 3-(aminomethyl)phenylboronic acid hydrochloride (6c) (167 mg, 1.105 mmol), tripotassium phosphate (1.3M, 1.7 mL, 2.21 mmol), tricyclohexylphosphine (62 mg, 0.221 mmol) and Pd$_2$(dba)$_3$ (68 mg, 0.074 mmol) under an nitrogen atmosphere and heating at 125° C. for 60 min in a microwave. This gave after workup, purification by flash column chromatography [silica (12 g), eluting 0 to 100% DMA80 in DCM] ethyl 2-(2-((7-(3-(aminomethyl)phenyl)benzofuran-5-yl)methoxy)-6-fluorophenyl)acetate (328e) (176 mg, 55% yield). $^1$H NMR (300 MHz, DMSO-$d_6$) δ 8.10 (d, J=2.2 Hz, 1H), 7.82 (s, 1H), 7.76-7.67 (m, 2H), 7.58 (d, J=1.7 Hz, 1H), 7.47 (t, J=7.6 Hz, 1H), 7.40 (d, J=7.6 Hz, 1H), 7.31 (td, J=8.3, 6.9 Hz, 1H), 7.09-6.97 (m, 2H), 6.83 (t, J=8.7 Hz, 1H), 5.29 (s, 2H), 3.96 (q, J=7.1 Hz, 2H), 3.81 (s, 2H), 3.65 (s, 2H), 1.01 (t, J=7.1 Hz, 3H); $^{19}$F NMR (282 MHz, DMSO) δ−116.84; MS (ES+): 434.1 (M+1).

Step-5: Preparation of 2-(2-((7-(3-(aminomethyl)phenyl)benzofuran-5-yl)methoxy)-6-fluorophenyl)acetic Acid (328f)

Compound 328f was prepared according to the procedure reported in step-6 of scheme-1 from ethyl 2-(2-((7-(3-(aminomethyl)phenyl)benzofuran-5-yl)methoxy)-6-fluorophenyl)acetate (328e) (175 mg, 0.404 mmol) in MeOH (4 mL), THF (4 mL) using 2N lithium hydroxide (0.807 mL, 1.615 mmol). This gave after workup and purification by reverse phase column [C18 (50g), eluting with ACN in water (containing 0.1% HCl) from 0-100%] 2-(2-((7-(3-(aminomethyl)phenyl)benzofuran-5-yl)methoxy)-6-fluorophenyl)acetic acid (328f) (57 mg, 35% yield) HCl salt as a white solid; $^1$H NMR (300 MHz, DMSO-$d_6$) δ 8.47 (s, 3H), 8.12 (d, J=2.2 Hz, 1H), 8.04-7.98 (m, 1H), 7.92 (dt, J=7.0, 2.0 Hz, 1H), 7.77 (d, J=1.6 Hz, 1H), 7.65 (d, J=1.7 Hz, 1H), 7.63-7.53 (m, 2H), 7.36-7.22 (m, 1H), 7.07 (d, J=2.2 Hz, 1H), 7.00 (d, J=8.3 Hz, 1H), 6.82 (t, J=8.7 Hz, 1H), 5.31 (s, 2H), 4.14 (s, 2H), 3.61 (s, 2H); $^{19}$F NMR (282 MHz, DMSO-$d_6$) δ−116.60; MS (ES+): 406.1 (M+1); Analysis calculated for C$_{24}$H$_{20}$FNO$_4$.HCl.1.25H$_2$O: C, 62.07; H, 5.10; N, 3.02; Found: C, 62.26; H, 4.88; N, 3.07.

Scheme-329

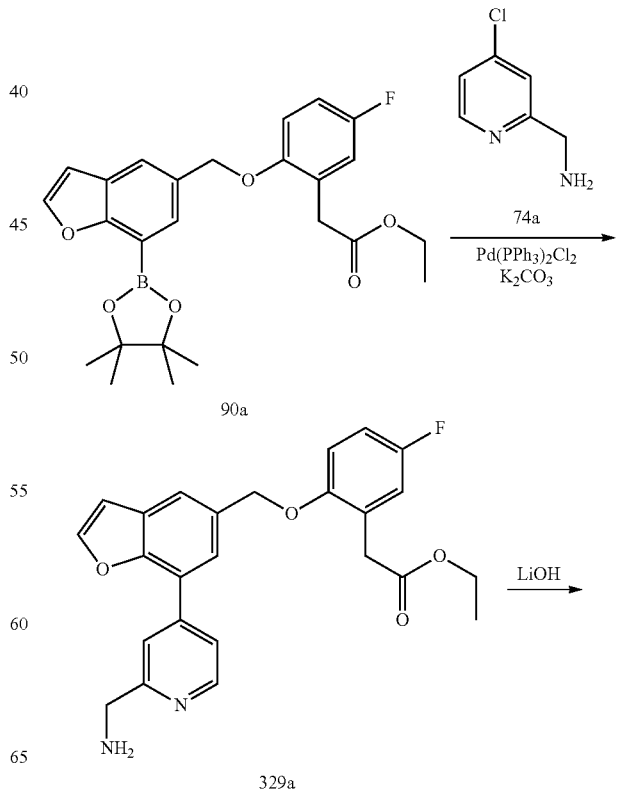

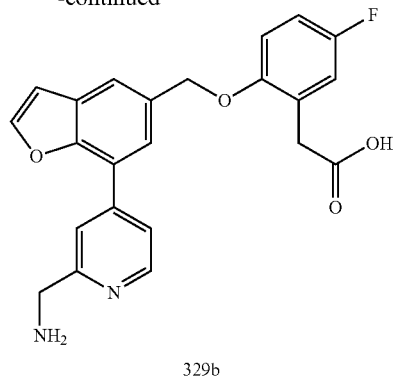

329b

Preparation of 2-(2-((7-(2-(aminomethyl)pyridin-4-yl)benzofuran-5-yl)methoxy)-5-fluorophenyl)acetic Acid (329b)

Step-1: Preparation of Ethyl 2-(2-((7-(2-(aminomethyl)pyridin-4-yl)benzofuran-5-yl)methoxy)-5-fluorophenyl)acetate (329a)

Compound 329a was prepared according to the procedure reported in step-3 of scheme-1 from ethyl 2-(5-fluoro-2-((7-(4,4,5,5-tetramethyl-1,3,2-dioxaborolan-2-yl)benzofuran-5-yl)methoxy)phenyl)acetate (90a) (0.21 g, 0.46 mmol) in dioxane (4 mL) using (4-chloropyridin-2-yl)methanamine (74a) (0.10 g, 0.69 mmol), bis(triphenylphosphine)palladium(II) chloride (0.05 g, 0.07 mmol) and a solution of $K_2CO_3$ (0.16 g, 1.16 mmol) in water (0.5 mL) under an Ar atmosphere and heating at 90° C. for 3 h on oil bath. This gave after workup, purification by flash column chromatography [silica (12 g), eluting with methanol in DCM from 0-50%] ethyl 2-(2-((7-(2-(aminomethyl)pyridin-4-yl)benzofuran-5-yl)methoxy)-5-fluorophenyl)acetate (329a) (0.12 g, 59% yield) as a white solid; MS (ES+): 435.2 (M+1); MS (ES−): 433.2 (M−1).

Step-2: Preparation of 2-(2-((7-(2-(aminomethyl)pyridin-4-yl)benzofuran-5-yl)methoxy)-5-fluorophenyl)acetic Acid (329b)

Compound 329b was prepared according to the procedure reported in step-6 of scheme-1 from ethyl 2-(2-((7-(2-(aminomethyl)pyridin-4-yl)benzofuran-5-yl)methoxy)-5-fluorophenyl)acetate (329a) (0.12 g, 0.27 mmol) in MeOH/THF (4 mL) using a solution of lithium hydroxide monohydrate (0.09 g, 2.17 mmol) in water (1 mL). This gave after workup and purification by reverse phase column [C18 (50g), eluting with ACN in water (containing 0.1% HCl) from 0-100%] 2-(2-((7-(2-(aminomethyl)pyridin-4-yl)benzofuran-5-yl)methoxy)-5-fluorophenyl)acetic acid (329b) (0.07 g, 59% yield) HCl salt as a white solid; $^1$H NMR (300 MHz, DMSO-$d_6$) δ 8.78 (dd, J=5.3, 0.7 Hz, 1H), 8.52 (s, 3H), 8.17 (d, J=2.2 Hz, 1H), 8.09 (t, J=1.2 Hz, 1H), 7.99 (dd, J=5.3, 1.7 Hz, 1H), 7.86 (d, J=1.6 Hz, 1H), 7.81 (d, J=1.6 Hz, 1H), 7.21-7.01 (m, 4H), 5.27 (s, 2H), 4.31 (d, J=5.7 Hz, 2H), 3.62 (s, 2H); $^{19}$F NMR (282 MHz, DMSO-$d_6$) δ −124.05; MS (ES+): 407.9 (M+1); Analysis calculated for: $C_{23}H_{19}FN_2O_4 \cdot 1.75HCl \cdot 1.5H_2O$: C, 55.56; H, 4.81; Cl, 12.48; N, 5.63; Found: C, 55.22; H, 4.58; Cl, 12.48; N, 5.67.

Scheme-330

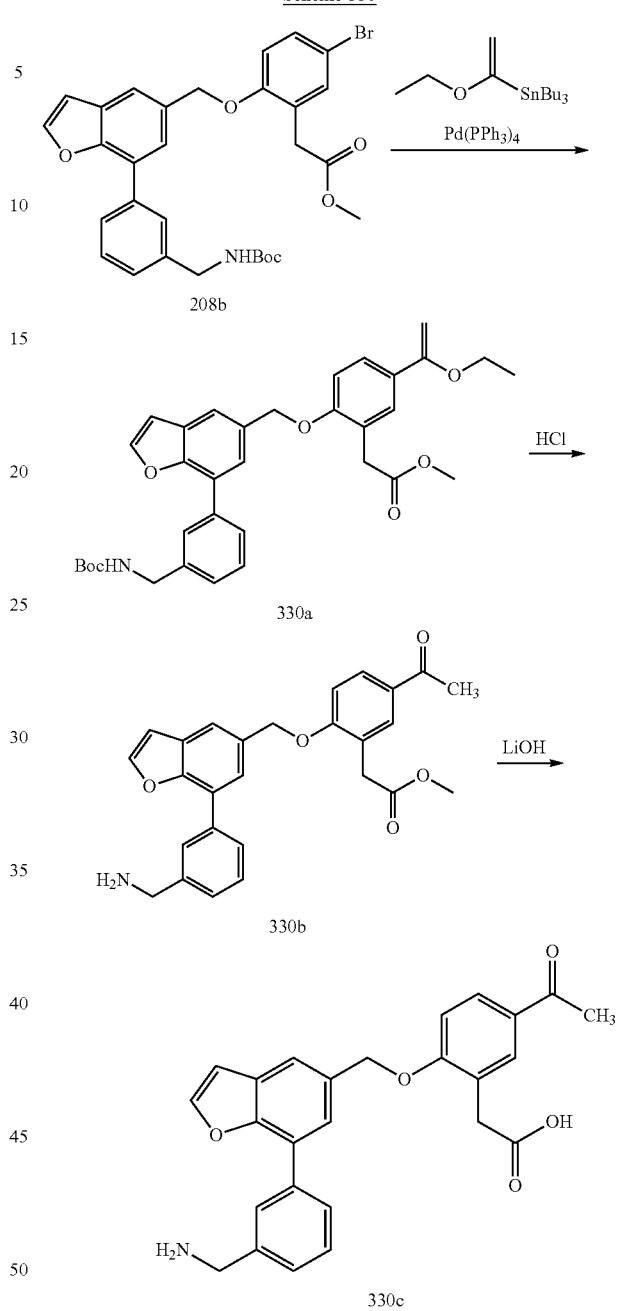

Preparation of 2-(5-acetyl-2-((7-(3-(aminomethyl)phenyl)benzofuran-5-yl)methoxy)phenyl)acetic Acid (330c)

Step-1: Preparation of methyl 2-(2-((7-(3-(((tert-butoxycarbonyl)amino)methyl)phenyl)benzofuran-5-yl)methoxy)-5-(1-ethoxyvinyl)phenyl)acetate (330a)

To a solution of methyl 2-(5-bromo-2-((7-(3-(((tert-butoxycarbonyl)amino)methyl)phenyl)benzofuran-5-yl)methoxy)phenyl)acetate (208b) (0.2 g, 0.35 mmol) in DMF (4 mL) was added tributyl(1-ethoxyvinyl)stannane (0.153 mL, 0.45 mmol) and Pd(PPh$_3$)$_4$ (0.04 g, 0.03 mmol), the resulting mixture was stirred at 100° C. for 2 h under argon atmosphere. The reaction mixture was cooled to room temperature, diluted with EtOAc (100 mL), washed with water (2×50 mL), brine (50 mL), dried, filtered and evaporated to dryness. The residue obtained was purified by flash column chromatography [silica gel, 12 g, eluting with ethyl acetate in hexanes from 0-50%] to furnish methyl 2-(2-((7-(3-(((tert-butoxycarbonyl)amino)methyl)phenyl)benzofuran-5-yl)methoxy)-5-(1-ethoxyvinyl)phenyl)acetate (330a) (0.05 g, 25% yield) as a white solid. MS (ES+): 494.9 (M-Boc+Na).

Step-2: Preparation of methyl 2-(5-acetyl-2-((7-(3-(aminomethyl)phenyl)benzofuran-5-yl)methoxy)phenyl)acetate (330b)

Compound 330b was prepared according to the procedure reported in step-10 of scheme-257 from methyl 2-(2-((7-(3-(((tert-butoxycarbonyl)amino)methyl)phenyl)benzofuran-5-yl)methoxy)-5-(1-ethoxyvinyl)phenyl)acetate (330a) (0.05 g, 0.09 mmol) in methanol (3 mL) using hydrochloric acid (4M in 1,4-dioxane, 0.66 mL, 2.62 mmol). This gave after workup methyl 2-(5-acetyl-2-((7-(3-(aminomethyl)phenyl)benzofuran-5-yl)methoxy)phenyl)acetate (330b) (0.04 g, 100% yield) as a yellow solid; MS (ES+): 440.0 (M+1).

Step-3: Preparation of 2-(5-acetyl-2-((7-(3-(aminomethyl)phenyl)benzofuran-5-yl)methoxy)phenyl) acetic Acid (330c)

Compound 330c was prepared according to the procedure reported in step-6 of scheme-1 from methyl 2-(5-acetyl-2-((7-(3-(aminomethyl)phenyl)benzofuran-5-yl)methoxy)phenyl)acetate (330b) (0.05 g, 0.11 mmol) in THF (4 mL) and methanol (4 mL) using lithium hydroxide hydrate (0.04 g, 0.90 mmol) in water (1 mL). This gave after workup and purification by flash column chromatography [silica gel, 12 g, eluting with methanol in DCM from 0-50%] followed by reverse phase column chromatography [C18 (50g), eluting with ACN in water (containing 0.1% HCl) from 0-100%] 2-(5-acetyl-2-((7-(3-(aminomethyl)phenyl)benzofuran-5-yl)methoxy)phenyl)acetic acid (330c) (0.02 g, 41% yield) HCl salt as a white solid; $^1$H NMR (300 MHz, DMSO-$d_6$) δ 12.35 (s, 1H), 8.28 (s, 3H), 8.11 (d, J=2.2 Hz, 1H), 7.99 (s, 1H), 7.97-7.83 (m, 3H), 7.77 (d, J=1.6 Hz, 1H), 7.64 (d, J=1.6 Hz, 1H), 7.60 (t, J=7.7 Hz, 1H), 7.53 (d, J=7.7 Hz, 1H), 7.21 (d, J=8.6 Hz, 1H), 7.07 (d, J=2.2 Hz, 1H), 5.39 (s, 2H), 4.14 (s, 2H), 3.67 (s, 2H), 2.51 (s, 3H); MS (ES+): 430.0 (M+1).

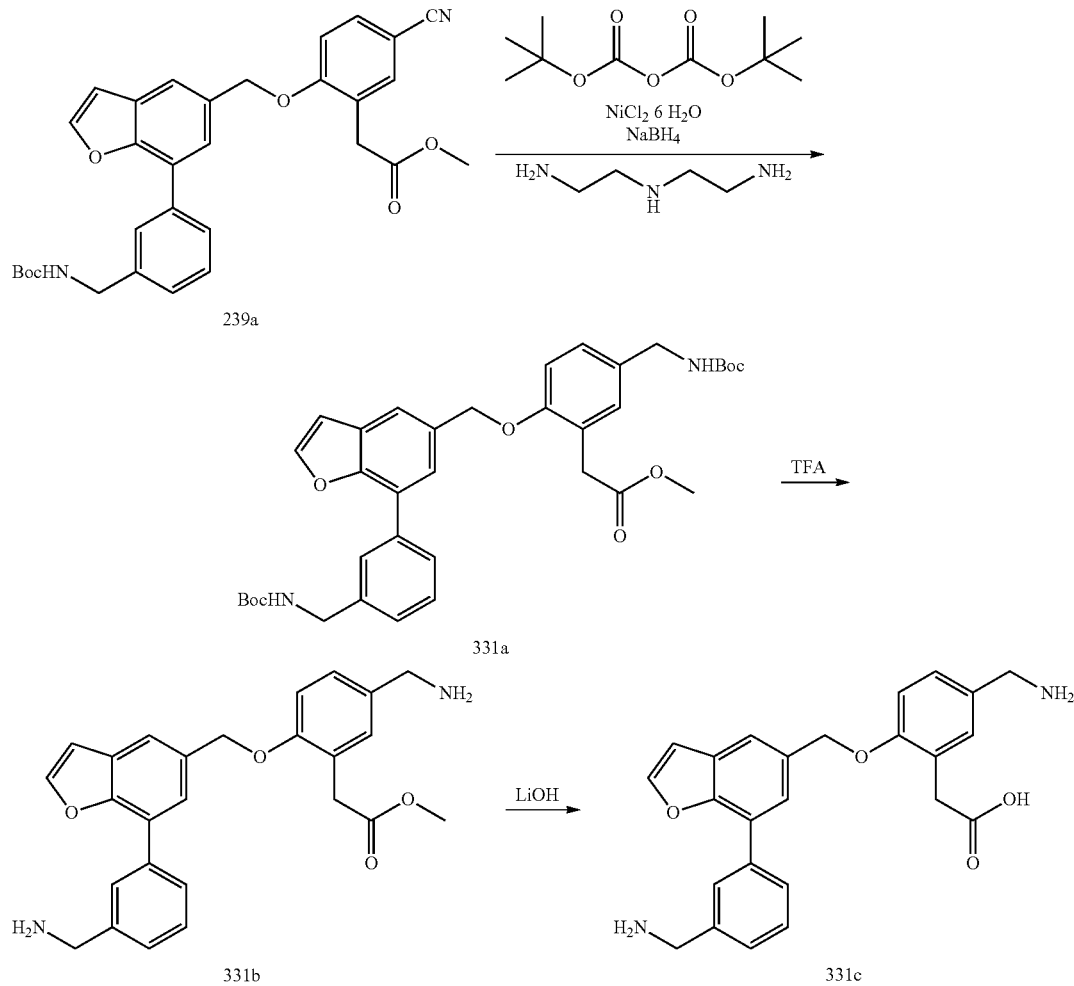

Scheme-331

Preparation of 2-(5-(aminomethyl)-2-((7-(3-(aminomethyl)phenyl)benzofuran-5-yl)methoxy)phenyl) acetic Acid (331c)

Step-1: Preparation of methyl 2-(5-(((tert-butoxycarbonyl)amino)methyl)-2-((7-(3-(((tert-butoxycarbonyl)amino)methyl)phenyl)benzofuran-5-yl) methoxy)phenyl)acetate (331a)

Compound 331a was prepared according to the procedure reported in step-2 of scheme-256 from methyl 2-(2-((7-(3-(((tert-butoxycarbonyl)amino)methyl)phenyl)benzofuran-5-yl)methoxy)-5 cyanophenyl)acetate (239a) (0.06 g, 0.11 mmol) in anhydrous methanol (5 mL) using nickel(II) chloride hexahydrate (7 mg, 0.03 mmol), di-tert-butyl dicarbonate [(Boc)$_2$O)] (0.08 g, 0.34 mmol), sodium borohydride (0.03 g, 0.68 mmol) and quenching with N1-(2-aminoethyl)ethane-1,2-diamine (0.03 mL, 0.23 mmol). This gave after workup and purification by flash column chromatography (silica gel, 4 g, eluting with ethyl acetate/hexanes from 0 to 60%) methyl 2-(5-(((tert-butoxycarbonyl)amino)methyl)-2-((7-(3-(((tert-butoxycarbonyl)amino)methyl)phenyl)benzofuran-5-yl)methoxy)phenyl)acetate (331a) (0.03 g, 47% yield) as a pale yellow wax; MS (ES+): 531.0 (M-Boc+1).

Step-2: Preparation of methyl 2-(5-(aminomethyl)-2-((7-(3-(aminomethyl)phenyl)benzofuran-5-yl)methoxy)phenyl)acetate (331b)

Compound 331b was prepared according to the procedure reported in step-5 of scheme-1 from methyl 2-(5-(((tert-butoxycarbonyl)amino)methyl)-2-((7-(3-(((tert-butoxycarbonyl)amino)methyl)phenyl)benzofuran-5-yl)methoxy)phenyl)acetate (331a) (0.03 g, 0.05 mmol) in DCM (3 mL) using TFA (0.08 mL, 1.08 mmol). This gave after workup and purification by flash column chromatography [silica gel, 12 g, eluting with MeOH in DCM from 0-50%] methyl 2-(5-(aminomethyl)-2-((7-(3-(aminomethyl)phenyl)benzofuran-5-yl)methoxy)phenyl)acetate (331b) (0.02 g, 100% yield) as a clear wax; MS (ES+): 431.1 (M+1).

Step-3: Preparation of 2-(5-(aminomethyl)-2-((7-(3-(aminomethyl)phenyl)benzofuran-5-yl)methoxy)phenyl)acetic Acid (331c)

Compound 331c was prepared according to the procedure reported in step-6 of scheme-1 from methyl 2-(5-(aminomethyl)-2-((7-(3-(aminomethyl)phenyl)benzofuran-5-yl)methoxy)phenyl)acetate (331b) (0.04 g, 0.09 mmol) in THF (4 mL) and methanol (4 mL) using a solution of lithium hydroxide hydrate (0.03 g, 0.74 mmol) in water (1 mL). This gave after workup and purification by reverse phase column chromatography [C-18, 50 g, eluting with 0.1% aq. HCl in water and acetonitrile from 0-100%] 2-(5-(aminomethyl)-2-((7-(3-(aminomethyl)phenyl)benzofuran-5-yl)methoxy)phenyl)acetic acid (331c) (0.02 g, 47% yield) HCl salt as a white solid; $^1$H NMR (300 MHz, DMSO-d$_6$) δ 12.33 (s, 1H), 8.45 (s, 3H), 8.26 (s, 3H), 8.11 (d, J=2.2 Hz, 1H), 8.01 (d, J=2.1 Hz, 1H), 7.92 (dt, J=7.1, 1.9 Hz, 1H), 7.75 (d, J=1.6 Hz, 1H), 7.65 (d, J=1.7 Hz, 1H), 7.63-7.58 (m, 1H), 7.57 (d, J=2.0 Hz, 1H), 7.40-7.27 (m, 2H), 7.14 (d, J=8.4 Hz, 1H), 7.06 (d, J=2.2 Hz, 1H), 5.31 (s, 2H), 4.13 (s, 2H), 3.92 (s, 2H), 3.60 (s, 2H); MS (ES+): 417.2 (M+1); MS (ES−): 415.1 (M−1); Analysis calculated for C$_{25}$H$_{24}$N$_2$O$_4$·3HCl·2H$_2$O: C, 55.25; H, 5.94; Cl, 13.05; N, 5.15; Found: C, 54.92; H, 5.64; Cl, 13.41; N, 5.17.

Scheme-332

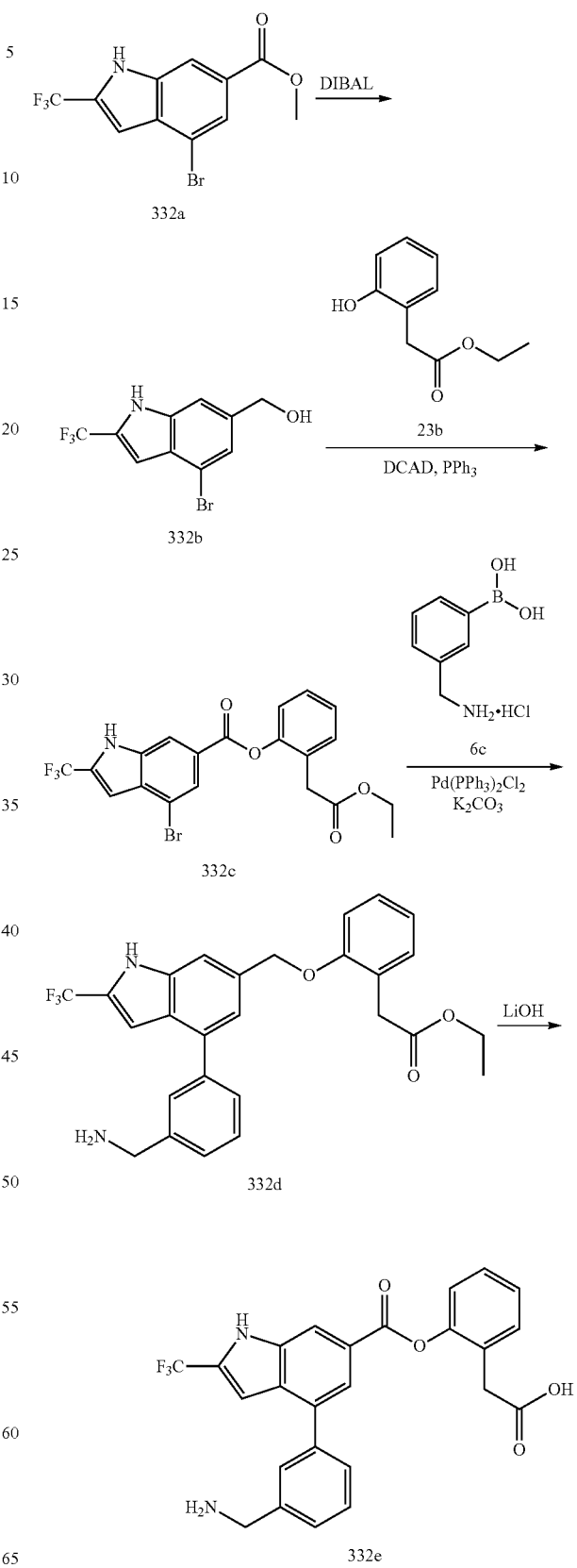

Preparation of 2-(2-((4-(3-(aminomethyl)phenyl)-2-(trifluoromethyl)-1H-indol-6-yl)methoxy)phenyl) acetic Acid (332e)

Step-1: Preparation of (4-bromo-2-(trifluoromethyl)-1H-indol-6-yl)methanol (332b)

Compound 332b was prepared according to the procedure reported in step-2 of scheme-212 from methyl 4-bromo-2-(trifluoromethyl)-1H-indole-6-carboxylate (332a) (1.29 g, 4.01 mmol; CAS #2089041-22-3; prepared according to the procedure reported by Yang, Xinye et al; in Faming Zhuanli Shenqing, 106478500, 8 Mar. 2017) in DCM (25 mL) using 1 M DIBAL-H in DCM (10.01 mL, 10.01 mmol). This gave after workup and purification by flash column chromatography (silica gel, 12 g, eluting with 0-50% EtOAc in Hexane) (4-bromo-2-(trifluoromethyl)-1H-indol-6-yl)methanol (332b) (1.05 g, 89% yield) as a brown solid; MS (ES−): 293.0 & 291.9 (M−1).

Step-2: Preparation of Ethyl 2-(2-((4-bromo-2-(trifluoromethyl)-1H-indol-6-yl)methoxy)phenyl)acetate (332c)

Compound 332c was prepared according to the procedure reported in step-2 of scheme-23 from (4-bromo-2-(trifluoromethyl)-1H-indol-6-yl)methanol (332b) (0.5 g, 1.70 mmol) in DCM (20 mL) using triphenylphosphine (0.58 g, 2.21 mmol), ethyl 2-(2-hydroxyphenyl) acetate (23b) (0.40 g, 2.21 mmol) and (E)-bis(4-chlorobenzyl) diazene-1,2-dicarboxylate (DCAD, 0.81 g, 2.21 mmol) in DCM (15 mL). This gave after workup and purification by flash column chromatography [silica gel 12 g column, eluting with EtOAc/MeOH=9:1 in hexanes from 0-30%] ethyl 2-(2-((4-bromo-2-(trifluoromethyl)-1H-indol-6-yl)methoxy)phenyl) acetate (332c) (0.15 g, 19% yield) as a white oil; MS (ES−): 456.0 & 454.0 (M−1).

Step-3: Preparation of Ethyl 2-(2-((4-(3-(aminomethyl)phenyl)-2-(trifluoromethyl)-1H-indol-6-yl)methoxy)phenyl)acetate (332d)

Compound 332d was prepared according to the procedure reported in step-3 of scheme-1 from ethyl 2-(2-((4-bromo-2-(trifluoromethyl)-1H-indol-6-yl)methoxy)phenyl)acetate (332c) (0.15 g, 0.33 mmol) in dioxane (4 mL) using 3-(aminomethyl)phenylboronic acid hydrochloride (6c) (0.09 g, 0.49 mmol), a solution of $K_2CO_3$ (0.46 g, 0.99 mmol) in water (2 mL), Pd(PPh$_3$)$_2$Cl$_2$ (0.04 g, 0.05 mmol) and heating under an Ar atmosphere at 90° C. for 2 h. This gave after workup and purification by flash column chromatography [silica (12 g), eluting with MeOH in DCM from 0-30%] ethyl 2-(2-((4-(3-(aminomethyl)phenyl)-2-(trifluoromethyl)-1H-indol-6-yl)methoxy)phenyl)acetate (332d) (0.1 g, 63% yield) as a white solid; MS (ES+): 483.2 (M+1).

Step-4: Preparation of 2-(2-((4-(3-(aminomethyl)phenyl)-2-(trifluoromethyl)-1H-indol-6-yl)methoxy)phenyl)acetic Acid (332e)

Compound 332e was prepared according to the procedure reported in step-6 of scheme-1 from ethyl 2-(2-((4-(3-(aminomethyl)phenyl)-2-(trifluoromethyl)-1H-indol-6-yl)methoxy)phenyl)acetate (332d) (0.1 g, 0.21 mmol) in THF (4 mL) and MeOH (4 mL) using a solution of lithium hydroxide hydrate (0.04 g, 0.83 mmol) in water (1 mL). This gave after workup and purification by reverse phase column [C18 (50 g), eluting with ACN in water (containing 0.1% HCl) from 0-100%] 2-(2-((4-(3-(aminomethyl)phenyl)-2-(trifluoromethyl)-1H-indol-6-yl)methoxy)phenyl)acetic acid (332e) (3 mg, 3% yield) HCl salt as a white solid; $^1$H NMR (300 MHz, DMSO-d$_6$) δ 12.56 (s, 1H), 12.18 (s, 1H), 8.23 (s, 3H), 7.82 (s, 1H), 7.70 (d, J=7.5 Hz, 1H), 7.62-7.55 (m, 2H), 7.51 (d, J=7.7 Hz, 1H), 7.34 (s, 1H), 7.23 (t, J=7.0 Hz, 2H), 7.17 (s, 1H), 7.09 (d, J=9.0 Hz, 1H), 6.90 (t, J=7.4 Hz, 1H), 5.31 (s, 2H), 4.16 (d, J=5.8 Hz, 2H), 3.60 (s, 2H); $^{19}$F NMR (282 MHz, DMSO) δ−58.73; MS (ES+): 455.1 (M+1); MS (ES−): 453.1 (M−1).

Scheme-333

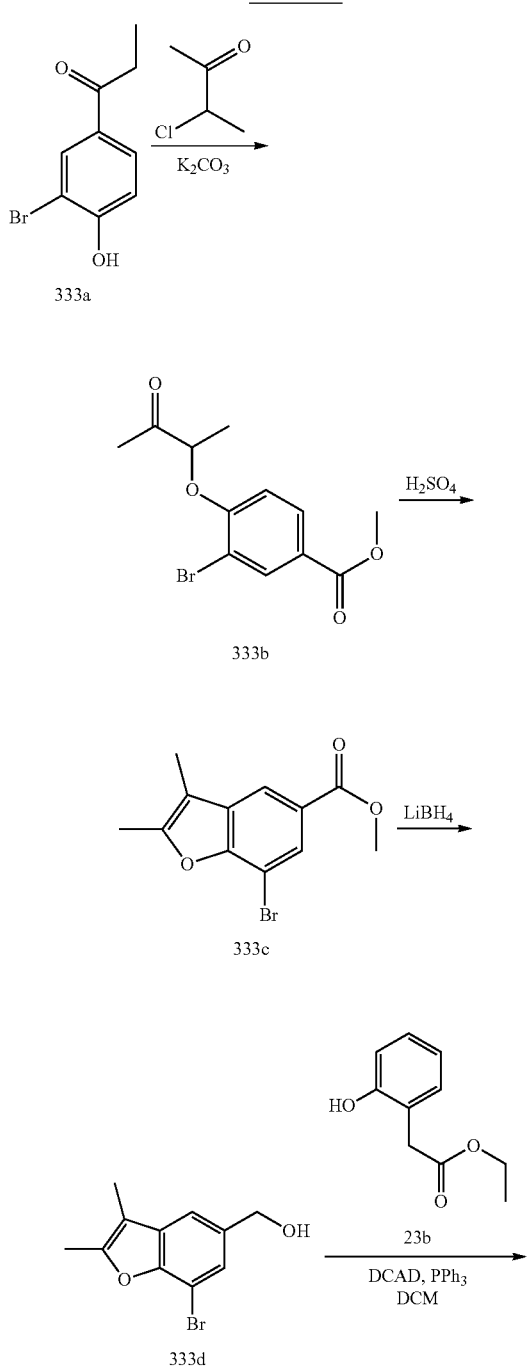

-continued

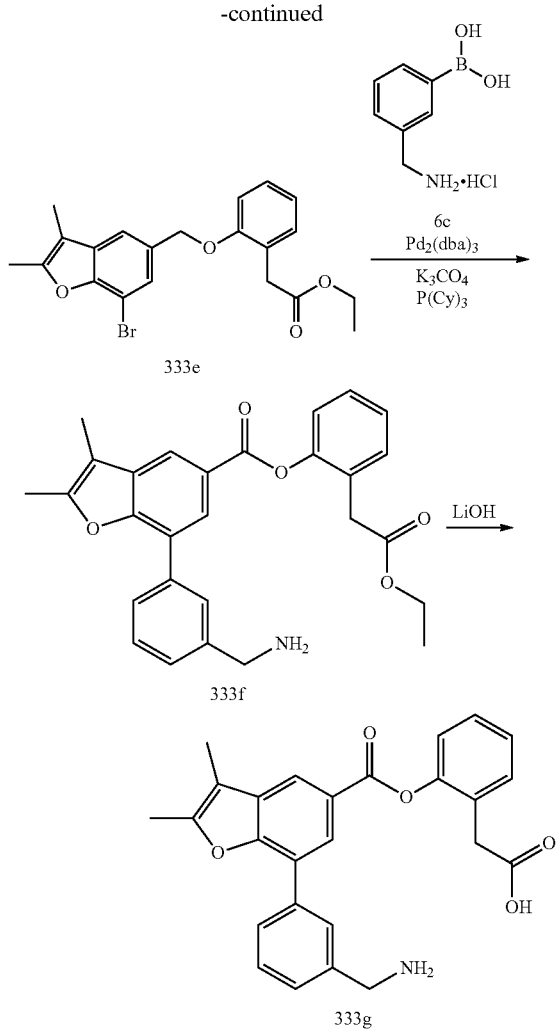

Preparation of 2-(2-((7-(3-(aminomethyl)phenyl)-2,3-dimethylbenzofuran-5-yl)methoxy)phenyl)acetic Acid (333g)

Step-1: Preparation of methyl 3-bromo-4-((3-oxobutan-2-yl)oxy)benzoate (333b)

To a solution of methyl 3-bromo-4-hydroxybenzoate (333a) (50g, 216 mmol) and 3-chlorobutan-2-one (21.86 mL, 216 mmol) in anhydrous acetone (240 mL) was added K$_2$CO$_3$ (90 g, 649 mmol) and heated at reflux for 24 h. The reaction mixture was cooled to room temperature and solid obtained was removed by filtration. The filtrate was concentrated in vacuum and the residue obtained was recrystallized from acetone-Hexane mixture. The solid was collected by filtration and mother liquor was purified by flash column chromatography [(silica gel, 320 g, eluting with ethyl acetate/hexanes from 0 to 30%)] to afford methyl 3-bromo-4-((3-oxobutan-2-yl)oxy)benzoate (333b) (56.1 g, 86% yield). $^1$H NMR (300 MHz, DMSO-d$_6$) δ 8.11 (d, J=2.1 Hz, 1H), 7.88 (dd, J=8.7, 2.2 Hz, 1H), 7.07 (d, J=8.8 Hz, 1H), 5.20 (q, J=6.9 Hz, 1H), 3.83 (s, 3H), 2.24 (s, 3H), 1.50 (d, J=6.8 Hz, 3H).

Step-2: Preparation of methyl 7-bromo-2,3-dimethylbenzofuran-5-carboxylate (333c)

To methyl 3-bromo-4-((3-oxobutan-2-yl)oxy)benzoate (333b) (56 g, 186 mmol) was added sulfuric acid (41.7 mL, 744 mmol) at ice-cold temperature. The reaction mixture was stirred at room temperature for one hour and heated at 50° C. for 1 h. The mixture was recrystallized from EtOH to afford methyl 7-bromo-2,3-dimethylbenzofuran-5-carboxylate (333c) (29.5 g, 56% yield). $^1$H NMR (300 MHz, DMSO-d$_6$) δ 8.11 (d, J=1.6 Hz, 1H), 7.98 (d, J=1.5 Hz, 1H), 3.88 (s, 3H), 2.45 (d, J=1.0 Hz, 3H), 2.19 (d, J=1.0 Hz, 3H).

Step-3: Preparation of (7-bromo-2,3-dimethylbenzofuran-5-yl)methanol (333d)

Compound 333d was prepared according to the procedure reported in step-2 of scheme-76 from methyl 7-bromo-2,3-dimethylbenzofuran-5-carboxylate (333c) (10 g, 35.3 mmol) in THF (150 mL) using LiBH$_4$ (17.66 mL, 70.6 mmol) and MeOH (2.86 mL, 70.6 mmol). This gave after workup and purification by flash column chromatography [silica (80 g), eluting with ethyl acetate in hexane from 0-60%] (7-bromo-2,3-dimethylbenzofuran-5-yl)methanol (333d) (7.05 g, 78% yield) as a white solid; $^1$H NMR (300 MHz, DMSO-d$_6$) δ 7.44-7.35 (m, 2H), 5.29 (t, J=5.8 Hz, 1H), 4.56 (dt, J=5.8, 0.7 Hz, 2H), 2.41 (d, J=1.0 Hz, 3H), 2.13 (d, J=0.9 Hz, 3H).

Step-4: Preparation of Ethyl 2-(2-((7-bromo-2,3-dimethylbenzofuran-5-yl)methoxy)phenyl)acetate (333e)

Compound 333e was prepared according to the procedure reported in step-2 of scheme-23 from (7-bromo-2,3-dimethylbenzofuran-5-yl)methanol (333d) (1 g, 3.92 mmol) in DCM (10 mL) using triphenylphosphine (1.131 g, 4.31 mmol), ethyl 2-(2-hydroxyphenyl) acetate (23b) (0.777 g, 4.31 mmol) and (E)-bis(4-chlorobenzyl) diazene-1,2-dicarboxylate (DCAD, 1.583 g, 4.31 mmol) in DCM (10 mL). This gave after workup and purification by flash column chromatography [silica (24g), eluting with ethyl acetate in hexane from 0-50%] ethyl 2-(2-((7-bromo-2,3-dimethylbenzofuran-5-yl)methoxy)phenyl)acetate (333e) (704 mg, 43% yield) as a white solid. $^1$HNMR (300 MHz, DMSO-d$_6$) δ 7.55 (d, J=1.5 Hz, 1H), 7.49 (d, J=1.5 Hz, 1H), 7.32-7.18 (m, 2H), 7.12-7.03 (m, 1H), 6.91 (td, J=7.4, 1.1 Hz, 1H), 5.16 (s, 2H), 4.02 (q, J=7.1 Hz, 2H), 3.62 (s, 2H), 2.42 (d, J=1.0 Hz, 3H), 2.14 (d, J=1.0 Hz, 3H), 1.08 (t, J=7.1 Hz, 3H).

Step-5: Preparation of Ethyl 2-(2-((7-(3-(aminomethyl)phenyl)-2,3-dimethylbenzofuran-5-yl)methoxy)phenyl)acetate (333f)

Compound 333f was prepared according to the procedure reported in step-3 of scheme-1 from ethyl 2-(2-((7-bromo-2,3-dimethylbenzofuran-5-yl)methoxy)phenyl)acetate (333e) (300 mg, 0.719 mmol) in dioxane (10 mL) using 3-(aminomethyl)phenylboronic acid hydrochloride (6c) (163 mg, 1.078 mmol), tripotassium phosphate (1.3M, 1.7 mL, 2.2 mmol), tricyclohexylphosphine (61 mg, 0.216 mmol) and Pd$_2$(dba)$_3$ (66 mg, 0.072 mmol) under a nitrogen atmosphere and heating at 125° C. for 60 min in a microwave. This gave after workup, purification by flash column chromatography [silica gel, 24 g, eluting with DCM/DMA80] ethyl 2-(2-((7-(3-(aminomethyl)phenyl)-2,3-dimethylbenzofuran-5-yl)methoxy)phenyl)acetate (333f) (164 mg, 51% yield). ¹H NMR (300 MHz, DMSO-d₆) δ 7.78 (s, 1H), 7.75-7.66 (m, 1H), 7.52 (d, J=1.7 Hz, 1H), 7.50-7.40 (m, 2H), 7.37 (d, J=7.7 Hz, 1H), 7.32-7.20 (m, 1H), 7.26-7.17 (m, 1H), 7.16-7.07 (m, 1H), 6.90 (td, J=7.4, 1.1 Hz, 1H), 5.22 (s, 2H), 3.93 (q, J=7.1 Hz, 2H), 3.80 (s, 2H), 3.63 (s, 2H), 2.41 (d, J=1.0 Hz, 3H), 2.17 (d, J=1.0 Hz, 3H), 0.99 (t, J=7.1 Hz, 3H); MS (ES+): 444.2 (M+1).

Step-6: Preparation of 2-(2-((7-(3-(aminomethyl)phenyl)-2,3-dimethylbenzofuran-5-yl)methoxy)phenyl)acetic Acid (333g)

Compound 333g was prepared according to the procedure reported in step-6 of scheme-1 from ethyl 2-(2-((7-(3-(aminomethyl)phenyl)-2,3-dimethylbenzofuran-5-yl)methoxy)phenyl)acetate (333f) (160 mg, 0.361 mmol) in MeOH/THF (5 mL each) using a solution of aqueous 1 N lithium hydroxide (1.082 mL, 1.082 mmol). This gave after workup and purification by reverse phase column [C18 (50g), eluting with ACN in water (containing 0.1% HCl) from 0-100%] 2-(2-((7-(3-(aminomethyl)phenyl)-2,3-dimethylbenzofuran-5-yl)methoxy)phenyl)acetic acid (333g) (120 mg, 80% yield) HCl salt as a white solid; ¹H NMR (300 MHz, DMSO-d₆) δ 8.00-7.87 (m, 2H), 7.64-7.47 (m, 4H), 7.30-7.18 (m, 2H), 7.09 (d, J=8.0 Hz, 1H), 6.90 (td, J=7.4, 1.1 Hz, 1H), 5.25 (s, 2H), 4.13 (s, 2H), 3.60 (s, 2H), 2.42 (s, 3H), 2.18 (s, 3H); MS (ES+): 416.2 (M+1); (ES-): 414.0 (M-1); Analysis Calculated for $C_{26}H_{25}NO_4 \cdot HCl \cdot 0.75H_2O$: C, 67.09; H, 5.96; Cl, 7.62; N, 3.01; found: C, 67.03; H, 5.89; Cl, 7.53; N, 3.04.

Scheme-334

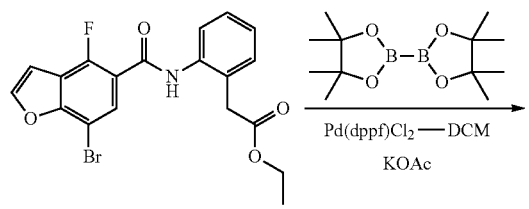

241a

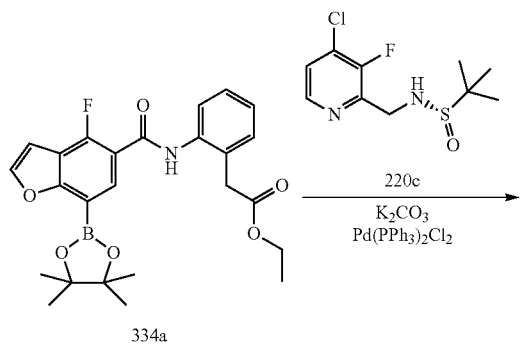

334a

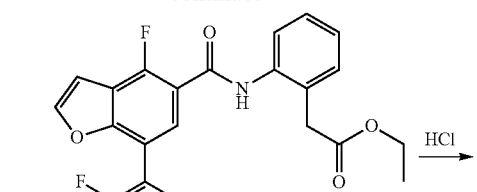

334b

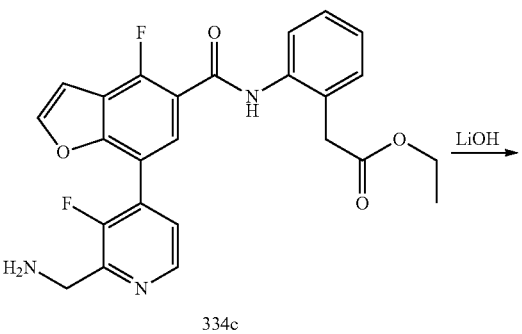

334c

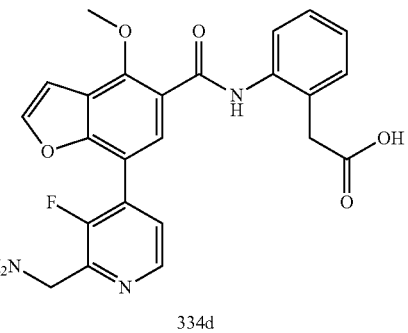

334d

Preparation of 2-(2-(7-(2-(aminomethyl)-3-fluoropyridin-4-yl)-4-methoxybenzofuran-5-carboxamido)phenyl)acetic Acid (334d)

Step-1: Preparation of Ethyl 2-(2-(4-fluoro-7-(4,4,5,5-tetramethyl-1,3,2-dioxaborolan-2-yl)benzofuran-5-carboxamido)phenyl)acetate (334a)

Compound 334a was prepared according to the procedure reported in step-1 of scheme-59 from ethyl 2-(2-(7-bromo-4-fluorobenzofuran-5-carboxamido)phenyl)acetate (241a) (193 mg, 0.459 mmol), using bis(pinacolato)diboron (178 mg, 0.701 mmol), potassium acetate (165 mg, 1.681 mmol) and Pd(dppf)Cl₂-DCM (66 mg, 0.081 mmol) in anhydrous dioxane (6 mL) under an argon atmosphere and heating at 90° C. overnight. This gave after workup and purification by flash column chromatography [silica (12 g), eluting with EtOAc in hexanes from 0-50%] ethyl 2-(2-(4-fluoro-7-(4,4,5,5-tetramethyl-1,3,2-dioxaborolan-2-yl)benzofuran-5-carboxamido)phenyl)acetate (334a) (128 mg, 60% yield) as pale-yellow oil. MS (ES+): 468.0 (M+1).

Step-2: Preparation of Ethyl 2-(2-(7-(2-((1,1-dimethylethylsulfinamido)methyl)-3-fluoropyridin-4-yl)-4-fluorobenzofuran-5-carboxamido)phenyl)acetate (334b)

Compound 334b was prepared according to the procedure reported in step-3 of scheme-1 from ethyl 2-(2-(4-fluoro-7-(4,4,5,5-tetramethyl-1,3,2-dioxaborolan-2-yl)benzofuran-5-carboxamido)phenyl)acetate (334a) (128 mg, 0.274 mmol) in dioxane (5 mL) using (+)-(S)—N-((4-chloro-3-fluoropyridin-2-yl)methyl)-2-methylpropane-2-sulfinamide (220c) (82 mg, 0.310 mmol), bis(triphenylphosphine)palladium(II) chloride (Pd(PPh₃)₂Cl₂) (45 mg, 0.064 mmol) and a solution of K₂CO₃ (134 mg, 0.970 mmol) in water (0.5 mL) under an argon atmosphere heating at 100° C. for 3 h on oil bath. This gave after workup, purification by flash column chromatography [silica(12 g), eluting with DMA/DCM from 0-80%] ethyl 2-(2-(7-(2-((1,1-dimethylethylsulfinamido)methyl)-3-fluoropyridin-4-yl)-4-fluorobenzofuran-5-carboxamido)phenyl)acetate (334b) (156 mg, 100% yield) as yellow oil; MS (ES+): 570.1 (M+1).

Step-3: Preparation of Ethyl 2-(2-(7-(2-(aminomethyl)-3-fluoropyridin-4-yl)-4-fluorobenzofuran-5-carboxamido)phenyl)acetate (334c)

Compound 334c was prepared according to the procedure reported in step-3 of scheme-305 from ethyl 2-(2-(7-(2-((1,1-dimethylethylsulfinamido)methyl)-3-fluoropyridin-4-yl)-4-fluorobenzofuran-5-carboxamido)phenyl)acetate (334b) (156 mg, 0.274 mmol) in methanol (8 mL) using HCl (4M in dioxane; 0.3 mL, 1.200 mmol) and stirring at room temperature for 30 mins. This gave after workup, purification by flash column chromatography [silica (12 g), eluting with DMA80/DCM from 0-100%] ethyl 2-(2-(7-(2-(aminomethyl)-3-fluoropyridin-4-yl)-4-fluorobenzofuran-5-carboxamido)phenyl)acetate (334c) (31 mg, 25% yield) as pale-yellow oil. MS (ES+): 452.1 (M+1).

Step-4: Preparation of 2-(2-(7-(2-(aminomethyl)-3-fluoropyridin-4-yl)-4-methoxybenzofuran-5-carboxamido)phenyl)acetic Acid (334d)

Compound 334d was prepared according to the procedure reported in step-6 of scheme-1 from ethyl 2-(2-(7-(2-(aminomethyl)-3-fluoropyridin-4-yl)-4-fluorobenzofuran-5-carboxamido)phenyl)acetate (334c) (31 mg, 0.069 mmol) in MeOH (6 mL), THF (6 mL) using a solution of lithium hydroxide (46 mg, 1.10 mmol) in water (2 mL). This gave after workup and purification by reverse phase column [C18 (50 g), eluting with ACN in water (containing 0.1% HCl) from 0-100%] 2-(2-(7-(2-(aminomethyl)-3-fluoropyridin-4-yl)-4-methoxybenzofuran-5-carboxamido)phenyl)acetic acid (334d) (11 mg, 36% yield) HCl salt as a white solid; $^1$H NMR (300 MHz, DMSO-d₆) δ 9.91 (s, 1H), 8.55 (d, J=5.0 Hz, 1H), 8.49 (s, 3H), 8.12 (d, J=2.4 Hz, 1H), 7.98 (d, J=1.0 Hz, 1H), 7.76 (t, J=5.3 Hz, 1H), 7.68 (d, J=7.7 Hz, 1H), 7.50 (d, J=2.3 Hz, 1H), 7.26 (t, J=7.6 Hz, 2H), 7.18-7.02 (m, 1H), 4.31 (d, J=6.0 Hz, 2H), 4.28 (s, 3H), 3.66 (s, 2H); MS (ES+): 450.1 (M+1); MS (ES−): 448.1 (M−1).

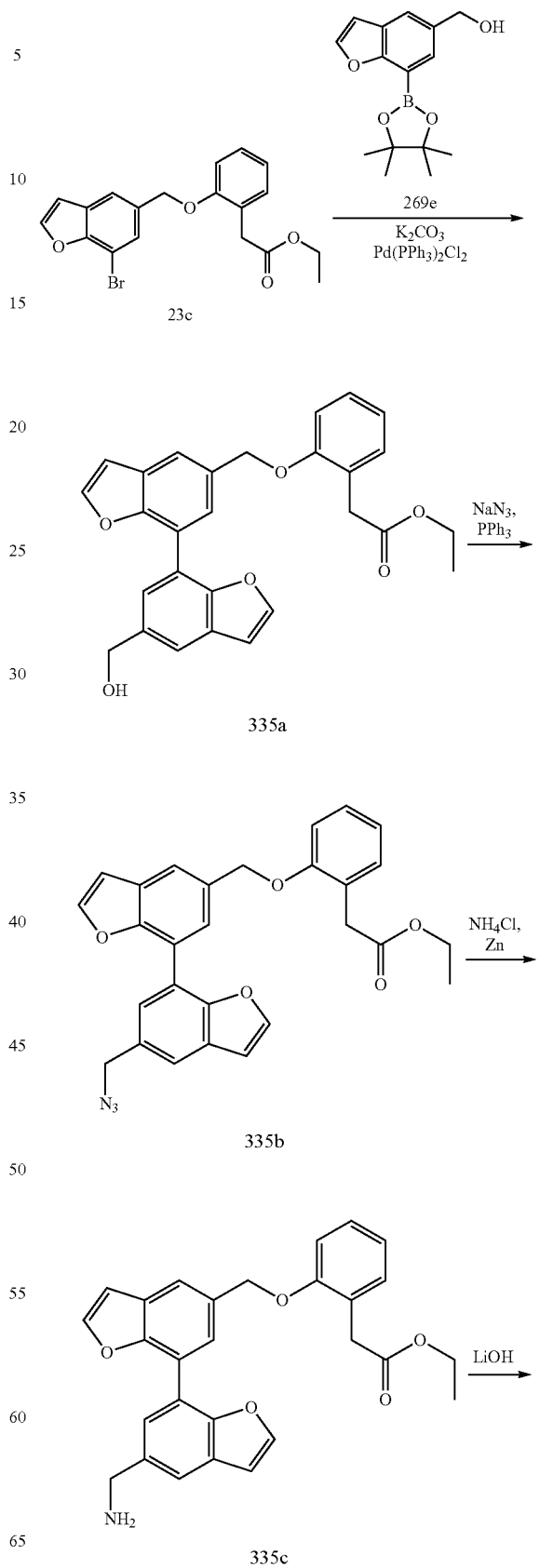

Scheme-335

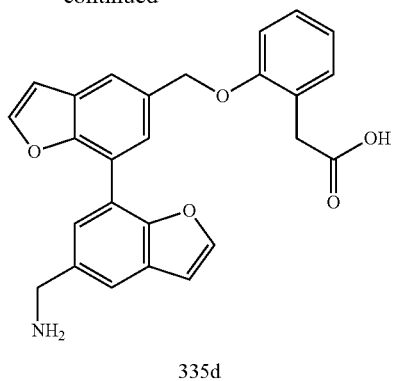

335d

Preparation of 2-(2-((5'-(aminomethyl)-[7,7'-bibenzofuran]-5-yl)methoxy)phenyl)acetic acid (335d)

Step-1: Preparation of Ethyl 2-(2-((5'-(hydroxymethyl)-[7,7'-bibenzofuran]-5-yl)methoxy)phenyl)acetate (335a)

Compound 335a was prepared according to the procedure reported in step-3 of scheme-1 from ethyl 2-(2-((7-bromobenzofuran-5-yl)methoxy)phenyl)acetate (23c) (464 mg, 1.192 mmol) in dioxane (5 mL) using (7-(4,4,5,5-tetramethyl-1,3,2-dioxaborolan-2-yl)benzofuran-5-yl)methanol (269e) (329 mg, 1.200 mmol), bis(triphenylphosphine)palladium(II) chloride (Pd(PPh$_3$)$_2$Cl$_2$) (111 mg, 0.158 mmol) and a solution of K$_2$CO$_3$ (530 mg, 3.83 mmol) in water (0.5 mL) under an argon atmosphere heating at 100° C. for 3 h on oil bath. This gave after workup, purification by flash column chromatography [silica(12 g), eluting with ethyl acetate in hexanes from 10-80%] ethyl 2-(2-((5'-(hydroxymethyl)-[7,7'-bibenzofuran]-5-yl)methoxy)phenyl)acetate (335a) (357 mg, 66% yield) as a pale-yellow oil. $^1$H NMR (300 MHz, DMSO-d$_6$) δ 8.08 (d, J=2.2 Hz, 1H), 8.02 (d, J=2.2 Hz, 1H), 7.78 (d, J=1.6 Hz, 1H), 7.72 (d, J=1.7 Hz, 1H), 7.68 (d, J=1.7 Hz, 1H), 7.63 (d, J=1.5 Hz, 1H), 7.31-7.18 (m, 2H), 7.14 (d, J=8.1 Hz, 1H), 7.08 (d, J=2.2 Hz, 1H), 7.05 (d, J=2.2 Hz, 1H), 6.91 (td, J=7.4, 1.1 Hz, 1H), 5.30 (t, J=5.7 Hz, 3H), 4.66 (d, J=5.7 Hz, 2H), 3.85 (q, J=7.1 Hz, 2H), 3.62 (s, 2H), 0.92 (t, J=7.1 Hz, 3H).

Step-2: Preparation of Ethyl 2-(2-((5'-(azidomethyl)-[7,7'-bibenzofuran]-5-yl)methoxy)phenyl)acetate (335b)

To a solution of ethyl 2-(2-((5'-(hydroxymethyl)-[7,7'-bibenzofuran]-5-yl)methoxy)phenyl)acetate (335a) (352 mg, 0.771 mmol) in CCl$_4$(8 mL) DMF (2 mL) was added NaN$_3$ (82 mg, 1.261 mmol) and PPh$_3$ (486 mg, 1.853 mmol) and heated at 90° C. for 3 h. The mixture was cooled to room temperature, quenched with water (10 mL) and stirred for 10 min. The reaction mixture was diluted with ethyl acetate and washed with water, dried, filtered and concentrated in vacuum to dryness. The residue obtained was purified by flash column chromatography [silica(12 g), eluting with DMA/DCM from 0-50%] to provide ethyl 2-(2-((5'-(azidomethyl)-[7,7'-bibenzofuran]-5-yl)methoxy)phenyl)acetate (335b) (253 mg, 68% yield) as a colorless oil; $^1$H NMR (300 MHz, DMSO-d$_6$) δ 8.14-8.04 (m, 2H), 7.87-7.67 (m, 4H), 7.34-7.18 (m, 2H), 7.18-7.05 (m, 3H), 6.97-6.86 (m, 1H), 5.27 (s, 2H), 4.97 (s, 1H), 4.63 (s, 1H), 3.83 (q, J=7.1, 1.9 Hz, 2H), 3.62 (s, 2H), 0.90 (t, J=7.1, 2.6 Hz, 3H).

Step-3: Preparation of Ethyl 2-(2-((5'-(aminomethyl)-[7,7'-bibenzofuran]-5-yl)methoxy)phenyl)acetate (335c)

To the solution of ethyl 2-(2-((5'-(azidomethyl)-[7,7'-bibenzofuran]-5-yl)methoxy)phenyl)acetate (335b) (195 mg, 0.405 mmol) in EtOH (8 mL), water (3 mL) was added ammonium chloride (113 mg, 2.112 mmol), Zinc (90 mg, 1.376 mmol) and heated at reflux for 90 min. The reaction was stirred at room temperature and concentrated in vacuum to remove ethanol. The residue was dissolved in ethyl acetate washed with brine, dried filtered and concentrated in vacuum to dryness. The residue obtained was purified by flash column chromatography [silica (12 g), eluting with DMA80 in DCM from 0-70%] to give ethyl 2-(2-((5'-(aminomethyl)-[7,7'-bibenzofuran]-5-yl)methoxy)phenyl) acetate (335c) (72 mg, 39.0% yield) as a colorless oil; $^1$H NMR (300 MHz, DMSO-d$_6$) δ 8.07 (d, J=2.2 Hz, 1H), 8.02 (d, J=2.2 Hz, 1H), 7.78 (d, J=1.7 Hz, 1H), 7.72 (d, J=1.7 Hz, 1H), 7.70 (d, J=1.7 Hz, 1H), 7.66 (d, J=1.7 Hz, 1H), 7.31-7.18 (m, 2H), 7.18-7.11 (m, 1H), 7.07 (dd, J=8.0, 2.2 Hz, 2H), 6.91 (td, J=7.3, 1.1 Hz, 1H), 5.27 (s, 2H), 3.97 (s, 2H), 3.86 (q, J=7.1 Hz, 2H), 3.63 (s, 2H), 0.93 (t, J=7.1 Hz, 3H); MS (ES+): 456.2 (M+1).

Step-4: Preparation of 2-(2-((5'-(aminomethyl)-[7,7'-bibenzofuran]-5-yl)methoxy)phenyl)acetic Acid (335d)

Compound 335d was prepared according to the procedure reported in step-6 of scheme-1 from ethyl 2-(2-((5'-(aminomethyl)-[7,7'-bibenzofuran]-5-yl)methoxy)phenyl)acetate (335c) (70 mg, 0.154 mmol) in MeOH (6 mL), THF (6 mL) using a solution of lithium hydroxide hydrate (68 mg, 1.62 mmol) in water (2 mL). This gave after workup and purification by reverse phase column [C18 (50 g), eluting with ACN in water (containing 0.1% HCl) from 0-100%] 2-(2-((5'-(aminomethyl)-[7,7'-bibenzofuran]-5-yl)methoxy) phenyl)acetic acid (335d) (51 mg, 78% yield) HCl salt as a white solid. $^1$H NMR (300 MHz, DMSO-d$_6$) δ 8.50 (s, 2H), 8.02 (dd, J=7.3, 2.2 Hz, 2H), 7.82 (d, J=1.7 Hz, 1H), 7.78 (d, J=1.7 Hz, 1H), 7.73 (d, J=1.8 Hz, 1H), 7.67 (d, J=1.7 Hz, 1H), 7.25-7.10 (m, 2H), 7.10-6.97 (m, 3H), 6.84 (td, J=7.4, 1.1 Hz, 1H), 5.22 (s, 2H), 4.13 (s, 2H), 3.54 (s, 2H); MS (ES+): 428.2 (M+1); MS(ES-): 426.1 (M-1); Analysis calculated for C$_{26}$H$_{21}$NO$_5$.HCl.H$_2$O: C, 64.80; H, 5.02; Cl, 7.36; N, 2.91; Found: C, 64.54; H, 4.84; Cl, 7.59; N, 2.89.

Scheme-336

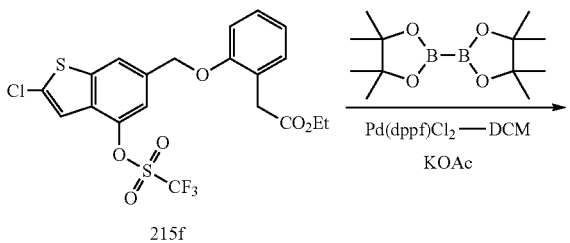

215f

Preparation of 2-(2-((4-(2-(aminomethyl)pyridin-4-yl)-2-chlorobenzo[b]thiophen-6-yl)methoxy)phenyl)acetic acid (336c)

Step-1: Preparation of Ethyl 2-(2-((2-chloro-4-(4,4,5,5-tetramethyl-1,3,2-dioxaborolan-2-yl)benzo[b]thiophen-6-yl)methoxy)phenyl)acetate (336a)

Compound 336a was prepared according to the procedure reported in step-1 of scheme-59 from ethyl 2-(2-((2-chloro-4-(((trifluoromethyl)sulfonyl)oxy)benzo[b]thiophen-6-yl)methoxy)phenyl)acetate (215f) (200 mg, 0.393 mmol), using bis(pinacolato)diboron (150 mg, 0.589 mmol), potassium acetate (116 mg, 1.179 mmol) and Pd(dppf)Cl$_2$-DCM (32 mg, 0.039 mmol) in anhydrous dioxane (5 mL) under an argon atmosphere and heating at 100° C. for 16 h. This gave after workup and purification by flash column chromatography [silica (12 g), eluting with 0-4% EtOAc in hexane] ethyl 2-(2-((2-chloro-4-(4,4,5,5-tetramethyl-1,3,2-dioxaborolan-2-yl)benzo[b]thiophen-6-yl)methoxy)phenyl)acetate (336a) (117 mg, 61% yield) as a colorless oil; $^1$H NMR (300 MHz, Chloroform-d) δ 7.90 (dq, J=1.5, 0.8 Hz, 1H), 7.83 (dd, J=5.0, 1.2 Hz, 2H), 7.25-7.20 (m, 2H), 6.99-6.89 (m, 2H), 5.17 (s, 2H), 4.12 (q, J=7.1 Hz, 2H), 3.68 (s, 2H), 1.40 (s, 12H), 1.19 (t, J=7.1 Hz, 3H).

Step-2: Preparation of Ethyl 2-(2-((4-(2-(aminomethyl)pyridin-4-yl)-2-chlorobenzo[b]thiophen-6-yl)methoxy)phenyl)acetate (336b)

Compound 336b was prepared according to the procedure reported in step-3 of scheme-1 from ethyl 2-(2-((2-chloro-4-(4,4,5,5-tetramethyl-1,3,2-dioxaborolan-2-yl)benzo[b]thiophen-6-yl)methoxy)phenyl)acetate (336a) (154 mg, 0.316 mmol) in dioxane (4 mL) using (4-chloropyridin-2-yl)methanamine (74a) (50 mg, 0.348 mmol), bis(triphenylphosphine)palladium(II) chloride (Pd(PPh$_3$)$_2$Cl$_2$) (22 mg, 0.032 mmol) and a solution of K$_2$CO$_3$ (131 mg, 0.949 mmol) in water (1 mL) under a nitrogen atmosphere heating at 100° C. for 16 h on oil bath. This gave after workup, purification by flash column chromatography [silica(12 g), eluting with 0-4% MeOH in DCM] ethyl 2-(2-((4-(2-(aminomethyl)pyridin-4-yl)-2-chlorobenzo[b]thiophen-6-yl)methoxy)phenyl)acetate (336b) (23 mg) as a pale-yellow oil (23 mg); MS (ES+): 467/469 (M+1).

Step-3: Preparation of 2-(2-((4-(2-(aminomethyl)pyridin-4-yl)-2-chlorobenzo[b]thiophen-6-yl)methoxy)phenyl)acetic Acid (336c)

Compound 336c was prepared according to the procedure reported in step-4 of scheme-4 from ethyl 2-(2-((4-(2-(aminomethyl)pyridin-4-yl)-2-chlorobenzo[b]thiophen-6-yl)methoxy)phenyl)acetate (336b) (23 mg, from above step-2) in MeOH (3 mL), using a solution of NaOH (63.3 mg, 1.582 mmol) in water (1 mL). This gave after workup and purification by reverse phase column (C18, 100 g, 0-60% MeCN in H$_2$O containing 0.1% HCl) 2-(2-((4-(2-(aminomethyl)pyridin-4-yl)-2-chlorobenzo[b]thiophen-6-yl)methoxy)phenyl)acetic acid (336c) (14 mg, 10% yield) HCl salt as a pale green solid; $^1$H NMR (300 MHz, DMSO-d$_6$) δ 8.76 (dd, J=5.2, 0.8 Hz, 1H), 8.46 (s, 3H), 8.15 (dd, J=1.5, 0.8 Hz, 1H), 7.77 (dd, J=1.8, 0.8 Hz, 1H), 7.65 (dd, J=5.2, 1.7 Hz, 1H), 7.62 (t, J=1.3 Hz, 2H), 7.32-7.17 (m, 2H), 7.14-7.01 (m, 1H), 6.92 (td, J=7.4, 1.1 Hz, 1H), 5.30 (s, 2H), 4.32 (t, J=5.5 Hz, 2H), 3.61 (s, 2H). HPLC purity: 100%; MS (ES+): 439/441 (M+1), (ES−): 437/439 (M−1).

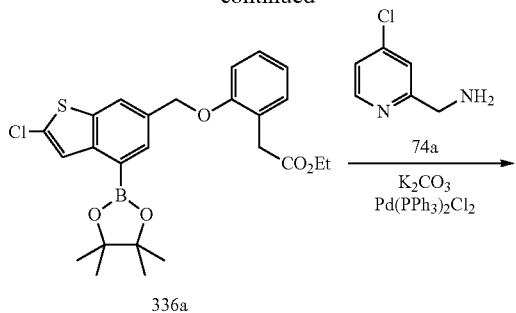

336a

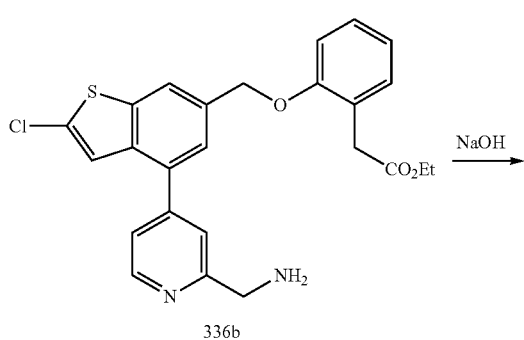

336b

336c

Scheme-337

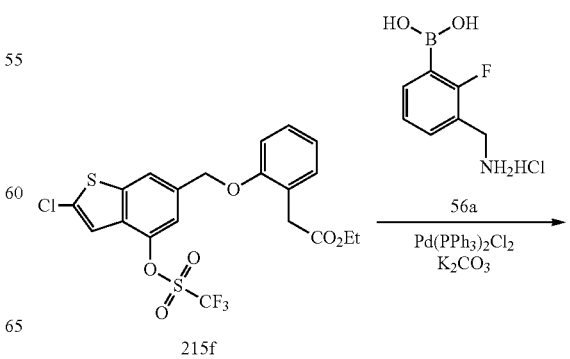

215f

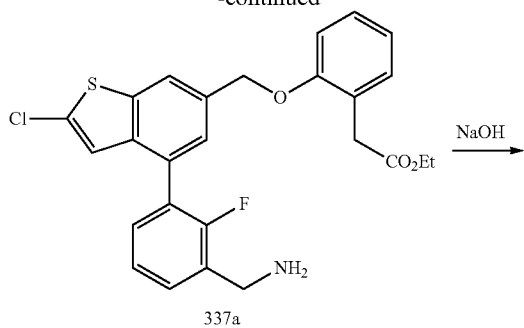

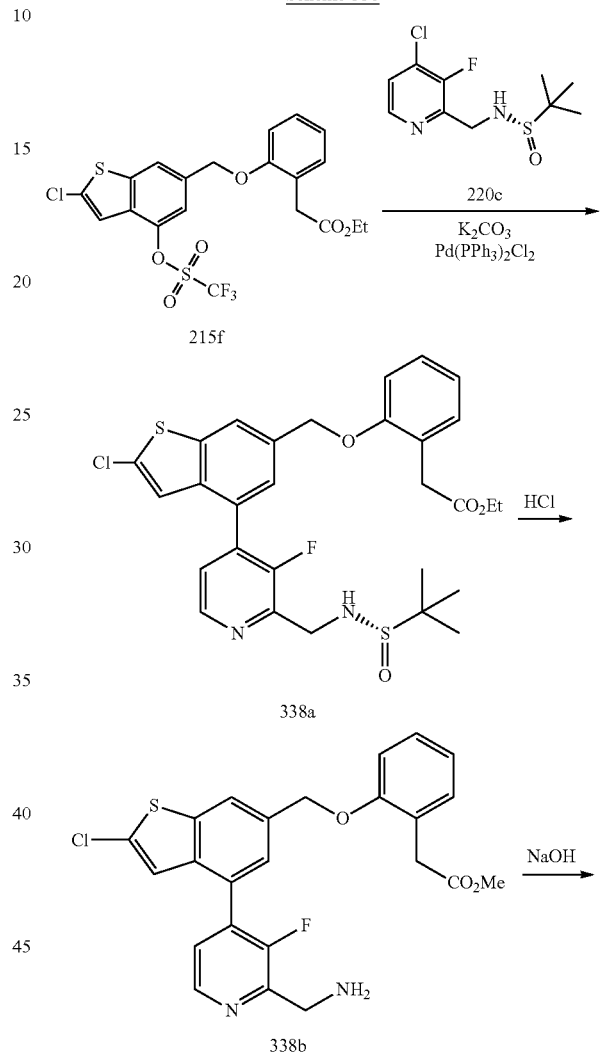

(dd, J=1.5, 0.8 Hz, 1H), 7.66 (td, J=7.1, 1.7 Hz, 1H), 7.55 (td, J=7.5, 2.0 Hz, 1H), 7.49 (d, J=1.5 Hz, 1H), 7.42 (t, J=7.6 Hz, 1H), 7.30 (dd, J=3.3, 0.7 Hz, 1H), 7.23 (t, J=7.5 Hz, 2H), 7.11-7.03 (m, 1H), 6.91 (td, J=7.4, 1.1 Hz, 1H), 5.29 (s, 2H), 4.16 (s, 2H), 3.59 (s, 2H); MS (ES+): 456/458 (M+1); (ES−): 454/456 (M−1).

Scheme-338

Preparation of 2-(2-((4-(3-(aminomethyl)-2-fluoro-phenyl)-2-chlorobenzo[b]thiophen-6-yl)methoxy) phenyl)acetic Acid (337b)

Step-1: Preparation of Ethyl 2-(2-((4-(3-(aminomethyl)-2-fluorophenyl)-2-chlorobenzo[b]thiophen-6-yl)methoxy)phenyl)acetate (337a)

Compound 337a was prepared according to the procedure reported in step-3 of scheme-1 from ethyl 2-(2-((2-chloro-4-(((trifluoromethyl)sulfonyl)oxy)benzo[b]thiophen-6-yl)methoxy)phenyl)acetate (215f) (143 mg, 0.281 mmol) in dioxane (4 mL) using (3-(aminomethyl)-2-fluorophenyl) boronic acid hydrochloride (56a) (64 mg, 0.309 mmol), bis(triphenylphosphine)palladium(II) chloride (Pd(PPh$_3$)$_2$Cl$_2$) (20 mg, 0.028 mmol) and a solution of K$_2$CO$_3$ (117 mg, 0.843 mmol) in water (1 mL) under a nitrogen atmosphere heating at 100° C. for 16 h on oil bath. This gave after workup, purification by flash column chromatography [silica (12 g), eluting with 0-4% MeOH in DCM] ethyl 2-(2-((4-(3-(aminomethyl)-2-fluorophenyl)-2-chlorobenzo[b]thiophen-6-yl)methoxy)phenyl)acetate (337a) (62 mg) as a clear pale-yellow oil (62 mg); MS (ES+): 484/486 (M+1).

Step-2: Preparation of 2-(2-((4-(3-(aminomethyl)-2-fluorophenyl)-2-chlorobenzo[b]thiophen-6-yl) methoxy)phenyl)acetic Acid (337b)

Compound 337b was prepared according to the procedure reported in step-4 of scheme-4 from ethyl 2-(2-((4-(3-(aminomethyl)-2-fluorophenyl)-2-chlorobenzo[b]thiophen-6-yl)methoxy)phenyl)acetate (337a) (62 mg, from above step-1) in MeOH (3 mL), using a solution of NaOH (23 mg, 0.562 mmol) in water (1 mL). This gave after workup and purification by reverse phase column (C18, 100 g, 0-60% MeCN in H$_2$O containing 0.1% HCl) 2-(2-((4-(3-(aminomethyl)-2-fluorophenyl)-2-chlorobenzo[b]thiophen-6-yl) methoxy)phenyl)acetic acid (337b) (45 mg, 35% yield) HCl salt as a white solid; $^1$H NMR (300 MHz, DMSO-d$_6$) δ 8.10

1095

Preparation of 2-(2-((4-(2-(aminomethyl)-3-fluoropyridin-4-yl)-2-chlorobenzo[b]thiophen-6-yl)methoxy)phenyl)acetic Acid (338c)

Step-1: Preparation of (+)-(S)-ethyl 2-(2-((2-chloro-4-(2-((1,1-dimethylethylsulfinamido)methyl)-3-fluoropyridin-4-yl)benzo[b]thiophen-6-yl)methoxy)phenyl)acetate (338a)

Compound 338a was prepared according to the procedure reported in step-3 of scheme-1 from ethyl 2-(2-((2-chloro-4-(((trifluoromethyl)sulfonyl)oxy)benzo[b]thiophen-6-yl)methoxy)phenyl)acetate (215f) (117 mg, 0.240 mmol) in dioxane (4 mL) using (+)-(S)—N-((4-chloro-3-fluoropyridin-2-yl)methyl)-2-methylpropane-2-sulfinamide (220c) (70.0 mg, 0.264 mmol), bis(triphenylphosphine)palladium (II) chloride (Pd(PPh$_3$)$_2$Cl$_2$) (17 mg, 0.024 mmol) and a solution of K$_2$CO$_3$ (100 mg, 0.721 mmol) in water (1 mL) under a nitrogen atmosphere heating at 100° C. for 16 h on oil bath. This gave after workup, purification by flash column chromatography [silica gel (12 g), eluting with 0-2% MeOH in DCM] (+)-(S)-ethyl 2-(2-((2-chloro-4-(2-((1,1-dimethylethylsulfinamido)methyl)-3-fluoropyridin-4-yl)benzo[b]thiophen-6-yl)methoxy)phenyl)acetate (338a) (145 mg) as a pale-yellow oil (145 mg); MS (ES+) 589/591; Optical rotation [t]D=+20.0 (c=0.03, MeOH)

Step-2: Preparation of methyl 2-(2-((4-(2-(aminomethyl)-3-fluoropyridin-4-yl)-2-chlorobenzo[b]thiophen-6-yl)methoxy)phenyl)acetate (338b)

Compound 338b was prepared according to the procedure reported in step-3 of scheme-305 from (+)-(S)-ethyl 2-(2-((2-chloro-4-(2-((1,1-dimethylethylsulfinamido)methyl)-3-fluoropyridin-4-yl)benzo[b]thiophen-6-yl)methoxy)phenyl)acetate (338a) (145 mg, from step-1 above) in methanol (5 mL) using HCl (4M in dioxane; 0.18 mL, 0.721 mmol) and heating at 60° C. for 1 h. This gave after workup, purification by flash column chromatography [silica (12 g), eluting with 0-6% MeOH in DCM] methyl 2-(2-((4-(2-(aminomethyl)-3-fluoropyridin-4-yl)-2-chlorobenzo[b]thiophen-6-yl)methoxy)phenyl)acetate (338b) (25 mg) as a pale-yellow oil; MS (ES+): 471/473 (methyl ester, M+1).

Step-3: Preparation of 2-(2-((4-(2-(aminomethyl)-3-fluoropyridin-4-yl)-2-chlorobenzo[b]thiophen-6-yl)methoxy)phenyl)acetic Acid (338c)

Compound 338c was prepared according to the procedure reported in step-4 of scheme-4 from methyl 2-(2-((4-(2-(aminomethyl)-3-fluoropyridin-4-yl)-2-chlorobenzo[b]thiophen-6-yl)methoxy)phenyl)acetate (338b) (25 mg, from step-2 above) in MeOH (2 mL), THF (1 mL) using a solution of NaOH (28.8 mg, 0.721 mmol) in water (1 mL). This gave after workup and purification by reverse phase column [C18 (100 g), eluting with ACN in water (containing 0.1% HCl) from 0-60%] 2-(2-((4-(2-(aminomethyl)-3-fluoropyridin-4-yl)-2-chlorobenzo[b]thiophen-6-yl)methoxy)phenyl)acetic acid (338c) (13 mg, 12% yield) HCl salt as a pale-green solid; $^1$H NMR (300 MHz, DMSO-d$_6$) δ 8.61 (d, J=4.9 Hz, 1H), 8.19 (d, J=1.4 Hz, 1H), 7.66 (t, J=5.3 Hz, 1H), 7.59 (d, J=1.4 Hz, 1H), 7.38 (d, J=3.2 Hz, 1H), 7.23 (d, J=7.5 Hz, 2H), 7.07 (d, J=8.1 Hz, 1H), 6.96-6.88 (m, 1H), 5.30 (s, 2H), 4.37 (d, J=1.8 Hz, 2H), 3.60 (s, 2H); MS (ES+): 457/459, (ES−): 455/457.

1096

Scheme-339

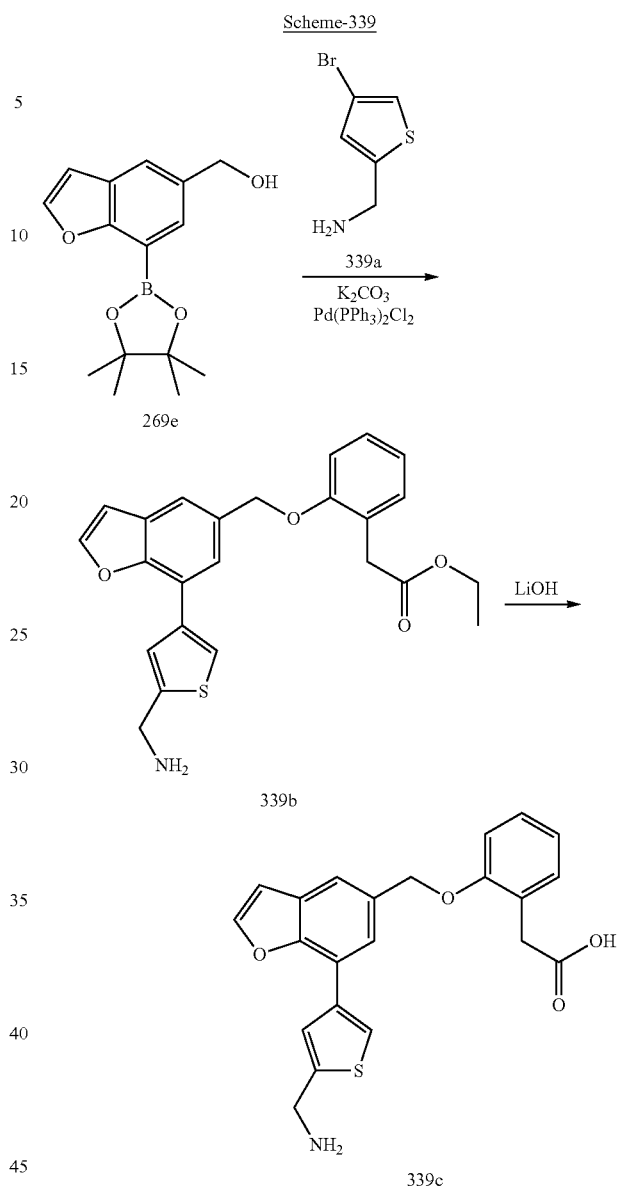

Preparation of 2-(2-((7-(5-(aminomethyl)thiophen-3-yl)benzofuran-5-yl)methoxy)phenyl)acetic Acid (339c)

Step-1: Preparation of Ethyl 2-(2-((7-(5-(aminomethyl)thiophen-3-yl)benzofuran-5-yl)methoxy)phenyl)acetate (339b)

Compound 339b was prepared according to the procedure reported in step-3 of scheme-1 from (4-bromothiophen-2-yl)methanamine (339a) (300 mg, 1.562 mmol; CAS #479090-38-5) in dioxane (5 mL) using (7-(4,4,5,5-tetramethyl-1,3,2-dioxaborolan-2-yl)benzofuran-5-yl)methanol (269e) (496 mg, 1.137 mmol), bis(triphenylphosphine)palladium(II) chloride (Pd(PPh$_3$)$_2$Cl$_2$) (127 mg, 0.181 mmol) and a solution of K$_2$CO$_3$ (498 mg, 3.60 mmol) in water (0.5 mL) under an argon atmosphere heating at 100° C. for 3 h on oil bath. This gave after workup, purification by flash column chromatography [silica (12 g), eluting with MeOH/

DCM from 0-20%] ethyl 2-(2-((7-(5-(aminomethyl)thiophen-3-yl)benzofuran-5-yl)methoxy)phenyl)acetate (339b) (475 mg, 99% yield) as a yellow oil. MS(ES+): 422.1 (M+1), MS(ES−): 420.1 (M−1).

Step-2: Preparation of 2-(2-((7-(5-(aminomethyl)thiophen-3-yl)benzofuran-5-yl)methoxy)phenyl)acetic Acid (339c)

Compound 339c was prepared according to the procedure reported in step-6 of scheme-1 from ethyl 2-(2-((7-(5-(aminomethyl)thiophen-3-yl)benzofuran-5-yl)methoxy)phenyl)acetate (339b) (380 mg, 0.902 mmol) in MeOH (6 mL), THF (6 mL) using a solution of lithium hydroxide hydrate (152 mg, 3.62 mmol) in water (2 mL). This gave after workup and purification by reverse phase column [C18 (50 g), eluting with ACN in water (containing 0.1% HCl) from 0-100%] 2-(2-((7-(5-(aminomethyl)thiophen-3-yl)benzofuran-5-yl)methoxy)phenyl)acetic acid (339c) (155 mg, 44% yield) HCl salt as a white solid. $^1$H NMR (300 MHz, DMSO-d$_6$/D$_2$O) δ 8.20 (d, J=1.5 Hz, 1H), 8.13 (d, J=2.2 Hz, 1H), 7.98 (d, J=1.5 Hz, 1H), 7.80-7.64 (m, 2H), 7.31-7.18 (m, 2H), 7.15-7.02 (m, 2H), 6.92 (t, J=7.4 Hz, 1H), 5.26 (s, 2H), 4.34 (s, 2H), 3.63 (s, 2H); MS (ES+): 394.1 (M+1); MS (ES−): 392.1 (M−1); Analysis calculated for: C$_{22}$H$_{19}$NO$_4$S.HCl.1.25 H$_2$O: C, 58.40; H, 5.01; Cl, 7.84; N, 3.10; Found: C, 58.52; H, 5.07; Cl, 8.09, N, 3.20.

Scheme-340

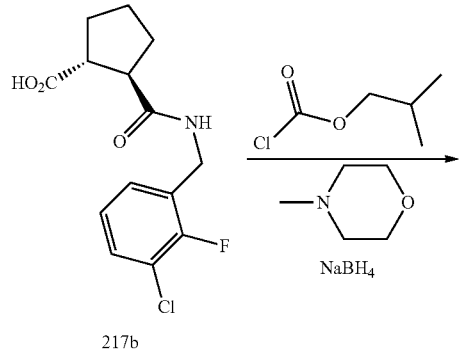

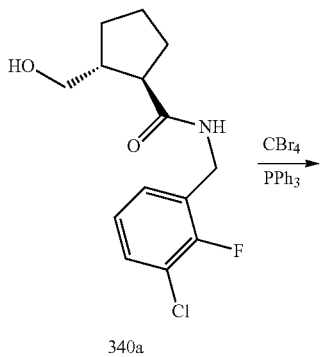

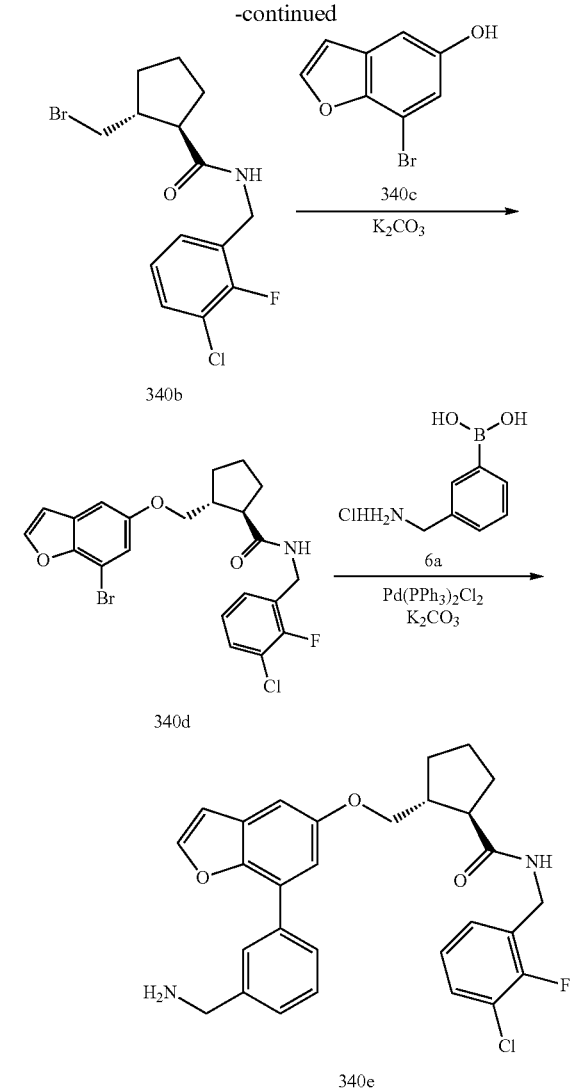

Preparation of (trans)-2-(((7-(3-(aminomethyl)phenyl)benzofuran-5-yl)oxy)methyl)-N-(3-chloro-2-fluorobenzyl)cyclopentanecarboxamide (340e)

Step-1: Preparation of (trans)-N-(3-chloro-2-fluorobenzyl)-2-(hydroxymethyl)cyclopentanecarboxamide (340a)

Compound 340a was prepared according to the procedure reported in step-1 of scheme-23 from (trans)-2-((3-chloro-2-fluorobenzyl)carbamoyl)cyclopentanecarboxylic acid (217b) (1.2 g, 2.91 mmol) using N-methylmorpholine (0.202 g, 2.002 mmol) in THF (15 mL), isobutyl chloroformate (0.262 mL, 2.002 mmol) and NaBH$_4$ (0.189 g, 5.0 mmol) in water (2 mL). This gave after workup and purification by flash column chromatography (silica gel, 12 g, eluting with 0-3% MeOH in DCM) (trans)-N-(3-chloro-2-fluorobenzyl)-2-(hydroxymethyl)cyclopentanecarboxamide (340a) (0.30 g, 63% yield) as a colorless oil. $^1$H NMR (300 MHz, DMSO-d$_6$) δ 8.41 (t, J=5.9 Hz, 0H), 7.47 (td, J=7.5, 1.9 Hz, 1H), 7.35-7.08 (m, 2H), 4.42-4.21 (m, 2H), 3.34 (qd, J=10.6, 6.4 Hz, 2H), 2.35 (q, J=7.8 Hz, 1H), 2.16 (h, J=7.3

Hz, 1H), 1.93-1.43 (m, 4H), 1.33 (dq, J=13.6, 7.2 Hz, 1H). $^{19}$F NMR (282 MHz, DMSO-d$_6$) δ –121.75; MS (ES+): 286/288 (M+1).

Step-2: Preparation of (trans)-2-(bromomethyl)-N-(3-chloro-2-fluorobenzyl)cyclopentanecarboxamide (340b)

Compound 340b was prepared according to the procedure reported in step-1 of scheme-152 from (trans)-N-(3-chloro-2-fluorobenzyl)-2-(hydroxymethyl)cyclopentanecarboxamide (340a) (0.30 g, 1.050 mmol) in DCM (10 mL) using triphenylphosphine (0.303 g, 1.155 mmol), CBr$_4$ (0.383 g, 1.155 mmol) and stirring at room temperature for 2 h. This gave after workup and purification by flash column chromatography (silica gel, 12 g, eluting with 0-20% EtOAc in hexane) (trans)-2-(bromomethyl)-N-(3-chloro-2-fluorobenzyl)cyclopentanecarboxamide (340b) (0.21 g, 57% yield) as a colorless oil; MS (ES+): 348/350 (M+1).

Step-3: Preparation of (trans)-2-(((7-bromobenzofuran-5-yl)oxy)methyl)-N-(3-chloro-2-fluorobenzyl)cyclopentanecarboxamide (340d)

Compound 340d was prepared according to the procedure reported in step-2 of scheme-152 from (trans)-2-(bromomethyl)-N-(3-chloro-2-fluorobenzyl)cyclopentanecarboxamide (340b) (0.21 g, 0.602 mmol) using 7-bromobenzofuran-5-ol (340c) (0.128 g, 0.602 mmol; CAS #603311-31-5), K$_2$CO$_3$ (0.250 g, 1.807 mmol) in MeCN (10 mL) and heating at 80° C. for 5 h. This gave after workup and purification by flash column chromatography (silica gel, 12 g, eluting with 0-30% EtOAc in hexane) (trans)-2-(((7-bromobenzofuran-5-yl)oxy)methyl)-N-(3-chloro-2-fluorobenzyl)cyclopentanecarboxamide (340d) (150 mg, 52% yield) as a white solid; $^1$H NMR (300 MHz, DMSO-d$_6$) δ 8.41 (t, J=5.8 Hz, 1H), 8.06 (dd, J=2.1, 0.5 Hz, 1H), 7.47 (ddd, J=7.9, 7.2, 1.8 Hz, 1H), 7.27 (ddd, J=7.7, 6.7, 1.7 Hz, 1H), 7.19-7.10 (m, 2H), 7.07 (dd, J=2.4, 0.5 Hz, 1H), 6.99 (d, J=2.2 Hz, 1H), 4.48-4.24 (m, 2H), 4.01-3.84 (m, 2H), 1.97-1.78 (m, 2H), 1.78-1.54 (m, 4H), 1.45 (dt, J=13.0, 7.0 Hz, 1H). $^{19}$F NMR (282 MHz, DMSO-d$_6$) δ –121.58; MS (ES+): 480/482 (M+1), (ES–): 478/480 (M–1).

Step-4: Preparation of (trans)-2-(((7-(3-(aminomethyl)phenyl)benzofuran-5-yl)oxy)methyl)-N-(3-chloro-2-fluorobenzyl)cyclopentanecarboxamide (340e)

Compound 340e was prepared according to the procedure reported in step-3 of scheme-1 from (trans)-2-(((7-bromobenzofuran-5-yl)oxy)methyl)-N-(3-chloro-2-fluorobenzyl)cyclopentanecarboxamide (340d) (150 mg, 0.312 mmol) in dioxane (4 mL) using 3-(aminomethyl)phenylboronic acid hydrochloride (6c) (64 mg, 0.343 mmol), bis(triphenylphosphine)palladium(II) chloride (Pd(PPh$_3$)$_2$Cl$_2$) (22 mg, 0.031 mmol) and K$_2$CO$_3$ (129 mg, 0.936 mmol) in water (1 mL) under a nitrogen atmosphere heating at 100° C. for 16 h on oil bath. This gave after workup, purification by flash column chromatography [silica gel, eluting with methanol in DCM] followed by purification by reverse phase flash column chromatography (C18, 100 g, 0-60% MeCN in H$_2$O containing 0.1% HCl) (trans)-2-(((7-(3-(aminomethyl)phenyl)benzofuran-5-yl)oxy)methyl)-N-(3-chloro-2-fluorobenzyl)cyclopentanecarboxamide (340e) (108 mg, 68% yield) HCl salt as a white solid; $^1$HNMR (300 MHz, DMSO-d$_6$) δ 8.50 (t, J=5.8 Hz, 1H), 8.40 (s, 3H), 8.04 (d, J=2.2 Hz, 1H), 7.98 (d, J=1.9 Hz, 1H), 7.91 (dt, J=7.2, 1.8 Hz, 1H), 7.62-7.49 (m, 2H), 7.43 (ddd, J=8.0, 7.1, 1.7 Hz, 1H), 7.32-7.23 (m, 1H), 7.19-7.05 (m, 3H), 6.96 (d, J=2.2 Hz, 1H), 4.35 (d, J=5.8 Hz, 2H), 4.13 (s, 2H), 4.06-3.90 (m, 2H), 2.56 (t, J=5.3 Hz, 2H), 1.92 (t, J=6.4 Hz, 1H), 1.81-1.59 (m, 4H), 1.51 (dt, J=12.8, 6.8 Hz, 1H). $^{19}$F NMR (282 MHz, DMSO-d$_6$) δ –121.60; MS (ES+): 507/509 (M+1), (ES–): 505/507 (M–1).

Scheme-341

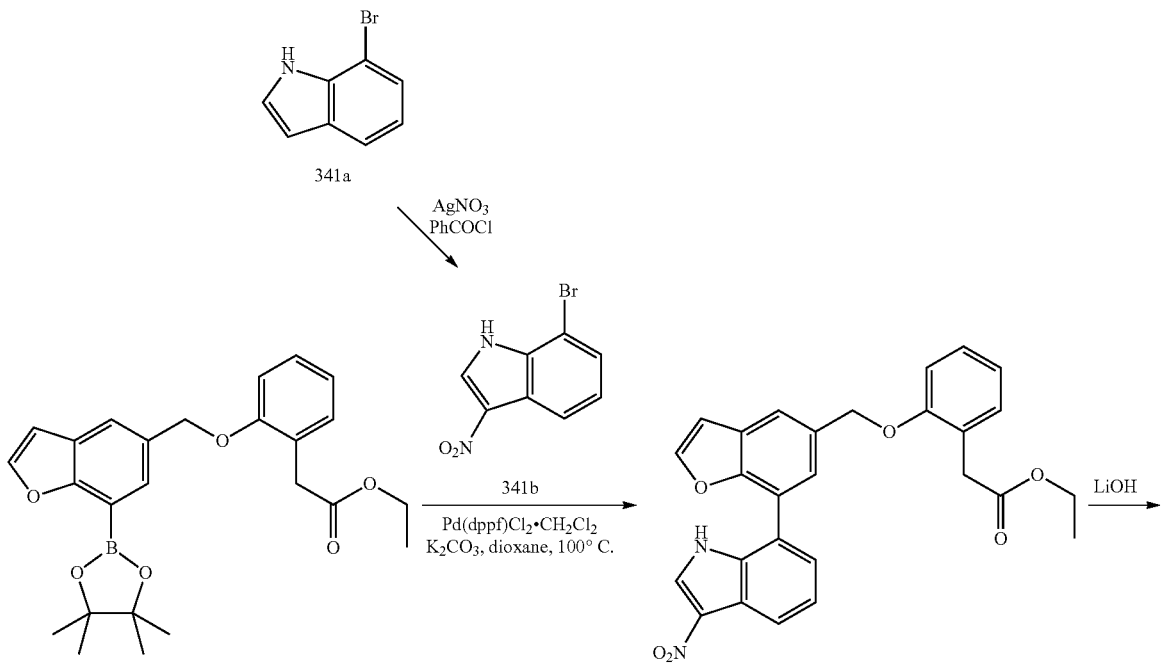

1101

1102

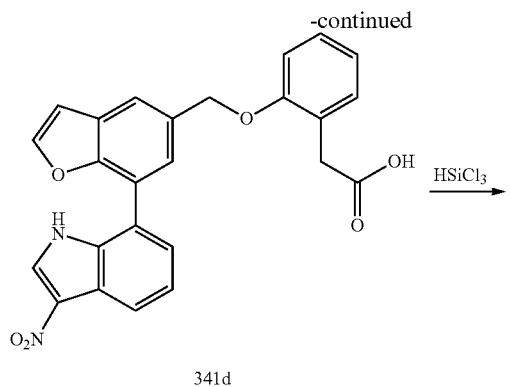

341d

-continued

HSiCl₃ →

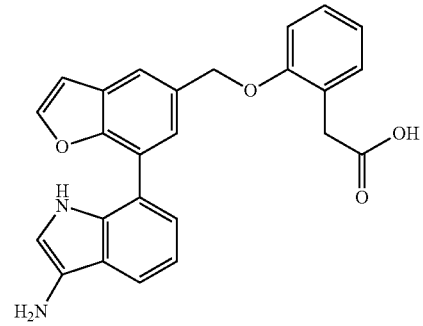

341e

Preparation of 2-(2-((7-(3-amino-1H-indol-7-yl)benzofuran-5-yl)methoxy)phenyl)acetic acid (341e)

Step-1: Preparation of 7-bromo-3-nitro-1H-indole (341b)

To a suspension of 7-bromo-1H-indole (341a) (2.0 g, 10.20 mmol; CAS #: 51417-51-7) AgNO₃ (1.9 g, 11.18 mmol) in acetonitrile (16 mL) at 0° C. was added benzoyl chloride (1.35 mL, 11.63 mmol) and stirred at 0° C. for 45 min. The mixture was diluted with water and extracted with ethyl acetate. The combined organic layers were washed with saturated aqueous NaHCO₃ solution, 2 M HCl solution, dried, filtered and concentrated in vacuum. The residue obtained was purified by flash column chromatography [silica (40g), eluting with ethyl acetate in hexane from 0-60%] followed by purification by reverse phase column chromatography [C18 (150g), eluting with ACN in water (containing 0.1% HCl) from 0-100%] to provide 7-bromo-3-nitro-1H-indole (341b) (547 mg, 22% yield) as a yellow solid; $^1$H NMR (300 MHz, DMSO-d₆) δ 13.00 (s, 1H), 8.69 (s, 1H), 8.11 (dd, J=8.0, 1.0 Hz, 1H), 7.61 (dd, J=7.8, 1.0 Hz, 1H), 7.32 (t, J=7.9 Hz, 1H).

Step-2: Preparation of Ethyl 2-(2-((7-(3-nitro-1H-indol-7-yl)benzofuran-5-yl)methoxy)phenyl)acetate (341c)

To a degassed solution of ethyl 2-(2-((7-(4,4,5,5-tetramethyl-1,3,2-dioxaborolan-2-yl)benzofuran-5-yl)methoxy)phenyl)acetate (59a) (377 mg, 0.864 mmol) in dioxane (5 mL) was added 7-bromo-3-nitro-1H-indole (341b) (202 mg, 0.838 mmol), Pd(dppf)Cl₂—CH₂Cl2 Adduct (109 mg, 0.133 mmol) and K₂CO₃ (380 mg, 2.75 mmol) in water (0.5 mL). The mixture was degassed and filled with argon then heated at 100° C. overnight. The reaction mixture was cooled to room temperature, diluted with EA, washed with water and brine. The organic layer was dried, filtered and concentrated. The residue obtained was purified by flash column chromatography [silica (12 g), eluting with EA/hex from 0-60%] to give ethyl 2-(2-((7-(3-nitro-1H-indol-7-yl)benzofuran-5-yl)methoxy)phenyl)acetate (341c) (394 mg, 100% yield) as a yellow syrup. MS (ES+): 471.1 (M+1), MS (ES−): 469.1 (M−1).

Step-3: Preparation of 2-(2-((7-(3-nitro-1H-indol-7-yl)benzofuran-5-yl)methoxy)phenyl)acetic Acid (341d)

Compound 341d was prepared according to the procedure reported in step-6 of scheme-1 from ethyl 2-(2-((7-(3-nitro-1H-indol-7-yl)benzofuran-5-yl)methoxy)phenyl)acetate (341c) (50 mg, 0.106 mmol) in MeOH (3 mL), THF (3 mL) using a solution of lithium hydroxide hydrate (15 mg, 0.357 mmol) in water (1 mL). This gave after workup 2-(2-((7-(3-nitro-1H-indol-7-yl)benzofuran-5-yl)methoxy)phenyl)acetic acid (341d) (47 mg, 100% yield) as a yellow solid. MS (ES+): 443.1 (M+1); MS (ES−): 441.1 (M−1).

Step-4: Preparation of 2-(2-((7-(3-amino-1H-indol-7-yl)benzofuran-5-yl)methoxy)phenyl)acetic Acid (341e)

To a solution of 2-(2-((7-(3-nitro-1H-indol-7-yl)benzofuran-5-yl)methoxy)phenyl)acetic acid (341d) (44 mg, 0.099 mmol), DIEA (0.128 mL, 0.735 mmol) in anhydrous acetonitrile (3 mL) was added trichlorosilane (0.13 mL, 1.267 mmol) at 0° C. and allowed to warm to room temperature overnight. The reaction mixture was concentrated to dryness and the residue obtained was purified by reverse phase flash column chromatography [C18 (50g), eluting with ACN in water (containing 0.1% HCl) from 0-100%] to provide 2-(2-((7-(3-amino-1H-indol-7-yl)benzofuran-5-yl)methoxy)phenyl)acetic acid (341e) (8 mg, 20% yield) HCl salt as a white solid. $^1$H NMR (300 MHz, DMSO-d₆) δ 10.99 (d, J=2.9 Hz, 1H), 10.22 (s, 2H), 7.94 (d, J=2.2 Hz, 1H), 7.76 (d, J=1.6 Hz, 1H), 7.68 (d, J=7.9 Hz, 1H), 7.50 (d, J=1.7 Hz, 1H), 7.40-7.29 (m, 2H), 7.26-7.10 (m, 3H), 7.10-7.01 (m, 1H), 6.99 (d, J=2.2 Hz, 1H), 6.83 (td, J=7.3, 1.1 Hz, 1H), 5.23 (s, 2H), 3.52 (s, 2H); MS (ES+): 413.1 (M+1); MS (ES−): 411.1 (M−1).

Scheme-342

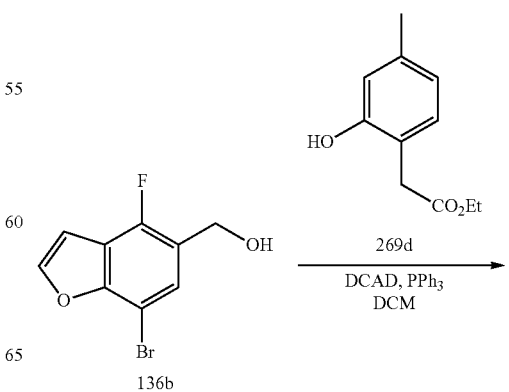

136b

269d

DCAD, PPh₃
DCM

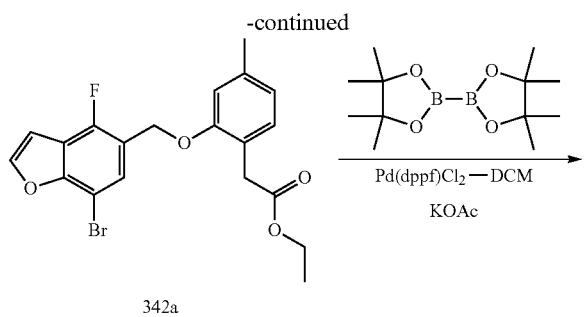

Preparation of 2-(2-((7-(2-(aminomethyl)-3-fluoro-pyridin-4-yl)-4-fluorobenzofuran-5-yl)methoxy)-4-methylphenyl)acetic Acid (342e)

Step-1: Preparation of Ethyl 2-(2-((7-bromo-4-fluorobenzofuran-5-yl)methoxy)-4-methylphenyl)acetate (342a)

Compound 342a was prepared according to the procedure reported in step-2 of scheme-23 from (7-bromo-4-fluorobenzofuran-5-yl)methanol (136b) (1.0 g, 4.08 mmol) in DCM (40 mL) using triphenylphosphine (1.177 g, 4.49 mmol), ethyl 2-(2-hydroxy-4-methylphenyl)acetate (269d) (0.951 g, 4.90 mmol) and (E)-bis(4-chlorobenzyl) diazene-1,2-dicarboxylate (DCAD, 1.648 g, 4.49 mmol) in DCM (15 mL). This gave after workup and purification by flash column chromatography (silica gel, eluting with EtOAc in hexane from 0-40%) ethyl 2-(2-((7-bromo-4-fluorobenzofuran-5-yl)methoxy)-4-methylphenyl)acetate (342a) (972 mg, 57% yield) as a yellow solid; $^1$H NMR (300 MHz, DMSO-$d_6$) δ 8.22 (d, J=2.3 Hz, 1H), 7.70 (d, J=6.0 Hz, 1H), 7.28 (d, J=2.3 Hz, 1H), 7.08 (d, J=7.5 Hz, 1H), 7.00 (d, J=1.3 Hz, 1H), 6.75 (ddd, J=7.5, 1.6, 0.8 Hz, 1H), 5.18 (d, J=1.4 Hz, 2H), 3.95 (q, J=7.1 Hz, 2H), 3.51 (s, 2H), 2.31 (s, 3H), 1.01 (t, J=7.1 Hz, 3H); $^{19}$F NMR (282 MHz, DMSO-$d_6$) δ −124.72.

Step-2: Preparation of Ethyl 2-(2-((4-fluoro-7-(4,4,5,5-tetramethyl-1,3,2-dioxaborolan-2-yl)benzofuran-5-yl)methoxy)-4-methylphenyl)acetate (342b)

Compound 342b was prepared according to the procedure reported in step-1 of scheme-59 from ethyl 2-(2-((7-bromo-4-fluorobenzofuran-5-yl)methoxy)-4-methylphenyl)acetate (342a) (472 mg, 1.120 mmol), using bis(pinacolato)diboron (427 mg, 1.681 mmol), potassium acetate (330 mg, 3.36 mmol) and Pd(dppf)Cl$_2$-DCM (137 mg, 0.168 mmol) in anhydrous dioxane (10 mL) under an argon atmosphere and heating at 90° C. overnight. This gave after workup and purification by flash column chromatography [silica gel (24g), eluting with EtOAc in hexanes from 0-40%] ethyl 2-(2-((4-fluoro-7-(4,4,5,5-tetramethyl-1,3,2-dioxaborolan-2-yl)benzofuran-5-yl)methoxy)-4-methylphenyl)acetate (342b) (466 mg, 89% yield) as a yellow solid; $^1$H NMR (300 MHz, DMSO-$d_6$) δ 8.14 (d, J=2.3 Hz, 1H), 7.74 (d, J=7.7 Hz, 1H), 7.13 (d, J=2.3 Hz, 1H), 7.10-6.97 (m, 2H), 6.74 (d, J=7.6 Hz, 1H), 5.17 (s, 2H), 3.91 (q, J=7.1 Hz, 2H), 3.45 (s, 2H), 2.31 (s, 3H), 1.33 (s, 12H), 0.96 (t, J=7.1 Hz, 3H); $^{19}$F NMR (282 MHz, DMSO-$d_6$) δ −119.10.

Step-3: Preparation of Ethyl 2-(2-((7-(2-((1,1-dimethylethylsulfinamido)methyl)-3-fluoropyridin-4-yl)-4-fluorobenzofuran-5-yl)methoxy)-4-methylphenyl)acetate (342c)

Compound 342c was prepared according to the procedure reported in step-3 of scheme-1 from ethyl 2-(2-((4-fluoro-7-(4,4,5,5-tetramethyl-1,3,2-dioxaborolan-2-yl)benzofuran-5-yl)methoxy)-4-methylphenyl)acetate (342b) (460 mg, 0.982 mmol) in dioxane (5 mL) using (+)-(S)—N-((4-chloro-3-fluoropyridin-2-yl)methyl)-2-methylpropane-2-sulfinamide (220c) (312 mg, 1.179 mmol), bis(triphenylphosphine)palladium(II) chloride (Pd(PPh$_3$)$_2$Cl$_2$) (103 mg, 0.147 mmol) and a solution of K$_2$CO$_3$ (407 mg, 2.95 mmol) in water (0.5 mL) under an argon atmosphere heating at 100° C. for 3 h on oil bath. This gave after workup, purification by flash column chromatography [silica gel (24g), eluting with MeOH/DCM from 0-15%] ethyl 2-(2-((7-(2-((1,1-dimethylethylsulfinamido)methyl)-3-fluoropyridin-4-yl)-4-fluorobenzofuran-5-yl)methoxy)-4-methylphenyl)acetate (342c) (561 mg, 100% yield) as a brown oil. MS (ES+): 571.2 (M+1).

Step-4: Preparation of Ethyl 2-(2-((7-(2-(aminomethyl)-3-fluoropyridin-4-yl)-4-fluorobenzofuran-5-yl)methoxy)-4-methylphenyl)acetate (342d)

Compound 342d was prepared according to the procedure reported in step-3 of scheme-305 from ethyl 2-(2-((7-(2-((1,1-dimethylethylsulfinamido)methyl)-3-fluoropyridin-4-yl)-4-fluorobenzofuran-5-yl)methoxy)-4-methylphenyl)acetate (342c) (555 mg, 0.973 mmol) in methanol (10 mL) using HCl (4M in dioxane; 1 mL, 4.00 mmol) and stirring at room temperature for 1 h. This gave after workup, purification by flash column chromatography [silica (12 g), eluting with DMA80/DCM from 0-70%] ethyl 2-(2-((7-(2-(aminomethyl)-3-fluoropyridin-4-yl)-4-fluorobenzofuran-5-yl)methoxy)-4-methylphenyl)acetate (342d) (268 mg, 59% yield) as a pale yellow oil; $^1$H NMR (300 MHz, DMSO-d$_6$) δ 8.52 (d, J=4.9 Hz, 1H), 8.18 (d, J=2.2 Hz, 1H), 7.66 (d, J=6.7 Hz, 1H), 7.63-7.52 (m, 1H), 7.25 (d, J=2.3 Hz, 1H), 7.15-6.99 (m, 2H), 6.75 (d, J=7.5 Hz, 1H), 5.26 (d, J=3.0 Hz, 2H), 3.94 (d, J=2.1 Hz, 2H), 3.86-3.78 (m, 2H), 3.51 (s, 2H), 2.32 (s, 3H), 0.90 (t, J=7.1 Hz, 3H); $^{19}$F NMR (282 MHz, DMSO-d$_6$) δ−122.08, −130.74. MS (ES+): 467.2 (M+1).

Step-5: Preparation of 2-(2-((7-(2-(aminomethyl)-3-fluoropyridin-4-yl)-4-fluorobenzofuran-5-yl)methoxy)-4-methylphenyl)acetic Acid (342e)

Compound 342e was prepared according to the procedure reported in step-6 of scheme-1 from ethyl 2-(2-((7-(2-(aminomethyl)-3-fluoropyridin-4-yl)-4-fluorobenzofuran-5-yl)methoxy)-4-methylphenyl)acetate (342d) (263 mg, 0.564 mmol) in MeOH (6 mL), THF (6 mL) using a solution of lithium hydroxide (89 mg, 2.121 mmol) in water (2 mL). This gave after workup and purification by reverse phase column [C18 (50 g), eluting with ACN in water (containing 0.1% HCl) from 0-100%] 2-(2-((7-(2-(aminomethyl)-3-fluoropyridin-4-yl)-4-fluorobenzofuran-5-yl)methoxy)-4-methylphenyl)acetic acid (342e) (166 mg, 67% yield) HCl salt as a white solid; $^1$H NMR (300 MHz, DMSO-d$_6$) δ 11.94 (s, 1H), 8.73 (t, J=5.8 Hz, 3H), 8.63 (d, J=4.9 Hz, 1H), 8.21 (d, J=2.3 Hz, 1H), 7.85-7.67 (m, 2H), 7.27 (d, J=2.3 Hz, 1H), 7.09 (d, J=7.5 Hz, 1H), 7.03 (d, J=1.6 Hz, 1H), 6.82-6.65 (m, 1H), 5.29 (s, 2H), 4.36 (d, J=5.8 Hz, 2H), 3.49 (s, 2H), 2.31 (s, 3H); $^{19}$F NMR (282 MHz, DMSO-d$_6$) δ−121.44, −128.49; MS (ES+): 439.1 (M+1); MS (ES−): 437.1 (M−1); Analysis calculated for C$_{24}$H$_{20}$F$_2$N$_2$O$_4$.1.1HCl.0.25H$_2$O: C, 59.68; H, 4.51; Cl, 8.07; N, 5.80; Found: C, 59.61; H, 4.19; Cl, 8.21; N, 5.87.

Scheme-343

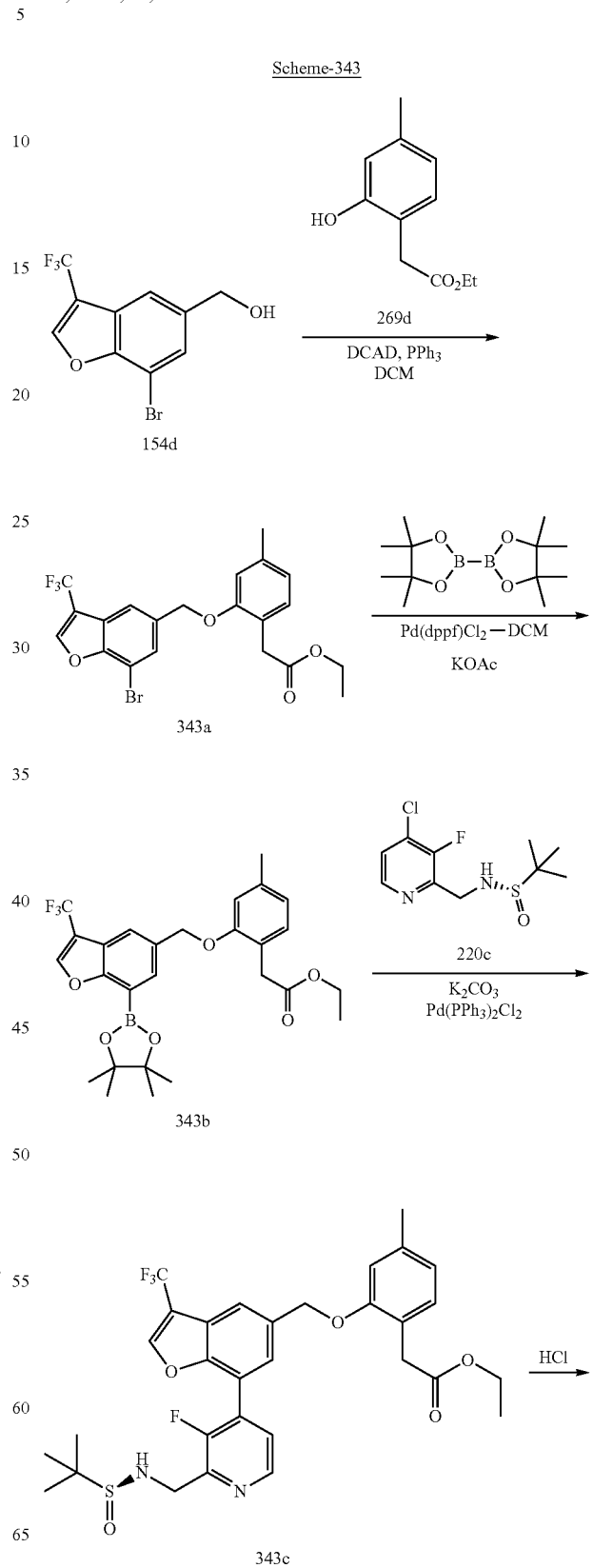

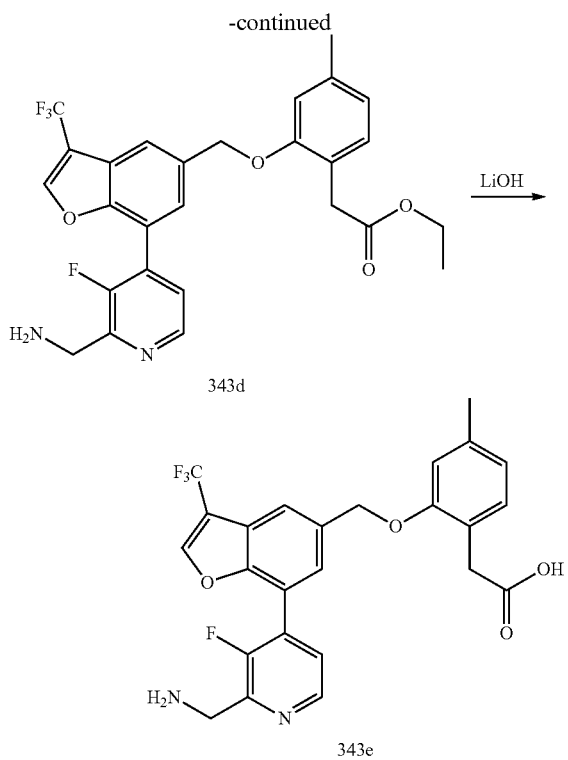

Preparation of 2-(2-((7-(2-(aminomethyl)-3-fluoropyridin-4-yl)-3-(trifluoromethyl)benzofuran-5-yl)methoxy)-4-methylphenyl)acetic Acid (343e)

Step-1: Preparation of Ethyl 2-(2-((7-bromo-3-(trifluoromethyl)benzofuran-5-yl)methoxy)-4-methylphenyl)acetate (343a)

Compound 343a was prepared according to the procedure reported in step-2 of scheme-23 from (7-bromo-3-(trifluoromethyl)benzofuran-5-yl)methanol (154d) (1.4 g, 4.74 mmol) in DCM (20 mL) using triphenylphosphine (1.369 g, 5.22 mmol), ethyl 2-(2-hydroxy-4-methylphenyl)acetate (269d) (1.106 g, 5.69 mmol) and (E)-bis(4-chlorobenzyl) diazene-1,2-dicarboxylate (DCAD, 1.916 g, 5.22 mmol) in DCM (5 mL). This gave after workup and purification by flash column chromatography [silica gel, eluting with (EtOAc: MeOH 9:1)/hexane from 0-40%] ethyl 2-(2-((7-bromo-3-(trifluoromethyl)benzofuran-5-yl)methoxy)-4-methylphenyl)acetate (343a) (953 mg, 43% yield) as a white solid; $^1$H NMR (300 MHz, DMSO-$d_6$) δ 8.96 (d, J=1.7 Hz, 1H), 7.80 (d, J=2.2 Hz, 2H), 7.10 (d, J=7.5 Hz, 1H), 6.93 (s, 1H), 6.74 (d, J=7.3 Hz, 1H), 5.22 (s, 2H), 3.99 (q, J=7.1 Hz, 2H), 3.57 (s, 2H), 2.29 (s, 3H), 1.06 (t, J=7.1 Hz, 3H); $^{19}$F NMR (282 MHz, DMSO-$d_6$) δ −58.24.

Step-2: Preparation of Ethyl 2-(4-methyl-2-((7-(4,4,5,5-tetramethyl-1,3,2-dioxaborolan-2-yl)-3-(trifluoromethyl)benzofuran-5-yl)methoxy)phenyl)acetate (343b)

Compound 343b was prepared according to the procedure reported in step-1 of scheme-59 from ethyl 2-(2-((7-bromo-3-(trifluoromethyl)benzofuran-5-yl)methoxy)-4-methylphenyl)acetate (343a) (493 mg, 1.046 mmol), using bis(pinacolato)diboron (398 mg, 1.569 mmol), potassium acetate (308 mg, 3.14 mmol) and Pd(dppf)Cl$_2$-DCM (128 mg, 0.157 mmol) in anhydrous dioxane (10 mL) under an argon atmosphere and heating at 90° C. overnight. This gave after workup and purification by flash column chromatography [silica gel (24g), eluting with EtOAc in hexanes from 0-40%] ethyl 2-(4-methyl-2-((7-(4,4,5,5-tetramethyl-1,3,2-dioxaborolan-2-yl)-3-(trifluoromethyl)benzofuran-5-yl)methoxy)phenyl)acetate (343b) (534 mg, 98% yield) as a colorless oil; $^1$H NMR (300 MHz, DMSO-$d_6$) δ 8.85 (q, J=1.7 Hz, 1H), 7.92 (d, J=1.7 Hz, 1H), 7.81 (d, J=1.8 Hz, 1H), 7.08 (d, J=7.5 Hz, 1H), 6.97 (d, J=1.6 Hz, 1H), 6.81-6.67 (m, 1H), 5.21 (s, 2H), 3.97 (q, J=7.1 Hz, 2H), 3.53 (s, 2H), 2.30 (s, 3H), 1.35 (s, 12H), 1.02 (t, J=7.1 Hz, 3H); $^{19}$F NMR (282 MHz, DMSO-$d_6$) δ−57.99.

Step-3: Preparation of Ethyl 2-(2-((7-(2-(((1,1-dimethylethylsulfinamido)methyl)-3-fluoropyridin-4-yl)-3-(trifluoromethyl)benzofuran-5-yl)methoxy)-4-methylphenyl)acetate (343c)

Compound 343c was prepared according to the procedure reported in step-3 of scheme-1 from ethyl 2-(4-methyl-2-((7-(4,4,5,5-tetramethyl-1,3,2-dioxaborolan-2-yl)-3-(trifluoromethyl)benzofuran-5-yl)methoxy)phenyl)acetate (343b) (513 mg, 0.990 mmol) in dioxane (6 mL) using (+)-(S)—N-((4-chloro-3-fluoropyridin-2-yl)methyl)-2-methylpropane-2-sulfinamide (220c) (314 mg, 1.188 mmol), bis(triphenylphosphine)palladium(II) chloride (Pd(PPh$_3$)$_2$Cl$_2$) (104 mg, 0.148 mmol) and a solution of K$_2$CO$_3$ (410 mg, 2.97 mmol) in water (0.6 mL) under an argon atmosphere heating at 100° C. for 3 h on oil bath. This gave after workup, purification by flash column chromatography [silica gel (24g), eluting with MeOH/DCM from 0-15%] ethyl 2-(2-((7-(2-(((1,1-dimethylethylsulfinamido)methyl)-3-fluoropyridin-4-yl)-3-(trifluoromethyl)benzofuran-5-yl)methoxy)-4-methylphenyl)acetate (343c) (614 mg, 100% yield) as a brown oil. MS (ES+): 621.2 (M+1).

Step-4: Preparation of Ethyl 2-(2-((7-(2-(aminomethyl)-3-fluoropyridin-4-yl)-3-(trifluoromethyl)benzofuran-5-yl)methoxy)-4-methylphenyl)acetate (343d)

Compound 343d was prepared according to the procedure reported in step-3 of scheme-305 from ethyl 2-(2-((7-(2-((1,1-dimethylethylsulfinamido)methyl)-3-fluoropyridin-4-yl)-3-(trifluoromethyl)benzofuran-5-yl)methoxy)-4-methylphenyl)acetate (343c) (610 mg, 0.983 mmol) in methanol (10 mL) using HCl (4M in dioxane; 1 mL, 4.00 mmol) and stirring at room temperature for 1 h. This gave after workup, purification by flash column chromatography [silica (12 g), eluting with DMA80/DCM from 0-70%] ethyl 2-(2-((7-(2-(aminomethyl)-3-fluoropyridin-4-yl)-3-(trifluoromethyl)benzofuran-5-yl)methoxy)-4-methylphenyl)acetate (343d) (302 mg, 60% yield) as a pale yellow oil; $^1$H NMR (300 MHz, DMSO-$d_6$) δ 8.91 (d, J=1.9 Hz, 1H), 8.55 (d, J=4.9 Hz, 1H), 7.93 (s, 1H), 7.72 (s, 1H), 7.62 (q, J=4.9 Hz, 1H), 7.09 (d, J=7.6 Hz, 1H), 6.98 (s, 1H), 6.74 (d, J=7.4 Hz, 1H), 5.29 (s, 2H), 3.96-3.85 (m, 4H), 3.57 (s, 2H), 2.30 (s, 3H), 1.02-0.88 (m, 3H); $^{19}$F NMR (282 MHz, DMSO-$d_6$) δ−58.09, −130.71; MS (ES+): 517.2 (M+1).

Step-5: Preparation of 2-(2-((7-(2-(aminomethyl)-3-fluoropyridin-4-yl)-3-(trifluoromethyl)benzofuran-5-yl)methoxy)-4-methylphenyl)acetic Acid (343e)

Compound 343e was prepared according to the procedure reported in step-6 of scheme-1 from ethyl 2-(2-((7-(2-

(aminomethyl)-3-fluoropyridin-4-yl)-3-(trifluoromethyl)benzofuran-5-yl)methoxy)-4-methylphenyl)acetate (343d) (300 mg, 0.581 mmol) in MeOH (6 mL), THF (6 mL) using a solution of lithium hydroxide (97 mg, 2.323 mmol) in water (2 mL). This gave after workup and purification by reverse phase column [C18 (50 g), eluting with ACN in water (containing 0.1% HCl) from 0-100%] 2-(2-((7-(2-(aminomethyl)-3-fluoropyridin-4-yl)-3-(trifluoromethyl)benzofuran-5-yl)methoxy)-4-methylphenyl)acetic acid (343e) (165 mg, 58% yield) HCl salt as a white solid; $^1$H NMR (300 MHz, DMSO-$d_6$) δ 8.94 (q, J=1.6 Hz, 1H), 8.66 (d, J=4.9 Hz, 1H), 8.62 (d, J=5.9 Hz, 3H), 8.01 (s, 1H), 7.83 (t, J=5.3 Hz, 1H), 7.79 (s, 1H), 7.09 (d, J=7.5 Hz, 1H), 6.97 (d, J=1.6 Hz, 1H), 6.74 (d, J=7.5 Hz, 1H), 5.32 (s, 2H), 4.47-4.29 (m, 2H), 3.53 (s, 2H), 2.30 (s, 3H); $^{19}$F NMR (282 MHz, DMSO-$d_6$) δ−58.03, −128.51; MS (ES+): 489.1 (M+1); MS (ES−): 487.1 (M−1); Analysis calculated for: $C_{25}H_{20}F_4N_2O_4 \cdot 1.3HCl \cdot H_2O$: C, 54.22; H, 4.24; Cl, 8.32; N, 5.06; Found: C, 54.29; H, 4.12; Cl, 8.50, N, 5.05.

Scheme-344

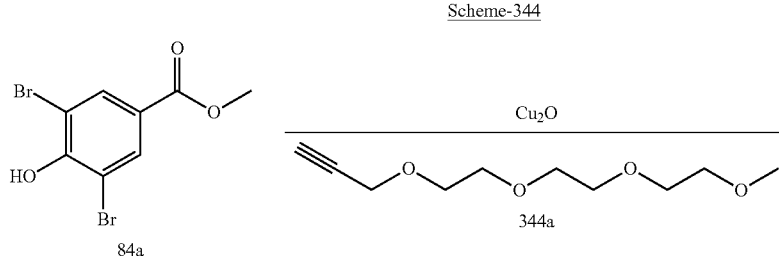

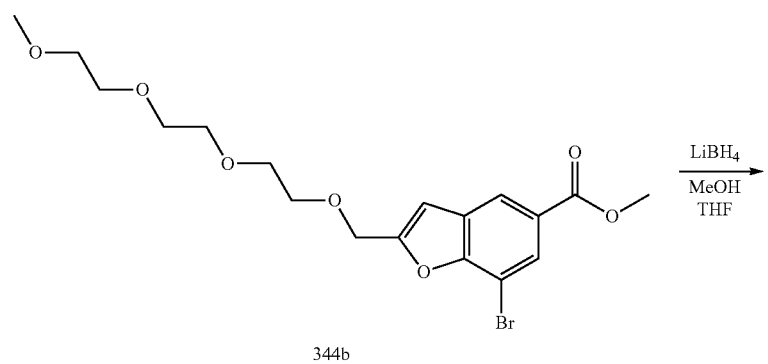

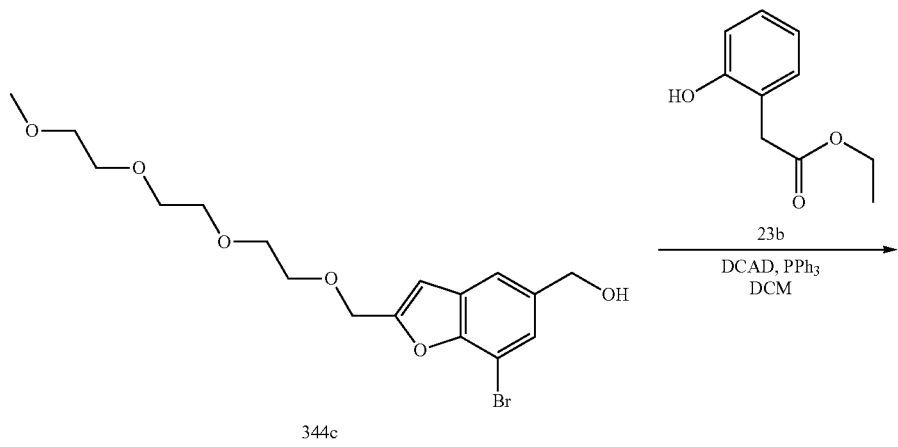

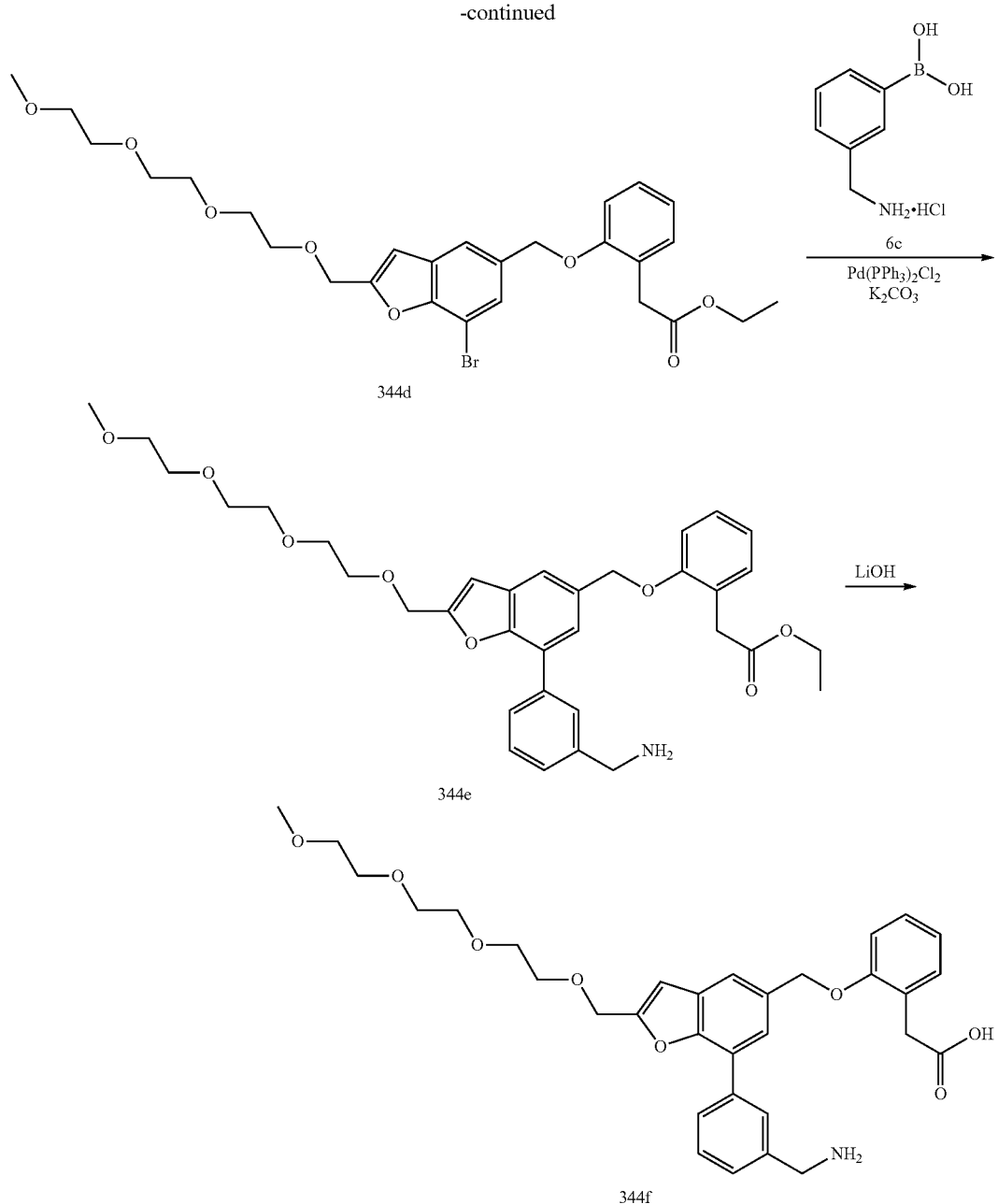

Preparation of 2-(2-((7-(3-aminomethyl)phenyl-2-(2,5,8,11-tetraoxadodecyl)benzofuran-5-yl)methoxy)phenyl)acetic Acid (344f)

Step-1: Preparation of methyl 7-bromo-2-(2,5,8,11-tetraoxadodecyl)benzofuran-5-carboxylate (344b)

Compound 344b was prepared according to the procedure reported in step-1 of scheme-55, from methyl 3,5-dibromo-4-hydroxybenzoate (84a) (7.66 g, 24.72 mmol) in pyridine (150 mL) 2,5,8,11-tetraoxatetradec-13-yne (344a) (5 g, 24.72 mmol), copper(I) oxide (1.769 g, 12.36 mmol) and heating at 120° C. for 3 h in 350 mL sealed flask on an oil bath. This gave after workup and purification by flash column chromatography [silica (80 g), eluting with EtOAc in hexane from 0-80%] methyl 7-bromo-2-(2,5,8,11-tetraoxadodecyl)benzofuran-5-carboxylate (344b) (7.5 g, 70% yield) as a clear oil; $^1$HNMR (300 MHz, DMSO-$d_6$) δ 8.30 (d, J=1.5 Hz, 1H), 8.06 (d, J=1.5 Hz, 1H), 7.17 (s, 1H), 4.73-4.67 (m, 2H), 3.87 (s, 3H), 3.68-3.63 (m, 2H), 3.60-3.55 (m, 2H), 3.53-3.48 (m, 6H), 3.44-3.39 (m, 2H), 3.22 (s, 3H).

Step-2: Preparation of (7-bromo-2-(2,5,8,11-tetraoxadodecyl)benzofuran-5-yl)methanol (344c)

Compound 344c was prepared according to the procedure reported in step-2 of scheme-76 from methyl 7-bromo-2-(2,5,8,11-tetraoxadodecyl)benzofuran-5-carboxylate (344b) (3.7 g, 8.58 mmol) in THF (40 mL) using LiBH$_4$ (6.43 mL, 25.7 mmol, 4 M solution in THF) and MeOH (1.041 mL, 25.7 mmol). This gave after workup and purification by flash column chromatography [silica (40 g), eluting with 0-60% EtOAc in hexane] (7-bromo-2-(2,5,8,11-tetraoxadodecyl) benzofuran-5-yl)methanol (344c) (3.1 g, 90% yield) as a clear oil; ¹H NMR (300 MHz, DMSO-d₆) δ 7.56 (dd, J=1.5, 0.8 Hz, 1H), 7.48 (dd, J=1.5, 0.7 Hz, 1H), 7.01 (s, 1H), 5.32 (t, J=5.8 Hz, 1H), 4.66-4.61 (m, 2H), 4.56 (d, J=5.4 Hz, 2H), 3.65-3.60 (m, 2H), 3.60-3.54 (m, 2H), 3.52-3.47 (m, 6H), 3.43-3.38 (m, 2H), 3.22 (s, 3H); MS (ES+): 436.2 (M+Na).

Step-3: Preparation of Ethyl 2-(2-((7-bromo-2-(2,5,8,11-tetraoxadodecyl)benzofuran-5-yl)methoxy) phenyl)acetate (344d)

Compound 344d was prepared according to the procedure reported in step-2 of scheme-23 from (7-bromo-2-(2,5,8,11-tetraoxadodecyl)benzofuran-5-yl)methanol (344c) (1.85 g, 4.59 mmol) in DCM (50 mL) using triphenylphosphine (1.32 g, 5.05 mmol), ethyl 2-(2-hydroxyphenyl) acetate (23b) (0.91 g, 5.05 mmol) and (E)-bis(4-chlorobenzyl) diazene-1,2-dicarboxylate (DCAD, 1.85 g, 5.05 mmol) in DCM (20 mL). This gave after workup and purification by flash column chromatography [silica (40g), eluting with EtOAc/MeOH (9:1) in hexane from 0-80%] ethyl 2-(2-((7-bromo-2-(2,5,8,11-tetraoxadodecyl)benzofuran-5-yl)methoxy)phenyl)acetate (344d) (1.3 g, 50% yield) as a clear oil; MS (ES+): 587.1 and 589.1 (M+Na).

Step-4: Preparation of Ethyl 2-(2-((7-(3-(aminomethyl)phenyl)-2-(2,5,8,11-tetraoxadodecyl)benzofuran-5-yl)methoxy)phenyl)acetate (344e)

Compound 344e was prepared according to the procedure reported in step-3 of scheme-1 from ethyl 2-(2-((7-bromo-2-(2,5,8,11-tetraoxadodecyl)benzofuran-5-yl)methoxy)phenyl)acetate (344d) (500 mg, 0.88 mmol) in dioxane (15 mL) using 3-(aminomethyl)phenylboronic acid hydrochloride (6c) (298 mg, 1.592 mmol), a solution of K₂CO₃ (367 mg, 2.65 mmol) in water (3 mL), bis(triphenylphosphine)palladium(II) chloride (93 mg, 0.13 mmol) and heating at 100° C. for 3h on oil bath. This gave after workup, purification by flash column chromatography [silica (40 g), eluting with DMA80 in DCM from 0-50%] ethyl 2-(2-((7-(3-(aminomethyl)phenyl)-2-(2,5,8,11-tetraoxadodecyl)benzofuran-5-yl)methoxy)phenyl)acetate (344e) (186 mg, 36% yield) as a clear oil, MS (ES+): 592.3 (M+1).

Step-5: Preparation of 2-(2-((7-(3-(aminomethyl) phenyl)-2-(2,5,8,11-tetraoxadodecyl)benzofuran-5-yl)methoxy)phenyl)acetic Acid (344f)

Compound 344f was prepared according to the procedure reported in step-6 of scheme-1 from ethyl 2-(2-((7-(3-(aminomethyl)phenyl)-2-(2,5,8,11-tetraoxadodecyl)benzofuran-5-yl)methoxy)phenyl)acetate (344e) (93 mg, 0.157 mmol) in MeOH/THF (6 mL, each) using a solution of lithium hydroxide monohydrate (111 mg, 2.65 mmol) in water (2 mL). This gave after workup and purification by reverse-phase column chromatography [EZ-PREP, C-18 column, 30 g, eluting with 0.1% aqueous HCl in water and acetonitrile from 0-100%] 2-(2-((7-(3-(aminomethyl)phenyl)-2-(2,5,8,11-tetraoxadodecyl)benzofuran-5-yl)methoxy) phenyl)acetic acid (344f) (80 mg, 85% yield) HCl salt as a white solid; ¹H NMR (300 MHz, DMSO-d₆) δ 12.25 (s, 1H, D₂O exchangeable), 8.50 (s, 3H, D₂O exchangeable), 7.97 (d, J=1.9 Hz, 1H), 7.93 (dt, J=6.7, 2.1 Hz, 1H), 7.72 (d, J=1.6 Hz, 1H), 7.64 (d, J=1.7 Hz, 1H), 7.61-7.55 (m, 2H), 7.24 (dd, J=8.4, 6.5 Hz, 2H), 7.14-7.06 (m, 1H), 6.99 (s, 1H), 6.91 (td, J=7.4, 1.1 Hz, 1H), 5.26 (s, 2H), 4.67 (s, 2H), 4.13 (q, J=5.8 Hz, 2H), 3.66-3.58 (m, 4H), 3.58-3.53 (m, 2H), 3.52-3.46 (m, 6H), 3.41-3.39 (m, 2H), 3.20 (s, 3H); MS (ES+): 564.3 (M+1); (ES−): 562.2 (M−1); Analysis calculated for C₃₂H₃₇NO₈·HCl·H₂O: C, 62.18; H, 6.52; Cl, 5.74; N, 2.27; Found: C, 61.84; H, 6.47; Cl, 5.89; N, 2.37.

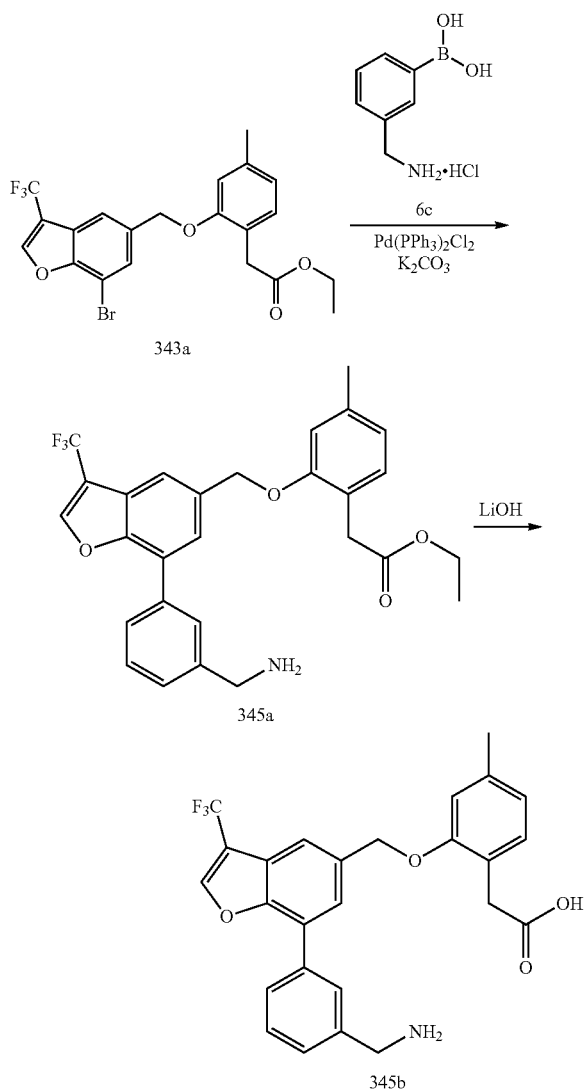

Scheme-345

Preparation of 2-(2-((7-(3-(aminomethyl)phenyl)-3-(trifluoromethyl)benzofuran-5-yl)methoxy)-4-methylphenyl)acetic Acid (345b)

Step-1: Preparation of Ethyl 2-(2-((7-(3-(aminomethyl)phenyl)-3-(trifluoromethyl)benzofuran-5-yl) methoxy)-4-methylphenyl)acetate (345a)

Compound 345a was prepared according to the procedure reported in step-3 of scheme-1 from ethyl 2-(2-((7-bromo-3-(trifluoromethyl)benzofuran-5-yl)methoxy)-4-methylphenyl)acetate (343a) (147 mg, 0.312 mmol) in dioxane (5 mL) using 3-(aminomethyl)phenylboronic acid hydrochloride (6c) (71 mg, 0.468 mmol), a solution of K₂CO₃ (129 mg, 0.936 mmol) in water (0.5 mL), bis(triphenylphosphine) palladium(II) chloride (33 mg, 0.047 mmol) and heating at 100° C. for 3h on oil bath. This gave after workup, purification by flash column chromatography [silica (24 g), eluting with DMA80 in DCM from 0-70%] ethyl 2-(2-((7-(3-(aminomethyl)phenyl)-3-(trifluoromethyl)benzofuran-5-yl)methoxy)-4-methylphenyl)acetate (345a) (104 mg, 67% yield) as a dark oil. $^1$H NMR (300 MHz, DMSO-d$_6$) δ 8.89 (q, J=1.6 Hz, 1H), 7.86-7.66 (m, 4H), 7.55-7.41 (m, 2H), 7.09 (d, J=7.5 Hz, 1H), 6.98 (d, J=1.4 Hz, 1H), 6.74 (dd, J=7.5, 1.4 Hz, 1H), 5.28 (s, 2H), 3.90 (q, J=7.1 Hz, 2H), 3.82 (s, 2H), 3.57 (s, 2H), 2.30 (s, 3H), 0.96 (t, J=7.1 Hz, 3H); $^{19}$F NMR (282 MHz, DMSO-d$_6$) δ−58.08. MS (ES+): 498.1 (M+1).

Step-2: Preparation of 2-(2-((7-(3-(aminomethyl)phenyl)-3-(trifluoromethyl)benzofuran-5-yl)methoxy)-4-methylphenyl)acetic Acid (345b)

Compound 345b was prepared according to the procedure reported in step-6 of scheme-1 from ethyl 2-(2-((7-(3-(aminomethyl)phenyl)-3-(trifluoromethyl)benzofuran-5-yl)methoxy)-4-methylphenyl)acetate (345a) (101 mg, 0.203 mmol) in MeOH/THF (6 mL, each) using a solution of lithium hydroxide monohydrate (60 mg, 1.43 mmol) in water (2 mL). This gave after workup and purification by reverse-phase column chromatography [C-18 column, 50 g, eluting with 0.1% aqueous HCl in water and acetonitrile from 0-100%] 2-(2-((7-(3-(aminomethyl)phenyl)-3-(trifluoromethyl)benzofuran-5-yl)methoxy)-4-methylphenyl)acetic acid (345b) (69 mg, 72% yield) HCl salt as a white solid. $^1$H NMR (300 MHz, DMSO-d$_6$) δ 12.00 (s, 1H), 8.83 (q, J=1.7 Hz, 1H), 8.49 (s, 2H), 7.94 (d, J=2.0 Hz, 1H), 7.85 (ddd, J=5.0, 3.2, 1.8 Hz, 1H), 7.81-7.71 (m, 2H), 7.62-7.49 (m, 2H), 7.03 (d, J=7.5 Hz, 1H), 6.90 (d, J=1.5 Hz, 1H), 6.67 (d, J=7.6 Hz, 1H), 5.23 (s, 2H), 4.07 (s, 2H), 3.48 (s, 2H), 2.22 (s, 3H); $^{19}$F NMR (282 MHz, DMSO-d$_6$) δ−58.01; MS (ES+): 470.1 (M+1); MS (ES−): 468.1 (M−1); Analysis calculated for $C_{26}H_{22}F_3NO_4 \cdot HCl \cdot 0.25H_2O$: C, 61.18; H, 4.64; Cl, 6.95; N, 2.74; Found: C, 61.17; H, 4.48; Cl, 6.91; N, 2.72.

Scheme-346

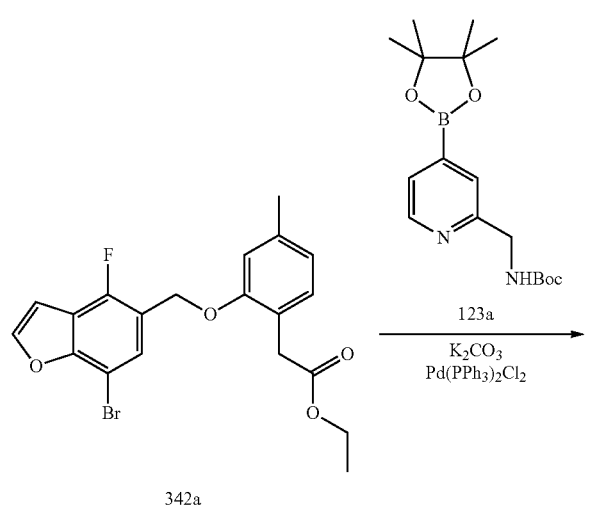

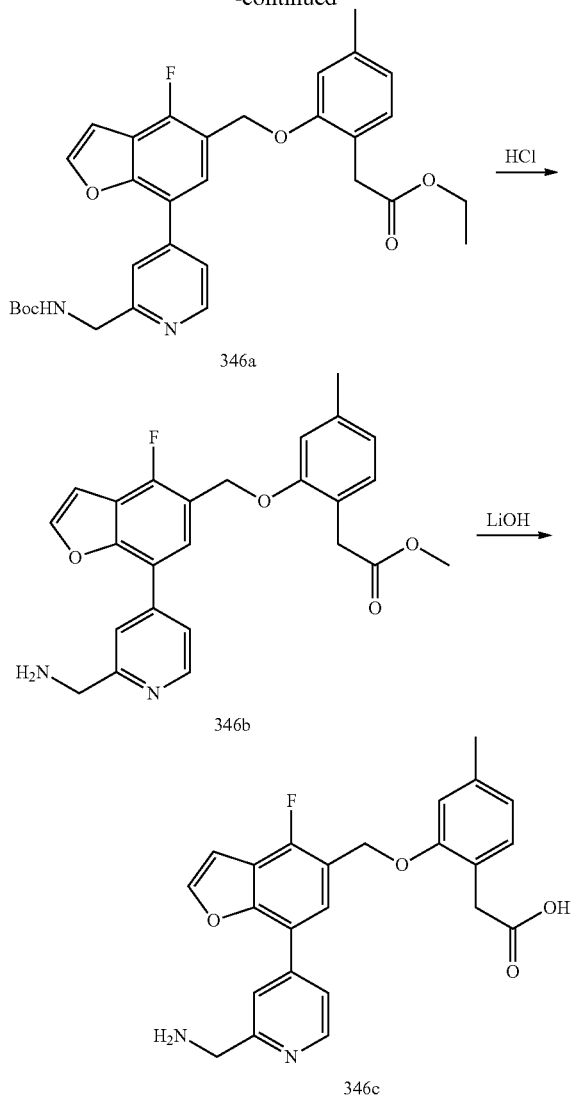

Preparation of 2-(2-((7-(2-(aminomethyl)pyridin-4-yl)-4-fluorobenzofuran-5-yl)methoxy)-4-methylphenyl)acetic Acid (346c)

Step-1: Preparation of Ethyl 2-(2-((7-(2-(((tert-butoxycarbonyl)amino)methyl)pyridin-4-yl)-4-fluorobenzofuran-5-yl)methoxy)-4-methylphenyl)acetate (346a)

Compound 346a was prepared according to the procedure reported in step-3 of scheme-1 from ethyl 2-(2-((7-bromo-4-fluorobenzofuran-5-yl)methoxy)-4-methylphenyl)acetate (342a) (186 mg, 0.442 mmol) in dioxane (5 mL) using tert-butyl ((4-(4,4,5,5-tetramethyl-1,3,2-dioxaborolan-2-yl)pyridin-2-yl)methyl)carbamate (123a) (221 mg, 0.662 mmol), bis(triphenylphosphine)palladium(II) chloride (Pd(PPh$_3$)$_2$Cl$_2$) (47 mg, 0.066 mmol) and a solution of K$_2$CO$_3$ (183 mg, 1.325 mmol) in water (0.5 mL) under an argon atmosphere heating at 100° C. for 3 h on oil bath. This gave after workup, purification by flash column chromatography [silica gel (24g), eluting with DMA80 in DCM from 0-50%] ethyl 2-(2-((7-(2-(((tert-butoxycarbonyl)amino)methyl)pyridin-4-yl)-4-fluorobenzofuran-5-yl)methoxy)-4-methylphenyl)acetate (346a) (242 mg, 100% yield) as a dark oil. MS (ES+): 549.2 (M+1).

Step-2: Preparation of methyl 2-(2-((7-(2-(aminomethyl)pyridin-4-yl)-4-fluorobenzofuran-5-yl)methoxy)-4-methylphenyl)acetate (346b)

Compound 346b was prepared according to the procedure reported in step-3 of scheme-305 from ethyl 2-(2-((7-(2-(((tert-butoxycarbonyl)amino)methyl)pyridin-4-yl)-4-fluorobenzofuran-5-yl)methoxy)-4-methylphenyl)acetate (346a) (240 mg, 0.437 mmol) in methanol (6 mL) using HCl (4M in dioxane; 0.6 mL, 2.4 mmol) and stirring at room temperature overnight. This gave after workup, purification by flash column chromatography [silica (12 g), eluting with DMA80/DCM from 0-100%] methyl 2-(2-((7-(2-(aminomethyl)pyridin-4-yl)-4-fluorobenzofuran-5-yl)methoxy)-4-methylphenyl)acetate (346b) (152 mg, 80% yield) as clear oil. $^1$H NMR (300 MHz, DMSO-$d_6$) δ 8.63 (d, J=5.2 Hz, 1H), 8.22 (d, J=2.3 Hz, 1H), 8.00-7.94 (m, 1H), 7.87 (d, J=6.8 Hz, 1H), 7.75 (dd, J=5.2, 1.8 Hz, 1H), 7.26 (d, J=2.3 Hz, 1H), 7.09 (d, J=7.5 Hz, 1H), 7.05 (d, J=1.5 Hz, 1H), 6.80-6.65 (m, 1H), 5.27 (d, J=1.3 Hz, 2H), 3.93 (s, 2H), 3.55 (s, 2H), 3.40 (s, 3H), 2.32 (s, 3H); $^{19}$F NMR (282 MHz, DMSO) δ−122.71. MS (ES+): 435.2 (M+1).

Step-3: Preparation of 2-(2-((7-(2-(aminomethyl)pyridin-4-yl)-4-fluorobenzofuran-5-yl)methoxy)-4-methylphenyl)acetic Acid (346c)

Compound 346c was prepared according to the procedure reported in step-6 of scheme-1 from methyl 2-(2-((7-(2-(aminomethyl)pyridin-4-yl)-4-fluorobenzofuran-5-yl)methoxy)-4-methylphenyl)acetate (346b) (150 mg, 0.334 mmol) in MeOH (6 mL), THF (6 mL) using a solution of lithium hydroxide (88 mg, 2.097 mmol) in water (2 mL). This gave after workup and purification by reverse phase column [C18 (50 g), eluting with ACN in water (containing 0.1% HCl) from 0-100%] 2-(2-((7-(2-(aminomethyl)pyridin-4-yl)-4-fluorobenzofuran-5-yl)methoxy)-4-methylphenyl)acetic acid (346c) (128 mg, 91% yield) HCl salt as a white solid. $^1$H NMR (300 MHz, DMSO-$d_6$) δ 8.75 (d, J=5.5 Hz, 1H), 8.69 (s, 3H), 8.18 (dd, J=4.1, 2.0 Hz, 2H), 8.01 (dd, J=5.5, 1.7 Hz, 1H), 7.95 (d, J=6.7 Hz, 1H), 7.21 (d, J=2.3 Hz, 1H), 7.02 (d, J=7.5 Hz, 1H), 6.96 (d, J=1.6 Hz, 1H), 6.76-6.60 (m, 1H), 5.22 (s, 2H), 4.28 (s, 2H), 3.45 (s, 2H), 2.24 (s, 3H); $^{19}$F NMR (282 MHz, DMSO-$d_6$) δ−120.99; MS (ES+): 421.1 (M+1); MS (ES−): 419.1 (M−1); Analysis calculated for $C_{24}H_{21}FN_2O_4$·1.9HCl·1.25H$_2$O: C, 56.28; H, 5.00; Cl, 13.15; N, 5.47; Found: C, 56.15; H, 4.64; Cl, 13.06; N, 5.31.

Scheme-347

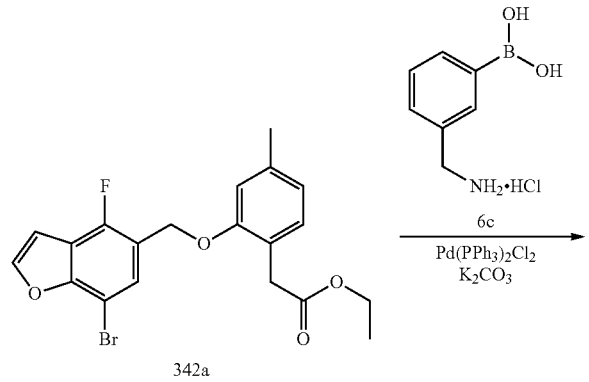

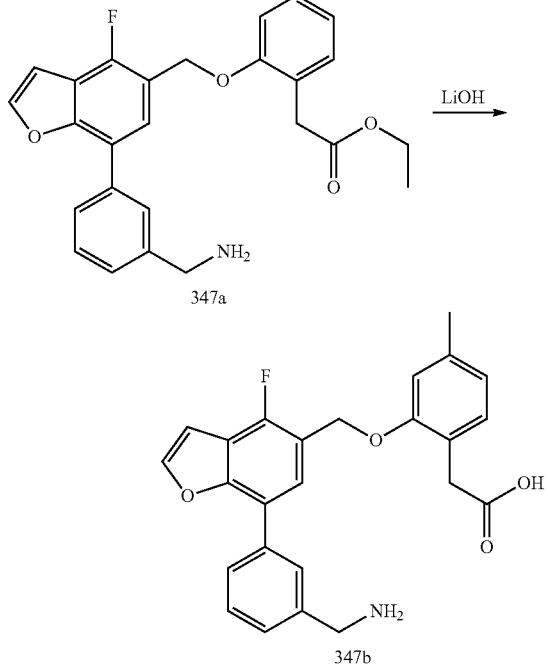

Preparation of 2-(2-((7-(3-(aminomethyl)phenyl)-4-fluorobenzofuran-5-yl)methoxy)-4-methylphenyl)acetic Acid (347b)

Step-1: Preparation of Ethyl 2-(2-((7-(3-(aminomethyl)phenyl)-4-fluorobenzofuran-5-yl)methoxy)-4-methylphenyl)acetate (347a)

Compound 347a was prepared according to the procedure reported in step-3 of scheme-1 from ethyl 2-(2-((7-bromo-4-fluorobenzofuran-5-yl)methoxy)-4-methylphenyl)acetate (342a) (147 mg, 0.349 mmol) in dioxane (5 mL) using 3-(aminomethyl)phenylboronic acid hydrochloride (6c) (79 mg, 0.523 mmol), a solution of K$_2$CO$_3$ (145 mg, 1.047 mmol) in water (0.5 mL), bis(triphenylphosphine)palladium (II) chloride (37 mg, 0.052 mmol) and heating at 100° C. for 3h on oil bath. This gave after workup, purification by flash column chromatography [silica (12 g), eluting with DMA80 in DCM from 0-70%] ethyl 2-(2-((7-(3-(aminomethyl)phenyl)-4-fluorobenzofuran-5-yl)methoxy)-4-methylphenyl)acetate (347a) (102 mg, 65% yield) as a dark oil; $^1$H NMR (300 MHz, DMSO-$d_6$) δ 8.17 (d, J=2.3 Hz, 1H), 7.79 (s, 1H), 7.72-7.63 (m, 2H), 7.46 (t, J=7.5 Hz, 1H), 7.40 (d, J=7.7 Hz, 1H), 7.20 (d, J=2.3 Hz, 1H), 7.08 (d, J=7.5 Hz, 1H), 7.04 (d, J=1.5 Hz, 1H), 6.74 (d, J=7.5 Hz, 1H), 5.25 (s, 2H), 3.90-3.76 (m, 4H), 3.51 (s, 2H), 2.32 (s, 3H), 0.90 (t, J=7.1 Hz, 3H); $^{19}$F NMR (282 MHz, DMSO-$d_6$) δ−125.59. MS (ES+): 448.2 (M+1).

Step-2: Preparation of 2-(2-((7-(3-(aminomethyl)phenyl)-4-fluorobenzofuran-5-yl)methoxy)-4-methylphenyl)acetic Acid (347b)

Compound 347b was prepared according to the procedure reported in step-6 of scheme-1 from ethyl 2-(2-((7-(3-(aminomethyl)phenyl)-4-fluorobenzofuran-5-yl)methoxy)-

4-methylphenyl)acetate (347a) (100 mg, 0.223 mmol) in MeOH/THF (6 mL, each) using a solution of lithium hydroxide monohydrate (52 mg, 1.239 mmol) in water (2 mL). This gave after workup and purification by reverse-phase column chromatography [C-18 column, 50 g, eluting with 0.1% aqueous HCl in water and acetonitrile from 0-100%] 2-(2-((7-(3-(aminomethyl)phenyl)-4-fluorobenzofuran-5-yl)methoxy)-4-methylphenyl)acetic acid (347b) (76 mg, 81% yield) HCl salt as a white solid. $^1$H NMR (300 MHz, DMSO-$d_6$, $D_2O$ Exchange) δ 8.09 (d, J=2.3 Hz, 1H), 7.92 (d, J=1.8 Hz, 1H), 7.88 (dd, J=7.6, 1.6 Hz, 1H), 7.69 (d, J=6.8 Hz, 1H), 7.64-7.45 (m, 2H), 7.17 (d, J=2.3 Hz, 1H), 7.06 (d, J=7.5 Hz, 1H), 6.99 (d, J=1.5 Hz, 1H), 6.73 (d, J=7.5 Hz, 1H), 5.23 (s, 2H), 4.11 (s, 2H), 3.47 (s, 2H), 2.28 (s, 3H); $^{19}$F NMR (282 MHz, DMSO-$d_6$) δ−124.86; MS (ES+): 420.1 (M+1); MS (ES−): 418.1 (M−1); Analysis calculated for $C_{25}H_{22}FNO_4$·HCl·0.25$H_2O$: C, 65.22; H, 5.14; Cl, 7.70; N, 3.04; Found: C, 65.15; H, 5.10; Cl, 7.85; N, 3.09.

Preparation of 2-(2-((7-(3-(aminomethyl)-2-fluorophenyl)-4-fluorobenzofuran-5-yl)methoxy)-4-methylphenyl)acetic Acid (348b)

Step-1: Preparation of Ethyl 2-(2-((7-(3-(aminomethyl)-2-fluorophenyl)-4-fluorobenzofuran-5-yl)methoxy)-4-methylphenyl)acetate (348a)

Compound 348a was prepared according to the procedure reported in step-3 of scheme-1 from ethyl 2-(2-((7-bromo-4-fluorobenzofuran-5-yl)methoxy)-4-methylphenyl)acetate (342a) (150 mg, 0.356 mmol) in dioxane (5 mL) using (3-(aminomethyl)-2-fluorophenyl)boronic acid hydrochloride (56a) (110 mg, 0.534 mmol), a solution of $K_2CO_3$ (148 mg, 1.068 mmol) in water (0.5 mL), bis(triphenylphosphine)palladium(II) chloride (38 mg, 0.053 mmol) and heating at 100° C. for 3h on oil bath. This gave after workup, purification by flash column chromatography [silica (12 g), eluting with DMA80 in DCM from 0-70%] ethyl 2-(2-((7-(3-(aminomethyl)-2-fluorophenyl)-4-fluorobenzofuran-5-yl)methoxy)-4-methylphenyl)acetate (348a) (132 mg, 80% yield) as a dark oil. MS (ES+): 466.1 (M+1).

Step-2: Preparation of 2-(2-((7-(3-(aminomethyl)-2-fluorophenyl)-4-fluorobenzofuran-5-yl)methoxy)-4-methylphenyl)acetic Acid (348b)

Compound 348b was prepared according to the procedure reported in step-6 of scheme-1 from ethyl 2-(2-((7-(3-(aminomethyl)-2-fluorophenyl)-4-fluorobenzofuran-5-yl)methoxy)-4-methylphenyl)acetate (348a) (129 mg, 0.277 mmol) in MeOH/THF (6 mL, each) using a solution of lithium hydroxide monohydrate (75 mg, 1.787 mmol) in water (2 mL). This gave after workup and purification by reverse-phase column chromatography [C-18 column, 50 g, eluting with 0.1% aqueous HCl in water and acetonitrile from 0-100%] 2-(2-((7-(3-(aminomethyl)-2-fluorophenyl)-4-fluorobenzofuran-5-yl)methoxy)-4-methylphenyl)acetic acid (348b) (56 mg, 46% yield) HCl salt as a white solid; $^1$H NMR (300 MHz, DMSO-$d_6$, $D_2O$ exchange) δ 8.09 (d, J=2.3 Hz, 1H), 7.67 (qd, J=7.8, 1.8 Hz, 2H), 7.58 (d, J=6.7 Hz, 1H), 7.45 (t, J=7.7 Hz, 1H), 7.21 (d, J=2.3 Hz, 1H), 7.08 (d, J=7.5 Hz, 1H), 7.03 (d, J=1.6 Hz, 1H), 6.83-6.67 (m, 1H), 5.27 (s, 2H), 4.19 (s, 2H), 3.48 (s, 2H), 2.31 (s, 3H); $^{19}$F NMR (282 MHz, DMSO-$d_6$) δ−118.52, −123.72. MS (ES+): 438.1 (M+1); MS (ES−): 436.1 (M−1); Analysis calculated for $C_{25}H_{21}F_2NO_4$·HCl·0.75$H_2O$: C, 61.60; H, 4.86; Cl, 7.27; N, 2.87; Found: C, 61.59; H, 4.85; Cl, 7.40; N, 2.91.

Scheme-348

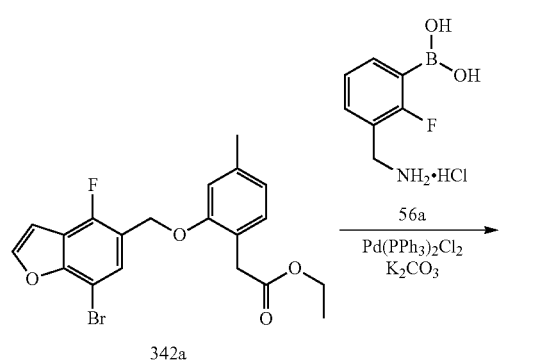

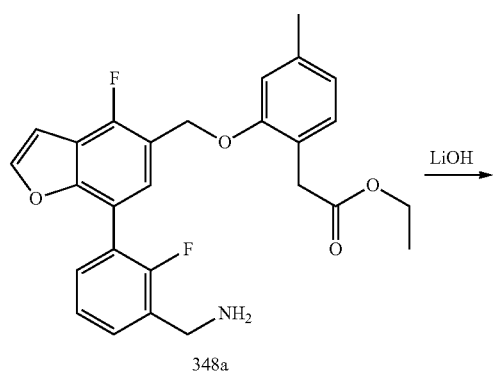

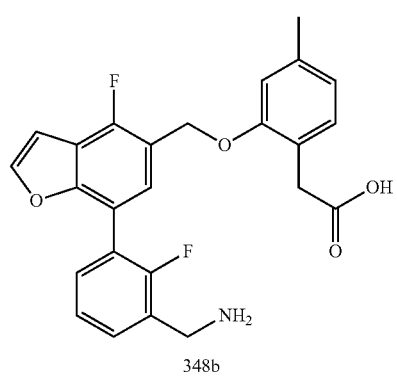

Scheme-348

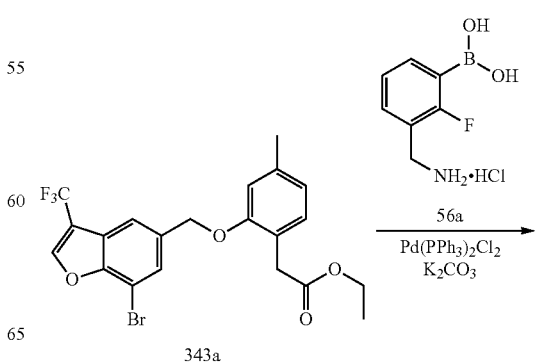

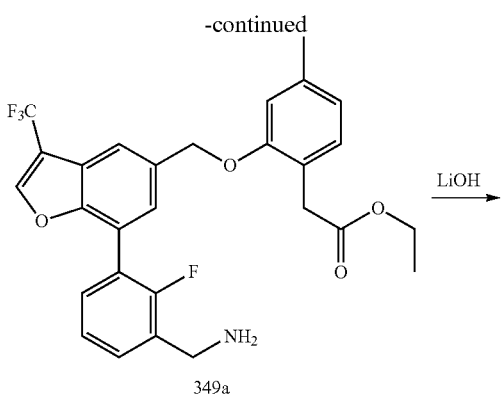

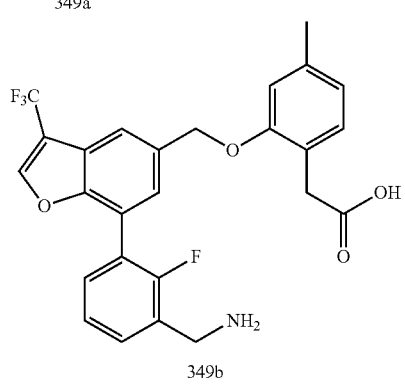

Preparation of 2-(2-((7-(3-(aminomethyl)-2-fluoro-phenyl)-3-(trifluoromethyl)benzofuran-5-yl)methoxy)-4-methylphenyl)acetic Acid (349b)

Step-1: Preparation of Ethyl 2-(2-((7-(3-(aminomethyl)-2-fluorophenyl)-3-(trifluoromethyl)benzofuran-5-yl)methoxy)-4-methylphenyl)acetate (349a)

Compound 349a was prepared according to the procedure reported in step-3 of scheme-1 from ethyl 2-(2-((7-bromo-3-(trifluoromethyl)benzofuran-5-yl)methoxy)-4-methylphenyl)acetate (343a) (154 mg, 0.327 mmol) in dioxane (5 mL) using (3-(aminomethyl)-2-fluorophenyl)boronic acid hydrochloride (56a) (101 mg, 0.490 mmol), a solution of $K_2CO_3$ (135 mg, 0.98 mmol) in water (0.5 mL), bis(triphenylphosphine)palladium(II) chloride (34 mg, 0.049 mmol) and heating at 100° C. for 3h on oil bath. This gave after workup, purification by flash column chromatography [silica (12 g), eluting with DMA80 in DCM from 0-70%] ethyl 2-(2-((7-(3-(aminomethyl)-2-fluorophenyl)-3-(trifluoromethyl)benzofuran-5-yl)methoxy)-4-methylphenyl)acetate (349a) (145 mg, 86% yield) as a dark oil. MS (ES+): 516.2 (M+1).

Step-2: Preparation of 2-(2-((7-(3-(aminomethyl)-2-fluorophenyl)-3-(trifluoromethyl)benzofuran-5-yl)methoxy)-4-methylphenyl)acetic Acid (349b)

Compound 349b was prepared according to the procedure reported in step-6 of scheme-1 from ethyl 2-(2-((7-(3-(aminomethyl)-2-fluorophenyl)-3-(trifluoromethyl)benzofuran-5-yl)methoxy)-4-methylphenyl)acetate (349a) (142 mg, 0.275 mmol) in MeOH/THF (6 mL, each) using a solution of lithium hydroxide monohydrate (105 mg, 2.502 mmol) in water (2 mL). This gave after workup and purification by reverse-phase column chromatography [C-18 column, 50 g, eluting with 0.1% aqueous HCl in water and acetonitrile from 0-100%] 2-(2-((7-(3-(aminomethyl)-2-fluorophenyl)-3-(trifluoromethyl)benzofuran-5-yl)methoxy)-4-methylphenyl)acetic acid (349b) (61 mg, 45% yield) HCl salt as a white solid. $^1$H NMR (300 MHz, DMSO-$d_6$, $D_2O$ exchange) δ 8.78 (t, J=1.8 Hz, 1H), 7.93 (s, 1H), 7.79-7.63 (m, 3H), 7.48 (t, J=7.7 Hz, 1H), 7.10 (d, J=7.5 Hz, 1H), 6.98 (d, J=1.5 Hz, 1H), 6.77 (dd, J=7.7, 1.4 Hz, 1H), 5.30 (s, 2H), 4.21 (s, 2H), 3.54 (s, 2H), 2.30 (s, 3H); $^{19}$F NMR (282 MHz, DMSO-$d_6$) δ −58.02, −118.61. MS (ES+): 488.1 (M+1); MS (ES−): 486.1 (M−1); Analysis calculated for $C_{26}H_{21}F_4NO_4 \cdot HCl \cdot 0.5H_2O$: C, 58.60; H, 4.35; Cl, 6.65; N, 2.63; Found: C, 58.81; H, 4.37; Cl, 6.49; N, 2.64.

Scheme-350

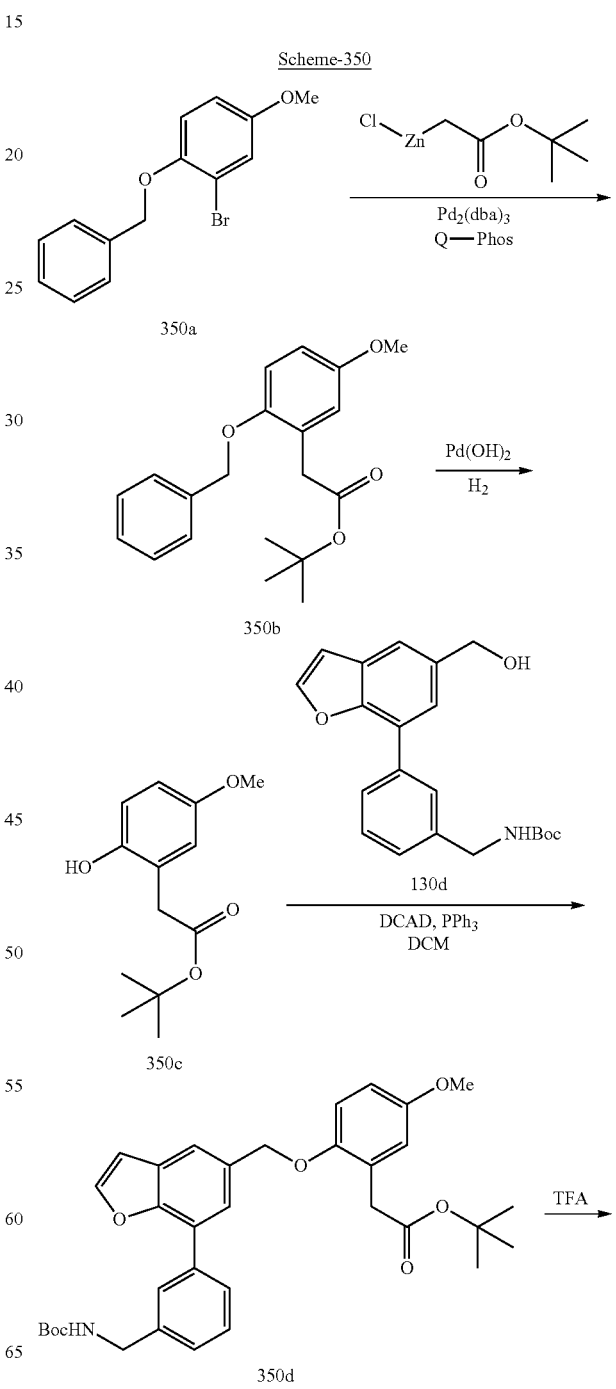

Preparation of 2-(2-((7-(3-(aminomethyl)phenyl)
benzofuran-5-yl)methoxy)-5-methoxyphenyl)acetic
Acid (350e)

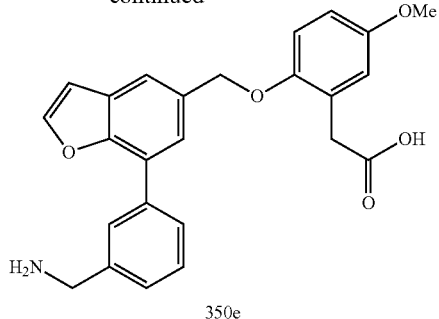

350e

Step-1: Preparation of tert-butyl 2-(2-(benzyloxy)-
5-methoxyphenyl)acetate (350b)

To a stirred suspension of 1-(benzyloxy)-2-bromo-4-methoxybenzene (350a) (0.5 g, 1.71 mmol; CAS #151039-11-1), Pd$_2$(dba)$_3$ (0.16 g, 0.17 mmol) and Q-Phos (0.12 g, 0.17 mmol) in THF (10 mL) was added (2-tert-butoxy-2-oxoethyl)zinc(II) chloride (0.5 M solution in ether; 6.82 mL, 3.41 mmol) and heated at 70° C. for 2 h under an argon atmosphere. The reaction was cooled to room temperature, diluted with ethyl acetate (30 mL) and brine (5 mL). The mixture was stirred for 10 min and filtered through a small pad of Celite. The organic layer was separated, and aqueous layer was extracted with ethyl acetate (50 mL). The combined organic layers were washed with brine (25 mL), dried and concentrated. The crude residue obtained was purified by flash column chromatography (silica gel, 12 g, eluting with ethyl acetate in hexanes 0-50%) to afford tert-butyl 2-(2-(benzyloxy)-5-methoxyphenyl)acetate (350b) (0.5 g, 89% yield) as an oil; $^1$H NMR (300 MHz, DMSO-d$_6$) δ 7.49-7.30 (m, 5H), 6.95 (d, J=8.7 Hz, 1H), 6.82 (d, J=3.0 Hz, 1H), 6.78 (dd, J=8.7, 3.1 Hz, 1H), 5.03 (s, 2H), 3.69 (s, 3H), 3.51 (s, 2H), 1.33 (s, 9H). MS (ES+): 351.1 (M+Na).

Step-2: Preparation of tert-butyl
2-(2-hydroxy-5-methoxyphenyl)acetate (350c)

To a solution of tert-butyl 2-(2-(benzyloxy)-5-methoxyphenyl)acetate (350b) (0.5 g, 1.52 mmol) in MeOH (15 mL) was added Palladium hydroxide on carbon, 20 wt. % loading (dry basis), matrix carbon, wet support (0.107 g, 0.152 mmol) and hydrogenated at atmospheric pressure for 18 h. The reaction mixture was filtered through Celite to remove catalyst and concentrated in vacuum to afford tert-butyl 2-(2-hydroxy-5-methoxyphenyl)acetate (350c) (0.25 g, 69% yield) as a light red oil; $^1$H NMR (300 MHz, DMSO-d$_6$) δ 8.97-8.95 (m, 1H), 6.72-6.66 (m, 2H), 6.66-6.60 (m, 1H), 3.64 (s, 3H), 3.41 (s, 2H), 1.39 (s, 9H). MS (ES+): 261.1 (M+Na).

Step-3: Preparation of tert-butyl 2-(2-((7-(3-(((tert-butoxycarbonyl)amino)methyl)phenyl)benzofuran-5-yl)methoxy)-5-methoxyphenyl)acetate (350d)

Compound 350d was prepared according to the procedure reported in step-2 of scheme-23 from tert-butyl 3-(5-(hydroxymethyl)benzofuran-7-yl)benzylcarbamate (130d) (0.18 g, 0.51 mmol) in DCM (5 mL) using triphenylphosphine (0.17 g, 0.66 mmol), tert-butyl 2-(2-hydroxy-5-methoxyphenyl)acetate (350c) (0.16 g, 0.66 mmol) and (E)-bis(4-chlorobenzyl) diazene-1,2-dicarboxylate (DCAD, 0.24 g, 0.66 mmol) in DCM (5 mL). This gave after workup and purification by flash column chromatography [silica (12 g), eluting with EtOAc in hexane from 0-30%] tert-butyl 2-(2-((7-(3-(((tert-butoxycarbonyl)amino)methyl)phenyl)benzofuran-5-yl)methoxy)-5-methoxyphenyl)acetate (350d) (0.1 g, 34% yield) as a white oil. MS (ES+) 474.2 (M-Boc+1), 596.2 (M+Na).

Step-4: Preparation of 2-(2-((7-(3-(aminomethyl)
phenyl)benzofuran-5-yl)methoxy)-5-methoxyphenyl)acetic Acid (350e)

Compound 350e was prepared according to the procedure reported in step-5 of scheme-1 from tert-butyl 2-(2-((7-(3-(((tert-butoxycarbonyl)amino)methyl)phenyl)benzofuran-5-yl)methoxy)-5-methoxyphenyl)acetate (350d) (0.1 g, 0.17 mmol) in DCM (3 mL) using TFA (0.27 mL, 3.49 mmol) and stirring at room temperature for 12h. This gave after workup and purification by reverse column chromatography [C18 (50 g), eluting with ACN in water (containing 0.1% HCl) from 0-100%] 2-(2-((7-(3-(aminomethyl)phenyl)benzofuran-5-yl)methoxy)-5-methoxyphenyl)acetic acid (350e) (0.03 g, 43% yield) HCl salt as a white solid; $^1$H NMR (300 MHz, DMSO-d$_6$) δ 12.26 (s, 1H), 8.34 (s, 3H), 8.10 (d, J=2.2 Hz, 1H), 7.99 (s, 1H), 7.97-7.88 (m, 1H), 7.74 (d, J=1.6 Hz, 1H), 7.67-7.50 (m, 3H), 7.06 (d, J=2.2 Hz, 1H), 7.03 (s, 1H), 6.85 (d, J=3.1 Hz, 1H), 6.79 (dd, J=8.8, 3.1 Hz, 1H), 5.19 (s, 2H), 4.14 (s, 2H), 3.69 (s, 3H), 3.57 (s, 2H); MS (ES+): 418.1 (M+1); MS (ES−): 416.1 (M−1); Analysis calculated for: C$_{25}$H$_{23}$NO$_5$.HCl.H$_2$O: C, 63.63; H, 5.55; Cl, 7.51; N, 2.97; Found: C, 63.68; H, 5.30; Cl, 7.78; N, 3.00.

Scheme-351

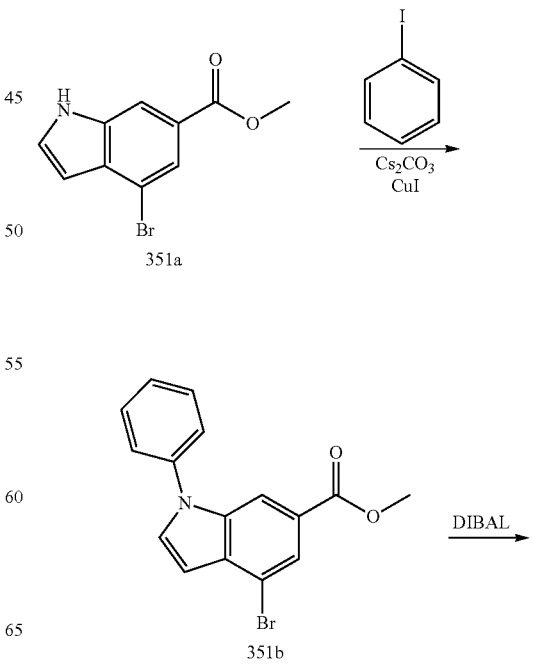

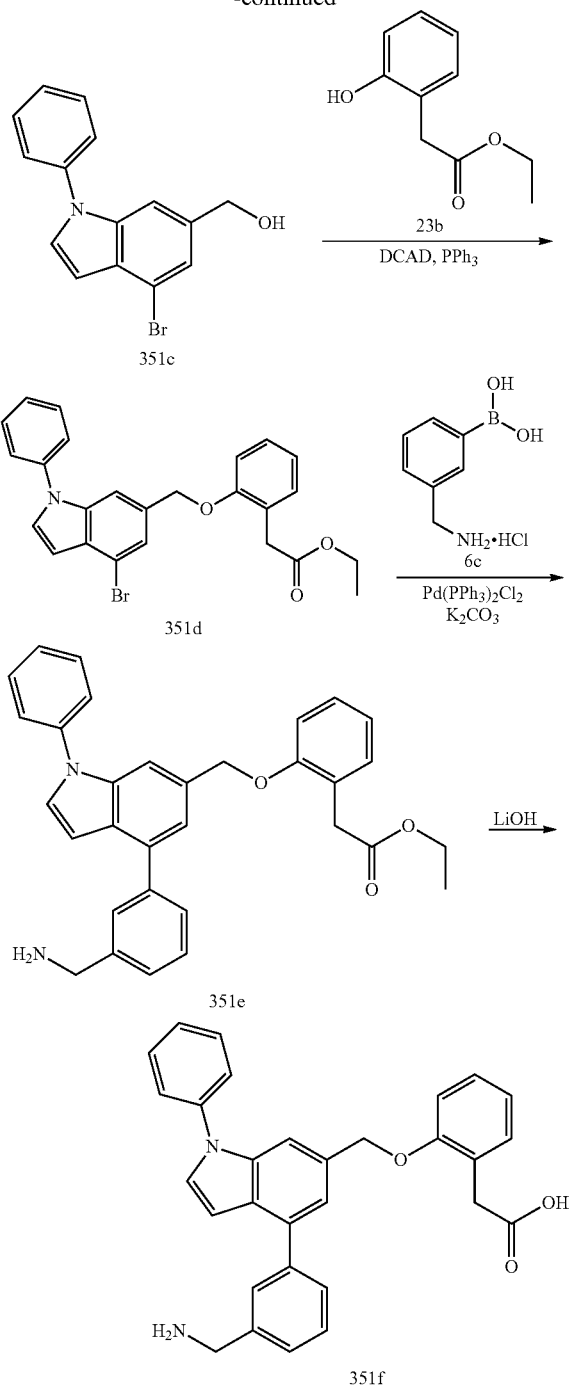

Preparation of 2-(2-((4-(3-(aminomethyl)phenyl)-1-phenyl-1H-indol-6-yl)methoxy)phenyl)acetic Acid (351f)

Step-1: Preparation of methyl 4-bromo-1-phenyl-1H-indole-6-carboxylate (351b)

To a solution of methyl 4-bromo-1H-indole-6-carboxylate (351a) (0.8 g, 3.15 mmol; CAS #882679-96-1) and iodobenzene (0.77 g, 3.78 mmol) in DMF (10 mL) added cesium carbonate (1.54 g, 4.72 mmol) and copper(I) iodide (0.15 g, 0.79 mmol). The mixture was heated at 140° C. for 60 min under microwave condition. The mixture was cooled to room temperature, diluted with water and extracted with ethyl acetate (3×100 mL). The combined organic layers were washed with water (50 mL), brine (30 mL), dried and concentrated. The residue obtained was purified by flash column chromatography (silica gel, 24 g eluting with EtOAc in hexanes from 0-50%) to give methyl 4-bromo-1-phenyl-1H-indole-6-carboxylate (351b) (0.23 g, 23% yield) as a white solid; $^1$H NMR (300 MHz, DMSO-$d_6$) δ 8.07-8.01 (m, 2H), 7.90 (d, J=1.2 Hz, 1H), 7.75-7.58 (m, 4H), 7.58-7.47 (m, 1H), 6.78 (dd, J=3.2, 0.9 Hz, 1H), 3.85 (d, J=2.5 Hz, 3H); MS (ES+): 330.0 & 332.0 (M+1).

Step-2: Preparation of (4-bromo-1-phenyl-1H-indol-6-yl)methanol (351c)

Compound 351c was prepared according to the procedure reported in step-2 of scheme-212 from methyl 4-bromo-1-phenyl-1H-indole-6-carboxylate (351b) (0.38 g, 1.15 mmol) in DCM (10 mL) using 1 M DIBAL-H in DCM (2.88 mL, 2.88 mmol). This gave after workup and purification by flash column chromatography (silica gel 12 g, eluting with 0-50% EtOAc in Hexane) (4-bromo-1-phenyl-1H-indol-6-yl)methanol (351c) (0.3 g, 86% yield) as a white solid; MS (ES+): 303.9 (M+1).

Step-3: Preparation of Ethyl 2-(2-((4-bromo-1-phenyl-1H-indol-6-yl)methoxy)phenyl)acetate (351d)

Compound 351d was prepared according to the procedure reported in step-2 of scheme-23 from (4-bromo-1-phenyl-1H-indol-6-yl)methanol (351c) (0.3 g, 0.99 mmol) in DCM (10 mL) using triphenylphosphine (0.34 g, 1.29 mmol), ethyl 2-(2-hydroxyphenyl) acetate (23b) (0.23 g, 1.29 mmol) and (E)-bis(4-chlorobenzyl) diazene-1,2-dicarboxylate (DCAD, 0.47 g, 1.29 mmol) in DCM (10 mL). This gave after workup and purification by flash column chromatography [silica gel 12 g, eluting with EtOAc in hexanes from 0-50%] ethyl 2-(2-((4-bromo-1-phenyl-1H-indol-6-yl)methoxy)phenyl)acetate (351d) (0.21 g, 46% yield) as a colorless oil; MS (ES+): 487.1 (M+Na); MS (ES−): 463.1 & 465.0 (M−1).

Step-4: Preparation of Ethyl 2-(2-((4-(3-(aminomethyl)phenyl)-1-phenyl-1H-indol-6-yl)methoxy)phenyl)acetate (351e)

Compound 351e was prepared according to the procedure reported in step-3 of scheme-1 from ethyl 2-(2-((4-bromo-1-phenyl-1H-indol-6-yl)methoxy)phenyl)acetate (351d) (0.2 g, 0.43 mmol) in dioxane (5 mL) using 3-(aminomethyl)phenylboronic acid hydrochloride (6c) (0.12 g, 0.65 mmol), a solution of $K_2CO_3$ (0.18 g, 1.29 mmol) in water (2 mL), Pd(PPh$_3$)$_2$Cl$_2$ (0.05 g, 0.07 mmol) and heating under an Ar atmosphere at 100° C. for 2 h. This gave after workup and purification by flash column chromatography [silica (12 g), eluting with MeOH in DCM from 0-20%] followed by reverse phase column chromatography [C18 (50 g), eluting with ACN in water (containing 0.1% HCl) from 0-100%] ethyl 2-(2-((4-(3-(aminomethyl)phenyl)-1-phenyl-1H-indol-6-yl)methoxy)phenyl)acetate (351e) (0.15 g, 71% yield) as a white solid; $^1$H NMR (300 MHz, DMSO-$d_6$) δ 7.74 (d, J=3.3 Hz, 1H), 7.68 (q, J=1.5 Hz, 1H), 7.63 (q, J=3.2 Hz, 5H), 7.55-7.41 (m, 3H), 7.41-7.34 (m, 1H), 7.32-7.17 (m, 3H), 7.11 (dd, J=8.3, 1.2 Hz, 1H), 6.89 (td, J=7.4, 1.1 Hz, 1H), 6.82 (dd, J=3.4, 0.8 Hz, 1H), 5.24 (s, 2H), 3.82 (d, J=2.8 Hz, 2H), 3.80-3.72 (m, 2H), 3.58 (s, 2H), 0.90 (t, J=7.1 Hz, 3H); MS (ES+): 491.2 (M+1).

Step-5: Preparation of 2-(2-((4-(3-(aminomethyl) phenyl)-1-phenyl-1H-indol-6-yl)methoxy)phenyl) acetic Acid (351f)

Compound 351f was prepared according to the procedure reported in step-6 of scheme-1 from ethyl 2-(2-((4-(3-(aminomethyl)phenyl)-1-phenyl-1H-indol-6-yl)methoxy) phenyl)acetate (351e) (0.15 g, 0.31 mmol) in THF (6 mL) and MeOH (6 mL) using a solution of lithium hydroxide hydrate (0.10 g, 2.45 mmol) in water (2 mL). This gave after workup and purification by reverse phase column [C18 (50 g), eluting with ACN in water (containing 0.1% HCl) from 0-100%] 2-(2-((4-(3-(aminomethyl)phenyl)-1-phenyl-1H-indol-6-yl)methoxy)phenyl)acetic acid (351f) (0.04 g, 27% yield) HCl salt as a white solid; $^1$H NMR (300 MHz, DMSO-$d_6$) δ 7.85 (d, J=1.8 Hz, 1H), 7.79 (d, J=3.3 Hz, 1H), 7.75-7.68 (m, 2H), 7.67-7.60 (m, 4H), 7.60-7.50 (m, 2H), 7.46 (dtd, J=6.8, 4.9, 3.2 Hz, 1H), 7.36 (d, J=1.3 Hz, 1H), 7.22 (dd, J=8.9, 6.5 Hz, 2H), 7.09 (d, J=8.1 Hz, 1H), 6.94-6.85 (m, 2H), 5.26 (s, 2H), 4.14 (s, 2H), 3.56 (s, 2H); MS (ES+): 925.3 (2M+1); MS (ES−): 461.2 (M−1); Analysis calculated for: $C_{30}H_{26}N_2O_3 \cdot HCl \cdot 1.5H_2O$: C, 68.50; H, 5.75; N, 5.33; Found: C, 68.54; H, 5.59; N, 5.49.

Scheme-352

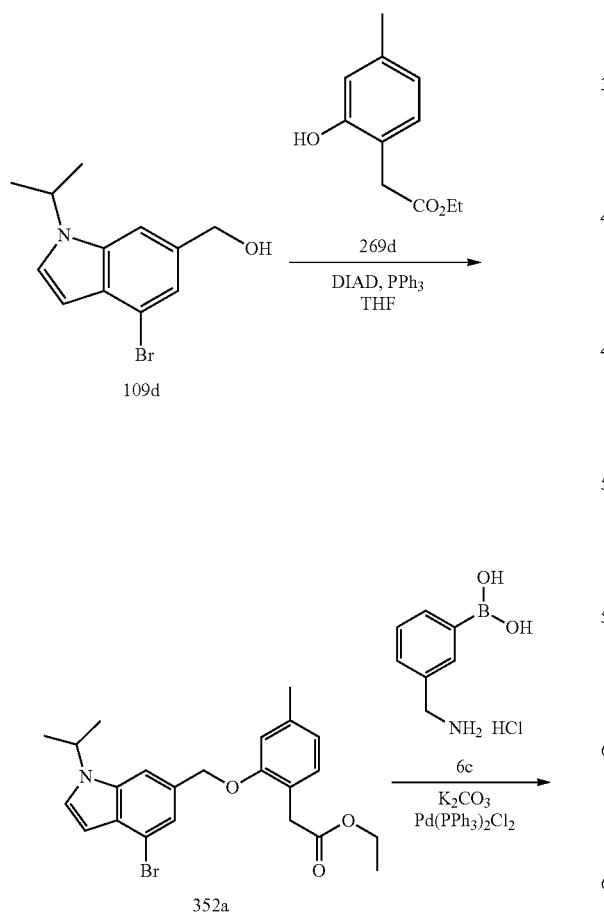

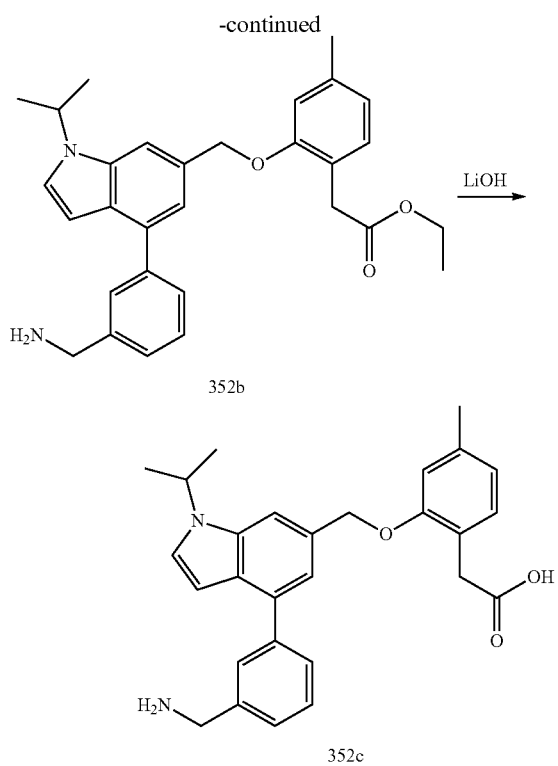

Preparation of 2-(2-((4-(3-(aminomethyl)phenyl)-1-isopropyl-1H-indol-6-yl)methoxy)-4-methylphenyl) acetic Acid (352c)

Step-1: Preparation of Ethyl 2-(2-((4-bromo-1-isopropyl-1H-indol-6-yl)methoxy)-4-methylphenyl) acetate (352a)

Compound 352a was prepared according to the procedure reported in step-2 of scheme-23 from (4-bromo-1-isopropyl-1H-indol-6-yl)methanol (109d) (200 mg, 0.75 mmol) in THF (8 mL) using triphenylphosphine (489 mg, 1.87 mmol), ethyl 2-(2-hydroxy-4-methylphenyl)acetate (269d) (362 mg, 1.87 mmol) and DIAD (0.36 mL, 1.87 mmol). This gave after workup and purification by flash column chromatography [silica gel, eluting with EtOAc/methanol (9:1) in hexane from 0-40%] ethyl 2-(2-((4-bromo-1-isopropyl-1H-indol-6-yl)methoxy)-4-methylphenyl)acetate (352a) (140 mg, 42% yield) as a light yellow oil; $^1$H NMR (300 MHz, DMSO-$d_6$) δ 7.64 (d, J=3.3 Hz, 2H), 7.28 (d, J=1.1 Hz, 1H), 7.08 (d, J=7.5 Hz, 1H), 6.94 (d, J=1.5 Hz, 1H), 6.74-6.67 (m, 1H), 6.43-6.38 (m, 1H), 5.16 (s, 2H), 4.76 (p, J=6.7 Hz, 1H), 4.01 (q, J=7.1 Hz, 2H), 3.56 (s, 2H), 2.29 (s, 3H), 1.47 (d, J=6.6 Hz, 6H), 1.06 (t, J=7.1 Hz, 3H); MS (ES+): 444.1 & 446.1 (M+1).

Step-2: Preparation of Ethyl 2-(2-((4-(3-(aminomethyl)phenyl)-1-isopropyl-1H-indol-6-yl)methoxy)-4-methylphenyl)acetate (352b)

Compound 352b was prepared according to the procedure reported in step-3 of scheme-1 from ethyl 2-(2-((4-bromo- 1-isopropyl-1H-indol-6-yl)methoxy)-4-methylphenyl)acetate (352a) (140 mg, 0.32 mmol) in dioxane (5 mL) using (3-(aminomethyl)phenyl)boronic acid hydrochloride (6c) (71 mg, 0.47 mmol), bis(triphenylphosphine)palladium(II) chloride (Pd(PPh$_3$)$_2$Cl$_2$) (33 mg, 0.05 mmol) and a solution of K$_2$CO$_3$ (131 mg, 0.95 mmol) in water (0.5 mL) under an argon atmosphere heating at 90° C. for 3 h on oil bath. This gave after workup, purification by flash column chromatography [silica gel, 12 g, eluting with DMA80 in DCM from 0-50%] ethyl 2-(2-((4-(3-(aminomethyl)phenyl)-1-isopropyl-1H-indol-6-yl)methoxy)-4-methylphenyl)acetate (352b) (70 mg, 47% yield) as a yellow syrup; δ 7.63 (s, 1H), 7.60 (s, 1H), 7.57 (d, J=3.3 Hz, 1H), 7.49 (d, J=7.4 Hz, 1H), 7.42 (t, J=7.4 Hz, 1H), 7.33 (d, J=7.2 Hz, 1H), 7.16 (d, J=1.3 Hz, 1H), 7.07 (d, J=7.5 Hz, 1H), 6.99 (s, 1H), 6.71 (d, J=7.4 Hz, 1H), 6.58 (d, J=3.3 Hz, 1H), 5.22 (s, 2H), 4.80 (p, J=6.5 Hz, 1H), 3.90 (dt, J=8.1, 6.6 Hz, 2H), 3.79 (s, 2H), 3.56 (s, 2H), 2.29 (s, 3H), 1.50 (d, J=6.6 Hz, 6H), 0.97 (td, J=7.1, 1.0 Hz, 3H); MS (ES+): 471.2 (M+1).

Step-3: Preparation of 2-(2-((4-(3-(aminomethyl)phenyl)-1-isopropyl-1H-indol-6-yl)methoxy)-4-methylphenyl)acetic Acid (352c)

Compound 352c was prepared according to the procedure reported in step-6 of scheme-1 ethyl 2-(2-((4-(3-(aminomethyl)phenyl)-1-isopropyl-1H-indol-6-yl)methoxy)-4-methylphenyl)acetate (352b) (140 mg, 0.30 mmol) in MeOH (4 mL), THF (4 mL) using a solution of lithium hydroxide (100 mg, 2.38 mmol) in water (1 mL). This gave after workup and purification by reverse phase column [C18 (50 g), eluting with ACN in water (containing 0.1% HCl) from 0-100%] 2-(2-((4-(3-(aminomethyl)phenyl)-1-isopropyl-1H-indol-6-yl)methoxy)-4-methylphenyl)acetic acid (352c) (78 mg, 59% yield) HCl salt as a white solid; $^1$H NMR (300 MHz, DMSO-d$_6$) δ 8.41 (s, 2H), 7.81 (s, 1H), 7.68 (d, J=7.6 Hz, 2H), 7.60 (d, J=3.3 Hz, 1H), 7.56 (t, J=7.6 Hz, 1H), 7.48 (d, J=7.5 Hz, 1H), 7.22 (d, J=1.2 Hz, 1H), 7.08 (d, J=7.5 Hz, 1H), 6.99-6.96 (m, 1H), 6.71 (d, J=7.6 Hz, 1H), 6.67 (d, J=3.2 Hz, 1H), 5.24 (s, 2H), 4.82 (p, J=6.6 Hz, 1H), 4.12 (s, 2H), 3.53 (s, 2H), 2.29 (s, 3H), 1.49 (d, J=6.6 Hz, 6H); MS (ES+): 885.4 (2M+1), MS (ES−): 441.2 (M−1); analysis calculated for: C$_{28}$H$_{30}$N$_2$O$_3$.HCl.H$_2$O. C, 67.66; H, 6.69; Cl, 7.13; N, 5.64; found: C, 67.90; H, 6.47; Cl, 7.29; N, 5.66.

Scheme-353

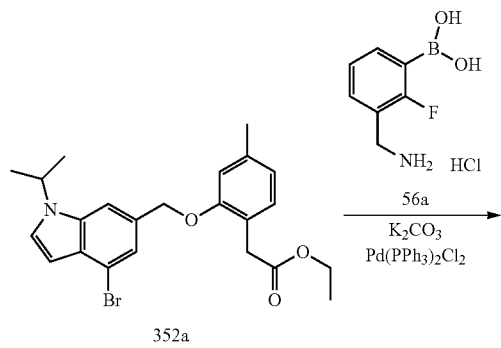

352a

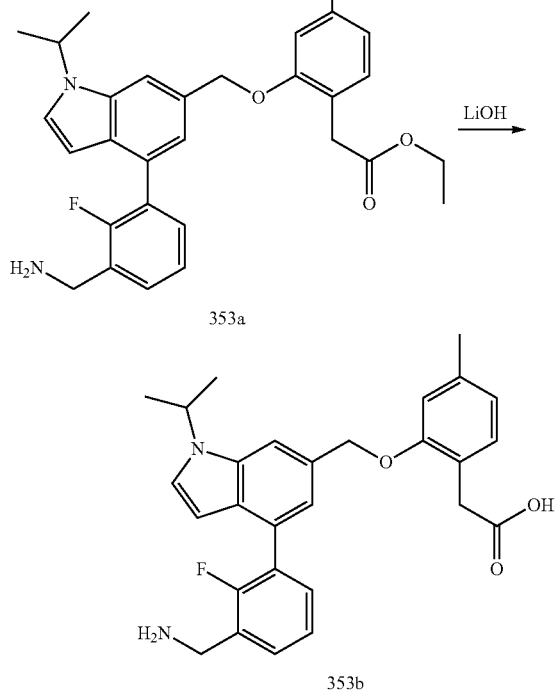

353a

353b

Preparation of 2-(2-((4-(3-(aminomethyl)-2-fluorophenyl)-1-isopropyl-1H-indol-6-yl)methoxy)-4-methylphenyl)acetic Acid (353b)

Step-1: Preparation of Ethyl 2-(2-((4-(3-(aminomethyl)-2-fluorophenyl)-1-isopropyl-1H-indol-6-yl)methoxy)-4-methylphenyl)acetate (353a)

Compound 353a was prepared according to the procedure reported in step-3 of scheme-1 from ethyl 2-(2-((4-bromo-1-isopropyl-1H-indol-6-yl)methoxy)-4-methylphenyl)acetate (352a) (200 mg, 0.45 mmol) in dioxane (5 mL) using (3-(aminomethyl)-2-fluorophenyl)boronic acid hydrochloride (56a) (139 mg, 0.68 mmol), bis(triphenylphosphine) palladium(II) chloride (Pd(PPh$_3$)$_2$Cl$_2$) (47 mg, 0.07 mmol) and a solution of K$_2$CO$_3$ (187 mg, 1.35 mmol) in water (1 mL) under a nitrogen atmosphere heating at 90° C. for 2 h on oil bath. This gave after workup, purification by flash column chromatography [silica gel, 12 g, eluting with DMA80 in DCM from 0-50%] ethyl 2-(2-((4-(3-(aminomethyl)-2-fluorophenyl)-1-isopropyl-1H-indol-6-yl)methoxy)-4-methylphenyl)acetate (353a) (160 mg, 73% yield) as a yellow syrup; MS (ES+): 489.2 (M+1).

Step-2: Preparation of 2-(2-((4-(3-(aminomethyl)-2-fluorophenyl)-1-isopropyl-1H-indol-6-yl)methoxy)-4-methylphenyl)acetic Acid (353b)

Compound 353b was prepared according to the procedure reported in step-6 of scheme-1 from ethyl 2-(2-((4-(3-(aminomethyl)-2-fluorophenyl)-1-isopropyl-1H-indol-6-yl)methoxy)-4-methylphenyl)acetate (353a) (160 mg, 0.33 mmol) in MeOH (4 mL), THF (4 mL) using a solution of lithium hydroxide (110 mg, 2.62 mmol) in water (1 mL). This gave after workup and purification by reverse phase column [C18 (50 g), eluting with ACN in water (containing 0.1% HCl) from 0-100%] 2-(2-((4-(3-(aminomethyl)-2-fluorophenyl)-1-isopropyl-1H-indol-6-yl)methoxy)-4-methylphenyl)acetic acid (353b) (95 mg, 63% yield) HCl salt as a white solid; $^1$H NMR (300 MHz, DMSO-$d_6$) δ 9.27 (s, 2H), 7.72 (s, 1H), 7.65 (td, J=7.3, 1.8 Hz, 1H), 7.61-7.49 (m, 2H), 7.37 (t, J=7.6 Hz, 1H), 7.15 (s, 1H), 7.08 (d, J=7.5 Hz, 1H), 6.97 (d, J=1.6 Hz, 1H), 6.74-6.66 (m, 1H), 6.38 (t, J=3.0 Hz, 1H), 5.24 (s, 2H), 4.82 (p, J=6.6 Hz, 1H), 4.14 (s, 2H), 3.53 (s, 2H), 2.29 (s, 3H), 1.49 (d, J=6.6 Hz, 6H); $^{19}$F NMR (282 MHz, DMSO-$d_6$) δ−118.93; MS (ES−): 459.2 (M−1); Analysis calculated for $C_{28}H_{29}FN_2O_3 \cdot HCl \cdot H_2O$: C, 65.30; H, 6.26; Cl, 6.88; N, 5.44; Found: C, 65.48; H, 6.19; Cl, 6.76; N, 5.49.

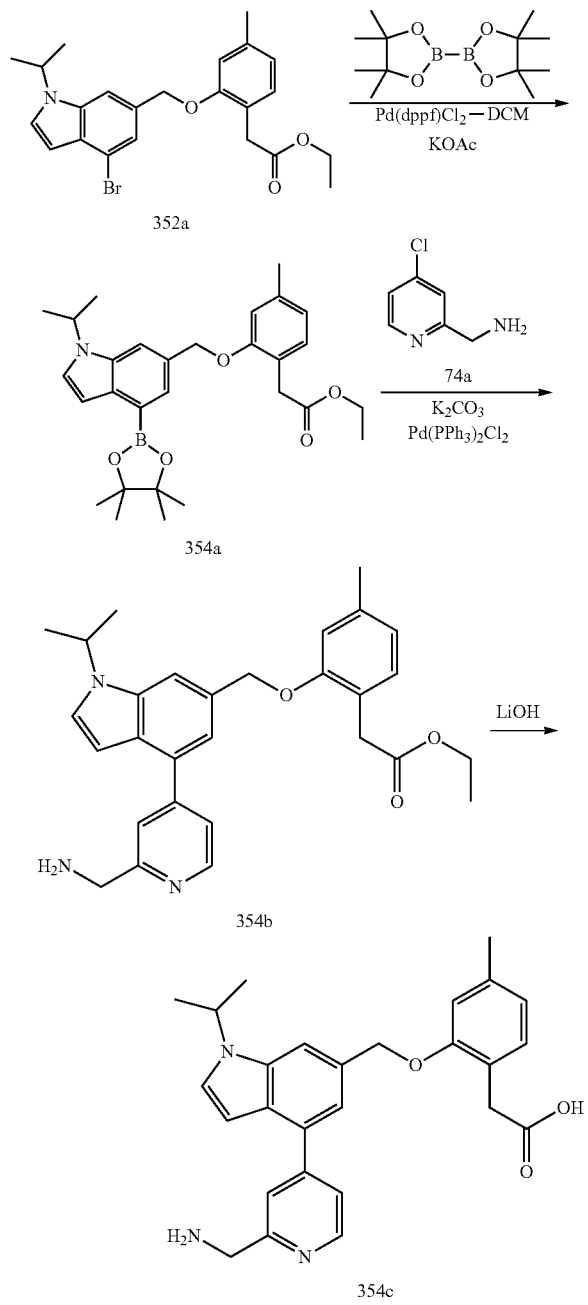

Scheme-354

Preparation of 2-(2-((4-(2-(aminomethyl)pyridin-4-yl)-1-isopropyl-1H-indol-6-yl)methoxy)-4-methylphenyl)acetic Acid (354c)

Step-1: Preparation of Ethyl 2-(2-((1-isopropyl-4-(4,4,5,5-tetramethyl-1,3,2-dioxaborolan-2-yl)-1H-indol-6-yl)methoxy)-4-methylphenyl)acetate (354a)

Compound 354a was prepared according to the procedure reported in step-1 of scheme-59 from ethyl 2-(2-((4-bromo-1-isopropyl-1H-indol-6-yl)methoxy)-4-methylphenyl)acetate (352a) (510 mg, 1.15 mmol), using bis(pinacolato)diboron (437 mg, 1.72 mmol), potassium acetate (338 mg, 3.44 mmol) and Pd(dppf)Cl$_2$-DCM (141 mg, 0.17 mmol) in anhydrous dioxane (10 mL) under an argon atmosphere and heating at 100° C. overnight. This gave after workup and purification by flash column chromatography [silica gel (24g), eluting with EtOAc/methanol (9:1) in hexanes from 0-10%] ethyl 2-(2-((1-isopropyl-4-(4,4,5,5-tetramethyl-1,3,2-dioxaborolan-2-yl)-1H-indol-6-yl)methoxy)-4-methylphenyl)acetate (354a) (310 mg, 55% yield) as a yellow solid; MS (ES$^+$) 514.2 (M+Na).

Step-2: Preparation of Ethyl 2-(2-((4-(2-(aminomethyl)pyridin-4-yl)-1-isopropyl-1H-indol-6-yl)methoxy)-4-methylphenyl)acetate (354b)

Compound 354b was prepared according to the procedure reported in step-3 of scheme-1 from ethyl 2-(2-((1-isopropyl-4-(4,4,5,5-tetramethyl-1,3,2-dioxaborolan-2-yl)-1H-indol-6-yl)methoxy)-4-methylphenyl)acetate (354a) (150 mg, 0.31 mmol) in dioxane (4 mL) using (4-chloropyridin-2-yl)methanamine (74a) (131 mg, 0.92 mmol), bis(triphenylphosphine)palladium(II) chloride (Pd(PPh$_3$)$_2$Cl$_2$) (32 mg, 0.05 mmol) and a solution of K$_2$CO$_3$ (127 mg, 0.26 mmol) in water (1 mL) under a nitrogen atmosphere heating at 90° C. for 2 h on oil bath. This gave after workup, purification by flash column chromatography [silica gel (12 g), eluting with DMA80 in DCM from 0-50%] ethyl 2-(2-((4-(2-(aminomethyl)pyridin-4-yl)-1-isopropyl-1H-indol-6-yl)methoxy)-4-methylphenyl)acetate (354b) (30 mg, 21% yield) as a yellow syrup; MS (ES+): 472.2 (M+1).

Step-3: Preparation of 2-(2-((4-(2-(aminomethyl)pyridin-4-yl)-1-isopropyl-1H-indol-6-yl)methoxy)-4-methylphenyl)acetic Acid (354c)

Compound 354c was prepared according to the procedure reported in step-6 of scheme-1 from ethyl 2-(2-((4-(2-(aminomethyl)pyridin-4-yl)-1-isopropyl-1H-indol-6-yl)methoxy)-4-methylphenyl)acetate (354b) (30 mg, 0.06 mmol) in MeOH (2 mL), THF (2 mL) using a solution of lithium hydroxide (22 mg, 0.51 mmol) in water (0.5 mL). This gave after workup and purification by reverse phase column [C18 (50 g), eluting with ACN in water from 0-100%] 2-(2-((4-(2-(aminomethyl)pyridin-4-yl)-1-isopropyl-1H-indol-6-yl)methoxy)-4-methylphenyl)acetic acid (354c) (7 mg, 25% yield) as a white solid; $^1$H NMR (300 MHz, DMSO-$d_6$) δ 8.65 (d, J=5.2 Hz, 1H), 7.97 (s, 1H), 7.78-7.70 (m, 2H), 7.67 (d, J=3.3 Hz, 1H), 7.45 (d, J=1.2 Hz, 1H), 7.04 (d, J=7.5 Hz, 1H), 6.91 (s, 1H), 6.72 (d, J=3.3 Hz, 1H), 6.71-6.63 (m, 1H), 5.26 (s, 2H), 4.84 (p, J=6.6 Hz, 1H), 4.19 (s, 2H), 3.46 (s, 2H), 2.27 (s, 3H), 1.50 (d, J=6.6 Hz, 6H); MS (ES+): 444.2 (M+1), MS (ES−): 442.2 (M−1).

Scheme-355

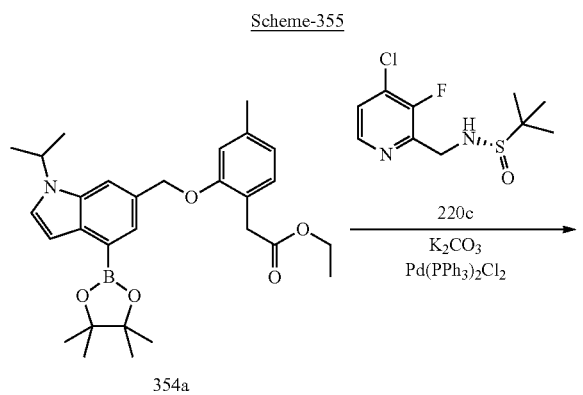

354a

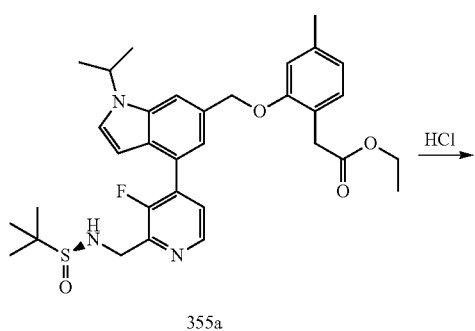

355a

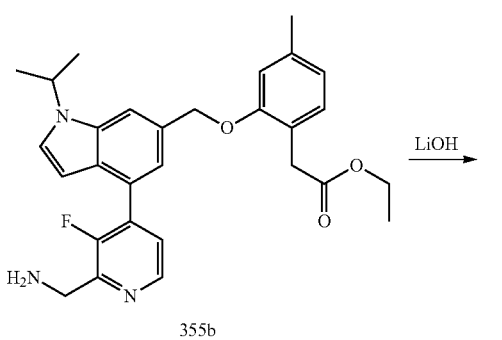

355b

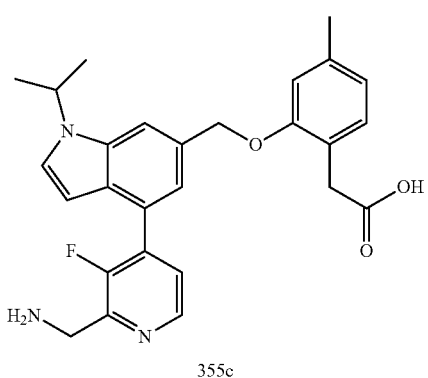

355c

Preparation of 2-(2-((4-(2-(aminomethyl)-3-fluoropyridin-4-yl)-1-isopropyl-1H-indol-6-yl)methoxy)-4-methylphenyl)acetic Acid (355c)

Step-1: Preparation of Ethyl 2-(2-((4-(2-((1,1-dimethylethylsulfinamido)methyl)-3-fluoropyridin-4-yl)-1-isopropyl-1H-indol-6-yl)methoxy)-4-methylphenyl)acetate (355a)

Compound 355a was prepared according to the procedure reported in step-3 of scheme-1 from ethyl 2-(2-((1-isopropyl-4-(4,4,5,5-tetramethyl-1,3,2-dioxaborolan-2-yl)-1H-indol-6-yl)methoxy)-4-methylphenyl)acetate (354a) (190 mg, 0.39 mmol) in dioxane (4 mL) using (+)-(S)—N-((4-chloro-3-fluoropyridin-2-yl)methyl)-2-methylpropane-2-sulfinamide (220c) (205 mg, 0.77 mmol), bis(triphenylphosphine)palladium(II) chloride ($Pd(PPh_3)_2Cl_2$) (41 mg, 0.06 mmol) and a solution of $K_2CO_3$ (160 mg, 1.16 mmol) in water (1 mL) under an argon atmosphere heating at 90° C. for 3 h on oil bath. This gave after workup, purification by flash column chromatography [silica gel (24g), eluting with MeOH/DCM from 0-15%] ethyl 2-(2-((4-(2-((1,1-dimethylethylsulfinamido)methyl)-3-fluoropyridin-4-yl)-1-isopropyl-1H-indol-6-yl)methoxy)-4-methylphenyl)acetate (355a) (100 mg, 44% yield) as a yellow oil; MS (ES+): 594.3 (M+1).

Step-2: Preparation of Ethyl 2-(2-((4-(2-(aminomethyl)-3-fluoropyridin-4-yl)-1-isopropyl-1H-indol-6-yl)methoxy)-4-methylphenyl)acetate (355b)

Compound 355b was prepared according to the procedure reported in step-3 of scheme-305 from ethyl 2-(2-((4-(2-((1,1-dimethylethylsulfinamido)methyl)-3-fluoropyridin-4-yl)-1-isopropyl-1H-indol-6-yl)methoxy)-4-methylphenyl)acetate (355a) (150 mg, 0.25 mmol) in DCM (5 mL) using HCl (4M in dioxane; 0.19 mL, 0.76 mmol) and stirring at room temperature for 1 h. This gave after workup, purification by flash column chromatography [silica (12 g), eluting with DMA80/DCM from 0-70%] ethyl 2-(2-((4-(2-(aminomethyl)-3-fluoropyridin-4-yl)-1-isopropyl-1H-indol-6-yl)methoxy)-4-methylphenyl)acetate (355b) (95 mg, 77% yield) as a pale-yellow oil; MS (ES+): 490.3 (M+1).

Step-3: Preparation of 2-(2-((4-(2-(aminomethyl)-3-fluoropyridin-4-yl)-1-isopropyl-1H-indol-6-yl)methoxy)-4-methylphenyl)acetic Acid (355c)

Compound 355c was prepared according to the procedure reported in step-6 of scheme-1 from ethyl 2-(2-((4-(2-(aminomethyl)-3-fluoropyridin-4-yl)-1-isopropyl-1H-indol-6-yl)methoxy)-4-methylphenyl)acetate (355b) (90 mg, 0.18 mmol) in MeOH (4 mL), THF (4 mL) using a solution of lithium hydroxide (62 mg, 1.47 mmol) in water (0.5 mL). This gave after workup and purification by reverse phase column [C18 (50 g), eluting with ACN in water from 0-100%] 2-(2-((4-(2-(aminomethyl)-3-fluoropyridin-4-yl)-1-isopropyl-1H-indol-6-yl)methoxy)-4-methylphenyl)acetic acid (355c) (30 mg, 35% yield) free base as a white solid; $^1$H NMR (300 MHz, DMSO-$d_6$) δ 8.46 (d, J=4.9 Hz, 1H), 7.77 (s, 1H), 7.61 (d, J=3.3 Hz, 1H), 7.51 (t, J=5.3 Hz, 1H),

1135

7.27 (s, 1H), 7.07 (d, J=7.5 Hz, 1H), 6.95 (s, 1H), 6.70 (d, J=7.5 Hz, 1H), 6.37 (d, J=2.6 Hz, 1H), 5.25 (s, 2H), 4.83 (p, J=6.7 Hz, 1H), 3.97 (s, 2H), 3.51 (s, 2H), 2.28 (s, 3H), 1.49 (d, J=6.5 Hz, 6H); $^{19}$F NMR (282 MHz, DMSO-d$_6$) δ −130.86; MS (ES+): 462.2 (M+1), MS (ES−): 460.2 (M−1); analysis calculated for C$_{27}$H$_{28}$FN$_3$O$_3$·H$_2$O. C, 67.62; H, 6.31; N, 8.76 found: C, 67.63; H, 6.21; N, 8.80.

Scheme-356

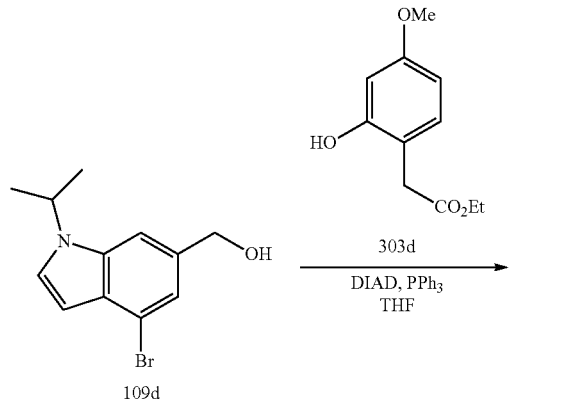

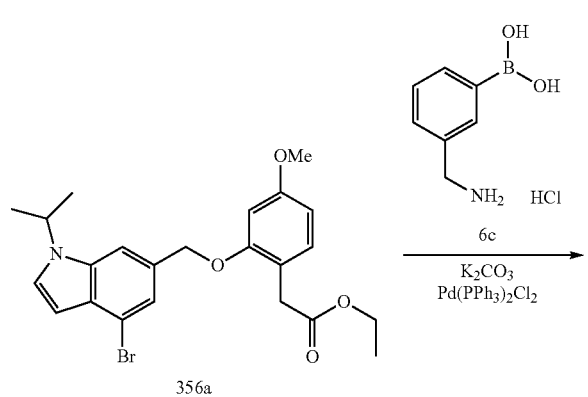

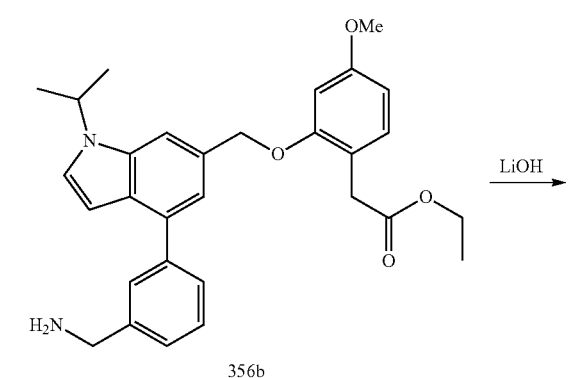

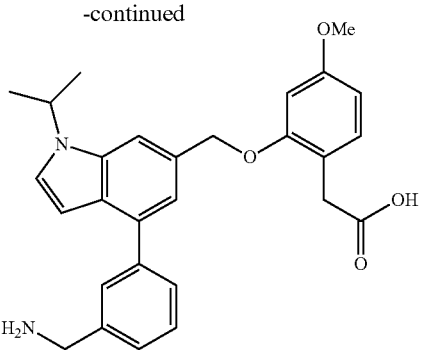

356c

Preparation of 2-(2-((4-(3-(aminomethyl)phenyl)-1-isopropyl-1H-indol-6-yl)methoxy)-4-methoxyphenyl)acetic Acid (356c)

Step-1: Preparation of Ethyl 2-(2-((4-bromo-1-isopropyl-1H-indol-6-yl)methoxy)-4-methoxyphenyl)acetate (356a)

Compound 356a was prepared according to the procedure reported in step-2 of scheme-23 from (4-bromo-1-isopropyl-1H-indol-6-yl)methanol (109d) (0.8 g, 2.98 mmol) in THF (15 mL) using triphenylphosphine (1.57 g, 5.97 mmol), ethyl 2-(2-hydroxy-4-methoxyphenyl)acetate (303d) (1.25 g, 5.97 mmol) and DIAD (1.16 mL, 5.97 mmol). This gave after workup and purification by flash column chromatography [silica gel, eluting with EtOAc/methanol (9:1) in hexane from 0-40%] ethyl 2-(2-((4-bromo-1-isopropyl-1H-indol-6-yl)methoxy)-4-methoxyphenyl)acetate (356a) (0.53 g, 39% yield) as a light yellow oil; $^1$H NMR (300 MHz, DMSO-d$_6$) δ 7.68-7.61 (m, 2H), 7.29 (d, J=1.1 Hz, 1H), 7.11 (d, J=8.3 Hz, 1H), 6.67 (d, J=2.4 Hz, 1H), 6.48 (dt, J=8.3, 2.9 Hz, 1H), 6.41 (dd, J=3.2, 0.8 Hz, 1H), 5.17 (s, 2H), 4.74 (h, J=6.7 Hz, 1H), 4.04-3.97 (m, 2H), 3.74 (s, 3H), 3.54 (s, 2H), 1.47 (d, J=6.6 Hz, 6H), 1.07 (t, J=7.1 Hz, 3H); MS (ES$^+$) 460.1 & 462.1 (M+1); 482.1 & 484.1 (M+Na); MS (ES$^+$) 458.1 & 460.1 (M−1).

Step-2: Preparation of Ethyl 2-(2-((4-(3-(aminomethyl)phenyl)-1-isopropyl-1H-indol-6-yl)methoxy)-4-methoxyphenyl)acetate (356b)

Compound 356b was prepared according to the procedure reported in step-3 of scheme-1 from ethyl 2-(2-((4-bromo-1-isopropyl-1H-indol-6-yl)methoxy)-4-methoxyphenyl)acetate (356a) (0.27 g, 0.59 mmol) in dioxane (5 mL) using (3-(aminomethyl)phenyl)boronic acid hydrochloride (6c) (0.13 g, 0.88 mmol), bis(triphenylphosphine)palladium(II) chloride (Pd(PPh$_3$)$_2$Cl$_2$) (0.06 g, 0.09 mmol) and a solution of K$_2$CO$_3$ (0.24 g, 1.76 mmol) in water (1 mL) under a nitrogen atmosphere heating at 90° C. for 3 h on oil bath. This gave after workup, purification by flash column chromatography [silica gel (24g), eluting with DMA80 in DCM from 0-50%] ethyl 2-(2-((4-(3-(aminomethyl)phenyl)-1-isopropyl-1H-indol-6-yl)methoxy)-4-methoxyphenyl)acetate (356b) (0.13 g, 46% yield) as a yellow syrup; $^1$H NMR (300 MHz, DMSO-d$_6$) δ 7.63 (s, 1H), 7.59 (s, 1H), 7.57 (d, J=3.3 Hz, 1H), 7.51-7.46 (m, 1H), 7.42 (t, J=7.5 Hz, 1H), 7.33 (d, J=7.6 Hz, 1H), 7.16 (d, J=1.3 Hz, 1H), 7.10 (d, J=8.3 Hz, 1H), 6.71 (d, J=2.5 Hz, 1H), 6.58 (d, J=3.3 Hz, 1H), 6.47 (dd, J=8.3, 2.4 Hz, 1H), 5.24 (s, 2H), 4.80 (p, J=6.7 Hz, 1H), 3.91 (q, J=7.1 Hz, 2H), 3.80 (s, 2H), 3.74 (s, 3H), 3.54 (s, 2H), 1.49 (d, J=6.7 Hz, 6H), 0.98 (t, J=7.1 Hz, 3H); MS (ES+): 487.3 (M+1).

Step-3: Preparation of 2-(2-((4-(3-(aminomethyl)phenyl)-1-isopropyl-1H-indol-6-yl)methoxy)-4-methoxyphenyl)acetic Acid (356c)

Compound 356c was prepared according to the procedure reported in step-6 of scheme-1 from ethyl 2-(2-((4-(3-(aminomethyl)phenyl)-1-isopropyl-1H-indol-6-yl)methoxy)-4-methoxyphenyl)acetate (356b) (120 mg, 0.28 mmol) in MeOH (2 mL), THF (2 mL) using a solution of lithium hydroxide (83 mg, 1.97 mmol) in water (0.5 mL). This gave after workup and purification by reverse phase column [C18 (50 g), eluting with ACN in water from 0-100%] 2-(2-((4-(3-(aminomethyl)phenyl)-1-isopropyl-1H-indol-6-yl)methoxy)-4-methoxyphenyl)acetic acid (356c) (60 mg, 53% yield) as a white solid; $^1$H NMR (300 MHz, DMSO-$d_6$) δ 8.08 (d, J=1.8 Hz, 1H), 7.74 (dt, J=7.9, 1.4 Hz, 1H), 7.62 (s, 1H), 7.57 (d, J=3.3 Hz, 1H), 7.48-7.39 (m, 2H), 7.30 (dt, J=7.7, 1.3 Hz, 1H), 7.00 (d, J=8.2 Hz, 1H), 6.63 (dd, J=3.3, 0.7 Hz, 1H), 6.59 (d, J=2.4 Hz, 1H), 6.38 (dd, J=8.2, 2.4 Hz, 1H), 5.25 (s, 2H), 4.80 (p, J=6.6 Hz, 1H), 3.97 (s, 2H), 3.69 (s, 3H), 3.32 (s, 2H), 1.50 (d, J=6.6 Hz, 6H); MS (ES+): 459.2 (M+1), 917.4 (2M+1), MS (ES-): 457.2 (M-1); Analysis calculated for: $C_{28}H_{30}N_2O_4 \cdot 0.5HCl \cdot 0.25H_2O$. C, 70.55; H, 6.61; Cl, 1.86; N, 5.88; Found: C, 70.78; H, 6.44; Cl, 1.76; N, 6.03.

Scheme-357

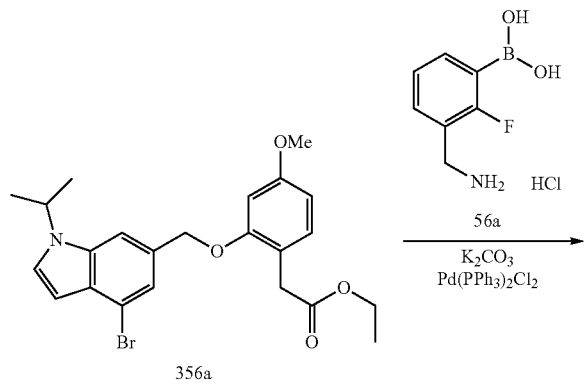

356a

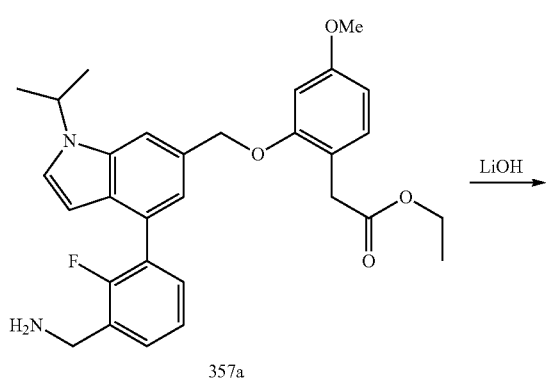

357a

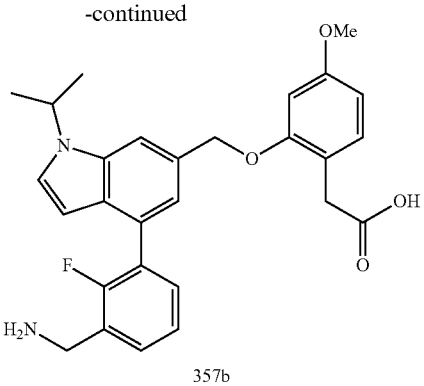

357b

Preparation of 2-(2-((4-(3-(aminomethyl)-2-fluorophenyl)-1-isopropyl-1H-indol-6-yl)methoxy)-4-methoxyphenyl)acetic Acid (357b)

Step-1: Preparation of Ethyl 2-(2-((4-(3-(aminomethyl)-2-fluorophenyl)-1-isopropyl-1H-indol-6-yl)methoxy)-4-methoxyphenyl)acetate (357a)

Compound 357a was prepared according to the procedure reported in step-3 of scheme-1 from ethyl 2-(2-((4-bromo-1-isopropyl-1H-indol-6-yl)methoxy)-4-methoxyphenyl)acetate (356a) (0.27 g, 0.59 mmol) in dioxane (5 mL) using (3-(aminomethyl)-2-fluorophenyl)boronic acid hydrochloride (56a) (0.18 g, 0.88 mmol), bis(triphenylphosphine)palladium(II) chloride (Pd(PPh$_3$)$_2$Cl$_2$) (0.06 g, 0.09 mmol) and a solution of K$_2$CO$_3$ (0.24 g, 1.76 mmol) in water (1 mL) under a nitrogen atmosphere heating at 90° C. for 2 h on oil bath. This gave after workup, purification by flash column chromatography [silica gel, 12 g, eluting with DMA80 in DCM from 0-50%] ethyl 2-(2-((4-(3-(aminomethyl)-2-fluorophenyl)-1-isopropyl-1H-indol-6-yl)methoxy)-4-methoxyphenyl)acetate (357a) (0.22 g, 74% yield) as a yellow syrup; $^1$H NMR (300 MHz, DMSO-$d_6$) δ 7.63 (s, 1H), 7.54 (d, J=3.2 Hz, 1H), 7.53-7.48 (m, 1H), 7.37 (td, J=7.0, 2.6 Hz, 1H), 7.26 (t, J=7.5 Hz, 1H), 7.12-7.07 (m, 2H), 6.71 (d, J=2.4 Hz, 1H), 6.47 (dt, J=8.3, 2.5 Hz, 1H), 6.28 (t, J=2.8 Hz, 1H), 5.23 (s, 2H), 4.80 (p, J=6.7 Hz, 1H), 3.89 (q, J=7.1 Hz, 2H), 3.82 (s, 2H), 3.74 (s, 3H), 3.53 (s, 2H), 1.49 (d, J=6.6 Hz, 6H), 0.97 (t, J=7.1 Hz, 3H); MS (ES+): 505.2 (M+1); 527.2 (M+Na).

Step-2: Preparation of 2-(2-((4-(3-(aminomethyl)-2-fluorophenyl)-1-isopropyl-1H-indol-6-yl)methoxy)-4-methoxyphenyl)acetic Acid (357b)

Compound 357b was prepared according to the procedure reported in step-6 of scheme-1 ethyl 2-(2-((4-(3-(aminomethyl)-2-fluorophenyl)-1-isopropyl-1H-indol-6-yl)methoxy)-4-methoxyphenyl)acetate (357a) (0.22 g, 0.44 mmol) in MeOH (2 mL), THF (2 mL) using a solution of lithium hydroxide (0.15 g, 3.49 mmol) in water (0.5 mL). This gave after workup and purification by reverse phase column [C18 (50 g), eluting with ACN in water from 0-100%] 2-(2-((4-(3-(aminomethyl)-2-fluorophenyl)-1-isopropyl-1H-indol-6-yl)methoxy)-4-methoxyphenyl)acetic acid (357b) (65 mg, 31% yield) free base as a white solid; $^1$H NMR (300 MHz, DMSO-$d_6$) δ 7.66 (s, 1H), 7.54 (d, J=3.3 Hz, 1H), 7.51-7.38 (m, 2H), 7.27 (t, J=7.6 Hz, 1H), 7.19 (d, J=1.5 Hz, 1H), 7.09 (d, J=8.3 Hz, 1H), 6.67 (d, J=2.4 Hz, 1H), 6.46 (dd, J=8.3, 2.4 Hz, 1H), 6.30 (t, J=2.7 Hz, 1H), 5.25 (s, 2H), 4.80 (p, J=6.7 Hz, 1H), 3.85 (s, 2H), 3.73 (s, 3H), 3.47 (s, 2H), 1.49 (d, J=6.6 Hz, 6H); $^{19}$F NMR (282 MHz, DMSO-$d_6$) δ −121.69; MS (ES+): 477.2 (M+1), MS (ES−): 475.2 (M−1); Analysis calculated for: $C_{28}H_{29}FN_2O_4 \cdot 0.5H_2O$. C, 69.26; H, 6.23; N, 5.77; Found: C, 69.13; H, 6.24; N, 5.67.

Scheme-358

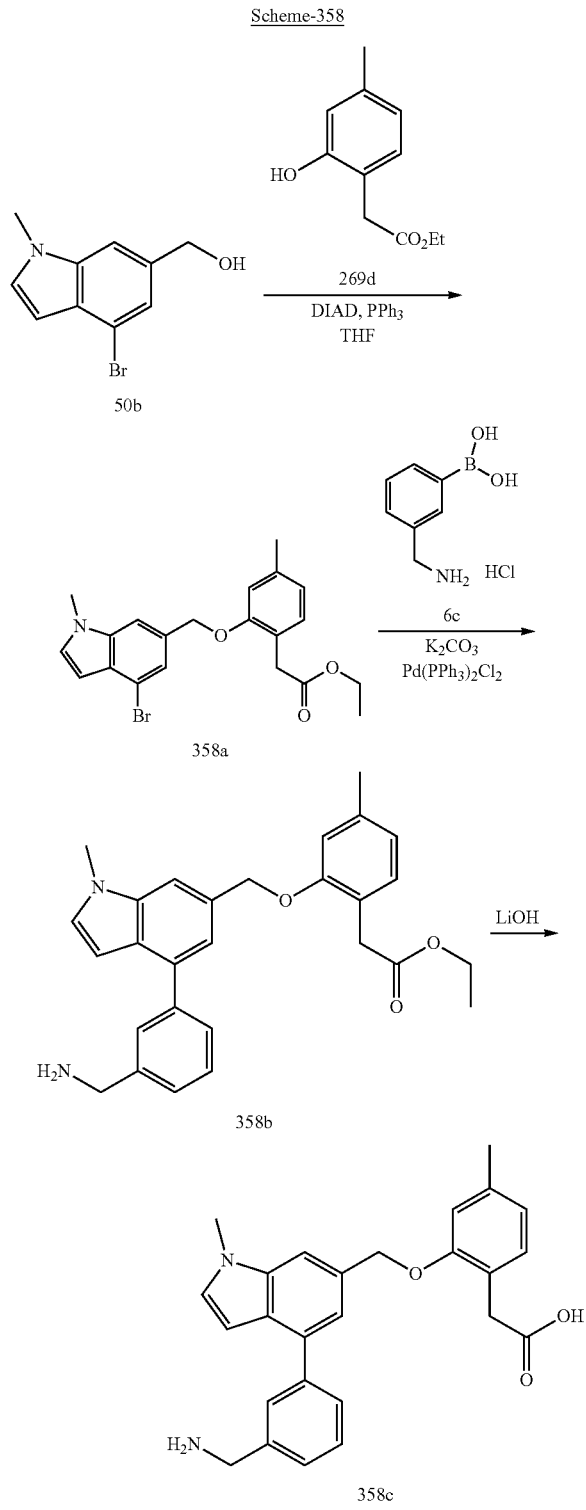

Preparation of 2-(2-((4-(3-(aminomethyl)phenyl)-1-methyl-1H-indol-6-yl)methoxy)-4-methylphenyl) acetic Acid (358c)

Step-1: Preparation of Ethyl 2-(2-((4-bromo-1-methyl-1H-indol-6-yl)methoxy)-4-methylphenyl) acetate (358a)

Compound 358a was prepared according to the procedure reported in step-2 of scheme-23 from (4-bromo-1-methyl-1H-indol-6-yl)methanol (50b) (1.3 g, 5.41 mmol) in THF (30 mL) using triphenylphosphine (2.13 g, 8.12 mmol), ethyl 2-(2-hydroxy-4-methylphenyl)acetate (269d) (1.58 g, 8.12 mmol) and DIAD (1.58 mL, 8.12 mmol). This gave after workup and purification by flash column chromatography [silica gel, 40 g, eluting with EtOAc/MeOH (9:1) in hexane from 0-40%] ethyl 2-(2-((4-bromo-1-methyl-1H-indol-6-yl)methoxy)-4-methylphenyl)acetate (358a) (1.4 g, 62% yield) as a light yellow oil; $^1$H NMR (300 MHz, DMSO-$d_6$) δ 7.56 (t, J=1.1 Hz, 1H), 7.47 (d, J=3.1 Hz, 1H), 7.30 (d, J=1.2 Hz, 1H), 7.08 (d, J=7.5 Hz, 1H), 6.97 (s, 1H), 6.72 (ddd, J=7.5, 1.6, 0.8 Hz, 1H), 6.38 (dd, J=3.1, 0.8 Hz, 1H), 5.16 (s, 2H), 4.03-3.99 (m, 2H), 3.57 (s, 2H), 3.47 (s, 3H), 2.29 (s, 3H), 1.07 (t, J=7.1 Hz, 3H); MS (ES+): 417.1 & 419.0 (M+1); 439.0 & 441.1 (M+Na); MS (ES−): 414.1 & 416.1 (M−1).

Step-2: Preparation of Ethyl 2-(2-((4-(3-(aminomethyl)phenyl)-1-methyl-1H-indol-6-yl)methoxy)-4-methylphenyl)acetate (358b)

Compound 358b was prepared according to the procedure reported in step-3 of scheme-1 from ethyl 2-(2-((4-bromo-1-methyl-1H-indol-6-yl)methoxy)-4-methylphenyl)acetate (358a) (250 mg, 0.60 mmol) in dioxane (5 mL) using (3-(aminomethyl)phenyl)boronic acid hydrochloride (6c) (118 mg, 0.78 mmol), bis(triphenylphosphine)palladium(II) chloride (Pd(PPh$_3$)$_2$Cl$_2$) (63 mg, 0.09 mmol) and a solution of K$_2$CO$_3$ (249 mg, 1.80 mmol) in water (1 mL) under a nitrogen atmosphere heating at 90° C. for 3 h on oil bath. This gave after workup, purification by flash column chromatography [silica gel (24g), eluting with DMA80 in DCM from 0-50%] ethyl 2-(2-((4-(3-(aminomethyl)phenyl)-1-methyl-1H-indol-6-yl)methoxy)-4-methylphenyl)acetate (358b) (130 mg, 49% yield) as a yellow syrup; $^1$H NMR (300 MHz, DMSO-$d_6$) δ 7.66-7.62 (m, 1H), 7.53-7.47 (m, 2H), 7.43-7.39 (m, 2H), 7.33 (d, J=7.5 Hz, 1H), 7.19 (d, J=1.3 Hz, 1H), 7.08 (d, J=7.5 Hz, 1H), 6.98 (d, J=1.6 Hz, 1H), 6.72 (dd, J=7.5, 1.4 Hz, 1H), 6.56 (dd, J=3.2, 0.9 Hz, 1H), 5.22 (s, 2H), 3.91 (q, J=7.1 Hz, 2H), 3.84 (s, 3H), 3.57 (s, 2H), 3.32 (s, 2H), 2.30 (s, 3H), 0.97 (t, J=7.1 Hz, 3H); MS (ES+): 443.2 (M+1)

Step-3: Preparation of 2-(2-((4-(3-(aminomethyl)phenyl)-1-methyl-1H-indol-6-yl)methoxy)-4-methylphenyl)acetic Acid (358c)

Compound 358c was prepared according to the procedure reported in step-6 of scheme-1 from ethyl 2-(2-((4-(3-(aminomethyl)phenyl)-1-methyl-1H-indol-6-yl)methoxy)-4-methylphenyl)acetate (358b) (130 mg, 0.29 mmol) in MeOH (4 mL), THF (4 mL) using a solution of lithium hydroxide (99 mg, 2.35 mmol) in water (1 mL). This gave after workup and purification by reverse phase column [C18 (50 g), eluting with ACN in water from 0-100%] 2-(2-((4-(3-(aminomethyl)phenyl)-1-methyl-1H-indol-6-yl)methoxy)-4-methylphenyl)acetic acid (358c) (70 mg, 58% yield) free base as a white solid; $^1$H NMR (300 MHz, DMSO-$d_6$) δ 8.12 (t, J=1.8 Hz, 1H), 7.75 (dt, J=7.9, 1.4 Hz, 1H), 7.50 (s, 2H), 7.48-7.37 (m, 2H), 7.29 (dt, J=7.5, 1.4 Hz, 1H), 6.97 (d, J=7.5 Hz, 1H), 6.82 (d, J=1.6 Hz, 1H), 6.62 (dd, J=6.9, 2.2 Hz, 2H), 5.24 (s, 2H), 3.96 (s, 2H), 3.85 (s, 3H), 3.34 (s, 2H), 2.24 (s, 3H); MS (ES-): 413.2 (M-1); Analysis calculated for: $C_{26}H_{26}N_2O_3 \cdot H_2O$. C, 72.20; H, 6.53; N, 6.48; Found: C, 72.19; H, 6.52; N, 6.50.

Scheme-359

358a

359a

359b

Preparation of 2-(2-((4-(3-(aminomethyl)-2-fluorophenyl)-1-methyl-1H-indol-6-yl)methoxy)-4-methylphenyl)acetic Acid (359b)

Step-1: Preparation of Ethyl 2-(2-((4-(3-(aminomethyl)-2-fluorophenyl)-1-methyl-1H-indol-6-yl)methoxy)-4-methylphenyl)acetate (359a)

Compound 359a was prepared according to the procedure reported in step-3 of scheme-1 from ethyl 2-(2-((4-bromo-1-methyl-1H-indol-6-yl)methoxy)-4-methylphenyl)acetate (358a) (250 mg, 0.60 mmol) in dioxane (5 mL) using (3-(aminomethyl)-2-fluorophenyl)boronic acid hydrochloride (56a) (160 mg, 0.78 mmol), bis(triphenylphosphine) palladium(II) chloride (Pd(PPh$_3$)$_2$Cl$_2$) (63 mg, 0.09 mmol) and a solution of K$_2$CO$_3$ (249 mg, 1.80 mmol) in water (1 mL) under a nitrogen atmosphere heating at 90° C. for 3 h on oil bath. This gave after workup, purification by flash column chromatography [silica gel (12 g), eluting with DMA80 in DCM from 0-50%] ethyl 2-(2-((4-(3-(aminomethyl)-2-fluorophenyl)-1-methyl-1H-indol-6-yl)methoxy)-4-methylphenyl)acetate (359a) (160 mg, 58% yield) as a yellow syrup; $^1$H NMR (300 MHz, DMSO-$d_6$) δ 7.55 (q, J=2.5, 1.8 Hz, 1H), 7.53-7.50 (m, 1H), 7.38 (d, J=3.2 Hz, 1H), 7.27 (t, J=7.5 Hz, 2H), 7.13 (q, J=1.6 Hz, 1H), 7.10-7.04 (m, 1H), 7.01-6.95 (m, 1H), 6.71 (ddd, J=7.5, 1.6, 0.8 Hz, 1H), 6.25 (ddd, J=3.2, 2.3, 0.9 Hz, 1H), 5.21 (s, 2H), 3.91 (t, J=7.1 Hz, 2H), 3.84 (s, 3H), 3.56 (s, 2H), 3.17 (d, J=4.5 Hz, 2H), 2.30 (s, 3H), 0.97 (t, J=7.1 Hz, 3H); MS (ES+): 461.2 (M+1).

Step-2: Preparation of 2-(2-((4-(3-(aminomethyl)-2-fluorophenyl)-1-methyl-1H-indol-6-yl)methoxy)-4-methylphenyl)acetic Acid (359b)

Compound 359b was prepared according to the procedure reported in step-6 of scheme-1 from ethyl 2-(2-((4-(3-(aminomethyl)-2-fluorophenyl)-1-methyl-1H-indol-6-yl)methoxy)-4-methylphenyl)acetate (359a) (160 mg, 0.35 mmol) in MeOH (4 mL), THF (4 mL) using a solution of lithium hydroxide (117 mg, 2.78 mmol) in water (1 mL). This gave after workup and purification by reverse phase column [C18 (50 g), eluting with ACN in water from 0-100%] 2-(2-((4-(3-(aminomethyl)-2-fluorophenyl)-1-methyl-1H-indol-6-yl)methoxy)-4-methylphenyl)acetic acid (359b) (80 mg, 53% yield) as a white solid; $^1$H NMR (300 MHz, DMSO-$d_6$) δ 7.62 (d, J=1.2 Hz, 1H), 7.50 (td, J=7.3, 1.9 Hz, 1H), 7.40 (td, J=7.4, 1.9 Hz, 1H), 7.36 (d, J=3.1 Hz, 1H), 7.26 (t, J=7.6 Hz, 1H), 7.19 (t, J=1.4 Hz, 1H), 7.05 (d, J=7.5 Hz, 1H), 6.91 (d, J=1.6 Hz, 1H), 6.70-6.65 (m, 1H), 6.29-6.23 (m, 1H), 5.22 (s, 2H), 3.84 (s, 2H), 3.83 (s, 3H), 3.45 (s, 2H), 2.27 (s, 3H); $^{19}$F NMR (282 MHz, DMSO-$d_6$) δ−121.94; MS (ES+): 433.2 (M−1); MS (ES−): 431.2 (M−1); Analysis calculated for: $C_{26}H_{25}FN_2O_3 \cdot 1.75H_2O$. C, 67.30; H, 6.19; N, 6.04; Found: C, 67.35; H, 5.91; N, 6.16.

Scheme-360

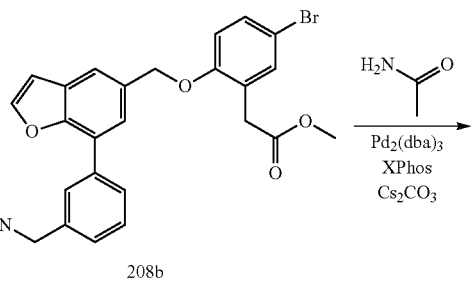

208b

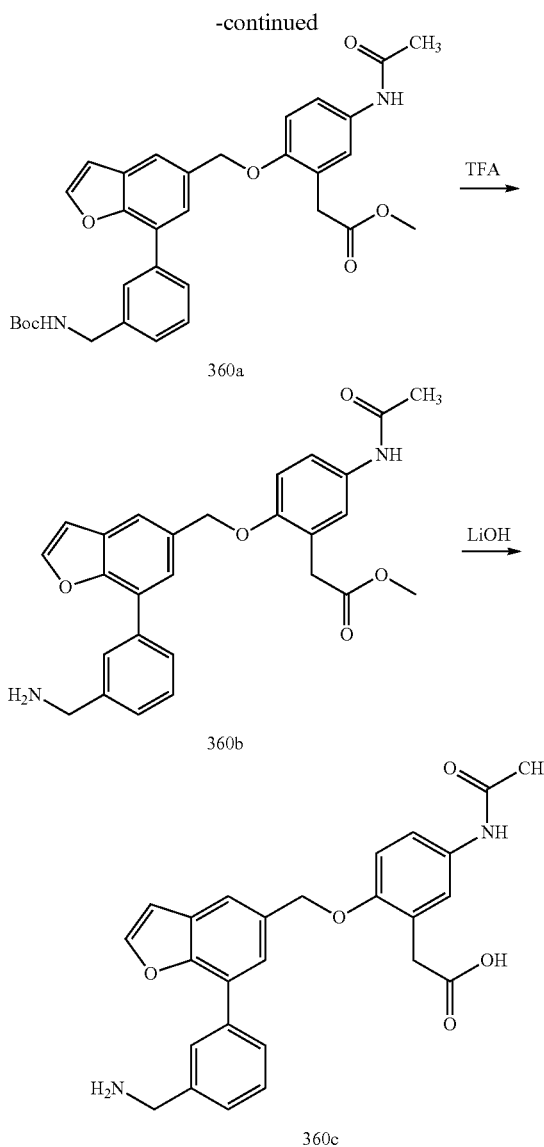

Preparation of 2-(5-acetamido-2-((7-(3-(aminomethyl)phenyl)benzofuran-5-yl)methoxy)phenyl)acetic Acid (360c)

Step-1: Preparation of methyl 2-(5-acetamido-2-((7-(3-(((tert-butoxycarbonyl)amino)methyl)phenyl)benzofuran-5-yl)methoxy)phenyl)acetate (360a)

Compound 360a was prepared according to the procedure reported in step-1 of scheme-224 from methyl 2-(5-bromo-2-((7-(3-(((tert-butoxycarbonyl)amino)methyl)phenyl)benzofuran-5-yl)methoxy)phenyl)acetate (208b) (0.3 g, 0.505 mmol) in anhydrous toluene (3 mL) using acetamide (0.05 g, 0.86 mmol), $Cs_2CO_3$ (0.17 g, 0.517 mmol), dicyclohexyl (2',4',6'-triisopropylbiphenyl-2-yl)phosphine (X-PHOS) (0.02 g, 0.03 mmol), $Pd_2(dba)_3$ (0.02 g, 0.03 mmol) and heating in a microwave at 120° C. for 90 min. This gave after workup and purification by flash column chromatography [silica gel, 12 g, eluting with EtOAc in Hexane from 0 to 50%] methyl 2-(5-acetamido-2-((7-(3-(((tert-butoxycarbonyl)amino)methyl)phenyl)benzofuran-5-yl)methoxy)phenyl)acetate (360a) (0.01 g, 11% yield) as an orange syrup; MS (ES+): 459.2 (M-Boc+1), 581.2 (M+Na); MS (ES−): 557.2 (M−1).

Step-2: Preparation of methyl 2-(5-acetamido-2-((7-(3-(aminomethyl)phenyl)benzofuran-5-yl)methoxy)phenyl)acetate (360b)

Compound 360b was prepared according to the procedure reported in step-5 of scheme-1 from methyl 2-(5-acetamido-2-((7-(3-(((tert-butoxycarbonyl)amino)methyl)phenyl)benzofuran-5-yl)methoxy)phenyl)acetate (360a) (0.04 g, 0.07 mmol) in DCM (3 mL) using TFA (0.11 mL, 1.36 mmol). This gave after workup and purification by reverse phase column chromatography [C18 (50 g), eluting with ACN in water (containing 0.1% HCl) from 0-100%] methyl 2-(5-acetamido-2-((7-(3-(aminomethyl)phenyl)benzofuran-5-yl)methoxy)phenyl)acetate (360b) (0.03 g, 100% yield) as a white solid; MS (ES+): 459.2 (M+1); MS (ES−): 457.1 (M−1).

Step-3: Preparation of 2-(5-acetamido-2-((7-(3-(aminomethyl)phenyl)benzofuran-5-yl)methoxy)phenyl)acetic Acid (360c)

Compound 360c was prepared according to the procedure reported in step-6 of scheme-1 from methyl 2-(5-acetamido-2-((7-(3-(aminomethyl)phenyl)benzofuran-5-yl)methoxy)phenyl)acetate (360b) (0.03 g, 0.07 mmol) in THF (4 mL) and methanol (4 mL) using lithium hydroxide hydrate (0.02 g, 0.41 mmol) in water (1 mL). This gave after workup and purification by reverse phase column [C18 (30g), eluting with ACN in water (containing 0.1% HCl) from 0-100%] 2-(5-acetamido-2-((7-(3-(aminomethyl)phenyl)benzofuran-5-yl)methoxy)phenyl)acetic acid (360c) (0.01 g, 43% yield) HCl salt as a white solid; $^1$H NMR (300 MHz, DMSO-$d_6$) δ 12.27 (s, 1H), 9.81 (s, 1H), 8.32 (s, 3H), 8.11 (d, J=2.2 Hz, 1H), 7.98 (d, J=1.7 Hz, 1H), 7.93 (dt, J=7.6, 1.6 Hz, 1H), 7.75 (d, J=1.6 Hz, 1H), 7.66-7.50 (m, 3H), 7.48-7.37 (m, 2H), 7.06 (d, J=2.2 Hz, 1H), 7.03 (d, J=8.8 Hz, 1H), 5.22 (s, 2H), 4.19-4.10 (m, 2H), 3.56 (s, 2H), 1.99 (s, 3H); MS (ES+): 445.1 (M+1), 889.3 (2M+1); MS (ES−): 443.1 (M−1), 887.3 (2M−1).

Scheme-361

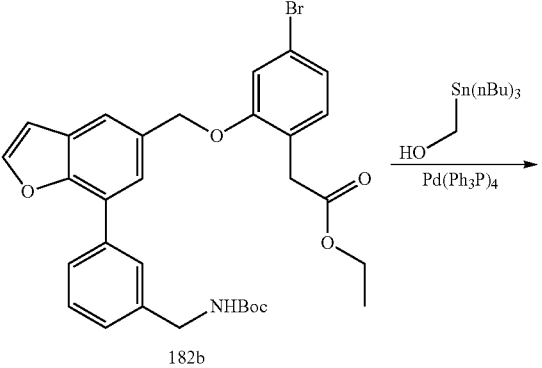

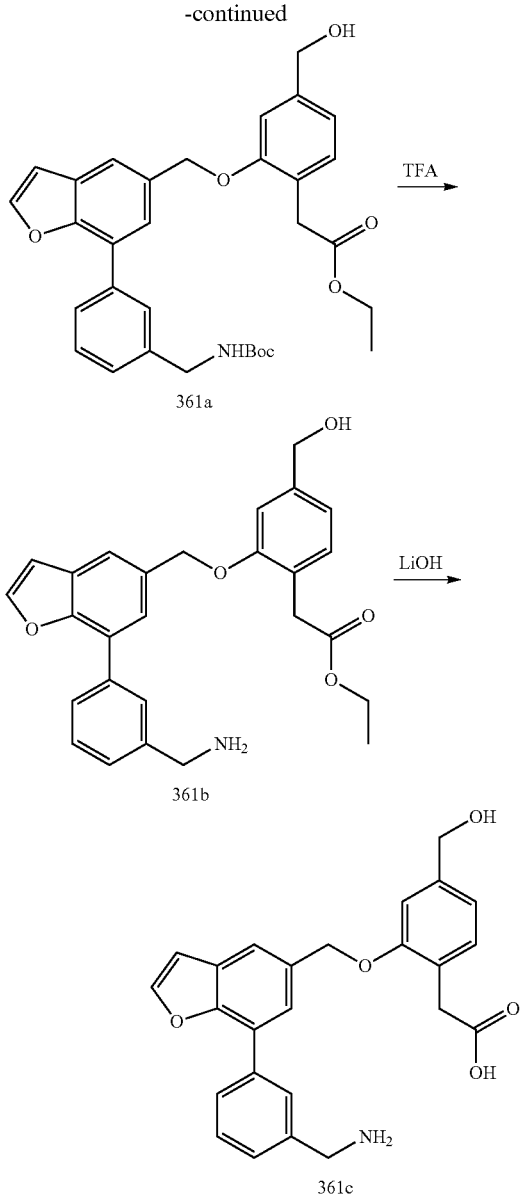

Preparation of 2-(2-((7-(3-(aminomethyl)phenyl)
benzofuran-5-yl)methoxy)-4-(hydroxymethyl)phenyl)acetic Acid (361c)

Step-1: Preparation of Ethyl 2-(2-((7-(3-(((tert-butoxycarbonyl)amino)methyl)phenyl)benzofuran-5-yl)methoxy)-4-(hydroxymethyl)phenyl)acetate (361a)

Compound 361a was prepared according to the procedure reported in step-1 of scheme-236 from ethyl 2-(4-bromo-2-((7-(3-(((tert-butoxycarbonyl)amino)methyl)phenyl)benzofuran-5-yl)methoxy)phenyl)acetate (182b) (0.05 g, 0.084 mmol) in DMF (4 mL) using (tributylstannyl)methanol (0.04 g, 0.13 mmol), Pd(Ph₃P)₄ (0.02 g, 0.02 mmol) and heating at 120° C. for 1 h in a microwave. This gave after workup and purification by flash column chromatography (silica gel, 12 g, eluting with MeOH in DCM from 0 to 60%) ethyl 2-(2-((7-(3-(((tert-butoxycarbonyl)amino)methyl)phenyl)benzofuran-5-yl)methoxy)-4-(hydroxymethyl)phenyl)
acetate (361a) (0.03 g, 65% yield) as a white solid; MS (ES+): 446.2 (M-Boc+1), 568.2 (M+Na); MS (ES−): 544.2 (M−1).

Step-2: Preparation of Ethyl 2-(2-((7-(3-(aminomethyl)phenyl)benzofuran-5-yl)methoxy)-4-(hydroxymethyl)phenyl)acetate (361b)

Compound 361b was prepared according to the procedure reported in step-5 of scheme-1 from ethyl 2-(2-((7-(3-(((tert-butoxycarbonyl)amino)methyl)phenyl)benzofuran-5-yl)methoxy)-4-(hydroxymethyl)phenyl)acetate (361a) (0.09 g, 0.17 mmol) in DCM (3 mL) using TFA (0.25 mL, 3.30 mmol). This gave after workup and purification by reverse phase column chromatography [C18 (50 g), eluting with ACN in water (containing 0.1% HCl) from 0-100%] ethyl 2-(2-((7-(3-(aminomethyl)phenyl)benzofuran-5-yl)methoxy)-4-(hydroxymethyl)phenyl)acetate (361b) (0.07 g, 100% yield) as a white solid; MS (ES+): 446.2 (M+1); MS (ES−): 444.1 (M−1).

Step-3: Preparation of 2-(2-((7-(3-(aminomethyl)phenyl)benzofuran-5-yl)methoxy)-4-(hydroxymethyl)phenyl)acetic Acid (361c)

Compound 361c was prepared according to the procedure reported in step-6 of scheme-1 from ethyl 2-(2-((7-(3-(aminomethyl)phenyl)benzofuran-5-yl)methoxy)-4-(hydroxymethyl)phenyl)acetate (361b) (73 mg, 0.16 mmol) in THF/methanol (4 mL, each) using a solution of lithium hydroxide hydrate (83 mg, 1.97 mmol) in water (1 mL). This gave after workup and purification by reverse phase column chromatography [C18 (50 g), eluting with ACN in water (containing 0.1% HCl) from 0-100%] 2-(2-((7-(3-(aminomethyl)phenyl)benzofuran-5-yl)methoxy)-4-(hydroxymethyl)phenyl)acetic acid (361c) (0.03 g, 42% yield) HCl salt as a white solid; ¹H NMR (300 MHz, DMSO-d₆) δ 12.19 (s, 1H), 8.36 (s, 3H), 8.11 (d, J=2.2 Hz, 1H), 8.00 (d, J=1.7 Hz, 1H), 7.94 (dt, J=7.5, 1.6 Hz, 1H), 7.77 (d, J=1.6 Hz, 1H), 7.66 (d, J=1.6 Hz, 1H), 7.60 (t, J=7.6 Hz, 1H), 7.54 (dt, J=7.7, 1.6 Hz, 1H), 7.16 (d, J=7.6 Hz, 1H), 7.09 (d, J=1.5 Hz, 1H), 7.07 (d, J=2.2 Hz, 1H), 6.86 (dd, J=7.5, 1.4 Hz, 1H), 5.25 (s, 2H), 5.21 (t, J=5.7 Hz, 1H), 4.47 (d, J=5.4 Hz, 2H), 4.14 (s, 2H), 3.57 (s, 2H); MS (ES+): 418.2 (M+1), 835.3 (2M+1); MS (ES−): 416.1 (M−1); Analysis calculated for: C₂₅H₂₃NO₅.1HCl.1.25H₂O: C, 63.02; H, 5.61; Cl, 7.44; N, 2.94; Found: C, 63.16; H, 5.35; Cl, 7.63; N, 3.00.

Scheme-362

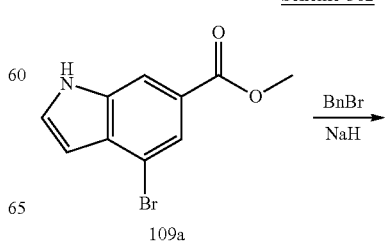

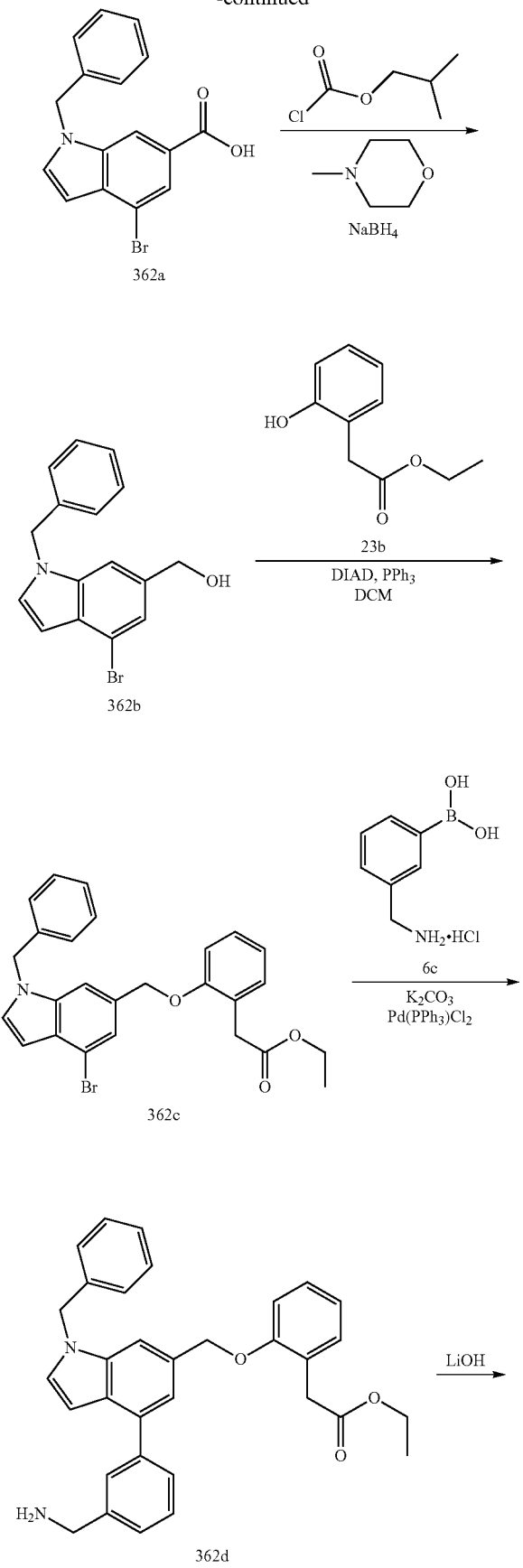
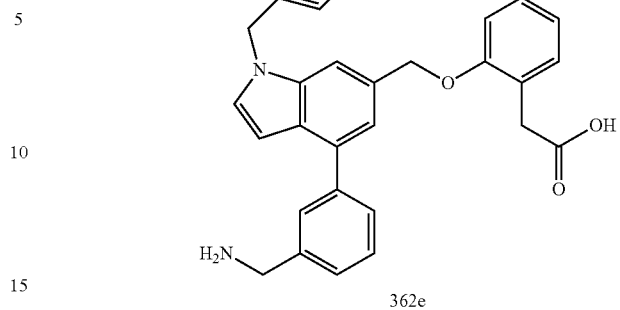

Preparation of 2-(2-((4-(3-(aminomethyl)phenyl)-1-benzyl-1H-indol-6-yl)methoxy)phenyl)acetic Acid (362e)

Step-1: Preparation of 1-benzyl-4-bromo-1H-indole-6-carboxylic Acid (362a)

Compound 362a was prepared according to the procedure reported in step-1 of scheme-40 from methyl 4-bromo-1H-indole-6-carboxylate (109a) (2 g, 7.87 mmol) in DMF (25 mL) using NaH (60% in mineral oil) (0.94 g, 23.61 mmol) and (bromomethyl)benzene (1.40 mL, 11.81 mmol). This gave after workup and purification by flash column chromatography [silica (24 g), eluting with EtOAc in Hexane from 0-100%] 1-benzyl-4-bromo-1H-indole-6-carboxylic Acid (362a) (2.5 g, 96% yield) as a white solid; $^1$H NMR (300 MHz, DMSO-$d_6$) δ 12.94 (s, 1H), 8.10 (t, J=1.0 Hz, 1H), 7.89 (d, J=3.1 Hz, 1H), 7.78 (d, J=1.2 Hz, 1H), 7.38-7.22 (m, 3H), 7.22-7.13 (m, 2H), 6.56 (dd, J=3.1, 0.9 Hz, 1H), 5.58 (s, 2H); MS (ES+): 331.0 & 333.0 (M+1); MS (ES−): 329.0 & 331.0 (M−1).

Step-2: Preparation of (1-benzyl-4-bromo-1H-indol-6-yl)methanol (362b)

Compound 362b was prepared according to the procedure reported in step-1 of scheme-23 from 1-benzyl-4-bromo-1H-indole-6-carboxylic acid (362a) (2 g, 6.06 mmol) using N-methylmorpholine (0.80 mL, 7.27 mmol) in THF (50 mL), isobutyl chloroformate (0.955 mL, 7.27 mmol) and NaBH$_4$ (0.69 g, 18.17 mmol) in water (0.8 mL). This gave after workup and purification by flash column chromatography [silica (12 g), eluting with EtOAc in Hexane from 0-100%] (1-benzyl-4-bromo-1H-indol-6-yl)methanol (362b) (1.58 g, 82% yield) as a white solid; $^1$H NMR (300 MHz, DMSO-$d_6$) δ 7.59 (d, J=3.2 Hz, 1H), 7.44-7.41 (m, 1H), 7.35-7.21 (m, 4H), 7.19-7.12 (m, 2H), 6.43 (dd, J=3.2, 0.9 Hz, 1H), 5.44 (s, 2H), 5.24 (t, J=5.8 Hz, 1H), 4.54 (d, J=5.7 Hz, 2H). MS (ES+): 339.1 & 341.0 (M+Na); MS (ES−): 314.0 & 316.1 (M−1).

Step-3: Preparation of Ethyl 2-(2-((1-benzyl-4-bromo-1H-indol-6-yl)methoxy)phenyl)acetate (362c)

Compound 362c was prepared according to the procedure reported in step-2 of scheme-23 from (1-benzyl-4-bromo-1H-indol-6-yl)methanol (362b) (1 g, 3.16 mmol) in DCM (20 mL) using triphenylphosphine (1.08 g, 4.11 mmol), ethyl 2-(2-hydroxyphenyl) acetate (23b) (0.74 g, 4.11 mmol) and a solution of (E)-bis(4-chlorobenzyl) diazene-1,2-dicarboxylate (DCAD, 1.51 g, 4.11 mmol) in DCM (20 mL). This gave after workup and purification by flash column chromatography [silica (12 g), eluting with EtOAc in hexanes from 0-50%] ethyl 2-(2-((1-benzyl-4-bromo-1H-indol-6-yl)methoxy)phenyl)acetate (362c) (0.28 g, 18% yield) as a white oil; $^1$H NMR (300 MHz, DMSO-$d_6$) δ 7.66 (d, J=3.2 Hz, 1H), 7.62 (t, J=1.0 Hz, 1H), 7.34-7.16 (m, 8H), 7.03 (dd, J=8.8, 1.1 Hz, 1H), 6.90 (td, J=7.4, 1.1 Hz, 1H), 6.45 (dd, J=3.2, 0.8 Hz, 1H), 5.44 (s, 2H), 5.15 (s, 2H), 3.98 (q, J=7.1 Hz, 2H), 3.60 (s, 2H), 1.04 (t, J=7.1 Hz, 3H). MS (ES+): 478.1 & 480.0 (M+1).

Step-4: Preparation of Ethyl 2-(2-((4-(3-(aminomethyl)phenyl)-1-benzyl-1H-indol-6-yl)methoxy)phenyl)acetate (362d)

Compound 362d was prepared according to the procedure reported in step-3 of scheme-1 from ethyl 2-(2-((1-benzyl-4-bromo-1H-indol-6-yl)methoxy)phenyl)acetate (362c) (0.27 g, 0.56 mmol) in dioxane (5 mL) using 3-(aminomethyl)phenylboronic acid hydrochloride (6c) (0.16 g, 0.85 mmol), $K_2CO_3$ (0.23 g, 1.69 mmol) in water (2 mL) and bis(triphenylphosphine)Palladium(II) chloride (0.06 g, 0.09 mmol) under an Ar atmosphere and heating at 100° C. for 3 h in an oil bath. This gave after workup, purification by flash column chromatography [silica (12 g), eluting with MeOH in DCM from 0-20%] followed by twice purification by reverse phase column [C18 (50 g), eluting with ACN in water (containing 0.1% HCl) from 0-100%] ethyl 2-(2-((4-(3-(aminomethyl)phenyl)-1-benzyl-1H-indol-6-yl)methoxy)phenyl)acetate (362d) (0.17 g, 58% yield) HCl salt as a white solid; MS (ES+) 505.2 (M+1); 527.2 (M+Na).

Step-5: Preparation of 2-(2-((4-(3-(aminomethyl)phenyl)-1-benzyl-1H-indol-6-yl)methoxy)phenyl) acetic Acid (362e)

Compound 362e was prepared according to the procedure reported in step-6 of scheme-1 from ethyl 2-(2-((4-(3-(aminomethyl)phenyl)-1-benzyl-1H-indol-6-yl)methoxy)phenyl)acetate (362d) (0.16 g, 0.32 mmol) in THF/MeOH (6 mL, each) using a solution of lithium hydroxide hydrate (0.11 g, 2.54 mmol) in water (2 mL). This gave after workup and purification by reverse phase column [C18 (50 g), eluting with ACN in water (containing 0.1% HCl) from 0-100%] 2-(2-((4-(3-(aminomethyl)phenyl)-1-benzyl-1H-indol-6-yl)methoxy)phenyl)acetic acid (362e) (0.04 g, 25% yield) HCl salt as a white solid; $^1$H NMR (300 MHz, DMSO-$d_6$) δ 12.24 (s, 1H), 8.34 (s, 3H), 7.81 (d, J=1.8 Hz, 1H), 7.67 (ddd, J=12.2, 7.7, 2.4 Hz, 3H), 7.60-7.45 (m, 2H), 7.36-7.15 (m, 8H), 7.06 (d, J=8.1 Hz, 1H), 6.94-6.85 (m, 1H), 6.70 (d, J=3.2 Hz, 1H), 5.46 (s, 2H), 5.24 (s, 2H), 4.12 (s, 2H), 3.59 (s, 2H); MS (ES+): 953.4 (2M+1); MS (ES−): 475.2 (M−1); Analysis calculated for: $C_{31}H_{28}N_2O_3 \cdot 1.25HCl \cdot 1.25H_2O$. C, 68.36; H, 5.88; N, 5.14; Found: C, 68.57; H, 6.00; N, 5.22.

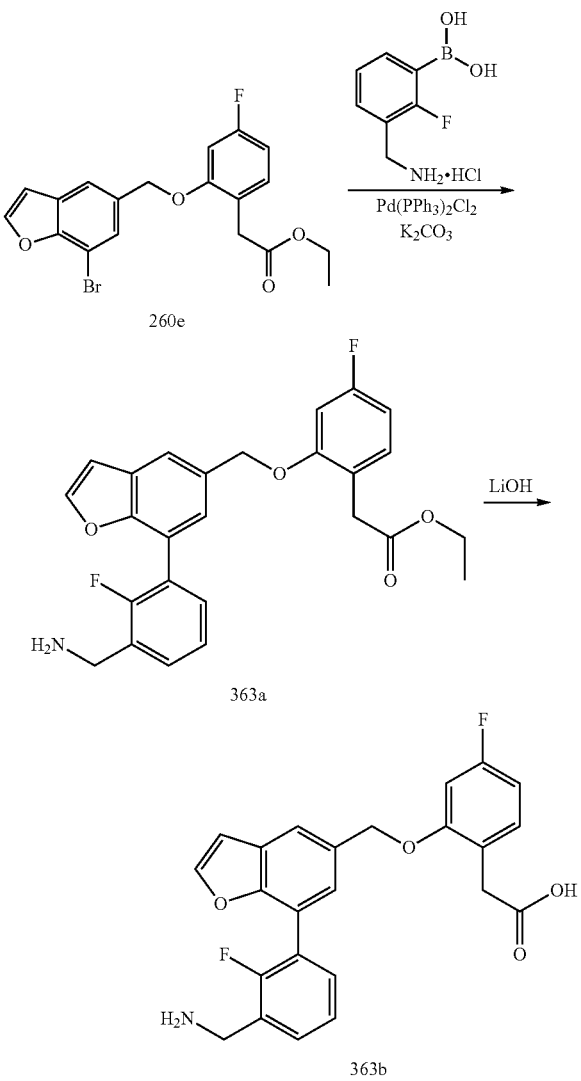

Scheme-363

Preparation of 2-(2-((7-(3-(aminomethyl)-2-fluorophenyl)benzofuran-5-yl)methoxy)-4-fluorophenyl) acetic Acid (363b)

Step-1: Preparation of Ethyl 2-(2-((7-(3-(aminomethyl)-2-fluorophenyl)benzofuran-5-yl)methoxy)-4-fluorophenyl)acetate (363a)

Compound 363a was prepared according to the procedure reported in step-3 of scheme-1 from ethyl 2-(2-((7-bromobenzofuran-5-yl)methoxy)-4-fluorophenyl)acetate (260e) (200 mg, 0.491 mmol) in dioxane (5 mL) using (3-(aminomethyl)-2-fluorophenyl)boronic acid hydrochloride (56a) (125 mg, 0.610 mmol), bis(triphenylphosphine)palladium(II) chloride (Pd(PPh$_3$)$_2$Cl$_2$) (52 mg, 0.074 mmol), potassium carbonate (204 mg, 1.473 mmol) in water (0.5 mL) under an argon atmosphere heating at 100° C. for 3 h on oil bath. This gave after workup, purification by flash column chromatography (silica gel, 24 g, eluting with DMA-80 in DCM from 0-50%) ethyl 2-(2-((7-(3-(aminomethyl)-2-fluorophenyl)benzofuran-5-yl)methoxy)-4-fluorophenyl)acetate (363a) (179 mg, 81% yield) as a clear oil. $^1$H NMR (300 MHz, DMSO-$d_6$) δ 8.05 (d, J=2.2 Hz, 1H), 7.75 (d, J=1.7 Hz, 1H), 7.66-7.55 (m, 1H), 7.51-7.18 (m, 4H), 7.13-6.97 (m, 2H), 6.74 (td, J=8.5, 2.5 Hz, 1H), 5.24 (s, 2H), 3.90 (q, J=7.1 Hz, 2H), 3.84 (s, 2H), 3.59 (s, 2H), 0.97 (t, J=7.1 Hz, 3H); $^{19}$F NMR (282 MHz, DMSO-$d_6$) δ−112.63, −121.77. MS (ES+): 452.1 (M+1).

Step-2: Preparation of 2-(2-((7-(3-(aminomethyl)-2-fluorophenyl)benzofuran-5-yl)methoxy)-4-fluorophenyl)acetic Acid (363b)

Compound 363b was prepared according to the procedure reported in step-6 of scheme-1 from ethyl 2-(2-((7-(3-(aminomethyl)-2-fluorophenyl)benzofuran-5-yl)methoxy)-4-fluorophenyl)acetate (363a) (175 mg, 0.388 mmol) in MeOH (5.5 mL), THF (5.5 mL) using 1 N lithium hydroxide (1.163 mL, 1.163 mmol). This gave after workup and purification by reverse phase column [C18 (50g), eluting with ACN in water (containing 0.1% HCl) from 0-100%] 2-(2-((7-(3-(aminomethyl)-2-fluorophenyl)benzofuran-5-yl)methoxy)-4-fluorophenyl)acetic acid (363b) (120 mg, 73% yield) hydrochloride salt as a white solid; $^1$H NMR (300 MHz, DMSO-$d_6$) δ 8.06 (d, J=2.2 Hz, 1H), 7.82 (d, J=1.6 Hz, 1H), 7.68 (t, J=7.4 Hz, 2H), 7.50-7.39 (m, 2H), 7.24 (dd, J=8.4, 6.9 Hz, 1H), 7.07 (d, J=2.2 Hz, 1H), 7.02 (dd, J=11.4, 2.5 Hz, 1H), 6.74 (td, J=8.5, 2.5 Hz, 1H), 5.28 (s, 2H), 4.18 (s, 2H), 3.55 (s, 2H). $^{19}$F NMR (282 MHz, DMSO) δ−112.98, −118.38. MS (ES+): 424.1 (M+1); (ES−): 422.1 (M−1); Analysis calculated for $C_{24}H_{19}F_2NO_4 \cdot HCl \cdot 0.5H_2O$: C, 61.48; H, 4.51; Cl, 7.56; N, 2.99; Found: C, 61.67; H, 4.54; Cl, 7.38; N, 2.98.

Scheme-364

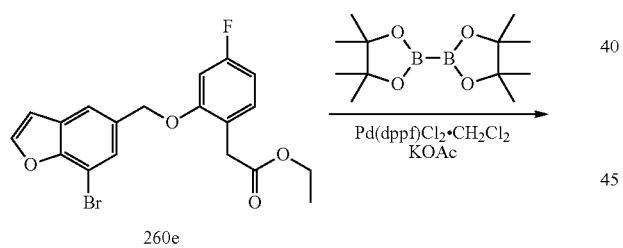

260e

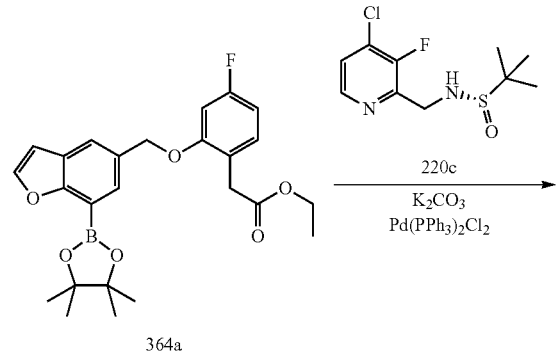

364a

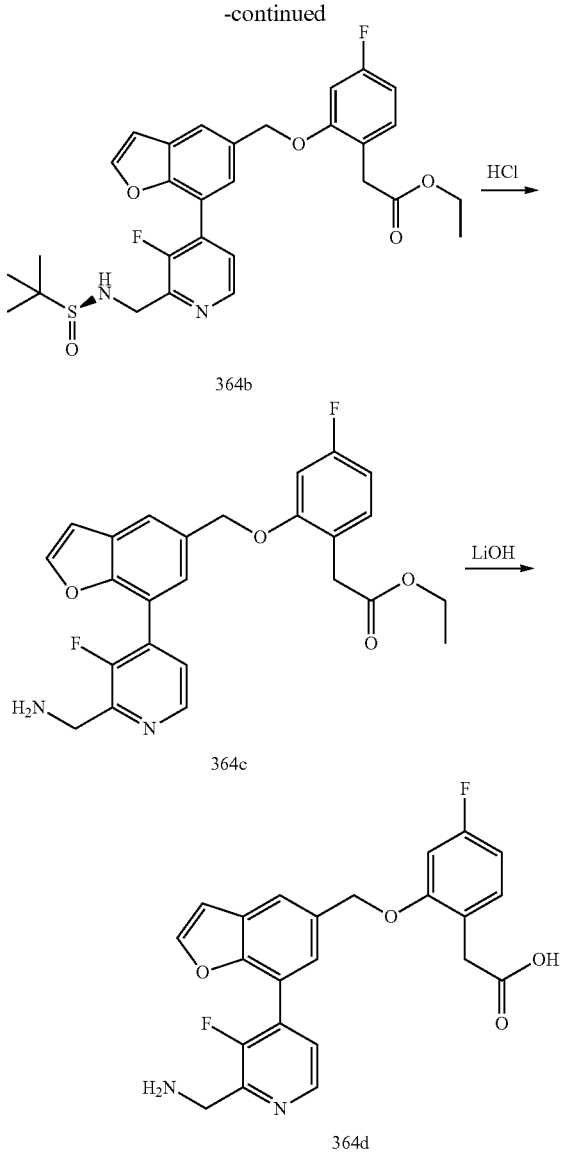

Preparation of 2-(2-((7-(2-(aminomethyl)-3-fluoropyridin-4-yl)benzofuran-5-yl)methoxy)-4-fluorophenyl)acetic Acid (364d)

Step-1: Preparation of Ethyl 2-(4-fluoro-2-((7-(4,4,5,5-tetramethyl-1,3,2-dioxaborolan-2-yl)benzofuran-5-yl)methoxy)phenyl)acetate (364a)

Compound 364a was prepared according to the procedure reported in step-1 of scheme-59 from ethyl 2-(2-((7-bromobenzofuran-5-yl)methoxy)-4-fluorophenyl)acetate (260e) (1.5 g, 3.68 mmol), using bis(pinacolato)diboron (1.403 g, 5.53 mmol), potassium acetate (1.084 g, 11.05 mmol) and Pd(dppf)Cl$_2$—CH$_2$Cl$_2$ (0.301 g, 0.368 mmol) in anhydrous dioxane (50 mL) under an argon atmosphere and heating at 90° C. overnight. This gave after workup and purification by flash column chromatography [silica gel (40g), eluting with EtOAc in hexanes from 0-40%] ethyl 2-(4-fluoro-2-((7-(4,4,5,5-tetramethyl-1,3,2-dioxaborolan-2-yl)benzofuran-5-yl)methoxy)phenyl)acetate (364a) (1.44 g, 86% yield) as a clear oil. ¹H NMR (300 MHz, DMSO-d₆) δ 8.07 (d, J=2.2 Hz, 1H), 7.83 (d, J=1.9 Hz, 1H), 7.65 (d, J=1.9 Hz, 1H), 7.24 (dd, J=8.4, 6.9 Hz, 1H), 7.03 (dd, J=11.4, 2.5 Hz, 1H), 6.97 (d, J=2.2 Hz, 1H), 6.74 (td, J=8.5, 2.5 Hz, 1H), 5.19 (s, 2H), 3.98 (q, J=7.1 Hz, 2H), 3.57 (d, J=1.7 Hz, 2H), 1.34 (s, 12H), 1.04 (t, J=7.1 Hz, 3H); ¹⁹F NMR (282 MHz, DMSO-d₆) δ −112.67.

Step-2: Preparation of Ethyl 2-(2-((7-(2-((1,1-dimethylethylsulfinamido)methyl)-3-fluoropyridin-4-yl)benzofuran-5-yl)methoxy)-4-fluorophenyl)acetate (364b)

Compound 364b was prepared according to the procedure reported in step-3 of scheme-1 from ethyl 2-(4-fluoro-2-((7-(4,4,5,5-tetramethyl-1,3,2-dioxaborolan-2-yl)benzofuran-5-yl)methoxy)phenyl)acetate (364a) (300 mg, 0.660 mmol) in dioxane (5 mL) using (+)-(S)—N-((4-chloro-3-fluoropyridin-2-yl)methyl)-2-methylpropane-2-sulfinamide (220c) (175 mg, 0.660 mmol), bis(triphenylphosphine)palladium (II) chloride (Pd(PPh₃)₂Cl₂) (70 mg, 0.099 mmol) and a solution of K₂CO₃ (274 mg, 1.981 mmol) in water (0.5 mL) under an argon atmosphere heating at 100° C. for 3 h on oil bath. This gave after workup, purification by flash column chromatography [silica gel (24g), eluting with DMA80 in DCM from 0-100%] ethyl 2-(2-((7-(2-((1,1-dimethylethylsulfinamido)methyl)-3-fluoropyridin-4-yl)benzofuran-5-yl)methoxy)-4-fluorophenyl)acetate (364b) (355 mg, 97% yield) as an brown oil; ¹H NMR (300 MHz, DMSO-d₆) δ 8.52 (dd, J=4.9, 0.7 Hz, 1H), 8.09 (d, J=2.2 Hz, 1H), 7.86 (d, J=1.6 Hz, 1H), 7.70-7.67 (m, 1H), 7.55-7.49 (m, 1H), 7.25 (dd, J=8.3, 6.9 Hz, 1H), 7.10 (d, J=2.2 Hz, 1H), 7.06 (dd, J=11.3, 2.5 Hz, 1H), 6.75 (td, J=8.5, 2.5 Hz, 1H), 5.93-5.75 (m, 1H), 5.27 (s, 2H), 4.41 (dd, J=5.9, 2.1 Hz, 2H), 3.91 (q, J=7.1 Hz, 2H), 3.60 (s, 2H), 1.11 (s, 9H), 0.97 (t, J=7.1 Hz, 3H); ¹⁹F NMR (282 MHz, DMSO-d₆) δ −112.59, −128.04. MS (ES+): 557.2 (M+1).

Step-3: Preparation of Ethyl 2-(2-((7-(2-(aminomethyl)-3-fluoropyridin-4-yl)benzofuran-5-yl)methoxy)-4-fluorophenyl)acetate (364c)

Compound 364c was prepared according to the procedure reported in step-3 of scheme-305 from ethyl 2-(2-((7-(2-((1,1-dimethylethylsulfinamido)methyl)-3-fluoropyridin-4-yl)benzofuran-5-yl)methoxy)-4-fluorophenyl)acetate (364b) (355 mg, 0.638 mmol) in methanol (10 mL) using HCl (4M in dioxane; 0.478 mL, 1.913 mmol) and stirring at room temperature for 30 mins. This gave after workup, ethyl 2-(2-((7-(2-(aminomethyl)-3-fluoropyridin-4-yl)benzofuran-5-yl)methoxy)-4-fluorophenyl)acetate (364c) (270 mg, 94% yield) as a yellow oil, which was used in the next reaction without further purification. MS (ES+): 453.1 (M+1).

Step-4: Preparation of 2-(2-((7-(2-(aminomethyl)-3-fluoropyridin-4-yl)benzofuran-5-yl)methoxy)-4-fluorophenyl)acetic Acid (364d)

Compound 364d was prepared according to the procedure reported in step-6 of scheme-1 from ethyl 2-(2-((7-(2-(aminomethyl)-3-fluoropyridin-4-yl)benzofuran-5-yl)methoxy)-4-fluorophenyl)acetate (364c) (270 mg, 0.597 mmol) in MeOH (10 mL), THF (10 mL) using 1 N lithium hydroxide (3.58 mL, 3.58 mmol). This gave after workup and purification by reverse phase column [C18 (50 g), eluting with 0.1% aqueous HCl in water and acetonitrile from 0-100%] 2-(2-((7-(2-(aminomethyl)-3-fluoropyridin-4-yl)benzofuran-5-yl)methoxy)-4-fluorophenyl)acetic acid (364d) (94 mg, 0.221 mmol, 37.1% yield) hydrochloride salt as a white solid; ¹H NMR (300 MHz, DMSO-d₆) δ 8.63 (d, J=5.0 Hz, 1H), 8.12 (d, J=2.2 Hz, 1H), 7.91 (d, J=1.6 Hz, 1H), 7.81 (t, J=5.3 Hz, 1H), 7.59 (d, J=1.5 Hz, 1H), 7.25 (dd, J=8.4, 6.9 Hz, 1H), 7.12 (d, J=2.2 Hz, 1H), 7.03 (dd, J=11.3, 2.5 Hz, 1H), 6.74 (td, J=8.5, 2.5 Hz, 1H), 5.30 (s, 2H), 4.41-4.32 (m, 2H), 3.56 (s, 2H). ¹⁹F NMR (282 MHz, DMSO) δ −112.95, −128.35. MS (ES+): 425.1 (M+1); (ES−): 423.1 (M−1); Analysis calculated for C₂₃H₁₈F₂N₂O₄.HCl.0.5H₂O: C, 58.79; H, 4.29; Cl, 7.55; N, 5.96; Found: C, 58.94; H, 4.24; Cl, 7.91; N, 6.17.

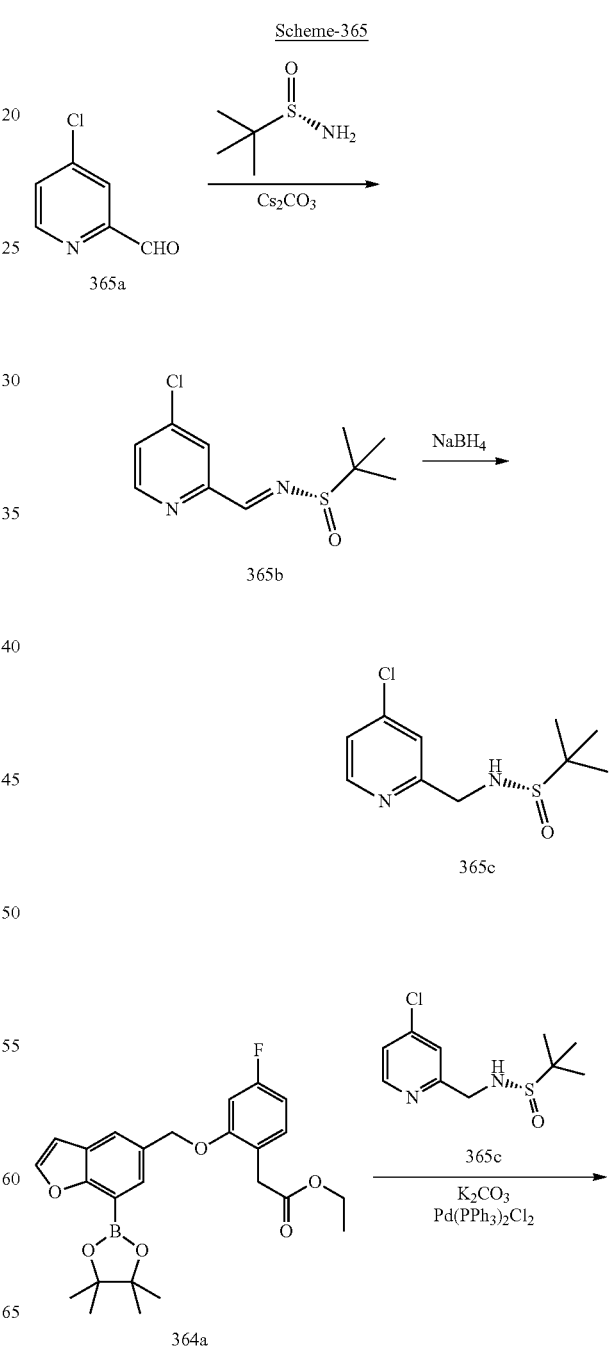

Scheme-365

1155

-continued

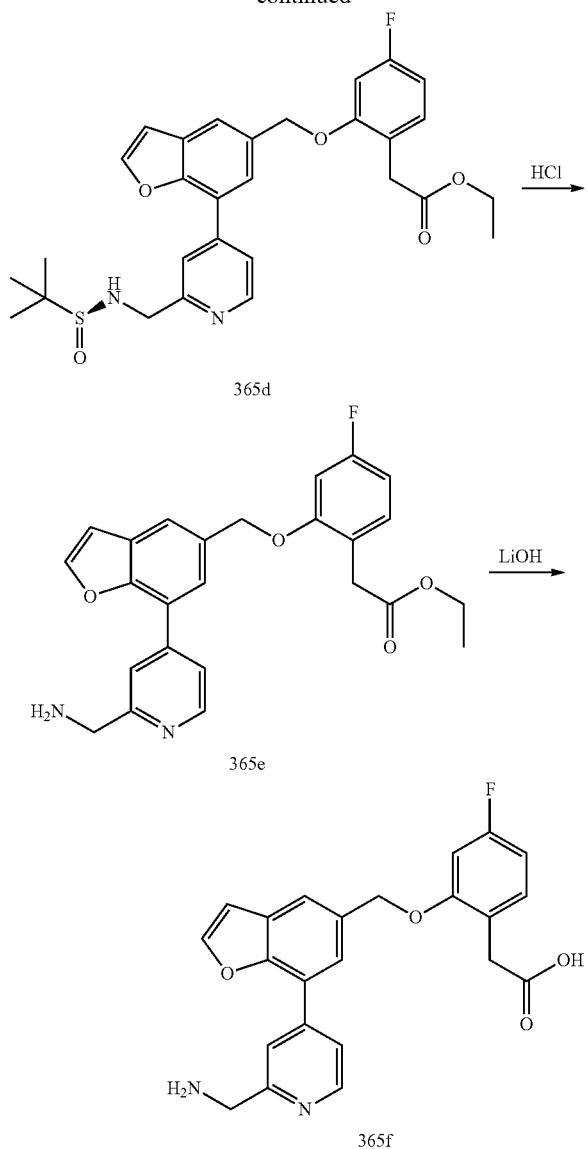

365d

365e

365f

Preparation of 2-(2-((7-(2-(aminomethyl)pyridin-4-yl)benzofuran-5-yl)methoxy)-4-fluorophenyl)acetic Acid (365f)

Step-1: Preparation of N-((4-chloropyridin-2-yl)methylene)-2-methylpropane-2-sulfinamide (365b)

Compound 365b was prepared according to the procedure reported in step-1 of scheme-220 from 4-chloropicolinaldehyde (365a) (15 g, 106 mmol) in DCM (100 mL) using Cs$_2$CO$_3$ (51.8 g, 159 mmol), (S)-2-methylpropane-2-sulfinamide (14.77 g, 122 mmol) and stirring at room temperature for 1 h. This gave after workup N-((4-chloropyridin-2-yl)methylene)-2-methylpropane-2-sulfinamide (365b) (25.9 g, 106 mmol, 100% yield) which was used as such in the next step; $^1$H NMR (300 MHz, DMSO-d$_6$) δ 8.75 (dd, J=5.3, 0.6 Hz, 1H), 8.48 (s, 1H), 8.13 (dd, J=2.1, 0.6 Hz, 1H), 7.76 (dd, J=5.3, 2.1 Hz, 1H), 1.22 (s, 9H).

1156

Step-2: Preparation of (+)-(S)—N-((4-chloropyridin-2-yl)methyl)-2-methylpropane-2-sulfinamide (365c)

Compound 365c was prepared according to the procedure reported in step-2 of scheme-220 from N-((4-chloropyridin-2-yl)methylene)-2-methylpropane-2-sulfinamide (365b) (18.5 g, 76 mmol) in methanol (300 mL) using NaBH$_4$ (2.86 g, 76 mmol). This gave after workup and purification by flash column chromatography [silica gel (120 g), eluting with a 9:1 mixture of ethyl acetate and methanol in hexanes] (+)-(S)—N-((4-chloropyridin-2-yl)methyl)-2-methylpropane-2-sulfinamide (365c) (15.7 g, 84%) as a white solid. $^1$H NMR (300 MHz, DMSO-d$_6$) δ 8.48 (dd, J=5.3, 0.6 Hz, 1H), 7.58 (dd, J=2.1, 0.7 Hz, 1H), 7.43 (dd, J=5.4, 2.1 Hz, 1H), 5.97 (t, J=6.3 Hz, 1H), 4.29 (dd, J=6.3, 3.3 Hz, 2H), 1.16 (s, 9H); Optical rotation [t]D=+45.4 (0.81, MeOH)

Step-3: Preparation of Ethyl 2-(2-((7-(2-((1,1-dimethylethylsulfinamido)methyl)pyridin-4-yl)benzofuran-5-yl)methoxy)-4-fluorophenyl)acetate (365d)

Compound 365d was prepared according to the procedure reported in step-3 of scheme-1 from ethyl 2-(4-fluoro-2-((7-(4,4,5,5-tetramethyl-1,3,2-dioxaborolan-2-yl)benzofuran-5-yl)methoxy)phenyl)acetate (364a) (300 mg, 0.660 mmol) in dioxane (5 mL) using (+)-(S)—N-((4-chloropyridin-2-yl)methyl)-2-methylpropane-2-sulfinamide (365c) (163 mg, 0.660 mmol), bis(triphenylphosphine)palladium(II) chloride (Pd(PPh$_3$)$_2$Cl$_2$) (70 mg, 0.099 mmol) and a solution of K$_2$CO$_3$ (274 mg, 1.981 mmol) in water (0.5 mL) under an argon atmosphere heating at 100° C. for 3 h on oil bath. This gave after workup, purification by flash column chromatography [silica gel (24g), eluting with DMA80 in DCM from 0-40%] ethyl 2-(2-((7-(2-((1,1-dimethylethylsulfinamido)methyl)pyridin-4-yl)benzofuran-5-yl)methoxy)-4-fluorophenyl)acetate (365d) (355 mg, 100% yield) as an brown oil; $^1$H NMR (300 MHz, DMSO-d$_6$) δ 8.65 (dd, J=5.2, 0.8 Hz, 1H), 8.12 (d, J=2.2 Hz, 1H), 8.06 (dd, J=1.8, 0.9 Hz, 1H), 7.83-7.75 (m, 2H), 7.72 (d, J=1.6 Hz, 1H), 7.25 (dd, J=8.4, 6.9 Hz, 1H), 7.11 (d, J=2.2 Hz, 1H), 7.05 (dd, J=11.3, 2.5 Hz, 1H), 6.75 (td, J=8.5, 2.5 Hz, 1H), 5.96 (t, J=6.1 Hz, 1H), 5.27 (s, 2H), 4.40-4.33 (m, 2H), 3.93-3.87 (m, 2H), 3.60 (s, 2H), 1.07 (s, 9H), 0.95 (t, J=7.1 Hz, 3H); $^{19}$F NMR (282 MHz, DMSO-d$_6$) δ−112.62. MS (ES+): 539.2 (M+1).

Step-4: Preparation of Ethyl 2-(2-((7-(2-(aminomethyl)pyridin-4-yl)benzofuran-5-yl)methoxy)-4-fluorophenyl)acetate (365e)

Compound 365e was prepared according to the procedure reported in step-3 of scheme-305 from ethyl 2-(2-((7-(2-((1,1-dimethylethylsulfinamido)methyl)pyridin-4-yl)benzofuran-5-yl)methoxy)-4-fluorophenyl)acetate (365d) (355 mg, 0.659 mmol) in methanol (10 mL) using HCl (4M in dioxane; 0.494 mL, 1.977 mmol) and stirring at room temperature for 30 mins. This gave after workup ethyl 2-(2-((7-(2-(aminomethyl)pyridin-4-yl)benzofuran-5-yl)methoxy)-4-fluorophenyl)acetate (365e) (270 mg, 94% yield) as a yellow oil, which was used as such in the next step without further purification. MS (ES+): 435.1 (M+1).

Step-5: Preparation of 2-(2-((7-(2-(aminomethyl)pyridin-4-yl)benzofuran-5-yl)methoxy)-4-fluorophenyl)acetic Acid (365f)

Compound 365f was prepared according to the procedure reported in step-6 of scheme-1 from ethyl 2-(2-((7-(2-

(aminomethyl)pyridin-4-yl)benzofuran-5-yl)methoxy)-4-fluorophenyl)acetate (365e) (270 mg, 0.621 mmol) in MeOH (12 mL), THF (12 mL) using 1 N lithium hydroxide (2.486 mL, 2.486 mmol). This gave after workup and purification by reverse phase column [C18 (50 g), eluting with 0.1% aqueous HCl in water and acetonitrile from 0-100%] 2-(2-((7-(2-(aminomethyl)pyridin-4-yl)benzofuran-5-yl)methoxy)-4-fluorophenyl)acetic acid (365f) (162 mg, 64% yield) hydrochloride salt as a pale yellow solid; $^1$H NMR (300 MHz, DMSO-$d_6$) δ 8.78 (dd, J=5.2, 0.8 Hz, 1H), 8.41 (s, 3H, D$_2$O exchangeable), 8.17 (d, J=2.2 Hz, 1H), 8.06 (d, J=1.6 Hz, 1H), 7.98 (dd, J=5.3, 1.7 Hz, 1H), 7.87 (d, J=1.6 Hz, 1H), 7.80 (d, J=1.7 Hz, 1H), 7.25 (dd, J=8.3, 6.9 Hz, 1H), 7.12 (d, J=2.2 Hz, 1H), 7.03 (dd, J=11.3, 2.5 Hz, 1H), 6.74 (td, J=8.5, 2.5 Hz, 1H), 5.31 (s, 2H), 4.32 (d, J=5.4 Hz, 2H), 3.57 (s, 2H); $^{19}$F NMR (282 MHz, DMSO-$d_6$) δ−112.92; MS (ES+): 407.1 (M+1); (ES−): 405.1 (M−1); Analysis calculated for $C_{23}H_{19}FN_2O_4 \cdot 1.35HCl \cdot 1.25H_2O$: C, 57.77; H, 4.82; Cl, 10.01; N, 5.86; Found: C, 57.46; H, 4.74; Cl, 10.18; N, 5.81.

Scheme-366

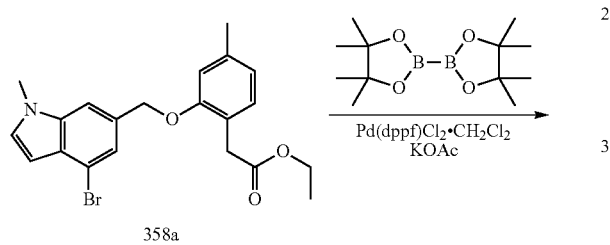

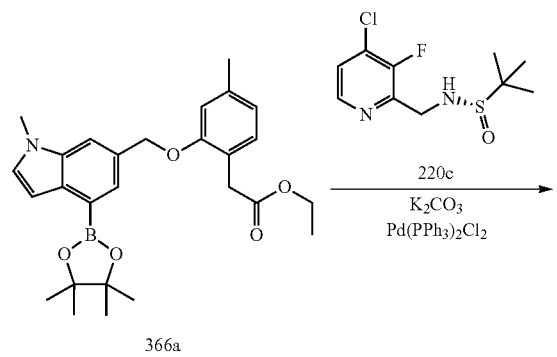

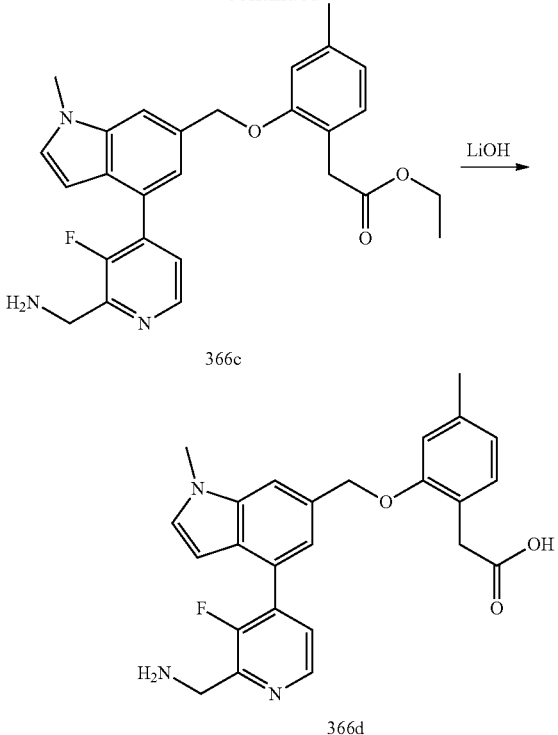

Preparation of 2-(2-((4-(2-(aminomethyl)-3-fluoropyridin-4-yl)-1-methyl-1H-indol-6-yl)methoxy)-4-methylphenyl)acetic Acid (366d)

Step-1: Preparation of Ethyl 2-(4-methyl-2-((1-methyl-4-(4,4,5,5-tetramethyl-1,3,2-dioxaborolan-2-yl)-1H-indol-6-yl)methoxy)phenyl)acetate (366a)

Compound 366a was prepared according to the procedure reported in step-1 of scheme-59 from ethyl 2-(2-((4-bromo-1-methyl-1H-indol-6-yl)methoxy)-4-methylphenyl)acetate (358a) (1.05 g, 2.52 mmol), using bis(pinacolato)diboron (0.96 g, 3.78 mmol), potassium acetate (0.74 g, 7.57 mmol) and Pd(dppf)Cl$_2$—CH$_2$Cl$_2$ (0.309 g, 0.378 mmol) in anhydrous dioxane (15 mL) under an argon atmosphere and heating at 100° C. overnight. This gave after workup and purification by flash column chromatography [silica gel (24g), eluting with EtOAc/MeOH (9:1) in hexanes from 0-10%] ethyl 2-(4-methyl-2-((1-methyl-4-(4,4,5,5-tetramethyl-1,3,2-dioxaborolan-2-yl)-1H-indol-6-yl)methoxy)phenyl)acetate (366a) (450 mg, 39% yield) as a yellow solid; $^1$H NMR (300 MHz, DMSO-$d_6$) δ 7.63 (d, J=1.3 Hz, 1H), 7.47 (d, J=1.4 Hz, 1H), 7.37 (d, J=3.1 Hz, 1H), 7.07 (d, J=7.5 Hz, 1H), 6.96 (d, J=2.0 Hz, 1H), 6.73 (d, J=0.9 Hz, 1H), 6.59 (d, J=1.2 Hz, 1H), 5.15 (s, 2H), 3.99 (m, 2H), 3.80 (s, 3H), 3.47 (s, 2H), 1.29 (s, 3H), 1.17 (s, 12H), 1.03 (t, J=7.1 Hz, 3H); MS (ES+): 464.3 (M+1); MS (ES+): 486.2 (M+Na).

Step-2: Preparation of Ethyl 2-(2-((4-(2-((1,1-dimethylethylsulfinamido)methyl)-3-fluoropyridin-4-yl)-1-methyl-1H-indol-6-yl)methoxy)-4-methylphenyl)acetate (366b)

Compound 366b was prepared according to the procedure reported in step-3 of scheme-1 from ethyl 2-(4-methyl-2-

((1-methyl-4-(4,4,5,5-tetramethyl-1,3,2-dioxaborolan-2-yl)-1H-indol-6-yl)methoxy)phenyl)acetate (366a) (200 mg, 0.432 mmol) in dioxane (4 mL) using (+)-(S)—N-((4-chloro-3-fluoropyridin-2-yl)methyl)-2-methylpropane-2-sulfinamide (220c) (137 mg, 0.518 mmol), bis(triphenylphosphine)palladium(II) chloride (Pd(PPh₃)₂Cl₂) (45 mg, 0.065 mmol) and a solution of K₂CO₃ (179 mg, 1.295 mmol) in water (1.0 mL) under an argon atmosphere heating at 90° C. for 3 h on oil bath. This gave after workup and purification by flash column chromatography [silica gel (12 g), eluting with DMA80 in DCM from 0-50%] ethyl 2-(2-((4-(2-((1,1-dimethylethylsulfinamido)methyl)-3-fluoropyridin-4-yl)-1-methyl-1H-indol-6-yl)methoxy)-4-methylphenyl)acetate (366b) (240 mg, 98% yield) as a yellow oil; ¹H NMR (300 MHz, DMSO-d₆) δ 8.47 (d, J=4.9 Hz, 1H), 8.36 (d, J=5.2 Hz, 1H), 7.63 (dd, J=2.1, 1.2 Hz, 1H), 7.60-7.58 (m, 1H), 7.46 (d, J=3.2 Hz, 1H), 7.23 (s, 1H), 7.08 (d, J=7.5 Hz, 1H), 6.98 (s, 1H), 6.72 (d, J=7.4 Hz, 1H), 6.35 (t, J=2.7 Hz, 1H), 5.24 (s, 2H), 4.44-4.37 (m, 2H), 4.10 (q, J=5.3 Hz, 2H), 3.93 (s, 2H), 3.86 (s, 3H), 3.57 (s, 9H), 2.30 (s, 3H), 0.96 (t, J=7.1 Hz, 3H); MS (ES+): 566.3 (M+1).

Step-3: Preparation of Ethyl 2-(2-((4-(2-(aminomethyl)-3-fluoropyridin-4-yl)-1-methyl-1H-indol-6-yl)methoxy)-4-methylphenyl)acetate (366c)

Compound 366c was prepared according to the procedure reported in step-3 of scheme-305 from ethyl 2-(2-((4-(2-((1,1-dimethylethylsulfinamido)methyl)-3-fluoropyridin-4-yl)-1-methyl-1H-indol-6-yl)methoxy)-4-methylphenyl)acetate (366b) (240 mg, 0.42 mmol) in DCM (5 mL) using HCl (4M in dioxane; 0.32 mL, 1.27 mmol) and stirring at room temperature for 1 h. This gave after workup and purification by flash column chromatography [silica (12 g), eluting with DMA80/DCM from 0-70%] ethyl 2-(2-((4-(2-(aminomethyl)-3-fluoropyridin-4-yl)-1-methyl-1H-indol-6-yl)methoxy)-4-methylphenyl)acetate (366c) (40 mg, 20% yield) as a pale-yellow oil; MS (ES+): 462.2 (M+1).

Step-4: Preparation of 2-(2-((4-(2-(aminomethyl)-3-fluoropyridin-4-yl)-1-methyl-1H-indol-6-yl)methoxy)-4-methylphenyl)acetic Acid (366d)

Compound 366d was prepared according to the procedure reported in step-6 of scheme-1 from ethyl 2-(2-((4-(2-(aminomethyl)-3-fluoropyridin-4-yl)-1-methyl-1H-indol-6-yl)methoxy)-4-methylphenyl)acetate (366c) (40 mg, 0.09 mmol) in MeOH (4 mL), THF (4 mL) using lithium hydroxide hydrate (29 mg, 0.69 mmol) in water (1 mL). This gave after workup and purification by reverse phase column [C18 (50 g), eluting with water in acetonitrile from 0-100%] 2-(2-((4-(2-(aminomethyl)-3-fluoropyridin-4-yl)-1-methyl-1H-indol-6-yl)methoxy)-4-methylphenyl)acetic acid (366d) (23 mg, 61% yield) free base as a white solid; ¹H NMR (300 MHz, DMSO-d₆) δ 8.46 (d, J=4.9 Hz, 1H), 7.69 (s, 1H), 7.50 (t, J=5.3 Hz, 1H), 7.44 (d, J=3.1 Hz, 1H), 7.28 (d, J=1.5 Hz, 1H), 7.07 (d, J=7.5 Hz, 1H), 6.94 (d, J=1.5 Hz, 1H), 6.70 (d, J=7.6 Hz, 1H), 6.34 (t, J=2.8 Hz, 1H), 5.25 (s, 2H), 3.96 (d, J=2.1 Hz, 2H), 3.85 (s, 3H), 3.60 (s, 2H), 2.28 (s, 3H). ¹⁹F NMR (282 MHz, DMSO) δ−130.86; MS (ES+): 434.2 (M+1); MS (ES−): 432.1 (M−1); Analysis calculated for: C₂₅H₂₄FN₃O₃.1.75H₂O. C, 64.57; H, 5.96; N, 9.04; Found: C, 64.56; H, 5.62; N, 9.09.

Scheme-367

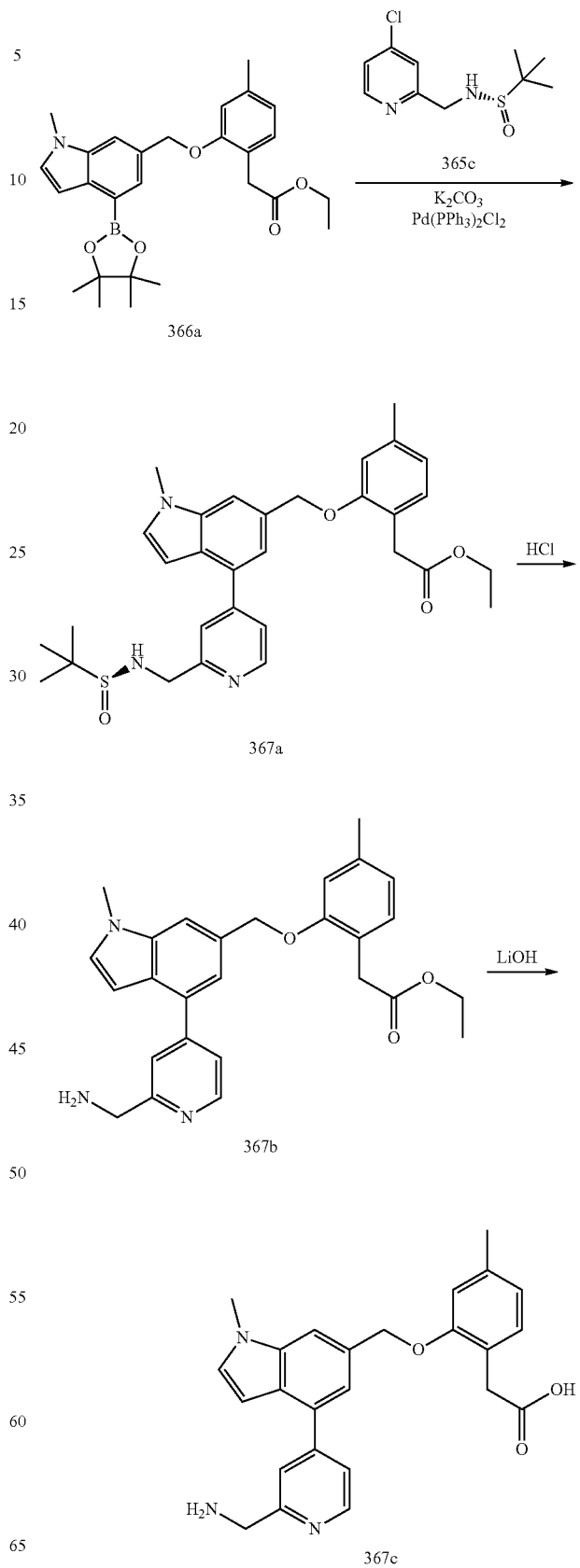

Preparation of 2-(2-((4-(2-(aminomethyl)pyridin-4-yl)-1-methyl-1H-indol-6-yl)methoxy)-4-methylphenyl)acetic Acid (367c)

Step-1: Preparation of Ethyl 2-(2-((4-(2-((1,1-dimethylethylsulfinamido)methyl)pyridin-4-yl)-1-methyl-1H-indol-6-yl)methoxy)-4-methylphenyl)acetate (367a)

Compound 367a was prepared according to the procedure reported in step-3 of scheme-1 from ethyl 2-(4-methyl-2-((1-methyl-4-(4,4,5,5-tetramethyl-1,3,2-dioxaborolan-2-yl)-1H-indol-6-yl)methoxy)phenyl)acetate (366a) (230 mg, 0.50 mmol) in dioxane (4 mL) using (+)-(S)—N-((4-chloropyridin-2-yl)methyl)-2-methylpropane-2-sulfinamide (365c) (147 mg, 0.60 mmol), bis(triphenylphosphine)palladium(II) chloride (Pd(PPh$_3$)$_2$Cl$_2$) (52 mg, 0.07 mmol) and a solution of K$_2$CO$_3$ (206 mg, 1.49 mmol) in water (1.0 mL) under an argon atmosphere heating at 90° C. for 3 h on oil bath. This gave after workup and purification by flash column chromatography [silica gel (12 g), eluting with DMA80 in DCM from 0-50%] ethyl 2-(2-((4-(2-((1,1-dimethylethylsulfinamido)methyl)pyridin-4-yl)-1-methyl-1H-indol-6-yl)methoxy)-4-methylphenyl)acetate (367a) (266 mg, 98% yield) as a yellow oil; $^1$H NMR (300 MHz, DMSO-d$_6$) δ 8.63-8.53 (m, 1H), 8.48 (dd, J=5.3, 0.6 Hz, 1H), 7.84 (s, 1H), 7.63 (s, 1H), 7.58 (dd, J=2.1, 0.6 Hz, 2H), 7.49 (d, J=3.2 Hz, 1H), 7.44 (dd, J=5.4, 2.1 Hz, 1H), 7.30 (d, J=1.3 Hz, 1H), 7.08 (d, J=7.5 Hz, 1H), 6.98 (s, 1H), 5.24 (s, 2H), 4.36 (q, J=5.1 Hz, 2H), 3.95-3.87 (m, 2H), 3.86 (s, 3H), 3.57 (s, 2H), 2.30 (s, 3H), 1.16 (s, 9H), 0.95 (t, J=7.1 Hz, 3H); MS (ES+): 548.3 (M+1).

Step-2: Preparation of Ethyl 2-(2-((4-(2-(aminomethyl)pyridin-4-yl)-1-methyl-1H-indol-6-yl)methoxy)-4-methylphenyl)acetate (367b)

Compound 367b was prepared according to the procedure reported in step-3 of scheme-305 from ethyl 2-(2-((4-(2-((1,1-dimethylethylsulfinamido)methyl)pyridin-4-yl)-1-methyl-1H-indol-6-yl)methoxy)-4-methylphenyl)acetate (367a) (266 mg, 0.49 mmol) in DCM (5 mL) using HCl (4 M in dioxane; 0.36 mL, 1.46 mmol) and stirring at room temperature for 2 h. This gave after workup and purification by flash column chromatography [silica (12 g), eluting with DMA80/DCM from 0-70%] ethyl 2-(2-((4-(2-(aminomethyl)pyridin-4-yl)-1-methyl-1H-indol-6-yl)methoxy)-4-methylphenyl)acetate (367b) (40 mg, 19% yield) as a pale-yellow oil; MS (ES+): 444.2 (M+1).

Step-3: Preparation of 2-(2-((4-(2-(aminomethyl)pyridin-4-yl)-1-methyl-1H-indol-6-yl)methoxy)-4-methylphenyl)acetic Acid (367c)

Compound 367c was prepared according to the procedure reported in step-6 of scheme-1 from ethyl 2-(2-((4-(2-(aminomethyl)pyridin-4-yl)-1-methyl-1H-indol-6-yl)methoxy)-4-methylphenyl)acetate (367b) (40 mg, 0.09 mmol) in MeOH (4 mL), THF (4 mL) using lithium hydroxide hydrate (30 mg, 0.72 mmol) in water (1 mL). This gave after workup and purification by reverse phase column [C18 (50 g), eluting with water in acetonitrile from 0-100%] 2-(2-((4-(2-(aminomethyl)pyridin-4-yl)-1-methyl-1H-indol-6-yl)methoxy)-4-methylphenyl)acetic acid (367c) (26 mg, 69% yield) free base as a white solid; $^1$H NMR (300 MHz, DMSO-d$_6$) δ 8.58 (d, J=5.2 Hz, 1H), 8.10 (s, 1H), 7.73 (dd, J=5.2, 1.6 Hz, 1H), 7.62 (s, 1H), 7.58 (d, J=1.3 Hz, 1H), 7.49 (d, J=3.2 Hz, 1H), 7.00 (d, J=7.5 Hz, 1H), 6.85 (d, J=1.5 Hz, 1H), 6.70 (d, J=3.1 Hz, 1H), 6.67-6.61 (m, 1H), 5.27 (s, 2H), 4.07 (s, 2H), 3.86 (s, 3H), 3.39 (s, 2H), 2.25 (s, 3H); MS (ES+): 416.2 (M+1); MS (ES−): 414.1 (M−1); Analysis calculated for: C$_{25}$H$_{25}$N$_3$O$_3$.2H$_2$O. C, 66.50; H, 6.47; N, 9.31; Found: C, 66.95; H, 6.10; N, 9.21.

Scheme-368

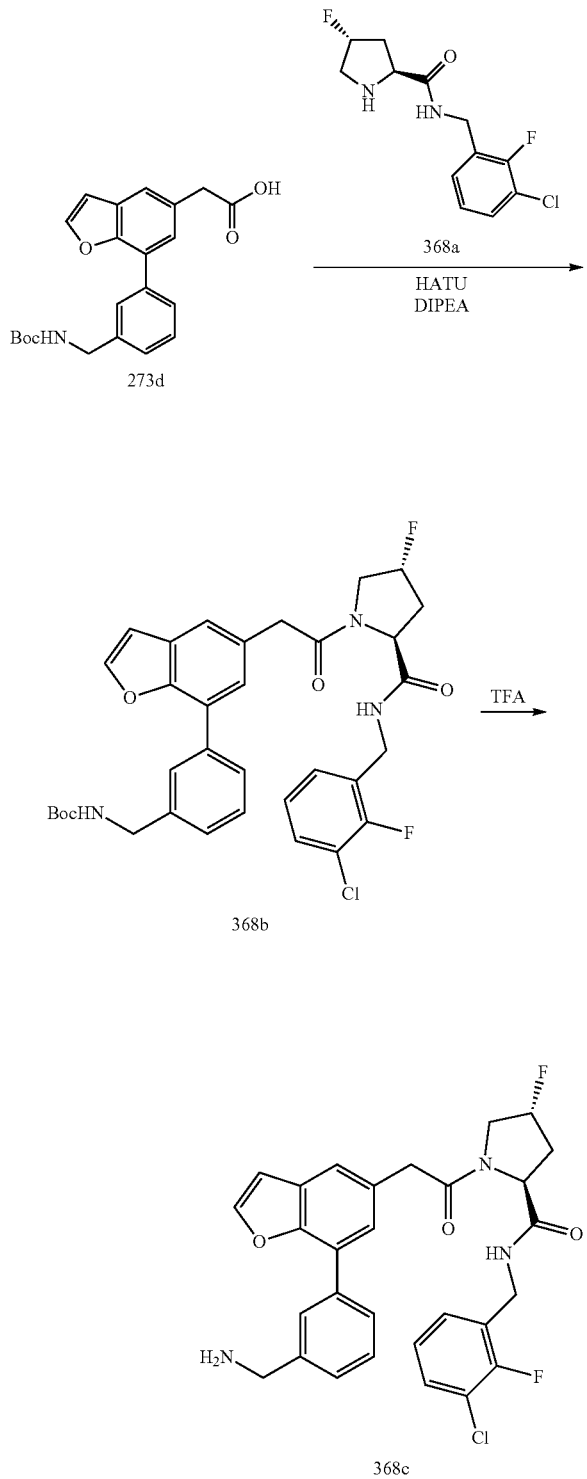

1163

Preparation of (2 S,4R)-1-(2-(7-(3-(aminomethyl)phenyl)benzofuran-5-yl)acetyl)-N-(3-chloro-2-fluorobenzyl)-4-fluoropyrrolidine-2-carboxamide (368c)

Step-1: Preparation of tert-butyl 3-(5-(2-((2S,4R)-2-((3-chloro-2-fluorobenzyl)carbamoyl)-4-fluoropyrrolidin-1-yl)-2-oxoethyl)benzofuran-7-yl)benzylcarbamate (368b)

Compound 368b was prepared according to the procedure reported in step-4 of scheme-1 from 2-(7-(3-(((tert-butoxycarbonyl)amino)methyl)phenyl)benzofuran-5-yl)acetic acid (273d) (50 mg, 0.13 mmol) in DMF (1 mL) using (2S,4R)—N-(3-chloro-2-fluorobenzyl)-4-fluoropyrrolidine-2-carboxamide (368a) (43.2 mg, 0.16 mmol; prepared according to the procedure reported by Altmann, Eva et al; in PCT Int Appl., 2012093101, 12 Jul. 2012), DIPEA (0.09 mL, 0.52 mmol) and HATU (74.8 mg, 0.20 mmol). This gave after workup and purification by flash column chromatography [silica (24 g), eluting with 0 to 50% DMA80/DCM] tert-butyl 3-(5-(2-((2 S,4R)-2-((3-chloro-2-fluorobenzyl)carbamoyl)-4-fluoropyrrolidin-1-yl)-2-oxoethyl)benzofuran-7-yl)benzylcarbamate (368b) (60 mg, 72% yield) as a white solid; MS (ES+): 538.1 & 540.1 (M-Boc+1), 660.3 (M+Na); MS (ES−): 636.2 & 638.3 (M−1).

Step-2: Preparation of (2S,4R)-1-(2-(7-(3-(aminomethyl)phenyl)benzofuran-5-yl)acetyl)-N-(3-chloro-2-fluorobenzyl)-4-fluoropyrrolidine-2-carboxamide (368c)

Compound 368c was prepared according to the procedure reported in step-5 of scheme-1 from tert-butyl 3-(5-(2-((2 S,4R)-2-((3-chloro-2-fluorobenzyl)carbamoyl)-4-fluoropyrrolidin-1-yl)-2-oxoethyl)benzofuran-7-yl)benzylcarbamate (368b) (60 mg, 0.09 mmol) in DCM (5 mL) using TFA (0.15 mL, 1.88 mmol). This gave after workup and purification by reverse phase column chromatography [C18 (50 g), eluting with ACN in water (containing 0.1% HCl) from 0-100%] (2 S,4R)-1-(2-(7-(3-(aminomethyl)phenyl)benzofuran-5-yl)acetyl)-N-(3-chloro-2-fluorobenzyl)-4-fluoropyrrolidine-2-carboxamide (368c) (35 mg, 69% yield) HCl salt as a white solid; $^1$H NMR (300 MHz, DMSO-$d_6$) δ 9.18 and 8.72 (2t, J=5.9 Hz, 1H), 8.46 (s, 3H), 8.06 (dd, J=2.3, 1.0 Hz, 1H), 7.96 (d, J=8.7 Hz, 1H), 7.87 (td, J=6.3, 5.5, 3.0 Hz, 1H), 7.63-7.49 (m, 3H), 7.49-7.27 (m, 3H), 7.19-6.96 (m, 2H), 5.53-5.15 (m, 1H), 4.52-4.24 (m, 3H), 4.24-3.94 (m, 3H), 3.93-3.63 (m, 3H), 2.75-2.53 (m, 1H), 2.46-1.85 (m, 1H); $^{19}$F NMR (282 MHz, DMSO-$d_6$) δ−121.47; MS (ES+): 538.2 (M+1); Analysis calculated for: $C_{29}H_{26}ClF_2N_3O_3 \cdot HCl \cdot 1.5H_2O$. C, 57.91; H, 5.03; Cl, 11.79; N, 6.99; Found: C, 57.74; H, 5.08; Cl, 11.94; N, 7.07.

Scheme-369

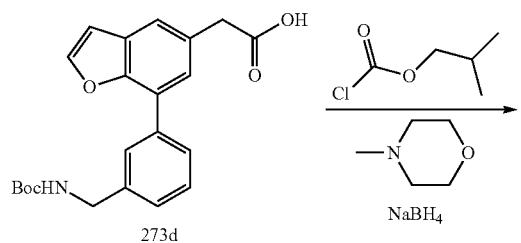

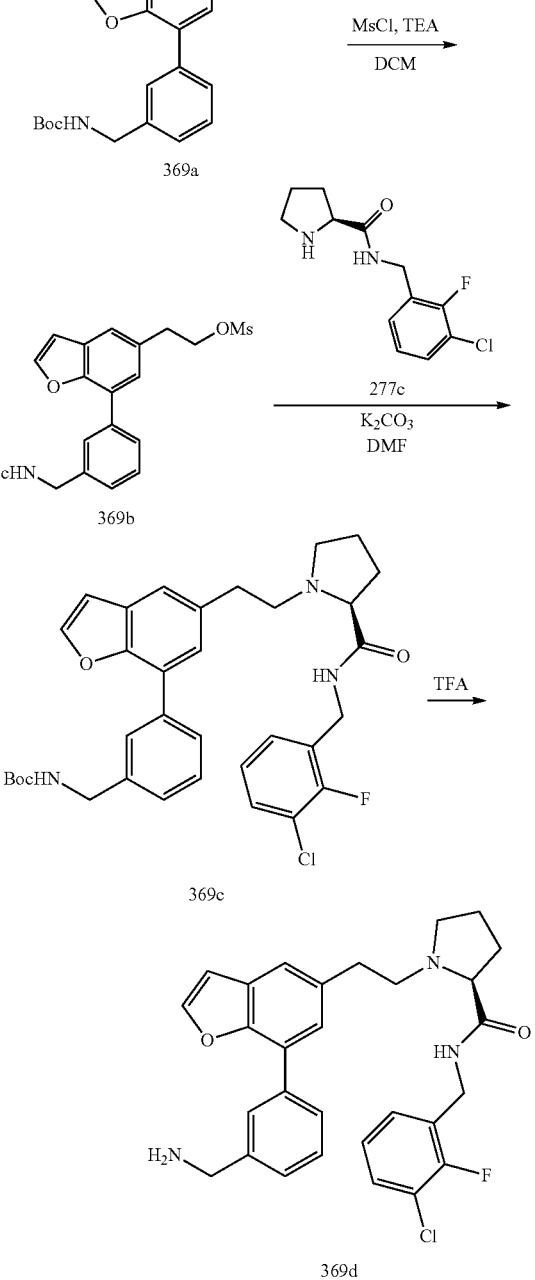

Preparation of (S)-1-(2-(7-(3-(aminomethyl)phenyl)benzofuran-5-yl)ethyl)-N-(3-chloro-2-fluorobenzyl)pyrrolidine-2-carboxamide (369d)

Step-1: Preparation of tert-butyl 3-(5-(2-hydroxyethyl)benzofuran-7-yl)benzylcarbamate (369a)

Compound 369a was prepared according to the procedure reported in step-1 of scheme-23 from 2-(7-(3-(((tert-butoxycarbonyl)amino)methyl)phenyl)benzofuran-5-yl)acetic acid (273d) (0.2 g, 0.52 mmol) using N-methylmorpholine (0.07 mL, 0.63 mmol) in THF (8 mL), isobutyl chloroformate (0.08 mL, 0.63 mmol) and NaBH$_4$ (0.06 g, 1.57 mmol) in water (0.5 mL). This gave after workup and purification by flash column chromatography [silica gel (12 g), eluting with EtOAc/MeOH=9:1 in Hexane from 0-100%] tert-butyl 3-(5-(2-hydroxyethyl)benzofuran-7-yl)benzylcarbamate (369a) (0.12 g, 62% yield) as a yellow solid; $^1$H NMR (300 MHz, DMSO-$d_6$) δ 8.00 (d, J=2.2 Hz, 1H), 7.71 (dt, J=9.5, 1.7 Hz, 2H), 7.52-7.41 (m, 3H), 7.32 (d, J=1.7 Hz, 1H), 7.27 (dt, J=7.7, 1.4 Hz, 1H), 6.98 (d, J=2.2 Hz, 1H), 4.67 (t, J=5.2 Hz, 1H), 4.22 (d, J=6.2 Hz, 2H), 3.67 (td, J=7.0, 5.1 Hz, 2H), 2.86 (t, J=7.0 Hz, 2H), 1.40 (s, 9H); MS (ES+): 390.2 (M+Na).

Step-2: Preparation of 2-(7-(3-(((tert-butoxycarbonyl)amino)methyl)phenyl)benzofuran-5-yl)ethyl methanesulfonate (369b)

To stirred a solution of tert-butyl 3-(5-(2-hydroxyethyl)benzofuran-7-yl)benzylcarbamate (369a) (110 mg, 0.30 mmol) in DCM (3 mL) was added at 0° C. methane sulfonyl chloride (0.03 mL, 0.33 mmol), triethylamine (0.063 mL, 0.449 mmol) and stirred at 0° C. for 30 mins. The reaction mixture was diluted with DCM, washed with brine, dried, filtered and concentrated in vacuum. The residue obtained was purified by flash column chromatography [silica (12 g), eluting with EtOAc/MeOH=9:1 in hexane from 0-100%] to give 2-(7-(3-(((tert-butoxycarbonyl)amino)methyl)phenyl)benzofuran-5-yl)ethyl methanesulfonate (369b) (116 mg, 87% yield) as a white solid; $^1$H NMR (300 MHz, DMSO-$d_6$) δ 8.04 (d, J=2.2 Hz, 1H), 7.77-7.69 (m, 2H), 7.58 (d, J=1.7 Hz, 1H), 7.52-7.41 (m, 3H), 7.32-7.24 (m, 1H), 7.02 (d, J=2.2 Hz, 1H), 4.49 (t, J=6.8 Hz, 2H), 4.22 (d, J=6.2 Hz, 2H), 3.18-3.14 (m, 2H), 3.13 (s, 3H), 1.40 (s, 9H); MS (ES+): 468.10 (M+Na)

Step-3: Preparation of (S)-tert-butyl 3-(5-(2-(2-((3-chloro-2-fluorobenzyl)carbamoyl)pyrrolidin-1-yl)ethyl)benzofuran-7-yl)benzylcarbamate (369c)

Compound 369c was prepared according to the procedure reported in step-2 of scheme-152 from 2-(7-(3-(((tert-butoxycarbonyl)amino)methyl)phenyl)benzofuran-5-yl)ethyl methanesulfonate (369b) (110 mg, 0.29 mmol) using (S)—N-(3-chloro-2-fluorobenzyl)pyrrolidine-2-carboxamide (277c) (146 mg, 0.57 mmol), K$_2$CO$_3$ (118 mg, 0.86 mmol) in DMF (2 mL) and stirring at 65° C. for 12 hr. This gave after workup and purification by flash column chromatography (silica gel, 40 g, eluting with ethyl acetate and hexanes) (S)-tert-butyl 3-(5-(2-(2-((3-chloro-2-fluorobenzyl)carbamoyl)pyrrolidin-1-yl)ethyl)benzofuran-7-yl)benzylcarbamate (369c) (35 mg, 20% yield) as a white solid; MS (ES+): 606.3 & 608.3 (M+1); MS (ES−): 640.3 & 642.2 (M+Cl).

Step-4: Preparation of (S)-1-(2-(7-(3-(aminomethyl)phenyl)benzofuran-5-yl)ethyl)-N-(3-chloro-2-fluorobenzyl)pyrrolidine-2-carboxamide (369d)

Compound 369d was prepared according to the procedure reported in step-5 of scheme-1 from (S)-tert-butyl 3-(5-(2-(2-((3-chloro-2-fluorobenzyl)carbamoyl)pyrrolidin-1-yl)ethyl)benzofuran-7-yl)benzylcarbamate (369c) (30 mg, 0.05 mmol) in DCM (5 mL) using TFA (0.08 mL, 0.99 mmol). This gave after workup and purification by reverse phase column chromatography [C18 (50 g), eluting with ACN in water (containing 0.1% HCl) from 0-100%](S)-1-(2-(7-(3-(aminomethyl)phenyl)benzofuran-5-yl)ethyl)-N-(3-chloro-2-fluorobenzyl)pyrrolidine-2-carboxamide (369d) (9 mg, 36% yield) HCl salt as a white solid; $^1$H NMR (300 MHz, DMSO-$d_6$) δ 9.76 (s, 1H), 9.41 (s, 1H), 8.48 (s, 3H), 8.09 (d, J=2.2 Hz, 1H), 8.05 (s, 1H), 7.90 (d, J=7.3 Hz, 1H), 7.64-7.45 (m, 5H), 7.36 (t, J=7.8 Hz, 1H), 7.19 (t, J=7.8 Hz, 1H), 7.04 (d, J=2.3 Hz, 1H), 4.45 (t, J=6.5 Hz, 2H), 4.41-4.25 (m, 1H), 4.13 (d, J=5.1 Hz, 2H), 3.76-3.62 (m, 1H), 3.62-3.43 (m, 2H), 3.15-2.98 (m, 2H), 2.33-2.20 (m, 1H), 2.14-2.01 (m, 2H), 1.98-1.80 (m, 2H); $^{19}$F NMR (282 MHz, DMSO-$d_6$) δ−121.07; MS (ES+): 506.2, 508.2 (M+1).

Scheme-370

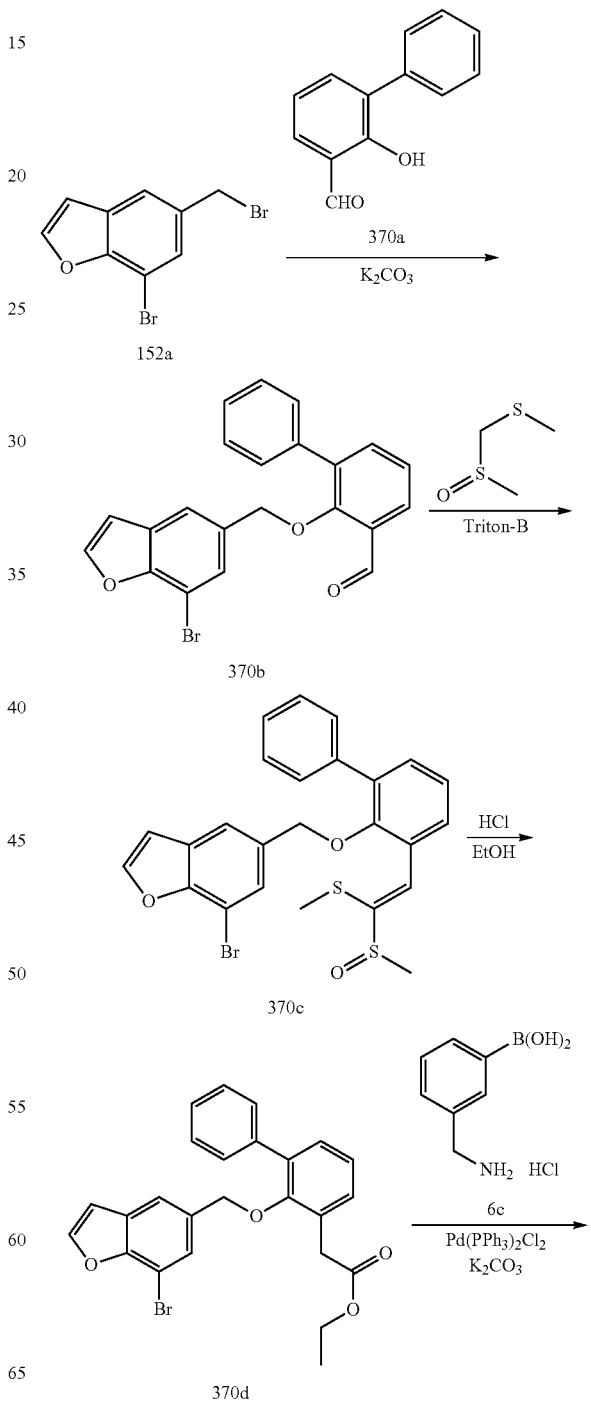

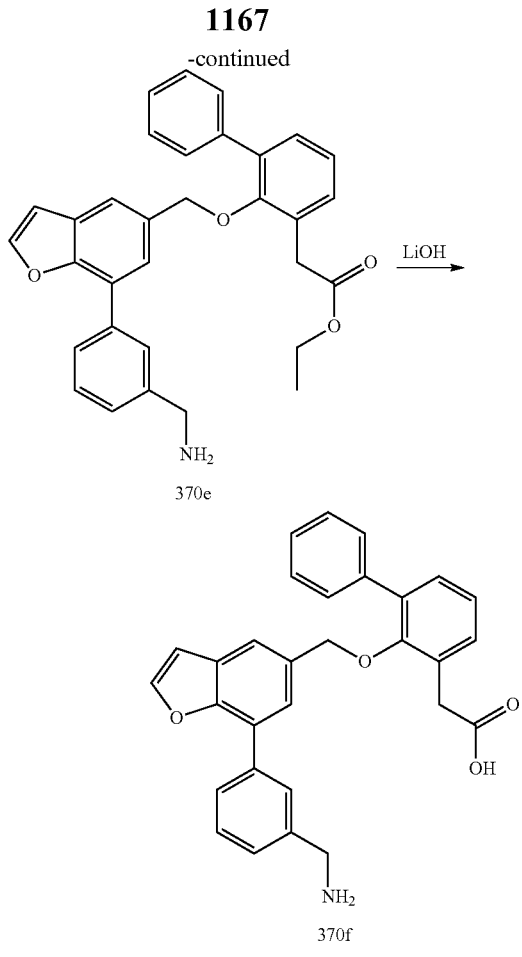

370e

370f

Preparation of 2-(2-((7-(3-(aminomethyl)phenyl)
benzofuran-5-yl)methoxy)-[1,1'-biphenyl]-3-yl)acetic Acid (370f)

Step-1: Preparation of 2-((7-bromobenzofuran-5-yl)methoxy)-[1,1'-biphenyl]-3-carbaldehyde (370b)

Compound 370b was prepared according to the procedure reported in step-2 of scheme-152 from 7-bromo-5-(bromomethyl)benzofuran (152a) (1.053 g, 3.63 mmol) using 2-hydroxy-[1,1'-biphenyl]-3-carbaldehyde (370a) (0.72 g, 3.63 mmol; CAS #14562-10-8), $K_2CO_3$ (1.506 g, 10.90 mmol) in DMF (20 mL) and stirring at room temperature for 16 h. This gave after workup and purification by flash column chromatography (silica gel, eluting with 0-5% ethyl acetate in hexanes) 2-((7-bromobenzofuran-5-yl)methoxy)-[1,1'-biphenyl]-3-carbaldehyde (370b) (1.38 g, 93% yield) as a white solid; $^1$H NMR (300 MHz, DMSO-$d_6$) δ 10.30 (t, J=0.8 Hz, 1H), 8.12 (d, J=2.1 Hz, 1H), 7.76 (ddt, J=9.4, 7.6, 1.4 Hz, 2H), 7.64-7.55 (m, 2H), 7.55-7.38 (m, 4H), 7.35 (d, J=1.5 Hz, 1H), 7.17 (d, J=1.5 Hz, 1H), 7.05 (dd, J=2.2, 0.8 Hz, 1H), 4.70 (s, 2H); MS (ES+): 429/431 (M+Na).

Step-2: Preparation of 7-bromo-5-(((3-(2-(methylsulfinyl)-2-(methylthio)vinyl)-[1,1'-biphenyl]-2-yl)oxy)methyl)benzofuran (370c)

Compound 370c was prepared according to the procedure reported in step-3 of scheme-266 from 2-((7-bromobenzofuran-5-yl)methoxy)-[1,1'-biphenyl]-3-carbaldehyde (370b) (2 g, 5.01 mmol) in THF (20 mL) using methyl(methylsulfinylmethyl)sulfane (0.674 g, 5.42 mmol), Triton-B (40% methanolic solution, 0.765 mL, 1.694 mmol) and heating at reflux for 16 h. This gave after workup and purification by flash column chromatography (Silica gel, 24 g, eluting with 0-40% EtOAc in hexane) 7-bromo-5-(((3-(2-(methylsulfinyl)-2-(methylthio)vinyl)-[1,1'-biphenyl]-2-yl)oxy)methyl)benzofuran (370c) (1.06 g, 61% yield) as an opaque oil; $^1$H NMR (300 MHz, DMSO-$d_6$) δ 8.10 (d, J=2.2 Hz, 1H), 8.06 (ddd, J=7.7, 1.8, 0.6 Hz, 1H), 7.86 (s, 1H), 7.62-7.54 (m, 2H), 7.53-7.42 (m, 4H), 7.36 (td, J=7.7, 0.5 Hz, 1H), 7.32 (d, J=1.5 Hz, 1H), 7.20-7.14 (m, 1H), 7.02 (d, J=2.2 Hz, 1H), 4.62-4.39 (m, 2H), 2.73 (s, 3H), 2.28 (s, 3H); MS (ES+): 513/515 (M+1).

Step-3: Preparation of Ethyl 2-(2-((7-bromobenzofuran-5-yl)methoxy)-[1,1'-biphenyl]-3-yl)acetate (370d)

Compound 370d was prepared according to the procedure reported in step-4 of scheme-266 from 7-bromo-5-(((3-(2-(methyl sulfinyl)-2-(methylthio)vinyl)-[1,1'-biphenyl]-2-yl)oxy)methyl)benzofuran (370c) (1.06 g, 2.064 mmol) in ethanol (20 mL) using HCl (4 M in 1,4-dioxane, 2.58 mL, 10.32 mmol) and heating at reflux for 16 h. This gave after workup and purification by flash column chromatography (silica gel, 24 g, eluting with 0-5% ethyl acetate and hexanes) ethyl 2-(2-((7-bromobenzofuran-5-yl)methoxy)-[1,1'-biphenyl]-3-yl)acetate (370d) (0.59 g, 61% yield) as an opaque oil; $^1$H NMR (300 MHz, DMSO-$d_6$) δ 8.11 (d, J=2.2 Hz, 1H), 7.61-7.53 (m, 2H), 7.52-7.40 (m, 3H), 7.36-7.27 (m, 3H), 7.22 (dd, J=8.3, 6.6 Hz, 1H), 7.17 (d, J=1.5 Hz, 1H), 7.07 (dd, J=2.2, 0.7 Hz, 1H), 4.42 (s, 2H), 4.03 (q, 2H), 3.74 (s, 2H), 1.12 (t, J=7.1, 0.7 Hz, 3H); MS (ES+): 465/467 (M+1).

Step-4: Preparation of Ethyl 2-(2-((7-(3-(aminomethyl)phenyl)benzofuran-5-yl)methoxy)-[1,1'-biphenyl]-3-yl)acetate (370e)

Compound 370e was prepared according to the procedure reported in step-3 of scheme-1 from ethyl 2-(2-((7-bromobenzofuran-5-yl)methoxy)-[1,1'-biphenyl]-3-yl)acetate (370d) (100 mg, 0.215 mmol) in dioxane (4 mL) water (1 mL) using 3-(aminomethyl)phenylboronic acid hydrochloride (6c) (60 mg, 0.322 mmol), bis(triphenylphosphine)palladium(II) chloride (Pd(PPh$_3$)$_2$Cl$_2$) (15.08 mg, 0.021 mmol), 3.3 M aqueous $K_2CO_3$ (0.195 mL, 0.645 mmol) under an argon atmosphere heating at 100° C. for 16 h on oil bath. This gave after workup, purification by flash column chromatography (silica gel, 12 g, eluting with 0-5% MeOH in DCM) ethyl 2-(2-((7-(3-(aminomethyl)phenyl)benzofuran-5-yl)methoxy)-[1,1'-biphenyl]-3-yl)acetate (370e) (74 mg, 70% yield) as a clear colorless oil. $^1$H NMR (300 MHz, DMSO-$d_6$) δ 8.07 (d, J=2.2 Hz, 1H), 7.75-7.69 (m, 1H), 7.62 (dt, J=8.2, 1.8 Hz, 3H), 7.49 (ddd, J=10.8, 6.6, 3.1 Hz, 3H), 7.44-7.37 (m, 2H), 7.33 (ddd, J=6.0, 4.3, 2.4 Hz, 3H), 7.27-7.18 (m, 1H), 7.14 (d, J=1.7 Hz, 1H), 7.01 (dd, J=2.2, 0.7 Hz, 1H), 4.48 (s, 2H), 4.01 (q, J=7.1 Hz, 2H), 3.83 (s, 2H), 3.75 (s, 2H), 1.15-0.97 (m, 3H); MS (ES+): 492 (M+1).

Step-5: Preparation of 2-(2-((7-(3-(aminomethyl)phenyl)benzofuran-5-yl)methoxy)-[1,1'-biphenyl]-3-yl)acetic Acid (370f)

Compound 370f was prepared according to the procedure reported in step-6 of scheme-1 from ethyl 2-(2-((7-(3-

(aminomethyl)phenyl)benzofuran-5-yl)methoxy)-[1,1'-biphenyl]-3-yl)acetate (370e) (74 mg, 0.151 mmol) in MeOH (3 mL), using a 2 M aqueous solution of lithium hydroxide (0.376 mL, 0.753 mmol). This gave after workup and purification by reverse phase column [C18 (100 g), eluting with ACN in water (containing 0.1% HCl) from 0-60%] 2-(2-((7-(3-(aminomethyl)phenyl)benzofuran-5-yl)methoxy)-[1,1'-biphenyl]-3-yl)acetic acid (370f) (57 mg, 82% yield) HCl salt as a white solid after lyophilization. $^1$H NMR (300 MHz, DMSO-$d_6$) δ 8.08 (d, J=2.2 Hz, 1H), 7.89 (d, J=1.8 Hz, 1H), 7.81 (dt, J=7.4, 1.7 Hz, 1H), 7.68-7.53 (m, 4H), 7.53-7.44 (m, 2H), 7.44-7.36 (m, 1H), 7.36-7.28 (m, 3H), 7.27-7.18 (m, 2H), 7.03 (d, J=2.2 Hz, 1H), 4.50 (s, 2H), 4.15 (s, 2H), 3.70 (s, 2H). HPLC purity: 99.4%; MS (ES+): 464 (M+1), (ES−): 462 (M−1); analysis calculated for $C_{30}H_{25}NO_4 \cdot HCl \cdot 1.25H_2O$: C, 68.96; H, 5.50; Cl, 6.79; N, 2.68; Found: C, 69.01; H, 5.56; Cl, 6.94; N, 2.82.

Scheme-371

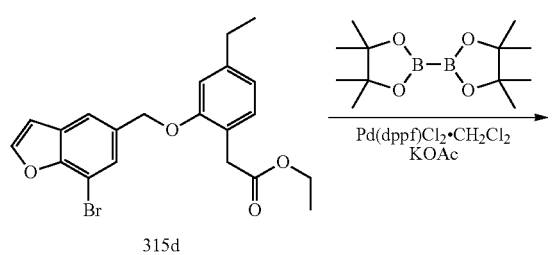

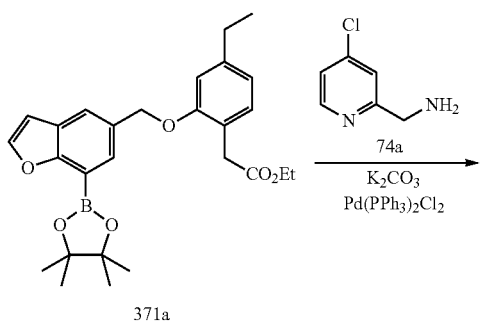

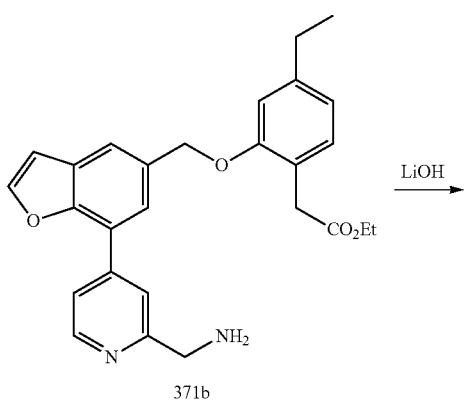

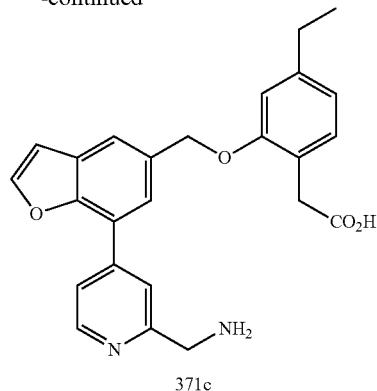

Preparation of 2-(2-((7-(2-(aminomethyl)pyridin-4-yl)benzofuran-5-yl)methoxy)-4-ethylphenyl)acetic Acid (371c)

Step-1: Preparation of Ethyl 2-(4-ethyl-2-((7-(4,4,5,5-tetramethyl-1,3,2-dioxaborolan-2-yl)benzofuran-5-yl)methoxy)phenyl)acetate (371a)

Compound 371a was prepared according to the procedure reported in step-1 of scheme-59 from ethyl 2-(2-((7-bromobenzofuran-5-yl)methoxy)-4-ethylphenyl)acetate (315d) (0.51 g, 1.222 mmol), using bis(pinacolato)diboron (0.466 g, 1.833 mmol), potassium acetate (0.360 g, 3.67 mmol) and Pd(dppf)Cl$_2$—CH$_2$Cl$_2$ (0.1 g, 0.122 mmol) in anhydrous dioxane (5 mL) under a nitrogen atmosphere and heating at 100° C. for 16 h. This gave after workup and purification by flash column chromatography [silica gel (24 g), eluting with EtOAc in hexanes from 0-10%] ethyl 2-(4-ethyl-2-((7-(4,4,5,5-tetramethyl-1,3,2-dioxaborolan-2-yl)benzofuran-5-yl)methoxy)phenyl)acetate (371a) (0.45 g, 79% yield) as a colorless oil; $^1$H NMR (300 MHz, DMSO-$d_6$) δ 8.06 (d, J=2.2 Hz, 1H), 7.84 (d, J=1.9 Hz, 1H), 7.66 (d, J=1.8 Hz, 1H), 7.09 (d, J=7.6 Hz, 1H), 6.98 (d, J=1.6 Hz, 1H), 6.97 (dd, J=2.3, 0.5 Hz, 1H), 6.75 (dd, J=7.6, 1.5 Hz, 1H), 5.16 (s, 2H), 3.99 (q, J=7.1 Hz, 2H), 3.53 (s, 2H), 2.58 (q, J=7.6 Hz, 2H), 1.34 (s, 12H), 1.19 (t, 3H), 1.05 (t, 3H); MS (ES+): 487 (M+Na).

Step-2: Preparation of Ethyl 2-(2-((7-(2-(aminomethyl)pyridin-4-yl)benzofuran-5-yl)methoxy)-4-ethylphenyl)acetate (371b)

Compound 371b was prepared according to the procedure reported in step-3 of scheme-1 from ethyl 2-(4-ethyl-2-((7-(4,4,5,5-tetramethyl-1,3,2-dioxaborolan-2-yl)benzofuran-5-yl)methoxy)phenyl)acetate (371a) (209 mg, 0.45 mmol) in dioxane (4 mL) using (4-chloropyridin-2-yl)methanamine (74a) (96 mg, 0.675 mmol), bis(triphenylphosphine)palladium(II) chloride (Pd(PPh$_3$)$_2$Cl$_2$) (31.6 mg, 0.045 mmol) and a solution of K$_2$CO$_3$ (0.409 mL, 1.35 mmol) in water (1.0 mL) under a nitrogen atmosphere heating at 100° C. for 16 h on oil bath. This gave after workup and purification by flash column chromatography [silica gel (12 g), eluting with 0-8% MeOH in DCM] ethyl 2-(2-((7-(2-(aminomethyl)pyridin-4-yl)benzofuran-5-yl)methoxy)-4-ethylphenyl)acetate (371b) (38 mg) as a pale-yellow oil, which was used as such in the next step; MS (ES+): 445 (M+1).

Step-3: Preparation of 2-(2-((7-(2-(aminomethyl)pyridin-4-yl)benzofuran-5-yl)methoxy)-4-ethylphenyl)acetic Acid (371c)

Compound 371c was prepared according to the procedure reported in step-6 of scheme-1 from ethyl 2-(2-((7-(2-(aminomethyl)pyridin-4-yl)benzofuran-5-yl)methoxy)-4-ethylphenyl)acetate (371b) (38 mg, 0.085 mmol) in MeOH (3 mL), THF (4 mL) using 2.0 M aqueous LiOH (0.214 mL, 0.427 mmol). This gave after workup and purification by reverse phase column [C18 (100 g), eluting with water in acetonitrile from 0-60%] 2-(2-((7-(2-(aminomethyl)pyridin-4-yl)benzofuran-5-yl)methoxy)-4-ethylphenyl)acetic acid (371c) (14 mg, 39% yield) HCl salt as a white solid; $^1$H NMR (300 MHz, DMSO-d$_6$) δ 8.78 (d, J=5.3 Hz, 1H), 8.62-8.34 (m, 3H), 8.17 (d, J=2.2 Hz, 1H), 8.09 (d, J=1.7 Hz, 1H), 7.99 (dd, J=5.3, 1.7 Hz, 1H), 7.88 (d, J=1.5 Hz, 1H), 7.83 (d, J=1.7 Hz, 1H), 7.16-7.06 (m, 2H), 6.98 (d, J=1.6 Hz, 1H), 6.76 (dd, J=7.6, 1.5 Hz, 1H), 5.28 (s, 2H), 4.31 (q, J=5.7, 5.3 Hz, 2H), 3.55 (s, 2H), 2.59 (q, J=7.7 Hz, 2H), 1.18 (t, J=7.6 Hz, 3H); MS (ES+): 417 (M+1), (ES-): 415 (M-1).

Scheme-372

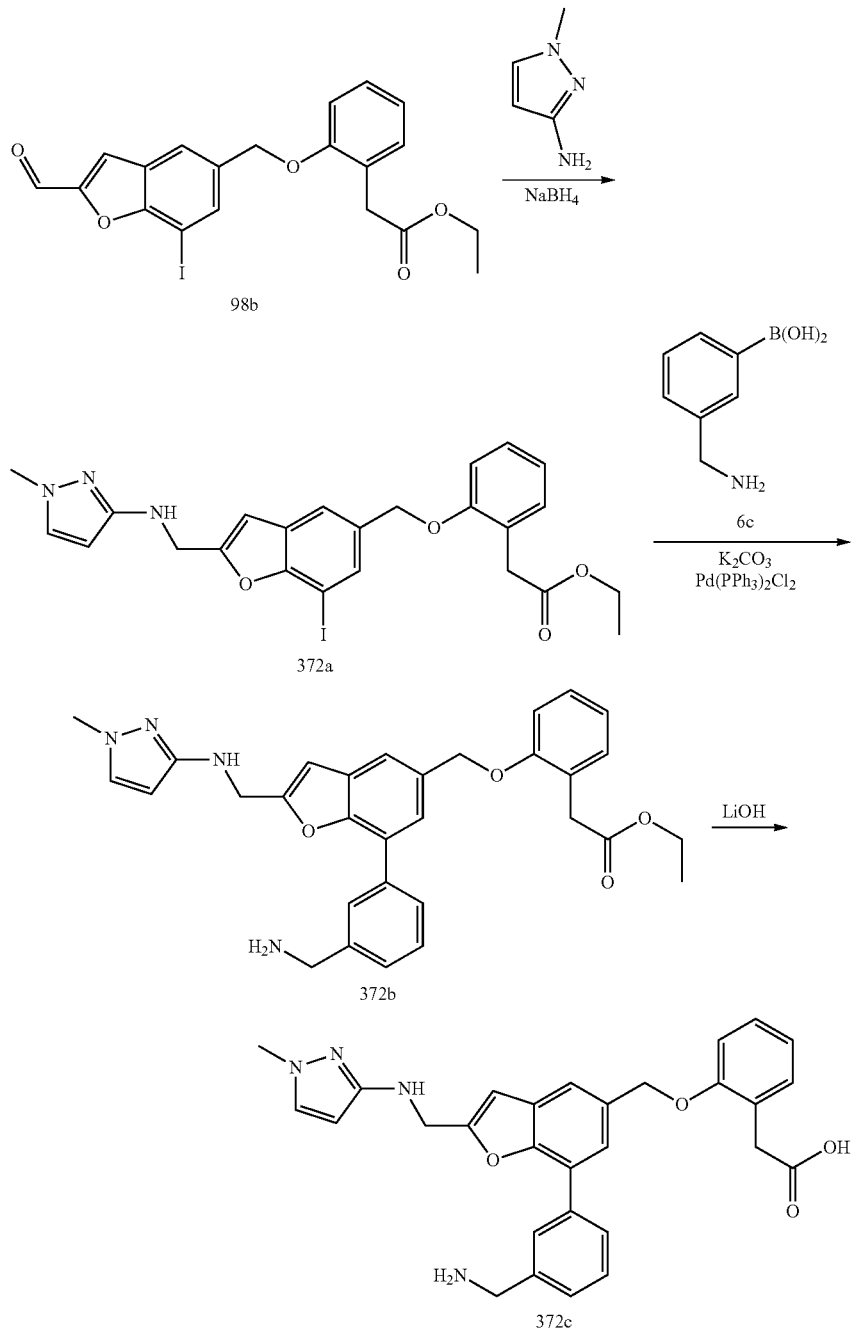

Preparation of 2-(2-((7-(3-(aminomethyl)phenyl)-2-(((1-methyl-1H-pyrazol-3-yl)amino)methyl)benzofuran-5-yl)methoxy)phenyl)acetic Acid (372c)

Step-1: Preparation of Ethyl 2-(2-((7-iodo-2-(((1-methyl-1H-pyrazol-3-yl)amino)methyl)benzofuran-5-yl)methoxy)phenyl)acetate (372a)

Compound 372a was prepared according to the procedure reported in step-1 of scheme-279 from ethyl 2-(2-((2-formyl-7-iodobenzofuran-5-yl)methoxy)phenyl)acetate (98b) (200 mg, 0.431 mmol) in ethanol (5 mL) using 1-methyl-1H-pyrazol-3-amine (46.0 mg, 0.474 mmol), sodium borohydride (32.6 mg, 0.862 mmol). This gave after workup and purification by flash column chromatography (silica gel, 25 g, eluting with DMA80 in DCM) ethyl 2-(2-((7-iodo-2-(((1-methyl-1H-pyrazol-3-yl)amino)methyl)benzofuran-5-yl)methoxy)phenyl)acetate (372a) (165 mg, 70% yield) as a brown solid; MS (ES+): 546.1 (M+1).

Step-2: Preparation of Ethyl 2-(2-((7-(3-(aminomethyl)phenyl)-2-(((1-methyl-1H-pyrazol-3-yl)amino)methyl)benzofuran-5-yl)methoxy)phenyl)acetate (372b)

Compound 372b was prepared according to the procedure reported in step-3 of scheme-1 from ethyl 2-(2-((7-iodo-2-(((1-methyl-1H-pyrazol-3-yl)amino)methyl)benzofuran-5-yl)methoxy)phenyl)acetate (372a) (160 mg, 0.293 mmol) in dioxane (10 mL) using 3-(aminomethyl)phenylboronic acid hydrochloride (6c) (88 mg, 0.469 mmol), bis(triphenylphosphine)palladium(II) chloride (Pd(PPh$_3$)$_2$Cl$_2$) (31 mg, 0.044 mmol) and a solution of K$_2$CO$_3$ (122 mg, 0.880 mmol) in Water (3 mL) under an N$_2$ atmosphere heating at 100° C. for 6 h on oil bath. This gave after workup, purification by flash column chromatography (silica gel, 40 g, eluting with DMA80 in DCM from 0-50%) ethyl 2-(2-((7-(3-(aminomethyl)phenyl)-2-(((1-methyl-1H-pyrazol-3-yl)amino)methyl)benzofuran-5-yl)methoxy)phenyl)acetate (372b) (45 mg, 29% yield) as a colorless gum; $^1$H NMR (300 MHz, DMSO-d$_6$) δ 7.80 (d, J=1.8 Hz, 1H), 7.72 (dt, J=7.6, 1.6 Hz, 1H), 7.58 (d, J=1.7 Hz, 1H), 7.50 (d, J=1.7 Hz, 1H), 7.48-7.35 (m, 2H), 7.32 (d, J=2.2 Hz, 1H), 7.22 (td, J=7.6, 1.8 Hz, 2H), 7.14-7.02 (m, 1H), 6.90 (td, J=7.4, 1.1 Hz, 1H), 6.73 (s, 1H), 5.78 (t, J=6.3 Hz, 1H), 5.51 (d, J=2.2 Hz, 1H), 5.21 (s, 2H), 4.38 (d, J=6.3 Hz, 2H), 3.92 (q, J=7.1 Hz, 2H), 3.80 (s, 2H), 3.62 (s, 2H), 3.59 (s, 3H), 0.98 (t, J=7.1 Hz, 3H); MS (ES+): 525.2 (M+1).

Step-3: Preparation of 2-(2-((7-(3-(aminomethyl)phenyl)-2-(((1-methyl-1H-pyrazol-3-yl)amino)methyl)benzofuran-5-yl)methoxy)phenyl)acetic Acid (372c)

Compound 372c was prepared according to the procedure reported in step-6 of scheme-1 from ethyl 2-(2-((7-(3-(aminomethyl)phenyl)-2-(((1-methyl-1H-pyrazol-3-yl)amino)methyl)benzofuran-5-yl)methoxy)phenyl)acetate (372b) (45 mg, 0.086 mmol) in THF/MeOH (2.5 mL, each) using a solution of lithium hydroxide hydrate (7 mg, 0.257 mmol) in water (0.5 mL). This gave after workup and purification by reverse phase column chromatography [C18 column, 50 g, eluting with water (containing 0.1% HCl)/acetonitrile (1:0 to 0:1)] 2-(2-((7-(3-(aminomethyl)phenyl)-2-(((1-methyl-1H-pyrazol-3-yl)amino)methyl)benzofuran-5-yl)methoxy)phenyl)acetic acid (372c) (30 mg, 70% yield) hydrochloride salt as a white solid; $^1$H NMR (300 MHz, DMSO-d$_6$) δ 8.53 (s, 3H), 8.03 (s, 1H), 7.91 (tt, J=4.9, 4.1, 1.8 Hz, 1H), 7.67 (q, J=2.0 Hz, 2H), 7.61 (d, J=1.6 Hz, 1H), 7.60-7.52 (m, 2H), 7.28-7.19 (m, 2H), 7.20 (s, 1H), 7.07 (d, J=8.1 Hz, 1H), 6.91 (dd, J=7.6, 0.9 Hz, 1H), 6.91-6.84 (m, 1H), 5.77 (d, J=2.6 Hz, 1H), 5.24 (s, 2H), 4.55 (s, 2H), 4.19-4.08 (m, 2H), 3.59 (s, 2H), 2.54 (s, 3H); MS (ES+): 497.2 (M+1), (ES−): 495.2 (M−1); Analysis calculated for C$_{29}$H$_{27}$ClFN$_3$O$_3$.HCl.1.5H$_2$O: C, 59.70; H, 5.36; Cl, 12.15; N, 7.20; Found C, 59.62; H, 5.25; Cl, 11.96; N, 7.15.

Scheme-373

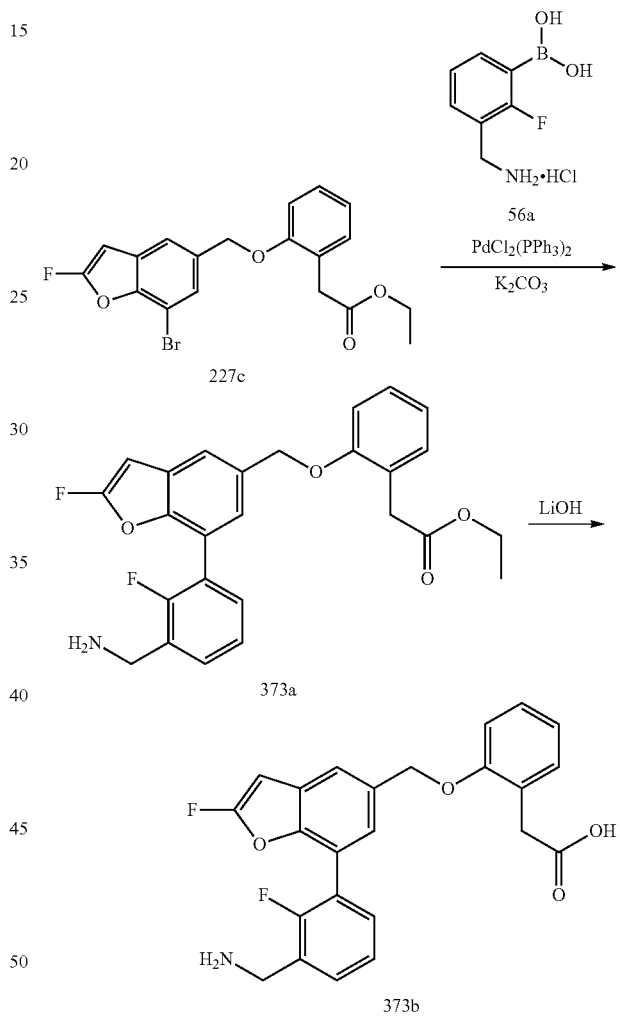

Preparation of 2-(2-((7-(3-(aminomethyl)-2-fluorophenyl)-2-fluorobenzofuran-5-yl)methoxy)phenyl) acetic Acid (373b)

Step-1: Preparation of Ethyl 2-(2-((7-(3-(aminomethyl)-2-fluorophenyl)-2-fluorobenzofuran-5-yl)methoxy)phenyl)acetate (373a)

Compound 373a was prepared according to the procedure reported in step-3 of scheme-1 from ethyl 2-(2-((7-bromo-2-fluorobenzofuran-5-yl)methoxy)phenyl)acetate (227c) (420 mg, 1.031 mmol) in dioxane (10 mL) using (3-(aminomethyl)-2-fluorophenyl)boronic acid hydrochloride (56a)

(244 mg, 1.186 mmol), a solution of K$_2$CO$_3$ (428 mg, 3.09 mmol) in water (2 mL), bis(triphenylphosphine)palladium (II) chloride (109 mg, 0.155 mmol) and heating at 100° C. for 7h on oil bath. This gave after workup, purification by flash column chromatography [silica (40g), eluting with DMA80 in DCM from 0-90%] ethyl 2-(2-((7-(3-(aminomethyl)-2-fluorophenyl)-2-fluorobenzofuran-5-yl)methoxy) phenyl)acetate (373a) (342 mg, 74% yield) as a pale yellow oil; $^1$H NMR (300 MHz, DMSO-d$_6$) δ 7.68 (d, J=1.7 Hz, 1H), 7.65-7.55 (m, 1H), 7.49-7.38 (m, 2H), 7.33 (d, J=7.6 Hz, 1H), 7.30-7.19 (m, 2H), 7.10 (dd, J=8.2, 1.1 Hz, 1H), 6.91 (td, J=7.4, 1.1 Hz, 1H), 6.45 (d, J=6.4 Hz, 1H), 5.21 (s, 2H), 3.91 (q, J=7.1 Hz, 2H), 3.83 (s, 2H), 3.62 (s, 2H), 0.99 (t, J=7.1 Hz, 3H); $^{19}$F NMR (282 MHz, DMSO-d$_6$) δ–111.69, –121.98; MS (ES+): 452.2 (M+1).

Step-2: Preparation of 2-(2-((7-(3-(aminomethyl)-2-fluorophenyl)-2-fluorobenzofuran-5-yl)methoxy) phenyl)acetic Acid (373b)

Compound 373b was prepared according to the procedure reported in step-6 of scheme-1, from ethyl 2-(2-((7-(3-(aminomethyl)-2-fluorophenyl)-2-fluorobenzofuran-5-yl)methoxy)phenyl)acetate (373a) (330 mg, 0.731 mmol) in MeOH/THF (2/10 mL each) using a solution of lithium hydroxide monohydrate (70.0 mg, 2.92 mmol) in water (2 mL). This gave after workup and purification by reverse phase column [C18 (150g), eluting with ACN in water (containing 0.1% HCl) from 0-100%] 2-(2-((7-(3-(aminomethyl)-2-fluorophenyl)-2-fluorobenzofuran-5-yl)methoxy) phenyl)acetic acid (373b) (210 mg, 68% yield) hydrochloride salt as a white solid; $^1$H NMR (300 MHz, DMSO-d$_6$) δ 7.75 (d, J=1.6 Hz, 1H), 7.71 (dd, J=7.8, 1.7 Hz, 1H), 7.66 (d, J=6.9 Hz, 1H), 7.49-7.40 (m, 2H), 7.23 (t, J=7.9 Hz, 2H), 7.08 (d, J=8.0 Hz, 1H), 6.90 (td, J=7.4, 1.1 Hz, 1H), 6.45 (d, J=6.5 Hz, 1H), 5.25 (s, 2H), 4.18 (s, 2H), 3.58 (s, 2H); $^{19}$F NMR (282 MHz, DMSO-d$_6$) δ–111.58, –118.50; MS (ES+) 420.10 (M+1), (ES–) 418.10 (M–1); MS (ES+): 424.10 (M+1), (ES–): 422.10 (M–1); Analysis calculated for C$_{24}$H$_{19}$F$_2$NO$_4$.HCl.0.75H$_2$O: C, 60.89; H, 4.58; Cl, 7.49; N, 2.96; Found; C, 60.82; H, 4.55; Cl, 7.19; N, 2.98.

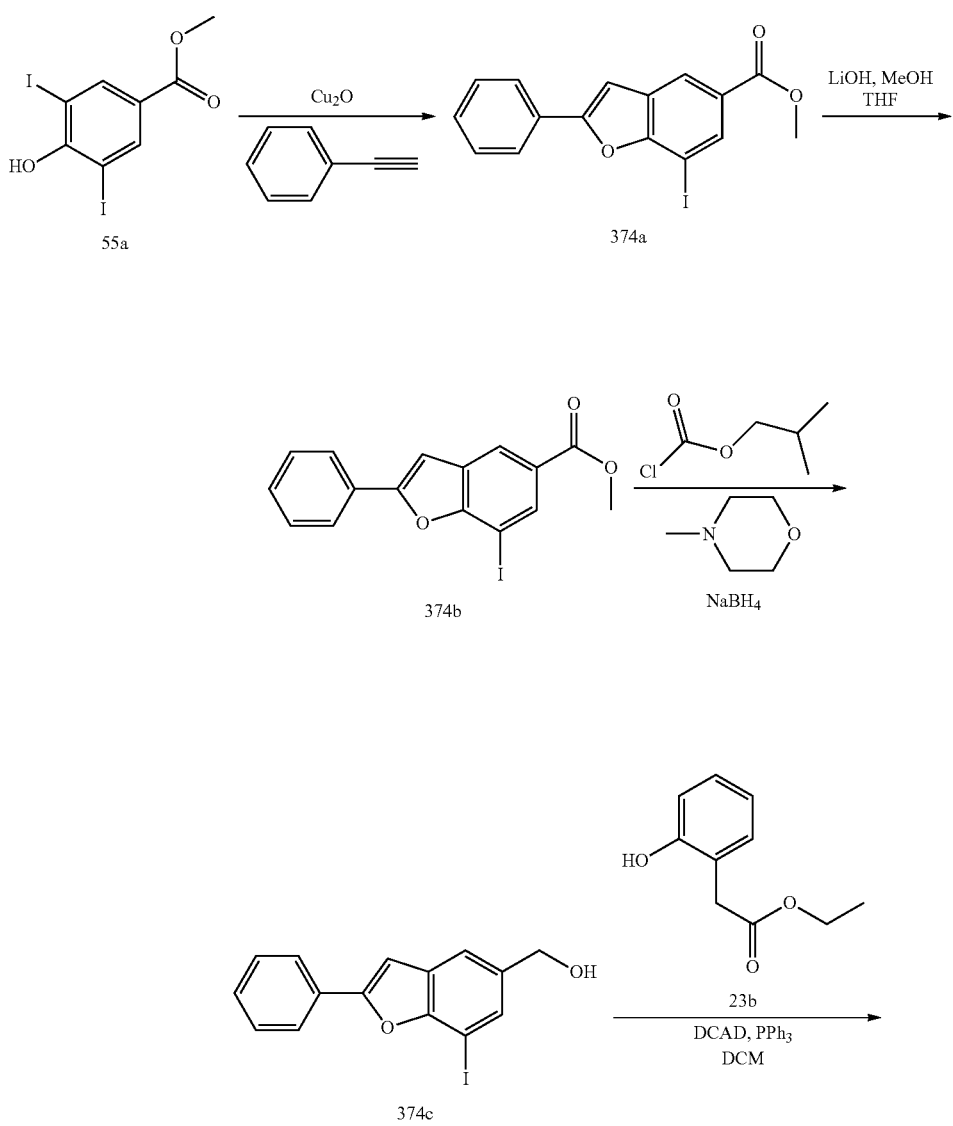

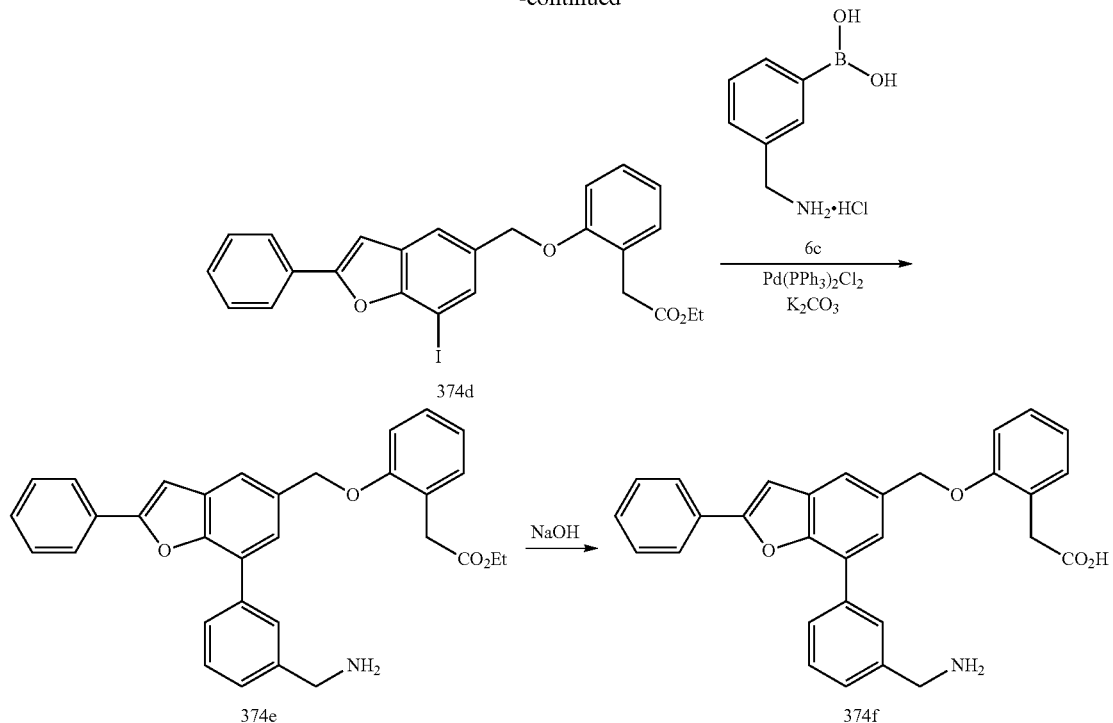

Preparation of 2-(2-((7-(3-(aminomethyl)phenyl)-2-phenylbenzofuran-5-yl)methoxy)phenyl)acetic Acid (374f)

Step-1: Preparation of methyl 7-iodo-2-phenylbenzofuran-5-carboxylate (374a)

Compound 374a was prepared according to the procedure reported in step-1 of scheme-55, from methyl 4-hydroxy-3,5-diiodobenzoate (55a) (6 g, 14.85 mmol) in pyridine (20 mL) using ethynylbenzene (1.52 g, 14.85 mmol) and copper (I) oxide (1.06 g, 7.43 mmol). This gave after workup and purification by flash column chromatography (silica gel, 120g, eluting with 0-10% EtOAc in hexanes) methyl 7-iodo-2-phenylbenzofuran-5-carboxylate (374a) (1.6 g, 57%) as an off-white solid; $^1$H NMR (300 MHz, DMSO-$d_6$) δ 8.29 (d, J=1.6 Hz, 1H), 8.23 (d, J=1.6 Hz, 1H), 7.97-7.91 (m, 2H), 7.70 (s, 1H), 7.61-7.41 (m, 3H), 3.89 (s, 3H).

Step-2: Preparation of 7-iodo-2-phenylbenzofuran-5-carboxylic Acid (374b)

Compound 374b was prepared according to the procedure reported in step-6 of scheme-1 from methyl 7-iodo-2-phenylbenzofuran-5-carboxylate (374a) (1.6 g, 4.23 mmol) in THF (10 mL) MeOH (10 mL) using a solution of lithium hydroxide hydrate (355 g, 8.46 mmol) in water (2 mL). This gave after workup 7-iodo-2-phenylbenzofuran-5-carboxylic acid (374b) (1.4 g, 91%) as a white solid; $^1$H NMR (300 MHz, DMSO-$d_6$) δ 8.23 (s, 1H), 8.14 (s, 1H), 7.93 (d, J=7.7 Hz, 2H), 7.62 (d, J=1.2 Hz, 1H), 7.58-7.40 (m, 3H).

Step-3: Preparation of (7-iodo-2-phenylbenzofuran-5-yl)methanol (374c)

Compound 374c was prepared according to the procedure reported in step-1 of scheme-23 7-iodo-2-phenylbenzofuran-5-carboxylic acid (374b) (1.4 g, 3.84 mmol) using N-methylmorpholine (0.466 g, 4.61 mmol) in THF (50 mL), isobutyl chloroformate (0.63 g, 4.61 mmol) and NaBH$_4$ (0.436 g, 11.53 mmol) in water (1 mL). This gave after workup and crystallization from ethyl acetate (7-iodo-2-phenylbenzofuran-5-yl)methanol (374c) (1.04 g, 77%) as a white solid. $^1$H NMR (300 MHz, DMSO-$d_6$) δ 7.89 (d, J=1.5 Hz, 1H), 7.86 (s, 1H), 7.62 (d, J=1.5 Hz, 1H), 7.58-7.38 (m, 5H), 4.52 (s, 2H).

Step-4: Preparation of Ethyl 2-(2-((7-iodo-2-phenylbenzofuran-5-yl)methoxy)phenyl)acetate (374d)

Compound 374d was prepared according to the procedure reported in step-2 of scheme-23 from (7-iodo-2-phenylbenzofuran-5-yl)methanol (374c) (0.3 g, 0.857 mmol) in DCM (10 mL) using triphenylphosphine (0.247 g, 0.942 mmol), ethyl 2-(2-hydroxyphenyl) acetate (23b) (0.170 g, 0.942 mmol) and bis(4-chlorobenzyl) diazene-1,2-dicarboxylate (DCAD, 0.346 g, 0.942 mmol) in DCM (10 mL). This gave after workup and purification by flash column chromatography (silica gel, eluting with EtOAc in hexane from 0-10%) ethyl 2-(2-((7-iodo-2-phenylbenzofuran-5-yl)methoxy)phenyl)acetate (374d) (0.206 g, 47% yield) as a colorless solid; $^1$H NMR (300 MHz, CDCl$_3$) δ 7.93-7.90 (m, 1H), 7.89 (t, J=1.4 Hz, 1H), 7.70 (d, J=1.5 Hz, 1H), 7.59 (dd, J=1.5, 0.8 Hz, 1H), 7.52-7.44 (m, 2H), 7.43-7.36 (m, 1H), 7.25-7.19 (m, 2H), 7.11 (s, 1H), 7.00-6.91 (m, 2H), 5.12 (s, 2H), 4.14 (q, J=7.1 Hz, 2H), 3.68 (d, J=2.1 Hz, 2H), 1.20 (t, J=7.1 Hz, 3H); MS (ES+): 535 (M+23), (ES−): 511 (M−1).

Step-5: Preparation of Ethyl 2-(2-((7-(3-(aminomethyl)phenyl)-2-phenylbenzofuran-5-yl)methoxy)phenyl)acetate (374e)

Compound 374e was prepared according to the procedure reported in step-3 of scheme-1 from ethyl 2-(2-((7-iodo-2- phenylbenzofuran-5-yl)methoxy)phenyl)acetate (374d) (200 mg, 0.390 mmol) in dioxane (4 mL) using 3-(aminomethyl)phenylboronic acid hydrochloride (6c) (80 mg, 0.429 mmol), a solution of K$_2$CO$_3$ (162 mg, 1.171 mmol) in water (mL), bis(triphenylphosphine)palladium(II) chloride (27 mg, 0.039 mmol) and heating at 100° C. for 8 h on oil bath. This gave after workup, purification by flash column chromatography [silica (12 g), eluting with methanol in DCM from 0-4%] ethyl 2-(2-((7-(3-(aminomethyl)phenyl)-2-phenylbenzofuran-5-yl)methoxy)phenyl)acetate (374e) (146 mg) as a colorless oil; MS (ES+) 492 (M+1).

Step-6: Preparation of 2-(2-((7-(3-(aminomethyl) phenyl)-2-phenylbenzofuran-5-yl)methoxy)phenyl) acetic Acid (374f)

Compound 374f was prepared according to the procedure reported in step-4 of scheme-4 from ethyl 2-(2-((7-(3-(aminomethyl)phenyl)-2-phenylbenzofuran-5-yl)methoxy) phenyl)acetate (374e) (146 mg, from above step-5) in MeOH (3 mL), water (1 mL) using sodium hydroxide (47 mg, 1.171 mmol). This gave after workup and purification by reverse-phase column chromatography [C-18 column, 100 g, eluting with 0.1% aqueous HCl in water and acetonitrile from 0-60%] 2-(2-((7-(3-(aminomethyl)phenyl)-2-phenylbenzofuran-5-yl)methoxy)phenyl)acetic acid (374f) (115 mg, 64% yield) HCl salt as a white solid; $^1$H NMR (300 MHz, DMSO-d$_6$) δ 8.09 (d, J=1.7 Hz, 1H), 8.04 (dt, J=7.7, 1.5 Hz, 1H), 8.01-7.92 (m, 2H), 7.77 (d, J=1.6 Hz, 1H), 7.71-7.62 (m, 2H), 7.62-7.49 (m, 4H), 7.49-7.39 (m, 1H), 7.25 (t, J=7.6 Hz, 2H), 7.11 (d, J=8.1 Hz, 1H), 6.91 (td, J=7.4, 1.1 Hz, 1H), 5.29 (s, 2H), 4.18 (s, 2H), 3.62 (s, 2H); MS (ES+): 464 (M+1), (ES−): 462 (M−1).

Scheme-375

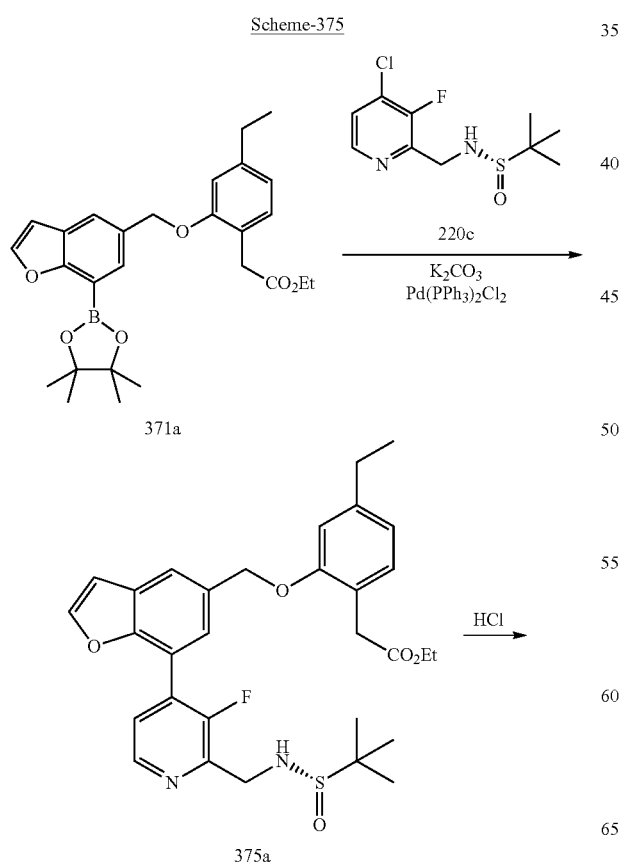

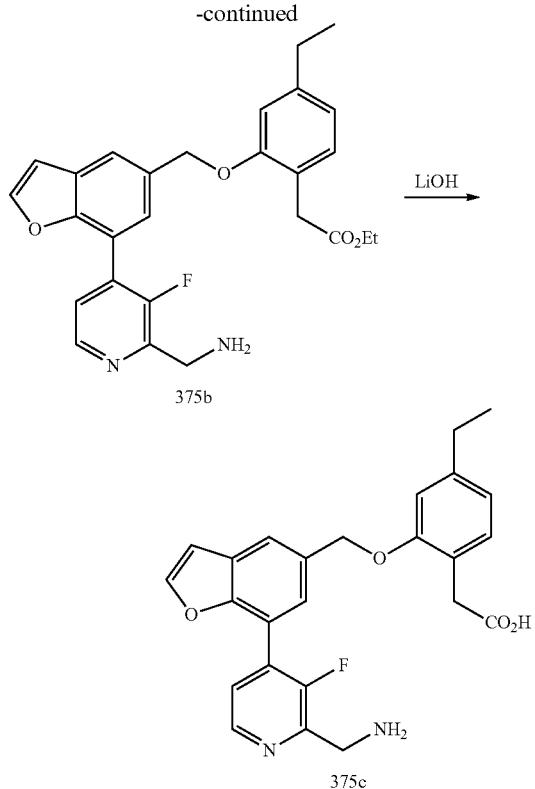

Preparation of 2-(2-((7-(2-(aminomethyl)-3-fluoropyridin-4-yl)benzofuran-5-yl)methoxy)-4-ethylphenyl)acetic Acid (375c)

Step-1: Preparation of Ethyl 2-(2-((7-(2-(((1,1-dimethylethylsulfinamido)methyl)-3-fluoropyridin-4-yl) benzofuran-5-yl)methoxy)-4-ethylphenyl)acetate (375a)

Compound 375a was prepared according to the procedure reported in step-3 of scheme-1 from ethyl 2-(4-ethyl-2-((7-(4,4,5,5-tetramethyl-1,3,2-dioxaborolan-2-yl)benzofuran-5-yl)methoxy)phenyl)acetate (371a) (224 mg, 0.482 mmol) in dioxane (4 mL) using (+)-(S)—N-((4-chloro-3-fluoropyridin-2-yl)methyl)-2-methylpropane-2-sulfinamide (220c) (192 mg, 0.724 mmol), bis(triphenylphosphine)palladium (II) chloride (Pd(PPh$_3$)$_2$Cl$_2$) (34 mg, 0.048 mmol) and a solution of K$_2$CO$_3$ (0.439 mL, 1.447 mmol) in water (1.0 mL) under a nitrogen atmosphere heating at 100° C. for 16 h on oil bath. This gave after workup and purification by flash column chromatography [silica gel (12 g), eluting with methanol in DCM from 0-4%] ethyl 2-(2-((7-(2-((1,1-dimethylethylsulfinamido)methyl)-3-fluoropyridin-4-yl)benzofuran-5-yl)methoxy)-4-ethylphenyl)acetate (375a) (189 mg) as a pale-yellow oil; MS (ES+): 567 (M+1).

Step-2: Preparation of Ethyl 2-(2-((7-(2-(aminomethyl)-3-fluoropyridin-4-yl)benzofuran-5-yl) methoxy)-4-ethylphenyl)acetate (375b)

Compound 375b was prepared according to the procedure reported in step-3 of scheme-305 from ethyl 2-(2-((7-(2-((1,1-dimethylethylsulfinamido)methyl)-3-fluoropyridin-4-yl) benzofuran-5-yl)methoxy)-4-ethylphenyl)acetate (375a)

(189 mg, 0.334 mmol) in dioxane (4 mL) using HCl (4 M in dioxane; 0.250 mL, 1.001 mmol) and stirring at room temperature for 16 h. This gave after workup ethyl 2-(2-((7-(2-(aminomethyl)-3-fluoropyridin-4-yl)benzofuran-5-yl)methoxy)-4-ethylphenyl)acetate (375b) which was used as such without purification in next step; MS (ES+): 463 (M+1).

Step-3: Preparation of 2-(2-((7-(2-(aminomethyl)-3-fluoropyridin-4-yl)benzofuran-5-yl)methoxy)-4-ethylphenyl)acetic Acid (375c)

Compound 375c was prepared according to the procedure reported in step-6 of scheme-1 from ethyl 2-(2-((7-(2-(aminomethyl)-3-fluoropyridin-4-yl)benzofuran-5-yl)methoxy)-4-ethylphenyl)acetate (375b) (from above step-2) in MeOH (3 mL) using 2.0 M aqueous LiOH (0.649 mL, 1.297 mmol). This gave after workup and purification by reverse phase column [C18 (100 g), eluting with water in acetonitrile from 0-60%] 2-(2-((7-(2-(aminomethyl)-3-fluoropyridin-4-yl)benzofuran-5-yl)methoxy)-4-ethylphenyl)acetic acid (375c) (26 mg, 23% yield) HCl salt as a pale-yellow solid after lyophilization. $^1$H NMR (300 MHz, DMSO-$d_6$) δ 8.64 (d, J=5.0 Hz, 1H), 8.60-8.40 (m, 3H), 8.12 (d, J=2.2 Hz, 1H), 7.92 (d, J=1.6 Hz, 1H), 7.81 (t, J=5.3 Hz, 1H), 7.61 (s, 1H), 7.18-7.04 (m, 2H), 6.98 (d, J=1.6 Hz, 1H), 6.76 (dd, J=7.5, 1.5 Hz, 1H), 5.27 (s, 2H), 4.47-4.27 (m, 2H), 3.55 (s, 2H), 2.57 (q, J=7.6 Hz, 2H), 1.18 (t, J=7.6 Hz, 3H). $^{19}$F NMR (282 MHz, DMSO-$d_6$) δ −128.37; MS (ES+): 435 (M+1), (ES−): 433 (M−1); Analysis calculated for $C_{25}H_{23}FN_2O_4 \cdot 1.35HCl \cdot 1.75H_2O$: C, 58.28; H, 5.45; Cl, 9.29; N, 5.44; Found: C, 58.38; H, 5.16; Cl, 9.38; N, 5.40.

Scheme-376

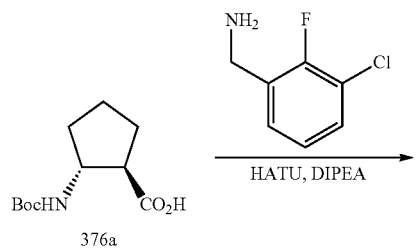

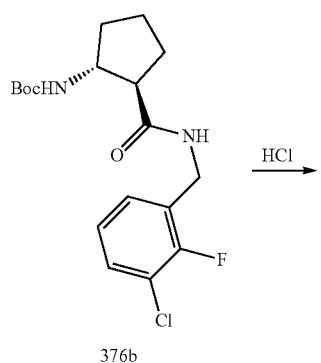

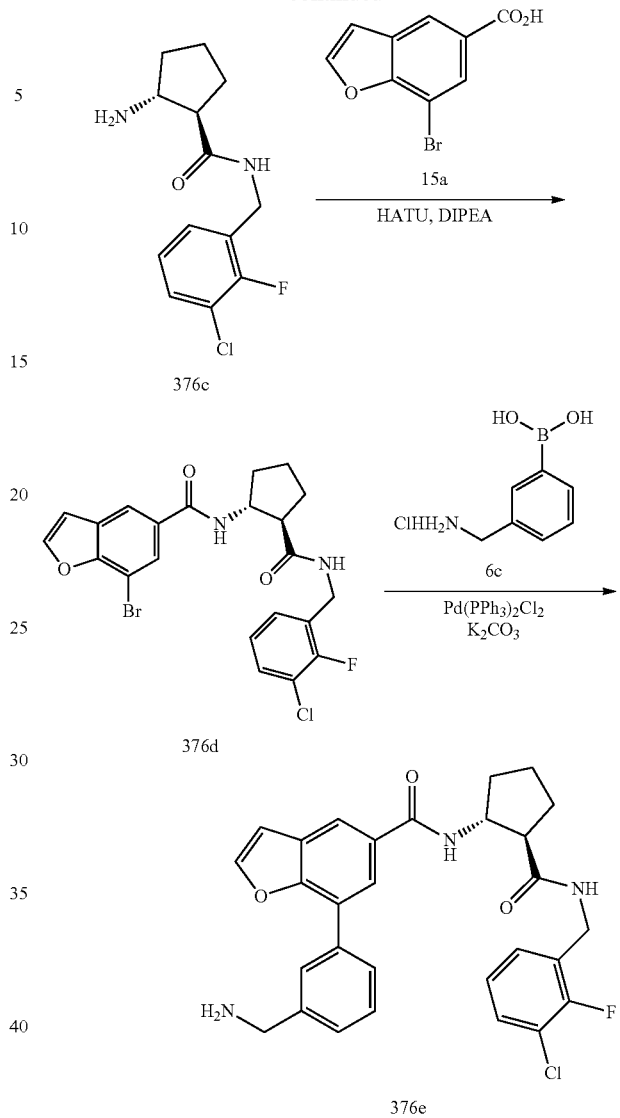

Preparation of 7-(3-(aminomethyl)phenyl)-N-((trans)-2-((3-chloro-2-fluorobenzyl)carbamoyl)cyclopentyl)benzofuran-5-carboxamide (376e)

Step-1: Preparation of tert-butyl ((trans)-2-((3-chloro-2-fluorobenzyl)carbamoyl)cyclopentyl)carbamate (376b)

Compound 376b was prepared according to the procedure reported in step-4 of scheme-1 from (trans)-2-((tert-butoxycarbonyl)amino)cyclopentanecarboxylic acid (376a) (0.46 g, 2.006 mmol; CAS #245115-25-7) in DCM (10 mL) using (3-chloro-2-fluorophenyl)methanamine (0.336 g, 2.107 mmol), DIPEA (1.051 mL, 6.02 mmol) and HATU (0.915 g, 2.408 mmol). This gave after workup and purification by flash column chromatography (silica gel, eluting with 0 to 30% EtOAc in hexane) tert-butyl ((trans)-2-((3-chloro-2-fluorobenzyl)carbamoyl)cyclopentyl)carbamate (376b) as an opaque oil; MS (ES+): 371/373 (M+1).

Step-2: Preparation of (trans)-2-amino-N-(3-chloro-2-fluorobenzyl)cyclopentanecarboxamide (376c)

Compound 376c was prepared according to the procedure reported in step-3 of scheme-305 from tert-butyl ((trans)-2-((3-chloro-2-fluorobenzyl)carbamoyl)cyclopentyl)carbamate (376b) (from above step-1) in methanol (10 mL) using HCl (4 M in dioxane; 10.03 mL, 40.1 mmol) and stirring at 40° C. for 1 h. This gave after workup and purification by flash column chromatography (silica gel, eluting with 0-10% MeOH in DCM) (trans)-2-amino-N-(3-chloro-2-fluorobenzyl)cyclopentanecarboxamide (376c) (60 mg, 11% yield) as a white solid; $^1$H NMR (300 MHz, DMSO-$d_6$) δ 8.77 (t, J=5.8 Hz, 1H), 8.25 (s, 3H), 7.49 (ddd, J=8.0, 7.2, 1.7 Hz, 1H), 7.40-7.27 (m, 1H), 7.20 (td, J=7.8, 1.1 Hz, 1H), 4.35 (qd, J=15.2, 5.7 Hz, 2H), 3.70 (dt, J=7.4, 5.7 Hz, 1H), 2.91-2.76 (m, 1H), 2.08 (td, J=11.5, 9.9, 4.9 Hz, 1H), 2.03-1.87 (m, 1H), 1.85-1.50 (m, 4H); MS (ES+): 271/273 (M+1).

Step-3: Preparation of 7-bromo-N-((trans)-2-((3-chloro-2-fluorobenzyl)carbamoyl)cyclopentyl)benzofuran-5-carboxamide (376d)

Compound 376d was prepared according to the procedure reported in step-4 of scheme-1 from (trans)-2-amino-N-(3-chloro-2-fluorobenzyl)cyclopentanecarboxamide (376c) (60 mg, 0.222 mmol) in DCM (10 mL) using 7-bromobenzofuran-5-carboxylic acid (15a) (59 mg, 0.244 mmol), DIPEA (0.116 mL, 0.665 mmol) and HATU (101 mg, 0.266 mmol). This gave after workup and purification by flash column chromatography (silica gel, eluting with 0 to 30% EtOAc in hexane) 7-bromo-N-((trans)-2-((3-chloro-2-fluorobenzyl)carbamoyl)cyclopentyl)benzofuran-5-carboxamide (376d) (90 mg, 82% yield); $^1$H NMR (300 MHz, DMSO-$d_6$) δ 8.53 (d, J=7.8 Hz, 1H), 8.41 (t, J=5.9 Hz, 1H), 8.20 (dd, J=6.0, 1.9 Hz, 2H), 8.05 (d, J=1.6 Hz, 1H), 7.41 (td, J=7.6, 1.7 Hz, 1H), 7.30-7.17 (m, 2H), 7.02 (td, J=7.9, 1.1 Hz, 1H), 4.54-4.19 (m, 3H), 2.76 (td, J=7.7, 5.2 Hz, 1H), 2.09-1.85 (m, 2H), 1.83-1.55 (m, 4H); MS (ES+): 493/495 (M+1); (ES−): 491/493 (M−1).

Step-4: Preparation of 7-(3-(aminomethyl)phenyl)-N-((trans)-2-((3-chloro-2-fluorobenzyl)carbamoyl)cyclopentyl)benzofuran-5-carboxamide (376e)

Compound 376e was prepared according to the procedure reported in step-3 of scheme-1 from -bromo-N-((trans)-2-((3-chloro-2-fluorobenzyl)carbamoyl)cyclopentyl)benzofuran-5-carboxamide (376d) (77 mg, 0.156 mmol) in dioxane (2 mL) using 3-(aminomethyl)phenylboronic acid hydrochloride (6c) (32 mg, 0.172 mmol), a solution of K$_2$CO$_3$ (65 mg, 0.468 mmol) in water (1 mL), bis(triphenylphosphine)palladium(II) chloride (11 mg, 0.016 mmol) and heating at 100° C. under an argon atmosphere for 16 h on oil bath. This gave after workup, purification by reverse phase column chromatography (C18, 100 g, eluting with 0-60% MeCN in H$_2$O containing 0.1% HCl) 7-(3-(aminomethyl)phenyl)-N-((trans)-2-((3-chloro-2-fluorobenzyl)carbamoyl)cyclopentyl)benzofuran-5-carboxamide (376e) (62 mg, 76% yield) HCl salt as a white solid; $^1$H NMR (300 MHz, DMSO-$d_6$) δ 8.61 (d, J=7.7 Hz, 1H), 8.53 (t, J=5.9 Hz, 1H), 8.38 (s, 3H), 8.22 (d, J=1.7 Hz, 1H), 8.18 (d, J=2.2 Hz, 1H), 8.13 (d, J=1.7 Hz, 1H), 8.08 (d, J=1.9 Hz, 1H), 7.97 (dt, J=7.6, 1.6 Hz, 1H), 7.66-7.52 (m, 2H), 7.37 (ddd, J=8.0, 7.1, 1.7 Hz, 1H), 7.30-7.21 (m, 1H), 7.17 (d, J=2.2 Hz, 1H), 6.95 (td, J=7.9, 1.1 Hz, 1H), 4.55-4.22 (m, 3H), 4.16 (q, J=5.5 Hz, 2H), 2.90 (q, J=8.1 Hz, 1H), 2.12-1.85 (m, 2H), 1.85-1.52 (m, 4H). MS (ES+): 520/522 (M+1), (ES−): 518/520; Analysis calculated for C$_{29}$H$_{27}$ClFN$_3$O$_3$.HCl.1.5H$_2$O: C, 59.70; H, 5.36; Cl, 12.15; N, 7.20; Found: C, 59.38; H, 5.09; Cl, 12.20; N, 7.13.

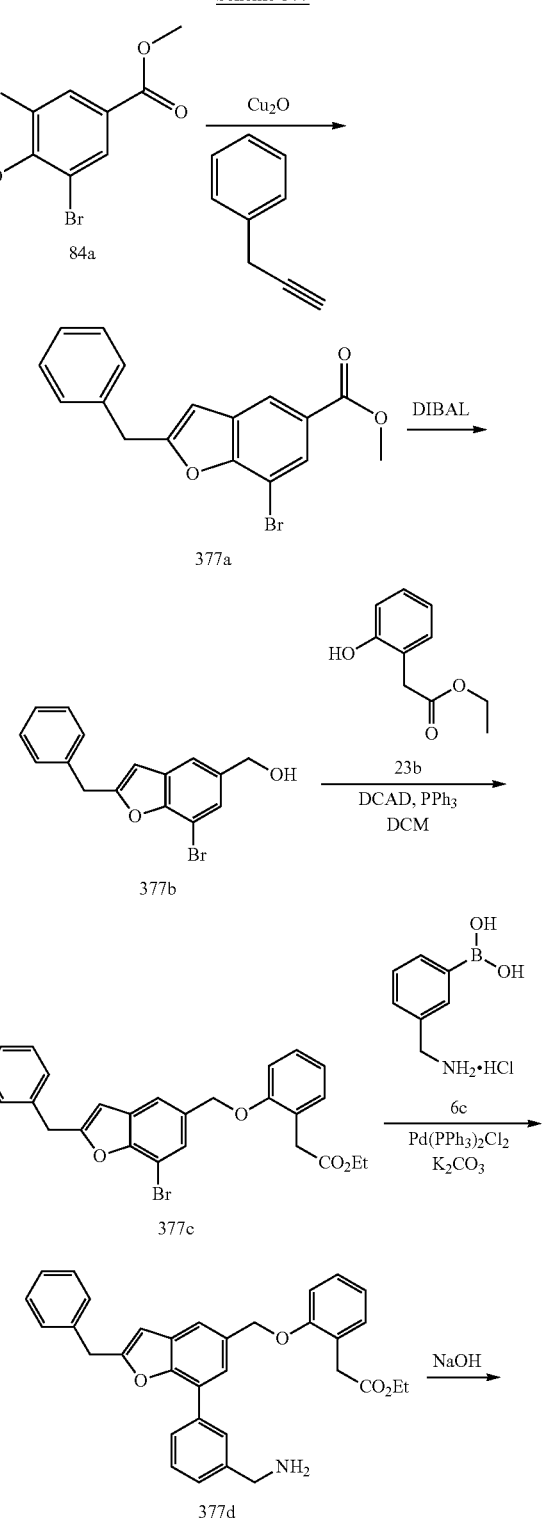

Scheme-377

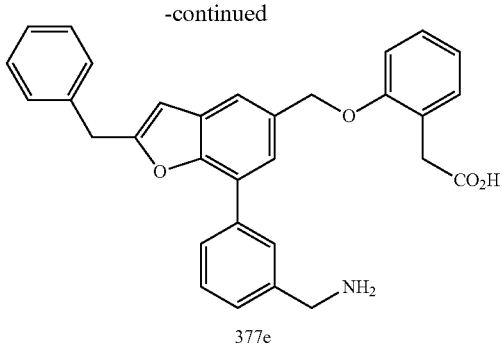

377e

Preparation of 2-(2-((7-(3-(aminomethyl)phenyl)-2-benzylbenzofuran-5-yl)methoxy)phenyl)acetic Acid (377e)

Step-1: Preparation of methyl 2-benzyl-7-bromobenzofuran-5-carboxylate (377a)

Compound 377a was prepared according to the procedure reported in step-1 of scheme-55 from methyl 3,5-dibromo-4-hydroxybenzoate (84a) (2.0 g, 6.45 mmol) in pyridine (17 mL) using prop-2-yn-1-ylbenzene (0.825 g, 7.10 mmol) and copper(I) oxide (0.462 g, 3.23 mmol). This gave after workup and purification by flash column chromatography (silica gel, 24 g, eluting with 0-3% EtOAc in hexanes) methyl 2-benzyl-7-bromobenzofuran-5-carboxylate (377a) (0.93 g, 42% yield) as a white solid. $^1$H NMR (300 MHz, CDCl$_3$) δ 8.11 (s, 2H), 7.41-7.27 (m, 5H), 6.43 (t, J=1.1 Hz, 1H), 4.16 (d, J=1.1 Hz, 2H), 3.92 (s, 3H); MS (ES+): 345/347 (M+1).

Step-2: Preparation of (2-benzyl-7-bromobenzofuran-5-yl)methanol (377b)

Compound 377b was prepared according to the procedure reported in step-2 of scheme-212 from methyl 2-benzyl-7-bromobenzofuran-5-carboxylate (377a) (0.93 g, 2.69 mmol) in DCM (10 mL) using 1 M DIBAL-H in DCM (6.74 mL, 6.74 mmol). This gave after workup and purification by flash column chromatography (silica gel, eluting with 0-20% EtOAc in Hexane) (2-benzyl-7-bromobenzofuran-5-yl)methanol (377b) (0.73 g, 85% yield) as a pale yellow oil; $^1$H NMR (300 MHz, CDCl$_3$) δ 7.43-7.26 (m, 8H), 6.34 (t, J=1.1 Hz, 1H), 4.70 (d, J=4.9 Hz, 2H), 4.14 (d, J=1.1 Hz, 2H); MS (ES+): 339/341 (M+Na).

Step-3: Preparation of Ethyl 2-(2-((2-benzyl-7-bromobenzofuran-5-yl)methoxy)phenyl)acetate (377c)

Compound 377c was prepared according to the procedure reported in step-2 of scheme-23 from (2-benzyl-7-bromobenzofuran-5-yl)methanol (377b) (0.73 g, 2.302 mmol) in DCM (20 mL) using triphenylphosphine (0.905 g, 3.45 mmol), ethyl 2-(2-hydroxyphenyl) acetate (23b) (0.622 g, 3.45 mmol) and bis(4-chlorobenzyl) diazene-1,2-dicarboxylate (DCAD, 1.268 g, 3.45 mmol). This gave after workup and purification by flash column chromatography (silica gel, eluting with EtOAc in hexane from 0-10%) ethyl 2-(2-((2-benzyl-7-bromobenzofuran-5-yl)methoxy)phenyl)acetate (377c) (0.81 g, 73% yield) as a pale-yellow oil; $^1$H NMR (300 MHz, DMSO-d$_6$) δ 7.60 (d, J=1.5 Hz, 1H), 7.51 (d, J=1.5 Hz, 1H), 7.40-7.18 (m, 7H), 7.06 (dd, J=8.3, 1.1 Hz, 1H), 6.91 (td, J=7.4, 1.1 Hz, 1H), 6.72 (d, J=0.9 Hz, 1H), 5.15 (s, 2H), 4.20 (s, 2H), 4.01 (q, J=7.1 Hz, 2H), 3.61 (s, 2H), 1.07 (t, J=7.1 Hz, 3H); MS (ES+): 501/503 (M+Na), (ES−): 477/479 (M−1).

Step-4: Preparation of Ethyl 2-(2-((7-(3-(aminomethyl)phenyl)-2-benzylbenzofuran-5-yl)methoxy)phenyl)acetate (377d)

Compound 377d was prepared according to the procedure reported in step-3 of scheme-1 from ethyl 2-(2-((2-benzyl-7-bromobenzofuran-5-yl)methoxy)phenyl)acetate (377c) (85 mg, 0.177 mmol) in dioxane (4 mL) using 3-(aminomethyl)phenylboronic acid hydrochloride (6c) (37 mg, 0.195 mmol), a solution of K$_2$CO$_3$ (74 mg, 0.532 mmol) in water (1 mL), bis(triphenylphosphine)palladium(II) chloride (13 mg, 0.018 mmol) and heating at 100° C. for 16 h on oil bath. This gave after workup, purification by flash column chromatography [silica (12 g), eluting with methanol in DCM from 0-6%] ethyl 2-(2-((7-(3-(aminomethyl)phenyl)-2-benzylbenzofuran-5-yl)methoxy)phenyl)acetate (377d) (48 mg) as a colorless oil; MS (ES+): 506 (M+1).

Step-5: Preparation of 2-(2-((7-(3-(aminomethyl)phenyl)-2-benzylbenzofuran-5-yl)methoxy)phenyl) acetic Acid (377e)

Compound 377e was prepared according to the procedure reported in step-4 of scheme-4 from ethyl 2-(2-((7-(3-(aminomethyl)phenyl)-2-benzylbenzofuran-5-yl)methoxy)phenyl)acetate (377d) (48 mg, from above step-4) in MeOH (3 mL), water (1 mL) using sodium hydroxide (22 mg, 0.532 mmol). This gave after workup and purification by reverse-phase column chromatography [C-18 column, 100 g, eluting with 0.1% aqueous HCl in water and acetonitrile from 0-60%] 2-(2-((7-(3-(aminomethyl)phenyl)-2-benzylbenzofuran-5-yl)methoxy)phenyl)acetic acid (377e) (41 mg, 48% yield) HCl salt as a white solid. $^1$H NMR (300 MHz, DMSO-d$_6$) δ 7.97-7.85 (m, 2H), 7.64 (d, J=1.6 Hz, 1H), 7.62-7.48 (m, 3H), 7.35 (d, J=4.4 Hz, 4H), 7.29-7.16 (m, 3H), 7.13-7.03 (m, 1H), 6.89 (td, J=7.3, 1.1 Hz, 1H), 6.65 (s, 1H), 5.23 (s, 2H), 4.20 (s, 2H), 4.11 (s, 2H), 3.58 (s, 2H); MS (ES+): 478 (M+1), (ES−): 476 (M−1); Analysis calculated for C$_{31}$H$_{27}$NO$_4$.HCl.H$_2$O: C, 69.98; H, 5.68; N, 2.63; Cl, 6.66; Found: C, 69.81; H, 5.33; N, 2.65; Cl, 7.01.

Scheme-378

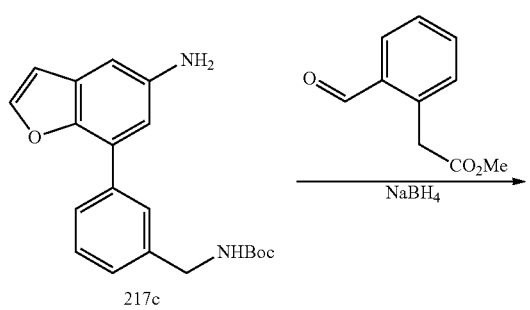

217c

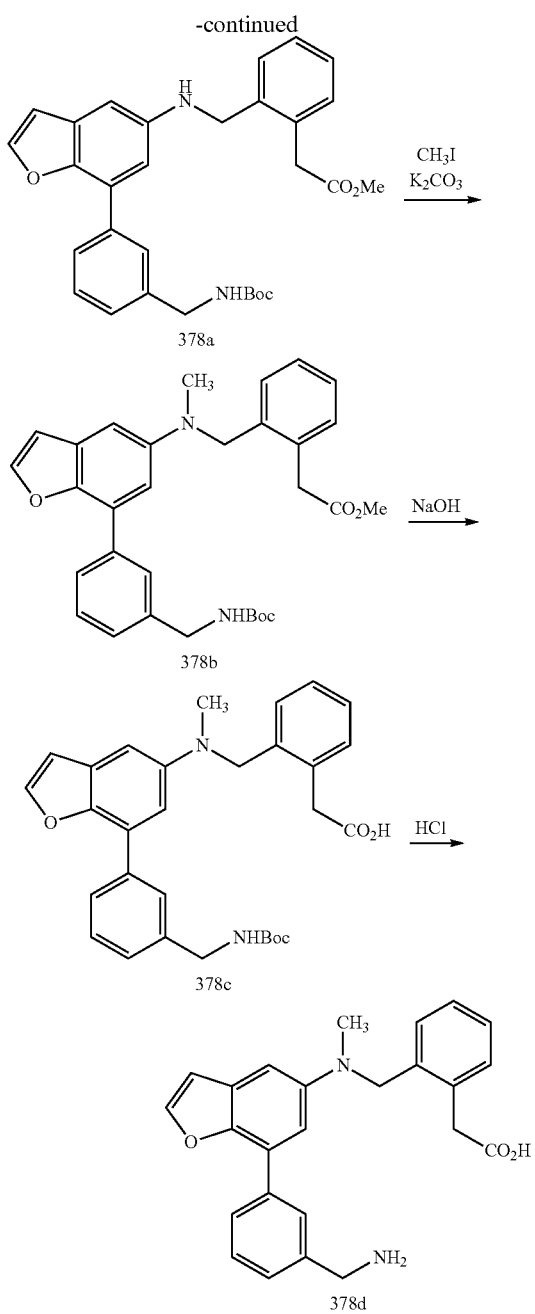

Preparation of 2-(2-(((7-(3-(aminomethyl)phenyl)benzofuran-5-yl)(methyl)amino)methyl)phenyl)acetic Acid (378d)

Step-1: Preparation of methyl 2-(2-(((7-(3-(((tert-butoxycarbonyl)amino)methyl)phenyl)benzofuran-5-yl)amino)methyl)phenyl)acetate (378a)

Compound 378a was prepared according to the procedure reported in step-1 of scheme-279 from tert-butyl 3-(5-aminobenzofuran-7-yl)benzylcarbamate (217c) (104 mg, 0.307 mmol) in DCM (10 mL) using methyl 2-(2-formylphenyl)acetate (66 mg, 0.369 mmol; CAS #63969-83-5) and sodium borohydride (58 mg, 1.537 mmol). This gave after workup, purification by flash column chromatography (silica gel, 12 g, eluting with 0-20% EtOAc in hexane) methyl 2-(2-(((7-(3-(((tert-butoxycarbonyl)amino)methyl)phenyl)benzofuran-5-yl)amino)methyl)phenyl)acetate (378a) (117 mg) as a colorless oil; MS (ES+) 501 (M+1).

Step-2: Preparation of methyl 2-(2-(((7-(3-(((tert-butoxycarbonyl)amino)methyl)phenyl)benzofuran-5-yl)(methyl)amino)methyl)phenyl)acetate (378b)

To a solution of methyl 2-(2-(((7-(3-(((tert-butoxycarbonyl)amino)methyl)phenyl)benzofuran-5-yl)amino)methyl)phenyl)acetate (378a) (117 mg, from step-1 above) in MeCN (10 mL) was added methyl iodide (218 mg, 1.537 mmol), $K_2CO_3$ (85 mg, 0.615 mmol) and heated at 40° C. for 48 h. The reaction mixture was cooled and evaporated to dryness. The residue was taken in water (25 mL) and extracted with EtOAc (3×25 mL). The combined organic layers were washed with $H_2O$ (25 mL), brine (25 mL), dried, filtered and concentrated in vacuum. The residue obtained was purified by flash column chromatography (silica gel, 12 g, eluting with 0-20% EtOAc in hexane) to provide methyl 2-(2-(((7-(3-(((tert-butoxycarbonyl)amino)methyl)phenyl)benzofuran-5-yl)(methyl)amino)methyl)phenyl)acetate (378b) (67 mg) as a colorless oil; MS (ES+): 515 (M+1).

Step-3: Preparation of 2-(2-(((7-(3-(((tert-butoxycarbonyl)amino)methyl)phenyl)benzofuran-5-yl)(methyl)amino)methyl)phenyl)acetic Acid (378c)

Compound 378c was prepared according to the procedure reported in step-4 of scheme-4, from methyl 2-(2-(((7-(3-(((tert-butoxycarbonyl)amino)methyl)phenyl)benzofuran-5-yl)(methyl)amino)methyl)phenyl)acetate (378b) (67 mg, from step-2 above) in MeOH (3 mL), water (1 mL) using NaOH (36.9 mg, 0.922 mmol) This gave after workup 2-(2-(((7-(3-(((tert-butoxycarbonyl)amino)methyl)phenyl)benzofuran-5-yl)(methyl)amino)methyl)phenyl)acetic acid (378c) which was used as such in next step; MS (ES+): 501 (M+1), (ES-): 499 (M-1).

Step-4: Preparation of 2-(2-(((7-(3-(aminomethyl)phenyl)benzofuran-5-yl)(methyl)amino)methyl)phenyl)acetic Acid (378d)

Compound 378d was prepared according to the procedure reported in step-3 of scheme-305 from 2-(2-(((7-(3-(((tert-butoxycarbonyl)amino)methyl)phenyl)benzofuran-5-yl)(methyl)amino)methyl)phenyl)acetic acid (378c) (from above step-3) in dioxane (5 mL) using HCl (4 M in dioxane; 0.768 mL, 3.07 mmol) and stirring at 60° C. for 1 h. This gave after workup and purification by reverse phase column chromatography (C18, 100 g, 0-60% MeCN in $H_2O$ containing 0.1% HCl) 2-(2-(((7-(3-(aminomethyl)phenyl)benzofuran-5-yl)(methyl)amino)methyl)phenyl)acetic acid (378d) (50 mg, 41% yield) HCl salt as a white solid; $^1H$ NMR (300 MHz, DMSO-$d_6$+$D_2O$) δ 7.94 (d, J=2.2 Hz, 1H), 7.89 (s, 1H), 7.83 (d, J=7.6 Hz, 1H), 7.57 (t, J=7.6 Hz, 1H), 7.50 (d, J=7.7 Hz, 1H), 7.23 (m, 3H), 7.14 (d, J=6.9 Hz, 1H), 7.05 (d, J=4.2 Hz, 2H), 6.90 (d, J=2.2 Hz, 1H), 4.65 (s, 2H), 4.12 (t, J=5.6 Hz, 2H), 3.73 (s, 2H), 3.11 (s, 3H); MS (ES+): 401 (M+1), (ES-): 399 (M-1).

Scheme-379

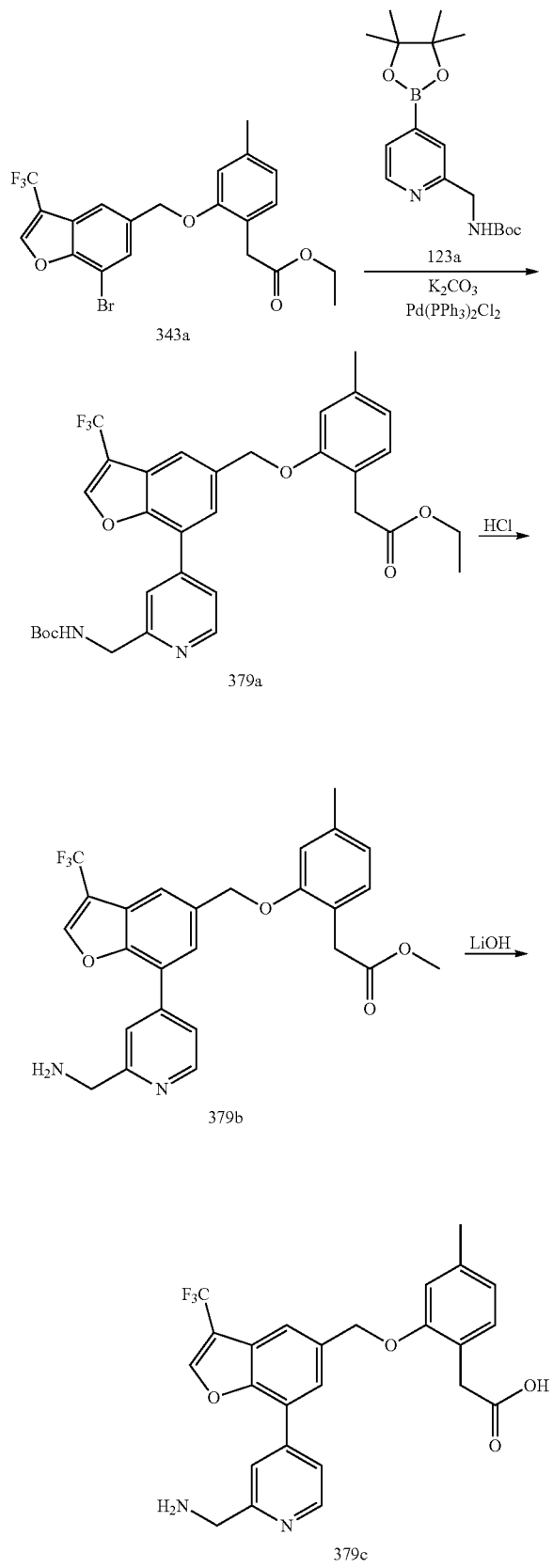

Preparation of 2-(2-((7-(2-(aminomethyl)pyridin-4-yl)-3-(trifluoromethyl)benzofuran-5-yl)methoxy)-4-methylphenyl)acetic Acid (379c)

Step-1: Preparation of Ethyl 2-(2-((7-(2-(((tert-butoxycarbonyl)amino)methyl)pyridin-4-yl)-3-(trifluoromethyl)benzofuran-5-yl)methoxy)-4-methylphenyl)acetate (379a)

Compound 379a was prepared according to the procedure reported in step-3 of scheme-1 from ethyl 2-(2-((7-bromo-3-(trifluoromethyl)benzofuran-5-yl)methoxy)-4-methylphenyl)acetate (343a) (141 mg, 0.299 mmol) in dioxane (5 mL) using tert-butyl ((4-(4,4,5,5-tetramethyl-1,3,2-dioxaborolan-2-yl)pyridin-2-yl)methyl)carbamate (123a) (150 mg, 0.449 mmol), bis(triphenylphosphine)palladium(II) chloride (Pd(PPh$_3$)$_2$Cl$_2$) (32 mg, 0.045 mmol) and a solution of K$_2$CO$_3$ (124 mg, 0.898 mmol) in water (0.5 mL) under an argon atmosphere heating at 100° C. for 3 h on oil bath. This gave after workup, purification by flash column chromatography [silica gel (24 g), eluting with DMA80 in DCM from 0-50%] ethyl 2-(2-((7-(2-(((tert-butoxycarbonyl)amino)methyl)pyridin-4-yl)-3-(trifluoromethyl)benzofuran-5-yl)methoxy)-4-methylphenyl)acetate (379a) (179 mg, 100% yield) as a dark oil; MS (ES+): 599.3 (M+1).

Step-2: Preparation of methyl 2-(2-((7-(2-(aminomethyl)pyridin-4-yl)-3-(trifluoromethyl)benzofuran-5-yl)methoxy)-4-methylphenyl)acetate (379b)

Compound 379b was prepared according to the procedure reported in step-3 of scheme-305 from ethyl 2-(2-((7-(2-(((tert-butoxycarbonyl)amino)methyl)pyridin-4-yl)-3-(trifluoromethyl)benzofuran-5-yl)methoxy)-4-methylphenyl)acetate (379a) (175 mg, 0.292 mmol) in methanol (6 mL) using HCl (4 M in dioxane; 0.6 mL, 2.4 mmol) and stirring at room temperature overnight. This gave after workup, purification by flash column chromatography [silica (12 g), eluting with DMA80/DCM from 0-80%] methyl 2-(2-((7-(2-(aminomethyl)pyridin-4-yl)-3-(trifluoromethyl)benzofuran-5-yl)methoxy)-4-methylphenyl)acetate (379b) (91 mg, 64% yield) as clear oil; $^1$H NMR (300 MHz, DMSO-d$_6$) δ 8.95 (q, J=1.7 Hz, 1H), 8.66 (d, J=5.2 Hz, 1H), 7.96 (s, 1H), 7.93-7.84 (m, 2H), 7.80-7.70 (m, 1H), 7.11 (d, J=7.5 Hz, 1H), 6.98 (d, J=1.6 Hz, 1H), 6.81-6.67 (m, 1H), 5.31 (s, 2H), 3.92 (s, 2H), 3.61 (s, 2H), 3.46 (s, 3H), 2.30 (s, 3H); $^{19}$F NMR (282 MHz, DMSO-d$_6$) δ−58.07. MS (ES+): 485.1 (M+1).

Step-3: Preparation of 2-(2-((7-(2-(aminomethyl)pyridin-4-yl)-3-(trifluoromethyl)benzofuran-5-yl)methoxy)-4-methylphenyl)acetic Acid (379c)

Compound 379c was prepared according to the procedure reported in step-6 of scheme-1 from methyl 2-(2-((7-(2-(aminomethyl)pyridin-4-yl)-3-(trifluoromethyl)benzofuran-5-yl)methoxy)-4-methylphenyl)acetate (379b) (89 mg, 0.184 mmol) in MeOH/THF (6 mL each), THF (6 mL) using a solution of lithium hydroxide (61 mg, 1.454 mmol) in water (2 mL). This gave after workup and purification by reverse phase column [C18 (50 g), eluting with ACN in water (containing 0.1% HCl) from 0-100%] 2-(2-((7-(2-(aminomethyl)pyridin-4-yl)-3-(trifluoromethyl)benzofuran-5-yl)methoxy)-4-methylphenyl)acetic acid (379c) (51 mg, 59% yield) HCl salt as a white solid; $^1$H NMR (300 MHz, DMSO-d$_6$) δ 8.98 (q, J=1.6 Hz, 1H), 8.81 (d, J=5.3 Hz, 1H), 8.61 (s, 3H), 8.08 (d, J=1.7 Hz, 1H), 7.97 (t, J=2.7 Hz, 3H),

1191

7.10 (d, J=7.5 Hz, 1H), 6.97 (d, J=1.5 Hz, 1H), 6.74 (d, J=7.3 Hz, 1H), 5.33 (s, 2H), 4.32 (d, J=5.5 Hz, 2H), 3.56 (d, J=2.4 Hz, 2H), 2.30 (s, 3H); $^{19}F$ NMR (282 MHz, DMSO-$d_6$) δ −57.99. MS (ES+): 471.1 (M+1); MS(ES−): 469.1 (M−1); Analysis calculated for $C_{25}H_{21}F_3N_2O_4 \cdot 1.25HCl \cdot 1.5H_2O$: C, 55.29; H, 4.69; N, 5.16, Cl, 8.16; Found: C, 55.20; H, 4.71; N, 5.20, Cl, 8.08.

Scheme-380

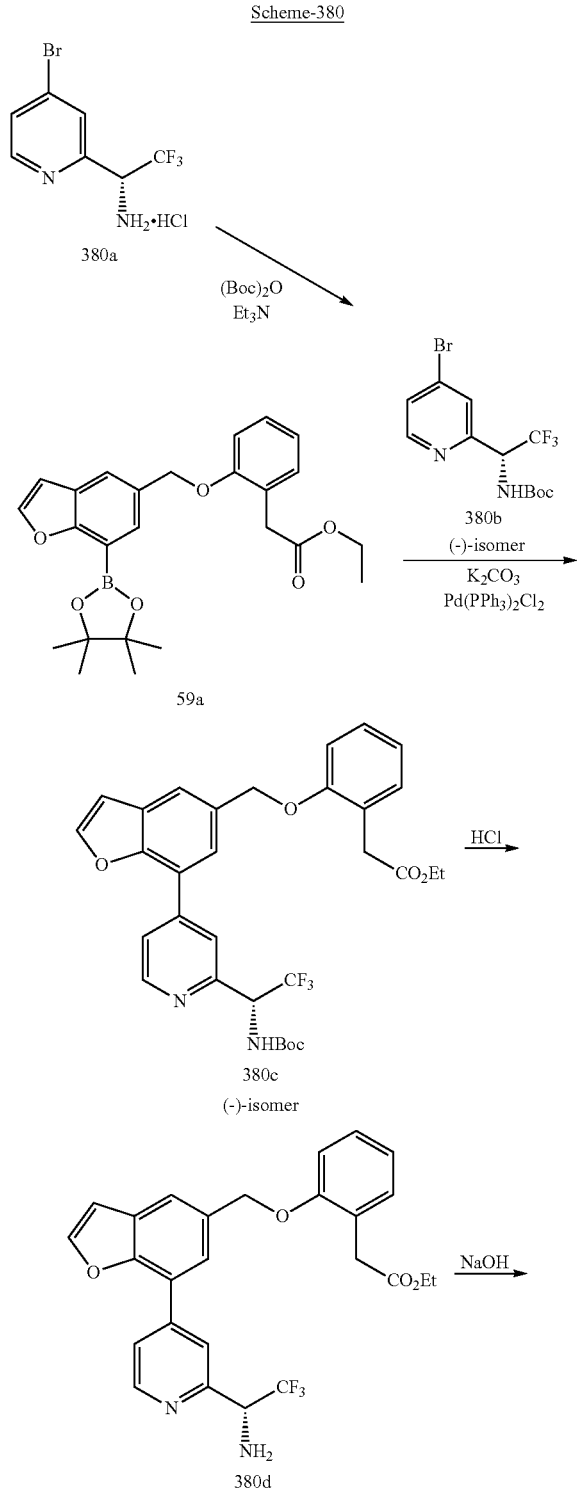

1192

-continued

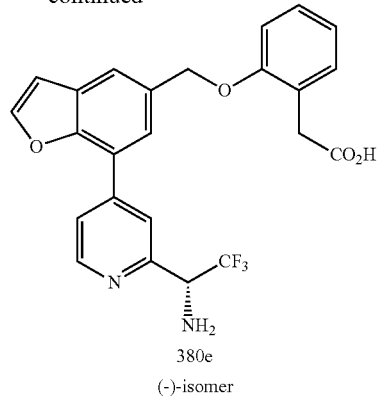

380e
(−)-isomer

Preparation of (R)-2-(2-((7-(2-(1-amino-2,2,2-trifluoroethyl)pyridin-4-yl)benzofuran-5-yl)methoxy)phenyl)acetic Acid (380e)

Step-1: Preparation of (R)-tert-butyl (1-(4-bromopyridin-2-yl)-2,2,2-trifluoroethyl)carbamate (380b)

To a solution of (R)-1-(4-bromopyridin-2-yl)-2,2,2-trifluoroethanamine hydrochloride (380a) (200 mg, 0.686 mmol; CAS #1213120-39-8) in DCM (10 mL) was added Boc anhydride (449 mg, 2.058 mmol), Et$_3$N (208 mg, 2.058 mmol) and stirred at room temperature for 16 h. The reaction was diluted with DCM (20 mL), washed with H$_2$O (2×25 mL), brine (25 mL), dried, filtered and concentrated in vacuum. The residue obtained was purified by flash column chromatography [silica gel, eluting with methanol in DCM from 0-5%] to provide the product (R)-tert-butyl (1-(4-bromopyridin-2-yl)-2,2,2-trifluoroethyl)carbamate (380b) (120 mg, 49% yield) as a yellow oil; $^1H$ NMR (300 MHz, DMSO-$d_6$) δ 8.50 (d, J=5.3 Hz, 1H), 8.23 (d, J=10.0 Hz, 1H), 8.04 (d, J=1.9 Hz, 1H), 7.77 (dd, J=5.3, 1.8 Hz, 1H), 5.53 (p, J=8.7 Hz, 1H), 1.41 (s, 9H); Optical rotation $[α]_D$=−65 (c=0.04, MeOH).

Step-2: Preparation of (R)-ethyl 2-(2-((7-(2-(1-((tert-butoxycarbonyl)amino)-2,2,2-trifluoroethyl)pyridin-4-yl)benzofuran-5-yl)methoxy)phenyl)acetate (380c)

Compound 380c was prepared according to the procedure reported in step-3 of scheme-1 from ethyl 2-(2-((7-(4,4,5,5-tetramethyl-1,3,2-dioxaborolan-2-yl)benzofuran-5-yl)methoxy)phenyl)acetate (59a) (134 mg, 0.307 mmol) in dioxane (4 mL) using (R)-tert-butyl (1-(4-bromopyridin-2-yl)-2,2,2-trifluoroethyl)carbamate (380b) (120 mg, 0.338 mmol), bis(triphenylphosphine)palladium(II) chloride (Pd(PPh$_3$)$_2$Cl$_2$) (22 mg, 0.031 mmol) and a solution of K$_2$CO$_3$ (127 mg, 0.922 mmol) in water (1 mL) under a nitrogen atmosphere heating at 100° C. for 16 h on oil bath. This gave after workup, purification by flash column chromatography [silica gel, eluting with 0-15% EtOAc in hexane] (R)-ethyl 2-(2-((7-(2-(1-((tert-butoxycarbonyl)amino)-2,2,2-trifluoroethyl)pyridin-4-yl)benzofuran-5-yl)methoxy)phenyl)acetate (380c) (97 mg, 54.0% yield) as a pale-green oil; $^1H$ NMR (300 MHz, DMSO-$d_6$) δ 8.76 (d, 1H), 8.35-8.13 (m, 3H), 8.01 (dd, J=5.2, 1.7 Hz, 1H), 7.85 (d, J=1.6 Hz, 1H), 7.76 (d, J=1.6 Hz, 1H), 7.32-7.19 (m, 2H), 7.13 (dd, J=7.3, 1.7 Hz, 2H), 6.92 (td, J=7.4, 1.1 Hz, 1H), 5.60 (t, J=8.9 Hz, 1H), 5.27 (s, 2H), 3.89 (q, J=7.1 Hz, 2H), 3.63 (s, 2H), 1.41 (s, 9H), 0.92 (t, J=7.1 Hz, 3H); MS (ES+): 585 (M+1); Optical rotation $[\alpha]_D$=−40 (c=0.015, MeOH).

Step-3: Preparation of (R)-ethyl 2-(2-((7-(2-(1-amino-2,2,2-trifluoroethyl)pyridin-4-yl)benzofuran-5-yl)methoxy)phenyl)acetate (380d)

Compound 380d was prepared according to the procedure reported in step-3 of scheme-305 from (R)-ethyl 2-(2-((7-(2-(1-((tert-butoxycarbonyl)amino)-2,2,2-trifluoroethyl)pyridin-4-yl)benzofuran-5-yl)methoxy)phenyl)acetate (380c) (97 mg, 0.166 mmol) in methanol (5 mL) using HCl (4 M in dioxane; 0.830 mL, 3.32 mmol) and stirring at 60° C. for 1 h. This gave after workup, (R)-ethyl 2-(2-((7-(2-(1-amino-2,2,2-trifluoroethyl)pyridin-4-yl)benzofuran-5-yl)methoxy)phenyl)acetate (380d) (80 mg) as a pale-yellow oil; MS (ES+): 485 (M+1).

Step-4: Preparation of (R)-2-(2-((7-(2-(1-amino-2,2,2-trifluoroethyl)pyridin-4-yl)benzofuran-5-yl)methoxy)phenyl)acetic Acid (380e)

Compound 380e was prepared according to the procedure reported in step-4 of scheme-4 from (R)-ethyl 2-(2-((7-(2-(1-amino-2,2,2-trifluoroethyl)pyridin-4-yl)benzofuran-5-yl)methoxy)phenyl)acetate (380d) (80 mg, from step-4 above) in MeOH (4 mL), water (1 mL) using 1 N aqueous NaOH (0.498 mL, 0.498 mmol). This gave after workup and purification by reverse phase column (C18, 100 g, 0-60% MeCN in H$_2$O containing 0.1% HCl) (R)-2-(2-((7-(2-(1-amino-2,2,2-trifluoroethyl)pyridin-4-yl)benzofuran-5-yl)methoxy)phenyl)acetic acid (380e) (65 mg, 86% yield) HCl salt as a pale-green solid; $^1$H NMR (300 MHz, DMSO-d$_6$) δ 8.89 (d, J=5.2 Hz, 1H), 8.29 (d, J=1.7 Hz, 1H), 8.19 (d, J=2.2 Hz, 1H), 8.13 (dd, J=5.2, 1.7 Hz, 1H), 7.91 (d, J=1.5 Hz, 1H), 7.83 (d, J=1.6 Hz, 1H), 7.30-7.18 (m, 2H), 7.17-7.07 (m, 2H), 6.92 (t, 1H), 5.84 (q, J=7.6 Hz, 1H), 5.31 (s, 2H), 3.61 (s, 2H); MS (ES+): 457 (M+1), (ES−): 455 (M−1); Analysis calculated for C$_{24}$H$_{19}$F$_3$N$_2$O$_4$.1.15HCl.2H$_2$O: C, 53.94; H, 4.56; Cl, 7.63; N, 5.24; Found: C, 53.97; H, 4.30; Cl, 7.96; N, 5.17; Optical rotation $[t]D$=−2.62 (c=0.305, MeOH).

Scheme-381

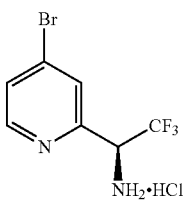
381a

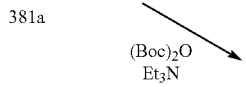

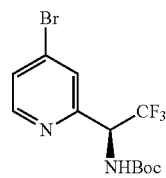
381b
(+)-isomer

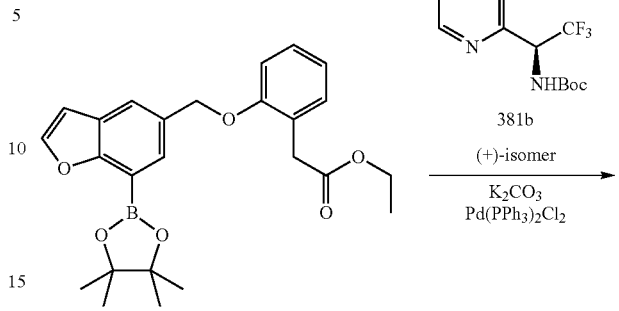
59a

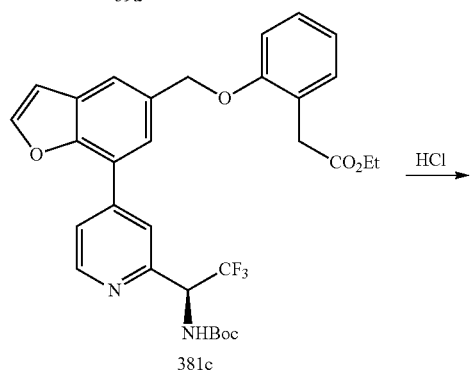
381c

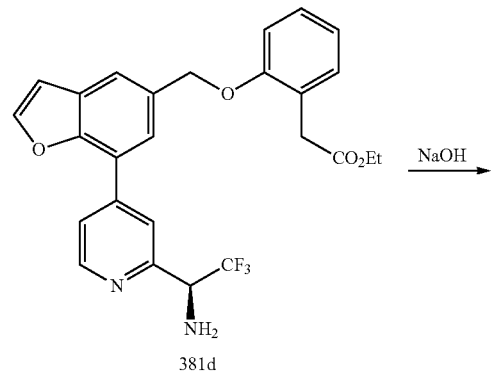
381d

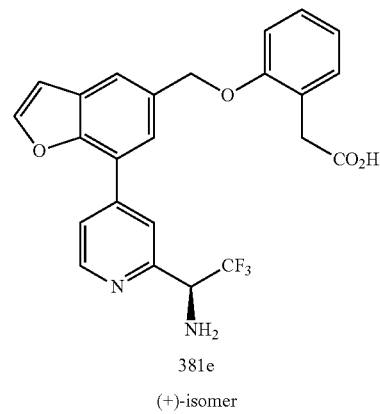
381e
(+)-isomer

Preparation of (S)-2-(2-((7-(2-(1-amino-2,2,2-trifluoroethyl)pyridin-4-yl)benzofuran-5-yl)methoxy)phenyl)acetic Acid (381e)

Step-1: Preparation of (S)-tert-butyl (1-(4-bromopyridin-2-yl)-2,2,2-trifluoroethyl)carbamate (381b)

Compound 381b was prepared according to the procedure reported in step-1 of scheme-380 from (S)-1-(4-bromopyridin-2-yl)-2,2,2-trifluoroethanamine hydrochloride (381a) (200 mg, 0.686 mmol; CAS #1213859-26-7) in DCM (10 mL) using Boc anhydride (449 mg, 2.058 mmol), Et$_3$N (208 mg, 2.058 mmol) and stirring at room temperature for 16 h. This gave after workup, purification by flash column chromatography (Silica gel, 0-5% MeOH in DCM) (S)-tert-butyl (1-(4-bromopyridin-2-yl)-2,2,2-trifluoroethyl)carbamate (381b) (70 mg, 29% yield) as a pale-yellow oil; $^1$H NMR (300 MHz, DMSO-d$_6$) δ 8.50 (d, J=5.3 Hz, 1H), 8.21 (d, J=10.0 Hz, 1H), 8.04 (d, J=1.9 Hz, 1H), 7.77 (dd, J=5.3, 1.9 Hz, 1H), 5.66-5.34 (m, 1H), 1.41 (s, 9H); Optical rotation [t]D=+36 (c=0.05, MeOH).

Step-2: Preparation of (S)-ethyl 2-(2-((7-(2-(1-((tert-butoxycarbonyl)amino)-2,2,2-trifluoroethyl)pyridin-4-yl)benzofuran-5-yl)methoxy)phenyl)acetate (381c)

Compound 381c was prepared according to the procedure reported in step-3 of scheme-1 from ethyl 2-(2-((7-(4,4,5,5-tetramethyl-1,3,2-dioxaborolan-2-yl)benzofuran-5-yl)methoxy)phenyl)acetate (59a) (80 mg, 0.183 mmol) in dioxane (4 mL) using (S)-tert-butyl (1-(4-bromopyridin-2-yl)-2,2,2-trifluoroethyl)carbamate (381b) (72 mg, 0.202 mmol), bis(triphenylphosphine)palladium(II) chloride (Pd(PPh$_3$)$_2$Cl$_2$) (13 mg, 0.018 mmol) and a solution of K$_2$CO$_3$ (76 mg, 0.550 mmol) in water (1 mL) under a nitrogen atmosphere heating at 100° C. for 16 h on oil bath. This gave after workup, purification by flash column chromatography [silica gel, eluting with 0-15% EtOAc in hexane] (S)-ethyl 2-(2-((7-(2-(1-((tert-butoxycarbonyl)amino)-2,2,2-trifluoroethyl)pyridin-4-yl)benzofuran-5-yl)methoxy)phenyl)acetate (381c) as a pale-green thick oil; MS (ES+): 585 (M+1).

Step-3: Preparation of (S)-ethyl 2-(2-((7-(2-(1-amino-2,2,2-trifluoroethyl)pyridin-4-yl)benzofuran-5-yl)methoxy)phenyl)acetate (381d)

Compound 381d was prepared according to the procedure reported in step-3 of scheme-305 from (S)-ethyl 2-(2-((7-(2-(1-((tert-butoxycarbonyl)amino)-2,2,2-trifluoroethyl)pyridin-4-yl)benzofuran-5-yl)methoxy)phenyl)acetate (381c) (from above step-2) in methanol (5 mL) using HCl (4 M in dioxane; 0.458 mL, 1.834 mmol) and stirring at 60° C. for 1 h. This gave after workup, (S)-ethyl 2-(2-((7-(2-(1-amino-2,2,2-trifluoroethyl)pyridin-4-yl)benzofuran-5-yl)methoxy)phenyl)acetate (381d) (20 mg) as a pale-yellow oil; MS (ES+): 485 (M+1).

Step-4: Preparation of (S)-2-(2-((7-(2-(1-amino-2,2,2-trifluoroethyl)pyridin-4-yl)benzofuran-5-yl)methoxy)phenyl)acetic Acid (381e)

Compound 381e was prepared according to the procedure reported in step-4 of scheme-4 from (S)-ethyl 2-(2-((7-(2-(1-amino-2,2,2-trifluoroethyl)pyridin-4-yl)benzofuran-5-yl)methoxy)phenyl)acetate (381d) (20 mg, from step-3 above) in MeOH (4 mL), water (1 mL) using NaOH (22.00 mg, 0.550 mmol). This gave after workup and purification by reverse phase column (C18, 100 g, 0-60% MeCN in H$_2$O containing 0.1% HCl) (S)-2-(2-((7-(2-(1-amino-2,2,2-trifluoroethyl)pyridin-4-yl)benzofuran-5-yl)methoxy)phenyl)acetic acid (381e) (15 mg, 18% yield) HCl salt as a pale-green solid; $^1$H NMR (300 MHz, DMSO-d$_6$) δ 9.64 (s, 3H, D$_2$O exchangeable), 8.89 (d, J=5.2 Hz, 1H), 8.30 (s, 1H), 8.19 (d, J=2.2 Hz, 1H), 8.13 (dd, J=5.2, 1.7 Hz, 1H), 7.90 (d, J=1.6 Hz, 1H), 7.83 (d, J=1.7 Hz, 1H), 7.27-7.20 (m, 2H), 7.15-7.08 (m, 2H), 6.91 (td, J=8.2, 7.7, 1.1 Hz, 2H), 5.94-5.80 (m, 1H), 5.30 (s, 2H), 3.60 (s, 2H); MS (ES+): 457 (M+1), (ES−): 455 (M−1); Optical rotation [t]D=+3.56 (c=0.225, MeOH).

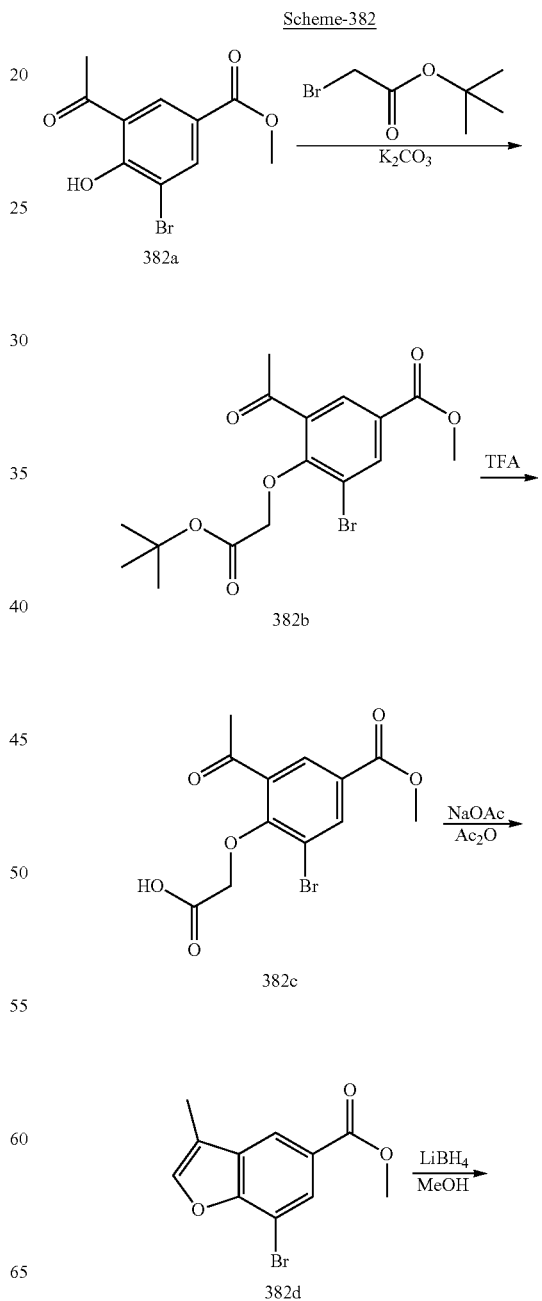

Scheme-382

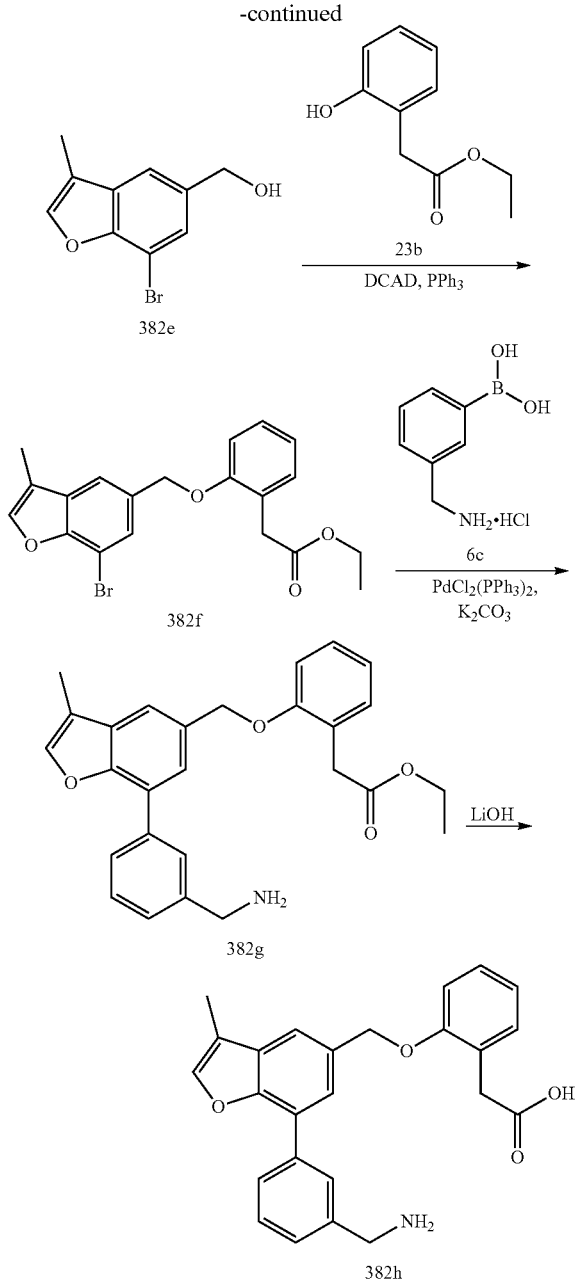

bromo-4-(2-(tert-butoxy)-2-oxoethoxy)benzoate (382b) (1.39 g, 95% yield) as pale yellow oil; $^1$H NMR (300 MHz, DMSO-$d_6$) δ 8.27 (d, J=2.1 Hz, 1H), 8.13 (d, J=2.2 Hz, 1H), 4.68 (s, 2H), 3.88 (s, 3H), 2.63 (s, 3H), 1.43 (s, 9H).

Step-2: Preparation of 2-(2-acetyl-6-bromo-4-(methoxycarbonyl)phenoxy)acetic Acid (382c)

Compound 382c was prepared according to the procedure reported in step-5 of scheme-1 from methyl 3-acetyl-5-bromo-4-(2-(tert-butoxy)-2-oxoethoxy)benzoate (382b) (1.38 g, 3.56 mmol) in DCM (20 mL) using TFA (10.98 mL, 143 mmol). This gave after workup and trituration of residue in hexanes 2-(2-acetyl-6-bromo-4-(methoxycarbonyl)phenoxy)acetic acid (382c) (1.18 g, 100% yield) as a gray solid; $^1$H NMR (300 MHz, DMSO-$d_6$) δ 8.27 (d, J=2.2 Hz, 1H), 8.12 (d, J=2.1 Hz, 1H), 4.72 (s, 2H), 3.88 (s, 3H), 2.63 (s, 3H).

Step-3: Preparation of methyl 7-bromo-3-methylbenzofuran-5-carboxylate (382d)

A mixture of 2-(2-acetyl-6-bromo-4-(methoxycarbonyl)phenoxy)acetic acid (382c) (1.1 g, 3.32 mmol) and anhydrous NaOAc (1.090 g, 13.29 mmol) in Ac$_2$O (25 mL, 265 mmol) was heated at reflux overnight. The reaction mixture was cooled to room temperature, diluted with water and extracted with ethyl acetate. The organic layer was washed with saturated aqueous NaHCO$_3$ solution, brine, dried, filtered and concentrated in vacuo. The residue obtained was purified by flash column chromatography [silica(24 g), eluting with ethyl acetate in hexanes 0-35%] to afford methyl 7-bromo-3-methylbenzofuran-5-carboxylate (382d) (424 mg, 47% yield) as a white solid; $^1$H NMR (300 MHz, DMSO-$d_6$) δ 8.25 (d, J=1.6 Hz, 1H), 8.08 (d, J=1.5 Hz, 1H), 8.04 (d, J=1.4 Hz, 1H), 3.90 (s, 3H), 2.27 (d, J=1.3 Hz, 3H).

Step-4: Preparation of (7-bromo-3-methylbenzofuran-5-yl)methanol (382e)

Compound 382e was prepared according to the procedure reported in step-2 of scheme-76 from methyl 7-bromo-3-methylbenzofuran-5-carboxylate (382d) (420 mg, 1.561 mmol) in THF (15 mL) using LiBH$_4$ (1.8 mL, 7.20 mmol) and MeOH (0.27 mL, 6.67 mmol). This gave after workup (7-bromo-3-methylbenzofuran-5-yl)methanol (382e) (376 mg, 100% yield) as a white solid; $^1$H NMR (300 MHz, DMSO-$d_6$) δ 7.87 (d, J=1.4 Hz, 1H), 7.57-7.52 (m, 1H), 7.49 (dd, J=1.4, 0.6 Hz, 1H), 5.33 (t, J=5.8 Hz, 1H), 4.58 (t, J=5.8, 0.7 Hz, 2H), 2.20 (s, 3H).

Preparation of 2-(2-((7-(3-(aminomethyl)phenyl)-3-methylbenzofuran-5-yl)methoxy)phenyl)acetic Acid (382h)

Step-1: Preparation of methyl 3-acetyl-5-bromo-4-(2-(tert-butoxy)-2-oxoethoxy)benzoate (382b)

A mixture of methyl 3-acetyl-5-bromo-4-hydroxybenzoate (382a) (1.03 g, 3.77 mmol), tert-butyl 2-bromoacetate (1.1 g, 5.64 mmol; CAS #160753-84-4) and K$_2$CO$_3$ (1.26 g, 9.12 mmol) in acetone (30 mL) was heated at reflux overnight. The reaction mixture was cooled to room temperature and solid was removed by filtration. The filtrate was concentrated in vacuum and the residue obtained was purified by flash column chromatography [silica (40g), eluting with EtOAc in hexane from 0-35%] to give methyl 3-acetyl-5-

Step-5: Preparation of Ethyl 2-(2-((7-bromo-3-methylbenzofuran-5-yl)methoxy)phenyl)acetate (382f)

Compound 382f was prepared according to the procedure reported in step-2 of scheme-23 from (7-bromo-3-methylbenzofuran-5-yl)methanol (382e) (370 mg, 1.535 mmol) in DCM (20 mL) using triphenylphosphine (443 mg, 1.688 mmol), ethyl 2-(2-hydroxyphenyl) acetate (23b) (332 mg, 1.842 mmol) and (E)-bis(4-chlorobenzyl) diazene-1,2-dicarboxylate (620 mg, 1.688 mmol) in DCM (5 mL). This gave after workup and purification by flash column chromatography [silica (12 g), eluting with EtOAc in hexane from 0-40%] ethyl 2-(2-((7-bromo-3-methylbenzofuran-5-yl)methoxy)phenyl)acetate (382f) (299 mg, 48% yield) as a white solid; $^1$H NMR (300 MHz, DMSO-$d_6$) δ 7.93 (d, J=1.4

Hz, 1H), 7.69 (d, J=1.5 Hz, 1H), 7.59 (d, J=1.5 Hz, 1H), 7.25 (ddd, J=14.1, 7.3, 1.7 Hz, 2H), 7.12-7.04 (m, 1H), 6.92 (td, J=7.4, 1.1 Hz, 1H), 5.19 (s, 2H), 4.02 (q, J=7.1 Hz, 2H), 3.63 (s, 2H), 2.22 (d, J=1.3 Hz, 3H), 1.07 (t, J=7.1 Hz, 3H).

Step-6: Preparation of Ethyl 2-(2-((7-(3-(aminomethyl)phenyl)-3-methylbenzofuran-5-yl)methoxy)phenyl)acetate (382g)

Compound 382g was prepared according to the procedure reported in step-3 of scheme-1 from ethyl 2-(2-((7-bromo-3-methylbenzofuran-5-yl)methoxy)phenyl)acetate (382f) (157 mg, 0.389 mmol) in dioxane (5 mL) using 3-(aminomethyl)phenylboronic acid hydrochloride (6c) (88 mg, 0.584 mmol), $K_2CO_3$ (161 mg, 1.168 mmol) in water (0.5 mL) and bis(triphenylphosphine)palladium(II)chloride (41 mg, 0.058 mmol) under an Ar atmosphere and heating at 100° C. for 3 h on oil bath. This gave after workup, purification by flash column chromatography [silica (24 g), eluting with DMA80 in DCM from 0-70%] ethyl 2-(2-((7-(3-(aminomethyl)phenyl)-3-methylbenzofuran-5-yl)methoxy)phenyl)acetate (382g) (167 mg, 100% yield) as a dark oil. MS (ES+): 430.2 (M+1).

Step-7: Preparation of 2-(2-((7-(3-(aminomethyl)phenyl)-3-methylbenzofuran-5-yl)methoxy)phenyl) acetic Acid (382h)

Compound 382h was prepared according to the procedure reported in step-6 of scheme-1 from ethyl 2-(2-((7-(3-(aminomethyl)phenyl)-3-methylbenzofuran-5-yl)methoxy)phenyl)acetate (382g) (163 mg, 0.38 mmol) in MeOH/THF (6 mL, each) using a solution of lithium hydroxide hydrate (70 mg, 1.668 mmol) in water (2 mL). This gave after workup and purification by reverse phase column chromatography [C18 (50 g), eluting with ACN in water (containing 0.1% HCl) from 0-100%] 2-(2-((7-(3-(aminomethyl)phenyl)-3-methylbenzofuran-5-yl)methoxy)phenyl)acetic acid (382h) (78 mg, 51% yield) HCl salt as a white solid; $^1$H NMR (300 MHz, DMSO-$d_6$) δ 12.11 (s, 1H), 8.56 (s, 2H), 8.01 (s, 1H), 7.97-7.83 (m, 2H), 7.74 (s, 1H), 7.67 (s, 1H), 7.63-7.49 (m, 2H), 7.34-7.17 (m, 2H), 7.11 (d, J=8.1 Hz, 1H), 6.91 (t, J=7.3 Hz, 1H), 5.28 (s, 2H), 4.13 (s, 2H), 3.62 (s, 2H), 2.27 (s, 3H); MS (ES+): 402.2 (M+1); MS (ES−): 400.2 (M−1); Analysis calculated for $C_{25}H_{23}NO_4 \cdot HCl \cdot H_2O$: C, 65.86; H, 5.75; Cl, 7.78; N, 3.07; Found: C, 66.12; H, 5.75; Cl, 7.61, N, 3.10.

Scheme-383

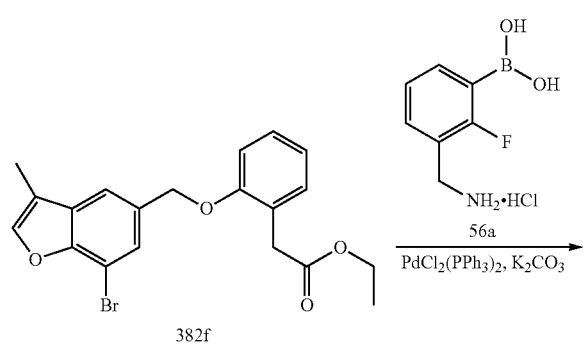

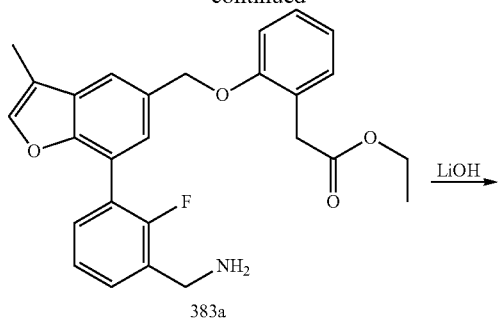

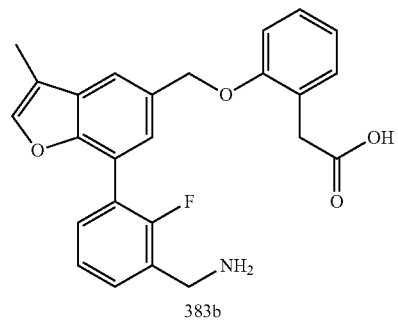

Preparation of 2-(2-((7-(3-(aminomethyl)-2-fluorophenyl)-3-methylbenzofuran-5-yl)methoxy)phenyl) acetic Acid (383b)

Step-1: Preparation of Ethyl 2-(2-((7-(3-(aminomethyl)-2-fluorophenyl)-3-methylbenzofuran-5-yl)methoxy)phenyl)acetate (383a)

Compound 383a was prepared according to the procedure reported in step-3 of scheme-1 from ethyl 2-(2-((7-bromo-3-methylbenzofuran-5-yl)methoxy)phenyl)acetate (382f) (139 mg, 0.345 mmol) in dioxane (5 mL) using 3-(aminomethyl)-2-fluorophenylboronic acid (56a) (106 mg, 0.517 mmol), $K_2CO_3$ (143 mg, 1.034 mmol) in water (0.5 mL) and bis(triphenylphosphine)palladium(II)chloride (36 mg, 0.052 mmol) under an Ar atmosphere and heating at 100° C. for 45 min on oil bath. This gave after workup, purification by flash column chromatography [silica (24 g), eluting with DMA80 in DCM from 0-70%] ethyl 2-(2-((7-(3-(aminomethyl)-2-fluorophenyl)-3-methylbenzofuran-5-yl)methoxy)phenyl)acetate (383a) (154 mg, 100% yield) as a dark oil. MS (ES+): 448.2 (M+1).

Step-2: Preparation of 2-(2-((7-(3-(aminomethyl)-2-fluorophenyl)-3-methylbenzofuran-5-yl)methoxy) phenyl)acetic Acid (383b)

Compound 383b was prepared according to the procedure reported in step-6 of scheme-1 from ethyl 2-(2-((7-(3-(aminomethyl)-2-fluorophenyl)-3-methylbenzofuran-5-yl)methoxy)phenyl)acetate (383a) (154 mg, 0.344 mmol) in MeOH/THF (6 mL, each) using a solution of lithium hydroxide hydrate (79 mg, 1.883 mmol) in water (2 mL). This gave after workup and purification by reverse phase column chromatography [C18 (50 g), eluting with ACN in water (containing 0.1% HCl) from 0-100%] 2-(2-((7-(3-(aminomethyl)-2-fluorophenyl)-3-methylbenzofuran-5-yl)methoxy)phenyl)acetic acid (383b) (85 mg, 59% yield) HCl salt as a white solid; $^1$H NMR (300 MHz, DMSO-$d_6$) δ 8.76

(s, 2H), 7.89-7.77 (m, 2H), 7.73 (t, J=6.9 Hz, 1H), 7.66 (t, J=7.7 Hz, 1H), 7.51-7.35 (m, 2H), 7.30-7.17 (m, 2H), 7.10 (d, J=8.0 Hz, 1H), 6.91 (t, J=7.3 Hz, 1H), 5.27 (s, 2H), 4.16 (s, 2H), 3.60 (s, 2H), 2.26 (s, 3H); $^{19}$F NMR (282 MHz, DMSO-d$_6$) δ–118.51; MS (ES+): 420.1 (M+1); MS (ES–): 418.1 (M–1); Analysis calculated for C$_{25}$H$_{22}$FNO$_4$·HCl·H$_2$O: C, 63.36; H, 5.32; Cl, 7.48; N, 2.96; Found: C, 63.51; H, 5.38; Cl, 7.79, N, 3.28.

Scheme-384

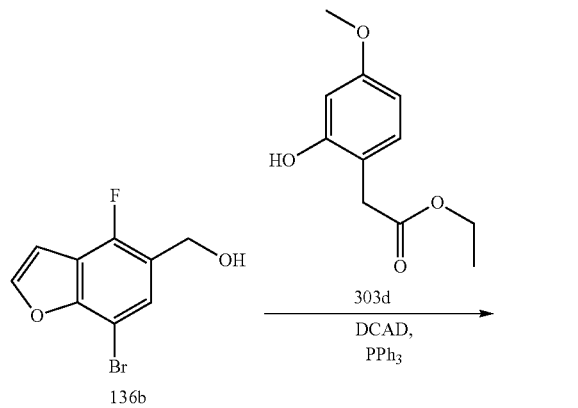

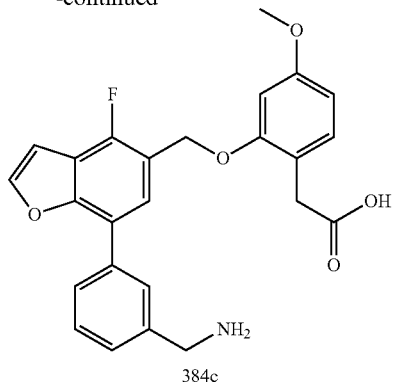

Preparation of 2-(2-((7-(3-(aminomethyl)phenyl)-4-fluorobenzofuran-5-yl)methoxy)-4-methoxyphenyl)acetic Acid (384c)

Step-1: Preparation of Ethyl 2-(2-((7-bromo-4-fluorobenzofuran-5-yl)methoxy)-4-methoxyphenyl)acetate (384a)

Compound 384a was prepared according to the procedure reported in step-2 of scheme-23 from (7-bromo-4-fluorobenzofuran-5-yl)methanol (136b) (594 mg, 2.424 mmol) in DCM (75 mL) using triphenylphosphine (699 mg, 2.67 mmol), ethyl 2-(2-hydroxy-4-methoxyphenyl)acetate (303d) (612 mg, 2.91 mmol) and (E)-bis(4-chlorobenzyl)diazene-1,2-dicarboxylate (DCAD, 979 mg, 2.67 mmol) in DCM (20 mL). This gave after workup and purification by flash column chromatography [silica (24 g), eluting with EtOAc in hexane from 0-50%] ethyl 2-(2-((7-bromo-4-fluorobenzofuran-5-yl)methoxy)-4-methoxyphenyl)acetate (384a) (703 mg, 66% yield) as a white solid. $^1$H NMR (300 MHz, DMSO-d$_6$) δ 8.22 (d, J=2.2 Hz, 1H), 7.70 (d, J=6.1 Hz, 1H), 7.28 (d, J=2.3 Hz, 1H), 7.11 (d, J=8.3 Hz, 1H), 6.74 (d, J=2.4 Hz, 1H), 6.51 (dd, J=8.3, 2.4 Hz, 1H), 5.20 (d, J=1.4 Hz, 2H), 3.95 (q, J=7.1 Hz, 2H), 3.76 (s, 3H), 3.48 (s, 2H), 1.01 (t, J=7.1 Hz, 3H); $^{19}$F NMR (282 MHz, DMSO-d$_6$) δ–124.53.

Step-2: Preparation of Ethyl 2-(2-((7-(3-(aminomethyl)phenyl)-4-fluorobenzofuran-5-yl)methoxy)-4-methoxyphenyl)acetate (384b)

Compound 384b was prepared according to the procedure reported in step-3 of scheme-1 from ethyl 2-(2-((7-bromo-4-fluorobenzofuran-5-yl)methoxy)-4-methoxyphenyl)acetate (384a) (150 mg, 0.343 mmol) in dioxane (5 mL) using 3-(aminomethyl)phenylboronic acid hydrochloride (6c) (78 mg, 0.515 mmol), K$_2$CO$_3$ (142 mg, 1.029 mmol) in water (0.5 mL) and bis(triphenylphosphine)palladium(II)chloride (36 mg, 0.051 mmol) under an Ar atmosphere and heating at 100° C. for 3 h on oil bath. This gave after workup, purification by flash column chromatography [silica (12 g), eluting with DMA80 in DCM from 0-70%] ethyl 2-(2-((7-(3-(aminomethyl)phenyl)-4-fluorobenzofuran-5-yl)methoxy)-4-methoxyphenyl)acetate (384b) (109 mg, 69% yield) as a colorless oil. $^1$H NMR (300 MHz, DMSO-d$_6$) δ 8.17 (d, J=2.2 Hz, 1H), 7.82-7.75 (m, 1H), 7.72-7.62 (m, 2H), 7.46 (t, J=7.5 Hz, 1H), 7.42-7.36 (m, 1H), 7.21 (d, J=2.3 Hz, 1H), 7.10 (d, J=8.3 Hz, 1H), 6.77 (d, J=2.4 Hz, 1H), 6.50 (dd, J=8.3, 2.4 Hz, 1H), 5.26 (s, 2H), 3.86 (q, J=7.1 Hz, 2H), 3.81 (s, 2H), 3.76 (s, 3H), 3.48 (s, 2H), 0.91 (t, J=7.1 Hz, 3H); $^{19}$F NMR (282 MHz, DMSO-$d_6$) δ −125.43. MS (ES+): 464.2 (M+1).

Step-3: Preparation of 2-(2-((7-(3-(aminomethyl)phenyl)-4-fluorobenzofuran-5-yl)methoxy)-4-methoxyphenyl)acetic Acid (384c)

Compound 384c was prepared according to the procedure reported in step-6 of scheme-1 from ethyl 2-(2-((7-(3-(aminomethyl)phenyl)-4-fluorobenzofuran-5-yl)methoxy)-4-methoxyphenyl)acetate (384b) (105 mg, 0.227 mmol) in MeOH/THF (6 mL, each) using a solution of lithium hydroxide hydrate (38 mg, 0.906 mmol) in water (2 mL). This gave after workup and purification by reverse phase column chromatography [C18 (50 g), eluting with ACN in water (containing 0.1% HCl) from 0-100%] 2-(2-((7-(3-(aminomethyl)phenyl)-4-fluorobenzofuran-5-yl)methoxy)-4-methoxyphenyl)acetic acid (384c) (79 mg, 80% yield) HCl salt as a white solid; $^1$H NMR (300 MHz, DMSO-$d_6$) δ 12.04 (s, 1H), 8.91-8.18 (m, 3H), 8.18-8.01 (m, 1H), 7.91 (s, 1H), 7.82 (t, J=4.6 Hz, 1H), 7.68 (d, J=6.7 Hz, 1H), 7.51 (d, J=4.6 Hz, 2H), 7.23-7.10 (m, 1H), 7.04 (d, J=8.3 Hz, 1H), 6.68 (s, 1H), 6.52-6.34 (m, 1H), 5.22 (s, 2H), 4.05 (s, 2H), 3.69 (s, 3H), 3.39 (s, 2H); $^{19}$F NMR (282 MHz, DMSO) δ −124.69; MS (ES+): 436.1 (M+1); MS (ES−): 434.2 (M−1); Analysis calculated for $C_{25}H_{22}FNO_5 \cdot HCl \cdot 0.25H_2O$: C, 63.03; H, 4.97; Cl, 7.44; N, 2.94; Found: C, 63.25; H, 4.82; Cl, 7.19; N, 2.92.

Scheme-385

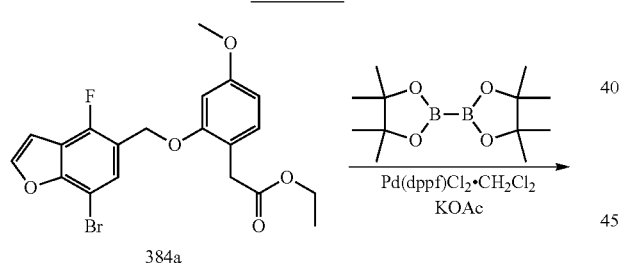

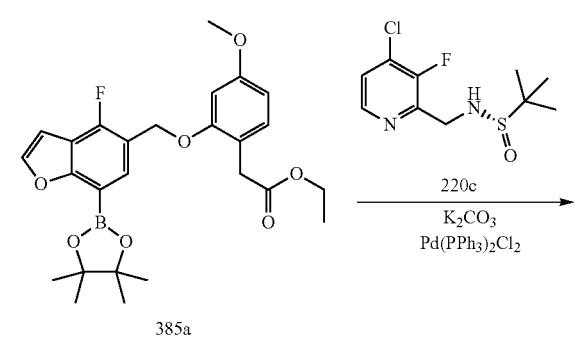

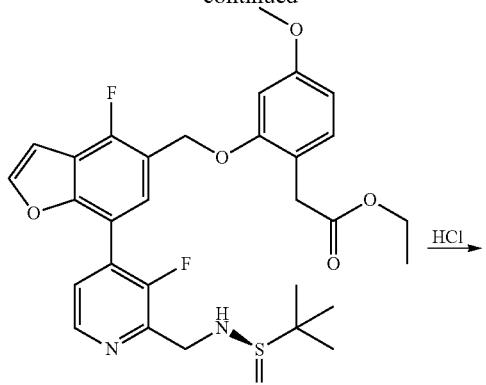

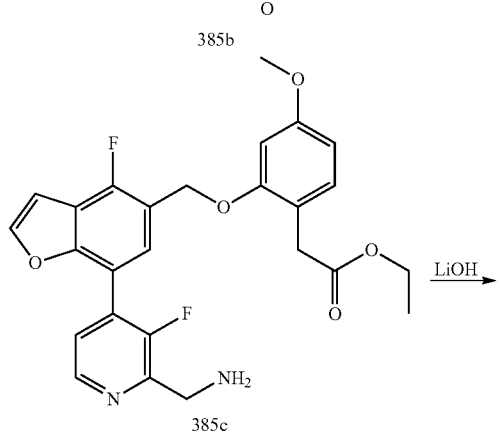

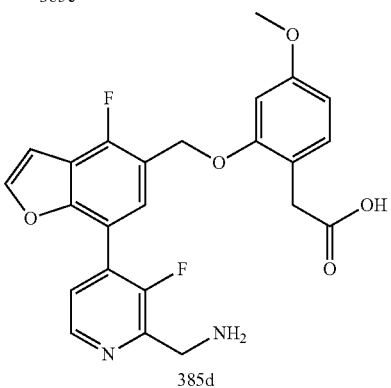

Preparation of 2-(2-((7-(2-(aminomethyl)-3-fluoropyridin-4-yl)-4-fluorobenzofuran-5-yl)methoxy)-4-methoxyphenyl)acetic Acid (385d)

Step-1: Preparation of Ethyl 2-(2-((4-fluoro-7-(4,4,5,5-tetramethyl-1,3,2-dioxaborolan-2-yl)benzofuran-5-yl)methoxy)-4-methoxyphenyl)acetate (385a)

Compound 385a was prepared according to the procedure reported in step-1 of scheme-59 from ethyl 2-(2-((7-bromo-4-fluorobenzofuran-5-yl)methoxy)-4-methoxyphenyl)acetate (384a) (250 mg, 0.572 mmol), using bis(pinacolato)diboron (218 mg, 0.858 mmol), potassium acetate (168 mg, 1.715 mmol) and Pd(dppf)Cl$_2$—CH$_2$Cl$_2$ (70 mg, 0.086 mmol) in anhydrous dioxane (6 mL) under an argon atmosphere and heating at 95° C. overnight. This gave after workup and purification by flash column chromatography [silica gel (24 g), eluting with EtOAc in hexane from 0-40%]

ethyl 2-(2-((4-fluoro-7-(4,4,5,5-tetramethyl-1,3,2-dioxaborolan-2-yl)benzofuran-5-yl)methoxy)-4-methoxyphenyl)acetate (385a) (189 mg, 68% yield) as a colorless oil; $^1$H NMR (300 MHz, DMSO-$d_6$) δ 8.14 (d, J=2.3 Hz, 1H), 7.75 (d, J=7.8 Hz, 1H), 7.13 (d, J=2.3 Hz, 1H), 7.08 (d, J=8.3 Hz, 1H), 6.77 (d, J=2.4 Hz, 1H), 6.49 (dd, J=8.3, 2.4 Hz, 1H), 5.19 (s, 2H), 3.92 (q, J=7.1 Hz, 2H), 3.77 (s, 3H), 3.42 (s, 2H), 1.33 (s, 12H), 0.97 (t, J=7.1 Hz, 3H); $^{19}$F NMR (282 MHz, DMSO-$d_6$) δ−118.86.

Step-2: Preparation of Ethyl 2-(2-((7-(2-(((1,1-dimethylethylsulfinamido)methyl)-3-fluoropyridin-4-yl)-4-fluorobenzofuran-5-yl)methoxy)-4-methoxyphenyl)acetate (385b)

Compound 385b was prepared according to the procedure reported in step-3 of scheme-1 from ethyl 2-(2-((4-fluoro-7-(4,4,5,5-tetramethyl-1,3,2-dioxaborolan-2-yl)benzofuran-5-yl)methoxy)-4-methoxyphenyl)acetate (385a) (185 mg, 0.382 mmol) in dioxane (5 mL) using (+)-(S)—N-((4-chloro-3-fluoropyridin-2-yl)methyl)-2-methylpropane-2-sulfinamide (220c) (121 mg, 0.458 mmol), bis(triphenylphosphine)palladium(II) chloride (Pd(PPh$_3$)$_2$Cl$_2$) (40 mg, 0.057 mmol) and a solution of K$_2$CO$_3$ (158 mg, 1.146 mmol) in water (0.5 mL) under an argon atmosphere heating at 100° C. for 3 h on oil bath. This gave after workup and purification by flash column chromatography [silica gel (12 g), eluting with MeOH in DCM from 0-15%] ethyl 2-(2-((7-(2-(((1,1-dimethylethylsulfinamido)methyl)-3-fluoropyridin-4-yl)-4-fluorobenzofuran-5-yl)methoxy)-4-methoxyphenyl)acetate (385b) (224 mg, 100% yield) as a pale-yellow oil. MS (ES+): 587.2 (M+1).

Step-3: Preparation of Ethyl 2-(2-((7-(2-(aminomethyl)-3-fluoropyridin-4-yl)-4-fluorobenzofuran-5-yl)methoxy)-4-methoxyphenyl)acetate (385c)

Compound 385c was prepared according to the procedure reported in step-3 of scheme-305 from ethyl 2-(2-((7-(2-(((1,1-dimethylethylsulfinamido)methyl)-3-fluoropyridin-4-yl)-4-fluorobenzofuran-5-yl)methoxy)-4-methoxyphenyl)acetate (385b) (224 mg, 0.382 mmol) in MeOH (8 mL) using HCl (4 M in dioxane; 0.5 mL, 2.0 mmol) and stirring at room temperature for 1.5 h. This gave after workup and purification by flash column chromatography [silica (12 g), eluting with DMA80/DCM from 0-70%] ethyl 2-(2-((7-(2-(aminomethyl)-3-fluoropyridin-4-yl)-4-fluorobenzofuran-5-yl)methoxy)-4-methoxyphenyl)acetate (385c) (79 mg, 43% yield) as a pale-yellow oil. MS (ES+): 483.1 (M+1).

Step-4: Preparation of 2-(2-((7-(2-(aminomethyl)-3-fluoropyridin-4-yl)-4-fluorobenzofuran-5-yl)methoxy)-4-methoxyphenyl)acetic Acid (385d)

Compound 385d was prepared according to the procedure reported in step-6 of scheme-1 from ethyl 2-(2-((7-(2-(aminomethyl)-3-fluoropyridin-4-yl)-4-fluorobenzofuran-5-yl)methoxy)-4-methoxyphenyl)acetate (385c) (75 mg, 0.155 mmol) in MeOH/THF (6 mL each), using lithium hydroxide hydrate (50 mg, 1.192 mmol) in water (2 mL). This gave after workup and purification by reverse phase column [C18 (50 g), eluting with water in acetonitrile from 0-100%] 2-(2-((7-(2-(aminomethyl)-3-fluoropyridin-4-yl)-4-fluorobenzofuran-5-yl)methoxy)-4-methoxyphenyl)acetic acid (385d) (42 mg, 60% yield) HCl salt as a white solid; $^1$H NMR (300 MHz, DMSO-$d_6$) δ 12.00 (s, 1H), 8.63 (d, J=5.5 Hz, 4H), 8.20 (d, J=2.3 Hz, 1H), 7.79 (t, J=5.3 Hz, 1H), 7.74 (d, J=6.6 Hz, 1H), 7.27 (d, J=2.3 Hz, 1H), 7.11 (d, J=8.3 Hz, 1H), 6.76 (d, J=2.4 Hz, 1H), 6.51 (dd, J=8.3, 2.4 Hz, 1H), 5.31 (s, 2H), 4.36 (d, J=5.5 Hz, 2H), 3.76 (s, 3H), 3.45 (s, 2H); $^{19}$F NMR (282 MHz, DMSO-$d_6$) δ−121.26, −128.47. MS (ES+): 455.1 (M+1); MS(ES−): 453.1 (M−1); Analysis calculated for C$_{24}$H$_{20}$F$_2$N$_2$O$_5$.HCl.2.5H$_2$O: C, 53.79; H, 4.89; Cl, 6.62; N, 5.23; Found: C, 53.73; H, 4.77; Cl, 6.83; N, 5.37.

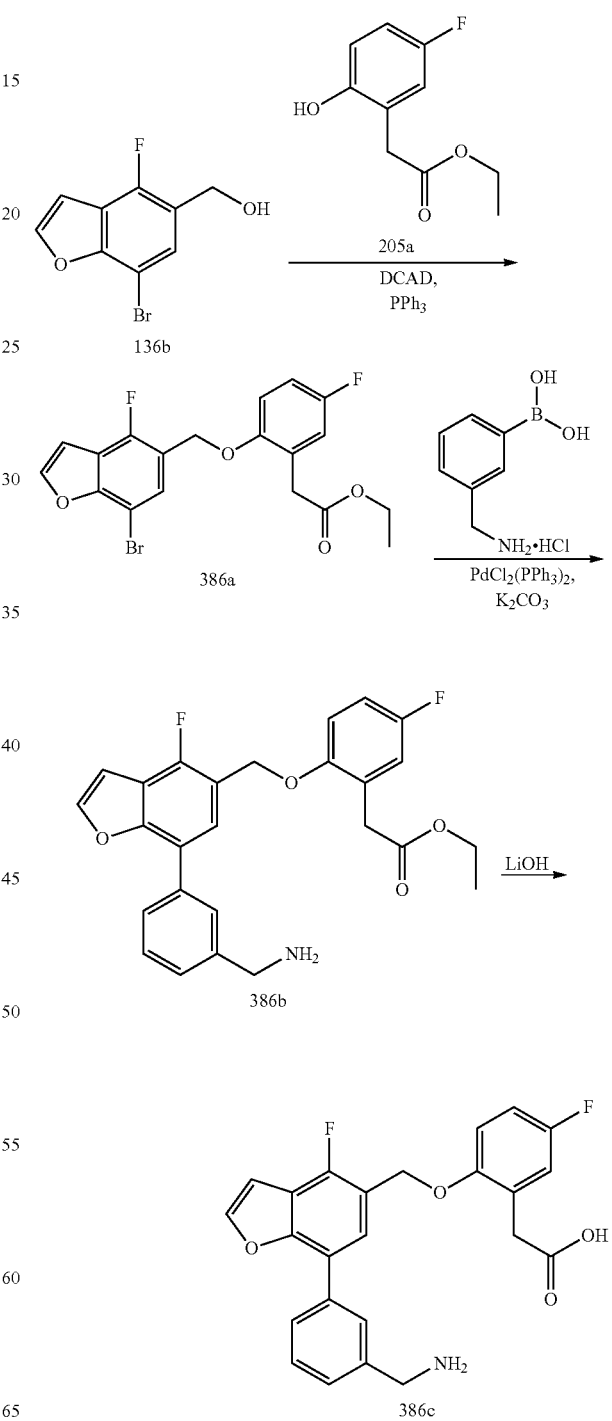

Scheme-386

Preparation of 2-(2-((7-(3-(aminomethyl)phenyl)-4-fluorobenzofuran-5-yl)methoxy)-5-fluorophenyl)acetic Acid (386c)

Step-1: Preparation of Ethyl 2-(2-((7-bromo-4-fluorobenzofuran-5-yl)methoxy)-5-fluorophenyl)acetate (386a)

Compound 386a was prepared according to the procedure reported in step-2 of scheme-23 from (7-bromo-4-fluorobenzofuran-5-yl)methanol (136b) (0.98 g, 4.00 mmol) in DCM (35 mL) using triphenylphosphine (1.154 g, 4.40 mmol), ethyl 2-(5-fluoro-2-hydroxyphenyl)acetate (205a) (0.951 g, 4.80 mmol) and (E)-bis(4-chlorobenzyl) diazene-1,2-dicarboxylate (DCAD, 1.615 g, 4.40 mmol) in DCM (15 mL). This gave after workup and purification by flash column chromatography [silica (40 g), eluting with EtOAc in hexane from 0-50%] ethyl 2-(2-((7-bromo-4-fluorobenzofuran-5-yl)methoxy)-5-fluorophenyl)acetate (386a) (1.65 g, 97% yield) as a white solid. $^1$H NMR (300 MHz, DMSO-$d_6$) δ 8.23 (d, J=2.3 Hz, 1H), 7.70 (d, J=6.2 Hz, 1H), 7.28 (d, J=2.3 Hz, 1H), 7.21-7.07 (m, 3H), 5.19 (s, 2H), 3.97 (q, J=7.1 Hz, 2H), 3.59 (s, 2H), 1.02 (t, J=7.1 Hz, 3H); $^{19}$F NMR (282 MHz, DMSO-$d_6$) δ −123.58, −124.55.

Step-2: Preparation of Ethyl 2-(2-((7-(3-(aminomethyl)phenyl)-4-fluorobenzofuran-5-yl)methoxy)-5-fluorophenyl)acetate (386b)

Compound 386b was prepared according to the procedure reported in step-3 of scheme-1 from ethyl 2-(2-((7-bromo-4-fluorobenzofuran-5-yl)methoxy)-5-fluorophenyl)acetate (386a) (150 mg, 0.353 mmol) in dioxane (5 mL) using 3-(aminomethyl)phenylboronic acid hydrochloride (6c) (80 mg, 0.529 mmol), $K_2CO_3$ (146 mg, 1.058 mmol) in water (0.5 mL) and bis(triphenylphosphine)palladium(II)chloride (37 mg, 0.053 mmol) under an Ar atmosphere and heating at 100° C. for 3 h on oil bath. This gave after workup, purification by flash column chromatography [silica (12 g), eluting with DMA80 in DCM from 0-70%] ethyl 2-(2-((7-(3-(aminomethyl)phenyl)-4-fluorobenzofuran-5-yl)methoxy)-5-fluorophenyl)acetate (386b) (127 mg, 80% yield) as a colorless oil; $^1$H NMR (300 MHz, DMSO-$d_6$) δ 8.17 (d, J=2.2 Hz, 1H), 7.78 (d, J=1.7 Hz, 1H), 7.67 (ddd, J=6.7, 3.9, 2.1 Hz, 2H), 7.46 (t, J=7.5 Hz, 1H), 7.42-7.36 (m, 1H), 7.22-7.17 (m, 2H), 7.12 (dd, J=8.8, 2.3 Hz, 2H), 5.25 (d, J=1.3 Hz, 2H), 3.87 (q, J=7.1 Hz, 2H), 3.80 (s, 2H), 3.59 (s, 2H), 0.92 (t, J=7.1 Hz, 3H); $^{19}$F NMR (282 MHz, DMSO-$d_6$) δ −123.74, −125.46. MS (ES+): 452.1 (M+1).

Step-3: Preparation of 2-(2-((7-(3-(aminomethyl)phenyl)-4-fluorobenzofuran-5-yl)methoxy)-5-fluorophenyl)acetic Acid (386c)

Compound 386c was prepared according to the procedure reported in step-6 of scheme-1 from ethyl 2-(2-((7-(3-(aminomethyl)phenyl)-4-fluorobenzofuran-5-yl)methoxy)-5-fluorophenyl)acetate (386b) (123 mg, 0.272 mmol) in MeOH/THF (6 mL, each) using a solution of lithium hydroxide hydrate (60 mg, 1.430 mmol) in water (2 mL). This gave after workup and purification by reverse phase column chromatography [C18 (50 g), eluting with ACN in water (containing 0.1% HCl) from 0-100%] 2-(2-((7-(3-(aminomethyl)phenyl)-4-fluorobenzofuran-5-yl)methoxy)-5-fluorophenyl)acetic acid (386c) (103 mg, 89% yield) HCl salt as a white solid. $^1$H NMR (300 MHz, DMSO-$d_6$) δ 12.19 (s, 1H), 8.46 (s, 2H), 8.11 (d, J=2.3 Hz, 1H), 7.91 (s, 1H), 7.82 (dq, J=7.3, 3.0, 2.1 Hz, 1H), 7.67 (d, J=6.8 Hz, 1H), 7.57-7.44 (m, 2H), 7.20-7.08 (m, 2H), 7.08-6.96 (m, 2H), 5.21 (s, 2H), 4.05 (s, 2H), 3.50 (s, 2H); $^{19}$F NMR (282 MHz, DMSO-$d_6$) δ −123.66, −124.66; MS (ES+): 424.1 (M+1); MS (ES−): 422.1 (M−1); Analysis calculated for $C_{24}H_{19}F_2NO_4·HCl·H_2O$: C, 60.32; H, 4.64; Cl, 7.42; N, 2.93; Found: C, 60.08; H, 4.80; Cl, 7.32; N, 2.96.

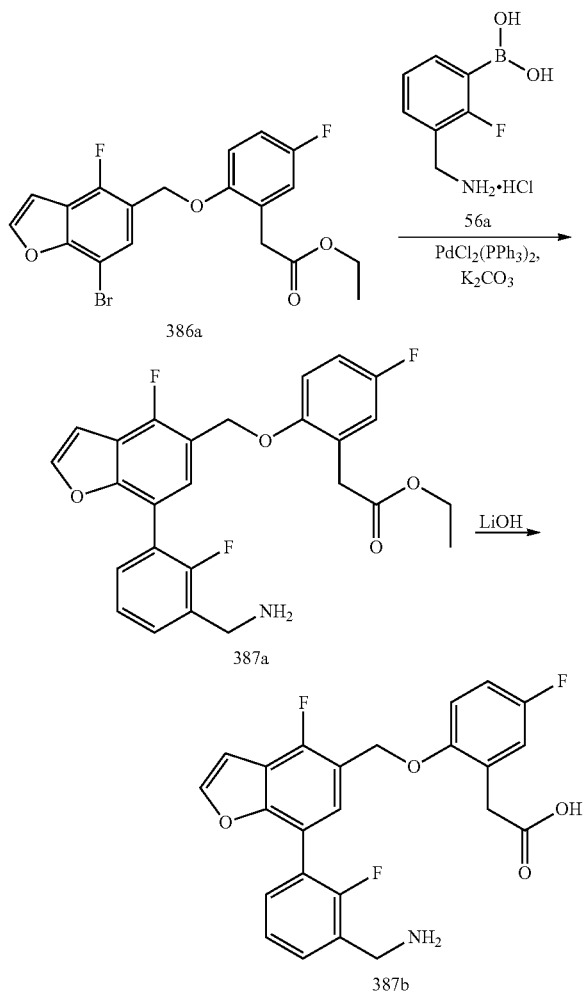

Scheme-387

Preparation of 2-(2-((7-(3-(aminomethyl)-2-fluorophenyl)-4-fluorobenzofuran-5-yl)methoxy)-5-fluorophenyl)acetic Acid (387b)

Step-1: Preparation of Ethyl 2-(2-((7-(3-(aminomethyl)-2-fluorophenyl)-4-fluorobenzofuran-5-yl)methoxy)-5-fluorophenyl)acetate (387a)

Compound 387a was prepared according to the procedure reported in step-3 of scheme-1 from ethyl 2-(2-((7-bromo-4-fluorobenzofuran-5-yl)methoxy)-5-fluorophenyl)acetate (386a) (156 mg, 0.367 mmol) in dioxane (5 mL) using (3-(aminomethyl)-2-fluorophenyl)boronic acid hydrochloride (56a) (93 mg, 0.550 mmol), $K_2CO_3$ (152 mg, 1.101 mmol) in water (0.5 mL) and bis(triphenylphosphine)palladium(II) chloride (39 mg, 0.055 mmol) under an Ar atmosphere and heating at 100° C. for 3 h on oil bath. This gave after workup, purification by flash column chromatography [silica (12 g), eluting with DMA80 in DCM from 0-70%] ethyl 2-(2-((7-(3-(aminomethyl)-2-fluorophenyl)-4-fluorobenzofuran-5-yl)methoxy)-5-fluorophenyl)acetate (387a) (153 mg, 89% yield) as a colorless oil; MS (ES+): 470.1 (M+1).

Step-2: Preparation of 2-(2-((7-(3-(aminomethyl)-2-fluorophenyl)-4-fluorobenzofuran-5-yl)methoxy)-5-fluorophenyl)acetic Acid (387b)

Compound 387b was prepared according to the procedure reported in step-6 of scheme-1 from ethyl 2-(2-((7-(3-(aminomethyl)-2-fluorophenyl)-4-fluorobenzofuran-5-yl)methoxy)-5-fluorophenyl)acetate (387a) (153 mg, 0.326 mmol) in MeOH/THF (6 mL, each) using a solution of lithium hydroxide hydrate (61 mg, 1.454 mmol) in water (2 mL). This gave after workup and purification by reverse phase column chromatography [C18 (50 g), eluting with ACN in water (containing 0.1% HCl) from 0-100%] 2-(2-((7-(3-(aminomethyl)-2-fluorophenyl)-4-fluorobenzofuran-5-yl)methoxy)-5-fluorophenyl)acetic acid (387b) (57 mg, 40% yield) HCl salt as a white solid; $^1$H NMR (300 MHz, DMSO-$d_6$) δ 12.09 (s, 1H), 8.84 (s, 2H), 8.06 (d, J=2.3 Hz, 1H), 7.70-7.54 (m, 2H), 7.50 (d, J=6.7 Hz, 1H), 7.35 (t, J=7.7 Hz, 1H), 7.15 (d, J=2.3 Hz, 1H), 7.13-7.08 (m, 1H), 7.08-6.97 (m, 2H), 5.20 (s, 2H), 4.10 (s, 2H), 3.48 (s, 2H); $^{19}$F NMR (282 MHz, DMSO) δ−118.49, −123.53, −123.60; MS(ES+): 442.1 (M+1), MS(ES−): 440.1 (M−1); Analysis calculated for $C_{24}H_{18}F_3NO_4 \cdot HCl \cdot 0.75H_2O$: C, 58.66; H, 4.21; Cl, 7.22; N, 2.85; Found: C, 58.74; H, 4.24; Cl, 7.38; N, 2.97.

Scheme-388

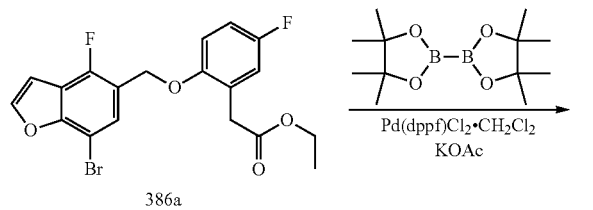

386a

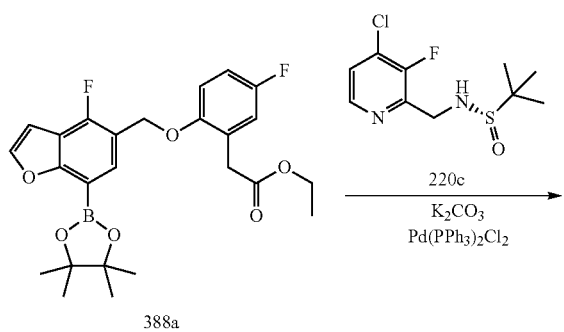

388a

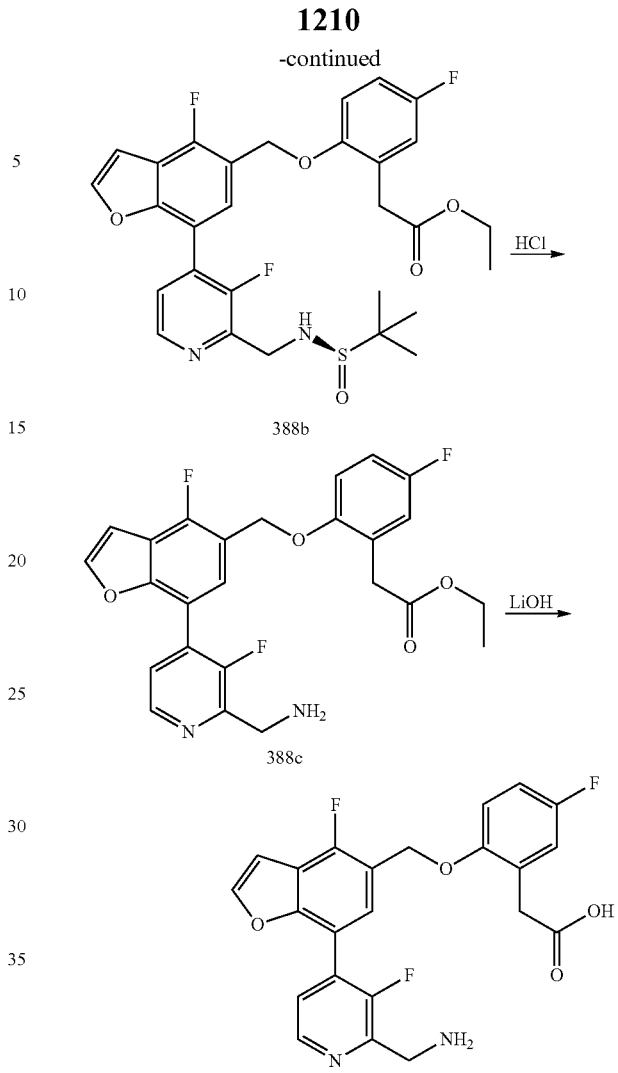

Preparation of 2-(2-((7-(2-(aminomethyl)-3-fluoropyridin-4-yl)-4-fluorobenzofuran-5-yl)methoxy)-5-fluorophenyl)acetic Acid (388d)

Step-1: Preparation of Ethyl 2-(5-fluoro-2-((4-fluoro-7-(4,4,5,5-tetramethyl-1,3,2-dioxaborolan-2-yl)benzofuran-5-yl)methoxy)phenyl)acetate (388a)

Compound 388a was prepared according to the procedure reported in step-1 of scheme-59 from ethyl 2-(2-((7-bromo-4-fluorobenzofuran-5-yl)methoxy)-5-fluorophenyl)acetate (386a) (630 mg, 1.482 mmol), using bis(pinacolato)diboron (564 mg, 2.222 mmol), potassium acetate (436 mg, 4.44 mmol) and Pd(dppf)Cl$_2$—CH$_2$Cl$_2$ (181 mg, 0.222 mmol) in anhydrous dioxane (12 mL) under an argon atmosphere and heating at 95° C. overnight. This gave after workup and purification by flash column chromatography [silica gel (24 g), eluting with EtOAc in hexane from 0-40%] ethyl 2-(5-fluoro-2-((4-fluoro-7-(4,4,5,5-tetramethyl-1,3,2-dioxaborolan-2-yl)benzofuran-5-yl)methoxy)phenyl)acetate (388a) (596 mg, 85% yield) as a white solid. $^1$H NMR (300 MHz, DMSO-$d_6$) δ 8.14 (d, J=2.3 Hz, 1H), 7.73 (d, J=7.8 Hz, 1H), 7.19 (dd, J=9.8, 4.8 Hz, 1H), 7.11 (qd, J=4.2, 3.8, 1.7 Hz, 3H), 5.17 (d, J=1.2 Hz, 2H), 3.95 (q, 2H), 3.53 (s, 2H), 1.33 (s, 12H), 0.98 (t, J=7.1 Hz, 3H); $^{19}$F NMR (282 MHz, DMSO) δ −118.98, −123.68.

Step-2: Preparation of Ethyl 2-(2-((7-(2-((1,1-dimethylethylsulfinamido)methyl)-3-fluoropyridin-4-yl)-4-fluorobenzofuran-5-yl)methoxy)-5-fluorophenyl)acetate (388b)

Compound 388b was prepared according to the procedure reported in step-3 of scheme-1 from ethyl 2-(5-fluoro-2-((4-fluoro-7-(4,4,5,5-tetramethyl-1,3,2-dioxaborolan-2-yl)benzofuran-5-yl)methoxy)phenyl)acetate (388a) (252 mg, 0.534 mmol) in dioxane (5 mL) using (+)-(S)—N-((4-chloro-3-fluoropyridin-2-yl)methyl)-2-methylpropane-2-sulfinamide (220c) (184 mg, 0.694 mmol), bis(triphenylphosphine)palladium(II) chloride (Pd(PPh$_3$)$_2$Cl$_2$) (40 mg, 0.057 mmol) and a solution of K$_2$CO$_3$ (221 mg, 1.601 mmol) in water (0.5 mL) under an argon atmosphere heating at 100° C. for 3 h on oil bath. This gave after workup and purification by flash column chromatography [silica gel (12 g), eluting with MeOH in DCM from 0-15%] ethyl 2-(2-((7-(2-((1,1-dimethylethylsulfinamido)methyl)-3-fluoropyridin-4-yl)-4-fluorobenzofuran-5-yl)methoxy)-5-fluorophenyl)acetate (388b) (307 mg, 100% yield) as a dark oil, used in the next step without further purification. MS (ES+): 575.2 (M+1).

Step-3: Preparation of Ethyl 2-(2-((7-(2-(aminomethyl)-3-fluoropyridin-4-yl)-4-fluorobenzofuran-5-yl)methoxy)-5-fluorophenyl)acetate (388c)

Compound 388c was prepared according to the procedure reported in step-3 of scheme-305 from ethyl 2-(2-((7-(2-((1,1-dimethylethylsulfinamido)methyl)-3-fluoropyridin-4-yl)-4-fluorobenzofuran-5-yl)methoxy)-5-fluorophenyl)acetate (388b) (307 mg, 0.534 mmol) in MeOH (8 mL) using HCl (4 M in dioxane; 0.6 mL, 2.40 mmol) and stirring at room temperature for 1 h. This gave after workup and purification by flash column chromatography [silica (12 g), eluting with DMA80/DCM from 0-100%] mixture of methyl and ethyl 2-(2-((7-(2-(aminomethyl)-3-fluoropyridin-4-yl)-4-fluorobenzofuran-5-yl)methoxy)-5-fluorophenyl)acetate (388c) as a colorless oil. MS (ES+): 471.1 (M+1).

Step-4: Preparation of 2-(2-((7-(2-(aminomethyl)-3-fluoropyridin-4-yl)-4-fluorobenzofuran-5-yl)methoxy)-5-fluorophenyl)acetic Acid (388d)

Compound 388d was prepared according to the procedure reported in step-6 of scheme-1 from ethyl 2-(2-((7-(2-(aminomethyl)-3-fluoropyridin-4-yl)-4-fluorobenzofuran-5-yl)methoxy)-5-fluorophenyl)acetate (388c) (138 mg, 0.293 mmol) in MeOH (6 mL), using lithium hydroxide hydrate (71 mg, 1.692 mmol) in water (2 mL). This gave after workup and purification by reverse phase column [C18 (50 g), eluting with water in acetonitrile (containing 0.1% HCl) from 0-100%] 2-(2-((7-(2-(aminomethyl)-3-fluoropyridin-4-yl)-4-fluorobenzofuran-5-yl)methoxy)-5-fluorophenyl)acetic acid (388d) (91 mg, 70% yield) HCl salt as a white solid. $^1$H NMR (300 MHz, DMSO-d$_6$) δ 12.28 (s, 1H), 8.63 (d, J=5.7 Hz, 4H), 8.20 (d, J=2.3 Hz, 1H), 7.79 (t, J=5.3 Hz, 1H), 7.73 (d, J=6.6 Hz, 1H), 7.27 (d, J=2.3 Hz, 1H), 7.20 (dd, J=8.7, 4.7 Hz, 1H), 7.16-7.05 (m, 2H), 5.30 (s, 2H), 4.37 (s, 2H), 3.56 (s, 2H); $^{19}$F NMR (282 MHz, DMSO-d$_6$) δ −121.24, −123.56, −128.49; MS (ES+): 443.1 (M+1); MS(ES−): 441.1 (M−1); Analysis calculated for C$_{23}$H$_{17}$F$_3$N$_2$O$_4$.HCl.0.5H$_2$O: C, 56.62; H, 3.93; Cl, 7.27; N, 5.74; Found: C, 56.53; H, 3.81; Cl, 7.25; N, 5.79.

Scheme-389

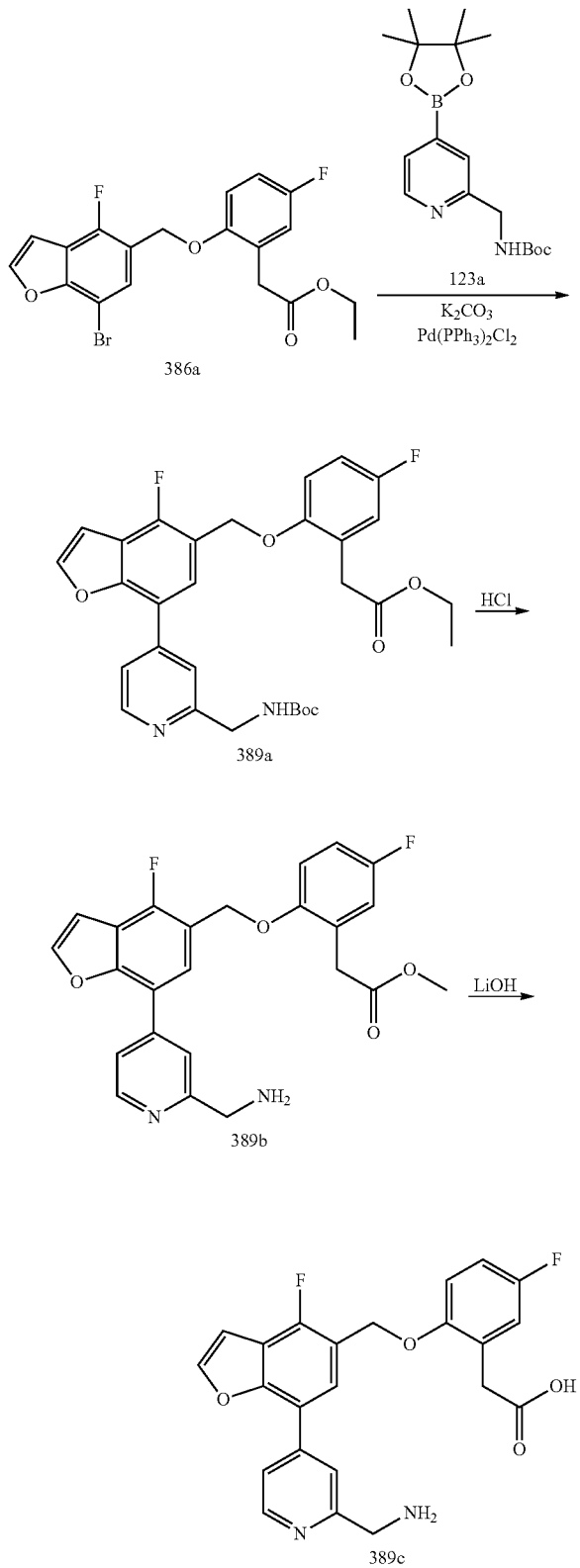

Preparation of 2-(2-((7-(2-(aminomethyl)pyridin-4-yl)-4-fluorobenzofuran-5-yl)methoxy)-5-fluorophenyl)acetic Acid (389c)

Step-1: Preparation of Ethyl 2-(2-((7-(2-(((tert-butoxycarbonyl)amino)methyl)pyridin-4-yl)-4-fluorobenzofuran-5-yl)methoxy)-5-fluorophenyl)acetate (389a)

Compound 389a was prepared according to the procedure reported in step-3 of scheme-1 from ethyl 2-(2-((7-bromo-4-fluorobenzofuran-5-yl)methoxy)-5-fluorophenyl)acetate (386a) (240 mg, 0.564 mmol) in dioxane (5 mL) using tert-butyl (4-(4,4,5,5-tetramethyl-1,3,2-dioxaborolan-2-yl)pyridin-2-yl)methylcarbamate (123a) (264 mg, 0.790 mmol), bis(triphenylphosphine)palladium(II) chloride (Pd (PPh$_3$)$_2$Cl$_2$) (59 mg, 0.085 mmol) and a solution of K$_2$CO$_3$ (234 mg, 1.693 mmol) in water (0.5 mL) under an argon atmosphere heating at 100° C. for 3 h on oil bath. This gave after workup and purification by flash column chromatography [silica gel (12 g), eluting with DMA-80 in DCM from 0-70%] ethyl 2-(2-((7-(2-(((tert-butoxycarbonyl)amino)methyl)pyridin-4-yl)-4-fluorobenzofuran-5-yl)methoxy)-5-fluorophenyl)acetate (389a) (288 mg, 92% yield) as a dark oil. MS (ES+): 553.2 (M+1).

Step-2: Preparation of methyl 2-(2-((7-(2-(aminomethyl)pyridin-4-yl)-4-fluorobenzofuran-5-yl)methoxy)-5-fluorophenyl)acetate (389b)

Compound 389b was prepared according to the procedure reported in step-3 of scheme-305 from ethyl 2-(2-((7-(2-(((tert-butoxycarbonyl)amino)methyl)pyridin-4-yl)-4-fluorobenzofuran-5-yl)methoxy)-5-fluorophenyl)acetate (389a) (288 mg, 0.521 mmol) in MeOH (6 mL) using HCl (4 M in dioxane; 1 mL, 4.0 mmol) and stirring at room temperature overnight. This gave after workup and purification by flash column chromatography [silica (12 g), eluting with DMA80/DCM from 0-100%] methyl 2-(2-((7-(2-(aminomethyl)pyridin-4-yl)-4-fluorobenzofuran-5-yl)methoxy)-5-fluorophenyl)acetate (389b) (229 mg, 100% yield) as a white yellow solid, which was used in the next step without further purification. MS (ES+): 439.1 (M+1).

Step-3: Preparation of 2-(2-((7-(2-(aminomethyl)pyridin-4-yl)-4-fluorobenzofuran-5-yl)methoxy)-5-fluorophenyl)acetic Acid (389c)

Compound 389c was prepared according to the procedure reported in step-6 of scheme-1 from methyl 2-(2-((7-(2-(aminomethyl)pyridin-4-yl)-4-fluorobenzofuran-5-yl)methoxy)-5-fluorophenyl)acetate (389b) ((229 mg, 0.506 mmol) in MeOH (6 mL), using lithium hydroxide hydrate (111 mg, 2.65 mmol) in water (2 mL). This gave after workup and purification by reverse phase column [C18 (50 g), eluting with ACN in water (containing 0.1% HCl) from 0-100%] 2-(2-((7-(2-(aminomethyl)pyridin-4-yl)-4-fluorobenzofuran-5-yl)methoxy)-5-fluorophenyl)acetic acid (389c) (132 mg, 62% yield) HCl salt as a white solid. $^1$H NMR (300 MHz, DMSO-d$_6$) δ 8.81 (d, J=5.4 Hz, 1H), 8.70 (s, 3H), 8.26 (d, J=2.3 Hz, 1H), 8.18 (d, J=1.7 Hz, 1H), 8.04 (dd, J=5.4, 1.7 Hz, 1H), 7.98 (d, J=6.7 Hz, 1H), 7.28 (d, J=2.3 Hz, 1H), 7.21 (dd, J=8.8, 4.7 Hz, 1H), 7.17-7.01 (m, 2H), 5.30 (s, 2H), 4.34 (d, J=5.2 Hz, 2H), 3.59 (s, 2H); $^{19}$F NMR (282 MHz, DMSO) δ−121.10, −123.60; MS (ES+): 425.1 (M+1); MS(ES−): 423.1 (M−1); Analysis calculated for C$_{23}$H$_{18}$F$_2$N2O$_4$.2HCl.H$_2$O: C, 53.61; H, 4.30; Cl, 13.76; N, 5.44; Found: C, 53.54; H, 4.13; Cl, 13.45; N, 5.43.

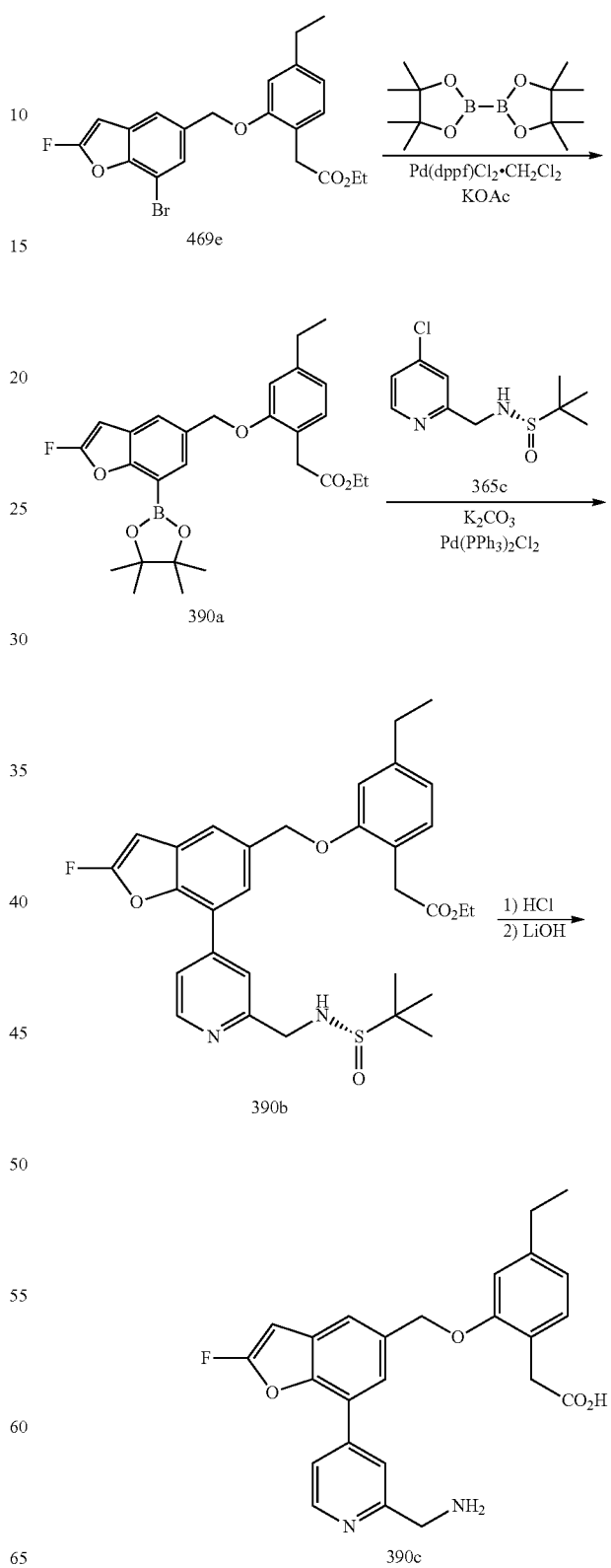

Scheme-390

Preparation of 2-(2-((7-(2-(aminomethyl)pyridin-4-yl)-2-fluorobenzofuran-5-yl)methoxy)-4-ethylphenyl)acetic Acid (390c)

Step-1: Preparation of Ethyl 2-(4-ethyl-2-((2-fluoro-7-(4,4,5,5-tetramethyl-1,3,2-dioxaborolan-2-yl)benzofuran-5-yl)methoxy)phenyl)acetate (390a)

Compound 390a was prepared according to the procedure reported in step-1 of scheme-59 from ethyl 2-(2-((7-bromo-2-fluorobenzofuran-5-yl)methoxy)-4-ethylphenyl)acetate (469e) (350 mg, 0.804 mmol) using bis(pinacolato)diboron (306 mg, 1.206 mmol), potassium acetate (237 mg, 2.412 mmol) and PdCl$_2$(dppf)-CH$_2$Cl$_2$ (66 mg, 0.080 mmol) in anhydrous dioxane (5 mL) under an nitrogen atmosphere and heating at 100° C. for 16 h. This gave after workup and purification by flash column chromatography [silica (24 g), eluting with EtOAc in hexane from 0-5%] ethyl 2-(4-ethyl-2-((2-fluoro-7-(4,4,5,5-tetramethyl-1,3,2-dioxaborolan-2-yl)benzofuran-5-yl)methoxy)phenyl)acetate (390a) (326 mg, 84% yield) as an opaque oil; $^1$H NMR (300 MHz, DMSO-d$_6$) δ 7.75 (s, 1H), 7.63 (s, 1H), 7.09 (d, J=7.5 Hz, 1H), 6.97 (s, 1H), 6.75 (d, J=7.6 Hz, 1H), 6.35 (d, J=6.4 Hz, 1H), 5.15 (s, 2H), 3.99 (q, J=7.1 Hz, 2H), 3.53 (s, 2H), 2.58 (q, J=7.7 Hz, 2H), 1.19-1.13 (m, 15H), 1.05 (t, J=7.1 Hz, 3H); $^{19}$F NMR (282 MHz, DMSO-d$_6$) δ −111.75; MS (ES+): 505.2 (M+Na).

Step-2: Preparation of (S)-ethyl 2-(2-((7-(2-((1,1-dimethylethylsulfinamido)methyl)pyridin-4-yl)-2-fluorobenzofuran-5-yl)methoxy)-4-ethylphenyl)acetate (390b)

Compound 390b was prepared according to the procedure reported in step-3 of scheme-1 from ethyl 2-(4-ethyl-2-((2-fluoro-7-(4,4,5,5-tetramethyl-1,3,2-dioxaborolan-2-yl)benzofuran-5-yl)methoxy)phenyl)acetate (390a) (156 mg, 0.323 mmol) in dioxane (4 mL) using (+)-(S)—N-((4-chloropyridin-2-yl)methyl)-2-methylpropane-2-sulfinamide (365c) (88 mg, 0.356 mmol), PdCl$_2$(PPh$_3$)$_2$ (23 mg, 0.032 mmol) and a solution of K$_2$CO$_3$ (134 mg, 0.970 mmol) in water (0.3 mL) under a nitrogen atmosphere heating at 100° C. for 16 h on oil bath. This gave after workup and purification by flash column chromatography [silica gel (12 g), eluting with MeOH in DCM from 0-3%] (S)-ethyl 2-(2-((7-(2-((1,1-dimethylethylsulfinamido)methyl)pyridin-4-yl)-2-fluorobenzofuran-5-yl)methoxy)-4-ethylphenyl)acetate (390b) (111 mg, 61% yield) as an orange oil; MS (ES+): 567.2 (M+1).

Step-3: Preparation of 2-(2-((7-(2-(aminomethyl)pyridin-4-yl)-2-fluorobenzofuran-5-yl)methoxy)-4-ethylphenyl)acetic Acid (390c)

Compound 390c was prepared from (S)-ethyl 2-(2-((7-(2-((1,1-dimethylethylsulfinamido)methyl)pyridin-4-yl)-2-fluorobenzofuran-5-yl)methoxy)-4-ethylphenyl)acetate (390b) (111 mg, 0.196 mmol) in THF (4 mL) using 4 M HCl in dioxane (0.147 mL, 0.588 mmol) and stirring at room temperature for 16 h. A solution of 2.0 M LiOH (0.378 mL, 0.757 mmol) was added and stirred at 40° C. for 16 h. This gave after workup and purification by reverse phase column [C-18 column, 100 g, eluting with acetonitrile in water (containing 0.1% HCl) from 0-60%] 2-(2-((7-(2-(aminomethyl)pyridin-4-yl)-2-fluorobenzofuran-5-yl)methoxy)-4-ethylphenyl)acetic acid (390c) (11 mg, 17% yield) as a white solid; $^1$H NMR (300 MHz, DMSO-d$_6$) δ 8.79 (d, J=5.3 Hz, 1H), 8.37 (s, 3H, D$_2$O exchangeable), 7.98 (s, 1H), 7.90 (d, 1H), 7.79 (d, 2H), 7.12 (d, J=7.5 Hz, 1H), 6.97 (s, 1H), 6.76 (d, J=7.9, 1.4 Hz, 1H), 6.50 (d, 1H), 5.26 (s, 2H), 4.37-4.26 (m, 2H), 3.54 (s, 2H), 2.60 (q, 2H), 1.18 (t, 3H); $^{19}$F NMR (282 MHz, DMSO-d$_6$) δ −111.21; LC, 2.069 min, 98.3%; MS (ES+): 435.2 (M+1); (ES−): 433.1 (M−1).

Scheme-391

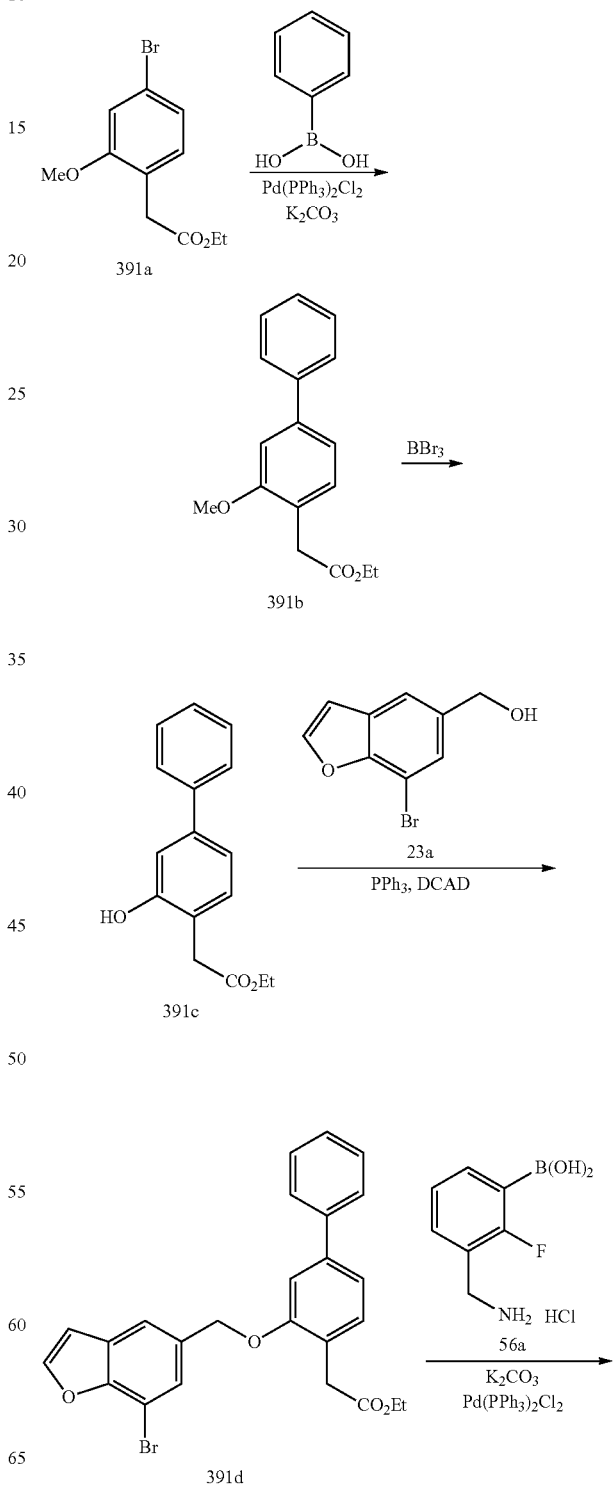

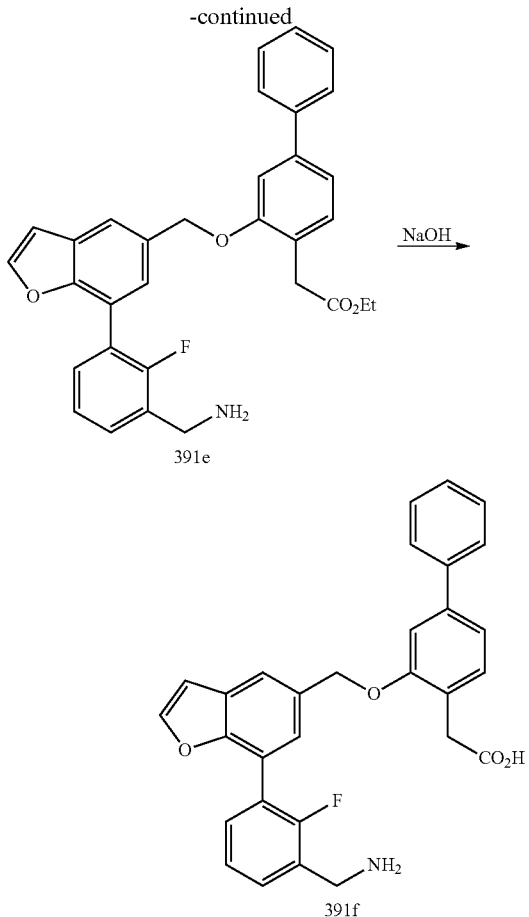

Preparation of 2-(3-((7-(3-(aminomethyl)-2-fluorophenyl)benzofuran-5-yl)methoxy)-[1,1'-biphenyl]-4-yl)acetic Acid (391f)

Step-1: Preparation of Ethyl 2-(3-methoxy-[1,1'-biphenyl]-4-yl)acetate (391b)

Compound 391b was prepared according to the procedure reported in step-3 of scheme-1 from ethyl 2-(4-bromo-2-methoxyphenyl)acetate (391a) (0.95 g, 3.48 mmol; CAS #1261570-38-0) in dioxane (8 mL) using phenylboronic acid (0.467 g, 3.83 mmol), bis(triphenylphosphine)palladium(II) chloride (Pd(PPh$_3$)$_2$Cl$_2$) (0.244 g, 0.348 mmol) and a solution of K$_2$CO$_3$ (1.442 g, 10.43 mmol) in water (2 mL) under an N$_2$ atmosphere heating at 100° C. for 16 h on oil bath. This gave after workup and purification by flash column chromatography (silica gel, eluting with ethyl acetate in hexane from 0-5%] ethyl 2-(3-methoxy-[1,1'-biphenyl]-4-yl)acetate (391b) (0.67 g, 71% yield) as a clear colorless thick oil; $^1$H NMR (300 MHz, DMSO-d$_6$) δ 7.69 (d, 2H), 7.47 (tq, J=6.8, 0.9 Hz, 2H), 7.42-7.33 (m, 1H), 7.27 (d, J=7.6 Hz, 1H), 7.24-7.16 (m, 2H), 4.07 (q, 2H), 3.85 (s, 3H), 3.61 (s, 2H), 1.19 (t, J=7.1, 0.8 Hz, 3H); MS (ES+): 293 (M+Na).

Step-2: Preparation of Ethyl 2-(3-hydroxy-[1,1'-biphenyl]-4-yl)acetate (391c)

Compound 391c was prepared according to the procedure reported in step-5 of scheme-257 from ethyl 2-(3-methoxy-[1,1'-biphenyl]-4-yl)acetate (391b)(0.67 g, 2.479 mmol) in dichloromethane (10 mL) using boron tribromide (4.96 mL, 4.96 mmol, 1M solution in DCM). This gave after workup and purification by flash column chromatography (Silica gel, eluting with 0-10% EtOAc in hexane) ethyl 2-(3-hydroxy-[1,1'-biphenyl]-4-yl)acetate (391c) (0.46 g, 72% yield) as a pale-yellow solid; $^1$H NMR (300 MHz, DMSO-d$_6$) δ 9.71 (s, 1H), 7.63-7.51 (m, 2H), 7.45 (dd, J=8.5, 6.7 Hz, 2H), 7.40-7.29 (m, 1H), 7.19 (d, J=7.5 Hz, 1H), 7.03 (d, J=7.5 Hz, 2H), 4.08 (q, J=7.1 Hz, 2H), 3.58 (s, 2H), 1.19 (t, J=7.1 Hz, 3H); MS (ES+): 257 (M+1).

Step-3: Preparation of Ethyl 2-(3-((7-bromobenzofuran-5-yl)methoxy)-[1,1'-biphenyl]-4-yl)acetate (391d)

Compound 391d was prepared according to the procedure reported in step-2 of scheme-23 from (7-bromobenzofuran-5-yl)methanol (23a) (0.448 g, 1.974 mmol) in DCM (10 mL) using triphenylphosphine (0.941 g, 3.59 mmol), ethyl 2-(3-hydroxy-[1,1'-biphenyl]-4-yl)acetate (391c) (0.46 g, 1.795 mmol) and (E)-bis(4-chlorobenzyl) diazene-1,2-dicarboxylate (DCAD, 1.318 g, 3.59 mmol) in DCM (25 mL). This gave after workup and purification by flash column chromatography (silica gel, eluting with EtOAc in hexane from 0-10%) ethyl 2-(3-((7-bromobenzofuran-5-yl)methoxy)-[1,1'-biphenyl]-4-yl)acetate (391d) (0.69 g, 83% yield) as a pale-green solid. $^1$H NMR (300 MHz, DMSO-d$_6$) δ 8.15 (d, J=2.2 Hz, 1H), 7.75 (d, J=1.5 Hz, 1H), 7.70 (d, J=1.5 Hz, 1H), 7.67 (d, J=1.1 Hz, 1H), 7.64 (d, J=1.5 Hz, 1H), 7.52-7.44 (m, 2H), 7.41-7.34 (m, 2H), 7.31 (d, J=7.8 Hz, 1H), 7.22 (dd, J=7.7, 1.6 Hz, 1H), 7.13 (d, J=2.2 Hz, 1H), 5.31 (s, 2H), 4.03 (q, J=7.1 Hz, 2H), 3.67 (s, 2H), 1.09 (t, J=7.1 Hz, 3H); MS (ES+): 487/489 (M+Na).

Step-4: Preparation of Ethyl 2-(3-((7-(3-(aminomethyl)-2-fluorophenyl)benzofuran-5-yl)methoxy)-[1,1'-biphenyl]-4-yl)acetate (391e)

Compound 391e was prepared according to the procedure reported in step-3 of scheme-1 from ethyl 2-(3-((7-bromobenzofuran-5-yl)methoxy)-[1,1'-biphenyl]-4-yl)acetate (391d) (135 mg, 0.290 mmol) in dioxane (4 mL) using 3-(aminomethyl)-2-fluorophenylboronic acid hydrochloride (56a) (66 mg, 0.319 mmol), bis(triphenylphosphine)palladium(II) chloride (Pd(PPh$_3$)$_2$Cl$_2$) (20 mg, 0.029 mmol) and a solution of K$_2$CO$_3$ (120 mg, 0.870 mmol) in water (1 mL) under an N$_2$ atmosphere heating at 100° C. for 16 h on oil bath. This gave after workup, purification by flash column chromatography (silica gel, eluting with MeOH in DCM from 0-5%] ethyl 2-(3-((7-(3-(aminomethyl)-2-fluorophenyl)benzofuran-5-yl)methoxy)-[1,1'-biphenyl]-4-yl)acetate (391e) (65 mg) as a clear pale-yellow oil; MS (ES+): 510 (M+1).

Step-5: Preparation of 2-(3-((7-(3-(aminomethyl)-2-fluorophenyl)benzofuran-5-yl)methoxy)-[1,1'-biphenyl]-4-yl)acetic Acid (391f)

Compound 391f was prepared according to the procedure reported in step-4 of scheme-4 from of ethyl 2-(3-((7-(3-(aminomethyl)-2-fluorophenyl)benzofuran-5-yl)methoxy)-[1,1'-biphenyl]-4-yl)acetate (391e) (65 mg, from above step-4) in MeOH (3 mL), using a solution of sodium hydroxide (23 mg, 0.58 mmol) in water (1 mL). This gave after workup and purification by reverse phase column [C18 (100 g), eluting with ACN in water (containing 0.1% HCl) from 0-60%] 2-(3-((7-(3-(aminomethyl)-2-fluorophenyl)benzofuran-5-yl)methoxy)-[1,1'-biphenyl]-4-yl)acetic acid (391f) (50 mg, 36% yield) HCl salt as a white solid; $^1$H NMR (300 MHz, DMSO-$d_6$) δ 8.06 (d, J=2.2 Hz, 1H), 7.86 (d, J=1.6 Hz, 1H), 7.74-7.61 (m, 4H), 7.52 (d, J=1.6 Hz, 1H), 7.50-7.41 (m, 3H), 7.41-7.33 (m, 2H), 7.31 (d, J=7.8 Hz, 1H), 7.20 (dd, J=7.7, 1.6 Hz, 1H), 7.08 (d, J=2.2 Hz, 1H), 5.40 (s, 2H), 4.18 (s, 2H), 3.62 (s, 2H); MS (ES+): 482 (M+1), (ES−): 480 (M−1); Analysis calculated for $C_{30}H_{24}FNO_4 \cdot HCl \cdot 2H_2O$: C, 65.04; H, 5.28; Cl, 6.40; N, 2.53: Found: C, 65.04; H, 5.00; Cl, 6.74; N, 2.61.

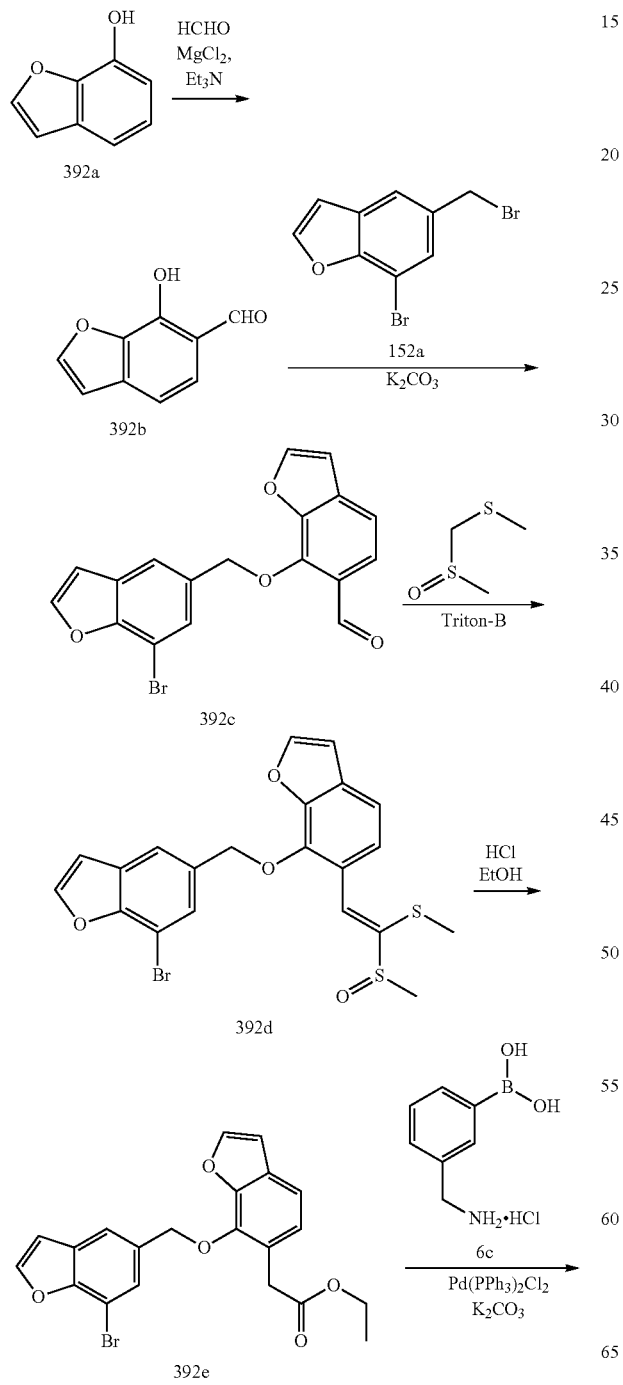

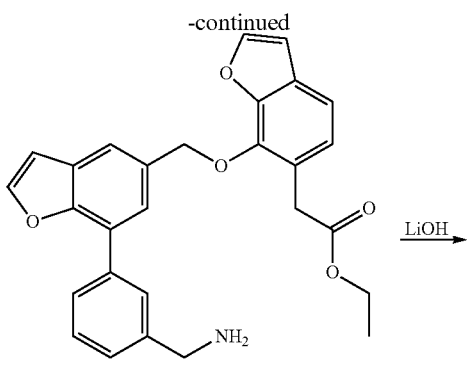

Preparation of 2-(7-((7-(3-(aminomethyl)phenyl)benzofuran-5-yl)methoxy)benzofuran-6-yl)acetic Acid (392g)

Step-1: Preparation of 7-hydroxybenzofuran-6-carbaldehyde (392b)

Compound 392b was prepared according to the procedure reported in step-1 of scheme-266 from benzofuran-7-ol (392a) (500 mg, 3.73 mmol; CAS #4790-81-2) using MgCl$_2$ (532 mg, 5.59 mmol), Et$_3$N (1.975 mL, 14.17 mmol), paraformaldehyde (2.239 g, 74.6 mmol) in anhydrous MeCN (25 mL) This gave after workup and purification by flash column chromatography (silica gel, 25 g, eluting with ethyl acetate and hexanes) 7-hydroxybenzofuran-6-carbaldehyde (392b) (133 mg, 22.00% yield) as a white solid; $^1$H NMR (300 MHz, DMSO-$d_6$) δ 11.50 (s, 1H), 10.27 (d, J=0.5 Hz, 1H), 8.25 (d, J=2.1 Hz, 1H), 7.55 (d, J=8.2 Hz, 1H), 7.24 (dd, J=8.2, 0.5 Hz, 1H), 7.06 (d, J=2.1 Hz, 1H).

Step-2: Preparation of 7-((7-bromobenzofuran-5-yl)methoxy)benzofuran-6-carbaldehyde (392c)

Compound 392c was prepared according to the procedure reported in step-2 of scheme-152 from 7-bromo-5-(bromomethyl)benzofuran (152a) (125 mg, 0.771 mmol) using 7-hydroxybenzofuran-6-carbaldehyde (392b) (224 mg, 0.771 mmol) and K$_2$CO$_3$ (320 mg, 2.313 mmol) in DMF (5 mL). This gave after workup and purification by flash column chromatography (Silica gel, 24 g, eluting with EtOAc in hexane) 7-((7-bromobenzofuran-5-yl)methoxy)benzofuran-6-carbaldehyde (392c) (255 mg, 89%) as a white solid; $^1$H NMR (300 MHz, DMSO-$d_6$) δ 10.34 (d, J=0.8 Hz, 1H), 8.34 (d, J=2.1 Hz, 1H), 8.14 (d, J=2.2 Hz, 1H), 7.82 (d, J=1.5 Hz, 1H), 7.74 (d, J=1.5 Hz, 1H), 7.58 (d, J=8.2 Hz, 1H), 7.44 (dd, J=8.2, 0.8 Hz, 1H), 7.13 (dd, J=5.5, 2.2 Hz, 2H), 5.72 (s, 2H).

Step-3: Preparation of (E)-7-bromo-5-(((6-(2-(methylsulfinyl)-2-(methylthio)vinyl)benzofuran-7-yl)oxy)methyl)benzofuran (392d)

Compound 392d was prepared according to the procedure reported in step-3 of scheme-266 from 7-((7-bromobenzofuran-5-yl)methoxy)benzofuran-6-carbaldehyde (392c) (250 mg, 0.674 mmol) using methyl(methylsulfinylmethyl)sulfane (134 mg, 1.078 mmol), Triton-B (40% methanolic solution) (0.153 mL, 0.337 mmol) in THF (10 mL) and heating at 70° C. for 12 h. This gave after workup and purification by flash column chromatography (Silica gel, 24 g, eluting with 0-40% EtOAc in hexane) (E)-7-bromo-5-(((6-(2-(methylsulfinyl)-2-(methylthio)vinyl)benzofuran-7-yl)oxy)methyl)benzofuran (392d) (322 mg, 100% yield) as a yellow syrup; MS (ES+): 477.0, 479.9 (M, M+2).

Step-4: Preparation of Ethyl 2-(7-((7-bromobenzofuran-5-yl)methoxy)benzofuran-6-yl)acetate (392e)

Compound 392e was prepared according to the procedure reported in step-4 of scheme-266 from (E)-7-bromo-5-(((6-(2-(methylsulfinyl)-2-(methylthio)vinyl)benzofuran-7-yl)oxy)methyl)benzofuran (392d) (322 mg, 0.674 mmol) in ethanol (20 mL) using HCl (4 M in 1,4-dioxane, 0.674 mL, 2.70 mmol) and heating at reflux for 12 h. This gave after workup and purification by flash column chromatography (silica gel, 40 g, eluting with ethyl acetate and hexanes) ethyl 2-(7-((7-bromobenzofuran-5-yl)methoxy)benzofuran-6-yl)acetate (392e) (135 mg, 47% yield) as a thick syrup; $^1$H NMR (300 MHz, DMSO-$d_6$) δ 8.15 (d, J=2.2 Hz, 1H), 8.05 (d, J=2.1 Hz, 1H), 7.75 (d, J=1.5 Hz, 1H), 7.65 (d, J=1.5 Hz, 1H), 7.30 (d, J=7.9 Hz, 1H), 7.14-7.07 (m, 2H), 6.99 (d, J=2.2 Hz, 1H), 5.45 (s, 2H), 3.99 (q, J=7.1 Hz, 2H), 3.71 (s, 2H), 1.09 (t, J=7.1 Hz, 3H).

Step-5: Preparation of Ethyl 2-(7-((7-(3-(aminomethyl)phenyl)benzofuran-5-yl)methoxy)benzofuran-6-yl)acetate (392f)

Compound 392f was prepared according to the procedure reported in step-3 of scheme-1 from ethyl 2-(7-((7-bromobenzofuran-5-yl)methoxy)benzofuran-6-yl)acetate (392e) (125 mg, 0.291 mmol) in dioxane (8 mL) using 3-(aminomethyl)phenylboronic acid hydrochloride (6c) (68 mg, 0.364 mmol), bis(triphenylphosphine)palladium(II) chloride (Pd(PPh$_3$)$_2$Cl$_2$) (31 mg, 0.044 mmol) and K$_2$CO$_3$ (121 mg, 0.894 mmol) in water (2 mL) under an N$_2$ atmosphere heating at 100° C. for 12 h on oil bath. This gave after workup, purification by flash column chromatography (silica gel, 24 g, eluting with DMA80 in DCM from 0-90%) ethyl 2-(7-((7-(3-(aminomethyl)phenyl)benzofuran-5-yl)methoxy)benzofuran-6-yl)acetate (392f) (70 mg, 53% yield) as an oil; $^1$H NMR (300 MHz, DMSO-$d_6$) δ 8.09 (d, J=2.2 Hz, 1H), 8.06 (d, J=2.2 Hz, 1H), 7.80 (d, J=2.0 Hz, 1H), 7.70 (dt, J=9.1, 1.7 Hz, 2H), 7.59 (d, J=1.7 Hz, 1H), 7.46 (t, J=7.6 Hz, 1H), 7.42-7.37 (m, 1H), 7.29 (d, J=7.9 Hz, 1H), 7.10 (d, J=7.9 Hz, 1H), 7.05 (d, J=2.2 Hz, 1H), 6.99 (d, J=2.2 Hz, 1H), 5.53 (s, 2H), 3.93 (q, J=7.1 Hz, 2H), 3.82 (s, 2H), 3.71 (s, 2H), 1.01 (t, J=7.1 Hz, 3H; MS (ES+): 456.1 (M+1).

Step-6: Preparation of 2-(7-((7-(3-(aminomethyl)phenyl)benzofuran-5-yl)methoxy)benzofuran-6-yl)acetic Acid (392g)

Compound 392g was prepared according to the procedure reported in step-6 of scheme-1 from ethyl 2-(7-((7-(3-(aminomethyl)phenyl)benzofuran-5-yl)methoxy)benzofuran-6-yl)acetate (392f) (68 mg, 0.149 mmol) in THF (10 mL), MeOH (2 mL), using a solution of lithium hydroxide (14 mg, 0.597 mmol) in water (2 mL). This gave after workup and purification by reverse phase column [C18 (100 g), eluting with ACN in water (containing 0.1% HCl) from 0-100%] 2-(7-((7-(3-(aminomethyl)phenyl)benzofuran-5-yl)methoxy)benzofuran-6-yl)acetic acid (392g) (52 mg, 81% yield) hydrochloride salt as a white solid; $^1$H NMR (300 MHz, DMSO-$d_6$) δ 12.31 (s, 1H), 8.50 (s, 3H), 8.11 (d, J=2.2 Hz, 1H), 8.06 (d, J=2.2 Hz, 1H), 7.99 (s, 1H), 7.97-7.87 (m, 1H), 7.80 (s, 1H), 7.68 (d, J=1.7 Hz, 1H), 7.65-7.50 (m, 2H), 7.30 (d, J=7.9 Hz, 1H), 7.19-7.04 (m, 2H), 6.99 (d, J=2.2 Hz, 1H), 5.52 (s, 2H), 4.14 (s, 2H), 3.68 (s, 2H); MS (ES+): 428.10 (M+1), (ES−): 426.10 (M−1); Analysis calculated for C$_{26}$H$_{21}$NO$_5$.HCl.1.25H$_2$O: C, 64.20; H, 5.08; Cl, 7.29; N, 2.88; Found: C, 64.27; H, 5.17; Cl, 7.35; N, 2.89.

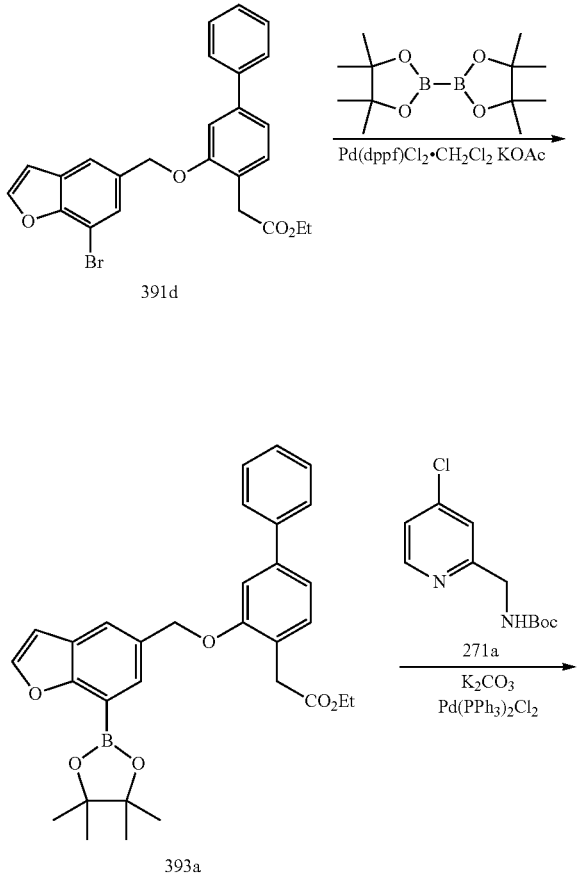

Scheme-393

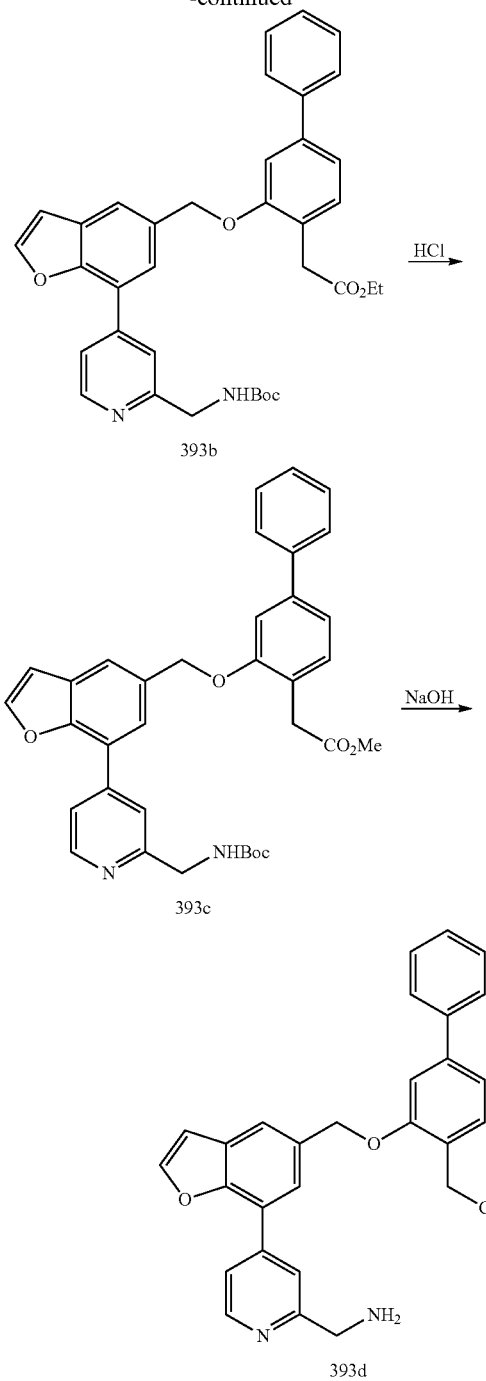

Preparation of 2-(3-((7-(2-(aminomethyl)pyridin-4-yl)benzofuran-5-yl)methoxy)-[1,1'-biphenyl]-4-yl)acetic Acid (393d)

Step-1: Preparation of Ethyl 2-(3-((7-(4,4,5,5-tetramethyl-1,3,2-dioxaborolan-2-yl)benzofuran-5-yl)methoxy)-[1,1'-biphenyl]-4-yl)acetate (393a)

Compound 393a was prepared according to the procedure reported in step-1 of scheme-59 from ethyl 2-(3-((7-bromobenzofuran-5-yl)methoxy)-[1,1'-biphenyl]-4-yl)acetate (391d) (328 mg, 0.705 mmol), using bis(pinacolato)diboron (268 mg, 1.057 mmol), potassium acetate (208 mg, 2.115 mmol) and Pd(dppf)Cl$_2$—CH$_2$Cl$_2$ (58 mg, 0.070 mmol) in anhydrous dioxane (5 mL) under an argon atmosphere and heating at 100° C. for 16 h. This gave after workup and purification by flash column chromatography [silica gel (12 g), eluting with EtOAc in hexane from 0-10%] ethyl 2-(3-((7-(4,4,5,5-tetramethyl-1,3,2-dioxaborolan-2-yl)benzofuran-5-yl)methoxy)-[1,1'-biphenyl]-4-yl)acetate (393a) (331 mg, 92% yield) as a colorless oil; $^1$H NMR (300 MHz, DMSO-d$_6$) δ 8.07 (d, J=2.2 Hz, 1H), 7.87 (d, J=1.9 Hz, 1H), 7.76-7.65 (m, 3H), 7.53-7.43 (m, 2H), 7.42-7.33 (m, 2H), 7.30 (d, J=7.8 Hz, 1H), 7.20 (dd, J=7.7, 1.6 Hz, 1H), 6.98 (d, J=2.3 Hz, 1H), 5.31 (s, 2H), 4.02 (q, J=7.1 Hz, 2H), 3.63 (s, 2H), 1.34 (s, 12H), 1.07 (t, J=7.1 Hz, 3H); MS (ES+): 535 (M+Na).

Step-2: Preparation of Ethyl 2-(3-((7-(2-(((tert-butoxycarbonyl)amino)methyl)pyridin-4-yl)benzofuran-5-yl)methoxy)-[1,1'-biphenyl]-4-yl)acetate (393b)

Compound 393b was prepared according to the procedure reported in step-3 of scheme-1 from ethyl 2-(3-((7-(4,4,5,5-tetramethyl-1,3,2-dioxaborolan-2-yl)benzofuran-5-yl)methoxy)-[1,1'-biphenyl]-4-yl)acetate (393a) (145 mg, 0.283 mmol) in dioxane (4 mL) using tert-butyl (4-chloropyridin-2-yl)methylcarbamate (271a) (76 mg, 0.311 mmol), bis(triphenylphosphine)palladium(II) chloride (Pd(PPh$_3$)$_2$Cl$_2$) (20 mg, 0.028 mmol) and a solution of K$_2$CO$_3$ (117 mg, 0.849 mmol) in water (1 mL) under an argon atmosphere heating at 100° C. for 16 h on oil bath. This gave after workup and purification by flash column chromatography [silica gel (12 g), eluting with 0-30% EtOAc in hexane] ethyl 2-(3-((7-(2-(((tert-butoxycarbonyl)amino)methyl)pyridin-4-yl)benzofuran-5-yl)methoxy)-[1,1'-biphenyl]-4-yl)acetate (393b) (35 mg) as a pale-yellow oil; MS (ES+): 593 (M+1).

Step-3: Preparation of methyl 2-(3-((7-(2-(((tert-butoxycarbonyl)amino)methyl)pyridin-4-yl)benzofuran-5-yl)methoxy)-[1,1'-biphenyl]-4-yl)acetate (393c)

Compound 393c was prepared according to the procedure reported in step-3 of scheme-305 from ethyl 2-(3-((7-(2-(((tert-butoxycarbonyl)amino)methyl)pyridin-4-yl)benzofuran-5-yl)methoxy)-[1,1'-biphenyl]-4-yl)acetate (393b) (35 mg, from above step-2) in MeOH (5 mL) using HCl (4 M in dioxane; 1.415 mL, 5.66 mmol) and stirring at 60° C. for 1 h. This gave after workup methyl 2-(3-((7-(2-(((tert-butoxycarbonyl)amino)methyl)pyridin-4-yl)benzofuran-5-yl)methoxy)-[1,1'-biphenyl]-4-yl)acetate (393c); MS (ES+): 479 (M+1).

Step-4: Preparation of 2-(3-((7-(2-(aminomethyl)pyridin-4-yl)benzofuran-5-yl)methoxy)-[1,1'-biphenyl]-4-yl)acetic Acid (393d)

Compound 393d was prepared according to the procedure reported in step-4 of scheme-4 from methyl 2-(3-((7-(2-(((tert-butoxycarbonyl)amino)methyl)pyridin-4-yl)benzofuran-5-yl)methoxy)-[1,1'-biphenyl]-4-yl)acetate (393c) (from above step-3) in MeOH (3 mL), using NaOH (34.0 mg, 0.849 mmol) in water (1 mL). This gave after workup and purification by reverse phase column (C18, 100 g, eluting with 0-60% MeCN in H$_2$O containing 0.1% HCl) 2-(3-((7-(2-(aminomethyl)pyridin-4-yl)benzofuran-5-yl)

methoxy)-[1,1'-biphenyl]-4-yl)acetic acid (393d) (10 mg, 8% yield) HCl salt as a pale green solid; $^1$H NMR (300 MHz, DMSO-d$_6$) δ 8.79 (d, J=5.3 Hz, 1H), 8.48-8.32 (m, 3H), 8.18 (d, J=2.2 Hz, 1H), 8.07 (s, 1H), 7.99 (dd, J=5.0, 1.7 Hz, 1H), 7.91 (d, J=1.6 Hz, 1H), 7.86 (d, J=1.6 Hz, 1H), 7.71-7.64 (m, 2H), 7.46 (dt, J=8.4, 6.7 Hz, 2H), 7.42-7.28 (m, 3H), 7.21 (dd, J=7.6, 1.5 Hz, 1H), 7.13 (d, J=2.2 Hz, 1H), 5.42 (s, 2H), 4.41-4.27 (m, 2H), 3.65 (s, 2H); MS (ES+): 465 (M+1), 463 (M−1).

Scheme-394

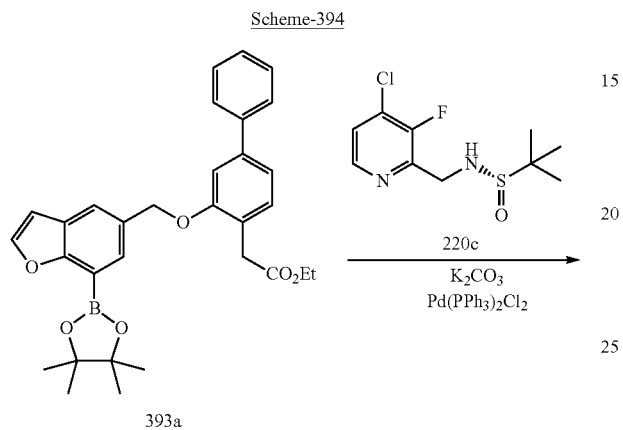

393a

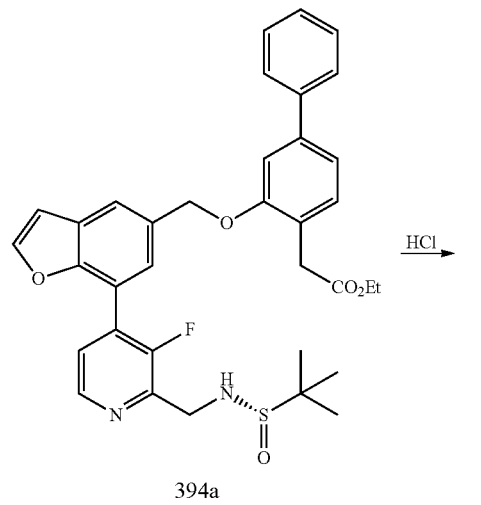

394a

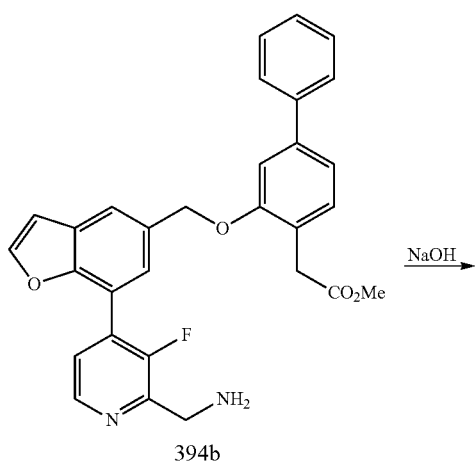

394b

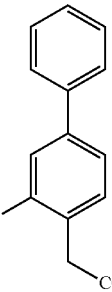

394c

Preparation of 2-(3-((7-(2-(aminomethyl)-3-fluoro-pyridin-4-yl)benzofuran-5-yl)methoxy)-[1,1'-biphe-nyl]-4-yl)acetic Acid (394c)

Step-1: Preparation of (S)-ethyl 2-(3-((7-(2-(((1,1-dimethylethylsulfinamido)methyl)-3-fluoropyridin-4-yl)benzofuran-5-yl)methoxy)-[1,1'-biphenyl]-4-yl)acetate (394a)

Compound 394a was prepared according to the procedure reported in step-3 of scheme-1 from ethyl 2-(3-((7-(4,4,5,5-tetramethyl-1,3,2-dioxaborolan-2-yl)benzofuran-5-yl)methoxy)-[1,1'-biphenyl]-4-yl)acetate (393a) (202 mg, 0.394 mmol) in dioxane (4 mL) using (+)-(S)—N-((4-chloro-3-fluoropyridin-2-yl)methyl)-2-methylpropane-2-sulfinamide (220c) (115 mg, 0.434 mmol), bis(triphenylphosphine)palladium(II) chloride (Pd(PPh$_3$)$_2$Cl$_2$) (28 mg, 0.039 mmol) and a solution of K$_2$CO$_3$ (163 mg, 1.183 mmol) in water (1 mL) under an argon atmosphere heating at 100° C. for 16 h on oil bath. This gave after workup and purification by flash column chromatography [silica gel (12 g), eluting with 0-4% MeOH in DCM] (S)-ethyl 2-(3-((7-(2-(((1,1-dimethylethylsulfinamido)methyl)-3-fluoropyridin-4-yl)benzofuran-5-yl)methoxy)-[1,1'-biphenyl]-4-yl)acetate (394a) (100 mg) as a pale-yellow oil; MS (ES+) 615 (M+1).

Step-2: Preparation of methyl 2-(3-((7-(2-(aminomethyl)-3-fluoropyridin-4-yl)benzofuran-5-yl)methoxy)-[1,1'-biphenyl]-4-yl)acetate (394b)

Compound 394b was prepared according to the procedure reported in step-3 of scheme-305 from (S)-ethyl 2-(3-((7-(2-(((1,1-dimethylethylsulfinamido)methyl)-3-fluoropyridin-4-yl)benzofuran-5-yl)methoxy)-[1,1'-biphenyl]-4-yl)acetate (394a) (100 mg, from above step-1) in MeOH (4 mL) using HCl (4 M in dioxane; 1.971 mL, 7.88 mmol) and stirring at 60° C. for 1 h. This gave after workup methyl 2-(3-((7-(2-(aminomethyl)-3-fluoropyridin-4-yl)benzofuran-5-yl)methoxy)-[1,1'-biphenyl]-4-yl)acetate (394b); MS (ES+): 497 (M+1).

Step-3: Preparation of 2-(3-((7-(2-(aminomethyl)-3-fluoropyridin-4-yl)benzofuran-5-yl)methoxy)-[1,1'-biphenyl]-4-yl)acetic Acid (394c)

Compound 394c was prepared according to the procedure reported in step-4 of scheme-4 from methyl 2-(3-((7-(2-(aminomethyl)-3-fluoropyridin-4-yl)benzofuran-5-yl)methoxy)-[1,1'-biphenyl]-4-yl)acetate (394b) (from above step-2) in MeOH (3 mL), using NaOH (47 mg, 1.183 mmol) in water (1 mL). This gave after workup and purification by reverse phase column (C18, 100 g, eluting with 0-60% MeCN in H$_2$O containing 0.1% HCl) 2-(3-((7-(2-(aminomethyl)-3-fluoropyridin-4-yl)benzofuran-5-yl)methoxy)-[1,1'-biphenyl]-4-yl)acetic acid (394c) (60 mg, 32% yield) HCl as a pale-green solid; $^1$H NMR (300 MHz, DMSO-d$_6$) δ 8.64 (d, J=5.0 Hz, 1H), 8.57-8.39 (m, 3H), 8.12 (d, J=2.2 Hz, 1H), 7.95 (d, J=1.6 Hz, 1H), 7.81 (t, J=5.3 Hz, 1H), 7.72-7.63 (m, 3H), 7.47 (dt, J=8.3, 6.6 Hz, 2H), 7.41-7.33 (m, 2H), 7.31 (d, J=7.8 Hz, 1H), 7.21 (dd, J=7.7, 1.6 Hz, 1H), 7.13 (d, J=2.2 Hz, 1H), 5.41 (s, 2H), 4.40 (h, J=4.7 Hz, 2H), 3.63 (s, 2H); MS (ES+) 483 (M+1), 481 (M−1); Analysis calculated for C$_{29}$H$_{23}$FN$_2$O$_4$.1.15HCl.H$_2$O: C, 64.21; H, 4.86; Cl, 7.52; N, 5.16; Found: C, 64.34; H, 4.85; Cl, 7.40; N, 5.18.

Scheme-395

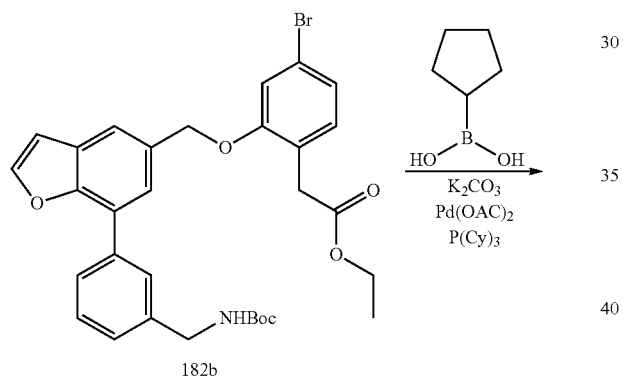

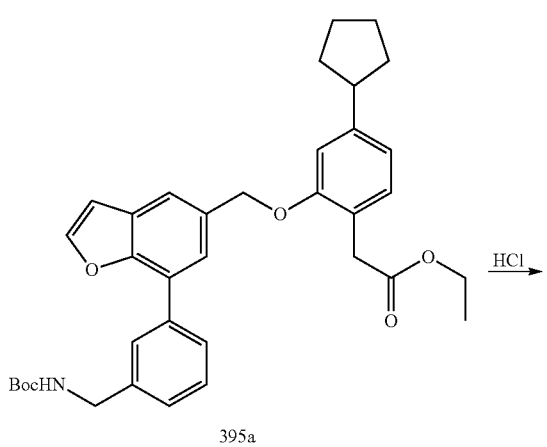

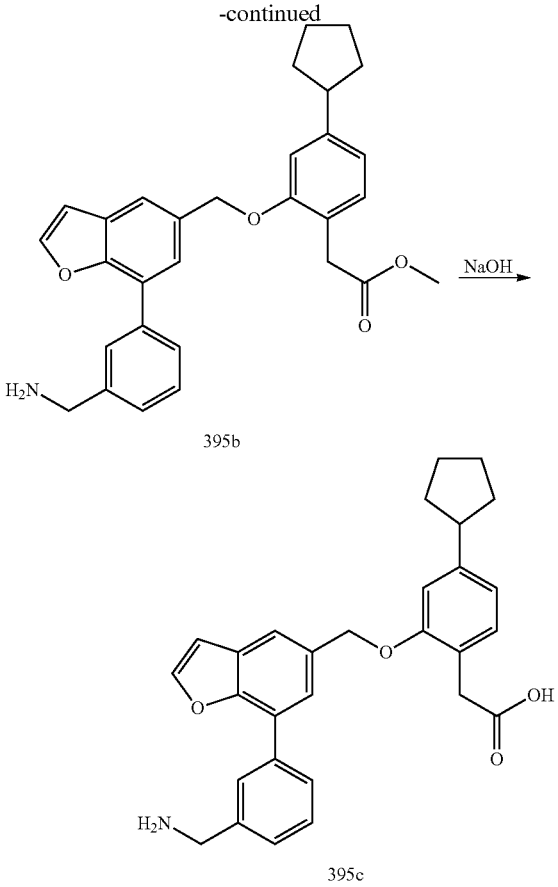

Preparation of 2-(2-((7-(3-(aminomethyl)phenyl)benzofuran-5-yl)methoxy)-4-cyclopentylphenyl)acetic Acid (395c)

Step-1: Preparation of Ethyl 2-(2-((7-(3-(((tert-butoxycarbonyl)amino)methyl)phenyl)benzofuran-5-yl)methoxy)-4-cyclopentylphenyl)acetate (395a)

Compound 395a was prepared according to the procedure reported in step-3 of scheme-1 from ethyl 2-(4-bromo-2-((7-(3-(((tert-butoxycarbonyl)amino)methyl)phenyl)benzofuran-5-yl)methoxy)phenyl)acetate (182b) (202 mg, 0.394 mmol) in PhMe (10 mL) using cyclopentylboronic acid (84 mg, 0.740 mmol), Pd(OAc)$_2$ (8.31 mg, 0.037 mmol), P(Cy)$_3$ (20.76 mg, 0.074 mmol) and a solution of K$_2$CO$_3$ (169 mg, 1.221 mmol) in water (1 mL) under a nitrogen atmosphere heating at 100° C. for 16 h on oil bath. This gave after workup and purification by flash column chromatography [silica gel (12 g), eluting with 0-15% EtOAc in hexane] ethyl 2-(2-((7-(3-(((tert-butoxycarbonyl)amino)methyl)phenyl)benzofuran-5-yl)methoxy)-4-cyclopentylphenyl)acetate (395a) (57 mg) as a colorless oil; MS (ES+): 606 (M+Na).

Step-2: Preparation of methyl 2-(2-((7-(3-(aminomethyl)phenyl)benzofuran-5-yl)methoxy)-4-cyclopentylphenyl)acetate (395b)

Compound 395b was prepared according to the procedure reported in step-3 of scheme-305 from ethyl 2-(2-((7-(3-(((tert-butoxycarbonyl)amino)methyl)phenyl)benzofuran-5-yl)methoxy)-4-cyclopentylphenyl)acetate (395a) (57 mg, from above step-1) in MeOH (5 mL) using HCl (4 M in dioxane; 0.463 mL, 1.850 mmol) and stirring at 40° C. for 1 h. This gave after workup methyl 2-(2-((7-(3-(aminomethyl)phenyl)benzofuran-5-yl)methoxy)-4-cyclopentylphenyl)acetate (395b); MS (ES+) 470 (M+1).

Step-3: Preparation of 2-(2-((7-(3-(aminomethyl)phenyl)benzofuran-5-yl)methoxy)-4-cyclopentylphenyl)acetic Acid (395c)

Compound 395c was prepared according to the procedure reported in step-4 of scheme-4 from methyl 2-(2-((7-(3-(aminomethyl)phenyl)benzofuran-5-yl)methoxy)-4-cyclopentylphenyl)acetate (395b) (from above step-2) in MeOH (3 mL), using NaOH (44 mg, 1.11 mmol) in water (1 mL). This gave after workup and purification by reverse phase column (C18, 100 g, eluting with 0-60% MeCN in H$_2$O containing 0.1% HCl) 2-(2-((7-(3-(aminomethyl)phenyl)benzofuran-5-yl)methoxy)-4-cyclopentylphenyl)acetic acid (395c) (20 mg, 12% yield) HCl salt as a white solid; $^1$H NMR (300 MHz, DMSO-d$_6$) δ 8.10 (d, J=2.2 Hz, 1H), 8.00 (d, J=1.7 Hz, 1H), 7.93 (dt, J=7.6, 1.5 Hz, 1H), 7.77 (d, J=1.6 Hz, 1H), 7.66 (d, J=1.7 Hz, 1H), 7.60 (t, J=7.6 Hz, 1H), 7.56-7.50 (m, 1H), 7.12-7.03 (m, 2H), 6.99 (d, J=1.6 Hz, 1H), 6.79 (dd, J=7.4, 1.6 Hz, 1H), 5.26 (s, 2H), 4.14 (s, 2H), 3.53 (s, 2H), 2.94 (t, J=8.1 Hz, 1H), 1.98 (s, 2H), 1.75 (dd, J=5.4, 2.7 Hz, 2H), 1.69-1.49 (m, 4H); MS (ES+): 456 (M+1), 454 (M−1).

Scheme-396

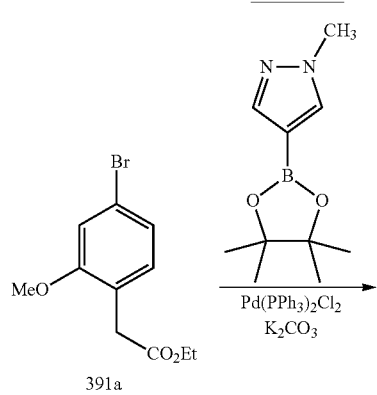

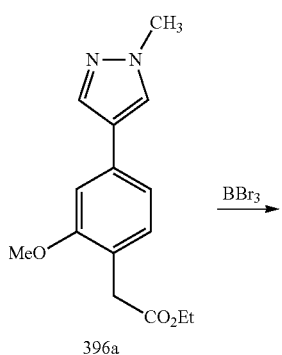

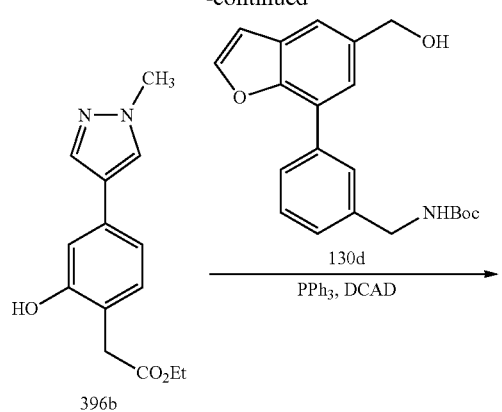

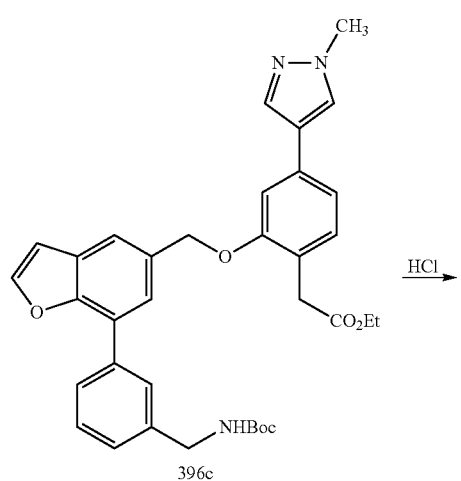

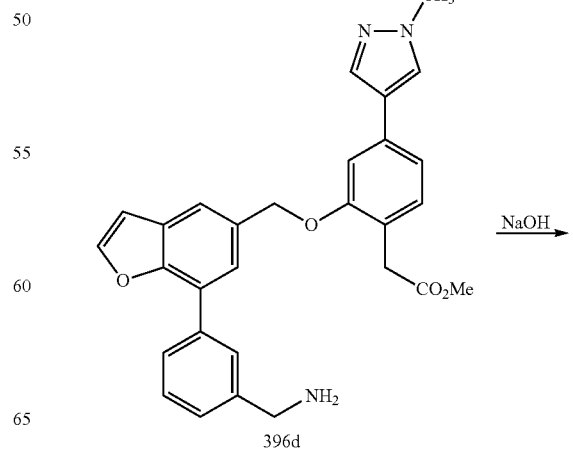

-continued

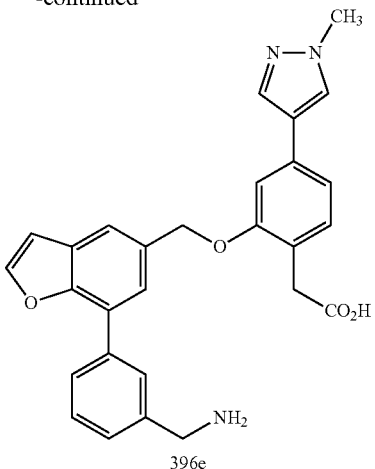

396e

Preparation of 2-(2-((7-(3-(aminomethyl)phenyl)benzofuran-5-yl)methoxy)-4-(1-methyl-1H-pyrazol-4-yl)phenyl)acetic Acid (396e)

Step-1: Preparation of Ethyl 2-(2-methoxy-4-(1-methyl-1H-pyrazol-4-yl)phenyl)acetate (396a)

Compound 396a was prepared according to the procedure reported in step-3 of scheme-1 from ethyl 2-(4-bromo-2-methoxyphenyl)acetate (391a) (406 mg, 1.486 mmol) in dioxane (8 mL) using 1-methyl-4-(4,4,5,5-tetramethyl-1,3,2-dioxaborolan-2-yl)-1H-pyrazole (340 mg, 1.634 mmol), bis(triphenylphosphine)palladium(II) chloride (Pd(PPh$_3$)$_2$Cl$_2$) (104 mg, 0.149 mmol) and a solution of K$_2$CO$_3$ (616 mg, 4.46 mmol) in water (2 mL) under an N$_2$ atmosphere heating at 100° C. for 16 h on oil bath. This gave after workup and purification by flash column chromatography (silica gel, eluting with ethyl acetate in hexane from 0-40%] ethyl 2-(2-methoxy-4-(1-methyl-1H-pyrazol-4-yl)phenyl)acetate (396a) (250 mg, 61% yield) as a colorless oil; $^1$H NMR (300 MHz, DMSO-d$_6$) δ 8.15 (d, J=0.8 Hz, 1H), 7.88 (d, J=0.8 Hz, 1H), 7.21-7.04 (m, 3H), 4.06 (q, J=7.1 Hz, 2H), 3.86 (s, 3H), 3.80 (s, 3H), 3.54 (s, 2H), 1.17 (t, J=7.1 Hz, 3H); MS (ES+): 275 (M+1).

Step-2: Preparation of Ethyl 2-(2-hydroxy-4-(1-methyl-1H-pyrazol-4-yl)phenyl)acetate (396b)

Compound 396b was prepared according to the procedure reported in step-5 of scheme-257 from ethyl 2-(2-methoxy-4-(1-methyl-1H-pyrazol-4-yl)phenyl)acetate (396a) (243 mg, 0.886 mmol) in dichloromethane (10 mL) using boron tribromide (1.772 mL, 1.772 mmol, 1M solution in DCM). This gave after workup and purification by flash column chromatography (silica gel, eluting with ethyl acetate in hexane from 0-50%) ethyl 2-(2-hydroxy-4-(1-methyl-1H-pyrazol-4-yl)phenyl)acetate (396b) (81 mg, 35% yield) as a white solid; $^1$H NMR (300 MHz, DMSO-d$_6$) δ 9.51 (s, 1H), 7.99 (s, 1H), 7.71 (d, J=0.8 Hz, 1H), 7.07 (d, J=7.6 Hz, 1H), 6.97-6.86 (m, 2H), 4.05 (q, 2H), 3.85 (s, 3H), 3.51 (s, 2H), 1.17 (t, J=7.1, 0.7 Hz, 3H); MS (ES+): 261 (M+1), (ES−): 259 (M−1).

Step-3: Preparation of Ethyl 2-(2-((7-(3-(((tert-butoxycarbonyl)amino)methyl)phenyl)benzofuran-5-yl)methoxy)-4-(1-methyl-1H-pyrazol-4-yl)phenyl)acetate (396c)

Compound 396c was prepared according to the procedure reported in step-2 of scheme-23 from tert-butyl 3-(5-(hydroxymethyl)benzofuran-7-yl)benzylcarbamate (130d) (121 mg, 0.342 mmol) in DCM (10 mL) using triphenylphosphine (163 mg, 0.622 mmol), ethyl 2-(2-hydroxy-4-(1-methyl-1H-pyrazol-4-yl)phenyl)acetate (396b) (81 mg, 0.311 mmol) and (E)-bis(4-chlorobenzyl) diazene-1,2-dicarboxylate (DCAD, 229 mg, 0.622 mmol). This gave after workup and purification by flash column chromatography (silica gel, eluting with EtOAc in hexane from 0-50%) ethyl 2-(2-((7-(3-(((tert-butoxycarbonyl)amino)methyl)phenyl)benzofuran-5-yl)methoxy)-4-(1-methyl-1H-pyrazol-4-yl)phenyl)acetate (396c) (138 mg) as a pale-yellow oil; MS (ES+) 596 (M+1).

Step-4: Preparation of methyl 2-(2-((7-(3-(aminomethyl)phenyl)benzofuran-5-yl)methoxy)-4-(1-methyl-1H-pyrazol-4-yl)phenyl)acetate (396d)

Compound 396d was prepared according to the procedure reported in step-3 of scheme-305 from ethyl 2-(2-((7-(3-(((tert-butoxycarbonyl)amino)methyl)phenyl)benzofuran-5-yl)methoxy)-4-(1-methyl-1H-pyrazol-4-yl)phenyl)acetate (396c) (138 mg, from above step-3) in MeOH (4 mL) using HCl (4 M in dioxane; 0.778 mL, 3.11 mmol) and stirring at 60° C. for 1 h. This gave after workup methyl 2-(2-((7-(3-(aminomethyl)phenyl)benzofuran-5-yl)methoxy)-4-(1-methyl-1H-pyrazol-4-yl)phenyl)acetate (396d); MS (ES+): 482 (M+1).

Step-5: Preparation of 2-(2-((7-(3-(aminomethyl)phenyl)benzofuran-5-yl)methoxy)-4-(1-methyl-1H-pyrazol-4-yl)phenyl)acetic Acid (396e)

Compound 396e was prepared according to the procedure reported in step-4 of scheme-4 from of methyl 2-(2-((7-(3-(aminomethyl)phenyl)benzofuran-5-yl)methoxy)-4-(1-methyl-1H-pyrazol-4-yl)phenyl)acetate (396d) (from above step-4) in MeOH (3 mL), using a solution of sodium hydroxide (25 mg, 0.622 mmol) in water (1 mL). This gave after workup and purification by reverse phase column [C18 (100 g), eluting with ACN in water (containing 0.1% HCl) from 0-60%] 2-(2-((7-(3-(aminomethyl)phenyl)benzofuran-5-yl)methoxy)-4-(1-methyl-1H-pyrazol-4-yl)phenyl)acetic acid (396e) (80 mg, 55% yield) HCl salt as a white solid; $^1$H NMR (300 MHz, DMSO-d$_6$) δ 8.44-8.22 (m, 3H), 8.15 (s, 1H), 8.11 (d, J=2.2 Hz, 1H), 8.00 (d, J=1.7 Hz, 1H), 7.94 (dt, J=7.6, 1.6 Hz, 1H), 7.88 (d, J=0.8 Hz, 1H), 7.80 (d, J=1.6 Hz, 1H), 7.68 (d, J=1.7 Hz, 1H), 7.61 (t, J=7.6 Hz, 1H), 7.57-7.51 (m, 1H), 7.33 (d, J=1.6 Hz, 1H), 7.18 (d, J=7.7 Hz, 1H), 7.14-7.05 (m, 2H), 5.33 (s, 2H), 4.15 (q, J=5.8 Hz, 2H), 3.86 (s, 3H), 3.57 (s, 2H); MS (ES+): 468 (M+1), 466 (M−1); Analysis calculated for C$_{28}$H$_{25}$N$_3$O$_4$.1.5HCl.3H$_2$O: C, 58.36; H, 5.68; Cl, 9.23; N, 7.29; Found: C, 58.20; H, 5.48; Cl, 9.32; N, 7.26.

Scheme-397

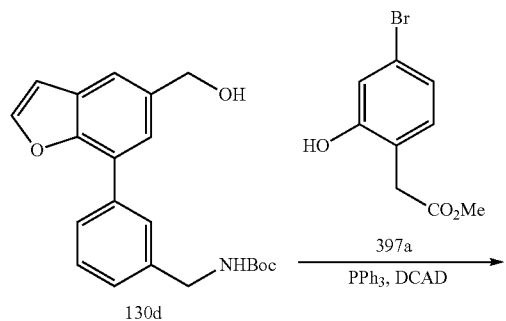

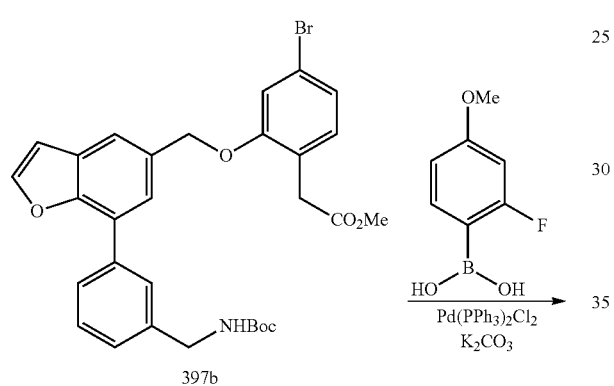

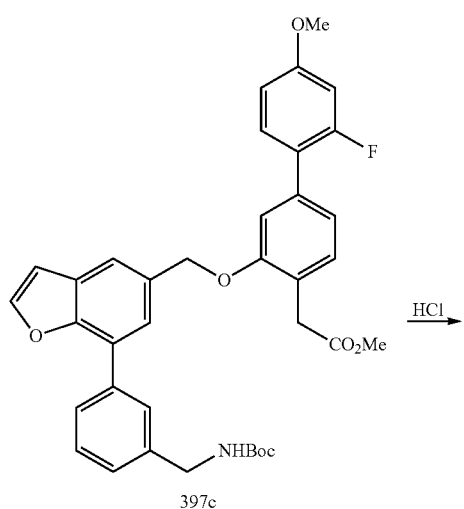

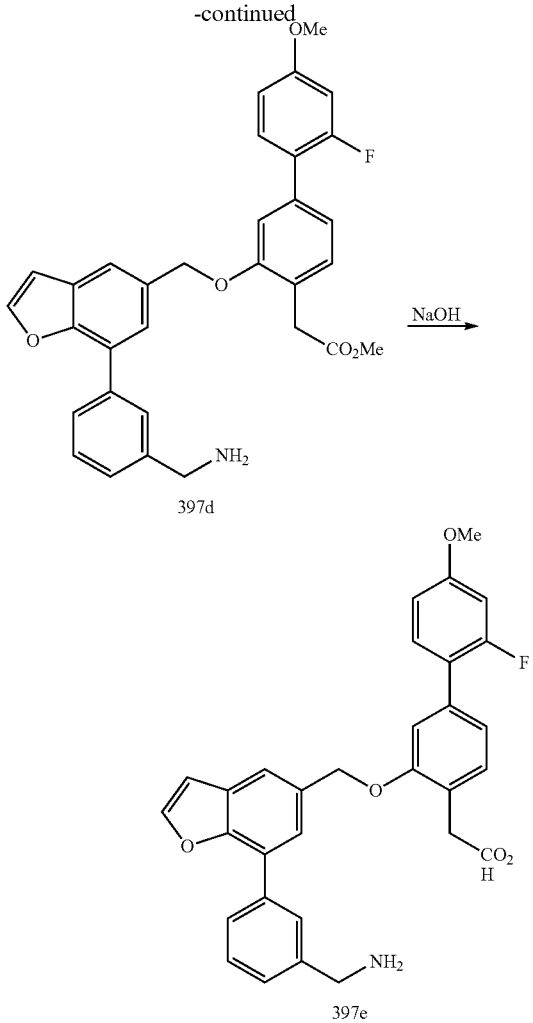

Preparation of 2-(3-((7-(3-(aminomethyl)phenyl)benzofuran-5-yl)methoxy)-2'-fluoro-4'-methoxy-[1,1'-biphenyl]-4-yl)acetic Acid (397e)

Step-1: Preparation of methyl 2-(4-bromo-2-((7-(3-(((tert-butoxycarbonyl)amino)methyl)phenyl)benzofuran-5-yl)methoxy)phenyl)acetate (397b)

Compound 397b was prepared according to the procedure reported in step-2 of scheme-23 from tert-butyl 3-(5-(hydroxymethyl)benzofuran-7-yl)benzylcarbamate (130d) (0.920 g, 2.60 mmol) in DCM (20 mL) using triphenylphosphine (1.241 g, 4.73 mmol), methyl 2-(4-bromo-2-hydroxyphenyl)acetate (397a) (0.58 g, 2.367 mmol) and (E)-bis(4-chlorobenzyl) diazene-1,2-dicarboxylate (DCAD, 1.738 g, 4.73 mmol). This gave after workup and purification by flash column chromatography (silica gel, eluting with ethyl acetate in hexanes from 0-20%) methyl 2-(4-bromo-2-((7-(3-(((tert-butoxycarbonyl)amino)methyl)phenyl)benzofuran-5-yl)methoxy)phenyl)acetate (397b) (1.08 g, 79% yield) as a white solid. $^1$H NMR (300 MHz, DMSO-$d_6$) δ 8.09 (d, J=2.2 Hz, 1H), 7.81-7.66 (m, 3H), 7.58-7.43 (m, 3H), 7.35 (d, J=1.9 Hz, 1H), 7.33-7.27 (m, 1H), 7.20 (d, J=8.0 Hz, 1H), 7.12 (dd, J=8.0, 1.8 Hz, 1H), 7.08 (d, J=2.2 Hz, 1H), 5.28 (s, 2H), 4.23 (d, J=6.2 Hz, 2H), 3.63 (s, 2H), 3.45 (s, 3H), 1.39 (s, 9H); MS (ES+): 602/604 (M+Na).

Step-2: Preparation of methyl 2-(3-((7-(3-(((tert-butoxycarbonyl)amino)methyl)phenyl)benzofuran-5-yl)methoxy)-2'-fluoro-4'-methoxy-[1,1'-biphenyl]-4-yl)acetate (397c)

Compound 397c was prepared according to the procedure reported in step-3 of scheme-1 from methyl 2-(4-bromo-2-((7-(3-(((tert-butoxycarbonyl)amino)methyl)phenyl)benzofuran-5-yl)methoxy)phenyl)acetate (397b) (200 mg, 0.345 mmol) in dioxane (4 mL) using (2-fluoro-4-methoxyphenyl)boronic acid (59 mg, 0.345 mmol), bis(triphenylphosphine)palladium(II) chloride (Pd(PPh$_3$)$_2$Cl$_2$) (24 mg, 0.034 mmol) and a solution of K$_2$CO$_3$ (143 mg, 1.034 mmol) in water (1 mL) under an N$_2$ atmosphere heating at 100° C. for 16 h on oil bath. This gave after workup and purification by flash column chromatography (silica gel, eluting with ethyl acetate in hexane from 0-20%) methyl 2-(3-((7-(3-(((tert-butoxycarbonyl)amino)methyl)phenyl)benzofuran-5-yl)methoxy)-2'-fluoro-4'-methoxy-[1,1'-biphenyl]-4-yl)acetate (397c) (120 mg) as a clear colorless oil; MS (ES+) 648 (M+Na).

Step-3: Preparation of methyl 2-(3-((7-(3-(aminomethyl)phenyl)benzofuran-5-yl)methoxy)-2'-fluoro-4'-methoxy-[1,1'-biphenyl]-4-yl)acetate (397d)

Compound 397d was prepared according to the procedure reported in step-3 of scheme-305 from methyl 2-(3-((7-(3-(((tert-butoxycarbonyl)amino)methyl)phenyl)benzofuran-5-yl)methoxy)-2'-fluoro-4'-methoxy-[1,1'-biphenyl]-4-yl)acetate (397c) (120 mg, from above step-2) in MeOH (5 mL) using HCl (4 M in dioxane; 0.861 mL, 3.45 mmol) and stirring at 40° C. for 1 h. This gave after workup methyl 2-(3-((7-(3-(aminomethyl)phenyl)benzofuran-5-yl)methoxy)-2'-fluoro-4'-methoxy-[1,1'-biphenyl]-4-yl)acetate (397d); MS (ES+): 526 (M+1).

Step-4: Preparation of 2-(3-((7-(3-(aminomethyl)phenyl)benzofuran-5-yl)methoxy)-2'-fluoro-4'-methoxy-[1,1'-biphenyl]-4-yl)acetic Acid (397e)

Compound 397e was prepared according to the procedure reported in step-4 of scheme-4 from methyl 2-(3-((7-(3-(aminomethyl)phenyl)benzofuran-5-yl)methoxy)-2'-fluoro-4'-methoxy-[1,1'-biphenyl]-4-yl)acetate (397d) (from above step-3) in MeOH (3 mL), using a solution of sodium hydroxide (41 mg, 1.034 mmol) in water (1 mL). This gave after workup and purification by reverse phase column [C18 (100 g), eluting with ACN in water (containing 0.1% HCl) from 0-60%] 2-(3-((7-(3-(aminomethyl)phenyl)benzofuran-5-yl)methoxy)-2'-fluoro-4'-methoxy-[1,1'-biphenyl]-4-yl)acetic acid (397e) (76 mg, 43% yield) HCl salt as a white solid; $^1$H NMR (300 MHz, DMSO-d$_6$) δ 8.11 (d, J=2.2 Hz, 1H), 8.00 (d, J=1.7 Hz, 1H), 7.94 (dt, J=7.6, 1.5 Hz, 1H), 7.78 (d, J=1.6 Hz, 1H), 7.67 (d, J=1.6 Hz, 1H), 7.60 (t, J=7.6 Hz, 1H), 7.53 (dt, J=7.7, 1.5 Hz, 1H), 7.46 (dd, J=9.3, 8.5 Hz, 1H), 7.29 (d, J=7.8 Hz, 1H), 7.22 (t, J=1.4 Hz, 1H), 7.11-7.01 (m, 2H), 6.93 (dd, J=12.9, 2.5 Hz, 1H), 6.90-6.84 (m, 1H), 5.33 (s, 2H), 4.14 (s, 2H), 3.81 (s, 3H), 3.63 (s, 2H); MS (ES+): 512 (M+1), 511 (M−1); Analysis calculated for C$_{31}$H$_{26}$FNO$_5$.HCl.1.25H$_2$O: C, 65.26; H, 5.21; Cl, 6.21; N, 2.46; Found: C, 65.26; H, 5.03; Cl: 6.19; N, 2.62.

Scheme-398

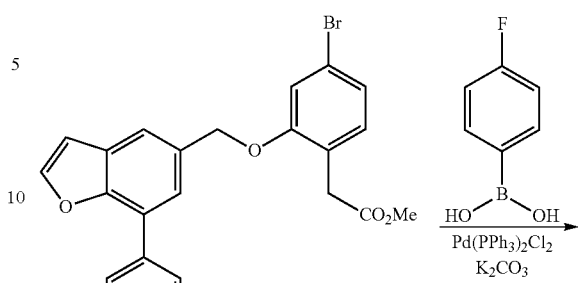

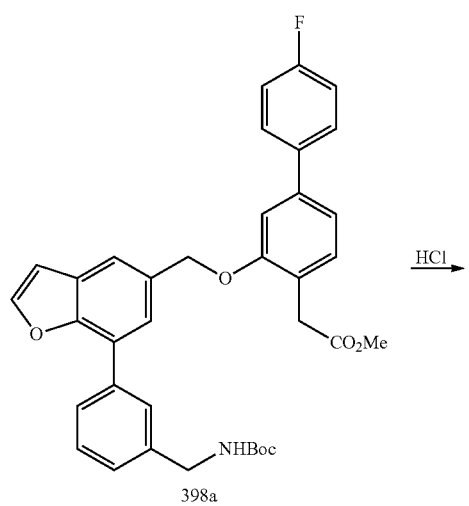

398a

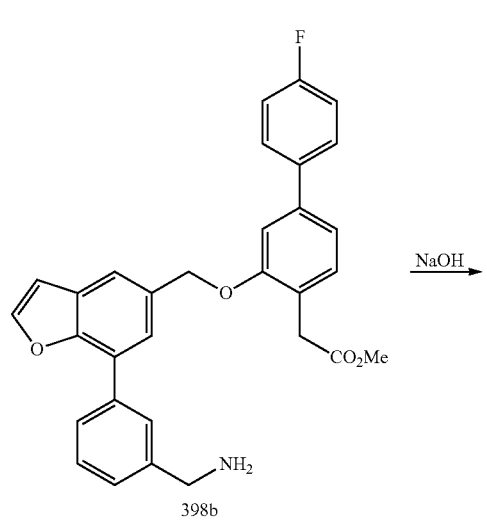

398b

1237

-continued

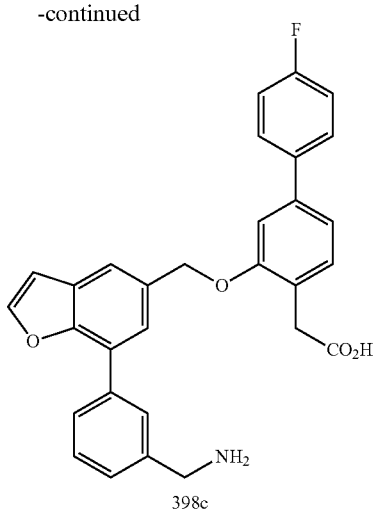

398c

Preparation of 2-(3-((7-(3-(aminomethyl)phenyl)
benzofuran-5-yl)methoxy)-4'-fluoro-[1,1'-biphenyl]-
4-yl)acetic Acid (398c)

Step-1: Preparation of methyl 2-(3-((7-(3-(((tert-
butoxycarbonyl)amino)methyl)phenyl)benzofuran-5-
yl)methoxy)-4'-fluoro-[1,1'-biphenyl]-4-yl)acetate
(398a)

Compound 398a was prepared according to the procedure reported in step-3 of scheme-1 from methyl 2-(4-bromo-2-((7-(3-(((tert-butoxycarbonyl)amino)methyl)phenyl)benzofuran-5-yl)methoxy)phenyl)acetate (397b) (193 mg, 0.332 mmol) in dioxane (4 mL) using 4-fluorophenylboronic acid (56 mg, 0.399 mmol; CAS #1765-93-1), bis(triphenylphosphine)palladium(II) chloride (Pd(PPh$_3$)$_2$Cl$_2$) (23 mg, 0.033 mmol) and a solution of K$_2$CO$_3$ (138 mg, 0.997 mmol) in water (1 mL) under an N$_2$ atmosphere heating at 100° C. for 16 h on oil bath. This gave after workup and purification by flash column chromatography (silica gel, 12g, eluting with ethyl acetate in hexane from 0-20%) methyl 2-(3-((7-(3-(((tert-butoxycarbonyl)amino)methyl)phenyl)benzofuran-5-yl)methoxy)-4'-fluoro-[1,1'-biphenyl]-4-yl)acetate (398a) (140 mg) as a clear colorless oil; MS (ES+): 618 (M+Na).

Step-2: Preparation of methyl 2-(3-((7-(3-(aminomethyl)phenyl)benzofuran-5-yl)methoxy)-4'-fluoro-[1,1'-biphenyl]-4-yl)acetate (398b)

Compound 398b was prepared according to the procedure reported in step-3 of scheme-305 from methyl 2-(3-((7-(3-(((tert-butoxycarbonyl)amino)methyl)phenyl)benzofuran-5-yl)methoxy)-4'-fluoro-[1,1'-biphenyl]-4-yl)acetate (398a) (140 mg, from above step-1) in MeOH (4 mL) using HCl (4 M in dioxane; 0.831 mL, 3.32 mmol) and stirring at 40° C. for 1 h. This gave after workup methyl 2-(3-((7-(3-(aminomethyl)phenyl)benzofuran-5-yl)methoxy)-4'-fluoro-[1,1'-biphenyl]-4-yl)acetate (398b); MS (ES+): 496 (M+1).

Step-3: Preparation of 2-(3-((7-(3-(aminomethyl)phenyl)benzofuran-5-yl)methoxy)-4'-fluoro-[1,1'-biphenyl]-4-yl)acetic Acid (398c)

Compound 398c was prepared according to the procedure reported in step-4 of scheme-4 from methyl 2-(3-((7-(3-(aminomethyl)phenyl)benzofuran-5-yl)methoxy)-4'-fluoro-[1,1'-biphenyl]-4-yl)acetate (398b) (from above step-2) in MeOH (3 mL), using a solution of sodium hydroxide (40 mg, 0.997 mmol) in water (1 mL). This gave after workup and purification by reverse phase column [C18 (100 g), eluting with ACN in water (containing 0.1% HCl) from 0-60%] 2-(3-((7-(3-(aminomethyl)phenyl)benzofuran-5-yl)methoxy)-4'-fluoro-[1,1'-biphenyl]-4-yl)acetic acid (398c) (41 mg, 26% yield) HCl salt as a white solid. $^1$H NMR (300 MHz, DMSO-d$_6$) δ 8.11 (d, J=2.2 Hz, 1H), 8.01 (t, J=1.6 Hz, 1H), 7.94 (dt, J=7.6, 1.5 Hz, 1H), 7.80 (d, J=1.6 Hz, 1H), 7.77-7.67 (m, 3H), 7.61 (t, J=7.6 Hz, 1H), 7.54 (dt, J=7.9, 1.6 Hz, 1H), 7.36 (d, J=1.7 Hz, 1H), 7.34-7.24 (m, 3H), 7.19 (dd, J=7.7, 1.6 Hz, 1H), 7.08 (d, J=2.2 Hz, 1H), 5.39 (s, 2H), 4.15 (s, 2H), 3.63 (s, 2H). $^{19}$F NMR (300 MHz, DMSO-d$_6$) δ −115.49; MS (ES+): 482 (M+1), 480 (M−1); Analysis calculated for C$_{30}$H$_{24}$FNO$_4$.HCl.H$_2$O: C, 67.23; H, 5.08; Cl, 6.61; N, 2.61; Found: C, 66.94; H, 4.91; Cl, 7.09; N, 2.69.

Scheme-399

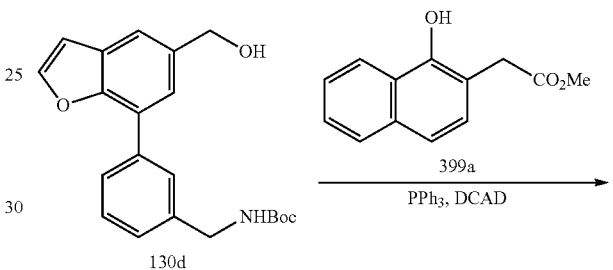

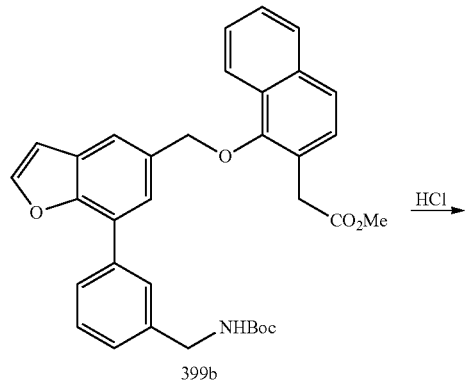

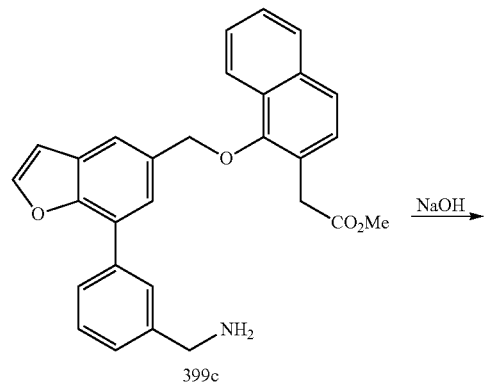

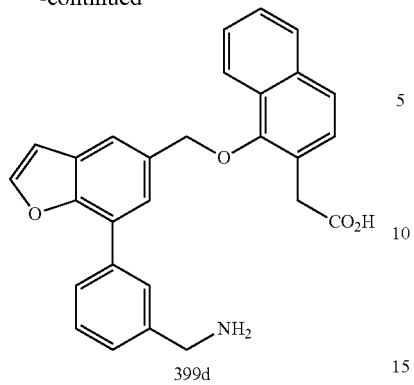

Preparation of 2-(1-((7-(3-(aminomethyl)phenyl) benzofuran-5-yl)methoxy)naphthalen-2-yl)acetic Acid (399d)

Step-1: Preparation of methyl 2-(1-((7-(3-(((tert-butoxycarbonyl)amino)methyl)phenyl)benzofuran-5-yl)methoxy)naphthalen-2-yl)acetate (399b)

Compound 399b was prepared according to the procedure reported in step-2 of scheme-23 from tert-butyl 3-(5-(hydroxymethyl)benzofuran-7-yl)benzylcarbamate (130d) (426 mg, 1.206 mmol) in DCM (20 mL) using triphenylphosphine (431 mg, 1.644 mmol) methyl 2-(1-hydroxynaphthalen-2-yl)acetate (399a) (237 mg, 1.096 mmol; CAS #888739-82-0) and E)-bis(4-chlorobenzyl) diazene-1,2-dicarboxylate (DCAD, 604 mg, 1.644 mmol). This gave after workup and purification by flash column chromatography (silica gel, eluting with ethyl acetate in hexanes from 0-20%) methyl 2-(1-((7-(3-(((tert-butoxycarbonyl)amino)methyl)phenyl)benzofuran-5-yl)methoxy)naphthalen-2-yl)acetate (399b) (75 mg) as a colorless oil; MS (ES+) 574 (M+Na).

Step-2: Preparation of methyl 2-(1-((7-(3-(aminomethyl)phenyl)benzofuran-5-yl)methoxy)naphthalen-2-yl)acetate (399c)

Compound 399c was prepared according to the procedure reported in step-3 of scheme-305 from methyl 2-(1-((7-(3-(((tert-butoxycarbonyl)amino)methyl)phenyl)benzofuran-5-yl)methoxy)naphthalen-2-yl)acetate (399b) (75 mg, from above step-1) in MeOH (5 mL) using HCl (4 M in dioxane; 1.096 mL, 4.38 mmol) and stirring at 40° C. for 1 h. This gave after workup methyl 2-(1-((7-(3-(aminomethyl)phenyl)benzofuran-5-yl)methoxy)naphthalen-2-yl)acetate (399c); MS (ES+): 452 (M+1).

Step-3: Preparation of 2-(1-((7-(3-(aminomethyl)phenyl)benzofuran-5-yl)methoxy)naphthalen-2-yl) acetic Acid (399d)

Compound 399d was prepared according to the procedure reported in step-4 of scheme-4 from methyl 2-(1-((7-(3-(aminomethyl)phenyl)benzofuran-5-yl)methoxy)naphthalen-2-yl)acetate (399c) (from above step-2) in MeOH (3 mL), using a solution of sodium hydroxide (132 mg, 3.29 mmol) in water (1 mL). This gave after workup and purification by reverse phase column [C18 (100 g), eluting with ACN in water (containing 0.1% HCl) from 0-60%] 2-(1-((7-(3-(aminomethyl)phenyl)benzofuran-5-yl)methoxy) naphthalen-2-yl)acetic acid (399d) (18 mg, 4% yield) HCl salt as a white solid; $^1$H NMR (300 MHz, DMSO-$d_6$) δ 8.19-8.07 (m, 2H), 8.05-8.00 (m, 1H), 8.00-7.87 (m, 3H), 7.79-7.67 (m, 2H), 7.67-7.51 (m, 4H), 7.47 (dd, J=8.4, 2.5 Hz, 1H), 7.13 (d, J=2.3 Hz, 1H), 5.17 (s, 2H), 4.16 (s, 2H), 3.84 (s, 2H); MS (ES+): 438 (M+1), 436 (M−1)

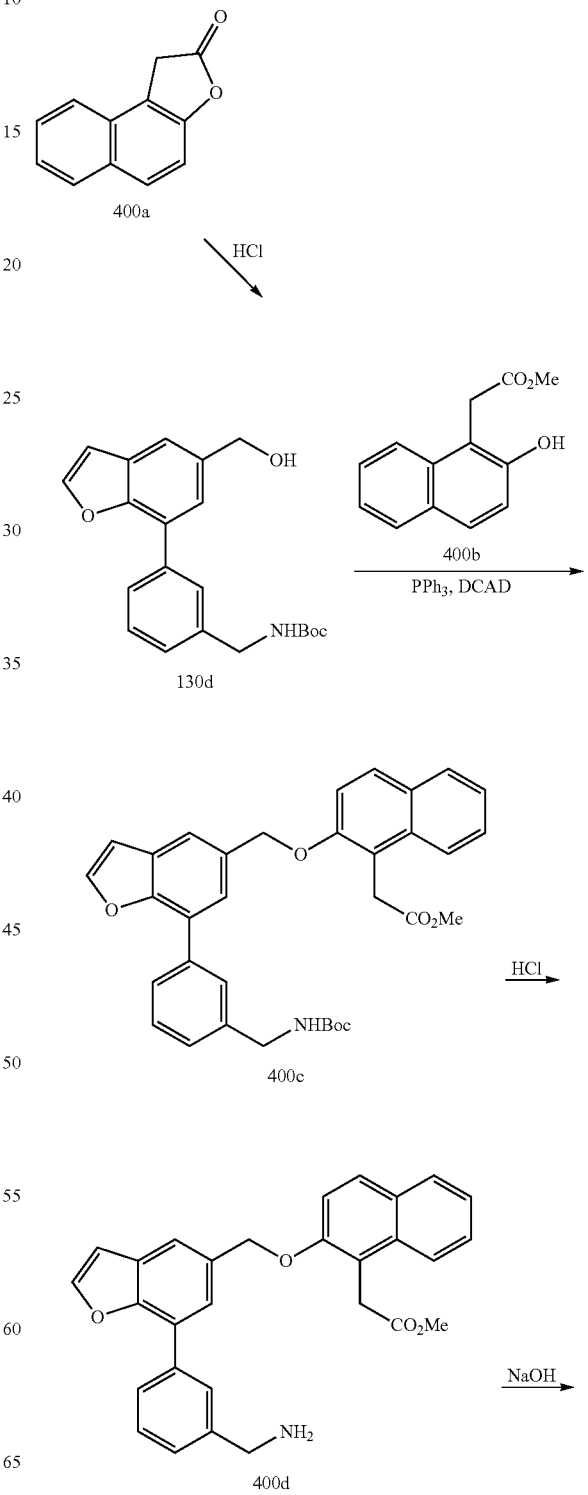

Scheme-400

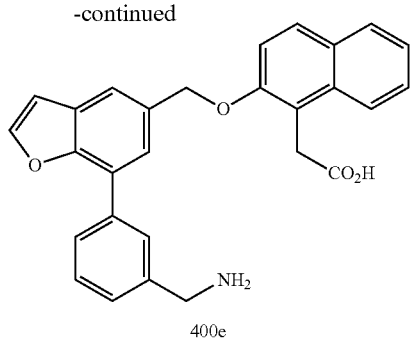

400e

Preparation of 2-(2-((7-(3-(aminomethyl)phenyl)benzofuran-5-yl)methoxy)naphthalen-1-yl)acetic Acid (400e)

Step-1: Preparation of methyl 2-(2-hydroxynaphthalen-1-yl)acetate (400b)

Compound 400b was prepared according to the procedure reported in step-3 of scheme-305 from naphtho[2,1-b]furan-2(1H)-one (400a) (170 mg, 0.923 mmol; CAS #4352-63-0) in MeOH (10 mL) using HCl (4 M in dioxane; 2.307 mL, 9.23 mmol) and stirring at 60° C. for 1 h. This gave after workup methyl 2-(2-hydroxynaphthalen-1-yl)acetate (400b) (200 mg, 100% yield) as a white solid. $^1$H NMR (300 MHz, DMSO-$d_6$) δ 9.82 (s, 1H), 7.78 (td, J=7.2, 6.6, 1.2 Hz, 2H), 7.71 (d, J=8.8 Hz, 1H), 7.44 (ddd, J=8.4, 6.8, 1.4 Hz, 1H), 7.28 (ddd, J=8.0, 6.8, 1.0 Hz, 1H), 7.19 (d, J=8.8 Hz, 1H), 4.03 (s, 2H), 3.59 (s, 3H).

Step-2: Preparation of methyl 2-(2-((7-(3-(((tert-butoxycarbonyl)amino)methyl)phenyl)benzofuran-5-yl)methoxy)naphthalen-1-yl)acetate (400c)

Compound 400c was prepared according to the procedure reported in step-2 of scheme-23 from tert-butyl 3-(5-(hydroxymethyl)benzofuran-7-yl)benzylcarbamate (130d) (345 mg, 0.977 mmol) in DCM (15 mL) using triphenylphosphine (349 mg, 1.332 mmol) methyl 2-(2-hydroxynaphthalen-1-yl)acetate (400b) (192 mg, 0.888 mmol) and E)-bis(4-chlorobenzyl) diazene-1,2-dicarboxylate (DCAD, 489 mg, 1.332 mmol). This gave after workup and purification by flash column chromatography (silica gel, eluting with ethyl acetate in hexanes from 0-20%) methyl 2-(2-((7-(3-(((tert-butoxycarbonyl)amino)methyl)phenyl)benzofuran-5-yl)methoxy)naphthalen-1-yl)acetate (400c) as a colorless oil; MS (ES+) 574 (M+Na).

Step-3: Preparation of methyl 2-(2-((7-(3-(aminomethyl)phenyl)benzofuran-5-yl)methoxy)naphthalen-1-yl)acetate (400d)

Compound 400d was prepared according to the procedure reported in step-3 of scheme-305 from methyl 2-(2-((7-(3-(((tert-butoxycarbonyl)amino)methyl)phenyl)benzofuran-5-yl)methoxy)naphthalen-1-yl)acetate (400c) (from above step-2) in MeOH (5 mL) using HCl (4 M in dioxane; 1.110 mL, 4.44 mmol) and stirring at 40° C. for 1 h. This gave after workup methyl 2-(2-((7-(3-(aminomethyl)phenyl)benzofuran-5-yl)methoxy)naphthalen-1-yl)acetate (400d); MS (ES+) 452 (M+1).

Step-4: Preparation of 2-(2-((7-(3-(aminomethyl)phenyl)benzofuran-5-yl)methoxy)naphthalen-1-yl)acetic Acid (400e)

Compound 400e was prepared according to the procedure reported in step-4 of scheme-4 from methyl 2-(2-((7-(3-(aminomethyl)phenyl)benzofuran-5-yl)methoxy)naphthalen-1-yl)acetate (400d) (from above step-3) in MeOH (3 mL), using a solution of sodium hydroxide (107 mg, 2.66 mmol) in water (1 mL). This gave after workup and purification by reverse phase column [C18 (100 g), eluting with ACN in water (containing 0.1% HCl) from 0-60%] 2-(2-((7-(3-(aminomethyl)phenyl)benzofuran-5-yl)methoxy)naphthalen-1-yl)acetic acid (400e) (53 mg, 14% yield) HCl salt as a white solid; $^1$H NMR (300 MHz, DMSO-$d_6$) δ 8.10 (d, J=2.2 Hz, 1H), 8.00 (d, J=1.8 Hz, 1H), 7.97-7.84 (m, 4H), 7.81 (d, J=1.6 Hz, 1H), 7.70 (d, J=1.7 Hz, 1H), 7.64-7.46 (m, 4H), 7.37 (ddd, J=8.0, 6.8, 1.1 Hz, 1H), 7.07 (d, J=2.2 Hz, 1H), 5.44 (s, 2H), 4.14 (s, 2H), 4.08 (s, 2H); MS (ES+): 438 (M+1), 436 (M−1); Analysis calculated for $C_{28}H_{23}NO_4 \cdot HCl \cdot 1.25 H_2O$: C, 67.74; H, 5.38; Cl, 7.14; N, 2.82; Found: C, 67.54; H, 5.31; Cl, 7.20; N, 2.93.

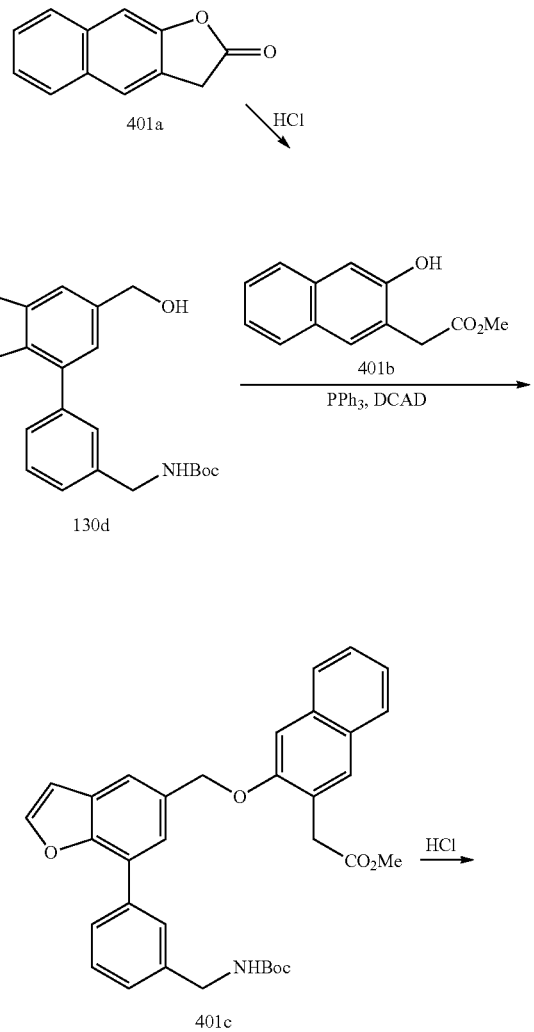

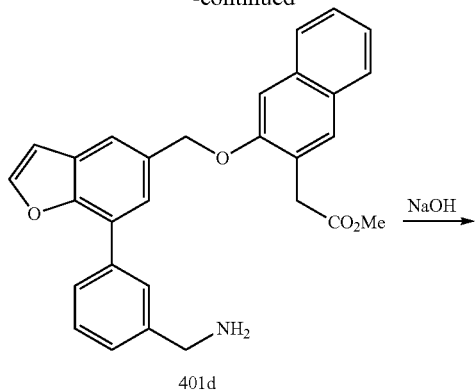

Preparation of 2-(3-((7-(3-(aminomethyl)phenyl) benzofuran-5-yl)methoxy)naphthalen-2-yl)acetic Acid (401e)

Step-1: Preparation of methyl 2-(3-hydroxynaphthalen-2-yl)acetate (401b)

Compound 401b was prepared according to the procedure reported in step-3 of scheme-305 from naphtho[2,3-b]furan-2(3H)-one (401a) (100 mg, 0.543 mmol; CAS #4420-43-3) in MeOH (10 mL) using HCl (4 M in dioxane; 1.357 mL, 5.43 mmol) and stirring at 60° C. for 1 h. This gave after workup methyl 2-(3-hydroxynaphthalen-2-yl)acetate (401b) (114 mg, 97% yield) as a magenta solid. $^1$H NMR (300 MHz, DMSO-$d_6$) δ 9.97 (s, 1H), 7.76-7.61 (m, 3H), 7.36 (ddd, J=8.1, 6.8, 1.4 Hz, 1H), 7.25 (ddd, J=8.1, 6.8, 1.3 Hz, 1H), 7.12 (s, 1H), 3.74 (s, 2H), 3.61 (s, 3H).

Step-2: Preparation of methyl 2-(3-((7-(3-(((tert-butoxycarbonyl)amino)methyl)phenyl)benzofuran-5-yl)methoxy)naphthalen-2-yl)acetate (401c)

Compound 401c was prepared according to the procedure reported in step-2 of scheme-23 from tert-butyl 3-(5-(hydroxymethyl)benzofuran-7-yl)benzylcarbamate (130d) (205 mg, 0.580 mmol) in DCM (20 mL) using triphenylphosphine (207 mg, 0.791 mmol), methyl 2-(3-hydroxynaphthalen-2-yl)acetate (401b) (114 mg, 0.527 mmol) and E)-bis(4-chlorobenzyl) diazene-1,2-dicarboxylate (DCAD, 290 mg, 0.791 mmol). This gave after workup and purification by flash column chromatography (silica gel, eluting with ethyl acetate in hexanes from 0-20%) methyl 2-(3-((7-(3-(((tert-butoxycarbonyl)amino)methyl)phenyl)benzofuran-5-yl) methoxy)naphthalen-2-yl)acetate (401c) (108 mg) as a colorless oil; MS (ES+) 574 (M+Na).

Step-3: Preparation of methyl 2-(3-((7-(3-(aminomethyl)phenyl)benzofuran-5-yl)methoxy)naphthalen-2-yl)acetate (401d)

Compound 401d was prepared according to the procedure reported in step-3 of scheme-305 from methyl 2-(3-((7-(3-(((tert-butoxycarbonyl)amino)methyl)phenyl)benzofuran-5-yl)methoxy)naphthalen-2-yl)acetate (401c) (108 mg, from above step-2) in MeOH (5 mL) using HCl (4 M in dioxane; 0.659 mL, 2.64 mmol) and stirring at 40° C. for 1 h. This gave after workup methyl 2-(3-((7-(3-(aminomethyl)phenyl)benzofuran-5-yl)methoxy)naphthalen-2-yl)acetate (401d); MS (ES+) 452 (M+1).

Step-4: Preparation of 2-(3-((7-(3-(aminomethyl) phenyl)benzofuran-5-yl)methoxy)naphthalen-2-yl) acetic Acid (401e)

Compound 401e was prepared according to the procedure reported in step-4 of scheme-4 from methyl 2-(3-((7-(3-(aminomethyl)phenyl)benzofuran-5-yl)methoxy)naphthalen-2-yl)acetate (401d) (from above step-3) in MeOH (3 mL), using a solution of sodium hydroxide (63 mg, 1.582 mmol) in water (1 mL). This gave after workup and purification by reverse phase column [C18 (100 g), eluting with ACN in water (containing 0.1% HCl) from 0-60%] 2-(3-((7-(3-(aminomethyl)phenyl)benzofuran-5-yl)methoxy) naphthalen-2-yl)acetic acid (401e) (49 mg, 21% yield) HCl salt as a pale-yellow solid. $^1$H NMR (300 MHz, DMSO-$d_6$) δ 8.12 (d, J=2.2 Hz, 1H), 8.02 (d, J=1.7 Hz, 1H), 7.96 (dt, J=7.5, 1.5 Hz, 1H), 7.85-7.80 (m, 2H), 7.80-7.75 (m, 2H), 7.71 (d, J=1.7 Hz, 1H), 7.61 (t, J=7.7 Hz, 1H), 7.53 (dt, J=7.5, 1.4 Hz, 1H), 7.50-7.40 (m, 2H), 7.35 (ddd, J=8.0, 6.9, 1.3 Hz, 1H), 7.08 (d, J=2.2 Hz, 1H), 5.40 (s, 2H), 4.15 (s, 2H), 3.77 (s, 2H); MS (ES+): 438 (M+1), 436 (M−1); Analysis calculated for $C_{28}H_{23}NO_4 \cdot HCl \cdot 1.5H_2O$: C, 67.13; H, 5.43; Cl, 7.08; N, 2.80; Found: C, 67.24; H, 5.24; Cl, 7.18; N, 2.90.

Scheme-402

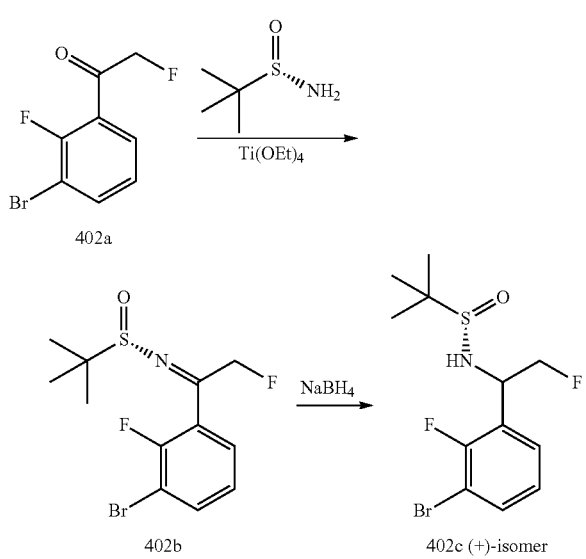

1245

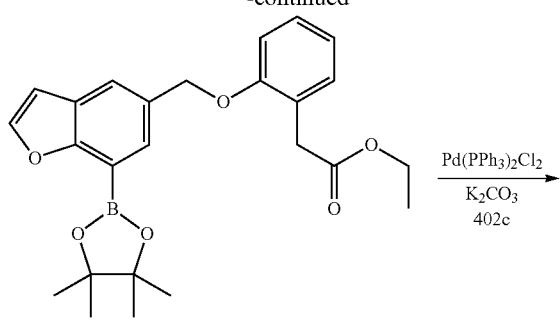

59a

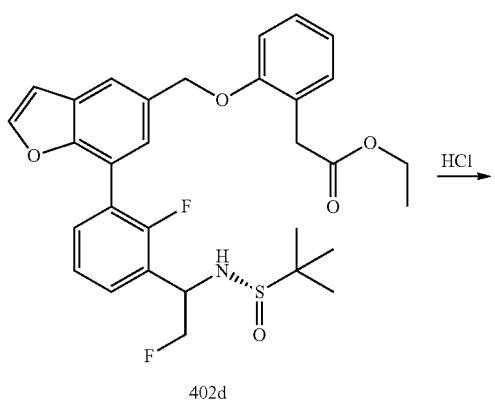

402d

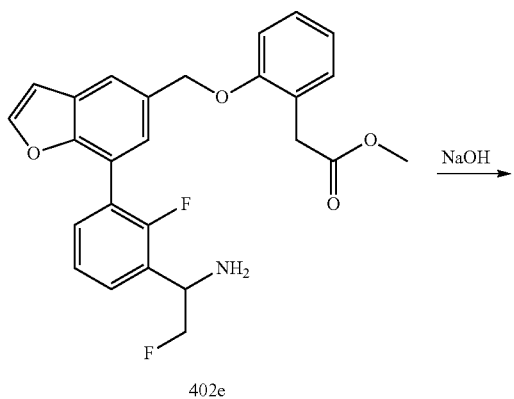

402e

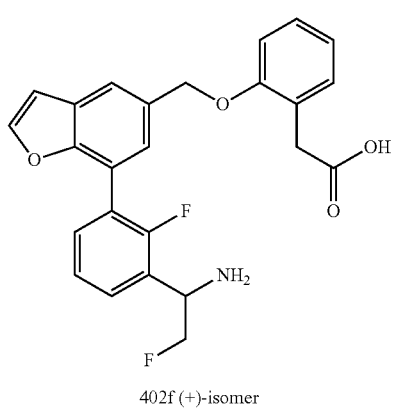

402f (+)-isomer

1246

Preparation of (+)-2-(2-((7-(3-(1-amino-2-fluoro-ethyl)-2-fluorophenyl)benzofuran-5-yl)methoxy)phenyl)acetic Acid (402f)

Step-1: Preparation of (S)—N-(1-(3-bromo-2-fluorophenyl)-2-fluoroethylidene)-2-methylpropane-2-sulfinamide (402b)

Compound 402b was prepared according to the procedure reported in step-1 of scheme-258 from 1-(3-bromo-2-fluorophenyl)-2-fluoroethanone (402a) (250 mg, 1.064 mmol; CAS #1646556-83-3; prepared according to the method reported by Belanger, David B. et al; in PCT Int. Appl., 2015009977, 22 Jan. 2015) and (S)-2-methylpropane-2-sulfinamide (258 mg, 2.127 mmol) in tetrahydrofuran (15 mL) using tetraethoxytitanium (728 mg, 3.19 mmol) and heating at 65° C. for 16 h. This gave after workup and purification by flash column chromatography (silica gel, eluting with ethyl acetate in hexanes 0 to 10%) (S)—N-(1-(3-bromo-2-fluorophenyl)-2-fluoroethylidene)-2-methylpropane-2-sulfinamide (402b) (80 mg) as a yellow oil; MS (ES+): 360/362 (M+Na).

Step-2: Preparation of (+)-(S)—N-(1-(3-bromo-2-fluorophenyl)-2-fluoroethyl)-2-methylpropane-2-sulfinamide (402c)

Compound 402c was prepared according to the procedure reported in step-2 of scheme-258 from (S)—N-(1-(3-bromo-2-fluorophenyl)-2-fluoroethylidene)-2-methylpropane-2-sulfinamide (402b) (80 mg, from above step-1) in tetrahydrofuran (5 mL) using sodium borohydride (80 mg, 2.127 mmol). This gave after workup and purification by flash column chromatography (silica gel, 24 g, eluting with ethyl acetate in hexanes 0 to 40%) (+)-(S)—N-(1-(3-bromo-2-fluorophenyl)-2-fluoroethyl)-2-methylpropane-2-sulfinamide (402c) (53 mg, 15% yield) as an orange oil. $^1$H NMR (300 MHz, DMSO-$d_6$) δ 7.67 (ddt, J=8.2, 6.8, 1.4 Hz, 1H), 7.57 (dtd, J=15.9, 7.2, 6.5, 1.6 Hz, 1H), 7.21 (tt, J=7.8, 1.6 Hz, 1H), 6.01 (dd, J=58.3, 8.1 Hz, 1H), 4.94-4.77 (m, 1H), 4.77-4.41 (m, 2H), 1.10 (d, J=5.4 Hz, 9H). $^{19}$F NMR (282 MHz, DMSO-$d_6$) δ –112.79, –218.57; MS (ES+) 340/342 (M+1); Optical rotation [t]D=+24 (c=0.025, MeOH)

Step-3: Preparation of Ethyl 2-(2-((7-(3-(1-((S)-1,1-dimethylethylsulfinamido)-2-fluoroethyl)-2-fluorophenyl)benzofuran-5-yl)methoxy)phenyl)acetate (402d)

Compound 402d was prepared according to the procedure reported in step-3 of scheme-1 from ethyl 2-(2-((7-(4,4,5,5-tetramethyl-1,3,2-dioxaborolan-2-yl)benzofuran-5-yl)methoxy)phenyl)acetate (59a) (75 mg, 0.171 mmol) in dioxane (4 mL) using (+)-(S)—N-(1-(3-bromo-2-fluorophenyl)-2-fluoroethyl)-2-methylpropane-2-sulfinamide (402c) (53 mg, 0.156 mmol), Pd(PPh$_3$)$_2$Cl$_2$ (11 mg, 0.016 mmol) and a solution of K$_2$CO$_3$ (65 mg, 0.467 mmol) in water (1 mL) under a nitrogen atmosphere and heating at 100° C. for 16 h on oil bath. This gave after workup and purification by flash column chromatography (silica gel, 12 g, eluting with 0-40% EtOAc in hexane ethyl 2-(2-((7-(3-(1-((S)-1,1-dimethylethylsulfinamido)-2-fluoroethyl)-2-fluorophenyl)benzofuran-5-yl)methoxy)phenyl)acetate (402d) (53 mg) as a colorless oil; MS (ES+): 570 (M+1).

Step-4: Preparation of methyl 2-(2-((7-(3-(1-amino-2-fluoroethyl)-2-fluorophenyl)benzofuran-5-yl)methoxy)phenyl)acetate (402e)

Compound 402e was prepared according to the procedure reported in step-10 of scheme-257 from ethyl 2-(2-((7-(3-(1-((S)-1,1-dimethylethylsulfinamido)-2-fluoroethyl)-2-fluorophenyl)benzofuran-5-yl)methoxy)phenyl)acetate (402d) (53 mg, from above step-3) in MeOH (5 mL) using HCl (4 M in 1,4-dioxane, 0.389 mL, 1.558 mmol) and heating at 40° C. for 1 h. This gave after workup methyl 2-(2-((7-(3-(1-amino-2-fluoroethyl)-2-fluorophenyl)benzofuran-5-yl)methoxy)phenyl)acetate (402e); MS (ES+) 452 (M+1);

Step-5: Preparation of (+)-2-(2-((7-(3-(1-amino-2-fluoroethyl)-2-fluorophenyl)benzofuran-5-yl)methoxy)phenyl)acetic Acid (402f)

Compound 402f was prepared according to the procedure reported in step-4 of scheme-4 from methyl 2-(2-((7-(3-(1-amino-2-fluoroethyl)-2-fluorophenyl)benzofuran-5-yl)methoxy)phenyl)acetate (402e) (from above step-4) in MeOH (3 mL) using a solution of NaOH (18.69 mg, 0.467 mmol) in water (1 mL). This gave after workup and purification by reverse phase column (C18, 100 g, 0-60% MeCN in H$_2$O containing 0.1% HCl) (+)-2-(2-((7-(3-(1-amino-2-fluoroethyl)-2-fluorophenyl)benzofuran-5-yl)methoxy)phenyl)acetic acid (402f) (31 mg, 46% yield) HCl salt as a white solid; $^1$H NMR (300 MHz, DMSO-d$_6$) δ 8.06 (d, J=2.2 Hz, 1H), 7.83 (d, J=1.6 Hz, 1H), 7.80-7.69 (m, 2H), 7.53-7.45 (m, 2H), 7.28-7.18 (m, 2H), 7.14-7.04 (m, 2H), 6.91 (td, J=7.4, 1.1 Hz, 1H), 5.27 (s, 2H), 5.07-4.89 (m, 2H), 4.83-4.74 (m, 1H), 3.58 (s, 2H); MS (ES+): 438 (M+1), 436 (M−1); Analysis calculated for C$_{25}$H$_{21}$F$_2$NO$_4$·1.15HCl·2H$_2$O: C, 58.26; H, 5.11; Cl, 7.91; N, 2.72; Found: C, 58.52; H, 4.85; Cl, 7.76; N, 2.73; Optical rotation [t]D=+3.02 (c=0.265, MeOH).

Scheme-403

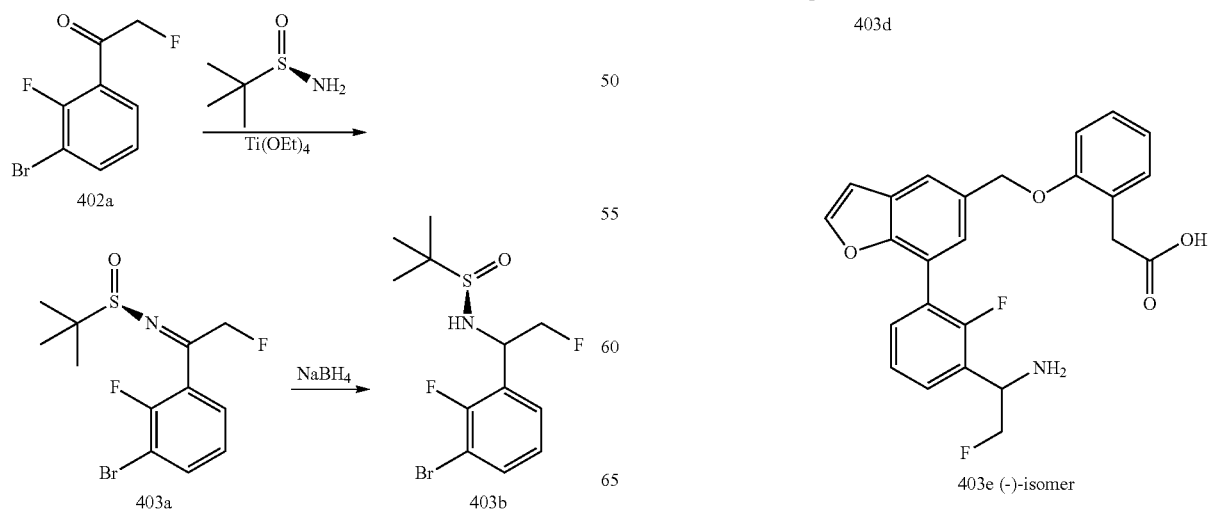

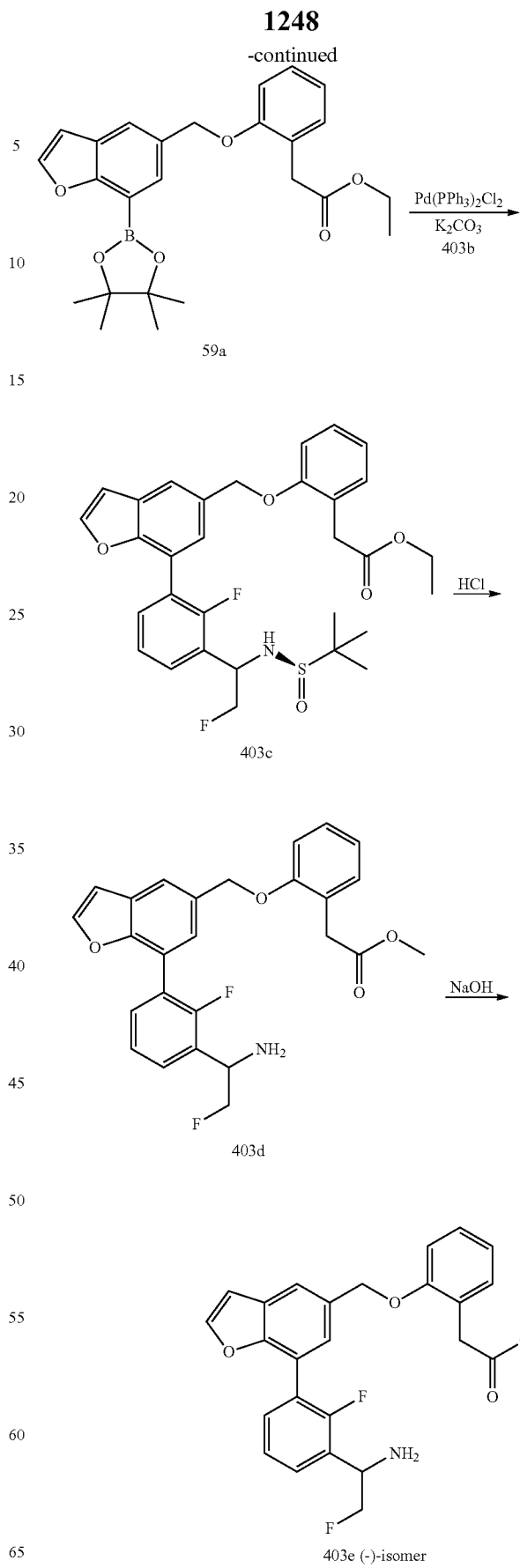

Preparation of (−)-2-(2-((7-(3-(1-amino-2-fluoro-ethyl)-2-fluorophenyl)benzofuran-5-yl)methoxy)phenyl)acetic Acid (403e)

Step-1: Preparation of (R)—N-(1-(3-bromo-2-fluorophenyl)-2-fluoroethylidene)-2-methylpropane-2-sulfinamide (403a)

Compound 403a was prepared according to the procedure reported in step-1 of scheme-258 from 1-(3-bromo-2-fluorophenyl)-2-fluoroethanone (402a) (729 mg, 3.10 mmol; CAS #1646556-83-3; prepared according to the method reported by Belanger, David B. et al; in PCT Int. Appl., 2015009977, 22 Jan. 2015) and (R)-2-methylpropane-2-sulfinamide (752 mg, 6.20 mmol) in tetrahydrofuran (15 mL) using tetraethoxytitanium (2123 mg, 9.31 mmol) and heating at 65° C. for 16 h. This gave after workup and purification by flash column chromatography (silica gel, eluting with ethyl acetate in hexanes 0 to 10%) (R)—N-(1-(3-bromo-2-fluorophenyl)-2-fluoroethylidene)-2-methylpropane-2-sulfinamide (403a) as a yellow oil; MS (ES+): 360/362 (M+Na).

Step-2: Preparation of (R)—N-(1-(3-bromo-2-fluorophenyl)-2-fluoroethyl)-2-methylpropane-2-sulfinamide (403b)

Compound 403b was prepared according to the procedure reported in step-2 of scheme-258 from (R)—N-(1-(3-bromo-2-fluorophenyl)-2-fluoroethylidene)-2-methylpropane-2-sulfinamide (403a) (from above step-1) in tetrahydrofuran (15 mL) using sodium borohydride (235 mg, 6.20 mmol). This gave after workup and purification by flash column chromatography (silica gel, 24 g, eluting with ethyl acetate in hexanes 0 to 40%) (R)—N-(1-(3-bromo-2-fluorophenyl)-2-fluoroethyl)-2-methylpropane-2-sulfinamide (403b) (202 mg, 19% yield) as an orange oil; $^1$H NMR (300 MHz, DMSO-$d_6$) δ 7.67 (ddt, J=8.1, 6.7, 1.3 Hz, 1H), 7.57 (dddd, J=15.8, 8.3, 6.6, 1.6 Hz, 1H), 7.21 (tdd, J=7.8, 1.9, 1.0 Hz, 1H), 6.01 (dd, J=58.4, 8.0 Hz, 1H), 4.86 (dt, J=14.7, 6.6 Hz, 1H), 4.77-4.40 (m, 2H), 1.10 (dd, J=5.5, 0.7 Hz, 9H). $^{19}$F NMR (282 MHz, DMSO-$d_6$) δ−112.78, −218.58; MS (ES+): 340/342 (M+1).

Step-3: Preparation of Ethyl 2-(2-((7-(3-(1-((R)-1,1-dimethylethylsulfinamido)-2-fluoroethyl)-2-fluorophenyl)benzofuran-5-yl)methoxy)phenyl)acetate (403c)

Compound 403c was prepared according to the procedure reported in step-3 of scheme-1 from ethyl 2-(2-((7-(4,4,5,5-tetramethyl-1,3,2-dioxaborolan-2-yl)benzofuran-5-yl)methoxy)phenyl)acetate (59a) (130 mg, 0.297 mmol) in dioxane (4 mL) using (R)—N-(1-(3-bromo-2-fluorophenyl)-2-fluoroethyl)-2-methylpropane-2-sulfinamide (403b) (92 mg, 0.270 mmol), Pd(PPh$_3$)$_2$Cl$_2$ (19 mg, 0.027 mmol) and a solution of K$_2$CO$_3$ (112 mg, 0.811 mmol) in water (1 mL) under a nitrogen atmosphere and heating at 100° C. for 16 h on oil bath. This gave after workup and purification by flash column chromatography (silica gel, 12 g, eluting with 0-20% EtOAc in hexane) ethyl 2-(2-((7-(3-(1-((R)-1,1-dimethylethylsulfinamido)-2-fluorophenyl)ben-zofuran-5-yl)methoxy)phenyl)acetate (403c) (103 mg) as a colorless oil; MS (ES+) 592 (M+Na).

Step-4: Preparation of methyl 2-(2-((7-(3-(1-amino-2-fluoroethyl)-2-fluorophenyl)benzofuran-5-yl)methoxy)phenyl)acetate (403d)

Compound 403d was prepared according to the procedure reported in step-10 of scheme-257 from ethyl 2-(2-((7-(3-(1-((R)-1,1-dimethylethylsulfinamido)-2-fluoroethyl)-2-fluorophenyl)benzofuran-5-yl)methoxy)phenyl)acetate (403c) (103 mg, from above step-3) in MeOH (5 mL) using HCl (4 M in 1,4-dioxane, 0.676 mL, 2.70 mmol) and heating at 40° C. for 1 h. This gave after workup methyl 2-(2-((7-(3-(1-amino-2-fluoroethyl)-2-fluorophenyl)benzofuran-5-yl)methoxy)phenyl)acetate (403d); MS (ES+) 452 (M+1).

Step-5: Preparation of (−)-2-(2-((7-(3-(1-amino-2-fluoroethyl)-2-fluorophenyl)benzofuran-5-yl)methoxy)phenyl)acetic Acid (403e)

Compound 403e was prepared according to the procedure reported in step-4 of scheme-4 from methyl 2-(2-((7-(3-(1-amino-2-fluoroethyl)-2-fluorophenyl)benzofuran-5-yl)methoxy)phenyl)acetate (403d) (from above step-4) in MeOH (3 mL) using a solution of NaOH (32 mg, 0.811 mmol) in water (1 mL). This gave after workup and purification by reverse phase column (C18, 100 g, 0-60% MeCN in H$_2$O containing 0.1% HCl) (−)-2-(2-((7-(3-(1-amino-2-fluoroethyl)-2-fluorophenyl)benzofuran-5-yl)methoxy)phenyl)acetic acid (403e) (73 mg, 62% yield) HCl salt as a white solid; $^1$H NMR (300 MHz, DMSO-$d_6$) δ 8.06 (d, J=2.2 Hz, 1H), 7.83 (d, J=1.6 Hz, 1H), 7.75 (dtd, J=12.4, 7.5, 1.7 Hz, 2H), 7.55-7.43 (m, 2H), 7.29-7.18 (m, 2H), 7.14-7.03 (m, 2H), 6.91 (td, J=7.4, 1.1 Hz, 1H), 5.27 (s, 2H), 5.09-4.87 (m, 2H), 4.86-4.71 (m, 1H), 3.58 (s, 2H); $^{19}$F NMR (282 MHz, DMSO-$d_6$) δ−118.21, −223.44; MS (ES+): 438 (M+1), (ES−): 436 (M−1); analysis calculated for C$_{25}$H$_{21}$F$_2$NO$_4$.HCl.1.75H$_2$O: C, 59.41; H, 5.09; Cl, 7.01; N, 2.77; Found: C, 59.46; H, 4.93; Cl, 7.12; N, 2.76; Optical rotation [α]$_D$=−1.724 (c=0.58, MeOH).

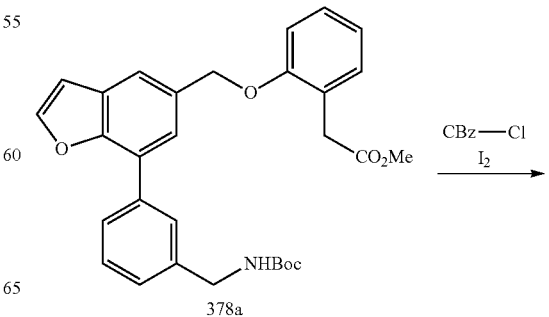

Scheme-404

-continued

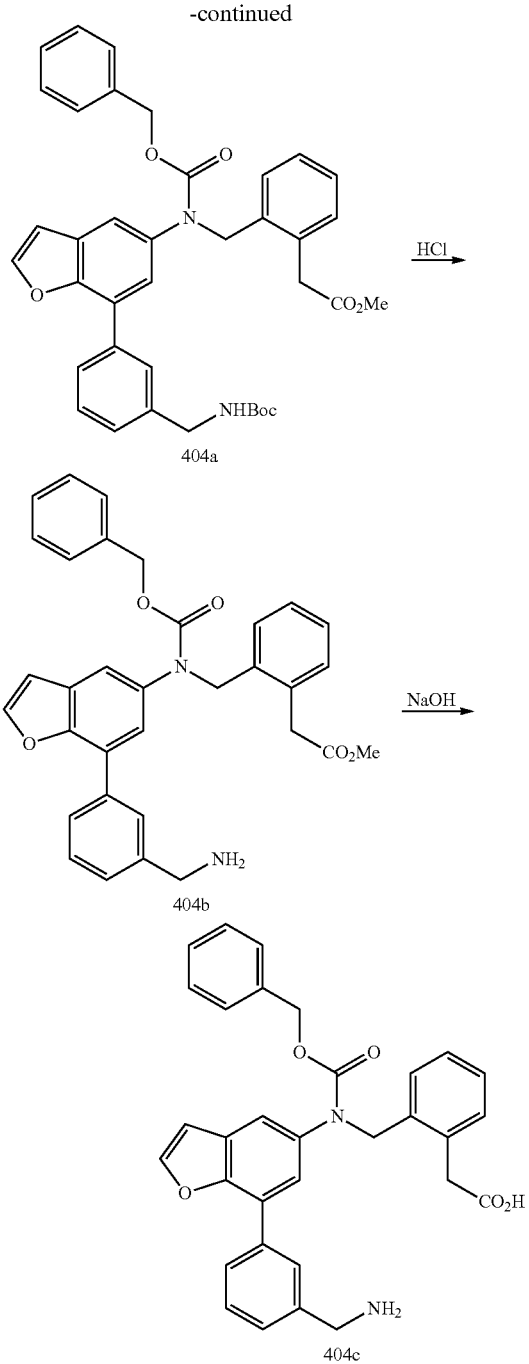

Preparation of 2-(2-(((7-(3-(aminomethyl)phenyl) benzofuran-5-yl)((benzyloxy)carbonyl)amino) methyl)phenyl)acetic Acid (404c)

Step-1: Preparation of methyl 2-(2-((((benzyloxy) carbonyl)(7-(3-(((tert-butoxycarbonyl)amino) methyl)phenyl)benzofuran-5-yl)amino)methyl)phenyl)acetate (404a)

To a solution of methyl 2-(2-(((7-(3-(((tert-butoxycarbonyl)amino)methyl)phenyl)benzofuran-5-yl)amino)methyl) phenyl)acetate (378a) (320 mgs, 0.64 mmol) in DCM (10 mL) was added 30% CBz-Cl in PhMe (0.757 mL, 1.279 mmol) and iodine (3.24 mg, 0.013 mmol) and stirred at room temperature for 16 h. The reaction was diluted with DCM (20 mL), washed with saturated $Na_2S_2O_3$ (25 mL), $H_2O$ (25 mL), brine (25 mL) dried, filtered and concentrated in vacuum to afford methyl 2-(2-((((benzyloxy)carbonyl)(7-(3-(((tert-butoxycarbonyl)amino)methyl)phenyl)benzofuran-5-yl)amino)methyl)phenyl)acetate (404a) (175 mg) as a colorless oil.

Step-2: Preparation of methyl 2-(2-(((7-(3-(aminomethyl)phenyl)benzofuran-5-yl)((benzyloxy)carbonyl)amino)methyl)phenyl)acetate (404b)

Compound 404b was prepared according to the procedure reported in step-3 of scheme-305 from methyl 2-(2-((((benzyloxy)carbonyl)(7-(3-(((tert-butoxycarbonyl)amino) methyl)phenyl)benzofuran-5-yl)amino)methyl)phenyl)acetate (404a) (175 mg, from above step-1) in methanol (5 mL) using HCl (4 M in dioxane; 0.160 mL, 0.639 mmol) and stirring at 40° C. for 1 h. This gave after workup methyl 2-(2-(((7-(3-(aminomethyl)phenyl)benzofuran-5-yl)((benzyloxy)carbonyl)amino)methyl)phenyl)acetate (404b).

Step-3: Preparation of 2-(2-(((7-(3-(aminomethyl) phenyl)benzofuran-5-yl)((benzyloxy)carbonyl) amino)methyl)phenyl)acetic Acid (404c)

Compound 404c was prepared according to the procedure reported in step-4 of scheme-4 from methyl 2-(2-(((7-(3-(aminomethyl)phenyl)benzofuran-5-yl)((benzyloxy)carbonyl)amino)methyl)phenyl)acetate (404b) (from step-2 above) in MeOH (3 mL), water (1 mL) using NaOH (26 mg, 0.639 mmol). This gave after workup and purification by reverse phase column chromatography (C18, 100 g, 0-60% MeCN in $H_2O$ containing 0.1% HCl) 2-(2-(((7-(3-(aminomethyl)phenyl)benzofuran-5-yl)((benzyloxy)carbonyl)amino) methyl)phenyl)acetic acid (404c) (85 mg, 26% yield) HCl salt as a white solid; $^1$H NMR (300 MHz, DMSO-$d_6$) δ 8.11 (d, J=2.2 Hz, 1H), 8.01 (t, J=1.6 Hz, 1H), 7.94 (dt, J=7.6, 1.5 Hz, 1H), 7.80 (d, J=1.6 Hz, 1H), 7.77-7.67 (m, 3H), 7.61 (t, J=7.6 Hz, 1H), 7.54 (dt, J=7.9, 1.6 Hz, 1H), 7.36 (d, J=1.7 Hz, 1H), 7.34-7.24 (m, 3H), 7.19 (dd, J=7.7, 1.6 Hz, 1H), 7.08 (d, J=2.2 Hz, 1H), 5.39 (s, 2H), 4.15 (s, 2H), 3.63 (s, 2H); MS (ES+): 521 (M+1), 519 (M−1).

Scheme-405

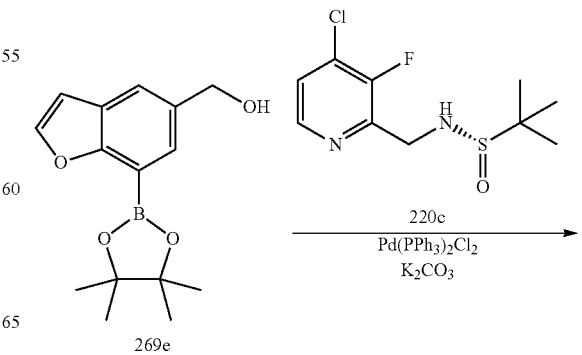

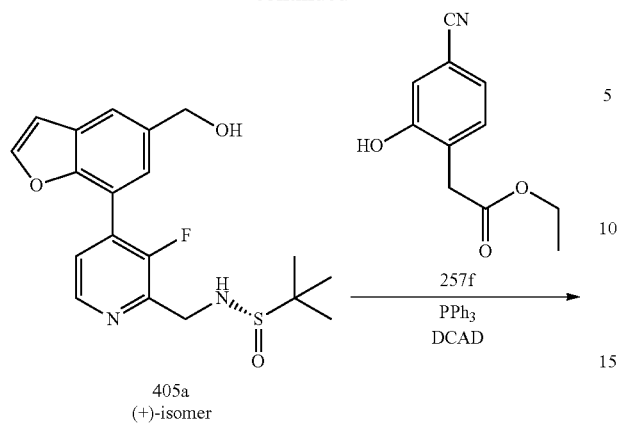

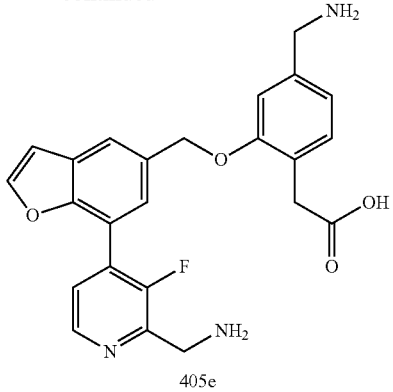

Preparation of 2-(4-(aminomethyl)-2-((7-(2-(aminomethyl)-3-fluoropyridin-4-yl)benzofuran-5-yl)methoxy)phenyl)acetic Acid (405e)

Step-1: Preparation of (+)-(S)—N-((3-fluoro-4-(5-(hydroxymethyl)benzofuran-7-yl)pyridin-2-yl)methyl)-2-methylpropane-2-sulfinamide (405a)

Compound 405a was prepared according to the procedure reported in step-3 of scheme-1 from (7-(4,4,5,5-tetramethyl-1,3,2-dioxaborolan-2-yl)benzofuran-5-yl)methanol (269e) (2.5 g, 9.12 mmol) in dioxane (50 mL) using (+)-(S)—N-((4-chloro-3-fluoropyridin-2-yl)methyl)-2-methylpropane-2-sulfinamide (220c) (2.90 g, 10.94 mmol), bis(triphenylphosphine)palladium(II) chloride (Pd(PPh$_3$)$_2$Cl$_2$) (0.960 g, 1.368 mmol) and a solution of K$_2$CO$_3$ (3.78 g, 27.4 mmol) in water (6 mL) under an N$_2$ atmosphere heating at 100° C. for 11.5 h on oil bath. This gave after workup, purification by flash column chromatography [silica gel, eluting with a 9:1 mixture of ethyl acetate and methanol in hexanes (1:0 to 1:2)] (+)-(S)—N-((3-fluoro-4-(5-(hydroxymethyl)benzofuran-7-yl)pyridin-2-yl)methyl)-2-methylpropane-2-sulfinamide (405a) (1.51 g, 44%) as a yellow solid: $^1$H NMR (300 MHz, DMSO-d$_6$) δ 8.50 (dd, J=4.9, 0.7 Hz, 1H), 8.04 (d, J=2.2 Hz, 1H), 7.74 (dd, J=1.7, 0.8 Hz, 1H), 7.65 (t, J=5.3 Hz, 1H), 7.42 (s, 1H), 7.06 (d, J=2.2 Hz, 1H), 5.85 (t, J=5.8 Hz, 1H), 5.33 (t, J=5.7 Hz, 1H), 4.64 (d, J=5.7 Hz, 2H), 4.40 (dd, J=5.8, 2.1 Hz, 2H), 1.11 (s, 9H); Optical rotation [t]D=+35.56 (c=0.315, MeOH)

Step-2: Preparation of (+)-(S)-ethyl 2-(4-cyano-2-((7-(2-((1,1-dimethylethylsulfinamido)methyl)-3-fluoropyridin-4-yl)benzofuran-5-yl)methoxy)phenyl)acetate (405b)

Compound 405b was prepared according to the procedure reported in step-2 of scheme-23 from (+)-(S)—N-((3-fluoro-4-(5-(hydroxymethyl)benzofuran-7-yl)pyridin-2-yl)methyl)-2-methylpropane-2-sulfinamide (405a) (440 mg, 1.170 mmol) in DCM (12 mL) using triphenylphosphine (460 mg, 1.754 mmol), ethyl 2-(4-cyano-2-hydroxyphenyl)acetate (257f) (240 mg, 1.170 mmol) and a solution of (E)-bis(4-chlorobenzyl) diazene-1,2-dicarboxylate (DCAD, 644 mg, 1.754 mmol) in DCM (12 mL). This gave after workup and purification by flash column chromatography [silica gel, eluting with a 9:1 mixture of ethyl acetate and methanol in hexanes (1:0 to 1:1)] (+)-(S)-ethyl 2-(4-cyano-2-((7-(2-((1,1-dimethylethylsulfinamido)methyl)-3-fluoropyridin-4-yl)benzofuran-5-yl)methoxy)phenyl)acetate (405b) (594 mg, 90%) as a yellow gum; $^1$H NMR (300 MHz, DMSO-$d_6$) δ 8.52 (d, J=4.9 Hz, 1H), 8.10 (d, J=2.2 Hz, 1H), 7.86 (d, J=1.6 Hz, 1H), 7.67 (t, J=5.2 Hz, 1H), 7.64 (d, J=1.3 Hz, 1H), 7.52 (s, 1H), 7.47-7.39 (m, 2H), 7.11 (d, J=2.2 Hz, 1H), 5.86 (t, J=5.7 Hz, 1H), 5.32 (s, 2H), 4.41 (dd, J=5.9, 2.0 Hz, 2H), 3.90 (q, J=7.1 Hz, 2H), 3.72 (s, 2H), 1.11 (s, 9H), 0.95 (t, J=7.1 Hz, 3H); MS (ES+): 564.20 (M+1); Optical rotation [t]D=+25.12 (c=0.43, MeOH)

Step-3: Preparation of (S)-ethyl 2-(4-(aminomethyl)-2-((7-(2-((1,1-dimethylethylsulfinamido)methyl)-3-fluoropyridin-4-yl)benzofuran-5-yl)methoxy)phenyl)acetate (405c)

Compound 405c was prepared according to the procedure reported in step-2 of scheme-256 from (+)-(S)-ethyl 2-(4-cyano-2-((7-(2-((1,1-dimethylethylsulfinamido)methyl)-3-fluoropyridin-4-yl)benzofuran-5-yl)methoxy)phenyl)acetate (405b) (500 mg, 0.887 mmol) in methanol (25 mL) using nickel (II) chloride hexahydrate (52.7 mg, 0.222 mmol) and sodium borohydride (201 mg, 5.32 mmol), using N1-(2-aminoethyl)ethane-1,2-diamine (0.192 mL, 1.774 mmol) for quenching. This gave after workup purified by flash column chromatography [silica gel, eluting with chloroform/DMA80 (1:0 to 0:1)] (S)-ethyl 2-(4-(aminomethyl)-2-((7-(2-((1,1-dimethylethylsulfinamido)methyl)-3-fluoropyridin-4-yl)benzofuran-5-yl)methoxy)phenyl)acetate (405c) (124 mg, 25%). MS (ES+): 568.20 (M+1).

Step-4: Preparation of Ethyl 2-(4-(aminomethyl)-2-((7-(2-(aminomethyl)-3-fluoropyridin-4-yl)benzofuran-5-yl)methoxy)phenyl)acetate (405d)

To a solution of (S)-ethyl 2-(4-(aminomethyl)-2-((7-(2-((1,1-dimethylethylsulfinamido)methyl)-3-fluoropyridin-4-yl)benzofuran-5-yl)methoxy)phenyl)acetate (405c) (120 mg, 0.211 mmol) in tetrahydrofuran (4 mL) was added 3 N aqueous HCl (0.211 mL, 0.634 mmol) at room temperature and stirred for 2 h. The reaction mixture was concentrated to dryness to give ethyl 2-(4-(aminomethyl)-2-((7-(2-(aminomethyl)-3-fluoropyridin-4-yl)benzofuran-5-yl)methoxy)phenyl)acetate (405d) which was used as such for next step.

Step-5: Preparation of 2-(4-(aminomethyl)-2-((7-(2-(aminomethyl)-3-fluoropyridin-4-yl)benzofuran-5-yl)methoxy)phenyl)acetic Acid (405e)

Compound 405e was prepared according to the procedure reported in step-6 of scheme-1 from ethyl 2-(4-(aminomethyl)-2-((7-(2-(aminomethyl)-3-fluoropyridin-4-yl)benzofuran-5-yl)methoxy)phenyl)acetate (405d) (0.211 mmol, from above step-4) in MeOH (5 mL) using a solution of lithium hydroxide hydrate (72.3 mg, 1.688 mmol) in water (5 mL). This gave after workup and purification by reverse phase column (C18, 100 g, eluting with (1:0 to 0:1) MeCN in H$_2$O containing 0.1% HCl) 2-(4-(aminomethyl)-2-((7-(2-(aminomethyl)-3-fluoropyridin-4-yl)benzofuran-5-yl)methoxy)phenyl)acetic acid (405e) (59 mg, 16% for 3 steps) HCl salt as a white solid; $^1$H NMR (300 MHz, DMSO-$d_6$) δ 8.67-8.54 (m, 4H), 8.47 (s, 3H), 8.13 (d, J=2.2 Hz, 1H), 7.94 (d, J=1.6 Hz, 1H), 7.82 (t, J=5.3 Hz, 1H), 7.62 (s, 1H), 7.42 (d, J=1.6 Hz, 1H), 7.25 (d, J=7.7 Hz, 1H), 7.11 (d, J=2.2 Hz, 1H), 7.02 (dd, J=7.7, 1.5 Hz, 1H), 5.29 (s, 2H), 4.45-4.30 (m, 2H), 4.03-3.94 (m, 2H), 3.59 (s, 2H); $^{19}$F NMR (282 MHz, DMSO-$d_6$) δ−128.35; MS (ES+): 436.10 (M+1); MS (ES−): 434.10 (M−1); Analysis calculated for C$_{24}$H$_{22}$FN$_3$O$_4$.3.0HCl.2.75 H$_2$O: C, 48.50; H, 5.17; N, 7.07; Found: C, 48.71; H, 5.55; N, 6.53.

Scheme-406

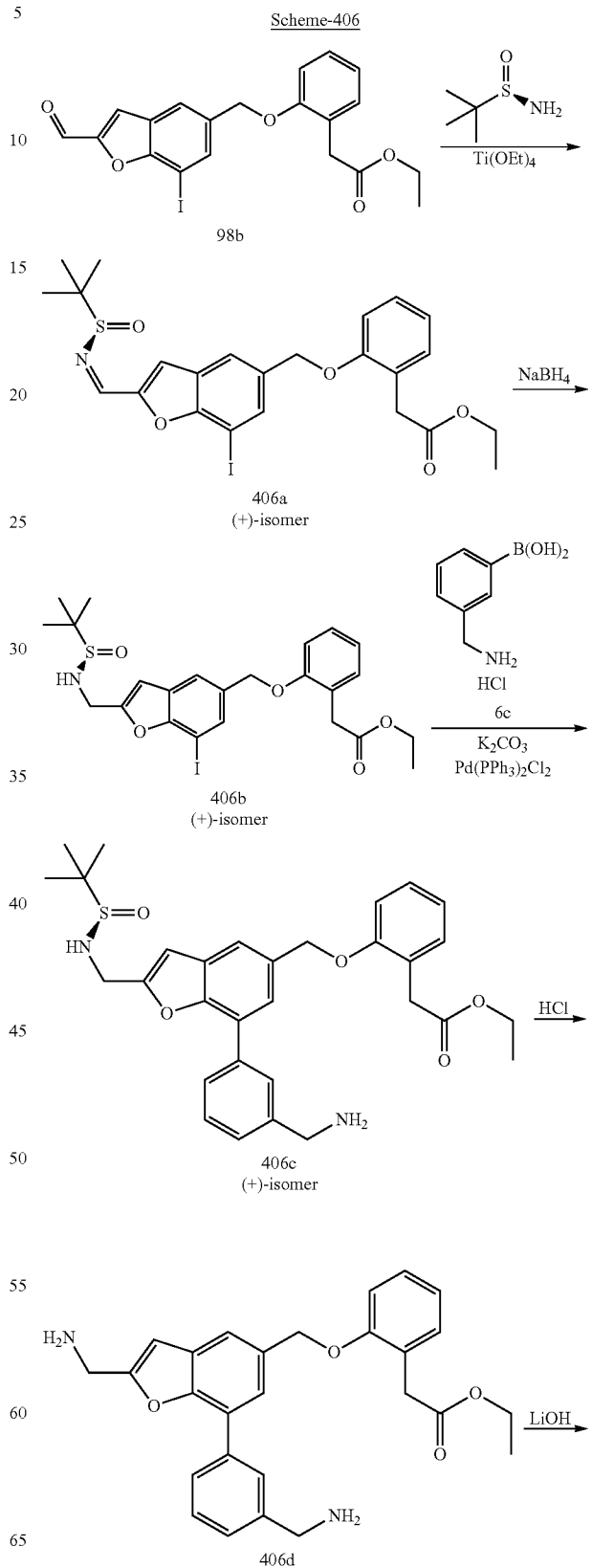

-continued

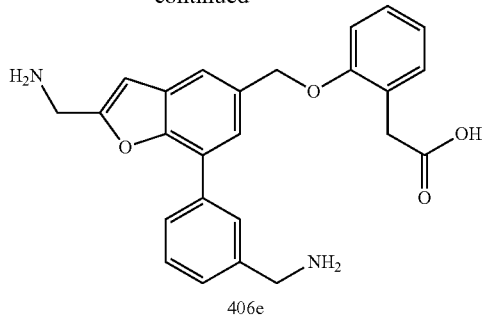

406e

Preparation of 2-(2-((2-(aminomethyl)-7-(3-(aminomethyl)phenyl)benzofuran-5-yl)methoxy)phenyl) acetic Acid (406e)

Step-1: Preparation of (+)-(R,Z)-ethyl 2-(2-((2-(((tert-butylsulfinyl)imino)methyl)-7-iodobenzofuran-5-yl)methoxy)phenyl)acetate (406a)

Compound 406a was prepared according to the procedure reported in step-1 of scheme-258 from ethyl 2-(2-((2-formyl-7-iodobenzofuran-5-yl)methoxy)phenyl)acetate (98b) (1.2 g, 2.58 mmol) and (R)-2-methylpropane-2-sulfinamide (0.394 g, 3.23 mmol) in tetrahydrofuran (15 mL) using tetraethoxytitanium (1.084 mL, 5.17 mmol) and heating at reflux for 14 h. This gave after workup and purification by flash column chromatography [silica gel, eluting with ethyl acetate in hexanes (1:0 to 2:1)] (+)-(R,Z)-ethyl 2-(2-((2-(((tert-butylsulfinyl)imino)methyl)-7-iodobenzofuran-5-yl)methoxy)phenyl)acetate (406a) (965 mg, 66%) as a yellow gum; $^1$H NMR (300 MHz, DMSO-d$_6$) δ 8.55 (s, 1H), 7.96 (s, 1H), 7.93 (d, J=1.5 Hz, 1H), 7.85 (d, J=1.5 Hz, 1H), 7.30-7.18 (m, 2H), 7.07 (dd, J=8.3, 1.1 Hz, 1H), 6.92 (td, J=7.4, 1.1 Hz, 1H), 5.18 (s, 2H), 4.15-3.94 (m, 2H), 3.63 (s, 2H), 1.21 (s, 9H), 1.09 (t, J=7.1 Hz, 3H); Optical rotation $[\alpha]_D$=+61.76 (c=0.34, MeOH)

Step-2: Preparation of (−)-(R)-ethyl 2-(2-((2-((1,1-dimethylethylsulfinamido)methyl)-7-iodobenzofuran-5-yl)methoxy)phenyl)acetate (406b)

Compound 406b was prepared according to the procedure reported in step-2 of scheme-258 from (+)-(R,Z)-ethyl 2-(2-((2-(((tert-butylsulfinyl)imino)methyl)-7-iodobenzofuran-5-yl)methoxy)phenyl)acetate (406a) (0.92 g, 1.621 mmol) in tetrahydrofuran (25 mL) using sodium borohydride (0.125 g, 3.24 mmol). This gave after workup and purification by flash column chromatography [silica gel, eluting with hexanes/10% methanol in ethyl acetate (1:0 to 1:1)] (−)-(R)-ethyl 2-(2-((2-((1,1-dimethylethylsulfinamido)methyl)-7-iodobenzofuran-5-yl)methoxy)phenyl)acetate (406b) (722 mg, 78%) as a colorless gum; $^1$H NMR (300 MHz, DMSO-d$_6$) δ 7.69 (d, J=1.6 Hz, 1H), 7.63 (d, J=1.5 Hz, 1H), 7.30-7.17 (m, 2H), 7.06 (d, J=8.4 Hz, 1H), 6.97-6.86 (m, 2H), 5.99 (t, J=5.7 Hz, 1H), 5.13 (s, 2H), 4.48-4.23 (m, 2H), 4.02 (q, J=7.1 Hz, 2H), 3.61 (s, 2H), 1.15 (s, 9H), 1.08 (t, J=7.1 Hz, 3H); MS (ES+): 570.00 (M+1); Optical rotation $[\alpha]_D$=−10.34 (c=0.29, MeOH)

Step-3: Preparation of (−)-(R)-ethyl 2-(2-((7-(3-(aminomethyl)phenyl)-2-((1,1-dimethylethylsulfinamido)methyl)benzofuran-5-yl)methoxy)phenyl)acetate (406c)

Compound 406c was prepared according to the procedure reported in step-3 of scheme-1 from (−)-(R)-ethyl 2-(2-((2-((1,1-dimethylethylsulfinamido)methyl)-7-iodobenzofuran-5-yl)methoxy)phenyl)acetate (406b) (500 mg, 0.878 mmol) in dioxane (15 mL) using 3-(aminomethyl)phenylboronic acid hydrochloride (6c) (247 mg, 1.317 mmol), Pd(PPh$_3$)$_2$Cl$_2$ (123 mg, 0.176 mmol) and a solution of K$_2$CO$_3$ (364 mg, 2.63 mmol) in water (1.8 mL) under a nitrogen atmosphere and heating at 100° C. for 3 h on oil bath. This gave after workup and purification by flash column chromatography [silica gel, eluting with dichloromethane/methanol (1:0 to 4:1)] (−)-(R)-ethyl 2-(2-((7-(3-(aminomethyl)phenyl)-2-((1,1-dimethylethylsulfinamido)methyl)benzofuran-5-yl)methoxy)phenyl)acetate (406c) (340 mg, 71%) as a colorless gum; $^1$H NMR (300 MHz, DMSO-d$_6$) δ 7.86 (s, 1H), 7.78-7.72 (m, 1H), 7.63 (d, J=1.6 Hz, 1H), 7.54 (d, J=1.7 Hz, 1H), 7.49-7.36 (m, 2H), 7.29-7.17 (m, 2H), 7.14-7.05 (m, 1H), 6.93-6.87 (m, 1H), 6.86 (s, 1H), 5.97 (t, J=5.4 Hz, 1H), 5.22 (s, 2H), 4.35 (d, J=5.6 Hz, 3H), 3.93 (q, J=7.1 Hz, 2H), 3.82 (s, 2H), 3.62 (s, 2H), 1.15 (s, 9H), 0.99 (t, J=7.1 Hz, 3H); MS (ES+): 549.20 (M+1); Optical rotation $[\alpha]_D$=−21.33 (c=0.15, MeOH)

Step-4: Preparation of Ethyl 2-(2-((2-(aminomethyl)-7-(3-(aminomethyl)phenyl)benzofuran-5-yl)methoxy)phenyl)acetate (406d)

Compound 406d was prepared according to the procedure reported in step-10 of scheme-257 from (−)-(R)-ethyl 2-(2-((7-(3-(aminomethyl)phenyl)-2-((1,1-dimethylethylsulfinamido)methyl)benzofuran-5-yl)methoxy)phenyl)acetate (406c) (310 mg, 0.565 mmol) in THF (5 mL) using 3 N aqueous HCl (0.565 mL, 1.695 mmol) and stirring at room temperature for 3 h. This gave after workup ethyl 2-(2-((2-(aminomethyl)-7-(3-(aminomethyl)phenyl)benzofuran-5-yl)methoxy)phenyl)acetate (406d) which was used as such in next step without further purification.

Step-5: Preparation of 2-(2-((2-(aminomethyl)-7-(3-(aminomethyl)phenyl)benzofuran-5-yl)methoxy) phenyl)acetic Acid (406e)

Compound 406e was prepared according to the procedure reported in step-6 of scheme-1 from ethyl 2-(2-((2-(aminomethyl)-7-(3-(aminomethyl)phenyl)benzofuran-5-yl)methoxy)phenyl)acetate (406d) (0.565 mmol, from above step-4) in MeOH/THF (10 mL, each) using a solution of lithium hydroxide hydrate (194 mg, 4.52 mmol) in water (10 mL) and stirring at room temperature for 15h. This gave after workup and purification by reverse phase column [C18, 100 g, eluting with MeCN in H$_2$O containing 0.1% HCl (1:0 to 0:1)] 2-(2-((2-(aminomethyl)-7-(3-(aminomethyl)phenyl)benzofuran-5-yl)methoxy)phenyl)acetic acid (406e) (115 mg, 81%) HCl salt as a white solid; $^1$H NMR (300 MHz, DMSO-d$_6$) δ 8.67 (s, 6H), 8.20-8.17 (m, 1H), 7.98 (dt, J=7.3, 1.8 Hz, 1H), 7.76 (d, J=1.6 Hz, 1H), 7.70 (d, J=1.6 Hz, 1H), 7.62-7.51 (m, 2H), 7.23 (s, 1H), 7.21 (s, 1H), 7.11-7.05 (m, 2H), 6.94-6.87 (m, 1H), 5.27 (s, 2H), 4.31 (s, 2H), 4.16 (s, 2H), 3.60 (s, 2H); MS (ES+): 417.10 (M+1); MS (ES−): 415.20 (M−1); Analysis calculated for C$_{25}$H$_{24}$N$_2$O$_4$·1.95HCl·1.5 H$_2$O: C, 58.35; H, 5.67; Cl, 13.43; N, 5.44; Found: C, 58.27; H, 5.37; N, 5.33; Cl, 13.13.

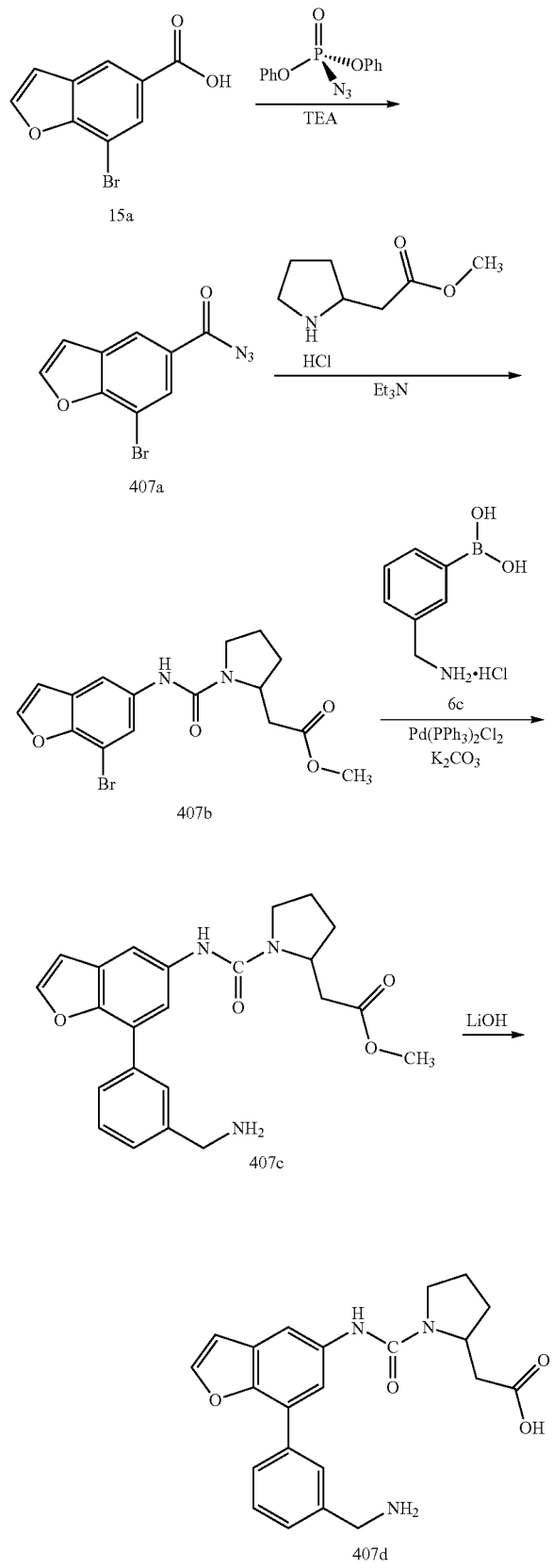

Scheme-407

Preparation of 2-(1-((7-(3-(aminomethyl)phenyl)benzofuran-5-yl)carbamoyl)pyrrolidin-2-yl)acetic Acid (407d)

Step-1: Preparation of 7-bromobenzofuran-5-carbonyl azide (407a)

Diphenyl phosphoryl azide (0.461 mL, 2.074 mmol) was added to a suspension of 7-bromobenzofuran-5-carboxylic acid (15a) (500 mg, 2.074 mmol), TEA (0.289 mL, 2.074 mmol) in THF (40 mL), stirred at room temperature for 18 h. The reaction mixture was concentrated in vacuum to furnish 7-bromobenzofuran-5-carbonyl azide (407a) which was used as such for next step.

Step-2: Preparation of methyl 2-(1-((7-bromobenzofuran-5-yl)carbamoyl)pyrrolidin-2-yl)acetate (407b)

A suspension of 7-bromobenzofuran-5-carbonyl azide (407a) (2.074 mmol, from above step-1) in toluene (60 mL) was heated at reflux for 0.5 h. The reaction mixture was cooled to room temperature and added triethylamine (0.442 mL, 3.17 mmol), methyl 2-(pyrrolidin-2-yl)acetate hydrochloride (120 mg, 0.635 mmol; CAS #1263378-78-4) and heated at reflux for 2 h. The reaction mixture was cooled to room temperature, diluted with ethyl acetate (120 mL), washed with water (75 mL), brine (75 mL), dried, filtered and concentrated in vacuum. The residue obtained was purified by flash column chromatography [silica gel, eluting with hexanes/ethyl acetate (1:0 to 1:1)] to give methyl 2-(1-((7-bromobenzofuran-5-yl)carbamoyl)pyrrolidin-2-yl)acetate (407b) (241 mg, 30% yield for 2-steps) as a white solid. $^1$H NMR (300 MHz, DMSO-$d_6$) δ 8.29 (s, 1H), 8.03 (d, J=2.2 Hz, 1H), 7.80 (d, J=1.9 Hz, 1H), 7.72 (dd, J=2.0, 0.5 Hz, 1H), 7.03 (d, J=2.2 Hz, 1H), 4.30-4.16 (m, 1H), 3.59 (s, 3H), 3.53-3.25 (m, 2H), 2.79 (dd, J=15.3, 4.0 Hz, 1H), 2.39 (dd, J=15.3, 9.5 Hz, 1H), 2.13-1.57 (m, 4H); MS (ES+): 381.00 & 382.00 (M+1).

Step-3: Preparation of methyl 2-(1-((7-(3-(aminomethyl)phenyl)benzofuran-5-yl)carbamoyl)pyrrolidin-2-yl)acetate (407c)

Compound 407c was prepared according to the procedure reported in step-3 of scheme-1 from methyl 2-(1-((7-bromobenzofuran-5-yl)carbamoyl)pyrrolidin-2-yl)acetate (407b) (235 mg, 0.616 mmol) in dioxane (12 mL) using 3-(aminomethyl)phenylboronic acid hydrochloride (6c) (173 mg, 0.925 mmol), a solution of $K_2CO_3$ (256 mg, 1.849 mmol) in water (1.2 mL), Pd(PPh$_3$)$_2$Cl$_2$ (87 mg, 0.123 mmol) and heating under a nitrogen atmosphere at 100° C. for 3 h. This gave after workup and purification by flash column chromatography [silica gel, eluting with dichloromethane/methanol (1:0 to 4:1)] methyl 2-(1-((7-(3-(aminomethyl)phenyl)benzofuran-5-yl)carbamoyl)pyrrolidin-2-yl)acetate (407c) (66 mg, 26% yield) as a white solid; MS (ES+): 408.20 (M+1).

Step-4: Preparation of 2-(1-((7-(3-(aminomethyl)phenyl)benzofuran-5-yl)carbamoyl)pyrrolidin-2-yl)acetic Acid (407d)

Compound 407d was prepared according to the procedure reported in step-6 of scheme-1 from methyl 2-(1-((7-(3-(aminomethyl)phenyl)benzofuran-5-yl)carbamoyl)pyrrolidin-2-yl)acetate (407c) (63 mg, 0.155 mmol) in MeOH/THF (4 mL, each) using a solution of lithium hydroxide hydrate (40 mg, 0.928 mmol) in water (4 mL) and stirring at room temperature for 19h. This gave after workup and purification by reverse phase column [C18, 100 g, eluting with MeCN in H₂O containing 0.1% HCl (1:0 to 0:1)] 2-(1-((7-(3-(aminomethyl)phenyl)benzofuran-5-yl)carbamoyl)pyrrolidin-2-yl)acetic acid (407d) (10 mg, 16%) HCl salt as a white solid; $^1$H NMR (300 MHz, DMSO-d₆) δ 12.25 (s, 1H), 8.31 (s, 1H), 8.00 (d, J=2.2 Hz, 1H), 7.93-7.90 (m, 1H), 7.84 (dt, J=7.5, 1.6 Hz, 1H), 7.76 (d, J=2.1 Hz, 1H), 7.71 (d, J=2.1 Hz, 1H), 7.63-7.50 (m, 2H), 7.00 (d, J=2.2 Hz, 1H), 4.30-4.18 (m, 1H), 4.18-4.06 (m, 2H), 3.57-3.45 (m, 2H), 2.79 (dd, J=15.7, 3.6 Hz, 1H), 2.29 (dd, J=15.6, 9.8 Hz, 1H), 2.10-1.65 (m, 4H); MS (ES+): 394.10 (M+1); MS (ES−): 392.15 (M−1).

Scheme-408

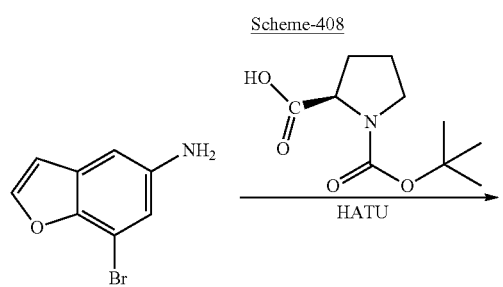

216b

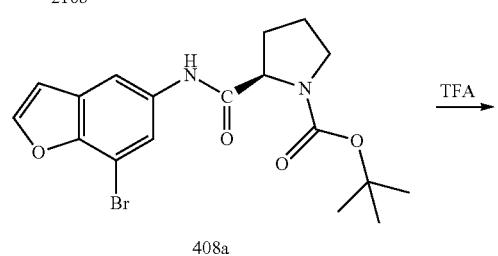

408a

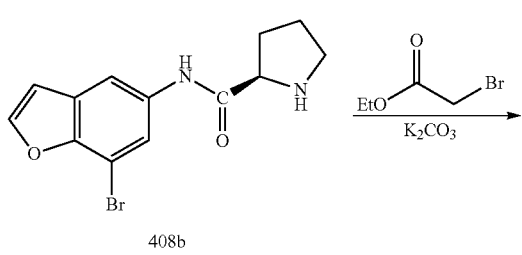

408b

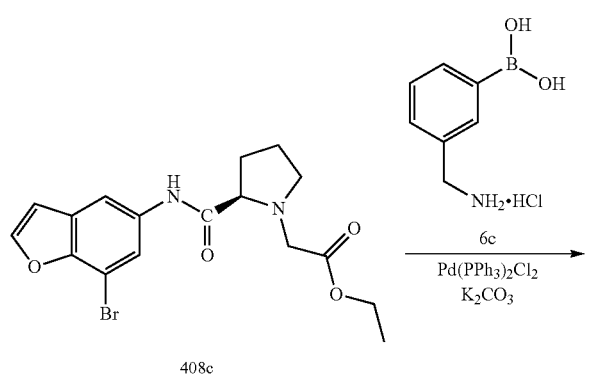

408c

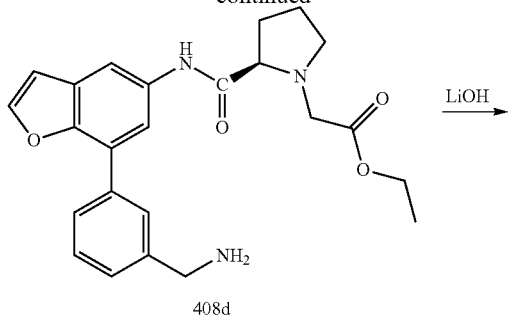

408d

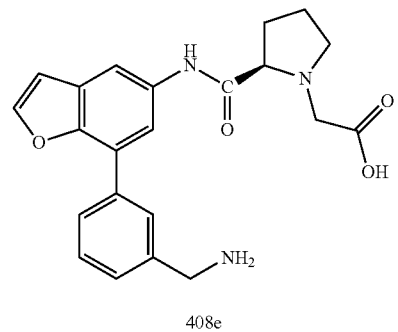

408e

Preparation of (R)-2-(2-((7-(3-(aminomethyl)phenyl)benzofuran-5-yl)carbamoyl)pyrrolidin-1-yl)acetic Acid (408e)

Step-1: Preparation of ((R)-tert-butyl 2-((7-bromobenzofuran-5-yl)carbamoyl)pyrrolidine-1-carboxylate (408a)

Compound 408a was prepared according to the procedure reported in step-4 of scheme-1, from 7-bromobenzofuran-5-amine hydrochloride (216b) (240 mg, 0.966 mmol) in DMF (12 mL) using (R)-1-(tert-butoxycarbonyl)pyrrolidine-2-carboxylic acid (260 mg, 1.207 mmol), DIPEA (0.673 mL, 3.86 mmol) and HATU (551 mg, 1.449 mmol) and stirring at room temperature for 19 h. This gave after workup and purification by flash column chromatography [silica, eluting with hexanes/ethyl acetate (1:0 to 2:1)] ((R)-tert-butyl 2-((7-bromobenzofuran-5-yl)carbamoyl)pyrrolidine-1-carboxylate (408a) (342 mg, 87%) as a colorless gum; $^1$H NMR (300 MHz, DMSO-d₆) δ 10.13 (s, 1H), 8.08 (d, J=2.2 Hz, 1H), 7.96-7.89 (m, 1H), 7.84-7.77 (m, 1H), 7.11-7.06 (m, 1H), 4.31-4.12 (m, 1H), 3.50-3.27 (m, 2H), 2.29-2.06 (m, 1H), 1.95-1.72 (m, 3H), 1.40 (s, 3H), 1.27 (s, 6H); MS (ES−): 406.90 (M−1).

Step-2: Preparation of (R)—N-(7-bromobenzofuran-5-yl)pyrrolidine-2-carboxamide (408b)

Compound 408b was prepared according to the procedure reported in step-5 of scheme-1 from ((R)-tert-butyl 2-((7-bromobenzofuran-5-yl)carbamoyl)pyrrolidine-1-carboxylate (408a) (330 mg, 0.806 mmol) using TFA (0.621 mL, 8.06 mmol) in DCM (15 mL). This gave after workup (R)—N-(7-bromobenzofuran-5-yl)pyrrolidine-2-carboxamide (408b) which was used as such for next step.

Step-3: Preparation of (R)-ethyl 2-(2-((7-bromobenzofuran-5-yl)carbamoyl)pyrrolidin-1-yl)acetate (408c)

Compound 408c was prepared according to the procedure reported in step-1 of scheme-382 (R)—N-(7-bromobenzofuran-5-yl)pyrrolidine-2-carboxamide (408b) (249 mg, 0.806 mmol), ethyl 2-bromoacetate (0.134 mL, 1.209 mmol), $K_2CO_3$ (557 mg, 4.03 mmol) in DMF (8 mL) and stirring at room temperature for 18 h. This gave after workup and purification by flash column chromatography [silica gel, eluting with hexanes/ethyl acetate (1:0 to 2:1)] (R)-ethyl 2-(2-((7-bromobenzofuran-5-yl)carbamoyl)pyrrolidin-1-yl)acetate (408c) (234 mg, 74% for two steps) as a colorless gum; $^1$H NMR (300 MHz, DMSO-$d_6$) δ 10.09 (s, 1H), 8.08 (d, J=2.2 Hz, 1H), 8.00 (d, J=1.9 Hz, 1H), 7.86 (d, J=1.9 Hz, 1H), 7.09 (d, J=2.2 Hz, 1H), 4.11 (q, J=7.1 Hz, 2H), 3.72-3.44 (m, 3H), 3.24-3.09 (m, 1H), 2.78-2.59 (m, 1H), 2.30-2.06 (m, 1H), 1.96-1.67 (m, 3H), 1.19 (t, J=7.1 Hz, 3H); MS (ES+): 395.00 (M+1).

Step-4: Preparation of (R)-ethyl 2-(2-((7-(3-(aminomethyl)phenyl)benzofuran-5-yl)carbamoyl)pyrrolidin-1-yl)acetate (408d)

Compound 408d was prepared according to the procedure reported in step-3 of scheme-1 from (R)-ethyl 2-(2-((7-bromobenzofuran-5-yl)carbamoyl)pyrrolidin-1-yl)acetate (408c) (220 mg, 0.557 mmol) in dioxane (10 mL) using 3-(aminomethyl)phenylboronic acid hydrochloride (6c) (156 mg, 0.835 mmol), $K_2CO_3$ (231 mg, 1.670 mmol) in water (1 mL) and bis(triphenylphosphine)palladium(II)chloride (78 mg, 0.111 mmol) under a nitrogen atmosphere and heating at 100° C. for 3 h on oil bath. This gave after workup, purification by flash column chromatography [silica gel, eluting with dichloromethane/methanol (1:0 to 9:1)] (R)-ethyl 2-(2-((7-(3-(aminomethyl)phenyl)benzofuran-5-yl)carbamoyl)pyrrolidin-1-yl)acetate (408d) (97 mg, 41%) as a colorless gum; $^1$H NMR (300 MHz, DMSO-$d_6$) δ 10.06 (s, 1H), 8.06 (d, J=2.1 Hz, 1H), 8.04 (d, J=2.1 Hz, 1H), 7.79-7.76 (m, 1H), 7.72-7.65 (m, 2H), 7.47 (t, J=7.5 Hz, 1H), 7.43-7.36 (m, 1H), 7.03 (d, J=2.2 Hz, 1H), 4.11 (q, J=7.1 Hz, 2H), 3.82 (s, 2H), 3.74-3.44 (m, 3H), 3.26-3.13 (m, 1H), 2.79-2.62 (m, 1H), 2.30-2.09 (m, 1H), 1.98-1.64 (m, 3H), 1.18 (t, J=7.1 Hz, 3H); MS (ES+): 422.100 (M+1).

Step-5: Preparation of (R)-2-(2-((7-(3-(aminomethyl)phenyl)benzofuran-5-yl)carbamoyl)pyrrolidin-1-yl)acetic Acid (408e)

Compound 408e was prepared according to the procedure reported in step-6 of scheme-1 from (R)-ethyl 2-(2-((7-(3-(aminomethyl)phenyl)benzofuran-5-yl)carbamoyl)pyrrolidin-1-yl)acetate (408d) (90 mg, 0.214 mmol) in MeOH/THF (5 mL, each) using a solution of lithium hydroxide hydrate (54.9 mg, 1.281 mmol) in water (5 mL). This gave after workup and purification by reverse phase column [C18 (50 g), eluting with (1:0 to 0:1) ACN in water (containing 0.1% HCl)] (R)-2-(2-((7-(3-(aminomethyl)phenyl)benzofuran-5-yl)carbamoyl)pyrrolidin-1-yl)acetic acid (408e) (14 mg, 17%) HCl salt as a white solid. $^1$H NMR (300 MHz, DMSO-$d_6$) δ 11.12 (s, 1H), 8.51 (s, 3H), 8.09 (d, J=2.2 Hz, 1H), 8.01 (d, J=2.0 Hz, 1H), 7.92 (s, 1H), 7.84-7.78 (m, 1H), 7.76 (d, J=2.1 Hz, 1H), 7.64-7.56 (m, 2H), 7.09 (d, J=2.2 Hz, 1H), 4.50 (s, 1H), 4.43-4.02 (m, 4H), 3.72 (s, 2H), 2.67-2.56 (m, 1H), 2.20-2.03 (m, 2H), 1.96 (s, 1H); MS (ES+): 394.20 (M+1); MS (ES−): 392.10 (M−1).

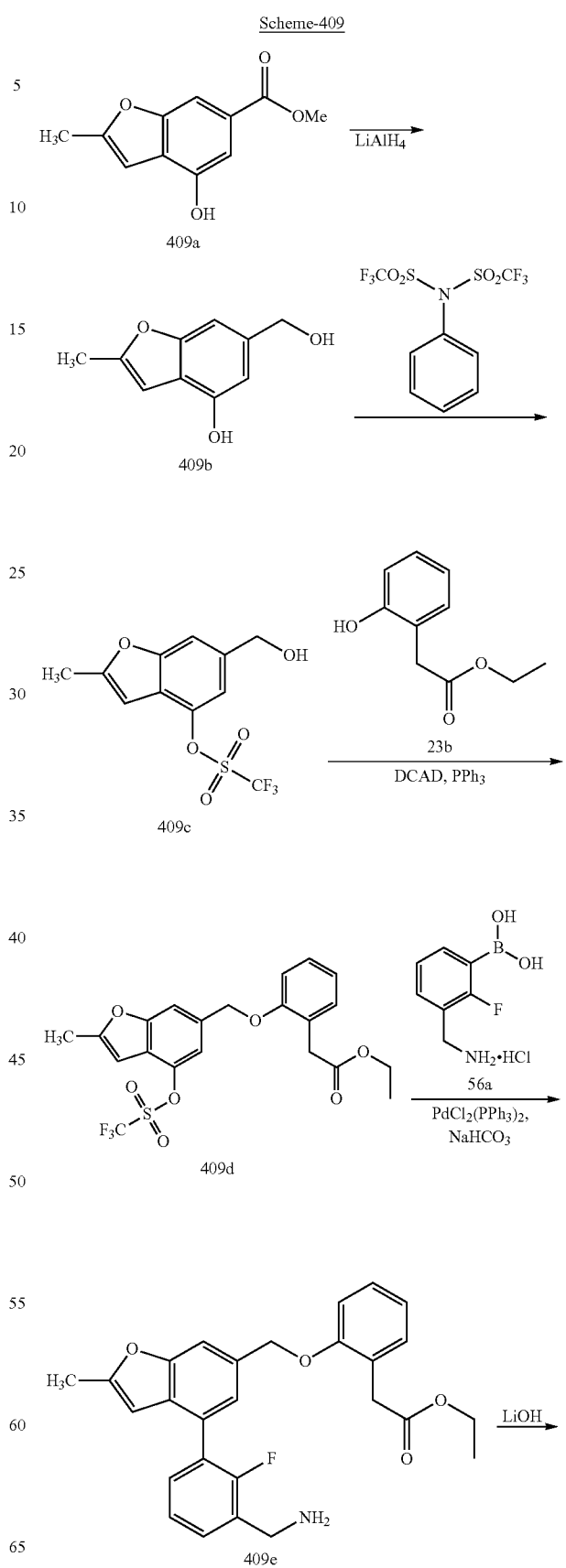

Scheme-409

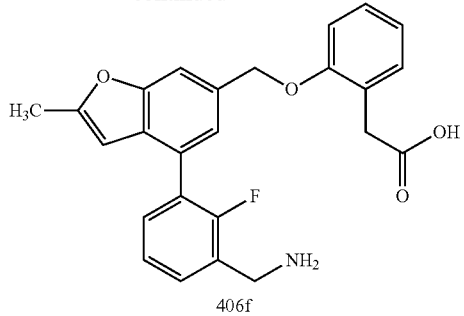

406f

Preparation of 2-(2-((4-(3-(aminomethyl)-2-fluorophenyl)-2-methylbenzofuran-6-yl)methoxy)phenyl) acetic Acid (409f)

Step-1: Preparation of 6-(hydroxymethyl)-2-methylbenzofuran-4-ol (409b)

Compound 409b was prepared according to the procedure reported in step-1 of scheme-115 from methyl 4-hydroxy-2-methylbenzofuran-6-carboxylate (409a) (2.4 g, 11.64 mmol; CAS #314725-17-2) in THF (40 mL) using lithium aluminum hydride (0.663 g, 17.46 mmol) and stirring at RT for 21 h. This gave after workup and purification by flash column chromatography [silica gel, eluting with hexanes/ethyl acetate (1:0 to 1:1)] 6-(hydroxymethyl)-2-methylbenzofuran-4-ol (409b) (1.40 g, 68%) as a yellow solid; $^1$H NMR (300 MHz, DMSO-$d_6$) δ 9.66 (s, 1H), 6.87-6.84 (m, 1H), 6.55-6.52 (m, 1H), 6.51-6.49 (m, 1H), 5.12 (t, J=5.8 Hz, 1H), 4.46 (d, J=5.8 Hz, 2H), 2.38 (d, J=1.2 Hz, 3H); MS (ES+): 201.20 (M+1).

Step-2: Preparation of 6-(hydroxymethyl)-2-methylbenzofuran-4-yl trifluoromethanesulfonate (409c)

Compound 409c was prepared according to the procedure reported in step-2 of scheme-115 from 6-(hydroxymethyl)-2-methylbenzofuran-4-ol (409b) (1.37 g, 7.69 mmol) in DMF (25 mL) using 1,1,1-trifluoro-N-phenyl-N-(trifluoromethylsulfonyl)methanesulfonamide (2.80 g, 7.69 mmol), triethylamine (2.143 mL, 15.38 mmol) and stirring at RT for 16 h. This gave after workup and purification by flash column chromatography [silica gel, eluting with hexanes/ethyl acetate (1:0 to 4:1)] 6-(hydroxymethyl)-2-methylbenzofuran-4-yl trifluoromethanesulfonate (409c) (1.747 g, 73%) as a yellow solid; $^1$H NMR (300 MHz, DMSO-$d_6$) δ 7.62-7.56 (m, 1H), 7.28 (d, J=1.0 Hz, 1H), 6.66 (t, J=1.2 Hz, 1H), 5.50 (s, 1H), 4.62 (s, 2H), 2.48 (d, J=1.2 Hz, 3H); MS (ES−): 309.80 (M−1).

Step-3: Preparation of Ethyl 2-(2-((2-methyl-4-(((trifluoromethyl)sulfonyl)oxy)benzofuran-6-yl)methoxy)phenyl)acetate (409d)

Compound 409d was prepared according to the procedure reported in step-2 of scheme-23 from 6-(hydroxymethyl)-2-methylbenzofuran-4-yl trifluoromethanesulfonate (409c) (1.7 g, 5.48 mmol) in DCM (40 mL) using triphenylphosphine (2.156 g, 8.22 mmol), ethyl 2-(2-hydroxyphenyl)acetate (23b) (1.481 g, 8.22 mmol) and (E)-bis(4-chlorobenzyl) diazene-1,2-dicarboxylate (DCAD, 3.02 g, 8.22 mmol).

This gave after workup and purification by flash column chromatography [silica gel, eluting with hexanes/ethyl acetate (1:0 to 5:1)] ethyl 2-(2-((2-methyl-4-(((trifluoromethyl)sulfonyl)oxy)benzofuran-6-yl)methoxy)phenyl)acetate (409d) (2.09 g, 81%) as a white solid; $^1$H NMR (300 MHz, DMSO-$d_6$) δ 7.74 (t, J=1.0 Hz, 1H), 7.42 (d, J=1.1 Hz, 1H), 7.31-7.18 (m, 2H), 7.09-7.01 (m, 1H), 6.92 (td, J=7.4, 1.1 Hz, 1H), 6.74-6.67 (m, 1H), 5.26 (s, 2H), 4.04-3.96 (m, 2H), 3.65 (s, 2H), 2.50 (d, J=1.0 Hz, 3H), 1.08 (t, J=7.1 Hz, 3H); MS (ES+): 473.00 (M+1).

Step-4: Preparation of Ethyl 2-(2-((4-(3-(aminomethyl)-2-fluorophenyl)-2-methylbenzofuran-6-yl) methoxy)phenyl)acetate (409e)

Compound 409e was prepared according to the procedure reported in step-3 of scheme-1 from ethyl 2-(2-((2-methyl-4-(((trifluoromethyl)sulfonyl)oxy)benzofuran-6-yl) methoxy)phenyl)acetate (409d) (600 mg, 1.270 mmol) in dioxane (12 mL) using 3-(aminomethyl)-2-fluorophenylboronic acid hydrochloride (56a) (391 mg, 1.905 mmol), a solution of sodium bicarbonate (320 mg, 3.81 mmol) in water (1.2 mL), Pd(PPh$_3$)$_2$Cl$_2$ (267 mg, 0.381 mmol) and heating under a nitrogen atmosphere at 100° C. for 3 h. This gave after workup, purification by flash column chromatography [silica gel, eluting with dichloromethane/methanol (1:0 to 19:1)] ethyl 2-(2-((4-(3-(aminomethyl)-2-fluorophenyl)-2-methylbenzofuran-6-yl)methoxy)phenyl)acetate (409e) (208 mg, 37%) as brown gum; $^1$H NMR (300 MHz, DMSO-$d_6$) δ 7.63-7.50 (m, 2H), 7.37 (td, J=7.4, 2.0 Hz, 1H), 7.32-7.17 (m, 4H), 7.11-7.07 (m, 1H), 6.90 (td, J=7.4, 1.1 Hz, 1H), 6.44 (dt, J=2.3, 1.1 Hz, 1H), 5.23 (s, 2H), 3.93 (q, J=7.1 Hz, 2H), 3.83 (s, 2H), 3.63 (s, 2H), 2.45 (d, J=1.1 Hz, 3H), 1.92 (s, 2H), 1.01 (t, J=7.1 Hz, 3H); MS (ES+): 448.20 (M+1).

Step-5: Preparation of 2-(2-((4-(3-(aminomethyl)-2-fluorophenyl)-2-methylbenzofuran-6-yl)methoxy) phenyl)acetic Acid (409f)

Compound 409f was prepared according to the procedure reported in step-6 of scheme-1 from ethyl 2-(2-((4-(3-(aminomethyl)-2-fluorophenyl)-2-methylbenzofuran-6-yl) methoxy)phenyl)acetate (409e) (180 mg, 0.402 mmol) in THF/MeOH (8 mL, each) using a solution of lithium hydroxide hydrate (101 mg, 2.413 mmol) in water (8 mL) and stirring at room temperature for 19 h. This gave after workup and purification by reverse phase column chromatography [C18 column, eluting with water (containing 0.1% HCl)/acetonitrile (1:0 to 0:1)] 2-(2-((4-(3-(aminomethyl)-2-fluorophenyl)-2-methylbenzofuran-6-yl)methoxy)phenyl) acetic acid (409f) (128 mg, 70%) HCl salt as a white solid. $^1$H NMR (300 MHz, DMSO-$d_6$) δ 7.67-7.64 (m, 1H), 7.64-7.54 (m, 2H), 7.40 (t, J=7.7 Hz, 1H), 7.36 (s, 1H), 7.23 (s, 1H), 7.20 (s, 1H), 7.07 (d, J=8.0 Hz, 1H), 6.93-6.87 (m, 1H), 6.58-6.54 (m, 1H), 5.27 (s, 2H), 4.16 (s, 2H), 3.58 (s, 2H), 2.46 (d, J=1.1 Hz, 3H); $^{19}$F NMR (282 MHz, DMSO-$d_6$) δ−118.94; MS (ES+): 420.10 (M+1); MS (ES−): 418.10 (M−1); Analysis calculated for C$_{25}$H$_{22}$FNO$_4$·1.0 HCl: C, 65.86; H, 5.08; N, 3.07; Cl, 7.78; Found: C, 65.42; H, 4.80; N, 3.15; Cl, 7.89.

Scheme-410

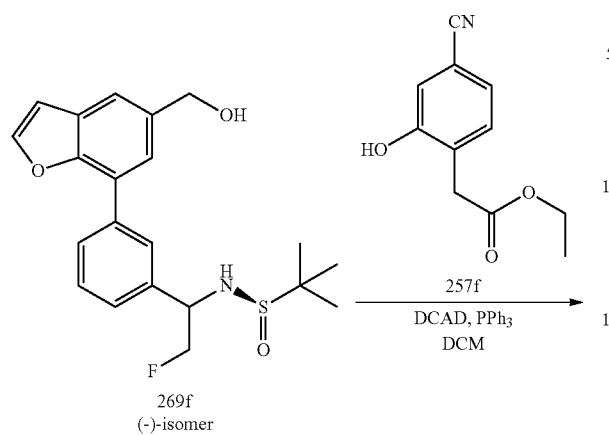

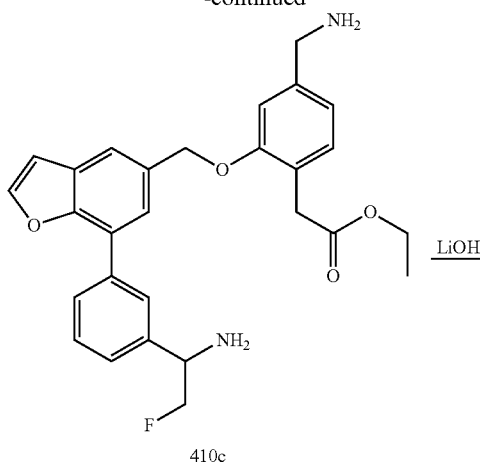

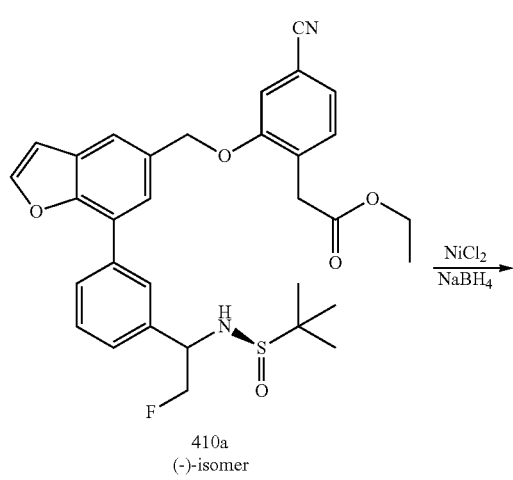

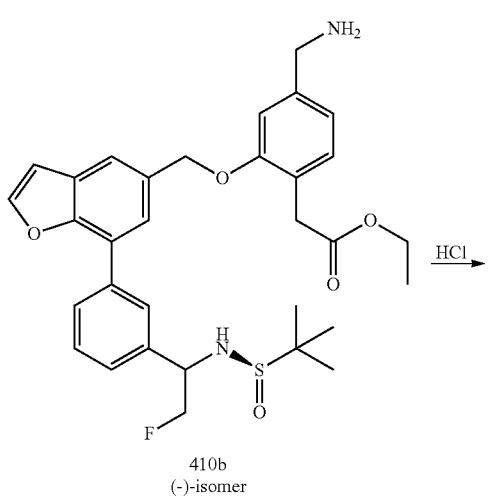

Preparation of (+)-2-(2-((7-(3-(1-amino-2-fluoroethyl)phenyl)benzofuran-5-yl)methoxy)-4-(aminomethyl)phenyl)acetic Acid (410d)

Step-1: Preparation of (−)-ethyl 2-(4-cyano-2-((7-(3-(1-((R)-1,1-dimethylethylsulfinamido)-2-fluoroethyl)phenyl)benzofuran-5-yl)methoxy)phenyl)acetate (410a)

Compound 410a was prepared according to the procedure reported in step-2 of scheme-23 from (−)-(R)—N-(2-fluoro-1-(3-(5-(hydroxymethyl)benzofuran-7-yl)phenyl)ethyl)-2-methylpropane-2-sulfinamide (269f) (547 mg, 1.403 mmol) in DCM (12 mL) using triphenylphosphine (460 mg, 1.754 mmol), ethyl 2-(4-cyano-2-hydroxyphenyl)acetate (257f) (240 mg, 1.170 mmol) and a solution of (E)-bis(4-chlorobenzyl) diazene-1,2-dicarboxylate (DCAD, 644 mg, 1.754 mmol) in DCM (12 mL). This gave after workup and purification by flash column chromatography [silica gel, eluting with a 9:1 mixture of ethyl acetate and methanol in hexanes (1:0 to 1:1)] (−)-ethyl 2-(4-cyano-2-((7-(3-(1-((R)-1,1-dimethylethylsulfinamido)-2-fluoroethyl)phenyl)benzofuran-5-yl)methoxy)phenyl)acetate (410a) (661 mg) as a white solid; MS (ES+): 577.20 (M+1); Optical rotation $[\alpha]_D = -3.12$ (c=0.685, MeOH)

Step-2: Preparation of (−)-ethyl 2-(4-(aminomethyl)-2-((7-(3-(1-((R)-1,1-dimethylethylsulfinamido)-2-fluoroethyl)phenyl)benzofuran-5-yl)methoxy)phenyl)acetate (410b)

Compound 410b was prepared according to the procedure reported in step-2 of scheme-256 from (−)-ethyl 2-(4-cyano-2-((7-(3-(1-((R)-1,1-dimethylethylsulfinamido)-2-fluoroethyl)phenyl)benzofuran-5-yl)methoxy)phenyl)acetate (410a) (420 mg, 0.728 mmol) in methanol (22 mL) using nickel (II) chloride hexahydrate (43 mg, 0.182 mmol) and sodium borohydride (165 mg, 4.37 mmol), using N1-(2-aminoethyl)ethane-1,2-diamine (0.157 mL, 1.457 mmol) for quenching. This gave after workup and purification by flash column chromatography [silica gel, eluting with chloroform/methanol (1:0 to 6:1)] (−)-ethyl 2-(4-(aminomethyl)-2-((7-(3-(1-((R)-1,1-dimethylethylsulfinamido)-2-fluoroethyl)phenyl)benzofuran-5-yl)methoxy)phenyl)acetate (410b) (128 mg) as a white solid; MS (ES+): 581.30 (M+1); Optical rotation [t]D=−2.20 (c=0.27, MeOH)

Step-3: Preparation of Ethyl 2-(2-((7-(3-(1-amino-2-fluoroethyl)phenyl)benzofuran-5-yl)methoxy)-4-(aminomethyl)phenyl)acetate (410c)

Compound 410c was prepared according to the procedure reported in step-4 of scheme-405 from (−)-ethyl 2-(4-(aminomethyl)-2-((7-(3-(1-((R)-1,1-dimethylethylsulfinamido)-2-fluoroethyl)phenyl)benzofuran-5-yl)methoxy)phenyl)acetate (410b) (120 mg, 0.207 mmol) in tetrahydrofuran (4 mL) using 3 N aqueous HCl (0.207 mL, 0.620 mmol) and stirring at room temperature for 3 h. This gave after workup ethyl 2-(2-((7-(3-(1-amino-2-fluoroethyl)phenyl)benzofuran-5-yl)methoxy)-4-(aminomethyl)phenyl)acetate (410c) which was used as such for next step. MS (ES+): 477.10 (M+1).

Step-4: Preparation of (+)-2-(2-((7-(3-(1-amino-2-fluoroethyl)phenyl)benzofuran-5-yl)methoxy)-4-(aminomethyl)phenyl)acetic Acid (410d)

Compound 410d was prepared according to the procedure reported in step-6 of scheme-1 from ethyl 2-(2-((7-(3-(1-amino-2-fluoroethyl)phenyl)benzofuran-5-yl)methoxy)-4-(aminomethyl)phenyl)acetate (410c) (0.099 g, 0.207 mmol) in MeOH (5 mL) using a solution of lithium hydroxide hydrate (0.071 g, 1.656 mmol) in water (5 mL) and stirring at room temperature for 20 h. This gave after workup and purification by reverse phase column (C18, 100 g, eluting with (1:0 to 0:1) MeCN in $H_2O$ containing 0.1% HCl) (+)-2-(2-((7-(3-(1-amino-2-fluoroethyl)phenyl)benzofuran-5-yl)methoxy)-4-(aminomethyl)phenyl)acetic acid (410d) (43 mg, 13% for 4 steps) HCl salt as a white solid. $^1$H NMR (300 MHz, DMSO-$d_6$) δ 12.27 (s, 1H), 9.01 (s, 3H), 8.46 (s, 3H), 8.13-8.10 (m, 2H), 8.04-7.90 (m, 1H), 7.78 (d, J=1.6 Hz, 1H), 7.70 (d, J=1.7 Hz, 1H), 7.66-7.60 (m, 2H), 7.42 (d, J=1.6 Hz, 1H), 7.25 (d, J=7.7 Hz, 1H), 7.07 (d, J=2.2 Hz, 1H), 7.02 (dd, J=7.7, 1.5 Hz, 1H), 5.28 (s, 2H), 4.98-4.72 (m, 3H), 4.07-3.93 (m, 2H), 3.60 (s, 2H); $^{19}$F NMR (282 MHz, DMSO-$d_6$) δ−222.72; MS (ES+): 449.10 (M+1); MS (ES−): 447.10 (M−1); Analysis calculated for $C_{26}H_{25}FN_2O_4 \cdot 1.85HCl \cdot 3H_2O$: C, 54.79; H, 5.81; N, 4.91; Cl, 11.51; Found: C, 54.41; H, 5.64; N, 4.71; Cl, 11.15; Optical rotation $[\alpha]_D$=+20.69 (c=0.145, MeOH).

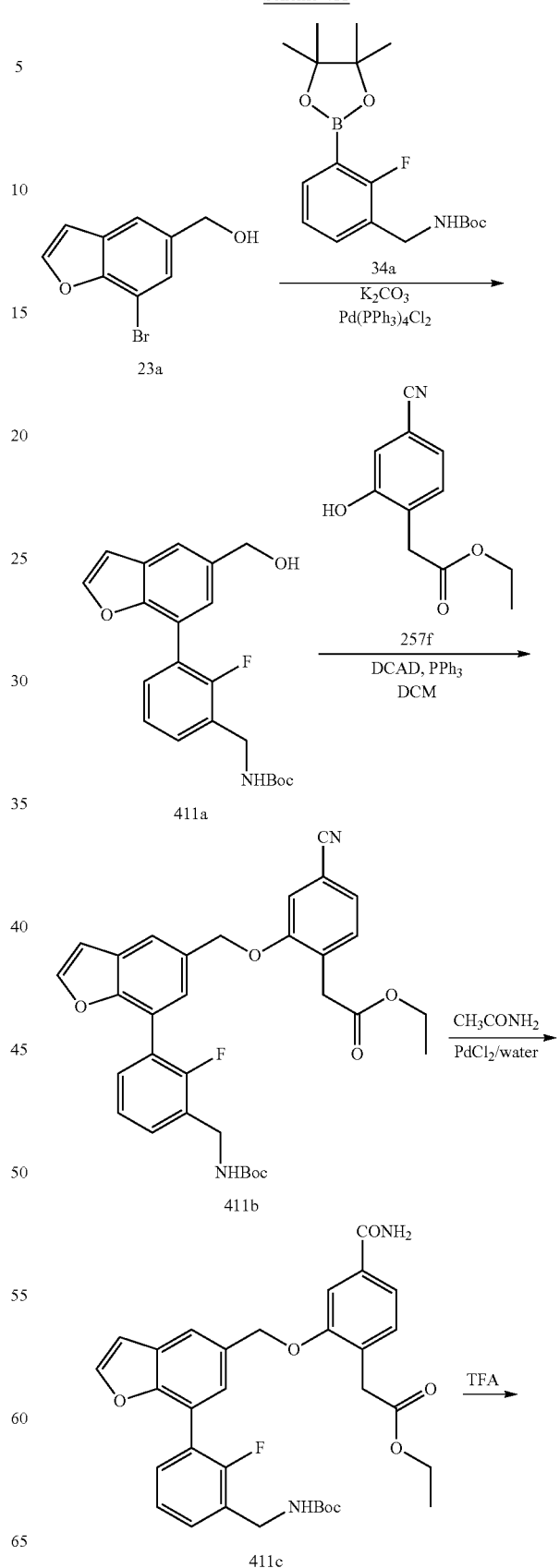

Scheme-411

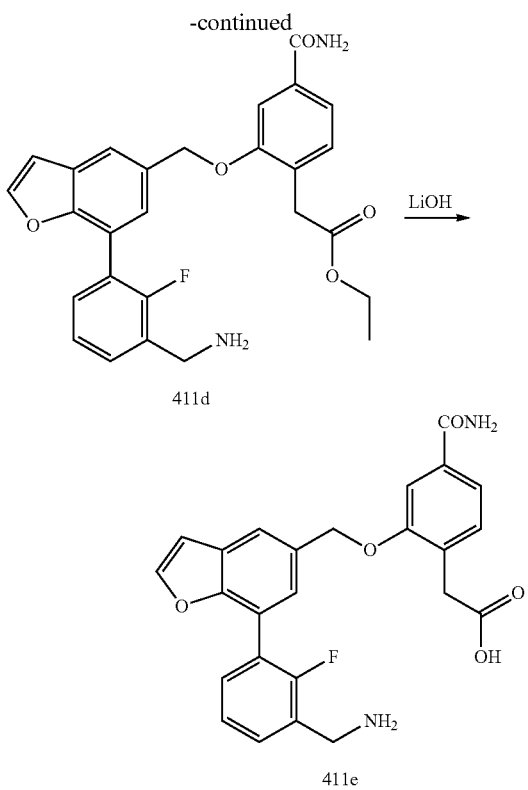

Preparation of 2-(2-((7-(3-(aminomethyl)-2-fluorophenyl)benzofuran-5-yl)methoxy)-4-carbamoylphenyl)acetic Acid (411e)

Step-1: Preparation of tert-butyl 2-fluoro-3-(5-(hydroxymethyl)benzofuran-7-yl)benzylcarbamate (411a)

Compound 411a was prepared according to the procedure reported in step-3 of scheme-1 from (7-bromobenzofuran-5-yl)methanol (23a) (4.1 g, 18.06 mmol) in dioxane (150 mL) using tert-butyl 2-fluoro-3-(4,4,5,5-tetramethyl-1,3,2-dioxaborolan-2-yl)benzylcarbamate (34a) (6.34 g, 18.06 mmol), a solution of potassium carbonate (7.49 g, 54.2 mmol) in water (15 mL), Pd(PPh$_3$)$_2$Cl$_2$ (1.901 g, 2.71 mmol) and heating under a nitrogen atmosphere at 100° C. for 3 h. This gave after workup, purification by flash column chromatography (silica gel, 120 g, eluting with 0 to 35% ethyl acetate in hexanes) tert-butyl 2-fluoro-3-(5-(hydroxymethyl)benzofuran-7-yl)benzylcarbamate (411a) (3.14 g, 47% yield) as a light brown gummy solid; $^1$H NMR (300 MHz, DMSO-d$_6$) δ 7.99 (d, J=2.2 Hz, 1H), 7.65 (dd, J=1.7, 0.9 Hz, 1H), 7.52-7.24 (m, 4H), 7.01 (d, J=2.2 Hz, 1H), 5.28 (t, J=5.8 Hz, 1H), 4.68-4.58 (m, 2H), 4.26 (d, J=6.1 Hz, 2H), 1.41 (s, 9H); $^{19}$F NMR (282 MHz, DMSO-d$_6$) δ−120.94.

Step-2: Preparation of Ethyl 2-(2-((7-(3-(((tert-butoxycarbonyl)amino)methyl)-2-fluorophenyl)benzofuran-5-yl)methoxy)-4-cyanophenyl)acetate (411b)

Compound 411b was prepared according to the procedure reported in step-2 of scheme-23 from tert-butyl 2-fluoro-3-(5-(hydroxymethyl)benzofuran-7-yl)benzylcarbamate (411a) (434 mg, 1.170 mmol) in DCM (12 mL) using triphenylphosphine (460 mg, 1.754 mmol), ethyl 2-(4-cyano-2-hydroxyphenyl)acetate (257f) (240 mg, 1.170 mmol) and a solution of (E)-bis(4-chlorobenzyl) diazene-1,2-dicarboxylate (DCAD, 644 mg, 1.754 mmol) in DCM (12 mL). This gave after workup and purification by flash column chromatography (silica gel, 40 g, eluting with 30% ethyl acetate in hexanes) ethyl 2-(2-((7-(3-(((tert-butoxycarbonyl)amino)methyl)-2-fluorophenyl)benzofuran-5-yl)methoxy)-4-cyanophenyl)acetate (411b) (527 mg, 81% yield) as a clear oil; $^1$H NMR (300 MHz, DMSO-d$_6$) δ 8.06 (d, J=2.2 Hz, 1H), 7.77 (d, J=1.6 Hz, 1H), 7.63 (d, J=1.3 Hz, 1H), 7.54-7.29 (m, 7H), 7.07 (d, J=2.2 Hz, 1H), 5.30 (s, 2H), 4.26 (d, J=6.1 Hz, 2H), 3.88 (q, J=7.1 Hz, 2H), 3.71 (s, 2H), 1.41 (s, 9H), 0.94 (t, J=7.1 Hz, 3H); $^{19}$F NMR (282 MHz, DMSO-d$_6$) δ−120.79; MS (ES+): 581.20 (M+Na).

Step-3: Preparation of Ethyl 2-(2-((7-(3-(((tert-butoxycarbonyl)amino)methyl)-2-fluorophenyl)benzofuran-5-yl)methoxy)-4-carbamoylphenyl)acetate (411c)

Compound 411c was prepared according to the procedure reported in step-1 of scheme-238 from ethyl 2-(2-((7-(3-(((tert-butoxycarbonyl)amino)methyl)-2-fluorophenyl)benzofuran-5-yl)methoxy)-4-cyanophenyl)acetate (411b) (200 mg, 0.358 mmol) in THF (9 mL) and water (0.8 mL), using acetamide (127 mg, 2.148 mmol), palladium(II) chloride (19 mg, 0.107 mmol) and stirring at room temperature for 18 h. This gave after workup and purification by flash column chromatography (silica gel, 12 g, eluting with methanol in DCM from 0 to 5%] ethyl 2-(2-((7-(3-(((tert-butoxycarbonyl)amino)methyl)-2-fluorophenyl)benzofuran-5-yl)methoxy)-4-carbamoylphenyl)acetate (411c) (130 mg, 63.0%) as a white solid; $^1$H NMR (300 MHz, DMSO-d$_6$) δ 8.06 (d, J=2.2 Hz, 1H), 7.99 (s, 1H), 7.78 (d, J=1.6 Hz, 1H), 7.63 (d, 1H), 7.55-7.26 (m, 8H), 7.06 (d, J=2.2 Hz, 1H), 5.28 (s, 2H), 4.26 (d, J=6.1 Hz, 2H), 3.89 (q, J=7.1 Hz, 2H), 3.66 (s, 2H), 1.41 (s, 9H), 0.96 (t, J=7.1 Hz, 3H); $^{19}$F NMR (282 MHz, DMSO-d$_6$) δ−120.70; MS (ES+): 599.20 (M+Na).

Step-4: Preparation of Ethyl 2-(2-((7-(3-(aminomethyl)-2-fluorophenyl)benzofuran-5-yl)methoxy)-4-carbamoylphenyl)acetate (411d)

Compound 411d was prepared according to the procedure reported in step-5 of scheme-1 from ethyl 2-(2-((7-(3-(((tert-butoxycarbonyl)amino)methyl)-2-fluorophenyl)benzofuran-5-yl)methoxy)-4-carbamoylphenyl)acetate (411c) (120 mg, 0.208 mmol) in DCM (8 mL) using TFA (0.309 mL, 4.16 mmol). This gave after workup ethyl 2-(2-((7-(3-(aminomethyl)-2-fluorophenyl)benzofuran-5-yl)methoxy)-4-carbamoylphenyl)acetate (411d) which was used as such for next step. MS (ES+): 477.20 (M+1).

Step-5: Preparation of 2-(2-((7-(3-(aminomethyl)-2-fluorophenyl)benzofuran-5-yl)methoxy)-4-carbamoylphenyl)acetic Acid (411e)

Compound 411e was prepared according to the procedure reported in step-6 of scheme-1 from ethyl 2-(2-((7-(3-(aminomethyl)-2-fluorophenyl)benzofuran-5-yl)methoxy)-4-carbamoylphenyl)acetate (411d) (0.208 mmol, from above step-4) in THF/methanol (5 mL, 1:1 each) using solution of lithium hydroxide hydrate (0.071 g, 1.664 mmol) in water (5 mL) and stirring at room temperature for 15h.

1273

This gave after workup and purification by reverse-phase column chromatography [C-18 column, eluting with water (containing 0.1% HCl)/acetonitrile (1:0 to 0:1)] 2-(2-((7-(3-(aminomethyl)-2-fluorophenyl)benzofuran-5-yl)methoxy)-4-carbamoylphenyl)acetic acid (411e) (56 mg, 60% for 2 steps) HCl salt as a white solid; $^1$H NMR (300 MHz, DMSO-$d_6$) δ 12.30 (s, 1H), 8.48 (s, 3H), 8.06 (d, J=2.2 Hz, 1H), 8.00 (s, 1H), 7.84 (d, J=1.6 Hz, 1H), 7.69 (t, J=7.4 Hz, 2H), 7.61 (d, J=1.6 Hz, 1H), 7.49 (s, 1H), 7.47-7.35 (m, 3H), 7.29 (d, J=7.8 Hz, 1H), 7.07 (d, J=2.2 Hz, 1H), 5.32 (s, 2H), 4.23-4.12 (m, 2H), 3.63 (s, 2H); $^{19}$F NMR (282 MHz, DMSO-$d_6$) δ–118.26; MS (ES+): 449.10 (M+1); Analysis calculated for $C_{25}H_{21}FN_2O_4$·HCl·2H$_2$O: C, 57.64; H, 5.03; N, 5.38; Cl, 6.81; Found: C, 57.38; H, 4.84; N, 5.31; Cl, 6.55.

Scheme-412

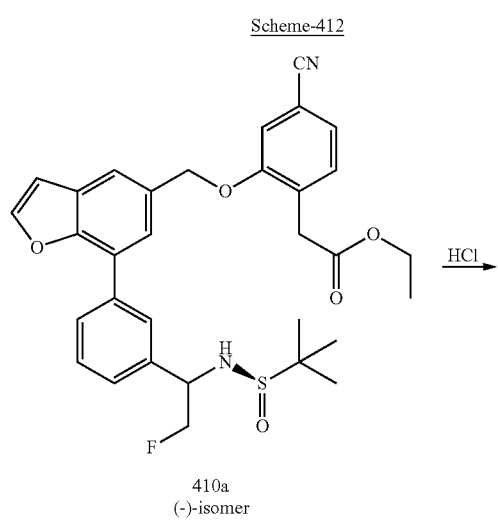

410a
(–)-isomer

412a

1274

-continued

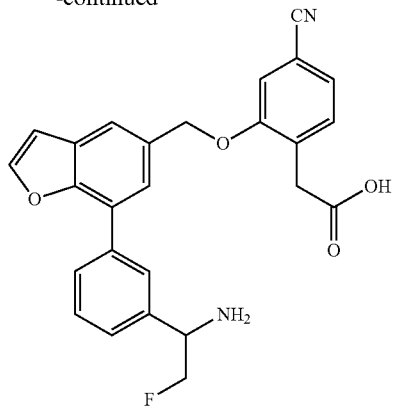

412b (+)-isomer

Preparation of (+)-2-(2-((7-(3-(1-amino-2-fluoroethyl)phenyl)benzofuran-5-yl)methoxy)-4-cyanophenyl)acetic Acid (412b)

Step-1: Preparation of Ethyl 2-(2-((7-(3-(1-amino-2-fluoroethyl)phenyl)benzofuran-5-yl)methoxy)-4-cyanophenyl)acetate (412a)

Compound 412a was prepared according to the procedure reported in step-4 of scheme-405 from (–)-ethyl 2-(4-cyano-2-((7-(3-(1-((R)-1,1-dimethylethylsulfinamido)-2-fluoroethyl)phenyl)benzofuran-5-yl)methoxy)phenyl)acetate (410a) (88 mg, 0.153 mmol) in THF (4 mL) using 3 N aqueous HCl (0.153 mL, 0.458 mmol) and stirring at room temperature for 4 h. This gave after workup ethyl 2-(2-((7-(3-(1-amino-2-fluoroethyl)phenyl)benzofuran-5-yl)methoxy)-4-cyanophenyl)acetate (412a) which was used as such for next step. MS (ES+): 473.20 (M+1).

Step-2: Preparation of (+)-2-(2-((7-(3-(1-amino-2-fluoroethyl)phenyl)benzofuran-5-yl)methoxy)-4-cyanophenyl)acetic Acid (412b)

Compound 412b was prepared according to the procedure reported in step-6 of scheme-1 from ethyl 2-(2-((7-(3-(1-amino-2-fluoroethyl)phenyl)benzofuran-5-yl)methoxy)-4-cyanophenyl)acetate (412a) (0.153 mmol; from above step-1) in MeOH/THF (4 mL, each) using a solution of lithium hydroxide hydrate (0.052 g, 1.224 mmol) in water (4 mL) and stirring at room temperature for 16 h. This gave after workup and purification by reverse phase column [C18 column, eluting with water (containing 0.1% HCl)/acetonitrile (1:0 to 0:1)] (+)-2-(2-((7-(3-(1-amino-2-fluoroethyl)phenyl)benzofuran-5-yl)methoxy)-4-cyanophenyl)acetic acid (412b) HCl salt (30 mg, 44% yield for 2 steps) HCl as a white solid. $^1$H NMR (300 MHz, DMSO-$d_6$) δ 8.12 (d, J=2.2 Hz, 1H), 8.05-8.02 (m, 1H), 7.97 (dt, J=7.3, 1.7 Hz, 1H), 7.77 (d, J=1.6 Hz, 1H), 7.68-7.56 (m, 4H), 7.48-7.38 (m, 2H), 7.08 (d, J=2.2 Hz, 1H), 5.35 (s, 2H), 4.94-4.69 (m, 3H), 3.69 (s, 2H); $^{19}$F NMR (282 MHz, DMSO-$d_6$) δ–222.51; MS (ES+): 445.10 (M+1); Analysis calculated for $C_{26}H_{21}FN_2O_4$·HCl·1.75H$_2$O: C, 60.94; H, 5.02; N, 5.47; Found: C, 61.00; H, 4.96; N, 5.45; Optical rotation [t]D=+16.521 (c=0.115, MeOH).

Scheme-413
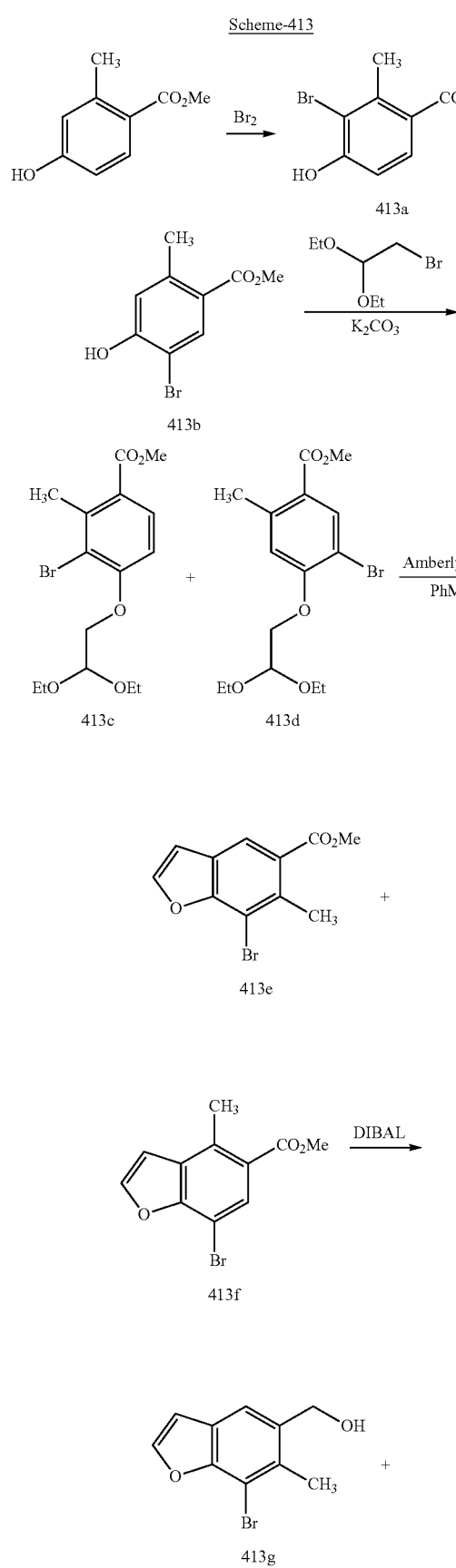
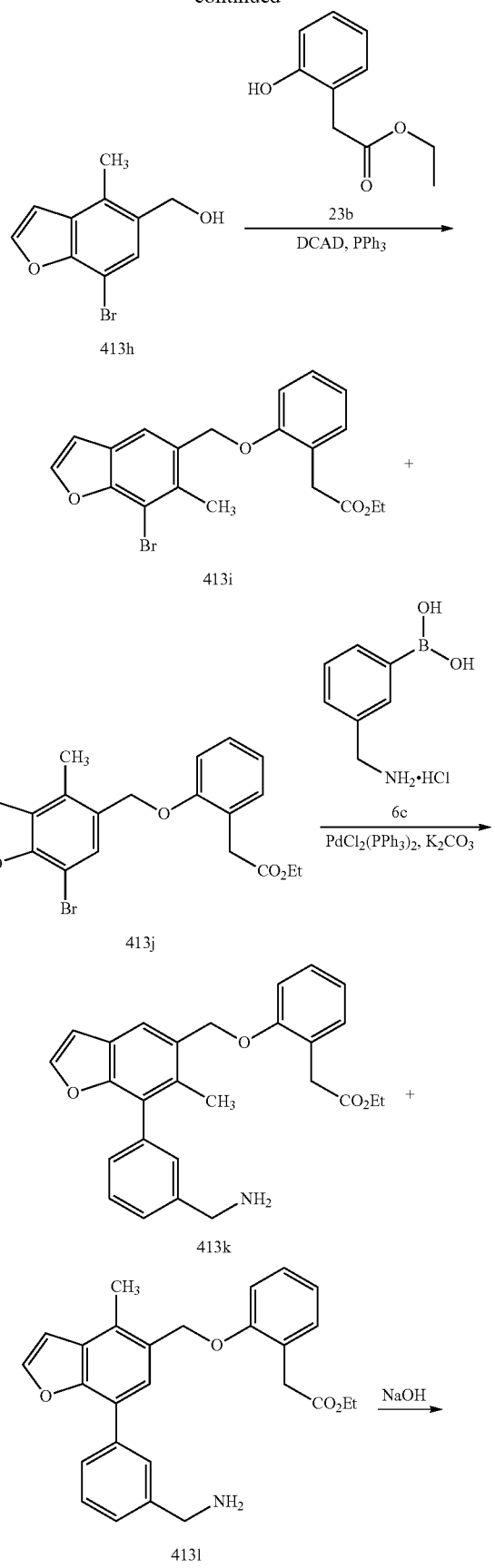

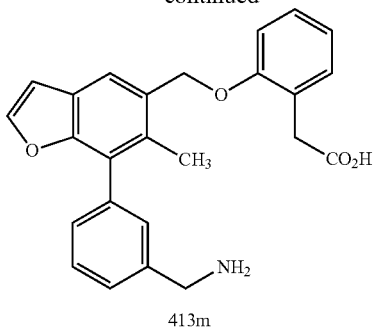

413m

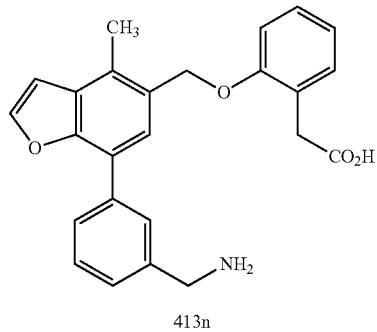

413n

Preparation of 2-(2-((7-(3-(aminomethyl)phenyl)-6-methylbenzofuran-5-yl)methoxy)phenyl)acetic Acid (413m) and 2-(2-((7-(3-(aminomethyl)phenyl)-4-methylbenzofuran-5-yl)methoxy)phenyl)acetic Acid (413n)

Step-1: Preparation of methyl 3-bromo-4-hydroxy-2-methylbenzoate (413a) and methyl 5-bromo-4-hydroxy-2-methylbenzoate (413b)

To a solution of methyl 4-hydroxy-2-methylbenzoate (2.0 g, 12.04 mmol; CAS #57556-31-7) in DCM (10 mL) at 0° C. was added bromine (2.116 g, 13.24 mmol) in DCM (5 mL) dropwise over a period of 1 h. The resulting mixture was stirred at rt for 2 h, quenched with ice (30 g). The organic layer was separated, washed with $H_2O$ (25 mL), brine (25 mL), dried, filtered and concentrated in vacuum. The residue obtained was purified by flash column chromatography (silica gel, 40 g, eluting with 0-10% EtOAc in hexane) to provide an inseparable 1:1 mixture of methyl 5-bromo-4-hydroxy-2-methylbenzoate (413b) and methyl 3-bromo-4-hydroxy-2-methylbenzoate (413a) (2.90 g, 98% yield) as a white solid. $^1$H NMR (300 MHz, DMSO-$d_6$) 11.28-10.81 (m, 2H), 7.97 (d, J=1.0 Hz, 1H), 7.68 (dd, J=8.6, 1.0 Hz, 1H), 6.94-6.76 (m, 2H), 3.77 (dd, J=3.2, 1.0 Hz, 6H), 2.59 (s, 3H), 2.43 (s, 3H). LC-MS: t=2.38-2.41 min; MS (ES−): 243/245.

Step-2: Preparation of methyl 3-bromo-4-(2,2-diethoxyethoxy)-2-methylbenzoate (413c) and methyl 5-bromo-4-(2,2-diethoxyethoxy)-2-methylbenzoate (413d)

Compounds 413c and 413d were prepared according to the procedure reported in step-1 of scheme-382 from a mixture containing methyl 3-bromo-4-hydroxy-2-methylbenzoate (413a) and methyl 5-bromo-4-hydroxy-2-methylbenzoate (413b) (2.90 g, 11.83 mmol; from above step-1), bromoacetaldehyde diethyl acetal (3.50 g, 17.75 mmol), $K_2CO_3$ (3.27 g, 23.67 mmol) in DMF (10 mL) and heating at 80° C. for 16 h. This gave after workup and purification by flash column chromatography [silica (24 g), eluting with EtOAc in hexane from 0-15%] an inseparable 1:1.2 mixture of methyl 3-bromo-4-(2,2-diethoxyethoxy)-2-methylbenzoate (413c) and methyl 5-bromo-4-(2,2-diethoxyethoxy)-2-methylbenzoate (413d) (3.08 g, 72.1% yield) as a clear colorless oil: $^1$H NMR (300 MHz, DMSO-$d_6$, for pure compound 413d) δ 8.01 (s, 1H), 7.15 (s, 1H), 4.85 (t, J=5.3 Hz, 1H), 4.10 (d, J=5.3 Hz, 2H), 3.79 (s, 3H), 3.78-3.55 (m, 4H), 2.51 (s, 3H), 1.15 (t, J=7.0 Hz, 6H); MS (ES+): 383/385.

Step-3: Preparation of methyl 7-bromo-6-methylbenzofuran-5-carboxylate (413e) and methyl 7-bromo-4-methylbenzofuran-5-carboxylate (413f)

Compounds 413e and 413f were prepared according to the procedure reported in step-2 of scheme-390 from a mixture containing methyl 3-bromo-4-(2,2-diethoxyethoxy)-2-methylbenzoate (413c) and methyl 5-bromo-4-(2,2-diethoxyethoxy)-2-methylbenzoate (413d) (3.08 g, 8.53 mmol; from above step-2) in anhydrous PhMe (30 mL) using Amberlyst 15 (0.869 g, 8.53 mmol) and heating at 130° C. for 16 h with concomitant removal of water using a Dean-Stark apparatus. This gave after workup and purification by flash column chromatography [silica (24 g), eluting with EtOAc in hexane from 0-11%] an inseparable 1:1.8 mixture of methyl 7-bromo-6-methylbenzofuran-5-carboxylate (413e) and methyl 7-bromo-4-methylbenzofuran-5-carboxylate (413f) (0.59 g, 26% yield) as a white solid; $^1$H NMR (300 MHz, DMSO-$d_6$; 1:1.8 mixture) δ 8.21 (d, J=2.1 Hz, 0.65H), 8.16 (d, J=2.2 Hz, 0.35H), 8.11 (d, J=4.0 Hz, 0.35H), 7.98 (s, 0.65H), 7.37 (dd, J=2.3, 1.2 Hz, 0.65H), 7.16 (dd, J=2.2, 1.3 Hz, 0.35H), 3.86 (s, 1.05H), 3.85 (3, 1.95H), 2.69 (s, 1.95H), 2.65 (s, 0.35H).

Step-4: Preparation of (7-bromo-6-methylbenzofuran-5-yl)methanol (413g) and (7-bromo-4-methylbenzofuran-5-yl)methanol (413h)

Compounds 413g and 413h were prepared according to the procedure reported in step-2 of scheme-212 from a mixture containing methyl 7-bromo-6-methylbenzofuran-5-carboxylate (413e) and methyl 7-bromo-4-methylbenzofuran-5-carboxylate (413f) (0.47 g, 1.747 mmol) in DCM (10 mL) using 1 M DIBAL-H in DCM (4.02 mL, 4.02 mmol). This gave after workup and purification by flash column chromatography (silica gel, eluting with 0-20% EtOAc in Hexane) an inseparable 1:1.8 mixture of (7-bromo-6-methylbenzofuran-5-yl)methanol (413g) and (7-bromo-4-methylbenzofuran-5-yl)methanol (413h) (0.38 g, 90% yield) as a white solid; $^1$H NMR (300 MHz, DMSO-$d_6$ for pure compound 413h) δ 8.06 (d, J=2.2 Hz, 1H), 7.52 (s, 1H), 7.18 (dd, J=2.3, 0.6 Hz, 1H), 5.22 (t, J=5.4 Hz, 1H), 4.57 (d, J=5.0 Hz, 2H), 2.39 (s, 3H).

Step-5: Preparation of Ethyl 2-(2-((7-bromo-6-methylbenzofuran-5-yl)methoxy)phenyl)acetate (413i) and ethyl 2-(2-((7-bromo-4-methylbenzofuran-5-yl)methoxy)phenyl)acetate (413j)

Compounds 413i and 413j were prepared according to the procedure reported in step-2 of scheme-23 from a mixture containing (7-bromo-6-methylbenzofuran-5-yl)methanol (413g) and (7-bromo-4-methylbenzofuran-5-yl)methanol (413h) (380 mg, 1.576 mmol) in DCM (10 mL) using triphenylphosphine (827 mg, 3.15 mmol), ethyl 2-(2-hydroxyphenyl) acetate (23b) (369 mg, 2.049 mmol) and (E)-bis(4-chlorobenzyl) diazene-1,2-dicarboxylate (DCAD, 1158 mg, 3.15 mmol). This gave after workup and purification by flash column chromatography (silica gel, eluting with EtOAc in hexane from 0-15%) an inseparable 1:1.8 mixture of ethyl 2-(2-((7-bromo-6-methylbenzofuran-5-yl)methoxy)phenyl)acetate (413i) and ethyl 2-(2-((7-bromo-4-methylbenzofuran-5-yl)methoxy)phenyl)acetate (413j) (500 mg, 1.240 mmol, 79% yield) as a colorless oil that solidified upon standing in air; $^1$H NMR (300 MHz, DMSO-$d_6$ for pure compound 413j) δ 8.08 (d, J=2.2 Hz, 1H), 7.73 (s, 1H), 7.29 (dd, J=8.8, 7.1 Hz, 1H), 7.25-7.19 (m, 1H), 7.19-7.13 (m, 1H), 7.06 (dd, J=2.3, 1.6 Hz, 1H), 6.93 (dd, J=7.9, 6.8 Hz, 1H), 5.19 (s, 2H), 3.91 (q, J=7.1 Hz, 2H), 3.57 (s, 2H), 1.03-0.99 (m, 3H). LC-MS: t=2.97 min; MS (ES+): 425/427 (M+Na).

Step-6: Preparation of Ethyl 2-(2-((7-(3-(aminomethyl)phenyl)-6-methylbenzofuran-5-yl)methoxy)phenyl)acetate (413k) and ethyl 2-(2-((7-(3-(aminomethyl)phenyl)-4-methylbenzofuran-5-yl)methoxy)phenyl)acetate (413l)

Compounds 413k and 413l were prepared according to the procedure reported in step-3 of scheme-1 from a mixture containing ethyl 2-(2-((7-bromo-6-methylbenzofuran-5-yl)methoxy)phenyl)acetate (413i) and ethyl 2-(2-((7-bromo-4-methylbenzofuran-5-yl)methoxy)phenyl)acetate (413j) (290 mg, 0.719 mmol) in dioxane (4 mL) using 3-(aminomethyl)phenylboronic acid hydrochloride (6c) (162 mg, 0.863 mmol), K$_2$CO$_3$ (298 mg, 2.157 mmol) in water (1 mL) and bis(triphenylphosphine)palladium(II)chloride (51 mg, 0.072 mmol) under an Ar atmosphere and heating at 100° C. for 16 h on oil bath. This gave after workup, purification by flash column chromatography [silica gel, eluting with 0-5% MeOH in DCM] an inseparable mixture of compounds 413k and 413l (272 mg) as a pale colorless oil (272 mg); MS (ES+): 430 (M+1).

Step-7: Preparation of 2-(2-((7-(3-(aminomethyl)phenyl)-6-methylbenzofuran-5-yl)methoxy)phenyl)acetic Acid (413m) and 2-(2-((7-(3-(aminomethyl)phenyl)-4-methylbenzofuran-5-yl)methoxy)phenyl)acetic Acid (413n)

Compounds 413m and 413n were prepared according to the procedure reported in step-4 of scheme-4 from a mixture containing ethyl 2-(2-((7-(3-(aminomethyl)phenyl)-6-methylbenzofuran-5-yl)methoxy)phenyl)acetate (413k) and ethyl 2-(2-((7-(3-(aminomethyl)phenyl)-4-methylbenzofuran-5-yl)methoxy)phenyl)acetate (413l) (272 mg, from above step-6) in MeOH (4 mL) using NaOH (86 mg, 2.157 mmol) in water (1 mL). This gave after workup and purification by reverse phase column chromatography (C18 100g, eluting with 0-60% MeCN in H$_2$O containing 0.1% HCl) 2-(2-((7-(3-(aminomethyl)phenyl)-6-methylbenzofuran-5-yl)methoxy)phenyl)acetic acid (413m) (12 mg, 0.030 mmol, 4% yield) HCl salt as a white solid: $^1$H NMR (300 MHz, DMSO-$d_6$) δ 7.89 (d, J=2.2 Hz, 1H), 7.79 (s, 1H), 7.63-7.49 (m, 3H), 7.41 (dt, J=6.9, 1.8 Hz, 1H), 7.31-7.14 (m, 3H), 6.97 (d, J=2.2 Hz, 1H), 6.92 (td, J=7.4, 1.2 Hz, 1H), 5.22 (s, 2H), 4.13 (s, 2H), 3.56 (s, 2H), 2.24 (s, 3H); MS (ES+): 402 (M+1), (ES-): 400 (M-1) and 2-(2-((7-(3-(aminomethyl)phenyl)-4-methylbenzofuran-5-yl)methoxy)phenyl)acetic acid (413n) (40 mg, 14% yield) HCl salt as white solid; $^1$H NMR (300 MHz, DMSO-$d_6$) δ 8.10 (d, J=2.3 Hz, 1H), 8.00 (t, J=1.8 Hz, 1H), 7.93 (dt, J=7.9, 1.5 Hz, 1H), 7.70 (s, 1H), 7.57 (t, J=7.6 Hz, 1H), 7.50 (dt, J=7.7, 1.5 Hz, 1H), 7.32-7.14 (m, 4H), 6.92 (td, J=7.3, 1.2 Hz, 1H), 5.24 (s, 2H), 4.13 (s, 2H), 3.54 (s, 2H), 2.54 (s, 3H); MS (ES+): 402 (M+1) (ES-): 400 (M-1).

Scheme-414

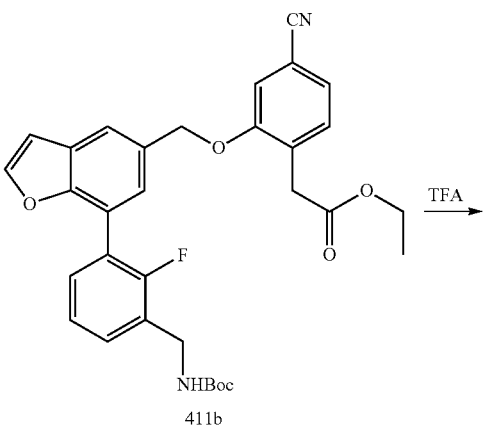

411b

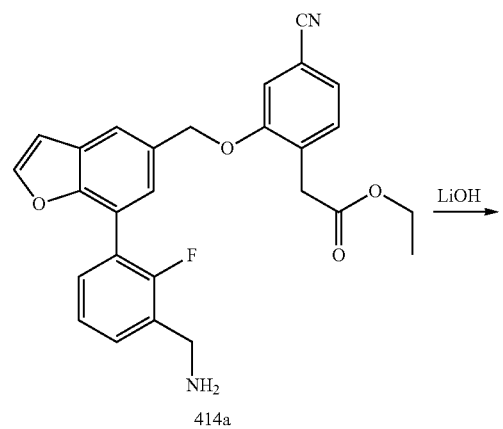

414a

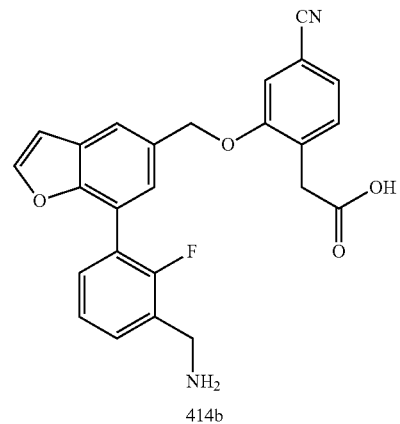

414b

Preparation of 2-(2-((7-(3-(aminomethyl)-2-fluoro-phenyl)benzofuran-5-yl)methoxy)-4-cyanophenyl) acetic Acid (414b)

Step-1: Preparation of Ethyl 2-(2-((7-(3-(aminomethyl)-2-fluorophenyl)benzofuran-5-yl)methoxy)-4-cyanophenyl)acetate (414a)

Compound 414a was prepared according to the procedure reported in step-5 of scheme-1 from ethyl 2-(2-((7-(3-(((tert-butoxycarbonyl)amino)methyl)-2-fluorophenyl)benzofuran-5-yl)methoxy)-4-cyanophenyl)acetate (411b) (200 mg, 0.358 mmol) in DCM (10 mL) using TFA (0.532 mL, 7.16 mmol). This gave after workup ethyl 2-(2-((7-(3-(aminomethyl)-2-fluorophenyl)benzofuran-5-yl)methoxy)-4-cyanophenyl)acetate (414a) which was used as such for next step. MS (ES+): 459.15 (M+1).

Step-2: Preparation of 2-(2-((7-(3-(aminomethyl)-2-fluorophenyl)benzofuran-5-yl)methoxy)-4-cyanophenyl)acetic Acid (414b)

Compound 414b was prepared according to the procedure reported in step-6 of scheme-1 from ethyl 2-(2-((7-(3-(aminomethyl)-2-fluorophenyl)benzofuran-5-yl)methoxy)-4-cyanophenyl)acetate (414a) (0.358 mmol; from above step-1) in MeOH/THF (5 mL, 1:1 each) using a solution of lithium hydroxide hydrate (123 mg, 2.86 mmol) in water (5 mL) and stirring at room temperature for 16 h. This gave after workup and purification by reverse phase column [C18 column, eluting with water (containing 0.1% HCl)/acetonitrile (1:0 to 0:1)] 2-(2-((7-(3-(aminomethyl)-2-fluorophenyl)benzofuran-5-yl)methoxy)-4-cyanophenyl)acetic acid (414b) (74 mg, 48% yield) (74 mg, 48%) HCl salt as a white solid; $^1$H NMR (300 MHz, DMSO-$d_6$) δ 8.65 (s, 3H), 8.07 (d, J=2.2 Hz, 1H), 7.82 (d, J=1.6 Hz, 1H), 7.77-7.63 (m, 2H), 7.60 (d, J=1.4 Hz, 1H), 7.49-7.31 (m, 4H), 7.07 (d, J=2.2 Hz, 1H), 5.34 (s, 2H), 4.17 (s, 2H), 3.68 (s, 2H); $^{19}$F NMR (282 MHz, DMSO-$d_6$) δ −118.46; MS (ES+): 446.20 (M+1); MS (ES−): 431.10 (M−1); Analysis calculated $C_{25}H_{19}FN_2O_4 \cdot HCl \cdot 1.25H_2O$: C, 61.35; H, 4.63; N, 5.72; Found: C, 61.22; H, 4.47; N, 5.60.

Scheme-415

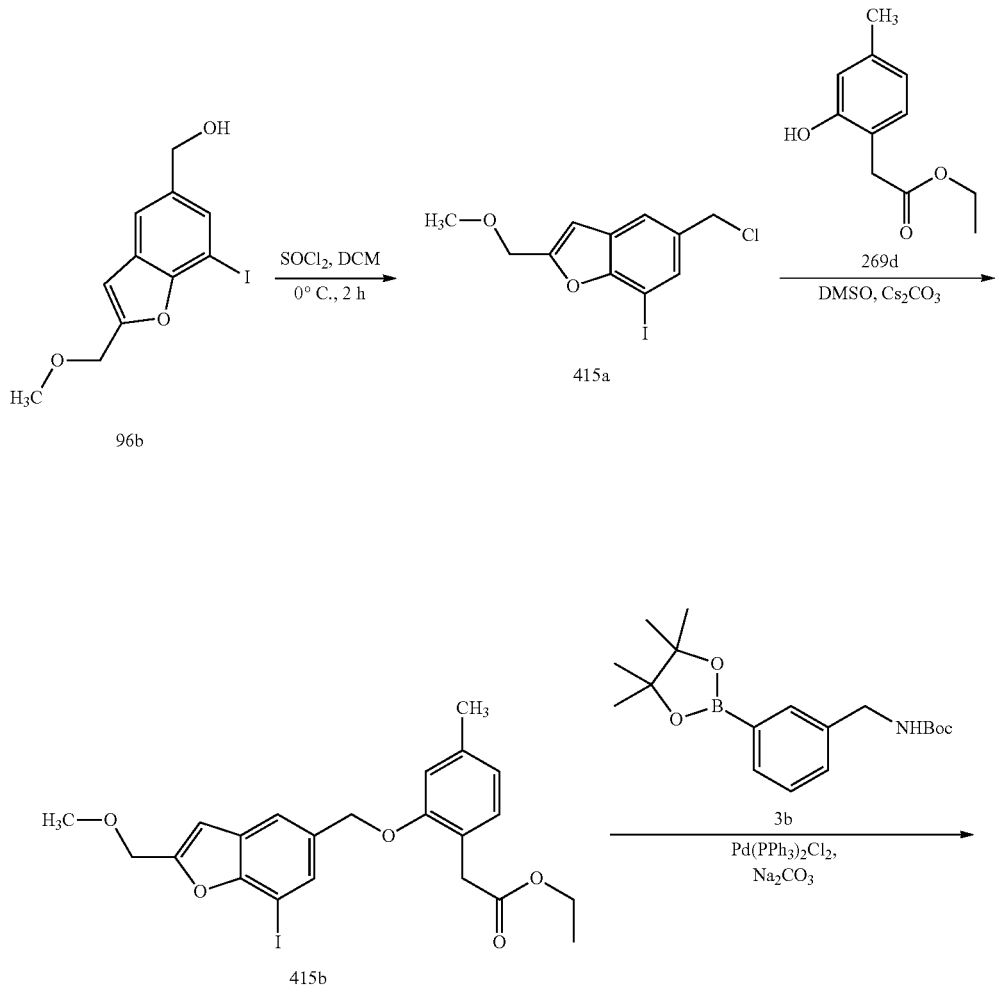

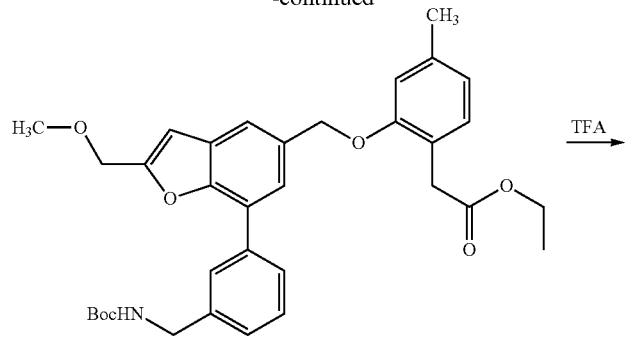

415c

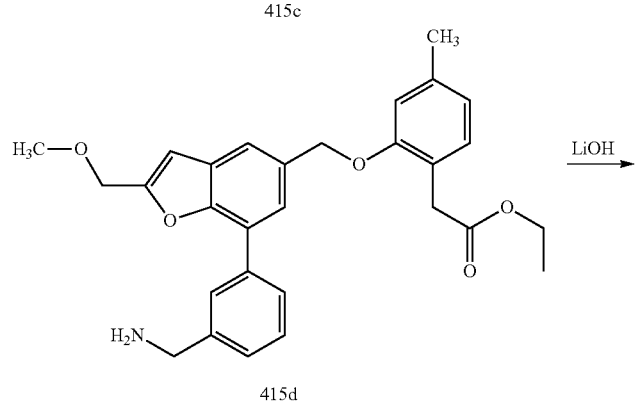

415d

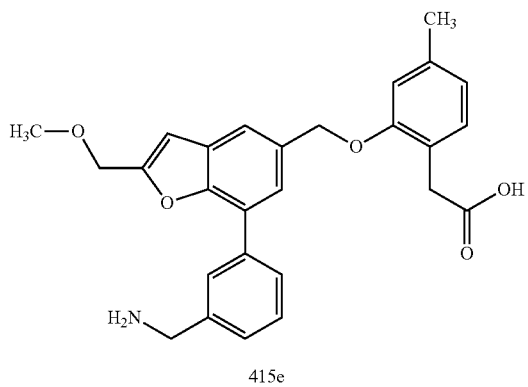 [SMILES: COCc1cc2cc(COc3cc(C)ccc3CC(=O)O)cc(-c3cccc(CN)c3)c2o1]

415e

Preparation of 2-(2-((7-(3-(aminomethyl)phenyl)-2-(methoxymethyl)benzofuran-5-yl)methoxy)-4-methylphenyl)acetic Acid (415e)

Step-1: Preparation of 5-(chloromethyl)-7-iodo-2-(methoxymethyl)benzofuran (415a)

Compound 415a was prepared according to the procedure reported in step-4 of scheme-257 from (7-iodo-2-(methoxymethyl)benzofuran-5-yl)methanol (96b) (1.0 g, 3.14 mmol) in DCM (10 mL) was added at 0° C. SOCl$_2$ (0.748 g, 6.28 mmol). This gave after workup and purification by flash column chromatography (Silica gel, eluting with 1-2% EtOAc in n-heptane) 5-(chloromethyl)-7-iodo-2-(methoxymethyl)benzofuran (415a) (0.90 g, 85.71%) as an off-white solid; $^1$H NMR (300 MHz, DMSO-d$_6$) δ 7.79 (d, J=1.6 Hz, 1H), 7.72 (d, J=1.6 Hz, 1H), 7.08 (s, 1H), 4.85 (s, 2H), 4.56 (s, 2H), 3.34 (s, 3H).

Step-2: Preparation of Ethyl 2-(2-((7-iodo-2-(methoxymethyl)benzofuran-5-yl)methoxy)-4-methylphenyl)acetate (415b)

Compound 415b was prepared according to the procedure reported in step-6 of scheme-257 from 5-(chloromethyl)-7-iodo-2-(methoxymethyl)benzofuran (415a) (0.5 g, 1.48 mmol) using ethyl 2-(2-hydroxy-4-methylphenyl)acetate (269d) (0.431 g, 2.22 mmol), CS$_2$CO$_3$ (0.482 g, 1.48 mmol) in DMSO (5 mL) and stirring at room temperature for 24 h. This gave after workup and purification by flash column chromatography (Silica gel, eluting with 1-3% EtOAc in n-heptane) ethyl 2-(2-((7-iodo-2-(methoxymethyl)benzofuran-5-yl)methoxy)-4-methylphenyl)acetate (415b) (0.5 g, 68.49%) as an off-white solid; $^1$H NMR (300 MHz, DMSO-d$_6$) δ 7.73 (s, 1H), 7.66 (s, 1H), 7.09 (d, J=7.0 Hz, 2H), 6.92 (s, 1H), 6.73 (d, J=7.6 Hz, 1H), 5.12 (s, 2H), 4.56 (s, 2H), 4.07-3.94 (m, 2H), 3.55 (s, 2H), 3.35 (s, 3H), 2.29 (s, 3H), 1.07 (t, J=7.1 Hz, 3H).

Step-3: Preparation of Ethyl 2-(2-((7-(3-(((tert-butoxycarbonyl)amino)methyl)phenyl)-2-(methoxymethyl)benzofuran-5-yl)methoxy)-4-methylphenyl)acetate (415c)

Compound 415c was prepared according to the procedure reported in step-3 of scheme-1 from ethyl 2-(2-((7-iodo-2-(methoxymethyl)benzofuran-5-yl)methoxy)-4-methylphenyl)acetate (415b) (0.5 g, 1.01 mmol) in acetonitrile (12.5 mL) using tert-butyl 3-(4,4,5,5-tetramethyl-1,3,2-dioxaborolan-2-yl)benzylcarbamate (3b) (0.505 g, 1.51 mmol), Pd(PPh$_3$)$_2$Cl$_2$ (0.070 g, 0.10 mmol) and a solution of Na$_2$CO$_3$ (0.32 g, 3.03 mmol) in water (4 mL) and heating under a nitrogen atmosphere at 90° C. for 2 h on an oil bath. This gave after workup, purification by flash column chromatography (silica gel, eluting with 1-3% EtOAc in n-heptane) ethyl 2-(2-((7-(3-(((tert-butoxycarbonyl)amino)methyl)phenyl)-2-(methoxymethyl)benzofuran-5-yl)methoxy)-4-methylphenyl)acetate (415c) (0.30 g, 513%) as an off white semi-solid; $^1$H NMR (300 MHz, DMSO-d$_6$) δ 7.78-7.65 (m, 3H), 7.58-7.43 (m, 3H), 7.31 (d, J=7.6 Hz, 1H), 7.09 (d, J=7.5 Hz, 1H), 6.98 (d, J=9.7 Hz, 2H), 6.73 (d, J=7.5 Hz, 1H), 5.20 (s, 2H), 4.57 (s, 2H), 4.23 (d, J=6.3 Hz, 2H), 3.90 (q, J=7.2 Hz, 2H), 3.56 (s, 2H), 3.33 (s, 3H), 2.30 (s, 3H), 1.39 (s, 9H), 0.96 (t, J=7.1 Hz, 3H).

Step-4: Preparation of Ethyl 2-(2-((7-(3-(aminomethyl)phenyl)-2-(methoxymethyl)benzofuran-5-yl)methoxy)-4-methylphenyl)acetate (415d)

Compound 415d was prepared according to the procedure reported in step-5 of scheme-1 from ethyl 2-(2-((7-(3-(((tert-butoxycarbonyl)amino)methyl)phenyl)-2-(methoxymethyl)benzofuran-5-yl)methoxy)-4-methylphenyl)acetate (415c) (150 mg, 0.261 mmol) in DCM (10 mL) using TFA (0.388 mL, 5.23 mmol). This gave after workup ethyl 2-(2-((7-(3-(aminomethyl)phenyl)-2-(methoxymethyl)benzofuran-5-yl)methoxy)-4-methylphenyl)acetate (415d), which was used as such for next step. MS (ES+): 474.20 (M+1).

Step-5: Preparation of 2-(2-((7-(3-(aminomethyl)phenyl)-2-(methoxymethyl)benzofuran-5-yl)methoxy)-4-methylphenyl)acetic Acid (415e)

Compound 415e was prepared according to the procedure reported in step-6 of scheme-1 from ethyl 2-(2-((7-(3-(aminomethyl)phenyl)-2-(methoxymethyl)benzofuran-5-yl)methoxy)-4-methylphenyl)acetate (415d) (0.262 mmol; from above step-4) in MeOH/THF (5 mL, each) using a solution of lithium hydroxide hydrate (90 mg, 2.095 mmol) in water (5 mL) and stirring at room temperature for 16 h. This gave after workup and purification by reverse phase column [C18 column, eluting with water (containing 0.1% HCl)/acetonitrile (1:0 to 0:1)] 2-(2-((7-(3-(aminomethyl)phenyl)-2-(methoxymethyl)benzofuran-5-yl)methoxy)-4-methylphenyl)acetic acid (415e) (33 mg, 28%) HCl salt as a white solid; $^1$H NMR (300 MHz, DMSO-d$_6$) δ 12.19 (s, 1H), 8.45 (s, 3H), 7.96 (t, J=1.5 Hz, 1H), 7.92 (dt, J=7.3, 1.7 Hz, 1H), 7.72 (d, J=1.6 Hz, 1H), 7.63 (d, J=1.6 Hz, 1H), 7.61-7.52 (m, 2H), 7.09 (d, J=7.5 Hz, 1H), 7.00 (s, 1H), 6.94 (d, J=1.6 Hz, 1H), 6.72 (ddd, J=7.5, 1.5, 0.8 Hz, 1H), 5.23 (s, 2H), 4.58 (s, 2H), 4.13 (s, 2H), 3.54 (s, 2H), 3.33 (s, 3H), 2.29 (s, 3H); MS (ES+): 446.20 (M+1); MS (ES−): 444.10 (M−1); Analysis calculated for C$_{27}$H$_{27}$NO$_5$.HCl.H$_2$O: C, 64.86; H, 6.05; N, 2.80; Found: C, 64.48; H, 5.85; N, 2.82.

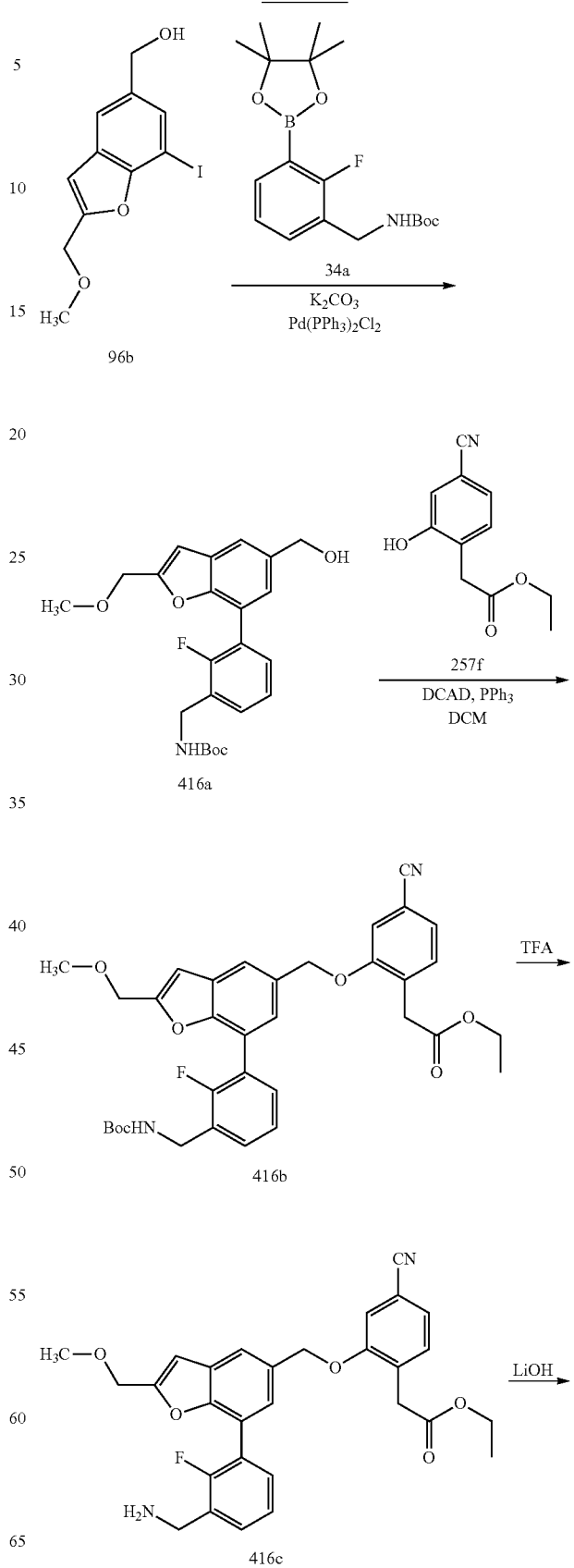

Scheme-416

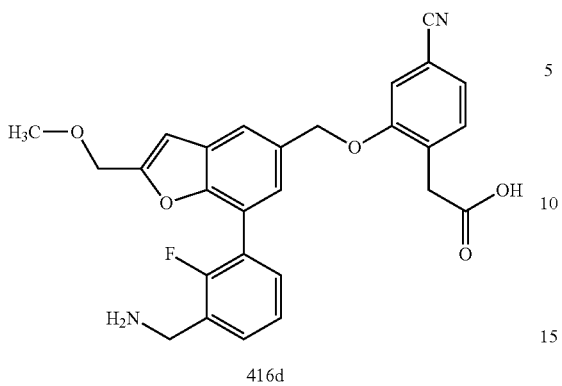

Preparation of 2-(2-((7-(3-(aminomethyl)-2-fluorophenyl)-2-(methoxymethyl)benzofuran-5-yl)methoxy)-4-cyanophenyl)acetic Acid (416d)

Step-1: Preparation of tert-butyl 2-fluoro-3-(5-(hydroxymethyl)-2-(methoxymethyl)benzofuran-7-yl)benzylcarbamate (416a)

Compound 416a was prepared according to the procedure reported in step-3 of scheme-1 from (7-iodo-2-(methoxymethyl)benzofuran-5-yl)methanol (96b) (4.0 g, 12.57 mmol) in dioxane (75 mL) using tert-butyl 2-fluoro-3-(4,4,5,5-tetramethyl-1,3,2-dioxaborolan-2-yl)benzylcarbamate (34a) (4.42 g, 12.57 mmol), a solution of potassium carbonate (5.21 g, 37.7 mmol) in water (9 mL), Pd(PPh$_3$)$_2$Cl$_2$ (1.324 g, 1.886 mmol) and heating under a nitrogen atmosphere at 100° C. for 3 h. This gave after workup and purification by flash column chromatography (silica gel, 120g, eluting with 0 to 50% ethyl acetate in hexanes) tert-butyl 2-fluoro-3-(5-(hydroxymethyl)-2-(methoxymethyl)benzofuran-7-yl)benzylcarbamate (416a) (3.54 g, 68% yield) as a light brown gummy solid; $^1$H NMR (300 MHz, DMSO-d$_6$) δ 7.61 (d, J=1.6 Hz, 1H), 7.53-7.23 (m, 5H), 6.96 (s, 1H), 5.27 (t, J=5.7 Hz, 1H), 4.62 (d, J=5.7 Hz, 2H), 4.50 (s, 2H), 4.26 (d, J=6.0 Hz, 2H), 3.28 (s, 3H), 1.41 (s, 9H); $^{19}$F NMR (282 MHz, DMSO-d$_6$) δ –121.16.

Step-2: Preparation of Ethyl 2-(2-((7-(3-(((tert-butoxycarbonyl)amino)methyl)-2-fluorophenyl)-2-(methoxymethyl)benzofuran-5-yl)methoxy)-4-cyanophenyl)acetate (416b)

Compound 416b was prepared according to the procedure reported in step-2 of scheme-23 from tert-butyl 2-fluoro-3-(5-(hydroxymethyl)-2-(methoxymethyl)benzofuran-7-yl)benzylcarbamate (416a) (875 mg, 2.105 mmol) in DCM (20 mL) using triphenylphosphine (690 mg, 2.63 mmol), ethyl 2-(4-cyano-2-hydroxyphenyl)acetate (257f) (360 mg, 1.754 mmol) and a solution of (E)-bis(4-chlorobenzyl) diazene-1,2-dicarboxylate (DCAD, 966 mg, 2.63 mmol) in DCM (20 mL). This gave after workup and purification by flash column chromatography (silica gel, 40 g, eluting with 0 to 30% ethyl acetate in hexanes) ethyl 2-(2-((7-(3-(((tert-butoxycarbonyl)amino)methyl)-2-fluorophenyl)-2-(methoxymethyl)benzofuran-5-yl)methoxy)-4-cyanophenyl)acetate (416b) (1.41 g) as an off-white waxy solid; $^1$H NMR (300 MHz, DMSO-d$_6$) δ 9.29 (s, 1H), 7.73 (d, J=1.6 Hz, 1H), 7.63 (d, J=1.3 Hz, 1H), 7.52-7.29 (m, 6H), 7.01 (s, 1H), 5.29 (s, 2H), 4.52 (s, 2H), 4.26 (d, J=6.1 Hz, 2H), 3.88 (q, J=7.1 Hz, 2H), 3.71 (s, 2H), 3.29 (s, 3H), 1.41 (s, 9H), 0.95 (t, J=7.1 Hz, 3H).

Step-3: Preparation of Ethyl 2-(2-((7-(3-(aminomethyl)-2-fluorophenyl)-2-(methoxymethyl)benzofuran-5-yl)methoxy)-4-cyanophenyl)acetate (416c)

Compound 416c was prepared according to the procedure reported in step-5 of scheme-1 from ethyl 2-(2-((7-(3-(((tert-butoxycarbonyl)amino)methyl)-2-fluorophenyl)-2-(methoxymethyl)benzofuran-5-yl)methoxy)-4-cyanophenyl)acetate (416b) (230 mg, 0.382 mmol) in DCM (15 mL) using TFA (0.567 mL, 7.63 mmol). This gave after workup ethyl 2-(2-((7-(3-(aminomethyl)-2-fluorophenyl)-2-(methoxymethyl)benzofuran-5-yl)methoxy)-4-cyanophenyl)acetate (416c) which was used as such for next step. MS (ES+): 503.20 (M+1).

Step-4: Preparation of 2-(2-((7-(3-(aminomethyl)-2-fluorophenyl)-2-(methoxymethyl)benzofuran-5-yl)methoxy)-4-cyanophenyl)acetic Acid (416d)

Compound 416d was prepared according to the procedure reported in step-6 of scheme-1 from ethyl 2-(2-((7-(3-(aminomethyl)-2-fluorophenyl)-2-(methoxymethyl)benzofuran-5-yl)methoxy)-4-cyanophenyl)acetate (416c) (0.382 mmol, from above step-3) in THF/methanol (7 mL, 1:1 each) using solution of lithium hydroxide hydrate (128 mg, 3.06 mmol) in water (7 mL) and stirring at room temperature for 20h. This gave after workup and purification by reverse-phase column chromatography [C-18 column, eluting with water (containing 0.1% HCl)/acetonitrile (1:0 to 0:1)] 2-(2-((7-(3-(aminomethyl)-2-fluorophenyl)-2-(methoxymethyl)benzofuran-5-yl)methoxy)-4-cyanophenyl)acetic acid (416d) (54 mg, 30% yield) HCl salt as a white solid; $^1$H NMR (300 MHz, DMSO-d$_6$) δ 8.60 (s, 3H), 7.79 (d, J=1.6 Hz, 1H), 7.75-7.62 (m, 2H), 7.59 (d, J=1.4 Hz, 1H), 7.48-7.29 (m, 4H), 7.02 (s, 1H), 5.33 (s, 2H), 4.52 (s, 2H), 4.17 (s, 2H), 3.68 (s, 2H), 3.29 (s, 3H); $^{19}$F NMR (282 MHz, DMSO-d$_6$) δ–118.72; MS (ES+): 475.20 (M+1); Analysis calculated for C$_{27}$H$_{23}$FN$_2$O$_5$.HCl.1.75 H$_2$O: C, 59.78; H, 5.11; N, 5.16; Cl, 6.54; Found: C, 59.58; H, 4.73; N, 4.94; Cl, 6.83.

Scheme-417

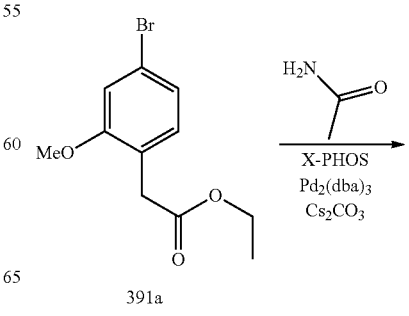

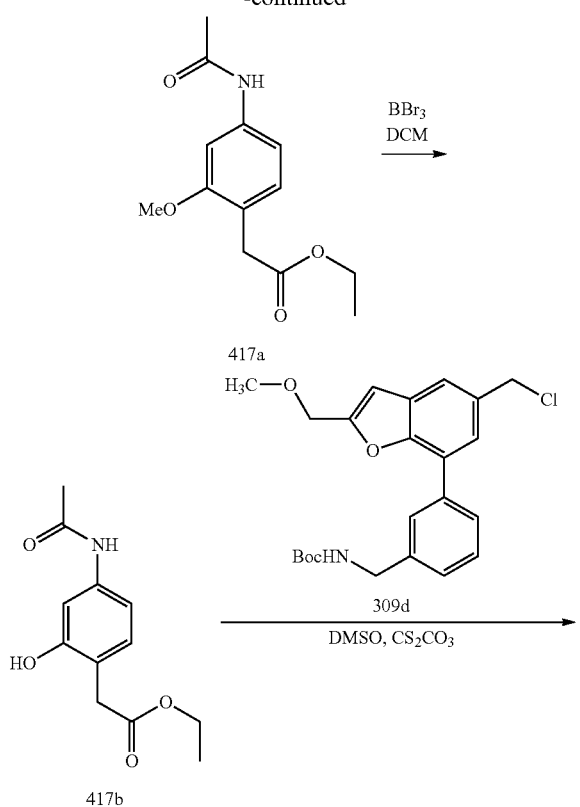

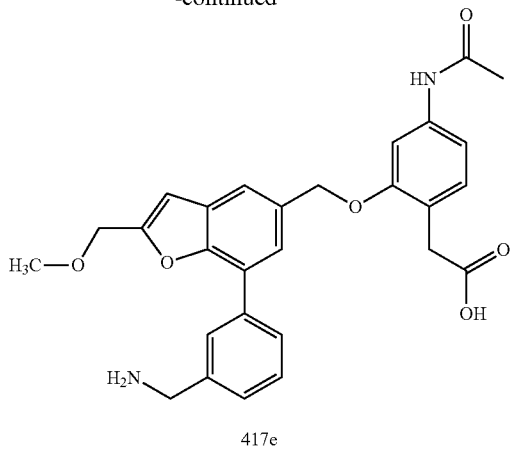

Preparation of 2-(4-acetamido-2-((7-(3-(aminomethyl)phenyl)-2-(methoxymethyl)benzofuran-5-yl)methoxy)phenyl)acetic Acid (417e)

Step-1: Preparation of Ethyl 2-(4-acetamido-2-methoxyphenyl)acetate (417a)

Compound 417a was prepared according to the procedure reported in step-1 of scheme-224 from ethyl 2-(4-bromo-2-methoxyphenyl)acetate (391a) (3.5 g, 12.81 mmol) in dioxane (52.5 mL) using acetamide (1.53 g, 25.90 mmol), (Note: acetamide was dried over $P_2O_5$ prior to use), $Cs_2CO_3$ (12.52 μm 38.42 mmol), dicyclohexyl(2',4',6'-triisopropyl-biphenyl-2-yl)phosphine (X-PHOS) (2.74 g, 5.74 mmol), $Pd_2(dba)_3$ (1.76 g, 1.92 mmol) and heating at 105-110° C. for 6 h. This gave after workup and purification by flash column chromatography (Silica gel, eluting with 25% EtOAc in n-heptane) ethyl 2-(4-acetamido-2-methoxyphenyl)acetate (417a) (2.5 g, 78%) as yellow oil; $^1$H NMR (300 MHz, DMSO-$d_6$) δ 9.93 (s, 1H), 7.30 (s, 1H), 7.07 (s, 1H), 4.04 (q, J=7.1, Hz, 2H), 3.70 (s, 3H), 3.50 (s, 2H), 2.01 (s, 3H), 1.17 (t, J=7.1, Hz, 3H); MS (ES+): 252.1 (M+1); (ES−) 250.1 (M−1).

Step-2: Preparation of Ethyl 2-(4-acetamido-2-hydroxyphenyl)acetate (417b)

Compound 417b was prepared according to the procedure reported in step-5 of scheme-257 from ethyl 2-(4-acetamido-2-methoxyphenyl)acetate (417a) (350 mg, 1.39 mmol) in dichloromethane (7 mL) using boron tribromide (0.6 mL, 1.395 g, 5.57 mmol). This gave after workup and purification by flash column chromatography (Silica gel, eluting with 25% EtOAc in n-heptane) ethyl 2-(4-acetamido-2-hydroxyphenyl)acetate (417b) (240 mg, 73%) as an oily mass. $^1$H NMR (300 MHz, DMSO-$d_6$) δ 9.78 (s, 1H), 9.50 (s, 1H), 7.28 (d, J=2.0 Hz, 1H), 6.97 (d, J=8.2 Hz, 1H), 6.83 (dd, J=8.2, 2.1 Hz, 1H), 4.04 (q, J=7.1 Hz, 2H), 3.45 (s, 2H), 2.01 (s, 3H), 1.27-1.11 (t, 3H).

Step-3: Preparation of Ethyl 2-(4-acetamido-2-((7-(3-(((tert-butoxycarbonyl)amino)methyl)phenyl)-2-(methoxymethyl)benzofuran-5-yl)methoxy)phenyl)acetate (417c)

Compound 417c was prepared according to the procedure reported in step-6 of scheme-257 from tert-butyl 3-(5-

(chloromethyl)-2-(methoxymethyl)benzofuran-7-yl)benzyl-carbamate (309d) (0.45 g, 1.08 mmol) using ethyl 2-(4-acetamido-2-hydroxyphenyl)acetate (417b) (0.385 g, 1.62 mmol), CS₂CO₃ (0.351 g, 1.08 mmol) in DMSO (4.5 mL) and stirring at room temperature for 16 h. This gave after workup and purification by flash column chromatography (Silica gel, eluting with 70-75% EtOAc in n-heptane) ethyl 2-(4-acetamido-2-((7-(3-(((tert-butoxycarbonyl)amino) methyl)phenyl)-2-(methoxymethyl)benzofuran-5-yl) methoxy)phenyl)acetate (417c) (0.3 g, 46%) as a thick syrup; ¹H NMR (300 MHz, DMSO-d₆) δ 9.94 (s, 1H), 7.74 (d, J=8.2 Hz, 2H), 7.67 (d, J=1.6 Hz, 1H), 7.57-7.41 (m, 4H), 7.30 (d, J=7.8 Hz, 1H), 7.16-7.03 (m, 2H), 6.99 (s, 1H), 5.16 (s, 2H), 4.57 (s, 2H), 4.23 (d, J=6.2 Hz, 2H), 3.91 (q, J=7.1 Hz, 2H), 3.55 (s, 3H), 3.33 (s, 2H), 2.03 (s, 3H), 1.39 (s, 9H), 0.97 (t, J=7.1 Hz, 3H). MS (ES+): 617.2 (M+1), (ES−): 615.2 (M−1).

Step-4: Preparation of Ethyl 2-(4-acetamido-2-((7-(3-(aminomethyl)phenyl)-2-(methoxymethyl)benzofuran-5-yl)methoxy)phenyl)acetate (417d)

Compound 417d was prepared according to the procedure reported in step-5 of scheme-1 from ethyl 2-(4-acetamido-2-((7-(3-(((tert-butoxycarbonyl)amino)methyl)phenyl)-2-(methoxymethyl)benzofuran-5-yl)methoxy)phenyl)acetate (417c) (250 mg, 0.405 mmol) in DCM (15 mL) using TFA (0.602 mL, 8.11 mmol). This gave after workup ethyl 2-(4-acetamido-2-((7-(3-(aminomethyl)phenyl)-2-(methoxymethyl)benzofuran-5-yl)methoxy)phenyl)acetate (417d) which was used in the next step without further purification; MS (ES+): 517.20 (M+1).

Step-5: Preparation of 2-(4-acetamido-2-((7-(3-(aminomethyl)phenyl)-2-(methoxymethyl)benzofuran-5-yl)methoxy)phenyl)acetic Acid (417e)

Compound 417e was prepared according to the procedure reported in step-6 of scheme-1 from ethyl 2-(4-acetamido-2-((7-(3-(aminomethyl)phenyl)-2-(methoxymethyl)benzofuran-5-yl)methoxy)phenyl)acetate (417d) (0.381 mmol; from above step-4) in MeOH/THF (5 mL, each) using a solution of lithium hydroxide hydrate (131 mg, 3.05 mmol) in water (5 mL) and stirring at room temperature for 16 h. This gave after workup and purification by reverse phase column [C18 column, eluting with water (containing 0.1% HCl)/acetonitrile (1:0 to 0:1)] 2-(4-acetamido-2-((7-(3-(aminomethyl)phenyl)-2-(methoxymethyl)benzofuran-5-yl) methoxy)phenyl)acetic acid (417e) (32 mg, 17% yield) HCl salt as a white solid; ¹H NMR (300 MHz, DMSO-d₆) δ 9.96 (s, 1H), 7.99-7.91 (m, 2H), 7.73 (d, J=1.6 Hz, 1H), 7.63 (d, J=1.8 Hz, 1H), 7.59 (d, J=7.6 Hz, 1H), 7.56-7.49 (m, 2H), 7.11 (d, J=8.1 Hz, 1H), 7.03 (dd, J=8.2, 1.8 Hz, 1H), 7.00 (s, 1H), 5.19 (s, 2H), 4.58 (s, 2H), 4.14 (s, 2H), 3.52 (s, 2H), 3.33 (s, 3H), 2.03 (s, 3H); MS (ES+): 489.20 (M+1); MS (ES−): 487.15 (M−1); Analysis calculated for C₂₈H₂₈N₂O₆·HCl·3H₂O: C, 58.08; H, 6.09; N, 4.84; Cl, 6.12; Found: C, 58.19; H, 5.89; N, 4.88; Cl, 6.37.

Scheme-418

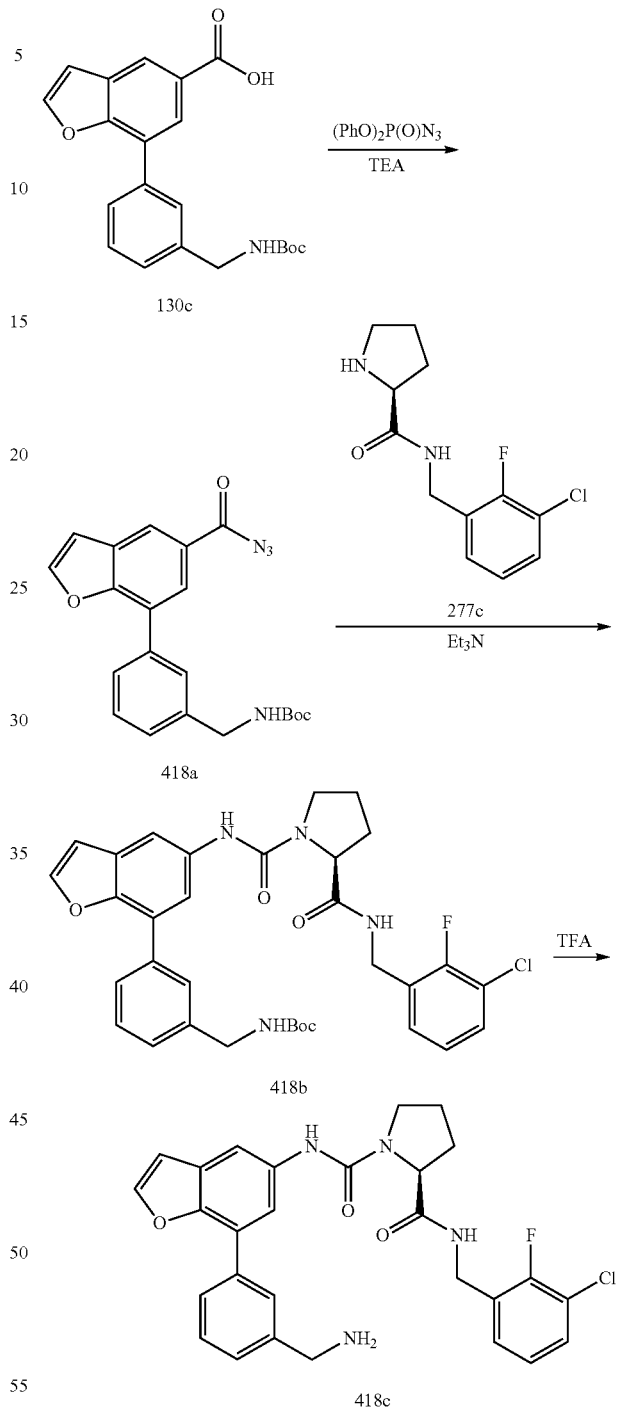

Preparation of (S)-N1-(7-(3-(aminomethyl)phenyl) benzofuran-5-yl)-N2-(3-chloro-2-fluorobenzyl)pyr-rolidine-1,2-dicarboxamide (418c)

Step-1: Preparation of tert-butyl 3-(5-(azidocarbo-nyl)benzofuran-7-yl)benzylcarbamate (418a)

Compound 418a was prepared according to the procedure reported in step-1 of scheme-143 from 7-(3-(((tert-butoxycarbonyl)amino)methyl)phenyl)benzofuran-5-carboxylic acid (130c) (1 g, 2.72 mmol) in toluene (15 mL) using triethylamine (0.379 µL, 2.72 mmol), diphenyl phosphorazidate (0.607 mL, 2.72 mmol) and stirred at room temperature for 25 h. This gave after workup and purification by flash column chromatography (silica gel, 4g, eluting with DCM) tert-butyl 3-(5-(azidocarbonyl)benzofuran-7-yl)benzylcarbamate (418a) (0.8 g, 75% yield); $^1$H NMR (300 MHz, DMSO-d$_6$) δ 8.35 (d, J=1.8 Hz, 1H), 8.23 (d, J=2.2 Hz, 1H), 8.06 (d, J=1.8 Hz, 1H), 7.79-7.68 (m, 2H), 7.47 (q, J=1.1 Hz, 1H), 7.36 (t, J=1.2 Hz, 1H), 7.23 (d, J=2.2 Hz, 1H), 5.76 (s, 1H), 4.24 (d, J=6.2 Hz, 2H), 1.41 (s, 9H).

Step-2: Preparation of (S)-tert-butyl 3-(5-(2-((3-chloro-2-fluorobenzyl)carbamoyl)pyrrolidine-1-carboxamido)benzofuran-7-yl)benzylcarbamate (418b)

A solution of tert-butyl 3-(5-(azidocarbonyl)benzofuran-7-yl)benzylcarbamate (418a) (80 mg, 0.204 mmol) in toluene (10 mL) was heated at reflux for 1.5 h cooled to room temperature and added a solution of (S)—N-(3-chloro-2-fluorobenzyl)pyrrolidine-2-carboxamide (277c) (52 mg, 0.204 mmol) in THF (5 mL), triethylamine (0.057 mL, 0.408 mmol) and stirred at room temperature for 3 h. The reaction mixture was concentrated in vacuum and residue obtained was purified by flash column chromatography [silica(24 g), eluting with DMA80 in DCM from 0-50%] to give (S)-tert-butyl 3-(5-(2-((3-chloro-2-fluorobenzyl)carbamoyl)pyrrolidine-1-carboxamido)benzofuran-7-yl)benzylcarbamate (418b) (117 mg, 0.188 mmol, 92% yield); $^1$H NMR (300 MHz, DMSO-d$_6$) δ 8.49 (t, J=6.0 Hz, 1H), 8.34 (s, 1H), 7.98 (d, J=2.2 Hz, 1H), 7.85 (d, J=2.1 Hz, 1H), 7.72-7.62 (m, 3H), 7.53-7.21 (m, 5H), 7.20-7.06 (m, 1H), 6.99 (d, J=2.2 Hz, 1H), 4.44-4.29 (m, 3H), 4.22 (d, J=6.2 Hz, 2H), 3.74-3.58 (m, 1H), 3.50 (q, J=8.5, 7.9 Hz, 1H), 2.19-2.03 (m, 1H), 2.03-1.79 (m, 3H), 1.40 (s, 9H); MS (ES+): 643.2 (M+Na).

Step-3: Preparation of (S)-N1-(7-(3-(aminomethyl) phenyl)benzofuran-5-yl)-N2-(3-chloro-2-fluorobenzyl)pyrrolidine-1,2-dicarboxamide (418c)

Compound 418c was prepared according to the procedure reported in step-5 of scheme-1 from (S)-tert-butyl 3-(5-(2-((3-chloro-2-fluorobenzyl)carbamoyl)pyrrolidine-1-carboxamido)benzofuran-7-yl)benzylcarbamate (418b) (117 mg, 0.188 mmol) in DCM (3 mL) using TFA (0.290 mL, 3.77 mmol). This gave after workup and purification by reverse phase column chromatography [C18 (50 g), eluting with ACN in water (containing 0.1% HCl) from 0-100%] (S)-N1-(7-(3-(aminomethyl)phenyl)benzofuran-5-yl)-N2-(3-chloro-2-fluorobenzyl)pyrrolidine-1,2-dicarboxamide (418c) (45 mg, 46% yield) HCl salt as a white solid; $^1$H NMR (300 MHz, DMSO-d$_6$) δ 8.52 (t, J=5.9 Hz, 1H), 8.37 (s, 1H), 8.31 (s, 3H, D$_2$O exchangeable), 8.01 (d, J=2.2 Hz, 1H), 7.92 (s, 1H), 7.85-7.78 (m, 2H), 7.74 (d, J=2.1 Hz, 1H), 7.60 (t, J=7.6 Hz, 1H), 7.54 (d, J=7.6 Hz, 1H), 7.47-7.41 (m, 1H), 7.39-7.29 (m, 1H), 7.14-7.06 (m, 1H), 7.01 (d, J=2.2 Hz, 1H), 4.44-4.24 (m, 3H), 4.14 (s, 2H), 3.66 (dt, J=11.1, 5.7 Hz, 1H), 3.55-3.44 (m, 1H), 2.14 (dd, J=11.3, 7.6 Hz, 1H), 2.01-1.80 (m, 3H). $^{19}$F NMR (282 MHz, DMSO-d$_6$) δ-121.77. MS (ES+): 521.2 (M+1); (ES-): 519.1 (M-1), 555.1 (M+Cl); Analysis calculated for $C_{28}H_{26}ClFN_4O_3 \cdot HCl \cdot 2H_2O$: C, 56.67; H, 5.26; Cl, 11.95; N, 9.44; Found: C, 56.67; H, 5.08; Cl, 11.95; N, 9.34.

Scheme-419

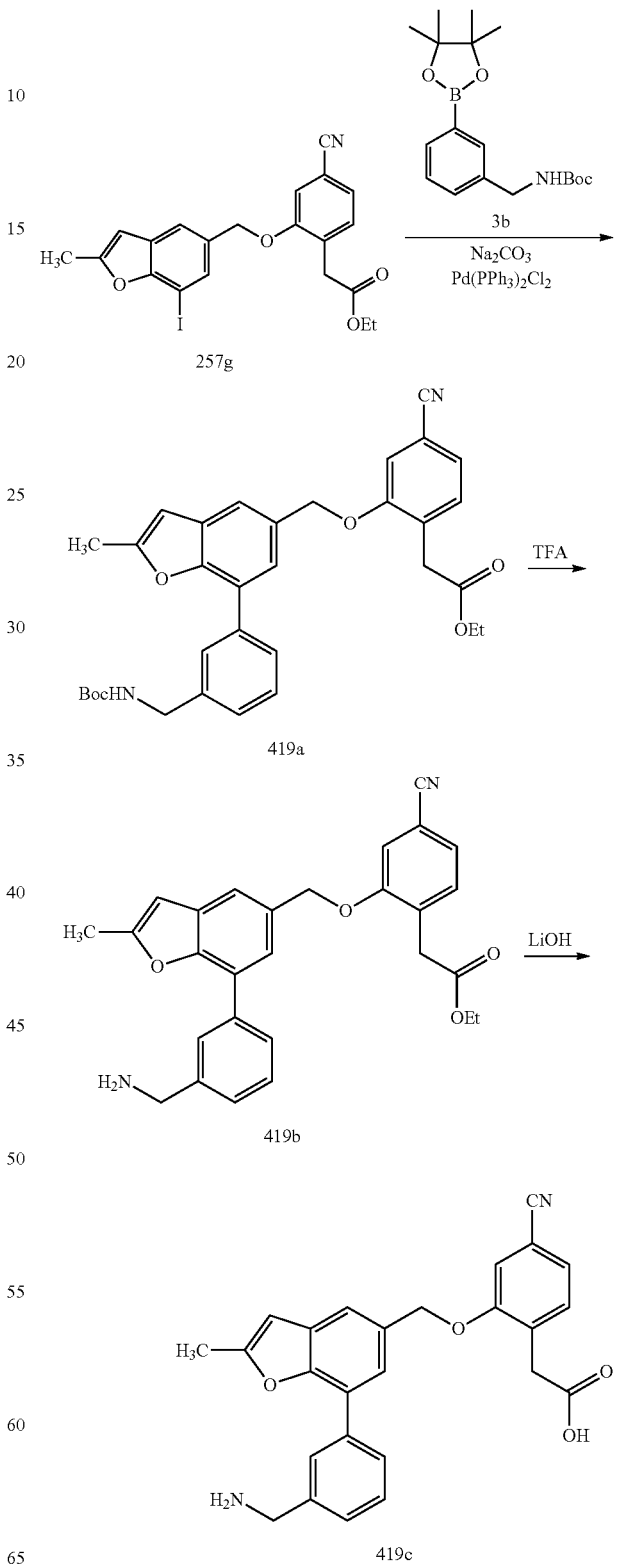

Preparation of 2-(2-((7-(3-(aminomethyl)phenyl)-2-methylbenzofuran-5-yl)methoxy)-4-cyanophenyl) acetic Acid (419c)

Step-1: Preparation of Ethyl 2-(2-((7-(3-(((tert-butoxycarbonyl)amino)methyl)phenyl)-2-methylbenzofuran-5-yl)methoxy)-4-cyanophenyl)acetate (419a)

Compound 419a was prepared according to the procedure reported in step-3 of scheme-1 from ethyl 2-(4-cyano-2-((7-iodo-2-methylbenzofuran-5-yl)methoxy)phenyl)acetate (257g) (1.2 g, 2.52 mmol) in acetonitrile (24 mL) using tert-butyl 3-(4,4,5,5-tetramethyl-1,3,2-dioxaborolan-2-yl)benzylcarbamate (3b) (1.0 g, 3.02 mmol), a solution of $Na_2CO_3$ (0.668 g, 6.31 mmol) in water (1.2 mL), $Pd(PPh_3)_2Cl_2$ (0.265 g, 0.378 mmol) and heating under a nitrogen atmosphere at 90° C. for 4 h. This gave after workup and purification by flash column chromatography (silica gel, eluting with 40% ethyl acetate in hexanes) ethyl 2-(2-((7-(3-(((tert-butoxycarbonyl)amino)methyl)phenyl)-2-methylbenzofuran-5-yl)methoxy)-4-cyanophenyl)acetate (419a) (550 mg, 40%) as an oil; $^1$H NMR (300 MHz, DMSO-$d_6$) δ 7.75-7.68 (m, 2H), 7.61 (d, J=1.4 Hz, 1H), 7.56 (d, J=1.6 Hz, 1H), 7.54-7.37 (m, 4H), 7.29 (d, J=7.7 Hz, 1H), 6.67 (d, J=1.2 Hz, 1H), 5.27 (s, 2H), 4.23 (d, J=6.2 Hz, 2H), 3.90 (q, J=7.1 Hz, 2H), 3.71 (s, 2H), 2.48 (s, 3H), 1.39 (s, 9H), 0.95 (t, J=7.1 Hz, 3H); MS (ES+): (553.2); (ES−): (M−1).

Step-3: Preparation of Ethyl 2-(2-((7-(3-(aminomethyl)phenyl)-2-methylbenzofuran-5-yl)methoxy)-4-cyanophenyl)acetate (419b)

Compound 419b was prepared according to the procedure reported in step-5 of scheme-1 ethyl 2-(2-((7-(3-(((tert-butoxycarbonyl)amino)methyl)phenyl)-2-methylbenzofuran-5-yl)methoxy)-4-cyanophenyl)acetate (419a) (320 mg, 0.577 mmol) in DCM (15 mL) using TFA (0.857 mL, 11.54 mmol). This gave after workup ethyl 2-(2-((7-(3-(aminomethyl)phenyl)-2-methylbenzofuran-5-yl)methoxy)-4-cyanophenyl)acetate (419b) which was used in the next step without further purification; MS (ES+): 455.20 (M+1)

Step-4: Preparation of 2-(2-((7-(3-(aminomethyl)phenyl)-2-methylbenzofuran-5-yl)methoxy)-4-cyanophenyl)acetic Acid (419c)

Compound 419c was prepared according to the procedure reported in step-6 of scheme-1 from ethyl 2-(2-((7-(3-(aminomethyl)phenyl)-2-methylbenzofuran-5-yl)methoxy)-4-cyanophenyl)acetate (419b) (0.577 mmol; from above step-3) in MeOH/THF (5 mL, each) using a solution of lithium hydroxide hydrate (198 mg, 4.62 mmol) in water (5 mL) and stirring at room temperature for 16 h. This gave after workup and purification by reverse phase column [C18 column, eluting with water (containing 0.1% HCl)/acetonitrile (1:0 to 0:1)] 2-(2-((7-(3-(aminomethyl)phenyl)-2-methylbenzofuran-5-yl)methoxy)-4-cyanophenyl)acetic acid (419c) (11 mg, 4%) HCl salt as a white solid; $^1$H NMR (300 MHz, DMSO-$d_6$, $D_2O$ exchange) δ 7.95-7.88 (m, 2H), 7.62-7.55 (m, 3H), 7.53-7.48 (m, 2H), 7.44 (d, J=7.7 Hz, 1H), 7.39 (dd, J=7.7, 1.4 Hz, 1H), 6.67 (d, J=1.2 Hz, 1H), 5.30 (s, 2H), 4.13 (s, 2H), 3.67 (s, 2H), 2.48 (d, J=1.0 Hz, 3H); MS (ES+): 427.10 (M+1).

Scheme-420

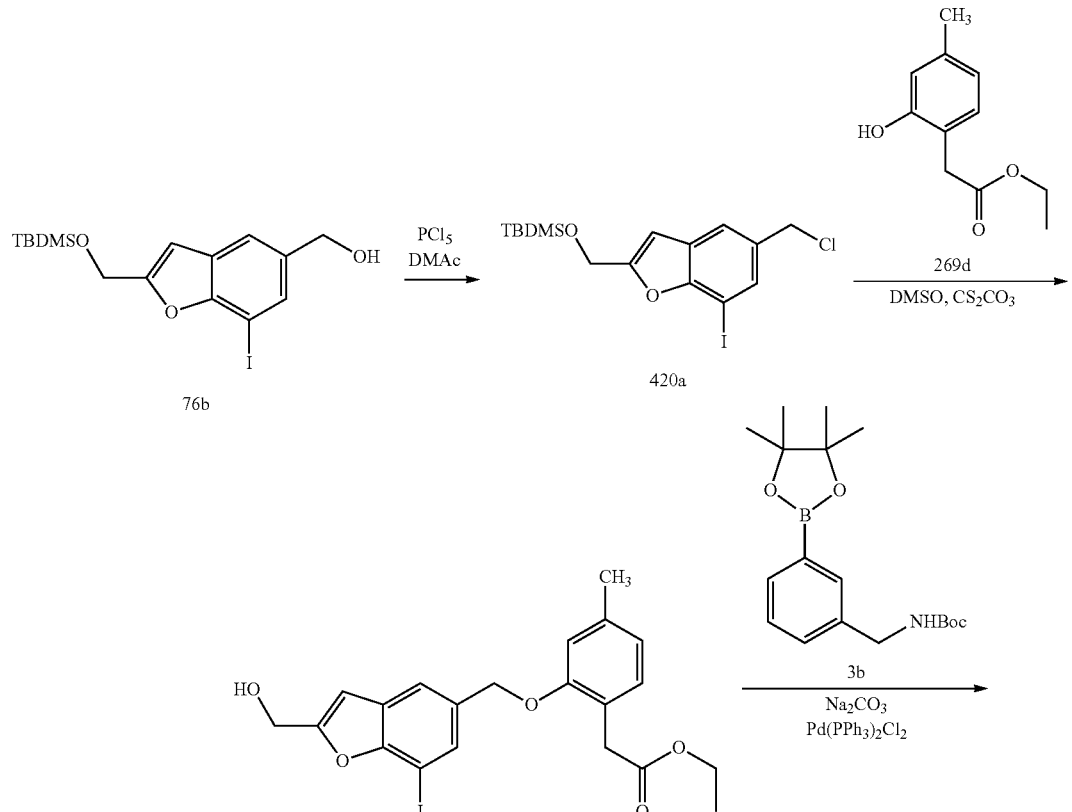

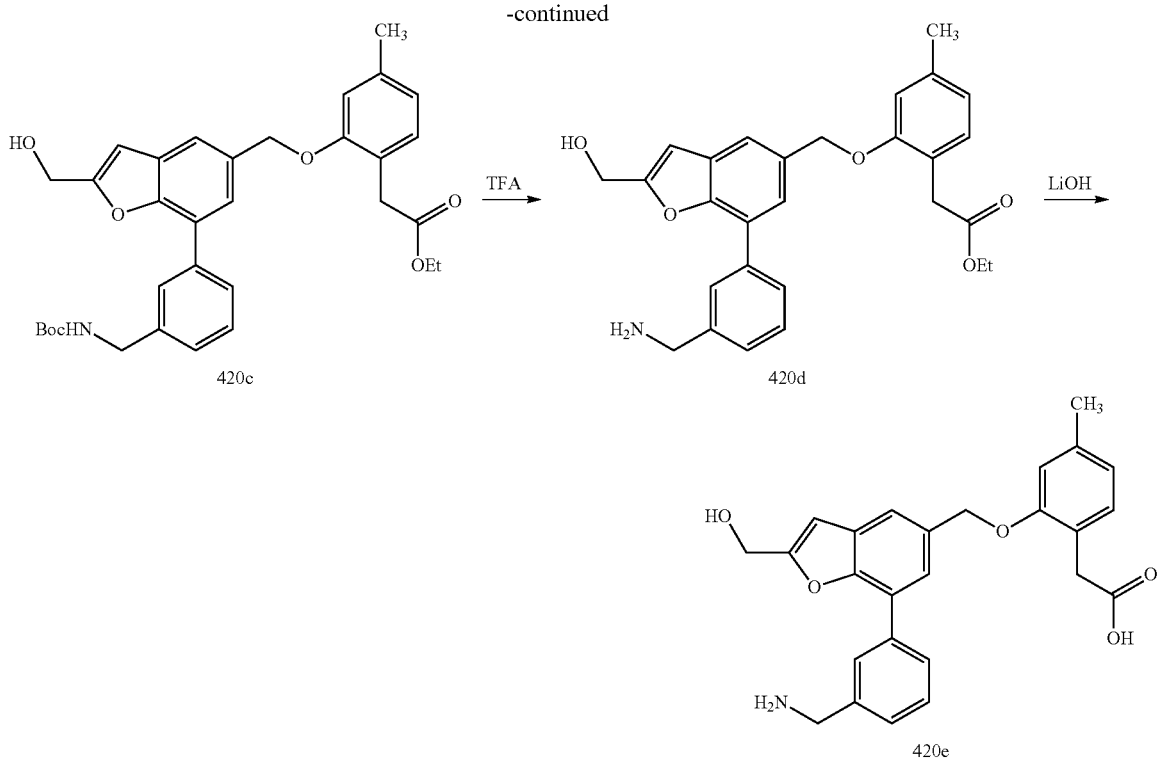

Preparation of 2-(2-((7-(3-(aminomethyl)phenyl)-2-(hydroxymethyl)benzofuran-5-yl)methoxy)-4-methylphenyl)acetic Acid (420e)

Step-1: Preparation of tert-butyl((5-(chloromethyl)-7-iodobenzofuran-2-yl)methoxy)dimethylsilane (420a)

To a solution of (2-(((tert-butyldimethylsilyl)oxy)methyl)-7-iodobenzofuran-5-yl)methanol (76b) (11.5 g, 27.49 mmol) in DMAc (396 mL) cooled to 0° C. was added $PCl_5$ (8.58 g, 41.21 mmol) and stirred for 1 h at 0° C. The reaction mixture was poured into ice water (200 mL) basified with saturated aqueous solution of $NaHCO_3$ (200 mL). The aqueous layer was extracted with ethyl acetate (2×200 mL). The combined organic layer was washed with brine (100 mL), dried, concentrated in vacuum. The residue obtained was purified by flash column chromatography (5% EtOAc in n-heptane) to give tert-butyl((5-(chloromethyl)-7-iodobenzofuran-2-yl)methoxy)dimethylsilane (420a) (6.0 g, 75%) as a colorless oil; $^1H$ NMR (300 MHz, DMSO-$d_6$) δ 7.64 (d, J=1.7 Hz, 1H), 7.57 (d, J=1.6 Hz, 1H), 6.85 (s, 1H), 4.71 (s, 2H), 4.70 (s, 2H), 0.76 (s, 9H), 0.00 (s, 6H).

Step-2: Preparation of Ethyl 2-(2-((2-(hydroxymethyl)-7-iodobenzofuran-5-yl)methoxy)-4-methylphenyl)acetate (420b)

Compound 420b was prepared according to the procedure reported in step-6 of scheme-257 from tert-butyl((5-(chloromethyl)-7-iodobenzofuran-2-yl)methoxy)dimethylsilane (420a) (1.09 g, 3.379 mmol) using ethyl 2-(2-hydroxy-4-methylphenyl)acetate (269d) (0.78 g, 4.01 mmol) $Cs_2CO_3$ (2.20 g, 6.75 mmol) in DMSO (21 mL) and stirring at room temperature for 18 h. This gave after workup and purification by flash column chromatography (Silica gel, eluting with 15% EtOAc in n-heptane) ethyl 2-(2-((2-(hydroxymethyl)-7-iodobenzofuran-5-yl)methoxy)-4-methylphenyl)acetate (420b) (1.0 g, 65.53%) as a yellow oil; $^1H$ NMR (300 MHz, DMSO-$d_6$) δ 7.69 (d, J=1.4 Hz, 1H), 7.63 (s, 1H), 7.08 (d, J=7.5 Hz, 1H), 6.91 (s, 2H), 6.73 (d, J=7.5 Hz, 1H), 5.57 (t, J=5.8 Hz, 1H), 5.11 (s, 2H), 4.60 (d, J=5.9 Hz, 2H), 4.01 (q, J=7.1 Hz, 2H), 3.55 (s, 2H), 2.29 (s, 3H), 1.08 (t, J=7.1 Hz, 3H).

Step-3: Preparation of Ethyl 2-(2-((7-(3-(((tert-butoxycarbonyl)amino)methyl)phenyl)-2-(hydroxymethyl)benzofuran-5-yl)methoxy)-4-methylphenyl)acetate (420c)

Compound 420c was prepared according to the procedure reported in step-3 of scheme-1 from ethyl 2-(2-((2-(hydroxymethyl)-7-iodobenzofuran-5-yl)methoxy)-4-methylphenyl)acetate (420b) (1.0 g, 2.08 mmol) in acetonitrile (25 mL) using tert-butyl 3-(4,4,5,5-tetramethyl-1,3,2-dioxaborolan-2-yl)benzylcarbamate (3b) (1.03 g, 3.12 mmol), a solution of $Na_2CO_3$ (0.66 g, 6.24 mmol) in water (1.2 mL), $Pd(PPh_3)_2Cl_2$ (0.14 g, 0.20 mmol) and heating under a nitrogen atmosphere at 90° C. overnight. This gave after workup and purification by flash column chromatography (silica gel, eluting with 40% ethyl acetate in heptane) ethyl ethyl 2-(2-((7-(3-(((tert-butoxycarbonyl)amino)methyl)phenyl)-2-(hydroxymethyl)benzofuran-5-yl)methoxy)-4-methylphenyl)acetate (420c) (570 mg, 49%) as a yellow oil; $^1H$ NMR (300 MHz, DMSO-$d_6$) δ 7.82-7.68 (m, 2H), 7.63 (d, J=1.6 Hz, 1H), 7.54-7.43 (m, 3H), 7.30 (d, J=7.6 Hz, 1H), 7.08 (d, J=7.5 Hz, 1H), 6.96 (s, 1H), 6.84 (s, 1H), 6.73 (d, J=7.5 Hz, 1H), 5.51 (t, J=5.9 Hz, 1H), 5.19 (s, 2H), 4.60 (d, J=5.9 Hz, 2H), 4.23 (d, J=6.2 Hz, 2H), 3.90 (q, J=7.1 Hz, 2H), 3.56 (s, 2H), 2.30 (s, 3H), 1.39 (s, 9H), 0.97 (t, J=7.1 Hz, 3H).

Step-4: Preparation of Ethyl 2-(2-((7-(3-(aminomethyl)phenyl)-2-(hydroxymethyl)benzofuran-5-yl)methoxy)-4-methylphenyl)acetate (420d)

Compound 420d was prepared according to the procedure reported in step-5 of scheme-1 from ethyl 2-(2-((7-(3-(((tert-butoxycarbonyl)amino)methyl)phenyl)-2-(hydroxymethyl)benzofuran-5-yl)methoxy)-4-methylphenyl)acetate (420c) (390 mg, 0.697 mmol) in DCM (15 mL) using TFA (1.035 mL, 13.94 mmol). This gave after workup ethyl 2-(2-((7-(3-(aminomethyl)phenyl)-2-(hydroxymethyl)benzofuran-5-yl)methoxy)-4-methylphenyl)acetate (420d) which was used in the next step without further purification; MS (ES+): 460.20 (M+1).

Step-5: Preparation of 2-(2-((7-(3-(aminomethyl)phenyl)-2-(hydroxymethyl)benzofuran-5-yl)methoxy)-4-methylphenyl)acetic Acid (420e)

Compound 420e was prepared according to the procedure reported in step-6 of scheme-1 from ethyl 2-(2-((7-(3-(aminomethyl)phenyl)-2-(hydroxymethyl)benzofuran-5-yl)methoxy)-4-methylphenyl)acetate (420d) (0.680 mmol; from above step-4) in MeOH/THF (5 mL, each) using a solution of lithium hydroxide hydrate (233 mg, 5.44 mmol) in water (5 mL) and stirring at room temperature for 16 h. This gave after workup and purification by reverse phase column [C18 column, eluting with water (containing 0.1% HCl)/acetonitrile (1:0 to 0:1)] 2-(2-((7-(3-(aminomethyl)phenyl)-2-(hydroxymethyl)benzofuran-5-yl)methoxy)-4-methylphenyl)acetic acid (420e) (69 mg, 24%) HCl salt as a white solid; $^1$H NMR (300 MHz, DMSO-$d_6$) δ 12.16 (s, 1H), 8.45 (s, 3H), 7.99 (d, J=1.6 Hz, 1H), 7.94 (dt, J=7.3, 1.7 Hz, 1H), 7.69 (d, J=1.6 Hz, 1H), 7.63-7.52 (m, 3H), 7.09 (d, J=7.5 Hz, 1H), 6.94 (d, J=1.6 Hz, 1H), 6.85 (s, 1H), 6.77-6.68 (m, 1H), 5.55 (s, 1H), 5.22 (s, 2H), 4.61 (s, 2H), 4.14 (d, J=5.8 Hz, 2H), 3.54 (s, 2H), 2.29 (s, 3H); MS (ES+): 432.20 (M+1); MS (ES−): 430.15 (M−1); Analysis calculated for $C_{26}H_{25}NO_5 \cdot HCl \cdot H_2O$: C, 63.09; H, 5.91; N, 2.83; Cl, 7.09; Found: C, 63.00; H, 5.79; N, 2.88; Cl, 7.09.

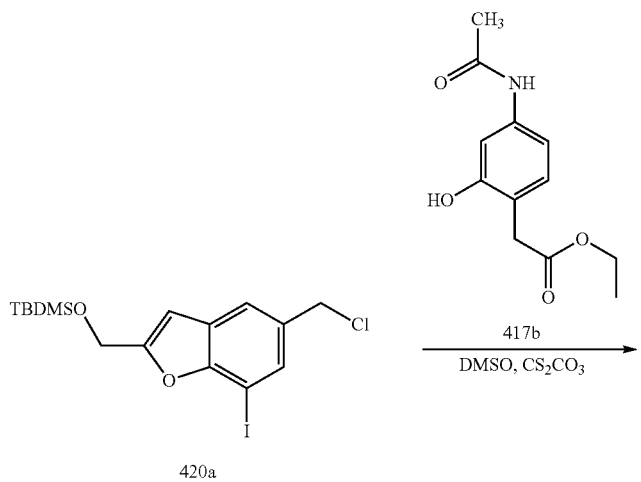

Scheme-421

420a

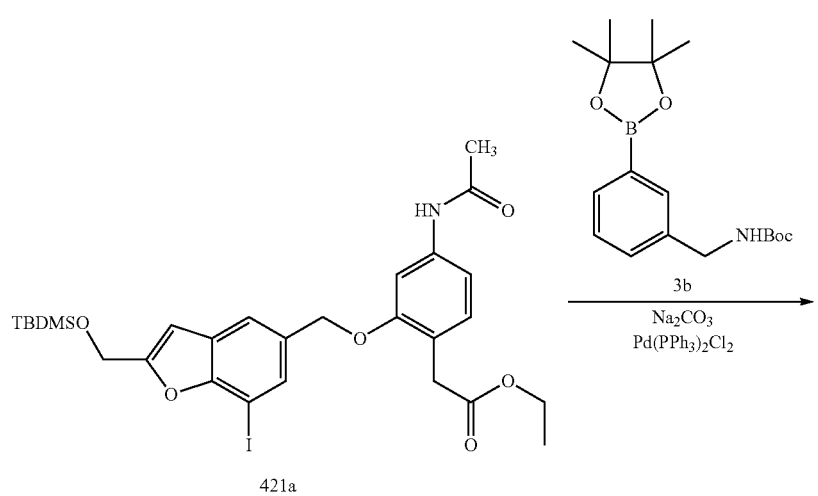

421a

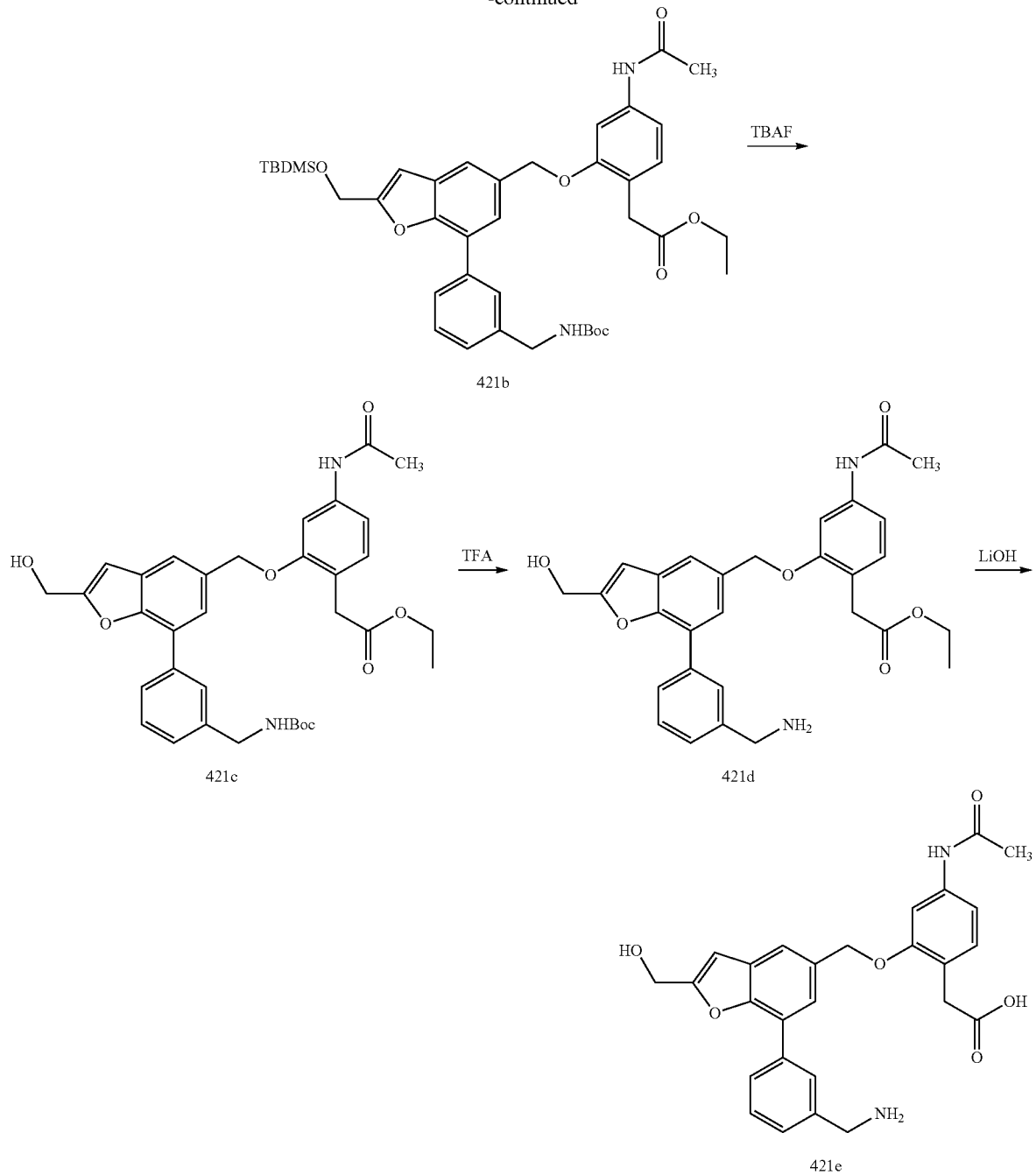

Preparation of 2-(4-acetamido-2-((7-(3-(aminomethyl)phenyl)-2-(hydroxymethyl)benzofuran-5-yl)methoxy)phenyl)acetic Acid (421e)

Step-1: Preparation of Ethyl 2-(4-acetamido-2-((2-(((tert-butyldimethylsilyl)oxy)methyl)-7-iodobenzofuran-5-yl)methoxy)phenyl)acetate (421a)

Compound 421a was prepared according to the procedure reported in step-6 of scheme-257 from tert-butyl(((5-(chloromethyl)-7-iodobenzofuran-2-yl)methoxy)dimethylsilane (420a) (0.215 g, 0.492 mmol) using ethyl 2-(4-acetamido-2-hydroxyphenyl)acetate (417b) (0.13 g, 0.55 mmol), $Cs_2CO_3$ (0.24 g, 0.736 mmol) in DMSO (2 mL) and stirring at room temperature overnight. This gave after workup and purification by flash column chromatography (Silica gel, eluting with 25% EtOAc in n-heptane) ethyl 2-(4-acetamido-2-(((tert-butyldimethylsilyl)oxy)methyl)-7-iodobenzofuran-5-yl)methoxy)phenyl)acetate (421a) 0.24 g, 0.736 mmol (0.12 g, 38%) as a dark brown oil; $^1$H NMR (300 MHz, DMSO-$d_6$) δ 9.94 (s, 1H), 7.71 (s, 1H), 7.65 (s, 1H), 7.39 (s, 1H), 7.10 (s, 2H), 6.96 (s, 1H), 5.07 (s, 2H), 4.83 (s, 2H), 4.00 (q, J=7.1 Hz, 2H), 3.54 (s, 2H), 2.03 (s, 3H), 1.07 (t, J=7.1 Hz, 3H), 0.90 (s, 9H), 0.13 (s, 6H).

Step-2: Preparation of Ethyl 2-(4-acetamido-2-((7-(3-(((tert-butoxycarbonyl)amino)methyl)phenyl)-2-(((tert-butyldimethylsilyl)oxy)methyl)benzofuran-5-yl)methoxy)phenyl)acetate (421b)

Compound 421b was prepared according to the procedure reported in step-3 of scheme-1 from ethyl 2-(4-acetamido-2-((2-(((tert-butyldimethylsilyl)oxy)methyl)-7-iodobenzofuran-5-yl)methoxy)phenyl)acetate (421a) (0.12 g, 0.22 mmol) in acetonitrile (3 mL) using tert-butyl 3-(4,4,5,5-tetramethyl-1,3,2-dioxaborolan-2-yl)benzylcarbamate (3b) (0.09 g, 0.34 mmol), a solution of $Na_2CO_3$ (0.07g, 0.68 mmol) in water (2 mL), $Pd(PPh_3)_2Cl_2$ (0.016 g, 0.022 mmol) and heating under a nitrogen atmosphere at 90° C. for 12 h. This gave after workup and purification by flash column chromatography (silica gel, eluting with 50% ethyl acetate in hexanes) ethyl 2-(4-acetamido-2-((7-(3-(((tert-butoxycarbonyl)amino)methyl)phenyl)-2-(((tert-butyldimethyl silyl)oxy)methyl)benzofuran-5-yl)methoxy)phenyl)acetate (421b) (101 mg, 93%) as a light brown oil; $^1$H NMR (300 MHz, DMSO-$d_6$) δ 9.94 (s, 1H), 7.74 (s, 2H), 7.65 (s, 1H), 7.53 (s, 1H), 7.46 (d, J=7.9 Hz, 2H), 7.30 (d, J=7.4 Hz, 1H), 7.09 (d, J=3.8 Hz, 2H), 6.88 (s, 1H), 5.15 (s, 2H), 4.83 (s, 2H), 4.23 (d, J=6.3 Hz, 2H), 3.91 (q, J=7.1 Hz, 2H), 3.55 (s, 3H), 2.03 (s, 3H), 1.39 (s, 9H), 0.97 (t, J=7.1 Hz, 3H), 0.89 (s, 9H), 0.10 (s, 6H).

Step-3: Preparation of Ethyl 2-(4-acetamido-2-((7-(3-(((tert-butoxycarbonyl)amino)methyl)phenyl)-2-(hydroxymethyl)benzofuran-5-yl)methoxy)phenyl) acetate (421c)

To a solution of ethyl 2-(4-acetamido-2-((7-(3-(((tert-butoxycarbonyl)amino)methyl)phenyl)-2-(((tert-butyldimethylsilyl)oxy)methyl)benzofuran-5-yl)methoxy)phenyl)acetate (421b) (90 mg, 0.126 mmol) in THF (10 mL) was added at 0° C. TBAF (1M in THF) (0.157 mL, 0.157 mmol) and allowed to warm to RT over a period of 1.5 h. The reaction mixture was diluted with saturated $NH_4Cl$ solution (20 mL) and extracted with ethyl acetate (2×100 mL). The combined organic layers were washed with brine, dried, filtered, and evaporated to dryness. The resulting crude product was purified by flash column chromatography [silica gel, 4 g, eluting with ethyl acetate/MeOH (9:1) in hexanes from 0 to 50%] to afford ethyl 2-(4-acetamido-2-((7-(3-(((tert-butoxycarbonyl)amino)methyl)phenyl)-2-(hydroxymethyl)benzofuran-5-yl)methoxy)phenyl)acetate (421c) (61 mg, 81% yield) as a clear oil; MS (ES+): 625.25 (M+Na).

Step-4: Preparation of Ethyl 2-(4-acetamido-2-((7-(3-(aminomethyl)phenyl)-2-(hydroxymethyl)benzofuran-5-yl)methoxy)phenyl)acetate (421d)

Compound 421d was prepared according to the procedure reported in step-5 of scheme-1 from ethyl 2-(4-acetamido-2-((7-(3-(((tert-butoxycarbonyl)amino)methyl)phenyl)-2-(hydroxymethyl)benzofuran-5-yl)methoxy)phenyl)acetate (421c) (55 mg, 0.091 mmol) in DCM (7 mL) using TFA (0.136 mL, 1.825 mmol). This gave after workup ethyl 2-(4-acetamido-2-((7-(3-(aminomethyl)phenyl)-2-(hydroxymethyl)benzofuran-5-yl)methoxy)phenyl)acetate (421d) which was used in the next step without further purification; MS (ES+): 503.20 (M+1).

Step-5: Preparation of 2-(4-acetamido-2-((7-(3-(aminomethyl)phenyl)-2-(hydroxymethyl)benzofuran-5-yl)methoxy)phenyl)acetic Acid (421e)

Compound 421e was prepared according to the procedure reported in step-6 of scheme-1 from ethyl 2-(4-acetamido-2-((7-(3-(aminomethyl)phenyl)-2-(hydroxymethyl)benzofuran-5-yl)methoxy)phenyl)acetate (421d) (0.084 mmol; from above step-4) in MeOH/THF (3 mL, each) using a solution of lithium hydroxide hydrate (29 mg, 0.627 mmol) in water (3 mL) and stirring at room temperature for 16 h. This gave after workup and purification by reverse phase column [C18 column, eluting with water (containing 0.1% HCl)/acetonitrile (1:0 to 0:1)] 2-(4-acetamido-2-((7-(3-(aminomethyl)phenyl)-2-(hydroxymethyl)benzofuran-5-yl)methoxy)phenyl)acetic acid (421e) (12 mg, 30%) HCl salt as a white solid; $^1$H NMR (300 MHz, DMSO-$d_6$) δ 9.97 (s, 1H), 8.33 (s, 3H), 8.00-7.98 (m, 1H), 7.96 (dt, J=7.5, 1.6 Hz, 1H), 7.69 (d, J=1.6 Hz, 1H), 7.63-7.56 (m, 2H), 7.55-7.50 (m, 2H), 7.11 (d, J=8.2 Hz, 1H), 7.04 (dd, J=8.1, 1.8 Hz, 1H), 6.84 (s, 1H), 5.53 (t, J=5.9 Hz, 1H), 5.18 (s, 2H), 4.61 (d, J=5.7 Hz, 2H), 4.14 (s, 2H), 3.52 (s, 2H), 2.03 (s, 3H); MS (ES+): 475.20 (M+1); MS (ES−): 473.20 (M−1).

Scheme-422

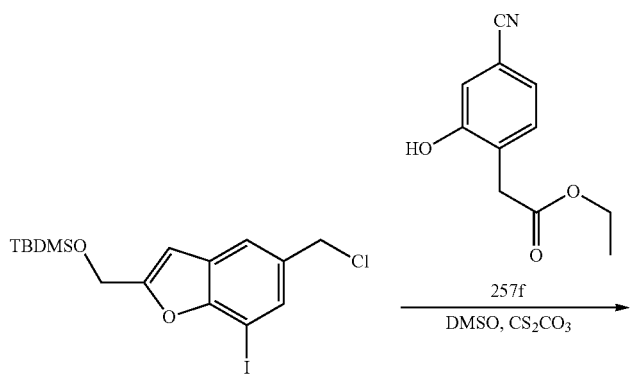

420a

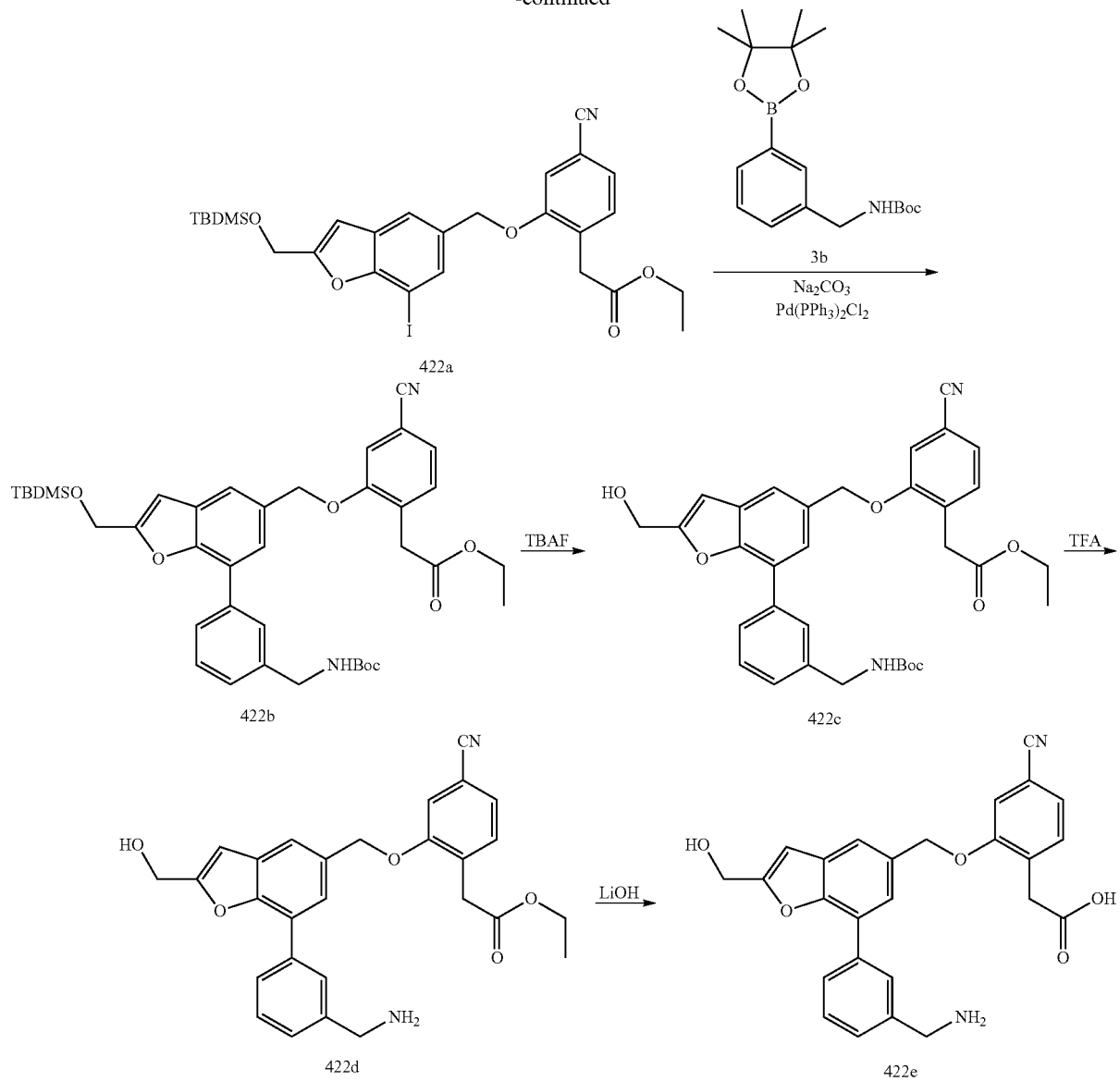

Preparation of 2-(2-((7-(3-(aminomethyl)phenyl)-2-(hydroxymethyl)benzofuran-5-yl)methoxy)-4-cyanophenyl)acetic Acid (422e)

Step-1: Preparation of Ethyl 2-(2-((2-(((tert-butyldimethylsilyl)oxy)methyl)-7-iodobenzofuran-5-yl)methoxy)-4-cyanophenyl)acetate (422a)

Compound 422a was prepared according to the procedure reported in step-6 of scheme-257 from tert-butyl((5-(chloromethyl)-7-iodobenzofuran-2-yl)methoxy)dimethylsilane (420a) (4.0 g, 9.16 mmol) using ethyl 2-(4-cyano-2-hydroxyphenyl)acetate (257f) (2.82 g, 13.74 mmol), $Cs_2CO_3$ (8.95 g, 27.48 mmol) in DMSO (40 mL) and stirring at room temperature for 18 h. This gave after workup and purification by flash column chromatography (Silica gel, eluting with 15% EtOAc in n-heptane) ethyl 2-(2-((2-(((tert-butyldimethylsilyl)oxy)methyl)-7-iodobenzofuran-5-yl)methoxy)-4-cyanophenyl)acetate (422a) (1.0 g, 13.36%) as light yellow oil; $^1$H NMR (300 MHz, DMSO-$d_6$) δ 7.58 (d, J=1.5 Hz, 1H), 7.52 (s, 1H), 7.45 (s, 1H), 7.35-7.26 (m, 2H), 6.85 (s, 1H), 5.08 (s, 2H), 4.70 (s, 2H), 3.88 (q, J=7.1 Hz, 2H), 3.58 (s, 2H), 0.92 (t, J=7.1 Hz, 3H), 0.76 (s, 9H), 0.00 (s, 6H); MS (ES+): 605.5 (M+1), (ES−): 604.5 (M−1).

Step-2: Preparation of Ethyl 2-(2-((7-(3-(((tert-butoxycarbonyl)amino)methyl)phenyl)-2-(((tert-butyldimethylsilyl)oxy)methyl)benzofuran-5-yl)methoxy)-4-cyanophenyl)acetate (422b)

Compound 422b was prepared according to the procedure reported in step-3 of scheme-1 from ethyl 2-(2-((2-(((tert-butyldimethyl silyl)oxy)methyl)-7-iodobenzofuran-5-yl)methoxy)-4-cyanophenyl)acetate (422a) (1.0 g, 1.65 mmol) in acetonitrile (25 mL) using tert-butyl 3-(4,4,5,5-tetramethyl-1,3,2-dioxaborolan-2-yl)benzylcarbamate (3b) (1.03 g, 3.12 mmol), a solution of $Na_2CO_3$ (0.66 g, 6.24 mmol) in water (5 mL), $Pd(PPh_3)_2Cl_2$ (0.14 g, 0.20 mmol) and heating under a nitrogen atmosphere at 90° C. overnight. This gave after workup and purification by flash column chromatography (silica gel, eluting with 40% ethyl acetate in n-heptane) ethyl 2-(2-((7-(3-(((tert-butoxycarbonyl)amino)methyl)phenyl)-2-(((tert-butyldimethylsilyl)oxy)methyl)benzofuran-5-yl)methoxy)-4-cyanophenyl)acetate (422b) (620 mg, 54.86%) as a light yellow oil; $^1$H NMR (300 MHz, DMSO-$d_6$) δ 7.77-7.69 (m, 2H), 7.64 (dd, J=8.1, 1.5 Hz, 2H), 7.55-7.40 (m, 4H), 7.30 (d, J=7.6 Hz, 1H), 6.90 (s, 1H), 5.29 (s, 2H), 4.83 (s, 2H), 4.25-4.16 (m, 2H), 3.89 (q, J=7.1 Hz, 2H), 3.72 (s, 2H), 1.38 (s, 9H), 0.93 (t, J=7.1 Hz, 3H), 0.89 (s, 9H), 0.10 (s, 6H).

Step-3: Preparation of Ethyl 2-(2-((7-(3-(((tert-butoxycarbonyl)amino)methyl)phenyl)-2-(hydroxymethyl)benzofuran-5-yl)methoxy)-4-cyanophenyl)acetate (422c)

Compound 422c was prepared according to the procedure reported in step-3 of scheme-421 from ethyl 2-(2-((7-(3-(((tert-butoxycarbonyl)amino)methyl)phenyl)-2-(((tert-butyldimethylsilyl)oxy)methyl)benzofuran-5-yl)methoxy)-4-cyanophenyl)acetate (422b) (220 mg, 0.321 mmol) in THF (10 mL) using TBAF (1M in THF) (0.402 mL, 0.402 mmol). This gave after workup and purification by flash column chromatography (silica gel, 4g, eluting with 0 to 50% ethyl acetate in hexanes) ethyl 2-(2-((7-(3-(((tert-butoxycarbonyl)amino)methyl)phenyl)-2-(hydroxymethyl)benzofuran-5-yl)methoxy)-4-cyanophenyl)acetate (422c) (151 mg, 82% yield) as a colorless oil.

$^1$H NMR (300 MHz, DMSO-$d_6$) δ 7.79-7.67 (m, 2H), 7.64 (d, J=1.6 Hz, 1H), 7.62 (d, J=1.3 Hz, 1H), 7.52-7.38 (m, 5H), 7.30 (d, J=7.7 Hz, 1H), 6.85 (d, J=0.8 Hz, 1H), 5.51 (t, J=5.7 Hz, 1H), 5.29 (s, 2H), 4.60 (d, J=5.3 Hz, 2H), 4.23 (d, J=6.2 Hz, 2H), 3.90 (q, J=7.1 Hz, 2H), 3.72 (s, 2H), 1.38 (s, 9H), 0.94 (t, J=7.1 Hz, 3H); MS (ES+): 593.20 (M+Na).

Step-4: Preparation of Ethyl 2-(2-((7-(3-(aminomethyl)phenyl)-2-(hydroxymethyl)benzofuran-5-yl)methoxy)-4-cyanophenyl)acetate (422d)

Compound 422d was prepared according to the procedure reported in step-5 of scheme-1 from ethyl 2-(2-((7-(3-(((tert-butoxycarbonyl)amino)methyl)phenyl)-2-(hydroxymethyl)benzofuran-5-yl)methoxy)-4-cyanophenyl)acetate (422c) (130 mg, 0.228 mmol) in DCM (7 mL) using TFA (0.338 mL, 4.56 mmol). This gave after workup ethyl 2-(2-((7-(3-(aminomethyl)phenyl)-2-(hydroxymethyl)benzofuran-5-yl)methoxy)-4-cyanophenyl)acetate (422d) which was used in the next step without further purification; MS (ES+): 471.20 (M+1).

Step-5: Preparation of 2-(2-((7-(3-(aminomethyl)phenyl)-2-(hydroxymethyl)benzofuran-5-yl)methoxy)-4-cyanophenyl)acetic Acid (422e)

Compound 422e was prepared according to the procedure reported in step-6 of scheme-1 from ethyl 2-(2-((7-(3-(aminomethyl)phenyl)-2-(hydroxymethyl)benzofuran-5-yl)methoxy)-4-cyanophenyl)acetate (422d) (0.228 mmol; from above step-4) in MeOH/THF (5 mL, each) using a solution of lithium hydroxide hydrate (69 mg, 1.6 mmol) in water (5 mL) and stirring at room temperature for 16 h. This gave after workup and purification by reverse phase column [C18 column, eluting with water (containing 0.1% HCl)/acetonitrile (1:0 to 0:1)] 2-(2-((7-(3-(aminomethyl)phenyl)-2-(hydroxymethyl)benzofuran-5-yl)methoxy)-4-cyanophenyl)acetic acid (422e) (41 mg, 41%) HCl salt as a white solid; $^1$H NMR (300 MHz, DMSO-$d_6$) δ 7.99-7.97 (m, 1H), 7.94 (dt, J=7.7, 1.5 Hz, 1H), 7.69 (d, J=1.6 Hz, 1H), 7.64-7.50 (m, 4H), 7.47-7.37 (m, 2H), 6.86 (s, 1H), 5.53 (t, J=5.8 Hz, 1H), 5.33 (s, 2H), 4.61 (d, J=5.6 Hz, 2H), 4.14 (s, 2H), 3.68 (s, 2H); MS (ES+): 443.10 (M+1); Analysis calculated for $C_{26}H_{22}N_2O_5 \cdot HCl \cdot 0.9\ H_2O$: C, 63.07; H, 5.05; N, 5.66; Cl, 7.16; Found: C, 63.12; H, 4.85; N, 5.50; Cl, 6.97.

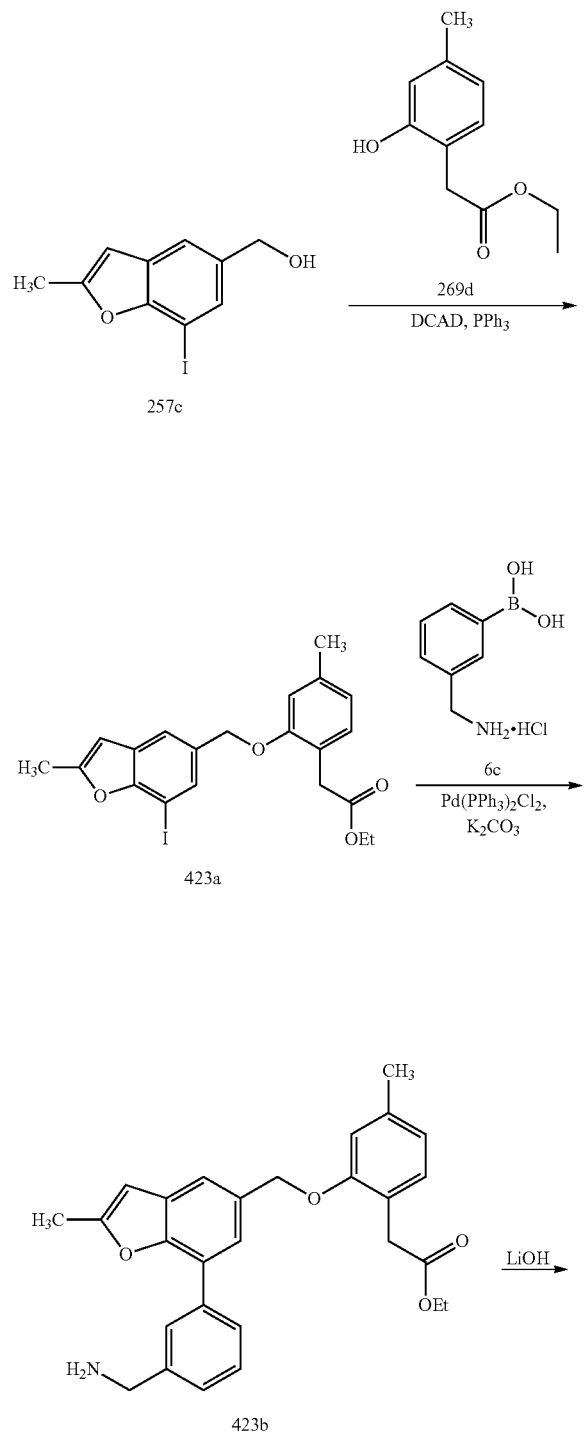

Scheme-423

1309

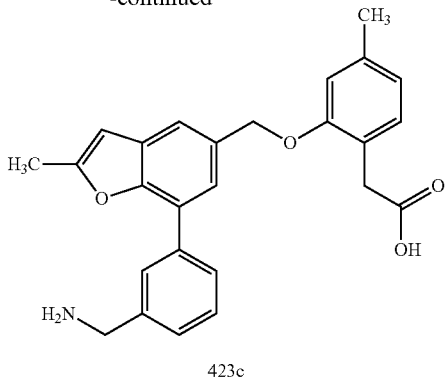

423c

Preparation of 2-(2-((7-(3-(aminomethyl)phenyl)-2-methylbenzofuran-5-yl)methoxy)-4-methylphenyl) acetic Acid (423c)

Step-1: Preparation of Ethyl 2-(2-((7-iodo-2-methylbenzofuran-5-yl)methoxy)-4-methylphenyl)acetate (423a)

Compound 423a was prepared according to the procedure reported in step-2 of scheme-23 from (7-iodo-2-methylbenzofuran-5-yl)methanol (257c) (1.5 g, 5.21 mmol) in DCM (40 mL) using triphenylphosphine (1.775 g, 6.77 mmol) ethyl 2-(2-hydroxy-4-methylphenyl)acetate (269d) (1.315 g, 6.77 mmol) and (E)-bis(4-chlorobenzyl) diazene-1,2-dicarboxylate (DCAD, 2.485 g, 6.77 mmol). This gave after workup and purification by flash column chromatography (silica gel, eluting with EtOAc in hexane from 0-8%) ethyl 2-(2-((7-iodo-2-methylbenzofuran-5-yl)methoxy)-4-methylphenyl)acetate (423a) (1.85 g, 77% yield). $^1$H NMR (300 MHz, DMSO-$d_6$) δ 7.63 (d, J=1.5 Hz, 1H), 7.55 (d, J=1.5 Hz, 1H), 7.07 (d, 1H), 6.91 (d, J=1.4 Hz, 1H), 6.76-6.70 (m, 2H), 5.09 (s, 2H), 4.01 (q, J=7.1 Hz, 2H), 3.55 (s, 2H), 2.48 (d, J=1.1 Hz, 3H), 2.29 (s, 3H), 1.08 (t, J=7.1 Hz, 3H); MS: 487.00 (M+Na).

Step-2: Preparation of Ethyl 2-(2-((7-(3-(aminomethyl)phenyl)-2-methylbenzofuran-5-yl)methoxy)-4-methylphenyl)acetate (423b)

Compound 423b was prepared according to the procedure reported in step-3 of scheme-1 from ethyl 2-(2-((7-iodo-2-methylbenzofuran-5-yl)methoxy)-4-methylphenyl)acetate (423a) (1.8 g, 3.88 mmol) in dioxane (25 mL) using 3-(aminomethyl)phenylboronic acid hydrochloride (6c) (1.09 g, 5.82 mmol), $K_2CO_3$ (1.607 g, 11.63 mmol) in water (4 mL) and bis(triphenylphosphine)palladium(II)chloride (0.408 g, 0.582 mmol) under an Ar atmosphere and heating at 100° C. for 3 h on oil bath. This gave after workup, purification by flash column chromatography [silica gel, eluting with 0-5% MeOH in DCM] ethyl 2-(2-((7-(3-(aminomethyl)phenyl)-2-methylbenzofuran-5-yl)methoxy)-4-methylphenyl)acetate (423b) (1.05 g, 61% yield) as a yellow oil; $^1$H NMR (300 MHz, DMSO-$d_6$) δ 7.81-7.77 (m, 1H), 7.71 (dt, J=7.6, 1.6 Hz, 1H), 7.54 (d, J=1.6 Hz, 1H), 7.52-7.34 (m, 3H), 7.08 (d, J=7.5 Hz, 1H), 6.96-6.94 (m, 1H), 6.72 (ddd, J=7.4, 1.6, 0.8 Hz, 1H), 6.67-6.63 (m, 1H), 5.18 (s, 2H), 3.92 (q, J=7.1 Hz, 2H), 3.82 (s, 2H), 3.56 (s, 2H), 2.47 (d, J=1.1 Hz, 3H), 2.29 (s, 3H), 0.99 (t, J=7.1 Hz, 3H); MS (ES+): 444.20 (M+1).

1310

Step-3: Preparation of 2-(2-((7-(3-(aminomethyl)phenyl)-2-methylbenzofuran-5-yl)methoxy)-4-methylphenyl)acetic Acid (423c)

Compound 423c was prepared according to the procedure reported in step-6 of scheme-1 from ethyl 2-(2-((7-(3-(aminomethyl)phenyl)-2-methylbenzofuran-5-yl)methoxy)-4-methylphenyl)acetate (423b) (500 mg, 1.127 mmol) in MeOH (10 mL) using a solution of lithium hydroxide hydrate (386 mg, 9.02 mmol) in water (10 mL) and stirring for 16 h. This gave after workup and purification by reverse phase column chromatography (C18 100g, eluting with 0-60% MeCN in $H_2O$ containing 0.1% HCl) 2-(2-((7-(3-(aminomethyl)phenyl)-2-methylbenzofuran-5-yl)methoxy)-4-methylphenyl)acetic acid (423c) (408 mg, 87%) HCl salt as a white solid; $^1$H NMR (300 MHz, DMSO-$d_6$) δ 7.99-7.94 (m, 1H), 7.92 (dt, J=7.4, 1.7 Hz, 1H), 7.61 (d, J=1.5 Hz, 1H), 7.60-7.47 (m, 3H), 7.08 (d, J=7.5 Hz, 1H), 6.93 (d, J=1.6 Hz, 1H), 6.75-6.69 (m, 1H), 6.67 (d, J=1.2 Hz, 1H), 5.20 (s, 2H), 4.13 (s, 2H), 3.53 (s, 2H), 2.49 (s, 3H), 2.28 (s, 3H); MS (ES+): 416.20 (M+1); MS (ES−): 414.20 (M−1); Analysis calculated for $C_{26}H_{25}NO_4 \cdot HCl \cdot 0.5H_2O$: C, 67.75; H, 5.90; N, 3.04; Cl, 7.69; Found: C, 67.66; H, 6.04; N, 3.01; Cl, 7.53.

Scheme-424

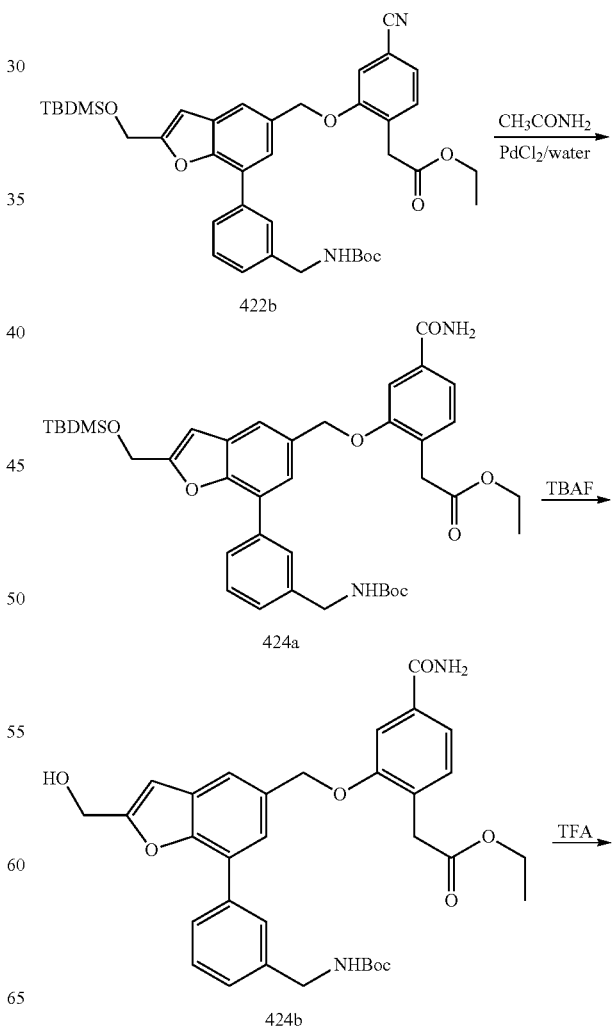

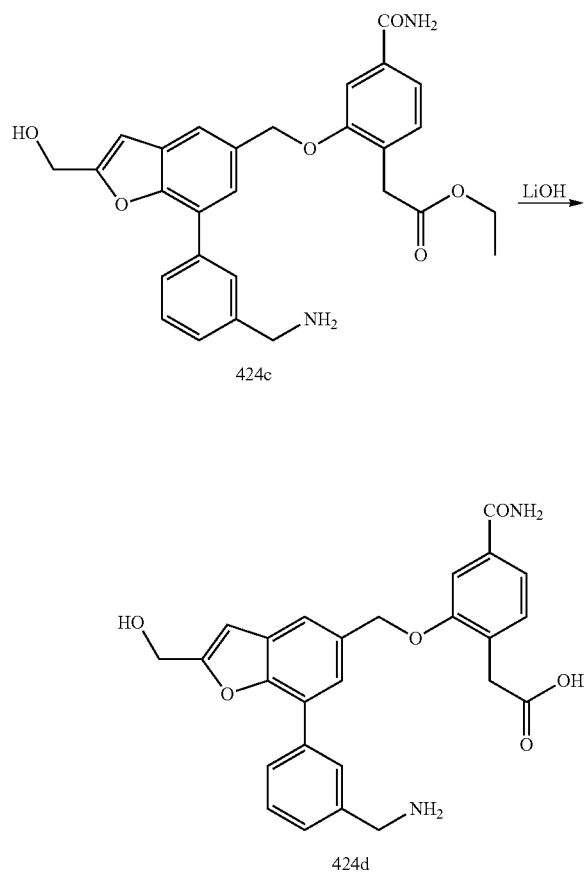

Preparation of 2-(2-((7-(3-(aminomethyl)phenyl)-2-(hydroxymethyl)benzofuran-5-yl)methoxy)-4-carbamoylphenyl)acetic Acid (424d)

Step-1: Preparation of Ethyl 2-(2-((7-(3-(((tert-butoxycarbonyl)amino)methyl)phenyl)-2-(((tert-butyldimethylsilyl)oxy)methyl)benzofuran-5-yl)methoxy)-4-carbamoylphenyl)acetate (424a)

Compound 424a was prepared according to the procedure reported in step-1 of scheme-238 from ethyl 2-(2-((7-(3-(((tert-butoxycarbonyl)amino)methyl)phenyl)-2-(((tert-butyldimethylsilyl)oxy)methyl)benzofuran-5-yl)methoxy)-4-cyanophenyl)acetate (422b) (300 mg, 0.438 mmol) in THF (15 mL) and water (1.2 mL), using acetamide (155 mg, 2.63 mmol), palladium(II) chloride (23 mg, 0.131 mmol) and stirring at room temperature for 18 h. This gave after workup and purification by flash column chromatography (silica gel, 12 g, eluting with methanol in DCM from 0 to 5%) ethyl 2-(2-((7-(3-(((tert-butoxycarbonyl)amino)methyl)phenyl)-2-(((tert-butyldimethylsilyl)oxy)methyl)benzofuran-5-yl)methoxy)-4-carbamoylphenyl)acetate (424a) (76 mg, 25% yield) as a colorless oil; $^1$H NMR (300 MHz, DMSO-$d_6$) δ 7.98 (s, 1H), 7.80-7.71 (m, 2H), 7.66 (d, J=1.6 Hz, 1H), 7.64-7.63 (m, 1H), 7.55 (d, J=1.7 Hz, 1H), 7.51-7.39 (m, 3H), 7.37 (s, 1H), 7.32-7.31 (m, 1H), 7.30-7.27 (m, 1H), 6.90-6.89 (m, 1H), 5.27 (s, 2H), 4.83 (s, 2H), 4.22 (d, J=6.2 Hz, 2H), 3.90 (q, J=7.1 Hz, 2H), 3.67 (s, 2H), 1.39 (s, 9H), 0.95 (t, J=7.1 Hz, 3H), 0.89 (s, 9H), 0.10 (s, 6H).

Step-2: Preparation of Ethyl 2-(2-((7-(3-(((tert-butoxycarbonyl)amino)methyl)phenyl)-2-(hydroxymethyl)benzofuran-5-yl)methoxy)-4-carbamoylphenyl)acetate (424b)

Compound 424b was prepared according to the procedure reported in step-3 of scheme-421 from ethyl 2-(2-((7-(3-(((tert-butoxycarbonyl)amino)methyl)phenyl)-2-(((tert-butyldimethylsilyl)oxy)methyl)benzofuran-5-yl)methoxy)-4-carbamoylphenyl)acetate (424a) (70 mg, 0.100 mmol) in THF (10 mL) using TBAF (33 mg, 0.124 mmol). This gave after workup and purification by flash column chromatography (silica gel, 4g, eluting with 0 to 50% methanol in dichloromethane) ethyl 2-(2-((7-(3-(((tert-butoxycarbonyl)amino)methyl)phenyl)-2-(hydroxymethyl)benzofuran-5-yl)methoxy)-4-carbamoylphenyl)acetate (424b) (58 mg, 99% yield) as a colorless oil; $^1$H NMR (300 MHz, DMSO-$d_6$) δ 7.98 (s, 1H), 7.79-7.69 (m, 2H), 7.65 (d, J=1.6 Hz, 1H), 7.63-7.62 (m, 1H), 7.51 (d, J=1.8 Hz, 1H), 7.49-7.42 (m, 3H), 7.37 (s, 1H), 7.31 (s, 1H), 7.28 (s, 1H), 6.85-6.83 (m, 1H), 5.50 (t, J=5.9 Hz, 1H), 5.26 (d, J=1.6 Hz, 2H), 4.60 (d, J=6.0 Hz, 2H), 4.23 (d, J=6.2 Hz, 2H), 3.91 (q, J=7.1 Hz, 2H), 3.67 (s, 2H), 1.39 (s, 9H), 1.02-0.93 (m, 3H); MS: 611.20 (M+Na).

Step-3: Preparation of Ethyl 2-(2-((7-(3-(aminomethyl)phenyl)-2-(hydroxymethyl)benzofuran-5-yl)methoxy)-4-carbamoylphenyl)acetate (424c)

Compound 424c was prepared according to the procedure reported in step-5 of scheme-1 from ethyl 2-(2-((7-(3-(((tert-butoxycarbonyl)amino)methyl)phenyl)-2-(hydroxymethyl)benzofuran-5-yl)methoxy)-4-carbamoylphenyl)acetate (424b) (52 mg, 0.088 mmol) in DCM (7 mL) using TFA (0.131 mL, 1.767 mmol). This gave after workup ethyl 2-(2-((7-(3-(aminomethyl)phenyl)-2-(hydroxymethyl)benzofuran-5-yl)methoxy)-4-carbamoylphenyl)acetate (424c) (92 mg) which was used as such for next step without further purification; MS (ES+): 489.10 (M+1).

Step-4: Preparation of 2-(2-((7-(3-(aminomethyl)phenyl)-2-(hydroxymethyl)benzofuran-5-yl)methoxy)-4-carbamoylphenyl)acetic Acid (424d)

Compound 424d was prepared according to the procedure reported in step-6 of scheme-1 from ethyl 2-(2-((7-(3-(aminomethyl)phenyl)-2-(hydroxymethyl)benzofuran-5-yl)methoxy)-4-carbamoylphenyl)acetate (424c) (0.08 mmol; from above step-3) in MeOH/THF (5 mL, each) using a solution of lithium hydroxide hydrate (27 mg, 0.640 mmol) in water (5 mL) and stirring at room temperature for 16 h. This gave after workup and purification by reverse phase column [C18 column, eluting with water (containing 0.1% HCl)/acetonitrile (1:0 to 0:1)] 2-(2-((7-(3-(aminomethyl)phenyl)-2-(hydroxymethyl)benzofuran-5-yl)methoxy)-4-carbamoylphenyl)acetic acid (424d) (3 mg, 7%) HCl salt as a white solid; $^1$H NMR (300 MHz, DMSO-$d_6$) δ 8.02-7.93 (m, 3H), 7.69 (s, 1H), 7.66-7.55 (m, 3H), 7.54-7.47 (m, 1H), 7.44 (d, J=7.9 Hz, 1H), 6.85 (s, 1H), 7.35 (s, 1H), 7.28 (d, J=7.6 Hz, 1H), 5.51 (t, J=5.8 Hz, 1H), 5.30 (s, 2H), 4.64-4.58 (m, 2H), 4.14 (s, 2H), 3.62 (s, 2H); MS (ES+): 461.10 (M+1).

Scheme-425

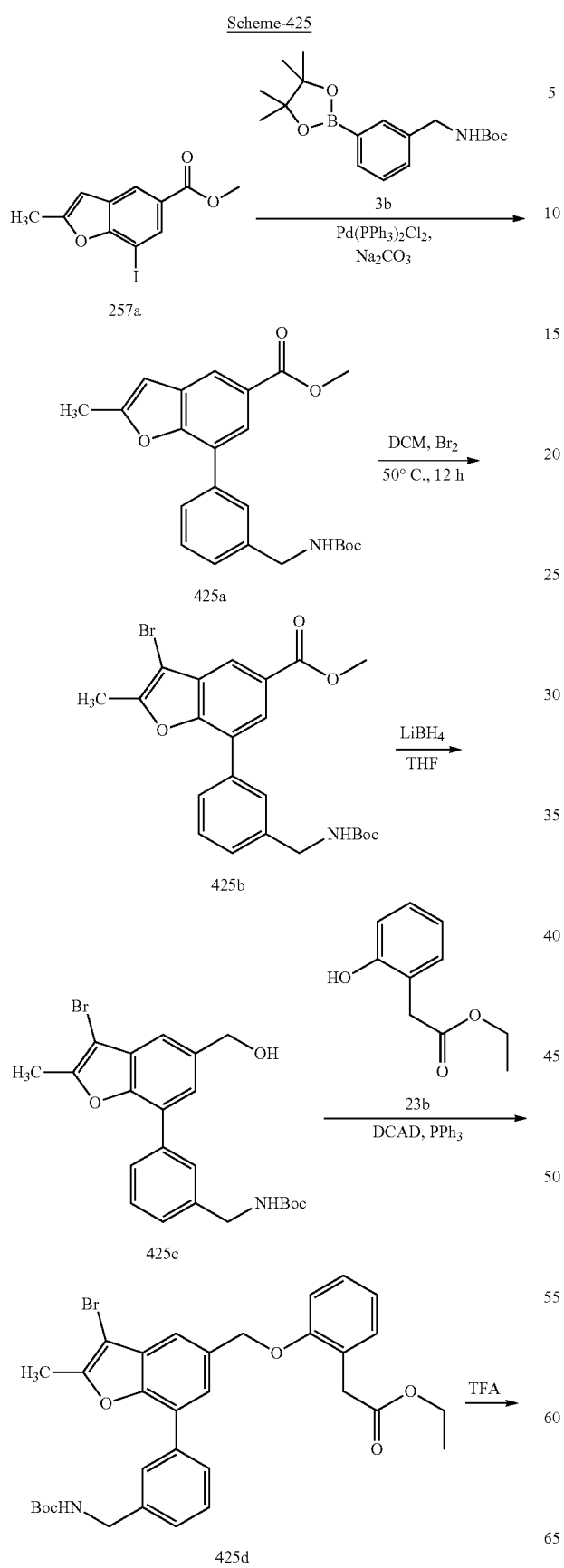

Preparation of 2-(2-((7-(3-(aminomethyl)phenyl)-3-bromo-2-methylbenzofuran-5-yl)methoxy)phenyl)acetic Acid (425f)

Step-1: Preparation of methyl 7-(3-(((tert-butoxycarbonyl)amino)methyl)phenyl)-2-methylbenzofuran-5-carboxylate (425a)

Compound 425a was prepared according to the procedure reported in step-3 of scheme-1 from methyl 7-iodo-2-methylbenzofuran-5-carboxylate (257a) (3.0 g, 9.49 mmol) in acetonitrile (60 mL) using tert-butyl 3-(4,4,5,5-tetramethyl-1,3,2-dioxaborolan-2-yl)benzylcarbamate (3b) (3.79 g, 11.38 mmol), a solution of $Na_2CO_3$ (3.01 g, 28.47 mmol) in water (6.0 mL), $Pd(PPh_3)_2Cl_2$ (1.33 g, 1.89 mmol) and heating under a nitrogen atmosphere at 90° C. for 12 h. This gave after workup and purification by flash column chromatography (silica gel, eluting with 0 to 40% ethyl acetate in n-heptane) methyl 7-(3-(((tert-butoxycarbonyl)amino)methyl)phenyl)-2-methylbenzofuran-5-carboxylate (425a) (2.1 g, 56%) as an oil; $^1$H NMR (300 MHz, DMSO-$d_6$) δ 8.26-8.11 (m, 1H), 8.04-7.90 (m, 1H), 7.82-7.65 (m, 2H), 7.49 (dd, J=13.2, 6.4 Hz, 2H), 7.41-7.25 (m, 1H), 6.80 (td, J=6.1, 1.2 Hz, 1H), 4.37-4.09 (m, 2H), 3.88 (s, 3H), 2.50 (s, 3H), 1.39 (s, 9H).

Step-2: Preparation of methyl 3-bromo-7-(3-(((tert-butoxycarbonyl)amino)methyl)phenyl)-2-methylbenzofuran-5-carboxylate (425b)

To a solution of methyl 7-(3-(((tert-butoxycarbonyl)amino)methyl)phenyl)-2-methylbenzofuran-5-carboxylate (425a) (10.0 g, 25.28 mmol) in DCM (300 mL) was added at room temperature $Br_2$ (4.04 g, 25.28 mmol) and heated at 50° C. for 12 h. The reaction mixture was cooled to room temperature, poured into saturated aqueous sodium thiosulphate (300 mL) and extracted with DCM (2×500 mL). The combined organic extracts were washed with brine (500 mL)

dried, filtered and concentrated in vacuum. The residue obtained was purified by flash column chromatography (silica gel, eluting with 0 to 40% ethyl acetate in n-heptane) to afford methyl 3-bromo-7-(3-(((tert-butoxycarbonyl) amino)methyl)phenyl)-2-methylbenzofuran-5-carboxylate (425b) (4.0 g, 34%) as an oil; $^1$H NMR (300 MHz, DMSO-d$_6$) δ 8.06 (d, J=1.7 Hz, 1H), 7.98 (d, J=1.7 Hz, 1H), 7.74 (d, J=7.7 Hz, 1H), 7.68 (s, 1H), 7.51 (t, J=7.5 Hz, 2H), 7.35 (d, J=7.7 Hz, 1H), 4.24 (d, J=6.2 Hz, 2H), 3.92 (s, 3H), 2.53 (s, 3H), 1.40 (s, 9H).

Step-3: Preparation of tert-butyl 3-(3-bromo-5-(hydroxymethyl)-2-methylbenzofuran-7-yl)benzylcarbamate (425c)

Compound 425c was prepared according to the procedure reported in step-2 of scheme-76 from methyl 3-bromo-7-(3-(((tert-butoxycarbonyl)amino)methyl)phenyl)-2-methylbenzofuran-5-carboxylate (425b) (10.0 g, 25.28 mmol) in THF (160 mL) using LiBH$_4$ (4.04 g, 25.28 mmol). This gave after workup and purification by flash column chromatography [silica gel, eluting with 40% EtOAc in n-heptane] tert-butyl 3-(3-bromo-5-(hydroxymethyl)-2-methylbenzofuran-7-yl) benzylcarbamate (425c) (3.3 g, 87%) as an oil; $^1$H NMR (300 MHz, DMSO-d$_6$) δ 7.76-7.61 (m, 2H), 7.57-7.43 (m, 3H), 7.41-7.36 (m, 1H), 7.30 (d, J=7.6 Hz, 1H), 5.35 (t, J=5.8 Hz, 1H), 4.66 (d, J=5.6 Hz, 2H), 4.22 (d, J=6.2 Hz, 2H), 2.52 (s, 3H), 1.40 (s, 9H).

Step-4: Preparation of Ethyl 2-(2-((3-bromo-7-(3-(((tert-butoxycarbonyl)amino)methyl)phenyl)-2-methylbenzofuran-5-yl)methoxy)phenyl)acetate (425d)

Compound 425d was prepared according to the procedure reported in step-2 of scheme-23 from tert-butyl 3-(3-bromo-5-(hydroxymethyl)-2-methylbenzofuran-7-yl)benzylcarbamate (425c) (3.3 g, 7.39 mmol) in DCM (75 mL) using triphenylphosphine (2.52 g, 9.61 mmol), ethyl 2-(2-hydroxyphenyl)acetate (23b) (1.732 g, 9.61 mmol) and a solution of (E)-bis(4-chlorobenzyl) diazene-1,2-dicarboxylate (DCAD, 3.53 g, 9.61 mmol) in DCM (60 mL). This gave after workup and purification by flash column chromatography (silica gel, eluting with 0 to 20% ethyl acetate in hexanes) ethyl 2-(2-((3-bromo-7-(3-(((tert-butoxycarbonyl) amino)methyl)phenyl)-2-methylbenzofuran-5-yl)methoxy) phenyl)acetate (425d) (3.40 g, 76% yield). $^1$H NMR (300 MHz, DMSO-d$_6$) δ 7.78-7.65 (m, 2H), 7.57 (d, J=1.7 Hz, 1H), 7.54-7.42 (m, 3H), 7.34-7.28 (m, 1H), 7.28-7.19 (m, 2H), 7.12 (dd, J=8.0, 1.1 Hz, 1H), 6.91 (td, J=7.4, 1.1 Hz, 1H), 5.26 (s, 2H), 4.23 (d, J=6.2 Hz, 2H), 3.93 (q, J=7.1 Hz, 2H), 3.62 (s, 2H), 2.51-2.49 (m, 3H), 1.39 (s, 9H), 0.97 (t, J=7.1 Hz, 3H).

Step-5: Preparation of Ethyl 2-(2-((7-(3-(aminomethyl)phenyl)-3-bromo-2-methylbenzofuran-5-yl)methoxy)phenyl)acetate (425e)

Compound 425e was prepared according to the procedure reported in step-5 of scheme-1 from ethyl 2-(2-((3-bromo-7-(3-(((tert-butoxycarbonyl)amino)methyl)phenyl)-2-methylbenzofuran-5-yl)methoxy)phenyl)acetate (425d) (250 mg, 0.411 mmol) in DCM (10 mL) using TFA (0.61 mL, 8.22 mmol). This gave after workup ethyl 2-(2-((7-(3-(aminomethyl)phenyl)-3-bromo-2-methylbenzofuran-5-yl)methoxy) phenyl)acetate (425e) which was used as such for next step; MS (ES+): 509.10 (M+1).

Step-6: Preparation of 2-(2-((7-(3-(aminomethyl) phenyl)-3-bromo-2-methylbenzofuran-5-yl) methoxy)phenyl)acetic Acid (425f)

Compound 425f was prepared according to the procedure reported in step-6 of scheme-1 from ethyl 2-(2-((7-(3-(aminomethyl)phenyl)-3-bromo-2-methylbenzofuran-5-yl) methoxy)phenyl)acetate (425e) (0.411 mmol, from above step-5) in THF/methanol (7 mL, each) using solution of lithium hydroxide hydrate (141 mg, 3.29 mmol) in water (7 mL) and stirring at room temperature for 16 h. This gave after workup and purification by reverse-phase column chromatography [C-18 column, eluting with water (containing 0.1% HCl)/acetonitrile (1:0 to 0:1)] 2-(2-((7-(3-(aminomethyl)phenyl)-3-bromo-2-methylbenzofuran-5-yl) methoxy)phenyl)acetic acid (425f) (91 mg, 46%) HCl salt as a white solid; $^1$H NMR (300 MHz, DMSO-d$_6$) δ 8.41 (s, 3H), 7.98-7.93 (m, 1H), 7.90 (dt, J=7.4, 1.7 Hz, 1H), 7.66 (d, J=1.7 Hz, 1H), 7.60 (t, J=7.5 Hz, 1H), 7.57-7.53 (m, 2H), 7.24 (s, 1H), 7.21 (s, 1H), 7.09 (d, J=8.1 Hz, 1H), 6.91 (td, J=7.4, 1.1 Hz, 1H), 5.30 (s, 2H), 4.14 (s, 2H), 3.60 (s, 2H), 2.52 (s, 3H); MS (ES+): 480.10 (M+1); MS (ES−): 478.05 (M−1); Analysis calculated for C$_{25}$H$_{22}$BrNO$_4$.HCl.H$_2$O: C, 56.14; H, 4.71; N, 2.62; Cl, 6.63; Found: C, 56.17; H, 4.67; N, 2.58; Cl, 6.49.

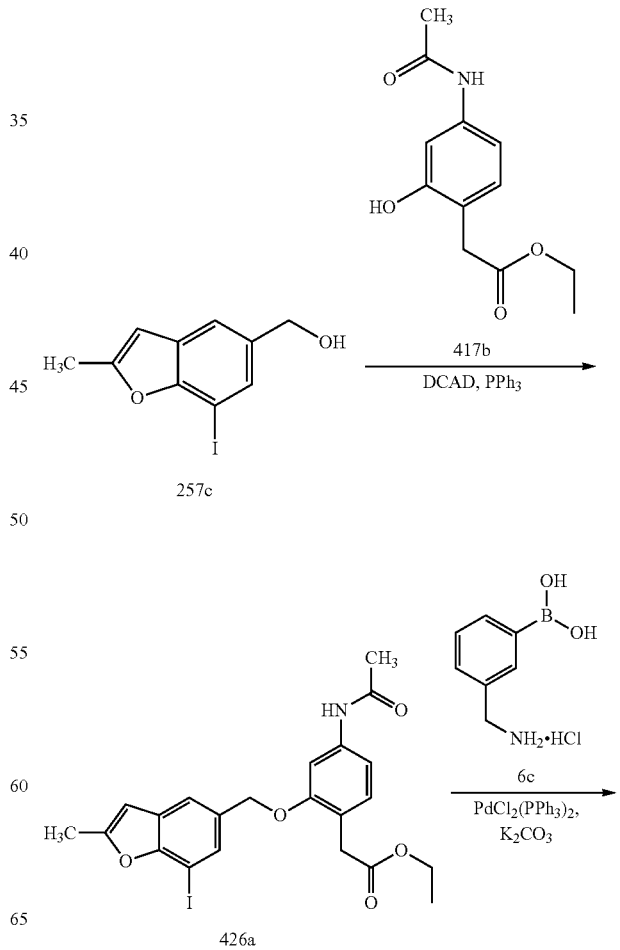

Scheme-426

-continued

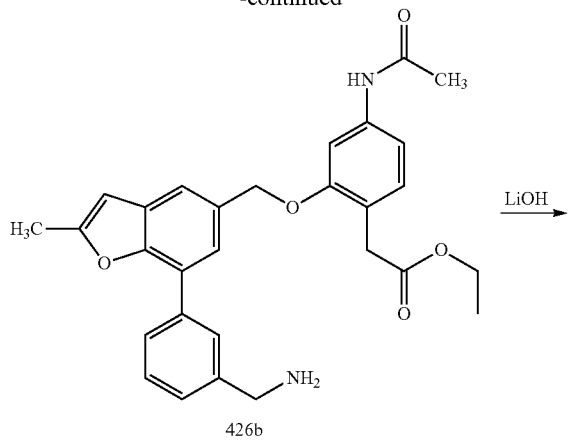

426b

↓ LiOH

426c

Preparation of 2-(4-acetamido-2-((7-(3-(aminomethyl)phenyl)-2-methylbenzofuran-5-yl)methoxy)phenyl)acetic Acid (426c)

Step-1: Preparation of Ethyl 2-(4-acetamido-2-((7-iodo-2-methylbenzofuran-5-yl)methoxy)phenyl)acetate (426a)

Compound 426a was prepared according to the procedure reported in step-2 of scheme-23 from (7-iodo-2-methylbenzofuran-5-yl)methanol (257c) (486 mg, 1.686 mmol) in DCM (20 mL) using triphenylphosphine (575 mg, 2.192 mmol), ethyl 2-(4-acetamido-2-hydroxyphenyl)acetate (417b) (400 mg, 1.686 mmol) and (E)-bis(4-chlorobenzyl) diazene-1,2-dicarboxylate (DCAD, 805 mg, 2.192 mmol) in DCM (15 mL). This gave after workup and purification by flash column chromatography (silica gel, 80 g, eluting with 0 to 100% ethyl acetate in hexanes) ethyl 2-(4-acetamido-2-((7-iodo-2-methylbenzofuran-5-yl)methoxy)phenyl)acetate (426a) (472 mg, 55% yield). $^1$H NMR (300 MHz, DMSO-$d_6$) δ 9.92 (s, 1H), 7.63 (d, J=1.6 Hz, 1H), 7.55 (d, J=1.5 Hz, 1H), 7.38 (s, 1H), 7.11-7.09 (m, 2H), 6.73 (d, J=1.2 Hz, 1H), 5.05 (s, 2H), 4.01 (q, J=7.1 Hz, 2H), 3.54 (s, 2H), 2.48 (d, J=1.3 Hz, 3H), 2.02 (s, 3H), 1.08 (t, J=7.1 Hz, 3H); MS (ES+): 508.00 (M+1).

Step-2: Preparation of Ethyl 2-(4-acetamido-2-((7-(3-(aminomethyl)phenyl)-2-methylbenzofuran-5-yl)methoxy)phenyl)acetate (426b)

Compound 426b was prepared according to the procedure reported in step-3 of scheme-1 from ethyl 2-(4-acetamido-2-((7-iodo-2-methylbenzofuran-5-yl)methoxy)phenyl)acetate (426a) (450 mg, 0.887 mmol) in dioxane (15 mL) using 3-(aminomethyl)phenylboronic acid hydrochloride (6c) (249 mg, 1.331 mmol), $K_2CO_3$ (368 mg, 2.66 mmol) in water (4 mL) and bis(triphenylphosphine)palladium(II)chloride (93 mg, 0.133 mmol) under a nitrogen atmosphere and heating at 100° C. for 3 h on oil bath. This gave after workup, purification by flash column chromatography (silica gel, 24 g, eluting with 0 to 12% methanol in dichloromethane) ethyl 2-(4-acetamido-2-((7-(3-(aminomethyl)phenyl)-2-methylbenzofuran-5-yl)methoxy)phenyl)acetate (426b) (258 mg, 60% yield) as a light-yellow oil. $^1$H NMR (300 MHz, DMSO-$d_6$) δ 9.92 (s, 1H), 7.80 (s, 1H), 7.75-7.70 (m, 1H), 7.54 (d, 1H), 7.49-7.34 (m, 4H), 7.14-7.05 (m, 2H), 6.65 (d, J=1.2 Hz, 1H), 5.14 (s, 2H), 3.93 (q, J=7.2 Hz, 2H), 3.82 (s, 2H), 3.55 (s, 2H), 2.48 (d, 3H), 2.03 (s, 3H), 1.00 (t, J=7.1 Hz, 3H); MS (ES+): 487.20 (M+1).

Step-3: Preparation of 2-(4-acetamido-2-((7-(3-(aminomethyl)phenyl)-2-methylbenzofuran-5-yl)methoxy)phenyl)acetic Acid (426c)

Compound 426c was prepared according to the procedure reported in step-6 of scheme-1 from ethyl 2-(4-acetamido-2-((7-(3-(aminomethyl)phenyl)-2-methylbenzofuran-5-yl)methoxy)phenyl)acetate (426b) (240 mg, 0.493 mmol) in MeOH (10 mL) using a solution of lithium hydroxide hydrate (169 mg, 3.95 mmol) in water (10 mL) and stirring for 16 h. This gave after workup and purification by reverse phase column chromatography (C-18, eluting with 0-100% MeCN in $H_2O$ containing 0.1% HCl) 2-(4-acetamido-2-((7-(3-(aminomethyl)phenyl)-2-methylbenzofuran-5-yl)methoxy)phenyl)acetic acid (426c) (157 mg, 69%) HCl salt as a white solid; $^1$H NMR (300 MHz, DMSO-$d_6$, $D_2O$ exchange) δ 10.00 (s, 1H), 7.98-7.88 (m, 2H), 7.62-7.54 (m, 2H), 7.53-7.46 (m, 3H), 7.10 (d, J=8.2 Hz, 1H), 7.02 (dd, J=8.0, 1.8 Hz, 1H), 6.65 (d, J=1.2 Hz, 1H), 5.16 (s, 2H), 4.13 (s, 2H), 3.51 (s, 2H), 2.46 (d, J=1.1 Hz, 3H), 2.02 (s, 3H); MS (ES+): 459.20 (M+1); MS (ES−): 457.15 (M−1); Analysis calculated for $C_{27}H_{26}N_2O_5$·HCl·1.25$H_2O$: C, 62.67; H, 5.75; N, 5.41; Cl, 6.85; Found: C, 62.86; H, 5.58; N, 5.28; Cl, 6.79.

Scheme-427

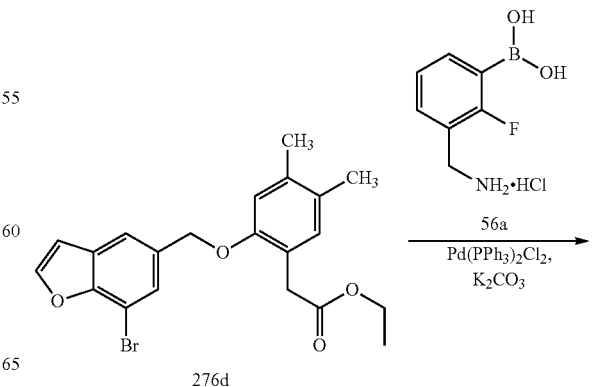

276d → 56a, Pd(PPh$_3$)$_2$Cl$_2$, $K_2CO_3$

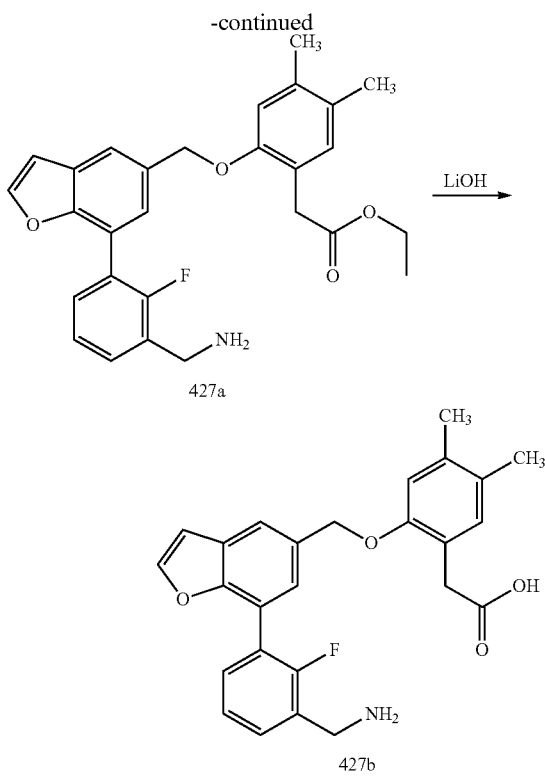

427a

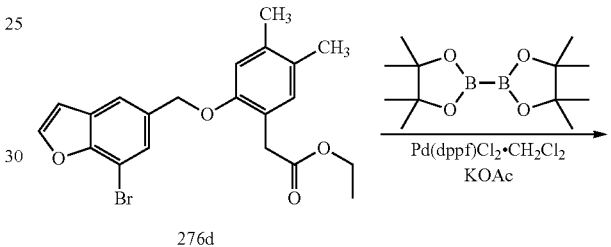

427b

Preparation of 2-(2-((7-(3-(aminomethyl)-2-fluorophenyl)benzofuran-5-yl)methoxy)-4,5-dimethylphenyl)acetic Acid (427b)

Step-1: Preparation of Ethyl 2-(2-((7-(3-(aminomethyl)-2-fluorophenyl)benzofuran-5-yl)methoxy)-4,5-dimethylphenyl)acetate (427a)

Compound 427a was prepared according to the procedure reported in step-3 of scheme-1 from ethyl 2-(2-((7-bromobenzofuran-5-yl)methoxy)-4,5-dimethylphenyl)acetate (276d) (400 mg, 0.959 mmol) in dioxane (5 mL) using (3-(aminomethyl)-2-fluorophenyl)boronic acid hydrochloride (56a) (295 mg, 1.438 mmol), K$_2$CO$_3$ (397 mg, 2.88 mmol) in water (0.5 mL) and bis(triphenylphosphine)palladium(II)chloride (101 mg, 0.144 mmol) under a nitrogen atmosphere and heating at 100° C. for 3 h on oil bath. This gave after workup, purification by flash column chromatography (silica gel, 24 g, eluting with DMA80 in DCM from 0-30%) ethyl 2-(2-((7-(3-(aminomethyl)-2-fluorophenyl)benzofuran-5-yl)methoxy)-4,5-dimethylphenyl)acetate (427a) (232 mg, 52% yield) as a clear oil; $^1$H NMR (300 MHz, DMSO-d$_6$) δ 8.03 (d, J=2.2 Hz, 1H), 7.74 (d, J=1.7 Hz, 1H), 7.59 (td, J=7.4, 1.9 Hz, 1H), 7.45 (td, J=7.4, 1.9 Hz, 1H), 7.41-7.39 (m, 1H), 7.31 (t, J=7.6 Hz, 1H), 7.04 (d, J=2.2 Hz, 1H), 6.94 (d, J=2.7 Hz, 2H), 5.17 (s, 2H), 3.90 (q, J=7.1 Hz, 2H), 3.84 (s, 2H), 3.53 (s, 2H), 2.20 (s, 3H), 2.13 (s, 3H), 0.98 (t, J=7.1 Hz, 3H). $^{19}$F NMR (282 MHz, DMSO-d$_6$) δ−121.77; MS: 362.20 (M+1).

Step-2: Preparation of 2-(2-((7-(3-(aminomethyl)-2-fluorophenyl)benzofuran-5-yl)methoxy)-4,5-dimethylphenyl)acetic Acid (427b)

Compound 427b was prepared according to the procedure reported in step-6 of scheme-1 from ethyl 2-(2-((7-(3-(aminomethyl)-2-fluorophenyl)benzofuran-5-yl)methoxy)-4,5-dimethylphenyl)acetate (427a) (210 mg, 0.455 mmol) in THF/MeOH (10 mL, each) using a solution of lithium hydroxide hydrate (117 mg, 2.73 mmol) in water (10 mL) and stirring for 16 h. This gave after workup and purification by reverse phase column chromatography (C-18, eluting with 0-100% MeCN in H$_2$O containing 0.1% HCl) 2-(2-((7-(3-(aminomethyl)-2-fluorophenyl)benzofuran-5-yl)methoxy)-4,5-dimethylphenyl)acetic acid (427b) (91 mg, 46%) HCl salt as a white solid; $^1$H NMR (300 MHz, DMSO-d$_6$) δ 9.32 (s, 3H), 8.05 (d, J=2.2 Hz, 1H), 7.81 (d, J=1.6 Hz, 1H), 7.73 (td, J=7.4, 1.7 Hz, 1H), 7.67 (td, J=7.5, 1.7 Hz, 1H), 7.47 (s, 1H), 7.42 (t, J=7.7 Hz, 1H), 7.05 (d, J=2.2 Hz, 1H), 6.95 (s, 1H), 6.92 (s, 1H), 5.20 (s, 2H), 4.16 (s, 2H), 3.49 (s, 2H), 2.19 (s, 3H), 2.12 (s, 3H); $^{19}$F NMR (282 MHz, DMSO-d$_6$) δ−118.49; MS (ES+): 434.20 (M+1); MS (ES−): 432.20 (M−1); Analysis calculated for C$_{26}$H$_{24}$FNO$_4$.HCl.0.75H$_2$O: C, 64.59; H, 5.53; N, 2.90; Cl, 7.33; Found: C, 64.93; H, 5.31; N, 2.81; Cl, 6.99.

Scheme-428

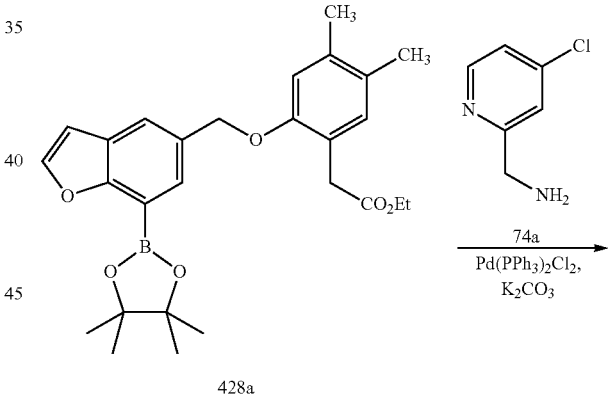

276d

428a

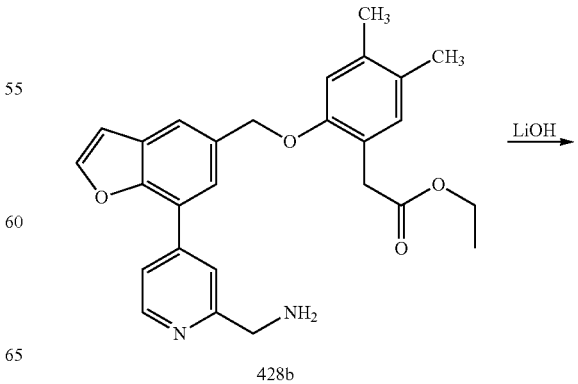

428b

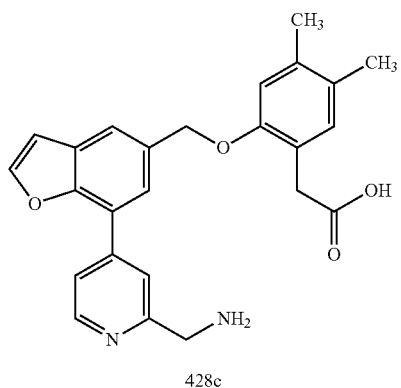

428c

Preparation of 2-(2-((7-(2-(aminomethyl)pyridin-4-yl)benzofuran-5-yl)methoxy)-4,5-dimethylphenyl)acetic Acid (428c)

Step-1: Preparation of Ethyl 2-(4,5-dimethyl-2-((7-(4,4,5,5-tetramethyl-1,3,2-dioxaborolan-2-yl)benzofuran-5-yl)methoxy)phenyl)acetate (428a)

Compound 428a was prepared according to the procedure reported in step-1 of scheme-59 from ethyl 2-(2-((7-bromobenzofuran-5-yl)methoxy)-4,5-dimethylphenyl)acetate (276d) (1.00 g, 2.396 mmol), using bis(pinacolato)diboron (0.913 g, 3.59 mmol), potassium acetate (0.706 g, 7.19 mmol) and PdC$_2$(dppf)-CH$_2$Cl$_2$ (0.196 g, 0.240 mmol) in anhydrous dioxane (25 mL) under a nitrogen atmosphere and heating at 90° C. for 18 h. This gave after workup and purification by flash column chromatography [silica gel (40g), eluting with EtOAc in hexane from 0-12%] ethyl 2-(4,5-dimethyl-2-((7-(4,4,5,5-tetramethyl-1,3,2-dioxaborolan-2-yl)benzofuran-5-yl)methoxy)phenyl)acetate (428a) (939 mg, 84% yield) as a light brown oil. H NMR (300 MHz, DMSO-d$_6$) δ 8.05 (d, J=2.2 Hz, 1H), 7.81 (d, J=1.8 Hz, 1H), 7.64 (d, J=1.9 Hz, 1H), 6.96 (d, J=2.2 Hz, 1H), 6.94 (s, 1H), 6.92 (s, 1H), 5.11 (s, 2H), 4.07-3.94 (m, 2H), 3.50 (s, 2H), 2.19 (s, 3H), 2.13 (s, 3H), 1.34 (s, 12H), 1.05 (t, J=7.1 Hz, 3H); MS: (ES+): 487.20 (M+Na).

Step-2: Preparation of Ethyl 2-(2-((7-(2-(aminomethyl)pyridin-4-yl)benzofuran-5-yl)methoxy)-4,5-dimethylphenyl)acetate (428b)

Compound 428b was prepared according to the procedure reported in step-3 of scheme-1 from ethyl 2-(4,5-dimethyl-2-((7-(4,4,5,5-tetramethyl-1,3,2-dioxaborolan-2-yl)benzofuran-5-yl)methoxy)phenyl)acetate (428a) (450 mg, 0.969 mmol) in dioxane (10 mL) using (4-chloropyridin-2-yl)methanamine (74a) (138 mg, 0.969 mmol), K$_2$CO$_3$ (402 mg, 2.91 mmol) in water (1 mL) and bis(triphenylphosphine)palladium(II)chloride (102 mg, 0.145 mmol) under a nitrogen atmosphere and heating at 100° C. for 16 h on oil bath. This gave after workup, purification by flash column chromatography [silica gel, eluting with ethyl acetate in hexanes (0 to 100%) then dichloromethane/DMA 80 (0 to 25%)] ethyl 2-(2-((7-(2-(aminomethyl)pyridin-4-yl)benzofuran-5-yl)methoxy)-4,5-dimethylphenyl)acetate (428b) (50 mg, 12% yield). $^1$H NMR (300 MHz, DMSO-d$_6$) δ 8.62 (d, J=5.2 Hz, 1H), 8.14 (d, J=2.2 Hz, 1H), 7.97 (s, 1H), 7.79 (d, J=1.6 Hz, 1H), 7.78-7.71 (m, 2H), 7.09 (d, J=2.2 Hz, 1H), 6.96 (s, 1H), 6.94 (s, 1H), 5.21 (s, 2H), 4.00-3.85 (m, 4H), 3.55 (s, 2H), 2.20 (s, 3H), 2.13 (s, 3H), 0.99 (t, J=7.1 Hz, 3H); MS (ES+): 445.15 (M+1)

Step-3: Preparation of 2-(2-((7-(2-(aminomethyl)pyridin-4-yl)benzofuran-5-yl)methoxy)-4,5-dimethylphenyl)acetic Acid (428c)

Compound 428c was prepared according to the procedure reported in step-6 of scheme-1 from ethyl 2-(2-((7-(2-(aminomethyl)pyridin-4-yl)benzofuran-5-yl)methoxy)-4,5-dimethylphenyl)acetate (428b) (45 mg, 0.101 mmol) in THF/methanol (5 mL each) using a solution of lithium hydroxide hydrate (26.0 mg, 0.607 mmol) in water (5 mL) and stirring at room temperature for 16 h. This gave after workup and purification by reverse-phase column chromatography [C-18 column, eluting with water (containing 0.1% HCl)/acetonitrile (1:0 to 0:1)] 2-(2-((7-(2-(aminomethyl)pyridin-4-yl)benzofuran-5-yl)methoxy)-4,5-dimethylphenyl)acetic acid (428c) (21 mg, 50%) HCl salt as a white solid; $^1$H NMR (300 MHz, DMSO-d$_6$, D$_2$O exchange) δ 8.75 (dd, J=5.3, 0.8 Hz, 1H), 8.09 (d, J=2.2 Hz, 1H), 8.03-7.98 (m, 1H), 7.96 (dd, J=5.3, 1.8 Hz, 1H), 7.84 (d, J=1.6 Hz, 1H), 7.76 (d, J=1.6 Hz, 1H), 7.08 (d, J=2.2 Hz, 1H), 6.94 (s, 1H), 6.90 (s, 1H), 5.20 (s, 2H), 4.29 (s, 2H), 3.49 (s, 2H), 2.16 (s, 3H), 2.10 (s, 3H); MS (ES+): 417.15 (M+1); MS (ES−): 415.20 (M−1).

Scheme-429

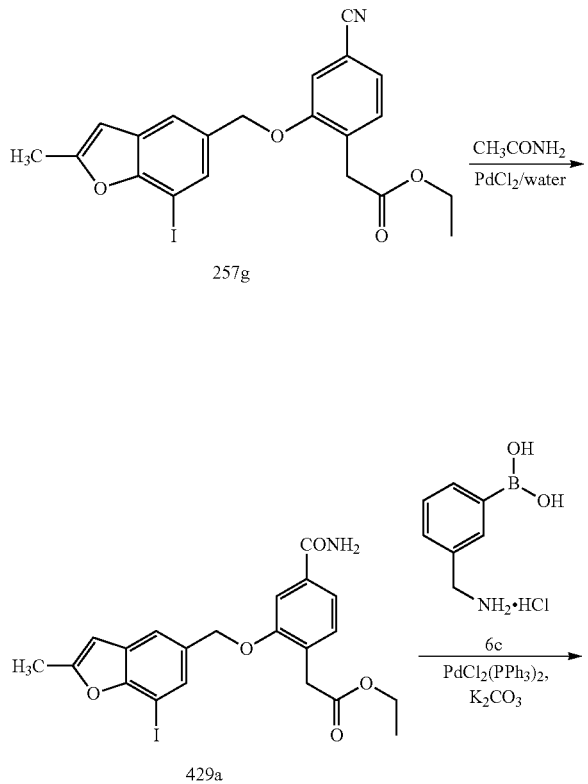

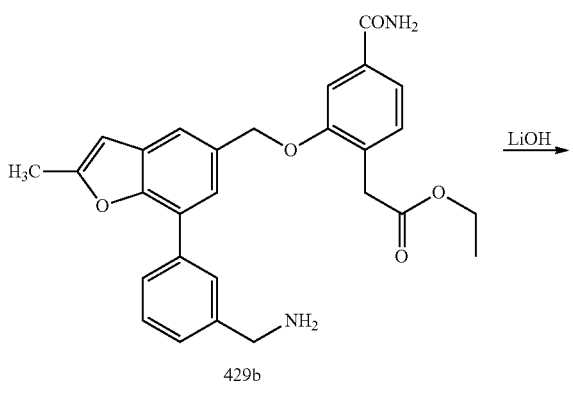

429b

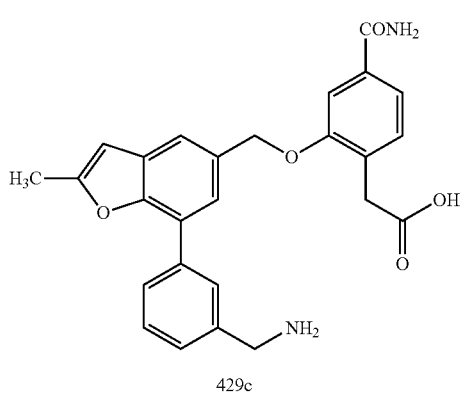

429c

Preparation of 2-(2-((7-(3-(aminomethyl)phenyl)-2-methylbenzofuran-5-yl)methoxy)-4-carbamoylphenyl)acetic Acid (429c)

Step-1: Preparation of Ethyl 2-(4-carbamoyl-2-((7-iodo-2-methylbenzofuran-5-yl)methoxy)phenyl)acetate (429a)

Compound 429a was prepared according to the procedure reported in step-1 of scheme-238 from ethyl 2-(4-cyano-2-((7-iodo-2-methylbenzofuran-5-yl)methoxy)phenyl)acetate (257g) (500 mg, 1.052 mmol) in THF (20 mL) and water (1.5 mL), using acetamide (373 mg, 6.31 mmol), palladium (II) chloride (56.0 mg, 0.316 mmol) and stirring at room temperature for 16 h. This gave after workup and purification by flash column chromatography (silica gel, 24 g, eluting with methanol in DCM from 0 to 6%] ethyl 2-(4-carbamoyl-2-((7-iodo-2-methylbenzofuran-5-yl)methoxy)phenyl)acetate (429a) (468 mg, 90% yield) as an off-white solid. $^1$H NMR (300 MHz, DMSO-$d_6$) δ 7.98 (s, 1H), 7.65 (d, J=1.5 Hz, 1H), 7.60-7.53 (m, 2H), 7.45 (dd, J=7.7, 1.5 Hz, 1H), 7.39 (s, 1H), 7.29 (d, J=7.8 Hz, 1H), 6.75 (d, J=1.2 Hz, 1H), 5.17 (s, 2H), 4.02 (q, J=7.1 Hz, 2H), 3.66 (s, 2H), 2.48 (d, 3H), 1.08 (t, J=7.1 Hz, 3H); MS: 516.00 (M+Na).

Step-2: Preparation of Ethyl 2-(2-((7-(3-(aminomethyl)phenyl)-2-methylbenzofuran-5-yl)methoxy)-4-carbamoylphenyl)acetate (429b)

Compound 429b was prepared according to the procedure reported in step-3 of scheme-1 from ethyl 2-(4-carbamoyl-2-((7-iodo-2-methylbenzofuran-5-yl)methoxy)phenyl)acetate (429a) (450 mg, 0.912 mmol) in dioxane (20 mL) using 3-(aminomethyl)phenylboronic acid hydrochloride (6c) (256 mg, 1.368 mmol), $K_2CO_3$ (378 mg, 2.74 mmol) in water (4 mL) and bis(triphenylphosphine)palladium(II)chloride (96 mg, 0.137 mmol) under a nitrogen atmosphere and heating at 100° C. for 3 h on oil bath. This gave after workup, purification by flash column chromatography (silica gel, 24 g, eluting with 0 to 10% methanol in dichloromethane) ethyl 2-(2-((7-(3-(aminomethyl)phenyl)-2-methylbenzofuran-5-yl)methoxy)-4-carbamoylphenyl)acetate (429b) (262 mg, 61% yield). $^1$H NMR (300 MHz, DMSO-$d_6$) δ 7.99 (s, 1H), 7.81-7.78 (m, 1H), 7.75-7.70 (m, 1H), 7.62 (d, J=1.6 Hz, 1H), 7.56 (d, J=1.6 Hz, 1H), 7.51-7.35 (m, 5H), 7.29 (d, J=7.8 Hz, 1H), 6.66 (d, J=1.2 Hz, 1H), 5.26 (s, 2H), 3.93 (q, J=7.1 Hz, 2H), 3.84 (s, 2H), 3.67 (s, 2H), 2.48 (d, J=1.1 Hz, 3H), 0.98 (t, J=7.1 Hz, 3H); MS: 473.20 (M+1).

Step-3: Preparation of 2-(2-((7-(3-(aminomethyl)phenyl)-2-methylbenzofuran-5-yl)methoxy)-4-carbamoylphenyl)acetic Acid (429c)

Compound 429c was prepared according to the procedure reported in step-6 of scheme-1 from ethyl 2-(2-((7-(3-(aminomethyl)phenyl)-2-methylbenzofuran-5-yl)methoxy)-4-carbamoylphenyl)acetate (429b) (250 mg, 0.529 mmol) in THF/MeOH (10 mL, each) using a solution of lithium hydroxide hydrate (136 mg, 3.17 mmol) in water (10 mL) and stirring for 16 h. This gave after workup and purification by reverse phase column chromatography [C18 column chromatography with water (containing 0.1% HCl)/acetonitrile (1:0 to 0:1)] 2-(2-((7-(3-(aminomethyl)phenyl)-2-methylbenzofuran-5-yl)methoxy)-4-carbamoylphenyl)acetic acid (429c) (151 mg, 64%) HCl salt as a white solid; $^1$H NMR (300 MHz, DMSO-$d_6$, $D_2O$ exchange) δ 7.94-7.87 (m, 2H), 7.61-7.55 (m, 3H), 7.53-7.47 (m, 2H), 7.42 (dd, J=7.7, 1.5 Hz, 1H), 7.28 (d, J=7.8 Hz, 1H), 6.65 (d, J=1.3 Hz, 1H), 5.27 (s, 2H), 4.12 (s, 2H), 3.62 (s, 2H), 2.46 (d, J=1.0 Hz, 3H); MS (ES+): 445.15 (M+1); Analysis calculated for $C_{26}H_{24}N_2O_5 \cdot 1.45HCl \cdot 1.5H_2O$: C, 59.55; H, 5.47; Cl, 9.80; N, 5.34; Found: C, 59.42; H, 5.53; Cl, 9.59; N, 5.37.

Scheme-430

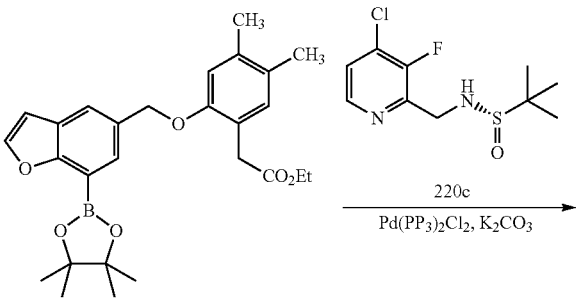

428a

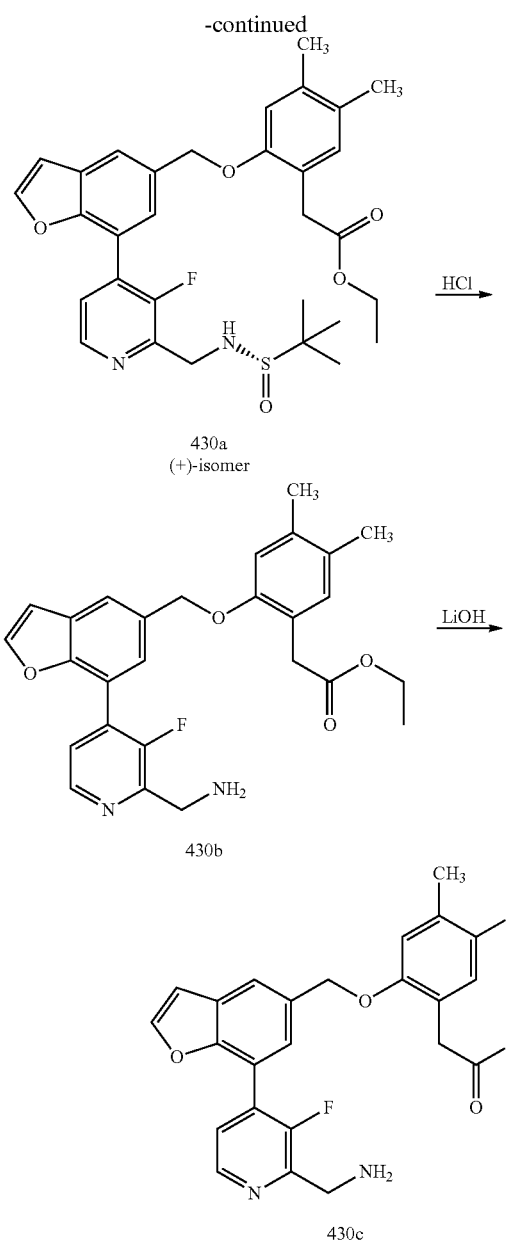

430a
(+)-isomer

430b

430c

Preparation of 2-(2-((7-(2-(aminomethyl)-3-fluoropyridin-4-yl)benzofuran-5-yl)methoxy)-4,5-dimethylphenyl)acetic Acid (430c)

Step-1: Preparation of (+)-(S)-ethyl 2-(2-((7-(2-((1,1-dimethylethylsulfinamido)methyl)-3-fluoropyridin-4-yl)benzofuran-5-yl)methoxy)-4,5-dimethylphenyl)acetate (430a)

Compound 430a was prepared according to the procedure reported in step-3 of scheme-1 from ethyl 2-(4,5-dimethyl-2-((7-(4,4,5,5-tetramethyl-1,3,2-dioxaborolan-2-yl)benzofuran-5-yl)methoxy)phenyl)acetate (428a) (430 mg, 0.926 mmol) in dioxane (15 mL) using (+)-(S)—N-((4-chloro-3-fluoropyridin-2-yl)methyl)-2-methylpropane-2-sulfinamide (220c) (294 mg, 1.111 mmol), bis(triphenylphosphine)palladium(II) chloride (Pd(PPh$_3$)$_2$Cl$_2$) (97 mg, 0.139 mmol)

and a solution of K$_2$CO$_3$ (384 mg, 2.78 mmol) in water (1.2 mL) under an N$_2$ atmosphere heating at 100° C. for 16 h on oil bath. This gave after workup, purification by flash column chromatography (silica gel, 40g, eluting with 0 to 3% methanol in DCM) (+)-(S)-ethyl 2-(2-((7-(2-((1,1-dimethylethylsulfinamido)methyl)-3-fluoropyridin-4-yl)benzofuran-5-yl)methoxy)-4,5-dimethylphenyl)acetate (430a) (448 mg, 85% yield); MS: 567.30 (M+1); Optical rotation [t]D=+36.667 (c=0.06, MeOH).

Step-2: Preparation of Ethyl 2-(2-((7-(2-(aminomethyl)-3-fluoropyridin-4-yl)benzofuran-5-yl)methoxy)-4,5-dimethylphenyl)acetate (430b)

To a solution of (+)-(S)-ethyl 2-(2-((7-(2-((1,1-dimethylethylsulfinamido)methyl)-3-fluoropyridin-4-yl)benzofuran-5-yl)methoxy)-4,5-dimethylphenyl)acetate (430a) (420 mg, 0.741 mmol) in tetrahydrofuran (15 mL) was added conc HCl (0.741 mL, 2.223 mmol) at room temperature and stirred for 2 h. The reaction mixture was concentrated to dryness to give ethyl 2-(2-((7-(2-(aminomethyl)-3-fluoropyridin-4-yl)benzofuran-5-yl)methoxy)-4,5-dimethylphenyl)acetate (430b); MS (ES+): 463.20 (M+1).

Step-3: Preparation of 2-(2-((7-(2-(aminomethyl)-3-fluoropyridin-4-yl)benzofuran-5-yl)methoxy)-4,5-dimethylphenyl)acetic Acid (430c)

Compound 430c was prepared according to the procedure reported in step-6 of scheme-1 from ethyl 2-(2-((7-(2-(aminomethyl)-3-fluoropyridin-4-yl)benzofuran-5-yl)methoxy)-4,5-dimethylphenyl)acetate (430b) (0.741 mmol, from above step-2) in MeOH/THF (7 mL, each) using a solution of lithium hydroxide hydrate (254 mg, 5.93 mmol) in water (7 mL). This gave after workup and purification by reverse phase column (C18, eluting with (1:0 to 0:1) MeCN in H$_2$O containing 0.1% HCl) 2-(2-((7-(2-(aminomethyl)-3-fluoropyridin-4-yl)benzofuran-5-yl)methoxy)-4,5-dimethylphenyl)acetic acid (430c) (83 mg, 26%) HCl salt as a white solid; $^1$H NMR (300 MHz, DMSO-d$_6$) δ 12.14 (s, 1H), 8.63 (d, J=5.0 Hz, 1H), 8.61-8.51 (m, 3H), 8.11 (d, J=2.2 Hz, 1H), 7.90 (d, J=1.6 Hz, 1H), 7.80 (t, J=5.3 Hz, 1H), 7.60 (d, J=1.4 Hz, 1H), 7.10 (d, J=2.2 Hz, 1H), 6.95 (s, 1H), 6.92 (s, 1H), 5.22 (s, 2H), 4.44-4.31 (m, 2H), 3.49 (s, 2H), 2.19 (s, 3H), 2.12 (s, 3H); $^{19}$F NMR (282 MHz, DMSO-d$_6$) δ–128.43; MS (ES+): 435.20 (M+1); MS (ES–): 433.10 (M–1); Analysis calculated for C$_{25}$H$_{23}$FN$_2$O$_4$.HCl.1.25H$_2$O: C, 60.85; H, 5.41; N, 5.68; Cl, 7.18; Found: C, 60.63; H, 5.15; N, 5.65; Cl, 6.94.

Scheme-431

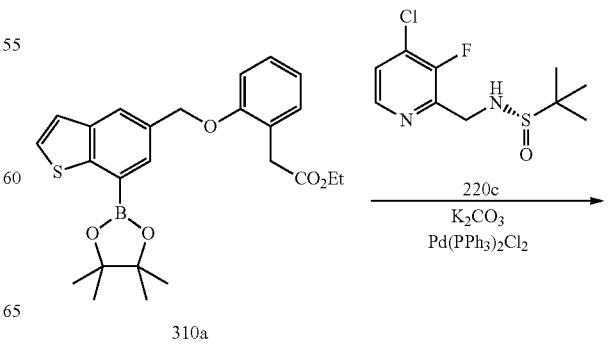

310a

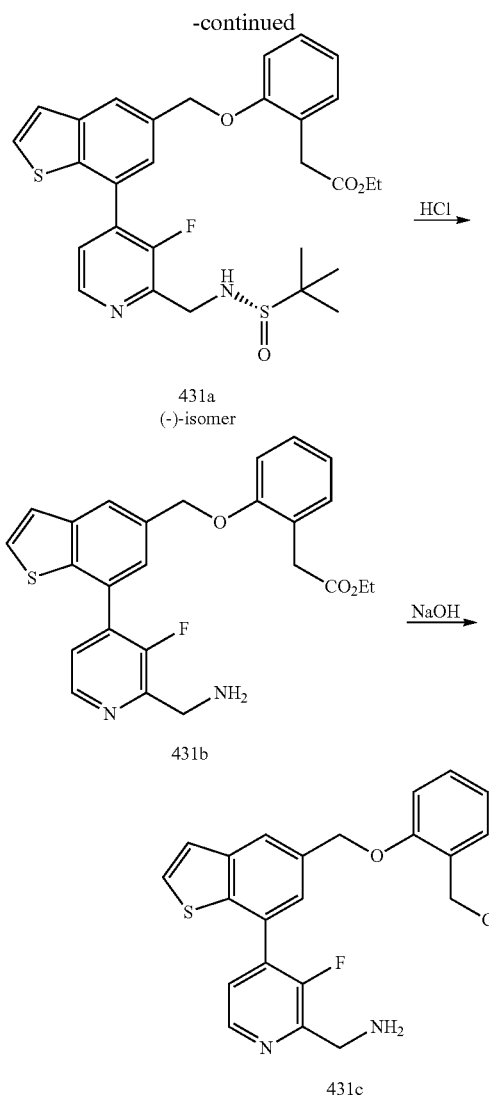

431a
(−)-isomer

431b

431c

Preparation of 2-(2-((7-(2-(aminomethyl)-3-fluoropyridin-4-yl)benzo[b]thiophen-5-yl)methoxy)phenyl)acetic Acid (431c)

Step-1: Preparation of (−)-(S)-ethyl 2-(2-((7-(2-((1,1-dimethylethylsulfinamido)methyl)-3-fluoropyridin-4-yl)benzo[b]thiophen-5-yl)methoxy)phenyl)acetate (431a)

Compound 431a was prepared according to the procedure reported in step-3 of scheme-1 from ethyl 2-(2-((7-(4,4,5,5-tetramethyl-1,3,2-dioxaborolan-2-yl)benzo[b]thiophen-5-yl)methoxy)phenyl)acetate (310a) (100 mg, 0.221 mmol) in dioxane (4 mL) using (+)-(S)—N-((4-chloro-3-fluoropyridin-2-yl)methyl)-2-methylpropane-2-sulfinamide (220c) (64 mg, 0.243 mmol), bis(triphenylphosphine)palladium(II) chloride (Pd(PPh$_3$)$_2$Cl$_2$) (16 mg, 0.022 mmol) and a solution of K$_2$CO$_3$ (92 mg, 0.663 mmol) in water (1.0 mL) under a nitrogen atmosphere heating at 100° C. for 16 h on oil bath. This gave after workup and purification by flash column chromatography [silica gel (12 g), eluting with 0-5% MeOH in DCM] (−)-(S)-ethyl 2-(2-((7-(2-((1,1-dimethylethylsulfinamido)methyl)-3-fluoropyridin-4-yl)benzo[b]thiophen-5-yl)methoxy)phenyl)acetate (431a) as a pale-yellow oil; MS (ES+): 555 (M+1); Optical rotation $[\alpha]_D = -8.00$ (c=0.05, MeOH).

Step-2: Preparation of Ethyl 2-(2-((7-(2-(aminomethyl)-3-fluoropyridin-4-yl)benzo[b]thiophen-5-yl)methoxy)phenyl)acetate (431b)

To a solution of (−)-(S)-ethyl 2-(2-((7-(2-((1,1-dimethylethylsulfinamido)methyl)-3-fluoropyridin-4-yl)benzo[b]thiophen-5-yl)methoxy)phenyl)acetate (431a) (81 mg; from above step-1) in MeOH (2 mL) was added 4 M HCl in dioxane (0.553 mL, 2.211 mmol) at room temperature and stirred for 1 h. The reaction mixture was concentrated to dryness and purified by flash column chromatography (silica gel, 12g, eluting with 0-8% MeOH in DCM) to give ethyl 2-(2-((7-(2-(aminomethyl)-3-fluoropyridin-4-yl)benzo[b]thiophen-5-yl)methoxy)phenyl)acetate (431b) (55 mg) as a pale-yellow oil; MS (ES+): 451.00 (M+1).

Step-3: Preparation of 2-(2-((7-(2-(aminomethyl)-3-fluoropyridin-4-yl)benzo[b]thiophen-5-yl)methoxy)phenyl)acetic Acid (431c)

Compound 431c was prepared according to the procedure reported in step-4 of scheme-4 from ethyl 2-(2-((7-(2-(aminomethyl)-3-fluoropyridin-4-yl)benzo[b]thiophen-5-yl)methoxy)phenyl)acetate (431b) (55 mg, from above step-2) in MeOH (3 mL) water (1 mL) using NaOH (44 mg, 1.105 mmol). This gave after workup and purification by reverse phase column [C18 (100 g), eluting with water in acetonitrile from 0-60%] 2-(2-((7-(2-(aminomethyl)-3-fluoropyridin-4-yl)benzo[b]thiophen-5-yl)methoxy)phenyl)acetic acid (431c) (15 mg, 16% yield) HCl salt as a pale green solid; $^1$H NMR (300 MHz, DMSO-d$_6$) δ 8.66 (d, J=5.0 Hz, 1H), 8.50 (d, J=5.9 Hz, 3H), 8.13 (d, J=1.5 Hz, 1H), 7.90 (d, J=5.5 Hz, 1H), 7.83 (t, J=5.3 Hz, 1H), 7.64-7.54 (m, 2H), 7.29-7.19 (m, 2H), 7.10 (d, J=7.8 Hz, 1H), 6.91 (td, J=7.4, 1.1 Hz, 1H), 5.32 (s, 2H), 4.47-4.33 (m, 2H), 3.59 (s, 2H); MS (ES+): 423 (M+1), (ES−): 422 (M−1).

Scheme-432

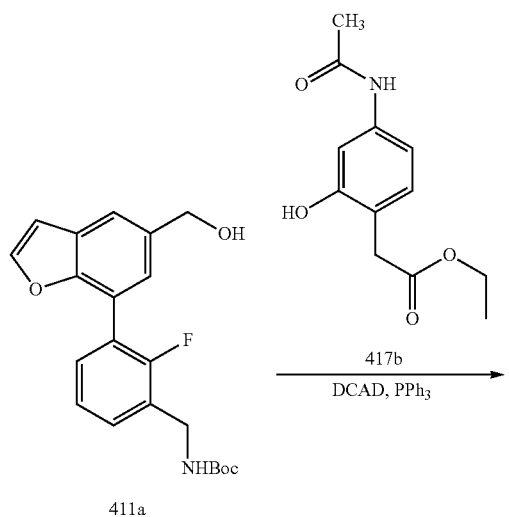

411a 417b
DCAD, PPh$_3$

1329

-continued

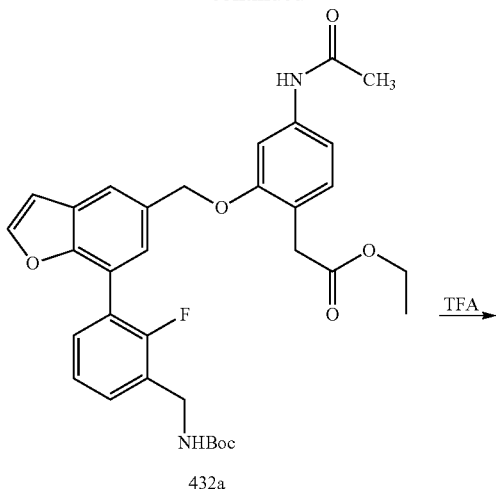
432a

↓ TFA

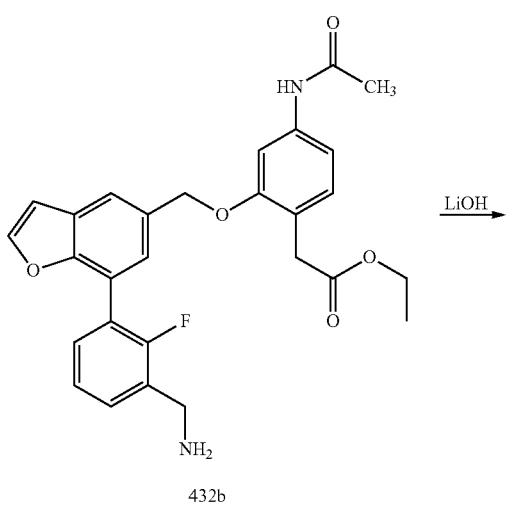
432b

↓ LiOH

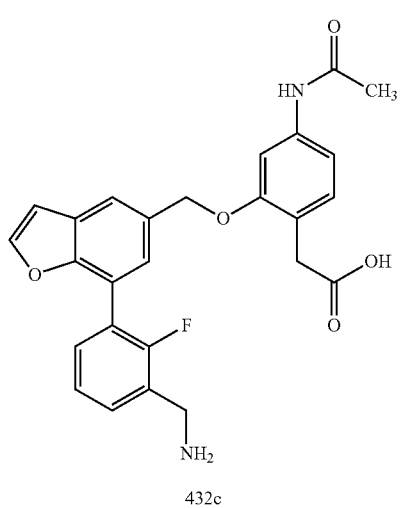 [SMILES: CC(=O)Nc1ccc(CC(=O)O)c(OCc2cc(-c3cccc(CN)c3F)c3occc3c2)c1]
432c

1330

Preparation of 2-(4-acetamido-2-((7-(3-(aminomethyl)-2-fluorophenyl)benzofuran-5-yl)methoxy)phenyl)acetic Acid (432c)

Step-1: Preparation of Ethyl 2-(4-acetamido-2-((7-(3-(((tert-butoxycarbonyl)amino)methyl)-2-fluorophenyl)benzofuran-5-yl)methoxy)phenyl)acetate (432a)

Compound 432a was prepared according to the procedure reported in step-2 of scheme-23 from tert-butyl 2-fluoro-3-(5-(hydroxymethyl)benzofuran-7-yl)benzylcarbamate (411a) (352 mg, 0.948 mmol) in DCM (8 mL) using triphenylphosphine (249 mg, 0.948 mmol), ethyl 2-(4-acetamido-2-hydroxyphenyl)acetate (417b) (150 mg, 0.632 mmol) and (E)-bis(4-chlorobenzyl) diazene-1,2-dicarboxylate (DCAD, 348 mg, 0.948 mmol) in DCM (8 mL). This gave after workup and purification by flash column chromatography [silica gel, eluting with hexanes/ethyl acetate (1:0 to 2:1), then hexanes/10% methanol in ethyl acetate (1:1)] ethyl 2-(4-acetamido-2-((7-(3-(((tert-butoxycarbonyl)amino)methyl)-2-fluorophenyl)benzofuran-5-yl)methoxy)phenyl)acetate (432a) (309 mg) as a light brown gum; MS (ES+): 613.20 (M+1).

Step-2: Preparation of Ethyl 2-(4-acetamido-2-((7-(3-(aminomethyl)-2-fluorophenyl)benzofuran-5-yl)methoxy)phenyl)acetate (432b)

Compound 432b was prepared according to the procedure reported in step-5 of scheme-1 from ethyl 2-(4-acetamido-2-((7-(3-(((tert-butoxycarbonyl)amino)methyl)-2-fluorophenyl)benzofuran-5-yl)methoxy)phenyl)acetate (432a) (290 mg, 0.491 mmol) in DCM (15 mL) using TFA (0.729 mL, 9.82 mmol). This gave after workup ethyl 2-(4-acetamido-2-((7-(3-(aminomethyl)-2-fluorophenyl)benzofuran-5-yl)methoxy)phenyl)acetate (432b) which was used as such for next step. MS (ES+): 491.20 (M+1).

Step-3: Preparation of 2-(4-acetamido-2-((7-(3-(aminomethyl)-2-fluorophenyl)benzofuran-5-yl)methoxy)phenyl)acetic Acid (432c)

Compound 432c was prepared according to the procedure reported in step-6 of scheme-1 from ethyl 2-(4-acetamido-2-((7-(3-(aminomethyl)-2-fluorophenyl)benzofuran-5-yl)methoxy)phenyl)acetate (432b) (0.491 mmol; from above step-2) in THF/MeOH (10 mL each) using a solution of lithium hydroxide hydrate (0.168 g, 3.93 mmol) in water (10 mL) and stirring for 21 h. This gave after workup and purification by reverse phase column chromatography [C-18, eluting with water (containing 0.1% HCl)/acetonitrile (1:0 to 0:1)] 2-(4-acetamido-2-((7-(3-(aminomethyl)-2-fluorophenyl)benzofuran-5-yl)methoxy)phenyl)acetic acid (432c) (45 mg, 17%) HCl salt as an off-white solid; $^1$H NMR (300 MHz, DMSO-$d_6$) δ 12.17 (s, 1H), 9.99 (s, 1H), 8.46 (s, 3H), 8.06 (d, J=2.2 Hz, 1H), 7.82 (d, J=1.7 Hz, 1H), 7.74-7.63 (m, 2H), 7.49 (d, J=1.8 Hz, 1H), 7.48-7.38 (m, 2H), 7.14-7.02 (m, 3H), 5.19 (s, 2H), 4.25-4.07 (m, 2H), 3.51 (s, 2H), 2.03 (s, 3H); $^{19}$F NMR (282 MHz, DMSO-$d_6$) δ −118.20; MS (ES+): 463.10 (M+1); MS (ES−): 461.15 (M−1); Analysis calculated for $C_{26}H_{23}FN_2O_5 \cdot HCl \cdot 2.25H_2O$: C, 57.89; H, 5.32; N, 5.19; Cl, 6.57; Found: C, 57.81; H, 5.27; N, 5.07; Cl, 6.30.

Scheme-433

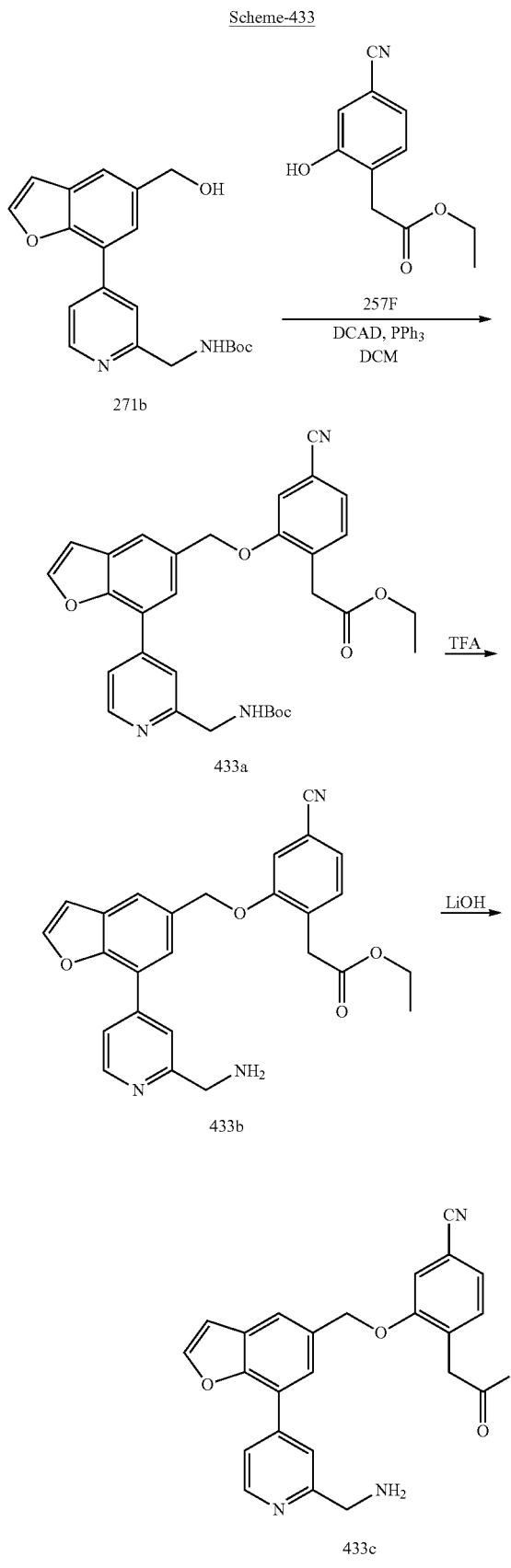

Preparation of 2-(2-((7-(2-(aminomethyl)pyridin-4-yl)benzofuran-5-yl)methoxy)-4-cyanophenyl)acetic Acid (433c)

Step-1: Preparation of Ethyl 2-(2-((7-(2-(((tert-butoxycarbonyl)amino)methyl)pyridin-4-yl)benzofuran-5-yl)methoxy)-4-cyanophenyl)acetate (433a)

Compound 433a was prepared according to the procedure reported in step-2 of scheme-23 from tert-butyl ((4-(5-(hydroxymethyl)benzofuran-7-yl)pyridin-2-yl)methyl)carbamate (271b) (518 mg, 1.462 mmol) in DCM (15 mL) using triphenylphosphine (575 mg, 2.193 mmol), ethyl 2-(4-cyano-2-hydroxyphenyl)acetate (257f) (300 mg, 1.462 mmol) and a solution of (E)-bis(4-chlorobenzyl) diazene-1,2-dicarboxylate (DCAD, 805 mg, 2.193 mmol) in DCM (15 mL). This gave after workup and purification by flash column chromatography [silica gel, eluting with hexanes/ethyl acetate (1:0 to 1:1)] ethyl 2-(2-((7-(2-(((tert-butoxycarbonyl)amino)methyl)pyridin-4-yl)benzofuran-5-yl)methoxy)-4-cyanophenyl)acetate (433a) (332 mg, 42%) as a light pink gum; $^1$H NMR (300 MHz, DMSO-$d_6$) δ 8.65-8.62 (m, 1H), 8.13 (d, J=2.2 Hz, 1H), 7.85-7.78 (m, 2H), 7.77-7.74 (m, 1H), 7.69-7.68 (m, 1H), 7.64-7.63 (m, 1H), 7.56-7.35 (m, 3H), 7.12 (d, J=2.2 Hz, 1H), 5.32 (s, 2H), 4.32 (d, J=6.1 Hz, 2H), 3.89 (q, J=7.1 Hz, 2H), 3.72 (s, 2H), 1.39 (s, 9H), 0.91 (t, J=7.1 Hz, 3H); MS (ES+): 542.20 (M+1).

Step-2: Preparation of Ethyl 2-(2-((7-(2-(aminomethyl)pyridin-4-yl)benzofuran-5-yl)methoxy)-4-cyanophenyl)acetate (433b)

Compound 433b was prepared according to the procedure reported in step-5 of scheme-1 from ethyl 2-(2-((7-(2-(((tert-butoxycarbonyl)amino)methyl)pyridin-4-yl)benzofuran-5-yl)methoxy)-4-cyanophenyl)acetate (433a) (110 mg, 0.203 mmol) in DCM (10 mL) using TFA (0.302 mL, 4.06 mmol). This gave after workup ethyl 2-(2-((7-(2-(aminomethyl)pyridin-4-yl)benzofuran-5-yl)methoxy)-4-cyanophenyl)acetate (433b) which was used as such for next step; MS (ES+): 442.20 (M+1).

Step-3: Preparation of 2-(2-((7-(2-(aminomethyl)pyridin-4-yl)benzofuran-5-yl)methoxy)-4-cyanophenyl)acetic Acid (433c)

Compound 433c was prepared according to the procedure reported in step-6 of scheme-1 from ethyl 2-(2-((7-(2-(aminomethyl)pyridin-4-yl)benzofuran-5-yl)methoxy)-4-cyanophenyl)acetate (433b) (0.203 mmol; from above step-2) in MeOH/THF (5 mL each) using a solution of lithium hydroxide hydrate (0.070 g, 1.624 mmol) in water (6 mL) and stirring at room temperature for 19 h. This gave after workup and purification by reverse phase column [C-18 column eluting with water (containing 0.1% HCl)/acetonitrile (1:0 to 0:1)] 2-(2-((7-(2-(aminomethyl)pyridin-4-yl)benzofuran-5-yl)methoxy)-4-cyanophenyl)acetic acid (433c) (51 mg, 61%) HCl salt as an off-white solid; $^1$H NMR (300 MHz, DMSO-$d_6$) δ 8.80-8.77 (m, 1H), 8.43 (s, 3H), 8.18 (d, J=2.2 Hz, 1H), 8.08-8.03 (m, 1H), 7.98 (dd, J=5.3, 1.7 Hz, 1H), 7.87 (d, J=1.6 Hz, 1H), 7.80 (d, J=1.7 Hz, 1H), 7.60 (d, J=1.4 Hz, 1H), 7.49-7.39 (m, 2H), 7.13 (d, J=2.2 Hz, 1H), 5.37 (s, 2H), 4.39-4.24 (m, 2H), 3.70 (s, 2H); MS (ES+): 414.10 (M+1); Analysis calculated for $C_{24}H_{19}N_3O_4 \cdot 1.75HCl \cdot 2.5H_2O$: C, 55.19; H, 4.97; N, 8.05; Cl, 11.88; Found: C, 54.88; H, 4.67; N, 7.91; Cl, 11.92.

Scheme-434

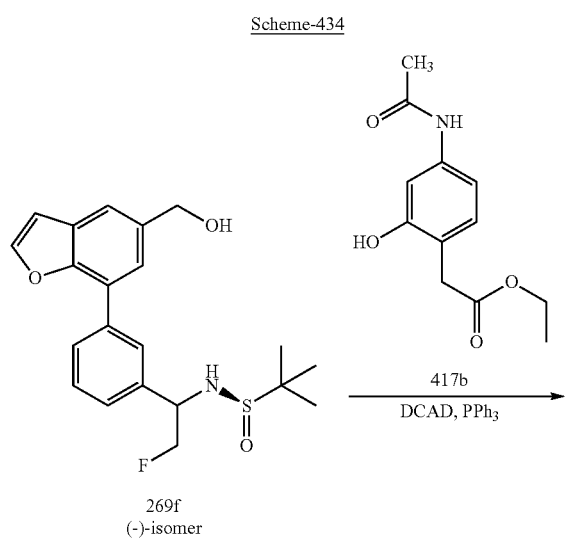

269f
(−)-isomer

417b
DCAD, PPh₃ →

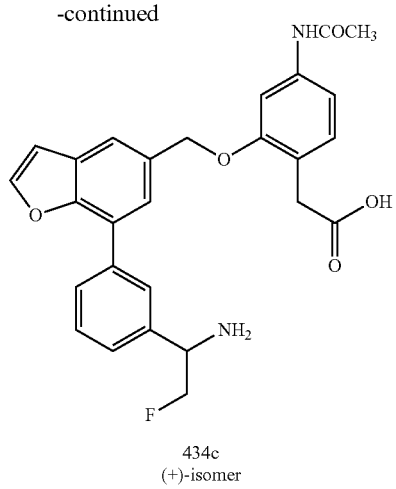

434c
(+)-isomer

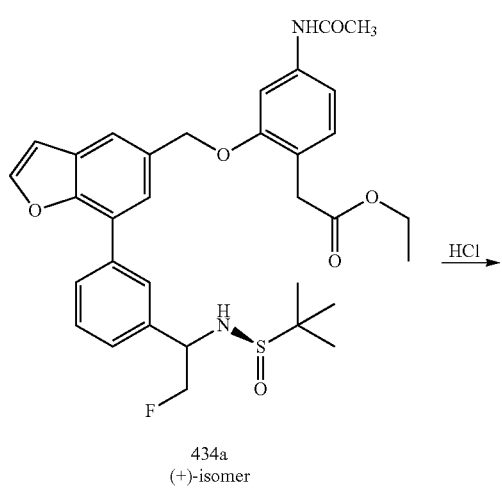

434a
(+)-isomer

HCl →

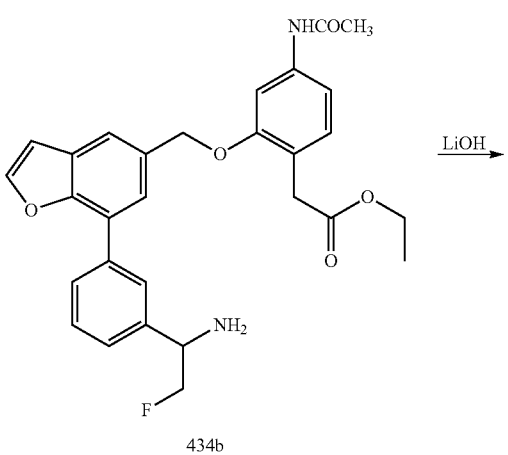

434b

LiOH →

Preparation of (+)-2-(4-acetamido-2-((7-(3-(1-amino-2-fluoroethyl)phenyl)benzofuran-5-yl)methoxy)phenyl)acetic Acid (434c)

Step-1: Preparation of (+)-ethyl 2-(4-acetamido-2-((7-(3-(1-((R)-1,1-dimethylethylsulfinamido)-2-fluoroethyl)phenyl)benzofuran-5-yl)methoxy)phenyl)acetate (434a)

Compound 434a was prepared according to the procedure reported in step-2 of scheme-23 from (−)-(R)—N-(2-fluoro-1-(3-(5-(hydroxymethyl)benzofuran-7-yl)phenyl)ethyl)-2-methylpropane-2-sulfinamide (269f) (260 mg, 0.668 mmol) in DCM (8 mL) using triphenylphosphine (219 mg, 0.835 mmol), ethyl 2-(4-acetamido-2-hydroxyphenyl)acetate (417b) (132 mg, 0.556 mmol) and a solution of (E)-bis(4-chlorobenzyl) diazene-1,2-dicarboxylate (DCAD, 306 mg, 0.835 mmol) in DCM (8 mL). This gave after workup and purification by flash column chromatography [silica gel, 25 g, eluting with hexanes/ethyl acetate (1:0 to 2:1), then hexanes/10% methanol in ethyl acetate (1:1)] (+)-ethyl 2-(4-acetamido-2-((7-(3-(1-((R)-1,1-dimethylethylsulfinamido)-2-fluoroethyl)phenyl)benzofuran-5-yl)methoxy)phenyl)acetate (434a) (150 mg, 44%) as a light yellow solid; $^1$H NMR (300 MHz, DMSO-$d_6$) δ 9.95 (s, 1H), 8.10 (d, J=2.2 Hz, 1H), 7.94 (s, 1H), 7.87–7.80 (m, 1H), 7.71 (d, J=1.6 Hz, 1H), 7.60 (d, J=1.7 Hz, 1H), 7.56–7.47 (m, 3H), 7.14–7.07 (m, 2H), 7.06 (d, J=2.2 Hz, 1H), 6.04 (d, J=8.2 Hz, 1H), 5.18 (s, 2H), 4.79–4.47 (m, 3H), 3.91 (q, J=7.1 Hz, 2H), 3.56 (s, 2H), 2.03 (s, 3H), 1.14 (s, 9H), 0.97 (t, J=7.1 Hz, 3H); $^{19}$F NMR (282 MHz, DMSO-$d_6$) δ −216.97; MS (ES+): 609.20 (M+1); Optical rotation $[\alpha]_D$=+1.9 (c=0.21, MeOH).

Step-2: Preparation of Ethyl 2-(4-acetamido-2-((7-(3-(1-amino-2-fluoroethyl)phenyl)benzofuran-5-yl)methoxy)phenyl)acetate (434b)

Compound 434b was prepared according to the procedure reported in step-4 of scheme-405 from (+)-ethyl 2-(4-acetamido-2-((7-(3-(1-((R)-1,1-dimethylethylsulfinamido)-2-fluoroethyl)phenyl)benzofuran-5-yl)methoxy)phenyl)acetate (434a) (140 mg, 0.230 mmol) in THF (7 mL) using 3 N aqueous HCl (0.230 mL, 0.690 mmol) and stirring at room temperature for 3 h. This gave after workup ethyl 2-(4-acetamido-2-((7-(3-(1-amino-2-fluoroethyl)phenyl)benzofuran-5-yl)methoxy)phenyl)acetate (434b) which was used as such for next step. MS (ES+): 505.20 (M+1).

Step-3: Preparation of (+)-2-(4-acetamido-2-((7-(3-(1-amino-2-fluoroethyl)phenyl)benzofuran-5-yl)methoxy)phenyl)acetic Acid (434c)

Compound 434c was prepared according to the procedure reported in step-6 of scheme-1 from ethyl 2-(4-acetamido-2-((7-(3-(1-amino-2-fluoroethyl)phenyl)benzofuran-5-yl)methoxy)phenyl)acetate (434b) (0.23 mmol; from above step-2) in MeOH/THF (5 mL each) using a solution of lithium hydroxide hydrate (0.079 g, 1.840 mmol) in water (5 mL) and stirring at room temperature for 19 h. This gave after workup and purification by reverse phase column [C18 column, eluting with water (containing 0.1% HCl)/acetonitrile (1:0 to 0:1)] (+)-2-(4-acetamido-2-((7-(3-(1-amino-2-fluoroethyl)phenyl)benzofuran-5-yl)methoxy)phenyl)acetic acid (434c) (38 mg, 35%) HCl salt as a white solid; $^1$H NMR (300 MHz, DMSO-$d_6$) δ 10.01 (s, 1H), 8.89 (s, 3H), 8.11 (d, J=2.2 Hz, 1H), 8.10-8.05 (m, 1H), 8.00 (dt, J=7.1, 1.8 Hz, 1H), 7.77 (d, J=1.6 Hz, 1H), 7.67-7.60 (m, 3H), 7.53 (d, J=1.9 Hz, 1H), 7.13-7.01 (m, 3H), 5.21 (s, 2H), 4.97-4.66 (m, 3H), 3.53 (s, 2H), 2.03 (s, 3H); $^{19}$F NMR (282 MHz, DMSO-$d_6$) δ−222.45; MS (ES+): 477.15 (M+1); MS (ES−): 475.10 (M−1); Analysis calculated for $C_{27}H_{25}FN_2O_5 \cdot HCl \cdot 2.25H_2O$: C, 58.59; H, 5.55; N, 5.06; Cl, 6.41; Found: C, 58.54; H, 5.51; N, 5.01; Cl, 6.58; Optical rotation [α]$_D$=+11.11 (c=0.27, MeOH).

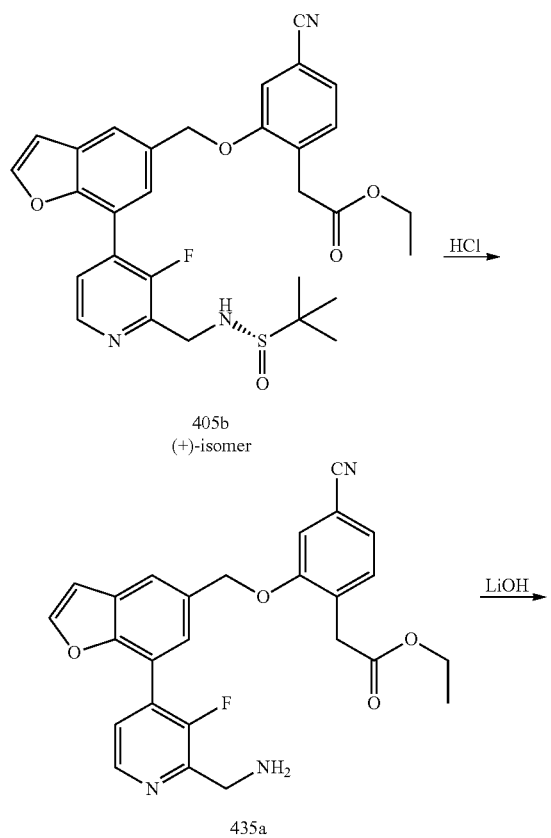

Scheme-435

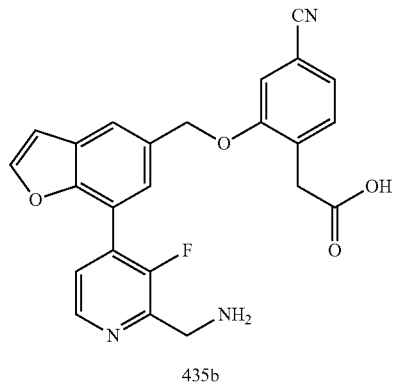

435b

Preparation of 2-(2-((7-(2-(aminomethyl)-3-fluoropyridin-4-yl)benzofuran-5-yl)methoxy)-4-cyanophenyl)acetic Acid (435b)

Step-1: Preparation of Ethyl 2-(2-((7-(2-(aminomethyl)-3-fluoropyridin-4-yl)benzofuran-5-yl)methoxy)-4-cyanophenyl)acetate (435a)

To a solution of (+)-(S)-ethyl 2-(4-cyano-2-((7-(2-((1,1-dimethylethylsulfinamido)methyl)-3-fluoropyridin-4-yl)benzofuran-5-yl)methoxy)phenyl)acetate (405b) (215 mg, 0.381 mmol) in tetrahydrofuran (10 mL) was added 3 N aqueous HCl (0.381 mL, 1.144 mmol) at room temperature and stirred for 5 h. The reaction mixture was concentrated to dryness to give ethyl 2-(2-((7-(2-(aminomethyl)-3-fluoropyridin-4-yl)benzofuran-5-yl)methoxy)-4-cyanophenyl)acetate (435a) which was used as such for next step. MS (ES+): 460.20 (M+1).

Step-2: Preparation of 2-(2-((7-(2-(aminomethyl)-3-fluoropyridin-4-yl)benzofuran-5-yl)methoxy)-4-cyanophenyl)acetic Acid (435b)

Compound 435b was prepared according to the procedure reported in step-6 of scheme-1 from ethyl 2-(2-((7-(2-(aminomethyl)-3-fluoropyridin-4-yl)benzofuran-5-yl)methoxy)-4-cyanophenyl)acetate (435a) (0.381 mmol, from above step-1) in THF/MeOH (8 mL, each) using a solution of lithium hydroxide hydrate (0.131 g, 3.05 mmol) in water (12 mL). This gave after workup and purification by reverse phase column (C18, 100 g, eluting with (1:0 to 0:1) MeCN in H$_2$O containing 0.1% HCl) 2-(2-((7-(2-(aminomethyl)-3-fluoropyridin-4-yl)benzofuran-5-yl)methoxy)-4-cyanophenyl)acetic acid (435b) (112 mg, 68%) HCl salt as a white solid; $^1$H NMR (300 MHz, DMSO-$d_6$) δ 8.63 (d, J=5.0 Hz, 1H), 8.60-8.49 (m, 3H), 8.13 (d, J=2.2 Hz, 1H), 7.91 (d, J=1.6 Hz, 1H), 7.81 (t, J=5.3 Hz, 1H), 7.62-7.59 (m, 2H), 7.48-7.37 (m, 2H), 7.12 (d, J=2.2 Hz, 1H), 5.36 (s, 2H), 4.44-4.30 (m, 2H), 3.68 (s, 2H); $^{19}$F NMR (282 MHz, DMSO-$d_6$) δ−128.40; MS (ES+): 432.10 (M+1); Analysis calculated for $C_{24}H_{18}FN_3O_4 \cdot 1.5 HCl \cdot 2.0H_2O$: C, 55.21; H, 4.54; N, 8.05; Cl, 10.18; Found: C, 54.97; H, 4.33; N, 7.93; Cl, 10.32.

Scheme-436

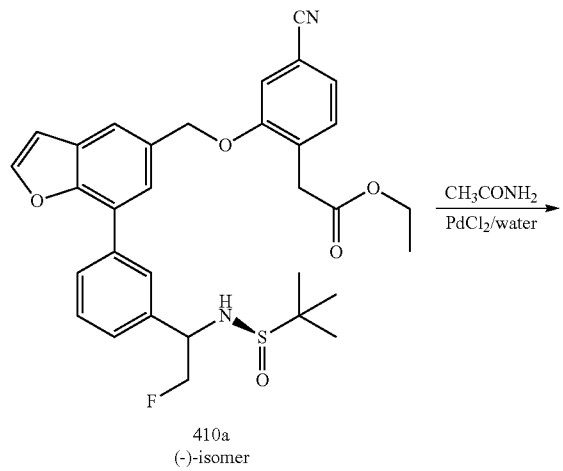

410a
(−)-isomer

→ CH₃CONH₂ / PdCl₂/water

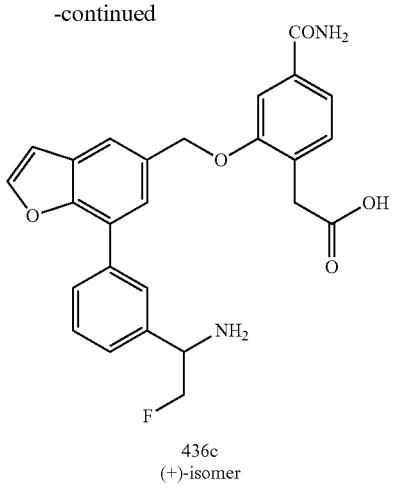

436c
(+)-isomer

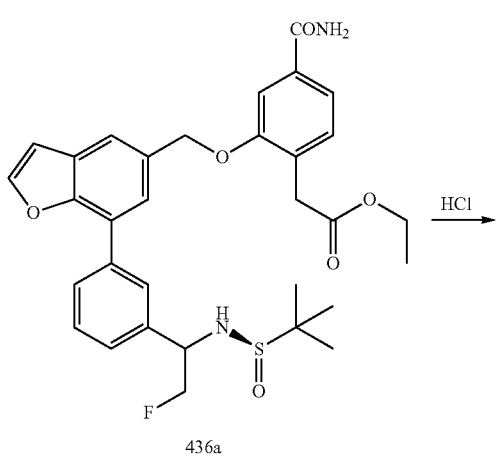

436a

→ HCl

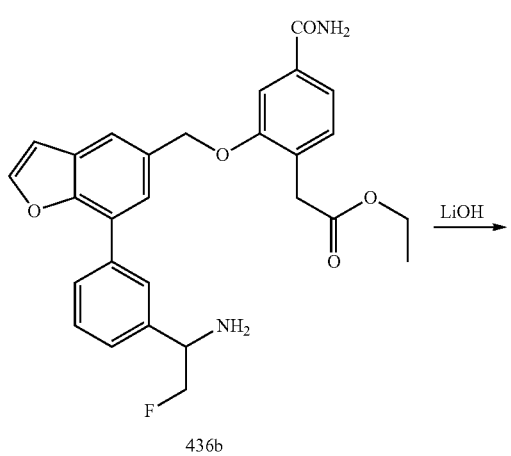

436b

→ LiOH

Preparation of (+)-2-(2-((7-(3-(1-amino-2-fluoro-ethyl)phenyl)benzofuran-5-yl)methoxy)-4-carbamoylphenyl)acetic Acid (436c)

Step-1: Preparation of Ethyl 2-(4-carbamoyl-2-((7-(3-(1-((R)-1,1-dimethylethylsulfinamido)-2-fluoroethyl)phenyl)benzofuran-5-yl)methoxy)phenyl)acetate (436a)

Compound 436a was prepared according to the procedure reported in step-1 of scheme-238 from (−)-ethyl 2-(4-cyano-2-((7-(3-(1-((R)-1,1-dimethylethylsulfinamido)-2-fluoroethyl)phenyl)benzofuran-5-yl)methoxy)phenyl)acetate (410a) (200 mg, 0.347 mmol) in THF (9 mL) and water (0.8 mL), using acetamide (123 mg, 2.081 mmol), palladium(II) chloride (19 mg, 0.104 mmol) and stirring at room temperature for 18 h. This gave after workup and purification by flash column chromatography (silica gel, 12 g, eluting with 9:1 EtOAc/MeOH in hexanes from 0 to 50%) ethyl 2-(4-carbamoyl-2-((7-(3-(1-((R)-1,1-dimethylethylsulfinamido)-2-fluoroethyl)phenyl)benzofuran-5-yl)methoxy)phenyl)acetate (436a) (73 mg, 35%) as a clear oil; $^1$H NMR (300 MHz, DMSO-$d_6$) δ 8.10 (d, J=2.2 Hz, 1H), 8.00 (s, 1H), 7.93 (s, 1H), 7.86-7.81 (m, 1H), 7.74-7.72 (m, 1H), 7.64-7.62 (m, 1H), 7.62-7.60 (m, 1H), 7.54 (s, 1H), 7.52 (s, 1H), 7.48-7.43 (m, 1H), 7.39 (s, 1H), 7.30 (d, J=7.8 Hz, 1H), 7.07 (d, J=2.2 Hz, 1H), 6.05 (d, J=8.2 Hz, 1H), 5.29 (s, 2H), 4.80-4.43 (m, 3H), 3.91 (q, J=7.1 Hz, 2H), 3.68 (s, 2H), 1.13 (s, 9H), 0.95 (t, J=7.1 Hz, 3H); $^{19}$F NMR (282 MHz, DMSO-$d_6$) δ−217.01; MS (ES+): 595.20 (M+1).

Step-2: Preparation of Ethyl 2-(2-((7-(3-(1-amino-2-fluoroethyl)phenyl)benzofuran-5-yl)methoxy)-4-carbamoylphenyl)acetate (436b)

To a solution of ethyl 2-(4-carbamoyl-2-((7-(3-(1-((R)-1,1-dimethylethylsulfinamido)-2-fluoroethyl)phenyl)benzofuran-5-yl)methoxy)phenyl)acetate (436a) (65 mg, 0.109 mmol) in THF (4 mL) was added 3 N aqueous HCl (0.109 mL, 0.328 mmol) at room temperature and stirred for 2 h. The reaction mixture was concentrated to dryness to give ethyl 2-(2-((7-(3-(1-amino-2-fluoroethyl)phenyl)benzofuran-5-yl)methoxy)-4-carbamoylphenyl)acetate (436b) which was used as such for next step. MS (ES+): 491.20 (M+1).

1339

Step-3: Preparation of (+)-2-(2-((7-(3-(1-amino-2-fluoroethyl)phenyl)benzofuran-5-yl)methoxy)-4-carbamoylphenyl)acetic Acid (436c)

Compound 436c was prepared according to the procedure reported in step-6 of scheme-1 from ethyl 2-(2-((7-(3-(1-amino-2-fluoroethyl)phenyl)benzofuran-5-yl)methoxy)-4-carbamoylphenyl)acetate (436b) (0.109 mmol, from above step-2) in THF/MeOH (3 mL, each) using a solution of lithium hydroxide hydrate (37 mg, 0.872 mmol) in water (3 mL). This gave after workup and purification by reverse phase column (C18, 100 g, eluting with (1:0 to 0:1) MeCN in H$_2$O containing 0.1% HCl) (+)-2-(2-((7-(3-(1-amino-2-fluoroethyl)phenyl)benzofuran-5-yl)methoxy)-4-carbamoylphenyl)acetic acid (436c) (18 mg, 36%) HCl salt as a light yellow solid; $^1$H NMR (300 MHz, DMSO-d$_6$) δ 12.34 (s, 1H), 8.88 (s, 3H), 8.11 (d, J=2.2 Hz, 1H), 8.08-8.03 (m, 1H), 8.02-7.94 (m, 2H), 7.78 (d, J=1.6 Hz, 1H), 7.67 (d, J=1.8 Hz, 1H), 7.63 (d, J=7.3 Hz, 3H), 7.45 (dd, J=7.8, 1.5 Hz, 1H), 7.37 (s, 1H), 7.30 (d, J=7.8 Hz, 1H), 7.07 (d, J=2.2 Hz, 1H), 5.33 (s, 2H), 4.97-4.68 (m, 3H), 3.65 (s, 2H); $^{19}$F NMR (282 MHz, DMSO-d$_6$) δ −222.61; MS (ES+): 463.15 (M+1); Optical rotation [t]D=+7.75 (c=0.155, MeOH).

Scheme-437

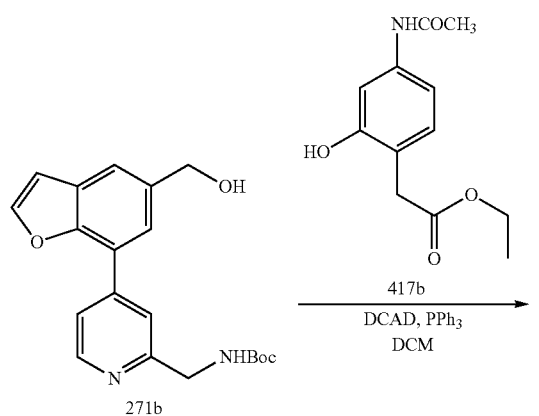

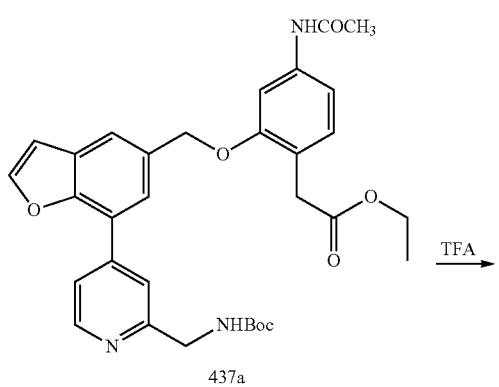

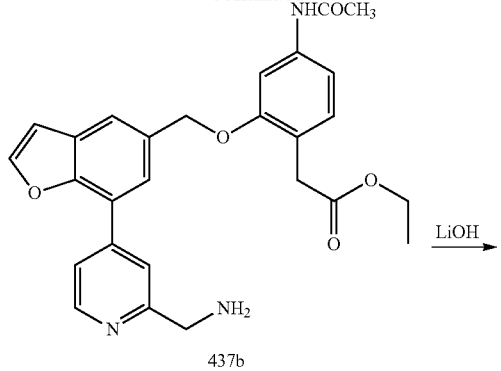

Preparation of 2-(4-acetamido-2-((7-(2-(aminomethyl)pyridin-4-yl)benzofuran-5-yl)methoxy)phenyl)acetic Acid (437c)

Step-1: Preparation of Ethyl 2-(4-acetamido-2-((7-(2-(((tert-butoxycarbonyl)amino)methyl)pyridin-4-yl)benzofuran-5-yl)methoxy)phenyl)acetate (437a)

Compound 437a was prepared according to the procedure reported in step-2 of scheme-23 from tert-butyl ((4-(5-(hydroxymethyl)benzofuran-7-yl)pyridin-2-yl)methyl)carbamate (271b) (269 mg, 0.759 mmol) in DCM (9 mL) using triphenylphosphine (249 mg, 0.948 mmol), ethyl 2-(4-acetamido-2-hydroxyphenyl)acetate (417b) (150 mg, 0.632 mmol) and a solution of (E)-bis(4-chlorobenzyl) diazene-1,2-dicarboxylate (DCAD, 348 mg, 0.948 mmol) in DCM (9 mL). This gave after workup and purification by flash column chromatography [silica gel, eluting with hexanes/10% methanol in ethyl acetate (1:0 to 1:1)] ethyl 2-(4-acetamido-2-((7-(2-(((tert-butoxycarbonyl)amino)methyl)pyridin-4-yl)benzofuran-5-yl)methoxy)phenyl)acetate (437a) (178 mg, 49%) as a colorless gum; $^1$H NMR (300 MHz, DMSO-d$_6$) δ 9.95 (s, 1H), 8.63 (dd, J=5.2, 0.8 Hz, 1H), 8.12 (d, J=2.2 Hz, 1H), 7.83 (s, 1H), 7.81 (d, J=1.5 Hz, 1H), 7.77 (dd, J=5.2, 1.7 Hz, 1H), 7.70 (d, J=1.6 Hz, 1H), 7.54-7.42 (m, 2H), 7.16-7.02 (m, 3H), 5.19 (s, 2H), 4.32 (d, J=6.1 Hz, 2H), 3.91 (q, J=7.1 Hz, 2H), 3.56 (s, 2H), 2.03 (s, 3H), 1.40 (s, 9H), 0.95 (t, J=7.1 Hz, 3H); MS (ES+): 574.20 (M+1).

1341

Step-2: Preparation of Ethyl 2-(4-acetamido-2-((7-(2-(aminomethyl)pyridin-4-yl)benzofuran-5-yl)methoxy)phenyl)acetate (437b)

Compound 437b was prepared according to the procedure reported in step-5 of scheme-1 from ethyl 2-(4-acetamido-2-((7-(2-(((tert-butoxycarbonyl)amino)methyl)pyridin-4-yl)benzofuran-5-yl)methoxy)phenyl)acetate (437a) (165 mg, 0.288 mmol) in DCM (15 mL) using TFA (0.427 mL, 5.75 mmol). This gave after workup ethyl 2-(4-acetamido-2-((7-(2-(aminomethyl)pyridin-4-yl)benzofuran-5-yl)methoxy)phenyl)acetate (437b) which was used as such for next step. MS (ES+): 474.20 (M+1).

Step-3: Preparation of 2-(4-acetamido-2-((7-(2-(aminomethyl)pyridin-4-yl)benzofuran-5-yl)methoxy)phenyl)acetic Acid (437c)

Compound 437c was prepared according to the procedure reported in step-6 of scheme-1, from ethyl 2-(4-acetamido-2-((7-(2-(aminomethyl)pyridin-4-yl)benzofuran-5-yl)methoxy)phenyl)acetate (437b) (0.288 mmol; from above step-2) in THF/MeOH (6 mL, each) using a solution of lithium hydroxide hydrate (99 mg, 2.304 mmol) in water (6 mL). This gave after workup and purification by reverse phase column chromatography [C18 column, 50 g, eluting with water (containing 0.1% HCl)/acetonitrile (1:0 to 0:1)] 2-(4-acetamido-2-((7-(2-(aminomethyl)pyridin-4-yl)benzofuran-5-yl)methoxy)phenyl)acetic acid (437c) (61 mg, 48%) HCl salt as a yellow solid; $^1$H NMR (300 MHz, DMSO-$d_6$) δ 10.02 (s, 1H), 8.78 (d, J=5.3 Hz, 1H), 8.47 (s, 3H), 8.17 (d, J=2.2 Hz, 1H), 8.13-8.07 (m, 1H), 8.01 (dd, J=5.3, 1.7 Hz, 1H), 7.88 (d, J=1.5 Hz, 1H), 7.83 (d, J=1.6 Hz, 1H), 7.54 (d, J=1.9 Hz, 1H), 7.14-7.01 (m, 3H), 5.23 (s, 2H), 4.37-4.26 (m, 2H), 3.54 (s, 2H), 2.03 (s, 3H); MS (ES+): 446.20 (M+1); MS (ES−): 444.10 (M−1); Analysis calculated for $C_{25}H_{23}N_3O_5$ 0.2HCl.3H$_2$O: C, 52.45; H, 5.46; N, 7.34; Cl, 12.39; Found: C, 52.43; H, 5.44; N, 7.23; Cl, 12.18.

Scheme-438

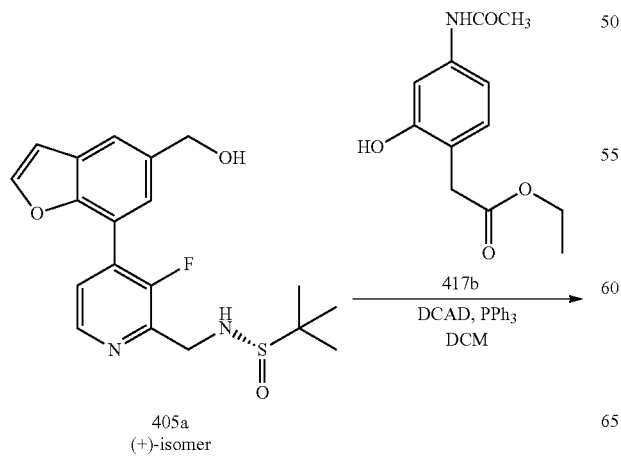

1342

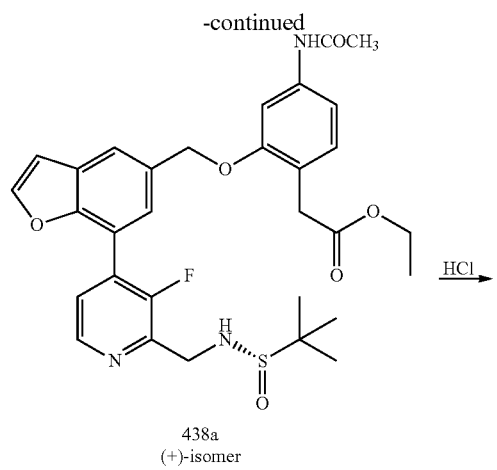

438a
(+)-isomer

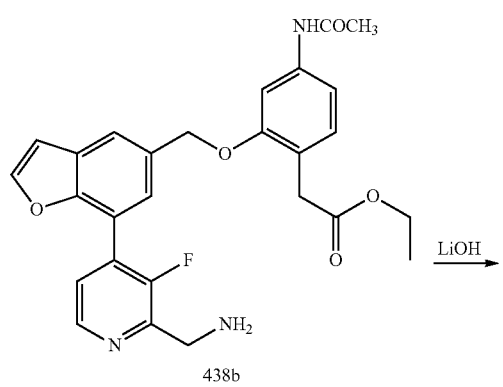

438b

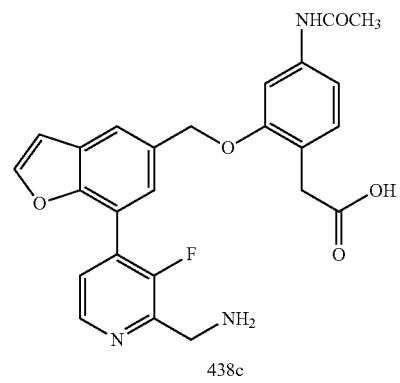

438c

Preparation of 2-(4-acetamido-2-((7-(2-(aminomethyl)-3-fluoropyridin-4-yl)benzofuran-5-yl)methoxy)phenyl)acetic Acid (438c)

Step-1: Preparation of (+)-(S)-ethyl 2-(4-acetamido-2-((7-(2-(((1,1-dimethylethylsulfinamido)methyl)-3-fluoropyridin-4-yl)benzofuran-5-yl)methoxy)phenyl)acetate (438a)

Compound 438a was prepared according to the procedure reported in step-2 of scheme-23 from (+)-(S)—N-((3-fluoro-4-(5-(hydroxymethyl)benzofuran-7-yl)pyridin-2-yl)

methyl)-2-methylpropane-2-sulfinamide (405a) (286 mg, 0.759 mmol) in DCM (9 mL)/THF (3.5 mL) using triphenylphosphine (249 mg, 0.948 mmol), ethyl 2-(4-acetamido-2-hydroxyphenyl)acetate (417b) (150 mg, 0.632 mmol) and a solution of (E)-bis(4-chlorobenzyl) diazene-1,2-dicarboxylate (DCAD, 348 mg, 0.948 mmol) in DCM (9 mL). This gave after workup and purification by flash column chromatography [silica gel, eluting with a 9:1 mixture of ethyl acetate and methanol in hexanes (1:0 to 0:1)] (+)-(S)-ethyl 2-(4-acetamido-2-((7-(2-((1,1-dimethylethylsulfinamido)methyl)-3-fluoropyridin-4-yl)benzofuran-5-yl)methoxy)phenyl)acetate (438a) (85 mg, 23%) as an off-white solid; $^1$H NMR (300 MHz, DMSO-$d_6$) δ 9.95 (s, 1H), 8.52 (d, J=4.9 Hz, 1H), 8.09 (d, J=2.2 Hz, 1H), 7.85 (d, J=1.6 Hz, 1H), 7.68 (t, J=5.2 Hz, 1H), 7.53 (s, 1H), 7.47 (d, J=1.7 Hz, 1H), 7.16-6.98 (m, 3H), 5.86 (t, J=5.8 Hz, 1H), 5.18 (s, 2H), 4.43-4.38 (m, 2H), 3.90 (q, J=7.1 Hz, 2H), 3.55 (s, 2H), 2.03 (s, 3H), 1.11 (s, 9H), 0.97 (t, J=7.1 Hz, 3H); $^{19}$F NMR (282 MHz, DMSO-$d_6$) δ −127.79; MS (ES+): 596.20 (M+1); Optical rotation [t]D=+36.67 (c=0.24, MeOH).

Step-2: Preparation of Ethyl 2-(4-acetamido-2-((7-(2-(aminomethyl)-3-fluoropyridin-4-yl)benzofuran-5-yl)methoxy)phenyl)acetate (438b)

To a solution of (+)-(S)-ethyl 2-(4-acetamido-2-((7-(2-((1,1-dimethylethylsulfinamido)methyl)-3-fluoropyridin-4-yl)benzofuran-5-yl)methoxy)phenyl)acetate (438a) (80 mg, 0.134 mmol) in tetrahydrofuran (5 mL) was added 3 N aqueous HCl (0.134 mL, 0.403 mmol) at room temperature and stirred for 2 h. The reaction mixture was concentrated to dryness to give ethyl 2-(4-acetamido-2-((7-(2-(aminomethyl)-3-fluoropyridin-4-yl)benzofuran-5-yl)methoxy)phenyl)acetate (438b) which was used as such for next step. MS (ES+): 492.10 (M+1).

Step-3: Preparation of 2-(4-acetamido-2-((7-(2-(aminomethyl)-3-fluoropyridin-4-yl)benzofuran-5-yl)methoxy)phenyl)acetic Acid (438c)

Compound 438c was prepared according to the procedure reported in step-6 of scheme-1 from ethyl 2-(4-acetamido-2-((7-(2-(aminomethyl)-3-fluoropyridin-4-yl)benzofuran-5-yl)methoxy)phenyl)acetate (438b) (0.134 mmol, from above step-2) in MeOH/THF (4 mL each) using a solution of lithium hydroxide hydrate (46 mg, 1.072 mmol) in water (4 mL). This gave after workup and purification by reverse phase column [C18, 100 g, eluting with water (containing 0.1% HCl)/acetonitrile (1:0 to 0:1)] 2-(4-acetamido-2-((7-(2-(aminomethyl)-3-fluoropyridin-4-yl)benzofuran-5-yl)methoxy)phenyl)acetic acid (438c) (72 mg, 94%) HCl salt as a white solid; $^1$H NMR (300 MHz, DMSO-$d_6$) δ 10.00 (s, 1H), 8.63 (d, J=5.0 Hz, 1H), 8.57-8.49 (m, 3H), 8.12 (d, J=2.2 Hz, 1H), 7.92 (d, J=1.6 Hz, 1H), 7.82 (t, J=5.3 Hz, 1H), 7.61-7.59 (m, 1H), 7.51 (d, J=1.8 Hz, 1H), 7.16-7.00 (m, 3H), 5.21 (s, 2H), 4.46-4.26 (m, 2H), 3.52 (s, 2H), 2.03 (s, 3H); $^{19}$F NMR (282 MHz, DMSO-$d_6$) δ −128.15; MS (ES+): 464.15 (M+1); MS (ES−): 462.15 (M−1); Analysis calculated for $C_{25}H_{22}FN_3O_5 \cdot 1.5HCl \cdot 3H_2O$: C, 52.48; H, 5.20; N, 7.34; Cl, 9.29; Found: C, 52.56; H, 5.02; N, 7.31; Cl, 8.98.

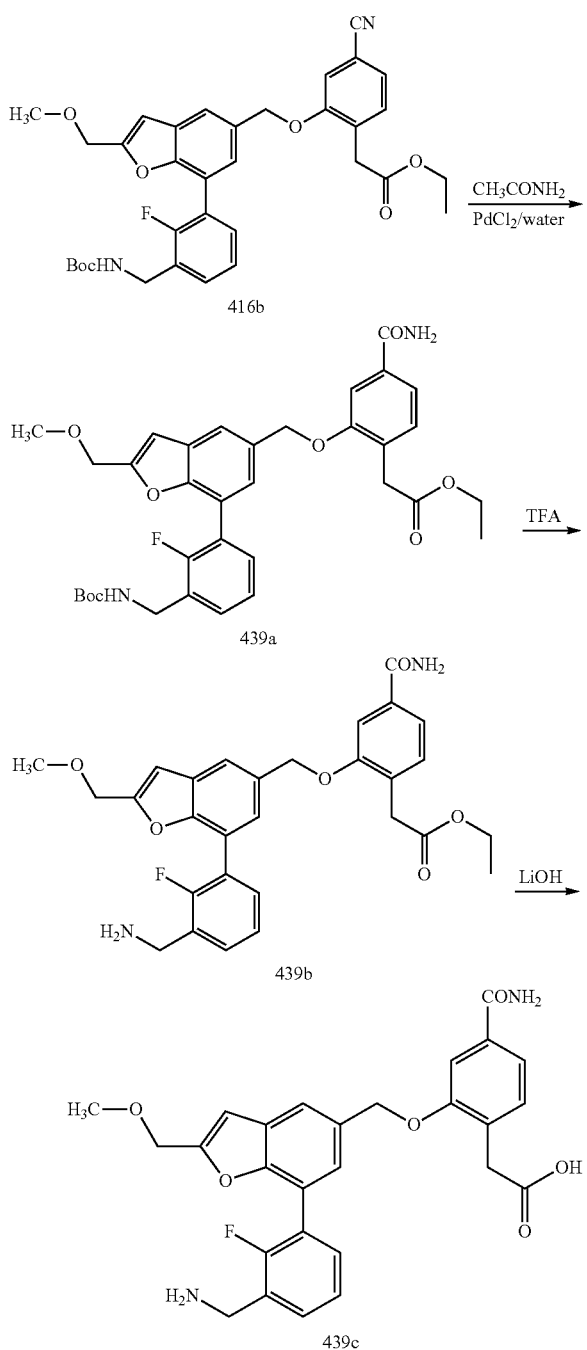

Preparation of 2-(2-((7-(3-(aminomethyl)-2-fluorophenyl)-2-(methoxymethyl)benzofuran-5-yl)methoxy)-4-carbamoylphenyl)acetic Acid (439c)

Step-1: Preparation of Ethyl 2-(2-((7-(3-(((tert-butoxycarbonyl)amino)methyl)-2-fluorophenyl)-2-(methoxymethyl)benzofuran-5-yl)methoxy)-4-carbamoylphenyl)acetate (439a)

Compound 439a was prepared according to the procedure reported in step-1 of scheme-238 from ethyl 2-(2-((7-(3-

(((tert-butoxycarbonyl)amino)methyl)-2-fluorophenyl)-2-(methoxymethyl)benzofuran-5-yl)methoxy)-4-cyanophenyl)acetate (416b) (300 mg, 0.498 mmol) in THF (9 mL) and water (0.8 mL), using acetamide (176 mg, 2.99 mmol), palladium(II) chloride (27 mg, 0.149 mmol) and stirring at room temperature for 18 h. This gave after workup and purification by flash column chromatography (silica gel, 24 g, eluting with 9:1 EtOAc/MeOH in hexanes from 0 to 60%) ethyl 2-(2-((7-(3-(((tert-butoxycarbonyl)amino)methyl)-2-fluorophenyl)-2-(methoxymethyl)benzofuran-5-yl)methoxy)-4-carbamoylphenyl)acetate (439a) (214 mg, 69%) as an off white waxy oil; $^{1}$H NMR (300 MHz, DMSO-$d_6$) δ 7.99 (s, 1H), 7.74 (d, J=1.6 Hz, 1H), 7.62 (d, 1H), 7.55-7.25 (m, 8H), 7.00 (s, 1H), 5.27 (s, 2H), 4.52 (s, 2H), 4.26 (d, J=6.1 Hz, 2H), 3.89 (q, J=7.1 Hz, 2H), 3.66 (s, 2H), 3.29 (s, 3H), 1.41 (s, 9H), 0.96 (t, J=7.1 Hz, 3H); $^{19}$F NMR (282 MHz, DMSO-$d_6$) δ−118.72.

Step-2: Preparation of Ethyl 2-(2-((7-(3-(aminomethyl)-2-fluorophenyl)-2-(methoxymethyl)benzofuran-5-yl)methoxy)-4-carbamoylphenyl)acetate (439b)

Compound 439b was prepared according to the procedure reported in step-5 of scheme-1 from ethyl 2-(2-((7-(3-(((tert-butoxycarbonyl)amino)methyl)-2-fluorophenyl)-2-(methoxymethyl)benzofuran-5-yl)methoxy)-4-carbamoylphenyl)acetate (439a) (180 mg, 0.290 mmol) in DCM (15 mL) using TFA (0.431 mL, 5.80 mmol). This gave after workup ethyl 2-(2-((7-(3-(aminomethyl)-2-fluorophenyl)-2-(methoxymethyl)benzofuran-5-yl)methoxy)-4-carbamoylphenyl)acetate (439b) which was used as such for next step. MS (ES+): 521.20 (M+1).

Step-3: Preparation of 2-(2-((7-(3-(aminomethyl)-2-fluorophenyl)-2-(methoxymethyl)benzofuran-5-yl)methoxy)-4-carbamoylphenyl)acetic Acid (439c)

Compound 439c was prepared according to the procedure reported in step-6 of scheme-1 from ethyl 2-(2-((7-(3-(aminomethyl)-2-fluorophenyl)-2-(methoxymethyl)benzofuran-5-yl)methoxy)-4-carbamoylphenyl)acetate (439b) (0.29 mmol, from above step-2) in THF/MeOH (6 mL, each) using a solution of lithium hydroxide hydrate (0.099 g, 2.320 mmol) in water (6 mL). This gave after workup and purification by reverse phase column [C18, eluting with water (containing 0.1% HCl)/acetonitrile (1:0 to 0:1)] 2-(2-((7-(3-(aminomethyl)-2-fluorophenyl)-2-(methoxymethyl)benzofuran-5-yl)methoxy)-4-carbamoylphenyl)acetic acid (439c) (80 mg, 56%) HCl salt as a white solid; $^{1}$H NMR (300 MHz, DMSO-$d_6$) δ 12.29 (s, 1H), 8.45 (s, 3H), 7.99 (s, 1H), 7.80 (d, J=1.6 Hz, 1H), 7.74-7.63 (m, 2H), 7.61 (d, J=1.5 Hz, 1H), 7.49-7.41 (m, 3H), 7.37 (s, 1H), 7.29 (d, J=7.8 Hz, 1H), 7.01 (s, 1H), 5.30 (s, 2H), 4.52 (s, 2H), 4.18 (s, 2H), 3.62 (s, 2H), 3.29 (s, 3H); MS (ES+): 493.10 (M+1); Analysis calculated for $C_{27}H_{25}FN_2O_6 \cdot HCl \cdot 3H_2O$: C, 55.62; H, 5.53; N, 4.81; Cl, 6.08; Found: C, 55.89; H, 5.15; N, 4.72; Cl, 6.15.

Scheme-440

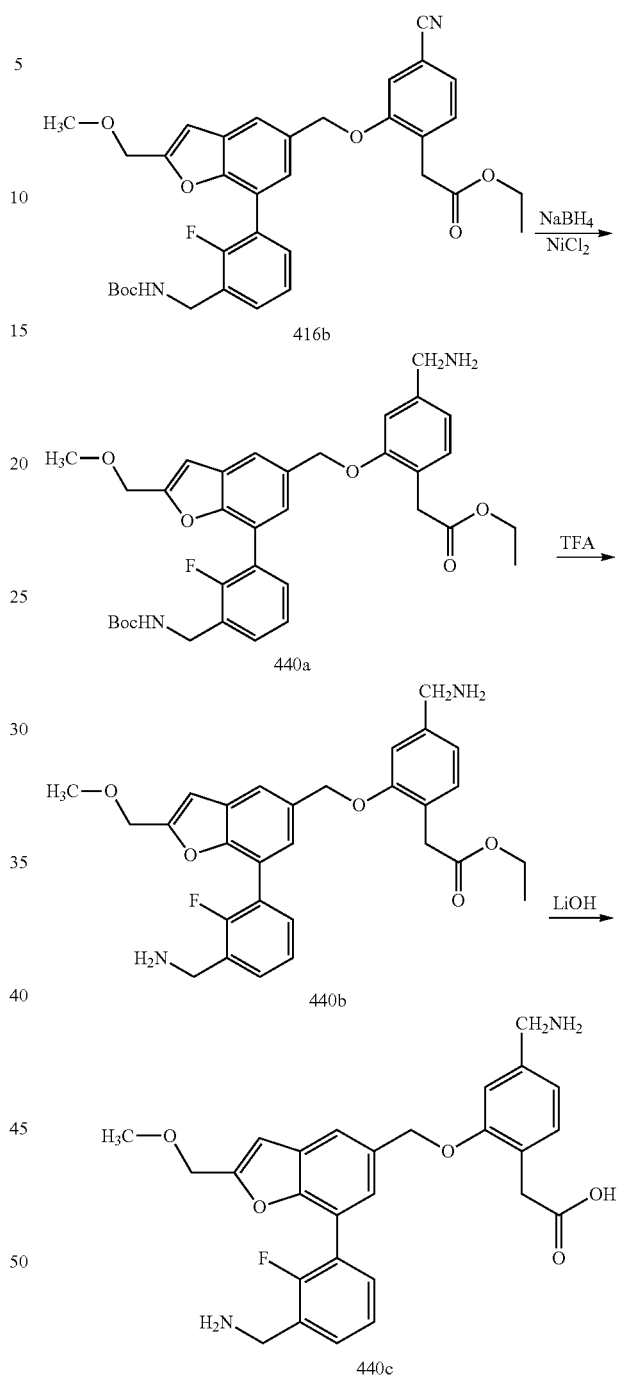

Preparation of 2-(4-(aminomethyl)-2-((7-(3-(aminomethyl)-2-fluorophenyl)-2-(methoxymethyl)benzofuran-5-yl)methoxy)phenyl)acetic Acid (440c)

Step-1: Preparation of Ethyl 2-(4-(aminomethyl)-2-((7-(3-(((tert-butoxycarbonyl)amino)methyl)-2-fluorophenyl)-2-(methoxymethyl)benzofuran-5-yl)methoxy)phenyl)acetate (440a)

Compound 440a was prepared according to the procedure reported in step-2 of scheme-256 from ethyl 2-(2-((7-(3-

(((tert-butoxycarbonyl)amino)methyl)-2-fluorophenyl)-2-(methoxymethyl)benzofuran-5-yl)methoxy)-4-cyanophenyl)acetate (416b) (400 mg, 0.664 mmol) in methanol (20 mL) using nickel (II) chloride hexahydrate (39 mg, 0.166 mmol) and sodium borohydride (151 mg, 3.98 mmol), using N1-(2-aminoethyl)ethane-1,2-diamine (0.143 mL, 1.327 mmol) for quenching. This gave after workup and purification by flash column chromatography [silica gel, eluting with chloroform/methanol (1:0 to 9:1)] ethyl 2-(4-(aminomethyl)-2-((7-(3-(((tert-butoxycarbonyl)amino)methyl)-2-fluorophenyl)-2-(methoxymethyl)benzofuran-5-yl)methoxy)phenyl)acetate (440a) (166 mgs) as a colorless gum; MS (ES+): 607.30 (M+1).

Step-2: Preparation of Ethyl 2-(4-(aminomethyl)-2-((7-(3-(aminomethyl)-2-fluorophenyl)-2-(methoxymethyl)benzofuran-5-yl)methoxy)phenyl) acetate (440b)

Compound 440b was prepared according to the procedure reported in step-5 of scheme-1 from ethyl 2-(4-(aminomethyl)-2-((7-(3-(((tert-butoxycarbonyl)amino)methyl)-2-fluorophenyl)-2-(methoxymethyl)benzofuran-5-yl)methoxy)phenyl)acetate (440a) (150 mg, 0.247 mmol) in DCM (12 mL) using TFA (0.367 mL, 4.94 mmol). This gave after workup ethyl 2-(4-(aminomethyl)-2-((7-(3-(aminomethyl)-2-fluorophenyl)-2-(methoxymethyl)benzofuran-5-yl)methoxy)phenyl)acetate (440b) which was used as such for next step. MS (ES+): 507.20 (M+1).

Step-3: Preparation of 2-(4-(aminomethyl)-2-((7-(3-(aminomethyl)-2-fluorophenyl)-2-(methoxymethyl)benzofuran-5-yl)methoxy)phenyl)acetic Acid (440c)

Compound 440c was prepared according to the procedure reported in step-6 of scheme-1 from ethyl 2-(4-(aminomethyl)-2-((7-(3-(aminomethyl)-2-fluorophenyl)-2-(methoxymethyl)benzofuran-5-yl)methoxy)phenyl)acetate (440b) (0.247 mmol, from above step-2) in THF/MeOH (6 mL, each) using a solution of lithium hydroxide hydrate (85 mg, 1.976 mmol) in water (6 mL) stirring at room temperature for 16 h. This gave after workup and purification by reverse phase column [C18, eluting with water (containing 0.1% HCl)/acetonitrile (1:0 to 0:1)] 2-(4-(aminomethyl)-2-((7-(3-(aminomethyl)-2-fluorophenyl)-2-(methoxymethyl)benzofuran-5-yl)methoxy)phenyl)acetic acid (440c) (88 mg, 75%) HCl salt as a white solid; $^1$H NMR (300 MHz, DMSO-$d_6$) δ 8.56 (s, 6H), 7.81 (d, J=1.6 Hz, 1H), 7.75-7.61 (m, 2H), 7.51-7.38 (m, 3H), 7.24 (d, J=7.7 Hz, 1H), 7.04-6.99 (m, 2H), 5.26 (s, 2H), 4.52 (s, 2H), 4.17 (s, 2H), 3.99 (s, 2H), 3.58 (s, 2H), 3.29 (s, 3H); $^{19}$F NMR (282 MHz, DMSO-$d_6$) δ−118.70; MS (ES+): 479.20 (M+1); MS (ES−): 477.20 (M−1); Analysis calculated for $C_{27}H_{27}FN_2O_5 \cdot 2HCl \cdot 2.5H_2O$: C, 54.37; H, 5.75; N, 4.70; Cl, 11.89; Found: C, 54.24; H, 5.70; N, 4.76; Cl, 11.94.

Scheme-441

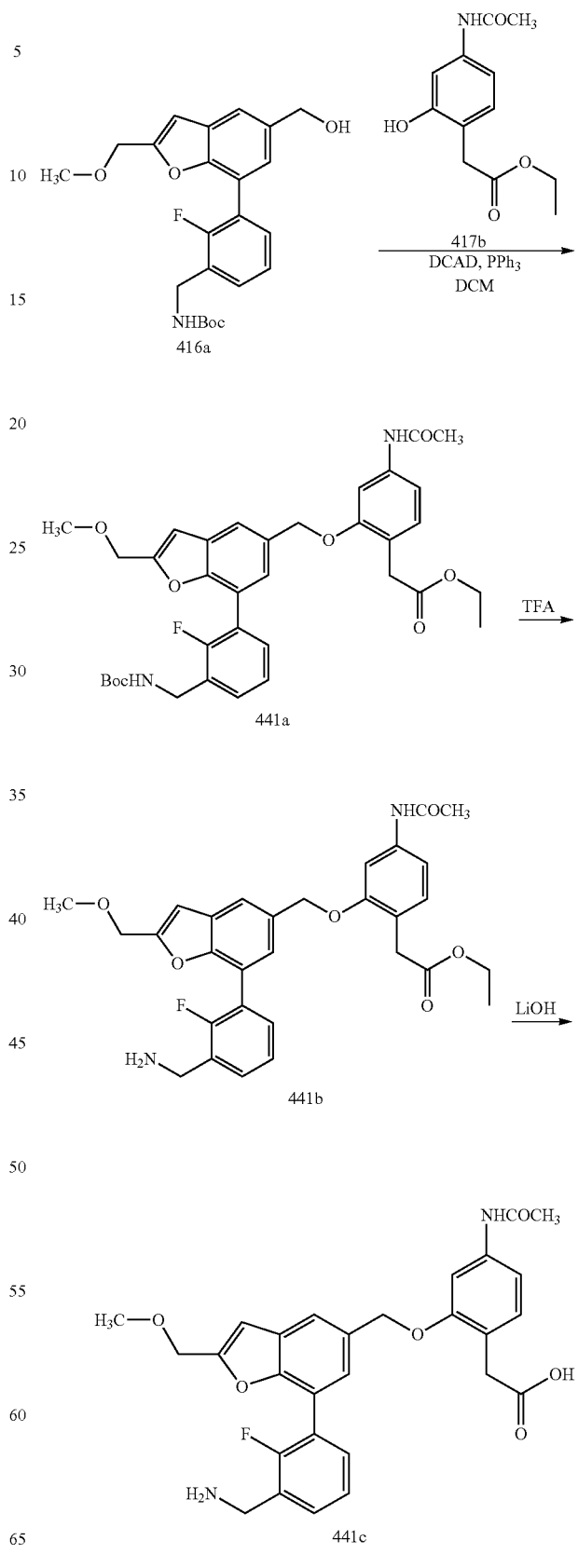

Preparation of 2-(4-acetamido-2-((7-(3-(aminomethyl)-2-fluorophenyl)-2-(methoxymethyl)benzofuran-5-yl)methoxy)phenyl)acetic Acid (441c)

Step-1: Preparation of Ethyl 2-(4-acetamido-2-((7-(3-(((tert-butoxycarbonyl)amino)methyl)-2-fluorophenyl)-2-(methoxymethyl)benzofuran-5-yl)methoxy)phenyl)acetate (441a)

Compound 441a was prepared according to the procedure reported in step-2 of scheme-23 from tert-butyl 2-fluoro-3-(5-(hydroxymethyl)-2-(methoxymethyl)benzofuran-7-yl)benzylcarbamate (416a) (360 mg, 0.867 mmol) in DCM (9 mL)/THF (3.5 mL) using triphenylphosphine (257 mg, 0.980 mmol), ethyl 2-(4-acetamido-2-hydroxyphenyl)acetate (417b) (155 mg, 0.653 mmol) and a solution of (E)-bis(4-chlorobenzyl) diazene-1,2-dicarboxylate (DCAD, 360 mg, 0.980 mmol) in DCM (9 mL). This gave after workup and purification by flash column chromatography (silica gel, eluting with 0 to 50% of 9:1 ethyl acetate/methanol in hexanes) ethyl 2-(4-acetamido-2-((7-(3-(((tert-butoxycarbonyl)amino)methyl)-2-fluorophenyl)-2-(methoxymethyl)benzofuran-5-yl)methoxy)phenyl)acetate (441a) (195 mg, 47%) as a clear oil; $^1$H NMR (300 MHz, DMSO-d$_6$) δ 9.95 (s, 1H), 7.73 (d, J=1.7 Hz, 1H), 7.55-7.27 (m, 6H), 7.10 (s, 2H), 7.00 (s, 1H), 5.15 (s, 2H), 4.52 (s, 2H), 4.26 (d, J=6.4 Hz, 2H), 3.89 (q, J=7.0 Hz, 2H), 3.54 (s, 2H), 3.29 (s, 3H), 2.03 (s, 3H), 1.41 (s, 9H), 0.97 (t, J=7.1 Hz, 3H); MS (ES+): 657.25 (M+Na).

Step-2: Preparation of Ethyl 2-(4-acetamido-2-((7-(3-(aminomethyl)-2-fluorophenyl)-2-(methoxymethyl)benzofuran-5-yl)methoxy)phenyl)acetate (441b)

Compound 441b was prepared according to the procedure reported in step-5 of scheme-1 from ethyl 2-(4-acetamido-2-((7-(3-(((tert-butoxycarbonyl)amino)methyl)-2-fluorophenyl)-2-(methoxymethyl)benzofuran-5-yl)methoxy)phenyl)acetate (441a) (100 mg, 0.158 mmol) in DCM (10 mL) using TFA (0.234 mL, 3.15 mmol). This gave after workup ethyl 2-(4-acetamido-2-((7-(3-(aminomethyl)-2-fluorophenyl)-2-(methoxymethyl)benzofuran-5-yl)methoxy)phenyl)acetate (441b) which was used as such for next step. MS (ES+): 535.20 (M+1).

Step-3: Preparation of 2-(4-acetamido-2-((7-(3-(aminomethyl)-2-fluorophenyl)-2-(methoxymethyl)benzofuran-5-yl)methoxy)phenyl)acetic Acid (441c)

Compound 441c was prepared according to the procedure reported in step-6 of scheme-1 from ethyl 2-(4-acetamido-2-((7-(3-(aminomethyl)-2-fluorophenyl)-2-(methoxymethyl)benzofuran-5-yl)methoxy)phenyl)acetate (441b) (0.158 mmol, from above step-2) in THF/methanol (4 mL, 1:1 each) using solution of lithium hydroxide hydrate (54 mg, 1.264 mmol) in water (4 mL) and stirring at room temperature for 17.5 h. This gave after workup and purification by reverse-phase column chromatography [C-18 column, eluting with water (containing 0.1% HCl)/acetonitrile (1:0 to 0:1)] 2-(4-acetamido-2-((7-(3-(aminomethyl)-2-fluorophenyl)-2-(methoxymethyl)benzofuran-5-yl)methoxy)phenyl)acetic acid (441c) (72 mg, 90%) HCl salt as a white solid; $^1$H NMR (300 MHz, DMSO-d$_6$) δ 12.16 (s, 1H), 9.97 (s, 1H), 8.44 (s, 3H), 7.79 (d, J=1.6 Hz, 1H), 7.74-7.61 (m, 2H), 7.49 (d, J=1.8 Hz, 1H), 7.47-7.39 (m, 2H), 7.15-7.03 (m, 2H), 7.00 (s, 1H), 5.18 (s, 2H), 4.52 (s, 2H), 4.23-4.10 (m, 2H), 3.50 (s, 2H), 3.29 (s, 3H), 2.03 (s, 3H); $^{19}$F NMR (282 MHz, DMSO-d$_6$) δ−118.48; MS (ES+): 507.20 (M+1); MS (ES−): 505.20 (M−1); Analysis calculated for $C_{28}H_{27}FN_2O_6 \cdot HCl \cdot 2.5H_2O$: C, 57.19; H, 5.66; N, 4.76; Cl, 6.03; Found: C, 57.04; H, 5.22; N, 4.71; Cl, 5.89.

Scheme-442

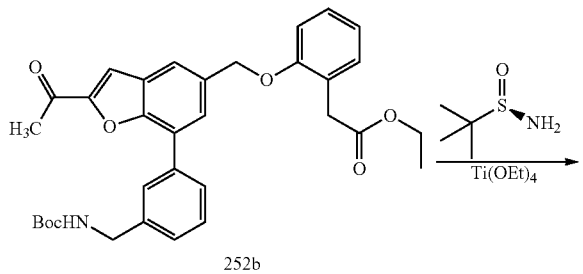

252b

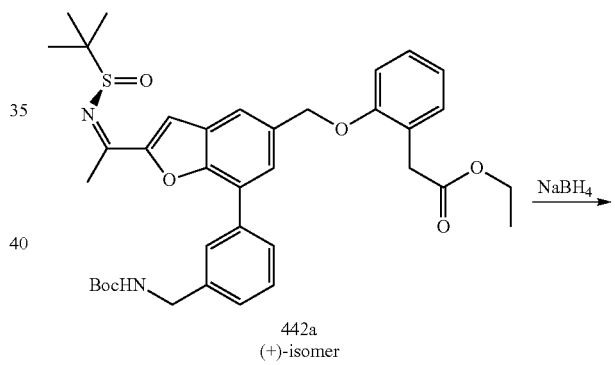

442a
(+)-isomer

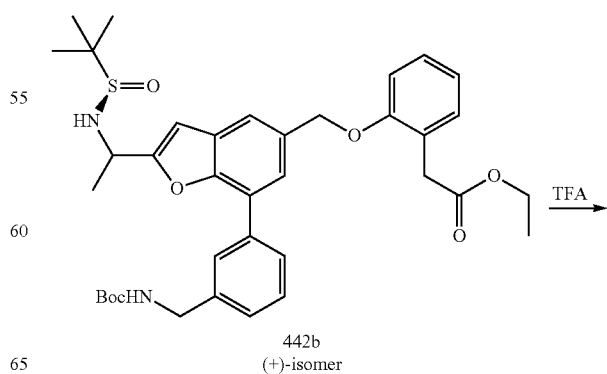

442b
(+)-isomer

-continued

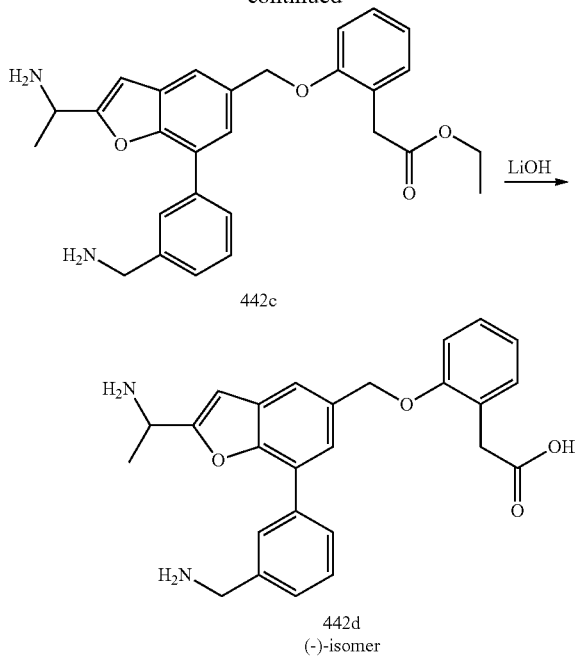

442c 442d
(−)-isomer

Preparation of (−)-2-(2-((2-(1-aminoethyl)-7-(3-(aminomethyl)phenyl)benzofuran-5-yl)methoxy)phenyl)acetic Acid (442d)

Step-1: Preparation of (+)-(R,Z)-ethyl 2-(2-((7-(3-(((tert-butoxycarbonyl)amino)methyl)phenyl)-2-(1-((tert-butylsulfinyl)imino)ethyl)benzofuran-5-yl)methoxy)phenyl)acetate (442a)

Compound 442a was prepared according to the procedure reported in step-1 of scheme-258 from ethyl 2-(2-((2-acetyl-7-(3-(((tert-butoxycarbonyl)amino)methyl)phenyl)benzofuran-5-yl)methoxy)phenyl)acetate (252b) (500 mg, 0.897 mmol) and (R)-2-methylpropane-2-sulfinamide (137 mg, 1.121 mmol) in tetrahydrofuran (10 mL) using tetraethoxytitanium (0.376 mL, 1.793 mmol) and heating at reflux for 16 h. This gave after workup and purification by flash column chromatography [silica gel, eluting with hexanes/ethyl acetate (1:0 to 2:1)] (+)-(R,Z)-ethyl 2-(2-((7-(3-(((tert-butoxycarbonyl)amino)methyl)phenyl)-2-(1-((tert-butylsulfinyl)imino)ethyl)benzofuran-5-yl)methoxy)phenyl)acetate (442a) (391 mg, 66%) as a yellow gum; $^1$H NMR (300 MHz, DMSO-$d_6$) δ 7.92-7.78 (m, 4H), 7.78-7.76 (m, 1H), 7.54-7.40 (m, 2H), 7.36-7.19 (m, 3H), 7.14-7.09 (m, 1H), 6.92 (td, J=7.4, 1.1 Hz, 1H), 5.26 (s, 2H), 4.22 (d, J=6.2 Hz, 2H), 3.92 (q, J=7.1 Hz, 2H), 3.63 (s, 2H), 2.73 (s, 3H), 1.38 (s, 9H), 1.26 (s, 9H), 0.96 (t, J=7.1 Hz, 3H); Optical rotation [t]D=+48.00 (c=0.3, MeOH).

Step-2: Preparation of (−)-ethyl 2-(2-((7-(3-(((tert-butoxycarbonyl)amino)methyl)phenyl)-2-(1-((R)-1,1-dimethylethylsulfinamido)ethyl)benzofuran-5-yl)methoxy)phenyl)acetate (442b)

Compound 442b was prepared according to the procedure reported in step-2 of scheme-258 from (+)-(R,Z)-ethyl 2-(2-((7-(3-(((tert-butoxycarbonyl)amino)methyl)phenyl)-2-(1-((tert-butylsulfinyl)imino)ethyl)benzofuran-5-yl)methoxy)phenyl)acetate (442a) (350 mg, 0.530 mmol) in tetrahydrofuran (12 mL) using sodium borohydride (41 mg, 1.059 mmol) and stirring at room temperature for 10 h. This gave after workup and purification by flash column chromatography [silica gel, eluting with hexanes/10% methanol in ethyl acetate (1:0 to 1:1)] (−)-ethyl 2-(2-((7-(3-(((tert-butoxycarbonyl)amino)methyl)phenyl)-2-(1-((R)-1,1-dimethylethylsulfinamido)ethyl)benzofuran-5-yl)methoxy)phenyl)acetate (442b) (215 mg, 61%) as a white solid; $^1$H NMR (300 MHz, DMSO-$d_6$) δ 7.87 (s, 1H), 7.78 (d, J=7.7 Hz, 1H), 7.64 (d, J=1.6 Hz, 1H), 7.55-7.40 (m, 3H), 7.31-7.17 (m, 3H), 7.10 (d, J=8.1 Hz, 1H), 6.94-6.83 (m, 2H), 5.92 (d, J=8.0 Hz, 1H), 5.22 (s, 2H), 4.67-4.45 (m, 1H), 4.23 (d, J=6.3 Hz, 2H), 3.92 (q, J=7.1 Hz, 2H), 3.62 (s, 2H), 1.56 (d, J=6.9 Hz, 3H), 1.38 (s, 9H), 1.14 (s, 9H), 0.98 (t, J=7.1 Hz, 3H); MS (ES+): 685.20 (M+Na); Optical rotation [α]$_D$=−26.67 (c=0.06, MeOH).

Step-3: Preparation of Ethyl 2-(2-((2-(1-aminoethyl)-7-(3-(aminomethyl)phenyl)benzofuran-5-yl)methoxy)phenyl)acetate (442c)

Compound 442c was prepared according to the procedure reported in step-5 of scheme-1 from (−)-ethyl 2-(2-((7-(3-(((tert-butoxycarbonyl)amino)methyl)phenyl)-2-(1-((R)-1,1-dimethylethylsulfinamido)ethyl)benzofuran-5-yl)methoxy)phenyl)acetate (442b) (200 mg, 0.302 mmol) in DCM (15 mL) using TFA (0.448 mL, 6.03 mmol) and stirring at room temperature for 19 h. This gave after workup ethyl 2-(2-((2-(1-aminoethyl)-7-(3-(aminomethyl)phenyl)benzofuran-5-yl)methoxy)phenyl)acetate (442c) which was used as such for next step. MS (ES+): 459.20 (M+1).

Step-4: Preparation of (−)-2-(2-((2-(1-aminoethyl)-7-(3-(aminomethyl)phenyl)benzofuran-5-yl)methoxy)phenyl)acetic Acid (442d)

Compound 442d was prepared according to the procedure reported in step-6 of scheme-1 from ethyl 2-(2-((2-(1-aminoethyl)-7-(3-(aminomethyl)phenyl)benzofuran-5-yl)methoxy)phenyl)acetate (442c) (0.302 mmol, from above step-3) in MeOH/THF (6 mL; 1:1) using a solution of lithium hydroxide hydrate (0.103 g, 2.416 mmol) in water (6 mL) and stirring at room temperature for 20 h. This gave after workup and purification by reverse phase column [C18, 100 g, eluting with acetonitrile in H$_2$O containing 0.1% HCl (1:0 to 0:1)] (−)-2-(2-((2-(1-aminoethyl)-7-(3-(aminomethyl)phenyl)benzofuran-5-yl)methoxy)phenyl)acetic acid (442d) (40 mg, 31%) HCl salt as a white solid; $^1$H NMR (300 MHz, DMSO-$d_6$) δ 8.96-8.70 (m, 3H), 8.52 (s, 3H), 8.27-8.11 (m, 1H), 7.99 (dt, J=7.4, 1.7 Hz, 1H), 7.76 (d, J=1.6 Hz, 1H), 7.70 (d, J=1.7 Hz, 1H), 7.63-7.51 (m, 2H), 7.28-7.19 (m, 2H), 7.11-7.06 (m, 2H), 6.90 (td, J=7.4, 1.1 Hz, 1H), 5.27 (s, 2H), 4.82-4.65 (m, 1H), 4.23-4.08 (m, 2H), 3.59 (s, 2H), 1.66 (d, J=6.8 Hz, 3H); MS (ES+): 431.10 (M+1); MS (ES−): 429.20 (M−1); Analysis calculated for $C_{26}H_{26}N_2O_4$·HCl·0.5CF$_3$COOH·3.0H$_2$O: C, 56.10; H, 5.84; N, 4.85; Cl, 6.13; Found: C, 56.22; H, 5.89; N, 4.61; Cl, 6.09; Chiral HPLC 89.06% ee; [Method: ethanol/heptane 90:10 [0.1% DEA in heptane: 0.1% DEA in Ethanol], Temperature: 15° C., UV detection: =242 nM; flow rate: 1 mL/min; runtime: 70 mins; Compound (452d) (R$_t$=45.273 mins, 5.47%) Compound (442d) (R$_t$=51.833 mins; 94.53%)]; Optical rotation [ct]D=−8.0 (c=0.05, MeOH).

Scheme-443
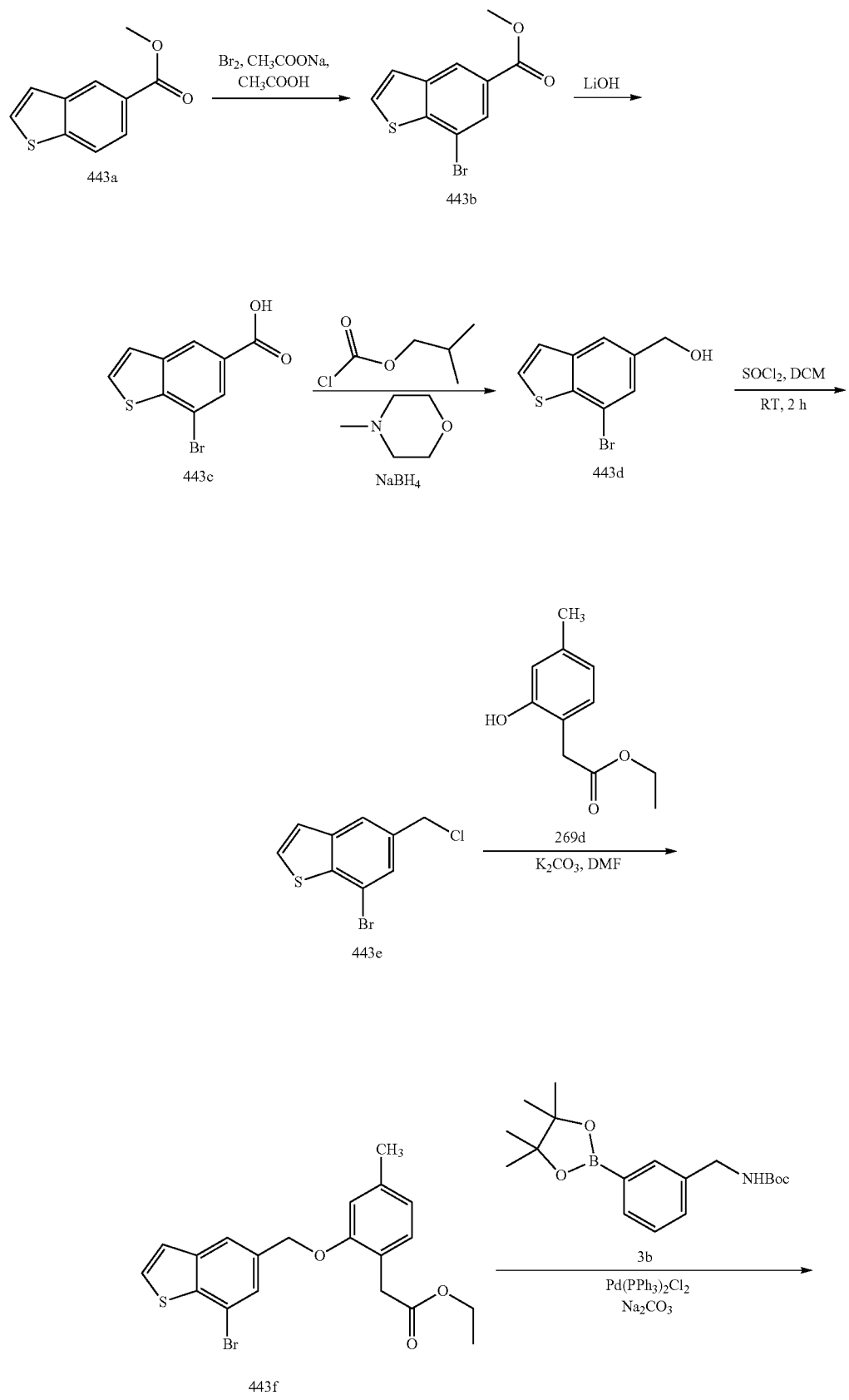

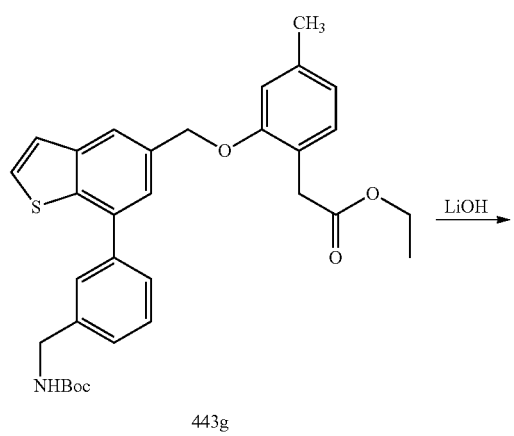

443g

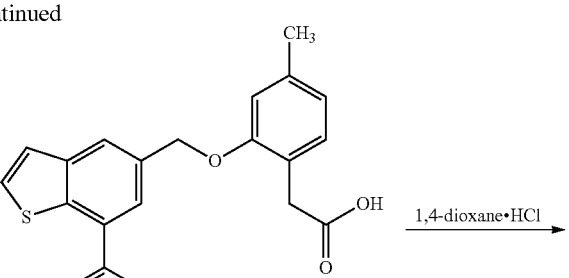

443h

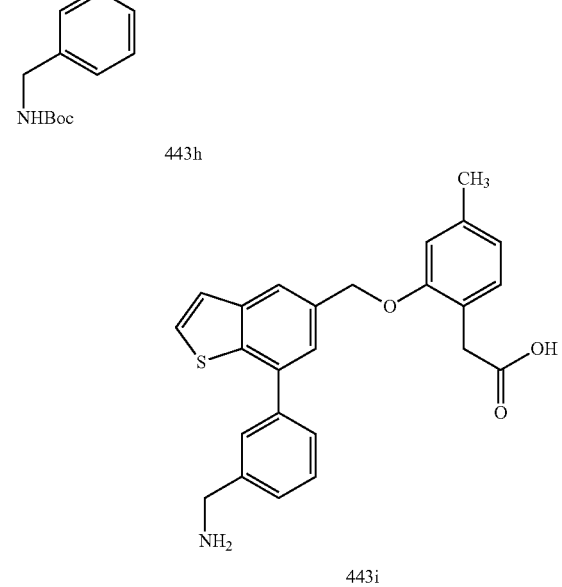

443i

Preparation of 2-(2-((7-(3-(aminomethyl)phenyl)benzo[b]thiophen-5-yl)methoxy)-4-methylphenyl)acetic Acid (443i)

Step-1: Preparation of methyl 7-bromobenzo[b]thiophene-5-carboxylate (443b)

To a stirred solution of methyl benzo[b]thiophene-5-carboxylate (443a) (1.00 g, 5.20 mmol) in AcOH (20.0 mL) was added at room temperature sodium acetate (1.70 g, 20.71 mmol), Br$_2$ (1.66 g, 10.38 mmol) and stirred at room temperature for 2 h. The reaction mixture was poured into water (100 mL) and extracted with EtOAc (2×100 mL). The combined organic layer was dried, filtered and concentrated in vacuum. The residue obtained was purified by over Na$_2$SO$_4$ and concentrated to afford crude product which was purified by flash column chromatography (silica gel, eluting with 1% EtOAc in n-heptane) to afford methyl 7-bromobenzo[b]thiophene-5-carboxylate (443b) (0.80 g, 57%) as an off-white solid; $^1$H NMR (300 MHz, DMSO-d$_6$) δ 8.26 (d, J=1.6 Hz, 1H), 8.19 (d, J=8.5 Hz, 1H), 8.11 (s, 1H), 7.95 (dd, J=8.5, 1.6 Hz, 1H), 3.86 (s, 3H).

Step-2: Preparation of 7-bromobenzo[b]thiophene-5-carboxylic Acid (443c)

Compound 443c was prepared according to the procedure reported in step-6 of scheme-1 from methyl 7-bromobenzo[b]thiophene-5-carboxylate (443b) (2.20 g, 8.11 mmol) in THF/MeOH (6.6 mL each) using a solution of LiOH (0.680 g, 16.20 mmol) in water (6.6 mL). This gave after workup 7-bromobenzo[b]thiophene-5-carboxylic acid (443c) (2.00 g, 96%) as an off-white solid; $^1$H NMR (300 MHz, DMSO-d$_6$) δ 8.32 (s, 1H), 8.21 (d, J=8.4 Hz, 1H), 8.14 (s, 1H), 8.00 (d, J=8.5 Hz, 1H).

Step-3: Preparation of (7-bromobenzo[b]thiophen-5-yl)methanol (443d)

Compound 443d was prepared according to the procedure reported in step-1 of scheme-23 from 7-bromobenzo[b]thiophene-5-carboxylic acid (443c) (2.00 g, 7.77 mmol) using N-methylmorpholine (0.868 g, 8.55 mmol) in THF (20 mL), isobutyl chloroformate (1.168 g, 8.55 mmol) and NaBH$_4$ (0.441 g, 11.65 mmol). This gave after workup and purification by flash column chromatography (silica gel, eluting with 2-4% EtOAc in n-heptane) (7-bromobenzo[b]thiophen-5-yl)methanol (443d) (1.10 g, 58%) as an off-white solid; $^1$H NMR (300 MHz, DMSO-d$_6$) δ 8.02 (d, J=8.3 Hz, 2H), 7.74 (s, 1H), 7.46-7.37 (m, 1H), 5.40 (t, J=5.8 Hz, 1H), 4.67 (d, J=5.8 Hz, 2H).

Step-4: Preparation of 7-bromo-5-(chloromethyl)benzo[b]thiophene (443e)

Compound 443e was prepared according to the procedure reported in step-4 of scheme-257 from(7-bromobenzo[b]thiophen-5-yl)methanol (443d) (3.0 g, 12.34 mmol) in DCM (30 mL) using SOCl$_2$ (2.93 g, 24.62 mmol), DMF (0.5 mL) and stirring reaction at room temperature for 2 h. This gave after workup and purification by flash column chromatography (silica gel, eluting with 1-2% EtOAc in n-heptane) 7-bromo-5-(chloromethyl)benzo[b]thiophene (443e) (2.90 g, 90%) as an off-white solid; $^1$H NMR (300 MHz, DMSO-$d_6$) δ 8.15-7.92 (m, 2H), 7.89-7.78 (m, 1H), 7.60-7.42 (m, 1H), 4.98 (s, 2H).

Step-5: Preparation of Ethyl 2-(2-((7-bromobenzo[b]thiophen-5-yl)methoxy)-4-methylphenyl)acetate (443f)

Compound 443f was prepared according to the procedure reported in step-2 of scheme-152 from 7-bromo-5-(chloromethyl)benzo[b]thiophene (443e) (1.0 g, 3.82 mmol) using ethyl 2-(2-hydroxy-4-methylphenyl)acetate (269d) (1.85 g, 9.55 mmol) in DMF (20 mL) using $K_2CO_3$ (0.792 g, 5.73 mmol) and stirring at room temperature for 24h. This gave after workup and purification by flash column chromatography (silica gel, eluting with 1-3% EtOAc in n-heptane) ethyl 2-(2-((7-bromobenzo[b]thiophen-5-yl)methoxy)-4-methylphenyl)acetate (443f) (1.14 g, 71%) as an off-white solid; $^1$H NMR (300 MHz, Chloroform-d) δ 7.84-7.60 (m, 2H), 7.42 (dd, J=8.4, 1.7 Hz, 1H), 7.19 (s, 1H), 7.03 (d, J=7.5 Hz, 1H), 6.76-6.66 (m, 2H), 5.13 (d, J=5.9 Hz, 2H), 4.02 (q, J=7.1 Hz, 2H), 3.57 (s, 2H), 2.27 (s, 3H), 1.08 (t, J=7.1 Hz, 3H).

Step-6: Preparation of Ethyl 2-(2-((7-(3-(((tert-butoxycarbonyl)amino)methyl)phenyl)benzo[b]thiophen-5-yl)methoxy)-4-methylphenyl)acetate (443g)

Compound 443g was prepared according to the procedure reported in step-3 of scheme-1 from ethyl 2-(2-((7-bromobenzo[b]thiophen-5-yl)methoxy)-4-methylphenyl)acetate (443f) (1.0 g, 2.38 mmol) in acetonitrile (25 mL) using tert-butyl 3-(4,4,5,5-tetramethyl-1,3,2-dioxaborolan-2-yl)benzylcarbamate (3b) (1.18 g, 3.57 mmol), Pd(PPh$_3$)$_2$Cl$_2$ (0.167 g, 0.237 mmol) and a solution of Na$_2$CO$_3$ (0.756 g, 7.14 mmol) in water (8 mL) and heating under an nitrogen atmosphere at 90° C. for 2 h on an oil bath. This gave after workup, purification by flash column chromatography (silica gel, eluting with 1-3% EtOAc in n-heptane) ethyl 2-(2-((7-(3-(((tert-butoxycarbonyl)amino)methyl)phenyl)benzo[b]thiophen-5-yl)methoxy)-4-methylphenyl)acetate (443g) (1.0 g, 77%) as an off white semi-solid; $^1$H NMR (300 MHz, DMSO-$d_6$) δ 8.10 (d, J=8.3 Hz, 1H), 7.97 (s, 1H), 7.82 (s, 1H), 7.53-7.43 (m, 5H), 7.31 (d, J=4.4 Hz, 1H), 7.07 (d, J=7.5 Hz, 1H), 6.94 (s, 1H), 6.77-6.68 (m, 1H), 5.19 (s, 2H), 4.23 (d, J=6.2 Hz, 2H), 3.84 (q, J=7.1 Hz, 2H), 3.53 (s, 2H), 2.28 (s, 3H), 1.37 (s, 9H), 0.97 (t, J=7.1 Hz, 3H).

Step-7: Preparation of 2-(2-((7-(3-(((tert-butoxycarbonyl)amino)methyl)phenyl)benzo[b]thiophen-5-yl)methoxy)-4-methylphenyl)acetic Acid (443h)

Compound 443h was prepared according to the procedure reported in step-6 of scheme-1 from ethyl 2-(2-((7-(3-(((tert-butoxycarbonyl)amino)methyl)phenyl)benzo[b]thiophen-5-yl)methoxy)-4-methylphenyl)acetate (443g) (0.9 g, 1.64 mmol) in MeOH/THF (4.5 mL, 1:1 each) using a solution of lithium hydroxide hydrate (0.173 g, 4.12 mmol) in water (4.5 mL) and stirring at room temperature for 2 h. This gave after workup 2-(2-((7-(3-(((tert-butoxycarbonyl)amino)methyl)phenyl)benzo[b]thiophen-5-yl)methoxy)-4-methylphenyl)acetic acid (443h) (0.7 g, 82%) as an off white solid; $^1$H NMR (300 MHz, DMSO-$d_6$) δ 12.06 (s, 1H), 8.08 (d, J=8.3 Hz, 1H), 7.98 (s, 1H), 7.82 (s, 1H), 7.57-7.41 (m, 5H), 7.31 (t, J=4.6 Hz, 1H), 7.07 (d, J=7.5 Hz, 1H), 6.92 (s, 1H), 6.71 (d, J=7.5 Hz, 1H), 5.21 (s, 2H), 4.23 (d, J=6.2 Hz, 2H), 3.50 (s, 2H), 2.27 (s, 3H), 1.38 (s, 9H).

Step-8: Preparation of 2-(2-((7-(3-(aminomethyl)phenyl)benzo[b]thiophen-5-yl)methoxy)-4-methylphenyl)acetic Acid (443i)

Compound 443i was prepared according to the procedure reported in step-10 of scheme-257 from 2-(2-((7-(3-(((tert-butoxycarbonyl)amino)methyl)phenyl)benzo[b]thiophen-5-yl)methoxy)-4-methylphenyl)acetic acid (443h) (0.7 g, 1.35 mmol) in 1,4-dioxane (35 mL) using a solution of 1,4-dioxane.HCl (28%, 3.5 mL) and stirring for 4 h at room temperature. This gave after workup and purification by reverse phase column chromatography [C-18, eluting with water (containing 0.1% HCl)/acetonitrile (1:0 to 0:1)] 2-(2-((7-(3-(aminomethyl)phenyl)benzo[b]thiophen-5-yl)methoxy)-4-methylphenyl)acetic acid (443i) (22 mg) HCl salt as a white solid; $^1$H NMR (300 MHz, DMSO-$d_6$) δ 8.10 (d, J=8.3 Hz, 1H), 8.03 (s, 1H), 7.87 (s, 1H), 7.77 (s, 1H), 7.67-7.49 (m, 4H), 7.07 (d, J=7.5 Hz, 1H), 6.92 (s, 1H), 6.71 (d, J=7.5 Hz, 1H), 5.22 (s, 2H), 4.14 (s, 2H), 3.48 (s, 2H), 2.27 (s, 3H); MS (ES+): 418.10 (M+1); MS (ES-): 416.10 (M-1).

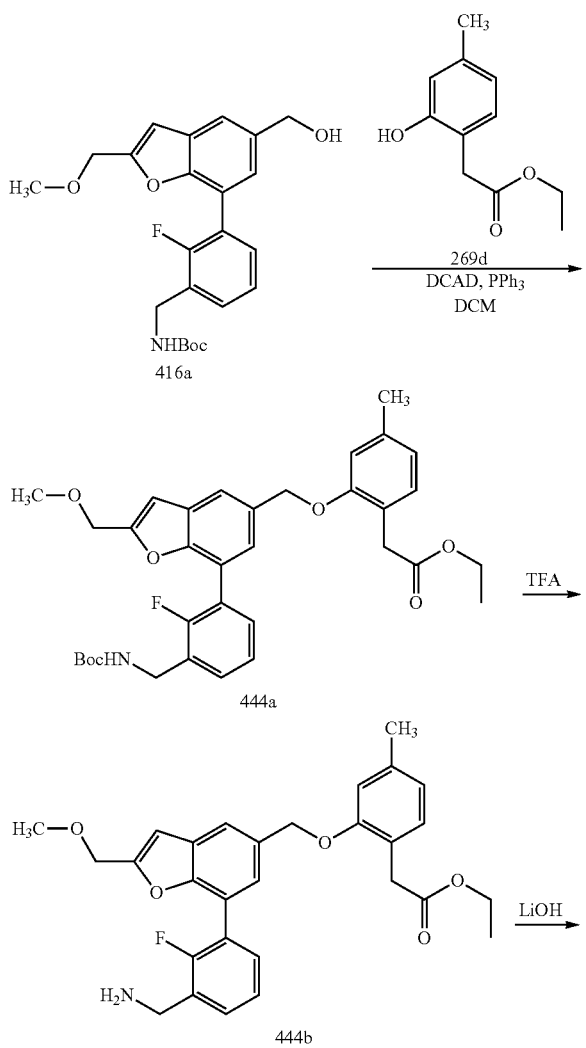

Scheme-444

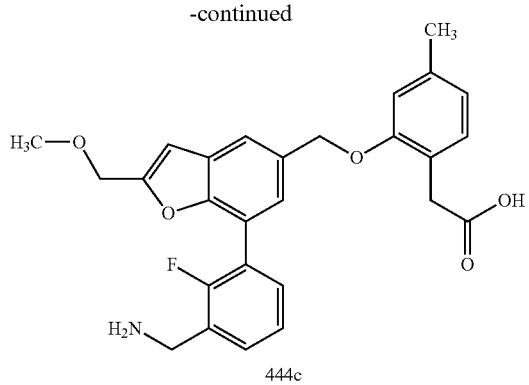

Preparation of 2-(2-((7-(3-(aminomethyl)-2-fluorophenyl)-2-(methoxymethyl)benzofuran-5-yl)methoxy)-4-methylphenyl)acetic Acid (444c)

Step-1: Preparation of Ethyl 2-(2-((7-(3-(((tert-butoxycarbonyl)amino)methyl)-2-fluorophenyl)-2-(methoxymethyl)benzofuran-5-yl)methoxy)-4-methylphenyl)acetate (444a)

Compound 444a was prepared according to the procedure reported in step-2 of scheme-23 from tert-butyl 2-fluoro-3-(5-(hydroxymethyl)-2-(methoxymethyl)benzofuran-7-yl)benzylcarbamate (416a) (513 mg, 1.236 mmol) in DCM (10 mL) using triphenylphosphine (405 mg, 1.545 mmol), ethyl 2-(2-hydroxy-4-methylphenyl)acetate (269d) (200 mg, 1.03 mmol) and a solution of (E)-bis(4-chlorobenzyl) diazene-1,2-dicarboxylate (DCAD, 567 mg, 1.545 mmol) in DCM (10 mL). This gave after workup and purification by flash column chromatography [silica gel, 40 g, eluting with hexanes/ethyl acetate (1:0 to 3:1 to 1:1)] ethyl 2-(2-((7-(3-(((tert-butoxycarbonyl)amino)methyl)-2-fluorophenyl)-2-(methoxymethyl)benzofuran-5-yl)methoxy)-4-methylphenyl)acetate (444a) (413 mg, 68%) as a colorless gum; $^1$H NMR (300 MHz, DMSO-$d_6$) δ 7.72 (d, J=1.6 Hz, 1H), 7.56-7.27 (m, 5H), 7.08 (d, J=7.5 Hz, 1H), 7.00 (s, 1H), 6.96 (d, J=1.4 Hz, 1H), 6.75-6.69 (m, 1H), 5.19 (s, 2H), 4.52 (s, 2H), 4.26 (d, J=6.1 Hz, 2H), 3.88 (q, J=7.1 Hz, 2H), 3.55 (s, 2H), 3.29 (s, 3H), 2.30 (s, 3H), 1.41 (s, 9H), 0.96 (t, J=7.1 Hz, 3H); $^{19}$F NMR (282 MHz, DMSO-$d_6$) δ−121.01; MS (ES+): 614.20 (M+Na).

Step-2: Preparation of Ethyl 2-(2-((7-(3-(aminomethyl)-2-fluorophenyl)-2-(methoxymethyl)benzofuran-5-yl)methoxy)-4-methylphenyl)acetate (444b)

Compound 444b was prepared according to the procedure reported in step-5 of scheme-1 from ethyl 2-(2-((7-(3-(((tert-butoxycarbonyl)amino)methyl)-2-fluorophenyl)-2-(methoxymethyl)benzofuran-5-yl)methoxy)-4-methylphenyl)acetate (444a) (395 mg, 0.668 mmol) in DCM (20 mL) using TFA (0.992 mL, 13.35 mmol). This gave after workup ethyl 2-(2-((7-(3-(aminomethyl)-2-fluorophenyl)-2-(methoxymethyl)benzofuran-5-yl)methoxy)-4-methylphenyl)acetate (444b) which was used as such for next step. MS (ES+): 492.20 (M+1).

Step-3: Preparation of 2-(2-((7-(3-(aminomethyl)-2-fluorophenyl)-2-(methoxymethyl)benzofuran-5-yl)methoxy)-4-methylphenyl)acetic Acid (444c)

Compound 444c was prepared according to the procedure reported in step-6 of scheme-1 from ethyl 2-(2-((7-(3-(aminomethyl)-2-fluorophenyl)-2-(methoxymethyl)benzofuran-5-yl)methoxy)-4-methylphenyl)acetate (444b) (0.668 mmol, from above step-2) in THF/methanol (10 mL, 1:1 each) using solution of lithium hydroxide hydrate (0.229 g, 5.34 mmol) in water (10 mL) and stirring at room temperature for 14 h. This gave after workup and purification by reverse-phase column chromatography [C-18 column, eluting with water (containing 0.1% HCl)/acetonitrile (1:0 to 0:1)] 2-(2-((7-(3-(aminomethyl)-2-fluorophenyl)-2-(methoxymethyl)benzofuran-5-yl)methoxy)-4-methylphenyl)acetic acid (444c) (165 mg, 53%) HCl salt as a white solid; $^1$H NMR (300 MHz, DMSO-$d_6$) δ 8.69 (s, 3H), 7.78 (d, J=1.6 Hz, 1H), 7.73 (td, J=7.4, 1.7 Hz, 1H), 7.66 (td, J=7.5, 1.7 Hz, 1H), 7.49-7.37 (m, 2H), 7.08 (d, J=7.5 Hz, 1H), 7.00 (s, 1H), 6.95-6.93 (m, 1H), 6.74-6.70 (m, 1H), 5.22 (s, 2H), 4.52 (s, 2H), 4.16 (s, 2H), 3.52 (s, 2H), 3.29 (s, 3H), 2.28 (s, 3H); $^{19}$F NMR (282 MHz, DMSO-$d_6$) δ−118.73; MS (ES+): 464.20 (M+1); MS (ES−): 462.20 (M−1); Analysis calculated for $C_{27}H_{26}FNO_5 \cdot HCl \cdot H_2O$: C, 62.61; H, 5.64; N, 2.70; Cl, 6.84; Found: C, 62.31; H, 5.53; N, 2.86; Cl, 7.08.

Scheme-445

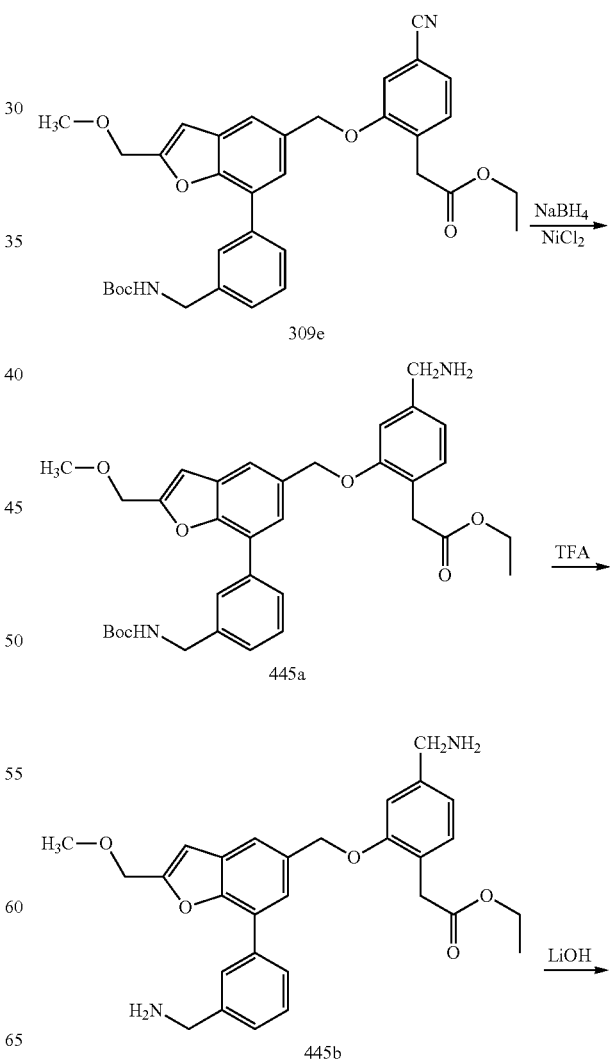

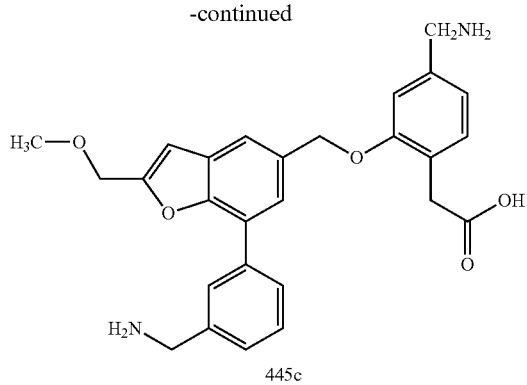

445c

Preparation of 2-(4-(aminomethyl)-2-((7-(3-(aminomethyl)phenyl)-2-(methoxymethyl)benzofuran-5-yl)methoxy)phenyl)acetic Acid (445c)

Step-1: Preparation of Ethyl 2-(4-(aminomethyl)-2-((7-(3-(((tert-butoxycarbonyl)amino)methyl)phenyl)-2-(methoxymethyl)benzofuran-5-yl)methoxy)phenyl)acetate (445a)

Compound 445a was prepared according to the procedure reported in step-2 of scheme-256 from ethyl 2-(2-((7-(3-(((tert-butoxycarbonyl)amino)methyl)phenyl)-2-(methoxymethyl)benzofuran-5-yl)methoxy)-4-cyanophenyl)acetate (309e) (300 mg, 0.513 mmol) in methanol (15 mL) using nickel (II) chloride hexahydrate (31 mg, 0.128 mmol) and sodium borohydride (116 mg, 3.08 mmol), using N1-(2-aminoethyl)ethane-1,2-diamine (0.111 mL, 1.026 mmol) for quenching. This gave after workup and purification by flash column chromatography [silica gel, eluting with chloroform/methanol (1:0 to 19:1)] ethyl 2-(4-(aminomethyl)-2-((7-(3-(((tert-butoxycarbonyl)amino)methyl)phenyl)-2-(methoxymethyl)benzofuran-5-yl)methoxy)phenyl)acetate (445a) (117 mgs); MS (ES+): 589.30 (M+1).

Step-2: Preparation of Ethyl 2-(4-(aminomethyl)-2-((7-(3-(aminomethyl)phenyl)-2-(methoxymethyl)benzofuran-5-yl)methoxy)phenyl)acetate (445b)

Compound 445b was prepared according to the procedure reported in step-5 of scheme-1 from ethyl 2-(4-(aminomethyl)-2-((7-(3-(((tert-butoxycarbonyl)amino)methyl)phenyl)-2-(methoxymethyl)benzofuran-5-yl)methoxy)phenyl)acetate (445a) (110 mg, 0.187 mmol) in DCM (10 mL) using TFA (0.278 mL, 3.74 mmol). This gave after workup ethyl 2-(4-(aminomethyl)-2-((7-(3-(aminomethyl)phenyl)-2-(methoxymethyl)benzofuran-5-yl)methoxy)phenyl)acetate (445b) which was used as such for next step. MS (ES+): 489.20 (M+1).

Step-3: Preparation of 2-(4-(aminomethyl)-2-((7-(3-(aminomethyl)phenyl)-2-(methoxymethyl)benzofuran-5-yl)methoxy)phenyl)acetic Acid (445c)

Compound 445c was prepared according to the procedure reported in step-6 of scheme-1 from ethyl 2-(4-(aminomethyl)-2-((7-(3-(aminomethyl)phenyl)-2-(methoxymethyl)benzofuran-5-yl)methoxy)phenyl)acetate (445b) (0.187 mmol, from above step-2) in THF/MeOH (4 mL, each) using a solution of lithium hydroxide hydrate (0.064 g, 1.496 mmol) in water (6 mL) stirring at room temperature for 19 h. This gave after workup and purification by reverse phase column [C18, eluting with water (containing 0.1% HCl)/acetonitrile (1:0 to 0:1)] 2-(4-(aminomethyl)-2-((7-(3-(aminomethyl)phenyl)-2-(methoxymethyl)benzofuran-5-yl)methoxy)phenyl)acetic acid (445c) (53 mg, 24% for three steps) HCl salt as a white solid; $^1$H NMR (300 MHz, DMSO-$d_6$) δ 8.46 (s, 6H), 8.02-7.99 (m, 1H), 7.93 (dt, J=7.4, 1.7 Hz, 1H), 7.74 (d, J=1.6 Hz, 1H), 7.67 (d, J=1.7 Hz, 1H), 7.63-7.53 (m, 2H), 7.40 (d, J=1.6 Hz, 1H), 7.25 (d, J=7.6 Hz, 1H), 7.05-6.96 (m, 2H), 5.27 (s, 2H), 4.59 (s, 2H), 4.14 (s, 2H), 4.00 (s, 2H), 3.60 (s, 2H), 3.33 (s, 3H); MS (ES+): 461.20 (M+1); MS (ES−): 460.20 (M−1); Analysis calculated for $C_{27}H_{28}N_2O_5 \cdot 2.0HCl \cdot 2.6H_2O$: C, 55.88; H, 6.11; N, 4.83; Cl, 12.22; Found: C, 55.84; H, 5.84; N, 4.79; Cl, 12.00.

Scheme-446

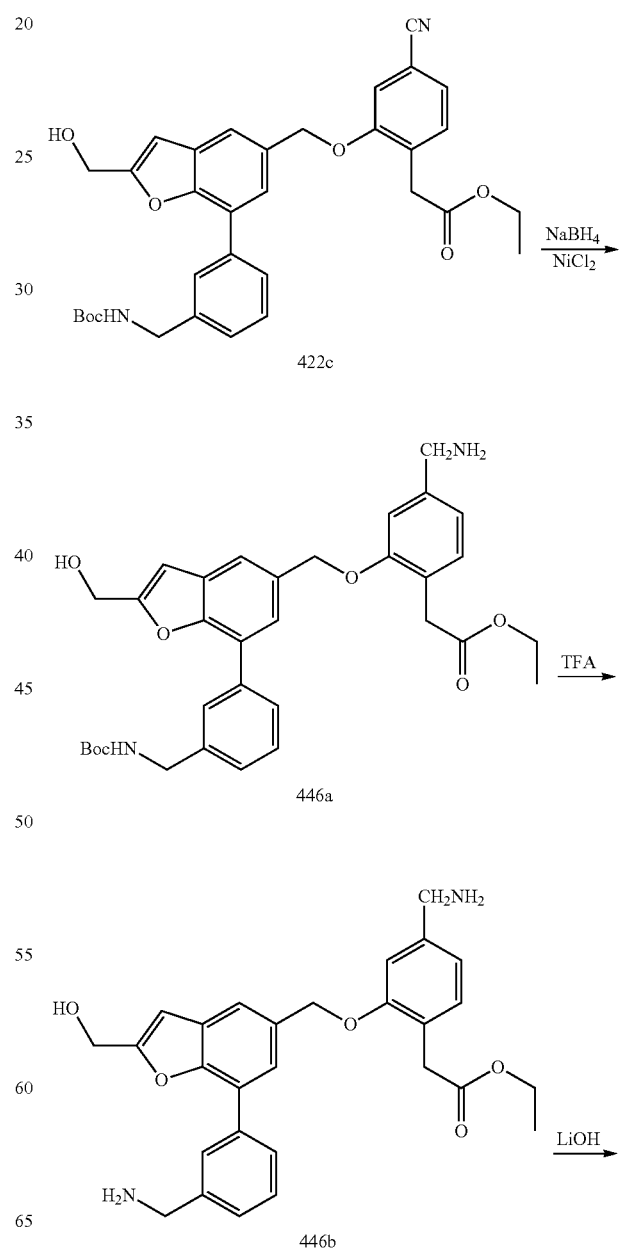

1363

-continued

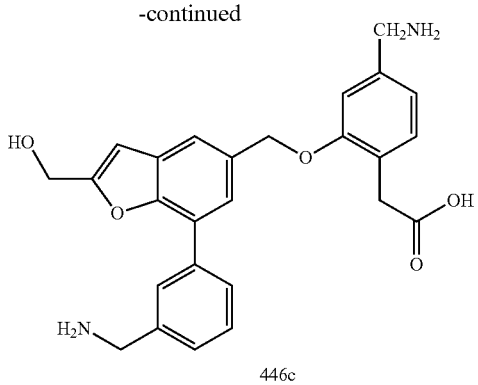

446c

Preparation of 2-(4-(aminomethyl)-2-((7-(3-(aminomethyl)phenyl)-2-(hydroxymethyl)benzofuran-5-yl)methoxy)phenyl)acetic Acid (446c)

Step-1: Preparation of Ethyl 2-(4-(aminomethyl)-2-((7-(3-(((tert-butoxycarbonyl)amino)methyl)phenyl)-2-(hydroxymethyl)benzofuran-5-yl)methoxy)phenyl)acetate (446a)

Compound 446a was prepared according to the procedure reported in step-2 of scheme-256 from ethyl 2-(2-((7-(3-(((tert-butoxycarbonyl)amino)methyl)phenyl)-2-(hydroxymethyl)benzofuran-5-yl)methoxy)-4-cyanophenyl)acetate (422c) (320 mg, 0.561 mmol) in methanol (15 mL) using nickel (II) chloride hexahydrate (33 mg, 0.140 mmol) and sodium borohydride (127 mg, 3.36 mmol), using N1-(2-aminoethyl)ethane-1,2-diamine (0.111 mL, 1.026 mmol) for quenching. This gave after workup and purification by flash column chromatography [silica gel, eluting with chloroform/methanol (1:0 to 19:1)] ethyl 2-(4-(aminomethyl)-2-((7-(3-(((tert-butoxycarbonyl)amino)methyl)phenyl)-2-(hydroxymethyl)benzofuran-5-yl)methoxy)phenyl)acetate (446a) (84 mg) as a colorless gum.

Step-2: Preparation of Ethyl 2-(4-(aminomethyl)-2-((7-(3-(aminomethyl)phenyl)-2-(hydroxymethyl)benzofuran-5-yl)methoxy)phenyl)acetate (446b)

Compound 446b was prepared according to the procedure reported in step-5 of scheme-1 from ethyl 2-(4-(aminomethyl)-2-((7-(3-(((tert-butoxycarbonyl)amino)methyl)phenyl)-2-(hydroxymethyl)benzofuran-5-yl)methoxy)phenyl)acetate (446a) (80 mg, 0.139 mmol) in DCM (10 mL) using TFA (0.207 mL, 2.78 mmol) and stirring at room temperature for 20 h. This gave after workup ethyl 2-(4-(aminomethyl)-2-((7-(3-(aminomethyl)phenyl)-2-(hydroxymethyl)benzofuran-5-yl)methoxy)phenyl)acetate (446b) which was used as such for next step.

Step-3: Preparation of 2-(4-(aminomethyl)-2-((7-(3-(aminomethyl)phenyl)-2-(hydroxymethyl)benzofuran-5-yl)methoxy)phenyl)acetic Acid (446c)

Compound 446c was prepared according to the procedure reported in step-6 of scheme-1 from ethyl 2-(4-(aminomethyl)-2-((7-(3-(aminomethyl)phenyl)-2-(hydroxymethyl)benzofuran-5-yl)methoxy)phenyl)acetate (446b) (0.139 mmol, from above step-2) in THF/MeOH (4 mL, each) using a solution of lithium hydroxide hydrate (0.048 g, 1.112 mmol) in water (6 mL) stirring at room temperature for 19 h. This gave after workup and purification by reverse phase column [C18, eluting with water (containing 0.1% HCl)/acetonitrile (1:0 to 0:1)] 2-(4-(aminomethyl)-2-((7-(3-(aminomethyl)phenyl)-2-(hydroxymethyl)benzofuran-5-yl)methoxy)phenyl)acetic acid (446c) (32 mg, 52%) HCl salt as a white solid; $^1$H NMR (300 MHz, DMSO-$d_6$) δ 12.27 (s, 1H), 8.44 (s, 6H), 8.04-8.02 (m, 1H), 7.95 (dt, J=7.4, 1.7 Hz, 1H), 7.70 (d, J=1.6 Hz, 1H), 7.63 (d, J=1.7 Hz, 1H), 7.62-7.51 (m, 2H), 7.39 (d, J=1.6 Hz, 1H), 7.25 (d, J=7.7 Hz, 1H), 7.01 (dd, J=7.7, 1.5 Hz, 1H), 6.85 (s, 1H), 5.56 (t, J=5.9 Hz, 1H), 5.26 (s, 2H), 4.62 (d, J=5.7 Hz, 2H), 4.14 (s, 2H), 4.00 (s, 2H), 3.60 (s, 2H); MS (ES+): 447.10 (M+1); MS (ES−): 445.10 (M−1); Analysis calculated for $C_{26}H_{26}N_2O_5 \cdot 2HCl \cdot 1.5H_2O$: C, 57.15; H, 5.72; N, 5.13; Cl, 12.98; Found: C, 57.12; H, 5.44; N, 5.13; Cl, 12.74.

Scheme-447

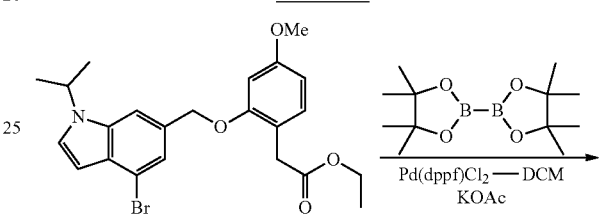

356a

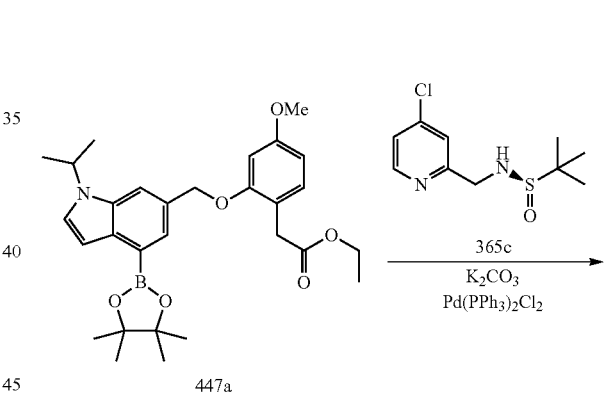

447a

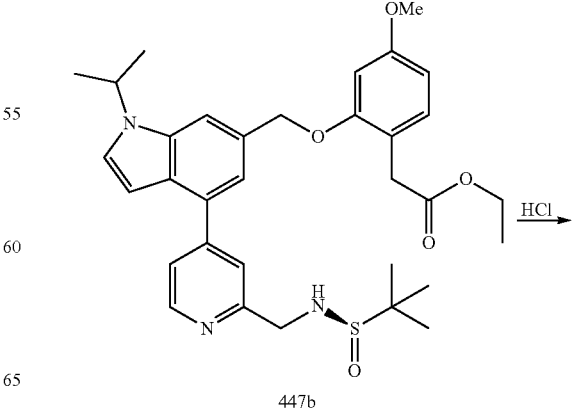

447b

-continued

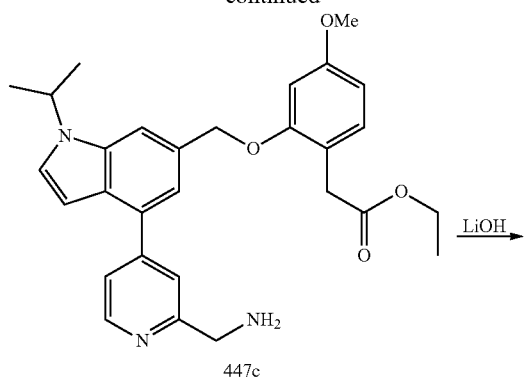

447c

447d

Preparation of 2-(2-((4-(2-(aminomethyl)pyridin-4-yl)-1-isopropyl-1H-indol-6-yl)methoxy)-4-methoxyphenyl)acetic Acid (447d)

Step-1: Preparation of Ethyl 2-(2-((1-isopropyl-4-(4,4,5,5-tetramethyl-1,3,2-dioxaborolan-2-yl)-1H-indol-6-yl)methoxy)-4-methoxyphenyl)acetate (447a)

Compound 447a was prepared according to the procedure reported in step-1 of scheme-59 from ethyl 2-(2-((4-bromo-1-isopropyl-1H-indol-6-yl)methoxy)-4-methoxyphenyl)acetate (356a) (0.85 g, 1.85 mmol), using bis(pinacolato) diboron (0.70 g, 2.77 mmol), potassium acetate (0.54 g, 5.54 mmol) and Pd(dppf)Cl2-DCM (0.23 g, 0.28 mmol) in anhydrous dioxane (15 mL) under an argon atmosphere and heating at 100° C. overnight. This gave after workup and purification by flash column chromatography [silica gel (24 g), eluting with EtOAc/methanol (9:1) in hexanes from 0-10%] ethyl 2-(2-((1-isopropyl-4-(4,4,5,5-tetramethyl-1,3,2-dioxaborolan-2-yl)-1H-indol-6-yl)methoxy)-4-methoxyphenyl)acetate (447a) (0.7 g, 75% yield) as a yellow solid; $^1$H NMR (300 MHz, DMSO-$d_6$) δ 7.70 (d, J=1.4 Hz, 1H), 7.53 (d, J=3.2 Hz, 1H), 7.47 (d, J=1.4 Hz, 1H), 7.09 (d, J=8.3 Hz, 1H), 6.76 (dd, J=3.1, 0.7 Hz, 1H), 6.70 (d, J=2.4 Hz, 1H), 6.46 (dd, J=8.3, 2.4 Hz, 1H), 5.17 (s, 2H), 4.76 (p, J=6.6 Hz, 1H), 4.00 (q, J=7.1 Hz, 2H), 3.74 (s, 3H), 3.51 (s, 2H), 1.45 (d, J=6.7 Hz, 6H), 1.32 (s, 12H), 1.05 (t, J=7.1 Hz, 3H); MS (ES+): 508.2 (M+1); 530.2 (M+Na).

Step-2: Preparation of Ethyl 2-(2-((4-(2-((1,1-dimethylethylsulfinamido)methyl)pyridin-4-yl)-1-isopropyl-1H-indol-6-yl)methoxy)-4-methoxyphenyl)acetate (447b)

Compound 447b was prepared according to the procedure reported in step-3 of scheme-1 from ethyl 2-(2-((1-isopropyl-4-(4,4,5,5-tetramethyl-1,3,2-dioxaborolan-2-yl)-1H-indol-6-yl)methoxy)-4-methoxyphenyl)acetate (447a) (350 mg, 0.69 mmol) in dioxane (4 mL) using (+)-(S)—N-((4-chloropyridin-2-yl)methyl)-2-methylpropane-2-sulfinamide (365c) (204 mg, 0.83 mmol), bis(triphenylphosphine)palladium(II) chloride (Pd(PPh$_3$)$_2$Cl$_2$) (73 mg, 0.10 mmol) and a solution of K$_2$CO$_3$ (286 mg, 2.07 mmol) in water (1 mL) under a nitrogen atmosphere heating at 90° C. for 3 h on oil bath. This gave after workup and purification by flash column chromatography [silica gel (12 g), eluting with DMA80 in DCM from 0-50%] ethyl 2-(2-((4-(2-((1,1-dimethylethylsulfinamido)methyl)pyridin-4-yl)-1-isopropyl-1H-indol-6-yl)methoxy)-4-methoxyphenyl)acetate (447b) (300 mg, 74% yield) as a yellow oil; MS (ES+): 592.3 (M+1).

Step-3: Preparation of Ethyl 2-(2-((4-(2-(aminomethyl)pyridin-4-yl)-1-isopropyl-1H-indol-6-yl)methoxy)-4-methoxyphenyl)acetate (447c)

Compound 447c was prepared according to the procedure reported in step-3 of scheme-305 from ethyl 2-(2-((4-(2-((1,1-dimethylethylsulfinamido)methyl)pyridin-4-yl)-1-isopropyl-1H-indol-6-yl)methoxy)-4-methoxyphenyl)acetate (447b) (300 mg, 0.51 mmol) in DCM (5 mL) using HCl (4 M in dioxane; 0.380 mL, 1.52 mmol) and stirring at room temperature for 1 h. purification by flash column chromatography [silica gel (12 g), eluting with DMA80 in DCM from 0-70%] ethyl 2-(2-((4-(2-(aminomethyl)pyridin-4-yl)-1-isopropyl-1H-indol-6-yl)methoxy)-4-methoxyphenyl)acetate (447c) (170 mg, 69% yield) as a pale yellow oil; MS (ES+): 488.3 (M+1).

Step-4: Preparation of 2-(2-((4-(2-(aminomethyl)pyridin-4-yl)-1-isopropyl-1H-indol-6-yl)methoxy)-4-methoxyphenyl)acetic Acid (447d)

Compound 447d was prepared according to the procedure reported in step-6 of scheme-1 from ethyl 2-(2-((4-(2-(aminomethyl)pyridin-4-yl)-1-isopropyl-1H-indol-6-yl)methoxy)-4-methoxyphenyl)acetate (447c) (170 mg, 0.35 mmol) in MeOH/THF (4 mL each) using a solution of lithium hydroxide (117 mg, 2.79 mmol) in water (1 mL). This gave after workup and purification by reverse phase column [C18 (50 g), eluting with ACN in water from 0-100%] 2-(2-((4-(2-(aminomethyl)pyridin-4-yl)-1-isopropyl-1H-indol-6-yl)methoxy)-4-methoxyphenyl)acetic acid (447d) (105 mg, 66% yield) free base as a white solid; $^1$H NMR (300 MHz, DMSO-$d_6$) δ 8.58 (d, J=5.1 Hz, 1H), 8.13-8.07 (m, 1H), 7.72 (d, J=3.5 Hz, 2H), 7.64 (d, J=3.3 Hz, 1H), 7.54 (d, J=1.2 Hz, 1H), 7.02 (d, J=8.2 Hz, 1H), 6.74-6.70 (m, 1H), 6.60 (d, J=2.4 Hz, 1H), 6.40 (dd, J=8.2, 2.4 Hz, 1H), 5.27 (s, 2H), 4.83 (p, J=6.6 Hz, 1H), 4.05 (s, 2H), 3.70 (s, 3H), 3.36 (s, 2H), 1.50 (d, J=6.6 Hz, 6H); MS (ES+): 460.2 (M+1); MS (ES−): 458.2 (M−1); Analysis calculated for $C_{27}H_{29}N_3O_4 \cdot H_2O$: C, 67.91; H, 6.54; N, 8.80; Found: C, 68.04; H, 6.46; N, 8.80.

Scheme-448

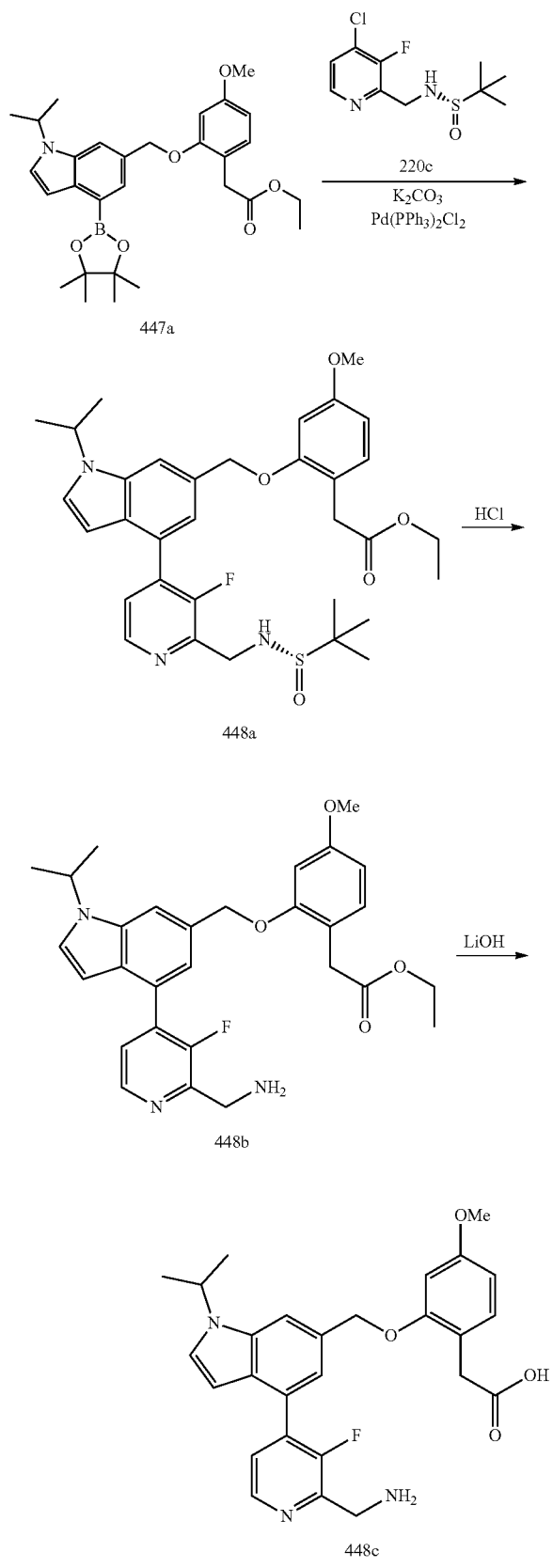

Preparation of 2-(2-((4-(2-(aminomethyl)-3-fluoropyridin-4-yl)-1-isopropyl-1H-indol-6-yl)methoxy)-4-methoxyphenyl)acetic Acid (448c)

Step-1: Preparation of Ethyl 2-(2-((4-(2-((1,1-dimethylethylsulfinamido)methyl)-3-fluoropyridin-4-yl)-1-isopropyl-1H-indol-6-yl)methoxy)-4-methoxyphenyl)acetate (448a)

Compound 448a was prepared according to the procedure reported in step-3 of scheme-1 from ethyl 2-(2-((1-isopropyl-4-(4,4,5,5-tetramethyl-1,3,2-dioxaborolan-2-yl)-1H-indol-6-yl)methoxy)-4-methoxyphenyl)acetate (447a) (350 mg, 0.69 mmol) in dioxane (4 mL) using (+)-(S)—N-((4-chloro-3-fluoropyridin-2-yl)methyl)-2-methylpropane-2-sulfinamide (220c) (219 mg, 0.83 mmol), bis(triphenylphosphine)palladium(II) chloride (Pd(PPh$_3$)$_2$Cl$_2$) (73 mg, 0.10 mmol) and a solution of K$_2$CO$_3$ (286 mg, 2.07 mmol) in water (1 mL) under a nitrogen atmosphere heating at 90° C. for 3 h on oil bath. This gave after workup and purification by flash column chromatography [silica gel (12 g), eluting with DMA80 in DCM from 0-50%] ethyl 2-(2-((4-(2-((1,1-dimethylethylsulfinamido)methyl)-3-fluoropyridin-4-yl)-1-isopropyl-1H-indol-6-yl)methoxy)-4-methoxyphenyl)acetate (448a) (300 mg, 71% yield) as a yellow oil; MS (ES+): 610.3 (M+1); 622.3 (M+Na).

Step-2: Preparation of Ethyl 2-(2-((4-(2-(aminomethyl)-3-fluoropyridin-4-yl)-1-isopropyl-1H-indol-6-yl)methoxy)-4-methoxyphenyl)acetate (448b)

Compound 448b was prepared according to the procedure reported in step-3 of scheme-305 from ethyl 2-(2-((4-(2-((1,1-dimethylethylsulfinamido)methyl)-3-fluoropyridin-4-yl)-1-isopropyl-1H-indol-6-yl)methoxy)-4-methoxyphenyl)acetate (448a) (300 mg, 0.49 mmol) in DCM (5 mL) using HCl (4 M in dioxane; 0.37 mL, 1.48 mmol) and stirring at room temperature for 1 h. purification by flash column chromatography [silica gel (12 g), eluting with DMA80 in DCM from 0-70%] ethyl 2-(2-((4-(2-(aminomethyl)-3-fluoropyridin-4-yl)-1-isopropyl-1H-indol-6-yl)methoxy)-4-methoxyphenyl)acetate (448b) (240 mg, 96% yield) as a pale yellow oil; $^1$H NMR (300 MHz, DMSO-d$_6$) δ 8.46 (d, J=4.9 Hz, 1H), 8.35 (d, J=5.2 Hz, 1H), 7.74 (s, 1H), 7.48 (t, J=5.3 Hz, 1H), 7.21 (t, J=1.3 Hz, 1H), 7.10 (d, J=8.3 Hz, 1H), 6.71 (d, J=2.4 Hz, 1H), 6.47 (dd, J=8.3, 2.4 Hz, 1H), 6.36 (t, J=3.0 Hz, 1H), 5.25 (s, 2H), 4.82 (p, J=6.7 Hz, 1H), 3.95-3.92 (m, 2H), 3.91-3.86 (m, 2H), 3.54 (s, 2H), 3.17 (s, 3H), 1.50 (d, J=6.7 Hz, 6H), 0.97 (t, J=7.1 Hz, 3H); MS (ES+): 506.2 (M+1).

Step-3: Preparation of 2-(2-((4-(2-(aminomethyl)-3-fluoropyridin-4-yl)-1-isopropyl-1H-indol-6-yl)methoxy)-4-methoxyphenyl)acetic Acid (448c)

Compound 448c was prepared according to the procedure reported in step-6 of scheme-1 from ethyl 2-(2-((4-(2-(aminomethyl)-3-fluoropyridin-4-yl)-1-isopropyl-1H-indol-6-yl)methoxy)-4-methoxyphenyl)acetate (448b) (170 mg, 0.35 mmol) in MeOH/THF (4 mL each) using a solution of lithium hydroxide (159 mg, 3.80 mmol) in water (1 mL). This gave after workup and purification by reverse phase column [C18 (50 g), eluting with ACN in water from 0-100%] 2-(2-((4-(2-(aminomethyl)-3-fluoropyridin-4-yl)-1-isopropyl-1H-indol-6-yl)methoxy)-4-methoxyphenyl) acetic acid (448c) (135 mg, 60% yield) as a white solid; $^1$H NMR (300 MHz, DMSO-d$_6$) δ 8.46 (d, J=5.0 Hz, 1H), 7.77

(s, 1H), 7.61 (d, J=3.3 Hz, 1H), 7.51 (t, J=5.3 Hz, 1H), 7.27 (t, J=1.3 Hz, 1H), 7.09 (d, J=8.3 Hz, 1H), 6.68 (d, J=2.4 Hz, 1H), 6.46 (dd, J=8.3, 2.4 Hz, 1H), 6.37 (t, J=2.9 Hz, 1H), 5.26 (s, 2H), 4.82 (h, J=6.6 Hz, 1H), 3.98 (d, J=2.1 Hz, 2H), 3.73 (s, 3H), 3.47 (s, 2H), 1.49 (d, J=6.6 Hz, 6H); $^{19}$F NMR (282 MHz, DMSO) δ −130.79; MS (ES+): 478.2 (M+1); MS (ES−): 476.2 (M−1); Analysis calculated for $C_{27}H_{28}FN_3O_4 \cdot 0.5H_2O$: C, 66.65; H, 6.01; N, 8.64; Found: C, 66.45; H, 5.96; N, 8.57.

Scheme-449

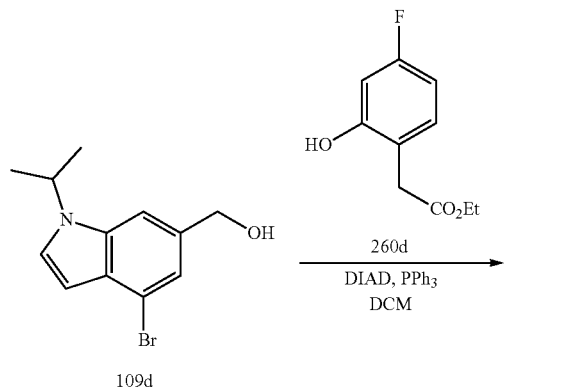

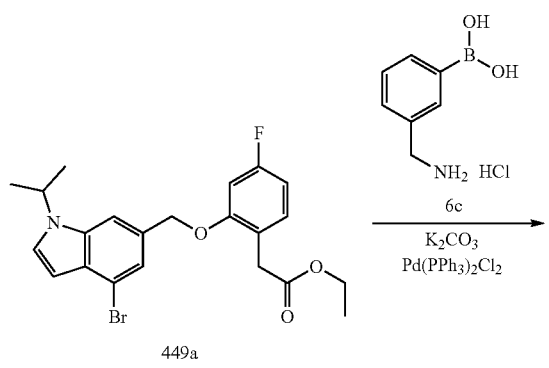

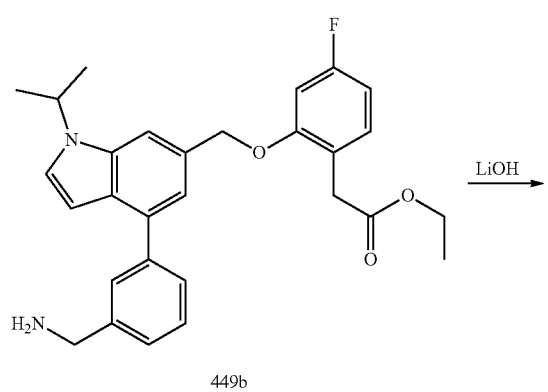

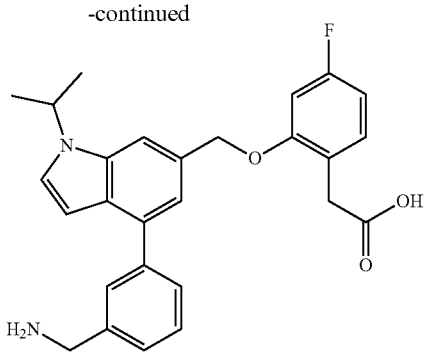

449c

Preparation of 2-(2-((4-(3-(aminomethyl)phenyl)-1-isopropyl-1H-indol-6-yl)methoxy)-4-fluorophenyl) acetic Acid (449c)

Step-1: Preparation of Ethyl 2-(2-((4-bromo-1-isopropyl-1H-indol-6-yl)methoxy)-4-fluorophenyl)acetate (449a)

Compound 449a was prepared according to the procedure reported in step-2 of scheme-23 from (4-bromo-1-isopropyl-1H-indol-6-yl)methanol (109d) (1.56 g, 5.82 mmol) in THF using triphenylphosphine (1.68 g, 6.40 mmol), ethyl 2-(4-fluoro-2-hydroxyphenyl)acetate (260d) (1.27 g, 6.40 mmol) and DIAD (1.24 mL, 6.40 mmol). This gave after workup and purification by flash column chromatography [silica gel, 40 g, eluting with EtOAc/methanol (9:1) in hexane from 0-30%] ethyl 2-(2-((4-bromo-1-isopropyl-1H-indol-6-yl)methoxy)-4-fluorophenyl)acetate (449a) (1 g, 38% yield) as a light yellow oil; $^1$H NMR (300 MHz, DMSO-$d_6$) δ 7.66-7.63 (m, 2H), 7.28 (d, J=1.1 Hz, 1H), 7.24 (dd, J=8.4, 6.9 Hz, 1H), 7.02 (dd, J=11.4, 2.5 Hz, 1H), 6.73 (td, J=8.5, 2.5 Hz, 1H), 6.42 (dd, J=3.3, 0.8 Hz, 1H), 5.20 (s, 2H), 4.75 (h, J=6.6 Hz, 1H), 4.02 (q, J=7.1 Hz, 2H), 3.60 (s, 2H), 1.47 (d, J=6.6 Hz, 6H), 1.07 (t, J=7.1 Hz, 3H); MS (ES+): 449.1 (M+1); MS (ES−): 447.0 (M−1).

Step-2: Preparation of Ethyl 2-(2-((4-(3-(aminomethyl)phenyl)-1-isopropyl-1H-indol-6-yl)methoxy)-4-fluorophenyl)acetate (449b)

Compound 449b was prepared according to the procedure reported in step-3 of scheme-1 from ethyl 2-(2-((4-bromo-1-isopropyl-1H-indol-6-yl)methoxy)-4-fluorophenyl)acetate (449a) (150 mg, 0.34 mmol) in dioxane (5 mL) using (3-(aminomethyl)phenyl)boronic acid hydrochloride (6c) (82 mg, 0.44 mmol), bis(triphenylphosphine)palladium(II) chloride (Pd(PPh$_3$)$_2$Cl$_2$) (35.2 mg, 0.05 mmol) and a solution of K$_2$CO$_3$ (139 mg, 1.00 mmol) in water (1.0 mL) under an argon atmosphere heating at 90° C. for 3 h on oil bath. This gave after workup, purification by flash column chromatography [silica gel, 12 g, eluting with DMA80 in DCM from 0-50%] ethyl 2-(2-((4-(3-(aminomethyl)phenyl)-1-isopropyl-H-indol-6-yl)methoxy)-4-fluorophenyl)acetate (449b) (110 mg, 69% yield) as a white solid; $^1$H NMR (300 MHz, DMSO-$d_6$) δ 7.63 (s, 1H), 7.61-7.56 (m, 2H), 7.48 (d, J=7.7 Hz, 1H), 7.42 (t, J=7.4 Hz, 1H), 7.33 (d, J=7.5 Hz, 1H), 7.23 (dd, J=8.3, 6.9 Hz, 1H), 7.16 (d, J=1.3 Hz, 1H), 7.05 (dd, J=11.4, 2.6 Hz, 1H), 6.72 (td, J=8.4, 2.5 Hz, 1H), 6.59 (d, J=3.3 Hz, 1H), 5.26 (s, 2H), 4.80 (p, J=6.6 Hz, 1H), 3.90 (q, J=7.1 Hz, 2H), 3.80 (s, 2H), 3.60 (s, 2H), 1.49 (d, J=6.6 Hz, 6H), 0.97 (t, J=7.1 Hz, 3H); MS (ES+): 475.2 (M+1).

Step-3: Preparation of 2-(2-((4-(3-(aminomethyl) phenyl)-1-isopropyl-1H-indol-6-yl)methoxy)-4-fluorophenyl)acetic Acid (449c)

Compound 449c was prepared according to the procedure reported in step-6 of scheme-1 from ethyl 2-(2-((4-(3-(aminomethyl)phenyl)-1-isopropyl-1H-indol-6-yl) methoxy)-4-fluorophenyl)acetate (449b) (110 mg, 0.23 mmol) in MeOH (4 mL), THF (4 mL) using a solution of lithium hydroxide (78 mg, 1.85 mmol) in water (1 mL). This gave after workup and purification by reverse phase column [C18 (50 g), eluting with ACN in water from 0-100%] 2-(2-((4-(3-(aminomethyl)phenyl)-1-isopropyl-1H-indol-6-yl)methoxy)-4-fluorophenyl)acetic acid (449c) (70 mg, 68% yield) as a white solid; $^1$H NMR (300 MHz, DMSO-d$_6$) δ 8.12 (t, J=1.8 Hz, 1H), 7.76 (dt, J=7.8, 1.4 Hz, 1H), 7.62 (s, 1H), 7.57 (d, J=3.2 Hz, 1H), 7.47-7.39 (m, 2H), 7.29 (dt, J=7.6, 1.4 Hz, 1H), 7.09 (dd, J=8.3, 7.1 Hz, 1H), 6.88 (dd, J=11.5, 2.5 Hz, 1H), 6.66-6.55 (m, 2H), 5.28 (s, 2H), 4.81 (hept, J=6.5 Hz, 1H), 3.97 (s, 2H), 3.38 (s, 2H), 1.50 (d, J=6.6 Hz, 6H); $^{19}$F NMR (282 MHz, DMSO-d$_6$) δ−115.20; MS (ES−): 445.2 (M−1); Analysis calculated for C$_{27}$H$_{27}$FN$_2$O$_3$.0.5H$_2$O: C, 71.19; H, 6.20; N, 6.15; Found: C, 71.04; H, 6.29; N, 6.12.

Scheme-450

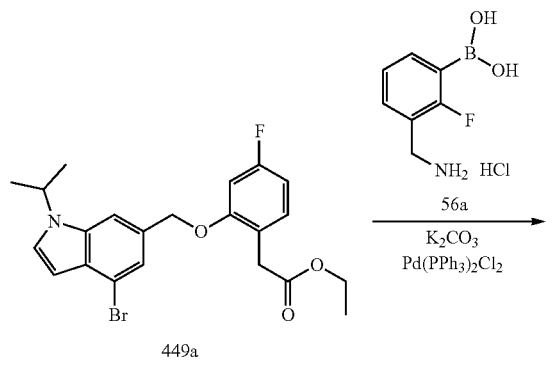

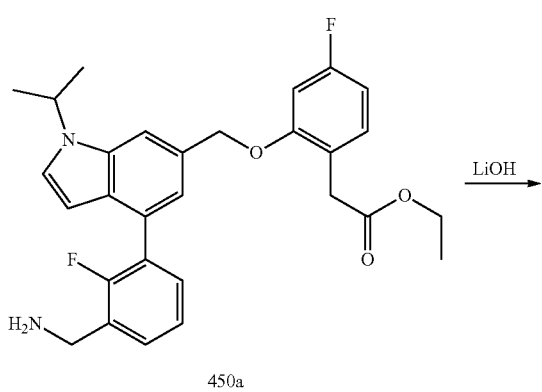

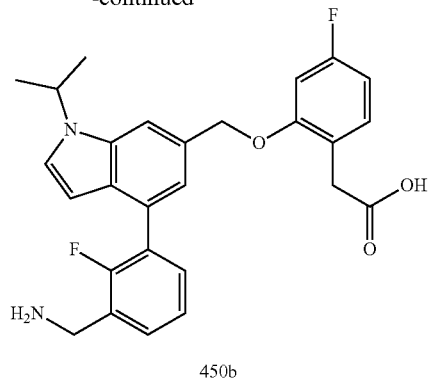

450b

Preparation of 2-(2-((4-(3-(aminomethyl)-2-fluorophenyl)-1-isopropyl-1H-indol-6-yl)methoxy)-4-fluorophenyl)acetic Acid (450b)

Step-1: Preparation of Ethyl 2-(2-((4-(3-(aminomethyl)-2-fluorophenyl)-1-isopropyl-1H-indol-6-yl) methoxy)-4-fluorophenyl)acetate (450a)

Compound 450a was prepared according to the procedure reported in step-3 of scheme-1 from ethyl 2-(2-((4-bromo-1-isopropyl-1H-indol-6-yl)methoxy)-4-fluorophenyl)acetate (449a) (150 mg, 0.34 mmol) in dioxane (5 mL) using 3-(aminomethyl)-2-fluorophenylboronic acid hydrochloride (56a) (89 mg, 0.44 mmol), bis(triphenylphosphine)palladium(II) chloride (Pd(PPh$_3$)$_2$Cl$_2$) (35 mg, 0.05 mmol) and a solution of K$_2$CO$_3$ (139 mg, 1.00 mmol) in water (1.0 mL) under an argon atmosphere heating at 90° C. for 3 h on oil bath. This gave after workup, purification by flash column chromatography [silica gel, 12 g, eluting with DMA80 in DCM from 0-50%] ethyl 2-(2-((4-(3-(aminomethyl)-2-fluorophenyl)-1-isopropyl-1H-indol-6-yl)methoxy)-4-fluorophenyl)acetate (450a) (130 mg, 79% yield) as a yellow syrup; $^1$H NMR (300 MHz, DMSO-d$_6$) δ 7.60-7.57 (m, 1H), 7.56-7.53 (m, 2H), 7.37 (td, J=7.4, 2.0 Hz, 1H), 7.30-7.19 (m, 2H), 7.10 (t, J=1.3 Hz, 1H), 7.05 (dd, J=11.4, 2.5 Hz, 1H), 6.72 (td, J=8.5, 2.5 Hz, 1H), 6.31-6.26 (m, 1H), 5.25 (s, 2H), 4.80 (p, J=6.7 Hz, 1H), 3.89 (q, J=7.1 Hz, 2H), 3.83 (s, 2H), 3.59 (s, 2H), 1.49 (d, J=6.6 Hz, 6H), 0.97 (t, J=7.1 Hz, 3H); $^{19}$F NMR (282 MHz, DMSO-d$_6$) δ−112.71, 122.60; MS (ES+): 493.2 (M+1).

Step-2: Preparation of 2-(2-((4-(3-(aminomethyl)-2-fluorophenyl)-1-isopropyl-1H-indol-6-yl)methoxy)-4-fluorophenyl)acetic Acid (450b)

Compound 450b was prepared according to the procedure reported in step-6 of scheme-1 from ethyl 2-(2-((4-(3-(aminomethyl)-2-fluorophenyl)-1-isopropyl-1H-indol-6-yl) methoxy)-4-fluorophenyl)acetate (450a) (130 mg, 0.26 mmol) in MeOH (4 mL), THF (4 mL) using a solution of lithium hydroxide (89 mg, 2.11 mmol) in water (1 mL). This gave after workup and purification by reverse phase column [C18 (50 g), eluting with ACN in water from 0-100%] 2-(2-((4-(3-(aminomethyl)-2-fluorophenyl)-1-isopropyl-1H-indol-6-yl)methoxy)-4-fluorophenyl)acetic acid (450b) (105 mg, 86% yield) as a white solid; $^1$H NMR (300 MHz, DMSO-d$_6$) δ 7.66 (d, J=3.1 Hz, 1H), 7.54 (d, J=3.3 Hz, 1H), 7.53-7.41 (m, 2H), 7.30-7.16 (m, 3H), 6.98 (dd, J=11.4, 2.5 Hz, 1H), 6.68 (td, J=8.5, 2.5 Hz, 1H), 6.32 (dd, J=3.3, 1.9

Hz, 1H), 5.27 (s, 2H), 4.81 (h, J=6.6 Hz, 1H), 3.88 (s, 2H), 3.49 (s, 2H), 1.48 (d, J=6.6 Hz, 6H); $^{19}$F NMR (282 MHz, DMSO) δ−113.77, 121.06; MS (ES+): 465.2 (M+1); MS (ES−): 463.2 (M−1); Analysis calculated for $C_{27}H_{26}F_2N_2O_3 \cdot 0.25H_2O$: C, 69.14; H, 5.70; N, 5.97; Found: C, 69.33; H, 5.66; N, 5.67.

Scheme-451

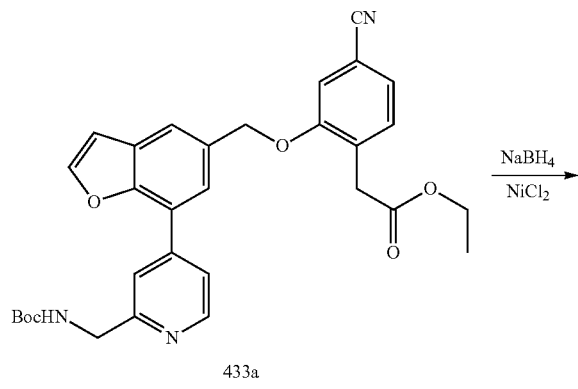

433a

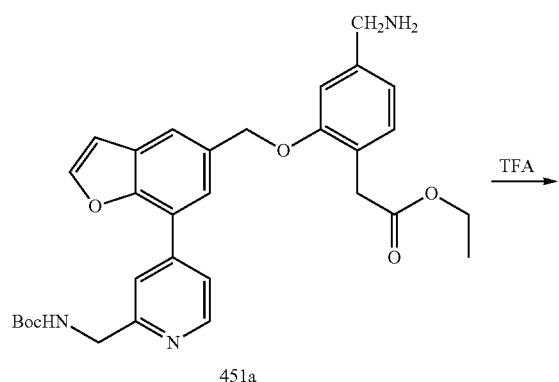

451a

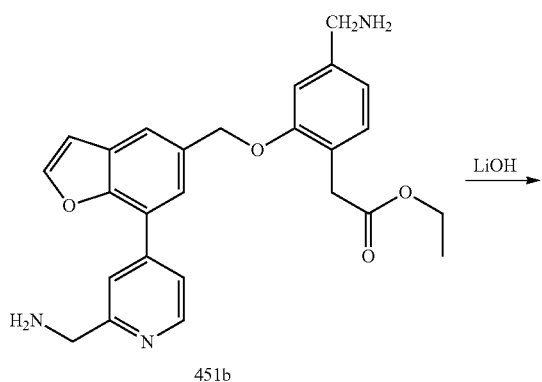

451b

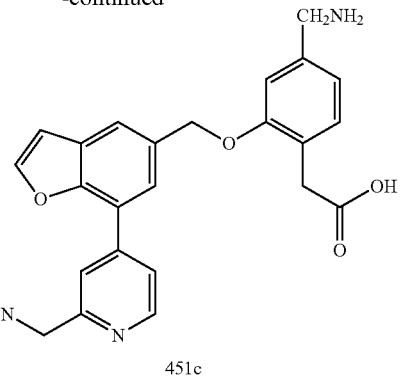

451c

Preparation of 2-(4-(aminomethyl)-2-((7-(2-(aminomethyl)pyridin-4-yl)benzofuran-5-yl)methoxy)phenyl)acetic Acid (451c)

Step-1: Preparation of Ethyl 2-(4-(aminomethyl)-2-((7-(2-(((tert-butoxycarbonyl)amino)methyl)pyridin-4-yl)benzofuran-5-yl)methoxy)phenyl)acetate (451a)

Compound 451a was prepared according to the procedure reported in step-2 of scheme-256 from ethyl 2-(2-((7-(2-(((tert-butoxycarbonyl)amino)methyl)pyridin-4-yl)benzofuran-5-yl)methoxy)-4-cyanophenyl)acetate (433a) (350 mg, 0.646 mmol) in methanol (20 mL) using nickel (II) chloride hexahydrate (38 mg, 0.162 mmol) and sodium borohydride (147 mg, 3.88 mmol), using N1-(2-aminoethyl)ethane-1,2-diamine (0.140 mL, 1.292 mmol) for quenching. This gave after workup and purification by flash column chromatography [silica gel, eluting with chloroform/methanol (1:0 to 4:1)] ethyl 2-(4-(aminomethyl)-2-((7-(2-(((tert-butoxycarbonyl)amino)methyl)pyridin-4-yl)benzofuran-5-yl)methoxy)phenyl)acetate (451a) (83 mg) as a colorless gum.

Step-2: Preparation of Ethyl 2-(4-(aminomethyl)-2-((7-(2-(aminomethyl)pyridin-4-yl)benzofuran-5-yl)methoxy)phenyl)acetate (451b)

Compound 451b was prepared according to the procedure reported in step-5 of scheme-1 from ethyl 2-(4-(aminomethyl)-2-((7-(2-(((tert-butoxycarbonyl)amino)methyl)pyridin-4-yl)benzofuran-5-yl)methoxy)phenyl)acetate (451a) (83 mg, 0.152 mmol) in DCM (8 mL) using TFA (0.226 mL, 3.04 mmol) and stirring at room temperature for 22 h. This gave after workup ethyl 2-(4-(aminomethyl)-2-((7-(2-(aminomethyl)pyridin-4-yl)benzofuran-5-yl)methoxy)phenyl)acetate (451b) which was used as such for next step. MS (ES+): 446.20 (M+1).

Step-3: Preparation of 2-(4-(aminomethyl)-2-((7-(2-(aminomethyl)pyridin-4-yl)benzofuran-5-yl)methoxy)phenyl)acetic Acid (451c)

Compound 451c was prepared according to the procedure reported in step-6 of scheme-1 from ethyl 2-(4-(aminomethyl)-2-((7-(2-(aminomethyl)pyridin-4-yl)benzofuran-5-yl)methoxy)phenyl)acetate (451b) (0.068 g, 0.152 mmol) in THF/MeOH (4 mL, each) using a solution of lithium hydroxide hydrate (0.052 g, 1.216 mmol) in water (4 mL) stirring at room temperature for 17 h. This gave after workup and purification by reverse phase column [C18, eluting with water (containing 0.1% HCl)/acetonitrile (1:0 to 0:1)] 2-(4-(aminomethyl)-2-((7-(2-(aminomethyl)pyridin-4-yl)benzofuran-5-yl)methoxy)phenyl)acetic acid (451c) (38 mg, 14% for 3 steps) HCl salt as a white solid; $^1$H NMR (300 MHz, DMSO-$d_6$) δ 8.78 (d, J=5.3 Hz, 1H), 8.51 (2s, 6H), 8.18 (d, J=2.2 Hz, 1H), 8.14-8.12 (m, 1H), 8.02 (dd, J=5.3, 1.7 Hz, 1H), 7.93-7.82 (m, 2H), 7.43 (d, J=1.6 Hz, 1H), 7.25 (d, J=7.6 Hz, 1H), 7.12 (d, J=2.2 Hz, 1H), 7.02 (dd, J=7.6, 1.5 Hz, 1H), 5.30 (s, 2H), 4.37-4.26 (m, 2H), 4.04-3.93 (m, 2H), 3.60 (s, 2H); MS (ES+): 418.10 (M+1); MS (ES−): 416.10 (M−1); Analysis calculated for $C_{24}H_{23}N_3O_4 \cdot 2.75HCl \cdot 3H_2O$: C, 50.41; H, 5.60; N, 7.35; Cl, 17.05; Found: C, 50.07; H, 5.53; N, 7.22; Cl, 17.01.

Scheme-452

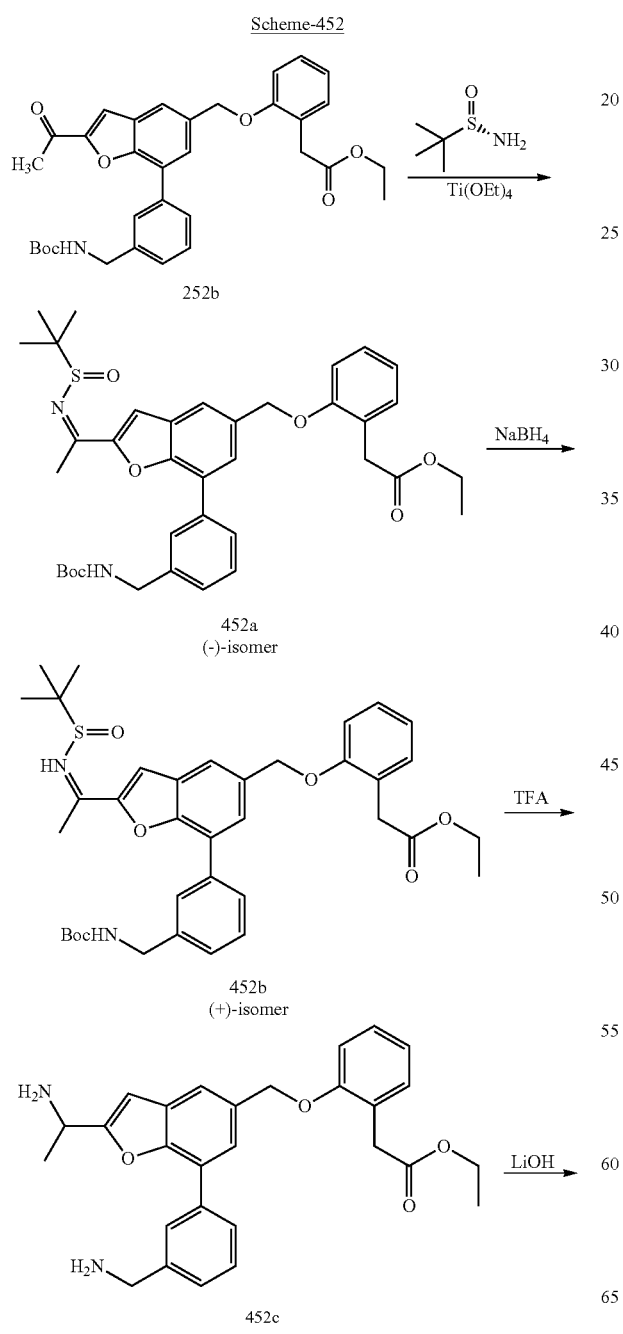

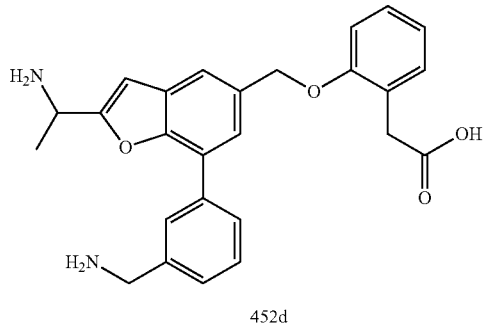 [SMILES: CC(N)c1cc2cc(COc3ccccc3CC(=O)O)cc(-c3cccc(CN)c3)c2o1]

452d

Preparation of 2-(2-((2-(1-aminoethyl)-7-(3-(aminomethyl)phenyl)benzofuran-5-yl)methoxy)phenyl) acetic Acid (452d)

Step-1: Preparation of (−)-(S,Z)-ethyl 2-(2-((7-(3-(((tert-butoxycarbonyl)amino)methyl)phenyl)-2-(1-((tert-butylsulfinyl)imino)ethyl)benzofuran-5-yl) methoxy)phenyl)acetate (452a)

Compound 452a was prepared according to the procedure reported in step-1 of scheme-258 from ethyl 2-(2-((2-acetyl-7-(3-(((tert-butoxycarbonyl)amino)methyl)phenyl)benzofuran-5-yl)methoxy)phenyl)acetate (252b) (500 mg, 0.897 mmol) and (S)-2-methylpropane-2-sulfinamide (136 mg, 1.121 mmol) in tetrahydrofuran (10 mL) using tetraethoxytitanium (0.376 mL, 1.793 mmol) and heating at reflux for 16 h. This gave after workup and purification by flash column chromatography [silica gel, eluting with hexanes/ethyl acetate (1:0 to 2:1)] (−)-(S,Z)-ethyl 2-(2-((7-(3-(((tert-butoxycarbonyl)amino)methyl)phenyl)-2-(1-((tert-butylsulfinyl)imino)ethyl)benzofuran-5-yl)methoxy)phenyl)acetate (452a) (319 mg, 64%) as a yellow gum; $^1$H NMR (300 MHz, DMSO-$d_6$) δ 7.92-7.74 (m, 5H), 7.52-7.39 (m, 2H), 7.34-7.20 (m, 3H), 7.15-7.07 (m, 1H), 6.96-6.88 (m, 1H), 5.27 (s, 2H), 4.22 (d, J=6.2 Hz, 2H), 3.93 (q, J=7.1 Hz, 2H), 3.64 (s, 2H), 2.73 (s, 3H), 1.38 (s, 9H), 1.26 (s, 9H), 0.97 (t, J=7.1 Hz, 3H); Optical rotation [α]$_D$=−45.13 (c=0.195, MeOH).

Step-2: Preparation of (+)-ethyl 2-(2-((7-(3-(((tert-butoxycarbonyl)amino)methyl)phenyl)-2-(1-((S)-1,1-dimethylethylsulfinamido)ethyl)benzofuran-5-yl) methoxy)phenyl)acetate (452b)

Compound 452b was prepared according to the procedure reported in step-2 of scheme-258 from (−)-(S,Z)-ethyl 2-(2-((7-(3-(((tert-butoxycarbonyl)amino)methyl)phenyl)-2-(1-((tert-butylsulfinyl)imino)ethyl)benzofuran-5-yl)methoxy)phenyl)acetate (452a) (300 mg, 0.454 mmol) in tetrahydrofuran (10 mL) using sodium borohydride (35 mg, 0.908 mmol) and stirring at room temperature for 18 h. This gave after workup and purification by flash column chromatography [silica gel, eluting with hexanes/10% methanol in ethyl acetate (1:0 to 1:1)] (+)-ethyl 2-(2-((7-(3-(((tert-butoxycarbonyl)amino)methyl)phenyl)-2-(1-((S)-1,1-dimethylethylsulfinamido)ethyl)benzofuran-5-yl)methoxy)phe nyl)acetate (452b) (160 mg, 53%) as a white solid; ¹H NMR (300 MHz, DMSO-d₆) δ 7.87 (s, 1H), 7.78 (d, J=7.8 Hz, 1H), 7.64 (d, J=1.6 Hz, 1H), 7.56-7.40 (m, 3H), 7.33-7.24 (m, 2H), 7.21 (dd, J=6.2 Hz, 1H), 7.11 (d, J=8.1 Hz, 1H), 6.94-6.85 (m, 2H), 5.91 (d, J=8.1 Hz, 1H), 5.22 (s, 2H), 4.64-4.48 (m, 1H), 4.23 (d, J=6.2 Hz, 2H), 3.93 (q, J=7.1 Hz, 2H), 3.62 (s, 2H), 1.56 (d, J=6.9 Hz, 3H), 1.38 (s, 9H), 1.14 (s, 9H), 0.99 (t, J=7.1 Hz, 3H); Optical rotation [α]$_D$=+14.4 (c=0.125, MeOH).

Step-3: Preparation of Ethyl 2-(2-((2-(1-amino-ethyl)-7-(3-(aminomethyl)phenyl)benzofuran-5-yl)methoxy)phenyl)acetate (452c)

Compound 452c was prepared according to the procedure reported in step-5 of scheme-1 from (+)-ethyl 2-(2-((7-(3-(((tert-butoxycarbonyl)amino)methyl)phenyl)-2-(1-((S)-1,1-dimethylethylsulfinamido)ethyl)benzofuran-5-yl)methoxy)phenyl)acetate (452b) (150 mg, 0.226 mmol) in DCM (12 mL) using TFA (0.336 mL, 4.53 mmol) and stirring at room temperature for 18 h. This gave after workup ethyl 2-(2-((2-(1-aminoethyl)-7-(3-(aminomethyl)phenyl)benzofuran-5-yl)methoxy)phenyl)acetate (452c) which was used as such for next step. MS (ES+): 459.20 (M+1).

Step-4: Preparation of 2-(2-((2-(1-aminoethyl)-7-(3-(aminomethyl)phenyl)benzofuran-5-yl)methoxy)phenyl)acetic Acid (452d)

Compound 452d was prepared according to the procedure reported in step-6 of scheme-1 from ethyl 2-(2-((2-(1-aminoethyl)-7-(3-(aminomethyl)phenyl)benzofuran-5-yl)methoxy)phenyl)acetate (452c) (0.226 mmol, from above step-3) in MeOH/THF (5 mL, each) using a solution of lithium hydroxide hydrate (77 mg, 1.808 mmol) in water (5 mL) and stirring at room temperature for 16 h. This gave after workup and purification by reverse phase column [C18, 100 g, eluting with MeCN in H₂O containing 0.1% HCl (1:0 to 0:1)] 2-(2-((2-(1-aminoethyl)-7-(3-(aminomethyl)phenyl)benzofuran-5-yl)methoxy)phenyl)acetic acid (452d)(20 mg, 21%) HCl salt as a white solid; ¹H NMR (300 MHz, DMSO-d₆) δ 12.21 (s, 1H), 8.92-8.82 (m, 3H), 8.66-8.48 (m, 3H), 8.22-8.19 (m, 1H), 7.98 (dt, J=7.3, 1.8 Hz, 1H), 7.76 (d, J=1.6 Hz, 1H), 7.70 (d, J=1.7 Hz, 1H), 7.62-7.51 (m, 2H), 7.23 (s, 1H), 7.21 (s, 1H), 7.11-7.05 (m, 2H), 6.90 (td, J=7.4, 1.1 Hz, 1H), 5.27 (s, 2H), 4.86-4.61 (m, 1H), 4.27-4.06 (m, 2H), 3.59 (s, 2H), 1.66 (d, J=6.9 Hz, 3H); MS (ES+): 431.20 (M+1); MS (ES−): 429.15 (M−1).

Scheme-453

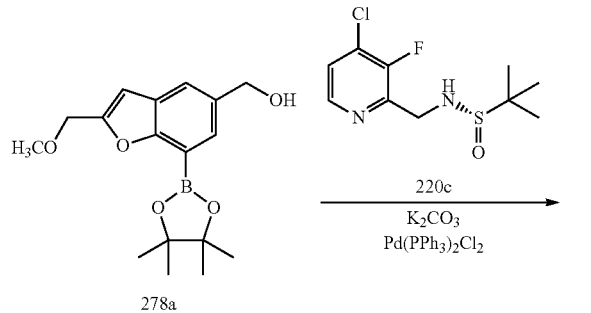

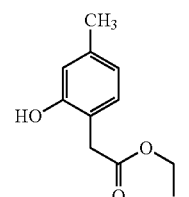

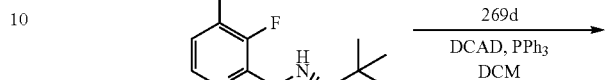

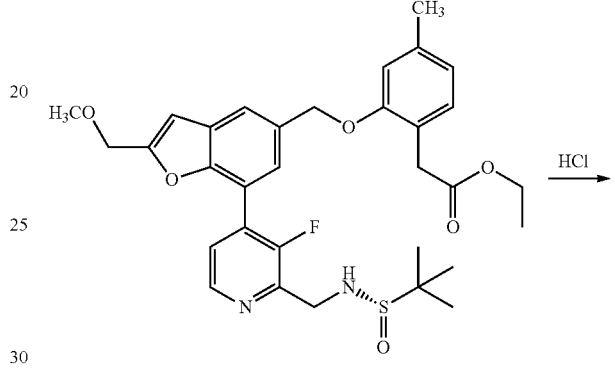

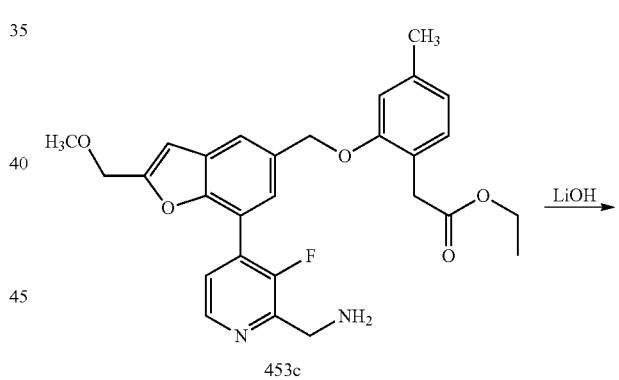

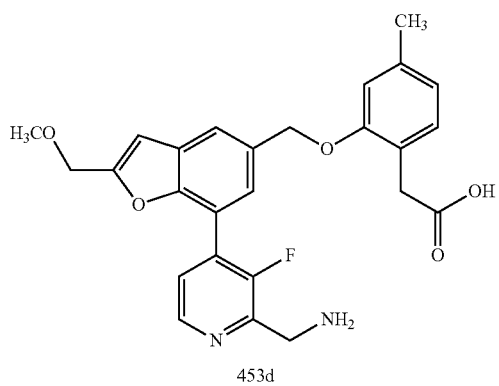 [SMILES: COCc1cc2cc(COc3cc(C)ccc3CC(=O)O)cc(-c3ccnc(CN)c3F)c2o1]

Preparation of 2-(2-((7-(2-(aminomethyl)-3-fluoro-pyridin-4-yl)-2-(methoxymethyl)benzofuran-5-yl)methoxy)-4-methylphenyl)acetic Acid (453d)

Step-1: Preparation of (+)-(S)—N-((3-fluoro-4-(5-(hydroxymethyl)-2-(methoxymethyl)benzofuran-7-yl)pyridin-2-yl)methyl)-2-methylpropane-2-sulfinamide (453a)

Compound 453a was prepared according to the procedure reported in step-3 of scheme-1 from (2-(methoxymethyl)-7-(4,4,5,5-tetramethyl-1,3,2-dioxaborolan-2-yl)benzofuran-5-yl)methanol (278a) (1.5 g, 4.71 mmol) in dioxane (25 mL) using (+)-(S)—N-((4-chloro-3-fluoropyridin-2-yl)methyl)-2-methylpropane-2-sulfinamide (220c) (1.248 g, 4.71 mmol), bis(triphenylphosphine)palladium(II) chloride (Pd(PPh$_3$)$_2$Cl$_2$) (0.496 g, 0.707 mmol) and a solution of K$_2$CO$_3$ (1.955 g, 14.14 mmol) in water (3 mL) under an argon atmosphere heating at 100° C. for 18 h on oil bath. This gave after workup, purification by flash column chromatography [silica gel, eluting with hexanes/10% methanol in ethyl acetate (1:0 to 1:2)] (+)-(S)—N-((3-fluoro-4-(5-(hydroxymethyl)-2-(methoxymethyl)benzofuran-7-yl)pyridin-2-yl)methyl)-2-methylpropane-2-sulfinamide (453a) (517 mg, 26%) as a brown gum; $^1$H NMR (300 MHz, DMSO-d$_6$) δ 8.50 (dd, J=4.9, 0.7 Hz, 1H), 7.71-7.69 (m, 1H), 7.63 (dd, J=5.6, 4.9 Hz, 1H), 7.39 (t, J=1.4 Hz, 1H), 7.00 (s, 1H), 5.83 (t, J=5.8 Hz, 1H), 5.31 (t, J=5.7 Hz, 1H), 4.63 (d, J=5.7 Hz, 2H), 4.51 (s, 2H), 4.40 (dd, J=5.8, 2.1 Hz, 2H), 3.29 (s, 3H), 1.11 (s, 9H); $^{19}$F NMR (282 MHz, DMSO-d$_6$) δ−128.27; MS (ES+): 421.10 (M+1); Optical rotation [α]$_D$=+35.56 (c=0.045, MeOH).

Step-2: Preparation of (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-4-methylphenyl)acetate (453b)

Compound 453b was prepared according to the procedure reported in step-2 of scheme-23 from (+)-(S)—N-((3-fluoro-4-(5-(hydroxymethyl)-2-(methoxymethyl)benzofuran-7-yl)pyridin-2-yl)methyl)-2-methylpropane-2-sulfinamide (453a) (476 mg, 1.133 mmol) in DCM (10 mL) using triphenylphosphine (405 mg, 1.545 mmol), ethyl 2-(2-hydroxy-4-methylphenyl)acetate (269d) (200 mg, 1.030 mmol) and (E)-bis(4-chlorobenzyl) diazene-1,2-dicarboxylate (DCAD, 567 mg, 1.545 mmol) in DCM (10 mL). This gave after workup and purification by flash column chromatography [silica gel, eluting with hexanes/10% methanol in ethyl acetate (1:0 to 1:1)] (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-4-methylphenyl)acetate (453b) (215 mg, 35%) as a colorless gum; $^1$H NMR (300 MHz, DMSO-d$_6$) δ 8.52 (d, J=5.0 Hz, 1H), 7.81 (d, J=1.6 Hz, 1H), 7.65 (t, J=5.2 Hz, 1H), 7.50 (s, 1H), 7.08 (d, J=7.6 Hz, 1H), 7.04 (s, 1H), 6.98-6.95 (m, 1H), 6.75-6.71 (m, 1H), 5.84 (t, J=5.7 Hz, 1H), 5.21 (s, 2H), 4.52 (s, 2H), 4.43-4.39 (m, 2H), 3.90 (q, J=7.1 Hz, 2H), 3.56 (s, 2H), 3.30 (s, 3H), 2.30 (s, 3H), 1.11 (s, 9H), 0.97 (t, J=7.1 Hz, 3H); $^{19}$F NMR (282 MHz, DMSO-d$_6$) δ−128.11; MS (ES+): 597.20 (M+1); Optical rotation [α]$_D$=+34.78 (c=0.115, MeOH).

Step-3: Preparation of Ethyl 2-(2-((7-(2-(aminomethyl)-3-fluoropyridin-4-yl)-2-(methoxymethyl)benzofuran-5-yl)methoxy)-4-methylphenyl)acetate (453c)

Compound 453c was prepared according to the procedure reported in step-3 of scheme-305 from (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-4-methylphenyl)acetate (453b) (205 mg, 0.344 mmol) in THF (7 mL) using HCl (3M aqueous; 0.344 mL, 1.031 mmol) and stirring at room temperature for 2h. This gave after workup ethyl 2-(2-((7-(2-(aminomethyl)-3-fluoropyridin-4-yl)-2-(methoxymethyl)benzofuran-5-yl)methoxy)-4-methylphenyl)acetate (453c), which was used as such for next step. MS (ES+): 493.20 (M+1).

Step-4: Preparation of 2-(2-((7-(2-(aminomethyl)-3-fluoropyridin-4-yl)-2-(methoxymethyl)benzofuran-5-yl)methoxy)-4-methylphenyl)acetic Acid (453d)

Compound 453d was prepared according to the procedure reported in step-6 of scheme-1 from ethyl 2-(2-((7-(2-(aminomethyl)-3-fluoropyridin-4-yl)-2-(methoxymethyl)benzofuran-5-yl)methoxy)-4-methylphenyl)acetate (453c) (0.344 mmol; from above step-3) in MeOH (7 mL), THF (7 mL) using a solution of lithium hydroxide (0.118 g, 2.75 mmol) in water (7 mL) and stirring at room temperature for 16 h. This gave after workup and purification by reverse phase column [C18 column, eluting with water (containing 0.1% HCl)/acetonitrile (1:0 to 0:1)] 2-(2-((7-(2-(aminomethyl)-3-fluoropyridin-4-yl)-2-(methoxymethyl)benzofuran-5-yl)methoxy)-4-methylphenyl)acetic acid (453d) (81 mg, 51%) HCl salt as a light yellow solid; $^1$H NMR (300 MHz, DMSO-d$_6$) δ 8.64 (d, J=5.0 Hz, 1H), 8.60-8.53 (m, 3H), 7.87 (d, J=1.6 Hz, 1H), 7.79 (t, J=5.3 Hz, 1H), 7.59-7.57 (m, 1H), 7.08 (d, J=7.6 Hz, 1H), 7.05 (s, 1H), 6.94 (s, 1H), 6.75-6.70 (m, 1H), 5.24 (s, 2H), 4.54 (s, 2H), 4.42-4.32 (m, 2H), 3.52 (s, 2H), 3.30 (s, 3H), 2.29 (s, 3H); $^{19}$F NMR (282 MHz, DMSO-d$_6$) δ−128.62; MS (ES+): 465.10 (M+1); MS (ES−): 463.10 (M−1); Analysis calculated for C$_{26}$H$_{25}$FN$_2$O$_5$.1.25HCl.1.75H$_2$O: C, 57.66; H, 5.54; N, 5.17; Cl, 8.18; Found: C, 57.68; H, 5.40; N, 5.12; Cl, 8.19.

Scheme-454

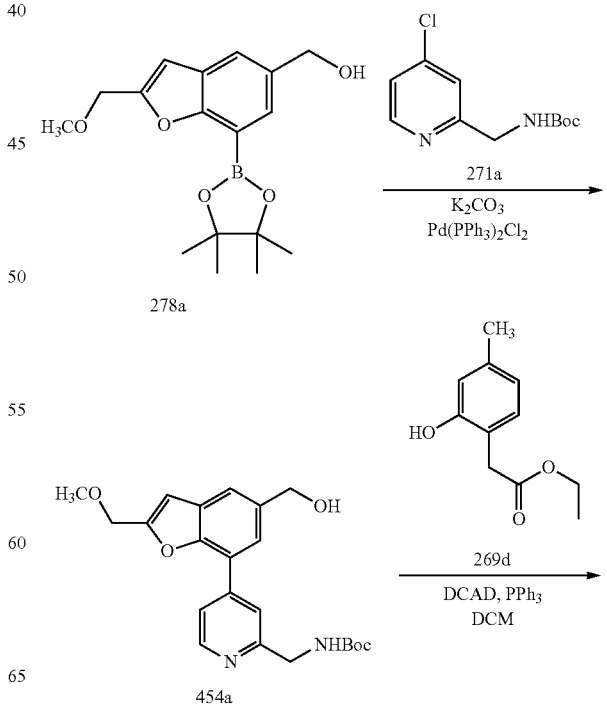

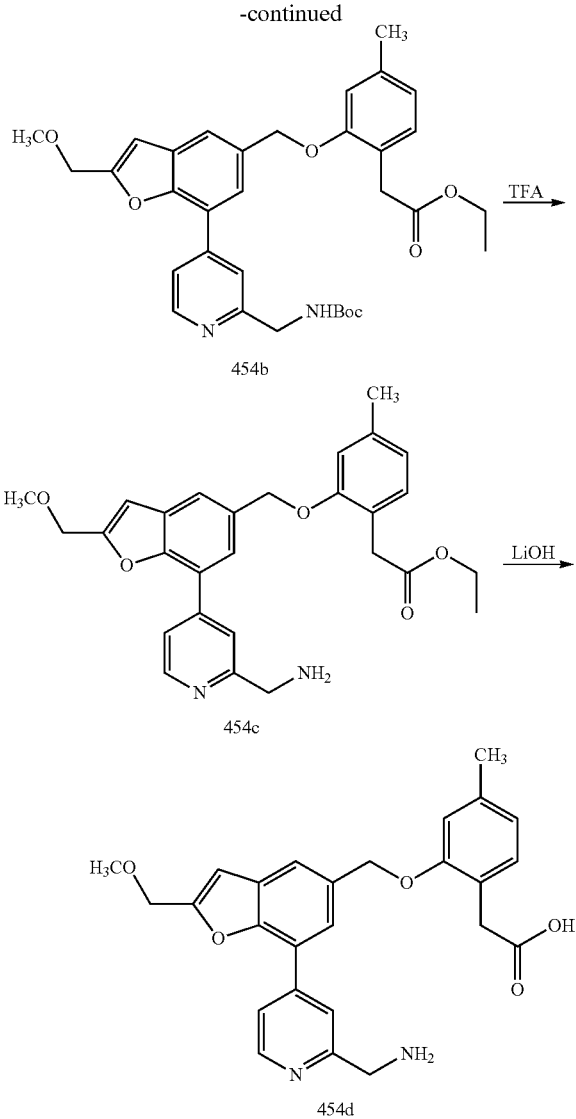

Preparation of 2-(2-((7-(2-(aminomethyl)pyridin-4-yl)-2-(methoxymethyl)benzofuran-5-yl)methoxy)-4-methylphenyl)acetic Acid (454d)

Step-1: Preparation of tert-butyl ((4-(5-(hydroxymethyl)-2-(methoxymethyl)benzofuran-7-yl)pyridin-2-yl)methyl)carbamate (454a)

Compound 454a was prepared according to the procedure reported in step-3 of scheme-1 from (2-(methoxymethyl)-7-(4,4,5,5-tetramethyl-1,3,2-dioxaborolan-2-yl)benzofuran-5-yl)methanol (278a) (1241 mg, 3.90 mmol) in dioxane (20 mL) using tert-butyl ((4-chloropyridin-2-yl)methyl)carbamate (271a) (885 mg, 3.65 mmol), bis(triphenylphosphine)palladium(II) chloride (Pd(PPh$_3$)$_2$Cl$_2$) (384 mg, 0.547 mmol) and a solution of K$_2$CO$_3$ (1512 mg, 10.94 mmol) in water (2.4 mL) under a nitrogen atmosphere heating at 100° C. for 18 h on oil bath. This gave after workup, purification by flash column chromatography [silica gel, eluting with dichloromethane/methanol (1:0 to 19:1)] tert-butyl ((4-(5-(hydroxymethyl)-2-(methoxymethyl)benzofuran-7-yl)pyridin-2-yl)methyl)carbamate (454a) (941 mg) as a brown gum; MS (ES+): 399.20 (M+1).

Step-2: Preparation of Ethyl 2-(2-((7-(2-(((tert-butoxycarbonyl)amino)methyl)pyridin-4-yl)-2-(methoxymethyl)benzofuran-5-yl)methoxy)-4-methylphenyl)acetate (454b)

Compound 454b was prepared according to the procedure reported in step-2 of scheme-23 from tert-butyl ((4-(5-(hydroxymethyl)-2-(methoxymethyl)benzofuran-7-yl)pyridin-2-yl)methyl)carbamate (454a) (900 mg, 2.259 mmol) in DCM (20 mL) using triphenylphosphine (889 mg, 3.39 mmol), ethyl 2-(2-hydroxy-4-methylphenyl)acetate (269d) (570 mg, 2.94 mmol) and (E)-bis(4-chlorobenzyl) diazene-1,2-dicarboxylate (DCAD, 1244 mg, 3.39 mmol) in DCM (20 mL). This gave after workup and purification by flash column chromatography [silica gel, eluting with hexanes/10% methanol in ethyl acetate (1:0 to 1:1)] ethyl 2-(2-((7-(2-(((tert-butoxycarbonyl)amino)methyl)pyridin-4-yl)-2-(methoxymethyl)benzofuran-5-yl)methoxy)-4-methylphenyl)acetate (454b) (374 mg, 19% for two steps) as a colorless gum; $^1$H NMR (300 MHz, DMSO-d$_6$) δ 8.64 (dd, J=5.2, 0.8 Hz, 1H), 7.85-7.52 (m, 4H), 7.45 (t, J=6.0 Hz, 1H), 7.09 (d, J=7.5 Hz, 1H), 7.04 (s, 1H), 6.96 (s, 1H), 6.73 (d, J=7.4 Hz, 1H), 5.21 (s, 2H), 4.59 (s, 2H), 4.33 (d, J=6.1 Hz, 2H), 3.90 (q, J=7.1 Hz, 2H), 3.56 (s, 2H), 3.34 (s, 3H), 2.30 (s, 3H), 1.39 (s, 9H), 0.95 (t, J=7.1 Hz, 3H); MS (ES+): 447.20 (M+1).

Step-3: Preparation of Ethyl 2-(2-((7-(2-(aminomethyl)pyridin-4-yl)-2-(methoxymethyl)benzofuran-5-yl)methoxy)-4-methylphenyl)acetate (454c)

Compound 454c was prepared according to the procedure reported in step-5 of scheme-1 from ethyl 2-(2-((7-(2-(((tert-butoxycarbonyl)amino)methyl)pyridin-4-yl)-2-(methoxymethyl)benzofuran-5-yl)methoxy)-4-methylphenyl)acetate (454b) (360 mg, 0.626 mmol) in DCM (25 mL) using TFA (0.931 mL, 12.53 mmol) and stirring at room temperature for 20 h. This gave after workup ethyl 2-(2-((7-(2-(aminomethyl)pyridin-4-yl)-2-(methoxymethyl)benzofuran-5-yl)methoxy)-4-methylphenyl)acetate (454c) which was used as such for next step. MS (ES+): 475.20 (M+1).

Step-4: Preparation of 2-(2-((7-(2-(aminomethyl)pyridin-4-yl)-2-(methoxymethyl)benzofuran-5-yl)methoxy)-4-methylphenyl)acetic Acid (454d)

Compound 454d was prepared according to the procedure reported in step-6 of scheme-1 from ethyl 2-(2-((7-(2-(aminomethyl)pyridin-4-yl)-2-(methoxymethyl)benzofuran-5-yl)methoxy)-4-methylphenyl)acetate (454c) (0.626 mmol; from above step-3) in MeOH (10 mL), THF (10 mL) using a solution of lithium hydroxide (214 mg, 5.01 mmol) in water (10 mL) and stirring at room temperature for 19 h. This gave after workup and purification by reverse phase column [C18 column, eluting with water (containing 0.1% HCl)/acetonitrile (1:0 to 0:1)] 2-(2-((7-(2-(aminomethyl)pyridin-4-yl)-2-(methoxymethyl)benzofuran-5-yl)methoxy)-4-methylphenyl)acetic acid (454d) (161 mg, 58%) HCl salt as a light yellow solid; $^1$H NMR (300 MHz, DMSO-d$_6$) δ 8.79 (d, J=5.3 Hz, 1H), 8.54 (s, 3H), 8.06-8.04 (m, 1H), 7.99 (dd, J=5.3, 1.7 Hz, 1H), 7.83 (d, J=1.5 Hz, 1H), 7.80 (d, J=1.6 Hz, 1H), 7.09 (d, J=7.5 Hz, 1H), 7.05 (s, 1H), 6.94 (s, 1H), 6.73 (d, J=7.5 Hz, 1H), 5.25 (s, 2H), 4.61 (s, 2H), 4.41-4.20 (m, 2H), 3.55 (s, 2H), 3.34 (s, 3H), 2.29

(s, 3H); MS (ES+): 447.20 (M+1); MS (ES−): 445.20 (M−1); Analysis calculated for C$_{26}$H$_{26}$N$_2$O$_5$.1.25HCl.1.75H$_2$O: C, 59.64; H, 5.92; N, 5.35; Cl, 8.46; Found: C, 59.67; H, 5.70; N, 5.30; Cl, 8.67.

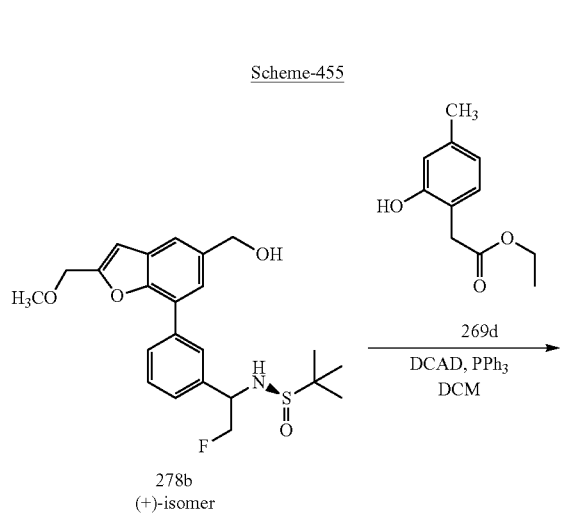

Scheme-455

278b (+)-isomer 455a (+)-isomer

455b 455c (+)-isomer

Preparation of (+)-2-(2-((7-(3-(1-amino-2-fluoro-ethyl)phenyl)-2-(methoxymethyl)benzofuran-5-yl)methoxy)-4-methylphenyl)acetic Acid (455c)

Step-1: Preparation of (+)-ethyl 2-(2-((7-(3-(1-((R)-1,1-dimethylethylsulfinamido)-2-fluoroethyl)phenyl)-2-(methoxymethyl)benzofuran-5-yl)methoxy)-4-methylphenyl)acetate (455a)

Compound 455a was prepared according to the procedure reported in step-2 of scheme-23 from (+)-(R)—N-(2-fluoro-1-(3-(5-(hydroxymethyl)-2-(methoxymethyl)benzofuran-7-yl)phenyl)ethyl)-2-methylpropane-2-sulfinamide (278b) (1.0 g, 2.307 mmol) in DCM (20 mL) using triphenylphosphine (0.907 g, 3.46 mmol), ethyl 2-(2-hydroxy-4-methylphenyl)acetate (269d) (0.582 g, 3.00 mmol) and a solution of (E)-bis(4-chlorobenzyl) diazene-1,2-dicarboxylate (DCAD, 1.270 g, 3.46 mmol) in DCM (20 mL). This gave after workup and purification by flash column chromatography [silica gel, eluting with ethyl acetate in hexanes (1:0 to 1:1)] (+)-ethyl 2-(2-((7-(3-(1-((R)-1,1-dimethylethylsulfinamido)-2-fluoroethyl)phenyl)-2-(methoxymethyl)benzofuran-5-yl)methoxy)-4-methylphenyl)acetate (455a) (556 mg, 40%) as a white solid; $^1$H NMR (300 MHz, DMSO-d$_6$) δ 7.90 (s, 1H), 7.85-7.77 (m, 1H), 7.67 (d, J=1.6 Hz, 1H), 7.57 (d, J=1.7 Hz, 1H), 7.55-7.50 (m, 2H), 7.09 (d, J=7.5 Hz, 1H), 6.99 (s, 1H), 6.97 (s, 1H), 6.75-6.70 (m, 1H), 6.02 (d, J=8.1 Hz, 1H), 5.21 (s, 2H), 4.78-4.46 (m, 5H), 3.90 (q, J=7.1 Hz, 2H), 3.57 (s, 2H), 3.32 (s, 3H), 2.30 (s, 3H), 1.14 (s, 9H), 0.96 (t, J=7.1 Hz, 3H); $^{19}$F NMR (282 MHz, DMSO-d$_6$) δ−217.17; MS (ES+): 632.30 (M+Na); Optical rotation [α]$_D$=+4.66 (c=0.815, MeOH).

Step-2: Preparation of Ethyl 2-(2-((7-(3-(1-amino-2-fluoroethyl)phenyl)-2-(methoxymethyl)benzofuran-5-yl)methoxy)-4-methylphenyl)acetate (455b)

To a stirred solution of (+)-ethyl 2-(2-((7-(3-(1-((R)-1,1-dimethylethylsulfinamido)-2-fluoroethyl)phenyl)-2-(methoxymethyl)benzofuran-5-yl)methoxy)-4-methylphenyl)acetate (455a) (470 mg, 0.771 mmol) in THF (15 mL) was added 3 N aqueous HCl (0.771 mL, 2.312 mmol) at room temperature and stirred for 3 h. Reaction was concentrated in vacuum to dryness to afford ethyl 2-(2-((7-(3-(1-amino-2-fluoroethyl)phenyl)-2-(methoxymethyl)benzofuran-5-yl)methoxy)-4-methylphenyl)acetate (455b) which was used as such for next step. MS (ES+): 506.20 (M+1).

Step-3: Preparation of (+)-2-(2-((7-(3-(1-amino-2-fluoroethyl)phenyl)-2-(methoxymethyl)benzofuran-5-yl)methoxy)-4-methylphenyl)acetic Acid (455c)

Compound 455c was prepared according to the procedure reported in step-6 of scheme-1 from ethyl 2-(2-((7-(3-(1-amino-2-fluoroethyl)phenyl)-2-(methoxymethyl)benzofuran-5-yl)methoxy)-4-methylphenyl)acetate (455b) (0.771 mmol; from above step-2) in THF/MeOH (10 mL, each) using a solution of lithium hydroxide hydrate (0.264 g, 6.17 mmol) in water (10 mL). This gave after workup and purification by reverse phase column chromatography [C18 column, eluting with water (containing 0.1% HCl)/acetonitrile (1:0 to 0:1)] (+)-2-(2-((7-(3-(1-amino-2-fluoroethyl)phenyl)-2-(methoxymethyl)benzofuran-5-yl)methoxy)-4-methylphenyl)acetic acid (455c) (168 mg, 57%) HCl salt as a light yellow solid; $^1$H NMR (300 MHz, DMSO-$d_6$) δ 8.04 (s, 1H), 7.97 (td, J=4.4, 1.7 Hz, 1H), 7.73 (d, J=1.6 Hz, 1H), 7.68-7.59 (m, 3H), 7.09 (d, J=7.5 Hz, 1H), 7.00 (s, 1H), 6.96-6.94 (m, 1H), 6.72 (ddd, J=7.5, 1.6, 0.8 Hz, 1H), 5.23 (s, 2H), 4.99-4.72 (m, 3H), 4.58 (s, 2H), 3.54 (s, 2H), 3.33 (s, 3H), 2.29 (s, 3H); $^{19}$F NMR (282 MHz, DMSO-$d_6$) δ−222.70; MS (ES+): 478.20 (M+1); MS (ES−): 476.20 (M−1); Analysis calculated for $C_{28}H_{28}FNO_5$.0.95HCl.1.75H$_2$O: C, 61.86; H, 6.02; N, 2.58; Cl, 6.19; Found: C, 61.91; H, 5.71; N, 2.53; Cl, 6.07; Optical rotation [t]D=+14.58 (c=0.48, MeOH).

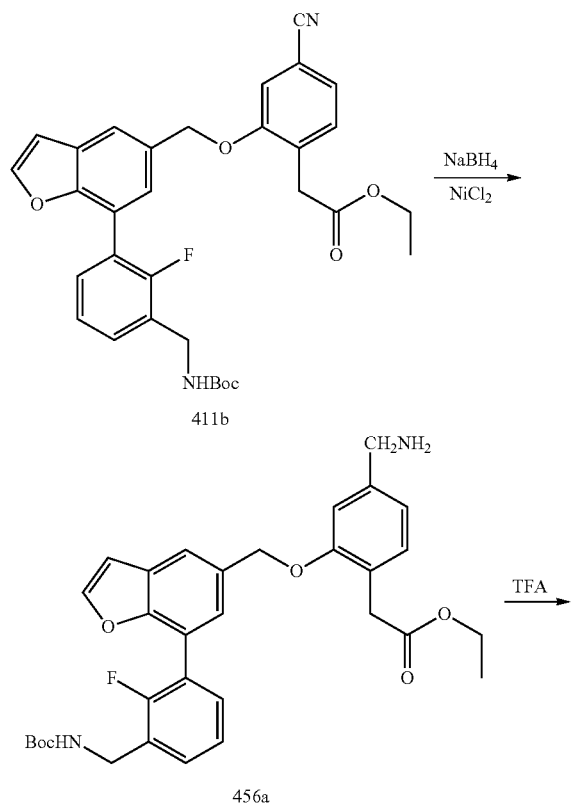

Scheme-456

411b

456a

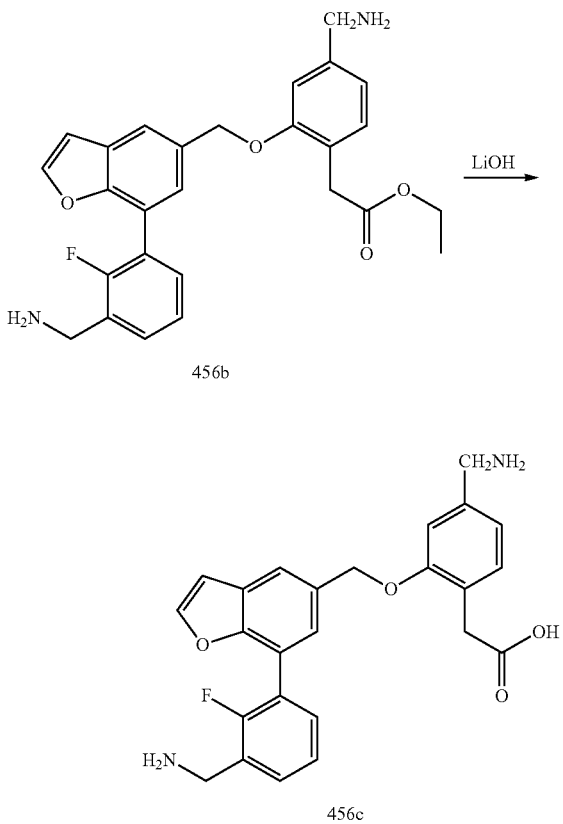

456b

456c

Preparation of 2-(4-(aminomethyl)-2-((7-(3-(aminomethyl)-2-fluorophenyl)benzofuran-5-yl)methoxy)phenyl)acetic Acid (456c)

Step-1: Preparation of Ethyl 2-(4-(aminomethyl)-2-((7-(3-(((tert-butoxycarbonyl)amino)methyl)-2-fluorophenyl)benzofuran-5-yl)methoxy)phenyl)acetate (456a)

Compound 456a was prepared according to the procedure reported in step-2 of scheme-256 from ethyl 2-(2-((7-(3-((tert-butoxycarbonylamino)methyl)-2-fluorophenyl)benzofuran-5-yl)methoxy)-4-cyanophenyl)acetate (411b) (310 mg, 0.555 mmol) in methanol using nickel (II) chloride hexahydrate (33 mg, 0.139 mmol) and sodium borohydride (126 mg, 3.33 mmol), using N1-(2-aminoethyl)ethane-1,2-diamine (0.12 mL, 1.110 mmol) for quenching. This gave after workup and purification by flash column chromatography [silica gel, eluting with chloroform/methanol (1:0 to 4:1)] ethyl 2-(4-(aminomethyl)-2-((7-(3-(((tert-butoxycarbonyl)amino)methyl)-2-fluorophenyl)benzofuran-5-yl)methoxy)phenyl)acetate (456a) (141 mg) as a white solid; MS (ES+): 563.30 (M+1).

Step-2: Preparation of Ethyl 2-(4-(aminomethyl)-2-((7-(3-(aminomethyl)-2-fluorophenyl)benzofuran-5-yl)methoxy)phenyl)acetate (456b)

Compound 456b was prepared according to the procedure reported in step-5 of scheme-1 from ethyl 2-(4-(aminom ethyl)-2-((7-(3-(((tert-butoxycarbonyl)amino)methyl)-2-fluorophenyl)benzofuran-5-yl)methoxy)phenyl)acetate (456a) (135 mg, 0.240 mmol) in DCM (8 mL) using TFA (0.356 mL, 4.80 mmol) and stirring at room temperature for 20 h. This gave after workup ethyl 2-(4-(aminomethyl)-2-((7-(3-(aminomethyl)-2-fluorophenyl)benzofuran-5-yl)methoxy)phenyl)acetate (456b) which was used as such for next step; MS (ES+): 463.20 (M+1).

Step-3: Preparation of 2-(4-(aminomethyl)-2-((7-(3-(aminomethyl)-2-fluorophenyl)benzofuran-5-yl)methoxy)phenyl)acetic Acid (456c)

Compound 456c was prepared according to the procedure reported in step-6 of scheme-1 from ethyl 2-(4-(aminomethyl)-2-((7-(3-(aminomethyl)-2-fluorophenyl)benzofuran-5-yl)methoxy)phenyl)acetate (456b) (0.111 g, 0.240 mmol) in THF/MeOH (5 mL, each) using a solution of lithium hydroxide hydrate (0.082 g, 1.920 mmol) in water (5 mL) stirring at room temperature for 20 h. This gave after workup and purification by reverse phase column [C18, eluting with water (containing 0.1% HCl)/acetonitrile (1:0 to 0:1)] 2-(4-(aminomethyl)-2-((7-(3-(aminomethyl)-2-fluorophenyl)benzofuran-5-yl)methoxy)phenyl)acetic acid (456c) (69 mg, 30% for 3 steps) HCl salt as a white solid; $^1$H NMR (300 MHz, DMSO-$d_6$) δ 12.25 (s, 1H), 8.57 (s, 3H), 8.50 (s, 3H), 8.07 (d, J=2.2 Hz, 1H), 7.85 (d, J=1.6 Hz, 1H), 7.75-7.64 (m, 2H), 7.49 (s, 1H), 7.47-7.38 (m, 2H), 7.24 (d, J=7.6 Hz, 1H), 7.07 (d, J=2.2 Hz, 1H), 7.04-6.98 (m, 1H), 5.27 (s, 2H), 4.17 (s, 2H), 3.99 (s, 2H), 3.58 (s, 2H); MS (ES+): 435.10 (M+1); MS (ES−): 433.20 (M−1); Analysis calculated for $C_{25}H_{23}FN_2O_4 \cdot 2HCl \cdot 1.25H_2O$: C, 56.66; H, 5.23; N, 5.29; Cl, 13.38; Found: C, 56.69; H, 4.98; N, 5.16; Cl, 12.84.

Scheme-457

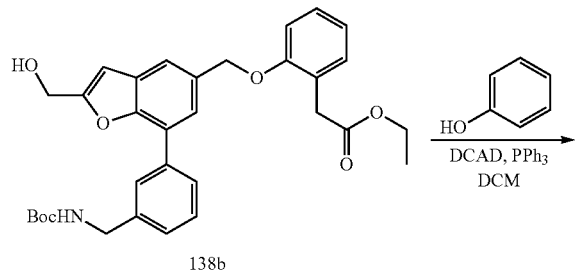

138b

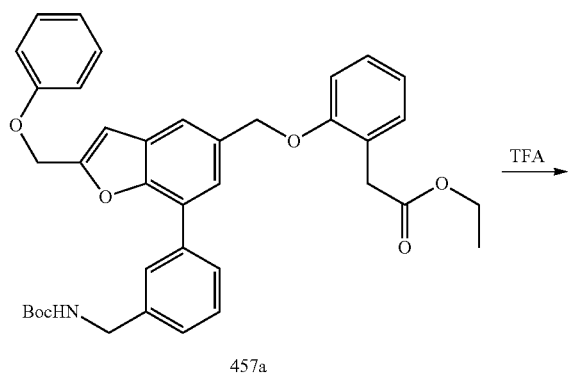

457a

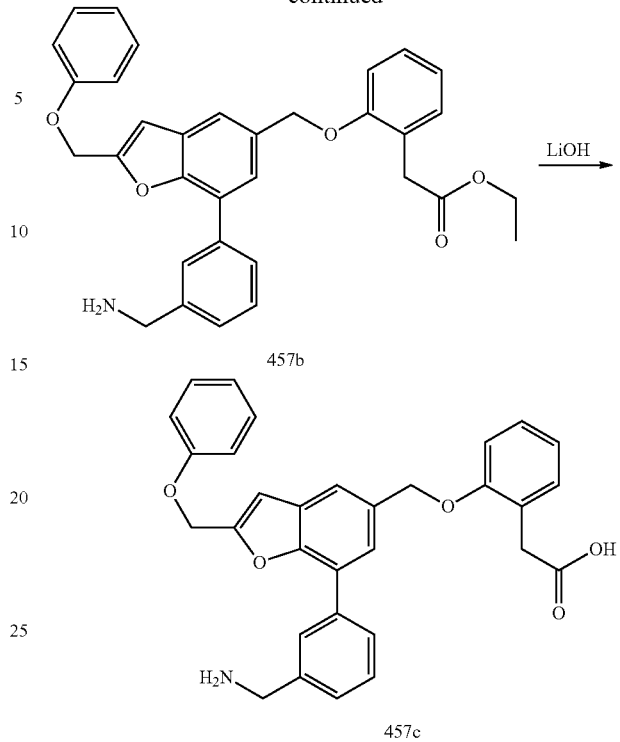

457b

457c

Preparation of 2-(2-((7-(3-(aminomethyl)phenyl)-2-(phenoxymethyl)benzofuran-5-yl)methoxy)phenyl)acetic Acid (457c)

Step-1: Preparation of Ethyl 2-(2-((7-(3-(((tert-butoxycarbonyl)amino)methyl)phenyl)-2-(phenoxymethyl)benzofuran-5-yl)methoxy)phenyl)acetate (457a)

Compound 457a was prepared according to the procedure reported in step-2 of scheme-23 from ethyl 2-(2-((7-(3-(((tert-butoxycarbonyl)amino)methyl)phenyl)-2-(hydroxymethyl)benzofuran-5-yl)methoxy)phenyl)acetate (138b) (300 mg, 0.550 mmol) in DCM (8 mL) using triphenylphosphine (216 mg, 0.825 mmol), phenol (67.3 mg, 0.715 mmol) and a solution of(E)-bis(4-chlorobenzyl) diazene-1,2-dicarboxylate (DCAD, 303 mg, 0.825 mmol) in DCM (8 mL). This gave after workup and purification by flash column chromatography [silica gel, eluting with ethyl acetate in hexanes (1:0 to 3:1)] ethyl 2-(2-((7-(3-(((tert-butoxycarbonyl)amino)methyl)phenyl)-2-(phenoxymethyl)benzofuran-5-yl)methoxy)phenyl)acetate (457a) (202 mg, 59%) as a colorless gum; $^1$H NMR (300 MHz, DMSO-$d_6$) δ 7.75-7.67 (m, 3H), 7.55 (d, J=1.7 Hz, 1H), 7.51-7.38 (m, 2H), 7.35-7.19 (m, 5H), 7.13-7.05 (m, 4H), 7.01-6.94 (m, 1H), 6.94-6.88 (m, 1H), 5.30 (s, 2H), 5.22 (s, 2H), 4.22 (d, J=6.3 Hz, 2H), 3.91 (q, J=7.1 Hz, 2H), 3.62 (s, 2H), 1.38 (s, 9H), 0.96 (t, J=7.1 Hz, 3H).

Step-2: Preparation of Ethyl 2-(2-((7-(3-(aminomethyl)phenyl)-2-(phenoxymethyl)benzofuran-5-yl)methoxy)phenyl)acetate (457b)

Compound 457b was prepared according to the procedure reported in step-5 of scheme-1 from ethyl 2-(2-((7-(3-(((tert-butoxycarbonyl)amino)methyl)phenyl)-2-(phenoxymethyl) benzofuran-5-yl)methoxy)phenyl)acetate (457a) (190 mg, 0.306 mmol) in DCM (15 mL) using TFA (0.454 mL, 6.11 mmol) and stirring at room temperature for 18 h. This gave after workup ethyl 2-(2-((7-(3-(aminomethyl)phenyl)-2-(phenoxymethyl)benzofuran-5-yl)methoxy)phenyl)acetate (457b) which was used as such for next step; MS (ES+): 522.20 (M+1).

Step-3: Preparation of 2-(2-((7-(3-(aminomethyl) phenyl)-2-(phenoxymethyl)benzofuran-5-yl) methoxy)phenyl)acetic Acid (457c)

Compound 457c was prepared according to the procedure reported in step-6 of scheme-1 from ethyl 2-(2-((7-(3-(aminomethyl)phenyl)-2-(phenoxymethyl)benzofuran-5-yl) methoxy)phenyl)acetate (457b) (0.306 mmol; from above step-2) in THF/MeOH (5 mL, each) using a solution of lithium hydroxide hydrate (105 mg, 2.448 mmol) in water (5 mL). This gave after workup and purification by reverse phase column chromatography [C18 column, eluting with water (containing 0.1% HCl)/acetonitrile (1:0 to 0:1)] 2-(2-((7-(3-(aminomethyl)phenyl)-2-(phenoxymethyl)benzofuran-5-yl)methoxy)phenyl)acetic acid (457c) (20 mg, 13%) HCl salt as an off-white solid; $^1$H NMR (300 MHz, DMSO-$d_6$) δ 8.38 (s, 3H), 7.97-7.94 (m, 1H), 7.91 (dt, J=7.4, 1.7 Hz, 1H), 7.75 (d, J=1.6 Hz, 1H), 7.65 (d, J=1.6 Hz, 1H), 7.62-7.51 (m, 2H), 7.36-7.28 (m, 2H), 7.22 (d, J=7.4 Hz, 2H), 7.13 (s, 1H), 7.12-7.04 (m, 3H), 7.02-6.95 (m, 1H), 6.94-6.85 (m, 1H), 5.32 (s, 2H), 5.26 (s, 2H), 4.12 (s, 2H), 3.59 (s, 2H); MS (ES+): 494.15 (M+1); MS (ES-): 492.20 (M-1).

Scheme-458

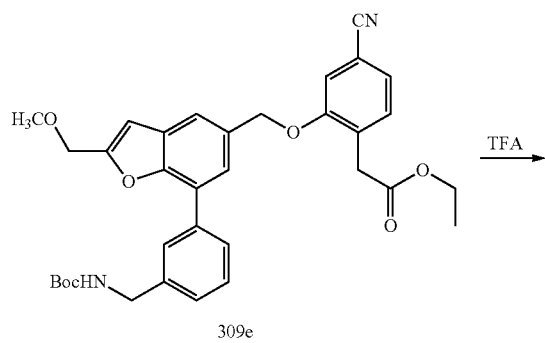

309e

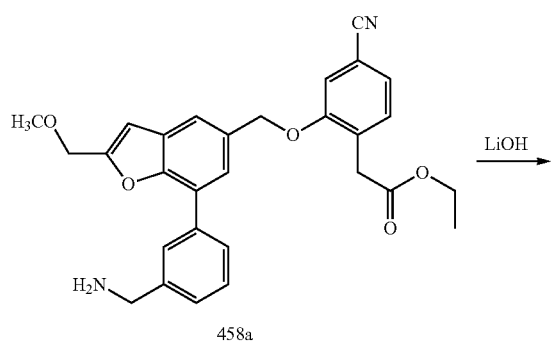

458a

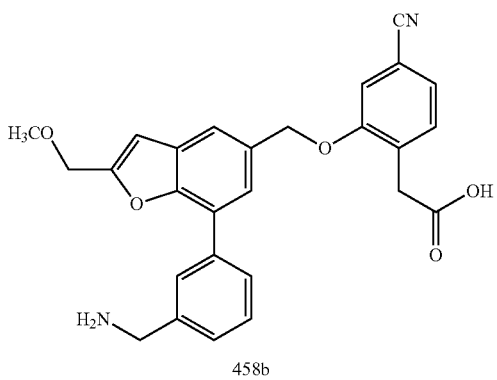

458b

Preparation of 2-(2-((7-(3-(aminomethyl)phenyl)-2-(methoxymethyl)benzofuran-5-yl)methoxy)-4-cyanophenyl)acetic Acid (458b)

Step-1: Preparation of Ethyl 2-(2-((7-(3-(aminomethyl)phenyl)-2-(methoxymethyl)benzofuran-5-yl) methoxy)-4-cyanophenyl)acetate (458a)

Compound 458a was prepared according to the procedure reported in step-5 of scheme-1 from ethyl 2-(2-((7-(3-(((tert-butoxycarbonyl)amino)methyl)phenyl)-2-(methoxymethyl) benzofuran-5-yl)methoxy)-4-cyanophenyl)acetate (309e) (0.250 g, 0.427 mmol) in DCM (7.5 mL) using TFA (7.5 mL). This gave after workup ethyl 2-(2-((7-(3-(aminomethyl)phenyl)-2-(methoxymethyl)benzofuran-5-yl) methoxy)-4-cyanophenyl)acetate (458a) (0.1 g, 48%) as an off white solid; $^1$H NMR (300 MHz, DMSO-$d_6$) δ 7.91-7.80 (m, 2H), 7.69 (s, 1H), 7.63 (s, 1H), 7.55 (d, J=8.5 Hz, 2H), 7.46 (dd, J=12.7, 5.6 Hz, 3H), 7.02 (s, 1H), 5.31 (s, 2H), 4.58 (s, 2H), 4.02 (s, 2H), 3.92 (q, J=7.1 Hz, 2H), 3.73 (s, 2H), 3.33 (s, 3H), 0.96 (t, J=7.1 Hz, 3H).

Step-2: Preparation of 2-(2-((7-(3-(aminomethyl) phenyl)-2-(methoxymethyl)benzofuran-5-yl) methoxy)-4-cyanophenyl)acetic Acid (458b)

Compound 458b was prepared according to the procedure reported in step-6 of scheme-1 from ethyl 2-(2-((7-(3-(aminomethyl)phenyl)-2-(methoxymethyl)benzofuran-5-yl) methoxy)-4-cyanophenyl)acetate (458a) (0.1 g, 0.206 mmol) in THF/MeOH (7.5 mL, each) using a solution of lithium hydroxide hydrate (0.0173 g, 0.412 mmol) in water (7.5 mL) stirring at room temperature for 2 h. This gave after workup 2-(2-((7-(3-(aminomethyl)phenyl)-2-(methoxymethyl)benzofuran-5-yl)methoxy)-4-cyanophenyl)acetic acid (458b) (0.015 g, 17%) HCl salt as an off white solid; $^1$H NMR (300 MHz, DMSO-$d_6$) δ 8.12 (s, 1H), 8.00 (d, J=7.9 Hz, 1H), 7.72 (d, J=6.0 Hz, 2H), 7.60-7.53 (m, 1H), 7.50 (s, 1H), 7.48-7.42 (m, 1H), 7.36 (s, 2H), 7.02 (s, 1H), 5.34 (s, 2H), 4.58 (s, 2H), 4.09 (s, 2H), 3.58 (s, 2H), 3.33 (s, 3H).

Scheme-459
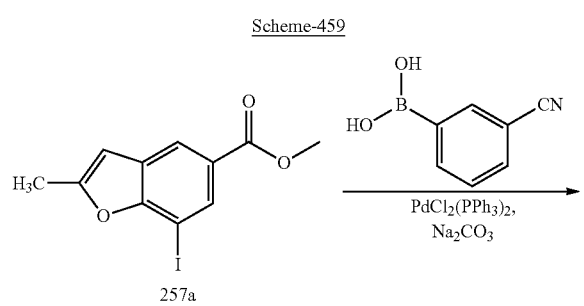
257a
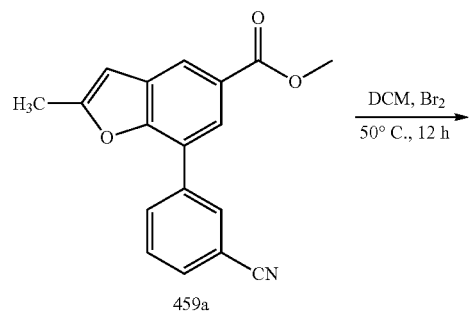
459a
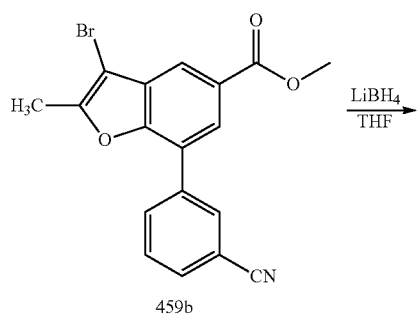
459b
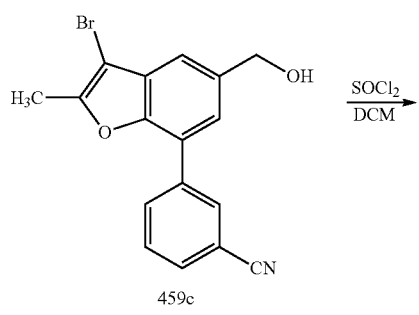
459c
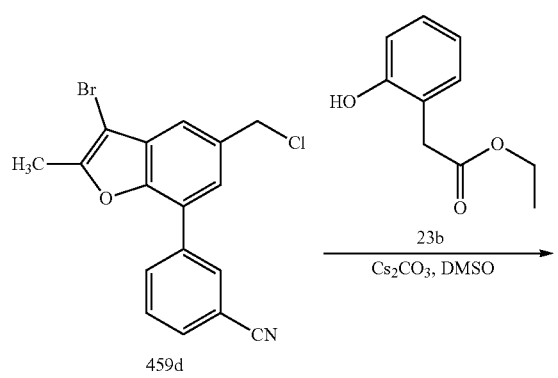
459d
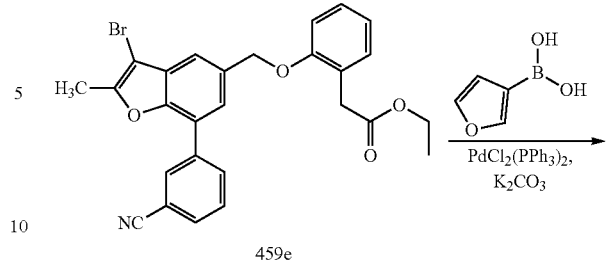
459e
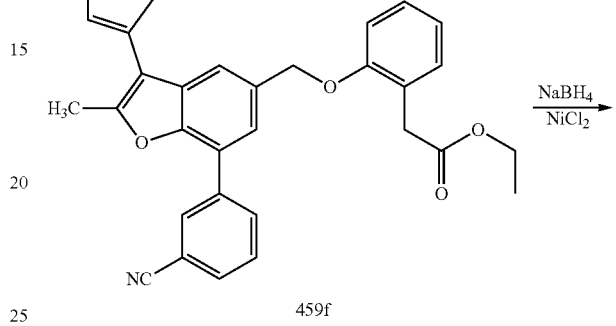
459f
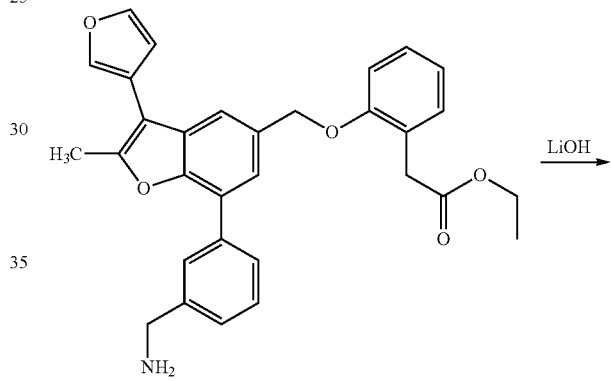
459g
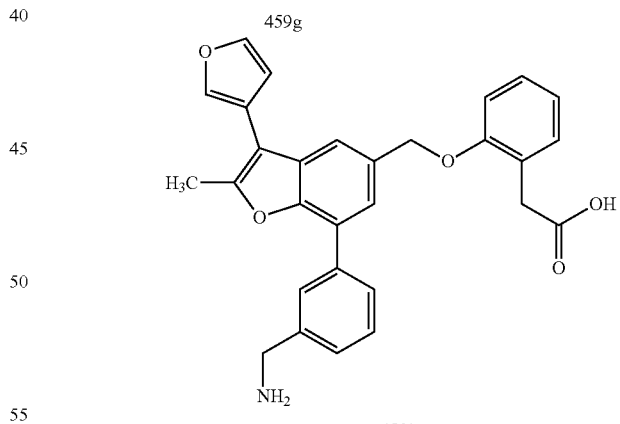
459h
Preparation of 2-(2-((7-(3-(aminomethyl)phenyl)-3-(furan-3-yl)-2-methylbenzofuran-5-yl)methoxy)phenyl)acetic Acid (459h)
Step-1: Preparation of methyl 7-(3-cyanophenyl)-2-methylbenzofuran-5-carboxylate (459a)
Compound 459a was prepared according to the procedure reported in step-3 of scheme-1 from methyl 7-iodo-2-methylbenzofuran-5-carboxylate (257a) (10 g, 31.63 mmol) in acetonitrile (60 mL) using (3-cyanophenyl)boronic acid (5.57 g, 37.96 mmol), a solution of $Na_2CO_3$ (310.5 g, 94.90 mmol) in water (20.0 mL), $Pd(PPh_3)_2Cl_2$ (4.44 g, 6.32 mmol) and heating under a nitrogen atmosphere at 90° C. for 12 h. This gave after workup and purification by flash column chromatography (silica gel, eluting with 0 to 40% ethyl acetate in n-heptane) methyl 7-(3-cyanophenyl)-2-methylbenzofuran-5-carboxylate (459a) (6.0 g, 65%) as an oil; $^1$H NMR (300 MHz, DMSO-$d_6$) δ 8.34-8.27 (m, 1H), 8.24-8.19 (m, 2H), 8.04 (d, J=1.7 Hz, 1H), 7.97-7.90 (m, 1H), 7.82-7.71 (m, 1H), 6.91-6.74 (m, 1H), 3.90 (s, 3H), 2.52 (s, 3H).

Step-2: Preparation of methyl 3-bromo-7-(3-cyanophenyl)-2-methylbenzofuran-5-carboxylate (459b)

Compound 459b was prepared according to the procedure reported in step-2 of scheme-425 from methyl 7-(3-cyanophenyl)-2-methylbenzofuran-5-carboxylate (459a) (1.0 g, 3.43 mmol) in DCM (30 mL) using $Br_2$ (540 mg, 3.43 mmol) and heating at 50° C. for 12 h. This gave after workup and purification by flash column chromatography (silica gel, eluting with 0 to 40% ethyl acetate in n-heptane) methyl 3-bromo-7-(3-cyanophenyl)-2-methylbenzofuran-5-carboxylate (459b) (1.2 g, 34%) as an off white solid; $^1$H NMR (300 MHz, Chloroform-d) δ 8.16-8.05 (m, 3H), 7.99 (ddd, J=7.8, 1.9, 1.3 Hz, 1H), 7.65 (dt, J=7.7, 1.4 Hz, 1H), 7.56 (td, J=7.7, 0.6 Hz, 1H), 3.92 (s, 3H), 2.48 (s, 3H).

Step-3: Preparation of 3-(3-bromo-5-(hydroxymethyl)-2-methylbenzofuran-7-yl)benzonitrile (459c)

Compound 459c was prepared according to the procedure reported in step-2 of scheme-76 from methyl 3-bromo-7-(3-cyanophenyl)-2-methylbenzofuran-5-carboxylate (459b) (1.0 g, 2.70 mmol) in THF (30 mL) using $LiBH_4$ (0.472 g, 21.60 mmol) and stirring at room temperature for 12 h. This gave after workup and purification by flash column chromatography [silica gel, eluting with 40% EtOAc in n-heptane] 3-(3-bromo-5-(hydroxymethyl)-2-methylbenzofuran-7-yl)benzonitrile (459c) (0.6 g, 65%) as an off-white solid; $^1$H NMR (300 MHz, DMSO-$d_6$) δ 8.30-8.23 (m, 1H), 8.25-8.12 (m, 1H), 7.91 (dt, J=7.8, 1.3 Hz, 1H), 7.76 (td, J=7.8, 0.6 Hz, 1H), 7.57 (d, J=1.6 Hz, 1H), 7.45 (d, J=1.6 Hz, 1H), 5.37 (t, J=5.8 Hz, 1H), 4.68 (d, J=5.6 Hz, 2H), 2.50 (s, 3H).

Step-4: Preparation of 3-(3-bromo-5-(chloromethyl)-2-methylbenzofuran-7-yl)benzonitrile (459d)

Compound 459d was prepared according to the procedure reported in step-4 of scheme-257 from 3-(3-bromo-5-(hydroxymethyl)-2-methylbenzofuran-7-yl)benzonitrile (459c) (3.2 g, 9.35 mmol) in DCM (64 mL) using $SOCl_2$ (2.22 g, 18.70 mmol) and stirring reaction at 0° C. for 2 h. This gave after workup and purification by flash column chromatography (silica gel, eluting with 10% EtOAc in n-heptane) 3-(3-bromo-5-(chloromethyl)-2-methylbenzofuran-7-yl) benzonitrile (459d) (3.2 g, 95%) as an off-white solid; $^1$H NMR (300 MHz, DMSO-$d_6$) δ 8.33-8.26 (m, 1H), 8.26-8.16 (m, 1H), 7.97-7.88 (m, 1H), 7.83-7.71 (m, 2H), 7.63-7.56 (m, 1H), 4.97 (s, 2H), 2.52 (s, 3H).

Step-5: Preparation of Ethyl 2-(2-((3-bromo-7-(3-cyanophenyl)-2-methylbenzofuran-5-yl)methoxy) phenyl)acetate (459e)

Compound 459e was prepared according to the procedure reported in step-6 of scheme-257 from 3-(3-bromo-5-(chloromethyl)-2-methylbenzofuran-7-yl)benzonitrile (459d) (3.2 g, 8.87 mmol) using ethyl 2-(2-hydroxyphenyl)acetate (23b) (1.59 g, 8.87 mmol) in DMF (32 mL) using $Cs_2CO_3$ (2.89 g, 8.87 mmol) and stirring at room temperature for 12h. This gave after workup and purification by flash column chromatography (silica gel, eluting with 20% EtOAc in n-heptane) ethyl 2-(2-((3-bromo-7-(3-cyanophenyl)-2-methylbenzofuran-5-yl)methoxy)phenyl)acetate (459e) (3.2 g, 72%) as an off-white solid; $^1$H NMR (300 MHz, DMSO-$d_6$) δ 8.30 (t, J=1.7 Hz, 1H), 8.23 (dt, J=8.0, 1.4 Hz, 1H), 7.93 (dt, J=7.8, 1.4 Hz, 1H), 7.77 (t, J=7.8 Hz, 1H), 7.71 (d, J=1.6 Hz, 1H), 7.56 (d, J=1.6 Hz, 1H), 7.33-7.19 (m, 2H), 7.11 (d, J=8.1 Hz, 1H), 6.96-6.85 (m, 1H), 5.28 (s, 2H), 3.96 (q, J=7.1 Hz, 2H), 3.64 (s, 2H), 2.52 (s, 3H), 1.00 (t, J=7.1 Hz, 3H).

Step-6: Preparation of Ethyl 2-(2-((7-(3-cyanophenyl)-3-(furan-3-yl)-2-methylbenzofuran-5-yl) methoxy)phenyl)acetate (459f)

Compound 459f was prepared according to the procedure reported in step-3 of scheme-1 from ethyl 2-(2-((3-bromo-7-(3-cyanophenyl)-2-methylbenzofuran-5-yl)methoxy)phenyl)acetate (459e) (504 mg, 1 mmol) in 1,4-dioxane (20 mL) using furan-3-ylboronic acid (168 mg, 1.500 mmol), a solution of $K_2CO_3$ (415 mg, 3.00 mmol) in water (20.0 mL), $Pd(PPh_3)_2Cl_2$ (140 mg, 0.2 mmol) and heating under a nitrogen atmosphere at 100° C. for 16 h. This gave after workup and purification by flash column chromatography [silica gel, eluting with hexanes/ethyl acetate (1:0 to 9:1)] ethyl 2-(2-((7-(3-cyanophenyl)-3-(furan-3-yl)-2-methylbenzofuran-5-yl)methoxy)phenyl)acetate (459f) (368 mg, 75%) as a yellow gum; $^1$H NMR (300 MHz, DMSO-$d_6$) δ 8.35-8.31 (m, 1H), 8.29-8.25 (m, 1H), 8.19-8.17 (m, 1H), 7.95-7.88 (m, 2H), 7.82 (d, 1H), 7.78 (t, J=7.8 Hz, 1H), 7.67-7.65 (m, 1H), 7.30-7.17 (m, 2H), 7.12 (d, J=8.1 Hz, 1H), 6.95 (dd, J=1.8, 0.9 Hz, 1H), 6.93-6.86 (m, 1H), 5.27 (s, 2H), 3.88 (q, J=7.1 Hz, 2H), 3.63 (s, 2H), 2.61 (s, 3H), 0.94 (t, J=7.1 Hz, 3H).

Step-7: Preparation of Ethyl 2-(2-((7-(3-(aminomethyl)phenyl)-3-(furan-3-yl)-2-methylbenzofuran-5-yl)methoxy)phenyl)acetate (459g)

Compound 459g was prepared according to the procedure reported in step-2 of scheme-256 from ethyl 2-(2-((7-(3-cyanophenyl)-3-(furan-3-yl)-2-methylbenzofuran-5-yl) methoxy)phenyl)acetate (459f) (350 mg, 0.712 mmol) in methanol (20 mL) using nickel (II) chloride hexahydrate (42 mg, 0.178 mmol) and sodium borohydride (162 mg, 4.27 mmol), using N1-(2-aminoethyl)ethane-1,2-diamine (0.154 mL, 1.424 mmol) for quenching. This gave after workup and purification by flash column chromatography [silica gel, eluting with chloroform/methanol (1:0 to 9:1)] ethyl 2-(2-((7-(3-(aminomethyl)phenyl)-3-(furan-3-yl)-2-methylbenzofuran-5-yl)methoxy)phenyl)acetate (459g) (31 mg) as a light-yellow solid; MS (ES+): 496.20 (M+1).

Step-8: Preparation of 2-(2-((7-(3-(aminomethyl) phenyl)-3-(furan-3-yl)-2-methylbenzofuran-5-yl) methoxy)phenyl)acetic Acid (459h)

Compound 459h was prepared according to the procedure reported in step-6 of scheme-1 from ethyl 2-(2-((7-(3-(aminomethyl)phenyl)-3-(furan-3-yl)-2-methylbenzofuran-5-yl)methoxy)phenyl)acetate (459g) (29 mg, 0.059 mmol) in THF/methanol (3 mL, each) using solution of lithium hydroxide hydrate (15 mg, 0.351 mmol) in water (3 mL) and stirring at room temperature for 17 h. This gave after workup and purification by reverse-phase column chromatography [C-18 column, eluting with water (containing 0.1% HCl)/acetonitrile (1:0 to 0:1)] 2-(2-((7-(3-(aminomethyl)phenyl)-3-(furan-3-yl)-2-methylbenzofuran-5-yl)methoxy)phenyl) acetic acid (459h) (12 mg, 44%) HCl salt as a white solid; $^1$H NMR (300 MHz, DMSO-d$_6$) δ 12.20 (s, 1H), 8.32 (s, 3H), 8.20-8.17 (m, 1H), 7.99-7.96 (m, 1H), 7.96-7.92 (m, 1H), 7.89 (t, J=1.7 Hz, 1H), 7.82-7.80 (m, 1H), 7.66-7.50 (m, 3H), 7.29-7.18 (m, 2H), 7.10 (d, J=8.0 Hz, 1H), 6.95 (dd, J=1.8, 0.9 Hz, 1H), 6.93-6.87 (m, 1H), 5.28 (s, 2H), 4.15 (s, 2H), 3.60 (s, 2H), 2.60 (s, 3H); MS (ES+): 468.10 (M+1); MS (ES−): 466.10 (M−1).

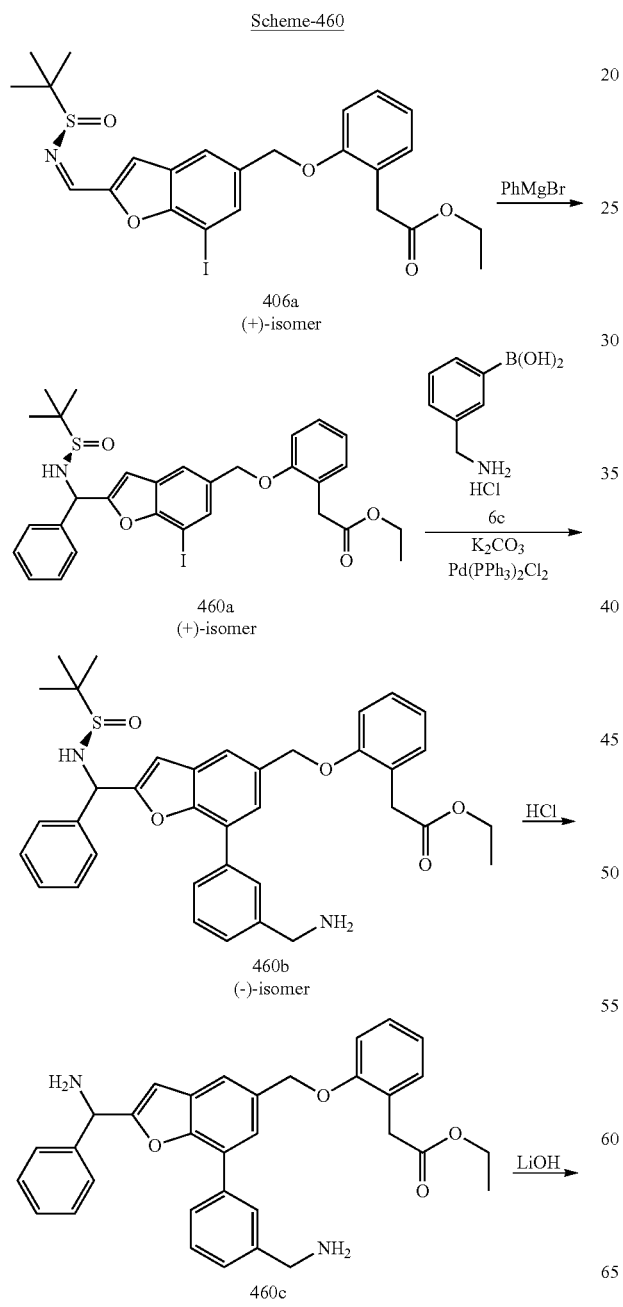

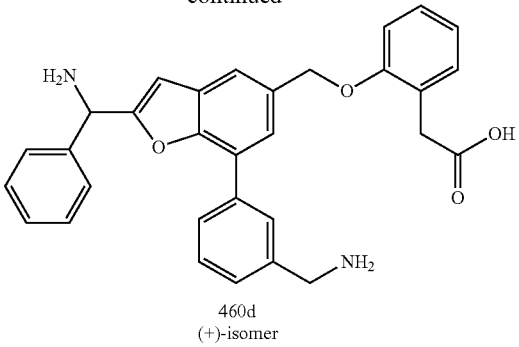

460d
(+)-isomer

Preparation of (+)-2-(2-((2-(amino(phenyl)methyl)-7-(3-(aminomethyl)phenyl)benzofuran-5-yl) methoxy)phenyl)acetic Acid (460d)

Step-1: Preparation of (+)-ethyl 2-(2-((2-(((R)-1,1-dimethylethylsulfinamido)(phenyl)methyl)-7-iodo-benzofuran-5-yl)methoxy)phenyl)acetate (460a)

To a solution of (+)-(R,Z)-ethyl 2-(2-((2-(((tert-butylsulfi-nyl)imino)methyl)-7-iodobenzofuran-5-yl)methoxy)phenyl) acetate (406a) (1.4 g, 2.467 mmol) in toluene (30 mL) cooled to −8° C. was added phenyl magnesium bromide (2.467 mL, 2.467 mmol), stirred at −8° C. for 2 h and allowed to warm to room temperature over a period of 14 h. The reaction mixture was quenched with saturated aqueous NH$_4$Cl (60 mL), water (30 mL) and extracted with ethyl acetate (120 mL). The organic layer was washed with brine (60 mL), dried, filtered and concentrated in vacuum. The residue obtained was purified by flash column chromatography [silica gel, eluting with hexanes/ethyl acetate (1:0 to 1:1)] to give (+)-ethyl 2-(2-((2-(((R)-1,1-dimethylethylsul-finamido)(phenyl)methyl)-7-iodobenzofuran-5-yl)methoxy) phenyl)acetate (460a) (717 mg, 45%) as a colorless gum; $^1$H NMR (300 MHz, DMSO-d$_6$) δ 7.68 (d, J=1.6 Hz, 1H), 7.62 (d, J=1.5 Hz, 1H), 7.59-7.50 (m, 2H), 7.44-7.29 (m, 3H), 7.28-7.16 (m, 2H), 7.05 (d, J=8.1 Hz, 1H), 6.90 (td, J=7.4, 1.1 Hz, 1H), 6.85 (d, J=0.8 Hz, 1H), 6.32 (d, J=6.5 Hz, 1H), 5.78 (d, J=6.4 Hz, 1H), 5.11 (s, 2H), 4.10-3.89 (m, 2H), 3.59 (s, 2H), 1.18 (s, 9H), 1.06 (t, J=7.1 Hz, 3H); MS (ES+): 646.10 (M+1); Optical rotation [α]$_D$=+5.52 (c=0.905, MeOH).

Step-2: Preparation of (−)-ethyl 2-(2-((7-(3-(ami-nomethyl)phenyl)-2-(((R)-1,1-dimethylethylsulfina-mido)(phenyl)methyl)benzofuran-5-yl)methoxy) phenyl)acetate (460b)

Compound 460b was prepared according to the procedure reported in step-3 of scheme-1 from (+)-ethyl 2-(2-((2-(((R)-1,1-dimethylethylsulfinamido)(phenyl)methyl)-7-iodoben-zofuran-5-yl)methoxy)phenyl)acetate (460a) (480 mg, 0.744 mmol) in dioxane (20 mL) using 3-(aminomethyl) phenylboronic acid hydrochloride (6c) (209 mg, 1.115 mmol), Pd(PPh$_3$)$_2$Cl$_2$ (104 mg, 0.149 mmol) and a solution of K$_2$CO$_3$ (308 mg, 2.231 mmol) in water (2 mL) under a nitrogen atmosphere and heating at 100° C. for 3 h on oil bath. This gave after workup and purification by flash column chromatography [silica gel, eluting with chloroform/methanol (1:0 to 9:1)] (−)-ethyl 2-(2-((7-(3-(aminomethyl) phenyl)-2-(((R)-1,1-dimethylethylsulfinamido)(phenyl)

methyl)benzofuran-5-yl)methoxy)phenyl)acetate (460b) (301 mg, 65%) as a colorless gum; $^1$H NMR (300 MHz, DMSO-d$_6$) δ 7.81-7.79 (m, 1H), 7.73-7.68 (m, 1H), 7.61 (d, J=1.7 Hz, 1H), 7.55 (dt, J=5.6, 1.7 Hz, 3H), 7.47-7.18 (m, 7H), 7.11-7.07 (m, 1H), 6.89 (td, J=7.4, 1.1 Hz, 1H), 6.75 (d, J=0.8 Hz, 1H), 6.38 (d, J=6.8 Hz, 1H), 5.78 (d, J=6.7 Hz, 1H), 5.20 (s, 2H), 3.91 (q, J=7.1 Hz, 2H), 3.79 (s, 2H), 3.61 (s, 2H), 1.15 (s, 9H), 0.96 (t, J=7.1 Hz, 3H); MS (ES+): 625.30 (M+1); Optical rotation [ ]D D=−12.17 (c=0.115, MeOH).

Step-3: Preparation of Ethyl 2-(2-((2-(amino(phenyl)methyl)-7-(3-(aminomethyl)phenyl)benzofuran-5-yl)methoxy)phenyl)acetate (460c)

Compound 460c was prepared according to the procedure reported in step-10 of scheme-257 from (−)-ethyl 2-(2-((7-(3-(aminomethyl)phenyl)-2-(((R)-1,1-dimethylethylsulfinamido)(phenyl)methyl)benzofuran-5-yl)methoxy)phenyl)acetate (460b) (280 mg, 0.448 mmol) in THF (5 mL) using 3 N aqueous HCl (0.448 mL, 1.344 mmol) and stirring at room temperature for 4 h. This gave after workup ethyl 2-(2-((2-(amino(phenyl)methyl)-7-(3-(aminomethyl)phenyl)benzofuran-5-yl)methoxy)phenyl)acetate (460c) which was used as such for next step.

Step-4: Preparation of (+)-2-(2-((2-(amino(phenyl)methyl)-7-(3-(aminomethyl)phenyl)benzofuran-5-yl)methoxy)phenyl)acetic Acid (460d)

Compound 460d was prepared according to the procedure reported in step-6 of scheme-1 from ethyl 2-(2-((2-(amino(phenyl)methyl)-7-(3-(aminomethyl)phenyl)benzofuran-5-yl)methoxy)phenyl)acetate (460c) (0.448 mmol, from above step-3) in MeOH/THF (5 mL, each) using a solution of lithium hydroxide hydrate (123 mg, 2.87 mmol) in water (5 mL) and stirring at room temperature for 18 h. This gave after workup and purification by reverse phase column [C18, eluting with water (containing 0.1% HCl)/acetonitrile (1:0 to 0:1)] (+)-2-(2-((2-(amino(phenyl)methyl)-7-(3-(aminomethyl)phenyl)benzofuran-5-yl)methoxy)phenyl)acetic acid (460d) solid (129 mg, 59%) HCl salt as a white; $^1$H NMR (300 MHz, DMSO-d$_6$) δ 9.60 (s, 3H), 8.66 (s, 3H), 8.18 (s, 1H), 7.98-7.87 (m, 1H), 7.79-7.67 (m, 4H), 7.56 (d, J=4.8 Hz, 2H), 7.52-7.39 (m, 3H), 7.27-7.16 (m, 2H), 7.10-7.03 (m, 1H), 6.97 (s, 1H), 6.89 (td, J=7.4, 1.1 Hz, 1H), 5.99 (s, 1H), 5.26 (s, 2H), 4.15 (s, 2H), 3.59 (s, 2H); MS (ES−): 491.20 (M−1); Analysis calculated for C$_{31}$H$_{28}$N$_2$O$_4$.2HCl.H$_2$O: C, 63.81; H, 5.53; N, 4.80; Cl, 12.15; Found: C, 63.89; H, 5.29; N, 4.71; Cl, 12.02; Optical rotation [t]D=+16.07 (c=0.56, MeOH).

Scheme-461

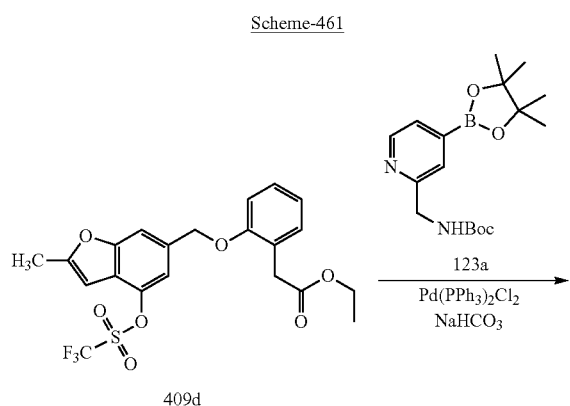

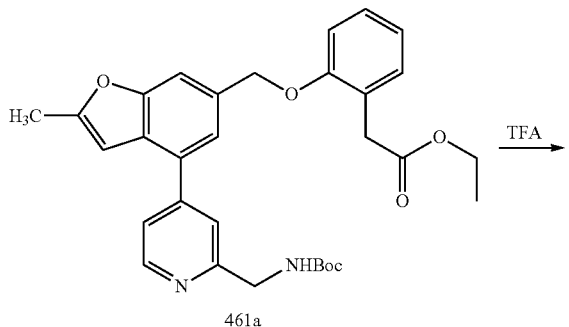

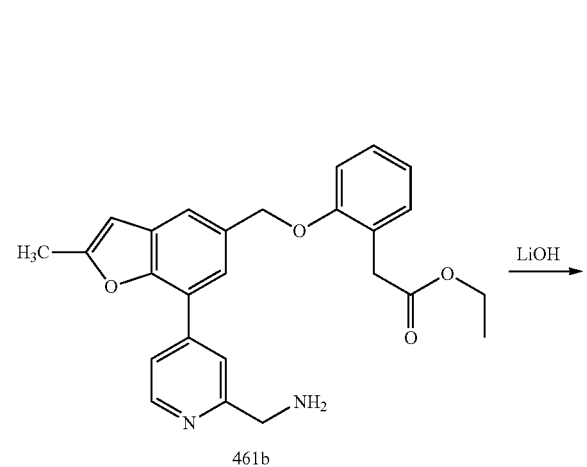

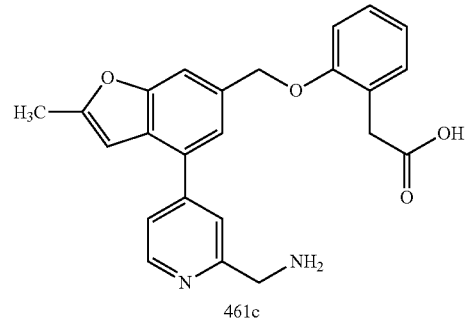

Preparation of 2-(2-((4-(2-(aminomethyl)pyridin-4-yl)-2-methylbenzofuran-6-yl)methoxy)phenyl)acetic Acid (461c)

Step-1: Preparation of Ethyl 2-(2-((4-(2-(((tert-butoxycarbonyl)amino)methyl)pyridin-4-yl)-2-methylbenzofuran-6-yl)methoxy)phenyl)acetate (461a)

Compound 461a was prepared according to the procedure reported in step-3 of scheme-1 from ethyl 2-(2-((2-methyl-4-(((trifluoromethyl)sulfonyl)oxy)benzofuran-6-yl)methoxy)phenyl)acetate (409d) (515 mg, 1.090 mmol) in dioxane (10 mL) using tert-butyl (4-(4,4,5,5-tetramethyl-1,3,2-dioxaborolan-2-yl)pyridin-2-yl)methylcarbamate (123a) (546 mg, 1.635 mmol), a solution of sodium bicarbonate (275 mg, 3.27 mmol) in water (1 mL), Pd(PPh$_3$)$_2$Cl$_2$ (230 mg, 0.327 mmol) and heating under a nitrogen atmosphere at 100° C. for 3.5 h. This gave after workup and twice purification by flash column chromatography (silica gel, 24 g, eluting with 0-5% methanol in DCM), (silica gel, 24 g, eluting with 0-50%, ethyl acetate in hexanes) ethyl 2-(2-((4-(2-(((tert-butoxycarbonyl)amino)methyl)pyridin-4-yl)-2-methylbenzofuran-6-yl)methoxy)phenyl)acetate (461a) (404 mg, 70% yield) as a yellowish solid. $^1$H NMR (300 MHz, DMSO-d$_6$) δ 8.60 (dd, J=5.0, 0.9 Hz, 1H), 7.66 (t, J=1.1 Hz, 1H), 7.58-7.51 (m, 3H), 7.49 (d, J=1.3 Hz, 1H), 7.29-7.19 (m, 2H), 7.11-7.07 (m, 1H), 6.91 (td, J=7.4, 1.1 Hz, 1H), 6.77-6.74 (m, 1H), 5.25 (s, 2H), 4.31 (d, J=6.1 Hz, 2H), 3.93 (q, J=7.1 Hz, 2H), 3.63 (s, 2H), 2.48 (d, J=1.0 Hz, 3H), 1.41 (s, 9H), 0.99 (t, J=7.1 Hz, 3H); MS (ES+): 531.30 (M+1).

Step-2: Preparation of Ethyl 2-(2-((4-(2-(aminomethyl)pyridin-4-yl)-2-methylbenzofuran-6-yl)methoxy)phenyl)acetate (461b)

Compound 461b was prepared according to the procedure reported in step-5 of scheme-1 from ethyl 2-(2-((4-(2-(((tert-butoxycarbonyl)amino)methyl)pyridin-4-yl)-2-methylbenzofuran-6-yl)methoxy)phenyl)acetate (461a) (390 mg, 0.735 mmol) in DCM (25 mL) using TFA (0.566 mL, 7.35 mmol). This gave after workup and purification by flash column chromatography [silica(12 g), eluting with Methanol in DCM from 0-10%] ethyl 2-(2-((4-(2-(aminomethyl)pyridin-4-yl)-2-methylbenzofuran-6-yl)methoxy)phenyl)acetate (461b) (290 mg, 92% yield) as a clear oil; $^1$H NMR (300 MHz, DMSO-d$_6$) δ 8.73 (d, J=5.1 Hz, 1H), 8.08 (s, 3H), 7.80 (s, 1H), 7.72-7.67 (m, 2H), 7.54 (s, 1H), 7.30-7.20 (m, 2H), 7.09 (d, J=8.1 Hz, 1H), 6.95-6.87 (m, 2H), 5.27 (s, 2H), 4.29 (s, 2H), 3.95 (q, J=7.1 Hz, 2H), 3.64 (s, 2H), 2.51 (s, 3H), 1.02 (t, J=7.1 Hz, 3H); MS (ES+): 431.15 (M+1).

Step-3: Preparation of 2-(2-((4-(2-(aminomethyl)pyridin-4-yl)-2-methylbenzofuran-6-yl)methoxy)phenyl)acetic Acid (461c)

Compound 461c was prepared according to the procedure reported in step-6 of scheme-1 from ethyl 2-(2-((4-(2-(aminomethyl)pyridin-4-yl)-2-methylbenzofuran-6-yl)methoxy)phenyl)acetate (461b) (280 mg, 0.650 mmol) in THF/MeOH (8 mL, each) using a solution of lithium hydroxide hydrate (109 mg, 2.60 mmol) in water (8 mL) and stirring at room temperature for 18 h. This gave after workup and purification by reverse phase column chromatography (C-18, 50 g column, eluting with 0 to 100% acetonitrile in 0.1% HCl/water) 2-(2-((4-(2-(aminomethyl)pyridin-4-yl)-2-methylbenzofuran-6-yl)methoxy)phenyl)acetic acid (461c) (125 mg, 48% yield) HCl salt as a white solid; $^1$H NMR (300 MHz, DMSO-d$_6$) δ 8.73 (dd, J=5.2, 0.8 Hz, 1H), 8.47 (s, 3H), 7.85-7.82 (m, 1H), 7.75-7.70 (m, 2H), 7.59 (d, J=1.3 Hz, 1H), 7.27-7.19 (m, 2H), 7.09-7.04 (m, 1H), 6.94 (t, J=1.1 Hz, 1H), 6.90 (td, J=7.4, 1.1 Hz, 1H), 5.29 (s, 2H), 4.36-4.21 (m, 2H), 3.60 (s, 2H), 2.50 (s, 3H); Analysis calculated for C$_{24}$H$_{22}$N$_2$O$_4$.1.75HCl.H$_2$O: C, 59.52; H, 5.36; Cl, 12.81; N, 5.78; found: C, 59.51; H, 5.21; Cl, 12.45; N, 5.83.

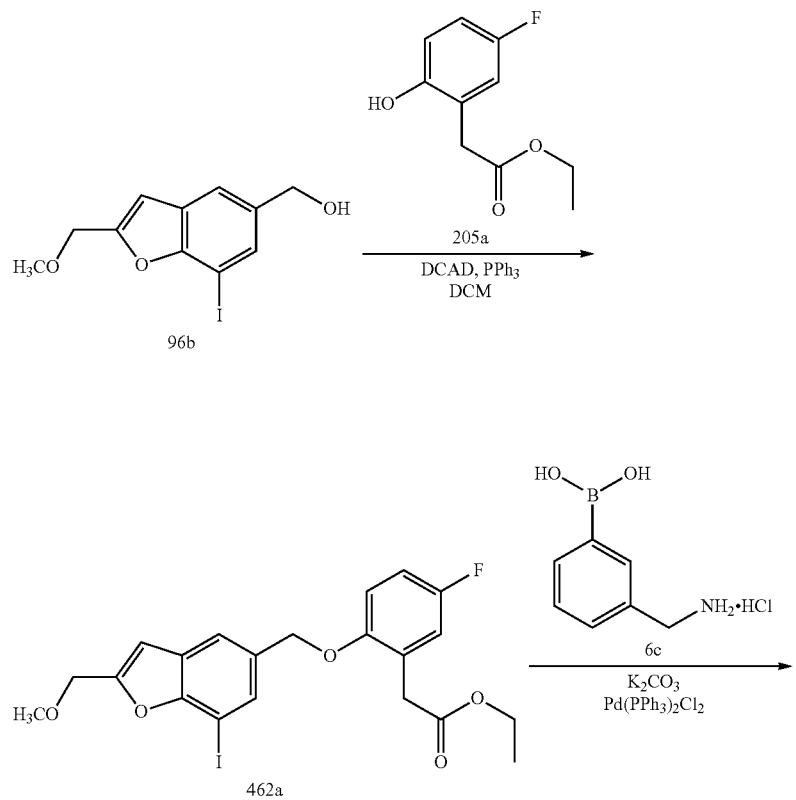

Scheme-462

-continued

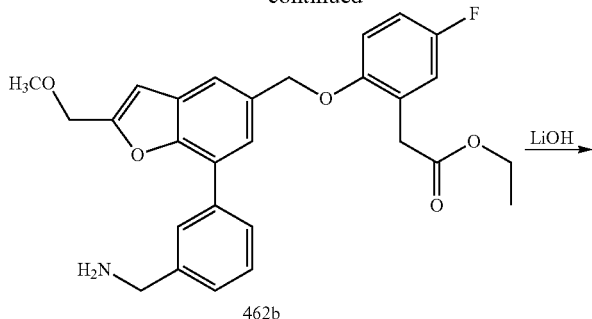
462b

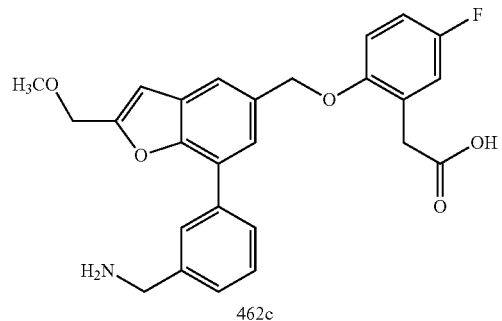
462c

Preparation of 2-(2-((7-(3-(aminomethyl)phenyl)-2-(methoxymethyl)benzofuran-5-yl)methoxy)-5-fluorophenyl)acetic Acid (462c)

Step-1: Preparation of Ethyl 2-(5-fluoro-2-((7-iodo-2-(methoxymethyl)benzofuran-5-yl)methoxy)phenyl)acetate (462a)

Compound 462a was prepared according to the procedure reported in step-2 of scheme-23 from (7-iodo-2-(methoxymethyl)benzofuran-5-yl)methanol (96b) (2.00 g, 6.29 mmol) in DCM (60 mL) using triphenylphosphine (1.786 g, 6.81 mmol), ethyl 2-(5-fluoro-2-hydroxyphenyl)acetate (205a) (1.038 g, 5.24 mmol) and a solution of (E)-bis(4-chlorobenzyl) diazene-1,2-dicarboxylate (DCAD, 2.501 g, 6.81 mmol) in DCM (60 mL). This gave after workup and purification by flash column chromatography (silica gel, 120 g, eluting with 0 to 20% ethyl acetate in hexanes) ethyl 2-(5-fluoro-2-((7-iodo-2-(methoxymethyl)benzofuran-5-yl)methoxy)phenyl)acetate (462a) (2.18 g, 84% yield) as a clear oil which solidified upon standing. $^1$H NMR (300 MHz, DMSO-$d_6$) δ 7.73 (d, J=1.6 Hz, 1H), 7.65 (d, J=1.5 Hz, 1H), 7.16-7.04 (m, 4H), 5.12 (s, 2H), 4.59-4.52 (m, 2H), 4.03 (qd, J=7.1, 0.6 Hz, 2H), 3.63 (s, 2H), 3.33 (s, 3H), 1.08 (t, J=7.1 Hz, 3H); $^{19}$F NMR (282 MHz, DMSO-$d_6$) δ−123.93; MS (ES+): 521.00 (M+Na).

Step-2: Preparation of Ethyl 2-(2-((7-(3-(aminomethyl)phenyl)-2-(methoxymethyl)benzofuran-5-yl)methoxy)-5-fluorophenyl)acetate (462b)

Compound 462b was prepared according to the procedure reported in step-3 of scheme-1 from ethyl 2-(5-fluoro-2-((7-iodo-2-(methoxymethyl)benzofuran-5-yl)methoxy)phenyl)acetate (462a) (400 mg, 0.803 mmol) in dioxane (15 mL) using (3-(aminomethyl)phenyl)boronic acid hydrochloride (6c) (226 mg, 1.204 mmol), a solution of potassium carbonate (333 mg, 2.408 mmol) in water (1.8 mL), Pd(PPh$_3$)$_2$Cl$_2$ (113 mg, 0.161 mmol) and heating under a nitrogen atmosphere at 100° C. for 3 h. This gave after workup and purification by flash column chromatography (silica gel, 12g, eluting with 0 to 5% methanol in DCM) ethyl 2-(2-((7-(3-(aminomethyl)phenyl)-2-(methoxymethyl)benzofuran-5-yl)methoxy)-5-fluorophenyl)acetate (462b) (70 mg, 19% yield); $^1$H NMR (300 MHz, DMSO-$d_6$) δ 7.78 (d, J=1.8 Hz, 1H), 7.71 (dt, J=7.6, 1.6 Hz, 1H), 7.64 (d, J=1.6 Hz, 1H), 7.55 (d, J=1.7 Hz, 1H), 7.47 (t, J=7.6 Hz, 1H), 7.43-7.37 (m, 1H), 7.17-7.03 (m, 3H), 6.98 (s, 1H), 5.21 (s, 2H), 4.57 (s, 2H), 3.94 (q, J=7.1 Hz, 2H), 3.81 (s, 2H), 3.64 (s, 2H), 3.32 (s, 3H), 0.99 (t, J=7.1 Hz, 3H); $^{19}$F NMR (282 MHz, DMSO-$d_6$) δ−124.07; MS (ES+): 478.20 (M+1).

Step-3: Preparation of 2-(2-((7-(3-(aminomethyl)phenyl)-2-(methoxymethyl)benzofuran-5-yl)methoxy)-5-fluorophenyl)acetic Acid (462c)

Compound 462c was prepared according to the procedure reported in step-6 of scheme-1 from ethyl 2-(2-((7-(3-(aminomethyl)phenyl)-2-(methoxymethyl)benzofuran-5-yl)methoxy)-5-fluorophenyl)acetate (462b) (66 mg, 0.138 mmol) in THF/methanol (5 mL, each) using solution of lithium hydroxide hydrate (36 mg, 0.829 mmol) in water (5 mL) and stirring at room temperature for 16 h. This gave after workup and purification by reverse-phase column chromatography [C-18 column, eluting with water (0.1% HCl)/acetonitrile from 0 to 70%] 2-(2-((7-(3-(aminomethyl)phenyl)-2-(methoxymethyl)benzofuran-5-yl)methoxy)-5-fluorophenyl)acetic acid (462c) (30 mg, 48% yield) HCl salt as a white solid; $^1$H NMR (300 MHz, DMSO-$d_6$) δ 8.40 (s, 3H), 7.95 (d, J=1.7 Hz, 1H), 7.93-7.87 (m, 1H), 7.71 (d, J=1.6 Hz, 1H), 7.65-7.51 (m, 3H), 7.15-7.05 (m, 3H), 7.00 (s, 1H), 5.23 (s, 2H), 4.58 (s, 2H), 4.13 (s, 2H), 3.61 (s, 2H), 3.32 (s, 3H); $^{19}$F NMR (282 MHz, DMSO-$d_6$) δ−124.07; MS (ES+): 450.2 (M+1); Analysis calculated for $C_{26}H_{24}FNO_5$·HCl·H$_2$O: C, 61.97; H, 5.40; Cl, 7.04; N, 2.78; Found: C, 62.00; H, 5.27; Cl, 6.91; N, 2.84.

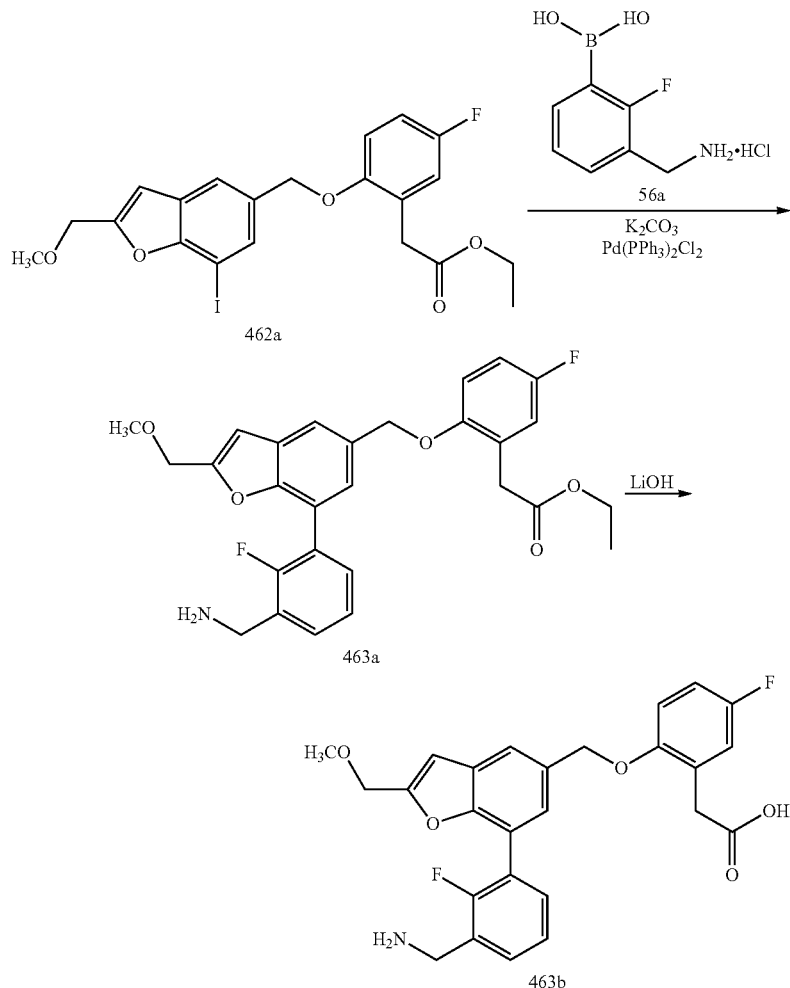

Preparation of 2-(2-((7-(3-(aminomethyl)-2-fluorophenyl)-2-(methoxymethyl)benzofuran-5-yl)methoxy)-5-fluorophenyl)acetic Acid (463b)

Step-1: Preparation of Ethyl 2-(2-((7-(3-(aminomethyl)-2-fluorophenyl)-2-(methoxymethyl)benzofuran-5-yl)methoxy)-5-fluorophenyl)acetate (463a)

Compound 463a was prepared according to the procedure reported in step-3 of scheme-1 from ethyl 2-(5-fluoro-2-((7-iodo-2-(methoxymethyl)benzofuran-5-yl)methoxy)phenyl)acetate (462a) (400 mg, 0.803 mmol) in dioxane (15 mL) using 3-(aminomethyl)-2-fluorophenylboronic acid hydrochloride (56a) (136 mg, 0.803 mmol), a solution of potassium carbonate (333 mg, 2.408 mmol) in water (1.8 mL), Pd(PPh$_3$)$_2$Cl$_2$ (113 mg, 0.161 mmol) and heating under a nitrogen atmosphere at 100° C. for 3 h. This gave after workup and purification by flash column chromatography (silica gel, 24 g, eluting with 0 to 7% methanol in DCM) ethyl 2-(2-((7-(3-(aminomethyl)-2-fluorophenyl)-2-(methoxymethyl)benzofuran-5-yl)methoxy)-5-fluorophenyl)acetate (463a) (127 mg, 32% yield) as a brown oil; $^1$H NMR (300 MHz, DMSO-d$_6$) δ 7.70 (d, J=1.7 Hz, 1H), 7.60 (t, J=7.2 Hz, 1H), 7.44 (t, J=6.5 Hz, 1H), 7.38 (s, 1H), 7.32 (t, J=7.6 Hz, 1H), 7.15-7.07 (m, 3H), 6.99 (s, 1H), 5.19 (s, 2H), 4.51 (s, 2H), 3.91 (q, J=7.1 Hz, 2H), 3.83 (s, 2H), 3.63 (s, 2H), 3.32 (s, 3H), 0.99 (t, J=7.1 Hz, 3H); $^{19}$F NMR (282 MHz, DMSO-d$_6$) δ –121.95, –124.03; MS (ES+): 496.10 (M+1).

Step-2: Preparation of 2-(2-((7-(3-(aminomethyl)-2-fluorophenyl)-2-(methoxymethyl)benzofuran-5-yl)methoxy)-5-fluorophenyl)acetic Acid (463b)

Compound 463b was prepared according to the procedure reported in step-6 of scheme-1 from ethyl 2-(2-((7-(3-(aminomethyl)-2-fluorophenyl)-2-(methoxymethyl)benzofuran-5-yl)methoxy)-5-fluorophenyl)acetate (463a) (120 mg, 0.242 mmol) in THF/methanol (5 mL, each) using solution of lithium hydroxide hydrate (62 mg, 1.453 mmol) in water (5 mL) and stirring at room temperature for 16 h. This gave after workup and purification by reverse-phase column chromatography [C-18 column, eluting with water (0.1% HCl)/acetonitrile from 0 to 70%] 2-(2-((7-(3-(aminomethyl)-2-fluorophenyl)-2-(methoxymethyl)benzofuran-5-yl)methoxy)-5-fluorophenyl)acetic acid (463b) (84 mg, 74% yield) HCl salt as a white solid; $^1$H NMR (300 MHz, DMSO-d$_6$) δ 8.61 (s, 3H), 7.77 (d, J=1.6 Hz, 1H), 7.74-7.62

(m, 2H), 7.47-7.38 (m, 2H), 7.15-7.02 (m, 3H), 7.00 (s, 1H), 5.22 (s, 2H), 4.52 (s, 2H), 4.17 (s, 2H), 3.59 (s, 2H), 3.29 (s, 3H); $^{19}$F NMR (282 MHz, DMSO-$d_6$) δ −118.68, −124.03; MS (ES+): 468.10 (M+1); Analysis calculated for $C_{26}H_{23}F_2NO_5$·HCl·1.25H$_2$O C, 59.32; H, 5.07; Cl, 6.73; N, 2.66; found: C, 59.55; H, 4.93; N, 2.74; Cl, 6.81.

Scheme-464

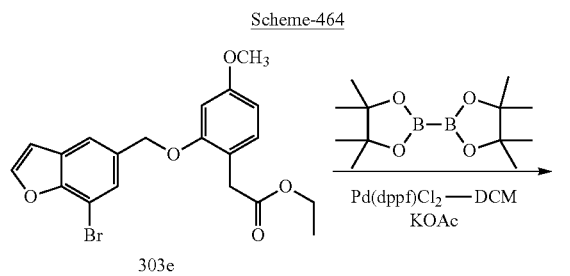

303e

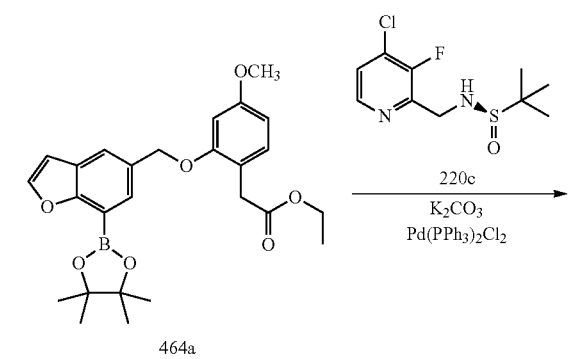

464a

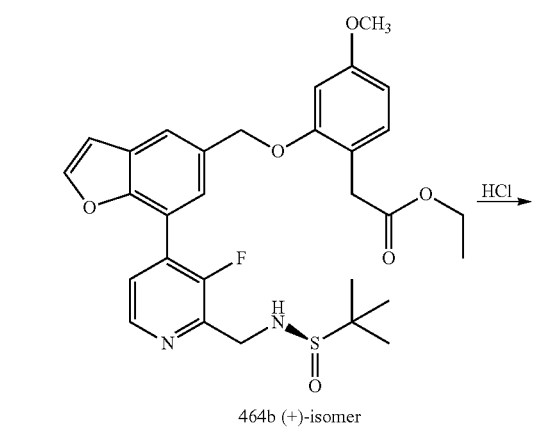

464b (+)-isomer

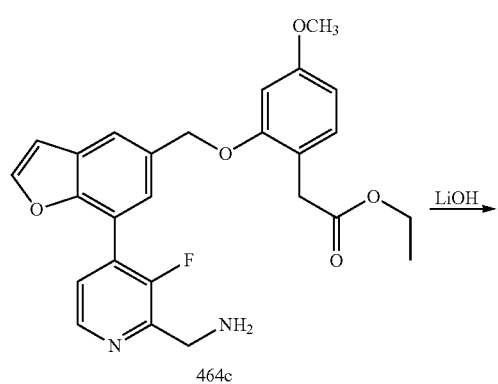

464c

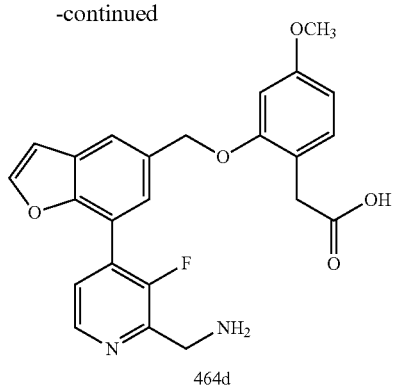

464d

Preparation of 2-(2-((7-(2-(aminomethyl)-3-fluoropyridin-4-yl)benzofuran-5-yl)methoxy)-4-methoxyphenyl)acetic Acid (464d)

Step-1: Preparation of Ethyl 2-(4-methoxy-2-((7-(4,4,5,5-tetramethyl-1,3,2-dioxaborolan-2-yl)benzofuran-5-yl)methoxy)phenyl)acetate (464a)

Compound 464a was prepared according to the procedure reported in step-1 of scheme-59 from ethyl 2-(2-((7-bromobenzofuran-5-yl)methoxy)-4-methoxyphenyl)acetate (303e) (4.0 g, 9.54 mmol), using bis(pinacolato)diboron (3.63 g, 14.31 mmol), potassium acetate (2.81 g, 28.6 mmol) and Pd(dppf)Cl$_2$-DCM (0.779 g, 0.954 mmol) in anhydrous dioxane (100 mL) under a nitrogen atmosphere and heating at 90° C. for 12 h. This gave after workup and purification by flash column chromatography (silica gel, 120 g, eluting with 0 to 15% ethyl acetate in hexanes) ethyl 2-(4-methoxy-2-((7-(4,4,5,5-tetramethyl-1,3,2-dioxaborolan-2-yl)benzofuran-5-yl)methoxy)phenyl)acetate (464a) (3.61 g, 81% yield); $^1$H NMR (300 MHz, DMSO-$d_6$) δ 8.06 (d, J=2.2 Hz, 1H), 7.83 (d, J=1.9 Hz, 1H), 7.65 (d, J=1.9 Hz, 1H), 7.10 (d, J=8.3 Hz, 1H), 6.97 (d, J=2.3 Hz, 1H), 6.68 (d, J=2.4 Hz, 1H), 6.48 (dd, J=8.3, 2.4 Hz, 1H), 5.16 (s, 2H), 3.99 (q, J=7.1 Hz, 2H), 3.74 (s, 3H), 3.50 (s, 2H), 1.34 (s, 12H), 1.10-1.00 (m, 3H).

Step-2: Preparation of (+)-(S)-ethyl 2-(2-((7-(2-((1,1-dimethylethylsulfinamido)methyl)-3-fluoropyridin-4-yl)benzofuran-5-yl)methoxy)-4-methoxyphenyl)acetate (464b)

Compound 464b was prepared according to the procedure reported in step-3 of scheme-1 from ethyl 2-(4-methoxy-2-((7-(4,4,5,5-tetramethyl-1,3,2-dioxaborolan-2-yl)benzofuran-5-yl)methoxy)phenyl)acetate (464a) (1.00 g, 2.144 mmol) in dioxane (30 mL) using (+)-(S)—N-((4-chloro-3-fluoropyridin-2-yl)methyl)-2-methylpropane-2-sulfinamide (220c) (0.681 g, 2.57 mmol), bis(triphenylphosphine)palladium(II) chloride (Pd(PPh$_3$)$_2$Cl$_2$) (0.226 g, 0.322 mmol) and a solution of K$_2$CO$_3$ (0.889 g, 6.43 mmol) in water (3 mL) under a nitrogen atmosphere heating at 90° C. for 3 h on oil bath. This gave after workup and purification by flash column chromatography (silica gel, 40 g, eluting with 0 to 3.5% methanol in DCM) (+)-(S)-ethyl 2-(2-((7-(2-((1,1-dimethylethylsulfinamido)methyl)-3-fluoropyridin-4-yl) benzofuran-5-yl)methoxy)-4-methoxyphenyl)acetate (464b) (689 mg, 57% yield) as a gummy light brown solid; $^1$H NMR (300 MHz, DMSO-$d_6$) δ 8.52 (d, J=4.9 Hz, 1H), 8.09

(d, J=2.2 Hz, 1H), 7.85 (d, J=1.6 Hz, 1H), 7.67 (t, J=5.2 Hz, 1H), 7.52 (s, 1H), 7.16-7.02 (m, 2H), 6.70 (d, J=2.4 Hz, 1H), 6.49 (dd, J=8.3, 2.4 Hz, 1H), 5.86 (t, J=5.8 Hz, 1H), 5.24 (s, 2H), 4.41 (dd, J=5.9, 2.0 Hz, 2H), 3.90 (q, J=7.1 Hz, 2H), 3.74 (s, 3H), 3.53 (s, 2H), 1.11 (s, 9H), 0.97 (t, J=7.1 Hz, 3H); $^{19}$F NMR (282 MHz, DMSO-d$_6$) δ−127.99; MS (ES+): 569.20 (M+1); Optical rotation [t]D=+28.27 (c=0.375, MeOH).

Step-3: Preparation of Ethyl 2-(2-((7-(2-(aminomethyl)-3-fluoropyridin-4-yl)benzofuran-5-yl)methoxy)-4-methoxyphenyl)acetate (464c)

Compound 464c was prepared according to the procedure reported in step-3 of scheme-305 from (+)-(S)-ethyl 2-(2-((7-(2-((1,1-dimethylethylsulfinamido)methyl)-3-fluoropyridin-4-yl)benzofuran-5-yl)methoxy)-4-methoxyphenyl)acetate (464b) (650 mg, 1.143 mmol) in THF (15 mL) using HCl (3M aqueous; 1.143 mL, 3.43 mmol) and stirring at room temperature for 2 h. This gave after workup ethyl 2-(2-((7-(2-(aminomethyl)-3-fluoropyridin-4-yl)benzofuran-5-yl)methoxy)-4-methoxyphenyl)acetate (464c) which was used as such for next step; $^1$H NMR (300 MHz, DMSO-d$_6$) δ 8.68-8.52 (m, 5H), 8.12 (d, J=2.2 Hz, 1H), 7.88 (d, J=1.6 Hz, 1H), 7.80 (t, J=5.3 Hz, 1H), 7.55 (d, J=1.6 Hz, 1H), 7.16-7.07 (m, 2H), 6.69 (d, J=2.4 Hz, 1H), 6.49 (dd, J=8.3, 2.4 Hz, 1H), 5.25 (s, 2H), 3.91 (q, J=7.1 Hz, 2H), 3.74 (s, 3H), 3.53 (s, 2H), 0.98 (t, J=7.1 Hz, 3H); $^{19}$F NMR (282 MHz, DMSO-d$_6$) δ−128.55; MS (ES+): 465.15 (M+1).

Step-4: Preparation of 2-(2-((7-(2-(aminomethyl)-3-fluoropyridin-4-yl)benzofuran-5-yl)methoxy)-4-methoxyphenyl)acetic Acid (464d)

Compound 464d was prepared according to the procedure reported in step-6 of scheme-1 from ethyl 2-(2-((7-(2-(aminomethyl)-3-fluoropyridin-4-yl)benzofuran-5-yl)methoxy)-4-methoxyphenyl)acetate (464c) (1.143 mmol; from above step-3) in MeOH/THF (10 mL each) using a solution of lithium hydroxide (392 mg, 9.14 mmol) in water (10 mL). This gave after workup and purification by reverse phase column [C18 column, eluting with water (containing 0.1% HCl)/acetonitrile (1:0 to 0:1)] 2-(2-((7-(2-(aminomethyl)-3-fluoropyridin-4-yl)benzofuran-5-yl)methoxy)-4-methoxyphenyl)acetic acid (464d) (353 mg, 71%) HCl salt as a light yellow solid; $^1$H NMR (300 MHz, DMSO-d$_6$) δ 12.23 (s, 1H), 8.66-8.59 (m, 4H), 8.12 (d, J=2.2 Hz, 1H), 7.91 (d, J=1.6 Hz, 1H), 7.80 (t, J=5.3 Hz, 1H), 7.61-7.58 (m, 1H), 7.15-7.06 (m, 2H), 6.68 (d, J=2.4 Hz, 1H), 6.48 (dd, J=8.3, 2.4 Hz, 1H), 5.27 (s, 2H), 4.44-4.24 (m, 2H), 3.73 (s, 3H), 3.50 (s, 2H); $^{19}$F NMR (282 MHz, DMSO-d$_6$) δ−128.40; MS (ES+): 437.10 (M+1); MS (ES−): 435.10 (M−1); Analysis calculated for C$_{24}$H$_{21}$FN$_2$O$_5$·1.1HCl·1.25H$_2$O: C, 57.76; H, 4.97; N, 5.61; Cl, 7.81; Found: C, 57.56; H, 5.09; N, 5.64; Cl, 7.95.

Scheme-465

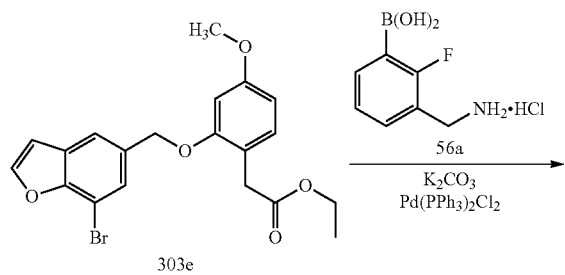

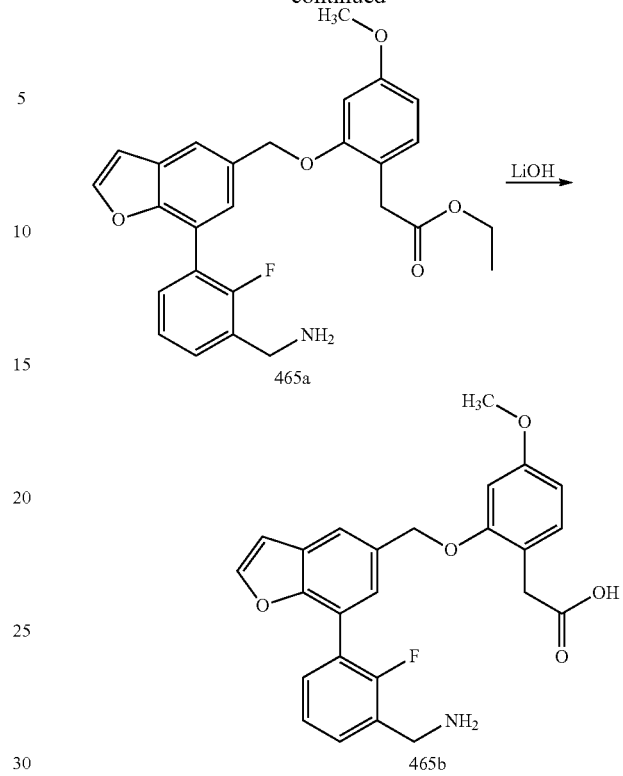

Preparation of 2-(2-((7-(3-(aminomethyl)-2-fluorophenyl)benzofuran-5-yl)methoxy)-4-methoxyphenyl)acetic Acid (465b)

Step-1: Preparation of Ethyl 2-(2-((7-(3-(aminomethyl)-2-fluorophenyl)benzofuran-5-yl)methoxy)-4-methoxyphenyl)acetate (465a)

Compound 465a was prepared according to the procedure reported in step-3 of scheme-1 from ethyl 2-(2-((7-bromobenzofuran-5-yl)methoxy)-4-methoxyphenyl)acetate (303e) (300 mg, 0.716 mmol) in dioxane (5 mL) using 3-(aminomethyl)-2-fluorophenylboronic acid hydrochloride (56a) (220 mg, 1.073 mmol), bis(triphenylphosphine)palladium(II) chloride (Pd(PPh$_3$)$_2$Cl$_2$) (75 mg, 0.107 mmol) and a solution of K$_2$CO$_3$ (297 mg, 2.147 mmol) in water (0.5 mL) under a nitrogen atmosphere heating at 90° C. for 3 h on oil bath. This gave after workup and purification by flash column chromatography (silica gel, 24 g, eluting with 0 to 5% methanol in DCM) ethyl 2-(2-((7-(3-(aminomethyl)-2-fluorophenyl)benzofuran-5-yl)methoxy)-4-methoxyphenyl)acetate (465a) (138 mg, 42% yield) as a clear oil. $^1$H NMR (300 MHz, DMSO-d$_6$) δ 8.05 (d, J=2.2 Hz, 1H), 7.75 (d, J=1.7 Hz, 1H), 7.63-7.56 (m, 1H), 7.45 (td, J=7.4, 1.9 Hz, 1H), 7.40 (s, 1H), 7.31 (t, J=7.6 Hz, 1H), 7.10 (d, J=8.3 Hz, 1H), 7.05 (d, J=2.2 Hz, 1H), 6.70 (d, J=2.4 Hz, 1H), 6.48 (dd, J=8.3, 2.4 Hz, 1H), 5.22 (s, 2H), 3.89 (q, J=7.1 Hz, 2H), 3.83 (s, 2H), 3.74 (s, 3H), 3.52 (s, 2H), 0.97 (t, J=7.1 Hz, 3H); $^{19}$F NMR (282 MHz, DMSO-d$_6$) δ−121.75; MS (ES+): 464.10 (M+1).

Step-2: Preparation of 2-(2-((7-(3-(aminomethyl)-2-fluorophenyl)benzofuran-5-yl)methoxy)-4-methoxyphenyl)acetic Acid (465b)

Compound 465b was prepared according to the procedure reported in step-6 of scheme-1 from ethyl 2-(2-((7-(3-

(aminomethyl)-2-fluorophenyl)benzofuran-5-yl)methoxy)-4-methoxyphenyl)acetate (465a) (125 mg, 0.270 mmol) in MeOH/THF (5 mL each) using a solution of lithium hydroxide (69 mg, 1.618 mmol) in water (5 mL). This gave after workup and purification by reverse phase column [C18 column, eluting with water (containing 0.1% HCl)/acetonitrile (1:0 to 0:1)] 2-(2-((7-(3-(aminomethyl)-2-fluorophenyl)benzofuran-5-yl)methoxy)-4-methoxyphenyl)acetic acid (465b) (104 mg, 89% yield) HCl salt as a white solid; $^1$H NMR (300 MHz, DMSO-$d_6$) δ 9.03 (s, 3H), 8.06 (d, J=2.2 Hz, 1H), 7.82 (d, J=1.6 Hz, 1H), 7.75-7.62 (m, 2H), 7.47-7.45 (m, 1H), 7.42 (t, J=7.7 Hz, 1H), 7.10 (d, J=8.3 Hz, 1H), 7.06 (d, J=2.2 Hz, 1H), 6.67 (d, J=2.4 Hz, 1H), 6.48 (dd, J=8.3, 2.4 Hz, 1H), 5.25 (s, 2H), 4.17 (s, 2H), 3.73 (s, 3H), 3.49 (s, 2H); $^{19}$F NMR (282 MHz, DMSO-$d_6$) δ—118.42; MS (ES+): 436.10 (M+1); Analysis calculated for $C_{25}H_{22}FNO_5 \cdot HCl \cdot 0.75 H_2O$: C, 61.86; H, 5.09; Cl, 7.30; N, 2.89; Found: C, 61.53; H, 5.23; N, 2.92; Cl, 7.62.

Scheme-466

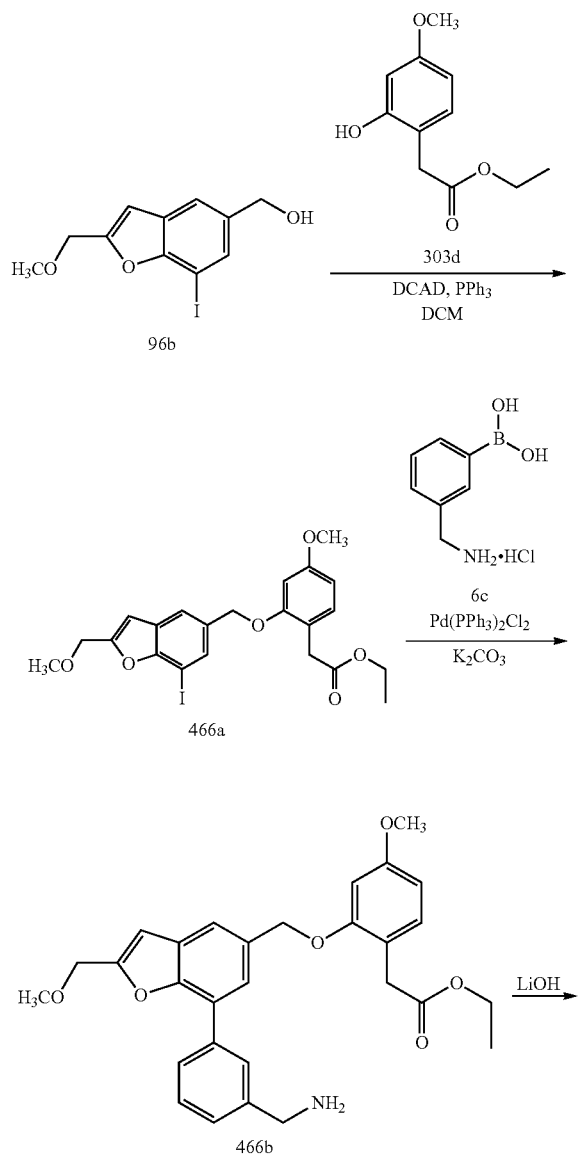

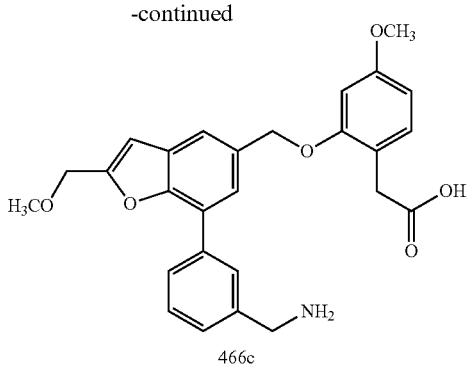

Preparation of 2-(2-((7-(3-(aminomethyl)phenyl)-2-(methoxymethyl)benzofuran-5-yl)methoxy)-4-methoxyphenyl)acetic Acid (466c)

Step-1: Preparation of Ethyl 2-(2-((7-iodo-2-(methoxymethyl)benzofuran-5-yl)methoxy)-4-methoxyphenyl)acetate (466a)

Compound 466a was prepared according to the procedure reported in step-2 of scheme-23 from (7-iodo-2-(methoxymethyl)benzofuran-5-yl)methanol (96b) (2.00 g, 6.29 mmol) in DCM (60 mL) using triphenylphosphine (1.786 g, 6.81 mmol), ethyl 2-(2-hydroxy-4-methoxyphenyl)acetate (303d) (1.101 g, 5.24 mmol) and a solution of (E)-bis(4-chlorobenzyl) diazene-1,2-dicarboxylate (DCAD, 2.501 g, 6.81 mmol) in DCM (60 mL). This gave after workup and purification by flash column chromatography (silica gel, 120 g, eluting with 0 to 20% ethyl acetate in hexanes) ethyl 2-(2-((7-iodo-2-(methoxymethyl)benzofuran-5-yl)methoxy)-4-methoxyphenyl)acetate (466a) (2.24 g, 84% yield) as a white solid; $^1$H NMR (300 MHz, DMSO-$d_6$) δ 7.73 (d, J=1.5 Hz, 1H), 7.66 (d, J=1.5 Hz, 1H), 7.11 (d, J=8.3 Hz, 1H), 7.07 (s, 1H), 6.65 (d, J=2.4 Hz, 1H), 6.48 (dd, J=8.3, 2.4 Hz, 1H), 5.13 (s, 2H), 4.56 (s, 2H), 4.07-3.94 (m, 2H), 3.74 (s, 3H), 3.52 (s, 2H), 3.33 (s, 3H), 1.08 (t, J=7.1 Hz, 3H); MS (ES+): 511.00 (M+1).

Step-2: Preparation of Ethyl 2-(2-((7-(3-(aminomethyl)phenyl)-2-(methoxymethyl)benzofuran-5-yl)methoxy)-4-methoxyphenyl)acetate (466b)

Compound 466b was prepared according to the procedure reported in step-3 of scheme-1 from ethyl 2-(2-((7-iodo-2-(methoxymethyl)benzofuran-5-yl)methoxy)-4-methoxyphenyl)acetate (466a) (500 mg, 0.980 mmol) in dioxane (15 mL) using (3-(aminomethyl)phenyl)boronic acid hydrochloride (6c) (275 mg, 1.470 mmol), a solution of potassium carbonate (406 mg, 2.94 mmol) in water (1.8 mL), Pd(PPh$_3$)$_2$Cl$_2$ (138 mg, 0.196 mmol) and heating under a nitrogen atmosphere at 100° C. for 3 h. This gave after workup and purification by flash column chromatography (silica gel, 24 g, eluting with 0 to 10% methanol in DCM) ethyl 2-(2-((7-(3-(aminomethyl)phenyl)-2-(methoxymethyl)benzofuran-5-yl)methoxy)-4-methoxyphenyl)acetate (466b) (375 mg, 78% yield) as a brown oil. $^1$H NMR (300 MHz, DMSO-$d_6$) δ 7.78 (d, J=1.9 Hz, 1H), 7.71 (dt, J=7.6, 1.6 Hz, 1H), 7.65 (d, J=1.6 Hz, 1H), 7.56 (d, J=1.7 Hz, 1H), 7.47 (t, J=7.6 Hz, 1H), 7.40 (d, J=7.8 Hz, 1H), 7.11 (d, J=8.3 Hz, 1H), 6.99 (s, 1H), 6.69 (d, J=2.4 Hz, 1H), 6.48 (dd, J=8.3, 2.4 Hz, 1H), 5.76 (s, 2H), 5.22 (s, 2H), 4.57 (s, 2H), 3.92 (q, J=7.1 Hz, 2H), 3.81 (s, 3H), 3.74 (s, 3H), 3.54 (s, 2H), 0.98 (t, J=7.1 Hz, 3H); MS (ES+): 490.20 (M+1).

Step-3: Preparation of 2-(2-((7-(3-(aminomethyl) phenyl)-2-(methoxymethyl)benzofuran-5-yl) methoxy)-4-methoxyphenyl)acetic Acid (466c)

Compound 466c was prepared according to the procedure reported in step-6 of scheme-1 from ethyl 2-(2-((7-(3-(aminomethyl)phenyl)-2-(methoxymethyl)benzofuran-5-yl) methoxy)-4-methoxyphenyl)acetate (466b) (350 mg, 0.715 mmol) in THF/methanol (5 mL, 1:1 each) using solution of lithium hydroxide hydrate (184 mg, 4.29 mmol) in water (5 mL) and stirring at room temperature for 16 h. This gave after workup and purification by reverse-phase column chromatography [C-18 column, eluting with water (containing 0.1% HCl)/acetonitrile (1:0 to 0:1)] 2-(2-((7-(3-(aminomethyl)phenyl)-2-(methoxymethyl)benzofuran-5-yl) methoxy)-4-methoxyphenyl)acetic acid (466c) (175 mg, 53.0% yield) HCl salt as a white solid. $^1$H NMR (300 MHz, DMSO-$d_6$) δ 8.72 (s, 3H), 7.99-7.96 (m, 1H), 7.95-7.88 (m, 1H), 7.72 (d, J=1.6 Hz, 1H), 7.64 (d, J=1.7 Hz, 1H), 7.62-7.54 (m, 2H), 7.11 (d, J=8.3 Hz, 1H), 7.00 (s, 1H), 6.67 (d, J=2.4 Hz, 1H), 6.48 (dd, J=8.3, 2.4 Hz, 1H), 5.25 (s, 2H), 4.58 (s, 2H), 4.12 (s, 2H), 3.73 (s, 3H), 3.51 (s, 2H), 3.33 (s, 3H); MS (ES+): 462.10 (M+1); MS (ES-): 460.20 (M-1); Analysis calculated for $C_{27}H_{27}NO_6 \cdot HCl \cdot 0.5H_2O$: C, 63.97; H, 5.77; N, 2.76; Cl, 6.99; Found: C, 63.90; H, 5.65; N, 2.74; Cl, 6.84.

Scheme-467

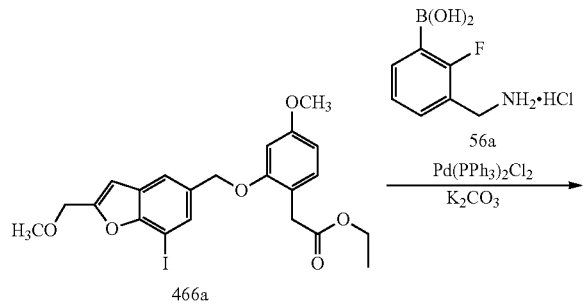

466a

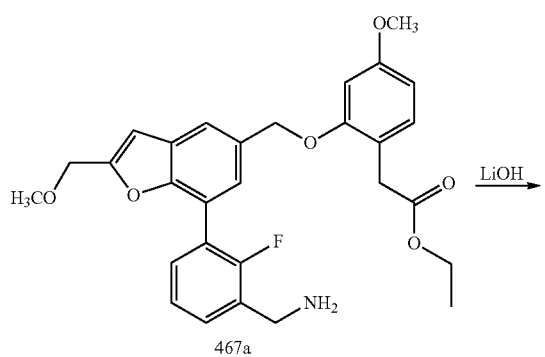

467a

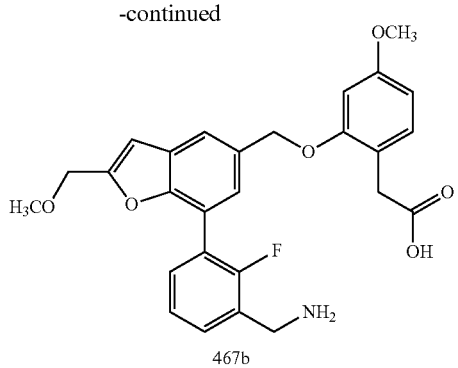

467b

Preparation of 2-(2-((7-(3-(aminomethyl)-2-fluorophenyl)-2-(methoxymethyl)benzofuran-5-yl) methoxy)-4-methoxyphenyl)acetic Acid (467b)

Step-1: Preparation of Ethyl 2-(2-((7-(3-(aminomethyl)-2-fluorophenyl)-2-(methoxymethyl)benzofuran-5-yl)methoxy)-4-methoxyphenyl)acetate (467a)

Compound 467a was prepared according to the procedure reported in step-3 of scheme-1 from ethyl 2-(2-((7-iodo-2-(methoxymethyl)benzofuran-5-yl)methoxy)-4-methoxyphenyl)acetate (466a) (500 mg, 0.980 mmol) in dioxane (15 mL) using 3-(aminomethyl)-2-fluorophenylboronic acid hydrochloride (56a) (166 mg, 0.980 mmol), a solution of potassium carbonate (406 mg, 2.94 mmol) in water (1.8 mL), Pd(PPh$_3$)$_2$Cl$_2$ (138 mg, 0.196 mmol) and heating under a nitrogen atmosphere at 100° C. for 3 h. This gave after workup and purification by flash column chromatography (silica gel, 24 g, eluting with 0 to 7% methanol in DCM) ethyl 2-(2-((7-(3-(aminomethyl)-2-fluorophenyl)-2-(methoxymethyl)benzofuran-5-yl)methoxy)-4-methoxyphenyl)acetate (467a) (227 mg, 46% yield) as a brown oil. $^1$H NMR (300 MHz, DMSO-$d_6$) δ 7.71 (d, J=1.7 Hz, 1H), 7.63-7.54 (m, 1H), 7.44 (td, J=7.4, 1.9 Hz, 1H), 7.39 (t, J=1.3 Hz, 1H), 7.31 (t, J=7.6 Hz, 1H), 7.10 (d, J=8.3 Hz, 1H), 6.98 (s, 1H), 6.70 (d, J=2.4 Hz, 1H), 6.48 (dd, J=8.3, 2.4 Hz, 1H), 5.21 (s, 2H), 4.52 (s, 2H), 3.90 (q, J=7.1 Hz, 2H), 3.83 (s, 2H), 3.74 (s, 3H), 3.52 (s, 2H), 3.29 (s, 3H), 0.99 (t, J=7.1 Hz, 3H); $^{19}$F NMR (282 MHz, DMSO-$d_6$) δ −121.97; MS (ES+): 508.20 (M+1).

Step-2: Preparation of 2-(2-((7-(3-(aminomethyl)-2-fluorophenyl)-2-(methoxymethyl)benzofuran-5-yl) methoxy)-4-methoxyphenyl)acetic Acid (467b)

Compound 467b was prepared according to the procedure reported in step-6 of scheme-1 from ethyl 2-(2-((7-(3-(aminomethyl)-2-fluorophenyl)-2-(methoxymethyl)benzofuran-5-yl)methoxy)-4-methoxyphenyl)acetate (467a) (200 mg, 0.394 mmol) in THF/methanol (5 mL, each) using a solution of lithium hydroxide hydrate (101 mg, 2.364 mmol) in water (5 mL) and stirring at room temperature for 16 h. This gave after workup and purification by reverse-phase column chromatography [C-18 column, eluting with water (containing 0.1% HCl)/acetonitrile (1:0 to 0:1)] 2-(2-((7-(3-(aminomethyl)-2-fluorophenyl)-2-(methoxymethyl)benzofuran-5-yl)methoxy)-4-methoxyphenyl)acetic acid (467b) (76 mg, 40% yield) HCl salt as a white solid. $^1$H NMR (300 MHz, DMSO-$d_6$) δ 8.87 (s, 3H), 7.78 (d, J=1.6 Hz, 1H), 7.73-7.61 (m, 2H), 7.51-7.37 (m, 2H), 7.10 (d, J=8.3 Hz, 1H), 7.00 (s, 1H), 6.67 (d, J=2.4 Hz, 1H), 6.48 (dd, J=8.3, 2.4 Hz, 1H), 5.24 (s, 2H), 4.52 (s, 2H), 4.17 (s, 2H), 3.73 (s, 3H), 3.49 (s, 2H), 3.29 (s, 3H); $^{19}$F NMR (282 MHz, DMSO-$d_6$) δ −118.66; MS (ES+): 480.20 (M+1); MS (ES−): 478.20 (M−1); Analysis calculated for $C_{27}H_{26}FNO_6$·HCl·0.5$H_2O$: C, 61.77; H, 5.38; N, 2.67; Cl, 6.75; Found: C, 61.67; H, 5.37; N, 2.64; Cl, 6.66.

Scheme-468

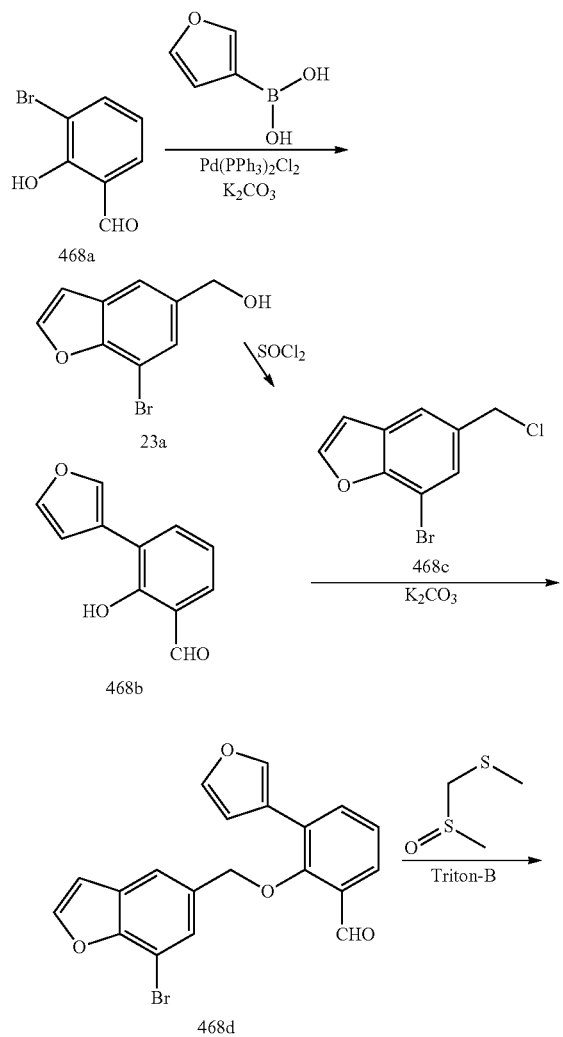

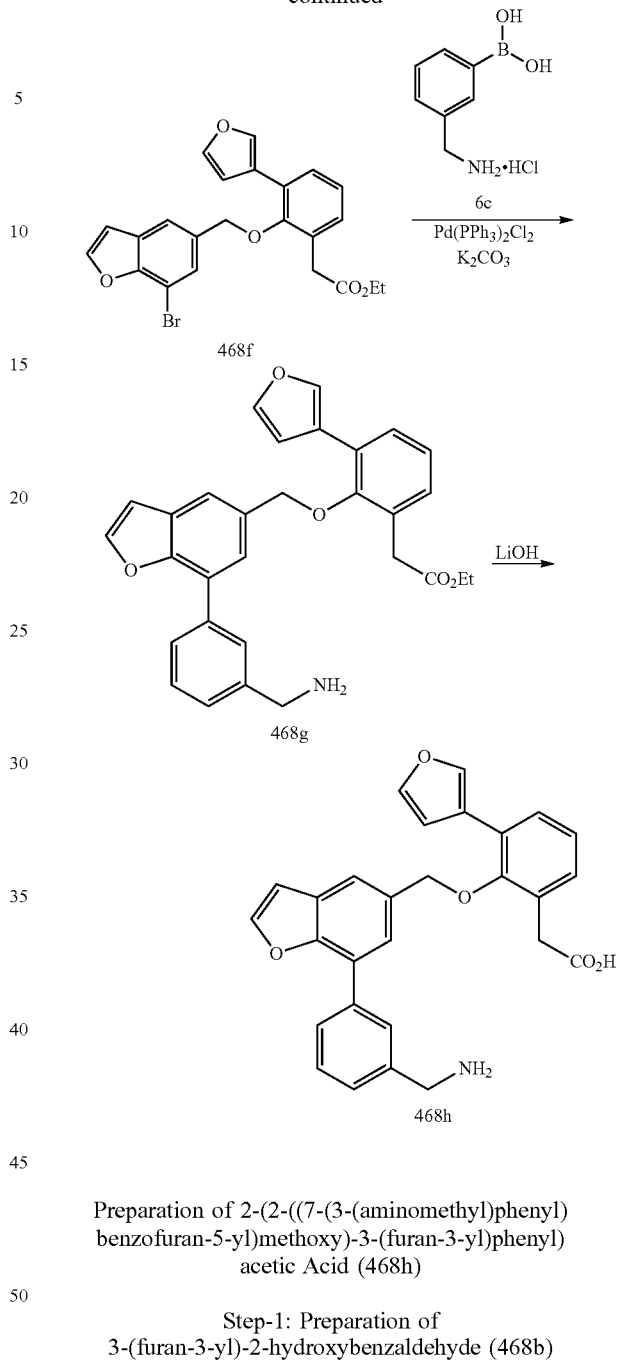

Preparation of 2-(2-((7-(3-(aminomethyl)phenyl)benzofuran-5-yl)methoxy)-3-(furan-3-yl)phenyl)acetic Acid (468h)

Step-1: Preparation of 3-(furan-3-yl)-2-hydroxybenzaldehyde (468b)

Compound 468b was prepared according to the procedure reported in step-3 of scheme-1 from 3-bromo-2-hydroxybenzaldehyde (468a) (1.0 g, 4.97 mmol; CAS #1829-34-1) in dioxane (15 mL) using furan-3-ylboronic acid (0.835 g, 7.46 mmol), bis(triphenylphosphine)palladium(II) chloride (Pd(PPh$_3$)$_2$Cl$_2$) (0.349 g, 0.497 mmol) and 3.3 M aqueous K$_2$CO$_3$ (4.52 mL, 14.92 mmol) under an N$_2$ atmosphere heating at 100° C. for 16 h on oil bath. This gave after workup, purification by flash column chromatography (silica gel, 24 g, eluting with 0-1% EtOAc in hexane) 3-(furan-3-yl)-2-hydroxybenzaldehyde (468b) (0.69 g, 74% yield) as a clear yellow oil that solidified upon drying under vacuum; $^1$H NMR (300 MHz, DMSO-$d_6$) δ 11.78 (s, 1H), 10.06 (s, 1H), 8.25 (dd, J=1.6, 0.8 Hz, 1H), 7.98 (dd, J=7.7, 1.7 Hz, 1H), 7.78 (t, J=1.7 Hz, 1H), 7.73 (dd, J=7.7, 1.7 Hz, 1H), 7.16 (t, J=7.7 Hz, 1H), 7.09 (dd, J=2.0, 0.9 Hz, 1H).

Step-3: Preparation of 7-bromo-5-(chloromethyl)benzofuran (468c)

Compound 468c was prepared according to the procedure reported in step-4 of scheme-257 from (7-bromobenzofuran-5-yl)methanol (23a) (5.00 g, 22.02 mmol) in DCM (100 mL) using $SOCl_2$ (3.21 mL, 44.0 mmol), DMF (0.3 mL) and stirring reaction at room temperature for 5 h. This gave after workup 7-bromo-5-(chloromethyl)benzofuran (468c) (4.88 g, 90% yield) as an off-white solid; $^1$H NMR (300 MHz, DMSO-$d_6$) δ 8.16 (d, J=2.2 Hz, 1H), 7.77 (d, J=1.6 Hz, 1H), 7.66 (d, J=1.6 Hz, 1H), 7.12 (d, J=2.2 Hz, 1H), 4.88 (s, 2H).

Step-3: Preparation of 2-((7-bromobenzofuran-5-yl)methoxy)-3-(furan-3-yl)benzaldehyde (468d)

Compound 468d was prepared according to the procedure reported in step-2 of scheme-152 from 3-(furan-3-yl)-2-hydroxybenzaldehyde (468b) (0.69 g, 3.67 mmol) using 7-bromo-5-(chloromethyl)benzofuran (468c) (0.9 g, 3.67 mmol) and $K_2CO_3$ (1.52 g, 11.0 mmol) in DMF (20 mL) and stirring at room temperature for 16 h. This gave after workup and purification by flash column chromatography (Silica gel, 24 g, eluting with 0-5% EtOAc in hexane) 2-((7-bromobenzofuran-5-yl)methoxy)-3-(furan-3-yl)benzaldehyde (468d) (0.82 g, 56% yield) as a white solid. $^1$H NMR (300 MHz, DMSO-$d_6$) δ 10.19 (d, J=0.8 Hz, 1H), 8.23-8.09 (m, 2H), 7.95 (dd, J=7.7, 1.8 Hz, 1H), 7.82 (t, J=1.7 Hz, 1H), 7.76-7.63 (m, 2H), 7.56 (d, J=1.5 Hz, 1H), 7.39 (td, J=7.7, 0.8 Hz, 1H), 7.11 (d, J=2.2 Hz, 1H), 7.02 (dd, J=1.9, 0.8 Hz, 1H), 4.99 (s, 2H); MS (ES+): 397/399 (M+1).

Step-4: Preparation of 7-bromo-5-((2-(furan-3-yl)-6-(2-(methylsulfinyl)-2-(methylthio)vinyl)phenoxy)methyl)benzofuran (468e)

Compound 468e was prepared according to the procedure reported in step-3 of scheme-266 from 2-((7-bromobenzofuran-5-yl)methoxy)-3-(furan-3-yl)benzaldehyde (468d) (0.82 g, 2.064 mmol) in THF (20 mL) using methyl(methylsulfinylmethyl)sulfane (0.410 g, 3.30 mmol), Triton-B (40 wt. % in methanol) (0.432 g, 1.032 mmol) and heating at 70° C. for 16 h. This gave after workup and purification by flash column chromatography (Silica gel, 24 g, eluting with 0-40% EtOAc in hexane) 7-bromo-5-((2-(furan-3-yl)-6-(2-(methylsulfinyl)-2-(methylthio)vinyl)phenoxy)methyl)benzofuran (468e) (0.67 g, 65% yield) as a pale-yellow oil; $^1$H NMR (300 MHz, DMSO-$d_6$) δ 8.14 (d, J=2.2 Hz, 1H), 8.11 (dt, J=1.6, 0.9 Hz, 1H), 7.97 (dd, J=8.0, 1.6 Hz, 1H), 7.85 (s, 1H), 7.82-7.77 (m, 1H), 7.73-7.64 (m, 2H), 7.59 (d, J=1.4 Hz, 1H), 7.33 (t, J=7.7 Hz, 1H), 7.10 (dd, J=2.2, 0.9 Hz, 1H), 7.00 (dd, J=1.9, 0.9 Hz, 1H), 4.83-4.71 (m, 2H), 2.71 (d, J=0.9 Hz, 3H), 2.28 (d, J=0.9 Hz, 3H); MS (ES+): 503/505 (M+1).

Step-5: Preparation of Ethyl 2-(2-((7-bromobenzofuran-5-yl)methoxy)-3-(furan-3-yl)phenyl)acetate (468f)

Compound 468f was prepared according to the procedure reported in step-4 of scheme-266 from 7-bromo-5-((2-(furan-3-yl)-6-(2-(methylsulfinyl)-2-(methylthio)vinyl)phenoxy)methyl)benzofuran (468e) (0.67 g, 1.331 mmol) in EtOH (20 mL) using 4 M HCl in dioxane (1.664 mL, 6.65 mmol) and heating at 80° C. for 16 h. This gave after workup and purification by flash column chromatography (Silica gel, 24 g, eluting with 0-5% EtOAc in hexane) ethyl 2-(2-((7-bromobenzofuran-5-yl)methoxy)-3-(furan-3-yl)phenyl)acetate (468f) (474 mg, 78% yield) as a colorless oil; $^1$H NMR (300 MHz, DMSO-$d_6$) δ 8.15 (d, J=2.1 Hz, 1H), 8.08-8.02 (m, 1H), 7.77 (t, J=1.7 Hz, 1H), 7.65 (d, J=1.5 Hz, 1H), 7.58-7.49 (m, 2H), 7.26 (dd, J=7.6, 1.9 Hz, 1H), 7.19 (t, J=7.5 Hz, 1H), 7.13 (d, J=2.2 Hz, 1H), 6.94 (dd, J=1.9, 0.8 Hz, 1H), 4.74 (s, 2H), 4.04 (q, J=7.1 Hz, 2H), 3.73 (s, 2H), 1.11 (t, J=7.1 Hz, 3H); MS (ES+): 455/457 (M+1).

Step-6: Preparation of Ethyl 2-(2-((7-(3-(aminomethyl)phenyl)benzofuran-5-yl)methoxy)-3-(furan-3-yl)phenyl)acetate (468g)

Compound 468g was prepared according to the procedure reported in step-3 of scheme-1 from ethyl 2-(2-((7-bromobenzofuran-5-yl)methoxy)-3-(furan-3-yl)phenyl)acetate (468f) (109 mg, 0.239 mmol) in dioxane (4 mL)/water (1 mL) using 3-(aminomethyl)phenylboronic acid hydrochloride (6c) (67 mg, 0.359 mmol), bis(triphenylphosphine)palladium(II) chloride ($Pd(PPh_3)_2Cl_2$) (17 mg, 0.024 mmol) and 3.3 M aqueous $K_2CO_3$ (0.218 mL, 0.718 mmol) under an $N_2$ atmosphere heating at 100° C. for 16 h on oil bath. This gave after workup, purification by flash column chromatography (silica gel 12 g, eluting with methanol in DCM from 0-6%) ethyl 2-(2-((7-(3-(aminomethyl)phenyl)benzofuran-5-yl)methoxy)-3-(furan-3-yl)phenyl)acetate (468g) (81 mg, 70% yield) as a colorless oil, which was used as such in the next reaction; MS (ES+): 482 (M+1).

Step-7: Preparation of 2-(2-((7-(3-(aminomethyl)phenyl)benzofuran-5-yl)methoxy)-3-(furan-3-yl)phenyl)acetic Acid (468h)

Compound 468h was prepared according to the procedure reported in step-6 of scheme-1 from ethyl 2-(2-((7-(3-(aminomethyl)phenyl)benzofuran-5-yl)methoxy)-3-(furan-3-yl)phenyl)acetate (468g) (81 mg, 0.168 mmol) in MeOH (3 mL), using a 2M aqueous solution of lithium hydroxide (0.421 mL, 0.841 mmol). This gave after workup and purification by reverse phase column [C18 (100 g), eluting with 0-60% MeCN in $H_2O$ containing 0.1% HCl] 2-(2-((7-(3-(aminomethyl)phenyl)benzofuran-5-yl)methoxy)-3-(furan-3-yl)phenyl)acetic acid (468h) (70 mg, 92% yield) HCl salt as a white solid; $^1$H NMR (300 MHz, DMSO-$d_6$) δ 8.12 (d, J=2.2 Hz, 1H), 8.09 (dd, J=1.6, 0.8 Hz, 1H), 7.97 (d, J=1.8 Hz, 1H), 7.90 (dt, J=7.6, 1.6 Hz, 1H), 7.78 (t, J=1.7 Hz, 1H), 7.71 (d, J=1.6 Hz, 1H), 7.62 (t, J=7.6 Hz, 1H), 7.58-7.49 (m, 3H), 7.27 (dd, J=7.6, 1.9 Hz, 1H), 7.19 (t, J=7.5 Hz, 1H), 7.10 (d, J=2.2 Hz, 1H), 6.99 (dd, J=1.9, 0.8 Hz, 1H), 4.82 (s, 2H), 4.15 (s, 2H), 3.70 (s, 2H); MS (ES+): 454 (M+1), (ES−): 452 (M−1); Analysis calculated for $C_{28}H_{23}NO_5 \cdot HCl \cdot 1.5H_2O$: C, 65.05; H, 5.26; Cl, 6.86; N, 2.71; Found: C, 65.11; H, 5.21; Cl, 6.99; N, 2.78.

Scheme-469

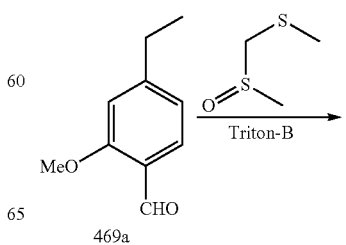

469a

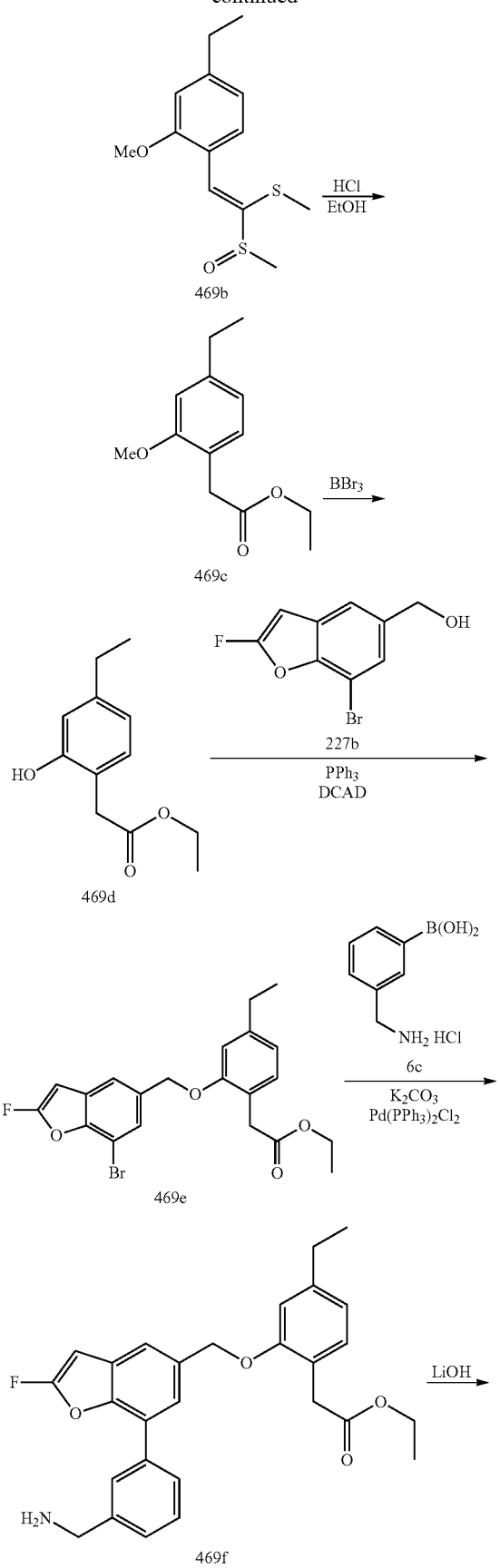

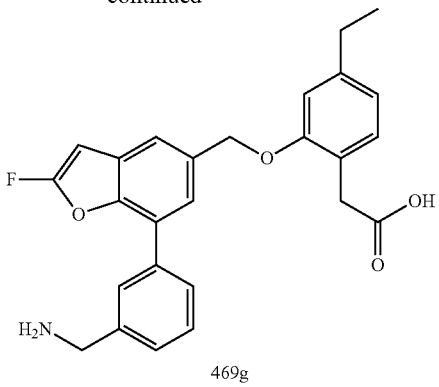

Preparation of 2-(2-((7-(3-(aminomethyl)phenyl)-2-fluorobenzofuran-5-yl)methoxy)-4-ethylphenyl)acetic Acid (469g)

Step-1: Preparation of (2-(4-ethyl-2-methoxyphenyl)-1-(methylsulfinyl)vinyl)(methyl)sulfane (469b)

Compound 469b was prepared according to the procedure reported in step-3 of scheme-266 from 4-ethyl-2-methoxybenzaldehyde (469a) (1.82 g, 11.08 mmol; CAS #142224-35-9) in THF (20 mL) using methyl(methylsulfinylmethyl)sulfane (2.203 g, 17.73 mmol), Triton-B (40% methanolic solution; 2.317 g, 5.54 mmol) and heating at 70° C. for 16 h. This gave after workup and purification by flash column chromatography (silica gel, 24 g, eluting with 0-40% EtOAc in hexane) (2-(4-ethyl-2-methoxyphenyl)-1-(methylsulfinyl)vinyl)(methyl)sulfane (469b) (2.66 g, 89% yield) as a pale-yellow oil; $^1$H NMR (300 MHz, DMSO-d$_6$) δ 8.01 (d, J=7.9 Hz, 1H), 7.75 (s, 1H), 6.95 (d, J=1.6 Hz, 1H), 6.93-6.83 (m, 1H), 3.84 (s, 3H), 2.71 (s, 3H), 2.64 (q, J=7.6 Hz, 2H), 2.28 (s, 3H), 1.22 (t, J=7.6 Hz, 3H); MS (ES+): 271 (M+1).

Step-2: Preparation of Ethyl 2-(4-ethyl-2-methoxyphenyl)acetate (469c)

Compound 469c was prepared according to the procedure reported in step-4 of scheme-266 from (2-(4-ethyl-2-methoxyphenyl)-1-(methylsulfinyl)vinyl)(methyl)sulfane (469b) (2.66 g, 9.84 mmol) in ethanol (20 mL) using 4 M HCl in dioxane (12.30 mL, 49.2 mmol) and heating at 80° C. for 16 h. This gave after workup and purification by flash column chromatography (silica gel, 24 g, eluting with 0-2% EtOAc in hexane) ethyl 2-(4-ethyl-2-methoxyphenyl)acetate (469c) (1.61 g, 74% yield) as a colorless liquid; $^1$H NMR (300 MHz, DMSO-d$_6$) δ 7.06 (d, J=7.5 Hz, 1H), 6.82 (d, J=1.6 Hz, 1H), 6.73 (dd, J=7.5, 1.6 Hz, 1H), 4.05 (q, J=7.1 Hz, 2H), 3.74 (s, 3H), 3.51 (s, 2H), 2.58 (q, J=7.6 Hz, 2H), 1.22-1.13 (m, 6H); MS (ES+): 245 (M+Na).

Step-3: Preparation of Ethyl 2-(4-ethyl-2-hydroxyphenyl)acetate (469d)

Compound 469d was prepared according to the procedure reported in step-5 of scheme-257 from ethyl 2-(4-ethyl-2-methoxyphenyl)acetate (469c) (1.61 g, 7.24 mmol) in dichloromethane (15 mL) using boron tribromide (14.49 mL, 14.49 mmol; 1M solution in DCM) and stirring at 0° C. for 2 h. This gave after workup purification by flash column chromatography (silica gel, eluting with 0-10% EtOAc in hexane) to provide the product ethyl 2-(4-ethyl-2-hydroxyphenyl)acetate (469d) (472 mg, 2.266 mmol, 31% yield) as a yellow oil; $^1$H NMR (300 MHz, DMSO-d$_6$) δ 9.32 (s, 1H), 6.98 (d, J=7.6 Hz, 1H), 6.62 (d, J=1.7 Hz, 1H), 6.58 (dd, J=7.6, 1.7 Hz, 1H), 4.05 (q, J=7.1 Hz, 2H), 3.48 (s, 2H), 2.49-2.43 (m, 2H), 1.15 (dt, J=10.4, 7.3 Hz, 6H); MS (ES+): 209 (M+1).

Step-4: Preparation of Ethyl 2-(2-((7-bromo-2-fluorobenzofuran-5-yl)methoxy)-4-ethylphenyl)acetate (469e)

Compound 469e was prepared according to the procedure reported in step-2 of scheme-23 from (7-bromo-2-fluorobenzofuran-5-yl)methanol (227b) (555 mg, 2.266 mmol) in DCM (20 mL) using triphenylphosphine (892 mg, 3.40 mmol), ethyl 2-(4-ethyl-2-hydroxyphenyl)acetate (469d) (472 mg, 2.266 mmol) and a solution of (E)-bis(4-chlorobenzyl) diazene-1,2-dicarboxylate (DCAD, 1248 mg, 3.40 mmol) in DCM (20 mL). This gave after workup and purification by flash column chromatography (silica gel, 24 g, eluting with 0 to 5% ethyl acetate in hexanes) ethyl 2-(2-((7-bromo-2-fluorobenzofuran-5-yl)methoxy)-4-ethylphenyl)acetate (469e) (575 mg, 58% yield) as a pale-yellow oil. $^1$H NMR (300 MHz, DMSO-d$_6$) δ 7.64 (d, J=1.5 Hz, 1H), 7.60 (d, J=1.5 Hz, 1H), 7.11 (d, J=7.5 Hz, 1H), 6.94 (d, J=1.6 Hz, 1H), 6.76 (dd, J=7.6, 1.5 Hz, 1H), 6.54 (d, J=6.4 Hz, 1H), 5.16 (s, 2H), 4.01 (q, J=7.1 Hz, 2H), 3.57 (s, 2H), 2.58 (q, J=7.7 Hz, 2H), 1.18 (t, J=7.6 Hz, 3H), 1.08 (t, J=7.1 Hz, 3H). $^{19}$F NMR (282 MHz, DMSO-d$_6$) δ−110.50; MS (ES+): 435/437 (M+1).

Step-5: Preparation of Ethyl 2-(2-((7-(3-(aminomethyl)phenyl)-2-fluorobenzofuran-5-yl)methoxy)-4-ethylphenyl)acetate (469f)

Compound 469f was prepared according to the procedure reported in step-3 of scheme-1 from ethyl 2-(2-((7-bromo-2-fluorobenzofuran-5-yl)methoxy)-4-ethylphenyl)acetate (469e) (100 mg, 0.230 mmol) in dioxane (4 mL) using (3-(aminomethyl)phenyl)boronic acid hydrochloride (6c) (52 mg, 0.276 mmol), bis(triphenylphosphine)palladium(II) chloride (Pd(PPh$_3$)$_2$Cl$_2$) (16 mg, 0.023 mmol) and a solution of K$_2$CO$_3$ (0.209 mL, 0.689 mmol) in water (1 mL) under an N$_2$ atmosphere heating at 100° C. for 16 h on oil bath. This gave after workup, purification by flash column chromatography (silica gel, 12 g, eluting with 0-6% MeOH in DCM) ethyl 2-(2-((7-(3-(aminomethyl)phenyl)-2-fluorobenzofuran-5-yl)methoxy)-4-ethylphenyl)acetate (469f) (55 mg, 52% yield) as a clear colorless oil. $^1$H NMR (300 MHz, DMSO-d$_6$) δ 7.76 (s, 1H), 7.68-7.59 (m, 2H), 7.56 (d, J=1.8 Hz, 1H), 7.51-7.37 (m, 2H), 7.10 (dd, J=7.8, 2.0 Hz, 1H), 6.99 (d, J=1.8 Hz, 1H), 6.75 (d, 1H), 6.44 (dd, J=6.5, 1.6 Hz, 1H), 5.21 (s, 2H), 3.91 (q, J=7.2, 1.9 Hz, 2H), 3.81 (s, 2H), 3.57 (s, 2H), 2.59 (q, J=7.6 Hz, 2H), 1.18 (t, 3H), 0.98 (t, J=7.9, 7.5, 2.1 Hz, 3H). $^{19}$F NMR (282 MHz, DMSO-d$_6$) δ−111.77; MS (ES+): 462 (M+1).

Step 6: Preparation of 2-(2-((7-(3-(aminomethyl)phenyl)-2-fluorobenzofuran-5-yl)methoxy)-4-ethylphenyl)acetic Acid (469g)

Compound 469g was prepared according to the procedure reported in step-6 of scheme-1 from ethyl 2-(2-((7-(3-(aminomethyl)phenyl)-2-fluorobenzofuran-5-yl)methoxy)-4-ethylphenyl)acetate (469f) (55 mg, 0.119 mmol) in THF (3 mL) and H$_2$O (1 mL) using a solution 2.0 M aqueous LiOH (0.596 mL, 1.192 mmol). This gave after workup and purification by reverse phase column [C18 column, 100 g, eluting with 0-60% MeCN in H$_2$O containing 0.1% HCl) 2-(2-((7-(3-(aminomethyl)phenyl)-2-fluorobenzofuran-5-yl)methoxy)-4-ethylphenyl)acetic acid (469g) (31 mg, 60% yield) HCl salt as a white solid; $^1$H NMR (300 MHz, DMSO-d$_6$) δ 8.53 (s, 3H), 7.96 (d, J=1.5 Hz, 1H), 7.85 (m, 1H), 7.69 (d, J=1.6 Hz, 1H), 7.64 (d, J=1.7 Hz, 1H), 7.62-7.54 (m, 2H), 7.11 (d, J=7.6 Hz, 1H), 6.97 (d, J=1.6 Hz, 1H), 6.76 (dd, J=7.6, 1.5 Hz, 1H), 6.45 (d, J=6.4 Hz, 1H), 5.23 (s, 2H), 4.13 (s, 2H), 3.54 (s, 2H), 2.58 (q, J=7.6 Hz, 2H), 1.18 (t, J=7.6 Hz, 3H). $^{19}$F NMR (282 MHz, DMSO-d$_6$) δ−111.61; MS (ES+): 434 (M+1), (ES−): 432 (M−1); Analysis calculated for C$_{26}$H$_{24}$FNO$_4$.HCl.2H$_2$O$_2$: C, 61.72; H, 5.78; Cl, 7.01; N, 2.77; Found: C, 61.60; H, 5.63; Cl, 7.40; N, 2.89.

Scheme-470

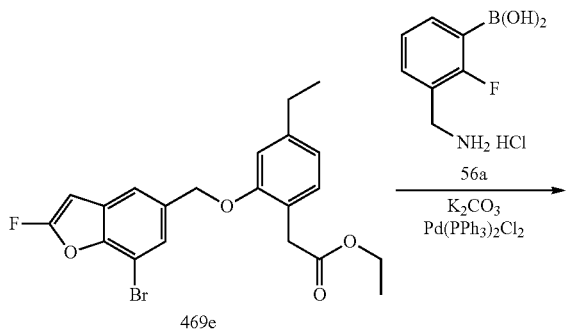

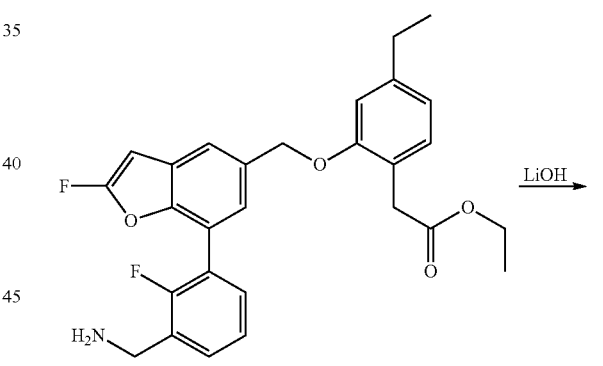

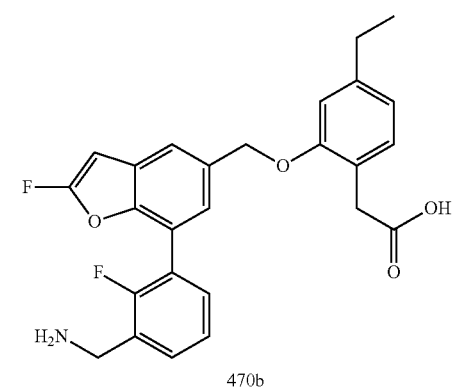

Preparation of 2-(2-((7-(3-(aminomethyl)-2-fluorophenyl)-2-fluorobenzofuran-5-yl)methoxy)-4-ethylphenyl)acetic Acid (470b)

Step-1: Preparation of Ethyl 2-(2-((7-(3-(aminomethyl)-2-fluorophenyl)-2-fluorobenzofuran-5-yl)methoxy)-4-ethylphenyl)acetate (470a)

Compound 470a was prepared according to the procedure reported in step-3 of scheme-1 from ethyl 2-(2-((7-bromo-2-fluorobenzofuran-5-yl)methoxy)-4-ethylphenyl)acetate (469e) (100 mg, 0.230 mmol) in dioxane (4 mL) using 3-(aminomethyl)-2-fluorophenylboronic acid hydrochloride (56a) (57 mg, 0.276 mmol), bis(triphenylphosphine)palladium(II) chloride (Pd(PPh$_3$)$_2$Cl$_2$) (16 mg, 0.023 mmol) and a solution of K$_2$CO$_3$ (0.209 mL, 0.689 mmol) in water (1 mL) under an N$_2$ atmosphere heating at 100° C. for 16 h on oil bath. This gave after workup, purification by flash column chromatography (silica gel, 12 g, eluting with 0-3% MeOH in DCM) ethyl 2-(2-((7-(3-(aminomethyl)-2-fluorophenyl)-2-fluorobenzofuran-5-yl)methoxy)-4-ethylphenyl)acetate (470a) (38 mg, 34.5% yield) as a colorless oil; MS (ES+): 480 (M+1).

Step-2: Preparation of 2-(2-((7-(3-(aminomethyl)-2-fluorophenyl)-2-fluorobenzofuran-5-yl)methoxy)-4-ethylphenyl)acetic Acid (470b)

Compound 470b was prepared according to the procedure reported in step-6 of scheme-1 from of ethyl 2-(2-((7-(3-(aminomethyl)-2-fluorophenyl)-2-fluorobenzofuran-5-yl)methoxy)-4-ethylphenyl)acetate (470a) (38 mg, 0.079 mmol) in THF (3 mL) and H$_2$O (1 mL) using a solution 2.0 M aqueous LiOH (0.198 mL, 0.396 mmol) and stirring at 40° C. for 16 h. This gave after workup and purification by reverse phase column [C18 column, 100 g, eluting with 0-60% MeCN in H$_2$O containing 0.1% HCl) 2-(2-((7-(3-(aminomethyl)-2-fluorophenyl)-2-fluorobenzofuran-5-yl)methoxy)-4-ethylphenyl)acetic acid (470b) (20 mg, 56% yield) HCl salt as a white solid; $^1$H NMR (300 MHz, DMSO-d$_6$) δ 12.16 (s, 1H), 8.64 (s, 3H), 7.82-7.70 (m, 2H), 7.67 (td, J=7.4, 1.8 Hz, 1H), 7.54-7.38 (m, 2H), 7.11 (d, J=7.6 Hz, 1H), 6.97 (d, J=1.5 Hz, 1H), 6.76 (dd, J=7.6, 1.5 Hz, 1H), 6.45 (d, J=6.4 Hz, 1H), 5.23 (s, 2H), 4.17 (s, 2H), 3.53 (s, 2H), 2.58 (q, J=7.6 Hz, 2H), 1.18 (t, J=7.6 Hz, 3H). $^{19}$F NMR (282 MHz, DMSO-d$_6$) δ –111.63, –118.62; MS (ES+): 452 (M+1), (ES–): 450 (M–1).

Scheme-471

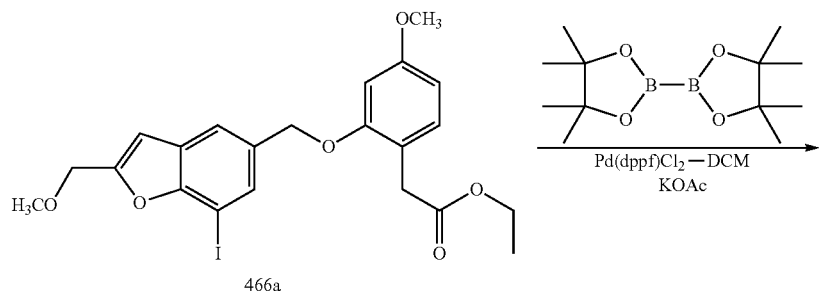

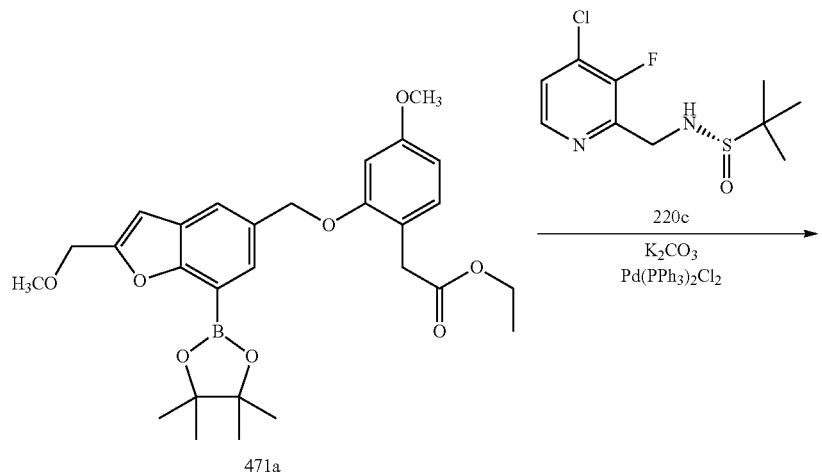

1423

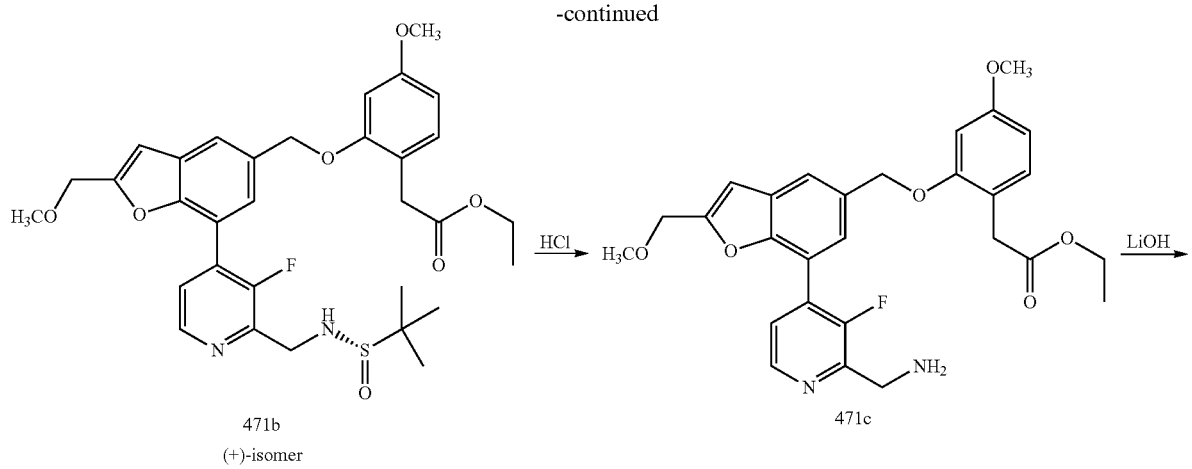

471b
(+)-isomer

1424
-continued

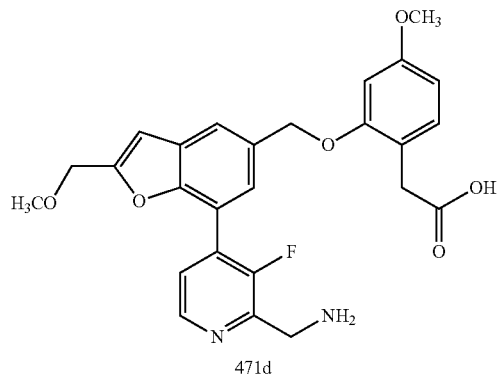

471c

471d

Preparation of 2-(2-((7-(2-(aminomethyl)-3-fluoropyridin-4-yl)-2-(methoxymethyl)benzofuran-5-yl)methoxy)-4-methoxyphenyl)acetic Acid (471d)

Step-1: Preparation of Ethyl 2-(4-methoxy-2-((2-(methoxymethyl)-7-(4,4,5,5-tetramethyl-1,3,2-dioxaborolan-2-yl)benzofuran-5-yl)methoxy)phenyl)acetate (471a)

Compound 471a was prepared according to the procedure reported in step-1 of scheme-59 from ethyl 2-(2-((7-iodo-2-(methoxymethyl)benzofuran-5-yl)methoxy)-4-methoxyphenyl)acetate (466a) (1.01 g, 1.979 mmol), using bis(pinacolato)diboron (0.754 g, 2.97 mmol), potassium acetate (0.583 g, 5.94 mmol) and Pd(dppf)Cl$_2$-DCM (0.242 g, 0.297 mmol) in anhydrous dioxane (20 mL) under a nitrogen atmosphere and heating at 90° C. for 18 h. This gave after workup and purification by flash column chromatography [silica gel, eluting with hexanes/ethyl acetate (1:0 to 2:1)] ethyl 2-(4-methoxy-2-((2-(methoxymethyl)-7-(4,4,5,5-tetramethyl-1,3,2-dioxaborolan-2-yl)benzofuran-5-yl)methoxy)phenyl)acetate (471a) (1.05 g) as a brown gum; MS (ES+): 533.20 (M+Na).

Step-2: Preparation of (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-4-methoxyphenyl)acetate (471b)

Compound 471b was prepared according to the procedure reported in step-3 of scheme-1 from ethyl 2-(4-methoxy-2-((2-(methoxymethyl)-7-(4,4,5,5-tetramethyl-1,3,2-dioxaborolan-2-yl)benzofuran-5-yl)methoxy)phenyl)acetate (471a) (500 mg, 0.980 mmol) in dioxane (20 mL) using (+)-(S)—N-((4-chloro-3-fluoropyridin-2-yl)methyl)-2-methylpropane-2-sulfinamide (220c) (311 mg, 1.176 mmol), bis(triphenylphosphine)palladium(II) chloride (Pd(PPh$_3$)$_2$Cl$_2$) (103 mg, 0.147 mmol) and a solution of K$_2$CO$_3$ (406 mg, 2.94 mmol) in water (2.4 mL) under a nitrogen atmosphere heating at 100° C. for 19 h on oil bath. This gave after workup and purification by flash column chromatography [silica gel, eluting with hexanes/10% methanol in ethyl acetate (1:0 to 1:2)] (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-4-methoxyphenyl)acetate (471b) (113 mg, 20% for 2 steps) as a light yellow gum; $^1$H NMR (300 MHz, DMSO-d$_6$) δ 8.52 (d, J=4.9 Hz, 1H), 7.81 (d, J=1.6 Hz, 1H), 7.65 (t, J=5.2 Hz, 1H), 7.50 (s, 1H), 7.11 (d, J=8.3 Hz, 1H), 7.04 (s, 1H), 6.70 (d, J=2.4 Hz, 1H), 6.49 (dd, J=8.2, 2.4 Hz, 1H), 5.84 (t, J=5.7 Hz, 1H), 5.23 (s, 2H), 4.52 (s, 2H), 4.44-4.36 (m, 2H), 3.90 (q, J=7.1 Hz, 2H), 3.74 (s, 3H), 3.53 (s, 2H), 3.30 (s, 3H), 1.11 (s, 9H), 0.98 (t, J=7.1 Hz, 3H); $^{19}$F NMR (282 MHz, DMSO-d$_6$) δ−128.10; MS (ES+): 613.30 (M+1); Optical rotation [t]D=+26.67 (c=0.09, MeOH).

Step-3: Preparation of Ethyl 2-(2-((7-(2-(aminomethyl)-3-fluoropyridin-4-yl)-2-(methoxymethyl)benzofuran-5-yl)methoxy)-4-methoxyphenyl)acetate (471c)

Compound 471c was prepared according to the procedure reported in step-3 of scheme-305 from (+)-(S)-ethyl 2-(2-((7-(2-((1,1-dimethylethylsulfinamido)methyl)-3-fluoropyridin-4-yl)-2-(methoxymethyl)benzofuran-5-yl)
methoxy)-4-methoxyphenyl)acetate (471b) (105 mg, 0.171
mmol) in THF (5 mL) using HCl (3M aqueous; 0.171 mL,
0.514 mmol) and stirring at room temperature for 3 h. This
gave after workup ethyl 2-(2-((7-(2-(aminomethyl)-3-fluoropyridin-4-yl)-2-(methoxymethyl)benzofuran-5-yl)
methoxy)-4-methoxyphenyl)acetate (471c) which was used
as such for next step. MS (ES+): 509.20 (M+1).

Step-4: Preparation of 2-(2-((7-(2-(aminomethyl)-3-fluoropyridin-4-yl)-2-(methoxymethyl)benzofuran-5-yl)methoxy)-4-methoxyphenyl)acetic Acid (471d)

Compound 471d was prepared according to the procedure reported in step-6 of scheme-1 from ethyl 2-(2-((7-(2-(aminomethyl)-3-fluoropyridin-4-yl)-2-(methoxymethyl)benzofuran-5-yl)methoxy)-4-methoxyphenyl)acetate (471c) (0.171 mmol; from above step-3) in MeOH/THF (3 mL each) using a solution of lithium hydroxide (59 mg, 1.368 mmol) in water (3 mL). This gave after workup and purification by reverse phase column [C18 column, eluting with water (containing 0.1% HCl)/acetonitrile (1:0 to 0:1)] 2-(2-((7-(2-(aminomethyl)-3-fluoropyridin-4-yl)-2-(methoxymethyl)benzofuran-5-yl)methoxy)-4-methoxyphenyl)acetic acid (471d) (36 mg, 44% for 2 steps) HCl salt as a light yellow solid; $^1$H NMR (300 MHz, DMSO-$d_6$) δ 8.63 (d, J=5.0 Hz, 1H), 8.62-8.54 (m, 3H), 7.87 (d, J=1.6 Hz, 1H), 7.79 (t, J=5.3 Hz, 1H), 7.58 (t, J=1.4 Hz, 1H), 7.11 (d, J=8.3 Hz, 1H), 7.05 (s, 1H), 6.67 (d, J=2.4 Hz, 1H), 6.49 (dd, J=8.3, 2.4 Hz, 1H), 5.26 (s, 2H), 4.54 (s, 2H), 4.44-4.25 (m, 2H), 3.73 (s, 3H), 3.49 (s, 2H), 3.30 (s, 3H); $^{19}$F NMR (282 MHz, DMSO-$d_6$) δ −128.61; MS (ES+): 481.20 (M+1); MS (ES−): 479.20 (M−1); Analysis calculated for $C_{26}H_{25}FN_2O_6$·1.15HCl1.25H$_2$O: C, 57.31; H, 5.30; Cl, 7.48; F, 3.49; N, 5.14; Found: C, 57.32; H, 5.07; N, 5.15; Cl, 7.52.

Scheme-472

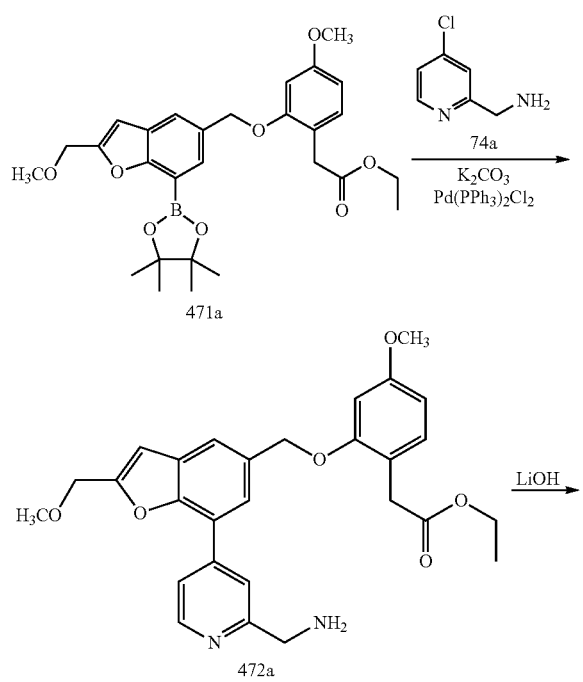

Preparation of 2-(2-((7-(2-(aminomethyl)pyridin-4-yl)-2-(methoxymethyl)benzofuran-5-yl)methoxy)-4-methoxyphenyl)acetic Acid (472b)

Step-1: Preparation of Ethyl 2-(2-((7-(2-(aminomethyl)pyridin-4-yl)-2-(methoxymethyl)benzofuran-5-yl)methoxy)-4-methoxyphenyl)acetate (472a)

Compound 472a was prepared according to the procedure reported in step-3 of scheme-1 from ethyl 2-(4-methoxy-2-((2-(methoxymethyl)-7-(4,4,5,5-tetramethyl-1,3,2-dioxaborolan-2-yl)benzofuran-5-yl)methoxy)phenyl)acetate (471a) (510 mg, 0.999 mmol) in dioxane (20 mL) using (4-chloropyridin-2-yl)methanamine (74a) (171 mg, 1.199 mmol), bis(triphenylphosphine)palladium(II) chloride (Pd(PPh$_3$)$_2$Cl$_2$) (140 mg, 0.200 mmol) and a solution of K$_2$CO$_3$ (414 mg, 3.00 mmol) in water (2.4 mL) under a nitrogen atmosphere heating at 100° C. for 19 h on oil bath. This gave after workup and purification by flash column chromatography [silica gel, eluting with dichloromethane/DMA 80 (1:0 to 3:1)] ethyl 2-(2-((7-(2-(aminomethyl)pyridin-4-yl)-2-(methoxymethyl)benzofuran-5-yl)methoxy)-4-methoxyphenyl)acetate (472a) (104 mg) as a light-yellow gum; MS (ES+): 613.30 (M+1).

Step-2: Preparation of 2-(2-((7-(2-(aminomethyl)pyridin-4-yl)-2-(methoxymethyl)benzofuran-5-yl)methoxy)-4-methoxyphenyl)acetic Acid (472b)

Compound 472b was prepared according to the procedure reported in step-6 of scheme-1 from ethyl 2-(2-((7-(2-(aminomethyl)pyridin-4-yl)-2-(methoxymethyl)benzofuran-5-yl)methoxy)-4-methoxyphenyl)acetate (472a) (100 mg, 0.204 mmol) in MeOH/THF (3 mL each) using a solution of lithium hydroxide (52 mg, 1.223 mmol) in water (3 mL). This gave after workup and purification by reverse phase column [C18 column, eluting with water (containing 0.1% HCl)/acetonitrile (1:0 to 0:1)] 2-(2-((7-(2-(aminomethyl)pyridin-4-yl)-2-(methoxymethyl)benzofuran-5-yl)methoxy)-4-methoxyphenyl)acetic acid (472b) (12 mg, 3% for 2 steps) HCl salt as a light yellow solid; $^1$H NMR (300 MHz, DMSO-$d_6$) δ 8.85-8.74 (m, 1H), 8.42 (s, 3H), 8.02 (s, 1H), 7.97 (dd, J=5.2, 1.7 Hz, 1H), 7.83 (d, J=1.6 Hz, 1H), 7.78 (d, J=1.7 Hz, 1H), 7.12 (d, J=8.3 Hz, 1H), 7.05 (s, 1H), 6.67 (d, J=2.4 Hz, 1H), 6.49 (dd, J=8.3, 2.4 Hz, 1H), 5.27 (s, 2H), 4.61 (s, 2H), 4.35-4.27 (m, 2H), 3.73 (s, 3H), 3.51 (s, 2H), 3.34 (s, 3H); MS (ES+): 463.20 (M+1); MS (ES−): 461.10 (M−1).

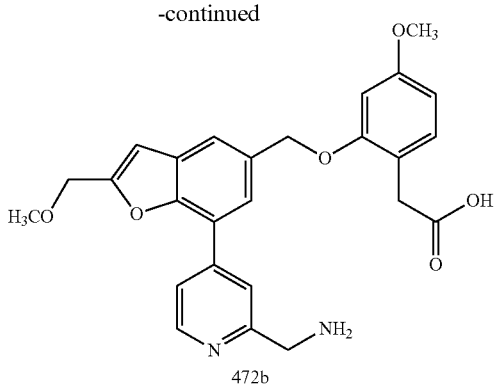

Scheme-473

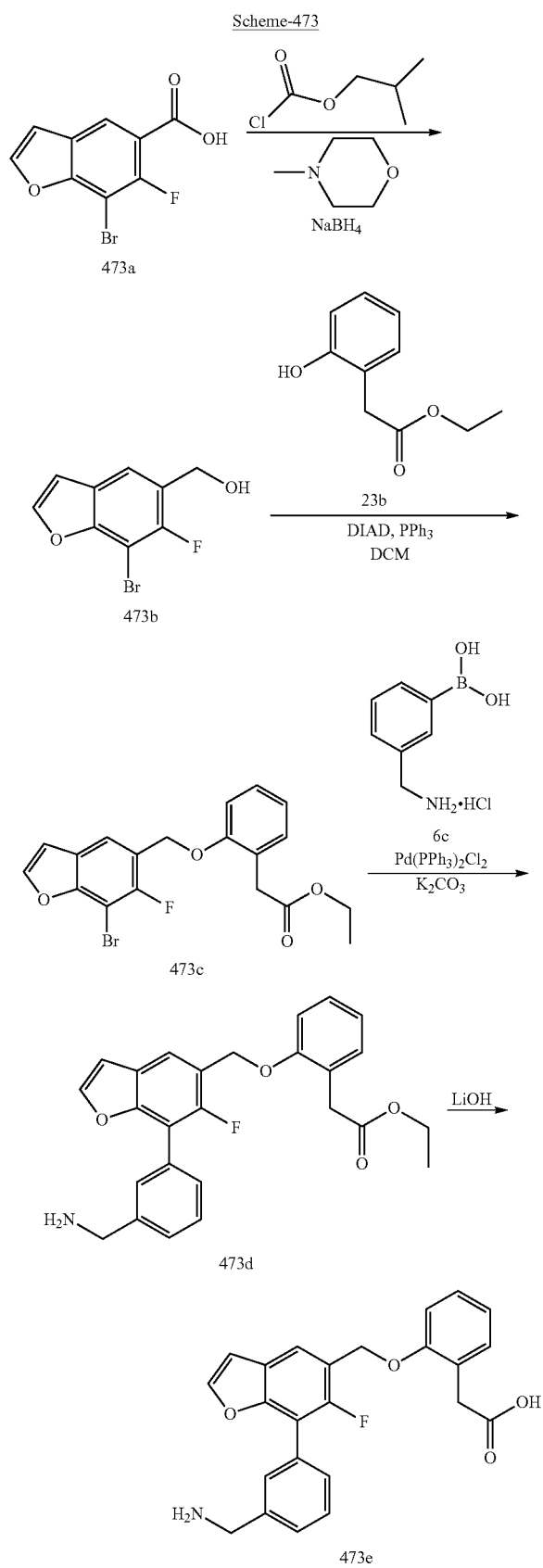

Preparation of 2-(2-((7-(3-(aminomethyl)phenyl)-6-fluorobenzofuran-5-yl)methoxy)phenyl)acetic Acid (473e)

Step-1: Preparation of (7-bromo-6-fluorobenzofuran-5-yl)methanol (473b)

Compound 473b was prepared according to the procedure reported in step-1 of scheme-23 from 7-bromo-6-fluorobenzofuran-5-carboxylic acid (473a) (200 mg, 0.772 mmol) using N-methylmorpholine (0.102 mL, 0.927 mmol) in THF (6 mL), isobutyl chloroformate (0.122 mL, 0.927 mmol) and NaBH$_4$ (88 mg, 2.316 mmol) in water (2 mL). This gave after workup and purification by flash column chromatography [silica (12 g), eluting with EtOAc in hexane from 0-50%] (7-bromo-6-fluorobenzofuran-5-yl)methanol (473b) (179 mg, 95% yield) as a white solid; $^1$H NMR (300 MHz, DMSO-d$_6$) δ 8.12 (d, J=2.2 Hz, 1H), 7.71 (dt, J=6.9, 0.9 Hz, 1H), 7.12 (d, J=2.2 Hz, 1H), 5.39 (t, J=5.7 Hz, 1H), 4.63 (ddd, J=5.8, 1.6, 0.8 Hz, 2H); $^{19}$F NMR (282 MHz, DMSO-d$_6$) δ−121.17.

Step-2: Preparation of Ethyl 2-(2-((7-bromo-6-fluorobenzofuran-5-yl)methoxy)phenyl)acetate (473c)

Compound 473c was prepared according to the procedure reported in step-2 of scheme-23 from (7-bromo-6-fluorobenzofuran-5-yl)methanol (473b) (175 mg, 0.714 mmol) in DCM (8 mL) using triphenylphosphine (206 mg, 0.786 mmol), ethyl 2-(2-hydroxyphenyl) acetate (23b) (167 mg, 0.928 mmol) and (E)-bis(4-chlorobenzyl) diazene-1,2-dicarboxylate (DIAD, 288 mg, 0.786 mmol) and stirring at room temperature for 1 h. This gave after workup and purification by flash column chromatography [silica (24 g), eluting with EtOAc in hexane from 0-50%] ethyl 2-(2-((7-bromo-6-fluorobenzofuran-5-yl)methoxy)phenyl)acetate (473c) (244 mg, 84% yield) as a pale yellow oil; $^1$H NMR (300 MHz, DMSO-d$_6$) δ 8.17 (d, J=2.2 Hz, 1H), 7.81 (d, J=6.7 Hz, 1H), 7.31-7.03 (m, 4H), 6.93 (td, J=7.4, 1.1 Hz, 1H), 5.23 (t, J=0.9 Hz, 2H), 3.95 (q, J=7.1 Hz, 2H), 3.57 (s, 2H), 1.01 (t, J=7.1 Hz, 3H); $^{19}$F NMR (282 MHz, DMSO-d$_6$) δ−119.47.

Step-3: Preparation of Ethyl 2-(2-((7-(3-(aminomethyl)phenyl)-6-fluorobenzofuran-5-yl)methoxy)phenyl)acetate (473d)

Compound 473d was prepared according to the procedure reported in step-3 of scheme-1 ethyl 2-(2-((7-bromo-6-fluorobenzofuran-5-yl)methoxy)phenyl)acetate (473c) (240 mg, 0.589 mmol) in dioxane (5 mL) using 3-(aminomethyl)phenylboronic acid hydrochloride (6c) (133 mg, 0.884 mmol), Pd(Ph$_3$)$_2$Cl$_2$ (62 mg, 0.088 mmol) and a solution of K$_2$CO$_3$ (244 mg, 1.768 mmol) in water (0.5 mL) under an Ar atmosphere and heating at 100° C. for 3 h. This gave after workup purification by flash column chromatography [silica (12 g), eluting with DMA80 in DCM from 0-50%] ethyl 2-(2-((7-(3-(aminomethyl)phenyl)-6-fluorobenzofuran-5-yl)methoxy)phenyl)acetate (473d) (255 mg, 100% yield) as a yellow oil which was used in the next step without further purification. MS (ES+): 434.1 (M+1).

Step-4: Preparation of 2-(2-((7-(3-(aminomethyl)phenyl)-6-fluorobenzofuran-5-yl)methoxy)phenyl)acetic Acid (473e)

Compound 473e was prepared according to the procedure reported in step-6 of scheme-1, ethyl 2-(2-((7-(3-(aminom-

1429 ethyl)phenyl)-6-fluorobenzofuran-5-yl)methoxy)phenyl)acetate (473d) (255 mg, 0.588 mmol) in MeOH/THF (6 mL) using a solution of lithium hydroxide (99 mg, 2.353 mmol) in water (2 mL). This gave after workup and purification by reverse phase column [C18 (50 g), eluting with ACN in water (containing 0.1% HCl) from 0-100%] 2-(2-((7-(3-(aminomethyl)phenyl)-6-fluorobenzofuran-5-yl)methoxy)phenyl)acetic acid (473e) (77 mg, 32% yield) HCl salt as a white solid. $^1$H NMR (300 MHz, DMSO-$d_6$) δ 8.52 (s, 2H), 8.00 (d, J=2.2 Hz, 1H), 7.78 (d, J=6.8 Hz, 1H), 7.73 (s, 1H), 7.66-7.48 (m, 3H), 7.23-7.12 (m, 2H), 7.07 (d, J=8.1 Hz, 1H), 6.99 (d, J=2.3 Hz, 1H), 6.86 (td, J=7.3, 1.1 Hz, 1H), 5.21 (s, 2H), 4.05 (s, 2H), 3.50 (s, 2H); $^{19}$F NMR (282 MHz, DMSO-$d_6$) δ−128.50; MS (ES+): 406.1 (M+1); MS (ES−): 404.1 (M−1); Analysis calculated for: $C_{24}H_{20}FNO_4 \cdot HCl \cdot 1.25H_2O$: C, 62.07; H, 5.10; Cl, 7.63; N, 3.02; Found: C, 62.02; H, 5.12; Cl, 7.87, N, 3.20.

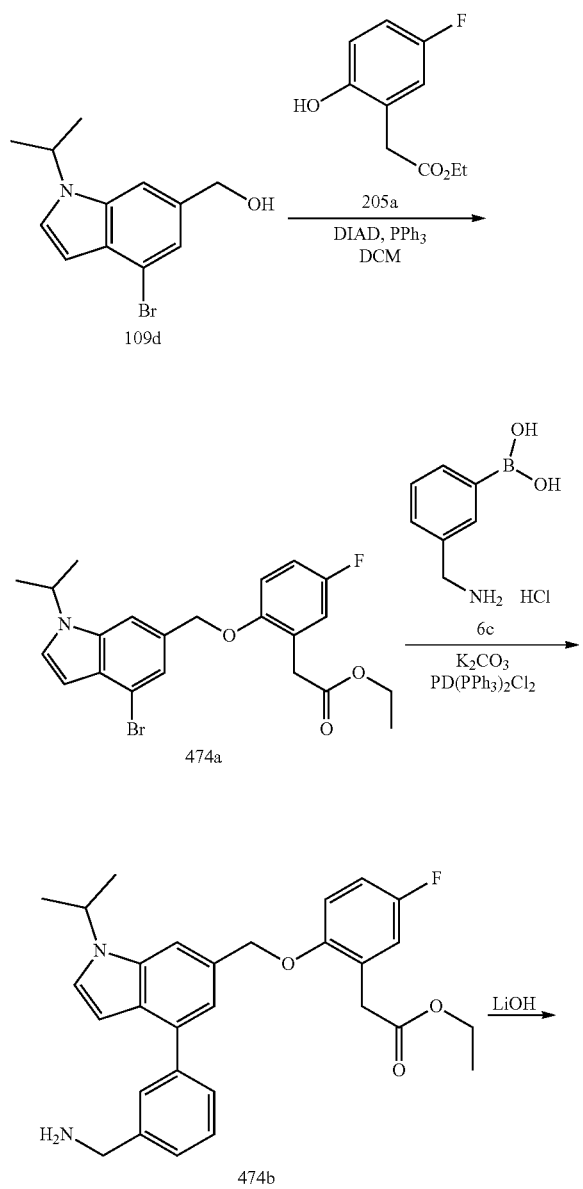

Scheme-474

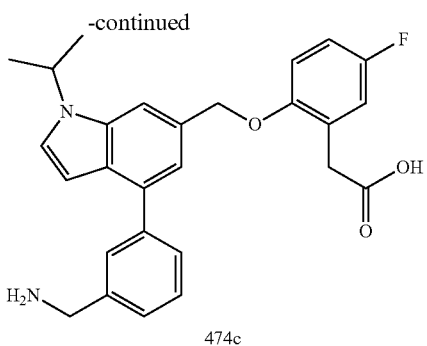

Preparation of 2-(2-((4-(3-(aminomethyl)phenyl)-1-isopropyl-1H-indol-6-yl)methoxy)-5-fluorophenyl)acetic Acid (474c)

Step-1: Preparation of Ethyl 2-(2-((4-bromo-1-isopropyl-1H-indol-6-yl)methoxy)-5-fluorophenyl)acetate (474a)

Compound 474a was prepared according to the procedure reported in step-2 of scheme-23 from (4-bromo-1-isopropyl-1H-indol-6-yl)methanol (109d) (0.62 g, 2.312 mmol) in toluene (20 mL) using triphenylphosphine (1.213 g, 4.62 mmol), ethyl 2-(5-fluoro-2-hydroxyphenyl)acetate (205a) (0.458 g, 2.312 mmol) and DIAD (0.935 g, 4.62 mmol). This gave after workup and purification by flash column chromatography [silica gel, 24 g, eluting with 0-5% EtOAc in hexane] ethyl 2-(2-((4-bromo-1-isopropyl-1H-indol-6-yl)methoxy)-5-fluorophenyl)acetate (474a) (0.58 g, 56% yield) as a pale-yellow oil. $^1$H NMR (300 MHz, DMSO-$d_6$) δ 7.69-7.60 (m, 2H), 7.28 (d, J=0.8 Hz, 1H), 7.17-7.04 (m, 3H), 6.42 (d, J=3.2 Hz, 1H), 5.16 (s, 2H), 4.75 (hept, J=6.7 Hz, 1H), 4.02 (q, 2H), 3.64 (s, 2H), 1.48 (s, 3H), 1.45 (s, 3H), 1.07 (t, J=7.1 Hz, 3H). $^{19}$F NMR (282 MHz, DMSO-$d_6$) δ−124.07; MS (ES+): 448/450.

Step-2: Preparation of Ethyl 2-(2-((4-(3-(aminomethyl)phenyl)-1-isopropyl-1H-indol-6-yl)methoxy)-5-fluorophenyl)acetate (474b)

Compound 474b was prepared according to the procedure reported in step-3 of scheme-1 from ethyl 2-(2-((4-bromo-1-isopropyl-1H-indol-6-yl)methoxy)-5-fluorophenyl)acetate (474a) (104 mg, 0.232 mmol) in dioxane (4 mL)/water (1 mL) using (3-(aminomethyl)phenyl)boronic acid hydrochloride (6c) (65 mg, 0.348 mmol), bis(triphenylphosphine)palladium(II) chloride (Pd(PPh$_3$)$_2$Cl$_2$) (16 mg, 0.023 mmol) and 3.3 M aqueous K$_2$CO$_3$ (0.211 mL, 0.696 mmol) under a nitrogen atmosphere heating at 100° C. for 16 h on oil bath. This gave after workup, purification by flash column chromatography (silica gel, 12 g, eluting with 0-6% MeOH in DCM) ethyl 2-(2-((4-(3-(aminomethyl)phenyl)-1-isopropyl-1H-indol-6-yl)methoxy)-5-fluorophenyl)acetate (474b) (72 mg, 65% yield) as a colorless oil; MS (ES+) 475 (M+1).

Step-3: Preparation of 2-(2-((4-(3-(aminomethyl)phenyl)-1-isopropyl-1H-indol-6-yl)methoxy)-5-fluorophenyl)acetic Acid (474c)

Compound 474c was prepared according to the procedure reported in step-6 of scheme-1 from ethyl 2-(2-((4-(3-(aminomethyl)phenyl)-1-isopropyl-1H-indol-6-yl)

methoxy)-5-fluorophenyl)acetate (474b) (72 mg, 0.152 mmol) in MeOH (3 mL), using a 2 M aqueous solution of lithium hydroxide (0.379 mL, 0.759 mmol) and stirring at room temperature for 16 h. This gave after workup and purification by reverse phase column [C18 (100 g), eluting with 0-60% MeCN in H₂O] 2-(2-((4-(3-(aminomethyl)phenyl)-1-isopropyl-1H-indol-6-yl)methoxy)-5-fluorophenyl)acetic acid (474c) (54 mg, 80% yield) HCl salt as a white solid. $^1$H NMR (300 MHz, DMSO-$d_6$) δ 7.96 (d, J=1.8 Hz, 1H), 7.76-7.69 (m, 1H), 7.62 (s, 1H), 7.59 (d, J=3.3 Hz, 1H), 7.50 (t, J=7.6 Hz, 1H), 7.43-7.36 (m, 1H), 7.32 (d, J=1.3 Hz, 1H), 7.00 (dtt, J=20.0, 8.5, 3.9 Hz, 3H), 6.65 (d, J=3.3 Hz, 1H), 5.24 (s, 2H), 4.81 (hept, J=6.9 Hz, 1H), 4.06 (s, 2H), 3.50 (s, 2H), 1.51 (s, 3H), 1.48 (s, 3H). $^{19}$F NMR (282 MHz, DMSO-$d_6$) δ −124.84; MS (ES+): 447 (M+1), (ES−): 445 (M−1); Analysis calculated for: $C_{27}H_{27}FN_2O_3 \cdot 0.65HCl \cdot 1.25H_2O$. C, 65.81; H, 6.17; Cl, 4.68; N, 5.69; found: C, 66.19; H, 6.05; Cl, 4.67; N, 5.73.

Scheme-475

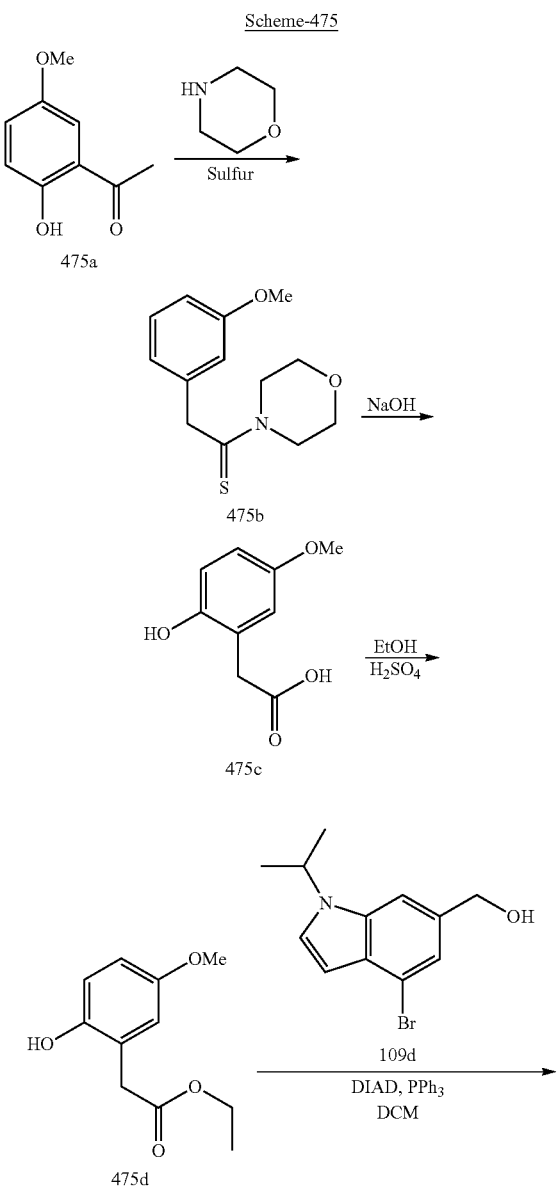

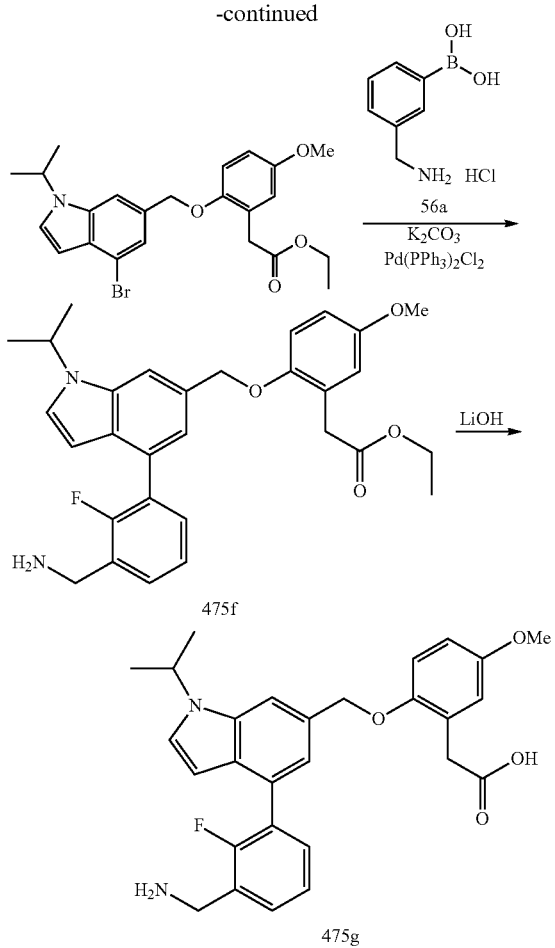

Preparation of 2-(2-((4-(3-(aminomethyl)-2-fluorophenyl)-1-isopropyl-1H-indol-6-yl)methoxy)-5-methoxyphenyl)acetic Acid (475g)

Step-1: Preparation of 2-(3-methoxyphenyl)-1-morpholinoethanethione (475b)

Compound 475b was prepared according to the procedure reported in step-1 of scheme-265 from 1-(2-hydroxy-5-methoxyphenyl)ethanone (475a) (2 g, 12.04 mmol; CAS #705-15-7) in N-Methyl-2-pyrrolidinone (6 mL) using sulfur powder (0.772 g, 24.07 mmol), morpholine (2.097 g, 24.07 mmol) and heating at 130° C. for 16 h. This gave after workup and purification by flash column chromatography (silica gel, 24 g, eluting with 0-30% ethyl acetate and hexanes) 2-(3-methoxyphenyl)-1-morpholinoethanethione (475b) (1.30 g, 40% yield) as a red semisolid; $^1$H NMR (300 MHz, DMSO-$d_6$) δ 9.22 (s, 1H), 6.79 (d, J=3.0 Hz, 1H), 6.75 (d, J=8.7 Hz, 1H), 6.67 (dd, J=8.7, 3.0 Hz, 1H), 4.28-4.18 (m, 2H), 4.10 (s, 2H), 3.68-3.61 (m, 7H), 3.45-3.36 (m, 2H); MS (ES+) 268 (M+1).

Step-2: Preparation of 2-(2-hydroxy-5-methoxyphenyl)acetic Acid (475c)

Compound 475c was prepared according to the procedure reported in step-2 of scheme-265 from 2-(3-methoxyphenyl)-1-morpholinoethanethione (475b) (1.30 g, 4.86 mmol) in ethanol (20 mL) using 4 M aqueous NaOH (3.65 mL, 14.59 mmol) and heating at reflux for 16 h. This gave after workup 2-(2-hydroxy-5-methoxyphenyl)acetic acid (475c) (0.87 g, 98% yield) as a black semisolid, which was used in the next step without further purification.

Step-3: Preparation of Ethyl 2-(2-hydroxy-5-methoxyphenyl)acetate (475d)

Compound 475d was prepared according to the procedure reported in step-3 of scheme-265 from 2-(2-hydroxy-5-methoxyphenyl)acetic acid (475c) (0.87 g, 4.78 mmol) in ethanol (20 mL) using sulfuric acid (1 mL) and heating at reflux for 16 h. This gave after workup and purification by flash column chromatography (silica gel, 24 g, eluting with 0-20% ethyl acetate in hexanes) ethyl 2-(2-hydroxy-5-methoxyphenyl)acetate (475d) (0.49 g, 49% yield) as an orange oil; $^1$H NMR (300 MHz, DMSO-$d_6$) δ 8.98 (s, 1H), 6.77-6.60 (m, 3H), 4.06 (q, J=7.1 Hz, 2H), 3.65 (s, 3H), 3.51 (s, 2H), 1.17 (t, J=7.1 Hz, 3H); MS (ES+): 211 (M+1).

Step-4: Preparation of Ethyl 2-(2-((4-bromo-1-isopropyl-1H-indol-6-yl)methoxy)-5-methoxyphenyl)acetate (475e)

Compound 475e was prepared according to the procedure reported in step-2 of scheme-23 from (4-bromo-1-isopropyl-1H-indol-6-yl)methanol (109d) (0.688 g, 2.56 mmol) in toluene (5 mL) using triphenylphosphine (1.223 g, 4.66 mmol), ethyl 2-(2-hydroxy-5-methoxyphenyl)acetate (475d) (0.49 g, 2.331 mmol) and DIAD (0.943 g, 4.66 mmol) in toluene (20 mL) and stirring at room temperature for 16 h. This gave after workup and purification by flash column chromatography [silica gel, 24 g, eluting with 0-10% EtOAc in hexane] ethyl 2-(2-((4-bromo-1-isopropyl-1H-indol-6-yl)methoxy)-5-methoxyphenyl)acetate (475e) (455 mg, 42% yield) as an orange oil; $^1$H NMR (300 MHz, DMSO-$d_6$) δ 7.68-7.59 (m, 2H), 7.28 (d, J=1.1 Hz, 1H), 7.01 (d, J=8.8 Hz, 1H), 6.85 (d, J=3.1 Hz, 1H), 6.80 (dd, J=8.8, 3.1 Hz, 1H), 6.41 (d, J=3.2 Hz, 1H), 5.11 (s, 2H), 4.75 (hept, J=6.7 Hz, 1H), 4.03 (q, 2H), 3.69 (s, 3H), 3.61 (s, 2H), 1.48 (s, 3H), 1.46 (s, 3H), 1.09 (t, J=7.1, 0.7 Hz, 3H); MS (ES+): 482/484 (M+Na).

Step-5: Preparation of Ethyl 2-(2-((4-(3-(aminomethyl)-2-fluorophenyl)-1-isopropyl-1H-indol-6-yl)methoxy)-5-methoxyphenyl)acetate (475f)

Compound 475f was prepared according to the procedure reported in step-3 of scheme-1 from ethyl 2-(2-((4-bromo-1-isopropyl-1H-indol-6-yl)methoxy)-5-methoxyphenyl)acetate (475e) (100 mg, 0.217 mmol) in dioxane (4 mL), water (1 mL) using 3-(aminomethyl)-2-fluorophenylboronic acid hydrochloride (56a) (66.9 mg, 0.326 mmol), bis(triphenylphosphine)palladium(II) chloride (Pd(PPh$_3$)$_2$Cl$_2$) (15 mg, 0.022 mmol) and 3.3 M aqueous K$_2$CO$_3$ (0.197 mL, 0.652 mmol) under a nitrogen atmosphere heating at 100° C. for 16 h on oil bath. This gave after workup, purification by flash column chromatography (silica gel, 12 g, eluting with 0-6% MeOH in DCM) ethyl 2-(2-((4-(3-(aminomethyl)-2-fluorophenyl)-1-isopropyl-1H-indol-6-yl)methoxy)-5-methoxyphenyl)acetate (475f) (73 mg, 67% yield) as a clear colorless oil; MS (ES+): 505 (M+1).

Step-6: Preparation of 2-(2-((4-(3-(aminomethyl)-2-fluorophenyl)-1-isopropyl-1H-indol-6-yl)methoxy)-5-methoxyphenyl)acetic Acid (475g)

Compound 475g was prepared according to the procedure reported in step-6 of scheme-1 from ethyl 2-(2-((4-(3-(aminomethyl)-2-fluorophenyl)-1-isopropyl-1H-indol-6-yl)methoxy)-5-methoxyphenyl)acetate (475f) (73 mg, 0.145 mmol) in MeOH (3 mL) using 2.0 M aqueous LiOH (0.362 mL, 0.723 mmol) and stirring at room temperature for 16 h. This gave after workup and purification by reverse phase column [C18 (100 g), eluting with 0-60% MeCN in H$_2$O] 2-(2-((4-(3-(aminomethyl)-2-fluorophenyl)-1-isopropyl-1H-indol-6-yl)methoxy)-5-methoxyphenyl)acetic acid (475g) (42 mg, 61% yield) HCl salt as a white solid; $^1$H NMR (300 MHz, DMSO-$d_6$) δ 7.64 (s, 1H), 7.51 (dd, J=11.6, 2.5 Hz, 2H), 7.42 (td, J=7.4, 1.8 Hz, 1H), 7.26 (t, J=7.6 Hz, 1H), 7.19 (d, J=1.5 Hz, 1H), 7.00 (d, J=8.8 Hz, 1H), 6.81 (d, J=3.1 Hz, 1H), 6.75 (dd, J=8.8, 3.1 Hz, 1H), 6.31 (d, J=2.7 Hz, 1H), 5.18 (s, 2H), 4.80 (hept, J=6.6 Hz, 1H), 3.86 (s, 2H), 3.68 (s, 3H), 3.52 (s, 2H), 1.49 (s, 3H), 1.47 (s, 3H). $^{19}$F NMR (282 MHz, DMSO-$d_6$) δ−121.45; MS (ES+): 477 (M+1), (ES−): 475 (M−1); Analysis calculated for $C_{28}H_{29}FN_2O_4 \cdot H_2O$: C, 66.78; H, 6.41; N, 5.56; Found: C, 66.87; H, 6.16; N, 5.62.

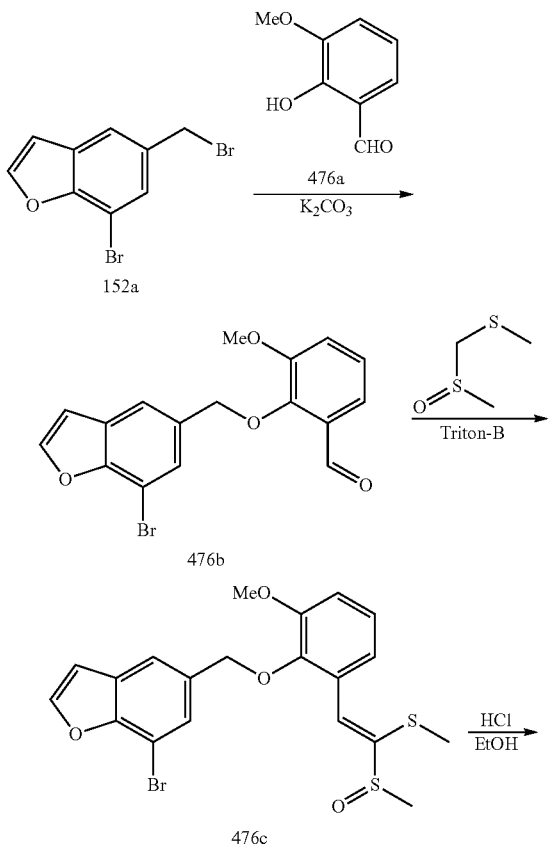

Scheme-476

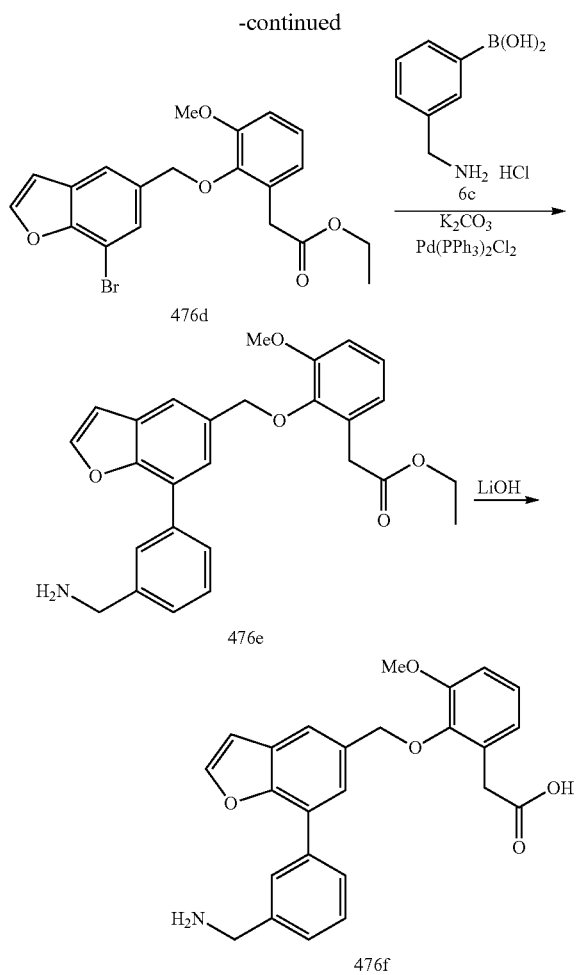

Preparation of 2-(2-((7-(3-(aminomethyl)phenyl) benzofuran-5-yl)methoxy)-3-methoxyphenyl)acetic Acid (476f)

Step-1: Preparation of 2-((7-bromobenzofuran-5-yl) methoxy)-3-methoxybenzaldehyde (476b)

Compound 476b was prepared according to the procedure reported in step-2 of scheme-152 from 7-bromo-5-(bromomethyl)benzofuran (152a) (2.0 g, 8.15 mmol) using 2-hydroxy-3-methoxybenzaldehyde (476a) (1.239 g, 8.15 mmol; CAS #148-53-8), $K_2CO_3$ (3.38 g, 24.44 mmol) in DMF (20 mL) and stirring at room temperature for 4 h. This gave after workup and purification by flash column chromatography (silica gel, 24 g, eluting with 0-10% EtOAc in hexane) 2-((7-bromobenzofuran-5-yl)methoxy)-3-methoxybenzaldehyde (476b) (2.32 g, 79% yield) as a white solid. $^1$H NMR (300 MHz, DMSO-$d_6$) δ 10.16 (d, J=0.6 Hz, 1H), 8.14 (d, J=2.2 Hz, 1H), 7.73 (d, J=1.5 Hz, 1H), 7.66 (d, J=1.5 Hz, 1H), 7.44 (dd, J=6.4, 3.3 Hz, 1H), 7.26-7.21 (m, 2H), 7.11 (d, J=2.2 Hz, 1H), 5.24 (s, 2H), 3.94 (s, 3H); MS (ES+): 383/385 (M+Na).

Step-2: Preparation of 7-bromo-5-((2-methoxy-6-(2-(methylsulfinyl)-2-(methylthio)vinyl)phenoxy) methyl)benzofuran (476c)

Compound 476c was prepared according to the procedure reported in step-3 of scheme-266 from 2-((7-bromobenzofuran-5-yl)methoxy)-3-methoxybenzaldehyde (476b) (2.32 g, 6.42 mmol) in THF (20 mL) using methyl(methylsulfinylmethyl)sulfane (1.277 g, 10.28 mmol), Triton-B (40% methanolic solution; 1.451 mL, 3.21 mmol) and heating at reflux for 16 h. This gave after workup and purification by flash column chromatography (silica gel 24 g, eluting with 0-40% EtOAc in hexane) 7-bromo-5-((2-methoxy-6-(2-(methylsulfinyl)-2-(methylthio)vinyl)phenoxy)methyl)benzofuran (476c) (2.00 g, 67% yield) as a pale-yellow oil. $^1$H NMR (300 MHz, DMSO-$d_6$) δ 8.12 (d, J=2.2 Hz, 1H), 7.71 (s, 1H), 7.67 (d, J=1.5 Hz, 1H), 7.66-7.58 (m, 1H), 7.56 (d, J=1.5 Hz, 1H), 7.18 (d, J=1.5 Hz, 1H), 7.16 (s, 1H), 7.07 (d, J=2.2 Hz, 1H), 5.14-5.00 (m, 2H), 3.90 (s, 3H), 2.64 (s, 3H), 2.13 (s, 3H); MS (ES+): 467/469 (M+1).

Step-3: Preparation of Ethyl 2-(2-((7-bromobenzofuran-5-yl)methoxy)-3-methoxyphenyl)acetate (476d)

Compound 476d was prepared according to the procedure reported in step-4 of scheme-266 from 7-bromo-5-((2-methoxy-6-(2-(methylsulfinyl)-2-(methylthio)vinyl)phenoxy)methyl)benzofuran (476c) (2.00 g, 4.28 mmol) in ethanol (20 mL) using HCl (4 M in 1,4-dioxane, 5.35 mL, 21.40 mmol) and heating at reflux for 16 h. This gave after workup and purification by flash column chromatography (silica gel 24 g, eluting with ethyl acetate and hexanes) ethyl 2-(2-((7-bromobenzofuran-5-yl)methoxy)-3-methoxyphenyl)acetate (476d) (0.74 g, 41% yield) as a clear colorless oil. $^1$H NMR (300 MHz, DMSO-$d_6$) δ 8.14 (d, J=2.1 Hz, 1H), 7.70 (d, J=1.5 Hz, 1H), 7.61 (d, J=1.4 Hz, 1H), 7.12 (d, J=2.2 Hz, 1H), 7.04 (d, J=2.9 Hz, 1H), 7.03 (s, 1H), 6.83 (dd, J=5.9, 3.2 Hz, 1H), 5.01 (s, 2H), 3.97 (q, J=7.1 Hz, 2H), 3.86 (s, 3H), 3.58 (s, 2H), 1.08 (t, J=7.1 Hz, 3H); MS (ES+): 419/421 (M+1).

Step-4: Preparation of Ethyl 2-(2-((7-(3-(aminomethyl)phenyl)benzofuran-5-yl)methoxy)-3-methoxyphenyl)acetate (476e)

Compound 476e was prepared according to the procedure reported in step-3 of scheme-1 from ethyl 2-(2-((7-bromobenzofuran-5-yl)methoxy)-3-methoxyphenyl)acetate (476d) (109 mg, 0.260 mmol) in dioxane (4 mL), water (1 mL) using (3-(aminomethyl)phenyl)boronic acid hydrochloride (6c) (59 mg, 0.312 mmol), bis(triphenylphosphine) palladium(II) chloride (Pd(PPh$_3$)$_2$Cl$_2$) (18 mg, 0.026 mmol) and a 3.3 M aqueous $K_2CO_3$ (0.236 mL, 0.780 mmol) under an $N_2$ atmosphere heating at 100° C. for 16 h on oil bath. This gave after workup, purification by flash column chromatography (silica gel, 12 g, eluting with 0-6% MeOH in DCM) ethyl 2-(2-((7-(3-(aminomethyl)phenyl)benzofuran-5-yl)methoxy)-3-methoxyphenyl)acetate (476e) (92 mg, 79% yield) as a clear colorless oil; MS (ES+): 446 (M+1).

Step-5: Preparation of 2-(2-((7-(3-(aminomethyl) phenyl)benzofuran-5-yl)methoxy)-3-methoxyphenyl)acetic Acid (476f)

Compound 476f was prepared according to the procedure reported in step-6 of scheme-1 from ethyl 2-(2-((7-(3-(aminomethyl)phenyl)benzofuran-5-yl)methoxy)-3-methoxyphenyl)acetate (476e) (92 mg, 0.207 mmol) in MeOH (3 mL) using a 2.0 M aqueous LiOH (0.516 mL, 1.033 mmol) and stirring at room temperature for 16 h. This gave after workup and purification by reverse phase column

[C18 (100 g), eluting with 0-60% MeCN in H$_2$O containing 0.1% HCl] 2-(2-((7-(3-(aminomethyl)phenyl)benzofuran-5-yl)methoxy)-3-methoxyphenyl)acetic acid (476f) (68 mg, 79% yield) HCl salt as a white solid; $^1$H NMR (300 MHz, DMSO-d$_6$) δ 8.40 (s, 3H), 8.10 (d, J=2.2 Hz, 1H), 7.97 (d, J=1.7 Hz, 1H), 7.91 (dt, J=7.4, 1.7 Hz, 1H), 7.75 (d, J=1.6 Hz, 1H), 7.66-7.52 (m, 3H), 7.08 (d, J=2.2 Hz, 1H), 7.06-6.99 (m, 2H), 6.84 (dd, J=6.0, 3.2 Hz, 1H), 5.09 (s, 2H), 4.15 (s, 2H), 3.87 (s, 3H), 3.54 (s, 2H); MS (ES+): 418 (M+1), (ES−): 416 (M−1); Analysis calculated for C$_{25}$H$_{23}$NO$_5$·HCl·1.75H$_2$O: C, 61.85; H, 5.71; Cl, 7.30; N, 2.89; Found: C, 62.03; H, 5.48; Cl, 7.35; N, 2.98.
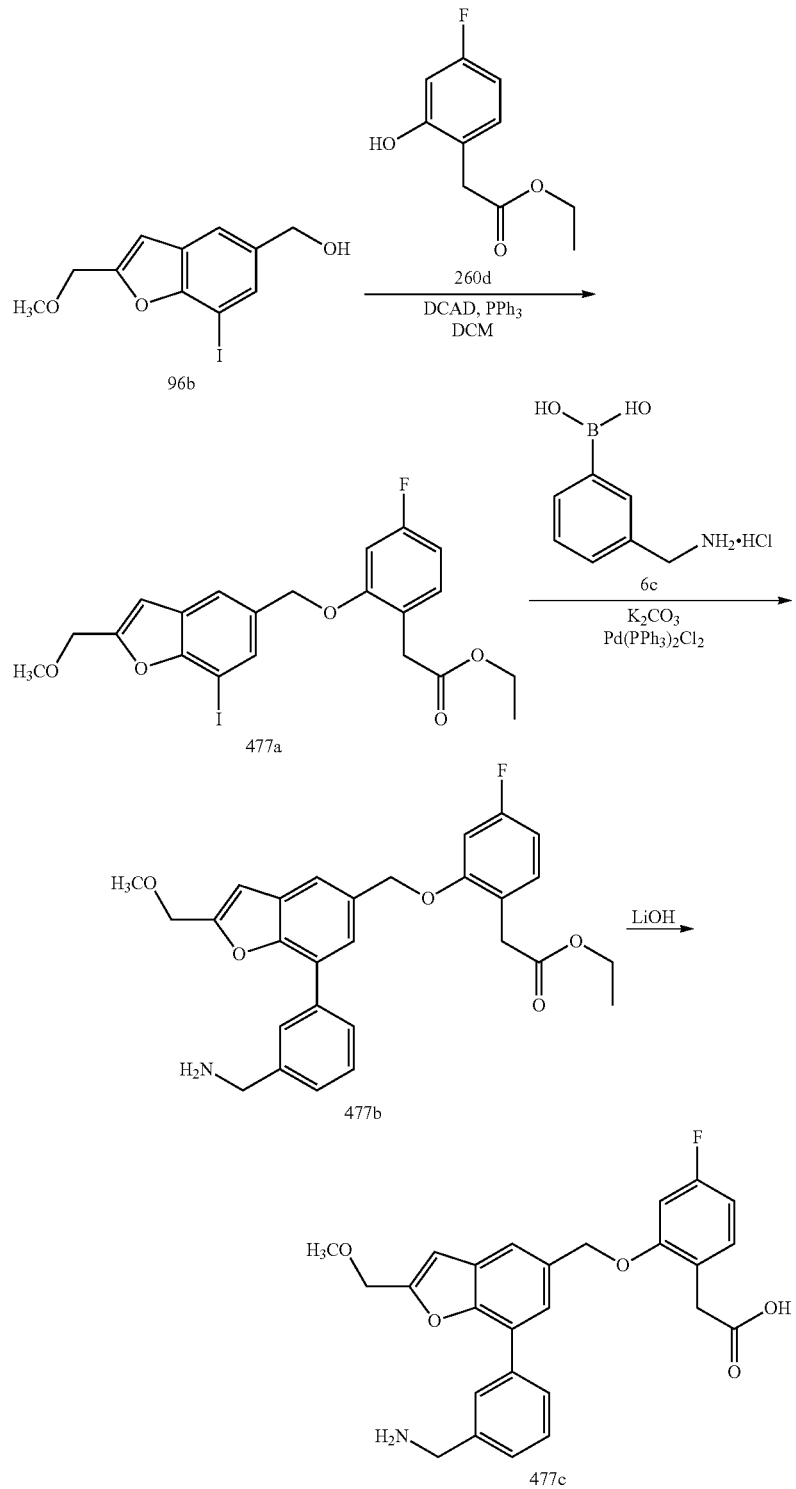

Preparation of 2-(2-((7-(3-(aminomethyl)phenyl)-2-(methoxymethyl)benzofuran-5-yl)methoxy)-4-fluorophenyl)acetic Acid (477c)

Step-1: Preparation of Ethyl 2-(4-fluoro-2-((7-iodo-2-(methoxymethyl)benzofuran-5-yl)methoxy)phenyl)acetate (477a)

Compound 477a was prepared according to the procedure reported in step-2 of scheme-23 from (7-iodo-2-(methoxymethyl)benzofuran-5-yl)methanol (96b) (2.00 g, 6.29 mmol) in DCM (60 mL) using triphenylphosphine (1.786 g, 6.81 mmol), ethyl 2-(4-fluoro-2-hydroxyphenyl)acetate (260d) (1.038 g, 5.24 mmol) and a solution of (E)-bis(4-chlorobenzyl) diazene-1,2-dicarboxylate (DCAD, 2.501 g, 6.81 mmol) in DCM (60 mL). This gave after workup and purification by flash column chromatography (silica gel, 120 g, eluting with 0 to 25% ethyl acetate in hexanes) ethyl 2-(4-fluoro-2-((7-iodo-2-(methoxymethyl)benzofuran-5-yl)methoxy)phenyl)acetate (477a) (2.15 g, 82% yield) as a clear oil which solidified into a white solid upon standing. $^1$H NMR (300 MHz, DMSO-$d_6$) δ 7.73 (d, J=1.6 Hz, 1H), 7.66 (d, J=1.5 Hz, 1H), 7.25 (dd, J=8.4, 6.9 Hz, 1H), 7.08 (s, 1H), 7.00 (dd, J=11.3, 2.5 Hz, 1H), 6.74 (td, J=8.5, 2.5 Hz, 1H), 5.15 (s, 2H), 4.56 (s, 2H), 4.02 (q, J=7.1 Hz, 2H), 3.59 (s, 2H), 3.33 (s, 3H), 1.07 (t, J=7.1 Hz, 3H); $^{19}$F NMR (282 MHz, DMSO-$d_6$) δ−112.64; MS: 521.00 (M+Na).

Step-2: Preparation of Ethyl 2-(2-((7-(3-(aminomethyl)phenyl)-2-(methoxymethyl)benzofuran-5-yl)methoxy)-4-fluorophenyl)acetate (477b)

Compound 477b was prepared according to the procedure reported in step-3 of scheme-1 from ethyl 2-(4-fluoro-2-((7-iodo-2-(methoxymethyl)benzofuran-5-yl)methoxy)phenyl)acetate (477a) (400 mg, 0.803 mmol) in dioxane (15 mL) using (3-(aminomethyl)phenyl)boronic acid hydrochloride (6c) (226 mg, 1.204 mmol), a solution of potassium carbonate (333 mg, 2.408 mmol) in water (1.8 mL), Pd(PPh$_3$)$_2$Cl$_2$ (113 mg, 0.161 mmol) and heating under a nitrogen atmosphere at 100° C. for 3 h. This gave after workup and purification by flash column chromatography (silica gel, 12g, eluting with 0 to 5% methanol in DCM) ethyl 2-(2-((7-(3-(aminomethyl)phenyl)-2-(methoxymethyl)benzofuran-5-yl)methoxy)-4-fluorophenyl)acetate (477b) (176 mg, 46% yield). $^1$H NMR (300 MHz, DMSO-$d_6$) δ 7.80-7.77 (m, 1H), 7.71 (dt, J=7.6, 1.6 Hz, 1H), 7.65 (d, J=1.6 Hz, 1H), 7.55 (d, J=1.7 Hz, 1H), 7.47 (t, J=7.6 Hz, 1H), 7.42-7.36 (m, 1H), 7.24 (dd, J=8.3, 6.9 Hz, 1H), 7.04 (dd, J=11.3, 2.5 Hz, 1H), 6.99 (s, 1H), 6.74 (td, J=8.5, 2.5 Hz, 1H), 5.24 (s, 2H), 4.57 (s, 2H), 3.92 (q, J=7.1 Hz, 2H), 3.81 (s, 2H), 3.60 (s, 2H), 3.33 (s, 3H), 0.97 (t, J=7.1 Hz, 3H); $^{19}$F NMR (282 MHz, DMSO-$d_6$) δ−112.65; MS: 478.20 (M+1).

Step-3: Preparation of 2-(2-((7-(3-(aminomethyl)phenyl)-2-(methoxymethyl)benzofuran-5-yl)methoxy)-4-fluorophenyl)acetic Acid (477c)

Compound 477c was prepared according to the procedure reported in step-6 of scheme-1 from ethyl 2-(2-((7-(3-(aminomethyl)phenyl)-2-(methoxymethyl)benzofuran-5-yl)methoxy)-4-fluorophenyl)acetate (477b) (160 mg, 0.335 mmol) in THF/methanol (5 mL, 1:1 each) using a solution of lithium hydroxide hydrate (86 mg, 2.010 mmol) in water (5 mL) and stirring at room temperature for 16 h. This gave after workup and purification by reverse-phase column chromatography [C-18 column, eluting with water (0.1% HCl)/acetonitrile from 0 to 70%] 2-(2-((7-(3-(aminomethyl)phenyl)-2-(methoxymethyl)benzofuran-5-yl)methoxy)-4-fluorophenyl)acetic acid (477c) (137 mg, 91% yield) HCl salt as a white solid. $^1$H NMR (300 MHz, DMSO-$d_6$) δ 7.98-7.94 (m, 1H), 7.92 (dt, J=7.4, 1.7 Hz, 1H), 7.72 (d, J=1.6 Hz, 1H), 7.62 (d, J=1.8 Hz, 1H), 7.61-7.52 (m, 2H), 7.24 (dd, J=8.4, 6.9 Hz, 1H), 7.05-6.97 (m, 2H), 6.73 (td, J=8.5, 2.5 Hz, 1H), 5.27 (s, 2H), 4.58 (s, 2H), 4.13 (s, 2H), 3.56 (s, 2H), 3.33 (s, 3H); $^{19}$F NMR (282 MHz, DMSO-$d_6$) δ−113.00; MS (ES+): 450.20 (M+1); Analysis calculated for $C_{26}H_{24}FNO_5 \cdot HCl \cdot 1.5H_2O$: C, 60.88; H, 5.50; N, 2.73; Cl, 6.91; Found: C, 60.72; H, 5.36; N, 2.72; Cl, 6.95.

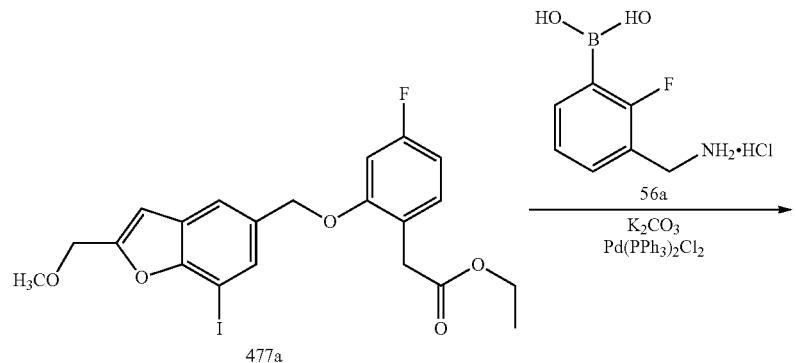

Scheme-478

-continued

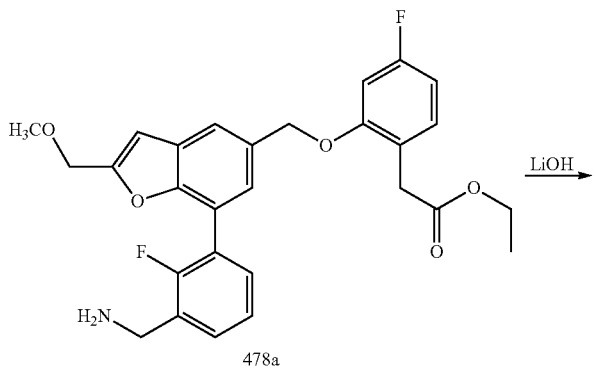

478a

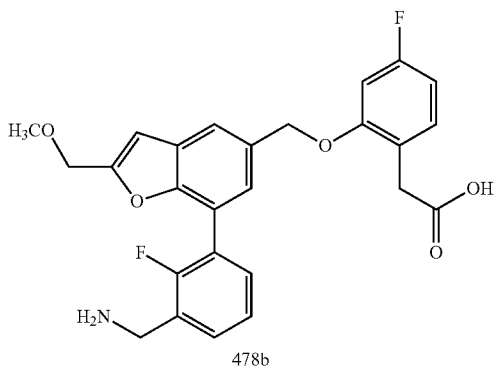

478b

Preparation of 2-(2-((7-(3-(aminomethyl)-2-fluorophenyl)-2-(methoxymethyl)benzofuran-5-yl)methoxy)-4-fluorophenyl)acetic Acid (478b)

Step-1: Preparation of Ethyl 2-(2-((7-(3-(aminomethyl)-2-fluorophenyl)-2-(methoxymethyl)benzofuran-5-yl)methoxy)-4-fluorophenyl)acetate (478a)

Compound 478a was prepared according to the procedure reported in step-3 of scheme-1 from ethyl 2-(4-fluoro-2-((7-iodo-2-(methoxymethyl)benzofuran-5-yl)methoxy)phenyl)acetate (477a) (400 mg, 0.803 mmol) in dioxane (15 mL) using 3-(aminomethyl)-2-fluorophenylboronic acid hydrochloride (56a) (136 mg, 0.803 mmol), a solution of potassium carbonate (333 mg, 2.408 mmol) in water (1.8 mL), Pd(PPh$_3$)$_2$Cl$_2$ (113 mg, 0.161 mmol) and heating under a nitrogen atmosphere at 100° C. for 3 h. This gave after workup and purification by flash column chromatography (silica gel, 12g, eluting with 0 to 5% methanol in DCM) ethyl 2-(2-((7-(3-(aminomethyl)-2-fluorophenyl)-2-(methoxymethyl)benzofuran-5-yl)methoxy)-4-fluorophenyl)acetate (478a) (260 mg, 65% yield) as a brown oil. $^1$H NMR (300 MHz, DMSO-d$_6$) δ 7.71 (d, J=1.7 Hz, 1H), 7.64-7.56 (m, 1H), 7.44 (td, J=7.3, 1.9 Hz, 1H), 7.39 (t, J=1.3 Hz, 1H), 7.32 (t, J=7.6 Hz, 1H), 7.24 (dd, J=8.4, 6.9 Hz, 1H), 7.04 (dd, J=11.3, 2.5 Hz, 1H), 6.99 (s, 1H), 6.74 (td, J=8.5, 2.5 Hz, 1H), 5.23 (s, 2H), 4.52 (s, 2H), 3.89 (q, J=7.1 Hz, 2H), 3.83 (s, 2H), 3.58 (s, 2H), 3.29 (s, 3H), 1.99 (s, 2H), 0.97 (t, J=7.1 Hz, 3H); $^{19}$F NMR (282 MHz, DMSO-d$_6$) δ −112.65, −121.98; MS (ES+): 496.15 (M+1).

Step-2: Preparation of 2-(2-((7-(3-(aminomethyl)-2-fluorophenyl)-2-(methoxymethyl)benzofuran-5-yl)methoxy)-4-fluorophenyl)acetic Acid (478b)

Compound 478b was prepared according to the procedure reported in step-6 of scheme-1 from ethyl 2-(2-((7-(3-(aminomethyl)-2-fluorophenyl)-2-(methoxymethyl)benzofuran-5-yl)methoxy)-4-fluorophenyl)acetate (478a) (245 mg, 0.494 mmol) in THF/methanol (5 mL, 1:1 each) using solution of lithium hydroxide hydrate (127 mg, 2.97 mmol) in water (5 mL) and stirring at room temperature for 16 h. This gave after workup and purification by reverse-phase column chromatography [C-18 column, eluting with water (0.1% HCl)/acetonitrile from 0 to 70%] 2-(2-((7-(3-(aminomethyl)-2-fluorophenyl)-2-(methoxymethyl)benzofuran-5-yl)methoxy)-4-fluorophenyl)acetic acid (478b) (138 mg, 60% yield) HCl salt as a white solid; $^1$H NMR (300 MHz, DMSO-d$_6$) δ 7.78 (d, J=1.6 Hz, 1H), 7.74-7.62 (m, 2H), 7.48-7.38 (m, 2H), 7.24 (dd, J=8.4, 6.9 Hz, 1H), 7.05-6.97 (m, 2H), 6.73 (td, J=8.5, 2.5 Hz, 1H), 5.27 (s, 2H), 4.52 (s, 2H), 4.17 (s, 2H), 3.55 (s, 2H), 3.29 (s, 3H); $^{19}$F NMR (282 MHz, DMSO-d$_6$) δ −113.00, −118.72; MS (ES+): 468.10 (M+1); Analysis calculated for C$_{26}$H$_{23}$F$_2$NO$_5$.HCl.0.25H$_2$O: C, 61.42; H, 4.86; N, 2.75; Cl, 6.97; Found: C, 61.45; H, 4.96; N, 2.71; Cl, 6.85.

Scheme-479

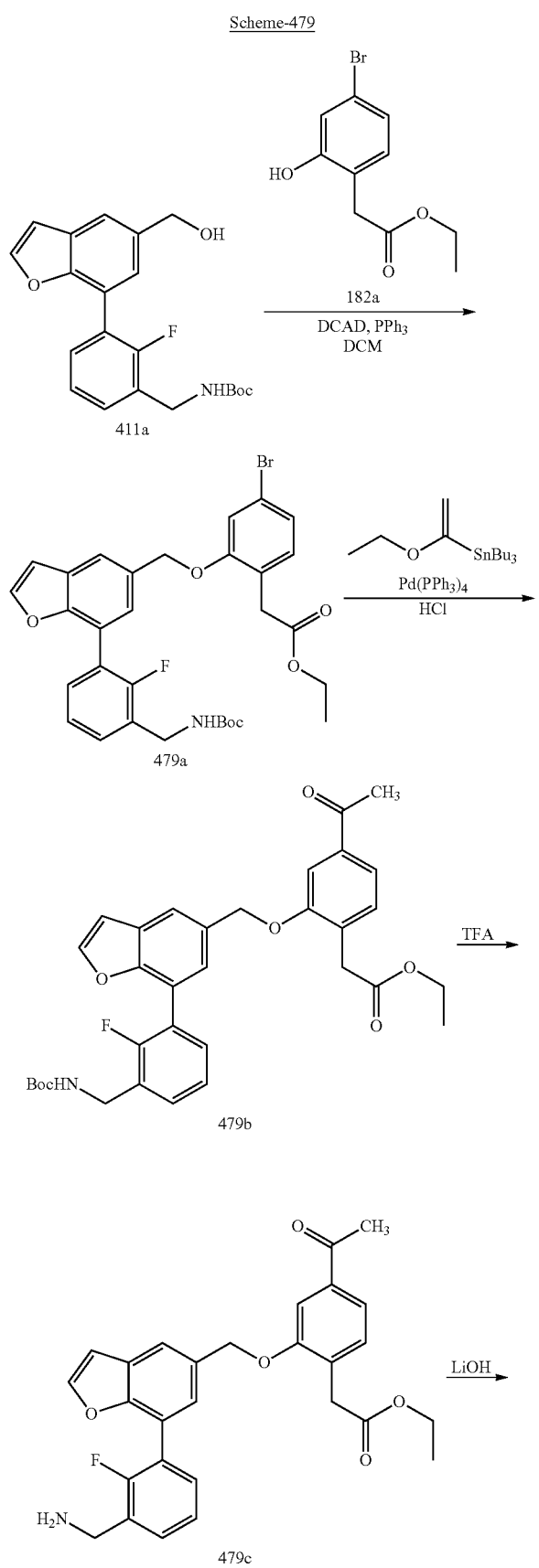

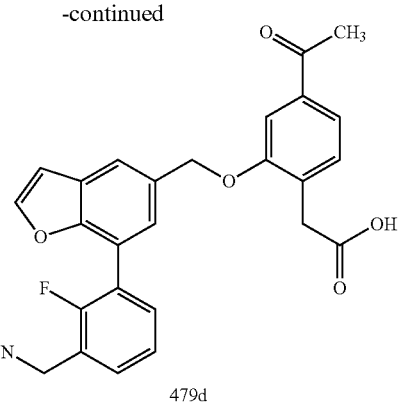

Preparation of 2-(4-acetyl-2-((7-(3-(aminomethyl)-2-fluorophenyl)benzofuran-5-yl)methoxy)phenyl) acetic Acid (479d)

Step-1: Preparation of Ethyl 2-(4-bromo-2-((7-(3-(((tert-butoxycarbonyl)amino)methyl)-2-fluorophenyl)benzofuran-5-yl)methoxy)phenyl)acetate (479a)

Compound 479a was prepared according to the procedure reported in step-2 of scheme-23 from tert-butyl 2-fluoro-3-(5-(hydroxymethyl)benzofuran-7-yl)benzylcarbamate (411a) (1.00 g, 2.69 mmol) in DCM (30 mL) using triphenylphosphine (0.835 g, 3.18 mmol), ethyl 2-(4-bromo-2-hydroxyphenyl)acetate (182a) (0.634 g, 2.448 mmol) and a solution of (E)-bis(4-chlorobenzyl) diazene-1,2-dicarboxylate (DCAD, 1.168 g, 3.18 mmol) in DCM (30 mL). This gave after workup and purification by flash column chromatography (silica gel, 80 g, eluting with 0 to 25% ethyl acetate in hexanes) ethyl 2-(4-bromo-2-((7-(3-(((tert-butoxycarbonyl)amino)methyl)-2-fluorophenyl)benzofuran-5-yl)methoxy)phenyl)acetate (479a) (760 mg, 51% yield) as a light brown oil; $^1$H NMR (300 MHz, DMSO-$d_6$) δ 8.05 (d, J=2.2 Hz, 1H), 7.75 (d, J=1.6 Hz, 1H), 7.53-7.44 (m, 2H), 7.43-7.27 (m, 4H), 7.19 (d, J=8.0 Hz, 1H), 7.12 (dd, J=8.0, 1.8 Hz, 1H), 7.06 (d, J=2.2 Hz, 1H), 5.26 (s, 2H), 4.26 (d, J=6.1 Hz, 2H), 3.88 (q, J=7.1 Hz, 2H), 3.59 (s, 2H), 1.41 (s, 9H), 0.96 (t, J=7.1 Hz, 3H); $^{19}$F NMR (282 MHz, DMSO-$d_6$) δ −120.76.

Step-2: Preparation of Ethyl 2-(4-acetyl-2-((7-(3-(((tert-butoxycarbonyl)amino)methyl)-2-fluorophenyl)benzofuran-5-yl)methoxy)phenyl)acetate (479b)

Compound 479b was prepared according to the procedure reported in step-1 of scheme-262 from ethyl 2-(4-bromo-2-((7-(3-(((tert-butoxycarbonyl)amino)methyl)-2-fluorophenyl)benzofuran-5-yl)methoxy)phenyl)acetate (479a) (400 mg, 0.653 mmol) in toluene (15 mL) using tributyl(1-ethoxyvinyl)stannane (0.291 mL, 0.816 mmol) and Pd(PPh$_3$)$_4$ (75 mg, 0.065 mmol) and heating at reflux for 24 h under a nitrogen atmosphere, followed by hydrolysis using 3 N aqueous HCl (0.653 mL, 1.959 mmol). This gave after workup and purification by flash column chromatography (silica gel, 24 g, eluting with 0 to 35% ethyl acetate in hexanes) ethyl 2-(4-acetyl-2-((7-(3-(((tert-butoxycarbonyl)amino)methyl)-2-fluorophenyl)benzofuran-5-yl)methoxy) phenyl)acetate (479b) (170 mg, 45% yield) as a clear oil; $^1$H NMR (300 MHz, DMSO-$d_6$) δ 8.05 (d, J=2.2 Hz, 1H), 7.78 (d, J=1.6 Hz, 1H), 7.63 (d, J=1.6 Hz, 1H), 7.58 (dd, J=7.7, 1.5 Hz, 1H), 7.53-7.28 (m, 6H), 7.06 (d, J=2.2 Hz, 1H), 5.32 (s, 2H), 4.26 (d, J=6.1 Hz, 2H), 3.90 (q, J=7.1 Hz, 2H), 3.71 (s, 2H), 2.59 (s, 3H), 1.41 (s, 9H), 0.97 (t, J=7.1 Hz, 3H); $^{19}$F NMR (282 MHz, DMSO-d$_6$) δ −120.72.

Step-3: Preparation of Ethyl 2-(4-acetyl-2-((7-(3-(aminomethyl)-2-fluorophenyl)benzofuran-5-yl)methoxy)phenyl)acetate (479c)

Compound 479c was prepared according to the procedure reported in step-5 of scheme-1 from ethyl 2-(4-acetyl-2-((7-(3-(((tert-butoxycarbonyl)amino)methyl)-2-fluorophenyl)benzofuran-5-yl)methoxy)phenyl)acetate (479b) (160 mg, 0.278 mmol) in DCM (10 mL) using TFA (0.413 mL, 5.56 mmol). This gave after workup ethyl 2-(4-acetyl-2-((7-(3-(aminomethyl)-2-fluorophenyl)benzofuran-5-yl)methoxy)phenyl)acetate (479c) which was used as such for next step. MS (ES+): 476.10 (M+1).

Step-4: Preparation of 2-(4-acetyl-2-((7-(3-(aminomethyl)-2-fluorophenyl)benzofuran-5-yl)methoxy)phenyl)acetic Acid (479d)

Compound 479d was prepared according to the procedure reported in step-6 of scheme-1 from ethyl 2-(4-acetyl-2-((7-(3-(aminomethyl)-2-fluorophenyl)benzofuran-5-yl)methoxy)phenyl)acetate (479c) (132 mg, 0.278 mmol) in THF/MeOH (5 mL each) using a solution of lithium hydroxide hydrate (95 mg, 2.224 mmol) in water (5 mL) and stirring at room temperature for 16 h. This gave after workup and purification by reverse phase column chromatography [C-18 column, eluting with water (0.1% HCl)/acetonitrile from 0 to 50%] 2-(4-acetyl-2-((7-(3-(aminomethyl)-2-fluorophenyl)benzofuran-5-yl)methoxy)phenyl)acetic acid (479d) (67 mg, 54% yield) HCl salt as a white solid. $^1$H NMR (300 MHz, DMSO-d$_6$) δ 8.63 (s, 3H), 8.06 (d, J=2.2 Hz, 1H), 7.85 (d, J=1.6 Hz, 1H), 7.75-7.63 (m, 2H), 7.61-7.55 (m, 2H), 7.51-7.49 (m, 1H), 7.48-7.36 (m, 2H), 7.06 (d, J=2.2 Hz, 1H), 5.36 (s, 2H), 4.17 (s, 2H), 3.67 (s, 2H), 2.57 (s, 3H); $^{19}$F NMR (282 MHz, DMSO-d$_6$) δ −118.35; MS (ES+): 448.20 (M+1); Analysis calculated for C$_{26}$H$_{22}$FNO$_5$.HCl.1.25H$_2$O: C, 61.66; H, 5.08; Cl, 7.00; N, 2.77; Found: C, 61.56; H, 5.16; Cl, 7.00; N, 2.81.

Scheme-480

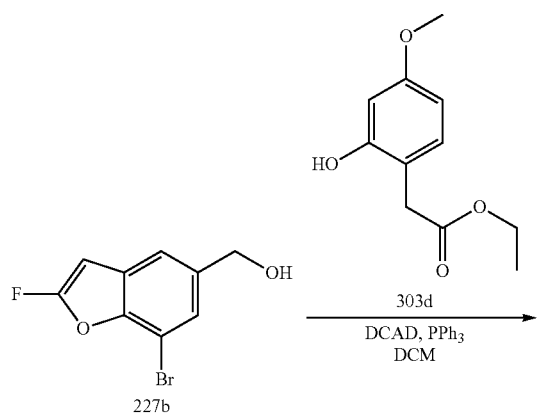

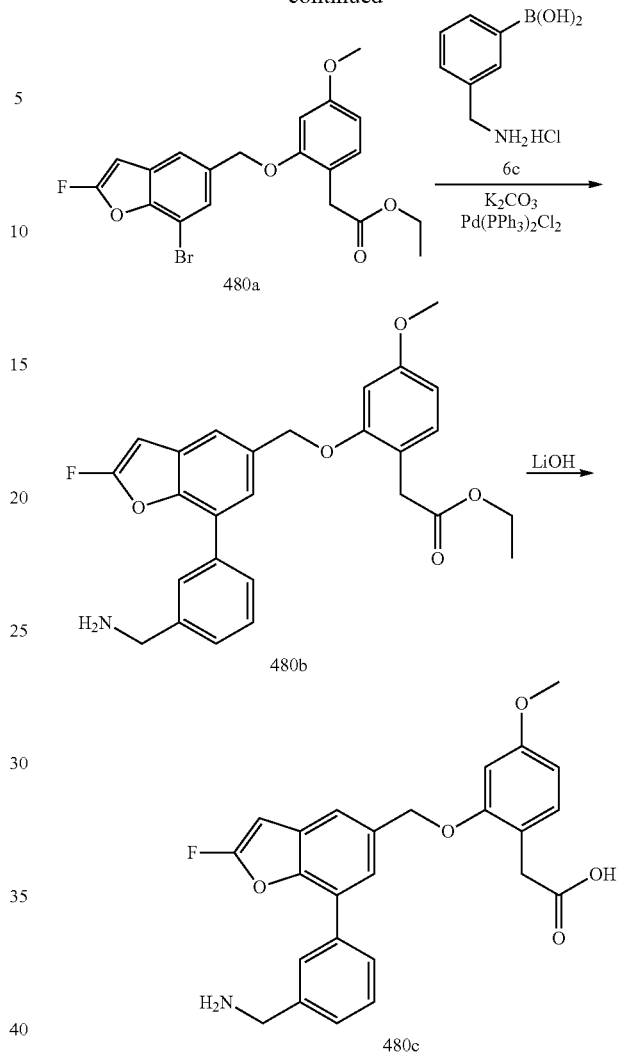

Preparation of 2-(2-((7-(3-(aminomethyl)phenyl)-2-fluorobenzofuran-5-yl)methoxy)-4-methoxyphenyl)acetic Acid (480c)

Step-1: Preparation of Ethyl 2-(2-((7-bromo-2-fluorobenzofuran-5-yl)methoxy)-4-methoxyphenyl)acetate (480a)

Compound 480a was prepared according to the procedure reported in step-2 of scheme-23 from (7-bromo-2-fluorobenzofuran-5-yl)methanol (227b) (1.42 g, 5.79 mmol) in DCM (60 mL) using triphenylphosphine (1.672 g, 6.37 mmol), ethyl 2-(2-hydroxy-4-methoxyphenyl)acetate (303d) (1.462 g, 6.95 mmol) and a solution of (E)-bis(4-chlorobenzyl) diazene-1,2-dicarboxylate (DCAD, 2.341 g, 6.37 mmol) in DCM (60 mL). This gave after workup and purification by flash column chromatography (silica gel, 120 g, eluting with 0 to 20% ethyl acetate in hexanes) ethyl 2-(2-((7-bromo-2-fluorobenzofuran-5-yl)methoxy)-4-methoxyphenyl)acetate (480a) (1.75 g, 69% yield) as a white solid; $^1$H NMR (300 MHz, DMSO-d$_6$) δ 7.63 (d, J=1.5 Hz, 1H), 7.58 (d, J=1.5 Hz, 1H), 7.12 (d, J=8.3 Hz, 1H), 6.64 (d, J=2.4 Hz, 1H), 6.54 (d, J=6.4 Hz, 1H), 6.49 (dd, J=8.3, 2.4 Hz, 1H), 5.16 (s, 2H), 4.01 (q, J=7.1 Hz, 2H), 3.74 (s, 3H), 3.54 (s, 2H), 1.09 (t, J=7.1 Hz, 3H). $^{19}$F NMR (282 MHz, DMSO-d$_6$) δ−110.46.

Step-2: Preparation of Ethyl 2-(2-((7-(3-(aminomethyl)phenyl)-2-fluorobenzofuran-5-yl)methoxy)-4-methoxyphenyl)acetate (480b)

Compound 480b was prepared according to the procedure reported in step-3 of scheme-1 from ethyl 2-(2-((7-bromo-2-fluorobenzofuran-5-yl)methoxy)-4-methoxyphenyl)acetate (480a) (200 mg, 0.457 mmol) in dioxane (5 mL) using (3-(aminomethyl)phenyl)boronic acid hydrochloride (6c) (103 mg, 0.549 mmol), bis(triphenylphosphine)palladium (II) chloride (Pd(PPh$_3$)$_2$Cl$_2$) (48 mg, 0.069 mmol) and a solution of K$_2$CO$_3$ (190 mg, 1.372 mmol) in water (0.5 mL) under an argon atmosphere heating at 100° C. for 3 h on oil bath. This gave after workup, purification by flash column chromatography (silica gel, 24 g, eluting with DMA80 in DCM from 0-50%) ethyl 2-(2-((7-(3-(aminomethyl)phenyl)-2-fluorobenzofuran-5-yl)methoxy)-4-methoxyphenyl) acetate (480b) (90 mg, 43% yield) as a clear oil. $^1$H NMR (300 MHz, DMSO-d$_6$) δ 7.77 (d, J=2.2 Hz, 1H), 7.66 (dt, J=8.0, 1.9 Hz, 1H), 7.61 (d, J=1.7 Hz, 1H), 7.55 (d, J=1.7 Hz, 1H), 7.48 (t, J=7.5 Hz, 1H), 7.45-7.39 (m, 1H), 7.11 (d, J=8.3 Hz, 1H), 6.68 (d, J=2.4 Hz, 1H), 6.49 (dd, J=8.3, 2.4 Hz, 1H), 6.44 (d, J=6.4 Hz, 1H), 5.22 (s, 2H), 3.93 (q, J=7.1 Hz, 2H), 3.83 (s, 2H), 3.74 (s, 3H), 3.54 (s, 2H), 1.00 (t, J=7.1 Hz, 3H). $^{19}$F NMR (282 MHz, DMSO-d$_6$) δ−111.73. MS (ES+): 464.1 (M+1).

Step-3: Preparation of 2-(2-((7-(3-(aminomethyl)phenyl)-2-fluorobenzofuran-5-yl)methoxy)-4-methoxyphenyl)acetic Acid (480c)

Compound 480c was prepared according to the procedure reported in step-6 of scheme-1 from of ethyl 2-(2-((7-(3-(aminomethyl)phenyl)-2-fluorobenzofuran-5-yl)methoxy)-4-methoxyphenyl)acetate (480b) (89 mg, 0.192 mmol) in THF/MeOH (3 mL each) using a solution 1.0 M aqueous LiOH (0.576 mL, 0.576 mmol). This gave after workup and purification by reverse phase column [C18 column, 50 g, eluting with 0.1% aqueous HCl in water and acetonitrile from 0-100%] 2-(2-((7-(3-(aminomethyl)phenyl)-2-fluorobenzofuran-5-yl)methoxy)-4-methoxyphenyl)acetic acid (480c) (22 mg, 26% yield) HCl salt as a white solid; $^1$H NMR (300 MHz, DMSO-d$_6$) δ 8.42 (s, 2H, D$_2$O exchangeable), 7.94 (s, 1H), 7.85 (dt, J=6.9, 2.0 Hz, 1H), 7.68 (d, J=1.6 Hz, 1H), 7.62-7.56 (m, 3H), 7.11 (d, J=8.3 Hz, 1H), 6.66 (d, J=2.4 Hz, 1H), 6.56-6.37 (m, 2H), 5.24 (s, 2H), 4.14 (s, 2H), 3.73 (s, 3H), 3.51 (s, 2H). $^{19}$F NMR (282 MHz, DMSO-d$_6$) δ−111.56. MS (ES+): 436.1 (M+1); (ES−): 434.2 (M−1).

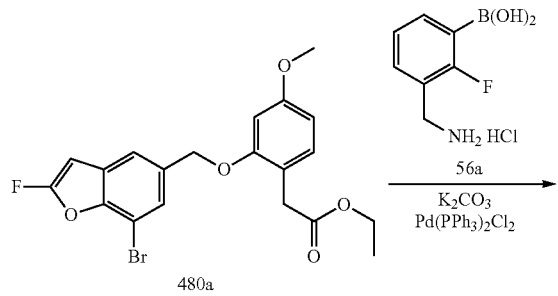

Scheme-481

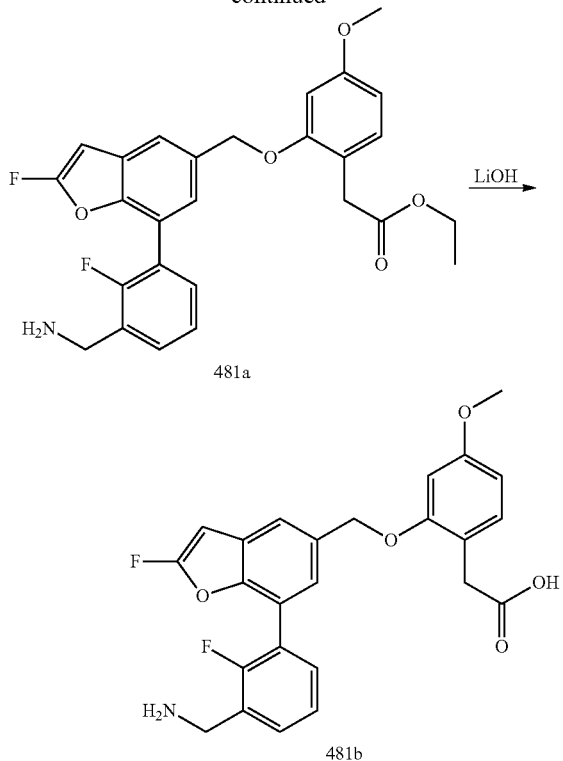

Preparation of 2-(2-((7-(3-(aminomethyl)-2-fluorophenyl)-2-fluorobenzofuran-5-yl)methoxy)-4-methoxyphenyl)acetic Acid (481b)

Step-1: Preparation of Ethyl 2-(2-((7-(3-(aminomethyl)-2-fluorophenyl)-2-fluorobenzofuran-5-yl)methoxy)-4-methoxyphenyl)acetate (481a)

Compound 481a was prepared according to the procedure reported in step-3 of scheme-1 from ethyl 2-(2-((7-bromo-2-fluorobenzofuran-5-yl)methoxy)-4-methoxyphenyl)acetate (480a) (200 mg, 0.457 mmol) in dioxane (5 mL) using (3-(aminomethyl)-2-fluorophenyl)boronic acid hydrochloride (56a) (94 mg, 0.457 mmol), bis(triphenylphosphine)palladium(II) chloride (Pd(PPh$_3$)$_2$Cl$_2$) (48 mg, 0.069 mmol) and a solution of K$_2$CO$_3$ (190 mg, 1.372 mmol) in water (0.5 mL) under an argon atmosphere heating at 100° C. for 3 h on oil bath. This gave after workup, purification by flash column chromatography (silica gel, 24 g, eluting with DMA80 in DCM from 0-50%) ethyl 2-(2-((7-(3-(aminomethyl)-2-fluorophenyl)-2-fluorobenzofuran-5-yl)methoxy)-4-methoxyphenyl)acetate (481a) (80 mg, 36% yield) as a clear oil; $^1$H NMR (300 MHz, DMSO-d$_6$) δ 7.67 (d, J=1.7 Hz, 1H), 7.62 (t, J=7.2 Hz, 1H), 7.46 (td, J=7.3, 1.9 Hz, 1H), 7.40 (d, J=1.6 Hz, 1H), 7.33 (t, J=7.6 Hz, 1H), 7.11 (d, J=8.3 Hz, 1H), 6.69 (d, J=2.4 Hz, 1H), 6.49 (dd, J=8.3, 2.4 Hz, 1H), 6.45 (d, J=6.4 Hz, 1H), 5.20 (s, 2H), 3.90 (q, J=7.1 Hz, 2H), 3.85 (s, 2H), 3.74 (s, 3H), 3.53 (s, 2H), 0.99 (t, J=7.1 Hz, 3H). $^{19}$F NMR (282 MHz, DMSO-d$_6$) δ−111.68, −121.86. MS (ES+): 482.2 (M+1).

Step-2: Preparation of 2-(2-((7-(3-(aminomethyl)-2-fluorophenyl)-2-fluorobenzofuran-5-yl)methoxy)-4-methoxyphenyl)acetic Acid (481b)

Compound 481b was prepared according to the procedure reported in step-6 of scheme-1 from ethyl 2-(2-((7-(3-

(aminomethyl)-2-fluorophenyl)-2-fluorobenzofuran-5-yl) methoxy)-4-methoxyphenyl)acetate (481a) (79 mg, 0.164 mmol) in THF/MeOH (2.5 mL each) using a solution 1.0 M aqueous LiOH (0.492 mL, 0.492 mmol). This gave after workup and purification by reverse phase column [C18 column, 50 g, eluting with 0.1% aqueous HCl in water and acetonitrile from 0-100%] 2-(2-((7-(3-(aminomethyl)-2-fluorophenyl)-2-fluorobenzofuran-5-yl)methoxy)-4-methoxyphenyl)acetic acid (481b) (35 mg, 47% yield) HCl salt as a white solid; $^1$H NMR (300 MHz, DMSO-d$_6$) δ 8.52 (s, 3H, D$_2$O exchangeable), 7.78-7.61 (m, 3H), 7.51-7.38 (m, 2H), 7.11 (d, J=8.3 Hz, 1H), 6.66 (d, J=2.4 Hz, 1H), 6.51-6.40 (m, 2H), 5.24 (s, 2H), 4.22-4.12 (m, 2H), 3.73 (s, 3H), 3.49 (s, 2H). $^{19}$F NMR (282 MHz, DMSO-d$_6$) δ –111.89, –118.52. MS (ES+): 454.1 (M+1); (ES–): 452.2 (M–1); Analysis calculated for C$_{25}$H$_{21}$F$_2$NO$_5$·1.5HCl·2H$_2$O: C, 55.18; H, 4.91; N, 2.57; found: C, 54.94; H, 5.11; N, 2.63.

Scheme-482

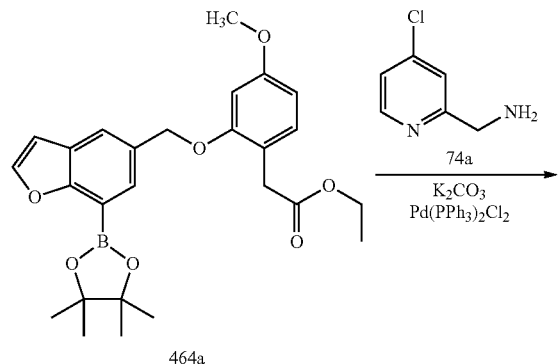

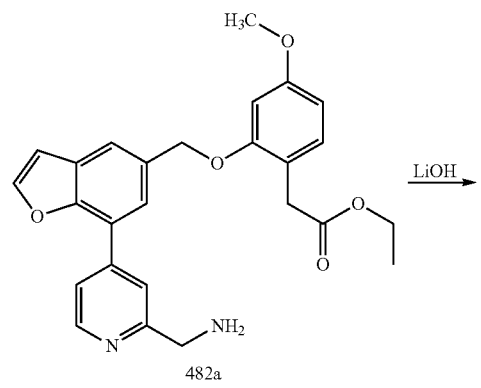

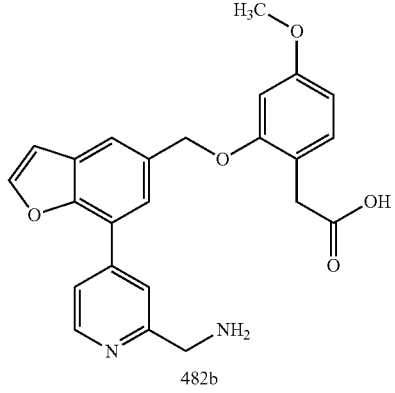

Preparation of 2-(2-((7-(2-(aminomethyl)pyridin-4-yl)benzofuran-5-yl)methoxy)-4-methoxyphenyl) acetic Acid (482b)

Step-1: Preparation of Ethyl 2-(2-((7-(2-(aminomethyl)pyridin-4-yl)benzofuran-5-yl)methoxy)-4-methoxyphenyl)acetate (482a)

Compound 482a was prepared according to the procedure reported in step-3 of scheme-1 from ethyl 2-(4-methoxy-2-((7-(4,4,5,5-tetramethyl-1,3,2-dioxaborolan-2-yl)benzofuran-5-yl)methoxy)phenyl)acetate (464a) (1.00 g, 2.144 mmol) in dioxane (25 mL) using (4-chloropyridin-2-yl) methanamine (74a) (0.306 g, 2.144 mmol), bis(triphenylphosphine)palladium(II) chloride (Pd(PPh$_3$)$_2$Cl$_2$) (0.226 g, 0.322 mmol) and a solution of K$_2$CO$_3$ (0.889 g, 6.43 mmol) in water (2.5 mL) under a nitrogen atmosphere heating at 100° C. for 16 h on oil bath. This gave after workup, purification by flash column chromatography (silica gel, 80 g, eluting with 0 to 100% ethyl acetate in hexanes, then 0 to 40% DMA80 in DCM) ethyl 2-(2-((7-(2-(aminomethyl)pyridin-4-yl)benzofuran-5-yl)methoxy)-4-methoxyphenyl)acetate (482a) (526 mg, 55% yield) as a yellow semi-solid. $^1$H NMR (300 MHz, DMSO-d$_6$) δ 8.62 (dd, J=5.3, 0.8 Hz, 1H), 8.15 (d, J=2.2 Hz, 1H), 7.98-7.96 (m, 1H), 7.80 (d, J=1.6 Hz, 1H), 7.77-7.71 (m, 2H), 7.14-7.08 (m, 2H), 6.70 (d, J=2.4 Hz, 1H), 6.49 (dd, J=8.3, 2.4 Hz, 1H), 5.25 (s, 2H), 3.97-3.87 (m, 4H), 3.74 (s, 3H), 3.55 (s, 2H), 0.98 (t, J=7.1 Hz, 3H); MS (ES+): 447.20 (M+1).

Step-2: Preparation of 2-(2-((7-(2-(aminomethyl) pyridin-4-yl)benzofuran-5-yl)methoxy)-4-methoxyphenyl)acetic Acid (482b)

Compound 482b was prepared according to the procedure reported in step-6 of scheme-1 from ethyl 2-(2-((7-(2-(aminomethyl)pyridin-4-yl)benzofuran-5-yl)methoxy)-4-methoxyphenyl)acetate (482a) (500 mg, 1.120 mmol) in THF/MeOH (8 mL each) using a solution of lithium hydroxide hydrate (288 mg, 6.72 mmol) in water (8 mL) and stirring at room temperature for 16 h. This gave after workup and purification by reverse phase column [C18 column, eluting with water (containing 0.1% HCl)/acetonitrile (1:0 to 0:1)] 2-(2-((7-(2-(aminomethyl)pyridin-4-yl)benzofuran-5-yl)methoxy)-4-methoxyphenyl)acetic acid (482b) (254 mg, 54%) HCl salt as a white solid; $^1$H NMR (300 MHz, DMSO-d$_6$) δ 8.78 (dd, J=5.3, 0.8 Hz, 1H), 8.49 (s, 3H), 8.17 (d, J=2.2 Hz, 1H), 8.09-8.08 (m, 1H), 8.00 (dd, J=5.3, 1.7 Hz, 1H), 7.87 (d, J=1.6 Hz, 1H), 7.81 (d, J=1.6 Hz, 1H), 7.17-7.04 (m, 2H), 6.67 (d, J=2.4 Hz, 1H), 6.49 (dd, J=8.3, 2.4 Hz, 1H), 5.28 (s, 2H), 4.36-4.27 (m, 2H), 3.73 (s, 3H), 3.52 (s, 2H); MS (ES+): 419.10 (M+1); MS (ES–): 417.20 (M–1); Analysis calculated for C$_{24}$H$_{22}$N$_2$O$_5$·1.75HCl·1.75H$_2$O: C, 56.11; H, 5.35; N, 5.45; Cl, 12.08; Found: C, 56.30; H, 5.29; N, 5.51; Cl, 11.94.

Scheme-483

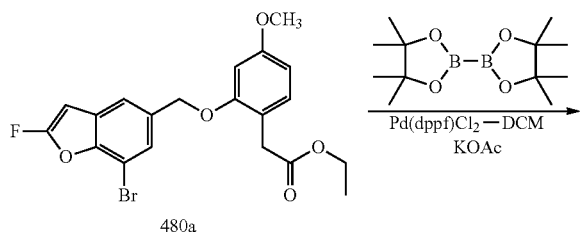

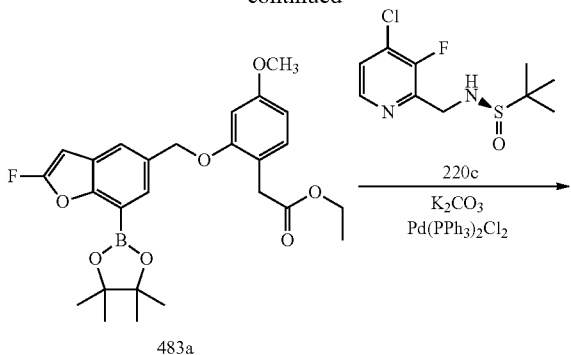

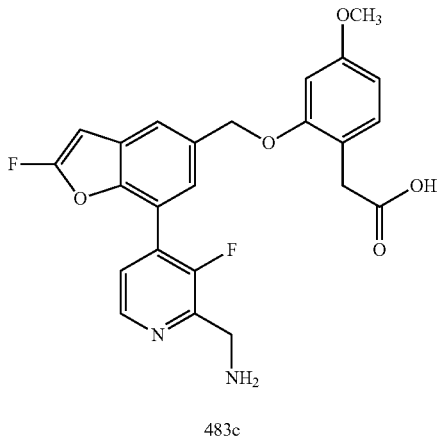

Preparation of 2-(2-((7-(2-(aminomethyl)-3-fluoro-pyridin-4-yl)-2-fluorobenzofuran-5-yl)methoxy)-4-methoxyphenyl)acetic Acid (483c)

Step-1: Preparation of Ethyl 2-(2-((2-fluoro-7-(4,4,5,5-tetramethyl-1,3,2-dioxaborolan-2-yl)benzofuran-5-yl)methoxy)-4-methoxyphenyl)acetate (483a)

Compound 483a was prepared according to the procedure reported in step-1 of scheme-59 from ethyl 2-(2-((7-bromo-2-fluorobenzofuran-5-yl)methoxy)-4-methoxyphenyl)acetate (480a) (1.15 g, 2.63 mmol), using bis(pinacolato)diboron (1.002 g, 3.95 mmol), potassium acetate (0.774 g, 7.89 mmol) and Pd(dppf)Cl$_2$-DCM (0.215 g, 0.263 mmol) in anhydrous dioxane (35 mL) under an argon atmosphere and heating at 90° C. overnight. This gave after workup and purification by flash column chromatography [silica (40g), eluting with EtOAc in hexane from 0-40%] ethyl 2-(2-((2-fluoro-7-(4,4,5,5-tetramethyl-1,3,2-dioxaborolan-2-yl)benzofuran-5-yl)methoxy)-4-methoxyphenyl)acetate (483a) (1.10g, 86% yield) as a clear oil; 1H NMR (300 MHz, DMSO-d$_6$) δ 7.75 (d, J=1.9 Hz, 1H), 7.62 (d, J=1.9 Hz, 1H), 7.10 (d, J=8.3 Hz, 1H), 6.67 (d, J=2.4 Hz, 1H), 6.48 (dd, J=8.3, 2.4 Hz, 1H), 6.35 (d, J=6.4 Hz, 1H), 5.15 (s, 2H), 4.06-3.91 (m, 2H), 3.74 (s, 3H), 3.51 (s, 2H), 1.34 (s, 12H), 1.06 (t, J=7.1 Hz, 3H).

Step-2: Preparation of (S)-ethyl 2-(2-((7-(2-(((1,1-dimethylethylsulfinamido)methyl)-3-fluoropyridin-4-yl)-2-fluorobenzofuran-5-yl)methoxy)-4-methoxyphenyl)acetate (483b)

Compound 483b was prepared according to the procedure reported in step-3 of scheme-1 from ethyl 2-(2-((2-fluoro-7-(4,4,5,5-tetramethyl-1,3,2-dioxaborolan-2-yl)benzofuran-5-yl)methoxy)-4-methoxyphenyl)acetate (483a) (260 mg, 0.537 mmol) in dioxane (10 mL) using (+)-(S)—N-((4-chloro-3-fluoropyridin-2-yl)methyl)-2-methylpropane-2-sulfinamide (220c) (142 mg, 0.537 mmol), Pd(PPh$_3$)$_2$Cl$_2$ (57 mg, 0.081 mmol) and a solution of K$_2$CO$_3$ (223 mg, 1.611 mmol) in water (1 mL) under a nitrogen atmosphere heating at 100° C. for 15 h on oil bath. This gave after workup and purification by reverse phase column chromatography [C18 (50 g), eluting with ACN in water (containing 0.1% HCl) from 0-100%] (S)-ethyl 2-(2-((7-(2-(((1,1-dimethylethylsulfinamido)methyl)-3-fluoropyridin-4-yl)-2-fluorobenzofuran-5-yl)methoxy)-4-methoxyphenyl)acetate (483b) (165 mg, 52% yield) as an brown gum; 1H NMR (300 MHz, DMSO-d$_6$) δ 8.53 (d, J=4.9 Hz, 1H), 7.77 (d, J=1.6 Hz, 1H), 7.66 (t, J=5.2 Hz, 1H), 7.53-7.50 (m, 1H), 7.11 (d, J=8.3 Hz, 1H), 6.69 (d, J=2.4 Hz, 1H), 6.54-6.45 (m, 2H), 5.86 (t, J=5.8 Hz, 1H), 5.23 (s, 2H), 4.41 (dd, J=5.8, 2.1 Hz, 2H), 3.91 (q, J=7.1 Hz, 2H), 3.74 (s, 3H), 3.54 (s, 2H), 1.11 (s, 9H), 0.99 (t, J=7.1 Hz, 3H); MS (ES+): 587.2 (M+1).

Step-3: Preparation of 2-(2-((7-(2-(aminomethyl)-3-fluoropyridin-4-yl)-2-fluorobenzofuran-5-yl)methoxy)-4-methoxyphenyl)acetic Acid (483c)

To a stirred solution of (S)-ethyl 2-(2-((7-(2-(((1,1-dimethylethylsulfinamido)methyl)-3-fluoropyridin-4-yl)-2-fluorobenzofuran-5-yl)methoxy)-4-methoxyphenyl)acetate (483b) (165 mg, 0.281 mmol) in THF (5 mL) was added hydrochloric acid (4.M in 1-4-dioxane, 0.141 mL, 0.563 mmol), stirred at room temperature for 30 minutes and concentrated in vacuum to dryness. The residue obtained was dissolved in THF (5 mL), acetonitrile (1 mL) and water (1 mL) and added lithium hydroxide monohydrate (59.0 mg, 1.406 mmol). The reaction mixture was stirred for 48 h at room temperature and concentrated to remove THF and acetonitrile. The reaction was diluted with water (2 mL) and acidified to pH 4 using 1M HCl. The solid separated out was decanted and purified by reverse-phase column chromatography [C-18 column, 50 g, eluting with 0.1% aqueous HCl in water and acetonitrile from 0-100%] to afford 2-(2-((7-(2-(aminomethyl)-3-fluoropyridin-4-yl)-2-fluorobenzofuran-5-yl)methoxy)-4-methoxyphenyl)acetic acid (483c) (79 mg, 62% yield) HCl salt as a pale yellow solid; $^1$H NMR (300 MHz, DMSO-d$_6$) δ 8.64 (d, J=4.9 Hz, 1H), 8.54 (s, 3H, D$_2$O exchangeable), 7.83 (d, J=1.6 Hz, 1H), 7.80 (t, J=5.3 Hz, 1H), 7.58 (d, J=1.4 Hz, 1H), 7.11 (d, J=8.3 Hz, 1H), 6.67 (d, J=2.4 Hz, 1H), 6.53-6.46 (m, 2H), 5.26 (s, 2H), 4.39 (d, J=6.0 Hz, 2H), 3.73 (s, 3H), 3.50 (s, 2H). $^{19}$F NMR (282 MHz, DMSO) δ−111.19, −128.49. MS (ES+): 455.1 (M+1); (ES−): 453.1 (M−1); Analysis calculated for

1453

$C_{24}H_{20}F_2N_2O_5 \cdot 1.2HCl \cdot H_2O$: C, 55.84; H, 4.53; Cl, 8.24; F, 7.36; N, 5.43; Found: C, 55.72; H, 4.53; Cl, 8.10; N, 5.29.

Scheme-484

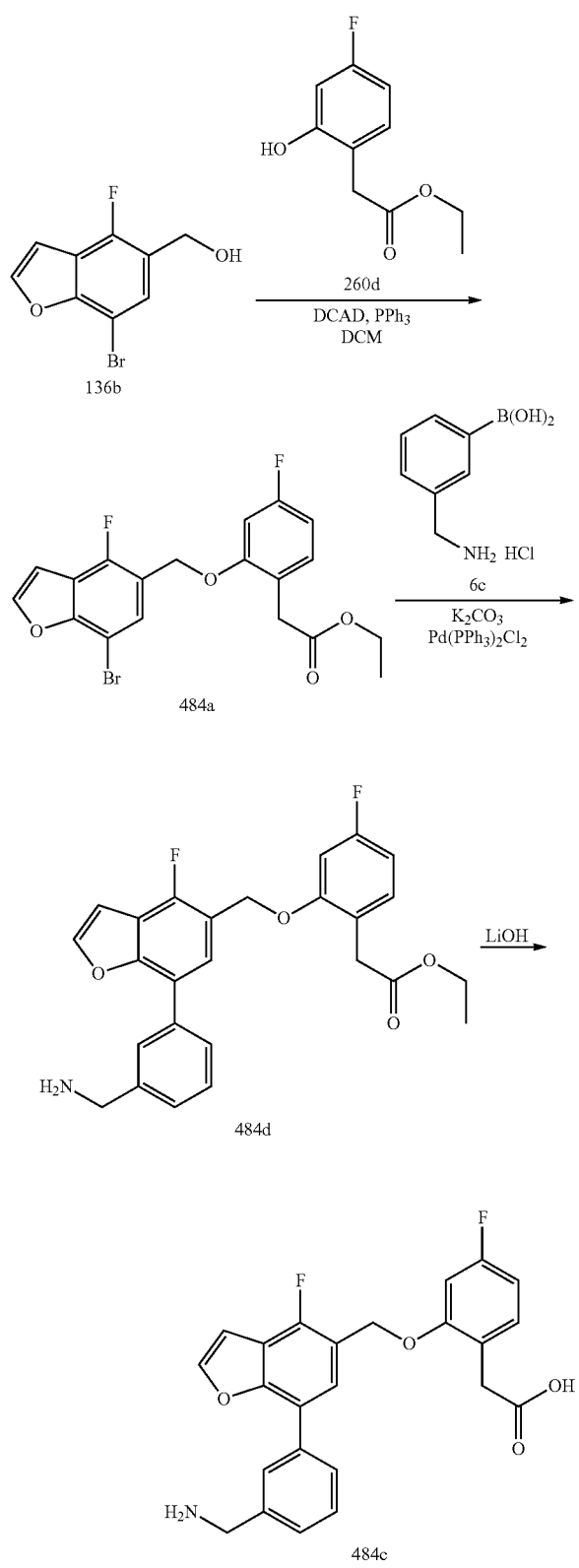

1454

Preparation of 2-(2-((7-(3-(aminomethyl)phenyl)-4-fluorobenzofuran-5-yl)methoxy)-4-fluorophenyl) acetic Acid (484c)

Step-1: Preparation of Ethyl 2-(2-((7-bromo-4-fluorobenzofuran-5-yl)methoxy)-4-fluorophenyl)acetate (484a)

Compound 484a was prepared according to the procedure reported in step-2 of scheme-23 from (7-bromo-4-fluorobenzofuran-5-yl)methanol (136b) (792 mg, 3.23 mmol) in DCM (35 mL) using triphenylphosphine (1017 mg, 3.88 mmol), ethyl 2-(4-fluoro-2-hydroxyphenyl)acetate (260d) (705 mg, 3.56 mmol) and a solution of (E)-bis(4-chlorobenzyl) diazene-1,2-dicarboxylate (DCAD, 1424 mg, 3.88 mmol) in DCM (15 mL) and stirring at room temperature for 1 h. This gave after workup and purification by flash column chromatography (silica gel, 40 g, eluting with 0 to 50% ethyl acetate in hexanes) ethyl 2-(2-((7-bromo-4-fluorobenzofuran-5-yl)methoxy)-4-fluorophenyl)acetate (484a) (1.07 g, 78% yield) as a pale yellow oil which solidified on standing; $^1$H NMR (300 MHz, DMSO-$d_6$) δ 8.22 (d, J=2.2 Hz, 1H), 7.72 (d, J=6.2 Hz, 1H), 7.28 (d, J=2.3 Hz, 1H), 7.26-7.20 (m, 1H), 7.12 (dd, J=11.2, 2.5 Hz, 1H), 6.77 (td, J=8.5, 2.5 Hz, 1H), 5.22 (d, J=1.4 Hz, 2H), 3.95 (q, J=7.1 Hz, 2H), 3.54 (s, 2H), 1.01 (t, J=7.1 Hz, 3H); $^{19}$F NMR (282 MHz, DMSO-$d_6$) δ −112.54, −124.37.

Step-2: Preparation of Ethyl 2-(2-((7-(3-(aminomethyl)phenyl)-4-fluorobenzofuran-5-yl)methoxy)-4-fluorophenyl)acetate (484b)

Compound 484b was prepared according to the procedure reported in step-3 of scheme-1 from ethyl 2-(2-((7-bromo-4-fluorobenzofuran-5-yl)methoxy)-4-fluorophenyl)acetate (484a) (153 mg, 0.360 mmol) in dioxane (5 mL) using (3-(aminomethyl)phenyl)boronic acid hydrochloride (6c) (81 mg, 0.540 mmol), Pd(PPh$_3$)$_2$Cl$_2$ (37.9 mg, 0.054 mmol) and a solution of K$_2$CO$_3$ (149 mg, 1.079 mmol) in water (0.5 mL) under an argon atmosphere heating at 100° C. for 3 h on oil bath. This gave after workup, purification by flash column chromatography [silica(12 g), eluting with DMA80 in DCM from 0-70%] ethyl 2-(2-((7-(3-(aminomethyl)phenyl)-4-fluorobenzofuran-5-yl)methoxy)-4-fluorophenyl)acetate (484b) (117 mg, 72% yield) as a dark oil. MS (ES+): 452.1 (M+1).

Step-3: Preparation of 2-(2-((7-(3-(aminomethyl) phenyl)-4-fluorobenzofuran-5-yl)methoxy)-4-fluorophenyl)acetic Acid (484c)

Compound 484c was prepared according to the procedure reported in step-6 of scheme-1 from ethyl 2-(2-((7-(3-(aminomethyl)phenyl)-4-fluorobenzofuran-5-yl)methoxy)-4-fluorophenyl)acetate (484b) (117 mg, 0.259 mmol) in THF/MeOH (6 mL each) using a solution LiOH (65 mg, 1.549 mmol) in water (2 mL) and stirring at room temperature overnight. This gave after workup and purification by reverse phase column [C18 column, 50 g, eluting with 0.1% aqueous HCl in water and acetonitrile from 0-100%] 2-(2-((7-(3-(aminomethyl)phenyl)-4-fluorobenzofuran-5-yl) methoxy)-4-fluorophenyl)acetic acid (484c) (98 mg, 0.231 mmol, 89% yield) HCl salt as a white solid. $^1$H NMR (300 MHz, DMSO-$d_6$) δ 12.17 (s, 1H), 8.39 (s, 2H), 8.19 (d, J=2.2 Hz, 1H), 7.97 (d, J=1.8 Hz, 1H), 7.89 (dt, J=7.4, 1.7 Hz, 1H), 7.74 (d, J=6.8 Hz, 1H), 7.64-7.50 (m, 2H), 7.30-7.19 (m, 2H), 7.13 (dd, J=11.3, 2.5 Hz, 1H), 6.76 (td, J=8.5, 2.5 Hz, 1H), 5.31 (s, 2H), 4.13 (s, 2H), 3.51 (s, 2H); $^{19}$F NMR (282 MHz, DMSO) δ −112.88, −124.44; MS (ES+): 424.1 (M+1); MS(ES−): 422.1 (M−1); Analysis calculated for $C_{24}H_{19}F_2NO_4 \cdot HCl \cdot 1.75H_2O$: C, 58.66; H, 4.82; Cl, 7.21; N, 2.85; Found: C, 58.67; H, 4.38; Cl, 6.88; N, 2.83.

Scheme-485

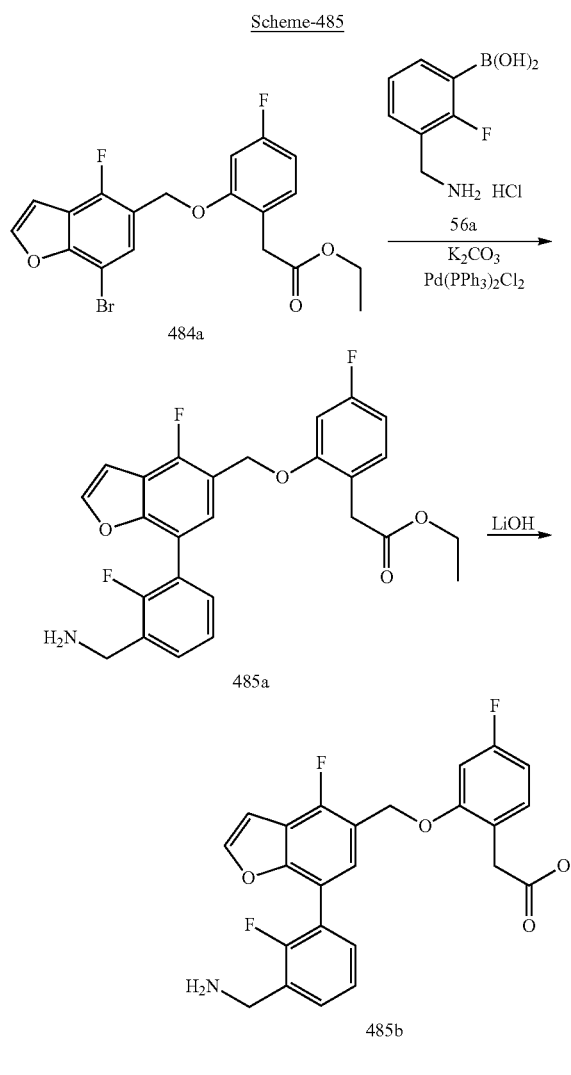

Preparation of 2-(2-((7-(3-(aminomethyl)-2-fluorophenyl)-4-fluorobenzofuran-5-yl)methoxy)-4-fluorophenyl)acetic Acid (485b)

Step-1: Preparation of Ethyl 2-(2-((7-(3-(aminomethyl)-2-fluorophenyl)-4-fluorobenzofuran-5-yl)methoxy)-4-fluorophenyl)acetate (485a)

Compound 485a was prepared according to the procedure reported in step-3 of scheme-1 from ethyl 2-(2-((7-bromo-4-fluorobenzofuran-5-yl)methoxy)-4-fluorophenyl)acetate (484a) (150 mg, 0.353 mmol) in dioxane (5 mL) using (3-(aminomethyl)-2-fluorophenyl)boronic acid hydrochloride (56a) (89 mg, 0.529 mmol), Pd(PPh$_3$)$_2$Cl$_2$ (37 mg, 0.053 mmol) and a solution of K$_2$CO$_3$ (146 mg, 1.058 mmol) in water (0.5 mL) under an argon atmosphere heating at 100° C. for 3 h on oil bath. This gave after workup, purification by flash column chromatography [silica (12 g), eluting with DMA80 in DCM from 0-70%] ethyl 2-(2-((7-(3-(aminomethyl)-2-fluorophenyl)-4-fluorobenzofuran-5-yl)methoxy)-4-fluorophenyl)acetate (485a) (125 mg, 75% yield) as a pale-yellow oil. MS (ES+): 470.1 (M+1).

Step-2: Preparation of 2-(2-((7-(3-(aminomethyl)-2-fluorophenyl)-4-fluorobenzofuran-5-yl)methoxy)-4-fluorophenyl)acetic Acid (485b)

Compound 485b was prepared according to the procedure reported in step-6 of scheme-1 from ethyl 2-(2-((7-(3-(aminomethyl)-2-fluorophenyl)-4-fluorobenzofuran-5-yl)methoxy)-4-fluorophenyl)acetate (485a) (125 mg, 0.266 mmol) in THF/MeOH (6 mL each) using a solution LiOH (75 mg, 1.787 mmol) in water (2 mL) and stirring at room temperature overnight. This gave after workup and purification by reverse phase column [C18 column, 50 g, eluting with 0.1% aqueous HCl in water and acetonitrile from 0-100%] 2-(2-((7-(3-(aminomethyl)-2-fluorophenyl)-4-fluorobenzofuran-5-yl)methoxy)-4-fluorophenyl)acetic acid (485b) (98 mg, 83% yield) HCl salt as a white solid; $^1$H NMR (300 MHz, DMSO-d$_6$) δ 12.18 (s, 1H), 8.60 (s, 3H), 8.15 (d, J=2.3 Hz, 1H), 7.79-7.62 (m, 2H), 7.59 (d, J=6.7 Hz, 1H), 7.43 (t, J=7.7 Hz, 1H), 7.32-7.18 (m, 2H), 7.13 (dd, J=11.3, 2.5 Hz, 1H), 6.76 (td, J=8.5, 2.5 Hz, 1H), 5.32 (s, 2H), 4.17 (s, 2H), 3.50 (s, 2H); $^{19}$F NMR (282 MHz, DMSO) δ −112.89, −118.53, −123.30; MS (ES+): 442.1 (M+1); MS (ES−): 440.1 (M−1); Analysis calculated for $C_{24}H_{18}F_3NO_4 \cdot HCl$: C, 60.32; H, 4.01; Cl, 7.42; N, 2.93; Found: C, 59.98; H, 3.88; Cl, 7.40; N, 3.17.

Scheme-486

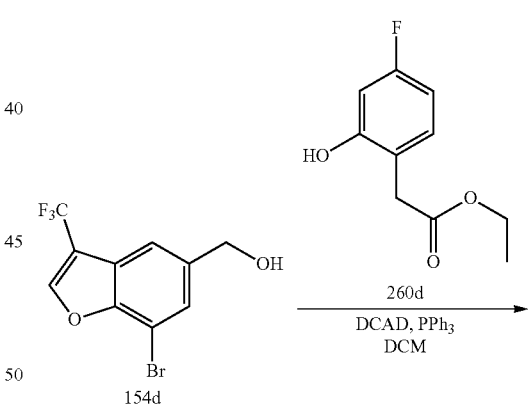

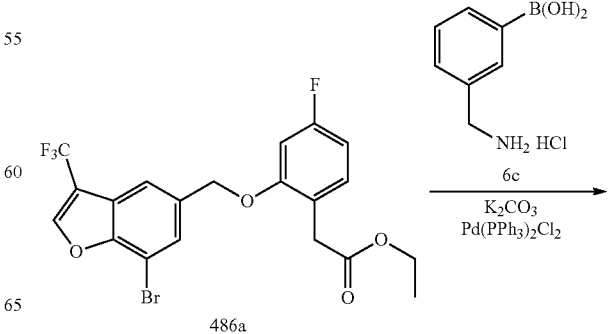

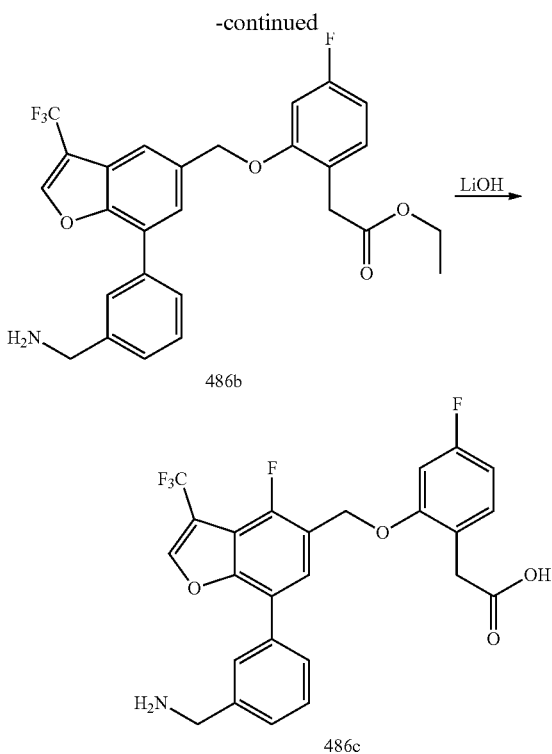

Preparation of 2-(2-((7-(3-(aminomethyl)phenyl)-3-(trifluoromethyl)benzofuran-5-yl)methoxy)-4-fluorophenyl)acetic Acid (486c)

Step-1: Preparation of Ethyl 2-(2-((7-bromo-3-(trifluoromethyl)benzofuran-5-yl)methoxy)-4-fluorophenyl)acetate (486a)

Compound 486a was prepared according to the procedure reported in step-2 of scheme-23 from (7-bromo-3-(trifluoromethyl)benzofuran-5-yl)methanol (154d) (2 g, 6.78 mmol) in DCM (70 mL) using triphenylphosphine (1.956 g, 7.46 mmol), ethyl 2-(4-fluoro-2-hydroxyphenyl)acetate (260d) (1.612 g, 8.13 mmol) and a solution of (E)-bis(4-chlorobenzyl) diazene-1,2-dicarboxylate (DCAD, 2.74 g, 7.46 mmol) in DCM (70 mL) and stirring at room temperature for 1 h. This gave after workup and purification by flash column chromatography (silica gel, 120 g, eluting with 0 to 20% ethyl acetate in hexanes) ethyl 2-(2-((7-bromo-3-(trifluoromethyl)benzofuran-5-yl)methoxy)-4-fluorophenyl)acetate (486a) (2.3 g, 71% yield) as a white solid; 1H NMR (300 MHz, DMSO-$d_6$) δ 8.97 (q, J=1.6 Hz, 1H), 7.93-7.60 (m, 2H), 7.26 (dd, J=8.3, 6.9 Hz, 1H), 7.02 (dd, J=11.3, 2.5 Hz, 1H), 6.76 (td, J=8.5, 2.5 Hz, 1H), 5.26 (s, 2H), 4.01 (q, J=7.1 Hz, 2H), 3.61 (s, 2H), 1.07 (t, J=7.1 Hz, 3H); $^{19}$F NMR (282 MHz, DMSO-$d_6$) δ−58.24, −112.61.

Step-2: Preparation of Ethyl 2-(2-((7-(3-(aminomethyl)phenyl)-3-(trifluoromethyl)benzofuran-5-yl)methoxy)-4-fluorophenyl)acetate (486b)

Compound 486b was prepared according to the procedure reported in step-3 of scheme-1 ethyl 2-(2-((7-bromo-3-(trifluoromethyl)benzofuran-5-yl)methoxy)-4-fluorophenyl)acetate (486a) (220 mg, 0.463 mmol) in dioxane (8 mL) using (3-(aminomethyl)phenyl)boronic acid hydrochloride (6c) (104 mg, 0.556 mmol), Pd(PPh$_3$)$_2$Cl$_2$ (49 mg, 0.069 mmol) and a solution of K$_2$CO$_3$ (192 mg, 1.389 mmol) in water (0.8 mL) under an argon atmosphere heating at 100° C. for 4 h on oil bath. This gave after workup, purification by flash column chromatography [silica gel (24 g), eluting with DMA80 in DCM from 0-50%] ethyl 2-(2-((7-(3-(aminomethyl)phenyl)-3-(trifluoromethyl)benzofuran-5-yl)methoxy)-4-fluorophenyl)acetate (486b) (192 mg, 83% yield) as a clear oil; $^1$H NMR (300 MHz, DMSO-$d_6$) δ 8.89 (q, J=1.6 Hz, 1H), 7.84-7.79 (m, 1H), 7.78-7.75 (m, 1H), 7.75 (s, 2H), 7.54-7.41 (m, 2H), 7.26 (dd, J=8.4, 6.9 Hz, 1H), 7.06 (dd, J=11.3, 2.5 Hz, 1H), 6.75 (td, J=8.4, 2.5 Hz, 1H), 5.32 (s, 2H), 3.91 (q, J=7.1 Hz, 2H), 3.82 (s, 2H), 3.61 (s, 2H), 0.96 (t, J=7.1 Hz, 3H); $^{19}$F NMR (282 MHz, DMSO-$d_6$) δ−58.08, −112.60; MS (ES+): 502.1 (M+1).

Step-3: Preparation of 2-(2-((7-(3-(aminomethyl)phenyl)-3-(trifluoromethyl)benzofuran-5-yl)methoxy)-4-fluorophenyl)acetic Acid (486c)

Compound 486c was prepared according to the procedure reported in step-6 of scheme-1 from ethyl 2-(2-((7-(3-(aminomethyl)phenyl)-3-(trifluoromethyl)benzofuran-5-yl)methoxy)-4-fluorophenyl)acetate (486b) (0.192 g, 0.383 mmol) in THF (2 mL), acetonitrile (1 mL) and water (1 mL) using lithium hydroxide monohydrate (0.048 g, 1.149 mmol) and stirring at room temperature overnight. This gave after workup and purification by reverse phase column [C18 column, 50 g, eluting with 0.1% aqueous HCl in water and acetonitrile from 0-100%] 2-(2-((7-(3-(aminomethyl)phenyl)-3-(trifluoromethyl)benzofuran-5-yl)methoxy)-4-fluorophenyl)acetic acid (486c) (135 mg, 75% yield) HCl salt as a white solid; $^1$H NMR (300 MHz, DMSO-$d_6$) δ 12.18 (s, 1H, D$_2$O exchangeable), 8.91 (q, J=1.6 Hz, 1H), 8.41 (s, 3H, D$_2$O exchangeable), 7.98 (s, 1H), 7.91 (dt, J=6.9, 2.0 Hz, 1H), 7.85 (s, 1H), 7.81-7.78 (m, 1H), 7.67-7.55 (m, 2H), 7.25 (dd, J=8.4, 6.9 Hz, 1H), 7.03 (dd, J=11.3, 2.5 Hz, 1H), 6.75 (td, J=8.5, 2.5 Hz, 1H), 5.35 (s, 2H), 4.14 (s, 2H), 3.57 (s, 2H); $^1$H NMR (300 MHz, DMSO-$d_6$/D$_2$O) δ 8.72 (d, J=1.9 Hz, 1H), 7.94-7.85 (m, 2H), 7.80 (s, 1H), 7.73 (d, J=1.6 Hz, 1H), 7.60 (t, J=7.6 Hz, 1H), 7.51 (d, J=7.8 Hz, 1H), 7.21 (dd, J=8.4, 6.9 Hz, 1H), 6.96 (dd, J=11.2, 2.5 Hz, 1H), 6.72 (td, J=8.5, 2.5 Hz, 1H), 5.29 (s, 2H), 4.11 (s, 3H), 3.54 (s, 2H); $^{19}$F NMR (282 MHz, DMSO-$d_6$) δ−57.99, −112.97. MS (ES+): 474.1 (M+1); (ES−): 472.1 (M−1); LC, 2.18 min, 99.83%; Analysis calculated for C$_{25}$H$_{19}$F$_4$NO$_4$.HCl.0.25H$_2$O: C, 58.37; H, 4.02; Cl, 6.89; N, 2.72; Found: C, 58.47; H, 3.80; Cl, 7.06; N, 2.82.

Scheme-487

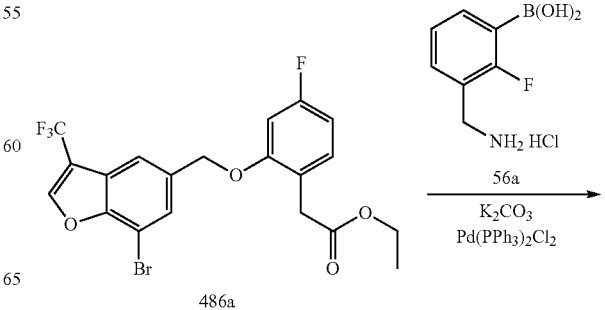

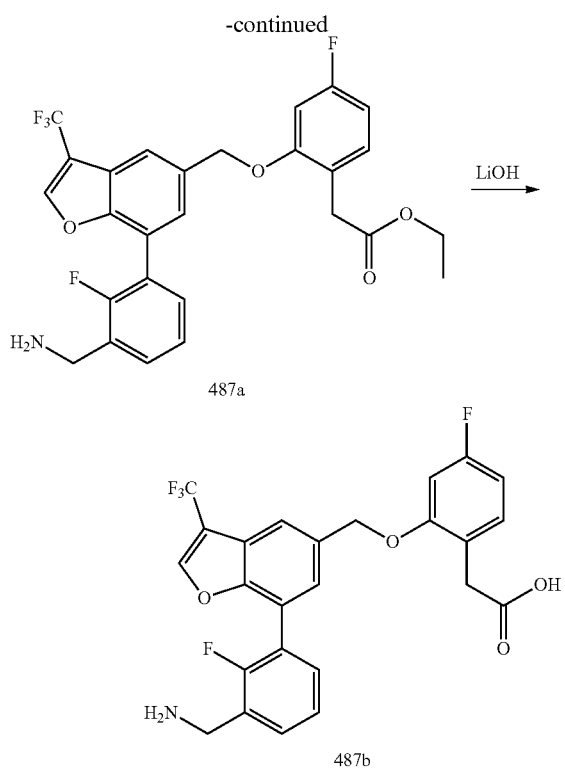

Preparation of 2-(2-((7-(3-(aminomethyl)-2-fluorophenyl)-3-(trifluoromethyl)benzofuran-5-yl)methoxy)-4-fluorophenyl)acetic Acid (487b)

Step-1: Preparation of Ethyl 2-(2-((7-(3-(aminomethyl)-2-fluorophenyl)-3-(trifluoromethyl)benzofuran-5-yl)methoxy)-4-fluorophenyl)acetate (487a)

Compound 487a was prepared according to the procedure reported in step-3 of scheme-1 from ethyl 2-(2-((7-bromo-3-(trifluoromethyl)benzofuran-5-yl)methoxy)-4-fluorophenyl)acetate (486a) (220 mg, 0.463 mmol) in dioxane (8 mL) using (3-(aminomethyl)-2-fluorophenyl)boronic acid hydrochloride (56a) (114 mg, 0.556 mmol), Pd(PPh$_3$)$_2$Cl$_2$ (49 mg, 0.069 mmol) and a solution of K$_2$CO$_3$ (192 mg, 1.389 mmol) in water (0.5 mL) under an argon atmosphere heating at 100° C. for 4 h on oil bath. This gave after workup, purification by flash column chromatography [silica gel (24 g), eluting with DMA80 in DCM from 0-50%] ethyl 2-(2-((7-(3-(aminomethyl)-2-fluorophenyl)-3-(trifluoromethyl)benzofuran-5-yl)methoxy)-4-fluorophenyl)acetate (487a) (158 mg, 66% yield) as a clear oil; $^1$H NMR (300 MHz, DMSO-d$_6$) δ 8.86 (q, J=1.6 Hz, 1H), 7.87-7.80 (m, 1H), 7.68-7.57 (m, 2H), 7.48 (td, J=7.4, 1.9 Hz, 1H), 7.35 (t, J=7.6 Hz, 1H), 7.25 (dd, J=8.3, 6.9 Hz, 1H), 7.06 (dd, J=11.3, 2.5 Hz, 1H), 6.75 (td, J=8.5, 2.5 Hz, 1H), 5.31 (s, 2H), 3.94-3.79 (m, 4H), 3.59 (s, 2H), 0.96 (t, J=7.1 Hz, 3H); $^{19}$F NMR (282 MHz, DMSO-d$_6$) δ −58.09, −112.59, −121.93; MS (ES+): 520.1 (M+1).

Step-2: Preparation of 2-(2-((7-(3-(aminomethyl)-2-fluorophenyl)-3-(trifluoromethyl)benzofuran-5-yl)methoxy)-4-fluorophenyl)acetic Acid (487b)

Compound 487b was prepared according to the procedure reported in step-6 of scheme-1 from ethyl 2-(2-((7-(3-(aminomethyl)-2-fluorophenyl)-3-(trifluoromethyl)benzofuran-5-yl)methoxy)-4-fluorophenyl)acetate (487a) (0.158 g, 0.304 mmol) in THF (2 mL), acetonitrile (1 mL), water (1 mL) using lithium hydroxide monohydrate (0.038 g, 0.912 mmol) and stirring at room temperature overnight. This gave after workup and purification by reverse phase column [C18 column, 50 g, eluting with 0.1% aqueous HCl in water and acetonitrile from 0-100%] 2-(2-((7-(3-(aminomethyl)-2-fluorophenyl)-3-(trifluoromethyl)benzofuran-5-yl)methoxy)-4-fluorophenyl)acetic acid (487b) (121 mg, 81% yield) HCl salt as a white solid; $^1$H NMR (300 MHz, DMSO-d$_6$) δ 8.88 (q, J=1.7 Hz, 1H), 7.97-7.88 (m, 1H), 7.77-7.67 (m, 2H), 7.67-7.63 (m, 1H), 7.46 (t, J=7.7 Hz, 1H), 7.25 (dd, J=8.4, 6.9 Hz, 1H), 7.03 (dd, J=11.3, 2.5 Hz, 1H), 6.75 (td, J=8.5, 2.5 Hz, 1H), 5.35 (s, 2H), 4.19 (s, 2H), 3.55 (s, 2H). $^{19}$F NMR (282 MHz, DMSO-d$_6$) δ−58.01, −112.91, −118.55. MS (ES+): 492.1 (M+1); (ES−): 490.1 (M−1); Analysis calculated for C$_{25}$H$_{18}$F$_5$NO$_4$.HCl: C, 56.88; H, 3.63; Cl, 6.72; N, 2.65; Found: C, 56.87; H, 3.48; Cl, 7.01; N, 2.78.

Scheme-488

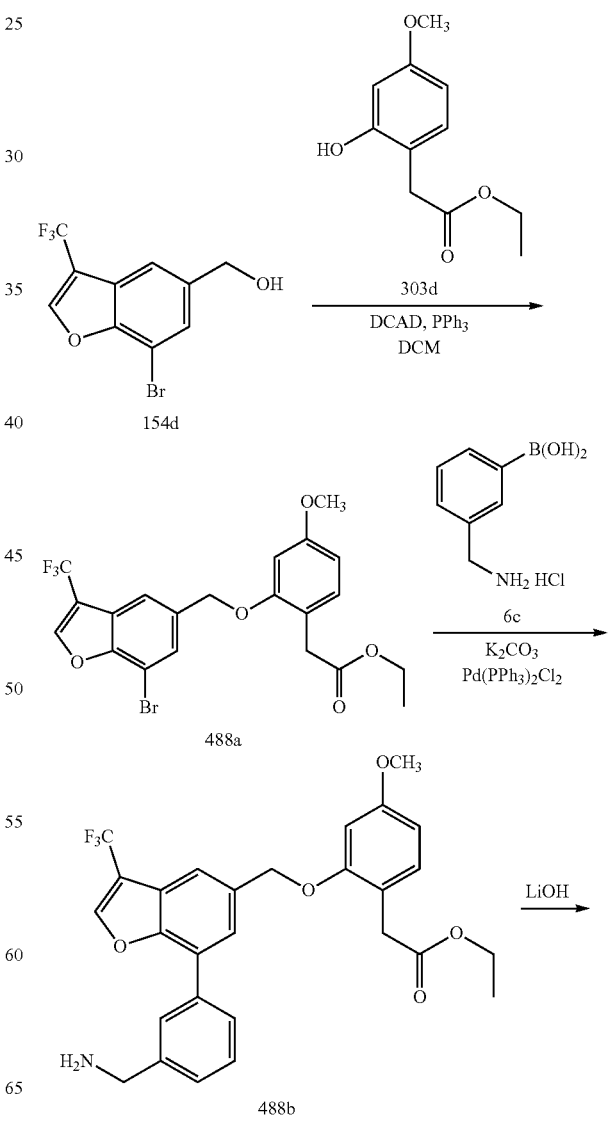

-continued

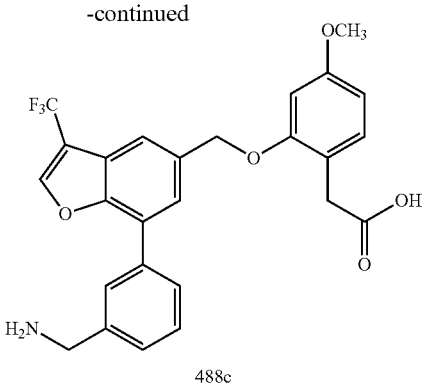

488c

Preparation of 2-(2-((7-(3-(aminomethyl)phenyl)-3-(trifluoromethyl)benzofuran-5-yl)methoxy)-4-methoxyphenyl)acetic Acid (488c)

Step-1: Preparation of Ethyl 2-(2-((7-bromo-3-(trifluoromethyl)benzofuran-5-yl)methoxy)-4-methoxyphenyl)acetate (488a)

Compound 488a was prepared according to the procedure reported in step-2 of scheme-23 from (7-bromo-3-(trifluoromethyl)benzofuran-5-yl)methanol (154d) (2 g, 6.78 mmol) in DCM (70 mL) using triphenylphosphine (1.956 g, 7.46 mmol), ethyl 2-(2-hydroxy-4-methoxyphenyl)acetate (303d) (1.710 g, 8.13 mmol) and a solution of (E)-bis(4-chlorobenzyl) diazene-1,2-dicarboxylate (DCAD, 2.74 g, 7.46 mmol) in DCM (70 mL) and stirring at room temperature for 1 h. This gave after workup and purification by flash column chromatography (silica gel, 120 g, eluting with 0 to 20% ethyl acetate in hexanes) ethyl 2-(2-((7-bromo-3-(trifluoromethyl)benzofuran-5-yl)methoxy)-4-methoxyphenyl)acetate (488a) (1.738 g, 53% yield) as a white solid; $^1$H NMR (300 MHz, DMSO-$d_6$) δ 8.96 (q, J=1.6 Hz, 1H), 7.85-7.72 (m, 2H), 7.12 (d, J=8.3 Hz, 1H), 6.67 (d, J=2.4 Hz, 1H), 6.50 (dd, J=8.3, 2.4 Hz, 1H), 5.24 (s, 2H), 4.01 (q, J=7.1 Hz, 2H), 3.74 (s, 3H), 3.54 (s, 2H), 1.07 (t, J=7.1 Hz, 3H); $^{19}$F NMR (282 MHz, DMSO-$d_6$) δ −58.25.

Step-2: Preparation of Ethyl 2-(2-((7-(3-(aminomethyl)phenyl)-3-(trifluoromethyl)benzofuran-5-yl)methoxy)-4-methoxyphenyl)acetate (488b)

Compound 488b was prepared according to the procedure reported in step-3 of scheme-1 from ethyl 2-(2-((7-bromo-3-(trifluoromethyl)benzofuran-5-yl)methoxy)-4-methoxyphenyl)acetate (488a) (225 mg, 0.462 mmol) in dioxane (8 mL) using (3-(aminomethyl)phenyl)boronic acid hydrochloride (6c) (104 mg, 0.554 mmol), Pd(PPh$_3$)$_2$Cl$_2$ (49 mg, 0.069 mmol) and a solution of K$_2$CO$_3$ (191 mg, 1.385 mmol) in water (0.8 mL) under an argon atmosphere heating at 100° C. for 4 h on oil bath. This gave after workup, purification by flash column chromatography [silica gel (24 g), eluting with DMA80 in DCM from 0-50%] ethyl 2-(2-((7-(3-(aminomethyl)phenyl)-3-(trifluoromethyl)benzofuran-5-yl)methoxy)-4-methoxyphenyl)acetate (488b) (135 mg, 57% yield) as a clear oil; $^1$H NMR (300 MHz, DMSO-$d_6$) δ 8.89 (q, J=1.7 Hz, 1H), 7.87-7.63 (m, 4H), 7.54-7.38 (m, 2H), 7.12 (d, J=8.3 Hz, 1H), 6.71 (d, J=2.4 Hz, 1H), 6.49 (dd, J=8.3, 2.4 Hz, 1H), 5.30 (s, 2H), 3.91 (q, J=7.1 Hz, 2H), 3.83 (s, 2H), 3.75 (s, 3H), 3.55 (s, 2H), 0.97 (t, J=7.1 Hz, 3H); $^{19}$F NMR (282 MHz, DMSO-$d_6$) δ −58.08; MS (ES+): 514.1 (M+1).

Step-3: Preparation of 2-(2-((7-(3-(aminomethyl)phenyl)-3-(trifluoromethyl)benzofuran-5-yl)methoxy)-4-methoxyphenyl)acetic Acid (488c)

Compound 488c was prepared according to the procedure reported in step-6 of scheme-1 from ethyl 2-(2-((7-(3-(aminomethyl)phenyl)-3-(trifluoromethyl)benzofuran-5-yl)methoxy)-4-methoxyphenyl)acetate (488b) (0.132g, 0.257 mmol) in THF (1.54 mL), acetonitrile (0.77 mL) using lithium hydroxide monohydrate 1 N aqueous (0.771 mL, 0.771 mmol) and stirring at room temperature overnight. This gave after workup and purification by reverse phase column [C18 column, 50 g, eluting with 0.1% aqueous HCl in water and acetonitrile from 0-100%] 2-(2-((7-(3-(aminomethyl)phenyl)-3-(trifluoromethyl)benzofuran-5-yl)methoxy)-4-methoxyphenyl)acetic acid (488c) (117 mg, 94% yield) HCl salt as a white solid; $^1$H NMR (300 MHz, DMSO-$d_6$) δ 12.10 (s, 1H, D$_2$O exchangeable), 8.91 (q, J=1.6 Hz, 1H), 8.37 (s, 3H, D$_2$O exchangeable), 7.98 (d, J=1.8 Hz, 1H), 7.91 (dt, J=7.2, 1.8 Hz, 1H), 7.85 (s, 1H), 7.80 (d, J=1.6 Hz, 1H), 7.68-7.54 (m, 2H), 7.12 (d, J=8.3 Hz, 1H), 6.69 (d, J=2.4 Hz, 1H), 6.49 (dd, J=8.3, 2.4 Hz, 1H), 5.32 (s, 2H), 4.15 (s, 2H), 3.74 (s, 3H), 3.51 (s, 2H). $^{19}$F NMR (282 MHz, DMSO-$d_6$) δ −58.10. MS (ES+): 486.1 (M+1); (ES−): 484.1 (M−1); Analysis calculated for C$_{26}$H$_{22}$F$_3$NO$_5$.HCl.H$_2$O: C, 57.84; H, 4.67; Cl, 6.57; N, 2.59; Found: C, 58.06; H, 4.41; Cl, 6.59; N, 2.73.

Scheme-489

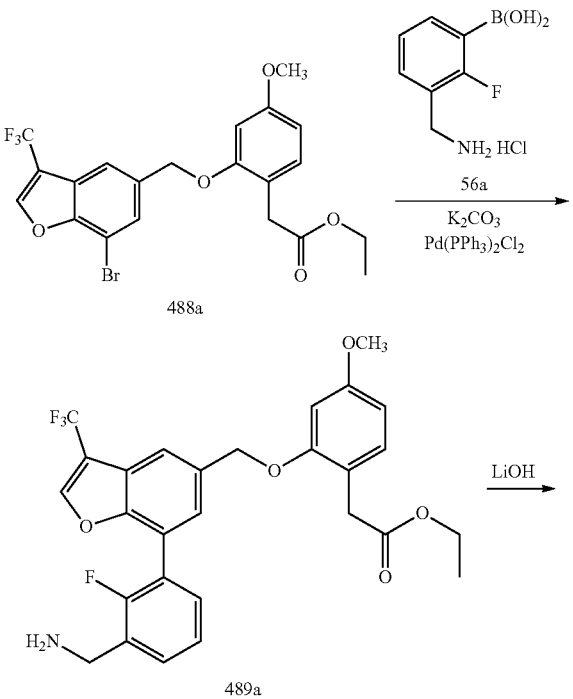

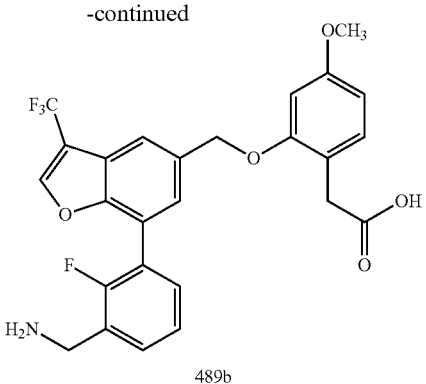

489b

Preparation of 2-(2-((7-(3-(aminomethyl)-2-fluorophenyl)-3-(trifluoromethyl)benzofuran-5-yl)methoxy)-4-methoxyphenyl)acetic Acid (489b)

Step-1: Preparation of Ethyl 2-(2-((7-(3-(aminomethyl)-2-fluorophenyl)-3-(trifluoromethyl)benzofuran-5-yl)methoxy)-4-methoxyphenyl)acetate (489a)

Compound 489a was prepared according to the procedure reported in step-3 of scheme-1 from ethyl 2-(2-((7-bromo-3-(trifluoromethyl)benzofuran-5-yl)methoxy)-4-methoxyphenyl)acetate (488a) (225 mg, 0.462 mmol) in dioxane (8 mL) using (3-(aminomethyl)-2-fluorophenyl)boronic acid hydrochloride (56a) (114 mg, 0.556 mmol), Pd(PPh$_3$)$_2$Cl$_2$ (49 mg, 0.069 mmol) and a solution of K$_2$CO$_3$ (191 mg, 1.385 mmol) in water (0.5 mL) under an argon atmosphere heating at 100° C. for 4 h on oil bath. This gave after workup, purification by flash column chromatography [silica gel (24 g), eluting with DMA80 in DCM from 0-50%] ethyl 2-(2-((7-(3-(aminomethyl)-2-fluorophenyl)-3-(trifluoromethyl)benzofuran-5-yl)methoxy)-4-methoxyphenyl)acetate (489a) (140 mg, 57% yield) as a clear oil; $^1$H NMR (300 MHz, DMSO-d$_6$) δ 8.85 (t, J=1.8 Hz, 1H), 7.84 (s, 1H), 7.62 (d, J=11.9 Hz, 2H), 7.54-7.43 (m, 1H), 7.34 (t, J=7.6 Hz, 1H), 7.11 (d, J=8.3 Hz, 1H), 6.71 (d, J=2.4 Hz, 1H), 6.49 (dd, J=8.3, 2.4 Hz, 1H), 5.29 (s, 2H), 3.96-3.82 (m, 4H), 3.75 (s, 3H), 3.53 (s, 2H), 0.96 (t, J=7.1 Hz, 3H); $^{19}$F NMR (282 MHz, DMSO d$_6$) δ −58.10, −121.91; MS (ES+): 532.2 (M+1).

Step-2: Preparation of 2-(2-((7-(3-(aminomethyl)-2-fluorophenyl)-3-(trifluoromethyl)benzofuran-5-yl)methoxy)-4-methoxyphenyl)acetic Acid (489b)

Compound 489b was prepared according to the procedure reported in step-6 of scheme-1 from ethyl 2-(2-((7-(3-(aminomethyl)-2-fluorophenyl)-3-(trifluoromethyl)benzofuran-5-yl)methoxy)-4-methoxyphenyl)acetate (489a) (0.137g, 0.258 mmol) in THF (1.55 mL), acetonitrile (0.773 mL) using lithium hydroxide monohydrate 1 N aqueous (0.773 mL, 0.773 mmol) and stirring at room temperature overnight. This gave after workup and purification by reverse phase column [C18 column, 50 g, eluting with 0.1% aqueous HCl in water and acetonitrile from 0-100%] 2-(2-((7-(3-(aminomethyl)-2-fluorophenyl)-3-(trifluoromethyl)benzofuran-5-yl)methoxy)-4-methoxyphenyl)acetic acid (489b) (115 mg, 89% yield) HCl salt as a white solid; $^1$H NMR (300 MHz, DMSO-d$_6$) δ 8.87 (q, J=1.7 Hz, 1H), 7.92 (s, 1H), 7.76-7.66 (m, 2H), 7.66 (s, 1H), 7.46 (t, J=7.7 Hz, 1H), 7.11 (d, J=8.3 Hz, 1H), 6.69 (d, J=2.4 Hz, 1H), 6.50 (dd, J=8.3, 2.4 Hz, 1H), 5.32 (s, 2H), 4.19 (s, 2H), 3.74 (s, 3H), 3.49 (s, 2H). $^{19}$F NMR (282 MHz, DMSO d$_6$) δ −58.02, −118.53. MS (ES+): 504.1 (M+1); (ES−): 502.1 (M−1); Analysis calculated for C$_{26}$H$_{21}$F$_4$NO$_5$.HCl: C, 57.84; H, 4.11; Cl, 6.57; N, 2.59; Found: C, 57.47; H, 4.02; Cl, 6.53; N, 2.61.

Scheme-490

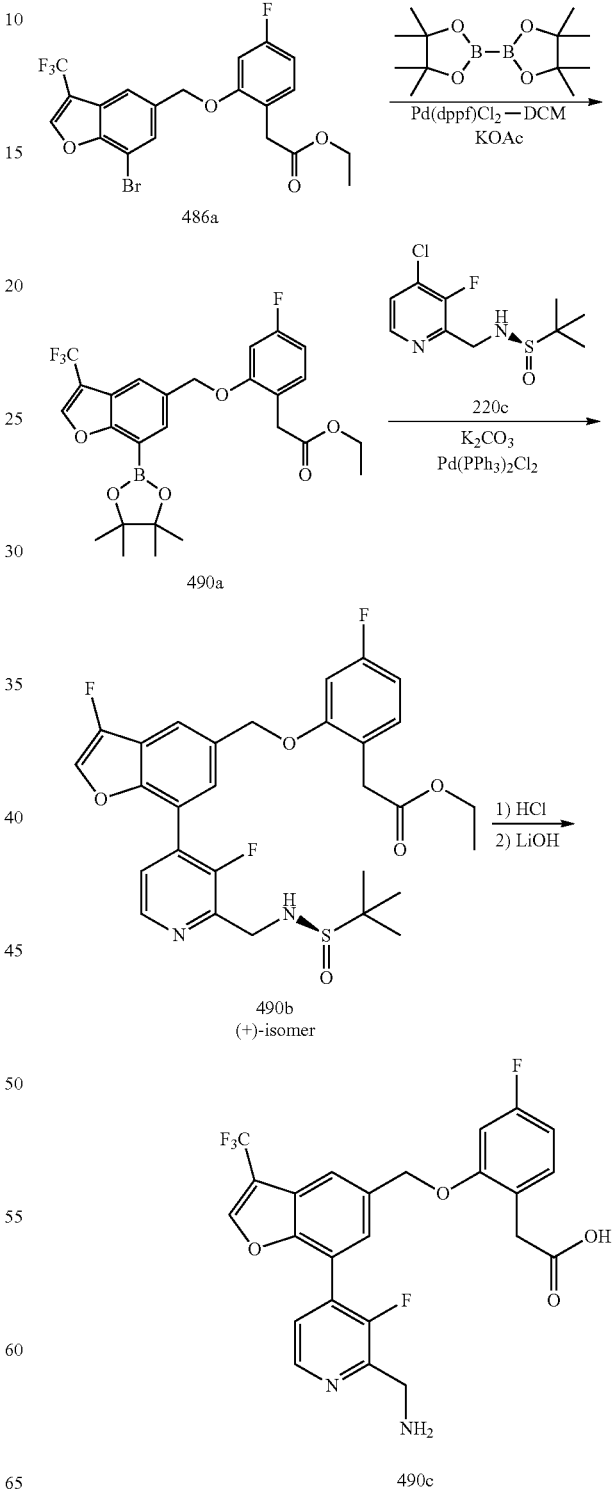

Preparation of 2-(2-((7-(2-(aminomethyl)-3-fluoropyridin-4-yl)-3-(trifluoromethyl)benzofuran-5-yl)methoxy)-4-fluorophenyl)acetic Acid (490c)

Step-1: Preparation of Ethyl 2-(4-fluoro-2-((7-(4,4,5,5-tetramethyl-1,3,2-dioxaborolan-2-yl)-3-(trifluoromethyl)benzofuran-5-yl)methoxy)phenyl)acetate (490a)

Compound 490a was prepared according to the procedure reported in step-1 of scheme-59 from ethyl 2-(2-((7-bromo-3-(trifluoromethyl)benzofuran-5-yl)methoxy)-4-fluorophenyl)acetate (486a) (1.5 g, 3.16 mmol), using bis(pinacolato)diboron (1.202 g, 4.73 mmol), potassium acetate (0.929 g, 9.47 mmol) and Pd(dppf)Cl$_2$-DCM (0.258 g, 0.316 mmol) in anhydrous dioxane (50 mL) under an argon atmosphere and heating at 90° C. overnight. This gave after workup and purification by flash column chromatography [silica (40g), eluting with EtOAc in hexane from 0-40%] ethyl 2-(4-fluoro-2-((7-(4,4,5,5-tetramethyl-1,3,2-dioxaborolan-2-yl)-3-(trifluoromethyl)benzofuran-5-yl)methoxy)phenyl)acetate (490a) (1.46 g, 89% yield) as a clear oil; $^1$H NMR (300 MHz, DMSO-d$_6$) δ 8.86 (q, J=1.6 Hz, 1H), 7.93 (dd, J=1.9, 1.0 Hz, 1H), 7.82 (d, J=1.8 Hz, 1H), 7.25 (dd, J=8.3, 6.9 Hz, 1H), 7.05 (dd, J=11.3, 2.5 Hz, 1H), 6.75 (td, J=8.5, 2.5 Hz, 1H), 5.26 (s, 2H), 3.99 (q, J=7.0 Hz, 2H), 3.57 (s, 2H), 1.35 (s, 12H), 1.03 (t, J=7.1 Hz, 3H); $^{19}$F NMR (282 MHz, DMSO-d$_6$) δ−57.99, −112.64.

Step-2: Preparation of (+)-(S)-ethyl 2-(2-((7-(2-((1,1-dimethylethylsulfinamido)methyl)-3-fluoropyridin-4-yl)-3-(trifluoromethyl)benzofuran-5-yl)methoxy)-4-fluorophenyl)acetate (490b)

Compound 490b was prepared according to the procedure reported in step-3 of scheme-1 from ethyl 2-(4-fluoro-2-((7-(4,4,5,5-tetramethyl-1,3,2-dioxaborolan-2-yl)-3-(trifluoromethyl)benzofuran-5-yl)methoxy)phenyl)acetate (490a) (280 mg, 0.536 mmol) in dioxane (10 mL) using (+)-(S)—N-((4-chloro-3-fluoropyridin-2-yl)methyl)-2-methylpropane-2-sulfinamide (220c) (142 mg, 0.536 mmol), Pd(PPh$_3$)$_2$Cl$_2$ (56 mg, 0.080 mmol) and a solution of K$_2$CO$_3$ (222 mg, 1.608 mmol) in water (1 mL) under a nitrogen atmosphere heating at 100° C. for 6 h on oil bath. This gave after workup and purification by flash column chromatography [silica gel (24 g), eluting with DMA80 in DCM from 0-30%] (+)-(S)-ethyl 2-(2-((7-(2-((1,1-dimethylethylsulfinamido)methyl)-3-fluoropyridin-4-yl)-3-(trifluoromethyl)benzofuran-5-yl)methoxy)-4-fluorophenyl)acetate (490b) (282 mg, 84% yield) as an brown oil; $^1$H NMR (300 MHz, DMSO-d$_6$) δ 8.92 (q, J=1.6 Hz, 1H), 8.56 (d, J=4.9 Hz, 1H), 7.94 (s, 1H), 7.74-7.68 (m, 2H), 7.25 (dd, J=8.4, 6.9 Hz, 1H), 7.06 (dd, J=11.3, 2.5 Hz, 1H), 6.76 (td, J=8.5, 2.5 Hz, 1H), 5.92-5.79 (m, 1H), 5.34 (s, 2H), 4.42 (dd, J=5.8, 2.0 Hz, 2H), 3.90 (q, J=7.1 Hz, 2H), 3.60 (s, 2H), 1.11 (s, 9H), 0.96 (t, J=7.1 Hz, 3H). MS (ES+): 625.1 (M+1);). $^{19}$F NMR (282 MHz, DMSO-d$_6$) δ−58.07, −112.54, −128.19; Optical rotation [t]D=+24 (c=0.1, MeOH).

Step-3: Preparation of 2-(2-((7-(2-(aminomethyl)-3-fluoropyridin-4-yl)-3-(trifluoromethyl)benzofuran-5-yl)methoxy)-4-fluorophenyl)acetic Acid (490c)

To a stirred solution of (+)-(S)-ethyl 2-(2-((7-(2-((1,1-dimethylethylsulfinamido)methyl)-3-fluoropyridin-4-yl)-3-(trifluoromethyl)benzofuran-5-yl)methoxy)-4-fluorophenyl)acetate (490b) (280 mg, 0.448 mmol) in THF (7.5 mL) was added hydrochloric acid (4.M in 1-4-dioxane, 0.224 mL, 0.897 mmol), stirred at room temperature for 30 minutes and concentrated in vacuum to dryness. The residue obtained was dissolved in THF (5 mL), acetonitrile (2.5 mL) and water (2.5 mL) and added lithium hydroxide monohydrate (105 mg, 2.501 mmol). The reaction mixture was stirred for 21 h at room temperature and concentrated to remove THF and acetonitrile. The reaction was diluted with water (2 mL) and acidified to pH 4 using 1M HCl. The solid separated out was decanted and purified by reverse-phase column chromatography [C-18 column, 50 g, eluting with 0.1% aqueous HCl in water and acetonitrile from 0-100%] to afford 2-(2-((7-(2-(aminomethyl)-3-fluoropyridin-4-yl)-3-(trifluoromethyl)benzofuran-5-yl)methoxy)-4-fluorophenyl)acetic acid (490c) (51 mg, 23% yield) HCl salt as a white solid; $^1$H NMR (300 MHz, DMSO-d$_6$) δ 12.18 (s, 1H, D$_2$O exchangeable), 8.95 (q, J=1.6 Hz, 1H), 8.67 (d, J=5.0 Hz, 1H), 8.52 (s, 3H, D$_2$O exchangeable), 8.12-7.95 (m, 1H), 7.83 (t, J=5.3 Hz, 1H), 7.78 (s, 1H), 7.25 (dd, J=8.4, 6.9 Hz, 1H), 7.04 (dd, J=11.3, 2.5 Hz, 1H), 6.76 (td, J=8.5, 2.5 Hz, 1H), 5.37 (s, 2H), 4.39 (s, 2H), 3.56 (s, 2H). $^{19}$F NMR (282 MHz, DMSO-d$_6$) δ−58.02, −112.91, −128.49. MS (ES+): 493.1 (M+1); (ES−): 491.1 (M−1); Analysis calculated for C$_{24}$H$_{17}$F$_5$N$_2$O$_4$.HCl.0.5H$_2$O: C, 53.59; H, 3.56; Cl, 6.59; N, 5.21; Found: C, 53.53; H, 3.43; Cl, 6.62; N, 5.30.

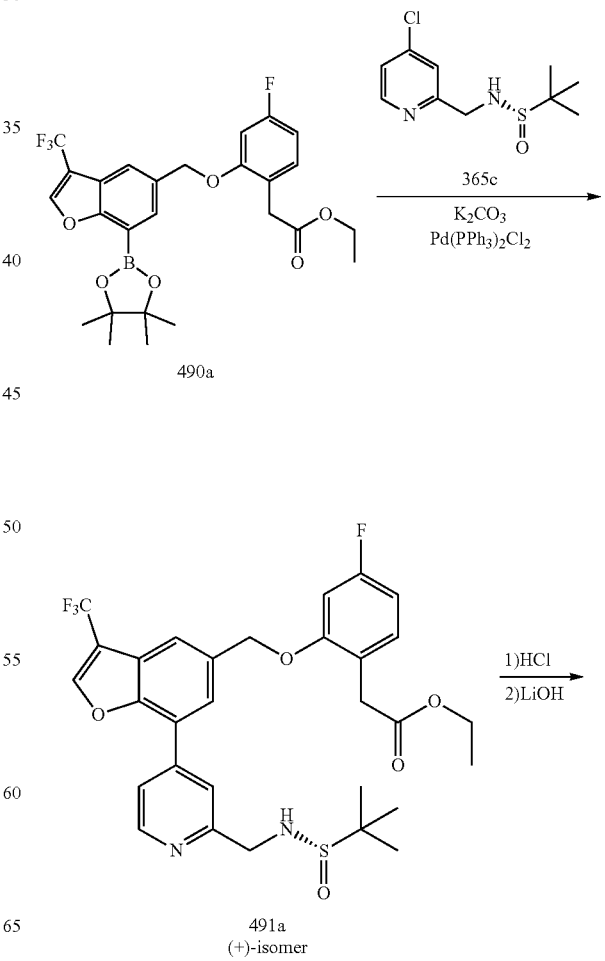

Scheme-491

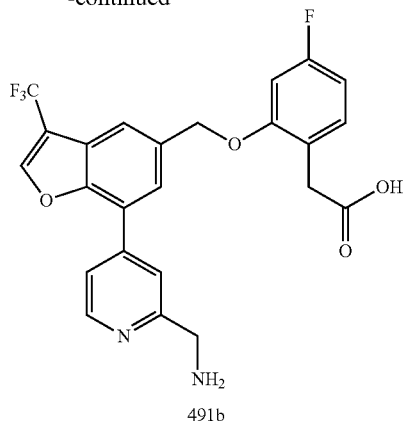

Preparation of 2-(2-((7-(2-(aminomethyl)pyridin-4-yl)-3-(trifluoromethyl)benzofuran-5-yl)methoxy)-4-fluorophenyl)acetic Acid (491b)

Step-1: Preparation of (+)-(S)-ethyl 2-(2-((7-(2-((1,1-dimethylethylsulfinamido)methyl)pyridin-4-yl)-3-(trifluoromethyl)benzofuran-5-yl)methoxy)-4-fluorophenyl)acetate (491a)

Compound 491a was prepared according to the procedure reported in step-3 of scheme-1 from ethyl 2-(4-fluoro-2-((7-(4,4,5,5-tetramethyl-1,3,2-dioxaborolan-2-yl)-3-(trifluoromethyl)benzofuran-5-yl)methoxy)phenyl)acetate (490a) (280 mg, 0.536 mmol) in dioxane (10 mL) using (+)-(S)—N-((4-chloropyridin-2-yl)methyl)-2-methylpropane-2-sulfinamide (365c) (132 mg, 0.536 mmol), Pd(PPh$_3$)$_2$Cl$_2$ (56 mg, 0.080 mmol) and a solution of K$_2$CO$_3$ (222 mg, 1.608 mmol) in water (1 mL) under a nitrogen atmosphere heating at 100° C. for 6 h on oil bath. This gave after workup and purification by flash column chromatography [silica gel (24 g), eluting with DMA80 in DCM from 0-30%] (+)-(S)-ethyl 2-(2-((7-(2-((1,1-dimethylethylsulfinamido)methyl)pyridin-4-yl)-3-(trifluoromethyl)benzofuran-5-yl)methoxy)-4-fluorophenyl)acetate (491a) (235 mg, 72% yield) as an brown oil; $^1$H NMR (300 MHz, DMSO-d$_6$) δ 8.94 (q, J=1.6 Hz, 1H), 8.68 (dd, J=5.2, 0.8 Hz, 1H), 8.01 (s, 1H), 7.93-7.84 (m, 2H), 7.78 (dd, J=5.2, 1.7 Hz, 1H), 7.26 (dd, J=8.3, 6.9 Hz, 1H), 7.06 (dd, J=11.3, 2.5 Hz, 1H), 6.76 (td, J=8.5, 2.5 Hz, 1H), 5.96 (t, J=6.0 Hz, 1H), 5.34 (s, 2H), 4.38 (dd, J=6.1, 4.1 Hz, 2H), 3.92-3.86 (m, 2H), 3.61 (s, 2H), 1.17 (s, 9H), 0.95 (t, J=7.1 Hz, 3H); MS (ES+): 607.2 (M+1); Optical rotation [t]D=+10 (c=0.15, MeOH).

Step-2: Preparation of 2-(2-((7-(2-(aminomethyl)pyridin-4-yl)-3-(trifluoromethyl)benzofuran-5-yl)methoxy)-4-fluorophenyl)acetic Acid (491b)

To a stirred solution of (+)-(S)-ethyl 2-(2-((7-(2-((1,1-dimethylethylsulfinamido)methyl)pyridin-4-yl)-3-(trifluoromethyl)benzofuran-5-yl)methoxy)-4-fluorophenyl)acetate (491a) (231 mg, 0.381 mmol) in THF (6 mL) was added hydrochloric acid (4.M in 1-4-dioxane, 0.190 mL, 0.762 mmol), stirred at room temperature for 30 minutes and concentrated in vacuum to dryness. The residue obtained was dissolved in THF (4 mL), acetonitrile (2 mL) and water (2 mL) and added lithium hydroxide monohydrate (84 mg, 1.999 mmol). The reaction mixture was stirred for 21 h at room temperature and concentrated to remove THF and acetonitrile. The reaction was diluted with water (2 mL) and acidified to pH 4 using 1M HCl. The solid separated out was decanted and purified by reverse-phase column chromatography [C-18 column, 50 g, eluting with 0.1% aqueous HCl in water and acetonitrile from 0-100%] to afford 2-(2-((7-(2-(aminomethyl)pyridin-4-yl)-3-(trifluoromethyl)benzofuran-5-yl)methoxy)-4-fluorophenyl)acetic acid (491b) (93 mg, 52% yield) HCl salt as a white solid; $^1$H NMR (300 MHz, DMSO-d$_6$) δ 8.98 (q, J=1.6 Hz, 1H), 8.81 (dd, J=5.3, 0.8 Hz, 1H), 8.48 (s, 3H), 8.04 (dd, J=1.7, 0.8 Hz, 1H), 7.99-7.90 (m, 3H), 7.26 (dd, J=8.4, 6.9 Hz, 1H), 7.03 (dd, J=11.3, 2.5 Hz, 1H), 6.76 (td, J=8.5, 2.5 Hz, 1H), 5.37 (s, 2H), 4.32 (d, J=5.7 Hz, 2H), 3.59 (s, 2H); $^{19}$F NMR (282 MHz, DMSO-d$_6$) δ−57.80, −112.92. MS (ES+): 475.1 (M+1); (ES−): 473.1 (M−1); Analysis calculated for C$_{24}$H$_{18}$F$_4$N$_2$O$_4$·1.25HCl1.5H$_2$O: C, 52.70; H, 4.10; Cl, 8.10; N, 5.12; Found: C, 52.50; H, 3.92; Cl, 8.50; N, 5.06.

Scheme-492

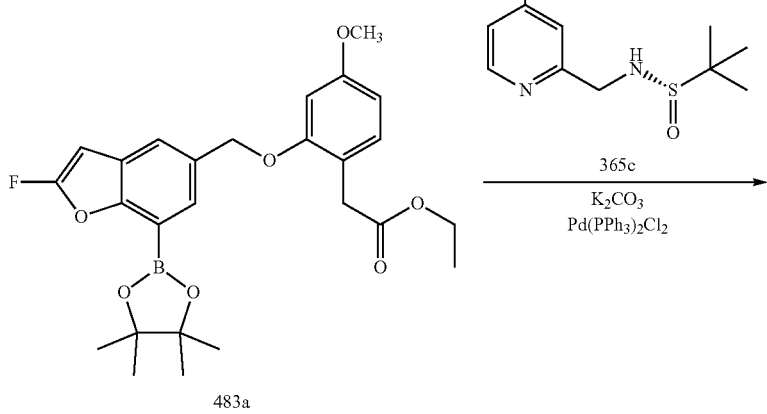

1469

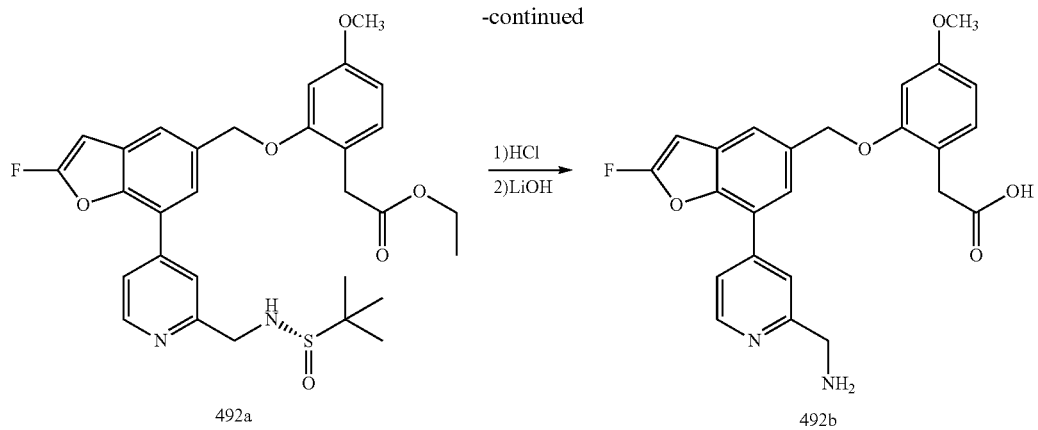

492a

1470

-continued

492b

Preparation of 2-(2-((7-(2-(aminomethyl)pyridin-4-yl)-2-fluorobenzofuran-5-yl)methoxy)-4-methoxyphenyl)acetic Acid (492b)

Step-1: Preparation of (S)-ethyl 2-(2-((7-(2-(((1,1-dimethylethylsulfinamido)methyl)pyridin-4-yl)-2-fluorobenzofuran-5-yl)methoxy)-4-methoxyphenyl)acetate (492a)

Compound 492a was prepared according to the procedure reported in step-3 of scheme-1 from ethyl 2-(2-((2-fluoro-7-(4,4,5,5-tetramethyl-1,3,2-dioxaborolan-2-yl)benzofuran-5-yl)methoxy)-4-methoxyphenyl)acetate (483a) (260 mg, 0.537 mmol) in dioxane (10 mL) using (+)-(S)—N-((4-chloropyridin-2-yl)methyl)-2-methylpropane-2-sulfinamide (365c) (132 mg, 0.537 mmol), Pd(PPh$_3$)$_2$Cl$_2$ (57 mg, 0.081 mmol) and a solution of K$_2$CO$_3$ (223 mg, 1.611 mmol) in water (1 mL) under an argon atmosphere heating at 100° C. for 15 h on oil bath. This gave after workup and purification by flash column chromatography [silica gel (24 g), eluting with DMA80 in DCM from 0-30%](S)-ethyl 2-(2-((7-(2-(((1,1-dimethylethylsulfinamido)methyl)pyridin-4-yl)-2-fluorobenzofuran-5-yl)methoxy)-4-methoxyphenyl)acetate (492a) (168 mg, 55% yield) as an brown oil; $^1$H NMR (300 MHz, DMSO-d$_6$) δ 8.76 (dd, J=22.9, 5.3 Hz, 1H), 8.36 (s, 1H), 8.03 (d, J=31.6 Hz, 1H), 7.93-7.81 (m, 1H), 7.78-7.69 (m, 2H), 7.12 (dd, J=8.3, 1.9 Hz, 1H), 6.68 (t, J=2.0 Hz, 1H), 6.56-6.43 (m, 2H), 5.24 (s, 2H), 4.37 (dd, J=29.3, 4.9 Hz, 2H), 3.93 (qd, J=7.1, 3.9 Hz, 2H), 3.74 (s, 3H), 3.55 (d, J=1.7 Hz, 2H), 1.18 (s, 9H), 1.02-0.93 (m, 3H); MS (ES+): 569.2 (M+1).

Step-2: Preparation of 2-(2-((7-(2-(aminomethyl)pyridin-4-yl)-2-fluorobenzofuran-5-yl)methoxy)-4-methoxyphenyl)acetic Acid (492b)

To a stirred solution of (S)-ethyl 2-(2-((7-(2-(((1,1-dimethylethylsulfinamido)methyl)pyridin-4-yl)-2-fluorobenzofuran-5-yl)methoxy)-4-methoxyphenyl)acetate (492a) (168 mg, 0.295 mmol) in THF (5 mL) was added hydrochloric acid (4.M in 1-4-dioxane, 0.148 mL, 0.591 mmol), stirred at room temperature for 30 minutes and concentrated in vacuum to dryness. The residue obtained was dissolved in THF (5 mL), acetonitrile (1 mL) and water (1 mL) and added lithium hydroxide monohydrate (62 mg, 1.477 mmol). The reaction mixture was stirred for 48 h at room temperature and concentrated to remove THF and acetonitrile. The reaction was diluted with water (2 mL) and acidified to pH 4 using 1M HCl. The solid separated out was decanted and purified by reverse-phase column chromatography [C-18 column, 50 g, eluting with 0.1% aqueous HCl in water and acetonitrile from 0-100%] to afford 2-(2-((7-(2-(aminomethyl)pyridin-4-yl)-2-fluorobenzofuran-5-yl)methoxy)-4-methoxyphenyl)acetic acid (492b) (77 mg, 60% yield) HCl salt as a pale yellow solid; $^1$H NMR (300 MHz, DMSO-d$_6$) δ 8.79 (dd, J=5.2, 0.8 Hz, 1H), 8.39 (s, 3H, D$_2$O exchangeable), 7.98 (s, 1H), 7.90 (dd, J=5.2, 1.7 Hz, 1H), 7.79-7.74 (m, 2H), 7.12 (d, J=8.3 Hz, 1H), 6.66 (d, J=2.4 Hz, 1H), 6.53-6.45 (m, 2H), 5.26 (s, 2H), 4.32 (d, J=5.7 Hz, 2H), 3.73 (s, 3H), 3.51 (s, 2H). $^{19}$F NMR (282 MHz, DMSO) δ–111.16. MS (ES+): 437.1 (M+1); (ES−): 435.1 (M−1); Analysis calculated for C$_{24}$H$_{21}$FN$_2$O$_5$·1.75HCl·2H$_2$O: C, 53.75; H, 5.03; Cl, 11.57; N, 5.22; Found, 53.83; H, 4.80; Cl, 11.84; N, 5.19.

Scheme-493

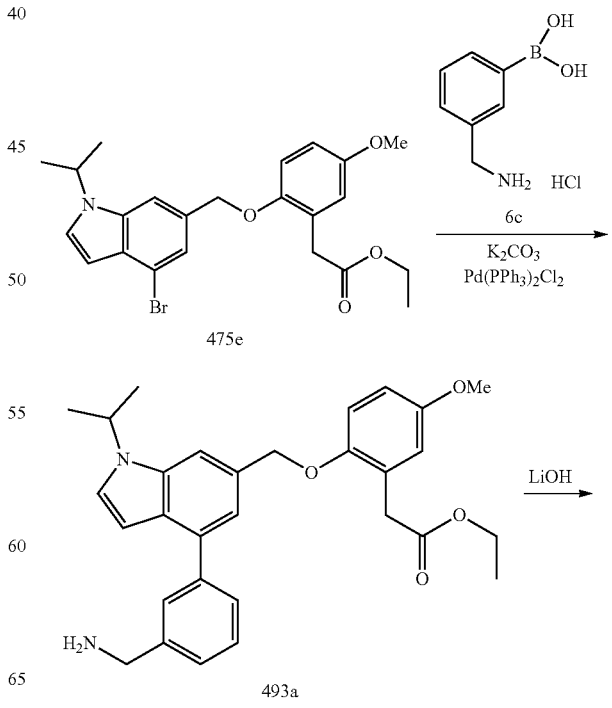

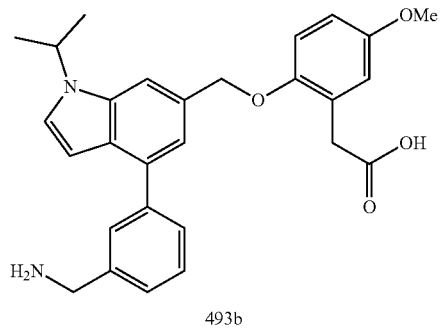

Preparation of 2-(2-((4-(3-(aminomethyl)phenyl)-1-isopropyl-1H-indol-6-yl)methoxy)-5-methoxyphenyl)acetic Acid (493b)

Step-1: Preparation of Ethyl 2-(2-((4-(3-(aminomethyl)phenyl)-1-isopropyl-1H-indol-6-yl)methoxy)-5-methoxyphenyl)acetate (493a)

Compound 493a was prepared according to the procedure reported in step-3 of scheme-1 from ethyl 2-(2-((4-bromo-1-isopropyl-1H-indol-6-yl)methoxy)-5-methoxyphenyl)acetate (475e) (100 mg, 0.217 mmol) in dioxane (4 mL), water (1 mL) using (3-(aminomethyl)phenyl)boronic acid hydrochloride (6c) (61 mg, 0.326 mmol), bis(triphenylphosphine)palladium(II) chloride (Pd(PPh$_3$)$_2$Cl$_2$) (15 mg, 0.022 mmol) and 3.3 M aqueous K$_2$CO$_3$ (0.197 mL, 0.652 mmol) under a nitrogen atmosphere heating at 100° C. for 16 h on oil bath. This gave after workup, purification by flash column chromatography (silica gel, 12 g, eluting with 0-6% MeOH in DCM) ethyl 2-(2-((4-(3-(aminomethyl)phenyl)-1-isopropyl-H-indol-6-yl)methoxy)-5-methoxyphenyl)acetate (493a) (83 mg, 79% yield) as a colorless oil; MS (ES+): 487 (M+1).

Step-2: Preparation of 2-(2-((4-(3-(aminomethyl)phenyl)-1-isopropyl-1H-indol-6-yl)methoxy)-5-methoxyphenyl)acetic Acid (493b)

Compound 493b was prepared according to the procedure reported in step-6 of scheme-1 from ethyl 2-(2-((4-(3-(aminomethyl)phenyl)-1-isopropyl-1H-indol-6-yl)methoxy)-5-methoxyphenyl)acetate (493a) (83 mg, 0.171 mmol) in MeOH (3 mL) using 2.0 M aqueous LiOH (0.426 mL, 0.853 mmol) and stirring at room temperature for 16 h. This gave after workup and purification by reverse phase column [C18 (100 g), eluting with 0-60% MeCN in H$_2$O] 2-(2-((4-(3-(aminomethyl)phenyl)-1-isopropyl-1H-indol-6-yl)methoxy)-5-methoxyphenyl)acetic acid (493b) (60 mg, 77% yield) free base as a white solid; $^1$H NMR (300 MHz, DMSO-d$_6$) δ 8.13 (s, 1H), 7.75 (d, J=7.8 Hz, 1H), 7.58 (s, 1H), 7.56 (d, J=3.3 Hz, 1H), 7.46 (d, J=1.4 Hz, 1H), 7.42 (d, J=7.6 Hz, 1H), 7.30 (d, J=7.6 Hz, 1H), 6.88 (d, J=8.9 Hz, 1H), 6.70 (d, J=3.1 Hz, 1H), 6.66-6.57 (m, 2H), 5.20 (s, 2H), 4.81 (p, J=6.6 Hz, 1H), 3.98 (s, 2H), 3.66 (s, 3H), 3.36 (s, 2H), 1.50 (d, J=6.6 Hz, 6H); MS (ES+): 459 (M+1), (ES−): 457 (M−1).

Scheme-494

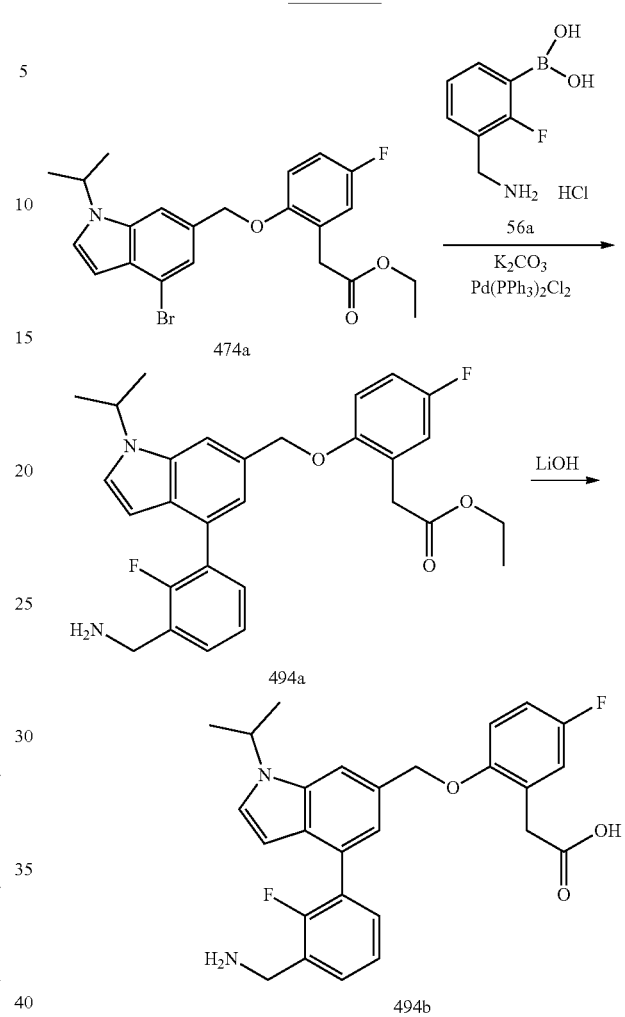

Preparation of 2-(2-((4-(3-(aminomethyl)-2-fluorophenyl)-1-isopropyl-1H-indol-6-yl)methoxy)-5-fluorophenyl)acetic Acid (494b)

Step-1: Preparation of Ethyl 2-(2-((4-(3-(aminomethyl)-2-fluorophenyl)-1-isopropyl-1H-indol-6-yl)methoxy)-5-fluorophenyl)acetate (494a)

Compound 494a was prepared according to the procedure reported in step-3 of scheme-1 from ethyl 2-(2-((4-bromo-1-isopropyl-1H-indol-6-yl)methoxy)-5-fluorophenyl)acetate (474a) (110 mg, 0.245 mmol) in dioxane (4 mL)/water (1 mL) using (3-(aminomethyl)-2-fluorophenyl)boronic acid hydrochloride (56a) (76 mg, 0.368 mmol), bis(triphenylphosphine)palladium(II) chloride (Pd(PPh$_3$)$_2$Cl$_2$) (17 mg, 0.025 mmol) and 3.3 M aqueous K$_2$CO$_3$ (0.223 mL, 0.736 mmol) under a nitrogen atmosphere heating at 100° C. for 16 h on oil bath. This gave after workup, purification by flash column chromatography (silica gel, 12 g, eluting with 0-3% MeOH in DCM) ethyl 2-(2-((4-(3-(aminomethyl)-2-fluorophenyl)-1-isopropyl-1H-indol-6-yl)methoxy)-5-fluorophenyl)acetate (494a) (86 mg, 71% yield) as a colorless oil; MS (ES+): 493 (M+1).

Step-2: Preparation of 2-(2-((4-(3-(aminomethyl)-2-fluorophenyl)-1-isopropyl-1H-indol-6-yl)methoxy)-5-fluorophenyl)acetic Acid (494b)

Compound 494b was prepared according to the procedure reported in step-6 of scheme-1 from ethyl 2-(2-((4-(3-(aminomethyl)-2-fluorophenyl)-1-isopropyl-1H-indol-6-yl)methoxy)-5-fluorophenyl)acetate (494a) (86 mg, 0.175 mmol) in MeOH (3 mL), using a 2 M aqueous solution of lithium hydroxide (0.436 mL, 0.873 mmol) and stirring at room temperature for 16 h. This gave after workup and purification by reverse phase column [C18 (100 g), eluting with 0-60% MeCN in H$_2$O] 2-(2-((4-(3-(aminomethyl)-2-fluorophenyl)-1-isopropyl-1H-indol-6-yl)methoxy)-5-fluorophenyl)acetic acid (494b) (63 mg, 78% yield) free base as a white solid; $^1$H NMR (300 MHz, DMSO-d$_6$) δ 7.70 (s, 1H), 7.58-7.46 (m, 2H), 7.40 (td, J=7.3, 1.9 Hz, 1H), 7.26 (t, J=7.6 Hz, 1H), 7.15 (s, 1H), 7.08-6.97 (m, 2H), 6.95-6.85 (m, 1H), 6.28 (t, J=2.6 Hz, 1H), 5.19 (s, 2H), 4.83 (p, J=6.6 Hz, 1H), 3.83 (s, 2H), 3.34 (s, 2H), 1.47 (d, J=6.6 Hz, 6H); $^{19}$F NMR (282 MHz, DMSO-d$_6$) δ −122.06, −124.61; MS (ES+): 465 (M+1), (ES−): 463 (M−1).

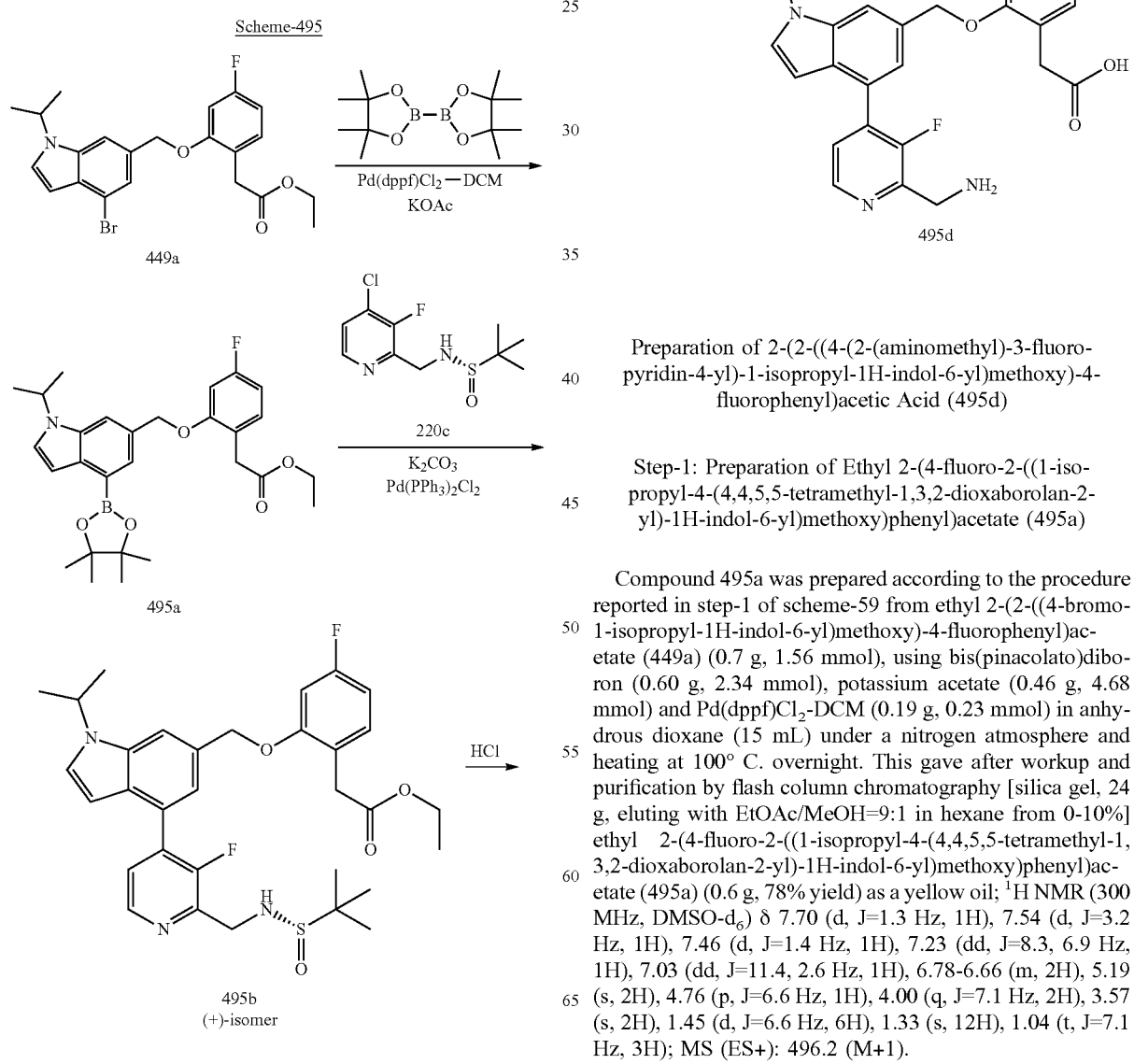

Preparation of 2-(2-((4-(2-(aminomethyl)-3-fluoropyridin-4-yl)-1-isopropyl-1H-indol-6-yl)methoxy)-4-fluorophenyl)acetic Acid (495d)

Step-1: Preparation of Ethyl 2-(4-fluoro-2-((1-isopropyl-4-(4,4,5,5-tetramethyl-1,3,2-dioxaborolan-2-yl)-1H-indol-6-yl)methoxy)phenyl)acetate (495a)

Compound 495a was prepared according to the procedure reported in step-1 of scheme-59 from ethyl 2-(2-((4-bromo-1-isopropyl-1H-indol-6-yl)methoxy)-4-fluorophenyl)acetate (449a) (0.7 g, 1.56 mmol), using bis(pinacolato)diboron (0.60 g, 2.34 mmol), potassium acetate (0.46 g, 4.68 mmol) and Pd(dppf)Cl$_2$-DCM (0.19 g, 0.23 mmol) in anhydrous dioxane (15 mL) under a nitrogen atmosphere and heating at 100° C. overnight. This gave after workup and purification by flash column chromatography [silica gel, 24 g, eluting with EtOAc/MeOH=9:1 in hexane from 0-10%] ethyl 2-(4-fluoro-2-((1-isopropyl-4-(4,4,5,5-tetramethyl-1,3,2-dioxaborolan-2-yl)-1H-indol-6-yl)methoxy)phenyl)acetate (495a) (0.6 g, 78% yield) as a yellow oil; $^1$H NMR (300 MHz, DMSO-d$_6$) δ 7.70 (d, J=1.3 Hz, 1H), 7.54 (d, J=3.2 Hz, 1H), 7.46 (d, J=1.4 Hz, 1H), 7.23 (dd, J=8.3, 6.9 Hz, 1H), 7.03 (dd, J=11.4, 2.6 Hz, 1H), 6.78-6.66 (m, 2H), 5.19 (s, 2H), 4.76 (p, J=6.6 Hz, 1H), 4.00 (q, J=7.1 Hz, 2H), 3.57 (s, 2H), 1.45 (d, J=6.6 Hz, 6H), 1.33 (s, 12H), 1.04 (t, J=7.1 Hz, 3H); MS (ES+): 496.2 (M+1).

Step-2: Preparation of (+)-(S)-ethyl 2-(2-((4-(2-((1,1-dimethylethylsulfinamido)methyl)-3-fluoropyridin-4-yl)-1-isopropyl-1H-indol-6-yl)methoxy)-4-fluorophenyl)acetate (495b)

Compound 495b was prepared according to the procedure reported in step-3 of scheme-1 from ethyl 2-(4-fluoro-2-((1-isopropyl-4-(4,4,5,5-tetramethyl-1,3,2-dioxaborolan-2-yl)-1H-indol-6-yl)methoxy)phenyl)acetate (495a) (300 mg, 0.61 mmol) in dioxane (4 mL) using (+)-(S)—N-((4-chloro-3-fluoropyridin-2-yl)methyl)-2-methylpropane-2-sulfinamide (220c) (192 mg, 0.73 mmol), Pd(PPh$_3$)$_2$Cl$_2$ (32 mg, 0.045 mmol) and a solution of K$_2$CO$_3$ (251 mg, 1.82 mmol) in water (1 mL) under a nitrogen atmosphere heating at 90° C. for 3 h on oil bath. This gave after workup and purification by flash column chromatography (silica gel, 12 g, eluting with DMA80 in DCM from 0-50%) (+)-(S)-ethyl 2-(2-((4-(2-((1,1-dimethylethylsulfinamido)methyl)-3-fluoropyridin-4-yl)-1-isopropyl-1H-indol-6-yl)methoxy)-4-fluorophenyl)acetate (495b) (300 mg, 83% yield) as a yellow oil; MS (ES+) 598.3 (M+1); Optical rotation [t]D=+22 (c=0.1, MeOH).

Step-3: Preparation of Ethyl 2-(2-((4-(2-(aminomethyl)-3-fluoropyridin-4-yl)-1-isopropyl-1H-indol-6-yl)methoxy)-4-fluorophenyl)acetate (495c)

Compound 495c was prepared according to the procedure reported in step-3 of scheme-305 from (+)-(S)-ethyl 2-(2-((4-(2-((1,1-dimethylethylsulfinamido)methyl)-3-fluoropyridin-4-yl)-1-isopropyl-1H-indol-6-yl)methoxy)-4-fluorophenyl)acetate (495b) (300 mg, 0.50 mmol) in DCM (4 mL) using 4 M HCl in dioxane (0.38 mL, 1.51 mmol) and stirring at room temperature for 1 h. This gave after workup and purification by flash column chromatography [silica (12 g), eluting with DMA80/DCM from 0-70%] ethyl 2-(2-((4-(2-(aminomethyl)-3-fluoropyridin-4-yl)-1-isopropyl-1H-indol-6-yl)methoxy)-4-fluorophenyl)acetate (495c) (200 mg, 81% yield) as a pale-yellow oil; MS (ES+): 494.2 (M+1).

Step-4: Preparation of 2-(2-((4-(2-(aminomethyl)-3-fluoropyridin-4-yl)-1-isopropyl-1H-indol-6-yl)methoxy)-4-fluorophenyl)acetic Acid (495d)

Compound 495d was prepared according to the procedure reported in step-6 of scheme-1 from ethyl 2-(2-((4-(2-(aminomethyl)-3-fluoropyridin-4-yl)-1-isopropyl-1H-indol-6-yl)methoxy)-4-fluorophenyl)acetate (495c) (200 mg, 0.41 mmol) in THF/MeOH (8 mL each) using a solution of lithium hydroxide hydrate (136 mg, 3.24 mmol) in water (2 mL) and stirring at room temperature for 16 h. This gave after workup and purification by reverse phase column [C-18, 50g, column eluting with acetonitrile in water 0-100%] 2-(2-((4-(2-(aminomethyl)-3-fluoropyridin-4-yl)-1-isopropyl-1H-indol-6-yl)methoxy)-4-fluorophenyl)acetic acid (495d) (140 mg, 74% yield) as a white solid; $^1$H NMR (300 MHz, DMSO-d$_6$) δ 8.45 (d, J=4.9 Hz, 1H), 7.76 (s, 1H), 7.62 (d, J=3.3 Hz, 1H), 7.51 (t, J=5.4 Hz, 1H), 7.26 (s, 1H), 7.21 (t, J=7.7 Hz, 1H), 7.00 (dd, J=11.6, 2.5 Hz, 1H), 6.70 (td, J=8.6, 2.5 Hz, 1H), 6.37 (t, J=2.9 Hz, 1H), 5.28 (s, 2H), 4.83 (p, J=6.7 Hz, 1H), 3.97 (s, 2H), 3.52 (s, 2H), 1.49 (d, J=6.6 Hz, 6H); $^{19}$F NMR (282 MHz, DMSO-d$_6$) δ −113.44, −130.73; MS (ES+): 466.20 (M+1); (ES−): 464.20 (M−1).

Scheme-496

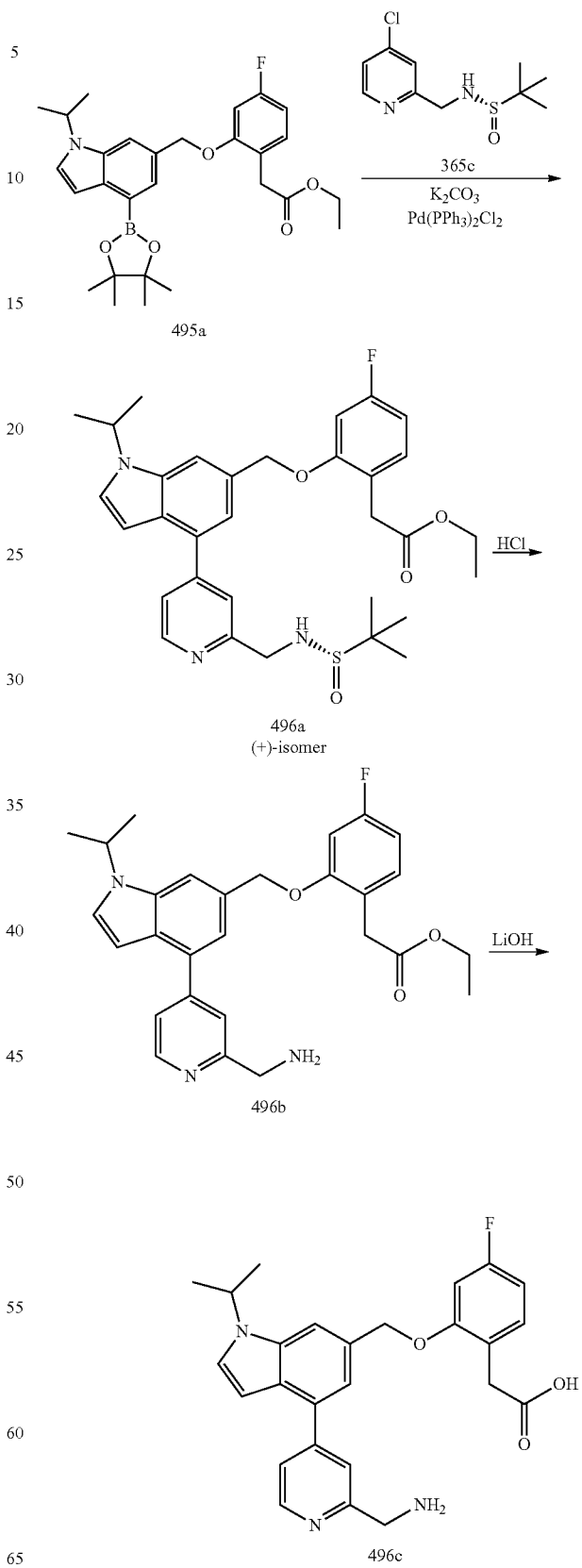

Preparation of 2-(2-((4-(2-(aminomethyl)pyridin-4-yl)-1-isopropyl-1H-indol-6-yl)methoxy)-4-fluorophenyl)acetic Acid (496c)

Step-1: Preparation of (+)-(S)-ethyl 2-(2-((4-(2-((1,1-dimethylethylsulfinamido)methyl)pyridin-4-yl)-1-isopropyl-1H-indol-6-yl)methoxy)-4-fluorophenyl)acetate (496a)

Compound 496a was prepared according to the procedure reported in step-3 of scheme-1 from ethyl 2-(4-fluoro-2-((1-isopropyl-4-(4,4,5,5-tetramethyl-1,3,2-dioxaborolan-2-yl)-1H-indol-6-yl)methoxy)phenyl)acetate (495a) (300 mg, 0.61 mmol) in dioxane (4 mL) using (+)-(S)—N-((4-chloropyridin-2-yl)methyl)-2-methylpropane-2-sulfinamide (365c) (179 mg, 0.73 mmol), Pd(PPh$_3$)$_2$Cl$_2$ (64 mg, 0.09 mmol) and a solution of K$_2$CO$_3$ (251 mg, 1.82 mmol) in water (1 mL) under a nitrogen atmosphere heating at 90° C. for 3 h on oil bath. This gave after workup and purification by flash column chromatography (silica gel, 12 g, eluting with DMA80 in DCM from 0-50%) (+)-(S)-ethyl 2-(2-((4-(2-((1,1-dimethylethylsulfinamido)methyl)pyridin-4-yl)-1-isopropyl-1H-indol-6-yl)methoxy)-4-fluorophenyl)acetate (496a) (300 mg, 85% yield) as a yellow oil; MS (ES+): 580.3 (M+1); Optical rotation [t]D=+21 (c=0.1, MeOH).

Step-2: Preparation of Ethyl 2-(2-((4-(2-(aminomethyl)pyridin-4-yl)-1-isopropyl-1H-indol-6-yl)methoxy)-4-fluorophenyl)acetate (496b)

Compound 496b was prepared according to the procedure reported in step-3 of scheme-305 from (+)-(S)-ethyl 2-(2-((4-(2-((1,1-dimethylethylsulfinamido)methyl)pyridin-4-yl)-1-isopropyl-1H-indol-6-yl)methoxy)-4-fluorophenyl)acetate (496a) (300 mg, 0.52 mmol) in DCM (5 mL) using 4 M HCl in dioxane (0.39 mL, 1.55 mmol) and stirring at room temperature for 1 h. This gave after workup and purification by flash column chromatography [silica (12 g), eluting with DMA80/DCM from 0-70%] ethyl 2-(2-((4-(2-(aminomethyl)pyridin-4-yl)-1-isopropyl-1H-indol-6-yl)methoxy)-4-fluorophenyl)acetate (496b) (200 mg, 81% yield) as a pale-yellow oil; MS (ES+): 476.2 (M+1).

Step-3: Preparation of 2-(2-((4-(2-(aminomethyl)pyridin-4-yl)-1-isopropyl-1H-indol-6-yl)methoxy)-4-fluorophenyl)acetic Acid (496c)

Compound 496c was prepared according to the procedure reported in step-6 of scheme-1 from ethyl 2-(2-((4-(2-(aminomethyl)pyridin-4-yl)-1-isopropyl-1H-indol-6-yl)methoxy)-4-fluorophenyl)acetate (496b) (200 mg, 0.42 mmol) in THF/MeOH (8 mL each) using a solution of lithium hydroxide hydrate (141 mg, 3.36 mmol) in water (2 mL) and stirring at room temperature for 16 h. This gave after workup and purification by reverse phase column [C-18 (50 g), column eluting with acetonitrile in water 0-100%] 2-(2-((4-(2-(aminomethyl)pyridin-4-yl)-1-isopropyl-1H-indol-6-yl)methoxy)-4-fluorophenyl)acetic acid (496c) (140 mg, 74% yield) free base as a white solid; $^1$H NMR (300 MHz, DMSO-d$_6$) δ 8.57 (d, J=5.2 Hz, 1H), 8.16 (s, 1H), 7.74 (d, J=7.9 Hz, 2H), 7.65 (d, J=3.3 Hz, 1H), 7.55 (s, 1H), 7.11 (t, J=7.7 Hz, 1H), 6.90 (dd, J=11.5, 2.5 Hz, 1H), 6.73 (d, J=3.3 Hz, 1H), 6.62 (td, J=8.3, 2.4 Hz, 1H), 5.30 (s, 2H), 4.83 (p, J=6.6 Hz, 1H), 4.06 (s, 2H), 3.38 (s, 2H), 1.51 (d, J=6.6 Hz, 6H); $^{19}$F NMR (282 MHz, DMSO-d$_6$) δ −114.91; MS (ES+): 448.20 (M+1); (ES−): 446.15 (M−1).

Scheme-497

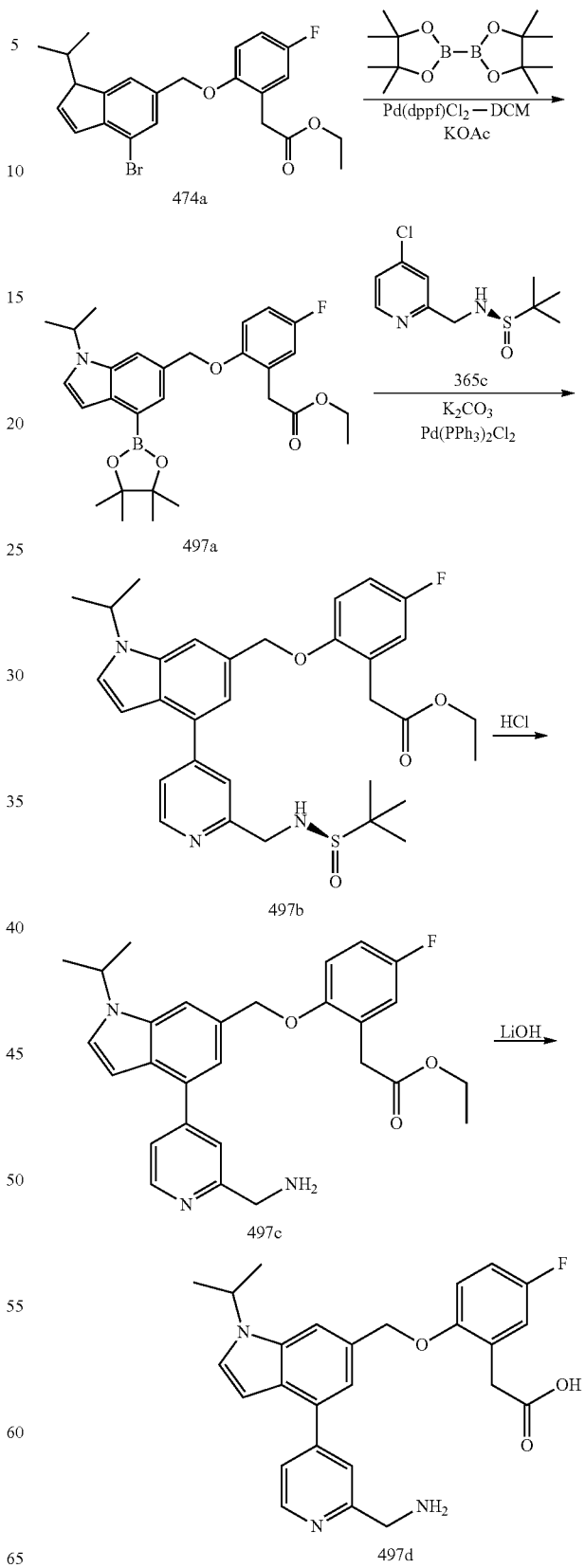

1479

Preparation of 2-(2-((4-(2-(aminomethyl)pyridin-4-yl)-1-isopropyl-1H-indol-6-yl)methoxy)-5-fluorophenyl)acetic Acid (497d)

Step-1: Preparation of Ethyl 2-(5-fluoro-2-((1-isopropyl-4-(4,4,5,5-tetramethyl-1,3,2-dioxaborolan-2-yl)-1H-indol-6-yl)methoxy)phenyl)acetate (497a)

Compound 497a was prepared according to the procedure reported in step-1 of scheme-59 from ethyl 2-(2-((4-bromo-1-isopropyl-1H-indol-6-yl)methoxy)-5-fluorophenyl)acetate (474a) (0.57 g, 1.271 mmol), using bis(pinacolato)diboron (0.484 g, 1.907 mmol), potassium acetate (0.374 g, 3.81 mmol) and Pd(dppf)Cl$_2$-DCM (0.104 g, 0.127 mmol) in anhydrous dioxane (5 mL) under a nitrogen atmosphere and heating at 100° C. for 16 h. This gave after workup and purification by flash column chromatography (silica gel, 24 g, eluting with ethyl acetate in hexanes 0-6%) ethyl 2-(5-fluoro-2-((1-isopropyl-4-(4,4,5,5-tetramethyl-1,3,2-dioxaborolan-2-yl)-1H-indol-6-yl)methoxy)phenyl)acetate (497a) (471 mg, 75% yield) as a pale-yellow oil; $^1$H NMR (300 MHz, DMSO-d$_6$) δ 7.68 (d, J=1.4 Hz, 1H), 7.53 (dd, J=3.2, 0.8 Hz, 1H), 7.45 (t, J=1.1 Hz, 1H), 7.17-7.01 (m, 3H), 6.76 (d, J=3.2 Hz, 1H), 5.16 (s, 2H), 4.85-4.67 (m, 1H), 4.01 (qd, J=7.1, 0.8 Hz, 2H), 3.62 (s, 2H), 1.46 (s, 3H), 1.44 (s, 3H), 1.33 (s, 12H), 1.06 (d, J=7.1 Hz, 3H). $^{19}$F NMR (282 MHz, DMSO-d$_6$) δ−124.26; LC-MS: t=3.23 min; MS (ES+): 496 (M+1).

Step-2: Preparation of (+)-(S)-ethyl 2-(2-((4-(2-((1,1-dimethylethylsulfinamido)methyl)pyridin-4-yl)-1-isopropyl-1H-indol-6-yl)methoxy)-5-fluorophenyl)acetate (497b)

Compound 497b was prepared according to the procedure reported in step-3 of scheme-1 from ethyl 2-(5-fluoro-2-((1-isopropyl-4-(4,4,5,5-tetramethyl-1,3,2-dioxaborolan-2-yl)-1H-indol-6-yl)methoxy)phenyl)acetate (497a) (224 mg, 0.452 mmol) in dioxane (4 mL) using (+)-(S)—N-((4-chloropyridin-2-yl)methyl)-2-methylpropane-2-sulfinamide (365c) (145 mg, 0.588 mmol), Pd(PPh$_3$)$_2$Cl$_2$ (32 mg, 0.045 mmol) and 3.3 M aqueous K$_2$CO$_3$ (0.411 mL, 1.357 mmol) under a nitrogen atmosphere heating at 100° C. for 16 h on oil bath. This gave after workup and purification by flash column chromatography (silica gel, 12 g, eluting with 0-3% MeOH in DCM) (+)-(S)-ethyl 2-(2-((4-(2-((1,1-dimethylethylsulfinamido)methyl)pyridin-4-yl)-1-isopropyl-1H-indol-6-yl)methoxy)-5-fluorophenyl)acetate (497b) (255 mg, 97% yield) as an orange oil; MS (ES+) 580 (M+1); Optical rotation [t]D=+40 (c=0.01, MeOH).

Step-3: Preparation of Ethyl 2-(2-((4-(2-(aminomethyl)pyridin-4-yl)-1-isopropyl-1H-indol-6-yl)methoxy)-5-fluorophenyl)acetate (497c)

Compound 497c was prepared according to the procedure reported in step-3 of scheme-305 from (+)-(S)-ethyl 2-(2-((4-(2-((1,1-dimethylethylsulfinamido)methyl)pyridin-4-yl)-1-isopropyl-1H-indol-6-yl)methoxy)-5-fluorophenyl)acetate (497b) (255 mg, 0.440 mmol) in DCM (4 mL) using 4 M HCl in dioxane (0.275 mL, 1.100 mmol) and stirring at room temperature for 3 h. This gave after workup ethyl 2-(2-((4-(2-(aminomethyl)pyridin-4-yl)-1-isopropyl-1H-indol-6-yl)methoxy)-5-fluorophenyl)acetate (497c) (148 mg, 71% yield) as a yellow semisolid; MS (ES+): 476 (M+1).

Step-4: Preparation of 2-(2-((4-(2-(aminomethyl)pyridin-4-yl)-1-isopropyl-1H-indol-6-yl)methoxy)-5-fluorophenyl)acetic Acid (497d)

Compound 497d was prepared according to the procedure reported in step-6 of scheme-1 from ethyl 2-(2-((4-(2-(aminomethyl)pyridin-4-yl)-1-isopropyl-1H-indol-6-yl)methoxy)-5-fluorophenyl)acetate (497c) (148 mg, 0.311 mmol) in MeOH (3 mL) using a solution of 2.0 M aqueous LiOH (0.778 mL, 1.556 mmol) and stirring at room temperature for 16 h. This gave after workup and purification by reverse phase column (C-18, 100g, column eluting with acetonitrile in water 0-60%) 2-(2-((4-(2-(aminomethyl)pyridin-4-yl)-1-isopropyl-1H-indol-6-yl)methoxy)-5-fluorophenyl)acetic Acid (497d) (50 mg, 36% yield) free base as a pale-yellow solid; $^1$H NMR (300 MHz, DMSO-d$_6$) δ 8.58 (d, J=5.2 Hz, 1H), 8.17 (s, 1H), 7.79-7.73 (m, 1H), 7.71 (s, 1H), 7.65 (d, J=3.3 Hz, 1H), 7.56 (s, 1H), 7.02-6.86 (m, 3H), 6.73 (d, J=3.2 Hz, 1H), 5.27 (s, 2H), 4.91-4.75 (m, 1H), 4.08 (s, 2H), 3.41 (s, 2H), 1.52 (s, 3H), 1.50 (s, 3H). $^{19}$F NMR (282 MHz, DMSO-d$_6$) δ−125.21; MS (ES+): 448 (M+1), (ES−): 446 (M−1); Analysis calculated for C$_{26}$H$_{26}$FN$_3$O$_3$.0.75H$_2$O: C, 67.74; H, 6.01; N, 9.11; Found: C, 67.54; H, 5.99; N, 9.13.

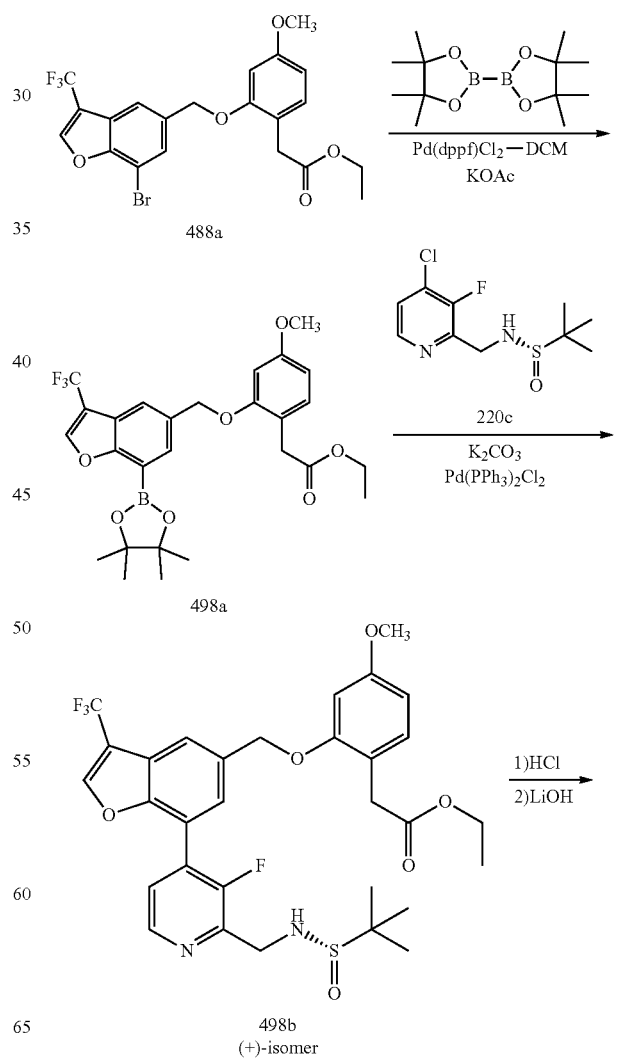

Scheme-498

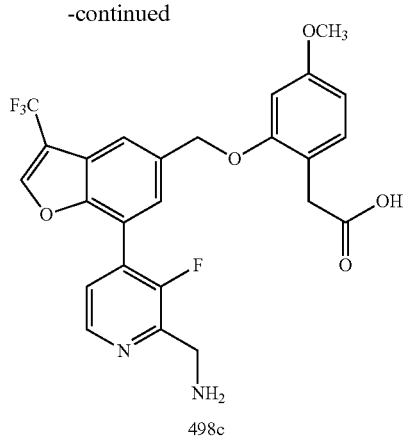

498c

Preparation of 2-(2-((7-(2-(aminomethyl)-3-fluoropyridin-4-yl)-3-(trifluoromethyl)benzofuran-5-yl)methoxy)-4-methoxyphenyl)acetic Acid (498c)

Step-1: Preparation of Ethyl 2-(4-methoxy-2-((7-(4,4,5,5-tetramethyl-1,3,2-dioxaborolan-2-yl)-3-(trifluoromethyl)benzofuran-5-yl)methoxy)phenyl)acetate (498a)

Compound 498a was prepared according to the procedure reported in step-1 of scheme-59 from ethyl 2-(2-((7-bromo-3-(trifluoromethyl)benzofuran-5-yl)methoxy)-4-methoxyphenyl)acetate (488a) (0.9 g, 1.847 mmol) using bis(pinacolato)diboron (0.704 g, 2.77 mmol), potassium acetate (0.544 g, 5.54 mmol) and Pd(dppf)Cl$_2$-DCM (0.151 g, 0.185 mmol) in anhydrous dioxane (50 mL) under an argon atmosphere and heating at 90° C. overnight. This gave after workup and purification by flash column chromatography [silica (40g), eluting with EtOAc in hexane from 0-40%] ethyl 2-(4-methoxy-2-((7-(4,4,5,5-tetramethyl-1,3,2-dioxaborolan-2-yl)-3-(trifluoromethyl)benzofuran-5-yl)methoxy)phenyl)acetate (498a) (797 mg, 81% yield) as a clear oil. $^1$H NMR (300 MHz, DMSO-d$_6$) δ 8.85 (q, J=1.7 Hz, 1H), 7.93 (dd, J=2.0, 1.0 Hz, 1H), 7.82 (d, J=1.8 Hz, 1H), 7.11 (d, J=8.3 Hz, 1H), 6.71 (d, J=2.4 Hz, 1H), 6.49 (dd, J=8.3, 2.4 Hz, 1H), 5.24 (s, 2H), 4.05-3.97 (m, 2H), 3.75 (s, 3H), 3.51 (s, 2H), 1.35 (s, 12H), 1.04 (t, J=7.1 Hz, 3H). $^{19}$F NMR (282 MHz, DMSO-d$_6$) δ−57.99.

Step-2: Preparation of (+)-(S)-ethyl 2-(2-((7-(2-((1,1-dimethylethylsulfinamido)methyl)-3-fluoropyridin-4-yl)-3-(trifluoromethyl)benzofuran-5-yl)methoxy)-4-methoxyphenyl)acetate (498b)

Compound 498b was prepared according to the procedure reported in step-3 of scheme-1 from ethyl 2-(4-methoxy-2-((7-(4,4,5,5-tetramethyl-1,3,2-dioxaborolan-2-yl)-3-(trifluoromethyl)benzofuran-5-yl)methoxy)phenyl)acetate (498a) (265 mg, 0.496 mmol) in dioxane (10 mL) using (+)-(S)—N-((4-chloro-3-fluoropyridin-2-yl)methyl)-2-methylpropane-2-sulfinamide (220c) (131 mg, 0.496 mmol), Pd(PPh$_3$)$_2$Cl$_2$ (52.2 mg, 0.074 mmol) and a solution of K$_2$CO$_3$ (206 mg, 1.488 mmol) in water (1 mL) under a nitrogen atmosphere heating at 100° C. for 4 h on oil bath. This gave after workup and purification by flash column chromatography [silica gel (24 g), eluting with DMA80 in DCM from 0-30%] (+)-(S)-ethyl 2-(2-((7-(2-((1,1-dimethylethylsulfinamido)methyl)-3-fluoropyridin-4-yl)-3-(trifluoromethyl)benzofuran-5-yl)methoxy)-4-methoxyphenyl)acetate (498b) (203 mg, 64% yield) as a brown oil. $^1$H NMR (300 MHz, DMSO-d$_6$) δ 8.95-8.87 (m, 1H), 8.55 (d, J=4.9 Hz, 1H), 7.95 (s, 1H), 7.71 (s, 1H), 7.66-7.64 (m, 1H), 7.12 (d, J=8.3 Hz, 1H), 6.72 (d, J=2.4 Hz, 1H), 6.50 (dd, J=8.3, 2.4 Hz, 1H), 5.84 (q, J=6.3 Hz, 1H), 5.31 (s, 2H), 4.42 (dd, J=5.9, 2.0 Hz, 2H), 3.92-3.85 (m, 2H), 3.75 (s, 3H), 3.54 (s, 2H), 1.11 (s, 9H), 0.97 (t, J=7.1 Hz, 3H); $^{19}$F NMR (282 MHz, DMSO-d$_6$) δ−58.08, −128.17; MS (ES+): 637.2 (M+1); Optical rotation [t]D=+25.10 (c=0.255, MeOH).

Step-3: Preparation of 2-(2-((7-(2-(aminomethyl)-3-fluoropyridin-4-yl)-3-(trifluoromethyl)benzofuran-5-yl)methoxy)-4-methoxyphenyl)acetic Acid (498c)

To a stirred solution of (+)-(S)-ethyl 2-(2-((7-(2-((1,1-dimethylethylsulfinamido)methyl)-3-fluoropyridin-4-yl)-3-(trifluoromethyl)benzofuran-5-yl)methoxy)-4-methoxyphenyl)acetate (498b) (200 mg, 0.314 mmol) in THF (5.25 mL) was added hydrochloric acid (4.M in 1-4-dioxane, 0.157 mL, 0.628 mmol), stirred at room temperature for 30 minutes and concentrated in vacuum to dryness. The residue obtained was dissolved in THF (3.5 mL), acetonitrile (1.75 mL) and water (1.75 mL) and added lithium hydroxide monohydrate (73 mg, 1.75 mmol). The reaction mixture was stirred for 21 h at room temperature and concentrated to remove THF and acetonitrile. The reaction was diluted with water (2 mL) and acidified to pH 4 using 1M HCl.

The solid separated out was decanted and purified by reverse-phase column chromatography [C-18 column, 50 g, eluting with 0.1% aqueous HCl in water and acetonitrile from 0-100%] to afford 2-(2-((7-(2-(aminomethyl)-3-fluoropyridin-4-yl)-3-(trifluoromethyl)benzofuran-5-yl)methoxy)-4-methoxyphenyl)acetic acid (498c) (22 mg, 14% yield) HCl salt as a white solid; $^1$H NMR (300 MHz, DMSO-d$_6$) δ 8.94 (d, J=1.8 Hz, 1H), 8.66 (d, J=5.0 Hz, 1H), 8.01 (s, 1H), 7.82 (t, J=5.3 Hz, 1H), 7.78 (s, 1H), 7.12 (d, J=8.2 Hz, 1H), 6.70 (d, J=2.4 Hz, 1H), 6.50 (dd, J=8.3, 2.3 Hz, 1H), 5.34 (s, 2H), 4.39 (s, 2H), 3.74 (s, 3H), 3.50 (s, 2H); $^{19}$F NMR (282 MHz, DMSO-d$_6$) δ−58.03, −128.47; MS (ES+): 505.1 (M+1); (ES−): 503.1 (M−1); Analysis calculated for C$_{25}$H$_{20}$F$_4$N$_2$O$_5$.HCl.1.75H$_2$O: C, 52.46; H, 4.31; Cl, 6.19; N, 4.89; Found: C, 52.52; H, 4.00; Cl, 6.36; N, 5.16.

Scheme-499

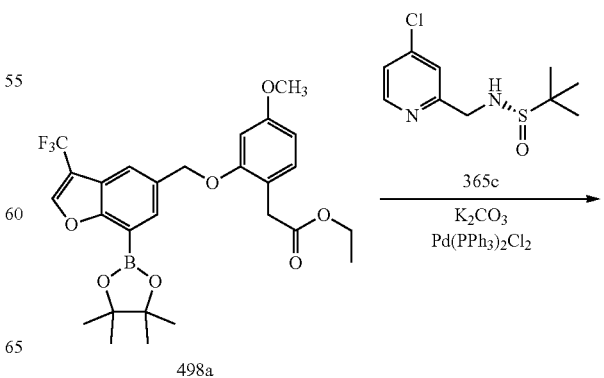

498a

-continued

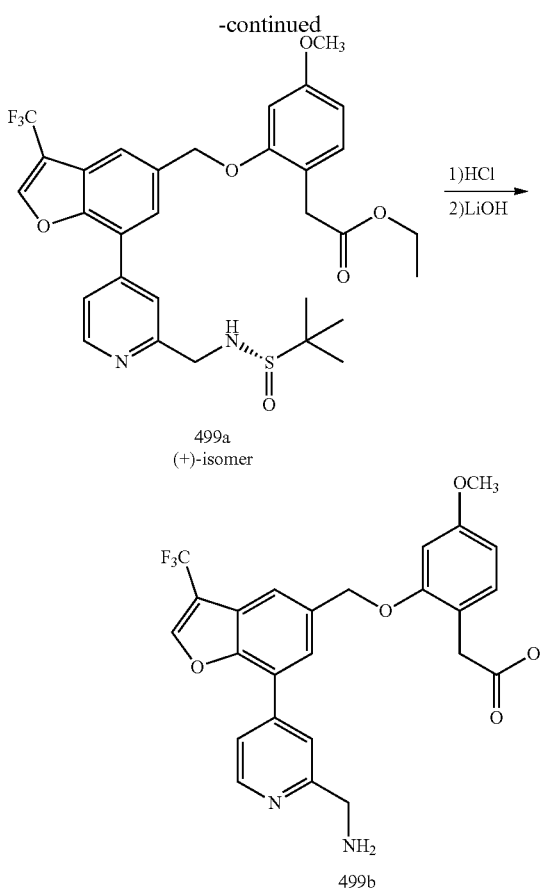

499a
(+)-isomer

499b

Preparation of 2-(2-((7-(2-(aminomethyl)pyridin-4-yl)-3-(trifluoromethyl)benzofuran-5-yl)methoxy)-4-methoxyphenyl)acetic Acid (499b)

Step-1: Preparation of (+)-(S)-ethyl 2-(2-((7-(2-((1,1-dimethylethylsulfinamido)methyl)pyridin-4-yl)-3-(trifluoromethyl)benzofuran-5-yl)methoxy)-4-methoxyphenyl)acetate (499a)

Compound 499a was prepared according to the procedure reported in step-3 of scheme-1 from ethyl 2-(4-methoxy-2-((7-(4,4,5,5-tetramethyl-1,3,2-dioxaborolan-2-yl)-3-(trifluoromethyl)benzofuran-5-yl)methoxy)phenyl)acetate (498a) (265 mg, 0.496 mmol) in dioxane (10 mL) using (+)-(S)—N-((4-chloropyridin-2-yl)methyl)-2-methylpropane-2-sulfinamide (365c) (122 mg, 0.496 mmol), Pd(PPh$_3$)$_2$Cl$_2$ (52.2 mg, 0.074 mmol) and a solution of K$_2$CO$_3$ (206 mg, 1.488 mmol) in water (1 mL) under a nitrogen atmosphere heating at 100° C. for 4 h on oil bath. This gave after workup and purification by flash column chromatography [silica gel (24 g), eluting with DMA80 in DCM from 0-30%] (+)-(S)-ethyl 2-(2-((7-(2-((1,1-dimethylethylsulfinamido)methyl)pyridin-4-yl)-3-(trifluoromethyl)benzofuran-5-yl)methoxy)-4-methoxyphenyl)acetate (499a) (147 mg, 48% yield) as a brown oil. $^1$H NMR (300 MHz, DMSO-d$_6$) δ 8.93 (d, J=1.7 Hz, 1H), 8.68 (dd, J=5.2, 0.8 Hz, 1H), 8.04-7.98 (m, 1H), 7.92-7.83 (m, 2H), 7.78 (dd, J=5.2, 1.8 Hz, 1H), 7.12 (d, J=8.3 Hz, 1H), 6.71 (d, J=2.4 Hz, 1H), 6.50 (dd, J=8.3, 2.4 Hz, 1H), 5.95 (t, J=5.9 Hz, 1H), 5.31 (s, 2H), 4.38 (dd, J=6.1, 4.2 Hz, 2H), 3.92-3.86 (m, 2H), 3.74 (s, 3H), 3.55 (s, 2H), 1.07 (s, 9H), 0.96 (t, J=7.1 Hz, 3H); $^{19}$F NMR (282 MHz, DMSO-d$_6$) δ −58.05; MS (ES+): 619.2 (M+1); Optical rotation [α]$_D$=+16.84 (c=0.095, MeOH).

Step-2: Preparation of 2-(2-((7-(2-(aminomethyl)pyridin-4-yl)-3-(trifluoromethyl)benzofuran-5-yl)methoxy)-4-methoxyphenyl)acetic Acid (499b)

To a stirred solution of (+)-(S)-ethyl 2-(2-((7-(2-((1,1-dimethylethylsulfinamido)methyl)pyridin-4-yl)-3-(trifluoromethyl)benzofuran-5-yl)methoxy)-4-methoxyphenyl)acetate (499a) (140 mg, 0.226 mmol) in THF (3.75 mL) was added hydrochloric acid (4.0 M in 1-4-dioxane, 0.113 mL, 0.453 mmol), stirred at room temperature for 30 minutes and concentrated in vacuum to dryness. The residue obtained was dissolved in THF (2.5 mL), acetonitrile (1.25 mL) and water (1.25 mL) and added lithium hydroxide monohydrate (52.5 mg, 1.25 mmol). The reaction mixture was stirred for 21 h at room temperature and concentrated to remove THF and acetonitrile. The reaction was diluted with water (2 mL) and acidified to pH 4 using 1M HCl. The solid separated out was decanted and purified by reverse-phase column chromatography [C-18 column, 50 g, eluting with 0.1% aqueous HCl in water and acetonitrile from 0-100%] to afford 2-(2-((7-(2-(aminomethyl)pyridin-4-yl)-3-(trifluoromethyl)benzofuran-5-yl)methoxy)-4-methoxyphenyl)acetic acid (499b) (67 mg, 61% yield) HCl salt as a pale yellow solid; $^1$H NMR (300 MHz, DMSO-d$_6$) δ 8.97 (s, 1H), 8.81 (d, J=5.2 Hz, 1H), 8.43 (s, 3H, D$_2$O exchangeable), 8.03 (s, 1H), 7.96 (d, J=5.2 Hz, 3H), 7.13 (d, J=8.2 Hz, 1H), 6.69 (d, J=2.3 Hz, 1H), 6.55-6.44 (m, 1H), 5.35 (s, 2H), 4.32 (d, J=5.7 Hz, 2H), 3.74 (s, 3H), 3.52 (s, 2H); $^{19}$F NMR (282 MHz, DMSO-d$_6$) δ −58.00; MS (ES+): 487.1 (M+1); (ES−): 485.1 (M−1); Analysis calculated for C$_{25}$H$_{21}$F$_3$N$_2$O$_5$.1.5HCl.3H$_2$O: C, 50.45; H, 4.83; Cl, 8.94; N, 4.71; Found: C, 50.32; H, 4.63; Cl, 8.70; N, 4.38.

Scheme-500

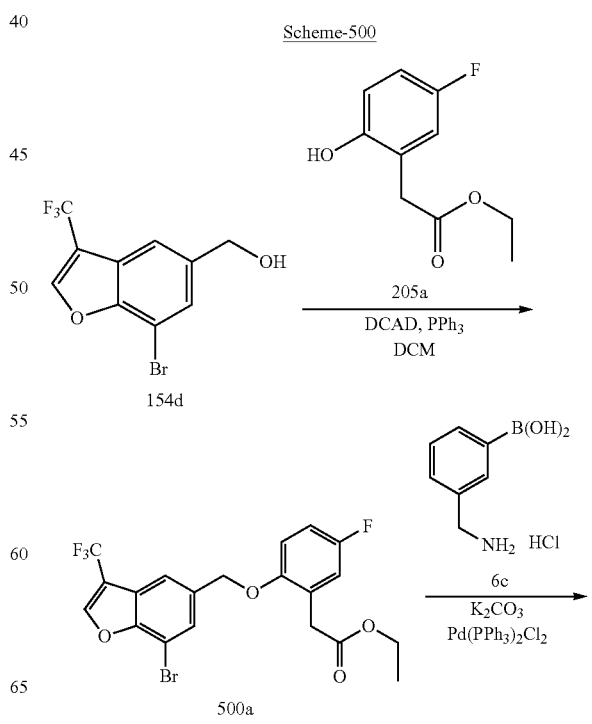

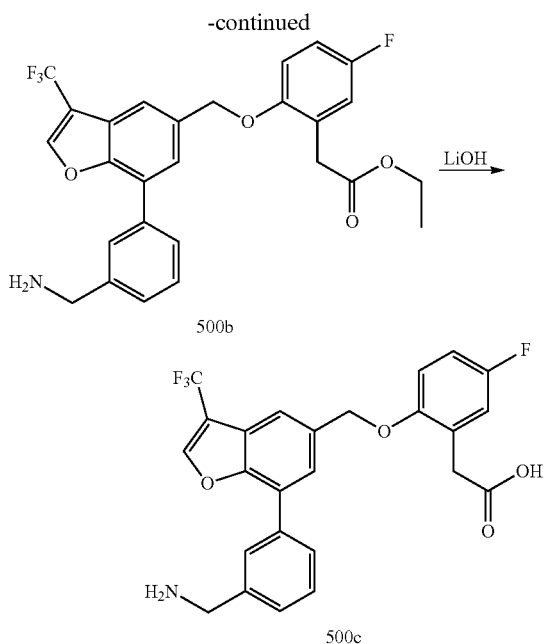

Preparation of 2-(2-((7-(3-(aminomethyl)phenyl)-3-(trifluoromethyl)benzofuran-5-yl)methoxy)-5-fluorophenyl)acetic Acid (500c)

Step-1: Preparation of Ethyl 2-(2-((7-bromo-3-(trifluoromethyl)benzofuran-5-yl)methoxy)-5-fluorophenyl)acetate (500a)

Compound 500a was prepared according to the procedure reported in step-2 of scheme-23 from (7-bromo-3-(trifluoromethyl)benzofuran-5-yl)methanol (154d) (1g, 3.39 mmol) in DCM (35 mL) using triphenylphosphine (0.978 g, 3.73 mmol), ethyl 2-(5-fluoro-2-hydroxyphenyl)acetate (205a) (0.806 g, 4.07 mmol) and a solution of (E)-bis(4-chlorobenzyl) diazene-1,2-dicarboxylate (DCAD, 1.369 g, 3.73 mmol) in DCM (35 mL) and stirring at room temperature for 1 h. This gave after workup and purification by flash column chromatography (silica gel, 40 g, eluting with 0 to 20% ethyl acetate in hexanes) ethyl 2-(2-((7-bromo-3-(trifluoromethyl)benzofuran-5-yl)methoxy)-5-fluorophenyl)acetate (500a) (1.16 g, 72.0% yield) as a white solid. $^1$H NMR (300 MHz, DMSO-$d_6$) δ 8.97 (q, J=1.6 Hz, 1H), 7.79 (s, 2H), 7.23-6.98 (m, 3H), 5.23 (s, 2H), 4.02 (q, J=7.1 Hz, 2H), 3.65 (s, 2H), 1.07 (t, J=7.1 Hz, 3H); $^{19}$F NMR (282 MHz, DMSO-$d_6$) δ −58.23, −123.71.

Step-2: Preparation of Ethyl 2-(2-((7-(3-(aminomethyl)phenyl)-3-(trifluoromethyl)benzofuran-5-yl)methoxy)-5-fluorophenyl)acetate (500b)

Compound 500b was prepared according to the procedure reported in step-3 of scheme-1 from ethyl 2-(2-((7-bromo-3-(trifluoromethyl)benzofuran-5-yl)methoxy)-5-fluorophenyl)acetate (500a) (225 mg, 0.473 mmol) in dioxane (8 mL) using (3-(aminomethyl)phenyl)boronic acid hydrochloride (6c) (106 mg, 0.568 mmol), Pd(PPh$_3$)$_2$Cl$_2$ (49.8 mg, 0.071 mmol) and a solution of K$_2$CO$_3$ (196 mg, 1.420 mmol) in water (0.8 mL) under an argon atmosphere heating at 100° C. for 4 h on oil bath. This gave after workup and purification by flash column chromatography [silica gel (24 g), eluting with DMA80 in DCM from 0-50%] ethyl 2-(2-((7-(3-(aminomethyl)phenyl)-3-(trifluoromethyl)benzofuran-5-yl)methoxy)-5-fluorophenyl)acetate (500b) (135 mg, 57% yield) as a clear oil. $^1$H NMR (300 MHz, DMSO-$d_6$) δ 8.97-8.82 (m, 1H), 7.81 (s, 1H), 7.75 (d, J=6.4 Hz, 2H), 7.70 (d, J=7.2 Hz, 1H), 7.52-7.41 (m, 2H), 7.18-7.08 (m, 3H), 5.28 (s, 2H), 3.91 (t, J=7.1 Hz, 2H), 3.82 (s, 2H), 3.65 (s, 2H), 0.97 (t, J=7.1 Hz, 3H); MS (ES+): 502.1 (M+1).

Step-3: Preparation of 2-(2-((7-(3-(aminomethyl)phenyl)-3-(trifluoromethyl)benzofuran-5-yl)methoxy)-5-fluorophenyl)acetic Acid (500c)

Compound 500c was prepared according to the procedure reported in step-6 of scheme-1 from ethyl 2-(2-((7-(3-(aminomethyl)phenyl)-3-(trifluoromethyl)benzofuran-5-yl)methoxy)-5-fluorophenyl)acetate (500b) (0.13 g, 0.259 mmol) in THF (1.6 mL), acetonitrile (0.8 mL) using lithium hydroxide monohydrate 1 N aqueous (0.8 mL, 0.8 mmol) and stirring at room temperature for 24 hours. This gave after workup and purification by reverse phase column [C18 column, 50 g, eluting with 0.1% aqueous HCl in water and acetonitrile from 0-100%] 2-(2-((7-(3-(aminomethyl)phenyl)-3-(trifluoromethyl)benzofuran-5-yl)methoxy)-5-fluorophenyl)acetic acid (500c) (85 mg, 69% yield) HCl salt as a white solid; $^1$H NMR (300 MHz, DMSO-$d_6$) δ 8.91 (s, 1H), 8.00 (s, 1H), 7.95-7.86 (m, 1H), 7.83 (s, 1H), 7.81 (s, 1H), 7.67-7.55 (m, 2H), 7.18-7.01 (m, 3H), 5.31 (s, 2H), 4.14 (s, 2H), 3.62 (s, 2H); $^{19}$F NMR (282 MHz, DMSO-$d_6$) δ −57.98, −123.90; MS (ES+): 474.1 (M+1); (ES−): 472.1 (M−1); Analysis calculated for C$_{25}$H$_{19}$F$_4$NO$_4$.HCl.0.5H$_2$O: C, 57.87; H, 4.08; Cl, 6.83; N, 2.70; Found: C, 58.06; H, 3.96; Cl, 6.62; N, 2.72.

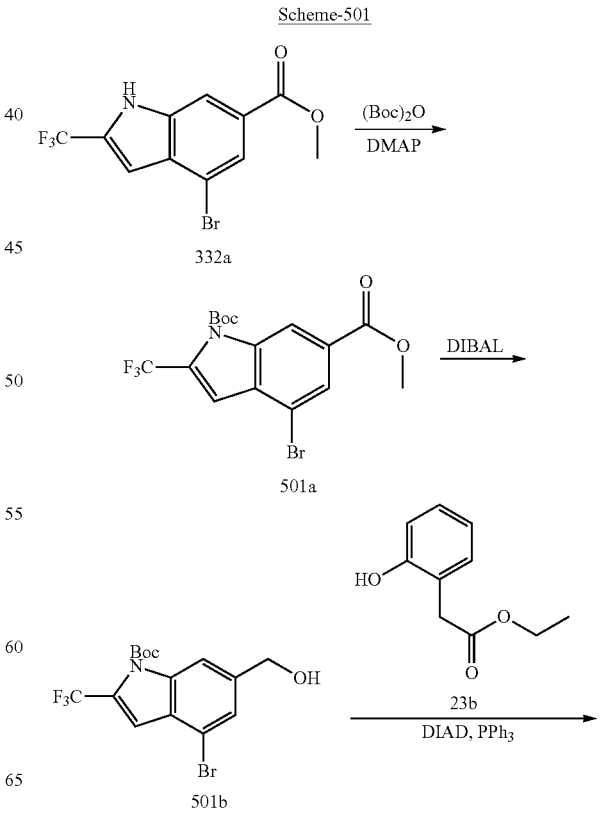

Scheme-501

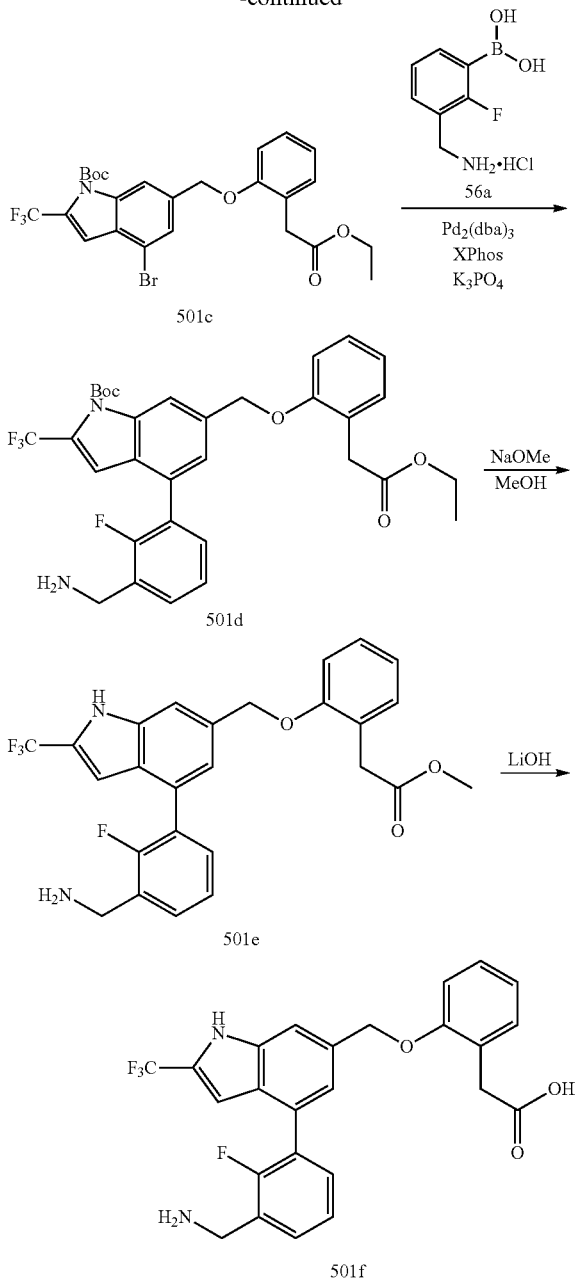

Preparation of 2-(2-((4-(3-(aminomethyl)-2-fluorophenyl)-2-(trifluoromethyl)-1H-indol-6-yl)methoxy)phenyl)acetic Acid (501f)

Step-1: Preparation of 1-tert-butyl 6-methyl 4-bromo-2-(trifluoromethyl)-1H-indole-1,6-dicarboxylate (501a)

To a suspension of methyl 4-bromo-2-(trifluoromethyl)-1H-indole-6-carboxylate (332a) (1.05 g, 3.26 mmol) and (Boc)$_2$O (1.067 g, 4.89 mmol) in DCM (20 mL) at room temperature was added DMAP (0.040 g, 0.326 mmol) stirred for 1 h at room temperature and quenched with saturated aqueous NH$_4$Cl (25 mL). The organic layer was separated washed with brine (25 mL), dried, filtered and concentrated in vacuum. The residue obtained was purified by flash column chromatography (silica gel, 24 g column, eluting with 0-3% EtOAc in hexane) to afford 1-tert-butyl 6-methyl 4-bromo-2-(trifluoromethyl)-1H-indole-1,6-dicarboxylate (501a) (1.31 g, 95% yield) as a white solid. $^1$H NMR (300 MHz, DMSO-d$_6$) δ 8.86-8.76 (m, 1H), 8.00 (dt, J=43.0, 0.9 Hz, 1H), 7.51 (d, J=36.8 Hz, 1H), 3.93 (s, 3H), 1.65 (s, 9H). $^{19}$F NMR (282 MHz, DMSO-d$_6$) δ−57.51.

Step-2: Preparation of tert-butyl 4-bromo-6-(hydroxymethyl)-2-(trifluoromethyl)-1H-indole-1-carboxylate (501b)

Compound 501b was prepared according to the procedure reported in step-2 of scheme-212 from 1-tert-butyl 6-methyl 4-bromo-2-(trifluoromethyl)-1H-indole-1,6-dicarboxylate (501a) (1.31 g, 3.10 mmol) in DCM (15 mL) using 1 M DIBAL-H in DCM (7.76 mL, 7.76 mmol). This gave after workup and purification by flash column chromatography (silica gel, 24 g, eluting with 0-15% EtOAc in Hexane) tert-butyl 4-bromo-6-(hydroxymethyl)-2-(trifluoromethyl)-1H-indole-1-carboxylate (501b) (0.89 g, 73% yield) as a white solid. $^1$H NMR (300 MHz, DMSO-d$_6$) δ 8.19 (d, 1H), 7.52 (d, 1H), 7.38 (d, 1H), 5.50 (t, J=5.8 Hz, 1H), 4.65 (d, J=5.7 Hz, 2H), 1.64 (s, 9H). $^{19}$F NMR (282 MHz, DMSO-d$_6$) δ−57.06; MS (ES−): 292/294 (M-Boc-1).

Step-3: Preparation of tert-butyl 4-bromo-6-((2-(2-ethoxy-2-oxoethyl)phenoxy)methyl)-2-(trifluoromethyl)-1H-indole-1-carboxylate (501c)

Compound 501c was prepared according to the procedure reported in step-2 of scheme-23 from tert-butyl 4-bromo-6-(hydroxymethyl)-2-(trifluoromethyl)-1H-indole-1-carboxylate (501b) (0.89 g, 2.258 mmol) in toluene (20 mL) using triphenylphosphine (1.184 g, 4.52 mmol), ethyl 2-(2-hydroxyphenyl) acetate (23b) (0.407 g, 2.258 mmol) and DIAD (0.913 g, 4.52 mmol) in toluene (5 mL). This gave after workup and purification by flash column chromatography (silica gel, 24 g column, eluting with EtOAc in hexanes from 0-5%) tert-butyl 4-bromo-6-((2-(2-ethoxy-2-oxoethyl)phenoxy)methyl)-2-(trifluoromethyl)-1H-indole-1-carboxylate (501c) (0.84 g, 67% yield) as a colorless oil. $^1$H NMR (300 MHz, DMSO-d$_6$) δ 8.24 (d, J=12.4 Hz, 1H), 7.61 (dd, J=44.2, 1.2 Hz, 1H), 7.42 (d, J=34.6 Hz, 1H), 7.31-7.20 (m, 2H), 7.09 (dd, J=8.3, 1.1 Hz, 1H), 6.93 (td, J=7.4, 1.1 Hz, 1H), 5.27 (s, 2H), 4.02 (qd, J=7.1, 1.1 Hz, 2H), 3.64 (s, 2H), 1.63 (s, 9H), 1.07 (t, J=7.1 Hz, 3H). $^{19}$F NMR (282 MHz, DMSO-d$_6$) δ−57.18; MS (ES−): 454/456 (M-Boc-1).

Step-4: Preparation of tert-butyl 4-(3-(aminomethyl)-2-fluorophenyl)-6-((2-(2-ethoxy-2-oxoethyl)phenoxy)methyl)-2-(trifluoromethyl)-1H-indole-1-carboxylate (501d)

Compound 501d was prepared according to the procedure reported in step-3 of scheme-1 from tert-butyl 4-bromo-6-((2-(2-ethoxy-2-oxoethyl)phenoxy)methyl)-2-(trifluoromethyl)-1H-indole-1-carboxylate (501c) (193 mg, 0.347 mmol) in dioxane (4 mL) using 3-(aminomethyl)-2-fluorophenylboronic acid hydrochloride (56a) (107 mg, 0.520 mmol), a solution of 1.27 M aqueous K$_3$PO$_4$ (0.546 mL, 0.694 mmol) in water, Pd$_2$(dba)$_3$ (32 mg, 0.035 mmol), XPhos (33 mg, 0.069 mmol) and heating under a nitrogen atmosphere at 100° C. for 16 h. This gave after workup and purification by flash column chromatography [silica (12 g), eluting with MeOH in DCM from 0-3%] tert-butyl 4-(3-(aminomethyl)-2-fluorophenyl)-6-((2-(2-ethoxy-2-oxoethyl)phenoxy)methyl)-2-(trifluoromethyl)-1H-indole-1-carboxylate (501d) (220 mg, 106% yield) as a pale-yellow oil. $^1$H NMR (300 MHz, DMSO-d$_6$) δ 8.32 (s, 1H), 7.61 (td, J=7.1, 2.3 Hz, 1H), 7.47 (t, J=1.1 Hz, 1H), 7.36 (dt, J=9.3, 6.3 Hz, 2H), 7.31-7.18 (m, 2H), 7.17-7.09 (m, 2H), 6.92 (td, J=7.4, 1.1 Hz, 1H), 5.31 (s, 2H), 3.96-3.76 (m, 4H), 3.62 (s, 2H), 1.64 (s, 9H), 0.95 (t, J=7.1 Hz, 3H). $^{19}$F NMR (282 MHz, DMSO-d$_6$) δ−56.88, −122.89; MS (ES+): 601 (M+1).

Step-5: Preparation of methyl 2-(2-((4-(3-(aminomethyl)-2-fluorophenyl)-2-(trifluoromethyl)-1H-indol-6-yl)methoxy)phenyl)acetate (501e)

To a solution of tert-butyl 4-(3-(aminomethyl)-2-fluorophenyl)-6-((2-(2-ethoxy-2-oxoethyl)phenoxy)methyl)-2-(trifluoromethyl)-1H-indole-1-carboxylate (501d) (220 mg, 0.366 mmol) in MeOH (5 mL) was added NaOMe (25 wt. % in MeOH) (0.251 mL, 1.099 mmol), stirred at room temperature for 16 h and evaporated to dryness to afford methyl 2-(2-((4-(3-(aminomethyl)-2-fluorophenyl)-2-(trifluoromethyl)-1H-indol-6-yl)methoxy)phenyl)acetate (501e) (134 mg, 75% yield) as a pale-yellow oil, which was used as such in next step without further purification; MS (ES+): 487 (M+1), (ES−): 485 (M−1).

Step-6: Preparation of 2-(2-((4-(3-(aminomethyl)-2-fluorophenyl)-2-(trifluoromethyl)-1H-indol-6-yl)methoxy)phenyl)acetic Acid (501f)

Compound 501f was prepared according to the procedure reported in step-6 of scheme-1 from methyl 2-(2-((4-(3-(aminomethyl)-2-fluorophenyl)-2-(trifluoromethyl)-1H-indol-6-yl)methoxy)phenyl)acetate (501e) (134 mg, 0.275 mmol) in MeOH (3 mL) using 2.0 M aqueous LiOH (0.413 mL, 0.826 mmol) and stirring at room temperature for 16 h. This gave after workup and purification by reverse phase column [C18 (100 g), eluting with 0-60% acetonitrile in water] 2-(2-((4-(3-(aminomethyl)-2-fluorophenyl)-2-(trifluoromethyl)-1H-indol-6-yl)methoxy)phenyl)acetic acid (501f) (50 mg, 38% yield) lithium salt as a white solid; $^1$H NMR (300 MHz, DMSO-d$_6$+D$_2$O) δ 7.83 (s, 1H), 7.59-7.49 (m, 1H), 7.49-7.41 (m, 1H), 7.35 (d, J=7.6 Hz, 1H), 7.29 (s, 1H), 7.18 (d, J=7.2 Hz, 1H), 7.10 (t, J=7.7 Hz, 1H), 6.96 (d, J=7.8 Hz, 1H), 6.84 (dd, J=14.4, 6.9 Hz, 2H), 5.30 (s, 2H), 3.89 (s, 2H), 3.39 (s, 2H). $^{19}$F NMR (282 MHz, DMSO-d$_6$) δ−58.88, −121.66; MS (ES+): 472 (M+1), (ES−): 471 (M−1).

Scheme-502

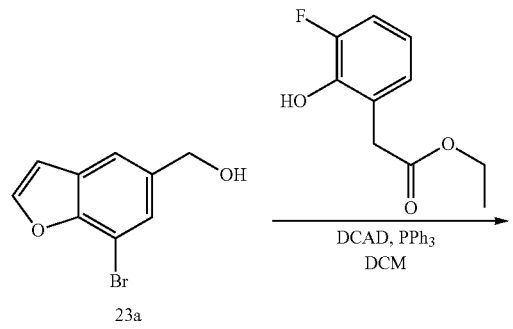

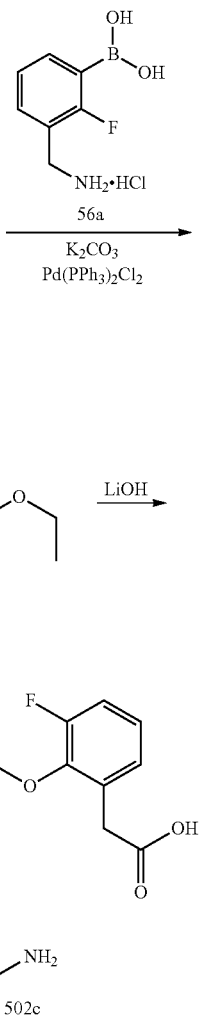

Preparation of 2-(2-((7-(3-(aminomethyl)-2-fluorophenyl)benzofuran-5-yl)methoxy)-3-fluorophenyl) acetic Acid (502c)

Step-1: Preparation of Ethyl 2-(2-((7-bromobenzofuran-5-yl)methoxy)-3-fluorophenyl)acetate (502a)

Compound 502a was prepared according to the procedure reported in step-2 of scheme-23 from (7-bromobenzofuran-5-yl)methanol (23a) (699 mg, 3.08 mmol) in DCM (8 mL) using triphenylphosphine (801 mg, 3.05 mmol), ethyl 2-(3-fluoro-2-hydroxyphenyl)acetate (604 mg, 3.05 mmol; CAS #1261451-84-6) and a solution of (E)-bis(4-chlorobenzyl) diazene-1,2-dicarboxylate (DCAD, 1.15 g, 3.13 mmol) in DCM (2 mL) and stirring at room temperature for 1 h. This gave after workup and purification by flash column chromatography (silica gel, 24 g, eluting with 0 to 50% ethyl acetate in hexanes) ethyl 2-(2-((7-bromobenzofuran-5-yl)methoxy)-3-fluorophenyl)acetate (502a) (633 mg, 51% yield) as a colorless oil; $^1$H NMR (300 MHz, DMSO-d$_6$) δ 8.15 (d, J=2.3 Hz, 1H), 7.72 (d, J=1.5 Hz, 1H), 7.62 (d, J=1.5 Hz, 1H), 7.23 (ddd, J=11.8, 6.1, 3.8 Hz, 1H), 7.16-7.06 (m, 3H), 5.20-5.05 (m, 2H), 3.98 (q, J=7.1 Hz, 2H), 3.66 (s, 2H), 1.08 (t, J=7.1 Hz, 3H); $^{19}$F NMR (282 MHz, DMSO-d$_6$) δ−129.82.

Step-2: Preparation of Ethyl 2-(2-((7-(3-(aminomethyl)-2-fluorophenyl)benzofuran-5-yl)methoxy)-3-fluorophenyl)acetate (502b)

Compound 502b was prepared according to the procedure reported in step-3 of scheme-1 from ethyl 2-(2-((7-bromobenzofuran-5-yl)methoxy)-3-fluorophenyl)acetate (502a) (150 mg, 0.368 mmol) in dioxane (5 mL) using (3-(aminomethyl)-2-fluorophenyl)boronic acid hydrochloride (56a) (93 mg, 0.553 mmol), Pd(PPh$_3$)$_2$Cl$_2$ (39 mg, 0.055 mmol) and a solution of K$_2$CO$_3$ (153 mg, 1.105 mmol) in water (0.5 mL) under an argon atmosphere heating at 100° C. for 3 h on oil bath. This gave after workup and purification by flash column chromatography [silica gel, 12g, eluting with DMA80 in DCM from 0-70%] ethyl 2-(2-((7-(3-(aminomethyl)-2-fluorophenyl)benzofuran-5-yl)methoxy)-3-fluorophenyl)acetate (502b) (149 mg, 90% yield) as a yellow oil. MS (ES+): 452.2 (M+1).

Step-3: Preparation of 2-(2-((7-(3-(aminomethyl)-2-fluorophenyl)benzofuran-5-yl)methoxy)-3-fluorophenyl)acetic Acid (502c)

Compound 502c was prepared according to the procedure reported in step-6 of scheme-1 from ethyl 2-(2-((7-(3-(aminomethyl)-2-fluorophenyl)benzofuran-5-yl)methoxy)-3-fluorophenyl)acetate (502b) (149 mg, 0.330 mmol) in THF/acetonitrile (6 mL each) using a solution of lithium hydroxide monohydrate (82 mg, 1.954 mmol) in water (2 mL) and stirring at room temperature overnight. This gave after workup and purification by reverse phase column [C18 column, 50 g, eluting with 0.1% aqueous HCl in water and acetonitrile from 0-100%] 2-(2-((7-(3-(aminomethyl)-2-fluorophenyl)benzofuran-5-yl)methoxy)-3-fluorophenyl) acetic acid (502c) (79 mg, 57% yield) HCl salt as a white solid. $^1$H NMR (300 MHz, DMSO-d$_6$) δ 9.07 (s, 2H), 8.11-8.02 (m, 1H), 7.82 (s, 1H), 7.77-7.58 (m, 2H), 7.52-7.35 (m, 2H), 7.28-7.14 (m, 1H), 7.14-6.98 (m, 3H), 5.17 (s, 2H), 4.17 (s, 2H), 3.61 (s, 2H); $^{19}$F NMR (282 MHz, DMSO) δ -118.58, -129.89. MS (ES+): 424.1 (M+1); MS (ES-): 422.1 (M-1); Analysis calculated for C$_{24}$H$_{19}$F$_2$NO$_4$.1.1HCl.1.25H$_2$O: C, 59.31; H, 4.69; Cl, 8.02; N, 2.88; Found: C, 59.32; H, 4.59; Cl, 7.94; N, 3.06.

Scheme-503

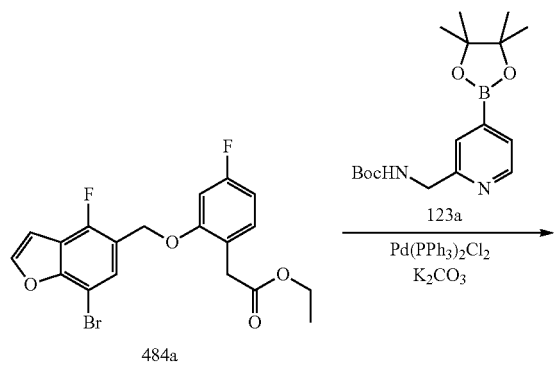

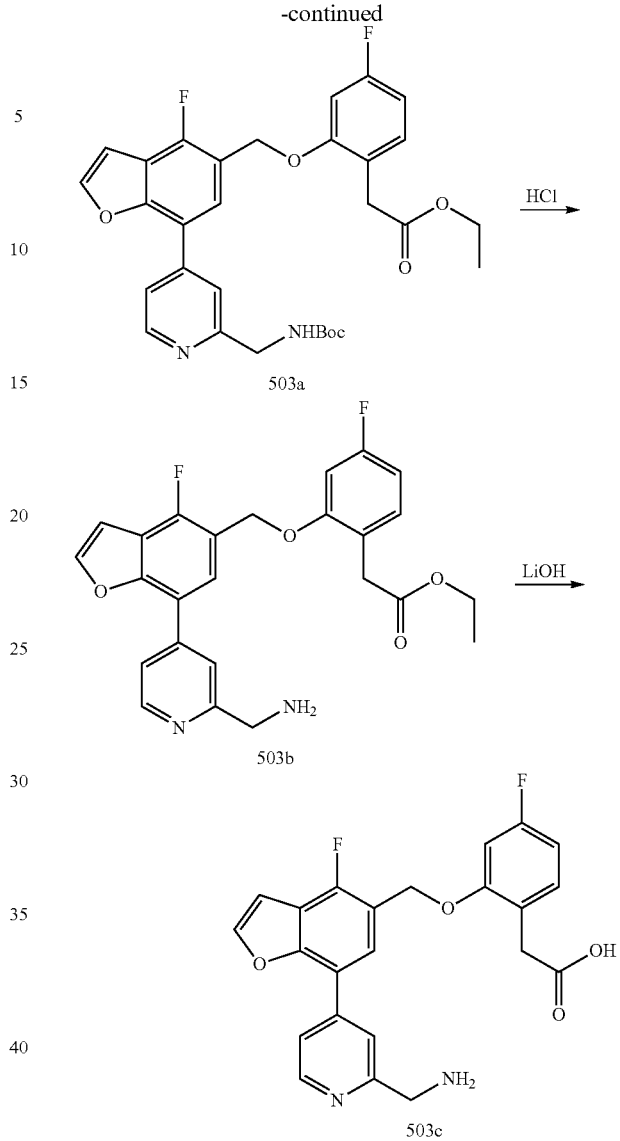

Preparation of 2-(2-((7-(2-(aminomethyl)pyridin-4-yl)-4-fluorobenzofuran-5-yl)methoxy)-4-fluorophenyl)acetic Acid (503c)

Step-1: Preparation of Ethyl 2-(2-((7-(2-(((tert-butoxycarbonyl)amino)methyl)pyridin-4-yl)-4-fluorobenzofuran-5-yl)methoxy)-4-fluorophenyl)acetate (503a)

Compound 503a was prepared according to the procedure reported in step-3 of scheme-1 from ethyl 2-(2-((7-bromo-4-fluorobenzofuran-5-yl)methoxy)-4-fluorophenyl)acetate (484a) (177 mg, 0.416 mmol) in dioxane (5 mL) using tert-butyl ((4-(4,4,5,5-tetramethyl-1,3,2-dioxaborolan-2-yl)pyridin-2-yl)methyl)carbamate (123a) (145 mg, 0.434 mmol), Pd(PPh$_3$)$_2$Cl$_2$ (44 mg, 0.062 mmol) and a solution of K$_2$CO$_3$ (173 mg, 1.249 mmol) in water (0.5 mL) under an argon atmosphere heating at 100° C. for 3 h on oil bath. This gave after workup and purification by flash column chromatography (silica gel, 12 g, eluting with DMA80 in DCM from 0-70%) ethyl 2-(2-((7-(2-((((tert-butoxycarbonyl)

amino)methyl)pyridin-4-yl)-4-fluorobenzofuran-5-yl) methoxy)-4-fluorophenyl)acetate (503a) (193 mg, 84% yield) as a dark oil; MS (ES+): 553.2 (M+1).

Step-2: Preparation of Ethyl 2-(2-((7-(2-(aminomethyl)pyridin-4-yl)-4-fluorobenzofuran-5-yl) methoxy)-4-fluorophenyl)acetate (503b)

Compound 503b was prepared according to the procedure reported in step-3 of scheme-305 from ethyl 2-(2-((7-(2-(((tert-butoxycarbonyl)amino)methyl)pyridin-4-yl)-4-fluorobenzofuran-5-yl)methoxy)-4-fluorophenyl)acetate (503a) (193 mg, 0.349 mmol) in ethanol (6 mL) using 4 M HCl in dioxane (0.873 mL, 3.49 mmol) and stirring at room temperature overnight. This gave after workup ethyl 2-(2-((7-(2-(aminomethyl)pyridin-4-yl)-4-fluorobenzofuran-5-yl) methoxy)-4-fluorophenyl)acetate (503b) (127 mg, 80% yield) as a yellow solid. MS (ES+): 453.2 (M+1).

Step-3: Preparation of 2-(2-((7-(2-(aminomethyl) pyridin-4-yl)-4-fluorobenzofuran-5-yl)methoxy)-4-fluorophenyl)acetic Acid (503c)

Compound 503c was prepared according to the procedure reported in step-6 of scheme-1 from ethyl 2-(2-((7-(2-(aminomethyl)pyridin-4-yl)-4-fluorobenzofuran-5-yl) methoxy)-4-fluorophenyl)acetate (503b) (127 mg, 0.281 mmol) in MeOH/THF (6 mL each) using a solution of LiOH (78 mg, 1.859 mmol) in water (2 mL) and stirring at room temperature overnight. This gave after workup and purification by reverse phase column [C-18 column, 50 g, eluting with acetonitrile in water (containing 0.1% HCl) from 0-100%] 2-(2-((7-(2-(aminomethyl)pyridin-4-yl)-4-fluorobenzofuran-5-yl)methoxy)-4-fluorophenyl)acetic acid (503c) (78 mg, 66% yield) HCl salt as a white solid. $^1$H NMR (300 MHz, DMSO-$d_6$) δ 8.80 (d, J=5.4 Hz, 1H), 8.66 (s, 3H), 8.31-8.21 (m, 1H), 8.16 (s, 1H), 8.07-7.92 (m, 2H), 7.31-7.21 (m, 2H), 7.14 (dd, J=11.2, 2.5 Hz, 1H), 6.77 (td, J=8.4, 2.4 Hz, 1H), 5.34 (s, 2H), 4.33 (d, J=5.6 Hz, 2H), 3.54 (s, 2H); $^{19}$F NMR (282 MHz, DMSO-$d_6$) δ−112.82, −121.04. MS (ES+): 425.1 (M+1); MS (ES−): 423.1 (M−1); Analysis calculated for $C_{23}H_{18}F_2N_2O_4 \cdot 1.9HCl \cdot 2H_2O$: C, 52.15; H, 4.55; Cl, 12.72; N, 5.29; Found: C, 52.50; H, 4.26; Cl, 12.88; N, 5.45.

Scheme-504

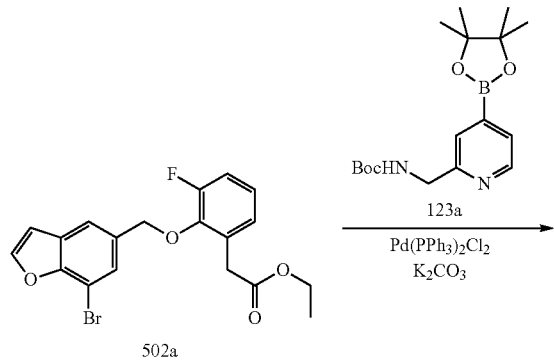

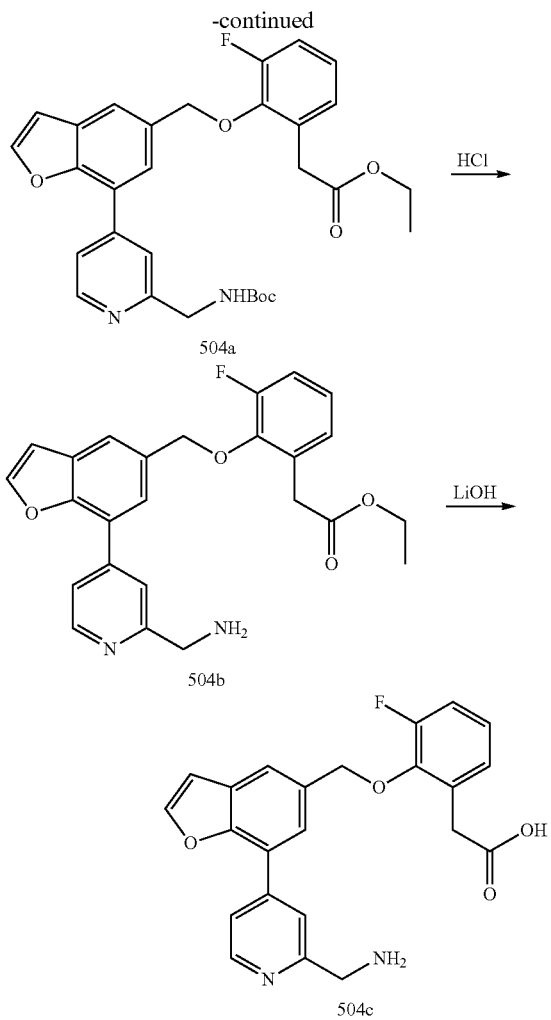

Preparation of 2-(2-((7-(2-(aminomethyl)pyridin-4-yl)benzofuran-5-yl)methoxy)-3-fluorophenyl)acetic Acid (504c)

Step-1: Preparation of Ethyl 2-(2-((7-(2-(((tert-butoxycarbonyl)amino)methyl)pyridin-4-yl)benzofuran-5-yl)methoxy)-3-fluorophenyl)acetate (504a)

Compound 504a was prepared according to the procedure reported in step-3 of scheme-1 from ethyl 2-(2-((7-bromobenzofuran-5-yl)methoxy)-3-fluorophenyl)acetate (502a) (163 mg, 0.4 mmol) in dioxane (5 mL) using tert-butyl ((4-(4,4,5,5-tetramethyl-1,3,2-dioxaborolan-2-yl)pyridin-2-yl)methyl)carbamate (123a) (169 mg, 0.506 mmol), Pd(PPh$_3$)$_2$Cl$_2$ (42 mg, 0.06 mmol) and a solution of K$_2$CO$_3$ (166 mg, 1.201 mmol) in water (0.5 mL) under an argon atmosphere heating at 100° C. for 3 h on oil bath. This gave after workup and purification by flash column chromatography (silica gel, 12 g, eluting with DMA80 in DCM from 0-70%) ethyl 2-(2-((7-(2-(((tert-butoxycarbonyl)amino) methyl)pyridin-4-yl)benzofuran-5-yl)methoxy)-3-fluorophenyl)acetate (504a) (214 mg, 100% yield) as a dark oil; MS (ES+): 535.2 (M+1). Step-2: Preparation of Ethyl 2-(2-((7-(2-(aminomethyl)pyridin-4-yl)benzofuran-5-yl) methoxy)-3-fluorophenyl)acetate (504b)

1495

Compound 504b was prepared according to the procedure reported in step-3 of scheme-305 from ethyl 2-(2-((7-(2-(((tert-butoxycarbonyl)amino)methyl)pyridin-4-yl)benzofuran-5-yl)methoxy)-3-fluorophenyl)acetate (504a) (214 mg, 0.4 mmol) in ethanol (6 mL) using 4 M HCl in dioxane (1.0 mL, 4 mmol) and stirring at room temperature for 72 h. This gave after workup and purification by flash column chromatography [silica (12 g), eluting with DMA80 in DCM from 0-90%] ethyl 2-(2-((7-(2-(aminomethyl)pyridin-4-yl)benzofuran-5-yl)methoxy)-3-fluorophenyl)acetate (504b) (70 mg, 40% yield) as a colorless oil. MS (ES+): 435.1 (M+1).

Step-3: Preparation of 2-(2-((7-(2-(aminomethyl) pyridin-4-yl)benzofuran-5-yl)methoxy)-3-fluorophenyl)acetic Acid (504c)

Compound 504c was prepared according to the procedure reported in step-6 of scheme-1 from ethyl 2-(2-((7-(2-(aminomethyl)pyridin-4-yl)benzofuran-5-yl)methoxy)-3-fluorophenyl)acetate (504b) (70 mg, 0.161 mmol) in MeOH/THF (6 mL each) using a solution of LiOH (65 mg, 1.549 mmol) in water (2 mL) and stirring at room temperature overnight. This gave after workup and purification by reverse phase column [C-18 column, 50 g, eluting with acetonitrile in water (containing 0.1% HCl) from 0-100%] 2-(2-((7-(2-(aminomethyl)pyridin-4-yl)benzofuran-5-yl)methoxy)-3-fluorophenyl)acetic acid (504c) (45 mg, 69% yield) HCl salt as a white solid. $^1$H NMR (300 MHz, DMSO-$d_6$) δ 8.80 (d, J=5.3 Hz, 1H), 8.61 (s, 3H), 8.19 (d, J=2.2 Hz, 1H), 8.13 (s, 1H), 8.02 (d, J=5.4 Hz, 1H), 7.89 (s, 1H), 7.83 (s, 1H), 7.30-7.18 (m, 1H), 7.18-6.99 (m, 3H), 5.21 (s, 2H), 4.33 (s, 2H), 3.64 (s, 2H); $^{19}$F NMR (282 MHz, DMSO-$d_6$) δ−129.81. MS (ES+): 407.1 (M+1); MS (ES−): 405.2 (M−1); Analysis calculated for $C_{23}H_{19}FN_2O_4 \cdot 1.9HCl \cdot 1.5H_2O$: C, 54.95; H, 4.79; Cl, 13.40; N, 5.57; Found: C, 54.86; H, 4.56; Cl, 13.21; N, 5.60.

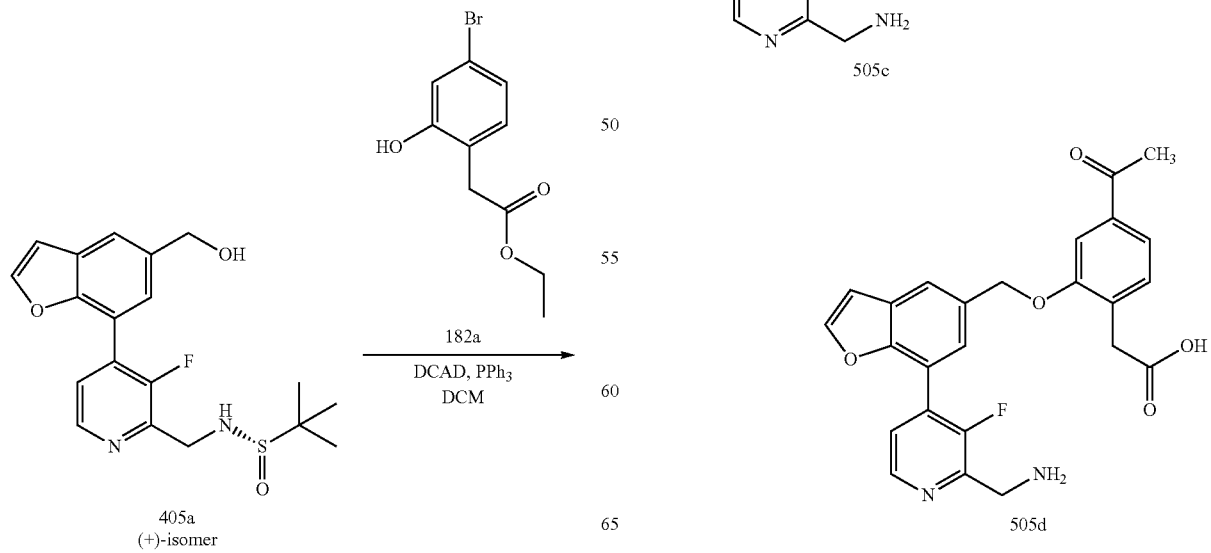

Preparation of 2-(4-acetyl-2-((7-(2-(aminomethyl)-3-fluoropyridin-4-yl)benzofuran-5-yl)methoxy)phenyl)acetic Acid (505d)

Step-1: Preparation of (+)-(S)-ethyl 2-(4-bromo-2-((7-(2-((1,1-dimethylethylsulfinamido)methyl)-3-fluoropyridin-4-yl)benzofuran-5-yl)methoxy)phenyl)acetate (505a)

Compound 505a was prepared according to the procedure reported in step-2 of scheme-23 from (+)-(S)—N-((3-fluoro-4-(5-(hydroxymethyl)benzofuran-7-yl)pyridin-2-yl)methyl)-2-methylpropane-2-sulfinamide (405a) (900 mg, 2.391 mmol) in DCM (30 mL) using triphenylphosphine (776 mg, 2.96 mmol), ethyl 2-(4-bromo-2-hydroxyphenyl)acetate (182a) (590 mg, 2.277 mmol) and a solution of (E)-bis(4-chlorobenzyl) diazene-1,2-dicarboxylate (DCAD, 1087 mg, 2.96 mmol) in DCM (30 mL). This gave after workup and purification by flash column chromatography (silica gel, 80 g, eluting with 0 to 50% ethyl acetate in hexanes) (+)-(S)-ethyl 2-(4-bromo-2-((7-(2-((1,1-dimethylethylsulfinamido)methyl)-3-fluoropyridin-4-yl)benzofuran-5-yl)methoxy)phenyl)acetate (505a) (710 mg, 51% yield) as a light yellowish gum; $^1$H NMR (300 MHz, DMSO-$d_6$) δ 8.52 (dd, J=4.9, 0.7 Hz, 1H), 8.09 (d, J=2.2 Hz, 1H), 7.85 (d, J=1.6 Hz, 1H), 7.68-7.64 (m, 1H), 7.52 (q, J=1.6 Hz, 1H), 7.35 (d, J=1.8 Hz, 1H), 7.23-7.05 (m, 3H), 5.84 (t, J=5.8 Hz, 1H), 5.28 (s, 2H), 4.41 (dd, J=5.8, 2.1 Hz, 2H), 3.90 (q, J=7.1 Hz, 2H), 3.60 (s, 2H), 1.11 (s, 9H), 0.96 (t, J=7.1 Hz, 3H); $^{19}$F NMR (282 MHz, DMSO-$d_6$) δ−128.02; MS (ES+): 617.20; Optical rotation [t]D=+19.78 (c=0.445, MeOH).

Step-2: Preparation of (S)-ethyl 2-(4-acetyl-2-((7-(2-((1,1-dimethylethylsulfinamido)methyl)-3-fluoropyridin-4-yl)benzofuran-5-yl)methoxy)phenyl)acetate (505b)

Compound 505b was prepared according to the procedure reported in step-1 of scheme-262 from (+)-(S)-ethyl 2-(4-bromo-2-((7-(2-((1,1-dimethylethylsulfinamido)methyl)-3-fluoropyridin-4-yl)benzofuran-5-yl)methoxy)phenyl)acetate (505a) (650 mg, 1.053 mmol) in toluene (15 mL) using tributyl(1-ethoxyvinyl)stannane (0.469 mL, 1.316 mmol) and Pd(PPh$_3$)$_4$ (122 mg, 0.105 mmol) and heating at reflux for 24 h under a nitrogen atmosphere, followed by hydrolysis using 3 N aqueous HCl (1.053 mL, 3.16 mmol). This gave after workup and purification by flash column chromatography (Silica gel, 24 g, eluting with 0% to 50% to 100% in 9:1 ethyl acetate/methanol in hexanes) (S)-ethyl 2-(4-acetyl-2-((7-(2-((1,1-dimethylethylsulfinamido)methyl)-3-fluoropyridin-4-yl)benzofuran-5-yl)methoxy)phenyl)acetate (505b) (32 mg, 5%); MS (ES+): 581.20 (M+1).

Step-3: Preparation of Ethyl 2-(4-acetyl-2-((7-(2-(aminomethyl)-3-fluoropyridin-4-yl)benzofuran-5-yl)methoxy)phenyl)acetate (505c)

To a solution of (S)-ethyl 2-(4-acetyl-2-((7-(2-((1,1-dimethylethylsulfinamido)methyl)-3-fluoropyridin-4-yl)benzofuran-5-yl)methoxy)phenyl)acetate (505b) (30 mg, 0.052 mmol) in tetrahydrofuran (5 mL) was added 3 N HCl (0.052 mL, 0.155 mmol) at room temperature and stirred for 2 h. The reaction mixture was concentrated to dryness to give ethyl 2-(4-acetyl-2-((7-(2-(aminomethyl)-3-fluoropyridin-4-yl)benzofuran-5-yl)methoxy)phenyl)acetate (505c) which was used as such for next step without further purification.

Step-4: Preparation of 2-(4-acetyl-2-((7-(2-(aminomethyl)-3-fluoropyridin-4-yl)benzofuran-5-yl)methoxy)phenyl)acetic Acid (505d)

Compound 505d was prepared according to the procedure reported in step-6 of scheme-1 from ethyl 2-(4-acetyl-2-((7-(2-(aminomethyl)-3-fluoropyridin-4-yl)benzofuran-5-yl)methoxy)phenyl)acetate (505c) (25 mg, 0.052 mmol) in THF/MeOH (5 mL each) using a solution of lithium hydroxide hydrate (18 mg, 0.416 mmol) in water (5 mL) and stirring at room temperature for 16 h. This gave after workup and purification by reverse phase column chromatography [C-18 column, eluting with water (0.1% HCl)/acetonitrile from 0 to 50%] 2-(4-acetyl-2-((7-(2-(aminomethyl)-3-fluoropyridin-4-yl)benzofuran-5-yl)methoxy)phenyl)acetic acid (505d) (4 mg, 19% yield) HCl salt as a white solid; $^1$H NMR (300 MHz, DMSO-$d_6$) δ 8.64 (d, J=5.0 Hz, 1H), 8.43 (s, 3H), 8.13-8.09 (m, 1H), 7.94 (s, 1H), 7.81 (t, J=5.5 Hz, 1H), 7.65-7.53 (m, 3H), 7.39 (d, J=7.5 Hz, 1H), 7.12-7.10 (m, 1H), 5.38 (s, 2H), 4.45-4.34 (m, 2H), 3.68 (s, 2H), 2.57 (s, 3H); $^{19}$F NMR (282 MHz, DMSO-$d_6$) δ−128.28; MS (ES+): 449.15 (M+1).

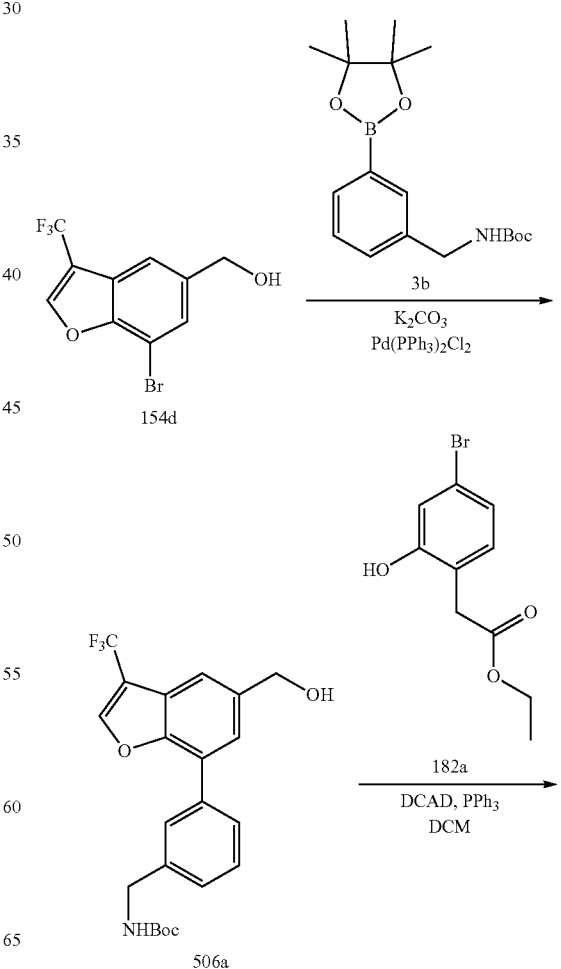

Scheme-506

1499

-continued

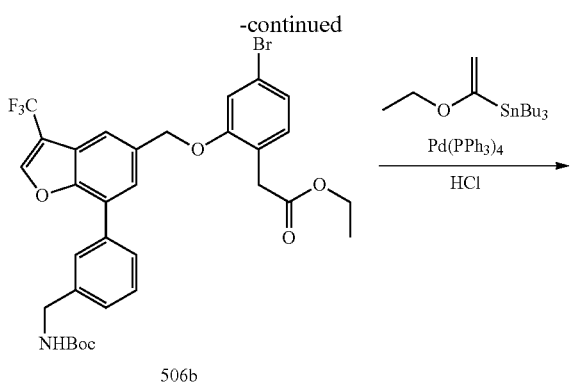

506b

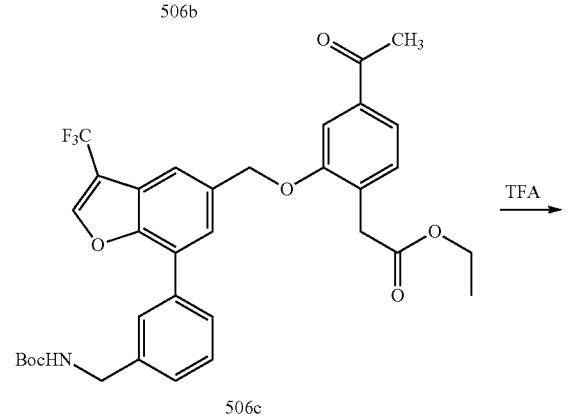

506c

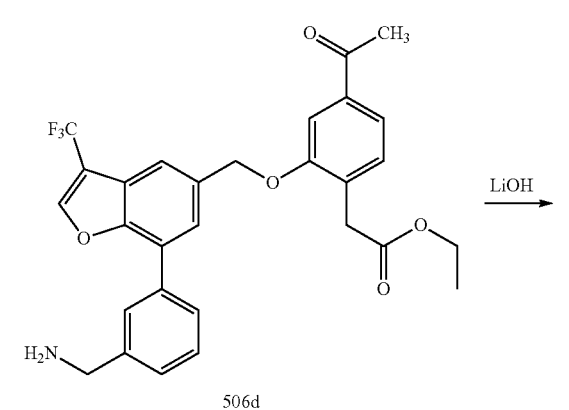

506d

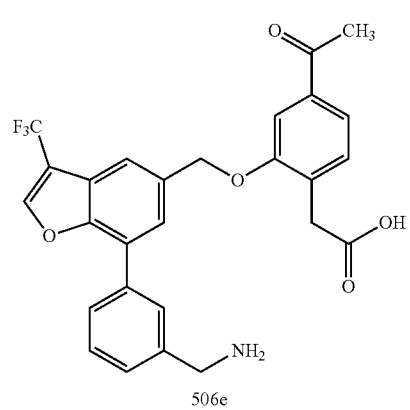

506e

1500

Preparation of 2-(4-acetyl-2-((7-(3-(aminomethyl) phenyl)-3-(trifluoromethyl)benzofuran-5-yl) methoxy)phenyl)acetic Acid (506e)

Step-1: Preparation of tert-butyl 3-(5-(hydroxymethyl)-3-(trifluoromethyl)benzofuran-7-yl)benzylcarbamate (506a)

Compound 506a was prepared according to the procedure reported in step-3 of scheme-1 from (7-bromo-3-(trifluoromethyl)benzofuran-5-yl)methanol (154d)(1.0 g, 3.39 mmol) in dioxane (30 mL) using tert-butyl 3-(4,4,5,5-tetramethyl-1,3,2-dioxaborolan-2-yl)benzylcarbamate (3b) (1.129 g, 3.39 mmol), Pd(PPh$_3$)$_2$Cl$_2$ (357 mg, 0.508 mmol) and a solution of K$_2$CO$_3$ (1.405 g, 10.17 mmol)) in water (3 mL) under a nitrogen atmosphere heating at 100° C. for 3 h on oil bath. This gave after workup and purification by flash column chromatography [silica gel (40g), eluting with 0 to 35% ethyl acetate in hexanes)] to give tert-butyl 3-(5-(hydroxymethyl)-3-(trifluoromethyl)benzofuran-7-yl)benzylcarbamate (506a) (1.05 g, 74% yield) as a light brown gummy solid. $^1$H NMR (300 MHz, DMSO-d$_6$) δ 8.83 (q, J=1.6 Hz, 1H), 7.77-7.66 (m, 2H), 7.65 (s, 1H), 7.59 (s, 1H), 7.47 (dq, J=12.6, 7.0, 6.2 Hz, 2H), 7.40-7.23 (m, 1H), 5.40 (t, J=5.7 Hz, 1H), 4.69 (d, J=5.7 Hz, 2H), 4.23 (d, J=6.2 Hz, 2H), 1.40 (s, 9H); $^{19}$F NMR (282 MHz, DMSO-d$_6$) δ−58.10; MS (ES+): 444.1 (M+Na).

Step-2: Preparation of Ethyl 2-(4-bromo-2-((7-(3-(((tert-butoxycarbonyl)amino)methyl)phenyl)-3-(trifluoromethyl)benzofuran-5-yl)methoxy)phenyl) acetate (506b)

Compound 506b was prepared according to the procedure reported in step-2 of scheme-23 from tert-butyl 3-(5-(hydroxymethyl)-3-(trifluoromethyl)benzofuran-7-yl)benzylcarbamate (506a) (550 mg, 1.305 mmol) in DCM (20 mL) using triphenylphosphine (445 mg, 1.697 mmol), ethyl 2-(4-bromo-2-hydroxyphenyl)acetate (182a) (338 mg, 1.305 mmol) and a solution of (E)-bis(4-chlorobenzyl) diazene-1,2-dicarboxylate (DCAD, 623 mg, 1.697 mmol) in DCM (20 mL). This gave after workup and purification by flash column chromatography (silica gel, 40 g, eluting with 0 to 25% ethyl acetate in hexanes) to give ethyl 2-(4-bromo-2-((7-(3-(((tert-butoxycarbonyl)amino)methyl)phenyl)-3-(trifluoromethyl)benzofuran-5-yl)methoxy)phenyl)acetate (506b) (695 mg, 80% yield) as a light brown oil. $^1$H NMR (300 MHz, DMSO-d$_6$) δ 8.95-8.78 (m, 1H), 7.78 (s, 1H), 7.75-7.68 (m, 3H), 7.57-7.42 (m, 2H), 7.39-7.31 (m, 2H), 7.24-7.10 (m, 2H), 5.33 (s, 2H), 4.23 (d, J=6.2 Hz, 2H), 3.89 (q, J=7.1 Hz, 2H), 3.60 (s, 2H), 1.39 (s, 9H), 0.93 (t, J=7.1 Hz, 3H); $^{19}$F NMR (282 MHz, DMSO-d$_6$) δ−58.07.

Step-3: Preparation of Ethyl 2-(4-acetyl-2-((7-(3-(((tert-butoxycarbonyl)amino)methyl)phenyl)-3-(trifluoromethyl)benzofuran-5-yl)methoxy)phenyl) acetate (506c)

Compound 506c was prepared according to the procedure reported in step-1 of scheme-262 from ethyl 2-(4-bromo-2-((7-(3-(((tert-butoxycarbonyl)amino)methyl)phenyl)-3-(trifluoromethyl)benzofuran-5-yl)methoxy)phenyl)acetate (506b) (570 mg, 0.860 mmol) in toluene (20 mL) using tributyl(1-ethoxyvinyl)stannane (0.383 mL, 1.075 mmol) and Pd(PPh$_3$)$_4$ (99 mg, 0.086 mmol) and heating at reflux for 24 h under a nitrogen atmosphere, followed by hydrolysis using 3 N aqueous HCl (0.86 mL, 2.58 mmol). This gave after workup and purification by flash column chromatography (Silica gel, 40 g, eluting with ethyl acetate in hexanes from 0-35%] to give ethyl 2-(4-acetyl-2-((7-(3-(((tert-butoxycarbonyl)amino)methyl)phenyl)-3-(trifluoromethyl)benzofuran-5-yl)methoxy)phenyl)acetate (506c) (290 mg, 5% yield) as a clear oil. $^1$H NMR (300 MHz, DMSO-$d_6$) δ 8.89 (s, 1H), 7.83 (s, 1H), 7.78-7.71 (m, 3H), 7.68-7.32 (m, 6H), 5.40 (s, 2H), 4.24 (d, J=6.2 Hz, 2H), 3.91 (q, J=7.1 Hz, 2H), 3.72 (s, 2H), 2.59 (s, 3H), 1.39 (s, 9H), 0.95 (t, J=7.1 Hz, 3H); $^{19}$F NMR (282 MHz, DMSO) δ−58.08.

Step-4: Preparation of Ethyl 2-(4-acetyl-2-((7-(3-(aminomethyl)phenyl)-3-(trifluoromethyl)benzofuran-5-yl)methoxy)phenyl)acetate (506d)

Compound 506d was prepared according to the procedure reported in step-5 of scheme-1 from ethyl 2-(4-acetyl-2-((7-(3-(((tert-butoxycarbonyl)amino)methyl)phenyl)-3-(trifluoromethyl)benzofuran-5-yl)methoxy)phenyl)acetate (506c) (270 mg, 0.432 mmol) in DCM (6.5 mL) using TFA (0.665 mL, 8.63 mmol). This gave after workup ethyl 2-(4-acetyl-2-((7-(3-(aminomethyl)phenyl)-3-(trifluoromethyl)benzofuran-5-yl)methoxy)phenyl)acetate (506d) (225 mg, 99% yield). $^1$H NMR (300 MHz, DMSO-$d_6$) δ 8.92 (q, J=1.7 Hz, 1H), 8.25 (s, 2H), 7.97 (s, 1H), 7.91 (d, J=7.5 Hz, 1H), 7.86 (s, 1H), 7.79 (s, 1H), 7.66-7.58 (m, 2H), 7.41 (d, J=7.7 Hz, 1H), 7.26-7.16 (m, 2H), 5.42 (s, 2H), 4.16 (d, J=5.9 Hz, 2H), 3.93 (q, J=7.1 Hz, 2H), 3.74 (s, 2H), 2.59 (s, 3H), 0.97 (t, J=7.1 Hz, 3H); $^{19}$F NMR (282 MHz, DMSO-$d_6$) δ−58.06; MS (ES+): 526.2 (M+1).

Step-5: Preparation of 2-(4-acetyl-2-((7-(3-(aminomethyl)phenyl)-3-(trifluoromethyl)benzofuran-5-yl)methoxy)phenyl)acetic Acid (506e)

Compound 506e was prepared according to the procedure reported in step-6 of scheme-1 from ethyl 2-(4-acetyl-2-((7-(3-(aminomethyl)phenyl)-3-(trifluoromethyl)benzofuran-5-yl)methoxy)phenyl)acetate (506d) (220 mg, 0.419 mmol) in THF (2.5 mL), acetonitrile (1.25 mL) using aqueous 1 N lithium hydroxide monohydrate (1.25 mL, 1.25 mmol) and stirring the reaction for 24 h. This gave after workup and purification by reverse phase column chromatography [C-18 column, eluting with water (0.1% HCl)/acetonitrile from 0 to 100%] to afford 2-(4-acetyl-2-((7-(3-(aminomethyl)phenyl)-3-(trifluoromethyl)benzofuran-5-yl)methoxy)phenyl)acetic acid (506e) (167 mg, 80% yield) HCl salt as a white solid; $^1$H NMR (300 MHz, DMSO-$d_6$) δ 8.92 (s, 1H), 8.02 (s, 1H), 7.96-7.80 (m, 3H), 7.68-7.54 (m, 4H), 7.41 (d, J=7.6 Hz, 1H), 5.43 (s, 2H), 4.14 (s, 2H), 3.70 (s, 2H), 2.51 (s, 3H); $^{19}$F NMR (282 MHz, DMSO-$d_6$) δ−58.01; MS (ES+): 498.2 (M+1).

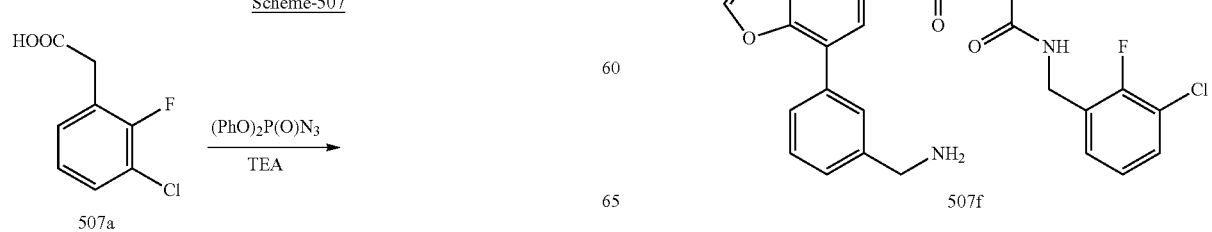

Scheme-507

Preparation of (S)-N2-(7-(3-(aminomethyl)phenyl)benzofuran-5-yl)-N1-(3-chloro-2-fluorobenzyl)pyrrolidine-1,2-dicarboxamide (507f)

Step-1: Preparation of 2-(3-chloro-2-fluorophenyl)acetyl azide (507b)

Diphenyl phosphoryl azide (1.182 mL, 5.30 mmol) was added to a suspension of 2-(3-chloro-2-fluorophenyl)acetic acid (507a) (1 g, 5.30 mmol), TEA (0.739 mL, 5.30 mmol) in Toluene (15 mL) stirred at room temperature for 18 h. The reaction mixture was concentrated in vacuum then purified by quick column chromatography on silica gel (4g, DCM) yielding 2-(3-chloro-2-fluorophenyl)acetyl azide (507b) (1.1 g, 97% yield). $^1$H NMR (300 MHz, DMSO-$d_6$) δ 7.57-7.50 (m, 1H), 7.37-7.31 (m, 1H), 7.22-7.18 (m, 1H), 3.92 (s, 2H).

Step-2: Preparation of (S)-tert-butyl 1-((3-chloro-2-fluorobenzyl)carbamoyl)pyrrolidine-2-carboxylate (507c)

A suspension of 2-(3-chloro-2-fluorophenyl)acetyl azide (507b) (1.1 g, 5.15 mmol) in toluene (20 mL) was heated at reflux for 1.5 h. The reaction mixture was cooled to room temperature and added triethylamine (1.436 mL, 10.30 mmol), (S)-tert-butyl pyrrolidine-2-carboxylate (882 mg, 5.15 mmol) in THF (10 mL) followed by stirring at RT for 1.5 h. The mixture was concentrated, the obtained residue was purified by chromatography [silica, (40g), eluting with hexanes/10% methanol in ethyl acetate (1:0 to 1:1)] to give (S)-tert-butyl 1-((3-chloro-2-fluorobenzyl)carbamoyl)pyrrolidine-2-carboxylate (507c) (1.45 g, 4.06 mmol, 79% yield) as a pale-yellow oil. $^1$H NMR (300 MHz, DMSO-$d_6$) δ 7.44 (t, J=7.5 Hz, 1H), 7.29 (q, J=6.8, 6.3 Hz, 1H), 7.17 (t, J=7.8 Hz, 1H), 6.89 (t, J=5.9 Hz, 1H), 4.37-4.18 (m, 2H), 4.13 (dd, J=8.7, 2.9 Hz, 1H), 3.45-3.32 (m, 2H), 2.19-2.03 (m, 1H), 1.94-1.67 (m, 3H), 1.36 (d, J=1.1 Hz, 9H); $^{19}$F NMR (282 MHz, DMSO-$d_6$) δ−122.15; MS (ES+): 379.1 (M+Na).

Step-3: Preparation of (S)-1-((3-chloro-2-fluorobenzyl)carbamoyl)pyrrolidine-2-carboxylic acid (507d)

Compound 507d was prepared according to the procedure reported in step-5 of scheme-1 from (S)-tert-butyl 1-((3-chloro-2-fluorobenzyl)carbamoyl)pyrrolidine-2-carboxylate (507c) (1.42g, 3.98 mmol) in DCM (30 mL) using TFA (4.60 mL, 59.7 mmol). This gave after workup (S)-1-((3-chloro-2-fluorobenzyl)carbamoyl)pyrrolidine-2-carboxylic acid (507d) (1.19 g, 99% yield) as colorless foam, which was used as such for next step. MS (ES+): 301.1 (M+1).

Step-4: Preparation of (S)-tert-butyl 3-(5-(1-((3-chloro-2-fluorobenzyl)carbamoyl)pyrrolidine-2-carboxamido)benzofuran-7-yl)benzylcarbamate (507e)

Compound 507e was prepared according to the procedure reported in step-4 of scheme-1 from (S)-1-((3-chloro-2-fluorobenzyl)carbamoyl)pyrrolidine-2-carboxylic acid (507d) (80 mg, 0.266 mmol) in DMF (1 mL) using tert-butyl 3-(5-aminobenzofuran-7-yl)benzylcarbamate (217c) (90 mg, 0.266 mmol), DIPEA (0.185 mL, 1.064 mmol) and HATU (152 mg, 0.399 mmol). This gave after workup and purification by flash column chromatography [silica (24 g), eluting with 0 to 50% ethyl acetate/Hexane) yielding (S)-tert-butyl 3-(5-(1-((3-chloro-2-fluorobenzyl)carbamoyl)pyrrolidine-2-carboxamido)benzofuran-7-yl)benzylcarbamate (507e) (22 mg, 13% yield) as a light brown gum. MS (ES+): 643.2 (M+Na).

Step-5: Preparation of (S)-N2-(7-(3-(aminomethyl)phenyl)benzofuran-5-yl)-N1-(3-chloro-2-fluorobenzyl)pyrrolidine-1,2-dicarboxamide (507f)

Compound 507f was prepared according to the procedure reported in step-5 of scheme-1 from (S)-tert-butyl 3-(5-(1-((3-chloro-2-fluorobenzyl)carbamoyl)pyrrolidine-2-carboxamido)benzofuran-7-yl)benzylcarbamate (507e) (21 mg, 0.034 mmol) in DCM (0.6 mL) using TFA (0.052 mL, 0.676 mmol). This gave after workup and purification by reverse column [C18 (50 g), eluting with ACN in water (containing 0.1% HCl) from 0-100%] (S)-N2-(7-(3-(aminomethyl)phenyl)benzofuran-5-yl)-N1-(3-chloro-2-fluorobenzyl)pyrrolidine-1,2-dicarboxamide (507f) (9 mg, 51% yield) HCl salt as a white solid; $^1$H NMR (300 MHz, DMSO-$d_6$) δ 10.07 (s, 1H), 8.28 (s, 3H, $D_2O$ exchangeable), 8.04 (t, J=1.6 Hz, 1H), 7.92-7.85 (m, 2H), 7.85-7.74 (m, 2H), 7.58 (dt, J=15.5, 7.7 Hz, 2H), 7.42 (t, J=7.6 Hz, 1H), 7.35 (t, J=7.3 Hz, 1H), 7.15 (t, J=7.9 Hz, 1H), 7.04 (t, J=1.7 Hz, 1H), 6.99 (t, J=5.9 Hz, 1H, $D_2O$ exchangeable), 4.53-4.04 (m, 5H), 3.63-3.36 (m, 2H), 2.21-1.88 (m, 4H); $^{19}$F NMR (282 MHz, DMSO-$d_6$) δ−122.16; MS (ES+): 521.2 (M+1); (ES−): 519.1 (M−1), 555.1 (M+Cl).

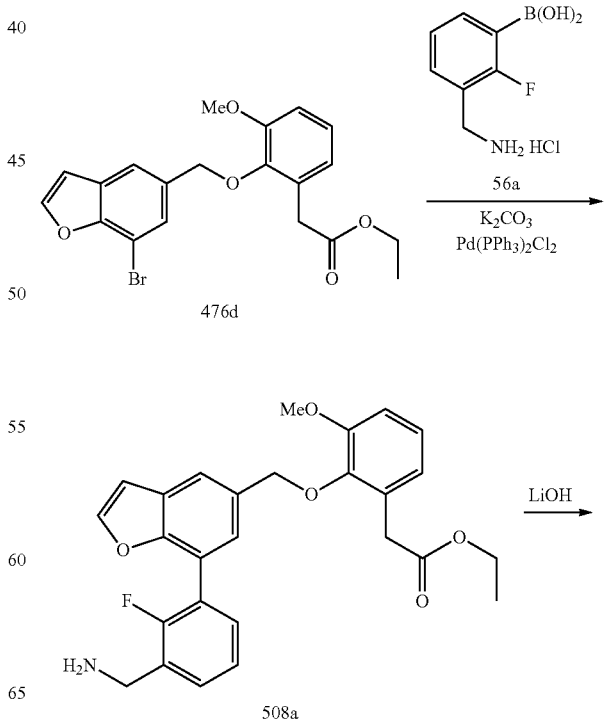

Scheme-508

-continued

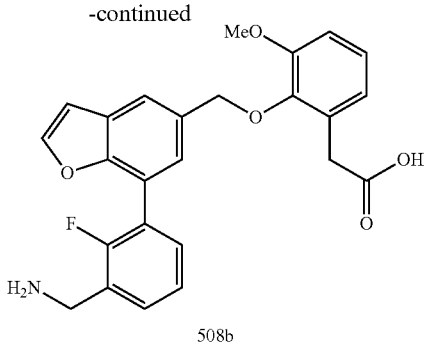

508b

Preparation of 2-(2-((7-(3-(aminomethyl)-2-fluorophenyl)benzofuran-5-yl)methoxy)-3-methoxyphenyl)acetic Acid (508b)

Step-1: Preparation of Ethyl 2-(2-((7-(3-(aminomethyl)-2-fluorophenyl)benzofuran-5-yl)methoxy)-3-methoxyphenyl)acetate (508a)

Compound 508a was prepared according to the procedure reported in step-3 of scheme-1 from ethyl 2-(2-((7-bromobenzofuran-5-yl)methoxy)-3-methoxyphenyl)acetate (476d) (160 mg, 0.382 mmol) in dioxane (4 mL), water (1 mL) using (3-(aminomethyl)-2-fluorophenyl)boronic acid hydrochloride (56a) (118 mg, 0.572 mmol), $Pd(PPh_3)_2Cl_2$ (27 mg, 0.038 mmol) and a 3.3 M aqueous $K_2CO_3$ (0.347 mL, 1.145 mmol) under an $N_2$ atmosphere heating at 100° C. for 16 h on oil bath. This gave after workup, purification by flash column chromatography (silica gel, 12 g, eluting with 0-3% MeOH in DCM) ethyl 2-(2-((7-(3-(aminomethyl)-2-fluorophenyl)benzofuran-5-yl)methoxy)-3-methoxyphenyl)acetate (508a) (127 mg, 72% yield) as a colorless oil. $^1$H NMR (300 MHz, DMSO-$d_6$) δ 8.03 (t, J=1.7 Hz, 1H), 7.73 (d, J=1.7 Hz, 1H), 7.67-7.55 (m, 1H), 7.50-7.38 (m, 2H), 7.31 (t, J=7.7 Hz, 1H), 7.13-7.00 (m, 3H), 6.82 (t, J=4.3 Hz, 1H), 5.06 (s, 2H), 3.97-3.88 (m, 2H), 3.86 (s, 3H), 3.84 (s, 2H), 3.58 (s, 2H), 1.01 (d, J=7.1 Hz, 3H). $^{19}$F NMR (282 MHz, DMSO-$d_6$) δ−121.88; LC-MS: t=2.16 min; MS (ES+): 464 (M+1).

Step-2: Preparation of 2-(2-((7-(3-(aminomethyl)-2-fluorophenyl)benzofuran-5-yl)methoxy)-3-methoxyphenyl)acetic Acid (508b)

Compound 508b was prepared according to the procedure reported in step-6 of scheme-1 from ethyl 2-(2-((7-(3-(aminomethyl)-2-fluorophenyl)benzofuran-5-yl)methoxy)-3-methoxyphenyl)acetate (508a) (127 mg, 0.274 mmol) in MeOH (3 mL) using a 2.0 M aqueous LiOH (0.685 mL, 1.370 mmol) and stirring at room temperature for 16 h. This gave after workup and purification by reverse phase column [C18 (100 g), eluting with 0-60% MeCN in $H_2O$ containing 0.1% HCl] 2-(2-((7-(3-(aminomethyl)-2-fluorophenyl)benzofuran-5-yl)methoxy)-3-methoxyphenyl)acetic acid (508b) (60 mg, 50% yield) HCl salt as a white solid; $^1$H NMR (300 MHz, DMSO-$d_6$) δ 8.62 (s, 2H), 8.06 (d, J=2.1 Hz, 1H), 7.80 (s, 1H), 7.76-7.60 (m, 2H), 7.52-7.36 (m, 2H), 7.08 (d, J=2.1 Hz, 1H), 7.06-6.97 (m, 2H), 6.83 (dd, J=6.5, 2.7 Hz, 1H), 5.07 (s, 2H), 4.18 (s, 2H), 3.86 (s, 3H), 3.54 (s, 2H). $^{19}$F NMR (282 MHz, DMSO-$d_6$) δ−118.58; MS (ES+): 436 (M+1), (ES−): 434 (M−1); Analysis calculated for $C_{25}H_{22}FNO_5 \cdot 1.1HCl \cdot H_2O$: C, 60.84; H, 5.13; Cl, 7.90; N, 2.84; Found: C, 61.09; H, 4.94; Cl, 7.78; N, 3.15.

Scheme-509

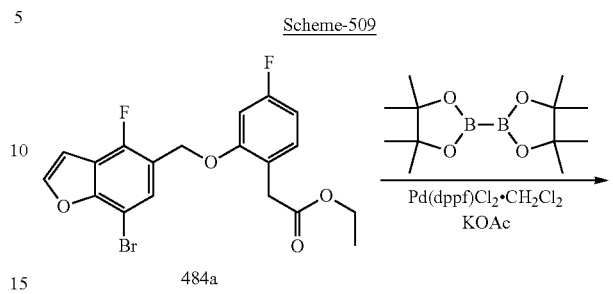

484a

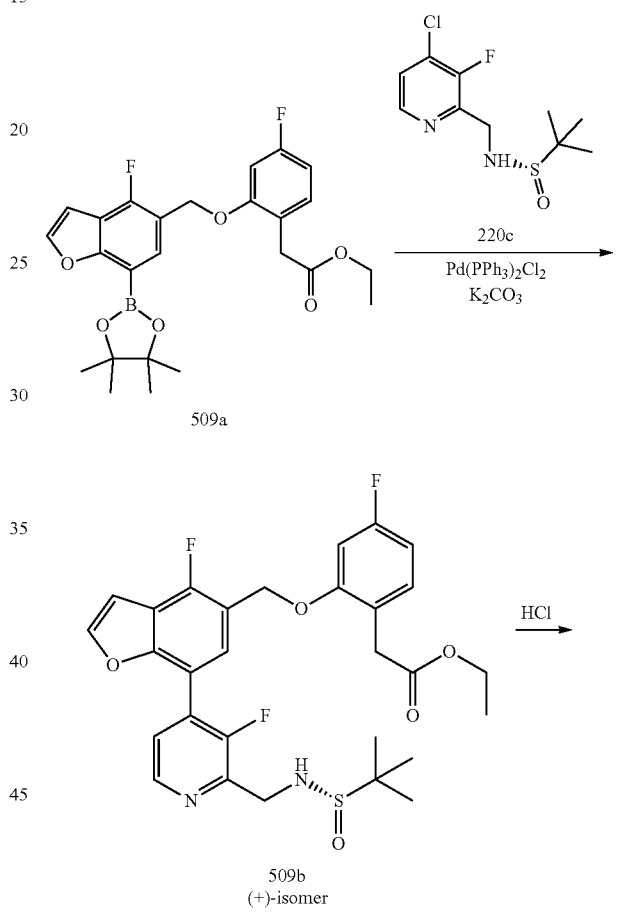

509a 509b
(+)-isomer

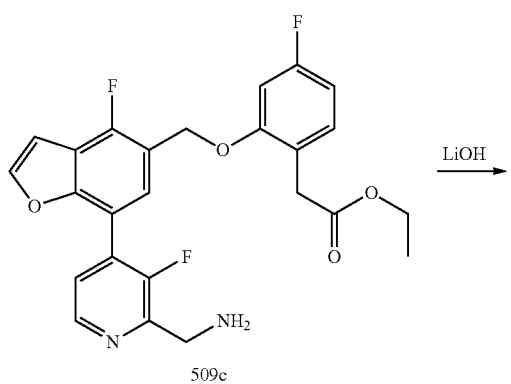

509c

-continued

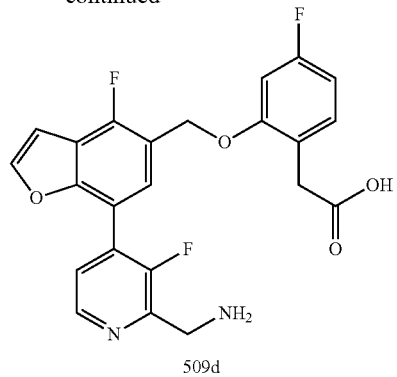

509d

Preparation of 2-(2-((7-(2-(aminomethyl)-3-fluoro-pyridin-4-yl)-4-fluorobenzofuran-5-yl)methoxy)-4-fluorophenyl)acetic Acid (509d)

Step-1: Preparation of Ethyl 2-(4-fluoro-2-((4-fluoro-7-(4,4,5,5-tetramethyl-1,3,2-dioxaborolan-2-yl)benzofuran-5-yl)methoxy)phenyl)acetate (509a)

Compound 509a was prepared according to the procedure reported in step-1 of scheme-59 from ethyl 2-(2-((7-bromo-4-fluorobenzofuran-5-yl)methoxy)-4-fluorophenyl)acetate (484a) (299 mg, 0.703 mmol) using bis(pinacolato)diboron (268 mg, 1.055 mmol), potassium acetate (207 mg, 2.109 mmol) and Pd(dppf)Cl$_2$—CH$_2$Cl$_2$ (86 mg, 0.105 mmol) in anhydrous dioxane (12 mL) under an argon atmosphere and heating at 95° C. overnight. This gave after workup and purification by flash column chromatography [silica (12 g), eluting with EtOAc in hexane from 0-40%] ethyl 2-(4-fluoro-2-((4-fluoro-7-(4,4,5,5-tetramethyl-1,3,2-dioxaborolan-2-yl)benzofuran-5-yl)methoxy)phenyl)acetate (509a) (265 mg, 80% yield) as a white solid. $^1$H NMR (300 MHz, DMSO-d$_6$) δ 8.14 (d, J=2.3 Hz, 1H), 7.74 (d, J=7.8 Hz, 1H), 7.23 (dd, J=8.4, 6.9 Hz, 1H), 7.16-7.06 (m, 2H), 6.75 (td, J=8.5, 2.5 Hz, 1H), 5.26-5.13 (m, 2H), 3.91 (q, J=7.1 Hz, 2H), 3.48 (s, 2H), 1.33 (s, 12H), 0.95 (t, J=7.1 Hz, 3H); $^{19}$F NMR (282 MHz, DMSO-d$_6$) δ −112.65, −118.76.

Step-2: Preparation of (+)-(S)-ethyl 2-(2-((7-(2-((1,1-dimethylethylsulfinamido)methyl)-3-fluoropyridin-4-yl)-4-fluorobenzofuran-5-yl)methoxy)-4-fluorophenyl)acetate (509b)

Compound 509b was prepared according to the procedure reported in step-3 of scheme-1 from ethyl 2-(4-fluoro-2-((4-fluoro-7-(4,4,5,5-tetramethyl-1,3,2-dioxaborolan-2-yl)benzofuran-5-yl)methoxy)phenyl)acetate (509a) (262 mg, 0.555 mmol) in dioxane (5 mL) using (+)-(S)—N-((4-chloro-3-fluoropyridin-2-yl)methyl)-2-methylpropane-2-sulfinamide (220c) (191 mg, 0.721 mmol), Pd(PPh$_3$)$_2$Cl$_2$ (58 mg, 0.083 mmol) and a solution of K$_2$CO$_3$ (230 mg, 1.664 mmol) in water (0.5 mL) under a nitrogen atmosphere heating at 100° C. for 3 h on oil bath. This gave after workup and purification by flash column chromatography [silica gel (12 g), eluting with methanol in DCM from 0-15%] (+)-(S)-ethyl 2-(2-((7-(2-((1,1-dimethylethylsulfinamido)methyl)-3-fluoropyridin-4-yl)-4-fluorobenzofuran-5-yl)methoxy)-4-fluorophenyl)acetate (509b) (319 mg, 100% yield) as a dark oil; MS (ES+): 575.2 (M+1); Optical rotation [t]D=+18.56 (c=0.485, MeOH).

Step-3: Preparation of Ethyl 2-(2-((7-(2-(aminomethyl)-3-fluoropyridin-4-yl)-4-fluorobenzofuran-5-yl)methoxy)-4-fluorophenyl)acetate (509c)

Compound 509c was prepared according to the procedure reported in step-3 of scheme-305 from (+)-(S)-ethyl 2-(2-((7-(2-(((1,1-dimethylethylsulfinamido)methyl)-3-fluoropyridin-4-yl)-4-fluorobenzofuran-5-yl)methoxy)-4-fluorophenyl)acetate (509b) (310 mg, 0.539 mmol) in ethanol (8 mL) using 4 M HCl in dioxane (0.8 mL, 3.20 mmol) and stirring at room temperature for 1 h. This gave after workup and purification by flash column chromatography [silica gel (12 g), eluting with DMA-80/DCM from 0-100%] ethyl 2-(2-((7-(2-(aminomethyl)-3-fluoropyridin-4-yl)-4-fluorobenzofuran-5-yl)methoxy)-4-fluorophenyl)acetate (509c) (143 mg, 56% yield) as pale yellow oil; $^1$H NMR (300 MHz, DMSO-d$_6$) δ 8.52 (d, J=4.9 Hz, 1H), 8.18 (d, J=1.9 Hz, 1H), 7.67 (d, J=6.6 Hz, 1H), 7.59 (t, J=5.3 Hz, 1H), 7.30-7.19 (m, 2H), 7.15 (dd, J=11.4, 2.5 Hz, 1H), 6.76 (td, J=9.7, 9.0, 2.4 Hz, 1H), 5.29 (s, 2H), 3.94 (s, 2H), 3.84 (q, J=7.1 Hz, 2H), 3.53 (s, 2H), 0.90 (t, J=7.7, 6.5 Hz, 3H); $^{19}$F NMR (282 MHz, DMSO-d$_6$) δ −112.55, −121.74, −130.73. MS (ES+): 471.2 (M+1).

Step-4: Preparation of 2-(2-((7-(2-(aminomethyl)-3-fluoropyridin-4-yl)-4-fluorobenzofuran-5-yl)methoxy)-4-fluorophenyl)acetic Acid (509d)

Compound 509d was prepared according to the procedure reported in step-6 of scheme-1 from ethyl 2-(2-((7-(2-(aminomethyl)-3-fluoropyridin-4-yl)-4-fluorobenzofuran-5-yl)methoxy)-4-fluorophenyl)acetate (509c) (140 mg, 0.298 mmol) in MeOH/THF (3 mL, each) using LiOH (60 mg, 1.430 mmol) in water (2 mL) and stirring at room temperature overnight. This gave after workup and purification by reverse phase column [C-18 column, 50g, eluting with acetonitrile in water (containing 0.1% HCl) from 0-100%] 2-(2-((7-(2-(aminomethyl)-3-fluoropyridin-4-yl)-4-fluorobenzofuran-5-yl)methoxy)-4-fluorophenyl)acetic acid (509d) (89 mg, 68% yield) HCl salt as a white solid. $^1$H NMR (300 MHz, DMSO-d$_6$) δ 12.06 (s, 1H), 8.84-8.48 (m, 4H), 8.29-8.11 (m, 1H), 7.91-7.66 (m, 2H), 7.31-7.19 (m, 2H), 7.14 (dd, J=11.4, 2.5 Hz, 1H), 6.77 (td, J=8.4, 2.4 Hz, 1H), 5.34 (s, 2H), 4.36 (d, J=5.9 Hz, 2H), 3.51 (s, 2H); $^{19}$F NMR (282 MHz, DMSO-d$_6$) δ −112.87, −121.02, −128.52; MS (ES+): 443.1 (M+1); MS (ES−): 441.1 (M−1).

Scheme-510

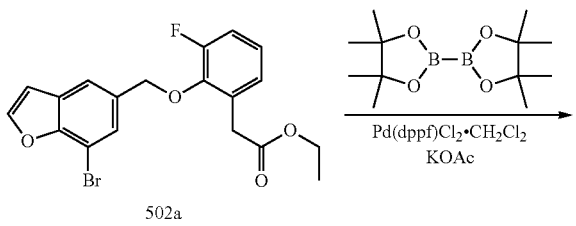

502a

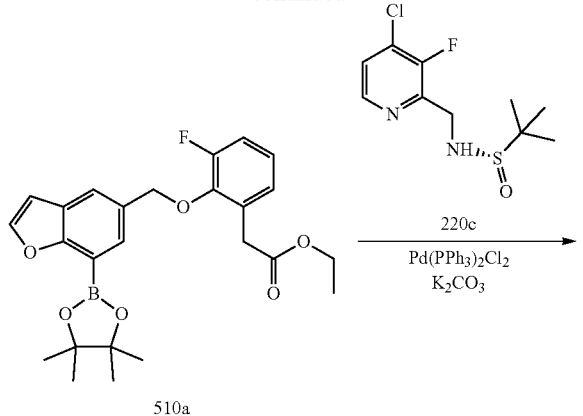

510a

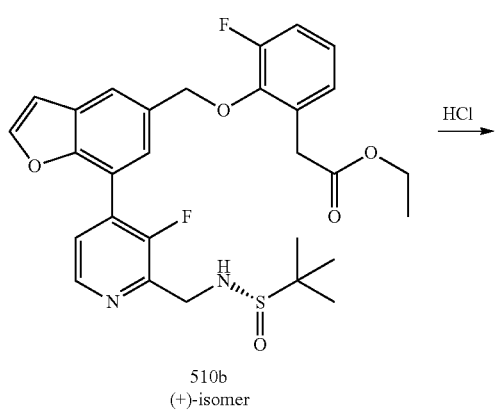

510b
(+)-isomer

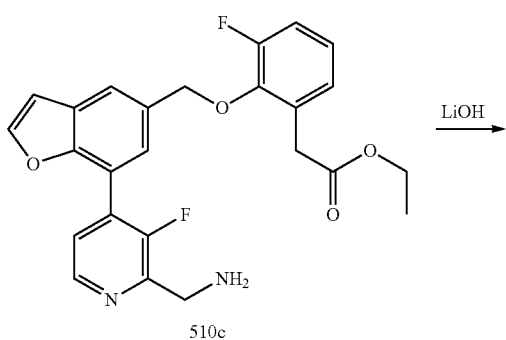

510c

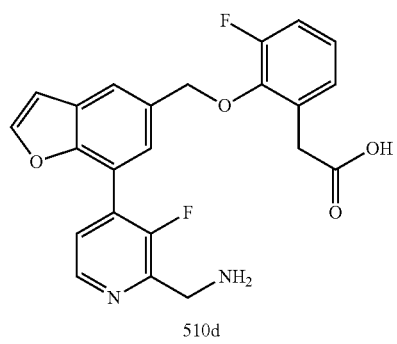

510d

Preparation of 2-(2-((7-(2-(aminomethyl)-3-fluoropyridin-4-yl)benzofuran-5-yl)methoxy)-3-fluorophenyl)acetic Acid (510d)

Step-1: Preparation of Ethyl 2-(3-fluoro-2-((7-(4,4,5,5-tetramethyl-1,3,2-dioxaborolan-2-yl)benzofuran-5-yl)methoxy)phenyl)acetate (510a)

Compound 510a was prepared according to the procedure reported in step-1 of scheme-59 from ethyl 2-(2-((7-bromobenzofuran-5-yl)methoxy)-3-fluorophenyl)acetate (502a) (338 mg, 0.830 mmol) using bis(pinacolato)diboron (316 mg, 1.245 mmol), potassium acetate (244 mg, 2.490 mmol) and Pd(dppf)Cl$_2$—CH$_2$Cl$_2$ (102 mg, 0.124 mmol) in anhydrous dioxane (12 mL) under an argon atmosphere and heating at 95° C. overnight. This gave after workup and purification by flash column chromatography [silica (12 g), eluting with EtOAc in hexane from 0-40%] ethyl 2-(3-fluoro-2-((7-(4,4,5,5-tetramethyl-1,3,2-dioxaborolan-2-yl)benzofuran-5-yl)methoxy)phenyl)acetate (510a) (305 mg, 81% yield) as a transparent oil. $^1$H NMR (300 MHz, DMSO-d$_6$) δ 8.07 (d, J=2.2 Hz, 1H), 7.83 (d, J=1.9 Hz, 1H), 7.67 (d, J=1.9 Hz, 1H), 7.23 (ddd, J=11.7, 6.1, 3.8 Hz, 1H), 7.08 (td, J=3.3, 2.4 Hz, 2H), 6.99 (d, J=2.2 Hz, 1H), 5.11 (s, 2H), 4.00 (q, J=7.1 Hz, 2H), 3.63 (s, 2H), 1.34 (s, 12H), 1.09 (t, J=7.1 Hz, 3H); $^{19}$F NMR (282 MHz, DMSO-d$_6$) δ−129.76.

Step-2: Preparation of (+)-(S)-ethyl 2-(2-((7-(2-((1,1-dimethylethylsulfinamido)methyl)-3-fluoropyridin-4-yl)benzofuran-5-yl)methoxy)-3-fluorophenyl)acetate (510b)

Compound 510b was prepared according to the procedure reported in step-3 of scheme-1 from ethyl 2-(3-fluoro-2-((7-(4,4,5,5-tetramethyl-1,3,2-dioxaborolan-2-yl)benzofuran-5-yl)methoxy)phenyl)acetate (510a) (300 mg, 0.660 mmol) in dioxane (5 mL) using (+)-(S)—N-((4-chloro-3-fluoropyridin-2-yl)methyl)-2-methylpropane-2-sulfinamide (220c) (227 mg, 0.858 mmol), Pd(PPh$_3$)$_2$Cl$_2$ (70 mg, 0.099 mmol) and a solution of K$_2$CO$_3$ (274 mg, 1.981 mmol) in water (0.5 mL) under a nitrogen atmosphere heating at 100° C. for 3 h on oil bath. This gave after workup and purification by flash column chromatography [silica gel (12 g), eluting with methanol in DCM from 0-15%] (+)-(S)-ethyl 2-(2-((7-(2-((1,1-dimethylethylsulfinamido)methyl)-3-fluoropyridin-4-yl)benzofuran-5-yl)methoxy)-3-fluorophenyl)acetate (510b) (368 mg, 100% yield) as a dark oil; MS (ES+): 557.2 (M+1); Optical rotation [t]D=+18.69 (c=0.76, MeOH).

Step-3: Preparation of Ethyl 2-(2-((7-(2-(aminomethyl)-3-fluoropyridin-4-yl)benzofuran-5-yl)methoxy)-3-fluorophenyl)acetate (510c)

Compound 510c was prepared according to the procedure reported in step-3 of scheme-305 from (+)-(S)-ethyl 2-(2-((7-(2-((1,1-dimethylethylsulfinamido)methyl)-3-fluoropyridin-4-yl)benzofuran-5-yl)methoxy)-3-fluorophenyl)acetate (510b) (360 mg, 0.647 mmol) in ethanol (8 mL) using 4 M HCl in dioxane (0.8 mL, 3.20 mmol) and stirring at room temperature for 1 h. This gave after workup and purification by flash column chromatography [silica gel (12 g), eluting with DMA-80/DCM from 0-100%] ethyl 2-(2-((7-(2-(aminomethyl)-3-fluoropyridin-4-yl)benzofuran-5-yl)methoxy)-3-fluorophenyl)acetate (510c) (180 mg, 62% yield) as a pale yellow oil; $^1$H NMR (300 MHz, DMSO-d$_6$) δ 8.54 (d, J=5.0 Hz, 1H), 8.15-8.06 (m, 1H), 7.86 (s, 1H), 7.62 (t, J=5.3 Hz, 1H), 7.54 (s, 1H), 7.30-7.16 (m, 1H), 7.16-7.01 (m, 3H), 5.20 (s, 2H), 4.02 (s, 2H), 3.94 (q, 2H), 3.66 (s, 2H), 1.01 (t, J=7.1, 1.1 Hz, 3H); $^{19}$F NMR (282 MHz, DMSO-$d_6$) δ −129.75, −130.33. MS (ES+): 553.2 (M+1).

Step-4: Preparation of 2-(2-((7-(2-(aminomethyl)-3-fluoropyridin-4-yl)benzofuran-5-yl)methoxy)-3-fluorophenyl)acetic Acid (510d)

Compound 510d was prepared according to the procedure reported in step-6 of scheme-1 from ethyl 2-(2-((7-(2-(aminomethyl)-3-fluoropyridin-4-yl)benzofuran-5-yl)methoxy)-3-fluorophenyl)acetate (510c) (175 mg, 0.387 mmol) in MeOH/THF (3 mL, each) using LiOH (83 mg, 1.978 mmol) in water (2 mL) and stirring at room temperature overnight. This gave after workup and purification by reverse phase column [C-18 column, 50g, eluting with acetonitrile in water (containing 0.1% HCl) from 0-100%] 2-(2-((7-(2-(aminomethyl)-3-fluoropyridin-4-yl)benzofuran-5-yl)methoxy)-3-fluorophenyl)acetic acid (510d) (115 mg, 70% yield) HCl salt as a white solid; $^1$H NMR (300 MHz, DMSO-$d_6$) δ 8.63 (s, 3H), 8.56 (d, J=5.0 Hz, 1H), 8.12-8.03 (m, 1H), 7.85 (s, 1H), 7.73 (t, J=5.3 Hz, 1H), 7.54 (s, 1H), 7.22-7.10 (m, 1H), 7.10-6.95 (m, 3H), 5.13 (s, 2H), 4.30 (d, J=5.9 Hz, 2H), 3.55 (s, 2H); $^{19}$F NMR (282 MHz, DMSO-$d_6$) δ −128.52, −129.88. MS (ES+): 425.1 (M+1); MS (ES−): 423.1 (M−1).

Scheme-511

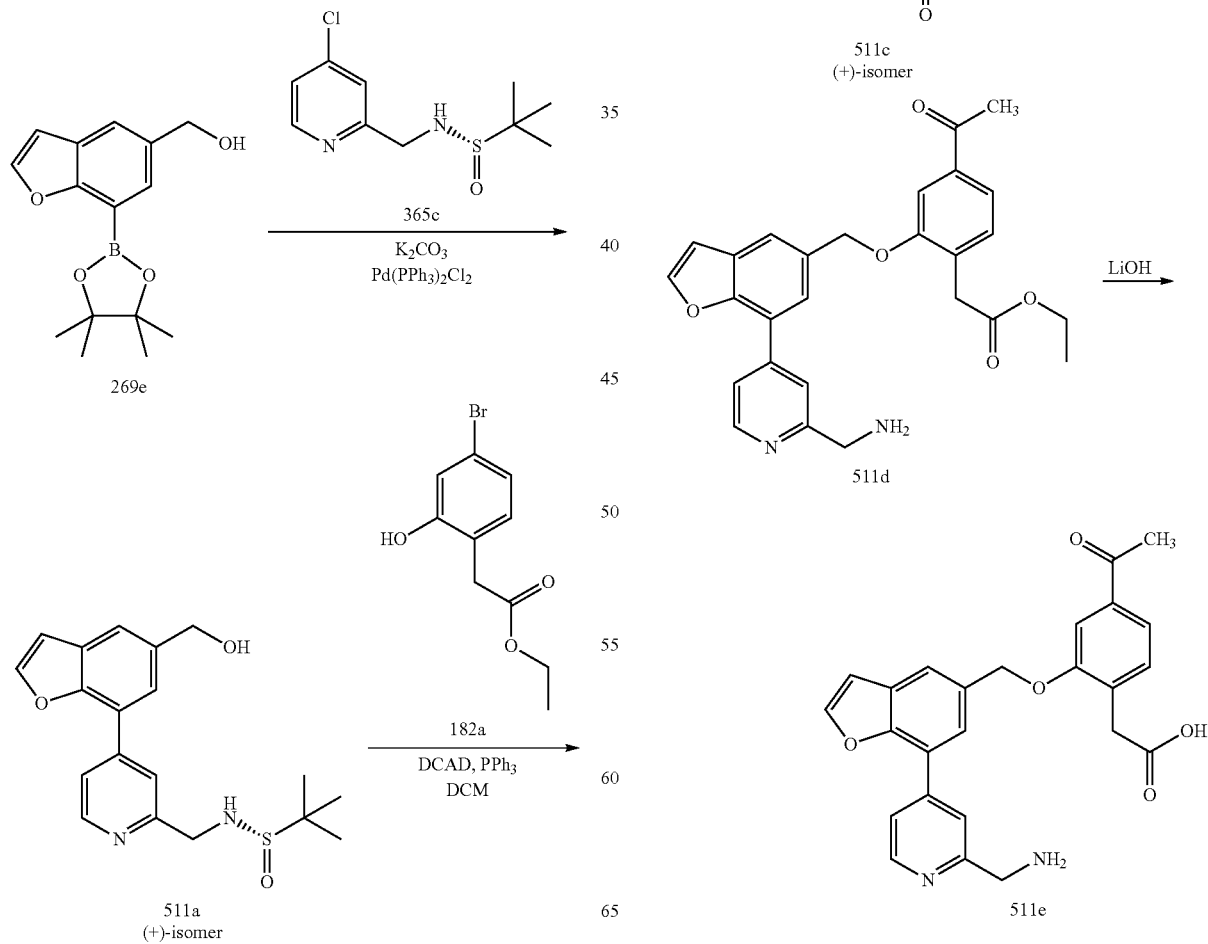

Preparation of 2-(4-acetyl-2-((7-(2-(aminomethyl) pyridin-4-yl)benzofuran-5-yl)methoxy)phenyl)acetic Acid (511e)

Step-1: Preparation of (+)-(S)—N-((4-(5-(hydroxymethyl)benzofuran-7-yl)pyridin-2-yl)methyl)-2-methylpropane-2-sulfinamide (511a)

Compound 511a was prepared according to the procedure reported in step-3 of scheme-1 from (7-(4,4,5,5-tetramethyl-1,3,2-dioxaborolan-2-yl)benzofuran-5-yl)methanol (269e) (1.5 g, 5.47 mmol) in dioxane (60 mL) using (+)-(S)—N-((4-chloropyridin-2-yl)methyl)-2-methylpropane-2-sulfinamide (365c) (1.620 g, 6.57 mmol), Pd(PPh$_3$)$_2$Cl$_2$ (0.576 g, 0.821 mmol) and a solution of potassium carbonate (2.269 g, 16.42 mmol) in water (7 mL) under a nitrogen atmosphere heating at 100° C. for 16 h on oil bath. This gave after workup and purification by flash column chromatography [silica gel (80 g), eluting with methanol in DCM from 0-7%] (+)-(S)—N-((4-(5-(hydroxymethyl)benzofuran-7-yl)pyridin-2-yl)methyl)-2-methylpropane-2-sulfinamide (511a) (875 mg, 45% yield) as an off-white gummy solid; $^1$H NMR (300 MHz, DMSO-d$_6$) δ 8.63 (dd, J=5.2, 0.8 Hz, 1H), 8.07 (d, J=2.2 Hz, 1H), 8.04-8.03 (m, 1H), 7.78 (dd, J=5.2, 1.8 Hz, 1H), 7.72-7.69 (m, 1H), 7.62 (d, J=1.6 Hz, 1H), 7.07 (d, J=2.2 Hz, 1H), 5.98 (t, J=6.1 Hz, 1H), 5.31 (t, J=5.7 Hz, 1H), 4.65 (dt, J=5.7, 0.7 Hz, 2H), 4.45-4.28 (m, 2H), 1.19 (s, 9H); MS (ES+): 359.10 (M+1); Optical rotation [α]$_D$=+32.77 (c=0.47, MeOH).

Step-2: Preparation of (+)-(S)-ethyl 2-(4-bromo-2-((7-(2-((1,1-dimethylethylsulfinamido)methyl)pyridin-4-yl)benzofuran-5-yl)methoxy)phenyl)acetate (511 b)

Compound 511b was prepared according to the procedure reported in step-2 of scheme-23 from (+)-(S)—N-((4-(5-(hydroxymethyl)benzofuran-7-yl)pyridin-2-yl)methyl)-2-methylpropane-2-sulfinamide (511a) (750 mg, 2.092 mmol) in DCM (25 mL) using triphenylphosphine (713 mg, 2.72 mmol), ethyl 2-(4-bromo-2-hydroxyphenyl)acetate (182a) (542 mg, 2.092 mmol) and a solution of (E)-bis(4-chlorobenzyl) diazene-1,2-dicarboxylate (DCAD, 999 mg, 2.72 mmol) in DCM (25 mL). This gave after workup and purification by flash column chromatography (silica gel, 40 g, eluting with 0 to 5% methanol in DCM) (+)-(S)-ethyl 2-(4-bromo-2-((7-(2-((1,1-dimethylethylsulfinamido)methyl)pyridin-4-yl)benzofuran-5-yl)methoxy)phenyl)acetate (511 b) (906 mg, 72% yield) as a clear oil; $^1$H NMR (300 MHz, DMSO-d$_6$) δ 8.65 (dd, J=5.2, 0.8 Hz, 1H), 8.12 (d, J=2.2 Hz, 1H), 8.07-8.04 (m, 1H), 7.81 (d, J=1.6 Hz, 1H), 7.78 (dd, J=5.3, 1.8 Hz, 1H), 7.72 (d, J=1.6 Hz, 1H), 7.35 (d, J=1.8 Hz, 1H), 7.20 (d, J=8.0 Hz, 1H), 7.15-7.10 (m, 2H), 5.96 (t, J=6.1 Hz, 1H), 5.28 (s, 2H), 4.47-4.28 (m, 2H), 3.95-3.86 (m, 2H), 3.61 (s, 2H), 1.18 (s, 9H), 0.94 (t, J=7.1 Hz, 3H); MS (ES+): 599.10 (M+1); Optical rotation [α]$_D$=+18.6 (c=0.5, MeOH).

Step-3: Preparation of (+)-(S)-ethyl 2-(4-acetyl-2-((7-(2-((1,1-dimethylethylsulfinamido)methyl)pyridin-4-yl)benzofuran-5-yl)methoxy)phenyl)acetate (511c)

Compound 511c was prepared according to the procedure reported in step-1 of scheme-262 from (+)-(S)-ethyl 2-(4-bromo-2-((7-(2-((1,1-dimethylethylsulfinamido)methyl) pyridin-4-yl)benzofuran-5-yl)methoxy)phenyl)acetate (511b) (800 mg, 1.334 mmol) in toluene (25 mL) using tributyl(1-ethoxyvinyl)stannane (0.594 mL, 1.668 mmol) and Pd(PPh$_3$)$_4$ (154 mg, 0.133 mmol) and heating at reflux for 24 h under a nitrogen atmosphere, followed by hydrolysis using 3 N aqueous HCl (1.334 mL, 4.00 mmol). This gave after workup and purification by flash column chromatography (Silica gel, 24 g, eluting with 0-5% methanol in DCM) (+)-(S)-ethyl 2-(4-acetyl-2-((7-(2-((1,1-dimethylethylsulfinamido)methyl)pyridin-4-yl)benzofuran-5-yl)methoxy)phenyl)acetate (511c) (211 mg, 28% yield) as a clear oil; $^1$H NMR (300 MHz, DMSO-d$_6$) δ 8.65 (d, J=5.2 Hz, 1H), 8.14-8.10 (m, 1H), 8.07 (s, 1H), 7.84 (s, 1H), 7.81-7.74 (m, 2H), 7.62 (s, 1H), 7.59 (d, J=7.9 Hz, 1H), 7.40 (d, J=7.7 Hz, 1H), 7.12-7.10 (m, 1H), 5.95 (t, J=6.1 Hz, 1H), 5.35 (s, 2H), 4.48-4.25 (m, 2H), 3.99-3.85 (m, 2H), 3.73 (s, 2H), 2.58 (s, 3H), 1.18 (s, 9H), 0.96 (t, J=7.1 Hz, 3H); MS (ES+): 563.30 (M+1); Optical rotation [α]$_D$=+25 (c=0.04, MeOH).

Step-4: Preparation of Ethyl 2-(4-acetyl-2-((7-(2-(aminomethyl)pyridin-4-yl)benzofuran-5-yl)methoxy)phenyl)acetate (511d)

To a solution of (+)-(S)-ethyl 2-(4-acetyl-2-((7-(2-((1,1-dimethylethylsulfinamido)methyl)pyridin-4-yl)benzofuran-5-yl)methoxy)phenyl)acetate (511c) (195 mg, 0.347 mmol) in tetrahydrofuran (10 mL) was added 3 N HCl (0.347 mL, 1.040 mmol) at room temperature and stirred for 2 h. The reaction mixture was concentrated to dryness to give ethyl 2-(4-acetyl-2-((7-(2-(aminomethyl)pyridin-4-yl)benzofuran-5-yl)methoxy)phenyl)acetate (511d) (232 mg) which was used as such in next step without further purification; MS (ES+): 459.20 (M+1); (ES−) 457.20 (M−1).

Step-5: Preparation of 2-(4-acetyl-2-((7-(2-(aminomethyl)pyridin-4-yl)benzofuran-5-yl)methoxy) phenyl)acetic Acid (511e)

Compound 511e was prepared according to the procedure reported in step-6 of scheme-1 from of ethyl 2-(4-acetyl-2-((7-(2-(aminomethyl)pyridin-4-yl)benzofuran-5-yl)methoxy)phenyl)acetate (511d) (159 mg, 0.347 mmol) in THF/MeOH (5 mL each) using a solution of lithium hydroxide hydrate (119 mg, 2.78 mmol) in water (5 mL) and stirring at room temperature for 16 h. This gave after workup and purification by reverse phase column chromatography [C-18 column, eluting with water (0.1% HCl)/acetonitrile from 0 to 50%] 2-(4-acetyl-2-((7-(2-(aminomethyl)pyridin-4-yl)benzofuran-5-yl)methoxy)phenyl)acetic acid (511e) (84 mg, 56% yield) HCl salt as a white solid; $^1$H NMR (300 MHz, DMSO-d$_6$) δ 8.78 (d, J=5.2 Hz, 1H), 8.37 (s, 3H), 8.17 (s, 1H), 8.06 (s, 1H), 7.98 (d, J=5.1 Hz, 1H), 7.90 (s, 1H), 7.84 (s, 1H), 7.63-7.56 (m, 2H), 7.41 (d, J=7.6 Hz, 1H), 7.12 (s, 1H), 5.39 (s, 2H), 4.38-4.26 (m, 2H), 3.70 (s, 2H), 2.57 (s, 3H); MS (ES+): 431.10 (M+1).

Scheme-512

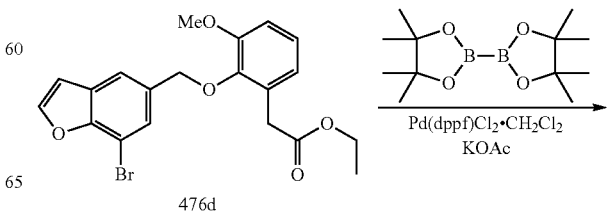

476d

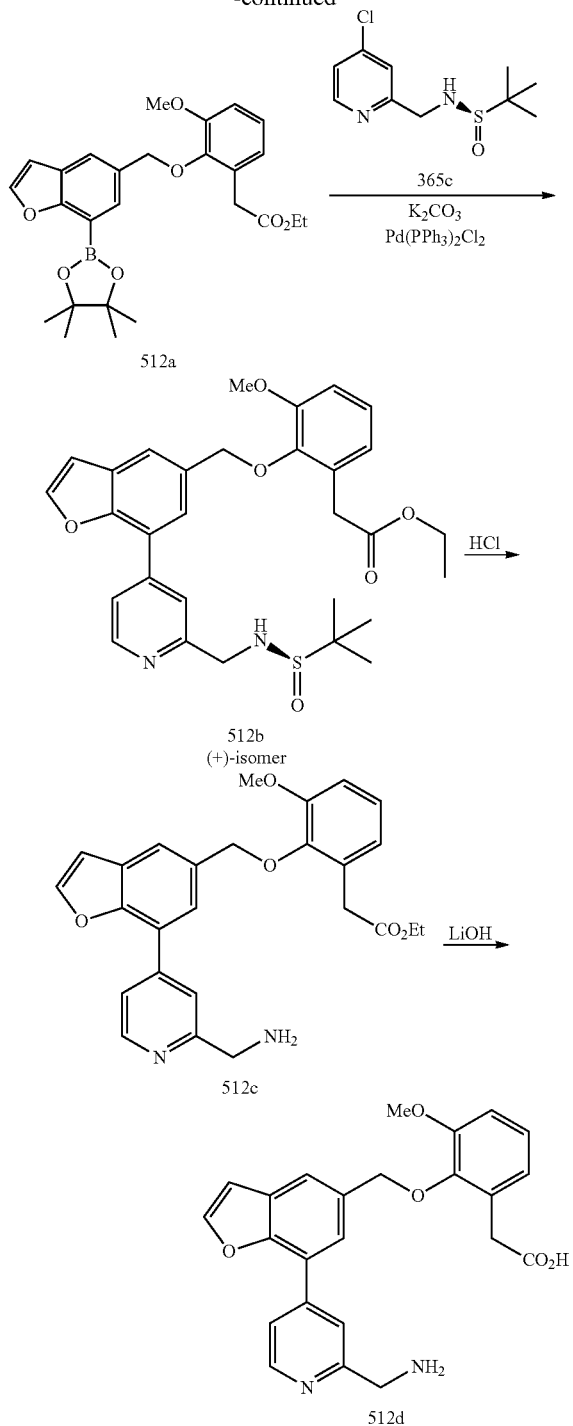

Preparation of 2-(2-((7-(2-(aminomethyl)pyridin-4-yl)benzofuran-5-yl)methoxy)-3-methoxyphenyl)acetic Acid (512d)

Step-1: Preparation of Ethyl 2-(3-methoxy-2-((7-(4,4,5,5-tetramethyl-1,3,2-dioxaborolan-2-yl)benzofuran-5-yl)methoxy)phenyl)acetate (512a)

Compound 512a was prepared according to the procedure reported in step-1 of scheme-59 from ethyl 2-(2-((7-bromobenzofuran-5-yl)methoxy)-3-methoxyphenyl)acetate (476d) (600 mg, 1.431 mmol) using bis(pinacolato)diboron (545 mg, 2.147 mmol), potassium acetate (421 mg, 4.29 mmol) and Pd(dppf)Cl$_2$—CH$_2$Cl$_2$ (117 mg, 0.143 mmol) in anhydrous dioxane (5 mL) under an argon atmosphere and heating at 100° C. for 16 h. This gave after workup and purification by flash column chromatography [silica (24 g), eluting with EtOAc in hexane from 0-15%] ethyl 2-(3-methoxy-2-((7-(4,4,5,5-tetramethyl-1,3,2-dioxaborolan-2-yl)benzofuran-5-yl)methoxy)phenyl)acetate (512a) (670 mg, 100% yield) as a colorless oil; $^1$H NMR (300 MHz, DMSO-d$_6$) δ 8.05 (t, J=1.7 Hz, 1H), 7.82 (d, J=1.8 Hz, 1H), 7.69 (d, J=1.7 Hz, 1H), 7.06-7.00 (m, 2H), 6.98 (t, J=1.7 Hz, 1H), 6.82 (dd, J=5.6, 3.6 Hz, 1H), 5.00 (s, 2H), 3.99 (q, J=7.1 Hz, 2H), 3.87 (s, 3H), 3.57 (s, 2H), 1.35 (s, 12H), 1.12-1.05 (m, 3H); MS (ES+): 489 (M+Na).

Step-2: Preparation of (+)-(S)-ethyl 2-(2-((7-(2-((1,1-dimethylethylsulfinamido)methyl)pyridin-4-yl)benzofuran-5-yl)methoxy)-3-methoxyphenyl)acetate (512b)

Compound 512b was prepared according to the procedure reported in step-3 of scheme-1 from ethyl 2-(3-methoxy-2-((7-(4,4,5,5-tetramethyl-1,3,2-dioxaborolan-2-yl)benzofuran-5-yl)methoxy)phenyl)acetate (512a) (325 mg, 0.697 mmol) in dioxane (4 mL) using (+)-(S)—N-((4-chloropyridin-2-yl)methyl)-2-methylpropane-2-sulfinamide (365c) (189 mg, 0.767 mmol), Pd(PPh$_3$)$_2$Cl$_2$ (49 mg, 0.070 mmol) and 3.3 M aqueous K$_2$CO$_3$ (0.634 mL, 2.091 mmol) under a nitrogen atmosphere heating at 100° C. for 16 h on oil bath. This gave after workup and purification by flash column chromatography [silica gel (12 g), eluting with methanol in DCM from 0-3%] (+)-(S)-ethyl 2-(2-((7-(2-((1,1-dimethylethylsulfinamido)methyl)pyridin-4-yl)benzofuran-5-yl)methoxy)-3-methoxyphenyl)acetate (512b) (273 mg, 71% yield) as an orange oil; MS (ES+) 551 (M+1); Optical rotation [t]D=+24 (c=0.05, MeOH).

Step-3: Preparation of Ethyl 2-(2-((7-(2-(aminomethyl)pyridin-4-yl)benzofuran-5-yl)methoxy)-3-methoxyphenyl)acetate (512c)

Compound 512c was prepared according to the procedure reported in step-3 of scheme-305 from (+)-(S)-ethyl 2-(2-((7-(2-((1,1-dimethylethylsulfinamido)methyl)pyridin-4-yl)benzofuran-5-yl)methoxy)-3-methoxyphenyl)acetate (512b) (273 mg, 0.496 mmol) in ethanol (4 mL) using 4 M HCl in dioxane (0.372 mL, 1.487 mmol) and stirring at room temperature for 1 h. This gave after workup ethyl 2-(2-((7-(2-(aminomethyl)pyridin-4-yl)benzofuran-5-yl)methoxy)-3-methoxyphenyl)acetate (512c) (200 mg, 90% yield) as a pale-orange oil, which was used as such in the next reaction; MS (ES+) 447 (M+1).

Step-4: Preparation of 2-(2-((7-(2-(aminomethyl)pyridin-4-yl)benzofuran-5-yl)methoxy)-3-methoxyphenyl)acetic Acid (512d)

Compound 512d was prepared according to the procedure reported in step-6 of scheme-1 from ethyl 2-(2-((7-(2-(aminomethyl)pyridin-4-yl)benzofuran-5-yl)methoxy)-3-methoxyphenyl)acetate (512c) (200 mg, 0.448 mmol) in ethanol (3 mL) using 2.0 M aqueous LiOH (1.12 mL, 2.24 mmol) and stirring at room temperature for 16 h. This gave after workup and purification by reverse phase column [C-18 column, 100g, eluting with acetonitrile in water (containing 0.1% HCl) from 0-60%] 2-(2-((7-(2-(aminomethyl)pyridin-4-yl)benzofuran-5-yl)methoxy)-3-methoxyphenyl)acetic acid (512d) (145 mg, 77% yield) HCl salt as a pale-green solid; $^1$H NMR (300 MHz, DMSO-$d_6$) δ 8.79 (d, J=5.3 Hz, 1H), 8.65-8.29 (m, 3H), 8.17 (d, J=2.0 Hz, 1H), 8.07 (s, 1H), 7.98 (d, J=5.6 Hz, 1H), 7.87 (s, 1H), 7.79 (s, 1H), 7.13 (d, J=2.0 Hz, 1H), 7.04 (d, J=3.5 Hz, 2H), 6.91-6.78 (m, 1H), 5.11 (s, 2H), 4.32 (q, J=5.2 Hz, 2H), 3.87 (s, 3H), 3.55 (s, 2H); MS (ES+): 419 (M+1), (ES−): 417 (M−1).

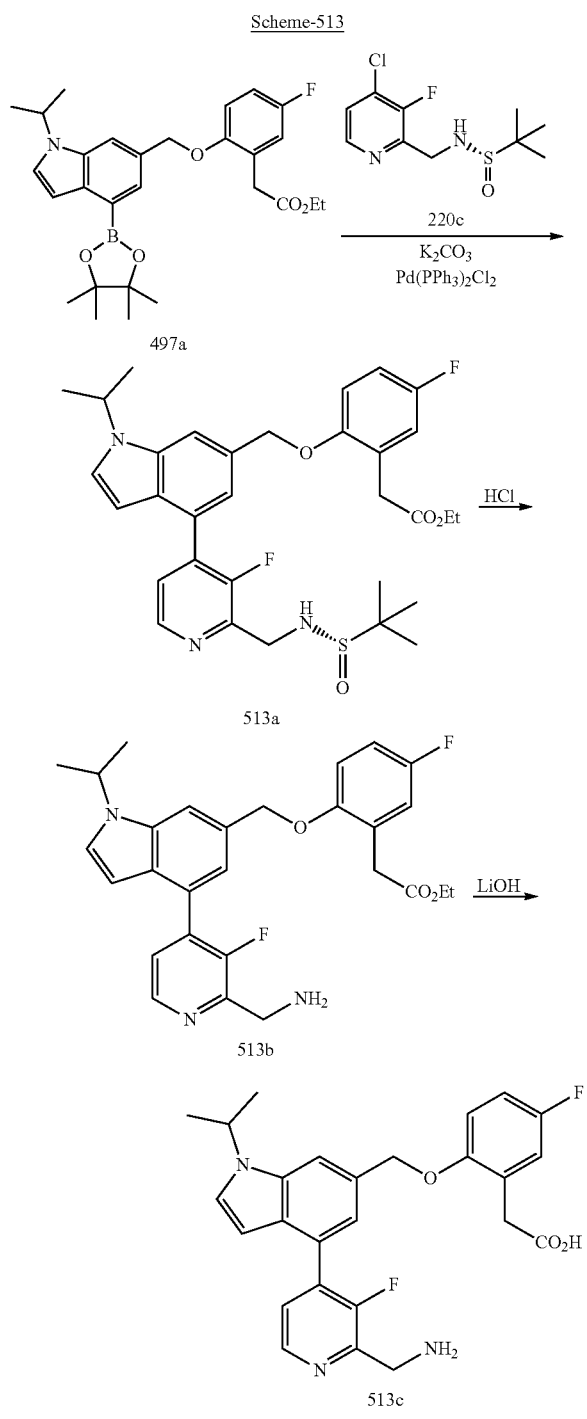

Scheme-513

Preparation of 2-(2-((4-(2-(aminomethyl)-3-fluoropyridin-4-yl)-1-isopropyl-1H-indol-6-yl)methoxy)-5-fluorophenyl)acetic Acid (513c)

Step 1-Preparation of (S)-ethyl 2-(2-((4-(2-((1,1-dimethylethylsulfinamido)methyl)-3-fluoropyridin-4-yl)-1-isopropyl-1H-indol-6-yl)methoxy)-5-fluorophenyl)acetate (513a)

Compound 513a was prepared according to the procedure reported in step-3 of scheme-1 from ethyl 2-(5-fluoro-2-((1-isopropyl-4-(4,4,5,5-tetramethyl-1,3,2-dioxaborolan-2-yl)-1H-indol-6-yl)methoxy)phenyl)acetate (497a) (270 mg, 0.545 mmol) in dioxane (4 mL) using (+)-(S)—N-((4-chloro-3-fluoropyridin-2-yl)methyl)-2-methylpropane-2-sulfinamide (220c) (188 mg, 0.709 mmol), Pd(PPh$_3$)$_2$Cl$_2$ (38.3 mg, 0.055 mmol) and 3.3 M aqueous K$_2$CO$_3$ (0.495 mL, 1.635 mmol) under a nitrogen atmosphere heating at 100° C. for 16 h on oil bath. This gave after workup and purification by flash column chromatography [silica gel (12g), eluting with methanol in DCM from 0-3%] (S)-ethyl 2-(2-((4-(2-((1,1-dimethylethylsulfinamido)methyl)-3-fluoropyridin-4-yl)-1-isopropyl-1H-indol-6-yl)methoxy)-5-fluorophenyl)acetate (513a) (407 mg, 125% yield) as an orange oil; MS (ES+) 598 (M+1).

Step-2: Preparation of Ethyl 2-(2-((4-(2-(aminomethyl)-3-fluoropyridin-4-yl)-1-isopropyl-1H-indol-6-yl)methoxy)-5-fluorophenyl)acetate (513b)

Compound 513b was prepared according to the procedure reported in step-3 of scheme-305 from (S)-ethyl 2-(2-((4-(2-((1,1-dimethylethylsulfinamido)methyl)-3-fluoropyridin-4-yl)-1-isopropyl-1H-indol-6-yl)methoxy)-5-fluorophenyl)acetate (513a) (407 mg, 0.681 mmol), 4 M HCl in dioxane (0.426 mL, 1.7 mmol) in dioxane (4 mL) and water (1 mL) and stirring at room temperature for 1 h. This gave after workup ethyl 2-(2-((4-(2-(aminomethyl)-3-fluoropyridin-4-yl)-1-isopropyl-1H-indol-6-yl)methoxy)-5-fluorophenyl)acetate (513b) as a pale-orange oil, which was used as such in the next reaction; MS (ES+): 505 (M+1).

Step-3: Preparation of 2-(2-((4-(2-(aminomethyl)-3-fluoropyridin-4-yl)-1-isopropyl-1H-indol-6-yl)methoxy)-5-fluorophenyl)acetic Acid (513c)

Compound 513c was prepared according to the procedure reported in step-6 of scheme-1 from ethyl 2-(2-((4-(2-(aminomethyl)-3-fluoropyridin-4-yl)-1-isopropyl-1H-indol-6-yl)methoxy)-5-fluorophenyl)acetate (513b) (176 mg, 0.357 mmol) in MeOH (5 mL) using a 2.0 M aqueous solution of lithium hydroxide (0.892 mL, 1.783 mmol) and stirring at room temperature for 16 h. This gave after workup and purification by reverse phase column [C-18 column, 50g, eluting with acetonitrile in water 0-60%] 2-(2-((4-(2-(aminomethyl)-3-fluoropyridin-4-yl)-1-isopropyl-1H-indol-6-yl)methoxy)-5-fluorophenyl)acetic acid (513c) (17 mg, 10% yield) free base as a white solid; $^1$H NMR (300 MHz, DMSO-$d_6$) δ 8.44 (d, J=4.9 Hz, 1H), 7.78 (s, 1H), 7.70-7.56 (m, 1H), 7.51 (t, J=5.4 Hz, 1H), 7.25 (s, 1H), 7.11-7.00 (m, 2H), 7.00-6.74 (m, 1H), 6.36 (s, 1H), 5.22 (s, 2H), 4.98-4.73 (m, 1H), 3.94 (s, 2H), 3.44 (s, 2H), 1.47 (d, J=6.6 Hz, 6H); $^{19}$F NMR (282 MHz, DMSO-$d_6$) δ−124.42, −130.91; MS (ES+): 466.1 (M+1), (ES−): 464.1 (M−1).

Scheme-514
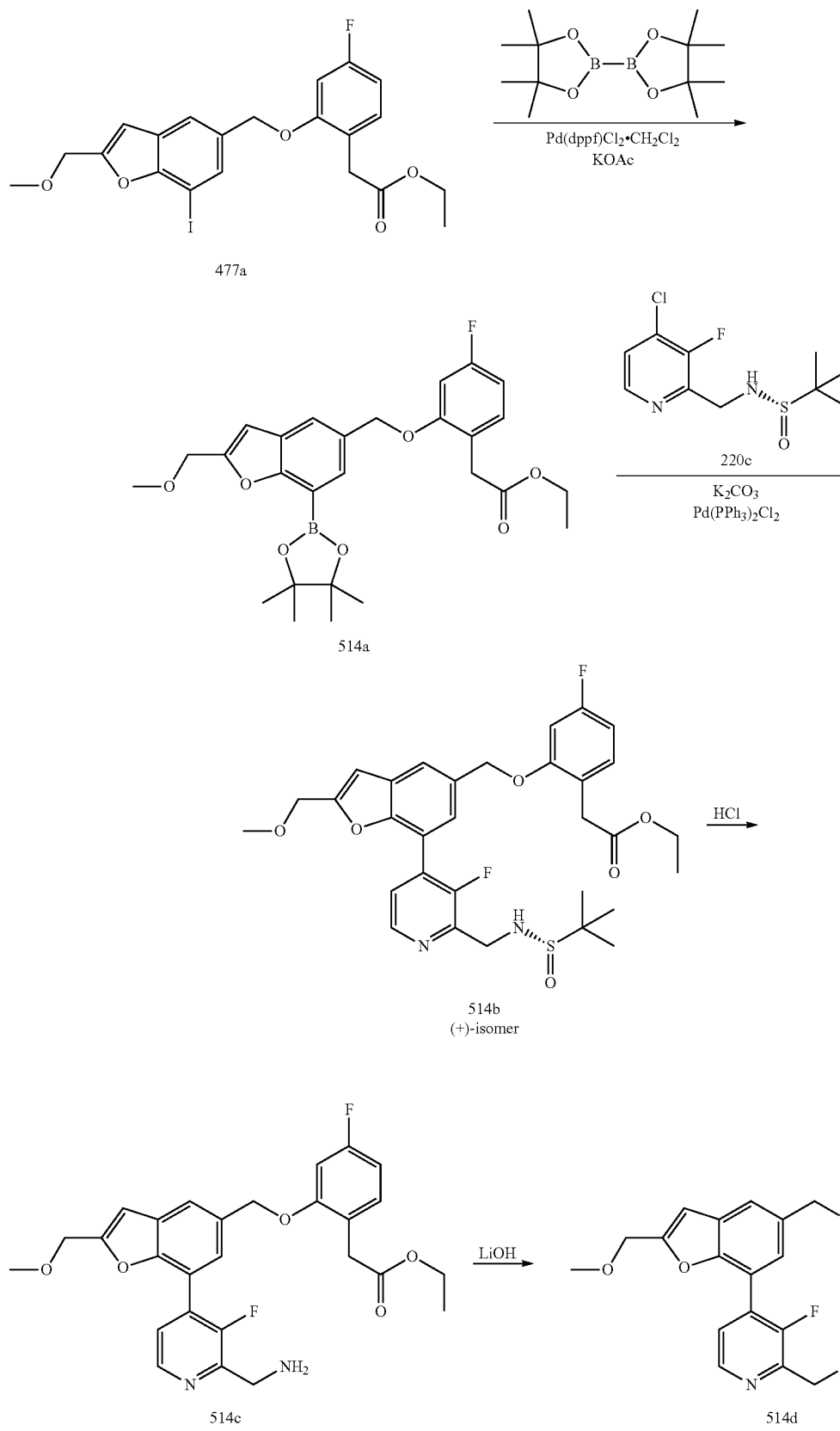

Preparation of 2-(2-((7-(2-(aminomethyl)-3-fluoro-pyridin-4-yl)-2-(methoxymethyl)benzofuran-5-yl)methoxy)-4-fluorophenyl)acetic Acid (514d)

Step 1. Preparation of ethyl 2-(4-fluoro-2-((2-(methoxymethyl)-7-(4,4,5,5-tetramethyl-1,3,2-dioxaborolan-2-yl)benzofuran-5-yl)methoxy)phenyl)acetate (514a)

Compound 514a was prepared according to the procedure reported in step-1 of scheme-59 from ethyl 2-(4-fluoro-2-((7-iodo-2-(methoxymethyl)benzofuran-5-yl)methoxy)phenyl)acetate (477a) (1.2 g, 2.408 mmol) using bis(pinacolato)diboron (1.835 g, 7.22 mmol), potassium acetate (0.709 g, 7.22 mmol) and Pd(dppf)Cl$_2$—CH$_2$Cl$_2$ (0.295 g, 0.361 mmol) in anhydrous dioxane (25 mL) under an argon atmosphere and heating at 100° C. for 16 h. This gave after workup and purification by flash column chromatography (silica gel, eluting with EtOAc in hexane from 0-25%) ethyl 2-(4-fluoro-2-((2-(methoxymethyl)-7-(4,4,5,5-tetramethyl-1,3,2-dioxaborolan-2-yl)benzofuran-5-yl)methoxy)phenyl)acetate (514a) (1.05 g, 87% yield) as a brown gum; MS (ES+): 521 (M+Na).

Step 2-Preparation of (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-4-fluorophenyl)acetate (514b)

Compound 514b was prepared according to the procedure reported in step-3 of scheme-1 from ethyl 2-(4-fluoro-2-((2-(methoxymethyl)-7-(4,4,5,5-tetramethyl-1,3,2-dioxaborolan-2-yl)benzofuran-5-yl)methoxy)phenyl)acetate (514a) (450 mg, 0.903 mmol) in dioxane (20 mL) using (+)-(S)—N-((4-chloro-3-fluoropyridin-2-yl)methyl)-2-methylpropane-2-sulfinamide (220c) (287 mg, 1.084 mmol), Pd(PPh$_3$)$_2$Cl$_2$ (95 mg, 0.135 mmol) and a solution of K$_2$CO$_3$ (374 mg, 2.71 mmol) in water (2.4 mL) under a nitrogen atmosphere heating at 100° C. for 15 h on oil bath. This gave after workup and purification by flash column chromatography (silica gel, eluting with hexanes/10% methanol in ethyl acetate (ratio 1:0 to 1:1)] (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-4-fluorophenyl)acetate (514b) (215 mg, 40% yield) as a colorless gum; $^1$H NMR (300 MHz, DMSO-d$_6$) δ 8.52 (d, J=4.9 Hz, 1H), 7.81 (s, 1H), 7.65 (t, J=5.2 Hz, 1H), 7.50 (s, 1H), 7.24 (t, J=7.6 Hz, 1H), 7.09-7.00 (m, 2H), 6.78-6.70 (m, 1H), 5.84 (t, J=5.7 Hz, 1H), 5.25 (s, 2H), 4.52 (s, 2H), 4.40 (d, J=5.8 Hz, 2H), 3.90 (q, J=7.1 Hz, 2H), 3.59 (s, 2H), 3.30 (s, 3H), 1.11 (s, 9H), 0.97 (t, J=7.1 Hz, 3H); $^{19}$F NMR (282 MHz, DMSO-d$_6$) δ −112.62, −128.12; MS (ES+) 601.2 (M+1); Optical rotation [t]D=+28.57 (c=0.105, MeOH).

Step-3: Preparation of Ethyl 2-(2-((7-(2-(aminomethyl)-3-fluoropyridin-4-yl)-2-(methoxymethyl)benzofuran-5-yl)methoxy)-4-fluorophenyl)acetate (514c)

Compound 514c was prepared according to the procedure reported in step-3 of scheme-305 from (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-4-fluorophenyl)acetate (514b) (205 mg, 0.341 mmol) in THF (10 mL) using 3 M aqueous HCl (0.341 mL, 1.024 mmol) and stirring at room temperature for 6 h. This gave after workup ethyl 2-(2-((7-(2-(aminomethyl)-3-fluoropyridin-4-yl)-2-(methoxymethyl)benzofuran-5-yl)methoxy)-4-fluorophenyl)acetate (514c), which was used as such in the next reaction; MS (ES+) 497.2 (M+1).

Step-4: Preparation of 2-(2-((7-(2-(aminomethyl)-3-fluoropyridin-4-yl)-2-(methoxymethyl)benzofuran-5-yl)methoxy)-4-fluorophenyl)acetic Acid (514d)

Compound 514d was prepared according to the procedure reported in step-6 of scheme-1 from ethyl 2-(2-((7-(2-(aminomethyl)-3-fluoropyridin-4-yl)-2-(methoxymethyl)benzofuran-5-yl)methoxy)-4-fluorophenyl)acetate (514c) (0.341 mmol) in THF (6 mL) and MeOH (6 mL) using a solution of LiOH (117 mg, 2.73 mmol) in water (6 mL) and stirring at room temperature for 19 h. This gave after workup and purification by reverse phase column [C-18 column, 100g, eluting with acetonitrile in water (containing 0.1% HCl) from 0-100%] 2-(2-((7-(2-(aminomethyl)-3-fluoropyridin-4-yl)-2-(methoxymethyl)benzofuran-5-yl)methoxy)-4-fluorophenyl)acetic acid (514d) (49 mg, 31% yield for two steps) HCl salt as a white solid; $^1$H NMR (300 MHz, DMSO-d$_6$) δ 12.23 (s, 1H), 8.64 (d, J=5.0 Hz, 1H), 8.61-8.43 (m, 3H), 7.88 (s, 1H), 7.79 (t, J=5.3 Hz, 1H), 7.57 (s, 1H), 7.24 (t, J=7.6 Hz, 1H), 7.10-6.95 (m, 2H), 6.81-6.62 (m, 1H), 5.29 (s, 2H), 4.54 (s, 2H), 4.44-4.31 (m, 2H), 3.56 (s, 2H), 3.30 (s, 3H); $^{19}$F NMR (282 MHz, DMSO-d$_6$) δ −112.98, −128.63; MS (ES+) 469.1 (M+1); Analysis calculated for C$_{25}$H$_{22}$F$_2$N$_2$O$_5$.HCl.0.5H$_2$O: C, 58.43; H, 4.71; Cl, 6.90; N, 5.45; Found: C, 58.37; H, 4.72; Cl, 7.14; N, 5.44.

Scheme-515

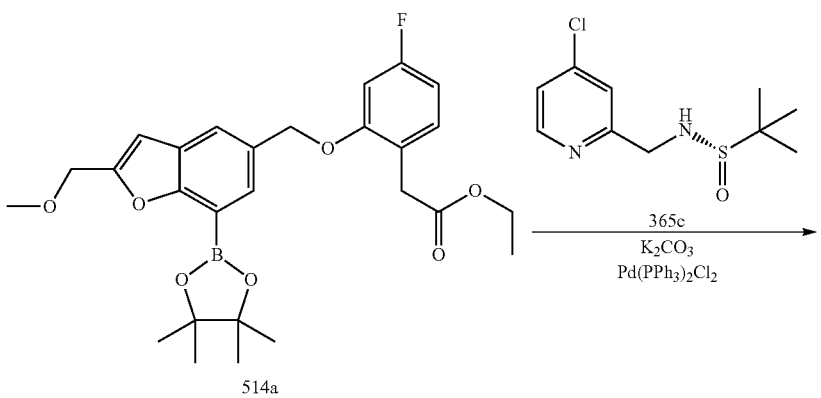

514a

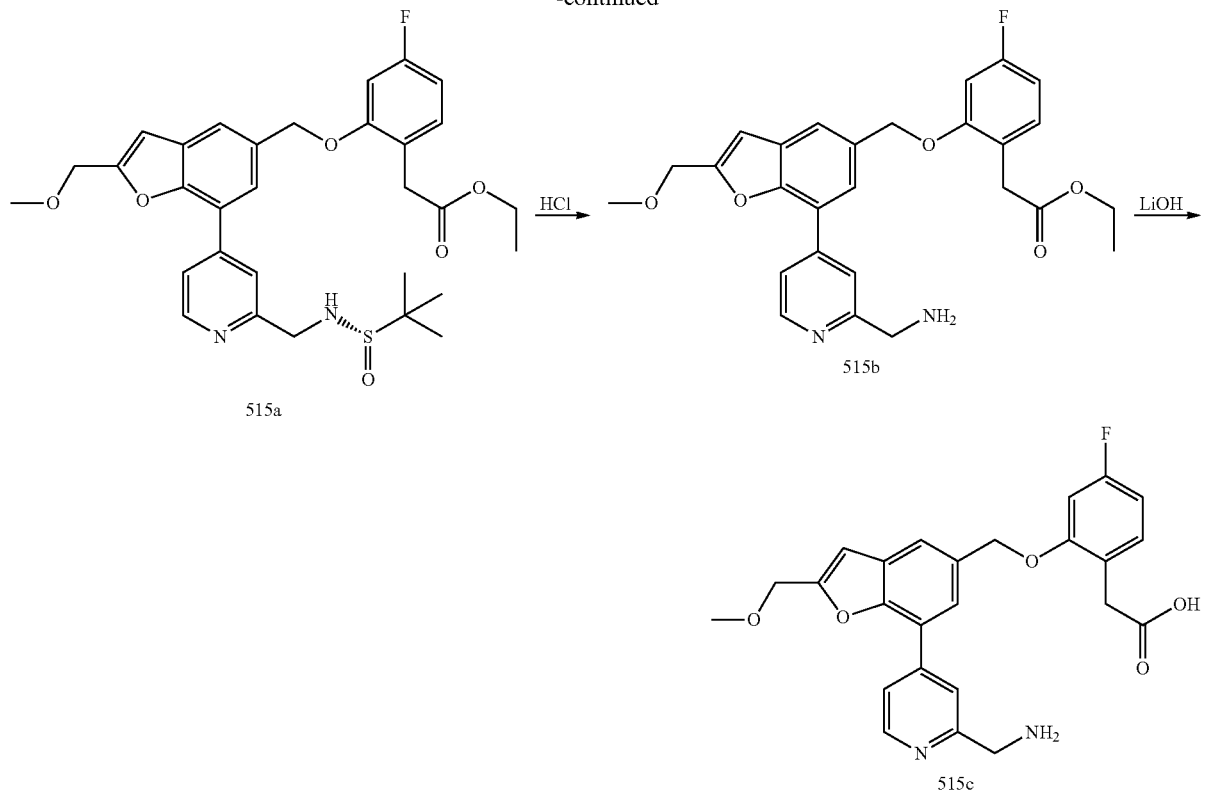

Preparation of 2-(2-((7-(2-(aminomethyl)pyridin-4-yl)-2-(methoxymethyl)benzofuran-5-yl)methoxy)-4-fluorophenyl)acetic Acid (515c)

Step 1-Preparation of (S)-ethyl 2-(2-((7-(2-((1,1-dimethylethylsulfinamido)methyl)pyridin-4-yl)-2-(methoxymethyl)benzofuran-5-yl)methoxy)-4-fluorophenyl)acetate (515a)

Compound 515a was prepared according to the procedure reported in step-3 of scheme-1 from ethyl 2-(4-fluoro-2-((2-(methoxymethyl)-7-(4,4,5,5-tetramethyl-1,3,2-dioxaborolan-2-yl)benzofuran-5-yl)methoxy)phenyl)acetate (514a) (495 mg, 0.993 mmol) in dioxane (20 mL) using (+)-(S)—N-((4-chloropyridin-2-yl)methyl)-2-methylpropane-2-sulfinamide (365c) (294 mg, 1.192 mmol), Pd(PPh$_3$)$_2$Cl$_2$ (105 mg, 0.149 mmol) and a solution of K$_2$CO$_3$ (412 mg, 2.98 mmol) in water (2.4 mL) under a nitrogen atmosphere heating at 100° C. for 13 h on oil bath. This gave after workup and purification by flash column chromatography [silica gel, eluting with hexanes/10% methanol in ethyl acetate (ratio 1:0 to 1:1)] (S)-ethyl 2-(2-((7-(2-((1,1-dimethylethylsulfinamido)methyl)pyridin-4-yl)-2-(methoxymethyl)benzofuran-5-yl)methoxy)-4-fluorophenyl)acetate (515a) (135 mg, 23% yield) as a colorless gum; $^1$H NMR (300 MHz, DMSO-d$_6$) δ 8.65 (d, J=5.2 Hz, 1H), 8.01 (s, 1H), 7.79-7.73 (m, 2H), 7.68 (s, 1H), 7.25 (t, J=7.6 Hz, 1H), 7.10-6.99 (m, 2H), 6.79-6.70 (m, 1H), 5.95 (t, J=6.1 Hz, 1H), 5.25 (s, 2H), 4.58 (s, 2H), 4.46-4.27 (m, 2H), 3.91 (q, J=7.1 Hz, 2H), 3.60 (s, 2H), 3.32 (s, 3H), 1.17 (s, 9H), 0.98-0.92 (m, 3H); $^{19}$F NMR (282 MHz, DMSO-d$_6$) δ −112.61; MS (ES+): 583.2 (M+1).

Step-2: Preparation of Ethyl 2-(2-((7-(2-(aminomethyl)pyridin-4-yl)-2-(methoxymethyl)benzofuran-5-yl)methoxy)-4-fluorophenyl)acetate (515b)

Compound 515b was prepared according to the procedure reported in step-3 of scheme-305 from (S)-ethyl 2-(2-((7-(2-((1,1-dimethylethylsulfinamido)methyl)pyridin-4-yl)-2-(methoxymethyl)benzofuran-5-yl)methoxy)-4-fluorophenyl)acetate (515a) (130 mg, 0.223 mmol) in THF (10 mL) using 3 M aqueous HCl (0.223 mL, 0.669 mmol) and stirring at room temperature for 6 h. This gave after workup ethyl 2-(2-((7-(2-(aminomethyl)pyridin-4-yl)-2-(methoxymethyl)benzofuran-5-yl)methoxy)-4-fluorophenyl)acetate (515b), which was used as such in the next reaction; MS (ES+): 479.2 (M+1).

Step-3: Preparation of 2-(2-((7-(2-(aminomethyl)pyridin-4-yl)-2-(methoxymethyl)benzofuran-5-yl)methoxy)-4-fluorophenyl)acetic Acid (515c)

Compound 515c was prepared according to the procedure reported in step-6 of scheme-1 from ethyl 2-(2-((7-(2-(aminomethyl)pyridin-4-yl)-2-(methoxymethyl)benzofuran-5-yl)methoxy)-4-fluorophenyl)acetate (515b) (0.223 mmol) in THF (4 mL) and MeOH (4 mL) using a solution of aqueous LiOH (76 mg, 1.784 mmol) in water (4 mL) and stirring at room temperature for 19 h. This gave after workup and purification by reverse phase column [C-18 column, 100g, eluting with acetonitrile in water (containing 0.1% HCl) from 0-100%] 2-(2-((7-(2-(aminomethyl)pyridin-4-yl)-2-(methoxymethyl)benzofuran-5-yl)methoxy)-4-fluorophenyl)acetic acid (515c) (49 mg, 31% yield for two steps) HCl salt as a yellow solid; $^1$H NMR (300 MHz, DMSO-d$_6$)

δ 8.79 (d, J=5.2 Hz, 1H), 8.43 (s, 3H), 8.02 (s, 1H), 7.97 (d, J=5.4 Hz, 1H), 7.83 (s, 1H), 7.78 (s, 1H), 7.25 (t, J=7.6 Hz, 1H), 7.06 (s, 1H), 7.02 (dd, J=11.6, 2.5 Hz, 1H), 6.78-6.70 (m, 1H), 5.29 (s, 2H), 4.61 (s, 2H), 4.39-4.19 (m, 2H), 3.57 (s, 2H), 3.34 (s, 3H); $^{19}$F NMR (282 MHz, DMSO-$d_6$) δ−112.95; MS (ES+) 451.1 (M+1); Analysis calculated for $C_{25}H_{23}FN_2O_5 \cdot 1.45HCl \cdot H_2O$: C, 57.60; H, 5.11; Cl, 9.86; N, 5.37; Found: C, 57.46; H, 5.10; Cl, 9.60; N, 5.36.

from 0-70%] ethyl 2-(2-((7-(3-(aminomethyl)-2-fluorophenyl)-6-fluorobenzofuran-5-yl)methoxy)phenyl)acetate (516b) (101 mg, 61% yield) as a colorless oil which was used in the next step without further purification. $^1$H NMR (300 MHz, DMSO-$d_6$) δ 8.09-7.99 (m, 1H), 7.85 (d, J=6.8 Hz, 1H), 7.65 (t, J=7.4 Hz, 1H), 7.43 (t, J=7.0 Hz, 1H), 7.37-7.13 (m, 4H), 7.10-7.03 (m, 1H), 6.93 (t, J=7.4 Hz, 1H), 5.25 (s, 2H), 3.93 (q, J=7.1 Hz, 2H), 3.83 (s, 2H), 3.60 (s, 2H), 1.00 (t, J=7.6, 6.5 Hz, 3H). MS (ES+): 452.1 (M+1).

Step-2: Preparation of 2-(2-((7-(3-(aminomethyl)-2-fluorophenyl)-6-fluorobenzofuran-5-yl)methoxy)phenyl)acetic Acid (516c)

Compound 516c was prepared according to the procedure reported in step-6 of scheme-1, from ethyl 2-(2-((7-(3-(aminomethyl)-2-fluorophenyl)-6-fluorobenzofuran-5-yl)methoxy)phenyl)acetate (516b) (98 mg, 0.217 mmol) in acetonitrile/THF (6 mL) using a solution of lithium hydroxide (72 mg, 1.716 mmol) in water (2 mL). This gave after workup and purification by reverse phase column [C18 (50 g), eluting with ACN in water (containing 0.1% HCl) from 0-100%] 2-(2-((7-(3-(aminomethyl)-2-fluorophenyl)-6-fluorobenzofuran-5-yl)methoxy)phenyl)acetic acid (516c) (70 mg, 76% yield) HCl salt as a white solid. $^1$H NMR (300 MHz, DMSO-$d_6$) δ 8.06 (s, 1H), 7.93 (d, J=6.8 Hz, 1H), 7.79 (t, J=7.4 Hz, 1H), 7.65 (t, J=7.2 Hz, 1H), 7.46 (t, 1H), 7.33-7.19 (m, 2H), 7.15 (d, J=8.0 Hz, 1H), 7.07 (s, 1H), 6.93 (t, J=7.5 Hz, 1H), 5.28 (s, 2H), 4.18 (s, 2H), 3.57 (s, 2H). $^{19}$F NMR (282 MHz, DMSO-$d_6$) δ−117.07, −125.48; MS (ES+): 424.1 (M+1); MS (ES−): 422.1 (M−1); Analysis calculated for $C_{24}H_{19}F_2NO_4$: C, 60.32; H, 4.64; Cl, 7.42; N, 2.93; Found: C, 60.06; H, 4.49; Cl, 7.46; N, 3.04.

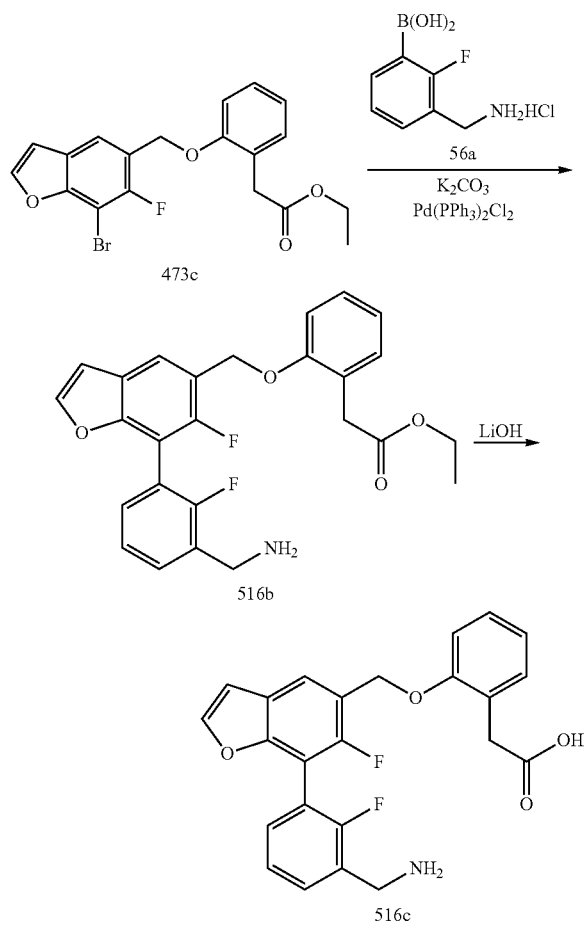

Scheme-516

Preparation of 2-(2-((7-(3-(aminomethyl)-2-fluorophenyl)-6-fluorobenzofuran-5-yl)methoxy)phenyl)acetic Acid (516c)

Step-1: Preparation of Ethyl 2-(2-((7-(3-(aminomethyl)-2-fluorophenyl)-6-fluorobenzofuran-5-yl)methoxy)phenyl)acetate (516b)

Compound 516b was prepared according to the procedure reported in step-3 of scheme-1 from ethyl 2-(2-((7-bromo-6-fluorobenzofuran-5-yl)methoxy)phenyl)acetate (473c) (150 mg, 0.368 mmol) in dioxane (5 mL) using (3-(aminomethyl)-2-fluorophenyl)boronic acid hydrochloride (56a) (93 mg, 0.553 mmol), Pd(PPh$_3$)$_2$Cl$_2$ (38.8 mg, 0.055 mmol) and a solution of K$_2$CO$_3$ (153 mg, 1.105 mmol) in water (0.5 mL) under an Ar atmosphere and heating at 100° C. for 3 h. This gave after workup and purification by flash column chromatography [silica (12g), eluting with DMA80 in DCM

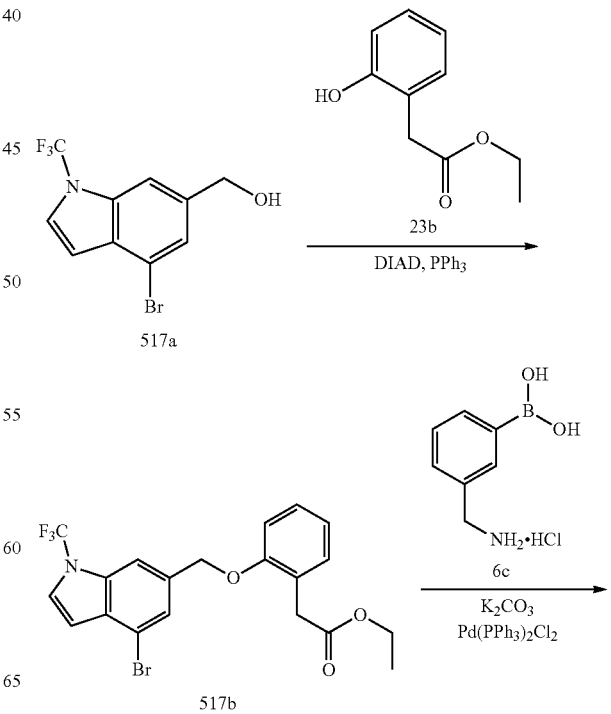

Scheme-517

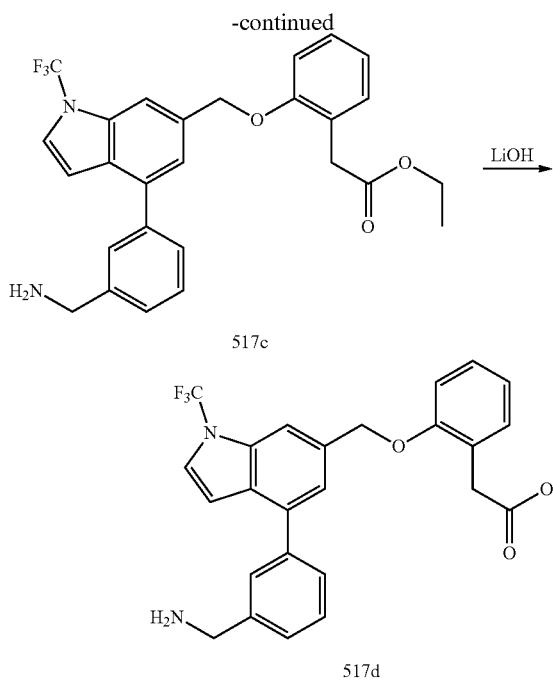

Preparation of 2-(2-((4-(3-(aminomethyl)phenyl)-1-(trifluoromethyl)-1H-indol-6-yl)methoxy)phenyl) acetic Acid (517d)

Step-1: Preparation of Ethyl 2-(2-((4-bromo-1-(trifluoromethyl)-1H-indol-6-yl)methoxy)phenyl)acetate (517b)

Compound 517b was prepared according to the procedure reported in step-2 of scheme-23 from (4-bromo-1-(trifluoromethyl)-1H-indol-6-yl)methanol (517a) (0.4 g, 1.360 mmol) using triphenylphosphine (0.464 g, 1.768 mmol), ethyl 2-(2-hydroxyphenyl) acetate (23b) (0.319 g, 1.768 mmol) and DIAD (0.358 mg, 1.768 mmol) in THF (15 mL). This gave after workup and purification by flash column chromatography (silica gel, 40 g, eluting with EtOAc/MeOH (9:1) in hexanes from 0-40%) ethyl 2-(2-((4-bromo-1-(trifluoromethyl)-1H-indol-6-yl)methoxy)phenyl)acetate (517b) (0.4 g, 65% yield) as a light yellow oil; $^1$H NMR (300 MHz, DMSO-$d_6$) δ 7.92 (d, J=3.7 Hz, 1H), 7.75 (s, 1H), 7.60 (s, 1H), 7.31-7.19 (m, 2H), 7.07 (d, J=8.1 Hz, 1H), 6.92 (t, J=7.4 Hz, 1H), 6.79 (d, J=3.7 Hz, 1H), 5.25 (s, 2H), 4.07-3.94 (m, 2H), 3.63 (s, 2H), 1.06 (td, J=7.1, 1.1 Hz, 3H); $^{19}$F NMR (282 MHz, DMSO-$d_6$) δ−55.23; MS (ES+): 479 (M+Na).

Step-2: Preparation of Ethyl 2-(2-((4-(3-(aminomethyl)phenyl)-1-(trifluoromethyl)-1H-indol-6-yl)methoxy)phenyl)acetate (517c)

Compound 517c was prepared according to the procedure reported in step-3 of scheme-1 from ethyl 2-(2-((4-bromo-1-(trifluoromethyl)-1H-indol-6-yl)methoxy)phenyl)acetate (517b) (200 mg, 0.438 mmol) in dioxane (5 mL) using (3-(aminomethyl)phenyl)boronic acid hydrochloride (6c) (79 mg, 0.526 mmol), Pd(PPh$_3$)$_2$Cl$_2$ (46.2 mg, 0.066 mmol) and a solution of K$_2$CO$_3$ (182 mg, 1.315 mmol) in water (1 mL) heating under a nitrogen atmosphere at 90° C. for 4 h. This gave after workup and purification by flash column chromatography [silica (12 g), eluting with DMA80 in DCM from 0-50%] ethyl 2-(2-((4-(3-(aminomethyl)phenyl)-1-(trifluoromethyl)-1H-indol-6-yl)methoxy)phenyl)acetate (517c) (212 mg, 71% yield) as a pale-yellow oil. $^1$H NMR (300 MHz, DMSO-$d_6$) δ 7.83 (d, J=3.8 Hz, 1H), 7.71 (s, 1H), 7.62 (s, 1H), 7.51-7.42 (m, 3H), 7.42-7.34 (m, 1H), 7.30-7.18 (m, 2H), 7.12 (d, J=8.1 Hz, 1H), 6.95-6.85 (m, 2H), 5.30 (s, 2H), 3.90 (q, J=7.1 Hz, 2H), 3.81 (s, 2H), 3.63 (s, 2H), 1.03-0.88 (m, 3H); $^{19}$F NMR (282 MHz, DMSO-$d_6$) δ−55.14; MS (ES+): 483.10 (M+1).

Step-3: Preparation of 2-(2-((4-(3-(aminomethyl)phenyl)-1-(trifluoromethyl)-1H-indol-6-yl)methoxy)phenyl)acetic Acid (517d)

Compound 517d was prepared according to the procedure reported in step-6 of scheme-1 from ethyl 2-(2-((4-(3-(aminomethyl)phenyl)-1-(trifluoromethyl)-1H-indol-6-yl)methoxy)phenyl)acetate (517c) (150 mg, 0.311 mmol) in THF/MeOH (6 mL, each) using a solution of LiOH (104 mg, 2.487 mmol) in water (2 mL) and stirring at room temperature for 16 h. This gave after workup and purification by reverse phase column [C18 (50 g), eluting with acetonitrile in water from 0-100%] 2-(2-((4-(3-(aminomethyl)phenyl)-1-(trifluoromethyl)-1H-indol-6-yl)methoxy)phenyl)acetic acid (517d) (105 mg, 74% yield) free base as a white solid; $^1$H NMR (300 MHz, DMSO-$d_6$) δ 8.14 (s, 1H), 7.83 (d, J=3.7 Hz, 1H), 7.77-7.66 (m, 3H), 7.47 (t, J=7.6 Hz, 1H), 7.35 (d, J=7.5 Hz, 1H), 7.09 (t, J=6.9 Hz, 2H), 7.00-6.93 (m, 2H), 6.80 (t, J=7.3 Hz, 1H), 5.32 (s, 2H), 3.98 (s, 2H), 3.38 (s, 2H); $^{19}$F NMR (282 MHz, DMSO-$d_6$) δ−55.10; MS (ES+): 455.2 (M+1), (ES−): 453.10 (M−1); Analysis calculated for $C_{25}H_{21}F_3N_2O_3 \cdot 0.75H_2O$: C, 64.17; H, 4.85; N, 5.99; Found: C, 63.92; H, 4.75; N, 6.00.

Scheme-518

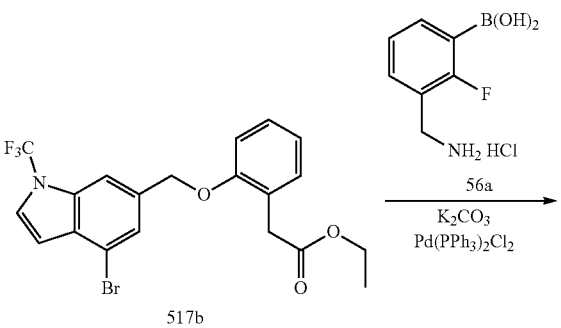

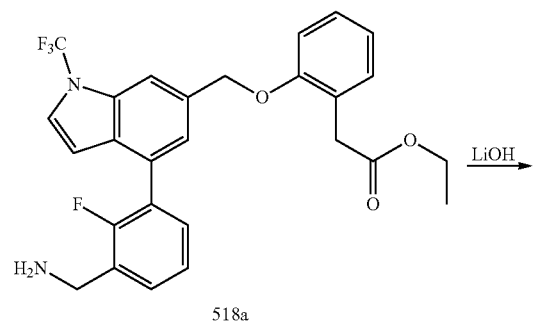

-continued

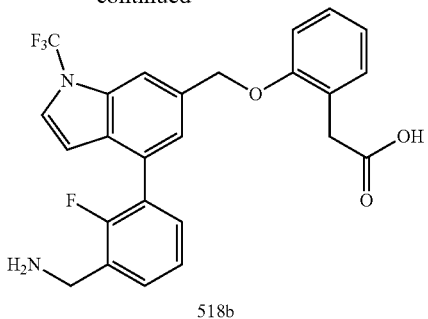

518b

Preparation of 2-(2-((4-(3-(aminomethyl)-2-fluorophenyl)-1-(trifluoromethyl)-1H-indol-6-yl)methoxy)phenyl)acetic Acid (518b)

Step-1: Preparation of Ethyl 2-(2-((4-(3-(aminomethyl)-2-fluorophenyl)-1-(trifluoromethyl)-1H-indol-6-yl)methoxy)phenyl)acetate (518a)

Compound 518a was prepared according to the procedure reported in step-3 of scheme-1 from ethyl 2-(2-((4-bromo-1-(trifluoromethyl)-1H-indol-6-yl)methoxy)phenyl)acetate (517b) (200 mg, 0.438 mmol) in dioxane (5 mL) using (3-(aminomethyl)-2-fluorophenyl)boronic acid hydrochloride (56a) (117 mg, 0.57 mmol), Pd(PPh$_3$)$_2$Cl$_2$ (46.2 mg, 0.066 mmol) and a solution of K$_2$CO$_3$ (182 mg, 1.315 mmol) in water (1 mL) heating under a nitrogen atmosphere at 90° C. for 3 h. This gave after workup and purification by flash column chromatography [silica (12 g), eluting with DMA80 in DCM from 0-50%] ethyl 2-(2-((4-(3-(aminomethyl)-2-fluorophenyl)-1-(trifluoromethyl)-1H-indol-6-yl)methoxy)phenyl)acetate (518a) (180 mg, 82% yield) as a yellow syrup; $^{19}$F NMR (282 MHz, DMSO-d$_6$) δ –55.09, –122.64; MS (ES+): 501.20 (M+1).

Step-2: Preparation of 2-(2-((4-(3-(aminomethyl)-2-fluorophenyl)-1-(trifluoromethyl)-1H-indol-6-yl)methoxy)phenyl)acetic Acid (518b)

Compound 518b was prepared according to the procedure reported in step-6 of scheme-1 from ethyl 2-(2-((4-(3-(aminomethyl)-2-fluorophenyl)-1-(trifluoromethyl)-1H-indol-6-yl)methoxy)phenyl)acetate (518a) (180 mg, 0.360 mmol) in THF/MeOH (8 mL, each) using a solution of LiOH (121 mg, 2.88 mmol) in water (2 mL) and stirring at room temperature for 16 h. This gave after workup and purification by reverse phase column [C18 (50 g), eluting with acetonitrile in water from 0-100%] 2-(2-((4-(3-(aminomethyl)-2-fluorophenyl)-1-(trifluoromethyl)-1H-indol-6-yl)methoxy)phenyl)acetic acid (518b) (135 mg, 79% yield) free base as a white solid; $^1$H NMR (300 MHz, DMSO-d$_6$) δ 7.82-7.75 (m, 2H), 7.59-7.50 (m, 2H), 7.43 (t, J=7.5 Hz, 1H), 7.30 (t, J=7.5 Hz, 1H), 7.24-7.15 (m, 2H), 7.06 (d, J=8.4 Hz, 1H), 6.88 (t, J=7.4 Hz, 1H), 6.67-6.63 (m, 1H), 5.32 (s, 2H), 3.87 (s, 2H), 3.53 (s, 2H); $^{19}$F NMR (282 MHz, DMSO-d$_6$) δ –55.05, –121.11; MS (ES+): 473.1 (M+1), (ES–): 471.1 (M–1); Analysis calculated for C$_{25}$H$_{20}$F$_4$N$_2$O$_3$·0.5H$_2$O: C, 62.37; H, 4.40; N, 5.82; Found: C, 62.33; H, 4.32; N, 5.89.

Scheme-519

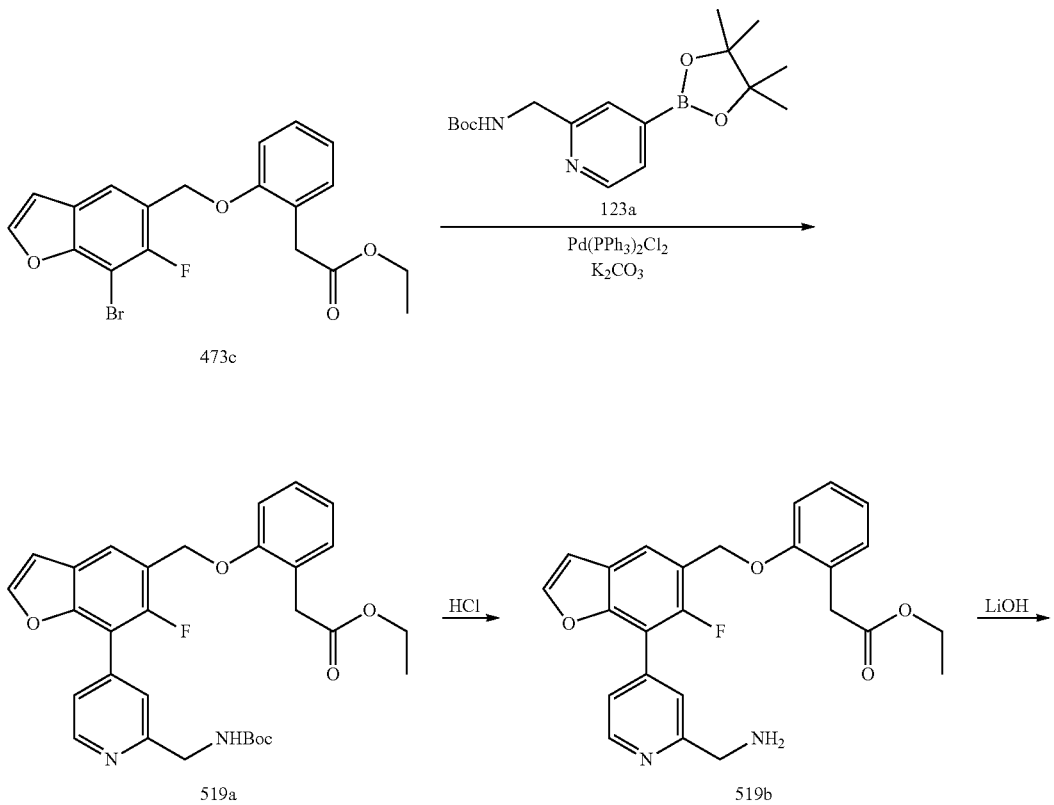

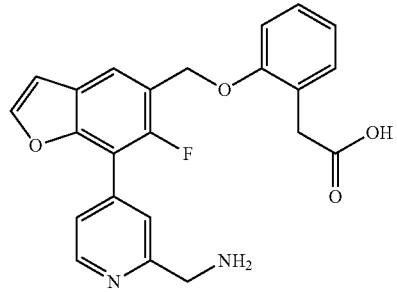

519c

Preparation of 2-(2-((7-(2-(aminomethyl)pyridin-4-yl)-6-fluorobenzofuran-5-yl)methoxy)phenyl)acetic Acid (519c)

Step-1: Preparation of Ethyl 2-(2-((7-(2-(((tert-butoxycarbonyl)amino)methyl)pyridin-4-yl)-6-fluorobenzofuran-5-yl)methoxy)phenyl)acetate (519a)

Compound 519a was prepared according to the procedure reported in step-3 of scheme-1 from ethyl 2-(2-((7-bromo-6-fluorobenzofuran-5-yl)methoxy)phenyl)acetate (473c) (154 mg, 0.378 mmol) in dioxane (5 mL) using tert-butyl (4-(4,4,5,5-tetramethyl-1,3,2-dioxaborolan-2-yl)pyridin-2-yl)methylcarbamate (123a) (171 mg, 0.512 mmol), a solution of $K_2CO_3$ (157 mg, 1.134 mmol) in water (0.5 mL), bis(triphenylphosphine)palladium(II) chloride (39.8 mg, 0.057 mmol) and heating under a nitrogen atmosphere at 100° C. for 3 h on an oil bath. This gave after workup, purification by flash column chromatography [silica (12 g), eluting with methanol in DCM from 0-15%] ethyl 2-(2-((7-(2-(((tert-butoxycarbonyl)amino)methyl)pyridin-4-yl)-6-fluorobenzofuran-5-yl)methoxy)phenyl)acetate (519a) (202 mg, 100% yield) as a dark oil; MS (ES+): 535.20 (M+1).

Step-2: Preparation of Ethyl 2-(2-((7-(2-(aminomethyl)pyridin-4-yl)-6-fluorobenzofuran-5-yl)methoxy)phenyl)acetate (519b)

Compound 519b was prepared according to the procedure reported in step-5 of scheme-1 from ethyl 2-(2-((7-(2-(((tert-butoxycarbonyl)amino)methyl)pyridin-4-yl)-6-fluorobenzofuran-5-yl)methoxy)phenyl)acetate (519a) (202 mg, 0.378 mmol) in ethanol (6 mL) using 4M HCl (0.945 mL, 3.78 mmol) in dioxane followed by stirring at room temperature for 36 h. This gave after workup ethyl 2-(2-((7-(2-(aminomethyl)pyridin-4-yl)-6-fluorobenzofuran-5-yl)methoxy)phenyl)acetate (519b) (164 mg, 100% yield) HCl salt as a brown solid, which was used as such in next step-3; MS (ES+): 435.15 (M+1).

Step-3: Preparation of 2-(2-((7-(2-(aminomethyl)pyridin-4-yl)-6-fluorobenzofuran-5-yl)methoxy)phenyl)acetic Acid (519c)

Compound 519c was prepared according to the procedure reported in step-6 of scheme-1 from ethyl 2-(2-((7-(2-(aminomethyl)pyridin-4-yl)-6-fluorobenzofuran-5-yl)methoxy)phenyl)acetate (519b) (164 mg, 0.377 mmol) in THF (3 mL) and acetonitrile (3 mL) using a solution of lithium hydroxide hydrate (72 mg, 1.716 mmol) in water (2 mL). This gave after workup and purification by reverse-phase column chromatography [C18 (50 g), eluting with ACN in water (containing 0.1% HCl) from 0-100%] 2-(2-((7-(2-(aminomethyl)pyridin-4-yl)-6-fluorobenzofuran-5-yl)methoxy)phenyl)acetic acid (519c) (48 mg, 31% yield) HCl salt as a white solid; $^1$H NMR (300 MHz, DMSO-$d_6$) δ 8.82 (d, J=5.2 Hz, 1H), 8.63 (s, 3H), 8.12 (s, 1H), 8.01-7.86 (m, 2H), 7.79 (d, J=5.2 Hz, 1H), 7.32-7.18 (m, 2H), 7.15 (d, J=8.1 Hz, 1H), 7.10 (s, 1H), 6.93 (t, J=7.3 Hz, 1H), 5.29 (s, 2H), 4.40-4.23 (m, 2H), 3.56 (s, 2H); $^{19}$F NMR (282 MHz, DMSO-$d_6$) δ −127.48; MS (ES+): 407.1 (M+1); MS (ES−): 405.1 (M−1); Analysis calculated for $C_{23}H_{19}FN_2O_4 \cdot 1.75HCl \cdot 2.5H_2O$: C, 53.61; H, 5.04; Cl, 12.04; N, 5.44; Found: C, 53.53; H, 4.86; Cl, 11.89; N, 5.42.

Scheme-520

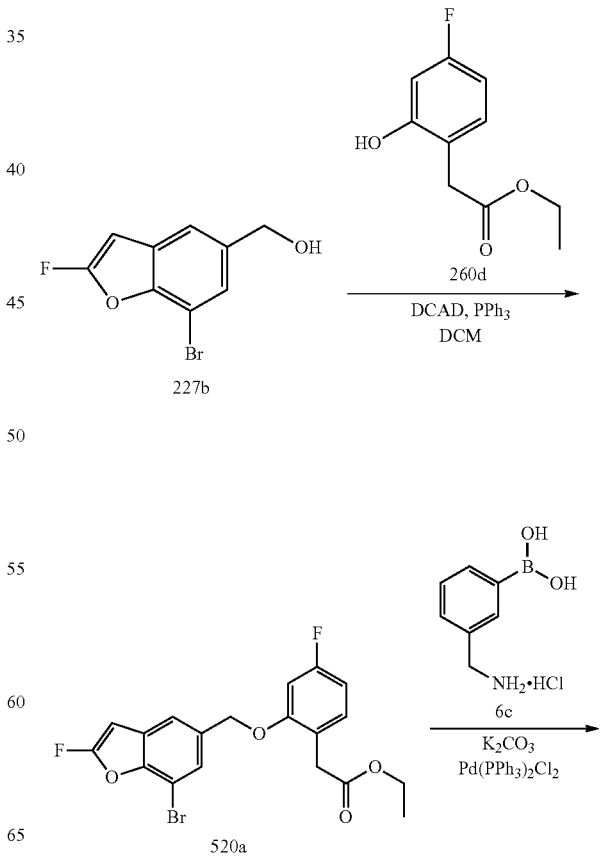

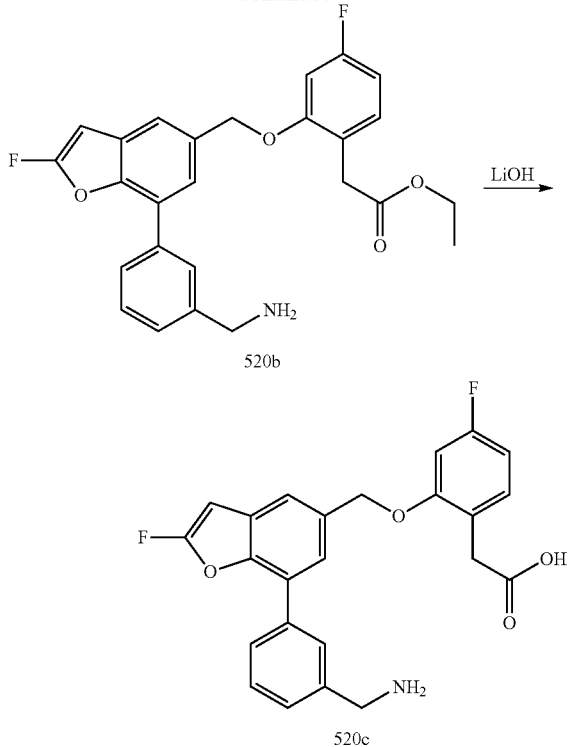

Preparation of 2-(2-((7-(3-(aminomethyl)phenyl)-2-fluorobenzofuran-5-yl)methoxy)-4-fluorophenyl) acetic Acid (520c)

Step-1: Preparation of Ethyl 2-(2-((7-bromo-2-fluorobenzofuran-5-yl)methoxy)-4-fluorophenyl)acetate (520a)

Compound 520a was prepared according to the procedure reported in step-2 of scheme-23 from (7-bromo-2-fluorobenzofuran-5-yl)methanol (227b) (1.3 g, 5.31 mmol) in DCM (60 mL) using triphenylphosphine (1.531 g, 5.84 mmol), ethyl 2-(4-fluoro-2-hydroxyphenyl)acetate (260d) (1.262 g, 6.37 mmol) and a solution of (E)-bis(4-chlorobenzyl) diazene-1,2-dicarboxylate (DCAD, 2.143 g, 5.84 mmol) in DCM (30 mL). This gave after workup and purification by flash column chromatography (silica gel, 80 g, eluting with ethyl acetate in hexanes from 0 to 25%) ethyl 2-(2-((7-bromo-2-fluorobenzofuran-5-yl)methoxy)-4-fluorophenyl) acetate (520a)(1.44 g, 63.8% yield) as a white solid. $^1$H NMR (300 MHz, DMSO-$d_6$) δ 7.64 (s, 1H), 7.58 (s, 1H), 7.25 (t, J=7.6 Hz, 1H), 7.00 (dd, J=11.3, 2.5 Hz, 1H), 6.75 (td, J=8.4, 2.4 Hz, 1H), 6.54 (d, J=6.4, 1.1 Hz, 1H), 5.18 (s, 2H), 4.03 (q, 2H), 3.60 (s, 2H), 1.08 (t, J=7.1, 1.1 Hz, 3H); $^{19}$F NMR (282 MHz, DMSO-$d_6$) δ−110.37, −110.39; MS (ES+): 448.9 (M+1).

Step-2: Preparation of Ethyl 2-(2-((7-(3-(aminomethyl)phenyl)-2-fluorobenzofuran-5-yl)methoxy)-4-fluorophenyl)acetate (520b)

Compound 520b was prepared according to the procedure reported in step-3 of scheme-1 from ethyl 2-(2-((7-bromo-2-fluorobenzofuran-5-yl)methoxy)-4-fluorophenyl)acetate (520a) (220 mg, 0.475 mmol) in dioxane (8 mL) using (3-(aminomethyl)phenyl)boronic acid hydrochloride (6c) (107 mg, 0.570 mmol), Pd(PPh$_3$)$_2$Cl$_2$ (50.0 mg, 0.071 mmol) and a solution of K$_2$CO$_3$ (197 mg, 1.425 mmol) in water (0.8 mL) heating under an argon atmosphere at 100° C. for 4 h. This gave after workup and purification by flash column chromatography [silica (24 g), eluting with DMA80 in DCM from 0-50%] ethyl 2-(2-((7-(3-(aminomethyl)phenyl)-2-fluorobenzofuran-5-yl)methoxy)-4-fluorophenyl)acetate (520b) (197 mg, 92% yield) as a clear oil; $^1$H NMR (300 MHz, DMSO-$d_6$) δ 7.76 (s, 1H), 7.67-7.59 (m, 2H), 7.55 (s, 1H), 7.45 (dt, J=14.3, 7.5 Hz, 2H), 7.25 (t, J=7.6 Hz, 1H), 7.03 (dd, J=11.3, 2.5 Hz, 1H), 6.74 (td, J=8.5, 2.6 Hz, 1H), 6.44 (d, J=6.4 Hz, 1H), 5.24 (s, 2H), 3.92 (q, J=7.1 Hz, 2H), 3.81 (s, 2H), 3.60 (s, 2H), 0.99 (t, 3H). $^{19}$F NMR (282 MHz, DMSO-$d_6$) δ−111.64, −112.65; MS (ES+): 452.20 (M+1).

Step-3: Preparation of 2-(2-((7-(3-(aminomethyl)phenyl)-2-fluorobenzofuran-5-yl)methoxy)-4-fluorophenyl)acetic Acid (520c)

Compound 520c was prepared according to the procedure reported in step-6 of scheme-1 from ethyl 2-(2-((7-(3-(aminomethyl)phenyl)-2-fluorobenzofuran-5-yl)methoxy)-4-fluorophenyl)acetate (520b) (195 mg, 0.432 mmol) in THF (2.60 mL) and acetonitrile (1.3 mL) using 1 N aqueous LiOH (1.296 mL, 1.296 mmol) and stirring at room temperature for 35 h. This gave after workup and purification by reverse phase column [C18 (50 g), eluting with acetonitrile in water (0.1% HCl) from 0-100%] 2-(2-((7-(3-(aminomethyl)phenyl)-2-fluorobenzofuran-5-yl)methoxy)-4-fluorophenyl)acetic acid (520c) (101 mg, 55% yield) HCl salt as a white solid; $^1$H NMR (300 MHz, DMSO-$d_6$) δ 12.25 (s, 1H, D$_2$O exchangeable), 8.40 (s, 3H, D$_2$O exchangeable), 7.94 (s, 1H), 7.85 (dd, J=7.2, 2.3 Hz, 1H), 7.68 (s, 1H), 7.65-7.54 (m, 3H), 7.25 (t, J=7.6 Hz, 1H), 7.01 (dd, J=11.2, 2.5 Hz, 1H), 6.74 (td, J=8.6, 2.5 Hz, 1H), 6.45 (d, J=6.4 Hz, 1H), 5.27 (s, 2H), 4.14 (s, 2H), 3.57 (s, 2H); $^{19}$F NMR (282 MHz, DMSO-$d_6$) δ−111.46, −112.93; MS (ES+): 424.1 (M+1), (ES−): 422.1 (M−1); Analysis calculated for C$_{24}$H$_{19}$F$_2$NO$_4$·HCl·H$_2$O: C, 60.32; H, 4.64; Cl, 7.42; N, 2.93; Found: C, 60.41; H, 4.62; Cl, 7.28; N, 2.92.

Scheme-521

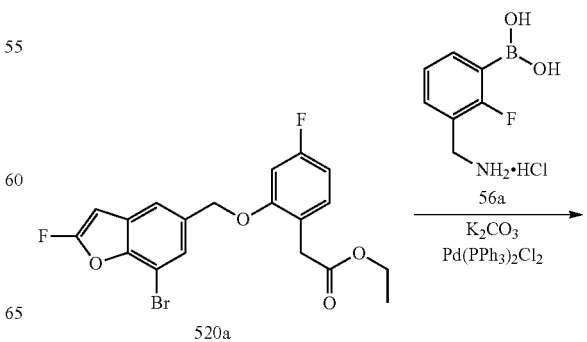

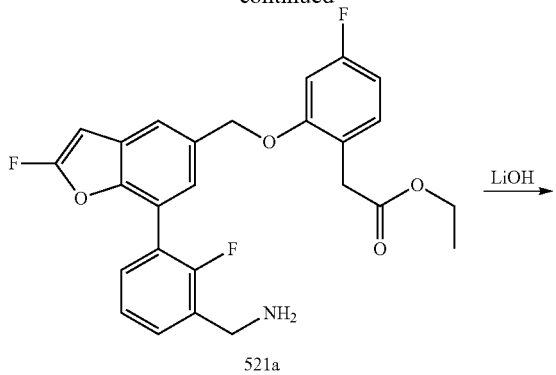

Preparation of 2-(2-((7-(3-(aminomethyl)-2-fluorophenyl)-2-fluorobenzofuran-5-yl)methoxy)-4-fluorophenyl)acetic Acid (521b)

Step-1: Preparation of Ethyl 2-(2-((7-(3-(aminomethyl)-2-fluorophenyl)-2-fluorobenzofuran-5-yl)methoxy)-4-fluorophenyl)acetate (521a)

Compound 521a was prepared according to the procedure reported in step-3 of scheme-1 from ethyl 2-(2-((7-bromo-2-fluorobenzofuran-5-yl)methoxy)-4-fluorophenyl)acetate (520a) (202 mg, 0.475 mmol) in dioxane (8 mL) using (3-(aminomethyl)-2-fluorophenyl)boronic acid hydrochloride (56a) (117 mg, 0.570 mmol), Pd(PPh$_3$)$_2$Cl$_2$ (50.0 mg, 0.071 mmol) and a solution of K$_2$CO$_3$ (197 mg, 1.425 mmol) in water (0.8 mL) heating under an argon atmosphere at 100° C. for 4 h. This gave after workup and purification by flash column chromatography [silica (24 g), eluting with DMA80 in DCM from 0-50%] ethyl 2-(2-((7-(3-(aminomethyl)-2-fluorophenyl)-2-fluorobenzofuran-5-yl)methoxy)-4-fluorophenyl)acetate (521a) (220 mg, 99% yield) as a clear oil; $^1$H NMR (300 MHz, DMSO-d$_6$) δ 7.64-7.60 (m, 2H), 7.45 (t, J=7.4 Hz, 1H), 7.40 (s, 1H), 7.32 (t, J=7.6 Hz, 1H), 7.24 (t, J=7.6 Hz, 1H), 7.10-6.95 (m, 1H), 6.74 (td, J=8.5, 2.4 Hz, 1H), 6.52-6.38 (m, 1H), 5.23 (s, 2H), 3.95-3.86 (m, 2H), 3.84 (s, 2H), 3.59 (s, 2H), 0.98 (td, J=7.1, 1.1 Hz, 3H); $^{19}$F NMR (282 MHz, DMSO-d$_6$) δ−111.61, −112.65, −122.02; MS (ES+): 470.1 (M+1).

Step-2: Preparation of 2-(2-((7-(3-(aminomethyl)-2-fluorophenyl)-2-fluorobenzofuran-5-yl)methoxy)-4-fluorophenyl)acetic Acid (521b)

Compound 521b was prepared according to the procedure reported in step-6 of scheme-1 from ethyl 2-(2-((7-(3-(aminomethyl)-2-fluorophenyl)-2-fluorobenzofuran-5-yl)methoxy)-4-fluorophenyl)acetate (521a) (217 mg, 0.462 mmol) in THF (2.8 mL) and acetonitrile (1.4 mL) using 1 N aqueous LiOH (1.387 mL, 1.387 mmol) and stirring at room temperature for 35 h. This gave after workup and purification by reverse phase column [C18 (50 g), eluting with acetonitrile in water (0.1% HCl) from 0-100%] 2-(2-((7-(3-(aminomethyl)-2-fluorophenyl)-2-fluorobenzofuran-5-yl)methoxy)-4-fluorophenyl)acetic acid (521b) (101 mg, 55% yield) HCl salt as a white solid; $^1$H NMR (300 MHz, DMSO-d$_6$) δ 7.77-7.62 (m, 3H), 7.47 (s, 1H), 7.43 (t, J=7.7 Hz, 1H), 7.24 (t, J=7.6 Hz, 1H), 7.01 (dd, J=11.3, 2.5 Hz, 1H), 6.74 (td, J=8.5, 2.5 Hz, 1H), 6.46 (d, J=6.5, 1.1 Hz, 1H), 5.27 (s, 2H), 4.15 (s, 2H), 3.55 (s, 2H); $^{19}$F NMR (282 MHz, DMSO-d$_6$) δ−111.51, −113.03, −118.73; MS (ES+): 442.1 (M+1), (ES−): 440.1 (M−1); Analysis calculated for C$_{24}$H$_{18}$F$_3$NO$_4$.0.85HCl.H$_2$O: C, 58.78; H, 4.29; Cl, 6.14; N, 2.86; Found: C, 59.07; H, 4.39; Cl, 6.42; N, 2.85.

Scheme-522

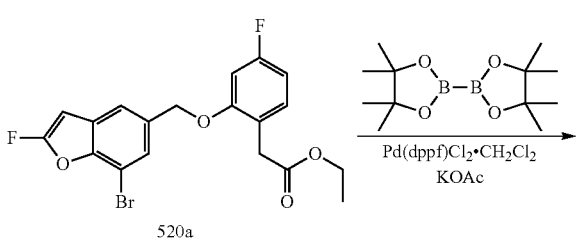

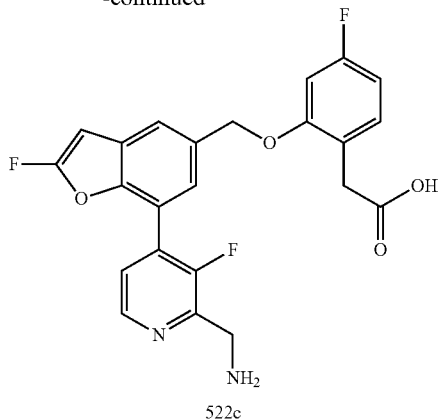

522c

Preparation of 2-(2-((7-(2-(aminomethyl)-3-fluoro-pyridin-4-yl)-2-fluorobenzofuran-5-yl)methoxy)-4-fluorophenyl)acetic Acid (522c)

Step 1. Preparation of ethyl 2-(4-fluoro-2-((2-fluoro-7-(4,4,5,5-tetramethyl-1,3,2-dioxaborolan-2-yl)benzofuran-5-yl)methoxy)phenyl)acetate (522a)

Compound 522a was prepared according to the procedure reported in step-1 of scheme-59 from ethyl 2-(2-((7-bromo-2-fluorobenzofuran-5-yl)methoxy)-4-fluorophenyl)acetate (520a) (0.84 g, 1.975 mmol) using bis(pinacolato)diboron (0.752 g, 2.96 mmol), potassium acetate (0.582 g, 5.93 mmol) and Pd(dppf)Cl$_2$—CH$_2$Cl$_2$ (0.161 g, 0.198 mmol) in anhydrous dioxane (25 mL) under an argon atmosphere and heating at 90° C. for 16 h. This gave after workup and purification by flash column chromatography [silica (40 g), eluting with EtOAc in hexane from 0-40%] ethyl 2-(4-fluoro-2-((2-fluoro-7-(4,4,5,5-tetramethyl-1,3,2-dioxaborolan-2-yl)benzofuran-5-yl)methoxy)phenyl)acetate (522a) as a colorless oil; $^1$H NMR (300 MHz, DMSO-d$_6$) δ 7.75 (s, 1H), 7.61 (s, 1H), 7.24 (t, J=7.6 Hz, 1H), 7.02 (dd, J=10.3, 2.1 Hz, 1H), 6.74 (td, J=8.4 Hz, 1H), 6.36 (d, J=6.3 Hz, 1H), 5.17 (s, 2H), 4.00 (q, J=7.1 Hz, 2H), 3.57 (s, 2H), 1.34 (s, 12H), 1.05 (t, J=7.1 Hz, 3H); $^{19}$F NMR (282 MHz, DMSO-d$_6$) δ−111.63, −112.69.

Step 2-Preparation of (+)-(S)-ethyl 2-(2-((7-(2-((1,1-dimethylethylsulfinamido)methyl)-3-fluoropyridin-4-yl)-2-fluorobenzofuran-5-yl)methoxy)-4-fluorophenyl)acetate (522b)

Compound 522b was prepared according to the procedure reported in step-3 of scheme-1 from ethyl 2-(4-fluoro-2-((2-fluoro-7-(4,4,5,5-tetramethyl-1,3,2-dioxaborolan-2-yl)benzofuran-5-yl)methoxy)phenyl)acetate (522a) (220 mg, 0.466 mmol) in dioxane (10 mL) using (+)-(S)—N-((4-chloro-3-fluoropyridin-2-yl)methyl)-2-methylpropane-2-sulfinamide (220c) (123 mg, 0.466 mmol), Pd(PPh$_3$)$_2$Cl$_2$ (49 mg, 0.070 mmol) and a solution of K$_2$CO$_3$ (193 mg, 1.397 mmol) in water (1 mL) under a nitrogen atmosphere heating at 100° C. for 4 h on oil bath. This gave after workup and purification by flash column chromatography [silica gel (24 g), eluting with DMA80 in DCM from 0-30%] (+)-(S)-ethyl 2-(2-((7-(2-((1,1-dimethylethylsulfinamido)methyl)-3-fluoropyridin-4-yl)-2-fluorobenzofuran-5-yl)methoxy)-4-fluorophenyl)acetate (522b) (160 mg, 60% yield) as a brown oil; MS (ES+) 575.2 (M+1); Optical rotation [t]D=+18.46 (c=0.065, MeOH).

Step-3: Preparation of 2-(2-((7-(2-(aminomethyl)-3-fluoropyridin-4-yl)-2-fluorobenzofuran-5-yl)methoxy)-4-fluorophenyl)acetic Acid (522c)

Compound 522c was prepared according to the procedure reported in step-2 of scheme-499 from (+)-(S)-ethyl 2-(2-((7-(2-((1,1-dimethylethylsulfinamido)methyl)-3-fluoropyridin-4-yl)-2-fluorobenzofuran-5-yl)methoxy)-4-fluorophenyl)acetate (522b) (155 mg, 0.27 mmol) in THF (4.50 mL) using 4 M HCl in 1,4-dioxane (0.135 mL, 0.539 mmol), and stirring at room temperature for 30 min. The reaction was concentrated in vacuum to dryness. The residue obtained was dissolved in THF (3.0 mL) and acetonitrile (1.5 mL), added 1 N aqueous LiOH (1.5 mL, 1.5 mmol) and stirred at room temperature for 48 h. This gave after workup and purification by reverse phase column [C-18 column, 50 g, eluting with acetonitrile in water (containing 0.1% HCl) from 0-100%] 2-(2-((7-(2-(aminomethyl)-3-fluoropyridin-4-yl)-2-fluorobenzofuran-5-yl)methoxy)-4-fluorophenyl)acetic acid (522c) (43 mg, 36% yield) HCl salt as a white solid; $^1$H NMR (300 MHz, DMSO-d$_6$) δ 8.64 (d, J=5.0 Hz, 1H), 8.59-8.49 (m, 3H, D$_2$O exchangeable), 7.86-7.76 (m, 2H), 7.58 (s, 1H), 7.25 (t, J=7.6 Hz, 1H), 7.02 (dd, J=11.5, 2.5 Hz, 1H), 6.74 (td, J=8.5, 2.5 Hz, 1H), 6.51 (d, J=6.3 Hz, 1H), 5.29 (s, 2H), 4.51-4.20 (m, 2H), 3.56 (s, 2H); $^{19}$F NMR (282 MHz, DMSO) δ−111.11, −112.90, −128.53; MS (ES+): 443.1 (M+1); (ES−): 441.1 (M−1); Analysis calculated for C$_{23}$H$_{17}$F$_3$N$_2$O$_4$.HCl.1.5H$_2$O: C, 54.61; H, 4.18; Cl, 7.01; N, 5.54; Found: C, 54.87; H, 4.17; Cl, 6.94; N, 5.50.

Scheme-523

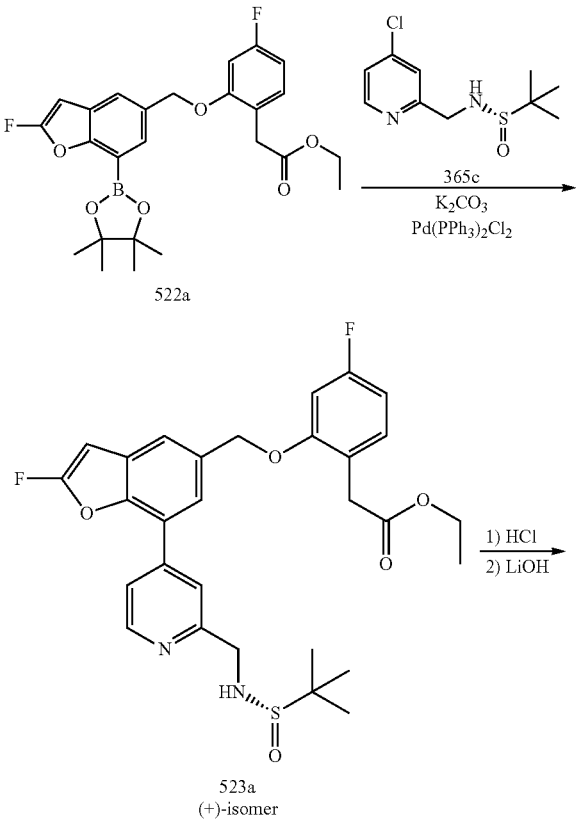

522a 523a
(+)-isomer

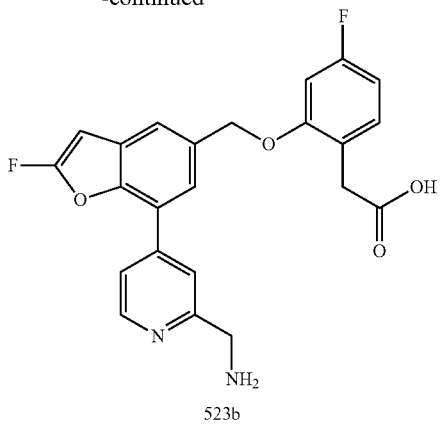

523b

Preparation of 2-(2-((7-(2-(aminomethyl)pyridin-4-yl)-2-fluorobenzofuran-5-yl)methoxy)-4-fluorophenyl)acetic Acid (523b)

Step 1-Preparation of (+)-(S)-ethyl 2-(2-((7-(2-((1,1-dimethylethylsulfinamido)methyl)pyridin-4-yl)-2-fluorobenzofuran-5-yl)methoxy)-4-fluorophenyl)acetate (523a)

Compound 523a was prepared according to the procedure reported in step-3 of scheme-1 from ethyl 2-(4-fluoro-2-((2-fluoro-7-(4,4,5,5-tetramethyl-1,3,2-dioxaborolan-2-yl)benzofuran-5-yl)methoxy)phenyl)acetate (522a) (220 mg, 0.466 mmol) in dioxane (10 mL) using (+)-(S)—N-((4-chloropyridin-2-yl)methyl)-2-methylpropane-2-sulfinamide (365c) (115 mg, 0.466 mmol), Pd(PPh$_3$)$_2$Cl$_2$ (49 mg, 0.070 mmol) and a solution of K$_2$CO$_3$ (193 mg, 1.397 mmol) in water (1 mL) under a nitrogen atmosphere heating at 100° C. for 4 h on oil bath. This gave after workup and purification by flash column chromatography [silica gel (24 g), eluting with DMA80 in DCM from 0-30%] (+)-(S)-ethyl 2-(2-((7-(2-((1,1-dimethylethylsulfinamido)methyl)pyridin-4-yl)-2-fluorobenzofuran-5-yl)methoxy)-4-fluorophenyl)acetate (523a) (140 mg, 54% yield) as a brown oil; MS (ES+) 557.2 (M+1); Optical rotation [t]D=+27.69 (c=0.065, MeOH).

Step-3: Preparation of 2-(2-((7-(2-(aminomethyl)pyridin-4-yl)-2-fluorobenzofuran-5-yl)methoxy)-4-fluorophenyl)acetic Acid (523b)

Compound 523b was prepared according to the procedure reported in step-2 of scheme-499 from (+)-(S)-ethyl 2-(2-((7-(2-((1,1-dimethylethylsulfinamido)methyl)pyridin-4-yl)-2-fluorobenzofuran-5-yl)methoxy)-4-fluorophenyl)acetate (523a) (135 mg, 0.243 mmol) in THF (3.75 mL) using 4 M HCl in 1,4-dioxane, (0.121 mL, 0.485 mmol) and stirring at room temperature for 30 min. The reaction was concentrated in vacuum to dryness. The residue obtained was dissolved in THF (2.5 mL) and acetonitrile (1.25 mL), added 1 N aqueous LiOH (1.25 mL, 1.250 mmol) and stirred at room temperature for 48 h. This gave after workup and purification by reverse phase column [C-18 column, 50 g, eluting with acetonitrile in water (containing 0.1% HCl) from 0-100%] 2-(2-((7-(2-(aminomethyl)pyridin-4-yl)-2-fluorobenzofuran-5-yl)methoxy)-4-fluorophenyl)acetic acid (523b) (53 mg, 52% yield) HCl salt as a white solid; $^1$H NMR (300 MHz, DMSO-d$_6$) δ 8.79 (d, J=5.3 Hz, 1H), 8.47 (s, 3H, D$_2$O exchangeable), 8.00 (s, 1H), 7.90 (d, J=5.3 Hz, 1H), 7.77 (d, J=8.6 Hz, 2H), 7.25 (t, J=7.6 Hz, 1H), 7.01 (dd, J=11.3, 2.5 Hz, 1H), 6.75 (td, J=8.5, 2.5 Hz, 1H), 6.51 (d, J=6.4 Hz, 1H), 5.29 (s, 2H), 4.44-4.21 (m, 2H), 3.57 (s, 2H); $^{19}$F NMR (282 MHz, DMSO) δ–111.05, –112.94; MS (ES+): 425.1 (M+1); (ES–): 423.1 (M–1); Analysis calculated for C$_{23}$H$_{18}$F$_2$N$_2$O$_4$.1.5HCl.1.75H$_2$O: C, 54.10; H, 4.54; Cl, 10.41; N, 5.49; Found: C, 58.72; H, 4.32; Cl, 10.77; N, 5.49.

Scheme-524

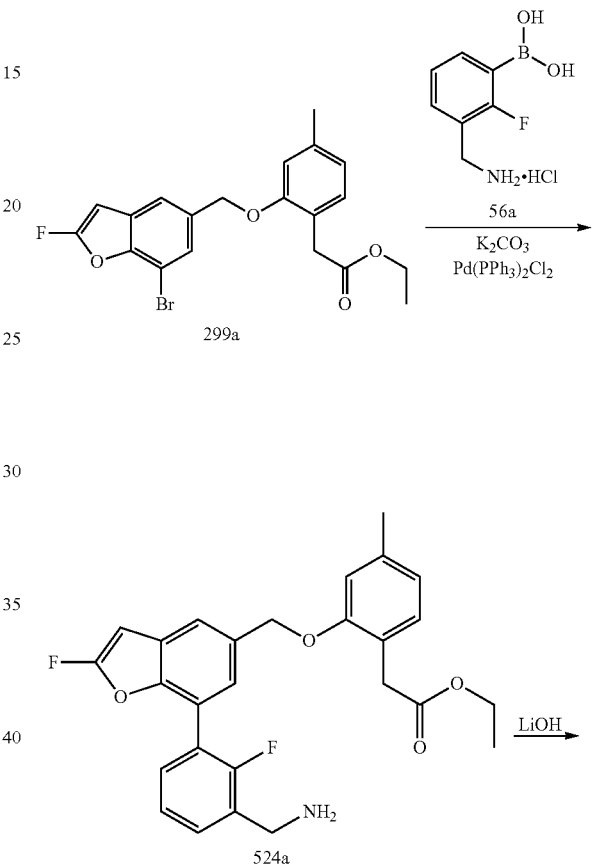

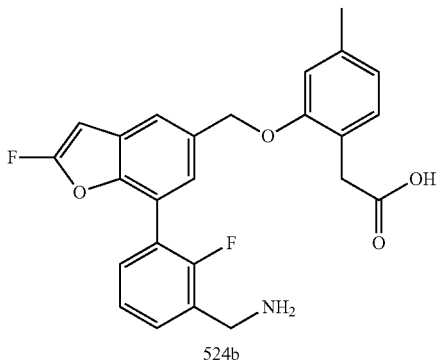

524b

Preparation of 2-(2-((7-(3-(aminomethyl)-2-fluorophenyl)-2-fluorobenzofuran-5-yl)methoxy)-4-methylphenyl)acetic Acid (524b)

Step-1: Preparation of Ethyl 2-(2-((7-(3-(aminomethyl)-2-fluorophenyl)-2-fluorobenzofuran-5-yl)methoxy)-4-methylphenyl)acetate (524a)

Compound 524a was prepared according to the procedure reported in step-3 of scheme-1 from ethyl 2-(2-((7-bromo-2-fluorobenzofuran-5-yl)methoxy)-4-methylphenyl)acetate (299a) (200 mg, 0.475 mmol) in dioxane (8 mL) using (3-(aminomethyl)-2-fluorophenyl)boronic acid hydrochloride (56a) (117 mg, 0.570 mmol), a solution of $K_2CO_3$ (197 mg, 1.424 mmol) in water (0.8 mL), bis(triphenylphosphine)palladium(II) chloride (50.0 mg, 0.071 mmol) and heating at 100° C. for 4 h on oil bath. This gave after workup and purification by flash column chromatography [silica (24 g), eluting with DMA80 in DCM from 0-50%] ethyl 2-(2-((7-(3-(aminomethyl)-2-fluorophenyl)-2-fluorobenzofuran-5-yl)methoxy)-4-methylphenyl)acetate (524a) (125 mg, 57% yield) as a clear oil; $^1$H NMR (300 MHz, DMSO-$d_6$) δ 7.67 (s, 1H), 7.61 (t, J=7.3 Hz, 1H), 7.45 (t, J=7.3 Hz, 1H), 7.41 (s, 1H), 7.32 (t, J=7.6 Hz, 1H), 7.08 (d, J=7.5 Hz, 1H), 6.95 (s, 1H), 6.73 (d, J=7.5 Hz, 1H), 6.45 (d, J=6.5 Hz, 1H), 5.19 (s, 2H), 3.90 (q, J=7.1 Hz, 2H), 3.84 (s, 2H), 3.56 (s, 2H), 2.30 (s, 3H), 0.98 (t, 3H); $^{19}$F NMR (282 MHz, DMSO-$d_6$) δ−111.72, −122.00; MS (ES+): 466.2 (M+1).

Step-2: Preparation of 2-(2-((7-(3-(aminomethyl)-2-fluorophenyl)-2-fluorobenzofuran-5-yl)methoxy)-4-methylphenyl)acetic Acid (524b)

Compound 524b was prepared according to the procedure reported in step-6 of scheme-1 from ethyl 2-(2-((7-(3-(aminomethyl)-2-fluorophenyl)-2-fluorobenzofuran-5-yl)methoxy)-4-methylphenyl)acetate (524a) (120 mg, 0.258 mmol) in acetonitrile/THF (0.45/0.90 mL) using a solution of 1 N lithium hydroxide monohydrate (0.773 mL, 0.773 mmol) and stirring the reaction at room temperature for 35 h. This gave after workup and purification by reverse-phase column chromatography [C-18 column, 50 g, eluting with acetonitrile in water (containing 0.1% aqueous HCl) from 0-100%] 2-(2-((7-(3-(aminomethyl)-2-fluorophenyl)-2-fluorobenzofuran-5-yl)methoxy)-4-methylphenyl)acetic acid (524b) (90 mg, 80% yield) hydrochloride salt as a white solid. $^1$H NMR (300 MHz, DMSO-$d_6$) δ 7.77-7.61 (m, 3H), 7.49-7.40 (m, 2H), 7.08 (d, J=7.5 Hz, 1H), 6.94 (s, 1H), 6.73 (d, J=7.5 Hz, 1H), 6.45 (d, J=6.4 Hz, 1H), 5.22 (s, 2H), 4.17 (s, 2H), 3.52 (s, 2H), 2.29 (s, 3H); $^{19}$F NMR (282 MHz, DMSO-$d_6$) δ−111.62, −118.60; MS (ES+): 438.10 (M+1), (ES−): 436.10 (M−1); Analysis calculated for $C_{25}H_{21}F_2NO_4 \cdot HCl \cdot H_2O$: C, 61.04; H, 4.92; Cl, 7.21; F, 7.72; N, 2.85; Found: C, 61.05; H, 4.78; Cl, 7.19; N, 2.93.

Scheme-525

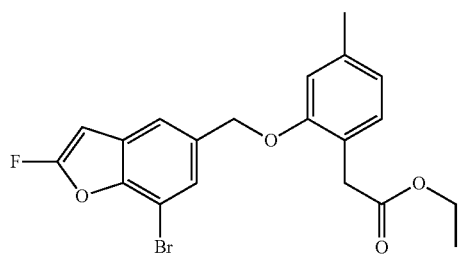

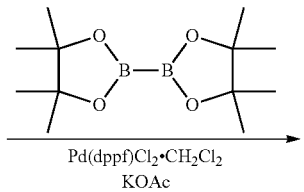

299a

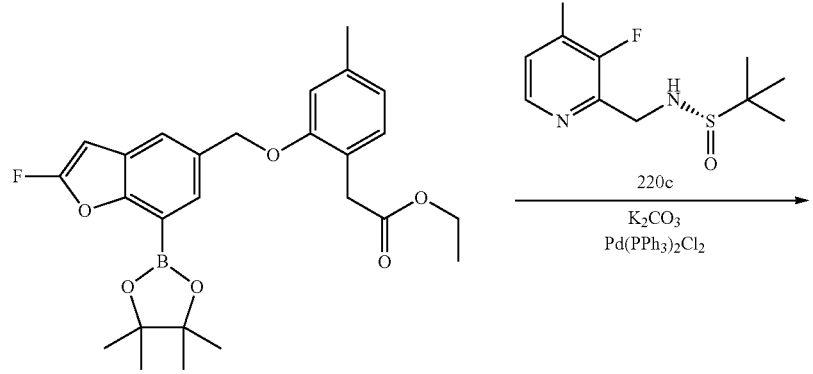

525a

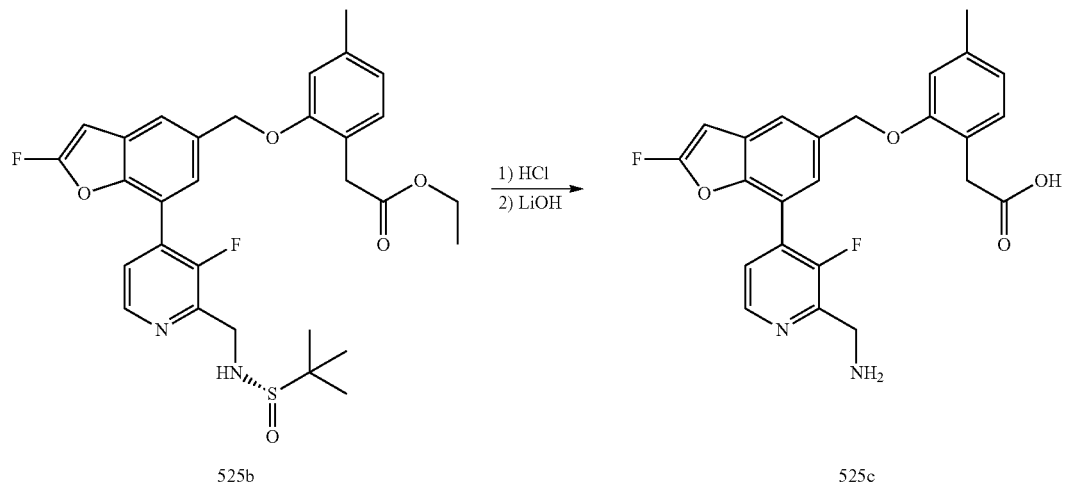

525b → 1) HCl  2) LiOH → 525c

Preparation of 2-(2-((7-(2-(aminomethyl)-3-fluoro-pyridin-4-yl)-2-fluorobenzofuran-5-yl)methoxy)-4-methylphenyl)acetic Acid (525c)

Step 1. Preparation of ethyl 2-(2-((2-fluoro-7-(4,4,5,5-tetramethyl-1,3,2-dioxaborolan-2-yl)benzofuran-5-yl)methoxy)-4-methylphenyl)acetate (525a)

Compound 525a was prepared according to the procedure reported in step-1 of scheme-59 from ethyl 2-(2-((7-bromo-2-fluorobenzofuran-5-yl)methoxy)-4-methylphenyl)acetate (299a) (1 g, 2.374 mmol) using bis(pinacolato)diboron (0.904 g, 3.56 mmol), potassium acetate (0.699 g, 7.12 mmol) and Pd(dppf)Cl$_2$—CH$_2$Cl$_2$ (0.194 g, 0.237 mmol) in anhydrous dioxane (35 mL) under an argon atmosphere and heating at 90° C. for 16 h. This gave after workup and purification by flash column chromatography [silica (40 g), eluting with EtOAc in hexane from 0-40%] ethyl 2-(2-((2-fluoro-7-(4,4,5,5-tetramethyl-1,3,2-dioxaborolan-2-yl)benzofuran-5-yl)methoxy)-4-methylphenyl)acetate (525a) as a colorless oil; $^1$H NMR (300 MHz, DMSO-d$_6$) δ 7.74 (s, 1H), 7.61 (s, 1H), 7.08 (d, J=7.5 Hz, 1H), 6.93 (s, 1H), 6.72 (d, J=7.5 Hz, 1H), 6.38-6.33 (m, 1H), 5.13 (s, 2H), 3.99 (q, J=6.7 Hz, 2H), 3.53 (s, 2H), 2.29 (s, 3H), 1.34 (s, 12H), 1.05 (t, 3H); $^{19}$F NMR (282 MHz, DMSO-d$_6$) δ−111.72.

Step 2-Preparation of (+)-(S)-ethyl 2-(2-((7-(2-((1,1-dimethylethylsulfinamido)methyl)-3-fluoropyridin-4-yl)-2-fluorobenzofuran-5-yl)methoxy)-4-methylphenyl)acetate (525b)

Compound 525b was prepared according to the procedure reported in step-3 of scheme-1 from ethyl 2-(2-((2-fluoro-7-(4,4,5,5-tetramethyl-1,3,2-dioxaborolan-2-yl)benzofuran-5-yl)methoxy)-4-methylphenyl)acetate (525a) (220 mg, 0.470 mmol) in dioxane (10 mL) using (+)-(S)—N-((4-chloro-3-fluoropyridin-2-yl)methyl)-2-methylpropane-2-sulfinamide (220c) (124 mg, 0.470 mmol), Pd(PPh$_3$)$_2$Cl$_2$ (49.5 mg, 0.070 mmol) and a solution of K$_2$CO$_3$ (195 mg, 1.409 mmol) in water (1.0 mL) under a nitrogen atmosphere heating at 100° C. for 4 h on oil bath. This gave after workup and purification by flash column chromatography [silica gel (24 g), eluting with DMA80 in DCM from 0-30%] (+)-(S)-ethyl 2-(2-((7-(2-((1,1-dimethylethylsulfinamido)methyl)-3-fluoropyridin-4-yl)-2-fluorobenzofuran-5-yl)methoxy)-4-methylphenyl)acetate (525b) (230 mg, 86% yield) as a brown oil; MS (ES+) 571.2 (M+1); Optical rotation [α]$_D$=+21.33 (c=0.075, MeOH).

Step-3: Preparation of 2-(2-((7-(2-(aminomethyl)-3-fluoropyridin-4-yl)-2-fluorobenzofuran-5-yl)methoxy)-4-methylphenyl)acetic Acid (525c)

Compound 525c was prepared according to the procedure reported in step-2 of scheme-499 from (+)-(S)-ethyl 2-(2-((7-(2-((1,1-dimethylethylsulfinamido)methyl)-3-fluoropyridin-4-yl)-2-fluorobenzofuran-5-yl)methoxy)-4-methylphenyl)acetate (525b) (225 mg, 0.394 mmol) in THF (4 mL) using 4 M HCl in 1,4-dioxane (0.197 mL, 0.789 mmol) and stirring at room temperature for 30 min. The reaction was concentrated in vacuum to dryness. The residue obtained was dissolved in THF (4 mL) and acetonitrile (2 mL), added 1 N aqueous LiOH (2.0 mL, 2.000 mmol) and stirred at room temperature for 48 h. This gave after workup and purification by reverse phase column [C-18 column, 50 g, eluting with acetonitrile in water (containing 0.1% HCl) from 0-100%] 2-(2-((7-(2-(aminomethyl)-3-fluoropyridin-4-yl)-2-fluorobenzofuran-5-yl)methoxy)-4-methylphenyl)acetic acid (525c) (53 mg, 31% yield) HCl salt as a white solid; $^1$H NMR (300 MHz, DMSO-d$_6$) δ 8.64 (d, J=5.0 Hz, 1H), 8.57 (s, 3H, D$_2$O exchangeable), 7.86-7.75 (m, 2H), 7.59 (s, 1H), 7.09 (d, J=7.5 Hz, 1H), 6.94 (s, 1H), 6.73 (d, J=7.5 Hz, 1H), 6.51 (d, J=6.4 Hz, 1H), 5.24 (s, 2H), 4.44-4.31 (m, 2H), 3.52 (s, 2H), 2.29 (s, 3H); $^{19}$F NMR (282 MHz, DMSO-d$_6$) δ−111.19, −128.53; MS (ES+): 439.1 (M+1); (ES−): 437.1 (M−1); Analysis calculated for C$_{24}$H$_{20}$F$_2$N$_2$O$_4$.HCl.H$_2$O: C, 58.48; H, 4.70; Cl, 7.19; N, 5.68; Found: C, 58.18; H, 4.57; Cl, 6.91; N, 5.67.

Scheme-526

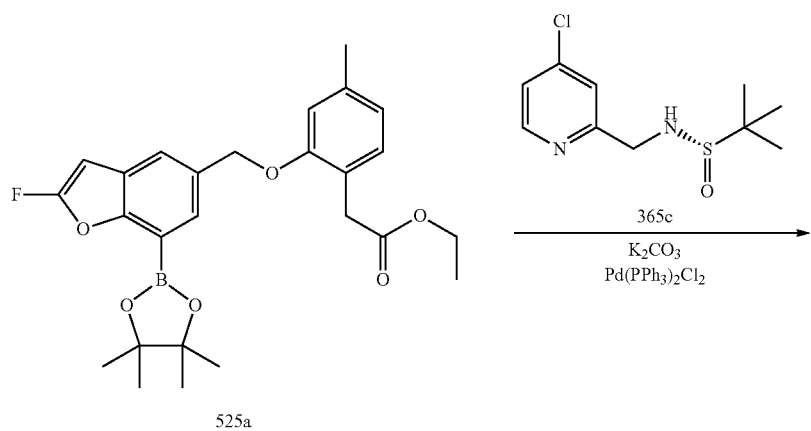

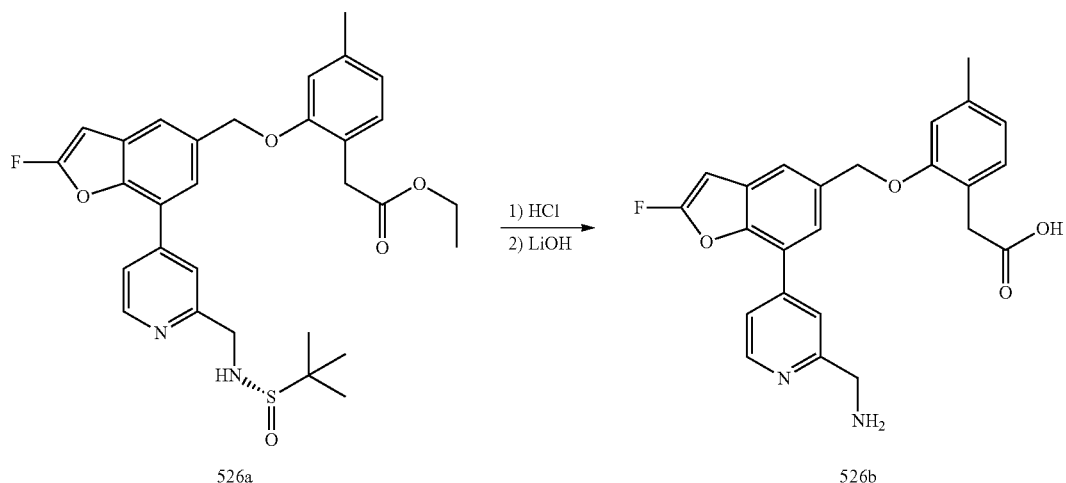

Preparation of 2-(2-((7-(2-(aminomethyl)pyridin-4-yl)-2-fluorobenzofuran-5-yl)methoxy)-4-methylphenyl)acetic Acid (526b)

Step 1-Preparation of (+)-(S)-ethyl 2-(2-((7-(2-((1,1-dimethylethylsulfinamido)methyl)pyridin-4-yl)-2-fluorobenzofuran-5-yl)methoxy)-4-methylphenyl)acetate (526a)

Compound 526a was prepared according to the procedure reported in step-3 of scheme-1 from ethyl 2-(2-((2-fluoro-7-(4,4,5,5-tetramethyl-1,3,2-dioxaborolan-2-yl)benzofuran-5-yl)methoxy)-4-methylphenyl)acetate (525a) (220 mg, 0.470 mmol) in dioxane (10 mL) using (+)-(S)—N-((4-chloropyridin-2-yl)methyl)-2-methylpropane-2-sulfinamide (365c) (116 mg, 0.470 mmol), Pd(PPh$_3$)$_2$Cl$_2$ (49.5 mg, 0.070 mmol) and a solution of K$_2$CO$_3$ (195 mg, 1.409 mmol) in water (1 mL) under a nitrogen atmosphere heating at 100° C. for 4 h on oil bath. This gave after workup and purification by flash column chromatography [silica gel (24 g), eluting with DMA80 in DCM from 0-30%] (+)-(S)-ethyl 2-(2-((7-(2-((1,1-dimethylethylsulfinamido)methyl)pyridin-4-yl)-2-fluorobenzofuran-5-yl)methoxy)-4-methylphenyl)acetate (526a) (120 mg, 46% yield) as a brown oil; MS (ES+): 553.2 (M+1); Optical rotation [o]D=+57.14 (c=0.035, MeOH).

Step-3: Preparation of 2-(2-((7-(2-(aminomethyl)pyridin-4-yl)-2-fluorobenzofuran-5-yl)methoxy)-4-methylphenyl)acetic Acid (526b)

Compound 526b was prepared according to the procedure reported in step-2 of scheme-499 from (+)-(S)-ethyl 2-(2-((7-(2-((1,1-dimethylethylsulfinamido)methyl)pyridin-4-yl)-2-fluorobenzofuran-5-yl)methoxy)-4-methylphenyl)acetate (526a) (115 mg, 0.208 mmol) in THF (3.30 mL) using 4 M HCl in 1,4-dioxane, (0.104 mL, 0.416 mmol) and stirring at room temperature for 30 min. The reaction was concentrated in vacuum to dryness. The residue obtained was dissolved in THF (2.2 mL) and acetonitrile (1.1 mL), added 1 N aqueous LiOH (1.1 mL, 1.100 mmol) and stirred at room temperature for 48 h. This gave after workup and purification by reverse phase column [C-18 column, 50 g, eluting with acetonitrile in water (containing 0.1% HCl) from 0-100%] 2-(2-((7-(2-(aminomethyl)pyridin-4-yl)-2-fluorobenzofuran-5-yl)methoxy)-4-methylphenyl)acetic acid (526b) (35 mg, 40% yield) HCl salt as a white solid; $^1$H NMR (300 MHz, DMSO-$d_6$) δ 8.79 (d, J=5.3 Hz, 1H), 8.48 (s, 3H, $D_2O$ exchangeable), 8.01 (s, 1H), 7.91 (d, J=5.3 Hz, 1H), 7.78 (d, J=4.5 Hz, 2H), 7.10 (d, J=7.5 Hz, 1H), 6.94 (s, 1H), 6.73 (d, J=7.5 Hz, 1H), 6.51 (d, J=6.4 Hz, 1H), 5.25 (s, 2H), 4.38-4.23 (m, 2H), 3.55 (s, 2H), 2.29 (s, 3H); $^{19}$F NMR (282 MHz, DMSO) δ−111.18; MS (ES+): 421.1 (M+1); (ES−): 419.1 (M−1); Analysis calculated for $C_{24}H_{21}FN_2O_4 \cdot 1.65HCl \cdot 1.5H_2O$: C, 56.79; H, 5.09; Cl, 11.52; N, 5.52; Found: C, 56.45; H, 4.99; Cl, 11.25; N, 5.64.

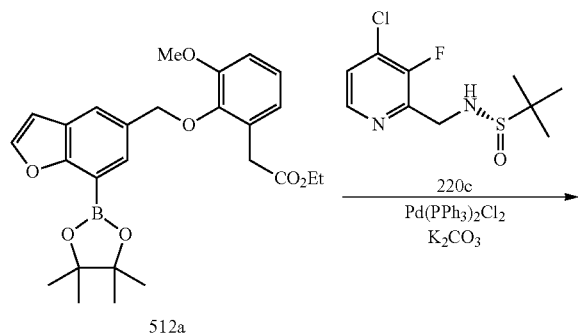

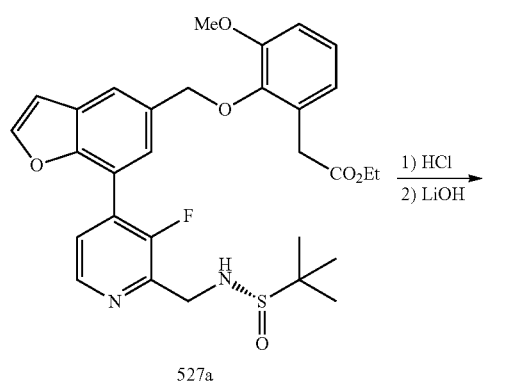

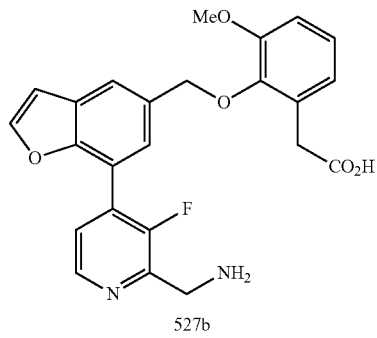

Preparation of 2-(2-((7-(2-(aminomethyl)-3-fluoropyridin-4-yl)benzofuran-5-yl)methoxy)-3-methoxyphenyl)acetic Acid (527b)

Step-1: Preparation of (+)-(S)-ethyl 2-(2-((7-(2-((1,1-dimethylethylsulfinamido)methyl)-3-fluoropyridin-4-yl)benzofuran-5-yl)methoxy)-3-methoxyphenyl)acetate (527a)

Compound 527a was prepared according to the procedure reported in step-3 of scheme-1 from ethyl 2-(3-methoxy-2-((7-(4,4,5,5-tetramethyl-1,3,2-dioxaborolan-2-yl)benzofuran-5-yl)methoxy)phenyl)acetate (512a) (407 mg, 0.873 mmol) in dioxane (4 mL) using (+)-(S)—N-((4-chloro-3-fluoropyridin-2-yl)methyl)-2-methylpropane-2-sulfinamide (220c) (254 mg, 0.960 mmol), Pd(PPh$_3$)$_2$Cl$_2$ (61.3 mg, 0.087 mmol) and a solution of K$_2$CO$_3$ (362.1 mg, 2.62 mmol) in water (0.8 mL) under a nitrogen atmosphere heating at 100° C. for 16 h on oil bath. This gave after workup and purification by flash column chromatography [(silica gel 12 g, eluting with MeOH in DCM from 0-3%)] (+)-(S)-ethyl 2-(2-((7-(2-((1,1-dimethylethylsulfinamido)methyl)-3-fluoropyridin-4-yl)benzofuran-5-yl)methoxy)-3-methoxyphenyl)acetate (527a) (412 mg, 83% yield) as an orange oil; MS (ES+) 569.2 (M+1); Optical rotation [t]D=+36.19 (c=0.105, MeOH).

Step-2: Preparation of 2-(2-((7-(2-(aminomethyl)-3-fluoropyridin-4-yl)benzofuran-5-yl)methoxy)-3-methoxyphenyl)acetic Acid (527b)

Compound 527b was prepared according to the procedure reported in step-2 of scheme-499 from (+)-(S)-ethyl 2-(2-((7-(2-((1,1-dimethylethylsulfinamido)methyl)-3-fluoropyridin-4-yl)benzofuran-5-yl)methoxy)-3-methoxyphenyl)acetate (527a) (412 mg, 0.725 mmol) in EtOH (4 mL) using 4 M HCl in dioxane (0.543 mL, 2.174 mmol) and stirring at room temperature for 16 h. To this reaction mixture was added EtOH (3 mL), 2.0 M solution of lithium hydroxide hydrate (1.545 mL, 3.09 mmol) and stirred at room temperature for 16 h. This gave after workup and purification by reverse phase column [C-18 column, 100g, eluting with acetonitrile in water (containing 0.1% aqueous HCl) from 0-60%] 2-(2-((7-(2-(aminomethyl)-3-fluoropyridin-4-yl)benzofuran-5-yl)methoxy)-3-methoxyphenyl)acetic acid (527b) (119 mg, 44% yield) HCl salt as a yellow solid; $^1$H NMR (300 MHz, DMSO-$d_6$) δ 8.73-8.49 (m, 4H, 3H $D_2O$ exchangeable), 8.12 (s, 1H), 7.90 (s, 1H), 7.81 (t, J=5.5 Hz, 1H), 7.60 (s, 1H), 7.13 (s, 1H), 7.09-6.96 (m, 2H), 6.91-6.77 (m, 1H), 5.09 (s, 2H), 4.48-4.30 (m, 2H), 3.86 (s, 3H), 3.54 (s, 2H); $^{19}$F NMR (282 MHz, DMSO-$d_6$) δ−128.56; MS (ES+): 437.1 (M+1); (ES−): 435.1 (M−1); Analysis calculated for $C_{24}H_{21}FN_2O_5 \cdot 1.3HCl \cdot H_2O$: C, 57.44; H, 4.88; Cl, 9.18; N, 5.58; Found: C, 57.22; H, 4.68; Cl, 9.18; N, 5.62.

Scheme-528
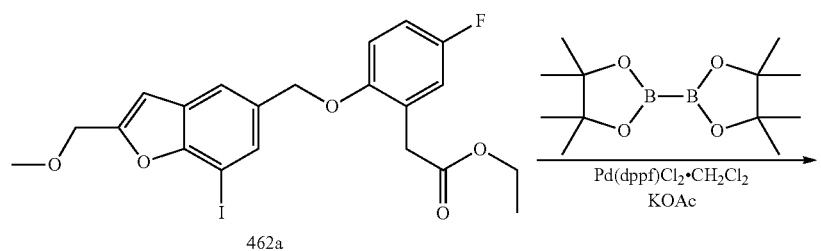
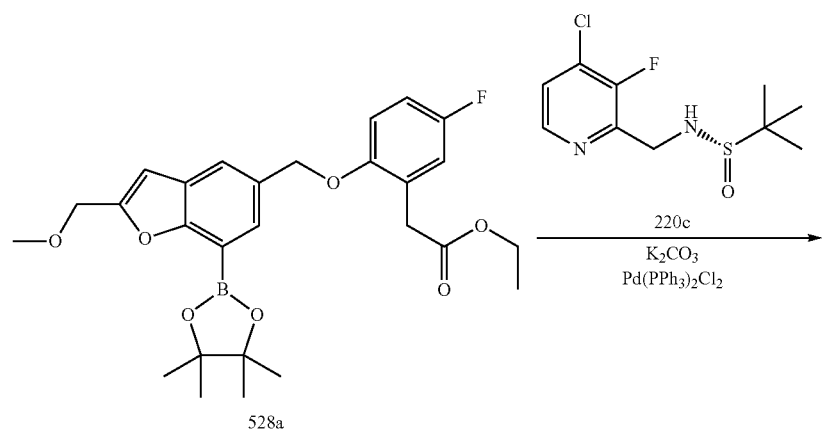
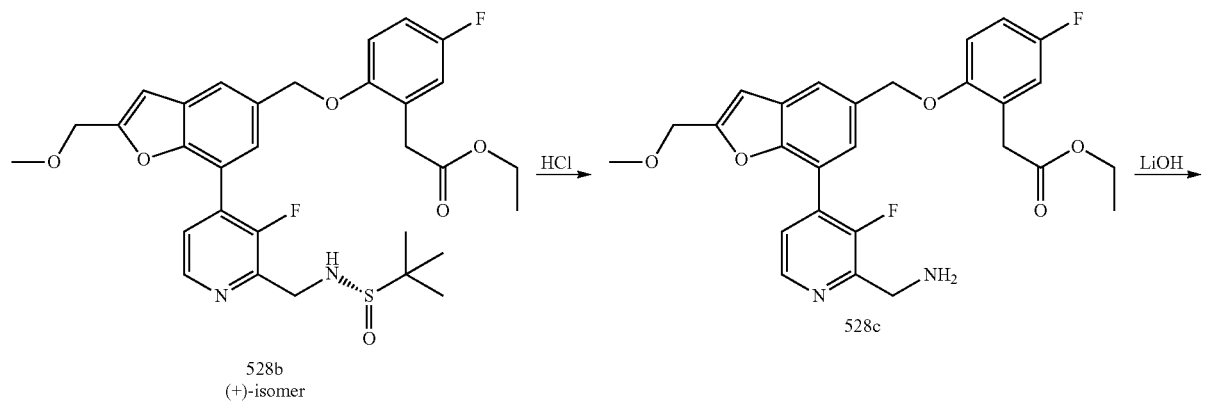
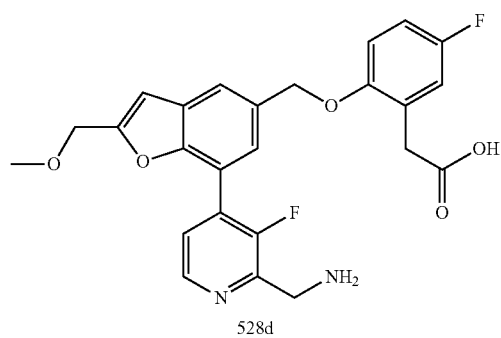

Preparation of 2-(2-((7-(2-(aminomethyl)-3-fluoropyridin-4-yl)-2-(methoxymethyl)benzofuran-5-yl)methoxy)-5-fluorophenyl)acetic Acid (528c)

Step-1: Preparation of Ethyl 2-(5-fluoro-2-((2-(methoxymethyl)-7-(4,4,5,5-tetramethyl-1,3,2-dioxaborolan-2-yl)benzofuran-5-yl)methoxy)phenyl)acetate (528a)

Compound 528a was prepared according to the procedure reported in step-1 of scheme-59 from ethyl 2-(5-fluoro-2-((7-iodo-2-(methoxymethyl)benzofuran-5-yl)methoxy)phenyl)acetate (462a) (1.2 g, 2.408 mmol) using bis(pinacolato)diboron (1.835 g, 7.22 mmol), potassium acetate (0.709 g, 7.22 mmol) and Pd(dppf)Cl$_2$—CH$_2$Cl$_2$ (0.295 g, 0.361 mmol) in anhydrous dioxane (25 mL) under an argon atmosphere and heating at 100° C. for 62 h. This gave after workup and purification by flash column chromatography (silica gel, eluting with EtOAc in hexane from 0-33%) ethyl 2-(5-fluoro-2-((2-(methoxymethyl)-7-(4,4,5,5-tetramethyl-1,3,2-dioxaborolan-2-yl)benzofuran-5-yl)methoxy)phenyl)acetate (528a) (898 mg, 75% yield) as a brown gum; $^1$H NMR (300 MHz, DMSO-d$_6$) δ 7.78 (d, J=1.9 Hz, 1H), 7.64 (d, J=1.9 Hz, 1H), 7.16-7.03 (m, 3H), 6.91 (s, 1H), 5.14 (s, 2H), 4.55 (s, 2H), 4.07-3.96 (m, 2H), 3.61 (s, 2H), 3.33 (s, 3H), 1.34 (s, 12H), 1.10-1.01 (m, 3H); $^{19}$F NMR (282 MHz, DMSO-d$_6$) δ−124.05; MS (ES+): 521.20 (M+Na).

Step-2: Preparation of (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-5-fluorophenyl)acetate (528b)

Compound 528b was prepared according to the procedure reported in step-3 of scheme-1 from ethyl 2-(5-fluoro-2-((2-(methoxymethyl)-7-(4,4,5,5-tetramethyl-1,3,2-dioxaborolan-2-yl)benzofuran-5-yl)methoxy)phenyl)acetate (528a) (420 mg, 0.843 mmol) in dioxane (18 mL) using (+)-(S)—N-((4-chloro-3-fluoropyridin-2-yl)methyl)-2-methylpropane-2-sulfinamide (220c) (268 mg, 1.011 mmol), Pd(PPh$_3$)$_2$Cl$_2$ (89 mg, 0.126 mmol) and a solution of K$_2$CO$_3$ (349 mg, 2.53 mmol) in water (2.2 mL) under a nitrogen atmosphere heating at 100° C. for 20 h on oil bath. This gave after workup and purification by flash column chromatography (silica gel, eluting with hexanes/10% methanol in ethyl acetate (ratio 1:0 to 1:1)] (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-5-fluorophenyl)acetate (528b) (250 mg, 49% yield) as a colorless gum; $^1$H NMR (300 MHz, DMSO-d$_6$) δ 8.52 (d, J=4.9 Hz, 1H), 7.81 (d, J=1.6 Hz, 1H), 7.65 (t, J=5.2 Hz, 1H), 7.49 (s, 1H), 7.16-7.06 (m, 3H), 7.04 (s, 1H), 5.84 (t, J=5.7 Hz, 1H), 5.22 (s, 2H), 4.52 (s, 2H), 4.44-4.36 (m, 2H), 3.92 (q, J=7.1 Hz, 2H), 3.64 (s, 2H), 3.30 (s, 3H), 1.11 (s, 9H), 0.98 (t, J=7.1 Hz, 3H); $^{19}$F NMR (282 MHz, DMSO-d$_6$) δ−123.94, −128.08; MS (ES+): 601.2 (M+1); Optical rotation [t]D=+24.24 (c=0.165, MeOH).

Step-3: Preparation of 2-(2-((7-(2-(aminomethyl)-3-fluoropyridin-4-yl)-2-(methoxymethyl)benzofuran-5-yl)methoxy)-5-fluorophenyl)acetic Acid (528c)

Compound 528c was prepared according to the procedure reported in step-3 of scheme-305 from (+)-(S)-ethyl 2-(2-((7-(2-((1,1-dimethylethylsulfinamido)methyl)-3-fluoropyridin-4-yl)-2-(methoxymethyl)benzofuran-5-yl)methoxy)-5-fluorophenyl)acetate (528b) (245 mg, 0.408 mmol) in THF (10 mL) using 3 M aqueous HCl (0.408 mL, 1.224 mmol) and stirring at room temperature for 5 h. The reaction was concentrated in vacuum to dryness. The residue obtained was dissolved in THF (7 mL) and MeOH (7 mL), added a solution of LiOH (140 mg, 3.26 mmol) in water (7 mL) and stirred at room temperature for 20 h. This gave after workup and purification by reverse phase column [C-18 column, eluting with acetonitrile in water (containing 0.1% HCl) from 0-100%] 2-(2-((7-(2-(aminomethyl)-3-fluoropyridin-4-yl)-2-(methoxymethyl)benzofuran-5-yl)methoxy)-5-fluorophenyl)acetic acid (528c) (77 mg, 40% yield for two steps) HCl salt as a light yellow solid; $^1$H NMR (300 MHz, DMSO-d$_6$) δ 8.72-8.59 (m, 4H), 7.86 (s, 1H), 7.78 (t, J=5.3 Hz, 1H), 7.57 (s, 1H), 7.16-7.01 (m, 4H), 5.24 (s, 2H), 4.54 (s, 2H), 4.42-4.30 (m, 2H), 3.60 (s, 2H), 3.30 (s, 3H); $^{19}$F NMR (282 MHz, DMSO-d$_6$) δ−123.98, −128.59; MS (ES+): 469.1 (M+1).

Scheme-529

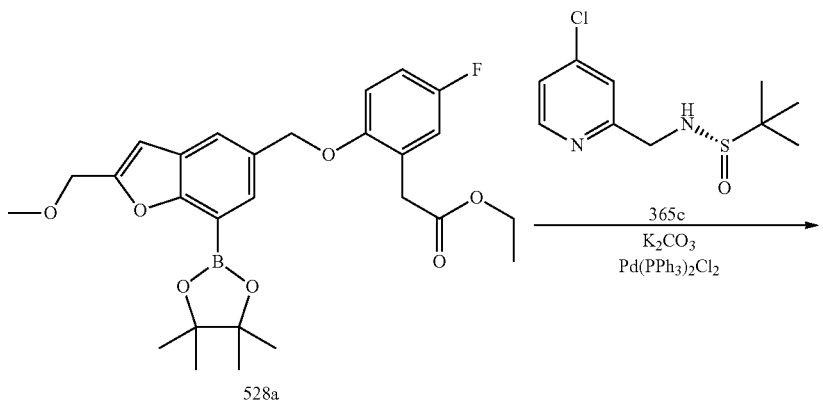

528a

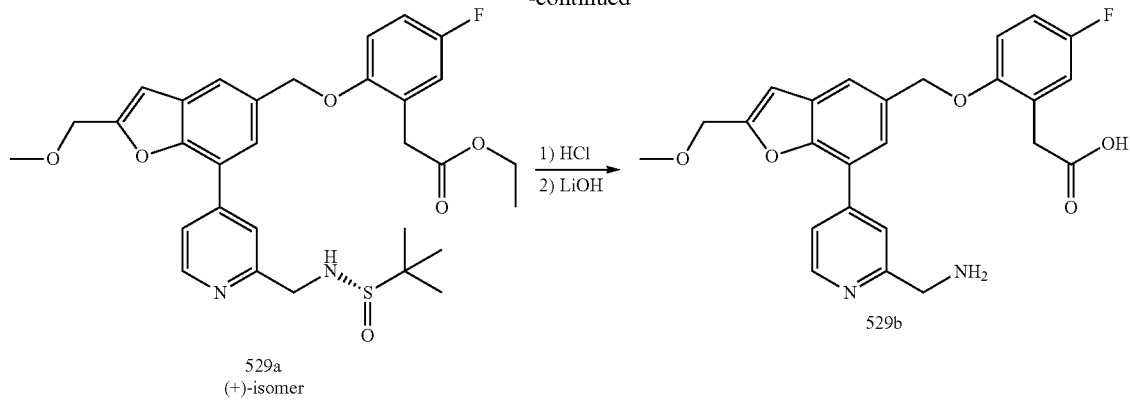

529a
(+)-isomer

529b

Preparation of 2-(2-((7-(2-(aminomethyl)pyridin-4-yl)-2-(methoxymethyl)benzofuran-5-yl)methoxy)-5-fluorophenyl)acetic Acid (529b)

Step-1: Preparation of (+)-(S)-ethyl 2-(2-((7-(2-((1,1-dimethylethylsulfinamido)methyl)pyridin-4-yl)-2-(methoxymethyl)benzofuran-5-yl)methoxy)-5-fluorophenyl)acetate (529a)

Compound 529a was prepared according to the procedure reported in step-3 of scheme-1 from ethyl 2-(5-fluoro-2-((2-(methoxymethyl)-7-(4,4,5,5-tetramethyl-1,3,2-dioxaborolan-2-yl)benzofuran-5-yl)methoxy)phenyl)acetate (528a) (440 mg, 0.883 mmol) in dioxane (20 mL) using (+)-(S)—N-((4-chloropyridin-2-yl)methyl)-2-methylpropane-2-sulfinamide (365c) (261 mg, 1.06 mmol), Pd(PPh$_3$)$_2$Cl$_2$ (93 mg, 0.132 mmol) and a solution of K$_2$CO$_3$ (366 mg, 2.65 mmol) in water (2.4 mL) under a nitrogen atmosphere heating at 100° C. for 16 h on oil bath. This gave after workup and purification by flash column chromatography [silica gel, eluting with hexanes/10% methanol in ethyl acetate from 0-33%] (+)-(S)-ethyl 2-(2-((7-(2-((1,1-dimethylethylsulfinamido)methyl)pyridin-4-yl)-2-(methoxymethyl)benzofuran-5-yl)methoxy)-5-fluorophenyl)acetate (529a) (278 mg, 54% yield) as a colorless gum; $^1$H NMR (300 MHz, DMSO-d$_6$) δ 8.65 (d, J=5.2 Hz, 1H), 8.01 (s, 1H), 7.79-7.74 (m, 2H), 7.68 (d, J=1.7 Hz, 1H), 7.16-7.07 (m, 3H), 7.04 (s, 1H), 5.94 (t, J=6.2 Hz, 1H), 5.22 (s, 2H), 4.58 (s, 2H), 4.46-4.26 (m, 2H), 3.93 (q, J=7.1 Hz, 2H), 3.65 (s, 2H), 3.33 (s, 3H), 1.17 (s, 9H), 0.97 (t, J=7.1 Hz, 3H); $^{19}$F NMR (282 MHz, DMSO) δ−123.97, MS (ES+) 583.3 (M+1); Optical rotation [α]$_D$=+20.69 (c=0.145, MeOH).

Step-2: Preparation of 2-(2-((7-(2-(aminomethyl)pyridin-4-yl)-2-(methoxymethyl)benzofuran-5-yl)methoxy)-5-fluorophenyl)acetic Acid (529b)

Compound 529b was prepared according to the procedure reported in step-2 of scheme-499 from (+)-(S)-ethyl 2-(2-((7-(2-((1,1-dimethylethylsulfinamido)methyl)pyridin-4-yl)-2-(methoxymethyl)benzofuran-5-yl)methoxy)-5-fluorophenyl)acetate (529a) (250 mg, 0.429 mmol) in THF (10.0 mL) using 3 M HCl (0.429 mL, 0.1.287 mmol) and stirring at room temperature for 30 min. The reaction was concentrated in vacuum to dryness. The residue obtained was dissolved in THF (7 mL) and methanol (7.0 mL) added 1 N aqueous LiOH (147 mg, 3.43 mmol) and stirred at room temperature for 12 h. This gave after workup and purification by reverse phase column [C-18 column, 50 g, eluting with acetonitrile in water (containing 0.1% HCl) from 0-100%] 2-(2-((7-(2-(aminomethyl)pyridin-4-yl)-2-(methoxymethyl)benzofuran-5-yl)methoxy)-5-fluorophenyl)acetic acid (529b) (73 mg, 38% yield) HCl salt as a light yellow solid; $^1$H NMR (300 MHz, DMSO-d$_6$) δ 8.79 (d, J=5.3 Hz, 1H), 8.53 (s, 3H), 8.06 (s, 1H), 7.99 (d, J=5.4 Hz, 1H), 7.83 (s, 1H), 7.79 (s, 1H), 7.19-7.01 (m, 4H), 5.26 (s, 2H), 4.61 (s, 2H), 4.35-4.25 (m, 2H), 3.62 (s, 2H), 3.34 (s, 3H); $^{19}$F NMR (282 MHz, DMSO-d$_6$) δ−124.00; MS (ES+): 451.15 (M+1); (ES−): 449.20 (M−1).

Scheme-530

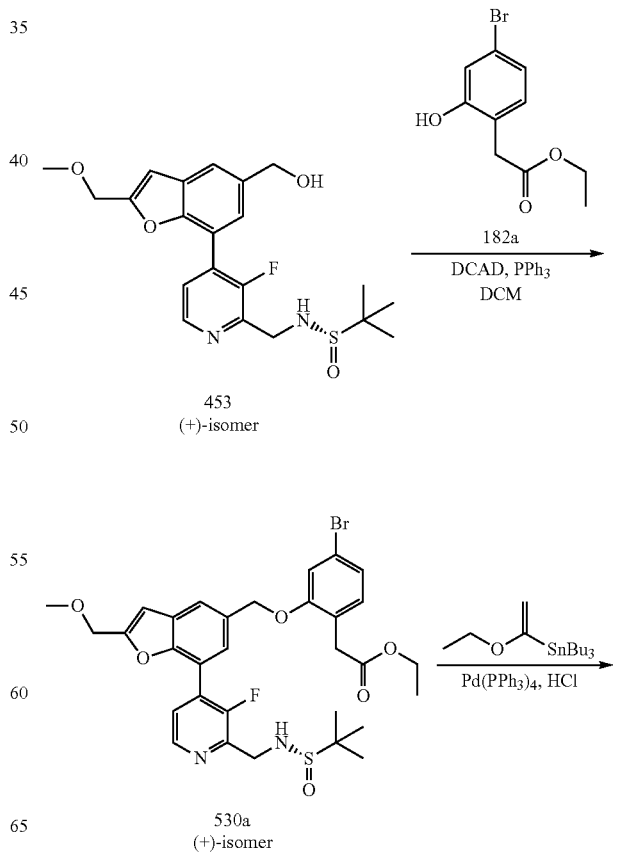

453
(+)-isomer 530a
(+)-isomer

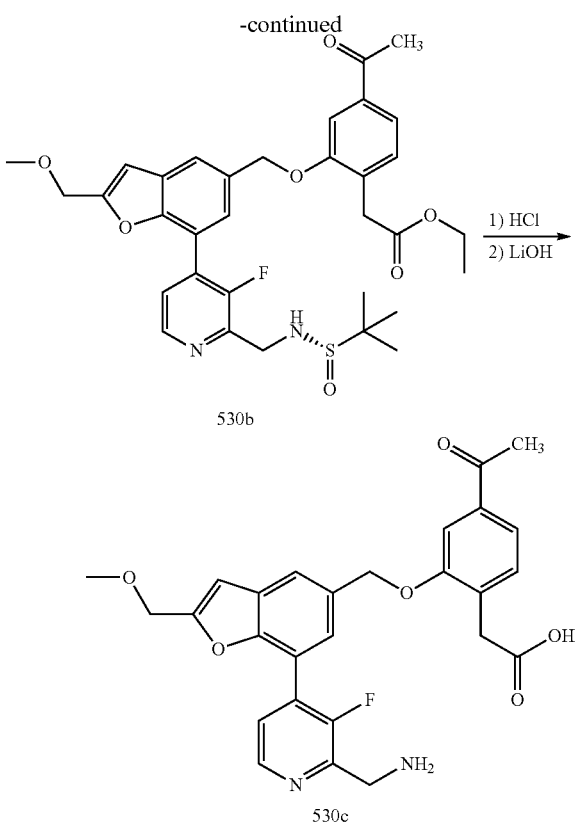

Preparation of 2-(4-acetyl-2-((7-(2-(aminomethyl)-3-fluoropyridin-4-yl)-2-(methoxymethyl)benzofuran-5-yl)methoxy)phenyl)acetic Acid (530c)

Step-1: Preparation of (+)-(S)-ethyl 2-(4-bromo-2-((7-(2-((1,1-dimethylethylsulfinamido)methyl)-3-fluoropyridin-4-yl)-2-(methoxymethyl)benzofuran-5-yl)methoxy)phenyl)acetate (530a)

Compound 530a was prepared according to the procedure reported in step-2 of scheme-23 from (+)-(S)—N-((3-fluoro-4-(5-(hydroxymethyl)-2-(methoxymethyl)benzofuran-7-yl)pyridin-2-yl)methyl)-2-methylpropane-2-sulfinamide (453a) (1.05 g, 2.497 mmol) in DCM (30 mL) using triphenylphosphine (0.851 g, 3.25 mmol), ethyl 2-(4-bromo-2-hydroxyphenyl)acetate (182a) (0.647 g, 2.497 mmol) and (E)-bis(4-chlorobenzyl) diazene-1,2-dicarboxylate (DCAD) (1.192 g, 3.25 mmol) in DCM (10 mL). This gave after workup and purification by flash column chromatography [silica gel, 40 g, eluting with ethyl acetate/methanol (9:1) in hexanes from 0-50%] (+)-(S)-ethyl 2-(4-bromo-2-((7-(2-((1,1-dimethylethylsulfinamido)methyl)-3-fluoropyridin-4-yl)-2-(methoxymethyl)benzofuran-5-yl)methoxy)phenyl)acetate (530a) (1.33 g, 81%); $^1$H NMR (300 MHz, DMSO-$d_6$) δ 8.52 (d, J=4.9 Hz, 1H), 7.81 (s, 1H), 7.65 (t, J=5.3 Hz, 1H), 7.50 (s, 1H), 7.34 (s, 1H), 7.19 (d, J=8.3 Hz, 1H), 7.12 (d, J=7.7 Hz, 1H), 7.05 (s, 1H), 5.84 (t, J=5.8 Hz, 1H), 5.27 (s, 2H), 4.52 (s, 2H), 4.46-4.34 (m, 2H), 3.90 (q, J=7.1 Hz, 2H), 3.60 (s, 2H), 3.30 (s, 3H), 1.11 (s, 9H), 0.96 (t, J=7.1 Hz, 3H); MS (ES+): 662.1 (M+1); Optical rotation $[\alpha]_D$=+22.35 (c=0.68, MeOH)

Step-2: Preparation of (+)-(S)-ethyl 2-(4-acetyl-2-((7-(2-((1,1-dimethylethylsulfinamido)methyl)-3-fluoropyridin-4-yl)-2-(methoxymethyl)benzofuran-5-yl)methoxy)phenyl)acetate (530b)

Compound 530b was prepared from (+)-(S)-ethyl 2-(4-bromo-2-((7-(2-((1,1-dimethylethylsulfinamido)methyl)-3-fluoropyridin-4-yl)-2-(methoxymethyl)benzofuran-5-yl)methoxy)phenyl)acetate (530a) (1.3 g, 1.965 mmol) in toluene (10 mL), using tributyl(1-ethoxyvinyl)stannane (0.875 mL, 2.456 mmol), Pd(PPh$_3$)$_4$ (0.227 g, 0.196 mmol) and heating at 120° C. for 22 h. This gave after workup and purification by flash column chromatography [silica gel, 40 g, eluting with ethyl acetate/methanol (9:1) in hexanes from 0-50%] (+)-(S)-ethyl 2-(4-acetyl-2-((7-(2-((1,1-dimethylethylsulfinamido)methyl)-3-fluoropyridin-4-yl)-2-(methoxymethyl)benzofuran-5-yl)methoxy)phenyl)acetate (530b) (485 mg, 40%) as a colorless oil; $^1$H NMR (300 MHz, DMSO-$d_6$) δ 8.53 (d, J=4.9 Hz, 1H), 7.84 (s, 1H), 7.65 (t, J=5.3 Hz, 1H), 7.62 (s, 1H), 7.58 (d, J=7.8 Hz, 1H), 7.54 (s, 1H), 7.39 (d, J=7.6 Hz, 1H), 7.05 (s, 1H), 5.84 (t, J=5.8 Hz, 1H), 5.33 (s, 2H), 4.52 (s, 2H), 4.43-4.38 (m, 2H), 3.92 (q, J=7.1 Hz, 2H), 3.71 (s, 2H), 3.30 (s, 3H), 2.58 (s, 3H), 1.11 (s, 9H), 1.00-0.93 (m, 3H); $^{19}$F NMR (282 MHz, DMSO-$d_6$) δ−128.05; MS (ES+): 625.25 (M+1); Optical rotation [t]D=+8 (c=0.1, MeOH).

Step-3: Preparation of 2-(4-acetyl-2-((7-(2-(aminomethyl)-3-fluoropyridin-4-yl)-2-(methoxymethyl)benzofuran-5-yl)methoxy)phenyl)acetic Acid (530c)

Compound 530c was prepared according to the procedure reported in step-2 of scheme-499 from (+)-(S)-ethyl 2-(4-acetyl-2-((7-(2-((1,1-dimethylethylsulfinamido)methyl)-3-fluoropyridin-4-yl)-2-(methoxymethyl)benzofuran-5-yl)methoxy)phenyl)acetate (530b) (450 mg, 0.720 mmol) in THF (15 mL) using 3 M HCl (0.720 mL, 2.161 mmol) and stirring at room temperature for 2 h. The reaction was concentrated in vacuum to dryness. The residue obtained was dissolved in THF (7 mL) and methanol (7 mL), added a solution of LiOH (247 mg, 5.76 mmol) in water (7 mL) and stirred at room temperature for 16 h. This gave after workup and purification by reverse phase column [C-18 column, eluting with acetonitrile in water (containing 0.1% HCl) from 0-40%] 2-(4-acetyl-2-((7-(2-(aminomethyl)-3-fluoropyridin-4-yl)-2-(methoxymethyl)benzofuran-5-yl)methoxy)phenyl)acetic acid (530c) (259 mg, 73% yield) HCl salt as a white solid; $^1$H NMR (300 MHz, DMSO-$d_6$) δ 8.64 (d, J=5.0 Hz, 1H), 8.53 (t, J=5.9 Hz, 3H, D$_2$O exchangeable), 7.90 (s, 1H), 7.79 (t, J=5.3 Hz, 1H), 7.64-7.55 (m, 3H), 7.39 (d, J=7.6 Hz, 1H), 7.05 (s, 1H), 5.36 (s, 2H), 4.54 (s, 2H), 4.44-4.31 (m, 2H), 3.67 (s, 2H), 3.30 (s, 3H), 2.57 (s, 3H); $^{19}$F NMR (282 MHz, DMSO-$d_6$) δ−128.57; MS (ES+): 493.1 (M+1); (ES−).

Scheme-531

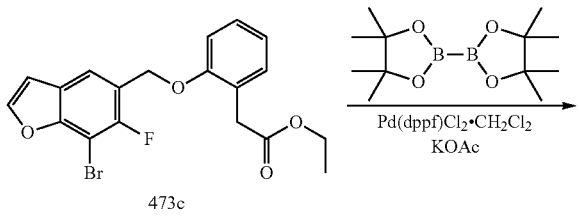

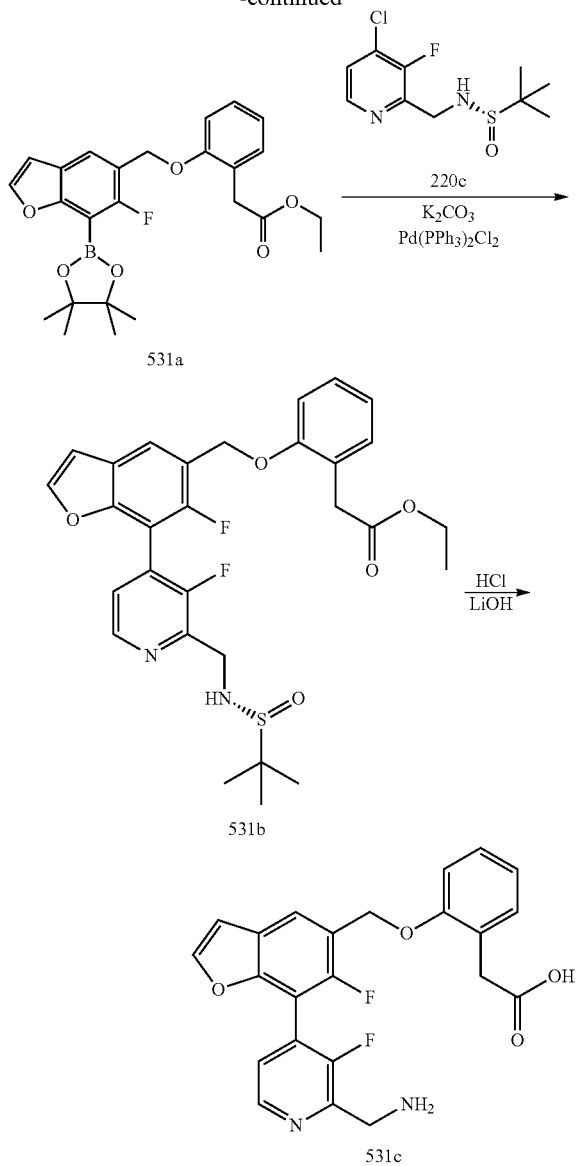

Preparation of 2-(2-((7-(2-(aminomethyl)-3-fluoro-pyridin-4-yl)-6-fluorobenzofuran-5-yl)methoxy)phenyl)acetic Acid (531c)

Step-1: Preparation of Ethyl 2-(2-((6-fluoro-7-(4,4,5,5-tetramethyl-1,3,2-dioxaborolan-2-yl)benzofuran-5-yl)methoxy)phenyl)acetate (531a)

Compound 531a was prepared according to the procedure reported in step-1 of scheme-59 from ethyl 2-(2-((7-bromo-6-fluorobenzofuran-5-yl)methoxy)phenyl)acetate (473c) (314 mg, 0.771 mmol) using bis(pinacolato)diboron (294 g, 1.157 mmol), potassium acetate (227 mg, 2.313 mmol) and Pd(dppf)Cl$_2$—CH$_2$Cl$_2$ (94 mg, 0.116 mmol) in anhydrous dioxane (12 mL) under an argon atmosphere and heating at 95° C. for 16 h. This gave after workup and purification by flash column chromatography [silica (12 g), eluting with EtOAc in hexane from 0-40%] ethyl 2-(2-((6-fluoro-7-(4,4,5,5-tetramethyl-1,3,2-dioxaborolan-2-yl)benzofuran-5-yl)methoxy)phenyl)acetate (531a) (181 mg, 52%) as a colorless oil; $^1$H NMR (300 MHz, DMSO-d$_6$) δ 8.10-8.03 (m, 1H), 7.88 (d, J=7.1 Hz, 1H), 7.32-7.18 (m, 2H), 7.13 (d, J=8.2 Hz, 1H), 7.00-6.96 (m, 1H), 6.92 (t, J=7.4 Hz, 1H), 5.17 (s, 2H), 3.96 (q, J=6.9 Hz, 2H), 3.57 (s, 2H), 1.35 (s, 12H), 1.03 (t, J=7.1 Hz, 3H); $^{19}$F NMR (282 MHz, DMSO-d$_6$) δ −111.29;

Step-2: Preparation of Ethyl 2-(2-((7-(2-((1,1-dimethylethylsulfinamido)methyl)-3-fluoropyridin-4-yl)-6-fluorobenzofuran-5-yl)methoxy)phenyl)acetate (531b)

Compound 531b was prepared according to the procedure reported in step-3 of scheme-1 from ethyl 2-(2-((6-fluoro-7-(4,4,5,5-tetramethyl-1,3,2-dioxaborolan-2-yl)benzofuran-5-yl)methoxy)phenyl)acetate (531a) (178 mg, 0.392 mmol) in dioxane (5 mL) using (+)-(S)—N-((4-chloro-3-fluoropyridin-2-yl)methyl)-2-methylpropane-2-sulfinamide (220c) (156 mg, 0.588 mmol), Pd(PPh$_3$)$_2$Cl$_2$ (41 mg, 0.059 mmol) and a solution of K$_2$CO$_3$ (162 mg, 1.175 mmol) in water (0.5 mL) under a nitrogen atmosphere heating at 100° C. for 3 h on oil bath. This gave after workup and purification by flash column chromatography [silica gel (12 g), eluting with methanol/DCM from 0-15%] ethyl 2-(2-((7-(2-((1,1-dimethylethylsulfinamido)methyl)-3-fluoropyridin-4-yl)-6-fluorobenzofuran-5-yl)methoxy)phenyl)acetate (531b) (218 mg, 100% yield) as a yellow oil; MS (ES+): 557.2 (M+1).

Step-3: Preparation of 2-(2-((7-(2-(aminomethyl)-3-fluoropyridin-4-yl)-6-fluorobenzofuran-5-yl)methoxy)phenyl)acetic Acid (531c)

Compound 531c was prepared according to the procedure reported in step-2 of scheme-499 from ethyl 2-(2-((7-(2-((1,1-dimethylethylsulfinamido)methyl)-3-fluoropyridin-4-yl)-6-fluorobenzofuran-5-yl)methoxy)phenyl)acetate (531b) (218 mg, 0.392 mmol), in ethanol (6 mL) using 4 M HCl in dioxane (1 mL, 4.0 mmol) and stirring at room temperature for 1 h. The reaction was concentrated in vacuum to dryness. The residue obtained was dissolved in THF (3 mL) and methanol (3 mL), added a solution of LiOH (153 mg, 3.65 mmol) in water (2 mL) and stirred at room temperature for 16 h. This gave after workup and purification by reverse phase column [C-18 column, eluting with acetonitrile in water (containing 0.1% HCl) from 0-100%] 2-(2-((7-(2-(aminomethyl)-3-fluoropyridin-4-yl)-6-fluorobenzofuran-5-yl)methoxy)phenyl)acetic acid (531c) (11 mg, 7% yield) HCl salt as a white yellow solid; $^1$H NMR (300 MHz, DMSO-d$_6$) δ 12.21 (s, 1H), 8.75-8.55 (m, 4H), 8.12 (d, J=2.2 Hz, 1H), 8.01 (d, J=6.9 Hz, 1H), 7.82 (t, J=5.1 Hz, 1H), 7.32-7.19 (m, 2H), 7.19-7.06 (m, 2H), 6.93 (t, J=7.3 Hz, 1H), 5.30 (s, 2H), 4.39 (d, J=5.9 Hz, 2H), 3.57 (s, 2H); $^{19}$F NMR (282 MHz, DMSO-d$_6$) δ −124.79, −126.55; MS (ES+): 425.1 (M+1); MS (ES−): 423.1 (M−1).

Scheme 532

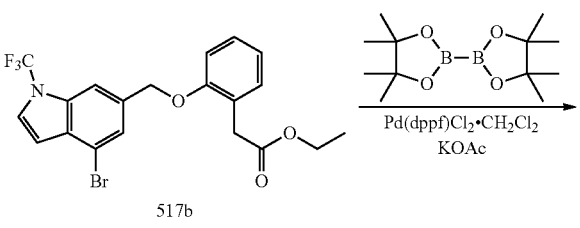

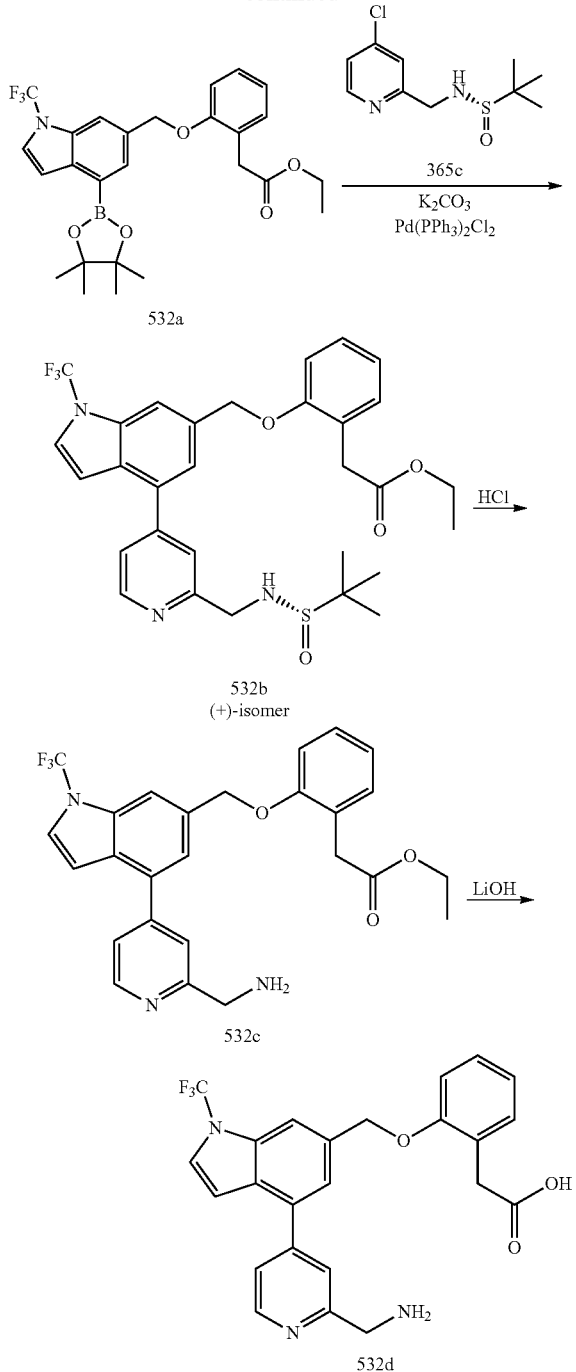

Preparation of 2-(2-((4-(2-(aminomethyl)pyridin-4-yl)-1-(trifluoromethyl)-1H-indol-6-yl)methoxy)phenyl)acetic Acid (532d)

Step-1: Preparation of Ethyl 2-(2-((4-(4,4,5,5-tetramethyl-1,3,2-dioxaborolan-2-yl)-1-(trifluoromethyl)-1H-indol-6-yl)methoxy)phenyl)acetate (532a)

Compound 532a was prepared according to the procedure reported in step-1 of scheme-59 from ethyl 2-(2-((4-bromo-1-(trifluoromethyl)-1H-indol-6-yl)methoxy)phenyl)acetate (517b) (0.72 g, 1.578 mmol) using bis(pinacolato)diboron (0.601 g, 2.367 mmol), potassium acetate (0.465 g, 4.73 mmol) and Pd(dppf)Cl$_2$—CH$_2$Cl$_2$ (0.193 g, 0.237 mmol) in anhydrous dioxane (15 mL) under an argon atmosphere and heating at 100° C. for 16 h. This gave after workup and purification by flash column chromatography [silica (24 g), eluting with EtOAc/MeOH (9:1) in hexane from 0-10%] ethyl 2-(2-((4-(4,4,5,5-tetramethyl-1,3,2-dioxaborolan-2-yl)-1-(trifluoromethyl)-1H-indol-6-yl)methoxy)phenyl)acetate (532a) (0.76 g, 96% yield) as a yellow solid; $^1$H NMR (300 MHz, DMSO-d$_6$) δ 7.83 (s, 1H), 7.79 (d, J=3.6 Hz, 1H), 7.70 (s, 1H), 7.30-7.19 (m, 2H), 7.10 (s, 1H), 7.08-7.05 (m, 1H), 6.91 (t, J=7.4 Hz, 1H), 5.24 (s, 2H), 4.03-3.94 (m, 2H), 3.60 (s, 2H), 1.34 (s, 12H), 1.03 (t, J=7.1, 1.2 Hz, 3H); $^{19}$F NMR (282 MHz, DMSO-d$_6$) δ−54.99.

Step-2: Preparation of (+)-(S)-ethyl 2-(2-((4-(2-((1,1-dimethylethylsulfinamido)methyl)pyridin-4-yl)-1-(trifluoromethyl)-1H-indol-6-yl)methoxy)phenyl)acetate (532b)

Compound 532b was prepared according to the procedure reported in step-3 of scheme-1 from ethyl 2-(2-((4-(4,4,5,5-tetramethyl-1,3,2-dioxaborolan-2-yl)-1-(trifluoromethyl)-1H-indol-6-yl)methoxy)phenyl)acetate (532a) (0.38 g, 0.755 mmol) in dioxane (6 mL) using (+)-(S)—N-((4-chloropyridin-2-yl)methyl)-2-methylpropane-2-sulfinamide (365c) (0.186 g, 0.755 mmol), Pd(PPh$_3$)$_2$Cl$_2$ (0.079 g, 0.113 mmol) and a solution of K$_2$CO$_3$ (0.313 g, 2.265 mmol) in water (2.0 mL) under a nitrogen atmosphere heating at 90° C. for 3 h on oil bath. This gave after workup and purification by flash column chromatography [silica gel (12 g), eluting with DMA80 in DCM from 0-50%] (+)-(S)-ethyl 2-(2-((4-(2-((1,1-dimethylethylsulfinamido)methyl)pyridin-4-yl)-1-(trifluoromethyl)-1H-indol-6-yl)methoxy)phenyl)acetate (532b) (0.4 g, 90% yield) as a yellow oil; $^{19}$F NMR (282 MHz, DMSO) δ−55.10; MS (ES+): 588.2 (M+1); optical rotation [t]$_D$=+19.05 (c=0.21, MeOH).

Step-3: Preparation of Ethyl 2-(2-((4-(2-(aminomethyl)pyridin-4-yl)-1-(trifluoromethyl)-1H-indol-6-yl)methoxy)phenyl)acetate (532c)

Compound 532c was prepared according to the procedure reported in step-3 of scheme-305 from (+)-(S)-ethyl 2-(2-((4-(2-((1,1-dimethylethylsulfinamido)methyl)pyridin-4-yl)-1-(trifluoromethyl)-1H-indol-6-yl)methoxy)phenyl)acetate (532b) (0.4 g, 0.681 mmol) in DCM (5 mL) using 4 M HCl in dioxane (0.511 mL, 2.042 mmol) and stirring at room temperature for 1 h. This gave after workup and purification by flash column chromatography [silica gel (12g), eluting with DMA-80/DCM from 0-70%] ethyl 2-(2-((4-(2-(aminomethyl)pyridin-4-yl)-1-(trifluoromethyl)-1H-indol-6-yl)methoxy)phenyl)acetate (532c) (0.3 g, 91% yield) as a pale-yellow oil; MS (ES+): 484.2 (M+1).

Step 4: Preparation of 2-(2-((4-(2-(aminomethyl)pyridin-4-yl)-1-(trifluoromethyl)-1H-indol-6-yl)methoxy)phenyl)acetic Acid (532d)

Compound 532d was prepared according to the procedure reported in step-6 of scheme-1 from ethyl 2-(2-((4-(2-(aminomethyl)pyridin-4-yl)-1-(trifluoromethyl)-1H-indol-6-yl)methoxy)phenyl)acetate (532c) (0.3 g, 0.620 mmol) in MeOH/THF (3 mL, each) using a solution of LiOH hydrate (0.208 g, 4.96 mmol) in water (2 mL) and stirring at room temperature for 16 h. This gave after workup and purification by reverse phase column [C-18 column, 50g, eluting with acetonitrile in water from 0-100%] 2-(2-((4-(2-(aminomethyl)pyridin-4-yl)-1-(trifluoromethyl)-1H-indol-6-yl)methoxy)phenyl)acetic acid (532d) (0.08 g, 28% yield) free base as a white solid; $^1$H NMR (300 MHz, DMSO-$d_6$) δ 8.62 (d, J=5.1 Hz, 1H), 8.14 (s, 1H), 7.91 (d, J=3.7 Hz, 1H), 7.82 (s, 2H), 7.70 (d, J=5.2 Hz, 1H), 7.12 (dt, J=7.6, 3.8 Hz, 2H), 7.05 (d, J=3.8 Hz, 1H), 6.99 (d, J=8.5 Hz, 1H), 6.83 (t, J=7.3 Hz, 1H), 5.34 (s, 2H), 4.07 (s, 2H), 3.43 (s, 2H); $^{19}$F NMR (282 MHz, DMSO-$d_6$) δ−55.06; MS (ES+): 456.15 (M+1); (ES−): 454.10 (M−1).

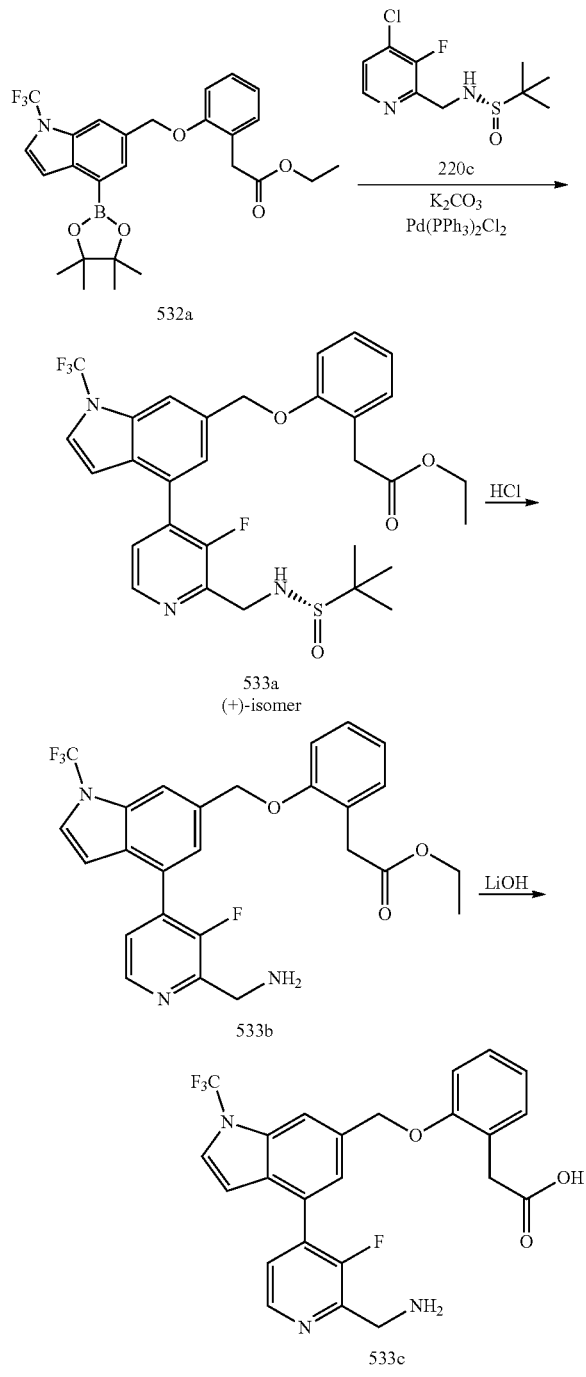

Scheme 533

Preparation of 2-(2-((4-(2-(aminomethyl)-3-fluoropyridin-4-yl)-1-(trifluoromethyl)-1H-indol-6-yl)methoxy)phenyl)acetic Acid (533c)

Step-1: Preparation of (+)-(S)-ethyl 2-(2-((4-(2-((1,1-dimethylethylsulfinamido)methyl)-3-fluoropyridin-4-yl)-1-(trifluoromethyl)-1H-indol-6-yl)methoxy)phenyl)acetate (533a)

Compound 533a was prepared according to the procedure reported in step-3 of scheme-1 from ethyl 2-(2-((4-(4,4,5,5-tetramethyl-1,3,2-dioxaborolan-2-yl)-1-(trifluoromethyl)-1H-indol-6-yl)methoxy)phenyl)acetate (532a) (0.38 g, 0.755 mmol) in dioxane (6 mL) using (+)-(S)—N-((4-chloro-3-fluoropyridin-2-yl)methyl)-2-methylpropane-2-sulfinamide (220c) (0.200 g, 0.755 mmol), Pd(PPh$_3$)$_2$Cl$_2$ (0.079 g, 0.113 mmol) and a solution of K$_2$CO$_3$ (0.313 g, 2.265 mmol) in water (2.0 mL) under an argon atmosphere heating at 90° C. for 3 h on oil bath. This gave after workup and purification by flash column chromatography [silica gel (12 g), eluting with DMA80 in DCM from 0-50%] (+)-(S)-ethyl 2-(2-((4-(2-((1,1-dimethylethylsulfinamido)methyl)-3-fluoropyridin-4-yl)-1-(trifluoromethyl)-1H-indol-6-yl)methoxy)phenyl)acetate (533a) (0.4 g, 87% yield) as a yellow oil; $^{19}$F NMR (282 MHz, DMSO-$d_6$) δ−55.06, −128.45; MS (ES+): 606.2 (M+1); (ES−): 604.2 (M−1); optical rotation [α]$_D$=+27.41 (c=0.27, MeOH).

Step-2: Preparation of Ethyl 2-(2-((4-(2-(aminomethyl)-3-fluoropyridin-4-yl)-1-(trifluoromethyl)-1H-indol-6-yl)methoxy)phenyl)acetate (533b)

Compound 533b was prepared according to the procedure reported in step-3 of scheme-305 from (+)-(S)-ethyl 2-(2-((4-(2-((1,1-dimethylethylsulfinamido)methyl)-3-fluoropyridin-4-yl)-1-(trifluoromethyl)-1H-indol-6-yl)methoxy)phenyl)acetate (533a) (0.4 g, 0.660 mmol) in DCM (5 mL) using 4 M HCl in dioxanes (0.495 mL, 1.981 mmol) and stirring at room temperature for 1 h. This gave after workup and purification by flash column chromatography [silica gel (12g), eluting with DMA-80/DCM from 0-70%] ethyl 2-(2-((4-(2-(aminomethyl)-3-fluoropyridin-4-yl)-1-(trifluoromethyl)-1H-indol-6-yl)methoxy)phenyl)acetate (533b) (0.3 g, 91% yield) as a pale yellow oil; MS (ES+): 502.15 (M+1).

Step-3: Preparation of 2-(2-((4-(2-(aminomethyl)-3-fluoropyridin-4-yl)-1-(trifluoromethyl)-1H-indol-6-yl)methoxy)phenyl)acetic Acid (533c)

Compound 533c was prepared according to the procedure reported in step-6 of scheme-1 from ethyl 2-(2-((4-(2-(aminomethyl)-3-fluoropyridin-4-yl)-1-(trifluoromethyl)-1H-indol-6-yl)methoxy)phenyl)acetate (533b) (0.3 g, 0.598 mmol) in MeOH/THF (3 mL, each) using a solution of LiOH hydrate (0.201 g, 4.79 mmol) in water (2 mL) and stirring at room temperature for 16 h. This gave after workup and purification by reverse phase column [C-18 column, 50g, eluting with acetonitrile in water from 0-100%] 2-(2-((4-(2-(aminomethyl)-3-fluoropyridin-4-yl)-1-(trifluoromethyl)-1H-indol-6-yl)methoxy)phenyl)acetic Acid (533c) (0.1 g, 35% yield) free base as a white solid; $^1$H NMR (300 MHz, DMSO-$d_6$) δ 12.14 (s, 1H, D$_2$O exchangeable), 8.61 (d, J=4.9 Hz, 1H), 8.51 (s, 3H, D$_2$O exchangeable), 7.93 (d, J=4.0 Hz, 2H), 7.69 (t, J=5.3 Hz, 1H), 7.56 (s, 1H), 7.24 (t, J=8.8 Hz, 2H), 7.10 (d, J=8.1 Hz, 1H), 6.92 (t, J=7.4 Hz, 1H), 6.77 (t, J=3.5 Hz, 1H), 5.35 (s, 2H), 4.37 (s, 2H), 3.59

(s, 2H); $^{19}$F NMR (282 MHz, DMSO-d$_6$) δ −55.06, −128.60, MS (ES+): 474.15 (M+1); (ES−): 472.10 (M−1).

Example 534

The IC$_{50}$ value of a compound (i.e., the concentration of the compound that inhibits 50% of the enzymatic activity) was calculated according to the procedure reported in U.S. Pat. No. 6,653,340 B1, e.g., column 74 (incorporated by reference).

Specifically, the compounds were dissolved in a stock solution of DMSO at 10.0 or 100 mM. A portion of this stock solution was added to assay buffer in a final volume of 50 μL. Controls included buffer alone and enzyme solutions to which DMSO was added. Substrate was added to the reaction wells immediately or after incubation at room temperature. The reaction rates were measured spectrophotometrically by the generation of product at 405 nm for 600 sec. Background absorbance at 690 nm was measured and subtracted from the absorbance at 405 nm for each well.

The reaction rate for enzyme alone was compared to the rate of enzyme in the presence of inhibitor and the percent inhibition was calculated as shown below:

Percent Inhibition=[Rate without inhibitor−Rate with inhibitor)/(Rate without inhibitor)]×100

Factor D Esterolytic Assay:

An established esterolytic assay for the measurement of Factor D activity and inhibition of Factor D activity was used (Kam, C. M.; McRae, B. J.; Harper, J. W.; Niemann, M. A.; Volanakis, J. E.; Powers, J. C. Human complement proteins D, C2, and B Active site mapping with peptide thioester substrates. J Biol. Chem. 1987, 262, 3444-3451). For this assay Z-Lys-SBzl, 1.29 mM (Kim, S.; Narayana, S. V. L; Volanakis, J. E. Mutational analysis of the substrate binding site of human complement Factor D. Biochemistry. 1994, 33, 14393-14399.) was used as the substrate for Factor D (104 mM). Hydrolysis of this compound by Factor D liberated a free sulfhydryl group which is then reacted with 5,5'-dithiobis(2nitrobenzoic acid) producing an intense yellow color (Habeeb, A. F. S. A. Reaction of protein sulfhydryl groups with Ellman's Reagent. Methods in Enzymol. 1976, 25, 457-464.). The assays were performed in 96 well microtiter plates and rates of hydrolysis were monitored at 405 nm on a Biotek Synergy H1 plate reader. Hydrolysis rates were reported as change in mOD/min. The assay was conducted in 100 mM HEPES, 500 mM NaCl, pH 7.5 containing 10% DMSO in a final volume of 50 μL per well.

An IC$_{50}$, a compound concentration which inhibits 50% of the enzymatic activity, was calculated. Compounds in the examples were tested a minimum of three times. In the table below, three plus symbols (+++) are used to indicate compounds with an IC$_{50}$ value of less than 1 micromolar; two plus symbols (++) indicate compounds with an IC$_{50}$ value between 1 and 10 micromolar; and one plus symbol (+) indicates compounds with an IC$_{50}$ value greater than 10 micromolar.

TABLE 1

Measured Ki (IC$_{50}$) Value for Compounds.
Three (+++) is used to denote compounds with an IC$_{50}$ value of less than 1 micromolar concentration; Two (++) indicate compounds with an IC$_{50}$ value between 1 and 10 micromolar concentration; One (+) indicate compounds with an IC$_{50}$ value greater than 10 micromolar concentration.

| Compound | IC$_{50}$ | Compound | IC$_{50}$ | Compound | IC$_{50}$ |
| --- | --- | --- | --- | --- | --- |
| 1h | +++ | 16i | +++ | 39d | +++ |
| 2e | + | 17c | + | 40e | +++ |
| 2f | +++ | 18f | +++ | 41d | +++ |
| 3i | +++ | 19c | +++ | 36h | +++ |
| 4e | +++ | 20e | + | 37c | +++ |
| 5g | +++ | 21d | +++ | 42d | +++ |
| 6e | ++ | 23e | +++ | 44c | +++ |
| 7d | +++ | 25c | ++ | 45e | +++ |
| 8e | +++ | 26d | +++ | 71e | +++ |
| 9d | +++ | 27f | + | 46g | ++ |
| 10d | +++ | 28d | +++ | 47f | ++ |
| 13c | ++ | 29d | ++ | 48h | ++ |
| 11a | + | 30d | + | 157d | + |
| 11b | +++ | 31f | +++ | 49f | +++ |
| 14c | + | 32h | +++ | 50e | +++ |
| 14d | ++ | 33f | +++ | 51c | +++ |
| 15c | + | 34f | +++ | 102g | +++ |
| 15d | +++ | 35f | ++ | 52a | +++ |
| 53d | +++ | 68c | +++ | 158c | ++ |
| 124g | +++ | 70a | +++ | 146g | ++ |
| 54d | + | 72c | +++ | 82f | +++ |
| 55g | +++ | 73c | +++ | 83h | +++ |
| 56c | +++ | 143g | + | 147c | +++ |
| 57c | +++ | 144d | +++ | 84f | +++ |
| 59d | +++ | 74c | +++ | 85d | ++ |
| 60c | +++ | 156b | +++ | 85c | +++ |
| 142d | +++ | 75c | +++ | 93h | +++ |
| 61f | ++ | 76f | +++ | 86b | +++ |
| 62c | +++ | 77c | +++ | 87c | + |
| 58b | +++ | 78c | +++ | 88b | +++ |
| 125c | + | 145c | +++ | 128g | +++ |
| 63c | +++ | 79c | +++ | 89c | +++ |
| 64f | +++ | 126h | +++ | 160e | +++ |
| 65c | +++ | 80e | +++ | 129e | +++ |
| 66c | +++ | 81d | + | 161e | +++ |
| 67c | +++ | 127b | +++ | 91h | +++ |
| 92b | +++ | 108f | +++ | 131b | +++ |
| 94c | +++ | 187f | +++ | 132b | +++ |
| 95c | +++ | 109g | +++ | 123d | +++ |
| 96e | +++ | 165f | +++ | 133c | +++ |
| 97b | +++ | 110c | +++ | 134b | +++ |
| 98e | +++ | 111b | +++ | 135c | +++ |
| 130g | +++ | 166d | +++ | 136e | +++ |
| 99b | +++ | 112c | +++ | 137b | +++ |
| 159f | ++ | 113c | +++ | 138f | +++ |
| 100c | ++ | 114j | +++ | 139c | +++ |
| 162e | +++ | 115f | +++ | 140c | +++ |
| 103d | +++ | 167e | +++ | 141c | +++ |
| 163d | +++ | 116f | +++ | 148e | +++ |
| 164e | +++ | 118c | +++ | 149b | +++ |
| 104e | +++ | 119e | +++ | 150b | +++ |
| 105c | +++ | 120c | +++ | 151c | +++ |
| 106c | ++ | 121b | +++ | 168c | +++ |
| 107f | +++ | 122b | +++ | 153b | +++ |
| 188b | +++ | 176c | ++ | 198b | +++ |
| 154g | +++ | 178g | +++ | 201b | +++ |
| 155c | +++ | 179b | +++ | 199f | +++ |
| 204e | + | 180e | +++ | 202c | +++ |
| 169f | +++ | 181d | +++ | 203c | +++ |
| 43d | +++ | 182d | +++ | 222f | +++ |
| 69e | +++ | 200e | +++ | 206c | +++ |
| 170b | +++ | 183c | + | 211c | +++ |
| 189c | +++ | 184c | ++ | 210c | +++ |
| 171c | +++ | 185c | +++ | 218f | + |
| 172b | +++ | 186c | +++ | 214f | +++ |
| 152d | +++ | 191h | +++ | 207c | +++ |
| 173b | +++ | 192e | +++ | 208d | +++ |
| 174c | +++ | 193c | ++ | 209c | +++ |
| 190c | +++ | 194d | +++ | 223e | +++ |
| 117b | +++ | 195d | +++ | 205d | +++ |
| 175c | +++ | 196d | +++ | 215h | +++ |
| 177f | +++ | 197c | +++ | 217e | +++ |
| 224c | +++ | 238c | +++ | 12c | +++ |
| 237b | +++ | 234f | +++ | 22a | +++ |
| 225h | +++ | 98f | +++ | 256c | +++ |
| 212e | +++ | 235b | +++ | 24b | +++ |
| 213b | +++ | 239c | +++ | 38f | +++ |

TABLE 1-continued

Measured Ki (IC$_{50}$) Value for Compounds.
Three (+++) is used to denote compounds with an IC$_{50}$ value of less than 1 micromolar concentration; Two (++) indicate compounds with an IC$_{50}$ value between 1 and 10 micromolar concentration; One (+) indicate compounds with an IC$_{50}$ value greater than 10 micromolar concentration.

| | | | | | |
|---|---|---|---|---|---|
| 211e | +++ | 98g | +++ | 101c | +++ |
| 226c | +++ | 240d | +++ | 251c | ++ |
| 227e | +++ | 241c | +++ | 252d | +++ |
| 228e | +++ | 242b | +++ | 255c | ++ |
| 229b | +++ | 243d | + | 253f | +++ |
| 219c | +++ | 244c | ++ | 90d | +++ |
| 220g | +++ | 245g | +++ | 254c | +++ |
| 221c | +++ | 250f | ++ | | |
| 216d | + | 246b | +++ | | |
| 230e | ++ | 247b | +++ | | |
| 231c | +++ | 248c | +++ | | |
| 232c | +++ | 249f | +++ | | |
| 233c | +++ | 236d | +++ | | |
| 334d | ++ | 261c | +++ | 377e | +++ |
| 329b | +++ | 262c | +++ | 270c | +++ |
| 330c | +++ | 263c | +++ | 271e | +++ |
| 258f | +++ | 431c | +++ | 272e | +++ |
| 259e | +++ | 310c | +++ | 309h | +++ |
| 331c | +++ | 361c | +++ | 380e | + |
| 260g | +++ | 407d | + | 406e | +++ |
| 409f | +++ | 339c | +++ | 405e | +++ |
| 267h | +++ | 303g | +++ | 451c | +++ |
| 332e | +++ | 341e | +++ | 456c | +++ |
| 335d | + | 376e | +++ | 410d | +++ |
| 350e | +++ | 336c | +++ | 273g | +++ |
| 408e | + | 338c | +++ | 411e | +++ |
| 337b | +++ | 362e | +++ | 412b | +++ |
| 340e | ++ | 264c | +++ | 436c | +++ |
| 360c | +++ | 351f | +++ | 390c | +++ |
| 268h | +++ | 374f | +++ | 257k | +++ |
| 461c | +++ | 269h | +++ | 414b | +++ |
| 432c | +++ | 328f | +++ | 442d | +++ |
| 274g | +++ | 278e | +++ | 444c | +++ |
| 391f | +++ | 277e | +++ | 404c | +++ |
| 282f | +++ | 372c | +++ | 445c | +++ |
| 378d | +++ | 439c | +++ | 397e | +++ |
| 381e | + | 440c | +++ | 398c | +++ |
| 314f | +++ | 458b | +++ | 283c | +++ |
| 435b | +++ | 413m | +++ | 446c | +++ |
| 434c | +++ | 396e | +++ | 423c | +++ |
| 275e | ++ | 413n | +++ | 284f | +++ |
| 276f | +++ | 321f | +++ | 400e | +++ |
| 433c | +++ | 279c | +++ | 452d | +++ |
| 308h | +++ | 443i | +++ | 453d | +++ |
| 437c | +++ | 441c | +++ | 429c | +++ |
| 438c | +++ | 415e | +++ | 417e | +++ |
| 393d | +++ | 280c | +++ | 421e | +++ |
| 394c | +++ | 281c | +++ | 399d | +++ |
| 416d | +++ | 420e | +++ | 401e | +++ |
| 454d | +++ | 322c | +++ | 318c | +++ |
| 419c | +++ | 322d | +++ | 316b | +++ |
| 402f | +++ | 287c | +++ | 293c | +++ |
| 457c | +++ | 288f | +++ | 379c | +++ |
| 395c | +++ | 320c | +++ | 426c | +++ |
| 455c | +++ | 324c | +++ | 427b | +++ |
| 403e | +++ | 289d | +++ | 294f | +++ |
| 286g | +++ | 290c | +++ | 295c | +++ |
| 285e | +++ | 291g | +++ | 296c | +++ |
| 342e | +++ | 333g | +++ | 313c | +++ |
| 326g | ++ | 347b | +++ | 312b | +++ |
| 327d | +++ | 319c | +++ | 297c | +++ |
| 422e | +++ | 325a | +++ | 428c | +++ |
| 424d | +++ | 292f | +++ | 311b | + |
| 343e | +++ | 349b | +++ | 307f | +++ |
| 323c | +++ | 348b | +++ | 298f | +++ |
| 345b | +++ | 317f | +++ | 315f | +++ |
| 346c | +++ | 425f | +++ | 383b | +++ |
| 382h | +++ | 459h | +++ | 385d | +++ |
| 368c | +++ | 460h | +++ | 386c | +++ |
| 369d | +++ | 467b | +++ | 387b | +++ |
| 299c | +++ | 356c | +++ | 344f | +++ |
| 373b | +++ | 384c | +++ | 365f | +++ |
| 301b | +++ | 466c | +++ | 471d | +++ |
| 300c | +++ | 392g | +++ | 472b | +++ |
| 306f | +++ | 357b | +++ | 462c | +++ |
| 266g | +++ | 355c | +++ | 463b | +++ |
| 265g | +++ | 370f | +++ | 389c | +++ |
| 430c | +++ | 305d | +++ | 388d | +++ |
| 352c | +++ | 363c | +++ | 366d | +++ |
| 353b | +++ | 364d | +++ | 367c | +++ |
| 482b | +++ | 304b | +++ | 477c | +++ |
| 354c | +++ | 375c | +++ | 478b | +++ |
| 464d | +++ | 371c | +++ | 447d | +++ |
| 465b | +++ | 358c | +++ | 448c | +++ |
| 302f | +++ | 359b | +++ | 473e | +++ |
| 480c | +++ | 492b | +++ | 507f | ++ |
| 481b | +++ | 484c | +++ | 508b | +++ |
| 449c | +++ | 485b | +++ | 509d | +++ |
| 450b | +++ | 493b | +++ | 510d | +++ |
| 468h | +++ | 494b | +++ | 511e | +++ |
| 469g | +++ | 418c | +++ | 512d | +++ |
| 470b | +++ | 497d | +++ | 513c | +++ |
| 479d | +++ | 496c | +++ | 514d | +++ |
| 474c | +++ | 495d | +++ | 515c | +++ |
| 475g | +++ | 498c | +++ | 520c | +++ |
| 476f | +++ | 499b | +++ | 521b | +++ |
| 486c | +++ | 500c | +++ | 522c | +++ |
| 487b | +++ | 501f | +++ | 523b | +++ |
| 488c | +++ | 502c | +++ | 527b | +++ |
| 489b | +++ | 503c | +++ | 524b | +++ |
| 490c | +++ | 504c | +++ | 525c | +++ |
| 491b | +++ | 505d | +++ | 526b | +++ |
| 483c | +++ | 506e | +++ | 517d | +++ |

| Compound | IC$_{50}$ |
|---|---|
| 518b | +++ |
| 516c | +++ |
| 519c | +++ |
| 530c | +++ |
| 529b | +++ |
| 528d | +++ |
| 531c | +++ |
| 532d | +++ |
| 533c | +++ |

INCORPORATION BY REFERENCE

All of the U.S. patents and U.S. and PCT published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound, or a pharmaceutically acceptable salt thereof, selected from the group consisting of:

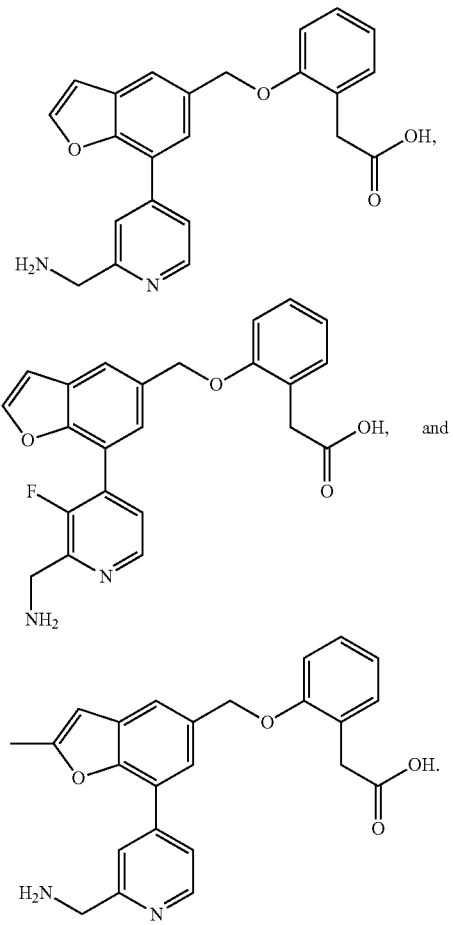

and

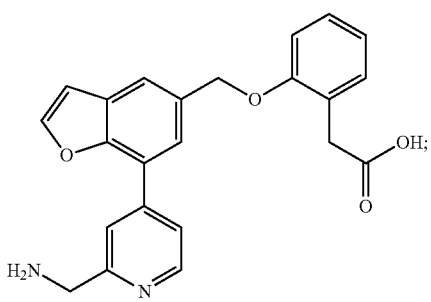 [SMILES: NCc1cc(-c2cc(COc3ccccc3CC(=O)O)cc3ccoc23)ccn1]

or a pharmaceutically acceptable salt thereof.

2. The compound of claim 1, wherein the compound is in the form of a hydrochloride salt.

3. The compound of claim 1, wherein the compound is

4. The compound of claim 3, wherein the compound is in the form of a hydrochloride salt.

5. The compound of claim 1, wherein the compound is

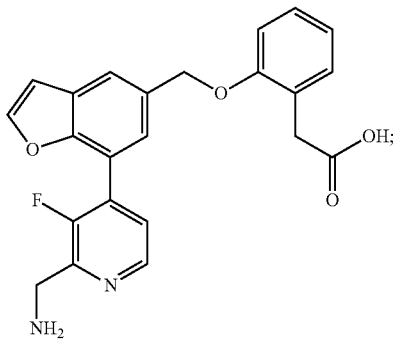 [SMILES: NCc1nccc(-c2cc(COc3ccccc3CC(=O)O)cc3ccoc23)c1F]

or a pharmaceutically acceptable salt thereof.

6. The compound of claim 5, wherein the compound is in the form of a hydrochloride salt.

7. The compound of claim 1, wherein the compound is

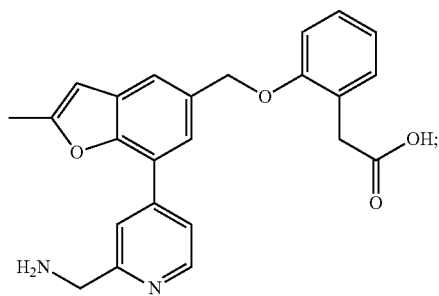 [SMILES: Cc1cc2cc(COc3ccccc3CC(=O)O)cc(-c3ccnc(CN)c3)c2o1]

or a pharmaceutically acceptable salt thereof.

8. The compound of claim 7, wherein the compound is in the form of a hydrochloride salt.

9. A pharmaceutical composition, comprising the compound of claim 1, or a pharmaceutically acceptable salt thereof, and a pharmaceutically acceptable carrier.

10. A pharmaceutical composition, comprising the compound of claim 3, or a pharmaceutically acceptable salt thereof, and a pharmaceutically acceptable carrier.

11. A pharmaceutical composition, comprising the compound of claim 5, or a pharmaceutically acceptable salt thereof, and a pharmaceutically acceptable carrier.

12. A pharmaceutical composition, comprising the compound of claim 7, or a pharmaceutically acceptable salt thereof, and a pharmaceutically acceptable carrier.

* * * * *